(12) United States Patent
Tanada et al.

(10) Patent No.: US 12,371,454 B2
(45) Date of Patent: Jul. 29, 2025

(54) CYCLIC PEPTIDE COMPOUND HAVING KRAS INHIBITORY ACTION

(71) Applicant: CHUGAI SEIYAKU KABUSHIKI KAISHA, Tokyo (JP)

(72) Inventors: Mikimasa Tanada, Gotemba (JP); Koji Takano, Kamakura (JP); Atsushi Matsuo, Kamakura (JP); Minoru Tamiya, Gotemba (JP); Aya Chiyoda, Gotemba (JP); Toshiya Ito, Gotemba (JP); Takeo Iida, Singapore (SG)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 18/773,066

(22) Filed: Jul. 15, 2024

(65) Prior Publication Data
US 2024/0400617 A1 Dec. 5, 2024

Related U.S. Application Data

(63) Continuation of application No. 17/773,733, filed as application No. PCT/JP2020/041277 on Nov. 5, 2020.

(30) Foreign Application Priority Data

Nov. 7, 2019 (JP) .................. 2019-202407

(51) Int. Cl.
| | | |
|---|---|---|
| *A61K 38/00* | (2006.01) |
| *C07C 271/22* | (2006.01) |
| *C07C 317/04* | (2006.01) |
| *C07C 323/09* | (2006.01) |
| *C07D 205/04* | (2006.01) |
| *C07D 211/38* | (2006.01) |
| *C07D 213/55* | (2006.01) |
| *C07D 213/61* | (2006.01) |
| *C07D 213/64* | (2006.01) |
| *C07D 213/65* | (2006.01) |
| *C07D 295/15* | (2006.01) |
| *C07D 309/12* | (2006.01) |
| *C07D 333/28* | (2006.01) |
| *C07D 409/12* | (2006.01) |

(Continued)

(52) U.S. Cl.
CPC ............. *C07K 7/64* (2013.01); *C07C 271/22* (2013.01); *C07C 317/04* (2013.01); *C07C 323/09* (2013.01); *C07D 205/04* (2013.01); *C07D 211/38* (2013.01); *C07D 213/55* (2013.01); *C07D 213/61* (2013.01); *C07D 213/64* (2013.01); *C07D 213/65* (2013.01); *C07D 295/15* (2013.01); *C07D 309/12* (2013.01); *C07D 333/28* (2013.01); *C07D 409/12* (2013.01); *C07F 5/025* (2013.01); *A61K 38/00* (2013.01); *C07C 2601/02* (2017.05); *C07C 2601/04* (2017.05); *C07C 2601/08* (2017.05); *C07C 2603/18* (2017.05)

(58) Field of Classification Search
CPC ......... A61K 38/00; A61K 38/12; A61P 35/00; A61P 43/00; C07C 2601/02; C07C 2601/04; C07C 2601/08; C07C 2603/18; C07C 271/22; C07C 317/04; C07C 323/09; C07C 229/12; C07C 229/36; C07C 229/46; C07C 237/06; C07C 255/19; C07C 255/21; C07C 2601/14; C07C 323/57; C07C 323/62; C07D 205/04; C07D 207/06; C07D 207/10; C07D 207/16; C07D 211/10; C07D 211/18; C07D 211/38; C07D 213/55; C07D 213/61; C07D 213/62; C07D 213/64; C07D 213/65; C07D 263/04; C07D 295/15; C07D 295/185; C07D 305/08; C07D 309/12; C07D 333/28; C07D 333/68; C07D 409/12; C07D 491/08; C07D 205/06; C07D 207/04; C07D 209/08; C07D 211/14; C07D 213/38; C07D 215/12; C07D 295/10; C07D 307/79; C07D 317/46; C07F 5/025; C07K 7/54; C07K 7/56; C07K 7/64; C07K 5/0202; C07K 5/0215; C07K 7/50
See application file for complete search history.

(56) References Cited

U.S. PATENT DOCUMENTS

| | | |
|---|---|---|
| 4,859,736 A | 8/1989 | Rink |
| 5,057,415 A | 10/1991 | Schuetz et al. |
| 5,059,679 A | 10/1991 | Yajima et al. |

(Continued)

FOREIGN PATENT DOCUMENTS

| | | |
|---|---|---|
| EP | 1277755 A1 | 1/2003 |
| EP | 1424395 A1 | 6/2004 |

(Continued)

OTHER PUBLICATIONS

Afonso, A., et al., "Solid-Phase Synthesis of Biaryl Cyclic Peptides Containing a 3-Aryltyrosine," Eur J Org Chem., 31:6204-6211 (2012).

(Continued)

*Primary Examiner* — Aradhana Sasan
*Assistant Examiner* — Mercy H Sabila
(74) *Attorney, Agent, or Firm* — Nixon & Vanderhye P.C.

(57) ABSTRACT

The present inventors found cyclic peptide compounds that interact with Ras, and non-natural amino acids useful for the production of the cyclic peptide compounds. The inventors also found that the cyclic peptide compounds inhibit the binding between Ras and SOS. In addition, the inventors found specific non-natural amino acids contained in the cyclic peptide compounds and methods for production thereof.

12 Claims, No Drawings

(51) Int. Cl.
*C07F 5/02* (2006.01)
*C07K 7/64* (2006.01)

(56) References Cited

U.S. PATENT DOCUMENTS

| | | |
|---|---|---|
| 6,057,289 A | 5/2000 | Mulye |
| 7,288,372 B2 | 10/2007 | Olejnik et al. |
| 7,439,222 B2 | 10/2008 | Guinn et al. |
| 8,518,666 B2 | 8/2013 | Wang et al. |
| 8,809,280 B2 | 8/2014 | Strom et al. |
| 9,133,245 B2 | 9/2015 | Gao et al. |
| 9,409,952 B2 | 8/2016 | Kariyuki et al. |
| 9,701,993 B2 | 7/2017 | Suga et al. |
| 10,711,268 B2 | 7/2020 | Murakami et al. |
| 10,815,489 B2 | 10/2020 | Ohta et al. |
| 11,492,369 B2 | 11/2022 | Nomura et al. |
| 11,542,299 B2 | 1/2023 | Nomura et al. |
| 11,732,002 B2 | 8/2023 | Iwasaki et al. |
| 11,787,836 B2 | 10/2023 | Nomura et al. |
| 11,891,457 B2 | 2/2024 | Kariyuki et al. |
| 12,071,396 B2 | 8/2024 | Wadamoto |
| 2003/0219780 A1 | 11/2003 | Olejnik et al. |
| 2005/0165217 A1 | 7/2005 | Guinn et al. |
| 2008/0044854 A1 | 2/2008 | Wang et al. |
| 2008/0221303 A1 | 9/2008 | Katzhendler et al. |
| 2010/0137561 A1 | 6/2010 | Chen |
| 2010/0292435 A1 | 11/2010 | Chen et al. |
| 2013/0035296 A1 | 2/2013 | Strom et al. |
| 2013/0217599 A1 | 8/2013 | Suga et al. |
| 2013/0274205 A1 | 10/2013 | Guerlavais et al. |
| 2014/0128572 A1 | 5/2014 | Monnaie et al. |
| 2014/0194369 A1 | 7/2014 | Gao et al. |
| 2015/0008054 A1 | 1/2015 | Hoshino et al. |
| 2015/0080549 A1 | 3/2015 | Kariyuki et al. |
| 2016/0264627 A1 | 9/2016 | Henning et al. |
| 2016/0272964 A1 | 9/2016 | Murakami et al. |
| 2016/0311858 A1 | 10/2016 | Kariyuki et al. |
| 2018/0127761 A1 | 5/2018 | Ohta et al. |
| 2019/0338050 A1 | 11/2019 | Nakano et al. |
| 2020/0040372 A1 | 2/2020 | Tanaka et al. |
| 2020/0131669 A1 | 4/2020 | Muraoka et al. |
| 2020/0277327 A1 | 9/2020 | Nomura et al. |
| 2020/0339623 A1 | 10/2020 | Nomura et al. |
| 2021/0024579 A1 | 1/2021 | Shipman |
| 2021/0061860 A1 | 3/2021 | Kariyuki et al. |
| 2021/0087572 A1 | 3/2021 | Ohta et al. |
| 2022/0017456 A1 | 1/2022 | Ishizawa |
| 2022/0024972 A1 | 1/2022 | Iwasaki et al. |
| 2022/0144762 A1 | 5/2022 | Wadamoto |
| 2022/0205009 A1 | 6/2022 | Shinohara et al. |
| 2022/0411462 A1 | 12/2022 | Hou et al. |
| 2023/0026641 A1 | 1/2023 | Nomura et al. |
| 2023/0056969 A1 | 2/2023 | Kondo et al. |
| 2023/0096766 A1 | 3/2023 | Muraoka et al. |
| 2023/0108274 A1 | 4/2023 | Kagotani et al. |
| 2023/0138226 A1 | 5/2023 | Nomura et al. |
| 2023/0151060 A1 | 5/2023 | Tanada et al. |
| 2023/0295221 A1 | 9/2023 | Iwasaki et al. |
| 2023/0303619 A1 | 9/2023 | Iwaskai et al. |
| 2023/0391818 A1 | 12/2023 | Nomura et al. |
| 2023/0406879 A1 | 12/2023 | Nomura et al. |
| 2024/0052340 A1 | 2/2024 | Nishimura et al. |
| 2024/0067674 A1 | 2/2024 | Sekita et al. |
| 2024/0124121 A1 | 4/2024 | Morita et al. |
| 2024/0148821 A1 | 5/2024 | Tanada et al. |
| 2024/0158446 A1 | 5/2024 | Kawada et al. |
| 2024/0166689 A1 | 5/2024 | Kariyuki et al. |
| 2024/0239842 A1 | 7/2024 | Hayashi et al. |

FOREIGN PATENT DOCUMENTS

| | | |
|---|---|---|
| EP | 1964916 A1 | 9/2008 |
| EP | 2088202 A1 | 8/2009 |
| EP | 2141175 A1 | 1/2010 |
| EP | 2177533 A1 | 4/2010 |
| EP | 2380596 A1 | 10/2011 |
| EP | 2492344 A1 | 8/2012 |
| EP | 2610348 A1 | 7/2013 |
| EP | 2615455 A1 | 7/2013 |
| EP | 2088202 B1 | 8/2013 |
| EP | 2647720 A1 | 10/2013 |
| EP | 2813512 A1 | 12/2014 |
| EP | 2492344 B1 | 4/2016 |
| EP | 3031915 A1 | 6/2016 |
| EP | 2141175 B1 | 7/2016 |
| EP | 3424941 A1 | 1/2019 |
| EP | 3031915 B1 | 3/2019 |
| EP | 3636656 A1 | 4/2020 |
| EP | 3636807 A1 | 4/2020 |
| EP | 2813512 B1 | 3/2021 |
| EP | 3896056 A1 | 10/2021 |
| EP | 4043478 A1 | 8/2022 |
| JP | S57159747 A | 10/1982 |
| JP | S60169451 A | 9/1985 |
| JP | S62289 A | 1/1987 |
| JP | S62143698 A | 6/1987 |
| JP | S63260946 A | 10/1988 |
| JP | H01222795 A | 9/1989 |
| JP | H01250396 A | 10/1989 |
| JP | H0259146 B2 | 12/1990 |
| JP | H0681759 B2 | 10/1994 |
| JP | 2513775 B2 | 7/1996 |
| JP | 2001048866 A | 2/2001 |
| JP | 2002513750 A | 5/2002 |
| JP | 2002537317 A | 11/2002 |
| JP | 2003508408 A | 3/2003 |
| JP | 2003531199 A | 10/2003 |
| JP | 2005095013 A | 4/2005 |
| JP | 3662926 B2 | 6/2005 |
| JP | 2006022112 A1 | 1/2006 |
| JP | 2006501208 A | 1/2006 |
| JP | 2007319064 A | 12/2007 |
| JP | 2008125396 A | 6/2008 |
| JP | 2009096791 A | 5/2009 |
| JP | 2009528824 A | 8/2009 |
| JP | 4490663 B2 | 6/2010 |
| JP | 4502293 B2 | 7/2010 |
| JP | 2011139667 A | 7/2011 |
| JP | 2012506909 A | 3/2012 |
| JP | 2012510486 A | 5/2012 |
| JP | 2012525348 A | 10/2012 |
| JP | 5200241 B2 | 6/2013 |
| JP | 5592893 B2 | 9/2014 |
| JP | 2015509940 A | 4/2015 |
| JP | 5808882 B2 | 11/2015 |
| JP | 2018509172 A | 4/2018 |
| JP | 2020105162 A | 7/2020 |
| WO | WO-9504541 A1 | 2/1995 |
| WO | WO9525504 A1 | 9/1995 |
| WO | WO-9831700 A1 | 7/1998 |
| WO | WO9956727 A2 | 11/1999 |
| WO | WO0015656 A1 | 3/2000 |
| WO | WO0050007 A1 | 8/2000 |
| WO | WO-0181325 A2 | 11/2001 |
| WO | WO-02085923 A2 | 10/2002 |
| WO | WO-03014354 A1 | 2/2003 |
| WO | WO-03068990 A1 | 8/2003 |
| WO | WO-03089454 A2 | 10/2003 |
| WO | WO2004012716 A1 | 2/2004 |
| WO | WO-2005063791 A2 | 7/2005 |
| WO | WO-2007066627 A1 | 6/2007 |
| WO | WO-2007103307 A2 | 9/2007 |
| WO | WO-2007120614 A2 | 10/2007 |
| WO | WO-2008117833 A1 | 10/2008 |
| WO | WO2009054463 A1 | 4/2009 |
| WO | WO-2010053050 A1 | 5/2010 |
| WO | WO-2010062590 A2 | 6/2010 |
| WO | WO-2010063604 A1 | 6/2010 |
| WO | WO-2010125079 A2 | 11/2010 |
| WO | WO-2011049157 A1 | 4/2011 |
| WO | WO-2011051692 A1 | 5/2011 |
| WO | WO-2011058122 A1 | 5/2011 |
| WO | WO-2012026566 A1 | 3/2012 |
| WO | WO-2012033154 A1 | 3/2012 |

(56) References Cited

FOREIGN PATENT DOCUMENTS

| | | |
|---|---|---|
| WO | WO-2012074130 A1 | 6/2012 |
| WO | WO-2012122059 A1 | 9/2012 |
| WO | WO-2013100132 A1 | 7/2013 |
| WO | WO2013123266 A1 | 8/2013 |
| WO | WO-2014033466 A1 | 3/2014 |
| WO | WO-2014181888 A1 | 11/2014 |
| WO | WO-2015019192 A2 | 2/2015 |
| WO | WO-2015019999 A1 | 2/2015 |
| WO | WO-2015155676 A1 | 10/2015 |
| WO | WO-2015179434 A1 | 11/2015 |
| WO | WO-2015185162 A1 | 12/2015 |
| WO | WO2016071515 A1 | 5/2016 |
| WO | WO-2016100608 A1 | 6/2016 |
| WO | WO-2016115168 A1 | 7/2016 |
| WO | WO-2016148044 A1 | 9/2016 |
| WO | WO-2016154675 A1 | 10/2016 |
| WO | WO-2017150732 A1 | 9/2017 |
| WO | WO-2017181061 A1 | 10/2017 |
| WO | WO2018031730 A2 | 2/2018 |
| WO | WO-2018100561 A1 | 6/2018 |
| WO | WO-2018143145 A1 | 8/2018 |
| WO | WO-2018225851 A1 | 12/2018 |
| WO | WO-2018225864 A1 | 12/2018 |
| WO | WO-2019117274 A1 | 6/2019 |
| WO | WO-2020095983 A1 | 5/2020 |
| WO | WO-2020106647 A1 | 5/2020 |
| WO | WO-2020111238 A1 | 6/2020 |
| WO | WO-2020122182 A1 | 6/2020 |
| WO | WO-2020138336 A1 | 7/2020 |
| WO | WO-2020189540 A1 | 9/2020 |
| WO | WO-2021030855 A1 | 2/2021 |
| WO | WO2021090855 A1 | 5/2021 |
| WO | WO-2021090856 A1 | 5/2021 |
| WO | WO-2021132545 A1 | 7/2021 |
| WO | WO-2021132546 A1 | 7/2021 |
| WO | WO-2021246471 A1 | 12/2021 |
| WO | WO-2021261577 A1 | 12/2021 |
| WO | WO-2022097540 A1 | 5/2022 |
| WO | WO-2022138891 A1 | 6/2022 |
| WO | WO-2022145444 A1 | 7/2022 |
| WO | WO-2022234850 A1 | 11/2022 |
| WO | WO-2022234851 A1 | 11/2022 |
| WO | WO-2022234852 A1 | 11/2022 |
| WO | WO-2022234853 A1 | 11/2022 |
| WO | WO-2023127869 A1 | 7/2023 |
| WO | WO-2023140329 A1 | 7/2023 |
| WO | WO2023190748 A1 | 10/2023 |
| WO | WO2023214576 A1 | 11/2023 |
| WO | WO2023214577 A1 | 11/2023 |

OTHER PUBLICATIONS

Alakhov, Y. B., et al., "Butylation of the Tryptophan Indole Ring: a Side Reaction During the Removal of t-Butyloxycarbonyl and t-Butyl Protecting Groups in Peptide Synthesis," J Chem Soc D., 7:406b-407 (1970).

Albericio, F., et al., "Fmoc Methodology: Cleavage from the Resin and Final Deprotection," Amino Acids, Peptides and Proteins in Organic Chemistry, 3:349-369 (2011).

Alex, A., et al., "Intramolecular hydrogen bonding to improve membrane permeability and absorption in beyond rule of five chemical space," Med Chem Commun., 2:669-674 (2011).

Alvaro, G., et al., "A Novel Activity of Immobilized Penicillin G Acylase: Removal of Benzyloxycarbonyl Amino Protecting Group," Biocatalysis and Biotransformation, 18(3):253-238 (2000).

Bastiaans, H. M. M., et al., "Flexible and Convergent Total Synthesis of Cyclotheonamide B," J Org Chem., 62:3880-3889 (1997).

Beck, J. G., et al., "Intestinal Permeability of Cyclic Peptides: Common Key Backbone Motifs Identified," J Amer Chem Soc., 134(29):12125-12133 (2012).

Behrendt, R., et al., "Advances in Fmoc Solid-phase Peptide Synthesis," J Pep Sci., 22(1):4-27 (2016).

Bock, J. E., et al., "Getting in Shape: Controlling Peptide Bioactivity and Bioavailability Using Conformational Constraints," ACS Chem Biol., 8(3):488-499 (2013).

Bockus, A. T., et al., "Form and Function in Cyclic Peptide Natural Products: A Pharmacokinetic Perspective," Curr Top Med Chem., 13:821-836 (2013).

Boehm, M., et al., "Discovery of Potent and Orally Bioavailable Macrocyclic Peptide-Peptoid Hybrid CXCR7 Modulators," J Med Chem., 60:9653-9663 (2017).

Bolek, S. and Ignatowska, J., "Ring opening reactions of cyclic sulfamidates. Synthesis of β-fluoroaryl alanines and derivatives of 4,4-difluoroglutamic acid," Journal of Fluorine Chemistry, 27:13-21 (2019).

Brandt, W., et al., "Systematic Conformational Investigations of Peptoids and Peptoid-Peptide Chimeras," Biopolymers (Pept Sci), 96(5):651-668 (2011).

Brunner, J., "Biosynthetic Incorporation of Non-natural Amino Acids into Proteins," Chemical Society Reviews, 22(3):183-189 (1993).

Brown, Z.Z., et al., "Exploiting an Inherent Neighboring Group Effect of α-Amino Acids to Synthesize Extremely Hindered Dipeptides," J Am Chem Soc., 130(44):14382-14383 (2008).

Burkholder, T. P., et al., "Acid-catalyzed O-allylation of β-Hydroxy-α-Amino Acids: An Entry into Conformationally Constrained Dipeptide Surrogates," Bioorganic & Medicinal Chemistry Letters, 2(6):579-582 (1992).

Carpino, L.A., et al., "Protected Amnio Acid Chlorides vs Protected Amino Acid Fluorides: Reactivity Comparisons," Tetrahedron Letters, 39:241-244 (1998).

Carpino, L.A., et al., "Dramatically Enhanced N→O Acyl Migration During the Trifluoroacetic Acid-based Deprotection Step in Solid Phase Peptide Synthesis," Tetrahedron Letters, 46(8):1361-1364 (2005).

Chatterjee, J., et al., "N-Methylation of Peptides: A New Perspective in Medicinal Chemistry," Accounts of Chemical Research, 41(10):1331-1342 (2008).

Chen, C.C., et al., "A Mild Removal of Fmoc Group Using Sodium Azide," Amino Acids, 46(2):367-374 (2014).

Chen, J.F., et al., "Effect of Alanine-293 Replacement on the Activity, ATP Binding, and Editing of *Escherichia coli* Leucyl-tRNA Synthetase," Biochemistry, 40(5):1144-1149 (2001).

Chen, S., et al., "Structurally Diverse Cyclisation Linkers Impose Different Backbone Conformations in Bicyclic Peptides," Chembiochem, 13(7):1032-1038 (2012).

Cornella, J., et al., "Practical Ni-Catalyzed Aryl-Alkyl Cross-Coupling of Secondary Redox-Active Esters," J Amer Chem Soc., 138(7):2174-2177 (2016).

Cox, A. A., et al., "Drugging the Undruggable RAS: Mission Possible?," Nat Rev Drug Dis., 13(11):828-851 (2014).

Creighton, C. J., et al., "Mechanistic Studies of an Unusual Amide Bond Scission," J Amer Chem Soc., 121(29):6786-6791 (1999).

Cudic, M. and Fields, G. B., "Solid-Phase Peptide Synthesis," Molecular Biomethods Handbook, 515-546 (2008).

Cusack, S., et al., "The 2 a Crystal Structure of Leucyl-tRNA Synthetase and Its Complex With a Leucyl-adenylate Analogue," The EMBO Journal, 19(10):2351-2361 (2000).

Dailler, D., et al., "Divergent Synthesis of Aeruginosas Based on a C(sp(3)-H Activation Strategy," Chem Eur J., 21(26):9370-9379 (2015).

Das, M. and Himaja, M. ,"Design, Synthesis and Biological Evaluation of Linear Tetrapepide D-Ala-L-(Gly-Val-Val) (AGVV)," UJPB, 01(02):21-24 (2013).

Dawson, P.E., et al., "Synthesis of Proteins by Native Chemical Ligation," Science, 266(5186):776-779 (1994).

Di Gioia, M. L., et al., "N-Methylation of Peptides of Selected Positions during the Elongation of the Peptide Chain in Solution Phase," J Org Chem., 70:3892-3897 (2005).

Doi, Y., et al., "Elongation Factor Tu Mutants Expand Amino Acid Tolerance of Protein Biosynthesis System," J Amer Chem Soc., 129(46):14458-14462 (2007).

Doublie, S., et al., "Tryptophanyl-tRNA Synthetase Crystal Structure Reveals an Unexpected Homology to Tyrosyl-tRNA Synthetase," Structure, 3(1):17-31 (1995).

(56) References Cited

OTHER PUBLICATIONS

Eberhard, H., et al., "N—O-acyl Shift in Fmoc-based Synthesis of Phosphopeptides," Org Biomol Chem., 6(8):1349-1355 (2008).

Fang, W. J., et al., "Deletion of Ac-NMePhe(1) From [NMePhe(1)] Arodyn Under Acidic Conditions, Part 1: Effects of Cleavage Conditions and N-terminal Functionality," Biopolymers, 96(1):97-102 (2011).

Frankel, A., et al., "Encodamers: Unnatural Peptide Oligomers Encoded in RNA," Chemistry & Biology, 10(11):1043-1050 (2003).

Fujii, N., et al., "Trimethylsilyl Trifluoromethanesulphonate as a Useful Deprotecting Reagent in Both Solution and Solid Phase Peptide Syntheses," Journal of the Chemical Society, Chemical Communications, 4:274-275 (1987).

Fujino, M., et al., "Further Studies on the Use of Multi-substituted Benzenesulfonyl Groups for Protection of the Guanidino Function of Arginine," Chemical and Pharmaceutical Bulletin, 29(10):2825-2831 (1981).

Fujino, T., et al., "Reevaluation of the D-amino Acid Compatibility With the Elongation Event in Translation," Journal of the American Chemical Society, 135(5):1830-1837 (2013).

Fujino, T., et al., "Ribosomal Synthesis of Peptides with Multiple β-Amino Acids," Journal of the American Chemical Society, 138(6):1962-1969 (2016).

Fukai, S., et al., "Mechanism of Molecular Interactions for Trna(Val) Recognition by Valyl-trna Synthetase," RNA, 9(1):100-111 (2003).

Fukai, S., et al., "Structural Basis for Double-sieve Discrimination of L-valine From L-isoleucine and L-threonine by the Complex of Trna(Val) and Valyl-trna Synthetase," Cell, 103(5):793-803 (2000).

Fukunaga, R., et al., "Structural Basis for Non-cognate Amino Acid Discrimination by the Valyl-trna Synthetase Editing Domain," J Biol Chem., 280(33):29937-29945 (2005).

Ganesan, A., et al., "The Impact of Natural Products Upon Modern Drug Discovery," Current Opinion in Chemical Biology, 12(3):306-317 (2008).

GenBank, "Valine-tRNA ligase [Thermus thermophilus]," Accession No. P96142, accessed on Jan. 27, 2021.

Gilon, C., et al., "Backbone Cyclization: a New Method for Conferring Conformational Constraint on Peptides," Biopolymers, 31(6):745-750 (1991).

Goto, et al., "Ribosomal Synthesis of Combinatorial Polypeptides Containing Unusual Amino Acid Blocks," Kagaku Kogyo, 58(4):255-262 (2007).

Goto, Y., et al., "Flexizymes for Genetic Code Reprogramming," Nature Protocols, 6(6):779-790 (2011).

Goto, Y., et al., "Translation Initiation With Initiator Trna Charged With Exotic Peptides," Journal of the American Chemical Society, 131(14):5040-5041 (2009).

Gracia, S.R., et al., "Synthesis of chemically modified bioactive peptides: recent advances, challenges and developments for medicinal chemistry," Future Medicinal Chemistry, 1(7):1289-1310 (2009).

Gravestock, et al., "Novel branched isocyanides as useful building blocks in the Passerini-amine deprotection-acyl migration (PADAM) synthesis of potential HIV-1 protease inhibitors," Tetrahedron Letters, 53(26):3225-3229 (2012).

Grosjean, H. and Bjork, G.R., "Enzymatic Conversion of Cytidine to Lysidine in Anticodon of Bacterial Isoleucyl-tRNA—an Alternative Way of RNA Editing," Trends in Biochemical Sciences, 29(4):165-168 (2004).

Hartman, M.C.T., et al., "An Expanded Set of Amino Acid Analogs for the Ribosomal Translation of Unnatural Peptides," PLoS One, 2(10):e972 (2007).

Hartman, M.C.T., et al., "Enzymatic Aminoacylation of Trna With Unnatural Amino Acids," Proceedings of the National Academy of Sciences of the United States of America, 103(12):4356-4361 (2006).

Hayashi, G., et al., "[Ribosomal Synthesis of Nonstandard Cyclic Peptides and Its Application to Drug Discovery]," Seikagaku. The Journal of Japanese Biochemical Society, 82(6):505-514 (2010).

Hecht, S.M., et al., "Chemical Aminoacylation" of Trna's," The Journal of Biological Chemistry," 253(13):4517-4520 (1978).

Heinis, C., et al., "Phage-encoded Combinatorial Chemical Libraries Based on Bicyclic Peptides," Nature Chemical Biology, 5(7):502-507 (2009).

Higuchi, T. and Suga, H., "Programmed Synthesis of Natural Product-Like Non-Standard Peptides Using the Translation System and Its Application," Journal of Synthetic Organic Chemistry, 68(3):217-227 (2010).

Hoogenboom, H.R., et al., "Selecting and Screening Recombinant Antibody Libraries," Nature Biotechnology, 23(9):1105-1116 (2005).

Hountondji, C., et al., "Crucial Role of Conserved Lysine 277 in the Fidelity of Trna Aminoacylation by *Escherichia coli* Valyl-trna Synthetase," Biochemistry, 41(50):14856-14865 (2002).

Hountondji, C., et al., "Valyl-trna Synthetase From *Escherichia coli* Maldi-ms Identification of the Binding Sites for L-valine or for Noncognate Amino Acids Upon Qualitative Comparative Labeling With Reactive Amino-acid Analogs," European Journal of Biochemistry, 267(15):4789-98 (2000).

Hruby, V.J., et al., "Emerging Approaches in the Molecular Design of Receptor-selective Peptide Ligands: Conformational, Topographical and Dynamic Considerations," The Biochemical Journal, 268(2):249-262 (1990).

Huang, Y., et al., "RNA Display Methods for the Discovery of Bioactive Macrocycles," Chem Rev., 119:10360-10391 (2019).

Huihui, K.M.M., et al., "Decarboxylative Cross-Electrophile Coupling of N-Hydroxyphthalimide Esters With Aryl Iodides," Journal of the American Chemical Society, 138(15):5016-5019 (2016).

Ikeuchi, Y., et al., "Agmatine-conjugated Cytidine in a tRNA Anticodon Is Essential for AUA Decoding in Archaea," Nature Chemical Biology, 6(4):277-282 (2010).

Ikeuchi, Y., et al., "Molecular Mechanism of Lysidine Synthesis That Determines tRNA Identity and Codon Recognition," Molecular Cell, 19(2):235-246 (2005).

Isidro-Llobet, A., et al., "Amino Acid-protecting Groups," Chemical Reviews, 109(6):2455-2504 (2009).

Itoh, Y., et al., "Crystallographic and Mutational Studies of Seryl-trna Synthetase From the Archaeon Pyrococcus Horikoshii," RNA Biology, 5(3):169-177 (2008).

Iwane, Y., et al., "Expanding the Amino Acid Repertoire of Ribosomal Polypeptide Synthesis via the Artificial Division of Codon Boxes," Nature Chemistry, 8(4):317-325 (2016).

Jaradat, D.M.M., et al., "Thirteen Decades of Peptide Synthesis: Key Developments in Solid Phase Peptide Synthesis and Amide Bond Formation Utilized in Peptide Ligation," Amino Acids, 50(1):39-68 (2018).

Jones, A.B., et al., "A Formal Synthesis of FK-506. Exploration of Some Alternatives to Macrolactamization," The Journal of Organic Chemistry, 55(9):2786-2797 (1990).

Josephson, K., et al., "mRNA Display: From Basic Principles to Macrocycle Drug Discovery," Drug Discovery Today, 19(4):388-399 (2014).

Josephson, K., et al., "Ribosomal Synthesis of Unnatural Peptides," Journal of the American Chemical Society, 127(33):11727-11735 (2005).

Kato, et al., Yakubutsutaishagaku. 2nd edition, pp. 9-13 (2000).

Kato, et al., Yakubutsutaishagaku. 3rd edition, pp. 43-46 (2010).

Katoh, T., et al., "Ribosomal Synthesis of Backbone Macrocyclic Peptides," Chemical Communications (Cambridge, England), 47(36):9946-9958 (2011).

Kawakami, T. and Aimoto, S., "Sequential Peptide Ligation by Using a Controlled Cysteinyl Prolyl Ester (CPE) Autoactivating Unit," Tetrahedron Letters, 48(11):1903-1905 (2007).

Kawakami, T., et al., "Diverse Backbone-cyclized Peptides via Codon Reprogramming," Nature Chemical Biology, 5(12):888-890 (2009).

Kawakami, T., et al., "In Vitro Selection of Multiple Libraries Created by Genetic Code Reprogramming to Discover Macrocyclic Peptides That Antagonize VEGFR2 Activity in Living Cells," ACS Chemical Biology, 8(6):1205-1214 (2013).

Kawakami, T., et al., "Incorporation of Electrically Charged N-alkyl Amino Acids Into Ribosomally Synthesized Peptides via Post-translational Conversion," Chemical Science, 5(3):887-893 (2014).

(56) References Cited

OTHER PUBLICATIONS

Kawakami, T., et al., "Messenger RNA-programmed Incorporation of Multiple N-methyl-amino Acids Into Linear and Cyclic Peptides," Chemistry & Biology, 15(1):32-42 (2008).
Kawakami, T., et al., "Ribosomal Synthesis of Polypeptoids and Peptoid-peptide Hybrids," Journal of the American Chemical Society, 130(50):16861-16863 (2008).
Kiho, T., et al., "Total Synthesis of Pleofugin A, a Potent Inositol Phosphorylceramide Synthase Inhibitor," Organic Letters, 20(15):4637-4640 (2018).
Kleineweischede, R., et al., "Chemoselective Peptide Cyclization by Traceless Staudinger Ligation," Angewandte Chemie (International ed. in English), 47(32):5984-5988 (2008).
Kobayashi, T., et al., "Recognition of Non-alpha-amino Substrates by Pyrrolysyl-tRNA Synthetase," Journal of Molecular Biology, 385(5):1352-1360 (2009).
Kopina, B.J. and Lauhon, C.T., "Efficient Preparation of 2,4-diaminopyrimidine Nucleosides: Total Synthesis of Lysidine and Agmatidine," Organic Letters, 14(16):4118-4121 (2012).
Kuhn, B., et al., "Intramolecular Hydrogen Bonding in Medicinal Chemistry," Journal of Medicinal Chemistry, 53(6):2601-2611 (2010).
Lajoie, M.J., et al., "Overcoming Challenges in Engineering the Genetic Code," Journal of Molecular Biology, 428(5PtB):1004-1021 (2016).
Lambert, J.N., et al., "The synthesis of cyclic peptides," J Chem Soc, Perkin Trans., 1:471-484 (2001).
Lassak, J., et al., "Stall No More at Polyproline Stretches With the Translation Elongation Factors EF-P and IF-5A," Molecular Microbiology, 99(2):219-235 (2016).
Laufer, B., et al., "The Impact of Amino Acid Side Chain Mutations in Conformational Design of Peptides and Proteins," Chemistry, 16(18):5385-5390 (2010).
Lee, K.W., et al., "Molecular Modeling Study of the Editing Active Site of *Escherichia coli* Leucyl-tRNA Synthetase: Two Amino Acid Binding Sites in the Editing Domain," Proteins, 54(4):693-704 (2004).
Lejeune, V., et al., "Towards a Selective Boc Deprotection on Acid Cleavable Wang Resin," Tetrahedron Letters, 44(25):4757-4759 (2003).
Lenzi, A., et al., "Synthesis of N-Boc-α-amino Acids With Nucleobase Residues as Building Blocks for the Preparation of Chiral PNA (Peptidic Nucleic Acids)," Tetrahedron Letters, 36(10):1713-1716 (1995).
Li, H., et al., "Ni-Catalyzed Electrochemical Decarboxylative C—C Couplings in Batch and Continuous Flow", Organic Letters, 20(5):1338-1341 (2018).
Li, S., et al., "In Vitro Selection of Mrna Display Libraries Containing an Unnatural Amino Acid," Journal of the American Chemical Society, 124(34):9972-9973 (2002).
Li, X., et al., "Salicylaldehyde Ester-induced Chemoselective Peptide Ligations: Enabling Generation of Natural Peptidic Linkages at the Serine/threonine Sites," Organic Letters, 12(8):1724-1727 (2010).
Liniger, M., et al., "Total Synthesis and Characterization of 7-Hypoquinuclidonium Tetrafluoroborate and 7-Hypoquinuclidone BF3 Complex," Journal of the American Chemical Society, 138(3):969-974 ( 2016).
Liu, D.R., et al., "Engineering a tRNA and Aminoacyl-tRNA Synthetase for the Site-specific Incorporation of Unnatural Amino Acids Into Proteins in Vivo," Proceedings of the National Academy of Sciences of the United States of America, 94(19):10092-10097 (1997).
Liu, Z., et al., "N-Boc Deprotection and Isolation Method for Water-soluble Zwitterionic Compounds," The Journal of Organic Chemistry, 79(23):11792-11796 (2014).
Lodder, M., et al., "The N-pentenoyl Protecting Group for Aminoacyl-tRNAs," Methods, 36(3):245-251 (2005).
Loos, P., et al., "Unified Azoline and Azole Syntheses by Optimized Aza-Wittig Chemistry," European Journal of Organic Chemistry, 2013(16):3290-3315 (2013).
Lundquist, K.Y., et al., "Improved Solid-phase Peptide Synthesis Method Utilizing Alpha-azide-protected Amino Acids," Organic Letters, 3(5):781-783 (2001).
Luo, D., et al., "Total Synthesis of the Potent Marine-Derived Elastase Inhibitor Lyngbyastatin 7 and in Vitro Biological Evaluation in Model Systems for Pulmonary Diseases," The Journal of Organic Chemistry, 81(2):532-544 (2016).
Maini, R., et al., "Protein Synthesis with Ribosomes Selected for the Incorporation of β-Amino Acids," Biochemistry, 54(23):3694-3706 (2015).
Maini, R., et al., "Ribosome-mediated Synthesis of Natural Product-like Peptides via Cell-free Translation," Current Opinion in Chemical Biology, 34:44-52 (2016).
Malhotra, R., et al., "Efficient asymmetric synthesis of N-protected-β-aryloxyamino acids via regioselective ring opening of serine sulfamidate carboxylic acid," Organic & Biomolecular Chemistry, 12(33):6507-6515 (2014).
Manfredini, S., et al., "Design and Synthesis of Phosphonoacetic Acid (PPA) Ester and Amide Bioisosters of Ribofuranosylnucleoside Diphosphates as Potential Ribonucleotide Reductase Inhibitors and Evaluation of Their Enzyme Inhibitory, Cytostatic and Antiviral Activity," Antiviral Chemistry and Chemotherapy, 14(4):183-194 (2003).
Mangold, S.L., et al., "Z-Selective olefin metathesis on peptides: investigation of side-chain influence, preorganization, and guidelines in substrate selection," Journal of the American Chemical Society, 136(35):12469-12478 (2014).
Marcucci, E., "Solid-Phase Synthesis of NMe-IB-01212, a Highly N-Methylated Cyclic Peptide," Organic letters, 14(2):612-615 (2012).
Mas-Moruno, C., et al., "Cilengitide: the First Anti-angiogenic Small Molecule Drug Candidate Design, Synthesis and Clinical Evaluation," Anti-cancer agents in Medicinal Chemistry, 10(10):753-768 (2010).
Meinnel, T., et al., "Methionine as Translation Start Signal: a Review of the Enzymes of the Pathway in *Escherichia coli*," Biochimie, 75(12):1061-1075 (1993).
Mermershtain, I., et al., "Idiosyncrasy and Identity in the Prokaryotic Phe-system: Crystal Structure of *E. coli* Phenylalanyl-tRNA Synthetase Complexed With Phenylalanine and AMP," Protein Science, 20(1):160-167 (2011).
Merryman, C., et al., "Transformation of Aminoacyl tRNAs for the in Vitro Selection of "Drug-like" Molecules," Chemistry & Biology, 11(4):575-582 (2004).
Miller, S.C. and Scanlan, T.S., "Site-Selective N-Methylation of Peptides on Solid Support," J Am Chem Soc., 119:2301-2302 (1997).
Millward, S.W., et al., "A General Route for Post-translational Cyclization of mRNA Display Libraries," Journal of the American Chemical Society, 127(41):14142-14143 (2005).
Millward, S.W., et al., "Design of Cyclic Peptides That Bind Protein Surfaces With Antibody-like Affinity," ACS Chemical Biology, 2(9):625-634 (2007).
Miyake, A., et al., "Design and Synthesis of N-[n-[(S)-1-ethoxycarbonyl-3-phenylpropyl]-I-alanyl]-n-(Indan-2-yl)glycine (Cv-3317), a New, Potent Angiotensin Converting Enzyme Inhibitor," Chemical & Pharmaceutical Bulletin (Tokyo), 34(7):2852-2858 (1986).
Montalbetti, C.A.G.N. and Falque, V., "Amide Bond Formation and Peptide Coupling," Tetrahedron, 61(46):10827-10852 (2005).
Morieux, P., et al., "The structure-activity relationship of the 3-oxy site in the anticonvulsant (R)-N-benzyl 2-acetamido-3-methoxypropionamide," Journal of Medicinal Chemistry, 53(15):5716-5726 (2010).
Muramatsu, T., et al., "A Novel Lysine-Substituted Nucleoside in the First Position of the Anticodon of Minor Isoleucine tRNA from *Escherichia coli*," The Journal of Biological Chemistry, 263(19):9261-9267 (1988).
Murashige, R., et al., "Asymmetric and Efficient Synthesis of Homophenylalanine Derivatives via Friedel-Crafts Reaction With Trifluoromethanesulfonic Acid," Tetrahedron Letters, 49(46):6566-6568 (2008).
Navo, C.D., et al., "Oxygen by Carbon Replacement at the Glycosidic Linkage Modulates the Sugar Conformation in Tn Antigen Mimics," ACS Omega, 3(12):18142-18152 (2018).

(56) References Cited

OTHER PUBLICATIONS

Niida, A., et al., "Investigation of the Structural Requirements of K-ras(G12d) Selective Inhibitory Peptide Krpep-2d Using Alanine Scans and Cysteine Bridging," Bioorganic & Medicinal Chemistry Letters, 27(12):2757-2761 (2017).
Ohta, A., et al., "Synthesis of Polyester by Means of Genetic Code Reprogramming," Chemistry & Biology, 14(12):1315-1322 (2007).
Ohtsuki, T., et al., "Phototriggered Protein Syntheses by Using (7-diethylaminocoumarin-4-yl)Methoxycarbonyl-Caged Aminoacyl tRNAs," Nature communications, 7:12501 (2016).
Ohwada, T., et al., "On the Planarity of Amide Nitrogen. Intrinsic Pyramidal Nitrogen of N-acyl-7-azabicyclo[2.2.1]heptanes," Tetrahedron Letters, 39(8):865-868 (1998).
Orain, D., et al., "Protecting Groups in Solid-phase Organic Synthesis," Journal of Combinatorial Chemistry, 4(1):1-16 (2002).
Osawa, T., et al., "Structural Basis of tRNA Agmatinylation Essential for AUA Codon Decoding," Nature Structural & Molecular Biology, 18(11):1275-1280 (2011).
Ostrem, J.M.L., et al., "Direct Small-molecule Inhibitors of Kras: From Structural Insights to Mechanism-based Design," Nature Reviews. Drug Discovery, 15(11):771-785 (2016).
Ovadia, O., et al., "Improvement of Drug-like Properties of Peptides: the Somatostatin Paradigm," Expert Opinion on Drug Discovery, 5(7):655-671 (2010).
Parthasarathy, R., et al., "Sortase a as a Novel Molecular "Stapler" for Sequence-specific Protein Conjugation," Bioconjugate Chemistry, 18(2):469-476 (2007).
Peacock, J.R., et al., "Amino Acid-dependent Stability of the Acyl Linkage in Aminoacyl-tRNA," RNA, 20(6):758-764 (2014).
Perona, J.J., et al., "Structural Diversity and Protein Engineering of the Aminoacyl-tRNA Synthetases," Biochemistry, 51(44):8705-8729 (2012).
Peschke, B., et al., "New Highly Potent Dipeptidic Growth Hormone Secretagogues With Low Molecular Weight," European Journal of Medicinal Chemistry, 35(6):599-618 (2000).
Piszkiewicz, D., et al., "Anomalous Cleavage of Aspartyl-proline Peptide Bonds During Amino Acid Sequence Determination," Biochemical and Biophysical Research Communications, 40(5):1173-1178 (1970).
Rader, A.F.B., et al., "Improving oral bioavailability of cyclic peptides by N-methylation," Bioorg Med Chem., 26:2766-2773 (2018).
Rader, A.F.B., et al., "Orally Active Peptides: Is There a Magic Bullet?," Angewandte Chemie (International ed. in English), 57(44):14414-14438 (2018).
Rafi, S.B., et al., "Predicting and Improving the Membrane Permeability of Peptidic Small Molecules," Journal of Medicinal Chemistry, 55(7):3163-3169 (2012).
Reddy, P.R., et al., "Synthesis of Small Cyclic Peptides via Intramolecular Heck Reactions," Tetrahedron Letters, 44(2):353-356 (2003).
Rezai, T., et al., "Testing the Conformational Hypothesis of Passive Membrane Permeability Using Synthetic Cyclic Peptide Diastereomers," Journal of the American Chemical Society, 128(8):2510-2511 (2006).
Rodriguez, H., et al., "A Convenient Microwave-enhanced Solid-phase Synthesis of Short Chain N-methyl-rich Peptides," Journal of Peptide Science, 16(3):136-140 (2010).
Roodbeen, R., et al., "Microwave Heating in the Solid-Phase Synthesis of N-Methylated Peptides: When Is Room Temperature Better?," European Journal of Organic Chemistry, 2012(36):7106-7111 (2012).
Sakamoto, K., et al., "K-ras(G12d)-selective Inhibitory Peptides Generated by Random Peptide T7 Phage Display Technology," Biochemical and Biophysical Research Communication, 484(3):605-611 (2017).
Salowe, S.P., et al., "The Catalytic Flexibility of Trnaile-Lysidine Synthetase Can Generate Alternative tRNA Substrates for Isoleucyl-tRNA Synthetase," The Journal of Biological Chemistry, 284(15):9656-9662 (2009).

Samatar, A.A., et al., "Targeting Ras-erk Signalling in Cancer: Promises and Challenges," Nature Reviews. Drug Discovery, 13(12):928-942 (2014).
Sang-Aroon, W., et al., "Theoretical Study on Isomerization and Peptide Bond Cleavage at Aspartic Residue," Journal of Molecular Modeling, 19(9):3627-3636 (2013).
Sankaranarayanan, R., et al., "The Structure of Threonyl-tRNA Synthetase-tRNA(Thr) Complex Enlightens Its Repressor Activity and Reveals an Essential Zinc Ion in the Active Site," Cell, 97(3):371-381 (1999).
Satyanarayanajois, S.D., et al., "Medicinal chemistry for 2020," Future Medicinal Chemistry, 3(14):1765-1786 (2011).
Schlippe, Y.V.G., et al., "In Vitro Selection of Highly Modified Cyclic Peptides That Act as Tight Binding Inhibitors," Journal of the American Chemical Society, 134(25):10469-10477 (2012).
Sever, S., et al., "*Escherichia coli* Tryptophanyl-tRNA Synthetase Mutants Selected for Tryptophan Auxotrophy Implicate the Dimer Interface in Optimizing Amino Acid Binding," Biochemistry, 35(1):32-40 (1996).
Shankaramma, S.C., et al., "A family of macrocyclic antibiotics with a mixed peptide-peptoid β-hairpin backbone conformation," Chem Commun., 15:1842-1843 (2003).
Shimizu, Y., et al., "Cell-Free Translation Reconstituted With Purified Components," Nature Biotechnology, 19(8):751-755 (2001).
Shukla, G.S., et al., "Phage-displayed Combinatorial Peptide Libraries in Fusion to Beta-lactamase as Reporter for an Accelerated Clone Screening: Potential Uses of Selected Enzyme-linked Affinity Reagents in Downstream Applications," Combinatorial Chemistry & High Throughput Screening, 13(1):75-87 (2010).
Sogabe, S., et al., "Crystal Structure of a Human K-Ras G12D Mutant in Complex with GDP and the Cyclic Inhibitory Peptide KRpep-2d," ACS Medicinal Chemisty Letters, 8(7):732-736 (2017).
Starosta, A.L., et al., "A Conserved Proline Triplet in Val-tRNA Synthetase and the Origin of Elongation Factor P," Cell Reports, 9(2):476-483 (2014).
Stetsenko, D.A., et al., "Removal of Acid-Labile Protecting or Anchoring Groups in the Presence of Polyfluorinated Alcohol: Application to Solid-Phase Peptide Synthesis," Russian Journal of Bioorganic Chemistry, 42(2):143-152 (2016).
Struck, A.W., et al., "An Enzyme Cascade for Selective Modification of Tyrosine Residues in Structurally Diverse Peptides and Proteins," Journal of the American Chemical Society, 138(9):3038-3045 (2016).
Subtelny, A.O., et al., "Optimal Codon Choice Can Improve the Efficiency and Fidelity of N-methyl Amino Acid Incorporation Into Peptides by in-vitro Translation," Angewandte Chemie (International ed. English), 50(14):3164-3167 (2011).
Subtelny, A.O., et al., "Ribosomal Synthesis of N-methyl Peptides," Journal of the American Chemical Society, 130(19):6131-6136 (2008).
Suenaga, K., et al., "Aurilide, a Cytotoxic Depsipeptide From the Sea Hare *Dolabella auricularia*: Isolation, Structure Determination, Synthesis, and Biological Activity," Tetrahedron, 60(38):8509-8527 (2004).
Suenaga, K., et al., "Synthesis and Cytotoxicity of Aurilide Analogs," Bioorganic & Medicinal Chemistry Letters, 18(14):3902-3205 (2008).
Suzuki, T., et al., "Discovery and Characterization of tRNAIle Lysidine Synthetase (TilS)," FEBS Letters, 584(2):272-277 (2010).
Suzuki, T., "How to Decipher AUA Codon in Archaea," Kagaku to Seibutsu, 50(1):36-43 (2012).
Tam, J.P., et al., "Cyclohexyl Ester as a New Protecting Group for Aspartyl Peptides to Minimize Aspartimide Formation in Acidic and Basic Treatments," Tetrahedron Letters, 20(42):4033-4036 (1979).
Tan, Z., et al., "Amino Acid Backbone Specificity of the *Escherichia coli* Translation Machinery," Journal of the American Chemical Society, 126(40):12752-12753 (2004).
Teixido, M., et al., "Solid-phase Synthesis and Characterization of N-methyl-rich Peptides," The Journal of Peptide Research, 65(2):153-166 (2005).
Terasaka, et al., "Construction of Nonstandard Peptide Library by Genetic Code Reprogramming and Bioactive Peptide Discovery," Experimental Medicine, 29(7):1063-70 (2011).

(56) References Cited

OTHER PUBLICATIONS

Terasaka, N., et al., "Recent Developments of Engineered Translational Machineries for the Incorporation of Non-canonical Amino Acids Into Polypeptides," International Journal of Molecular Sciences, 20;16(3):6513-6531 (2015).
Toriyama, F., et al., "Redox-Active Esters in Fe-catalyzed C—C Coupling," Journal of the American Chemical Society, 138(35):11132-11135 (2016).
Tsuda, et al., "Amino Acids, Peptides and Proteins in Organic Chemistry," 3:201-406, 495-517, 549-569 (2011).
Tsukiji, S. and Nagamune, T., "Sortase-mediated Ligation: A Gift From Gram-positive Bacteria to Protein Engineering," Chembiochem, 10(5):787-798 (2009).
Turner, R.A., et al., "Selective, On-Resin N-Methylation of Peptide N-Trifluoroacetamides," Org Lett., 15(19):5012-5015 (2013).
Urban, J., et al., "Lability of N-alkylated Peptides Towards TFA Cleavage," International Journal of Peptide and Protein Research, 47(3):182-189 (1996).
Vaisar, T. and Urban, J., "Gas-Phase Fragmentation of Protonated Mono-n-Methylated Peptides. Analogy With Solution-Phase Acid-Catalyzed Hydrolysis," Journal of Mass Spectrometry, 33(6):505-524 (1998).
Van Der Auwera, C. and Anteunis, M. J. O., "Easy cleavage of C'-terminal iminoacids from peptide acids through acidic hydrolysis," Int J Peptide Protein Res., 31:186-191 (1988).
Wang, J., et al., "Kinetics of Ribosome-Catalyzed Polymerization Using Artificial Aminoacyl-tRNA Substrates Clarifies Inefficiencies and Improvements," ACS Chemical Biology, 10(10):2187-2192 (2015).
Wang, S., et al., "Iridium/f-Amphox-Catalyzed Asymmetric Hydrogenation of Styrylglyoxylamides," Synlett, 29(16):2203-2207 (2018).
Wang, T., et al., "Revisiting Oxytocin Through the Medium of Isonitriles," Journal of the American Chemical Society, 134(32):13244-13247 (2012).
Watanabe, E., et al., "A Practical Method for Continuous Production of sp3-Rich Compounds from (Hetero)Aryl Halides and Redox-Active Esters," Chemistry, 26(1):186-191 (2020).
Weber, F., et al., "A Potato Mitochondrial Isoleucine tRNA is Coded for by a Mitochondrial Gene Possessing a Methionine Anticodon," Nucleic Acids Research, 18(17):5027-5030 (1990).
Wells, J.A., et al., "Reaching for High-hanging Fruit in Drug Discovery at Protein-protein Interfaces," Nature, 450(7172):1001-1009 (2007).
Wenschuh, H., et al., "Stepwise Automated Solid Phase Synthesis of Naturally Occurring Peptaibols Using FMOC Amino Acid Fluorides," The Journal of Organic Chemistry, 60(2):405-410 (1995).
Wermuth, C. G., editor, "The Practice of Medicinal Chemistry," $2^{nd}$ Edition, 52-53, 87-88 (2003).
White, C.J., et al., "Contemporary Strategies for Peptide Macrocyclization," Nature Chemistry, 3(7):509-524 (2011).
White, T.R., et al., "On-resin N-methylation of Cyclic Peptides for Discovery of Orally Bioavailable Scaffolds," Nature Chemical Biology, 7(11):810-817 (2011).
Wu, J., et al., "Intrinsic Basicity of Oligomeric Peptides That Contain Glycine, Alanine, and Valine-the Effects of the Alkyl Side Chain on Proton Transfer Reactions," Journal of the American Society for Mass Spectrometry, 6(2):91-101 (1995).
Wu, N., et al., "A genetically encoded photocaged amino acid," Journal of the American Chemical Society, 126(44):14306-14307 (2004).
Yajima, et al,, "New Strategy for the Chemical Synthesis of Proteins," Tetrahedron, 44(3):805-819 (1988).
Yamagishi, Y., et al., "Natural Product-like Macrocyclic N-methyl-peptide Inhibitors Against a Ubiquitin Ligase Uncovered From a Ribosome-expressed De Novo Library," Chemisty & Biology, 18(12):1562-1570 (2011).
Yamanoi, K., et al., "Synthesis of Trans and cis-α-(carboxycyclopropyl)Glycines Novel Neuroinhibitory Amino Acids as L-Glutamate Analogue," Tetrahedron Letters, 29(10):1181-1184 (1988).
Yanagisawa, T., et al., "Multistep Engineering of Pyrrolysyl-tRNA Synthetase to Genetically Encode N(Epsilon)-(O-azidobenzyloxycarbonyl) Lysine for Site-specific Protein Modification," Chemistry & Biology, 15(11):1187-1197 (2008).
Yang, Y., "Side Reactions in Peptide Synthesis," 1-31 (2015).
Yang, Y., "Side Reactions in Peptide Synthesis," 246 (2016).
Yao, G., et al., "Efficient Synthesis and Stereochemical Revision of Coibamide A," Journal of the American Chemical Society, 137(42):13488-13491 (2015).
Zhai, Y., et al., "Two Conserved Threonines Collaborate in the *Escherichia coli* Leucyl-tRNA Synthetase Amino Acid Editing Mechanism," Biochemistry, 44(47):15437-15443 (2005).
Zhang, A.J., et al., "A Method for Removal of N-BOC Protecting Groups from Substrates on TFA-Sensitive Resins," Tetrahedron Letters, 39(41):7439-7442 (1998).
Zhang, B., et al., "Specificity of Translation for N-alkyl Amino Acids," Journal of the American Chemical Society, 129(37):11316-11317 (2007).
Zhang, K., et al., "Ab Initio Studies of Neutral and Protonated Triglycines: Comparison of Calculated and Experimental Gas-Phase Basicity," Journal of the American Chemical Society, 116(25):11512-11521 (1994).
Zhang, Z., et al., "GTP-State-Selective Cyclic Peptide Ligands of K-Ras(G12D) Block Its Interaction with Raf," ACS Cent Sci., 6:1753-1761 (2020).
U.S. Appl. No. 07/251,176, filed Sep. 30, 1988, Schuetz, et al.
U.S. Appl. No. 10/345,664, filed Jan. 16, 2003, Olejnik et al.
U.S. Appl. No. 11/682,272, filed Mar. 5, 2007, Wang et al.
U.S. Appl. No. 13/505,625, filed Oct. 22, 2012, Strom et al.
U.S. Appl. No. 13/816,911, filed Feb. 13, 2013, Suga et al.
U.S. Appl. No. 14/125,906, filed Mar. 10, 2014, Gao et al.
U.S. Appl. No. 14/368,564, filed Jun. 25, 2014, Kariyuki et al., related application.
U.S. Appl. No. 14/889,868, filed Mar. 7, 2016, Murakami et al.
U.S. Appl. No. 15/166,550, filed May 27, 2016, Kariyuki et al., related application.
U.S. Appl. No. 15/557,532, filed Sep. 12, 2017, Ohta et al., related application.
U.S. Appl. No. 16/081,522, filed Jul. 8, 2019, Nakano et al., related application.
U.S. Appl. No. 16/479,736, filed Jul. 22, 2019, Tanaka et al., related application.
U.S. Appl. No. 16/619,014, filed Dec. 3, 2019, Muraoka et al., related application.
U.S. Appl. No. 16/619,388, filed Dec. 4, 2019, Nomura et al., related application.
U.S. Appl. No. 16/771,335, filed Jun. 10, 2020, Nomura et al., related application.
U.S. Appl. No. 17/011,815, filed Sep. 3, 2020, Kariyuki et al., related application.
U.S. Appl. No. 17/024,944, filed Sep. 18, 2020, Ohta et al., related application.
U.S. Appl. No. 17/291,099, filed Jun. 3, 2021, Ishizawa, related application.
U.S. Appl. No. 17/297,231, filed May 26, 2021, Iwasaki et al., related application.
U.S. Appl. No. 17/312,296, filed Jun. 9, 2021, Muraoka et al., related application.
U.S. Appl. No. 17/417,822, filed Jun. 24, 2021, Shinohara et al., related application.
U.S. Appl. No. 17/437,535, filed Sep. 9, 2021, Wadamoto et al., related application.
U.S. Appl. No. 17/738,283, filed May 6, 2022, Hou et al., related application.
U.S. Appl. No. 17/773,734, filed May 2, 2022, Nomura et al., related application.
U.S. Appl. No. 17/787,809, filed Jun. 21, 2022, Kagotani et al., related application.
U.S. Appl. No. 17/788,506, filed Jun. 23, 2022, Kondo et al., related application.
U.S. Appl. No. 17/928,759, filed Nov. 30, 2022, Iwasaki et al., related application.

(56) References Cited

OTHER PUBLICATIONS

U.S. Appl. No. 17/976,942, filed Oct. 31, 2022, Nomura et al., related application.
U.S. Appl. No. 18/010,608, filed Dec. 15, 2022, Nishimura et al., related application.
U.S. Appl. No. 18/034,424, filed Apr. 28, 2023, Nomura et al., related application.
U.S. Appl. No. 18/203,371, filed May 30, 2023, Iwasaki et al., related application.
U.S. Appl. No. 18/268,737, filed Jun. 21, 2023, Morita et al., related application.
U.S. Appl. No. 18/269,334, filed Jun. 23, 2023, Sekita et al., related application.
U.S. Appl. No. 18/289,071, filed Oct. 31, 2023, Hayashi et al., related application.
U.S. Appl. No. 18/289,392, filed Nov. 3, 2023, Ueto et al., related application.
U.S. Appl. No. 18/289,451, filed Nov. 3, 2023, Tanada et al., related application.
U.S. Appl. No. 18/289,592, filed Nov. 6, 2023, Kawada et al., related application.
U.S. Appl. No. 18/459,998, filed Sep. 1, 2023, Nomura et al., related application.
U.S. Appl. No. 18/460,300, filed Sep. 1, 2023, Kariyuki et al., related application.
Osumi, H., et al., "Cetuximab treatment for metastatic colorectal cancer with KRAS p.G13D mutations improves progression-free survival," Mol Clin Oncol., 3:1053-1057 (2015).
Tabernero, J., et al., "KRYSTAL-10: A randomized phase 3 study of adagrasib (MRTX849) in combination with cetuximab vs chemotherapy in patients with previously treated advanced colorectal cancer with KRASG12C mutation," Ann Oncol., 32(S3):S121 (2021).
Tejpar, S., et al., "Association of KRAS G13D Tumor Mutations with Outcome in Patients with Metastatic Colorectal Cancer Treated with First-Line Chemotherapy with or without Cetuximab," J Clin Oncol., 30(29):3570-3577 (2012).
Furumoto, K., et al., "Establishment of High-Throughput Screening Method for Excipients to Improve Solubility of Poorly Soluble Compounds," Journal of Pharmaceutical Science and Technology, Japan, 70 Suppl:192 (2010).
Yang, Y., "Side Reactions in Peptide Synthesis," Chapter 5, pp. 95-118; Chapter 10, pp. 235-256; Chapter 11, pp. 257-292; and Chapter 14, pp. 311-322 (2015).
Boltromeūk, V.V., "General chemistry," Minsk, Vyšejšaāškola, 65 (2012).
Nomura, K., et al., "Broadly Applicable and Comprehensive Synthetic Method for N-Alkyl-Rich Drug-like Cyclic Peptides," J Med Chem., 65:13401-13412 (2022).
Purkey, H., "Discovery of GDC 6036, a clinical stage treatment for KRAS G12C-positive cancers," AACR Annual Meeting, 11-17 (2022).
Purkey, H., "Abstract ND11: Discovery of GDC-6036, a clinical stage treatment for KRAS G12C-positive cancers," Cancer Res., 82(12_Supplement):ND11 (2022).
Xu, J., et al., "Atroposelective Negishi Coupling Optimization Guided by Multivariate Linear Regression Analysis: Asymmetric Synthesis of KRAS G12C Covalent Inhibitor GDC-6036," J Am Chem Soc., 144:20955-20963 (2022).
U.S. Appl. No. 18/829,566, filed Sep. 10, 2024, Kawada et al., related application.
U.S. Appl. No. 18/860,859, filed Oct. 28, 2024, Kage et al., related application.
Aboulfotouh, K., et al., "Role of self-emulsifying drug delivery systems in optimizing the oral delivery of hydrophilic macromolecules and reducing interindividual variability," Colloids and Surfaces B: Biointerfaces, 167:82-92 (2018).
Aoki, M., et al., "Elucidation of Solubility Decrease Phenomenon by Cocrystal Formation between APIs and Excipients—Solubility Decrease Induced by Crystallization between APIs and Excipients," Lecture abstracts of the Annual Meeting of the Academy of Pharmaceutical Science and Technology, Japan, vol. 29, p. 20-32, p. 193 (2014).
Berkowitz, W. F. and John, T. V., "An Internal Imino-Diels-Alder Route to a Tetrahydroisoquinoline," J Org Chem., 49(26):5269-5271 (1984).
Chatterjee, J., et al., "N-Methylation of Peptides and Proteins: An Important Element for Modulating Biological Functions," Angew Chem Int Ed., 52:254-269 (2013).
Chen, D., et al., "Selective N-terminal functionalization of native peptides and proteins," Chem Sci., 8:2717-2722 (2017).
Date, A. A., et al., "Self-nanoemulsifying drug delivery systems: formulation insights, applications and advances," Nanomedicine, 5(10):1595-1616 (2010).
Deal, M. J., et al., "Conformationally Constrained Tachykinin Analogues: Potent and Highly Selective Neurokinin NK-2 Receptor Agonists," J Med Chem., 35(22):4195-4204 (1992).
Eggen, I. F., et al., "A novel method for repetitive peptide synthesis in solution without isolation of intermediates," J Peptide Sci., 11:633-641 (2005).
Fattah, S. and Brayden, D. J., "Progress in the formulation and delivery of somatostatin analogs for acromegaly," Ther Deliv., 8(10):867-878 (2017).
Han, Y. and Chorev, M., "A Novel, One-Pot Reductive Alkylation of Amines by S-Ethyl Thioesters Mediated by Triethylsilane and Sodium Triacetoxyborohydride in the Presence of Palladium on Carbon," J Org Chem., 64:1972-1978 (1999).
Ikawa, T., et al., "Selective N-alkylation of amines using nitriles under hydrogenation conditions: facile synthesis of secondary and tertiary amines," Org Biomol Chem., 10:293-304 (2012).
Lazo, J. S. and Sharlow, E. R., "Drugging Undruggable Molecular Cancer Targets," Annu Rev Pharmacol Toxicol., 56:23-40 (2016).
Leonaviciute, G., et al., "Impact of lipases on the protective effect of SEDDS for incorporated peptide drugs towards intestinal peptidases," Int J Pharmaceut., 508:102-108 (2016).
Lipinski, C. A., et al., "Experimental and computational approaches to estimate solubility and permeability in drug discovery and development settings," Adv Drug Del Rev., 23:3-25 (1997).
Paradís-Bas, M., et al., "The road to the synthesis of difficult peptides," Chem Soc Rev., 45:631-654 (2016).
Sajiki, H., et al., "Reductive and Catalytic Monoalkylation of Primary Amines Using Nitriles as an Alkylating Reagent," Org Lett., 6(26):4977-4980 (2004).
Sharma, A., et al., "N-methylation in amino acids and peptides: Scope and limitations," Biopolymers, 109:e23110 (2018).
Tanaka, M., "Design and Conformation of Peptides Containing α,α-Disubstituted α-Amino Acids," J Syn Org Chem., 60(2):125-136 (2002).
Wegner, K., et al., "Evaluation of greener solvents for solid-phase peptide synthesis," Green Chem Lett Rev., 14(1):153-164 (2021).
U.S. Appl. No. 18/699,488, filed Apr. 8, 2024, Nakae et al., related application.
U.S. Appl. No. 18/723,993, filed Jun. 25, 2024, Komiya et al., related application.
U.S. Appl. No. 18/728,922, filed Jul. 15, 2024, Sase et al., related application.
U.S. Appl. No. 18/781,112, filed Jul. 23, 2024, Wadamoto, related application.

CYCLIC PEPTIDE COMPOUND HAVING KRAS INHIBITORY ACTION

CROSS-REFERENCE TO RELATED APPLICATIONS

This application is a continuation of U.S. patent application Ser. No. 17/773,733, filed May 2, 2022, which is a U.S. National Phase of PCT Application No. PCT/JP2020/041277, filed Nov. 5, 2020, which claims the benefit of Japanese Patent Application No. 2019-202407, filed Nov. 7, 2019, each of which is incorporated herein by reference in its entirety.

TECHNICAL FIELD

The present invention relates to cyclic peptide compounds having Kras inhibitory action, non-natural amino acids for use in the production of cyclic peptide compounds, and production methods therefor.

BACKGROUND ART

Ras is a protein belonging to the small GTPase family, and Kras, Nras, and Hras are known. Ras is in an inactive state or an active state according to whether it is bound to GTP or GDP. It is activated by the exchange reaction from GDP to GTP by GEFs (guanine nucleotide exchange factors) and inactivated by the hydrolysis reaction of GTP by GAPs (GTPase-activating proteins) (NPL 1). Activated Ras induces cell proliferation, survival, and differentiation by activating various downstream signals in the MAPK pathway, PI3K/Akt pathway, RAL pathway, and such, and the constitutive activation of Ras plays an important role in the development and progression of cancer. In cancer, it is known that the Ras-RAF-MEK-ERK pathway is activated by the activation of an upstream signal of Ras, constitutive activation of Ras, and/or activating mutations of Ras (NPL 2). These activating mutations of Ras have been found in numerous cancer types. G12, G13, and Q61 are known as hot spots of Ras mutation, and G12 is frequently found mutated in Kras and Q61 in Nras. These mutations are also known to be associated with the prognosis of patients (NPL 3).

When it comes to access to a tough target, as typified by inhibition of a protein-protein interaction, medium sized molecules (having a molecular weight of 500 to 2000) may be superior to low molecular weight compounds. Also, medium sized molecules may be superior to antibodies in that they can migrate into cells. Among biologically active medium sized molecules, peptide drugs are highly valuable molecular species, with more than 40 peptide drugs being already commercially available (NPL 4). Representative examples of such peptide drugs include cyclosporin A and polymyxin B, which are peptides containing some non-natural amino acids. A non-natural amino acid refers to an amino acid that is not naturally encoded on mRNA. It is highly interesting that non-natural amino acids that are not encoded on mRNA are contained in naturally-occurring cyclosporin A and polymyxin B.

Since the discovery of the pharmaceutical utility of naturally-occurring peptides, peptides having pharmacological activity and bioabsorbability have been attracting attention, and those having a molecular weight of about 500 to 2000 have been actively researched (NPL 5).

There is a report on conditions for medium molecular weight peptides to have increased membrane permeability and metabolic stability, which may contribute to improving their biokinetics (conditions necessary for satisfying drug-likeness) (PTL 1).

Moreover, as for the conditions that may contribute to improving the biokinetics of medium molecular weight peptides, conditions necessary for cyclic peptides to satisfy drug-likeness have been shown (PTL 2).

Peptides that bind to Ras have been found, and the binding site between a cyclic peptide and Ras has been studied by X-ray structural analysis (NPL 6, NPL 7, and NPL 8). Also, cyclic peptides that apparently inhibit binding between Ras and SOS have been found (PTL 3). Moreover, a competition assay for binding with Ras has suggested that some cyclic peptides inhibit binding between a particular compound and Ras (PTL 4).

CITATION LIST

Patent Literature

[PTL 1] WO 2013/100132
[PTL 2] WO 2018/225864
[PTL 3] WO 2012/122059
[PTL 4] WO 2017/181061

Non-Patent Literature

[NPL 1] Nat. Rev. Drug Discov. 2014 November; 13(11): 828-851.
[NPL 2] Nat. Rev. Drug Discov. 2014 December; 13(12): 928-942.
[NPL 3] Nat. Rev. Drug Discov. 2016 November; 15(11): 771-785.
[NPL 4] Future Med. Chem. 2009, 1, 1289-1310.
[NPL 5] Current Topics in Medicinal Chemistry, 2013, Vol. 13, No. 7, 821-836.
[NPL 6] Biochem. Biophys. Res. Commun. 2017, 484, 605-611.
[NPL 7] Bioorg. Med. Chem. Lett. 2017, 27, 2757-2761.
[NPL 8] ACS Med. Chem. Lett. 2017, 8, 732-736.

SUMMARY OF INVENTION

Technical Problem

The present invention provides compounds effective for Ras-mutant cancer and non-natural amino acids useful for the production thereof.

PTL 1 and PTL 2 describe drug-like peptides, but do not describe a peptide having an antitumor effect on cancers including Ras-mutant cancer.

PTL 3 describes the inhibition of binding between Ras and SOS, and PTL 4 describes a peptide competing with a compound that binds to Ras. However, none of these documents shows any pharmacological action, especially action on tumor cells. These documents do not describe drug-like peptides, either.

NPL 1 shows the relationship between Ras and cancer in detail. This document describes molecules that bind to Ras. Although their efficacy was shown in preclinical studies, no compound was shown to be effective as a drug specifically on Ras-mutant cancer. Also, no drug-like cyclic peptide is disclosed.

NPL 2 provides detailed descriptions about Ras and the RAF-MEK-ERK pathway, which is downstream of Ras. Although this document suggests the possibility of treating Ras-mutant cancer with RAF, MEK, and ERK inhibitors, it does not show any compound that directly inhibits Ras.

NPL 3 describes a compound that binds to the GTP/GDP binding site of Ras and inhibits the function of Ras, and the mechanism thereof. This document describes the interaction with the GTP/GDP binding site in detail, but does not show pharmacological action, especially action on tumor cells.

NPL 4 describes peptides that are used as drugs, but does not describe a drug-like peptide or a peptide useful for Ras-mutant cancer.

NPL 5 describes the molecular form and pharmacokinetics of cyclic peptides, but does not describe a compound useful for Ras-mutant cancer.

NPLs 6 to 8 describe peptides that bind to Ras, but their action on tumor cells is limited, and, in addition, a drug-like peptide is not described.

Despite the fact that Ras-mutant cancer has no effective treatment and the unmet need is strong, a drug that directly inhibits Ras and exhibits a clinical therapeutic effect has not been developed yet. Also, a peptide that satisfies drug-likeness has not been found.

The peptide compounds of interest in the present invention are breakthrough drugs that directly bind to Ras and inhibit its interaction with SOS, whereby they suppress the activation of Ras and inhibit the proliferation of cancer cells having Ras mutation.

Solution to Problem

As a result of dedicated research for seeking cyclic peptide compounds having Ras inhibitory activity, the present inventors found cyclic peptide compounds that interact with Ras. The inventors also found that those cyclic peptide compounds inhibit the binding between Ras and SOS. In addition, the inventors found specific non-natural amino acids contained in the cyclic peptide compounds and methods for production thereof. The inventors found that the cyclic peptide compounds have, as a pharmacological effect, a proliferation inhibitory effect on tumor cells having Ras mutation.

The present invention encompasses the following in one non-limiting specific embodiment:

[1] A cyclic peptide compound represented by formula (1) below or a salt thereof, or a solvate thereof:

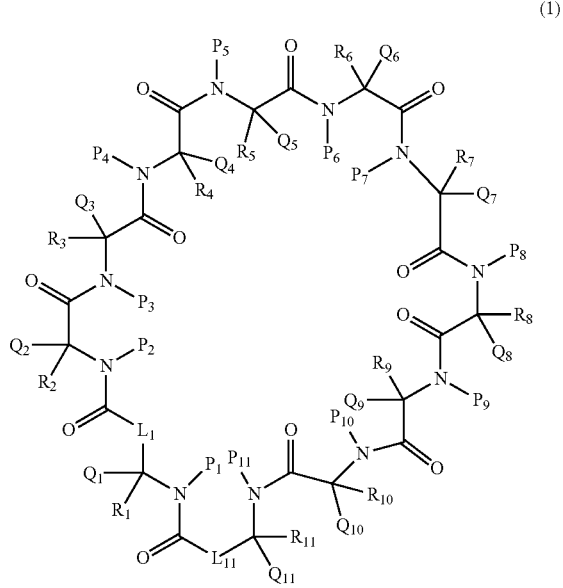

(1)

wherein, $L_1$ is a single bond, or —$CHM_1$—, —$(CH_2)_nS(CH_2)_m$—, —$(CH_2)_nS(O)(CH_2)_m$—, or —$(CH_2)_nS(O)_2(CH_2)_m$—, wherein n and m are each independently 1 or 2, $R_1$ is hydrogen, $C_1$-$C_6$ alkyl, $C_2$-$C_6$ alkynyl, $C_1$-$C_6$ alkoxy$C_1$-$C_6$ alkyl, $C_3$-$C_8$ cycloalkyl, $C_3$-$C_8$ cycloalkyl$C_1$-$C_6$ alkyl, or $C_3$-$C_8$ cycloalkoxy$C_1$-$C_6$ alkyl, each of which is optionally substituted with one or more groups independently selected from the group consisting of halogen, hydroxy, aminocarbonyl (wherein the amino is —$NH_2$, mono-$C_1$-$C_6$ alkylamino, di-$C_1$-$C_6$ alkylamino, or 4- to 8-membered cyclic amino), and $C_1$-$C_6$ alkylsulfonyl, or $R_1$ and $P_1$, together with the carbon atom to which $R_1$ is attached and the nitrogen atom to which $P_1$ is attached, form a 4- to 7-membered saturated heterocyclic ring, or $R_1$ and $Q_1$, together with the carbon atom to which they are attached, form a 3- to 8-membered alicyclic ring or a 4- to 7-membered saturated heterocyclic ring, or $R_1$ and $M_1$, together with the carbon atom to which $R_1$ is attached and the carbon atom to which $M_1$ is attached, form a 3- to 8-membered alicyclic ring, except when $R_1$ and $P_1$ form a 4- to 7-membered saturated heterocyclic ring, $P_1$ is hydrogen or $C_1$-$C_6$ alkyl, wherein the $C_1$-$C_6$ alkyl is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino), except when $R_1$ and $Q_1$ form a 3- to 8-membered alicyclic ring or a 4- to 7-membered saturated heterocyclic ring, $Q_1$ is hydrogen or $C_1$-$C_6$ alkyl, and except when $R_1$ and $M_1$ form a 3- to 8-membered alicyclic ring, $M_1$ is hydrogen, $R_2$ is $C_1$-$C_6$ alkyl, $C_2$-$C_6$ alkenyl, $C_2$-$C_6$ alkynyl, $C_1$-$C_6$ alkoxy$C_1$-$C_6$ alkyl, $C_3$-$C_8$ cycloalkyl, $C_3$-$C_8$ cycloalkyl$C_1$-$C_6$ alkyl, or $C_3$-$C_8$ cycloalkoxy$C_1$-$C_6$ alkyl, each of which is optionally substituted with one or more groups independently selected from the group consisting of halogen, hydroxy, cyano, and $C_1$-$C_6$ alkylsulfonyl, or $R_2$ and $P_2$, together with the carbon atom to which $R_2$ is attached and the nitrogen atom to which $P_2$ is attached, form a 4- to 7-membered saturated heterocyclic ring, or $R_2$ and $Q_2$, together with the carbon atom to which they are attached, form a 3- to 8-membered alicyclic ring or a 4- to 7-membered saturated heterocyclic ring, or except when $R_2$ and $P_2$ form a 4- to 7-membered saturated heterocyclic ring, $P_2$ is hydrogen or $C_1$-$C_6$ alkyl, wherein the $C_1$-$C_6$ alkyl is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino), except when $R_2$ and $Q_2$ form a 3- to 8-membered alicyclic ring or a 4- to 7-membered saturated heterocyclic ring, $Q_2$ is hydrogen or $C_1$-$C_6$ alkyl, $R_3$ is hydrogen, $C_1$-$C_6$ alkyl, $C_1$-$C_6$ alkoxy$C_1$-$C_6$ alkyl, $C_3$-$C_8$ cycloalkyl, $C_3$-$C_8$ cycloalkyl$C_1$-$C_6$ alkyl, $C_3$-$C_8$ cycloalkoxy$C_1$-$C_6$ alkyl, or $C_7$-$C_{14}$ aralkyl, each of which is optionally substituted with one or more groups independently selected from the group consisting of hydroxy and aminocarbonyl (wherein the amino is —$NH_2$, mono-$C_1$-$C_6$ alkylamino, di-$C_1$-$C_6$ alkylamino, or 4- to 8-membered cyclic amino), or $R_3$ and $P_3$, together with the carbon atom to which $R_3$ is attached and the nitrogen atom to which $P_3$ is attached, form a 4- to 7-membered saturated heterocyclic ring, or $R_3$ and $Q_3$, together with the carbon atom to which they are attached, form a 3- to 8-membered alicyclic ring or a 4- to 7-membered saturated heterocyclic ring, or except when $R_3$ and $P_3$ form a 4- to 7-membered saturated heterocyclic ring, $P_3$ is hydrogen, $C_1$-$C_6$ alkyl, $C_1$-$C_6$ alkoxy$C_1$-$C_6$ alkyl, or $C_3$-$C_8$ cycloalkyl, each of which is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and $C_1$-$C_6$ aminoalkyl (wherein the amino is —$NH_2$, mono-$C_1$-$C_6$ alkylamino, di-$C_1$-$C_6$ alkylamino, or 4- to 8-membered cyclic amino, wherein the 4- to 8-membered cyclic amino is optionally substituted with one or more halogens), except when $R_3$ and $Q_3$ form a 3- to 8-membered alicyclic ring or a 4- to 7-membered saturated heterocyclic ring, $Q_3$ is hydrogen or $C_1$-$C_6$ alkyl, $R_4$ is hydrogen or $C_1$-$C_6$ alkyl, or $R_4$ and $P_4$, together with the carbon atom to which $R_4$ is attached and the nitrogen atom to which $P_4$ is attached, form a 4- to 7-membered saturated heterocyclic ring, or $R_4$ and $Q_4$, together with the carbon atom to which they are attached, form a 3- to 8-membered alicyclic ring or a 4- to 7-membered saturated heterocyclic ring, or except when $R_4$ and $P_4$ form a 4- to 7-membered saturated heterocyclic ring, $P_4$ is hydrogen, $C_1$-$C_6$ alkyl, or $C_1$-$C_6$ alkoxy$C_1$-$C_6$ alkyl, each of which is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino), except when $R_4$ and $Q_4$ form a 3- to 8-membered alicyclic ring or a 4- to 7-membered saturated heterocyclic ring, $Q_4$ is hydrogen or $C_1$-$C_6$ alkyl, $R_5$ is $C_1$-$C_6$ alkyl, $C_2$-$C_6$ alkenyl, $C_2$-$C_6$ alkynyl, $C_1$-$C_6$ alkoxy$C_1$-$C_6$ alkyl, $C_3$-$C_8$ cycloalkyl, $C_3$-$C_8$ cycloalkyl$C_1$-$C_6$ alkyl, $C_3$-$C_8$ cycloalkoxy$C_1$-$C_6$ alkyl, $C_7$-$C_{14}$ aralkyl, $C_6$-$C_{10}$ aryloxy$C_1$-$C_6$ alkyl, $C_7$-$C_{14}$ aralkoxy$C_1$-$C_6$ alkyl, or 5- to 10-membered heteroaryl$C_1$-$C_6$ alkyl, each of which is optionally substituted with one or more groups independently selected from the group consisting of halogen, hydroxy, $C_1$-$C_6$ alkyl, $C_1$-$C_6$ haloalkyl, $C_1$-$C_6$ alkoxy, $C_1$-$C_6$ haloalkoxy, cyano, and $C_1$-$C_6$ alkylsulfonyl, or $R_5$ together with $R_5$ forms $C_4$-$C_5$ alkylene, or $R_5$ and $P_5$, together with the carbon atom to which $R_5$ is attached and the nitrogen atom to which $P_5$ is attached, form a 4- to 7-membered saturated heterocyclic ring, or $R_5$ and $Q_5$, together with the carbon atom to which they are attached, form a 3- to 8-membered alicyclic ring or a 4- to 7-membered saturated heterocyclic ring, or except when $R_5$ and $P_5$ form a 4- to 7-membered saturated heterocyclic ring, $P_5$ is hydrogen or $C_1$-$C_6$ alkyl, wherein the $C_1$-$C_6$ alkyl is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino), except when $R_5$ and $Q_5$ form a 3- to 8-membered alicyclic ring or a 4- to 7-membered saturated heterocyclic ring, $Q_5$ is hydrogen or $C_1$-$C_6$ alkyl, $R_6$ is hydrogen or $C_1$-$C_6$ alkyl, or $R_6$ and $P_6$, together with the carbon atom to which $R_6$ is attached and the nitrogen atom to which $P_6$ is attached, form a 4- to 7-membered saturated heterocyclic ring, or $R_6$ and $Q_6$, together with the carbon atom to which they are attached, form a 3- to 8-membered alicyclic ring or a 4- to 7-membered saturated heterocyclic ring, or except when $R_6$ and $P_6$ form a 4- to 7-membered saturated heterocyclic ring, $P_6$ is $C_1$-$C_6$ alkyl or $C_3$-$C_8$ cycloalkyl, each of which is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino), except when $R_6$ and $Q_6$ form a 3- to 8-membered alicyclic ring or a 4- to 7-membered saturated heterocyclic ring, $Q_6$ is hydrogen or $C_1$-$C_6$ alkyl, $R_7$ is $C_6$-$C_{10}$ aryloxy$C_1$-$C_6$ alkyl, $C_7$-$C_{14}$ aralkyl, $C_7$-$C_{14}$ aralkoxy$C_1$-$C_6$ alkyl, or 5- to 10-membered heteroaryl$C_1$-$C_6$ alkyl, each of which is optionally substituted with one or more groups independently selected from the group consisting of halogen, $C_1$-$C_6$ alkyl, $C_1$-$C_6$ haloalkyl, $C_2$-$C_6$ alkynyl, $C_1$-$C_6$ alkoxy, $C_1$-$C_6$ haloalkoxy, cyano, $C_1$-$C_6$ alkylsulfonyl, and $SF_5$, or $R_7$ and $P_7$, together with the carbon atom to which $R_7$ is attached and the nitrogen atom to which $P_7$ is attached, form a 4- to 7-membered saturated heterocyclic ring, or $R_7$ and $Q_7$, together with the carbon atom to which they are attached, form a 3- to 8-membered alicyclic ring or a 4- to 7-membered saturated heterocyclic ring, or except when $R_7$ and $P_7$ form a 4- to 7-membered saturated heterocyclic ring, $P_7$ is hydrogen or $C_1$-$C_6$ alkyl, wherein the $C_1$-$C_6$ alkyl is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino), except when $R_7$ and $Q_7$ form a 3- to 8-membered alicyclic ring or a 4- to 7-membered saturated heterocyclic ring, $Q_7$ is hydrogen or $C_1$-$C_6$ alkyl, $R_8$ is hydrogen, $C_1$-$C_6$ alkyl, $C_2$-$C_6$ alkenyl, $C_2$-$C_6$ alkynyl, $C_1$-$C_6$ alkoxy$C_1$-$C_6$ alkyl, $C_2$-$C_6$ alkenyloxycarbonyl$C_1$-$C_6$ alkyl, $C_3$-$C_8$ cycloalkyl, $C_3$-$C_8$ cycloalkyl$C_1$-$C_6$ alkyl, $C_6$-$C_{10}$ aryloxy$C_1$-$C_6$ alkyl, $C_7$-$C_{14}$ aralkyl, $C_7$-$C_{14}$ aralkoxy$C_1$-$C_6$ alkyl, 5- to 10-membered heteroaryl$C_1$-$C_6$ alkyl, or 5- to 10-membered heteroaryl$C_1$-$C_6$ alkoxy$C_1$-$C_6$ alkyl, each of which is optionally substituted with one or more groups independently selected from the group consisting of halogen, hydroxy, carboxy, $C_1$-$C_6$ alkyl, $C_1$-$C_6$ haloalkyl, $C_2$-$C_6$ alkynyl, $C_1$-$C_6$ alkoxy, $C_1$-$C_6$ haloalkoxy, cyano, amino (wherein the amino is —$NH_2$, protected amino, mono-$C_1$-$C_6$ alkylamino, di-$C_1$-$C_6$ alkylamino, or 4- to 8-membered cyclic amino, each of which is optionally substituted with halogen), aminocarbonyl (wherein the amino is —$NH_2$, mono-$C_1$-$C_6$ alkylamino, di-$C_1$-$C_6$ alkylamino, or 4- to 8-membered cyclic amino, each of which is optionally substituted with halogen), 4- to 7-membered heterocycloalkylidene, protected 4- to 7-membered heterocycloalkylidene, 4- to 7-membered heterocyclyl, and protected 4- to 7-membered heterocyclyl, or $R_8$ together with $R_5$ forms $C_4$-$C_5$ alkylene, or $R_8$ and $P_8$, together with the carbon atom to which $R_8$ is attached and the nitrogen atom to which $P_8$ is attached, form a 4- to 7-membered saturated heterocyclic ring, wherein the 4- to 7-membered saturated heterocyclic ring is optionally fused with a saturated carbon ring or an aromatic ring, the 4- to 7-membered saturated heterocyclic ring is optionally substituted with halogen, oxo, $C_6$-$C_{10}$ aryl, 5- to 10-membered heteroaryl, 4- to 8-membered cyclic amino (wherein the cyclic amino is optionally substituted with one or more halogens), or $OS_8$, and $S_8$ is hydrogen, $C_1$-$C_6$ alkyl, $C_1$-$C_6$ haloalkyl, $C_1$-$C_6$ hydroxyalkyl, $C_7$-$C_{14}$ aralkyl (wherein the aralkyl is optionally substituted with one or more halogens, $C_1$-$C_6$ alkyl, $C_1$-$C_6$ alkoxy, or $C_1$-$C_6$ haloalkoxy), or 5- to 10-membered heteroaryl$C_1$-$C_6$ alkyl, or $R_8$ and $Q_8$, together with the carbon atom to which they are attached, form a 3- to 8-membered alicyclic ring or a 4- to 7-membered saturated heterocyclic ring, or except when $R_8$ and $P_8$ form a 4- to 7-membered saturated heterocyclic ring, $P_5$ is hydrogen, $C_1$-$C_6$ alkyl, $C_1$-$C_6$ alkoxy$C_1$-$C_6$ alkyl, $C_2$-$C_6$ alkenyl, $C_1$-$C_6$ alkoxy$C_2$-$C_6$ alkenyl, $C_3$-$C_8$ cycloalkyl, 4- to 7-membered heterocyclyl, 4- to 7-membered heterocyclyl$C_1$-$C_6$ alkyl, $C_6$-$C_{10}$ aryl, $C_7$-$C_{14}$ aralkyl, 5- to 10-membered heteroaryl, or 5- to 10-membered heteroaryl$C_1$-$C_6$ alkyl, each of which is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen or $C_1$-$C_6$ alkyl), and aminocarbonyl (wherein the amino is —$NH_2$, mono-$C_1$-$C_6$ alkylamino, di-$C_1$-$C_6$ alkylamino, or 4- to 8-membered cyclic amino), except when $R_8$ and $Q_8$ form a 3- to 8-membered alicyclic ring or a 4- to 7-membered saturated heterocyclic ring, $Q_8$ is hydrogen or $C_1$-$C_6$ alkyl, $R_9$ is hydrogen, $C_1$-$C_6$ alkyl, $C_2$-$C_6$ alkenyl, $C_1$-$C_6$ alkoxy$C_1$-$C_6$ alkyl, $C_3$-$C_8$ cycloalkyl$C_1$-$C_6$ alkyl, $C_7$-$C_{14}$ aralkyl, or 5- to 10-membered heteroaryl$C_1$-$C_6$ alkoxy$C_1$-$C_6$ alkyl, each of which is optionally substituted with one or more groups independently selected from the group consisting of halogen, hydroxy, $C_1$-$C_6$ alkyl, $C_1$-$C_6$ haloalkyl, $C_1$-$C_6$ alkoxy, $C_1$-$C_6$ haloalkoxy, aminocarbonyl (wherein the amino is —$NH_2$, mono-$C_1$-$C_6$ alkylamino, di-$C_1$-$C_6$ alkylamino, or 4- to 8-membered cyclic amino), and $C_1$-$C_6$ alkylsulfonyl, or $R_9$ and $P_9$, together with the carbon atom to which $R_9$ is attached and the nitrogen atom to which $P_9$ is attached, form a 4- to 7-membered saturated heterocyclic ring, or $R_9$ and $Q_9$, together with the carbon atom to which they are attached, form a 3- to 8-membered alicyclic ring or a 4- to 7-membered saturated heterocyclic ring, or except when $R_9$ and $P_9$ form a 4- to 7-membered saturated heterocyclic ring, $P_9$ is hydrogen or $C_1$-$C_6$ alkyl, wherein the $C_1$-$C_6$ alkyl is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino), except when $R_9$ and $Q_9$ form a 3- to 8-membered alicyclic ring or a 4- to 7-membered saturated heterocyclic ring, $Q_9$ is hydrogen or $C_1$-$C_6$ alkyl, $R_{10}$ is $C_1$-$C_6$ alkyl, $C_2$-$C_6$ alkynyl, $C_1$-$C_6$ alkoxy$C_1$-$C_6$ alkyl, $C_3$-$C_8$ cycloalkyl, $C_3$-$C_8$ cycloalkyl$C_1$-$C_6$ alkyl, $C_3$-$C_8$ cycloalkoxy$C_1$-$C_6$ alkyl, or $C_7$-$C_{14}$ aralkyl, each of which is optionally substituted with one or more groups independently selected from the group consisting of halogen, hydroxy, and $C_1$-$C_6$ alkylsulfonyl, or $R_{10}$ and $P_{10}$, together with the carbon atom to which $R_{10}$ is attached and the nitrogen atom to which $P_{10}$ is attached, form a 4- to 7-membered saturated heterocyclic ring, or $R_{10}$ and $Q_{10}$, together with the carbon atom to which they are attached, form a 3- to 8-membered alicyclic ring or a 4- to 7-membered saturated heterocyclic ring, or except when $R_{10}$ and $P_{10}$ form a 4- to 7-membered saturated heterocyclic ring, $P_{10}$ is hydrogen or $C_1$-$C_6$ alkyl, wherein the $C_1$-$C_6$ alkyl is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alky lamino, or 4- to 8-membered cyclic amino, each of which is optionally substituted with halogen), and aminocarbonyl (wherein the amino is —NH$_2$, mono-C$_1$-C$_6$ alkylamino, di-C$_1$-C$_6$ alkylamino, or 4- to 8-membered cyclic amino), except when R$_{10}$ and Q$_{10}$ form a 3- to 8-membered alicyclic ring or a 4- to 7-membered saturated heterocyclic ring, Q$_{10}$ is hydrogen or C$_1$-C$_6$ alkyl, and L$_{11}$ is a single bond, or —CHM$_{11}$—, —(CH$_2$)$_n$S(CH$_2$)$_m$—, —(CH$_2$)$_n$S(O)(CH$_2$)$_m$—, or —(CH$_2$)$_n$S(O)$_2$(CH$_2$)$_m$—, wherein n and m are each independently 1 or 2, R$_{11}$ is hydrogen, C$_1$-C$_6$ alkyl, C$_2$-C$_6$ alkenyl, C$_2$-C$_6$ alkynyl, C$_1$-C$_6$ alkoxyC$_1$-C$_6$ alkyl, C$_7$-C$_{14}$ aralkyl, or aminocarbonyl (wherein the amino is —NH$_2$, mono C$_1$-C$_6$ alkylamino, di-C$_1$-C$_6$ alkylamino, or 4- to 8-membered cyclic amino), each of which is optionally substituted with one or more groups independently selected from the group consisting of halogen, oxo, hydroxy, C$_1$-C$_6$ alkyl, 4- to 7-membered heterocyclyl, aminocarbonyl (wherein the amino is —NH$_2$, mono-C$_1$-C$_6$ alkylamino, di-C$_1$-C$_6$ alkylamino, or 4- to 8-membered cyclic amino), and C$_1$-C$_6$ alkylsulfonyl, or R$_{11}$ is a peptide chain comprising 1 to 4 amino acid residues, or R$_{11}$ and P$_{11}$, together with the carbon atom to which R$_{11}$ is attached and the nitrogen atom to which P$_{11}$ is attached, form a 4- to 7-membered saturated heterocyclic ring, or R$_{11}$ and Q$_{11}$, together with the carbon atom to which they are attached, form a 3- to 8-membered alicyclic ring or a 4- to 7-membered saturated heterocyclic ring, or R$_{11}$ and M$_{11}$, together with the carbon atom to which R$_{11}$ is attached and the carbon atom to which M$_{11}$ is attached, form a 3- to 8-membered alicyclic ring, except when R$_{11}$ and P$_{11}$ form a 4- to 7-membered saturated heterocyclic ring, P$_{11}$ is hydrogen or C$_1$-C$_6$ alkyl, wherein the C$_1$-C$_6$ alkyl is optionally substituted with one or more groups independently selected from the group consisting of halogen, hydroxy, C$_1$-C$_6$ alkoxy, amino (wherein the amino is —NH$_2$, mono-C$_1$-C$_6$ alkylamino, di-C$_1$-C$_6$ alkylamino, or 4- to 8-membered cyclic amino, each of which is optionally substituted with halogen), and aminocarbonyl (wherein the amino is —NH$_2$, mono-C$_1$-C$_6$ alkylamino, di-C$_1$-C$_6$ alkylamino, or 4- to 8-membered cyclic amino), except when R$_{11}$ and Q$_{11}$ form a 3- to 8-membered alicyclic ring or a 4- to 7-membered saturated heterocyclic ring, Q$_{11}$ is hydrogen or C$_1$-C$_6$ alkyl, except when R$_{11}$ and M$_{11}$ form a 3- to 8-membered alicyclic ring, M$_{11}$ is hydrogen, wherein, when L$_1$ is a single bond, L$_{11}$ is —CHM$_{11}$—, —(CH$_2$)$_n$S(CH$_2$)$_m$—, —(CH$_2$)$_n$S(O)(CH$_2$)$_m$—, or —(CH$_2$)$_n$S(O)$_2$(CH$_2$)$_m$—, and when L$_1$ is —CHM$_{11}$—, —(CH$_2$)$_n$S(CH$_2$)$_m$—, —(CH$_2$)$_n$S(O)(CH$_2$)$_m$—, or —(CH$_2$)$_n$S(O)$_2$(CH$_2$)$_m$—, L$_{11}$ is a single bond, and at least three of P$_1$ to P$_{11}$ are not hydrogen.

[2] The cyclic peptide compound, or salt thereof, or solvate thereof according to [1], wherein the compound is represented by formula (2) below:

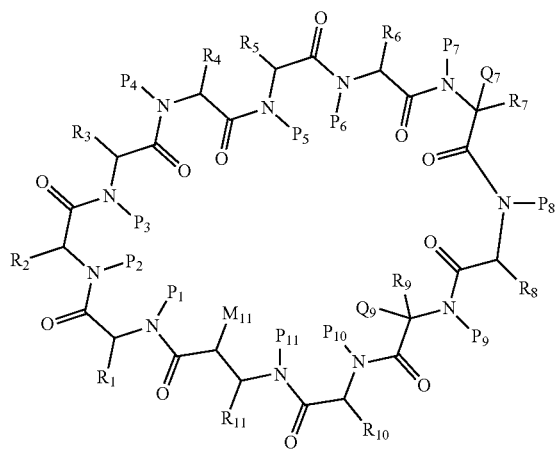

(2)

wherein,

R$_1$ is C$_1$-C$_6$ alkyl, C$_1$-C$_6$ haloalkyl, C$_1$-C$_6$ hydroxyalkyl, C$_1$-C$_6$ alkylsulfonylC$_1$-C$_6$ alkyl, C$_2$-C$_6$ alkynyl, C$_1$-C$_6$ alkoxyC$_1$-C$_6$ alkyl (wherein the C$_1$-C$_6$ alkoxyC$_1$-C$_6$ alkyl is optionally substituted with one or more halogens, aminocarbonyl (wherein the amino is —NH$_2$, mono-C$_1$-C$_6$ alkylamino, di-C$_1$-C$_6$ alkylamino, or 4- to 8-membered cyclic amino), or hydroxy), C$_3$-C$_8$ cycloalkyl, C$_3$-C$_8$ cycloalkylC$_1$-C$_6$ alkyl, or C$_3$-C$_8$ cycloalkoxyC$_1$-C$_6$ alkyl, or R$_1$ and P$_1$, together with the nitrogen atom to which P$_1$ is attached and the carbon atom to which R$_1$ is attached, form a 4- to 7-membered saturated heterocyclic ring, or except when R$_1$ and P$_1$ form a 4- to 7-membered saturated heterocyclic ring, P$_1$ is hydrogen or C$_1$-C$_6$ alkyl, R$_2$ is C$_1$-C$_6$ alkyl, C$_1$-C$_6$ haloalkyl, C$_1$-C$_6$ hydroxyalkyl, C$_1$-C$_6$ alkylsulfonylC$_1$-C$_6$ alkyl, C$_1$-C$_6$ cyanoalkyl, C$_2$-C$_6$ alkenyl, C$_2$-C$_6$ alkynyl, C$_1$-C$_6$ alkoxyC$_1$-C$_6$ alkyl optionally substituted with one or more halogens, C$_3$-C$_8$ cycloalkyl, C$_3$-C$_8$ cycloalkylC$_1$-C$_6$ alkyl, or C$_3$-C$_8$ cycloalkoxyC$_1$-C$_6$ alkyl, P$_2$ is hydrogen, R$_3$ is hydrogen, C$_1$-C$_6$ alkyl, C$_1$-C$_6$ hydroxyalkyl, C$_1$-C$_6$ alkoxyC$_1$-C$_6$ alkyl (wherein the C$_1$-C$_6$ alkoxyC$_1$-C$_6$ alkyl is optionally substituted with aminocarbonyl (wherein the amino is —NH$_2$, mono-C$_1$-C$_6$ alkylamino, di-C$_1$-C$_6$ alkylamino, or 4- to 8-membered cyclic amino) or hydroxy), aminocarbonylC$_1$-C$_6$ alkyl (wherein the amino is —NH$_2$, mono-C$_1$-C$_6$ alkylamino, di-C$_1$-C$_6$ alkylamino, or 4- to 8-membered cyclic amino), C$_3$-C$_8$ cycloalkyl, C$_3$-C$_8$ cycloalkylC$_1$-C$_6$ alkyl, C$_3$-C$_8$ cycloalkoxyC$_1$-C$_6$ alkyl, or C$_7$-C$_{14}$ aralkyl, or R$_3$ and P$_3$, together with the nitrogen atom to which P$_3$ is attached and the carbon atom to which R$_3$ is attached, form a 4- to 7-membered saturated heterocyclic ring, except when R$_3$ and P$_3$ form a 4- to 7-membered saturated heterocyclic ring, P$_3$ is hydrogen, C$_1$-C$_6$ alkyl, C$_1$-C$_6$ alkoxyC$_1$-C$_6$ alkyl, C$_1$-C$_6$ aminoalkyl (wherein the amino is —NH$_2$, protected amino, mono-C$_1$-C$_6$ alkylamino, di-C$_1$-C$_6$ alkylamino, or 4- to 8-membered cyclic amino, each of which is optionally substituted with one or more halogens), or $C_3$-$C_8$ cycloalkyl, $R_4$ is hydrogen or $C_1$-$C_6$ alkyl, or $R_4$ and $P_4$ together with the nitrogen atom to which $P_4$ is attached and the carbon atom to which $R_4$ is attached form a 4- to 7-membered saturated heterocyclic ring, except when $R_4$ and $P_4$ form a 4- to 7-membered saturated heterocyclic ring, $P_4$ is $C_1$-$C_6$ alkyl or $C_1$-$C_6$ alkoxy$C_1$-$C_6$ alkyl, $R_5$ is $C_1$-$C_6$ alkyl, $C_1$-$C_6$ haloalkyl, $C_1$-$C_6$ hydroxyalkyl, $C_2$-$C_6$ alkenyl, $C_1$-$C_6$ alkylsulfonyl$C_1$-$C_6$ alkyl, $C_2$-$C_6$ alkynyl, $C_1$-$C_6$ alkoxy$C_1$-$C_6$ alkyl optionally substituted with one or more halogens, $C_3$-$C_8$ cycloalkyl, $C_3$-$C_8$ cycloalkyl$C_1$-$C_6$ alkyl, $C_3$-$C_8$ cycloalkoxy$C_1$-$C_6$ alkyl, $C_7$-$C_{14}$ aralkyl (wherein the $C_7$-$C_{14}$ aralkyl is optionally substituted with one or more halogens, $C_1$-$C_6$ alkyl, $C_1$-$C_6$ alkoxy, $C_1$-$C_6$ haloalkyl, $C_1$-$C_6$ haloalkoxy, or cyano), $C_6$-$C_{10}$ aryloxy$C_1$-$C_6$ alkyl optionally substituted with one or more halogens, $C_7$-$C_{14}$ aralkoxy$C_1$-$C_6$ alkyl, or 5- to 10-membered heteroaryl$C_1$-$C_6$ alkyl, or $R_5$ together with $R_8$ forms $C_4$-$C_8$ alkylene, $P_5$ is hydrogen or $C_1$-$C_6$ alkyl, $R_6$ is hydrogen or $C_1$-$C_6$ alkyl, or $R_6$ and $P_6$, together with the nitrogen atom to which $P_6$ is attached and the carbon atom to which $R_6$ is attached, form a 4- to 7-membered saturated heterocyclic ring, except when $R_6$ and $P_6$ form a 4- to 7-membered saturated heterocyclic ring, $P_6$ is $C_1$-$C_6$ alkyl or $C_3$-$C_8$ cycloalkyl, $R_7$ is $C_6$-$C_{10}$ aryloxy$C_1$-$C_6$ alkyl (wherein the $C_6$-$C_{10}$ aryloxy$C_1$-$C_6$ alkyl is optionally substituted with one or more groups independently selected from the group consisting of halogen and $C_1$-$C_6$ haloalkyl), $C_7$-$C_{14}$ aralkyl (wherein the $C_7$-$C_{14}$ aralkyl is optionally substituted with one or more groups independently selected from the group consisting of halogen, $C_1$-$C_6$ alkyl, $C_1$-$C_6$ haloalkyl, $C_1$-$C_6$ alkoxy, $C_1$-$C_6$ haloalkoxy, $C_2$-$C_6$ alkynyl, cyano, $C_1$-$C_6$ alkylsulfonyl, and $SF_5$), $C_7$-$C_{14}$ aralkoxy$C_1$-$C_6$ alkyl optionally substituted with one or more halogens, or 5- to 10-membered heteroaryl$C_1$-$C_6$ alkyl (wherein the 5- to 10-membered heteroaryl$C_1$-$C_6$ alkyl is optionally substituted with one or more halogens, $C_1$-$C_6$ alkyl, $C_1$-$C_6$ haloalkyl, or $C_1$-$C_6$ alkoxy), $Q_7$ is hydrogen or $C_1$-$C_6$ alkyl, $P_7$ is hydrogen, $R_8$ is hydrogen, $C_1$-$C_6$ alkyl, $C_1$-$C_6$ haloalkyl, $C_1$-$C_6$ hydroxyalkyl, $C_1$-$C_6$ carboxyalkyl, $C_1$-$C_6$ aminoalkyl (wherein the amino is —NH$_2$, protected amino, mono-$C_1$-$C_6$ alkylamino, di-$C_1$-$C_6$ alkylamino, or 4- to 8-membered cyclic amino, each of which is optionally substituted with one or more halogens), aminocarbonyl$C_1$-$C_6$ alkyl (wherein the amino is —NH$_2$, mono-$C_1$-$C_6$ alkylamino, di-$C_1$-$C_6$ alkylamino, or 4- to 8-membered cyclic amino, each of which is optionally substituted with one or more halogens), optionally protected 4- to 7-membered heterocyclyl$C_1$-$C_6$ alkyl, optionally protected 4- to 7-membered heterocycloalkylidene $C_1$-$C_6$ alkyl, $C_1$-$C_6$ alkoxy$C_1$-$C_6$ alkyl (wherein the $C_1$-$C_6$ alkoxy$C_1$-$C_6$ alkyl is optionally substituted with aminocarbonyl (wherein the amino is —NH$_2$, mono-$C_1$-$C_6$ alkylamino, di-$C_1$-$C_6$ alkylamino, or 4- to 8-membered cyclic amino) or hydroxy), $C_3$-$C_8$ cycloalkyl, $C_3$-$C_8$ cycloalkyl$C_1$-$C_6$ alkyl, $C_2$-$C_6$ alkenyl, $C_2$-$C_6$ alkenyloxycarbonyl$C_1$-$C_6$ alkyl, $C_2$-$C_6$ alkynyl, $C_6$-$C_{10}$ aryloxy$C_1$-$C_6$ alkyl, $C_7$-$C_{14}$ aralkyl (wherein the $C_7$-$C_{14}$ aralkyl is optionally substituted with one or more groups independently selected from the group consisting of halogen, hydroxy, $C_1$-$C_6$ alkyl, $C_1$-$C_6$ haloalkyl, $C_1$-$C_6$ alkoxy, $C_1$-$C_6$ haloalkoxy, and cyano), 5- to 10-membered heteroarylalkyl (wherein the 5- to 10-membered heteroarylalkyl is optionally substituted with one or more groups selected from the group consisting of $C_1$-$C_6$ alkyl, $C_1$-$C_6$ haloalkyl, $C_1$-$C_6$ alkoxy, and cyano), or 5- to 10-membered heteroaryl$C_1$-$C_6$ alkoxy$C_1$-$C_6$ alkyl optionally substituted with one or more halogens, or $R_8$ together with $R_5$ forms $C_4$-$C_8$ alkylene, or $R_8$ and $P_8$, together with the nitrogen atom to which $P_8$ is attached and the carbon atom to which $R_8$ is attached, form a 4- to 7-membered saturated heterocyclic ring, wherein the 4- to 7-membered saturated heterocyclic ring is optionally fused with a 3- to 8-membered saturated carbon ring or a 6- to 10-membered aromatic ring, and the 4- to 7-membered saturated heterocyclic ring is optionally substituted with one or more halogens, hydroxy, oxo, $C_1$-$C_6$ alkoxy, $C_1$-$C_6$ haloalkoxy, $C_1$-$C_6$ hydroxyalkoxy, $C_6$-$C_{10}$ aryl, 5- to 10-membered heteroaryl$C_1$-$C_6$ alkoxy, $C_7$-$C_{14}$ aralkoxy (wherein the $C_7$-$C_{14}$ aralkoxy is optionally substituted with one or more halogens, $C_1$-$C_6$ alkyl, $C_1$-$C_6$ alkoxy, or $C_1$-$C_6$ haloalkoxy), 4- to 8-membered cyclic amino optionally substituted with one or more halogens, or 5- to 10-membered heteroaryl, or except when $R_8$ and $P_8$ form a 4- to 7-membered saturated heterocyclic ring, $P_8$ is hydrogen, $C_1$-$C_6$ alkyl, $C_1$-$C_6$ hydroxyalkyl, $C_1$-$C_6$ alkoxy$C_1$-$C_6$ alkyl (wherein the $C_1$-$C_6$ alkoxy$C_1$-$C_6$ alkyl is optionally substituted with one or more halogens, hydroxy, di-$C_1$-$C_6$ alkylaminocarbonyl, $C_1$-$C_6$ alkoxy, or amino (wherein the amino is —NH$_2$, mono-$C_1$-$C_6$ alkylamino, di-$C_1$-$C_6$ alkylamino, or 4- to 8-membered cyclic amino)), aminocarbonyl$C_1$-$C_6$ alkyl (wherein the amino is —NH$_2$, mono-$C_1$-$C_6$ alkylamino, di-$C_1$-$C_6$ alkylamino, or 4- to 8-membered cyclic amino, each of which is optionally substituted with one or more halogens), $C_1$-$C_6$ aminoalkyl (wherein the amino is —NH$_2$, mono-$C_1$-$C_6$ alkylamino, di-$C_1$-$C_6$ alkylamino, or 4- to 8-membered cyclic amino, each of which is optionally substituted with one or more halogens or $C_1$-$C_6$ alkyl), $C_2$-$C_6$ alkenyl, $C_2$-$C_6$ hydroxyalkenyl, aminocarbonyl$C_2$-$C_6$ alkenyl (wherein the amino is —NH$_2$, mono-$C_1$-$C_6$ alkylamino, di-$C_1$-$C_6$ alkylamino, or 4- to 8-membered cyclic amino), $C_1$-$C_6$ alkoxy$C_2$-$C_6$ alkenyl, $C_3$-$C_8$ cycloalkyl optionally substituted with one or more halogens, 4- to 7-membered heterocyclyl, 4- to 7-membered heterocyclyl$C_1$-$C_6$ alkyl, $C_6$-$C_{10}$ aryl optionally substituted with one or more halogens, $C_7$-$C_{14}$ aralkyl, 5- to 10-membered heteroaryl, or 5- to 10-membered heteroaryl$C_1$-$C_6$ alkyl, $R_9$ is hydrogen, $C_1$-$C_6$ alkyl, $C_1$-$C_6$ haloalkyl, $C_2$-$C_6$ alkenyl, $C_1$-$C_6$ alkoxy$C_1$-$C_6$ alkyl (wherein the $C_1$-$C_6$ alkoxy$C_1$-$C_6$ alkyl is optionally substituted with aminocarbonyl (wherein the amino is —NH$_2$, mono-$C_1$-$C_6$ alkylamino, di-$C_1$-$C_6$ alkylamino, or 4- to 8-membered cyclic amino), hydroxy, or 5- to 10-membered heteroaryl optionally substituted with one or more halogens), $C_3$-$C_8$ cycloalkyl$C_1$-$C_6$ alkyl, or $C_7$-$C_{14}$ aralkyl (wherein the $C_7$-$C_{14}$ aralkyl is optionally substituted with one or more groups independently selected from the group consisting of halogens, $C_1$-$C_6$ alkyl, $C_1$-$C_6$ haloalkyl, $C_1$-$C_6$ alkoxy, $C_1$-$C_6$ haloalkoxy, and cyano), or $R_9$ and $Q_9$, together with the carbon atom to which they are attached, form a 3- to 8-membered alicyclic ring or a 4- to 7-membered saturated heterocyclic ring, or $R_9$ and $P_9$, together with the nitrogen atom to which $P_9$ is attached and the carbon atom to which $R_9$ is attached, form a 4- to 7-membered saturated heterocyclic ring, except when $R_9$ and $Q_9$ form a 3- to 8-membered alicyclic ring or a 4- to 7-membered saturated heterocyclic ring, $Q_9$ is hydrogen or $C_1$-$C_6$ alkyl, except when $R_9$ and $P_9$ form a 4- to 7-membered saturated heterocyclic ring, $P_9$ is hydrogen or $C_1$-$C_6$ alkyl, $R_{10}$ is $C_1$-$C_6$ alkyl, $C_1$-$C_6$ haloalkyl, $C_1$-$C_6$ hydroxyalkyl, $C_1$-$C_6$ alkylsulfonyl$C_1$-$C_6$ alkyl, $C_2$-$C_6$ alkynyl, $C_1$-$C_6$ alkoxy$C_1$-$C_6$ alkyl optionally substituted with one or more halogens, $C_3$-$C_8$ cycloalkyl, $C_3$-$C_8$ cycloalkyl$C_1$-$C_6$ alkyl, $C_3$-$C_8$ cycloalkoxy$C_1$-$C_6$ alkyl, or $C_7$-$C_{14}$ aralkyl, or $R_{10}$ and $P_{10}$, together with the nitrogen atom to which $P_{10}$ is attached and the carbon atom to which $R_{10}$ is attached, form a 4- to 7-membered saturated heterocyclic ring, except when $R_{10}$ and $P_{10}$ form a 4- to 7-membered saturated heterocyclic ring, $P_{10}$ is hydrogen or $C_1$-$C_6$ alkyl, $R_{11}$ is hydrogen, $C_1$-$C_6$ alkyl, $C_1$-$C_6$ haloalkyl, $C_2$-$C_6$ alkenyl, $C_2$-$C_6$ alkynyl, $C_1$-$C_6$ alkoxy$C_1$-$C_6$ alkyl (wherein the $C_1$-$C_6$ alkoxy$C_1$-$C_6$ alkyl is optionally substituted with hydroxy or aminocarbonyl (wherein the amino is —$NH_2$, mono-$C_1$-$C_6$ alkylamino, di-$C_1$-$C_6$ alkylamino, or 4- to 8-membered cyclic amino)), $C_7$-$C_{14}$ aralkyl optionally substituted with one or more halogens, or aminocarbonyl (wherein the amino is —$NH_2$, mono-$C_1$-$C_6$ alkylamino, di-$C_1$-$C_6$ alkylamino, or 4- to 8-membered cyclic amino, wherein the cyclic amino is optionally further substituted with one or more halogens, one or more oxo, one or more $C_1$-$C_6$ alkyl, or 4- to 7-membered heterocyclyl), or $R_{11}$ and $M_{11}$, together with the carbon atom to which $R_{11}$ is attached and the carbon atom to which $M_{11}$ is attached, form a 3- to 8-membered alicyclic ring, $R_{11}$ and $P_{11}$, together with the nitrogen atom to which $P_{11}$ is attached and the carbon atom to which $R_{11}$ is attached, form a 4- to 7-membered saturated heterocyclic ring, except when $R_{11}$ and $M_{11}$ form a 3- to 8-membered alicyclic ring, $M_{11}$ is hydrogen, except when $R_{11}$ and $P_{11}$ form a 4- to 7-membered saturated heterocyclic ring, $P_{11}$ is hydrogen or $C_1$-$C_6$ alkyl.

[3] The cyclic peptide compound or salt thereof, or solvate thereof according to any one of [1] and [2], wherein $R_{11}$ is —$CONR_{11A}R_{11B}$, wherein $R_{11A}$ and $R_{11B}$ are each independently hydrogen or $C_1$-$C_6$ alkyl, or $R_{11A}$ and $R_{11B}$, together with the nitrogen atom to which they are attached, form a 4- to 8-membered saturated heterocyclic ring, wherein the 4- to 8-membered saturated heterocyclic ring is optionally substituted with one or more groups independently selected from the group consisting of halogen, oxo, $C_1$-$C_6$ alkyl, and 4- to 7-membered heterocyclyl.

[4] The cyclic peptide compound or salt thereof, or solvate thereof according to any one of [1] to [3], wherein $R_7$ is —$(CH_2)_x$—$O_y$—$(CH_2)_{z1}$—$C_6$-$C_{10}$ aryl or —$(CH_2)_x$—$O_y$—$(CH_2)_{z2}$-5- to 10-membered heteroaryl optionally substituted with one to five groups independently selected from the group consisting of halogen, $C_1$-$C_4$ alkyl, $C_2$-$C_4$ alkynyl, $C_1$-$C_3$ haloalkyl, $C_1$-$C_3$ haloalkoxy, $C_1$-$C_4$ alkoxy, —CN, $C_1$-$C_3$ alkylsulfonyl, hydroxy, and $SF_5$, wherein x is 1, 2, or 3, y is 0 or 1, z1 is 0, 1, 2, or 3, and z2 is 1, 2, or 3, provided that the sum of x, y, and z1 or z2 is 1 to 4.

[5] The cyclic peptide compound or salt thereof, or solvate thereof according to any one of [1] to [4], wherein $R_4$ and $P_4$, together with the nitrogen atom to which $P_4$ is attached and the carbon atom to which $R_4$ is attached, form a 4- to 7-membered saturated heterocyclic ring.

[6] The cyclic peptide compound or salt thereof, or solvate thereof according to any one of [1] to [5], wherein $R_8$ and $P_8$, together with the nitrogen atom to which $P_8$ is attached and the carbon atom to which $R_8$ is attached, form a 4- to 7-membered saturated heterocyclic ring.

[7] The cyclic peptide compound or salt thereof, or solvate thereof according to any one of [1] to [6], wherein $R_8$ is —$(CH_2)_x$—$O_y$—$(CH_2)_{z1}$—$C_6$-$C_{10}$ aryl or —$(CH_2)_x$—$O_y$—$(CH_2)_{z2}$-5- to 10-membered heteroaryl optionally substituted with one to five groups independently selected from the group consisting of halogen, $C_1$-$C_4$ alkyl, $C_2$-$C_4$ alkynyl, $C_1$-$C_3$ haloalkyl, $C_1$-$C_3$ haloalkoxy, $C_1$-$C_4$ alkoxy, —CN, $C_1$-$C_3$ alkylsulfonyl, hydroxy, and $SF_5$, wherein x is 1, 2, or 3, y is 0 or 1, z1 is 0, 1, 2, or 3, and z2 is 1, 2, or 3, provided that the sum of x, y, and z1 or z2 is 1 to 4.

[8] The cyclic peptide compound or salt thereof, or solvate thereof according to any one of [1] to [7], wherein $R_9$ is $C_1$-$C_6$ alkyl, $C_2$-$C_6$ alkenyl, or $C_7$-$C_{14}$ aralkyl, and $Q_9$ is $C_1$-$C_6$ alkyl, or $R_9$ and $Q_9$ together with the carbon atom to which they are attached form a 3- to 8-membered alicyclic ring or a 4- to 7-membered saturated heterocyclic ring.

[9] The cyclic peptide compound or salt thereof, or solvate thereof according to any one of [1] to [8], wherein at least three of $P_1$, $P_3$ to $P_6$, and $P_8$ to $P_{11}$ are alkyl.

[10] The cyclic peptide compound or salt thereof, or solvate thereof according to any one of [1] to [9], wherein $R_2$ and $R_3$ are $C_1$-$C_6$ alkyl.

[11] The cyclic peptide compound or salt thereof, or solvate thereof according to [1], wherein the compound is represented by formula (3) below:

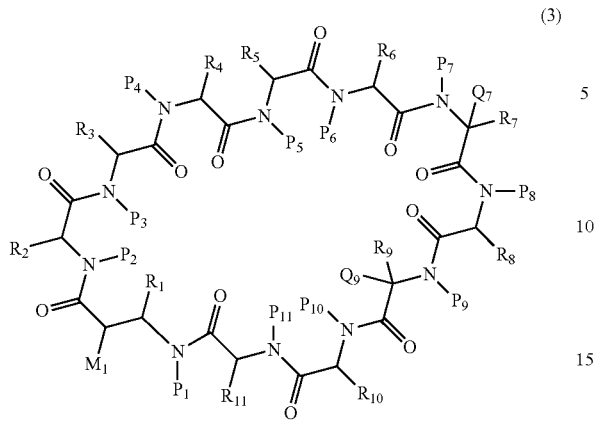

(3)

wherein,
- $R_1$ is hydrogen or $C_1$-$C_6$ alkyl,
- $P_1$ is hydrogen or $C_1$-$C_6$ alkyl,
- $M_1$ is hydrogen,
- $R_2$ is $C_1$-$C_6$ alkyl, $C_1$-$C_6$ haloalkyl, $C_1$-$C_6$ hydroxyalkyl, $C_1$-$C_6$ alkylsulfonyl$C_1$-$C_6$ alkyl, $C_1$-$C_6$ cyanoalkyl, $C_2$-$C_6$ alkenyl, $C_2$-$C_6$ alkynyl, $C_1$-$C_6$ alkoxy$C_1$-$C_6$ alkyl optionally substituted with one or more halogens, $C_3$-$C_8$ cycloalkyl, $C_3$-$C_8$ cycloalkyl$C_1$-$C_6$ alkyl, or $C_3$-$C_8$ cycloalkoxy$C_1$-$C_6$ alkyl,
- $P_2$ is hydrogen,
- $R_3$ is hydrogen, $C_1$-$C_6$ alkyl, $C_1$-$C_6$ hydroxyalkyl, $C_1$-$C_6$ alkoxy$C_1$-$C_6$ alkyl (wherein the $C_1$-$C_6$ alkoxy$C_1$-$C_6$ alkyl is optionally substituted with aminocarbonyl (wherein the amino is —$NH_2$, mono-$C_1$-$C_6$ alkylamino, di-$C_1$-$C_6$ alkylamino, or 4- to 8-membered cyclic amino) or hydroxy), aminocarbonyl$C_1$-$C_6$ alkyl (wherein the amino is —$NH_2$, mono-$C_1$-$C_6$ alkylamino, di-$C_1$-$C_6$ alkylamino, or 4- to 8-membered cyclic amino), $C_3$-$C_8$ cycloalkyl, $C_3$-$C_8$ cycloalkyl$C_1$-$C_6$ alkyl, $C_3$-$C_8$ cycloalkoxy$C_1$-$C_6$ alkyl, or $C_7$-$C_{14}$ aralkyl, or
- $R_3$ and $P_3$, together with the nitrogen atom to which $P_3$ is attached and the carbon atom to which $R_3$ is attached, form a 4- to 7-membered saturated heterocyclic ring,
- except when $R_3$ and $P_3$ form a 4- to 7-membered saturated heterocyclic ring, $P_3$ is hydrogen, $C_1$-$C_6$ alkyl, $C_1$-$C_6$ aminoalkyl (wherein the amino is —$NH_2$, protected amino, mono-$C_1$-$C_6$ alkylamino, di-$C_1$-$C_6$ alkylamino, or 4- to 8-membered cyclic amino, each of which is optionally substituted with one or more halogens), or $C_3$-$C_8$ cycloalkyl,
- $R_4$ is hydrogen or $C_1$-$C_6$ alkyl, or
- $R_4$ and $P_4$, together with the nitrogen atom to which $P_4$ is attached and the carbon atom to which $R_4$ is attached, form a 4- to 7-membered saturated heterocyclic ring,
- except when $R_4$ and $P_4$ form a 4- to 7-membered saturated heterocyclic ring, $P_4$ is $C_1$-$C_6$ alkyl or $C_1$-$C_6$ alkoxy$C_1$-$C_6$ alkyl,
- $R_5$ is $C_1$-$C_6$ alkyl, $C_1$-$C_6$ haloalkyl, $C_1$-$C_6$ hydroxyalkyl, $C_2$-$C_6$ alkenyl, $C_1$-$C_6$ alkylsulfonyl$C_1$-$C_6$ alkyl, $C_2$-$C_6$ alkynyl, $C_1$-$C_6$ alkoxy$C_1$-$C_6$ alkyl optionally substituted with one or more halogens, $C_3$-$C_8$ cycloalkyl, $C_3$-$C_8$ cycloalkyl$C_1$-$C_6$ alkyl, $C_3$-$C_8$ cycloalkoxy$C_1$-$C_6$ alkyl, $C_7$-$C_{14}$ aralkyl (wherein the $C_7$-$C_{14}$ aralkyl is optionally substituted with one or more halogens, $C_1$-$C_6$ alkyl, $C_1$-$C_6$ alkoxy, $C_1$-$C_6$ haloalkyl, $C_1$-$C_6$ haloalkoxy, or cyano), $C_6$-$C_{10}$ aryloxy$C_1$-$C_6$ alkyl optionally substituted with one or more halogens, $C_7$-$C_{14}$ aralkoxy$C_1$-$C_6$ alkyl, or 5- to 10-membered heteroaryl$C_1$-$C_6$ alkyl, or $R_5$ together with $R_8$ forms $C_4$-$C_8$ alkylene,
- $P_5$ is hydrogen or $C_1$-$C_6$ alkyl,
- $R_6$ is hydrogen or $C_1$-$C_6$ alkyl, or
- $R_6$ and $P_6$, together with the nitrogen atom to which $P_6$ is attached and the carbon atom to which $R_6$ is attached, form a 4- to 7-membered saturated heterocyclic ring,
- except when $R_6$ and $P_6$ form a 4- to 7-membered saturated heterocyclic ring, $P_6$ is $C_1$-$C_6$ alkyl or $C_3$-$C_8$ cycloalkyl,
- $R_7$ is $C_6$-$C_{10}$ aryloxy$C_1$-$C_6$ alkyl (wherein the $C_6$-$C_{10}$ aryloxy$C_1$-$C_6$ alkyl is optionally substituted with one or more groups independently selected from the group consisting of halogen and $C_1$-$C_6$ haloalkyl), $C_7$-$C_{14}$ aralkyl (wherein the $C_7$-$C_{14}$ aralkyl is optionally substituted with one or more groups independently selected from the group consisting of halogen, $C_1$-$C_6$ alkyl, $C_1$-$C_6$ haloalkyl, $C_1$-$C_6$ alkoxy, $C_1$-$C_6$ haloalkoxy, $C_2$-$C_6$ alkynyl, cyano, $C_1$-$C_6$ alkylsulfonyl, and $SF_5$), $C_7$-$C_{14}$ aralkoxy$C_1$-$C_6$ alkyl optionally substituted with one or more halogens, or 5- to 10-membered heteroaryl$C_1$-$C_6$ alkyl (wherein the 5- to 10-membered heteroaryl$C_1$-$C_6$ alkyl may be substituted with one or more halogens, $C_1$-$C_6$ alkyl, $C_1$-$C_6$ haloalkyl, or $C_1$-$C_6$ alkoxy),
- $Q_7$ is hydrogen or $C_1$-$C_6$ alkyl,
- $P_7$ is hydrogen,
- $R_8$ is hydrogen, $C_1$-$C_6$ alkyl, $C_1$-$C_6$ haloalkyl, $C_1$-$C_6$ hydroxyalkyl, $C_1$-$C_6$ carboxyalkyl, $C_1$-$C_6$ aminoalkyl (wherein the amino is —$NH_2$, protected amino, mono-$C_1$-$C_6$ alkylamino, di-$C_1$-$C_6$ alkylamino, or 4- to 8-membered cyclic amino, each of which is optionally substituted with one or more halogens), $C_1$-$C_6$ aminocarbonyl$C_1$-$C_6$ alkyl (wherein the amino is —$NH_2$, mono-$C_1$-$C_6$ alkylamino, di-$C_1$-$C_6$ alkylamino, or 4- to 8-membered cyclic amino, each of which is optionally substituted with one or more halogens), optionally protected 4- to 7-membered heterocyclyl$C_1$-$C_6$ alkyl, optionally protected 4- to 7-membered heterocycloalkylidene$C_1$-$C_6$ alkyl, $C_1$-$C_6$ alkoxy$C_1$-$C_6$ alkyl (wherein the $C_1$-$C_6$ alkoxy$C_1$-$C_6$ alkyl is optionally substituted with aminocarbonyl (wherein the amino is —$NH_2$, mono-$C_1$-$C_6$ alkylamino, di-$C_1$-$C_6$ alkylamino, or 4- to 8-membered cyclic amino) or hydroxy), $C_3$-$C_8$ cycloalkyl, $C_3$-$C_8$ cycloalkyl$C_1$-$C_6$ alkyl, $C_2$-$C_6$ alkenyl, $C_2$-$C_6$ alkenyloxycarbonyl$C_1$-$C_6$ alkyl, $C_2$-$C_6$ alkynyl, $C_6$-$C_{10}$ aryloxy$C_1$-$C_6$ alkyl, $C_7$-$C_{14}$ aralkyl (wherein the $C_7$-$C_{14}$ aralkyl is optionally substituted with one or more groups independently selected from the group consisting of halogen, hydroxy, $C_1$-$C_6$ alkyl, $C_1$-$C_6$ haloalkyl, $C_1$-$C_6$ alkoxy, $C_1$-$C_6$ haloalkoxy, and cyano), 5- to 10-membered heteroarylalkyl (wherein the 5- to 10-membered heteroarylalkyl is optionally substituted with one or more groups selected from the group consisting of $C_1$-$C_6$ alkyl, $C_1$-$C_6$ haloalkyl, $C_1$-$C_6$ alkoxy, and cyano), or 5- to 10-membered heteroaryl$C_1$-$C_6$ alkoxy$C_1$-$C_6$ alkyl optionally substituted with one or more halogens, or $R_8$ together with $R_5$ forms $C_4$-$C_8$ alkylene, or $R_8$ and $P_8$, together with the nitrogen atom to which $P_8$ is attached and the carbon atom to which $R_8$ is attached, form a 4- to 7-membered saturated heterocyclic ring, wherein the 4- to 7-membered saturated heterocyclic ring is optionally fused with a 3- to 8-membered saturated carbon ring or a 6- to 10-membered aromatic ring, and the 4- to 7-membered saturated heterocyclic ring is optionally substituted with one or more halogens, hydroxy, oxo, $C_1$-$C_6$ alkoxy, $C_1$-$C_6$ haloalkoxy, $C_1$-$C_6$ hydroxyalkoxy, $C_6$-$C_{10}$ aryl, 5- to 10-membered heteroaryl$C_1$-$C_6$ alkoxy, $C_7$-$C_{14}$ aralkoxy (wherein the $C_7$-$C_{14}$ aralkoxy is optionally substituted with one or more halogens, $C_1$-$C_6$ alkyl, $C_1$-$C_6$ alkoxy, or $C_1$-$C_6$ haloalkoxy), 4- to 8-membered cyclic amino optionally substituted with one or more halogens, or 5- to 10-membered heteroaryl, or except when $R_8$ and $P_8$ form a 4- to 7-membered saturated heterocyclic ring, $P_8$ is hydrogen, $C_1$-$C_6$ alkyl, $C_1$-$C_6$ hydroxyalkyl, $C_1$-$C_6$ alkoxy$C_1$-$C_6$ alkyl (wherein the $C_1$-$C_6$ alkoxy$C_1$-$C_6$ alkyl is optionally substituted with one or more halogens, hydroxy, di-$C_1$-$C_6$ alkylaminocarbonyl, or $C_1$-$C_6$ alkoxy), aminocarbonyl$C_1$-$C_6$ alkyl (wherein the amino is —NH$_2$, mono-$C_1$-$C_6$ alkylamino, di-$C_1$-$C_6$ alkylamino, or 4- to 8-membered cyclic amino, each of which is optionally substituted with one or more halogens), $C_1$-$C_6$ aminoalkyl (wherein the amino is —NH$_2$, mono-$C_1$-$C_6$ alkylamino, di-$C_1$-$C_6$ alkylamino, or 4- to 8-membered cyclic amino, each of which is optionally substituted with one or more halogens), $C_2$-$C_6$ alkenyl, $C_2$-$C_6$ hydroxyalkenyl, aminocarbonyl$C_2$-$C_6$ alkenyl (wherein the amino is —NH$_2$, mono-$C_1$-$C_6$ alkylamino, di-$C_1$-$C_6$ alkylamino, or 4- to 8-membered cyclic amino), $C_1$-$C_6$ alkoxy$C_2$-$C_6$ alkenyl, $C_3$-$C_8$ cycloalkyl optionally substituted with one or more halogens, 4- to 7-membered heterocyclyl, 4- to 7-membered heterocyclyl$C_1$-$C_6$ alkyl, $C_6$-$C_{10}$ aryl optionally substituted with one or more halogens, $C_7$-$C_{14}$ aralkyl, 5- to 10-membered heteroaryl, or 5- to 10-membered heteroaryl$C_1$-$C_6$ alkyl, $R_9$ is hydrogen, $C_1$-$C_6$ alkyl, $C_1$-$C_6$ haloalkyl, $C_2$-$C_6$ alkenyl, $C_1$-$C_6$ alkoxy$C_1$-$C_6$ alkyl (wherein the $C_1$-$C_6$ alkoxy$C_1$-$C_6$ alkyl is optionally substituted with aminocarbonyl (wherein the amino is —NH$_2$, mono-$C_1$-$C_6$ alkylamino, di-$C_1$-$C_6$ alkylamino, or 4- to 8-membered cyclic amino) or hydroxy), $C_3$-$C_8$ cycloalkyl$C_1$-$C_6$ alkyl, $C_7$-$C_{14}$ aralkyl (wherein the $C_7$-$C_{14}$ aralkyl is optionally substituted with one or more groups independently selected from the group consisting of halogens, $C_1$-$C_6$ alkyl, $C_1$-$C_6$ haloalkyl, $C_1$-$C_6$ alkoxy, $C_1$-$C_6$ haloalkoxy, and cyano), or 5- to 10-membered heteroaryl$C_1$-$C_6$ alkoxy$C_1$-$C_6$ alkyl optionally substituted with one or more halogens, or $R_9$ and $Q_9$, together with the carbon atom to which they are attached, form a 3- to 8-membered alicyclic ring or a 4- to 7-membered saturated heterocyclic ring, or $R_9$ and $P_9$, together with the nitrogen atom to which $P_9$ is attached and the carbon atom to which $R_9$ is attached, form a 4- to 7-membered saturated heterocyclic ring.

except when $R_9$ and $Q_9$ form a 4- to 7-membered saturated heterocyclic ring, $Q_9$ is hydrogen or $C_1$-$C_6$ alkyl, except when $R_9$ and $P_9$ form a 4- to 7-membered saturated heterocyclic ring, $P_9$ is hydrogen or $C_1$-$C_6$ alkyl, $R_{10}$ is $C_1$-$C_6$ alkyl, $C_1$-$C_6$ haloalkyl, $C_1$-$C_6$ hydroxyalkyl, $C_1$-$C_6$ alkylsulfonyl$C_1$-$C_6$ alkyl, $C_2$-$C_6$ alkynyl, $C_1$-$C_6$ alkoxy$C_1$-$C_6$ alkyl optionally substituted with one or more halogens, $C_3$-$C_8$ cycloalkyl, $C_3$-$C_8$ cycloalkyl$C_1$-$C_6$ alkyl, $C_3$-$C_8$ cycloalkoxy$C_1$-$C_6$ alkyl, or $C_7$-$C_{14}$ aralkyl, or $R_{10}$ and $P_{10}$, together with the nitrogen atom to which $P_{10}$ is attached and the carbon atom to which $R_{10}$ is attached, form a 4- to 7-membered saturated heterocyclic ring, except when $R_{10}$ and $P_{10}$ form a 4- to 7-membered saturated heterocyclic ring, $P_{10}$ is hydrogen or $C_1$-$C_6$ alkyl, $R_{11}$ is hydrogen, $C_1$-$C_6$ alkoxy$C_1$-$C_6$ alkyl optionally substituted with hydroxy, or $C_7$-$C_{14}$ aralkyl optionally substituted with one or more halogens, and $P_{11}$ is hydrogen or $C_1$-$C_6$ alkyl.

[12] A cyclic peptide compound represented by formula (1') below or a salt thereof, or a solvate thereof:

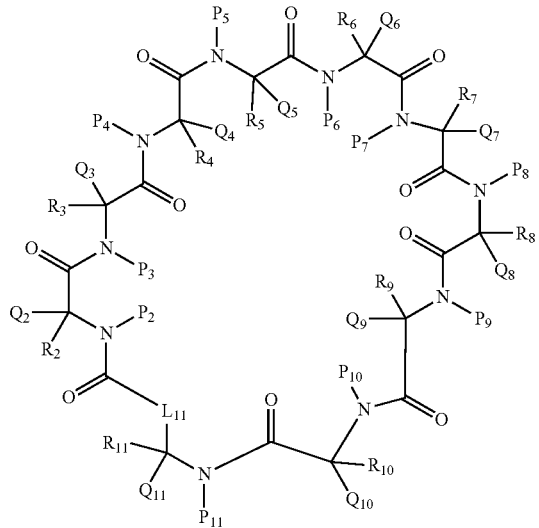

(1')

wherein, $R_2$ is $C_1$-$C_6$ alkyl, $C_2$-$C_6$ alkenyl, $C_2$-$C_6$ alkynyl, $C_1$-$C_6$ alkoxy$C_1$-$C_6$ alkyl, $C_3$-$C_8$ cycloalkyl, $C_3$-$C_8$ cycloalkyl$C_1$-$C_6$ alkyl, or $C_3$-$C_8$ cycloalkoxy$C_1$-$C_6$ alkyl, each of which is optionally substituted with one or more groups independently selected from the group consisting of halogen, hydroxy, cyano, and $C_1$-$C_6$ alkylsulfonyl, or $R_2$ and $P_2$, together with the carbon atom to which $R_2$ is attached and the nitrogen atom to which $P_2$ is attached, form a 4- to 7-membered saturated heterocyclic ring, or $R_2$ and $Q_2$, together with the carbon atom to which they are attached, form a 3- to 8-membered alicyclic ring or a 4- to 7-membered saturated heterocyclic ring, or except when $R_2$ and $P_2$ form a 4- to 7-membered saturated heterocyclic ring, $P_2$ is hydrogen or $C_1$-$C_6$ alkyl, wherein the $C_1$-$C_6$ alkyl is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino), except when $R_2$ and $Q_2$ form a 3- to 8-membered alicyclic ring or a 4- to 7-membered saturated heterocyclic ring, $Q_2$ is hydrogen or $C_1$-$C_6$ alkyl, $R_3$ is hydrogen, $C_1$-$C_6$ alkyl, $C_1$-$C_6$ alkoxy$C_1$-$C_6$ alkyl, $C_3$-$C_8$ cycloalkyl, $C_3$-$C_8$ cycloalkyl$C_1$-$C_6$ alkyl, $C_3$-$C_8$ cycloalkoxy$C_1$-$C_6$ alkyl, or $C_7$-$C_{14}$ aralkyl, each of which is optionally substituted with one or more groups independently selected from the group consisting of hydroxy and aminocarbonyl (wherein the amino is —$NH_2$, mono-$C_1$-$C_6$ alkylamino, di-$C_1$-$C_6$ alkylamino, or 4- to 8-membered cyclic amino), or $R_3$ and $P_3$, together with the carbon atom to which $R_3$ is attached and the nitrogen atom to which $P_3$ is attached, form a 4- to 7-membered saturated heterocyclic ring, or $R_3$ and $Q_3$, together with the carbon atom to which they are attached, form a 3- to 8-membered alicyclic ring or a 4- to 7-membered saturated heterocyclic ring, or except when $R_3$ and $P_3$ form a 4- to 7-membered saturated heterocyclic ring, $P_3$ is hydrogen, $C_1$-$C_6$ alkyl, $C_1$-$C_6$ alkoxy$C_1$-$C_6$ alkyl, or $C_3$-$C_8$ cycloalkyl, each of which is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and $C_1$-$C_6$ aminoalkyl (wherein the amino is —$NH_2$, mono-$C_1$-$C_6$ alkylamino, di-$C_1$-$C_6$ alkylamino, or 4- to 8-membered cyclic amino, wherein the 4- to 8-membered cyclic amino is optionally substituted with one or more halogens), except when $R_3$ and $Q_3$ form a 3- to 8-membered alicyclic ring or a 4- to 7-membered saturated heterocyclic ring, $Q_3$ is hydrogen or $C_1$-$C_6$ alkyl, $R_4$ is hydrogen or $C_1$-$C_6$ alkyl, or $R_4$ and $P_4$, together with the carbon atom to which $R_4$ is attached and the nitrogen atom to which $P_4$ is attached, form a 4- to 7-membered saturated heterocyclic ring, or $R_4$ and $Q_4$, together with the carbon atom to which they are attached, form a 3- to 8-membered alicyclic ring or a 4- to 7-membered saturated heterocyclic ring, or except when $R_4$ and $P_4$ form a 4- to 7-membered saturated heterocyclic ring, $P_4$ is hydrogen, $C_1$-$C_6$ alkyl, or $C_1$-$C_6$ alkoxy$C_1$-$C_6$ alkyl, each of which is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino), except when $R_4$ and $Q_4$ form a 3- to 8-membered alicyclic ring or a 4- to 7-membered saturated heterocyclic ring, $Q_4$ is hydrogen or $C_1$-$C_6$ alkyl, $R_5$ is $C_1$-$C_6$ alkyl, $C_2$-$C_6$ alkenyl, $C_2$-$C_6$ alkynyl, $C_1$-$C_6$ alkoxy$C_1$-$C_6$ alkyl, $C_3$-$C_8$ cycloalkyl, $C_3$-$C_8$ cycloalkyl$C_1$-$C_6$ alkyl, $C_3$-$C_8$ cycloalkoxy$C_1$-$C_6$ alkyl, $C_7$-$C_{14}$ aralkyl, $C_6$-$C_{10}$ aryloxy$C_1$-$C_6$ alkyl, $C_7$-$C_{14}$ aralkoxy$C_1$-$C_6$ alkyl, or 5- to 10-membered heteroaryl$C_1$-$C_6$ alkyl, each of which is optionally substituted with one or more groups independently selected from the group consisting of halogen, hydroxy, $C_1$-$C_6$ alkyl, $C_1$-$C_6$ haloalkyl, $C_1$-$C_6$ alkoxy, $C_1$-$C_6$ haloalkoxy, cyano, and $C_1$-$C_6$ alkylsulfonyl, or $R_5$ together with $R_8$ forms $C_4$-$C_8$ alkylene, or $R_5$ and $P_5$, together with the carbon atom to which $R_5$ is attached and the nitrogen atom to which $P_5$ is attached, form a 4- to 7-membered saturated heterocyclic ring, or $R_5$ and $Q_5$, together with the carbon atom to which they are attached, form a 3- to 8-membered alicyclic ring or a 4- to 7-membered saturated heterocyclic ring, or except when $R_5$ and $P_5$ form a 4- to 7-membered saturated heterocyclic ring, $P_5$ is hydrogen or $C_1$-$C_6$ alkyl, wherein the $C_1$-$C_6$ alkyl is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino), except when $R_5$ and $Q_5$ form a 3- to 8-membered alicyclic ring or a 4- to 7-membered saturated heterocyclic ring, $Q_5$ is hydrogen or $C_1$-$C_6$ alkyl, $R_6$ is hydrogen or $C_1$-$C_6$ alkyl, or $R_6$ and $P_6$, together with the carbon atom to which $R_6$ is attached and the nitrogen atom to which $P_6$ is attached, form a 4- to 7-membered saturated heterocyclic ring, or $R_6$ and $Q_6$, together with the carbon atom to which they are attached, form a 3- to 8-membered alicyclic ring or a 4- to 7-membered saturated heterocyclic ring, or except when $R_6$ and $P_6$ form a 4- to 7-membered saturated heterocyclic ring, $P_6$ is $C_1$-$C_6$ alkyl or $C_3$-$C_8$ cycloalkyl, each of which is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino), except when $R_6$ and $Q_6$ form a 3- to 8-membered alicyclic ring or a 4- to 7-membered saturated heterocyclic ring, $Q_6$ is hydrogen or $C_1$-$C_6$ alkyl, $R_7$ is $C_6$-$C_{10}$ aryloxy$C_1$-$C_6$ alkyl, $C_7$-$C_{14}$ aralkyl, $C_7$-$C_{14}$ aralkoxy$C_1$-$C_6$ alkyl, or 5- to 10-membered heteroaryl$C_1$-$C_6$ alkyl, each of which is optionally substituted with one or more groups independently selected from the group consisting of halogen, $C_1$-$C_6$ alkyl, $C_1$-$C_6$ haloalkyl, $C_2$-$C_6$ alkynyl, $C_1$-$C_6$ alkoxy, $C_1$-$C_6$ haloalkoxy, cyano, $C_1$-$C_6$ alkylsulfonyl, and $SF_5$, or $R_7$ and $P_7$, together with the carbon atom to which $R_7$ is attached and the nitrogen atom to which $P_7$ is attached, form a 4- to 7-membered saturated heterocyclic ring, or $R_7$ and $Q_7$, together with the carbon atom to which they are attached, form a 3- to 8-membered alicyclic ring or a 4- to 7-membered saturated heterocyclic ring, or except when $R_7$ and $P_7$ form a 4- to 7-membered saturated heterocyclic ring, $P_7$ is hydrogen or $C_1$-$C_6$ alkyl, wherein the $C_1$-$C_6$ alkyl is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino), except when $R_7$ and $Q_7$ form a 3- to 8-membered alicyclic ring or a 4- to 7-membered saturated heterocyclic ring, $Q_7$ is hydrogen or $C_1$-$C_6$ alkyl, $R_8$ is hydrogen, $C_1$-$C_6$ alkyl, $C_2$-$C_6$ alkenyl, $C_2$-$C_6$ alkynyl, $C_1$-$C_6$ alkoxy$C_1$-$C_6$ alkyl, $C_2$-$C_6$ alkenyloxycarbonyl$C_1$-$C_6$ alkyl, $C_3$-$C_8$ cycloalkyl, $C_3$-$C_8$ cycloalkyl$C_1$-$C_6$ alkyl, $C_6$-$C_{10}$aryloxy$C_1$-$C_6$ alkyl, $C_7$-$C_{14}$ aralkyl, $C_7$-$C_{14}$ aralkoxy$C_1$-$C_6$ alkyl, 5- to 10-membered heteroaryl$C_1$-$C_6$ alkyl, or 5- to 10-membered heteroaryl$C_1$-$C_6$ alkoxy$C_1$-$C_6$ alkyl, each of which is optionally substituted with one or more groups independently selected from the group consisting of halogen, hydroxy, carboxy, $C_1$-$C_6$ alkyl, $C_1$-$C_6$ haloalkyl, $C_2$-$C_6$ alkynyl, $C_1$-$C_6$ alkoxy, $C_1$-$C_6$ haloalkoxy, cyano, amino (wherein the amino is —$NH_2$, protected amino, mono-$C_1$-$C_6$ alkylamino, di-$C_1$-$C_6$ alkylamino, or 4- to 8-membered cyclic amino, each of which is optionally substituted with halogen), aminocarbonyl (wherein the amino is —$NH_2$, mono-$C_1$-$C_6$ alkylamino, di-$C_1$-$C_6$ alkylamino, or 4- to 8-membered cyclic amino, each of which is optionally substituted with halogen), 4- to 7-membered heterocycloalkylidene, protected 4- to 7-membered heterocycloalkylidene, 4- to 7-membered heterocyclyl, and protected 4- to 7-membered heterocyclyl, or $R_8$ together with $R_5$ forms $C_4$-$C_8$ alkylene, or $R_8$ and $P_8$, together with the carbon atom to which $R_8$ is attached and the nitrogen atom to which $P_8$ is attached, form a 4- to 7-membered saturated heterocyclic ring, wherein the 4- to 7-membered saturated heterocyclic ring is optionally fused with a saturated carbon ring or an aromatic ring, the 4- to 7-membered saturated heterocyclic ring is optionally substituted with halogen, oxo, $C_6$-$C_{10}$ aryl, 5- to 10-membered heteroaryl, 4- to 8-membered cyclic amino (wherein the cyclic amino is optionally substituted with one or more halogens), or $OS_8$, and $S_8$ is hydrogen, $C_1$-$C_6$ alkyl, $C_1$-$C_6$ haloalkyl, $C_1$-$C_6$ hydroxyalkyl, $C_7$-$C_{14}$ aralkyl (wherein the aralkyl is optionally substituted with one or more halogens, $C_1$-$C_6$ alkyl, $C_1$-$C_6$ alkoxy, or $C_1$-$C_6$ haloalkoxy), or 5- to 10-membered heteroaryl$C_1$-$C_6$ alkyl, or $R_8$ and $Q_8$, together with the carbon atom to which they are attached, form a 3- to 8-membered alicyclic ring or a 4- to 7-membered saturated heterocyclic ring, or except when $R_8$ and $P_8$ form a 4- to 7-membered saturated heterocyclic ring, $P_8$ is hydrogen, $C_1$-$C_6$ alkyl, $C_1$-$C_6$ alkoxy$C_1$-$C_6$ alkyl, $C_2$-$C_6$ alkenyl, $C_1$-$C_6$ alkoxy$C_2$-$C_6$ alkenyl, $C_3$-$C_8$ cycloalkyl, 4- to 7-membered heterocyclyl, 4- to 7-membered heterocyclyl$C_1$-$C_6$ alkyl, $C_6$-$C_{10}$ aryl, $C_7$-$C_{14}$ aralkyl, 5- to 10-membered heteroaryl, or 5- to 10-membered heteroaryl$C_1$-$C_6$ alkyl, each of which is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen or $C_1$-$C_6$ alkyl), and aminocarbonyl (wherein the amino is —$NH_2$, mono-$C_1$-$C_6$ alkylamino, di-$C_1$-$C_6$ alkylamino, or 4- to 8-membered cyclic amino), except when $R_8$ and $Q_8$ form a 3- to 8-membered alicyclic ring or a 4- to 7-membered saturated heterocyclic ring, $Q_8$ is hydrogen or $C_1$-$C_6$ alkyl, $R_9$ is hydrogen, $C_1$-$C_6$ alkyl, $C_2$-$C_6$ alkenyl, $C_1$-$C_6$ alkoxy$C_1$-$C_6$ alkyl, $C_3$-$C_8$ cycloalkyl$C_1$-$C_6$ alkyl, $C_7$-$C_{14}$ aralkyl, or 5- to 10-membered heteroaryl$C_1$-$C_6$ alkoxy$C_1$-$C_6$ alkyl, each of which is optionally substituted with one or more groups independently selected from the group consisting of halogen, hydroxy, $C_1$-$C_6$ alkyl, $C_1$-$C_6$ haloalkyl, $C_1$-$C_6$ alkoxy, $C_1$-$C_6$ haloalkoxy, aminocarbonyl (wherein the amino is —$NH_2$, mono-$C_1$-$C_6$ alkylamino, di-$C_1$-$C_6$ alkylamino, or 4- to 8-membered cyclic amino), and $C_1$-$C_6$ alkylsulfonyl, or $R_9$ and $P_9$, together with the carbon atom to which $R_9$ is attached and the nitrogen atom to which $P_9$ is attached, form a 4- to 7-membered saturated heterocyclic ring, or $R_9$ and $Q_9$, together with the carbon atom to which they are attached, form a 3- to 8-membered alicyclic ring or a 4- to 7-membered saturated heterocyclic ring, or except when $R_9$ and $P_9$ form a 4- to 7-membered saturated heterocyclic ring, $P_9$ is hydrogen or $C_1$-$C_6$ alkyl, wherein the $C_1$-$C_6$ alkyl is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino), except when $R_9$ and $Q_9$ form a 3- to 8-membered alicyclic ring or a 4- to 7-membered saturated heterocyclic ring, $Q_9$ is hydrogen or $C_1$-$C_6$ alkyl, $R_{10}$ is $C_1$-$C_6$ alkyl, $C_2$-$C_6$ alkynyl, $C_1$-$C_6$ alkoxy$C_1$-$C_6$ alkyl, $C_3$-$C_8$ cycloalkyl, $C_3$-$C_8$ cycloalkyl$C_1$-$C_6$ alkyl, $C_3$-$C_8$ cycloalkoxy$C_1$-$C_6$ alkyl, or $C_7$-$C_{14}$ aralkyl, each of which is optionally substituted with one or more groups independently selected from the group consisting of halogen, hydroxy, and $C_1$-$C_6$ alkylsulfonyl, or $R_{10}$ and $P_{10}$, together with the carbon atom to which $R_{10}$ is attached and the nitrogen atom to which $P_{10}$ is attached, form a 4- to 7-membered saturated heterocyclic ring, or $R_{10}$ and $Q_{10}$, together with the carbon atom to which they are attached, form a 3- to 8-membered alicyclic ring or a 4- to 7-membered saturated heterocyclic ring, or except when $R_{10}$ and $P_{10}$ form a 4- to 7-membered saturated heterocyclic ring, $P_{10}$ is hydrogen or $C_1$-$C_6$ alkyl, wherein the $C_1$-$C_6$ alkyl is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino), except when $R_{10}$ and $Q_{10}$ form a 3- to 8-membered alicyclic ring or a 4- to 7-membered saturated heterocyclic ring, $Q_{10}$ is hydrogen or $C_1$-$C_6$ alkyl, and $L_{11}$ is —$CHM_{11}$-, —$(CH_2)_nS(CH_2)_m$—, —$(CH_2)_nS(O)(CH_2)_m$—, or —$(CH_2)_nS(O)_2(CH_2)_m$—, wherein n and m are each independently 1 or 2, $R_{11}$ is hydrogen, $C_1$-$C_6$ alkyl, $C_2$-$C_6$ alkenyl, $C_2$-$C_6$ alkynyl, $C_1$-$C_6$ alkoxy$C_1$-$C_6$ alkyl, $C_7$-$C_{14}$ aralkyl, or aminocarbonyl (wherein the amino is —$NH_2$, mono $C_1$-$C_6$ alkylamino, di-$C_1$-$C_6$ alkylamino, or 4- to 8-membered cyclic amino), each of which is optionally substituted with one or more groups independently selected from the group consisting of halogen, oxo, hydroxy, $C_1$-$C_6$ alkyl, 4- to 7-membered heterocyclyl, aminocarbonyl (wherein the amino is —$NH_2$, mono-$C_1$-$C_6$ alkylamino, di-$C_1$-$C_6$ alkylamino, or 4- to 8-membered cyclic amino), and $C_1$-$C_6$ alkylsulfonyl, or $R_{11}$ is a peptide chain comprising 1 to 4 amino acid residues, or $R_{11}$ and $P_{11}$, together with the carbon atom to which $R_{11}$ is attached and the nitrogen atom to which $P_{11}$ is attached, form a 4- to 7-membered saturated heterocyclic ring, or $R_{11}$ and $Q_{11}$, together with the carbon atom to which they are attached, form a 3- to 8-membered alicyclic ring or a 4- to 7-membered saturated heterocyclic ring, or $R_{11}$ and $M_{11}$, together with the carbon atom to which $R_{11}$ is attached and the carbon atom to which $M_{11}$ is attached, form a 3- to 8-membered alicyclic ring, except when $R_{11}$ and $P_{11}$ form a 4- to 7-membered saturated heterocyclic ring, $P_{11}$ is hydrogen or $C_1$-$C_6$ alkyl, wherein the $C_1$-$C_6$ alkyl is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino), except when $R_{11}$ and $Q_{11}$ form a 3- to 8-membered alicyclic ring or a 4- to 7-membered saturated heterocyclic ring, $Q_{11}$ is hydrogen or $C_1$-$C_6$ alkyl, except when $R_{11}$ and $M_{11}$ form a 3- to 8-membered alicyclic ring, $M_{11}$ is hydrogen, and at least three of $P_2$ to $P_1$ are not hydrogen.

[13] The cyclic peptide compound or salt thereof, or solvate thereof according to [1] or [12], wherein the compound is selected from the group consisting of cyclic peptide compounds set forth in Table 24.

[14] A pharmaceutical composition comprising the cyclic peptide compound or salt thereof, or solvate thereof according to any one of [1] to [13].

[15] An amino acid set forth in Table 5 or Table 6 or a salt thereof, or a solvate thereof.

[16] An inhibitor of binding between Kras and SOS, comprising an effective amount of the cyclic peptide compound or salt thereof, or solvate thereof according to any one of [1] to [13].

[17] A pharmaceutical composition for treating or preventing cancer in a subject, the pharmaceutical composition comprising an effective amount of the cyclic peptide compound or salt thereof, or solvate thereof according to any one of [1] to [13].

[18] The pharmaceutical composition according to [17], wherein the cancer is pancreatic cancer.

[19] The pharmaceutical composition according to any one of [17] to [18], wherein the subject is a human.

Effects of the Invention

The present invention can provide novel cyclic peptide compounds having anti-tumor action, non-natural amino acids for use in the production of the cyclic peptide compounds, and production methods therefor.

DESCRIPTION OF EMBODIMENTS

Abbreviations

The abbreviations used herein are as follows.
AA: Ammonium acetate
Alloc group: Allyloxycarbonyl group
Boc group: tert-Butoxycarbonyl group
Cbz group: Benzyloxycarbonyl group
CSA: (+)-10-Camphorsulfonic acid
DBU: 1,8-Diazabicyclo[5.4.0]-7-undecene
DCC: N,N'-Dicyclohexylcarbodiimide
DCM: Dichloromethane
DCE: 1,2-Dichloroethane
DEAD: Diethyl azodicarboxylate
DMA: Dimethylacetamide
DMF: N,N-Dimethylformamide
DIAD: Diisopropyl azodicarboxylate
DIC: N,N'-Diisopropylcarbodiimide
DIPEA: N,N-Diisopropylethylamine
DMAP: N,N-Dimethyl-4-aminopyridine
t-Bu group: tert-Butyl group
dtbbpy: 4,4'-Di-tert-butyl-2,2'-dipyridyl
EDTA: Ethylenediaminetetraacetic acid
FA: Formic acid
Fmoc group: 9-Fluorenylmethyloxycarbonyl group
NMP: N-Methyl-2-pyrrolidone
TBME: t-Butyl methyl ether
TES: Triethylsilane
TFA: Trifluoroacetic acid
TFE: 2,2,2-Trifluoroethanol
THF: Tetrahydrofuran
THP: Tetrahydropyranyl
TMSCl: Trimethylsilyl chloride
HFIP: 1,1,1,3,3,3-Hexafluoroisopropyl alcohol
HOAt: 1-Hydroxy-7-azabenzotriazole
HOBt: 1-Hydroxybenzotriazole
HOOBt: 3,4-Dihydro-3-hydroxy-4-oxo-1,2,3-benzotriazine
IPAC: Isopropyl acetate
oxyma: Ethyl cyano(hydroxyimino)acetate
PPTS: Pyridinium p-toluenesulfonate
Pis: 2-Phenylisopropyl WSCI·HCl: 1-Ethyl-3-(3-dimethylaminopropyl)carbodiimide hydrochloride
TIPS: Triisopropylsilane
TfOH: Trifluoromethanesulfonic acid
HATU: O-(7-Aza-1H-benzotriazole-1-yl)-N,N,N',N'-tetramethyluronium hexafluorophosphate
DMSO: Dimethylsulfoxide
Fmoc-Cl: (9H-Fluoren-9-yl)methyl carbonochloridate
Fmoc-OSu: 9-Fluorenylmethyl N-succinimidyl carbonate
Ns group: o-Nitrobenzenesulfonyl group
Trt group: Triphenylmethyl group
Troc group: 2,2,2-Trichloroethoxycarbonyl group Definitions of Functional Groups and the Like Examples of "halogen atoms" herein include F, Cl, Br, and I.

"Alkyl" herein means a monovalent group derived by removing any one hydrogen atom from an aliphatic hydrocarbon, and has a subset of hydrocarbyl or hydrocarbon group structures not containing either a heteroatom (which refers to an atom other than carbon and hydrogen atoms) or an unsaturated carbon-carbon bond but containing hydrogen and carbon atoms in its backbone. The alkyl includes linear and branched alkyls. Specifically, the alkyl has 1 to 20 carbon atoms ($C_1$-$C_{20}$, hereinafter "$C_p$-$C_q$" means that the number of carbon atoms is p to q), and is preferably $C_1$-$C_{10}$ alkyl, and more preferably $C_1$-$C_6$ alkyl. Specific examples of alkyl include methyl, ethyl, n-propyl, i-propyl, n-butyl, s-butyl, t-butyl, isobutyl (2-methylpropyl), n-pentyl, s-pentyl (1-methylbutyl), t-pentyl (1,1-dimethylpropyl), neopentyl (2,2-dimethylpropyl), isopentyl (3-methylbutyl), 3-pentyl (1-ethylpropyl), 1,2-dimethylpropyl, 2-methylbutyl, n-hexyl, 1,1,2-trimethylpropyl, 1,2,2-trimethylpropyl, 1,1,2,2-tetramethylpropyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, and 2-ethylbutyl.

"Alkenyl" herein means a monovalent group having at least one double bond (two adjacent $SP^2$ carbon atoms). Depending on the configuration of a double bond and a substituent (if present), the geometrical form of the double bond can be entgegen (E) or zusammen (Z) as well as cis or trans configuration. The alkenyl includes linear and branched alkenyls. The alkenyl is preferably $C_2$-$C_{10}$ alkenyl, and more preferably $C_2$-$C_6$ alkenyl, and specific examples include vinyl, allyl, 1-propenyl, 2-propenyl, 1-butenyl, 2-butenyl (including cis and trans forms), 3-butenyl, pentenyl, 3-methyl-2-butenyl, and hexenyl.

"Alkynyl" herein means a monovalent group having at least one triple bond (two adjacent SP carbon atoms). The alkynyl includes linear and branched alkynyls. The alkynyl is preferably $C_2$-$C_{10}$ alkynyl, and more preferably $C_2$-$C_6$ alkynyl, and specific examples include ethynyl, 1-propynyl, propargyl, 3-butynyl, pentynyl, hexynyl, 3-phenyl-2-propynyl, 3-(2'-fluorophenyl)-2-propynyl, 2-hydroxy-2-propynyl, 3-(3-fluorophenyl)-2-propynyl, and 3-methyl-(5-phenyl)-4-pentynyl.

"Cycloalkyl" herein means a saturated or partially saturated cyclic monovalent aliphatic hydrocarbon group and includes a monocyclic ring, a bicyclo ring, and a spiro ring. The cycloalkyl is preferably $C_3$-$C_8$ cycloalkyl, and specific examples include cyclopropyl, cyclobutyl, cyclopentyl, cyclohexyl, cycloheptyl, cyclooctyl, bicyclo[2.2.1]heptyl, and spiro[3.3]heptyl.

"Aryl" herein means a monovalent aromatic hydrocarbon ring, and is preferably $C_6$-$C_{10}$ aryl. Specific examples of the aryl include phenyl and naphthyl (e.g., 1-naphthyl and 2-naphthyl).

"Heterocyclyl" herein means a non-aromatic cyclic monovalent group containing 1 to 5 hetero atoms in addition to carbon atoms. The heterocyclyl may have a double and/or triple bond within the ring, a carbon atom within the ring may be oxidized to form carbonyl, and heterocyclyl may be a monocyclic ring or a condensed ring. The number of atoms constituting the ring is preferably 4 to 10 (4- to 10-membered heterocyclyl), and more preferably 4 to 7 (4- to 7-membered heterocyclyl). Specific examples of the heterocyclyl include azetidinyl, oxiranyl, oxetanyl, azetidinyl, dihydrofuryl, tetrahydrofuryl, dihydropyranyl, tetrahydropyranyl, tetrahydropyridyl, tetrahydropyrimidyl, morpholinyl, thiomorpholinyl, pyrrolidinyl, piperidinyl, piperazinyl, pyrazolidinyl, imidazolinyl, imidazolidinyl, oxazolidinyl, isoxazolidinyl, thiazolidinyl, isothiazolidinyl, 1,2-thiazinane, thiadiazolidinyl, azetidinyl, oxazolidone, benzodioxanyl, benzoxazolyl, dioxolanyl, dioxanyl, tetrahydropyrrolo[1,2-c]imidazole, thietanyl, 3,6-diazabicyclo[3.1.1]heptanyl, 2,5-diazabicyclo[2.2.1]heptanyl, 3-oxa-8-azabicyclo[3.2.1]octanyl, sultam, and 2-oxaspiro[3.3]heptyl.

"Protected heterocyclyl" herein means a group in which one or more functional groups, such as an amino group, contained in the above-defined "heterocyclyl" are protected with a protecting group, and is preferably 4- to 7-membered protected heterocyclyl. Specific examples of the protecting group include Boc, Fmoc, Cbz, Troc, and Alloc, and specific examples of the protected heterocyclyl include Boc-protected azetidine.

"Heterocycloalkylidene" herein means a divalent group obtained by removing two hydrogen atoms from one carbon atom of the above-defined "heterocyclyl", in which a free valence forms a part of a double bond. The heterocycloalkylidene is preferably 4- to 7-membered heterocycloalkylidene, and specific examples include tetrahydropyran-4-ylidene and azetidin-3-ylidene.

"Protected heterocycloalkylidene" herein means a group in which one or more functional groups, such as an amino group, contained in the above-defined "heterocycloalkylidene" are protected with a protecting group, and is preferably 4- to 7-membered protected heterocycloalkylidene. Specific examples of the protecting group include Boc, Fmoc, Cbz, Troc, and Alloc, and specific examples of the protected heterocycloalkylidene include Boc-protected azetidin-3-ylidene.

"Heteroaryl" herein means an aromatic cyclic monovalent group containing 1 to 5 heteroatoms in addition to carbon atoms. The ring may be a monocyclic ring, may be a condensed ring formed with another ring, or may be partially saturated. The number of atoms constituting the ring is preferably 5 to 10 (5- to 10-membered heteroaryl) and more preferably 5 to 7 (5- to 7-membered heteroaryl). Specific examples of the heteroaryl include furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyrimidyl, pyridazinyl, pyrazinyl, triazinyl, benzofuranyl, benzothienyl, benzothiadiazolyl, benzothiazolyl, benzoxazolyl, benzoxadiazolyl, benzoimidazolyl, indolyl, isoindolyl, indazolyl, quinolyl, isoquinolyl, cinnolinyl, quinazolinyl, quinoxalinyl, benzodioxolyl, indolizinyl, and imidazopyridyl.

"Alkoxy" herein means an oxy group to which the above-defined "alkyl" is bonded, and is preferably $C_1$-$C_6$ alkoxy.

Specific examples of the alkoxy include methoxy, ethoxy, 1-propoxy, 2-propoxy, n-butoxy, i-butoxy, s-butoxy, t-butoxy, pentyloxy, and 3-methylbutoxy.

"Alkenyloxy" herein means an oxy group to which the above-defined "alkenyl" is bonded, and is preferably $C_2$-$C_6$ alkenyloxy. Specific examples of the alkenyloxy include vinyloxy, allyloxy, 1-propenyloxy, 2-propenyloxy, 1-butenyloxy, 2-butenyloxy (including cis and trans forms), 3-butenyloxy, pentenyloxy, and hexenyloxy.

"Cycloalkoxy" herein means an oxy group to which the above-defined "cycloalkyl" is bonded, and is preferably $C_3$-$C_8$ cycloalkoxy. Specific examples of the cycloalkoxy include cyclopropoxy, cyclobutoxy, and cyclopentyloxy.

"Aryloxy" herein means an oxy group to which the above-defined "aryl" is bonded, and is preferably $C_6$-$C_{10}$ aryloxy. Specific examples of the aryloxy include phenoxy, 1-naphthyloxy, and 2-naphthyloxy.

"Amino" herein means —$NH_2$ in a narrow sense and —NRR' in a broad sense, wherein R and R' are independently selected from hydrogen, alkyl, alkenyl, alkynyl, cycloalkyl, heterocyclyl, aryl, or heteroaryl, or R and R', together with the nitrogen atom to which they are attached, form a ring. The amino is preferably —$NH_2$, mono-$C_1$-$C_6$ alkylamino, di-$C_1$-$C_6$ alkylamino, 4- to 8-membered cyclic amino, or the like.

"Monoalkylamino" herein means a group corresponding to the above-defined "amino" wherein R is hydrogen and R' is the above-defined "alkyl", and is preferably mono-$C_1$-$C_6$ alkylamino. Specific examples of the monoalkylamino include methylamino, ethylamino, n-propylamino, i-propylamino, n-butylamino, s-butylamino, and t-butylamino.

"Dialkylamino" herein means a group corresponding to the above-defined "amino" wherein R and R' are independently the above-defined "alkyl", and is preferably di-$C_1$-$C_6$ alkylamino. Specific examples of the dialkylamino include dimethylamino and diethylamino.

"Cyclic amino" herein means a group corresponding to the above-defined "amino" wherein R and R', together with the nitrogen atom to which they are attached, form a ring, and is preferably 4- to 8-membered cyclic amino. Specific examples of the cyclic amino include 1-azetidyl, 1-pyrrolidyl, 1-piperidyl, 1-piperazyl, 4-morpholinyl, 3-oxazolidyl, 1,1-dioxidethiomorpholinyl-4-yl, and 3-oxa-8-azabicyclo[3.2.1]octan-8-yl.

"Protected amino" herein means an amino group protected with any protecting group. Specific examples of the protected amino include amino protected with a protecting group such as Boc, Fmoc, Cbz, Troc, or Alloc.

"Aminocarbonyl" herein means a carbonyl group to which the above-defined "amino" is bonded, and is preferably —$CONH_2$, mono-$C_1$-$C_6$ alkylaminocarbonyl, di-$C_1$-$C_6$ alkylaminocarbonyl, and 4- to 8-membered cyclic aminocarbonyl. Specific examples of the aminocarbonyl include —$CONH_2$, dimethylaminocarbonyl, 1-azetidinylcarbonyl, 1-pyrrolidinylcarbonyl, 1-piperidinylcarbonyl, 1-piperazinylcarbonyl, 4-morpholinylcarbonyl, 3-oxazolidinylcarbonyl, 1,1-dioxidethiomorpholinyl-4-ylcarbonyl, and 3-oxa-8-azabicyclo[3.2.1]octan-8-ylcarbonyl.

"Alkenyloxycarbonyl" herein means a carbonyl group to which the above-defined "alkenyloxy" is bonded, and is preferably $C_2$-$C_6$ alkenyloxycarbonyl. Specific examples of the alkenyloxycarbonyl include vinyloxycarbonyl, allyloxycarbonyl, 1-propenyloxycarbonyl, 2-propenyloxycarbonyl, 1-butenyloxycarbonyl, 2-butenyloxycarbonyl (including cis and trans forms), 3-butenyloxycarbonyl, pentenyloxycarbonyl, and hexenyloxycarbonyl.

"Alkylsulfonyl" herein means a sulfonyl group to which the above-defined "alkyl" is bonded, and is preferably $C_1$-$C_6$ alkylsulfonyl. Specific examples of the alkylsulfonyl include methylsulfonyl.

"Hydroxyalkyl" herein means a group in which one or more hydrogens of the above-defined "alkyl" are replaced with hydroxyl groups, and is preferably $C_1$-$C_6$ hydroxyalkyl. Specific examples of the hydroxyalkyl include hydroxymethyl, 1-hydroxyethyl, 2-hydroxyethyl, 2-hydroxy-2-methylpropyl, and 5-hydroxypentyl.

"Haloalkyl" herein means a group in which one or more hydrogens of the above-defined "alkyl" are replaced with halogen, and is preferably $C_1$-$C_6$ haloalkyl, and more preferably $C_1$-$C_6$ fluoroalkyl. Specific examples of the haloalkyl include difluoromethyl, trifluoromethyl, 2,2-difluoroethyl, 2,2,2-trifluoroethyl, 3,3-difluoropropyl, 4,4-difluorobutyl, and 5,5-difluoropentyl.

"Cyanoalkyl" herein means a group in which one or more hydrogens of the above-defined "alkyl" are replaced with cyano, and is preferably $C_1$-$C_6$ cyanoalkyl. Specific examples of the cyanoalkyl include cyanomethyl and 2-cyanoethyl.

"Aminoalkyl" herein means a group in which one or more hydrogens of the above-defined "alkyl" are replaced with the above-defined "amino", and is preferably $C_1$-$C_6$ aminoalkyl. Specific examples of the aminoalkyl include 1-pyridylmethyl, 2-(1-piperidyl)ethyl, 3-(1-piperidyl)propyl, and 4-aminobutyl.

"Carboxyalkyl" herein means a group in which one or more hydrogens of the above-defined "alkyl" are replaced with carboxy, and is preferably $C_2$-$C_6$ carboxyalkyl. Specific examples of the carboxyalkyl include carboxymethyl.

"Alkenyloxycarbonylalkyl" herein means a group in which one or more hydrogens of the above-defined "alkyl" are replaced with the above-defined "alkenyloxycarbonyl", and is preferably $C_2$-$C_6$ alkenyloxycarbonyl $C_1$-$C_6$ alkyl, and more preferably $C_2$-$C_6$ alkenyloxycarbonyl $C_1$-$C_2$ alkyl. Specific examples of the alkenyloxycarbonylalkyl include allyloxycarbonylmethyl and 2-(allyloxycarbonyl)ethyl.

"Alkoxyalkyl" herein means a group in which one of more hydrogens of the above-defined "alkyl" are replaced with the above-defined "alkoxy", and is preferably $C_1$-$C_6$ alkoxy $C_1$-$C_6$alkyl, and more preferably $C_1$-$C_6$ alkoxy $C_1$-$C_2$ alkyl. Specific examples of the alkoxyalkyl include methoxymethyl, ethoxymethyl, 1-propoxymethyl, 2-propoxymethyl, n-butoxymethyl, i-butoxymethyl, s-butoxymethyl, t-butoxymethyl, pentyloxymethyl, 3-methylbutoxymethyl, 1-methoxyethyl, 2-methoxyethyl, and 2-ethoxyethyl.

"Cycloalkylalkyl" herein means a group in which one or more hydrogens of the above-defined "alkyl" are replaced with the above-defined "cycloalkyl", and is preferably $C_3$-$C_8$ cycloalkyl $C_1$-$C_6$ alkyl, and more preferably $C_3$-$C_6$ cycloalkyl $C_1$-$C_2$ alkyl. Specific examples of the cycloalkylalkyl include cyclopropylmethyl, cyclobutylmethyl, cyclopentylmethyl, and cyclohexylmethyl.

"Cycloalkoxyalkyl" herein means a group in which one or more hydrogens of the above-defined "alkyl" are replaced with the above-defined "cycloalkoxy", and is preferably $C_3$-$C_8$ cycloalkoxy $C_1$-$C_6$ alkyl, and more preferably $C_3$-$C_6$ cycloalkoxy $C_1$-$C_2$ alkyl. Specific examples of the cycloalkoxyalkyl include cyclopropoxymethyl and cyclobutoxymethyl.

"Heterocyclylalkyl" herein means a group in which one or more hydrogens of the above-defined "alkyl" are replaced with the above-defined "heterocyclyl", and is preferably 4- to 7-membered heterocyclyl $C_1$-$C_6$ alkyl, and more preferably 4- to 7-membered heterocyclyl $C_1$-$C_2$ alkyl. Specific examples of the heterocyclylalkyl include 2-(tetrahydro-2H-pyran-4-yl)ethyl and 2-(azetidin-3-yl)ethyl.

"Alkylsulfonylalkyl" herein means a group in which one or more hydrogens of the above-defined "alkyl" are replaced with the above-defined "alkylsulfonyl", and is preferably $C_1$-$C_6$ alkylsulfonyl $C_1$-$C_6$ alkyl, and more preferably $C_1$-$C_6$ alkylsulfonyl $C_1$-$C_2$ alkyl. Specific examples of the alkylsulfonylalkyl include methylsulfonylmethyl and 2-(methylsulfonyl)ethyl.

"Aminocarbonylalkyl" herein means a group in which one or more hydrogens of the above-defined "alkyl" are replaced with the above-defined "aminocarbonyl", and is preferably aminocarbonyl $C_1$-$C_6$ alkyl, and more preferably aminocarbonyl $C_1$-$C_4$ alkyl. Specific examples of the aminocarbonylalkyl include methylaminocarbonylmethyl, dimethylaminocarbonylmethyl, t-butylaminocarbonylmethyl, 1-azetidinylcarbonylmethyl, 1-pyrrolidinylcarbonylmethyl, 1-piperidinylcarbonylmethyl, 4-morpholinylcarbonylmethyl, 2-(methylaminocarbonyl)ethyl, 2-(dimethylaminocarbonyl)ethyl, 2-(1-azetidinylcarbonyl)ethyl, 2-(1-pyrrolidinylcarbonyl)ethyl, 2-(4-morpholinylcarbonyl)ethyl, 3-(dimethylaminocarbonyl)propyl, and 4-(dimethylaminocarbonyl)butyl.

"Aryloxyalkyl" herein means a group in which one or more hydrogens of the above-defined "alkyl" are replaced with the above-defined "aryloxy", and is preferably $C_6$-$C_{10}$ aryloxy $C_1$-$C_6$ alkyl, and more preferably $C_6$-$C_{10}$ aryloxy $C_1$-$C_2$ alkyl. Specific examples of the aryloxyalkyl include phenoxymethyl and 2-phenoxyethyl.

"Aralkyl (arylalkyl)" herein means a group in which one or more hydrogen atoms of the above-defined "alkyl" are replaced with the above-defined "aryl", and is preferably $C_7$-$C_{14}$ aralkyl, and more preferably $C_7$-$C_{10}$ aralkyl. Specific examples of the aralkyl include benzyl, phenethyl, and 3-phenylpropyl.

"Aralkoxy" herein means an oxy group to which the above-defined "aralkyl" is bonded, and is preferably $C_7$-$C_{14}$ aralkoxy, and more preferably $C_7$-$C_{10}$ aralkoxy. Specific examples of the aralkoxy include benzyloxy, phenethyloxy, and 3-phenylpropoxy.

"Aralkoxyalkyl" herein means a group in which one or more hydrogens of the above-defined "alkyl" are replaced with the above-defined "aralkoxy", and is preferably $C_7$-$C_{14}$ aralkoxy $C_1$-$C_6$ alkyl, and more preferably $C_7$-$C_{14}$ aralkoxy $C_1$-$C_2$ alkyl. Specific examples of the aralkoxyalkyl include benzyloxymethyl and 1-(benzyloxy)ethyl.

"Heteroarylalkyl" herein means a group in which one or more hydrogen atoms of the above-defined "alkyl" are replaced with the above-defined "heteroaryl", and is preferably 5- to 10-membered heteroaryl $C_1$-$C_6$ alkyl, and more preferably 5- to 10-membered heteroaryl $C_1$-$C_2$ alkyl. Specific examples of the heteroarylalkyl include 3-thienylmethyl, 4-thiazolylmethyl, 2-pyridylmethyl, 3-pyridylmethyl, 4-pyridylmethyl, 2-(2-pyridyl)ethyl, 2-(3-pyridyl)ethyl, 2-(4-pyridyl)ethyl, 2-(6-quinolyl)ethyl, 2-(7-quinolyl)ethyl, 2-(6-indolyl)ethyl, 2-(5-indolyl)ethyl, and 2-(5-benzofuranyl)ethyl.

"Heteroarylalkoxy" herein means an oxy group to which the above-defined "heteroarylalkyl" is bonded, and is preferably 5- to 10-membered heteroaryl $C_1$-$C_6$ alkoxy, and more preferably 5- to 10-membered heteroaryl $C_1$-$C_2$ alkoxy. Specific examples of the heteroarylalkoxy include 3-thienylmethoxy and 3-pyridylmethoxy.

"Heteroarylalkoxyalkyl" herein means a group in which one or more hydrogens of the above-defined "alkyl" are replaced with the above-defined "heteroarylalkoxy", and is preferably 5- to 10-membered heteroaryl $C_1$-$C_6$ alkoxy $C_1$-$C_6$ alkyl, and more preferably 5- to 10-membered heteroaryl $C_1$-$C_2$ alkoxy $C_1$-$C_2$ alkyl. Specific examples of the heteroarylalkoxyalkyl include 3-pyridylmethoxymethyl.

"Heterocycloalkylidenealkyl" herein means a group in which one or more hydrogens of the above-defined "alkyl" are replaced with the above-defined "heterocycloalkylidene", and is preferably 4- to 7-membered heterocycloalkylidene $C_1$-$C_6$ alkyl, and more preferably 4- to 7-membered heterocycloalkylidene $C_1$-$C_2$ alkyl. Specific examples of the heterocycloalkylidenealkyl include tetrahydro-4H-pyran-4-ylidenemethyl and azetidin-3-ylidenemethyl.

"Alkoxyalkenyl" herein means a group in which one or more hydrogens of the above-defined "alkenyl" are replaced with the above-defined "alkoxy", and is preferably $C_1$-$C_6$ alkoxy $C_2$-$C_6$ alkenyl. Specific examples of the alkoxyalkenyl include (E)-4-methoxybut-2-en-1-yl.

"Aminocarbonylalkenyl" herein means a group in which one or more hydrogens of the above-defined "alkenyl" are replaced with the above-defined "aminocarbonyl", and is preferably aminocarbonyl $C_2$-$C_6$ alkenyl. Specific examples of the aminocarbonylalkenyl include (E)-3-(dimethylaminocarbonylcarbonyl)-prop-2-en-1-yl.

"Haloalkoxy" herein means a group in which one or more hydrogens of the above-defined "alkoxy" are replaced with halogen, and is preferably $C_1$-$C_6$ haloalkoxy. Specific examples of the haloalkoxy include difluoromethoxy, trifluoromethoxy, 2,2-difluoroethoxy, and 2,2,2-trifluoroethoxy.

"Alkylene" herein means a divalent group derived by further removing any one hydrogen atom from the above "alkyl", and is preferably $C_4$-$C_8$ alkylene. Specific examples of the alkylene include —$CH_2$—, —$(CH_2)_2$—, —$(CH_2)_3$—, —$CH(CH_3)CH_2$—, —$C(CH_3)_2$—, —$(CH_2)_4$—, —$CH(CH_3)CH_2CH_2$—, —$C(CH_3)_2CH_2$—, —$CH_2CH(CH_3)CH_2$—, —$CH_2C(CH_3)_2$—, —$CH_2CH_2CH(CH_3)$—, —$(CH_2)_5$—, —$(CH_2)_6$—, —$(CH_2)_7$—, and —$(CH_2)_8$—.

"Alicyclic ring" herein means a non-aromatic hydrocarbon ring. The alicyclic ring may have an unsaturated bond within the ring, and may be a polycyclic ring having two or more rings. A carbon atom constituting the ring may be oxidized to form carbonyl. The alicyclic ring is preferably a 3- to 8-membered alicyclic ring, and specific examples include a cyclopropane ring, a cyclobutane ring, a cyclopentane ring, a cyclohexane ring, a cycloheptane ring, a cyclooctane ring, and a bicyclo[2.2.1]heptane ring.

"Saturated heterocyclic ring" herein means a non-aromatic heterocyclic ring containing 1 to 5 hetero atoms in addition to carbon atoms and not containing a double bond and/or a triple bond within the ring. The saturated heterocyclic ring may be a monocyclic ring, or may form a condensed ring with another ring, e.g., an aromatic ring such as a benzene ring. When the saturated heterocyclic ring forms a condensed ring, the saturated heterocyclic ring is preferably a 4- to 7-membered saturated heterocyclic ring, and specific examples include an azetidine ring, an oxetane ring, a tetrahydrofuran ring, a tetrahydropyran ring, a morpholine ring, a thiomorpholine ring, a pyrrolidine ring, a 4-oxopyrrolidine ring, a piperidine ring, a 4-oxopiperidine ring, a piperazine ring, a pyrazolidine ring, an imidazolidine ring, an oxazolidine ring, an isoxazolidine ring, a thiazolidine ring, an isothiazolidine ring, a thiadiazolidine ring, an oxazolidone ring, a dioxolane ring, a dioxane ring, a thietane ring, an octahydroindole ring, and an indoline ring.

"Peptide chain" herein refers to a peptide chain in which 1, 2, 3, 4, or more natural amino acids and/or non-natural amino acids are connected by an amide bond and/or an ester bond. The peptide chain is preferably a peptide chain comprising 1 to 4 amino acid residues, and more preferably a peptide chain consisting of 1 to 4 amino acid residues.

"Optionally substituted" herein means that a group may be substituted with any substituent.

"Optionally protected" herein means that a group may be protected with any protecting group.

"One or more" herein means one or two or more. When "one or more" is used in a context relating to the substituent of a group, the phrase means a number encompassing one to the maximum number of substituents permitted by that group. Specific examples of "one or more" include 1, 2, 3, 4, 5, 6, 7, 8, 9, 10, and/or a greater number.

The compound of the present invention can be a salt thereof, and preferably a chemically or pharmaceutically acceptable salt thereof. Also, the compound of the present invention or a salt thereof can be a solvate thereof, and preferably a chemically or pharmaceutically acceptable solvate thereof. Examples of salts of the compound of the present invention include hydrochloride; hydrobromide; hydroiodide; phosphate; phosphonate; sulfate; sulfonates such as methanesulfonate and p-toluenesulfonate; carboxylates such as acetate, citrate, malate, tartrate, succinate, and salicylate; alkali metal salts such as a sodium salt and a potassium salt; alkaline earth metal salts such as a magnesium salt and a calcium salt; and ammonium salts such as an ammonium salt, an alkylammonium salt, a dialkylammonium salt, a trialkylammonium salt, and a tetraalkylammonium salt. These salts are produced by, for example, bringing the compound into contact with an acid or a base usable in the production of pharmaceutical products. In the present invention, a solvate of a compound refers to a phenomenon in which solute molecules strongly attract solvent molecules in a solution and form one molecular group, and is called a hydrate when the solvent is water. The solvate of the compound of the present invention is preferably a hydrate, and specific examples of such hydrates include mono- to deca-hydrates, preferably mono- to penta-hydrates, and more preferably mono- to tri-hydrates. The solvate of the compound of the present invention includes not only a solvate formed of a single solvent such as water, alcohol (e.g., methanol, ethanol, 1-propanol, or 2-propanol), or dimethylformamide, but also a solvate formed of a plurality of solvents.

The term "amino acid" as used herein includes natural and unnatural amino acids. The term "natural amino acid" as used herein refers to Gly, Ala, Ser, Thr, Val, Leu, Ile, Phe, Tyr, Trp, His, Glu, Asp, Gln, Asn, Cys, Met, Lys, Arg, or Pro. Examples of the unnatural amino acid include, but are not particularly limited to, β-amino acids, γ-amino acids, D-amino acids, N-substituted amino acids, α, α-disubstituted amino acids, amino acids having side chains that are different from those of natural amino acids, and hydroxycarboxylic acids. Amino acids herein may have any conformation. There is no particular limitation on the selection of amino acid side chain, but in addition to a hydrogen atom, it can be freely selected from, for example, an alkyl group, an alkenyl group, an alkynyl group, an aryl group, a heteroaryl group, an aralkyl group, and a cycloalkyl group. One or two non-adjacent methylene groups in such a group are optionally substituted with an oxygen atom, a carbonyl group (—CO—), or a sulfonyl group (—SO$_2$—). Each group may have a substituent, and there are no limitations on the substituent. For example, one or more substituents may be freely and independently selected from any substituents including a halogen atom, an O atom, an S atom, an N atom, a B atom, an Si atom, or a P atom. Examples include an optionally substituted alkyl group, alkenyl group, alkynyl group, aryl group, heteroaryl group, aralkyl group, and cycloalkyl group. In a non-limiting embodiment, amino acids herein may be compounds having a carboxy group and an amino group in the same molecule (even in this case, imino acids such as proline and hydroxyproline are also included in amino acids).

The main chain amino group of an amino acid may be unsubstituted (an NH$_2$ group) or substituted (i.e., an —NHR group, where R represents alkyl, alkenyl, alkynyl, aryl, heteroaryl, aralkyl, or cycloalkyl which may have a substituent, one or two non-adjacent methylene groups in such a group may be substituted with an oxygen atom, a carbonyl group (—CO—), or a sulfonyl group (—SO$_2$—), and the carbon chain bonded to the N atom and the carbon atom at the position a may form a ring, as in proline). The R substituent is selected as the substituent in the aforementioned amino acid side chain is selected. When the main chain amino group is substituted, the R is included in the "amino acid side chain" as used herein. Such amino acids in which the main chain amino group is substituted are herein called "N-substituted amino acids." Preferred examples of the "N-substituted amino acids" as used herein include, but are not limited to, N-alkylamino acids, N—$C_1$-$C_6$ alkylamino acids, N—$C_1$-$C_4$ alkylamino acids, and N-methylamino acids.

"Amino acids" as used herein which constitute a peptide compound include all isotopes corresponding to each amino acid. The isotope of the "amino acid" refers to one having at least one atom replaced with an atom of the same atomic number (number of protons) and different mass number (total number of protons and neutrons). Examples of isotopes contained in the "amino acid" constituting the peptide compounds of the present invention include a hydrogen atom, a carbon atom, a nitrogen atom, an oxygen atom, a phosphorus atom, a sulfur atom, a fluorine atom, and a chlorine atom, which respectively include $^2$H and $^3$H; $^{13}$C and $^4$C; $^{15}$N; $^{17}$O and $^{18}$O; $^{31}$P and $^{32}$P; $^{35}$S; $^{18}$F; and $^{36}$Cl.

Substituents containing a halogen atom as used herein include include a halogen-substituted alkyl group, cycloalkyl group, alkenyl group, alkynyl group, aryl group, heteroaryl group, or aralkyl group. More specific examples include fluoroalkyl, difluoroalkyl, and trifluoroalkyl.

Substituents containing an O atom include groups such as hydroxy (—OH), oxy (—OR), carbonyl (—C=O—R), carboxy (—CO$_2$H), oxycarbonyl (—C=O—OR), carbonyloxy (—O—C=O—R), thiocarbonyl (—C=O—SR), carbonylthio (—S—C=O—R), aminocarbonyl (—C=O—NHR), carbonylamino (—NH—C=O—R), oxycarbonylamino (—NH—C=O—OR), sulfonylamino (—NH—SO$_2$—R), aminosulfonyl (—SO$_2$—NHR), sulfamoylamino (—NH—SO$_2$—NHR), thiocarboxyl (—C=O—SH), and carboxylcarbonyl (—C=O—CO$_2$H).

Examples of oxy (—OR) include alkoxy, cycloalkoxy, alkenyloxy, alkynyloxy, aryloxy, heteroaryloxy, and aralkyloxy. The alkoxy is preferably $C_1$-$C_4$ alkoxy and $C_1$-$C_2$ alkoxy, and particularly preferably methoxy or ethoxy.

Examples of carbonyl (—C=O—R) include formyl (—C=O—H), alkylcarbonyl, cycloalkylcarbonyl, alkenylcarbonyl, alkynylcarbonyl, arylcarbonyl, heteroarylcarbonyl, and aralkylcarbonyl.

Examples of oxycarbonyl (—C=O—OR) include alkyloxycarbonyl, cycloalkyloxycarbonyl, alkenyloxycarbonyl, alkynyloxycarbonyl, aryloxycarbonyl, heteroaryloxycarbonyl, and aralkyloxycarbonyl.

Examples of carbonyloxy (—O—C=O—R) include alkylcarbonyloxy, cycloalkylcarbonyloxy, alkenylcarbonyloxy, alkynylcarbonyloxy, arylcarbonyloxy, heteroarylcarbonyloxy, and aralkylcarbonyloxy.

Examples of thiocarbonyl (—C=O—SR) include alkylthiocarbonyl, cycloalkylthiocarbonyl, alkenylthiocarbonyl, alkynylthiocarbonyl, arylthiocarbonyl, heteroarylthiocarbonyl, and aralkylthiocarbonyl.

Examples of carbonylthio (—S—C=O—R) include alkylcarbonylthio, cycloalkylcarbonylthio, alkenylcarbonylthio, alkynylcarbonylthio, arylcarbonylthio, heteroarylcarbonylthio, and aralkylcarbonylthio.

Examples of aminocarbonyl (—C=O—NHR) include alkylaminocarbonyl (examples of which include $C_1$-$C_6$ or $C_1$-$C_4$ alkylaminocarbonyl, in particular, ethylaminocarbonyl and methylaminocarbonyl), cycloalkylaminocarbonyl, alkenylaminocarbonyl, alkynylaminocarbonyl, arylaminocarbonyl, heteroarylaminocarbonyl, and aralkylaminocarbonyl. Additional examples include compounds in which the H atom bonded to the N atom in —C=O—NHR is further replaced with alkyl, cycloalkyl, alkenyl, alkynyl, aryl, heteroaryl, or aralkyl.

Examples of carbonylamino (—NH—C=O—R) include alkylcarbonylamino, cycloalkylcarbonylamino, alkenylcarbonylamino, alkynylcarbonylamino, arylcarbonylamino, heteroarylcarbonylamino, and aralkylcarbonylamino. Additional examples include compounds in which the H atom bonded to the N atom in —NH—C=O—R is further replaced with alkyl, cycloalkyl, alkenyl, alkynyl, aryl, heteroaryl, or aralkyl.

Examples of oxycarbonylamino (—NH—C=O—OR) include alkoxycarbonylamino, cycloalkoxycarbonylamino, alkenyloxycarbonylamino, alkynyloxycarbonylamino, aryloxycarbonylamino, heteroaryloxycarbonylamino, and aralkyloxycarbonylamino. Additional examples include compounds in which the H atom bonded to the N atom in —NH—C=O—OR is further replaced with alkyl, cycloalkyl, alkenyl, alkynyl, aryl, heteroaryl, or aralkyl.

Examples of sulfonylamino (—NH—SO$_2$—R) include alkylsulfonylamino, cycloalkylsulfonylamino, alkenylsulfonylamino, alkynylsulfonylamino, arylsulfonylamino, heteroarylsulfonylamino, and aralkylsulfonylamino. Additional examples include compounds in which the H atom attached to the N atom in —NH—SO$_2$—R is further replaced with alkyl, cycloalkyl, alkenyl, alkynyl, aryl, heteroaryl, or aralkyl.

Examples of aminosulfonyl (—SO$_2$—NHR) include alkylaminosulfonyl, cycloalkylaminosulfonyl, alkenylaminosulfonyl, alkynylaminosulfonyl, arylaminosulfonyl, heteroarylaminosulfonyl, and aralkylaminosulfonyl. Additional examples include compounds in which the H atom attached to the N atom in —SO$_2$—NHR is further replaced with alkyl, cycloalkyl, alkenyl, alkynyl, aryl, heteroaryl, or aralkyl.

Examples of sulfamoylamino (—NH—SO$_2$—NHR) include alkylsulfamoylamino, cycloalkylsulfamoylamino, alkenylsulfamoylamino, alkynylsulfamoylamino, arylsulfamoylamino, heteroarylsulfamoylamino, and aralkylsulfamoylamino. The two H atoms bonded to the N atoms in —NH—SO$_2$—NHR may be further replaced with substituents independently selected from the group consisting of alkyl, cycloalkyl, alkenyl, alkynyl, aryl, heteroaryl, and aralkyl, and these two substituents may form a ring.

Substituents containing an S atom include groups such as thiol (—SH), thio (—S—R), sulfinyl (—S=O—R), sulfonyl (—SO$_2$—R), and sulfo (—SO$_3$H).

Examples of thio (—S—R) include alkylthio, cycloalkylthio, alkenylthio, alkynylthio, arylthio, heteroarylthio, and aralkylthio.

Examples of sulfonyl (—SO$_2$—R) include alkylsulfonyl, cycloalkylsulfonyl, alkenylsulfonyl, alkynylsulfonyl, arylsulfonyl, heteroarylsulfonyl, and aralkylsulfonyl.

Substituents containing an N atom include groups such as azido (—N$_3$, also called "azido group"), cyano (—CN), primary amino (—NH$_2$), secondary amino (—NH—R; also called monosubstituted amino), tertiary amino (—NR(R'); also called disubstituted amino), amidino (—C(=NH)—NH$_2$), substituted amidino (—C(=NR)—NR'R"), guanidino (—NH—C(=NH)—NH$_2$), substituted guanidino (—NR—C(=NR''')—NR'R"), aminocarbonylamino (—NR—CO—NR'R"), pyridyl, piperidino, morpholino, and azetidinyl.

Examples of secondary amino (—NH—R; monosubstituted amino) include alkylamino, cycloalkylamino, alkenylamino, alkynylamino, arylamino, heteroarylamino, and aralkylamino.

Examples of tertiary amino (—NR(R'); disubstituted amino) include amino groups having any two substituents each independently selected from alkyl, cycloalkyl, alkenyl, alkynyl, aryl, heteroaryl, and aralkyl, such as alkyl(aralkyl) amino, where any two such substituents may form a ring. Specific examples include dialkylamino, in particular, $C_1$-$C_6$ dialkylamino, $C_1$-$C_4$ dialkylamino, dimethylamino, and diethylamino. The term "$C_p$-$C_q$ dialkylamino group" as used herein refers to an amino group substituted with two $C_p$-$C_q$ alkyl groups, where the two $C_p$-$C_q$ alkyl groups may be the same or different.

Examples of substituted amidino (—C(=NR)—NR'R") include groups in which three substituents R, R', and R" on the N atom are each independently selected from alkyl, cycloalkyl, alkenyl, alkynyl, aryl, heteroaryl, and aralkyl, such as alkyl(aralkyl)(aryl)amidino.

Examples of substituted guanidino (—NR—C(=NR''')—NR'R") include groups in which R, R', R", and R''' are each independently selected from alkyl, cycloalkyl, alkenyl, alkynyl, aryl, heteroaryl, and aralkyl, or groups in which these substituents form a ring.

Examples of aminocarbonylamino (—NR—CO—NR'R") include groups in which R, R', and R" are each independently selected from a hydrogen atom, alkyl, cycloalkyl, alkenyl, alkynyl, aryl, heteroaryl, and aralkyl, or groups in which these substituents form a ring.

Herein, an "amino acid residue" constituting the peptide compound may be simply referred to as an "amino acid".

In an embodiment, the present invention relates to a cyclic peptide compound represented by formula (1) below or a salt thereof, or a solvate thereof.

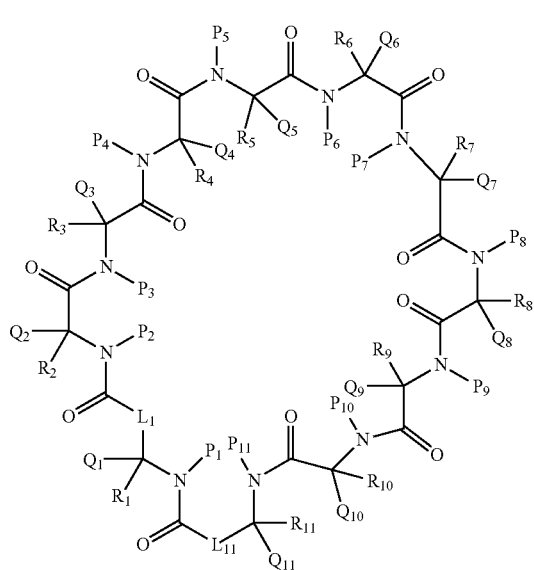

(1)

In formula (1), the ring is composed of 11 amino acid residues. Herein, the amino acid residue having $P_1$, $Q_1$, $R_1$, and $L_1$ in the formula may be referred to as core 1, the amino acid residue having $P_2$, $Q_2$, and $R_2$ as core 2, the amino acid residue having $P_3$, $Q_3$, and $R_3$ as core 3, the amino acid residue having $P_4$, $Q_4$, and $R_4$ as core 4, the amino acid residue having $P_5$, $Q_5$, and $R_5$ as core 5, the amino acid residue having $P_6$, $Q_6$, and $R_6$ as core 6, the amino acid residue having $P_7$, $Q_7$, and $R_7$ as core 7, the amino acid residue having $P_8$, $Q_8$, and $R_8$ as core 8, the amino acid residue having $P_9$, $Q_9$, and $R_9$ as core 9, the amino acid residue having $P_{10}$, $Q_{10}$, and $R_{10}$ as core 10, and the amino acid residue having $P_{11}$, $Q_{11}$, $R_{11}$, and $L_{11}$ as core 11.

In an embodiment, in formula (1), $L_1$ is a single bond or is —$CHM_1$-, —$(CH_2)_nS(CH_2)_m$—, —$(CH_2)_nS(O)(CH_2)_m$—, or —$(CH_2)_nS(O)_2(CH_2)_m$—, and $L_{11}$ is a single bond or is —$CHM_{11}$-, —$(CH_2)_nS(CH_2)_m$—, —$(CH_2)_nS(O)(CH_2)_m$—, or —$(CH_2)_nS(O)_2(CH_2)_m$—, wherein one of $L_1$ and $L_{11}$ is a single bond. That is, when $L_1$ is a single bond, $L_{11}$ is —$CHM_{11}$-, —$(CH_2)_nS(CH_2)_m$—, —$(CH_2)_nS(O)(CH_2)_m$—, or —$(CH_2)_nS(O)_2(CH_2)_m$—, and when $L_{11}$ is a single bond, $L_1$ is —$CHM_1$-, —$(CH_2)_nS(CH_2)_m$—, —$(CH_2)_nS(O)(CH_2)_m$—, or —$(CH_2)_nS(O)_2(CH_2)_m$—. $M_1$ is hydrogen except when $R_1$ and $M_1$ form a 3- to 8-membered alicyclic ring, and $M_{11}$ is hydrogen except when $R_{11}$ and $M_1$ form a 3- to 8-membered alicyclic ring.

When $L_1$ or $L_{11}$ is —$(CH_2)_nS(CH_2)_m$—, specific examples of —$(CH_2)_nS(CH_2)_m$— include —$CH_2SCH_2$—, —$CH_2CH_2SCH_2$—, —$CH_2SCH_2CH_2$—, and —$CH_2CH_2SCH_2CH_2$—.

When $L_1$ or $L_{11}$ is —$(CH_2)_nS(O)(CH_2)_m$—, specific examples of —$(CH_2)_nS(O)(CH_2)_m$— include —$CH_2S(O)CH_2$—, —$CH_2CH_2S(O)CH_2$—, —$CH_2S(O)CH_2CH_2$—, and —$CH_2CH_2S(O)CH_2CH_2$—.

When $L_1$ or $L_{11}$ is —$(CH_2)_nS(O)_2(CH_2)_m$—, specific examples of —$(CH_2)_nS(O)_2(CH_2)_m$— include —$CH_2S(O)_2CH_2$—, —$CH_2CH_2S(O)_2CH_2$—, —$CH_2S(O)_2CH_2CH_2$—, and —$CH_2CH_2S(O)_2CH_2CH_2$—.

In an embodiment, in formula (1), $R_1$ is hydrogen, $C_1$-$C_6$ alkyl, $C_2$-$C_6$ alkynyl, $C_1$-$C_6$ alkoxy$C_1$-$C_6$ alkyl, $C_3$-$C_8$ cycloalkyl, $C_3$-$C_8$ cycloalkyl$C_1$-$C_6$ alkyl, or $C_3$-$C_8$ cycloalkoxy$C_1$-$C_6$ alkyl, each of which is optionally substituted with one or more groups independently selected from the group consisting of halogen, hydroxy, aminocarbonyl (wherein the amino is —$NH_2$, mono-$C_1$-$C_6$ alkylamino, di-$C_1$-$C_6$ alkylamino, or 4- to 8-membered cyclic amino), and $C_1$-$C_6$ alkylsulfonyl.

When core 1 is α-amino acid (i.e., $L_1$ is a single bond), $R_1$ is preferably $C_1$-$C_6$ alkyl, $C_1$-$C_6$ haloalkyl, $C_1$-$C_6$ hydroxyalkyl, $C_1$-$C_6$ alkylsulfonyl$C_1$-$C_6$ alkyl, $C_2$-$C_6$ alkynyl, $C_1$-$C_6$ alkoxy$C_1$-$C_6$ alkyl (wherein the $C_1$-$C_6$ alkoxy$C_1$-$C_6$ alkyl is optionally substituted with one or more halogens, aminocarbonyl (wherein the amino is —$NH_2$, mono-$C_1$-$C_6$ alkylamino, di-$C_1$-$C_6$ alkylamino, or 4- to 8-membered cyclic amino), or hydroxy), $C_3$-$C_8$ cycloalkyl, $C_3$-$C_8$ cycloalkyl$C_1$-$C_6$ alkyl, or $C_3$-$C_8$ cycloalkoxy$C_1$-$C_6$ alkyl.

In this embodiment, $R_1$ is more preferably $C_1$-$C_6$ alkyl, $C_1$-$C_6$ fluoroalkyl, $C_1$-$C_4$ hydroxyalkyl, methylsulfonyl$C_1$-$C_2$ alkyl, $C_2$-$C_3$ alkynyl; $C_1$-$C_6$ alkoxy$C_1$-$C_2$ alkyl optionally substituted with one or more fluorines, mono-$C_1$-$C_4$ alkylaminocarbonyl, or hydroxy; $C_3$-$C_6$ cycloalkyl, $C_3$-$C_6$ cycloalkyl$C_1$-$C_2$ alkyl, or $C_3$-$C_6$ cycloalkoxy$C_1$-$C_2$ alkyl.

In this embodiment, specific examples of $R_1$ include methyl, ethyl, i-propyl, n-propyl, 2-methylpropyl, 1-methylpropyl, n-butyl, n-hexyl, 3-methylbutyl, 2-methylbutyl, n-pentyl, but-3-yn-1-yl, propargyl, (2-hydroxy-2-methylpropyloxy)methyl, (2-(t-butylamino)-2-oxoethoxy)methyl, 3,3-difluorobutyl, n-propoxymethyl, hydroxymethyl, 2,2,2-trifluoroethyl, 5,5-difluoropentyl, methoxymethyl, 3-methylbutoxymethyl, 1-hydroxyethyl, cyclobutoxymethyl, (2,2,2-trifluoroethoxy)methyl, 1-methoxyethyl, 2-methoxyethyl, 2-methylsulfonylethyl, cyclohexyl, cyclobutyl, cyclopropyl, cyclopentyl, cyclohexylmethyl, cyclopentylmethyl, cyclobutylmethyl, cyclopropylmethyl, and cyclopropoxymethyl.

When core 1 is β-amino acid (i.e., $L_1$ is —$CHM_1$-), $R_1$ is preferably hydrogen.

In an embodiment, in formula (1), $R_1$ and $P_1$, together with the carbon atom to which $R_1$ is attached and the nitrogen atom to which $P_1$ is attached, can form a 4- to 7-membered saturated heterocyclic ring.

When $R_1$ and $P_1$ form a 4- to 7-membered saturated heterocyclic ring, the 4- to 7-membered saturated heterocyclic ring is preferably an azetidine ring, a pyrrolidine ring, a piperidine ring, a piperazine ring, or a morpholine ring.

In an embodiment, in formula (1), $R_1$ and $Q_1$, together with the carbon atom to which they are attached, can form a 3- to 8-membered alicyclic ring or a 4- to 7-membered saturated heterocyclic ring.

When $R_1$ and $Q_1$ form a 3- to 8-membered alicyclic ring or a 4- to 7-membered saturated heterocyclic ring, the 3- to 8-membered alicyclic ring is preferably a cyclopropane ring, a cyclobutane ring, a cyclopentane ring, or a cyclohexane ring, and the 4- to 7-membered saturated heterocyclic ring is preferably a tetrahydrofuran ring or a tetrahydropyran ring.

In an embodiment, in formula (1), when core 1 is n-amino acid, $R_1$ and $M_1$, together with the carbon atom to which $R_1$ is attached and the carbon atom to which $M_1$ is attached, can form a 3- to 8-membered alicyclic ring.

When $R_1$ and $M_1$ form a 3- to 8-membered alicyclic ring, the 3- to 8-membered alicyclic ring is preferably a cyclopentane ring or a cyclohexane ring.

In an embodiment, in formula (1), when core 1 is n-amino acid, $M_1$ is hydrogen except when $R_1$ and $M_1$ form a 3- to 8-membered alicyclic ring.

In an embodiment, in formula (1), except when $R_1$ and $P_1$ form a 4- to 7-membered saturated heterocyclic ring, $P_1$ is hydrogen or $C_1$-$C_6$ alkyl, wherein the $C_1$-$C_6$ alkyl is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino).

$P_1$ is preferably hydrogen or $C_1$-$C_6$ alkyl. Specific examples of such $P_1$ include hydrogen, methyl, ethyl, and n-propyl.

In an embodiment, except when $R_1$ and $Q_1$ form a 3- to 8-membered alicyclic ring or a 4- to 7-membered saturated heterocyclic ring, $Q_1$ is hydrogen or $C_1$-$C_6$ alkyl, and preferably hydrogen.

When core 1 is α-amino acid, specific examples of core 1 include MeAla, Ala, Pic(2), MeLeu, MeCha, MeVal, EtAla, nPrAla, MeSer(tBuOH), MeSer(NtBu-Aca), MeAla (cPent), MeAla(cBu), MeAla(cPr), MeChg, MeGly(cPent), MeGly(cBu), MeGly(cPr), MeAbu, MeNva, MeNle, Val, Leu, MeAOC(2), MeNva(5-F2), MeHle, MeIle, MeSer (nPr), MeSer(cPr), MeSer, MeAbu(4-F3), MeHnl, MeHnl (7-F2), MePRA, MeSer(Me), MeSer(iPen), MeThr, MeSer (cBu), MeSer(Tfe), MeThr(Me), MeHse(Me), MeMet(O2), MeAhxy(2), and EtLeu.

When core 1 is β-amino acid, specific examples of core 1 include bAla and bMeAla.

In an embodiment, in formula (1), $R_2$ is $C_1$-$C_6$ alkyl, $C_2$-$C_6$ alkenyl, $C_2$-$C_6$ alkynyl, $C_1$-$C_6$ alkoxy$C_1$-$C_6$ alkyl, $C_3$-$C_8$ cycloalkyl, $C_3$-$C_8$ cycloalkyl$C_1$-$C_6$ alkyl, or $C_3$-$C_8$ cycloalkoxy$C_1$-$C_6$ alkyl, each of which is optionally substituted with one or more groups independently selected from the group consisting of halogen, hydroxy, cyano, and $C_1$-$C_6$ alkylsulfonyl.

$R_2$ is preferably $C_1$-$C_6$ alkyl, $C_1$-$C_6$ haloalkyl, $C_1$-$C_6$ hydroxyalkyl, $C_1$-$C_6$ alkylsulfonyl$C_1$-$C_6$ alkyl, $C_1$-$C_6$ cyanoalkyl, $C_2$-$C_6$ alkenyl, $C_2$-$C_6$ alkynyl, $C_1$-$C_6$ alkoxy$C_1$-$C_6$ alkyl optionally substituted with one or more halogens, $C_3$-$C_8$ cycloalkyl, $C_3$-$C_8$ cycloalkyl$C_1$-$C_6$ alkyl, or $C_3$-$C_8$ cycloalkoxy$C_1$-$C_6$ alkyl.

$R_2$ is more preferably $C_1$-$C_6$ alkyl, $C_1$-$C_6$ fluoroalkyl, $C_1$-$C_4$ hydroxyalkyl, methylsulfonyl$C_1$-$C_2$ alkyl, $C_2$-$C_6$ alkenyl, $C_2$-$C_3$ alkynyl, $C_1$-$C_6$ alkoxy$C_1$-$C_2$ alkyl, $C_3$-$C_6$ cycloalkyl, $C_3$-$C_6$ cycloalkyl$C_1$-$C_2$ alkyl, or $C_3$-$C_6$ cycloalkoxy$C_1$-$C_2$ alkyl.

Specific examples of $R_2$ include methyl, ethyl, n-propyl, i-propyl, n-butyl, 2-methylpropyl, 1-methylpropyl, n-pentyl, 3-methylbutyl, 2-methylbutyl, pentan-3-yl, n-propoxymethyl, cyclopropoxymethyl, hydroxymethyl, 2,2,2-trifluoroethyl, 5,5-difluoropentyl, methoxymethyl, 3-methyl-butoxymethyl, 2-hydroxyethyl, cyclobutoxymethyl, (2,2,2-trifluoroethoxy)methyl, cyanomethyl, 1-methoxyethyl, 2-methoxyethyl, 2-methylsulfonylethyl, allyl, 3-methylbut-2-en-1-yl, propargyl, cyclohexyl, cyclopentyl, cyclobutyl, cyclopropyl, cyclohexylmethyl, cyclopentylmethyl, cyclobutylmethyl, and cyclopropylmethyl.

In an embodiment, in formula (1), $R_2$ and $P_2$, together with the carbon atom to which $R_2$ is attached and the nitrogen atom to which $P_2$ is attached, can form a 4- to 7-membered saturated heterocyclic ring.

When $R_2$ and $P_2$ form a 4- to 7-membered saturated heterocyclic ring, the 4- to 7-membered saturated heterocyclic ring is preferably an azetidine ring, a pyrrolidine ring, a piperidine ring, a piperazine ring, or a morpholine ring.

In an embodiment, in formula (1), $R_2$ and $Q_2$, together with the carbon atom to which they are attached, can form a 3- to 8-membered alicyclic ring or a 4- to 7-membered saturated heterocyclic ring.

When $R_2$ and $Q_2$ form a 3- to 8-membered alicyclic ring or a 4- to 7-membered saturated heterocyclic ring, the 3- to 8-membered alicyclic ring is preferably a cyclopropane ring, a cyclobutane ring, a cyclopentane ring, or a cyclohexane ring, and the 4- to 7-membered saturated heterocyclic ring is preferably a tetrahydrofuran ring or a tetrahydropyran ring.

In an embodiment, in formula (1), except when $R_2$ and $P_2$ form a 4- to 7-membered saturated heterocyclic ring, $P_2$ is hydrogen or $C_1$-$C_6$ alkyl, wherein the $C_1$-$C_6$ alkyl is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino). $P_2$ is preferably hydrogen.

In an embodiment, except when $R_2$ and $Q_2$ form a 3- to 8-membered alicyclic ring or a 4- to 7-membered saturated heterocyclic ring, $Q_2$ is hydrogen or $C_1$-$C_6$ alkyl, and preferably hydrogen.

Specific examples of core 2 include Ala, Val, Leu, Ile, Nle, PRA, Chg, Cha, Ala(cPent), Ala(cBu), Ala(cPr), Gly(cPent), Gly(cBu), Gly(cPr), Hle, Ser(nPr), Ser(cPr), Ser, Abu(4-F3), Ahp(2), Abu, Nva, Hnl(7-F2), Ser(Me), Ser(iPen), Thr, Algly, Pregly, Ser(cBu), Ser(Tfe), Ala(CN), Thr(Me), Hse (Me), Met(O2), and Nva(3-Et).

In an embodiment, in formula (1), $R_3$ is hydrogen, $C_1$-$C_6$ alkyl, $C_1$-$C_6$ alkoxy$C_1$-$C_6$ alkyl, $C_3$-$C_8$ cycloalkyl, $C_3$-$C_8$ cycloalkyl$C_1$-$C_6$ alkyl, $C_3$-$C_8$ cycloalkoxy$C_1$-$C_6$ alkyl, or $C_7$-$C_{14}$ aralkyl, each of which is optionally substituted with one or more groups independently selected from the group consisting of hydroxy and aminocarbonyl (wherein the amino is —$NH_2$, mono-$C_1$-$C_6$ alkylamino, di-$C_1$-$C_6$ alkylamino, or 4- to 8-membered cyclic amino).

$R_3$ is preferably hydrogen, $C_1$-$C_6$ alkyl, $C_1$-$C_6$ hydroxyalkyl, $C_1$-$C_6$ alkoxy$C_1$-$C_6$ alkyl (wherein the $C_1$-$C_6$ alkoxy$C_1$-$C_6$ alkyl is optionally substituted with aminocarbonyl (wherein the amino is —$NH_2$, mono-$C_1$-$C_6$ alkylamino, di-$C_1$-$C_6$ alkylamino, or 4- to 8-membered cyclic amino) or hydroxy), aminocarbonyl$C_1$-$C_6$ alkyl (wherein the amino is —$NH_2$, mono-$C_1$-$C_6$ alkylamino, di-$C_1$-$C_6$ alkylamino, or 4- to 8-membered cyclic amino), $C_3$-$C_8$ cycloalkyl, $C_3$-$C_8$ cycloalkyl$C_1$-$C_6$ alkyl, $C_3$-$C_8$ cycloalkoxy$C_1$-$C_6$ alkyl, or $C_7$-$C_{14}$ aralkyl.

$R_3$ is more preferably hydrogen, $C_1$-$C_6$ alkyl, $C_1$-$C_4$ hydroxyalkyl, $C_1$-$C_6$ alkoxy$C_1$-$C_2$ alkyl optionally substituted with mono-$C_1$-$C_4$ alkylaminocarbonyl or hydroxy, mono-$C_1$-$C_4$ alkylaminocarbonyl$C_1$-$C_2$ alkyl, $C_3$-$C_6$ cycloalkyl, $C_3$-$C_6$ cycloalkyl$C_1$-$C_2$ alkyl, benzyl, or phenethyl.

Specific examples of $R_3$ include hydrogen, methyl, ethyl, n-propyl, i-propyl, n-butyl, 2-methylpropyl, 3-methylbutyl, (2-hydroxy-2-methyl-propyloxy)methyl, (2-(tert-butylamino)-2-oxoethoxy)methyl, n-propoxymethyl, cyclopropoxymethyl, 3-methylbutoxymethyl, 1-hydroxyethyl, 3-methylamino-3-oxo-propyl, cyclohexyl, cyclobutyl, cyclopropyl, cyclopropylmethyl, cyclobutylmethyl, cyclopentylmethyl, cyclohexylmethyl, benzyl, and phenethyl.

In an embodiment, in formula (1), $R_3$ and $P_3$, together with the carbon atom to which $R_3$ is attached and the nitrogen atom to which $P_3$ is attached, can form a 4- to 7-membered saturated heterocyclic ring.

When $R_3$ and $P_3$ form a 4- to 7-membered saturated heterocyclic ring, the 4- to 7-membered saturated heterocyclic ring is preferably an azetidine ring, a pyrrolidine ring, a piperidine ring, a piperazine ring, or a morpholine ring.

In an embodiment, in formula (1), $R_3$ and $Q_3$, together with the carbon atom to which they are attached, can form a 3- to 8-membered alicyclic ring or a 4- to 7-membered saturated heterocyclic ring.

When $R_3$ and $Q_3$ form a 3- to 8-membered alicyclic ring or a 4- to 7-membered saturated heterocyclic ring, the 3- to 8-membered alicyclic ring is preferably a cyclopropane ring, a cyclobutane ring, a cyclopentane ring, or a cyclohexane ring, and the 4- to 7-membered saturated heterocyclic ring is preferably a tetrahydrofuran ring or a tetrahydropyran ring.

In an embodiment, in formula (1), except when $R_3$ and $P_3$ form a 4- to 7-membered saturated heterocyclic ring, $P_3$ is hydrogen, $C_1$-$C_6$ alkyl, $C_1$-$C_6$ alkoxy$C_1$-$C_6$ alkyl, or $C_3$-$C_8$ cycloalkyl, each of which is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino).

$P_3$ is preferably hydrogen, $C_1$-$C_6$ alkyl, $C_1$-$C_6$ aminoalkyl (wherein the amino is —$NH_2$, protected amino, mono-$C_1$-$C_6$ alkylamino, di-$C_1$-$C_6$ alkylamino, or 4- to 8-membered cyclic amino, each of which is optionally substituted with one or more halogens), or $C_3$-$C_8$ cycloalkyl.

$P_3$ is more preferably hydrogen, $C_1$-$C_6$ alkyl, $C_1$-$C_4$ alkoxy$C_1$-$C_2$ alkyl, 4- to 8-membered cyclic amino$C_1$-$C_2$ alkyl optionally substituted with one or more halogens, or $C_3$-$C_6$ cycloalkyl. Specific examples of such $P_3$ include hydrogen, methyl, ethyl, n-propyl, i-propyl, cyclopropyl, n-butyl, i-butyl, 2-ethoxyethyl, and 2-(4,4-difluoro-1-piperidyl)ethyl.

In an embodiment, except when $R_3$ and $Q_3$ form a 3- to 8-membered alicyclic ring or a 4- to 7-membered saturated heterocyclic ring, $Q_3$ is hydrogen or $C_1$-$C_6$ alkyl, and preferably hydrogen.

Specific examples of core 3 include MeAla, Ala, Pic(2), MeLeu, MeCha, MeVal, EtAla, MeSer(tBuOH), MeSer(NtBu-Aca), MeAla(cPent), MeAla(cBu), MeAla(cPr), MeChg, MeGly, MeGly(cBu), MeGly(cPr), MeAbu, MeNva, MeNle, MeHle, MeSer(nPr), MeSer(cPr), MeSer(iPen), MeThr, Abu, MeGly, EtGly, Gly, nBuGly, iPrGly, cPrGly, nPrGly, iBuGly, (EtOEt)NGly, 2-(pip-4-F2)-EtGly, Pro, Aze(2), MeGln(Me), MePhe, and MeHph.

In one embodiment, in formula (1), $R_4$ is hydrogen or $C_1$-$C_6$ alkyl, and preferably hydrogen or $C_1$-$C_4$ alkyl. Specific examples of $R_4$ include hydrogen and methyl.

In an embodiment, in formula (1), $R_4$ and $P_4$, together with the carbon atom to which $R_4$ is attached and the nitrogen atom to which $P_4$ is attached, can form a 4- to 7-membered saturated heterocyclic ring (preferably, 4- or 5-membered saturated heterocyclic ring).

When $R_4$ and $P_4$ form a 4- to 7-membered saturated heterocyclic ring, the 4- to 7-membered saturated heterocyclic ring is preferably an azetidine ring, a pyrrolidine ring, a piperidine ring, a piperazine ring, or a morpholine ring.

In an embodiment, in formula (1), $R_4$ and $Q_4$, together with the carbon atom to which they are attached, can form a 3- to 8-membered alicyclic ring or a 4- to 7-membered saturated heterocyclic ring.

When $R_4$ and $Q_4$ form a 3- to 8-membered alicyclic ring or a 4- to 7-membered saturated heterocyclic ring, the 3- to 8-membered alicyclic ring is preferably a cyclopropane ring, a cyclobutane ring, a cyclopentane ring, or a cyclohexane ring, and the 4- to 7-membered saturated heterocyclic ring is preferably a tetrahydrofuran ring or a tetrahydropyran ring.

In an embodiment, in formula (1), except when $R_4$ and $P_4$ form a 4- to 7-membered saturated heterocyclic ring, $P_4$ is hydrogen, $C_1$-$C_6$ alkyl, or $C_1$-$C_6$ alkoxy$C_1$-$C_6$ alkyl, each of which is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino).

$P_4$ is preferably $C_1$-$C_6$ alkyl or $C_1$-$C_6$ alkoxy$C_1$-$C_6$ alkyl.

$P_4$ is more preferably hydrogen, $C_1$-$C_6$ alkyl, or $C_1$-$C_4$ alkoxy$C_1$-$C_2$ alkyl. Specific examples of $P_4$ include methyl, ethyl, n-propyl, n-butyl, i-propyl, i-pentyl, and 2-ethoxyethyl.

In an embodiment, except when $R_4$ and $Q_4$ form a 3- to 8-membered alicyclic ring or a 4- to 7-membered saturated heterocyclic ring, $Q_4$ is hydrogen or $C_1$-$C_6$ alkyl, and preferably hydrogen.

Specific examples of core 4 include MeAla, Pic(2), MeGly, EtGly, nBuGly, nPrGly, (EtOEt)NGly, Pro, Aze(2), and iPenGly.

In an embodiment, in formula (1), $R_5$ is $C_1$-$C_6$ alkyl, $C_2$-$C_6$ alkenyl, $C_2$-$C_6$ alkynyl, $C_1$-$C_6$ alkoxy$C_1$-$C_6$ alkyl, $C_3$-$C_8$ cycloalkyl, $C_3$-$C_8$ cycloalkyl$C_1$-$C_6$ alkyl, $C_3$-$C_8$ cycloalkoxy$C_1$-$C_6$ alkyl, $C_7$-$C_{14}$ aralkyl, $C_6$-$C_{10}$ aryloxy$C_1$-$C_6$ alkyl, $C_7$-$C_{14}$ aralkoxy$C_1$-$C_6$ alkyl, or 5- to 10-membered heteroaryl$C_1$-$C_6$ alkyl, each of which is optionally substituted with one or more groups independently selected from the group consisting of halogen, hydroxy, $C_1$-$C_6$ alkyl, $C_1$-$C_6$ haloalkyl, $C_1$-$C_6$ alkoxy, $C_1$-$C_6$ haloalkoxy, cyano, and $C_1$-$C_6$ alkylsulfonyl.

$R_5$ is preferably $C_1$-$C_6$ alkyl, $C_1$-$C_6$ haloalkyl, $C_1$-$C_6$ hydroxyalkyl, $C_2$-$C_6$ alkenyl, $C_1$-$C_6$ alkylsulfonyl$C_1$-$C_6$ alkyl, $C_2$-$C_6$ alkynyl, $C_1$-$C_6$ alkoxy$C_1$-$C_6$ alkyl optionally substituted with one or more halogens, $C_3$-$C_8$ cycloalkyl, $C_3$-$C_8$ cycloalkyl$C_1$-$C_6$ alkyl, $C_3$-$C_8$ cycloalkoxy$C_1$-$C_6$ alkyl, $C_7$-$C_{14}$ aralkyl (wherein the $C_7$-$C_{14}$ aralkyl is optionally substituted with one or more halogens, $C_1$-$C_6$ alkyl, $C_1$-$C_6$ alkoxy, $C_1$-$C_6$ haloalkyl, $C_1$-$C_6$ haloalkoxy, or cyano), $C_6$-$C_{10}$ aryloxy$C_1$-$C_6$ alkyl optionally substituted with one or more halogens, $C_7$-$C_{14}$ aralkoxy$C_1$-$C_6$ alkyl, or 5- to 10-membered heteroaryl$C_1$-$C_6$ alkyl.

$R_5$ is more preferably $C_1$-$C_6$ alkyl, $C_1$-$C_6$ fluoroalkyl, $C_1$-$C_4$ hydroxyalkyl, $C_2$-$C_3$ alkenyl, $C_2$-$C_3$ alkynyl, methylalkylsulfonyl$C_1$-$C_2$ alkyl, $C_1$-$C_6$ alkoxy$C_1$-$C_2$ alkyl optionally substituted with one or more fluorines, $C_3$-$C_6$ cycloalkyl, $C_3$-$C_6$ cycloalkyl$C_1$-$C_2$ alkyl, $C_3$-$C_6$ cycloalkoxy$C_1$-$C_2$ alkyl, benzyl or phenethyl optionally substituted with one or more halogens, methyl, methoxy, trifluoromethyl, trifluoromethoxy, or cyano, phenoxy$C_1$-$C_2$ alkyl optionally substituted with one or more halogens, benzyloxy$C_1$-$C_2$ alkyl, and 5- to 6-membered heteroaryl$C_1$-$C_2$ alkyl.

Specific examples of $R_5$ include methyl, ethyl, n-propyl, i-propyl, n-butyl, 2-methylpropyl, 1-methylpropyl, 2-methylbutyl, 3-methylbutyl, n-pentyl, propargyl, 3,3-difluorobutyl, n-propoxymethyl, cyclopropoxymethyl, hydroxymethyl, 2,2,2-trifluoroethyl, 5,5-difluorobutyl, methoxymethyl, 3-methylbutoxymethyl, 1-hydroxyethyl, cyclobutoxymethyl, (2,2,2-trifluoroethoxy)methyl, 1-methoxyethyl, 2-methoxyethyl, 2-methylsulfonylethyl, (2-chlorophenoxy)methyl, allyl, cyclopropyl, cyclobutyl, cyclohexyl, cyclopentyl, cyclopentylmethyl, cyclohexylmethyl, cyclobutylmethyl, cyclopropylmethyl, pyridin-3-ylmethyl, phenethyl, 4-chlorobenzyl, 2-cyanobenzyl, 3-cyanobenzyl, 4-ethynylbenzyl, 2-fluorobenzyl, 2-chlorobenzyl, 3-chlorobenzyl, 3-bromobenzyl, 4-bromobenzyl, 2-methylbenzyl, 3-methylbenzyl, 4-methylbenzyl, 2-(trifluoromethyl)benzyl, 3-(trifluoromethyl)benzyl, 4-(trifluoromethyl)benzyl, 4-methoxybenzyl, 2-(trifluoromethoxy)benzyl, 3-(trifluoromethoxy)benzyl, 4-(trifluoromethoxy)benzyl, 3,4-difluorobenzyl, 4-iodobenzyl, benzyl, 3-fluorobenzyl, and 4-fluorobenzyl.

In an embodiment, in formula (1), $R_5$ together with $R_8$ can form $C_4$-$C_8$ alkylene. $C_4$-$C_8$ alkylene is preferably —$(CH_2)_8$—.

In an embodiment, in formula (1), $R_5$ and $P_5$, together with the carbon atom to which $R_5$ is attached and the nitrogen atom to which $P_5$ is attached, can form a 4- to 7-membered saturated heterocyclic ring.

When $R_5$ and $P_5$ form a 4- to 7-membered saturated heterocyclic ring, the 4- to 7-membered saturated heterocyclic ring is preferably an azetidine ring, a pyrrolidine ring, a piperidine ring, a piperazine ring, or a morpholine ring.

In an embodiment, in formula (1), $R_5$ and $Q_5$, together with the carbon atom to which they are attached, can form a 3- to 8-membered alicyclic ring or a 4- to 7-membered saturated heterocyclic ring.

When $R_5$ and $Q_5$ form a 3- to 8-membered alicyclic ring or a 4- to 7-membered saturated heterocyclic ring, the 3- to 8-membered alicyclic ring is preferably a cyclopropane ring, a cyclobutane ring, a cyclopentane ring, or a cyclohexane ring, and the 4- to 7-membered saturated heterocyclic ring is preferably a tetrahydrofuran ring or a tetrahydropyran ring.

In an embodiment, in formula (1), except when $R_5$ and $P_5$ form a 4- to 7-membered saturated heterocyclic ring, $P_5$ is hydrogen or $C_1$-$C_6$ alkyl, wherein the $C_1$-$C_6$ alkyl is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino).

$P_5$ is preferably hydrogen or $C_1$-$C_2$ alkyl, and specific examples include hydrogen, methyl, and ethyl.

In an embodiment, except when $R_5$ and $Q_5$ form a 3- to 8-membered alicyclic ring or a 4- to 7-membered saturated heterocyclic ring, $Q_5$ is hydrogen or $C_1$-$C_6$ alkyl, and preferably hydrogen.

Specific examples of core 5 include MeAla, MeLeu, MeCha, MeVal, MeAla(cPent), MeAla(cBu), MeAla(cPr), MeChg, MeGly(cPent), MeGly(cBu), MeGly(cPr), MeAbu, MeNva, MeNle, MeNva(5-F2), MeHle, MeIle, MeSer(nPr), MeSer(cPr), MeSer, MeAbu(4-F3), MeHnl, MeHnl(7-F2), MePRA, MeSer(Me), MeSer(iPen), MeThr, MeSer(cBu), MeSer(Tfe), MeThr(Me), MeHse(Me), MeMet(O2), MePhe, MeHph, MePhe(4-Cl), MeThr(Bn), EtPhe(4-Cl), MePhe(2-CN), MePhe(3-CN), MePhe(4-CN), MePhe(2-F), MePhe(3-F), MePhe(4-F), MePhe(2-Cl), MePhe(3-Cl), MePhe(3-Br), MePhe(4-Br), MePhe(2-Me), MePhe(3-Me), MePhe(4-Me), MePhe(2-CF3), MePhe(3-CF3), MePhe(4-CF3), MeTyr(Me), MePhe(2-OCF3), MePhe(3-OCF3), MePhe(4-OCF3), MeSer(Ph-2-Cl), MeAlgly, MePhe(34-F2), MeAla(3-Pyr), MePhe(4-I), EtCha, EtPhe(4-Me), EtPhe(4-CF3), and Phe(4-Me).

In an embodiment, in formula (1), $R_6$ is hydrogen or $C_1$-$C_6$ alkyl, and preferably hydrogen or $C_1$-$C_3$ alkyl. Specific examples of $R_6$ include hydrogen and methyl.

In an embodiment, in formula (1), $R_6$ and $P_6$, together with the carbon atom to which $R_6$ is attached and the nitrogen atom to which $P_6$ is attached, can form a 4- to 7-membered saturated heterocyclic ring.

When $R_6$ and $P_6$ form a 4- to 7-membered saturated heterocyclic ring, the 4- to 7-membered saturated heterocyclic ring is preferably an azetidine ring, a pyrrolidine ring, a piperidine ring, a piperazine ring, or a morpholine ring.

In an embodiment, in formula (1), $R_6$ and $Q_6$, together with the carbon atom to which they are attached, can form a 3- to 8-membered alicyclic ring or a 4- to 7-membered saturated heterocyclic ring.

When $R_6$ and $Q_6$ form a 3- to 8-membered alicyclic ring or a 4- to 7-membered saturated heterocyclic ring, the 3- to 8-membered alicyclic ring is preferably a cyclopropane ring, a cyclobutane ring, a cyclopentane ring, or a cyclohexane ring, and the 4- to 7-membered saturated heterocyclic ring is preferably a tetrahydrofuran ring or a tetrahydropyran ring.

In an embodiment, in formula (1), except when $R_6$ and $P_6$ form a 4- to 7-membered saturated heterocyclic ring, $P_6$ is $C_1$-$C_6$ alkyl or $C_3$-$C_8$ cycloalkyl, each of which is optionally substituted with one or more groups independently selected from the group consisting of halogen, hydroxy, $C_1$-$C_6$ alkoxyamino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino).

$P_6$ is preferably $C_1$-$C_6$ alkyl or $C_3$-$C_8$ cycloalkyl, and more preferably $C_1$-$C_4$ alkyl or $C_3$-$C_6$ cycloalkyl. Specific examples of such $P_6$ include methyl, ethyl, and cyclopropyl.

In an embodiment, except when $R_6$ and $Q_6$ form a 3- to 8-membered alicyclic ring or a 4- to 7-membered saturated heterocyclic ring, $Q_6$ is hydrogen or $C_1$-$C_6$ alkyl, and preferably hydrogen.

Specific examples of core 6 include MeAla, MeGly, EtGly, cPrGly, D-Pro, D-MeAla, and D-Pic(2).

In an embodiment, in formula (1), $R_7$ is $C_6$-$C_{10}$ aryloxy$C_1$-$C_6$ alkyl, $C_7$-$C_{14}$ aralkyl, $C_7$-$C_{14}$ aralkoxy$C_1$-$C_6$ alkyl, or 5- to 10-membered heteroaryl$C_1$-$C_6$ alkyl, each of which is optionally substituted with one or more groups independently selected from the group consisting of halogen, $C_1$-$C_6$ alkyl, $C_1$-$C_6$ haloalkyl, $C_2$-$C_6$ alkynyl, $C_1$-$C_6$ alkoxy, $C_1$-$C_6$ haloalkoxy, cyano, $C_1$-$C_6$ alkylsulfonyl, and $SF_5$.

$R_7$ is preferably $C_6$-$C_{10}$ aryloxy$C_1$-$C_6$ alkyl (wherein the $C_6$-$C_{10}$ aryloxy$C_1$-$C_6$ alkyl is optionally substituted with one or more groups independently selected from the group consisting of halogen and $C_1$-$C_6$ haloalkyl), $C_7$-$C_{14}$ aralkyl (wherein the $C_7$-$C_{14}$ aralkyl is optionally substituted with one or more groups independently selected from the group consisting of halogen, $C_1$-$C_6$ alkyl, $C_1$-$C_6$ haloalkyl, $C_1$-$C_6$ alkoxy, $C_1$-$C_6$ haloalkoxy, $C_2$-$C_6$ alkynyl, cyano, $C_1$-$C_6$ alkylsulfonyl, and $SF_5$), $C_7$-$C_{14}$ aralkoxy$C_1$-$C_6$ alkyl optionally substituted with one or more halogens, or 5- to 10-membered heteroaryl$C_1$-$C_6$ alkyl (wherein the 5- to 10-membered heteroaryl$C_1$-$C_6$ alkyl is optionally substituted with one or more halogens, $C_1$-$C_6$ alkyl, $C_1$-$C_6$ haloalkyl, or $C_1$-$C_6$ alkoxy).

$R_7$ is preferably —$(CH_2)_x$—$O_y$—$(CH_2)_{z1}$—$C_6$-$C_{10}$ aryl or —$(CH_2)_x$—$O_y$—$(CH_2)_{z2}$-5- to 10-membered heteroaryl optionally substituted with one to five groups independently selected from the group consisting of halogen, $C_1$-$C_4$ alkyl (preferably methyl), $C_2$-$C_4$ alkynyl (preferably ethynyl), $C_1$-$C_3$ haloalkyl (preferably difluoromethyl, trifluoromethyl), $C_1$-$C_3$ haloalkoxy (preferably difluoromethoxy, trifluoromethoxy), $C_1$-$C_4$ alkoxy (preferably methoxy, ethoxy, isopropoxy, n-butoxy, t-butoxy), —CN, $C_1$-$C_3$ alkylsulfonyl (preferably methylsulfonyl), and $SF_5$, wherein x is 1, 2, or 3, y is 0 or 1, and z1 is 0, 1, 2, or 3, provided that the sum of x, y, and z1 or z2 is 1 to 4. Such —$(CH_2)_x$—$O_y$—$(CH_2)_{z1}$—$C_6$-$C_{10}$ aryl or —$(CH_2)_x$—$O_y$—$(CH_2)_{z2}$-5- to 10-membered heteroaryl is preferably —$CH_2$—$C_6$-$C_{10}$ aryl or —$(CH_2)_2$-$C_6$-$C_{10}$ aryl, which is optionally substituted with the above-mentioned group(s). When —$(CH_2)_x$—$O_y$—$(CH_2)_{z1}$—$C_6$-$C_{10}$ aryl has a substituent, the substituent is preferably on $C_6$-$C_{10}$ aryl in the group, and when —$(CH_2)_x$—$O_y$—$(CH_2)_{z2}$-5- to 10-membered heteroaryl has a substituent, the substituent is preferably on 5- to 10-membered heteroaryl in the group.

Specific examples of $R_7$ include ((4-chlorobenzyl)oxy)methyl, 2-(4-chlorophenoxy)ethyl, 2-(3,4-dichlorophenoxy)ethyl, 2-(4-(trifluoromethylphenoxy))ethyl, (4-chlorophenoxy)methyl, ((3-chlorobenzyl)oxy)methyl, ((2-chlorobenzyl)oxy)methyl, 3-iodobenzyl, 3-chlorobenzyl, 3-methylbenzyl, 3-fluorobenzyl, 3,5-difluorobenzyl, 4-methylphenethyl, 4-(trifluoromethyl)phenethyl, 3-chloro-5-fluorobenzyl, 3-cyanobenzyl, 3-(trifluoromethoxy)benzyl, benzyl, 4-fluorophenethyl, 2-fluoro-4-(trifluoromethyl)phenethyl, 3-chlorophenethyl, 4-chlorophenethyl, 3-fluoro-4-(trifluoromethyl)phenethyl, 2,3,4,5,6-pentafluorophenethyl, 2,4,5-trifluorophenethyl, 2,5-difluorophenethyl, 2-fluoro-4-chlorophenethyl, 2,4-difluorophenethyl, 2-fluoro-6-chlorophenethyl, 2,4,6-trifluorophenethyl, 3-chloro-4-(trifluoromethyl)phenethyl, 3-trifluoromethylphenethyl, 4-(pentafluoro-λ6-sulfanyl)phenethyl, 3,5-difluoro-4-(trifluoromethyl)phenethyl, 3-methoxybenzyl, 3,5-dichlorobenzyl, 3-chloro-4-fluorobenzyl, phenethyl, 3,4-dichlorophenethyl, 3-bromobenzyl, 4-fluorobenzyl, 2-fluoro-5-iodobenzyl, 2-chloro-5-iodobenzyl, 3-ethynylbenzyl, 3-fluorophenethyl, 3-phenylpropyl, 2-fluorobenzyl, 2-fluoro-3-iodobenzyl, 2-fluoro-3-bromobenzyl, 3-iodo-5-fluorobenzyl, 3-iodo-5-chlorobenzyl, 3-bromo-5-fluorobenzyl, 2-bromo-5-iodobenzyl, 2-methyl-5-iodobenzyl, 2-fluoro-5-methylbenzyl, 2-chloro-5-bromobenzyl, 2-methyl-5-bromobenzyl, 2,3-difluorobenzyl, 2,5-difluorobenzyl, 2,6-difluorobenzyl, 3-fluoro-4-(difluoromethoxy)phenethyl, 3-cyano-4-(trifluoromethyl)phenethyl, 3-methoxy-4-(trifluoromethyl)phenethyl, 2-(2,2-difluorobenzo[d][1,3]dioxol-5-yl)ethyl, 3-chloro-4-(trifluoromethoxy)phenethyl, 3-fluoro-4-(trifluoromethoxy)phenethyl, 4-(methylsulfonyl)phenethyl, 3-fluoro-4-(difluoromethyl)phenethyl, 3,4,5-trichlorophenethyl, 3,4-dichloro-5-methoxyphenethyl, 3,4-dichloro-5-cyanophenethyl, 3,4-dichloro-5-isopropoxyphenethyl, 3,4-dichloro-5-(n-butoxy)phenethyl, 3,4-dichloro-5-(t-butoxy)phenethyl, 3-(4-(trifluoromethyl)phenyl)propyl, (5-chlorothiophen-2-yl)methyl, (5-bromothiophen-2-yl)methyl, (5-bromopyridin-3-yl)methyl, 2-(6-(trifluoromethyl)pyridin-3-yl)ethyl, 2-(quinolin-6-yl)ethyl, 2-(1-methyl-1H-indol-6-yl)ethyl, 2-(1-methyl-1H-indol-5-yl)ethyl, 2-(6-methoxypyridin-3-yl)ethyl, 2-(benzofuran-5-yl)ethyl, 2-(6-(difluoromethyl)pyridin-3-yl)ethyl, 2-(5-(trifluoromethyl)pyridin-2-yl)ethyl, and 2-(quinolin-7-yl)ethyl.

In an embodiment, in formula (1), $R_7$ and $P_7$, together with the carbon atom to which $R_7$ is attached and the nitrogen atom to which $P_7$ is attached, can form a 4- to 7-membered saturated heterocyclic ring.

When $R_7$ and $P_7$ form a 4- to 7-membered saturated heterocyclic ring, the 4- to 7-membered saturated heterocyclic ring is preferably an azetidine ring, a pyrrolidine ring, a piperidine ring, a piperazine ring, or a morpholine ring.

In an embodiment, in formula (1), $R_7$ and $Q_7$, together with the carbon atom to which they are attached, can form a 3- to 8-membered alicyclic ring or a 4- to 7-membered saturated heterocyclic ring.

When $R_7$ and $Q_7$ form a 3- to 8-membered alicyclic ring or a 4- to 7-membered saturated heterocyclic ring, the 3- to 8-membered alicyclic ring is preferably a cyclopropane ring, a cyclobutane ring, a cyclopentane ring, or a cyclohexane ring, and the 4- to 7-membered saturated heterocyclic ring is preferably a tetrahydrofuran ring or a tetrahydropyran ring.

In an embodiment, in formula (1), except when $R_7$ and $P_7$ form a 4- to 7-membered saturated heterocyclic ring, $P_7$ is hydrogen or $C_1$-$C_6$ alkyl, wherein the $C_1$-$C_6$ alkyl is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino). $P_7$ is preferably hydrogen.

In an embodiment, except when $R_7$ and $Q_7$ form a 3- to 8-membered alicyclic ring or a 4- to 7-membered saturated heterocyclic ring, $Q_7$ is hydrogen, $C_1$-$C_6$ alkyl, or $C_7$-$C_{14}$ aralkyl, and is preferably hydrogen.

Specific examples of core 7 include Phe(3-Cl), Phe(3-Me), Phe(3-F), Phe(35-F2), Hph(4-Me), Hph(4-CF3), Phe(3-Cl-5-F), Phe(3-I), Phe(3-CN), Phe(3-OCF3), Phe, Hph(4-F), Hph(4-CF3-2-F), Hph(3-Cl), Hph(4-Cl), Hph(4-CF3-3-F), Hph(F5), Hph(245-F3), Hph(2-F-5-Cl), Hph(2-F-4-Cl), Hph(24-F2), Hph(2-F-6-Cl), Hph(246-F3), Hph(4-CF3-3-Cl), Hph(3-CF3), Hph(4-$SF_5$), Hph(4-CF3-35-F2), Phe(3-OMe), Phe(35-Cl2), Phe(3-Cl-4-F), Hph, Hph(34-Cl2), Phe(3-Br), Phe(4-F), Phe(2-F-5-I), Phe(2-Cl-5-I), Ala(2-Thie-5-Cl), Ala(2-Thie-5-Br), (Me)Phe(3-I), Phe(3-C#C), Hph(3-F), Phe3, Phe(2-F), Phe(2-F-3-I), Phe(2-F-3-Br), Phe(3-I-5-F), Phe(3-I-5-Cl), Ala(3-Pyr-5-Br), Phe(3-Br-5-F), Phe(2-Br-5-I), Phe(2-Me-5-I), Phe(2-F-5-Br), Phe(2-Cl-5-Br), Phe(2-Me-5-Br), Phe(23-F2), Phe(25-F2), Phe(26-F2), Hph(3-F-4-OCHF2), Hph(3-CN-4-CF3), Hph(3-OMe-4-CF3), Abu(3-Pyr-4-CF3), Abu(34-Cate(CF2)), Hph(3-Cl-4-OCF3), Hph(3-F-4-OCF3), Abu(6-Quino), Abu(1-Me-6-Indo), Abu(1-Me-5-Indo), Abu(3-Pyr-4-OMe), Abu(5-Bzfr), Abu(3-Pyr-4-CHF2), Abu(2-Pyr-4-CF3), Hph(4-SO2Me), Hph(3-F-4-CHF2), Abu(7-Quino), Hph(345-Cl3), Hph(34-Cl2-5-OMe), Hph(34-Cl2-5-CN), Hph(34-Cl2-5-OiPr), Hph(34-Cl2-5-OnBu), Hph(34-Cl2-5-OtBu), Phe3(4-CF3), Ser(Bn-4-Cl), Hse(Ph-4-Cl), Hse(Ph-34-Cl2), Hse(Ph-4-CF3), Ser(Ph-4-Cl), Ser(Bn-3-Cl), and Ser(Bn-2-Cl).

In an embodiment, in formula (1), $R_8$ is hydrogen, $C_1$-$C_6$ alkyl, $C_2$-$C_6$ alkenyl, $C_2$-$C_6$ alkynyl, $C_1$-$C_6$ alkoxy$C_1$-$C_6$ alkyl, $C_2$-$C_6$ alkenyloxycarbonyl$C_1$-$C_6$ alkyl, $C_3$-$C_8$ cycloalkyl, $C_3$-$C_8$ cycloalkyl$C_1$-$C_6$ alkyl, $C_6$-$C_{10}$ aryloxy$C_1$-$C_6$ alkyl, $C_7$-$C_{14}$ aralkyl, $C_7$-$C_{14}$ aralkoxy$C_1$-$C_6$ alkyl, 5- to 10-membered heteroaryl$C_1$-$C_6$ alkyl, or 5- to 10-membered heteroaryl$C_1$-$C_6$ alkoxy$C_1$-$C_6$ alkyl, each of which is optionally substituted with one or more groups independently selected from the group consisting of halogen, hydroxy, carboxy, $C_1$-$C_6$ alkyl, $C_1$-$C_6$ haloalkyl, $C_2$-$C_6$ alkynyl, $C_1$-$C_6$ alkoxy, $C_1$-$C_6$ haloalkoxy, cyano, amino (wherein the amino is —$NH_2$, protected amino, mono-$C_1$-$C_6$ alkylamino, di-$C_1$-$C_6$ alkylamino, or 4- to 8-membered cyclic amino, each of which is optionally substituted with halogen), aminocarbonyl (wherein the amino is —$NH_2$, mono-$C_1$-$C_6$ alkylamino, di-$C_1$-$C_6$ alkylamino, or 4- to 8-membered cyclic amino, each of which is optionally substituted with halogen), 4- to 7-membered heterocycloalkylidene, protected 4- to 7-membered heterocycloalkylidene, 4- to 7-membered heterocyclyl, and protected 4- to 7-membered heterocyclyl.

$R_8$ is preferably hydrogen, $C_1$-$C_6$ alkyl, $C_1$-$C_6$ haloalkyl, $C_1$-$C_6$ hydroxyalkyl, $C_1$-$C_6$ carboxyalkyl, $C_1$-$C_6$ aminoalkyl (wherein the amino is —$NH_2$, protected amino, mono-$C_1$-$C_6$ alkylamino, di-$C_1$-$C_6$ alkylamino, or 4- to 8-membered cyclic amino, each of which is optionally substituted with one or more halogen atoms), aminocarbonyl$C_1$-$C_6$ alkyl (wherein the amino is —$NH_2$, mono-$C_1$-$C_6$ alkylamino, di-$C_1$-$C_6$ alkylamino, or 4- to 8-membered cyclic amino, each of which is optionally substituted with one or more halogen atoms), optionally protected 4- to 7-membered heterocyclyl$C_1$-$C_6$ alkyl, optionally protected 4- to 7-membered heterocycloalkylidene$C_1$-$C_6$ alkyl, $C_1$-$C_6$ alkoxy$C_1$-$C_6$ alkyl (wherein the $C_1$-$C_6$ alkoxy$C_1$-$C_6$ alkyl is optionally substituted with aminocarbonyl (wherein the amino is —$NH_2$, mono-$C_1$-$C_6$ alkylamino, di-$C_1$-$C_6$ alkylamino, or 4- to 8-membered cyclic amino) or hydroxy), $C_3$-$C_8$ cycloalkyl, $C_3$-$C_8$ cycloalkyl$C_1$-$C_6$ alkyl, $C_2$-$C_6$ alkenyl, $C_2$-$C_6$ alkenyloxycarbonyl$C_1$-$C_6$ alkyl, $C_2$-$C_6$ alkynyl, $C_6$-$C_{10}$ aryloxy$C_1$-$C_6$ alkyl, $C_7$-$C_{14}$ aralkyl (wherein the $C_7$-$C_{14}$ aralkyl is optionally substituted with one or more groups independently selected from the group consisting of halogen, hydroxy, $C_1$-$C_6$ alkyl, $C_1$-$C_6$ haloalkyl, $C_1$-$C_6$ alkoxy, $C_1$-$C_6$ haloalkoxy, and cyano), 5- to 10-membered heteroaryl$C_1$-$C_6$ alkyl (wherein the 5- to 10-membered heteroarylalkyl is optionally substituted with one or more groups selected from the group consisting of $C_1$-$C_6$ alkyl, $C_1$-$C_6$ haloalkyl, $C_1$-$C_6$ alkoxy, and cyano), or 5- to 10-membered heteroaryl$C_1$-$C_6$ alkoxy$C_1$-$C_6$ alkyl optionally substituted with one or more halogen atoms.

$R_5$ is more preferably hydrogen, $C_1$-$C_6$ alkyl, $C_1$-$C_6$ fluoroalkyl, $C_1$-$C_4$ hydroxyalkyl, $C_1$-$C_4$ carboxyalkyl, protected amino$C_1$-$C_4$ alkyl, mono-$C_1$-$C_4$ alkylaminocarbonyl$C_1$-$C_2$ alkyl, di-$C_1$-$C_4$ alkylaminocarbonyl$C_1$-$C_2$ alkyl, 4- to 8-membered cyclic aminocarbonyl$C_1$-$C_2$ alkyl optionally substituted with one or more fluorine atoms, 4- to 8-membered cyclic amino$C_1$-$C_2$ alkyl optionally substituted with one or more fluorine atoms, optionally protected 4- to 7-membered heterocyclyl$C_1$-$C_2$ alkyl, optionally protected 4- to 7-membered heterocycloalkylidene$C_1$-$C_2$ alkyl, mono-$C_1$-$C_4$ alkylaminocarbonylmethyloxy$C_1$-$C_2$ alkyl, $C_1$-$C_4$ alkoxy$C_1$-$C_2$ alkyl optionally substituted with hydroxy, $C_3$-$C_6$ cycloalkyl, $C_3$-$C_6$ cycloalkyl$C_1$-$C_2$ alkyl, $C_2$-$C_6$ alkenyl, $C_2$-$C_3$ alkynyl, $C_2$-$C_3$ alkenyloxycarbonyl$C_1$-$C_2$ alkyl, phenoxy$C_1$-$C_2$ alkyl; benzyl or phenethyl optionally substituted with one or more groups independently selected from the group consisting of halogen, hydroxy, methyl, difluoromethyl, trifluoromethyl, methoxy, trifluoromethoxy, hydroxy, and cyano; 5- to 6-membered heteroaryl$C_1$-$C_2$ alkyl optionally substituted with one or more groups selected from the group consisting of methyl, trifluoromethyl, methoxy, and cyano; or 5- to 6-membered heteroarylmethoxy$C_1$-$C_2$ alkyl optionally substituted with one or more halogen atoms.

In an embodiment, $R_5$ is preferably —$(CH_2)_x$—$O_y$—$(CH_2)_{z1}$—$C_6$-$C_{10}$ aryl or —$(CH_2)_x$—$O_y$—$(CH_2)_{z2}$-5- to 10-membered heteroaryl optionally substituted with one to five groups independently selected from the group consisting of halogen, $C_1$-$C_4$ alkyl (preferably methyl), $C_2$-$C_4$ alkynyl (preferably ethynyl), $C_1$-$C_3$ haloalkyl (preferably difluoromethyl, trifluoromethyl), $C_1$-$C_3$ haloalkoxy (preferably trifluoromethoxy), $C_1$-$C_4$ alkoxy (preferably methoxy), —CN, $C_1$-$C_3$ alkylsulfonyl (preferably methylsulfonyl), hydroxy, and $SF_5$, wherein provided that the sum of x, y, and z1 or z2 is 1 to 4, x is 1, 2, or 3, y is 0 or 1, z1 is 0, 1, 2, or 3, and z2 is 1, 2, or 3. When —$(CH_2)_x$—$O_y$—$(CH_2)_{z1}$—$C_6$-$C_{10}$ aryl has a substituent, the substituent is preferably on $C_6$-$C_{10}$ aryl in the group, and when —$(CH_2)_x$—$O_y$—$(CH_2)_{z2}$-5- to 10-membered heteroaryl has a substituent, the substituent is preferably on 5- to 10-membered heteroaryl in the group.

Specific examples of $R_8$ include hydrogen, methyl, ethyl, i-propyl, n-propyl, n-butyl, 2-methylpropyl, 1-methylpropyl, neopentyl, (2-hydroxy-2-methyl-propyloxy)methyl, (2-(tert-butylamino)-2-oxoethoxy)methyl, 3,3-difluorobutyl, n-propoxymethyl, 3-methylbutoxymethyl, 1-hydroxyethyl, 2-methoxyethyl, 2-methylbutyl, 5,5-difluoropentyl, 3-methylamino-3-oxo-propyl, ((5-fluoripyridin-3-yl)methoxy)methyl, 4-(((allyloxy)carbonyl)amino)butyl, 2-hydroxy-2-oxoethyl, (5-fluoripyridin-3-yl)methyl, 2-(3,3-difluoropiperidinyl)ethyl, 2-(4,4-difluoropiperidinyl)-2-oxo-ethyl, 2-(allyloxy)-2-oxo-ethyl, phenoxymethyl, hydroxymethyl, 2-(tetrahydro-4H-pyran-4-ylidene)ethyl, 2-(tetrahydro-2H-pyran-4-yl)ethyl, 2-(1-(t-butoxycarbonyl)azetidin-3-ylidene)ethyl, 2-(1-(t-butoxycarbonyl)azetidin-3-yl)ethyl, 2-(3,3-difluoro-azetidin-1-yl)-2-oxoethyl, 2-(3,3-difluoro-azetidin-1-yl)-ethyl, 3-(dimethylamino)-3-oxopropyl, 3-(3,3-difluoro-azetidin-1-yl)-3-oxopropyl, 3-(azetidin-1-yl)-3-oxopropyl, 2-(piperidinyl)-2-oxo-propyl, 3-(pyrrolidin-1-yl)-3-oxopropyl, 3-(morpholin-1-yl)-3-oxopropyl, 2-(dimethylamino)-2-oxoethyl, 2-(azetidinyl)-2-oxo-ethyl, 2-(piperidinyl)-2-oxo-ethyl, 2-(pyrrolidinyl)-2-oxo-ethyl, 2-(morpholin-1-yl)-2-oxoethyl, allyl, 2-methylallyl, 3-methylbut-2-en-1-yl, pent-4-en-1-yl, propargyl, 3-allyloxy-3-oxo-propyl, cyclohexyl, cyclopentylmethyl, cyclopropylmethyl, benzyl, phenethyl, 4-chlorobenzyl, 3-cyanobenzyl, 4-ethynylbenzyl, 2-fluorobenzyl, 2-chlorobenzyl, 3-chlorobenzyl, 3-bromobenzyl, 4-bromobenzyl, 2-methylbenzyl, 3-methylbenzyl, 4-methylbenzyl, 4-methoxybenzyl, 3-(trifluoromethoxy)benzyl, 4-(trifluoromethoxy)benzyl, 3,4-difluorobenzyl, 4-iodobenzyl, 4-fluorobenzyl, 4-difluoromethylbenzyl, 3-fluoro-4-hydroxybenzyl, 4-(trifluoromethyl)benzyl, 2-trifluoromethylbenzyl, 2-methoxybenzyl, 3-trifluoromethylbenzyl, 2-(trifluoromethoxy)benzyl, 3-methoxybenzyl, 3-iodobenzyl, 3-fluorobenzyl, pyridin-3-ylmethyl, thiazol-4-ylmethyl, (6-cyanopyridin-3-yl)methyl, (6-methoxypyridin-3-yl)methyl, (6-trifluoromethylpyridin-3-yl)methyl, (5-methylpyridin-3-yl)methyl, (5-methoxypyridin-3-yl)methyl, (pyridin-4-yl)methyl, (6-methylpyridin-3-yl)methyl, 2-(pyridin-3-yl)ethyl, and 2-(pyridin-4-yl)ethyl.

In an embodiment, in formula (1), $R_8$, together with $R_5$, can form $C_4$-$C_8$ alkylene. $C_4$-$C_8$ alkylene is preferably —$(CH_2)_8$—.

In an embodiment, in formula (1), $R_8$ and $P_8$, together with the carbon atom to which $R_8$ is attached and the nitrogen atom to which $P_8$ is attached, can form a 4- to 7-membered saturated heterocyclic ring (preferably 4- or 5-membered saturated heterocyclic ring). The 4- to 7-membered saturated heterocyclic ring may be condensed with a saturated carbocyclic ring or an aromatic ring. The 4- to 7-membered saturated heterocyclic ring is optionally substituted with halogen, oxo, $C_6$-$C_{10}$ aryl, 5- to 10-membered heteroaryl, 4- to 8-membered cyclic amino (wherein the cyclic amino is optionally substituted with one or more halogen atoms), or $OS_8$. Here, $S_8$ is hydrogen, $C_1$-$C_6$ alkyl, $C_1$-$C_6$ haloalkyl, $C_1$-$C_6$ hydroxyalkyl, $C_7$-$C_{14}$ aralkyl (wherein the aralkyl is optionally substituted with one or more halogen atoms, $C_1$-$C_6$ alkyl, $C_1$-$C_6$ alkoxy, or $C_1$-$C_6$ haloalkoxy), or 5- to 10-membered heteroaryl$C_1$-$C_6$ alkyl.

When $R_8$ and $P_8$ form a 4- to 7-membered saturated heterocyclic ring, the 4- to 7-membered saturated heterocyclic ring is preferably an azetidine ring, a pyrrolidine ring, a piperidine ring, a piperazine ring, or a morpholine ring. These saturated heterocyclic rings may be condensed with a 3- to 8-membered saturated carbocyclic ring (preferably a cyclohexane ring) or a 6- to 10-membered aromatic ring (preferably a benzene ring). When the 4- to 7-membered saturated heterocyclic ring has one or more substituents, the 4- to 7-membered saturated heterocyclic ring is preferably substituted one or more halogen atoms, hydroxy, oxo, $C_1$-$C_6$ alkoxy, $C_1$-$C_6$ haloalkoxy, $C_1$-$C_6$ hydroxyalkoxy, $C_6$-$C_{10}$ aryl, 5- to 10-membered heteroaryl$C_1$-$C_6$ alkoxy, $C_7$-$C_{14}$ aralkoxy (wherein the $C_7$-$C_{14}$ aralkoxy is optionally substituted with one or more halogen atoms, $C_1$-$C_6$ alkyl, $C_1$-$C_6$ alkoxy, or $C_1$-$C_6$ haloalkoxy), 4- to 8-membered cyclic amino optionally substituted with one or more halogen atoms, or 5- to 10-membered heteroaryl. More preferable examples of the substituent of the 4- to 7-membered saturated heterocyclic ring include halogen, hydroxy, oxo, ethoxy, 2-hydroxyethyl, phenyl, difluoroethoxy; benzyloxy optionally substituted with one or more substituents independently selected from the group consisting of one or more halogen atoms, methyl, trifluoromethyl, methoxy, and difluoromethoxy; 5- to 6-membered heteroarylmethoxy, 4- to 8-membered cyclic amino optionally substituted with one or more fluorine atoms, phenyl, and 5- to 6-membered heteroaryl.

In an embodiment, in formula (1), $R_8$ and $Q_8$, together with the carbon atom to which they are attached, can form a 3- to 8-membered alicyclic ring or a 4- to 7-membered saturated heterocyclic ring.

When $R_8$ and $Q_8$ form a 3- to 8-membered alicyclic ring or a 4- to 7-membered saturated heterocyclic ring, the 3- to 8-membered alicyclic ring is preferably a cyclopropane ring, a cyclobutane ring, a cyclopentane ring, or a cyclohexane ring, and the 4- to 7-membered saturated heterocyclic ring is preferably a tetrahydrofuran ring or a tetrahydropyran ring.

In an embodiment, in formula (1), except when $R_8$ and $P_8$ form a 4- to 7-membered saturated heterocyclic ring, $P_8$ is hydrogen, $C_1$-$C_6$ alkyl, $C_1$-$C_6$ alkoxy$C_1$-$C_6$ alkyl, $C_2$-$C_6$ alkenyl, $C_1$-$C_6$ alkoxy$C_2$-$C_6$ alkenyl, $C_3$-$C_8$ cycloalkyl, 4- to 7-membered heterocyclyl, 4- to 7-membered heterocyclyl$C_1$-$C_6$ alkyl, $C_6$-$C_{10}$ aryl, $C_7$-$C_{14}$ aralkyl, 5- to 10-membered heteroaryl, or 5- to 10-membered heteroaryl$C_1$-$C_6$ alkyl, each of which is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen or $C_1$-$C_6$ alkyl), and aminocarbonyl (wherein the amino is —$NH_2$, mono-$C_1$-$C_6$ alkylamino, di-$C_1$-$C_6$ alkylamino, or 4- to 8-membered cyclic amino).

$P_8$ is preferably hydrogen, $C_1$-$C_6$ alkyl, $C_1$-$C_6$ hydroxyalkyl, $C_1$-$C_6$ alkoxy$C_1$-$C_6$ alkyl, (wherein the $C_1$-$C_6$ alkoxy$C_1$-$C_6$ alkyl is optionally substituted with one or more halogen atoms, hydroxy, di-$C_1$-$C_6$ alkylaminocarbonyl, $C_1$-$C_6$ alkoxy, or amino (wherein the amino is —$NH_2$, mono-$C_1$-$C_6$ alkylamino, di-$C_1$-$C_6$ alkylamino, or 4- to 8-membered cyclic amino)), aminocarbonyl$C_1$-$C_6$ alkyl (wherein the amino is —$NH_2$, mono-$C_1$-$C_6$ alkylamino, di-$C_1$-$C_6$ alkylamino, or 4- to 8-membered cyclic amino, each of which is optionally substituted with one or more halogen atoms), $C_1$-$C_6$ aminoalkyl (wherein the amino is —$NH_2$, mono-$C_1$-$C_6$ alkylamino, di-$C_1$-$C_6$ alkylamino, or 4- to 8-membered cyclic amino, each of which is optionally substituted with one or more halogen atoms or $C_1$-$C_6$ alkyl), $C_2$-$C_6$ alkenyl, $C_2$-$C_6$ hydroxyalkenyl, aminocarbonyl$C_2$-$C_6$ alkenyl (wherein the amino is —$NH_2$, mono-$C_1$-$C_6$ alkylamino, di-$C_1$-$C_6$ alkylamino, or 4- to 8-membered cyclic amino), $C_1$-$C_6$ alkoxy$C_2$-$C_6$ alkenyl, $C_3$-$C_8$ cycloalkyl optionally substituted with one or more halogen atoms, 4- to 7-membered heterocyclyl, 4- to 7-membered heterocyclyl$C_1$-$C_6$ alkyl, $C_6$-$C_{10}$ aryl optionally substituted with one or more halogen atoms, $C_7$-$C_{14}$ aralkyl, 5- to 10-membered heteroaryl, or 5- to 10-membered heteroaryl$C_1$-$C_6$ alkyl.

$P_8$ is more preferably hydrogen, $C_1$-$C_6$ alkyl, $C_1$-$C_6$ hydroxyalkyl; $C_1$-$C_4$ alkoxy$C_1$-$C_2$ alkyl optionally substituted with one or more fluorine atoms, hydroxy, dimethylaminocarbonyl, methoxy, amino, methylamino, or dimethylamino; dimethylaminocarbonyl$C_1$-$C_4$ alkyl, amino$C_1$-$C_4$ alkyl (wherein the amino is —$NH_2$), 4- to 8-membered cyclic amino$C_1$-$C_4$ alkyl optionally substituted with one or more fluorines or methyl, $C_2$-$C_3$ alkenyl, $C_2$-$C_6$ hydroxyalkenyl, dimethylaminocarbonyl$C_2$-$C_3$ alkenyl, methoxy$C_2$-$C_6$ alkenyl, $C_3$-$C_8$ cycloalkyl optionally substituted with one or more fluorine atoms, 4- to 7-membered heterocyclyl, 4- to 7-membered heterocyclyl$C_1$-$C_2$ alkyl, phenyl optionally substituted with one or more halogen atoms, benzyl, 5- to 6-membered heteroaryl, or 5- to 6-membered heteroaryl$C_1$-$C_2$ alkyl.

Specific examples of $P_8$ include hydrogen, methyl, ethyl, n-butyl, allyl, 2-hydroxyethyl, 2-ethoxyethyl, 2-(dimethylaminocarbonylmethoxy)ethyl, 2-(2-hydroxy-2-methylpropoxy)ethyl, 4-aminobutyl, 2-piperazin-1-ylethyl, 2-(4-methylpiperazin-1-yl)ethyl, 2-(2,2,2-trifluoroethoxy)ethyl, 2-(2-methoxyethoxy)ethyl, 2-(2,2-difluoroethoxy)ethyl, 2-(2-aminoethoxy)ethyl, 2-[2-(methylamino)ethoxy]ethyl, 2-[2-(dimethylamino)ethoxy]ethyl, 5-hydroxypentyl, phenyl, 3-chlorophenyl, 4-chlorophenyl, benzyl, (E)-3-(dimethylaminocarbonyl)-prop-2-en-1-yl, (E)-5-hydroxypent-2-en-1-yl, (E)-4-hydroxy-4-methyl-pent-2-en-1-yl, (E)-5-hydroxy-5-methyl-hex-2-en-1-yl, (E)-4-methoxybut-2-en-1-yl, 3-(dimethylaminocarbonyl)propyl, 2,2-difluorospiro[3.3]heptan-6-yl, 3-thienyl, 3-pyridylmethyl, 2-oxaspiro[3.3]heptan-6-yl, oxetan-3-ylmethyl, 2-(azetidin-3-yl)ethyl, 2-(4,4-difluoro-1-piperidyl)ethyl, and 3-(4,4-difluoro-1-piperidyl)propyl.

In an embodiment, except when $R_8$ and $Q_8$ form a 3- to 8-membered alicyclic ring or a 4- to 7-membered saturated heterocyclic ring, $Q_8$ is hydrogen or $C_1$-$C_6$ alkyl, and preferably hydrogen.

Specific examples of core 8 include MeAla, Ala, Pic(2), MeLeu, EtAla, MeSer(tBuOH), MeSer(NtBu-Aca), MeAla (cPent), MeAla(cPr), MeNva, MeNle, Val, Leu, MeNva(5-F2), MeSer(nPr), MeHnl(7-F2), MeSer(iPen), MeThr, MeHse(Me), Ile, Nle, PRA, Chg, Abu, Hnl(7-F2), Ser(iPen), Algly, Pregly, EtGly, nBuGly, (EtOEt)NGly, Pro, Aze(2), MeGln(Me), MePhe, MePhe(4-Cl), MePhe(3-CN), MePhe (4-CN), MePhe(2-F), MePhe(3-F), MePhe(4-F), MePhe(2-Cl), MePhe(3-Cl), MePhe(3-Br), MePhe(4-Br), MePhe(2-Me), MePhe(3-Me), MePhe(4-Me), MeTyr(Me), MePhe(3-OCF3), MePhe(4-OCF3), MeAlgly, MePhe(34-F2), MeAla (3-Pyr), MePhe(4-I), Phe(4-Me), D-MeAla, Phe(3-Me), Phe, Hph, Phe(4-F), Phe(2-F), Hyp(Et), Tle, Pro(4-F2), Ser(tBuOH), Ser(NtBu-Aca), Ser(3-F-5-Me-Pyr), Glu (OAl), Oic, Hyp, cisHyp, Lys(Alloc), Phe(4-CHF2), Hyp (Bzl), cisHyp(Et), Hyp(Bzl(2-Cl)), cisHyp(Bzl(2-Cl)), cis-Hyp(Bzl(3-Cl)), cisHyp(Bzl(4-Cl)), Hyp(Bzl(3-Cl)), Hyp (Bzl(4-Cl)), Hyp(Bzl(2-Me)), Hyp(Bzl(3-Me)), Hyp(Bzl(3-OMe)), Hyp(Bzl(4-Me)), Hyp(Bzl(4-OCHF2)), cisHyp(Bzl (2-Me)), cisHyp(Bzl(3-Me)), cisHyp(Bzl(3-OMe)), cisHyp (Bzl(4-Me)), cisHyp(Bzl(4-OCHF2)), Methagly, MeAsp, Pro(4-keto), Pic(2)(4-Oxo), Mor(3), Thiopro, MeAla(4-Thz), MeSer(3-F-5-Me-Pyr), MeTyr(3-F), MeAla(3-Pyr-4-CN), Ahpe(2), Hyp(3-Me-Pyr), cisHyp(3-Me-Pyr), cisHyp (Et(2-F2)), Hyp(Et(2-F2)), Tyr(Me), Phe(4-CF3), Phe(4-Cl), Phe(2-CF3), Phe(2-Cl), Phe(2-Me), Phe(2-OMe), Phe(3-CF3), MeAbu(pip-3-F2), MeAsn(pip-4-F2), Pro(4-pip-4-F2), cisPro(4-pip-4-F2), MeAsp(OAl), Pro(4R-Tri), Pro(4S-Tri), Ser(Ph), IDC, Pro(4R-Ph), Pro(4S-Ph), MeAla(3-Pyr-4-OMe), MeAla(3-Pyr-4-CF3), MeAla(3-Pyr-5-Me), MeAla(3-Pyr-5-OMe), MeAla(4-Pyr), MeAla(3-Pyr-4-Me), Hyp(3-thie-Me), PhGly, cisHyp(2-EtOH), Hyp(2-EtOH), Phe(2-OCF3), BnGly, (3-Thienyl)Gly, (Ph-3-Cl)Gly, (Ph-4-Cl)Gly, (F2cBucBu)Gly, (OxeMe)Gly, (OxecBu)Gly, D-Ala, D-MeSer(iPen), D-MeSer, D-Mor(3), D-MePhe, D-MeAbu, MePhe(4-CHF2), MeAbu(3-Pyr), MeAbu(4-Pyr), MeAbu(THPdene), MeAbu(THP), MeAbu(BocAzedene), MeAbu(BocAze), (pip(4-F2)Et)Gly, (pip(4-F2)nPr)Gly, (Et(2-F2)OEt)Gly, (MeOEtOEt)Gly, (Et(2-F3)OEt)Gly, (4-pyr-Et)Gly, (3-pyr-Et)Gly, (4-pyr-Me)Gly, (3-pyr-Me)Gly, AllylGly, (HOEt)Gly, (HOiPrallyl)Gly, (DMFallyl)Gly, (HOEtallyl)Gly, (5-OH-nPent)Gly, MeAsn(Aze-3-F2), MeAbu(Aze-3-F2), (Me2NCOnPr)Gly, (HOt-Buallyl)Gly, (HOtBuOEt)Gly, (DMAOEt)Gly, (MeOMeallyl)Gly, MeGln(Me2), MeGln(Aze-3-F2), MeGln(Aze), MeGln(pip), MeGln(pyrro), MeGln(mor), MeAsn(Me2), MeAsn(Aze), MeAsn(pip), MeAsn(pyrro), MeAsn(mor), MePhe(3-OMe), MePhe(3-I), EtPhe(2-Cl), (4-Me-piz-Et)Gly, (Aze(3)Et)Gly, (H2NEtOEt)Gly, (H2NnBu)Gly, (Me2NEtOEt)Gly, (MeNEtOEt)Gly, and (piz-Et)Gly.

In an embodiment, in formula (1), $R_9$ is hydrogen, $C_1$-$C_6$ alkyl, $C_2$-$C_6$ alkenyl, $C_1$-$C_6$ alkoxy$C_1$-$C_6$ alkyl, $C_3$-$C_8$ cycloalkyl$C_1$-$C_6$ alkyl, $C_7$-$C_{14}$ aralkyl, or 5- to 10-membered heteroaryl$C_1$-$C_6$ alkoxy$C_1$-$C_6$ alkyl, each of which is optionally substituted with one or more groups independently selected from the group consisting of halogen, hydroxy, $C_1$-$C_6$ alkyl, $C_1$-$C_6$ haloalkyl, $C_1$-$C_6$ alkoxy, $C_1$-$C_6$ haloalkoxy, aminocarbonyl (wherein the amino is —$NH_2$, mono-$C_1$-$C_6$ alkylamino, di-$C_1$-$C_6$ alkylamino, or 4- to 8-membered cyclic amino), and $C_1$-$C_6$ alkylsulfonyl.

$R_9$ is preferably hydrogen, $C_1$-$C_6$ alkyl, $C_1$-$C_6$ haloalkyl, $C_2$-$C_6$ alkenyl, $C_1$-$C_6$ alkoxy$C_1$-$C_6$ alkyl (wherein the $C_1$-$C_6$ alkoxy$C_1$-$C_6$ alkyl is optionally substituted with aminocarbonyl (wherein the amino is —$NH_2$, mono-$C_1$-$C_6$ alkylamino, di-$C_1$-$C_6$ alkylamino, or 4- to 8-membered cyclic amino), hydroxy, or 5- to 10-membered heteroaryl optionally substituted with one or more halogen atoms), $C_3$-$C_8$ cycloalkyl$C_1$-$C_6$ alkyl, or $C_7$-$C_{14}$ aralkyl (wherein the $C_7$-$C_{14}$ aralkyl is optionally substituted with one or more groups independently selected from the group consisting of one or more halogen atoms, $C_1$-$C_6$ alkyl, $C_1$-$C_6$ haloalkyl, $C_1$-$C_6$ alkoxy, $C_1$-$C_6$ haloalkoxy, and cyano).

$R_9$ is more preferably hydrogen, $C_1$-$C_6$ alkyl, $C_1$-$C_6$ fluoroalkyl, $C_2$-$C_3$ alkenyl; $C_1$-$C_6$ alkoxy$C_1$-$C_2$ alkyl optionally substituted with mono-$C_1$-$C_4$ alkylaminocarbonyl, hydroxy, or 5- to 6-membered heteroaryl optionally substituted with one or more fluorine atoms; and benzyl or phenethyl optionally substituted with one or more groups independently selected from the group consisting of $C_3$-$C_6$ cycloalkyl$C_1$-$C_2$ alkyl, halogen, methyl, trifluoromethyl, methoxy, trifluoromethoxy, and cyano.

More specific examples of $R_9$ include hydrogen, methyl, ethyl, i-propyl, 2-methylpropyl, 2,2,2-trifluoroethyl, 5,5-difluoropentyl, methoxymethyl, n-propoxymethyl, 3-methylbutoxymethyl, 3-(dimethylamino)3-oxopropyl, (2-hydroxy-2-methyl-propyloxy)methyl, (2-(tert-butylamino)-2-oxoethoxy)methyl, (5-fluoropyridin-3-yl)methyl, allyl, cyclohexylmethyl, benzyl, phenethyl, 2-chlorobenzyl, 3-chlorobenzyl, 4-chlorobenzyl, 2-fluorobenzyl, 3-fluorobenzyl, 4-fluorobenzyl, 2-methylbenzyl, 4-methylbenzyl, 2-methoxybenzyl, 4-methoxybenzyl, 2-(trifluoromethyl) benzyl, 3-(trifluoromethyl)benzyl, 4-(trifluoromethyl)benzyl, 2-(trifluoromethoxy)benzyl, 3-(trifluoromethoxy)benzyl, and 4-(trifluoromethoxy)benzyl.

In an embodiment, in formula (1), $R_9$ and $P_9$, together with the carbon atom to which $R_9$ is attached and the nitrogen atom to which $P_9$ is attached, can form a 4- to 7-membered saturated heterocyclic ring.

When $R_9$ and $P_9$ form a 4- to 7-membered saturated heterocyclic ring, the 4- to 7-membered saturated heterocyclic ring is preferably an azetidine ring, a pyrrolidine ring, a piperidine ring, a piperazine ring, or a morpholine ring.

In an embodiment, in formula (1), $R_9$ and $Q_9$, together with the carbon atom to which they are attached, can form a 3- to 8-membered alicyclic ring or a 4- to 7-membered saturated heterocyclic ring.

When $R_9$ and $Q_9$ form a 3- to 8-membered alicyclic ring or a 4- to 7-membered saturated heterocyclic ring, the 3- to 8-membered alicyclic ring is preferably a cyclopropane ring, a cyclobutane ring, a cyclopentane ring, or a cyclohexane ring, and the 4- to 7-membered saturated heterocyclic ring is preferably a tetrahydrofuran ring or a tetrahydropyran ring.

In an embodiment, in formula (1), except when $R_9$ and $P_9$ form a 4- to 7-membered saturated heterocyclic ring, $P_9$ is hydrogen or $C_1$-$C_6$ alkyl, wherein the $C_1$-$C_6$ alkyl is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino). $P_9$ is preferably hydrogen or $C_1$-$C_6$ alkyl, and more preferably hydrogen, methyl, n-propyl, or n-butyl.

In an embodiment, except when $R_9$ and $Q_9$ form a 3- to 8-membered alicyclic ring or a 4- to 7-membered saturated heterocyclic ring, $Q_9$ is hydrogen or $C_1$-$C_6$ alkyl, and preferably hydrogen or methyl.

Regarding $R_9$ and $Q_9$, preferably, $R_9$ is $C_1$-$C_6$ alkyl, $C_2$-$C_6$ alkenyl, or $C_7$-$C_{14}$ aralkyl, and $Q_9$ is $C_1$-$C_6$ alkyl; or $R_9$ and $Q_9$, together with the carbon atom to which they are attached, form a 3- to 8-membered alicyclic ring or a 4- to 7-membered saturated heterocyclic ring.

Specific examples of core 9 include MeAla, Ala, MeLeu, MeCha, MeVal, MeSer(tBuOH), MeSer(NtBu-Aca), Val, Leu, MeSer(nPr), MeHnl(7-F2), MeSer(iPen), Ser(nPr), Abu(4-F3), Abu, Ser(Me), Gly, nBuGly, nPrGly, MePhe, MeHph, MePhe(4-Cl), MePhe(2-F), MePhe(3-F), MePhe(4-F), MePhe(2-Cl), MePhe(3-Cl), MePhe(2-Me), MePhe(4-Me), MePhe(2-CF3), MePhe(3-CF3), MePhe(4-CF3), MeTyr(Me), MePhe(2-OCF3), MePhe(3-OCF3), MePhe(4-OCF3), D-Pro, Phe, Ser(NtBu-Aca), MeSer(3-F-5-Me-Pyr), D-Ala, MeGln(Me2), MeAib, Aib, cLeu, cHex, cVal, (Me)Phe, MecLeu, D-(Me)Abu, D-(Me)Algly, 1-ACPrC, (Me)Abu, (Me)Algly, (Me)Leu, Athpc, MePhe(2-OMe), Me(Me)Phe, D-Val, and D-Algly.

In an embodiment, in formula (1), $R_{10}$ is $C_1$-$C_6$ alkyl, $C_2$-$C_6$ alkynyl, $C_1$-$C_6$ alkoxy$C_1$-$C_6$ alkyl, $C_3$-$C_8$ cycloalkyl, $C_3$-$C_8$ cycloalkyl$C_1$-$C_6$ alkyl, $C_3$-$C_8$ cycloalkoxy$C_1$-$C_6$ alkyl, or $C_7$-$C_{14}$ aralkyl, each of which is optionally substituted with one or more groups independently selected from the group consisting of halogen, hydroxy, and $C_1$-$C_6$ alkylsulfonyl.

$R_{10}$ is preferably $C_1$-$C_6$ alkyl, $C_1$-$C_6$ haloalkyl, $C_1$-$C_6$ hydroxyalkyl, $C_1$-$C_6$ alkylsulfonyl$C_1$-$C_6$ alkyl, $C_2$-$C_6$ alkynyl, $C_1$-$C_6$ alkoxy$C_1$-$C_6$ alkyl optionally substituted with one or more halogen atoms, $C_3$-$C_8$ cycloalkyl, $C_3$-$C_8$ cycloalkyl$C_1$-$C_6$ alkyl, $C_3$-$C_8$ cycloalkoxy$C_1$-$C_6$ alkyl, or $C_7$-$C_{14}$ aralkyl.

$R_{10}$ is more preferably $C_1$-$C_6$ alkyl, $C_1$-$C_6$ fluoroalkyl, $C_1$-$C_4$ hydroxyalkyl, methylsulfonyl$C_1$-$C_2$ alkyl, $C_2$-$C_3$ alkynyl, $C_1$-$C_4$ alkoxy$C_1$-$C_2$ alkyl optionally substituted with one or more fluorine atoms, $C_3$-$C_6$ cycloalkyl, $C_3$-$C_6$ cycloalkyl$C_1$-$C_2$ alkyl, $C_3$-$C_6$ cycloalkoxy$C_1$-$C_2$ alkyl, benzyl, or phenethyl.

More specific examples of $R_{10}$ include methyl, ethyl, n-propyl, i-propyl, 2-methylpropyl, 1-methylpropyl, n-butyl, 2-methylbutyl, 3-methylbutyl, n-pentyl, propargyl, 3,3-difluorobutyl, 5,5-difluoropentyl, methoxymethyl, 1-methoxyethyl, 2-methoxyethyl, n-propoxymethyl, 1-hydroxyethyl, cyclopropoxymethyl, cyclobutoxymethyl, (2,2,2-trifluoroethoxy)methyl, 2-methylsulfonylethyl, cyclopropyl, cyclobutyl, cyclopentyl, cyclohexyl, cyclopropylmethyl, cyclobutylmethyl, cyclopentylmethyl, cyclohexylmethyl, benzyl, and phenethyl.

In an embodiment, in formula (1), $R_{10}$ and $P_{10}$, together with the carbon atom to which $R_{10}$ is attached and the nitrogen atom to which $P_{10}$ is attached, can form a 4- to 7-membered saturated heterocyclic ring.

When $R_{10}$ and $P_{10}$ form a 4- to 7-membered saturated heterocyclic ring, the 4- to 7-membered saturated heterocyclic ring is preferably an azetidine ring, a pyrrolidine ring, a piperidine ring, a piperazine ring, or a morpholine ring.

In an embodiment, in formula (1), $R_{10}$ and $Q_{10}$, together with the carbon atom to which they are attached, can form a 3- to 8-membered alicyclic ring or a 4- to 7-membered saturated heterocyclic ring.

When $R_{10}$ and $Q_{10}$ form a 3- to 8-membered alicyclic ring or a 4- to 7-membered saturated heterocyclic ring, the 3- to 8-membered alicyclic ring is preferably a cyclopropane ring, a cyclobutane ring, a cyclopentane ring, or a cyclohexane ring, and the 4- to 7-membered saturated heterocyclic ring is preferably a tetrahydrofuran ring or a tetrahydropyran ring.

In an embodiment, in formula (1), except when $R_{10}$ and $P_{10}$ form a 4- to 7-membered saturated heterocyclic ring, $P_{10}$ is hydrogen or $C_1$-$C_6$ alkyl, wherein the $C_1$-$C_6$ alkyl is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino). $P_{10}$ is preferably hydrogen or $C_1$-$C_2$ alkyl, and specific examples include hydrogen and methyl.

In an embodiment, except when $R_{10}$ and $Q_{10}$ form a 3- to 8-membered alicyclic ring or a 4- to 7-membered saturated heterocyclic ring, $Q_{10}$ is hydrogen or $C_1$-$C_6$ alkyl, and preferably hydrogen.

Specific examples of core 10 include MeAla, MeLeu, MeCha, MeVal, MeAla(cPent), MeAla(cBu), MeAla(cPr), MeChg, MeGly(cPent), MeGly(cBu), MeGly(cPr), MeAbu, MeNva, MeNle, Val, Leu, MeNva(5-F2), MeHle, MeIle, MeSer(nPr), MeSer(cPr), MeHnl, MeHnl(7-F2), MePRA, MeSer(Me), MeThr, MeSer(cBu), MeSer(Tfe), MeThr(Me), MeHse(Me), MeMet(O2), Ile, Nle, Chg, Ala(cBu), Gly (cPent), Hle, Nva, Phe, and Hph.

In an embodiment, in formula (1), $R_{11}$ is hydrogen, $C_1$-$C_6$ alkyl, $C_2$-$C_6$ alkenyl, $C_2$-$C_6$ alkynyl, $C_1$-$C_6$ alkoxy$C_1$-$C_6$ alkyl, $C_7$-$C_{14}$ aralkyl, or aminocarbonyl (wherein the amino is —$NH_2$, mono $C_1$-$C_6$ alkylamino, di-$C_1$-$C_6$ alkylamino, or 4- to 8-membered cyclic amino), each of which is optionally substituted with one or more groups independently selected from the group consisting of halogen, oxo, hydroxy, $C_1$-$C_6$ alkyl, 4- to 7-membered heterocyclyl, aminocarbonyl (wherein the amino is —$NH_2$, mono-$C_1$-$C_6$ alkylamino, di-$C_1$-$C_6$ alkylamino, or 4- to 8-membered cyclic amino), and $C_1$-$C_6$ alkylsulfonyl; or $R_{11}$ is a peptide chain containing 1 to 4 amino acid residues. When $R_{11}$ is a peptide chain containing 1 to 4 amino acid residues, the 1 to 4 amino acid residues constituting the peptide chain may be natural amino acid residues or non-natural amino acid residues, and may be the same or different.

When core 11 is α-amino acid (i.e., $L_{11}$ is a single bond), $R_{11}$ is preferably hydrogen, $C_1$-$C_6$ alkoxy$C_1$-$C_6$ alkyl optionally substituted with hydroxy, or $C_7$-$C_{14}$ aralkyl optionally substituted with one or more halogen atoms.

When core 11 is α-amino acid, $R_{11}$ is more preferably hydrogen, $C_1$-$C_6$ alkoxy$C_1$-$C_2$ alkyl optionally substituted with hydroxy, or benzyl optionally substituted with fluorine, and specific examples include hydrogen, (2-hydroxy-2-methyl-propyloxy)methyl, benzyl, 3-fluorobenzyl, and 4-fluorobenzyl.

When core 11 is R-amino acid (i.e., $L_{11}$ is —$CHM_{11}$-), $R_{11}$ is preferably hydrogen, $C_1$-$C_6$ alkyl, $C_1$-$C_6$ haloalkyl, $C_2$-$C_6$ alkenyl, $C_2$-$C_6$ alkynyl, $C_1$-$C_6$ alkoxy$C_1$-$C_6$ alkyl (wherein the $C_1$-$C_6$ alkoxy$C_1$-$C_6$ alkyl is optionally substituted with hydroxy or aminocarbonyl (wherein the amino is —$NH_2$, mono-$C_1$-$C_6$ alkylamino, di-$C_1$-$C_6$ alkylamino, or 4- to 8-membered cyclic amino)), $C_7$-$C_{14}$ aralkyl optionally substituted with one or more halogen atoms, or aminocarbonyl (wherein the amino is —$NH_2$, mono-$C_1$-$C_6$ alkylamino, di-$C_1$-$C_6$ alkylamino, or 4- to 8-membered cyclic amino, and the cyclic amino may be further substituted with one or more halogen atoms, one or more oxo groups, one or more $C_1$-$C_6$ alkyl groups, or 4- to 7-membered heterocyclyl).

When core 11 is R-amino acid, $R_{11}$ is more preferably hydrogen, $C_1$-$C_6$ alkyl, $C_1$-$C_6$ fluoroalkyl, $C_2$-$C_3$ alkenyl, $C_2$-$C_3$ alkynyl, $C_1$-$C_6$ alkoxy$C_1$-$C_2$ alkyl optionally substituted with mono-$C_1$-$C_4$ alkylaminocarbonyl, dimethylaminocarbonyl; 4- to 8-membered cyclic aminocarbonyl optionally substituted with one or more fluorine atoms, $C_1$-$C_4$ alkyl, or 4- to 7-membered heterocyclyl; benzyl or phenethyl.

When core 11 is R-amino acid, specific examples of $R_{11}$ include hydrogen, methyl, isobutyl, trifluoromethyl, allyl, prop-2-yn-1-yl, (isopentyloxy)methyl, {2-(t-butylamino)-2-oxoethoxy}methyl, dimethylaminocarbonyl, azetidinylcarbonyl, pyrrolidinylcarbonyl, 3,3-dimethylpyrrolidinylcarbonyl, 3,3,4,4-tetrafluoropyrrolidinylcarbonyl, 4-methylpiperidinylcarbonyl, 4-(t-butyl)-piperidinylcarbonyl, 3,3,4,4,5,5-hexafluoropiperidinylcarbonyl, 3,3-difluoropiperidinylcarbonyl, 4,4-difluoropiperidinylcarbonyl, piperidinylcarbonyl, morpholinocarbonyl, oxazolidin-3-ylcarbonyl, 3-oxa-8-azabicyclo[3.2.1]octan-8-ylcarbonyl, 1,1-dioxidethiomorpholinylcarbonyl, 1-(oxetan-3-yl)-piperazin-4-ylcarbonyl, and phenethyl.

When $L_1$ of core 11 is —$(CH_2)_nS(CH_2)_m$—, —$(CH_2)_nS(O)(CH_2)_m$, or —$(CH_2)_nS(O)_2(CH_2)_m$—, $R_{11}$ is preferably aminocarbonyl (wherein the amino is —$NH_2$, mono-$C_1$-$C_6$ alkylamino, di-$C_1$-$C_6$ alkylamino, or 4- to 8-membered cyclic amino).

In an embodiment, in formula (1), $R_{11}$ and $P_{11}$, together with the carbon atom to which $R_{11}$ is attached and the nitrogen atom to which $P_{11}$ is attached, can form a 4- to 7-membered saturated heterocyclic ring.

When $R_{11}$ and $P_{11}$ form a 4- to 7-membered saturated heterocyclic ring, the 4- to 7-membered saturated heterocyclic ring is preferably an azetidine ring, a pyrrolidine ring, a piperidine ring, a piperazine ring, or a morpholine ring.

In an embodiment, in formula (1), $R_{11}$ and $Q_{11}$, together with the carbon atom to which they are attached, can form a 3- to 8-membered alicyclic ring or a 4- to 7-membered saturated heterocyclic ring.

When $R_{11}$ and $Q_{11}$ form a 3- to 8-membered alicyclic ring or a 4- to 7-membered saturated heterocyclic ring, the 3- to 8-membered alicyclic ring is preferably a cyclopropane ring, a cyclobutane ring, a cyclopentane ring, or a cyclohexane ring, and the 4- to 7-membered saturated heterocyclic ring is preferably a tetrahydrofuran ring or a tetrahydropyran ring.

In an embodiment, in formula (1), when core 11 is R-amino acid, $R_{11}$ and $M_{11}$, together with the carbon atom to which $R_{11}$ is attached and the carbon atom to which $M_{11}$ is attached, can form a 3- to 8-membered alicyclic ring.

When $R_{11}$ and $M_{11}$ form a 3- to 8-membered alicyclic ring, the 3- to 8-membered alicyclic ring is preferably a cyclopentane ring or a cyclohexane ring.

In an embodiment, in formula (1), when core 11 is β-amino acid, $M_{11}$ is hydrogen except when $R_{11}$ and $M_{11}$ form a 3- to 8-membered alicyclic ring.

In an embodiment, in formula (1), except when $R_{11}$ and $P_{11}$ form a 4- to 7-membered saturated heterocyclic ring, $P_{11}$ is hydrogen or $C_1$-$C_6$ alkyl, wherein the $C_1$-$C_6$ alkyl is optionally substituted with one or more groups independently selected from the group consisting of halogen, hydroxy, $C_1$-$C_6$ alkoxy, amino (wherein the amino is —$NH_2$, mono-$C_1$-$C_6$ alkylamino, di-$C_1$-$C_6$ alkylamino, or 4- to 8-membered cyclic amino, each of which is optionally substituted with halogen), and aminocarbonyl (wherein the amino is —$NH_2$, mono-$C_1$-$C_6$ alkylamino, di-$C_1$-$C_6$ alkylamino, or 4- to 8-membered cyclic amino).

$P_{11}$ is preferably hydrogen or $C_1$-$C_6$ alkyl. Specific examples of such $P_{11}$ include hydrogen, methyl, ethyl, and n-propyl.

In an embodiment, except when $R_{11}$ and $Q_{11}$ form a 3- to 8-membered alicyclic ring or a 4- to 7-membered saturated heterocyclic ring, $Q_1$ is hydrogen or $C_1$-$C_6$ alkyl, and preferably hydrogen.

In an embodiment, $R_{11}$ is preferably —$CONR_{11A}R_{11B}$, wherein $R_{11A}$ and $R_{11B}$ are each independently hydrogen or $C_1$-$C_6$ alkyl (preferably methyl), or $R_{11A}$ and $R_{11B}$, together with the nitrogen atom to which they are attached, form a 4- to 8-membered saturated heterocyclic ring. The 4- to 8-membered saturated heterocyclic ring is optionally substituted with one or more groups independently selected from the group consisting of one or more halogen atoms (preferably fluorine), one or more oxo groups, one or more $C_1$-$C_6$ alkyl groups (preferably $C_1$-$C_4$ alkyl), and 4- to 7-membered heterocyclyl (preferably oxetan-3-yl).

When core 11 is α-amino acid, specific examples of core 11 include MeSer(tBuOH), MeGly, MePhe, MePhe(3-F), MePhe(4-F), and D-MePhe.

When core 11 is β-amino acid, specific examples of core 11 include bAla, bMeAla, 2-ACHxC, 2-ACPnC, 3-CF3-bAla, Asp-mor, Asp-mor(26-bicyc), Asp-mor(SO2), Asp-NMe2, Asp-oxz, Asp-pip, Asp-pip(345-F6), Asp-pip(4-Me), Asp-pip-tBu, Asp-piz(oxe), Asp-pyrro, Asp-pyrro(34-F4), Asp-pyrro(3-Me2), D-(Propargyl)Gly-(C#CH2), D-3-Abu, D-3-MeAbu, D-Gly(Allyl)-(C#CH2), D-Hph-(C#CH2), D-Leu-(C#CH2), D-MeAsp-pyrro, D-MeLeu-(C#CH2), D-Pic(2)-(C#CH2), D-Pro-(C#CH2), D-Ser(iPen)-(C#CH2), D-Ser(NtBu-Aca)-(C#CH2), EtAsp-pip, MeAsp-aze, MeAsp-mor, MeAsp-mor(26-bicyc), MeAsp-mor(SO2), MeAsp-NMe2, MeAsp-oxz, MeAsp-pip, MeAsp-pip(345-F6), MeAsp-pip(3-F2), MeAsp-pip(4-F2), MeAsp-pip(4-Me), MeAsp-piz(oxe), MeAsp-pyrro, MeAsp-pyrro(34-F4), MeAsp-pyrro(3-Me2), and nPrAsp-pip.

When $L_{11}$ is —$(CH_2)_nS(CH_2)_m$—, —$(CH_2)_nS(O)(CH_2)_m$—, or —$(CH_2)_nS(O)_2(CH_2)_m$—, specific examples of core 11 include MeCys(AcOH)—NMe2.

In an embodiment, in formula (1), at least three of $P_1$ to $P_{11}$ are not hydrogen.

In an embodiment, in formula (1), at least three, at least four, at least five, or at least six of $P_1$ to $P_{11}$ are preferably $C_1$-$C_6$ alkyl, wherein the $C_1$-$C_6$ alkyl is preferably methyl or ethyl.

In an embodiment, the present invention can be a compound having formula (1) wherein one of —$CO$-$L_1$- and —$CO$-$L_1$- is replaced with —$(CH_2)nC{\equiv}CCH_2S(CH_2)_m$—, —$(CH_2)_nCH{=}CHCH_2S(CH_2)_m$—, or —$(CH_2)_{n+3}S(CH_2)_m$—, wherein n is 1, 2, or 3, and m is 1 or 2. —S— may be oxidized to be —$S(O)$— or —$S(O)_2$—. Here, when —$CO$-$L_1$- is replaced with —$(CH_2)_nC{\equiv}CCH_2S(CH_2)_m$—, —$(CH_2)_nCH{=}CHCH_2S(CH_2)_m$—, or —$(CH_2)_{n+3}S(CH_2)_m$—, $L_{11}$ is a single bond, and when —$CO$-$L_{11}$- is replaced with —$(CH_2)_nC{\equiv}CCH_2S(CH_2)_m$—, —$(CH_2)_nCH{=}CHCH_2S(CH_2)_m$—, or —$(CH_2)_{n+3}S(CH_2)_m$—, $L_1$ is a single bond. Groups other than $L_1$ and $L_{11}$ in formula (1) are as described above.

In an embodiment, the present invention relates to a cyclic peptide compound represented by formula (1') below or a salt thereof, or a solvate thereof.

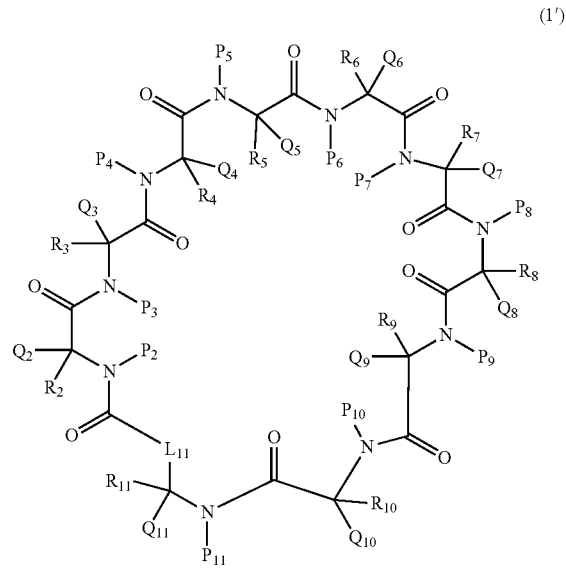

(1')

In formula (1'),
$L_{11}$ is —$CHM_{11}$-, —$(CH_2)_nS(CH_2)_m$—, —$(CH_2)_nS(O)(CH_2)_m$—, or —$(CH_2)_nS(O)_2(CH_2)_m$—,
n and m are each independently 1 or 2,
the definitions of $R_2$ to $R_{11}$, $P_2$ to $P_{11}$, $Q_2$ to $Q_{11}$, and $M_{11}$ are the same as the definitions of $R_2$ to $R_{11}$, $P_2$ to $P_{11}$, $Q_2$ to $Q_{11}$, and $M_{11}$ in formula (1), respectively.

In formula (1'), the ring is composed of 10 amino acid residues. As in formula (1), the amino acid residue having $P_2$, $Q_2$, and $R_2$ in the formula may be referred to as core 2, the amino acid residue having $P_3$, $Q_3$, and $R_3$ as core 3, the amino acid residue having $P_4$, $Q_4$, and $R_4$ as core 4, the amino acid residue having $P_5$, $Q_5$, and $R_5$ as core 5, the amino acid residue having $P_6$, $Q_6$, and $R_6$ as core 6, the amino acid residue having $P_7$, $Q_7$, and $R_7$ as core 7, the amino acid residue having $P_8$, $Q_8$, and $R_8$ as core 8, the amino acid residue having $P_9$, $Q_9$, and $R_9$ as core 9, the amino acid residue having $P_{10}$, $Q_{10}$, and $R_{10}$ as core 10, and the amino acid residue having $P_{11}$, $Q_{11}$, $R_{11}$, and $L_{11}$ as core 11.

In an embodiment, in formula (1'), $L_{11}$ is —$CHM_{11}$-, —$(CH_2)_nS(CH_2)_m$—, —$(CH_2)_nS(O)(CH_2)_m$—, or —$(CH_2)_nS(O)_2(CH_2)_m$—. $M_1$ is the same as $M_1$ in formula (1).

When $L_{11}$ is —$CHM_{11}$-, $M_1$ can be hydrogen, or $M_1$ can, together with $R_1$, the carbon atom to which $R_1$ is attached, and the carbon atom to which Mu is attached, form a 3- to 8-membered alicyclic ring. The 3- to 8-membered alicyclic ring is preferably a cyclopentane ring or a cyclohexane ring.

When $L_{11}$ is —$(CH_2)_nS(CH_2)_m$—, specific examples of —$(CH_2)_nS(CH_2)_m$— include —$CH_2SCH_2$—, —$CH_2CH_2SCH_2$—, —$CH_2SCH_2CH_2$—, and —$CH_2CH_2SCH_2CH_2$—.

When $L_{11}$ is —$(CH_2)_nS(O)(CH_2)_m$—, specific examples of —$(CH_2)_nS(O)(CH_2)_m$— include —$CH_2S(O)CH_2$—, —$CH_2CH_2S(O)CH_2$—, —$CH_2S(O)CH_2CH_2$—, and —$CH_2CH_2S(O)CH_2CH_2$—.

When $L_{11}$ is —$(CH_2)_nS(O)_2(CH_2)_m$—, specific examples of —$(CH_2)_nS(O)_2(CH_2)_m$— include —$CH_2S(O)_2CH_2$—, —$CH_2CH_2S(O)_2CH_2$—, —$CH_2S(O)_2CH_2CH_2$—, and —$CH_2CH_2S(O)_2CH_2CH_2$—.

When $L_{11}$ is —$(CH_2)_nS(CH_2)_m$—, —$(CH_2)_nS(O)(CH_2)_m$—, or —$(CH_2)_nS(O)_2(CH_2)_m$—, $R_{11}$ is preferably aminocarbonyl (wherein the amino is —$NH_2$, mono-$C_1$-$C_6$ alkylamino, di-$C_1$-$C_6$ alkylamino, or 4- to 8-membered cyclic amino).

When $L_{11}$ is —$(CH_2)_nS(CH_2)_m$—, —$(CH_2)_nS(O)(CH_2)_m$—, or —$(CH_2)_nS(O)_2(CH_2)_m$—, $R_{11}$ is more preferably —$CONR_{11A}R_{11b}$, wherein $R_{11A}$ and $R_{11B}$ are each independently hydrogen or $C_1$-$C_6$ alkyl (preferably methyl), or $R_{11A}$ and $R_{11B}$, together with the nitrogen atom to which they are attached, form a 4- to 8-membered saturated heterocyclic ring. The 4- to 8-membered saturated heterocyclic ring is optionally substituted with one or more groups independently selected from the group consisting of one or more halogen atoms (preferably fluorine atom(s)), one or more oxo groups, one or more $C_1$-$C_6$ alkyl groups (preferably $C_1$-$C_4$ alkyl group(s)), and 4- to 7-membered heterocyclyl (preferably oxetan-3-yl). Specific examples of $R_{11}$ include dimethylaminocarbonyl.

When $L_{11}$ is —$(CH_2)_nS(CH_2)_m$—, —$(CH_2)_nS(O)(CH_2)_m$—, or —$(CH_2)_nS(O)_2(CH_2)_m$—, $Q_{11}$ is preferably hydrogen or $C_1$-$C_6$ alkyl, and more preferably hydrogen.

When $L_{11}$ is —$(CH_2)_nS(CH_2)_m$—, —$(CH_2)_nS(O)(CH_2)_m$—, or —$(CH_2)_nS(O)_2(CH_2)_m$—, $P_{11}$ is preferably hydrogen or $C_1$-$C_6$ alkyl. Specific examples of such $P_{11}$ include hydrogen, methyl, ethyl, and n-propyl.

When $L_{11}$ is —$(CH_2)_nS(CH_2)_m$—, —$(CH_2)_nS(O)(CH_2)_m$—, or —$(CH_2)_nS(O)_2(CH_2)_m$—, specific examples of core 11 include MeCys(AcOH)—NMe2.

Preferable groups in each of cores 2 to 11 in formula (1') may be the same as the preferable groups in each corresponding core in formula (1). Further, the specific amino acids listed above as cores 2 to 11 of formula (1) can be used as amino acids of each corresponding core of formula (1').

Specific examples of the cyclic peptide compound represented by formula (1') include the following:

(2172) (3S,9S,18S,24R,27S,33S)-18-[(2S)-butan-2-yl]-3-[2-[3-chloro-4-(trifluoromethyl)phenyl]ethyl]-9-(cyclohexylmethyl)-27-cyclopentyl-N,N,7,10,13,16,25,28-octamethyl-2,5,8,11,14,17,20,26,29,32-decaoxospiro[22-thia-1,4,7,10,13,16,19,25,28,31-decazabicyclo[31.3.0]hexatriacontane-30,1'-cyclopentane]-24-carboxamide, and (2173) (3S,9S,18S,24R,27S,33S)-18,27-bis[(2S)-butan-2-yl]-3-[2-[3-chloro-4-(trifluoromethyl)phenyl]ethyl]-N,N,7,10,13,16,25,28-octamethyl-9-[(4-methylphenyl)methyl]-2,5,8,11,14,17,20,26,29,32-decaoxospiro[22-thia-1,4,7,10,13,16,19,25,28,31-decazabicyclo[31.3.0]hexatriacontane-30,1'-cyclopentane]-24-carboxamide.

In an embodiment, the present invention can be a cyclic peptide compound represented by formula (2) below that further specifies formula (1) above.

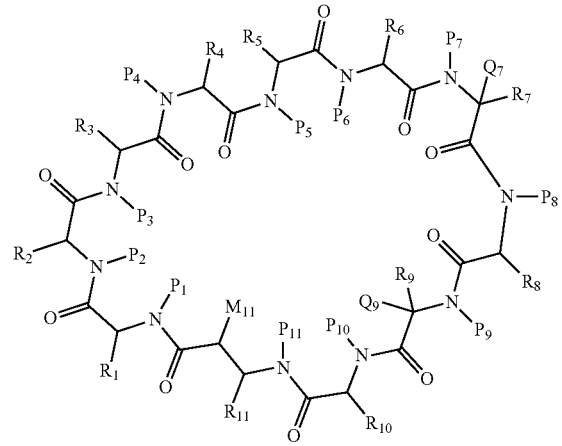

(2)

The definition of each group in formula (2) is the same as the definition of each group in formula (1). The cyclic peptide compound represented by formula (2) preferably has each of the following groups.

$R_1$ is $C_1$-$C_6$ alkyl (preferably $C_1$-$C_4$ alkyl, and more preferably methyl or 2-methylpropyl), and $P_1$ is $C_1$-$C_6$ alkyl (preferably $C_1$-$C_3$ alkyl, and more preferably methyl), and/or $R_2$ is $C_1$-$C_6$ alkyl (preferably $C_3$-$C_6$ alkyl, and more preferably 1-methylpropyl), and $P_2$ is hydrogen or $C_1$-$C_6$ alkyl (preferably hydrogen or $C_1$-$C_3$ alkyl, and more preferably hydrogen or methyl), and/or $R_3$ is hydrogen or $C_1$-$C_6$ alkyl (preferably $C_1$-$C_3$ alkyl, and more preferably methyl), and $P_3$ is hydrogen or $C_1$-$C_6$ alkyl (preferably $C_1$-$C_3$ alkyl, and more preferably methyl), and/or $R_4$ is hydrogen, and $P_4$ is $C_1$-$C_6$ alkyl (preferably $C_1$-$C_3$ alkyl, and more preferably methyl), or $R_4$ and $P_4$, together with the carbon atom to which $R_4$ is attached and the nitrogen atom to which $P_4$ is attached, form a 4- to 7-membered saturated heterocyclic ring (preferably, an azetidine ring, a pyrrolidine ring, or a piperidine ring, and more preferably an azetidine ring or a pyrrolidine ring), and/or $R_5$ is $C_1$-$C_6$ alkoxy$C_1$-$C_6$ alkyl (preferably $C_2$-$C_6$alkoxy $C_1$-$C_2$ alkyl, and more preferably $C_3$-$C_8$ alkoxymethyl); $C_7$-$C_{14}$ aralkyl (preferably benzyl or phenethyl, and more preferably benzyl) optionally substituted with a group independently selected from the group consisting of halogen (preferably fluorine or chlorine), $C_1$-$C_6$ alkyl (preferably $C_1$-$C_3$ alkyl, and more preferably methyl), $C_1$-$C_6$ haloalkyl (preferably $C_1$-$C_3$ fluoroalkyl, and more preferably trifluoromethyl), and $C_1$-$C_6$ alkoxy (preferably $C_1$-$C_3$ alkoxy, and more preferably methoxy); $C_3$-$C_8$ cycloalkyl (preferably $C_3$-$C_6$ cycloalkyl, and more preferably $C_5$-$C_6$ cycloalkyl), or $C_3$-$C_8$ cycloalkyl$C_1$-$C_6$ alkyl (preferably $C_3$-$C_6$ cycloalkyl$C_1$-$C_2$ alkyl, more preferably $C_5$-$C_6$ cycloalkylmethyl, and even more preferably cyclohexylmethyl), and $P_5$ is $C_1$-$C_2$ alkyl (preferably methyl or ethyl), and/or $R_6$ is hydrogen or $C_1$-$C_6$ alkyl (preferably $C_1$-$C_3$ alkyl, and more preferably methyl), and $P_6$ is $C_1$-$C_6$ alkyl (preferably $C_1$-$C_3$ alkyl, and more preferably methyl or ethyl), or $R_6$ and $P_6$, together with the carbon atom to which $R_6$ is attached and the nitrogen atom to which $P_6$ is attached, form a 4- to 7-membered saturated heterocyclic ring (preferably, an azetidine ring, a pyrrolidine ring, or a piperidine ring, and more preferably a pyrrolidine ring), and/or $R_7$ is $C_7$-$C_{14}$ aralkyl (preferably benzyl or phenethyl) optionally substituted with 1 to 5 (preferably 1 to 3) groups independently selected from the group consisting of halogen (preferably fluorine, chlorine, or iodine) and $C_1$-$C_6$ haloalkyl (preferably $C_1$-$C_3$ fluoroalkyl, and more preferably trifluoromethyl), $P_7$ is hydrogen, and $Q_7$ is hydrogen, and/or $R_8$ is $C_1$-$C_6$ alkyl (preferably $C_1$-$C_4$ alkyl, and more preferably 2-methylpropyl, isopropyl, or n-butyl), $C_2$-$C_6$ alkynyl (preferably $C_2$-$C_3$ alkynyl, and more preferably propargyl), 4- to 8-membered cyclic aminocarbonyl$C_1$-$C_6$ alkyl (preferably 4- to 8-membered cyclic aminocarbonyl$C_1$-$C_2$ alkyl, and more preferably 4- to 8-membered cyclic aminocarbonylmethyl) optionally substituted with 1 to 5 (preferably 1 to 3) fluorine atoms, 5- to 10-membered heteroaryl$C_1$-$C_6$ alkyl (preferably 5- to 10-membered heteroaryl$C_1$-$C_2$ alkyl, and more preferably 5- to 10-membered heteroarylmethyl), or $C_7$-$C_{14}$ aralkyl (preferably benzyl or phenethyl) optionally substituted with 1 to 3 halogen atoms (preferably chlorine), and $P_8$ is hydrogen, $C_1$-$C_6$ alkyl (preferably $C_1$-$C_3$ alkyl, and more preferably methyl), 4- to 8-membered cyclic amino$C_1$-$C_6$ alkyl optionally substituted with 1 to 5 (preferably 1 to 3) $C_1$-$C_6$ alkyl (preferably $C_1$-$C_3$ alkyl, and more preferably methyl) (preferably piperazyl$C_1$-$C_2$ alkyl), 4- to 7-membered heterocyclyl$C_1$-$C_6$ alkyl (preferably 4- to 7-membered heterocyclyl$C_1$-$C_2$ alkyl, more preferably azetidylethyl), $C_1$-$C_6$ alkoxy$C_1$-$C_6$ alkyl substituted with amino ($NH_2$), $C_1$-$C_6$ alkylamino (preferably methylamino), or di-$C_1$-$C_6$ alkylamino (preferably dimethylamino) (preferably $C_1$-$C_3$ alkoxy$C_1$-$C_2$ alkyl, and more preferably ethoxyethyl), or amino ($NH_2$) $C_1$-$C_6$ alkyl; or $R_8$ and $P_8$, together with the carbon atom to which $R_8$ is attached and the nitrogen atom to which $P_8$ is attached, form a 4- to 7-membered saturated heterocyclic ring (preferably an azetidine ring, a pyrrolidine ring, or a piperidine ring, and more preferably an azetidine ring or a pyrrolidine ring), wherein the 4- to 7-membered saturated heterocyclic ring is optionally substituted with 1 to 5 (preferably 1 to 3) halogen atoms (preferably fluorine) or $C_1$-$C_6$ alkoxy (preferably $C_1$-$C_3$ alkoxy, and more preferably methoxy or ethoxy), and/or $R_9$ is benzyl, and $Q_9$ is hydrogen; or $R_9$ and $Q_9$ are each independently $C_1$-$C_6$ alkyl (preferably $C_1$-$C_3$ alkyl, and more preferably methyl), or $R_9$ and $Q_9$, together with the carbon atom to which they are attached, form a 3- to 8-membered alicyclic ring (preferably a 3- to 6-membered alicyclic ring, more preferably a cyclobutane ring or a cyclopentane ring), and $P_9$ is hydrogen or $C_1$-$C_6$ alkyl (preferably $C_1$-$C_3$ alkyl, and more preferably methyl), and/or $R_{10}$ is $C_1$-$C_6$ alkyl (preferably $C_1$-$C_4$ alkyl, and more preferably isopropyl, 1-methylpropyl, or 2-methylpropyl) or $C_3$-$C_8$ cycloalkyl (preferably $C_3$-$C_6$ cycloalkyl, and more preferably cyclopentyl or cyclohexyl), and $P_{10}$ is hydrogen or $C_1$-$C_6$ alkyl (preferably $C_1$-$C_3$ alkyl, and more preferably methyl), and/or $R_{11}$ is $C_1$-$C_6$ alkyl (preferably $C_1$-$C_3$ alkyl, and more preferably methyl), di-$C_1$-$C_6$ alkylaminocarbonyl (preferably di-$C_1$-$C_3$ alkylaminocarbonyl, and more preferably dimethylaminocarbonyl), or 4- to 8-membered cyclic aminocarbonyl (preferably azetidinylcarbonyl, pyrrolidinylcarbonyl, piperidinylcarbonyl, 4-morpholinylcarbonyl, or 3-oxa-8-azabicyclo[3.2.1]octan-8-ylcarbonyl), $P_{11}$ is hydrogen or $C_1$-$C_6$ alkyl (preferably $C_1$-$C_3$ alkyl, and more preferably methyl), and $M_{11}$ is hydrogen.

In an embodiment, the present invention can be a cyclic peptide compound represented by formula (3) below that further specifies formula (1) above.

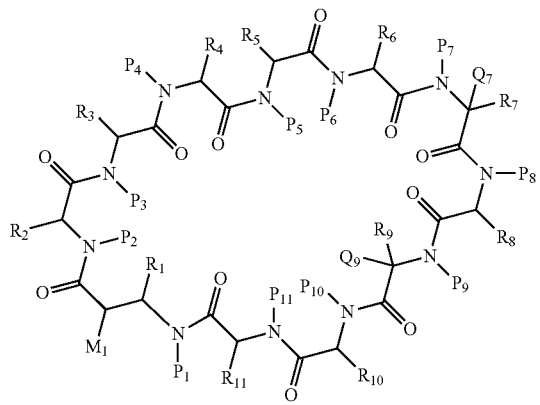

(3)

The definition of each group in formula (3) is the same as the definition of each group in formula (1). The cyclic peptide compound represented by formula (3) preferably has each of the following groups.

$R_1$ is hydrogen, $P_1$ is hydrogen or $C_1$-$C_6$ alkyl (preferably $C_1$-$C_3$ alkyl, and more preferably methyl), and $M_1$ is hydrogen, and/or $R_2$ is hydrogen or $C_1$-$C_6$ alkyl (preferably $C_3$-$C_6$ alkyl, and more preferably 1-methylpropyl), and $P_2$ is hydrogen or $C_1$-$C_6$ alkyl (preferably hydrogen or $C_1$-$C_3$ alkyl, and more preferably hydrogen or methyl), and/or $R_3$ is hydrogen, $P_3$ is $C_1$-$C_6$ alkyl (preferably $C_1$-$C_3$ alkyl, and more preferably methyl), and/or $R_4$ is hydrogen, $P_4$ is $C_1$-$C_6$ alkyl (preferably hydrogen or $C_1$-$C_3$ alkyl, and more preferably methyl), and/or $R_5$ is $C_3$-$C_8$ cycloalkyl$C_1$-$C_6$ alkyl (preferably $C_3$-$C_6$ cycloalkyl$C_1$-$C_2$ alkyl, and more preferably $C_5$-$C_6$ cycloalkylmethyl), and $P_5$ is $C_1$-$C_2$ alkyl (preferably methyl), and/or $R_6$ is hydrogen, and $P_6$ is $C_1$-$C_6$ alkyl (preferably $C_1$-$C_3$ alkyl, and more preferably methyl), and/or $R_7$ is $C_7$-$C_{14}$ aralkyl (preferably benzyl or phenethyl, and more preferably benzyl) optionally substituted with 1 to 5 (preferably 1 to 3) groups independently selected from the group consisting of halogen and $C_1$-$C_6$ haloalkyl (preferably $C_1$-$C_3$ fluoroalkyl, and more preferably trifluoromethyl), and $P_7$ is hydrogen, and $Q_7$ is hydrogen, and/or $R_8$ and $P_8$, together with the carbon atom to which $R_8$ is attached and the nitrogen atom to which $P_8$ is attached, form a 4- to 7-membered saturated heterocyclic ring (preferably an azetidine ring, a pyrrolidine ring, or a piperidine ring, and more preferably a pyrrolidine ring), and/or $R_9$ and $Q_9$, together with the carbon atom to which they are attached, form a 3- to 8-membered alicyclic ring (preferably a 3- to 6-membered alicyclic ring, and more preferably a cyclobutane ring or a cyclopentane ring), and $P_9$ is hydrogen, and/or $R_{10}$ is $C_3$-$C_8$ cycloalkyl (preferably $C_3$-$C_6$ cycloalkyl, and more preferably cyclopentyl or cyclohexyl), and $P_{10}$ is $C_1$-$C_6$ alkyl (preferably $C_1$-$C_3$ alkyl, and more preferably methyl), and/or $R_{11}$ is hydrogen, $C_7$-$C_{14}$ aralkyl (preferably benzyl or phenethyl, and more preferably benzyl) optionally substituted with 1 to 5 (preferably 1 to 3) halogen atoms (preferably fluorine), or $C_1$-$C_6$ alkoxy$C_1$-$C_6$ alkyl (preferably $C_2$-$C_6$ alkoxy$C_1$-$C_2$ alkyl, and more preferably $C_3$-$C_8$ alkoxymethyl) optionally substituted with one hydroxy group, and $P_{11}$ is $C_1$-$C_6$ alkyl (preferably $C_1$-$C_3$ alkyl, and more preferably methyl).

In an embodiment, the present invention can be a cyclic peptide compound represented by formula (4) below that further specifies formula (1) above.

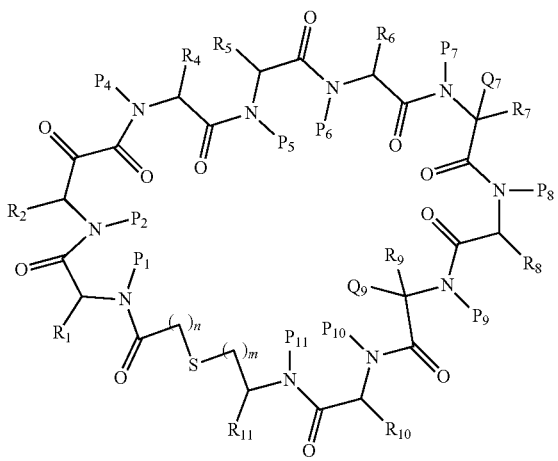

(4)

$R_1$ to $R_{11}$, $P_1$ to $P_{11}$, $Q_7$, and $Q_9$ in formula (4) are the same as $R_1$ to $R_{11}$, $P_1$ to $P_{11}$, $Q_7$, and $Q_9$ in formula (2) above, respectively, and n and m are each independently 1 or 2. Moreover, —S— in formula (4) may be oxidized to be —S(O)— or —S(O)$_2$—.

In an embodiment, the present invention can be a cyclic peptide compound represented by formula (5) below that further specifies formula (1) above.

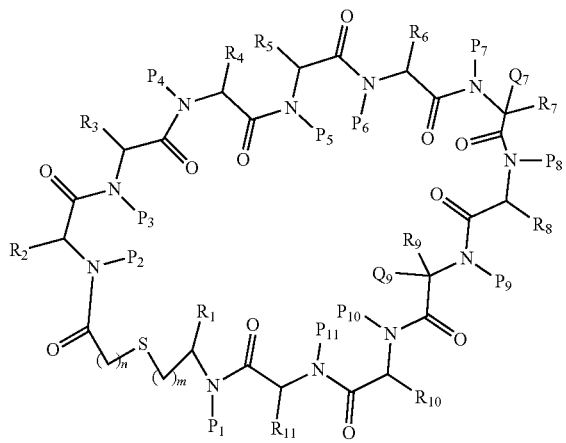

(5)

$R_1$ to $R_{11}$, $P_1$ to $P_{11}$, $Q_7$, and $Q_9$ in formula (5) are the same as $R_1$ to $R_{11}$, $P_1$ to $P_{11}$, $Q_7$, and $Q_9$ in formula (2) above, respectively, and n and m are each independently 1 or 2. Moreover, —S— in formula (5) may be oxidized to be —S(O)— or —S(O)$_2$—.

In an embodiment, the present invention can be formula (6) below wherein —CO-L$_1$- in formula (1) above is replaced with —(CH$_2$)$_n$C≡CCH$_2$S(CH$_2$)$_m$—, —(CH$_2$)$_n$CH═CHCH$_2$S(CH$_2$)$_m$—, or —(CH$_2$)$_{n+3}$S(CH$_2$)$_m$—, and L$_1$ is a single bond.

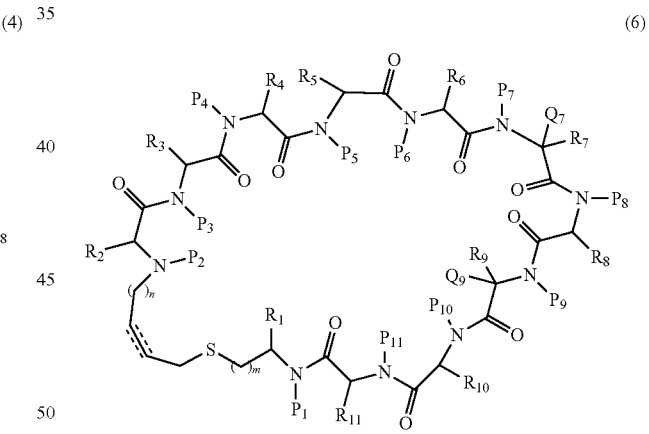

(6)

$R_1$ to $R_{11}$, $P_1$ to $P_{11}$, $Q_7$, and $Q_9$ in formula (6) are the same as $R_1$ to $R_{11}$, $P_1$ to $P_{11}$, $Q_7$, and $Q_9$ in formula (2) above, respectively,

-----
----- represents a single bond, a double bond, or a triple bond, n is 1, 2, or 3, and m is 1 or 2. Moreover, —S— in formula (6) may be oxidized to be —S(O)— or —S(O)$_2$—.

In an embodiment, the present invention can be formula (7) below wherein —CO-L$_{11}$- in formula (1) is replaced with —(CH$_2$)$_n$C≡CCH$_2$S(CH$_2$)$_m$—, —(CH$_2$)$_n$CH═CHCH$_2$S(CH$_2$)$_m$—, or —(CH$_2$)$_{n+3}$S(CH$_2$)$_m$—, and L$_1$ is a single bond.

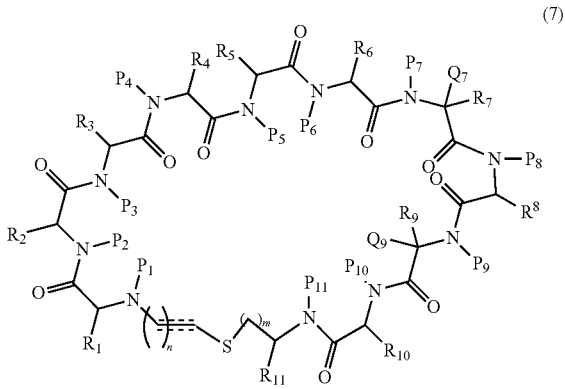

(7)

R$_1$ to R$_{11}$, P$_1$ to P$_{11}$, Q$_7$, and Q$_9$ in formula (7) are the same as R$_1$ to R$_{11}$, P$_1$ to P$_{11}$, Q$_7$, and Q$_9$ in formula (2), respectively, ===== ===== represents a single bond, a double bond, or a triple bond, n is 1, 2, or 3, and m is 1 or 2. Moreover, —S— in formula (7) may be oxidized to be —S(O)— or —S(O)$_2$—.

In an embodiment, the present invention can be a cyclic peptide compound represented by formula (8) below.

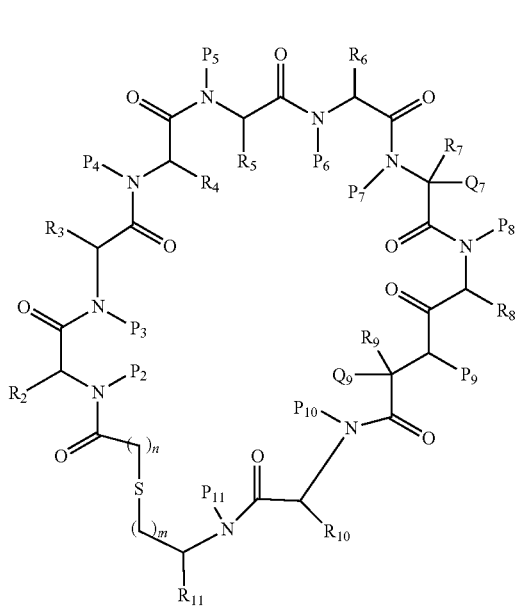

(8)

R$_2$ to R$_{11}$, P$_2$ to P$_{11}$, Q$_7$, and Q$_9$ in formula (8) are the same as R$_2$ to R$_{11}$, P$_2$ to P$_{11}$, Q$_7$, and Q$_9$ in the above-mentioned formula (1), respectively, and n and m are each independently 1 or 2. Further, —S— in formula (8) may be oxidized to be —S(O)— or —S(O)$_2$—.

Specific examples of the cyclic peptide compound of the present invention are as follows. The structural formulae of the following compounds (1) to (762), (764) to (845), (847) to (1027), (1029) to (1146), and (1148) to (2186) are shown in Table 24. That is, the numbers given to the following compounds correspond to the numbers given to the compounds shown in Table 24, respectively.

(1) (3S,9S,18S,21S,25S,28S,34S)-3-[2-[3-chloro-4-(trifluoromethyl)phenyl]ethyl]-28-cyclohexyl-9,18-bis(cyclohexylmethyl)-21-isobutyl-7,10,13,16,22,26,29-heptamethyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2) (8S,11S,17S,26S,29S,33R,36S)-17-(cyclohexylmethyl)-11-[2-[3-fluoro-4-(trifluoromethyl)phenyl]ethyl]-8,29,36-triisobutyl-6,15,18,21,24,30,33,34-octamethyl-26-[(1S)-1-methylpropyl]-6,9,12,15,18,21,24,27,30,34,37-undecazaspiro[4.33]octatriacontane-7,10,13,16,19,22,25,28,31,35,38-undecone, (3) (8S,11S,17S,26S,29S,33S,36S)-11-[2-[3-chloro-4-(trifluoromethyl)phenyl]ethyl]-17-(cyclohexylmethyl)-8-[2-(4,4-difluoro-1-piperidyl)-2-oxo-ethyl]-29-isobutyl-36-isopropyl-9,15,18,21,24,30,37-heptamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (4) (3S,6S,9S,13S,16S,19S,22S,25S,31S,34S)-25-[2-[3-chloro-4-(trifluoromethyl)phenyl]ethyl]-9-isobutyl-19-isopropyl-N,N,3,4,10,14,17,22,23,29,32-undecamethyl-6,16-bis[(1S)-1-methylpropyl]-2,5,8,11,15,18,21,24,27,30,33-undecaoxo-31-(p-tolylmethyl)-1,4,7,10,14,17,20,23,26,29,32-undecazabicyclo[32.2.0]hexatriacontane-13-carboxamide, (5) (5S,8S,11S,15S,18S,23aS,29S,35S,37aS)-8-((S)-sec-butyl)-29-(3-chloro-4-(trifluoromethyl)phenethyl)-18-cyclopentyl-33-ethyl-11-isobutyl-N,N,5,6,12,16,19,36-octamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (6) (6S,9S,13S,16S,22S,25S,31S,34S)-25-[2-[3-chloro-4-(trifluoromethyl)phenyl]ethyl]-16-cyclohexyl-31-(cyclohexylmethyl)-9-isobutyl-4,10,14,17,23,29,32-heptamethyl-6-[(1S)-1-methylpropyl]-13-(piperidine-1-carbonyl)-22-[[6-(trifluoromethyl)-3-pyridyl]methyl]spiro[1,4,7,10,14,17,20,23,26,29,32-undecazabicyclo[32.2.0]hexatriacontane-19,1'-cyclopentane]-2,5,8,11,15,18,21,24,27,30,33-undecone, (7) (5S,8S,11S,15S,18S,23aS,29S,35S,37aS)-29-(3-chloro-4-(trifluoromethyl)phenethyl)-35-(cyclohexylmethyl)-11-isobutyl-18-isopropyl-8-(methoxymethyl)-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (8) (5S,8S,11S,15R,18S,23aS,29S,35S,37aS)-8-((S)-sec-butyl)-29-(3-chloro-4-(trifluoromethyl)phenethyl)-35-(cyclohexylmethyl)-11-(cyclopentylmethyl)-18-isopropyl-5,6,12,15,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (9) (5S,8S,11S,15S,18S,23aS,29S,35S,37aS)-8-((S)-sec-butyl)-18-cyclopentyl-29-(3-fluoro-4-(trifluoromethyl)phenethyl)-11-isobutyl-5,6,12,16,19,33,36-heptamethyl-15-(morpholine-4-carbonyl)-35-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,

(10) (8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-9,15,18,21,24,30,34,37-octamethyl-26-[(1S)-1-methylpropyl]-33-(piperidine-1-carbonyl)-8-[[6-(trifluoromethyl)-3-pyridyl]methyl]-6,9,12,15,18,21,24,27,30,34,37-undecazaspiro[4.33]octatriacontane-7,10,13,16,19,22,25,28,31,35,38-undecone,

(11) (5S,8S,11S,15S,18S,23aS,29S,35S,37aS)-8-((S)-sec-butyl)-18-cyclopentyl-29-(3-chloro-4-(trifluoromethyl)phenethyl)-11-isobutyl-5,6,12,16,19,33,36-heptamethyl-15-(morpholine-4-carbonyl)-35-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,

(12) allyl N-[4-[(3S,9S,12S,18S,27S,30S,34R)-18-[(4-chlorophenyl)methyl]-3,30-diisobutyl-1,6,6,7,16,19,22,25,31,34-decamethyl-27-[(1S)-1-methylpropyl]-2,5,8,11,14,17,20,23,26,29,32-undecaoxo-12-[2-[4-(trifluoromethyl)phenyl]ethyl]-1,4,7,10,13,16,19,22,25,28,31-undecazacyclotetratriacont-9-yl]butyl]carbamate,

(13) (3S,9S,12S,18S,27S,30S,34S)-12-[(3-iodophenyl)methyl]-3,30-diisobutyl-1,6,6,7,16,19,22,25,31-nonamethyl-27-[(1S)-1-methylpropyl]-9-(2-phenylethyl)-34-(piperidine-1-carbonyl)-18-(p-tolylmethyl)-1,4,7,10,13,16,19,22,25,28,31-undecazacyclotetratriacontane-2,5,8,11,14,17,20,23,26,29,32-undecone,

(14) (3S,9S,18S,21S,25R,28S,34S)-3-[2-[3-chloro-4-(trifluoromethyl)phenyl]ethyl]-9-(cyclohexylmethyl)-28-cyclopropyl-21-isobutyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,

(15) (8S,11S,15S,18S,23aS,29S,35S,37aS)-8-((S)-sec-butyl)-29-(3-chloro-4-(trifluoromethyl)phenethyl)-35-(4-chlorobenzyl)-11-isobutyl-18-isopropyl-6,12,16,19,33,36-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,

(16) (5S,8S,11S,15S,18S,23aS,29S,35S,37aS)-8-((S)-sec-butyl)-18-cyclopentyl-29-(3-fluoro-4-(trifluoromethyl)phenethyl)-11-isobutyl-N,N,5,6,12,16,19,33,36-nonamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide,

(17) (5S,8S,11S,15S,18S,23aS,29S,35S,37aS)-29-(3-chloro-4-(trifluoromethyl)phenethyl)-35-(cyclohexylmethyl)-11-isobutyl-18-isopropyl-8-(2-methoxyethyl)-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,

(18) (3S,9S,18S,21S,25R,28S,31S,34S)-31-benzyl-28-isobutyl-7,10,13,16,21,22,25,29,32-nonamethyl-9,18-bis[(1S)-1-methylpropyl]-3-[2-[4-(trifluoromethyl)phenyl]ethyl]-1,4,7,10,13,16,19,22,26,29,32-undecazabicyclo[32.3.0]heptatriacontane-2,5,8,11,14,17,20,23,27,30,33-undecone,

(19) (3S,9S,12S,18S,27S,30S,34R)-12-[2-(4-chlorophenyl)ethyl]-18-[(4-chlorophenyl)methyl]-3,9-diisobutyl-4,6,6,10,16,19,22,25,30,31,34-undecamethyl-27-[(1S)-1-methylpropyl]-1,4,7,10,13,16,19,22,25,28,31-undecazacyclotetratriacontane-2,5,8,11,14,17,20,23,26,29,32-undecone,

(20) (5S,8S,11S,15S,18S,23aS,29S,35S,37aS)-8-((S)-sec-butyl)-18-cyclopentyl-29-(3-fluoro-4-(trifluoromethyl)phenethyl)-11-isobutyl-5,6,12,16,19,33,36-heptamethyl-35-(4-methylbenzyl)-15-(pyrrolidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,

(21) (3S,6S,9S,12S,18S,27S,30S,34S)-6,9-dibenzyl-18-[(4-chlorophenyl)methyl]-12-[(3,5-difluorophenyl)methyl]-3-isopropyl-4,7,16,19,22,25,30,31-octamethyl-27-[(1S)-1-methylpropyl]-34-(pyrrolidine-1-carbonyl)-1,4,7,10,13,16,19,22,25,28,31-undecazacyclotetratriacontane-2,5,8,11,14,17,20,23,26,29,32-undecone,

(22) (3S,9S,18S,21S,25R,28S,34S)-3-[2-[3-chloro-4-(trifluoromethyl)phenyl]ethyl]-9-(cyclohexylmethyl)-21-isobutyl-28-isopentyl-7,10,13,16,22,25,26,29-octamethyl-8-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,

(23) (5S,8S,11S,15S,18S,23aS,29S,35S,37aS)-8-((S)-sec-butyl)-29-(3-chloro-4-(trifluoromethyl)phenethyl)-35-(cyclohexylmethyl)-36-ethyl-11-isobutyl-18-isopropyl-5,6,12,16,19,33-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,

(24) (3S,6S,9S,13S,16S,19S,22R,25S,31S,34S)-25-[2-[3-chloro-4-(trifluoromethyl)phenyl]ethyl]-31-(cyclohexylmethyl)-16-cyclopentyl-9-isobutyl-19-isopropyl-N,N,3,4,10,14,17,22,29,32-decamethyl-6-[(1S)-1-methylpropyl]-2,5,8,11,15,18,21,24,27,30,33-undecaoxo-1,4,7,10,14,17,20,23,26,29,32-undecazabicyclo[32.2.0]hexatriacontane-13-carboxamide,

(25) (6S,12S,21S,24S,26aR,29aR,32S,35S,37aS)-35-benzyl-21-((S)-sec-butyl)-12-(4-chlorobenzyl)-32-isobutyl-10,13,16,19,24,25,33,36-octamethyl-6-(4-(trifluoromethyl)phenethyl)hexacosahydro-1H-cyclopenta[f1]pyrrolo[1,2-v][1,4,7,10,13,16,19,22,25,28,31]undecaazacyclotetratriacontin-5,8,11,14,17,20,23,26,31,34,37(37aH)-undecaone,

(26) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-22-[2-(4,4-difluoro-1-piperidyl)-2-oxoethyl]-9-isobutyl-3,4,10,14,17,23,29,32-octamethyl-6-[(1S)-1-methylpropyl]-13-(pyrrolidine-1-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone,

(27) (3S,6S,9S,13S,16S,22S,25S,31S,34S)-25-[2-[3-chloro-4-(trifluoromethyl)phenyl]ethyl]-9-isobutyl-22-(isopentyloxymethyl)-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide,

(28) (3S,9S,12S,18S,27S,30S,34R)-18-[(4-chlorophenyl)methyl]-12-[2-(4-fluorophenyl)ethyl]-3,9-diisobutyl-4,6,6,10,16,19,22,25,30,31,34-undecamethyl-27-[(1S)-1-methylpropyl]-1,4,7,10,13,16,19,22,25,28,31-undecazacyclotetratriacontane-2,5,8,11,14,17,20,23,26,29,32-undecone,

(29) (3S,6S,9S,12S,18S,27S,30S,34S)-6,9-dibenzyl-2-[(3-chlorophenyl)methyl]-18-[(4-chlorophenyl)methyl]-16-ethyl-3-isopropyl-4,7,19,22,25,30,31-heptamethyl-27-[(1S)-1-methylpropyl]-34-(pyrrolidine-1-carbonyl)-1,4,7,10,13,16,19,22,25,28,31-undecazacyclotetratriacontane-2,5,8,11,14,17,20,23,26,29,32-undecone,

(30) (3S,9S,18S,21S,25S,28S,34S)-3-[2-[3-chloro-4-(trifluoromethyl)phenyl]ethyl]-9-(cyclohexylmethyl)-28-(cyclopentylmethyl)-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,

(31) (4R,7S,13S,16S,22S,31S,34S)-22-(cyclohexylmethyl)-7,13-diisobutyl-4,8,10,10,14,20,23,26,29-nonamethyl-31-[(1S)-1-methylpropyl]-16-[2-[4-(trifluoromethyl)phenyl]ethyl]-1,5,8,11,14,17,20,23,26,29,32-undecazabicyclo[32.4.0]octatriacontane-2,6,9,12,15,18,21,24,27,30,33-undecone,

(32) (5S,8S,11S,15S,18S,23aS,29S,35S,37aS)-8-((S)-sec-butyl)-29-(3-chloro-4-(trifluoromethyl)phenethyl)-11-isobutyl-18-isopropyl-5,6,12,16,19,33,36-heptamethyl-15-(piperidine-1-carbonyl)-35-(prop-2-yn-1-yl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,

(33) (5S,8S,11S,15R,18S,23aS,25R,29S,35S,37aS)-8,18-di((S)-sec-butyl)-29-(3,5-difluoro-4-(trifluoromethyl)phenethyl)-25-ethoxy-36-ethyl-11-isobutyl-5,6,12,15,16,19,33-heptamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-(34) (5S,8S,11S,15R,18S,23aS,29S,35S,37aS)-8-((S)-sec-butyl)-18-cyclohexyl-29-(3,5-difluoro-4-(trifluoromethyl)phenethyl)-25,25-difluoro-11-isobutyl-5,6,12,15,16,19,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclobutan]-4,7,10,13,17,20,23,28,31,34,37(14H,22H)-undecaone,

(35) (8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-6,12,16,19,33,36-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,

(36) (8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-9,15,18,21,24,30,34,37-octamethyl-26-[(1S)-1-methylpropyl]-33-(piperidine-1-carbonyl)-8-(4-pyridylmethyl)-6,9,12,15,18,21,24,27,30,34,37-undecazaspiro[4.33]octatriacontane-7,10,13,16,19,22,25,28,31,35,38-undecone,

(37) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-(cyclopentylmethyl)-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,

(38) (5S,8S,11S,15R,18S,23aS,29S,35S,37aS)-8-((S)-sec-butyl)-29-(3-chloro-4-(trifluoromethyl)phenethyl)-11,35-bis(cyclohexylmethyl)-18-isopropyl-5,6,12,15,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,

(39) (5S,8S,11S,15R,18S,23aS,29S,35S,37aS)-8-((S)-sec-butyl)-18-cyclohexyl-29-(3,5-difluoro-4-(trifluoromethyl)phenethyl)-11-isobutyl-5,6,12,15,16,19,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,

(40) (5S,8S,11S,15S,18S,23aS,29S,35S,37aS)-8,18-di((S)-sec-butyl)-29-(3-chloro-4-(trifluoromethyl)phenethyl)-35-(cyclohexylmethyl)-11-isobutyl-5,6,12,16,19,33,36-heptamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,

(41) (3S,6S,9S,13S,16S,19S,22S,25S,31S,34S)-25-[2-[3-chloro-4-(trifluoromethyl)phenyl]ethyl]-31-(cyclohexylmethyl)-16-cyclopentyl-22-[2-(3,3-difluoroazetidin-1-yl)-2-oxo-ethyl]-9-isobutyl-N,N,3,4,10,14,17,23,29,32-decamethyl-6-[(1S)-1-methylpropyl]-2,5,8,11,15,18,21,24,27,30,33-undecaoxo-19-(propoxymethyl)-1,4,7,10,14,17,20,23,26,29,32-undecazabicyclo[32.2.0]hexatriacontane-13-carboxamide,

(42) (5S,8S,11S,15R,18S,23aS,29S,32R,35S,37aS)-8-((S)-sec-butyl)-29-(3-chloro-4-(trifluoromethyl)phenethyl)-35-(3-chlorobenzyl)-18-cyclopentyl-5,6,11,12,15,19,32,33,36-nonamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,

(43) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-22-[(2-fluorophenyl)methyl]-9-isobutyl-N,N,3,4,10,14,17,23,29,32-decamethyl-6-[(1S)-1-methylpropyl]-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide,

(44) (5S,8S,11S,15S,18S,23aS,29S,35S,37aS)-8,18-di((S)-sec-butyl)-29-(3-fluoro-4-(trifluoromethyl)phenethyl)-11-isobutyl-5,6,12,16,19,33,36-heptamethyl-35-(4-methylbenzyl)-15-(pyrrolidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,

(45) (5S,8S,11S,15S,18S,23aS,29S,35S,37aS)-29-(3-chloro-4-(trifluoromethyl)phenethyl)-8-(cyclobutoxymethyl)-35-(cyclohexylmethyl)-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,

(46) (3S,6S,9S,12S,18S,27S,30S,34S)-18-[(4-chlorophenyl)methyl]-3,6,9-triisobutyl-4,7,16,19,22,25,30,31-octamethyl-27-[(1S)-1-methylpropyl]-34-(pyrrolidine-1-carbonyl)-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone,

(47) (5S,8S,11S,15S,18S,23aS,29S,35S,37aS)-8,18-di((S)-sec-butyl)-29-(3-fluoro-4-(trifluoromethyl)phenethyl)-

11-isobutyl-5,6,12,16,19,33,36-heptamethyl-35-(4-methylbenzyl)-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,

(48) (3S,9S,18S,21S,25S,28S,34S)-3-[2-[3-chloro-4-(trifluoromethyl)phenyl]ethyl]-28-cyclohexyl-9-(cyclohexylmethyl)-36,36-difluoro-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,

(49) (5S,8S,11S,15R,18S,23aS,29S,35S,37aS)-8-((S)-sec-butyl)-35-(cyclohexylmethyl)-18-cyclopentyl-29-(3-fluoro-4-(trifluoromethyl)phenethyl)-11-isobutyl-5,6,12,15,16,19,33,36-octamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,

(50) (3S,6S,9S,12S,18S,27S,30S,34S)-6-benzyl-18-[(4-chlorophenyl)methyl]-3,9-diisobutyl-4,7,16,19,22,25,30,31-octamethyl-27-[(1S)-1-methylpropyl]-34-(pyrrolidine-1-carbonyl)-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone,

(51) (3S,6S,9S,12S,18S,27S,30S,34R)-6-benzyl-18-[(4-chlorophenyl)methyl]-9-isobutyl-3-isopropyl-4,7,10,16,19,22,25,30,31,34-decamethyl-27-[(1S)-1-methylpropyl]-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone,

(52) (3S,9S,18S,21S,25S,28S,34S)-3-[2-[3-chloro-4-(trifluoromethyl)phenyl]ethyl]-28-cyclohexyl-9-(cyclohexylmethyl)-7,10,13,16,22,26,29-heptamethyl-18-[(1S)-1-methylpropyl]-21-(2-methylsulfonylethyl)-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,

(53) N-tert-butyl-2-[[(3S,6S,9S,12S,18S,27S,30S,34S)-18-[(4-chlorophenyl)methyl]-3,9-diisobutyl-4,16,19,22,25,30,31-heptamethyl-27-[(1S)-1-methylpropyl]-2,5,8,11,14,17,20,23,26,29,32-undecaoxo-34-(pyrrolidine-1-carbonyl)-12-[2-[4-(trifluoromethyl)phenyl]ethyl]-1,4,7,10,13,16,19,22,25,28,31-undecazacyclotetratriacont-6-yl]methoxy]acetamide,

(54) (5S,8S,11S,15S,18S,23aS,29S,35S,37aS)-8,18-di((S)-sec-butyl)-29-(3-chloro-4-(trifluoromethyl)phenethyl)-5,12,16,19,33,36-hexamethyl-15-(morpholine-4-carbonyl)-11-pentyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,

(55) (5S,8S,11S,15S,18S,23aS,29S,35S,37aS)-15-(azetidine-1-carbonyl)-8-((S)-sec-butyl)-18-cyclopentyl-29-(3,5-difluoro-4-(trifluoromethyl)phenethyl)-36-ethyl-11-isobutyl-5,6,12,16,19,33-hexamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (56) (3S,9S,18S,21S,25S,28S,34S)-3-[2-[3-chloro-4-(trifluoromethyl)phenyl]ethyl]-9-(cyclohexylmethyl)-28-cyclopentyl-7,10,16,21,22,29-heptamethyl-18-[(1S)-1-methylpropyl]-25-(piperidine-1-carbonyl)-26-propyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone,

(57) (6S,9S,13R,16S,22S,25S,31S,34S)-25-[2-[3-chloro-4-(trifluoromethyl)phenyl]ethyl]-31-(cyclohexylmethyl)-9,16,22-triisobutyl-4,10,13,14,19,19,20,29,32-nonamethyl-6-[(1S)-1-methylpropyl]-1,4,7,10,14,17,20,23,26,29,32-undecazabicyclo[32.2.0]hexatriacontane-2,5,8,11,15,18,21,24,27,30,33-undecone,

(58) (5S,8S,11S,15S,18S,23aS,29S,35S,37aS)-8-((S)-sec-butyl)-29-(3-chloro-4-(trifluoromethyl)phenethyl)-11-cyclohexyl-35-(cyclohexylmethyl)-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,

(59) (3S,9S,18S,21S,25R,28S,34S)-3-[2-[3-chloro-4-(trifluoromethyl)phenyl]ethyl]-28-(cyclobutylmethyl)-9-(cyclohexylmethyl)-21-isobutyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,

(60) (3S,9S,18S,21S,25S,28S,34S)-3-[2-[3-chloro-4-(trifluoromethyl)phenyl]ethyl]-9-(cyclohexylmethyl)-21-(cyclopentylmethyl)-28-isopropyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,

(61) (8S,11S,17S,26S,29S,33R,36S)-11-[2-[3-chloro-4-(trifluoromethyl)phenyl]ethyl]-17-(cyclohexylmethyl)-8,36-diisobutyl-9,15,18,21,24,29,30,33,37-nonamethyl-26-[(1S)-1-methylpropyl]-6,9,12,15,18,21,24,27,30,34,37-undecazaspiro[4.33]octatriacontane-7,10,13,16,19,22,25,28,31,35,38-undecone,

(62) (3S,9S,18S,21S,25R,28S,34S)-3-[2-[3-chloro-4-(trifluoromethyl)phenyl]ethyl]-28-cyclopentyl-36,36-difluoro-21-isobutyl-7,10,13,16,22,25,26,29-octamethyl-18-[(1S)-1-methylpropyl]-9-[[4-(trifluoromethyl)phenyl]methyl]spiro[1,4,7,10,13,16,19,22,26,29,32-undecazabicyclo[32.3.0]heptatriacontane-31,1'-cyclobutane]-2,5,8,11,14,17,20,23,27,30,33-undecone,

(63) (8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-9,15,18,21,24,30,34,37-octamethyl-26-[(1S)-1-methylpropyl]-33-(piperidine-1-carbonyl)-8-(3-pyridylmethyl)-6,9,12,15,18,21,24,27,30,34,37-undecazaspiro[4.33]octatriacontane-7,10,13,16,19,22,25,28,31,35,38-undecone,

(64) (5S,8S,11S,15R,18S,23aS,29S,35S,37aS)-8-((S)-sec-butyl)-29-(3-chloro-4-(trifluoromethyl)phenethyl)-35-(cyclohexylmethyl)-18-cyclopentyl-11,15-diisobutyl-5,6,12,19,33,36-hexamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,

(65) (3S,6S,9S,12S,18S,27S,30S,34R)-6-benzyl-18-[(4-chlorophenyl)methyl]-12-[(3-iodophenyl)methyl]-3,9-diisobutyl-4,7,16,19,22,25,30,31,34-nonamethyl-27-[(1S)-1-methylpropyl]-1,4,7,10,13,16,19,22,25,28,31-undecazacyclotetratriacontane-2,5,8,11,14,17,20,23,26,29,32-undecone,

(66) (3S,9S,18S,21S,25R,28S,34S,36R)-28-cyclopentyl-3-[2-[3,5-difluoro-4-(trifluoromethyl)phenyl]ethyl]-36-ethoxy-21-isobutyl-7,10,13,16,22,25,26,29-octamethyl- 18-[(1S)-1-methylpropyl]-9-[[4-(trifluoromethyl)phenyl] methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,

(67) (3S,6S,9S,13S,16S,22R,25S,31S,34S)-25-[2-[3-chloro-4-(trifluoromethyl)phenyl]ethyl]-9-isobutyl-N,N,3,4,10,14,17,22,29,32-decamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide,

(68) (3S,9S,18S,21S,25S,28S,34S)-3-[2-[3-chloro-4-(trifluoromethyl)phenyl]ethyl]-28-cyclohexyl-9-(cyclohexylmethyl)-21-(cyclopropylmethyl)-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,

(69) (8S,11S,17S,26S,29S,33S,36S)-8-benzyl-11-[2-[3-chloro-4-(trifluoromethyl)phenyl]ethyl]-17-(cyclohexylmethyl)-36-isopropyl-9,15,18,21,24,29,30,34,37-nonamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone,

(70) N-(tert-butyl)-2-(((5S,8S,11S,15R,18S,23aS,29S,35S,37aS)-8-((S)-sec-butyl)-29-(3-chloro-4-(trifluoromethyl) phenethyl)-35-(cyclohexylmethyl)-11-isobutyl-18-isopropyl-6,12,15,19,33,36-hexamethyl-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentan]-5-yl)methoxy)acetamide,

(71) (3S,6S,10R,13S,16S,19S,22S,28S,34S)-16-benzyl-28-[(4-chlorophenyl)methyl]-19-isobutyl-13-isopropyl-6,7,10,14,17,20,26,29,32-nonamethyl-3-[(1S)-1-methylpropyl]-22-[2-[4-(trifluoromethyl)phenyl]ethyl]-1,4,7,11,14,17,20,23,26,29,32-undecazabicyclo[32.2.0]hexatriacontane-2,5,8,12,15,18,21,24,27,30,33-undecone,

(72) (3S,9S,18S,21S,25S,28S,34S)-28-cyclohexyl-9-(cyclohexylmethyl)-7,10,13,16,21,22,26,29-octamethyl-18-[(1S)-1-methylpropyl]-25-(piperidine-1-carbonyl)-3-[2-[4-(trifluoromethyl)phenyl]ethyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,

(73) (3S,9S,18S,21S,25S,28S,34S)-3-[2-[3-chloro-4-(trifluoromethyl)phenyl]ethyl]-21-cyclobutyl-28-cyclohexyl-7,10,13,16,22,26,29-heptamethyl-18-[(1S)-1-methylpropyl]-25-(pyrrolidine-1-carbonyl)-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,

(74) (3S,9S,18S,21S,25R,28S,34S,36R)-9-(cyclohexylmethyl)-28-cyclopentyl-3-[2-[3,5-difluoro-4-(trifluoromethyl)phenyl]ethyl]-36-ethoxy-21-isobutyl-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,

(75) (3S,9S,18S,21S,25R,28S,34S)-3-[2-[3-chloro-4-(trifluoromethyl)phenyl]ethyl]-9-(cyclobutylmethyl)-21-isobutyl-28-isopropyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,

(76) (6'S,15'S,18'S,22'R,25'S,30a'S,36'S,38a'R)-15'-((S)-sec-butyl)-36'-(3-chloro-4-(trifluoromethyl)phenethyl)-6'-(cyclohexylmethyl)-18'-isobutyl-25'-isopropyl-7',10',13',19',22',26'-hexamethyltetracosahydro-5'H-spiro[cyclopentane-1,28'-dipyrrolo[2,1-i:2',1'-o][1,4,7,10,13,16,19,22,25,28,31]undecaazacyclotetratriacontin]-5',8',11',14',17',20',24',27',30',35',38'(21'H,29'H)-undecaone,

(77) (8S,11S,15R,18S,23aS,29S,31aR,37S,39aS)-8-((S)-sec-butyl)-29-(3-chloro-4-(trifluoromethyl)phenethyl)-37-(cyclohexylmethyl)-18-isopropyl-6,11,12,15,19,38-hexamethyltetracosahydro-2H,4H-spiro[azeto[2,1-u] dipyrrolo[2,1-i:2',1'-o][1,4,7,10,13,16,19,22,25,28,31] undecaazacyclotetratriacontine-21,1'-cyclopentan]-4,7,10,13,17,20,23,28,31,36,39(14H,22H)-undecaone,

(78) (5S,8S,11S,15S,18S,23aS,29S,35S,37aS)-8-((S)-sec-butyl)-29-(3-chloro-4-(trifluoromethyl)phenethyl)-35-(5,5-difluoropentyl)-11-isobutyl-18-isopropyl-5,6,12,16,19,33,36-heptamethyl-15-(piperidine-1-carbonyl) docosahydro-2H,4H-spiro[azeto[2,1-u]pyrrolo[2,1-i][1,4,7,10,13,16,19,22,25,28,31] undecaazacyclotetratriacontine-21,1'-cyclopentan]-4,7,10,13,17,20,23,28,31,34,37(14H,22H)-undecaone,

(79) (5S,8S,11S,15R,18S,23aS,29S,35S,37aS)-8,18-di((S)-sec-butyl)-29-(3-chloro-4-(trifluoromethyl)phenethyl)-35-cyclopentyl-11-isobutyl-5,6,12,15,16,19,33,36-octamethyldocosahydro-2H,4H-spiro[azeto[2,1-i]pyrrolo[2,1-i][1,4,7,10,13,16,19,22,25,28,31] undecaazacyclotetratriacontine-21,1'-cyclopentan]-4,7,10,13,17,20,23,28,31,34,37(14H,22H)-undecaone,

(80) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-isopropyl-11-((R)-1-methoxyethyl)-5,6,12,16,19,33,36-heptamethyl-15-(piperidine-1-carbonyl)docosahydro-2H,4H-spiro[azeto[2,1-u]pyrrolo [2,1-i][1,4,7,10,13,16,19,22,25,28,31] undecaazacyclotetratriacontine-21,1'-cyclopentan]-4,7,10,13,17,20,23,28,31,34,37(14H,22H)-undecaone,

(81) (3S,9S,18S,21S,25R,28S,34S)-3-[2-[3-chloro-4-(trifluoromethyl)phenyl]ethyl]-9-(cyclohexylmethyl)-21-isobutyl-28-isopropyl-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,1'-cyclohexane]-2,5,8,11,14,17,20,23,27,30,33-undecone,

(82) (9'S,12'S,16'R,19'S,24a'S,30'S,36'S,38a'S)-9'-((S)-sec-butyl)-30'-(3-chloro-4-(trifluoromethyl)phenethyl)-36'-(2-chlorobenzyl)-19'-cyclopentyl-7',12',13',16',20',34',37'-heptamethyltetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone,

(83) (3S,9S,12S,18S,27S,30S,34R)-3-butyl-8-[(4-chlorophenyl)methyl]-12-[2-[3-fluoro-4-(trifluoromethyl)phenyl]ethyl]-9,30-diisobutyl-1,6,6,7,16,19,22,25,31,34-decamethyl-27-[(1S)-1-methylpropyl]-1,4,7,10,13,16,19,22,25,28,31-undecazacyclotetratriacontane-2,5,8,11,14,17,20,23,26,29,32-undecone,

(84) (5S,8S,11S,15S,18S,23aS,29S,35S,37aS)-29-(3-chloro-4-(trifluoromethyl)phenethyl)-35-(cyclohexylmethyl)-8-(cyclopentylmethyl)-11-isobutyl-18-isopropyl-5,6,12,16,19,33,36-heptamethyl-15-(piperidine-1-carbonyl)docosahydro-2H,4H-spiro[azeto[2,1-u]pyrrolo [2,1-i][1,4,7,10,13,16,19,22,25,28,31] undecaazacyclotetratriacontine-21,1'-cyclopentan]-4,7,10,13,17,20,23,28,31,34,37(14H,22H)-undecaone,

(85) (5S,8S,11S,15R,18S,23aS,29S,35S,37aS)-8,18-di((S)-sec-butyl)-29-(3,5-difluoro-4-(trifluoromethyl)phenethyl)-36-ethyl-25,25-difluoro-11-isobutyl-5,6,12,15,16, 19,33-heptamethyl-35-(4-(trifluoromethyl)benzyl) docosahydro-2H4H-spiro[azeto[2,1-u]pyrrolo[2,1-i][1,4, 7,10,13,16,19,22,25,28,31] undecaazacyclotetratriacontine-21,1'-cyclobutan]-4,7,10, 13,17,20,23,28,31,34,37(14H,22H)-undecaone,

(86) (5S,8S,11S,15S,18S,23aS,29S,35S,37aS)-8-((S)-sec-butyl)-29-(3-chloro-4-(trifluoromethyl)phenethyl)-35-(cyclohexylmethyl)-5-((2-hydroxy-2-methylpropoxy)methyl)-11-isobutyl-18-isopropyl-6,12,16,19,33,36-hexamethyl-15-(piperidine-1-carbonyl)docosahydro-2H, 4H-spiro[azeto[2,1-u]pyrrolo[2,1-i][1,4,7,10,13,16,19, 22,25,28,31]undecaazacyclotetratriacontine-21,1'-cyclopentan]-4,7,10,13,17,20,23,28,31,34,37(14H,22H)-undecaone,

(87) (5S,8S,11S,15S,18S,23aS,29S,35S,37aS)-8-((S)-sec-butyl)-29-(3-chloro-4-(trifluoromethyl)phenethyl)-18,35-bis(cyclohexylmethyl)-11-isobutyl-5,6,12,16,19,33,36-heptamethyl-15-(piperidine-1-carbonyl)docosahydro-2H, 4H-spiro[azeto[2,1-u]pyrrolo[2,1-i][1,4,7,10,13,16,19, 22,25,28,31]undecaazacyclotetratriacontine-21,1'-cyclopentan]-4,7,10,13,17,20,23,28,31,34,37(14H,22H)-undecaone,

(88) (3S,9S,18S,21S,25R,28S,34S)-3-[2-[3-chloro-4-(trifluoromethyl)phenyl]ethyl]-9-(cyclopentylmethyl)-21-isobutyl-28-isopropyl-7,10,13,16,22,25,26,29-octamethyl-8-[(1S)-1-methylpropyl]spiro[1,4,7,10,13,16,19,22, 26,29,32-undecazabicyclo[32.3.0]heptatriacontane-31,1'-cyclopentane]-2,5,8,11,14,17,20,23,27,30,33-undecone,

(89) (5S,8S,11S,15S,18S,23aS,29S,35S,37aS)-11-(but-3-yn-1-yl)-8-((S)-sec-butyl)-29-(3-chloro-4-(trifluoromethyl)phenethyl)-18-cyclohexyl-35-(4-iodobenzyl)-5,6, 12,16,19,33,36-heptamethyl-15-(piperidine-1-carbonyl)docosahydro-2H,4H-spiro[azeto[2,1-u]pyrrolo[2,1-i][1,4, 7,10,13,16,19,22,25,28,31] undecaazacyclotetratriacontine-21,1'-cyclopentan]-4,7, 10,13,17,20,23,28,31,34,37(14H,22H)-undecaone,

(90) (3S,9S,18S,21S,25S,28S,34S,36S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-36-phenyl-25-(piperidine-1-carbonyl)spiro[1,4,7,10,13,16,19,22,26,29, 32-undecazabicyclo[32.3.0]heptatriacontane-31,1'-cyclopentane]-2,5,8,11,14,17,20,23,27,30,33-undecone,

(91) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-((R)-1-hydroxyethyl)-18-isopropyl-5,6,12,16,19,33,36-heptamethyl-15-(piperidine-1-carbonyl)docosahydro-2H,4H-spiro[azeto[2,1-u]pyrrolo [2,1-i][1,4,7,10,13,16,19,22,25,28,31] undecaazacyclotetratriacontine-21,1'-cyclopentan]-4,7, 10,13,17,20,23,28,31,34,37(14H,22H)-undecaone,

(92) (3S,9S,18S,21S,25S,28S,34S)-3-[2-[3-chloro-4-(trifluoromethyl)phenyl]ethyl]-28-cyclohexyl-9-(cyclohexylmethyl)-18-(5,5-difluoropentyl)-21-isobutyl-7,10,13,16, 22,26,29-heptamethyl-25-(piperidine-1-carbonyl)spiro[1, 4,7,10,13,16,19,22,26,29,32-undecazabicyclo[32.3.0] heptatriacontane-31,1'-cyclopentane]-2,5,8,11,14,17,20, 23,27,30,33-undecone,

(93) (3S,9S,18S,21S,25R,28S,34S)-3-[2-[3-chloro-4-(trifluoromethyl)phenyl]ethyl]-9-(cyclohexylmethyl)-28-isopropyl-7,10,13,16,21,22,25,29,31,31,32-undecamethyl-18-[(1S)-1-methylpropyl]-1,4,7,10,13,16,19,22,26,29,32-undecazabicyclo[32.3.0]heptatriacontane-2,5,8,11,14,17, 20,23,27,30,33-undecone,

(94) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-(5,5-difluoropentyl)-18-isopropyl-5,6,12,16,19,33,36-heptamethyl-15-(piperidine-1-carbonyl)docosahydro-2H,4H-spiro[azeto[2,1-u]pyrrolo [2,1-i][1,4,7,10,13,16,19,22,25,28,31] undecaazacyclotetratriacontine-21,1'-cyclopentan]-4,7, 10,13,17,20,23,28,31,34,37(14H,22H)-undecaone,

(95) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-22-[(3-fluorophenyl)methyl]-9-isobutyl-N,N,3,4,10,14,17,23,29,32-decamethyl-6-[(1S)-1-methylpropyl]-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide,

(96) (3S,9S,12S,18S,27S,30S,34S)-18-[(4-chlorophenyl)methyl]-12-[2-[3-fluoro-4-(trifluoromethyl)phenyl] ethyl]-3,9,30-triisobutyl-6,6,7,16,19,22,25,31-octamethyl-27-[(1S)-1-methylpropyl]-34-(pyrrolidine-1-carbonyl)-1,4,7,10,13,16,19,22,25,28,31-undecazacyclotetratriacontane-2,5,8,11,14,17,20,23,26, 29,32-undecone,

(97) (8S,11S,17S,26S,29S,33S,36S)-11-[2-[3-chloro-4-(trifluoromethyl)phenyl]ethyl]-17-(cyclohexylmethyl)-8-[2-(4,4-difluoro-1-piperidyl)-2-oxo-ethyl]-29-isobutyl-36-isopropyl-N,N,9,15,18,21,24,30,37-nonamethyl-26-[(1S)-1-methylpropyl]-7,10,13,16,19,22,25,28,31,35,38-undecaoxo-6,9,12,15,18,21,24,27,30,34,37-undecazaspiro[4.33]octatriacontane-33-carboxamide,

(98) (5S,8S,11S,15R,18S,23aS,29S,32R,35S,37aS)-8-((S)-sec-butyl)-29-(3-chloro-4-(trifluoromethyl)phenethyl)-18-cyclopentyl-35-isobutyl-5,6,11,12,15,19,32,33,36-nonamethyldocosahydro-2H,4H-spiro[azeto[2,1-u] pyrrolo[2,1-i][1,4,7,10,13,16,19,22,25,28,31] undecaazacyclotetratriacontine-21,1'-cyclopentan]-4,7, 10,13,17,20,23,28,31,34,37(14H,22H)-undecaone,

(99) (5S,8S,11S,15R,18S,23aS,25R,29S,35S,37aS)-8,18-di((S)-sec-butyl)-29-(3-chloro-4-(trifluoromethyl)phenethyl)-25-ethoxy-11-isobutyl-5,6,12,15,16,19,33,36-octamethyl-35-(4-(trifluoromethyl)benzyl)docosahydro-2H,4H-spiro[azeto[2,1-u]pyrrolo[2,1-i][1,4,7,10,13,16, 19,22,25,28,31]undecaazacyclotetratriacontine-21,1'-cyclobutan]-(100) (5S,8S,11S,15S,18S,23aS,29S,35S, 37aS)-8-((S)-sec-butyl)-29-(3-chloro-4-(trifluoromethyl) phenethyl)-35-(cyclohexylmethyl)-11-cyclopropyl-18-isopropyl-5,6,12,16,19,33,36-heptamethyl-15-(piperidine-1-carbonyl)docosahydro-2H,4H-spiro[azeto [2,1-u]pyrrolo[2,1-i][1,4,7,10,13,16,19,22,25,28,31] undecaazacyclotetratriacontine-21,1'-cyclopentan]-4,7, 10,13,17,20,23,28,31,34,37(14H,22H)-undecaone, (101) (3S,9S,18S,21S,25R,28S,34S)-3-[2-[3-chloro-4-(trifluoromethyl)phenyl]ethyl]-9-(cyclohexylmethyl)-18-cyclopropyl-21-isobutyl-28-isopropyl-7,10,13,16,22,25,29-heptamethyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone, (102) (3S,6S,9S,13S,16S,19S,22S,25S,31S,34S)-25-[2-[3-chloro-4-(trifluoromethyl)phenyl]ethyl]-31-(cyclohexylmethyl)-16-cyclopentyl-9-isobutyl-19-isopropyl-N,N,3, 4,10,14,17,22,23,29,32-undecamethyl-6-[(1S)-1-methylpropyl]-2,5,8,11,15,18,21,24,27,30,33-undecaoxo-1,4,7,10,14,17,20,23,26,29,32-undecazabicyclo[32.2.0]hexatriacontane-13-carboxamide, (103) (2aS,5S,11S,14S,20S,23S,30aS,33S,36S)-33-((S)-sec-butyl)-14-butyl-11-(3-chloro-4-(trifluoromethyl) phenethyl)-5-(4-chlorobenzyl)-20-isobutyl-4,7,16,17,17, 22,35,36-octamethyl-23-(piperidine-1-carbonyl)

tetracosahydroazeto[1,2-j]pyrido[1,2-a][1,4,7,10,13,16,19,22,25,28,31]undecaazacyclotetratriacontin-3,6,9,12,15,18,21,25,31,34,37(1H,22H,27H)-undecaone, (104) (3S,6S,9S,13S,16S,19S,22S,25S,31S,34S)-25-[2-[3-chloro-4-(trifluoromethyl)phenyl]ethyl]-31-(cyclohexylmethyl)-16-cyclopentyl-22-[2-(3,3-difluoroazetidin-1-yl)ethyl]-9-isobutyl-N,N,3,4,10,14,17,23,29,32-decamethyl-6-[(1S)-1-methylpropyl]-2,5,8,11,15,18,21,24,27,30,33-undecaoxo-19-(2,2,2-trifluoroethyl)-1,4,7,10,14,17,20,23,26,29,32-undecazabicyclo[32.2.0]hexatriacontane-13-carboxamide, (105) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-22-[2-(4,4-difluoro-1-piperidyl)-2-oxo-ethyl]-9-isobutyl-3,4,10,14,17,23,29,32-octamethyl-6-[(1S)-1-methylpropyl]-13-(morpholine-4-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (106) (3S,9S,18S,21S,25S,28S,34S)-3-[2-[3-chloro-4-(trifluoromethyl)phenyl]ethyl]-21-cyclohexyl-9-(cyclohexylmethyl)-28-isopropyl-7,10,13,16,22,26,29-heptamethyl-8-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (107) (3S,9S,18S,21S,25R,28S,34S)-3-[2-[3-chloro-4-(trifluoromethyl)phenyl]ethyl]-9-(cyclohexylmethyl)-28-cyclopentyl-36,36-difluoro-21-isobutyl-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (108) (3S,9S,18S,21S,25S,28S,34S)-9-(cyclohexylmethyl)-21-isobutyl-28-isopropyl-7,10,13,16,22,26,29-heptamethyl-18-[(1S)-1-methylpropyl]-25-(piperidine-1-carbonyl)-3-[2-[4-(trifluoromethyl)phenyl]ethyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (109) (3S,6R,9S,18S,21S,25R,28S,34S)-3-[2-[3-chloro-4-(trifluoromethyl)phenyl]ethyl]-28-cyclopentyl-9-isopropyl-6,7,10,13,16,21,22,25,29-nonamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (110) (3S,9S,18S,21S,25R,28S,34S)-21-but-3-ynyl-3-[2-[3-chloro-4-(trifluoromethyl)phenyl]ethyl]-28-cyclohexyl-9-[(4-iodophenyl)methyl]-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (111) (3S,6S,9S,12S,18S,27S,30S,34S)-9-butyl-18-[(4-chlorophenyl)methy]-12-[(3-iodophenyl)methyl]-3,30-diisobutyl-1,7,16,19,22,25,31-heptamethyl-27-[(1S)-1-methylpropyl]-34-(piperidine-1-carbonyl)-6-[[2-(trifluoromethoxy)phenyl]methyl]-1,4,7,10,13,16,19,22,25,28,31-undecazacyclotetratriacontane-2,5,8,11,14,17,20,23,26,29,32-undecone, (112) (5S,8S,12S,15S,20aS,26S,32S,37aS)-5-((S)-sec-butyl)-26-(4-chlorophenethyl)-32-(cyclohexylmethyl)-8-isobutyl-15-isopropyl-9,13,16,30,33,36-hexamethyl-12-(piperidine-1-carbonyl)docosahydrospiro[azeto[1,2-g]pyrrolo[1,2-v][1,4,7,10,13,16,19,22,25,28,31]undecaazacyclotetratriacontine-18,1'-cyclopentan]-4,7,10,14,17,20,25,28,31,34,37(2H,11H,19H)-undecaone, (113) (8S,11S,17S,26S,29S,33R,36S)-17-[(4-chlorophenyl)methyl]-8,33,36-triisobutyl-29-isopropyl-9,15,18,21,24,30,37-heptamethyl-26-[(1S)-1-methylpropyl]-11-[2-[4-(trifluoromethyl)phenyl]ethyl]-6,9,12,15,18,21,24,27,30,34,37-undecazaspiro[4.33]octatriacontane-7,10,13,16,19,22,25,28,31,35,38-undecone, (114) (3S,9S,18S,21S,25R,28S,34S)-3-[2-[3-chloro-4-(trifluoromethyl)phenyl]ethyl]-9-(cyclohexylmethyl)-28-isopropyl-7,10,13,16,21,25,29-heptamethyl-18-[(1S)-1-methylpropyl]-22-propyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone, (115) (8S,11S,15S,18S,23aS,29S,32R,35S,37aS)-8-((S)-sec-butyl)-29-(3-chloro-4-(trifluoromethyl)phenethyl)-35-(cyclohexylmethyl)-18-isopropyl-6,11,12,16,19,32,33,36-octamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (116) (3S,9S,18S,21S,25R,28S,34S)-3-[2-[3-chloro-4-(trifluoromethyl)phenyl]ethyl]-9-(cyclohexylmethyl)-21-isobutyl-28-isopropyl-7,10,13,22,25,29-hexamethyl-18-[(1S)-1-methylpropyl]-16-propyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone, (117) (5S,8S,11S,15R,18S,23aS,29S,32R,35S,37aS)-8-((S)-sec-butyl)-29-(3-chloro-4-(trifluoromethyl)phenethyl)-18-cyclopentyl-5,6,11,12,15,19,32,33,36-nonamethyl-35-(3-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (118) (8S,11S,17S,26S,29S,33S,36S)-11-[2-[3-chloro-4-(trifluoromethyl)phenyl]ethyl]-36-cyclohexyl-17-(cyclohexylmethyl)-8-[(1R)-1-hydroxyethyl]-29-isobutyl-9,15,18,21,24,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (119) (3S,9S,12S,18S,27S,30S,34R)-18-(cyclohexylmethyl)-12-[2-[3,5-difluoro-4-(trifluoromethyl)phenyl]ethyl]-3,9,30-triisobutyl-4,6,6,10,16,19,22,25,31,34-decamethyl-27-[(1S)-1-methylpropyl]-1,4,7,10,13,16,19,22,25,28,31-undecazacyclotetratriacontane-2,5,8,11,14,17,20,23,26,29,32-undecone, (120) (5S,8S,11S,15S,18S,23aS,29S,35S,37aS)-8-((S)-sec-butyl)-29-(3-chloro-4-(trifluoromethyl)phenethyl)-35-(4-chlorobenzyl)-18-cyclopentyl-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (121) (3S,9S,18S,21S,25R,28S,34S)-9-[(4-chlorophenyl)methyl]-3-[2-[3-chloro-4-(trifluoromethyl)phenyl]ethyl]-21-isobutyl-28-isopropyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (122) (3S,9S,18S,21S,25R,28S,34S)-3-[2-[3-chloro-4-(trifluoromethyl)phenyl]ethyl]-9-(cyclohexylmethyl)-28-cyclopentyl-21-isobutyl-7,10,13,16,22,25,29-heptamethyl-18-[(1S)-1-methylpropyl]spiro[1,4,7,10,13,16,19,22,26, 29,32-undecazabicyclo[32.3.0]heptatriacontane-31,1'-cyclopentane]-2,5,8,11,14,17,20,23,27,30,33-undecone,
(123) (3S,9S,18S,21S,25R,28S,34S)-16-butyl-3-[2-[3-chloro-4-(trifluoromethyl)phenyl]ethyl]-9-(cyclohexylmethyl)-21-isobutyl-28-isopropyl-7,10,13,22,25,29-hexamethyl-8-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(124) (3S,6S,9S,12S,18S,27S,30S,34R)-6-benzyl-18-[(4-chlorophenyl)methyl]-9,30-diisobutyl-3-isopropyl-4,7,10,16,19,22,25,31,34-nonamethyl-27-[(1S)-1-methylpropyl]-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone,
(125) (3S,6S,9S,12S,18S,27S,30S,34S)-6-benzyl-9-butyl-12-[(3-iodophenyl)methyl]-3,30-diisobutyl-18-[(4-methoxyphenyl)methyl]-1,6,7,16,19,22,25,31-octamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone,
(126) (3S,9S,18S,21S,25S,28S,34S)-3-[2-[3-chloro-4-(trifluoromethyl)phenyl]ethyl]-21-cyclobutyl-28-cyclohexyl-7,10,13,16,22,26,29-heptamethyl-18-[(1S)-1-methylpropyl]-9-(propoxymethyl)-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(127) (5S,8S,11S,15S,18S,23aS,29S,35S,37aS)-8-((S)-sec-butyl)-29-(3-chloro-4-(trifluoromethyl)phenethyl)-35-cyclobutyl-18-cyclopentyl-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(128) (5S,8S,11S,15S,18S,23aS,29S,35S,37aS)-15-(azetidine-1-carbonyl)-8-((S)-sec-butyl)-29-(3-chloro-4-(trifluoromethyl)phenethyl)-35-(cyclohexylmethyl)-18-cyclopentyl-11-isobutyl-5,12,16,19,33,36-hexamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(129) (3S,6S,9S,12S,18S,27S,30S,34S)-12-[2-[3-chloro-4-(trifluoromethyl)phenyl]ethyl]-18-(cyclohexylmethyl)-9-[2-(3,3-difluoroazetidin-1-yl)-2-oxo-ethyl]-3-isopropyl-1,4,10,16,19,22,25,30,31-nonamethyl-27-[(1S)-1-methylpropyl]-34-(piperidine-1-carbonyl)-6-(propoxymethyl)-1,4,7,10,13,16,19,22,25,28,31-undecazacyclotetratriacontane-2,5,8,11,14,17,20,23,26,29,32-undecone,
(130) (3S,6S,9S,13S,16S,19S,22S,25S,31S,34S)-25-[2-[3-chloro-4-(trifluoromethyl)phenyl]ethyl]-31-(cyclohexylmethyl)-16-cyclopentyl-22-[2-(3,3-difluoroazetidin-1-yl)ethyl]-9-isobutyl-19-(methoxymethyl)-N,N,3,4,10,14,17,23,29,32-decamethyl-6-[(1S)-1-methylpropyl]-2,5,8,11,15,18,21,24,27,30,33-undecaoxo-1,4,7,10,14,17,20,23,26,29,32-undecazabicyclo[32.2.0]hexatriacontane-13-carboxamide,
(131) (3S,9S,18S,21S,25S,28S,34S)-3-[2-[3-chloro-4-(trifluoromethyl)phenyl]ethyl]-9-(cyclohexylmethyl)-28-isopropyl-7,10,13,16,21,26,29-heptamethyl-18-[(1S)-1-methylpropyl]-25-(piperidine-1-carbonyl)-22-propyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(132) (5S,8S,11S,15R,18S,23aS,25R,29S,35S,37aS)-8-((S)-sec-butyl)-18-cyclopentyl-29-(3,5-difluoro-4-(trifluoromethyl)phenethyl)-25-ethoxy-36-ethyl-11-isobutyl-5,6,12,15,16,19,33-heptamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclobutan]-4,7,10,13,17,20,23,28,31,34,37(14H,22H)-undecaone,
(133) (3S,9S,18S,21S,25R,28S,34S)-9-(cyclohexylmethyl)-3-[2-[3-fluoro-4-(trifluoromethyl)phenyl]ethyl]-21,28-diisobutyl-7,10,13,16,22,25,29-heptamethyl-8-[(1S)-1-methylpropyl]spiro[1,4,7,10,13,16,19,22,26,29,32-undecazabicyclo[32.3.0]heptatriacontane-31,1'-cyclobutane]-2,5,8,11,14,17,20,23,27,30,33-undecone,
(134) (5S,8S,11S,15S,18S,23aS,29S,35S,37aS)-8-((S)-sec-butyl)-18,35-dicyclopentyl-29-(3-fluoro-4-(trifluoromethyl)phenethyl)-11-isobutyl-N,N,5,6,12,16,19,33,36-nonamethyl-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide,
(135) (6'S,15'S,18'S,22'S,25'S,30a'S,36'S,38a'R)-15'-((S)-sec-butyl)-36'-(3-chloro-4-(trifluoromethyl)phenethyl)-6'-(cyclohexylmethyl)-25'-isopropyl-7',10',13',18',19',23',26'-heptamethyl-22'-(piperidine-1-carbonyl)tetracosahydro-5'H-spiro[cyclopentane-1,28'-dipyrrolo[2,1-i:2',1'-o][1,4,7,10,13,16,19,22,25,28,31]undecaazacyclotetratriacontin]-5',8',11',14',17',20',24',27',30',35',38'(21'H,29'H)-undecaone,
(136) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-(cyclopropylmethyl)-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(137) (3S,9S,18S,21S,25S,28S,34S)-3-[2-[3-chloro-4-(trifluoromethyl)phenyl]ethyl]-28-cyclohexyl-9-(cyclohexylmethyl)-22-ethyl-21-isobutyl-7,10,13,16,26,29-hexamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(138) (5S,8S,11S,15R,18S,23aS,29S,35S,37aS)-8-((S)-sec-butyl)-29-(3-chloro-4-(trifluoromethyl)phenethyl)-18-cyclohexyl-36-ethyl-25,25-difluoro-11-isobutyl-5,12,15,16,19,33-hexamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclobutan]-4,7,10,13,17,20,23,28,31,34,37(14H,22H)-undecaone,
(139) (5S,8S,12S,15S,20aS,26S,32S,37aS)-5-((S)-sec-butyl)-32-(cyclohexylmethyl)-26-(3-fluoro-4-(trifluoromethyl)phenethyl)-8-isobutyl-15-isopropyl-9,13,16,30,33,36-hexamethyl-12-(piperidine-1-carbonyl)docosahydrospiro[azeto[1,2-g]pyrrolo[1,2-v][1,4,7,10,13,16,19,22,25,28,31]undecaazacyclotetratriacontine-18,1'-cyclopentan]-4,7,10,14,17,20,25,28,31,34,37(2H,11H,19H)-undecaone,
(140) (3S,9S,18S,21S,25S,28S,34S)-3-[2-[3-chloro-4-(trifluoromethyl)phenyl]ethyl]-21-cyclobutyl-28-cyclohexyl-7,10,13,16,22,26,29-heptamethyl-18-[(1S)-1-methylpropyl]-25-(3-oxa-8-azabicyclo[3.2.1]octane-8-carbonyl)-9-

(propoxymethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (141) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-(2-methoxyethyl)-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (142) (6'S,12'S,21'S,24'S,27a'R,34'S,39a'S)-21'-((S)-sec-butyl)-12'-(cyclohexylmethyl)-6'-(3-fluoro-4-(trifluoromethyl)phenethyl)-24'-isobutyl-34'-isopropyl-10',13',16',19',25',35'-hexamethylhexacosahydrospiro[cyclopentane-1,37'-pyrido[1,2-e]pyrrolo[1,2-v][1,4,7,10,13,16,19,22,25,28,31]undecaazacyclotetratriacontin]-5',8',11',14',17',20',23',26',33',36',39'(38'H)-undecaone, (143) (3S,6S,9S,12S,18S,27S,30S,34S)-9-butyl-18-[(4-chlorophenyl)methyl]-12-[(3-iodophenyl)methyl]-3,30-diisobutyl-1,7,16,19,22,25,31-heptamethyl-27-[(1S)-1-methylpropyl]-34-(piperidine-1-carbonyl)-6-[[3-(trifluoromethoxy)phenyl]methyl]-1,4,7,10,13,16,19,22,25,28,31-undecazacyclotetratriacontane-2,5,8,11,14,17,20,23,26,29,32-undecone, (144) (5S,8S,11S,15S,18S,23aS,29S,35S,37aS)-15-(azetidine-1-carbonyl)-8-((S)-sec-butyl)-29-(3-chloro-4-(trifluoromethyl)phenethyl)-35-(cyclohexylmethyl)-18-cyclopentyl-5,6,12,16,19,33,36-heptamethyl-11-pentyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (145) (5S,8S,11S,15S,18S,23aS,29S,35S,37aS)-29-(3-chloro-4-(trifluoromethyl)phenethyl)-35-(cyclohexylmethyl)-8-(5,5-difluoropentyl)-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (146) (9'S,12'S,16'R,19'S,24a'S,30'S,36'S,38a'S)-9'-((S)-sec-butyl)-30'-(3-chloro-4-(trifluoromethyl)phenethyl)-19'-cyclopentyl-36'-(4-fluorobenzyl)-7',12',13',16',20',34',37'-heptamethyltetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone, (147) (8S,11S,15S,18S,23aS,25S,29S,35S,37aS)-8-((S)-sec-butyl)-29-(3-chloro-4-(trifluoromethyl)phenethyl)-18-cyclohexyl-35-(cyclohexylmethyl)-11-isobutyl-6,12,16,19,33,36-hexamethyl-25-phenyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (148) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-18-(methoxymethyl)-7,10,13,16,22,26,29-heptamethyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (149) (3S,9S,18S,21S,25R,28S,31S,34S)-3-[2-[3-chloro-4-(trifluoromethyl)phenyl]ethyl]-9-(cyclohexylmethyl)-31-ethyl-21-isobutyl-28-isopropyl-7,10,13,16,22,25,29,31-octamethyl-18-[(1S)-1-methylpropyl]-1,4,7,10,13,16,19,22,26,29,32-undecazabicyclo[32.3.0]heptatriacontane-2,5,8,11,14,17,20,23,27,30,33-undecone, (150) (5S,8S,11S,15S,18S,23aS,29S,35S,37aS)-15-(azetidine-1-carbonyl)-8,18-di((S)-sec-butyl)-29-(3-chloro-4-(trifluoromethyl)phenethyl)-35-(cyclohexylmethyl)-11-isobutyl-5,6,12,16,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (151) (9'S,12'S,16'R,19'S,24a'S,30'S,36'S,38a'S)-9'-((S)-sec-butyl)-30'-(3-chloro-4-(trifluoromethyl)phenethyl)-19'-cyclopentyl-7',12',13',16',20',34',37'-heptamethyl-36'-(4-methylbenzyl)tetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone, (152) (3S,6S,9S,12S,18S,27S,30S,34S)-6-benzyl-18-[(4-chlorophenyl)methyl]-9-isobutyl-3-isopropyl-4,7,10,16,19,22,25,30,31-nonamethyl-27-[(1S)-1-methylpropyl]-34-(pyrrolidine-1-carbonyl)-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (153) (3S,9S,12S,18S,27S,30S,34R)-12-[2-(3-chlorophenyl)ethyl]-18-[(4-chlorophenyl)methyl]-3,9-diisobutyl-4,6,6,10,16,19,22,25,30,31,34-undecamethyl-27-[(1S)-1-methylpropyl]-1,4,7,10,13,16,19,22,25,28,31-undecazacyclotetratriacontane-2,5,8,11,14,17,20,23,26,29,32-undecone, (154) (3S,6S,9S,12S,18S,27S,30S,34S)-12-[2-[3-chloro-4-(trifluoromethyl)phenyl]ethyl]-18-(cyclohexylmethyl)-9-[2-(3,3-difluoroazetidin-1-yl)ethyl]-3-isopropyl-1,4,10,16,19,22,25,30,31-nonamethyl-27-[(1S)-1-methylpropyl]-34-(piperidine-1-carbonyl)-6-(propoxymethyl)-1,4,7,10,13,16,19,22,25,28,31-undecazacyclotetratriacontane-2,5,8,11,14,17,20,23,26,29,32-undecone, (155) (5S,8S,11S,15S,18S,23aS,29S,35S,37aS)-15-(azetidine-1-carbonyl)-8-((S)-sec-butyl)-29-(3-chloro-4-(trifluoromethyl)phenethyl)-35-(cyclohexylmethyl)-18-cyclopentyl-5,12,16,19,33,36-hexamethyl-11-pentyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (156) (8S,11S,17S,26S,29S,33S,36S)-11-[2-[3-chloro-4-(trifluoromethyl)phenyl]ethyl]-17-(cyclohexylmethyl)-29-isobutyl-36-isopropyl-8,15,18,21,24,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (157) (5S,8S,11S,15S,18S,23aS,29S,35S,37aS)-29-(3-chloro-4-(trifluoromethyl)phenethyl)-8-cyclobutyl-35-(cyclohexylmethyl)-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (158) (6S,9S,13R,16S,22S,25S,31S,34S)-31-[(4-chlorophenyl)methyl]-25-[2-[3-chloro-4-(trifluoromethyl)phenyl]ethyl]-16,22-diisobutyl-9-isopropyl-4,10,13,17,23,29,32-heptamethyl-6-[(1S)-1-methylpropyl]spiro[1,4,7,10,14, 17,20,23,26,29,32-undecazabicyclo[32.2.0]
hexatriacontane-19,1'-cyclopentane]-2,5,8,11,15,18,21,
24,27,30,33-undecone,
(159) (3S,9S,18S,21S,25S,28S,34S)-3-[2-[3-chloro-4-(trifluoromethyl)phenyl]ethyl]-28-cyclohexyl-21-isobutyl-9-(2-methoxyethyl)-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(160) (11S,17S,26S,29S,33S,36S)-11-[2-[3-chloro-4-(trifluoromethyl)phenyl]ethyl]-36-cyclohexyl-17-(cyclohexylmethyl)-9-ethyl-29-isobutyl-15,18,21,24,30,34,37-heptamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone,
(161) (3S,9S,18S,21S,25S,28S,34S)-21-but-3-ynyl-3-[2-[3-chloro-4-(trifluoromethyl)phenyl]ethyl]-28-cyclohexyl-9-[(4-iodophenyl)methyl]-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(162) (3S,9S,18S,21S,25S,28S,34S)-3-[2-[3-chloro-4-(trifluoromethyl)phenyl]ethyl]-9-(cyclohexylmethyl)-21-isobutyl-7,10,13,16,22,26,29-heptamethyl-18-[(1S)-1-methylpropyl]-28-(2-methylsulfonylethyl)-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(163) (5S,8S,11S,15S,18S,23aS,29S,35S,37aS)-15-(3-oxa-8-azabicyclo[3.2.1]octane-8-carbonyl)-8-((S)-sec-butyl)-29-(3-chloro-4-(trifluoromethyl)phenethyl)-18-cyclopentyl-5,12,16,19,33,36-hexamethyl-11-pentyl-35-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(164) (3S,9S,18S,21S,25S,28S,34S)-18-allyl-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(165) (3S,9S,12S,18S,27S,30S,34R)-9-butyl-8-[(4-chlorophenyl)methyl]-12-[2-[3-fluoro-4-(trifluoromethyl)phenyl]ethyl]-3,30-diisobutyl-1,6,6,7,16,19,22,25,31,34-decamethyl-27-[(1S)-1-methylpropyl]-1,4,7,10,13,16,19,22,25,28,31-undecazacyclotetratriacontane-2,5,8,11,14,17,20,23,26,29,32-undecone,
(166) (3S,9S,12S,18S,27S,30S,34S)-18-(cyclohexylmethyl)-12-[(3-iodophenyl)methyl]-3,30-diisobutyl-1,6,6,7,16,19,22,25,31-nonamethyl-27-[(1S)-1-methylpropyl]-34-(piperidine-1-carbonyl)-9-(p-tolylmethyl)-1,4,7,10,13,16,19,22,25,28,31-undecazacyclotetratriacontane-2,5,8,11,14,17,20,23,26,29,32-undecone,
(167) (3S,9S,18S,21S,25S,28S,34S)-3-[2-(4-chlorophenyl)ethyl]-9-(cyclopentylmethyl)-21-isobutyl-28-isopropyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(168) (3S,6S,9S,12S,18S,27S,30S,34S)-9-butyl-6-[(2-chlorophenyl)methyl]-18-[(4-chlorophenyl)methyl]-12-[(3-iodophenyl)methyl]-3,30-diisobutyl-1,7,16,19,22,25,31-heptamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone,
(169) (3S,6S,9S,13S,16S,22S,25S,31S,34S)-31-(cyclohexylmethyl)-25-[(3-iodophenyl)methyl]-9,16-diisobutyl-22-[(4-methoxyphenyl)methyl]-3,4,10,14,19,19,20,29,32-nonamethyl-6-[(1S)-1-methylpropyl]-13-(piperidine-1-carbonyl)-1,4,7,10,14,17,20,23,26,29,32-undecazabicyclo[32.2.0]hexatriacontane-2,5,8,11,15,18,21,24,27,30,33-undecone,
(170) (3S,9S,12S,18S,27S,30S,34R)-18-[(4-chlorophenyl)methyl]-3,9-diisobutyl-1,6,6,16,19,22,25,30,31,34-decamethyl-27-[(1S)-1-methylpropyl]-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone,
(171) (8S,11S,17S,26S,29S,33S,36S)-11-[2-[3-chloro-4-(trifluoromethyl)phenyl]ethyl]-17-(cyclohexylmethyl)-8-[(3,4-difluorophenyl)methyl]-36-isopropyl-9,15,18,21,24,29,30,34,37-nonamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone,
(172) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-(cyclopropylmethyl)-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(173) (3S,9S,18S,21S,25S,28S,34S)-3-[2-[3-chloro-4-(trifluoromethyl)phenyl]ethyl]-28-cyclohexyl-7,10,13,16,22,26,29-heptamethyl-18-[(1S)-1-methylpropyl]-25-(3-oxa-8-azabicyclo[3.2.1]octane-8-carbonyl)-21-(2,2,2-trifluoroethyl)-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(174) (5S,8S,11S,15S,18S,23aS,29S,35S,37aS)-29-(3-chloro-4-(trifluoromethyl)phenethyl)-35-(cyclohexylmethyl)-11-isobutyl-18-isopropyl-5,6,12,16,19,33,36-heptamethyl-8-(2-(methylsulfonyl)ethyl)-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(175) (5S,8S,11S,15S,18S,23aS,29S,35S,37aS)-8-((S)-sec-butyl)-29-(3-chloro-4-(trifluoromethyl)phenethyl)-11-isobutyl-18-isopropyl-35-(2-methoxyethyl)-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(176) (5S,8S,11S,15S,18S,23aS,29S,35S,37aS)-15-(3-oxa-8-azabicyclo[3.2.1]octane-8-carbonyl)-8-((S)-sec-butyl)-29-(3-chloro-4-(trifluoromethyl)phenethyl)-18-cyclopentyl-11-isobutyl-5,6,12,16,19,33,36-heptamethyl-35-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(177) (8S,11S,17S,26S,29S,33S,36S)-11-[2-(4-chlorophenyl)ethyl]-17-(cyclohexylmethyl)-8-[2-(4,4-difluoro-1- piperidyl)-2-oxo-ethyl]-29-isobutyl-36-isopropyl-9,15, 18,21,24,30,34,37-octamethyl-26-[(1S)-1-methylpropyl]-33-(piperidine-1-carbonyl)-6,9,12,15,18,21,24,27,30,34, 37-undecazaspiro[4.33]octatriacontane-7,10,13,16,19,22, 25,28,31,35,38-undecone, (178) (6S,9S,13R,16S,22S,25S,31S,34S)-31-(cyclohexylmethyl)-25-[2-[3-fluoro-4-(trifluoromethyl)phenyl]ethyl]-9,16,22-triisobutyl-4,10,13,14,19,19,20,29,32-nonamethyl-6-[(1S)-1-methylpropyl]-1,4,7,10,14,17,20,23,26, 29,32-undecazabicyclo[32.2.0]hexatriacontane-2,5,8,11, 15,18,21,24,27,30,33-undecone, (179) (3S,6S,9S,13S,16S,22S,25S,31S,34S)-22-[(3-chlorophenyl)methyl]-25-[2-[3-chloro-4-(trifluoromethyl)phenyl]ethyl]-31-(cyclohexylmethyl)-16-cyclopentyl-9-isobutyl-N,N,3,4,10,14,17,23,29,32-decamethyl-6-[(1S)-1-methylpropyl]-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide, (180) 3-((5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-6,12, 16,19,33,36-hexamethyl-4,7,10,13,17,20,23,28,31,34,37-undecaoxo-15-(piperidine-1-carbonyl) tetratriacontahydro-2H,4H-spiro[azeto[2,1-u]pyrrolo[2, 1-i][1,4,7,10,13,16,19,22,25,28,31] undecaazacyclotetratriacontine-21,1'-cyclopentan]-5-yl)-N-methylpropanamide, (181) (5S,8S,12R,15S,20aS,26S,32S,34aS,38aS)-5-((S)-sec-butyl)-26-(3-chloro-4-(trifluoromethyl)phenethyl)-32-(cyclohexylmethyl)-8-isobutyl-15-isopropyl-9,12,16, 30,33-pentamethyldocosahydro-25H-spiro[bis(azeto)[1, 2-g:1',2'-j]pyrrolo[1,2-v][1,4,7,10,13,16,19,22,25,28,31] undecaazacyclotetratriacontine-18,1'-cyclopentan]-4,7, 10,14,17,20,25,28,31,34,38(2H,11H,19H,34aH)-undecaone, (182) (5S,8S,11S,15S,18S,23aS,29S,35S,37aS)-8-((S)-sec-butyl)-29-(3-chloro-4-(trifluoromethyl)phenethyl)-18,35-dicyclopentyl-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25, 28,31]undecaazacyclotetratriacontine-21,1'-cyclopentan]-4,7,10,13,17,20,23,28,31,34,37(14H,22H)-undecaone, (183) (3S,9S,18S,21S,25R,28S,34S)-3-[2-[3-chloro-4-(trifluoromethyl)phenyl]ethyl]-28-cyclobutyl-9-(cyclohexylmethyl)-21-isobutyl-7,10,13,16,22,25,29-heptamethyl-18-[(1S)-1-methylpropyl]spiro[1,4,7,10,13,16,19,22,26, 29,32-undecazabicyclo[32.3.0]heptatriacontane-31,1'-cyclopentane]-2,5,8,11,14,17,20,23,27,30,33-undecone, (184) (3S,6S,9S,12S,18S,27S,30S,34S)-6,9-dibenzyl-8-[(4-chlorophenyl)methyl]-12-[(3-fluorophenyl)methyl]-3-isopropyl-4,7,16,19,22,25,30,31-octamethyl-27-[(1S)-1-methylpropyl]-34-(pyrrolidine-1-carbonyl)-1,4,7,10,13, 16,19,22,25,28,31-undecazacyclotetracontane-2,5,8, 11,14,17,20,23,26,29,32-undecone, (185) (6'S,9'S,13'R,16'S,21a'S,27'S,33'S,38a'S)-6'-((S)-sec-butyl)-27'-(3-chloro-4-(trifluoromethyl)phenethyl)-33'-(cyclohexylmethyl)-9'-isobutyl-16'-isopropyl-10',13',17', 31',34',37'-hexamethyldocosahydro-1'H-spiro [cyclopentane-1,19'-dipyrrolo[1,2-g:1',2'-v][1,4,7,10,13, 16,19,22,25,28,31]undecaazacyclotetratriacontin]-5',8', 11',15',18',21',26',29',32',35',38'(12'H,20'H,38a'H)-undecaone, (186) (9'S,12'S,16'R,19'S,24a'S,30'S,36'S,38a'S)-9'-((S)-sec-butyl)-30'-(3-chloro-4-(trifluoromethyl)phenethyl)-36'-(3-chlorobenzyl)-19'-cyclopentyl-7',12',13',16',20', 34',37'-heptamethyltetracosahydro-5'H-spiro [cyclopentane-1,22'-dipyrrolo[2,1-i:2',1'-u][1,4,7,10,13, 16,19,22,25,28,31]undecaazacyclotetratriacontin]-5',8', 11',14',18',21',24',29',32',35',38'(15'H,23'H)-undecaone, (187) (3S,9S,18S,21S,25S,28S,34S)-3-[2-[3-chloro-4-(trifluoromethyl)phenyl]ethyl]-28-cyclohexyl-21-isobutyl-7, 10,13,16,22,26,29-heptamethyl-18-[(1S)-1-methylpropyl]-25-(piperidine-1-carbonyl)-9-propyl-spiro[1,4,7,10, 13,16,19,22,26,29,32-undecazabicyclo[32.3.0] heptatriacontane-31,1'-cyclopentane]-2,5,8,11,14,17,20, 23,27,30,33-undecone, (188) (6S,9S,13S,16S,22S,25S,31S,34S)-25-[(3-iodophenyl)methyl]-9,16-diisobutyl-22-[(4-methoxyphenyl) methyl]-4,10,14,19,19,20,29,32-octamethyl-6-[(1S)-1-methylpropyl]-13-(piperidine-1-carbonyl)-31-(p-tolylmethyl)-1,4,7,10,14,17,20,23,26,29,32-undecazabicyclo[32.2.0]hexatriacontane-2,5,8,11,15,18, 21,24,27,30,33-undecone, (189) (3S,9S,12S,18S,27S,30S,34R)-18-[(4-chlorophenyl) methyl]-3,9-diisobutyl-30-isopropyl-4,10,16,19,22,25, 31-heptamethyl-27-[(1S)-1-methylpropyl]-12-[2-[4-(trifluoromethyl)phenyl]ethyl]spiro[1,4,7,10,13,16,19,22,25, 28,31-undecazabicyclo[32.4.0]octatriacontane-6,1'-cyclopentane]-2,5,8,11,14,17,20,23,26,29,32-undecone, (190) (3S,6S,9S,12S,18S,27S,30S,34S)-12-[2-[3-chloro-4-(trifluoromethyl)phenyl]ethyl]-18-(cyclohexylmethyl)-9-[2-(3,3-difluoroazetidin-1-yl)-2-oxo-ethyl]-6-isobutyl-3-isopropyl-1,4,10,16,19,22,25,30,31-nonamethyl-27-[(1S)-1-methylpropyl]-34-(piperidine-1-carbonyl)-1,4,7, 10,13,16,19,22,25,28,31-undecazacyclotetratriacontane-2,5,8,11,14,17,20,23,26,29,32-undecone, (191) (3S,6S,9S,13S,16S,22R,25S,31S,34S)-25-[2-[3-chloro-4-(trifluoromethyl)phenyl]ethyl]-31-(cyclohexylmethyl)-16-cyclopentyl-9-isobutyl-N,N,3,4,10,14,17,22, 29,32-decamethyl-6-[(1S)-1-methylpropyl]-2,5,8,11,15, 18,21,24,27,30,33-undecaoxo-spiro[1,4,7,10,14,17,20, 23,26,29,32-undecazabicyclo[32.2.0]hexatriacontane-19, 1'-cyclopentane]-13-carboxamide, (192) (8S,11S,17S,26S,29S,33S,36S)-11-[2-[3-chloro-4-(trifluoromethyl)phenyl]ethyl]-17-(cyclohexylmethyl)-36-isopropyl-9,15,18,21,24,29,30,34,37-nonamethyl-26-[(1S)-1-methylpropyl]-8-(m-tolylmethyl)-33-(piperidine-1-carbonyl)-6,9,12,15,18,21,24,27,30,34,37-undecazaspiro[4.33]octatriacontane-7,10,13,16,19,22,25, 28,31,35,38-undecone, (193) (5S,8S,11S,15S,18S,23aS,29S,35S,37aS)-18-((S)-sec-butyl)-29-(3-chloro-4-(trifluoromethyl)phenethyl)-11-isobutyl-N,N,5,6,12,16,19,33,36-nonamethyl-35-(4-methylbenzyl)-4,7,10,13,17,20,23,28,31,34,37-undecaoxo-8-(pentan-3-yl)hexatriacontahydro-2H-azeto [2,1-u]pyrrolo[2,1-i][1,4,7,10,13,16,19,22,25,28,31] undecaazacyclotetratriacontine-15-carboxamide, (194) (9'S,12'S,16'R,19'S,24a'S,30'S,36'S,38a'S)-9'-((S)-sec-butyl)-30'-(3-chloro-4-(trifluoromethyl)phenethyl)-19'-cyclopentyl-36'-(3-fluorobenzyl)-7',12',13',16',20', 34',37'-heptamethyltetracosahydro-5'H-spiro [cyclopentane-1,22'-dipyrrolo[2,1-i:2',1'-u][1,4,7,10,13, 16,19,22,25,28,31]undecaazacyclotetratriacontin]-5',8', 11',14',18',21',24',29',32',35',38'(15'H,23'H)-undecaone, (195) (5S,8S,11S,15S,18S,23aS,29S,35S,37aS)-8-((S)-sec-butyl)-29-(3-chloro-4-(trifluoromethyl)phenethyl)-35-(cyclopropylmethyl)-11-isobutyl-18-isopropyl-5,6,12,16, 19,33,36-heptamethyl-15-(piperidine-1-carbonyl) docosahydro-2H,4H-spiro[azeto[2,1-u]pyrrolo[2,1-i][1,4, 7,10,13,16,19,22,25,28,31] undecaazacyclotetratriacontine-21,1'-cyclopentan]-4,7, 10,13,17,20,23,28,31,34,37(14H,22H)-undecaone, (196) (3S,9S,18S,21S,25R,28S,34S)-3-[2-[3-chloro-4-(trifluoromethyl)phenyl]ethyl]-9-(cyclohexylmethyl)-22-ethyl-28-isopropyl-7,10,13,16,21,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (197) (3S,9S,18S,21S,25S,28S,34S)-3-[2-[3-chloro-4-(trifluoromethyl)phenyl]ethyl]-9-(cyclohexylmethyl)-28-cyclopropyl-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (198) (3S,9S,18S,21S,25R,28S,34S)-9-(cyclohexylmethyl)-28-cyclopentyl-3-[2-[3,5-difluoro-4-(trifluoromethyl)phenyl]ethyl]-36,36-difluoro-21-isobutyl-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (199) (3S,6S,9S,12S,18S,27S,30S,34S)-6-benzyl-18-[(4-chlorophenyl)methyl]-3,9-diisobutyl-4,7,10,16,19,22,25,30,31-nonamethyl-27-[(1S)-1-methylpropyl]-34-(pyrrolidine-1-carbonyl)-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (200) (8S,11S,17S,26S,29S,33S,36S)-11-[2-[3-chloro-4-(trifluoromethyl)phenyl]ethyl]-36-cyclohexyl-17-(cyclohexylmethyl)-8-(cyclopropylmethyl)-29-isobutyl-9,15,18,21,24,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (201) (5S,8S,11S,15S,18S,23aS,29S,35S,37aS)-8-((S)-sec-butyl)-29-(3-chloro-4-(trifluoromethyl)phenethyl)-18,35-dicyclopentyl-11-isobutyl-5,6,12,16,19,33,36-heptamethyl-15-(pyrrolidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (202) (3S,9S,12S,18S,27S,30S,34S)-9-butyl-12-[(3-chloro-5-fluoro-phenyl)methyl]-18-[(4-chlorophenyl)methyl]-3,30-diisobutyl-1,6,6,7,16,19,22,25,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (203) (5S,8S,11S,15S,18S,23aS,29S,35S,37aS)-8-((S)-sec-butyl)-18-cyclohexyl-29-(3,5-difluoro-4-(trifluoromethyl)phenethyl)-36-ethyl-25,25-difluoro-11-isobutyl-5,12,15,16,19,33-hexamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclobutan]-4,7,10,13,17,20,23,28,31,34,37(14H,22H)-undecaone, (204) (3S,9S,18S,21S,25R,28S,34S)-3-[2-[3-chloro-4-(trifluoromethyl)phenyl]ethyl]-9-(cyclohexylmethyl)-7-cyclopropyl-21-isobutyl-28-isopropyl-10,13,16,22,25,29-hexamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (205) (8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-8,15,18,21,24,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (206) (3S,6R,9S,18S,21S,25R,28S,34S)-3-[2-[3-chloro-4-(trifluoromethyl)phenyl]ethyl]-28-cyclopentyl-9-[(4-fluorophenyl)methyl]-6,7,10,13,16,21,22,25,29-nonamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (207) (8S,11S,15R,18S,23aS,29S,35S,37aS)-8-((S)-sec-butyl)-29-(3-chloro-4-(trifluoromethyl)phenethyl)-35-(4-chlorobenzyl)-11-isobutyl-18-isopropyl-6,12,15,19,33,36-hexamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (208) (3S,9S,18S,21S,25S,28S,34S)-3-[2-[3-chloro-4-(trifluoromethyl)phenyl]ethyl]-9-(cyclohexylmethyl)-21-isobutyl-7,10,13,16,22,26,29-heptamethyl-18-[(1S)-1-methylpropyl]-25-(piperidine-1-carbonyl)-28-(2,2,2-trifluoroethoxymethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (209) (5S,8S,11S,15S,18S,23aS,29S,35S,37aS)-8,18-di((S)-sec-butyl)-29-(3-chloro-4-(trifluoromethyl)phenethyl)-5,12,16,19,33,36-hexamethyl-11-pentyl-15-(pyrrolidine-1-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (210) (3S,9S,18S,21S,25R,28S,34S)-3-[2-[3-chloro-4-(trifluoromethyl)phenyl]ethyl]-9-(cyclohexylmethyl)-16-ethyl-21-isobutyl-28-isopropyl-7,10,13,22,25,29-hexamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (211) (8S,11S,15R,18S,23aS,29S,35S,37aS)-8-((S)-sec-butyl)-35-(cyclohexylmethyl)-29-(3-fluoro-4-(trifluoromethyl)phenethyl)-11-isobutyl-18-isopropyl-6,12,15,19,33,36-hexamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (212) (3S,9S,18S,21S,25R,28S,34S)-3-[2-[3-chloro-4-(trifluoromethyl)phenyl]ethyl]-9-(cyclobutylmethyl)-21-isobutyl-28-isopropyl-7,10,13,16,22,25,26,29-octamethyl-18-(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (213) (4R,7S,13S,16S,22S,31S,34S)-16-[2-[3-chloro-4-(trifluoromethyl)phenyl]ethyl]-22-(cyclohexylmethyl)-7,13-diisobutyl-4,8,14,20,23,26,29-heptamethyl-31-[(1S)-1-methylpropyl]spiro[1,5,8,11,14,17,20,23,26,29,32-undecazabicyclo[32.4.0]octatriacontane-10,1'-cyclopentane]-2,6,9,12,15,18,21,24,27,30,33-undecone, (214) (3S,6S,9S,12S,18S,27S,30S,34R)-6-benzyl-18-[(4-chlorophenyl)methyl]-3,9-diisobutyl-1,7,16,19,22,25,30,31,34-nonamethyl-27-[(1S)-1-methylpropyl]-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (215) (5S,8S,11S,15S,18S,23aS,29S,35S,37aS)-8,18-di((S)-sec-butyl)-22-butyl-29-(3-chloro-4-(trifluoromethyl)

phenethyl)-11-isobutyl-N,N,5,6,12,16,19,33,36-nonamethyl-35-(4-methylbenzyl)-4,7,10,13,17,20,23,28,31,34,37-undecaoxohexatriacontahydro-2H-azeto[2,1-u]pyrrolo[2,1-i][1,4,7,10,13,16,19,22,25,28,31]undecaazacyclotetratriacontine-15-carboxamide, (216) (3S,6S,9S,13S,16S,22S,25S,31S,34S)-22-[(2-chlorophenyl)methyl]-25-[2-[3-chloro-4-(trifluoromethyl)phenyl]ethyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (217) (8S,11S,17S,26S,29S,33R,36S)-11-[2-[3-chloro-4-(trifluoromethyl)phenyl]ethyl]-17-(cyclohexylmethyl)-8,29,36-triisobutyl-9,15,18,21,24,30,33,37-octamethyl-26-[(1S)-1-methylpropyl]-6,9,12,15,18,21,24,27,30,34,37-undecazaspiro[4.33]octatriacontane-7,10,13,16,19,22,25,28,31,35,38-undecone, (218) (8S,11S,17S,26S,29S,33S,36S)-11-[2-[3-chloro-4-(trifluoromethyl)phenyl]ethyl]-17-(cyclohexylmethyl)-8-[2-(4,4-difluoro-1-piperidyl)-2-oxo-ethyl]-29-isobutyl-36-isopropyl-N,N,9,15,18,21,24,30,34,37-decamethyl-26-[(1S)-1-methylpropyl]-7,10,13,16,19,22,25,28,31,35,38-undecaoxo-6,9,12,15,18,21,24,27,30,34,37-undecazaspiro[4.33]octatriacontane-33-carboxamide, (219) (3S,9S,12S,18S,27S,30S,34R)-18-(cyclohexylmethyl)-3,9-diisobutyl-4,6,6,10,16,19,22,25,30,31,34-undecamethyl-27-[(1S)-1-methylpropyl]-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (220) (3S,9S,18S,21S,25S,28S,34S)-3-[2-[3-chloro-4-(trifluoromethyl)phenyl]ethyl]-9-(cyclopentylmethyl)-21-isobutyl-28-isopropyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (221) (3S,9S,18S,21S,25S,28S,34S)-3-[2-[3-chloro-4-(trifluoromethyl)phenyl]ethyl]-18-cyclobutyl-9-(cyclohexylmethyl)-21-isobutyl-28-isopropyl-7,10,13,16,22,26,29-heptamethyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (222) (3S,6S,9S,13S,16S,19S,22S,25S,31S,34S)-25-[2-[3-chloro-4-(trifluoromethyl)phenyl]ethyl]-31-(cyclohexylmethyl)-16-cyclopentyl-22-[2-(3,3-difluoroazetidin-1-yl)-2-oxo-ethyl]-9-isobutyl-N,N,3,4,10,14,17,23,29,32-decamethyl-6-[(1S)-1-methylpropyl]-2,5,8,11,15,18,21,24,27,30,33-undecaoxo-19-(2,2,2-trifluoroethyl)-1,4,7,10,14,17,20,23,26,29,32-undecazabicyclo[32.2.0]hexatriacontane-13-carboxamide, (223) (3S,9S,18S,21S,25R,28S,31R,34S)-3-[2-[3-chloro-4-(trifluoromethyl)phenyl]ethyl]-9-(cyclohexylmethyl)-31-ethyl-21-isobutyl-28-isopropyl-7,10,13,16,22,25,26,29,31-nonamethyl-18-[(1S)-1-methylpropyl]-1,4,7,10,13,16,19,22,26,29,32-undecazabicyclo[32.3.0]heptatriacontane-2,5,8,11,14,17,20,23,27,30,33-undecone, (224) (3S,6S,9S,12S,18S,27S,30S,34S)-6,9-dibenzyl-12-[(3-chlorophenyl)methyl]-18-[(4-chlorophenyl)methyl]-25-ethyl-3-isopropyl-4,7,16,19,22,30,31-heptamethyl-27-[(1S)-1-methylpropyl]-34-(pyrrolidine-1-carbonyl)-1,4,7,10,13,16,19,22,25,28,31-undecazacyclotetratriacontane-2,5,8,11,14,17,20,23,26,29,32-undecone, (225) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-cyclopentyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (226) (3S,9S,18S,21S,25S,28S,34S)-3-[2-[3-chloro-4-(trifluoromethyl)phenyl]ethyl]-18-(cyclobutoxymethyl)-28-cyclohexyl-9-(cyclohexylmethyl)-21-isobutyl-7,10,13,16,22,26,29-heptamethyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (227) (6'S,12'S,21'S,23a'S,31'R,34'S,39a'S)-21'-((S)-sec-butyl)-12'-(4-chlorobenzyl)-34'-isobutyl-10',13',16',19',31',35'-hexamethyl-6'-(4-(trifluoromethyl)phenethyl)tetracosahydrospiro[cyclopentane-1,37'-pyrido[1,2-a]pyrrolo[1,2-v][1,4,7,10,13,16,19,22,25,28,31]undecaazacyclotetratriacontin]-5',8',11',14',17',20',23',29',33',36',39'(23a'H,30'H,38'H)-undecaone, (228) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-((R)-1-hydroxyethyl)-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (229) (3S,9S,18S,21S,25S,28S,34S)-9-[(4-chlorophenyl)methyl]-3-[2-[3-fluoro-4-(trifluoromethyl)phenyl]ethyl]-21-isobutyl-28-isopropyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (230) (3S,9S,18S,21S,25R,28S,34S)-3-[2-[3-chloro-4-(trifluoromethyl)phenyl]ethyl]-21-(cyclobutylmethyl)-9-(cyclohexylmethyl)-28-isopropyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (231) (3S,9S,18S,21S,25R,28S,34S)-9-(cyclohexylmethyl)-3-[2-[3-fluoro-4-(trifluoromethyl)phenyl]ethyl]-21,28-diisobutyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclohexane]-2,5,8,11,14,17,20,23,27,30,33-undecone, (232) (3S,6S,9S,12S,18S,27S,30S,34S)-9-butyl-12-[(3-iodophenyl)methyl]-3,30-diisobutyl-1,6,7,16,19,22,25,31-octamethyl-27-[(1S)-1-methylpropyl]-34-(piperidine-1-carbonyl)-18-(p-tolylmethyl)-1,4,7,10,13,16,19,22,25,28,31-undecazacyclotetratriacontane-2,5,8,11,14,17,20,23,26,29,32-undecone, (233) 2-[[(3S,6S,9S,12S,18S,27S,30S,34S)-6-benzyl-18-[(4-chlorophenyl)methyl]-3-isobutyl-4,7,16,19,22,25,30,31-octamethyl-27-[(1S)-1-methylpropyl]-2,5,8,11,14,17,20,23,26,29,32-undecaoxo-34-(pyrrolidine-1-carbonyl)-12-[2-[4-(trifluoromethyl)phenyl]ethyl]-1,4,7,10,13,16,19,22,25,28,31-undecazacyclotetratriacont-9-yl]methoxy]-N-tert-butyl-acetamide, (234) (3S,9S,18S,21S,25S,28S,34S)-3-[2-[3-chloro-4-(trifluoromethyl)phenyl]ethyl]-28-cyclohexyl-9-(cyclopropylmethyl)-21-isobutyl-7,10,13,16,22,26,29-heptamethyl-18-[(1S)-1-methylpropyl]-25-(piperidine-1-carbonyl)

spiro[1,4,7,10,13,16,19,22,26,29,32-undecazabicyclo[32.3.0]heptatriacontane-31,1'-cyclopentane]-2,5,8,11,14,17,20,23,27,30,33-undecone, (235) (5S,8S,11S,15S,18S,23aS,29S,35S,37aS)-8-((S)-sec-butyl)-29-(3-chloro-4-(trifluoromethyl)phenethyl)-11-isobutyl-18-isopropyl-5,6,12,16,19,33,36-heptamethyl-35-(2-(methylsulfonyl)ethyl)-15-(piperidine-1-carbonyl)docosahydro-2H4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (236) (5S,8S,11S,15S,18S,23aS,29S,35S,37aS)-8,18-di((S)-sec-butyl)-29-(3-fluoro-4-(trifluoromethyl)phenethyl)-11-isobutyl-5,6,12,16,19,33,36-heptamethyl-15-(piperidine-1-carbonyl)-35-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (237) (3S,9S,18S,25S,28S,34S)-3-[2-[3-chloro-4-(trifluoromethyl)phenyl]ethyl]-28-cyclohexyl-9-(cyclohexylmethyl)-25-[(3-fluorophenyl)methyl]-7,10,13,16,26,29-hexamethyl-18-[(1S)-1-methylpropyl]spiro[1,4,7,10,13,16,19,23,26,29,32-undecazabicyclo[32.3.0]heptatriacontane-31,1'-cyclopentane]-2,5,8,11,14,17,20,24,27,30,33-undecone, (238) 3-[[(3S,9S,18S,21S,25R,28S,34S)-3-[2-[3-chloro-4-(trifluoromethyl)phenyl]ethyl]-21-isobutyl-28-isopropyl-7,10,13,16,22,25,26,29-octamethyl-18-[(1S)-1-methylpropyl]-2,5,8,11,14,17,20,23,27,30,33-undecaoxo-spiro[1,4,7,10,13,16,19,22,26,29,32-undecazabicyclo[32.3.0]heptatriacontane-31,1'-cyclopentane]-9-yl]methyl]benzonitrile, (239) (3S,9S,18S,21S,25S,28S,34S)-3-[2-[3-chloro-4-(trifluoromethyl)phenyl]ethyl]-21-cyclobutyl-28-cyclohexyl-7,10,13,16,22,26,29-heptamethyl-18-[(1S)-1-methylpropyl]-25-(3-oxa-8-azabicyclo[3.2.1]octane-8-carbonyl)-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (240) (3S,6S,9S,12S,18S,27S,30S,34S)-12-[2-[3-chloro-4-(trifluoromethyl)phenyl]ethyl]-18-(cyclohexylmethyl)-9-[2-(4,4-difluoro-1-piperidyl)-2-oxo-ethyl]-6-ethyl-30-isobutyl-3-isopropyl-1,4,10,16,19,22,25,31-octamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (241) (3S,9S,18S,21S,25R,28S,34S)-3-[2-[3-chloro-4-(trifluoromethyl)phenyl]ethyl]-28-cyclohexyl-9-(cyclohexylmethyl)-36,36-difluoro-21-isobutyl-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,1'-cyclobutane]-2,5,8,11,14,17,20,23,27,30,33-undecone, (242) (3S,9S,18S,21S,25R,28S,31S,34S)-31-allyl-3-[2-[3-chloro-4-(trifluoromethyl)phenyl]ethyl]-9-(cyclohexylmethyl)-21-isobutyl-28-isopropyl-7,10,13,16,22,25,29,31-octamethyl-18-[(1S)-1-methylpropyl]-1,4,7,10,13,16,19,22,26,29,32-undecazabicyclo[32.3.0]heptatriacontane-2,5,8,11,14,17,20,23,27,30,33-undecone, (243) (3S,6S,9S,13S,16S,22S,25S,31S,34S)-25-[2-[3-chloro-4-(trifluoromethyl)phenyl]ethyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)-22-(3-pyridylmethyl)spiro[1,4,7,10,14,17,20,23,26,29,32-undecazabicyclo[32.2.0]hexatriacontane-19,1'-cyclopentane]-13-carboxamide, (244) (3S,9S,18S,25S,28S,34S)-3-[2-[3-chloro-4-(trifluoromethyl)phenyl]ethyl]-9-(cyclohexylmethyl)-28-cyclopentyl-25-[(2-hydroxy-2-methyl-propoxy)methyl]-7,10,13,16,23,26,29-heptamethyl-18-[(1S)-1-methylpropyl]spiro[1,4,7,10,13,16,19,23,26,29,32-undecazabicyclo[32.3.0]heptatriacontane-31,1'-cyclopentane]-2,5,8,11,14,17,20,24,27,30,33-undecone, (245) (3S,9S,18S,21S,25S,28S,34S)-3-[2-[3-chloro-4-(trifluoromethyl)phenyl]ethyl]-28-cyclohexyl-7,10,13,16,22,26,29-heptamethyl-18-[(1S)-1-methylpropyl]-25-(pyrrolidine-1-carbonyl)-21-(2,2,2-trifluoroethyl)-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (246) (3S,9S,18S,21S,25S,28S,34S)-3-[2-[3-chloro-4-(trifluoromethyl)phenyl]ethyl]-9-(cyclohexylmethyl)-28-cyclopentyl-7,10,13,16,21,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (247) (3S,9S,12S,18S,27S,30S,34S)-12-[(3-iodophenyl)methyl]-3,30-diisobutyl-9-[(4-methoxyphenyl)methyl]-1,6,6,7,16,19,22,25,31-nonamethyl-27-[(1S)-1-methylpropyl]-34-(piperidine-1-carbonyl)-18-(p-tolylmethyl)-1,4,7,10,13,16,19,22,25,28,31-undecazacyclotetratriacontane-2,5,8,11,14,17,20,23,26,29,32-undecone, (248) (3S,9S,18S,21S,25R,28S,34S)-3-[2-[3-chloro-4-(trifluoromethyl)phenyl]ethyl]-9-(cyclohexylmethyl)-21-(cyclopropylmethyl)-28-isopropyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (249) (5S,8S,11S,15S,18S,23aS,29S,35S,37aS)-8-((S)-sec-butyl)-29-(3-chloro-4-(trifluoromethyl)phenethyl)-18-cyclohexyl-35-(cyclohexylmethyl)-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (250) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-9-isobutyl-22-(isopentyloxymethyl)-N,N,3,4,10,14,17,23,29,32-decamethyl-6-[(1S)-1-methylpropyl]-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide, (251) (7S,10S,16S,25S,28S,32S,35S)-10-[2-[3-chloro-4-(trifluoromethyl)phenyl]ethyl]-16-(cyclohexylmethyl)-7-[2-(4,4-difluoro-1-piperidyl)-2-oxo-ethyl]-28-isobutyl-35-isopropyl-8,14,17,20,23,29,33,36-octamethyl-25-[(1S)-1-methylpropyl]-32-(piperidine-1-carbonyl)-5,8,11,14,17,20,23,26,29,33,36-undecazaspiro[3.33]heptatriacontane-6,9,12,15,18,21,24,27,30,34,37-undecone, (252) 3-[[(3S,6S,9S,12S,18S,27S,30S,34S)-6-benzyl-18-[(4-chlorophenyl)methyl]-3,9-diisobutyl-4,7,16,19,22,25,30,31-octamethyl-27-[(1S)-1-methylpropyl]-2,5,8,11,14,17,20,23,26,29,32-undecaoxo-34-(piperidine-1- carbonyl)-1,4,7,10,13,16,19,22,25,28,31-undecazacyclotetratriacont-12-yl]methyl]benzonitrile, (253) (5S,8S,11S,15S,18S,23aS,29S,35S,37aS)-8,18-di((S)-sec-butyl)-29-(3-chloro-4-(trifluoromethyl)phenethyl)-35-(4-chlorobenzyl)-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (254) (5S,8S,11S,15S,18S,23aS,29S,35S,37aS)-8-((S)-sec-butyl)-29-(3-chloro-4-(trifluoromethyl)phenethyl)-11-isobutyl-18-isopropyl-5,6,12,16,19,33,36-heptamethyl-15-(piperidine-1-carbonyl)-35-((2,2,2-trifluoroethoxy)methyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (255) (9'S,12'S,16'S,19'S,24a'S,26'S,30'S,36'S,38a'S)-9'-((S)-sec-butyl)-30'-(3-chloro-4-(trifluoromethyl)phenethyl)-19'-cyclohexyl-36'-(cyclohexylmethyl)-12'-isobutyl-7',13',17',20',34',37'-hexamethyl-26'-phenyl-16'-(piperidine-1-carbonyl)tetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone, (256) (5S,8S,11S,15S,18S,23aS,29S,35S,37aS)-15-(azetidine-1-carbonyl)-8-((S)-sec-butyl)-29-(3-chloro-4-(trifluoromethyl)phenethyl)-35-(cyclohexylmethyl)-11-isobutyl-18-isopropyl-5,6,12,16,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (257) (3S,9S,12S,18S,27S,30S,34R)-9-butyl-18-[(4-chlorophenyl)methyl]-19-ethyl-12-[2-[3-fluoro-4-(trifluoromethyl)phenyl]ethyl]-3,30-diisobutyl-1,6,6,7,16,22,25,31,34-nonamethyl-27-[(1S)-1-methylpropyl]-1,4,7,10,13,16,19,22,25,28,31-undecazacyclotetratriacontane-2,5,8,11,14,17,20,23,26,29,32-undecone, (258) (3S,9S,18S,21S,25R,28S,34S)-9-[(4-chlorophenyl)methyl]-21,28-diisobutyl-7,10,13,16,22,25,29-heptamethyl-18-[(1S)-1-methylpropyl]-3-[2-[4-(trifluoromethyl)phenyl]ethyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (259) (3S,6S,9S,12S,18S,27S,30S,34S)-9-butyl-18-[(4-chlorophenyl)methyl]-12-[(3-iodophenyl)methyl]-3,30-diisobutyl-6-[(2-methoxyphenyl)methyl]-1,7,16,19,22,25,31-heptamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (260) (5S,8S,11S,15R,18S,23aS,29S,35S,37aS)-8-((S)-sec-butyl)-29-(3-chloro-4-(trifluoromethyl)phenethyl)-35-(cyclohexylmethyl)-5-((R)-1-hydroxyethyl)-11-isobutyl-18-isopropyl-6,12,15,19,33,36-hexamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (261) (3S,9S,12S,18S,27S,30S,34R)-18-[(4-chlorophenyl)methyl]-3,9,30-triisobutyl-4,6,6,10,16,19,22,25,31,34-decamethyl-27-[(1S)-1-methylpropyl]-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (262) (3S,9S,12S,18S,27S,30S,34R)-18-(cyclohexylmethyl)-3,9,30-triisobutyl-1,6,6,7,16,19,22,25,31,34-decamethyl-27-[(1S)-1-methylpropyl]-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (263) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-cyclopentyl-5,12,16,19,33,36-hexamethyl-15-(morpholine-4-carbonyl)-11-pentyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (264) (3S,9S,18S,21S,25R,28S,34S)-3-[2-[3-chloro-4-(trifluoromethyl)phenyl]ethyl]-9-(cyclohexylmethyl)-22-ethyl-28-isopropyl-7,10,13,16,21,25,26,29-octamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (265) (3S,9S,18S,21S,25S,28S,34S)-9-(cyclohexylmethyl)-21-isobutyl-28-isopropyl-7,10,13,16,22,26,29-heptamethyl-18-[(1S)-1-methylpropyl]-3-(2-phenylethyl)-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (266) (3S,9S,18S,21S,25S,28S,34S)-9-(cyclohexylmethyl)-3-[2-[3-fluoro-4-(trifluoromethyl)phenyl]ethyl]-28-isopropyl-7,10,13,16,21,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (267) (8S,11S,15R,18S,23aS,29S,31aR,38S,40aS)-8-((S)-sec-butyl)-29-(3-chloro-4-(trifluoromethyl)phenethyl)-38-(cyclohexylmethyl)-18-isopropyl-6,11,12,15,19,39-hexamethyltetracosahydro-2H,4H,28H-spiro[azeto[2,1-u]pyrido[2,1-o]pyrrolo[2,1-i][1,4,7,10,13,16,19,22,25,28,31]undecaazacyclotetratriacontine-21,1'-cyclopentan]-4,7,10,13,17,20,23,28,31,37,40(14H,22H,31aH)-undecaone, (268) (3S,9S,18S,21S,25R,28S,34S)-3-[2-[3-chloro-4-(trifluoromethyl)phenyl]ethyl]-9-(cyclohexylmethyl)-21-isobutyl-28-isopropyl-7,10,13,16,22,25,26,29-octamethyl-8-[(1S)-1-methylpropyl]spiro[1,4,7,10,13,16,19,22,26,29,32-undecazabicyclo[32.3.0]heptatriacontane-31,1'-cyclopropane]-2,5,8,11,14,17,20,23,27,30,33-undecone, (269) (3S,9S,18S,21S,25R,28S,34S)-28-cyclopentyl-3-[2-[3,5-difluoro-4-(trifluoromethyl)phenyl]ethyl]-36,36-difluoro-21-isobutyl-7,10,13,16,22,25,26,29-octamethyl-18-[(1S)-1-methylpropyl]-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (270) (5S,8S,11S,15S,18S,23aS,29S,35S,37aS)-8-((S)-sec-butyl)-29-(3-chloro-4-(trifluoromethyl)phenethyl)-11-cyclobutyl-35-(cyclohexylmethyl)-18-cyclopentyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (271) (3S,6S,9S,12S,18S,27S,30S,34R)-6-benzyl-18-[(4-chlorophenyl)methyl]-3,9-diisobutyl-4,7,16,19,22,25,30,31,34-nonamethyl-27-[(1S)-1-methylpropyl]-12-[2-[4-

(trifluoromethyl)phenyl]ethyl]-1,4,7,10,13,16,19,22,25, 28,31-undecazacyclotetratriacane-2,5,8,11,14,17,20, 23,26,29,32-undecone, (272) (3S,9S,18S,21S,25S,28S,34S)-3-[2-[3-chloro-4-(trifluoromethyl)phenyl]ethyl]-21-cyclobutyl-28-cyclohexyl-7,10,13,16,22,26,29-heptamethyl-18-[(1S)-1-methylpropyl]-25-(morpholine-4-carbonyl)-9-[[4-(trifluoromethyl) phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (273) (3S,9S,18S,21S,25R,28S,34S)-3-[2-[3-chloro-4-(trifluoromethyl)phenyl]ethyl]-9-(cyclohexylmethyl)-21-isobutyl-28-isopropyl-7,10,13,16,22,29-hexamethyl-18-[(1S)-1-methylpropyl]-25-prop-2-ynyl-spiro[1,4,7,10,13, 16,19,22,26,29,32-undecazabicyclo[32.3.0] heptatriacontane-31,1'-cyclopentane]-2,5,8,11,14,17,20, 23,27,30,33-undecone, (274) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-9-isobutyl-N,N,3,4,10,14,17,22, 23,29,32-undecamethyl-6-[(1S)-1-methylpropyl]-2,5,8, 11,15,18,21,24,27,30,33-undecaoxo-spiro[1,4,7,10,14, 17,20,23,26,29,32-undecazabicyclo[32.2.0] hexatriacontane-19,1'-cyclopentane]-13-carboxamide, (275) (3S,9S,18S,21S,25R,28S,31R,34S)-3-[2-[3-chloro-4-(trifluoromethyl)phenyl]ethyl]-9-(cyclohexylmethyl)-31-ethyl-21-isobutyl-28-isopropyl-7,10,13,16,22,25,29,31-octamethyl-18-[(1S)-1-methylpropyl]-1,4,7,10,13,16,19, 22,26,29,32-undecazabicyclo[32.3.0]heptatriacontane-2, 5,8,11,14,17,20,23,27,30,33-undecone, (276) (5S,8S,11S,15S,18S,23aS,29S,35S,37aS)-8,18-di((S)-sec-butyl)-29-(3-chloro-4-(trifluoromethyl)phenethyl)-11-isobutyl-5,6,12,16,19,33,36-heptamethyl-15-(morpholine-4-carbonyl)-35-(4-(trifluoromethyl)benzyl) docosahydro-2H,4H-spiro[azeto[2,1-u]pyrrolo[2,1-i][1,4, 7,10,13,16,19,22,25,28,31] undecaazacyclotetratriacontine-21,1'-cyclopentan]-4,7, 10,13,17,20,23,28,31,34,37(14H,22H)-undecaone, (277) (8R,11S,17S,26S,29S,33S,36S)-11-[2-[3-chloro-4-(trifluoromethyl)phenyl]ethyl]-36-cyclohexyl-17-(cyclohexylmethyl)-29-isobutyl-8,15,18,21,24,30,34,37-octamethyl-26-[(1S)-1-methylpropyl]-33-(piperidine-1-carbonyl)-6,9,12,15,18,21,24,27,30,34,37-undecazaspiro [4.33]octatriacontane-7,10,13,16,19,22,25,28,31,35,38-undecone, (278) 2-((5S,8S,11S,15S,18S,23aS,29S,35S,37aS)-29-(3-chloro-4-(trifluoromethyl)phenethyl)-35-(cyclohexylmethyl)-11-isobutyl-18-isopropyl-5,6,12,16,19,33,36-heptamethyl-4,7,10,13,17,20,23,28,31,34,37-undecaoxo-15-(piperidine-1-carbonyl)tetratriacontahydro-2H,4H-spiro [azeto[2,1-u]pyrrolo[2,1-i][1,4,7,10,13,16,19,22,25,28, 31]undecaazacyclotetratriacontine-21,1'-cyclopentan]-8-yl)acetonitrile, (279) (5S,8S,11S,15S,18S,23aS,29S,35S,37aS)-8-((S)-secbutyl)-29-(3-chloro-4-(trifluoromethyl)phenethyl)-18-cyclopentyl-36-ethyl-11-isobutyl-N,N,5,6,12,16,19,33-octamethyl-35-(4-methylbenzyl)-4,7,10,13,17,20,23,28,31, 34,37-undecaoxotetratriacontahydro-2H,4H-spiro[azeto [2,1-u]pyrrolo[2,1-i][1,4,7,10,13,16,19,22,25,28,31] undecaazacyclotetratriacontine-21,1'-cyclopentane]-15-carboxamide, (280) (5S,8S,11S,15S,18S,23aS,29S,35S,37aS)-29-(3-chloro-4-(trifluoromethyl)phenethyl)-35-(cyclohexylmethyl)-8-cyclopropyl-11-isobutyl-18-isopropyl-5,6,12,16, 19,33,36-heptamethyl-15-(piperidine-1-carbonyl) docosahydro-2H-spiro[azeto[2,1-u]pyrrolo[2,1-i][1,4, 7,10,13,16,19,22,25,28,31] undecaazacyclotetratriacontine-21,1'-cyclopentan]-4,7, 10,13,17,20,23,28,31,34,37(14H,22H)-undecaone, (281) (3S,9S,18S,21S,25S,28S,34S)-3-[2-[3-chloro-4-(trifluoromethyl)phenyl]ethyl]-18-cyclohexyl-9-(cyclohexylmethyl)-21-isobutyl-28-isopropyl-7,10,13,16,22,26,29-heptamethyl-25-(piperidine-1-carbonyl)spiro[1,4,7,10, 13,16,19,22,26,29,32-undecazabicyclo[32.3.0] heptatriacontane-31,1'-cyclopentane]-2,5,8,11,14,17,20, 23,27,30,33-undecone, (282) (8S,11S,17S,26S,29S,33S,36S)-8-[(3-chlorophenyl) methyl]-11-[2-[3-chloro-4-(trifluoromethyl)phenyl] ethyl]-17-(cyclohexylmethyl)-36-isopropyl-9,15,18,21, 24,29,30,34,37-nonamethyl-26-[(1S)-1-methylpropyl]-33-(piperidine-1-carbonyl)-6,9,12,15,18,21,24,27,30,34, 37-undecazaspiro[4.33]octatriacontane-7,10,13,16,19,22, 25,28,31,35,38-undecone, (283) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-(2-methylsulfonylethyl)-25-(piperidine-1-carbonyl) spiro[1,4,7,10,13,16,19,22,26,29,32-undecazabicyclo [32.3.0]heptatriacontane-31,1'-cyclopentane]-2,5,8,11, 14,17,20,23,27,30,33-undecone, (284) (3S,9S,18S,21S,25S,28S,34S)-3-[2-[3-chloro-4-(trifluoromethyl)phenyl]ethyl]-9-(cyclohexylmethyl)-21-isobutyl-7,10,13,16,22,26,29-heptamethyl-18-[(1S)-1-methylpropyl]-25-(piperidine-1-carbonyl)-28-prop-2-ynyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone, (285) (3S,9S,18S,21S,25R,28S,34S)-3-[2-[3-chloro-4-(trifluoromethyl)phenyl]ethyl]-9,21-bis(cyclohexylmethyl)-28-isopropyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (286) (4R,7S,13S,16S,22S,31S,34S)-22-[(4-chlorophenyl) methyl]-7,13-diisobutyl-4,8,10,10,14,20,23,26,29-nonamethyl-31-[(1S)-1-methylpropyl]-16-[2-[4-(trifluoromethyl)phenyl]ethyl]-1,5,8,11,14,17,20,23,26,29,32-undecazabicyclo[32.4.0]octatriacontane-2,6,9,12,15,18, 21,24,27,30,33-undecone, (287) (3S,9S,18S,21S,25S,28S,31R,34S)-31-allyl-3-[2-[3-chloro-4-(trifluoromethyl)phenyl]ethyl]-9-(cyclohexylmethyl)-21-isobutyl-28-isopropyl-7,10,13,16,22,26,29,31-octamethyl-18-[(1S)-1-methylpropyl]-25-(piperidine-1-carbonyl)-1,4,7,10,13,16,19,22,26,29,32-undecazabicyclo[32.3.0]heptatriacontane-2,5,8,11,14,17, 20,23,27,30,33-undecone, (288) (3S,6S,9S,13S,16S,22R,25S,31S,34S)-25-[2-[3-chloro-4-(trifluoromethyl)phenyl]ethyl]-9-isobutyl-N,N, 3,4,10,14,17,22,23,29,32-undecamethyl-6,16-bis[(1S)-1-methylpropyl]-2,5,8,11,15,18,21,24,27,30,33-undecaoxo-31-(p-tolylmethyl)spiro[1,4,7,10,14,17,20,23, 26,29,32-undecazabicyclo[32.2.0]hexatriacontane-19,1'-cyclopentane]-13-carboxamide, (289) (5S,8S,11S,15S,18S,23aS,29S,35S,37aS)-8-((S)-secbutyl)-18-cyclopentyl-29-(3-fluoro-4-(trifluoromethyl) phenethyl)-11-isobutyl-N,N,5,6,12,16,19,33,36-nonamethyl-4,7,10,13,17,20,23,28,31,34,37-undecaoxo-35-(propoxymethyl)tetratriacontahydro-2H,4H-spiro[azeto [2,1-u]pyrrolo[2,1-i][1,4,7,10,13,16,19,22,25,28,31] undecaazacyclotetratriacontine-21,1'-cyclopentane]-15-carboxamide, (290) (3S,9S,18S,21S,25R,28S,34S)-3-[2-[3-chloro-4-(trifluoromethyl)phenyl]ethyl]-18-(cyclobutylmethyl)-9-(cyclohexylmethyl)-21-isobutyl-28-isopropyl-7,10,13,16,22, 25,29-heptamethyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone, (291) (5S,8S,11S,15R,18S,23aS,29S,35S,37aS)-8-((S)-sec-butyl)-29-(3-chloro-4-(trifluoromethyl)phenethyl)-18-cyclohexyl-35-(cyclohexylmethyl)-5,6,11,12,15,19,21,21,22,33,36-undecamethyltetracosahydro-2H-azeto[2,1-u]pyrrolo[2,1-i][1,4,7,10,13,16,19,22,25,28,31]undecaazacyclotetratriacontin-4,7,10,13,17,20,23,28,31,34,37(14H)-undecaone, (292) (3S,9S,18S,21S,25S,28S,34S)-3-[2-(4-chlorophenyl)ethyl]-28-cyclohexyl-9-(cyclohexylmethyl)-7,10,13,16,21,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (293) (5S,8S,11S,15S,18S,23aS,29S,31aR,37S,39aS)-8-((S)-sec-butyl)-29-(3-chloro-4-(trifluoromethyl)phenethyl)-37-(cyclohexylmethyl)-18-isopropyl-5,6,11,12,16,19,38-heptamethyl-15-(piperidine-1-carbonyl)tetracosahydro-2H,4H-spiro[azeto[2,1-u]dipyrrolo[2,1-i:2',1'-o][1,4,7,10,13,16,19,22,25,28,31]undecaazacyclotetratriacontine-21,1'-cyclopentan]-4,7,10,13,17,20,23,28,31,36,39(14H,22H)-undecaone, (294) (8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-8,9,15,18,21,24,30,34,37-nonamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (295) (3S,9S,12S,18S,27S,30S,34S)-18-[(4-chlorophenyl)methyl]-12-[(3-iodophenyl)methyl]-3,9,30-triisobutyl-1,6,6,7,16,19,22,25,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (296) (5S,8S,11S,15R,18S,23aS,25R,29S,35S,37aS)-8-((S)-sec-butyl)-29-(3-chloro-4-(trifluoromethyl)phenethyl)-18-cyclohexyl-25-ethoxy-36-ethyl-11-isobutyl-5,6,12,15,16,19,33-heptamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclobutan]-4,7,10,13,17,20,23,28,31,34,37(14H,22H)-undecaone, (297) (6'S,9'S,13'S,16'S,25'S,31'S,33a'S,37a'S,38a'S)-16'-((S)-sec-butyl)-31'-(3-chloro-4-(trifluoromethyl)phenethyl)-6'-cyclohexyl-25'-(cyclohexylmethyl)-13'-isobutyl-5',8',12',18',21',24',27'-heptamethyl-9'-(piperidine-1-carbonyl)hexacosahydro-4'H-spiro[cyclopentane-1,3'-[1,4,7,10,13,16,19,22,25,28,31]undecaazacyclotetratriacontino[10,9-a]indol]-1',4',7',11',14',17',20',23',26',29',32'(2'H,8'H)-undecaone, (298) (3S,9S,18S,21S,25S,28S,34S)-9-(cyclohexylmethyl)-3-[2-[3-fluoro-4-(trifluoromethyl)phenyl]ethyl]-21,28-diisobutyl-7,10,13,16,22,29-hexamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (299) (3S,9S,18S,21S,25R,28S,31S,34S)-31-benzyl-9-[(4-chlorophenyl)methyl]-28-isobutyl-7,10,13,16,21,22,25,29,32-nonamethyl-8-[(1S)-1-methylpropyl]-3-[2-[4-(trifluoromethyl)phenyl]ethyl]-1,4,7,10,13,16,19,22,26,29,32-undecazabicyclo[32.4.0]octatriacontane-2,5,8,11,14,17,20,23,27,30,33-undecone, (300) (3S,9S,18S,21S,25R,28S,34S)-21-but-3-ynyl-3-[2-[3-chloro-4-(trifluoromethyl)phenyl]ethyl]-28-cyclohexyl-9-[(4-iodophenyl)methyl]-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (301) (5S,8S,11S,15R,18S,23aS,25R,29S,35S,37aS)-8,18-di((S)-sec-butyl)-29-(3-chloro-4-(trifluoromethyl)phenethyl)-25-ethoxy-11-isobutyl-5,6,12,15,16,19,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (302) (5S,8S,11S,15S,18S,23aS,29S,35S,37aS)-8-((S)-sec-butyl)-29-(3-chloro-4-(trifluoromethyl)phenethyl)-18,35-dicyclopentyl-11-isobutyl-5,6,12,16,19,33,36-heptamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (303) (5S,8S,11S,15S,18S,23aS,29S,35S,37aS)-8-((S)-sec-butyl)-29-(3-chloro-4-(trifluoromethyl)phenethyl)-18-cyclopentyl-11-isopentyl-N,N,5,12,16,19,33,36-octamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (304) (5S,8S,11S,15S,18S,23aS,29S,35S,37aS)-29-(3-chloro-4-(trifluoromethyl)phenethyl)-35-(cyclohexylmethyl)-11-isobutyl-18-isopropyl-5,6,12,16,19,33,36-heptamethyl-15-(piperidine-1-carbonyl)-8-((2,2,2-trifluoroethoxy)methyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (305) (3S,9S,18S,21S,25R,28S,34S)-3-[2-[3-chloro-4-(trifluoromethyl)phenyl]ethyl]-9-(cyclohexylmethyl)-21-isobutyl-16,28-diisopropyl-7,10,13,22,25,29-hexamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (306) allyl 3-[(3S,6S,9S,12S,18S,27S,30S,34S)-6-benzyl-18-[(4-chlorophenyl)methyl]-3-isobutyl-4,7,16,19,22,25,30,31-octamethyl-27-[(1S)-1-methylpropyl]-2,5,8,11,14,17,20,23,26,29,32-undecaoxo-34-(pyrrolidine-1-carbonyl)-12-[2-[4-(trifluoromethyl)phenyl]ethyl]-1,4,7,10,13,16,19,22,25,28,31-undecazacyclotetratriacont-9-yl]propanoate, (307) (9'S,12'S,16'S,19'S,24a'S,30'S,33'R,36'S,38a'S)-9'-((S)-sec-butyl)-30'-(3-chloro-4-(trifluoromethyl)phenethyl)-36'-(cyclohexylmethyl)-19'-isopropyl-7',12',13',17',20',33',34',37'-octamethyl-16'-(piperidine-1-carbonyl)tetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone, (308) (5S,8S,11S,15S,18S,23aS,29S,35S,37aS)-8,18-di((S)-sec-butyl)-29-(3-chloro-4-(trifluoromethyl)phenethyl)-11-isopentyl-N,N,5,12,16,19,33,36-octamethyl-35-(4-methylbenzyl)-4,7,10,13,17,20,23,28,31,34,37-undecaoxotetratriacontahydro-2H,4H-spiro[azeto[2,1-u]

pyrrolo[2,1-i][1,4,7,10,13,16,19,22,25,28,31]
undecaazacyclotetratriacontine-21,1'-cyclopentane]-15-carboxamide,
(309) (3S,9S,18S,21S,25S,28S,34S)-3-[2-[3-chloro-4-(trifluoromethyl)phenyl]ethyl]-9-(cyclobutoxymethyl)-28-cyclohexyl-21-isobutyl-7,10,13,16,22,26,29-heptamethyl-8-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(310) (5S,8S,11S,15R,18S,23aS,29S,32R,35S,37aS)-8-((S)-sec-butyl)-29-(3-chloro-4-(trifluoromethyl)phenethyl)-18-cyclopentyl-35-(3,4-difluorobenzyl)-5,6,11,12,15,19,32,33,36-nonamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(311) (3S,9S,18S,21S,25S,28S,34S)-3-[2-[3-chloro-4-(trifluoromethyl)phenyl]ethyl]-9-(cyclohexylmethyl)-21-isobutyl-7,10,13,16,22,26,29-heptamethyl-18,28-bis[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(312) (3S,9S,12S,18S,27S,30S,34S)-18-(cyclohexylmethyl)-12-[2-[3-fluoro-4-(trifluoromethyl)phenyl]ethyl]-3,9,30-triisobutyl-1,6,6,7,16,19,22,25,31-nonamethyl-27-I(1S)-1-methylpropyl]-34-(pyrrolidine-1-carbonyl)-1,4,7,10,13,16,19,22,25,28,31-undecazacyclotetratriacontane-2,5,8,11,14,17,20,23,26,29,32-undecone,
(313) (5S,8S,11S,15S,18S,23aS,29S,35S,37aS)-8,18-di((S)-sec-butyl)-35-cyclopentyl-29-(3-fluoro-4-(trifluoromethyl)phenethyl)-11-isobutyl-5,6,12,16,19,33,36-heptamethyl-15-(pyrrolidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(314) (5S,8S,11S,15S,18S,21S,23aS,29S,35S,37aS)-8-((S)-sec-butyl)-29-(3-chloro-4-(trifluoromethyl)phenethyl)-35-(cyclohexylmethyl)-18-cyclopentyl-11-isobutyl-N,N,5,6,12,16,19,21,33,36-decamethyl-4,7,10,13,17,20,23,28,31,34,37-undecaoxohexatriacontahydro-2H-azeto[2,1-u]pyrrolo[2,1-i][1,4,7,10,13,16,19,22,25,28,31]undecaazacyclotetratriacontine-15-carboxamide,
(315) (3S,9S,12S,18S,27S,30S,34R)-18-[(4-chlorophenyl)methyl]-3,9,30-triisobutyl-1,6,6,7,16,19,22,25,31,34-decamethyl-27-[(1S)-1-methylpropyl]-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone,
(316) (5S,8S,11S,15S,18S,23aS,29S,35S,37aS)-8,18-di((S)-sec-butyl)-29-(3-fluoro-4-(trifluoromethyl)phenethyl)-11-isobutyl-N,N,5,6,12,16,19,33,36-nonamethyl-4,7,10,13,17,20,23,28,31,34,37-undecaoxo-35-(propoxymethyl)tetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide,
(317) (8S,11S,17S,26S,29S,33S,36S)-8-[(2-chlorophenyl)methyl]-11-[2-[3-chloro-4-(trifluoromethyl)phenyl]ethyl]-17-(cyclohexylmethyl)-36-isopropyl-N,N,9,15,18,21,24,29,30,34,37-undecamethyl-26-[(1S)-1-methylpropyl]-4,7,10,13,16,19,22,25,28,31,35,38-undecaoxo-6,9,12,15,18,21,24,27,30,34,37-undecazaspiro[4.33]octatriacontane-33-carboxamide, (318) (5S,8S,12S,15S,20aS,26S,32S,34aS,38aS)-5-((S)-sec-butyl)-26-(3-chloro-4-(trifluoromethyl)phenethyl)-32-(cyclohexylmethyl)-8-isobutyl-15-isopropyl-9,13,16,30,33-pentamethyl-12-(piperidine-1-carbonyl)docosahydro-25H-spiro[bis(azeto)[1,2-g:1',2'-j]pyrrolo[1,2-v][1,4,7,10,13,16,19,22,25,28,31]undecaazacyclotetratriacontine-18,1'-cyclopentan]-4,7,10,14,17,20,25,28,31,34,38(2H,11H,19H,34aH)-undecaone,
(319) (5S,8S,11S,15R,18S,23aS,29S,35S,37aS)-8-((S)-sec-butyl)-29-(3-chloro-4-(trifluoromethyl)phenethyl)-18-cyclohexyl-25,25-difluoro-11-isobutyl-5,6,12,15,16,19,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(320) (3S,9S,12S,18S,27S,30S,34S)-18-(cyclohexylmethyl)-12-[(3-iodophenyl)methyl]-3,30-diisobutyl-9-1[(4-methoxyphenyl)methyl]-1,6,6,7,16,19,22,25,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone,
(321) (3S,9S,18S,21S,25S,28S,34S)-3-[2-[3-chloro-4-(trifluoromethyl)phenyl]ethyl]-9,21-bis(cyclohexylmethyl)-28-isopropyl-7,10,13,16,22,26,29-heptamethyl-8-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(322) (3S,9S,18S,21S,25R,28S,31S,34S,36R)-31-benzyl-9-[(4-chlorophenyl)methyl]-36-ethoxy-28-isobutyl-7,10,13,16,21,22,25,29,32-nonamethyl-18-[(1S)-1-methylpropyl]-3-[2-[4-(trifluoromethyl)phenyl]ethyl]-1,4,7,10,13,16,19,22,26,29,32-undecazabicyclo[32.3.0]heptatriacontane-2,5,8,11,14,17,20,23,27,30,33-undecone,
(323) (3S,9S,12S,18S,27S,30S,34R)-18-[(4-chlorophenyl)methyl]-3,9-diisobutyl-1,6,6,7,16,19,22,25,30,31,34-undecamethyl-27-[(1S)-1-methylpropyl]-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone,
(324) (10'S,13'S,17'S,20'S,25a'S,31'S,37'S,39a'S)-10'-((S)-sec-butyl)-37'-(cyclohexylmethyl)-31'-(3,4-dichlorophenethyl)-13'-isobutyl-20'-isopropyl-8',14',18',21',35',38'-hexamethyl-17'-(piperidine-1-carbonyl)tetracosahydro-2'H6'H-spiro[cyclopentane-1,23'-pyrido[2,1-u]pyrrolo[2,1-i][1,4,7,10,13,16,19,22,25,28,31]undecaazacyclotetratriacontin]-6',9',12',15',19',22',25',30',33',36',39'(16'H,24'H)-undecaone,
(325) (3S,9S,18S,21S,25S,28S,34S)-3-[2-[3-chloro-4-(trifluoromethyl)phenyl]ethyl]-9-(cyclopropylmethyl)-21-isobutyl-28-isopropyl-7,10,13,16,22,26,29-heptamethyl-8-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(326) (3S,9S,18S,21S,25S,28S,34S)-3-[2-[3-chloro-4-(trifluoromethyl)phenyl]ethyl]-28-cyclohexyl-9-(cyclopentylmethyl)-7,10,13,16,22,26,29-heptamethyl-8-[(1S)-1-methylpropyl]-25-(pyrrolidine-1-carbonyl)-21-(2,2,2-trifluoroethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (327) (3S,9S,18S,21S,25S,28S,34S)-3-[2-[3-chloro-4-(trifluoromethyl)phenyl]ethyl]-21-cyclobutyl-28-cyclohexyl-9-(cyclopentylmethyl)-7,10,13,16,22,26,29-heptamethyl-18-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (328) (3S,9S,18S,21S,25S,28S,34S)-9-[(4-chlorophenyl)methyl]-10-ethyl-3-[2-[3-fluoro-4-(trifluoromethyl)phenyl]ethyl]-21,28-diisobutyl-7,13,16,22,26,29-hexamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (329) (3S,9S,18S,21S,25R,28S,34S)-3-[2-[3-chloro-4-(trifluoromethyl)phenyl]ethyl]-9-(cyclohexylmethyl)-16-(2-ethoxyethyl)-21-isobutyl-28-isopropyl-7,10,13,22,25,29-hexamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (330) (3S,9S,12S,18S,27S,30S,34S)-9-[(4-chlorophenyl)methyl]-18-(cyclohexylmethyl)-12-[(3-iodophenyl)methyl]-3,30-diisobutyl-1,6,6,7,16,19,22,25,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (331) (3S,6S,9S,12S,18S,27S,30S,34S)-12-[2-[3-chloro-4-(trifluoromethyl)phenyl]ethyl]-18-(cyclohexylmethyl)-9-[2-(3,3-difluoroazetidin-1-yl)ethyl]-6-isobutyl-3-isopropyl-1,4,10,16,19,22,25,30,31-nonamethyl-27-1[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone.

(332) (3S,9S,12S,18S,27S,30S,34R)-18-[(4-chlorophenyl)methyl]-12-[2-[3-fluoro-4-(trifluoromethyl)phenyl]ethyl]-3,30-diisobutyl-1,6,6,7,16,19,22,25,31,34-decamethyl-9,27-bis[(1S)-1-methylpropyl]-1,4,7,10,13,16,19,22,25,28,31-undecazacyclotetratriacontane-2,5,8,11,14,17,20,23,26,29,32-undecone, (333) (3S,9S,18S,21S,25R,28S,34S)-3-[2-[3-chloro-4-(trifluoromethyl)phenyl]ethyl]-9-(cyclohexylmethyl)-18-cyclopentyl-21-isobutyl-28-isopropyl-7,10,13,16,22,25,29-heptamethyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone, (334) (5S,8S,11S,15S,18S,23aS,29S,35S,37aS)-8-((S)-sec-butyl)-35-(cyclohexylmethyl)-18-cyclopentyl-29-(3-fluoro-4-(trifluoromethyl)phenethyl)-11-isobutyl-N,N,5,6,12,16,19,33,36-nonamethyl-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (335) (6S,9S,13S,16S,22S,25S,31S,34S)-25-[(3-iodophenyl)methyl]-9,16-diisobutyl-4,10,14,19,19,20,29,32-octamethyl-6-[(1S)-1-methylpropyl]-22-(o-tolylmethyl)-13-(piperidine-1-carbonyl)-31-(p-tolylmethyl)-1,4,7,10,14,17,20,23,26,29,32-undecazabicyclo[32.2.0]hexatriacontane-2,5,8,11,15,18,21,24,27,30,33-undecone, (336) (3S,9S,12S,18S,27S,30S,34S)-18-(cyclohexylmethyl)-12-[(3-iodophenyl)methyl]-3,30-diisobutyl-1,6,6,7,16,19,22,25,31-nonamethyl-27-[(1S)-1-methylpropyl]-34-(piperidine-1-carbonyl)-9-[[4-(trifluoromethyl)phenyl]methyl]-1,4,7,10,13,16,19,22,25,28,31-undecazacyclotetratriacontane-2,5,8,11,14,17,20,23,26,29,32-undecone, (337) (3S,9S,18S,21S,25R,28S,34S)-9-(cyclohexylmethyl)-3-[2-[3-fluoro-4-(trifluoromethyl)phenyl]ethyl]-21-isobutyl-28-isopropyl-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (338) (3S,6S,9S,13S,16S,22S,25S,31S,34S)-25-[2-[3-chloro-4-(trifluoromethyl)phenyl]ethyl]-16-cyclohexyl-31-(cyclohexylmethyl)-9-isobutyl-3,4,10,14,17,23,29,32-octamethyl-6-[(1S)-1-methylpropyl]-22-[(5-methyl-3-pyridyl)methyl]-13-(piperidine-1-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (339) (3S,9S,18S,21S,25S,28S,34S)-3-[2-[3-chloro-4-(trifluoromethyl)phenyl]ethyl]-21-cyclobutyl-28-cyclohexyl-7,10,13,16,22,26,29-heptamethyl-18-[(1S)-1-methylpropyl]-9-(p-tolylmethyl)-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone.

(340) (3S,6S,9S,13S,16S,22S,25S,31S,34S)-25-[2-[3-chloro-4-(trifluoromethyl)phenyl]ethyl]-9-isobutyl-N,N,3,4,10,14,17,23,29,32-decamethyl-6,16-bis[(1S)-1-methylpropyl]-2,5,8,11,15,18,21,24,27,30,33-undecaoxo-22,31-bis(p-tolylmethyl)spiro[1,4,7,10,14,17,20,23,26,29,32-undecazabicyclo[32.2.0]hexatriacontane-19,1'-cyclopentane]-13-carboxamide, (341) (5S,8S,11S,15R,18S,23aS,29S,35S,37aS)-8-((S)-sec-butyl)-29-(3-chloro-4-(trifluoromethyl)phenethyl)-35-(cyclohexylmethyl)-18-isopropyl-5,6,11,12,15,16,19,21,21,22,33,36-dodecamethyltetracosahydro-2H-azeto[2,1-u]pyrrolo[2,1-i][1,4,7,10,13,16,19,22,25,28,31]undecaazacyclotetratriacontin-4,7,10,13,17,20,23,28,31,34,37(14H)-undecaone, (342) (5S,8S,11S,15S,18S,23aS,29S,35S,37aS)-8,18-di((S)-sec-butyl)-29-(3-chloro-4-(trifluoromethyl)phenethyl)-N,N,5,12,16,19,33,36-octamethyl-35-(4-methylbenzyl)-4,7,10,13,17,20,23,28,31,34,37-undecaoxo-11-pentyltetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (343) (5S,8S,11S,15S,18S,23aS,29S,35S,37aS)-8-((S)-sec-butyl)-29-(3-chloro-4-(trifluoromethyl)phenethyl)-18,35-dicyclopentyl-5,6,12,16,19,33,36-heptamethyl-15-(morpholine-4-carbonyl)-11-pentyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (344) (5S,8S,11S,15R,18S,23aS,25R,29S,35S,37aS)-8-((S)-sec-butyl)-18-cyclopentyl-29-(3,5-difluoro-4-(trifluoromethyl)phenethyl)-25-ethoxy-11-isobutyl-5,6,12,15,16,19,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (345) (5S,8S,11S,15R,18S,23aS,29S,35S,37aS)-8-((S)-sec-butyl)-29-(3-chloro-4-(trifluoromethyl)phenethyl)-18-cyclohexyl-36-ethyl-25,25-difluoro-11-isobutyl-5,6,12,15,16,19,33-heptamethyl-35-(4-(trifluoromethyl)benzyl)docosahydro-2H,4H-spiro[azeto[2,1-u]pyrrolo[2,1-i][1,4, 7,10,13,16,19,22,25,28,31]undecaazacyclotetratriacontine-21,1'-cyclobutan]-4,7,10,13,17,20,23,28,31,34,37(14H,22H)-undecaone, (346) (8S,11S,17S,26S,29S,33S,36S)-11-[2-[3-chloro-4-(trifluoromethyl)phenyl]ethyl]-17-(cyclohexylmethyl)-36-isopropyl-9,15,18,21,24,29,30,34,37-nonamethyl-26-[(1S)-1-methylpropyl]-33-(piperidine-1-carbonyl)-8-(p-tolylmethyl)-6,9,12,15,18,21,24,27,30,34,37-undecazaspiro[4.33]octatriacontane-7,10,13,16,19,22,25,28,31,35,38-undecone, (347) (6'S,12'S,21'S,24'S,26a'R,29a'R,32'S,37a'S)-21'-((S)-sec-butyl)-6'-(3-chloro-4-(trifluoromethyl)phenethyl)-12'-(cyclohexylmethyl)-24'-isobutyl-32'-isopropyl-10',13',16',19',25',33'-hexamethylhexacosahydrospiro[cyclopenta[1,35'-cyclopenta[fi]pyrrolo[1,2-v][1,4,7,10,13,16,19,22,25,28,31]undecaazacyclotetratriacontin]-5',8',11',14',17',20',23',26',31',34',37'(36'H)-undecaone, (348) (5S,8S,11S,15R,18S,23aS,29S,35S,37aS)-8-((S)-sec-butyl)-29-(3-chloro-4-(trifluoromethyl)phenethyl)-18-cyclohexyl-11-isobutyl-5,6,12,15,16,19,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (349) (5S,8S,11S,15S,18S,23aS,29S,31aR,38S,40aS)-8-((S)-sec-butyl)-29-(3-chloro-4-(trifluoromethyl)phenethyl)-38-(cyclohexylmethyl)-18-isopropyl-5,6,11,12,16,19,39-heptamethyl-15-(piperidine-1-carbonyl)tetracosahydro-2H,4H,28H-spiro[azeto[2,1-u]pyrido[2,1-o]pyrrolo[2,1-i][1,4,7,10,13,16,19,22,25,28,31]undecaazacyclotetratriacontine-21,1'-cyclopentan]-4,7,10,13,17,20,23,28,31,37,40(14H,22H,31aH)-undecaone, (350) (8S,11S,17S,26S,29S,33R,36S)-11-[2-[3-chloro-4-(trifluoromethyl)phenyl]ethyl]-17-(cyclohexylmethyl)-8-[2-(4,4-difluoro-1-piperidyl)-2-oxo-ethyl]-29-isobutyl-36-isopropyl-9,15,18,21,24,30,33,34,37-nonamethyl-26-[(1S)-1-methylpropyl]-6,9,12,15,18,21,24,27,30,34,37-undecazaspiro[4.33]octatriacontane-7,10,13,16,19,22,25,28,31,35,38-undecone, (351) (3S,6S,9S,12S,18S,27S,30S)-6-benzyl-18-[(4-chlorophenyl)methyl]-9-isobutyl-3-isopropyl-4,7,10,16,19,22,25,30,31-nonamethyl-27-[(1S)-1-methylpropyl]-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (352) (2aS,5S,11S,14S,20S,23S,30aS,33S)-33-((S)-sec-butyl)-14-butyl-11-(3-chloro-4-(trifluoromethyl)phenethyl)-5-(4-chlorobenzyl)-20-isobutyl-4,7,16,17,17,22,35-heptamethyl-23-(piperidine-1-carbonyl)tetracosahydroazeto[1,2-j]pyrido[1,2-a][1,4,7,10,13,16,19,22,25,28,31]undecaazacyclotetratriacontin-3,6,9,12,15,18,21,25,31,34,37(1H,22H,27H)-undecaone, (353) (3S,9S,18S,21S,25S,28S,34S)-3-[2-[3-chloro-4-(trifluoromethyl)phenyl]ethyl]-21-cyclobutyl-28-cyclohexyl-7,10,13,16,22,26,29-heptamethyl-18-[(1S)-1-methylpropyl]-25-(3-oxa-8-azabicyclo[3.2.1]octane-8-carbonyl)-9-(p-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (354) (5S,8S,11S,15R,18S,23aS,29S,35S,37aS)-8-((S)-sec-butyl)-29-(3-chloro-4-(trifluoromethyl)phenethyl)-18-cyclopentyl-11-isobutyl-5,6,12,15,19,21,21,33,36-nonamethyl-35-(4-methylbenzyl)tetracosahydro-2H-azeto[2,1-u]pyrrolo[2,1-i][1,4,7,10,13,16,19,22,25,28,31]undecaazacyclotetratriacontin-4,7,10,13,17,20,23,28,31,34,37(14H)-undecaone, (355) (3S,6S,9S,13S,16S,19S,22S,25S,31S,34S)-25-[2-[3-chloro-4-(trifluoromethyl)phenyl]ethyl]-31-(cyclohexylmethyl)-16-cyclopentyl-9-isobutyl-19-isopropyl-N,N,3,4,10,14,17,23,29,32-decamethyl-6-[(1S)-1-methylpropyl]-2,5,8,11,15,18,21,24,27,30,33-undecaoxo-22-(thiazol-4-ylmethyl)-1,4,7,10,14,17,20,23,26,29,32-undecazabicyclo[32.2.0]hexatriacontane-13-carboxamide, (356) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,26,29-hexamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (357) 2-[[(3S,9S,18S,21S,25R,28S,34S)-3-[2-[3-chloro-4-(trifluoromethyl)phenyl]ethyl]-21-isobutyl-28-isopropyl-7,10,13,16,22,25,26,29-octamethyl-18-[(1S)-1-methylpropyl]-2,5,8,11,14,17,20,23,27,30,33-undecaoxo-spiro[1,4,7,10,13,16,19,22,26,29,32-undecazabicyclo[32.3.0]heptatriacontane-31,1'-cyclopentane]-9-yl]methyl]benzonitrile, (358) (5S,8S,11S,15S,18S,23aS,29S,35S,37aS)-29-(3-chloro-4-(trifluoromethyl)phenethyl)-35-(cyclohexylmethyl)-8-(cyclopropylmethyl)-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (359) (3S,9S,18S,21S,25R,28S,34S)-3-[2-[3-chloro-4-(trifluoromethyl)phenyl]ethyl]-28-cyclopentyl-36,36-difluoro-21-isobutyl-7,10,13,16,22,25,26,29-octamethyl-18-[(1S)-1-methylpropyl]-9-(p-tolylmethyl)spiro[1,4,7,10,13,16,19,22,26,29,32-undecazabicyclo[32.3.0]heptatriacontane-31,1'-cyclobutane]-2,5,8,11,14,17,20,23,27,30,33-undecone, (360) (3S,9S,18S,21S,25S,28S,34S)-3-[2-[3-chloro-4-(trifluoromethyl)phenyl]ethyl]-9-(cyclohexylmethyl)-28-isopropyl-7,10,13,16,21,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (361) (3S,6R,9S,18S,21S,25R,28S,34S)-3-[2-[3-chloro-4-(trifluoromethyl)phenyl]ethyl]-28-cyclopentyl-6,7,9,10,13,16,21,22,25,29-decamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (362) (5S,8S,11S,15R,18S,23aS,25R,29S,35S,37aS)-8,18-di((S)-sec-butyl)-29-(3,5-difluoro-4-(trifluoromethyl)phenethyl)-25-ethoxy-11-isobutyl-5,6,12,15,16,19,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (363) (5S,8S,11S,15S,18S,23aS,29S,35S,37aS)-8-((S)-sec-butyl)-29-(3-chloro-4-(trifluoromethyl)phenethyl)-18-cyclopentyl-11-isobutyl-N,N,5,12,16,19,33,36-octamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (364) (3S,9S,18S,21S,25R,28S,34S)-9-(cyclohexylmethyl)-3-[2-[3,5-difluoro-4-(trifluoromethyl)phenyl]ethyl]-21,28-diisobutyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (365) (5S,8S,11S,15R,18S,23aS,25R,29S,35S,37aS)-8-((S)-sec-butyl)-18-cyclohexyl-29-(3,5-difluoro-4-(trifluoromethyl)phenethyl)-25-ethoxy-11-isobutyl-5,6,12,15,16,19,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclobutan]-4,7,10,13,17,20,23,28,31,34,37(14H,22H)-undecaone, (366) (5S,8S,11S,15R,18S,23aS,29S,35S,37aS)-8-((S)-sec-butyl)-29-(3-chloro-4-(trifluoromethyl)phenethyl)-18-cyclopentyl-11-isobutyl-5,6,12,15,16,19,33,36-octamethyl-35-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (367) (3S,9S,18S,21S,25S,28S,34S)-3-[2-[3-chloro-4-(trifluoromethyl)phenyl]ethyl]-28-cyclohexyl-9-(cyclopentylmethyl)-7,10,13,16,22,26,29-heptamethyl-8-[(1S)-1-methylpropyl]-25-(morpholine-4-carbonyl)-21-(2,2,2-trifluoroethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (368) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,6,16,19,33,36-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (369) (3S,9S,18S,28S,34S)-3-[2-[3-chloro-4-(trifluoromethyl)phenyl]ethyl]-9-(cyclohexylmethyl)-28-cyclopentyl-7,10,13,16,23,26,29-heptamethyl-18-1(1S)-1-methylpropyl]spiro[1,4,7,10,13,16,19,23,26,29,32-undecazabicyclo[32.3.0]heptatriacontane-31,1'-cyclopentane]-2,5,8,11,14,17,20,24,27,30,33-undecone, (370) (5S,8S,11S,15S,18S,23aS,29S,35S,37aS)-8-((S)-sec-butyl)-29-(3-chloro-4-(trifluoromethyl)phenethyl)-18-cyclopentyl-11-isobutyl-5,6,12,16,19,33,36-heptamethyl-15-(piperidine-1-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (371) (5S,8S,11S,15R,18S,23aS,29S,35S,37aS)-8-((S)-sec-butyl)-18-cyclopentyl-29-(3,5-difluoro-4-(trifluoromethyl)phenethyl)-11-isobutyl-5,6,12,15,16,19,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (372) (3S,6S,9S,12S,18S,27S,30S,34S)-6-benzyl-18-[(4-chlorophenyl)methyl]-3,9-diisobutyl-7,16,19,22,25,30,31-heptamethyl-27-[(1S)-1-methylpropyl]-34-(pyrrolidine-1-carbonyl)-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (373) 3-[[(3S,6S,9S,12S,18S,27S,30S,34S)-6-benzyl-18-[(4-chlorophenyl)methyl]-3,9-diisobutyl-4,7,16,19,22,25,30,31-octamethyl-27-[(1S)-1-methylpropyl]-2,5,8,11,14,17,20,23,26,29,32-undecaoxo-34-(pyrrolidine-1-carbonyl)-1,4,7,10,13,16,19,22,25,28,31-undecazacyclotetratriacont-12-yl]methyl]benzonitrile, (374) (5S,8S,11S,15R,18S,23aS,25R,29S,35S,37aS)-8,18-di((S)-sec-butyl)-29-(3,5-difluoro-4-(trifluoromethyl)phenethyl)-25-ethoxy-36-ethyl-11-isobutyl-5,6,12,15,16,19,33-heptamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (375) (3S,9S,18S,21S,25R,28S,34S)-3-[2-[3-chloro-4-(trifluoromethyl)phenyl]ethyl]-28-cyclohexyl-36,36-difluoro-21-isobutyl-7,10,13,16,22,25,26,29-octamethyl-18-[(1S)-1-methylpropyl]-9-(p-tolylmethyl)spiro[1,4,7,10,13,16,19,22,26,29,32-undecazabicyclo[32.3.0]heptatriacontane-31,1'-cyclobutane]-2,5,8,11,14,17,20,23,27,30,33-undecone, (376) (3S,9S,12S,18S,27S,30S,34S)-12-[(3-iodophenyl)methyl]-3,30-diisobutyl-1,6,6,7,16,19,22,25,31-nonamethyl-27-1[(1S)-1-methylpropyl]-34-(piperidine-1-carbonyl)-18-(p-tolylmethyl)-9-[[3-(trifluoromethyl)phenyl]methyl]-1,4,7,10,13,16,19,22,25,28,31-undecazacyclotetratriacontane-2,5,8,11,14,17,20,23,26,29,32-undecone, (377) (5S,8S,11S,15R,18S,23aS,29S,35S,37aS)-8-((S)-sec-butyl)-18-cyclohexyl-29-(3,5-difluoro-4-(trifluoromethyl)phenethyl)-36-ethyl-25,25-difluoro-11-isobutyl-5,6,12,15,16,19,33-heptamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclobutan]-4,7,10,13,17,20,23,28,31,34,37(14H,22H)-undecaone, (378) (3S,6S,9S,13S,16S,22S,25S,31S,34S)-25-[2-[3-chloro-4-(trifluoromethyl)phenyl]ethyl]-9-isobutyl-N,N,3,4,10,14,17,22,23,29,32-undecamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (379) (3S,6S,9S,13S,16S,19S,22S,25S,31S,34S)-25-[2-[3-chloro-4-(trifluoromethyl)phenyl]ethyl]-22-[2-(3,3-difluoro-1-piperidyl)ethyl]-9-isobutyl-19-isopropyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)-1,4,7,10,14,17,20,23,26,29,32-undecazabicyclo[32.2.0]hexatriacontane-13-carboxamide, (380) (3S,6R,9S,18S,21S,25S,28S,34S)-3-[2-[3-chloro-4-(trifluoromethyl)phenyl]ethyl]-9-(cyclohexylmethyl)-28-isopropyl-6,7,10,13,16,21,22,26,29-nonamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (381) (5S,8S,11S,15S,18S,23aS,29S,35S,37aS)-8,18-di((S)-sec-butyl)-29-(3-chloro-4-(trifluoromethyl)phenethyl)-35-cyclopentyl-11-isobutyl-5,6,12,16,19,33,36-heptamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (382) (3S,6S,9S,13S,16S,19S,22R,25S,31S,34S)-25-[2-[3-chloro-4-(trifluoromethyl)phenyl]ethyl]-9-isobutyl-N,N,3,4,10,14,17,19,22,29,32-undecamethyl-6,16-bis[(1S)-1- methylpropyl]-2,5,8,11,15,18,21,24,27,30,33-undecaoxo-31-(p-tolylmethyl)-1,4,7,10,14,17,20,23,26,29,32-undecazabicyclo[32.2.0]hexatriacontane-13-carboxamide, (383) (3S,9S,18S,21S,25R,28S,31S,34S)-9-[(4-chlorophenyl)methyl]-31-(cyclohexylmethyl)-28-isobutyl-7,10,13,16,21,22,25,29,32-nonamethyl-18-[(1S)-1-methylpropyl]-3-[2-[4-(trifluoromethyl)phenyl]ethyl]-1,4,7,10,13,16,19,22,26,29,32-undecazabicyclo[32.3.0]heptatriacontane-2,5,8,11,14,17,20,23,27,30,33-undecone, (384) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-9-isobutyl-N,N,3,4,10,14,17,23,29,32-decamethyl-6-[(1S)-1-methylpropyl]-2,5,8,11,15,18,21,24,27,30,33-undecaoxo-22-(thiazol-4-ylmethyl)spiro[1,4,7,10,14,17,20,23,26,29,32-undecazabicyclo[32.2.0]hexatriacontane-19,1'-cyclopentane]-13-carboxamide, (385) (3S,6S,9S,13S,16S,22S,25S,31S,34S)-25-[2-[3-chloro-4-(trifluoromethyl)phenyl]ethyl]-22-[(4-fluorophenyl)methyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (386) (5S,8S,11S,15R,18S,23aS,29S,35S,37aS)-8-((S)-sec-butyl)-18,35-dicyclopentyl-29-(3-fluoro-4-(trifluoromethyl)phenethyl)-11-isobutyl-5,6,12,15,16,19,33,36-octamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (387) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-isopropyl-5,6,12,16,19,33,36-heptamethyl-15-(piperidine-1-carbonyl)-11-((2,2,2-trifluoroethoxy)methyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (388) (5S,8S,11S,15S,18S,23aS,29S,35S,37aS)-8-((S)-sec-butyl)-29-(3-chloro-4-(trifluoromethyl)phenethyl)-18-cyclopentyl-35-(4-fluorobenzyl)-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (389) (3S,6S,9S,13S,16S,19S,22S,25S,31S,34S)-25-[2-[3-chloro-4-(trifluoromethyl)phenyl]ethyl]-31-(cyclohexylmethyl)-16-cyclopentyl-22-[2-(3,3-difluoro-1-piperidyl)ethyl]-9-isobutyl-19-isopropyl-N,N,3,4,10,14,17,23,29,32-decamethyl-6-[(1S)-1-methylpropyl]-2,5,8,11,15,18,21,24,27,30,33-undecaoxo-1,4,7,10,14,17,20,23,26,29,32-undecazabicyclo[32.2.0]hexatriacontane-13-carboxamide, (390) (5S,8S,11S,15S,18S,23aS,29S,35S,37aS)-8-((S)-sec-butyl)-35-(cyclohexylmethyl)-18-cyclopentyl-29-(3-fluoro-4-(trifluoromethyl)phenethyl)-11-isobutyl-5,6,12,16,19,33,36-heptamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (391) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-cyclopentyl-5,6,12,16,19,33,36-heptamethyl-15-(piperidine-1-carbonyl)-11-propyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (392) (6S,9S,13S,16S,22S,25S,31S,34S)-25-[2-[3-chloro-4-(trifluoromethyl)phenyl]ethyl]-16-cyclohexyl-31-(cyclohexylmethyl)-9-isobutyl-4,10,14,17,23,29,32-heptamethyl-6-[(1S)-1-methylpropyl]-13-(piperidine-1-carbonyl)-22-propyl-spiro[1,4,7,10,14,17,20,23,26,29,32-undecazabicyclo[32.3.0]heptatriacontane-19,1'-cyclopentane]-2,5,8,11,15,18,21,24,27,30,33-undecone, (393) (3S,9S,18S,21S,25S,28S,34S)-3-[2-[3-chloro-4-(trifluoromethyl)phenyl]ethyl]-9-(cyclohexylmethyl)-21-cyclopentyl-28-isopropyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (394) (5S,8S,11S,15S,18S,21S,23aS,29S,35S,37aS)-8-((S)-sec-butyl)-29-(3-chloro-4-(trifluoromethyl)phenethyl)-35-(cyclohexylmethyl)-21-ethyl-11-isobutyl-18-isopropyl-5,6,12,16,19,21,33,36-octamethyl-15-(piperidine-1-carbonyl)tetracosahydro-2H-azeto[2,1-u]pyrrolo[2,1-i][1,4,7,10,13,16,19,22,25,28,31]undecaazacyclotetratriacontin-4,7,10,13,17,20,23,28,31,34,37(14H)-undecaone, (395) (3S,9S,18S,21S,25R,28S,34S)-3-[2-[3-chloro-4-(trifluoromethyl)phenyl]ethyl]-9-(cyclohexylmethyl)-7-ethyl-21-isobutyl-28-isopropyl-10,13,16,22,25,29-hexamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (396) (5S,8S,11S,15R,18S,23aS,29S,32R,35S,37aS)-8-((S)-sec-butyl)-29-(3-chloro-4-(trifluoromethyl)phenethyl)-18-cyclopentyl-5,6,11,12,15,19,32,33,35,36-decamethyl-docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (397) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-isopropyl-11-(2-methoxyethyl)-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (398) (3S,6S,9S,12S,18S,27S,30S,34S)-6-benzyl-18-[(4-chlorophenyl)methyl]-3,9-diisobutyl-4,7,16,19,22,25,30,31-octamethyl-27-[(1S)-1-methylpropyl]-12-[2-(p-tolyl)ethyl]-34-(pyrrolidine-1-carbonyl)-1,4,7,10,13,16,19,22,25,28,31-undecazacyclotetratriacontane-2,5,8,11,14,17,20,23,26,29,32-undecone, (399) (5S,8S,11S,15S,18S,23aS,29S,35S,37aS)-29-(3-chloro-4-(trifluoromethyl)phenethyl)-35-(cyclohexylmethyl)-8-cyclopentyl-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (400) (5S,8S,11S,15S,18S,23aS,29S,35S,37aS)-8,18-di((S)-sec-butyl)-29-(3-chloro-4-(trifluoromethyl)phenethyl)-11-(cyclopentylmethyl)-N,N,5,6,12,16,19,33,36-nonamethyl-35-(4-methylbenzyl)-4,7,10,13,17,20,23,28,31,34, 37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (401) (5S,8S,11S,15R,18S,23aS,25R,29S,35S,37aS)-8-((S)-sec-butyl)-29-(3-chloro-4-(trifluoromethyl)phenethyl)-18-cyclopentyl-25-ethoxy-36-ethyl-11-isobutyl-5,12,15, 16,19,33-hexamethyl-35-(4-(trifluoromethyl)benzyl)docosahydro-2H,4H-spiro[azeto[2,1-u]pyrrolo[2,1-i][1,4, 7,10,13,16,19,22,25,28,31]undecaazacyclotetratriacontine-21,1'-cyclopentan]-4,7, 10,13,17,20,23,28,31,34,37(14H,22H)-undecaone, (402) (3S,9S,18S,21S,25R,28S,34S)-9-(cyclohexylmethyl)-3-[2-[3-fluoro-4-(trifluoromethyl)phenyl]ethyl]-21,28-diisobutyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (403) (5S,8S,11S,15S,18S,23aS,29S,35S,37aS)-15-(3-oxa-8-azabicyclo[3.2.1]octane-8-carbonyl)-8,18-di((S)-sec-butyl)-29-(3-chloro-4-(trifluoromethyl)phenethyl)-11-isobutyl-5,6,12,16,19,33,36-heptamethyl-35-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7, 10,13,17,20,23,28,31,34,37(14H,22H)-undecaone, (404) (5S,8S,11S,15R,18S,23aS,29S,35S,37aS)-8,18-di((S)-sec-butyl)-29-(3-fluoro-4-(trifluoromethyl)phenethyl)-11-isobutyl-5,6,12,15,16,19,33,36-octamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7, 10,13,17,20,23,28,31,34,37(14H,22H)-undecaone, (405) (3S,9S,18S,21S,25R,28S,34S)-3-[2-[3-chloro-4-(trifluoromethyl)phenyl]ethyl]-9-(cyclohexylmethyl)-21-isobutyl-28-isopropyl-7,10,16,22,25,29-hexamethyl-18-[(1S)-1-methylpropyl]-13-propyl-spiro[1,4,7,10,13,16, 19,22,26,29,32-undecazabicyclo[32.3.0]heptatriacontane-31,1'-cyclopentane]-2,5,8,11,14,17,20, 23,27,30,33-undecone, (406) (3S,6S,9S,12S,18S,27S,30S,34R)-6-benzyl-18-[(4-chlorophenyl)methyl]-3,9-diisobutyl-1,4,7,16,19,22,25, 30,34-nonamethyl-27-[(1S)-1-methylpropyl]-12-[2-[4-(trifluoromethyl)phenyl]ethyl]-1,4,7,10,13,16,19,22,25, 28,31-undecazacyclotetracontane-2,5,8,11,14,17,20, 23,26,29,32-undecone, (407) (3S,9S,18S,21S,25R,28S,34S)-9-(cyclohexylmethyl)-3-[2-[3-fluoro-4-(trifluoromethyl)phenyl]ethyl]-21,28-diisobutyl-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,4'-tetrahydropyran]-2,5,8,11,14,17,20,23,27,30,33-undecone, (408) (5S,8S,11S,15S,18S,23aS,29S,35S,37aS)-15-(3-oxa-8-azabicyclo[3.2.1]octane-8-carbonyl)-8,18-di((S)-sec-butyl)-29-(3-fluoro-4-(trifluoromethyl)phenethyl)-11-isobutyl-5,6,12,16,19,33,36-heptamethyl-35-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7, 10,13,17,20,23,28,31,34,37(14H,22H)-undecaone, (409) (5S,8S,11S,15S,18S,23aS,29S,35S,37aS)-8,18-di((S)-sec-butyl)-35-(cyclohexylmethyl)-29-(3-fluoro-4-(trifluoromethyl)phenethyl)-11-isobutyl-5,6,12,16,19,33,36-heptamethyl-15-(piperidine-1-carbonyl)docosahydro-2H, 4H-spiro[azeto[2,1-u]pyrrolo[2,1-i][1,4,7,10,13,16,19, 22,25,28,31]undecaazacyclotetratriacontine-21,1'-cyclopentan]-4,7,10,13,17,20,23,28,31,34,37(14H,22H)-undecaone, (410) (3S,9S,18S,21S,25S,28S,34S)-3-[2-[3-chloro-4-(trifluoromethyl)phenyl]ethyl]-21-cyclobutyl-28-cyclohexyl-7,10,13,16,22,26,29-heptamethyl-18-[(1S)-1-methylpropyl]-25-(morpholine-4-carbonyl)-9-(p-tolylmethyl)spiro[1,4,7,10,13,16,19,22,26,29,32-undecazabicyclo[32.3.0]heptatriacontane-31,1'-cyclopentane]-2,5,8,11,14,17,20, 23,27,30,33-undecone, (411) (3S,9S,18S,21S,25S,28S,34S)-3-[2-[3-chloro-4-(trifluoromethyl)phenyl]ethyl]-18-cyclobutyl-28-cyclohexyl-9-(cyclohexylmethyl)-21-isobutyl-7,10,13,16,22,26,29-heptamethyl-25-(piperidine-1-carbonyl)spiro[1,4,7,10, 13,16,19,22,26,29,32-undecazabicyclo[32.3.0]heptatriacontane-31,1'-cyclopentane]-2,5,8,11,14,17,20, 23,27,30,33-undecone, (412) (6'S,15'S,18'S,22'R,25'S,30a'S,36'S,38a'R)-15'-((S)-sec-butyl)-36'-(3-chloro-4-(trifluoromethyl)phenethyl)-6'-(cyclohexylmethyl)-25'-isopropyl-7',10',13',18',19',22', 26'-heptamethyltetracosahydro-5'H-spiro[cyclopentane-1,28'-dipyrrolo[2,1-i:2',1'-o][1,4,7,10,13,16,19,22,25,28, 31]undecaazacyclotetratriacontin]-5',8',11',14',17',20',24', 27',30',35',38'(21'H,29'H)-undecaone, (413) (3S,6R,9S,18S,21S,25R,28S,34S)-3-[2-[3-chloro-4-(trifluoromethyl)phenyl]ethyl]-28-cyclopentyl-9-ethyl-6, 7,10,13,16,21,22,25,29-nonamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (414) (3S,9S,18S,21S,25R,28S,34S)-9-(cyclohexylmethyl)-21,28-diisobutyl-7,10,13,16,22,25,29-heptamethyl-8-[(1S)-1-methylpropyl]-3-[2-[4-(trifluoromethyl)phenyl]ethyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (415) (5S,8S,11S,15S,18S,23aS,29S,35S,37aS)-8-((S)-sec-butyl)-29-(3-chloro-4-(trifluoromethyl)phenethyl)-18-cyclopentyl-11-isobutyl-5,6,12,16,19,33,36-heptamethyl-15-(piperidine-1-carbonyl)-35-(propoxymethyl)docosahydro-2H,4H-spiro[azeto[2,1-u]pyrrolo[2,1-i][1,4, 7,10,13,16,19,22,25,28,31]undecaazacyclotetratriacontine-21,1'-cyclopentan]-4,7, 10,13,17,20,23,28,31,34,37(14H,22H)-undecaone, (416) (7S,10S,14R,17S,22aS,28S,34S,36aS,40aS)-7-((S)-sec-butyl)-28-(3-chloro-4-(trifluoromethyl)phenethyl)-34-(cyclohexylmethyl)-10-isobutyl-17-isopropyl-11,14, 18,32,35-pentamethyltetracosahydro-27H-spiro[azeto[1, 2-j]pyrido[1,2-g]pyrrolo[1,2-v][1,4,7,10,13,16,19,22,25, 28,31]undecaazacyclotetratriacontine-20,1'-cyclopentan]-6,9,12,16,19,22,27,30,33,36,40(2H,13H, 21H,36aH)-undecaone, (417) (3S,9S,18S,21S,25S,28S,34S)-3-[2-[3-chloro-4-(trifluoromethyl)phenyl]ethyl]-9-(cyclohexylmethyl)-21-isobutyl-28-isopropyl-7,10,13,16,22,29-hexamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20, 23,27,30,33-undecone, (418) (6S,9S,13R,16S,22S,25S,31S,34S)-31-[(4-chlorophenyl)methyl]-25-[2-[3-fluoro-4-(trifluoromethyl)phenyl]ethyl]-16,22-diisobutyl-9-isopropyl-4,10,13,17,23,29,32-heptamethyl-6-[(1S)-1-methylpropyl]spiro[1,4,7,10,14, 17,20,23,26,29,32-undecazabicyclo[32.2.0]hexatriacontane-19,1'-cyclopentane]-2,5,8,11,15,18,21, 24,27,30,33-undecone, (419) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-isopropyl-5,6,12,16,19,33,36-heptamethyl-11-(2-(methylsulfonyl)ethyl)-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (420) (3S,9S,18S,21S,25R,28S,34S)-3-[2-[3-chloro-4-(trifluoromethyl)phenyl]ethyl]-9-(cyclohexylmethyl)-28-cyclopentyl-21-isobutyl-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (421) (3S,9S,18S,21S,25S,28S,34S)-3-[2-[3-chloro-4-(trifluoromethyl)phenyl]ethyl]-9-(cyclohexylmethyl)-18-(cyclopropylmethyl)-21-isobutyl-28-isopropyl-7,10,13,16,22,26,29-heptamethyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (422) (5S,8S,11S,15S,18S,23aS,29S,35S,37aS)-15-(3-oxa-8-azabicyclo[3.2.1]octane-8-carbonyl)-8-((S)-sec-butyl)-29-(3-chloro-4-(trifluoromethyl)phenethyl)-18-cyclopentyl-11-isobutyl-5,6,12,16,19,33,36-heptamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (423) (3S,9S,12S,18S,27S,30S,34S)-9-butyl-18-[(4-chlorophenyl)methyl]-19-ethyl-12-[(3-iodophenyl)methyl]-3,30-diisobutyl-1,6,6,7,16,22,25,31-octamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (424) (5S,8S,11S,15R,18S,23aS,29S,35S,37aS)-8-((S)-sec-butyl)-18-cyclopentyl-29-(3,5-difluoro-4-(trifluoromethyl)phenethyl)-36-ethyl-11-isobutyl-5,6,12,15,16,19,33-heptamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (425) (3S,9S,18S,21S,25S,28S,34S)-3-[2-[3-chloro-4-(trifluoromethyl)phenyl]ethyl]-28-cyclohexyl-9-(cyclohexylmethyl)-21-(5,5-difluoropentyl)-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (426) (3S,9S,12S,18S,27S,30S,34S)-9-[(2-chlorophenyl)methyl]-12-[2-[3-chloro-4-(trifluoromethyl)phenyl]ethyl]-18-(cyclohexylmethyl)-3-isopropyl-1,4,6,6,10,16,19,22,25,30,31-undecamethyl-27-[(1S)-1-methylpropyl]-34-(pyrrolidine-1-carbonyl)-1,4,7,10,13,16,19,22,25,28,31-undecazacyclotetratriacontane-2,5,8,11,14,17,20,23,26,29,32-undecone, (427) (3S,9S,18S,21S,25S,28S,34S)-3-[2-[3-chloro-4-(trifluoromethyl)phenyl]ethyl]-28-cyclohexyl-9-[(1R)-1-hydroxyethyl]-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (428) (3S,9S,18S,21S,25S,28S,34S,36R)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-36-phenyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (429) (9'S,12'S,16'R,19'S,24a'S,30'S,36'S,38a'S)-9'-((S)-sec-butyl)-30'-(3-chloro-4-(trifluoromethyl)phenethyl)-19'-cyclopentyl-36'-isobutyl-7',12',13',16',20',34',37'-heptamethyltetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone, (430) (5S,8S,11S,15R,18S,23aS,25R,29S,35S,37aS)-8-((S)-sec-butyl)-18-cyclohexyl-29-(3,5-difluoro-4-(trifluoromethyl)phenethyl)-25-ethoxy-36-ethyl-11-isobutyl-5,6,12,15,16,19,33-heptamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclobutan]-4,7,10,13,17,20,23,28,31,34,37(14H,22H)-undecaone, (431) (3S,9S,12S,18S,27S,30S,34S)-9-butyl-18-[(4-chlorophenyl)methyl]-12-[(3,5-dichlorophenyl)methyl]-3,30-diisobutyl-1,6,6,7,16,19,22,25,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (432) (5S,8S,11S,15R,18S,23aS,25R,29S,35S,37aS)-8-((S)-sec-butyl)-18-cyclopentyl-29-(3,5-difluoro-4-(trifluoromethyl)phenethyl)-25-ethoxy-36-ethyl-11-isobutyl-5,6,12,15,16,19,33-heptamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (433) (6S,9S,13S,16S,22S,25S,31S,34S)-25-[2-[3-chloro-4-(trifluoromethyl)phenyl]ethyl]-16-cyclohexyl-31-(cyclohexylmethyl)-4,9,10,14,17,23,29,32-octamethyl-6-[(1S)-1-methylpropyl]-13-(piperidine-1-carbonyl)-22-(3-pyridylmethyl)spiro[1,4,7,10,14,17,20,23,26,29,32-undecazabicyclo[32.3.0]heptatriacontane-19,1'-cyclopentane]-2,5,8,11,15,18,21,24,27,30,33-undecone, (434) (3S,9S,18S,21S,25S,28S,34S)-3-[2-[3-chloro-4-(trifluoromethyl)phenyl]ethyl]-21-cyclobutyl-28-cyclohexyl-9-(cyclopentylmethyl)-7,10,13,16,22,26,29-heptamethyl-18-[(1S)-1-methylpropyl]-25-(morpholine-4-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (435) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-5-((isopentyloxy)methyl)-18-isopropyl-6,12,16,19,33,36-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (436) (3S,9S,12S,18S,27S,30S,34R)-25-butyl-18-[(4-chlorophenyl)methyl]-3,9-diisobutyl-4,6,6,10,16,19,22,30,31,34-decamethyl-27-[(1S)-1-methylpropyl]-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (437) (3S,9S,18S,21S,25S,28S,34S)-25-(azetidine-1-carbonyl)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-I[(1S)-1-methylpropyl]spiro

[1,4,7,10,13,16,19,22,26,29,32-undecazabicyclo[32.3.0] heptatriacontane-31,1'-cyclopentane]-2,5,8,11,14,17,20, 23,27,30,33-undecone, (438) (3S,9S,18S,21S,25S,28S,34S)-3-[2-[3-chloro-4-(trifluoromethyl)phenyl]ethyl]-9-(cyclohexylmethyl)-21-isobutyl-28-isopropyl-7,10,13,16,22,26,29-heptamethyl-18-[(1S)-1-methylpropyl]-25-(piperidine-1-carbonyl) spiro[1,4,7,10,13,16,19,22,26,29,32-undecazabicyclo [32.3.0]heptatriacontane-31,1'-cyclopentane]-2,5,8,11, 14,17,20,23,27,30,33-undecone, (439) (3S,9S,18S,21S,25R,28S,34S)-3-[2-[3-chloro-4-(trifluoromethyl)phenyl]ethyl]-9-(cyclohexylmethyl)-21-isobutyl-28-isopropyl-7,10,13,16,22,25,29-heptamethyl-18-[(1S)-1-methylpropyl]spiro[1,4,7,10,13,16,19,22,26, 29,32-undecazabicyclo[32.3.0]heptatriacontane-31,1'-cyclohexane]-2,5,8,11,14,17,20,23,27,30,33-undecone, (440) 2-[(3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-2,5,8,11,14,17,20,23,27,30,33-undecaoxo-25-(piperidine-1-carbonyl)spiro[1,4,7,10,13,16,19,22,26,29, 32-undecazabicyclo[32.3.0]heptatriacontane-31,1'-cyclopentane]-18-yl]acetonitrile, (441) (3S,6S,9S,13S,16S,22S,25S,31S,34S)-25-[2-[3-chloro-4-(trifluoromethyl)phenyl]ethyl]-9-isobutyl-N,N, 3,4,10,14,17,23,29,32-decamethyl-6,16-bis[(1S)-1-methylpropyl]-2,5,8,11,15,18,21,24,27,30,33-undecaoxo-31-(p-tolylmethyl)-22-(thiazol-4-ylmethyl)spiro[1,4,7,10,14, 17,20,23,26,29,32-undecazabicyclo[32.2.0] hexatriacontane-19,1'-cyclopentane]-13-carboxamide, (442) (6S,9S,13S,16S,22S,25S,31S,34S)-25-[(3-iodophenyl)methyl]-9,16-diisobutyl-4,10,14,19,19,20,29,32-octamethyl-6-[(1S)-1-methylpropyl]-22-(2-phenylethyl)-13-(piperidine-1-carbonyl)-31-(p-tolylmethyl)-1,4,7,10, 14,17,20,23,26,29,32-undecazabicyclo[32.2.0] hexatriacontane-2,5,8,11,15,18,21,24,27,30,33-undecone, (443) (5S,8S,11S,15S,18S,23aS,29S,35S,37aS)-8-((S)-sec-butyl)-29-(3-chloro-4-(trifluoromethyl)phenethyl)-35-(cyclohexylmethyl)-6-ethyl-11-isobutyl-18-isopropyl-5, 12,16,19,33,36-hexamethyl-15-(piperidine-1-carbonyl) docosahydro-2H,4H-spiro[azeto[2,1-u]pyrrolo[2,1-i][1,4, 7,10,13,16,19,22,25,28,31] undecaazacyclotetratriacontine-21,1'-cyclopentan]-4,7, 10,13,17,20,23,28,31,34,37(14H,22H)-undecaone, (444) (3S,6S,9S,12S,18S,27S,30S,34S)-12-[2-[3-chloro-4-(trifluoromethyl)phenyl]ethyl]-18-(cyclohexylmethyl)-9-[2-(4,4-difluoro-1-piperidyl)-2-oxo-ethyl]-30-isobutyl-3-isopropyl-1,4,6,10,16,19,22,25,31-nonamethyl-27-f(1S)-1-methylpropyl]-34-(piperidine-1-carbonyl)-1,4,7,10,13, 16,19,22,25,28,31-undecazacyclotetratriacontane-2,5,8, 11,14,17,20,23,26,29,32-undecone, (445) (3S,9S,18S,21S,25S,28S,34S)-3-[2-[3-chloro-4-(trifluoromethyl)phenyl]ethyl]-28-cyclohexyl-7,10,13,16,22, 26,29-heptamethyl-18-[(1S)-1-methylpropyl]-25-(morpholine-4-carbonyl)-9-(propoxymethyl)-21-(2,2,2-trifluoroethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (446) (5S,8S,11S,15S,18S,23aS,29S,35S,37aS)-8-((S)-sec-butyl)-29-(3-chloro-4-(trifluoromethyl)phenethyl)-35-cyclobutyl-11-isobutyl-18-isopropyl-5,6,12,16,19,33,36-heptamethyl-15-(piperidine-1-carbonyl)docosahydro-2H, 4H-spiro[azeto[2,1-u]pyrrolo[2,1-i][1,4,7,10,13,16,19, 22,25,28,31]undecaazacyclotetratriacontine-21,1'-cyclopentan]-4,7,10,13,17,20,23,28,31,34,37(14H,22H)-undecaone, (447) (8S,11S,15S,18S,23aS,29S,31aR,37S,39aS)-8-((S)-sec-butyl)-29-(3-chloro-4-(trifluoromethyl)phenethyl)-37-(cyclohexylmethyl)-18-isopropyl-6,11,12,16,19,38-hexamethyl-15-(piperidine-1-carbonyl)tetracosahydro-2H,4H-spiro[azeto[2,1-u]dipyrrolo[2,1-i:2',1'-o][1,4,7, 10,13,16,19,22,25,28,31]undecaazacyclotetratriacontine-21,1'-cyclopentan]-4,7,10,13,17,20,23,28,31,36,39(14H, 22H)-undecaone, (448) (3S,9S,18S,21S,25S,28S,34S)-3-[2-(4-chlorophenyl) ethyl]-9-(cyclohexylmethyl)-21-isobutyl-28-isopropyl-7, 10,13,16,22,26,29-heptamethyl-18-[(1S)-1-methylpropyl]-25-(piperidine-1-carbonyl)spiro[1,4,7,10,13,16,19, 22,26,29,32-undecazabicyclo[32.3.0]heptatriacontane-31,4'-tetrahydropyran]-2,5,8,11,14,17,20,23,27,30,33-undecone, (449) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-9-isobutyl-N,N,3,4,10,14,17,23, 29,32-decamethyl-6-[(1S)-1-methylpropyl]-22-(m-tolylmethyl)-2,5,8,11,15,18,21,24,27,30,33-undecaoxo-spiro[1,4,7,10,14,17,20,23,26,29,32-undecazabicyclo [32.2.0]hexatriacontane-19,1'-cyclopentane]-13-carboxamide, (450) (5S,8S,11S,15S,18S,23aS,29S,35S,37aS)-29-(3-chloro-4-(trifluoromethyl)phenethyl)-35-(cyclohexylmethyl)-8-((R)-1-hydroxyethyl)-11-isobutyl-18-isopropyl-5,6,12,16,19,33,36-heptamethyl-15-(piperidine-1-carbonyl)docosahydro-2H,4H-spiro[azeto[2,1-u]pyrrolo [2,1-i][1,4,7,10,13,16,19,22,25,28,31] undecaazacyclotetratriacontine-21,1'-cyclopentan]-4,7, 10,13,17,20,23,28,31,34,37(14H,22H)-undecaone, (451) (3S,9S,18S,21S,25S,28S,34S)-3-[2-[3-chloro-4-(trifluoromethyl)phenyl]ethyl]-18-(cyclobutylmethyl)-9-(cyclohexylmethyl)-21-isobutyl-28-isopropyl-7,10,13,16,22, 26,29-heptamethyl-25-(piperidine-1-carbonyl)spiro[1,4, 7,10,13,16,19,22,26,29,32-undecazabicyclo[32.3.0] heptatriacontane-31,1'-cyclopentane]-2,5,8,11,14,17,20, 23,27,30,33-undecone, (452) (8S,11S,17S,26S,29S,33R,36S)-11-[2-[3-chloro-4-(trifluoromethyl)phenyl]ethyl]-17-(cyclohexylmethyl)-8-[2-(4,4-difluoro-1-piperidyl)-2-oxo-ethyl]-29-isobutyl-36-isopropyl-9,15,18,21,24,30,33,37-octamethyl-26-[(1S)-1-methylpropyl]-6,9,12,15,18,21,24,27,30,34,37-undecazaspiro[4.33]octatriacontane-7,10,13,16,19,22,25, 28,31,35,38-undecone, (453) (5S,8S,11S,15S,18S,23aS,29S,35S,37aS)-8,18-di((S)-sec-butyl)-29-(3-chloro-4-(trifluoromethyl)phenethyl)-35-(cyclohexylmethyl)-11-isobutyl-5,6,12,19,33,36-hexamethyl-15-(pyrrolidine-1-carbonyl)docosahydro-2H, 4H-spiro[azeto[2,1-u]pyrrolo[2,1-i][1,4,7,10,13,16,19, 22,25,28,31]undecaazacyclotetratriacontine-21,1'-cyclopentan]-4,7,10,13,17,20,23,28,31,34,37(14H,22H)-undecaone, (454) (3S,9S,18S,21S,25R,28S,34S)-3-[2-[3-chloro-4-(trifluoromethyl)phenyl]ethyl]-28-cyclohexyl-9-(cyclohexylmethyl)-7,10,13,16,21,22,25,26,29,31,31,32-dodecamethyl-18-[(1S)-1-methylpropyl]-1,4,7,10,13,16,19,22,26, 29,32-undecazabicyclo[32.3.0]heptatriacontane-2,5,8,11, 14,17,20,23,27,30,33-undecone, (455) (5S,8S,11S,15R,18S,23aS,29S,35S,37aS)-8-((S)-sec-butyl)-29-(3-chloro-4-(trifluoromethyl)phenethyl)-11-(cyclobutylmethyl)-35-(cyclohexylmethyl)-18-isopropyl-5,6,12,15,19,33,36-heptamethyldocosahydro-2H,4H-spiro[azeto[2,1-u]pyrrolo[2,1-i][1,4,7,10,13,16,19,22,25, 28,31]undecaazacyclotetratriacontine-21,1'-cyclopentan]-4,7,10,13,17,20,23,28,31,34,37(14H,22H)-undecaone, (456) (3S,9S,18S,21S,25R,28S,34S)-3-[2-[3-chloro-4-(trifluoromethyl)phenyl]ethyl]-21-cyclohexyl-9-(cyclohexylmethyl)-28-isopropyl-7,10,13,16,22,25,29-heptamethyl-8-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (457) (3S,9S,12S,18S,27S,30S,34S)-18-[(4-chlorophenyl)methyl]-9-ethyl-12-[(3-iodophenyl)methyl]-3,30-diisobutyl-1,6,6,7,16,19,22,25,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (458) (5S,8S,11S,15S,18S,23aS,29S,35S,37aS)-8-((S)-sec-butyl)-35-(cyclohexylmethyl)-18-isopropyl-5,6,11,12,16,19,33,36-octamethyl-15-(piperidine-1-carbonyl)-29-(4-(trifluoromethyl)phenethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (459) (6S,9S,13S,16S,22S,25S,31S,34S)-25-[(3-iodophenyl)methyl]-9,16-diisobutyl-22-[(2-methoxyphenyl)methyl]-4,10,14,19,19,20,29,32-octamethyl-6-[(1S)-1-methylpropyl]-13-(piperidine-1-carbonyl)-31-(p-tolylmethyl)-1,4,7,10,14,17,20,23,26,29,32-undecazabicyclo[32.2.0]hexatriacontane-2,5,8,11,15,18,21,24,27,30,33-undecone, (460) (3S,9S,18S,21S,25S,28S,34S,36S)-3-[2-[3-chloro-4-(trifluoromethyl)phenyl]ethyl]-9-(cyclohexylmethyl)-36-(4,4-difluoro-1-piperidyl)-28-isopropyl-7,10,13,16,21,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (461) (3S,9S,18S,21S,25S,28S,34S)-3-[2-[3-chloro-4-(trifluoromethyl)phenyl]ethyl]-21-cyclobutyl-28-cyclohexyl-9-(cyclopentylmethyl)-7,10,13,16,22,26,29-heptamethyl-18-[(1S)-1-methylpropyl]-25-(3-oxa-8-azabicyclo[3.2.1]octane-8-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (462) (5S,8S,11S,15R,18S,23aS,29S,35S,37aS)-8,18-di((S)-sec-butyl)-29-(3-chloro-4-(trifluoromethyl)phenethyl)-25,25-difluoro-11-isobutyl-5,6,12,15,16,19,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclobutan]-4,7,10,13,17,20,23,28,31,34,37(14H,22H)-undecaone, (463) (3S,9S,12S,18S,27S,30S,34S)-12-[2-[3-chloro-4-(trifluoromethyl)phenyl]ethyl]-18-(cyclohexylmethyl)-9-[2-(4,4-difluoro-1-piperidyl)-2-oxo-ethyl]-30-isobutyl-3-isopropyl-1,4,6,6,10,16,19,22,25,31-decamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (464) (5S,8S,11S,15R,18S,23aS,29S,32R,35S,37aS)-8-((S)-sec-butyl)-29-(3-chloro-4-(trifluoromethyl)phenethyl)-35-(2-chlorobenzyl)-18-cyclopentyl-5,6,11,12,15,19,32,33,36-nonamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (465) (5S,8S,11S,15R,18S,23aS,29S,35S,37aS)-8-((S)-sec-butyl)-29-(3-chloro-4-(trifluoromethyl)phenethyl)-11-cyclobutyl-35-(cyclohexylmethyl)-18-isopropyl-5,6,12,15,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (466) (5S,8S,11S,15R,18S,23aS,25R,29S,35S,37aS)-8-((S)-sec-butyl)-18-cyclopentyl-29-(3,5-difluoro-4-(trifluoromethyl)phenethyl)-25-ethoxy-36-ethyl-11-isobutyl-5,6,12,15,16,19,33-heptamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (467) (3S,6S,9S,12S,18S,27S,30S,34S)-6,9-dibenzyl-18-[(4-chlorophenyl)methyl]-3-isopropyl-4,7,16,19,22,25,30,31-octamethyl-27-[(1S)-1-methylpropyl]-12-(m-tolylmethyl)-34-(pyrrolidine-1-carbonyl)-1,4,7,10,13,16,19,22,25,28,31-undecazacyclotetratriacontane-2,5,8,11,14,17,20,23,26,29,32-undecone, (468) (3S,9S,18S,21S,25S,28S,34S)-3-[2-[3-chloro-4-(trifluoromethyl)phenyl]ethyl]-9-(cyclohexylmethyl)-21-isobutyl-28-isopropyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopropane]-2,5,8,11,14,17,20,23,27,30,33-undecone, (469) (5S,8S,11S,15S,18S,23aS,29S,35S,37aS)-15-(3-oxa-8-azabicyclo[3.2.1]octane-8-carbonyl)-8,18-di((S)-sec-butyl)-29-(3-chloro-4-(trifluoromethyl)phenethyl)-35-(cyclohexylmethyl)-11-isobutyl-5,6,12,16,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (470) (5S,8S,11S,15S,18S,23aS,29S,35S,37aS)-8-((S)-sec-butyl)-29-(3-chloro-4-(trifluoromethyl)phenethyl)-11-isobutyl-35-((isopentyloxy)methyl)-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (471) (3S,9S,12S,18S,27S,30S,34R)-9-benzyl-8-[(4-chlorophenyl)methyl]-12-[2-[3-fluoro-4-(trifluoromethyl)phenyl]ethyl]-3,30-diisobutyl-1,6,6,7,16,19,22,25,31,34-decamethyl-27-[(1S)-1-methylpropyl]-1,4,7,10,13,16,19,22,25,28,31-undecazacyclotetratriacontane-2,5,8,11,14,17,20,23,26,29,32-undecone, (472) (6S,9S,13S,16S,19S,22S,25S,31S,34S)-19-benzyl-22-butyl-31-(cyclohexylmethyl)-25-[(3-iodophenyl)methyl]-9,16-diisobutyl-4,10,14,20,29,32-hexamethyl-6-[(1S)-1-methylpropyl]-13-(piperidine-1-carbonyl)-1,4,7,10,14,17,20,23,26,29,32-undecazabicyclo[32.2.0]hexatriacontane-2,5,8,11,15,18,21,24,27,30,33-undecone, (473) (3S,6S,9S,12S,18S,27S,30S,34S)-6-benzyl-18-[(4-chlorophenyl)methyl]-3,9-diisobutyl-4,7,16,19,22,25,30,31-octamethyl-27-[(1S)-1-methylpropyl]-34-(piperidine-1-carbonyl)-12-[[3-(trifluoromethoxy)phenyl]methyl]-1,4,7,10,13,16,19,22,25,28,31-undecazacyclotetratriacontane-2,5,8,11,14,17,20,23,26,29,32-undecone, (474) (5S,8S,11S,15R,18S,23aS,29S,35S,37aS)-29-(3-chloro-4-(trifluoromethyl)phenethyl)-35-(cyclohexylmethyl)-8-(cyclopropylmethyl)-11-isobutyl-18-isopropyl-5,6,12,15,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (475) (5S,8S,11S,15R,18S,23aS,29S,35S,37aS)-8-((S)-sec-butyl)-18-cyclohexyl-29-(3,5-difluoro-4-(trifluoromethyl)phenethyl)-36-ethyl-25,25-difluoro-11-isobutyl-5,6,12,15,16,19,33-heptamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclobutan]-4,7,10,13,17,20,23,28,31,34,37(14H,22H)-undecaone, (476) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (477) (6S,9S,13S,16S,22S,25S,31S,34S)-25-[2-[3-chloro-4-(trifluoromethyl)phenyl]ethyl]-16-cyclohexyl-31-(cyclohexylmethyl)-9-isobutyl-4,10,14,17,23,29,32-heptamethyl-6-[(1S)-1-methylpropyl]-22-[(5-methyl-3-pyridyl)methyl]-13-(piperidine-1-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (478) (6S,9S,13S,16S,22S,25S,31S,34S)-25-[2-[3-chloro-4-(trifluoromethyl)phenyl]ethyl]-16-cyclohexyl-31-(cyclohexylmethyl)-9-isobutyl-4,10,14,17,23,29,32-heptamethyl-6-[(1S)-1-methylpropyl]-13-(piperidine-1-carbonyl)-22-propyl-spiro[1,4,7,10,14,17,20,23,26,29,32-undecazabicyclo[32.2.0]hexatriacontane-19,1'-cyclopentane]-2,5,8,11,15,18,21,24,27,30,33-undecone, (479) (3S,6S,9S,13S,16S,22S,25S,31S,34S)-25-[2-[3-chloro-4-(trifluoromethyl)phenyl]ethyl]-16-cyclohexyl-31-(cyclohexylmethyl)-9-isobutyl-3,4,10,14,17,23,29,32-octamethyl-6-[(1S)-1-methylpropyl]-13-(piperidine-1-carbonyl)-22-[[6-(trifluoromethyl)-3-pyridyl]methyl]spiro[1,4,7,10,14,17,20,23,26,29,32-undecazabicyclo[32.2.0]hexatriacontane-19,1'-cyclopentane]-2,5,8,11,15,18,21,24,27,30,33-undecone, (480) (6S,9S,13S,16S,22S,25S,31S,34S)-25-[2-[3-chloro-4-(trifluoromethyl)phenyl]ethyl]-16-cyclohexyl-31-(cyclohexylmethyl)-9-isobutyl-4,10,14,17,23,29,32-heptamethyl-6-[(1S)-1-methylpropyl]-13-(piperidine-1-carbonyl)-22-(4-pyridylmethyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (481) (5S,8S,11S,15R,18S,23aS,29S,35S,37aS)-8-((S)-sec-butyl)-18-cyclopentyl-29-(3-fluoro-4-(trifluoromethyl)phenethyl)-11-isobutyl-5,6,12,15,16,19,33,36-octamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (482) (3S,6R,9S,18S,21S,25R,28S,34S)-9-benzyl-3-[2-[3-chloro-4-(trifluoromethyl)phenyl]ethyl]-28-cyclopentyl-6,7,10,13,16,21,22,25,29-nonamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (483) (3S,6S,9S,12S,18S,27S,30S,34S)-9-butyl-18-[(4-chlorophenyl)methy]-6-[(3-fluorophenyl)methyl]-12-[(3-iodophenyl)methyl]-3,30-diisobutyl-1,7,16,19,22,25,31-heptamethyl-27-1[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (484) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-(methoxymethyl)-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (485) (5S,8S,11S,15S,18S,23aS,29S,35S,37aS)-29-(3-chloro-4-(trifluoromethyl)phenethyl)-35-(cyclohexylmethyl)-11-isobutyl-8-((isopentyloxy)methyl)-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (486) (5S,8S,11S,15R,18S,23aS,25R,29S,35S,37aS)-8-((S)-sec-butyl)-18-cyclohexyl-29-(3,5-difluoro-4-(trifluoromethyl)phenethyl)-25-ethoxy-11-isobutyl-5,6,12,15,16,19,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (487) (5S,8S,11S,15S,18S,23aS,29S,35S,37aS)-8-((S)-sec-butyl)-29-(3-chloro-4-(trifluoromethyl)phenethyl)-11-isobutyl-18-isopropyl-35-(methoxymethyl)-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (488) (5S,8S,11S,15R,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,6,12,15,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (489) (9'S,12'S,16'R,19'S,24a'S,30'S,36'S,38a'S)-9'-((S)-sec-butyl)-30'-(3-chloro-4-(trifluoromethyl)phenethyl)-19'-cyclopentyl-7',12',13',16',20',34',37'-heptamethyl-36'-(pyridin-3-ylmethyl)tetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone, (490) (5S,8S,11S,15R,18S,23aS,29S,35S,37aS)-29-(3-chloro-4-(trifluoromethyl)phenethyl)-35-(cyclohexylmethyl)-8-cyclopropyl-11-isobutyl-18-isopropyl-5,6,12,15,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (491) (3S,9S,18S,21S,25S,28S,34S)-28-cyclohexyl-9-(cyclohexylmethyl)-3-[2-[3-fluoro-4-(trifluoromethyl)phenyl]ethyl]-7,10,13,16,21,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (492) (8S,11S,17S,26S,29S,33S,36S)-11-[2-[3-chloro-4-(trifluoromethyl)phenyl]ethyl]-17-(cyclohexylmethyl)-8-[(2-fluorophenyl)methyl]-36-isopropyl-9,15,18,21,24,29,30,34,37-nonamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (493) (3S,6R,9S,12S,18S,27S,30S,34S)-12-[2-[3-chloro-4-(trifluoromethyl)phenyl]ethyl]-18-(cyclohexylmethyl)-9-[2-(4,4-difluoro-1-piperidyl]-2-oxo-ethyl]-30-isobutyl-3-isopropyl-1,4,6,10,16,19,22,25,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (494) (5S,8S,11S,15R,18S,23aS,29S,35S,37aS)-8-((S)-sec-butyl)-29-(3-chloro-4-(trifluoromethyl)phenethyl)-18-cyclopentyl-36-ethyl-11-isobutyl-5,6,12,15,16,19,33-heptamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (495) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-25-(piperidine-1-carbonyl)-18-propyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone, (496) (5S,8S,11S,15S,18S,23aS,29S,35S,37aS)-8-((S)-sec-butyl)-29-(3-chloro-4-(trifluoromethyl)phenethyl)-35-(cyclohexylmethyl)-5-((R)-1-hydroxyethyl)-11-isobutyl-18-isopropyl-6,12,16,19,33,36-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (497) (5S,8S,11S,15S,18S,23aS,29S,35S,37aS)-29-(3-chloro-4-(trifluoromethyl)phenethyl)-35-(cyclohexylmethyl)-11-isobutyl-18-isopropyl-8-((R)-1-methoxyethyl)-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (498) (3S,6S,9S,12S,18S,27S,30S,34S)-9-butyl-18-[(4-chlorophenyl)methyl]-12-[(3-iodophenyl)methyl]-3,30-diisobutyl-1,7,16,19,22,25,31-heptamethyl-27-[(1S)-1-methylpropyl]-34-(piperidine-1-carbonyl)-6-[[4-(trifluoromethyl)phenyl]methyl]-1,4,7,10,13,16,19,22,25,28,31-undecazacyclotetratriacontane-2,5,8,11,14,17,20,23,26,29,32-undecone, (499) (3S,6S,9S,12S,18S,27S,30S,34S)-6-benzyl-12-[(3-chlorophenyl)methyl]-18-[(4-chlorophenyl)methyl]-3,9-diisobutyl-7,16,19,22,25,30,31-heptamethyl-27-[(1S)-1-methylpropyl]-34-(pyrrolidine-1-carbonyl)-1,4,7,10,13,16,19,22,25,28,31-undecazacyclotetratriacontane-2,5,8,11,14,17,20,23,26,29,32-undecone, (500) (8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-9,15,18,21,24,30,34,37-octamethyl-26-[(1S)-1-methylpropyl]-33-(piperidine-1-carbonyl)-8-(thiazol-4-ylmethyl)-6,9,12,15,18,21,24,27,30,34,37-undecazaspiro[4.33]octatriacontane-7,10,13,16,19,22,25,28,31,35,38-undecone, (501) (3S,9S,18S,21S,25R,28S,34S)-3-[2-[3-chloro-4-(trifluoromethyl)phenyl]ethyl]-9-(cyclohexylmethyl)-28-(cyclopentylmethyl)-21-isobutyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (502) (3S,6S,9S,12S,18S,27S,30S,34S)-6-benzyl-18-[(4-chlorophenyl)methyl]-9-[(2-hydroxy-2-methyl-propoxy)methyl]-3-isobutyl-4,7,16,19,22,25,30,31-octamethyl-27-[(1S)-1-methylpropyl]-34-(pyrrolidine-1-carbonyl)-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (503) (3S,9S,18S,21S,25R,28S,34S)-3-[2-[3,5-difluoro-4-(trifluoromethyl)phenyl]ethyl]-36,36-difluoro-21-isobutyl-7,10,13,16,22,25,26,29-octamethyl-18,28-bis[(1S)-1-methylpropyl]-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (504) (3S,9S,18S,21S,25R,28S,34S)-3-[2-[3-chloro-4-(trifluoromethyl)phenyl]ethyl]-9-(cyclohexylmethyl)-13-ethyl-21-isobutyl-28-isopropyl-7,10,16,22,25,29-hexamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (505) (5S,8S,11S,15R,18S,23aS,29S,35S,37aS)-8-((S)-sec-butyl)-29-(3-chloro-4-(trifluoromethyl)phenethyl)-18-cyclohexyl-25,25-difluoro-11-isobutyl-5,6,12,15,16,19,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclobutan]-4,7,10,13,17,20,23,28,31,34,37(14H,22H)-undecaone, (506) (5S,8S,11S,15S,18S,23aS,29S,35S,37aS)-15-(azetidine-1-carbonyl)-8-((S)-sec-butyl)-29-(3-chloro-4-(trifluoromethyl)phenethyl)-18-cyclopentyl-36-ethyl-11-isobutyl-5,6,12,16,19,33-hexamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (507) (3S,9S,18S,21S,25S,28S,34S)-3-[2-[3-chloro-4-(trifluoromethyl)phenyl]ethyl]-9-(cyclohexylmethyl)-28-isopropyl-7,10,13,16,21,22,26,29,31,31,32-undecamethyl-18-[(1S)-1-methylpropyl]-25-(piperidine-1-carbonyl)-1,4,7,10,13,16,19,22,26,29,32-undecazabicyclo[32.3.0]heptatriacontane-2,5,8,11,14,17,20,23,27,30,33-undecone, (508) (3S,9S,18S,21S,25S,28S,34S)-3-[2-[3-chloro-4-(trifluoromethyl)phenyl]ethyl]-9-(cyclohexylmethyl)-21-isobutyl-28-isopropyl-7,10,13,16,22,29-hexamethyl-8-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (509) (5S,8S,11S,15S,18S,23aS,29S,35S,37aS)-8,18-di((S)-sec-butyl)-29-(3-chloro-4-(trifluoromethyl)phenethyl)-5,6,12,16,19,33,36-heptamethyl-11-pentyl-15-(pyrrolidine-1-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (510) (3S,9S,18S,21S,25R,28S,34S,36R)-3-[2-[3-chloro-4-(trifluoromethyl)phenyl]ethyl]-9-(cyclohexylmethyl)-28-cyclopentyl-36-ethoxy-21-isobutyl-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (511) (3S,9S,18S,21S,25R,28S,34S)-3-[2-[3-chloro-4-(trifluoromethyl)phenyl]ethyl]-9-(cyclopropylmethyl)-21-isobutyl-28-isopropyl-7,10,13,16,22,25,29-heptamethyl-8-[(1S)-1-methylpropyl]spiro[1,4,7,10,13,16,19,22,26, 29,32-undecazabicyclo[32.3.0]heptatriacontane-31,1'-cyclopentane]-2,5,8,11,14,17,20,23,27,30,33-undecone,
(512) (3S,6S,9S,12S,18S,27S,30S,34R)-6-benzyl-18-[(4-chlorophenyl)methyl]-9-isobutyl-3-isopropyl-4,7,10,16,19,22,25,30,31-nonamethyl-27-[(1S)-1-methylpropyl]-12-[2-[4-(trifluoromethyl)phenyl]ethyl]-1,4,7,10,13,16,19,22,25,28,31-undecazabicyclo[32.4.0]octatriacontane-2,5,8,11,14,17,20,23,26,29,32-undecone,
(513) (3S,6S,9S,12S,18S,27S,30S,34S)-6-benzyl-18-[(4-chlorophenyl)methyl]-9-[(5-fluoro-3-pyridyl)methoxymethyl]-3-isobutyl-4,7,16,19,22,25,30,31-octamethyl-27-[(1S)-1-methylpropyl]-34-(pyrrolidine-1-carbonyl)-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone,
(514) (6'S,9'S,13'S,16'S,25'S,31'S,38a'S)-16'-((S)-sec-butyl)-31'-(3-chloro-4-(trifluoromethyl)phenethyl)-6'-cyclohexyl-25'-(cyclohexylmethyl)-13'-isobutyl-5',8',12',18',21',24',27'-heptamethyl-9'-(piperidine-1-carbonyl)-5',6',9',10',12',13',15',16',18',19',21',22',24',25',27',28',30',31',38',38a'-icosahydro-4'H-spiro[cyclopentane-1,3'-[1,4,7,10,13,16,19,22,25,28,31]undecaazacyclotetratriacontino[10,9-a]indol]-1',4',7',11',14',17',20',23',26',29',32'(2'H,8'H)-undecaone,
(515) (5S,8S,11S,15S,18S,23aS,29S,35S,37aS)-15-(azetidine-1-carbonyl)-8-((S)-sec-butyl)-29-(3-chloro-4-(trifluoromethyl)phenethyl)-35-(cyclohexylmethyl)-18-cyclopentyl-11-isobutyl-5,6,12,16,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(516) (9'S,12'S,16'R,19'S,24a'S,30'S,33'R,36'S,38a'S)-9'-((S)-sec-butyl)-30'-(3-chloro-4-(trifluoromethyl)phenethyl)-36'-(cyclohexylmethyl)-19'-isopropyl-7',12',13',16',20',33',34',37'-octamethyltetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone,
(517) (3S,6S,9S,12S,18S,27S,30S,34S)-18-[(4-chlorophenyl)methyl]-6-[(5-fluoro-3-pyridyl)methoxymethyl]-3,9-diisobutyl-4,7,16,19,22,25,30,31-octamethyl-27-[(1S)-1-methylpropyl]-34-(pyrrolidine-1-carbonyl)-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone,
(518) (3S,9S,18S,21S,25S,28S,34S)-3-[2-[3-chloro-4-(trifluoromethyl)phenyl]ethyl]-28-cyclohexyl-9-(cyclohexylmethyl)-7,10,13,16,22,26,29-heptamethyl-18-[(1S)-1-methylpropyl]-25-(piperidine-1-carbonyl)-21-(2,2,2-trifluoroethoxymethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(519) (8S,11S,17S,26S,29S,33S,36S)-11-[2-[3-chloro-4-(trifluoromethyl)phenyl]ethyl]-17-(cyclohexylmethyl)-36-isopropyl-9,15,18,21,24,29,30,34,37-nonamethyl-26-[(1S)-1-methylpropyl]-33-(piperidine-1-carbonyl)-8-(3-pyridylmethyl)-6,9,12,15,18,21,24,30,34,37-undecazaspiro[4.33]octatriacontane-7,10,13,16,19,22,25,28,31,35,38-undecone,
(520) (3S,9S,18S,21S,25R,28S,34S)-3-[2-[3-chloro-4-(trifluoromethyl)phenyl]ethyl]-9-(cyclohexylmethyl)-21-isobutyl-28-isopropyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclobutane]-2,5,8,11,14,17,20,23,27,30,33-undecone,
(521) (6S,9R,13S,16S,25S,31S,33aS,37aS,38aS)-16-((S)-sec-butyl)-25-(4-chlorobenzyl)-6-isobutyl-3,3,5,9,12,13,18,21,24,27-decamethyl-31-(4-(trifluoromethyl)phenethyl)octacosahydro-[1,4,7,10,13,16,19,22,25,28,31]undecaazacyclotetratriacontino[10,9-a]indol-1,4,7,11,14,17,20,23,26,29,32(8H)-undecaone,
(522) (3S,9S,18S,21S,25S,28S,34S)-9-(cyclohexylmethyl)-3-[2-[3-fluoro-4-(trifluoromethyl)phenyl]ethyl]-21-isobutyl-28-isopropyl-7,10,13,16,22,26,29,31,31-nonamethyl-18-[(1S)-1-methylpropyl]-25-(piperidine-1-carbonyl)-1,4,7,10,13,16,19,22,26,29,32-undecazabicyclo[32.3.0]heptatriacontane-2,5,8,11,14,17,20,23,27,30,33-undecone,
(523) (8S,11S,17S,26S,29S,33S,36S)-11-[2-[3-chloro-4-(trifluoromethyl)phenyl]ethyl]-36-cyclohexyl-17-(cyclohexylmethyl)-8-(3,3-difluoropropyl)-29-isobutyl-9,15,18,21,24,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone,
(524) (5S,8S,11S,15S,18S,23aS,29S,35S,37aS)-8-((S)-sec-butyl)-29-(3-chloro-4-(trifluoromethyl)phenethyl)-35-cyclobutyl-18-cyclopentyl-11-isobutyl-5,6,12,19,33,36-hexamethyl-15-(piperidine-1-carbonyl)-16-propyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(525) (5S,8S,11S,15R,18S,23aS,25R,29S,35S,37aS)-8-((S)-sec-butyl)-29-(3-chloro-4-(trifluoromethyl)phenethyl)-18-cyclopentyl-25-ethoxy-36-ethyl-11-isobutyl-5,12,15,16,19,33-hexamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(526) (5S,8S,11S,15S,18S,23aS,29S,35S,37aS)-8-((S)-sec-butyl)-29-(3-chloro-4-(trifluoromethyl)phenethyl)-35-cyclohexyl-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(527) (6S,9S,13S,16S,22S,25S,31S,34S)-22-benzyl-25-[2-[3-chloro-4-(trifluoromethyl)phenyl]ethyl]-16-cyclohexyl-31-(cyclohexylmethyl)-9-isobutyl-4,10,14,17,23,29,32-heptamethyl-6-[(1S)-1-methylpropyl]-13-(piperidine-1-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone,
(528) (3S,9S,18S,25S,28S,34S)-3-[2-[3-chloro-4-(trifluoromethyl)phenyl]ethyl]-28-cyclohexyl-9-(cyclohexylmethyl)-25-[(4-fluorophenyl)methyl]-7,10,13,16,26,29-hexamethyl-18-[(1S)-1-methylpropyl]spiro[1,4,7,10,13,16,19,23,26,29,32-undecazabicyclo[32.3.0]heptatriacontane-31,1'-cyclopentane]-2,5,8,11,14,17,20,24,27,30,33-undecone,
(529) (5S,8S,11S,15R,18S,23aS,29S,35S,37aS)-8,18-di((S)-sec-butyl)-29-(3-chloro-4-(trifluoromethyl)phenethyl)-11-isobutyl-5,6,12,15,16,19,33,36-octamethyl-35-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(530) (6'S,9'S,13'S,16'S,21a'S,27'S,33'S,38a'S)-6'-((S)-sec-butyl)-27'-(4-chlorophenethyl)-33'-(cyclohexylmethyl)-

9'-isobutyl-16'-isopropyl-10',14',17',31',34',37'-hexamethyl-13'-(piperidine-1-carbonyl)docosahydro-1'H-spiro[cyclopentane-1,19'-dipyrrolo[1,2-g:1',2'-v][1,4,7,10,13,16,19,22,25,28,31]undecaazacyclotetratriacontin]-5',8',11',15',18',21',26',29',32',35',38'(12'H,20'H,38a'H)-undecaone, (531) (5S,8S,11S,15R,18S,23aS,29S,35S,37aS)-8-((S)-sec-butyl)-29-(3-chloro-4-(trifluoromethyl)phenethyl)-18-cyclopentyl-12-ethyl-11-isobutyl-5,6,15,19,33,36-hexamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (532) (3S,9S,18S,21S,25S,28S,34S)-3-[2-[3-chloro-4-(trifluoromethyl)phenyl]ethyl]-9-(cyclohexylmethyl)-28-cyclopentyl-26-ethyl-7,10,13,16,21,22,29-heptamethyl-8-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (533) (3S,9S,18S,21S,25S,28S,34S)-3-[2-[3-chloro-4-(trifluoromethyl)phenyl]ethyl]-9-(cyclohexylmethyl)-18-cyclopropyl-21-isobutyl-28-isopropyl-7,10,13,16,22,26,29-heptamethyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (534) (5S,8S,11S,15S,18S,23aS,29S,35S,37aS)-29-(3-chloro-4-(trifluoromethyl)phenethyl)-35-(cyclohexylmethyl)-11-isobutyl-18-isopropyl-5,6,12,16,19,33,36-heptamethyl-15-(piperidine-1-carbonyl)-8-propyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (535) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-18-[(1R)-1-methoxyethyl]-7,10,13,16,22,26,29-heptamethyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (536) (3S,6S,9S,12S,18S,27S,30S,34S)-18-[(4-chlorophenyl)methyl]-6-(cyclohexylmethyl)-3,9-diisobutyl-4,7,16,19,22,25,30,31-octamethyl-27-[(1S)-1-methylpropyl]-34-(pyrrolidine-1-carbonyl)-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (537) (3S,9S,18S,21S,25R,28S,34S)-3-[2-[3-chloro-4-(trifluoromethyl)phenyl]ethyl]-9,18-bis(cyclohexylmethyl)-21-isobutyl-28-isopropyl-7,10,13,16,22,25,29-heptamethyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone, (538) (3S,6S,10R,13S,19S,22S,28S,34S)-28-[(4-chlorophenyl)methyl]-13,19-diisobutyl-6-isopropyl-7,10,14,20,26,29,32-heptamethyl-3-[(1S)-1-methylpropyl]-22-[2-[4-(trifluoromethyl)phenyl]ethyl]spiro[1,4,7,11,14,17,20,23,26,29,32-undecazabicyclo[32.2.0]hexatriacontane-16,1'-cyclopentane]-2,5,8,12,15,18,21,24,27,30,33-undecone, (539) (3S,6R,9S,18S,21S,25R,28S,34S)-9-[(2-chlorophenyl)methyl]-3-[2-[3-chloro-4-(trifluoromethyl)phenyl]ethyl]-28-cyclopentyl-6,7,10,13,16,21,22,25,29-nonamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (540) (3S,9S,18S,21S,25R,28S,34S)-9-(cyclohexylmethyl)-21-isobutyl-28-isopropyl-7,10,13,16,22,25,29-heptamethyl-8-[(1S)-1-methylpropyl]-3-[2-[4-(trifluoromethyl)phenyl]ethyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (541) (3S,9S,18S,21S,25R,28S,34S,36R)-3-[2-[3-chloro-4-(trifluoromethyl)phenyl]ethyl]-28-cyclopentyl-36-ethoxy-21-isobutyl-7,10,13,16,22,25,26,29-octamethyl-8-[(1S)-1-methylpropyl]-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (542) (3S,9S,18S,21S,25R,28S,34S)-3-[2-[3-chloro-4-(trifluoromethyl)phenyl]ethyl]-9-(cyclohexylmethyl)-16-cyclopropyl-21-isobutyl-28-isopropyl-7,10,13,22,25,29-hexamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (543) (3S,9S,18S,21S,25S,28S,34S)-3-[2-[3-chloro-4-(trifluoromethyl)phenyl]ethyl]-28-cyclohexyl-9-(cyclohexylmethyl)-10-ethyl-21-isobutyl-7,13,16,22,26,29-hexamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (544) (3S,9S,18S,21S,25S,28S,34S,36S)-9-(cyclohexylmethyl)-3-[2-[3-fluoro-4-(trifluoromethyl)phenyl]ethyl]-36-hydroxy-21,28-diisobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (545) (5S,8S,11S,15S,18S,23aS,29S,35S,37aS)-15-(3-oxa-8-azabicyclo[3.2.1]octane-8-carbonyl)-8,18-di((S)-sec-butyl)-29-(3-chloro-4-(trifluoromethyl)phenethyl)-11-isobutyl-5,6,12,16,19,33,36-heptamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (546) (3S,6S,9S,12S,18S,27S,30S,34R)-6-benzyl-18-[(4-chlorophenyl)methyl]-3,9-diisobutyl-4,7,10,16,19,22,25,30,31,34-decamethyl-27-[(1S)-1-methylpropyl]-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (547) (5S,8S,11S,15R,18S,23aS,25R,29S,35S,37aS)-8,18-di((S)-sec-butyl)-29-(3-chloro-4-(trifluoromethyl)phenethyl)-25-ethoxy-36-ethyl-11-isobutyl-5,6,12,15,16,19,33-heptamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclobutan]-4,7,10,13,17,20,23,28,31,34,37(14H,22H)-undecaone, (548) (3S,9S,18S,21S,25S,28S,34S)-3-[2-[3-chloro-4-(trifluoromethyl)phenyl]ethyl]-9-(cyclohexylmethyl)-21-isobutyl-7,10,13,16,22,26,29-heptamethyl-18-[(1S)-1-methylpropyl]-25-(piperidine-1-carbonyl)-28-propyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone, (549) (9'S,12'S,16'R,19'S,24a'S,30'S,36'S,38a'S)-9'-((S)-sec-butyl)-30'-(3-chloro-4-(trifluoromethyl)phenethyl)-36'-(4-chlorobenzyl)-19'-cyclopentyl-7',12',13',16',20', 34',37'-heptamethyltetracosahydro-5'H-spiro [cyclopentane-1,22'-dipyrrolo[2,1-i:2',1'-u][1,4,7,10,13, 16,19,22,25,28,31]undecaazacyclotetratriacontin]-5',8', 11',14',18',21',24',29',32',35',38'(15'H,23'H)-undecaone, (550) (3S,9S,18S,21S,25R,28S,34S)-3-[2-[3-chloro-4-(trifluoromethyl)phenyl]ethyl]-9-(cyclohexylmethyl)-18-(cyclopropylmethyl)-21-isobutyl-28-isopropyl-7,10,13,16, 22,25,29-heptamethyl-spiro[1,4,7,10,13,16,19,22,26,29, 32-undecazabicyclo[32.3.0]heptatriacontane-31,1' cyclopentane]-2,5,8,11,14,17,20,23,27,30,33-undecone, (551) (3S,9S,18S,21S,25S,28S,34S)-3-[2-[3-chloro-4-(trifluoromethyl)phenyl]ethyl]-28-cyclohexyl-9-(cyclohexylmethyl)-7,10,13,16,22,26,29-heptamethyl-18-[(1S)-1-methylpropyl]-25-(piperidine-1-carbonyl)-21-prop-2-ynyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone, (552) (3S,9S,18S,21S,25S,28S,34S)-3-[2-[3-chloro-4-(trifluoromethyl)phenyl]ethyl]-18,28-dicyclohexyl-9-(cyclohexylmethyl)-21-isobutyl-7,10,13,16,22,26,29-heptamethyl-25-(piperidine-1-carbonyl)spiro[1,4,7,10,13,16,19, 22,26,29,32-undecazabicyclo[32.3.0]heptatriacontane-31,1'-cyclopentane]-2,5,8,11,14,17,20,23,27,30,33-undecone, (553) (8S,11S,15S,18S,23aS,29S,31aR,38S,40aS)-8-((S)-sec-butyl)-29-(3-chloro-4-(trifluoromethyl)phenethyl)-38-(cyclohexylmethyl)-18-isopropyl-6,11,12,16,19,39-hexamethyl-15-(piperidine-1-carbonyl)tetracosahydro-2H,4H,28H-spiro[azeto[2,1-u]pyrido[2,1-o]pyrrolo[2,1-i][1,4,7,10,13,16,19,22,25,28,31] undecaazacyclotetratriacontine-21,1'-cyclopentan]-4,7, 10,13,17,20,23,28,31,37,40(14H,22H,31aH)-undecaone, (554) (3S,9S,18S,21S,25S,28S,34S)-3-[2-[3-chloro-4-(trifluoromethyl)phenyl]ethyl]-28-cyclohexyl-21-isobutyl-7, 10,13,16,22,26,29-heptamethyl-18-[(1S)-1-methylpropyl]-25-(piperidine-1-carbonyl)-9-prop-2-ynyl-spiro[11, 4,7,10,13,16,19,22,26,29,32-undecazabicyclo[32.3.0] heptatriacontane-31,1'-cyclopentane]-2,5,8,11,14,17,20, 23,27,30,33-undecone, (555) (5S,8S,11S,15S,18S,23aS,29S,35S,37aS)-8,18-di((S)-sec-butyl)-35-cyclopentyl-29-(3-fluoro-4-(trifluoromethyl)phenethyl)-11-isobutyl-N,N,5,6,12,16,19,33,36-nonamethyl-4,7,10,13,17,20,23,28,31,34,37-undecaoxotetratriacontahydro-2H,4H-spiro[azeto[2,1-u] pyrrolo[2,1-i][1,4,7,10,13,16,19,22,25,28,31] undecaazacyclotetratriacontine-21,1'-cyclopentane]-15-carboxamide, (556) (3S,9S,12S,18S,27S,30S,34S)-9-[(2-fluorophenyl) methyl]-12-[(3-iodophenyl)methyl]-3,30-diisobutyl-1,6, 6,7,16,19,22,25,31-nonamethyl-27-[(1S)-1-methylpropyl]-34-(piperidine-1-carbonyl)-18-(p-tolylmethyl)-1,4, 7,10,13,16,19,22,25,28,31-undecazacyclotetratriacontane-2,5,8,11,14,17,20,23,26, 29,32-undecone, (557) (3S,6S,9S,13S,16S,19S,22S,25S,31S,34S)-25-[2-[3-chloro-4-(trifluoromethyl)phenyl]ethyl]-9-isobutyl-N,N, 3,4,10,14,17,19,23,29,32-undecamethyl-6,16-bis[(1S)-1-methylpropyl]-2,5,8,11,15,18,21,24,27,30,33-undecaoxo-31-(p-tolylmethyl)-22-(3-pyridylmethyl)-1,4, 7,10,14,17,20,23,26,29,32-undecazabicyclo[32.2.0] hexatriacontane-13-carboxamide, (558) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-25-(piperidine-1-carbonyl) spiro[1,4,7,10,13,16,19,22,26,29,32-undecazabicyclo [32.3.0]heptatriacontane-31,1'-cyclopentane]-2,5,8,11, 14,17,20,23,27,30,33-undecone, (559) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-isopropyl-5,6,12,16,19,33,36-heptamethyl-15-(piperidine-1-carbonyl)-11-(prop-2-yn-1-yl)docosahydro-2H,4H-spiro[azeto[2,1-u]pyrrolo[2,1-i][1,4,7,10,13,16,19,22,25,28,31] undecaazacyclotetratriacontine-21,1'-cyclopentan]-4,7, 10,13,17,20,23,28,31,34,37(14H,22H)-undecaone, (560) (3S,9S,18S,21S,25R,28S,31S,34S)-9-[(4-chlorophenyl)methyl]-28-isobutyl-31-isopropyl-7,10,13,16,21,22, 25,29,32-nonamethyl-18-[(1S)-1-methylpropyl]-3-[2-[4-(trifluoromethyl)phenyl]ethyl]-1,4,7,10,13,16,19,22,26, 29,32-undecazabicyclo[32.3.0]heptatriacontane-2,5,8,11, 14,17,20,23,27,30,33-undecone, (561) (3S,9S,18S,21S,25S,28S,34S)-3-[2-[3-chloro-4-(trifluoromethyl)phenyl]ethyl]-9-(cyclohexylmethyl)-21-(cyclopropylmethyl)-28-isopropyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (562) (3S,9S,18S,21S,25S,28S,34S)-3-[2-[3-chloro-4-(trifluoromethyl)phenyl]ethyl]-21-cyclobutyl-28-cyclohexyl-9-(cyclohexylmethyl)-7,10,13,16,22,26,29-heptamethyl-18-[(1S)-1-methylpropyl]-25-(piperidine-1-carbonyl) spiro[1,4,7,10,13,16,19,22,26,29,32-undecazabicyclo [32.3.0]heptatriacontane-31,1'-cyclopentane]-2,5,8,11, 14,17,20,23,27,30,33-undecone, (563) (5S,8S,11S,15S,18S,23aS,29S,35S,37aS)-8-((S)-sec-butyl)-35-(cyclohexylmethyl)-18-cyclopentyl-29-(3-fluoro-4-(trifluoromethyl)phenethyl)-11-isobutyl-5,6,12, 16,19,33,36-heptamethyl-15-(piperidine-1-carbonyl) docosahydro-2H,4H-spiro azeto[2,1-u]pyrrolo[2,1-i][1,4, 7,10,13,16,19,22,25,28,31] undecaazacyclotetratriacontine-21,1'-cyclopentan]-4,7, 10,13,17,20,23,28,31,34,37(14H,22H)-undecaone, (564) 4-[[(3S,9S,18S,21S,25R,28S,34S)-3-[2-[3-chloro-4-(trifluoromethyl)phenyl]ethyl]-21-isobutyl-28-isopropyl-7,10,13,16,22,25,29-heptamethyl-18-[(1S)-1-methylpropyl]-2,5,8,11,14,17,20,23,27,30,33-undecaoxo-spiro[1,4, 7,10,13,16,19,22,26,29,32-undecazabicyclo[32.3.0] heptatriacontane-31,1'-cyclopentane]-9-yl]methyl] benzonitrile, (565) (5S,8S,11S,15R,18S,23aS,29S,35S,37aS)-8-((S)-sec-butyl)-29-(3-chloro-4-(trifluoromethyl)phenethyl)-35-(cyclohexylmethyl)-11-cyclopropyl-18-isopropyl-5,6,12, 15,19,33,36-heptamethyldocosahydro-2H,4H-spiro[azeto [2,1-u]pyrrolo[2,1-i][1,4,7,10,13,16,19,22,25,28,31] undecaazacyclotetratriacontine-21,1'-cyclopentan]-4,7, 10,13,17,20,23,28,31,34,37(14H,22H)-undecaone, (566) (3S,6S,9S,12S,18S,27S,30S,34R)-6-benzyl-9-butyl-18-[(4-chlorophenyl)methyl]-12-[2-[3-chloro-4-(trifluoromethyl)phenyl]ethyl]-3,30-diisobutyl-1,7,16,19,22,25, 31,34-octamethyl-27-[(1S)-1-methylpropyl]-1,4,7,10,13, 16,19,22,25,28,31-undecazacyclotetratriacontane-2,5,8, 11,14,17,20,23,26,29,32-undecone, (567) (5S,8S,11S,15S,18S,23aS,29S,35S,37aS)-8,18-di((S)-sec-butyl)-29-(3-chloro-4-(trifluoromethyl)phenethyl)-11-isobutyl-5,6,12,16,19,33,36-heptamethyl-35-(propoxymethyl)-15-(pyrrolidine-1-carbonyl) docosahydro-2H,4H-spiro[azeto[2,1-u]pyrrolo[2,1-i][1,4, 7,10,13,16,19,22,25,28,31]

undecaazacyclotetratriacontine-21,1'-cyclopentan]-4,7,
10,13,17,20,23,28,31,34,37(14H,22H)-undecanone,
(568) (5S,8S,11S,15S,18S,23aS,29S,35S,37aS)-8,18-di((S)-sec-butyl)-29-(3-chloro-4-(trifluoromethyl)phenethyl)-35-(cyclohexylmethyl)-11-isobutyl-N,N,5,6,12,19,33,36-octamethyl-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide,
(569) (6S,12S,21S,24S,26aR,30aR,33S,38aS)-21-((S)-sec-butyl)-6-(3-chloro-4-(trifluoromethyl)phenethyl)-12-(cyclohexylmethyl)-24-isobutyl-33-isopropyl-10,13,16,19,34-pentamethylhexacosahydro-5H-spiro[benzo[f1]pyrrolo[1,2-v][1,4,7,10,13,16,19,22,25,28,31]undecaazacyclotetratriacontine-36,1'-cyclopentan]-5,8,11,14,17,20,23,26,32,35,38(26aH,37H)-undecaone,
(570) (5S,8S,11S,15R,18S,23aS,29S,35S,37aS)-8-((S)-sec-butyl)-29-(3-chloro-4-(trifluoromethyl)phenethyl)-35-(cyclohexylmethyl)-11-cyclopentyl-18-isopropyl-5,6,12,15,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecanone,
(571) (5S,8S,11S,15S,18S,23aS,29S,35S,37aS)-8,18-di((S)-sec-butyl)-29-(3,5-difluoro-4-(trifluoromethyl)phenethyl)-36-ethyl-11-isobutyl-N,N,5,6,12,16,19,33-octamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide,
(572) (5S,8S,11S,15S,18S,23aS,29S,35S,37aS)-8-((S)-sec-butyl)-29-(3-chloro-4-(trifluoromethyl)phenethyl)-11,35-bis(cyclohexylmethyl)-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(573) (5S,8S,11S,15R,18S,23aS,25R,29S,35S,37aS)-8,18-di((S)-sec-butyl)-29-(3-chloro-4-(trifluoromethyl)phenethyl)-25-ethoxy-36-ethyl-11-isobutyl-5,12,15,16,19,33-hexamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(574) (5S,8S,11S,15R,18S,23aS,25R,29S,35S,37aS)-8,18-di((S)-sec-butyl)-29-(3,5-difluoro-4-(trifluoromethyl)phenethyl)-25-ethoxy-36-ethyl-11-isobutyl-5,12,15,16,19,33-hexamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(575) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-9-isobutyl-N,N,3,4,10,14,17,22,29,32-decamethyl-6-[(1S)-1-methylpropyl]-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide,
(576) (3S,9S,18S,21S,25R,28S,34S)-3-[2-(4-chlorophenyl)ethyl]-9-(cyclohexylmethyl)-21-isobutyl-28-isopropyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(577) (3S,9S,18S,21S,25S,28S,34S)-3-[2-[3-chloro-4-(trifluoromethyl)phenyl]ethyl]-9,28-bis(cyclohexylmethyl)-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(578) (3S,9S,18S,21S,25R,28S,34S)-9-[(4-chlorophenyl)methyl]-21-(cyclohexylmethyl)-28-isobutyl-7,10,13,16,22,25,29-heptamethyl-18-[(1S)-1-methylpropyl]-3-[2-[4-(trifluoromethyl)phenyl]ethyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(579) (3S,9S,18S,21S,25R,28S,34S)-28-cyclohexyl-3-[2-[3,5-difluoro-4-(trifluoromethyl)phenyl]ethyl]-36,36-difluoro-21-isobutyl-7,10,13,16,22,25,26,29-octamethyl-18-[(1S)-1-methylpropyl]-9-[[4-(trifluoromethyl)phenyl]methyl]spiro[1,4,7,10,13,16,19,22,26,29,32-undecazabicyclo[32.3.0]heptatriacontane-31,1'-cyclobutane]-2,5,8,11,14,17,20,23,27,30,33-undecone,
(580) (5S,8S,11S,15R,18S,23aS,29S,35S,37aS)-29-(3-chloro-4-(trifluoromethyl)phenethyl)-8-cyclobutyl-35-(cyclohexylmethyl)-11-isobutyl-18-isopropyl-5,6,12,15,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(581) (6'S,12'S,21'S,23a'S,31'R,34'S,39a'S)-21'-((S)-sec-butyl)-6'-(3-chloro-4-(trifluoromethyl)phenethyl)-12'-(cyclohexylmethyl)-34'-isopropyl-10',13',16',19',31',35'-hexamethyltetracosahydrospiro[cyclopentane-1,37'-pyrido[1,2-a]pyrrolo[1,2-v][1,4,7,10,13,16,19,22,25,28,31]undecaazacyclotetratriacontin]-5',8',11',14',17',20',23',29',33',36',39'(23a'H,30'H,38'H)-undecaone,
(582) (3S,6S,9S,12S,18S,27S,30S,34S)-18-[(4-chlorophenyl)methyl]-6-[(2-hydroxy-2-methyl-propoxy)methyl]-3,9-diisobutyl-4,7,16,19,22,25,30,31-octamethyl-27-[(1S)-1-methylpropyl]-34-(pyrrolidine-1-carbonyl)-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone,
(583) (8S,11S,17S,26S,29S,33R,36S)-17-[(4-chlorophenyl)methyl]-29-(cyclohexylmethyl)-8,36-diisobutyl-9,15,18,21,24,30,33,37-octamethyl-26-[(1S)-1-methylpropyl]-11-[2-[4-(trifluoromethyl)phenyl]ethyl]-6,9,12,15,18,21,24,27,30,34,37-undecazaspiro[4.33]octatriacontane-7,10,13,16,19,22,25,28,31,35,38-undecone,
(584) (5S,8S,11S,15R,18S,23aS,29S,32R,35S,37aS)-8-((S)-sec-butyl)-29-(3-chloro-4-(trifluoromethyl)phenethyl)-18-cyclopentyl-35-(4-fluorobenzyl)-5,6,11,12,15,19,32,33,36-nonamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(585) (3S,9S,18S,21S,25S,28S,34S)-3-[2-[3-chloro-4-(trifluoromethyl)phenyl]ethyl]-28-(cyclobutoxymethyl)-9-(cyclohexylmethyl)-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(586) (3S,9S,18S,21S,25R,28S,34S)-3-[2-[3-chloro-4-(trifluoromethyl)phenyl]ethyl]-9-(cyclohexylmethyl)-21-isobutyl-28-isopentyl-7,10,13,16,22,25,29-heptamethyl-18-[(1S)-1-methylpropyl]spiro[1,4,7,10,13,16,19,22,26, 29,32-undecazabicyclo[32.3.0]heptatriacontane-31,1'-cyclopentane]-2,5,8,11,14,17,20,23,27,30,33-undecone,
(587) (5S,8S,11S,15R,18S,23aS,29S,35S,37aS)-8-((S)-sec-butyl)-29-(3-chloro-4-(trifluoromethyl)phenethyl)-18-cyclopentyl-11-isobutyl-5,6,12,15,16,19,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(588) (3S,6S,9S,12S,18S,27S,30S,34R)-18-[(4-chlorophenyl)methyl]-3,9-diisobutyl-6-isopropyl-4,7,10,16,19,22,25,30,31,34-decamethyl-27-[(1S)-1-methylpropyl]-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone,
(589) (5S,8S,11S,15S,18S,23aS,29S,35S,37aS)-8-((S)-sec-butyl)-29-(3-chloro-4-(trifluoromethyl)phenethyl)-18-cyclopentyl-11-isobutyl-5,6,12,16,19,33,36-heptamethyl-15-(pyrrolidine-1-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(590) 3-[(8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-9,15,18,21,24,30,34,37-octamethyl-26-[(1S)-1-methylpropyl]-7,10,13,16,19,22,25,28,31,35,38-undecaoxo-33-(piperidine-1-carbonyl)-6,9,12,15,18,21,24,27,30,34,37-undecazaspiro[4.33]octatriacontan-8-yl]-N-methyl-propanamide,
(591) (3S,9S,18S,21S,25S,28S,31S,34S)-3-[2-[3-chloro-4-(trifluoromethyl)phenyl]ethyl]-28-cyclohexyl-9-(cyclohexylmethyl)-21-isobutyl-7,10,13,16,22,26,29,31-octamethyl-18-[(1S)-1-methylpropyl]-25-(piperidine-1-carbonyl)-1,4,7,10,13,16,19,22,26,29,32-undecazabicyclo[32.3.0]heptatriacontane-2,5,8,11,14,17,20,23,27,30,33-undecone,
(592) (8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-8-[(6-methoxy-3-pyridyl)methyl]-9,15,18,21,24,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone,
(593) (3S,9S,18S,21S,25R,28S,34S)-3-[2-[3-chloro-4-(trifluoromethyl)phenyl]ethyl]-28-cyclohexyl-9-(cyclohexylmethyl)-21-isobutyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(594) (5S,8S,11S,15R,18S,23aS,25R,29S,35S,37aS)-8-((S)-sec-butyl)-29-(3-chloro-4-(trifluoromethyl)phenethyl)-18-cyclopentyl-25-ethoxy-36-ethyl-11-isobutyl-5,6,12,15,16,19,33-heptamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclobutan]-4,7,10,13,17,20,23,28,31,34,37(14H,22H)-undecaone,
(595) (3S,9S,12S,18S,27S,30S,34R)-18-[(4-chlorophenyl)methyl]-30-(cyclohexylmethyl)-3,9-diisobutyl-1,6,6,7,16,19,22,25,31,34-decamethyl-27-[(1S)-1-methylpropyl]-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone,
(596) (3S,9S,12S,18S,27S,30S,34S)-12-[(3-iodophenyl)methyl]-3,30-diisobutyl-1,6,6,7,16,19,22,25,31-nonamethyl-27-[(1S)-1-methylpropyl]-9-(o-tolylmethyl)-34-(piperidine-1-carbonyl)-18-(p-tolylmethyl)-1,4,7,10,13,16,19,22,25,28,31-undecazacyclotetratriacontane-2,5,8,11,14,17,20,23,26,29,32-undecone,
(597) (9'S,12'S,16'R,19'S,24a'S,30'S,36'S,38a'S)-9'-((S)-sec-butyl)-30'-(3-chloro-4-(trifluoromethyl)phenethyl)-19'-cyclopentyl-36'-(3,4-difluorobenzyl)-7',12',13',16',20',34',37'-heptamethyltetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone,
(598) (5S,8S,11S,15R,18S,21R,23aS,29S,35S,37aS)-8-((S)-sec-butyl)-29-(3-chloro-4-(trifluoromethyl)phenethyl)-18-cyclopentyl-11-isobutyl-21-isopropyl-5,6,12,15,19,33,36-heptamethyl-35-(4-methylbenzyl)tetracosahydro-2H-azeto[2,1-u]pyrrolo[2,1-i][1,4,7,10,13,16,19,22,25,28,31]undecaazacyclotetratriacontin-4,7,10,13,17,20,23,28,31,34,37(14H)-undecaone,
(599) (8S,11S,15S,18S,23aS,29S,35S,37aS)-8-((S)-sec-butyl)-35-(cyclohexylmethyl)-29-(3-fluoro-4-(trifluoromethyl)phenethyl)-11-isobutyl-18-isopropyl-6,12,16,19,33,36-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(600) (3S,9S,18S,21S,25S,28S,34S)-3-[2-[3-chloro-4-(trifluoromethyl)phenyl]ethyl]-9-(cyclohexylmethyl)-21-isobutyl-28-isopropyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclohexane]-2,5,8,11,14,17,20,23,27,30,33-undecone,
(601) (8S,11S,15R,18S,23aS,29S,32R,35S,37aS)-8-((S)-sec-butyl)-29-(3-chloro-4-(trifluoromethyl)phenethyl)-35-(cyclohexylmethyl)-18-isopropyl-6,11,12,15,19,32,33,36-octamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(602) (3S,9S,12S,18S,27S,30S,34R)-22-butyl-18-[(4-chlorophenyl)methyl]-3,9-diisobutyl-4,6,6,10,16,19,25,30,31,34-decamethyl-27-[(1S)-1-methylpropyl]-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone,
(603) (3S,9S,18S,21S,25S,28S,34S)-3-[2-[3-chloro-4-(trifluoromethyl)phenyl]ethyl]-28-cyclohexyl-9-(cyclohexylmethyl)-18-[(1R)-1-hydroxyethyl]-21-isobutyl-7,10,13,16,22,26,29-heptamethyl-25-(piperidine-1-carbonyl)spiro[11,4,7,10,13,16,19,22,26,29,32-undecazabicyclo[32.3.0]heptatriacontane-31,1'-cyclopentane]-2,5,8,11,14,17,20,23,27,30,33-undecone,
(604) (3S,6S,9S,13S,16S,19S,22S,25S,31S,34S)-19-benzyl-25-[(3-iodophenyl)methyl]-16-isobutyl-31-[(4-methoxyphenyl)methyl]-3,4,9,10,14,20,22,29,32-nonamethyl-6-[(1S)-1-methylpropyl]-13-(pyrrolidine-1-carbonyl)-1,4,7,10,14,17,20,23,26,29,32-undecazabicyclo[32.2.0]hexatriacontane-2,5,8,11,15,18,21,24,27,30,33-undecone,
(605) (3S,9S,18S,25S,28S,34S)-3-[2-[3-chloro-4-(trifluoromethyl)phenyl]ethyl]-28-cyclohexyl-9-(cyclohexylmethyl)-25-[(2-hydroxy-2-methyl-propoxy)methyl]-7,10,13,16,26,29-hexamethyl-18-[(1S)-1-methylpropyl]spiro[1,4,7,10,13,16,19,23,26,29,32-undecazabicyclo[32.3.0]heptatriacontane-31,1'-cyclopentane]-2,5,8,11,14,17,20,24,27,30,33-undecone, (606) (5S,8S,11S,15R,18S,23aS,29S,35S,37aS)-8-((S)-sec-butyl)-18-cyclohexyl-29-(3,5-difluoro-4-(trifluoromethyl)phenethyl)-25,25-difluoro-11-isobutyl-5,6,12,15,16,19,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (607) (8S,11S,17S,26S,29S,33S,36S)-11-[2-(4-chlorophenyl)ethyl]-8-[(2-chlorophenyl)methyl]-17-(cyclohexylmethyl)-36-isopropyl-9,15,18,21,24,29,30,34,37-nonamethyl-26-[(1S)-1-methylpropyl]-33-(pyrrolidine-1-carbonyl)-6,9,12,15,18,21,24,27,30,34,37-undecazaspiro[4.33]octatriacontane-7,10,13,16,19,22,25,28,31,35,38-undecone, (608) (3S,9S,18S,21S,25R,28S,34S)-3-[2-[3-chloro-4-(trifluoromethyl)phenyl]ethyl]-9-(cyclohexylmethyl)-21-isobutyl-28-isopropyl-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (609) (3S,6S,9S,12S,18S,27S,30S,34S)-6-benzyl-12-[(3-chlorophenyl)methyl]-18-[(4-chlorophenyl)methyl]-3-isopropyl-4,7,16,19,22,25,30,31-octamethyl-27-[(1S)-1-methylpropyl]-9-(m-tolylmethyl)-34-(pyrrolidine-1-carbonyl)-1,4,7,10,13,16,19,22,25,28,31-undecazacyclotetratriacontane-2,5,8,11,14,17,20,23,26,29,32-undecone, (610) (8S,11S,17S,26S,29S,33S,36S)-17-[(4-chlorophenyl)methyl]-8,36-diisobutyl-29-isopropyl-9,15,18,21,24,30,37-heptamethyl-26-[(1S)-1-methylpropyl]-33-(piperidine-1-carbonyl)-11-[2-[4-(trifluoromethyl)phenyl]ethyl]-6,9,12,15,18,21,24,27,30,34,37-undecazaspiro[4.33]octatriacontane-7,10,13,16,19,22,25,28,31,35,38-undecone, (611) (3S,9S,18S,21S,25R,28S,34S)-3-[2-[3-chloro-4-(trifluoromethyl)phenyl]ethyl]-28-cyclopentyl-36,36-difluoro-21-isobutyl-7,10,13,16,22,25,26,29-octamethyl-18-[(1S)-1-methylpropyl]-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (612) (3S,6S,9S,12S,18S,27S,30S,34S)-6-benzyl-12-[(3-chlorophenyl)methyl]-18-[(4-chlorophenyl)methyl]-3-isopropyl-4,7,9,16,19,22,25,30,31-nonamethyl-27-[(1S)-1-methylpropyl]-34-(pyrrolidine-1-carbonyl)-1,4,7,10,13,16,19,22,25,28,31-undecazacyclotetratriacontane-2,5,8,11,14,17,20,23,26,29,32-undecone, (613) (3S,6S,9S,12S,18S,27S,30S,34S)-6,12-dibenzyl-18-[(4-chlorophenyl)methyl]-3,9-diisobutyl-4,7,16,19,22,25,30,31-octamethyl-27-[(1S)-1-methylpropyl]-34-(pyrrolidine-1-carbonyl)-1,4,7,10,13,16,19,22,25,28,31-undecazacyclotetratriacontane-2,5,8,11,14,17,20,23,26,29,32-undecone, (614) (6S,9S,13S,16S,22S,25S,31S,34S)-25-[2-[3-chloro-4-(trifluoromethyl)phenyl]ethyl]-16-cyclohexyl-31-(cyclohexylmethyl)-9-isobutyl-22-[(6-methoxy-3-pyridyl)methyl]-4,10,14,17,23,29,32-heptamethyl-6-[(1S)-1-methylpropyl]-13-(piperidine-1-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (615) (3S,9S,12S,18S,27S,30S,34R)-18-[(4-chlorophenyl)methyl]-30-(cyclohexylmethyl)-3,9-diisobutyl-4,6,6,10,16,19,22,25,31,34-decamethyl-27-[(1S)-1-methylpropyl]-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (616) (3S,6S,9S,13S,16S,22S,25S,31S,34S)-25-[2-[3-chloro-4-(trifluoromethyl)phenyl]ethyl]-22-[(2-fluorophenyl)methyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (617) (3S,6S,9S,13S,16S,22S,25S,31S,34S)-25-[(3-iodophenyl)methyl]-9,16-diisobutyl-3,4,10,14,19,19,20,29,32-nonamethyl-6-[(1S)-1-methylpropyl]-22-(2-phenylethyl)-13-(piperidine-1-carbonyl)-31-(p-tolylmethyl)-1,4,7,10,14,17,20,23,26,29,32-undecazabicyclo[32.2.0]hexatriacontane-2,5,8,11,15,18,21,24,27,30,33-undecone, (618) (3S,9S,18S,21S,25S,28S,34S)-28-cyclohexyl-9-(cyclohexylmethyl)-3-[2-(4-fluorophenyl)ethyl]-7,10,13,16,21,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (619) (3S,6S,9S,12S,18S,27S,30S,34S)-6-benzyl-12-[(3-iodophenyl)methyl]-3,30-diisobutyl-1,7,9,16,19,22,25,31-octamethyl-27-I[(1S)-1-methylpropyl]-34-(piperidine-1-carbonyl)-18-(p-tolylmethyl)-1,4,7,10,13,16,19,22,25,28,31-undecazacyclotetratriacontane-2,5,8,11,14,17,20,23,26,29,32-undecone, (620) (3S,9S,18S,21S,25S,28S,31S,34S)-3-[2-[3-chloro-4-(trifluoromethyl)phenyl]ethyl]-9-(cyclohexylmethyl)-31-ethyl-21-isobutyl-28-isopropyl-7,10,13,16,22,26,29,31-octamethyl-18-[(1S)-1-methylpropyl]-25-(piperidine-1-carbonyl)-1,4,7,10,13,16,19,22,26,29,32-undecazabicyclo[32.3.0]heptatriacontane-2,5,8,11,14,17,20,23,27,30,33-undecone, (621) (3S,6R,9S,18S,21S,25R,28S,34S)-3-[2-[3-chloro-4-(trifluoromethyl)phenyl]ethyl]-28-cyclopentyl-9-isobutyl-6,7,10,13,16,21,22,25,29-nonamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (622) (5S,8S,11S,15S,18S,23aS,29S,35S,37aS)-15-(3-oxa-8-azabicyclo[3.2.1]octane-8-carbonyl)-8-((S)-sec-butyl)-29-(3-chloro-4-(trifluoromethyl)phenethyl)-18-cyclopentyl-5,6,12,16,19,33,36-heptamethyl-11-pentyl-35-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (623) (3S,9S,18S,21S,25S,28S,34S)-3-[2-[3-chloro-4-(trifluoromethyl)phenyl]ethyl]-28-cyclohexyl-21-isobutyl-9-(methoxymethyl)-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (624) (3S,6S,9S,12S,18S,27S,30S,34S)-9-[(2-chlorophenyl)methyl]-12-[2-[3-chloro-4-(trifluoromethyl)phenyl]ethyl]-18-(cyclohexylmethyl)-3-isopropyl-1,4,6,10,16,19,22,25,30,31-decamethyl-27-[(1S)-1-methylpropyl]-34-(pyrrolidine-1-carbonyl)-1,4,7,10,13,16,19,22,25,28,31-undecazacyclotetratriacontane-2,5,8,11,14,17,20,23,26,29,32-undecone, (625) (5S,8S,11S,15S,18S,23aS,29S,35S,37aS)-8-((S)-sec-butyl)-29-(3-chlorophenethyl)-35-(cyclohexylmethyl)-18-isopropyl-5,6,11,12,16,19,33,36-octamethyl-15-(piperidine-1-carbonyl)docosahydro-2H,4H-spiro[azeto[2,1- u]pyrrolo[2,1-i][1,4,7,10,13,16,19,22,25,28,31] undecaazacyclotetratriacontine-21,1'-cyclopentan]-4,7, 10,13,17,20,23,28,31,34,37(14H,22H)-undecaone,
(626) (5S,8S,11S,15R,18S,23aS,25R,29S,35S,37aS)-8,18-di((S)-sec-butyl)-29-(3-chloro-4-(trifluoromethyl)phenethyl)-25-ethoxy-36-ethyl-11-isobutyl-5,6,12,15,16,19,33-heptamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclobutan]-4,7,10,13,17,20,23,28,31,34,37(14H,22H)-undecaone,
(627) (3S,9S,18S,21S,25S,28S,34S)-3-[2-[3-chloro-4-(trifluoromethyl)phenyl]ethyl]-9-(cyclohexylmethyl)-18-(cyclopentylmethyl)-21-isobutyl-28-isopropyl-7,10,13,16,22,26,29-heptamethyl-25-(piperidine-1-carbonyl)spiro[1 1,4,7,10,13,16,19,22,26,29,32-undecazabicyclo[32.3.0]heptatriacontane-31,1'-cyclopentane]-2,5,8,11,14,17,20,23,27,30,33-undecone,
(628) (5S,8S,11S,15R,18S,23aS,29S,35S,37aS)-8-((S)-sec-butyl)-35-(cyclohexylmethyl)-18-cyclopentyl-29-(3,5-difluoro-4-(trifluoromethyl)phenethyl)-25,25-difluoro-11-isobutyl-5,6,12,15,16,19,33,36-octamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(629) (3S,9S,18S,21S,25R,28S,34S)-3-[2-[3-chloro-4-(trifluoromethyl)phenyl]ethyl]-28-cyclohexyl-9-(cyclohexylmethyl)-21-isobutyl-7,10,13,16,22,25,26,29-octamethyl-8-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(630) (5S,8S,11S,15S,18S,23aS,29S,35S,37aS)-8,18-di((S)-sec-butyl)-29-(3-chloro-4-(trifluoromethyl)phenethyl)-11-isobutyl-5,6,12,16,19,33,36-heptamethyl-15-(piperidine-1-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(631) (3S,9S,18S,21S,25S,28S,34S)-3-[2-[3-chloro-4-(trifluoromethyl)phenyl]ethyl]-28-cyclohexyl-9-(5,5-difluoropentyl)-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(632) (6S,12S,21S,23aS,31R,34S,37S,39aS)-37-benzyl-21-((S)-sec-butyl)-12-(4-chlorobenzyl)-34-isobutyl-10,13,16,19,31,35,38-heptamethyl-6-(4-(trifluoromethyl)phenethyl)tetracosahydro-1H-pyrido[1,2-a]pyrrolo[1,2-v][1,4,7,10,13,16,19,22,25,28,31]undecaazacyclotetratriacontin-5,8,11,14,17,20,23,29,33,36,39(23aH,30H,39aH)-undecaone,
(633) (3S,9S,18S,21S,25S,28S,34S)-28-cyclohexyl-9-(cyclohexylmethyl)-7,10,13,16,21,22,26,29-octamethyl-18-[(1S)-1-methylpropyl]-3-(3-phenylpropyl)-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(634) (3S,9S,18S,21S,25S,28S,31S,34S,36R)-31-benzyl-9-[(4-chlorophenyl)methyl]-36-ethoxy-3-[(3-iodophenyl)methyl]-28-isobutyl-7,10,13,16,21,22,29,32-octamethyl-18-[(1S)-1-methylpropyl]-25-(pyrrolidine-1-carbonyl)-1,4,7,10,13,16,19,22,26,29,32-undecazabicyclo[32.3.0]heptatriacontane-2,5,8,11,14,17,20,23,27,30,33-undecone,
(635) (3S,9S,18S,21S,25R,28S,34S)-3-[2-[3-chloro-4-(trifluoromethyl)phenyl]ethyl]-9-(cyclohexylmethyl)-16-[2-(4,4-difluoro-1-piperidyl)ethyl]-21-isobutyl-28-isopropyl-7,10,13,22,25,29-hexamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(636) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-isopropyl-11-(methoxymethyl)-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(637) (3S,6S,9S,12S,18S,27S,30S,34S)-6-benzyl-18-[(4-chlorophenyl)methyl]-12-[(3-iodophenyl)methyl]-3,9-diisobutyl-4,7,16,19,22,25,30,31-octamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone,
(638) (6S,9S,13S,16S,22S,25S,31S,34S)-22-[(2-fluorophenyl)methyl]-25-[(3-iodophenyl)methyl]-9,16-diisobutyl-4,10,14,19,19,20,29,32-octamethyl-6-[(1S)-1-methylpropyl]-13-(piperidine-1-carbonyl)-31-(p-tolylmethyl)-1,4,7,10,14,17,20,23,26,29,32-undecazabicyclo[32.2.0]hexatriacontane-2,5,8,11,15,18,21,24,27,30,33-undecone,
(639) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-((R)-1-methoxyethyl)-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(640) (5S,8S,11S,15R,18S,23aS,25R,29S,35S,37aS)-8-((S)-sec-butyl)-29-(3-chloro-4-(trifluoromethyl)phenethyl)-18-cyclopentyl-25-ethoxy-11-isobutyl-5,6,12,15,16,19,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(641) (3S,9S,18S,21S,25R,28S,34S)-3-[2-[3-chloro-4-(trifluoromethyl)phenyl]ethyl]-9-(cyclohexylmethyl)-21-isobutyl-28-isopropyl-7,10,13,16,22,25,29,31,31-nonamethyl-18-[(1S)-1-methylpropyl]-1,4,7,10,13,16,19,22,26,29,32-undecazabicyclo[32.3.0]heptatriacontane-2,5,8,11,14,17,20,23,27,30,33-undecone,
(642) (5S,8S,11S,15S,18S,23aS,29S,35S,37aS)-29-(3-chloro-4-(trifluoromethyl)phenethyl)-8-cyclohexyl-35-(cyclohexylmethyl)-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(643) (8S,11S,17S,26S,29S,33S,36S)-11-[2-[3-chloro-4-(trifluoromethyl)phenyl]ethyl]-36-cyclohexyl-17-(cyclohexylmethyl)-8-(cyclopentylmethyl)-29-isobutyl-9,15,18,21,24,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone,
(644) (3S,9S,18S,21S,25R,28S,31S,34S)-31-allyl-3-[2-[3-chloro-4-(trifluoromethyl)phenyl]ethyl]-9-(cyclohexylmethyl)-21-isobutyl-28-isopropyl-7,10,13,16,22,25,26,29,31-nonamethyl-18-[(1S)-1-methylpropyl]-1,4,7,10,13,16,19,22,26,29,32-undecazabicyclo[32.3.0]heptatriacontane-2,5,8,11,14,17,20,23,27,30,33-undecone,
(645) (6S,9S,13R,16S,22S,25S,31S,34S)-31-[(4-chlorophenyl)methyl]-16,22-diisobutyl-9-isopropyl-4,10,13,17,23,29,32-heptamethyl-6-[(1S)-1-methylpropyl]-25-[2-[4-(trifluoromethyl)phenyl]ethyl]spiro[1,4,7,10,14,17,20,23,26,29,32-undecazabicyclo[32.2.0]hexatriacontane-19,1'-cyclopentane]-2,5,8,11,15,18,21,24,27,30,33-undecone,
(646) (3S,6S,9S,12S,18S,27S,30S,34S)-6-benzyl-18-[(4-chlorophenyl)methyl]-12-[2-(4-fluorophenyl)ethyl]-3,9-diisobutyl-4,7,16,19,22,25,30,31-octamethyl-27-[(1S)-1-methylpropyl]-34-(pyrrolidine-1-carbonyl)-1,4,7,10,13,16,19,22,25,28,31-undecazacyclotetratriacontane-2,5,8,11,14,17,20,23,26,29,32-undecone,
(647) (3S,9S,18S,21S,25S,28S,34S)-3-[2-[3-chloro-4-(trifluoromethyl)phenyl]ethyl]-28-cyclohexyl-9-(cyclohexylmethyl)-7,10,13,16,22,26,29-heptamethyl-18-[(1S)-1-methylpropyl]-25-(pyrrolidine-1-carbonyl)-21-(2,2,2-trifluoroethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(648) (5S,8S,11S,15R,18S,23aS,29S,35S,37aS)-8-((S)-sec-butyl)-29-(3-chloro-4-(trifluoromethyl)phenethyl)-18-cyclopentyl-11-isobutyl-5,6,15,19,33,36-hexamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(649) (4R,7S,13S,16S,22S,31S,34S)-22-(cyclohexylmethyl)-16-[2-[3-fluoro-4-(trifluoromethyl)phenyl]ethyl]-7,13-diisobutyl-4,5,10,10,11,20,23,26,29-nonamethyl-31-[(1S)-1-methylpropyl]-1,5,8,11,14,17,20,23,26,29,32-undecazabicyclo[32.4.0]octatriacontane-2,6,9,12,15,18,21,24,27,30,33-undecone,
(650) (3S,9S,18S,21S,25S,28S,34S)-3-[2-[3-chloro-4-(trifluoromethyl)phenyl]ethyl]-28-cyclohexyl-9-(cyclohexylmethyl)-21-(2-methoxyethyl)-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(651) (5S,8S,11S,15R,18S,23aS,29S,32R,35S,37aS)-8-((S)-sec-butyl)-29-(3-chloro-4-(trifluoromethyl)phenethyl)-18-cyclopentyl-35-ethyl-5,6,11,12,15,19,32,33,36-nonamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(652) (5S,8S,11S,15R,18S,23aS,25R,29S,35S,37aS)-8-((S)-sec-butyl)-29-(3-chloro-4-(trifluoromethyl)phenethyl)-18-cyclohexyl-25-ethoxy-11-isobutyl-5,6,12,15,16,19,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(653) (3S,9S,18S,21S,25S,28S,34S)-3-[2-[3-chloro-4-(trifluoromethyl)phenyl]ethyl]-9-(cyclohexylmethyl)-28-(5,5-difluoropentyl)-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(654) (3S,9S,18S,21S,25R,28S,31S,34S)-31-benzyl-9-[(4-chlorophenyl)methyl]-28-isobutyl-7,10,13,16,21,22,25,29,32-nonamethyl-18-[(1S)-1-methylpropyl]-3-[2-[4-(trifluoromethyl)phenyl]ethyl]-1,4,7,10,13,16,19,22,26,29,32-undecazabicyclo[32.2.0]hexatriacontane-2,5,8,11,14,17,20,23,27,30,33-undecone,
(655) (3S,6S,9S,12S,18S,27S,30S,34S)-12-[2-[3-chloro-4-(trifluoromethyl)phenyl]ethyl]-18-(cyclohexylmethyl)-9-[2-(3,3-difluoroazetidin-1-yl)ethyl]-3-isopropyl-6-(methoxymethyl)-1,4,10,16,19,22,25,30,31-nonamethyl-27-f[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone,
(656) (3S,6S,9S,13S,16S,22S,25S,31S,34S)-25-[2-[3-chloro-4-(trifluoromethyl)phenyl]ethyl]-16-cyclohexyl-31-(cyclohexylmethyl)-9-isobutyl-3,4,10,14,17,23,29,32-octamethyl-6-[(1S)-1-methylpropyl]-13-(piperidine-1-carbonyl)-22-(4-pyridylmethyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone,
(657) (3S,6S,9S,12S,18S,27S,30S,34S)-6-benzyl-12-[(3-chloro-5-fluoro-phenyl)methyl]-18-[(4-chlorophenyl)methyl]-3,9-diisobutyl-4,7,16,19,22,25,30,31-octamethyl-27-[(1S)-1-methylpropyl]-34-(pyrrolidine-1-carbonyl)-1,4,7,10,13,16,19,22,25,28,31-undecazacyclotetratriacontane-2,5,8,11,14,17,20,23,26,29,32-undecone,
(658) (3S,9S,12S,18S,27S,30S,34R)-18-[(4-chlorophenyl)methyl]-3,9-diisobutyl-30-isopropyl-4,6,6,10,16,19,22,25,31,34-decamethyl-27-[(1S)-1-methylpropyl]-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone,
(659) (5S,8S,11S,15S,18S,23aS,29S,35S,37aS)-8-((S)-sec-butyl)-35-(cyclohexylmethyl)-18-isopropyl-5,6,11,12,16,19,33,36-octamethyl-29-(3-phenylpropyl)-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(660) (5S,8S,11S,15S,18S,21S,23aS,29S,35S,37aS)-8,18-di((S)-sec-butyl)-29-(3-chloro-4-(trifluoromethyl)phenethyl)-11-isobutyl-21-isopropyl-N,N,5,6,12,16,19,33-octamethyl-35-(4-methylbenzyl)-4,7,10,13,17,20,23,28,31,34,37-undecaoxohexatriacontahydro-2H-azeto[2,1-u]pyrrolo[2,1-i][1,4,7,10,13,16,19,22,25,28,31]undecaazacyclotetratriacontine-15-carboxamide,
(661) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-((isopentyloxy)methyl)-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(662) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-25-(piperidine-1-carbonyl)spiro[36-oxa-1,4,7,10,13,16,19,22,26,29,32-undecazabicyclo[32.4.0]octatriacontane-31,1'-cyclopentane]-2,5,8,11,14,17,20,23,27,30,33-undecone,
(663) (8S,11S,15R,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-6,12,15,19, (664) (3S,9S,18S,21S,25R,28S,34S)-9-[(4-chlorophenyl) methyl]-28-isobutyl-7,10,13,16,21,22,25,29,31,31-decamethyl-18-[(1S)-1-methylpropyl]-3-[2-[4-(trifluoromethyl)phenyl]ethyl]-1,4,7,10,13,16,19,22,26,29,32-undecazabicyclo[32.3.0]heptatriacontane-2,5,8,11,14,17,20,23,27,30,33-undecone, (665) (3S,9S,18S,21S,25R,28S,31R,34S)-31-allyl-3-[2-[3-chloro-4-(trifluoromethyl)phenyl]ethyl]-9-(cyclohexylmethyl)-21-isobutyl-28-isopropyl-7,10,13,16,22,25,29,31-octamethyl-18-[(1S)-1-methylpropyl]-1,4,7,10,13,16,19,22,26,29,32-undecazabicyclo[32.3.0]heptatriacontane-2,5,8,11,14,17,20,23,27,30,33-undecone, (666) (9'S,12'S,16'R,19'S,24a'S,30'S,32a'R,38'S,40a'S)-9'-((S)-sec-butyl)-30'-(3-chloro-4-(trifluoromethyl)phenethyl)-38'-(cyclohexylmethyl)-19'-isopropyl-7',12',13',16',20',39'-hexamethylhexacosahydro-5'H-spiro [cyclopentane-1,22'-tripyrrolo[2,1-i:2',1'-o:2'',1''-u][1,4,7,10,13,16,19,22,25,28,31] undecaazacyclotetratriacontin]-5',8',11',14',18',21',24',29',32',37',40'(15'H,23'H)-undecaone, (667) (5S,8S,11S,15S,18S,23aS,29S,35S,37aS)-8-((S)-sec-butyl)-29-(3-chloro-4-(trifluoromethyl)phenethyl)-35-(cyclohexylmethyl)-12-ethyl-11-isobutyl-18-isopropyl-5,6,16,19,33,36-hexamethyl-15-(piperidine-1-carbonyl) docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (668) (5S,8S,11S,15R,18S,23aS,29S,35S,37aS)-8,18-di((S)-sec-butyl)-29-(3-chloro-4-(trifluoromethyl)phenethyl)-25,25-difluoro-11-isobutyl-5,6,12,15,16,19,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (669) (8S,11S,17S,26S,29S,33R,36S)-17-[(4-chlorophenyl) methyl]-8,36-diisobutyl-29-isopropyl-9,15,18,21,24,30,37-heptamethyl-26-[(1S)-1-methylpropyl]-33-prop-2-ynyl-1-[2-[4-(trifluoromethyl)phenyl]ethyl]-6,9,12,15,18,21,24,27,30,34,37-undecazaspiro[4.33] octatriacontane-7,10,13,16,19,22,25,28,31,35,38-undecone, (670) (6'S,12'S,21'S,23a'S,31'S,34'S,39a'S)-21'-((S)-sec-butyl)-12'-(cyclohexylmethyl)-6'-(3-fluoro-4-(trifluoromethyl)phenethyl)-34'-isopropyl-10',13',16',19',32',35'-hexamethyl-31'-(piperidine-1-carbonyl) tetracosahydrospiro[cyclopentane-1,37'-pyrido[1,2-a] pyrrolo[1,2-v][1,4,7,10,13,16,19,22,25,28,31] undecaazacyclotetratriacontin]-5',8',11',14',17',20',23',29',33',36',39'(23a'H,30'H,38'H)-undecaone, (671) (5S,8S,11S,15R,18S,23aS,29S,32R,35S,37aS)-35-benzyl-8-((S)-sec-butyl)-29-(3-chloro-4-(trifluoromethyl)phenethyl)-18-cyclopentyl-5,6,11,12,15,19,32,33,36-nonamethyldocosahydro-2H,4H-spiro[azeto[2,1-u] pyrrolo[2,1-i][1,4,7,10,13,16,19,22,25,28,31] undecaazacyclotetratriacontine-21,1'-cyclopentan]-4,7,10,13,17,20,23,28,31,34,37(14H,22H)-undecaone, (672) (5S,8S,11S,15S,18S,23aS,29S,35S,37aS)-8-((S)-sec-butyl)-29-(3-chloro-4-(trifluoromethyl)phenethyl)-18-cyclobutyl-35-(cyclohexylmethyl)-11-isobutyl-5,6,12,16,19,33,36-heptamethyl-15-(piperidine-1-carbonyl) docosahydro-2H,4H-spiro[azeto[2,1-u]pyrrolo[2,1-i][1,4,7,10,13,16,19,22,25,28,31] undecaazacyclotetratriacontine-21,1'-cyclopentan]-4,7,10,13,17,20,23,28,31,34,37(14H,22H)-undecaone, (673) (5S,8S,11S,15R,18S,23aS,25R,29S,35S,37aS)-8,18-di((S)-sec-butyl)-29-(3-chloro-4-(trifluoromethyl)phenethyl)-25-ethoxy-36-ethyl-11-isobutyl-5,12,15,16,19,33-hexamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (674) (5S,8S,11S,15S,18S,23aS,29S,35S,37aS)-8,18-di((S)-sec-butyl)-35-cyclopentyl-29-(3-fluoro-4-(trifluoromethyl)phenethyl)-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (675) (3S,6S,9S,12S,18S,27S,30S,34S)-18-[(4-chlorophenyl)methyl]-3,9-diisobutyl-6-(isopentyloxymethyl)-4,7,16,19,22,25,30,31-octamethyl-27-[(1S)-1-methylpropyl]-34-(pyrrolidine-1-carbonyl)-12-[2-[4-(trifluoromethyl) phenyl]ethyl]-1,4,7,10,13,16,19,22,25,28,31-undecazacyclotetratriacontane-2,5,8,11,14,17,20,23,26,29,32-undecone, (676) (5S,8S,11S,15S,18S,23aS,29S,35S,37aS)-8-((S)-sec-butyl)-29-(3-chloro-4-(trifluoromethyl)phenethyl)-35-(cyclohexylmethyl)-5-(cyclopropoxymethyl)-11-isobutyl-18-isopropyl-6,12,16,19,33,36-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (677) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-cyclopentyl-11-isobutyl-N,N,5,6,12,19,33,36-octamethyl-4,7,10,13,17,20,23,28,31,34,37-undecaoxotetratriacontahydro-2H,4H-spiro[azeto[2,1-u] pyrrolo[2,1-i][1,4,7,10,13,16,19,22,25,28,31] undecaazacyclotetratriacontine-21,1'-cyclopentane]-15-carboxamide, (678) (5S,8S,11S,15S,18S,23aS,29S,35S,37aS)-8,18-di((S)-sec-butyl)-29-(3-fluoro-4-(trifluoromethyl)phenethyl)-11-isobutyl-5,6,12,16,19,33,36-heptamethyl-35-(4-methylbenzyl)-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (679) (3S,6S,9S,12S,18S,27S,30S,34S)-12-[2-[3-chloro-4-(trifluoromethyl)phenyl]ethyl]-18-(cyclohexylmethyl)-9-[2-(3,3-difluoroazetidin-1-yl)-2-oxo-ethyl]-3-isopropyl-1,4,10,16,19,22,25,30,31-nonamethyl-27-[(1S)-1-methylpropyl]-34-(piperidine-1-carbonyl)-6-(2,2,2-trifluoroethyl)-1,4,7,10,13,16,19,22,25,28,31-undecazacyclotetratriacontane-2,5,8,11,14,17,20,23,26,29,32-undecone, (680) (5S,8S,11S,15S,18S,23aS,29S,35S,37aS)-8-((S)-sec-butyl)-29-(3-chloro-4-(trifluoromethyl)phenethyl)-35-(4-chlorobenzyl)-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (681) (3S,6S,9S,12S,18S,27S,30S,34S)-9-butyl-12-[(2-fluorophenyl)methyl]-3,30-diisobutyl-6,18-bis[(4-methoxyphenyl)methyl]-1,7,16,19,22,25,31-heptamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (682) (3S,6S,9S,13S,16S,22S,25S,31S,34S)-25-[2-[3-chloro-4-(trifluoromethyl)phenyl]ethyl]-31-(cyclohexylmethyl)-22-[2-(3,3-difluoro-1-piperidyl)ethyl]-16-isopropyl-3,4,9,10,14,17,23,29,32-nonamethyl-6-[(1S)-1-methylpropyl]-13-(piperidine-1-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (683) (3S,9S,18S,21S,25S,28S,34S)-3-[2-[3-chloro-4-(trifluoromethyl)phenyl]ethyl]-28-cyclohexyl-7,10,13,16,22,26,29-heptamethyl-18-[(1S)-1-methylpropyl]-25-(3-oxa-8-azabicyclo[3.2.1]octane-8-carbonyl)-9-(p-tolylmethyl)-21-(2,2,2-trifluoroethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (684) (5S,8S,11S,15S,18S,23aS,29S,35S,37aS)-8,18-di((S)-sec-butyl)-29-(3-fluoro-4-(trifluoromethyl)phenethyl)-11-isobutyl-5,6,12,16,19,33,36-heptamethyl-35-(propoxymethyl)-15-(pyrrolidine-1-carbonyl)docosahydro-2H,4H-spiro[azeto[2,1-u]pyrrolo[2,1-i][1,4,7,10,13,16,19,22,25,28,31]undecaazacyclotetracontine-21,1'-cyclopentan]-4,7,10,13,17,20,23,28,31,34,37(14H,22H)-undecaone, (685) (5S,8S,11S,15S,18S,23aS,29S,35S,37aS)-8-((S)-sec-butyl)-35-(cyclohexylmethyl)-29-(3-fluorophenethyl)-18-isopropyl-5,6,11,12,16,19,33,36-octamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetracontine-21,1'-cyclopentan]-4,7,10,13,17,20,23,28,31,34,37(14H,22H)-undecaone, (686) (3S,6S,9S,13R,16S,22S,25S,31S,34S)-31-(cyclohexylmethyl)-25-[2-[3-fluoro-4-(trifluoromethyl)phenyl]ethyl]-9,16,22-triisobutyl-3,4,10,13,14,19,19,20,29,32-decamethyl-6-[(1S)-1-methylpropyl]-1,4,7,10,14,17,20,23,26,29,32-undecazabicyclo[32.2.0]hexatriacontane-2,5,8,11,15,18,21,24,27,30,33-undecone, (687) (3S,9S,12S,18S,27S,30S,34R)-18-[(4-chlorophenyl)methyl]-12-[2-[3,5-difluoro-4-(trifluoromethyl)phenyl]ethyl]-3,9,30-triisobutyl-1,6,6,7,16,19,22,25,31,34-decamethyl-27-[(1S)-1-methylpropyl]-1,4,7,10,13,16,19,22,25,28,31-undecazacyclotetratriacontane-2,5,8,11,14,17,20,23,26,29,32-undecone, (688) 2-[(8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-9,15,18,21,24,30,34,37-octamethyl-26-[(1S)-1-methylpropyl]-7,10,13,16,19,22,25,28,31,35,38-undecaoxo-33-(piperidine-1-carbonyl)-6,9,12,15,18,21,24,27,30,34,37-undecazaspiro[4.33]octatriacontan-8-yl]acetic acid (689) (3S,9S,18S,21S,25S,28S,34S)-3-[2-[3-chloro-4-(trifluoromethyl)phenyl]ethyl]-28-cyclohexyl-9-(cyclohexylmethyl)-18-(cyclopropylmethyl)-21-isobutyl-7,10,13,16,22,26,29-heptamethyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (690) (5S,8S,11S,15S,18S,23aS,29S,35S,37aS)-8,18-di((S)-sec-butyl)-29-(3-chloro-4-(trifluoromethyl)phenethyl)-11-isobutyl-5,6,12,16,19,33,36-heptamethyl-15-(piperidine-1-carbonyl)-35-(propoxymethyl)docosahydro-2H,4H-spiro[azeto[2,1-u]pyrrolo[2,1-i][1,4,7,10,13,16,19,22,25,28,31]undecaazacyclotetracontine-21,1'-cyclopentan]-4,7,10,13,17,20,23,28,31,34,37(14H,22H)-undecaone, (691) (3S,6S,9S,13S,16S,22S,25S,31S,34S)-22-butyl-25-[2-[3-chloro-4-(trifluoromethyl)phenyl]ethyl]-31-(cyclopentylmethyl)-9,16-diisobutyl-3,4,10,14,19,19,20,29,32-nonamethyl-6-[(1S)-1-methylpropyl]-13-(piperidine-1-carbonyl)-1,4,7,10,14,17,20,23,26,29,32-undecazabicyclo[32.2.0]hexatriacontane-2,5,8,11,15,18,21,24,27,30,33-undecone, (692) (8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-9,15,18,21,24,30,34,37-octamethyl-26-[(1S)-1-methylpropyl]-33-(piperidine-1-carbonyl)-8-(propoxymethyl)-6,9,12,15,18,21,24,27,30,34,37-undecazaspiro[4.33]octatriacontane-7,10,13,16,19,22,25,28,31,35,38-undecone, (693) (5S,8S,11S,15S,18S,23aS,29S,35S,37aS)-8,18-di((S)-sec-butyl)-29-(3-chloro-4-(trifluoromethyl)phenethyl)-11-isobutyl-5,6,12,16,19,33,36-heptamethyl-15-(morpholine-4-carbonyl)-35-(propoxymethyl)docosahydro-2H,4H-spiro[azeto[2,1-u]pyrrolo[2,1-i][1,4,7,10,13,16,19,22,25,28,31]undecaazacyclotetracontine-21,1'-cyclopentan]-4,7,10,13,17,20,23,28,31,34,37(14H,22H)-undecaone, (694) (5S,8S,11S,15R,18S,23aS,29S,35S,37aS)-8,18-di((S)-sec-butyl)-29-(3-fluoro-4-(trifluoromethyl)phenethyl)-11-isobutyl-5,6,12,15,16,19,33,36-octamethyl-35-(propoxymethyl)docosahydro-2H,4H-spiro[azeto[2,1-u]pyrrolo[2,1-i][1,4,7,10,13,16,19,22,25,28,31]undecaazacyclotetracontine-21,1'-cyclopentan]-4,7,10,13,17,20,23,28,31,34,37(14H,22H)-undecaone, (695) (3S,9S,18S,21S,25R,28S,34S,36R)-3-[2-[3-chloro-4-(trifluoromethyl)phenyl]ethyl]-36-ethoxy-21-isobutyl-7,10,13,16,22,25,26,29-octamethyl-18,28-bis[(1S)-1-methylpropyl]-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (696) (3S,6S,9S,12S,18S,27S,30S,34S)-9-butyl-18-[(4-chlorophenyl)methy]-12-[(3-iodophenyl)methyl]-3,30-diisobutyl-1,7,16,19,22,25,31-heptamethyl-27-[(1S)-1-methylpropyl]-6-(o-tolylmethyl)-34-(piperidine-1-carbonyl)-1,4,7,10,13,16,19,22,25,28,31-undecazacyclotetratriacontane-2,5,8,11,14,17,20,23,26,29,32-undecone, (697) (3S,9S,18S,21S,25R,28S,34S)-3-[2-[3-chloro-4-(trifluoromethyl)phenyl]ethyl]-9-(cyclohexylmethyl)-28-isopropyl-7,10,13,16,21,22,25,29-octamethyl-8-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (698) (5S,8S,11S,15R,18S,23aS,25R,29S,35S,37aS)-8-((S)-sec-butyl)-29-(3-chloro-4-(trifluoromethyl)phenethyl)-18-cyclohexyl-25-ethoxy-11-isobutyl-5,6,12,15,16,19,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetracontine-21,1'-cyclobutan]-4,7,10,13,17,20,23,28,31,34,37(14H,22H)-undecaone, (699) (3S,9S,18S,21S,25S,28S,34S)-3-[2-[3-chloro-4-(trifluoromethyl)phenyl]ethyl]-21-(cyclobutoxymethyl)-28-cyclohexyl-9-(cyclohexylmethyl)-7,10,13,16,22,26,29-heptamethyl-18-[(1S)-1-methylpropyl]-25-(piperidine-1-carbonyl)spiro[1,4,7,10,13,16,19,22,26,29,32- undecazabicyclo[32.3.0]heptatriacontane-31,1'-cyclopentane]-2,5,8,11,14,17,20,23,27,30,33-undecone, (700) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-cyclopentyl-11-isobutyl-5,6,12,19,33,36-hexamethyl-15-(pyrrolidine-1-carbonyl) docosahydro-2H,4H-spiro[azeto[2,1-u]pyrrolo[2,1-i][1,4,7,10,13,16,19,22,25,28,31] undecaazacyclotetratriacontine-21,1'-cyclopentan]-4,7,10,13,17,20,23,28,31,34,37(14H,22H)-undecaone, (701) (3S,9S,18S,21S,25S,28S,34S)-3-[2-[3-chloro-4-(trifluoromethyl)phenyl]ethyl]-21-cyclobutyl-28-cyclohexyl-9-(cyclohexylmethyl)-7,10,13,16,22,26,29-heptamethyl-18-[(1S)-1-methylpropyl]-25-(3-oxa-8-azabicyclo[3.2.1]octane-8-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (702) (3S,6R,9S,12S,18S,27S,30S,34S)-9-[(2-chlorophenyl)methyl]-12-[2-[3-chloro-4-(trifluoromethyl)phenyl]ethyl]-18-(cyclohexylmethyl)-3-isopropyl-1,4,6,10,16,19,22,25,30,31-decamethyl-27-[(1S)-1-methylpropyl]-34-(pyrrolidine-1-carbonyl)-1,4,7,10,13,16,19,22,25,28,31-undecazacyclotetratriacontane-2,5,8,11,14,17,20,23,26,29,32-undecone, (703) (3S,6S,9S,13S,16S,22S,25S,31S,34S)-25-[(3-iodophenyl)methyl]-9,16-diisobutyl-22-[(4-methoxyphenyl)methyl]-3,4,10,14,19,19,20,29,32-nonamethyl-6-[(1S)-1-methylpropyl]-13-(piperidine-1-carbonyl)-31-(p-tolylmethyl)-1,4,7,10,14,17,20,23,26,29,32-undecazabicyclo[32.2.0]hexatriacontane-2,5,8,11,15,18,21,24,27,30,33-undecone, (704) (5S,8S,11S,15R,18S,23aS,25R,29S,35S,37aS)-8-((S)-sec-butyl)-35-(cyclohexylmethyl)-18-cyclopentyl-29-(3,5-difluoro-4-(trifluoromethyl)phenethyl)-25-ethoxy-11-isobutyl-5,6,12,15,16,19,33,36-octamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (705) (3S,9S,18S,21S,25R,28S,31S,34S)-3-[2-[3-chloro-4-(trifluoromethyl)phenyl]ethyl]-9-(cyclohexylmethyl)-21,31-diisobutyl-28-isopropyl-7,10,13,16,22,25,29,31-octamethyl-18-[(1S)-1-methylpropyl]-1,4,7,10,13,16,19,22,26,29,32-undecazabicyclo[32.3.0]heptatriacontane-2,5,8,11,14,17,20,23,27,30,33-undecone, (706) (3S,9S,12S,18S,27S,30S,34S)-9-[(2-chlorophenyl)methyl]-12-[(3-iodophenyl)methyl]-3,30-diisobutyl-1,6,6,7,16,19,22,25,31-nonamethyl-27-[(1S)-1-methylpropyl]-34-(piperidine-1-carbonyl)-18-(p-tolylmethyl)-1,4,7,10,13,16,19,22,25,28,31-undecazacyclotetratriacontane-2,5,8,11,14,17,20,23,26,29,32-undecone, (707) (3S,9S,18S,21S,25R,28S,34S)-3-[2-[3-chloro-4-(trifluoromethyl)phenyl]ethyl]-9-(cyclohexylmethyl)-28-(cyclopropylmethyl)-21-isobutyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (708) (3S,9S,18S,21S,25R,28S,34S)-3-[2-[3-chloro-4-(trifluoromethyl)phenyl]ethyl]-9-(cyclohexylmethyl)-21-isobutyl-7,10,13,16,22,25,29-heptamethyl-18,28-bis[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (709) (6S,9S,13S,16S,21aS,27S,33S,35aS,39aS)-6-((S)-sec-butyl)-27-(3-chloro-4-(trifluoromethyl)phenethyl)-33-(cyclohexylmethyl)-9-isobutyl-16-isopropyl-10,14,17,31,34-pentamethyl-13-(piperidine-1-carbonyl)docosahydro-1H,26H-spiro[azeto[1,2-j]dipyrrolo[1,2-g:1',2'-v][1,4,7,10,13,16,19,22,25,28,31]undecaazacyclotetratriacontine-19,1'-cyclopentan]-5,8,11,15,18,21,26,29,32,35,39(12H,20H,35aH,39aH)-undecaone, (710) 3-[[(3S,9S,18S,21S,25S,28S,34S)-3-[2-[3-chloro-4-(trifluoromethyl)phenyl]ethyl]-21-isobutyl-28-isopropyl-7,10,13,16,22,26,29-heptamethyl-18-[(1S)-1-methylpropyl]-2,5,8,11,14,17,20,23,27,30,33-undecaoxo-25-(piperidine-1-carbonyl)spiro[1,4,7,10,13,16,19,22,26,29,32-undecazabicyclo[32.3.0]heptatriacontane-31,1'-cyclopentane]-9-yl]methyl]benzonitrile, (711) (3S,9S,12S,18S,27S,30S,34S)-18-(cyclohexylmethyl)-9-[(4-fluorophenyl)methyl]-12-[(3-iodophenyl)methyl]-3,30-diisobutyl-1,6,6,7,16,19,22,25,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (712) (3S,9S,18S,21S,25S,28S,34S)-3-[2-[3-chloro-4-(trifluoromethyl)phenyl]ethyl]-9-(cyclohexylmethyl)-21-isobutyl-28-isopropyl-7,10,13,16,22,26,29-heptamethyl-8-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclobutane]-2,5,8,11,14,17,20,23,27,30,33-undecone, (713) (5S,8S,11S,15R,18S,23aS,25R,29S,35S,37aS)-8-((S)-sec-butyl)-29-(3-chloro-4-(trifluoromethyl)phenethyl)-18-cyclopentyl-25-ethoxy-36-ethyl-11-isobutyl-5,6,12,15,16,19,33-heptamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclobutan]-4,7,10,13,17,20,23,28,31,34,37(14H,22H)-undecaone, (714) (3S,9S,18S,21S,25R,28S,34S)-3-[2-[3-chloro-4-(trifluoromethyl)phenyl]ethyl]-9-(cyclohexylmethyl)-28-isopropyl-7,10,13,16,21,22,25,26,29-nonamethyl-8-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (715) (3S,6S,9S,13S,16S,19S,22S,25S,31S,34S)-25-[2-[3-chloro-4-(trifluoromethyl)phenyl]ethyl]-9-isobutyl-N,N,3,4,10,14,17,19,22,23,29,32-dodecamethyl-6,16-bis[(1S)-1-methylpropyl]-2,5,8,11,15,18,21,24,27,30,33-undecaoxo-31-(p-tolylmethyl)-1,4,7,10,14,17,20,23,26,29,32-undecazabicyclo[32.2.0]hexatriacontane-13-carboxamide, (716) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-25-(piperidine-1-carbonyl)-18-prop-2-ynyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone, (717) (5S,8S,11S,15R,18S,23aS,29S,35S,37aS)-8,18-di((S)-sec-butyl)-29-(3-chloro-4-(trifluoromethyl)phenethyl)-11-isobutyl-5,6,12,15,16,19,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (718) (8S,11S,17S,26S,29S,33S,36S)-8-[(4-chlorophenyl)methyl]-11-[2-[3-chloro-4-(trifluoromethyl)phenyl]ethyl]-17-(cyclohexylmethyl)-36-isopropyl-9,15,18,21,24,29,30,34,37-nonamethyl-26-[(1S)-1-methylpropyl]-

33-(piperidine-1-carbonyl)-6,9,12,15,18,21,24,27,30,34, 37-undecazaspiro[4.33]octatriacontane-7,10,13,16,19,22, 25,28,31,35,38-undecone, (719) (3S,6S,9S,13S,16S,22S,25S,31S,34S)-13-(azetidine-1-carbonyl)-25-[2-[3-chloro-4-(trifluoromethyl)phenyl] ethyl]-31-(cyclohexylmethyl)-16-cyclopentyl-22-[2-(4,4-difluoro-1-piperidyl)-2-oxo-ethyl]-9-isobutyl-3,4,10,14, 17,23,29,32-octamethyl-6-[(1S)-1-methylpropyl]spiro[1, 4,7,10,14,17,20,23,26,29,32-undecazabicyclo[32.2.0] hexatriacontane-19,1'-cyclopentane]-2,5,8,11,15,18,21, 24,27,30,33-undecone, (720) (5S,8S,11S,15R,18S,23aS,29S,32R,35S,37aS)-8-((S)-sec-butyl)-29-(3-chloro-4-(trifluoromethyl)phenethyl)-35-(4-chlorobenzyl)-18-cyclopentyl-5,6,11,12,15,19,32, 33,36-nonamethyldocosahydro-2H,4H-spiro[azeto[2,1-u]pyrrolo[2,1-i][1,4,7,10,13,16,19,22,25,28,31] undecaazacyclotetratriacontine-21,1'-cyclopentan]-4,7, 10,13,17,20,23,28,31,34,37(14H,22H)-undecaone, (721) (5S,8S,11S,15S,18S,23aS,29S,35S,37aS)-15-(3-oxa-8-azabicyclo[3.2.1]octane-8-carbonyl)-8-((S)-sec-butyl)-29-(3-chloro-4-(trifluoromethyl)phenethyl)-18,35-dicyclopentyl-11-isobutyl-5,6,12,16,19,33,36-heptamethyldocosahydro-2H,4H-spiro[azeto[2,1-u]pyrrolo[2,1-i][1,4,7,10,13,16,19,22,25,28,31] undecaazacyclotetratriacontine-21,1'-cyclopentan]-4,7, 10,13,17,20,23,28,31,34,37(14H,22H)-undecaone, (722) (3S,6S,9S,18S,21S,25S,28S,34S)-3-[2-[3-chloro-4-(trifluoromethyl)phenyl]ethyl]-28-cyclohexyl-9-(cyclohexylmethyl)-21-isobutyl-6,7,10,13,16,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (723) (3S,9S,18S,21S,25R,28S,34S)-3-[2-[3-chloro-4-(trifluoromethyl)phenyl]ethyl]-28-(cyclobutylmethyl)-9-(cyclohexylmethyl)-21-isobutyl-7,10,13,16,22,25,26,29-octamethyl-18-[(1S)-1-methylpropyl]spiro[1,4,7,10,13,16, 19,22,26,29,32-undecazabicyclo[32.3.0] heptatriacontane-31,1'-cyclopentane]-2,5,8,11,14,17,20, 23,27,30,33-undecone, (724) (5S,8S,11S,15R,18S,23aS,25R,29S,35S,37aS)-8-((S)-sec-butyl)-18-cyclohexyl-29-(3,5-difluoro-4-(trifluoromethyl)phenethyl)-25-ethoxy-36-ethyl-11-isobutyl-5,6,12, 15,16,19,33-heptamethyl-35-(4-methylbenzyl) docosahydro-2H,4H-spiro[azeto[2,1-u]pyrrolo[2,1-i][1,4, 7,10,13,16,19,22,25,28,31] undecaazacyclotetratriacontine-21,1'-cyclobutan]-4,7,10, 13,17,20,23,28,31,34,37(14H,22H)-undecaone, (725) (8S,11S,15S,18S,23aS,31S,37S,39aS)-8-((S)-sec-butyl)-31-(3-chloro-4-(trifluoromethyl)phenethyl)-18-cyclohexyl-37-(cyclohexylmethyl)-11-isobutyl-6,12,16,19, 35,38-hexamethyl-15-(piperidine-1-carbonyl)-1,5,6,8,9, 11,12,15,16,18,19,23a,24,31,32,34,35,37,38,39a-icosahydro-2H,4H-spiro[azeto[2',1':21,22][1,4,7,10,13, 16,19,22,25,28,31]undecaazacyclotetratriacontino[10,9-a]indole-21,1'-cyclopentan]-4,7,10,13,17,20,23,30,33,36, 39(14H,22H)-undecaone, (726) (5S,8S,11S,15S,18S,23aS,29S,35S,37aS)-15-(azetidine-1-carbonyl)-8-((S)-sec-butyl)-29-(3-chloro-4-(trifluoromethyl)phenethyl)-35-(cyclohexylmethyl)-18-cyclopentyl-33-ethyl-11-isobutyl-5,6,12,16,19,36-hexamethyldocosahydro-2H,4H-spiro[azeto[2,1-u]pyrrolo[2,1-i][1,4,7,10,13,16,19,22,25,28,31] undecaazacyclotetratriacontine-21,1'-cyclopentan]-4,7, 10,13,17,20,23,28,31,34,37(14H,22H)-undecaone, (727) N-tert-butyl-2-[[(8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-9,15,18,21,24, 30,34,37-octamethyl-26-[(1S)-1-methylpropyl]-7,10,13, 16,19,22,25,28,31,35,38-undecaoxo-33-(piperidine-1-carbonyl)-6,9,12,15,18,21,24,27,30,34,37-undecazaspiro [4.33]octatriacontan-8-yl]methoxy]acetamide, (728) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-25-(piperidine-1-carbonyl) spiro[1,4,7,10,13,16,19,22,26,29,32-undecazabicyclo [32.4.0]octatriacontane-31,1'-cyclopentane]-2,5,8,11,14, 17,20,23,27,30,33-undecone, (729) (5S,8S,11S,15S,18S,23aS,29S,35S,37aS)-29-(3-chloro-4-(trifluoromethyl)phenethyl)-35-(cyclohexylmethyl)-11-isobutyl-18-isopropyl-5,6,12,16,19,33,36-heptamethyl-8-(3-methylbut-2-en-1-yl)-15-(piperidine-1-carbonyl)docosahydro-2H,4H-spiro[azeto[2,1-u]pyrrolo [2,1-i][1,4,7,10,13,16,19,22,25,28,31] undecaazacyclotetratriacontine-21,1'-cyclopentan]-4,7, 10,13,17,20,23,28,31,34,37(14H,22H)-undecaone, (730) (8S,11S,17S,26S,29S,33S,36S)-8-butyl-11-[2-[3-chloro-4-(trifluoromethyl)phenyl]ethyl]-36-cyclohexyl-17-(cyclohexylmethyl)-29-isobutyl-9,15,18,21,24,30,34, 37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25, 28,31,35,38-undecone, (731) (5S,8S,11S,15R,18S,23aS,25R,29S,35S,37aS)-8,18-di((S)-sec-butyl)-29-(3,5-difluoro-4-(trifluoromethyl) phenethyl)-25-ethoxy-36-ethyl-11-isobutyl-5,6,12,15,16, 19,33-heptamethyl-35-(4-(trifluoromethyl)benzyl) docosahydro-2H,4H-spiro[azeto[2,1-u]pyrrolo[2,1-i][1,4, 7,10,13,16,19,22,25,28,31] undecaazacyclotetratriacontine-21,1'-cyclobutan]-4,7,10, 13,17,20,23,28,31,34,37(14H,22H)-undecaone, (732) (3S,9S,18S,21S,25S,28S,34S)-3-[2-[3-chloro-4-(trifluoromethyl)phenyl]ethyl]-28-cyclohexyl-21-isobutyl-7, 10,13,16,22,26,29-heptamethyl-18-[(1S)-1-methylpropyl]-25-(piperidine-1-carbonyl)-9-(2,2,2-trifluoroethoxymethyl)spiro[1,4,7,10,13,16,19,22,26,29, 32-undecazabicyclo[32.3.0]heptatriacontane-31,1'-cyclopentane]-2,5,8,11,14,17,20,23,27,30,33-undecone, (733) (5S,8S,11S,15S,18S,23aS,29S,35S,37aS)-29-(3-chloro-4-(trifluoromethyl)phenethyl)-8-(cyclobutylmethyl)-35-(cyclohexylmethyl)-11-isobutyl-18-isopropyl-5,6,12,16,19,33,36-heptamethyl-15-(piperidine-1-carbonyl)docosahydro-2H,4H-spiro[azeto[2,1-u]pyrrolo [2,1-i][1,4,7,10,13,16,19,22,25,28,31] undecaazacyclotetratriacontine-21,1'-cyclopentan]-4,7, 10,13,17,20,23,28,31,34,37(14H,22H)-undecaone, (734) (5S,8S,11S,15S,18S,23aS,29S,35S,37aS)-15-(3-oxa-8-azabicyclo[3.2.1]octane-8-carbonyl)-8-((S)-sec-butyl)-35-(cyclohexylmethyl)-18-cyclopentyl-29-(3-fluoro-4-(trifluoromethyl)phenethyl)-11-isobutyl-5,6,12,16,19,33, 36-heptamethyldocosahydro-2H,4H-spiro[azeto[2,1-u] pyrrolo[2,1-i][1,4,7,10,13,16,19,22,25,28,31] undecaazacyclotetratriacontine-21,1'-cyclopentan]-4,7, 10,13,17,20,23,28,31,34,37(14H,22H)-undecaone, (735) (3S,9S,18S,21S,25S,28S,34S)-3-[2-[3-chloro-4-(trifluoromethyl)phenyl]ethyl]-28-cyclohexyl-7,10,13,16,22, 26,29-heptamethyl-18-[(1S)-1-methylpropyl]-9-(propoxymethyl)-25-(pyrrolidine-1-carbonyl)-21-(2,2,2-trifluoroethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (736) (3S,6S,9S,13S,16S,19S,22R,25S,31S,34S)-25-[2-[3-chloro-4-(trifluoromethyl)phenyl]ethyl]-31-(cyclohexylmethyl)-16-cyclopentyl-9-isobutyl-N,N,3,4,10,14,17,19, 22,29,32-undecamethyl-6-[(1S)-1-methylpropyl]-2,5,8, 11,15,18,21,24,27,30,33-undecaoxo-1,4,7,10,14,17,20, 23,26,29,32-undecazabicyclo[32.2.0]hexatriacontane-13-carboxamide, (737) (3S,9S,18S,21S,25S,28S,34S)-25-(4-tert-butylpiperidine-1-carbonyl)-3-[2-[3-chloro-4-(trifluoromethyl)phenyl]ethyl]-9-(cyclohexylmethyl)-21-isobutyl-28-isopropyl-7,10,13,16,22,29-hexamethyl-18-(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (738) (3S,9S,18S,21S,25R,28S,34S)-28-cyclohexyl-9-(cyclohexylmethyl)-3-[2-[3,5-difluoro-4-(trifluoromethyl)phenyl]ethyl]-36,36-difluoro-21-isobutyl-7,10,13,16,22, 25,26,29-octamethyl-18-[(1S)-1-methylpropyl]spiro[1,4, 7,10,13,16,19,22,26,29,32-undecazabicyclo[32.3.0] heptatriacontane-31,1'-cyclobutane]-2,5,8,11,14,17,20, 23,27,30,33-undecone, (739) (3S,6S,9S,12S,18S,27S,30S,34S)-18-[(4-chlorophenyl)methyl]-3,9-diisobutyl-4,7,16,19,22,25,30,31-octamethyl-27-[(1S)-1-methylpropyl]-6-(propoxymethyl)-34-(pyrrolidine-1-carbonyl)-12-[2-[4-(trifluoromethyl)phenyl]ethyl]-1,4,7,10,13,16,19,22,25,28,31-undecazacyclotetratriacontane-2,5,8,11,14,17,20,23,26, 29,32-undecone, (740) (3S,9S,12S,18S,27S,30S,34R)-18-[(4-chlorophenyl)methyl]-12-[2-[3-chloro-4-(trifluoromethyl)phenyl] ethyl]-3,9-diisobutyl-30-isopropyl-4,6,6,10,16,19,22,25, 31,34-decamethyl-27-[(1S)-1-methylpropyl]-1,4,7,10,13, 16,19,22,25,28,31-undecazacyclotetratriacontane-2,5,8, 11,14,17,20,23,26,29,32-undecone, (741) (5S,8S,11S,15S,18S,21S,23aS,29S,35S,37aS)-8-((S)-sec-butyl)-29-(3-chloro-4-(trifluoromethyl)phenethyl)-35-(cyclohexylmethyl)-11-isobutyl-18,21-diisopropyl-5, 6,12,16,19,33,36-heptamethyl-15-(piperidine-1-carbonyl)tetracosahydro-2H-azeto[2,1-u]pyrrolo[2,1-i] [1,4,7,10,13,16,19,22,25,28,31] undecaazacyclotetratriacontin-4,7,10,13,17,20,23,28,31, 34,37(14H)-undecaone, (742) (3S,9S,18S,21S,25R,28S,34S)-3-[2-[3-chloro-4-(trifluoromethyl)phenyl]ethyl]-9-(cyclohexylmethyl)-21,28-diisobutyl-7,10,13,16,22,25,26,29-octamethyl-8-[(1S)-1-methylpropyl]spiro[1,4,7,10,13,16,19,22,26,29,32-undecazabicyclo[32.3.0]heptatriacontane-31,4'-tetrahydropyran]-2,5,8,11,14,17,20,23,27,30,33-undecone, (743) (5S,8S,11S,15R,18S,23aS,25R,29S,35S,37aS)-8-((S)-sec-butyl)-29-(3-chloro-4-(trifluoromethyl)phenethyl)-18-cyclohexyl-25-ethoxy-36-ethyl-11-isobutyl-5,12,15, 16,19,33-hexamethyl-35-(4-(trifluoromethyl)benzyl) docosahydro-2H,4H-spiro[azeto[2,1-u]pyrrolo[2,1-i][1,4, 7,10,13,16,19,22,25,28,31] undecaazacyclotetratriacontine-21,1'-cyclobutan]-4,7,10, 13,17,20,23,28,31,34,37(14H,22H)-undecaone, (744) (3S,9S,18S,21S,25S,28S,34S)-3-[2-[3-chloro-4-(trifluoromethyl)phenyl]ethyl]-9-(cyclohexylmethyl)-21-isobutyl-28-(2-methoxyethyl)-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (745) (5S,8S,11S,15S,18S,23aS,29S,35S,37aS)-8-allyl-29-(3-chloro-4-(trifluoromethyl)phenethyl)-35-(cyclohexylmethyl)-11-isobutyl-18-isopropyl-5,6,12,16,19,33,36-heptamethyl-15-(piperidine-1-carbonyl)docosahydro-2H, 4H-spiro[azeto[2,1-u]pyrrolo[2,1-i][1,4,7,10,13,16,19, 22,25,28,31]undecaazacyclotetratriacontine-21,1'-cyclopentan]-4,7,10,13,17,20,23,28,31,34,37(14H,22H)-undecaone, (746) (7'S,16'S,19'S,23'R,26'S,31a'S,37'S,39a'R)-16'-((S)-sec-butyl)-37'-(3-chloro-4-(trifluoromethyl)phenethyl)-7'-(cyclohexylmethyl)-26'-isopropyl-8',11',14',19',20',23', 27'-heptamethyltetracosahydro-2'H,6'H-spiro [cyclopentane-1,29'-pyrido[2,1-o]pyrrolo[2,1-i][1,4,7,10, 13,16,19,22,25,28,31]undecaazacyclotetratriacontin]-6', 9',12',15',18',21',25',28',31',36',39'(22'H,30'H)-undecaone, (747) (6'S,12'S,21'S,24'S,27a'R,34'S,39a'S)-21'-((S)-sec-butyl)-6'-(3-chloro-4-(trifluoromethyl)phenethyl)-12'-(cyclohexylmethyl)-24'-isopropyl-34'-isopropyl-10',13', 16',19',25',35'-hexamethylhexacosahydrospiro [cyclopentane-1,37'-pyrido[1,2-e1]pyrrolo[1,2-v][1,4,7, 10,13,16,19,22,25,28,31]undecaazacyclotetratriacontin]-5',8',11',14',17',20',23',26',33',36',39'(38'H)-undecaone, (748) (3S,6R,9S,12S,18S,27S,30S,34S)-6-allyl-9-[(2-chlorophenyl)methyl]-12-[2-[3-chloro-4-(trifluoromethyl) phenyl]ethyl]-18-(cyclohexylmethyl)-3-isopropyl-1,4,10, 16,19,22,25,30,31-nonamethyl-27-[(1S)-1-methylpropyl]-34-(pyrrolidine-1-carbonyl)-1,4,7,10,13, 16,19,22,25,28,31-undecazacyclotetratriacontane-2,5,8, 11,14,17,20,23,26,29,32-undecone, (749) (9'S,12'S,16'R,19'S,24a'S,30'S,36'S,38a'S)-9'-((S)-sec-butyl)-30'-(3-chloro-4-(trifluoromethyl)phenethyl)-19'-cyclopentyl-7',12',13',16',20',34',37'-heptamethyl-36'-(4-(trifluoromethyl)benzyl)tetracosahydro-5'H-spiro [cyclopentane-1,22'-dipyrrolo[2,1-i:2',1'-u][1,4,7,10,13, 16,19,22,25,28,31]undecaazacyclotetratriacontin]-5',8', 11',14',18',21',24',29',32',35',38'(15'H,23'H)-undecaone, (750) (3S,9S,18S,21S,25R,28S,34S)-3-[2-[3-chloro-4-(trifluoromethyl)phenyl]ethyl]-28-cyclohexyl-36,36-difluoro-21-isobutyl-7,10,13,16,22,25,26,29-octamethyl-18-[(1S)-1-methylpropyl]-9-[[4-(trifluoromethyl)phenyl] methyl]spiro[1,4,7,10,13,16,19,22,26,29,32-undecazabicyclo[32.3.0]heptatriacontane-31,1'-cyclobutane]-2,5,8,11,14,17,20,23,27,30,33-undecone, (751) (3S,9S,18S,21S,25R,28S,31S,34S)-31-benzyl-9-[(4-chlorophenyl)methyl]-28-isobutyl-7,10,13,16,21,22,25, 29,32-nonamethyl-8-[(1S)-1-methylpropyl]-3-[2-[4-(trifluoromethyl)phenyl]ethyl]-1,4,7,10,13,16,19,22,26,29, 32-undecazabicyclo[32.3.0]heptatriacontane-2,5,8,11,14, 17,20,23,27,30,33-undecone, (752) (3S,6S,9S,12S,18S,27S,30S,34S)-6-benzyl-18-[(4-chlorophenyl)methyl]-9-isobutyl-3-isopropyl-4,7,10,16, 19,22,25,30,31-nonamethyl-27-[(1S)-1-methylpropyl]-34-(piperidine-1-carbonyl)-12-[2-[4-(trifluoromethyl) phenyl]ethyl]-1,4,7,10,13,16,19,22,25,28,31-undecazacyclotetratriacontane-2,5,8,11,14,17,20,23,26, 29,32-undecone, (753) (3S,9S,18S,25R,28S,34S)-25-benzyl-3-[2-[3-chloro-4-(trifluoromethyl)phenyl]ethyl]-9-(cyclohexylmethyl)-28-cyclopentyl-7,10,13,16,23,26,29-heptamethyl-18-[(1S)-1-methylpropyl]spiro[1,4,7,10,13,16,19,23,26,29, 32-undecazabicyclo[32.3.0]heptatriacontane-31,1'-cyclopentane]-2,5,8,11,14,17,20,24,27,30,33-undecone, (754) (3S,6S,9S,13S,16S,22S,25S,31S,34S)-25-[(3-iodophenyl)methyl]-9,16-diisobutyl-22-[(2-methoxyphenyl) methyl]-3,4,10,14,19,19,20,29,32-nonamethyl-6-[(1S)-1-methylpropyl]-13-(piperidine-1-carbonyl)-31-(p-tolylmethyl)-1,4,7,10,14,17,20,23,26,29,32-undecazabicyclo[32.2.0]hexatriacontane-2,5,8,11,15,18, 21,24,27,30,33-undecone, (755) (5S,8S,11S,15S,18S,23aS,29S,35S,37aS)-8-((S)-sec-butyl)-29-(3-chloro-4-(trifluoromethyl)phenethyl)-11-

(cyclobutoxymethyl)-35-(cyclohexylmethyl)-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (756) (3S,9S,18S,21S,25S,28S,34S)-3-[2-[3-chloro-4-(trifluoromethyl)phenyl]ethyl]-28-cyclohexyl-9-(cyclohexylmethyl)-21-[(1R)-1-hydroxyethyl]-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (757) (6S,9S,13S,16S,22S,25S,31S,34S)-25-[2-[3-chloro-4-(trifluoromethyl)phenyl]ethyl]-16-cyclohexyl-31-(cyclohexylmethyl)-9-isobutyl-4,10,14,17,23,29,32-heptamethyl-6-[(1S)-1-methylpropyl]-13-(piperidine-1-carbonyl)-22-(3-pyridylmethyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (758) (3S,6S,9S,12S,18S,27S,30S,34S)-6-benzyl-12-[(3-chlorophenyl)methyl]-18-[(4-chlorophenyl)methyl]-3,9-diisobutyl-4,7,16,19,22,25,30,31-octamethyl-27-[(1S)-1-methylpropyl]-34-(pyrrolidine-1-carbonyl)-1,4,7,10,13,16,19,22,25,28,31-undecazacyclotetratriacontane-2,5,8,11,14,17,20,23,26,29,32-undecone, (759) N-tert-butyl-2-[[(8S,11S,17S,26S,29S,33S,36S)-17-[(4-chlorophenyl)methyl]-8,36-diisobutyl-29-isopropyl-9,15,18,21,24,30,37-heptamethyl-26-[(1S)-1-methylpropyl]-7,10,13,16,19,22,25,28,31,35,38-undecaoxo-11-[2-[4-(trifluoromethyl)phenyl]ethyl]-6,9,12,15,18,21,24,27,30,34,37-undecazaspiro[4.33]octatriacontan-33-yl]methoxy]acetamide, (760) (2aS,5S,11S,14S,20S,23S,30aS,33S)-33-((S)-sec-butyl)-14-butyl-11-(3-chloro-4-(trifluoromethyl)phenethyl)-5-(cyclohexylmethyl)-20-isobutyl-4,7,16,17,17,22,35-heptamethyl-23-(piperidine-1-carbonyl)tetracosahydroazeto[1,2-j]pyrido[1,2-a][1,4,7,10,13,16,19,22,25,28,31]undecaazacyclotetratriacontin-3,6,9,12,15,18,21,25,31,34,37(1H,22H,27H)-undecaone, (761) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-22-[2-(3,3-difluoroazetidin-1-yl)-2-oxo-ethyl]-9-isobutyl-N,N,3,4,10,14,17,23,29,32-decamethyl-6-[(1S)-1-methylpropyl]-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide, (762) (3S,9S,18S,21S,25S,28S,34S)-3-[2-[3-chloro-4-(trifluoromethyl)phenyl]ethyl]-9-(cyclohexylmethyl)-21-isobutyl-28-isopentyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (764) (3S,6S,9S,12S,18S,27S,30S,34R)-6-benzyl-9-tert-butyl-18-[(4-chlorophenyl)methyl]-3-isobutyl-4,7,16,19,22,25,30,31,34-nonamethyl-27-[(1S)-1-methylpropyl]-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (765) (3S,9S,12S,18S,27S,30S,34S)-3,9-dibutyl-8-[(4-chlorophenyl)methyl]-12-[(3-iodophenyl)methyl]-30-isobutyl-1,6,6,7,16,19,22,25,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (766) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-5,6,12,16,19,33,36-heptamethyl-15-(piperidine-1-carbonyl)-18-(prop-2-yn-1-yl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (767) 2-[[(3S,9S,18S,21S,25R,28S,34S)-3-[2-[3-chloro-4-(trifluoromethyl)phenyl]ethyl]-21-isobutyl-28-isopropyl-7,10,13,16,22,25,29-heptamethyl-18-[(1S)-1-methylpropyl]-2,5,8,11,14,17,20,23,27,30,33-undecaoxo-spiro[1,4,7,10,13,16,19,22,26,29,32-undecazabicyclo[32.3.0]heptatriacontane-31,1'-cyclopentane]-9-yl]methyl]benzonitrile, (768) (5S,8S,11S,15S,18S,23aS,29S,35S,37aS)-15-(azetidine-1-carbonyl)-8-((S)-sec-butyl)-29-(3-chloro-4-(trifluoromethyl)phenethyl)-35-(cyclohexylmethyl)-18-cyclopentyl-11-isopentyl-5,12,16,19,33,36-hexamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (769) (8S,11S,17S,26S,29S,33S,36S)-17-[(4-chlorophenyl)methyl]-8,36-diisobutyl-29-isopropyl-9,15,18,21,24,30,37-heptamethyl-26-[(1S)-1-methylpropyl]-33-(pyrrolidine-1-carbonyl)-11-[2-[4-(trifluoromethyl)phenyl]ethyl]-6,9,12,15,18,21,24,27,30,34,37-undecazaspiro[4.33]octatriacontane-7,10,13,16,19,22,25,28,31,35,38-undecone, (770) (6S,9S,13S,16S,22S,25S,31S,34S)-25-[2-[3-chloro-4-(trifluoromethyl)phenyl]ethyl]-16-cyclohexyl-31-(cyclohexylmethyl)-9-isobutyl-22-[(5-methoxy-3-pyridyl)methyl]-4,10,14,17,23,29,32-heptamethyl-6-[(1S)-1-methylpropyl]-13-(piperidine-1-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (771) (5S,8S,11S,15R,18S,23aS,29S,35S,37aS)-8-((S)-sec-butyl)-29-(3-chloro-4-(trifluoromethyl)phenethyl)-35-(cyclohexylmethyl)-11-(cyclopropylmethyl)-18-isopropyl-5,6,12,15,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (772) (3S,9S,12S,18S,27S,30S,34R)-18-[(4-chlorophenyl)methyl]-9-cyclohexyl-12-[2-[3-fluoro-4-(trifluoromethyl)phenyl]ethyl]-3,30-diisobutyl-1,6,6,7,16,19,22,25,31,34-decamethyl-27-[(1S)-1-methylpropyl]-1,4,7,10,13,16,19,22,25,28,31-undecazacyclotetratriacontane-2,5,8,11,14,17,20,23,26,29,32-undecone, (773) (3S,6R,9S,18S,21S,25R,28S,34S)-3-[2-[3-chloro-4-(trifluoromethyl)phenyl]ethyl]-9-(cyclohexylmethyl)-28-isopropyl-6,7,10,13,16,21,22,25,29-nonamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (774) (3S,9S,18S,21S,25S,28S,34S)-3-[2-[3-chloro-4-(trifluoromethyl)phenyl]ethyl]-28-cyclohexyl-9-(cyclohexylmethyl)-7,10,13,16,22,26,29-heptamethyl-18-[(1S)-1-methylpropyl]-25-(morpholine-4-carbonyl)-21-(2,2,2-trifluoroethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (775) (5S,8S,11S,15R,18S,23aS,25R,29S,35S,37aS)-8-((S)-sec-butyl)-29-(3-chloro-4-(trifluoromethyl)phenethyl)-18-cyclopentyl-25-ethoxy-36-ethyl-11-isobutyl-5,6,12,15,16,19,33-heptamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (776) (5S,8S,11S,15R,18S,23aS,29S,35S,37aS)-8-((S)-sec-butyl)-18-cyclopentyl-29-(3-fluoro-4-(trifluoromethyl)phenethyl)-11-isobutyl-5,6,12,15,16,19,33,36-octamethyl-35-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (777) (3S,6S,9S,13R,16S,22S,25S,31S,34S)-25-[2-[3-chloro-4-(trifluoromethyl)phenyl]ethyl]-31-(cyclohexylmethyl)-16-cyclopentyl-22-[2-(4,4-difluoro-1-piperidyl)-2-oxo-ethyl]-9-isobutyl-3,4,10,13,14,17,23,29,32-nonamethyl-6-[(1S)-1-methylpropyl]spiro[1,4,7,10,14,17,20,23,26,29,32-undecazabicyclo[32.2.0]hexatriacontane-19,1'-cyclopentane]-2,5,8,11,15,18,21,24,27,30,33-undecone, (778) (3S,9S,18S,21S,25S,28S,34S)-3-[2-[3-chloro-4-(trifluoromethyl)phenyl]ethyl]-28-cyclohexyl-9-(cyclohexylmethyl)-7,10,13,16,22,26,29-heptamethyl-18-[(1S)-1-methylpropyl]-25-(piperidine-1-carbonyl)-21-propylspiro[1,4,7,10,13,16,19,22,26,29,32-undecazabicyclo[32.3.0]heptatriacontane-31,1'-cyclopentane]-2,5,8,11,14,17,20,23,27,30,33-undecone, (779) (3S,6S,9S,12S,18S,27S,30S,34S)-18-[(4-chlorophenyl)methyl]-6-(5,5-difluoropentyl)-3,9-diisobutyl-4,7,16,19,22,25,30,31-octamethyl-27-[(1S)-1-methylpropyl]-34-(pyrrolidine-1-carbonyl)-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (780) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-22-[2-(4,4-difluoro-1-piperidyl)-2-oxo-ethyl]-13-(1,1-dioxo-1,4-thiazinane-4-carbonyl)-9-isobutyl-3,4,10,14,17,23,29,32-octamethyl-6-[(1S)-1-methylpropyl]spiro[1,4,7,10,14,17,20,23,26,29,32-undecazabicyclo[32.2.0]hexatriacontane-19,1'-cyclopentane]-2,5,8,11,15,18,21,24,27,30,33-undecone, (781) (6S,9S,13S,16S,22S,25S,31S,34S)-22-[(2-chlorophenyl)methyl]-25-[(3-iodophenyl)methyl]-9,16-diisobutyl-4,10,14,19,19,20,29,32-octamethyl-6-[(1S)-1-methylpropyl]-13-(piperidine-1-carbonyl)-31-(p-tolylmethyl)-1,4,7,10,14,17,20,23,26,29,32-undecazabicyclo[32.2.0]hexatriacontane-2,5,8,11,15,18,21,24,27,30,33-undecone, (782) (6S,9S,13R,16S,19S,22S,25S,31S,34S)-19-benzyl-31-[(4-chlorophenyl)methyl]-25-[2-[3-fluoro-4-(trifluoromethyl)phenyl]ethyl]-22-isobutyl-16-isopropyl-4,9,10,13,17,20,23,29,32-nonamethyl-6-[(1S)-1-methylpropyl]-1,4,7,10,14,17,20,23,26,29,32-undecazabicyclo[32.2.0]hexatriacontane-2,5,8,11,15,18,21,24,27,30,33-undecone, (783) (3S,6S,9S,13S,16S,22S,25S,31S,34S)-22-[(3-chlorophenyl)methyl]-25-[2-[3-chloro-4-(trifluoromethyl)phenyl]ethyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (784) (5S,8S,11S,15S,18S,21S,23aS,29S,35S,37aS)-8,18-di((S)-sec-butyl)-29-(3-chloro-4-(trifluoromethyl)phenethyl)-11-isobutyl-21-isopropyl-N,N,5,6,12,16,19,33,36-nonamethyl-35-(4-methylbenzyl)-4,7,10,13,17,20,23,28,31,34,37-undecaoxohexatriacontahydro-2H-azeto[2,1-u]pyrrolo[2,1-i][1,4,7,10,13,16,19,22,25,28,31]undecaazacyclotetratriacontine-15-carboxamide, (785) (5S,8S,11S,15R,18S,23aS,25R,29S,35S,37aS)-8-((S)-sec-butyl)-18-cyclopentyl-29-(3,5-difluoro-4-(trifluoromethyl)phenethyl)-25-ethoxy-36-ethyl-11-isobutyl-5,12,15,16,19,33-hexamethyl-35-(4-(trifluoromethyl)benzyl)docosahydro-2H4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (786) (6S,9S,13S,16S,22S,25S,31S,34S)-25-[2-[3-chloro-4-(trifluoromethyl)phenyl]ethyl]-16-cyclohexyl-31-(cyclohexylmethyl)-9-isobutyl-4,10,14,17,23,29,32-heptamethyl-6-[(1S)-1-methylpropyl]-22-[(6-methyl-3-pyridyl)methyl]-13-(piperidine-1-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (787) (3S,9S,18S,21S,25S,28S,34S)-3-[2-[3-chloro-4-(trifluoromethyl)phenyl]ethyl]-9-(cyclohexylmethyl)-28-(cyclopropylmethyl)-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (788) (3S,9S,12S,18S,27S,30S,34R)-18-[(4-chlorophenyl)methyl]-3,9-diisobutyl-4,6,6,10,16,19,22,25,30,31,34-undecamethyl-27-[(1S)-1-methylpropyl]-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (789) (8S,11S,17S,26S,29S,33S,36S)-11-[2-[3-chloro-4-(trifluoromethyl)phenyl]ethyl]-36-cyclohexyl-17-(cyclohexylmethyl)-8-I[(2-hydroxy-2-methyl-propoxy)methyl]-29-isobutyl-9,15,18,21,24,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (790) (5S,8S,11S,15S,18S,23aS,29S,35S,37aS)-8,18-di((S)-sec-butyl)-35-(cyclohexylmethyl)-29-(3-fluoro-4-(trifluoromethyl)phenethyl)-11-isobutyl-5,6,12,16,19,33,36-heptamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (791) (6S,9S,13S,16S,22S,25S,31S,34S)-25-[(3-iodophenyl)methyl]-9,16-diisobutyl-4,10,14,19,19,20,29,32-octamethyl-6-[(1S)-1-methylpropyl]-13-(piperidine-1-carbonyl)-31-(p-tolylmethyl)-22-[[2-(trifluoromethyl)phenyl]methyl]-1,4,7,10,14,17,20,23,26,29,32-undecazabicyclo[32.2.0]hexatriacontane-2,5,8,11,15,18,21,24,27,30,33-undecone, (792) allyl 2-[(8S,11S,17S,26S,29S,33S,36S)-11-[2-[3-chloro-4-(trifluoromethyl)phenyl]ethyl]-17-(cyclohexylmethyl)-36-isopropyl-9,15,18,21,24,29,30,34,37-nonamethyl-26-[(1S)-1-methylpropyl]-7,10,13,16,19,22,25,28,31,35,38-undecaoxo-33-(piperidine-1-carbonyl)-6,9,12,15,18,21,24,27,30,34,37-undecazaspiro[4.33]octatriacontan-8-yl]acetate, (793) (3S,6S,9S,12S,18S,27S,30S,34S)-12-[2-[3-chloro-4-(trifluoromethyl)phenyl]ethyl]-18-(cyclohexylmethyl)-9-[2-(3,3-difluoroazetidin-1-yl)-2-oxo-ethyl]-3-isopropyl-6-(methoxymethyl)-1,4,10,16,19,22,25,30,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (794) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-18-(isopentyloxymethyl)-7,10,13,16,22,26,29-heptamethyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (795) (5S,8S,11S,15R,18S,23aS,29S,32R,35S,37aS)-8-((S)-sec-butyl)-29-(3-chloro-4-(trifluoromethyl)phenethyl)-18-cyclopentyl-35-(3-fluorobenzyl)-5,6,11,12,15,19,32,33,36-nonamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (796) (8S,11S,17S,26S,29S,33S,36S)-11-[2-[3-chloro-4-(trifluoromethyl)phenyl]ethyl]-36-cyclohexyl-17-(cyclohexylmethyl)-8-(5,5-difluoropentyl)-29-isobutyl-9,15,18,21,24,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (797) (3S,9S,12S,18S,27S,30S,34R)-18-[(4-chlorophenyl)methyl]-12-[2-[3-fluoro-4-(trifluoromethyl)phenyl]ethyl]-3,9,30-triisobutyl-1,6,6,7,16,19,22,25,31,34-decamethyl-27-[(1S)-1-methylpropyl]-1,4,7,10,13,16,19,22,25,28,31-undecazacyclotetratriacontane-2,5,8,11,14,17,20,23,26,29,32-undecone, (798) (5S,8S,11S,15R,18S,23aS,29S,35S,37aS)-8,18-di((S)-sec-butyl)-29-(3-chloro-4-(trifluoromethyl)phenethyl)-35-(cyclohexylmethyl)-11,15-diisobutyl-5,6,12,19,33,36-hexamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (799) (5S,8S,11S,15S,18S,23aS,29S,35S,37aS)-8,18-di((S)-sec-butyl)-29-(3-chloro-4-(trifluoromethyl)phenethyl)-35-cyclopentyl-11-isobutyl-5,6,12,16,19,33,36-heptamethyl-15-(pyrrolidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (800) (3S,9S,12S,18S,27S,30S,34R)-18-[(4-chlorophenyl)methyl]-12-[2-[3-fluoro-4-(trifluoromethyl)phenyl]ethyl]-9,30-diisobutyl-1,6,6,7,16,19,22,25,31,34-decamethyl-3,27-bis[(1S)-1-methylpropyl]-1,4,7,10,13,16,19,22,25,28,31-undecazacyclotetratriacontane-2,5,8,11,14,17,20,23,26,29,32-undecone, (801) (3S,9S,18S,21S,25R,28S,34S)-3-[2-[3-chloro-4-(trifluoromethyl)phenyl]ethyl]-9-(cyclohexylmethyl)-21-isobutyl-13-isopentyl-28-isopropyl-7,10,16,22,25,29-hexamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (802) (3S,9S,18S,21S,25R,28S,34S)-3-[2-(4-chlorophenyl)ethyl]-9-(cyclohexylmethyl)-21,28-diisobutyl-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,4'-tetrahydropyran]-2,5,8,11,14,17,20,23,27,30,33-undecone, (803) (5S,8S,11S,15S,18S,23aS,29S,35S,37aS)-8-((S)-sec-butyl)-29-(3-chloro-4-(trifluoromethyl)phenethyl)-18-(cyclobutoxymethyl)-35-(cyclohexylmethyl)-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (804) (3S,9S,18S,21S,25S,28S,34S)-9-(cyclohexylmethyl)-3-[2-[3-fluoro-4-(trifluoromethyl)phenyl]ethyl]-21-isobutyl-28-isopropyl-7,10,13,16,22,26,29-heptamethyl-18-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (805) (3S,6S,9S,13S,16S,19S,22S,25S,31S,34S)-25-[2-[3-chloro-4-(trifluoromethyl)phenyl]ethyl]-31-(cyclohexylmethyl)-16-cyclopentyl-9-isobutyl-N,N,3,4,10,14,17,19,23,29,32-undecamethyl-6-[(1S)-1-methylpropyl]-2,5,8,11,15,18,21,24,27,30,33-undecaoxo-22-(thiazol-4-ylmethyl)-1,4,7,10,14,17,20,23,26,29,32-undecazabicyclo[32.2.0]hexatriacontane-13-carboxamide, (806) (5S,8S,11S,15S,18S,23aS,29S,35S,37aS)-15-(azetidine-1-carbonyl)-8-((S)-sec-butyl)-29-(3-chloro-4-(trifluoromethyl)phenethyl)-35-(cyclohexylmethyl)-18-cyclopentyl-11-isopentyl-5,6,12,16,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (807) (5S,8S,11S,15S,18S,23aS,29S,35S,37aS)-8,18-di((S)-sec-butyl)-29-(3-chloro-4-(trifluoromethyl)phenethyl)-35-cyclopentyl-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (808) (3S,6S,9S,12S,18S,27S,30S,34S)-6-benzyl-18-[(4-chlorophenyl)methyl]-3,9-diisobutyl-4,7,16,19,22,30,31-heptamethyl-27-f(1S)-1-methylpropyl]-34-(pyrrolidine-1-carbonyl)-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (809) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-6,12,16,19,33,36-hexamethyl-15-(piperidine-1-carbonyl)-5-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (810) 3-((5S,8S,11S,15R,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-6,12,15,19,33,36-hexamethyl-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentan]-5-yl)-N-methylpropanamide, (811) (3S,9S,18S,21S,25R,28S,34S)-3-[2-[3-chloro-4-(trifluoromethyl)phenyl]ethyl]-18-cyclobutyl-9-(cyclohexylmethyl)-21-isobutyl-28-isopropyl-7,10,13,16,22,25,29- heptamethyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(812) (5S,8S,11S,15S,18S,23aS,31S,37S,39aS)-8-((S)-sec-butyl)-31-(3-chloro-4-(trifluoromethyl)phenethyl)-18-cyclohexyl-37-(cyclohexylmethyl)-11-isobutyl-5,6,12,16,19,35,38-heptamethyl-15-(piperidine-1-carbonyl)-1,5,6,8,9,11,12,15,16,18,19,23a,24,31,32,34,35,37,38,39a-icosahydro-2H,4H-spiro[azeto[2',1':21,22][1,4,7,10,13,16,19,22,25,28,31]undecaazacyclotetratriacontino[10,9-a]indole-21,1'-cyclopentan]-4,7,10,13,17,20,23,30,33,36,39(14H,22H)-undecaone,
(813) (3S,6S,9S,12S,18S,27S,30S,34S)-9-butyl-18-[(4-chlorophenyl)methyl]-12-[(3-iodophenyl)methyl]-3,30-diisobutyl-1,7,16,19,22,25,31-heptamethyl-27-[(1S)-1-methylpropyl]-34-(piperidine-1-carbonyl)-6-[[2-(trifluoromethyl)phenyl]methyl]-1,4,7,10,13,16,19,22,25,28,31-undecazacyclotetratriacontane-2,5,8,11,14,17,20,23,26,29,32-undecone,
(814) (3S,9S,18S,21S,25S,28S,34S)-3-[2-[3-chloro-4-(trifluoromethyl)phenyl]ethyl]-28-cyclohexyl-7,10,13,16,22,26,29-heptamethyl-18-[(1S)-1-methylpropyl]-9-(p-tolylmethyl)-25-(pyrrolidine-1-carbonyl)-21-(2,2,2-trifluoroethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(815) (3S,9S,18S,21S,25R,28S,34S)-3-[2-[3-chloro-4-(trifluoromethyl)phenyl]ethyl]-21-cyclobutyl-9-(cyclohexylmethyl)-28-isopropyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(816) (5S,8S,11S,15R,18S,23aS,25R,29S,35S,37aS)-8-((S)-sec-butyl)-29-(3-chloro-4-(trifluoromethyl)phenethyl)-18-cyclopentyl-25-ethoxy-36-ethyl-11-isobutyl-5,6,12,15,16,19,33-heptamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(817) (3S,6S,9S,13S,16S,19S,22S,25S,31S,34S)-25-[2-[3-chloro-4-(trifluoromethyl)phenyl]ethyl]-31-(cyclohexylmethyl)-16-cyclopentyl-22-[2-(3,3-difluoroazetidin-1-yl)ethyl]-9-isobutyl-N,N,3,4,10,14,17,23,29,32-decamethyl-6-[(1S)-1-methylpropyl]-2,5,8,11,15,18,21,24,27,30,33-undecaoxo-19-(propoxymethyl)-1,4,7,10,14,17,20,23,26,29,32-undecazabicyclo[32.2.0]hexatriacontane-13-carboxamide,
(818) (3S,6S,9S,13S,16S,22S,25S,31S,34S)-25-[2-[3-chloro-4-(trifluoromethyl)phenyl]ethyl]-22-[2-(3,3-difluoro-1-piperidyl)ethyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide,
(819) (3S,6S,9S,12S,18S,27S,30S,34S)-9-butyl-18-[(4-chlorophenyl)methyl]-12-[(3-iodophenyl)methyl]-3,30-diisobutyl-1,7,16,19,22,25,31-heptamethyl-27-[(1S)-1-methylpropyl]-34-(piperidine-1-carbonyl)-6-[[4-(trifluoromethoxy)phenyl]methyl]-1,4,7,10,13,16,19,22,25,28,31-undecazacyclotetratriacontane-2,5,8,11,14,17,20,23,26,29,32-undecone,
(820) (3S,9S,18S,21S,25S,28S,34S)-3-[2-[3-chloro-4-(trifluoromethyl)phenyl]ethyl]-28-cyclohexyl-9-(cyclohexylmethyl)-21-[(1R)-1-methoxyethyl]-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(821) (8S,11S,17S,26S,29S,33S,36S)-11-[2-[3-chloro-4-(trifluoromethyl)phenyl]ethyl]-17-(cyclohexylmethyl)-8-[(4-fluorophenyl)methyl]-36-isopropyl-9,15,18,21,24,29,30,34,37-nonamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone,
(822) (5S,8S,11S,15S,18S,20aR,26S,29S,35S,37aS)-8-((S)-sec-butyl)-26-butyl-29-(3-iodobenzyl)-11,18-diisobutyl-5,6,12,16,33,36-hexamethyl-35-(4-methylbenzyl)-15-(piperidine-1-carbonyl)tetracosahydro-4H-azeto[2,1-u]pyrrolo[2,1-f][1,4,7,10,13,16,19,22,25,28,31]undecaazacyclotetratriacontin-4,7,10,13,17,20,25,28,31,34,37(2H,14H)-undecaone,
(823) (9'S,12'S,16'S,19'S,24a'S,30'S,32a'R,39'S,41a'S)-9'-((S)-sec-butyl)-30'-(3-chloro-4-(trifluoromethyl)phenethyl)-39'-(cyclohexylmethyl)-19'-isopropyl-7',12',13',17',20',40'-hexamethyl-16'-(piperidine-1-carbonyl)hexacosahydro-5'H,29'H-spiro[cyclopentane-1,22'-pyrido[2,1-o]dipyrrolo[2,1-i:2',1'-u][1,4,7,10,13,16,19,22,25,28,31]undecaazacyclotetratriacontin]-5',8',11',14',18',21',24',29',32',38',41'(15'H,23'H,32a'H)-undecaone,
(824) (3S,9S,18S,21S,25R,28S,34S)-3-[2-[3-chloro-4-(trifluoromethyl)phenyl]ethyl]-9-(cyclohexylmethyl)-28-isopropyl-7,10,13,16,21,25,26,29-octamethyl-18-[(1S)-1-methylpropyl]-22-propyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(825) (3S,9S,18S,21S,25S,28S,34S)-28-cyclohexyl-9-(cyclohexylmethyl)-3-[2-(3,4-dichlorophenyl)ethyl]-7,10,13,16,21,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(826) (3S,6S,9S,12S,18S,27S,30S,34S)-12-[2-[3-chloro-4-(trifluoromethyl)phenyl]ethyl]-18-(cyclohexylmethyl)-9-[2-(4,4-difluoro-1-piperidyl)-2-oxo-ethyl]-6-isobutyl-3-isopropyl-1,4,10,16,19,22,25,30,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29-undecone,
(827) (5S,8S,11S,15S,18S,23aS,29S,35S,37aS)-8-((S)-sec-butyl)-29-(3-fluoro-4-(trifluoromethyl)phenethyl)-11-isobutyl-5,6,12,16,19,33,36-heptamethyl-15-(morpholine-4-carbonyl)-35-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(828) (5S,8S,11S,15S,18S,23aS,29S,35S,37aS)-8,18-di((S)-sec-butyl)-29-(3-chloro-4-(trifluoromethyl)phenethyl)-11-isobutyl-N,N,5,6,12,16,19,33,36-nonamethyl-35-(4-methylbenzyl)-4,7,10,13,17,20,23,28,31,34,37-undecaoxohexatriacontahydro-2H-azeto[2,1-u]pyrrolo[2,1-i][1,4,7,10,13,16,19,22,25,28,31]undecaazacyclotetratriacontine-15-carboxamide,
(829) (5S,8S,11S,15S,18S,21S,23aS,29S,35S,37aS)-8,18-di((S)-sec-butyl)-29-(3-chloro-4-(trifluoromethyl)phenethyl)-11-isobutyl-N,N,5,6,12,16,19,21,33,36-decamethyl-35-(4-methylbenzyl)-4,7,10,13,17,20,23,28,31,34,37-undecaoxohexatriacontahydro-2H-azeto[2,1-u]pyrrolo[2,1-i][1,4,7,10,13,16,19,22,25,28,31]undecaazacyclotetratriacontine-15-carboxamide, (830) (3S,6R,9S,18S,21S,25R,28S,34S)-3-[2-[3-chloro-4-(trifluoromethyl)phenyl]ethyl]-28-cyclopentyl-9-[(3-fluorophenyl)methyl]-6,7,10,13,16,21,22,25,29-nonamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (831) (5S,8S,11S,15R,18S,23aS,29S,32R,35S,37aS)-8-((S)-sec-butyl)-29-(3-chloro-4-(trifluoromethyl)phenethyl)-35-(cyclohexylmethyl)-18-isopropyl-5,6,11,12,15,19,32,33,36-nonamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (832) (3S,9S,12S,18S,27S,30S)-18-(cyclohexylmethyl)-12-[2-[3-fluoro-4-(trifluoromethyl)phenyl]ethyl]-3,9,30-triisobutyl-1,6,6,7,16,19,22,25,31-nonamethyl-27-[(1S)-1-methylpropyl]-1,4,7,10,13,16,19,22,25,28,31-undecazacyclotetratriacontane-2,5,8,11,14,17,20,23,26,29,32-undecone, (833) (5S,8S,11S,15R,18S,23aS,29S,35S,37aS)-8,18-di((S)-sec-butyl)-29-(3-chloro-4-(trifluoromethyl)phenethyl)-36-ethyl-25,25-difluoro-11-isobutyl-5,6,12,15,16,19,33-heptamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclobutan]-4,7,10,13,17,20,23,28,31,34,37(14H,22H)-undecaone, (834) (9'S,12'S,16'R,19'S,24a'S,30'S,32a'R,39'S,41a'S)-9'-((S)-sec-butyl)-30'-(3-chloro-4-(trifluoromethyl)phenethyl)-39'-(cyclohexylmethyl)-19'-isopropyl-7',12',13',16',20',40'-hexamethylhexacosahydro-5'H,29'H-spiro[cyclopentane-1,22'-pyrido[2,1-o]dipyrrolo[2,1-i:2',1'-u][1,4,7,10,13,16,19,22,25,28,31]undecaazacyclotetratriacontin]-5',8',11',14',18',21',24',29',32',38',41'(15'H,23'H,32a'H)-undecaone, (835) (5S,8S,11S,15S,18S,23aS,29S,35S,37aS)-8-((S)-sec-butyl)-29-(3-chloro-4-(trifluoromethyl)phenethyl)-35-(cyclobutoxymethyl)-18-cyclopentyl-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (836) (5S,8S,11S,15S,18S,23aS,29S,35S,37aS)-8-((S)-sec-butyl)-29-(3-chloro-4-(trifluoromethyl)phenethyl)-18-cyclopentyl-11-isobutyl-5,6,12,16,19,33,36-heptamethyl-35-(propoxymethyl)-15-(pyrrolidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (837) (3S,9S,18S,21S,25R,28S,34S)-3-[2-[3-chloro-4-(trifluoromethyl)phenyl]ethyl]-9-(cyclohexylmethyl)-21-isobutyl-28-isopropyl-7,10,13,16,22,25,26,29-octamethyl-8-[(1S)-1-methylpropyl]spiro[1,4,7,10,13,16,19,22,26,29,32-undecazabicyclo[32.3.0]heptatriacontane-31,1'-cyclobutane]-2,5,8,11,14,17,20,23,27,30,33-undecone, (838) (3S,6S,9S,13S,16S,22S,25S,31S,34S)-22-[(4-chlorophenyl)methyl]-25-[2-[3-chloro-4-(trifluoromethyl)phenyl]ethyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (839) (3S,9S,12S,18S,27S,30S,34R)-18-(cyclohexylmethyl)-3,9,30-triisobutyl-4,6,6,10,16,19,22,25,31,34-decamethyl-27-[(1S)-1-methylpropyl]-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (840) (5S,8S,11S,15S,18S,23aS,29S,35S,37aS)-8,18-di((S)-sec-butyl)-29-(3-chloro-4-(trifluoromethyl)phenethyl)-11-isobutyl-N,N,5,12,16,19,33,36-octamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (841) (6'S,12'S,21'S,23a'S,31'S,34'S,39a'S)-21'-((S)-sec-butyl)-6'-(4-chlorophenethyl)-12'-(cyclohexylmethyl)-34'-isopropyl-10',13',16',19',32',35'-hexamethyl-31'-(piperidine-1-carbonyl)tetracosahydrospiro[cyclopentane-1,37'-pyrido[1,2-a]pyrrolo[1,2-v][1,4,7,10,13,16,19,22,25,28,31]undecaazacyclotetratriacontin]-5',8',11',14',17',20',23',29',33',36',39'(23a'H,30'H,38'H)-undecaone, (842) (3S,9S,12S,18S,27S,30S,34R)-18-(cyclohexylmethyl)-12-[2-[3-fluoro-4-(trifluoromethyl)phenyl]ethyl]-3,9-diisobutyl-1,6,6,7,16,19,22,25,30,31,34-undecamethyl-27-[(1S)-1-methylpropyl]-1,4,7,10,13,16,19,22,25,28,31-undecazacyclotetratriacontane-2,5,8,11,14,17,20,23,26,29,32-undecone, (843) (8S,11S,17S,26S,29S,33R,36S)-17-[(4-chlorophenyl)methyl]-8,29,36-triisobutyl-9,15,18,21,24,30,33,37-octamethyl-26-[(1S)-1-methylpropyl]-11-[2-[4-(trifluoromethyl)phenyl]ethyl]-6,9,12,15,18,21,24,27,30,34,37-undecazaspiro[4.33]octatriacontane-7,10,13,16,19,22,25,28,31,35,38-undecone, (844) (3S,9S,18S,21S,25R,28S,34S)-3-[2-[3-chloro-4-(trifluoromethyl)phenyl]ethyl]-9-(cyclohexylmethyl)-21-cyclopropyl-28-isopropyl-7,10,13,16,22,25,29-heptamethyl-8-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (845) (3S,9S,18S,21S,25R,28S,34S)-3-[2-[3-chloro-4-(trifluoromethyl)phenyl]ethyl]-28-cyclobutyl-9-(cyclohexylmethyl)-21-isobutyl-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (847) (4R,7S,13S,16S,22S,31S,34S)-22-[(4-chlorophenyl)methyl]-7,13-diisobutyl-4,8,14,20,23,26,29-heptamethyl-31-[(1S)-1-methylpropyl]-16-[2-[4-(trifluoromethyl)phenyl]ethyl]spiro[1,5,8,11,14,17,20,23,26,29,32-undecazabicyclo[32.4.0]octatriacontane-10,1'-cyclopentane]-2,6,9,12,15,18,21,24,27,30,33-undecone, (848) (11S,17S,26S,29S,33S,36S)-9-butyl-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (849) (3S,9S,18S,21S,25S,28S,34S)-3-[2-[3-chloro-4-(trifluoromethyl)phenyl]ethyl]-21,28-dicyclohexyl-9-(cyclohexylmethyl)-7,10,13,16,22,26,29-heptamethyl-8-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (850) (3S,9S,18S,21S,25S,28S,34S)-3-[2-[3-chloro-4-(trifluoromethyl)phenyl]ethyl]-9-(cyclohexylmethyl)-21-isobutyl-28-(methoxymethyl)-7,10,13,16,22,26,29-heptamethyl-18-[(1S)-1-methylpropyl]-25-(piperidine-1- carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (851) (8S,11S,17S,26S,29S,33R,36S)-17-[(4-chlorophenyl)methyl]-11-[2-[3-fluoro-4-(trifluoromethyl)phenyl]ethyl]-8,36-diisobutyl-29-isopropyl-9,15,18,21,24,30,33,37-octamethyl-26-[(1S)-1-methylpropyl]-6,9,12,15,18,21,24,27,30,34,37-undecazaspiro[4.33]octatriacontane-7,10,13,16,19,22,25,28,31,35,38-undecone, (852) (5S,8S,11S,15R,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-6,12,15,19,33,36-hexamethyl-5-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (853) (3S,9S,18S,21S,25S,28S,34S)-3-[2-[3-chloro-4-(trifluoromethyl)phenyl]ethyl]-21-cyclobutyl-28-cyclohexyl-7,10,13,16,22,26,29-heptamethyl-18-[(1S)-1-methylpropyl]-25-(morpholine-4-carbonyl)-9-(propoxymethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (854) (3S,6S,9S,13S,16S,22S,25S,31S,34S)-22-benzyl-25-[2-[3-chloro-4-(trifluoromethyl)phenyl]ethyl]-31-(cyclohexylmethyl)-16-cyclopentyl-9-isobutyl-N,N,3,4,10,14,17,23,29,32-decamethyl-6-[(1S)-1-methylpropyl]-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide, (855) (9'S,12'S,16'S,19'S,24a'S,32'S,38'S,40a'S)-9'-((S)-sec-butyl)-32'-(3-chloro-4-(trifluoromethyl)phenethyl)-19'-cyclohexyl-38'-(cyclohexylmethyl)-12'-isobutyl-7',13',17',20',36',39'-hexamethyl-16'-(piperidine-1-carbonyl)-1',2',3',6',7',9',10',12',13',16',17',19',20',24a',25',32',33',35',36',38',39',40a'-docosahydro-5'H-spiro[cyclopentane-1,22'-pyrrolo[2',1':21,22][1,4,7,10,13,16,19,22,25,28,31]undecaazacyclotetratriacontino[10,9-a]indol]-5',8',11',14',18',21',24',31',34',37',40'(15'H,23'H)-undecaone, (856) (3S,6S,9S,13S,16S,19S,22S,25S,31S,34S)-25-[2-[3-chloro-4-(trifluoromethyl)phenyl]ethyl]-9-isobutyl-N,N,3,4,10,14,17,19,23,29,32-undecamethyl-6,16-bis[(1S)-1-methylpropyl]-2,5,8,11,15,18,21,24,27,30,33-undecaoxo-31-(p-tolylmethyl)-22-(thiazol-4-ylmethyl)-1,4,7,10,14,17,20,23,26,29,32-undecazabicyclo[32.2.0]hexatriacontane-13-carboxamide, (857) (3S,9S,18S,21S,25R,28S,34S)-3-[2-[3-chloro-4-(trifluoromethyl)phenyl]ethyl]-9-(cyclohexylmethyl)-21-cyclopentyl-28-isopropyl-7,10,13,16,22,25,29-heptamethyl-8-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (858) (3S,9S,12S,18S,27S,30S,34R)-18-(cyclohexylmethyl)-9-[[4-(difluoromethyl)phenyl]methyl]-12-[2-[3-fluoro-4-(trifluoromethyl)phenyl]ethyl]-3,30-diisobutyl-1,6,6,7,16,19,22,25,31,34-decamethyl-27-[(1S)-1-methylpropyl]-1,4,7,10,13,16,19,22,25,28,31-undecazacyclotetratriacontane-2,5,8,11,14,17,20,23,26,29,32-undecone, (859) (5S,8S,11S,15R,18S,23aS,29S,35S,37aS)-8,18-di((S)-sec-butyl)-35-(cyclohexylmethyl)-29-(3-fluoro-4-(trifluoromethyl)phenethyl)-11-isobutyl-5,6,12,15,16,19,33,36-octamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (860) (5S,8S,11S,15S,18S,23aS,29S,35S,37aS)-8-((S)-sec-butyl)-35-(cyclohexylmethyl)-29-(4-fluorophenethyl)-18-isopropyl-5,6,11,12,16,19,33,36-octamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (861) (3S,6S,9S,12S,18S,27S,30S,34S)-6-benzyl-18-[(4-chlorophenyl)methyl]-12-[2-[3-chloro-4-(trifluoromethyl)phenyl]ethyl]-3,9-diisobutyl-4,7,16,19,22,25,30,31-octamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (862) (5S,8S,11S,15S,18S,23aS,29S,35S,37aS)-8-((S)-sec-butyl)-29-(3-chloro-4-(trifluoromethyl)phenethyl)-35-((R)-1-hydroxyethyl)-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (863) (5S,8S,11S,15R,18S,23aS,29S,35S,37aS)-8,18-di((S)-sec-butyl)-29-(3,5-difluoro-4-(trifluoromethyl)phenethyl)-25,25-difluoro-11-isobutyl-5,6,12,15,16,19,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (864) (3S,9S,18S,21S,25R,28S,34S)-3-[2-[3-chloro-4-(trifluoromethyl)phenyl]ethyl]-9-(cyclohexylmethyl)-13-(2-ethoxyethyl)-21-isobutyl-28-isopropyl-7,10,16,22,25,29-hexamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (865) (3S,9S,18S,21S,25R,28S,31S,34S)-31-benzyl-9-[(4-chlorophenyl)methyl]-28-isopropyl-7,10,13,16,21,22,25,29,32-nonamethyl-18-[(1S)-1-methylpropyl]-3-[2-[4-(trifluoromethyl)phenyl]ethyl]-1,4,7,10,13,16,19,22,26,29,32-undecazabicyclo[32.3.0]heptatriacontane-2,5,8,11,14,17,20,23,27,30,33-undecone, (866) (5S,8S,11S,15S,18S,23aS,29S,35S,37aS)-8,18-di((S)-sec-butyl)-29-(3-chloro-4-(trifluoromethyl)phenethyl)-36-ethyl-11-isobutyl-N,N,5,6,12,16,19,33-octamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (867) 4-[[(3S,9S,18S,21S,25S,28S,34S)-3-[2-[3-chloro-4-(trifluoromethyl)phenyl]ethyl]-21-isobutyl-28-isopropyl-7,10,13,16,22,26,29-heptamethyl-18-[(1S)-1-methylpropyl]-2,5,8,11,14,17,20,23,27,30,33-undecaoxo-25-(piperidine-1-carbonyl)spiro[1,4,7,10,13,16,19,22,26,29,32-undecazabicyclo[32.3.0]heptatriacontane-31,1'-cyclopentane]-9-yl]methyl]benzonitrile, (868) (5S,8S,11S,15S,18S,23aS,29S,35S,37aS)-8,18-di((S)-sec-butyl)-35-(cyclohexylmethyl)-29-(3-fluoro-4-(trifluoromethyl)phenethyl)-11-isobutyl-5,6,12,16,19,33,36-heptamethyl-15-(pyrrolidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (869) (3S,9S,18S,21S,25R,28S,34S)-3-[2-[3-chloro-4-(trifluoromethyl)phenyl]ethyl]-36,36-difluoro-21-isobutyl-7,10,13,16,22,25,26,29-octamethyl-18,28-bis[(1S)-1-methylpropyl]-9-(p-tolylmethyl)spiro[1,4,7,10,13,16,19,22,26,29,32-undecazabicyclo[32.3.0]heptatriacontane-31,1'-cyclobutane]-2,5,8,11,14,17,20,23,27,30,33-undecone, (870) (3S,9S,18S,21S,25R,28S,31S,34S)-31-benzyl-9-[(4-chlorophenyl)methyl]-36,36-difluoro-28-isobutyl-7,10,13,16,21,22,25,29,32-nonamethyl-8-[(1S)-1-methylpropyl]-3-[2-[4-(trifluoromethyl)phenyl]ethyl]-1,4,7,10,13,16,19,22,26,29,32-undecazabicyclo[32.3.0]heptatriacontane-2,5,8,11,14,17,20,23,27,30,33-undecone, (871) (5S,8S,11S,15S,18S,23aS,29S,35S,37aS)-8-((S)-sec-butyl)-18,35-dicyclopentyl-29-(3-fluoro-4-(trifluoromethyl)phenethyl)-11-isobutyl-5,6,12,16,19,33,36-heptamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (872) (11S,17S,26S,29S,33S,36S)-11-[2-[3-chloro-4-(trifluoromethyl)phenyl]ethyl]-36-cyclohexyl-17-(cyclohexylmethyl)-9-(2-ethoxyethyl)-29-isobutyl-15,18,21,24,30,34,37-heptamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (873) (5S,8S,11S,15R,18S,23aS,29S,35S,37aS)-8-((S)-sec-butyl)-29-(3-chloro-4-(trifluoromethyl)phenethyl)-11-cyclohexyl-35-(cyclohexylmethyl)-18-isopropyl-5,6,12,15,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (874) (3S,9S,18S,21S,25R,28S,34S)-3-[2-[3-chloro-4-(trifluoromethyl)phenyl]ethyl]-9-(cyclohexylmethyl)-28-cyclopropyl-21-isobutyl-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (875) (3S,9S,18S,21S,25S,28S,34S,36R)-9-(cyclohexylmethyl)-3-[2-[3-fluoro-4-(trifluoromethyl)phenyl]ethyl]-36-hydroxy-21,28-diisobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (876) (3S,6S,9S,12S,18S,27S,30S,34S)-9-butyl-18-[(4-chlorophenyl)methyl]-12-[(3-iodophenyl)methyl]-3,30-diisobutyl-1,7,16,19,22,25,31-heptamethyl-27-[(1S)-1-methylpropyl]-34-(piperidine-1-carbonyl)-6-(p-tolylmethyl)-1,4,7,10,13,16,19,22,25,28,31-undecazacyclotetratriacontane-2,5,8,11,14,17,20,23,26,29,32-undecone, (877) (3S,9S,18S,21S,25S,28S,34S)-3-[2-[3-chloro-4-(trifluoromethyl)phenyl]ethyl]-9,28-dicyclohexyl-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (878) (3S,6S,9S,12S,18S,27S,30S,34S)-18-[(4-chlorophenyl)methyl]-3,9-diisobutyl-4,7,16,19,22,25,30,31-octamethyl-27-[(1S)-1-methylpropyl]-6-(2-phenylethyl)-34-(pyrrolidine-1-carbonyl)-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (879) (3S,9S,18S,21S,28S,34S)-9-(cyclohexylmethyl)-3-[2-[3-fluoro-4-(trifluoromethyl)phenyl]ethyl]-21-isobutyl-28-isopropyl-7,10,13,16,22,26,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (880) (5S,8S,11S,15S,18S,23aS,29S,35S,37aS)-8-((S)-sec-butyl)-29-(3-chloro-4-(trifluoromethyl)phenethyl)-35-(cyclobutoxymethyl)-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (881) (3S,9S,18S,21S,25S,28S,34S)-3-[2-[3-chloro-4-(trifluoromethyl)phenyl]ethyl]-28-cyclohexyl-9-(cyclohexylmethyl)-7,10,13,16,22,26,29-heptamethyl-18-[(1S)-1-methylpropyl]-25-(3-oxa-8-azabicyclo[3.2.1]octane-8-carbonyl)-21-(2,2,2-trifluoroethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (882) (5S,8S,11S,15S,18S,23aS,29S,35S,37aS)-8,18-di((S)-sec-butyl)-29-(3-chloro-4-(trifluoromethyl)phenethyl)-11-isobutyl-5,6,12,16,19,33,36-heptamethyl-15-(pyrrolidine-1-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (883) (3S,9S,12S,18S,27S,30S,34R)-18-(cyclohexylmethyl)-12-[2-[3-fluoro-4-(trifluoromethyl)phenyl]ethyl]-3,9,30-triisobutyl-1,6,6,7,16,19,22,25,31,34-decamethyl-27-[(1S)-1-methylpropyl]-1,4,7,10,13,16,19,22,25,28,31-undecazacyclotetratriacontane-2,5,8,11,14,17,20,23,26,29,32-undecone, (884) (3S,6S,9S,12S,18S,27S,30S,34S)-6-benzyl-18-[(4-chlorophenyl)methyl]-12-[(3-iodophenyl)methyl]-3,9-diisobutyl-4,7,16,19,22,25,30,31-octamethyl-27-1(1S)-1-methylpropyl]-34-(pyrrolidine-1-carbonyl)-1,4,7,10,13,16,19,22,25,28,31-undecazacyclotetratriacontane-2,5,8,11,14,17,20,23,26,29,32-undecone, (885) (5S,8S,11S,15S,18S,23aS,29S,35S,37aS)-8,18-di((S)-sec-butyl)-29-(3-chloro-4-(trifluoromethyl)phenethyl)-35-(cyclobutoxymethyl)-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (886) (3S,6S,9S,13R,16S,22S,25S,31S,34S)-25-[2-[3-chloro-4-(trifluoromethyl)phenyl]ethyl]-31-(cyclohexylmethyl)-9,16,22-triisobutyl-3,4,10,13,14,19,19,20,29,32-decamethyl-6-[(1S)-1-methylpropyl]-1,4,7,10,14,17,20,23,26,29,32-undecazabicyclo[32.2.0]hexatriacontane-2,5,8,11,15,18,21,24,27,30,33-undecone, (887) (8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-8-[(5-methoxy-3-pyridyl)methyl]-9,15,18,21,24,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (888) 4-[[(3S,9S,18S,21S,25R,28S,34S)-3-[2-[3-chloro-4-(trifluoromethyl)phenyl]ethyl]-21-isobutyl-28-isopropyl-7,10,13,16,22,25,26,29-octamethyl-18-[(1S)-1-methylpropyl]-2,5,8,11,14,17,20,23,27,30,33-undecaoxo-spiro[1,4,7,10,13,16,19,22,26,29,32-undecazabicyclo[32.3.0]heptatriacontane-31,1'-cyclopentane]-9-yl]methyl] benzonitrile, (889) N-tert-butyl-2-[[(3S,6S,9S,12S,18S,27S,30S,34S)-18-[(4-chlorophenyl)methyl]-3,9-diisobutyl-4,7,16,19,22,25,30,31-octamethyl-27-[(1S)-1-methylpropyl]-2,5,8,11,14,17,20,23,26,29,32-undecaoxo-34-(pyrrolidine-1-carbonyl)-12-[2-[4-(trifluoromethyl)phenyl]ethyl]-1,4,7,10,13,16,19,22,25,28,31-undecazacyclotetratriacont-6-yl]methoxy]acetamide, (890) (3S,9S,18S,21S,25S,28S,34S)-3-[2-[3-chloro-4-(trifluoromethyl)phenyl]ethyl]-21-cyclobutyl-28-cyclohexyl-9-(cyclohexylmethyl)-7,10,13,16,22,26,29-heptamethyl-18-[(1S)-1-methylpropyl]-25-(morpholine-4-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (891) (3S,9S,18S,21S,25R,28S,34S)-3-[2-[3-chloro-4-(trifluoromethyl)phenyl]ethyl]-9-(cyclohexylmethyl)-36,36-difluoro-21-isobutyl-7,10,13,16,22,25,26,29-octamethyl-18,28-bis[(1S)-1-methylpropyl]spiro[1,4,7,10,13,16,19,22,26,29,32-undecazabicyclo[32.3.0]heptatriacontane-31,1'-cyclobutane]-2,5,8,11,14,17,20,23,27,30,33-undecone, (892) (8S,11S,17S,26S,29S,33R,36S)-11-[2-[3-chloro-4-(trifluoromethyl)phenyl]ethyl]-17-(cyclohexylmethyl)-8,36-diisobutyl-29-isopropyl-9,15,18,21,24,30,33,37-octamethyl-26-[(1S)-1-methylpropyl]-6,9,12,15,18,21,24,27,30,34,37-undecazaspiro[4.33]octatriacontane-7,10,13,16,19,22,25,28,31,35,38-undecone, (893) (3S,9S,18S,21S,25S,28S,34S)-3-[2-(4-chlorophenyl)ethyl]-9-(cyclohexylmethyl)-21-isobutyl-28-isopropyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (894) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-25-(piperidine-1-carbonyl)-18-(2,2,2-trifluoroethoxymethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (895) (3S,9S,12S,18S,27S,30S,34S)-9-butyl-18-[(4-chlorophenyl)methyl]-12-[2-[3-chloro-4-(trifluoromethyl)phenyl]ethyl]-19-ethyl-3,30-diisobutyl-1,6,6,7,16,22,25,31-octamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (896) (5S,8S,11S,15S,18S,23aS,29S,35S,37aS)-8,18-di((S)-sec-butyl)-29-(3-chloro-4-(trifluoromethyl)phenethyl)-N,N,5,6,12,16,19,33,36-nonamethyl-35-(4-methylbenzyl)-4,7,10,13,17,20,23,28,31,34,37-undecaoxo-11-pentyltetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (897) (3S,9S,12S,18S,27S,30S,34R)-18-[(4-chlorophenyl)methyl]-3-cyclohexyl-2-[2-[3-fluoro-4-(trifluoromethyl)phenyl]ethyl]-9,30-diisobutyl-1,6,6,7,16,19,22,25,31,34-decamethyl-27-[(1S)-1-methylpropyl]-1,4,7,10,13,16,19,22,25,28,31-undecazacyclotetratriacontane-2,5,8,11,14,17,20,23,26,29,32-undecone, (898) (5S,8S,11S,15R,18S,23aS,29S,35S,37aS)-8,18-di((S)-sec-butyl)-29-(3-chloro-4-(trifluoromethyl)phenethyl)-36-ethyl-11-isobutyl-5,6,12,15,16,19,33-heptamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (899) (11S,17S,26S,29S,33S,36S)-9-allyl-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (900) (5S,8S,11S,15R,18S,23aS,29S,35S,37aS)-8-((S)-sec-butyl)-18-cyclopentyl-29-(3,5-difluoro-4-(trifluoromethyl)phenethyl)-25,25-difluoro-11-isobutyl-5,6,12,15,16,19,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (901) (3S,9S,18S,21S,25R,28S,34S)-3-[2-[3-chloro-4-(trifluoromethyl)phenyl]ethyl]-9-(cyclohexylmethyl)-21-(cyclopentylmethyl)-28-isopropyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (902) (3S,9S,18S,21S,25R,28S,31S,34S)-9-[(4-chlorophenyl)methyl]-28,31-diisobutyl-7,10,13,16,21,22,25,29,32-nonamethyl-8-[(1S)-1-methylpropyl]-3-[2-[4-(trifluoromethyl)phenyl]ethyl]-1,4,7,10,13,16,19,22,26,29,32-undecazabicyclo[32.3.0]heptatriacontane-2,5,8,11,14,17,20,23,27,30,33-undecone, (903) (5S,8S,11S,15S,18S,23aS,29S,35S,37aS)-8-((S)-sec-butyl)-29-(4-chlorophenethyl)-35-(cyclohexylmethyl)-18-isopropyl-5,6,11,12,16,19,33,36-octamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (904) (3S,9S,18S,21S,25R,28S,34S)-3-[2-[3-chloro-4-(trifluoromethyl)phenyl]ethyl]-9-(cyclohexylmethyl)-21-isobutyl-7,10,13,16,22,25,26,29-octamethyl-18,28-bis[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (905) (3S,6S,10R,13S,19S,22S,28S,34S)-28-(cyclohexylmethyl)-22-[2-[3-fluoro-4-(trifluoromethyl)phenyl]ethyl]-6,13,19-triisobutyl-7,10,11,16,16,17,26,29,32-nonamethyl-3-[(1S)-1-methylpropyl]-1,4,7,11,14,17,20,23,26,29,32-undecazabicyclo[32.2.0]hexatriacontane-2,5,8,12,15,18,21,24,27,30,33-undecone, (906) (7S,10S,16S,25S,28S,32S,35S)-7-[(2-chlorophenyl)methyl]-10-[2-[3-chloro-4-(trifluoromethyl)phenyl]ethyl]-16-(cyclohexylmethyl)-35-isopropyl-8,14,17,20,23,28,29,33,36-nonamethyl-25-[(1S)-1-methylpropyl]-32-(pyrrolidine-1-carbonyl)-5,8,11,14,17,20,23,26,29,33,36-undecazaspiro[3.33]heptatriacontane-6,9,12,15,18,21,24,27,30,34,37-undecone, (907) (5S,8S,11S,15R,18S,23aS,29S,35S,37aS)-8,18-di((S)-sec-butyl)-29-(3,5-difluoro-4-(trifluoromethyl)phenethyl)-11-isobutyl-5,6,12,15,16,19,33,36-octamethyl-35-

(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (908) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-9-isobutyl-N,N,3,4,10,14,17,23,29,32-decamethyl-6-[(1S)-1-methylpropyl]-2,5,8,11,15,18,21,24,27,30,33-undecaoxo-22-(p-tolylmethyl)spiro[1,4,7,10,14,17,20,23,26,29,32-undecazabicyclo[32.2.0]hexatriacontane-19,1'-cyclopentane]-13-carboxamide, (909) (5S,8S,11S,15R,18S,23aS,29S,35S,37aS)-8,18-di((S)-sec-butyl)-35-cyclopentyl-29-(3-fluoro-4-(trifluoromethyl)phenethyl)-11-isobutyl-5,6,12,15,16,19,33,36-octamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (910) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-22-[2-(3,3-difluoro-1-piperidyl)ethyl]-9-isobutyl-N,N,3,4,10,14,17,23,29,32-decamethyl-6-[(1S)-1-methylpropyl]-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide, (911) (3S,9S,18S,21S,25S,28S,34S)-3-[2-[3-chloro-4-(trifluoromethyl)phenyl]ethyl]-21-(cyclobutylmethyl)-9-(cyclohexylmethyl)-28-isopropyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (912) (3S,6S,9S,13S,16S,22S,25S,31S,34S)-25-[2-[3-chloro-4-(trifluoromethyl)phenyl]ethyl]-9-isobutyl-N,N,3,4,10,14,17,23,29,32-decamethyl-6,16-bis[(1S)-1-methylpropyl]-22-(m-tolylmethyl)-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (913) (6S,9S,13R,16S,19S,22S,25S,31S,34S)-19-benzyl-31-[(4-chlorophenyl)methyl]-22-isobutyl-16-isopropyl-4,9,10,13,17,20,23,29,32-nonamethyl-6-[(1S)-1-methylpropyl]-25-[2-[4-(trifluoromethyl)phenyl]ethyl]-1,4,7,10,14,17,20,23,26,29,32-undecazabicyclo[32.2.0]hexatriacontane-2,5,8,11,15,18,21,24,27,30,33-undecone, (914) (3S,9S,18S,21S,25S,28S,34S,36R)-3-[2-[3-chloro-4-(trifluoromethyl)phenyl]ethyl]-9-(cyclohexylmethyl)-36-(4,4-difluoro-1-piperidyl)-28-isopropyl-7,10,13,16,21,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (915) (3S,6S,9S,13S,16S,19S,22R,25S,31S,34S)-25-[2-[3-chloro-4-(trifluoromethyl)phenyl]ethyl]-9-isobutyl-19-isopropyl-N,N,3,4,10,14,17,22,29,32-decamethyl-6,16-bis[(1S)-1-methylpropyl]-2,5,8,11,15,18,21,24,27,30,33-undecaoxo-31-(p-tolylmethyl)-1,4,7,10,14,17,20,23,26,29,32-undecazabicyclo[32.2.0]hexatriacontane-13-carboxamide, (916) (8S,11S,15S,18S,23aS,29S,35S,37aS)-8-((S)-sec-butyl)-29-(4-chlorophenethyl)-35-(cyclohexylmethyl)-11-isobutyl-18-isopropyl-6,12,16,19,33,36-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (917) (3S,9S,18S,21S,25S,28S,31R,34S)-3-[2-[3-chloro-4-(trifluoromethyl)phenyl]ethyl]-28-cyclohexyl-9-(cyclohexylmethyl)-21-isobutyl-7,10,13,16,22,26,29,31-octamethyl-8-[(1S)-1-methylpropyl]-25-(piperidine-1-carbonyl)-1,4,7,10,13,16,19,22,26,29,32-undecazabicyclo[32.3.0]heptatriacontane-2,5,8,11,14,17,20,23,27,30,33-undecone, (918) (5S,8S,11S,15S,18S,23aS,29S,35S,37aS)-8-((S)-sec-butyl)-18,35-dicyclopentyl-29-(3-fluoro-4-(trifluoromethyl)phenethyl)-11-isobutyl-5,6,12,16,19,33,36-heptamethyl-15-(pyrrolidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (919) (3S,6R,9S,18S,21S,25R,28S,34S)-3-[2-[3-chloro-4-(trifluoromethyl)phenyl]ethyl]-28-cyclopentyl-6,7,10,13,16,21,22,25,29-nonamethyl-18-[(1S)-1-methylpropyl]-9-(3-pyridylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (920) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-22-[(4-fluorophenyl)methyl]-9-isobutyl-N,N,3,4,10,14,17,23,29,32-decamethyl-6-[(1S)-1-methylpropyl]-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide, (921) (5S,8S,11S,15S,18S,23aS,29S,35S,37aS)-15-(azetidine-1-carbonyl)-8-((S)-sec-butyl)-29-(3-chloro-4-(trifluoromethyl)phenethyl)-35-(cyclohexylmethyl)-18-cyclopentyl-11-(cyclopentylmethyl)-5,12,16,19,33,36-hexamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (922) (6S,9R,13S,16S,25S,31S,33aS,37aS,38aS)-16-((S)-sec-butyl)-25-(4-chlorobenzyl)-6,13-diisobutyl-3,3,5,9,12,18,21,24,27-nonamethyl-31-(4-(trifluoromethyl)phenethyl)octacosahydro-[1,4,7,10,13,16,19,22,25,28,31]undecaazacyclotetratriacontino[10,9-a]indol-1,4,7,11,14,17,20,23,26,29,32(8H)-undecaone, (923) (8S,11S,17S,26S,29S,36S)-17-[(4-chlorophenyl)methyl]-8,36-diisobutyl-29-isopropyl-9,15,18,21,24,30,37-heptamethyl-26-[(1S)-1-methylpropyl]-11-[2-[4-(trifluoromethyl)phenyl]ethyl]-6,9,12,15,18,21,24,27,30,34,37-undecazaspiro[4.33]octatriacontane-7,10,13,16,19,22,25,28,31,35,38-undecone, (924) (3S,9S,18S,21S,25R,28S,34S)-3-[2-[3-chloro-4-(trifluoromethyl)phenyl]ethyl]-9-(cyclohexylmethyl)-18-(cyclopentylmethyl)-21-isobutyl-28-isopropyl-7,10,13,16,22,25,29-heptamethyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone, (925) (3S,9S,18S,21S,25S,28S,31S,34S,36R)-3-[(3-chlorophenyl)methyl]-9-[(4-chlorophenyl)methyl]-36-ethoxy-28-isobutyl-31-(isopentyloxymethyl)-7,10,13,16,21,22,29,32-octamethyl-18-[(1S)-1-methylpropyl]-25-(pyrrolidine-1-carbonyl)-1,4,7,10,13,16,19,22,26,29,32-undecazabicyclo[32.3.0]heptatriacontane-2,5,8,11,14,17,20,23,27,30,33-undecone, (926) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-cyclopentyl-11-isobutyl-5,6,12, 16,19,33,36-heptamethyl-15-(morpholine-4-carbonyl) docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (927) (3S,6S,9S,12S,18S,27S,30S,34R)-6-benzyl-18-[(4-chlorophenyl)methyl]-3,9-diisobutyl-1,4,7,16,19,22,25,30,31,34-decamethyl-27-[(1S)-1-methylpropyl]-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (928) (5S,8S,11S,15R,18S,23aS,25R,29S,35S,37aS)-8-((S)-sec-butyl)-29-(3-chloro-4-(trifluoromethyl)phenethyl)-18-cyclohexyl-25-ethoxy-36-ethyl-11-isobutyl-5,6,12,15,16,19,33-heptamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclobutan]-4,7,10,13,17,20,23,28,31,34,37(14H,22H)-undecaone, (929) (5S,8S,11S,15S,18S,23aS,29S,35S,37aS)-8-((S)-sec-butyl)-29-(3-chloro-4-(trifluoromethyl)phenethyl)-11-isobutyl-18-isopropyl-35-((R)-1-methoxyethyl)-5,6,12,16,19,33,36-heptamethyl-15-(piperidine-1-carbonyl) docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (930) (3S,9S,18S,21S,25R,28S,34S)-3-[2-[3-chloro-4-(trifluoromethyl)phenyl]ethyl]-9-(cyclopropylmethyl)-21-isobutyl-28-isopropyl-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (931) (6S,9S,13S,16S,22S,25S,31S,34S)-31-(cyclohexylmethyl)-25-[(3-iodophenyl)methyl]-9,16-diisobutyl-4,10,14,19,19,20,29,32-octamethyl-6-[(1S)-1-methylpropyl]-22-(2-phenylethyl)-13-(piperidine-1-carbonyl)-1,4,7,10,14,17,20,23,26,29,32-undecazabicyclo[32.2.0]hexatriacontane-2,5,8,11,15,18,21,24,27,30,33-undecone, (932) (5S,8S,11S,15R,18S,23aS,25R,29S,35S,37aS)-8,18-di((S)-sec-butyl)-29-(3-chloro-4-(trifluoromethyl)phenethyl)-25-ethoxy-36-ethyl-11-isobutyl-5,6,12,15,16,19,33-heptamethyl-35-(4-(trifluoromethyl)benzyl) docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (933) (5S,8S,11S,15R,18S,21S,23aS,29S,35S,37aS)-8-((S)-sec-butyl)-29-(3-chloro-4-(trifluoromethyl)phenethyl)-18-cyclopentyl-11-isobutyl-21-isopropyl-5,6,12,15,19,33,36-heptamethyl-35-(4-methylbenzyl)tetracosahydro-2H-azeto[2,1-u]pyrrolo[2,1-i][1,4,7,10,13,16,19,22,25,28,31]undecaazacyclotetratriacontin-4,7,10,13,17,20,23,28,31,34,37(14H)-undecaone, (934) (3S,6S,9S,12S,18S,27S,30S,34S)-9-butyl-6,18-bis[(4-chlorophenyl)methyl]-12-[(3-iodophenyl)methyl]-3,30-diisobutyl-1,7,16,19,22,25,31-heptamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (935) 2-[[(3S,9S,18S,21S,25S,28S,34S)-3-[2-[3-chloro-4-(trifluoromethyl)phenyl]ethyl]-21-isobutyl-28-isopropyl-7,10,13,16,22,26,29-heptamethyl-18-[(1S)-1-methylpropyl]-2,5,8,11,14,17,20,23,27,30,33-undecaoxo-25-(piperidine-1-carbonyl)spiro[1,4,7,10,13,16,19,22,26,29,32-undecazabicyclo[32.3.0]heptatriacontane-31,1'-cyclopentane]-9-yl]methyl]benzonitrile, (936) (3S,9S,18S,21S,25S,28S,34S)-3-[2-[3-chloro-4-(trifluoromethyl)phenyl]ethyl]-9-cyclobutyl-28-cyclohexyl-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (937) (3S,9S,18S,21S,25R,28S,34S)-3-[2-[3-chloro-4-(trifluoromethyl)phenyl]ethyl]-18-cyclohexyl-9-(cyclohexylmethyl)-21-isobutyl-28-isopropyl-7,10,13,16,22,25,29-heptamethyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone, (938) (5S,8S,11S,15S,18S,23aS,29S,35S,37aS)-8-((S)-sec-butyl)-18-cyclopentyl-29-(3-fluoro-4-(trifluoromethyl)phenethyl)-11-isobutyl-5,6,12,16,19,33,36-heptamethyl-35-(4-methylbenzyl)-15-(morpholine-4-carbonyl) docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (939) (8S,11S,17S,26S,29S,33S,36S)-11-[2-[3-chloro-4-(trifluoromethyl)phenyl]ethyl]-17-(cyclohexylmethyl)-29-isobutyl-36-isopropyl-8,9,15,18,21,24,30,34,37-nonamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (940) (8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-8-(isopentyloxymethyl)-9,15,18,21,24,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (941) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-18-(2-methoxyethyl)-7,10,13,16,22,26,29-heptamethyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (942) (6S,9S,13S,16S,22S,25S,31S,34S)-25-[2-[3-chloro-4-(trifluoromethyl)phenyl]ethyl]-16-cyclohexyl-31-(cyclohexylmethyl)-4,9,10,14,17,23,29,32-octamethyl-6-[(1S)-1-methylpropyl]-13-(piperidine-1-carbonyl)-22-(3-pyridylmethyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (943) (3S,9S,18S,21S,25S,28S,34S)-3-[2-[3-chloro-4-(trifluoromethyl)phenyl]ethyl]-28-cyclohexyl-7,10,13,16,22,26,29-heptamethyl-18-[(1S)-1-methylpropyl]-25-(3-oxa-8-azabicyclo[3.2.1]octane-8-carbonyl)-9-(propoxymethyl)-21-(2,2,2-trifluoroethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (944) (3S,9S,18S,21S,25R,28S,31S,34S)-3-[2-[3-chloro-4-(trifluoromethyl)phenyl]ethyl]-9-(cyclohexylmethyl)-31-ethyl-21-isobutyl-28-isopropyl-7,10,13,16,22,25,26,29,31-nonamethyl-18-[(1S)-1-methylpropyl]-1,4,7,10,13,16,19,22,26,29,32-undecazabicyclo[32.3.0]heptatriacontane-2,5,8,11,14,17,20,23,27,30,33-undecone, (945) (8S,11S,17S,26S,29S,33S,36S)-11-[2-[3-chloro-4-(trifluoromethyl)phenyl]ethyl]-17-(cyclohexylmethyl)-8-[(3-fluorophenyl)methyl]-36-isopropyl-9,15,18,21,24,29,30,34,37-nonamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (946) (5S,8S,11S,15S,18S,23aS,29S,35S,37aS)-29-(3-chloro-4-(trifluoromethyl)phenethyl)-35-(cyclohexylmethyl)-11-isobutyl-18-isopropyl-5,6,12,16,19,33,36-heptamethyl-15-(piperidine-1-carbonyl)-8-(prop-2-yn-1-yl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (947) (5S,8S,11S,15R,18S,23aS,29S,35S,37aS)-8-((S)-sec-butyl)-29-(3-chloro-4-(trifluoromethyl)phenethyl)-18-cyclohexyl-36-ethyl-25,25-difluoro-11-isobutyl-5,6,12,15,16,19,33-heptamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclobutan]-4,7,10,13,17,20,23,28,31,34,37(14H,22H)-undecaone, (948) (3S,9S,18S,21S,25S,28S,34S)-3-[2-[3-chloro-4-(trifluoromethyl)phenyl]ethyl]-21-cyclobutyl-9-(cyclohexylmethyl)-28-isopropyl-7,10,13,16,22,26,29-heptamethyl-8-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (949) (5S,8S,11S,15R,18S,23aS,29S,35S,37aS)-8-((S)-sec-butyl)-29-(3-chloro-4-(trifluoromethyl)phenethyl)-18-cyclopentyl-36-ethyl-25,25-difluoro-11-isobutyl-5,6,12,15,16,19,33-heptamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclobutan]-4,7,10,13,17,20,23,28,31,34,37(14H,22H)-undecaone, (950) (8S,11S,17S,26S,29S,33S,36S)-11-[2-[3-chloro-4-(trifluoromethyl)phenyl]ethyl]-36-cyclohexyl-17-(cyclohexylmethyl)-8-[(5-fluoro-3-pyridyl)methoxymethyl]-29-isobutyl-9,15,18,21,24,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (951) (5S,8S,11S,15R,18S,23aS,25R,29S,35S,37aS)-8,18-di((S)-sec-butyl)-29-(3-chloro-4-(trifluoromethyl)phenethyl)-25-ethoxy-36-ethyl-11-isobutyl-5,6,12,15,16,19,33-heptamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (952) (5S,8S,11S,15R,18S,23aS,29S,35S,37aS)-8-((S)-sec-butyl)-35-(cyclohexylmethyl)-29-(3-fluoro-4-(trifluoromethyl)phenethyl)-11-isobutyl-18-isopropyl-5,6,12,15,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (953) (9'S,12'S,16'S,19'S,24'aS,30'S,36'S,38'aS)-9'-((S)-sec-butyl)-30'-(4-chlorophenethyl)-36'-(cyclohexylmethyl)-12'-isobutyl-19'-isopropyl-7',13',17',20',34',37'-hexamethyl-16'-(piperidine-1-carbonyl)tetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone, (954) (3S,9S,18S,21S,25S,28S,34S)-3-[2-(3-chlorophenyl)ethyl]-28-cyclohexyl-9-(cyclohexylmethyl)-7,10,13,16,21,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (955) N-tert-butyl-2-[[(3S,9S,18S,21S,25S,28S,34S)-3-[2-[3-chloro-4-(trifluoromethyl)phenyl]ethyl]-9-(cyclohexylmethyl)-21-isobutyl-28-isopropyl-7,10,13,16,22,29-hexamethyl-18-[(1S)-1-methylpropyl]-2,5,8,11,14,17,20,23,27,30,33-undecaoxo-spiro[1,4,7,10,13,16,19,22,26,29,32-undecazabicyclo[32.3.0]heptatriacontane-31,1'-cyclopentane]-25-yl]methoxy]acetamide, (956) (3S,9S,12S,18S,27S,30S,34R)-18-[(4-chlorophenyl)methyl]-12-[2-[3-fluoro-4-(trifluoromethyl)phenyl]ethyl]-3,9,30-triisobutyl-27-isopropyl-1,6,6,7,16,19,22,25,31,34-decamethyl-1,4,7,10,13,16,19,22,25,28,31-undecazacyclotetracosane-2,5,8,11,14,17,20,23,26,29,32-undecone, (957) (3S,6S,9S,13S,16S,22S,25S,31S,34S)-25-[2-[3-chloro-4-(trifluoromethyl)phenyl]ethyl]-9-isobutyl-N,N,3,4,10,14,17,22,29,32-decamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (958) (3S,6S,9S,13S,16S,22S,25S,31S,34S)-22-benzyl-25-[2-[3-chloro-4-(trifluoromethyl)phenyl]ethyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (959) (5S,8S,11S,15S,18S,23aS,29S,35S,37aS)-8,18-di((S)-sec-butyl)-29-(3-chloro-4-(trifluoromethyl)phenethyl)-11-cyclobutyl-35-(cyclohexylmethyl)-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (960) (8S,11S,15S,18S,23aS,25R,29S,35S,37aS)-8-((S)-sec-butyl)-29-(3-chloro-4-(trifluoromethyl)phenethyl)-18-cyclohexyl-35-(cyclohexylmethyl)-11-isobutyl-6,12,16,19,33,36-hexamethyl-25-phenyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (961) (5S,8S,11S,15R,18S,23aS,29S,35S,37aS)-11-(but-3-yn-1-yl)-8-((S)-sec-butyl)-29-(3-chloro-4-(trifluoromethyl)phenethyl)-18-cyclohexyl-35-(4-iodobenzyl)-5,6,12,15,16,19,33,36-octamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (962) (3S,9S,18S,21S,25R,28S,34S)-3-[2-[3-chloro-4-(trifluoromethyl)phenyl]ethyl]-9-(cyclohexylmethyl)-28-cyclopentyl-36,36-difluoro-21-isobutyl-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,1'-cyclobutane]-2,5,8,11,14,17,20,23,27,30,33-undecone, (963) (8S,11S,17S,26S,29S,33S,36S)-8-[(2-chlorophenyl)methyl]-11-[2-[3-chloro-4-(trifluoromethyl)phenyl]ethyl]-17-(cyclohexylmethyl)-36-isopropyl-9,15,18,21,24,29,30,34,37-nonamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (964) (9'S,12'S,16'S,19'S,24a'S,30'S,32a'R,38'S,40a'S)-9'-((S)-sec-butyl)-30'-(3-chloro-4-(trifluoromethyl)phenethyl)-38'-(cyclohexylmethyl)-19'-isopropyl-7',12',13',17',20',39'-hexamethyl-16'-(piperidine-1-carbonyl)hexacosahydro-5'H-spiro[cyclopentane-1,22'-tripyrrolo[2,1-i:2',1'-o:2'',1'''-u][1,4,7,10,13,16,19,22,25,28,31]undecaazacyclotetratriacontin]-5',8',11',14',18',21',24',29',32',37',40'(15'H,23'H)-undecaone, (965) (5S,8S,11S,15S,18S,23aS,29S,35S,37aS)-8-((S)-sec-butyl)-18-cyclopentyl-29-(3,5-difluoro-4-(trifluoromethyl)phenethyl)-11-isobutyl-N,N,5,6,12,16,19,33,36-nonamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (966) (5S,8S,11S,15R,18S,23aS,29S,35S,37aS)-29-(3-chloro-4-(trifluoromethyl)phenethyl)-35-(cyclohexylmethyl)-8-cyclopentyl-11-isobutyl-18-isopropyl-5,6,12,15,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (967) (3S,9S,12S,18S,27S,30S,34R)-18-(cyclohexylmethyl)-12-[2-[3-fluoro-4-(trifluoromethyl)phenyl]ethyl]-9,30-diisobutyl-3-isopropyl-1,6,6,7,16,19,22,25,31,34-decamethyl-27-[(1S)-1-methylpropyl]-1,4,7,10,13,16,19,22,25,28,31-undecazacyclotetratriacontane-2,5,8,11,14,17,20,23,26,29,32-undecone, (968) (3S,9S,18S,21S,25S,28S,34S)-3-[2-[3-chloro-4-(trifluoromethyl)phenyl]ethyl]-28-(cyclobutylmethyl)-9-(cyclohexylmethyl)-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (969) (3S,9S,12S,18S,27S,30S,34S)-18-(cyclohexylmethyl)-12-[2-[3-fluoro-4-(trifluoromethyl)phenyl]ethyl]-3,9,30-triisobutyl-1,6,6,7,16,19,22,25,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (970) (3S,9S,18S,21S,25R,28S,34S)-3-[2-[3-chloro-4-(trifluoromethyl)phenyl]ethyl]-9-(cyclohexylmethyl)-16,21-diisobutyl-28-isopropyl-7,10,13,22,25,29-hexamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (971) (5S,8S,11S,15R,18S,23aS,29S,35S,37aS)-11-(but-3-yn-1-yl)-8-((S)-sec-butyl)-29-(3-chloro-4-(trifluoromethyl)phenethyl)-18-cyclohexyl-35-(4-iodobenzyl)-5,6,12,15,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (972) (3S,6S,9S,12S,18S,27S,30S,34R)-6-benzyl-18-[(4-chlorophenyl)methyl]-9,34-diisobutyl-3-isopropyl-4,7,10,16,19,22,25,30,31-nonamethyl-27-[(1S)-1-methylpropyl]-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (973) (5S,8S,11S,15S,18S,23aS,29S,35S,37aS)-15-(3-oxa-8-azabicyclo[3.2.1]octane-8-carbonyl)-8-((S)-sec-butyl)-29-(3-chloro-4-(trifluoromethyl)phenethyl)-35-(cyclohexylmethyl)-18-cyclopentyl-11-isobutyl-5,6,12,16,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (974) (5S,8S,11S,15S,18S,23aS,29S,35S,37aS)-8-((S)-sec-butyl)-29-(3-chloro-4-(trifluoromethyl)phenethyl)-18-cyclopentyl-11-isobutyl-5,6,12,16,19,33,36-heptamethyl-15-(morpholine-4-carbonyl)-35-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (975) 3-[[(3S,9S,18S,21S,25R,28S,34S)-3-[2-[3-chloro-4-(trifluoromethyl)phenyl]ethyl]-21-isobutyl-28-isopropyl-7,10,13,16,22,25,29-heptamethyl-18-1(1S)-1-methylpropyl]-2,5,8,11,14,17,20,23,27,30,33-undecaoxo-spiro[1,4,7,10,13,16,19,22,26,29,32-undecazabicyclo[32.3.0]heptatriacontane-31,1'-cyclopentane]-9-yl]methyl]benzonitrile, (976) (5S,8S,11S,15S,18S,23aS,29S,35S,37aS)-8-((S)-sec-butyl)-35-(cyclohexylmethyl)-18-isopropyl-5,6,11,12,16,19,33,36-octamethyl-29-(4-methylphenethyl)-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (977) (3S,9S,18S,21S,25S,28S,34S)-3-[2-[3-chloro-4-(trifluoromethyl)phenyl]ethyl]-21-cyclobutyl-28-cyclohexyl-9-(cyclohexylmethyl)-7,10,13,16,22,26,29-heptamethyl-18-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (978) (3S,6S,9S,12S,18S,27S,30S,34R)-6-benzyl-18-[(4-chlorophenyl)methyl]-3-isobutyl-4,7,9,10,16,19,22,25,30,31,34-undecamethyl-27-[(1S)-1-methylpropyl]-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (979) (3S,9S,18S,21S,28S,34S)-3-[2-[3-chloro-4-(trifluoromethyl)phenyl]ethyl]-9-(cyclohexylmethyl)-21-isobutyl-28-isopropyl-7,10,13,16,22,29-hexamethyl-8-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (980) (3S,9S,18S,21S,25S,28S,34S)-3-[2-[3-chloro-4-(trifluoromethyl)phenyl]ethyl]-9-(cyclohexylmethyl)-21-cyclopropyl-28-isopropyl-7,10,13,16,22,26,29-heptamethyl-8-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (981) (3S,9S,18S,21S,25S,28S,34S)-3-[2-[3-chloro-4-(trifluoromethyl)phenyl]ethyl]-28-cyclohexyl-7,10,13,16,22,26,29-heptamethyl-18-[(1S)-1-methylpropyl]-25-(morpholine-4-carbonyl)-21-(2,2,2-trifluoroethyl)-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (982) (3S,6S,9S,13S,16S,19S,22S,25S,31S,34S)-25-[2-[3-chloro-4-(trifluoromethyl)phenyl]ethyl]-9-isobutyl-19-isopropyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)-22-(thiazol-4-ylmethyl)-1,4,7,10,14,17,20,23,26,29,32-undecazabicyclo[32.2.0]hexatriacontane-13-carboxamide, (983) (3S,9S,18S,21S,25S,28S,34S)-3-[2-[3-chloro-4-(trifluoromethyl)phenyl]ethyl]-28-cyclohexyl-9,21-bis(cyclohexylmethyl)-7,10,13,16,22,26,29-heptamethyl-8-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (984) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-22-[2-(4,4-difluoro-1-piperidyl)-2-oxo-ethyl]-9-isobutyl-3,4,10,14,17,23,29,32-octamethyl-6-[(1S)-1-methylpropyl]-13-(piperidine-1-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (985) (3S,9S,18S,21S,25R,28S,34S)-3-[2-[3-chloro-4-(trifluoromethyl)phenyl]ethyl]-9-(cyclopentylmethyl)-21-isobutyl-28-isopropyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (986) (3S,9S,18S,21S,25S,28S,34S)-3-[2-[3-chloro-4-(trifluoromethyl)phenyl]ethyl]-9,18-bis(cyclohexylmethyl)-21-isobutyl-28-isopropyl-7,10,13,16,22,26,29-heptamethyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (987) (5S,8S,11S,15S,18S,23aS,29S,35S,37aS)-8-((S)-sec-butyl)-18-cyclopentyl-29-(3-fluoro-4-(trifluoromethyl)phenethyl)-11-isobutyl-5,6,12,16,19,33,36-heptamethyl-35-(propoxymethyl)-15-(pyrrolidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (988) (7S,10S,14S,17S,22aS,28S,34S,36aS,40aS)-7-((S)-sec-butyl)-28-(3-chloro-4-(trifluoromethyl)phenethyl)-34-(cyclohexylmethyl)-10-isobutyl-17-isopropyl-11,15,18,32,35-pentamethyl-14-(piperidine-1-carbonyl)tetracosahydro-27H-spiro[azeto[1,2-j]pyrido[1,2-g]pyrrolo[1,2-v][1,4,7,10,13,16,19,22,25,28,31]undecaazacyclotetratriacontine-20,1'-cyclopentan]-6,9,12,16,19,22,27,30,33,36,40(2H,13H,21H,36aH)-undecaone, (989) (3S,6S,9S,12S,18S,27S,30S,34S)-6-benzyl-18-[(4-chlorophenyl)methyl]-3,9-diisobutyl-4,7,16,19,22,25,30-heptamethyl-27-[(1S)-1-methylpropyl]-34-(pyrrolidine-1-carbonyl)-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (990) (5S,8S,11S,15R,18S,23aS,29S,32R,35S,37aS)-8-((S)-sec-butyl)-29-(3-chloro-4-(trifluoromethyl)phenethyl)-18-cyclopentyl-35-(2-fluorobenzyl)-5,6,11,12,15,19,32,33,36-nonamethyldocosahydro-2H4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (991) (3S,9S,18S,21S,25R,28S,34S)-3-[2-[3-chloro-4-(trifluoromethyl)phenyl]ethyl]-9-(cyclohexylmethyl)-28-(cyclopentylmethyl)-21-isobutyl-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (992) (3S,9S,18S,21S,25S,28S,34S)-3-[2-[3-chloro-4-(trifluoromethyl)phenyl]ethyl]-9-(cyclohexylmethyl)-21-isobutyl-25-(isopentyloxymethyl)-28-isopropyl-7,10,13,16,22,29-hexamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (993) (3S,6S,9S,13S,16S,19S,22S,25S,31S,34S)-25-[2-[3-chloro-4-(trifluoromethyl)phenyl]ethyl]-31-(cyclohexylmethyl)-16-cyclopentyl-9-isobutyl-N,N,3,4,10,14,17,19,22,23,29,32-dodecamethyl-6-[(1S)-1-methylpropyl]-2,5,8,11,15,18,21,24,27,30,33-undecaoxo-1,4,7,10,14,17,20,23,26,29,32-undecazabicyclo[32.2.0]hexatriacontane-13-carboxamide, (994) (6S,9S,13R,16S,19S,22S,25S,31S,34S)-19-benzyl-31-[(4-chlorophenyl)methyl]-25-[2-[3-chloro-4-(trifluoromethyl)phenyl]ethyl]-22-isobutyl-16-isopropyl-4,9,10,13,17,20,23,29,32-nonamethyl-6-[(1S)-1-methylpropyl]-1,4,7,10,14,17,20,23,26,29,32-undecazabicyclo[32.2.0]hexatriacontane-2,5,8,11,15,18,21,24,27,30,33-undecone, (995) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-5,6,12,16,19,33,36-heptamethyl-15-(piperidine-1-carbonyl)-18-propyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (996) (1R,4S,7S,16S,22S,25S,31S,34R)-16-[(4-chlorophenyl)methyl]-25,31-diisobutyl-4-isopropyl-3,9,12,15,18,24,30-heptamethyl-7-[(1S)-1-methylpropyl]-22-[2-[4-(trifluoromethyl)phenyl]ethyl]spiro[3,6,9,12,15,18,21,24,27,30,33-undecazabicyclo[32.3.0]heptatriacontane-28,1'-cyclopentane]-2,5,8,11,14,17,20,23,26,29,32-undecone, (997) (3S,6S,9S,12S,18S,27S,30S,34S)-9-butyl-18-[(4-chlorophenyl)methyl]-6-[(4-fluorophenyl)methyl]-12-[(3-iodophenyl)methyl]-3,30-diisobutyl-1,7,16,19,22,25,31-heptamethyl-27-1[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (998) N-(tert-butyl)-2-(((5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-6,12,16,19,33,36-hexamethyl-4,7,10,13,17,20,23,28,31,34,37-undecaoxo-15-(piperidine-1-carbonyl)tetratriacontahydro-2H,4H-spiro[azeto[2,1-u]pyrrolo[2,1-i][1,4,7,10,13,16,19,22,25,28,31]undecaazacyclotetratriacontine-21,1'-cyclopentan]-5-yl)methoxy)acetamide, (999) (5S,8S,11S,15S,18S,23aS,29S,35S,37aS)-8,18-di((S)-sec-butyl)-35-(cyclohexylmethyl)-29-(3-fluoro-4-(trifluoromethyl)phenethyl)-11-isobutyl-N,N,5,6,12,16,19,33,36-nonamethyl-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1000) (3S,6S,9S,13S,16S,22S,25S,31S,34S)-25-[2-[3-chloro-4-(trifluoromethyl)phenyl]ethyl]-22-[(3-fluorophenyl)methyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (1001) (3S,9S,18S,21S,25S,28S,34S)-3-[2-[3-chloro-4-(trifluoromethyl)phenyl]ethyl]-28-cyclohexyl-7,10,13,16,22,26,29-heptamethyl-18-[(1S)-1-methylpropyl]-25-(morpholine-4-carbonyl)-9-(p-tolylmethyl)-21-(2,2,2-trifluoroethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1002) (5S,8S,11S,15S,18S,23aS,29S,35S,37aS)-15-(3-oxa-8-azabicyclo[3.2.1]octane-8-carbonyl)-8,18-di((S)-sec-butyl)-29-(3-chloro-4-(trifluoromethyl)phenethyl)-35-cyclopentyl-11-isobutyl-5,6,12,16,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1003) (3S,9S,18S,21S,25R,28S,34S)-3-[2-[3-chloro-4-(trifluoromethyl)phenyl]ethyl]-36,36-difluoro-21-isobutyl-7,10,13,16,22,25,26,29-octamethyl-18,28-bis[(1S)-1-methylpropyl]-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1004) (9'S,12'S,16'R,19'S,24a'S,30'S,36'S,38a'S)-36'-benzyl-9'-((S)-sec-butyl)-30'-(3-chloro-4-(trifluoromethyl)phenethyl)-19'-cyclopentyl-7',12',13',16',20',34',37'-heptamethyltetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone, (1005) (8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-9,15,18,21,24,30,34,37-octamethyl-26-[(1S)-1-methylpropyl]-33-(piperidine-1-carbonyl)-8-propyl-6,9,12,15,18,21,24,27,30,34,37-undecazaspiro[4.33]octatriacontane-7,10,13,16,19,22,25,28,31,35,38-undecone, (1006) (5S,8S,11S,15R,18S,23aS,25R,29S,35S,37aS)-8-((S)-sec-butyl)-29-(3-chloro-4-(trifluoromethyl)phenethyl)-18-cyclopentyl-25-ethoxy-11-isobutyl-5,6,12,15,16,19,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclobutan]-4,7,10,13,17,20,23,28,31,34,37(14H,22H)-undecaone, (1007) (3S,9S,18S,25S,28S,34S)-25-benzyl-3-[2-[3-chloro-4-(trifluoromethyl)phenyl]ethyl]-28-cyclohexyl-9-(cyclohexylmethyl)-7,10,13,16,26,29-hexamethyl-18-[(1S)-1-methylpropyl]spiro[1,4,7,10,13,16,19,23,26,29,32-undecazabicyclo[32.3.0]heptatriacontane-31,1'-cyclopentane]-2,5,8,11,14,17,20,24,27,30,33-undecone, (1008) (5S,8S,11S,15S,18S,23aS,29S,35S,37aS)-8-((S)-sec-butyl)-18-cyclopentyl-29-(3-fluoro-4-(trifluoromethyl)phenethyl)-11-isobutyl-5,6,12,16,19,33,36-heptamethyl-35-(4-methylbenzyl)-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1009) (3S,6S,9S,13S,16S,22S,25S,31S,34S)-22-[(2-chlorophenyl)methyl]-25-[2-3-chloro-4-(trifluoromethyl)phenyl]ethyl]-31-(cyclohexylmethyl)-16-cyclopentyl-9-isobutyl-N,N,3,4,10,14,17,23,29,32-decamethyl-6-[(1S)-1-methylpropyl]-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide, (1010) (5S,8S,11S,15S,18S,21S,23aS,29S,35S,37aS)-8-((S)-sec-butyl)-29-(3-chloro-4-(trifluoromethyl)phenethyl)-35-(cyclohexylmethyl)-18-cyclopentyl-11-isobutyl-21-isopropyl-N,N,5,6,12,16,19,33,36-nonamethyl-4,7,10,13,17,20,23,28,31,34,37-undecaoxohexatriacontahydro-2H-azeto[2,1-u]pyrrolo[2,1-i][1,4,7,10,13,16,19,22,25,28,31]undecaazacyclotetratriacontine-15-carboxamide, (1011) (5S,8S,11S,15R,18S,23aS,29S,32R,35S,37aS)-8-((S)-sec-butyl)-29-(3-chloro-4-(trifluoromethyl)phenethyl)-18-cyclopentyl-5,6,11,12,15,19,32,33,36-nonamethyl-35-(pyridin-3-ylmethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1012) (8S,11S,17S,26S,29S,33S,36S)-11-[2-[3-chloro-4-(trifluoromethyl)phenyl]ethyl]-36-cyclohexyl-17-(cyclohexylmethyl)-9,15,18,21,24,29,30,34,37-nonamethyl-26-[(1S)-1-methylpropyl]-33-(piperidine-1-carbonyl)-8-(3-pyridylmethyl)-6,9,12,15,18,21,24,27,30,34,37-undecazaspiro[4.33]octatriacontane-7,10,13,16,19,22,25,28,31,35,38-undecone, (1013) (3S,9S,18S,21S,25R,28S,34S)-9-[(4-chlorophenyl)methyl]-21,28-diisobutyl-7,10,13,16,22,25,29,31,31-nonamethyl-18-[(1S)-1-methylpropyl]-3-[2-[4-(trifluoromethyl)phenyl]ethyl]-1,4,7,10,13,16,19,22,26,29,32-undecazabicyclo[32.3.0]heptatriacontane-2,5,8,11,14,17,20,23,27,30,33-undecone, (1014) (8S,11S,17S,26S,29S,33R,36S)-17-[(4-chlorophenyl)methyl]-11-[2-[3-chloro-4-(trifluoromethyl)phenyl]ethyl]-8,36-diisobutyl-29-isopropyl-9,15,18,21,24,30,33,37-octamethyl-26-[(1S)-1-methylpropyl]-6,9,12,15,18,21,24,27,30,34,37-undecazaspiro[4.33]octatriacontane-7,10,13,16,19,22,25,28,31,35,38-undecone, (1015) (3S,6S,9S,13S,16S,22S,25S,31S,34S)-22-benzyl-25-[(3-iodophenyl)methyl]-9,16-diisobutyl-3,4,10,14,19,19,20,29,32-nonamethyl-6-[(1S)-1-methylpropyl]-13-(piperidine-1-carbonyl)-31-(p-tolylmethyl)-1,4,7,10,14,17,20,23,26,29,32-undecazabicyclo[32.2.0]hexatriacontane-2,5,8,11,15,18,21,24,27,30,33-undecone, (1016) (5S,8S,11S,15S,18S,23aS,25S,29S,35S,37aS)-8-((S)-sec-butyl)-29-(3-chloro-4-(trifluoromethyl)phenethyl)-18-cyclohexyl-35-(cyclohexylmethyl)-11-isobutyl-5,6,12,16,19,33,36-heptamethyl-25-phenyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1017) (5S,8S,11S,15S,18S,23aS,29S,35S,37aS)-8,18-di((S)-sec-butyl)-29-(3-fluoro-4-(trifluoromethyl)phenethyl)-11-isobutyl-N,N,5,6,12,16,19,33,36-nonamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1018) (5S,8S,11S,15R,18S,23aS,29S,35S,37aS)-8-((S)-sec-butyl)-29-(3-chloro-4-(trifluoromethyl)phenethyl)-35-(4-chlorobenzyl)-11-isobutyl-18-isopropyl-5,6,12,15,19,33,36-heptamethyldocosahydro-2H,4H-spiro[azeto[2, 1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1019) (3S,9S,18S,21S,25R,28S,34S)-3-[2-[3-chloro-4-(trifluoromethyl)phenyl]ethyl]-9-(cyclohexylmethyl)-28-(cyclopropylmethyl)-21-isobutyl-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1020) (5S,8S,12R,15S,20aS,26S,32S,37aS)-5-((S)-sec-butyl)-26-(3-chloro-4-(trifluoromethyl)phenethyl)-32-(cyclohexylmethyl)-8-isobutyl-15-isopropyl-9,12,16,30,33,36-hexamethyldocosahydrospiro[azeto[1,2-g]pyrrolo[1,2-v][1,4,7,10,13,16,19,22,25,28,31]undecaazacyclotetratriacontine-18,1'-cyclopentan]-4,7,10,14,17,20,25,28,31,34,37(2H,11H,19H)-undecaone, (1021) (3S,9S,18S,21S,25R,28S,34S)-9-(cyclohexylmethyl)-21,28-diisobutyl-7,10,13,16,22,25,29-heptamethyl-18-[(1S)-1-methylpropyl]-3-[2-[4-(pentafluoro-□⁶-sulfanyl)phenyl]ethyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1022) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33,36-dodecone, (1023) (5S,8S,11S,15R,18S,23aS,29S,35S,37aS)-8-((S)-sec-butyl)-29-(3-chloro-4-(trifluoromethyl)phenethyl)-18-cyclopentyl-6-ethyl-11-isobutyl-5,12,15,19,33,36-hexamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1024) (5S,8S,11S,15S,18S,23aS,29S,35S,37aS)-8-((S)-sec-butyl)-35-(cyclohexylmethyl)-29-(3-fluoro-4-(trifluoromethyl)phenethyl)-18-isopropyl-5,6,11,12,16,19,33,36-octamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1025) (8R,11S,17S,26S,29S,33S,36S)-11-[2-[3-chloro-4-(trifluoromethyl)phenyl]ethyl]-17-(cyclohexylmethyl)-8-[2-(4,4-difluoro-1-piperidyl)-2-oxo-ethyl]-36-isopropyl-9,15,18,21,24,29,30,34,37-nonamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (1026) (3S,9S,18S,21S,25S,28S,34S)-3-[2-[3-chloro-4-(trifluoromethyl)phenyl]ethyl]-28-cyclohexyl-21-isobutyl-9-(isopentyloxymethyl)-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1027) (5S,8S,11S,15S,18S,23aS,29S,35S,37aS)-8-((S)-sec-butyl)-29-(3-chloro-4-(trifluoromethyl)phenethyl)-11-isobutyl-18-isopropyl-5,6,12,16,19,33,36-heptamethyl-15-(piperidine-1-carbonyl)-35-propyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1029) (5S,8S,11S,15S,18S,23aS,29S,35S,37aS)-8-((S)-sec-butyl)-18-cyclopentyl-29-(3-fluoro-4-(trifluoromethyl)phenethyl)-11-isobutyl-5,6,12,16,19,33,36-heptamethyl-15-(piperidine-1-carbonyl)-35-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1030) (5S,8S,11S,15S,18S,23aS,29S,35S,37aS)-15-(3-oxa-8-azabicyclo[3.2.1]octane-8-carbonyl)-8-((S)-sec-butyl)-18-cyclopentyl-29-(3-fluoro-4-(trifluoromethyl)phenethyl)-11-isobutyl-5,6,12,16,19,33,36-heptamethyl-35-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1031) (3S,9S,18S,21S,25R,28S,31S,34S)-31-benzyl-9-(cyclohexylmethyl)-28-isobutyl-7,10,13,16,21,22,25,29,32-nonamethyl-18-[(1S)-1-methylpropyl]-3-[2-[4-(trifluoromethyl)phenyl]ethyl]-1,4,7,10,13,16,19,22,26,29,32-undecazabicyclo[32.3.0]heptatriacontane-2,5,8,11,14,17,20,23,27,30,33-undecone, (1032) (3S,9S,18S,21S,25R,28S,34S)-3-[2-[3-chloro-4-(trifluoromethyl)phenyl]ethyl]-9-(cyclohexylmethyl)-21,25-diisobutyl-28-isopropyl-7,10,13,16,22,29-hexamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1033) (3S,9S,18S,21S,25R,28S,34S)-13-butyl-3-[2-[3-chloro-4-(trifluoromethyl)phenyl]ethyl]-9-(cyclohexylmethyl)-21-isobutyl-28-isopropyl-7,10,16,22,25,29-hexamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1034) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-isopropyl-5,6,11,12,16,19,21,21,22,33,36-undecamethyl-15-(piperidine-1-carbonyl)tetracosahydro-2H-azeto[2,1-u]pyrrolo[2,1-i][1,4,7,10,13,16,19,22,25,28,31]undecaazacyclotetratriacontin-4,7,10,13,17,20,23,28,31,34,37(14H)-undecaone, (1035) (3S,6S,9S,12S,18S,27S,30S,34S)-9-butyl-18-[(4-chlorophenyl)methy]-6-[(2-fluorophenyl)methyl]-12-[(3-iodophenyl)methyl]-3,30-diisobutyl-1,7,16,19,22,25,31-heptamethyl-27-1[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (1036) (5S,8S,11S,15S,18S,23aS,29S,35S,37aS)-8-((S)-sec-butyl)-29-(3-chloro-4-(trifluoromethyl)phenethyl)-11-cyclobutyl-35-(cyclohexylmethyl)-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1037) (3S,9S,18S,21S,25S,28S,34S)-3-[2-[3-chloro-4-(trifluoromethyl)phenyl]ethyl]-28-cyclohexyl-9-(cyclohexylmethyl)-21-(methoxymethyl)-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1038) (3S,9S,18S,21S,25R,28S,31R,34S)-31-allyl-3-[2-[3-chloro-4-(trifluoromethyl)phenyl]ethyl]-9-(cyclohexylmethyl)-21-isobutyl-28-isopropyl-7,10,13,16,22,25,26,29,31-nonamethyl-18-[(1S)-1-methylpropyl]-1,4,7,10,13,16,19,22,26,29,32-undecazabicyclo[32.3.0]heptatriacontane-2,5,8,11,14,17,20,23,27,30,33-undecone, (1039) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-22-[2-(4,4-difluoro-1-piperidyl)-2-oxo-ethyl]-9-isobutyl-3,4,10,14,17,23,29,32-octamethyl-6-[(1S)-1-methylpropyl]-13-(3-oxa-8-azabicyclo[3.2.1]octane-8-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (1040) (5S,8S,11S,15S,18S,23aS,29S,35S,37aS)-8-((S)-sec-butyl)-35-(cyclohexylmethyl)-29-(3-fluoro-4-(trifluoromethyl)phenethyl)-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1041) (3S,9S,18S,21S,25S,28S,34S)-3-[2-[3-chloro-4-(trifluoromethyl)phenyl]ethyl]-9-(cyclohexylmethyl)-28-1[(1R)-1-hydroxyethyl]-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1042) (5S,8S,11S,15S,18S,23aS,29S,35S,37aS)-8,18-di((S)-sec-butyl)-29-(3-chloro-4-(trifluoromethyl)phenethyl)-11-isopentyl-N,N,5,6,12,16,19,33,36-nonamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1043) (3S,9S,12S,18S,27S,30S,34S)-12-benzyl-9-butyl-18-[(4-chlorophenyl)methyl]-3,30-diisobutyl-1,6,6,7,16,19,22,25,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (1044) (3S,6S,9S,12S,18S,27S,30S,34S)-9-butyl-6-[(3-chlorophenyl)methyl]-18-[(4-chlorophenyl)methyl]-12-[(3-iodophenyl)methyl]-3,30-diisobutyl-1,7,16,19,22,25,31-heptamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (1045) (8S,11S,17S,26S,29S,33S,36S)-11-[2-[3-chloro-4-(trifluoromethyl)phenyl]ethyl]-36-cyclohexyl-17-(cyclohexylmethyl)-9-ethyl-29-isobutyl-8,15,18,21,24,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (1046) (5S,8S,11S,15R,18S,23aS,29S,35S,37aS)-8-((S)-sec-butyl)-29-(3-chloro-4-(trifluoromethyl)phenethyl)-18,35-dicyclopentyl-11-isobutyl-5,6,12,15,16,19,33,36-octamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1047) (5S,8S,11S,15S,18S,23aS,29S,35S,37aS)-8-((S)-sec-butyl)-29-(3-chloro-4-(trifluoromethyl)phenethyl)-35-cyclobutyl-18-cyclopentyl-16-ethyl-11-isobutyl-5,6,12,19,33,36-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1048) (3S,9S,18S,21S,25S,28S,31S,34S)-31-benzyl-9-[(4-chlorophenyl)methyl]-28-isobutyl-7,10,13,16,21,22,29,32-octamethyl-18-[(1S)-1-methylpropyl]-25-(pyrrolidine-1-carbonyl)-3-[2-[4-(trifluoromethyl)phenyl]ethyl]-1,4,7,10,13,16,19,22,26,29,32-undecazabicyclo[32.3.0]heptatriacontane-2,5,8,11,14,17,20,23,27,30,33-undecone, (1049) (5S,8S,11S,15R,18S,23aS,29S,35S,37aS)-8-((S)-sec-butyl)-18-cyclopentyl-29-(3,5-difluoro-4-(trifluoromethyl)phenethyl)-36-ethyl-25,25-difluoro-11-isobutyl-5,6,12,15,16,19,33-heptamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclobutan]-4,7,10,13,17,20,23,28,31,34,37(14H,22H)-undecaone, (1050) (9'S,12'S,16'R,19'S,24a'S,30'S,36'S,38a'S)-9'-((S)-sec-butyl)-30'-(3-chloro-4-(trifluoromethyl)phenethyl)-36'-(cyclohexylmethyl)-12'-isobutyl-19'-isopropyl-7',13',16',20',34',37'-hexamethyltetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone, (1051) (3S,9S,18S,21S,25S,28S,34S)-3-[2-[3-chloro-4-(trifluoromethyl)phenyl]ethyl]-9-(cyclohexylmethyl)-22-ethyl-28-isopropyl-7,10,13,16,21,26,29-heptamethyl-8-[(1S)-1-methylpropyl]-25-(piperidine-1-carbonyl)spiro 1,4,7,10,13,16,19,22,26,29,32-undecazabicyclo[32.3.0]heptatriacontane-31,1'-cyclopentane]-2,5,8,11,14,17,20,23,27,30,33-undecone, (1052) (3S,6S,9S,12S,18S,27S,30S,34S)-9-butyl-18-[(4-chlorophenyl)methy]-12-[(3-iodophenyl)methyl]-3,30-diisobutyl-1,7,16,19,22,25,31-heptamethyl-27-[(1S)-1-methylpropyl]-34-(piperidine-1-carbonyl)-6-[[3-(trifluoromethyl)phenyl]methyl]-1,4,7,10,13,16,19,22,25,28,31-undecazacyclotetratriacontane-2,5,8,11,14,17,20,23,26,29,32-undecone, (1053) (5S,8S,11S,15S,18S,23aS,25R,29S,35S,37aS)-8-((S)-sec-butyl)-29-(3-chloro-4-(trifluoromethyl)phenethyl)-18-cyclohexyl-35-(cyclohexylmethyl)-11-isobutyl-5,6,12,16,19,33,36-heptamethyl-25-phenyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1054) (3S,9S,12S,18S,27S,30S,34R)-18-[(4-chlorophenyl)methyl]-12-[2-[3-fluoro-4-(trifluoromethyl)phenyl]ethyl]-3,30-diisobutyl-9-isopropyl-1,6,6,7,16,19,22,25,31,34-decamethyl-27-[(1S)-1-methylpropyl]-1,4,7,10,13,16,19,22,25,28,31-undecazacyclotetratriacontane-2,5,8,11,14,17,20,23,26,29,32-undecone, (1055) (3S,9S,18S,21S,25S,28S,34S)-28-cyclohexyl-9-(cyclohexylmethyl)-7,10,13,16,21,22,26,29-octamethyl-18-[(1S)-1-methylpropyl]-25-(piperidine-1-carbonyl)-3-[2-(p-tolyl)ethyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1056) (9'S,12'S,16'R,19'S,24a'S,30'S,36'S,38a'S)-9'-((S)-sec-butyl)-30'-(3-chloro-4-(trifluoromethyl)phenethyl)-36'-(cyclohexylmethyl)-19'-isopropyl-7',12',13',16',20', 34',37'-heptamethyltetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone, (1057) (3S,9S,18S,21S,25S,28S,34S)-3-[2-[3-chloro-4-(trifluoromethyl)phenyl]ethyl]-28-cyclohexyl-9-(cyclopentylmethyl)-7,10,13,16,22,26,29-heptamethyl-18-[(1S)-1-methylpropyl]-25-(3-oxa-8-azabicyclo[3.2.1]octane-8-carbonyl)-21-(2,2,2-trifluoroethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1058) (6S,9S,13S,16S,19S,22S,25S,31S,34S)-19-benzyl-22-butyl-25-[(3-iodophenyl)methyl]-9,16-diisobutyl-31-[(4-methoxyphenyl)methyl]-4,10,14,19,20,29,32-heptamethyl-6-[(1S)-1-methylpropyl]-13-(piperidine-1-carbonyl)-1,4,7,10,14,17,20,23,26,29,32-undecazabicyclo[32.2.0]hexatriacontane-2,5,8,11,15,18,21,24,27,30,33-undecone, (1059) (5S,8S,11S,15S,18S,23aS,29S,35S,37aS)-8-((S)-sec-butyl)-29-(3-chloro-4-(trifluoromethyl)phenethyl)-18-cyclopentyl-N,N,5,12,16,19,33,36-octamethyl-35-(4-methylbenzyl)-4,7,10,13,17,20,23,28,31,34,37-undecaoxo-11-pentyltetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1060) (5S,8S,11S,15S,18S,23aS,29S,35S,37aS)-8,18-di((S)-sec-butyl)-29-(3-chloro-4-(trifluoromethyl)phenethyl)-35-(4-fluorobenzyl)-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1061) (3S,9S,18S,21S,25S,28S,34S)-9-[(4-chlorophenyl)methyl]-3-[2-[3-fluoro-4-(trifluoromethyl)phenyl]ethyl]-21,28-diisobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1062) (5S,8S,11S,15R,18S,23aS,29S,35S,37aS)-8-((S)-sec-butyl)-29-(3-chloro-4-(trifluoromethyl)phenethyl)-18-cyclopentyl-25,25-difluoro-11-isobutyl-5,6,12,15,16,19,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1063) (3S,6S,9S,13S,16S,22S,25S,31S,34S)-22-[(4-chlorophenyl)methyl]-25-[2-[3-chloro-4-(trifluoromethyl)phenyl]ethyl]-31-(cyclohexylmethyl)-16-cyclopentyl-9-isobutyl-N,N,3,4,10,14,17,23,29,32-decamethyl-6-[(1S)-1-methylpropyl]-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide, (1064) (3S,9S,18S,21S,25S,28S,34S)-3-[2-[3-chloro-4-(trifluoromethyl)phenyl]ethyl]-9-(cyclohexylmethyl)-18-cyclopentyl-21-isobutyl-28-isopropyl-7,10,13,16,22,26,29-heptamethyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1065) (3S,6S,9S,18S,21S,25R,28S,34S)-9-[(4-chlorophenyl)methyl]-3-[2-[3-chloro-4-(trifluoromethyl)phenyl]ethyl]-28-cyclopentyl-6,7,10,13,16,21,22,25,29-nonamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1066) (5S,8S,11S,15R,18S,23aS,29S,32R,35S,37aS)-8-((S)-sec-butyl)-29-(3-chloro-4-(trifluoromethyl)phenethyl)-18-cyclopentyl-35-isopropyl-5,6,11,12,15,19,32,33,36-nonamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1067) (3S,9S,12S,18S,27S,30S,34R)-18-[(1R)-1-benzyloxyethyl]-3,9-diisobutyl-4,6,6,10,16,19,22,25,30,31,34-undecamethyl-27-[(1S)-1-methylpropyl]-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (1068) (3S,9S,18S,21S,25R,28S,31S,34S)-3-[2-[3-chloro-4-(trifluoromethyl)phenyl]ethyl]-9-(cyclohexylmethyl)-21,31-diisobutyl-28-isopropyl-7,10,13,16,22,25,26,29,31-nonamethyl-18-[(1S)-1-methylpropyl]-1,4,7,10,13,16,19,22,26,29,32-undecazabicyclo[32.3.0]heptatriacontane-2,5,8,11,14,17,20,23,27,30,33-undecone, (1069) (8S,11S,17S,26S,29S,33R,36S)-17-[(4-chlorophenyl)methyl]-11-[2-[3-chloro-4-(trifluoromethyl)phenyl]ethyl]-8-isobutyl-29,36-diisopropyl-9,15,18,21,24,30,33,37-octamethyl-26-[(1S)-1-methylpropyl]-6,9,12,15,18,21,24,27,30,34,37-undecazaspiro[4.33]octatriacontane-7,10,13,16,19,22,25,28,31,35,38-undecone, (1070) (5S,8S,11S,15S,18S,23aS,29S,35S,37aS)-15-(azetidine-1-carbonyl)-8-((S)-sec-butyl)-35-(cyclohexylmethyl)-18-cyclopentyl-29-(3,5-difluoro-4-(trifluoromethyl)phenethyl)-11-isobutyl-5,6,12,16,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1071) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-9-isobutyl-N,N,3,4,10,14,17,23,29,32-decamethyl-6-[(1S)-1-methylpropyl]-2,5,8,11,15,18,21,24,27,30,33-undecaoxo-22-(3-pyridylmethyl)spiro[1,4,7,10,14,17,20,23,26,29,32-undecazabicyclo[32.2.0]hexatriacontane-19,1'-cyclopentane]-13-carboxamide, (1072) (3S,9S,18S,21S,25S,28S,34S)-3-[2-[3-chloro-4-(trifluoromethyl)phenyl]ethyl]-28-cyclohexyl-21-isobutyl-9-[(1R)-1-methoxyethyl]-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1073) (3S,9S,18S,21S,25S,28S,34S)-3-[2-[3-chloro-4-(trifluoromethyl)phenyl]ethyl]-9-(cyclohexylmethyl)-28-cyclopentyl-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1074) (3S,9S,18S,21S,25R,28S,34S)-3-[2-[3-chloro-4-(trifluoromethyl)phenyl]ethyl]-36,36-difluoro-21-isobutyl-7,10,13,16,22,25,26,29-octamethyl-18,28-bis[(1S)-1-methylpropyl]-9-[[4-(trifluoromethyl)phenyl]methyl]spiro[1,4,7,10,13,16,19,22,26,29,32-undecazabicyclo[32.3.0]heptatriacontane-31,1'-cyclobutane]-2,5,8,11,14,17,20,23,27,30,33-undecone, (1075) (3S,6R,9S,18S,21S,25R,28S,34S)-3-[2-[3-chloro-4-(trifluoromethyl)phenyl]ethyl]-28-cyclopentyl-9-[(3,4-difluorophenyl)methyl]-6,7,10,13,16,21,22,25,29-nonamethyl-8-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1076) (3S,9S,12S,18S,27S,30S,34R)-12-[2-[3-chloro-4-(trifluoromethyl)phenyl]ethyl]-18-(cyclohexylmethyl)-3,9,30-triisobutyl-1,6,6,7,16,19,22,25,31,34-decamethyl-27-[(1S)-1-methylpropyl]-1,4,7,10,13,16,19,22,25,28,31-undecazacyclotetratriacontane-2,5,8,11,14,17,20,23,26,29,32-undecone, (1077) (9'S,12'S,16'R,19'S,24a'S,30'S,36'S,38a'S)-9'-((S)-sec-butyl)-30'-(3-chloro-4-(trifluoromethyl)phenethyl)-19'-cyclopentyl-36'-(2-fluorobenzyl)-7',12',13',16',20',34',37'-heptamethyltetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone, (1078) (3S,6S,9S,12S,18S,27S,30S,34S)-12-[2-[3-chloro-4-(trifluoromethyl)phenyl]ethyl]-18-(cyclohexylmethyl)-9-[2-(4,4-difluoro-1-piperidyl)-2-oxo-ethyl]-30-isobutyl-3,6-diisopropyl-1,4,10,16,19,22,25,31-octamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (1079) (3S,6S,9S,12S,18S,27S,30S,34R)-6-benzyl-18-[(4-chlorophenyl)methyl]-12-[2-[3-chloro-4-(trifluoromethyl)phenyl]ethyl]-9-isobutyl-3-isopropyl-4,7,10,16,19,22,25,30,31,34-decamethyl-27-[(1S)-1-methylpropyl]-1,4,7,10,13,16,19,22,25,28,31-undecazacyclotetratriacontane-2,5,8,11,14,17,20,23,26,29,32-undecone, (1080) (5S,8S,11S,15S,18S,23aS,29S,35S,37aS)-8,18-di((S)-sec-butyl)-29-(3,5-difluoro-4-(trifluoromethyl)phenethyl)-11-isobutyl-N,N,5,6,12,16,19,33,36-nonamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1081) (3S,6S,9S,13S,16S,19S,22S,25S,31S,34S)-25-[2-[3-chloro-4-(trifluoromethyl)phenyl]ethyl]-31-(cyclohexylmethyl)-16-cyclopentyl-22-[2-(3,3-difluoro-1-piperidyl)ethyl]-9-isobutyl-N,N,3,4,10,14,17,19,23,29,32-undecamethyl-6-[(1S)-1-methylpropyl]-2,5,8,11,15,18,21,24,27,30,33-undecaoxo-1,4,7,10,14,17,20,23,26,29,32-undecazabicyclo[32.2.0]hexatriacontane-13-carboxamide, (1082) (6S,9S,13R,16S,21aS,27S,33S,35aS,39aS)-6-((S)-sec-butyl)-27-(3-chloro-4-(trifluoromethyl)phenethyl)-33-(cyclohexylmethyl)-9-isobutyl-16-isopropyl-10,13,17,31,34-pentamethyldocosahydro-1H,26H-spiro[azeto[1,2-j]dipyrrolo[1,2-g:1',2'-v][1,4,7,10,13,16,19,22,25,28,31]undecaazacyclotetratriacontine-19,1'-cyclopentan]-5,8,11,15,18,21,26,29,32,35,39(12H,20H,35aH,39aH)-undecaone, (1083) (9'S,12'S,16'R,19'S,24a'S,30'S,36'S,38a'S)-9'-((S)-sec-butyl)-30'-(3-chloro-4-(trifluoromethyl)phenethyl)-19'-cyclopentyl-7',12',13',16',20',34',37'-heptamethyl-36'-(3-methylbenzyl)tetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone, (1084) (3S,9S,12S,18S,27S,30S,34R)-18-[(4-chlorophenyl)methyl]-12-[2-[3-fluoro-4-(trifluoromethyl)phenyl]ethyl]-9,30-diisobutyl-3-isopropyl-1,6,6,7,16,19,22,25,31,34-decamethyl-27-[(1S)-1-methylpropyl]-1,4,7,10,13,16,19,22,25,28,31-undecazacyclotetratriacontane-2,5,8,11,14,17,20,23,26,29,32-undecone, (1085) (3S,6S,9S,12S,18S,27S,30S,34S)-6-benzyl-18-[(4-chlorophenyl)methyl]-3,9-diisobutyl-4,16,19,22,25,30,31-heptamethyl-27-[(1S)-1-methylpropyl]-34-(pyrrolidine-1-carbonyl)-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (1086) (3S,9S,18S,21S,28S,31S,34S)-31-benzyl-9-[(4-chlorophenyl)methyl]-28-isobutyl-7,10,13,16,21,22,29,32-octamethyl-8-[(1S)-1-methylpropyl]-3-[2-[4-(trifluoromethyl)phenyl]ethyl]-1,4,7,10,13,16,19,22,26,29,32-undecazabicyclo[32.3.0]heptatriacontane-2,5,8,11,14,17,20,23,27,30,33-undecone, (1087) (8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-9,15,18,21,24,30,34,37-octamethyl-26-[(1S)-1-methylpropyl]-8-[(5-methyl-3-pyridyl)methyl]-33-(piperidine-1-carbonyl)-6,9,12,15,18,21,24,27,30,34,37-undecazaspiro[4.33]octatriacontane-7,10,13,16,19,22,25,28,31,35,38-undecone, (1088) (3S,6R,9S,18S,21S,25R,28S,34S)-3-[2-[3-chloro-4-(trifluoromethyl)phenyl]ethyl]-28-cyclopentyl-6,7,10,13,16,21,22,25,29-nonamethyl-18-[(1S)-1-methylpropyl]-9-(m-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1089) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.4.0]octatriacontane-31,1'-cyclopentane]-2,5,8,11,14,17,20,23,27,30,33,36-dodecone, (1090) (3S,9S,18S,21S,25R,28S,34S)-9-(cyclohexylmethyl)-28-isobutyl-7,10,13,16,21,22,25,29-octamethyl-18-[(1S)-1-methylpropyl]-3-[2-[4-(trifluoromethyl)phenyl]ethyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1091) (5S,8S,11S,15S,18S,23aS,29S,35S,37aS)-8-((S)-sec-butyl)-35-(cyclohexylmethyl)-18-cyclopentyl-29-(3-fluoro-4-(trifluoromethyl)phenethyl)-11-isobutyl-5,6,12,16,19,33,36-heptamethyl-15-(pyrrolidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1092) (3S,6S,9S,12S,18S,27S,30S,34S)-6-benzyl-18-[(4-chlorophenyl)methyl]-9-(5,5-difluoropentyl)-3-isobutyl-4,7,16,19,22,25,30,31-octamethyl-27-[(1S)-1-methylpropyl]-34-(pyrrolidine-1-carbonyl)-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (1093) (3S,9S,18S,21S,25S,28S,34R)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-25-(piperidine-1-carbonyl)spiro[36-thia-1,4,7,10,13,16,19,22,26,29,32-undecazabicyclo[32.3.0]heptatriacontane-31,1'-cyclopentane]-2,5,8,11,14,17,20,23,27,30,33-undecone, (1094) (3S,9S,18S,21S,25S,28S,34S)-3-[2-[3-chloro-4-(trifluoromethyl)phenyl]ethyl]-28-cyclohexyl-21-isobutyl-7, 10,13,16,22,26,29-heptamethyl-18-[(1S)-1-methylpropyl]-9-(2-methylsulfonylethyl)-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1095) (3S,9S,12S,18S,27S,30S,34R)-18-(cyclohexylmethyl)-12-[2-[3-fluoro-4-(trifluoromethyl)phenyl]ethyl]-3,9,30-triisobutyl-6,6,7,16,19,22,25,31-octamethyl-27-[(1S)-1-methylpropyl]-1,4,7,10,13,16,19,22,25,28,31-undecazabicyclo[32.4.0]octatriacontane-2,5,8,11,14,17,20,23,26,29,32-undecone, (1096) (9'S,12'S,16'S,19'S,24a'S,26'R,30'S,36'S,38a'S)-9'-((S)-sec-butyl)-30'-(3-chloro-4-(trifluoromethyl)phenethyl)-19'-cyclohexyl-36'-(cyclohexylmethyl)-12'-isobutyl-7',13',17',20',34',37'-hexamethyl-26'-phenyl-16'-(piperidine-1-carbonyl)tetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone, (1097) (6'S,12'S,21'S,23a'S,31'R,34'S,39a'S)-21'-((S)-sec-butyl)-12'-(cyclohexylmethyl)-34'-isobutyl-10',13',16',19',31',35'-hexamethyl-6'-(4-(trifluoromethyl)phenethyl)tetracosahydrospiro[cyclopentane-1,37'-pyrido[1,2-a]pyrrolo[1,2-v][1,4,7,10,13,16,19,22,25,28,31]undecaazacyclotetratriacontin]-5',8',11',14',17',20',23',29',33',36',39'(23a'H,30'H,38'H)-undecaone, (1098) (5S,8S,11S,15S,18S,23aS,29S,35S,37aS)-8,18-di((S)-sec-butyl)-35-cyclopentyl-29-(3-fluoro-4-(trifluoromethyl)phenethyl)-11-isobutyl-5,6,12,16,19,33,36-heptamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1099) (5S,8S,11S,15S,18S,23aS,29S,35S,37aS)-8-((S)-sec-butyl)-18,35-dicyclopentyl-29-(3-fluoro-4-(trifluoromethyl)phenethyl)-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1100) (3S,9S,12S,18S,27S,30S,34S)-12-[(3-iodophenyl)methyl]-3,30-diisobutyl-9-[(2-methoxyphenyl)methyl]-1,6,6,7,16,19,22,25,31-nonamethyl-27-[(1S)-1-methylpropyl]-34-(piperidine-1-carbonyl)-18-(p-tolylmethyl)-1,4,7,10,13,16,19,22,25,28,31-undecazacyclotetratriacontane-2,5,8,11,14,17,20,23,26,29,32-undecone, (1101) (3S,9S,18S,21S,25S,28S,34S)-3-[2-[3-chloro-4-(trifluoromethyl)phenyl]ethyl]-9-(cyclohexylmethyl)-21-isobutyl-28-[(1R)-1-methoxyethyl]-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1102) (5S,8S,11S,15R,18S,23aS,29S,35S,37aS)-8-((S)-sec-butyl)-29-(3-chloro-4-(trifluoromethyl)phenethyl)-35-(cyclohexylmethyl)-5-(cyclopropoxymethyl)-11-isobutyl-18-isopropyl-6,12,15,19,33,36-hexamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1103) (5S,8S,11S,15S,18S,23aS,29S,32R,35S,37aS)-8-((S)-sec-butyl)-29-(3-chloro-4-(trifluoromethyl)phenethyl)-35-(cyclohexylmethyl)-18-isopropyl-5,6,11,12,16,19,32,33,36-nonamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1104) (3S,6S,9S,12S,18S,27S,30S,34S)-12-[2-[3-chloro-4-(trifluoromethyl)phenyl]ethyl]-18-(cyclohexylmethyl)-9-[2-(3,3-difluoroazetidin-1-yl)ethyl]-3-isopropyl-1,4,10,16,19,22,25,30,31-nonamethyl-27-[(1S)-1-methylpropyl]-34-(piperidine-1-carbonyl)-6-(2,2,2-trifluoroethyl)-1,4,7,10,13,16,19,22,25,28,31-undecazacyclotetratriacontane-2,5,8,11,14,17,20,23,26,29,32-undecone, (1105) (3S,6S,9S,12S,18S,27S,30S,34R)-6-benzyl-18-[(4-chlorophenyl)methyl]-12-[2-[3-fluoro-4-(trifluoromethyl)phenyl]ethyl]-9-isobutyl-3-isopropyl-4,7,10,16,19,22,25,30,31,34-decamethyl-27-[(1S)-1-methylpropyl]-1,4,7,10,13,16,19,22,25,28,31-undecazacyclotetratriacontane-2,5,8,11,14,17,20,23,26,29,32-undecone, (1106) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,6,12,16,33,36-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1107) (8S,11S,17S,26S,29S,33R,36S)-17-[(4-chlorophenyl)methyl]-8,36-diisobutyl-29-isopropyl-9,15,18,21,24,30,33,37-octamethyl-26-[(1S)-1-methylpropyl]-11-[2-[4-(trifluoromethyl)phenyl]ethyl]-6,9,12,15,18,21,24,27,30,34,37-undecazaspiro[4.33]octatriacontane-7,10,13,16,19,22,25,28,31,35,38-undecone, (1108) (3S,6S,9S,13S,16S,19S,22S,25,31S,34S)-25-[2-[3-chloro-4-(trifluoromethyl)phenyl]ethyl]-31-(cyclohexylmethyl)-16-cyclopentyl-22-[2-(3,3-difluoroazetidin-1-yl)-2-oxo-ethyl]-9-isobutyl-19-(methoxymethyl)-N,N,3,4,10,14,17,23,29,32-decamethyl-6-[(1S)-1-methylpropyl]-2,5,8,11,15,18,21,24,27,30,33-undecaoxo-1,4,7,10,14,17,20,23,26,29,32-undecazabicyclo[32.2.0]hexatriacontane-13-carboxamide, (1109) (3S,9S,18S,21S,25S,28S,31S,34S)-31-allyl-3-[2-[3-chloro-4-(trifluoromethyl)phenyl]ethyl]-9-(cyclohexylmethyl)-21-isobutyl-28-isopropyl-7,10,13,16,22,26,29,31-octamethyl-18-[(1S)-1-methylpropyl]-25-(piperidine-1-carbonyl)-1,4,7,10,13,16,19,22,26,29,32-undecazabicyclo[32.3.0]heptatriacontane-2,5,8,11,14,17,20,23,27,30,33-undecone, (1110) (4R,7S,10S,13S,16S,22S,31S,34S)-10-benzyl-22-[(4-chlorophenyl)methyl]-13-isobutyl-7-isopropyl-4,8,11,14,20,23,26,29-octamethyl-31-[(1S)-1-methylpropyl]-16-[2-[4-(trifluoromethyl)phenyl]ethyl]-1,5,8,11,14,17,20,23,26,29,32-undecazabicyclo[32.4.0]octatriacontane-2,6,9,12,15,18,21,24,27,30,33-undecone, (1111) (3S,9S,18S,21S,25R,28S,34S)-3-[2-[3-chloro-4-(trifluoromethyl)phenyl]ethyl]-9-(cyclohexylmethyl)-21-isobutyl-28-isopropyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopropane]-2,5,8,11,14,17,20,23,27,30,33-undecone, (1112) (5S,8S,11S,15S,18S,23aS,29S,35S,37aS)-15-(3-oxa-8-azabicyclo[3.2.1]octane-8-carbonyl)-8,18-di((S)-sec-butyl)-35-(cyclohexylmethyl)-29-(3-fluoro-4-(trifluoromethyl)phenethyl)-11-isobutyl-5,6,12,16,19,33,36-heptamethyldocosahydro-2H,4H-spiro[azeto[2,1-u]

pyrrolo[2,1-i][1,4,7,10,13,16,19,22,25,28,31]
undecaazacyclotetratriacontine-21,1'-cyclopentan]-4,7,
10,13,17,20,23,28,31,34,37(14H,22H)-undecaone, (1113) (3S,6S,9S,13S,16S,22S,25S,31S,34S)-25-[2-[3-chloro-4-(trifluoromethyl)phenyl]ethyl]-16-cyclohexyl-31-(cyclohexylmethyl)-9-isobutyl-3,4,10,14,17,23,29,32-octamethyl-6-[(1S)-1-methylpropyl]-13-(piperidine-1-carbonyl)-22-propyl-spiro[1,4,7,10,14,17,20,23,26,29,32-undecazabicyclo[32.2.0]hexatriacontane-19,1'-cyclopentane]-2,5,8,11,15,18,21,24,27,30,33-undecone, (1114) (5S,8S,11S,15S,18S,23aS,29S,35S,37aS)-8-((S)-sec-butyl)-29-(3-chloro-4-(trifluoromethyl)phenethyl)-11-(cyclobutylmethyl)-35-(cyclohexylmethyl)-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1115) (3S,9S,18S,21S,25S,28S,34S)-3-[2-[3-chloro-4-(trifluoromethyl)phenyl]ethyl]-28-cyclohexyl-9-(cyclohexylmethyl)-21-(isopentyloxymethyl)-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1116) (5S,8S,11S,15S,18S,23aS,29S,35S,37aS)-8-((S)-sec-butyl)-29-(3-chloro-4-(trifluoromethyl)phenethyl)-18-cyclopentyl-11-isobutyl-5,6,12,16,19,33,36-heptamethyl-15-(morpholine-4-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1117) (5S,8S,11S,15S,18S,23aS,29S,35S,37aS)-8-((S)-sec-butyl)-35-(cyclohexylmethyl)-18-cyclopentyl-29-(3-fluoro-4-(trifluoromethyl)phenethyl)-N,N,5,12,16,19,33,36-octamethyl-4,7,10,13,17,20,23,28,31,34,37-undecaoxo-11-pentyltetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1118) (7'S,16'S,19'S,23'S,26'S,31a'S,37'S,39a'R)-16'-((S)-sec-butyl)-37'-(3-chloro-4-(trifluoromethyl)phenethyl)-7'-(cyclohexylmethyl)-26'-isopropyl-8',11',14',19',20',24',27'-heptamethyl-23'-(piperidine-1-carbonyl)tetracosahydro-2'H,6'H-spiro[cyclopentane-1,29'-pyrido[2,1-o]pyrrolo[2,1-i][1,4,7,10,13,16,19,22,25,28,31]undecaazacyclotetratriacontin]-6',9',12',15',18',21',25',28',31',36',39'(22'H,30'H)-undecaone, (1119) (3S,6S,9S,12S,18S,27S,30S,34S)-6-benzyl-18-[(4-chlorophenyl)methyl]-3-isobutyl-9-(isopentyloxymethyl)-4,7,16,19,22,25,30,31-octamethyl-27-[(1S)-1-methylpropyl]-34-(pyrrolidine-1-carbonyl)-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (1120) (5S,8S,11S,15S,18S,23aS,29S,35S,37aS)-8,18-di((S)-sec-butyl)-29-(3-chloro-4-(trifluoromethyl)phenethyl)-33-ethyl-11-isobutyl-N,N,5,6,12,16,19,36-octamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1121) (9'S,12'S,16'S,19'S,24a'S,30'S,36'S,38a'S)-9'-((S)-sec-butyl)-30'-(3-chloro-4-(trifluoromethyl)phenethyl)-36'-(cyclohexylmethyl)-19'-isopropyl-7',12',13',17',20',34',37'-heptamethyl-16'-(piperidine-1-carbonyl)tetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone, (1122) (5S,8S,11S,15R,18S,23aS,29S,35S,37aS)-8-((S)-sec-butyl)-29-(3-chloro-4-(trifluoromethyl)phenethyl)-35-(cyclohexylmethyl)-5-((2-hydroxy-2-methylpropoxy)methyl)-11-isobutyl-18-isopropyl-6,12,15,19,33,36-hexamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1123) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-(5,5-difluoropentyl)-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1124) (3S,9S,18S,21S,25S,28S,34S)-3-[2-[3-chloro-4-(trifluoromethyl)phenyl]ethyl]-9-(cyclobutylmethyl)-21-isobutyl-28-isopropyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1125) (8S,11S,17S,26S,29S,33S,36S)-8-benzyl-11-[2-[3-chloro-4-(trifluoromethyl)phenyl]ethyl]-17-(cyclohexylmethyl)-36-isopropyl-15,18,21,24,29,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (1126) (1R,4S,7S,16S,22S,25S,31S,34R)-16-[(4-chlorophenyl)methyl]-25,31-diisobutyl-4-isopropyl-9,12,15,18,24,30-hexamethyl-7-[(1S)-1-methylpropyl]-22-[2-[4-(trifluoromethyl)phenyl]ethyl]spiro[3,6,9,12,15,18,21,24,27,30,33-undecazabicyclo[32.4.0]octatriacontane-28,1'-cyclopentane]-2,5,8,11,14,17,20,23,26,29,32-undecone, (1127) (3S,9S,12S,18S,27S,30S,34S)-12-[(3-iodophenyl)methyl]-3,30-diisobutyl-1,6,6,7,16,19,22,25,31-nonamethyl-27-[(1S)-1-methylpropyl]-34-(piperidine-1-carbonyl)-18-(p-tolylmethyl)-9-[[2-(trifluoromethyl)phenyl]methyl]-1,4,7,10,13,16,19,22,25,28,31-undecazacyclotetratriacontane-2,5,8,11,14,17,20,23,26,29,32-undecone, (1128) (3S,9S,18S,21S,25S,28S,34S)-3-[2-[3-chloro-4-(trifluoromethyl)phenyl]ethyl]-28-cyclobutyl-9-(cyclohexylmethyl)-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1129) (3S,6S,9S,13S,16S,22S,25S,31S,34S)-25-[(3-iodophenyl)methyl]-9,16-diisobutyl-3,4,10,14,19,19,20,29,32-nonamethyl-6-[(1S)-1-methylpropyl]-13-(piperidine-1-carbonyl)-31-(p-tolylmethyl)-22-[[2-(trifluoromethoxy)phenyl]methyl]-1,4,7,10,14,17,20,23,26,29,32-undecazabicyclo[32.2.0]hexatriacontane-2,5,8,11,15,18,21,24,27,30,33-undecone, (1130) (3S,9S,18S,21S,25S,28S,31R,34S)-3-[2-[3-chloro-4-(trifluoromethyl)phenyl]ethyl]-9-(cyclohexylmethyl)-31-ethyl-21-isobutyl-28-isopropyl-7,10,13,16,22,26,29,31-octamethyl-18-[(1S)-1-methylpropyl]-25-(piperidine- 1-carbonyl)-1,4,7,10,13,16,19,22,26,29,32-undecazabicyclo[32.3.0]heptatriacontane-2,5,8,11,14,17,20,23,27,30,33-undecone, (1131) (5S,8S,11S,15S,18S,23aS,29S,35S,37aS)-8,18-di((S)-sec-butyl)-29-(3-chloro-4-(trifluoromethyl)phenethyl)-11-isobutyl-N,N,5,6,12,16,19,33,36-nonamethyl-35-(4-methylbenzyl)-4,7,10,13,17,20,23,28,31,34,37-undecaoxo-22-propylhexatriacontahydro-2H-azeto[2,1-u]pyrrolo[2,1-i][1,4,7,10,13,16,19,22,25,28,31]undecaazacyclotetratriacontine-15-carboxamide, (1132) (5S,8S,11S,15S,18S,23aS,29S,35S,37aS)-8,18-di((S)-sec-butyl)-29-(3-chloro-4-(trifluoromethyl)phenethyl)-35-(cyclohexylmethyl)-5,6,12,16,19,33,36-heptamethyl-15-(piperidine-1-carbonyl)-11-propyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1133) (3S,9S,12S,18S,27S,30S,34R)-18-[(4-chlorophenyl)methyl]-27-cyclohexyl-2-[2-[3-fluoro-4-(trifluoromethyl)phenyl]ethyl]-3,9,30-triisobutyl-1,6,6,7,16,19,22,25,31,34-decamethyl-1,4,7,10,13,16,19,22,25,28,31-undecazacyclotetratriacontane-2,5,8,11,14,17,20,23,26,29,32-undecone, (1134) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-(3-methylbut-2-enyl)-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1135) (3S,6S,9S,13S,16S,19S,22S,25S,31S,34S)-25-[2-[3-chloro-4-(trifluoromethyl)phenyl]ethyl]-22-[2-(3,3-difluoro-1-piperidyl)ethyl]-9-isobutyl-N,N,3,4,10,14,17,19,23,29,32-undecamethyl-6,16-bis[(1S)-1-methylpropyl]-2,5,8,11,15,18,21,24,27,30,33-undecaoxo-31-(p-tolylmethyl)-1,4,7,10,14,17,20,23,26,29,32-undecazabicyclo[32.2.0]hexatriacontane-13-carboxamide, (1136) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,6,12,16,19,33,36-heptamethyl-15-(3,3,4,4-tetrafluoropyrrolidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1137) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-cyclopentyl-11-isobutyl-5,12,16,19,33,36-hexamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1138) (3S,9S,18S,21S,25S,28S,31R,34S)-3-[2-[3-chloro-4-(trifluoromethyl)phenyl]ethyl]-28-cyclohexyl-9-(cyclohexylmethyl)-21-isobutyl-31-isopropyl-7,10,13,16,22,26,29-heptamethyl-18-[(1S)-1-methylpropyl]-25-(piperidine-1-carbonyl)-1,4,7,10,13,16,19,22,26,29,32-undecazabicyclo[32.3.0]heptatriacontane-2,5,8,11,14,17,20,23,27,30,33-undecone, (1139) (3S,9S,18S,21S,25S,28S,34S,36R)-3-[2-[3-chloro-4-(trifluoromethyl)phenyl]ethyl]-28-cyclohexyl-36-ethoxy-7,10,13,16,22,26,29-heptamethyl-18-[(1S)-1-methylpropyl]-25-(pyrrolidine-1-carbonyl)-21-(2,2,2-trifluoroethyl)-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1140) (5S,8S,11S,15S,18S,23aS,29S,35S,37aS)-8-((S)-sec-butyl)-29-(3-chloro-4-(trifluoromethyl)phenethyl)-18,35-dicyclopentyl-12-ethyl-11-isobutyl-5,16,19,33,36-pentamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1141) (5S,8S,11S,15S,18S,23aS,29S,35S,37aS)-8,18-di((S)-sec-butyl)-29-(3-chloro-4-(trifluoromethyl)phenethyl)-11-(cyclopentylmethyl)-N,N,5,12,16,19,33,36-octamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1142) (5S,8S,11S,15S,18S,23aS,29S,35S,37aS)-8-((S)-sec-butyl)-29-(3-chloro-4-(trifluoromethyl)phenethyl)-18,35-dicyclopentyl-33-ethyl-11-isobutyl-5,6,12,16,19,36-hexamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1143) (5S,8S,11S,15S,18S,23aS,25R,29S,35S,37aS)-15-(azetidine-1-carbonyl)-8-((S)-sec-butyl)-35-(cyclohexylmethyl)-18-cyclopentyl-29-(3,5-difluoro-4-(trifluoromethyl)phenethyl)-25-ethoxy-11-isobutyl-5,6,12,16,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1144) (3S,9S,18S,21S,25S,28S,34S,36R)-21-cyclobutyl-28-cyclohexyl-9-(cyclohexylmethyl)-3-[2-[3,5-difluoro-4-(trifluoromethyl)phenyl]ethyl]-36-ethoxy-7,10,13,16,22,26,29-heptamethyl-18-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1145) (5S,8S,11S,15S,18S,23aS,29S,35S,37aS)-8-((S)-sec-butyl)-29-(3-chloro-4-(trifluoromethyl)phenethyl)-18,35-dicyclopentyl-11-(cyclopentylmethyl)-5,12,16,19,33,36-hexamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1146) (5S,8S,11S,15S,18S,23aS,29S,35S,37aS)-8,18-di((S)-sec-butyl)-29-(3-chloro-4-(trifluoromethyl)phenethyl)-12-ethyl-11-isobutyl-5,16,19,33,36-pentamethyl-15-(pyrrolidine-1-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1148) (5S,8S,11S,15S,18S,23aS,29S,35S,37aS)-8-((S)-sec-butyl)-29-(3-chloro-4-(trifluoromethyl)phenethyl)-18-cyclopentyl-12-ethyl-11-isobutyl-N,N,5,6,16,19,33,36-octamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1149) (3S,9S,18S,21S,25S,28S,34S,36R)-28-cyclohexyl-9-(cyclohexylmethyl)-3-[2-[3,5-difluoro-4-(trifluoromethyl)phenyl]ethyl]-36-ethoxy-7,10,13,16,22,26,29-heptamethyl-18-[(1S)-1-methylpropyl]-25-(pyrrolidine-1-carbonyl)-21-(2,2,2-trifluoroethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1150) (3S,9S,18S,21S,25S,28S,34S)-3-[2-[3-chloro-4-(trifluoromethyl)phenyl]ethyl]-28-cyclohexyl-9-(cyclohexylmethyl)-25-(3,3-dimethylpyrrolidine-1-carbonyl)-21-isobutyl-7,10,13,16,22,26,29-heptamethyl-18-I[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1151) (5S,8S,11S,15S,18S,23aS,29S,35S,37aS)-8,18-di((S)-sec-butyl)-29-(3-chloro-4-(trifluoromethyl)phenethyl)-33-ethyl-11-isobutyl-5,6,12,16,19,36-hexamethyl-15-(morpholine-4-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1152) (5S,8S,11S,15S,18S,23aS,29S,35S,37aS)-8-((S)-sec-butyl)-18-cyclopentyl-36-ethyl-29-(3-fluoro-4-(trifluoromethyl)phenethyl)-11-isobutyl-N,N,5,6,12,16,19,33-octamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1153) (3S,6S,9S,13R,16S,22S,25S,31S,34S)-25-[2-[3-chloro-4-(trifluoromethyl)phenyl]ethyl]-16-cyclopentyl-9-isobutyl-3,4,10,13,17,22,23,29,32-nonamethyl-6-[(1S)-1-methylpropyl]-31-(p-tolylmethyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (1154) (5S,8S,11S,15S,18S,23aS,29S,35S,37aS)-15-(3-oxa-8-azabicyclo[3.2.1]octane-8-carbonyl)-8-((S)-sec-butyl)-29-(3-chloro-4-(trifluoromethyl)phenethyl)-18-cyclopentyl-11-isopentyl-5,6,12,16,19,33,36-heptamethyl-35-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1155) (3S,6S,9S,13S,16S,22S,25S,31S,34S)-25-[(2-bromo-5-iodo-phenyl)methyl]-22-butyl-9-ethyl-16-isobutyl-31-[(4-methoxyphenyl)methyl]-3,4,10,14,19,19,20,29,32-nonamethyl-6-[(1S)-1-methylpropyl]-13-(piperidine-1-carbonyl)-1,4,7,10,14,17,20,23,26,29,32-undecazabicyclo[32.2.0]hexatriacontane-2,5,8,11,15,18,21,24,27,30,33-undecone, (1156) (3S,6S,9S,13S,16S,22S,25S,31S,34S)-22-butyl-25-[(3-chloro-5-iodo-phenyl)methyl]-9-ethyl-16-isobutyl-31-[(4-methoxyphenyl)methyl]-3,4,10,14,19,19,20,29,32-nonamethyl-6-[(1S)-1-methylpropyl]-13-(piperidine-1-carbonyl)-1,4,7,10,14,17,20,23,26,29,32-undecazabicyclo[32.2.0]hexatriacontane-2,5,8,11,15,18,21,24,27,30,33-undecone, (1157) (3S,9S,18S,21S,25S,28S,31S,34S)-3-[2-[3-chloro-4-(trifluoromethyl)phenyl]ethyl]-28-cyclohexyl-9-(cyclohexylmethyl)-21-isobutyl-31-isopropyl-7,10,13,16,22,26,29-heptamethyl-18-[(1S)-1-methylpropyl]-25-(piperidine-1-carbonyl)-1,4,7,10,13,16,19,22,26,29,32-undecazabicyclo[32.3.0]heptatriacontane-2,5,8,11,14,17,20,23,27,30,33-undecone, (1158) (5S,8S,11S,15S,18S,23aS,25R,29S,35S,37aS)-15-(azetidine-1-carbonyl)-8-((S)-sec-butyl)-29-(3-chloro-4-(trifluoromethyl)phenethyl)-35-(cyclohexylmethyl)-18-cyclopentyl-25-ethoxy-11-isobutyl-5,6,12,16,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1159) (5S,8S,11S,15S,18S,23aS,29S,35S,37aS)-8,18-di((S)-sec-butyl)-29-(3-chloro-4-(trifluoromethyl)phenethyl)-33-ethyl-11-isobutyl-5,6,12,16,19,36-hexamethyl-15-(pyrrolidine-1-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1160) (3S,9S,18S,21S,25S,28S,34S)-28-cyclohexyl-9-(cyclohexylmethyl)-3-[2-[3,5-difluoro-4-(trifluoromethyl)phenyl]ethyl]-36,36-difluoro-7,10,13,16,22,26,29-heptamethyl-18-[(1S)-1-methylpropyl]-21-propyl-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1161) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,6,12,19,33,36-hexamethyl-15-(4-methylpiperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1162) (3S,9S,18S,21S,25S,28S,34S,36R)-9-(cyclohexylmethyl)-28-cyclopentyl-3-[2-[3,5-difluoro-4-(trifluoromethyl)phenyl]ethyl]-36-ethoxy-21-isobutyl-7,10,13,16,22,26,29-heptamethyl-18-1[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1163) (3S,9S,18S,21S,25S,28S,34S)-3-[2-[3-chloro-4-(trifluoromethyl)phenyl]ethyl]-28-cyclohexyl-9-(cyclohexylmethyl)-36,36-difluoro-21-isobutyl-7,10,13,16,22,26,29-heptamethyl-18-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclobutane]-2,5,8,11,14,17,20,23,27,30,33-undecone, (1164) (5S,8S,11S,15S,18S,23aS,29S,35S,37aS)-8-((S)-sec-butyl)-35-(cyclohexylmethyl)-18-cyclopentyl-29-(3-fluoro-4-(trifluoromethyl)phenethyl)-11-isobutyl-N,N,5,12,16,19,33,36-octamethyl-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1165) (3S,9S,18S,21S,25S,28S,34S)-28-cyclohexyl-9-(cyclohexylmethyl)-3-[2-[3,5-difluoro-4-(trifluoromethyl)phenyl]ethyl]-21-isobutyl-7,10,13,16,22,26,29-heptamethyl-18-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclobutane]-2,5,8,11,14,17,20,23,27,30,33-undecone, (1166) (3S,9S,18S,21S,25S,28S,34S)-9-(cyclohexylmethyl)-28-cyclopentyl-3-[2-[3,5-difluoro-4-(trifluoromethyl)phenyl]ethyl]-36,36-difluoro-21-isobutyl-7,10,13,16,22,26,29-heptamethyl-18-[(1S)-1-methylpropyl]-25-

(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1167) (5S,8S,11S,15S,18S,23aS,29S,35S,37aS)-15-(3-oxa-8-azabicyclo[3.2.1]octane-8-carbonyl)-8-((S)-sec-butyl)-29-(3-chloro-4-(trifluoromethyl)phenethyl)-18-cyclopentyl-12-ethyl-11-isobutyl-5,16,19,33,36-pentamethyl-35-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1168) (3S,9S,18S,21S,25S,28S,34S)-3-[2-[3-chloro-4-(trifluoromethyl)phenyl]ethyl]-9-(cyclohexylmethyl)-21-isobutyl-7,10,13,16,22,29-hexamethyl-18,28-bis[(1S)-1-methylpropyl]-25-(3,3,4,4-tetrafluoropyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1169) (3S,9S,12S,18S,27S,30S,34S)-12-[(3-iodophenyl)methyl]-3,30-diisobutyl-18-[(4-methoxyphenyl)methyl]-1,6,6,7,16,19,22,25,31-nonamethyl-27-[(1S)-1-methylpropyl]-34-(piperidine-1-carbonyl)-9-prop-2-ynyl-1,4,7,10,13,16,19,22,25,28,31-undecazacyclotetratriacontane-2,5,8,11,14,17,20,23,26,29,32-undecone,
(1170) (5S,8S,11S,15S,18S,23aS,29S,35S,37aS)-8-((S)-sec-butyl)-35-(cyclohexylmethyl)-18-cyclopentyl-29-(3,5-difluoro-4-(trifluoromethyl)phenethyl)-11-isobutyl-N,N,5,6,12,16,19,33,36-nonamethyl-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide,
(1171) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-cyclopentyl-11-isopentyl-5,12,16,19,33,36-hexamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1172) (3S,9S,18S,21S,25S,28S,34S)-3-[2-[3-chloro-4-(trifluoromethyl)phenyl]ethyl]-9-(cyclohexylmethyl)-21-isobutyl-7,10,13,16,22,29-hexamethyl-25-(4-methylpiperidine-1-carbonyl)-18,28-bis[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1173) (5S,8S,11S,15S,18S,23aS,29S,35S,37aS)-8-((S)-sec-butyl)-29-(3-chloro-4-(trifluoromethyl)phenethyl)-18,35-dicyclopentyl-11-(cyclopentylmethyl)-5,6,12,16,19,33,36-heptamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1174) (5S,8S,11S,15S,18S,21R,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,6,12,16,19,21,33,36-octamethyl-15-(piperidine-1-carbonyl)tetracosahydro-2H-azeto[2,1-u]pyrrolo[2,1-i][1,4,7,10,13,16,19,22,25,28,31]undecaazacyclotetratriacontin-4,7,10,13,17,20,23,28,31,34,37(14H)-undecaone,
(1175) (5S,8S,11S,15S,18S,23aS,29S,35S,37aS)-8,18-di((S)-sec-butyl)-29-(3,5-difluoro-4-(trifluoromethyl)phenethyl)-36-ethyl-11-isobutyl-5,6,12,16,19,33-hexamethyl-15-(pyrrolidine-1-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1176) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-cyclopentyl-11-(cyclopentylmethyl)-5,12,16,19,33,36-hexamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1177) (3S,6S,9S,13S,16S,22S,25S,31S,34S)-25-[(5-bromo-2-fluoro-phenyl)methyl]-22-butyl-9-ethyl-16-isobutyl-31-[(4-methoxyphenyl)methyl]-3,4,10,14,19,19,20,29,32-nonamethyl-6-[(1S)-1-methylpropyl]-13-(piperidine-1-carbonyl)-1,4,7,10,14,17,20,23,26,29,32-undecazabicyclo[32.2.0]hexatriacontane-2,5,8,11,15,18,21,24,27,30,33-undecone,
(1178) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,6,12,16,19,33,36-heptamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1179) (3S,9S,18S,21S,25S,28S,34S)-3-[2-[3-chloro-4-(trifluoromethyl)phenyl]ethyl]-28-cyclohexyl-9-(cyclohexylmethyl)-36,36-difluoro-21-isobutyl-7,10,13,16,22,26,29-heptamethyl-18-[(1S)-1-methylpropyl]-25-(3-oxa-8-azabicyclo[3.2.1]octane-8-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1180) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-25-(oxazolidine-3-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1181) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,6,12,16,19,33,36-heptamethyl-15-(4-(oxetan-3-yl)piperazine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1182) (3S,9S,18S,21S,25S,28S,34S)-3-[2-[3-chloro-4-(trifluoromethyl)phenyl]ethyl]-28-cyclohexyl-36,36-difluoro-7,10,13,16,22,26,29-heptamethyl-18-[(1S)-1-methylpropyl]-25-(morpholine-4-carbonyl)-21-(2,2,2-trifluoroethyl)-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1183) (5S,8S,11S,15S,18S,23aS,29S,35S,37aS)-8,18-di((S)-sec-butyl)-29-(3-chloro-4-(trifluoromethyl)phenethyl)-11-(cyclopentylmethyl)-5,6,12,16,19,33,36-heptamethyl-15-(pyrrolidine-1-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1184) (3S,9S,12S,18S,27S,30S,34S)-18-benzyl-12-[(3-iodophenyl)methyl]-3,30-diisobutyl-1,6,6,7,16,19,22,25,31-nonamethyl-27-1[(1S)-1-methylpropyl]-34-(piperidine-1-carbonyl)-9-prop-2-ynyl-1,4,7,10,13,16,19,22,25,28,31-undecazacyclotetratriacontane-2,5,8,11,14,17,20,23,26,29,32-undecone, (1185) (6'S,12'S,21'S,24'S,27a'R,33'S,38a'S)-21'-((S)-sec-butyl)-6'-(3-chloro-4-(trifluoromethyl)phenethyl)-33'-cyclohexyl-12'-(cyclohexylmethyl)-24'-isobutyl-10',13',16',19',25',34'-hexamethyltetracosahydro-5'H-spiro[cyclopentane-1,36'-dipyrrolo[1,2-e1:1',2'-v][1,4,7,10,13,16,19,22,25,28,31]undecaazacyclotetratriacontin]-5',8',11',14',17',20',23',26',32',35',38'(27'H,37'H)-undecaone, (1186) (3S,9S,12S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,12,13,16,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30-undecone, (1187) (3S,6S,9S,13S,16S,22S,25S,31S,34S)-22-butyl-25-[(2,6-difluorophenyl)methyl]-9-ethyl-16-isobutyl-31-I[(4-methoxyphenyl)methyl]-3,4,10,14,19,19,20,29,32-nonamethyl-6-[(1S)-1-methylpropyl]-13-(piperidine-1-carbonyl)-1,4,7,10,14,17,20,23,26,29,32-undecazabicyclo[32.2.0]hexatriacontane-2,5,8,11,15,18,21,24,27,30,33-undecone, (1188) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,6,12,19,33,36-hexamethyl-15-(oxazolidine-3-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1189) (3S,9S,18S,21S,25S,28S,34S)-3-[2-[3-chloro-4-(trifluoromethyl)phenyl]ethyl]-28-cyclohexyl-9-(cyclohexylmethyl)-22-ethyl-21-isobutyl-7,10,13,16,26,29-hexamethyl-18-[(1S)-1-methylpropyl]-25-(morpholine-4-carbonyl)spiro[1,4,7,10,13,16,19,22,26,29,32-undecazabicyclo[32.3.0]heptatriacontane-31,1'-cyclopentane]-2,5,8,11,14,17,20,23,27,30-undecone, (1190) (5S,8S,11S,15S,18S,23aS,29S,35S,37aS)-8,18-di((S)-sec-butyl)-29-(3-chloro-4-(trifluoromethyl)phenethyl)-12-ethyl-11-isobutyl-5,6,16,19,33,36-hexamethyl-15-(pyrrolidine-1-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1191) (3S,9S,18S,21S,25S,28S,34S)-3-[2-[3-chloro-4-(trifluoromethyl)phenyl]ethyl]-9-(cyclohexylmethyl)-21-isobutyl-7,10,13,16,22,29-hexamethyl-18,28-bis[(1S)-1-methylpropyl]-25-[4-(oxetan-3-yl)piperazine-1-carbonyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1192) (3S,9S,18S,21S,25S,28S,34S)-28-cyclohexyl-9-(cyclohexylmethyl)-3-[2-[3,5-difluoro-4-(trifluoromethyl)phenyl]ethyl]-36,36-difluoro-21-isobutyl-7,10,13,16,22,26,29-heptamethyl-18-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclobutane]-2,5,8,11,14,17,20,23,27,30,33-undecone, (1193) (5S,8S,11S,15S,18S,23aS,29S,35S,37aS)-15-(3-oxa-8-azabicyclo[3.2.1]octane-8-carbonyl)-8-((S)-sec-butyl)-29-(3-chloro-4-(trifluoromethyl)phenethyl)-18-cyclopentyl-12-ethyl-11-isobutyl-5,6,16,19,33,36-hexamethyl-35-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1194) (3S,9S,18S,21S,25S,28S,34S)-3-[2-[3-chloro-4-(trifluoromethyl)phenyl]ethyl]-28-cyclohexyl-9-(cyclohexylmethyl)-36,36-difluoro-21-isobutyl-7,10,13,16,22,26,29-heptamethyl-18-[(1S)-1-methylpropyl]-25-(morpholine-4-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1195) (3S,6S,9S,13S,16S,22S,25S,31S,34S)-25-[(5-bromo-2-methyl-phenyl)methyl]-22-butyl-9-ethyl-16-isobutyl-31-[(4-methoxyphenyl)methyl]-3,4,10,14,19,19,20,29,32-nonamethyl-6-[(1S)-1-methylpropyl]-13-(piperidine-1-carbonyl)-1,4,7,10,14,17,20,23,26,29,32-undecazabicyclo[32.2.0]hexatriacontane-2,5,8,11,15,18,21,24,27,30,33-undecone, (1196) (3S,9S,18S,21S,25S,28S,34S)-3-[2-[3-chloro-4-(trifluoromethyl)phenyl]ethyl]-28-cyclohexyl-36,36-difluoro-7,10,13,16,22,26,29-heptamethyl-18-[(1S)-1-methylpropyl]-25-(pyrrolidine-1-carbonyl)-21-(2,2,2-trifluoroethyl)-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1197) (3S,9S,18S,21S,25S,28S,34S)-28-cyclohexyl-3-[2-[3,5-difluoro-4-(trifluoromethyl)phenyl]ethyl]-7,10,13,16,22,26,29-heptamethyl-18-[(1S)-1-methylpropyl]-21-propyl-9-(p-tolylmethyl)-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1198) (5S,8S,11S,15S,18S,23aS,29S,35S,37aS)-15-(azetidine-1-carbonyl)-8-((S)-sec-butyl)-29-(3-chloro-4-(trifluoromethyl)phenethyl)-35-(cyclohexylmethyl)-18-cyclopentyl-12-ethyl-11-isobutyl-5,6,16,19,33,36-hexamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1199) (5S,8S,11S,15S,18S,23aS,29S,35S,37aS)-15-(azetidine-1-carbonyl)-8-((S)-sec-butyl)-29-(3-chloro-4-(trifluoromethyl)phenethyl)-35-(cyclohexylmethyl)-18-cyclopentyl-11-(cyclopentylmethyl)-5,6,12,16,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1200) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,6,12,19,33,36-hexamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1201) (5S,8S,11S,15S,18S,23aS,25R,29S,35S,37aS)-8-((S)-sec-butyl)-35-(cyclohexylmethyl)-18-cyclopentyl-29-(3,5-difluoro-4-(trifluoromethyl)phenethyl)-25-ethoxy-11-isobutyl-N,N,5,6,12,16,19,33,36-nonamethyl-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1202) (3S,9S,12S,18S,27S,30S,34S)-9-butyl-8-[(4-chlorophenyl)methyl]-12-[(3-iodophenyl)methyl]-3,30-diisobutyl-1,6,6,7,12,16,19,22,25,31-decamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (1203) (3S,9S,18S,21S,25S,28S,34S)-3-[2-[3-chloro-4-(trifluoromethyl)phenyl]ethyl]-28-cyclohexyl-9-(cyclohexylmethyl)-7-ethyl-21-isobutyl-10,13,16,22,26,29-hexamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1204) (3S,9S,18S,21S,25S,28S,34S,36R)-3-[2-[3-chloro-4-(trifluoromethyl)phenyl]ethyl]-21-cyclobutyl-28-cyclohexyl-9-(cyclohexylmethyl)-36-ethoxy-7,10,13,16,22,26,29-heptamethyl-18-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1205) (5S,8S,11S,15S,18S,23aS,29S,35S,37aS)-8-((S)-sec-butyl)-35-(cyclohexylmethyl)-18-cyclopentyl-33-ethyl-29-(3-fluoro-4-(trifluoromethyl)phenethyl)-11-isobutyl-N,N,5,6,12,16,19,36-octamethyl-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1206) (3S,9S,18S,21S,25S,28S,34S,36R)-3-[2-[3-chloro-4-(trifluoromethyl)phenyl]ethyl]-28-cyclohexyl-36-ethoxy-7,10,13,16,22,26,29-heptamethyl-18-[(1S)-1-methylpropyl]-25-(morpholine-4-carbonyl)-21-(2,2,2-trifluoroethyl)-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1207) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-25-(3,3,4,4-tetrafluoropyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1208) (5S,8S,11S,15S,18S,23aS,29S,35S,37aS)-8-((S)-sec-butyl)-29-(3-chloro-4-(trifluoromethyl)phenethyl)-18,35-dicyclopentyl-12-ethyl-11-isobutyl-5,6,16,19,33,36-hexamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1209) (5S,8S,11S,15S,18S,23aS,29S,35S,37aS)-8,18-di((S)-sec-butyl)-29-(3,5-difluoro-4-(trifluoromethyl)phenethyl)-36-ethyl-11-isobutyl-5,6,12,16,19,33-hexamethyl-35-(4-methylbenzyl)-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1210) (5S,8S,11S,15S,18S,23aS,25R,29S,35S,37aS)-8,18-di((S)-sec-butyl)-29-(3,5-difluoro-4-(trifluoromethyl)phenethyl)-25-ethoxy-11-isobutyl-5,6,12,16,19,33,36-heptamethyl-15-(pyrrolidine-1-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1211) (5S,8S,11S,15S,18S,21S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,6,12,16,19,21,33,36-octamethyl-15-(piperidine-1-carbonyl)tetracosahydro-2H-azeto[2,1-u]pyrrolo[2,1-i][1,4,7,10,13,16,19,22,25,28,31]undecaazacyclotetratriacontin-4,7,10,13,17,20,23,28,31,34,37(14H)-undecaone, (1212) (3S,6S,9S,13S,16S,22S,25S,31S,34S)-25-[(5-bromo-2-chloro-phenyl)methyl]-22-butyl-9-ethyl-16-isobutyl-31-[(4-methoxyphenyl)methyl]-3,4,10,14,19,19,20,29,32-nonamethyl-6-[(1S)-1-methylpropyl]-13-(piperidine-1-carbonyl)-1,4,7,10,14,17,20,23,26,29,32-undecazabicyclo[32.2.0]hexatriacontane-2,5,8,11,15,18,21,24,27,30,33-undecone, (1213) (5S,8S,11S,15R,18S,23aS,29S,35S,37aS)-8-((S)-sec-butyl)-29-(3-chloro-4-(trifluoromethyl)phenethyl)-18-cyclopentyl-11-isobutyl-5,6,12,15,33,36-hexamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1214) (5S,8S,11S,15S,18S,23aS,29S,35S,37aS)-15-(3-oxa-8-azabicyclo[3.2.1]octane-8-carbonyl)-8-((S)-sec-butyl)-29-(3-chloro-4-(trifluoromethyl)phenethyl)-35-(cyclohexylmethyl)-11-isobutyl-18-isopropyl-5,6,12,19,33,36-hexamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1215) (5S,8S,11S,15S,18S,23aS,29S,35S,37aS)-15-(3-oxa-8-azabicyclo[3.2.1]octane-8-carbonyl)-8-((S)-sec-butyl)-18-cyclopentyl-29-(3,5-difluoro-4-(trifluoromethyl)phenethyl)-36-ethyl-11-isobutyl-5,6,12,16,19,33-hexamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1216) (3S,9S,12S,18S,27S,30S,34S)-12-[(5-bromo-2-thienyl)methyl]-9-butyl-8-[(4-chlorophenyl)methyl]-3,30-diisobutyl-1,6,6,7,16,19,22,25,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (1217) (5S,8S,11S,15S,18S,23aS,29S,35S,37aS)-8-((S)-sec-butyl)-18-cyclopentyl-29-(3,5-difluoro-4-(trifluoromethyl)phenethyl)-36-ethyl-11-isobutyl-N,N,5,6,12,16,19,33-octamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1218) (5S,8S,11S,15R,18S,23aS,29S,35S,37aS)-8-((S)-sec-butyl)-29-(3-chloro-4-(trifluoromethyl)phenethyl)-18-cyclopentyl-33-ethyl-11-isobutyl-5,6,12,15,19,36-hexamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1219) (3S,9S,12S,18S,27S,30S,34S)-12-[(3-iodophenyl)methyl]-3,30-diisobutyl-1,6,6,7,16,19,22,25,31-nonamethyl-27-[(1S)-1-methylpropyl]-34-(piperidine-1-carbonyl)-9-prop-2-ynyl-18-[[4-(trifluoromethoxy)phenyl]

methyl]-1,4,7,10,13,16,19,22,25,28,31-undecazacyclotetratriacontane-2,5,8,11,14,17,20,23,26, 29,32-undecone,
(1220) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-cyclopentyl-12-ethyl-11-isobutyl-5,6,16,19,33,36-hexamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7, 10,13,17,20,23,28,31,34,37(14H,22H)-undecaone,
(1221) (5S,8S,11S,15R,18S,21S,23aS,29S,35S,37aS)-8-((S)-sec-butyl)-29-(3-chloro-4-(trifluoromethyl)phenethyl)-18-cyclopentyl-11-isobutyl-5,6,12,15,19,21,33,36-octamethyl-35-(4-methylbenzyl)tetracosahydro-2H-azeto[2,1-u]pyrrolo[2,1-i][1,4,7,10,13,16,19,22,25,28,31]undecaazacyclotetratriacontin-4,7,10,13,17,20,23,28,31, 34,37(14H)-undecaone,
(1222) (5S,8S,11S,15R,18S,21R,23aS,29S,35S,37aS)-8-((S)-sec-butyl)-29-(3-chloro-4-(trifluoromethyl)phenethyl)-18-cyclopentyl-11-isobutyl-5,6,12,15,19,21,33,36-octamethyl-35-(4-methylbenzyl)tetracosahydro-2H-azeto[2,1-u]pyrrolo[2,1-i][1,4,7,10,13,16,19,22,25,28,31]undecaazacyclotetratriacontin-4,7,10,13,17,20,23,28,31, 34,37(14H)-undecaone,
(1223) (5S,8S,11S,15S,18S,23aS,29S,35S,37aS)-8-((S)-sec-butyl)-29-(3-chloro-4-(trifluoromethyl)phenethyl)-18,35-dicyclopentyl-11-isopentyl-5,12,16,19,33,36-hexamethyl-15-(morpholine-4-carbonyl)docosahydro-2H, 4H-spiro[azeto[2,1-u]pyrrolo[2,1-i][1,4,7,10,13,16,19, 22,25,28,31]undecaazacyclotetratriacontine-21,1'-cyclopentan]-4,7,10,13,17,20,23,28,31,34,37(14H,22H)-undecaone,
(1224) (3S,9S,18S,21S,25S,28S,34S,36R)-28-cyclohexyl-3-[2-[3,5-difluoro-4-(trifluoromethyl)phenyl]ethyl]-36-ethoxy-7,10,13,16,22,26,29-heptamethyl-18-[(1S)-1-methylpropyl]-21-propyl-9-(p-tolylmethyl)-25-(pyrrolidine-1-carbonyl)spiro[1,4,7,10,13,16,19,22,26, 29,32-undecazabicyclo[32.3.0]heptatriacontane-31,1'-cyclopentane]-2,5,8,11,14,17,20,23,27,30,33-undecone,
(1225) (5S,8S,11S,15R,18S,23aS,29S,35S,37aS)-29-(3-chloro-4-(trifluoromethyl)phenethyl)-18-cyclopentyl-11-isobutyl-5,6,8,12,15,19,33,36-octamethyl-35-(4-methylbenzyl)docosahydro-2H,4H-spiro[azeto[2, 1-i][1,4,7,10,13,16,19,22,25,28,31]undecaazacyclotetratriacontine-21,1'-cyclopentan]-4,7, 10,13,17,20,23,28,31,34,37(14H,22H)-undecaone,
(1226) (3S,6S,9S,13S,16S,22S,25S,31S,34S)-22-butyl-9-ethyl-25-[(3-fluoro-5-iodo-phenyl)methyl]-16-isobutyl-31-[(4-methoxyphenyl)methyl]-3,4,10,14,19,19,20,29, 32-nonamethyl-6-[(1S)-1-methylpropyl]-13-(piperidine-1-carbonyl)-1,4,7,10,14,17,20,23,26,29,32-undecazabicyclo[32.2.0]hexatriacontane-2,5,8,11,15,18, 21,24,27,30,33-undecone,
(1227) (3S,9S,18S,21S,25S,28S,34S)-3-[2-[3-chloro-4-(trifluoromethyl)phenyl]ethyl]-28-cyclohexyl-9-(cyclohexylmethyl)-13-ethyl-21-isobutyl-7,10,16,22,26,29-hexamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1228) (3S,9S,18S,21S,25S,28S,34S)-28-cyclohexyl-9-(cyclohexylmethyl)-3-[2-[3,5-difluoro-4-(trifluoromethyl)phenyl]ethyl]-7,10,13,16,22,26,29-heptamethyl-18-[(1S)-1-methylpropyl]-25-(pyrrolidine-1-carbonyl)-21-(2,2,2-trifluoroethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1229) (3S,9S,18S,21S,25S,28S,34S)-3-[2-[3-chloro-4-(trifluoromethyl)phenyl]ethyl]-28-cyclohexyl-9-(cyclohexylmethyl)-25-(3,3,4,4,5,5-hexafluoropiperidine-1-carbonyl)-21-isobutyl-7,10,13,16,22,26,29-heptamethyl-18-[(1S)-1-methylpropyl]spiro[1,4,7,10,13,16,19,22,26,29, 32-undecazabicyclo[32.3.0]heptatriacontane-31,1'-cyclopentane]-2,5,8,11,14,17,20,23,27,30,33-undecone,
(1230) (3S,6S,9S,13S,16S,22S,25S,31S,34S)-31-[(4-fluorophenyl)methyl]-25-[(3-iodophenyl)methyl]-9,16-diisobutyl-3,4,10,14,19,19,20,29,32-nonamethyl-6-[(1S)-1-methylpropyl]-13-(piperidine-1-carbonyl)-22-prop-2-ynyl-1,4,7,10,14,17,20,23,26,29,32-undecazabicyclo[32.2.0]hexatriacontane-2,5,8,11,15,18,21,24,27,30,33-undecone,
(1231) (5S,8S,11S,15S,18S,23aS,25R,29S,35S,37aS)-8-((S)-sec-butyl)-35-(cyclohexylmethyl)-18-cyclopentyl-25-ethoxy-29-(3-fluoro-4-(trifluoromethyl)phenethyl)-11-isobutyl-N,N,5,6,12,16,19,33,36-nonamethyl-4,7,10, 13,17,20,23,28,31,34,37-undecaoxotetratriacontahydro-2H,4H-spiro[azeto[2,1-u]pyrrolo[2,1-i][1,4,7,10,13,16, 19,22,25,28,31]undecaazacyclotetratriacontine-21,1'-cyclopentane]-15-carboxamide,
(1232) (3S,9S,18S,21S,25S,28S,34S)-3-[2-[3-chloro-4-(trifluoromethyl)phenyl]ethyl]-28-cyclohexyl-9-(cyclohexylmethyl)-36,36-difluoro-7,10,13,16,22,26,29-heptamethyl-18-[(1S)-1-methylpropyl]-21-propyl-25-(pyrrolidine-1-carbonyl)spiro[1,4,7,10,13,16,19,22,26, 29,32-undecazabicyclo[32.3.0]heptatriacontane-31,1'-cyclopentane]-2,5,8,11,14,17,20,23,27,30,33-undecone,
(1233) (5S,8S,11S,15S,18S,23aS,29S,35S,37aS)-8,18-di((S)-sec-butyl)-29-(3-chloro-4-(trifluoromethyl)phenethyl)-12-ethyl-11-isobutyl-5,16,19,33,36-pentamethyl-15-(morpholine-4-carbonyl)-35-(4-(trifluoromethyl)benzyl)docosahydro-2H,4H-spiro[azeto[2,1-u]pyrrolo[2, 1-i][1,4,7,10,13,16,19,22,25,28,31]undecaazacyclotetratriacontine-21,1'-cyclopentan]-4,7, 10,13,17,20,23,28,31,34,37(14H,22H)-undecaone,
(1234) (5S,8S,11S,15S,18S,23aS,29S,35S,37aS)-8,18-di((S)-sec-butyl)-29-(3-chloro-4-(trifluoromethyl)phenethyl)-12-ethyl-11-isobutyl-5,6,16,19,33,36-hexamethyl-15-(morpholine-4-carbonyl)-35-(4-(trifluoromethyl)benzyl)docosahydro-2H,4H-spiro[azeto[2,1-u]pyrrolo[2, 1-i][1,4,7,10,13,16,19,22,25,28,31]undecaazacyclotetratriacontine-21,1'-cyclopentan]-4,7, 10,13,17,20,23,28,31,34,37(14H,22H)-undecaone,
(1235) (5S,8S,11S,15S,18S,23aS,29S,35S,37aS)-15-(3-oxa-8-azabicyclo[3.2.1]octane-8-carbonyl)-8-((S)-sec-butyl)-29-(3-chloro-4-(trifluoromethyl)phenethyl)-35-(cyclohexylmethyl)-11-isobutyl-18-isopropyl-5,6,12,16,19,33, 36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7, 10,13,17,20,23,28,31,34,37(14H,22H)-undecaone,
(1236) (5S,8S,11S,15S,18S,23aS,29S,35S,37aS)-15-(3-oxa-8-azabicyclo[3.2.1]octane-8-carbonyl)-8-((S)-sec-butyl)-29-(3-chloro-4-(trifluoromethyl)phenethyl)-18-cyclopentyl-36-ethyl-11-isobutyl-5,6,12,16,19,33-hexamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7, 10,13,17,20,23,28,31,34,37(14H,22H)-undecaone,
(1237) (5S,8S,11S,15S,18S,23aS,29S,35S,37aS)-8-((S)-sec-butyl)-29-(3-chloro-4-(trifluoromethyl)phenethyl)-18,35-dicyclopentyl-11-isopentyl-5,6,12,16,19,33,36-heptamethyl-15-(morpholine-4-carbonyl)docosahydro- 2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1238) (5S,8S,11S,15S,18S,23aS,29S,35S,37aS)-8-((S)-sec-butyl)-29-(3-chloro-4-(trifluoromethyl)phenethyl)-35-(cyclohexylmethyl)-15-(1,1-dioxidothiomorpholine-4-carbonyl)-11-isobutyl-18-isopropyl-5,6,12,16,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1239) (5S,8S,11S,15R,18S,23aS,29S,35S,37aS)-8-((S)-sec-butyl)-29-(3-chloro-4-(trifluoromethyl)phenethyl)-11-isobutyl-5,6,12,15,18,19,33,36-octamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1240) (3S,6S,9S,13S,16S,22S,25S,31S,34S)-25-[(5-bromo-3-pyridyl)methyl]-22-butyl-9-ethyl-16-isobutyl-31-1[(4-methoxyphenyl)methyl]-3,4,10,14,19,19,20,29,32-nonamethyl-6-[(1S)-1-methylpropyl]-13-(piperidine-1-carbonyl)-1,4,7,10,14,17,20,23,26,29,32-undecazabicyclo[32.2.0]hexatriacontane-2,5,8,11,15,18,21,24,27,30,33-undecone, (1241) (3S,9S,18S,21S,25S,28S,34S,36R)-3-[2-[3-chloro-4-(trifluoromethyl)phenyl]ethyl]-28-cyclohexyl-9-(cyclohexylmethyl)-36-ethoxy-21-isobutyl-7,10,13,16,22,26,29-heptamethyl-18-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclobutane]-2,5,8,11,14,17,20,23,27,30,33-undecone, (1242) (5S,8S,11S,15S,18S,23aS,29S,35S,37aS)-8,18-di((S)-sec-butyl)-29-(3-chloro-4-(trifluoromethyl)phenethyl)-25,25-difluoro-11-isobutyl-5,6,12,16,19,33,36-heptamethyl-15-(pyrrolidine-1-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1243) (3S,6S,9S,13S,16S,22S,25S,31S,34S)-25-[2-[3-chloro-4-(trifluoromethyl)phenyl]ethyl]-31-(cyclohexylmethyl)-9-isobutyl-16-isopropyl-3,4,10,14,17,22,23,29,32-nonamethyl-6-[(1S)-1-methylpropyl]-13-(piperidine-1-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (1244) (3S,9S,18S,21S,25S,28S,34S)-28-cyclohexyl-3-[2-[3,5-difluoro-4-(trifluoromethyl)phenyl]ethyl]-7,10,13,16,22,26,29-heptamethyl-18-[(1S)-1-methylpropyl]-25-(pyrrolidine-1-carbonyl)-21-(2,2,2-trifluoroethyl)-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1245) (3S,9S,18S,21S,25S,28S,34S)-3-[2-[3-chloro-4-(trifluoromethyl)phenyl]ethyl]-28-cyclohexyl-36,36-difluoro-7,10,13,16,22,26,29-heptamethyl-18-[(1S)-1-methylpropyl]-9-(p-tolylmethyl)-25-(pyrrolidine-1-carbonyl)-21-(2,2,2-trifluoroethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1246) (6S,9S,13S,16S,22S,25S,31S,34S)-25-[(3-iodophenyl)methyl]-9,16-diisobutyl-31-[(4-methoxyphenyl)methyl]-4,10,14,19,19,20,29,32-octamethyl-6-[(1S)-1-methylpropyl]-13-(piperidine-1-carbonyl)-22-prop-2-ynyl-1,4,7,10,14,17,20,23,26,29,32-undecazabicyclo[32.2.0]hexatriacontane-2,5,8,11,15,18,21,24,27,30,33-undecone, (1247) (3S,9S,18S,21S,25S,28S,34S)-3-[2-[3-chloro-4-(trifluoromethyl)phenyl]ethyl]-9-(cyclohexylmethyl)-21-isobutyl-7,10,13,16,22,29-hexamethyl-18,28-bis[(1S)-1-methylpropyl]-25-(oxazolidine-3-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1248) (5S,8S,11S,15S,18S,23aS,29S,35S,37aS)-15-(azetidine-1-carbonyl)-8-((S)-sec-butyl)-35-(cyclohexylmethyl)-18-cyclopentyl-29-(3,5-difluoro-4-(trifluoromethyl)phenethyl)-25,25-difluoro-11-isobutyl-5,6,12,16,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1249) (3S,6S,9S,13S,16S,22S,25S,31S,34S)-22-butyl-9-ethyl-25-[(2-fluoro-3-iodo-phenyl)methyl]-16-isobutyl-31-[(4-methoxyphenyl)methyl]-3,4,10,14,19,19,20,29,32-nonamethyl-6-[(1S)-1-methylpropyl]-13-(piperidine-1-carbonyl)-1,4,7,10,14,17,20,23,26,29,32-undecazabicyclo[32.2.0]hexatriacontane-2,5,8,11,15,18,21,24,27,30,33-undecone, (1250) (5S,8S,11S,15S,18S,23aS,25R,29S,35S,37aS)-8-((S)-sec-butyl)-35-(cyclohexylmethyl)-18-cyclopentyl-29-(3,5-difluoro-4-(trifluoromethyl)phenethyl)-25-ethoxy-11-isobutyl-5,6,12,16,19,33,36-heptamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1251) (5S,8S,11S,15S,18S,23aS,29S,35S,37aS)-15-(3-oxa-8-azabicyclo[3.2.1]octane-8-carbonyl)-8-((S)-sec-butyl)-29-(3-chloro-4-(trifluoromethyl)phenethyl)-18-cyclopentyl-11-(cyclopentylmethyl)-5,6,12,16,19,33,36-heptamethyl-35-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1252) (5S,8S,11S,15S,18S,23aS,29S,35S,37aS)-8-((S)-sec-butyl)-35-(cyclohexylmethyl)-18-cyclopentyl-12-ethyl-29-(3-fluoro-4-(trifluoromethyl)phenethyl)-11-isobutyl-N,N,5,16,19,33,36-heptamethyl-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1253) (3S,9S,18S,21S,25S,28S,34S)-28-cyclohexyl-9-(cyclohexylmethyl)-3-[2-[3,5-difluoro-4-(trifluoromethyl)phenyl]ethyl]-7,10,13,16,22,26,29-heptamethyl-18-[(1S)-1-methylpropyl]-21-propyl-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1254) (5S,8S,11S,15S,18S,23aS,29S,35S,37aS)-8,18-di((S)-sec-butyl)-29-(3,5-difluoro-4-(trifluoromethyl)phenethyl)-25,25-difluoro-11-isobutyl-5,6,12,16,19,33,36-heptamethyl-15-(pyrrolidine-1-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1255) (3S,9S,18S,21S,25S,28S,34S)-3-[2-[3-chloro-4-(trifluoromethyl)phenyl]ethyl]-28-cyclohexyl-9-(cyclohexylmethyl)-16-ethyl-21-isobutyl-7,10,13,22,26,29-hexamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1256) (3S,6S,9S,13S,16S,22S,25S,31S,34S)-22-butyl-25-[(2,3-difluorophenyl)methyl]-9-ethyl-16-isobutyl-31-[(4-methoxyphenyl)methyl]-3,4,10,14,19,19,20,29,32-nonamethyl-6-[(1S)-1-methylpropyl]-13-(piperidine-1-carbonyl)-1,4,7,10,14,17,20,23,26,29,32-undecazabicyclo[32.2.0]hexatriacontane-2,5,8,11,15,18,21,24,27,30,33-undecone, (1257) (3S,9S,18S,21S,25S,28S,34S)-3-[2-[3-chloro-4-(trifluoromethyl)phenyl]ethyl]-9-(cyclohexylmethyl)-21-isobutyl-7,10,13,16,22,29-hexamethyl-18,28-bis[(1S)-1-methylpropyl]-25-(3-oxa-8-azabicyclo[3.2.1]octane-8-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1258) (3S,6S,9S,13S,16S,22S,25S,31S,34S)-25-[(3-iodophenyl)methyl]-9,16-diisobutyl-3,4,10,14,19,19,20,29,32-nonamethyl-6-[(1S)-1-methylpropyl]-13-(piperidine-1-carbonyl)-22-prop-2-ynyl-31-[[4-(trifluoromethyl)phenyl]methyl]-1,4,7,10,14,17,20,23,26,29,32-undecazabicyclo[32.2.0]hexatriacontane-2,5,8,11,15,18,21,24,27,30,33-undecone, (1259) (5S,8S,11S,15S,18S,23aS,25R,29S,35S,37aS)-8-((S)-sec-butyl)-29-(3-chloro-4-(trifluoromethyl)phenethyl)-35-(cyclohexylmethyl)-18-cyclopentyl-25-ethoxy-11-isobutyl-5,6,12,16,19,33,36-heptamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1260) (3S,9S,18S,21S,25S,28S,34S)-28-cyclohexyl-3-[2-[3,5-difluoro-4-(trifluoromethyl)phenyl]ethyl]-36,36-difluoro-7,10,13,16,22,26,29-heptamethyl-18-[(1S)-1-methylpropyl]-25-(morpholine-4-carbonyl)-21-(2,2,2-trifluoroethyl)-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1261) (5S,8S,11S,15S,18S,23aS,25R,29S,35S,37aS)-8,18-di((S)-sec-butyl)-29-(3,5-difluoro-4-(trifluoromethyl)phenethyl)-25-ethoxy-11-isobutyl-5,6,12,16,19,33,36-heptamethyl-15-(morpholine-4-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1262) (5S,8S,11S,15S,18S,23aS,29S,35S,37aS)-15-(azetidine-1-carbonyl)-8-((S)-sec-butyl)-29-(3-chloro-4-(trifluoromethyl)phenethyl)-35-(cyclohexylmethyl)-18-cyclopentyl-12-ethyl-11-isobutyl-5,16,19,33,36-pentamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1263) (3S,9S,18S,21S,25S,28S,34S)-3-[2-[3-chloro-4-(trifluoromethyl)phenyl]ethyl]-28-cyclohexyl-9-(cyclohexylmethyl)-25-(1,1-dioxo-1,4-thiazinane-4-carbonyl)-21-isobutyl-7,10,13,16,22,26,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1264) (5S,8S,11S,15S,18S,23aS,29S,35S,37aS)-8-((S)-sec-butyl)-35-(cyclohexylmethyl)-18-cyclopentyl-25,25-difluoro-29-(3-fluoro-4-(trifluoromethyl)phenethyl)-11-isobutyl-N,N,5,6,12,16,19,33,36-nonamethyl-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1265) (3S,9S,18S,21S,25S,28S,34S)-3-[2-[3-chloro-4-(trifluoromethyl)phenyl]ethyl]-9-(cyclohexylmethyl)-25-(3,3,4,4,5,5-hexafluoropiperidine-1-carbonyl)-21-isobutyl-7,10,13,16,22,29-hexamethyl-18,28-bis[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1266) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-cyclopentyl-12-ethyl-11-isobutyl-5,16,19,33,36-pentamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1267) (3S,9S,18S,21S,25S,28S,34S,36R)-3-[2-[3-chloro-4-(trifluoromethyl)phenyl]ethyl]-28-cyclohexyl-9-(cyclohexylmethyl)-36-ethoxy-7,10,13,16,22,26,29-heptamethyl-18-[(1S)-1-methylpropyl]-21-propyl-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1268) (3S,6S,9S,13S,16S,22S,25S,31S,34S)-22-butyl-25-[(2,5-difluorophenyl)methyl]-9-ethyl-16-isobutyl-31-I[(4-methoxyphenyl)methyl]-3,4,10,14,19,19,20,29,32-nonamethyl-6-[(1S)-1-methylpropyl]-13-(piperidine-1-carbonyl)-1,4,7,10,14,17,20,23,26,29,32-undecazabicyclo[32.2.0]hexatriacontane-2,5,8,11,15,18,21,24,27,30,33-undecone, (1269) (5S,8S,11S,15S,18S,23aS,29S,35S,37aS)-8-((S)-sec-butyl)-29-(3-chloro-4-(trifluoromethyl)phenethyl)-18-cyclopentyl-11-(cyclopentylmethyl)-N,N,5,12,16,19,33,36-octamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1270) (3S,9S,18S,21S,25S,28S,34S)-3-[2-[3-chloro-4-(trifluoromethyl)phenyl]ethyl]-9-(cyclohexylmethyl)-28-cyclopentyl-36,36-difluoro-21-isobutyl-7,10,13,16,22,26,29-heptamethyl-18-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1271) (3S,9S,18S,21S,25S,28S,34S,36R)-28-cyclohexyl-3-[2-[3,5-difluoro-4-(trifluoromethyl)phenyl]ethyl]-36-ethoxy-7,10,13,16,22,26,29-heptamethyl-18-[(1S)-1-methylpropyl]-25-(pyrrolidine-1-carbonyl)-21-(2,2,2-trifluoroethyl)-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1272) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-cyclopentyl-33-ethyl-11-isobutyl-5,6,12,16,19,36-hexamethyl-15-(morpholine-4-carbonyl)docosahydro-2H4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1273) (3S,9S,18S,21S,25S,28S,34S)-3-[2-[3-chloro-4-(trifluoromethyl)phenyl]ethyl]-9-(cyclohexylmethyl)-25-(3,3-dimethylpyrrolidine-1-carbonyl)-21-isobutyl-7,10,13,16,22,29-hexamethyl-18,28-bis[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1274) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,29-hexamethyl-8-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1275) (3S,9S,18S,21S,25S,28S,34S)-21-cyclobutyl-28-cyclohexyl-9-(cyclohexylmethyl)-3-[2-[3,5-difluoro-4-(trifluoromethyl)phenyl]ethyl]-7,10,13,16,22,26,29-heptamethyl-18-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1276) (5S,8S,11S,15S,18S,23aS,29S,35S,37aS)-8-((S)-sec-butyl)-29-(3-chloro-4-(trifluoromethyl)phenethyl)-35-(cyclohexylmethyl)-33-ethyl-11-isobutyl-18-isopropyl-5,6,12,16,19,36-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1277) (3S,9S,18S,21S,25S,28S,34S)-3-[2-[3-chloro-4-(trifluoromethyl)phenyl]ethyl]-9-(cyclohexylmethyl)-21-isobutyl-7,10,13,16,22,29-hexamethyl-18,28-bis[(1S)-1-methylpropyl]-25-(morpholine-4-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1278) (3S,9S,18S,21S,25S,28S,34S)-28-cyclohexyl-3-[2-[3,5-difluoro-4-(trifluoromethyl)phenyl]ethyl]-7,10,13,16,22,26,29-heptamethyl-18-[(1S)-1-methylpropyl]-9-(p-tolylmethyl)-25-(pyrrolidine-1-carbonyl)-21-(2,2,2-trifluoroethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1279) (3S,9S,18S,21S,25S,28S,34S)-3-[2-[3-chloro-4-(trifluoromethyl)phenyl]ethyl]-9-(cyclohexylmethyl)-25-(1,1-dioxo-1,4-thiazinane-4-carbonyl)-21-isobutyl-7,10,13,16,22,29-hexamethyl-18,28-bis[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1280) (5S,8S,11S,15S,18S,23aS,29S,35S,37aS)-8-((S)-sec-butyl)-29-(3-chloro-4-(trifluoromethyl)phenethyl)-35-(cyclohexylmethyl)-15-(3,3-dimethylpyrrolidine-1-carbonyl)-11-isobutyl-18-isopropyl-5,6,12,19,33,36-hexamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1281) (3S,9S,18S,21S,25S,28S,34S)-28-cyclohexyl-9-(cyclohexylmethyl)-3-[2-[3,5-difluoro-4-(trifluoromethyl)phenyl]ethyl]-36,36-difluoro-7,10,13,16,22,26,29-heptamethyl-18-[(1S)-1-methylpropyl]-25-(pyrrolidine-1-carbonyl)-21-(2,2,2-trifluoroethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1282) (5S,8S,11S,15S,18S,23aS,29S,35S,37aS)-8-((S)-sec-butyl)-29-(3-chloro-4-(trifluoromethyl)phenethyl)-18-cyclopentyl-12-ethyl-11-isobutyl-N,N,5,16,19,33,36-heptamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1283) (5S,8S,11S,15S,18S,23aS,29S,35S,37aS)-15-(azetidine-1-carbonyl)-8-((S)-sec-butyl)-29-(3-chloro-4-(trifluoromethyl)phenethyl)-35-(cyclohexylmethyl)-18-cyclopentyl-25,25-difluoro-11-isobutyl-5,6,12,16,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1284) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-25-[4-(oxetan-3-yl)piperazine-1-carbonyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1285) (3S,9S,18S,21S,25S,28S,34S,36R)-3-[2-[3-chloro-4-(trifluoromethyl)phenyl]ethyl]-28-cyclohexyl-36-ethoxy-7,10,13,16,22,26,29-heptamethyl-18-[(1S)-1-methylpropyl]-21-propyl-9-(p-tolylmethyl)-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1286) (3S,9S,12S,18S,27S,30S,34S)-9-butyl-18-[(4-chlorophenyl)methyl]-12-[(2-fluoro-5-iodo-phenyl)methyl]-3,30-diisobutyl-1,6,6,7,16,19,22,25,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (1287) (5S,8S,11S,15S,18S,23aS,29S,35S,37aS)-8,18-di((S)-sec-butyl)-29-(3-chloro-4-(trifluoromethyl)phenethyl)-12-ethyl-11-isobutyl-N,N,5,16,19,33,36-heptamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1288) (3S,6S,9S,13S,16S,22S,25S,31S,34S)-25-[(3-iodophenyl)methyl]-9,16-diisobutyl-3,4,10,14,19,19,20,29,32-nonamethyl-6-[(1S)-1-methylpropyl]-13-(piperidine-1-carbonyl)-22-prop-2-ynyl-31-[[4-(trifluoromethoxy)phenyl]methyl]-1,4,7,10,14,17,20,23,26,29,32-undecazabicyclo[32.2.0]hexatriacontane-2,5,8,11,15,18,21,24,27,30,33-undecone, (1289) (5S,8S,11S,15S,18S,23aS,29S,35S,37aS)-8,18-di((S)-sec-butyl)-29-(3-chloro-4-(trifluoromethyl)phenethyl)-11-isopentyl-5,6,12,16,19,33,36-heptamethyl-15-(pyrrolidine-1-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1290) (3S,9S,18S,21S,25S,28S,34S,36R)-28-cyclohexyl-9-(cyclohexylmethyl)-3-[2-[3,5-difluoro-4-(trifluoromethyl)phenyl]ethyl]-36-ethoxy-21-isobutyl-7,10,13,16,22,26,29-heptamethyl-18-[(1S)-1-methylpropyl]-25-(morpholine-4-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1291) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,6,12,16,19,33,36-heptamethyl-15-(4-methylpiperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1292) (5S,8S,11S,15S,18S,23aS,29S,35S,37aS)-8-((S)-sec-butyl)-35-(cyclohexylmethyl)-18-cyclopentyl-29-(3-fluoro-4-(trifluoromethyl)phenethyl)-11-isopentyl-N,N,5,12,16,19,33,36-octamethyl-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1293) (5S,8S,11S,15S,18S,23aS,29S,35S,37aS)-8,18-di((S)-sec-butyl)-29-(3-chloro-4-(trifluoromethyl)phenethyl)-11-isobutyl-5,12,16,19,33,36-hexamethyl-15-(morpholine-4-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1294) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,6,12,19,33,36-hexamethyl-15-(4-(oxetan-3-yl)piperazine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1295) (3S,9S,18S,21S,25S,28S,34S)-21-cyclobutyl-28-cyclohexyl-9-(cyclohexylmethyl)-3-[2-[3,5-difluoro-4-(trifluoromethyl)phenyl]ethyl]-36,36-difluoro-7,10,13,16,22,26,29-heptamethyl-18-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1296) (3S,9S,18S,21S,25S,28S,34S)-3-[2-[3-chloro-4-(trifluoromethyl)phenyl]ethyl]-28-cyclohexyl-36,36-difluoro-7,10,13,16,22,26,29-heptamethyl-18-[(1S)-1-methylpropyl]-21-propyl-9-(p-tolylmethyl)-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1297) (3S,9S,18S,21S,25S,28S,34S,36R)-28-cyclohexyl-3-[2-[3,5-difluoro-4-(trifluoromethyl)phenyl]ethyl]-36-ethoxy-7,10,13,16,22,26,29-heptamethyl-8-[(1S)-1-methylpropyl]-25-(morpholine-4-carbonyl)-21-(2,2,2-trifluoroethyl)-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1298) (6S,9S,13S,16S,22S,25S,31S,34S)-25-[(3-iodophenyl)methyl]-9,16-diisobutyl-4,10,14,19,19,20,29,32-octamethyl-6-[(1S)-1-methylpropyl]-13-(piperidine-1-carbonyl)-22-prop-2-ynyl-31-[[4-(trifluoromethoxy)phenyl]methyl]-1,4,7,10,14,17,20,23,26,29,32-undecazabicyclo[32.2.0]hexatriacontane-2,5,8,11,15,18,21,24,27,30,33-undecone, (1299) (5S,8S,11S,15S,18S,23aS,29S,35S,37aS)-15-(3-oxa-8-azabicyclo[3.2.1]octane-8-carbonyl)-8-((S)-sec-butyl)-29-(3-chloro-4-(trifluoromethyl)phenethyl)-18-cyclopentyl-11-isobutyl-5,12,16,19,33,36-hexamethyl-15-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1300) (5S,8S,11S,15R,18S,23aS,29S,35S,37aS)-8-((S)-sec-butyl)-29-(3-chloro-4-(trifluoromethyl)phenethyl)-18-cyclopentyl-11-isobutyl-5,6,12,15,19,33,35,36-octamethyldocosahydro-2H,4H-spiro[azeto[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1301) (3S,9S,18S,21S,25S,28S,34S,36R)-28-cyclohexyl-3-[2-[3,5-difluoro-4-(trifluoromethyl)phenyl]ethyl]-36-ethoxy-7,10,13,16,22,26,29-heptamethyl-18-[(1S)-1-methylpropyl]-9-(p-tolylmethyl)-25-(pyrrolidine-1-carbonyl)-21-(2,2,2-trifluoroethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1302) (3S,9S,18S,21S,25S,28S,31S,34S)-3-[2-[3-chloro-4-(trifluoromethyl)phenyl]ethyl]-28-cyclohexyl-9-(cyclohexylmethyl)-31-ethyl-21-isobutyl-7,10,13,16,22,26,29,31-octamethyl-18-[(1S)-1-methylpropyl]-25-(piperidine-1-carbonyl)-1,4,7,10,13,16,19,22,26,29,32-undecazabicyclo[32.3.0]heptatriacontane-2,5,8,11,14,17,20,23,27,30,33-undecone, (1303) (3S,9S,18S,21S,25S,28S,34S)-28-cyclohexyl-3-[2-[3,5-difluoro-4-(trifluoromethyl)phenyl]ethyl]-36,36-difluoro-7,10,13,16,22,26,29-heptamethyl-18-[(1S)-1-methylpropyl]-25-(pyrrolidine-1-carbonyl)-21-(2,2,2-trifluoroethyl)-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1304) (3S,6S,9S,13S,16S,22S,25S,31S,34S)-25-[(3-bromo-2-fluoro-phenyl)methyl]-22-butyl-9-ethyl-16-isobutyl-31-[(4-methoxyphenyl)methyl]-3,4,10,14,19,19,20,29,32-nonamethyl-6-[(1S)-1-methylpropyl]-13-(piperidine-1-carbonyl)-1,4,7,10,14,17,20,23,26,29,32-undecazabicyclo[32.2.0]hexatriacontane-2,5,8,11,15,18,21,24,27,30,33-undecone, (1305) (3S,9S,12S,18S,27S,30S,34S)-9-butyl-8-[(4-chlorophenyl)methyl]-12-[(4-fluorophenyl)methyl]-3,30-diisobutyl-1,6,6,7,16,19,22,25,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (1306) (3S,9S,18S,21S,25S,28S,34S)-28-cyclohexyl-3-[2-[3,5-difluoro-4-(trifluoromethyl)phenyl]ethyl]-36,36-difluoro-7,10,13,16,22,26,29-heptamethyl-18-[(1S)-1-methylpropyl]-21-propyl-9-(p-tolylmethyl)-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1307) (3S,6S,9S,13R,16S,22S,25S,31S,34S)-25-[2-[3-chloro-4-(trifluoromethyl)phenyl]ethyl]-16-cyclopentyl-9-isobutyl-3,4,10,13,17,22,29,32-octamethyl-6-[(1S)-1-methylpropyl]-31-(p-tolylmethyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (1308) (5S,8S,11S,15S,18S,23aS,29S,35S,37aS)-8-((S)-sec-butyl)-35-(cyclohexylmethyl)-18-cyclopentyl-29-(3,5-difluoro-4-(trifluoromethyl)phenethyl)-11-isobutyl-5,6,12,16,19,33,36-heptamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1309) (5S,8S,11S,15S,18S,23aS,29S,35S,37aS)-8-((S)-sec-butyl)-29-(3-chloro-4-(trifluoromethyl)phenethyl)-18,35-dicyclopentyl-11-isobutyl-5,12,16,19,33,36-hexamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1310) (5S,8S,11S,15S,18S,23aS,29S,35S,37aS)-8,18-di((S)-sec-butyl)-29-(3-chloro-4-(trifluoromethyl)phenethyl)-11-isopentyl-5,12,16,19,33,36-hexamethyl-15-(pyrrolidine-1-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1311) (5S,8S,11S,15S,18S,23aS,29S,35S,37aS)-8,18-di((S)-sec-butyl)-29-(3-chloro-4-(trifluoromethyl)phenethyl)-25,25-difluoro-11-isobutyl-5,6,12,16,19,33,36-heptamethyl-15-(morpholine-4-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1312) (5S,8S,11S,15S,18S,23aS,29S,35S,37aS)-8,18-di((S)-sec-butyl)-29-(3-chloro-4-(trifluoromethyl)phenethyl)-36-ethyl-11-isobutyl-5,6,12,16,19,33-hexamethyl-15-(morpholine-4-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1313) (3S,6S,9S,13S,16S,22S,25S,31S,34S)-31-benzyl-25-[(3-iodophenyl)methyl]-9,16-diisobutyl-3,4,10,14,19,19,20,29,32-nonamethyl-6-[(1S)-1-methylpropyl]-13-(piperidine-1-carbonyl)-22-prop-2-ynyl-1,4,7,10,14,17,20,23,26,29,32-undecazabicyclo[32.2.0]hexatriacontane-2,5,8,11,15,18,21,24,27,30,33-undecone, (1314) (3S,6S,9S,13S,16S,22R,25S,31S,34S)-25-[2-[3-chloro-4-(trifluoromethyl)phenyl]ethyl]-31-(cyclohexylmethyl)-9-isobutyl-16-isopropyl-3,4,10,14,17,22,29,32-octamethyl-6-[(1S)-1-methylpropyl]-13-(piperidine-1-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (1315) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,22,26,29-hexamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1316) (3S,6S,9S,13S,16S,22S,25S,31S,34S)-25-[2-[3-chloro-4-(trifluoromethyl)phenyl]ethyl]-31-(cyclohexylmethyl)-9-isobutyl-16-isopropyl-3,4,10,14,17,22,29,32-octamethyl-6-[(1S)-1-methylpropyl]-13-(piperidine-1-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (1317) (3S,9S,18S,21S,25S,28S,34S)-28-cyclohexyl-3-[2-[3,5-difluoro-4-(trifluoromethyl)phenyl]ethyl]-36,36-difluoro-7,10,13,16,22,26,29-heptamethyl-18-[(1S)-1-methylpropyl]-9-(p-tolylmethyl)-25-(pyrrolidine-1-carbonyl)-21-(2,2,2-trifluoroethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1318) (3S,9S,12S,18S,27S,30S,34S)-9-butyl-18-[(4-chlorophenyl)methyl]-12-[(5-chloro-2-thienyl)methyl]-3,30-diisobutyl-1,6,6,7,16,19,22,25,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (1319) (5S,8S,11S,15S,18S,23aS,29S,35S,37aS)-8,18-di((S)-sec-butyl)-29-(3-chloro-4-(trifluoromethyl)phenethyl)-36-ethyl-11-isobutyl-5,6,12,16,19,33-hexamethyl-15-(pyrrolidine-1-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1320) (5S,8S,11S,15S,18S,23aS,29S,35S,37aS)-8,18-di((S)-sec-butyl)-29-(3-chloro-4-(trifluoromethyl)phenethyl)-11-(cyclopentylmethyl)-5,12,16,19,33,36-hexamethyl-15-(pyrrolidine-1-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1321) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-25-(3-oxa-8-azabicyclo[3.2.1]octane-8-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1322) (5S,8S,11S,15S,18S,23aS,29S,35S,37aS)-8,18-di((S)-sec-butyl)-29-(3-chloro-4-(trifluoromethyl)phenethyl)-36-ethyl-11-isobutyl-5,6,12,16,19,33-hexamethyl-35-(4-methylbenzyl)-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1323) (5S,8S,11S,15S,18S,23aS,29S,35S,37aS)-8-((S)-sec-butyl)-29-(3-chloro-4-(trifluoromethyl)phenethyl)-35-(cyclohexylmethyl)-15-(3,3-dimethylpyrrolidine-1-carbonyl)-11-isobutyl-18-isopropyl-5,6,12,16,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1324) (5S,8S,11S,15S,18S,23aS,29S,35S,37aS)-8-((S)-sec-butyl)-35-(cyclohexylmethyl)-18-cyclopentyl-12-ethyl-29-(3-fluoro-4-(trifluoromethyl)phenethyl)-11-isobutyl-N,N,5,6,16,19,33,36-octamethyl-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1325) (5S,8S,11S,15S,18S,23aS,29S,35S,37aS)-8,18-di((S)-sec-butyl)-29-(3-chloro-4-(trifluoromethyl)phenethyl)-36-ethyl-11-isobutyl-5,6,12,16,19,33-hexamethyl-35-(4-methylbenzyl)-15-(pyrrolidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1326) (5S,8S,11S,15S,18S,23aS,29S,35S,37aS)-15-(3-oxa-8-azabicyclo[3.2.1]octane-8-carbonyl)-8-((S)-sec-butyl)-29-(3-chloro-4-(trifluoromethyl)phenethyl)-18-cyclopentyl-11-isopentyl-5,12,16,19,33,36-hexamethyl-35-(propoxymethyl)docosahydro-2H,4H-spiro[azeto[2,1-u]pyrrolo[2,1-i][1,4,7,10,13,16,19,22,25,28,31]

undecaazacyclotetratriacontine-21,1'-cyclopentan]-4,7,10,13,17,20,23,28,31,34,37(14H,22H)-undecaone, (1327) (3S,9S,12S,18S,27S,30S,34S)-18-[(4-fluorophenyl)methyl]-12-[(3-iodophenyl)methyl]-3,30-diisobutyl-1,6,6,7,16,19,22,25,31-nonamethyl-27-[(1S)-1-methylpropyl]-34-(piperidine-1-carbonyl)-9-prop-2-ynyl-1,4,7,10,13,16,19,22,25,28,31-undecazacyclotetratriacontane-2,5,8,11,14,17,20,23,26,29,32-undecone, (1328) (3S,6S,9S,13R,16S,22R,25S,31S,34S)-25-[2-[3-chloro-4-(trifluoromethyl)phenyl]ethyl]-16-cyclopentyl-9-isobutyl-3,4,10,13,17,22,29,32-octamethyl-6-[(1S)-1-methylpropyl]-31-(p-tolylmethyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (1329) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,6,12,16,19,33,36-heptamethyl-15-(oxazolidine-3-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1330) (5S,8S,11S,15S,18S,23aS,25R,29S,35S,37aS)-8,18-di((S)-sec-butyl)-29-(3-chloro-4-(trifluoromethyl)phenethyl)-25-ethoxy-11-isobutyl-5,6,12,16,19,33,36-heptamethyl-15-(morpholine-4-carbonyl)-35-(4-(trifluoromethyl)benzyl)docosahydro-2H4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1331) (5S,8S,11S,15R,18S,23aS,29S,35S,37aS)-8-((S)-sec-butyl)-29-(3-chloro-4-(trifluoromethyl)phenethyl)-18-cyclopentyl-11-isobutyl-5,12,15,19,33,36-hexamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1332) (5S,8S,11S,14aR,20S,25aS,31S,37S,39aS)-8-((S)-sec-butyl)-31-(3-chloro-4-(trifluoromethyl)phenethyl)-37-(cyclohexylmethyl)-11-isobutyl-20-isopropyl-5,6,12,21,35,38-hexamethyltetracosahydro-2H,4H-spiro[azeto[1,2-j]dipyrrolo[1,2-e1:1',2'-v][1,4,7,10,13,16,19,22,25,28,31]undecaazacyclotetratriacontine-23,1'-cyclopentan]-4,7,10,13,19,22,25,30,33,36,39(14H,24H)-undecaone, (1333) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-25-(morpholine-4-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1334) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,12,16,19,33,36-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1335) (5S,8S,11S,15S,18S,23aS,25R,29S,35S,37aS)-8,18-di((S)-sec-butyl)-29-(3-chloro-4-(trifluoromethyl)phenethyl)-25-ethoxy-11-isobutyl-5,6,12,16,19,33,36-heptamethyl-15-(pyrrolidine-1-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1336) (5S,8S,11S,15S,18S,23aS,29S,35S,37aS)-8-((S)-sec-butyl)-18,35-dicyclopentyl-29-(3,5-difluoro-4-(trifluoromethyl)phenethyl)-11-isobutyl-5,6,12,16,19,33,36-heptamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1337) (3S,9S,18S,21S,25S,28S,34S)-28-cyclohexyl-9-(cyclohexylmethyl)-3-[2-[3,5-difluoro-4-(trifluoromethyl)phenyl]ethyl]-36,36-difluoro-21-isobutyl-7,10,13,16,22,26,29-heptamethyl-18-[(1S)-1-methylpropyl]-25-(morpholine-4-carbonyl)spiro[1,4,7,10,13,16,19,22,26,29,32-undecazabicyclo[32.2.0]heptatriacontane-31,1'-cyclopentane]-2,5,8,11,14,17,20,23,27,30,33-undecone, (1338) (5S,8S,11S,15S,18S,23aS,29S,35S,37aS)-15-(3-oxa-8-azabicyclo[3.2.1]octane-8-carbonyl)-8-((S)-sec-butyl)-29-(3-chloro-4-(trifluoromethyl)phenethyl)-18-cyclopentyl-33-ethyl-11-isobutyl-5,6,12,16,19,36-hexamethyl-35-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1339) (3S,9S,18S,21S,25S,28S,34S,36R)-3-[2-[3-chloro-4-(trifluoromethyl)phenyl]ethyl]-28-cyclohexyl-36-ethoxy-7,10,13,16,22,26,29-heptamethyl-18-[(1S)-1-methylpropyl]-9-(p-tolylmethyl)-25-(pyrrolidine-1-carbonyl)-21-(2,2,2-trifluoroethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1340) (5S,8S,11S,15S,18S,23aS,29S,35S,37aS)-8-((S)-sec-butyl)-35-(cyclohexylmethyl)-18-cyclopentyl-11-(cyclopentylmethyl)-29-(3-fluoro-4-(trifluoromethyl)phenethyl)-N,N,5,12,16,19,33,36-octamethyl-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1341) (3S,9S,18S,21S,25S,28S,34S,36R)-28-cyclohexyl-9-(cyclohexylmethyl)-3-[2-[3,5-difluoro-4-(trifluoromethyl)phenyl]ethyl]-36-ethoxy-21-isobutyl-7,10,13,16,22,26,29-heptamethyl-18-[(1S)-1-methylpropyl]-25-(3-oxa-8-azabicyclo[3.2.1]octane-8-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1342) (3S,9S,18S,21S,25S,28S,34S)-9-(cyclohexylmethyl)-28-cyclopentyl-3-[2-[3,5-difluoro-4-(trifluoromethyl)phenyl]ethyl]-21-isobutyl-7,10,13,16,22,26,29-heptamethyl-8-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1343) (5S,8S,11S,15S,18S,23aS,29S,35S,37aS)-8,18-di((S)-sec-butyl)-29-(3,5-difluoro-4-(trifluoromethyl)phenethyl)-11-isobutyl-5,6,12,16,19,33,36-heptamethyl-15-(pyrrolidine-1-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1344) (6S,9S,13S,16S,22S,25S,31S,34S)-31-[(4-fluorophenyl)methyl]-25-[(3-iodophenyl)methyl]-9,16-diisobutyl-4,10,14,19,19,20,29,32-octamethyl-6-(1S)-1- methylpropyl]-13-(piperidine-1-carbonyl)-22-prop-2-ynyl-1,4,7,10,14,17,20,23,26,29,32-undecazabicyclo[32.2.0]hexatriacontane-2,5,8,11,15,18,21,24,27,30,33-undecone, (1345) (3S,9S,15S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,15,16,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1346) (5S,8S,11S,15S,18S,23aS,29S,35S,37aS)-8-((S)-sec-butyl)-35-(cyclohexylmethyl)-18-cyclopentyl-29-(3,5-difluoro-4-(trifluoromethyl)phenethyl)-25,25-difluoro-11-isobutyl-N,N,5,6,12,16,19,33,36-nonamethyl-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1347) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-25-(4-methylpiperidine-1-carbonyl)-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1348) (5S,8S,11S,15S,18S,23aS,29S,35S,37aS)-8,18-di((S)-sec-butyl)-29-(3,5-difluoro-4-(trifluoromethyl)phenethyl)-25,25-difluoro-11-isobutyl-5,6,12,16,19,33,36-heptamethyl-15-(morpholine-4-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1349) (5S,8S,11S,15S,18S,23aS,29S,35S,37aS)-8-((S)-sec-butyl)-29-(3-chloro-4-(trifluoromethyl)phenethyl)-35-(cyclohexylmethyl)-15-(1,1-dioxidothiomorpholine-4-carbonyl)-11-isobutyl-18-isopropyl-5,6,12,19,33,36-hexamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1350) (3S,6S,9S,13S,16S,22S,25S,31S,34S)-25-[(3-iodophenyl)methyl]-9,16-diisobutyl-31-[(4-methoxyphenyl)methyl]-3,4,10,14,19,19,20,29,32-nonamethyl-6-[(1S)-1-methylpropyl]-13-(piperidine-1-carbonyl)-22-prop-2-ynyl-1,4,7,10,14,17,20,23,26,29,32-undecazabicyclo[32.2.0]hexatriacontane-2,5,8,11,15,18,21,24,27,30,33-undecone, (1351) (5S,8S,11S,15S,18S,23aS,29S,35S,37aS)-8,18-di((S)-sec-butyl)-29-(3,5-difluoro-4-(trifluoromethyl)phenethyl)-36-ethyl-11-isobutyl-5,6,12,16,19,33,36-hexamethyl-35-(4-methylbenzyl)-15-(pyrrolidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1352) (3S,9S,12S,18S,27S,30S,34S)-9-butyl-12-[(2-chloro-5-iodo-phenyl)methyl]-18-[(4-chlorophenyl)methyl]-3,30-diisobutyl-1,6,6,7,16,19,22,25,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (1353) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,6,12,19,33,36-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1354) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26-hexamethyl-8-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1355) (5S,8S,11S,15S,18S,23aS,29S,35S,37aS)-15-(3-oxa-8-azabicyclo[3.2.1]octane-8-carbonyl)-8-((S)-sec-butyl)-18-cyclopentyl-29-(3,5-difluoro-4-(trifluoromethyl)phenethyl)-11-isobutyl-5,6,12,16,19,33,36-heptamethyl-35-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1356) (5S,8S,11S,15S,18S,23aS,29S,35S,37aS)-8,18-di((S)-sec-butyl)-29-(3-chloro-4-(trifluoromethyl)phenethyl)-11-isopentyl-5,12,16,19,33,36-hexamethyl-15-(morpholine-4-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1357) (3S,9S,18S,21S,25S,28S,34S)-3-[2-[3-chloro-4-(trifluoromethyl)phenyl]ethyl]-28-cyclohexyl-9-(cyclohexylmethyl)-36,36-difluoro-7,10,13,16,22,26,29-heptamethyl-18-[(1S)-1-methylpropyl]-25-(pyrrolidine-1-carbonyl)-21-(2,2,2-trifluoroethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1358) (3S,6S,9S,13S,16S,22S,25S,31S,34S)-22-butyl-9-ethyl-25-[(5-iodo-2-methyl-phenyl)methyl]-16-isobutyl-31-[(4-methoxyphenyl)methyl]-3,4,10,14,19,19,20,29,32-nonamethyl-6-[(1S)-1-methylpropyl]-13-(piperidine-1-carbonyl)-1,4,7,10,14,17,20,23,26,29,32-undecazabicyclo[32.2.0]hexatriacontane-2,5,8,11,15,18,21,24,27,30,33-undecone, (1359) (5S,8S,11S,15S,18S,23aS,29S,35S,37aS)-15-(3-oxa-8-azabicyclo[3.2.1]octane-8-carbonyl)-8-((S)-sec-butyl)-29-(3-chloro-4-(trifluoromethyl)phenethyl)-18-cyclopentyl-11-(cyclopentylmethyl)-5,12,16,19,33,36-hexamethyl-35-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1360) (5S,8S,11S,15S,18S,23aS,29S,35S,37aS)-8,18-di((S)-sec-butyl)-29-(3-chloro-4-(trifluoromethyl)phenethyl)-11-isobutyl-5,12,16,19,33,36-hexamethyl-15-(pyrrolidine-1-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1361) (3S,9S,12S,18S,27S,30S,34S)-12-[(3-iodophenyl)methyl]-3,30-diisobutyl-1,6,6,7,16,19,22,25,31-nonamethyl-27-[(1S)-1-methylpropyl]-34-(piperidine-1-carbonyl)-9-prop-2-ynyl-18-[[4-(trifluoromethyl)phenyl]methyl]-1,4,7,10,13,16,19,22,25,28,31-undecazacyclotetratriacontane-2,5,8,11,14,17,20,23,26,29,32-undecone, (1362) (5S,8S,11S,15S,18S,23aS,29S,35S,37aS)-8,18-di ((S)-sec-butyl)-29-(3,5-difluoro-4-(trifluoromethyl)phenethyl)-11-isobutyl-5,6,12,16,19,33,36-heptamethyl-15-(morpholine-4-carbonyl)-35-(4-(trifluoromethyl)benzyl) docosahydro-2H,4H-spiro[azeto[2,1-u]pyrrolo[2,1-i][1,4, 7,10,13,16,19,22,25,28,31] undecaazacyclotetratriacontine-21,1'-cyclopentan]-4,7, 10,13,17,20,23,28,31,34,37(14H,22H)-undecaone, (1363) (3S,9S,18S,21S,25S,28S,34S)-3-[2-[3-chloro-4-(trifluoromethyl)phenyl]ethyl]-21-cyclobutyl-28-cyclohexyl-9-(cyclohexylmethyl)-36,36-difluoro-7,10,13,16, 22,26,29-heptamethyl-18-1[(1S)-1-methylpropyl]-25-(pyrrolidine-1-carbonyl)spiro[1,4,7,10,13,16,19,22,26, 29,32-undecazabicyclo[32.3.0]heptatriacontane-31,1'-cyclopentane]-2,5,8,11,14,17,20,23,27,30,33-undecone, (1364) (5S,8S,11S,15S,18S,23aS,29S,35S,37aS)-8,18-di ((S)-sec-butyl)-29-(3,5-difluoro-4-(trifluoromethyl)phenethyl)-36-ethyl-11-isobutyl-5,6,12,16,19,33-hexamethyl-15-(morpholine-4-carbonyl)-35-(4-(trifluoromethyl) benzyl)docosahydro-2H,4H-spiro[azeto[2,1-u]pyrrolo[2, 1-i][1,4,7,10,13,16,19,22,25,28,31] undecaazacyclotetratriacontine-21,1'-cyclopentan]-4,7, 10,13,17,20,23,28,31,34,37(14H,22H)-undecaone, (1365) (5S,8S,11S,15S,18S,23aS,29S,35S,37aS)-8,18-di ((S)-sec-butyl)-29-(3-chloro-4-(trifluoromethyl)phenethyl)-12-ethyl-11-isobutyl-N,N,5,6,16,19,33,36-octamethyl-35-(4-methylbenzyl)-4,7,10,13,17,20,23,28,31,34, 37-undecaoxotetratriacontahydro-2H,4H-spiro[azeto[2,1-u]pyrrolo[2,1-i][1,4,7,10,13,16,19,22,25,28,31] undecaazacyclotetratriacontine-21,1'-cyclopentane]-15-carboxamide, (1366) (3S,9S,18S,21S,25S,28S,34S,36R)-28-cyclohexyl-9-(cyclohexylmethyl)-3-[2-[3,5-difluoro-4-(trifluoromethyl)phenyl]ethyl]-36-ethoxy-21-isobutyl-7,10,13,16, 22,26,29-heptamethyl-18-[(1S)-1-methylpropyl]-25-(pyrrolidine-1-carbonyl)spiro[1,4,7,10,13,16,19,22,26, 29,32-undecazabicyclo[32.3.0]heptatriacontane-31,1'-cyclobutane]-2,5,8,11,14,17,20,23,27,30,33-undecone, (1367) (3S,9S,18S,21S,25S,28S,34S,36R)-28-cyclohexyl-9-(cyclohexylmethyl)-3-[2-[3,5-difluoro-4-(trifluoromethyl)phenyl]ethyl]-36-ethoxy-7,10,13,16,22,26,29-heptamethyl-8-[(1S)-1-methylpropyl]-21-propyl-25-(pyrrolidine-1-carbonyl)spiro[1,4,7,10,13,16,19,22,26, 29,32-undecazabicyclo[32.3.0]heptatriacontane-31,1'-cyclopentane]-2,5,8,11,14,17,20,23,27,30,33-undecone, (1368) (5S,8S,11S,15S,18S,23aS,29S,35S,37aS)-8-((S)-sec-butyl)-18-cyclopentyl-29-(3,5-difluoro-4-(trifluoromethyl)phenethyl)-36-ethyl-11-isobutyl-5,6,12,16,19, 33-hexamethyl-35-(4-methylbenzyl)-15-(morpholine-4-carbonyl)docosahydro-2H,4H-spiro[azeto[2,1-u]pyrrolo [2,1-i][1,4,7,10,13,16,19,22,25,28,31] undecaazacyclotetratriacontine-21,1'-cyclopentan]-4,7, 10,13,17,20,23,28,31,34,37(14H,22H)-undecaone, (1369) (3S,9S,18S,21S,25S,28S,34S,36R)-3-[2-[3-chloro-4-(trifluoromethyl)phenyl]ethyl]-28-cyclohexyl-9-(cyclohexylmethyl)-36-ethoxy-7,10,13,16,22,26,29-heptamethyl-18-[(1S)-1-methylpropyl]-25-(pyrrolidine-1-carbonyl)-21-(2,2,2-trifluoroethyl)spiro[1,4,7,10,13,16, 19,22,26,29,32-undecazabicyclo[32.3.0] heptatriacontane-31,1'-cyclopentane]-2,5,8,11,14,17,20, 23,27,30,33-undecone, (1370) (3S,9S,18S,21S,25S,28S,34S,36R)-3-[2-[3-chloro-4-(trifluoromethyl)phenyl]ethyl]-9-(cyclohexylmethyl)-28-cyclopentyl-36-ethoxy-21-isobutyl-7,10,13,16,22,26, 29-heptamethyl-18-[(1S)-1-methylpropyl]-25-(pyrrolidine-1-carbonyl)spiro[1,4,7,10,13,16,19,22,26, 29,32-undecazabicyclo[32.3.0]heptatriacontane-31,1'-cyclopentane]-2,5,8,11,14,17,20,23,27,30,33-undecone, (1371) (5S,8S,11S,15S,18S,23aS,29S,35S,37aS)-8,18-di ((S)-sec-butyl)-29-(3-chloro-4-(trifluoromethyl)phenethyl)-11-(cyclopentylmethyl)-5,12,16,19,33,36-hexamethyl-15-(morpholine-4-carbonyl)-35-(4-(trifluoromethyl)benzyl)docosahydro-2H,4H-spiro[azeto [2,1-u]pyrrolo[2,1-i][1,4,7,10,13,16,19,22,25,28,31] undecaazacyclotetratriacontine-21,1'-cyclopentan]-4,7, 10,13,17,20,23,28,31,34,37(14H,22H)-undecaone, (1372) (3S,6S,9S,13S,16S,22S,25S,31S,34S)-25-[(3-bromo-5-fluoro-phenyl)methyl]-22-butyl-9-ethyl-16-isobutyl-31-[(4-methoxyphenyl)methyl]-3,4,10,14,19,19, 20,29,32-nonamethyl-6-[(1S)-1-methylpropyl]-13-(piperidine-1-carbonyl)-1,4,7,10,14,17,20,23,26,29,32-undecazabicyclo[32.2.0]hexatriacontane-2,5,8,11,15,18, 21,24,27,30,33-undecone, (1373) (3S,9S,18S,21S,25R,28S,31S,34S,36S)-31-benzyl-9-[(4-chlorophenyl)methyl]-36-hydroxy-28-isobutyl-7, 10,13,16,21,22,25,29,32-nonamethyl-18-[(1S)-1-methylpropyl]-3-[2-[4-(trifluoromethyl)phenyl]ethyl]-1,4,7,10, 13,16,19,22,26,29,32-undecazabicyclo[32.3.0] heptatriacontane-2,5,8,11,14,17,20,23,27,30,33-undecone, (1374) (3S,9S,18S,21S,25S,28S,34S,36S)-3-[2-[3-chloro-4-(trifluoromethyl)phenyl]ethyl]-28-cyclohexyl-9-(cyclohexylmethyl)-36-hydroxy-21-isobutyl-7,10,13,16,22,26, 29-heptamethyl-18-[(1S)-1-methylpropyl]-25-(piperidine-1-carbonyl)spiro[1,4,7,10,13,16,19,22,26,29, 32-undecazabicyclo[32.3.0]heptatriacontane-31,1'-cyclopentane]-2,5,8,11,14,17,20,23,27,30,33-undecone, (1375) (3S,9S,18S,21S,25R,28S,31S,34S,36R)-31-benzyl-9-[(4-chlorophenyl)methyl]-36-hydroxy-28-isobutyl-7, 10,13,16,21,22,25,29,32-nonamethyl-18-[(1S)-1-methylpropyl]-3-[2-[4-(trifluoromethyl)phenyl]ethyl]-1,4,7,10, 13,16,19,22,26,29,32-undecazabicyclo[32.3.0] heptatriacontane-2,5,8,11,14,17,20,23,27,30,33-undecone, (1376) (3S,9S,18S,21S,25S,28S,34S,36R)-3-[2-[3-chloro-4-(trifluoromethyl)phenyl]ethyl]-28-cyclohexyl-9-(cyclohexylmethyl)-36-hydroxy-21-isobutyl-7,10,13,16,22, 26,29-heptamethyl-18-[(1S)-1-methylpropyl]-25-(piperidine-1-carbonyl)spiro[1,4,7,10,13,16,19,22,26,29, 32-undecazabicyclo[32.3.0]heptatriacontane-31,1'-cyclopentane]-2,5,8,11,14,17,20,23,27,30,33-undecone, (1377) (6S,9S,13R,16S,22S,25S,31S,34S)-25-[2-[3-chloro-4-(trifluoromethyl)phenyl]ethyl]-16,22-diisobutyl-4,9,10, 13,14,19,19,20,29,32-decamethyl-6-[(1S)-1-methylpropyl]-31-(p-tolylmethyl)-1,4,7,10,14,17,20,23,26,29,32-undecazabicyclo[32.2.0]hexatriacontane-2,5,8,11,15,18, 21,24,27,30,33-undecone, (1378) (6S,9S,13R,16S,22S,25S,28R,31S,34S)-25-[2-[3-chloro-4-(trifluoromethyl)phenyl]ethyl]-31-(cyclohexylmethyl)-16,22-diisobutyl-4,9,10,13,14,19,19,20,28,29, 32-undecamethyl-6-[(1S)-1-methylpropyl]-1,4,7,10,14, 17,20,23,26,29,32-undecazabicyclo[32.2.0] hexatriacontane-2,5,8,11,15,18,21,24,27,30,33-undecone, (1379) (3S,6S,9S,13R,16S,22S,25S,31S,34S)-25-[2-[3-chloro-4-(trifluoromethyl)phenyl]ethyl]-9,16,22-triisobutyl-3,4,10,13,14,19,19,20,29,32-decamethyl-6-[(1S)-1-methylpropyl]-31-(p-tolylmethyl)-1,4,7,10,14, 17,20,23,26,29,32-undecazabicyclo[32.2.0] hexatriacontane-2,5,8,11,15,18,21,24,27,30,33-undecone, (1380) (3S,9S,12S,18S,27S,30S,34R)-12-[2-[3-chloro-4-(trifluoromethyl)phenyl]ethyl]-18-(cyclohexylmethyl)-3, 9-diisobutyl-1,6,6,7,16,19,22,25,30,31,34-undecamethyl-27-[(1S)-1-methylpropyl]-1,4,7,10,13,16,19,22,25,28,31-undecazacyclotetratriacontane-2,5,8,11,14,17,20,23,26,29,32-undecone, (1381) (3S,9S,12S,15R,18S,27S,30S,34R)-12-[2-[3-chloro-4-(trifluoromethyl)phenyl]ethyl]-3,9-diisobutyl-1,6,6,7,15,16,19,22,25,30,31,34-dodecamethyl-27-[(1S)-1-methylpropyl]-18-(p-tolylmethyl)-1,4,7,10,13,16,19,22,25,28,31-undecazacyclotetratriacontane-2,5,8,11,14,17,20,23,26,29,32-undecone, (1382) (6S,9S,13R,16S,22S,25S,28R,31S,34S)-25-[2-[3-chloro-4-(trifluoromethyl)phenyl]ethyl]-16,22-diisobutyl-4,9,10,13,14,19,19,20,28,29,32-undecamethyl-6-[(1S)-1-methylpropyl]-31-(p-tolylmethyl)-1,4,7,10,14,17,20,23,26,29,32-undecazabicyclo[32.2.0]hexatriacontane-2,5,8,11,15,18,21,24,27,30,33-undecone, (1383) (6S,9S,13R,16S,22S,25S,28R,31S,34S)-25-[2-[3-chloro-4-(trifluoromethyl)phenyl]ethyl]-16,22-diisobutyl-4,9,10,13,14,19,19,20,28,29,32-undecamethyl-6-[(1S)-1-methylpropyl]-31-[[4-(trifluoromethyl)phenyl]methyl]-1,4,7,10,14,17,20,23,26,29,32-undecazabicyclo[32.2.0]hexatriacontane-2,5,8,11,15,18,21,24,27,30,33-undecone, (1384) (3S,9S,12S,15R,18S,27S,30S,34R)-12-[2-[3-chloro-4-(trifluoromethyl)phenyl]ethyl]-3,9,30-triisobutyl-1,6,6,7,15,16,19,22,25,31,34-undecamethyl-27-[(1S)-1-methylpropyl]-18-(p-tolylmethyl)-1,4,7,10,13,16,19,22,25,28,31-undecazacyclotetratriacontane-2,5,8,11,14,17,20,23,26,29,32-undecone, (1385) (3S,9S,12S,15R,18S,27S,30S,34R)-12-[2-[3-chloro-4-(trifluoromethyl)phenyl]ethyl]-3,9-diisobutyl-1,6,6,7,15,16,19,22,25,30,31,34-dodecamethyl-27-[(1S)-1-methylpropyl]-18-[[4-(trifluoromethyl)phenyl]methyl]-1,4,7,10,13,16,19,22,25,28,31-undecazacyclotetratriacontane-2,5,8,11,14,17,20,23,26,29,32-undecone, (1386) (6S,9S,13R,16S,22S,25S,31S,34S)-25-[2-[3-chloro-4-(trifluoromethyl)phenyl]ethyl]-9,16,22-triisobutyl-4,10,13,14,19,19,20,29,32-nonamethyl-6-[(1S)-1-methylpropyl]-31-(p-tolylmethyl)-1,4,7,10,14,17,20,23,26,29,32-undecazabicyclo[32.2.0]hexatriacontane-2,5,8,11,15,18,21,24,27,30,33-undecone, (1387) (6S,9S,13R,16S,22S,25S,31S,34S)-25-[2-[3-chloro-4-(trifluoromethyl)phenyl]ethyl]-31-(cyclohexylmethyl)-16,22-diisobutyl-4,9,10,13,14,19,19,20,29,32-decamethyl-6-[(1S)-1-methylpropyl]-1,4,7,10,14,17,20,23,26,29,32-undecazabicyclo[32.2.0]hexatriacontane-2,5,8,11,15,18,21,24,27,30,33-undecone, (1388) (3S,9S,12S,18S,27S,30S,34R)-12-[2-[3-chloro-4-(trifluoromethyl)phenyl]ethyl]-3,9,30-triisobutyl-1,6,6,7,16,19,22,25,31,34-decamethyl-27-[(1S)-1-methylpropyl]-18-(p-tolylmethyl)-1,4,7,10,13,16,19,22,25,28,31-undecazacyclotetratriacontane-2,5,8,11,14,17,20,23,26,29,32-undecone, (1389) (3S,9S,12S,15R,18S,27S,30S,34R)-12-[2-[3-chloro-4-(trifluoromethyl)phenyl]ethyl]-18-(cyclohexylmethyl)-3,9,30-triisobutyl-1,6,6,7,15,16,19,22,25,31,34-undecamethyl-27-[(1S)-1-methylpropyl]-1,4,7,10,13,16,19,22,25,28,31-undecazacyclotetratriacontane-2,5,8,11,14,17,20,23,26,29,32-undecone, (1390) (3S,9S,12S,15R,18S,27S,30S,34R)-12-[2-[3-chloro-4-(trifluoromethyl)phenyl]ethyl]-18-(cyclohexylmethyl)-3,9-diisobutyl-1,6,6,7,15,16,19,22,25,30,31,34-dodecamethyl-27-[(1S)-1-methylpropyl]-1,4,7,10,13,16,19,22,25,28,31-undecazacyclotetratriacontane-2,5,8,11,14,17,20,23,26,29,32-undecone, (1391) (3S,6S,9S,13R,16S,22S,25S,31S,34S)-25-[2-[3-chloro-4-(trifluoromethyl)phenyl]ethyl]-31-(cyclohexylmethyl)-16,22-diisobutyl-3,4,9,10,13,14,19,19,20,29,32-undecamethyl-6-[(1S)-1-methylpropyl]-1,4,7,10,14,17,20,23,26,29,32-undecazabicyclo[32.2.0]hexatriacontane-2,5,8,11,15,18,21,24,27,30,33-undecone, (1392) (6S,9S,13R,16S,22S,25S,31S,34S)-25-[2-[3-chloro-4-(trifluoromethyl)phenyl]ethyl]-16,22-diisobutyl-4,9,10,13,14,19,19,20,29,32-decamethyl-6-[(1S)-1-methylpropyl]-31-[[4-(trifluoromethyl)phenyl]methyl]-1,4,7,10,14,17,20,23,26,29,32-undecazabicyclo[32.2.0]hexatriacontane-2,5,8,11,15,18,21,24,27,30,33-undecone, (1393) (3S,9S,12S,15R,18S,27S,30S,34R)-12-[2-[3-chloro-4-(trifluoromethyl)phenyl]ethyl]-3,9,30-triisobutyl-1,6,6,7,15,16,19,22,25,31,34-undecamethyl-27-[(1S)-1-methylpropyl]-18-[[4-(trifluoromethyl)phenyl]methyl]-1,4,7,10,13,16,19,22,25,28,31-undecazacyclotetratriacontane-2,5,8,11,14,17,20,23,26,29,32-undecone, (1394) (6S,9S,13R,16S,22S,25S,28R,31S,34S)-25-[2-[3-chloro-4-(trifluoromethyl)phenyl]ethyl]-9,16,22-triisobutyl-4,10,13,14,19,19,20,28,29,32-decamethyl-6-[(1S)-1-methylpropyl]-31-(p-tolylmethyl)-1,4,7,10,14,17,20,23,26,29,32-undecazabicyclo[32.2.0]hexatriacontane-2,5,8,11,15,18,21,24,27,30,33-undecone, (1395) (6S,9S,13R,16S,22S,25S,28R,31S,34S)-25-[2-[3-chloro-4-(trifluoromethyl)phenyl]ethyl]-9,16,22-triisobutyl-4,10,13,14,19,19,20,28,29,32-decamethyl-6-[(1S)-1-methylpropyl]-31-[[4-(trifluoromethyl)phenyl]methyl]-1,4,7,10,14,17,20,23,26,29,32-undecazabicyclo[32.2.0]hexatriacontane-2,5,8,11,15,18,21,24,27,30,33-undecone, (1396) (3S,9S,12S,18S,27S,30S,34R)-12-[2-[3-chloro-4-(trifluoromethyl)phenyl]ethyl]-3,9,30-triisobutyl-1,6,6,7,16,19,22,25,31,34-decamethyl-27-[(1S)-1-methylpropyl]-18-[[4-(trifluoromethyl)phenyl]methyl]-1,4,7,10,13,16,19,22,25,28,31-undecazacyclotetratriacontane-2,5,8,11,14,17,20,23,26,29,32-undecone, (1397) (3S,9S,12S,18S,27S,30S,34R)-12-[2-[3-chloro-4-(trifluoromethyl)phenyl]ethyl]-3,9-diisobutyl-1,6,6,7,16,19,22,25,30,31,34-undecamethyl-27-[(1S)-1-methylpropyl]-18-[[4-(trifluoromethyl)phenyl]methyl]-1,4,7,10,13,16,19,22,25,28,31-undecazacyclotetratriacontane-2,5,8,11,14,17,20,23,26,29,32-undecone, (1398) (3S,9S,12S,18S,27S,30S,34R)-12-[2-[3-chloro-4-(trifluoromethyl)phenyl]ethyl]-3,9-diisobutyl-1,6,6,7,16,19,22,25,30,31,34-undecamethyl-27-[(1S)-1-methylpropyl]-18-(p-tolylmethyl)-1,4,7,10,13,16,19,22,25,28,31-undecazacyclotetratriacontane-2,5,8,11,14,17,20,23,26,29,32-undecone, (1399) (3S,6S,9S,13R,16S,22S,25S,31S,34S)-25-[2-[3-chloro-4-(trifluoromethyl)phenyl]ethyl]-16,22-diisobutyl-3,4,9,10,13,14,19,19,20,29,32-undecamethyl-6-[(1S)-1-methylpropyl]-31-[[4-(trifluoromethyl)phenyl]methyl]-1,4,7,10,14,17,20,23,26,29,32-undecazabicyclo[32.2.0]hexatriacontane-2,5,8,11,15,18,21,24,27,30,33-undecone, (1400) (6S,9S,13R,16S,22S,25S,28R,31S,34S)-25-[2-[3-chloro-4-(trifluoromethyl)phenyl]ethyl]-31-(cyclohexylmethyl)-9,16,22-triisobutyl-4,10,13,14,19,19,20,28,29,32-decamethyl-6-[(1S)-1-methylpropyl]-1,4,7,10,14,17,20,23,26,29,32-undecazabicyclo[32.2.0]hexatriacontane-2,5,8,11,15,18,21,24,27,30,33-undecone, (1401) (3S,6S,9S,13R,16S,22S,25S,31S,34S)-25-[2-[3-chloro-4-(trifluoromethyl)phenyl]ethyl]-9,16,22-triisobutyl-3,4,10,13,14,19,19,20,29,32-decamethyl-6-

[(1S)-1-methylpropyl]-31-[[4-(trifluoromethyl)phenyl] methyl]-1,4,7,10,14,17,20,23,26,29,32-undecazabicyclo [32.2.0]hexatriacontane-2,5,8,11,15,18,21,24,27,30,33-undecone, (1402) (3S,6S,9S,13R,16S,22S,25S,31S,34S)-25-[2-[3-chloro-4-(trifluoromethyl)phenyl]ethyl]-16,22-diisobutyl-3,4,9,10,13,14,19,19,20,29,32-undecamethyl-6-[(1S)-1-methylpropyl]-31-(p-tolylmethyl)-1,4,7,10,14,17,20,23,26,29,32-undecazabicyclo[32.2.0] hexatriacontane-2,5,8,11,15,18,21,24,27,30,33-undecone, (1403) (6S,9S,13R,16S,22S,25S,31S,34S)-25-[2-[3-chloro-4-(trifluoromethyl)phenyl]ethyl]-9,16,22-triisobutyl-4,10,13,14,19,19,20,29,32-nonamethyl-6-[(1S)-1-methylpropyl]-31-[[4-(trifluoromethyl)phenyl]methyl]-1,4,7,10,14,17,20,23,26,29,32-undecazabicyclo[32.2.0] hexatriacontane-2,5,8,11,15,18,21,24,27,30,33-undecone, (1404) (3S,9S,12S,18S,27S,30S,34S)-12-[(3-bromophenyl) methyl]-9-butyl-18-[(4-chlorophenyl)methyl]-3,30-diisobutyl-1,6,6,7,16,19,22,25,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (1405) (3S,6S,9S,13S,16S,22S,25S,31S,34S)-31-(cyclopentylmethyl)-25-[(3-iodophenyl)methyl]-9,16-diisobutyl-3,4,10,14,19,19,20,29,32-nonamethyl-22-(2-methylallyl)-6-[(1S)-1-methylpropyl]-13-(piperidine-1-carbonyl)-1,4,7,10,14,17,20,23,26,29,32-undecazabicyclo[32.2.0] hexatriacontane-2,5,8,11,15,18,21,24,27,30,33-undecone, (1406) (3S,9S,12S,18S,27S,30S,34R)-12-[(3-iodophenyl) methyl]-3,30-diisobutyl-1,6,6,7,16,19,22,25,31,34-decamethyl-27-[(1S)-1-methylpropyl]-9-prop-2-ynyl-18-[[4-(trifluoromethyl)phenyl]methyl]-1,4,7,10,13,16,19,22,25,28,31-undecazacyclotetratriacontane-2,5,8,11,14,17,20,23,26,29,32-undecone, (1407) (3S,9S,12S,18S,27S,30S,34S)-9-butyl-12-[(3-chlorophenyl)methyl]-18-[(4-chlorophenyl)methyl]-3,30-diisobutyl-1,6,6,7,16,19,22,25,31-nonamethyl-27-[(1S)-1-methylpropyl]-34-(pyrrolidine-1-carbonyl)-1,4,7,10,13,16,19,22,25,28,31-undecazacyclotetratriacontane-2,5,8,11,14,17,20,23,26,29,32-undecone, (1408) (6S,9S,13R,16S,22S,25S,31S,34S)-31-[(4-chlorophenyl)methyl]-25-[(3-iodophenyl)methyl]-9,16-diisobutyl-4,10,13,14,19,19,20,29,32-nonamethyl-22-(3-methylbut-2-enyl)-6-[(1S)-1-methylpropyl]-1,4,7,10,14,17,20,23,26,29,32-undecazabicyclo[32.2.0] hexatriacontane-2,5,8,11,15,18,21,24,27,30,33-undecone, (1409) (3S,9S,12S,18S,27S,30S,34S)-3-benzyl-9-butyl-8-[(4-chlorophenyl)methyl]-12-[(3-iodophenyl)methyl]-30-isobutyl-1,6,6,7,16,19,22,25,31-nonamethyl-27-[(1S)-1-methylpropyl]-34-(pyrrolidine-1-carbonyl)-1,4,7,10,13,16,19,22,25,28,31-undecazacyclotetratriacontane-2,5,8,11,14,17,20,23,26,29,32-undecone, (1410) (3S,9S,12S,18S,27S,30S,34S)-9-butyl-18-[(4-chlorophenyl)methyl]-12-[(3-iodophenyl)methyl]-30-isobutyl-1,6,6,7,16,19,22,25,31-nonamethyl-27-[(1S)-1-methylpropyl]-3-propyl-34-(pyrrolidine-1-carbonyl)-1,4,7,10,13,16,19,22,25,28,31-undecazacyclotetratriacontane-2,5,8,11,14,17,20,23,26,29,32-undecone, (1411) (1S,7S,10S,14S,17S,26S,32S)-32-[(3-iodophenyl) methyl]-7,14-diisobutyl-3,4,4,9,13,19,22,25,28-nonamethyl-17-[(1S)-1-methylpropyl]-10-(piperidine-1-carbonyl)-3,6,9,13,16,19,22,25,28,31,34-undecazabicyclo [24.8.6]tetracontane-2,5,8,12,15,18,21,24,27,30,33-undecone, (1412) (3S,9S,12S,18S,27S,30S,34S)-9-butyl-18-[(4-chlorophenyl)methyl]-3,30-diisobutyl-12-[(3-methoxyphenyl)methyl]-1,6,6,7,16,19,22,25,31-nonamethyl-27-[(1S)-1-methylpropyl]-34-(pyrrolidine-1-carbonyl)-1,4,7,10,13,16,19,22,25,28,31-undecazacyclotetratriacontane-2,5,8,11,14,17,20,23,26,29,32-undecone, (1413) (3S,6S,9S,13S,16S,22S,25S,31S,34S)-22-butyl-31-(cyclobutylmethyl)-25-[(3-iodophenyl)methyl]-9,16-diisobutyl-3,4,10,14,19,19,20,29,32-nonamethyl-6-[(1S)-1-methylpropyl]-13-(piperidine-1-carbonyl)-1,4,7,10,14,17,20,23,26,29,32-undecazabicyclo[32.2.0] hexatriacontane-2,5,8,11,15,18,21,24,27,30,33-undecone, (1414) (6S,9S,13S,16S,22S,25S,31S,34S)-31-[(4-chlorophenyl)methyl]-25-[(3-iodophenyl)methyl]-9,16-diisobutyl-4,10,14,19,19,20,29,32-octamethyl-22-(2-methylallyl)-6-[(1S)-1-methylpropyl]-13-(piperidine-1-carbonyl)-1,4,7,10,14,17,20,23,26,29,32-undecazabicyclo[32.2.0]hexatriacontane-2,5,8,11,15,18,21,24,27,30,33-undecone, (1415) (3S,6S,9S,13S,16S,22S,25S,31S,34S)-25-[(3-bromophenyl)methyl]-22-butyl-31-[(4-chlorophenyl)methyl]-9,16-diisobutyl-3,4,10,14,19,19,20,29,32-nonamethyl-6-[(1S)-1-methylpropyl]-13-(piperidine-1-carbonyl)-1,4,7,10,14,17,20,23,26,29,32-undecazabicyclo[32.2.0] hexatriacontane-2,5,8,11,15,18,21,24,27,30,33-undecone, (1416) (3S,9S,12S,18S,27S,30S,34S)-9-butyl-18-(cyclohexylmethyl)-12-[(3-iodophenyl)methyl]-3,30-diisobutyl-1,6,6,7,16,19,22,25,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (1417) (6S,9S,13S,16S,22S,25S,31S,34S)-22-butyl-9-hexyl-25-[(3-iodophenyl)methyl]-16-isobutyl-31-[(4-methoxyphenyl)methyl]-4,10,14,19,19,20,29,32-octamethyl-6-f[(1S)-1-methylpropyl]-13-(piperidine-1-carbonyl)-1,4,7,10,14,17,20,23,26,29,32-undecazabicyclo[32.2.0]hexatriacontane-2,5,8,11,15,18,21,24,27,30,33-undecone, (1418) (3S,9S,12S,18S,27S,30S,34R)-18-[(4-chlorophenyl) methyl]-12-[(3-iodophenyl)methyl]-3,30-diisobutyl-1,6,6,7,16,19,22,25,31,34-decamethyl-9-(3-methylbut-2-enyl)-27-[(1S)-1-methylpropyl]-1,4,7,10,13,16,19,22,25,28,31-undecazacyclotetratriacontane-2,5,8,11,14,17,20,23,26,29,32-undecone, (1419) (3S,6S,9S,13S,16S,22S,25S,31S,34S)-31-[(4-chlorophenyl)methyl]-25-[(3-iodophenyl)methyl]-9,16-diisobutyl-3,4,10,14,19,19,20,29,32-nonamethyl-22-(3-methylbut-2-enyl)-6-[(1S)-1-methylpropyl]-13-(piperidine-1-carbonyl)-1,4,7,10,14,17,20,23,26,29,32-undecazabicyclo[32.2.0]hexatriacontane-2,5,8,11,15,18,21,24,27,30,33-undecone, (1420) (6S,9S,13S,16S,22S,25S,31S,34S)-22-butyl-31-(cyclohexylmethyl)-25-[(3-iodophenyl)methyl]-9,16-diisobutyl-4,10,14,19,19,20,29,32-octamethyl-6-[(1S)-1-methylpropyl]-13-(piperidine-1-carbonyl)-1,4,7,10,14,17,20,23,26,29,32-undecazabicyclo[32.2.0] hexatriacontane-2,5,8,11,15,18,21,24,27,30,33-undecone, (1421) (3S,9S,12S,18S,27S,30S,34S)-18-[(4-chlorophenyl) methyl]-12-[(3-iodophenyl)methyl]-3,30-diisobutyl-1,6,6,7,16,19,22,25,31-nonamethyl-9-(2-methylallyl)-27-[(1S)-1-methylpropyl]-34-(piperidine-1-carbonyl)-1,4,7, 10,13,16,19,22,25,28,31-undecazacyclotetratriacontane-2,5,8,11,14,17,20,23,26,29,32-undecone, (1422) (3S,9S,12S,18S,27S,30S,34S)-9-butyl-18-[(4-chlorophenyl)methyl]-3-(cyclobutylmethyl)-12-[(3-iodophenyl)methyl]-30-isobutyl-1,6,6,7,16,19,22,25,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (1423) (3S,9S,12S,18S,27S,30S,34S)-9-butyl-18-(cyclopentylmethyl)-12-[(3-iodophenyl)methyl]-3,30-diisobutyl-1,6,6,7,16,19,22,25,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (1424) (2aS,5S,11S,14S,20S,23S,30aS,33S,36S)-33-((S)-sec-butyl)-14-butyl-5-(cyclopentylmethyl)-11-(3-iodobenzyl)-20-isobutyl-4,7,16,17,17,22,35,36-octamethyl-23-(piperidine-1-carbonyl)tetracosahydroazeto[1,2-j]pyrido[1,2-a][1,4,7,10,13,16,19,22,25,28,31]undecaazacyclotetratriacontin-3,6,9,12,15,18,21,25,31,34,37(1H,22H,27H)-undecaone, (1425) (6S,9S,13S,16S,22S,25S,31S,34S)-25-[(3-iodophenyl)methyl]-9,16-diisobutyl-4,10,14,19,19,20,29,32-octamethyl-6-[(1S)-1-methylpropyl]-13-(piperidine-1-carbonyl)-22-prop-2-ynyl-31-[[4-(trifluoromethyl)phenyl]methyl]-1,4,7,10,14,17,20,23,26,29,32-undecazabicyclo[32.2.0]hexatriacontane-2,5,8,11,15,18,21,24,27,30,33-undecone, (1426) (3S,9S,12S,18S,27S,30S,34S)-18-[(4-chlorophenyl)methyl]-12-[(3-iodophenyl)methyl]-3,30-diisobutyl-1,6,6,7,16,19,22,25,31-nonamethyl-27-[(1S)-1-methylpropyl]-34-(piperidine-1-carbonyl)-9-prop-2-ynyl-1,4,7,10,13,16,19,22,25,28,31-undecazacyclotetratriacontane-2,5,8,11,14,17,20,23,26,29,32-undecone, (1427) (6S,9S,13R,16S,22S,25S,31S,34S)-25-[(3-iodophenyl)methyl]-9,16-diisobutyl-4,10,13,14,19,19,20,29,32-nonamethyl-6-[(1S)-1-methylpropyl]-22-prop-2-ynyl-31-[[4-(trifluoromethyl)phenyl]methyl]-1,4,7,10,14,17,20,23,26,29,32-undecazabicyclo[32.2.0]hexatriacontane-2,5,8,11,15,18,21,24,27,30,33-undecone, (1428) (3S,6S,9S,13S,16S,22S,25S,31S,34S)-31-[(4-chlorophenyl)methyl]-25-[(3-iodophenyl)methyl]-9,16-diisobutyl-3,4,10,14,19,19,20,29,32-nonamethyl-6-[(1S)-1-methylpropyl]-13-(piperidine-1-carbonyl)-22-prop-2-ynyl-1,4,7,10,14,17,20,23,26,29,32-undecazabicyclo[32.2.0]hexatriacontane-2,5,8,11,15,18,21,24,27,30,33-undecone, (1429) (3S,6S,9S,13S,16S,22S,25S,31S,34S)-31-[(4-chlorophenyl)methyl]-25-[(3-iodophenyl)methyl]-9,16-diisobutyl-3,4,10,14,19,19,20,29,32-nonamethyl-22-(2-methylallyl)-6-[(1S)-1-methylpropyl]-13-(piperidine-1-carbonyl)-1,4,7,10,14,17,20,23,26,29,32-undecazabicyclo[32.2.0]hexatriacontane-2,5,8,11,15,18,21,24,27,30,33-undecone, (1430) (3S,9S,12S,18S,27S,30S,34S)-9-butyl-18-[(4-chlorophenyl)methyl]-12-[(3-iodophenyl)methyl]-30-isobutyl-1,6,6,7,16,19,22,25,31-nonamethyl-27-[(1S)-1-methylpropyl]-3-(2-phenylethyl)-34-(pyrrolidine-1-carbonyl)-1,4,7,10,13,16,19,22,25,28,31-undecazacyclotetratriacontane-2,5,8,11,14,17,20,23,26,29,32-undecone, (1431) (3S,9S,12S,18S,27S,30S,34S)-9-allyl-18-[(4-chlorophenyl)methyl]-12-[(3-iodophenyl)methyl]-3,30-diisobutyl-1,6,6,7,16,19,22,25,31-nonamethyl-27-[(1S)-1-methylpropyl]-34-(pyrrolidine-1-carbonyl)-1,4,7,10,13,16,19,22,25,28,31-undecazacyclotetratriacontane-2,5,8,11,14,17,20,23,26,29,32-undecone, (1432) (3S,6S,9S,13S,16S,22S,25S,31S,34S)-22-butyl-31-(cyclopentylmethyl)-25-[(3-iodophenyl)methyl]-9,16-diisobutyl-3,4,10,14,19,19,20,29,32-nonamethyl-6-[(1S)-1-methylpropyl]-13-(piperidine-1-carbonyl)-1,4,7,10,14,17,20,23,26,29,32-undecazabicyclo[32.2.0]hexatriacontane-2,5,8,11,15,18,21,24,27,30,33-undecone, (1433) (3S,9S,12S,18S,27S,30S,34S)-9-butyl-12-[(3-iodophenyl)methyl]-30-isobutyl-3-isopentyl-1,6,6,7,16,19,22,25,31-nonamethyl-27-[(1S)-1-methylpropyl]-34-(piperidine-1-carbonyl)-18-[[4-(trifluoromethyl)phenyl]methyl]-1,4,7,10,13,16,19,22,25,28,31-undecazacyclotetratriacontane-2,5,8,11,14,17,20,23,26,29,32-undecone, (1434) (3S,6S,9S,13S,16S,22R,25S,31S,34S)-22-benzyl-25-[2-[3-chloro-4-(trifluoromethyl)phenyl]ethyl]-31-(cyclohexylmethyl)-16-cyclopentyl-9-isobutyl-3,4,10,14,17,23,29,32-octamethyl-6-[(1S)-1-methylpropyl]-13-(piperidine-1-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (1435) (8R,11S,17S,26S,29S,33S,36S)-11-[2-[3-chloro-4-(trifluoromethyl)phenyl]ethyl]-36-cyclohexyl-17-(cyclohexylmethyl)-8-ethyl-29-isobutyl-9,15,18,21,24,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (1436) (8R,11S,17S,26S,29S,33S,36S)-11-[2-[3-chloro-4-(trifluoromethyl)phenyl]ethyl]-36-cyclohexyl-17-(cyclohexylmethyl)-29-isobutyl-8-(isopentyloxymethyl)-9,15,18,21,24,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (1437) (3S,6S,9S,13S,16S,22R,25S,31S,34S)-25-[2-[3-chloro-4-(trifluoromethyl)phenyl]ethyl]-31-(cyclohexylmethyl)-9-isobutyl-22-(isopentyloxymethyl)-16-isopropyl-3,4,10,14,17,23,29,32-octamethyl-6-[(1S)-1-methylpropyl]-13-(piperidine-1-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (1438) (3S,6S,9S,13S,16S,22R,25S,31S,34S)-25-[2-[3-chloro-4-(trifluoromethyl)phenyl]ethyl]-31-(cyclohexylmethyl)-22-ethyl-9-isobutyl-16-isopropyl-3,4,10,14,17,23,29,32-octamethyl-6-[(1S)-1-methylpropyl]-13-(piperidine-1-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (1439) (8R,11S,17S,26S,29S,33S,36S)-11-[2-[3-chloro-4-(trifluoromethyl)phenyl]ethyl]-17-(cyclohexylmethyl)-36-cyclopentyl-8-ethyl-29-isobutyl-9,15,18,21,24,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (1440) (8R,11S,17S,26S,29S,33S,36S)-11-[2-[3-chloro-4-(trifluoromethyl)phenyl]ethyl]-17-(cyclohexylmethyl)-36-cyclopentyl-29-isobutyl-8-(isopentyloxymethyl)-9,15,18,21,24,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (1441) (3S,6S,9S,13S,16S,22R,25S,31S,34S)-25-[2-[3-chloro-4-(trifluoromethyl)phenyl]ethyl]-31-(cyclohexylmethyl)-16-cyclopentyl-22-ethyl-9-isobutyl-3,4,10,14,17,23,29,32-octamethyl-6-[(1S)-1-methylpropyl]-13-(piperidine-1-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (1442) (3S,6S,9S,13S,16S,22R,25S,31S,34S)-22-benzyl-25-[2-[3-chloro-4-(trifluoromethyl)phenyl]ethyl]-31-(cyclohexylmethyl)-9-isobutyl-16-isopropyl-3,4,10,14,17,23,29,32-octamethyl-6-[(1S)-1-methylpropyl]-13-(piperidine-1-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (1443) (3S,6S,9S,13S,16S,22R,25S,31S,34S)-25-[2-[3-chloro-4-(trifluoromethyl)phenyl]ethyl]-31-(cyclohexylmethyl)-16-cyclopentyl-9-isobutyl-22-(isopentyloxymethyl)-3,4,10,14,17,23,29,32-octamethyl-6-[(1S)-1-methylpropyl]-13-(piperidine-1-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (1444) (3S,6S,9S,13S,16S,22R,25S,31S,34S)-25-[2-[3-chloro-4-(trifluoromethyl)phenyl]ethyl]-31-(cyclohexylmethyl)-22-(hydroxymethyl)-9-isobutyl-16-isopropyl-3,4,10,14,17,23,29,32-octamethyl-6-[(1S)-1-methylpropyl]-13-(piperidine-1-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (1445) (3S,9S,18S,21S,25S,28S,34R)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-25-(piperidine-1-carbonyl)spiro[36-oxa-1,4,7,10,13,16,19,22,26,29,32-undecazabicyclo[32.4.0]octatriacontane-31,1'-cyclopentane]-2,5,8,11,14,17,20,23,27,30,33-undecone, (1446) (8R,11S,17S,26S,29S,33S,36S)-8-benzyl-11-[2-[3-chloro-4-(trifluoromethyl)phenyl]ethyl]-17-(cyclohexylmethyl)-36-cyclopentyl-29-isobutyl-9,15,18,21,24,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (1447) (3S,6S,9S,13S,16S,22S,25S,31S,34S)-22-allyl-25-[2-[3-chloro-4-(trifluoromethyl)phenyl]ethyl]-31-(cyclohexylmethyl)-9-isobutyl-16-isopropyl-3,4,10,14,17,23,29,32-octamethyl-6-[(1S)-1-methylpropyl]-13-(piperidine-1-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (1448) (8R,11S,17S,26S,29S,33S,36S)-11-[2-[3-chloro-4-(trifluoromethyl)phenyl]ethyl]-36-cyclohexyl-17-(cyclohexylmethyl)-8-(hydroxymethyl)-29-isobutyl-9,15,18,21,24,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (1449) (8S,11S,17S,26S,29S,33S,36S)-8-allyl-11-[2-[3-chloro-4-(trifluoromethyl)phenyl]ethyl]-36-cyclohexyl-17-(cyclohexylmethyl)-29-isobutyl-9,15,18,21,24,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (1450) (3S,6S,9S,12S,18S,27S,30S,34S)-6-benzyl-27-cyclohexyl-18-(5,5-difluoropentyl)-12-[2-[3-fluoro-4-(trifluoromethyl)phenyl]ethyl]-3,9,30-triisobutyl-4,6,10,16,19,22,25,31-octamethyl-34-(pyrrolidine-1-carbonyl)-1,4,7,10,13,16,19,22,25,28,31-undecazacyclotetratriacontane-2,5,8,11,14,17,20,23,26,29,32-undecone, (1451) (3S,9S,12S,18S,27S,30S,34R)-12-[2-[3-chloro-4-(trifluoromethyl)phenyl]ethyl]-18-(5,5-difluoropentyl)-3,9,30-triisobutyl-4,6,6,10,16,19,22,25,31,34-decamethyl-27-[(1S)-1-methylpropyl]-1,4,7,10,13,16,19,22,25,28,31-undecazacyclotetratriacontane-2,5,8,11,14,17,20,23,26,29,32-undecone, (1452) (3S,9S,18S,21S,25R,28S,34S)-3-[2-[3-chloro-4-(trifluoromethyl)phenyl]ethyl]-9-(cyclohexylmethyl)-21,28-diisobutyl-18-isopropyl-7,10,13,16,22,25,29-heptamethyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1453) (3S,9S,12S,18S,27S,30S,34S)-27-cyclohexyl-18-(5,5-difluoropentyl)-12-[2-[3-fluoro-4-(trifluoromethyl)phenyl]ethyl]-3,9,30-triisobutyl-4,6,6,10,16,19,22,25,31-nonamethyl-34-(pyrrolidine-1-carbonyl)-1,4,7,10,13,16,19,22,25,28,31-undecazacyclotetratriacontane-2,5,8,11,14,17,20,23,26,29,32-undecone, (1454) (3S,9S,18S,21S,25S,28S,34S)-9-(cyclohexylmethyl)-3-[2-[3-fluoro-4-(trifluoromethyl)phenyl]ethyl]-21-isobutyl-28-isopropyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1455) (3S,9S,12S,18S,27S,30S,34S)-18-(5,5-difluoropentyl)-12-[2-[3-fluoro-4-(trifluoromethyl)phenyl]ethyl]-3,9,30-triisobutyl-4,6,6,10,16,19,22,25,31-nonamethyl-27-[(1S)-1-methylpropyl]-34-(pyrrolidine-1-carbonyl)-1,4,7,10,13,16,19,22,25,28,31-undecazacyclotetratriacontane-2,5,8,11,14,17,20,23,26,29,32-undecone, (1456) (3S,9S,12S,18S,27S,30S,34S)-18-(5,5-difluoropentyl)-12-[2-[3-fluoro-4-(trifluoromethyl)phenyl]ethyl]-3,9,30-triisobutyl-1,4,6,6,10,16,19,22,25,31-decamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (1457) (3S,9S,18S,21S,25R,28S,34S)-3-[2-[3-chloro-4-(trifluoromethyl)phenyl]ethyl]-9-(cyclohexylmethyl)-21-isobutyl-28-isopropyl-7,10,13,16,22,25,29-heptamethyl-8-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1458) (3S,9S,18S,21S,25S,28S,34S)-9-(cyclohexylmethyl)-3-[2-[3-fluoro-4-(trifluoromethyl)phenyl]ethyl]-21,28-diisobutyl-18-isopropyl-7,10,13,16,22,26,29-heptamethyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1459) (3S,9S,15S,18S,21S,25R,28S,34S)-3-[2-[3-chloro-4-(trifluoromethyl)phenyl]ethyl]-9-(cyclohexylmethyl)-15-ethyl-21-isobutyl-28-isopropyl-7,10,13,22,25,29-hexamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1460) (3S,9S,12S,18S,27S,30S,34R)-27-cyclohexyl-18-(5,5-difluoropentyl)-12-[2-[3-fluoro-4-(trifluoromethyl)phenyl]ethyl]-3,9,30-triisobutyl-4,6,6,10,16,19,22,25,31, 34-decamethyl-1,4,7,10,13,16,19,22,25,28,31-undecazacyclotetratriacontane-2,5,8,11,14,17,20,23,26,29,32-undecone, (1461) (8S,11S,15R,18S,23aS,29S,32R,35S,37aS)-8-((S)-sec-butyl)-29-(3-chloro-4-(trifluoromethyl)phenethyl)-18-cyclopentyl-6,11,12,15,19,32,33,36-octamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1462) (8S,11S,15R,18S,23aS,29S,35S,37aS)-8-((S)-sec-butyl)-29-(3-chloro-4-(trifluoromethyl)phenethyl)-18-cyclopentyl-6,11,12,15,19,33,36-heptamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1463) (8S,11S,15R,18S,23aS,29S,35S,37aS)-8-((S)-sec-butyl)-29-(3-chloro-4-(trifluoromethyl)phenethyl)-18-cyclopentyl-6,11,12,15,19,33,36-heptamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1464) (8S,11S,17S,26S,29S,33R,36S)-11-[2-[3-chloro-4-(trifluoromethyl)phenyl]ethyl]-24-ethyl-8-[(2-hydroxy-2-methyl-propoxy)methyl]-29,36-diisobutyl-17-(isopentyloxymethyl)-9,15,18,21,30,33,37-heptamethyl-26-[(1S)-1-methylpropyl]-6,9,12,15,18,21,24,27,30,34,37-undecazaspiro[4.33]octatriacontane-7,10,13,16,19,22,25,28,31,35,38-undecone, (1465) (3S,6R,9S,18S,21S,25R,28S,34S)-3-[2-[3-chloro-4-(trifluoromethyl)phenyl]ethyl]-28-cyclopentyl-6,7,10,13,16,21,22,25,29-nonamethyl-18-[(1S)-1-methylpropyl]-9-(p-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1466) (3S,9S,18S,21S,25R,28S,34S)-3-[2-[3-chloro-4-(trifluoromethyl)phenyl]ethyl]-28-cyclopentyl-7,10,13,16,21,22,25,29-octamethyl-18-[(1S)-1-methylpropyl]-9-(p-tolylmethyl)spiro[1,4,7,10,13,16,19,22,26,29,32-undecazabicyclo[32.3.0]heptatriacontane-31,1'-cyclobutane]-2,5,8,11,14,17,20,23,27,30,33-undecone, (1467) N-tert-butyl-2-[[(3S,9S,12S,18S,27S,30S,34R)-12-[2-[3-chloro-4-(trifluoromethyl)phenyl]ethyl]-3,30-diisobutyl-18-(isopentyloxymethyl)-4,6,6,10,16,19,22,25,31,34-decamethyl-27-[(1S)-1-methylpropyl]-2,5,8,11,14,17,20,23,26,29,32-undecaoxo-1,4,7,10,13,16,19,22,25,28,31-undecazacyclotetratriacont-9-yl]methoxy]acetamide, (1468) (8S,11S,15R,18S,23aS,29S,32R,35S,37aS)-8-((S)-sec-butyl)-29-(3-chloro-4-(trifluoromethyl)phenethyl)-18-cyclopentyl-11-isobutyl-6,12,15,19,32,33,36-heptamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1469) (3S,9S,18S,21S,25R,28S,34S)-9-(cyclohexylmethyl)-28-ethyl-3-[2-[3-fluoro-4-(trifluoromethyl)phenyl]ethyl]-21-isobutyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1470) (6'S,15'S,18'S,22'R,25'S,30a'S,36'S,38a'R)-15'-((S)-sec-butyl)-36'-(3-chloro-4-(trifluoromethyl)phenethyl)-25'-cyclopentyl-7',10',13',18',19',22',26'-heptamethyl-6'-(4-(trifluoromethyl)benzyl)tetracosahydro-5'H-spiro[cyclopentane-1,28'-dipyrrolo[2,1-i:2',1'-o][1,4,7,10,13,16,19,22,25,28,31]undecaazacyclotetratriacontin]-5',8',11',14',17',20',24',27',30',35',38'(21'H,29'H)-undecaone, (1471) (3S,9S,18S,21S,25R,28S,34S)-3-[2-[3-chloro-4-(trifluoromethyl)phenyl]ethyl]-28-cyclopentyl-21-isobutyl-7,10,13,16,22,25,29-heptamethyl-18-[(1S)-1-methylpropyl]-9-(p-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1472) (6S,9S,13R,16S,22S,25S,31S,34S)-25-[2-[3-chloro-4-(trifluoromethyl)phenyl]ethyl]-4-ethyl-22-[(2-hydroxy-2-methyl-propoxy)methyl]-9,16-diisobutyl-31-(isopentyloxymethyl)-10,13,17,19,19,23,29,32-octamethyl-6-[(1S)-1-methylpropyl]-1,4,7,10,14,17,20,23,26,29,32-undecazabicyclo[32.2.0]hexatriacontane-2,5,8,11,15,18,21,24,27,30,33-undecone, (1473) (3S,9S,12S,18S,27S,30S,34R)-25-butyl-12-[2-[3-chloro-4-(trifluoromethyl)phenyl]ethyl]-9-1[(2-hydroxy-2-methyl-propoxy)methyl]-3,30-diisobutyl-18-(isopentyloxymethyl)-4,6,6,16,19,22,31,34-octamethyl-27-[(1S)-1-methylpropyl]-1,4,7,10,13,16,19,22,25,28,31-undecazacyclotetratriacontane-2,5,8,11,14,17,20,23,26,29,32-undecone, (1474) (3S,9S,12S,18S,27S,30S,34R)-18-(cyclohexylmethyl)-12-[2-[3-fluoro-4-(trifluoromethyl)phenyl]ethyl]-3,9,30-triisobutyl-4,6,6,10,16,19,22,25,31,34-decamethyl-27-prop-2-ynyl-1,4,7,10,13,16,19,22,25,28,31-undecazacyclotetratriacontane-2,5,8,11,14,17,20,23,26,29,32-undecone, (1475) (5S,8S,11S,15R,18S,23aS,29S,35S,37aS)-8-((S)-sec-butyl)-29-(3-chloro-4-(trifluoromethyl)phenethyl)-18-cyclopentyl-11-isobutyl-5,6,12,15,19,33,36-heptamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1476) (3S,9S,12S,18S,27S,30S,34R)-12-[2-[3-chloro-4-(trifluoromethyl)phenyl]ethyl]-25-ethyl-30-[(2-hydroxy-2-methyl-propoxy)methyl]-3,9-diisobutyl-18-(isopentyloxymethyl)-4,6,6,10,16,19,22,31,34-nonamethyl-27-[(1S)-1-methylpropyl]-1,4,7,10,13,16,19,22,25,28,31-undecazacyclotetratriacontane-2,5,8,11,14,17,20,23,26,29,32-undecone, (1477) (5S,8S,11S,15R,18S,23aS,29S,35S,37aS)-8-((S)-sec-butyl)-29-(3-chloro-4-(trifluoromethyl)phenethyl)-35-(cyclohexylmethyl)-18-cyclopentyl-11-isobutyl-5,6,12,15,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1478) (3S,9S,18S,21S,25R,28S,34S)-3-[2-[3-chloro-4-(trifluoromethyl)phenyl]ethyl]-9-(cyclohexylmethyl)-28-cyclopentyl-7,10,13,16,21,22,25,29-octamethyl-8-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1479) (8S,11S,15R,18S,23aS,29S,31aR,37S,39aS)-8-((S)-sec-butyl)-29-(3-chloro-4-(trifluoromethyl)phenethyl)-37-(cyclohexylmethyl)-18-cyclopentyl-6,11,12,15,19,38-hexamethyltetracosahydro-2H,4H-spiro[azeto[2,1-u]dipyrrolo[2,1-i:2',1'-o][1,4,7,10,13,16,19,22,25,28,31]undecaazacyclotetratriacontine-21,1'-cyclopentan]-4,7,10,13,17,20,23,28,31,36,39(14H,22H)-undecaone, (1480) N-tert-butyl-2-[[(3S,9S,12S,18S,27S,30S,34R)-12-[2-[3-chloro-4-(trifluoromethyl)phenyl]ethyl]-3,30-diisobutyl-18-(isopentyloxymethyl)-1,4,6,6,10,16,19,22, 25,31-decamethyl-27-[(1S)-1-methylpropyl]-2,5,8,11,14, 17,20,23,26,29,32-undecaoxo-34-(piperidine-1-carbonyl)-1,4,7,10,13,16,19,22,25,28,31-undecazacyclotetratriacont-9-yl]methoxy]acetamide, (1481) (8S,11S,15R,18S,23aS,29S,35S,37aS)-8-((S)-sec-butyl)-29-(3-chloro-4-(trifluoromethyl)phenethyl)-35-(cyclohexylmethyl)-18-cyclopentyl-6,11,12,15,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1482) (5S,8S,11S,15R,18S,23aS,29S,32R,35S,37aS)-8-((S)-sec-butyl)-29-(3-chloro-4-(trifluoromethyl)phenethyl)-18-cyclopentyl-11-isobutyl-5,6,12,15,19,32,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1483) (3S,9S,18S,21S,25R,28S,34S,36R)-9-(cyclohexylmethyl)-3-[2-[3-fluoro-4-(trifluoromethyl)phenyl]ethyl]-36-hydroxy-21,28-diisobutyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1484) (3S,9S,12S,18S,27S,30S,34R)-12-[2-[3-chloro-4-(trifluoromethyl)phenyl]ethyl]-22-ethyl-9-[(2-hydroxy-2-methyl-propoxy)methyl]-3,30-diisobutyl-18-(isopentyloxymethyl)-4,6,6,10,16,19,25,31,34-nonamethyl-27-[(1S)-1-methylpropyl]-1,4,7,10,13,16,19,22,25,28,31-undecazacyclotetratriacontane-2,5,8,11,14,17,20,23,26,29,32-undecone, (1485) (3S,9S,18S,21S,25R,28S,34S)-3-[2-[3-chloro-4-(trifluoromethyl)phenyl]ethyl]-28-cyclopentyl-7,10,13,16,21,22,25,29-octamethyl-18-[(1S)-1-methylpropyl]-9-(p-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1486) (3S,9S,18S,21S,25R,28S,34S)-3-[2-[3-chloro-4-(trifluoromethyl)phenyl]ethyl]-28-cyclopentyl-7,10,13,16,21,22,25,29-octamethyl-18-[(1S)-1-methylpropyl]-9-[[4-(trifluoromethyl)phenyl]methyl]spiro[1,4,7,10,13,16,19,22,26,29,32-undecazabicyclo[32.3.0]heptatriacontane-31,1'-cyclobutane]-2,5,8,11,14,17,20,23,27,30,33-undecone, (1487) (6'S,15'S,18'S,22'R,25'S,30a'S,36'S,38a'R)-15'-((S)-sec-butyl)-36'-(3-chloro-4-(trifluoromethyl)phenethyl)-25'-cyclopentyl-18'-isobutyl-7',10',13',19',22',26'-hexamethyl-6'-(4-methylbenzyl)tetracosahydro-5'H-spiro[cyclopentane-1,28'-dipyrrolo[2,1-i:2',1'-o][1,4,7,10,13,16,19,22,25,28,31]undecaazacyclotetratriacontin]-5',8',11',14',17',20',24',27',30',35',38'(21'H,29'H)-undecaone, (1488) (8S,11S,15R,18S,23aS,29S,31aR,37S,39aS)-8-((S)-sec-butyl)-29-(3-chloro-4-(trifluoromethyl)phenethyl)-18-cyclopentyl-11-isobutyl-6,12,15,19,38-pentamethyl-37-(4-methylbenzyl)tetracosahydro-2H,4H-spiro[azeto[2,1-u]dipyrrolo[2,1-i:2',1'-o][1,4,7,10,13,16,19,22,25,28,31]undecaazacyclotetratriacontine-21,1'-cyclopentan]-4,7,10,13,17,20,23,28,31,36,39(14H,22H)-undecaone, (1489) (3S,9S,18S,21S,25S,28S,34S)-9-(cyclohexylmethyl)-3-[2-[3-fluoro-4-(trifluoromethyl)phenyl]ethyl]-21,28-diisobutyl-7,10,13,16,22,29-hexamethyl-18-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1490) (3S,9S,18S,21S,25R,28S,34S)-18-butyl-9-(cyclohexylmethyl)-3-[2-[3-fluoro-4-(trifluoromethyl)phenyl]ethyl]-21,28-diisobutyl-7,10,13,16,22,25,29-heptamethyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1491) (5S,8S,11S,15R,18S,23aS,29S,35S,37aS)-8-((S)-sec-butyl)-29-(3-chloro-4-(trifluoromethyl)phenethyl)-35-(cyclohexylmethyl)-18-cyclopentyl-5,6,11,12,15,19,33,36-octamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1492) N-tert-butyl-2-[[(8S,11S,17S,26S,29S,33R,36S)-11-[2-[3-chloro-4-(trifluoromethyl)phenyl]ethyl]-29,36-diisobutyl-17-(isopentyloxymethyl)-9,15,18,21,24,30,33, 37-octamethyl-26-[(1S)-1-methylpropyl]-7,10,13,16,19, 22,25,28,31,35,38-undecaoxo-6,9,12,15,18,21,24,27,30, 34,37-undecazaspiro[4.33]octatriacontan-8-yl]methoxy]acetamide, (1493) (3S,9S,18S,21S,25R,28S,34S)-9-(cyclohexylmethyl)-3-[2-[3-fluoro-4-(trifluoromethyl)phenyl]ethyl]-21,28-diisobutyl-18-isopropyl-7,10,13,16,22,25,29-heptamethyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1494) (8S,11S,15R,18S,23aS,29S,31aR,37S,39aS)-8-((S)-sec-butyl)-29-(3-chloro-4-(trifluoromethyl)phenethyl)-18-cyclopentyl-6,11,12,15,19,38-hexamethyl-37-(4-methylbenzyl)tetracosahydro-2H,4H-spiro[azeto[2,1-u]dipyrrolo[2,1-i:2',1'-o][1,4,7,10,13,16,19,22,25,28,31]undecaazacyclotetratriacontine-21,1'-cyclopentan]-4,7,10,13,17,20,23,28,31,36,39(14H,22H)-undecaone, (1495) N-tert-butyl-2-[[(2S,5S,14S,20S,23S,29S,32R)-20-[2-[3-chloro-4-(trifluoromethyl)phenyl]ethyl]-7-ethyl-23,29-diisobutyl-14-(isopentyloxymethyl)-1,10,13,16,22,26,26,28,32-nonamethyl-5-[(1S)-1-methylpropyl]-3,6,9,12, 15,18,21,24,27,30,34-undecaoxo-1,4,7,10,13,16,19,22, 25,28,31-undecazacyclotetratriacont-2-yl]methoxy]acetamide, (1496) (8S,11S,15R,18S,23aS,29S,35S,37aS)-8-((S)-sec-butyl)-29-(3-chloro-4-(trifluoromethyl)phenethyl)-18-cyclopentyl-11-isobutyl-6,12,15,19,33,36-hexamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1497) (5S,8S,11S,15R,18S,23aS,29S,32R,35S,37aS)-8-((S)-sec-butyl)-29-(3-chloro-4-(trifluoromethyl)phenethyl)-18-cyclopentyl-5,6,11,12,15,19,32,33,36-nonamethyl-35-(4-(trifluoromethyl)benzyl)docosahydro-2H, 4H-spiro[azeto[2,1-u]pyrrolo[2,1-i][1,4,7,10,13,16,19, 22,25,28,31]undecaazacyclotetratriacontine-21,1'-cyclopentan]-4,7,10,13,17,20,23,28,31,34,37(14H,22H)-undecaone, (1498) (3S,9S,18S,21S,25R,28S,34S)-3-[2-[3-chloro-4-(trifluoromethyl)phenyl]ethyl]-28-cyclopentyl-21-isobutyl-7,10,13,16,22,25,29-heptamethyl-18-[(1S)-1-methylpropyl]-9-(p-tolylmethyl)spiro[1,4,7,10,13,16,19,22,26,29, 32-undecazabicyclo[32.3.0]heptatriacontane-31,1'-cyclobutane]-2,5,8,11,14,17,20,23,27,30,33-undecone, (1499) (8S,11S,15R,18S,23aS,29S,35S,37aS)-8-((S)-sec-butyl)-29-(3-chloro-4-(trifluoromethyl)phenethyl)-35-(cyclohexylmethyl)-18-cyclopentyl-11-isobutyl-6,12,15, 19,33,36-hexamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1500) (8S,11S,15R,18S,23aS,29S,35S,37aS)-8-((S)-sec-butyl)-29-(3-chloro-4-(trifluoromethyl)phenethyl)-18-cyclopentyl-11-isobutyl-6,12,15,19,33,36-hexamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1501) (3S,9S,18S,21S,25S,28S,34S)-9-(cyclohexylmethyl)-3-[2-[3-fluoro-4-(trifluoromethyl)phenyl]ethyl]-21,28-diisobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1502) N-tert-butyl-2-[[(3S,9S,12S,18S,27S,30S,34S)-3,30-diisobutyl-18-(isopentyloxymethyl)-1,4,6,6,10,16,19,22,25,31-decamethyl-27-[(1S)-1-methylpropyl]-2,5,8,11,14,17,20,23,26,29,32-undecaoxo-34-(piperidine-1-carbonyl)-12-[2-[4-(trifluoromethyl)phenyl]ethyl]-1,4,7,10,13,16,19,22,25,28,31-undecazacyclotetratriacont-9-yl]methoxy]acetamide, (1503) (3S,9S,18S,21S,25S,28S,34S)-3-[2-[3-chloro-4-(trifluoromethyl)phenyl]ethyl]-9-(cyclohexylmethyl)-21,28-diisobutyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1504) (5S,8S,11S,15R,18S,23aS,29S,32R,35S,37aS)-8-((S)-sec-butyl)-29-(3-chloro-4-(trifluoromethyl)phenethyl)-18-cyclopentyl-11-isobutyl-5,6,12,15,19,32,33,36-octamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1505) (3S,9S,12S,18S,27S,30S,34R)-25-butyl-12-[2-[3-chloro-4-(trifluoromethyl)phenyl]ethyl]-9-[(2-hydroxy-2-methyl-propoxy)methyl]-30-isobutyl-18-(isopentyloxymethyl)-3-isopropyl-4,6,6,10,16,19,22,31,34-nonamethyl-27-[(1S)-1-methylpropyl]-1,4,7,10,13,16,19,22,25,28,31-undecazacyclotetratriacontane-2,5,8,11,14,17,20,23,26,29,32-undecone, (1506) (3S,9S,18S,21S,25R,28S,34S)-3-[2-[3-chloro-4-(trifluoromethyl)phenyl]ethyl]-9-(cyclohexylmethyl)-28-cyclopentyl-7,10,13,16,21,22,25,29-octamethyl-18-[(1S)-1-methylpropyl]spiro[1,4,7,10,13,16,19,22,26,29,32-undecazabicyclo[32.3.0]heptatriacontane-31,1'-cyclobutane]-2,5,8,11,14,17,20,23,27,30,33-undecone, (1507) (8S,11S,15R,18S,23aS,29S,32R,35S,37aS)-8-((S)-sec-butyl)-29-(3-chloro-4-(trifluoromethyl)phenethyl)-18-cyclopentyl-6,11,12,15,19,32,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1508) (3S,9S,18S,21S,25R,28S,34S)-3-[2-[3-chloro-4-(trifluoromethyl)phenyl]ethyl]-28-cyclopentyl-21-isobutyl-7,10,13,16,22,25,29-heptamethyl-18-[(1S)-1-methylpropyl]-9-[[4-(trifluoromethyl)phenyl]methyl]spiro[1,4,7,10,13,16,19,22,26,29,32-undecazabicyclo[32.3.0]heptatriacontane-31,1'-cyclobutane]-2,5,8,11,14,17,20,23,27,30,33-undecone, (1509) (3S,9S,18S,21S,25R,28S,34S)-9-(cyclohexylmethyl)-36,36-difluoro-3-[2-[3-fluoro-4-(trifluoromethyl)phenyl]ethyl]-21,28-diisobutyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1510) (5S,8S,11S,15R,18S,23aS,29S,32R,35S,37aS)-8-((S)-sec-butyl)-29-(3-chloro-4-(trifluoromethyl)phenethyl)-35-(cyclohexylmethyl)-18-cyclopentyl-5,6,11,12,15,19,32,33,36-nonamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1511) (3S,9S,12S,18S,27S,30S,34R)-18-(cyclohexylmethyl)-12-[2-[3-fluoro-4-(trifluoromethyl)phenyl]ethyl]-3,9,30-triisobutyl-27-isopropyl-4,6,6,10,16,19,22,25,31,34-decamethyl-1,4,7,10,13,16,19,22,25,28,31-undecazacyclotetratriacontane-2,5,8,11,14,17,20,23,26,29,32-undecone, (1512) (5S,8S,11S,15R,18S,23aS,29S,35S,37aS)-8-((S)-sec-butyl)-29-(3-chloro-4-(trifluoromethyl)phenethyl)-18-cyclopentyl-5,6,11,12,15,19,33,36-octamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1513) N-tert-butyl-2-[[(6S,9S,13R,16S,22S,25S,31S,34S)-25-[2-[3-chloro-4-(trifluoromethyl)phenyl]ethyl]-4-ethyl-9,16-diisobutyl-31-(isopentyloxymethyl)-10,13,17,19,19,23,29,32-octamethyl-6-[(1S)-1-methylpropyl]-2,5,8,11,15,18,21,24,27,30,33-undecaoxo-1,4,7,10,14,17,20,23,26,29,32-undecazabicyclo[32.2.0]hexatriacontan-22-yl]methoxy]acetamide, (1514) (5S,8S,11S,15R,18S,23aS,29S,35S,37aS)-8-((S)-sec-butyl)-29-(3-chloro-4-(trifluoromethyl)phenethyl)-18-cyclopentyl-5,6,11,12,15,19,33,36-octamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1515) (3S,9S,18S,21S,25R,28S,34S)-9-(5,5-difluoropentyl)-3-[2-[3-fluoro-4-(trifluoromethyl)phenyl]ethyl]-21,28-diisobutyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1516) (3S,9S,12S,18S,27S,30S,34R)-12-[2-[3-chloro-4-(trifluoromethyl)phenyl]ethyl]-16-ethyl-9-[(2-hydroxy-2-methyl-propoxy)methyl]-3,30-diisobutyl-18-(isopentyloxymethyl)-4,6,6,10,19,22,25,31,34-nonamethyl-27-[(1S)-1-methylpropyl]-1,4,7,10,13,16,19,22,25,28,31-undecazacyclotetratriacontane-2,5,8,11,14,17,20,23,26,29,32-undecone, (1517) (8S,11S,15R,18S,23aS,29S,32R,35S,37aS)-8-((S)-sec-butyl)-29-(3-chloro-4-(trifluoromethyl)phenethyl)-18-cyclopentyl-11-isobutyl-6,12,15,19,32,33,36-heptamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1518) (3S,9S,18S,21S,25R,28S,34S)-28-butyl-9-(cyclohexylmethyl)-3-[2-[3-fluoro-4-(trifluoromethyl)phenyl]ethyl]-21-isobutyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1519) (3S,9S,12S,18S,27S,30S,34R)-12-[2-[3-chloro-4-(trifluoromethyl)phenyl]ethyl]-25-ethyl-9-[(2-hydroxy-2-methyl-propoxy)methyl]-3,30-diisobutyl-18-(isopentyloxymethyl)-4,6,6,10,16,19,22,31,34-nonamethyl-27-[(1S)-1-methylpropyl]-1,4,7,10,13,16,19,22,25,28,31-undecazacyclotetratriacontane-2,5,8,11,14,17,20,23,26,29,32-undecone, (1520) (3S,6R,9S,18S,21S,25R,28S,34S)-3-[2-[3-chloro-4-(trifluoromethyl)phenyl]ethyl]-28-cyclopentyl-6,7,10,13,16,21,22,25,29-nonamethyl-18-[(1S)-1-methylpropyl]-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1521) (3S,6R,9S,18S,21S,25R,28S,34S)-3-[2-[3-chloro-4-(trifluoromethyl)phenyl]ethyl]-28-cyclopentyl-21-isobutyl-6,7,10,13,16,22,25,29-octamethyl-18-[(1S)-1-methylpropyl]-9-(p-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1522) (8S,11S,15R,18S,23aS,29S,31aR,37S,39aS)-8-((S)-sec-butyl)-29-(3-chloro-4-(trifluoromethyl)phenethyl)-18-cyclopentyl-6,11,12,15,19,38-hexamethyl-37-(4-(trifluoromethyl)benzyl)tetracosahydro-2H,4H-spiro[azeto[2,1-u]dipyrrolo[2,1-i:2',1'-o][1,4,7,10,13,16,19,22,25,28,31]undecaazacyclotetratriacontine-21,1'-cyclopentan]-4,7,10,13,17,20,23,28,31,36,39(14H,22H)-undecaone, (1523) (3S,9S,18S,21S,25R,28S,34S)-3-[2-[3-chloro-4-(trifluoromethyl)phenyl]ethyl]-28-cyclopentyl-7,10,13,16,21,22,25,29-octamethyl-18-[(1S)-1-methylpropyl]-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1524) (3S,9S,18S,21S,25R,28S,34S)-3-[2-[3-chloro-4-(trifluoromethyl)phenyl]ethyl]-28-cyclopentyl-21-isobutyl-7,10,13,16,22,25,29-heptamethyl-18-[(1S)-1-methylpropyl]-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1525) (6'S,15'S,18'S,22'R,25'S,30a'S,36'S,38a'R)-15'-((S)-sec-butyl)-36'-(3-chloro-4-(trifluoromethyl)phenethyl)-25'-cyclopentyl-7',10',13',18',19',22',26'-heptamethyl-6'-(4-methylbenzyl)tetracosahydro-5'H-spiro[cyclopentane-1,28'-dipyrrolo[2,1-i:2',1'-o][1,4,7,10,13,16,19,22,25,28,31]undecaazacyclotetratriacontin]-5',8',11',14',17',20',24',27',30',35',38'(21'H,29'H)-undecaone, (1526) (3S,9S,12S,18S,27S,30S,34R)-18-(5,5-difluoropentyl)-12-[2-[3-fluoro-4-(trifluoromethyl)phenyl]ethyl]-3,9,30-triisobutyl-4,6,6,10,16,19,22,25,31,34-decamethyl-27-[(1S)-1-methylpropyl]-1,4,7,10,13,16,19,22,25,28,31-undecazacyclotetratriacontane-2,5,8,11,14,17,20,23,26,29,32-undecone, (1527) (3S,9S,18S,21S,25R,28S,34S)-18-cyclohexyl-9-(cyclohexylmethyl)-3-[2-[3-fluoro-4-(trifluoromethyl)phenyl]ethyl]-21,28-diisobutyl-7,10,13,16,22,25,29-heptamethyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1528) (3S,9S,12S,18S,27S,30S,34S)-25-ethyl-9-[(2-hydroxy-2-methyl-propoxy)methyl]-3,30-diisobutyl-18-(isopentyloxymethyl)-1,4,6,6,10,16,19,22,31-nonamethyl-27-[(1S)-1-methylpropyl]-34-(piperidine-1-carbonyl)-12-[2-[4-(trifluoromethyl)phenyl]ethyl]-1,4,7,10,13,16,19,22,25,28,31-undecazacyclotetratriacontane-2,5,8,11,14,17,20,23,26,29,32-undecone, (1529) (3S,9S,18S,21S,25R,28S,34S,36S)-9-(cyclohexylmethyl)-3-[2-[3-fluoro-4-(trifluoromethyl)phenyl]ethyl]-36-hydroxy-21,28-diisobutyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1530) (3S,6R,9S,18S,21S,25R,28S,34S)-3-[2-[3-chloro-4-(trifluoromethyl)phenyl]ethyl]-9-(cyclohexylmethyl)-28-cyclopentyl-21-isobutyl-6,7,10,13,16,22,25,29-octamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1531) (8S,11S,15R,18S,23aS,29S,32R,35S,37aS)-8-((S)-sec-butyl)-29-(3-chloro-4-(trifluoromethyl)phenethyl)-35-(cyclohexylmethyl)-18-cyclopentyl-11-isobutyl-6,12,15,19,32,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1532) (3S,9S,12S,18S,27S,30S,34S)-12-[2-[3-fluoro-4-(trifluoromethyl)phenyl]ethyl]-9-[(2-hydroxy-2-methyl-propoxy)methyl]-3,30-diisobutyl-18-(isopentyloxymethyl)-1,4,6,6,10,16,19,22,25,31-decamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (1533) (3S,9S,18S,21S,25R,28S,34S)-9-(cyclohexylmethyl)-3-[2-[3-fluoro-4-(trifluoromethyl)phenyl]ethyl]-21,28-diisobutyl-7,10,13,16,22,25,29-heptamethyl-18-prop-2-ynyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1534) (3S,9S,18S,21S,25R,28S,34S)-9-(cyclohexylmethyl)-3-[2-[3-fluoro-4-(trifluoromethyl)phenyl]ethyl]-21-isobutyl-28-isopropyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1535) (3S,6R,9S,18S,21S,25R,28S,34S)-3-[2-[3-chloro-4-(trifluoromethyl)phenyl]ethyl]-9-(cyclohexylmethyl)-28-cyclopentyl-6,7,10,13,16,21,22,25,29-nonamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1536) (5S,8S,11S,15R,18S,23aS,29S,32R,35S,37aS)-8-((S)-sec-butyl)-29-(3-chloro-4-(trifluoromethyl)phenethyl)-18-cyclopentyl-5,6,11,12,15,19,32,33,36-nonamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1537) (5S,8S,11S,15R,18S,23aS,29S,35S,37aS)-8-((S)-sec-butyl)-29-(3-chloro-4-(trifluoromethyl)phenethyl)-18-cyclopentyl-11-isobutyl-5,6,12,15,19,33,36-heptamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1538) N-tert-butyl-2-[[(2S,5S,14S,20S,23S,29S,32S)-2,23,29-triisobutyl-14-(isopentyloxymethyl)-1,7,10,13,16,22,26,26,28-nonamethyl-5-[(1S)-1-methylpropyl]-3,6,9,12,15,18,21,24,27,30,34-undecaoxo-20-[2-[4-

(trifluoromethyl)phenyl]ethyl]-1,4,7,10,13,16,19,22,25, 28,31-undecazacyclotetratriacont-32-yl]methoxy] acetamide,
(1539) (8S,11S,15R,18S,23aS,29S,32R,35S,37aS)-8-((S)-sec-butyl)-29-(3-chloro-4-(trifluoromethyl)phenethyl)-35-(cyclohexylmethyl)-18-cyclopentyl-6,11,12,15,19,32,33,36-octamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1540) (5S,8S,11S,15R,18S,23aS,29S,31aR,37S,39aS)-8-((S)-sec-butyl)-29-(3-chloro-4-(trifluoromethyl)phenethyl)-18-cyclopentyl-5,6,11,12,15,19,38-heptamethyl-37-(4-methylbenzyl)tetracosahydro-2H,4H-spiro[azeto[2,1-u]dipyrrolo[2,1-i:2',1'-o][1,4,7,10,13,16,19,22,25,28,31]undecaazacyclotetratriacontine-21,1'-cyclopentan]-4,7,10,13,17,20,23,28,31,36,39(14H,22H)-undecaone,
(1541) (3S,9S,12S,18S,27S,30S,34S)-12-[2-[3-chloro-4-(trifluoromethyl)phenyl]ethyl]-9-[(2-hydroxy-2-methylpropoxy)methyl]-3,30-diisobutyl-18-(isopentyloxymethyl)-1,4,6,6,10,16,19,22,25,31-decamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone,
(1542) (3S,6R,9S,18S,21S,25R,28S,34S)-3-[2-[3-chloro-4-(trifluoromethyl)phenyl]ethyl]-28-cyclopentyl-21-isobutyl-6,7,10,13,16,22,25,29-octamethyl-18-[(1S)-1-methylpropyl]-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1543) (6'S,15'S,18'S,22'R,25'S,30a'S,36'S,38a'R)-15'-((S)-sec-butyl)-36'-(3-chloro-4-(trifluoromethyl)phenethyl)-6'-(cyclohexylmethyl)-25'-cyclopentyl-7',10',13',18',19',22',26'-heptamethyltetracosahydro-5'H-spiro[cyclopentane-1,28'-dipyrrolo[2,1-i:2',1'-o][1,4,7,10,13,16,19,22,25,28,31]undecaazacyclotetratriacontin]-5',8',11',14',17',20',24',27',30',35',38'(21'H,29'H)-undecaone,
(1544) (3S,9S,18S,21S,25R,28S,34S)-3-[2-[3-chloro-4-(trifluoromethyl)phenyl]ethyl]-9-(cyclohexylmethyl)-28-cyclopentyl-21-isobutyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclobutane]-2,5,8,11,14,17,20,23,27,30,33-undecone,
(1545) (3S,9S,18S,21S,25R,28S,34S)-9-(cyclohexylmethyl)-3-[2-[3-fluoro-4-(trifluoromethyl)phenyl]ethyl]-21,28-diisobutyl-7,10,13,16,22,25,29-heptamethyl-18-[(1S)-1-methylpropyl]spiro[1,4,7,10,13,16,19,22,26,29,32-undecazabicyclo[32.2.0]hexatriacontane-31,1'-cyclopentane]-2,5,8,11,14,17,20,23,27,30,33-undecone,
(1546) (3S,9S,12S,18S,27S,30S,34R)-12-[2-[3-chloro-4-(trifluoromethyl)phenyl]ethyl]-9-[(2-hydroxy-2-methylpropoxy)methyl]-3,30-diisobutyl-18-(isopentyloxymethyl)-4,6,6,10,16,19,22,25,31,34-decamethyl-27-[(1S)-1-methylpropyl]-1,4,7,10,13,16,19,22,25,28,31-undecazacyclotetratriacontane-2,5,8,11,14,17,20,23,26,29,32-undecone,
(1547) (3S,9S,18S,21S,25R,28S,34S)-3-[2-[3-chloro-4-(trifluoromethyl)phenyl]ethyl]-21-isobutyl-28-isopropyl-7,10,13,16,22,25,29-heptamethyl-18-[(1S)-1-methylpropyl]-9-(m-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1548) (5S,8S,11S,15R,18S,23aS,29S,35S,37aS)-8-((S)-sec-butyl)-5-butyl-29-(3-chloro-4-(trifluoromethyl)phenethyl)-35-(cyclohexylmethyl)-11-isobutyl-18-isopropyl-6,12,15,19,33,36-hexamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1549) (3S,9S,18S,21S,25R,28S,34S)-3-[2-[3-chloro-4-(trifluoromethyl)phenyl]ethyl]-21-isobutyl-28-isopropyl-7,10,13,16,22,25,26,29-octamethyl-18-[(1S)-1-methylpropyl]-9-(p-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1550) (3S,9S,18S,21S,25R,28S,34S)-3-[2-[3-chloro-4-(trifluoromethyl)phenyl]ethyl]-21-isobutyl-28-isopropyl-7,10,13,16,22,25,26,29-octamethyl-18-[(1S)-1-methylpropyl]-9-(o-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1551) (3S,9S,18S,21S,25R,28S,34S)-3-[2-[3-chloro-4-(trifluoromethyl)phenyl]ethyl]-21-isobutyl-28-isopropyl-9-[(4-methoxyphenyl)methyl]-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1552) (5S,8S,11S,15S,18S,23aS,29S,35S,37aS)-8-((S)-sec-butyl)-29-(3-chloro-4-(trifluoromethyl)phenethyl)-35-(cyclohexylmethyl)-5-(cyclopentylmethyl)-11-isobutyl-18-isopropyl-6,12,16,19,33,36-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1553) (5S,8S,11S,15S,18S,23aS,29S,35S,37aS)-8-((S)-sec-butyl)-29-(3-chloro-4-(trifluoromethyl)phenethyl)-35-(cyclohexylmethyl)-5-cyclopropyl-11-isobutyl-18-isopropyl-6,12,16,19,33,36-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1554) (5S,8S,11S,15S,18S,23aS,29S,35S,37aS)-8-((S)-sec-butyl)-29-(3-chloro-4-(trifluoromethyl)phenethyl)-5-cyclobutyl-35-(cyclohexylmethyl)-11-isobutyl-18-isopropyl-6,12,16,19,33,36-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1555) (3S,9S,18S,21S,25S,28S,34S)-3-[2-[3-chloro-4-(trifluoromethyl)phenyl]ethyl]-21-isobutyl-28-isopropyl-7,10,13,16,22,26,29-heptamethyl-18-[(1S)-1-methylpropyl]-25-(piperidine-1-carbonyl)-9-[[3-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1556) (3S,9S,18S,21S,25R,28S,34S)-3-[2-[3-chloro-4-(trifluoromethyl)phenyl]ethyl]-9-[(3-fluorophenyl)methyl]-21-isobutyl-28-isopropyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1557) (3S,9S,18S,21S,25S,28S,34S)-3-[2-[3-chloro-4-(trifluoromethyl)phenyl]ethyl]-9-[(3-fluorophenyl)methyl]-21-isobutyl-28-isopropyl-7,10,13,16,22,26,29-heptamethyl-18-[(1S)-1-methylpropyl]-25-(piperidine-1-carbonyl)spiro[1,4,7,10,13,16,19,22,26,29,32- undecazabicyclo[32.3.0]heptatriacontane-31,1'-cyclopentane]-2,5,8,11,14,17,20,23,27,30,33-undecone, (1558) (5S,8S,11S,15S,18S,23aS,29S,35S,37aS)-8-((S)-sec-butyl)-29-(3-chloro-4-(trifluoromethyl)phenethyl)-35-(cyclohexylmethyl)-5,11-diisobutyl-18-isopropyl-6,12,16,19,33,36-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1559) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-isopropyl-6,11,12,16,19,33,36-heptamethyl-5-phenethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1560) (5S,8S,11S,15R,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-6,12,15,19,33,36-hexamethyl-5-propyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1561) (5S,8S,11S,15S,18S,23aS,29S,35S,37aS)-5-benzyl-8-((S)-sec-butyl)-29-(3-chloro-4-(trifluoromethyl)phenethyl)-35-(cyclohexylmethyl)-11-isobutyl-18-isopropyl-6,12,16,19,33,36-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1562) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-isopropyl-5,6,11,12,16,19,33,36-octamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1563) (3S,9S,18S,21S,25R,28S,34S)-3-[2-[3-chloro-4-(trifluoromethyl)phenyl]ethyl]-21-isobutyl-28-isopropyl-7,10,13,16,22,25,26,29-octamethyl-18-[(1S)-1-methylpropyl]-9-[[4-(trifluoromethoxy)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1564) (5S,8S,11S,15R,18S,23aS,29S,35S,37aS)-8-((S)-sec-butyl)-29-(3-chloro-4-(trifluoromethyl)phenethyl)-35-(cyclohexylmethyl)-18-isopropyl-5,6,12,15,19,33,36-heptamethyl-11-propyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1565) (3S,9S,18S,21S,25R,28S,34S)-3-[2-[3-chloro-4-(trifluoromethyl)phenyl]ethyl]-21-isobutyl-28-isopropyl-7,10,13,16,22,25,29-heptamethyl-18-[(1S)-1-methylpropyl]-9-[[4-(trifluoromethoxy)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1566) (5S,8S,11S,15S,18S,23aS,29S,35S,37aS)-8-((S)-sec-butyl)-29-(3-chloro-4-(trifluoromethyl)phenethyl)-35-(cyclohexylmethyl)-5-(cyclopentylmethyl)-18-isopropyl-6,11,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1567) (3S,9S,18S,21S,25R,28S,34S)-3-[2-[3-chloro-4-(trifluoromethyl)phenyl]ethyl]-21-isobutyl-28-isopropyl-7,10,13,16,22,25,26,29-octamethyl-18-[(1S)-1-methylpropyl]-9-[[2-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1568) (5S,8S,11S,15R,18S,23aS,29S,35S,37aS)-8-((S)-sec-butyl)-11-butyl-29-(3-chloro-4-(trifluoromethyl)phenethyl)-35-(cyclohexylmethyl)-18-isopropyl-5,6,12,15,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1569) (5S,8S,11S,15S,18S,23aS,29S,35S,37aS)-8-((S)-sec-butyl)-29-(3-chloro-4-(trifluoromethyl)phenethyl)-35-(cyclohexylmethyl)-5-ethyl-11-isobutyl-18-isopropyl-6,12,16,19,33,36-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1570) (3S,9S,18S,21S,25R,28S,34S)-3-[2-[3-chloro-4-(trifluoromethyl)phenyl]ethyl]-21-isobutyl-28-isopropyl-7,10,13,16,22,25,26,29-octamethyl-18-[(1S)-1-methylpropyl]-9-(m-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1571) (3S,9S,18S,21S,25R,28S,34S)-3-[2-[3-chloro-4-(trifluoromethyl)phenyl]ethyl]-9-[(4-fluorophenyl)methyl]-21-isobutyl-28-isopropyl-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1572) (3S,9S,18S,21S,25R,28S,34S)-3-[2-[3-chloro-4-(trifluoromethyl)phenyl]ethyl]-21-isobutyl-28-isopropyl-7,10,13,16,22,25,26,29-octamethyl-18-[(1S)-1-methylpropyl]-9-[[3-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1573) (3S,9S,18S,21S,25R,28S,34S)-3-[2-[3-chloro-4-(trifluoromethyl)phenyl]ethyl]-21-isobutyl-28-isopropyl-7,10,13,16,22,25,29-heptamethyl-18-[(1S)-1-methylpropyl]-9-[[3-(trifluoromethoxy)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1574) (5S,8S,11S,15S,18S,23aS,29S,35S,37aS)-8-((S)-sec-butyl)-29-(3-chloro-4-(trifluoromethyl)phenethyl)-5,35-bis(cyclohexylmethyl)-11-isobutyl-18-isopropyl-6,12,16,19,33,36-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1575) (3S,9S,18S,21S,25R,28S,34S)-3-[2-[3-chloro-4-(trifluoromethyl)phenyl]ethyl]-21-isobutyl-28-isopropyl-7,10,13,16,22,25,29-heptamethyl-18-[(1S)-1-methylpropyl]-9-[[3-(trifluoromethyl)phenyl]methyl]spiro[1,4,7, 10,13,16,19,22,26,29,32-undecazabicyclo[32.3.0]
heptatriacontane-31,1'-cyclopentane]-2,5,8,11,14,17,20,
23,27,30,33-undecone,
(1576) (3S,9S,18S,21S,25S,28S,34S)-9-[(4-bromophenyl)
methyl]-3-[2-[3-chloro-4-(trifluoromethyl)phenyl]ethyl]-
21-isobutyl-28-isopropyl-7,10,13,16,22,26,29-heptam-
ethyl-18-[(1S)-1-methylpropyl]-25-(piperidine-1-
carbonyl)spiro[1,4,7,10,13,16,19,22,26,29,32-
undecazabicyclo[32.3.0]heptatriacontane-31,1'-
cyclopentane]-2,5,8,11,14,17,20,23,27,30,33-undecone,
(1577) (5S,8S,11S,15S,18S,23aS,29S,35S,37aS)-8-((S)-
sec-butyl)-29-(3-chloro-4-(trifluoromethyl)phenethyl)-
35-(cyclohexylmethyl)-11-isobutyl-5-isopentyl-18-iso-
propyl-6,12,16,19,33,36-hexamethyl-15-(piperidine-1-
carbonyl)docosahydro-2H,4H-spiro[azeto[2,1-u]pyrrolo
[2,1-i][1,4,7,10,13,16,19,22,25,28,31]
undecaazacyclotetratriacontine-21,1'-cyclopentan]-4,7,
10,13,17,20,23,28,31,34,37(14H,22H)-undecaone,
(1578) (5S,8S,11S,15R,18S,23aS,29S,35S,37aS)-8-((S)-
sec-butyl)-29-(3-chloro-4-(trifluoromethyl)phenethyl)-
35-(cyclohexylmethyl)-18-isopropyl-5,6,11,12,15,19,33,
36-octamethyldocosahydro-2H,4H-spiro[azeto[2,1-u]
pyrrolo[2,1-i][1,4,7,10,13,16,19,22,25,28,31]
undecaazacyclotetratriacontine-21,1'-cyclopentan]-4,7,
10,13,17,20,23,28,31,34,37(14H,22H)-undecaone,
(1579) (3S,9S,18S,21S,25S,28S,34S)-3-[2-[3-chloro-4-(tri-
fluoromethyl)phenyl]ethyl]-21-isobutyl-28-isopropyl-7,
10,13,16,22,26,29-heptamethyl-18-[(1S)-1-methylpro-
pyl]-25-(piperidine-1-carbonyl)-9-[[2-(trifluoromethyl)
phenyl]methyl]spiro[1,4,7,10,13,16,19,22,26,29,32-
undecazabicyclo[32.3.0]heptatriacontane-31,1'-
cyclopentane]-2,5,8,11,14,17,20,23,27,30,33-undecone,
(1580) (5S,8S,11S,15S,18S,23aS,29S,35S,37aS)-8-((S)-
sec-butyl)-29-(3-chloro-4-(trifluoromethyl)phenethyl)-5,
35-bis(cyclohexylmethyl)-18-isopropyl-6,11,12,16,19,
33,36-heptamethyl-15-(piperidine-1-carbonyl)
docosahydro-2H,4H-spiro[azeto[2,1-u]pyrrolo[2,1-i][1,4,
7,10,13,16,19,22,25,28,31]
undecaazacyclotetratriacontine-21,1'-cyclopentan]-4,7,
10,13,17,20,23,28,31,34,37(14H,22H)-undecaone,
(1581) (5S,8S,11S,15R,18S,23aS,29S,35S,37aS)-8-((S)-
sec-butyl)-29-(3-chloro-4-(trifluoromethyl)phenethyl)-5,
35-bis(cyclohexylmethyl)-11-isobutyl-18-isopropyl-6,12,
15,19,33,36-hexamethyldocosahydro-2H,4H-spiro[azeto
[2,1-u]pyrrolo[2,1-i][1,4,7,10,13,16,19,22,25,28,31]
undecaazacyclotetratriacontine-21,1'-cyclopentan]-4,7,
10,13,17,20,23,28,31,34,37(14H,22H)-undecaone,
(1582) (3S,9S,18S,21S,25R,28S,34S)-9-[(2-chlorophe-
noxy)methyl]-3-[2-[3-chloro-4-(trifluoromethyl)phenyl]
ethyl]-21-isobutyl-28-isopropyl-7,10,13,16,22,25,29-
heptamethyl-18-[(1S)-1-methylpropyl]spiro[1,4,7,10,13,
16,19,22,26,29,32-undecazabicyclo[32.3.0]
heptatriacontane-31,1'-cyclopentane]-2,5,8,11,14,17,20,
23,27,30,33-undecone,
(1583) (3S,9S,18S,21S,25S,28S,34S)-3-[2-[3-chloro-4-(tri-
fluoromethyl)phenyl]ethyl]-9-[(2-fluorophenyl)methyl]-
21-isobutyl-28-isopropyl-7,10,13,16,22,26,29-heptam-
ethyl-18-[(1S)-1-methylpropyl]-25-(piperidine-1-
carbonyl)spiro[1,4,7,10,13,16,19,22,26,29,32-
undecazabicyclo[32.3.0]heptatriacontane-31,1'-
cyclopentane]-2,5,8,11,14,17,20,23,27,30,33-undecone,
(1584) (3S,9S,18S,21S,25S,28S,34S)-3-[2-[3-chloro-4-(tri-
fluoromethyl)phenyl]ethyl]-21-isobutyl-28-isopropyl-7,
10,13,16,22,26,29-heptamethyl-18-[(1S)-1-methylpro-
pyl]-9-(o-tolylmethyl)-25-(piperidine-1-carbonyl)spiro
[1,4,7,10,13,16,19,22,26,29,32-undecazabicyclo[32.3.0]
heptatriacontane-31,1'-cyclopentane]-2,5,8,11,14,17,20,
23,27,30,33-undecone,
(1585) (3S,9S,18S,21S,25R,28S,34S)-3-[2-[3-chloro-4-(tri-
fluoromethyl)phenyl]ethyl]-9-[(2-fluorophenyl)methyl]-
21-isobutyl-28-isopropyl-7,10,13,16,22,25,29-heptam-
ethyl-18-[(1S)-1-methylpropyl]spiro[1,4,7,10,13,16,19,
22,26,29,32-undecazabicyclo[32.3.0]heptatriacontane-
31,1'-cyclopentane]-2,5,8,11,14,17,20,23,27,30,33-
undecone,
(1586) (5S,8S,11S,15R,18S,23aS,29S,35S,37aS)-8-((S)-
sec-butyl)-29-(3-chloro-4-(trifluoromethyl)phenethyl)-
35-(cyclohexylmethyl)-5-cyclopropyl-11-isobutyl-18-
isopropyl-6,12,15,19,33,36-hexamethyldocosahydro-2H,
4H-spiro[azeto[2,1-u]pyrrolo[2,1-i][1,4,7,10,13,16,19,
22,25,28,31]undecaazacyclotetratriacontine-21,1'-
cyclopentan]-4,7,10,13,17,20,23,28,31,34,37(14H,22H)-
undecaone,
(1587) (3S,9S,18S,21S,25R,28S,34S)-9-[(3-bromophenyl)
methyl]-3-[2-[3-chloro-4-(trifluoromethyl)phenyl]ethyl]-
21-isobutyl-28-isopropyl-7,10,13,16,22,25,29-heptam-
ethyl-18-[(1S)-1-methylpropyl]spiro[1,4,7,10,13,16,19,
22,26,29,32-undecazabicyclo[32.3.0]heptatriacontane-
31,1'-cyclopentane]-2,5,8,11,14,17,20,23,27,30,33-
undecone,
(1588) (3S,9S,18S,21S,25S,28S,34S)-3-[2-[3-chloro-4-(tri-
fluoromethyl)phenyl]ethyl]-21-isobutyl-28-isopropyl-9-
[(4-methoxyphenyl)methyl]-7,10,13,16,22,26,29-hep-
tamethyl-18-[(1S)-1-methylpropyl]-25-(piperidine-1-
carbonyl)spiro[1,4,7,10,13,16,19,22,26,29,32-
undecazabicyclo[32.3.0]heptatriacontane-31,1'-
cyclopentane]-2,5,8,11,14,17,20,23,27,30,33-undecone,
(1589) (3S,9S,18S,21S,25R,28S,34S)-9-[(2-chlorophe-
noxy)methyl]-3-[2-[3-chloro-4-(trifluoromethyl)phenyl]
ethyl]-21-isobutyl-28-isopropyl-7,10,13,16,22,25,26,29-
octamethyl-18-[(1S)-1-methylpropyl]spiro[1,4,7,10,13,
16,19,22,26,29,32-undecazabicyclo[32.3.0]
heptatriacontane-31,1'-cyclopentane]-2,5,8,11,14,17,20,
23,27,30,33-undecone,
(1590) (3S,9S,18S,21S,25R,28S,34S)-9-[(4-bromophenyl)
methyl]-3-[2-[3-chloro-4-(trifluoromethyl)phenyl]ethyl]-
21-isobutyl-28-isopropyl-7,10,13,16,22,25,26,29-octam-
ethyl-18-[(1S)-1-methylpropyl]spiro[1,4,7,10,13,16,19,
22,26,29,32-undecazabicyclo[32.3.0]heptatriacontane-
31,1'-cyclopentane]-2,5,8,11,14,17,20,23,27,30,33-
undecone,
(1591) (3S,9S,18S,21S,25R,28S,34S)-9-[(2-chlorophenyl)
methyl]-3-[2-[3-chloro-4-(trifluoromethyl)phenyl]ethyl]-
21-isobutyl-28-isopropyl-7,10,13,16,22,25,29-heptam-
ethyl-18-[(1S)-1-methylpropyl]spiro[1,4,7,10,13,16,19,
22,26,29,32-undecazabicyclo[32.3.0]heptatriacontane-
31,1'-cyclopentane]-2,5,8,11,14,17,20,23,27,30,33-
undecone,
(1592) (5S,8S,11S,15S,18S,23aS,29S,35S,37aS)-8-((S)-
sec-butyl)-29-(3-chloro-4-(trifluoromethyl)phenethyl)-
35-(cyclohexylmethyl)-11-isobutyl-5,18-diisopropyl-6,
12,16,19,33,36-hexamethyl-15-(piperidine-1-carbonyl)
docosahydro-2H,4H-spiro[azeto[2,1-u]pyrrolo[2,1-i][1,4,
7,10,13,16,19,22,25,28,31]
undecaazacyclotetratriacontine-21,1'-cyclopentan]-4,7,
10,13,17,20,23,28,31,34,37(14H,22H)-undecaone,
(1593) (5S,8S,11S,15R,18S,23aS,29S,35S,37aS)-8-((S)-
sec-butyl)-29-(3-chloro-4-(trifluoromethyl)phenethyl)-
35-(cyclohexylmethyl)-5-ethyl-11-isobutyl-18-isopropyl-
6,12,15,19,33,36-hexamethyldocosahydro-2H,4H-spiro
[azeto[2,1-u]pyrrolo[2,1-i][1,4,7,10,13,16,19,22,25,28, 31]undecaazacyclotetratriacontine-21,1'-cyclopentan]-4,7,10,13,17,20,23,28,31,34,37(14H,22H)-undecaone,
(1594) (3S,9S,18S,21S,25S,28S,34S)-3-[2-[3-chloro-4-(trifluoromethyl)phenyl]ethyl]-21-isobutyl-28-isopropyl-7,10,13,16,22,26,29-heptamethyl-18-[(1S)-1-methylpropyl]-25-(piperidine-1-carbonyl)-9-(p-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1595) (5S,8S,11S,15S,18S,23aS,29S,35S,37aS)-8-((S)-sec-butyl)-29-(3-chloro-4-(trifluoromethyl)phenethyl)-35-(cyclohexylmethyl)-5-isopentyl-18-isopropyl-6,11,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1596) (5S,8S,11S,15S,18S,23aS,29S,35S,37aS)-8-((S)-sec-butyl)-5-butyl-29-(3-chloro-4-(trifluoromethyl)phenethyl)-35-(cyclohexylmethyl)-11-isobutyl-18-isopropyl-6,12,16,19,33,36-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1597) (3S,9S,18S,21S,25R,28S,34S)-9-[(3-bromophenyl)methyl]-3-[2-[3-chloro-4-(trifluoromethyl)phenyl]ethyl]-21-isobutyl-28-isopropyl-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1598) (3S,9S,18S,21S,25S,28S,34S)-9-benzyl-3-[2-[3-chloro-4-(trifluoromethyl)phenyl]ethyl]-21-isobutyl-28-isopropyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1599) (3S,9S,18S,21S,25R,28S,34S)-3-[2-[3-chloro-4-(trifluoromethyl)phenyl]ethyl]-9-[(2-fluorophenyl)methyl]-21-isobutyl-28-isopropyl-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1600) (5S,8S,11S,15S,18S,23aS,29S,35S,37aS)-8-((S)-sec-butyl)-29-(3-chloro-4-(trifluoromethyl)phenethyl)-5-cyclohexyl-35-(cyclohexylmethyl)-11-isobutyl-18-isopropyl-6,12,16,19,33,36-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1601) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-6,12,16,19,33,36-hexamethyl-15-(piperidine-1-carbonyl)-5-propyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1602) (3S,9S,18S,21S,25R,28S,34S)-3-[2-[3-chloro-4-(trifluoromethyl)phenyl]ethyl]-9-[(4-fluorophenyl)methyl]-21-isobutyl-28-isopropyl-7,10,13,16,22,25,26,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1603) (5S,8S,11S,15S,18S,23aS,29S,35S,37aS)-8-((S)-sec-butyl)-29-(3-chloro-4-(trifluoromethyl)phenethyl)-5-(cyclobutylmethyl)-35-(cyclohexylmethyl)-11-isobutyl-18-isopropyl-6,12,16,19,33,36-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1604) (3S,9S,18S,21S,25R,28S,34S)-9-benzyl-3-[2-[3-chloro-4-(trifluoromethyl)phenyl]ethyl]-21-isobutyl-28-isopropyl-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1605) (3S,9S,18S,21S,25R,28S,34S)-3-[2-[3-chloro-4-(trifluoromethyl)phenyl]ethyl]-21-isobutyl-28-isopropyl-9-[(4-methoxyphenyl)methyl]-7,10,13,16,22,25,29-heptamethyl-8-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1606) (3S,9S,18S,21S,25R,28S,34S)-9-benzyl-3-[2-[3-chloro-4-(trifluoromethyl)phenyl]ethyl]-21-isobutyl-28-isopropyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1607) (5S,8S,11S,15R,18S,23aS,29S,35S,37aS)-8-((S)-sec-butyl)-29-(3-chloro-4-(trifluoromethyl)phenethyl)-35-(cyclohexylmethyl)-11-ethyl-18-isopropyl-5,6,12,15,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1608) (3S,9S,18S,21S,25S,28S,34S)-3-[2-[3-chloro-4-(trifluoromethyl)phenyl]ethyl]-21-isobutyl-28-isopropyl-7,10,13,16,22,26,29-heptamethyl-18-[(1S)-1-methylpropyl]-9-(2-phenylethyl)-25-(piperidine-1-carbonyl)spiro[11,4,7,10,13,16,19,22,26,29,32-undecazabicyclo[32.3.0]heptatriacontane-31,1'-cyclopentane]-2,5,8,11,14,17,20,23,27,30,33-undecone,
(1609) (3S,9S,18S,21S,25S,28S,34S)-9-[(2-chlorophenoxy)methyl]-3-[2-[3-chloro-4-(trifluoromethyl)phenyl]ethyl]-21-isobutyl-28-isopropyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1610) (3S,9S,18S,21S,25R,28S,34S)-3-[2-[3-chloro-4-(trifluoromethyl)phenyl]ethyl]-9-[(3-fluorophenyl)methyl]-21-isobutyl-28-isopropyl-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1611) (3S,9S,18S,21S,25S,28S,34S)-9-[(3-chlorophenyl)methyl]-3-[2-[3-chloro-4-(trifluoromethyl)phenyl]ethyl]-21-isobutyl-28-isopropyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1612) (5S,8S,11S,15R,18S,23aS,29S,35S,37aS)-8-((S)-sec-butyl)-29-(3-chloro-4-(trifluoromethyl)phenethyl)-

35-(cyclohexylmethyl)-5-(cyclopropylmethyl)-11-isobutyl-18-isopropyl-6,12,15,19,33,36-hexamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1613) (3S,9S,18S,21S,25R,28S,34S)-3-[2-[3-chloro-4-(trifluoromethyl)phenyl]ethyl]-21-isobutyl-28-isopropyl-7,10,13,16,22,25,29-heptamethyl-18-[(1S)-1-methylpropyl]-9-[[2-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1614) (3S,9S,18S,21S,25R,28S,34S)-3-[2-[3-chloro-4-(trifluoromethyl)phenyl]ethyl]-21-isobutyl-28-isopropyl-7,10,13,16,22,25,29-heptamethyl-18-[(1S)-1-methylpropyl]-9-(o-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1615) (3S,9S,18S,21S,25R,28S,34S)-9-[(2-chlorophenyl)methyl]-3-[2-[3-chloro-4-(trifluoromethyl)phenyl]ethyl]-21-isobutyl-28-isopropyl-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1616) (5S,8S,11S,15S,18S,23aS,29S,35S,37aS)-8-((S)-sec-butyl)-11-butyl-29-(3-chloro-4-(trifluoromethyl)phenethyl)-35-(cyclohexylmethyl)-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1617) (3S,9S,18S,21S,25R,28S,34S)-3-[2-[3-chloro-4-(trifluoromethyl)phenyl]ethyl]-21-isobutyl-28-isopropyl-7,10,13,16,22,25,26,29-octamethyl-18-[(1S)-1-methylpropyl]-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1618) (5S,8S,11S,15R,18S,23aS,29S,35S,37aS)-8-((S)-sec-butyl)-29-(3-chloro-4-(trifluoromethyl)phenethyl)-35-(cyclohexylmethyl)-5-(cyclopentylmethyl)-11-isobutyl-18-isopropyl-6,12,15,19,33,36-hexamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1619) (5S,8S,11S,15R,18S,23aS,29S,35S,37aS)-8-((S)-sec-butyl)-29-(3-chloro-4-(trifluoromethyl)phenethyl)-35-(cyclohexylmethyl)-5,11-diisobutyl-18-isopropyl-6,12,15,19,33,36-hexamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1620) (3S,9S,18S,21S,25R,28S,34S)-3-[2-[3-chloro-4-(trifluoromethyl)phenyl]ethyl]-21-isobutyl-28-isopropyl-7,10,13,16,22,25,29-heptamethyl-18-[(1S)-1-methylpropyl]-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1621) (3S,9S,18S,21S,25R,28S,34S)-9-[(3-chlorophenyl)methyl]-3-[2-[3-chloro-4-(trifluoromethyl)phenyl]ethyl]-21-isobutyl-28-isopropyl-7,10,13,16,22,25,26,29-octamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1622) (5S,8S,11S,15S,18S,23aS,29S,35S,37aS)-8-((S)-sec-butyl)-29-(3-chloro-4-(trifluoromethyl)phenethyl)-5-cyclohexyl-35-(cyclohexylmethyl)-18-isopropyl-6,11,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1623) (3S,9S,18S,21S,25R,28S,34S)-9-[(3-chlorophenyl)methyl]-3-[2-[3-chloro-4-(trifluoromethyl)phenyl]ethyl]-21-isobutyl-28-isopropyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1624) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-6,12,16,19,33,36-hexamethyl-5-phenethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1625) (3S,9S,18S,21S,25R,28S,34S)-9-[(4-bromophenyl)methyl]-3-[2-[3-chloro-4-(trifluoromethyl)phenyl]ethyl]-21-isobutyl-28-isopropyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1626) (3S,9S,18S,21S,25S,28S,34S)-3-[2-[3-chloro-4-(trifluoromethyl)phenyl]ethyl]-21-isobutyl-28-isopropyl-7,10,13,16,22,26,29-heptamethyl-18-[(1S)-1-methylpropyl]-9-(m-tolylmethyl)-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1627) (3S,9S,18S,21S,25R,28S,34S)-3-[2-[3-chloro-4-(trifluoromethyl)phenyl]ethyl]-21-isobutyl-28-isopropyl-7,10,13,16,22,25,29-heptamethyl-18-[(1S)-1-methylpropyl]-9-(2-phenylethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1628) (5S,8S,11S,15R,18S,23aS,29S,35S,37aS)-5-benzyl-8-((S)-sec-butyl)-29-(3-chloro-4-(trifluoromethyl)phenethyl)-35-(cyclohexylmethyl)-11-isobutyl-18-isopropyl-6,12,15,19,33,36-hexamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1629) (3S,9S,18S,21S,25S,28S,34S)-3-[2-[3-chloro-4-(trifluoromethyl)phenyl]ethyl]-21-isobutyl-28-isopropyl-7,10,13,16,22,26,29-heptamethyl-18-[(1S)-1-methylpropyl]-25-(piperidine-1-carbonyl)-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1630) (3S,9S,18S,21S,25S,28S,34S)-3-[2-[3-chloro-4-(trifluoromethyl)phenyl]ethyl]-21-isobutyl-28-isopropyl-7,10,13,16,22,26,29-heptamethyl-18-[(1S)-1-methylpropyl]-25-(piperidine-1-carbonyl)-9-[[4-(trifluoromethoxy)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1631) (3S,9S,18S,21S,25S,28S,34S)-3-[2-[3-chloro-4-(trifluoromethyl)phenyl]ethyl]-9-[(4-fluorophenyl)methyl]-21-isobutyl-28-isopropyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1632) (3S,9S,18S,21S,25R,28S,34S)-3-[2-[3-chloro-4-(trifluoromethyl)phenyl]ethyl]-21-isobutyl-28-isopropyl-7,10,13,16,22,25,29-heptamethyl-18-[(1S)-1-methylpropyl]-9-(p-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1633) (3S,9S,18S,21S,25R,28S,34S)-3-[2-[3-chloro-4-(trifluoromethyl)phenyl]ethyl]-21-isobutyl-28-isopropyl-7,10,13,16,22,25,26,29-octamethyl-18-[(1S)-1-methylpropyl]-9-[[2-(trifluoromethoxy)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1634) (3S,9S,18S,21S,25R,28S,34S)-3-[2-[3-chloro-4-(trifluoromethyl)phenyl]ethyl]-21-isobutyl-28-isopropyl-7,10,13,16,22,25,26,29-octamethyl-18-[(1S)-1-methylpropyl]-9-(2-phenylethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1635) (3S,9S,18S,21S,25R,28S,34S)-3-[2-[3-chloro-4-(trifluoromethyl)phenyl]ethyl]-21-isobutyl-28-isopropyl-7,10,13,16,22,25,29-heptamethyl-18-[(1S)-1-methylpropyl]-9-[[2-(trifluoromethoxy)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1636) (3S,9S,18S,21S,25S,28S,34S)-9-[(2-chlorophenyl)methyl]-3-[2-[3-chloro-4-(trifluoromethyl)phenyl]ethyl]-21-isobutyl-28-isopropyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1637) (3S,9S,18S,21S,25R,28S,34S)-3-[2-[3-chloro-4-(trifluoromethyl)phenyl]ethyl]-21-isobutyl-28-isopropyl-7,10,13,16,22,25,26,29-octamethyl-18-[(1S)-1-methylpropyl]-9-[[3-(trifluoromethoxy)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1638) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-ethyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1639) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-isopropyl-5,6,12,16,19,33,36-heptamethyl-15-(piperidine-1-carbonyl)-11-propyldocosahydro-2H,4H-spiro[azeto[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1640) (3S,9S,18S,21S,25S,28S,34S)-3-[2-[3-chloro-4-(trifluoromethyl)phenyl]ethyl]-21-isobutyl-28-isopropyl-7,10,13,16,22,26,29-heptamethyl-18-[(1S)-1-methylpropyl]-25-(piperidine-1-carbonyl)-9-[[3-(trifluoromethoxy)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1641) (3S,9S,18S,21S,25S,28S,34S)-3-[2-[3-chloro-4-(trifluoromethyl)phenyl]ethyl]-21-isobutyl-28-isopropyl-7,10,13,16,22,26,29-heptamethyl-18-[(1S)-1-methylpropyl]-25-(piperidine-1-carbonyl)-9-[[2-(trifluoromethoxy)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1642) (5S,8S,11S,15S,18S,23aS,29S,35S,37aS)-8-((S)-sec-butyl)-29-(3-chloro-4-(trifluoromethyl)phenethyl)-35-(cyclohexylmethyl)-5-(cyclopropylmethyl)-11-isobutyl-18-isopropyl-6,12,16,19,33,36-hexamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1643) (3S,9S,18S,21S,25S,28S,34S)-9-[(3-bromophenyl)methyl]-3-[2-[3-chloro-4-(trifluoromethyl)phenyl]ethyl]-21-isobutyl-28-isopropyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1644) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclohexane]-2,5,8,11,14,17,20,23,27,30,33-undecone, (1645) (5S,8S,11S,15S,18S,23aS,29S,35S,37aS)-8,18-di((S)-sec-butyl)-29-(3-chloro-4-(trifluoromethyl)phenethyl)-11-isobutyl-5,6,12,16,19,33,36-heptamethyl-35-(4-methylbenzyl)-15-(pyrrolidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1646) (5S,8S,11S,15S,18S,23aS,29S,35S,37aS)-8-((S)-sec-butyl)-29-(3-chloro-4-(trifluoromethyl)phenethyl)-11-isobutyl-18-isopropyl-5,6,12,16,19,33,36-heptamethyl-15-(piperidine-1-carbonyl)-35-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1647) (3S,9S,18S,21S,25S,28S,34S)-3-[2-[3-chloro-4-(trifluoromethyl)phenyl]ethyl]-28-cyclohexyl-9-(3,3-difluoropropyl)-21-isobutyl-7,10,13,16,22,26,29-heptamethyl-8-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1648) (8S,11S,15R,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-6,12,15,16,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1649) (3S,9S,18S,21S,25S,28S,34S)-3-[2-[3-chloro-4-(trifluoromethyl)phenyl]ethyl]-21-isobutyl-7,10,13,16,22,26,29-heptamethyl-18,28-bis[(1S)-1-methylpropyl]-25-(piperidine-1-carbonyl)-9-(p-tolylmethyl)spiro[1,4,7,10, 13,16,19,22,26,29,32-undecazabicyclo[32.3.0] heptatriacontane-31,1'-cyclopentane]-2,5,8,11,14,17,20, 23,27,30,33-undecone, (1650) (3S,9S,18S,21S,25S,28S,34S)-3-[2-[3-chloro-4-(trifluoromethyl)phenyl]ethyl]-28-cyclohexyl-9-(cyclohexylmethyl)-18,21-diisobutyl-7,10,13,16,22,26,29-heptamethyl-25-(piperidine-1-carbonyl)spiro[1,4,7,10,13,16,19, 22,26,29,32-undecazabicyclo[32.3.0]heptatriacontane-31,1'-cyclopentane]-2,5,8,11,14,17,20,23,27,30,33-undecone, (1651) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-18-isopentyl-7,10,13,16,22,26,29-heptamethyl-25-(piperidine-1-carbonyl)spiro[1,4,7,10, 13,16,19,22,26,29,32-undecazabicyclo[32.3.0] heptatriacontane-31,1'-cyclopentane]-2,5,8,11,14,17,20, 23,27,30,33-undecone, (1652) (3S,9S,18S,21S,25S,28S,34S)-3-[2-[3-chloro-4-(trifluoromethyl)phenyl]ethyl]-28-cyclohexyl-9,21-diisobutyl-7,10,13,16,22,26,29-heptamethyl-18-[(1S)-1-methylpropyl]-25-(piperidine-1-carbonyl)spiro[1,4,7,10, 13,16,19,22,26,29,32-undecazabicyclo[32.3.0] heptatriacontane-31,1'-cyclopentane]-2,5,8,11,14,17,20, 23,27,30,33-undecone, (1653) (5S,8S,11S,15S,18S,23aS,29S,35S,37aS)-8-((S)-sec-butyl)-29-(3-chloro-4-(trifluoromethyl)phenethyl)-11-isobutyl-18-isopropyl-N,N,5,6,12,16,19,33,36-nonamethyl-35-(4-methylbenzyl)-4,7,10,13,17,20,23,28,31, 34,37-undecaoxotetratriacontahydro-2H,4H-spiro[azeto [2,1-u]pyrrolo[2,1-i][1,4,7,10,13,16,19,22,25,28,31] undecaazacyclotetratriacontine-21,1'-cyclopentane]-15-carboxamide, (1654) (5S,8S,11S,15R,18S,23aS,29S,35S,37aS)-8,18-di ((S)-sec-butyl)-29-(3-chloro-4-(trifluoromethyl)phenethyl)-35-(cyclohexylmethyl)-11-isobutyl-5,6,12,15,19, 33,36-heptamethyldocosahydro-2H,4H-spiro[azeto[2,1-u]pyrrolo[2,1-i][1,4,7,10,13,16,19,22,25,28,31] undecaazacyclotetratriacontine-21,1'-cyclopentan]-4,7, 10,13,17,20,23,28,31,34,37(14H,22H)-undecaone, (1655) (3S,6R,9S,18S,21S,25R,28S,34S)-3-[2-[3-chloro-4-(trifluoromethyl)phenyl]ethyl]-9-[(4-fluorophenyl) methyl]-28-isopropyl-6,7,10,13,16,21,22,25,29-nonamethyl-8-[(1S)-1-methylpropyl]spiro[1,4,7,10,13,16,19,22, 26,29,32-undecazabicyclo[32.3.0]heptatriacontane-31,1'-cyclopentane]-2,5,8,11,14,17,20,23,27,30,33-undecone, (1656) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,6,12, 16,19,33,36-heptamethyl-15-(pyrrolidine-1-carbonyl) docosahydro-2H,4H-spiro[azeto[2,1-u]pyrrolo[2,1-i][1,4, 7,10,13,16,19,22,25,28,31] undecaazacyclotetratriacontine-21,1'-cyclopentan]-4,7, 10,13,17,20,23,28,31,34,37(14H,22H)-undecaone, (1657) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11,18-diisobutyl-5,6,12,16,19,33, 36-heptamethyl-15-(piperidine-1-carbonyl)docosahydro-2H,4H-spiro[azeto[2,1-u]pyrrolo[2,1-i][1,4,7,10,13,16, 19,22,25,28,31]undecaazacyclotetratriacontine-21,1'-cyclopentan]-4,7,10,13,17,20,23,28,31,34,37(14H,22H)-undecaone, (1658) (3S,9S,18S,21S,25S,28S,34S)-3-[2-[3-chloro-4-(trifluoromethyl)phenyl]ethyl]-28-cyclohexyl-21-isobutyl-7, 10,13,16,22,26,29-heptamethyl-18-[(1S)-1-methylpropyl]-9-(p-tolylmethyl)-25-(pyrrolidine-1-carbonyl)spiro [1,4,7,10,13,16,19,22,26,29,32-undecazabicyclo[32.3.0] heptatriacontane-31,1'-cyclopentane]-2,5,8,11,14,17,20, 23,27,30,33-undecone, (1659) (3S,9S,18S,21S,25S,28S,34S)-3-[2-[3-chloro-4-(trifluoromethyl)phenyl]ethyl]-9-(cyclohexylmethyl)-28-cyclopentyl-21-isobutyl-N,N,7,10,13,16,22,26,29-nonamethyl-18-[(1S)-1-methylpropyl]-2,5,8,11,14,17,20,23,27, 30,33-undecaoxo-spiro[1,4,7,10,13,16,19,22,26,29,32-undecazabicyclo[32.3.0]heptatriacontane-31,1'-cyclopentane]-25-carboxamide, (1660) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-(3,3-difluoropropyl)-11-isobutyl-5,6,12,16,19,33,36-heptamethyl-15-(piperidine-1-carbonyl)docosahydro-2H,4H-spiro[azeto[2,1-u] pyrrolo[2,1-i][1,4,7,10,13,16,19,22,25,28,31] undecaazacyclotetratriacontine-21,1'-cyclopentan]-4,7, 10,13,17,20,23,28,31,34,37(14H,22H)-undecaone, (1661) (5S,8S,11S,15R,18S,23aS,29S,35S,37aS)-8,18-di ((S)-sec-butyl)-29-(3-chloro-4-(trifluoromethyl)phenethyl)-11-isobutyl-5,6,12,15,19,33,36-heptamethyl-35-(4-methylbenzyl)docosahydro-2H,4H-spiro[azeto[2,1-u] pyrrolo[2,1-i][1,4,7,10,13,16,19,22,25,28,31] undecaazacyclotetratriacontine-21,1'-cyclopentan]-4,7, 10,13,17,20,23,28,31,34,37(14H,22H)-undecaone, (1662) (3S,9S,18S,21S,25S,28S,34S)-3-[2-[3-chloro-4-(trifluoromethyl)phenyl]ethyl]-9-(cyclohexylmethyl)-21-isobutyl-7,10,13,16,22,26,29-heptamethyl-18,28-bis [(1S)-1-methylpropyl]-25-(pyrrolidine-1-carbonyl)spiro [1,4,7,10,13,16,19,22,26,29,32-undecazabicyclo[32.3.0] heptatriacontane-31,1'-cyclopentane]-2,5,8,11,14,17,20, 23,27,30,33-undecone, (1663) (3S,9S,18S,21S,25S,28S,34S)-3-[2-[3-chloro-4-(trifluoromethyl)phenyl]ethyl]-28-cyclohexyl-9-(cyclohexylmethyl)-21-(cyclopentylmethyl)-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1664) (5S,8S,11S,15S,18S,23aS,29S,32R,35S,37aS)-8-((S)-sec-butyl)-29-(3-chloro-4-(trifluoromethyl)phenethyl)-35-(cyclohexylmethyl)-18-isopropyl-5,6,11,12,16, 19,32,33,36-nonamethyl-15-(morpholine-4-carbonyl) docosahydro-2H,4H-spiro[azeto[2,1-u]pyrrolo[2,1-i][1,4, 7,10,13,16,19,22,25,28,31] undecaazacyclotetratriacontine-21,1'-cyclopentan]-4,7, 10,13,17,20,23,28,31,34,37(14H,22H)-undecaone, (1665) (5S,8S,11S,15S,18S,23aS,29S,35S,37aS)-8-((S)-sec-butyl)-29-(3-chloro-4-(trifluoromethyl)phenethyl)-11-isobutyl-18-isopropyl-5,6,12,16,19,33,36-heptamethyl-15-(piperidine-1-carbonyl)-35-(2,2,2-trifluoroethyl)docosahydro-2H,4H-spiro[azeto[2,1-u] pyrrolo[2,1-i][1,4,7,10,13,16,19,22,25,28,31] undecaazacyclotetratriacontine-21,1'-cyclopentan]-4,7, 10,13,17,20,23,28,31,34,37(14H,22H)-undecaone, (1666) (3S,9S,18S,21S,25S,28S,34S)-3-[2-[3-chloro-4-(trifluoromethyl)phenyl]ethyl]-28-cyclohexyl-9-cyclopropyl-21-isobutyl-7,10,13,16,22,26,29-heptamethyl-18-[(1S)-1-methylpropyl]-25-(piperidine-1-carbonyl)spiro [1,4,7,10,13,16,19,22,26,29,32-undecazabicyclo[32.3.0] heptatriacontane-31,1'-cyclopentane]-2,5,8,11,14,17,20, 23,27,30,33-undecone, (1667) (9'S,12'S,16'R,19'S,24a'S,30'S,32a'R,38'S,40a'S)-9'-((S)-sec-butyl)-30'-(3-chloro-4-(trifluoromethyl)phenethyl)-38'-(4-fluorobenzyl)-19'-isopropyl-7',12',13',16', 20',39'-hexamethylhexacosahydro-5'H-spiro [cyclopentane-1,22'-tripyrrolo[2,1-i:2',1'-o:2'',1''-u][1,4, 7,10,13,16,19,22,25,28,31]undecaazacyclotetratriacontin]-5',8',11',14',18',21',24',29',32',37',40'(15'H,23'H)-undecaone,
(1668) (3S,9S,18S,21S,25S,28S,34S)-3-[2-[3-chloro-4-(trifluoromethyl)phenyl]ethyl]-28-cyclohexyl-9-(cyclohexylmethyl)-7,10,13,16,22,26,29-heptamethyl-18-[(1S)-1-methylpropyl]-25-(piperidine-1-carbonyl)-21-(propoxymethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1669) (3S,9S,18S,21S,25S,28S,34S)-3-[2-[3-chloro-4-(trifluoromethyl)phenyl]ethyl]-28-cyclohexyl-9-cyclopentyl-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1670) (8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-6,12,16,19,33,36-hexamethyl-15-(pyrrolidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1671) (3S,9S,18S,21S,25S,28S,34S)-3-[2-[3-chloro-4-(trifluoromethyl)phenyl]ethyl]-28-cyclohexyl-9-(cyclohexylmethyl)-7,10,13,16,22,26,29-heptamethyl-18,21-bis[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1672) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclobutan]-4,7,10,13,17,20,23,28,31,34,37(14H,22H)-undecaone,
(1673) (5S,8S,11S,15R,18S,23aS,29S,35S,37aS)-8-((S)-sec-butyl)-29-(3-chloro-4-(trifluoromethyl)phenethyl)-18-cyclohexyl-11-isobutyl-5,6,12,15,16,19,33,36-octamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1674) (5S,8S,11S,15S,18S,23aS,29S,35S,37aS)-8-((S)-sec-butyl)-29-(3-chloro-4-(trifluoromethyl)phenethyl)-11-isobutyl-18-isopropyl-5,6,12,16,19,33,35,36-octamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1675) (5S,8S,11S,15S,18S,23aS,29S,35S,37aS)-8-((S)-sec-butyl)-29-(3-chloro-4-(trifluoromethyl)phenethyl)-18-cyclohexyl-35-(cyclohexylmethyl)-11-isobutyl-N,N,5,6,12,16,19,33,36-nonamethyl-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide,
(1676) (11S,17S,26S,29S,33S,36S)-9-benzyl-11-[2-[3-chloro-4-(trifluoromethyl)phenyl]ethyl]-17-(cyclohexylmethyl)-36-isopropyl-15,18,21,24,29,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone,
(1677) (5S,8S,11S,15S,18S,23aS,29S,35S,37aS)-8-((S)-sec-butyl)-29-(3-chloro-4-(trifluoromethyl)phenethyl)-35-cyclopropyl-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1678) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-ethyl-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1679) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-cyclopentyl-11-isobutyl-5,6,12,16,19,33,36-heptamethyl-15-(pyrrolidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1680) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29,31,31-nonamethyl-8-[(1S)-1-methylpropyl]-25-(piperidine-1-carbonyl)-1,4,7,10,13,16,19,22,26,29,32-undecazabicyclo[32.3.0]heptatriacontane-2,5,8,11,14,17,20,23,27,30,33-undecone,
(1681) (3S,9S,18S,21S,25S,28S,34S)-3-[2-[3-chloro-4-(trifluoromethyl)phenyl]ethyl]-28-cyclohexyl-21-isobutyl-7,9,10,13,16,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1682) (3S,9S,18S,21S,25R,28S,34S)-3-[2-[3-chloro-4-(trifluoromethyl)phenyl]ethyl]-28-cyclohexyl-21-isobutyl-7,10,13,16,22,25,26,29-octamethyl-18-[(1S)-1-methylpropyl]-9-(p-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1683) (5S,8S,11S,15R,18S,23aS,29S,32R,35S,37aS)-35-benzyl-8-((S)-sec-butyl)-29-(3-chloro-4-(trifluoromethyl)phenethyl)-18-isopropyl-5,6,11,12,15,19,32,33,36-nonamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1684) (5S,8S,11S,15S,18S,23aS,29S,35S,37aS)-8,35-di((S)-sec-butyl)-29-(3-chloro-4-(trifluoromethyl)phenethyl)-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1685) (5S,8S,11S,15S,18S,23aS,29S,35S,37aS)-8-((S)-sec-butyl)-29-(3-chloro-4-(trifluoromethyl)phenethyl)-18-cyclohexyl-11-isobutyl-N,N,5,6,12,16,19,33,36-nonamethyl-35-(4-methylbenzyl)-4,7,10,13,17,20,23,28,31,34,37-undecaoxotetratriacontahydro-2H,4H-spiro[azeto

[2,1-u]pyrrolo[2,1-i][1,4,7,10,13,16,19,22,25,28,31]undecaazacyclotetratriacontine-21,1'-cyclopentane]-15-carboxamide, (1686) (3S,9S,18S,21S,25S,28S,34S)-3-[2-[3-chloro-4-(trifluoromethyl)phenyl]ethyl]-28-cyclohexyl-21-isobutyl-7,10,13,16,22,26,29-heptamethyl-9,18-bis[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1687) (3S,9S,18S,21S,25S,28S,34S)-3-[2-[3-chloro-4-(trifluoromethyl)phenyl]ethyl]-28-cyclohexyl-9-(hydroxymethyl)-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1688) (3S,9S,18S,21S,25S,25R,28S,34S)-3-[2-[3-chloro-4-(trifluoromethyl)phenyl]ethyl]-28-cyclohexyl-9-(cyclohexylmethyl)-7,10,13,16,21,22,25,29-octamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1689) (3S,9S,18S,21S,25S,28S,34S)-3-[2-[3-chloro-4-(trifluoromethyl)phenyl]ethyl]-28-cyclohexyl-9-(cyclopentylmethyl)-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1690) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-(cyclopropoxymethyl)-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1691) (3S,6R,9S,18S,21S,25R,28S,34S)-9-benzyl-3-[2-[3-chloro-4-(trifluoromethyl)phenyl]ethyl]-28-isopropyl-6,7,10,13,16,21,22,25,29-nonamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1692) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-pentyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1693) (8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-9,15,18,21,24,30,34,37-octamethyl-26-[(1S)-1-methylpropyl]-8-(3-pyridylmethyl)-33-(pyrrolidine-1-carbonyl)-6,9,12,15,18,21,24,27,30,34,37-undecazaspiro[4.33]octatriacontane-7,10,13,16,19,22,25,28,31,35,38-undecone, (1694) (3S,9S,18S,21S,25R,28S,34S)-3-[2-[3-chloro-4-(trifluoromethyl)phenyl]ethyl]-28-cyclopentyl-21-isobutyl-7,10,13,16,22,25,26,29-octamethyl-18-[(1S)-1-methylpropyl]-9-(p-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1695) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopropan]-4,7,10,13,17,20,23,28,31,34,37(14H,22H)-undecaone, (1696) (3S,9S,18S,21S,25S,28S,34S)-3-[2-[3-chloro-4-(trifluoromethyl)phenyl]ethyl]-28-cyclohexyl-9-(cyclohexylmethyl)-7,10,13,16,21,22,26,29-octamethyl-8-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1697) (5S,8S,11S,15S,18S,23aS,29S,35S,37aS)-29-(3-chloro-4-(trifluoromethyl)phenethyl)-35-(cyclohexylmethyl)-11-isobutyl-8-isopentyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1698) (9'S,12'S,16'S,19'S,24a'S,30'S,36'S,38a'S)-9'-((S)-sec-butyl)-30'-(3-chloro-4-(trifluoromethyl)phenethyl)-36'-(4-fluorobenzyl)-19'-isopropyl-7',12',13',17',20',34',37'-heptamethyl-16'-(piperidine-1-carbonyl)tetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone, (1699) (3S,9S,18S,21S,25S,28S,34S)-3-[2-[3-chloro-4-(trifluoromethyl)phenyl]ethyl]-9-(cyclopentylmethyl)-21-isobutyl-28-isopropyl-7,10,13,16,22,26,29-heptamethyl-18-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1700) (3S,9S,18S,21S,25S,28S,34S)-3-[2-[3-chloro-4-(trifluoromethyl)phenyl]ethyl]-28-cyclohexyl-9-(cyclohexylmethyl)-21-(3,3-difluoropropyl)-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1701) (3S,9S,18S,21S,25S,28S,34S)-3-[2-[3-chloro-4-(trifluoromethyl)phenyl]ethyl]-28-cyclohexyl-9-(cyclohexylmethyl)-7,10,13,16,22,26,29-heptamethyl-8-[(1S)-1-methylpropyl]-25-(piperidine-1-carbonyl)-21-(2,2,2-trifluoroethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1702) (5S,8S,11S,15R,18S,23aS,29S,32R,35S,37aS)-8-((S)-sec-butyl)-29-(3-chloro-4-(trifluoromethyl)phenethyl)-35-(4-fluorobenzyl)-18-isopropyl-5,6,11,12,15,19,32,33,36-nonamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1703) (6S,9S,13S,16S,22S,25S,31S,34S)-25-[2-[3-chloro-4-(trifluoromethyl)phenyl]ethyl]-16-cyclohexyl-31-(cyclohexylmethyl)-4,9,10,14,17,23,29,32-octamethyl-6-[(1S)-1-methylpropyl]-13-(morpholine-4-carbonyl)-22-(3-pyridylmethyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (1704) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-isopropyl-5,6,12,16,19,33,36-heptamethyl-15-(piperidine-1-carbonyl)-11-(2,2,2- trifluoroethyl)docosahydro-2H,4H-spiro[azeto[2,1-u] pyrrolo[2,1-i][1,4,7,10,13,16,19,22,25,28,31] undecaazacyclotetratriacontine-21,1'-cyclopentan]-4,7,10,13,17,20,23,28,31,34,37(14H,22H)-undecaone, (1705) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-isopropyl-5,6,12,16,19,33,36-heptamethyl-11-pentyl-15-(piperidine-1-carbonyl) docosahydro-2H,4H-spiro[azeto[2,1-u]pyrrolo[2,1-i][1,4,7,10,13,16,19,22,25,28,31] undecaazacyclotetratriacontine-21,1'-cyclopentan]-4,7,10,13,17,20,23,28,31,34,37(14H,22H)-undecaone, (1706) (5S,8S,11S,15R,18S,23aS,29S,35S,37aS)-8-((S)-sec-butyl)-29-(3-chloro-4-(trifluoromethyl)phenethyl)-18-cyclohexyl-35-(cyclohexylmethyl)-11-isobutyl-5,6,12,15,19,33,36-heptamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1707) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-5,6,12,16,19,33,36-heptamethyl-18-pentyl-15-(piperidine-1-carbonyl) docosahydro-2H,4H-spiro[azeto[2,1-u]pyrrolo[2,1-i][1,4,7,10,13,16,19,22,25,28,31] undecaazacyclotetratriacontine-21,1'-cyclopentan]-4,7,10,13,17,20,23,28,31,34,37(14H,22H)-undecaone, (1708) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,6,12,16,19,33,36-heptamethyl-15-(piperidine-1-carbonyl) docosahydro-2H,4H-spiro[azeto[2,1-u]pyrrolo[2,1-i][1,4,7,10,13,16,19,22,25,28,31] undecaazacyclotetratriacontine-21,1'-cyclohexan]-4,7,10,13,17,20,23,28,31,34,37(14H,22H)-undecaone, (1709) (5S,8S,11S,15S,18S,23aS,29S,35S,37aS)-8-((S)-sec-butyl)-29-(3-chloro-4-(trifluoromethyl)phenethyl)-11-isobutyl-35-isopentyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1710) (5S,8S,11S,15R,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,6,12,16,19,33,36-heptamethyl-15-(pyrrolidine-1-carbonyl)docosahydro-2H,4H-spiro[azeto[2,1-u]pyrrolo[2,1-i][1,4,7,10,13,16,19,22,25,28,31] undecaazacyclotetratriacontine-21,1'-cyclopentan]-4,7,10,13,17,20,23,28,31,34,37(14H,22H)-undecaone, (1711) (3S,9S,18S,21S,25S,28S,34S)-3-[2-[3-chloro-4-(trifluoromethyl)phenyl]ethyl]-9-(cyclohexylmethyl)-21-isobutyl-28-isopropyl-7,10,13,16,22,26,29-heptamethyl-18-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1712) (5S,8S,11S,15S,18S,23aS,29S,35S,37aS)-8-((S)-sec-butyl)-35-butyl-29-(3-chloro-4-(trifluoromethyl) phenethyl)-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1713) (3S,9S,18S,21S,25S,28S,34S)-3-[2-[3-chloro-4-(trifluoromethyl)phenyl]ethyl]-28-cyclohexyl-9-(cyclohexylmethyl)-21-(hydroxymethyl)-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1714) (5S,8S,11S,15R,18S,23aS,29S,35S,37aS)-8-((S)-sec-butyl)-29-(3-chloro-4-(trifluoromethyl)phenethyl)-18-cyclopentyl-36-ethyl-11-isobutyl-5,6,12,15,19,33-hexamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1715) (9'S,12'S,16'S,19'S,24a'S,30'S,33'R,36'S,38a'S)-9'-((S)-sec-butyl)-30'-(3-chloro-4-(trifluoromethyl)phenethyl)-36'-(cyclohexylmethyl)-19'-isopropyl-7',12',13',17',20',33',34',37'-octamethyl-16'-(pyrrolidine-1-carbonyl)tetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone, (1716) (5S,8S,11S,15S,18S,23aS,29S,35S,37aS)-8-((S)-sec-butyl)-29-(3-chloro-4-(trifluoromethyl)phenethyl)-35-(cyclobutylmethyl)-11-isobutyl-18-isopropyl-5,6,12,16,19,33,36-heptamethyl-15-(piperidine-1-carbonyl) docosahydro-2H,4H-spiro[azeto[2,1-u]pyrrolo[2,1-i][1,4,7,10,13,16,19,22,25,28,31] undecaazacyclotetratriacontine-21,1'-cyclopentan]-4,7,10,13,17,20,23,28,31,34,37(14H,22H)-undecaone, (1717) (5S,8S,11S,15R,18S,23aS,29S,35S,37aS)-8-((S)-sec-butyl)-29-(3-chloro-4-(trifluoromethyl)phenethyl)-35-(cyclohexylmethyl)-18-cyclopentyl-11-isobutyl-5,6,12,15,16,19,33,36-octamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1718) (8S,11S,17S,26S,29S,33S,36S)-11-[2-[3-chloro-4-(trifluoromethyl)phenyl]ethyl]-36-cyclohexyl-17-(cyclohexylmethyl)-9,15,18,21,24,29,30,34,37-nonamethyl-26-[(1S)-1-methylpropyl]-33-(morpholine-4-carbonyl)-8-(3-pyridylmethyl)-6,9,12,15,18,21,24,27,30,34,37-undecazaspiro[4.33]octatriacontane-7,10,13,16,19,22,25,28,31,35,38-undecone, (1719) (3S,9S,18S,21S,25S,28S,34S)-3-[2-[3-chloro-4-(trifluoromethyl)phenyl]ethyl]-9-(cyclohexylmethyl)-21-isobutyl-7,10,13,16,22,26,29-heptamethyl-18-[(1S)-1-methylpropyl]-28-pentyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1720) (3S,9S,18S,21S,25S,28S,34S)-3-[2-[3-chloro-4-(trifluoromethyl)phenyl]ethyl]-28-cyclohexyl-9-(cyclohexylmethyl)-7,10,13,16,21,22,26,29-octamethyl-8-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1721) (5S,8S,11S,15S,18S,23aS,29S,35S,37aS)-8-((S)-sec-butyl)-29-(3-chloro-4-(trifluoromethyl)phenethyl)-35-(hydroxymethyl)-11-isobutyl-18-isopropyl-5,6,12,16,19,33,36-heptamethyl-15-(piperidine-1-carbonyl) docosahydro-2H,4H-spiro[azeto[2,1-u]pyrrolo[2,1-i][1,4,7,10,13,16,19,22,25,28,31] undecaazacyclotetratriacontine-21,1'-cyclopentan]-4,7,10,13,17,20,23,28,31,34,37(14H,22H)-undecaone, (1722) (5S,8S,11S,15S,18S,23aS,29S,35S,37aS)-8,18-di((S)-sec-butyl)-29-(3-chloro-4-(trifluoromethyl)phenethyl)-35-(cyclohexylmethyl)-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1723) (3S,9S,18S,21S,25S,28S,34S)-18-butyl-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1724) (5S,8S,11S,15S,18S,23aS,29S,32R,35S,37aS)-35-benzyl-8-((S)-sec-butyl)-29-(3-chloro-4-(trifluoromethyl)phenethyl)-18-isopropyl-5,6,11,12,16,19,32,33,36-nonamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1725) (9'S,12'S,16'S,19'S,24a'S,30'S,32a'R,38'S,40a'S)-9'-((S)-sec-butyl)-30'-(3-chloro-4-(trifluoromethyl)phenethyl)-38'-(4-fluorobenzyl)-19'-isopropyl-7',12',13',17',20',39'-hexamethyl-16'-(piperidine-1-carbonyl)hexacosahydro-5'H-spiro[cyclopentane-1,22'-tripyrrolo[2,1-i:2',1'-o:2",1"-u][1,4,7,10,13,16,19,22,25,28,31]undecaazacyclotetratriacontin]-5',8',11',14',18',21',24',29',32',37',40'(15'H,23'H)-undecaone, (1726) (5S,8S,11S,15S,18S,23aS,29S,35S,37aS)-8-((S)-sec-butyl)-29-(3-chloro-4-(trifluoromethyl)phenethyl)-18-cyclohexyl-35-(cyclohexylmethyl)-11-isobutyl-5,6,12,16,19,33,36-heptamethyl-15-(pyrrolidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1727) (5S,8S,11S,15S,18S,23aS,29S,35S,37aS)-8,18-di((S)-sec-butyl)-29-(3-chloro-4-(trifluoromethyl)phenethyl)-11-isobutyl-5,6,12,16,19,33,36-heptamethyl-35-(4-methylbenzyl)-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1728) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-N,N,5,6,12,16,19,33,36-nonamethyl-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1729) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-N,N,7,10,13,16,22,26,29-nonamethyl-18-[(1S)-1-methylpropyl]-2,5,8,11,14,17,20,23,27,30,33-undecaoxo-spiro[1,4,7,10,13,16,19,22,26,29,32-undecazabicyclo[32.3.0]heptatriacontane-31,1'-cyclopentane]-25-carboxamide, (1730) (9'S,12'S,16'R,19'S,24a'S,30'S,32a'R,38'S,40a'S)-38'-benzyl-9'-((S)-sec-butyl)-30'-(3-chloro-4-(trifluoromethyl)phenethyl)-19'-isopropyl-7',12',13',16',20',39'-hexamethylhexacosahydro-5'H-spiro[cyclopentane-1,22'-tripyrrolo[2,1-i:2',1'-o:2",1"-u][1,4,7,10,13,16,19,22,25,28,31]undecaazacyclotetratriacontin]-5',8',11',14',18',21',24',29',32',37',40'(15'H,23'H)-undecaone, (1731) (3S,9S,18S,21S,25S,28S,34S)-3-[2-[3-chloro-4-(trifluoromethyl)phenyl]ethyl]-28-cyclohexyl-9-(cyclopropoxymethyl)-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1732) (9'S,12'S,16'R,19'S,24a'S,30'S,36'S,38a'S)-9'-((S)-sec-butyl)-30'-(3-chloro-4-(trifluoromethyl)phenethyl)-36'-(4-fluorobenzyl)-19'-isopropyl-7',12',13',16',20',34',37'-heptamethyltetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone, (1733) (5S,8S,11S,15R,18S,23aS,29S,35S,37aS)-8,18-di((S)-sec-butyl)-29-(3-chloro-4-(trifluoromethyl)phenethyl)-35-(cyclohexylmethyl)-11-isobutyl-5,6,12,15,16,19,33,36-octamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1734) (5S,8S,11S,15R,18S,23aS,29S,35S,37aS)-8,18-di((S)-sec-butyl)-29-(3-chloro-4-(trifluoromethyl)phenethyl)-11-isobutyl-5,6,12,16,19,33,36-heptamethyl-15-(pyrrolidine-1-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1735) (3S,9S,18S,21S,25S,28S,34S)-3-[2-[3-chloro-4-(trifluoromethyl)phenyl]ethyl]-28-cyclohexyl-9-(cyclohexylmethyl)-7,10,13,16,22,26,29-heptamethyl-18-[(1S)-1-methylpropyl]-21-pentyl-25-(piperidine-1-carbonyl)spiro[11,4,7,10,13,16,19,22,26,29,32-undecazabicyclo[32.3.0]heptatriacontane-31,1'-cyclopentane]-2,5,8,11,14,17,20,23,27,30,33-undecone, (1736) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-25-(piperidine-1-carbonyl)-18-(propoxymethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1737) (5S,8S,11S,15S,18S,23aS,29S,35S,37aS)-8-((S)-sec-butyl)-29-(3-chloro-4-(trifluoromethyl)phenethyl)-11-isobutyl-18,35-diisopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1738) (5S,8S,11S,15S,18S,23aS,29S,35S,37aS)-8-((S)-sec-butyl)-29-(3-chloro-4-(trifluoromethyl)phenethyl)-35-(cyclopropoxymethyl)-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1739) (5S,8S,11S,15S,18S,23aS,29S,35S,37aS)-8-((S)-sec-butyl)-29-(3-chloro-4-(trifluoromethyl)phenethyl)-35-(cyclopentylmethyl)-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]

undecaazacyclotetratriacontine-21,1'-cyclopentan]-4,7,
10,13,17,20,23,28,31,34,37(14H,22H)-undecaone,
(1740) (3S,9S,18S,21S,25S,28S,34S)-21-butyl-3-[2-[3-chloro-4-(trifluoromethyl)phenyl]ethyl]-28-cyclohexyl-9-(cyclohexylmethyl)-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1741) (3S,9S,18S,21S,25S,28S,34S)-3-[2-[3-chloro-4-(trifluoromethyl)phenyl]ethyl]-9-(cyclohexylmethyl)-28-ethyl-21-isobutyl-7,10,13,16,22,26,29-heptamethyl-8-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1742) (9'S,12'S,16'R,19'S,24a'S,30'S,33'R,36'S,38a'S)-9'-((S)-sec-butyl)-30'-(3-chloro-4-(trifluoromethyl)phenethyl)-36'-(4-fluorobenzyl)-19'-isopropyl-7',12',13',16',20',33',34',37'-octamethyltetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone,
(1743) (3S,9S,18S,21S,25S,28S,34S)-3-[2-[3-chloro-4-(trifluoromethyl)phenyl]ethyl]-28-cyclohexyl-9-ethyl-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1744) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-25-(piperidine-1-carbonyl)-18-(2,2,2-trifluoroethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1745) (8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-9,15,18,21,24,30,34,37-octamethyl-26-[(1S)-1-methylpropyl]-33-(morpholine-4-carbonyl)-8-(3-pyridylmethyl)-6,9,12,15,18,21,24,27,30,34,37-undecazaspiro[4.33]octatriacontane-7,10,13,16,19,22,25,28,31,35,38-undecone,
(1746) (3S,9S,18S,21S,25S,28S,34S)-3-[2-[3-chloro-4-(trifluoromethyl)phenyl]ethyl]-21-(cyclobutylmethyl)-28-cyclohexyl-9-(cyclohexylmethyl)-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1747) (5S,8S,11S,15R,18S,23aS,29S,35S,37aS)-8-((S)-sec-butyl)-29-(3-chloro-4-(trifluoromethyl)phenethyl)-18-cyclohexyl-11-isobutyl-5,6,12,15,19,33,36-heptamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1748) (3S,9S,18S,21S,25S,28S,34S,36R)-3-[2-[3-chloro-4-(trifluoromethyl)phenyl]ethyl]-9-(cyclohexylmethyl)-36-ethoxy-21,28-diisobutyl-7,10,13,16,22,26,29-heptamethyl-18-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1749) (3S,9S,18S,21S,25S,28S,34S)-3-[2-[3-chloro-4-(trifluoromethyl)phenyl]ethyl]-21-isobutyl-28-isopropyl-7,10,13,16,22,26,29-heptamethyl-18-[(1S)-1-methylpropyl]-9-(p-tolylmethyl)-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1750) (5S,8S,11S,15R,18S,23aS,29S,35S,37aS)-8-((S)-sec-butyl)-29-(3-chloro-4-(trifluoromethyl)phenethyl)-18-cyclopentyl-11-isobutyl-5,6,12,15,16,19,33,36-octamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1751) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,6,12,16,19,21,21,33,36-nonamethyl-15-(piperidine-1-carbonyl)tetracosahydro-2H-azeto[2,1-u]pyrrolo[2,1-i][1,4,7,10,13,16,19,22,25,28,31]undecaazacyclotetratriacontin-4,7,10,13,17,20,23,28,31,34,37(14H)-undecaone,
(1752) (5S,8S,11S,15S,18S,23aS,29S,35S,37aS)-8-((S)-sec-butyl)-29-(3-chloro-4-(trifluoromethyl)phenethyl)-35-ethyl-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1753) (9'S,12'S,16'S,19'S,24a'S,30'S,36'S,38a'S)-36'-benzyl-9'-((S)-sec-butyl)-30'-(3-chloro-4-(trifluoromethyl)phenethyl)-19'-isopropyl-7',12',13',17',20',34',37'-heptamethyl-16'-(piperidine-1-carbonyl)tetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone,
(1754) (5S,8S,11S,15S,18S,23aS,29S,35S,37aS)-29-(3-chloro-4-(trifluoromethyl)phenethyl)-35-(cyclohexylmethyl)-8,11-diisobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1755) (3S,6R,9S,18S,21S,25S,28S,34S)-3-[2-[3-chloro-4-(trifluoromethyl)phenyl]ethyl]-9-[(4-fluorophenyl)methyl]-28-isopropyl-6,7,10,13,16,21,22,26,29-nonamethyl-8-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1756) (5S,8S,11S,15S,18S,23aS,29S,35S,37aS)-8-((S)-sec-butyl)-29-(3-chloro-4-(trifluoromethyl)phenethyl)-18-cyclopentyl-11-isobutyl-N,N,5,6,12,16,19,33,36-nonamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide,
(1757) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1758) (8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-6,12,16,19,33,36-hexamethyl-15-(morpholine-4-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1759) (3S,9S,18S,21S,25S,28S,34S)-3-[2-[3-chloro-4-(trifluoromethyl)phenyl]ethyl]-18-(cyclobutylmethyl)-28-cyclohexyl-9-(cyclohexylmethyl)-21-isobutyl-7,10,13,16,22,26,29-heptamethyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1760) (5S,8S,11S,15S,18S,23aS,29S,35S,37aS)-29-(3-chloro-4-(trifluoromethyl)phenethyl)-35-(cyclohexylmethyl)-8-ethyl-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1761) (3S,9S,18S,21S,25S,28S,34S)-3-[2-[3-chloro-4-(trifluoromethyl)phenyl]ethyl]-28-cyclopentyl-21-isobutyl-7,10,13,16,22,26,29-heptamethyl-18-[(1S)-1-methylpropyl]-9-(p-tolylmethyl)-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1762) (3S,9S,18S,21S,25S,28S,34S)-3-[2-[3-chloro-4-(trifluoromethyl)phenyl]ethyl]-28-cyclohexyl-21-isobutyl-N,N,7,10,13,16,22,26,29-nonamethyl-18-[(1S)-1-methylpropyl]-2,5,8,11,14,17,20,23,27,30,33-undecaoxo-9-(p-tolylmethyl)spiro[1,4,7,10,13,16,19,22,26,29,32-undecazabicyclo[32.3.0]heptatriacontane-31,1'-cyclopentane]-25-carboxamide, (1763) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-isopropyl-5,6,12,16,19,33,36-heptamethyl-15-(piperidine-1-carbonyl)-11-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1764) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-(cyclopropoxymethyl)-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1765) (5S,8S,11S,15R,18S,23aS,29S,35S,37aS)-8-((S)-sec-butyl)-29-(3-chloro-4-(trifluoromethyl)phenethyl)-18-cyclopentyl-11-isobutyl-5,6,12,16,19,33,36-heptamethyl-15-(pyrrolidine-1-carbonyl)-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1766) (3S,9S,18S,21S,25S,28S,34S)-3-[2-[3-chloro-4-(trifluoromethyl)phenyl]ethyl]-28-cyclohexyl-9-(cyclohexylmethyl)-18-(cyclopropoxymethyl)-21-isobutyl-7,10,13,16,22,26,29-heptamethyl-25-(piperidine-1-carbonyl)spiro[11,4,7,10,13,16,19,22,26,29,32-undecazabicyclo[32.3.0]heptatriacontane-31,1'-cyclopentane]-2,5,8,11,14,17,20,23,27,30,33-undecone, (1767) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11,18-diisopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1768) (5S,8S,11S,15S,18S,23aS,29S,35S,37aS)-29-(3-chloro-4-(trifluoromethyl)phenethyl)-35-(cyclohexylmethyl)-8-(hydroxymethyl)-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1769) (5S,8S,11S,15S,18S,23aS,29S,35S,37aS)-8-((S)-sec-butyl)-29-(3-chloro-4-(trifluoromethyl)phenethyl)-35-(3,3-difluoropropyl)-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1770) (3S,9S,18S,21S,25S,28S,34S)-3-[2-[3-chloro-4-(trifluoromethyl)phenyl]ethyl]-28-cyclohexyl-9-(cyclohexylmethyl)-21-ethyl-7,10,13,16,22,26,29-heptamethyl-8-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1771) (3S,9S,18S,21S,25S,28S,34S)-3-[2-[3-chloro-4-(trifluoromethyl)phenyl]ethyl]-9-(cyclohexylmethyl)-21-isobutyl-7,10,13,16,22,26,29-heptamethyl-18-[(1S)-1-methylpropyl]-25-(piperidine-1-carbonyl)-28-(propoxymethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1772) (5S,8S,11S,15S,18S,23aS,29S,35S,37aS)-8-((S)-sec-butyl)-29-(3-chloro-4-(trifluoromethyl)phenethyl)-18-cyclopentyl-11-isobutyl-5,6,12,16,19,33,36-heptamethyl-35-(4-methylbenzyl)-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1773) (5S,8S,11S,15R,18S,23aS,29S,32R,35S,37aS)-8-((S)-sec-butyl)-29-(3-chloro-4-(trifluoromethyl)phenethyl)-35-(cyclohexylmethyl)-18-isopropyl-5,6,11,12,15,16,19,32,33,36-decamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1774) (3S,9S,18S,21S,25R,28S,34S)-3-[2-[3-chloro-4-(trifluoromethyl)phenyl]ethyl]-21-isobutyl-7,10,13,16,22,25,29-heptamethyl-18,28-bis[(1S)-1-methylpropyl]-9-(p-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1775) (3S,9S,18S,21S,25S,28S,34S)-3-[2-[3-chloro-4-(trifluoromethyl)phenyl]ethyl]-28-cyclohexyl-9-(cyclohexylmethyl)-18-ethyl-21-isobutyl-7,10,13,16,22,26,29-heptamethyl-25-(piperidine-1-carbonyl)spiro[1,4,7,10,13,16, 19,22,26,29,32-undecazabicyclo[32.3.0]heptatriacontane-31,1'-cyclopentane]-2,5,8,11,14,17,20,23,27,30,33-undecone, (1776) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopentyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1777) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-cyclopentyl-11-isobutyl-N,N,5,6,12,16,19,33,36-nonamethyl-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1778) (9'S,12'S,16'R,19'S,24a'S,30'S,36'S,38a'S)-36'-benzyl-9'-((S)-sec-butyl)-30'-(3-chloro-4-(trifluoromethyl)phenethyl)-19'-isopropyl-7',12',13',16',20',34',37'-heptamethyltetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone, (1779) (3S,9S,18S,21S,25S,28S,34S)-3-[2-[3-chloro-4-(trifluoromethyl)phenyl]ethyl]-28-cyclopentyl-21-isobutyl-N,N,7,10,13,16,22,26,29-nonamethyl-18-[(1S)-1-methylpropyl]-2,5,8,11,14,17,20,23,27,30,33-undecaoxo-9-(p-tolylmethyl)spiro[1,4,7,10,13,16,19,22,26,29,32-undecazabicyclo[32.3.0]heptatriacontane-31,1'-cyclopentane]-25-carboxamide, (1780) (5S,8S,11S,15S,18S,23aS,29S,35S,37aS)-29-(3-chloro-4-(trifluoromethyl)phenethyl)-35-(cyclohexylmethyl)-11-isobutyl-18-isopropyl-5,6,8,12,16,19,33,36-octamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1781) (3S,9S,18S,21S,25R,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1782) (3S,9S,18S,21S,25S,28S,34S)-3-[2-[3-chloro-4-(trifluoromethyl)phenyl]ethyl]-9-(cyclohexylmethyl)-28-(3,3-difluoropropyl)-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1783) (9'S,12'S,16'R,19'S,24a'S,30'S,33'R,36'S,38a'S)-36'-benzyl-9'-((S)-sec-butyl)-30'-(3-chloro-4-(trifluoromethyl)phenethyl)-19'-isopropyl-7',12',13',16',20',33',34',37'-octamethyltetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone, (1784) (9'S,12'S,16'R,19'S,24a'S,30'S,33'S,36'S,38a'S)-9'-((S)-sec-butyl)-30'-(3-chloro-4-(trifluoromethyl)phenethyl)-36'-(cyclohexylmethyl)-19'-isopropyl-7',12',13',16',17',20',33',34',37'-nonamethyltetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone, (1785) (3S,9S,18S,21S,25S,28S,34S,36R)-3-[2-[3-chloro-4-(trifluoromethyl)phenyl]ethyl]-9-(cyclohexylmethyl)-36-ethoxy-21,28-diisobutyl-7,10,13,16,22,26,29-heptamethyl-18-[(1S)-1-methylpropyl]-25-(morpholine-4-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1786) (3S,9S,18S,21S,25S,28S,34S)-3-[2-[3-chloro-4-(trifluoromethyl)phenyl]ethyl]-28-cyclohexyl-9-(cyclohexylmethyl)-21-(cyclopropoxymethyl)-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1787) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-cyclopentyl-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1788) (9'S,12'S,16'S,19'S,24a'S,30'S,33'R,36'S,38a'S)-9'-((S)-sec-butyl)-30'-(3-chloro-4-(trifluoromethyl)phenethyl)-36'-(cyclohexylmethyl)-19'-isopropyl-7',12',13',17',20',33',34',37'-octamethyl-16'-(morpholine-4-carbonyl)tetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone, (1789) (3S,9S,18S,21S,25R,28S,34S,36R)-3-[2-[3-chloro-4-(trifluoromethyl)phenyl]ethyl]-9-(cyclohexylmethyl)-36-ethoxy-21,28-diisobutyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1790) (3S,9S,18S,21S,25S,28S,34S)-3-[2-[3-chloro-4-(trifluoromethyl)phenyl]ethyl]-21-isobutyl-7,10,13,16,22,26,29-heptamethyl-18,28-bis[(1S)-1-methylpropyl]-9-(p-tolylmethyl)-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1791) (5S,8S,11S,15S,18S,23aS,29S,35S,37aS)-29-(3-chloro-4-(trifluoromethyl)phenethyl)-35-(cyclohexylmethyl)-11-isobutyl-8,18-diisopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1792) (3S,9S,18S,21S,25R,28S,34S)-3-[2-[3-chloro-4-(trifluoromethyl)phenyl]ethyl]-21-isobutyl-7,10,13,16,22,25,26,29-octamethyl-18,28-bis[(1S)-1-methylpropyl]-9-(p-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1793) (5S,8S,11S,15R,18S,23aS,29S,35S,37aS)-8,18-di((S)-sec-butyl)-29-(3-chloro-4-(trifluoromethyl)phenethyl)-11-isobutyl-5,6,12,15,16,19,33,36-octamethyl-35-(4-methylbenzyl)docosahydro-2H,4H-spiro[azeto[2,1-u]pyrrolo[2,1-i][1,4,7,10,13,16,19,22,25,28,31]

undecaazacyclotetratriacontine-21,1'-cyclopentan]-4,7,
10,13,17,20,23,28,31,34,37(14H,22H)-undecaone,
(1794) (3S,9S,18S,21S,25R,28S,34S)-3-[2-[3-chloro-4-(trifluoromethyl)phenyl]ethyl]-9-(cyclohexylmethyl)-28-cyclopentyl-21-isobutyl-7,10,13,16,22,26,29-heptamethyl-18-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1795) (5S,8S,11S,15S,18S,23aS,29S,35S,37aS)-8-((S)-sec-butyl)-29-(3-chloro-4-(trifluoromethyl)phenethyl)-18-cyclohexyl-11-isobutyl-5,6,12,16,19,33,36-heptamethyl-35-(4-methylbenzyl)-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1796) (3S,9S,18S,21S,25S,28S,34S)-3-[2-[3-chloro-4-(trifluoromethyl)phenyl]ethyl]-28-cyclohexyl-9-(cyclohexylmethyl)-21-cyclopropyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1797) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-(3,3-difluoropropyl)-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1798) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-18-isopropyl-7,10,13,16,22,26,29-heptamethyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1799) (3S,9S,18S,21S,25S,28S,34S)-3-[2-[3-chloro-4-(trifluoromethyl)phenyl]ethyl]-28-cyclohexyl-9-(cyclohexylmethyl)-18-(hydroxymethyl)-21-isobutyl-7,10,13,16,22,26,29-heptamethyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1800) (5S,8S,11S,15R,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,6,12,15,16,19,33,36-octamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1801) (5S,8S,11S,15R,18S,23aS,29S,35S,37aS)-8-((S)-sec-butyl)-29-(3-chloro-4-(trifluoromethyl)phenethyl)-11-isobutyl-18-isopropyl-5,6,12,15,19,33,36-heptamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1802) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,18,22,26,29-octamethyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1803) (5S,8S,11S,15S,18S,23aS,29S,35S,37aS)-8-((S)-sec-butyl)-29-(3-chloro-4-(trifluoromethyl)phenethyl)-11,35-diisobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1804) (3S,9S,18S,21S,25S,28S,34S)-3-[2-[3-chloro-4-(trifluoromethyl)phenyl]ethyl]-28-cyclohexyl-21-isobutyl-7,10,13,16,22,26,29-heptamethyl-18-[(1S)-1-methylpropyl]-25-(piperidine-1-carbonyl)-9-(p-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1805) (3S,9S,18S,21S,25S,28S,34S)-3-[2-[3-chloro-4-(trifluoromethyl)phenyl]ethyl]-28-cyclohexyl-21-isobutyl-7,10,13,16,22,26,29-heptamethyl-18-[(1S)-1-methylpropyl]-25-(piperidine-1-carbonyl)-9-(propoxymethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1806) (9'S,12'S,16'S,19'S,24a'S,30'S,33'R,36'S,38a'S)-36'-benzyl-9'-((S)-sec-butyl)-30'-(3-chloro-4-(trifluoromethyl)phenethyl)-19'-isopropyl-7',12',13',17',20',33',34',37'-octamethyl-16'-(piperidine-1-carbonyl)tetracosahydro-5'H-spiro[cyclopentane-1,22'-dipyrrolo[2,1-i:2',1''-u][1,4,7,10,13,16,19,22,25,28,31]undecaazacyclotetratriacontin-5',8',11',14',18',21',24',29',32',35',38'(15'H,23'H)-undecaone,
(1807) (3S,9S,18S,21S,25S,28S,34S)-3-[2-[3-chloro-4-(trifluoromethyl)phenyl]ethyl]-28-cyclohexyl-9-(cyclohexylmethyl)-21-isopropyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1808) (3S,9S,18S,21S,25R,28S,34S)-3-[2-[3-chloro-4-(trifluoromethyl)phenyl]ethyl]-28-cyclohexyl-9-(cyclohexylmethyl)-7,10,13,16,21,22,25,26,29-nonamethyl-8-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1809) (5S,8S,11S,15R,18S,23aS,29S,35S,37aS)-8-((S)-sec-butyl)-29-(3-chloro-4-(trifluoromethyl)phenethyl)-11-isobutyl-18-isopropyl-5,6,12,15,16,19,33,36-octamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1810) (6S,9S,13S,16S,22S,25S,31S,34S)-25-[2-[3-chloro-4-(trifluoromethyl)phenyl]ethyl]-16-cyclohexyl-31-(cyclohexylmethyl)-4,9,10,14,17,23,29,32-octamethyl-6-[(1S)-1-methylpropyl]-22-(3-pyridylmethyl)-13-(pyrrolidine-1-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone,
(1811) (5S,8S,11S,15S,18S,23aS,29S,35S,37aS)-29-(3-chloro-4-(trifluoromethyl)phenethyl)-35-(cyclohexylmethyl)-8-(cyclopropoxymethyl)-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1812) (3S,9S,18S,21S,25S,28S,34S)-3-[2-[3-chloro-4-(trifluoromethyl)phenyl]ethyl]-9-(cyclohexylmethyl)-21- isobutyl-28-isopropyl-N,N,7,10,13,16,22,26,29-nonamethyl-18-[(1S)-1-methylpropyl]-2,5,8,11,14,17,20,23,27,30,33-undecaoxo-spiro[1,4,7,10,13,16,19,22,26,29,32-undecazabicyclo[32.3.0]heptatriacontane-31,1'-cyclopentane]-25-carboxamide, (1813) (5S,8S,11S,15R,18S,23aS,29S,35S,37aS)-8-((S)-sec-butyl)-29-(3-chloro-4-(trifluoromethyl)phenethyl)-18-cyclohexyl-35-(cyclohexylmethyl)-11-isobutyl-5,6,12,15,16,19,33,36-octamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1814) (3S,9S,18S,21S,25R,28S,34S)-3-[2-[3-chloro-4-(trifluoromethyl)phenyl]ethyl]-9-(cyclohexylmethyl)-21-isobutyl-7,10,13,16,22,26,29-heptamethyl-18,28-bis[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1815) (3S,9S,18S,21S,25S,28S,34S)-28-butyl-3-[2-[3-chloro-4-(trifluoromethyl)phenyl]ethyl]-9-(cyclohexylmethyl)-21-isobutyl-7,10,13,16,22,26,29-heptamethyl-8-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1816) (5S,8S,11S,15S,18S,23aS,29S,32R,35S,37aS)-8-((S)-sec-butyl)-29-(3-chloro-4-(trifluoromethyl)phenethyl)-35-(4-fluorobenzyl)-18-isopropyl-5,6,11,12,16,19,32,33,36-nonamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1817) (3S,9S,18S,21S,25S,28S,34S)-3-[2-[3-chloro-4-(trifluoromethyl)phenyl]ethyl]-9-(cyclobutylmethyl)-28-cyclohexyl-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1818) (3S,9S,18S,21S,25S,28S,34S)-3-[2-[3-chloro-4-(trifluoromethyl)phenyl]ethyl]-9-(cyclohexylmethyl)-28-cyclopentyl-21-isobutyl-7,10,13,16,22,26,29-heptamethyl-18-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1819) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-18-isopropyl-5,6,12,16,19,33,36-heptamethyl-15-(piperidine-1-carbonyl)icosahydro-2H,4H-spiro[azeto[2,1-u]pyrrolo[2,1-i][1,4,7,10,13,16,19,22,25,28,31]undecaazacyclotetratriacontine-21,1'-cyclopentane]-4,7,10,13,17,20,23,25,28,31,34,37(14H,22H,26H)-dodecaone, (1820) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-(cyclopentylmethyl)-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1821) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclobutane]-2,5,8,11,14,17,20,23,27,30,33-undecone, (1822) (5S,8S,11S,15S,18S,23aS,29S,35S,37aS)-8-((S)-sec-butyl)-29-(3-chloro-4-(trifluoromethyl)phenethyl)-35-(cyclohexylmethyl)-18-cyclopropyl-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1823) (5S,8S,11S,15S,18S,23aS,29S,35S,37aS)-8-butyl-29-(3-chloro-4-(trifluoromethyl)phenethyl)-35-(cyclohexylmethyl)-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1824) (3S,9S,18S,21S,25S,28S,34S)-3-[2-[3-chloro-4-(trifluoromethyl)phenyl]ethyl]-28-cyclohexyl-9-(cyclohexylmethyl)-18-cyclopentyl-21-isobutyl-7,10,13,16,22,26,29-heptamethyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1825) (5S,8S,11S,15S,18S,23aS,29S,35S,37aS)-8-((S)-sec-butyl)-29-(3-chloro-4-(trifluoromethyl)phenethyl)-35-cyclopentyl-11-isobutyl-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1826) (5S,8S,11S,15S,18S,23aS,29S,35S,37aS)-29-(3-chloro-4-(trifluoromethyl)phenethyl)-35-(cyclohexylmethyl)-11-isobutyl-18-isopropyl-5,6,12,16,19,33,36-heptamethyl-8-pentyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1827) (5S,8S,11S,15S,18S,23aS,29S,32R,35S,37aS)-8-((S)-sec-butyl)-29-(3-chloro-4-(trifluoromethyl)phenethyl)-35-(cyclohexylmethyl)-18-isopropyl-5,6,11,12,16,19,32,33,36-nonamethyl-15-(pyrrolidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1828) (5S,8S,11S,15S,18S,23aS,29S,35S,37aS)-8-((S)-sec-butyl)-29-(3-chloro-4-(trifluoromethyl)phenethyl)-11-isobutyl-18-isopropyl-5,6,12,16,19,33,36-heptamethyl-35-(4-methylbenzyl)-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1829) (3S,9S,18S,21S,25S,28S,34S)-3-[2-[3-chloro-4-(trifluoromethyl)phenyl]ethyl]-28-cyclohexyl-21-isobutyl-9-isopropyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1830) (3S,9S,18S,21S,25S,28S,34S)-3-[2-[3-chloro-4-(trifluoromethyl)phenyl]ethyl]-28-cyclohexyl-21-isobutyl-9-isopentyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1831) (5S,8S,11S,15S,18S,23aS,29S,35S,37aS)-29-(3-chloro-4-(trifluoromethyl)phenethyl)-35-(cyclohexylmethyl)-11-isobutyl-18-isopropyl-5,6,12,16,19,33,36-heptamethyl-15-(piperidine-1-carbonyl)-8-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1832) (3S,9S,18S,21S,25S,28S,34S)-9-butyl-3-[2-[3-chloro-4-(trifluoromethyl)phenyl]ethyl]-28-cyclohexyl-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1833) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isopentyl-18-isopropyl-5,6,12,16,19,33,36-heptamethyl-15-(piperidine-1-carbonyl)docosahydro-2H4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1834) (8S,11S,17S,26S,29S,33S,36S)-11-[2-[3-chloro-4-(trifluoromethyl)phenyl]ethyl]-36-cyclohexyl-17-(cyclohexylmethyl)-9,15,18,21,24,29,30,34,37-nonamethyl-26-[(1S)-1-methylpropyl]-8-(3-pyridylmethyl)-33-(pyrrolidine-1-carbonyl)-6,9,12,15,18,21,24,27,30,34,37-undecazaspiro[4.33]octatriacontane-7,10,13,16,19,22,25,28,31,35,38-undecone, (1835) (3S,9S,18S,21S,25S,28S,34S)-3-[2-[3-chloro-4-(trifluoromethyl)phenyl]ethyl]-28-cyclohexyl-9-(cyclohexylmethyl)-21-cyclopentyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1836) (3S,9S,18S,21S,25S,28S,34S)-3-[2-[3-chloro-4-(trifluoromethyl)phenyl]ethyl]-21-isobutyl-N,N,7,10,13,16,22,26,29-nonamethyl-18,28-bis[(1S)-1-methylpropyl]-2,5,8,11,14,17,20,23,27,30,33-undecaoxo-9-(p-tolylmethyl)spiro[1,4,7,10,13,16,19,22,26,29,32-undecazabicyclo[32.3.0]heptatriacontane-31,1'-cyclopentane]-25-carboxamide, (1837) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-(hydroxymethyl)-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1838) (3S,9S,18S,21S,25S,28S,34S)-3-[2-[3-chloro-4-(trifluoromethyl)phenyl]ethyl]-28-cyclohexyl-9-(cyclohexylmethyl)-18-(cyclopentylmethyl)-21-isobutyl-7,10,13,16,22,26,29-heptamethyl-25-(piperidine-1-carbonyl)spiro[11,4,7,10,13,16,19,22,26,29,32-undecazabicyclo[32.3.0]heptatriacontane-31,1'-cyclopentane]-2,5,8,11,14,17,20,23,27,30,33-undecone, (1839) (9'S,12'S,16'S,19'S,24a'S,30'S,32a'R,38'S,40a'S)-38'-benzyl-9'-((S)-sec-butyl)-30'-(3-chloro-4-(trifluoromethyl)phenethyl)-19'-isopropyl-7',12',13',17',20',39'-hexamethyl-16'-(piperidine-1-carbonyl)hexacosahydro-5'H-spiro[cyclopentane-1,22'-tripyrrolo[2,1-i:2',1'-o:2'',1''-u][1,4,7,10,13,16,19,22,25,28,31]undecaazacyclotetratriacontin]-5',8',11',14',18',21',24',29',32',37',40'(15'H,23'H)-undecaone, (1840) (5S,8S,11S,15S,18S,23aS,29S,35S,37aS)-8-((S)-sec-butyl)-29-(3-chloro-4-(trifluoromethyl)phenethyl)-18-cyclopentyl-11-isobutyl-5,6,12,16,19,33,36-heptamethyl-35-(4-methylbenzyl)-15-(pyrrolidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1841) (3S,9S,18S,21S,25S,28S,34S)-3-[2-[3-chloro-4-(trifluoromethyl)phenyl]ethyl]-28-cyclohexyl-21-isobutyl-7,10,13,16,22,26,29-heptamethyl-18-[(1S)-1-methylpropyl]-25-(piperidine-1-carbonyl)-9-(2,2,2-trifluoroethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1842) (5S,8S,11S,15S,18S,23aS,29S,35S,37aS)-8,18-di((S)-sec-butyl)-29-(3-chloro-4-(trifluoromethyl)phenethyl)-11-isobutyl-N,N,5,6,12,16,19,33,36-nonamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1843) (5S,8S,11S,15S,18S,23aS,29S,35S,37aS)-8,18-di((S)-sec-butyl)-29-(3-chloro-4-(trifluoromethyl)phenethyl)-35-(cyclohexylmethyl)-11-isobutyl-5,6,12,16,19,33,36-heptamethyl-15-(pyrrolidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1844) (3S,6R,9S,18S,21S,25S,28S,34S)-9-benzyl-3-[2-[3-chloro-4-(trifluoromethyl)phenyl]ethyl]-28-isopropyl-6,7,10,13,16,21,22,26,29-nonamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1845) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopropane]-2,5,8,11,14,17,20,23,27,30,33-undecone, (1846) (3S,9S,18S,21S,25S,28S,34S)-3-[2-[3-chloro-4-(trifluoromethyl)phenyl]ethyl]-28-cyclohexyl-21-isobutyl-7,10,13,16,22,26,29-heptamethyl-18-[(1S)-1-methylpropyl]-9-pentyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1847) (3S,9S,18S,21S,25S,28S,34S)-3-[2-[3-chloro-4-(trifluoromethyl)phenyl]ethyl]-28-cyclohexyl-9-(cyclohexylmethyl)-7,10,13,16,21,22,26,29-octamethyl-8-[(1S)-1-methylpropyl]-25-(morpholine-4-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1848) (3S,9S,18S,21S,25S,28S,34S)-3-[2-[3-chloro-4-(trifluoromethyl)phenyl]ethyl]-9-(cyclopentylmethyl)-21-isobutyl-28-isopropyl-7,10,13,16,22,26,29-heptamethyl-18-[(1S)-1-methylpropyl]-25-(morpholine-4-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1849) (8S,11S,17S,26S,29S,33R,36S)-11-[2-[3-chloro-4-(trifluoromethyl)phenyl]ethyl]-36-cyclohexyl-17-(cyclohexylmethyl)-29-isobutyl-9,15,18,21,24,30,33,34,37-nonamethyl-26-[(1S)-1-methylpropyl]-8-(3-pyridylmethyl)-6,9,12,15,18,21,24,27,30,34,37-undecazaspiro[4.33]octatriacontane-7,10,13,16,19,22,25,28,31,35,38-undecone, (1850) (3S,9S,18S,21S,25S,28S,34S)-3-[2-[3-chloro-4-(trifluoromethyl)phenyl]ethyl]-28-cyclopentyl-21-isobutyl-7,10,13,16,22,26,29-heptamethyl-18-[(1S)-1-methylpropyl]-25-(piperidine-1-carbonyl)-9-(p-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1851) (3S,9S,18S,21S,25R,28S,34S,36R)-3-[2-[3-chloro-4-(trifluoromethyl)phenyl]ethyl]-9-(cyclohexylmethyl)-36-ethoxy-21,28-diisobutyl-7,10,13,16,22,25,26,29-octamethyl-8-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1852) (5S,8S,11S,15S,18S,23aS,29S,35S,37aS)-8-((S)-sec-butyl)-29-(3-chloro-4-(trifluoromethyl)phenethyl)-18-cyclohexyl-11-isobutyl-5,6,12,16,19,33,36-heptamethyl-35-(4-methylbenzyl)-15-(pyrrolidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1853) (9'S,12'S,16'S,19'S,24'aS,30'S,33'R,36'S,38'aS)-9'-((S)-sec-butyl)-30'-(3-chloro-4-(trifluoromethyl)phenethyl)-36'-(4-fluorobenzyl)-19'-isopropyl-7',12',13',17',20',33',34',37'-octamethyl-16'-(piperidine-1-carbonyl)tetracosahydro-5'H-spiro[cyclopentane-1,22'-dipyrrolo[2,1-i:2',1'-u][1,4,7,10,13,16,19,22,25,28,31]undecaazacyclotetratriacontin]-5',8',11',14',18',21',24',29',32',35',38'(15'H,23'H)-undecaone, (1854) (5S,8S,11S,15S,18S,23aS,29S,35S,37aS)-8-((S)-sec-butyl)-29-(3-chloro-4-(trifluoromethyl)phenethyl)-11-isobutyl-18-isopropyl-5,6,12,16,19,33,36-heptamethyl-35-pentyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1855) (5S,8S,11S,15S,18S,23aS,29S,35S,37aS)-8-((S)-sec-butyl)-29-(3-chloro-4-(trifluoromethyl)phenethyl)-35-(cyclohexylmethyl)-11-isobutyl-5,6,12,16,19,33,36-heptamethyl-15-(piperidine-1-carbonyl)-18-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1856) (3S,9S,18S,21S,25R,28S,34S)-3-[2-[3-chloro-4-(trifluoromethyl)phenyl]ethyl]-28-cyclohexyl-21-isobutyl-7,10,13,16,22,25,29-heptamethyl-18-[(1S)-1-methylpropyl]-9-(p-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1857) (3S,9S,18S,21S,25S,28S,34S)-3-[2-[3-chloro-4-(trifluoromethyl)phenyl]ethyl]-9-(cyclohexylmethyl)-28-(cyclopropoxymethyl)-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1858) (5S,8S,11S,15S,18S,23aS,29S,35S,37aS)-8,18-di((S)-sec-butyl)-29-(3-chloro-4-(trifluoromethyl)phenethyl)-35-(cyclohexylmethyl)-11-isobutyl-N,N,5,6,12,16,19,33,36-nonamethyl-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1859) (5S,8S,11S,15S,18S,23aS,29S,35S,37aS)-8-((S)-sec-butyl)-18-butyl-29-(3-chloro-4-(trifluoromethyl)phenethyl)-35-(cyclohexylmethyl)-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1860) (5S,8S,11S,15S,18S,23aS,29S,35S,37aS)-8-((S)-sec-butyl)-29-(3-chloro-4-(trifluoromethyl)phenethyl)-18-(cyclobutylmethyl)-35-(cyclohexylmethyl)-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1861) (3S,9S,18S,21S,25S,28S,34S)-3-[2-[3-chloro-4-(trifluoromethyl)phenyl]ethyl]-28-cyclohexyl-9-(cyclohexylmethyl)-21-isopentyl-7,10,13,16,22,26,29-heptamethyl-8-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1862) (3S,9S,18S,21S,25S,28S,34S)-3-[2-[3-chloro-4-(trifluoromethyl)phenyl]ethyl]-28-cyclohexyl-9-(cyclohexylmethyl)-18-cyclopropyl-21-isobutyl-7,10,13,16,22,26,29-heptamethyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1863) (5S,8S,11S,15S,18S,23aS,29S,35S,37aS)-8,11-di((S)-sec-butyl)-29-(3-chloro-4-(trifluoromethyl)phenethyl)-35-(cyclohexylmethyl)-18-isopropyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1864) (5S,8S,11S,15S,18S,23aS,29S,35S,37aS)-29-(3-chloro-4-(trifluoromethyl)phenethyl)-35-(cyclohexylmethyl)-11-isobutyl-18-isopropyl-5,6,12,16,19,33,36-heptamethyl-15-(piperidine-1-carbonyl)-8-(2,2,2-trifluoroethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1865) (3S,9S,18S,21S,25S,28S,34S)-3-[2-[3-chloro-4-(trifluoromethyl)phenyl]ethyl]-9-(cyclohexylmethyl)-21-isobutyl-N,N,7,10,13,16,22,26,29-nonamethyl-18,28-bis[(1S)-1-methylpropyl]-2,5,8,11,14,17,20,23,27,30,33-undecaoxo-spiro[1,4,7,10,13,16,19,22,26,29,32- undecazabicyclo[32.3.0]heptatriacontane-31,1'-cyclopentane]-25-carboxamide,
(1866) (5S,8S,11S,15S,18S,23aS,29S,35S,37aS)-8-((S)-sec-butyl)-29-(3-chloro-4-(trifluoromethyl)phenethyl)-11-isobutyl-18-isopropyl-5,6,12,16,19,33,36-heptamethyl-35-(4-methylbenzyl)-15-(pyrrolidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1867) (3S,9S,18S,21S,25S,28S,34S)-3-[2-[3-chloro-4-(trifluoromethyl)phenyl]ethyl]-21-isobutyl-28-isopropyl-N,N,7,10,13,16,22,26,29-nonamethyl-18-[(1S)-1-methylpropyl]-2,5,8,11,14,17,20,23,27,30,33-undecaoxo-9-(p-tolylmethyl)spiro[1,4,7,10,13,16,19,22,26,29,32-undecazabicyclo[32.3.0]heptatriacontane-31,1'-cyclopentane]-25-carboxamide,
(1868) (5S,8S,11S,15R,18S,23aS,29S,35S,37aS)-8-((S)-sec-butyl)-29-(3-chloro-4-(trifluoromethyl)phenethyl)-35-(cyclohexylmethyl)-18-cyclopentyl-11-isobutyl-5,6,12,16,19,33,36-heptamethyl-15-(pyrrolidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1869) (3S,9S,18S,21S,25S,28S,34S)-3-[2-[3-chloro-4-(trifluoromethyl)phenyl]ethyl]-28-cyclohexyl-21-isobutyl-7,10,13,16,22,26,29-heptamethyl-18-[(1S)-1-methylpropyl]-25-(3-oxa-8-azabicyclo[3.2.1]octane-8-carbonyl)-9-(p-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1870) (3S,9S,18S,21S,25S,28S,34S)-28-cyclohexyl-9-(cyclohexylmethyl)-3-[2-[3-fluoro-4-(trifluoromethyl)phenyl]ethyl]-21-isobutyl-7,10,13,16,22,26,29-heptamethyl-8-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1871) (3S,9S,18S,21S,25S,28S,34S)-3-[2-[3-chloro-4-(trifluoromethyl)phenyl]ethyl]-28-cyclohexyl-7,10,13,16,22,26,29-heptamethyl-18-[(1S)-1-methylpropyl]-25-(morpholine-4-carbonyl)-21-propyl-9-(p-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1872) (3S,9S,18S,21S,25S,28S,34S)-3-[2-[3-chloro-4-(trifluoromethyl)phenyl]ethyl]-28-cyclohexyl-21-isobutyl-7,10,13,16,22,26,29-heptamethyl-18-[(1S)-1-methylpropyl]-25-(morpholine-4-carbonyl)-9-(p-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1873) (3S,6S,9S,13S,16S,22S,25S,31S,34S)-22-[(3-bromophenyl)methyl]-25-[2-[3-chloro-4-(trifluoromethyl)phenyl]ethyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide,
(1874) (5S,8S,11S,15R,18S,23aS,29S,35S,37aS)-8,18-di((S)-sec-butyl)-29-(3-chloro-4-(trifluoromethyl)phenethyl)-11-isobutyl-5,6,12,19,33,36-hexamethyl-35-(4-methylbenzyl)-15-phenethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone,
(1875) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-25-(morpholine-4-carbonyl)spiro[1,4,7,10,13,16,19,22,26,29,32-undecazabicyclo[32.3.0]heptatriacontane-31,1'-cyclobutane]-2,5,8,11,14,17,20,23,27,30,33-undecone,
(1876) (3S,6S,9S,13S,16S,22S,25S,31S,34S)-25-[2-[3-chloro-4-(trifluoromethyl)phenyl]ethyl]-22-[(4-fluorophenyl)methyl]-9-isobutyl-3,4,10,14,17,23,29,32-octamethyl-6,16-bis[(1S)-1-methylpropyl]-13-(piperidine-1-carbonyl)-31-(p-tolylmethyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone,
(1877) (3S,9S,18S,21S,25S,28S,34S)-3-[2-[3-chloro-4-(trifluoromethyl)phenyl]ethyl]-28-cyclohexyl-9-(cyclopentylmethyl)-21-ethyl-7,10,13,16,22,26,29-heptamethyl-18-[(1S)-1-methylpropyl]-25-(3-oxa-8-azabicyclo[3.2.1]octane-8-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1878) (3S,6S,9S,13S,16S,22S,25S,31S,34S)-25-[2-[3-chloro-4-(trifluoromethyl)phenyl]ethyl]-22-[(3,4-difluorophenyl)methyl]-N,N,3,4,9,10,14,17,23,29,32-undecamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide,
(1879) (3S,9S,18S,21S,25S,28S,34S)-3-[2-[3-chloro-4-(trifluoromethyl)phenyl]ethyl]-18-cyclobutyl-28-cyclohexyl-9-(cyclohexylmethyl)-21-isobutyl-7,10,13,16,22,26,29-heptamethyl-25-(3-oxa-8-azabicyclo[3.2.1]octane-8-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone,
(1880) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-9-isobutyl-N,N,3,4,10,14,17,23,29,32-decamethyl-6-[(1S)-1-methylpropyl]-22-(o-tolylmethyl)-2,5,8,11,15,18,21,24,27,30,33-undecaoxospiro[1,4,7,10,14,17,20,23,26,29,32-undecazabicyclo[32.2.0]hexatriacontane-19,1'-cyclopentane]-13-carboxamide,
(1881) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-9-isobutyl-N,N,3,4,10,14,17,23,29,32-decamethyl-6-[(1S)-1-methylpropyl]-2,5,8,11,15,18,21,24,27,30,33-undecaoxo-22-[2-(4-pyridyl)ethyl]spiro[1,4,7,10,14,17,20,23,26,29,32-undecazabicyclo[32.2.0]hexatriacontane-19,1'-cyclopentane]-13-carboxamide,
(1882) (3S,6S,9S,13S,16S,22S,25S,31S,34S)-25-[2-[3,5-difluoro-4-(trifluoromethyl)phenyl]ethyl]-22-[(4-fluorophenyl)methyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-[[4-(trifluoromethyl)phenyl]methyl]spiro[1,4,7,10,14,17,20,23,26,29,32-undecazabicyclo[32.2.0]hexatriacontane-19,1'-cyclopentane]-13-carboxamide,
(1883) (5S,8S,11S,15R,18S,23aS,29S,35S,37aS)-15-allyl-8,18-di((S)-sec-butyl)-29-(3-chloro-4-(trifluoromethyl)phenethyl)-11-isobutyl-5,6,12,19,33,36-hexamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1884) (3S,9S,18S,21S,25S,28S,34S)-3-[2-[3-chloro-4-(trifluoromethyl)phenyl]ethyl]-28-cyclohexyl-21-ethyl-7,10,13,16,22,26,29-heptamethyl-18-[(1S)-1-methylpropyl]-25-(morpholine-4-carbonyl)-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1885) (3S,6S,9S,13S,16S,22S,25S,31S,34S)-25-[2-[3-chloro-4-(trifluoromethyl)phenyl]ethyl]-22-[(4-fluorophenyl)methyl]-3,4,9,10,14,17,23,29,32-nonamethyl-6,16-bis[(1S)-1-methylpropyl]-13-(piperidine-1-carbonyl)-31-(p-tolylmethyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (1886) (3S,6S,9S,13S,16S,22S,25S,31S,34S)-25-[2-[3-chloro-4-(trifluoromethyl)phenyl]ethyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)-22-[2-(3-pyridyl)ethyl]spiro[1,4,7,10,14,17,20,23,26,29,32-undecazabicyclo[32.2.0]hexatriacontane-19,1'-cyclopentane]-13-carboxamide, (1887) (3S,6S,9S,13S,16S,22R,25S,31S,34S)-22-benzyl-25-[2-[3,5-difluoro-4-(trifluoromethyl)phenyl]ethyl]-3,4,9,10,14,17,23,29,32-nonamethyl-6,16-bis[(1S)-1-methylpropyl]-13-(piperidine-1-carbonyl)-31-(p-tolylmethyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (1888) (3S,6S,9S,13S,16S,22S,25S,31S,34S)-25-[2-[3-chloro-4-(trifluoromethyl)phenyl]ethyl]-22-[(4-iodophenyl)methyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (1889) (3S,6S,9S,13S,16S,22R,25S,31S,34S)-22-benzyl-25-[2-[3-chloro-4-(trifluoromethyl)phenyl]ethyl]-N,N,3,4,9,10,14,17,23,29,32-undecamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (1890) (3S,9S,18S,21S,25S,28S,34S)-3-[2-[3-chloro-4-(trifluoromethyl)phenyl]ethyl]-28-cyclohexyl-21-ethyl-7,10,13,16,22,26,29-heptamethyl-18-[(1S)-1-methylpropyl]-25-(pyrrolidine-1-carbonyl)-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1891) (5S,8S,11S,15R,18S,23aS,29S,35S,37aS)-8,18-di((S)-sec-butyl)-29-(3,5-difluoro-4-(trifluoromethyl)phenethyl)-11,15-diisobutyl-5,6,12,19,33,36-hexamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1892) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-9-isobutyl-N,N,3,4,10,14,17,23,29,32-decamethyl-6-[(1S)-1-methylpropyl]-2,5,8,11,15,18,21,24,27,30,33-undecaoxo-22-[2-(3-pyridyl)ethyl]spiro[1,4,7,10,14,17,20,23,26,29,32-undecazabicyclo[32.2.0]hexatriacontane-19,1'-cyclopentane]-13-carboxamide, (1893) (3S,6S,9S,13S,16S,22S,25S,31S,34S)-22-[(4-bromophenyl)methyl]-25-[2-[3-chloro-4-(trifluoromethyl)phenyl]ethyl]-N,N,3,4,9,10,14,17,23,29,32-undecamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (1894) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclobutane]-2,5,8,11,14,17,20,23,27,30,33-undecone, (1895) (3S,6S,9S,13S,16S,22R,25S,31S,34S)-22-benzyl-25-[2-[3,5-difluoro-4-(trifluoromethyl)phenyl]ethyl]-9-isobutyl-3,4,10,14,17,23,29,32-octamethyl-6,16-bis[(1S)-1-methylpropyl]-13-(piperidine-1-carbonyl)-31-(p-tolylmethyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (1896) (3S,9S,18S,21S,25S,28S,34S)-3-[2-[3-chloro-4-(trifluoromethyl)phenyl]ethyl]-28-cyclohexyl-21-ethyl-7,10,13,16,22,26,29-heptamethyl-18-[(1S)-1-methylpropyl]-25-(morpholine-4-carbonyl)-9-(propoxymethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1897) (3S,6S,9S,13S,16S,19S,22S,25S,31S,34S)-25-[2-[3-chloro-4-(trifluoromethyl)phenyl]ethyl]-9-isobutyl-19-isopropyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)-22-(4-pyridylmethyl)-1,4,7,10,14,17,20,23,26,29,32-undecazabicyclo[32.2.0]hexatriacontane-13-carboxamide, (1898) (3S,6S,9S,13S,16S,22S,25S,31S,34S)-25-[2-[3-chloro-4-(trifluoromethyl)phenyl]ethyl]-22-(3,3-difluoropropyl)-9-isobutyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (1899) (5S,8S,11S,15R,18S,23aS,29S,35S,37aS)-8,18-di((S)-sec-butyl)-29-(3-chloro-4-(trifluoromethyl)phenethyl)-11,15-diisobutyl-5,6,12,19,33,36-hexamethyl-35-(4-(trifluoromethyl)benzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1900) (3S,9S,18S,21S,25S,28S,34S)-3-[2-[3-chloro-4-(trifluoromethyl)phenyl]ethyl]-28-cyclohexyl-21-isobutyl-7,10,13,16,22,26,29-heptamethyl-18-[(1S)-1-methylpropyl]-25-(3-oxa-8-azabicyclo[3.2.1]octane-8-carbonyl)-9-(propoxymethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1901) (3S,9S,18S,21S,25S,28S,34S)-3-[2-[3-chloro-4-(trifluoromethyl)phenyl]ethyl]-28-cyclohexyl-9-(cyclohexylmethyl)-21-ethyl-7,10,13,16,22,26,29-heptamethyl-18-[(1S)-1-methylpropyl]-25-(3-oxa-8-azabicyclo[3.2.1]octane-8-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1902) (3S,6S,9S,13S,16S,22S,25S,31S,34S)-25-[2-[3-chloro-4-(trifluoromethyl)phenyl]ethyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)-22-[[4-(trifluoromethoxy)phenyl]methyl]

spiro[1,4,7,10,14,17,20,23,26,29,32-undecazabicyclo [32.2.0]hexatriacontane-19,1'-cyclopentane]-13-carboxamide, (1903) (3S,6S,9S,13S,16S,22S,25S,31S,34S)-25-[2-[3-chloro-4-(trifluoromethyl)phenyl]ethyl]-22-[(4-methoxyphenyl)methyl]-N,N,3,4,9,10,14,17,23,29,32-undecamethyl-6,16-bis[(1S)-1-methylpropyl]-2,5,8,11,15,18,21, 24,27,30,33-undecaoxo-31-(p-tolylmethyl)spiro[1,4,7, 10,14,17,20,23,26,29,32-undecazabicyclo[32.2.0] hexatriacontane-19,1'-cyclopentane]-13-carboxamide, (1904) (3S,9S,18S,21S,25S,28S,34S)-3-[2-[3-chloro-4-(trifluoromethyl)phenyl]ethyl]-28-cyclohexyl-21-ethyl-7,10, 13,16,22,26,29-heptamethyl-18-[(1S)-1-methylpropyl]-25-(morpholine-4-carbonyl)-9-(p-tolylmethyl)spiro[1,4, 7,10,13,16,19,22,26,29,32-undecazabicyclo[32.3.0] heptatriacontane-31,1'-cyclopentane]-2,5,8,11,14,17,20, 23,27,30,33-undecone, (1905) (3S,9S,18S,21S,25S,28S,34S)-3-[2-[3-chloro-4-(trifluoromethyl)phenyl]ethyl]-28-cyclohexyl-21-ethyl-7,10, 13,16,22,26,29-heptamethyl-18-[(1S)-1-methylpropyl]-9-(p-tolylmethyl)-25-(pyrrolidine-1-carbonyl)spiro[1,4,7, 10,13,16,19,22,26,29,32-undecazabicyclo[32.3.0] heptatriacontane-31,1'-cyclopentane]-2,5,8,11,14,17,20, 23,27,30,33-undecone, (1906) (3S,9S,18S,21S,25S,28S,34S)-3-[2-[3-chloro-4-(trifluoromethyl)phenyl]ethyl]-18-cyclobutyl-28-cyclohexyl-9-(cyclohexylmethyl)-21-isobutyl-7,10,13,16,22, 26,29-heptamethyl-25-(morpholine-4-carbonyl)spiro[1,4, 7,10,13,16,19,22,26,29,32-undecazabicyclo[32.3.0] heptatriacontane-31,1'-cyclopentane]-2,5,8,11,14,17,20, 23,27,30,33-undecone, (1907) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-22-(3,3-difluoropropyl)-9-isobutyl-N,N,3,4,10,14,17,23,29,32-decamethyl-6-[(1S)-1-methylpropyl]-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide, (1908) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-18-isopropyl-7,10,13,16,22,26,29-heptamethyl-25-(morpholine-4-carbonyl)spiro[1,4,7,10, 13,16,19,22,26,29,32-undecazabicyclo[32.3.0] heptatriacontane-31,1'-cyclopentane]-2,5,8,11,14,17,20, 23,27,30,33-undecone, (1909) (3S,6S,9S,13S,16S,22R,25S,31S,34S)-22-benzyl-25-[2-[3-chloro-4-(trifluoromethyl)phenyl]ethyl]-9-isobutyl-N,N,3,4,10,14,17,23,29,32-decamethyl-6,16-bis [(1S)-1-methylpropyl]-2,5,8,11,15,18,21,24,27,30,33-undecaoxo-31-(p-tolylmethyl)spiro[1,4,7,10,14,17,20,23, 26,29,32-undecazabicyclo[32.2.0]hexatriacontane-19,1'-cyclopentane]-13-carboxamide, (1910) (3S,6S,9S,13S,16S,22S,25S,31S,34S)-25-[2-[3-chloro-4-(trifluoromethyl)phenyl]ethyl]-22-[(3-iodophenyl)methyl]-9-isobutyl-N,N,3,4,10,14,17,23,29,32-decamethyl-6,16-bis[(1S)-1-methylpropyl]-2,5,8,11,15,18,21, 24,27,30,33-undecaoxo-31-(p-tolylmethyl)spiro[1,4,7, 10,14,17,20,23,26,29,32-undecazabicyclo[32.2.0] hexatriacontane-19,1'-cyclopentane]-13-carboxamide, (1911) (3S,6S,9S,13S,16S,22S,25S,31S,34S)-25-[2-[3-chloro-4-(trifluoromethyl)phenyl]ethyl]-9-isobutyl-N,N, 3,4,10,14,17,23,29,32-decamethyl-22-[3-(methylamino)-3-oxo-propyl]-6,16-bis[(1S)-1-methylpropyl]-2,5,8,11, 15,18,21,24,27,30,33-undecaoxo-31-(p-tolylmethyl)spiro [1,4,7,10,14,17,20,23,26,29,32-undecazabicyclo[32.2.0] hexatriacontane-19,1'-cyclopentane]-13-carboxamide, (1912) (5S,8S,11S,14aR,21S,26aS,32S,38S,40aS)-8,21-di ((S)-sec-butyl)-32-(3-chloro-4-(trifluoromethyl)phenethyl)-11-isobutyl-5,6,12,22,36,39-hexamethyl-38-(4-methylbenzyl)hexacosahydro-2H-spiro[azeto[1,2-j] pyrido[1,2-e1]pyrrolo[1,2-v][1,4,7,10,13,16,19,22,25,28, 31]undecaazacyclotetratriacontine-24,1'-cyclopentan]-4, 7,10,13,20,23,26,31,34,37,40(25H)-undecaone, (1913) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-9-isobutyl-N,N,3,4,10,14,17,23, 29,32-decamethyl-6-[(1S)-1-methylpropyl]-2,5,8,11,15, 18,21,24,27,30,33-undecaoxo-22-(4-pyridylmethyl)spiro [1,4,7,10,14,17,20,23,26,29,32-undecazabicyclo[32.2.0] hexatriacontane-19,1'-cyclopentane]-13-carboxamide, (1914) (3S,6S,9S,13S,16S,22S,25S,31S,34S)-25-[2-[3,5-difluoro-4-(trifluoromethyl)phenyl]ethyl]-22-[(4-fluorophenyl)methyl]-N,N,3,4,9,10,14,17,23,29,32-undecamethyl-6,16-bis[(1S)-1-methylpropyl]-2,5,8,11,15,18,21, 24,27,30,33-undecaoxo-31-(p-tolylmethyl)spiro[1,4,7, 10,14,17,20,23,26,29,32-undecazabicyclo[32.2.0] hexatriacontane-19,1'-cyclopentane]-13-carboxamide, (1915) (3S,9S,18S,21S,25S,28S,34S)-3-[2-[3-chloro-4-(trifluoromethyl)phenyl]ethyl]-28-cyclohexyl-9-(cyclohexylmethyl)-21-ethyl-7,10,13,16,22,26,29-heptamethyl-18-[(1S)-1-methylpropyl]-25-(morpholine-4-carbonyl)spiro [1,4,7,10,13,16,19,22,26,29,32-undecazabicyclo[32.3.0] heptatriacontane-31,1'-cyclopentane]-2,5,8,11,14,17,20, 23,27,30,33-undecone, (1916) (3S,9S,18S,21S,25S,28S,34S)-3-[2-[3-chloro-4-(trifluoromethyl)phenyl]ethyl]-28-cyclohexyl-9-(cyclopentylmethyl)-7,10,13,16,22,26,29-heptamethyl-18-[(1S)-1-methylpropyl]-25-(3-oxa-8-azabicyclo[3.2.1]octane-8-carbonyl)-21-propyl-spiro[1,4,7,10,13,16,19,22,26,29, 32-undecazabicyclo[32.3.0]heptatriacontane-31,1'-cyclopentane]-2,5,8,11,14,17,20,23,27,30,33-undecone, (1917) (3S,6S,9S,13S,16S,19S,22S,25S,31S,34S)-25-[2-[3-chloro-4-(trifluoromethyl)phenyl]ethyl]-31-(cyclohexylmethyl)-16-cyclopentyl-9-isobutyl-N,N,3,4,10,14,17,19, 23,29,32-undecamethyl-6-[(1S)-1-methylpropyl]-2,5,8, 11,15,18,21,24,27,30,33-undecaoxo-22-(4-pyridylmethyl)-1,4,7,10,14,17,20,23,26,29,32-undecazabicyclo[32.2.0]hexatriacontane-13-carboxamide, (1918) (5S,8S,11S,15R,18S,23aS,29S,35S,37aS)-8,18-di ((S)-sec-butyl)-29-(3,5-difluoro-4-(trifluoromethyl)phenethyl)-11,15-diisobutyl-5,6,12,19,33,36-hexamethyl-35-(4-(trifluoromethyl)benzyl)docosahydro-2H,4H-spiro [azeto[2,1-u]pyrrolo[2,1-i][1,4,7,10,13,16,19,22,25,28, 31]undecaazacyclotetratriacontine-21,1'-cyclopentan]-4, 7,10,13,17,20,23,28,31,34,37(14H,22H)-undecaone, (1919) (5S,8S,11S,15S,18S,23aS,29S,35S,37aS)-8,18-di ((S)-sec-butyl)-29-(3-chloro-4-(trifluoromethyl)phenethyl)-11-isobutyl-5,6,12,19,33,36-hexamethyl-35-(4-methylbenzyl)-15-(trifluoromethyl)docosahydro-2H,4H-spiro[azeto[2,1-u]pyrrolo[2,1-i][1,4,7,10,13,16,19,22,25, 28,31]undecaazacyclotetratriacontine-21,1'-cyclopentan]-4,7,10,13,17,20,23,28,31,34,37(14H,22H)-undecaone, (1920) (3S,6S,9S,13S,16S,22S,25S,31S,34S)-25-[2-[3-chloro-4-(trifluoromethyl)phenyl]ethyl]-N,N,3,4,9,10,14, 17,23,29,32-undecamethyl-6,16-bis[(1S)-1-methylpropyl]-2,5,8,11,15,18,21,24,27,30,33-undecaoxo-31-(p-tolylmethyl)-22-[[4-(trifluoromethoxy)phenyl]methyl] spiro[1,4,7,10,14,17,20,23,26,29,32-undecazabicyclo [32.2.0]hexatriacontane-19,1'-cyclopentane]-13-carboxamide, (1921) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-9-isobutyl-N,N,3,4,10,14,17,23,29,32-decamethyl-22-[3-(methylamino)-3-oxo-propyl]-6-[(1S)-1-methylpropyl]-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide, (1922) (3S,6S,9S,13S,16S,22S,25S,31S,34S)-25-[2-[3-chloro-4-(trifluoromethyl)phenyl]ethyl]-22-[(3-methoxyphenyl)methyl]-N,N,3,4,9,10,14,17,23,29,32-undecamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (1923) (3S,9S,18S,21S,25S,28S,34S)-3-[2-[3-chloro-4-(trifluoromethyl)phenyl]ethyl]-28-cyclohexyl-9-(cyclopentylmethyl)-21-isobutyl-7,10,13,16,22,26,29-heptamethyl-18-[(1S)-1-methylpropyl]-25-(morpholine-4-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1924) (3S,6S,9S,13S,16S,22S,25S,31S,34S)-25-[2-[3-chloro-4-(trifluoromethyl)phenyl]ethyl]-9-isobutyl-N,N,3,4,10,14,17,23,29,32-decamethyl-6,16-bis[(1S)-1-methylpropyl]-22-(o-tolylmethyl)-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (1925) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-18-isopropyl-7,10,13,16,22,26,29-heptamethyl-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1926) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-22-[[4-(difluoromethyl)phenyl]methyl]-9-isobutyl-N,N,3,4,10,14,17,23,29,32-decamethyl-6-[(1S)-1-methylpropyl]-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide, (1927) (3S,6S,9S,13S,16S,22S,25S,31S,34S)-25-[2-[3-chloro-4-(trifluoromethyl)phenyl]ethyl]-22-[(4-cyanophenyl)methyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (1928) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-18-isopropyl-7,10,13,16,22,26,29-heptamethyl-25-(3-oxa-8-azabicyclo[3.2.1]octane-8-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1929) (3S,9S,18S,21S,25S,28S,34S)-3-[2-[3-chloro-4-(trifluoromethyl)phenyl]ethyl]-28-cyclohexyl-21-ethyl-7,10,13,16,22,26,29-heptamethyl-18-[(1S)-1-methylpropyl]-9-(propoxymethyl)-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1930) (3S,6S,9S,13S,16S,22S,25S,31S,34S)-25-[2-[3-chloro-4-(trifluoromethyl)phenyl]ethyl]-22-[[4-(difluoromethyl)phenyl]methyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (1931) (3S,9S,18S,21S,25S,28S,34S)-3-[2-[3-chloro-4-(trifluoromethyl)phenyl]ethyl]-28-cyclohexyl-9-(cyclopentylmethyl)-21-ethyl-7,10,13,16,22,26,29-heptamethyl-18-I[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1932) (3S,9S,18S,21S,25S,28S,34S)-3-[2-[3-chloro-4-(trifluoromethyl)phenyl]ethyl]-28-cyclohexyl-21-isobutyl-7,10,13,16,22,26,29-heptamethyl-18-[(1S)-1-methylpropyl]-25-(3-oxa-8-azabicyclo[3.2.1]octane-8-carbonyl)-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1933) (3S,9S,18S,21S,25S,28S,34S)-3-[2-[3-chloro-4-(trifluoromethyl)phenyl]ethyl]-28-cyclohexyl-9-(cyclohexylmethyl)-7,10,13,16,22,26,29-heptamethyl-18-[(1S)-1-methylpropyl]-25-(3-oxa-8-azabicyclo[3.2.1]octane-8-carbonyl)-21-propyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1934) (3S,9S,18S,21S,25S,28S,34S)-3-[2-[3-chloro-4-(trifluoromethyl)phenyl]ethyl]-9-(cyclohexylmethyl)-21-isobutyl-28-isopropyl-7,10,13,16,22,26,29-heptamethyl-18-[(1S)-1-methylpropyl]-25-(morpholine-4-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1935) (3S,6S,9S,13S,16S,22S,25S,31S,34S)-25-[2-[3-chloro-4-(trifluoromethyl)phenyl]ethyl]-9-isobutyl-22-[(4-methoxyphenyl)methyl]-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (1936) (3S,9S,18S,21S,25S,28S,34S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-25-(3-oxa-8-azabicyclo[3.2.1]octane-8-carbonyl)spiro[1,4,7,10,13,16,19,22,26,29,32-undecazabicyclo[32.3.0]heptatriacontane-31,1'-cyclobutane]-2,5,8,11,14,17,20,23,27,30,33-undecone, (1937) (8S,11S,17S,26S,29S,33S,36S)-11-[2-[3-chloro-4-(trifluoromethyl)phenyl]ethyl]-36-cyclohexyl-17-(cyclopentylmethyl)-9,15,18,21,24,30,34,37-octamethyl-26-[(1S)-1-methylpropyl]-33-(morpholine-4-carbonyl)-29-propyl-8-(3-pyridylmethyl)-6,9,12,15,18,21,24,27,30,34,37-undecazaspiro[4.33]octatriacontane-7,10,13,16,19,22,25,28,31,35,38-undecone, (1938) (3S,9S,18S,21S,25S,28S,34S)-3-[2-[3-chloro-4-(trifluoromethyl)phenyl]ethyl]-9-(cyclohexylmethyl)-21-isobutyl-7,10,13,16,22,26,29-heptamethyl-18,28-bis[(1S)-1-methylpropyl]-25-(3-oxa-8-azabicyclo[3.2.1]octane-8-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1939) (3S,9S,18S,21S,25S,28S,34S)-28-cyclohexyl-9-(cyclohexylmethyl)-21-isobutyl-7,10,13,16,22,26,29-heptamethyl-18-[(1S)-1-methylpropyl]-25-(pyrrolidine-1-carbonyl)-3-[2-[4-(trifluoromethyl)phenyl]ethyl]spiro[1, (1940) (3S,9S,18S,21S,25S,28S,34S)-28-cyclohexyl-9-(cyclohexylmethyl)-21-isobutyl-7,10,13,16,22,26,29-heptamethyl-18-[(1S)-1-methylpropyl]-25-(3-oxa-8-azabicyclo[3.2.1]octane-8-carbonyl)-3-[2-[4-(trifluoromethyl)phenyl]ethyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1941) (3S,9S,18S,21S,25S,28S,34S)-3-[2-(4-chlorophenyl)ethyl]-28-cyclohexyl-9-(cyclohexylmethyl)-21-isobutyl-7,10,13,16,22,26,29-heptamethyl-18-[(1S)-1-methylpropyl]-25-(morpholine-4-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1942) (3S,6S,9S,13S,16S,22R,25S,31S,34S)-22-benzyl-25-[2-[3-chloro-4-(trifluoromethyl)phenyl]ethyl]-3,4,9,10,14,17,23,29,32-nonamethyl-6,16-bis[(1S)-1-methylpropyl]-13-(piperidine-1-carbonyl)-31-[[4-(trifluoromethyl)phenyl]methyl]spiro[1,4,7,10,14,17,20,23,26,29,32-undecazabicyclo[32.2.0]hexatriacontane-19,1'-cyclopentane]-2,5,8,11,15,18,21,24,27,30,33-undecone, (1943) (3S,6S,9S,13S,16S,22S,25S,31S,34S)-25-[2-[3-chloro-4-(trifluoromethyl)phenyl]ethyl]-22-[(3,4-difluorophenyl)methyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (1944) (3S,6S,9S,13S,16S,22S,25S,31S,34S)-25-[2-[3-chloro-4-(trifluoromethyl)phenyl]ethyl]-22-[(3-iodophenyl)methyl]-N,N,3,4,9,10,14,17,23,29,32-undecamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (1945) (3S,6S,9S,13S,16S,22S,25S,31S,34S)-25-[2-[3-chloro-4-(trifluoromethyl)phenyl]ethyl]-N,N,3,4,9,10,14,17,23,29,32-undecamethyl-6,16-bis[(1S)-1-methylpropyl]-2,5,8,11,15,18,21,24,27,30,33-undecaoxo-31-(p-tolylmethyl)-22-[[3-(trifluoromethoxy)phenyl]methyl]spiro[1,4,7,10,14,17,20,23,26,29,32-undecazabicyclo[32.2.0]hexatriacontane-19,1'-cyclopentane]-13-carboxamide, (1946) (8S,11S,17S,26S,29S,33S,36S)-11-[2-[3-chloro-4-(trifluoromethyl)phenyl]ethyl]-36-cyclohexyl-17-(cyclopentylmethyl)-9,15,18,21,24,30,34,37-octamethyl-26-[(1S)-1-methylpropyl]-29-propyl-8-(3-pyridylmethyl)-33-(pyrrolidine-1-carbonyl)-6,9,12,15,18,21,24,27,30,34,37-undecazaspiro[4.33]octatriacontane-7,10,13,16,19,22,25,28,31,35,38-undecone, (1947) (3S,9S,18S,21S,25S,28S,34S)-28-cyclohexyl-9-(cyclohexylmethyl)-21-isobutyl-7,10,13,16,22,26,29-heptamethyl-18-[(1S)-1-methylpropyl]-25-(morpholine-4-carbonyl)-3-[2-[4-(trifluoromethyl)phenyl]ethyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1948) (3S,9S,18S,21S,25S,28S,34S)-3-[2-[3-chloro-4-(trifluoromethyl)phenyl]ethyl]-28-cyclohexyl-21-isobutyl-7,10,13,16,22,26,29-heptamethyl-18-[(1S)-1-methylpropyl]-25-(morpholine-4-carbonyl)-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1949) (3S,9S,18S,21S,25S,28S,34S)-3-[2-[3-chloro-4-(trifluoromethyl)phenyl]ethyl]-28-cyclohexyl-7,10,13,16,22,26,29-heptamethyl-18-[(1S)-1-methylpropyl]-25-(morpholine-4-carbonyl)-9-(propoxymethyl)-21-propyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1950) (3S,9S,18S,21S,25S,28S,34S)-3-[2-(4-chlorophenyl)ethyl]-28-cyclohexyl-9-(cyclohexylmethyl)-21-isobutyl-7,10,13,16,22,26,29-heptamethyl-18-[(1S)-1-methylpropyl]-25-(3-oxa-8-azabicyclo[3.2.1]octane-8-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1951) (3S,6S,9S,13S,16S,22S,25S,31S,34S)-25-[2-[3-chloro-4-(trifluoromethyl)phenyl]ethyl]-22-[(4-fluorophenyl)methyl]-N,N,3,4,9,10,14,17,23,29,32-undecamethyl-6,16-bis[(1S)-1-methylpropyl]-2,5,8,11,15,18,21,24,27,30,33-undecaoxo-31-[[4-(trifluoromethyl)phenyl]methyl]spiro[1,4,7,10,14,17,20,23,26,29,32-undecazabicyclo[32.2.0]hexatriacontane-19,1'-cyclopentane]-13-carboxamide, (1952) (3S,6S,9S,13S,16S,22S,25S,31S,34S)-25-[2-[3,5-difluoro-4-(trifluoromethyl)phenyl]ethyl]-22-[(4-fluorophenyl)methyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (1953) (3S,6S,9S,13S,16S,22S,25S,31S,34S)-25-[2-[3-chloro-4-(trifluoromethyl)phenyl]ethyl]-22-[(4-iodophenyl)methyl]-N,N,3,4,9,10,14,17,23,29,32-undecamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (1954) (3S,9S,18S,21S,25S,28S,34S)-3-[2-[3-chloro-4-(trifluoromethyl)phenyl]ethyl]-9-(cyclohexylmethyl)-21-isobutyl-28-isopropyl-7,10,13,16,22,26,29-heptamethyl-18-[(1S)-1-methylpropyl]-25-(3-oxa-8-azabicyclo[3.2.1]octane-8-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1955) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-22-[2-[2-(4,4-difluoro-1-piperidyl)-2-oxo-ethyl]-9-isobutyl-N,N,3,4,10,14,17,23,29,32-decamethyl-6-[(1S)-1-methylpropyl]-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide, (1956) (3S,9S,18S,21S,25S,28S,34S)-3-[2-[3-chloro-4-(trifluoromethyl)phenyl]ethyl]-28-cyclohexyl-21-ethyl-7,10,13,16,22,26,29-heptamethyl-18-[(1S)-1-methylpropyl]-25-(3-oxa-8-azabicyclo[3.2.1]octane-8-carbonyl)-9-(propoxymethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1957) (3S,9S,18S,21S,25S,28S,34S)-28-cyclohexyl-9-(cyclohexylmethyl)-3-[2-[3-fluoro-4-(trifluoromethyl)phenyl]ethyl]-21-isobutyl-7,10,13,16,22,26,29-heptamethyl-18-[(1S)-1-methylpropyl]-25-(3-oxa-8-azabicyclo[3.2.1]octane-8-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1958) (3S,9S,18S,21S,25S,28S,34S)-3-[2-[3-chloro-4-(trifluoromethyl)phenyl]ethyl]-28-cyclohexyl-9-(cyclohexylmethyl)-21-ethyl-7,10,13,16,22,26,29-heptamethyl-18-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1959) (3S,6S,9S,13S,16S,22S,25S,31S,34S)-25-[2-[3-chloro-4-(trifluoromethyl)phenyl]ethyl]-22-[(4-cyanophenyl)methyl]-N,N,3,4,9,10,14,17,23,29,32-undecamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (1960) N-(tert-butyl)-2-((((5S,8S,11S,15S,18S,23aS,29S,35S,37aS)-8,18-di((S)-sec-butyl)-29-(3-chloro-4-(trifluoromethyl)phenethyl)-11-isobutyl-5,6,12,19,33,36-hexamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentan]-15-yl)methoxy)acetamide, (1961) (5S,8S,11S,15S,18S,23aS,29S,35S,37aS)-8,18-di((S)-sec-butyl)-29-(3-chloro-4-(trifluoromethyl)phenethyl)-35-cyclobutyl-11-isobutyl-N,N,5,6,12,16,19,33,36-nonamethyl-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide, (1962) (3S,6S,9S,13S,16S,22S,25S,31S,34S)-25-[2-[3-chloro-4-(trifluoromethyl)phenyl]ethyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)-22-(4-pyridylmethyl)spiro[1,4,7,10,14,17,20,23,26,29,32-undecazabicyclo[32.2.0]hexatriacontane-19,1'-cyclopentane]-13-carboxamide, (1963) (3S,9S,18S,21S,25S,28S,34S)-3-[2-[3-chloro-4-(trifluoromethyl)phenyl]ethyl]-28-cyclohexyl-21-ethyl-7,10,13,16,22,26,29-heptamethyl-18-[(1S)-1-methylpropyl]-25-(3-oxa-8-azabicyclo[3.2.1]octane-8-carbonyl)-9-(p-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1964) (3S,6S,9S,13S,16S,22S,25S,31S,34S)-22-[(4-bromophenyl)methyl]-25-[2-[3-chloro-4-(trifluoromethyl)phenyl]ethyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (1965) (3S,9S,18S,21S,25S,28S,34S)-28-cyclohexyl-9-(cyclohexylmethyl)-3-[2-[3-fluoro-4-(trifluoromethyl)phenyl]ethyl]-21-isobutyl-7,10,13,16,22,26,29-heptamethyl-18-[(1S)-1-methylpropyl]-25-(morpholine-4-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1966) (3S,9S,18S,21S,25S,28S,34S)-3-[2-[3-chloro-4-(trifluoromethyl)phenyl]ethyl]-28-cyclohexyl-21-isobutyl-7,10,13,16,22,26,29-heptamethyl-18-[(1S)-1-methylpropyl]-25-(morpholine-4-carbonyl)-9-(propoxymethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1967) (5S,8S,11S,15R,18S,23aS,29S,35S,37aS)-8,18-di((S)-sec-butyl)-29-(3-chloro-4-(trifluoromethyl)phenethyl)-11-isobutyl-5,6,12,19,33,36-hexamethyl-35-(4-methylbenzyl)-15-(prop-2-yn-1-yl)docosahydro-2H,4H-spiro[azeto[2,1-u]pyrrolo[2,1-i][1,4,7,10,13,16,19,22,25,28,31]undecaazacyclotetratriacontine-21,1'-cyclopentane]-4,7,10,13,17,20,23,28,31,34,37(14H,22H)-undecaone, (1968) (3S,9S,18S,21S,25S,28S,34S)-3-[2-(4-chlorophenyl)ethyl]-28-cyclohexyl-9-(cyclohexylmethyl)-21-isobutyl-7,10,13,16,22,26,29-heptamethyl-18-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1969) (3S,9S,18S,21S,25S,28S,34S)-3-[2-[3-chloro-4-(trifluoromethyl)phenyl]ethyl]-28-cyclohexyl-9-(cyclopentylmethyl)-21-isobutyl-7,10,13,16,22,26,29-heptamethyl-8-[(1S)-1-methylpropyl]-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1970) (3S,6S,9S,13S,16S,22S,25S,31S,34S)-25-[2-[3-chloro-4-(trifluoromethyl)phenyl]ethyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)-22-[[3-(trifluoromethoxy)phenyl]methyl]spiro[1,4,7,10,14,17,20,23,26,29,32-undecazabicyclo[32.2.0]hexatriacontane-19,1'-cyclopentane]-13-carboxamide, (1971) (3S,9S,18S,21S,25S,28S,34S)-3-[2-[3-chloro-4-(trifluoromethyl)phenyl]ethyl]-28-cyclohexyl-7,10,13,16,22,26,29-heptamethyl-18-[(1S)-1-methylpropyl]-25-(3-oxa-8-azabicyclo[3.2.1]octane-8-carbonyl)-9-(propoxymethyl)-21-propyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1972) (3S,9S,18S,21S,25S,28S,34S)-3-[2-[3-chloro-4-(trifluoromethyl)phenyl]ethyl]-28-cyclohexyl-7,10,13,16,22,26,29-heptamethyl-18-[(1S)-1-methylpropyl]-25-(morpholine-4-carbonyl)-21-propyl-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1973) (3S,6S,9S,13S,16S,19S,22S,25,31S,34S)-25-[2-[3-chloro-4-(trifluoromethyl)phenyl]ethyl]-9-isobutyl-N,N,3,4,10,14,17,19,23,29,32-undecamethyl-6,16-bis[(1S)-1-methylpropyl]-2,5,8,11,15,18,21,24,27,30,33-undecaoxo-31-(p-tolylmethyl)-22-(4-pyridylmethyl)-1,4,7,10,14,17,20,23,26,29,32-undecazabicyclo[32.2.0]hexatriacontane-13-carboxamide, (1974) (5S,8S,11S,15R,18S,23aS,29S,35S,37aS)-8,18-di((S)-sec-butyl)-29-(3-chloro-4-(trifluoromethyl)phenethyl)-11,15-diisobutyl-5,6,12,16,19,33,36-heptamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1975) (3S,9S,18S,21S,25S,28S,34S)-3-[2-[3-chloro-4-(trifluoromethyl)phenyl]ethyl]-28-cyclohexyl-9-(cyclopentylmethyl)-7,10,13,16,22,26,29-heptamethyl-18-[(1S)-1-methylpropyl]-21-propyl-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1976) (3S,9S,18S,21S,25S,28S,34S)-3-[2-[3-chloro-4-(trifluoromethyl)phenyl]ethyl]-28-cyclohexyl-9-(cyclopentylmethyl)-21-isobutyl-7,10,13,16,22,26,29-heptamethyl- 8-[(1S)-1-methylpropyl]-25-(3-oxa-8-azabicyclo[3.2.1]octane-8-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1977) (3S,9S,18S,21S,25S,28S,34S,36R)-3-[2-[3-chloro-4-(trifluoromethyl)phenyl]ethyl]-28-cyclohexyl-9-(cyclohexylmethyl)-36-ethoxy-21-isobutyl-7,10,13,16,22,26,29-heptamethyl-18-[(1S)-1-methylpropyl]-25-(3-oxa-8-azabicyclo[3.2.1]octane-8-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1978) (3S,9S,18S,21S,25S,28S,34S)-3-[2-[3-chloro-4-(trifluoromethyl)phenyl]ethyl]-28-cyclohexyl-21-isobutyl-7,10,13,16,22,26,29-heptamethyl-18-[(1S)-1-methylpropyl]-25-(pyrrolidine-1-carbonyl)-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1979) (3S,9S,18S,21S,25S,28S,34S)-3-[2-[3-chloro-4-(trifluoromethyl)phenyl]ethyl]-9-(cyclohexylmethyl)-21-isobutyl-7,10,13,16,22,26,29-heptamethyl-18,28-bis[(1S)-1-methylpropyl]-25-(morpholine-4-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1980) (3S,6S,9S,13S,16S,22S,25S,31S,34S)-25-[2-[3-chloro-4-(trifluoromethyl)phenyl]ethyl]-22-[2-(4,4-difluoro-1-piperidyl)-2-oxo-ethyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (1981) (3S,6S,9S,13S,16S,22S,25S,31S,34S)-25-[2-[3-chloro-4-(trifluoromethyl)phenyl]ethyl]-22-[(3-cyanophenyl)methyl]-N,N,3,4,9,10,14,17,23,29,32-undecamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (1982) (3S,6S,9S,13S,16S,19S,22S,25S,31S,34S)-25-[2-[3-chloro-4-(trifluoromethyl)phenyl]ethyl]-31-(cyclohexylmethyl)-16-cyclopentyl-9-isobutyl-19-isopropyl-N,N,3,4,10,14,17,23,29,32-decamethyl-6-[(1S)-1-methylpropyl]-2,5,8,11,15,18,21,24,27,30,33-undecaoxo-22-(4-pyridylmethyl)-1,4,7,10,14,17,20,23,26,29,32-undecazabicyclo[32.2.0]hexatriacontane-13-carboxamide, (1983) (3S,9S,18S,21S,25S,28S,34S)-3-[2-[3-chloro-4-(trifluoromethyl)phenyl]ethyl]-28-cyclohexyl-7,10,13,16,22,26,29-heptamethyl-18-[(1S)-1-methylpropyl]-25-(3-oxa-8-azabicyclo[3.2.1]octane-8-carbonyl)-21-propyl-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1984) (3S,9S,18S,21S,25S,28S,34S)-3-[2-[3-chloro-4-(trifluoromethyl)phenyl]ethyl]-28-cyclohexyl-7,10,13,16,22,26,29-heptamethyl-18-[(1S)-1-methylpropyl]-21-propyl-25-(pyrrolidine-1-carbonyl)-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1985) (3S,6S,9S,13S,16S,22S,25S,31S,34S)-25-[2-[3-chloro-4-(trifluoromethyl)phenyl]ethyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)-22-[2-(4-pyridyl)ethyl]spiro[1,4,7,10,14,17,20,23,26,29,32-undecazabicyclo[32.2.0]hexatriacontane-19,1'-cyclopentane]-13-carboxamide, (1986) (3S,6S,9S,13S,16S,22S,25S,31S,34S)-25-[2-[3,5-difluoro-4-(trifluoromethyl)phenyl]ethyl]-22-[(4-fluorophenyl)methyl]-N,N,3,4,9,10,14,17,23,29,32-undecamethyl-6,16-bis[(1S)-1-methylpropyl]-2,5,8,11,15,18,21,24,27,30,33-undecaoxo-31-[[4-(trifluoromethyl)phenyl]methyl]spiro[1,4,7,10,14,17,20,23,26,29,32-undecazabicyclo[32.2.0]hexatriacontane-19,1'-cyclopentane]-13-carboxamide, (1987) (3S,6S,9S,13S,16S,22S,25S,31S,34S)-25-[2-[3-chloro-4-(trifluoromethyl)phenyl]ethyl]-22-[(4-fluorophenyl)methyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-[[4-(trifluoromethyl)phenyl]methyl]spiro[1,4,7,10,14,17,20,23,26,29,32-undecazabicyclo[32.2.0]hexatriacontane-19,1'-cyclopentane]-13-carboxamide, (1988) (3S,9S,18S,21S,25S,28S,34S)-3-[2-[3-chloro-4-(trifluoromethyl)phenyl]ethyl]-18-cyclobutyl-28-cyclohexyl-9-(cyclohexylmethyl)-21-isobutyl-7,10,13,16,22,26,29-heptamethyl-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1989) (3S,6S,9S,13S,16S,22R,25S,31S,34S)-22-benzyl-25-[2-[3-chloro-4-(trifluoromethyl)phenyl]ethyl]-9-isobutyl-3,4,10,14,17,23,29,32-octamethyl-6,16-bis[(1S)-1-methylpropyl]-13-(piperidine-1-carbonyl)-31-(p-tolylmethyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (1990) (3S,9S,18S,21S,25S,28S,34S,36R)-3-[2-[3-chloro-4-(trifluoromethyl)phenyl]ethyl]-28-cyclohexyl-9-(cyclohexylmethyl)-36-ethoxy-21-isobutyl-7,10,13,16,22,26,29-heptamethyl-18-[(1S)-1-methylpropyl]-25-(morpholine-4-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1991) (3S,6S,9S,13S,16S,22S,25S,31S,34S)-25-[2-[3-chloro-4-(trifluoromethyl)phenyl]ethyl]-9-isobutyl-22-[(3-methoxyphenyl)methyl]-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (1992) (3S,6S,9S,13S,16S,22R,25S,31S,34S)-22-benzyl-25-[2-[3,5-difluoro-4-(trifluoromethyl)phenyl]ethyl]-3,4,9,10,14,17,23,29,32-nonamethyl-6,16-bis[(1S)-1-methylpropyl]-13-(piperidine-1-carbonyl)-31-[[4-(trifluoromethyl)phenyl]methyl]spiro[1,4,7,10,14,17,20,23,26,29,32-undecazabicyclo[32.2.0]hexatriacontane-19,1'-cyclopentane]-2,5,8,11,15,18,21,24,27,30,33-undecone, (1993) (3S,9S,18S,21S,25S,28S,34S)-3-[2-[3-chloro-4-(trifluoromethyl)phenyl]ethyl]-28-cyclohexyl-21-ethyl-7,10,13,16,22,26,29-heptamethyl-18-[(1S)-1-methylpropyl]-25-(3-oxa-8-azabicyclo[3.2.1]octane-8-carbonyl)-9-[[4-(trifluoromethyl)phenyl]methyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1994) (3S,9S,18S,21S,25S,28S,34S)-3-[2-[3-chloro-4-(trifluoromethyl)phenyl]ethyl]-28-cyclohexyl-7,10,13,16,22,26,29-heptamethyl-18-[(1S)-1-methylpropyl]-25-(3- oxa-8-azabicyclo[3.2.1]octane-8-carbonyl)-21-propyl-9-(p-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1995) (5S,8S,11S,15R,18S,23aS,29S,35S,37aS)-8,18-di((S)-sec-butyl)-29-(3-chloro-4-(trifluoromethyl)phenethyl)-11,15-diisobutyl-5,6,12,19,33,36-hexamethyl-35-(4-methylbenzyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (1996) (3S,9S,18S,21S,25S,28S,34S)-3-[2-[3-chloro-4-(trifluoromethyl)phenyl]ethyl]-28-cyclohexyl-9-(cyclohexylmethyl)-7,10,13,16,22,26,29-heptamethyl-18-[(1S)-1-methylpropyl]-25-(morpholine-4-carbonyl)-21-propyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1997) (3S,6S,9S,13S,16S,22R,25S,31S,34S)-22-benzyl-25-[2-[3-chloro-4-(trifluoromethyl)phenyl]ethyl]-3,4,9,10,14,17,23,29,32-nonamethyl-6,16-bis[(1S)-1-methylpropyl]-13-(piperidine-1-carbonyl)-31-(p-tolylmethyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (1998) (3S,9S,18S,21S,25S,28S,34S)-3-[2-[3-chloro-4-(trifluoromethyl)phenyl]ethyl]-28-cyclohexyl-9-(cyclopentylmethyl)-7,10,13,16,22,26,29-heptamethyl-18-[(1S)-1-methylpropyl]-25-(morpholine-4-carbonyl)-21-propyl-spiro[1,4,7,10,13,16,19,22,26,29,32-undecazabicyclo[32.3.0]heptatriacontane-31,1'-cyclopentane]-2,5,8,11,14,17,20,23,27,30,33-undecone, (1999) (3S,9S,18S,21S,25S,28S,34S)-3-[2-[3-chloro-4-(trifluoromethyl)phenyl]ethyl]-28-cyclohexyl-9-(cyclopentylmethyl)-21-ethyl-7,10,13,16,22,26,29-heptamethyl-18-[(1S)-1-methylpropyl]-25-(morpholine-4-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2000) (3S,6S,9S,13S,16S,22S,25S,31S,34S)-22-[(3-bromophenyl)methyl]-25-[2-[3-chloro-4-(trifluoromethyl)phenyl]ethyl]-N,N,3,4,9,10,14,17,23,29,32-undecamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (2001) (3S,9S,18S,21S,25S,28S,34S)-3-[2-[3-chloro-4-(trifluoromethyl)phenyl]ethyl]-28-cyclohexyl-9-(cyclohexylmethyl)-7,10,13,16,22,26,29-heptamethyl-18-[(1S)-1-methylpropyl]-21-propyl-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2002) (3S,6S,9S,13S,16S,22S,25S,31S,34S)-25-[2-[3-chloro-4-(trifluoromethyl)phenyl]ethyl]-22-[(3-cyanophenyl)methyl]-9-isobutyl-N,N,3,4,10,14,17,23,29,32-decamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (2003) (5S,8S,11S,14aR,20S,25aS,31S,37S,39aS)-8,20-di((S)-sec-butyl)-31-(3-chloro-4-(trifluoromethyl)phenethyl)-11-isobutyl-5,6,12,21,35,38-hexamethyl-37-(4-methylbenzyl)tetracosahydro-2H,4H-spiro[azeto[1,2-j]dipyrrolo[1,2-e1:1',2'-v][1,4,7,10,13,16,19,22,25,28,31]undecaazacyclotetratriacontine-23,1'-cyclopentan]-4,7,10,13,19,22,25,30,33,36,39(14H,24H)-undecaone, (2004) (3S,9S,18S,21S,25S,28S,34S)-3-[2-[3-chloro-4-(trifluoromethyl)phenyl]ethyl]-28-cyclohexyl-7,10,13,16,22,26,29-heptamethyl-18-[(1S)-1-methylpropyl]-21-propyl-9-(p-tolylmethyl)-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2005) (3S,9S,18S,21S,25S,28S,34S)-3-[2-[3-chloro-4-(trifluoromethyl)phenyl]ethyl]-28-cyclohexyl-7,10,13,16,22,26,29-heptamethyl-18-[(1S)-1-methylpropyl]-9-(propoxymethyl)-21-propyl-25-(pyrrolidine-1-carbonyl)spiro[11,4,7,10,13,16,19,22,26,29,32-undecazabicyclo[32.3.0]heptatriacontane-31,1'-cyclopentane]-2,5,8,11,14,17,20,23,27,30,33-undecone, (2006) (3S,9S,18S,21S,25S,28S,34S)-3-[2-[3-chloro-4-(trifluoromethyl)phenyl]ethyl]-28-cyclohexyl-21-isobutyl-7,10,13,16,22,26,29-heptamethyl-18-[(1S)-1-methylpropyl]-9-(propoxymethyl)-25-(pyrrolidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2007) (8S,11S,17S,26S,29S,33S,36S)-8-[(2-chlorophenyl)methyl]-11-[2-[3-chloro-4-(trifluoromethyl)phenyl]ethyl]-36-isopropyl-9,15,18,21,24,29,30,34,37-nonamethyl-26-[(1S)-1-methylpropyl]-33-(piperidine-1-carbonyl)-17-(p-tolylmethyl)-6,9,12,15,18,21,24,27,30,34,37-undecazaspiro[4.33]octatriacontane-7,10,13,16,19,22,25,28,31,35,38-undecone, (2008) (8S,11S,17S,26S,29S,33S,36S)-8-[(2-chlorophenyl)methyl]-11-[2-[3-chloro-4-(trifluoromethyl)phenyl]ethyl]-17-(cyclohexylmethyl)-36-isopropyl-9,15,18,21,24,29,30,34,37-nonamethyl-26-[(1S)-1-methylpropyl]-33-(pyrrolidine-1-carbonyl)-6,9,12,15,18,21,24,27,30,34,37-undecazaspiro[4.33]octatriacontane-7,10,13,16,19,22,25,28,31,35,38-undecone, (2009) (5S,8S,12R,15S,20aS,26S,29R,32S,34aS,39aS)-5-((S)-sec-butyl)-26-(3-chloro-4-(trifluoromethyl)phenethyl)-32-(cyclohexylmethyl)-15-isopropyl-8,9,12,16,29,30,33-heptamethyltetracosahydrospiro[azeto[1,2-g]dipyrrolo[1,2-j:1',2'-v][1,4,7,10,13,16,19,22,25,28,31]undecaazacyclotetratriacontine-18,1'-cyclopentan]-4,7,10,14,17,20,25,28,31,34,39(2H,11H,19H)-undecaone, (2010) (5S,8S,12R,15S,20aS,26S,29R,32S,37aS)-5-((S)-sec-butyl)-26-(3-chloro-4-(trifluoromethyl)phenethyl)-32-(cyclohexylmethyl)-15-isopropyl-8,9,12,16,29,30,33,36-octamethyldocosahydrospiro[azeto[1,2-g]pyrrolo[1,2-v][1,4,7,10,13,16,19,22,25,28,31]undecaazacyclotetratriacontine-18,1'-cyclopentan]-4,7,10,14,17,20,25,28,31,34,37(2H,11H,19H)-undecaone, (2011) (3S,6S,9S,13S,16S,22S,25S,31S,34S)-22-[(2-chlorophenyl)methyl]-25-[2-[3-chloro-4-(trifluoromethyl)phenyl]ethyl]-N,N,3,4,9,10,14,17,23,29,32-undecamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (2012) (5S,8S,11S,15R,18S,23aS,29S,32R,35S,37aS)-8-((S)-sec-butyl)-29-(3-chloro-4-(trifluoromethyl)phenethyl)-35-(cyclohexylmethyl)-5-ethyl-18-isopropyl-6,11,12,15,19,32,33,36-octamethyldocosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (2013) (5S,8S,12R,15S,20aS,26S,29R,32S,34aS,38aS)-5-((S)-sec-butyl)-26-(3-chloro-4-(trifluoromethyl)phenethyl)-32-(cyclohexylmethyl)-15-isopropyl-8,9,12,16,29,30,33-heptamethyldocosahydro-25H-spiro[bis(azeto)[1, 2-g:1',2'-j]pyrrolo[1,2-v][1,4,7,10,13,16,19,22,25,28,31] undecaazacyclotetratriacontine-18,1'-cyclopentan]-4,7, 10,14,17,20,25,28,31,34,38(2H,11H,19H,34aH)-undecaone, (2014) (9'S,12'S,16'R,19'S,24a'S,30'S,33'R,36'S,38a'S)-9'-((S)-sec-butyl)-30'-(3-chloro-4-(trifluoromethyl)phenethyl)-36'-(cyclohexylmethyl)-7'-ethyl-19'-isopropyl-12', 13',16',20',33',34',37'-heptamethyltetracosahydro-5'H-spiro[cyclopentane-1,22'-dipyrrolo[2,1-i:2',1'-u][1,4,7, 10,13,16,19,22,25,28,31]undecaazacyclotetratriacontin]-5',8',11',14',18',21',24',29',32',35',38'(15'H,23'H)-undecaone, (2015) (5S,8S,11S,15R,18S,23aS,29S,32R,35S,37aS)-8-((S)-sec-butyl)-29-(3-chloro-4-(trifluoromethyl)phenethyl)-5,35-bis(cyclohexylmethyl)-18-isopropyl-6,11,12, 15,19,32,33,36-octamethyldocosahydro-2H,4H-spiro [azeto[2,1-u]pyrrolo[2,1-i][1,4,7,10,13,16,19,22,25,28, 31]undecaazacyclotetratriacontine-21,1'-cyclopentan]-4, 7,10,13,17,20,23,28,31,34,37(14H,22H)-undecaone, (2016) (5S,8S,11S,15R,18S,23aS,29S,32R,35S,37aS)-8-((S)-sec-butyl)-29-(3-chloro-4-(trifluoromethyl)phenethyl)-35-(cyclohexylmethyl)-18-isopropyl-6,11,12,15, 19,32,33,36-octamethyl-5-(propoxymethyl)docosahydro-2H,4H-spiro[azeto[2,1-u]pyrrolo[2,1-i][1,4,7,10,13,16, 19,22,25,28,31]undecaazacyclotetratriacontine-21,1'-cyclopentan]-4,7,10,13,17,20,23,28,31,34,37(14H,22H)-undecaone, (2017) (5S,8S,11S,15R,18S,23aS,29S,32R,35S,37aS)-8-((S)-sec-butyl)-5-butyl-29-(3-chloro-4-(trifluoromethyl) phenethyl)-35-(cyclohexylmethyl)-18-isopropyl-6,11,12, 15,19,32,33,36-octamethyldocosahydro-2H,4H-spiro [azeto[2,1-u]pyrrolo[2,1-i][1,4,7,10,13,16,19,22,25,28, 31]undecaazacyclotetratriacontine-21,1'-cyclopentan]-4, 7,10,13,17,20,23,28,31,34,37(14H,22H)-undecaone, (2018) (5S,8S,11S,15R,18S,23aS,29S,32R,35S,37aS)-8-((S)-sec-butyl)-29-(3-chloro-4-(trifluoromethyl)phenethyl)-35-(cyclohexylmethyl)-5-isobutyl-18-isopropyl-6, 11,12,15,19,32,33,36-octamethyldocosahydro-2H,4H-spiro[azeto[2,1-u]pyrrolo[2,1-i][1,4,7,10,13,16,19,22,25, 28,31]undecaazacyclotetratriacontine-21,1'-cyclopentan]-4,7,10,13,17,20,23,28,31,34,37(14H,22H)-undecaone, (2019) (5S,8S,11S,15R,18S,23aS,29S,32R,35S,37aS)-5-benzyl-8-((S)-sec-butyl)-29-(3-chloro-4-(trifluoromethyl)phenethyl)-35-(cyclohexylmethyl)-18-isopropyl-6, 11,12,15,19,32,33,36-octamethyldocosahydro-2H,4H-spiro[azeto[2,1-u]pyrrolo[2,1-i][1,4,7,10,13,16,19,22,25, 28,31]undecaazacyclotetratriacontine-21,1'-cyclopentan]-4,7,10,13,17,20,23,28,31,34,37(14H,22H)-undecaone, (2020) (8S,11S,17S,26S,29S,33S,36S)-8-[(2-chlorophenyl) methyl]-11-[2-[3-chloro-4-(trifluoromethyl)phenyl] ethyl]-17-(cyclohexylmethyl)-36-isopropyl-9,15,18,21, 24,29,30,34,37-nonamethyl-26-[(1S)-1-methylpropyl]-33-(morpholine-4-carbonyl)-6,9,12,15,18,21,24,27,30, 34,37-undecazaspiro[4.33]octatriacontane-7,10,13,16,19, 22,25,28,31,35,38-undecone, (2021) (11S,17S,26S,29S,33S,36S)-11-[2-[3-chloro-4-(trifluoromethyl)phenyl]ethyl]-36-cyclohexyl-17-(cyclohexylmethyl)-9-[3-(4,4-difluoro-1-piperidyl)propyl]-29-isobutyl-15,18,21,24,30,34,37-heptamethyl-26-[(1S)-1-methylpropyl]-33-(piperidine-1-carbonyl)-6,9,12,15,18, 21,24,27,30,34,37-undecazaspiro[4.33]octatriacontane-7, 10,13,16,19,22,25,28,31,35,38-undecone, (2022) (11S,17S,26S,29S,33S,36S)-11-[2-[3-chloro-4-(trifluoromethyl)phenyl]ethyl]-36-cyclohexyl-17-(cyclohexylmethyl)-9-[2-(4,4-difluoro-1-piperidyl)ethyl]-29-isobutyl-15,18,21,24,30,34,37-heptamethyl-26-[(1S)-1-methylpropyl]-33-(piperidine-1-carbonyl)-6,9,12,15,18, 21,24,27,30,34,37-undecazaspiro[4.33]octatriacontane-7, 10,13,16,19,22,25,28,31,35,38-undecone, (2023) (3S,6S,9S,13S,16S,25S,31S,34S)-25-[2-[3-chloro-4-(trifluoromethyl)phenyl]ethyl]-31-(cyclohexylmethyl)-16-cyclopentyl-23-[2-(2-hydroxy-2-methyl-propoxy) ethyl]-9-isobutyl-N,N,3,4,10,14,17,29,32-nonamethyl-6-[(1S)-1-methylpropyl]-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide, (2024) (11S,17S,26S,29S,33S,36S)-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-33-(piperidine-1-carbonyl)-9-[2-(2,2,2-trifluoroethoxy)ethyl]-6,9,12,15, 18,21,24,27,30,34,37-undecazaspiro[4.33] octatriacontane-7,10,13,16,19,22,25,28,31,35,38-undecone, (2025) (11S,17S,26S,29S,33S,36S)-11-[2-[3-chloro-4-(trifluoromethyl)phenyl]ethyl]-36-cyclohexyl-17-(cyclohexylmethyl)-29-isobutyl-9-[2-(2-methoxyethoxy)ethyl]-15, 18,21,24,30,34,37-heptamethyl-26-[(1S)-1-methylpropyl]-33-(piperidine-1-carbonyl)-6,9,12,15,18, 21,24,27,30,34,37-undecazaspiro[4.33]octatriacontane-7, 10,13,16,19,22,25,28,31,35,38-undecone, (2026) (11S,17S,26S,29S,33S,36S)-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-33-(piperidine-1-carbonyl)-9-(3-pyridylmethyl)-6,9,12,15,18,21,24,27,30, 34,37-undecazaspiro[4.33]octatriacontane-7,10,13,16,19, 22,25,28,31,35,38-undecone, (2027) (3S,6S,9S,13R,16S,25S,31S,34S)-25-[2-[3-chloro-4-(trifluoromethyl)phenyl]ethyl]-23-[2-(2-hydroxy-2-methyl-propoxy)ethyl]-9-isobutyl-3,4,10,13,14,17,29,32-octamethyl-6,16-bis[(1S)-1-methylpropyl]-31-(propoxymethyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (2028) (3S,6S,9S,13S,16S,25S,31S,34S)-25-[2-[3-chloro-4-(trifluoromethyl)phenyl]ethyl]-31-(cyclohexylmethyl)-23-[2-(2-hydroxy-2-methyl-propoxy)ethyl]-9-isobutyl-N, N,3,4,10,14,17,29,32-nonamethyl-6,16-bis[(1S)-1-methylpropyl]-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide, (2029) (11S,17S,26S,29S,33S,36S)-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-33-(piperidine-1-carbonyl)-9-[2-(4-pyridyl)ethyl]-6,9,12,15,18,21,24,27, 30,34,37-undecazaspiro[4.33]octatriacontane-7,10,13,16, 19,22,25,28,31,35,38-undecone, (2030) (11S,17S,26S,29S,33S,36S)-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-9-(2-oxaspiro[3.3] heptan-6-yl)-33-(piperidine-1-carbonyl)-6,9,12,15,18,21, 24,27,30,34,37-undecazaspiro[4.33]octatriacontane-7,10, 13,16,19,22,25,28,31,35,38-undecone, (2031) (11S,17S,26S,29S,33S,36S)-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-9-(oxetan-3-ylmethyl)-

33-(piperidine-1-carbonyl)-6,9,12,15,18,21,24,27,30,34, 37-undecazaspiro[4.33]octatriacontane-7,10,13,16,19,22, 25,28,31,35,38-undecone, (2032) (11S,17S,26S,29S,33S,36S)-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-33-(piperidine-1-carbonyl)-9-[2-(3-pyridyl)ethyl]-6,9,12,15,18,21,24,27, 30,34,37-undecazaspiro[4.33]octatriacontane-7,10,13,16, 19,22,25,28,31,35,38-undecone, (2033) (11S,17S,26S,29S,33S,36S)-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-33-(piperidine-1-carbonyl)-9-(4-pyridylmethyl)-6,9,12,15,18,21,24,27,30, 34,37-undecazaspiro[4.33]octatriacontane-7,10,13,16,19, 22,25,28,31,35,38-undecone, (2034) (3S,6S,9S,13S,16S,25S,31S,34S)-25-[2-[3-chloro-4-(trifluoromethyl)phenyl]ethyl]-23-[2-(2-hydroxy-2-methyl-propoxy)ethyl]-9-isobutyl-N,N,3,4,10,14,17,29, 32-nonamethyl-6,16-bis[(1S)-1-methylpropyl]-2,5,8,11, 15,18,21,24,27,30,33-undecaoxo-31-(p-tolylmethyl)spiro [1,4,7,10,14,17,20,23,26,29,32-undecazabicyclo[32.2.0] hexatriacontane-19,1'-cyclopentane]-13-carboxamide, (2035) (11S,17S,26S,29S,33S,36S)-11-[2-[3-chloro-4-(trifluoromethyl)phenyl]ethyl]-36-cyclohexyl-17-(cyclohexylmethyl)-9-(2,2-difluorospiro[3.3]heptan-6-yl)-29-isobutyl-15,18,21,24,30,34,37-heptamethyl-26-[(1S)-1-methylpropyl]-33-(piperidine-1-carbonyl)-6,9,12,15,18, 21,24,27,30,34,37-undecazaspiro[4.33]octatriacontane-7, 10,13,16,19,22,25,28,31,35,38-undecone, (2036) (11S,17S,26S,29S,33S,36S)-11-[2-[3-chloro-4-(trifluoromethyl)phenyl]ethyl]-36-cyclohexyl-17-(cyclohexylmethyl)-9-[2-(2,2-difluoroethoxy)ethyl]-29-isobutyl-15,18,21,24,30,34,37-heptamethyl-26-[(1S)-1-methylpropyl]-33-(piperidine-1-carbonyl)-6,9,12,15,18, 21,24,27,30,34,37-undecazaspiro[4.33]octatriacontane-7, 10,13,16,19,22,25,28,31,35,38-undecone, (2037) (11S,17S,26S,29S,33S,36S)-11-[2-[3-chloro-4-(trifluoromethyl)phenyl]ethyl]-36-cyclohexyl-17-(cyclohexylmethyl)-9-(2-hydroxyethyl)-29-isobutyl-15,18,21,24, 30,34,37-heptamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25, 28,31,35,38-undecone, (2038) 2-[2-[(11S,17S,26S,29S,33S,36S)-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-7,10,13,16,19,22,25, 28,31,35,38-undecaoxo-33-(piperidine-1-carbonyl)-6,9, 12,15,18,21,24,27,30,34,37-undecazaspiro[4.33] octatriacontan-9-yl]ethoxy]-N,N-dimethyl-acetamide, (2039) (3S,9S,18S,21S,25S,28S,34S)-28-cyclohexyl-9-(cyclohexylmethyl)-3-[2-(3,4-dichlorophenoxy)ethyl]-7,10, 13,16,21,22,26,29-octamethyl-18-[(1S)-1-methylpropyl]-25-(piperidine-1-carbonyl)spiro[1,4,7,10,13,16,19,22,26, 29,32-undecazabicyclo[32.3.0]heptatriacontane-31,1'-cyclopentane]-2,5,8,11,14,17,20,23,27,30,33-undecone, (2040) (3S,9S,18S,21S,25S,28S,34S)-3-[2-(4-chlorophenoxy)ethyl]-28-cyclohexyl-9-(cyclohexylmethyl)-7,10, 13,16,21,22,26,29-octamethyl-18-[(1S)-1-methylpropyl]-25-(piperidine-1-carbonyl)spiro[1,4,7,10,13,16,19,22,26, 29,32-undecazabicyclo[32.3.0]heptatriacontane-31,1'-cyclopentane]-2,5,8,11,14,17,20,23,27,30,33-undecone, (2041) (3S,9S,18S,21S,25S,28S,34S)-28-cyclohexyl-9-(cyclohexylmethyl)-7,10,13,16,21,22,26,29-octamethyl-18-[(1S)-1-methylpropyl]-25-(piperidine-1-carbonyl)-3-[2-[4-(trifluoromethyl)phenoxy]ethyl]spiro[1,4,7,10,13,16, 19,22,26,29,32-undecazabicyclo[32.3.0] heptatriacontane-31,1'-cyclopentane]-2,5,8,11,14,17,20, 23,27,30,33-undecone, (2042) (3S,9S,18S,21S,25S,28S,34S)-3-[(4-chlorophenoxy) methyl]-28-cyclohexyl-9-(cyclohexylmethyl)-7,10,13,16, 21,22,26,29-octamethyl-18-[(1S)-1-methylpropyl]-25-(piperidine-1-carbonyl)spiro[1,4,7,10,13,16,19,22,26,29, 32-undecazabicyclo[32.3.0]heptatriacontane-31,1'-cyclopentane]-2,5,8,11,14,17,20,23,27,30,33-undecone, (2043) (3S,9S,18S,21S,25S,28S,34S)-3-[(2-chlorophenyl) methoxymethyl]-28-cyclohexyl-9-(cyclohexylmethyl)-7, 10,13,16,21,22,26,29-octamethyl-18-[(1S)-1-methylpropyl]-25-(piperidine-1-carbonyl)spiro[1,4,7,10,13,16,19, 22,26,29,32-undecazabicyclo[32.3.0]heptatriacontane-31,1'-cyclopentane]-2,5,8,11,14,17,20,23,27,30,33-undecone, (2044) (3S,9S,18S,21S,25S,28S,34S)-3-[(4-chlorophenyl) methoxymethyl]-28-cyclohexyl-9-(cyclohexylmethyl)-7, 10,13,16,21,22,26,29-octamethyl-18-[(1S)-1-methylpropyl]-25-(piperidine-1-carbonyl)spiro[1,4,7,10,13,16,19, 22,26,29,32-undecazabicyclo[32.3.0]heptatriacontane-31,1'-cyclopentane]-2,5,8,11,14,17,20,23,27,30,33-undecone, (2045) (3S,9S,18S,21S,25S,28S,34S)-3-[(3-chlorophenyl) methoxymethyl]-28-cyclohexyl-9-(cyclohexylmethyl)-7, 10,13,16,21,22,26,29-octamethyl-18-[(1S)-1-methylpropyl]-25-(piperidine-1-carbonyl)spiro[1,4,7,10,13,16,19, 22,26,29,32-undecazabicyclo[32.3.0]heptatriacontane-31,1'-cyclopentane]-2,5,8,11,14,17,20,23,27,30,33-undecone, (2046) (11S,17S,26S,29S,33S,36S)-11-[2-[3-chloro-4-(trifluoromethyl)phenyl]ethyl]-36-cyclohexyl-17-(cyclohexylmethyl)-9-(5-hydroxypent-2-enyl)-29-isobutyl-15,18, 21,24,30,34,37-heptamethyl-26-[(1S)-1-methylpropyl]-33-(piperidine-1-carbonyl)-6,9,12,15,18,21,24,27,30,34, 37-undecazaspiro[4.33]octatriacontane-7,10,13,16,19,22, 25,28,31,35,38-undecone, (2047) (11S,17S,26S,29S,33S,36S)-11-[2-[3-chloro-4-(trifluoromethyl)phenyl]ethyl]-36-cyclohexyl-17-(cyclohexylmethyl)-9-(4-hydroxy-4-methyl-pent-2-enyl)-29-isobutyl-15,18,21,24,30,34,37-heptamethyl-26-[(1S)-1-methylpropyl]-33-(piperidine-1-carbonyl)-6,9,12,15,18, 21,24,27,30,34,37-undecazaspiro[4.33]octatriacontane-7, 10,13,16,19,22,25,28,31,35,38-undecone, (2048) (8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-9,15,18,21,24,30,34,37-octamethyl-26-[(1S)-1-methylpropyl]-33-(piperidine-1-carbonyl)-8-(2-tetrahydropyran-4-ylethyl)-6,9,12,15,18, 21,24,27,30,34,37-undecazaspiro[4.33]octatriacontane-7, 10,13,16,19,22,25,28,31,35,38-undecone, (2049) (11S,17S,26S,29S,33S,36S)-11-[2-[3-chloro-4-(trifluoromethyl)phenyl]ethyl]-36-cyclohexyl-17-(cyclohexylmethyl)-9-(5-hydroxypentyl)-29-isobutyl-15,18,21,24, 30,34,37-heptamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25, 28,31,35,38-undecone, (2050) tert-butyl 3-[2-[(8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-9,15,18,21,24, 30,34,37-octamethyl-26-[(1S)-1-methylpropyl]-7,10,13, 16,19,22,25,28,31,35,38-undecaoxo-33-(piperidine-1-carbonyl)-6,9,12,15,18,21,24,27,30,34,37-undecazaspiro [4.33]octatriacontan-8-yl]ethylidene]azetidine-1-carboxylate, (2051) (11S,17S,26S,29S,33S,36S)-11-[2-[3-chloro-4-(trifluoromethyl)phenyl]ethyl]-36-cyclohexyl-17-(cyclohexylmethyl)-29-isobutyl-9-[(E)-4-methoxybut-2-enyl]-15,18,21,24,30,34,37-heptamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (2052) 4-[(11S,17S,26S,29S,33S,36S)-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-7,10,13,16,19,22,25,28,31,35,38-undecaoxo-33-(piperidine-1-carbonyl)-6,9,12,15,18,21,24,27,30,34,37-undecazaspiro[4.33]octatriacontan-9-yl]-N,N-dimethyl-butanamide, (2053) (8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-9,15,18,21,24,30,34,37-octamethyl-26-[(1S)-1-methylpropyl]-33-(piperidine-1-carbonyl)-8-(2-tetrahydropyran-4-ylideneethyl)-6,9,12,15,18,21,24,27,30,34,37-undecazaspiro[4.33]octatriacontane-7,10,13,16,19,22,25,28,31,35,38-undecone, (2054) 4-[(11S,17S,26S,29S,33S,36S)-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-7,10,13,16,19,22,25,28,31,35,38-undecaoxo-33-(piperidine-1-carbonyl)-6,9,12,15,18,21,24,27,30,34,37-undecazaspiro[4.33]octatriacontan-9-yl]-N,N-dimethyl-but-2-enamide, (2055) (3S,9S,18S,21S,25S,28S,34S)-28-cyclohexyl-9-(cyclohexylmethyl)-7,10,13,16,21,22,26,29-octamethyl-18-[(1S)-1-methylpropyl]-25-(piperidine-1-carbonyl)-3-[3-[4-(trifluoromethyl)phenyl]propyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2056) tert-butyl 3-[2-[(8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-9,15,18,21,24,30,34,37-octamethyl-26-[(1S)-1-methylpropyl]-7,10,13,16,19,22,25,28,31,35,38-undecaoxo-33-(piperidine-1-carbonyl)-6,9,12,15,18,21,24,27,30,34,37-undecazaspiro[4.33]octatriacontan-8-yl]ethyl]azetidine-1-carboxylate, (2057) (5S,8S,11S,15S,18S,23aS,29S,35S,37aS)-8-((S)-sec-butyl)-29-(3-chloro-4-(trifluoromethoxy)phenethyl)-35-(cyclohexylmethyl)-18-cyclopentyl-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (2058) (3S,9S,18S,21S,25S,28S,34S)-28-cyclohexyl-9-(cyclohexylmethyl)-21-isobutyl-7,10,13,16,22,26,29-heptamethyl-18-[(1S)-1-methylpropyl]-3-[2-(4-methylsulfonylphenyl)ethyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2059) (3S,9S,18S,21S,25S,28S,34S)-28-cyclohexyl-9-(cyclohexylmethyl)-7,10,13,16,21,22,26,29-octamethyl-18-[(1S)-1-methylpropyl]-25-(piperidine-1-carbonyl)-3-[2-(3,4,5-trichlorophenyl)ethyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2060) (5S,8S,11S,15S,18S,23aS,29S,35S,37aS)-8-((S)-sec-butyl)-35-(cyclohexylmethyl)-18-cyclopentyl-29-(2-(6-(difluoromethyl)pyridin-3-yl)ethyl)-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (2061) (3S,9S,18S,21S,25S,28S,34S)-9-(cyclohexylmethyl)-3-[2-(3,4-dichloro-5-methoxy-phenyl)ethyl]-28-isopropyl-7,10,13,16,21,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2062) (3S,9S,18S,21S,25S,28S,34S)-28-cyclohexyl-9-(cyclohexylmethyl)-3-[2-(3,4-dichloro-5-isopropoxy-phenyl)ethyl]-7,10,13,16,21,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2063) (5S,8S,11S,15S,18S,23aS,29S,35S,37aS)-29-(2-(benzofuran-5-yl)ethyl)-8-((S)-sec-butyl)-35-(cyclohexylmethyl)-18-cyclopentyl-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (2064) (5S,8S,11S,15S,18S,23aS,29S,35S,37aS)-8-((S)-sec-butyl)-35-(cyclohexylmethyl)-18-cyclopentyl-11-isobutyl-5,6,12,16,19,33,36-heptamethyl-29-(2-(1-methyl-1H-indol-5-yl)ethyl)-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (2065) (5S,8S,11S,15S,18S,23aS,29S,35S,37aS)-8-((S)-sec-butyl)-35-(cyclohexylmethyl)-18-cyclopentyl-11-isobutyl-5,6,12,16,19,33,36-heptamethyl-29-(2-(1-methyl-1H-indol-6-yl)ethyl)-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (2066) (3S,9S,18S,21S,25S,28S,34S)-3-[2-(3-butoxy-4,5-dichloro-phenyl)ethyl]-28-cyclohexyl-9-(cyclohexylmethyl)-7,10,13,16,21,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2067) (5S,8S,11S,15S,18S,23aS,29S,35S,37aS)-8-((S)-sec-butyl)-35-(cyclohexylmethyl)-18-cyclopentyl-29-(3-fluoro-4-(trifluoromethoxy)phenethyl)-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (2068) (3S,9S,18S,21S,25S,28S,34S)-9-(cyclohexylmethyl)-28-isopropyl-7,10,13,16,21,22,26,29-octamethyl-18-[(1S)-1-methylpropyl]-25-(piperidine-1-carbonyl)-3-[2-(3,4,5-trichlorophenyl)ethyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2069) (5S,8S,11S,15S,18S,23aS,29S,35S,37aS)-8-((S)-sec-butyl)-35-(cyclohexylmethyl)-18-cyclopentyl-11- isobutyl-5,6,12,16,19,33,36-heptamethyl-15-(piperidine-1-carbonyl)-29-(2-(5-(trifluoromethyl)pyridin-2-yl)ethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (2070) (5S,8S,11S,15S,18S,23aS,29S,35S,37aS)-8-((S)-sec-butyl)-35-(cyclohexylmethyl)-18-cyclopentyl-11-isobutyl-5,6,12,16,19,33,36-heptamethyl-15-(piperidine-1-carbonyl)-29-(2-(quinolin-6-yl)ethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (2071) 2,3-dichloro-5-[2-[(3S,9S,18S,21S,25S,28S,34S)-9-(cyclohexylmethyl)-28-isopropyl-7,10,13,16,21,22,26,29-octamethyl-18-[(1S)-1-methylpropyl]-2,5,8,11,14,17,20,23,27,30,33-undecaoxo-25-(piperidine-1-carbonyl)spiro[1,4,7,10,13,16,19,22,26,29,32-undecazabicyclo[32.3.0]heptatriacontane-31,1'-cyclopentane]-3-yl]ethyl]benzonitrile, (2072) 5-(2-((5S,8S,11S,15S,18S,23aS,29S,35S,37aS)-8-((S)-sec-butyl)-35-(cyclohexylmethyl)-18-cyclopentyl-11-isobutyl-5,6,12,16,19,33,36-heptamethyl-4,7,10,13,17,20,23,28,31,34,37-undecaoxo-15-(piperidine-1-carbonyl)tetratriacontahydro-2H,4H-spiro[azeto[2,1-u]pyrrolo[2,1-i][1,4,7,10,13,16,19,22,25,28,31]undecaazacyclotetratriacontine-21,1'-cyclopentan]-29-yl)ethyl)-2-(trifluoromethyl)benzonitrile, (2073) (3S,9S,18S,21S,25S,28S,34S)-3-[2-(3-tert-butoxy-4,5-dichloro-phenyl)ethyl]-9-(cyclohexylmethyl)-28-isopropyl-7,10,13,16,21,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2074) (5S,8S,11S,15S,18S,23aS,29S,35S,37aS)-8-((S)-sec-butyl)-35-(cyclohexylmethyl)-18-cyclopentyl-29-(2-(2,2-difluorobenzo[d][1,3]dioxol-5-yl)ethyl)-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (2075) 2,3-dichloro-5-[2-[(3S,9S,18S,21S,25S,28S,34S)-28-cyclohexyl-9-(cyclohexylmethyl)-7,10,13,16,21,22,26,29-octamethyl-18-[(1S)-1-methylpropyl]-2,5,8,11,14,17,20,23,27,30,33-undecaoxo-25-(piperidine-1-carbonyl)spiro[1,4,7,10,13,16,19,22,26,29,32-undecazabicyclo[32.3.0]heptatriacontane-31,1'-cyclopentane]-3-yl]ethyl]benzonitrile, (2076) (5S,8S,11S,15S,18S,23aS,29S,35S,37aS)-8-((S)-sec-butyl)-35-(cyclohexylmethyl)-18-cyclopentyl-29-(4-(difluoromethoxy)-3-fluorophenethyl)-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (2077) (5S,8S,11S,15S,18S,23aS,29S,35S,37aS)-8-((S)-sec-butyl)-35-(cyclohexylmethyl)-18-cyclopentyl-11-isobutyl-5,6,12,16,19,33,36-heptamethyl-15-(piperidine-1-carbonyl)-29-(2-(quinolin-7-yl)ethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (2078) (5S,8S,11S,15S,18S,23aS,29S,35S,37aS)-8-((S)-sec-butyl)-35-(cyclohexylmethyl)-18-cyclopentyl-11-isobutyl-5,6,12,16,19,33,36-heptamethyl-15-(piperidine-1-carbonyl)-29-(2-(6-(trifluoromethyl)pyridin-3-yl)ethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (2079) (3S,9S,18S,21S,25S,28S,34S)-9-(cyclohexylmethyl)-3-[2-(3,4-dichloro-5-isopropoxy-phenyl)ethyl]-28-isopropyl-7,10,13,16,21,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2080) (5S,8S,11S,15S,18S,23aS,29S,35S,37aS)-8-((S)-sec-butyl)-35-(cyclohexylmethyl)-18-cyclopentyl-11-isobutyl-29-(3-methoxy-4-(trifluoromethyl)phenethyl)-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (2081) (3S,9S,18S,21S,25S,28S,34S)-28-cyclohexyl-9-(cyclohexylmethyl)-3-[2-(3,4-dichloro-5-methoxy-phenyl)ethyl]-7,10,13,16,21,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2082) (3S,9S,18S,21S,25S,28S,34S)-3-[2-(3-tert-butoxy-4,5-dichloro-phenyl)ethyl]-28-cyclohexyl-9-(cyclohexylmethyl)-7,10,13,16,21,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2083) (3S,9S,18S,21S,25S,28S,34S)-3-[2-(3-butoxy-4,5-dichloro-phenyl)ethyl]-9-(cyclohexylmethyl)-28-isopropyl-7,10,13,16,21,22,26,29-octamethyl-8-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2084) (5S,8S,11S,15S,18S,23aS,29S,35S,37aS)-8-((S)-sec-butyl)-35-(cyclohexylmethyl)-18-cyclopentyl-11-isobutyl-29-(2-(6-methoxypyridin-3-yl)ethyl)-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (2085) (5S,8S,11S,15S,18S,23aS,29S,35S,37aS)-8-((S)-sec-butyl)-35-(cyclohexylmethyl)-18-cyclopentyl-29-(4-(difluoromethyl)-3-fluorophenethyl)-11-isobutyl-5,6,12,16,19,33,36-heptamethyl-15-(piperidine-1-carbonyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone, (2086) (3S,6S,9S,12S,18S,27S,30S,34R)-6-benzyl-12-[2-(4-chloro-2-fluoro-phenyl)ethyl]-18-[(4-chlorophenyl)methyl]-3,9-diisobutyl-4,7,16,19,22,25,30,31,34-nonamethyl-27-[(1S)-1-methylpropyl]-1,4,7,10,13,16,19,22,25,28,31-undecazacyclotetratriacontane-2,5,8,11,14,17,20,23,26,29,32-undecone, (2087) (3S,6S,9S,12S,18S,27S,30S,34R)-6-benzyl-18-[(4-chlorophenyl)methyl]-3,9-diisobutyl-4,7,16,19,22,25,30,31,34-nonamethyl-27-[(1S)-1-methylpropyl]-12-[2-(2,4,5-trifluorophenyl)ethyl]-1,4,7,10,13,16,19,22,25,28,31-undecazacyclotetratriacontane-2,5,8,11,14,17,20,23,26,29,32-undecone, (2088) (3S,6S,9S,12S,18S,27S,30S,34R)-6-benzyl-18-[(4-chlorophenyl)methyl]-12-[2-[3-chloro-4-(trifluoromethyl)phenyl]ethyl]-3,9-diisobutyl-4,7,16,19,22,25,30,31,34-nonamethyl-27-[(1S)-1-methylpropyl]-1,4,7,10,13,16,19,22,25,28,31-undecazacyclotetratriacontane-2,5,8,11,14,17,20,23,26,29,32-undecone, (2089) (3S,6S,9S,12S,18S,27S,30S,34R)-6-benzyl-18-[(4-chlorophenyl)methyl]-12-[2-(2,4-difluorophenyl)ethyl]-3,9-diisobutyl-4,7,16,19,22,25,30,31,34-nonamethyl-27-[(1S)-1-methylpropyl]-1,4,7,10,13,16,19,22,25,28,31-undecazacyclotetratriacontane-2,5,8,11,14,17,20,23,26,29,32-undecone, (2090) (3S,6S,9S,12S,18S,27S,30S,34R)-6-benzyl-18-[(4-chlorophenyl)methyl]-3,9-diisobutyl-4,7,16,19,22,25,30,31,34-nonamethyl-27-[(1S)-1-methylpropyl]-12-[2-(2,4,6-trifluorophenyl)ethyl]-1,4,7,10,13,16,19,22,25,28,31-undecazacyclotetratriacontane-2,5,8,11,14,17,20,23,26,29,32-undecone, (2091) (3S,6S,9S,12S,18S,27S,30S,34R)-6-benzyl-18-[(4-chlorophenyl)methyl]-3,9-diisobutyl-4,7,16,19,22,25,30,31,34-nonamethyl-27-[(1S)-1-methylpropyl]-12-[2-(2,3,4,5,6-pentafluorophenyl)ethyl]-1,4,7,10,13,16,19,22,25,28,31-undecazacyclotetratriacontane-2,5,8,11,14,17,20,23,26,29,32-undecone, (2092) (3S,6S,9S,12S,18S,27S,30S,34R)-6-benzyl-12-[2-(2-chloro-6-fluoro-phenyl)ethyl]-18-[(4-chlorophenyl)methyl]-3,9-diisobutyl-4,7,16,19,22,25,30,31,34-nonamethyl-27-[(1S)-1-methylpropyl]-1,4,7,10,13,16,19,22,25,28,31-undecazacyclotetratriacontane-2,5,8,11,14,17,20,23,26,29,32-undecone, (2093) (3S,6S,9S,12S,18S,27S,30S,34R)-6-benzyl-18-[(4-chlorophenyl)methyl]-12-[2-[3-fluoro-4-(trifluoromethyl)phenyl]ethyl]-3,9-diisobutyl-4,7,16,19,22,25,30,31,34-nonamethyl-27-[(1S)-1-methylpropyl]-1,4,7,10,13,16,19,22,25,28,31-undecazacyclotetratriacontane-2,5,8,11,14,17,20,23,26,29,32-undecone, (2094) (3S,6S,9S,12S,18S,27S,30S,34R)-6-benzyl-12-[2-(5-chloro-2-fluoro-phenyl)ethyl]-18-[(4-chlorophenyl)methyl]-3,9-diisobutyl-4,7,16,19,22,25,30,31,34-nonamethyl-27-[(1S)-1-methylpropyl]-1,4,7,10,13,16,19,22,25,28,31-undecazacyclotetratriacontane-2,5,8,11,14,17,20,23,26,29,32-undecone, (2095) (3S,6S,9S,12S,18S,27S,30S,34R)-6-benzyl-18-[(4-chlorophenyl)methyl]-3,9-diisobutyl-4,7,16,19,22,25,30,31,34-nonamethyl-27-[(1S)-1-methylpropyl]-12-[2-[3-(trifluoromethyl)phenyl]ethyl]-1,4,7,10,13,16,19,22,25,28,31-undecazacyclotetratriacontane-2,5,8,11,14,17,20,23,26,29,32-undecone, (2096) (3S,9S,18S,21S,25S,28S,31S,34S)-31-benzyl-9-[(4-chlorophenyl)methyl]-3-[2-[2-fluoro-4-(trifluoromethyl)phenyl]ethyl]-28-isobutyl-7,10,13,16,21,22,29,32-octamethyl-18-[(1S)-1-methylpropyl]-25-(pyrrolidine-1-carbonyl)-1,4,7,10,13,16,19,22,26,29,32-undecazabicyclo[32.3.0]heptatriacontane-2,5,8,11,14,17,20,23,27,30,33-undecone, (2097) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-9-isobutyl-N,N,3,4,10,14,17,23,29,32-decamethyl-6-[(1S)-1-methylpropyl]-2,5,8,11,15,18,21,24,27,30,33-undecaoxo-22-(2-oxo-2-pyrrolidin-1-yl-ethyl)spiro[1,4,7,10,14,17,20,23,26,29,32-undecazabicyclo[32.2.0]hexatriacontane-19,1'-cyclopentane]-13-carboxamide, (2098) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-22-[3-(3,3-difluoroazetidin-1-yl)-3-oxo-propyl]-9-isobutyl-3,4,10,14,17,23,29,32-octamethyl-6-[(1S)-1-methylpropyl]-13-(morpholine-4-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (2099) (3S,9S,12S,18S,27S,30S,34S)-34-(3,3-difluoropiperidine-1-carbonyl)-12-[(3-iodophenyl)methyl]-3,30-diisobutyl-9-[(4-methoxyphenyl)methyl]-1,6,6,7,16,19,22,25,31-nonamethyl-27-[(1S)-1-methylpropyl]-18-(p-tolylmethyl)-1,4,7,10,13,16,19,22,25,28,31-undecazacyclotetratriacontane-2,5,8,11,14,17,20,23,26,29,32-undecone, (2100) 3-[(3S,6S,9S,12S,18S,27S,30S,34S)-9-butyl-12-[(3-iodophenyl)methyl]-3,30-diisobutyl-1,7,16,19,22,25,31-heptamethyl-27-[(1S)-1-methylpropyl]-2,5,8,11,14,17,20,23,26,29,32-undecaoxo-34-(piperidine-1-carbonyl)-18-(p-tolylmethyl)-1,4,7,10,13,16,19,22,25,28,31-undecazacyclotetratriacont-6-yl]-N,N-dimethyl-propanamide, (2101) (3S,9S,12S,18S,27S,30S,34S)-34-(4,4-difluoropiperidine-1-carbonyl)-12-[(3-iodophenyl)methyl]-3,30-diisobutyl-9-[(4-methoxyphenyl)methyl]-1,6,6,7,16,19,22,25,31-nonamethyl-27-[(1S)-1-methylpropyl]-18-(p-tolylmethyl)-1,4,7,10,13,16,19,22,25,28,31-undecazacyclotetratriacontane-2,5,8,11,14,17,20,23,26,29,32-undecone, (2102) (3S,6S,9S,13S,16S,22S,25S,31S,34S)-22-[2-(azetidin-1-yl)-2-oxo-ethyl]-25-[2-[3-chloro-4-(trifluoromethyl)phenyl]ethyl]-31-(cyclohexylmethyl)-16-cyclopentyl-9-isobutyl-N,N,3,4,10,14,17,23,29,32-decamethyl-6-[(1S)-1-methylpropyl]-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide, (2103) (3S,6S,9S,13S,16S,22S,25S,31S,34S)-22-[3-(azetidin-1-yl)-3-oxo-propyl]-25-[2-[3-chloro-4-(trifluoromethyl)phenyl]ethyl]-31-(cyclohexylmethyl)-16-cyclopentyl-9-isobutyl-3,4,10,14,17,23,29,32-octamethyl-6-[(1S)-1-methylpropyl]-13-(morpholine-4-carbonyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (2104) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-9-isobutyl-3,4,10,14,17,23,29,32-octamethyl-6-[(1S)-1-methylpropyl]-13-(morpholine-4-carbonyl)-22-(3-oxo-3-pyrrolidin-1-yl-propyl)spiro[1,4,7,10,14,17,20,23,26,29,32-undecazabicyclo[32.2.0]hexatriacontane-19,1'-cyclopentane]-2,5,8,11,15,18,21,24,27,30,33-undecone, (2105) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-9-isobutyl-N,N,3,4,10,14,17,23,29,32-decamethyl-6-[(1S)-1-methylpropyl]-2,5,8,11,15,18,21,24,27,30,33-undecaoxo-22-[2-oxo-2-(1-piperidyl)ethyl]spiro[1,4,7,10,14,17,20,23,26,29,32-undecazabicyclo[32.2.0]hexatriacontane-19,1'-cyclopentane]-13-carboxamide, (2106) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-22-[2-(dimethylamino)-2-oxo-ethyl]-9-isobutyl-N,N,3,4,10,14,17,23,29,32- decamethyl-6-[(1S)-1-methylpropyl]-2,5,8,11,15,18,21, 24,27,30,33-undecaoxo-spiro[1,4,7,10,14,17,20,23,26, 29,32-undecazabicyclo[32.2.0]hexatriacontane-19,1'-cyclopentane]-13-carboxamide, (2107) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-9-isobutyl-3,4,10,14,17,23,29, 32-octamethyl-6-[(1S)-1-methylpropyl]-13-(morpholine-4-carbonyl)-22-(3-morpholino-3-oxo-propyl)spiro[1,4,7, 10,14,17,20,23,26,29,32-undecazabicyclo[32.2.0] hexatriacontane-19,1'-cyclopentane]-2,5,8,11,15,18,21, 24,27,30,33-undecone, (2108) 3-[(3S,6S,9S,13S,16S,22S,25S,31S,34S)-25-[2-[3-chloro-4-(trifluoromethyl)phenyl]ethyl]-31-(cyclohexylmethyl)-16-cyclopentyl-9-isobutyl-3,4,10,14,17,23,29, 32-octamethyl-6-[(1S)-1-methylpropyl]-13-(morpholine-4-carbonyl)-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-22-yl]-N,N-dimethyl-propanamide, (2109) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-9-isobutyl-N,N,3,4,10,14,17,23, 29,32-decamethyl-6-[(1S)-1-methylpropyl]-22-(2-morpholino-2-oxo-ethyl)-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide, (2110) 3-[(3S,6S,9S,13S,16S,19S,22S,25S,31S,34S)-22-butyl-25-[(3-iodophenyl)methyl]-9,16-diisobutyl-31-[(4-methoxyphenyl)methyl]-3,4,10,14,20,29,32-heptamethyl-6-[(1S)-1-methylpropyl]-2,5,8,11,15,18,21,24,27, 30,33-undecaoxo-13-(piperidine-1-carbonyl)-1,4,7,10, 14,17,20,23,26,29,32-undecazabicyclo[32.2.0] hexatriacontan-19-yl]-N,N-dimethyl-propanamide, (2111) 3-[(3S,6S,9S,13S,16S,22S,25S,31S,34S)-25-[2-[3-chloro-4-(trifluoromethyl)phenyl]ethyl]-31-(cyclohexylmethyl)-16-cyclopentyl-9-isobutyl-3,4,10,14,17,23,29, 32-octamethyl-6-[(1S)-1-methylpropyl]-13-(morpholine-4-carbonyl)-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-22-yl]-N-methyl-propanamide, (2112) (3S,6S,9S,13S,16S,22S,25S,31S,34S)-25-[2-[3-chloro-4-(trifluoromethyl)phenyl]ethyl]-31-(cyclohexylmethyl)-16-cyclopentyl-9-isobutyl-3,4,10,14,17,23,29, 32-octamethyl-6-[(1S)-1-methylpropyl]-13-(morpholine-4-carbonyl)-22-[3-oxo-3-(1-piperidyl)propyl]spiro[1,4,7, 10,14,17,20,23,26,29,32-undecazabicyclo[32.2.0] hexatriacontane-19,1'-cyclopentane]-2,5,8,11,15,18,21, 24,27,30,33-undecone, (2113) (3S,9S,18S,21S,25S,28S,34S,36R)-3-[2-[3-chloro-4-(trifluoromethyl)phenyl]ethyl]-9-(cyclopentylmethyl)-21-isobutyl-28-isopropyl-7,10,13,16,22,26,29-heptamethyl-18-[(1S)-1-methylpropyl]-25-(piperidine-1-carbonyl)-36-(triazol-1-yl)spiro[1,4,7,10,13,16,19,22,26, 29,32-undecazabicyclo[32.3.0]heptatriacontane-31,1'-cyclopentane]-2,5,8,11,14,17,20,23,27,30,33-undecone, (2114) (6S,9S,13S,16S,22S,25S,31S,34S)-25-[(3-iodophenyl)methyl]-9,16-diisobutyl-4,10,14,19,19,20,29,32-octamethyl-6-[(1S)-1-methylpropyl]-22-(phenoxymethyl)-13-(piperidine-1-carbonyl)-31-(p-tolylmethyl)-1,4,7,10, 14,17,20,23,26,29,32-undecazabicyclo[32.2.0] hexatriacontane-2,5,8,11,15,18,21,24,27,30,33-undecone, (2115) (3S,9S,18S,21S,25S,28S,34S,36S)-3-[2-[3-chloro-4-(trifluoromethyl)phenyl]ethyl]-9-(cyclopentylmethyl)-21-isobutyl-28-isopropyl-7,10,13,16,22,26,29-heptamethyl-18-[(1S)-1-methylpropyl]-25-(piperidine-1-carbonyl)-36-(triazol-1-yl)spiro[1,4,7,10,13,16,19,22,26, 29,32-undecazabicyclo[32.3.0]heptatriacontane-31,1'-cyclopentane]-2,5,8,11,14,17,20,23,27,30,33-undecone, (2116) (3S,9S,18S,21S,25R,28S,34S,36R)-36-benzyloxy-9-(cyclohexylmethyl)-3-[2-[3-fluoro-4-(trifluoromethyl)phenyl]ethyl]-21,28-diisobutyl-7,10,13,16,22,25,29-heptamethyl-18-[(1S)-1-methylpropyl]spiro[1,4,7,10,13,16, 19,22,26,29,32-undecazabicyclo[32.3.0] heptatriacontane-31,1'-cyclopentane]-2,5,8,11,14,17,20, 23,27,30,33-undecone, (2117) (3S,9S,18S,21S,25S,28S,34S,36S)-3-[2-[3-chloro-4-(trifluoromethyl)phenyl]ethyl]-28-cyclohexyl-9-(cyclohexylmethyl)-36-(2-hydroxyethoxy)-21-isobutyl-7,10, 13,16,22,26,29-heptamethyl-18-I[(1S)-1-methylpropyl]-25-(piperidine-1-carbonyl)spiro[1,4,7,10,13,16,19,22,26, 29,32-undecazabicyclo[32.3.0]heptatriacontane-31,1'-cyclopentane]-2,5,8,11,14,17,20,23,27,30,33-undecone, (2118) (3S,9S,18S,21S,25S,28S,34S,36R)-9-(cyclohexylmethyl)-36-ethoxy-3-[2-[3-fluoro-4-(trifluoromethyl)phenyl]ethyl]-21,28-diisobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2119) (3S,9S,18S,21S,25S,28S,34S,36R)-3-[2-[3-chloro-4-(trifluoromethyl)phenyl]ethyl]-28-cyclohexyl-9-(cyclohexylmethyl)-36-(2,2-difluoroethoxy)-21-isobutyl-7, 10,13,16,22,26,29-heptamethyl-18-[(1S)-1-methylpropyl]-25-(piperidine-1-carbonyl)spiro[1,4,7,10, 13,16,19,22,26,29,32-undecazabicyclo[32.3.0] heptatriacontane-31,1'-cyclopentane]-2,5,8,11,14,17,20, 23,27,30,33-undecone, (2120) (3S,9S,18S,21S,25S,28S,34S,36S)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-25-(piperidine-1-carbonyl)-36-(3-pyridylmethoxy)spiro[1,4,7,10,13,16,19, 22,26,29,32-undecazabicyclo[32.3.0]heptatriacontane-31,1'-cyclopentane]-2,5,8,11,14,17,20,23,27,30,33-undecone, (2121) (3S,9S,18S,21S,25S,28S,34S,36R)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-25-(piperidine-1-carbonyl)-36-(3-pyridylmethoxy)spiro[1,4,7,10,13,16,19, 22,26,29,32-undecazabicyclo[32.3.0]heptatriacontane-31,1'-cyclopentane]-2,5,8,11,14,17,20,23,27,30,33-undecone, (2122) (3S,9S,18S,21S,25S,28S,34S,36R)-3-[2-[3-chloro-4-(trifluoromethyl)phenyl]ethyl]-28-cyclohexyl-9-(cyclohexylmethyl)-36-(2-hydroxyethoxy)-21-isobutyl-7,10, 13,16,22,26,29-heptamethyl-18-[(1S)-1-methylpropyl]-25-(piperidine-1-carbonyl)spiro[1,4,7,10,13,16,19,22,26, 29,32-undecazabicyclo[32.3.0]heptatriacontane-31,1'-cyclopentane]-2,5,8,11,14,17,20,23,27,30,33-undecone, (2123) (3S,9S,18S,21S,25S,28S,34S,36S)-3-[2-[3-chloro-4-(trifluoromethyl)phenyl]ethyl]-28-cyclohexyl-9-(cyclohexylmethyl)-36-(2,2-difluoroethoxy)-21-isobutyl-7,10, 13,16,22,26,29-heptamethyl-18-1[(1S)-1-methylpropyl]-25-(piperidine-1-carbonyl)spiro[1,4,7,10,13,16,19,22,26, 29,32-undecazabicyclo[32.3.0]heptatriacontane-31,1'-cyclopentane]-2,5,8,11,14,17,20,23,27,30,33-undecone, (2124) (3S,9S,18S,21S,25S,28S,34S,36R)-3-[2-[3-chloro-4-(trifluoromethyl)phenyl]ethyl]-28-cyclohexyl-9-(cyclohexylmethyl)-21-isobutyl-7,10,13,16,22,26,29-heptamethyl-18-[(1S)-1-methylpropyl]-25-(piperidine-1-carbonyl)-36-(3-thienylmethoxy)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2125) (3S,9S,18S,21S,25S,28S,34S,36R)-9-(cyclohexylmethyl)-3-[2-[3-fluoro-4-(trifluoromethyl)phenyl]ethyl]-21,28-diisobutyl-7,10,13,16,22,26,29-heptamethyl-18-[(1S)-1-methylpropyl]-36-(m-tolylmethoxy)-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2126) (3S,9S,18S,21S,25S,28S,34S,36S)-36-[(3-chlorophenyl)methoxy]-9-(cyclohexylmethyl)-3-[2-[3-fluoro-4-(trifluoromethyl)phenyl]ethyl]-21,28-diisobutyl-7,10,13,16,22,26,29-heptamethyl-18-1[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2127) (3S,9S,18S,21S,25S,28S,34S,36S)-9-(cyclohexylmethyl)-36-ethoxy-3-[2-[3-fluoro-4-(trifluoromethyl)phenyl]ethyl]-21,28-diisobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2128) (3S,9S,18S,21S,25S,28S,34S,36R)-9-(cyclohexylmethyl)-36-[[4-(difluoromethoxy)phenyl]methoxy]-3-[2-[3-fluoro-4-(trifluoromethyl)phenyl]ethyl]-21,28-diisobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2129) (3S,9S,18S,21S,25S,28S,34S,36S)-36-[(4-chlorophenyl)methoxy]-9-(cyclohexylmethyl)-3-[2-[3-fluoro-4-(trifluoromethyl)phenyl]ethyl]-21,28-diisobutyl-7,10,13,16,22,26,29-heptamethyl-18-1[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2130) (3S,9S,18S,21S,25S,28S,34S,36R)-9-(cyclohexylmethyl)-3-[2-[3-fluoro-4-(trifluoromethyl)phenyl]ethyl]-21,28-diisobutyl-7,10,13,16,22,26,29-heptamethyl-18-[(1S)-1-methylpropyl]-25-(piperidine-1-carbonyl)-36-(p-tolylmethoxy)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2131) (3S,9S,18S,21S,25S,28S,34S,36R)-9-(cyclohexylmethyl)-3-[2-[3-fluoro-4-(trifluoromethyl)phenyl]ethyl]-21,28-diisobutyl-36-[(3-methoxyphenyl)methoxy]-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2132) (3S,9S,18S,21S,25S,28S,34S,36S)-36-[(2-chlorophenyl)methoxy]-9-(cyclohexylmethyl)-3-[2-[3-fluoro-4-(trifluoromethyl)phenyl]ethyl]-21,28-diisobutyl-7,10,13,16,22,26,29-heptamethyl-18-1[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2133) (3S,9S,18S,21S,25S,28S,34S,36R)-36-[(4-chlorophenyl)methoxy]-9-(cyclohexylmethyl)-3-[2-[3-fluoro-4-(trifluoromethyl)phenyl]ethyl]-21,28-diisobutyl-7,10,13,16,22,26,29-heptamethyl-18-1[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2134) (3S,9S,18S,21S,25S,28S,34S,36R)-36-[(3-chlorophenyl)methoxy]-9-(cyclohexylmethyl)-3-[2-[3-fluoro-4-(trifluoromethyl)phenyl]ethyl]-21,28-diisobutyl-7,10,13,16,22,26,29-heptamethyl-18-1[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2135) (3S,9S,18S,21S,25S,28S,34S,36S)-9-(cyclohexylmethyl)-36-[[4-(difluoromethoxy)phenyl]methoxy]-3-[2-[3-fluoro-4-(trifluoromethyl)phenyl]ethyl]-21,28-diisobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2136) (3S,9S,18S,21S,25S,28S,34S,36S)-9-(cyclohexylmethyl)-3-[2-[3-fluoro-4-(trifluoromethyl)phenyl]ethyl]-21,28-diisobutyl-36-[(3-methoxyphenyl)methoxy]-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2137) (3S,9S,18S,21S,25S,28S,34S,36S)-9-(cyclohexylmethyl)-3-[2-[3-fluoro-4-(trifluoromethyl)phenyl]ethyl]-21,28-diisobutyl-7,10,13,16,22,26,29-heptamethyl-18-[(1S)-1-methylpropyl]-36-(o-tolylmethoxy)-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2138) (3S,9S,18S,21S,25S,28S,34S,36R)-36-[(2-chlorophenyl)methoxy]-9-(cyclohexylmethyl)-3-[2-[3-fluoro-4-(trifluoromethyl)phenyl]ethyl]-21,28-diisobutyl-7,10,13,16,22,26,29-heptamethyl-18-1[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2139) (3S,9S,18S,21S,25S,28S,34S,36R)-9-(cyclohexylmethyl)-3-[2-[3-fluoro-4-(trifluoromethyl)phenyl]ethyl]-21,28-diisobutyl-7,10,13,16,22,26,29-heptamethyl-18-[(1S)-1-methylpropyl]-36-(o-tolylmethoxy)-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2140) (3S,9S,18S,21S,25S,28S,34S,36S)-9-(cyclohexylmethyl)-3-[2-[3-fluoro-4-(trifluoromethyl)phenyl]ethyl]-21,28-diisobutyl-7,10,13,16,22,26,29-heptamethyl-18-[(1S)-1-methylpropyl]-25-(piperidine-1-carbonyl)-36-(p-tolylmethoxy)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2141) (3S,9S,18S,21S,25S,28S,34S,36S)-9-(cyclohexylmethyl)-3-[2-[3-fluoro-4-(trifluoromethyl)phenyl]ethyl]-21,28-diisobutyl-7,10,13,16,22,26,29-heptamethyl-18-[(1S)-1-methylpropyl]-36-(m-tolylmethoxy)-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone, (2142) (3S,9S,12S,18S,27S,30S,34S)-9-butyl-18-[(4-chlorophenyl)methyl]-12-[(3-ethynylphenyl)methyl]-3,30-diisobutyl-1,6,6,7,16,19,22,25,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone, (2143) (11S,17S,26S,29S,33R,36S)-11-[2-[3-chloro-4-(trifluoromethyl)phenyl]ethyl]-36-cyclobutyl-17-(cyclohexylmethyl)-15,18,21,24,29,30,33,34,37-nonamethyl-26-[(1S)-1-methylpropyl]-9-phenyl-6,9,12,15,18,21,24,27,30,34,37-undecazaspiro[4.33]octatriacontane-7,10,13,16,19,22,25,28,31,35,38-undecone, (2144) (3S,6S,9S,13S,16S,25S,31S,34S)-25-[2-[3-chloro-4-(trifluoromethyl)phenyl]ethyl]-16,31-di(cyclobutyl)-3,4,9,10,14,17,19,19,20,29,32-undecamethyl-6-[(1S)-1-methylpropyl]-23-phenyl-13-(piperidine-1-carbonyl)-1,4,7,10,14,17,20,23,26,29,32-undecazabicyclo[32.2.0]hexatriacontane-2,5,8,11,15,18,21,24,27,30,33-undecone, (2145) (3S,12S,18S,27S,30S,34R)-12-[2-[3-chloro-4-(trifluoromethyl)phenyl]ethyl]-3-cyclobutyl-18-(cyclohexylmethyl)-1,4,6,6,7,16,19,22,25,30,31,34-dodecamethyl-27-[(1S)-1-methylpropyl]-10-phenyl-1,4,7,10,13,16,19,22,25,28,31-undecazacyclotetratriacontane-2,5,8,11,14,17,20,23,26,29,32-undecone, (2146) (3S,6S,9S,13S,16S,25S,31S,34S)-23-(3-chlorophenyl)-25-[2-[3-chloro-4-(trifluoromethyl)phenyl]ethyl]-16,31-di(cyclobutyl)-3,4,9,10,14,17,19,19,20,29,32-undecamethyl-6-[(1S)-1-methylpropyl]-13-(piperidine-1-carbonyl)-1,4,7,10,14,17,20,23,26,29,32-undecazabicyclo[32.2.0]hexatriacontane-2,5,8,11,15,18,21,24,27,30,33-undecone, (2147) (3S,6S,9S,13S,16S,25S,31S,34S)-23-(4-chlorophenyl)-25-[2-[3-chloro-4-(trifluoromethyl)phenyl]ethyl]-16,31-di(cyclobutyl)-3,4,9,10,14,17,19,19,20,29,32-undecamethyl-6-[(1S)-1-methylpropyl]-13-(piperidine-1-carbonyl)-1,4,7,10,14,17,20,23,26,29,32-undecazabicyclo[32.2.0]hexatriacontane-2,5,8,11,15,18,21,24,27,30,33-undecone, (2148) (3S,6S,9S,13R,16S,25S,31S,34S)-25-[2-[3-chloro-4-(trifluoromethyl)phenyl]ethyl]-16,31-di(cyclobutyl)-3,4,9,10,13,14,17,19,19,20,29,32-dodecamethyl-6-[(1S)-1-methylpropyl]-23-phenyl-1,4,7,10,14,17,20,23,26,29,32-undecazabicyclo[32.2.0]hexatriacontane-2,5,8,11,15,18,21,24,27,30,33-undecone, (2149) (11S,17S,26S,29S,33S,36S)-11-[2-[3-chloro-4-(trifluoromethyl)phenyl]ethyl]-36-cyclobutyl-17-(cyclohexylmethyl)-15,18,21,24,29,30,34,37-octamethyl-26-[(1S)-1-methylpropyl]-33-(piperidine-1-carbonyl)-9-(3-thienyl)-6,9,12,15,18,21,24,27,30,34,37-undecazaspiro[4.33]octatriacontane-7,10,13,16,19,22,25,28,31,35,38-undecohe, (2150) (3S,12S,18S,27S,30S,34S)-12-[2-[3-chloro-4-(trifluoromethyl)phenyl]ethyl]-3-cyclobutyl-18-(cyclohexylmethyl)-1,4,6,6,7,16,19,22,25,30,31-undecamethyl-27-f(1S)-1-methylpropyl]-10-phenyl-34-(piperidine-1-carbonyl)-1,4,7,10,13,16,19,22,25,28,31-undecazacyclotetratriacontane-2,5,8,11,14,17,20,23,26,29,32-undecone, (2151) (11S,17S,26S,29S,33S,36S)-11-[2-[3-chloro-4-(trifluoromethyl)phenyl]ethyl]-36-cyclobutyl-17-(cyclohexylmethyl)-15,18,21,24,29,30,34,37-octamethyl-26-[(1S)-1-methylpropyl]-9-phenyl-33-(piperidine-1-carbonyl)-6,9,12,15,18,21,24,27,30,34,37-undecazaspiro[4.33]octatriacontane-7,10,13,16,19,22,25,28,31,35,38-undecone, (2152) (5S,8S,11S,15R,18S,23aS,29S,35S,37aS)-8-((S)-sec-butyl)-29-(3-chloro-4-(trifluoromethyl)phenethyl)-18-(cyclobutylmethyl)-35-(cyclohexylmethyl)-5,6,11,12,15,16,19,21,21,22,33,36-dodecamethyltetracosahydro-2H-azeto[2,1-u]pyrrolo[2,1-i][1,4,7,10,13,16,19,22,25,28,31]undecaazacyclotetratriacontin-4,7,10,13,17,20,23,28,31,34,37(14H)-undecaone, (2153) (5S,8S,11S,15R,18S,23aS,29S,35S,37aS)-8,18-di((S)-sec-butyl)-29-(3-chloro-4-(trifluoromethyl)phenethyl)-35-(cyclohexylmethyl)-5,6,11,12,15,16,19,21,21,22,33,36-dodecamethyltetracosahydro-2H-azeto[2,1-u]pyrrolo[2,1-i][1,4,7,10,13,16,19,22,25,28,31]undecaazacyclotetratriacontin-4,7,10,13,17,20,23,28,31,34,37(14H)-undecaone, (2154) (5S,8S,11S,15R,18S,23aS,29S,35S,37aS)-8-((S)-sec-butyl)-29-(3-chloro-4-(trifluoromethyl)phenethyl)-35-(cyclohexylmethyl)-18-ethyl-5,6,11,12,15,16,19,21,21,22,33,36-dodecamethyltetracosahydro-2H-azeto[2,1-u]pyrrolo[2,1-i][1,4,7,10,13,16,19,22,25,28,31]undecaazacyclotetratriacontin-4,7,10,13,17,20,23,28,31,34,37(14H)-undecaone, (2155) (5S,8S,11S,15R,18S,23aS,29S,35S,37aS)-8-((S)-sec-butyl)-29-(3-chloro-4-(trifluoromethyl)phenethyl)-18-cyclohexyl-35-(cyclohexylmethyl)-5,6,11,12,15,16,19,21,21,22,33,36-dodecamethyltetracosahydro-2H-azeto[2,1-u]pyrrolo[2,1-i][1,4,7,10,13,16,19,22,25,28,31]undecaazacyclotetratriacontin-4,7,10,13,17,20,23,28,31,34,37(14H)-undecaone, (2156) (5S,8S,11S,15R,18S,23aS,29S,35S,37aS)-8-((S)-sec-butyl)-29-(3-chloro-4-(trifluoromethyl)phenethyl)-35-(cyclohexylmethyl)-18-cyclopentyl-5,6,11,12,15,16,19,21,21,22,33,36-dodecamethyltetracosahydro-2H-azeto[2,1-u]pyrrolo[2,1-i][1,4,7,10,13,16,19,22,25,28,31]undecaazacyclotetratriacontin-4,7,10,13,17,20,23,28,31,34,37(14H)-undecaone, (2157) (5S,8S,11S,15R,18S,23aS,29S,35S,37aS)-8-((S)-sec-butyl)-29-(3-chloro-4-(trifluoromethyl)phenethyl)-18-cyclobutyl-35-(cyclohexylmethyl)-5,6,11,12,15,16,19,21,21,22,33,36-dodecamethyltetracosahydro-2H-azeto[2,1-u]pyrrolo[2,1-i][1,4,7,10,13,16,19,22,25,28,31]undecaazacyclotetratriacontin-4,7,10,13,17,20,23,28,31,34,37(14H)-undecaone, (2158) (5S,8S,11S,15R,18S,23aS,29S,35S,37aS)-8-((S)-sec-butyl)-29-(3-chloro-4-(trifluoromethyl)phenethyl)-35-(cyclohexylmethyl)-18-(cyclopentylmethyl)-5,6,11,12,15,16,19,21,21,22,33,36-dodecamethyltetracosahydro-2H-azeto[2,1-u]pyrrolo[2,1-i][1,4,7,10,13,16,19,22,25,28,31]undecaazacyclotetratriacontin-4,7,10,13,17,20,23,28,31,34,37(14H)-undecaone, (2159) (5S,8S,11S,15R,18S,23aS,29S,35S,37aS)-8,11-di((S)-sec-butyl)-29-(3-chloro-4-(trifluoromethyl)phenethyl)-35-(cyclohexylmethyl)-18-isopropyl-5,6,12,15,16,19,21,21,22,33,36-undecamethyltetracosahydro-2H-azeto[2,1-u]pyrrolo[2,1-i][1,4,7,10,13,16,19,22,25,28,31]undecaazacyclotetratriacontin-4,7,10,13,17,20,23,28,31,34,37(14H)-undecaone, (2160) (5S,8S,11S,15R,18S,23aS,29S,35S,37aS)-8-((S)-sec-butyl)-29-(3-chloro-4-(trifluoromethyl)phenethyl)-35-(cyclohexylmethyl)-18-isobutyl-5,6,11,12,15,16,19,21,21,22,33,36-dodecamethyltetracosahydro-2H-azete[2,1-u]pyrrolo[2,1-i][1,4,7,10,13,16,19,22,25,28,31]undecaazacyclotetratoriacontin-4,7,10,13,17,20,23,28,31,34,37(14H)-undecaone, (2161) (8S,11S,17S,26S,29S,33S,36S)-8-[(2-chlorophenyl)methyl]-11-[2-[3-chloro-4-(trifluoromethyl)phenyl]ethyl]-17-(cyclohexylmethyl)-9-ethyl-36-isopropyl-15,18,21,24,29,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (2162) (8S,11S,17S,26S,29S,33S,36S)-8-[(2-chlorophenyl)methyl]-11-[2-[3-chloro-4-(trifluoromethyl)phenyl]ethyl]-17-(cyclohexylmethyl)-9-ethyl-36-isopropyl-15,18,21,24,29,30,34,37-octamethyl-26-[(1S)-1-methylpropyl]-33-(pyrrolidine-1-carbonyl)-6,9,12,15,18, (2163) (3S,6S,9S,13S,16S,22S,25S,31S,34S)-22-[(2-chlorophenyl)methyl]-25-[2-[3-chloro-4-(trifluoromethyl)phenyl]ethyl]-23-ethyl-N,N,3,4,9,10,14,17,29,32-decamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (2164) (8S,11S,17S,26S,29S,33S,36S)-8-[(2-chlorophenyl)methyl]-11-[2-[3-chloro-4-(trifluoromethyl)phenyl]ethyl]-17-(cyclohexylmethyl)-9-ethyl-36-isopropyl-N,N,15,18,21,24,29,30,34,37-decamethyl-26-[(1S)-1-methylpropyl]-7,10,13,16,19,22,25,28,31,35,38-undecaoxo-6,9,12,15,18,21,24,27,30,34,37-undecazaspiro[4.33]octatriacontane-33-carboxamide, (2165) (3S,6S,9S,13S,16S,22S,25S,31S,34S)-22-[(2-chlorophenyl)methyl]-25-[2-[3-chloro-4-(trifluoromethyl)phenyl]ethyl]-23-ethyl-9-isobutyl-N,N,3,4,10,14,17,29,32-nonamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (2166) (8S,11S,17S,26S,29S,33S,36S)-8-[(2-chlorophenyl)methyl]-11-[2-[3-chloro-4-(trifluoromethyl)phenyl]ethyl]-9-ethyl-36-isopropyl-15,18,21,24,29,30,34,37-octamethyl-26-[(1S)-1-methylpropyl]-33-(piperidine-1-carbonyl)-17-(p-tolylmethyl)-6,9,12,15,18,21,24,27,30,34,37-undecazaspiro[4.33]octatriacontane-7,10,13,16,19,22,25,28,31,35,38-undecone, (2167) (8S,11S,17S,26S,29S,33S,36S)-8-[(2-chlorophenyl)methyl]-11-[2-[3-chloro-4-(trifluoromethyl)phenyl]ethyl]-17-(cyclohexylmethyl)-9-ethyl-36-isopropyl-15,18,21,24,29,30,34,37-octamethyl-26-[(1S)-1-methylpropyl]-33-(morpholine-4-carbonyl)-6,9,12,15,18,21,24,27,30,34,37-undecazaspiro[4.33]octatriacontane-7,10,13,16,19,22,25,28,31,35,38-undecone, (2168) (8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-8-(2-methoxyethyl)-9,15,18,21,24,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (2169) 5-[[(8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-9,15,18,21,24,30,34,37-octamethyl-26-[(1S)-1-methylpropyl]-7,10,13,16,19,22,25,28,31,35,38-undecaoxo-33-(piperidine-1-carbonyl)-6,9,12,15,18,21,24,27,30,34,37-undecazaspiro[4.33]octatriacontan-8-yl]methyl]pyridine-2-carbonitrile, (2170) (8S,11S,17S,26S,29S,33S,36S)-11-[2-[3-chloro-4-(trifluoromethyl)phenyl]ethyl]-36-cyclohexyl-17-(cyclohexylmethyl)-8-[(3-fluoro-4-hydroxy-phenyl)methyl]-29-isobutyl-9,15,18,21,24,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (2171) (8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-8-[(4-methoxyphenyl)methyl]-9,15,18,21,24,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (2172) (3S,9S,18S,24R,27S,33S)-18-[(2S)-butan-2-yl]-3-[2-[3-chloro-4-(trifluoromethyl)phenyl]ethyl]-9-(cyclohexylmethyl)-27-cyclopentyl-N,N,7,10,13,16,25,28-octamethyl-2,5,8,11,14,17,20,26,29,32-decaoxospiro[22-thia-1,4,7,10,13,16,19,25,28,31-decazabicyclo[31.3.0]hexatriacontane-30,1'-cyclopentane]-24-carboxamide, (2173) (3S,9S,18S,24R,27S,33S)-18,27-bis[(2S)-butan-2-yl]-3-[2-[3-chloro-4-(trifluoromethyl)phenyl]ethyl]-N,N,7,10,13,16,25,28-octamethyl-9-[(4-methylphenyl)methyl]-2,5,8,11,14,17,20,26,29,32-decaoxospiro[22-thia-1,4,7,10,13,16,19,25,28,31-decazabicyclo[31.3.0]hexatriacontane-30,1'-cyclopentane]-24-carboxamide, (2174) (3S,9S,12S,17S,20S,23S,29R,32S,38S)-20-[(2S)-butan-2-yl]-32-cyclopentyl-3-[2-[3-fluoro-4-(trifluoromethyl)phenyl]ethyl]-N,N,7,10,17,18,24,30,33-nonamethyl-23-(2-methylpropyl)-2,5,8,11,16,19,22,25,31,34,37-undecaoxo-9-(propoxymethyl)spiro[27-thia-1,4,7,10,15,18,21,24,30,33,36-undecazatricyclo[36.3.0.0¹²,¹⁵]hentetracontane-35,1'-cyclopentane]-29-carboxamide, (2175) (3S,9S,18S,21S,27R,30S,36S)-18-[(2S)-butan-2-yl]-3-[2-[3-chloro-4-(trifluoromethyl)phenyl]ethyl]-9-(cyclohexylmethyl)-30-cyclopentyl-N,N,7,10,13,16,22,28,31-nonamethyl-21-(2-methylpropyl)-2,5,8,11,14,17,20,23,29,32,35-undecaoxospiro[25-thia-1,4,7,10,13,16,19,22,28,31,34-undecazabicyclo[34.3.0]nonatriacontane-33,1'-cyclopentane]-27-carboxamide, (2176) (3S,9S,12S,17S,20S,23S,29R,32S,38S,40R)-20-[(2S)-butan-2-yl]-9-(cyclohexylmethyl)-32-cyclopentyl-3-[2-[3,5-difluoro-4-(trifluoromethyl)phenyl]ethyl]-40-ethoxy-N,N,7,10,17,18,24,30,33-nonamethyl-23-(2-methylpropyl)-2,5,8,11,16,19,22,25,31,34,37-undecaoxospiro[27-thia-1,4,7,10,15,18,21,24,30,33,36-undecazatricyclo[36.3.0.0¹²,¹⁵]hentetracontane-35,1'-cyclopentane]-29-carboxamide, (2177) (3S,9S,12S,17S,20S,23S,29R,32S,38S)-20-[(2S)-butan-2-yl]-3-[2-[3-chloro-4-(trifluoromethyl)phenyl]ethyl]-32-cyclopentyl-N,N,7,10,17,18,24,30,33-nonamethyl-9-[(4-methylphenyl)methyl]-23-(2-methylpropyl)-2,5,8,11,16,19,22,25,31,34,37-undecaoxospiro[27-thia-1,4,7,10,15,18,21,24,30,33,36-undecazatricyclo[36.3.0.0¹²,¹⁵]hentetracontane-35,1'-cyclopentane]-29-carboxamide, (2178) (3S,9S,18S,21S,27R,30S,36S)-18,30-bis[(2S)-butan-2-yl]-3-[2-[3-chloro-4-(trifluoromethyl)phenyl]ethyl]-N,N,7,10,13,16,22,28,31-nonamethyl-9-[(4-methylphenyl)methyl]-21-(2-methylpropyl)-2,5,8,11,14,17,20,23,29,32,35-undecaoxospiro[25-thia-1,4,7,10,13,16,19,22,28,31,34-undecazabicyclo[34.3.0]nonatriacontane-33,1'-cyclopentane]-27-carboxamide, (2179) (3S,9S,12S,17S,20S,23S,29R,32S,38S)-20-[(2S)-butan-2-yl]-9,32-dicyclopentyl-3-[2-[3-fluoro-4-(trifluoromethyl)phenyl]ethyl]-N,N,7,10,17,18,24,30,33-nonamethyl-23-(2-methylpropyl)-2,5,8,11,16,19,22,25,31,34,37-undecaoxospiro[27-thia-1,4,7,10,15,18,21,24,30,33,36-undecazatricyclo[36.3.0.0¹²,¹⁵]hentetracontane-35,1'-cyclopentane]-29-carboxamide, (2180) (11S,17S,26S,29S,33S,36S)-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-9-[2-(4-methylpiperazin-1-yl)ethyl]-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, (2181) (3S,6S,9S,13S,16S,31S,34S)-25-[2-[3-chloro-4-(trifluoromethyl)phenyl]ethyl]-23-[2-[2-(dimethylamino)ethoxy]ethyl]-9-isobutyl-N,N,3,4,10,14,17,29,32-nonamethyl-6,16-bis[(1S)-1-methylpropyl]-2,5,8,11,15,18,21, 24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide, (2182) (3S,6S,9S,13S,16S,25S,31S,34S)-23-[2-(azetidin-3-yl)ethyl]-31-(cyclohexylmethyl)-16-cyclopentyl-25-[2-[3-fluoro-4-(trifluoromethyl)phenyl]ethyl]-9-isobutyl-N,N,3,4,10,14,17,29,32-nonamethyl-6-[(1S)-1-methylpropyl]-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide, (2183) (3S,6S,9S,13S,16S,25S,31S,34S)-25-[2-[3-chloro-4-(trifluoromethyl)phenyl]ethyl]-31-(cyclohexylmethyl)-16-cyclopentyl-9-isobutyl-N,N,3,4,10,14,17,29,32-nonamethyl-23-[2-[2-(methylamino)ethoxy]ethyl]-6-[(1S)-1-methylpropyl]-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide, (2184) (11S,17S,26S,29S,33S,36S)-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-9-(2-piperazin-1-ylethyl)-33-(piperidine-1-carbonyl)-6,9,12,15,18,21,24,27,30,34,37-undecazaspiro[4.33]octatriacontane-7,10,13,16,19,22,25,28,31,35,38-undecone, (2185) (11S,17S,26S,29S,33S,36S)-9-[2-(2-aminoethoxy)ethyl]-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone, and (2186) (11S,17S,26S,29S,33S,36S)-9-(4-aminobutyl)-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone.

The present invention also relates to a non-natural amino acid for use in the production of the cyclic peptide compound of the present invention. In an embodiment, the non-natural amino acid of the present invention is an N-protected non-natural amino acid for use in the production of the peptide compound using a solid-phase synthesis method, and in another embodiment, the non-natural amino acid of the present invention is a non-natural amino acid having a free amino group obtained by removing the protecting group from the N-protected non-natural amino acid. Examples of the protecting group of the N-protected non-natural amino acid include an Fmoc group, a Boc group, a Cbz group, an Alloc group, a nosyl group, a dinitronosyl group, a t-Bu group, a trityl group, and a cumyl group. Of these, an Fmoc group, a Boc group, a Cbz group, and an Alloc group are preferable, and an Fmoc group is more preferable.

In the present invention, specific examples of the N-protected non-natural amino acid having an Fmoc group as a protecting group include the following amino acids.

(001_aa053) 3-borono-2-(9H-fluoren-9-ylmethoxycarbonylamino)propanoic acid,
(002_aa134) 4-[3,5-difluoro-4-(trifluoromethyl)phenyl]-2-(9H-fluoren-9-ylmethoxycarbonylamino)butanoic acid,
(003_aa133) 2-(9H-fluoren-9-ylmethoxycarbonylamino)-4-[3-fluoro-4-(trifluoromethyl)phenyl]butanoic acid,
(004_aa132) 4-[3-chloro-4-(trifluoromethyl)phenyl]-2-(9H-fluoren-9-ylmethoxycarbonylamino)butanoic acid,
(005_aa049) 2-(9H-fluoren-9-ylmethoxycarbonylamino)-4-[4-(pentafluoro-$_6$-sulfanyl)phenyl]butanoic acid,
(006_aa154) 2-[9H-fluoren-9-ylmethoxycarbonyl(methyl)amino]-3-(3-iodophenyl)propanoic acid,
(007_aa151) 3-(3,4-difluorophenyl)-2-[9H-fluoren-9-ylmethoxycarbonyl(methyl)amino]propanoic acid,
(008_aa128) 3-(5-bromo-2-methyl-phenyl)-2-(9H-fluoren-9-ylmethoxycarbonylamino)propanoic acid,
(009_aa127) 2-(9H-fluoren-9-ylmethoxycarbonylamino)-3-(5-iodo-2-methyl-phenyl)propanoic acid,
(010_aa126) 3-(2-bromo-5-iodo-phenyl)-2-(9H-fluoren-9-ylmethoxycarbonylamino)propanoic acid,
(011_aa122) 3-(2-chloro-5-iodo-phenyl)-2-(9H-fluoren-9-ylmethoxycarbonylamino)propanoic acid,
(012_aa121) 2-(9H-fluoren-9-ylmethoxycarbonylamino)-3-(2-fluoro-5-iodo-phenyl)propanoic acid,
(013_aa120) 3-(3,5-dichlorophenyl)-2-(9H-fluoren-9-ylmethoxycarbonylamino)propanoic acid,
(014_aa118) 3-(2,5-difluorophenyl)-2-(9H-fluoren-9-ylmethoxycarbonylamino)propanoic acid,
(015_aa116) 3-(2,6-difluorophenyl)-2-(9H-fluoren-9-ylmethoxycarbonylamino)propanoic acid,
(016_aa114) 2-[ethyl(9H-fluoren-9-ylmethoxycarbonyl)amino]-3-[4-(trifluoromethyl)phenyl]propanoic acid,
(017_aa113) 2-[ethyl(9H-fluoren-9-ylmethoxycarbonyl)amino]-3-(p-tolyl)propanoic acid,
(018_aa110) 3-(4-chlorophenyl)-2-[ethyl(9H-fluoren-9-ylmethoxycarbonyl)amino]propanoic acid,
(019_aa106) 2-(9H-fluoren-9-ylmethoxycarbonylamino)-3-(3-fluoro-5-iodo-phenyl)propanoic acid,
(020_aa105) 2-(9H-fluoren-9-ylmethoxycarbonylamino)-3-(2-fluoro-3-iodo-phenyl)propanoic acid,
(021_aa104) 3-(3-chloro-5-iodo-phenyl)-2-(9H-fluoren-9-ylmethoxycarbonylamino)propanoic acid,
(022_aa097) 3-(3-bromophenyl)-2-[9H-fluoren-9-ylmethoxycarbonyl(methyl)amino]propanoic acid,
(023_aa096) 2-[9H-fluoren-9-ylmethoxycarbonyl(methyl)amino]-3-(4-iodophenyl)propanoic acid,
(024_aa095) 2-[9H-fluoren-9-ylmethoxycarbonyl(methyl)amino]-3-(2-fluorophenyl)propanoic acid,
(025_aa094) 3-(2-chlorophenyl)-2-[9H-fluoren-9-ylmethoxycarbonyl(methyl)amino]propanoic acid,
(026_aa090) 2-[9H-fluoren-9-ylmethoxycarbonyl(methyl)amino]-3-[4-(trifluoromethyl)phenyl]propanoic acid,
(027_aa087) 2-[9H-fluoren-9-ylmethoxycarbonyl(methyl)amino]-3-[3-(trifluoromethoxy)phenyl]propanoic acid,
(028_aa086) 3-(4-bromophenyl)-2-[9H-fluoren-9-ylmethoxycarbonyl(methyl)amino]propanoic acid,
(029_aa085) 2-[9H-fluoren-9-ylmethoxycarbonyl(methyl)amino]-3-(p-tolyl)propanoic acid,
(030_aa082) 2-[9H-fluoren-9-ylmethoxycarbonyl(methyl)amino]-3-(4-fluorophenyl)propanoic acid,
(031_aa081) 2-[9H-fluoren-9-ylmethoxycarbonyl(methyl)amino]-3-[4-(trifluoromethoxy)phenyl]propanoic acid,
(032_aa080) 2-[9H-fluoren-9-ylmethoxycarbonyl(methyl)amino]-3-(3-fluorophenyl)propanoic acid,
(033_aa077) 2-[9H-fluoren-9-ylmethoxycarbonyl(methyl)amino]-3-(o-tolyl)propanoic acid,
(034_aa074) 2-[9H-fluoren-9-ylmethoxycarbonyl(methyl)amino]-3-[2-(trifluoromethoxy)phenyl]propanoic acid,
(035_aa073) 2-[9H-fluoren-9-ylmethoxycarbonyl(methyl)amino]-3-[3-(trifluoromethyl)phenyl]propanoic acid,
(036_aa067) 2-[9H-fluoren-9-ylmethoxycarbonyl(methyl)amino]-3-(2-methoxyphenyl)propanoic acid,
(037_aa066) 3-[4-(difluoromethyl)phenyl]-2-[9H-fluoren-9-ylmethoxycarbonyl(methyl)amino]propanoic acid, (038_aa064) 3-(2-cyanophenyl)-2-[9H-fluoren-9-ylmethoxycarbonyl(methyl)amino]propanoic acid,
(039_aa063) 2-[9H-fluoren-9-ylmethoxycarbonyl(methyl)amino]-3-[2-(trifluoromethyl)phenyl]propanoic acid,
(040_aa061) 3-(4-cyanophenyl)-2-[9H-fluoren-9-ylmethoxycarbonyl(methyl)amino]propanoic acid,
(041_aa060) 3-(3-cyanophenyl)-2-[9H-fluoren-9-ylmethoxycarbonyl(methyl)amino]propanoic acid,
(042_aa108) 3-(9H-fluoren-9-ylmethoxycarbonylamino)-4-isopentyloxy-butanoic acid,
(043_aa107) 4-[2-(tert-butylamino)-2-oxo-ethoxy]-3-(9H-fluoren-9-ylmethoxycarbonylamino)butanoic acid,
(044_aa119) 2-(9H-fluoren-9-ylmethoxycarbonylamino)-3-(3-iodophenyl)-2-methyl-propanoic acid,
(045_aa098) 2-[9H-fluoren-9-ylmethoxycarbonyl(methyl)amino]-2-methyl-3-phenyl-propanoic acid,
(046_aa088) 1-[9H-fluoren-9-ylmethoxycarbonyl(methyl)amino]cyclopentanecarboxylic acid,
(047_aa102) 1-(9H-fluoren-9-ylmethoxycarbonyl)-4-hydroxy-pyrrolidine-2-carboxylic acid,
(048_aa101) 1-(9H-fluoren-9-ylmethoxycarbonyl)-4-hydroxy-pyrrolidine-2-carboxylic acid,
(049_aa149) 3-(9H-fluoren-9-ylmethoxycarbonylamino)-4-oxo-4-(1-piperidyl)butanoic acid,
(050_aa052) 3-[9H-fluoren-9-ylmethoxycarbonyl(propyl)amino]-4-oxo-4-(1-piperidyl)butanoic acid,
(051_aa033-b) 4-allyloxy-2-[9H-fluoren-9-ylmethoxycarbonyl(methyl)amino]-4-oxo-butanoic acid,
(052_aa032) 3-[ethyl(9H-fluoren-9-ylmethoxycarbonyl)amino]-4-oxo-4-(1-piperidyl)butanoic acid,
(053_aa031) 3-[9H-fluoren-9-ylmethoxycarbonyl(methyl)amino]-4-oxo-4-pyrrolidin-1-yl-butanoic acid,
(054_aa030) 3-[9H-fluoren-9-ylmethoxycarbonyl(methyl)amino]-4-oxazolidin-3-yl-4-oxo-butanoic acid,
(055_aa029) 3-(9H-fluoren-9-ylmethoxycarbonylamino)-4-oxazolidin-3-yl-4-oxo-butanoic acid,
(056_aa028) 3-((((9H-fluoren-9-yl)methoxy)carbonyl)(methyl)amino)-4-oxo-4-(3,3,4,4-tetrafluoropyrrolidin-1-yl)butanoic acid,
(057_aa027) 3-(9H-fluoren-9-ylmethoxycarbonylamino)-4-oxo-4-(3,3,4,4-tetrafluoropyrrolidin-1-yl)butanoic acid,
(058_aa026) 3-(9H-fluoren-9-ylmethoxycarbonylamino)-4-(3,3,4,4,5,5-hexafluoro-1-piperidyl)-4-oxo-butanoic acid,
(059_aa025) 3-[9H-fluoren-9-ylmethoxycarbonyl(methyl)amino]-4-(3,3,4,4,5,5-hexafluoro-1-piperidyl)-4-oxo-butanoic acid,
(060_aa024) 4-(3,3-dimethylpyrrolidin-1-yl)-3-(9H-fluoren-9-ylmethoxycarbonylamino)-4-oxo-butanoic acid,
(061_aa023) 3-(9H-fluoren-9-ylmethoxycarbonylamino)-4-(4-methyl-1-piperidyl)-4-oxo-butanoic acid,
(062_aa022) 3-(9H-fluoren-9-ylmethoxycarbonylamino)-4-morpholino-4-oxo-butanoic acid,
(063_aa021) 4-(1,1-dioxo-1,4-thiazinan-4-yl)-3-(9H-fluoren-9-ylmethoxycarbonylamino)-4-oxo-butanoic acid,
(064_aa020) 4-(4-tert-butyl-1-piperidyl)-3-(9H-fluoren-9-ylmethoxycarbonylamino)-4-oxo-butanoic acid,
(065_aa019) 4-(dimethylamino)-3-(9H-fluoren-9-ylmethoxycarbonylamino)-4-oxo-butanoic acid,
(066_aa018) 3-(9H-fluoren-9-ylmethoxycarbonylamino)-4-oxo-4-pyrrolidin-1-yl-butanoic acid,
(067_aa017) 3-(9H-fluoren-9-ylmethoxycarbonylamino)-4-(3-oxa-8-azabicyclo[3.2.1]octan-8-yl)-4-oxo-butanoic acid,
(068_aa016) 3-(9H-fluoren-9-ylmethoxycarbonylamino)-4-[4-(oxetan-3-yl)piperazin-1-yl]-4-oxo-butanoic acid,
(069_aa015) 4-(1,1-dioxo-1,4-thiazinan-4-yl)-3-[9H-fluoren-9-ylmethoxycarbonyl(methyl)amino]-4-oxo-butanoic acid,
(070_aa014) 3-[9H-fluoren-9-ylmethoxycarbonyl(methyl)amino]-4-(4-methyl-1-piperidyl)-4-oxo-butanoic acid,
(071_aa013) 3-[9H-fluoren-9-ylmethoxycarbonyl(methyl)amino]-4-oxo-4-pyrrolidin-1-yl-butanoic acid,
(072_aa012) 4-(azetidin-1-yl)-3-[9H-fluoren-9-ylmethoxycarbonyl(methyl)amino]-4-oxo-butanoic acid,
(073_aa011) 4-(dimethylamino)-3-[9H-fluoren-9-ylmethoxycarbonyl(methyl)amino]-4-oxo-butanoic acid,
(074_aa010) 3-[9H-fluoren-9-ylmethoxycarbonyl(methyl)amino]-4-(3-oxa-8-azabicyclo[3.2.1]octan-8-yl)-4-oxo-butanoic acid,
(075_aa009) 3-[9H-fluoren-9-ylmethoxycarbonyl(methyl)amino]-4-[4-(oxetan-3-yl)piperazin-1-yl]-4-oxo-butanoic acid,
(076_aa008) 4-(3,3-dimethylpyrrolidin-1-yl)-3-[9H-fluoren-9-ylmethoxycarbonyl(methyl)amino]-4-oxo-butanoic acid,
(077_aa007) 3-[9H-fluoren-9-ylmethoxycarbonyl(methyl)amino]-4-morpholino-4-oxo-butanoic acid,
(078_aa006) 3-[9H-fluoren-9-ylmethoxycarbonyl(methyl)amino]-4-oxo-4-(1-piperidyl)butanoic acid,
(079_aa040) 2-[9H-fluoren-9-ylmethoxycarbonyl(methyl)amino]-4-(4-pyridyl)butanoic acid,
(080_aa039) 2-[9H-fluoren-9-ylmethoxycarbonyl(methyl)amino]-4-(3-pyridyl)butanoic acid,
(081_aa125) 3-(5-bromo-2-thienyl)-2-(9H-fluoren-9-ylmethoxycarbonylamino)propanoic acid,
(082_aa124) 3-(5-chloro-2-thienyl)-2-(9H-fluoren-9-ylmethoxycarbonylamino)propanoic acid,
(083_aa068) 2-[9H-fluoren-9-ylmethoxycarbonyl(methyl)amino]-3-(3-pyridyl)propanoic acid,
(084_aa065) 2-[9H-fluoren-9-ylmethoxycarbonyl(methyl)amino]-3-(4-pyridyl)propanoic acid,
(085_aa038) 3-(5-bromo-3-pyridyl)-2-(9H-fluoren-9-ylmethoxycarbonylamino)propanoic acid,
(086_aa037) 2-[9H-fluoren-9-ylmethoxycarbonyl(methyl)amino]-3-(6-methyl-3-pyridyl)propanoic acid,
(087_aa036) 2-[9H-fluoren-9-ylmethoxycarbonyl(methyl)amino]-3-(6-methoxy-3-pyridyl)propanoic acid,
(088_aa035) 2-[9H-fluoren-9-ylmethoxycarbonyl(methyl)amino]-3-(5-methyl-3-pyridyl)propanoic acid,
(089_aa034) 2-[9H-fluoren-9-ylmethoxycarbonyl(methyl)amino]-3-(5-methoxy-3-pyridyl)propanoic acid,
(090_aa033) 2-[9H-fluoren-9-ylmethoxycarbonyl(methyl)amino]-3-[6-(trifluoromethyl)-3-pyridyl]propanoic acid,
(091_aa153) 4-(3,3-difluoroazetidin-1-yl)-2-[9H-fluoren-9-ylmethoxycarbonyl(methyl)amino]-4-oxo-butanoic acid,
(092_aa152) 4-(4,4-difluoro-1-piperidyl)-2-[9H-fluoren-9-ylmethoxycarbonyl(methyl)amino]-4-oxo-butanoic acid,
(093_aa092) 2-[9H-fluoren-9-ylmethoxycarbonyl(methyl)amino]-4-methylsulfonyl-butanoic acid,
(094_aa047) 4-(3,3-difluoroazetidin-1-yl)-2-[9H-fluoren-9-ylmethoxycarbonyl(methyl)amino]butanoic acid,
(095_aa093) 2-[9H-fluoren-9-ylmethoxycarbonyl(methyl)amino]-3-methoxy-butanoic acid,
(096_aa078) 2-[9H-fluoren-9-ylmethoxycarbonyl(methyl)amino]-4-methoxy-butanoic acid,
(097_aa069) 3-(cyclopropoxy)-2-[9H-fluoren-9-ylmethoxycarbonyl(methyl)amino]propanoic acid,
(098_aa062) 2-[9H-fluoren-9-ylmethoxycarbonyl(methyl)amino]-3-methoxy-propanoic acid,
(099_aa055) 2-[9H-fluoren-9-ylmethoxycarbonyl(methyl)amino]-3-isopentyloxy-propanoic acid, (100_aa054) 2-[9H-fluoren-9-ylmethoxycarbonyl(methyl)amino]-3-hydroxy-propanoic acid,
(101_aa045) 2-[9H-fluoren-9-ylmethoxycarbonyl(methyl)amino]-3-(2,2,2-trifluoroethoxy)propanoic acid,
(102_aa044) 2-(9H-fluoren-9-ylmethoxycarbonylamino)-3-(2,2,2-trifluoroethoxy)propanoic acid,
(103_aa043) 3-(cyclobutoxy)-2-(9H-fluoren-9-ylmethoxycarbonylamino)propanoic acid,
(104_aa042) 3-(cyclobutoxy)-2-[9H-fluoren-9-ylmethoxycarbonyl(methyl)amino]propanoic acid,
(105_aa041) 3-(cyclopropoxy)-2-(9H-fluoren-9-ylmethoxycarbonylamino)propanoic acid,
(106_aa150) 2-[9H-fluoren-9-ylmethoxycarbonyl(methyl)amino]-5,5-difluoro-pentanoic acid,
(107_aa091) 2-[9H-fluoren-9-ylmethoxycarbonyl(methyl)amino]-4,4,4-trifluoro-butanoic acid,
(108_aa089) 2-cyclopropyl-2-[9H-fluoren-9-ylmethoxycarbonyl(methyl)amino]acetic acid,
(109_aa079) 2-cyclopentyl-2-[9H-fluoren-9-ylmethoxycarbonyl(methyl)amino]acetic acid,
(110_aa075) 2-cyclobutyl-2-[9H-fluoren-9-ylmethoxycarbonyl(methyl)amino]acetic acid,
(111_aa083) 2-[9H-fluoren-9-ylmethoxycarbonyl(methyl)amino]pent-4-ynoic acid,
(112_aa076) 2-[9H-fluoren-9-ylmethoxycarbonyl(methyl)amino]hex-5-ynoic acid,
(113_aa048) 2-[9H-fluoren-9-ylmethoxycarbonyl(methyl)amino]pent-4-enoic acid,
(114_aa141) 3-(9H-fluoren-9-ylmethoxycarbonylamino)-5-methyl-hexanoic acid,
(115_aa131) 2-[9H-fluoren-9-ylmethoxycarbonyl(methyl)amino]-5-methyl-hexanoic acid,
(116_aa130) 2-[9H-fluoren-9-ylmethoxycarbonyl(methyl)amino]octanoic acid,
(117_aa112) 3-cyclohexyl-2-[ethyl(9H-fluoren-9-ylmethoxycarbonyl)amino]propanoic acid,
(118_aa111) 2-[ethyl(9H-fluoren-9-ylmethoxycarbonyl)amino]-4-methyl-pentanoic acid,
(119_aa109) 2-[ethyl(9H-fluoren-9-ylmethoxycarbonyl)amino]propanoic acid,
(120_aa084) 2-[9H-fluoren-9-ylmethoxycarbonyl(methyl)amino]heptanoic acid,
(121_aa072) 3-cyclobutyl-2-[9H-fluoren-9-ylmethoxycarbonyl(methyl)amino]propanoic acid,
(122_aa071) 3-cyclopentyl-2-[9H-fluoren-9-ylmethoxycarbonyl(methyl)amino]propanoic acid,
(123_aa070) 3-cyclopropyl-2-[9H-fluoren-9-ylmethoxycarbonyl(methyl)amino]propanoic acid,
(124_aa051) 3-[9H-fluoren-9-ylmethoxycarbonyl(methyl)amino]-5-methyl-hexanoic acid,
(125_aa050) 2-[9H-fluoren-9-ylmethoxycarbonyl(propyl)amino]propanoic acid,
(126_aa004) 2-[9H-fluoren-9-ylmethoxycarbonyl(isopropyl)amino]acetic acid,
(127_aa003) 2-[cyclopropyl(9H-fluoren-9-ylmethoxycarbonyl)amino]acetic acid,
(128_aa002) 2-[2-(4,4-difluoro-1-piperidyl)ethyl-(9H-fluoren-9-ylmethoxycarbonyl)amino]acetic acid,
(129_aa001) 2-[3-(4,4-difluoro-1-piperidyl)propyl-(9H-fluoren-9-ylmethoxycarbonyl)amino]acetic acid,
(130_aa155) 2-[3-(dimethylamino)-2-[9H-fluoren-9-ylmethoxycarbonyl(methyl)amino]-3-oxo-propyl]sulfanylacetic acid,
(131_aa157) 2-[2-(azetidin-3-yl)ethyl-(9H-fluoren-9-ylmethoxycarbonyl)amino]acetic acid,
(132_aa158) 2-[2-(2-aminoethoxy)ethyl-(9H-fluoren-9-ylmethoxycarbonyl)amino]acetic acid, and
(133_aa161) 2-[9H-fluoren-9-ylmethoxycarbonyl-[2-[2-(methylamino)ethoxy]ethyl]amino]acetic acid.

In the present invention, specific examples of the N-protected non-natural amino acid having a Cbz group as a protecting group include the following amino acids.
(z001) 2-(benzyloxycarbonylamino)-3-borono-propanoic acid,
(z002) 2-(benzyloxycarbonylamino)-4-[3,5-difluoro-4-(trifluoromethyl)phenyl]butanoic acid,
(z003) 2-(((benzyloxy)carbonyl)amino)-4-(3-fluoro-4-(trifluoromethyl)phenyl)butanoic acid,
(z004) 2-(((benzyloxy)carbonyl)amino)-4-(3-chloro-4-(trifluoromethyl)phenyl)butanoic acid,
(z005) 2-(benzyloxycarbonylamino)-4-[4-(pentafluoro-$\lambda^6$-sulfanyl)phenyl]butanoic acid,
(z006) 2-[benzyloxycarbonyl(methyl)amino]-3-(3-iodophenyl)propanoic acid,
(z007) 2-[benzyloxycarbonyl(methyl)amino]-3-(3,4-difluorophenyl)propanoic acid,
(z008) 2-(((benzyloxy)carbonyl)amino)-3-(5-bromo-2-methylphenyl)propanoic acid,
(z009) 2-(benzyloxycarbonylamino)-3-(5-iodo-2-methylphenyl)propanoic acid,
(z010) 2-(((benzyloxy)carbonyl)amino)-3-(2-bromo-5-iodophenyl)propanoic acid,
(z011) 2-(((benzyloxy)carbonyl)amino)-3-(2-chloro-5-iodophenyl)propanoic acid,
(z012) 2-(((benzyloxy)carbonyl)amino)-3-(2-fluoro-5-iodophenyl)propanoic acid,
(z013) 2-(((benzyloxy)carbonyl)amino)-3-(3,5-dichlorophenyl)propanoic acid,
(z014) 2-(((benzyloxy)carbonyl)amino)-3-(2,5-difluorophenyl)propanoic acid,
(z015) 2-(((benzyloxy)carbonyl)amino)-3-(2,6-difluorophenyl)propanoic acid,
(z016) 2-[benzyloxycarbonyl(ethyl)amino]-3-[4-(trifluoromethyl)phenyl]propanoic acid,
(z017) 2-[benzyloxycarbonyl(ethyl)amino]-3-(p-tolyl)propanoic acid,
(z018) 2-[benzyloxycarbonyl(ethyl)amino]-3-(4-chlorophenyl)propanoic acid,
(z019) 2-(((benzyloxy)carbonyl)amino)-3-(3-fluoro-5-iodophenyl)propanoic acid,
(z020) 2-(benzyloxycarbonylamino)-3-(2-fluoro-3-iodophenyl)propanoic acid,
(z021) 2-(benzyloxycarbonylamino)-3-(3-chloro-5-iodophenyl)propanoic acid,
(z022) 2-[benzyloxycarbonyl(methyl)amino]-3-(3-bromophenyl)propanoic acid,
(z023) 2-[benzyloxycarbonyl(methyl)amino]-3-(4-iodophenyl)propanoic acid,
(z024) 2-[benzyloxycarbonyl(methyl)amino]-3-(2-fluorophenyl)propanoic acid,
(z025) 2-[benzyloxycarbonyl(methyl)amino]-3-(2-chlorophenyl)propanoic acid,
(z026) 2-[benzyloxycarbonyl(methyl)amino]-3-[4-(trifluoromethyl)phenyl]propanoic acid,
(z027) 2-[benzyloxycarbonyl(methyl)amino]-3-[3-(trifluoromethoxy)phenyl]propanoic acid,
(z028) 2-[benzyloxycarbonyl(methyl)amino]-3-(4-bromophenyl)propanoic acid,
(z029) 2-[benzyloxycarbonyl(methyl)amino]-3-(p-tolyl)propanoic acid,
(z030) 2-[benzyloxycarbonyl(methyl)amino]-3-(4-fluorophenyl)propanoic acid,
(z031) 2-[benzyloxycarbonyl(methyl)amino]-3-[4-(trifluoromethoxy)phenyl]propanoic acid, (z032) 2-[benzyloxycarbonyl(methyl)amino]-3-(3-fluorophenyl)propanoic acid,
(z033) 2-[benzyloxycarbonyl(methyl)amino]-3-(o-tolyl)propanoic acid,
(z034) 2-[benzyloxycarbonyl(methyl)amino]-3-[2-(trifluoromethoxy)phenyl]propanoic acid,
(z035) 2-[benzyloxycarbonyl(methyl)amino]-3-[3-(trifluoromethyl)phenyl]propanoic acid,
(z036) 2-[benzyloxycarbonyl(methyl)amino]-3-(2-methoxyphenyl)propanoic acid,
(z037) 2-[benzyloxycarbonyl(methyl)amino]-3-[4-(difluoromethyl)phenyl]propanoic acid,
(z038) 2-[benzyloxycarbonyl(methyl)amino]-3-(2-cyanophenyl)propanoic acid,
(z039) 2-[benzyloxycarbonyl(methyl)amino]-3-[2-(trifluoromethyl)phenyl]propanoic acid,
(z040) 2-[benzyloxycarbonyl(methyl)amino]-3-(4-cyanophenyl)propanoic acid,
(z041) 2-[benzyloxycarbonyl(methyl)amino]-3-(3-cyanophenyl)propanoic acid,
(z042) 3-(benzyloxycarbonylamino)-4-isopentyloxy-butanoic acid,
(z043) 3-(benzyloxycarbonylamino)-4-[2-(tert-butylamino)-2-oxo-ethoxy]butanoic acid,
(z044) 2-(((benzyloxy)carbonyl)amino)-3-(3-iodophenyl)-2-methylpropanoic acid,
(z045) 2-(((benzyloxy)carbonyl)(methyl)amino)-2-methyl-3-phenylpropanoic acid,
(z046) 1-[benzyloxycarbonyl(methyl)amino]cyclopentanecarboxylic acid,
(z047) 1-((benzyloxy)carbonyl)-4-hydroxypyrrolidine-2-carboxylic acid,
(z048) 1-((benzyloxy)carbonyl)-4-hydroxypyrrolidine-2-carboxylic acid,
(z049) 3-(((benzyloxy)carbonyl)amino)-4-oxo-4-(piperidin-1-yl)butanoic acid,
(z050) 3-[benzyloxycarbonyl(propyl)amino]-4-oxo-4-(1-piperidyl)butanoic acid,
(z051) 4-allyloxy-2-[benzyloxycarbonyl(methyl)amino]-4-oxo-butanoic acid,
(z052) 3-[benzyloxycarbonyl(ethyl)amino]-4-oxo-4-(1-piperidyl)butanoic acid,
(z053) 3-[benzyloxycarbonyl(methyl)amino]-4-oxo-4-pyrrolidin-1-yl-butanoic acid,
(z054) 3-[benzyloxycarbonyl(methyl)amino]-4-oxazolidin-3-yl-4-oxo-butanoic acid,
(z055) 3-(benzyloxycarbonylamino)-4-oxazolidin-3-yl-4-oxo-butanoic acid,
(z056) 3-[benzyloxycarbonyl(methyl)amino]-4-oxo-4-(3,3,4,4-tetrafluoropyrrolidin-1-yl)butanoic acid,
(z057) 3-(((benzyloxy)carbonyl)amino)-4-oxo-4-(3,3,4,4-tetrafluoropyrrolidin-1-yl)butanoic acid,
(z058) 3-(benzyloxycarbonylamino)-4-(3,3,4,4,5,5-hexafluoro-1-piperidyl)-4-oxo-butanoic acid,
(z059) 3-[benzyloxycarbonyl(methyl)amino]-4-(3,3,4,4,5,5-hexafluoro-1-piperidyl)-4-oxo-butanoic acid,
(z060) 3-(((benzyloxy)carbonyl)amino)-4-(3,3-dimethylpyrrolidin-1-yl)-4-oxobutanoic acid,
(z061) 3-(((benzyloxy)carbonyl)amino)-4-(4-methylpiperidin-1-yl)-4-oxobutanoic acid,
(z062) 3-(((benzyloxy)carbonyl)amino)-4-morpholino-4-oxobutanoic acid,
(z063) 3-(((benzyloxy)carbonyl)amino)-4-(1,1-dioxidothiomorpholino)-4-oxobutanoic acid,
(z064) 3-(((benzyloxy)carbonyl)amino)-4-(4-(tert-butyl)piperidin-1-yl)-4-oxobutanoic acid,
(z065) 3-(((benzyloxy)carbonyl)amino)-4-oxo-4-(pyrrolidin-1-yl)butanoic acid,
(z066) 3-(((benzyloxy)carbonyl)amino)-4-oxo-4-(pyrrolidin-1-yl)butanoic acid,
(z067) 3-(benzyloxycarbonylamino)-4-(3-oxa-8-azabicyclo[3.2.1]octan-8-yl)-4-oxo-butanoic acid,
(z068) 3-(benzyloxycarbonylamino)-4-[4-(oxetan-3-yl)piperazin-1-yl]-4-oxo-butanoic acid,
(z069) 3-[benzyloxycarbonyl(methyl)amino]-4-(1,1-dioxo-1,4-thiazinan-4-yl)-4-oxo-butanoic acid,
(z070) 3-[benzyloxycarbonyl(methyl)amino]-4-(4-methyl-1-piperidyl)-4-oxo-butanoic acid,
(z071) 3-[benzyloxycarbonyl(methyl)amino]-4-oxo-4-pyrrolidin-1-yl-butanoic acid,
(z072) 4-(azetidin-1-yl)-3-[benzyloxycarbonyl(methyl)amino]-4-oxo-butanoic acid,
(z073) 3-[benzyloxycarbonyl(methyl)amino]-4-(dimethylamino)-4-oxo-butanoic acid,
(z074) 3-[benzyloxycarbonyl(methyl)amino]-4-(3-oxa-8-azabicyclo[3.2.1]octan-8-yl)-4-oxo-butanoic acid,
(z075) 3-[benzyloxycarbonyl(methyl)amino]-4-[4-(oxetan-3-yl)piperazin-1-yl]-4-oxo-butanoic acid,
(z076) 3-[benzyloxycarbonyl(methyl)amino]-4-(3,3-dimethylpyrrolidin-1-yl)-4-oxo-butanoic acid,
(z077) 3-[benzyloxycarbonyl(methyl)amino]-4-morpholino-4-oxo-butanoic acid,
(z078) 3-(((benzyloxy)carbonyl)(methyl)amino)-4-oxo-4-(piperidin-1-yl)butanoic acid,
(z079) 2-[benzyloxycarbonyl(methyl)amino]-4-(4-pyridyl)butanoic acid,
(z080) 2-[benzyloxycarbonyl(methyl)amino]-4-(3-pyridyl)butanoic acid,
(z081) 2-(((benzyloxy)carbonyl)amino)-3-(5-bromothiophen-2-yl)propanoic acid,
(z082) 2-(((benzyloxy)carbonyl)amino)-3-(5-chlorothiophen-2-yl)propanoic acid,
(z083) 2-[benzyloxycarbonyl(methyl)amino]-3-(3-pyridyl)propanoic acid,
(z084) 2-[benzyloxycarbonyl(methyl)amino]-3-(4-pyridyl)propanoic acid,
(z085) 2-(((benzyloxy)carbonyl)amino)-3-(5-bromopyridin-3-yl)propanoic acid,
(z086) 2-[benzyloxycarbonyl(methyl)amino]-3-(6-methyl-3-pyridyl)propanoic acid,
(z087) 2-[benzyloxycarbonyl(methyl)amino]-3-(6-methoxy-3-pyridyl)propanoic acid,
(z088) 2-[benzyloxycarbonyl(methyl)amino]-3-(5-methyl-3-pyridyl)propanoic acid,
(z089) 2-[benzyloxycarbonyl(methyl)amino]-3-(5-methoxy-3-pyridyl)propanoic acid,
(z090) 2-[benzyloxycarbonyl(methyl)amino]-3-[6-(trifluoromethyl)-3-pyridyl]propanoic acid,
(z091) 2-[benzyloxycarbonyl(methyl)amino]-4-(3,3-difluoroazetidin-1-yl)-4-oxo-butanoic acid,
(z092) 2-[benzyloxycarbonyl(methyl)amino]-4-(4,4-difluoro-1-piperidyl)-4-oxo-butanoic acid,
(z093) 2-[benzyloxycarbonyl(methyl)amino]-4-methylsulfonyl-butanoic acid,
(z094) 2-[benzyloxycarbonyl(methyl)amino]-4-(3,3-difluoroazetidin-1-yl)butanoic acid,
(z095) (2S,3R)-2-[benzyloxycarbonyl(methyl)amino]-3-methoxy-butanoic acid,
(z096) 2-[benzyloxycarbonyl(methyl)amino]-4-methoxy-butanoic acid,
(z097) 2-[benzyloxycarbonyl(methyl)amino]-3-(cyclopropoxy)propanoic acid, (z098) 2-[benzyloxycarbonyl(methyl)amino]-3-methoxy-propanoic acid,
(z099) 2-[benzyloxycarbonyl(methyl)amino]-3-isopentyloxy-propanoic acid,
(z100) 2-[benzyloxycarbonyl(methyl)amino]-3-hydroxy-propanoic acid,
(z101) 2-[benzyloxycarbonyl(methyl)amino]-3-(2,2,2-trifluoroethoxy)propanoic acid,
(z102) 2-(benzyloxycarbonylamino)-3-(2,2,2-trifluoroethoxy)propanoic acid,
(z103) 2-(benzyloxycarbonylamino)-3-(cyclobutoxy)propanoic acid,
(z104) 2-[benzyloxycarbonyl(methyl)amino]-3-(cyclobutoxy)propanoic acid,
(z105) 2-(benzyloxycarbonylamino)-3-(cyclopropoxy)propanoic acid,
(z106) 2-[benzyloxycarbonyl(methyl)amino]-5,5-difluoropentanoic acid,
(z107) 2-[benzyloxycarbonyl(methyl)amino]-4,4,4-trifluoro-butanoic acid,
(z108) 2-[benzyloxycarbonyl(methyl)amino]-2-cyclopropyl-acetic acid,
(z109) 2-[benzyloxycarbonyl(methyl)amino]-2-cyclopentyl-acetic acid,
(z110) 2-[benzyloxycarbonyl(methyl)amino]-2-cyclobutyl-acetic acid,
(z111) 2-[benzyloxycarbonyl(methyl)amino]pent-4-ynoic acid,
(z112) 2-[benzyloxycarbonyl(methyl)amino]hex-5-ynoic acid,
(z113) 2-[benzyloxycarbonyl(methyl)amino]pent-4-enoic acid,
(z114) 3-(((benzyloxy)carbonyl)amino)-5-methylhexanoic acid,
(z115) 2-(((benzyloxy)carbonyl)(methyl)amino)-5-methylhexanoic acid,
(z116) 2-(((benzyloxy)carbonyl)(methyl)amino)octanoic acid,
(z117) 2-[benzyloxycarbonyl(ethyl)amino]-3-cyclohexyl-propanoic acid,
(z118) 2-[benzyloxycarbonyl(ethyl)amino]-4-methyl-pentanoic acid,
(z119) N-((benzyloxy)carbonyl)-N-ethyl-alanine,
(z120) 2-[benzyloxycarbonyl(methyl)amino]heptanoic acid,
(z121) 2-[benzyloxycarbonyl(methyl)amino]-3-cyclobutyl-propanoic acid,
(z122) 2-[benzyloxycarbonyl(methyl)amino]-3-cyclopentyl-propanoic acid,
(z123) 2-[benzyloxycarbonyl(methyl)amino]-3-cyclopropyl-propanoic acid,
(z124) 3-(((benzyloxy)carbonyl)(methyl)amino)-5-methylhexanoic acid,
(z125) 2-[benzyloxycarbonyl(propyl)amino]propanoic acid,
(z126) N-((benzyloxy)carbonyl)-N-isopropylglycine
(z127) N-((benzyloxy)carbonyl)-N-cyclopropylglycine
(z128) 2-[benzyloxycarbonyl-[2-(4,4-difluoro-1-piperidyl)ethyl]amino]acetic acid,
(z129) 2-[benzyloxycarbonyl-[3-(4,4-difluoro-1-piperidyl)propyl]amino]acetic acid,
(z130) 2-[2-[benzyloxycarbonyl(methyl)amino]-3-(dimethylamino)-3-oxo-propyl]sulfanylacetic acid,
(z131) 2-[2-(azetidin-3-yl)ethyl-benzyloxycarbonyl-amino]acetic acid,
(z132) 2-[2-(2-aminoethoxy)ethyl-benzyloxycarbonyl-amino]acetic acid, and
(z133) 2-[benzyloxycarbonyl-[2-[2-(methylamino)ethoxy]ethyl]amino]acetic acid.

In the present invention, specific examples of the N-protected non-natural amino acid having a Boc group as a protecting group include the following amino acids:
(b001) 2-[tert-butoxycarbonyl(ethyl)amino]-3-[4-(trifluoromethyl)phenyl]propanoic acid,
(b002) 2-(tert-butoxycarbonylamino)-4-[3,5-difluoro-4-(trifluoromethyl)phenyl]butanoic acid,
(b003) 2-(tert-butoxycarbonylamino)-4-[3-fluoro-4-(trifluoromethyl)phenyl]butanoic acid,
(b004) 2-(tert-butoxycarbonylamino)-4-[3-chloro-4-(trifluoromethyl)phenyl]butanoic acid,
(b005) 2-(tert-butoxycarbonylamino)-4-[4-(pentafluoro-$\lambda^6$-sulfanyl)phenyl]butanoic acid,
(b006) 2-[tert-butoxycarbonyl(methyl)amino]-3-(3-iodophenyl)propanoic acid,
(b007) 2-[tert-butoxycarbonyl(methyl)amino]-3-(3,4-difluorophenyl)propanoic acid,
(b008) 2-(tert-butoxycarbonylamino)-3-(5-bromo-2-methyl-phenyl)propanoic acid,
(b009) 2-(tert-butoxycarbonylamino)-3-(5-iodo-2-methylphenyl)propanoic acid,
(b010) 2-(tert-butoxycarbonylamino)-3-(2-bromo-5-iodophenyl)propanoic acid,
(b011) 2-(tert-butoxycarbonylamino)-3-(2-chloro-5-iodophenyl)propanoic acid,
(b012) 2-(tert-butoxycarbonylamino)-3-(2-fluoro-5-iodophenyl)propanoic acid,
(b013) 2-(tert-butoxycarbonylamino)-3-(3,5-dichlorophenyl)propanoic acid,
(b014) 2-(tert-butoxycarbonylamino)-3-(2,5-difluorophenyl)propanoic acid,
(b015) 2-(tert-butoxycarbonylamino)-3-(2,6-difluorophenyl)propanoic acid,
(b016) 2-[tert-butoxycarbonyl(ethyl)amino]-3-[4-(trifluoromethyl)phenyl]propanoic acid,
(b017) 2-[tert-butoxycarbonyl(ethyl)amino]-3-(p-tolyl)propanoic acid,
(b018) 2-[tert-butoxycarbonyl(ethyl)amino]-3-(4-chlorophenyl)propanoic acid,
(b019) 2-(tert-butoxycarbonylamino)-3-(3-fluoro-5-iodophenyl)propanoic acid,
(b020) 2-(tert-butoxycarbonylamino)-3-(2-fluoro-3-iodophenyl)propanoic acid,
(b021) 2-(tert-butoxycarbonylamino)-3-(3-chloro-5-iodophenyl)propanoic acid,
(b022) 3-(3-bromophenyl)-2-[tert-butoxycarbonyl(methyl)amino]propanoic acid,
(b023) 2-[tert-butoxycarbonyl(methyl)amino]-3-(4-iodophenyl)propanoic acid,
(b024) 2-[tert-butoxycarbonyl(methyl)amino]-3-(2-fluorophenyl)propanoic acid,
(b025) 2-[tert-butoxycarbonyl(methyl)amino]-3-(2-chlorophenyl)propanoic acid,
(b026) 2-[tert-butoxycarbonyl(methyl)amino]-3-[4-(trifluoromethyl)phenyl]propanoic acid,
(b027) 2-[tert-butoxycarbonyl(methyl)amino]-3-[3-(trifluoromethoxy)phenyl]propanoic acid,
(b028) 3-(4-bromophenyl)-2-[tert-butoxycarbonyl(methyl)amino]propanoic acid,
(b029) 2-[tert-butoxycarbonyl(methyl)amino]-3-(p-tolyl)propanoic acid,
(b030) 2-[tert-butoxycarbonyl(methyl)amino]-3-(4-fluorophenyl)propanoic acid,
(b031) 2-[tert-butoxycarbonyl(methyl)amino]-3-[4-(trifluoromethoxy)phenyl]propanoic acid,
(b032) 2-[tert-butoxycarbonyl(methyl)amino]-3-(3-fluorophenyl)propanoic acid, (b033) 2-[tert-butoxycarbonyl(methyl)amino]-3-(o-tolyl)propanoic acid,
(b034) 2-[tert-butoxycarbonyl(methyl)amino]-3-[2-(trifluoromethoxy)phenyl]propanoic acid,
(b035) 2-[tert-butoxycarbonyl(methyl)amino]-3-[3-(trifluoromethyl)phenyl]propanoic acid,
(b036) 2-[tert-butoxycarbonyl(methyl)amino]-3-(2-methoxyphenyl)propanoic acid,
(b037) 2-[tert-butoxycarbonyl(methyl)amino]-3-[4-(difluoromethyl)phenyl]propanoic acid,
(b038) 2-[tert-butoxycarbonyl(methyl)amino]-3-(2-cyanophenyl)propanoic acid,
(b039) 2-[tert-butoxycarbonyl(methyl)amino]-3-[2-(trifluoromethyl)phenyl]propanoic acid,
(b040) 2-[tert-butoxycarbonyl(methyl)amino]-3-(4-cyanophenyl)propanoic acid,
(b041) 2-[tert-butoxycarbonyl(methyl)amino]-3-(3-cyanophenyl)propanoic acid,
(b042) 3-(tert-butoxycarbonylamino)-4-isopentyloxy-butanoic acid,
(b043) 3-(tert-butoxycarbonylamino)-4-[2-(tert-butylamino)-2-oxo-ethoxy]butanoic acid,
(b044) 2-(tert-butoxycarbonylamino)-3-(3-iodophenyl)-2-methyl-propanoic acid,
(b045) 2-[tert-butoxycarbonyl(methyl)amino]-2-methyl-3-phenyl-propanoic acid,
(b046) 1-[tert-butoxycarbonyl(methyl)amino]cyclopentanecarboxylic acid,
(b047) 1-tert-butoxycarbonyl-4-hydroxy-pyrrolidine-2-carboxylic acid,
(b048) 1-tert-butoxycarbonyl-4-hydroxy-pyrrolidine-2-carboxylic acid,
(b049) 3-(tert-butoxycarbonylamino)-4-oxo-4-(1-piperidyl)butanoic acid,
(b050) 3-[tert-butoxycarbonyl(propyl)amino]-4-oxo-4-(1-piperidyl)butanoic acid,
(b051) 4-allyloxy-2-I[tert-butoxycarbonyl(methyl)amino]-4-oxo-butanoic acid,
(b052) 3-[tert-butoxycarbonyl(ethyl)amino]-4-oxo-4-(1-piperidyl)butanoic acid,
(b053) 3-[tert-butoxycarbonyl(methyl)amino]-4-oxo-4-pyrrolidin-1-yl-butanoic acid,
(b054) 3-[tert-butoxycarbonyl(methyl)amino]-4-oxazolidin-3-yl-4-oxo-butanoic acid,
(b055) 3-(tert-butoxycarbonylamino)-4-oxazolidin-3-yl-4-oxo-butanoic acid,
(b056) 3-[tert-butoxycarbonyl(methyl)amino]-4-oxo-4-(3,3,4,4-tetrafluoropyrrolidin-1-yl)butanoic acid,
(b057) 3-(tert-butoxycarbonylamino)-4-(3,3,4,4,5,5-hexafluoro-1-piperidyl)-4-oxo-butanoic acid,
(b058) 3-(tert-butoxycarbonylamino)-4-(3,3,4,4,5,5-hexafluoro-1-piperidyl)-4-oxo-butanoic acid,
(b059) 3-[tert-butoxycarbonyl(methyl)amino]-4-(3,3,4,4,5,5-hexafluoro-1-piperidyl)-4-oxo-butanoic acid,
(b060) 3-(tert-butoxycarbonylamino)-4-(3,3-dimethylpyrrolidin-1-yl)-4-oxo-butanoic acid,
(b061) 3-(tert-butoxycarbonylamino)-4-(4-methyl-1-piperidyl)-4-oxo-butanoic acid,
(b062) 3-(tert-butoxycarbonylamino)-4-morpholino-4-oxo-butanoic acid,
(b063) 3-(tert-butoxycarbonylamino)-4-(1,1-dioxo-1,4-thiazinan-4-yl)-4-oxo-butanoic acid,
(b064) 3-(tert-butoxycarbonylamino)-4-(4-tert-butyl-1-piperidyl)-4-oxo-butanoic acid,
(b065) 3-(tert-butoxycarbonylamino)-4-(dimethylamino)-4-oxo-butanoic acid,
(b066) 3-(tert-butoxycarbonylamino)-4-oxo-4-pyrrolidin-1-yl-butanoic acid,
(b067) 3-(tert-butoxycarbonylamino)-4-(3-oxa-8-azabicyclo[3.2.1]octan-8-yl)-4-oxo-butanoic acid,
(b068) 3-(tert-butoxycarbonylamino)-4-[4-(oxetan-3-yl)piperazin-1-yl]-4-oxo-butanoic acid,
(b069) 3-[tert-butoxycarbonyl(methyl)amino]-4-(1,1-dioxo-1,4-thiazinan-4-yl)-4-oxo-butanoic acid,
(b070) 3-[tert-butoxycarbonyl(methyl)amino]-4-(4-methyl-1-piperidyl)-4-oxo-butanoic acid,
(b071) 3-[tert-butoxycarbonyl(methyl)amino]-4-oxo-4-pyrrolidin-1-yl-butanoic acid,
(b072) 4-(azetidin-1-yl)-3-[tert-butoxycarbonyl(methyl)amino]-4-oxo-butanoic acid,
(b073) 3-[tert-butoxycarbonyl(methyl)amino]-4-(dimethylamino)-4-oxo-butanoic acid,
(b074) 3-[tert-butoxycarbonyl(methyl)amino]-4-(3-oxa-8-azabicyclo[3.2.1]octan-8-yl)-4-oxo-butanoic acid,
(b075) 3-[tert-butoxycarbonyl(methyl)amino]-4-[4-(oxetan-3-yl)piperazin-1-yl]-4-oxo-butanoic acid,
(b076) 3-[tert-butoxycarbonyl(methyl)amino]-4-(3,3-dimethylpyrrolidin-1-yl)-4-oxo-butanoic acid,
(b077) 3-[tert-butoxycarbonyl(methyl)amino]-4-morpholino-4-oxo-butanoic acid,
(b078) 3-[tert-butoxycarbonyl(methyl)amino]-4-oxo-4-(1-piperidyl)butanoic acid,
(b079) 2-[tert-butoxycarbonyl(methyl)amino]-4-(4-pyridyl)butanoic acid,
(b080) 2-[tert-butoxycarbonyl(methyl)amino]-4-(3-pyridyl)butanoic acid,
(b081) 2-(tert-butoxycarbonylamino)-3-(5-bromo-2-thienyl)propanoic acid,
(b082) 2-(tert-butoxycarbonylamino)-3-(5-chloro-2-thienyl)propanoic acid,
(b083) 2-[tert-butoxycarbonyl(methyl)amino]-3-(3-pyridyl)propanoic acid,
(b084) 2-[tert-butoxycarbonyl(methyl)amino]-3-(4-pyridyl)propanoic acid,
(b085) 2-(tert-butoxycarbonylamino)-3-(5-bromo-3-pyridyl)propanoic acid,
(b086) 2-[tert-butoxycarbonyl(methyl)amino]-3-(6-methyl-3-pyridyl)propanoic acid,
(b087) 2-[tert-butoxycarbonyl(methyl)amino]-3-(6-methoxy-3-pyridyl)propanoic acid,
(b088) 2-[tert-butoxycarbonyl(methyl)amino]-3-(5-methyl-3-pyridyl)propanoic acid,
(b089) 2-[tert-butoxycarbonyl(methyl)amino]-3-(5-methoxy-3-pyridyl)propanoic acid,
(b090) 2-[tert-butoxycarbonyl(methyl)amino]-3-[6-(trifluoromethyl)-3-pyridyl]propanoic acid,
(b091) 2-[tert-butoxycarbonyl(methyl)amino]-4-(3,3-difluoroazetidin-1-yl)-4-oxo-butanoic acid,
(b092) 2-[tert-butoxycarbonyl(methyl)amino]-4-(4,4-difluoro-1-piperidyl)-4-oxo-butanoic acid,
(b093) 2-[tert-butoxycarbonyl(methyl)amino]-4-methylsulfonyl-butanoic acid,
(b094) 2-[tert-butoxycarbonyl(methyl)amino]-4-(3,3-difluoroazetidin-1-yl)butanoic acid,
(b095) (2S,3R)-2-[tert-butoxycarbonyl(methyl)amino]-3-methoxy-butanoic acid,
(b096) 2-[tert-butoxycarbonyl(methyl)amino]-4-methoxybutanoic acid,
(b097) 2-[tert-butoxycarbonyl(methyl)amino]-3-(cyclopropoxy)propanoic acid,
(b098) 2-[tert-butoxycarbonyl(methyl)amino]-3-methoxypropanoic acid, (b099) 2-[tert-butoxycarbonyl(methyl)amino]-3-isopentyloxy-propanoic acid,
(b100) 2-[tert-butoxycarbonyl(methyl)amino]-3-hydroxypropanoic acid,
(b101) 2-[tert-butoxycarbonyl(methyl)amino]-3-(2,2,2-trifluoroethoxy)propanoic acid,
(b102) 2-(tert-butoxycarbonylamino)-3-(2,2,2-trifluoroethoxy)propanoic acid,
(b103) 2-(tert-butoxycarbonylamino)-3-(cyclobutoxy)propanoic acid,
(b104) 2-[tert-butoxycarbonyl(methyl)amino]-3-(cyclobutoxy)propanoic acid,
(b105) 2-(tert-butoxycarbonylamino)-3-(cyclopropoxy)propanoic acid,
(b106) 2-[tert-butoxycarbonyl(methyl)amino]-5,5-difluoropentanoic acid,
(b107) 2-[tert-butoxycarbonyl(methyl)amino]-4,4,4-trifluoro-butanoic acid,
(b108) 2-[tert-butoxycarbonyl(methyl)amino]-2-cyclopropyl-acetic acid,
(b109) 2-[tert-butoxycarbonyl(methyl)amino]-2-cyclopentyl-acetic acid,
(b110) 2-[tert-butoxycarbonyl(methyl)amino]-2-cyclobutyl-acetic acid,
(b111) 2-[tert-butoxycarbonyl(methyl)amino]pent-4-ynoic acid,
(b112) 2-[tert-butoxycarbonyl(methyl)amino]hex-5-ynoic acid,
(b113) 2-[tert-butoxycarbonyl(methyl)amino]pent-4-enoic acid,
(b114) 3-(tert-butoxycarbonylamino)-5-methyl-hexanoic acid,
(b115) 2-[tert-butoxycarbonyl(methyl)amino]-5-methyl-hexanoic acid,
(b116) 2-[tert-butoxycarbonyl(methyl)amino]octanoic acid,
(b117) 2-[tert-butoxycarbonyl(ethyl)amino]-3-cyclohexyl-propanoic acid,
(b118) 2-[tert-butoxycarbonyl(ethyl)amino]-4-methyl-pentanoic acid,
(b119) 2-[tert-butoxycarbonyl(ethyl)amino]propanoic acid,
(b120) 2-[tert-butoxycarbonyl(methyl)amino]heptanoic acid,
(b121) 2-[tert-butoxycarbonyl(methyl)amino]-3-cyclobutyl-propanoic acid,
(b122) 2-[tert-butoxycarbonyl(methyl)amino]-3-cyclopentyl-propanoic acid,
(b123) 2-[tert-butoxycarbonyl(methyl)amino]-3-cyclopropyl-propanoic acid,
(b124) 3-[tert-butoxycarbonyl(methyl)amino]-5-methyl-hexanoic acid,
(b125) 2-[tert-butoxycarbonyl(propyl)amino]propanoic acid,
(b126) 2-[tert-butoxycarbonyl(isopropyl)amino]acetic acid,
(b127) 2-[tert-butoxycarbonyl(cyclopropyl)amino]acetic acid,
(b128) 2-[tert-butoxycarbonyl-[2-(4,4-difluoro-1-piperidyl)ethyl]amino]acetic acid,
(b129) 2-[tert-butoxycarbonyl-[3-(4,4-difluoro-1-piperidyl)propyl]amino]acetic acid,
(b130) 2-[2-[tert-butoxycarbonyl(methyl)amino]-3-(dimethylamino)-3-oxo-propyl]sulfanylacetic acid,
(b131) 2-[2-(azetidin-3-yl)ethyl-tert-butoxycarbonylamino]acetic acid,
(b132) 2-[2-(2-aminoethoxy)ethyl-tert-butoxycarbonylamino]acetic acid, and
(b133) 2-[tert-butoxycarbonyl-[2-[2-(methylamino)ethoxy]ethyl]amino]acetic acid.

(General Production Method)

General production methods for the cyclic peptide compound, and the non-natural amino acid for use in the production of the cyclic peptide compound of the present invention will be described below.

Chemical Synthesis Methods for Peptide Compounds

Examples of chemical synthesis methods for the peptide compounds or the cyclic peptide compounds herein include a liquid-phase synthesis method, a solid-phase synthesis method using Fmoc synthesis, Boc synthesis, or the like, and a combination thereof. In Fmoc synthesis, a basic unit is an amino acid in which a main-chain amino group is protected with an Fmoc group, and a side-chain functional group is protected as necessary with piperidine or a protecting group that is not cleaved by a base, such as a t-Bu group, a THP group, or a Trt group, and a main-chain carboxylic acid is not protected. The basic unit is not particularly limited as long as it is a combination having an Fmoc-protected amino group and a carboxyl group. For example, dipeptide may be a basic unit. The basic unit disposed at the N terminus may be a unit other than the Fmoc amino acid. For example, it may be a Boc amino acid or a carboxylic acid analog which does not have an amino group. The main-chain carboxyl group, or a side-chain carboxyl group of an amino acid that has a carboxyl group in a side chain and in which the main-chain carboxyl group is protected with a suitable protecting group, is supported on a solid phase by a chemical reaction with the functional group of a solid-phase carrier. Subsequently, the Fmoc group is deprotected by a base such as piperidine or DBU, and a newly produced amino group and a subsequently added, basic-unit protected amino acid having a carboxyl group are subjected to a condensation reaction to produce a peptide bond. In the condensation reaction, various combinations such as a combination of DIC and HOBt, a combination of DIC and HOAt, and a combination of HATU and DIPEA are possible as activating agents for the carboxyl group. The desired peptide sequence can be produced by repeating the Fmoc group deprotection and the subsequent peptide bond forming reaction. After the desired sequence is obtained, cleavage from the solid phase and deprotection of the optionally introduced protecting group of the side-chain functional group are conducted. Further, conformational conversion and cyclization of the peptide can be performed before cleaving from the solid phase. Cleaving from the solid phase and deprotection may be performed under the same conditions, e.g., in 90:10 TFA/$H_2O$, or deprotection may be performed under different conditions as necessary. Cleaving from the solid phase may be achieved using a weak acid such as 1% TFA in some cases, and Pd or the like may be used as a protecting group to utilize the orthogonality of both chemical reactions. During or at the end of these steps, a step such as cyclization can also be performed. For example, a side-chain carboxylic acid and an N-terminal main-chain amino group can be condensed, and a side-chain amino group and a C-terminal main-chain carboxylic acid can be condensed. In this case, reaction orthogonality is required between the carboxylic acid on the C-terminal side and the side-chain carboxylic acid to be cyclized, or between the main-chain amino group or hydroxy group on the N-terminal side and the side-chain amino group to be cyclized. As described above, the protecting group is selected in consideration of the orthogonality of the protecting group. The reaction product thus obtained can be purified by a reverse-phase column, a molecular sieve column, or the like. Details of these procedures are described in, for example, the Solid-Phase Synthesis Handbook published by Merck on May 1, 2002.

Commercially available resins for solid phase synthesis are usable, and examples include CTC resin, Wang resin, and SASRIN resin.

A general method for synthesizing an amino acid-supported resin for use in peptide synthesis by a peptide synthesizer will be described below.

An Fmoc amino acid can be supported on a resin by the method described in WO2013/100132 or WO2018/225864. Specifically, for example, 2-chlorotrityl chloride resin and a solvent (e.g., dehydrated dichloromethane) are introduced into a filter-equipped reaction vessel to swell the resin. Next, the solvent and the resin are separated, and then a mixture of the resin, a C-terminal free Fmoc amino acid dissolved in a solvent (e.g., dehydrated dichloromethane), a solvent (e.g., dehydrated methanol), and a base (e.g., diisopropylethylamine) is added to the reaction vessel and mixed to support the Fmoc amino acid on the resin. After the resin and the reaction solution are separated, the resin is mixed with a mixture of one or more solvents and a base (e.g., a mixture of dehydrated dichloromethane, dehydrated methanol, and diisopropylethylamine) to wash the resin. After the resin is washed with a solvent (e.g., dichloromethane) multiple times as necessary, the resin and the reaction solution are separated. By drying the resulting resin under reduced pressure overnight, an Fmoc amino acid-supported resin can be obtained.

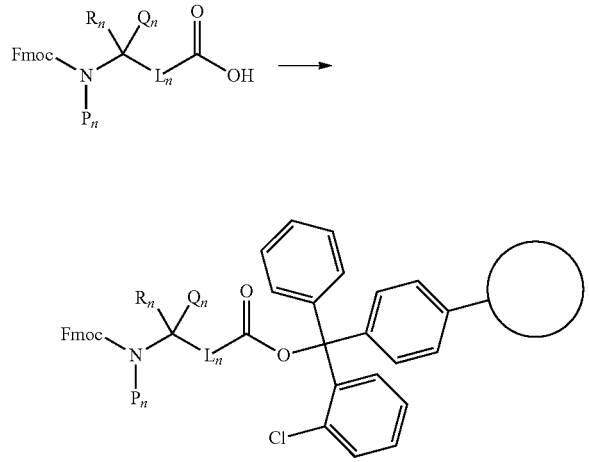

(wherein n represents an integer of 1 to 11; $P_1$ to $P_{11}$, $Q_1$ to $Q_{11}$, and $R_1$ to $R_{11}$ mean $P_1$ to $P_{11}$, $Q_1$ to $Q_{11}$, and $R_1$ to $R_{11}$ as defined herein, respectively; $L_1$ and $L_{11}$ mean $L_1$ and $L_{11}$ as described herein, respectively; $L_2$ to $L_{10}$ are single bonds; and ○ (circle) means a resin portion.)

The above structure shows that in the Fmoc-amino acid, the 2-chlorotrityl group on the resin is bonded to the carboxylic acid of the Fmoc amino acid via an ester bond.

In the production of the compound described herein, when the defined group undergoes undesired chemical conversion under the conditions of the performed method, the compound can be produced by means of, for example, protection and deprotection of a functional group. Selection and introduction/removal procedures of a protecting group can be performed according to, for example, the methods described in Greene's "Protective Groups in Organic Synthesis" (5th Ed., John Wiley & Sons, 2014), which may be suitably used depending on the reaction conditions. Further, the order of reaction steps such as introduction of a substituent can be changed as necessary. For example, the protecting group for an amino group is an Fmoc, Boc, Cbz, or Alloc group. These carbamate groups can be introduced by reacting an amino group with a carbamating agent in the presence of a basic catalyst. Examples of the carbamating agent include $Boc_2O$, BocOPh, FmocOSu, FmocCl, CbzCl, and AllocCl. Examples of the basic catalyst include lithium carbonate, sodium carbonate, sodium hydrogen carbonate, potassium carbonate, potassium hydrogen carbonate, cesium carbonate, cesium hydrogen carbonate, lithium hydroxide, sodium hydroxide, potassium hydroxide, cesium hydroxide, sodium phosphate, potassium phosphate, N-methylmorpholine, triethylamine, diisopropylethylamine, and N,N-dimethylaminopyridine. A carbamate group which is a protecting group for an amino group can be removed under basic conditions, acidic conditions, hydrogenolysis reaction conditions, or the like.

(Cyclization Methods for Cyclic Peptide Compounds)

A method for transforming a linear peptide compound into a cyclic peptide compound can be performed by carrying out a bond forming reaction within the molecule according to, for example, the method described in Comprehensive Organic Transformations, A Guide to Functional Group Preparations, 3rd Edition by R. C. Larock, or March's Advanced Organic Chemistry: Reactions, Mechanisms, and Structure, 7th Edition by M. B. March. After the bond forming reaction, further, a functional group transforming reaction can also be performed. Examples of the bond forming reaction include a C(O)—N bond formed from carboxylic acid and amine; a C—O—C bond, a C(O)—O bond, and a C(S)—O bond using an oxygen atom; a C(O)—S bond, a C(S)—S bond, a C—S—S—C bond, a C—S—C bond, a C—S(O)—C bond, and a C—S(O$_2$)—C bond using a sulfur atom; and a C—N—C bond, a C=N—C bond, an N—C(O)—N bond, an N—C(S)N bond, and a C(S)—N bond using a nitrogen atom. Furthermore, examples include C—C bond forming reactions catalyzed by a transition metal, such as Suzuki reaction, Heck reaction, and Sonogashira reaction. Examples of the functional group transforming reaction further performed after the bond forming reaction include an oxidation reaction and a reduction reaction. A specific example is a reaction for oxidizing a sulfur atom to transform it into a sulfoxide group or a sulfone group. Another example is a reduction reaction for reducing a triple bond or a double bond of carbon-carbon bonds to a double bond or a single bond. While a closed ring structure is formed by a peptide bond when two amino acids are bonded with the amino acid main chain, a covalent bond between two amino acids may be formed by bonding between side chains of two amino acids, bonding between a side chain and a main chain, or the like. A black circle or a black square below indicates an amino acid residue, and connected black circles or black squares represent a peptide chain connected by an amide bond. The number of amino acid residues constituting a peptide chain are not particularly limited, and the number of black circles or black squares below does not represent the number of amino acid residues.

Herein, a peptide compound having a cyclic moiety may be referred to as a "cyclic peptide compound". Herein, the "cyclic moiety" of a peptide compound means a cyclic portion formed of two or more connected amino acid residues.

(General Preparation Method 1 for Cyclic Peptide Compounds)

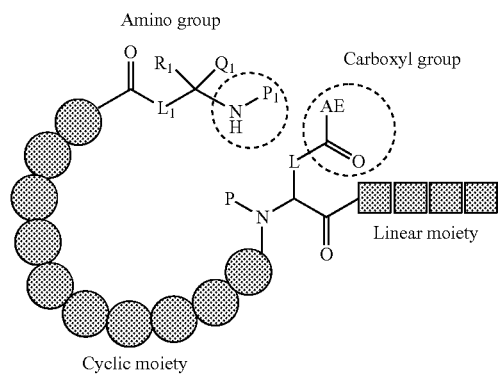

Cyclic moiety

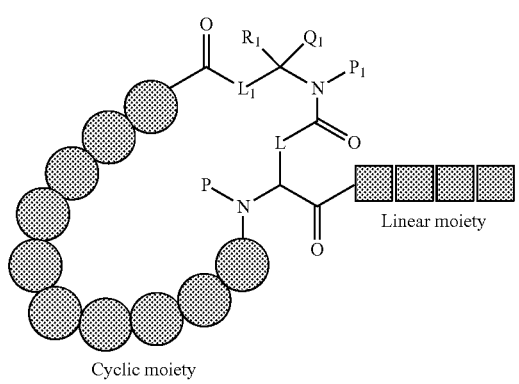

Cyclic moiety $R_1$ and $Q_1$ represent a side chain of amino acid. $P_1$ and P represent a hydrogen or an alkyl group. $L_1$ and L represent a linker. AE represents OH or active ester.

Cyclic moieties of cyclic peptide compounds having linear moieties can be cyclized by activating the N-terminal amino group and the C-terminal side chain carboxyl group (e.g., L=—$CH_2$— in the case of aspartic acid or its derivative, and L=—$CH_2CH_2$— in the case of glutamic acid or its derivative) with an activating reagent or converting them to active esters, and then condensing them in the molecule to form a C(O)—N bond.

(General Preparation Method 2 for Cyclic Peptide Compounds)

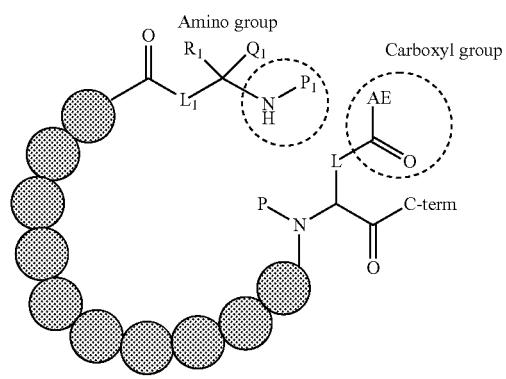

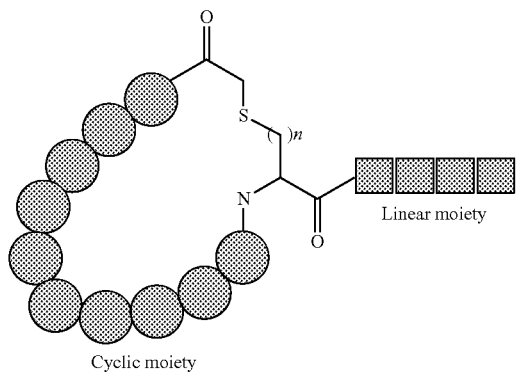

$R_1$ and $Q_1$ represent a side chain of amino acid. $P_1$ and P represent a hydrogen or an alkyl group. $L_1$ and L represent a linker. AE represents OH or active ester. C-Term represents OH, an alkoxy group, or an optionally substituted amino group.

Cyclic peptide compounds described in "General preparation method 1 for cyclic peptide compounds" in which the linear moiety is C-Term can be cyclized by activating the N-terminal amino group and the C-terminal side chain carboxyl group (e.g., L=—$CH_2$— in the case of aspartic acid or its derivative, and L=—$CH_2CH_2$— in the case of glutamic acid or its derivative) with an activating reagent or converting them to active esters, and then condensing them in the molecule to form a C(O)—N bond.

(General Preparation Method 3 for Cyclic Peptide Compounds)
(Method of Cyclizing with Haloalkyl and SH Groups)

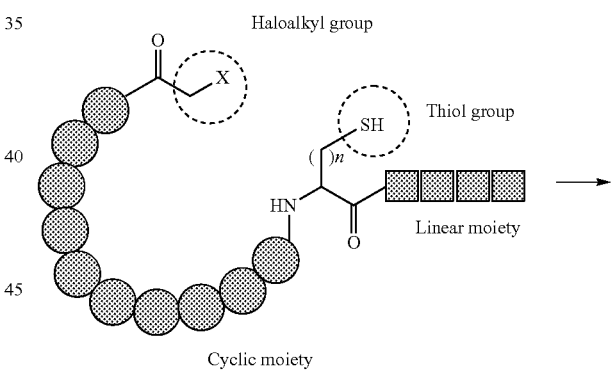

Cyclic moiety

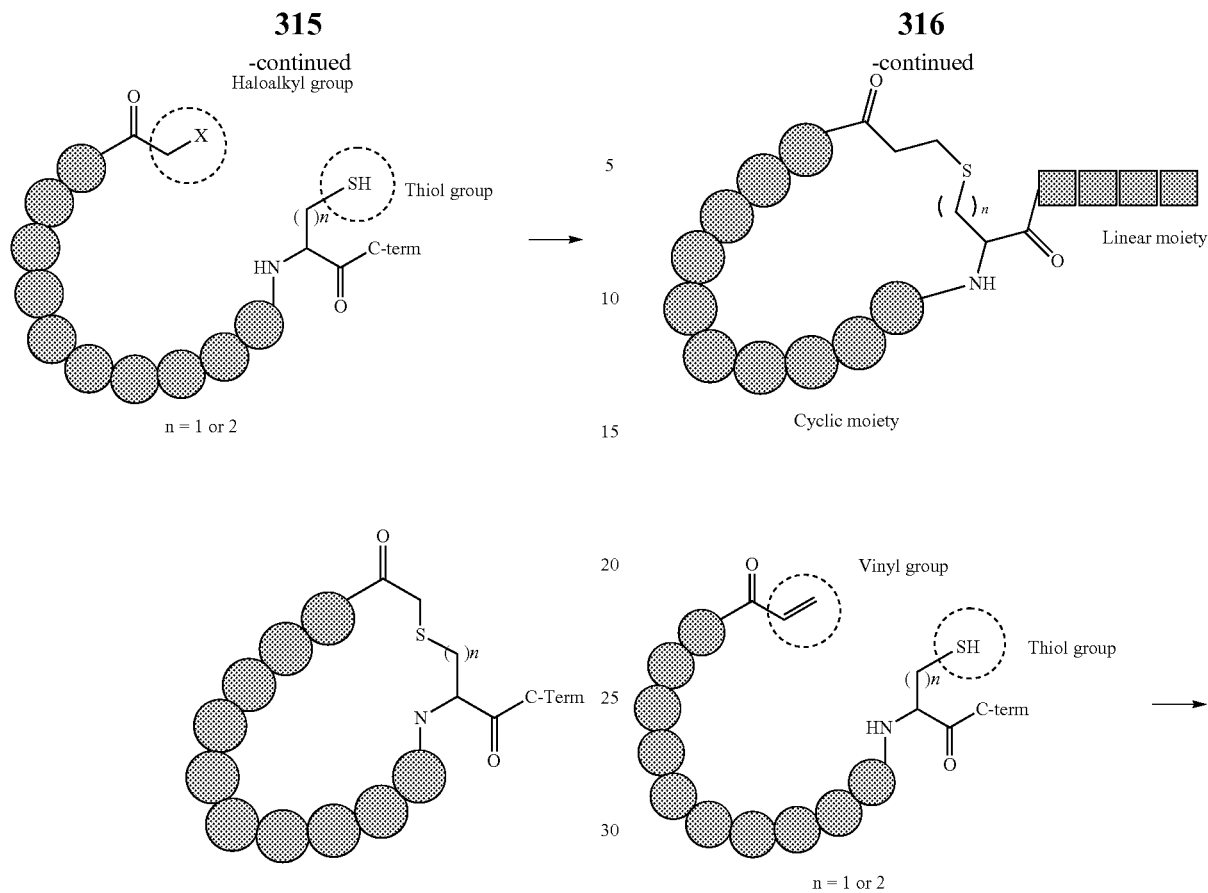

C-Term represents OH, an alkoxy group, or an optionally substituted amino group.

Cyclic moieties of cyclic peptide compounds having linear moieties can be cyclized by reacting the haloalkyl group of an amino acid residue with the thiol group of an amino acid residue in the molecule to form a C—S—C bond. Cyclic peptide compounds described in "General preparation method 1 for cyclic peptide compounds" in which the linear moiety is C-Term can also be similarly cyclized by reacting the haloalkyl group of an amino acid residue with the thiol group of an amino acid residue in the molecule to form a C—S—C bond. Further, a C—S(O)—C or C—S(O)$_2$—C bond can also be formed by oxidizing and converting a sulfur atom to a sulfoxide or sulfone.

(Method of Cyclizing with Vinyl and SH Groups)

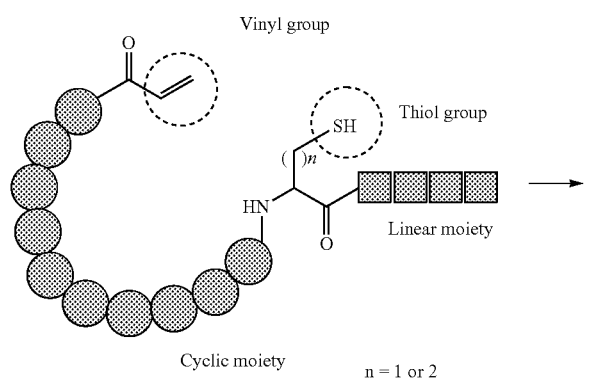

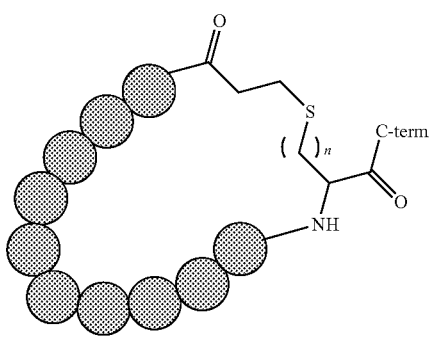

C-Term represents OH, an alkoxy group, or an optionally substituted amino group.

Cyclic moieties of cyclic peptide compounds having linear moieties can be cyclized by reacting the vinyl group of an amino acid residue with the thiol group of an amino acid residue in the molecule to form a C—S—C bond. Cyclic peptide compounds described in "General preparation method 1 for cyclic peptide compounds" in which the linear moiety is C-Term can also be similarly cyclized by reacting the vinyl group of an amino acid residue with the thiol group of an amino acid residue in the molecule to form a C—S—C bond. Further, a C—S(O)—C or C—S(O)$_2$—C bond can also be formed by oxidizing and converting a sulfur atom to a sulfoxide or sulfone.

(Method of Cyclizing with Ethynyl and SH Groups)

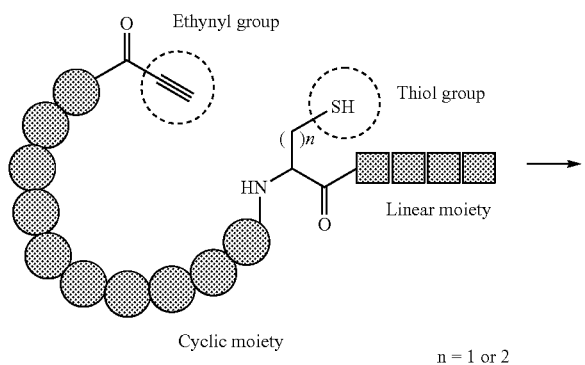

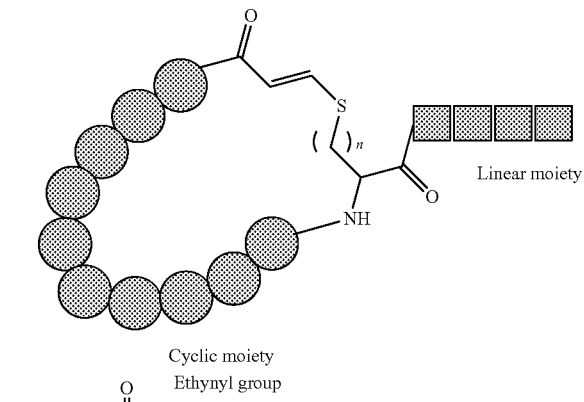

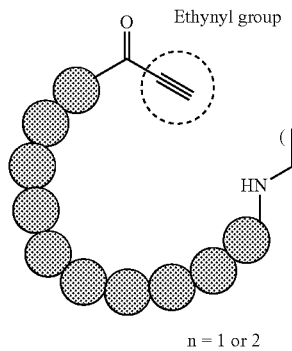

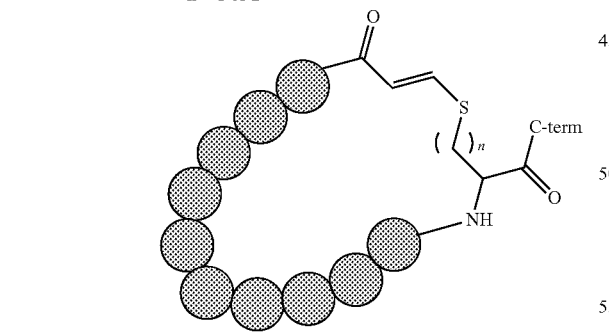

C-Term represents OH, an alkoxy group, or an optionally substituted amino group.

Cyclic moieties of cyclic peptide compounds having linear moieties can be cyclized by reacting the ethynyl group of an amino acid residue with the thiol group of an amino acid residue in the molecule to form a C—S—C bond. Cyclic peptide compounds described in "General preparation method 1 for cyclic peptide compounds" in which the linear moiety is C-Term can also be similarly cyclized by reacting the ethynyl group of an amino acid residue with the thiol group of an amino acid residue in the molecule to form a C—S—C bond. Further, a C—S(O)—C or C—S(O)$_2$—C bond can also be formed by oxidizing and converting a sulfur atom to a sulfoxide or sulfone. The double bond site can also be reduced and converted to a single bond.

(Method of Cyclizing with Vinyl and Vinyl Groups)

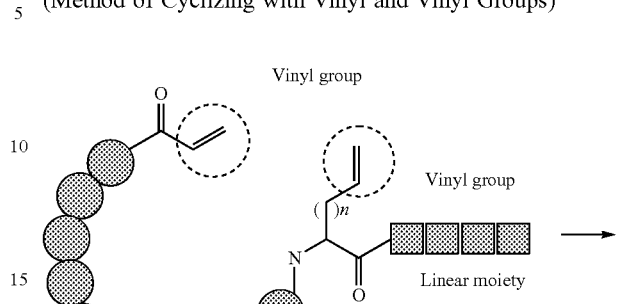

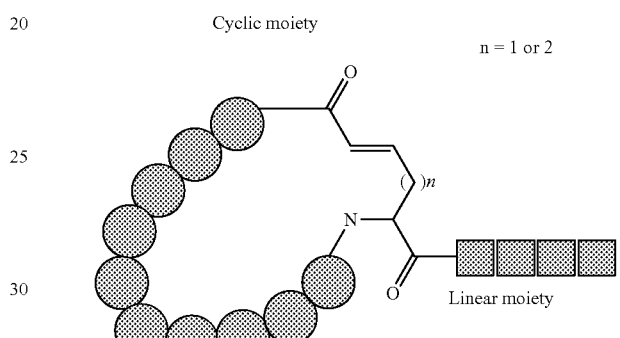

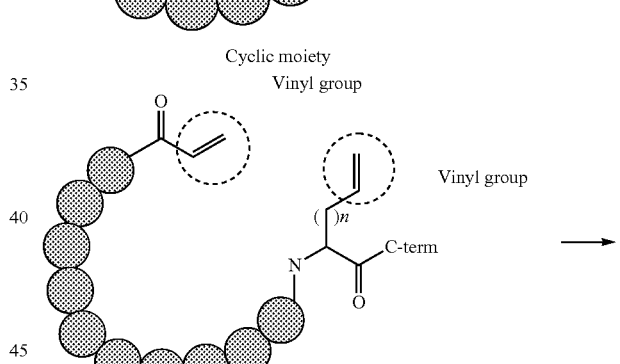

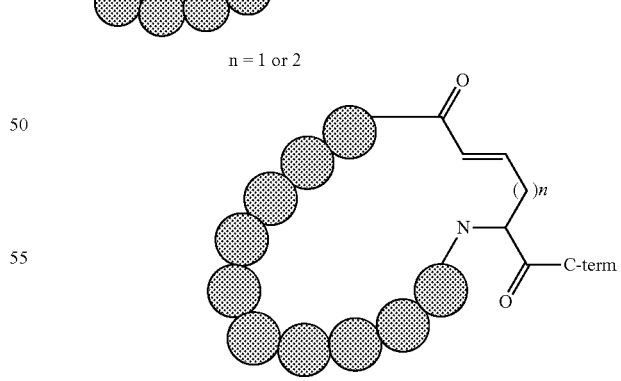

C-Term represents OH, an alkoxy group, or an optionally substituted amino group.

Cyclic moieties of cyclic peptide compounds having linear moieties can be cyclized by reacting different vinyl groups of amino acid residues with each other in the molecule to form a C—C bond. Cyclic peptide compounds described in "General preparation method 1 for cyclic peptide compounds" in which the linear moiety is C-Term can also be similarly cyclized by reacting different vinyl groups of amino acid residues with each other in the molecule to form a C—C bond.

(Method of Cyclizing by Forming a Triazole Ring with Azido and Ethynyl Groups)

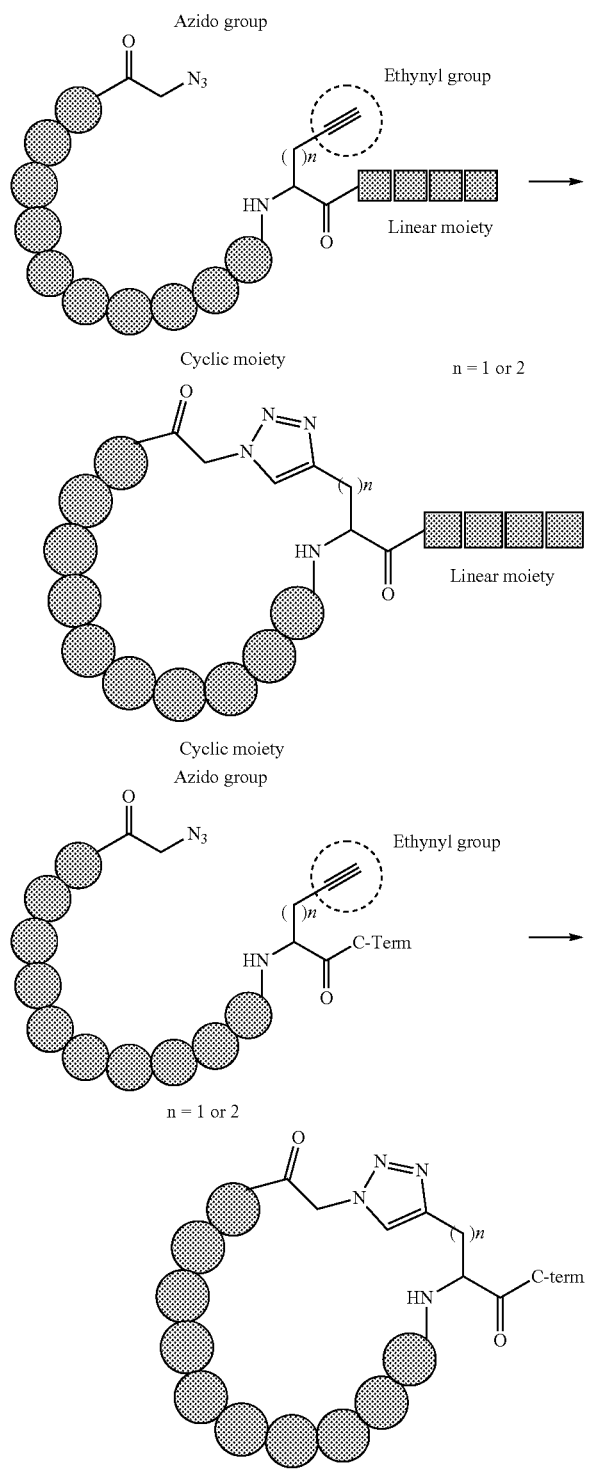

C-Term represents OH, an alkoxy group, or an optionally substituted amino group.

Cyclic moieties of cyclic peptide compounds having linear moieties can be cyclized by reacting the azido group of an amino acid residue with the ethynyl group of an amino acid residue in the molecule to form a triazole ring. Cyclic peptide compounds described in "General preparation method 1 for cyclic peptide compounds" in which the linear moiety is C-Term can also be similarly cyclized by reacting the azido group of an amino acid residue with the ethynyl group of an amino acid residue in the molecule to form a triazole ring.

General preparation methods for peptide compounds by peptide modification are shown below. In the following schemes, $P_n$ represents a substituent for a nitrogen atom, $R_n$ and $Q_n$ each represent an amino acid side chain, a black circle represents an amino acid residue, linked black circles represent a peptide chain linked by amide bonds, and m represents the number of amino acid residues and may be any integer of 1 or more.

(Method of Preparing Peptides Containing N-Alkylamino Acids)

Peptides containing N-alkylamino acids can be synthesized according to the general peptide synthesis method described in the present Examples using an Fmoc-protected N-alkylamino acid as a raw material, or alternatively can be prepared by alkylating the N-terminal nitrogen on a resin as illustrated below. Specifically, the target peptides having an N-alkylamino acid at the N-terminus can be prepared by reacting the nitrogen of the N-terminal Tfa amide (trifluoroacetamide) of a resin-loaded peptide with an alkyl halide under basic conditions, and then treating the peptide with a reducing agent by referring to Organic Letters, 2008, 10, 4815-4818 or the like. Further, cyclic peptide compounds can be prepared by elongating, cleaving from the resin, cyclizing, deprotecting, and purifying the peptide according to the general peptide synthesis method described in the present Examples.

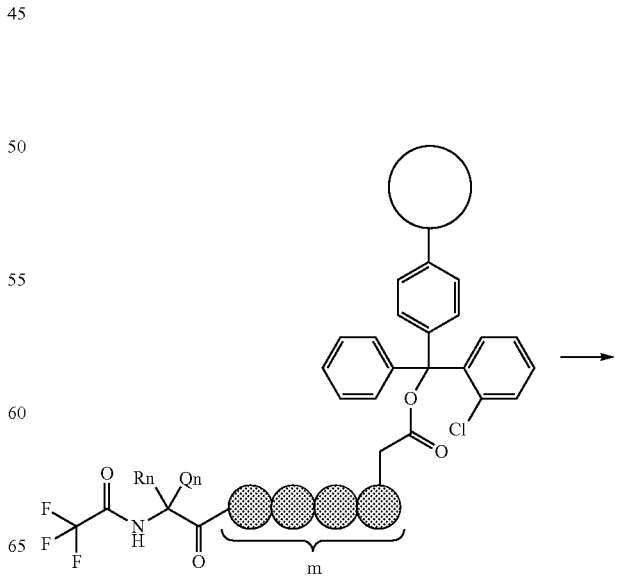

321
-continued

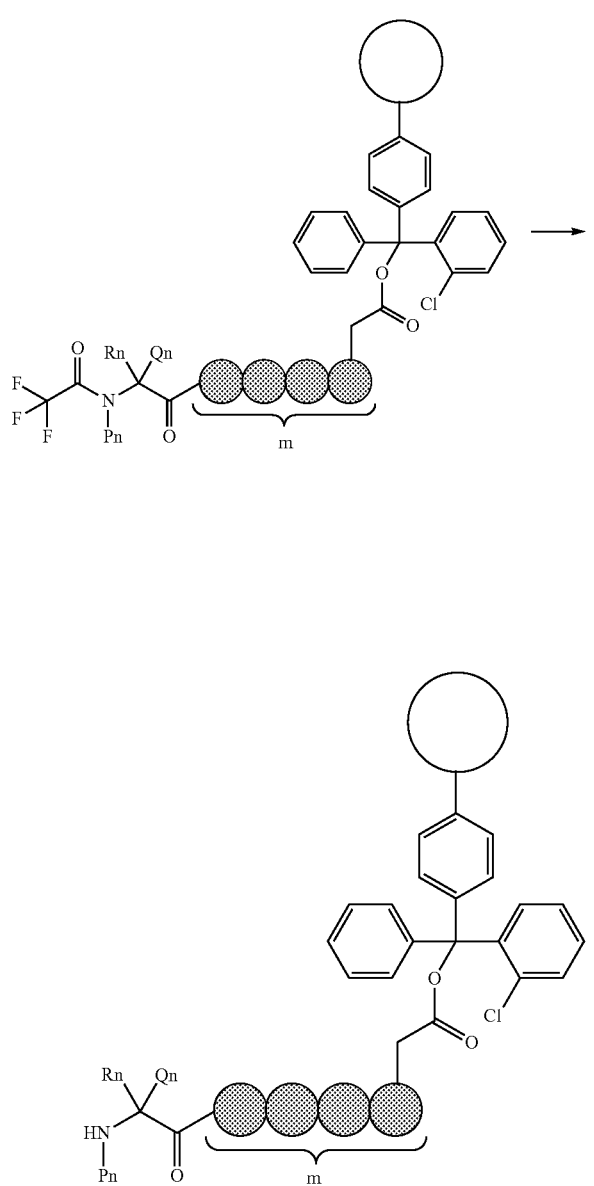

322

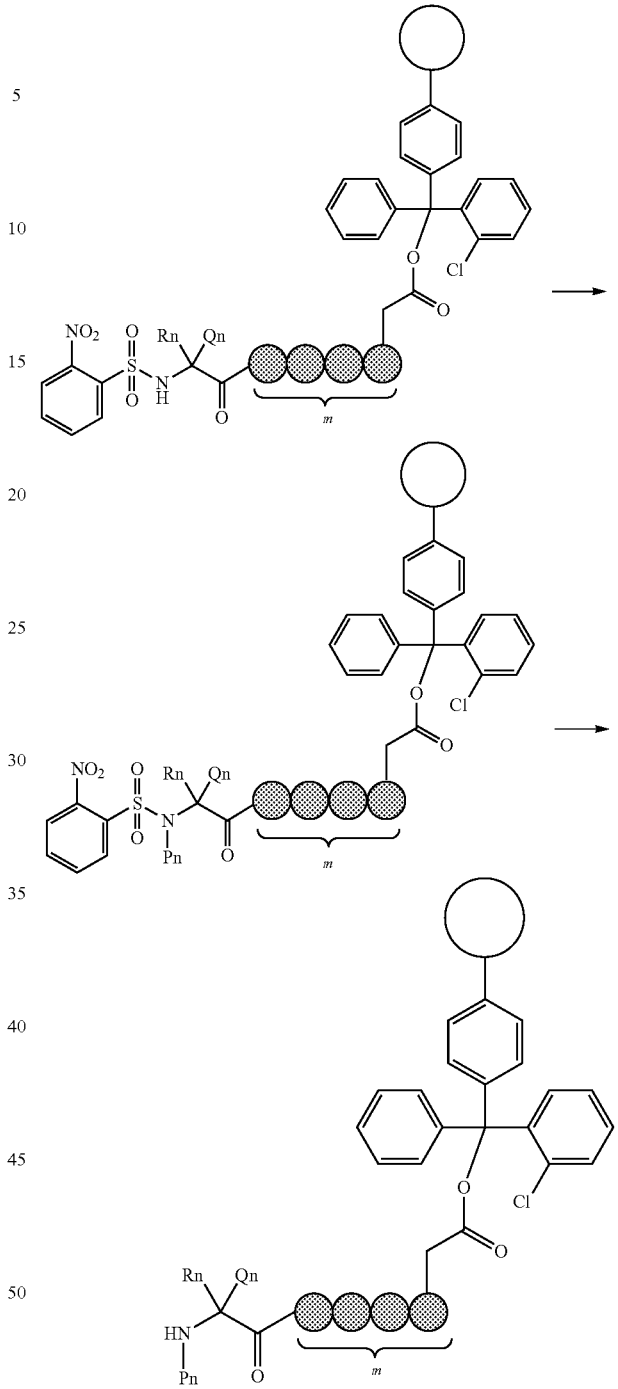

The method described in Nature Protocols, 2012, 7, 432-444 which is shown below can also be used as another method of introducing $P_n$ onto the N-terminal nitrogen. Specifically, the target peptides having $P_n$ at the N-terminus can be obtained by converting the N-terminal amine of a resin-loaded peptide to an Ns-substituted form, introducing $P_n$ by Mitsunobu reaction, and then deprotecting the Ns group. Further, cyclic peptide compounds can be prepared by elongating, cleaving from the resin, cyclizing, deprotecting, and purifying the peptide according to the general peptide synthesis method described in the present Examples.

Peptides containing glycine with $P_n$ introduced onto the nitrogen atom can be synthesized according to the general peptide synthesis method described in the present Examples using glycine with $P_n$ introduced onto the Fmoc-protected nitrogen atom as a raw material, or alternatively can be prepared by substitution reaction between the N-terminal halogenated carbon and an amine as illustrated below. Specifically, the target peptides having N-terminal glycine with $P_n$ introduced onto the nitrogen atom can be obtained by reacting the N-terminal amine with iodoacetic acid and then reacting it with any primary amine by referring to Organic Letters, 2010, 12, 4928-4931 or the like. Further, cyclic peptide compounds can be prepared by elongating, cleaving from the resin, cyclizing, deprotecting, and purifying the peptide according to the general peptide synthesis method described in the present Examples.

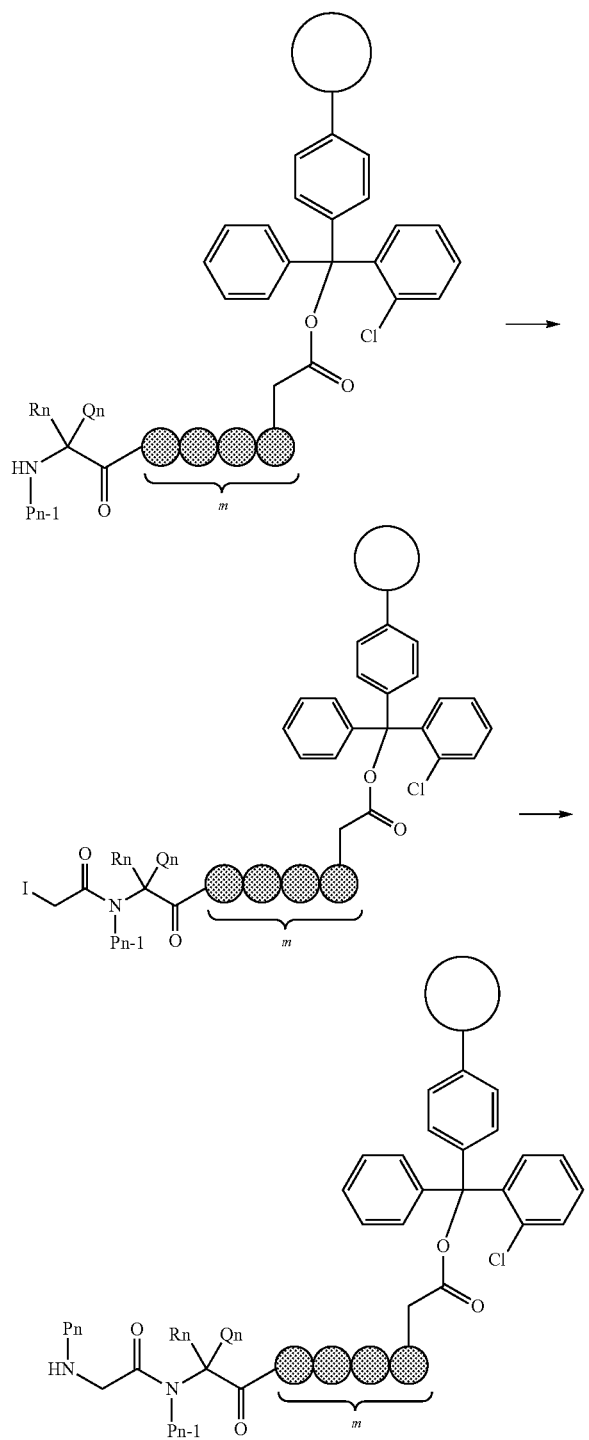

(Method of Preparing Peptides Containing an Aryloxy or Heteroaryloxy Group on the Side Chain)

Peptides containing an aryloxy or heteroaryloxy group on the side chain can be prepared according to the general peptide synthesis method described in the present Examples using an Fmoc amino acid having the target aryloxy or heteroaryloxy group on the side chain as a raw material, or alternatively can be prepared using a peptide having an alcohol on the side chain as a precursor by referring to Organic Letters, 2014, 16, 4944-4947, Tetrahedron Letters, 2003, 44, 3863-3865, or the like, as illustrated below. Specifically, peptides having an aryloxy or heteroaryloxy group on the side chain can be prepared by reacting a peptide having an alcohol on the side chain with triarylboroxane-pyridine complex in the presence of copper(II) acetate. n below represents the number of methylene groups and may be any integer of 1 or more.

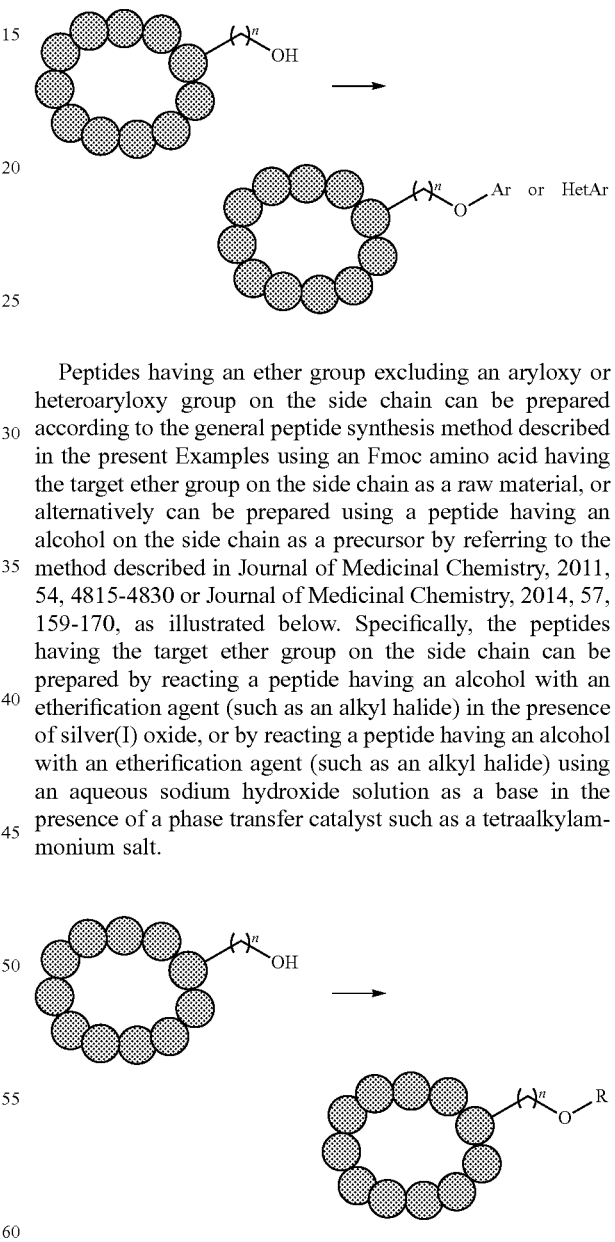

Peptides having an ether group excluding an aryloxy or heteroaryloxy group on the side chain can be prepared according to the general peptide synthesis method described in the present Examples using an Fmoc amino acid having the target ether group on the side chain as a raw material, or alternatively can be prepared using a peptide having an alcohol on the side chain as a precursor by referring to the method described in Journal of Medicinal Chemistry, 2011, 54, 4815-4830 or Journal of Medicinal Chemistry, 2014, 57, 159-170, as illustrated below. Specifically, the peptides having the target ether group on the side chain can be prepared by reacting a peptide having an alcohol with an etherification agent (such as an alkyl halide) in the presence of silver(I) oxide, or by reacting a peptide having an alcohol with an etherification agent (such as an alkyl halide) using an aqueous sodium hydroxide solution as a base in the presence of a phase transfer catalyst such as a tetraalkylammonium salt.

(Method of Preparing Peptides Containing an Aryl or Heteroaryl Group on the Side Chain)

Peptides having an aryl or heteroaryl group on the side chain can be prepared according to the general peptide synthesis method described in the present Examples using an Fmoc amino acid having the target aryl or heteroaryl group on the side chain as a raw material, or alternatively can be prepared using a peptide having a carboxylic acid on the side chain as a precursor by referring to the method described in J. Am. Chem. Soc., 2016, 138, 5016-5019 or the like, as illustrated below. Specifically, the peptides having the target aryl or heteroaryl group on the side chain can be prepared by activating a peptide having a carboxylic acid on the side chain with N-hydroxyphthalimide, and reacting it with any aryl halide or heteroaryl halide. n below represents the number of methylene groups and may be any integer of 1 or more.

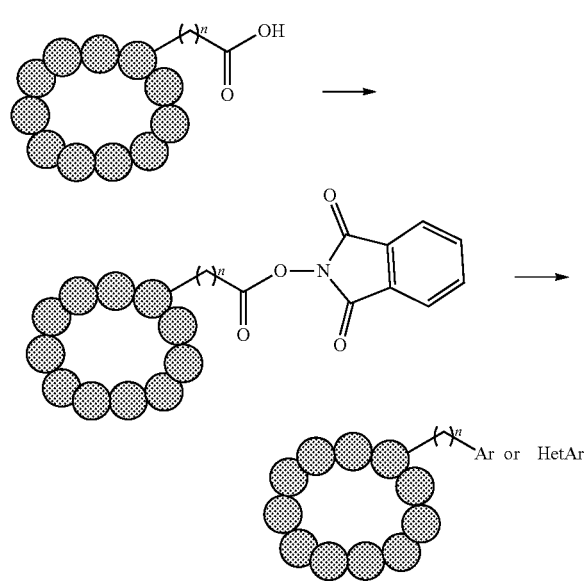

Alternatively, peptides having an aryl or heteroaryl group on the side chain can also be synthesized by Suzuki coupling using a peptide having a boronic acid on the side chain as a precursor, as illustrated below. Specifically, the target peptides having an aromatic ring on the side chain can be prepared by synthesizing a precursor peptide using an Fmoc amino acid having a boronic acid on the side chain as a raw material, and reacting it with any aryl halide in the presence of a palladium catalyst.

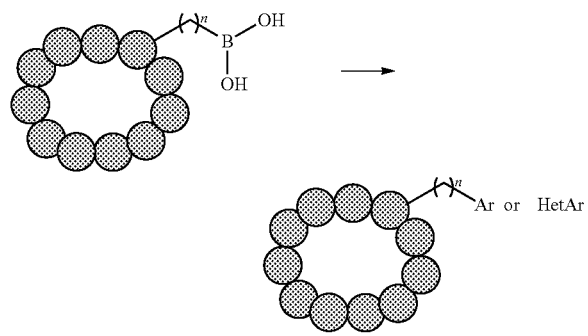

(Method of Preparing Peptides Containing an Amido Group on the Side Chain)

Peptides having an amido group on the side chain can be synthesized using an Fmoc amino acid having the target amido group on the side chain as a raw material, or alternatively can be synthesized by amidation of a peptide having a carboxylic acid on the side chain as a precursor, as illustrated below. Specifically, the target peptides having an amido group on the side chain can be obtained by deprotecting a peptide having a protected carboxylic acid on the side chain to synthesize a precursor peptide having a carboxylic acid on the side chain, and condensing it with any amine using a condensing agent such as HATU. n below represents the number of methylene groups and may be any integer of 1 or more.

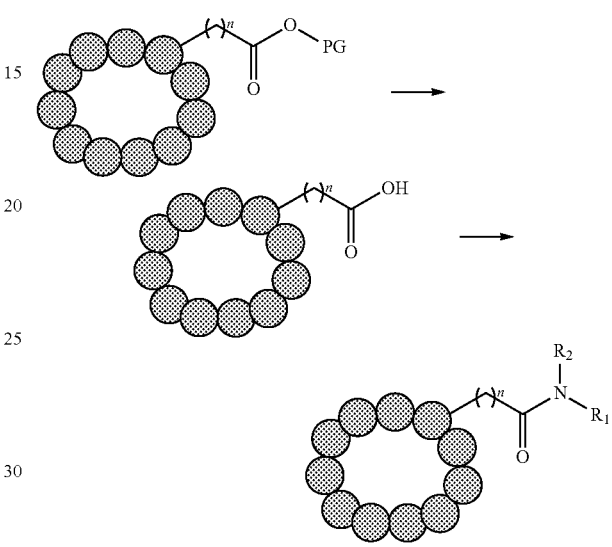

(Synthesis of Peptides Containing a Double Bond on the Side Chain)

Peptides having a double bond on the side chain can be synthesized using an Fmoc amino acid having the target double bond on the side chain as a raw material, or alternatively can be prepared by functionalization of a terminal olefin. Specifically, a peptide having a terminal olefin on the side chain can be synthesized according to the general peptide synthesis method described in the present Examples, and the side chain can be further converted to a side chain having a highly substituted olefin by coupling with a substrate having any terminal olefin by olefin metathesis reaction. Further, the side chain can be converted to a corresponding side chain by reducing the olefin by hydrogenation reaction. n below represents the number of methylene groups and may be any integer of 1 or more.

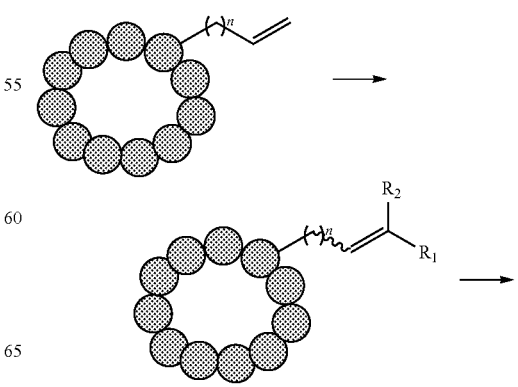

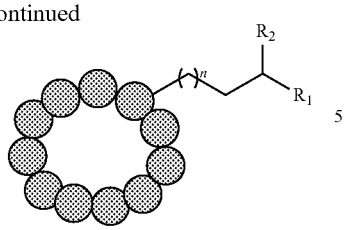

Peptide compounds with a peptide backbone crosslinked can also be prepared using a peptide having multiple double bonds on the side chain. Specifically, crosslinked compounds can be prepared by synthesizing a peptide having terminal olefins at two sites on the side chain according to the general peptide synthesis method described in the present Examples, and further crosslinking the two olefins by olefin metathesis reaction by referring to Nature Protocols, 2011, 6, 761-771. Further, compounds crosslinked with saturated alkylenes can be prepared by reducing the olefins by hydrogenation reaction. m and n below represent the number of methylene groups and may be independently any integer of 1 or more.

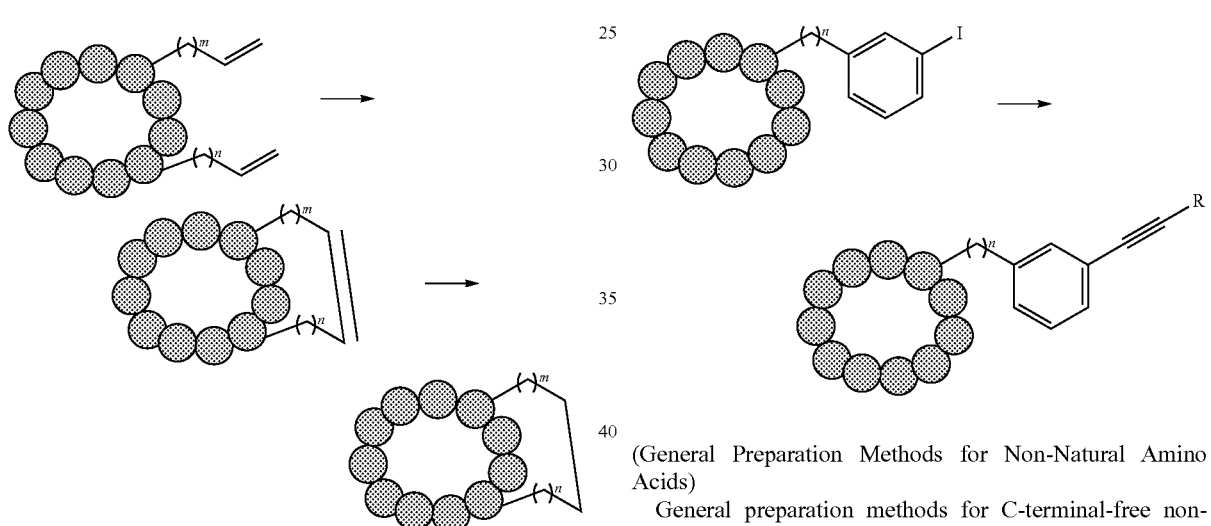

(Synthesis of Peptides Containing a Triazole on the Side Chain)

Peptides having a triazole on the side chain can be prepared by click reaction with an azido group. Specifically, peptide compounds having an azido group on the side chain can be prepared by synthesizing a peptide having an azido group on the side chain according to the general peptide synthesis method described in the present Examples, and coupling the peptide with any acetylene in the presence of copper(I) iodide by referring to Bioorganic & Medicinal Chemistry Letters, 2009, 19, 4130-4133 or the like. n below represents the number of methylene groups and may be any integer of 1 or more.

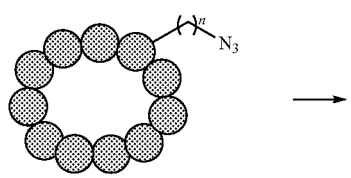

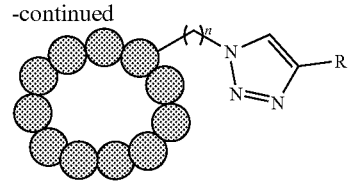

(Synthesis of Peptides Containing an Aryl Group Substituted with an Alkynyl Group on the Side Chain)

Peptides containing an aryl group substituted with an alkynyl group on the side chain can be synthesized by Sonogashira coupling reaction with an aryl halide group. Specifically, the conversion to peptide compounds having an aryl group substituted with an alkynyl group on the side chain can be conducted by synthesizing a peptide having an aryl iodide group on the side chain according to the general peptide synthesis method described in the present Examples, and coupling the peptide with any acetylene in the presence of copper(I) iodide. n below represents the number of methylene groups and may be any integer of 1 or more.

(General Preparation Methods for Non-Natural Amino Acids)

General preparation methods for C-terminal-free non-natural amino acids where the nitrogen atoms of the amino acids are protected are shown below. In the following schemes, $PG_1$ and $PG_1'$ each represent a protecting group for a nitrogen atom, $PG_2$ and $PG_2'$ each represent a protecting group for an oxygen atom, $PG_3$ and $PG_4$ each represent a protecting group for an amino acid side chain, $R_n$ and $Q_n$ each represent an amino acid side chain, $P_n$ represents a substituent for a nitrogen atom, P' represents $C_1$-$C_5$ alkyl, and R, R', R", and R'" each represent a substituent for a hydrogen or amino group. In the methods of preparing amino acids shown below, a functional group other than the target functional group may cause chemical reaction. In such a case, only the desired reaction can be allowed to proceed by introducing a protecting group onto a non-target functional group. Examples of such protecting group introduction and removal reactions include methods described in Greene's "Protective Groups in Organic Synthesis" (5th ed., John Wiley & Sons 2014). For conversion reactions of compound functional groups, one can refer to Larock's "Comprehensive Organic Transformations: A Guide to Functional Group Preparations" (5th ed.) or Smith's "March's Advanced Organic Chemistry: Reactions, Mechanisms, and Structure" (8th ed.).

Non-natural amino acids having a protecting group (PG$_1$) introduced onto the amino acid nitrogen atom can be prepared using the following method. The target C-terminal-free non-natural amino acids can be prepared by introducing a protecting group onto an N-terminal-free amino acid available from a commercial supplier and deprotecting it as necessary according to conventional methods.

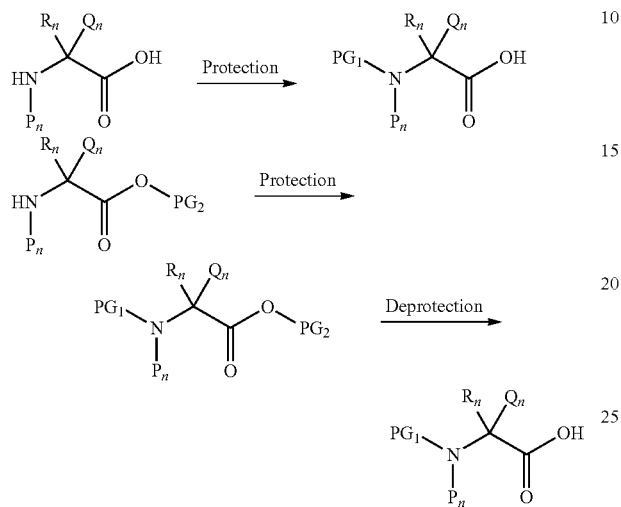

Non-natural amino acids having a protecting group (PG$_1$') introduced onto the amino acid nitrogen atom can be prepared using the following method. The target C-terminal-free non-natural amino acids can be prepared by deprotecting an amino acid that has a protecting group (PG$_1$) introduced onto the N-terminus which is available from a commercial supplier, and introducing a protecting group, according to conventional methods.

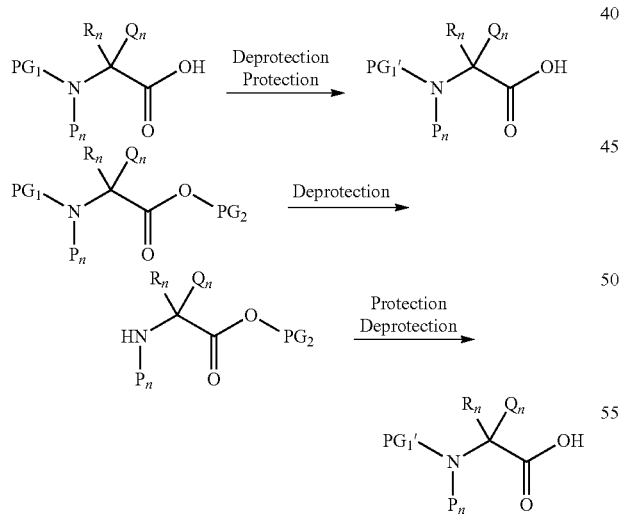

Non-natural amino acids having an aminoalkyl group introduced onto the substituent (P$_n$) of the amino acid nitrogen atom can be prepared using the following method. A bromoacetic acid ester derivative available from a commercial supplier is reacted with an amino alcohol according to the method of King et al. (Tetrahedron Letters, 2002, 43(11), 1987-1990), and then a protecting group (PG$_1$) is introduced onto the nitrogen atom. Next, the hydroxyl group is oxidized according to the method of Dess et al. (J. Org. Chem., 1983, 48(22), 4155-4156), and the aldehyde group is reductively aminated according to the method of Borch et al. (J. Org. Chem. 1972, 37(10), 1673-1674) to introduce an amino group. Next, the target C-terminal-free non-natural amino acid can be prepared by deprotecting the protecting group for the oxygen atom.

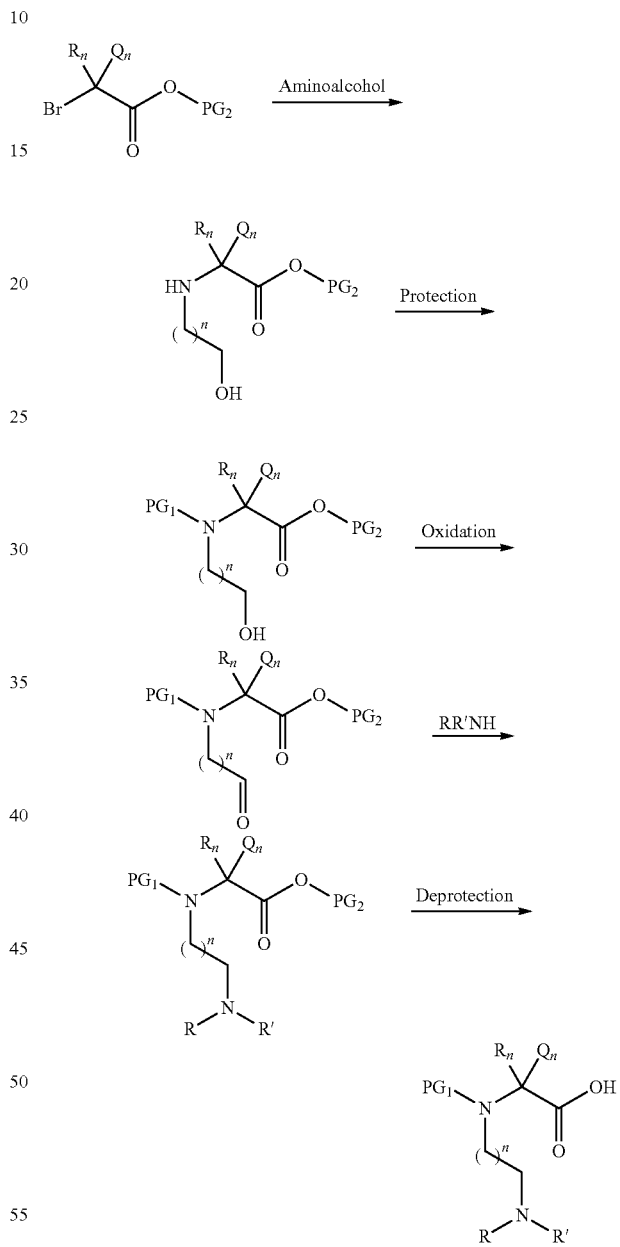

N-substituted amino acids can also be prepared by the following scheme of introducing a substituent (P$_n$) onto the amino acid nitrogen atom. A bromoacetic acid ester derivative available from a commercial supplier is reacted with an amine (P$_n$NH$_2$) in the presence of a base, and then a protecting group (PG$_1$) is introduced onto the nitrogen atom. Next, the target C-terminal-free non-natural amino acid can be prepared by deprotecting the protecting group for the oxygen atom.

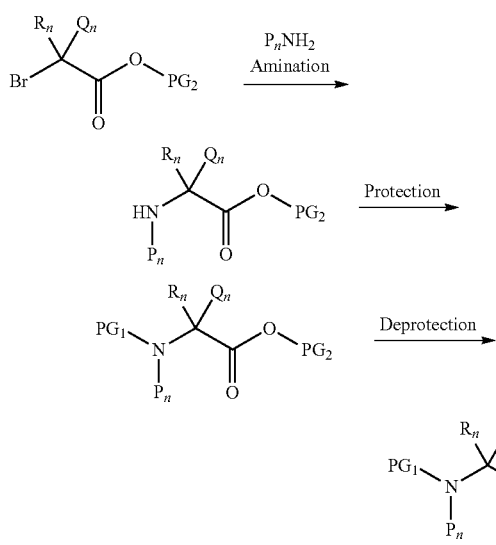

Non-natural amino acids having a —CH$_2$—P' group introduced onto the amino acid nitrogen atom can be prepared according to the following scheme. An oxazolidinone compound having an introduced cyclic protecting group can be obtained by allowing an aldehyde to act on a C-terminal-free amino acid available from a commercial supplier according to the method of Freidinger et al. (J. Org. Chem., 1983, 48(1), 77-81). Next, the target C-terminal-free non-natural amino acid can be prepared by ring-opening reaction.

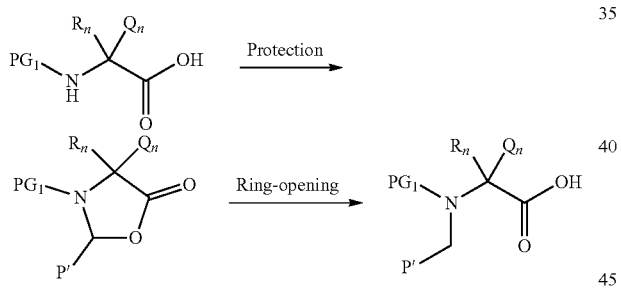

Non-natural amino acids having a P$_n$ group introduced onto the amino acid nitrogen atom can be prepared according to the following scheme. The P$_n$ group can be introduced onto a commercially available C-terminal-free amino acid by allowing an alkylating agent (P$_n$—X) to act on it in the presence of a base. Next, a C-terminal-free non-natural amino acid can be prepared by deprotecting the C-terminal protecting group.

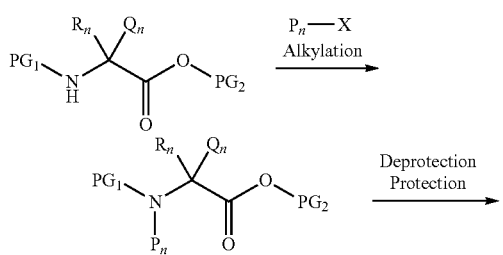

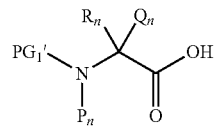

Non-natural amino acids having an amido group introduced onto the amino acid side chain can be prepared according to the following scheme. An amido group can be introduced onto the side chain by deprotecting a commercially available protected amino acid (n=1 or 2) and allowing an amine (R"R'"NH) to act on the resulting carboxylic acid. Next, a C-terminal-free non-natural amino acid can be prepared by deprotecting the C-terminal protecting group.

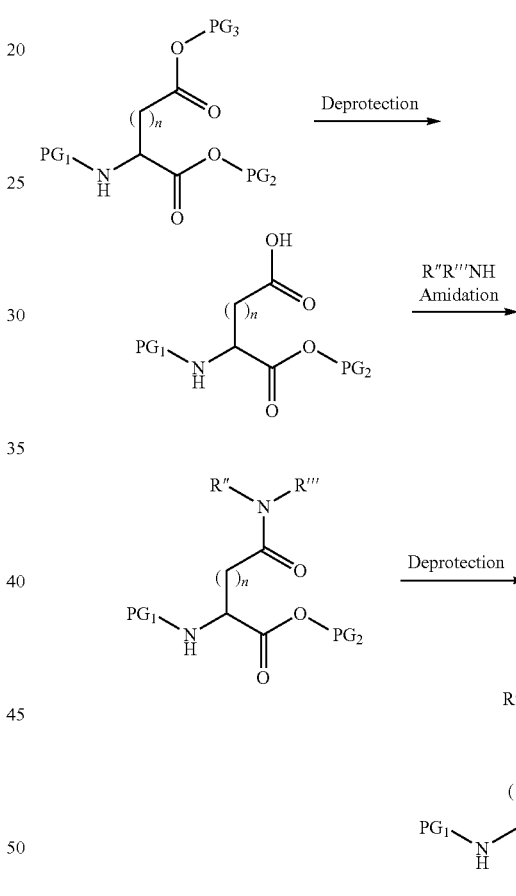

Non-natural amino acids having an amido group introduced onto the amino acid side chain and a —CH$_2$—P' group introduced onto the amino acid nitrogen atom can be prepared according to the following scheme. An oxazolidinone compound having an introduced cyclic protecting group can be obtained by allowing an aldehyde to act on a commercially available protected amino acid (n=1 or 2) according to the method of Freidinger et al. (J. Org. Chem., 1983, 48(1), 77-81). Next, an amide compound can be obtained by deprotecting the side-chain protecting group and then allowing an amine (R"R'"NH) to act on it. Next, the target C-terminal-free non-natural amino acid can be prepared by ring-opening reaction.

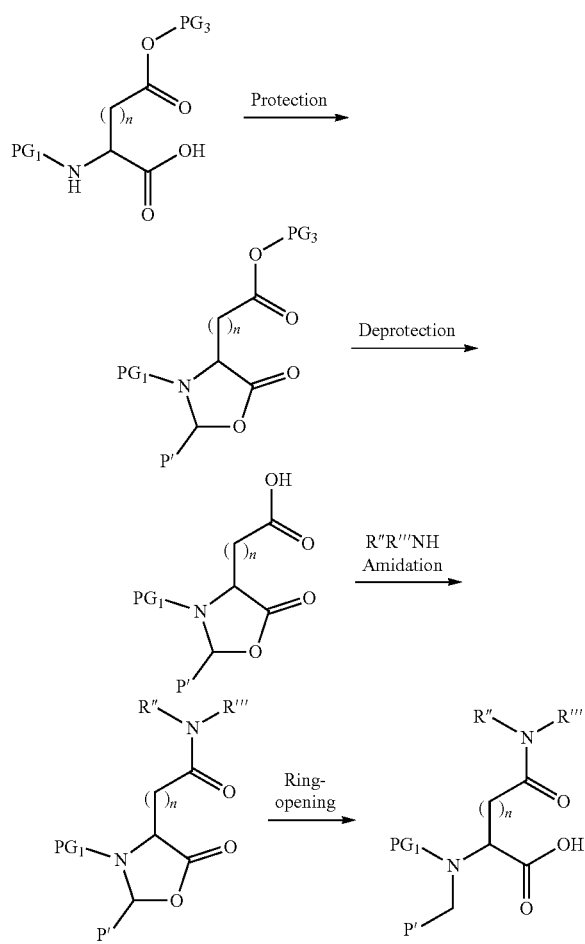

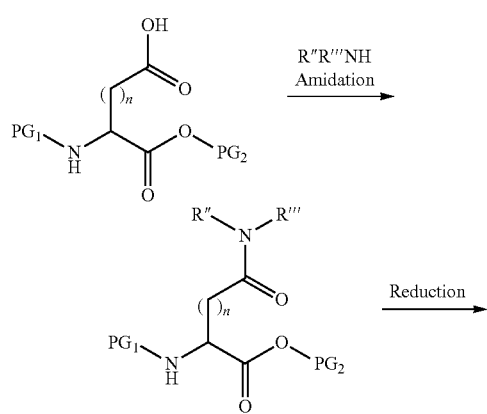

Non-natural amino acids having an amino group introduced onto the amino acid side chain can be prepared according to the following scheme. An amido group can be introduced onto the side chain by allowing an amine (R"R'"NH) to act on the carboxyl group of a commercially available protected amino acid (n=1 or 2). Next, a C-terminal-free non-natural amino acid can be prepared by conducting reduction reaction according to the method of Reeves et al. (Advanced Synthesis & Catalysis, 2013, 355(1), 47-52) and then deprotecting the C-terminal protecting group.

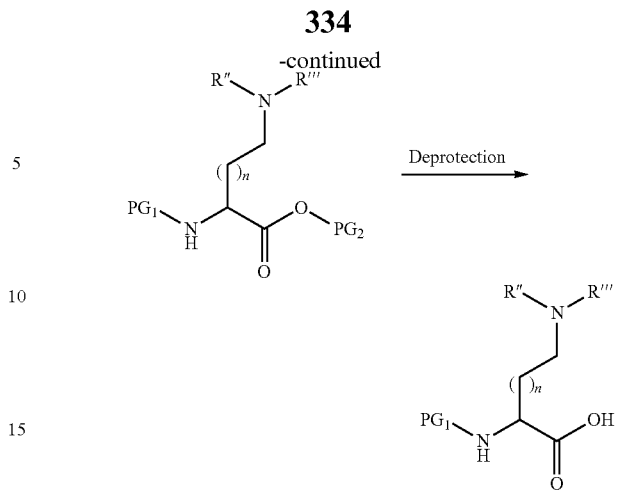

Non-natural amino acids having an amino group introduced onto the amino acid side chain and a —CH$_2$—P' group introduced onto the amino acid nitrogen atom can be prepared according to the following scheme. An amido group can be introduced onto the side chain by allowing an amine (R"R'"NH) to act on the carboxyl group of an amino acid protected by a cyclic protecting group (n=1 or 2). Next, the target C-terminal-free non-natural amino acid can be prepared by conducting reduction reaction according to the method of Reeves et al. (Advanced Synthesis & Catalysis, 2013, 355(1), 47-52) and then performing ring-opening reaction.

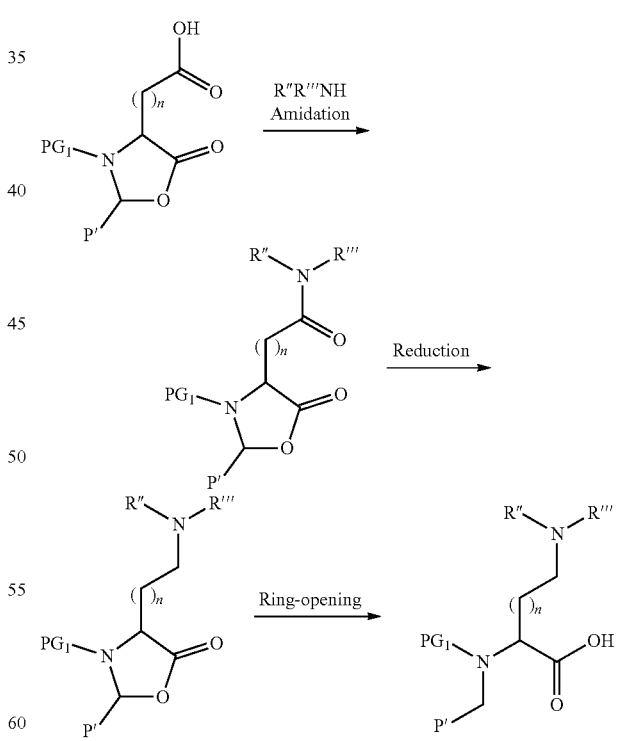

Non-natural amino acids having a fluoroalkyl group introduced onto the amino acid side chain can be prepared according to the following scheme. The carboxyl group of a commercially available protected amino acid (n=1 or 2) can be reduced and converted to an aldehyde group according to a conventional method, and the aldehyde group can be converted to a difluoromethyl group by introducing a fluorine atom according to a conventional method. Next, a C-terminal-free non-natural amino acid can be prepared by deprotecting the C-terminal protecting group.

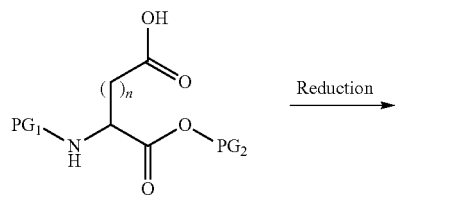

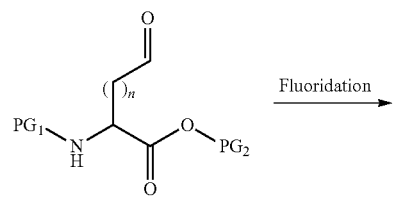

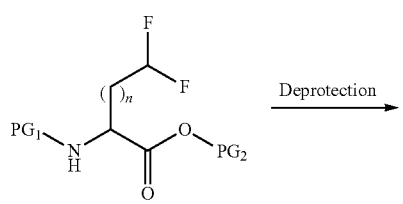

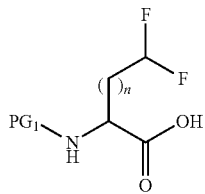

Non-natural amino acids having a fluoroalkyl group introduced onto the amino acid side chain and a —CH₂—P' group introduced onto the amino acid nitrogen atom can be prepared according to the following scheme. The carboxyl group of an amino acid protected by a cyclic protecting group (n=1 or 2) can be reduced and converted to an aldehyde group according to a conventional method, and the aldehyde group can be converted to a difluoromethyl group by introducing a fluorine atom according to a conventional method. Next, a C-terminal-free non-natural amino acid can be prepared by ring-opening of the C-terminal cyclic protecting group.

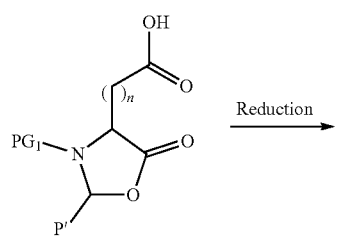

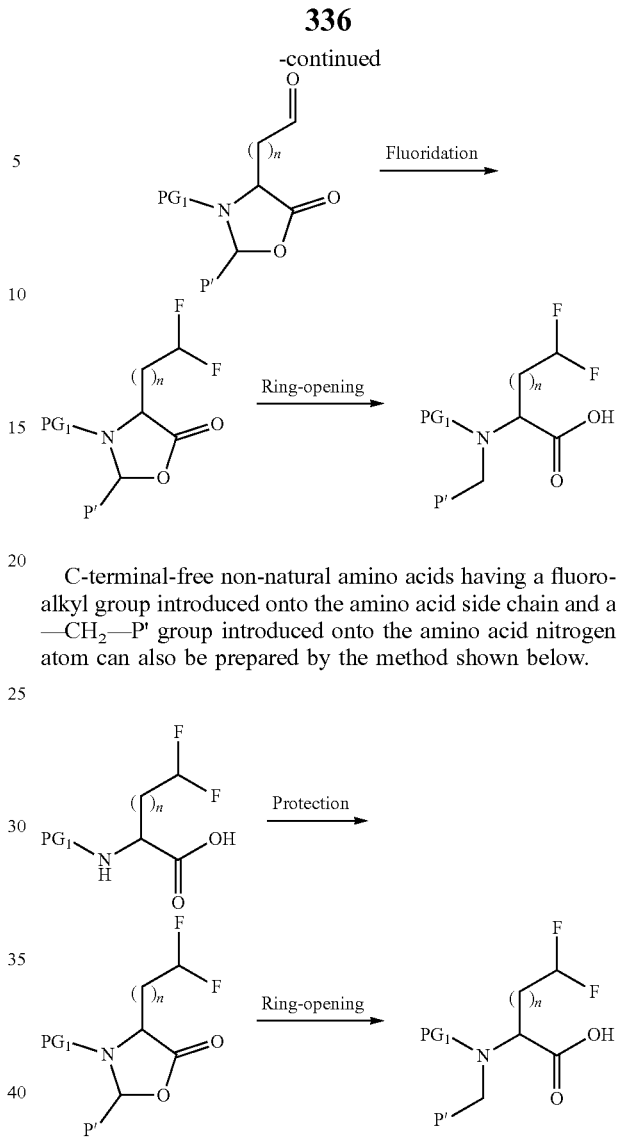

C-terminal-free non-natural amino acids having a fluoroalkyl group introduced onto the amino acid side chain and a —CH₂—P' group introduced onto the amino acid nitrogen atom can also be prepared by the method shown below.

Non-natural amino acids having an aryl or heteroaryl group (such groups are referred to as "Ar" in the scheme) introduced onto the amino acid side chain can be prepared according to the following scheme. An N-hydroxyphthalimide (NHPI) group can be introduced onto the side chain by allowing NHPI to act on the carboxyl group of a protected amino acid (n=1 or 2). A non-natural amino acid having an aryl or heteroaryl group introduced and possessing an aralkyl or heteroaralkyl group on the side chain can be prepared by allowing an aryl halide or heteroaryl halide to react according to the method of Huihui et al. (J. Am. Chem. Soc., 2016, 138(15), 5016-5019). Next, a C-terminal-free non-natural amino acid can be prepared by deprotecting the C-terminal protecting group.

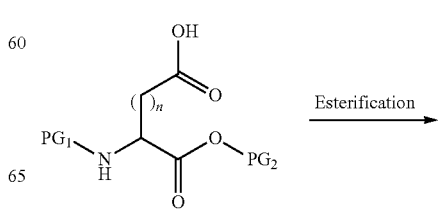

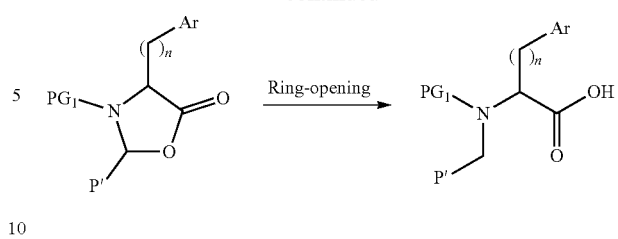

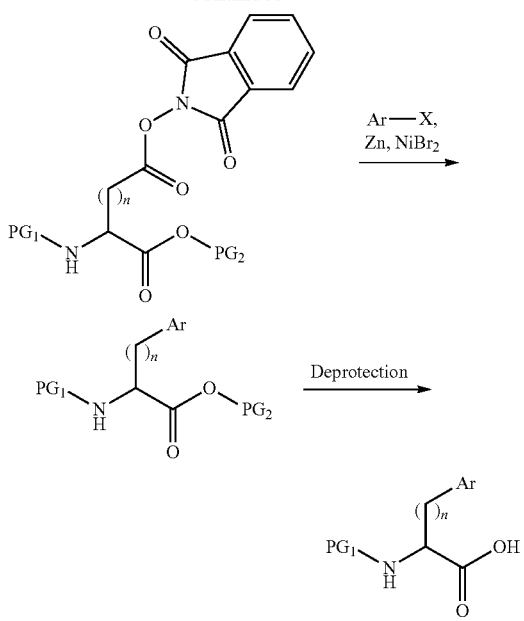

Non-natural amino acids having an aryl or heteroaryl group (such groups are referred to as "Ar" in the scheme) introduced onto the amino acid side chain and having a —CH₂—P' group introduced onto the amino acid nitrogen atom can be prepared according to the following scheme. An N-hydroxyphthalimide (NHPI) group can be introduced onto the side chain by allowing NHPI to act on the carboxyl group of an amino acid protected by a cyclic protecting group (n=1 or 2). A non-natural amino acid which has an aryl or heteroaryl group introduced, and has an aralkyl or heteroarylalkyl group on the side chain, and is protected by a cyclic protecting group, can be prepared by allowing an aryl halide or heteroaryl halide to react according to the method of Huihui et al. (J. Am. Chem. Soc., 2016, 138(15), 5016-5019). Next, the target C-terminal-free non-natural amino acid can be prepared by ring-opening reaction.

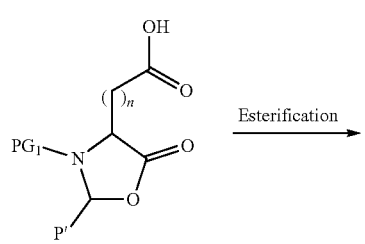

Non-natural amino acids having an aryl or heteroaryl group (such groups are referred to as "Ar" in the scheme) introduced onto the amino acid side chain can be prepared according to the following scheme. A non-natural amino acid having an aryl or heteroaryl group introduced and possessing an aralkyl or heteroaralkyl group on the side chain can be prepared by introducing a protecting group onto a commercially available protected amino group (n=0 or 1) and then allowing an aryl halide or heteroaryl halide to react according to the method of He et al. (Org. Lett. 2014, 16(24), 6488-6491). Next, the target C-terminal-free non-natural amino acid can be prepared by deprotection reaction and protecting group introduction reaction.

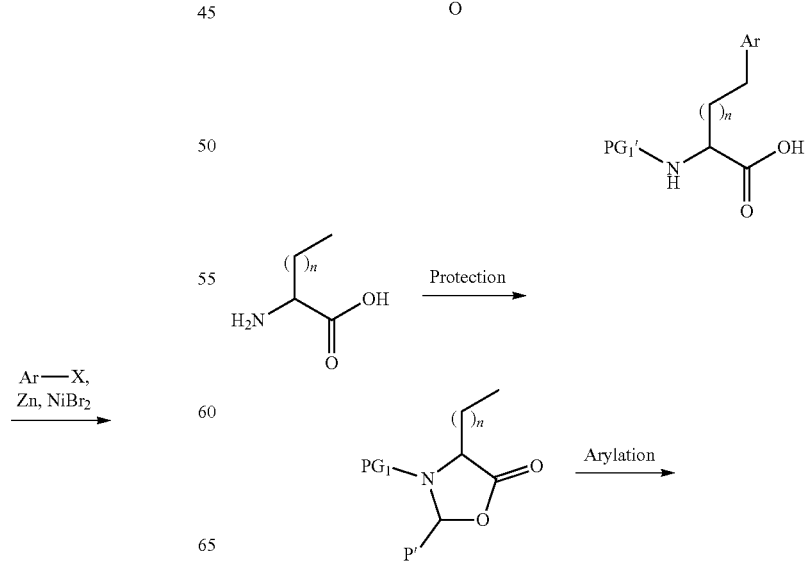

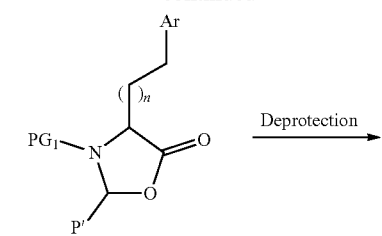

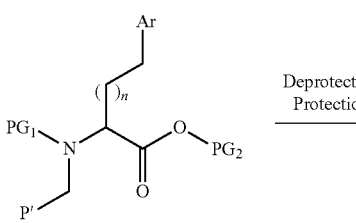

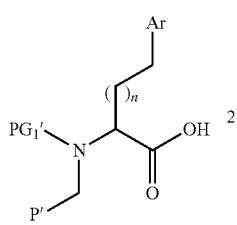

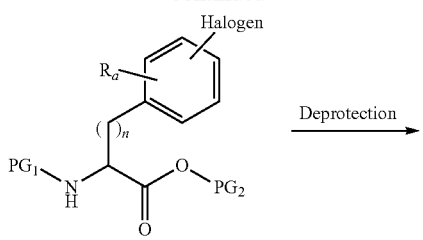

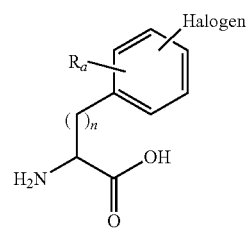

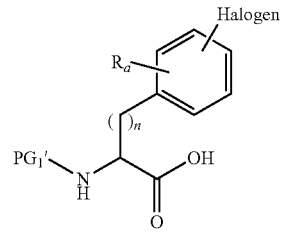

Non-natural amino acids having a halogen atom introduced onto the aralkyl group on the amino acid side chain can be prepared according to the following scheme. A boronic acid ester can be introduced onto the aralkyl group (n=1 to 3) which may have a substituent ($R_a$) on the amino acid side chain according to the method of Ishiyama et al. (J. Am. Chem. Soc. 2002, 124(3), 390-391). A halogen atom can be introduced onto the introduced boryl group using N-halosuccinimide according to the method of Lindner et al. (Chem. Eur. J., 2016, 22, 13218-13235). The target C-terminal-free non-natural amino acid can be prepared by appropriately introducing/removing a protecting group onto/from the obtained non-natural amino acid as necessary.

Non-natural amino acids having a halogen atom introduced onto the aralkyl group of the amino acid side chain and a —$CH_2$—P' group introduced onto the amino acid nitrogen atom can be prepared according to the following scheme. A boronic acid ester can be introduced onto the aryl group of the amino acid having an aralkyl group (n=1 to 3) which may have a substituent ($R_a$) on the amino acid side chain according to the method of Ishiyama et al. (J. Am. Chem. Soc. 2002, 124(3), 390-391). A halogen atom can be introduced onto the introduced boryl group using N-halosuccinimide according to the method of Lindner et al. (Chem. Eur. J., 2016, 22, 13218-13235). The target C-terminal-free non-natural amino acid can be prepared by appropriately introducing/removing a protecting group onto/from the obtained non-natural amino acid as necessary.

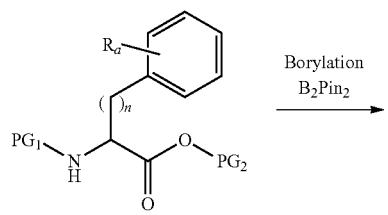

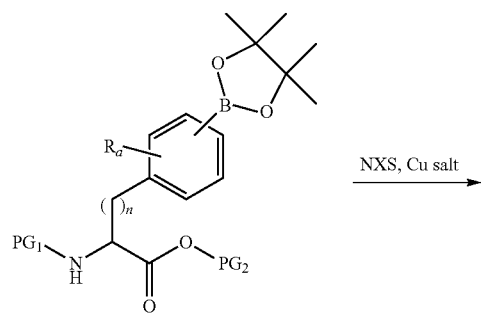

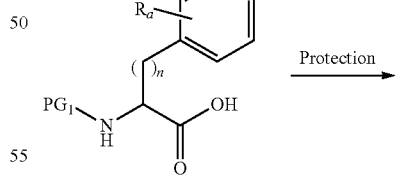

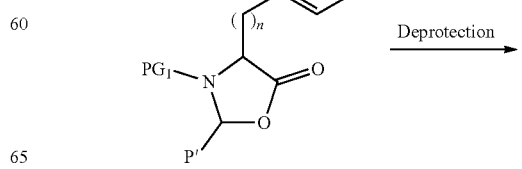

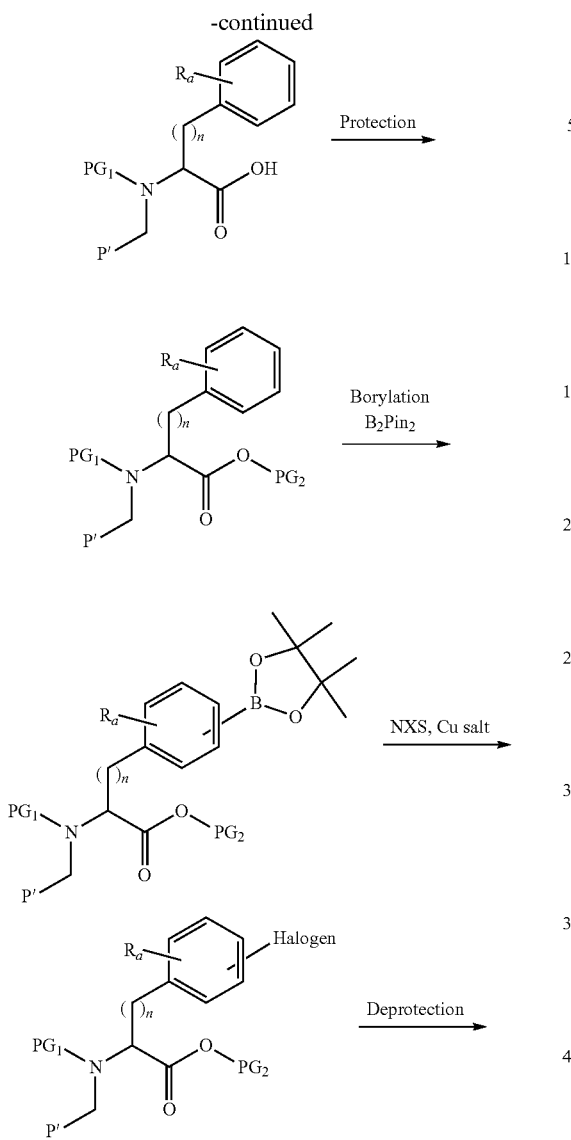

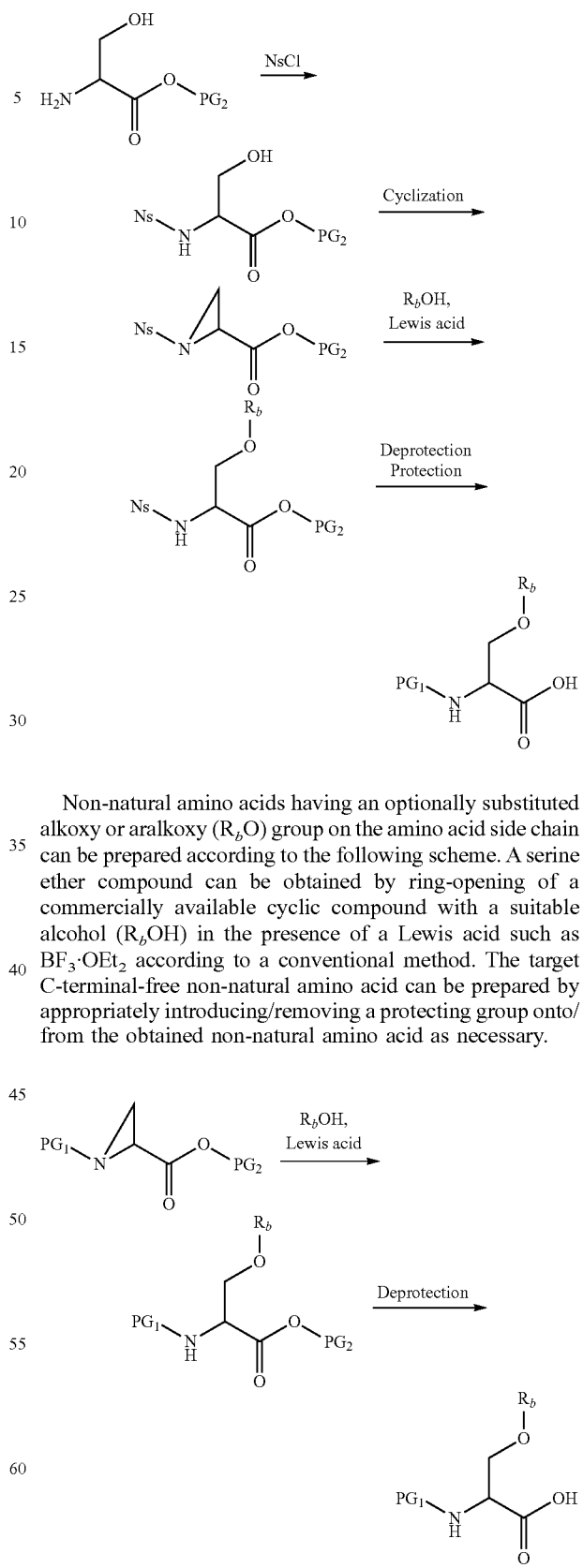

Non-natural amino acids having an optionally substituted alkoxy or aralkoxy ($R_bO$) group on the amino acid side chain can be prepared according to the following scheme. A cyclized compound can be obtained according to the method of Mitsunobu et al. (Synthesis, 1981, 1, 1-28) after introducing a nosyl (Ns) group onto a commercially available serine derivative according to a conventional method. A serine ether compound can be obtained by ring-opening of the cyclized compound with a suitable alcohol ($R_bOH$) in the presence of a Lewis acid such as $BF_3 \cdot OEt_2$. The target C-terminal-free non-natural amino acid can be prepared by appropriately introducing/removing a protecting group onto/from the obtained non-natural amino acid as necessary.

Non-natural amino acids having an optionally substituted alkoxy or aralkoxy ($R_bO$) group on the amino acid side chain can be prepared according to the following scheme. A serine ether compound can be obtained by ring-opening of a commercially available cyclic compound with a suitable alcohol ($R_bOH$) in the presence of a Lewis acid such as $BF_3 \cdot OEt_2$ according to a conventional method. The target C-terminal-free non-natural amino acid can be prepared by appropriately introducing/removing a protecting group onto/from the obtained non-natural amino acid as necessary.

Non-natural amino acids having an optionally substituted alkoxy or aralkoxy (—$OR_b$) group on the amino acid side chain can be prepared according to the following scheme. A serine ether compound can be obtained by allowing an alkylating agent ($R_b$—X) to act on a commercially available serine derivative (n=1 or 2) in the presence of a suitable base according to the method of Williamson et al. (Liebigs Ann. Chem. 1851, 77, 37-49). When $R_b$ has a further convertible functional group, $R_b$ can be converted to a target functional group by additional functional group conversion. Examples of such additional functional group conversion include multiple bond reduction reaction. Next, the target C-terminal-free non-natural amino acid can be prepared by deprotecting the obtained non-natural amino acid.

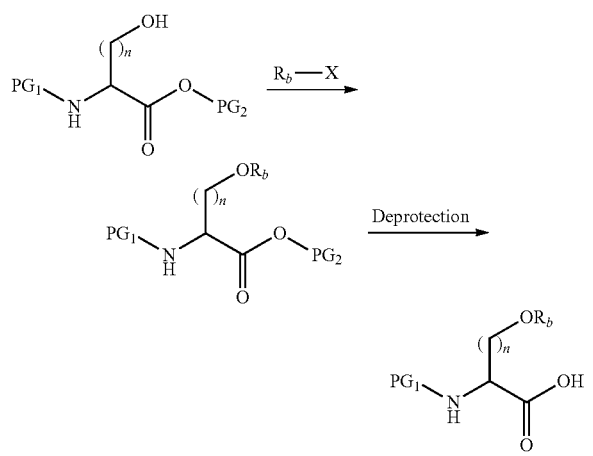

Non-natural amino acids having an optionally substituted alkoxy or aralkoxy (—$OR_b$) group on the amino acid side chain and having a group introduced onto the amino acid nitrogen atom can be prepared according to the following scheme. An oxazolidinone compound having a cyclic protecting group introduced can be obtained by allowing an aldehyde to act on a commercially available serine derivative or a serine derivative prepared by the above-described method (n=1 or 2) according to the method of Freidinger et al. (J. Org. Chem., 1983, 48(1), 77-81). Next, the target C-terminal-free non-natural amino acid can be prepared by ring-opening reaction.

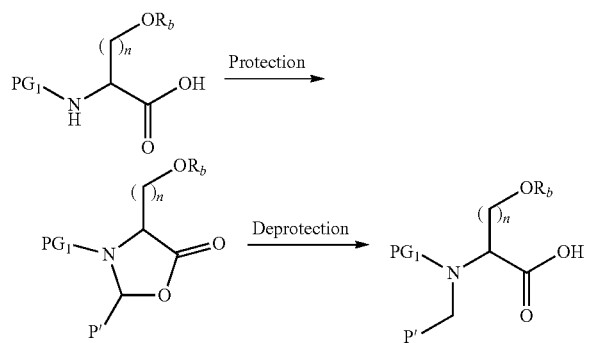

Non-natural amino acids having a protected hydroxy group on the amino acid side chain can be prepared according to the following scheme. The target C-terminal-free non-natural amino acid can be prepared by appropriately introducing/removing a protecting group onto/from a commercially available serine derivative or a serine derivative prepared by the above-described method (n=1 or 2).

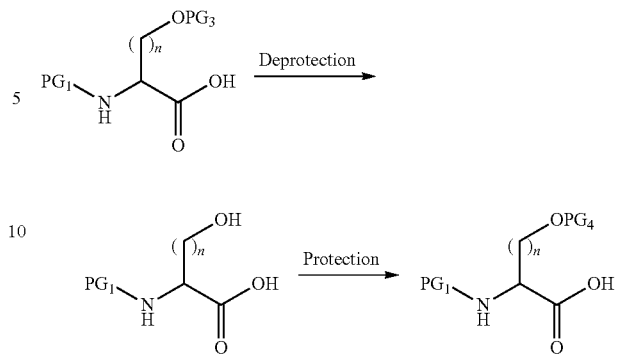

Non-natural amino acids having a protected hydroxy group on the amino acid side chain and a —$CH_2$—P' group introduced onto the amino acid nitrogen atom can be prepared according to the following scheme. An oxazolidinone compound having a cyclic protecting group introduced can be obtained by allowing an aldehyde to act on a commercially available serine derivative or a serine derivative prepared by the above-described method (n=1 or 2) according to the method of Freidinger et al. (J. Org. Chem., 1983, 48(1), 77-81). Next, the target C-terminal-free non-natural amino acid can be prepared by ring-opening reaction and protecting group introduction reaction.

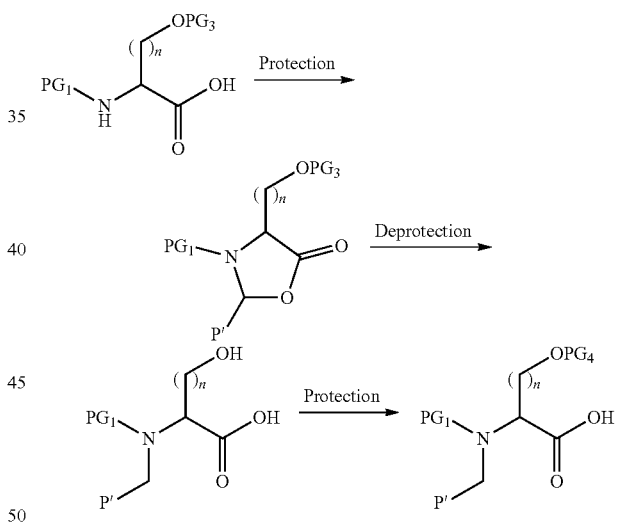

Cyclic non-natural amino acids having a substituent ($R_c$) introduced onto the hydroxyl group of the cyclic amino acid can be prepared according to the following scheme. The hydroxy group of a commercially available cyclic amino acid can be converted to the target —$OR_c$ group by appropriately introducing a functional group. As a reaction of converting the functional group, an ether bond can be produced by allowing an alkylating agent ($R_c$—X) to react in the presence of a suitable base according to the method of Williamson et al. (Liebigs Ann. Chem. 1851, 77, 37-49). When $R_c$ has a further convertible functional group, $R_c$ can be converted to a target functional group by additional functional group conversion. Next, the target C-terminal-free non-natural amino acid can be prepared by deprotection reaction.

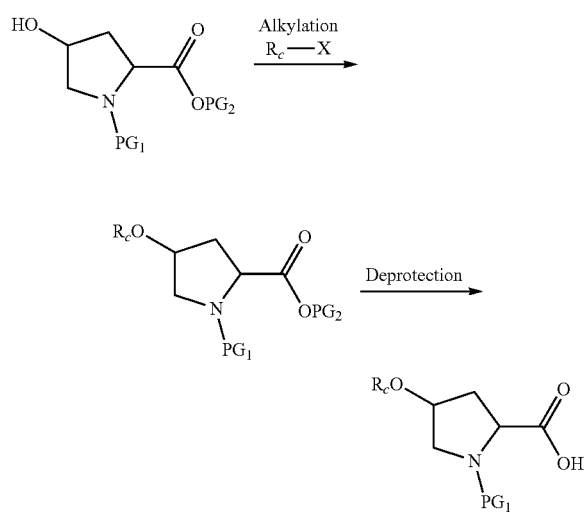

Cyclic non-natural amino acids having a protecting group (PG₃) introduced onto the hydroxyl group of the cyclic amino acid can be prepared according to the following scheme. The target C-terminal-free non-natural amino acid can be prepared by appropriately introducing/removing a protecting group onto/from a commercially available cyclic amino acid.

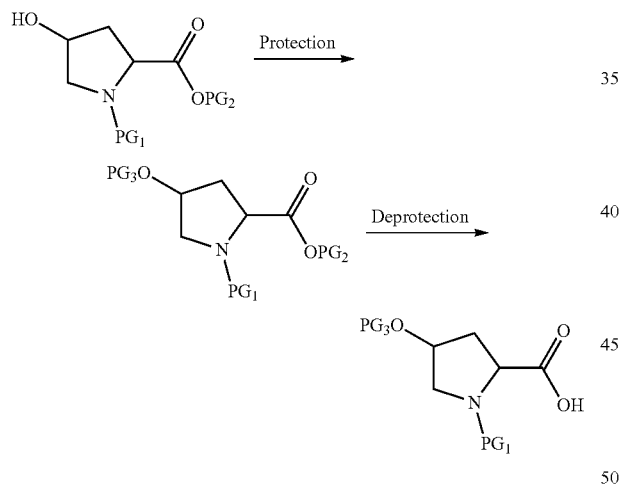

Non-natural amino acids having a boronic acid introduced onto the amino acid side chain can be prepared according to the following scheme. A non-natural amino acid having a boronic acid ester introduced can be obtained by allowing an aldehyde to act on a commercially available glycine derivative according to the method of Lee et al. (Bioorg. Med. Chem. Lett., 2009, 19(17), 4887-5274). Next, the target C-terminal-free non-natural amino acid can be prepared by appropriately introducing or removing a protecting group.

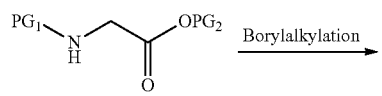

(Synthesis 1 of Fmoc non-natural amino acids having a carboxyl group on the side chain)

Fmoc non-natural amino acids having a carboxyl group on the side chain can be prepared according to the following scheme. The main chain carboxyl group of a starting material which is available from a commercial supplier and has a side chain carboxyl group protected by PG₃ (n=1 or 2) can be converted to an amido group by condensing it with an amine (R"R'"NH) in the presence of a condensing agent such as DIC. Next, the target Fmoc non-natural amino acid having a carboxyl group on the side chain can be prepared by deprotecting PG₃.

(Synthesis 2 of Fmoc Non-Natural Amino Acids Having a Carboxyl Group on the Side Chain)

Fmoc non-natural amino acids having a carboxyl group on the side chain and a —CH₂—P' group introduced onto the amino acid nitrogen atom can be prepared according to the following scheme. The main chain carboxyl group of a starting material which is available from a commercial supplier and has a side chain carboxyl group protected by PG₃ (n=1 or 2) can be converted to an amido group by condensing it with an amine (R"R'"NH) in the presence of a condensing agent such as DIC. Next, the target Fmoc non-natural amino acid having a carboxyl group on the side chain can be prepared by deprotecting $PG_3$.

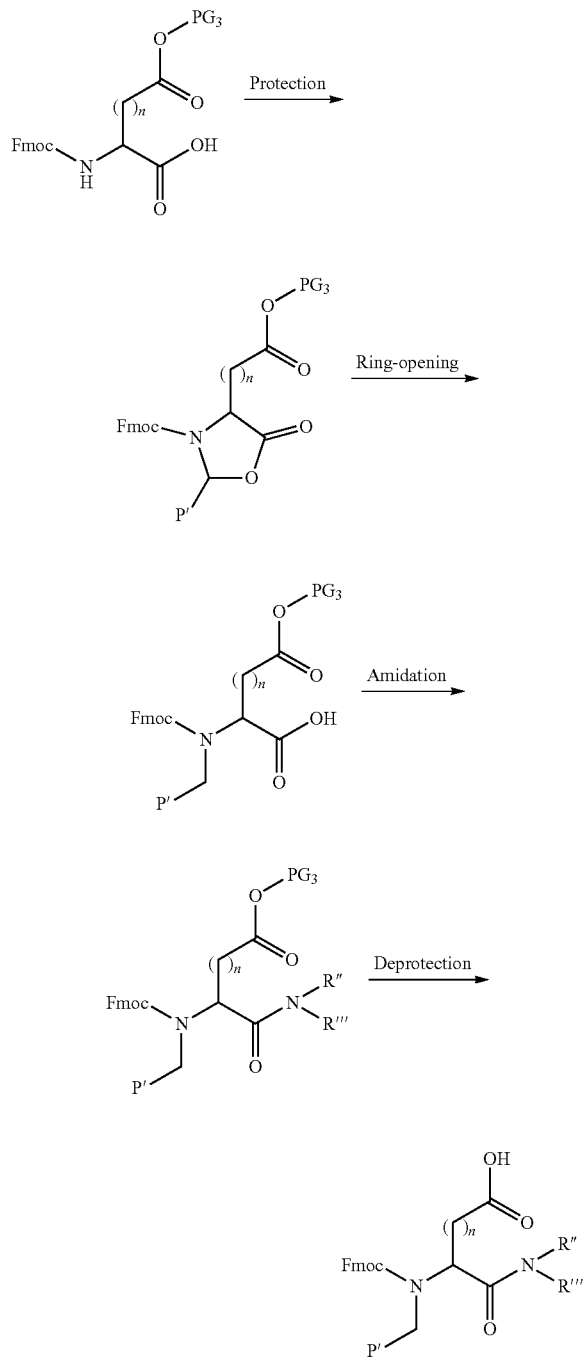

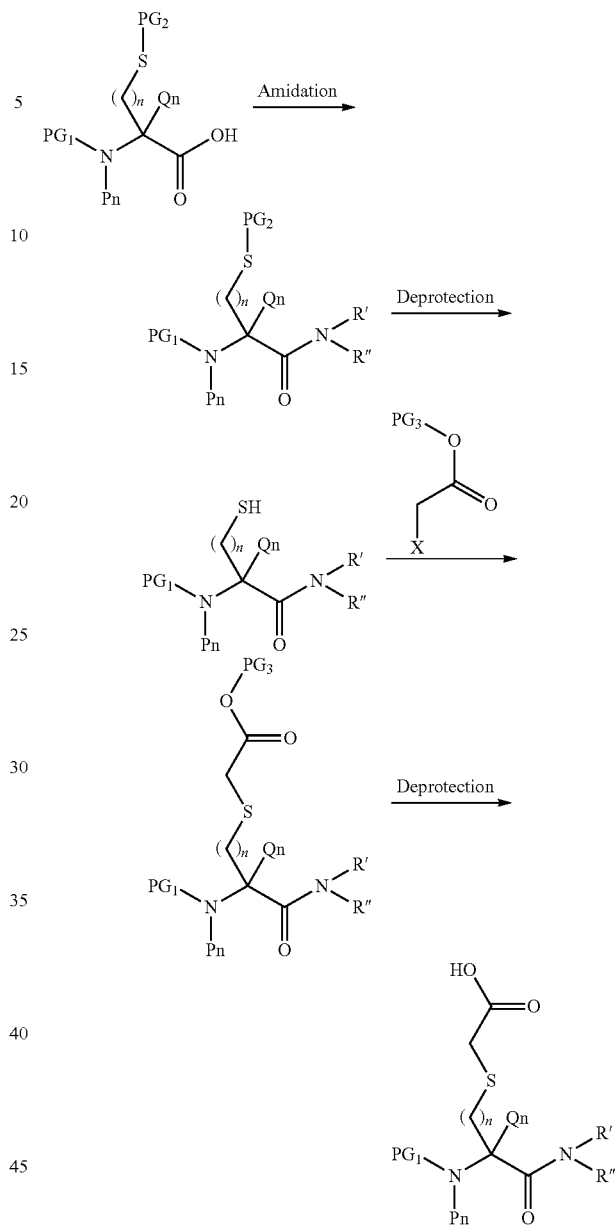

Non-natural amino acids (n=1 or 2) containing a thioether group on the side chain can be produced according to the following scheme. An amino acid having a protected side chain thiol group was subjected to carboxylic acid amidation, and following deprotection of the thiol group, halogenated acetic acid having a protected carboxylic acid was allowed to react to form a thioether bond. Next, the amino acid having a thioether group on the side chain can be produced by deprotecting the side chain carboxylic acid.

Peptides containing a thioether group on the peptide main chain can be produced by using as a raw material the aforementioned amino acid having a thioether group on the side chain, but alternatively, they can also be produced by the method of Roberts et al. in which an N-terminal bromoacetamide is reacted with a cysteine side chain (Tetrahedron Letters, 1998, 39, 8357-8360), or the method of Robey et al. in which an N-terminal chloroacetamide is reacted with a cysteine side chain (Journal of Peptide Research, 2000, 56, 115-120).

The compounds of the present invention and salts thereof, and solvates thereof include all stereoisomers (such as enantiomers and diastereomers (including cis and trans geometric isomers)) of the target compounds obtained through the above-described reaction steps, and racemates and other mixtures of such isomers. For example, the compounds of the present invention may have one or more asymmetric points, and the present invention encompasses racemic mixtures, diastereomeric mixtures, and enantiomers of such compounds.

When the compounds according to the present invention are obtained as free forms, they can be converted to salts that may be formed by such compounds, or hydrates or solvates thereof, according to conventional methods.

When the compounds according to the present invention are obtained as salts, hydrates, or solvates of such compounds, they can be converted to free forms of such compounds according to conventional methods.

<Pharmaceutical Compositions>

The present invention provides pharmaceutical compositions containing the cyclic peptide compounds of the present invention.

The pharmaceutical compositions of the present invention can be formulated by introducing a pharmaceutically acceptable carrier, in addition to the cyclic peptide compound of the present invention, a salt of the cyclic peptide compound, or a solvate thereof by conventional methods. Commonly used excipients, binders, lubricants, colorants, correctives, and as necessary, stabilizers, emulsifiers, absorption promoters, surfactants, pH adjusters, preservatives, antioxidants, and the like can be used for formulation, and they are blended with ingredients generally used as raw materials of pharmaceutical formulations, and formulated by conventional methods.

For example, oral formulations are prepared by adding the cyclic peptide compound of the present invention or a salt thereof, and an excipient, and as necessary, a binder, a disintegrant, a lubricant, a colorant, a corrective, and the like, and then formulating them into powder, fine granules, granules, tablets, coated tablets, capsules, and the like by a conventional method.

Examples of these ingredients include animal and vegetable oils such as soybean oil, beef tallow, and synthetic glyceride; hydrocarbons such as liquid paraffin, squalane, and solid paraffin; ester oils such as octyldodecyl myristate and isopropyl myristate; higher alcohols such as cetostearyl alcohol and behenyl alcohol; silicone resin; silicone oil; surfactants such as polyoxyethylene fatty acid ester, sorbitan fatty acid ester, glycerol fatty acid ester, polyoxyethylene sorbitan fatty acid ester, polyoxyethylene hydrogenated castor oil, and polyoxyethylene-polyoxypropylene block copolymer; water-soluble polymers such as hydroxyethylcellulose, polyacrylic acid, carboxyvinyl polymer, polyethylene glycol, polyvinylpyrrolidone, and methylcellulose; lower alcohols such as ethanol and isopropanol; polyhydric alcohols such as glycerol, propylene glycol, dipropylene glycol, and sorbitol; sugars such as glucose and sucrose; inorganic powders such as silicic anhydride, magnesium aluminum silicate, and aluminum silicate; and purified water.

Examples of the excipients include lactose, corn starch, white soft sugar, glucose, mannitol, sorbitol, microcrystalline cellulose, and silicon dioxide.

Examples of the binders include polyvinyl alcohol, polyvinyl ether, methylcellulose, ethylcellulose, acacia, tragacanth, gelatin, shellac, hydroxypropylmethylcellulose, hydroxypropylcellulose, polyvinylpyrrolidone, polypropylene glycol-polyoxyethylene block polymer, and meglumine.

Examples of the disintegrants include starch, agar, gelatin powder, microcrystalline cellulose, calcium carbonate, sodium bicarbonate, calcium citrate, dextrin, pectin, and carboxymethylcellulose calcium.

Examples of the lubricants include magnesium stearate, talc, polyethylene glycol, silica, and hydrogenated vegetable oil.

For colorants, those approved as additives to pharmaceuticals are used. For correctives, cocoa powder, peppermint camphor, empasm, mentha oil, borneol, powdered cinnamon bark, and the like are used.

Obviously, these tablets and granules may be sugar-coated or otherwise coated appropriately as necessary. When liquid formulations such as syrups and injectable formulations are prepared, they are formulated by adding pH adjusters, solubilizers, tonicity adjusting agents, and the like, and as necessary, solubilizing agents, stabilizers, and the like to the compounds according to the present invention or pharmacologically acceptable salts thereof using conventional methods.

For example, the pharmaceutical compositions can be parenterally used in the form of injectable sterile solutions or suspensions with water or other pharmaceutically acceptable liquids. For example, they would be formulated by appropriately combining with pharmacologically acceptable carriers or media, specifically, sterile water, saline, vegetable oils, emulsifiers, suspending agents, surfactants, stabilizers, flavoring agents, excipients, vehicles, preservatives, or binders, and blending in unit dosage forms required in generally approved formulation. Specifically, carriers may include light anhydrous silicic acid, lactose, microcrystalline cellulose, mannitol, starch, carmellose calcium, carmellose sodium, hydroxypropylcellulose, hydroxypropylmethylcellulose, polyvinyl acetal diethylaminoacetate, polyvinylpyrrolidone, gelatin, medium chain fatty acid triglyceride, polyoxyethylene hydrogenated castor oil 60, white soft sugar, carboxymethylcellulose, corn starch, and inorganic salts. The amount of the active ingredient in such a formulation is designed to provide a suitable dose within an indicated range.

Sterile compositions for injection can be formulated in a conventional formulation manner using a vehicle such as distilled water for injection.

Aqueous solutions for injection include, for example, isotonic solutions containing saline, glucose, and other adjuvants, such as D-sorbitol, D-mannose, D-mannitol, and sodium chloride, and may be used in combination with appropriate solubilizers, for example, alcohols, specifically, ethanol, polyalcohols, e.g., propylene glycol or polyethylene glycol, and nonionic surfactants, e.g., polysorbate 80 (registered trademark) or HCO-50.

Oily liquids include sesame oil and soybean oil, and may be used in combination with benzyl benzoate and benzyl alcohol as solubilizers. They may also be blended with buffering agents such as phosphate buffer and sodium acetate buffer; analgesics such as procaine hydrochloride; stabilizers such as benzyl alcohol and phenol; and antioxidants. Prepared injections are usually packed in suitable ampoules.

The administration method is preferably oral administration, but is not limited thereto. Specific examples of parenteral administration include dosage forms of injection, nasal administration, pulmonary administration, and transdermal administration. Examples of injection dosage forms include systemic or local administration by intravenous injection, intramuscular injection, intraperitoneal injection, subcutaneous injection, etc.

The administration method can also be selected according to the age and symptom of the patient. The dosage of the pharmaceutical composition containing the peptide compound prepared by the method of the present invention can be selected, for example, in the range of 0.0001 mg to 1000 mg per kg body weight per dose. Alternatively, the dosage can be selected, for example, in the range of 0.001 to 100000 mg/body per patient; however, it is not necessarily limited to such values. The dosage and the administration method vary according to the body weight, the age, the symptom, and the like of the patient, but can be appropriately selected by those skilled in the art.

In some embodiments, the compounds of the present invention can be used for inhibiting binding between Kras and SOS.

In some embodiments, the pharmaceutical compositions of the present invention can be used for treating or preventing cancer in a subject. Specific examples of the cancer include pancreatic cancer.

The term "subject" herein includes mammals, and mammals are preferably humans.

All prior art documents cited in the present specification are incorporated herein by reference.

EXAMPLE

The content of the present invention will be further described with reference to Examples and Reference Examples below, but it is not to be construed as being limited thereto. All starting materials and reagents were obtained from commercial suppliers or synthesized by known methods. The LC/MS analysis conditions are described in Table 1.

TABLE 1

| Analysis condition | Device | Column (I.D. × Length) (mm) | Mobile phase | Gradient (A/B) | Flow rate (mL/min) | Column temperature (° C.) | Wavelength | Remarks |
|---|---|---|---|---|---|---|---|---|
| SQDAA05 | Acquity UPLC/SQD or Acquity UPLC/SQD2 | Ascentis Express C18 (2.1 × 50) | A) 10 mM AcONH$_4$, water B) methanol | 95/5 (initial) =>0/100 (1.0 min) =>0/100 (0.4 min) | 1.0 | 35 | 210-400 nm | PDA total |
| SQDFA05 | Acquity UPLC/SQD or Acquity UPLC/SQD2 | Ascentis Express C18 (2.1 × 50) | A) 0.1% FA, water B) 0.1% FA, acetonitrile | 95/5 (initial) =>0/100 (1.0 min) =>0/100 (0.4 min) | 1.0 | 35 | 210-400 nm | PDA total |
| SQDAA50 | Acquity UPLC/SQD or Acquity UPLC/SQD2 | Ascentis Express C18 (2.1 × 50) | A) 10 mM AcONH$_4$, water B) methanol | 50/50 (initial) =>0/100 (0.7 min) =>0/100 (0.7 min) | 1.0 | 35 | 210-400 nm | PDA total |
| SQDFA50 | Acquity UPLC/SQD or Acquity UPLC/SQD2 | Ascentis Express C18 (2.1 × 50) | A) 0.1% FA, water B) 0.1% FA, acetonitrile | 50/50 (initial) =>0/100 (0.7 min) =>0/100 (0.7 min) | 1.0 | 35 | 210-400 nm | PDA total |
| SQDFA05long | Acquity UPLC/SQD2 | Ascentis Express C18 (2.1 × 50) | A) 0.1% FA, water B) 0.1% FA, acetonitrile | 95/5 (initial) =>0/100 (4.5 min) =>0/100 (0.5 min) | 1.0 | 35 | 210-400 nm | PDA total |
| SQDFA3080 | Acquity UPLC/SQD2 | Ascentis Express C18 (2.1 × 50) | A) 0.1% FA, water B) 0.1% FA, acetonitrile | 70/30 (initial) =>20/80 (4.5 min) =>0/100 (0.01 min) =>0/100 (0.49 min) | 1.0 (initial-4.51 min) 0.1 (4.51-5.00 min) | 35 | 210-400 nm | PDA total |
| SQDFA30long50deg | Acquity UPLC/SQD2 | Ascentis Express C18 (2.1 × 50) | A) 0.1% FA, water B) 0.1% FA, acetonitrile | 70/30 (initial) =>0/100 (8.0 min) =>0/100 (2.0 min) | 0.5 | 50 | 210-400 nm | PDA total |
| SMDmethod_01 | Shimadzu LCMS-2020 | Kinetex EVO C18 (2.1 × 50) | A) 6.5 mM NH$_4$HCO$_3$ water (pH = 10) B) acetonitrile | 90/10 (initial) =>50/50 (3.8 min) =>5/95 (0.4 min) =>5/95 (0.4 min) | 1.0 | 35 | 190-400 nm | PDA total |
| SMDmethod 02 | Shimadzu LCMS-2020 | Shim-Pack XR-ODS (3.0 × 50) | A) 0.05% TFA, water B) 0.05% TFA, acetonitrile | 60/40 (initial) =>5/95 (3.0 min) =>5/95 (0.7 min) | 1.2 | 40 | 190-400 nm | PDA total |
| SMDmethod_03 | Nexera/2020 | Ascentis Express C18 (2.1 × 50) | A) 0.1% FA, water B) 0.1% FA, acetonitrile | 95/5 (initial) =>0/100 (4.5 min) =>0/100 (0.5 min) | 1.0 | 35 | 210-400 nm | PDA total |
| SMDmethod_04 | Nexera/2020 | Ascentis Express C18 (2.1 × 50) | A) 0.1% FA, water B) 0.1% FA, acetonitrile | 95/5 (initial) =>0/100 (1.5 min) =>0/100 (0.5 min) | 1.0 | 35 | 210-400 nm | PDA total |
| SMDmethod_05 | Shimadzu LCMS-2020 | Shim-Pack XR-ODS (3.0 × 50) | A) 0.05% TFA, water B) 0.05% TFA, acetonitrile | 95/5 (initial) =>5/95 (2.0 min) =>5/95 (0.7 min) | 1.2 | 40 | 190-400 nm | PDA total |
| SMDmethod_06 | Nexera/2020 | Speed Core C18 (2.1 × 50) | A) 0.1% FA, water B) 0.1% FA, acetonitrile | 95/5(initial) =>0/100(1.5 min) =>0/100(0.5 min) | 1.0 | 35 | 210-400 nm | PDA total |
| SMDmethod_07 | Shimadzu LCMS-2020 | Shim-Pack XR-ODS (3.0 × 50) | A) 0.05% TFA, water B) 0.05% TFA, acetonitrile | 50/50 (initial) =>5/95 (3.8 min) =>5/95 (0.8 min) | 1.2 | 40 | 190-400 nm | PDA total |
| SMDmethod 08 | Shimadzu LCMS-2010EV | Shim-Pack XR-ODS (3.0 × 50) | A) 0.05% TFA, water B) 0.05% TFA, acetonitrile | 50/50 (initial) =>5/95 (2.0 min) =>5/95 (0.7 min) | 1.2 | 40 | 190-400 nm | PDA total |
| SMDmethod 09 | Shimadzu LCMS-2010EV | Shim-Pack XR-ODS (3.0 × 50) | A) 0.05% TFA, water B) 0.05% TFA, acetonitrile | 50/50 (initial) =>5/95 (4.1 min) =>5/95 (0.9 min) | 1.2 | 40 | 190-400 nm | PDA total |
| SMDmethod 10 | Shimadzu LCMS-2020 | Gemini-NX 3u C18 110A (3.0 × 50) | A) 6.5 mM NH$_4$HCO$_3$ water (pH = 10) B) acetonitrile | 70/30 (initial) =>20/80 (4.0 min) =>5/95 (0.5 min) =>5/95 (0.5 min) | 1.2 | 45 | 190-400 nm | PDA total |
| SMDmethod_11 | Shimadzu LCMS-2020 | Phenomenex kinetex C18 (3.0 × 50) | A) 0.1% FA, water B) 0.1% FA, acetonitrile | 90/10 (initial) =>5/95 (2.0 min) =>5/95 (0.7 min) | 1.5 | 40 | 190-400 nm | PDA total |
| SMDmethod_12 | Shimadzu LCMS-2020 | Shim-Pack XR-ODS (3.0 × 50) | A) 0.05% TFA, water B) 0.05% TFA, acetonitrile | 95/5 (initial) =>5/95 (3.0 min) =>5/95 (0.7 min) | 1.2 | 40 | 190-400 nm | PDA total |

TABLE 1-continued

| Analysis condition | Device | Column (I.D. × Length) (mm) | Mobile phase | Gradient (A/B) | Flow rate (mL/min) | Column temperature (° C.) | Wavelength | Remarks |
|---|---|---|---|---|---|---|---|---|
| SMDmethod_13 | Shimadzu LCMS-2020 | Shim-Pack XR-ODS (3.0 × 50) | A) 0.05% TFA, water B) 0.05% TFA, acetonitrile | 50/50 (initial) =>5/95 (2.0 min) =>5/95 (0.7 min) | 1.2 | 40 | 190-400 nm PDA total | |
| SMDmethod_14 | Shimadzu LCMS-2020 | Shim-Pack XR-ODS (3.0 × 50) | A) 0.05% TFA, water B) 0.05% TFA, acetonitrile | 70/30 (initial) =>20/80 (3.8 min) =>0/100 (0.3 min) =>0/100 (0.5 min) | 1.2 | 40 | 190-400 nm PDA total | |
| SMDmethod_15 | Shimadzu LCMS-2020 | Shim-Pack XR-ODS (3.0 × 50) | A) 0.05% TFA, water B) 0.05% TFA, acetonitrile | 95/5 (initial) =>0/100 (1.1 min) =>0/100 (0.6 min) | 1.2 | 40 | 190-400 nm PDA total | |
| SMDmethod_16 | Shimadzu LCMS-2020 | Accucore C18 (2.1 × 50) | A) 0.1% FA, water B) 0.1% FA, acetonitrile | 90/10 (initial) =>0/100 (1.1 min) =>0/100 (0.5 min) | 1.0 | 40 | 190-400 nm PDA total | |
| SMDmethod_17 | Shimadzu LCMS-2020 | Ascentis Express C18 (3.0 × 50) | A) 0.05% TFA, water B) 0.05% TFA, acetonitrile | 95/5 (initial) =>5/95 (2.7 min) =>5/95 (1.0 min) | 1.0 | 40 | 190-400 nm PDA total | |
| SMDmethod_18 | Shimadzu LCMS-2020 | CORTECS C18 (2.1 × 50) | A) 0.1% FA, water B) 0.1% FA, acetonitrile | 95/5 (initial) =>0/100 (1.0 min) =>0/100 (0.5 min) | 1.0 | 40 | 190-400 nm PDA total | |
| SMDmethod_19 | Shimadzu LCMS-2020 | ACQUITY BEH C18 (2.1 × 50) | A) 0.15% FA, water B) 0.15% FA, acetonitrile | 90/10 (initial) =>30/70 (3.6 min) =>30/70 (1.0 min) | 0.7 | 45 | 190-600 nm PDA total | |
| SMDmethod_20 | Shimadzu LCMS-2020 | Ascentis Express C18 (3.0 × 50) | A) 0.05% TFA, water B) 0.05% TFA, acetonitrile | 95/5 (initial) =>5/95 (1.1 min) =>5/95 (0.5 min) | 1.0 | 40 | 190-400 nm PDA total | |
| SMDmethod_21 | Shimadzu LCMS-2010EV | Shim-Pack XR-ODS (3.0 × 50) | A) 0.05% TFA, water B) 0.05% TFA, acetonitrile | 95/5 (initial) =>5/95 (2.0 min) =>5/95 (0.7 min) | 1.2 | 40 | 190-400 nm PDA total | |
| SMDmethod_22 | Shimadzu LCMS-2020 | ACQUITY BEH C18 (2.1 × 50) | A) 0.1% FA, water B) 0.05% FA, acetonitrile | 95/5 (initial) =>20/80 (4 min) =>20/80 (1.2 min) | 0.7 | 45 | 190-800 nm PDA total | |
| SMDmethod_23 | Shimadzu LCMS-2020 | Shim-Pack XR-ODS (3.0 × 50) | A) 0.05% TFA, water B) 0.05% TFA, acetonitrile | 95/5 (initial) =>0/100 (1.2 min) =>0/100 (1 min) | 1.0 | 40 | 190-400 nm PDA total | |
| SSC-AA-20 | Nexera UC/2020 | Ascentis Express C18 (2.1 × 50) | A) 10 mM AcONH$_4$, water B) methanol/1 M AcONH$_2$, water = 100/1 | 95/5 (initial) =>0/100 (1.75 min) =>0/100 (1.25 min) | 1.0 | 35 | 210-400 nm PDA total | |
| SSC-AF-00 | Nexera UC/2020 | Ascentis Express C18 (2.1 × 50) | A) 10 mM NH$_4$HCO$_2$ water B) methanol | 95/5 (initial) =>0/100 (1.75 min) =>0/100 (1.25 min) | 1.0 | 35 | 210-400 nm PDA total | |
| SSC-FA-03 | Nexera UC/2020 | XSelect CSH C18 (2.1 × 50) | A) 0.1% FA, water B) 0.1% FA, acetonitrile | 95/5 (initial) =>0/100 (1.75 min) =>0/100 (1.25 min) | 1.0 | 35 | 210-400 nm PDA total | |
| SSC-TFA-07 | Nexera/2020 | Ascentis Express C18 (2.1 × 50) | A) 0.05% TFA, water B) 0.05% TFA, acetonitrile | 95/5 (initial) =>0/100 (1.5 min) =>0/100 (0.5 min) | 1.0 | 35 | 210-400 nm PDA total | |
| SSC-A-AF-01 | Nexera UC/2020 | Ascentis Express C18 (2.1 × 50) | A) 10 mM NH$_4$HCO$_2$ water B) methanol | 70/30 (initial) =>0/100 (8.75 min) =>0/100 (1.25 min) | 0.5 | 50 | 210-400 nm PDA total | Loop injection |
| SSC-A-AF-02 | Nexera UC/2020 | Ascentis Express C18 (2.1 × 50) | A) 10 mM NH$_4$HCO$_2$, water B) methanol | 70/30 (initial) =>0/100 (8.75 min) =>0/100 (1.25 min) | 0.5 | 50 | 210-400 nm PDA total | Total volume injection |
| SSC-A-FA-01 | Nexera UC/2020 | XSelect CSH C18 (2.1 × 50) | A) 0.1% FA, water B) 0.1% FA, acetonitrile | 70/30 (initial) =>10/90 (7.5 min) =>0/100 (0.01 min) =>0/100 (2.49 min) | 0.5 | 50 | 210-400 nm PDA total | Loop injection |
| SSC-A-FA-02 | Nexera UC/2020 | XSelect CSH C18 (2.1 × 50) | A) 0.1% FA, water B) 0.1% FA, acetonitrile | 70/30 (initial) =>10/90 (7.5 min) =>0/100 (0.01 min) =>0/100 (2.49 min) | 0.5 | 50 | 210-400 nm PDA total | Total volume injection |
| SQDFA05 \| ong | Acquity UPLC/SQD2 | Ascentis Express C18 (2.1 × 50) | A) 0.1% FA, water B) 0.1% FA, acetonitrile | 95/5 (initial) =>0/100 (4.5 min) =>0/100 (0.5 min) | 1.0 | 35 | 210-400 nm PDA total | |
| SMDmethod_30 | Shimadzu LCMS-2020 | Halo C18 (3.0 × 30) | A) 0.05% TFA, water B) 0.05% TFA, acetonitrile | 95/5 (initial) =>0/100 (0.7 min) =>0/100 (0.4 min) | 1.2 | 45 | 190-400 nm PDA total | |
| SMDmethod_31 | Shimadzu LCMS-2020 | Ascentis Express C18 (3.0 × 50) | A) 0.05% TFA, water B) 0.05% TFA, acetonitrile | 95/5 (initial) =>0/100 (2.0 min) =>0/100 (0.7 min) | 1.5 | 40 | 190-400 nm PDA total | |

Example 1

Solid-Phase Synthesis of Peptide Compounds

Peptides were elongated by the following basic route (also called the basic peptide synthesis method) according to the peptide synthesis method by Fmoc methods described in WO 2013/100132 or WO 2018/225864, specifically, by the following five steps:

1) elongation reaction of the peptide by the Fmoc method from the N-terminal amino acid of Asp side chain carboxylic acid or peptide main chain carboxylic acid loaded onto 2-chlorotrityl resin;
2) cleavage of the peptide from the 2-chlorotrityl resin;
3) amide cyclization by condensation between the Asp side chain carboxylic acid or peptide main chain carboxylic acid released from the 2-chlorotrityl resin by the cleavage and the amino group of the peptide chain N-terminus (triangle unit);
4) deprotection of the protecting group of a side chain functional group contained in the peptide chain, as necessary; and
5) purification of the compound by preparative HPLC. In the present Examples, unless otherwise stated, peptide compounds were synthesized based on this basic route.

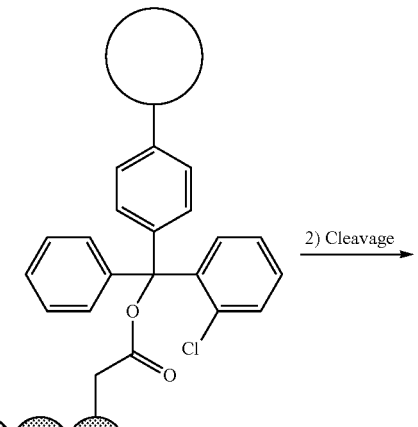

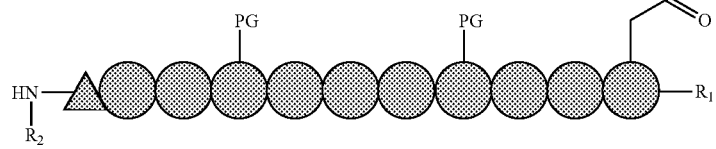

1) After Elongation

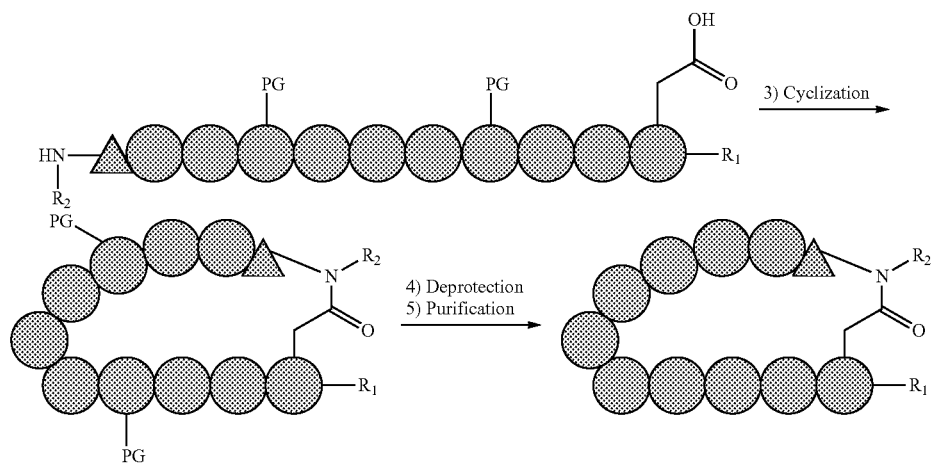

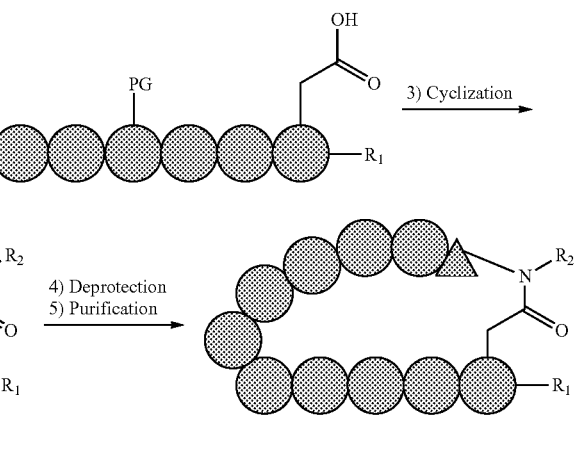

1-1. Fmoc Amino Acids Used in Peptide Synthesis by a Peptide Synthesizer

Fmoc amino acids described in Tables 2 to 5 were used in peptide syntheses described herein using a peptide synthesizer.

Fmoc amino acids described in Table 2 were synthesized according to the methods described in WO 2013/100132 or WO 2018/225864.

Fmoc amino acids described in Table 3 were purchased from commercial suppliers or synthesized according to the methods described in WO 2018/225864.

Fmoc amino acids described in Table 4 were purchased from commercial suppliers.

Fmoc amino acids described in Table 5 were synthesized according to the schemes provided below.

TABLE 2

| Abbreviation | Structural formula | Name |
| --- | --- | --- |
| Fmoc-MeAla(4-Thz)-OH | | (2S)-2-[9H-fluoren-9-yl methoxy carbonyl(methyl)amino]-3-(1,3-thiazol-4-yl)propanoic acid |
| Fmoc-MePhe(3-Cl)-OH | | (2S)-3-(3-chlorophenyl)-2-[9H-fluoren-9-yl methoxycarbonyl (methyl)amino]propanoic acid |
| Fmoc-nPrGly-OH | | 2-[9H-fluoren-9-yl methoxycarbonyl (propyl)amino]acetic acid |
| Fmoc-Hyp(Et)-OH | | (2S,4R)-4-ethoxy-1-(9H-fluoren-9-yl methoxycarbonyl)pyrrolidin-2-carboxylic acid |
| Fmoc-(EtOEt)NGly-OH | | 2-[2-ethoxyethyl(9H-fluoren-9-yl methoxycarbonyl)amino]acetic acid |

TABLE 2-continued

| Abbreviation | Structural formula | Name |
|---|---|---|
| Fmoc-cisPro(pip-4-F2)-OH | | (2S,4S)-4-(4,4-difluoropiperidin-1-yl)-1-(9H-fluoren-9-yl methoxycarbonyl) pyrrolidin-2-carboxylic acid |
| Fmoc-Hnl(7-F2)-OH | | (2S)-2-(9H-fluoren-9-yl methoxy carbonylamino)-7,7-difluoro heptanoic acid |
| Fmoc-iPenGly-OH | | 2-[9H-fluoren-9-yl methoxycarbonyl (3-methyl butyl)amino]acetic acid |
| Fmoc-MeAbu(pip-3-F2)-OH | | (2S)-4-(3,3-difluoropiperidin-1-yl)-2-[9H-fluoren-9-yl methoxycarbonyl (methyl)amino]butanoic acid |
| Fmoc-MeGln(Me)-OH | | (2S)-2-[9H-fluoren-9-yl methoxy carbonyl(methyl)amino]-5-(methyl amino)-5-oxopentanoic acid |

TABLE 2-continued

| Abbreviation | Structural formula | Name |
| --- | --- | --- |
| Fmoc-MeGln(Me2)-OH | | (2S)-5-(dimethyl amino)-2-[9H-fluoren-9-yl methoxycarbonyl(methyl)amino]-5-oxopentanoic acid |
| Fmoc-MeHnl(7-F2)-OH | | (2S)-2-[9H-fluoren-9-yl methoxycarbonyl(methyl)amino]-7,7-difluoro heptanoic acid |
| Fmoc-MeHph-OH | | (2S)-2-[9H-fluoren-9-yl methoxycarbonyl(methyl)amino]-4-phenyl butanoic acid |
| Fmoc-MePhe(4-Cl)-OH | | (2S)-3-(4-chlorophenyl)-2-[9H-fluoren-9-yl methoxycarbonyl (methyl) amino]propanoic acid |

TABLE 2-continued

| Abbreviation | Structural formula | Name |
|---|---|---|
| Fmoc-MeSer(THP)-OH | | (2S)-2-[9H-fluoren-9-yl methoxy carbonyl(methyl)amino]-3-(oxan-2-yloxy)propanoic acid |
| Fmoc-MeSer(3-F-5-Me-Pyr)-OH | | (2S)-2-[9H-fluoren-9-yl methoxy carbonyl(methyl)amino]-3-[(5-fluoro pyridin-3-yl)methoxy]propanoic acid |
| Fmoc-MeSer(iPen)-OH | | (2S)-2-[9H-fluoren-9-yl methoxy carbonyl(methyl)amino]-3-(3-methyl butoxy)propanoic acid |
| Fmoc-MeSer(nPr)-OH | | (2S)-2-[9H-fluoren-9-yl methoxy carbonyl(methyl)amino]-3-propoxy propanoic acid |

TABLE 2-continued

| Abbreviation | Structural formula | Name |
|---|---|---|
| Fmoc-MeSer(NtBu-Aca)-OH | | (2S)-3-[2-(tert-butyl amino)-2-oxo ethoxy]-2-[9H-fluoren-9-yl methoxy carbonyl(methyl)amino]propanoic acid |
| Fmoc-MeSer(Ph-2-Cl)-OH | | (2S)-3-(2-chlorophenoxy)-2-[9H-fluoren-9-yl methoxycarbonyl (methyl)amino]propanoic acid |
| Fmoc-MeSer(tBuOTHP)-OH | | (2S)-2-[9H-fluoren-9-yl methoxy carbonyl(methyl)amino]-3-[2-methyl-2-(oxan-2-yloxy)propoxy]propanoic acid |
| Fmoc-nBuGly-OH | | 2-[butyl(9H-fluoren-9-yl methoxy carbonyl)amino]acetic acid |

TABLE 2-continued

| Abbreviation | Structural formula | Name |
|---|---|---|
| Fmoc-Pro(4-pip-4-F2)-OH | | (2S,4R)-4-(4,4-difluoropiperidin-1-yl)-1-(9H-fluoren-9-yl methoxy carbonyl)pyrrolidin-2-carboxylic acid |
| Fmoc-Ser(3-F-5-Me-Pyr)-OH | | (2S)-2-(9H-fluoren-9-yl methoxy carbonyl amino)-3-[(5-fluoropyridin-3-yl)methoxy]propanoic acid |
| Fmoc-Ser(iPen)-OH | | (2S)-2-(9H-fluoren-9-yl methoxy carbonyl amino)-3-(3-methylbutoxy) propanoic acid |
| Fmoc-Ser(nPr)-OH | | (2S)-2-(9H-fluoren-9-yl methoxy carbonyl amino)-3-propoxypropanoic acid |

TABLE 2-continued

| Abbreviation | Structural formula | Name |
| --- | --- | --- |
| Fmoc-Ser(NtBu-Aca)-OH | | (2S)-3-[2-(tert-butyl amino)-2-oxo ethoxy]-2-(9H-fluoren-9-yl methoxy carbonyl amino)propanoic acid |
| Fmoc-Ser(tBuOTHP)-OH | | (2S)-2-(9H-fluoren-9-yl methoxy carbonyl amino)-3-[2-methyl-2-(oxan-2-yloxy)propoxy]propanoic acid |
| Fmoc-Thr(THP)-OH | | (2S,3R)-2-(9H-fluoren-9-yl methoxy carbonyl amino)-3-(oxan-2-yloxy) butanoic acid |
| Fmoc-Ser(THP)-OH | | (2S)-2-(9H-fluoren-9-yl methoxy carbonyl amino)-3-(oxan-2-yloxy) propanoic acid |

TABLE 2-continued

| Abbreviation | Structural formula | Name |
|---|---|---|
| Fmoc-Tyr(3-F,tBu)-OH | | (2S)-2-(9H-fluoren-9-yl methoxy carbonyl amino)-3-[3-fluoro-4-[(2-methyl propan-2-yl)oxy]phenyl] propanoic acid |

TABLE 3

| Abbreviation | Structural formula | Name |
|---|---|---|
| Fmoc-Hph(3-Cl)-OH | | (2S)-4-(3-chlorophenyl)-2-(9H-fluoren-9-yl methoxycarbonyl amino)butanoic acid |
| Fmoc-Hph(4-Cl)-OH | | (2S)-4-(4-chlorophenyl)-2-(9H-fluoren-9-yl methoxycarbonyl amino)butanoic acid |

TABLE 4

| Abbreviation | Structural formula | Name | CAS No. |
|---|---|---|---|
| Fmoc-Phe(4-CHF2)-OH | | (2S)-3-[4-(difluoromethyl)phenyl]-2-(9H-fluoren-9-yl methoxycarbonyl amino) propanoic acid | 1808268-08-7 |
| Fmoc-Phe(2-F-3-Br)-OH | | (2S)-3-(3-bromo-2-fluoro phenyl]-2-(9H-fluoren-9-yl methoxycarbonyl amino) propanoic acid | 2015410-80-5 |
| Fmoc-Phe(2-F-5-Br)-OH | | (2S)-3-(5-bromo-2-fluoro phenyl]-2-(9H-fluoren-9-yl methoxycarbonyl amino) propanoic acid | 1998646-62-0 |
| Fmoc-Phe(3-Br)-OH | | (2S)-3-(3-bromophenyl)-2-(9H-fluoren-9-yl methoxy carbonyl amino)propanoic acid | 220497-48-3 |

TABLE 4-continued

| Abbreviation | Structural formula | Name | CAS No. |
|---|---|---|---|
| Fmoc-Phe(3-Br-5-F)-OH | | (2S)-3-(3-bromo-5-fluoro phenyl]-2-(9H-fluoren-9-yl methoxycarbonyl amino) propanoic acid | 1998639-82-9 |
| Fmoc-Phe(3-Cl-5-F)-OH | | (2S)-3-(3-chloro-5-fluoro phenyl]-2-(9H-fluoren-9-yl methoxycarbonyl amino) propanoic acid | 1998650-51-3 |
| Fmoc-Phe(3-CN)-OH | | (2S)-3-(3-cyanophenyl)-2-(9H-fluoren-9-yl methoxy carbonyl amino)propanoic acid | 205526-36-9 |
| Fmoc-Phe(4-Cl)-OH | | (2S)-3-(4-chlorophenyl)-2-(9H-fluoren-9-yl methoxy carbonyl amino)propanoic acid | 175453-08-4 |
| Fmoc-(Me)Abu-OH | | (2S)-2-(9H-fluoren-9-yl methoxycarbonyl amino)-2-methylbutanoic acid | 857478-30-9 |

TABLE 4-continued

| Abbreviation | Structural formula | Name | CAS No. |
|---|---|---|---|
| Fmoc-(Me)Algly-OH | | (2S)-2-(9H-fluoren-9-yl methoxycarbonyl amino)-2-methyl pent-4-enoic acid | 288617-71-0 |
| Fmoc-(Me)Leu-OH | | (2S)-2-(9H-fluoren-9-yl methoxycarbonyl amino)-2,4-dimethyl pentanoic acid | 312624-65-0 |
| Fmoc-(Me)Phe-OH | | (2S)-2-(9H-fluoren-9-yl methoxycarbonyl amino)-2-methyl-3-phenyl propanoic acid | 135944-05-7 |
| Fmoc-1-ACPrC-OH | | 1-(9H-fluoren-9-yl methoxy carbonyl amino)cyclo propan-1-carboxylic acid | 126705-22-4 |
| Fmoc-Abu-OH | | (2S)-2-(9H-fluoren-9-yl methoxycarbonyl amino) butanoic acid | 135112-27-5 |
| Fmoc-Abu(4-F3)-OH | | (2S)-2-(9H-fluoren-9-yl methoxycarbonyl amino)-4,4,4-trifluorobutanoic acid | 181128-48-3 |

TABLE 4-continued

| Abbreviation | Structural formula | Name | CAS No. |
|---|---|---|---|
| Fmoc-Ahp(2)-OH | | (2S)-2-(9H-fluoren-9-yl methoxycarbonyl amino) heptanoic acid | 1197020-22-6 |
| Fmoc-Ahpe(2)-OH | | (2S)-2-(9H-fluoren-9-yl methoxycarbonyl amino) hept-6-enoic acid | 856412-22-1 |
| Fmoc-Aib-OH | | 2-(9H-fluoren-9-yl methoxy carbonyl amino)-2-methyl propanoic acid | 94744-50-0 |
| Fmoc-Ala-OH | | (2S)-2-(9H-fluoren-9-yl methoxycarbonyl amino) propanoic acid | 35661-39-3 |
| Fmoc-Ala(cBu)-OH | | (2S)-3-cyclobutyl-2-(9H-fluoren-9-yl methoxycarbonyl amino)propanoic acid | 478183-62-9 |

TABLE 4-continued

| Abbreviation | Structural formula | Name | CAS No. |
|---|---|---|---|
| Fmoc-Ala(CN)-OH | | (2S)-3-cyano-2-(9H-fluoren-9-yl methoxycarbonyl amino)propanoic acid | 127273-06-7 |
| Fmoc-Ala(cPent)-OH | | (2S)-3-cyclopentyl-2-(9H-fluoren-9-yl methoxycarbonyl amino)propanoic acid | 371770-32-0 |
| Fmoc-Ala(cPr)-OH | | (2S)-3-cyclopropyl-2-(9H-fluoren-9-yl methoxycarbonyl amino) propanoic acid | 214750-76-2 |
| Fmoc-Algly-OH | | (2S)-2-(9H-fluoren-9-yl methoxycarbonyl amino) pent-4-enoic acid | 146549-21-5 |
| Fmoc-AllylGly-OH | | 2-[9H-fluoren-9-yl methoxy carbonyl(prop-2-enyl)amino] acetic acid | 222725-35-1 |
| Fmoc-Athpc-OH | | 4-(9H-fluoren-9-yl methoxy carbonylamino)oxan-4-carboxylic acid | 285996-72-7 |

TABLE 4-continued

| Abbreviation | Structural formula | Name | CAS No. |
|---|---|---|---|
| Fmoc-Aze(2)-OH | | (2S)-1-(9H-fluoren-9-yl methoxycarbonyl)azetidin-2-carboxylic acid | 136552-06-2 |
| Fmoc-bAla-OH | | 3-(9H-fluoren-9-yl methoxy carbonyl amino)propanoic acid | 35737-10-1 |
| Fmoc-bMeAla-OH | | 3-[9H-fluoren-9-yl methoxy carbonyl(methyl)amino] propanoic acid | 172965-84-3 |
| Fmoc-BnGly-OH | | 2-[benzyl(9H-fluoren-9-yl methoxycarbonyl)amino] acetic acid | 141743-13-7 |
| Fmoc-Cha-OH | | (2S)-3-cyclohexyl-2-(9H-fluoren-9-yl methoxycarbonyl amino)propanoic acid | 135673-97-1 |
| Fmoc-cHex-OH | | 1-(9H-fluoren-9-yl methoxy carbonyl amino)cyclohexan-1-carboxylic acid | 162648-54-6 |

TABLE 4-continued

| Abbreviation | Structural formula | Name | CAS No. |
|---|---|---|---|
| Fmoc-Chg-OH | | (2S)-2-cyclohexyl-2-(9H-fluoren-9-yl methoxycarbonyl amino)acetic acid | 161321-36-4 |
| Fmoc-cLeu-OH | | 1-(9H-fluoren-9-yl methoxy carbonyl amino)cyclo pentan-1-carboxylic acid | 117322-30-2 |
| Fmoc-cVal-OH | | 1-(9H-fluoren-9-yl methoxy carbonylamino)cyclobutan-1-carboxylic acid | 885951-77-9 |
| Fmoc-D-(Me)Abu-OH | | (2R)-2-(9H-fluoren-9-yl methoxycarbonyl amino)-2-methylbutanoic acid | 1231709-22-0 |
| Fmoc-D-(Me)Algly-OH | | (2R)-2-(9H-fluoren-9-yl methoxycarbonyl amino)-2-methylpent-4-enoic acid | 288617-76-5 |
| Fmoc-D-Ala-OH | | (2R)-2-(9H-fluoren-9-yl methoxycarbonyl amino) propanoic acid | 79990-15-1 |

TABLE 4-continued

| Abbreviation | Structural formula | Name | CAS No. |
|---|---|---|---|
| Fmoc-D-Algly-OH | | (2R)-2-(9H-fluoren-9-yl methoxycarbonyl amino) pent-4-enoic acid | 170642-28-1 |
| Fmoc-D-MeAbu-OH | | (2R)-2-[9H-fluoren-9-yl methoxycarbonyl(methyl) amino]butanoic acid | 1210830-60-6 |
| Fmoc-D-MeAla-OH | | (2R)-2-[9H-fluoren-9-yl methoxycarbonyl(methyl) amino]propanoic acid | 138774-92-2 |
| Fmoc-D-MePhe-OH | | (2R)-2-[9H-fluoren-9-yl methoxycarbonyl(methyl) amino]-3-phenyl propanoic acid | 138775-05-0 |
| Fmoc-D-Mor(3)-OH | | (3R)-4-(9H-fluoren-9-yl methoxycarbonyl) morpholin-3-carboxylic acid | 942153-03-9 |
| Fmoc-D-Pic(2)-OH | | (2R)-1-(9H-fluoren-9-yl methoxycarbonyl) piperidin-2-carboxylic acid | 101555-63-9 |

TABLE 4-continued

| Abbreviation | Structural formula | Name | CAS No. |
|---|---|---|---|
| Fmoc-D-Pro-OH | | (2R)-1-(9H-fluoren-9-yl methoxycarbonyl) pyrrolidin-2-carboxylic acid | 101555-62-8 |
| Fmoc-D-Val-OH | | (2R)-2-(9H-fluoren-9-yl methoxycarbonyl amino)-3-methyl butanoic acid | 84624-17-9 |
| Fmoc-EtGly-OH | | 2-[ethyl(9H-fluoren-9-yl methoxycarbonyl)amino] acetic acid | 162545-29-1 |
| Fmoc-Glu(OAl)-OH | | (2S)-2-(9H-fluoren-9-yl methoxycarbonyl amino)-5-oxo-5-prop-2-enoxy pentanoic acid | 133464-46-7 |
| Fmoc-Gly-OH | | 2-(9H-fluoren-9-yl methoxy carbonyl amino)acetic acid | 29022-11-5 |
| Fmoc-Gly(cBu)-OH | | (2S)-2-cyclobutyl-2-(9H-fluoren-9-yl methoxycarbonyl amino)acetic acid | 1391630-31-1 |

TABLE 4-continued

| Abbreviation | Structural formula | Name | CAS No. |
|---|---|---|---|
| Fmoc-Gly(cPent)-OH | | (2S)-2-cyclopentyl-2-(9H-fluoren-9-yl methoxycarbonyl amino)acetic acid | 220497-61-0 |
| Fmoc-Gly(cPr)-OH | | (2S)-2-cyclopropyl-2-(9H-fluoren-9-yl methoxycarbonyl amino)acetic acid | 1212257-18-5 |
| Fmoc-Hle-OH | | (2S)-2-(9H-fluoren-9-yl methoxycarbonyl amino)-5-methyl hexanoic acid | 180414-94-2 |
| Fmoc-Hph-OH | | (2S)-2-(9H-fluoren-9-yl methoxycarbonyl amino)-4-phenyl butanoic acid | 132684-59-4 |
| Fmoc-Hph(34-Cl2)-OH | | (2S)-4-(3,4-dichlorophenyl)-2-(9H-fluoren-9-yl methoxy carbonyl amino)butanoic acid | 1260616-12-3 |

TABLE 4-continued

| Abbreviation | Structural formula | Name | CAS No. |
|---|---|---|---|
| Fmoc-Hph(3-F)-OH | | (2S)-2-(9H-fluoren-9-yl methoxycarbonyl amino)-4-(3-fluorophenyl)butanoic acid | 1260594-44-2 |
| Fmoc-Hph(4-CF3)-OH | | (2S)-2-(9H-fluoren-9-yl methoxycarbonyl amino)-4-[4-(trifluoromethyl)phenyl]butanoic acid | 1260591-49-8 |
| Fmoc-Hph(4-F)-OH | | (2S)-2-(9H-fluoren-9-yl methoxycarbonyl amino)-4-(4-fluorophenyl)butanoic acid | 1260608-85-2 |
| Fmoc-Hph(4-Me)-OH | | (2S)-2-(9H-fluoren-9-yl methoxycarbonyl amino)-4-(4-methyl phenyl)butanoic acid | 1260587-57-2 |

TABLE 4-continued

| Abbreviation | Structural formula | Name | CAS No. |
|---|---|---|---|
| Fmoc-Hse(Me)-OH | | (2S)-2-(9H-fluoren-9-yl methoxycarbonyl amino)-4-methoxybutanoic acid | 173212-86-7 |
| Fmoc-iBuGly-OH | | 2-[9H-fluoren-9-yl methoxy carbonyl(2-methyl propyl) amino]acetic acid | 141743-14-8 |
| Fmoc-IDC-OH | | (2S)-1-(9H-fluoren-9-yl methoxycarbonyl)-2,3-dihydroindol-2-carboxylic acid | 198560-38-2 |
| Fmoc-Ile-OH | | (2S,3S)-2-(9H-fluoren-9-yl methoxycarbonyl amino)-3-methyl pentanoic acid | 71989-23-6 |
| Fmoc-Leu-OH | | (2S)-2-(9H-fluoren-9-yl methoxycarbonyl amino)-4-methyl pentanoic acid | 35661-60-0 |

TABLE 4-continued

| Abbreviation | Structural formula | Name | CAS No. |
|---|---|---|---|
| Fmoc-Lys(Alloc)-OH | 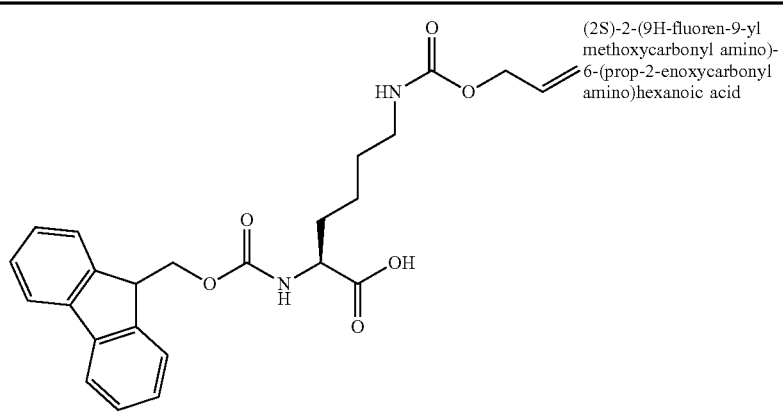 | (2S)-2-(9H-fluoren-9-yl methoxycarbonyl amino)-6-(prop-2-enoxycarbonyl amino)hexanoic acid | 146982-27-6 |
| Fmoc-MeAbu-OH | 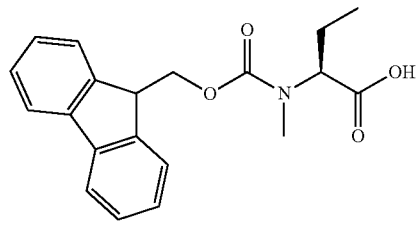 [SMILES: CC[C@H](NC(=O)OCC1c2ccccc2-c2ccccc21)C(=O)O] | (2S)-2-[9H-fluoren-9-yl methoxycarbonyl(methyl) amino]butanoic acid | 1310575-53-1 |
| Fmoc-MeAib-OH | 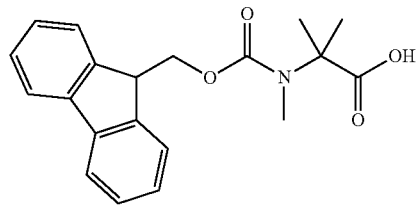 [SMILES: CN(C(=O)OCC1c2ccccc2-c2ccccc21)C(C)(C)C(=O)O] | 2-[9H-fluoren-9-yl methoxy carbonyl(methyl)amino]-2-methyl propanoic acid | 400779-65-9 |
| Fmoc-MeAla-OH | 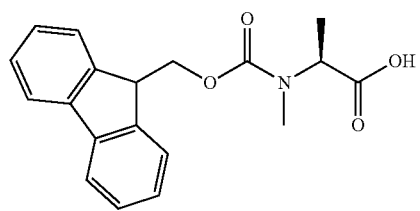 [SMILES: C[C@@H](C(=O)O)N(C)C(=O)OCC1c2ccccc2-c2ccccc21] | (2S)-2-[9H-fluoren-9-yl methoxycarbonyl(methyl) amino]propanoic acid | 84000-07-7 |
| Fmoc-MeCha-OH | 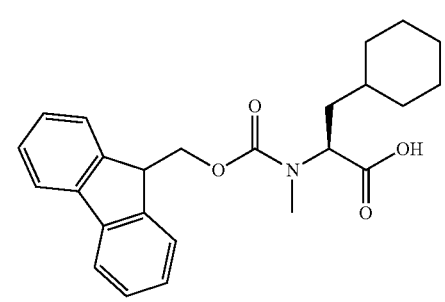 [SMILES: CN(C(=O)OCC1c2ccccc2-c2ccccc21)[C@@H](CC1CCCCC1)C(=O)O] | (2S)-3-cyclohexyl-2-[9H-fluoren-9-yl methoxycarbonyl (methyl)amino]propanoic acid | 148983-03-3 |

TABLE 4-continued

| Abbreviation | Structural formula | Name | CAS No. |
|---|---|---|---|
| Fmoc-MeChg-OH | 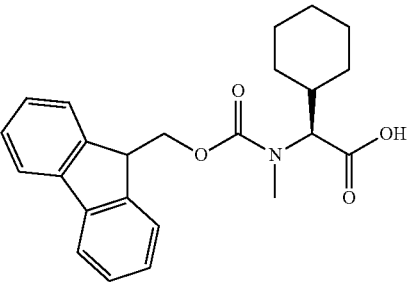 [SMILES: CN(C(=O)OCC1c2ccccc2-c2ccccc21)[C@H](C(=O)O)C1CCCCC1] | (2S)-2-cyclohexyl-2-[9H-fluoren-9-yl methoxycarbonyl(methyl)amino]acetic acid | 925240-97-7 |
| Fmoc-MeGly-OH | 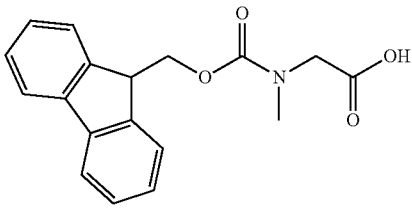 [SMILES: CN(CC(=O)O)C(=O)OCC1c2ccccc2-c2ccccc21] | 2-[9H-fluoren-9-yl methoxycarbonyl(methyl)amino]acetic acid | 77128-70-2 |
| Fmoc-MeIle-OH | 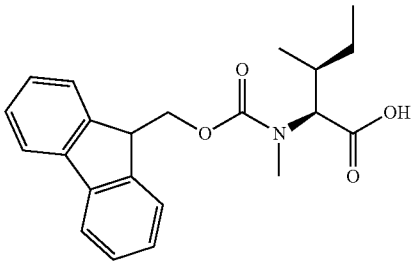 [SMILES: CC[C@H](C)[C@@H](C(=O)O)N(C)C(=O)OCC1c2ccccc2-c2ccccc21] | (2S,3S)-2-[9H-fluoren-9-yl methoxycarbonyl(methyl)amino]-3-methyl pentanoic acid | 138775-22-1 |
| Fmoc-MeLeu-OH | 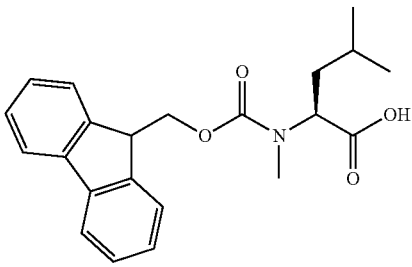 [SMILES: CC(C)C[C@@H](C(=O)O)N(C)C(=O)OCC1c2ccccc2-c2ccccc21] | (2S)-2-[9H-fluoren-9-yl methoxycarbonyl(methyl)amino]-4-methyl pentanoic acid | 103478-62-2 |
| Fmoc-MeNle-OH | 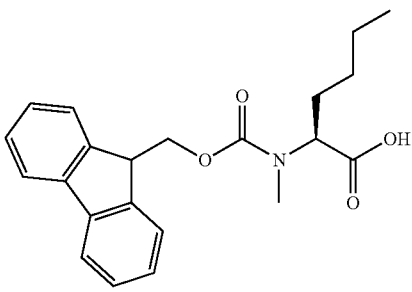 [SMILES: CCCC[C@@H](C(=O)O)N(C)C(=O)OCC1c2ccccc2-c2ccccc21] | (2S)-2-[9H-fluoren-9-yl methoxycarbonyl(methyl)amino]hexanoic acid | 112883-42-8 |

TABLE 4-continued

| Abbreviation | Structural formula | Name | CAS No. |
|---|---|---|---|
| Fmoc-MeNva-OH | | (2S)-2-[9H-fluoren-9-yl methoxycarbonyl(methyl) amino]pentanoic acid | 252049-05-1 |
| Fmoc-MePhe-OH | | (2S)-2-[9H-fluoren-9-yl methoxycarbonyl(methyl) amino]-3-phenyl propanoic acid | 77128-73-5 |
| Fmoc-MePhe(3-Me)-OH | | (2S)-2-[9H-fluoren-9-yl methoxycarbonyl(methyl) amino]-3-(3-methyl phenyl) propanoic acid | absent |
| Fmoc-Met(O2)-OH | | (2S)-2-(9H-fluoren-9-yl methoxycarbonyl amino)-4-methyl sulfonyl butanoic acid | 163437-14-7 |
| Fmoc-Methagly-OH | | (2S)-2-(9H-fluoren-9-yl methoxycarbonyl amino)-4-methyl pent-4-enoic acid | 87720-55-6 |

TABLE 4-continued

| Abbreviation | Structural formula | Name | CAS No. |
|---|---|---|---|
| Fmoc-MeThr-OH | | (2S,3R)-2-[9H-fluoren-9-yl methoxycarbonyl(methyl) amino]-3-hydroxybutanoic acid | 252049-06-2 |
| Fmoc-MeThr(Bn)-OH | | (2S,3R)-2-[9H-fluoren-9-yl methoxycarbonyl(methyl) amino]-3-phenyl methoxy butanoic acid | 198561-81-8 |
| Fmoc-MeTyr(Me)-OH | | (2S)-2-[9H-fluoren-9-yl methoxycarbonyl(methyl) amino]-3-(4-methoxyphenyl) propanoic acid | 1260595-45-6 |
| Fmoc-MeVal-OH | | (2S)-2-[9H-fluoren-9-yl methoxycarbonyl(methyl) amino]-3-methyl butanoic acid | 84000-11-3 |
| Fmoc-Mor(3)-OH | | (3S)-4-(9H-fluoren-9-yl methoxycarbonyl) morpholin-3-carboxylic acid | 281655-37-6 |

TABLE 4-continued

| Abbreviation | Structural formula | Name | CAS No. |
|---|---|---|---|
| Fmoc-Nle-OH | | (2S)-2-(9H-fluoren-9-yl methoxycarbonyl amino) hexanoic acid | 77284-32-3 |
| Fmoc-Nva-OH | | (2S)-2-(9H-fluoren-9-yl methoxycarbonyl amino) pentanoic acid | 135112-28-6 |
| Fmoc-Nva(3-Et)-OH | | (2S)-3-ethyl-2-(9H-fluoren-9-yl methoxycarbonyl amino)\| pentanoic acid | 1310680-47-7 |
| Fmoc-Oic-OH | | (2S,3aS,7aS)-1-(9H-fluoren-9-yl methoxycarbonyl)-2,3,3a,4,5,6,7,7a-octahydro indol-2-carboxylic acid | 130309-37-4 |
| Fmoc-Phe-OH | | (2S)-2-(9H-fluoren-9-yl methoxycarbonyl amino)-3-phenyl propanoic acid | 35661-40-6 |

TABLE 4-continued

| Abbreviation | Structural formula | Name | CAS No. |
|---|---|---|---|
| Fmoc-Phe(23-F2)-OH | | (2S)-3-(2,3-difluorophenyl)-2-(9H-fluoren-9-yl methoxy carbonyl amino)propanoic acid | 1260605-30-8 |
| Fmoc-Phe(2-CF3)-OH | | (2S)-2-(9H-fluoren-9-yl methoxycarbonyl amino)-3-[2-(trifluoromethyl)phenyl]propanoic acid | 352523-16-1 |
| Fmoc-Phe(2-Cl)-OH | | (2S)-3-(2-chlorophenyl)-2-(9H-fluoren-9-yl methoxy carbonyl amino)propanoic acid | 198560-41-7 |
| Fmoc-Phe(2-F)-OH | | (2S)-2-(9H-fluoren-9-yl methoxycarbonyl amino)-3-(2-fluorophenyl)propanoic acid | 205526-26-7 |
| Fmoc-Phe(2-Me)-OH | | (2S)-2-(9H-fluoren-9-yl methoxycarbonyl amino)-3-(2-methyl phenyl)propanoic acid | 211637-75-1 |

TABLE 4-continued

| Abbreviation | Structural formula | Name | CAS No. |
|---|---|---|---|
| Fmoc-Phe(2-OCF3)-OH | | (2S)-2-(9H-fluoren-9-yl methoxycarbonyl amino)-3-[2-(trifluoromethoxy) phenyl]propanoic acid | 1260593-24-5 |
| Fmoc-Phe(2-OMe)-OH | | (2S)-2-(9H-fluoren-9-yl methoxycarbonyl amino)-3-(2-methoxyphenyl) propanoic acid | 206060-41-5 |
| Fmoc-Phe(35-F2)-OH | | (2S)-3-(3,5-difluorophenyl)-2-(9H-fluoren-9-yl methoxy carbonyl amino)propanoic acid | 205526-24-5 |
| Fmoc-Phe(3-CF3)-OH | | (2S)-2-(9H-fluoren-9-yl methoxycarbonyl amino)-3-[3-(trifluoromethyl) phenyl]propanoic acid | 205526-27-8 |

TABLE 4-continued

| Abbreviation | Structural formula | Name | CAS No. |
|---|---|---|---|
| Fmoc-Phe(3-Cl)-OH | | (2S)-3-(3-chlorophenyl)-2-(9H-fluoren-9-yl methoxy carbonyl amino)propanoic acid | 198560-44-0 |
| Fmoc-Phe(3-F)-OH | | (2S)-2-(9H-fluoren-9-yl methoxycarbonyl amino)-3-(3-fluorophenyl)propanoic acid | 198560-68-8 |
| Fmoc-Phe(3-I)-OH | | (2S)-2-(9H-fluoren-9-yl methoxycarbonyl amino)-3-(3-iodophenyl)propanoic acid | 210282-31-8 |
| Fmoc-Phe(3-Me)-OH | | (2S)-2-(9H-fluoren-9-yl methoxycarbonyl amino)-3-(3-methyl phenyl) propanoic acid | 211637-74-0 |

TABLE 4-continued

| Abbreviation | Structural formula | Name | CAS No. |
|---|---|---|---|
| Fmoc-Phe(3-OCF3)-OH | 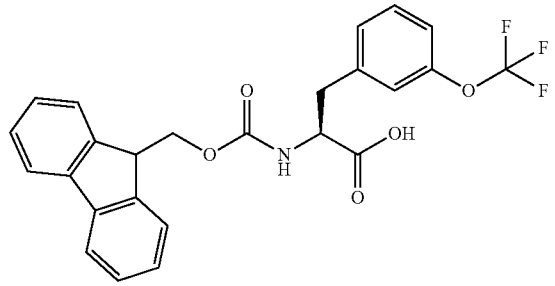 [SMILES: O=C(N[C@@H](Cc1cccc(OC(F)(F)F)c1)C(=O)O)OCC1c2ccccc2-c2ccccc21] | (2S)-2-(9H-fluoren-9-yl methoxycarbonyl amino)-3-[3-(trifluoromethoxy) phenyl]propanoic acid | 1260592-32-2 |
| Fmoc-Phe(3-OMe)-OH | 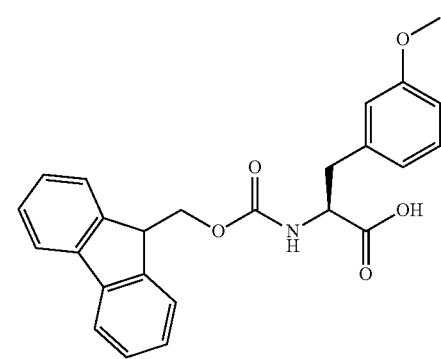 [SMILES: COc1cccc(C[C@H](NC(=O)OCC2c3ccccc3-c3ccccc32)C(=O)O)c1] | (2S)-2-(9H-fluoren-9-yl methoxycarbonyl amino)-3-(3-methoxyphenyl) propanoic acid | 206060-40-4 |
| Fmoc-Phe(4-CF3)-OH | 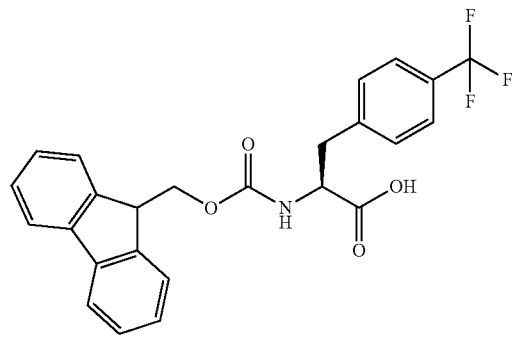 [SMILES: O=C(N[C@@H](Cc1ccc(C(F)(F)F)cc1)C(=O)O)OCC1c2ccccc2-c2ccccc21] | (2S)-2-(9H-fluoren-9-yl methoxycarbonyl amino)-3-[4-(trifluoromethyl)phenyl] propanoic acid | 247113-86-6 |
| Fmoc-Phe(4-F)-OH | 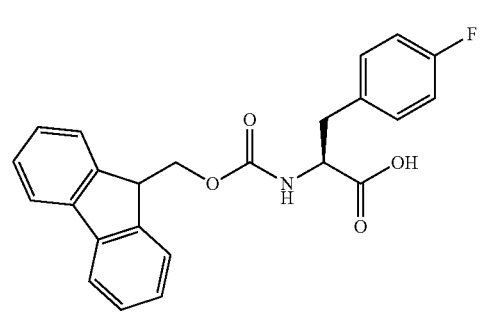 [SMILES: O=C(N[C@@H](Cc1ccc(F)cc1)C(=O)O)OCC1c2ccccc2-c2ccccc21] | (2S)-2-(9H-fluoren-9-yl methoxycarbonyl amino)-3-(4-fluorophenyl)propanoic acid | 169243-86-1 |
| Fmoc-Phe(4-Me)-OH | 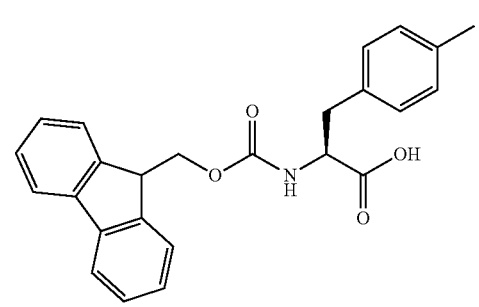 [SMILES: Cc1ccc(C[C@H](NC(=O)OCC2c3ccccc3-c3ccccc32)C(=O)O)cc1] | (2S)-2-(9H-fluoren-9-yl methoxycarbonyl amino)-3-(4-methyl phenyl) propanoic acid | 199006-54-7 |

TABLE 4-continued

| Abbreviation | Structural formula | Name | CAS No. |
|---|---|---|---|
| Fmoc-Phe3-OH | | (2S)-2-(9H-fluoren-9-yl methoxycarbonyl amino)-5-phenyl pentanoic acid | 959578-11-1 |
| Fmoc-Pic(2)-OH | | (2S)-1-(9H-fluoren-9-yl methoxycarbonyl) piperidin-2-carboxylic acid | 86069-86-5 |
| Fmoc-Pic(2)(4-Oxo)-OH | | (2S)-1-(9H-fluoren-9-yl methoxycarbonyl)-4-oxopiperidin-2-carboxylic acid | 1221793-43-6 |
| Fmoc-PRA-OH | | (2S)-2-(9H-fluoren-9-yl methoxycarbonyl amino) pent-4-ynoic acid | 198561-07-8 |
| Fmoc-Pregly-OH | | (2S)-2-(9H-fluoren-9-yl methoxycarbonyl amino)-5-methyl hex-4-enoic acid | 914486-08-1 |

TABLE 4-continued

| Abbreviation | Structural formula | Name | CAS No. |
|---|---|---|---|
| Fmoc-Pro-OH | | (2S)-1-(9H-fluoren-9-yl methoxycarbonyl) pyrrolidin-2-carboxylic acid | 71989-31-6 |
| Fmoc-Pro(4-F2)-OH | | (2S)-1-(9H-fluoren-9-yl methoxycarbonyl)-4,4-difluoropyrrolidin-2-carboxylic acid | 203866-21-1 |
| Fmoc-Pro(4-keto)-OH | | (2S)-1-(9H-fluoren-9-yl methoxycarbonyl)-4-oxopyrrolidin-2-carboxylic acid | 223581-83-7 |
| Fmoc-Pro(4R-Ph)-OH | | (2S,4R)-1-(9H-fluoren-9-yl methoxycarbonyl)-4-phenyl pyrrolidin-2-carboxylic acid | 1093651-96-7 |
| Fmoc-Pro(4S-Ph)-OH | | (2S,4S)-1-(9H-fluoren-9-yl methoxycarbonyl)-4-phenyl pyrrolidin-2-carboxylic acid | 269078-71-9 |
| Fmoc-Ser(Me)-OH | | (2S)-2-(9H-fluoren-9-yl methoxycarbonyl amino)-3-methoxypropanoic acid | 159610-93-2 |

TABLE 4-continued

| Abbreviation | Structural formula | Name | CAS No. |
|---|---|---|---|
| Fmoc-Thiopro-OH | | (4R)-3-(9H-fluoren-9-yl methoxycarbonyl)-1,3-thiazolidin-4-carboxylic acid | 133054-21-4 |
| Fmoc-Thr(Me)-OH | | (2S,3R)-2-(9H-fluoren-9-yl methoxycarbonyl amino)-3-methoxybutanoic acid | 928063-81-4 |
| Fmoc-Tle-OH | | (2S)-2-(9H-fluoren-9-yl methoxycarbonyl amino)-3,3-dimethyl butanoic acid | 132684-60-7 |
| Fmoc-Tyr(Me)-OH | | (2S)-2-(9H-fluoren-9-yl methoxycarbonyl amino)-3-(4-methoxyphenyl) propanoic acid | 77128-72-4 |
| Fmoc-Val-OH | | (2S)-2-(9H-fluoren-9-yl methoxycarbonyl amino)-3-methyl butanoic acid | 68858-20-8 |
| Fmoc-MePhe(3-OMe)-OH | | (2S)-2-[9H-fluoren-9-yl methoxycarbonyl(methyl) amino]-3-(3-methoxyphenyl) propanoic acid | absent |

TABLE 4-continued

| Abbreviation | Structural formula | Name | CAS No. |
| --- | --- | --- | --- |
| Fmoc-Phe(2-Cl-5-Br)-OH | | (2S)-3-(5-bromo-2-chloro phenyl)-2-(9H-fluoren-9-yl methoxycarbonyl amino) propanoic acid | 2002401-84-3 |

TABLE 5

| Compound No. | Abbreviation | Structural formula | Name |
| --- | --- | --- | --- |
| aa001 | Fmoc-(pip(4-F2)nPr)Gly-OH | | 2-[3-(4,4-difluoropiperidin-1-yl) propyl-(9H-fluoren-9-yl methoxycarbonyl)amino] acetic acid |
| aa002 | Fmoc-2-(pip-4-F2)-EtGly-OH | | 2-[2-(4,4-difluoropiperidin-1-yl) ethyl-(9H-fluoren-9-yl methoxycarbonyl)amino] acetic acid |
| aa003 | Fmoc-cPrGly-OH | | 2-[cyclopropyl(9H-fluoren-9-yl methoxycarbonyl)amino] acetic acid |
| aa004 | Fmoc-iPrGly-OH | | 2-[9H-fluoren-9-yl methoxycarbonyl(propan-2-yl) amino]acetic acid |

TABLE 5-continued

| Compound No. | Abbreviation | Structural formula | Name |
|---|---|---|---|
| aa033 | Fmoc-MeAla(3-Pyr-4-CF3)-OH | | (2S)-2-[9H-fluoren-9-yl methoxycarbonyl(methyl) amino]-3-[6-(trifluoromethyl) pyridin-3-yl]propanoic acid |
| aa034 | Fmoc-MeAla(3-Pyr-5-OMe)-OH | | (2S)-2-[9H-fluoren-9-yl methoxycarbonyl(methyl) amino]-3-(5-methoxypyridin-3-yl)propanoic acid |
| aa035 | Fmoc-MeAla(3-Pyr-5-Me)-OH | | (2S)-2-[9H-fluoren-9-yl methoxycarbonyl(methyl) amino]-3-(5-methyl pyridin-3-yl) propanoic acid |
| aa036 | Fmoc-MeAla(3-Pyr-4-OMe)-OH | | (2S)-2-[9H-fluoren-9-yl methoxycarbonyl(methyl) amino]-3-(6-methoxypyridin-3-yl)propanoic acid |

TABLE 5-continued

| Compound No. | Abbreviation | Structural formula | Name |
|---|---|---|---|
| aa037 | Fmoc-MeAla(3-Pyr-4-Me)-OH | | (2S)-2-[9H-fluoren-9-yl methoxycarbonyl(methyl) amino]-3-(6-methyl pyridin-3-yl) propanoic acid |
| aa038 | Fmoc-Ala(3-Pyr-5-Br)-OH | | (2S)-3-(5-bromopyridin-3-yl)-2-[9H-fluorene-9-yl methoxycarbonylamino] propanoic acid |
| aa039 | Fmoc-MeAbu(3-Pyr)-OH | | (2S)-2-[9H-fluoren-9-yl methoxycarbonyl(methyl) amino]-4-pyridin-3-yl butanoic acid |
| aa040 | Fmoc-MeAbu(4-Pyr)-OH | | (2S)-2-[9H-fluoren-9-yl methoxycarbonyl(methyl) amino]-4-pyridin-4-yl butanoic acid |

TABLE 5-continued

| Compound No. | Abbreviation | Structural formula | Name |
|---|---|---|---|
| aa041 | Fmoc-Ser(cPr)-OH | | (2S)-3-cyclopropyloxy-2-(9H-fluoren-9-yl methoxycarbonyl amino) propanoic acid |
| aa042 | Fmoc-MeSer(cBu)-OH | | (2S)-3-cyclobutyloxy-2-[9H-fluoren-9-yl methoxycarbonyl (methyl)amino]propanoic acid |
| aa043 | Fmoc-Ser(cBu)-OH | | (2S)-3-cyclobutyloxy-2-(9H-fluoren-9-yl methoxy carbonyl amino)propanoic acid |
| aa044 | Fmoc-Ser(Tfe)-OH | | (2S)-2-(9H-fluoren-9-yl methoxycarbonyl amino)-3-(2,2,2-trifluoroethoxy) propanoic acidtt |

TABLE 5-continued

| Compound No. | Abbreviation | Structural formula | Name |
|---|---|---|---|
| aa045 | Fmoc-MeSer(Tfe)-OH | | (2S)-2-[9H-fluoren-9-yl methoxycarbonyl(methyl) amino]-3-(2,2,2-trifluoroethoxy) propanoic acid |
| aa047 | Fmoc-MeAbu(Aze-3-F2)-OH | | (2S)-4-(3,3-difluoroazetidin-1-yl)-2-[9H-fluoren-9-yl methoxycarbonyl(methyl) amino]butanoic acid |
| aa048 | Fmoc-MeAlgly-OH | | (2S)-2-[9H-fluoren-9-yl methoxycarbonyl(methyl) amino]pent-4-enoic acid |
| aa049 | Fmoc-Hph(4-SF5)-OH | | (2S)-2-(9H-fluoren-9-yl methoxycarbonyl amino)-4-[4-(pentafluoro-λ6-sulfanyl)phenyl] butanoic acid |

TABLE 5-continued

| Compound No. | Abbreviation | Structural formula | Name |
|---|---|---|---|
| aa050 | Fmoc-nPrAla-OH | | (2S)-2-[9H-fluoren-9-yl methoxycarbonyl(propyl) amino]propanoic acid |
| aa053 | Fmoc-Ala(B(OH)2)-OH | | (2S)-3-borono-2-(9H-fluoren-9-yl methoxycarbonyl amino) propanoic acid |
| aa054 | Fmoc-D-MeSer(THP)-OH | | (2R)-2-[9H-fluoren-9-yl methoxycarbonyl(methyl) amino]-3-(oxan-2-yloxy) propanoic acid |
| aa055 | Fmoc-D-MeSer(iPen)-OH | | (2R)-2-[9H-fluoren-9-yl methoxycarbonyl(methyl) amino]-3-(3-methyl butoxy) propanoic acidt |
| aa060 | Fmoc-MePhe(3-CN)-OH | | (2S)-3-(3-cyanophenyl)-2-[9H-fluoren-9-yl methoxycarbonyl (methyl)amino]propanoic acid |

TABLE 5-continued

| Compound No. | Abbreviation | Structural formula | Name |
|---|---|---|---|
| aa061 | Fmoc-MePhe(4-CN)-OH | | (2S)-3-(4-cyanophenyl)-2-[9H-fluoren-9-yl methoxycarbonyl (methyl)amino]propanoic acid |
| aa062 | Fmoc-MeSer(Me)-OH | | (2S)-2-[9H-fluoren-9-yl methoxycarbonyl(methyl) amino]-3-methoxypropanoic acid |
| aa063 | Fmoc-MePhe(2-CF3)-OH | | (2S)-2-[9H-fluoren-9-yl methoxycarbonyl(methyl) amino]-3-[2-(trifluoromethyl) phenyl]propanoic acid |
| aa064 | Fmoc-MePhe(2-CN)-OH | | (2S)-3-(2-cyanophenyl)-2-[9H-fluoren-9-yl methoxycarbonyl (methyl)amino]propanoic acid |
| aa065 | Fmoc-MeAla(4-Pyr)-OH | | (2S)-2-[9H-fluoren-9-yl methoxycarbonyl(methyl) amino]-3-pyridin-4-yl propanoic acid |

TABLE 5-continued

| Compound No. | Abbreviation | Structural formula | Name |
|---|---|---|---|
| aa066 | Fmoc-MePhe(4-CHF2)-OH | | (2S)-3-[4-(difluoromethyl) phenyl]-2-[9H-fluoren-9-yl methoxycarbonyl(methyl) amino]propanoic acid |
| aa067 | Fmoc-MePhe(2-OMe)-OH | | (2S)-2-[9H-fluoren-9-yl methoxycarbonyl(methyl) amino]-3-(2-methoxyphenyl) propanoic acid |
| aa068 | Fmoc-MeAla(3-Pyr)-OH | | (2S)-2-[9H-fluoren-9-yl methoxycarbonyl(methyl) amino]-3-pyridin-3-yl propanoic acid |
| aa069 | Fmoc-MeSer(cPr)-OH | | (2S)-3-cyclopropyloxy-2-[9H-fluoren-9-yl methoxycarbonyl (methyl)amino]propanoic acid |
| aa070 | Fmoc-MeAla(cPr)-OH | | (2S)-3-cyclopropyl-2-[9H-fluoren-9-yl methoxycarbonyl (methyl)amino]propanoic acid |

TABLE 5-continued

| Compound No. | Abbreviation | Structural formula | Name |
|---|---|---|---|
| aa071 | Fmoc-MeAla(cPent)-OH | | (2S)-3-cyclopentyl-2-[9H-fluoren-9-yl methoxycarbonyl (methyl)amino]propanoic acid |
| aa072 | Fmoc-MeAla(cBu)-OH | | (2S)-3-cyclobutyl-2-[9H-fluoren-9-yl methoxycarbonyl(methyl) amino]propanoic acid |
| aa073 | Fmoc-MePhe(3-CF3)-OH | | (2S)-2-[9H-fluoren-9-yl methoxycarbonyl(methyl) amino]-3-[3-(trifluoromethyl) phenyl]propanoic acid |
| aa074 | Fmoc-MePhe(2-OCF3)-OH | | (2S)-2-[9H-fluoren-9-yl methoxycarbonyl(methyl) amino]-3-[2-(trifluoromethoxy) phenyl]propanoic acid |

TABLE 5-continued

| Compound No. | Abbreviation | Structural formula | Name |
|---|---|---|---|
| aa075 | Fmoc-MeGly(cBu)-OH | | (2S)-2-cyclobutyl-2-[9H-fluoren-9-yl methoxycarbonyl(methyl)amino]acetic acid |
| aa076 | Fmoc-MeAhxy(2)-OH | | (2S)-2-[9H-fluoren-9-yl methoxycarbonyl(methyl)amino]hex-5-ynoic acid |
| aa077 | Fmoc-MePhe(2-Me)-OH | | (2S)-2-[9H-fluoren-9-yl methoxycarbonyl(methyl)amino]-3-(2-methyl phenyl)propanoic acid |
| aa078 | Fmoc-MeHse(Me)-OH | | (2S)-2-[9H-fluoren-9-yl methoxycarbonyl(methyl)amino]-4-methoxybutanoic acid |
| aa079 | Fmoc-MeGly(cPent)-OH | | (2S)-2-cyclopentyl-2-[9H-fluoren-9-yl methoxycarbonyl(methyl)amino]acetic acid |

TABLE 5-continued

| Compound No. | Abbreviation | Structural formula | Name |
|---|---|---|---|
| aa080 | Fmoc-MePhe(3-F)-OH | | (2S)-2-[9H-fluoren-9-yl methoxycarbonyl(methyl) amino]-3-(3-fluorophenyl) propanoic acid |
| aa081 | Fmoc-MePhe(4-OCF3)-OH | | (2S)-2-[9H-fluoren-9-yl methoxycarbonyl(methyl) amino]-3-[4-(trifluoromethoxy) phenyl]propanoic acid |
| aa082 | Fmoc-MePhe(4-F)-OH | | (2S)-2-[9H-fluoren-9-yl methoxycarbonyl(methyl) amino]-3-(4-fluorophenyl) propanoic acid |
| aa083 | Fmoc-MePRA-OH | | (2S)-2-[9H-fluoren-9-yl methoxycarbonyl(methyl) amino]pent-4-ynoic acid |
| aa084 | Fmoc-MeHnl-OH | | (2S)-2-[9H-fluoren-9-yl methoxycarbonyl(methyl) amino]heptanoic acid |

TABLE 5-continued

| Compound No. | Abbreviation | Structural formula | Name |
|---|---|---|---|
| aa085 | Fmoc-MePhe(4-Me)-OH | | (2S)-2-[9H-fluoren-9-yl methoxycarbonyl(methyl) amino]-3-(4-methyl phenyl) propanoic acid |
| aa086 | Fmoc-MePhe(4-Br)-OH | | (2S)-3-(4-bromophenyl)-2-[9H-fluoren-9-yl methoxycarbonyl (methyl)amino]propanoic acid |
| aa087 | Fmoc-MePhe(3-OCF3)-OH | | (2S)-2-[9H-fluoren-9-yl methoxycarbonyl(methyl) amino]-3-[3-(trifluoromethoxy) phenyl]propanoic acid |
| aa088 | Fmoc-MecLeu-OH | | 1-[9H-fluoren-9-yl methoxycarbonyl(methyl) amino]cyclopentan-1-carboxylic acid |
| aa089 | Fmoc-MeGly(cPr)-OH | | (2S)-2-cyclopropyl-2-[9H-fluoren-9-yl methoxycarbonyl (methyl)amino]acetic acid |

TABLE 5-continued

| Compound No. | Abbreviation | Structural formula | Name |
|---|---|---|---|
| aa090 | Fmoc-MePhe(4-CF3)-OH | 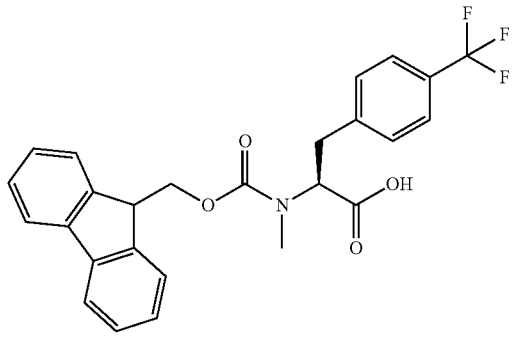 | (2S)-2-[9H-fluoren-9-yl methoxycarbonyl(methyl) amino]-3-[4-(trifluoromethyl) phenyl]propanoic acid |
| aa091 | Fmoc-MeAbu(4-F3)-OH | 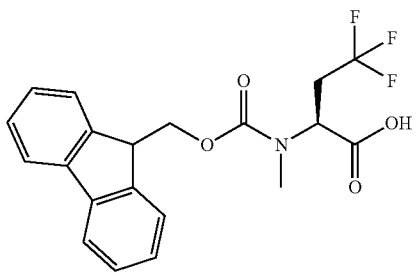 [SMILES: CN(C(=O)OCC1c2ccccc2-c2ccccc21)[C@@H](CC(F)(F)F)C(=O)O] | (2S)-2-[9H-fluoren-9-yl methoxycarbonyl(methyl) amino]-4,4,4-trifluorobutanoic acid |
| aa092 | Fmoc-MeMet(O2)-OH | 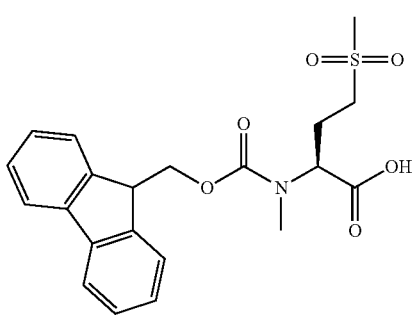 [SMILES: CN(C(=O)OCC1c2ccccc2-c2ccccc21)[C@@H](CCS(C)(=O)=O)C(=O)O] | (2S)-2-[9H-fluoren-9-yl methoxycarbonyl(methyl) amino]-4-methyl sulfonyl butanoic acid |
| aa093 | Fmoc-Me Thr(Me)-OH | 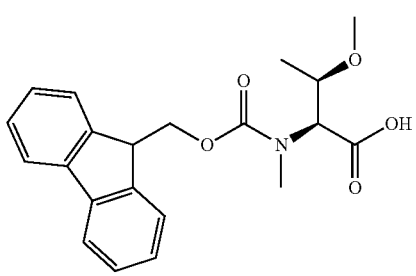 [SMILES: CO[C@H](C)[C@@H](C(=O)O)N(C)C(=O)OCC1c2ccccc2-c2ccccc21] | (2S,3R)-2-[9H-fluoren-9-yl methoxycarbonyl(methyl) amino]-3-methoxybutanoic acid |
| aa094 | Fmoc-MePhe(2-Cl)-OH | 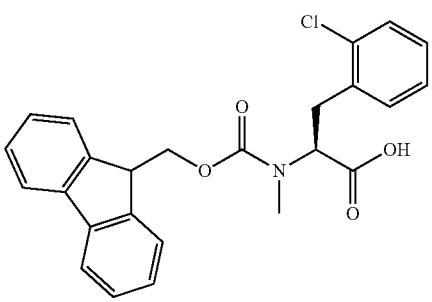 [SMILES: CN(C(=O)OCC1c2ccccc2-c2ccccc21)[C@@H](Cc1ccccc1Cl)C(=O)O] | (2S)-3-(2-chlorophenyl)-2-[9H-fluoren-9-yl methoxycarbonyl (methyl)amino]propanoic acid |

TABLE 5-continued

| Compound No. | Abbreviation | Structural formula | Name |
| --- | --- | --- | --- |
| aa095 | Fmoc-MePhe(2-F)-OH | | (2S)-2-[9H-fluoren-9-yl methoxycarbonyl(methyl) amino]-3-(2-fluorophenyl) propanoic acid |
| aa096 | Fmoc-MePhe(4-I)-OH | | (2S)-2-[9H-fluoren-9-yl methoxycarbonyl(methyl) amino]-3-(4-iodophenyl) propanoic acid |
| aa097 | Fmoc-MePhe(3-Br)-OH | | (2S)-3-(3-bromophenyl)-2-[9H-fluoren-9-yl methoxycarbonyl (methyl)amino]propanoic acid |
| aa098 | Fmoc-Me(Me)Phe-OH | | (2S)-2-[9H-fluoren-9-yl methoxycarbonyl(methyl) amino]-2-methyl-3-phenyl propanoic acid |
| aa033-b | Fmoc-MeAsp(OAl)-OH | | (2S)-2-[9H-fluoren-9-yl methoxycarbonyl(methyl) amino]-4-oxo-4-prop-2-enoxybutanoic acid |

TABLE 5-continued

| Compound No. | Abbreviation | Structural formula | Name |
|---|---|---|---|
| aa101 | Fmoc-cisHyp(THP)-OH | | (2S,4S)-1-(9H-fluoren-9-yl methoxycarbonyl)-4-(oxan-2-yloxy)pyrrolidin-2-carboxylic acid |
| aa102 | Fmoc-Hyp(THP)-OH | | (2S,4R)-1-(9H-fluoren-9-yl methoxycarbonyl)-4-(oxan-2-yloxy)pyrrolidin-2-carboxylic acid |
| aa104 | Fmoc-Phe(3-I-5-Cl)-OH | | (2S)-3-(3-chloro-5-iodophenyl)-2-(9H-fluoren-9-yl methoxycarbonyl amino) propanoic acid |
| aa105 | Fmoc-Phe(2-F-3-I)-OH | | (2S)-2-(9H-fluoren-9-yl methoxycarbonyl amino)-3-(2-fluoro-3-iodophenyl)propanoic acid |

TABLE 5-continued

| Compound No. | Abbreviation | Structural formula | Name |
|---|---|---|---|
| aa106 | Fmoc-Phe(3-I-5-F)-OH | | (2S)-2-(9H-fluoren-9-yl methoxycarbonyl amino)-3-(3-fluoro-5-iodophenyl)propanoic acid |
| aa109 | Fmoc-EtAla-OH | | (2S)-2-[ethyl(9H-fluoren-9-yl methoxycarbonyl)amino] propanoic acid |
| aa110 | Fmoc-EtPhe(4-Cl)-OH | | (2S)-3-(4-chlorophenyl)-2-[ethyl(9H-fluoren-9-yl methoxycarbonyl)amino] propanoic acid |
| aa111 | Fmoc-EtLeu-OH | | (2S)-2-[ethyl(9H-fluoren-9-yl methoxycarbonyl)amino]-4-methyl pentanoic acid |
| aa112 | Fmoc-EtCha-OH | | (2S)-3-cyclohexyl-2-[ethyl(9H-fluoren-9-yl methoxycarbonyl)amino]propanoic acid |

TABLE 5-continued

| Compound No. | Abbreviation | Structural formula | Name |
|---|---|---|---|
| aa113 | Fmoc-EtPhe(4-Me)-OH | | (2S)-2-[ethyl(9H-fluoren-9-yl methoxycarbonyl)amino]-3-(4-methyl phenyl)propanoic acid |
| aa114 | Fmoc-EtPhe(4-CF3)-OH | | (2S)-2-[ethyl(9H-fluoren-9-yl methoxycarbonyl)amino]-3-[4-(trifluoromethyl)phenyl] propanoic acid |
| aa116 | Fmoc-Phe(26-F2)-OH | | (2S)-3-(2,6-difluorophenyl)-2-(9H-fluoren-9-yl methoxycarbonyl amino) propanoic acid |
| aa118 | Fmoc-Phe(25-F2)-OH | | (2S)-3-(2,5-difluorophenyl)-2-(9H-fluoren-9-yl methoxycarbonyl amino) propanoic acid |
| aa119 | Fmoc-(Me)Phe(3-I)-OH | | (2S)-2-(9H-fluoren-9-yl methoxycarbonyl amino)-3-(3-iodophenyl)-2-methyl propanoic acid |

TABLE 5-continued

| Compound No. | Abbreviation | Structural formula | Name |
| --- | --- | --- | --- |
| aa120 | Fmoc-Phe(35-Cl2)-OH | | (2S)-3-(3,5-dichlorophenyl)-2-(9H-fluoren-9-yl methoxycarbonyl amino) propanoic acid |
| aa121 | Fmoc-Phe(2-F-5-I)-OH | | (2S)-2-(9H-fluoren-9-yl methoxycarbonyl amino)-3-(2-fluoro-5-iodophenyl) propanoic acid |
| aa122 | Fmoc-Phe(2-Cl-5-I)-OH | | (2S)-3-(2-chloro-5-iodophenyl)-2-(9H-fluoren-9-yl methoxycarbonyl amino) propanoic acid |
| aa124 | Fmoc-Ala(2-Thie-5-Cl)-OH | | (2S)-3-(5-chlorothiophen-2-yl)-2-(9H-fluoren-9-yl methoxycarbonyl amino) propanoic acid |
| aa125 | Fmoc-Ala(2-Thie-5-Br)-OH | | (2S)-3-(5-bromothiophen-2-yl)-2-(9H-fluoren-9-yl methoxycarbonyl amino) propanoic acid |

TABLE 5-continued

| Compound No. | Abbreviation | Structural formula | Name |
|---|---|---|---|
| aa126 | Fmoc-Phe(2-Br-5-I)-OH | | (2S)-3-(2-bromo-5-iodophenyl)-2-(9H-fluoren-9-yl methoxycarbonyl amino) propanoic acid |
| aa127 | Fmoc-Phe(2-Me-5-I)-OH | | (2S)-2-(9H-fluoren-9-yl methoxycarbonyl amino)-3-(5-iodo-2-methyl phenyl) propanoic acid |
| aa128 | Fmoc-Phe(2-Me-5-Br)-OH | | (2S)-3-(5-bromo-2-methyl phenyl)-2-(9H-fluoren-9-yl methoxycarbonyl amino) propanoic acid |
| aa130 | Fmoc-MeAOC(2)-OH | | (2S)-2-[9H-fluoren-9-yl methoxycarbonyl(methyl) amino]octanoic acid |
| aa131 | Fmoc-MeHle-OH | | (2S)-2-[9H-fluoren-9-yl methoxycarbonyl(methyl) amino]-5-methyl hexanoic acid |

TABLE 5-continued

| Compound No. | Abbreviation | Structural formula | Name |
|---|---|---|---|
| aa132 | Fmoc-Hph(4-CF3-3-Cl)-OH | | (2S)-4-[3-chloro-4-(trifluoromethyl)phenyl]-2-(9H-fluoren-9-yl methoxycarbonyl amino) butanoic acid |
| aa133 | Fmoc-Hph(4-CF3-3-F)-OH | | (2S)-2-(9H-fluoren-9-yl methoxycarbonyl amino)-4-[3-fluoro-4-(trifluoromethyl)phenyl] butanoic acid |
| aa134 | Fmoc-Hph(4-CF3-35-F2)-OH | | (2S)-4-[3,5-difluoro-4-(trifluoromethyl)phenyl]-2-(9H-fluoren-9-yl methoxycarbonyl amino) butanoic acid |

TABLE 5-continued

| Compound No. | Abbreviation | Structural formula | Name |
|---|---|---|---|
| aa150 | Fmoc-MeNva(5-F2)-OH | | (2S)-2-[9H-fluoren-9-yl methoxycarbonyl(methyl) amino]-5,5-difluoropentanoic acid |
| aa151 | Fmoc-MePhe(34-F2)-OH | | (2S)-3-(3,4-difluorophenyl)-2-[9H-fluoren-9-yl methoxycarbonyl(methyl) amino]propanoic acid |
| aa152 | Fmoc-MeAsn(pip-4-F2)-OH | | (2S)-4-(4,4-difluoropiperidin-1-yl)-2-[9H-fluoren-9-yl methoxycarbonyl(methyl) amino]-4-oxobutanoic acid |
| aa153 | Fmoc-MeAsn(Aze-3-F2)-OH | | (2S)-4-(3,3-difluoroazetidin-1-yl)-2-[9H-fluoren-9-yl methoxycarbonyl(methyl) amino]-4-oxobutanoic acid |

TABLE 5-continued

| Compound No. | Abbreviation | Structural formula | Name |
|---|---|---|---|
| aa154 | Fmoc-MePhe(3-I)-OH | | (2S)-2-[9H-fluoren-9-yl methoxycarbonyl(methyl) amino]-3-(3-iodophenyl) propanoic acid |
| aa156 | Fmoc-(4-Me-piz-Et)Gly-OH | | 2-[9H-fluorene-9-yl methoxycarbonyl-[2-(4-methylpiperazin-1-yl) ethyl]amino]acetic acid |
| aa157 | Fmoc-(Aze(3)Et)Gly-OH | | 2-[2-(azetidine-3-yl) ethyl-(9H-fluorene-9-yl methoxycarbonyl)amino] acetic acid |
| aa158 | Fmoc-(H2NEtOEt)Gly-OH | | 2-[2-(2-aminoethoxy) ethyl-(9H-fluorene-9-yl methoxycarbonyl)amino] acetic acid |

TABLE 5-continued

| Compound No. | Abbreviation | Structural formula | Name |
|---|---|---|---|
| aa159 | Fmoc-(H2NnBu)Gly-OH | | 2-[4-aminobutyl (9H-fluorene-9-yl methoxycarbonyl) amino] acetic acid |
| aa160 | Fmoc-(Me2NEtOEt)Gly-OH | | 2-[2-[2-(dimethylamino) ethoxy]ethyl-(9H-fluorene-9-yl methoxycarbonyl) amino]acetic acid |
| aa161 | Fmoc-(MeNEtOEt)Gly-OH | | 2-[9H-fluorene-9-yl methoxycarbonyl-[2-[2-(methylamino)ethoxy] ethyl]amino]acetic acid |
| aa162 | Fmoc-(piz-Et)Gly-OH | | 2-[9H-fluorene-9-yl methoxycarbonyl (2-piperazin-1-yl ethyl) amino]acetic acid |

Synthesis of Fmoc Amino Acids

Synthesis of Compound aa001, 2-[3-(4,4-difluoropiperidin-1-yl)propyl-(9H-fluoren-9-ylmethoxycarbonyl)amino]acetic acid (Fmoc-(pip(4-F2)nPr)Gly-OH)

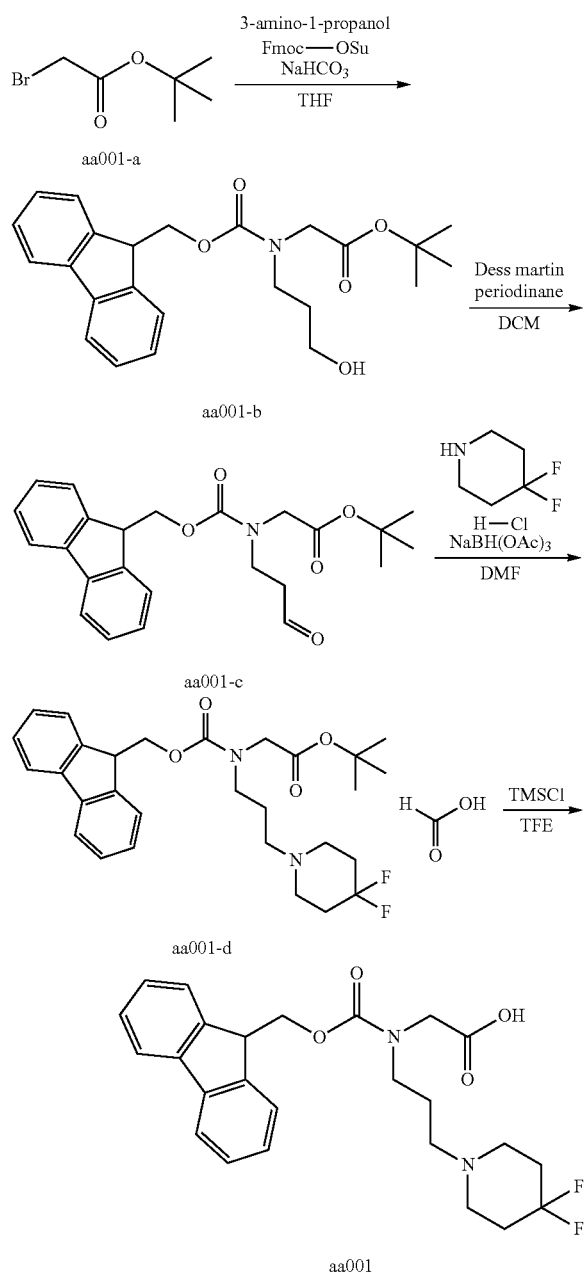

3-Amino-1-propanol (3.85 g, 51.3 mmol) was dissolved in anhydrous tetrahydrofuran (51.2 ml) under a nitrogen atmosphere and cooled to 0° C., after which a solution of Compound aa001-a (tert-butyl bromoacetate) (5.0 g, 25.6 mmol) in anhydrous tetrahydrofuran (33.3 ml) was added dropwise. The mixture was stirred at 0° C. for 10 min and then stirred at room temperature for one hour. After cooling again to 0° C., water (81.9 ml), sodium bicarbonate (4.74 g, 56.4 mmol), and N-(9-fluorenylmethoxycarbonyloxy)succinimide (Fmoc-OSu) (17.29 g, 51.3 mmol) were sequentially added and the mixture was stirred at room temperature overnight. The mixture was cooled to 0° C. and then extracted with ethyl acetate (500 ml) and a saturated aqueous ammonium chloride solution (500 ml). The organic layer was washed with water (500 ml) and brine (500 ml), dried over anhydrous sodium sulfate, and the solvent was evaporated under reduced pressure. The resulting concentrate was purified by normal phase chromatography (n-hexane/ethyl acetate) to give Compound aa001-b (7.37 g, 70%).

LCMS (ESI) m/z=434 (M+Na)+

Retention time: 0.88 min (analysis condition SQDFA05)

Compound aa001-b (6.37 g, 15.5 mmol) was dissolved in anhydrous dichloromethane (51.6 ml), Dess-Martin periodinane (7.22 g, 17.0 mmol) was added at 0° C., and the mixture was stirred for 10 minutes and then warmed to room temperature. After one hour, the mixture was cooled to 0° C. and extracted with ethyl acetate (500 ml) and an aqueous sodium bicarbonate solution (500 ml). The organic layer was washed with an aqueous sodium thiosulfate solution (500 ml) and brine (500 ml), dried over anhydrous sodium sulfate, and the solvent was evaporated under reduced pressure. The resulting concentrate was purified by normal phase chromatography (n-hexane/ethyl acetate) to give Compound aa001-c (5.58 g, 88%).

LCMS (ESI) m/z=410 (M+H)+

Retention time: 0.96 min (analysis condition SQDFA05)

Compound aa001-c (0.97 g, 2.37 mmol) and 4,4-difluoropiperidine hydrochloride (0.44 g, 2.77 mmol) were dissolved in N,N-dimethylformamide (7.9 ml), sodium triacetoxyborohydride (0.75 g, 3.55 mmol) was added, and the mixture was stirred for 30 minutes. The reaction solution was purified by reverse phase chromatography (acetonitrile with 0.1% formic acid/distilled water with 0.1% formic acid) to give Compound aa001-d (0.65 g, 49%).

LCMS (ESI) m/z=515.5 (M+H)+

Retention time: 0.68 min (analysis condition SQDFA05)

Compound aa001-d (0.64 g, 1.14 mmol) was dissolved in 2,2,2-trifluoroethanol (5.7 ml), and trimethylsilyl chloride (TMSCl) (0.43 ml, 3.42 mmol) was added thereto. The mixture was stirred at room temperature for one hour, and the solvent was then evaporated under reduced pressure to give Compound aa001 (2-[3-(4,4-difluoropiperidin-1-yl)propyl-(9H-fluoren-9-ylmethoxycarbonyl)amino]acetic acid, Fmoc-(pip(4-F2)nPr)Gly-OH) (0.52 g, 99%).

LCMS (ESI) m/z=459 (M+H)+

Retention time: 0.54 min (analysis condition SQDFA05)

Synthesis of Compound aa002, 2-[2-(4,4-difluoropiperidin-1-yl)ethyl-(9H-fluoren-9-ylmethoxycarbonyl)amino]acetic acid (Fmoc-(pip(4-F2)Et)Gly-OH)

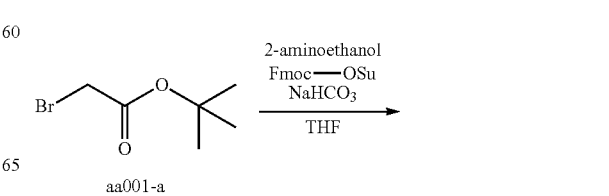

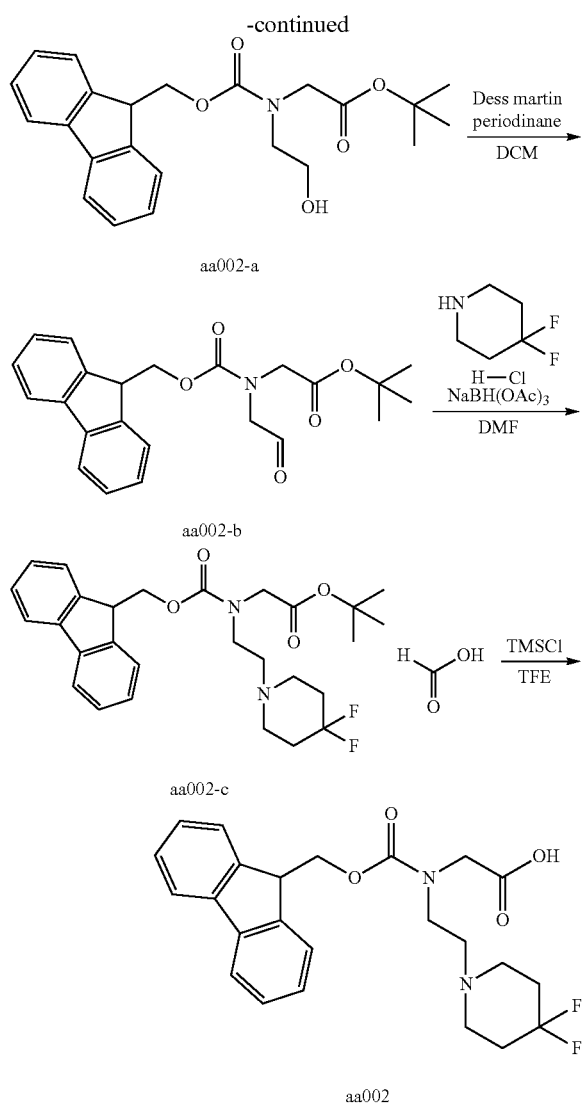

aa002-a aa002-b aa002-c aa002

Compound aa002-a (8.59 g, 84%) was obtained by the same method as in the synthesis of Compound aa001-b using Compound aa001-a (tert-butyl bromoacetate) (5.00 g, 25.6 mmol) as a starting material and using 2-aminoethanol instead of 3-amino-1-propanol.

LCMS (ESI) m/z=420 (M+Na)+
Retention time: 0.88 min (analysis condition SQDFA05)

Compound aa002-b was obtained as a crude product (5.58 g) under the same reaction conditions as in the synthesis of Compound aa001-c using the obtained Compound aa002-a (2.35 g, 5.91 mmol). The next reaction was performed without further purification.

LCMS (ESI) m/z=396 (M+H)+
Retention time: 0.96 min (analysis condition SQDFA05)

Compound aa002-c (1.33 g, 82%) was obtained under the same reaction conditions as in the synthesis of Compound aa001-d using Compound aa002-b (2.79 g, 2.955 mmol equivalents) obtained in the above reaction.

LCMS (ESI) m/z=501.5 (M+H)+
Retention time: 0.67 min (analysis condition SQDFA05)

Compound aa002 (2-[2-(4,4-difluoropiperidin-1-yl)ethyl-(9H-fluoren-9-ylmethoxycarbonyl)amino]acetic acid, Fmoc-(pip(4-F2)Et)Gly-OH) (1.08 g, 99%) was obtained under the same reaction conditions as in the synthesis of Compound aa001 using the obtained Compound aa002-c (1.33 g, 2.433 mmol).

LCMS (ESI) m/z=445 (M+H)+
Retention time: 0.58 min (analysis condition SQDFA05)

Synthesis of Compound aa003, 2-[cyclopropyl(9H-fluoren-9-ylmethoxycarbonyl)amino]acetic acid (Fmoc-cPrGly-OH)

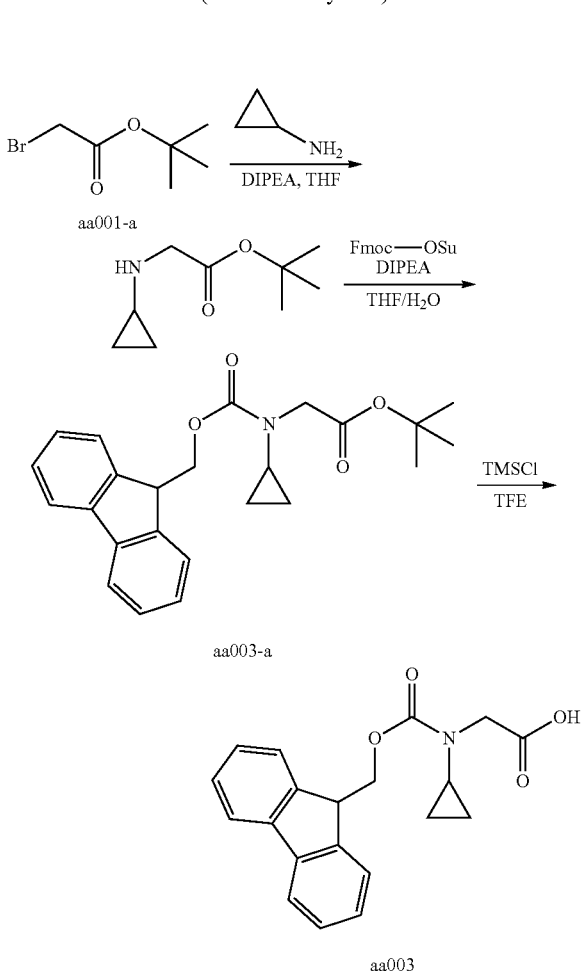

aa001-a aa003-a aa003

Cyclopropylamine (1.756 g, 30.8 mmol) was dissolved in anhydrous tetrahydrofuran (40 ml) under a nitrogen atmosphere and cooled to 0° C., after which a solution of Compound aa001-a (tert-butyl bromoacetate) (3.0 g, 15.38 mmol) in anhydrous tetrahydrofuran (THF) (10 mL) was added dropwise. The mixture was then stirred at room temperature overnight. Water (30 mL), diisopropylethylamine (DIPEA) (5.96 g, 46.1 mmol), and N-(9-fluorenyl-methoxycarbonyloxy)succinimide (Fmoc-OSu) (10.38 g, 30.8 mmol) were sequentially added and the mixture was stirred at room temperature for one hour. Dimethyl sulfoxide and a 20% aqueous formic acid solution were added to the reaction solution, and the tetrahydrofuran was then evaporated under reduced pressure. The resulting concentrate was purified by reverse phase chromatography (acetonitrile with 0.1% formic acid/0.1% aqueous formic acid solution) to give Compound aa003-a (2.72 g, 45%).

LCMS (ESI) m/z=394 (M+H)+
Retention time: 1.06 min (analysis condition SQDFA05)

Compound aa003-a (2.72 g, 6.91 mmol) was dissolved in 2,2,2-trifluoroethanol (TFE) (34.6 mL), and trimethylsilyl chloride (TMSCl) (2.63 ml, 20.74 mmol) was added. The mixture was stirred at room temperature for 40 minutes, and the solvent was then evaporated under reduced pressure. The resulting concentrate was purified by reverse phase chromatography (acetonitrile with 0.1% formic acid/0.1% aqueous formic acid solution) to give Compound aa003 (2-[cyclopropyl(9H-fluoren-9-ylmethoxycarbonyl)amino]acetic acid, Fmoc-cPrGly-OH) (1.74 g, 75%).

LCMS (ESI) m/z=338 (M+H)+
Retention time: 0.79 min (analysis condition SQDFA05)

Synthesis of Compound aa004, 2-[9H-fluoren-9-ylmethoxycarbonyl(propan-2-yl)amino]acetic acid (Fmoc-iPrGly-OH)

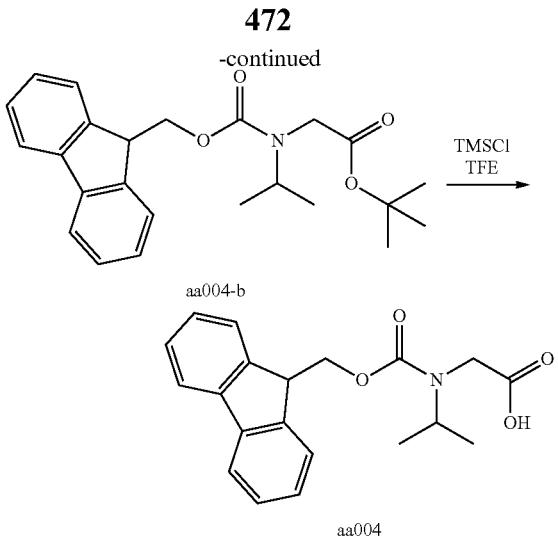

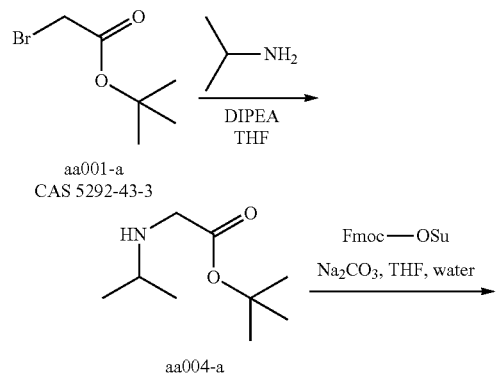

Compound aa004 (2-[9H-fluoren-9-ylmethoxycarbonyl(propan-2-yl)amino]acetic acid, Fmoc-iPrGly-OH) (7.0 g, 48% through three steps) was obtained by the same method as in the synthesis of Compound aa003 using Compound aa001-a (tert-butyl bromoacetate) (6.6 g, 33.8 mmol) as a starting material and using sodium carbonate instead of DIPEA as a base for Fmoc addition in the second step.

LCMS (ESI) m/z=340 (M+H)+
Retention time: 0.80 min (analysis condition SQDFA05)

Synthesis of Compound aa033, (2S)-2-[9H-fluoren-9-ylmethoxycarbonyl(methyl)amino]-3-[6-(trifluoromethyl)pyridin-3-yl]propanoic acid (Fmoc-MeAla(3-Pyr-4-CF3)-OH)

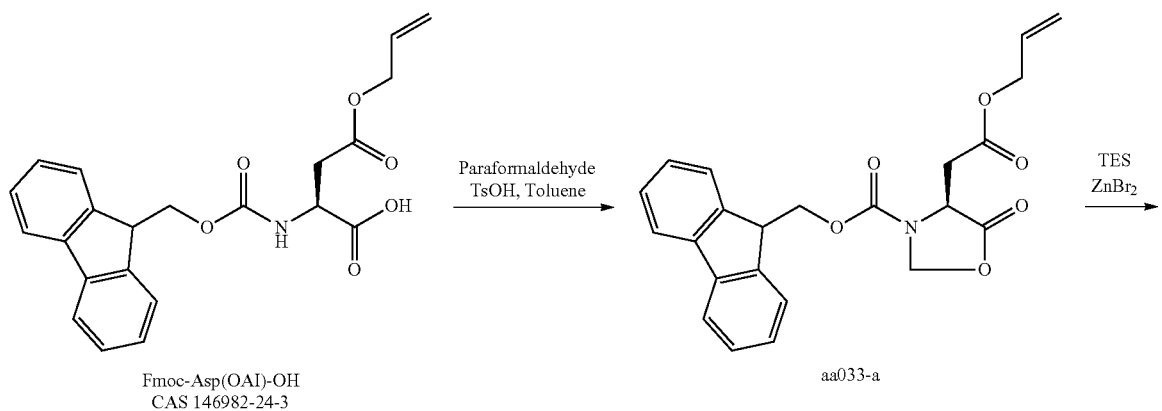

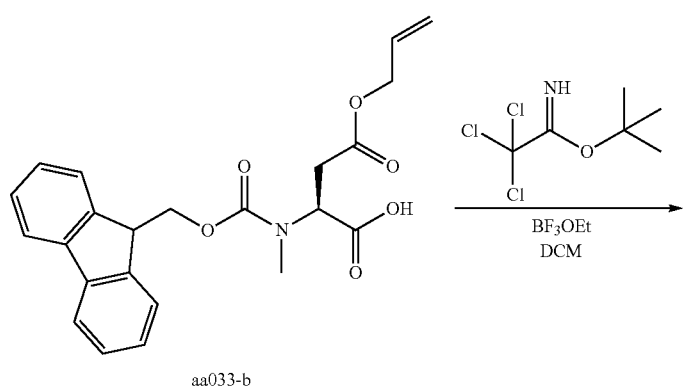

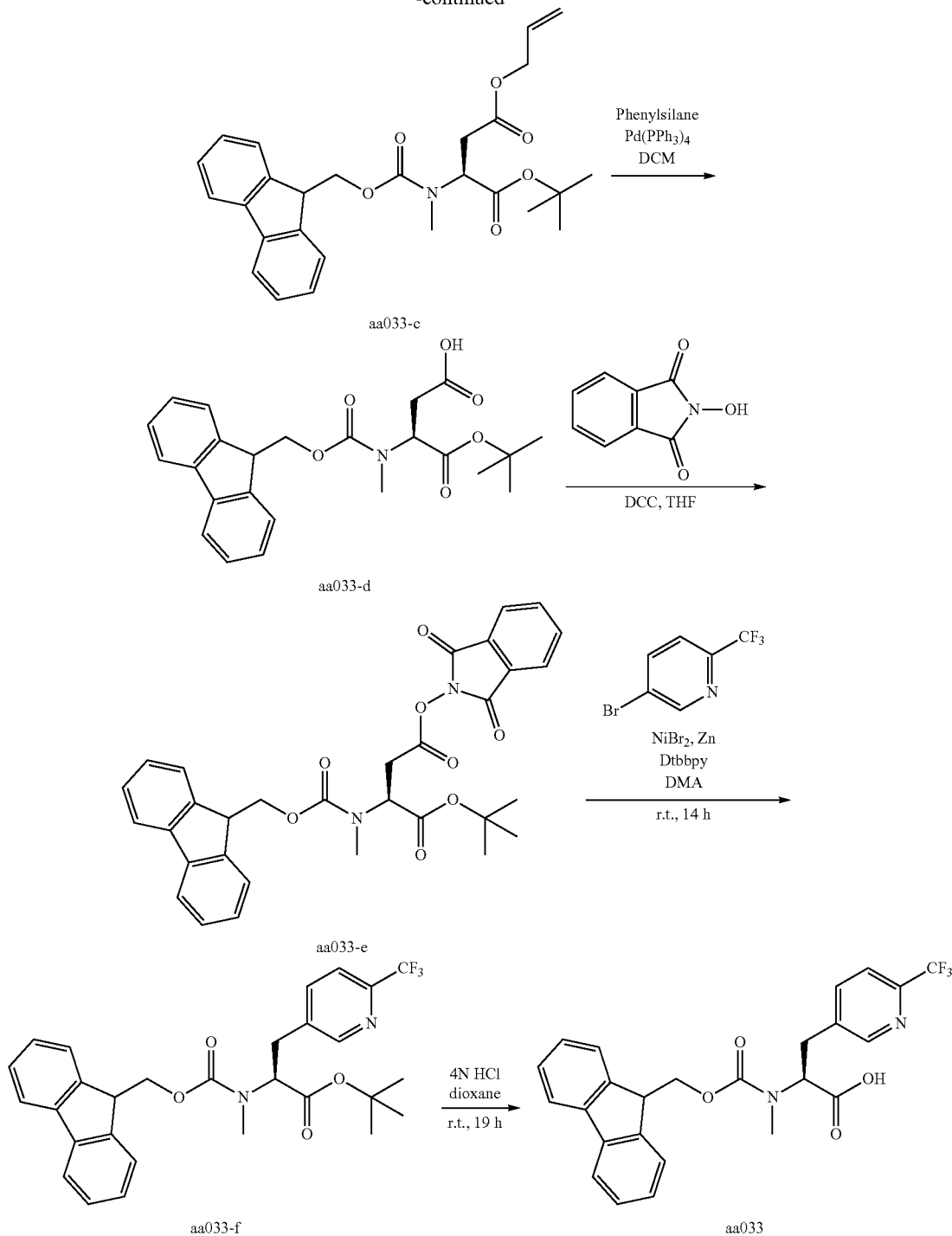

Fmoc-Asp(OA1)-OH((2S)-2-(9H-fluoren-9-ylmethoxy-carbonylamino)-4-oxo-4-prop-2-enoxybutanoic acid, CAS No. 146982-24-3) (200 g, 506 mmol), p-toluenesulfonic acid (5.7 g, 0.05 equivalents), and paraformaldehyde (45.6 g, 3 equivalents) were mixed with toluene and the mixture was stirred at 110° C. for 16 hours. The solvent was evaporated from the reaction solution under reduced pressure, and the residue was dissolved in ethyl acetate and washed with an aqueous sodium bicarbonate solution twice. The organic layer was dried over anhydrous sodium sulfate and the solvent was then evaporated under reduced pressure. The residue was purified by silica gel column chromatography (ethyl acetate/petroleum ether, 0/100 to 30/70) to give Compound aa033-a (9H-fluoren-9-ylmethyl (4S)-5-oxo-4-(2-oxo-2-prop-2-enoxyethyl)-1,3-oxazolidine-3-carboxy-late) (175 g, 85%). This was mixed with another batch synthesized in the same manner and was used for the next reaction.

LCMS (ESI) m/z=408 (M+H)+

Retention time: 1.407 min (analysis condition SMD-method_20)

A mixed solution of Compound aa033-a (100 g, 245 mmol), zinc bromide (ZnBr$_2$) (110 g, 496 mmol), and triethylsilane (TES) (56 g, 481.6 mmol) in dichloromethane (DCM) (1 L) was stirred at room temperature for 48 hours under a nitrogen atmosphere. Four batches of the reaction solution on the same scale were mixed and the solvent was evaporated under reduced pressure. The residue was dissolved in TBME and extracted with 0.5 M phosphate buffer (pH=approximately 7.5) ten times. The aqueous layers were combined, adjusted to pH 2 with 5 M aqueous hydrochloric acid, and extracted with isopropyl acetate (IPAC) twice. The organic layers were combined and dried over anhydrous sodium sulfate, and the solvent was then evaporated under reduced pressure. To remove the IPAC, TBME was added to the resulting residue and the solvent was evaporated under reduced pressure. This operation was repeated six times to give Compound aa033-b ((2S)-2-[9H-fluoren-9-ylmethoxycarbonyl(methyl)amino]-4-oxo-4-prop-2-enoxybutanoic acid) (270 g, 54%).

LCMS (ESI) m/z=410 (M+H)+
Retention time: 1.956 min (analysis condition SMD-method_05)

Under a nitrogen atmosphere, a solution of tert-butyl 2,2,2-trichloroacetimidate (106.73 g, 488.5 mmol) in cyclohexane (480 mL) and boron trifluoride-diethyl ether complex (BF$_3$—OEt$_2$) (346.6 mg, 2.442 mmol) were added to a solution of Compound aa033-b (100 g, 244 mmol) in DCM (240 mL) at 0° C., and the mixture was warmed to room temperature and stirred for one hour. The reaction was quenched by adding pyridine to the reaction solution, and the solid was removed by filtration. TBME was added to the filtrate and the resulting solution was sequentially washed with saturated aqueous sodium bicarbonate and brine. The organic layers were combined and dried over anhydrous sodium sulfate, and the solvent was then evaporated under reduced pressure to give Compound aa033-c as a crude product (102 g, 90%).

LCMS (ESI) m/z=488 (M+Na)+
Retention time: 1.574 min (analysis condition SMD-method_15)

Under a nitrogen atmosphere, phenylsilane (2.01 g, 18.6 mmol) was added dropwise to a mixture of Compound aa033-c (12 g, 26.6 mmol) and tetrakis(triphenylphosphine)palladium(0) (0.92 g, 0.797 mmol) in DCM (110 mL) at room temperature and the mixture was stirred for 40 minutes. The solvent was evaporated from the reaction solution under reduced pressure, and the resulting residue was dissolved in TBME and extracted with saturated aqueous sodium carbonate. The aqueous layer was adjusted to pH=2 with phosphoric acid and extracted with TBME. The resulting organic layer was washed with brine and then dried over anhydrous sodium sulfate, and the solvent was evaporated under reduced pressure. The resulting residue was purified by silica gel column chromatography (ethyl acetate/petroleum ether, 0/100 to 40/60) to give Compound aa033-d (10.2 g, 93%). This was mixed with another batch synthesized in the same manner and was used for the next reaction.

LCMS (ESI) m/z=448 (M+Na)+
Retention time: 2.042 min (analysis condition SMD-method_05)

Compound aa033-d (200 g, 470 mmol), DCC (96.99 g, 470 mmol), and N-hydroxyphthalimide (84.35 g, 517.062 mmol) were dissolved in THF (2 L), and the mixture was stirred at room temperature for one hour. The solid in the reaction solution was removed by filtration, and the solvent was evaporated from the filtrate under reduced pressure. The resulting residue was purified by silica gel column chromatography (ethyl acetate/petroleum ether, 0/100 to 40/60) to give Compound aa033-e (1-O-tert-butyl 4-O-(1,3-dioxoisoindol-2-yl) (2S)-2-[9H-fluoren-9-ylmethoxycarbonyl(methyl)amino]butanedioate) (200 g, 73%).

LCMS (ESI) m/z=593 (M+Na)+
Retention time: 2.706 min (analysis condition SMD-method_07)

1H-NMR (400 MHz, DMSO-d6) δ 8.04-7.84 (m, 6H), 7.69-7.59 (m, 2H), 7.44-7.28 (m, 4H), 4.91-4.65 (m, 1H), 4.63-4.14 (m, 3H), 3.31-3.09 (m, 1H), 3.07 (s, 2H), 2.81 (s, 3H), 1.38 (s, 9H), 1.10 (s, 4H).

Under a nitrogen atmosphere, nickel bromide trihydrate (NiBr$_2$·3H$_2$O) (0.287 g, 1.052 mmol) and 4,4'-di-tert-butyl-2,2'-bipyridyl (0.282 g, 1.052 mmol) were dissolved in DMA (16 mL) to prepare a Ni solution.

Under a nitrogen atmosphere, DMA (16 mL) was added to Compound aa033-e (2.0 g, 3.51 mmol), zinc powder (1.146 g, 17.53 mmol), and 5-bromo-2-(trifluoromethyl)pyridine (2.376 g, 10.52 mmol), after which the previously prepared Ni solution was added and the mixture was stirred at room temperature for 14 hours. The reaction solution was then diluted with TBME (250 mL), and the solid component was removed by filtration. The resulting TBME/DMA solution was washed with an aqueous EDTA solution (1 g dissolved in 100 mL of water) twice, and the organic layer was dried over anhydrous sodium sulfate, filtered, and concentrated under reduced pressure. The resulting residue was purified by reverse phase column chromatography (acetonitrile with 0.1% formic acid/distilled water with 0.1% formic acid), and the fractions were lyophilized to give Compound aa033-f (1.15 g, 62.3%).

LCMS (ESI) m/z=527 (M+H)+
Retention time: 1.08 min (analysis condition SQDFA05)

The obtained Compound aa033-f (1.15 g, 2.184 mmol) was dissolved in a 4N hydrochloric acid/1,4-dioxane solution (10.92 mL, 43.7 mmol), and the mixture was stirred at room temperature for 19 hours and then the reaction solution was concentrated under reduced pressure to give Compound aa033 ((2S)-2-[9H-fluoren-9-ylmethoxycarbonyl(methyl)amino]-3-[6-(trifluoromethyl)pyridin-3-yl]propanoic acid, Fmoc-MeAla(3-Pyr-4-CF3)-OH) (1.20 g, quant.).

LCMS (ESI) m/z=471 (M+H)+
Retention time: 0.87 min (analysis condition SQDFA05)

Herein, conversion of NH amino acid protected by Fmoc group to N-methylamino acid was carried out according to the basic two-step synthesis route provided below. Examples of synthesis by N-methylation reaction will be described herein for each amino acid, but any methods described in different parts of the present specification may be used.

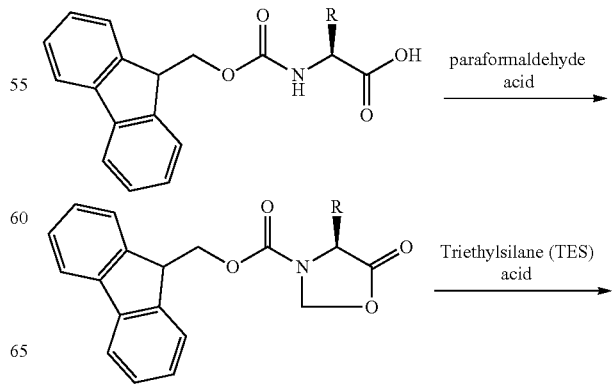

-continued

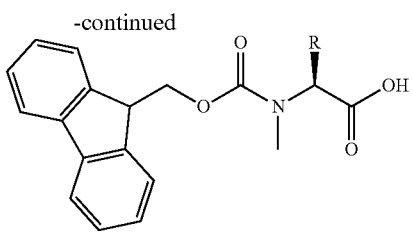

Synthesis of Compound aa034, (2S)-2-[9H-fluoren-9-ylmethoxycarbonyl(methyl)amino]-3-(5-methoxy-pyridin-3-yl)propanoic acid (Fmoc-MeAla(3-Pyr-5-OMe)-OH)

LCMS (ESI) m/z=489 (M+H)+
Retention time: 0.89 min (analysis condition SQDFA05)

Compound aa034 ((2S)-2-[9H-fluoren-9-ylmethoxycarbonyl(methyl)amino]-3-(5-methoxypyridin-3-yl)propanoic acid, Fmoc-MeAla(3-Pyr-5-OMe)-OH) (807.4 mg, quant.) was obtained by the same method as in the synthesis of Compound aa033 using Compound aa034-a (0.72 g, 1.474 mmol) as a raw material.

LCMS (ESI) m/z=433 (M+H)+
Retention time: 0.63 min (analysis condition SQDFA05)

Synthesis of Compound aa035, (2S)-2-[9H-fluoren-9-ylmethoxycarbonyl(methyl)amino]-3-(5-methylpyridin-3-yl)propanoic acid (Fmoc-MeAla(3-Pyr-5-Me)-OH)

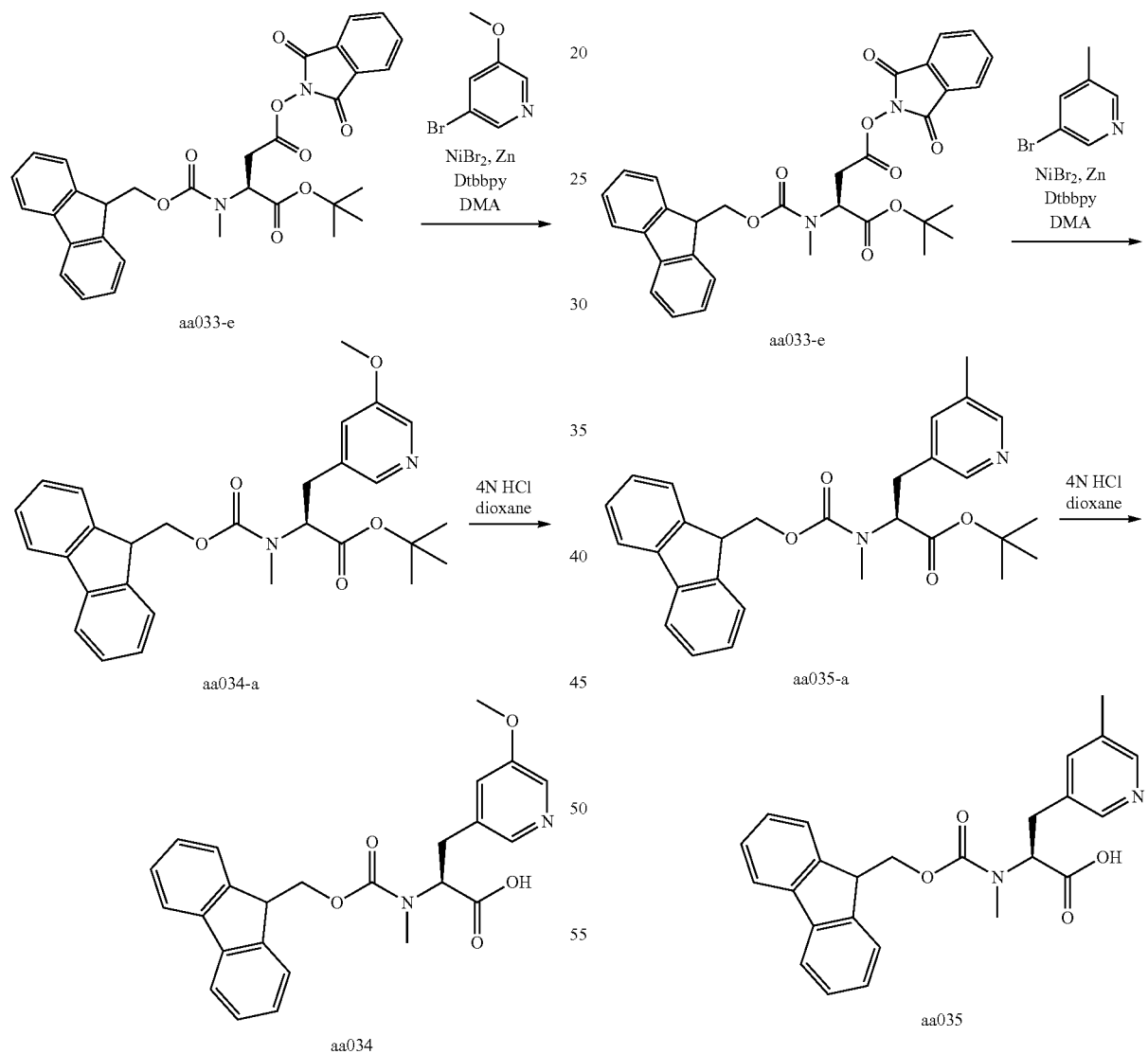

Compound aa034-a (0.72 g, 42%) was obtained by the same method as in the synthesis of Compound aa033-f using Compound aa033-e (1-O-tert-butyl 4-O-(1,3-dioxoisoindol-2-yl) (2S)-2-[9H-fluoren-9-ylmethoxycarbonyl(methyl)amino]butanedioate) (2 g, 3.51 mmol) and 3-bromo-5-methoxypyridine as raw materials.

Compound aa035-a (0.49 g, 29.6%) was obtained by the same method as in the synthesis of Compound aa033-f using Compound aa033-e (1-O-tert-butyl 4-O-(1,3-dioxoisoindol-2-yl) (2S)-2-[9H-fluoren-9-ylmethoxycarbonyl(methyl)amino]butanedioate) (2.0 g, 3.51 mmol) and 3-bromo-5-methylpyridine as raw materials.

LCMS (ESI) m/z=473 (M+H)+

Retention time: 0.78 min (analysis condition SQDFA05)

Compound aa035 ((2S)-2-[9H-fluoren-9-ylmethoxycarbonyl(methyl)amino]-3-(5-methylpyridin-3-yl)propanoic acid, Fmoc-MeAla(3-Pyr-5-Me)-OH) (1.14 g, quant.) was obtained by the same method as in the synthesis of Compound aa033 using Compound aa035-a (1.03 g, 2.18 mmol) as a raw material.

LCMS (ESI) m/z=417 (M+H)+
Retention time: 0.60 min (analysis condition SQDFA05)

Synthesis of Compound aa036, (2S)-2-[9H-fluoren-9-ylmethoxycarbonyl(methyl)amino]-3-(6-methoxypyridin-3-yl)propanoic acid (Fmoc-MeAla(3-Pyr-4-OMe)-OH)

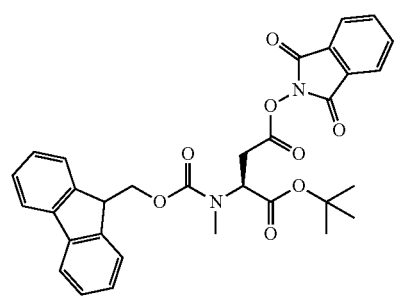

aa033-e

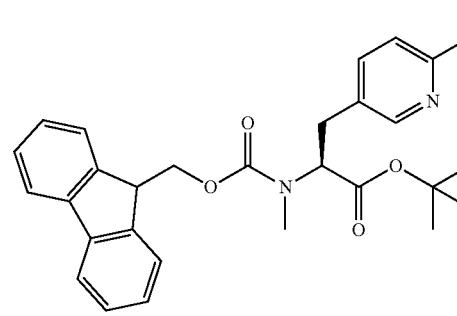

aa036-a

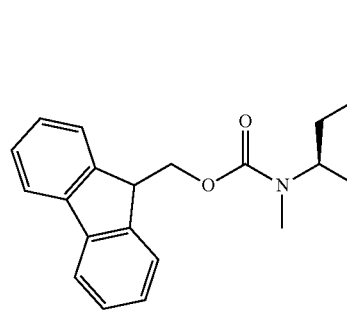

aa036

Compound aa036-a (752 mg, 43.9%) was obtained by the same method as in the synthesis of Compound aa033-f using Compound aa033-e (1-O-tert-butyl 4-O-(1,3-dioxoisoindol-2-yl) (2S)-2-[9H-fluoren-9-ylmethoxycarbonyl(methyl)amino]butanedioate) (2 g, 3.51 mmol) and 5-bromo-2-methoxypyridine as raw materials.

LCMS (ESI) m/z=489 (M+H)+
Retention time: 1.08 min (analysis condition SQDFA05)

Compound aa036 ((2S)-2-[9H-fluoren-9-ylmethoxycarbonyl(methyl)amino]-3-(6-methoxypyridin-3-yl)propanoic acid, Fmoc-MeAla(3-Pyr-4-OMe)-OH) (715 mg, 99%) was obtained by the same method as in the synthesis of Compound aa033 using Compound aa036-a (752 mg, 1.539 mmol) as a raw material.

LCMS (ESI) m/z=433 (M+H)+
Retention time: 0.82 min (analysis condition SQDFA05)

Synthesis of Compound aa037, (2S)-2-[9H-fluoren-9-ylmethoxycarbonyl(methyl)amino]-3-(6-methylpyridin-3-yl)propanoic acid (Fmoc-MeAla(3-Pyr-4-Me)-OH)

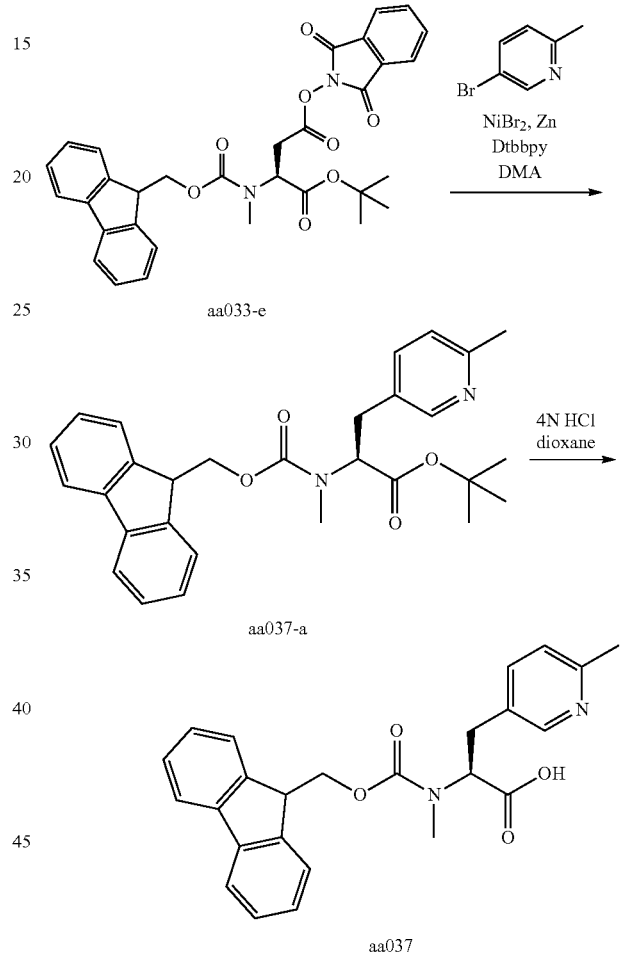

A crude product obtained by the same method as in the synthesis of Compound aa033-f using Compound aa033-e (1-O-tert-butyl 4-O-(1,3-dioxoisoindol-2-yl) (2S)-2-[9H-fluoren-9-ylmethoxycarbonyl(methyl)amino]butanedioate) (2 g, 3.51 mmol) and 5-bromo-2-methylpyridine as raw materials was purified by silica gel column chromatography (hexane/ethyl acetate) to give Compound aa037-a (780 mg, 47.1%).

LCMS (ESI) m/z=473 (M+H)+
Retention time: 0.73 min (analysis condition SQDFA05)

Compound aa037 ((2S)-2-[9H-fluoren-9-ylmethoxycarbonyl(methyl)amino]-3-(6-methylpyridin-3-yl)propanoic acid, Fmoc-MeAla(3-Pyr-4-Me)-OH) (686 mg, 92%) was obtained by the same method as in the synthesis of Compound aa033 using Compound aa037-a (780 mg, 1.65 mmol) as a raw material.

LCMS (ESI) m/z=417 (M+H)+
Retention time: 0.56 min (analysis condition SQDFA05)

Synthesis of Compound aa038, (2S)-3-(5-bromopyridin-3-yl)-2-[9H-fluoren-9-ylmethoxycarbonylamino]propanoic acid (Fmoc-Ala(3-Pyr-5-Br)—OH)

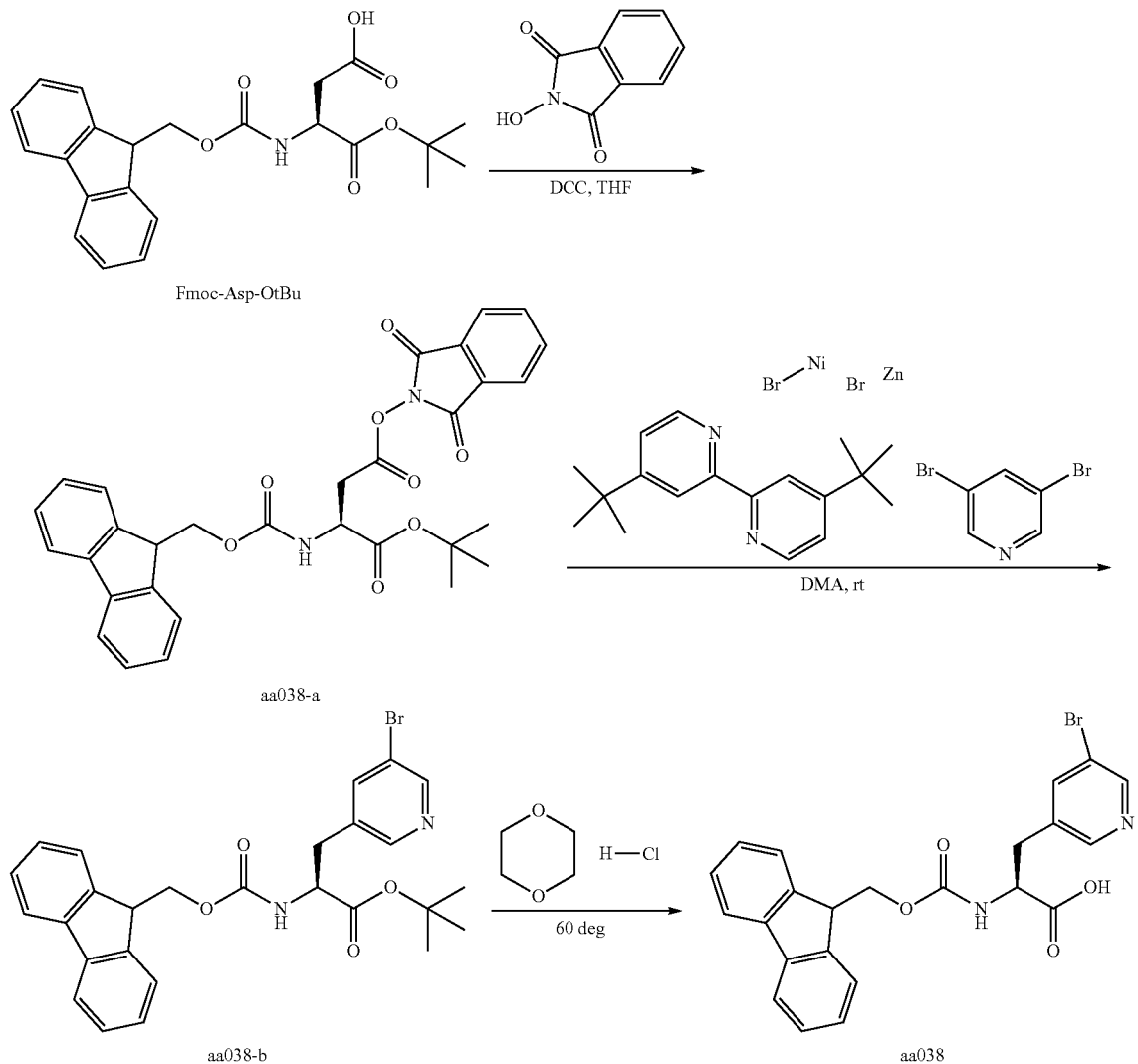

Fmoc-Asp-OtBu ((3S)-3-[19H-fluoren-9-ylmethoxycarbonylamino]-4-[1(2-methylpropan-2-yl)oxy]-4-oxobutanoic acid, CAS No. 129460-09-9) (300 g, 729 mmol) and N-hydroxyphthalimide (130.8 g, 801.8 mmol) were added to THF (3 L), DCC (181.8 g, 1.1 mol) was further added thereto, and the mixture was stirred at room temperature for three hours. The solvent was evaporated from the reaction solution under reduced pressure. Toluene was added to the residue, and the solid was removed by filtration. The solvent was evaporated from the filtrate under reduced pressure, and the resulting residue was purified by silica gel column chromatography (hexane/ethyl acetate) to give Compound aa038-a (272 g, 67%).

LCMS (ESI) m/z=578.7 (M+Na)+

Retention time: 1.728 min (analysis condition SMD-method_08)

Compound aa038-b (722 mg, 30%) was obtained by the same method as in the synthesis of Compound aa033-f using Compound aa038-a (2.6 g, 4.67 mmol) and 3,5-dibromopyridine as raw materials.

LCMS (ESI) m/z=523 (M+H)+

Retention time: 1.08 min (analysis condition SQDFA05)

A concentrate of Compound aa038 was obtained by the same method as in the synthesis of Compound aa033 using Compound aa038-b (722 mg, 1.379 mmol). The resulting concentrate was purified by reverse phase chromatography (acetonitrile/distilled water) to give Compound aa038 ((2S)-3-(5-bromopyridin-3-yl)-2-[9H-fluoren-9-ylmethoxycarbonylamino]propanoic acid, Fmoc-Ala(3-Pyr-5-Br)—OH) (300 mg, 40%).

LCMS (ESI) m/z=467 (M+H)+

Retention time: 0.77 min (analysis condition SQDFA05)

Synthesis of Compound aa039, (2S)-2-[9H-fluoren-9-ylmethoxycarbonyl(methyl)amino]-4-pyridin-3-ylbutanoic acid (Fmoc-MeAbu(3-Pyr)-OH)

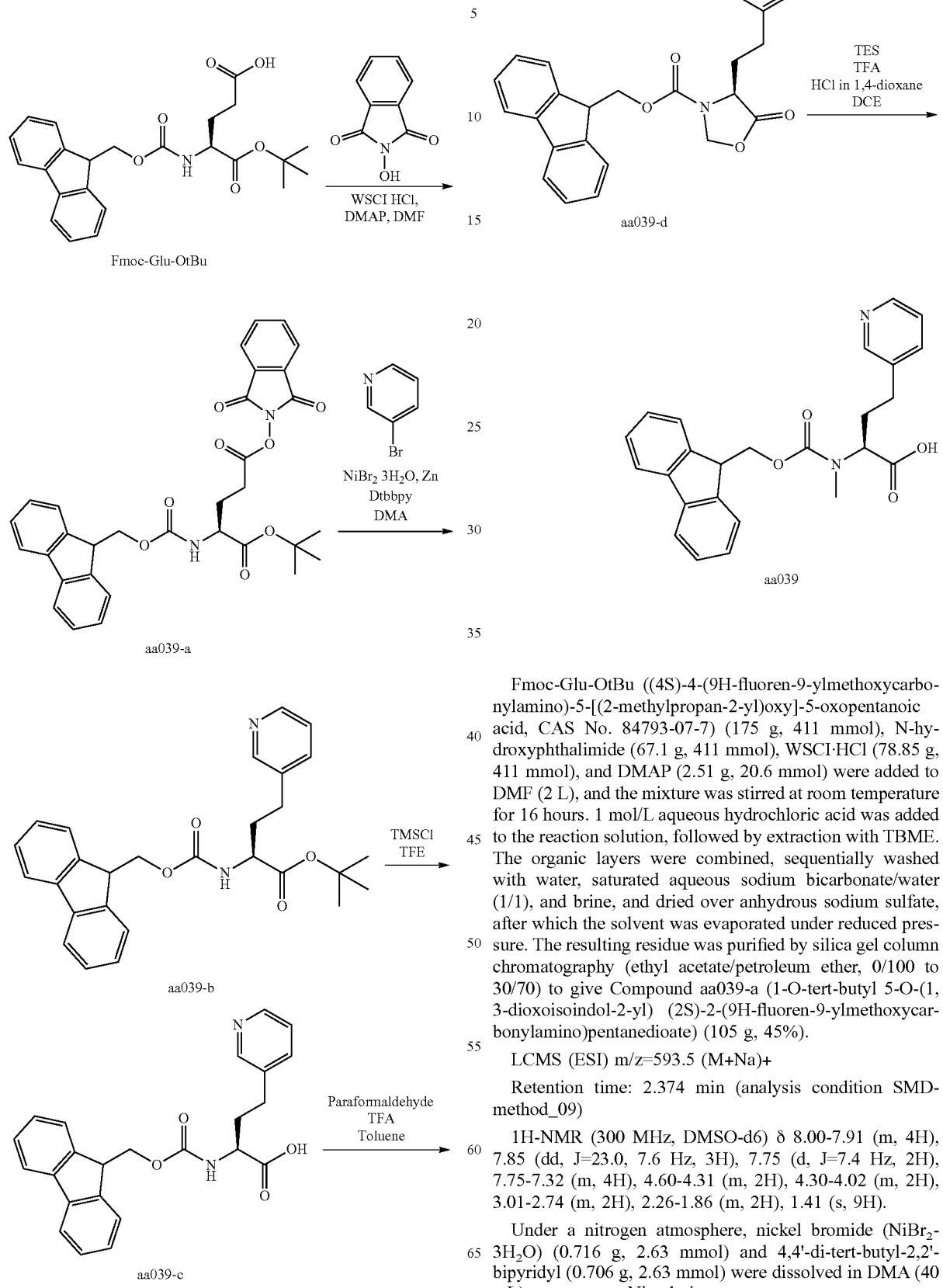

Fmoc-Glu-OtBu ((4S)-4-(9H-fluoren-9-ylmethoxycarbonylamino)-5-[(2-methylpropan-2-yl)oxy]-5-oxopentanoic acid, CAS No. 84793-07-7) (175 g, 411 mmol), N-hydroxyphthalimide (67.1 g, 411 mmol), WSCI·HCl (78.85 g, 411 mmol), and DMAP (2.51 g, 20.6 mmol) were added to DMF (2 L), and the mixture was stirred at room temperature for 16 hours. 1 mol/L aqueous hydrochloric acid was added to the reaction solution, followed by extraction with TBME. The organic layers were combined, sequentially washed with water, saturated aqueous sodium bicarbonate/water (1/1), and brine, and dried over anhydrous sodium sulfate, after which the solvent was evaporated under reduced pressure. The resulting residue was purified by silica gel column chromatography (ethyl acetate/petroleum ether, 0/100 to 30/70) to give Compound aa039-a (1-O-tert-butyl 5-O-(1,3-dioxoisoindol-2-yl) (2S)-2-(9H-fluoren-9-ylmethoxycarbonylamino)pentanedioate) (105 g, 45%).

LCMS (ESI) m/z=593.5 (M+Na)+

Retention time: 2.374 min (analysis condition SMD-method_09)

1H-NMR (300 MHz, DMSO-d6) δ 8.00-7.91 (m, 4H), 7.85 (dd, J=23.0, 7.6 Hz, 3H), 7.75 (d, J=7.4 Hz, 2H), 7.75-7.32 (m, 4H), 4.60-4.31 (m, 2H), 4.30-4.02 (m, 2H), 3.01-2.74 (m, 2H), 2.26-1.86 (m, 2H), 1.41 (s, 9H).

Under a nitrogen atmosphere, nickel bromide (NiBr$_2$·3H$_2$O) (0.716 g, 2.63 mmol) and 4,4'-di-tert-butyl-2,2'-bipyridyl (0.706 g, 2.63 mmol) were dissolved in DMA (40 mL) to prepare a Ni solution.

Under a nitrogen atmosphere, DMA (40 mL) was added to Compound aa039-a (5.0 g, 8.76 mmol), zinc powder (2.86 g, 43.8 mmol), and 3-bromopyridine (2.55 mL, 26.3 mmol), after which the previously prepared Ni solution was added and the mixture was stirred at room temperature for 14 hours. The reaction solution was then diluted with TBME (150 mL), after which the resulting TBME/DMA solution was washed with an aqueous EDTA solution (16 g dissolved in 250 mL of water) and then washed with saturated aqueous sodium carbonate/water (1/1, 80 mL). The organic layer was dried over anhydrous sodium sulfate, filtered, and then concentrated under reduced pressure. The resulting residue was purified by reverse phase column chromatography (acetonitrile with 0.1% formic acid/distilled water with 0.1% formic acid), and the fractions were lyophilized to give Compound aa039-b (2.5 g, 62.2%).

LCMS (ESI) m/z=459 (M+H)+

Retention time: 0.69 min (analysis condition SQDFA05)

The obtained Compound aa039-b (2.5 g, 5.45 mmol) was dissolved in TFE (27.3 mL), and TMSCl (2.1 mL, 16.4 mmol) was added. The reaction solution was stirred at room temperature for one hour and then concentrated under reduced pressure. The resulting residue was dissolved in TBME (1 mL) and concentrated. This operation was performed three times to give the target Compound aa039-c as a crude product (2.38 g, 99%).

LCMS (ESI) m/z=403.2 (M+H)+

Retention time: 0.51 min (analysis condition SQDFA05)

The obtained Compound aa039-c (2.38 g, 5.42 mmol) and paraformaldehyde (0.488 g, 16.3 mmol) were dissolved in toluene (6.57 mL), TFA (3.76 mL, 48.8 mmol) was added, and the mixture was warmed to 40° C. The reaction solution was stirred at 40° C. for five hours and cooled to room temperature. The reaction solution was concentrated under reduced pressure to give a residue, which was then dissolved in ethyl acetate (20 mL), washed with a saturated aqueous sodium carbonate solution (20 mL), and then washed with brine (20 mL). The organic layer was dried over anhydrous sodium sulfate, filtered, and then concentrated under reduced pressure. The residue was purified by normal phase column chromatography (hexane/ethyl acetate), and the resulting fractions were concentrated to give the target Compound aa039-d (1.33 g, 59%).

LCMS (ESI) m/z=415 (M+H)+

Retention time: 0.58 min (analysis condition SQDFA05)

The obtained Compound aa039-d (1.33 g, 3.21 mmol) was dissolved in dichloroethane (DCE) (6.7 mL) and HCl/1,4-dioxane (4N, 6.9 mL), triethylsilane (4.58 mL, 28.9 mmol) was added, and TFA (6.68 mL, 87 mmol) was then added. The reaction solution was warmed to 70° C. and stirred for two hours. The reaction solution was cooled to room temperature and then concentrated under reduced pressure. The residue was purified by reverse phase column chromatography (acetonitrile with 0.05% TFA/distilled water with 0.05% TFA), and the fractions were lyophilized. The resulting TFA salt was desalted through purification by reverse phase column chromatography (acetonitrile/distilled water) to give Compound aa039 ((2S)-2-[9H-fluoren-9-ylmethoxycarbonyl(methyl)amino]-4-pyridin-3-ylbutanoic acid, Fmoc-MeAbu(3-Pyr)-OH) (1.01 g, 69.5%).

LCMS (ESI) m/z=417 (M+H)+

Retention time: 0.52 min (analysis condition SQDFA05)

Synthesis of Compound aa040, (2S)-2-[9H-fluoren-9-ylmethoxycarbonyl(methyl)amino]-4-pyridin-4-ylbutanoic acid (Fmoc-MeAbu(4-Pyr)-OH)

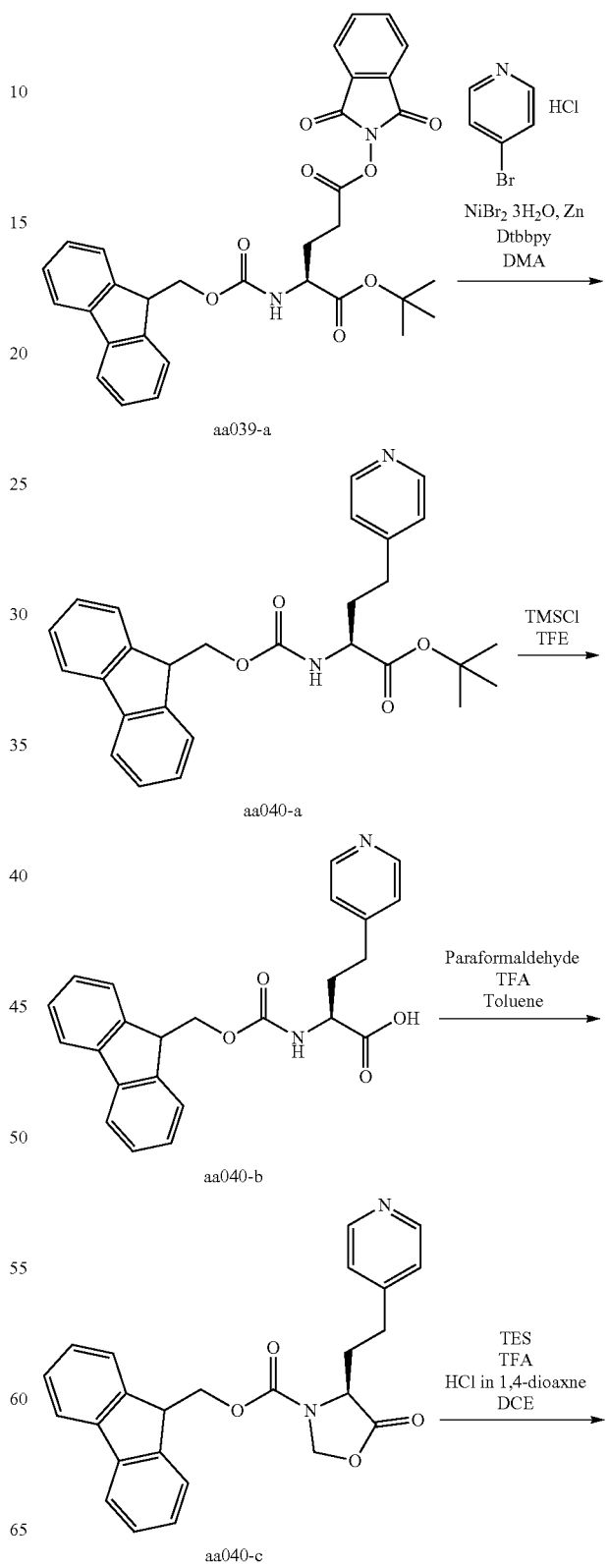

487

-continued

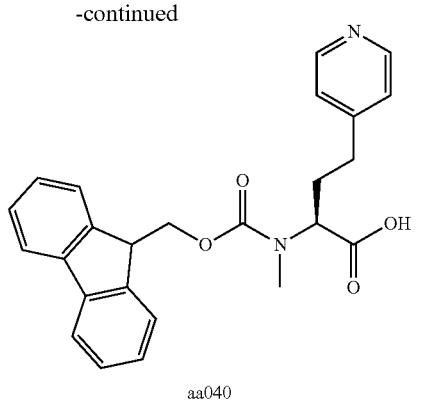

aa040

Under a nitrogen atmosphere, nickel bromide (NiBr$_2$·3H$_2$O) (0.615 g, 2.26 mmol) and 4,4'-di-tert-butyl-2,2'-bipyridyl (0.605 g, 2.26 mmol) were dissolved in DMA (37 mL) to prepare a Ni solution.

4-Bromopyridine hydrochloride (4.39 g, 22.6 mmol) was desalted by dissolving it in toluene (10 mL), a 5N aqueous sodium hydroxide solution (5 mL), and water (5 mL) and an organic layer was prepared as a 4-bromopyridine solution.

Under a nitrogen atmosphere, Compound aa039-a (1-O-tert-butyl 5-O-(1,3-dioxoisoindol-2-yl) (2S)-2-(9H-fluoren-9-ylmethoxycarbonylamino)pentanedioate) (4.3 g, 7.52 mmol) and zinc powder (2.46 g, 37.6 mmol) were added to DMA (37 mL), followed by stirring. The previously prepared 4-bromopyridine solution (10 mL, 22.6 mmol) was added, the previously prepared Ni solution was then added, and the mixture was stirred at room temperature for 14 hours. The reaction solution was then diluted with TBME (150 mL), after which the resulting TBME/DMA solution was washed with an aqueous EDTA·2Na solution (16 g dissolved in 250 mL of water) and then washed with saturated aqueous sodium carbonate/water (1/1, 80 mL). The organic layer was dried over anhydrous sodium sulfate, filtered, and then concentrated under reduced pressure. The resulting residue was purified by silica gel column chromatography (hexane/ethyl acetate), and the fractions were concentrated under reduced pressure to give Compound aa040-a (2.7 g, 78%).

LCMS (ESI) m/z=459 (M+H)+

Retention time: 0.65 min (analysis condition SQDFA05)

Compound aa040-b (2.7 g, quant.) was obtained by the same method as in the synthesis of Compound aa039-c using Compound aa040-a (2.7 g, 5.89 mmol) as a raw material.

LCMS (ESI) m/z=401 (M−H)−

Retention time: 0.55 min (analysis condition SQDFA05)

Compound aa040-c (1.8 g, 75%) was obtained by the same method as in the synthesis of Compound aa039-d using Compound aa040-b (2.55 g, 5.81 mmol) as a raw material.

LCMS (ESI) m/z=415 (M+H)+

Retention time: 0.55 min (analysis condition SQDFA05)

Compound aa040 ((2S)-2-[9H-fluoren-9-ylmethoxycarbonyl(methyl)amino]-4-pyridin-4-ylbutanoic acid, Fmoc-MeAbu(4-Pyr)-OH) (860 mg, 47%) was obtained by the same method as in the synthesis of Compound aa039 using Compound aa040-c (1.81 g, 4.37 mmol) as a raw material.

LCMS (ESI) m/z=417 (M+H)+

Retention time: 0.51 min (analysis condition SQDFA05)

488

Synthesis of Compound aa041, (2S)-3-cyclopropyloxy-2-(9H-fluoren-9-ylmethoxycarbonylamino)propanoic acid (Fmoc-Ser(cPr)—OH)

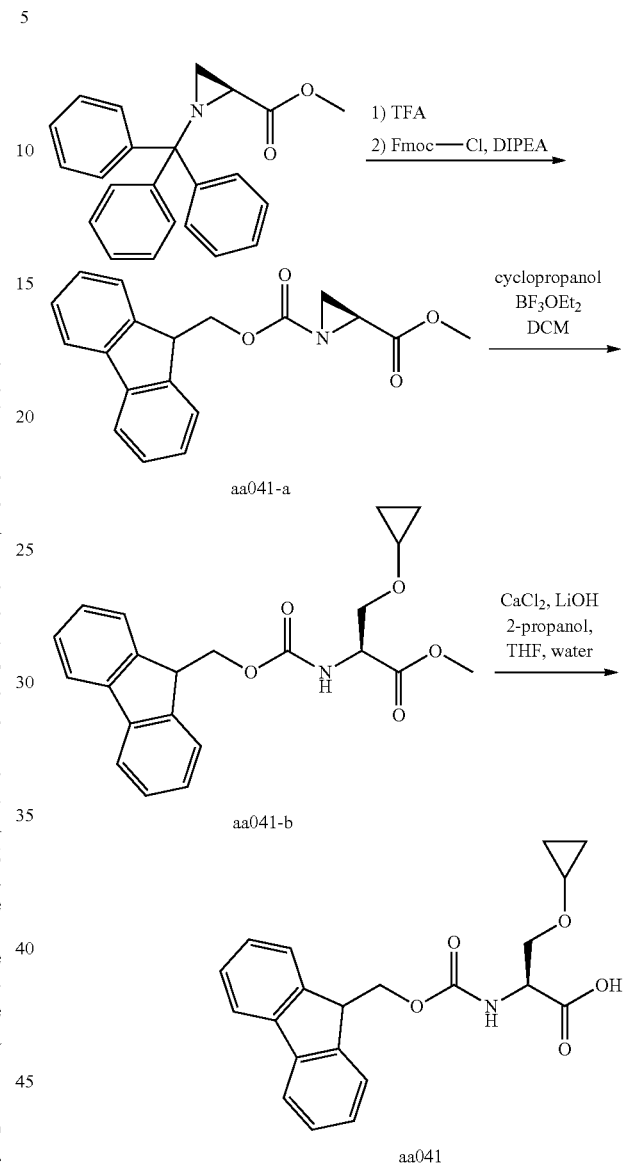

Methyl (S)—N-tritylaziridine-2-carboxylate (CAS No. 75154-68-6) (50 g, 146 mmol) was added to a mixed solution of chloroform (145 mL) and methanol (145 mL), trifluoroacetic acid (TFA) (33 mL, 3 equivalents) was added dropwise at 0° C. under a nitrogen atmosphere, and the mixture was stirred for seven hours. DIPEA (127 mL, 5 equivalents) was added to the reaction solution at 0° C., a solution of fluorenylmethyloxycarbonyl chloride (Fmoc-Cl) (36 g, 139 mmol) in 1,4-dioxane (145 mL) was further added dropwise, and the mixture was stirred at 0° C. for 90 minutes under a nitrogen atmosphere. The reaction solution was concentrated under reduced pressure, diluted with ethyl acetate, and then sequentially washed with water, an aqueous ammonium chloride solution, an aqueous sodium bicarbonate solution, and brine. The resulting organic layer was dried over anhydrous sodium sulfate and the solvent was then evaporated under reduced pressure. The resulting residue was purified by silica gel column chromatography (ethyl acetate/petroleum ether, 0/100 to 10/90) to give Compound aa041-a (1-0-(9H-fluoren-9-ylmethyl) 2-O-methyl (2S)-aziridine-1,2-dicarboxylate) (40 g, 85%).

LCMS (ESI) m/z=323.9 (M+H)+

Retention time: 2.631 min (analysis condition SMD-method_10)

Compound aa041-a (1-O-(9H-fluoren-9-ylmethyl) 2-O-methyl (2S)-aziridine-1,2-dicarboxylate) (5 g, 15.46 mmol) was dissolved in DCM (30.9 mL) under a nitrogen atmosphere, cyclopropanol (1.665 mL, 26.3 mmol) was added, and then boron trifluoride-diethyl ether complex (BF$_3$·OEt$_2$) (0.291 mL, 2.319 mmol) was added with ice-cooling. The reaction solution was reacted for two hours on ice and then the reaction was quenched with water and a saturated aqueous sodium bicarbonate solution. The aqueous layer was removed by a phase separator, and the organic layer was concentrated under reduced pressure. The resulting residue was purified by column chromatography (n-hexane/ethyl acetate=4/1) to give Compound aa041-b (4.6 g, 78%).

LCMS (ESI) m/z=382 (M+H)+

Retention time: 0.89 min (analysis condition SQDFA05)

Calcium chloride (20.08 g, 181 mmol) was dissolved in water (50.2 mL), lithium hydroxide monohydrate (2.024 g, 48.2 mmol) was added thereto, and the mixture was stirred at room temperature for five minutes to prepare an aqueous solution A. Compound aa041-b (4.6 g, 12.06 mmol) was dissolved in isopropanol (201 mL) and THF (50.2 mL), the previously prepared aqueous solution A was added, and the mixture was stirred at room temperature for five hours. 1 mol/L aqueous hydrochloric acid (36.2 mL) was then added to the reaction solution, after which isopropanol and THF were removed by concentration under reduced pressure. The resulting aqueous layer was diluted with water (50.2 mL) and extracted with ethyl acetate three times (total volume: 100 mL). The organic layers were washed with water and brine, dried over anhydrous sodium sulfate, and filtered, and the filtrate was then concentrated under reduced pressure. The resulting residue was washed with ethyl acetate/n-hexane (1/2, 20 v/w) to give the titled Compound aa041 ((2S)-3-cyclopropyloxy-2-(9H-fluoren-9-ylmethoxycarbonylamino)propanoic acid, Fmoc-Ser(cPr)—OH) (3.5 g, 79%).

LCMS (ESI) m/z=368 (M+H)+

Retention time: 0.78 min (analysis condition SQDFA05)

Synthesis of Compound aa042, (2S)-3-cyclobutyloxy-2-[9H-fluoren-9-ylmethoxycarbonyl(methyl)amino]propanoic acid (Fmoc-MeSer(cBu)-OH)

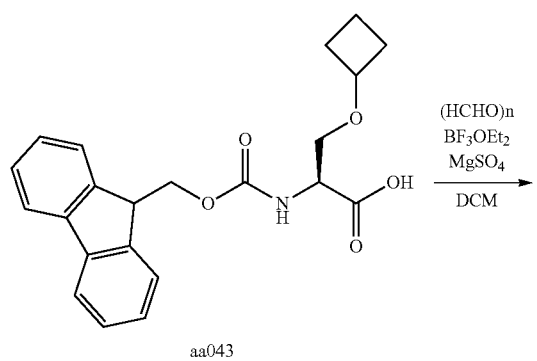

Compound aa042-a was obtained as a crude product by the same method as in the synthesis of Compound aa069-b using Compound aa043 ((2S)-3-cyclobutyloxy-2-(9H-fluoren-9-ylmethoxycarbonylamino)propanoic acid) (10.61 g, 27.8 mmol) as a starting material.

LCMS (ESI) m/z=394.5 (M+H)+

Retention time: 1.01 min (analysis condition SQDFA05)

Compound aa042 ((2S)-3-cyclobutyloxy-2-[9H-fluoren-9-ylmethoxycarbonyl(methyl)amino]propanoic acid, Fmoc-MeSer(cBu)-OH) (10.6 g, 96% through two steps) was obtained by the same method as in the synthesis of Compound aa069 using the total amount of Compound aa042-a obtained above.

LCMS (ESI) m/z=396 (M+H)+

Retention time: 0.87 min (analysis condition SQDFA05)

Synthesis of Compound aa043, (2S)-3-cyclobutyloxy-2-(9H-fluoren-9-ylmethoxycarbonylamino)propanoic acid (Fmoc-Ser(cBu)-OH)

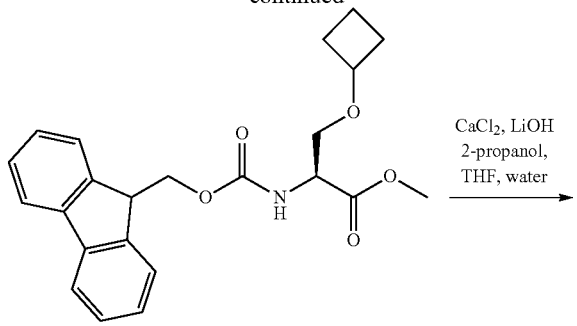

aa043-a

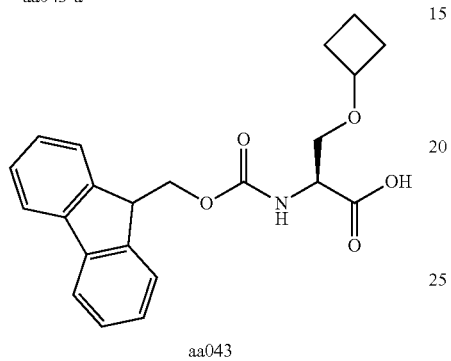

aa043

Compound aa043-a (4.54 g, 74.2%) was obtained by the same method as in the synthesis of Compound aa041-b using Compound aa041-a (1-O-(9H-fluoren-9-ylmethyl) 2-O-methyl (2S)-aziridine-1,2-dicarboxylate) (5 g, 15.46 mmol) and cyclobutanol as raw materials.

LCMS (ESI) m/z=396 (M+H)+

Retention time: 0.94 min (analysis condition SQDFA05)

Compound aa043 ((2S)-3-cyclobutyloxy-2-(9H-fluoren-9-ylmethoxycarbonylamino)propanoic acid, Fmoc-Ser (cBu)-OH) (3.78 g, 86%) was obtained by the same method as in the synthesis of Compound aa041 using Compound aa043-a (4.54 g, 11.48 mmol) as a raw material.

LCMS (ESI) m/z=382 (M+H)+

Retention time: 0.82 min (analysis condition SQDFA05)

Synthesis of Compound aa044, (2S)-2-(9H-fluoren-9-ylmethoxycarbonylamino)-3-(2,2,2-trifluoroethoxy)propanoic acid (Fmoc-Ser(Tfe)-OH)

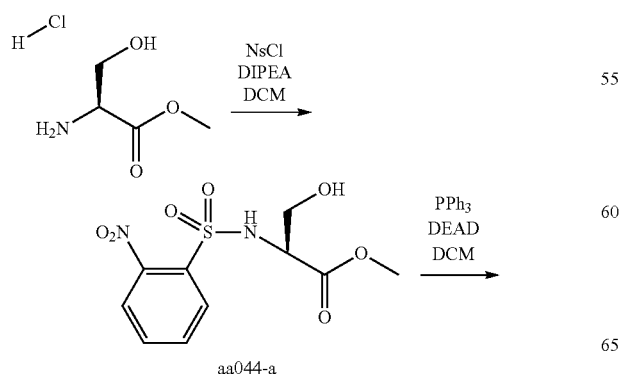

aa044-a

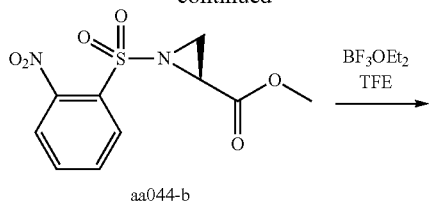

aa044-b

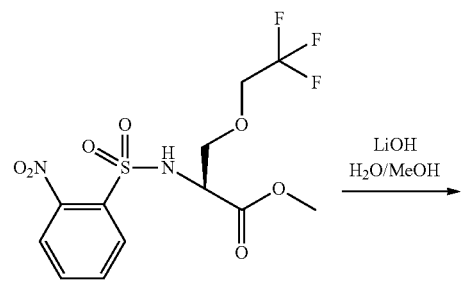

aa044-c

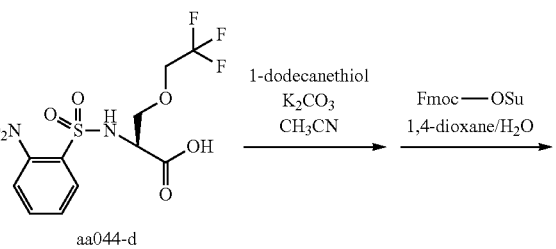

aa044-d

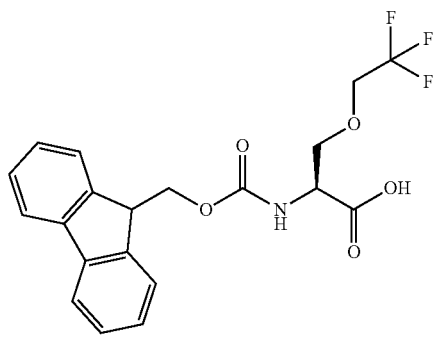

aa044

2-Nitrobenzenesulfonyl chloride (NsCl) (32.37 g, 146 mmol) and L-serine methyl ester hydrochloride (25 g, 161 mmol, CAS No. 5680-80-8) were dissolved in DCM (874 mL), and DIPEA (51 mL, 292 mmol) was added at 5° C. After stirring at room temperature for one hour, the reaction solution was washed with water (440 mL) twice, washed with brine/water (1/1, 440 mL) once, and then dried over magnesium sulfate. The magnesium sulfate was filtered off and the filtrate was concentrated under reduced pressure to give Compound aa044-a (39.4 g, 89%) as a crude product.

LCMS (ESI) m/z=302.9 (M−H)−

Retention time: 0.729 min (analysis condition SMD-method_06)

Compound aa044-a (23 g, 75.6 mmol) was dissolved in DCM (598 mL), and triphenylphosphine (31.7 g, 121 mmol) was added at room temperature. After cooling to −14° C., DEAD (55.0 mL, 121 mmol) was added over 10 minutes, and the mixture was then stirred at −5° C. for 50 minutes. n-Hexane (300 mL) was added and the precipitate was filtered off. The filtrate was purified by silica gel column chromatography (n-hexane/DCM=50:50 to 0:100) to give Compound aa044-b (13.3 g, 62%).

LCMS (ESI) m/z=287 (M+H)+

Retention time: 0.872 min (analysis condition SMD-method_06)

Compound aa044-b (10.7 g, 37.3 mmol) was dissolved in TFE (75 mL), boron trifluoride-diethyl ether complex (BF$_3$·OEt$_2$) (0.469 mL, 3.73 mmol) was added, and the mixture was then stirred at 70° C. for 30 minutes. TFE was evaporated under reduced pressure, and the resulting crude product was purified by reverse phase column chromatography (acetonitrile with 0.1% formic acid/distilled water with 0.1% formic acid) to give Compound aa044-c (12.3 g, 85%).

LCMS (ESI) m/z=387 (M+H)+

Retention time: 0.72 min (analysis condition SQDFA05)

Compound aa044-c (12 g, 31.1 mmol) was dissolved in methanol (47 mL), and a solution of lithium hydroxide monohydrate (5.21 g, 124 mmol) in water (31 mL) was added. The reaction solution was stirred at room temperature for 90 minutes, followed by addition of formic acid (11.7 mL, 311 mmol). The reaction solution was diluted with water (30 mL) and then purified by reverse phase column chromatography (acetonitrile with 0.1% formic acid/distilled water with 0.1% formic acid) to give Compound aa044-d (7.90 g, 68%).

LCMS (ESI) m/z=373 (M+H)+

Retention time: 0.63 min (analysis condition SQDFA05)

Compound aa044-d (7.72 g, 20.7 mmol) was dissolved in acetonitrile (104 mL), potassium carbonate (7.17 g, 51.8 mmol) and dodecanethiol (7.44 mL, 31.1 mmol) were added, and the mixture was then stirred at room temperature for 74 hours. This was diluted with water (100 mL) and washed with TBME (200 mL) twice. A solution of Fmoc-OSu (3.5 g) in 1,4-dioxane (150 mL) was added to the resulting aqueous solution, and the mixture was stirred for 25 minutes. A solution of Fmoc-OSu (700 mg) in 1,4-dioxane (10 mL) was further added, and the mixture was stirred for five minutes. A solution of Fmoc-OSu (350 mg) in 1,4-dioxane (5 mL) was further added, and the mixture was stirred for five minutes. A solution of Fmoc-OSu (350 mg) in 1,4-dioxane (5 mL) was further added, and the mixture was stirred for five minutes, after which formic acid (3.9 mL) was added and the solvent was evaporated under reduced pressure. The resulting crude product was purified by reverse phase column chromatography (acetonitrile with 0.1% formic acid/distilled water with 0.1% formic acid) to give Compound aa044 ((2S)-2-(9H-fluoren-9-ylmethoxycarbonylamino)-3-(2,2,2-trifluoroethoxy)propanoic acid, Fmoc-Ser(Tfe)-OH) (5.67 g, 67%).

LCMS (ESI) m/z=410 (M+H)+

Retention time: 2.35 min (analysis condition SQDFA05long)

Synthesis of Compound aa045, (2S)-2-[9H-fluoren-9-ylmethoxycarbonyl(methyl)amino]-3-(2,2,2-trifluoroethoxy)propanoic acid (Fmoc-MeSer(Tfe)-OH)

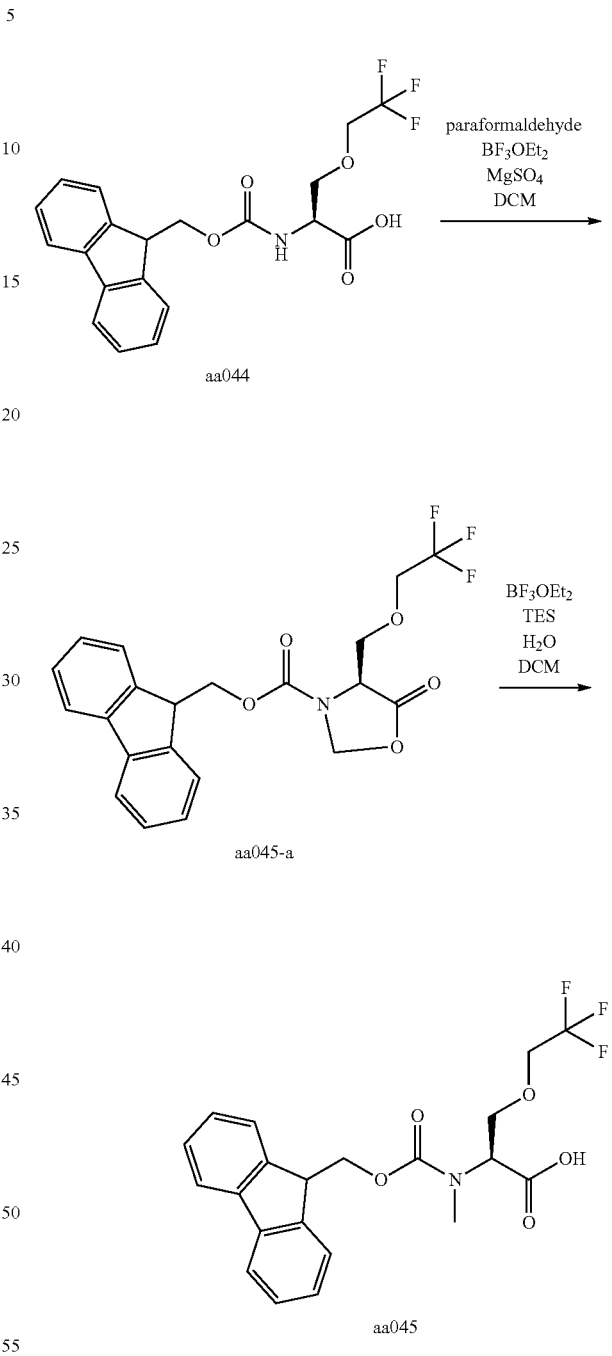

Compound aa045-a was obtained as a crude product by the same method as in the synthesis of Compound aa069-b using Compound aa044 (2.00 g, 4.89 mmol) as a starting material. In addition, Compound aa045 ((2S)-2-[9H-fluoren-9-ylmethoxycarbonyl(methyl)amino]-3-(2,2,2-trifluoroethoxy)propanoic acid, Fmoc-MeSer(Tfe)-OH) (1.80 g, 87% through two steps) was obtained by the same method as in the synthesis of Compound aa069.

LCMS (ESI) m/z=424 (M+H)+

Retention time: 0.84 min (analysis condition SQDFA05)

Synthesis of Compound aa047, (2S)-4-(3,3-difluoroazetidin-1-yl)-2-[9H-fluoren-9-ylmethoxycarbonyl(methyl)amino]butanoic acid (Fmoc-MeAbu(Aze-3-F2)-OH)

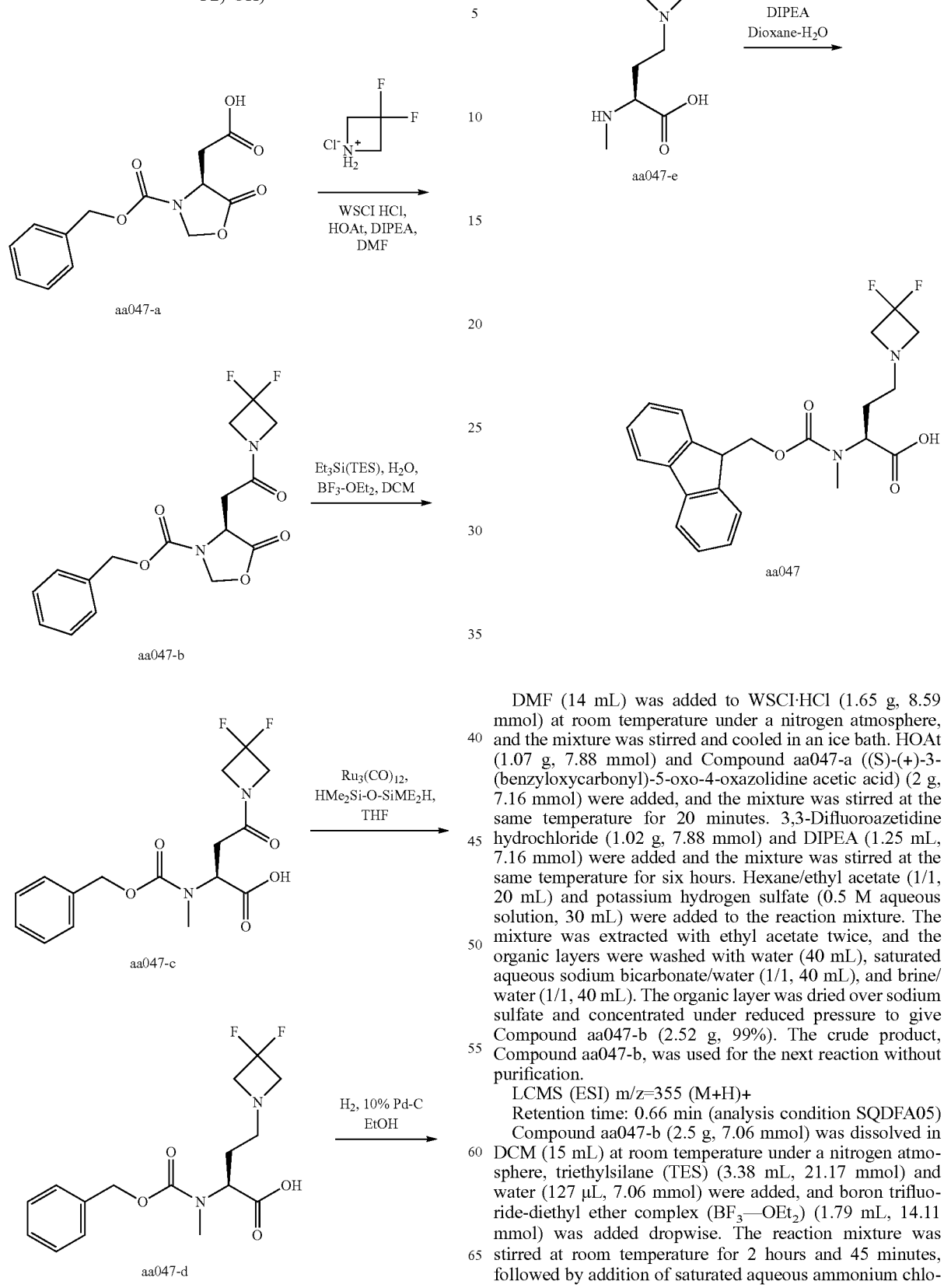

DMF (14 mL) was added to WSCI·HCl (1.65 g, 8.59 mmol) at room temperature under a nitrogen atmosphere, and the mixture was stirred and cooled in an ice bath. HOAt (1.07 g, 7.88 mmol) and Compound aa047-a ((S)-(+)-3-(benzyloxycarbonyl)-5-oxo-4-oxazolidine acetic acid) (2 g, 7.16 mmol) were added, and the mixture was stirred at the same temperature for 20 minutes. 3,3-Difluoroazetidine hydrochloride (1.02 g, 7.88 mmol) and DIPEA (1.25 mL, 7.16 mmol) were added and the mixture was stirred at the same temperature for six hours. Hexane/ethyl acetate (1/1, 20 mL) and potassium hydrogen sulfate (0.5 M aqueous solution, 30 mL) were added to the reaction mixture. The mixture was extracted with ethyl acetate twice, and the organic layers were washed with water (40 mL), saturated aqueous sodium bicarbonate/water (1/1, 40 mL), and brine/water (1/1, 40 mL). The organic layer was dried over sodium sulfate and concentrated under reduced pressure to give Compound aa047-b (2.52 g, 99%). The crude product, Compound aa047-b, was used for the next reaction without purification.

LCMS (ESI) m/z=355 (M+H)+

Retention time: 0.66 min (analysis condition SQDFA05)

Compound aa047-b (2.5 g, 7.06 mmol) was dissolved in DCM (15 mL) at room temperature under a nitrogen atmosphere, triethylsilane (TES) (3.38 mL, 21.17 mmol) and water (127 µL, 7.06 mmol) were added, and boron trifluoride-diethyl ether complex (BF$_3$—OEt$_2$) (1.79 mL, 14.11 mmol) was added dropwise. The reaction mixture was stirred at room temperature for 2 hours and 45 minutes, followed by addition of saturated aqueous ammonium chloride/water (1/1, 6 mL). The mixture was stirred for 10 minutes and then extracted with DCM, and the organic layer was washed with saturated aqueous ammonium chloride/water (1/1, 8 mL) and brine/water (1/1, 8 mL). The organic layer was dried over sodium sulfate and concentrated under reduced pressure. The resulting crude product was dissolved in acetonitrile and washed with hexane (5 mL) twice. The acetonitrile layer was concentrated under reduced pressure, and the resulting crude product was reverse-phase purified (eluent: water containing 0.1% formic acid-acetonitrile) to give Compound aa047-c ((2S)-4-(3,3-difluoroazetidin-1-yl)-2-[methyl(phenylmethoxycarbonyl)amino]-4-oxobutanoic acid) (2.20 g, 88%).

LCMS (ESI) m/z=357 (M+H)+

Retention time: 0.58 min (analysis condition SQDFA05)

1,1,3,3-Tetramethyldisiloxane (10.27 mL, 58.1 mmol) was added to a solution of Compound aa047-c (1.38 g, 3.87 mmol) and triruthenium dodecacarbonyl (Ru₃(CO)₁₂) (0.248 g, 0.387 mmol) in THF (15 mL) at room temperature under a nitrogen atmosphere. The reaction mixture was stirred at a temperature between 35° C. and 40° C. for 2 hours and 45 minutes. The reaction solution was left to cool at room temperature and was added dropwise to 2 mol/L aqueous hydrochloric acid (5 mL) cooled and stirred in an ice bath. The mixture was stirred at the same temperature for 25 minutes and then concentrated under reduced pressure. The crude product was purified by a reverse-phase column chromatography (acetonitrile with 0.1% formic acid/distilled water with 0.1% formic acid) to give Compound aa047-d (365.2 mg, 28%).

LCMS (ESI) m/z=341 (M−H)−

Retention time: 0.39 min (analysis condition SQDFA05)

A suspension of Compound aa047-d (360 mg, 1.05 mmol) and 10% palladium on carbon (50 w/w % water) (72 mg) in ethanol was stirred at room temperature for 3 hours and 45 minutes under a hydrogen atmosphere, after which 10% palladium on carbon (50 w/w % water) (72 mg) was added and the mixture was stirred at room temperature for 15 hours and 15 minutes under a hydrogen atmosphere. 10% palladium on carbon (50 w/w % water) (72 mg) was further added and the mixture was stirred at room temperature for 10 hours under a hydrogen atmosphere. The reaction mixture was filtered through celite and washed with ethanol. The resulting filtrate was concentrated under reduced pressure to give Compound aa047-e (208.7 mg, 95%). The crude product, Compound aa047-e, was used for the next reaction without purification.

LCMS (ESI) m/z=207 (M−H)−

(Analysis condition SQDFA05)

Water (3 mL), DIPEA (0.69 mL, 3.94 mmol), and 1,4-dioxane (3 mL) were added to Compound aa047-e (205 mg, 0.985 mmol), and the mixture was stirred at room temperature. Fmoc-OSu (332 mg, 0.985 mmol) was added and the reaction mixture was stirred for about 40 minutes. Formic acid (1 mL) was added to the reaction mixture, and the mixture was purified by a reverse-phase column chromatography (acetonitrile with 0.1% formic acid/distilled water with 0.1% formic acid) to give Compound aa047 ((2S)-4-(3,3-difluoroazetidin-1-yl)-2-[9H-fluoren-9-ylmethoxycarbonyl(methyl)amino]butanoic acid, Fmoc-MeAbu(Aze-3-F2)-OH) (352.7 mg, 83%).

LCMS (ESI) m/z=431 (M+H)+

Retention time: 0.54 min (analysis condition SQDFA05)

Synthesis of Compound aa048, (2S)-2-[9H-fluoren-9-ylmethoxycarbonyl(methyl)amino]pent-4-enoic acid (Fmoc-MeAlgly-OH)

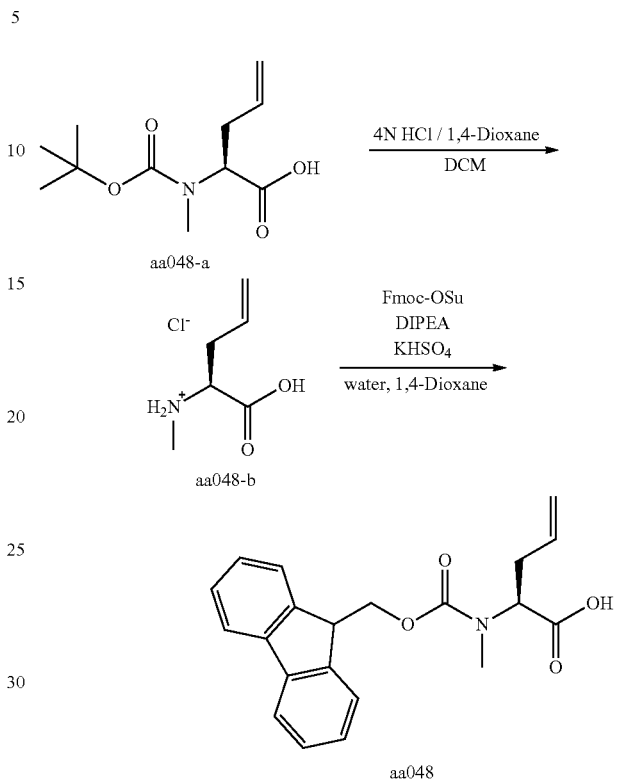

4N Hydrochloric acid-1,4-dioxane (8.23 ml, 32.9 mmol) was added to a solution of Compound aa048-a ((2S)-2-[methyl-[(2-methylpropan-2-yl)oxycarbonyl]amino]pent-4-enoic acid and Boc-MeAlgly-OH) (1.51 g, 6.59 mmol) in dichloromethane (6 ml), and the mixture was stirred at room temperature for 3.5 hours. The reaction solution was concentrated to give Compound aa048-b as a crude product (1.55 g). The next reaction was performed without further purification.

LCMS (ESI) m/z=130 (M+H)+

Retention time: 0.14 min (analysis condition SQDFA05)

Compound aa048-b (6.59 mmol) was dissolved in water (9 ml), DIPEA (5.17 ml, 29.7 mmol), 1,4-dioxane (12 ml), and Fmoc-OSu (2.223 g, 6.59 mmol) were added, and the mixture was stirred at room temperature for 30 minutes. Water (25 ml) and diethyl ether/n-hexane (1/3, 18 ml) were added to the reaction solution, and the aqueous layer was washed with diethyl ether/n-hexane (1/3, 20 ml) twice. The aqueous layer was adjusted to pH 1.4 by adding potassium hydrogen sulfate (KHSO₄) and extracted with ethyl acetate. The organic layer was washed with brine/water (1/1) twice and dried over sodium sulfate, and the solvent was then evaporated under reduced pressure. The resulting crude product was purified by reverse phase column chromatography (acetonitrile with 0.1% formic acid/distilled water with 0.1% formic acid) to give Compound aa048 ((2S)-2-[9H-fluoren-9-ylmethoxycarbonyl(methyl)amino]pent-4-enoic acid, Fmoc-MeAlgly-OH) (2.62 g, 85%)

LCMS (ESI) m/z=352 (M+H)+

Retention time: 0.84 min (analysis condition SQDFA05)

Synthesis of Compound aa049, (2S)-2-(9H-fluoren-9-ylmethoxycarbonylamino)-4-[4-(pentafluoro-λ6-sulfanyl)phenyl]butanoic acid (Fmoc-Hph(4-SF₅)—OH)

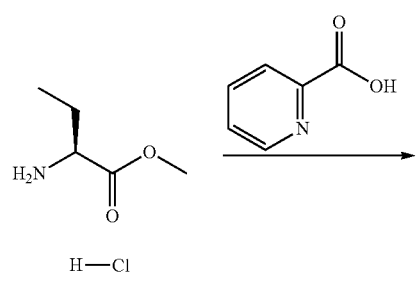

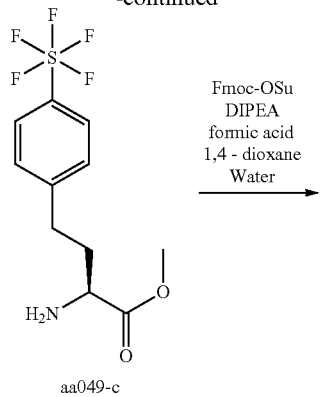

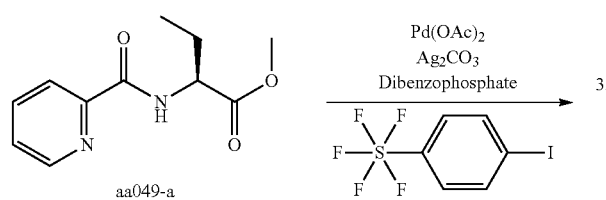

DIPEA (161.5 mL, 3.00 equivalents) was added dropwise to a mixture of L-2-aminobutyric acid methyl ester hydrochloride (CAS No. 56545-22-3) (50 g, 325.51 mmol), pyridine-2-carboxylic acid (44.2 g, 359.03 mmol, 1.10 equivalents), and HATU (136.5 g, 358.99 mmol, 1.10 equivalents) in DCM (1 L) at room temperature, and the mixture was stirred for 16 hours. Water was added to the reaction solution, and the mixture was extracted with DCM three times. The organic layers were combined, sequentially washed with water and brine, and dried over anhydrous sodium sulfate, after which the solvent was evaporated under reduced pressure. The resulting residue was purified by silica gel column chromatography (ethyl acetate/petroleum ether, 0/100 to 15/85) to give Compound aa049-a (209 g).

LCMS (ESI) m/z=223 (M+H)+

Retention time: 1.011 min (analysis condition SMD-method_11)

1H-NMR (400 MHz, DMSO-d6): 8.87 (d, J=6.0 Hz, 1H), 8.70-8.68 (m, 1H), 8.06-8.00 (m, 2H), 7.66-7.63 (m, 1H), 4.49-4.44 (q, 1H), 3.67 (s, 3H), 1.99-1.83 (m, 2H), 0.90 (t, J=5.7 Hz, 3H)

Compound aa049-a (1.35 g, 6.07 mmol), palladium(II) acetate (Pd(OAc)₂, 0.273 g, 1.215 mmol), silver(I) carbonate (1.675 g, 6.07 mmol), dibenzyl phosphate (0.676 g, 2.43 mmol), 4-iodophenylsulfur pentafluoride (CAS No. 286947-68-0) (5.01 g, 15.2 mmol), and 2-methyl-2-butanol (35 mL)

were mixed at room temperature, and the mixture was stirred at 115° C. for 5 hours and 15 minutes. The reaction solution was left to cool to room temperature, ethyl acetate was added, and the mixture was filtered through celite. The solvent was evaporated from the filtrate under reduced pressure to give Compound aa049-b (5.55 g) as a crude product.

LCMS (ESI) m/z=425 (M+H)+

Retention time: 0.87 min (analysis condition SQDFA05)

Methanesulfonic acid (6.92 g, 72 mmol) and water (8.11 mL) were sequentially added to a mixture of Compound aa049-b (2.55 g, 6 mmol equivalents) in acetic acid (8.59 mL) at room temperature, and the mixture was stirred at a temperature between 110° C. and 115° C. for 24 hours. The reaction solution was left to cool to room temperature and concentrated under reduced pressure. The resulting residue was purified by reverse phase column chromatography (acetonitrile with 0.1% formic acid/distilled water with 0.1% formic acid) to give Compound aa049-c (1.13 g, 62%).

LCMS (ESI) m/z=306 (M+H)+

Retention time: 0.47 min (analysis condition SQDFA05)

DIPEA (0.572 mL, 3.28 mmol), 1,4-dioxane (4 mL), and Fmoc-OSu (0.442 g, 1.31 mmol) were sequentially added to a solution of Compound aa049-c (0.4 g, 1.31 mmol) in water (3 mL) at room temperature, and the mixture was stirred for one hour. Formic acid was added to the reaction solution, and the reaction solution was purified by reverse phase column chromatography (acetonitrile with 0.1% formic acid/distilled water with 0.1% formic acid) to give Compound aa049 ((2S)-2-(9H-fluoren-9-ylmethoxycarbonylamino)-4-[4-(pentafluoro-X6-sulfanyl)phenyl]butanoic acid) (0.564 g, 82%).

LCMS (ESI) m/z=528 (M+H)+

Retention time: 0.98 min (analysis condition SQDFA05)

Synthesis of Compound aa050, (2S)-2-[9H-fluoren-9-ylmethoxycarbonyl(propyl)amino]propanoic acid (Fmoc-nPrAla-OH)

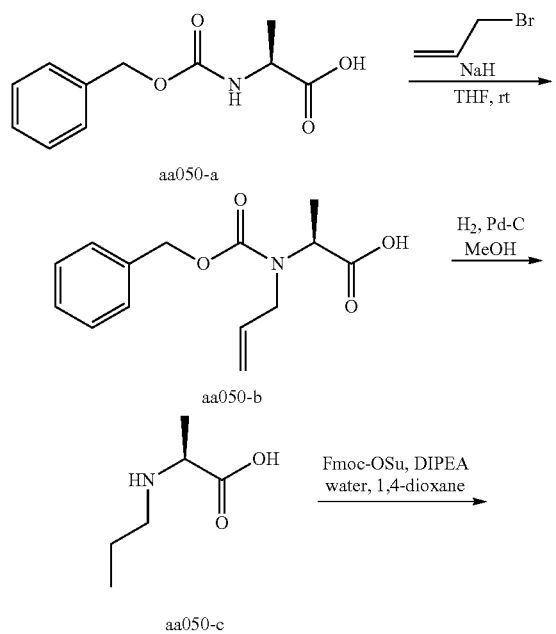

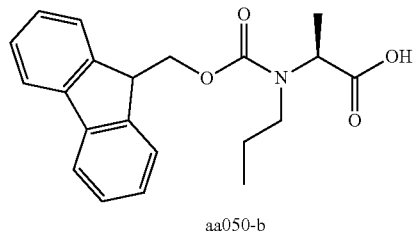

Allyl bromide (4.74 ml, 56.0 mmol) was added to a solution of Compound aa050-a (N-carbobenzoxy-L-alanine, Z-Ala-OH, CAS No. 1142-20-7) (5 g, 22.40 mmol) in tetrahydrofuran (74.7 ml) at room temperature, after which sodium hydride (2.69 g, 67.2 mmol) was added at 10° C. or below for 15 minutes or longer. The reaction solution was stirred at 10° C. or below for one hour, after which tetrahydrofuran (THF) (74.7 ml) was added and the mixture was stirred at room temperature for 65 hours. A saturated aqueous ammonium chloride solution and water were added to the reaction solution, and the mixture was then extracted with ethyl acetate. The organic layers were combined, washed with a saturated aqueous sodium chloride solution, dried over anhydrous sodium sulfate, and concentrated under reduced pressure. The resulting residue was purified by reverse phase column chromatography (acetonitrile with 0.1% formic acid/distilled water with 0.1% formic acid) to give Compound aa050-b (3.91 g, 66%).

LCMS (ESI) m/z=264 (M+H)+

Retention time: 0.68 min (analysis condition SQDFA05)

A suspension of Compound aa050-b (3.81 g, 14.47 mmol) and 10 wt % palladium on carbon (0.41 g) in methanol (45 ml) was stirred at room temperature for two hours under a hydrogen atmosphere. The reaction solution was filtered through celite, and the filtrate was concentrated under reduced pressure to give Compound aa050-c (1.72 g, 91%).

LCMS (ESI) m/z=132 (M+H)+

Retention time: 0.13 min (analysis condition SQDFA05)

Compound aa050-c (1.72 g, 13.11 mmol) was suspended in water (45 ml), DIPEA (10.28 ml, 59.0 mmol), 1,4-dioxane (60 ml), and N-(9-fluorenylmethoxycarbonyloxy)succinimide (Fmoc-OSu) (4.42 g, 13.11 mmol) were added to the suspension, and then the mixture was stirred at room temperature for 30 minutes. Distilled water with 20% formic acid was added to the reaction solution, the mixture was then concentrated under reduced pressure, 1,4-dioxane was evaporated, and the resultant was purified by reverse phase column chromatography (acetonitrile with 0.1% formic acid/distilled water with 0.1% formic acid) to give Compound aa050 ((2S)-2-[9H-fluoren-9-ylmethoxycarbonyl(propyl)amino]propanoic acid, Fmoc-nPrAla-OH) (3.94 g, 85%).

LCMS (ESI) m/z=354 (M+H)+

Retention time: 0.86 min (analysis condition SQDFA05)

Synthesis of Compound aa053, (2S)-3-borono-2-(9H-fluoren-9-ylmethoxycarbonylamino)propanoic acid (Fmoc-Ala(B(OH)2)-OH)
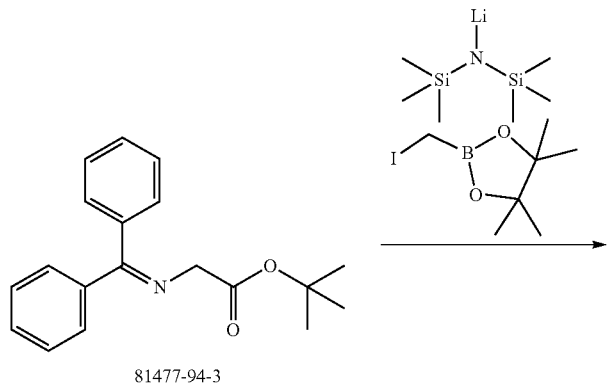
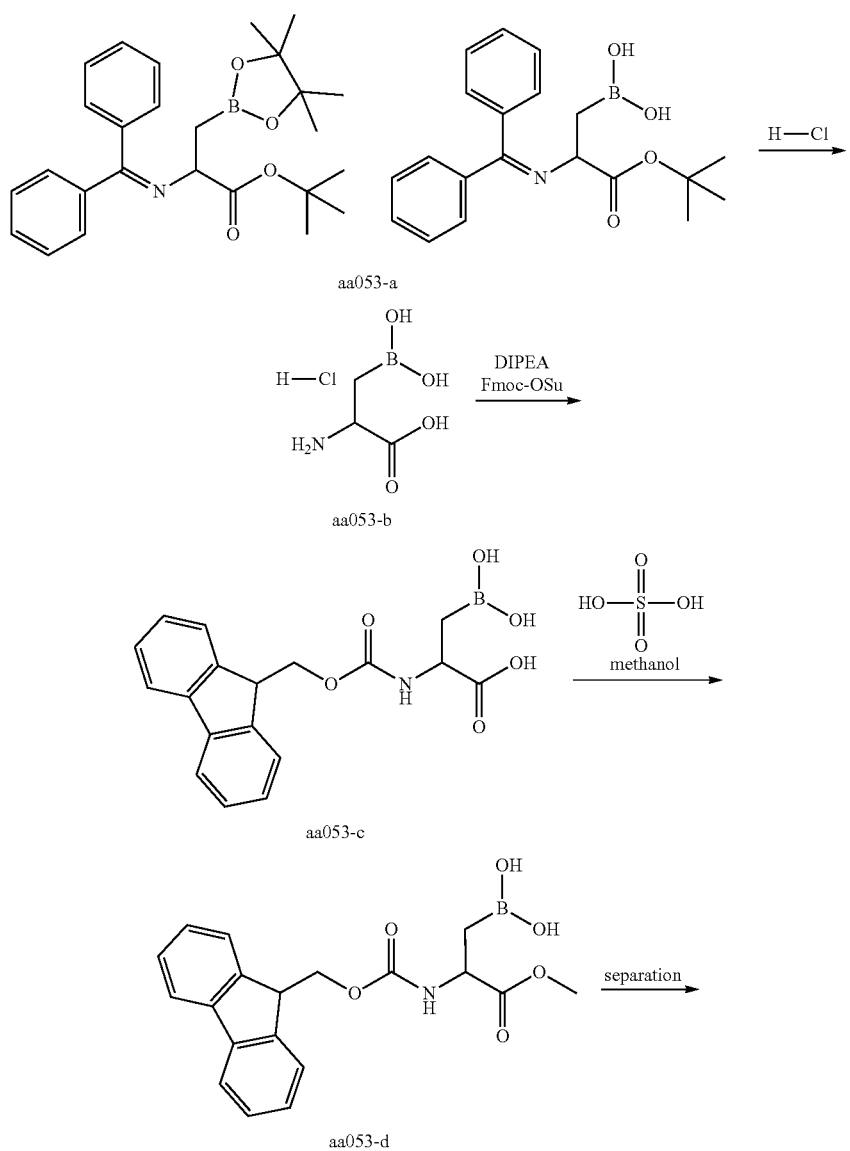

-continued

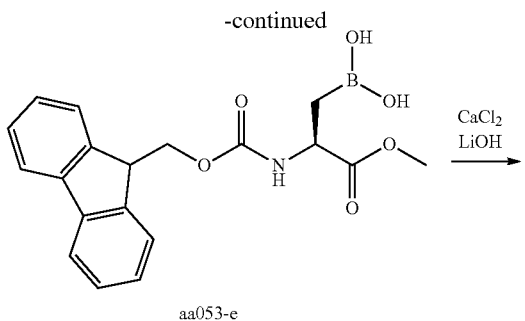

aa053-e

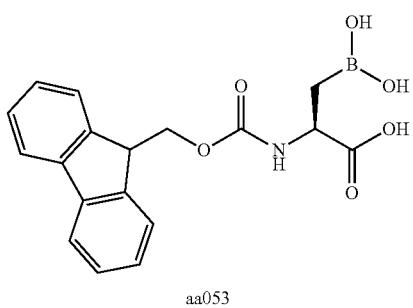

aa053

A 1 M solution of lithium bis(trimethylsilyl)amide (LHMDS) in THF (78 ml, 78 mmol) was added to a solution of N-(diphenylmethylene)glycine tert-butyl (CAS No. 81477-94-3) (21 g, 71.1 mmol) in THF (237 mL) at −78° C. over 10 minutes under a nitrogen atmosphere, and the mixture was then stirred for 10 minutes. 2-(Iodomethyl)-4,4,5,5-tetramethyl-1,3,2-dioxaborolane (22.9 g, 85 mmol) was added over 10 minutes, and the mixture was stirred for a further one hour. The reaction was quenched by adding water (300 mL), after which the reaction solution was warmed to room temperature and extracted with ethyl acetate (200 mL). The resulting organic layer was washed with brine/water (1/1, 50 mL) and dried over magnesium sulfate, and the solvent was then evaporated under reduced pressure. The resulting crude product containing Compound aa053-a was used for the next experiment without purification.

6 mol/L Aqueous hydrochloric acid (71 mL) was added to the crude product containing Compound aa053-a, which was then heated to 70° C., stirred for five hours. The reaction solution was cooled to room temperature and the reaction solution was then washed with dichloromethane (155 mL) twice. The resulting aqueous layer containing Compound aa053-b was used as it is for the next reaction without purification.

The aqueous layer containing Compound aa053-b was neutralized by adding a 6 mol/L aqueous sodium hydroxide solution at 0° C., after which dioxane (142 mL), DIPEA (37.2 mL, 214 mmol), and Fmoc-OSu (24 g, 71 mmol) were added and the mixture was stirred at room temperature for one hour. The reaction solution was concentrated under reduced pressure, then diluted with a water/acetonitrile/formic acid (25/75/0.1) solution and DMSO. The solution was purified by reverse phase column chromatography (acetonitrile with 0.1% formic acid/distilled water with 0.1% formic acid), after which the acetonitrile was evaporated under reduced pressure and then lyophilized to give Compound aa053-c (24.8 g, 98% through three steps).

LCMS (ESI) m/z=354 (M−H)−

Retention time: 0.83 min (analysis condition SQDAA05)

Concentrated sulfuric acid (5.40 ml, 101 mmol) was added to a solution of Compound aa053-c (18 g, 50.7 mmol) in methanol (169 mL), and the mixture was stirred at 70° C. for 30 minutes. The reaction solution was cooled to 10° C., and water (255 mL) was then added over 30 minutes. The resulting precipitate was collected by filtration and then washed with water (54 ml) three times. The precipitate was dried to give Compound aa053-d (17.75 g, 95%). This was mixed with another lot synthesized in the same manner, and purified by following chiral column chromatography.

LCMS (ESI) m/z=392 (M+Na)+

Retention time: 0.95 min (analysis condition SQDAA05)

Compound aa053-d (20.8 g) was preparatively purified by chiral column chromatography (SFC CHIRALPAK AD-H (20 mm×250 mm), CO$_2$/MeOH=75/25, 15 mL/min; or LC CHIRALPAK OJ-RH (20 mm×250 mm), water/acetonitrile=55/45, 20 mL/min) to give Compound aa053-e (13.8 g).

Lithium hydroxide (2.41 g, 57.4 mmol) was added to a 3 mol/L aqueous calcium chloride solution (71.8 ml), and the mixture was stirred at room temperature for five minutes. Isopropyl alcohol (240 mL) and a solution of Compound aa053-f (5.30 g, 14.7 mmol) in THF (60 mL) were sequentially added to the resulting solution, and the mixture was stirred for one hour. The reaction was quenched with 5 M hydrochloric acid, the reaction solution was extracted with isopropyl acetate twice, and the resulting organic layers were dried over magnesium sulfate. The solution was filtered, and the solvent was then evaporated under reduced pressure to give Compound aa053 ((2S)-3-borono-2-(9H-fluoren-9-ylmethoxycarbonylamino)propanoic acid, Fmoc-Ala(B(OH)2)-OH) (5.6 g, quant.).

LCMS (ESI) m/z=354 (M−H)−

Retention time: 0.80 min (analysis condition SQDAA05)

Synthesis of Compound aa054, (2R)-2-[9H-fluoren-9-ylmethoxycarbonyl(methyl)amino]-3-(oxan-2-yloxy)propanoic acid (Fmoc-D-MeSer(THP)-OH)

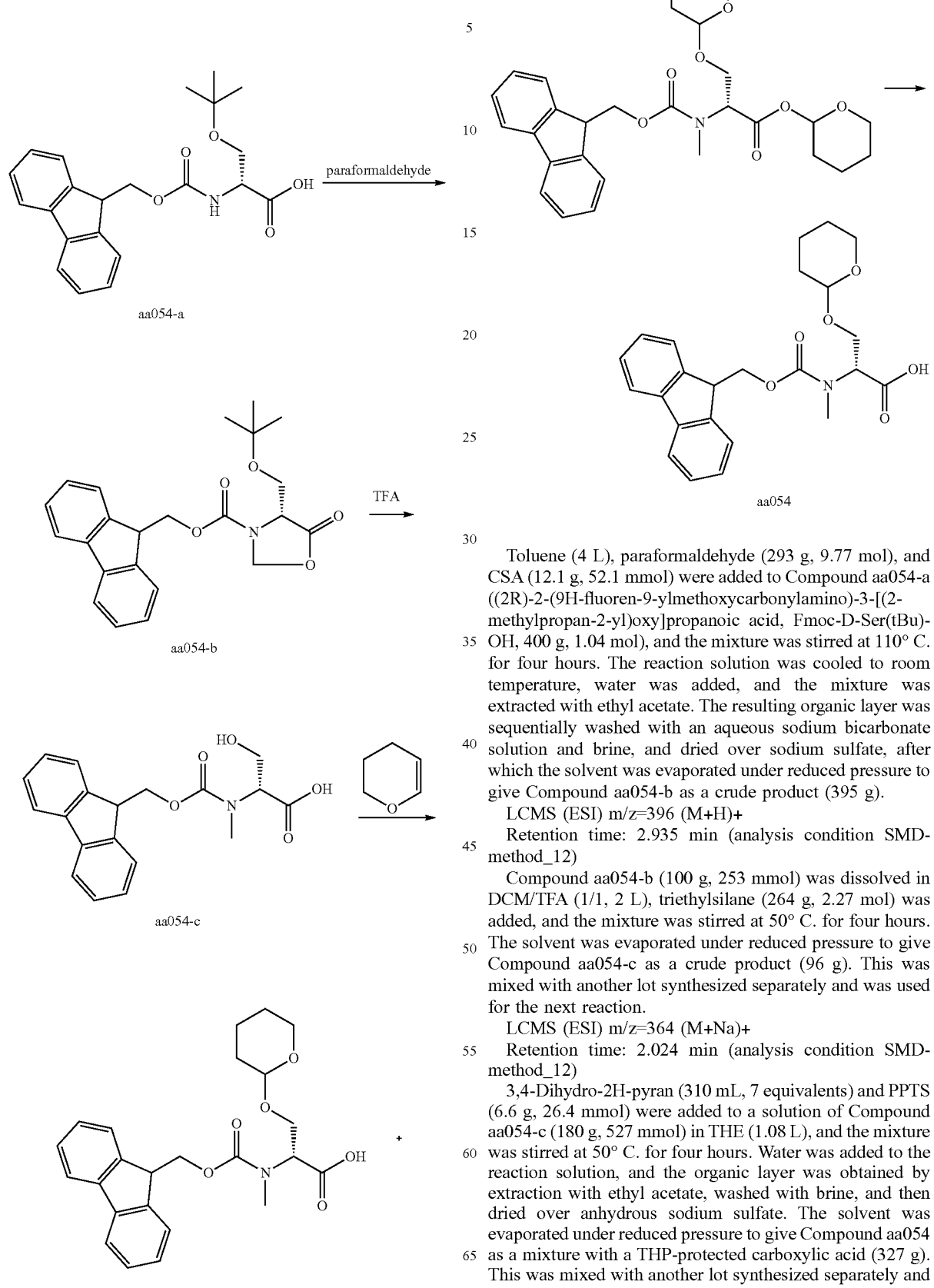

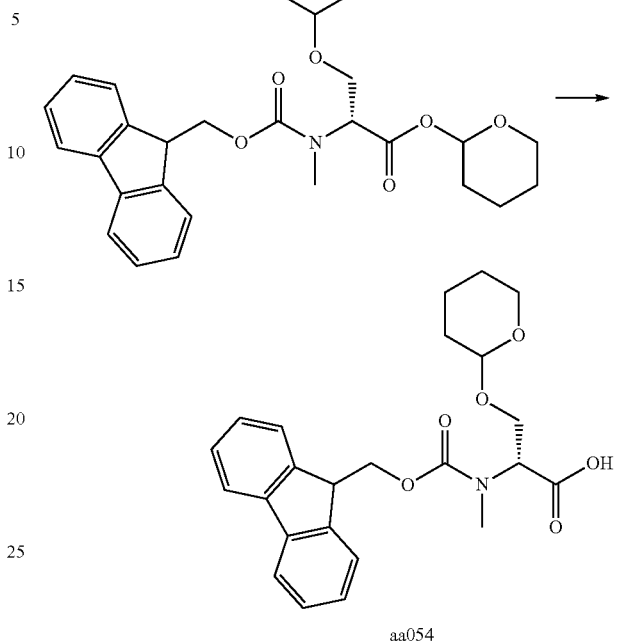

Toluene (4 L), paraformaldehyde (293 g, 9.77 mol), and CSA (12.1 g, 52.1 mmol) were added to Compound aa054-a ((2R)-2-(9H-fluoren-9-ylmethoxycarbonylamino)-3-[(2-methylpropan-2-yl)oxy]propanoic acid, Fmoc-D-Ser(tBu)-OH, 400 g, 1.04 mol), and the mixture was stirred at 110° C. for four hours. The reaction solution was cooled to room temperature, water was added, and the mixture was extracted with ethyl acetate. The resulting organic layer was sequentially washed with an aqueous sodium bicarbonate solution and brine, and dried over sodium sulfate, after which the solvent was evaporated under reduced pressure to give Compound aa054-b as a crude product (395 g).

LCMS (ESI) m/z=396 (M+H)+

Retention time: 2.935 min (analysis condition SMD-method_12)

Compound aa054-b (100 g, 253 mmol) was dissolved in DCM/TFA (1/1, 2 L), triethylsilane (264 g, 2.27 mol) was added, and the mixture was stirred at 50° C. for four hours. The solvent was evaporated under reduced pressure to give Compound aa054-c as a crude product (96 g). This was mixed with another lot synthesized separately and was used for the next reaction.

LCMS (ESI) m/z=364 (M+Na)+

Retention time: 2.024 min (analysis condition SMD-method_12)

3,4-Dihydro-2H-pyran (310 mL, 7 equivalents) and PPTS (6.6 g, 26.4 mmol) were added to a solution of Compound aa054-c (180 g, 527 mmol) in THF (1.08 L), and the mixture was stirred at 50° C. for four hours. Water was added to the reaction solution, and the organic layer was obtained by extraction with ethyl acetate, washed with brine, and then dried over anhydrous sodium sulfate. The solvent was evaporated under reduced pressure to give Compound aa054 as a mixture with a THP-protected carboxylic acid (327 g). This was mixed with another lot synthesized separately and was used for the next reaction.

Phosphate buffer (pH=8, 3 L) was added to a solution of the above mixture (490 g) in THF (3 L), and the mixture was stirred at 50° C. for four hours. The reaction solution was extracted with ethyl acetate, and the resulting organic layer was washed with brine and then dried over anhydrous sodium sulfate, after which the solvent was evaporated under reduced pressure. The resulting solid was recrystallized from ether/heptane to give Compound aa054 sodium salt (500 g). TBME (8 L) and an aqueous phosphoric acid solution (110 g/22.5 L) were added thereto and the mixture was stirred at room temperature for 20 minutes. The reaction solution was extracted with TBME, and the resulting organic layer was washed with brine and then dried over anhydrous sodium sulfate, and the solvent was evaporated under reduced pressure to give Compound aa054 ((2R)-2-[9H-fluoren-9-ylmethoxycarbonyl(methyl)amino]-3-(oxan-2-yloxy)propanoic acid, Fmoc-D-MeSer(THP)-OH) as a white solid (366 g, 77%).

LCMS (ESI) m/z=448 (M+Na)+

Retention time: 2.095 min (analysis condition SMD-method_01)

Synthesis of Compound aa055, (2R)-2-[9H-fluoren-9-ylmethoxycarbonyl(methyl)amino]-3-(3-methylbutoxy)propanoic acid (Fmoc-D-MeSer(iPen)-OH)

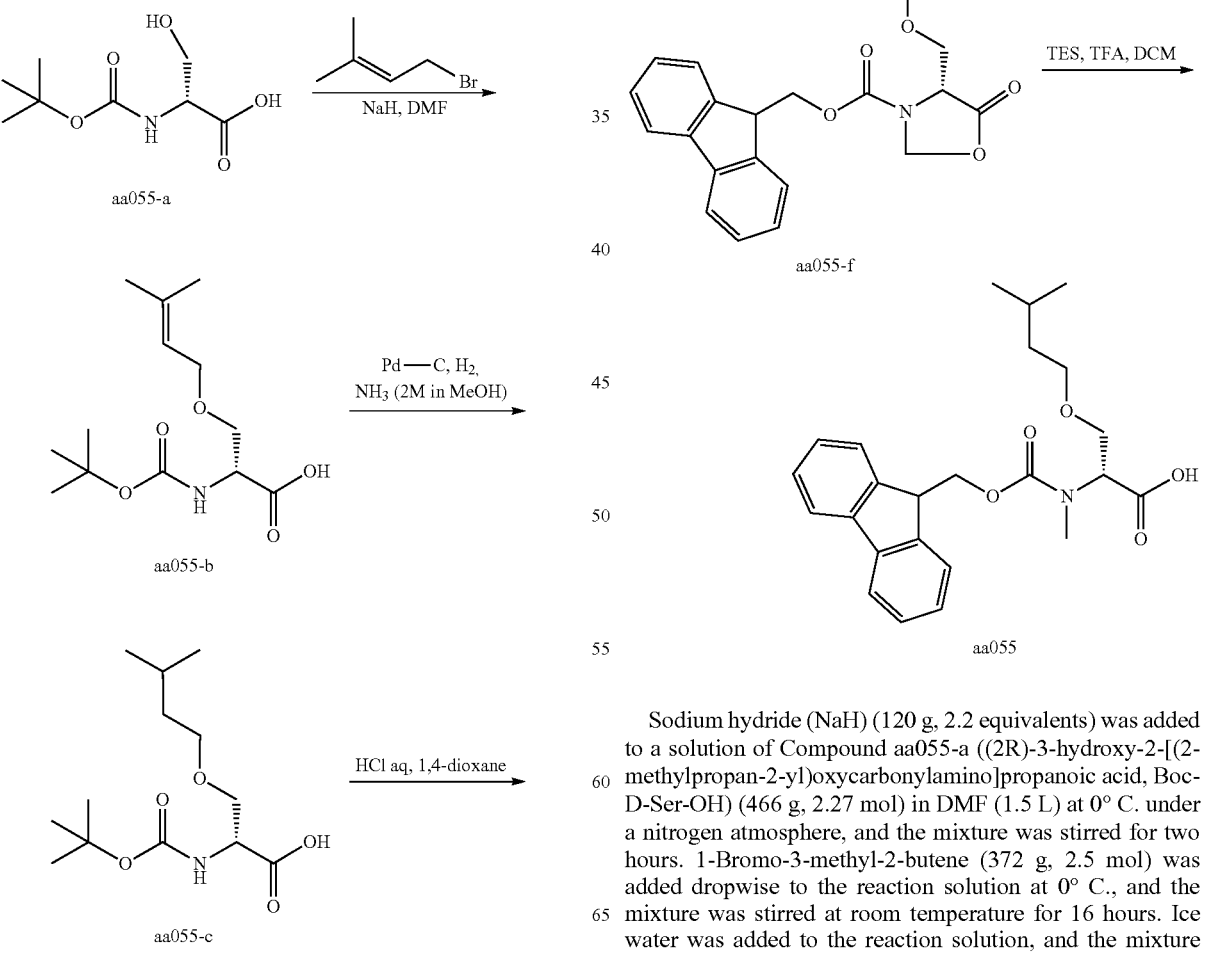

Sodium hydride (NaH) (120 g, 2.2 equivalents) was added to a solution of Compound aa055-a ((2R)-3-hydroxy-2-[(2-methylpropan-2-yl)oxycarbonylamino]propanoic acid, Boc-D-Ser-OH) (466 g, 2.27 mol) in DMF (1.5 L) at 0° C. under a nitrogen atmosphere, and the mixture was stirred for two hours. 1-Bromo-3-methyl-2-butene (372 g, 2.5 mol) was added dropwise to the reaction solution at 0° C., and the mixture was stirred at room temperature for 16 hours. Ice water was added to the reaction solution, and the mixture was adjusted to pH=2 with concentrated hydrochloric acid.

The reaction solution was extracted with ethyl acetate, the organic layer was washed with water and dried over sodium sulfate, and the solvent was then evaporated under reduced pressure. The resulting crude product was purified by silica gel column chromatography (ethyl acetate/petroleum ether) to give Compound aa055-b as a red oiled substance (530 g, 85%).

LCMS (ESI) m/z=296 (M+Na)+

Retention time: 1.259 min (analysis condition SMD-method_15)

Compound aa055-b (420 g, 1.54 mol) was dissolved in methanol (3 L), ammonia (2 M methanol solution, 1.2 L, 67.7 mmol) and palladium on carbon (85 g, 0.52 equivalents) were added, and the mixture was stirred for 16 hours under a hydrogen atmosphere. The reaction solution was filtered, and the solvent was evaporated from the filtrate under reduced pressure to give Compound aa055-c as a colorless oiled substance (360 g). The resulting crude product was used for the next experiment without purification. This was mixed with another lot synthesized separately and was used for the next reaction.

Concentrated hydrochloric acid (1.6 L, 52.7 mol) was added to a solution of Compound aa055-c (670 g, 2.43 mol) in 1,4-dioxane (3 L), and the mixture was stirred at room temperature for four hours. The reaction solution was concentrated to give Compound aa055-d as an aqueous solution. This was adjusted to pH=7 with potassium carbonate, and diluted with 1,4-dioxane (3 L) and water (2 L). Fmoc-OSu (738 g, 2.2 mol) and potassium carbonate (677 g, 4.86 mol) were added thereto, and the mixture was stirred at room temperature for 16 hours. TBME/n-hexane (1/3, 2 L) was added to the reaction solution, and the precipitated solid was removed by filtration. The filtrate was adjusted to pH 1 with concentrated hydrochloric acid and extracted with ethyl acetate. The organic layer was dried over anhydrous sodium sulfate and the solvent was then evaporated under reduced pressure to give Compound aa055-e as a white solid (450 g). The resulting crude product was used for the next experiment without purification.

Toluene (1.5 L), paraformaldehyde (30 g, 1.15 mol), and p-toluenesulfonic acid (4.5 g, 26 mmol) were added to Compound aa055-e (150 g, 377 mmol) under a nitrogen atmosphere, and the mixture was stirred at 110° C. for 16 hours. The reaction solution was cooled to room temperature, followed by addition of ethyl acetate. The mixture was washed with an aqueous sodium bicarbonate solution and dried over sodium sulfate, and the solvent was then evaporated under reduced pressure. The resulting crude product was purified by silica gel column chromatography (ethyl acetate/petroleum ether) to give Compound aa055-f as a white solid (110 g, 65%).

LCMS (ESI) m/z=410 (M+H)+

Retention time: 1.556 min (analysis condition SMD-method_15)

Triethylsilane (102 g, 876 mmol) was added to a solution of Compound aa055-f (120 g, 293 mmol) in DCM/TFA (1/1, 2.4 L) at room temperature under a nitrogen atmosphere, the mixture was stirred for 48 hours, and the solvent was then evaporated under reduced pressure. The resulting residue was adjusted to pH=10 by adding an aqueous potassium carbonate solution. The solution was washed with n-hexane and then adjusted to pH 1 with concentrated hydrochloric acid. The residue was dissolved in acetonitrile and washed with n-heptane. The solvent was evaporated from the resulting acetonitrile layer under reduced pressure to give Compound aa055 ((2R)-2-[9H-fluoren-9-ylmethoxycarbonyl (methyl)amino]-3-(3-methylbutoxy)propanoic acid, Fmoc-D-MeSer(iPen)-OH) as a yellow oiled substance (120 g, 98%).

LCMS (ESI) m/z=412 (M+H)+

Retention time: 2.259 min (analysis condition SMD-method_02)

Synthesis of Compound aa060, (2S)-3-(3-cyanophenyl)-2-[9H-fluoren-9-ylmethoxycarbonyl(methyl) amino]propanoic acid (Fmoc-MePhe(3-CN)—OH)

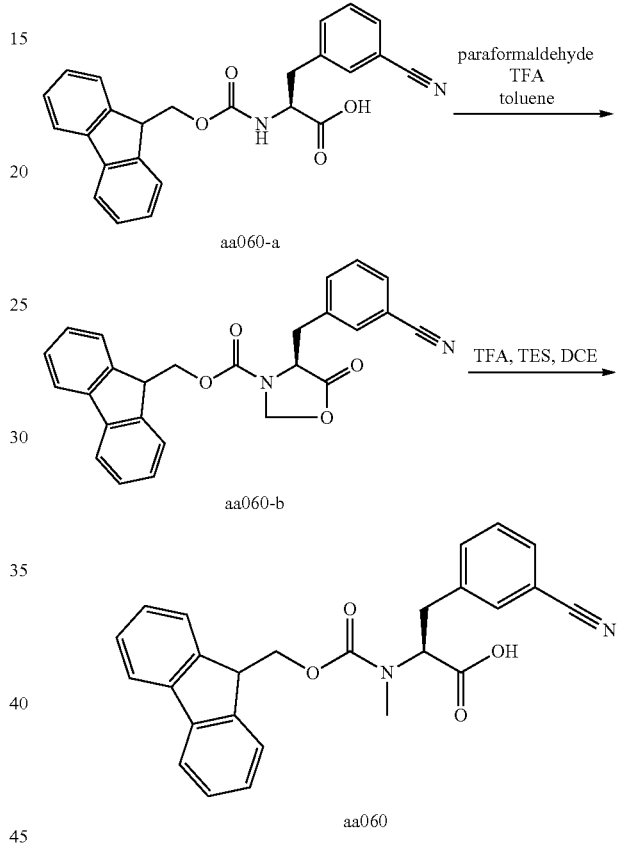

Paraformaldehyde (172 mg, 5.74 mmol) and trifluoroacetic acid (TFA) (1.326 mL, 17.22 mmol) were added to a solution of commercially available (S)-2-((((9H-fluoren-9-yl)methoxy)carbonyl)amino)-3-(3-cyanophenyl)propanoic acid (Fmoc-Phe(3-CN)—OH) (789 mg, 1.913 mmol) in toluene (5.7 mL) under a nitrogen atmosphere, and the mixture was stirred at room temperature for 5 hours and 30 minutes. The reaction solution was concentrated under reduced pressure, and diluted with dichloromethane (DCM). After the solution was washed with a saturated aqueous sodium bicarbonate solution, it was dried over anhydrous magnesium sulfate, and then filtered. The resulting solution was concentrated under reduced pressure to give a crude product, Compound aa060-b (859 mg). This was used for the next reaction without further purification.

Triethylsilane (TES) (2.75 mL, 17.22 mmol) and trifluoroacetic acid (TFA) (3.98 mL, 51.7 mmol) were added to a solution of the above crude product, Compound aa060-b (853 mg), in dichloroethane (DCE) (10 mL) at room temperature under a nitrogen atmosphere, and the mixture was stirred at 60° C. for five hours. The reaction solution was cooled to room temperature, and the solvent was evaporated under reduced pressure. t-Butyl methyl ether/n-hexane=1/1 was added to the resulting crude product, and the mixture was extracted with a saturated aqueous sodium bicarbonate solution five times. The resulting aqueous layer was adjusted to an acidic pH with concentrated hydrochloric acid and then extracted with ethyl acetate three times. The organic layers were washed with brine, dried over anhydrous magnesium sulfate, and filtered. The solvent was then evaporated under reduced pressure to give Compound aa060 ((2S)-3-(3-cyanophenyl)-2-[9H-fluoren-9-ylmethoxycarbonyl(methyl)amino]propanoic acid, Fmoc-MePhe(3-CN)—OH) (811 mg, 99% through two steps). The obtained Compound aa060 was used for peptide synthesis without further purification.

LCMS (ESI) m/z=427 (M+H)+
Retention time: 0.83 min (analysis condition SQDFA05)

Synthesis of Compound aa061, (2S)-3-(4-cyanophenyl)-2-[9H-fluoren-9-ylmethoxycarbonyl(methyl)amino]propanoic acid (Fmoc-MePhe(4-CN)—OH)

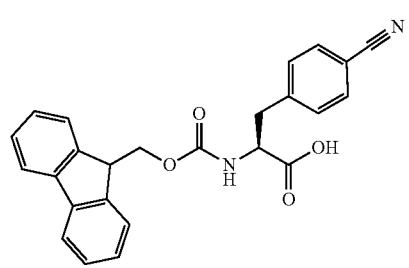

Compound aa061 ((2S)-3-(4-cyanophenyl)-2-[9H-fluoren-9-ylmethoxycarbonyl(methyl)amino]propanoic acid, Fmoc-MePhe(4-CN)—OH) was obtained as a crude product (1.14 g, 108% through two steps) by the same method as in the synthesis of Compound aa060 using Compound aa061-a ((2S)-3-(4-cyanophenyl)-2-(9H-fluoren-9-ylmethoxycarbonylamino)propanoic acid, Fmoc-Phe(4-CN)—OH) (1 g, 2.425 mmol) as a starting material. The obtained Compound aa061 was used for peptide synthesis without further purification.

LCMS (ESI) m/z=427 (M+H)+
Retention time: 0.82 min (analysis condition SQDFA05)

Synthesis of Compound aa062, (2S)-2-[9H-fluoren-9-ylmethoxycarbonyl(methyl)amino]-3-methoxypropanoic acid (Fmoc-MeSer(Me)-OH)

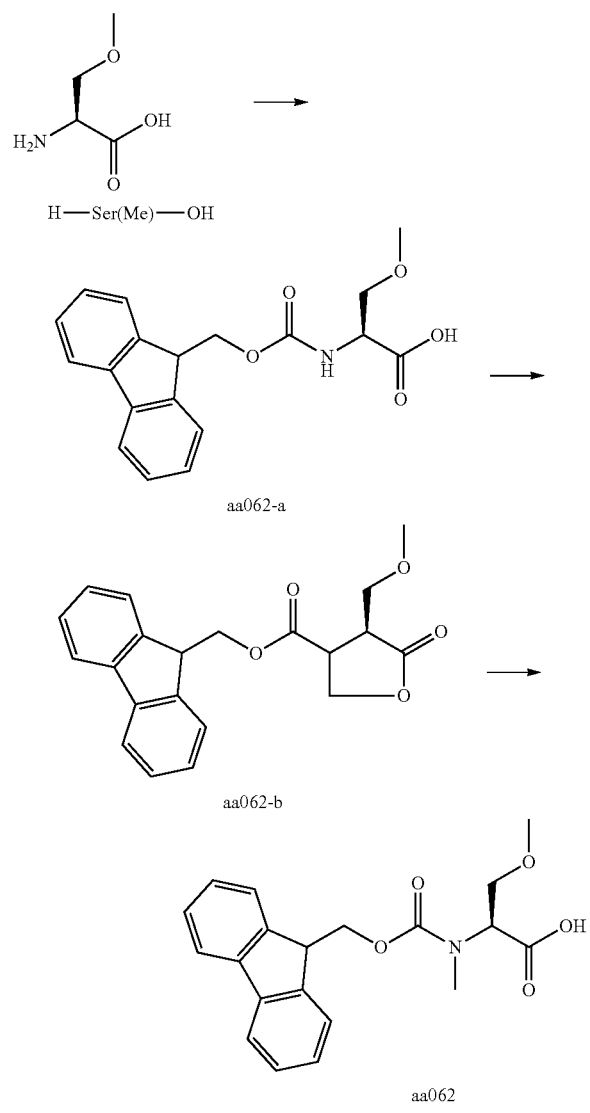

Commercially available O-methyl-L-serine (H-Ser(Me)-OH) (498 mg, 4.18 mmol) and sodium carbonate (1.329 g, 12.54 mmol) were dissolved in water (8 mL), after which a solution of N-(9-fluorenylmethoxycarbonyloxy)succinimide (Fmoc-OSu) (1.41 g, 4.18 mmol) in 1,4-dioxane (12 mL) was added at room temperature and the mixture was stirred overnight. Water was added to the reaction solution, and the mixture was washed with t-butyl methyl ether/n-hexane=1/10. 1N Aqueous hydrochloric acid was added to the resulting aqueous layer until the pH was acidic, and the mixture was extracted with ethyl acetate twice. The resulting organic layers were washed with brine, dried over anhydrous magnesium sulfate, and filtered. The solvent was then evaporated under reduced pressure to give Compound aa062-a (Fmoc-Ser(Me)-OH) (1.46 g) as a crude product. The obtained Compound aa062-a was used for the next reaction without further purification.

Trifluoroacetic acid (TFA) (2.90 mL, 37.6 mmol) was added to a solution of the above crude product, Compound aa062-a (1.46 g), and paraformaldehyde (377 mg, 12.54 mmol) in toluene (12 mL), and the mixture was stirred at room temperature overnight. The solvent was evaporated under reduced pressure, after which ethyl acetate was added. The organic layer was washed with a saturated aqueous sodium bicarbonate solution and then washed with brine. The resulting organic layer was dried over anhydrous magnesium sulfate and then filtered. The solvent was evaporated from the resulting filtrate under reduced pressure to give a crude product, Compound aa062-b (2.13 g). The obtained Compound aa062-b was used for the next reaction without further purification.

Triethylsilane (TES) (6.02 mL, 37.7 mmol) and trifluoroacetic acid (TFA) (8.72 mL, 113 mmol) were added to a solution of the above crude product, Compound aa062-b (2.13 g), in dichloroethane (DCE) (15 mL) at room temperature, and the mixture was stirred at 60° C. for three hours. The reaction solution was cooled to room temperature, and the solvent was evaporated under reduced pressure. t-Butyl methyl ether/n-hexane=1/4 was added to the resulting crude product, and a saturated aqueous sodium bicarbonate solution was added, resulting in formation of a white solid. The organic solvent was evaporated under reduced pressure, and dimethyl sulfoxide was added to the aqueous layer. The resulting solution was purified by reverse phase column chromatography (0.1% aqueous formic acid solution/0.1% formic acid-acetonitrile solution) to give Compound aa062 ((2S)-2-[9H-fluoren-9-ylmethoxycarbonyl(methyl)amino]-3-methoxypropanoic acid, Fmoc-MeSer(Me)-OH) (782 mg, 53% through three steps).

LCMS (ESI) m/z=356 (M+H)+

Retention time: 0.76 min (analysis condition SQDFA05)

Synthesis of Compound aa063, (2S)-2-[9H-fluoren-9-ylmethoxycarbonyl(methyl)amino]-3-[2-(trifluoromethyl)phenyl]propanoic acid (Fmoc-MePhe(2-CF3)-OH)

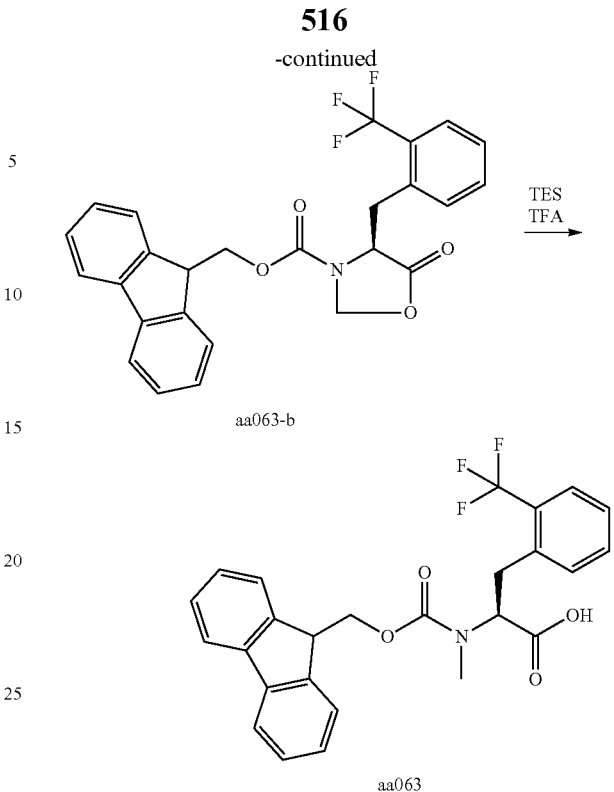

Compound aa063-b was obtained as a crude product by the same method as in the synthesis of Compound aa060-b using Compound aa063-a ((2S)-2-(9H-fluoren-9-ylmethoxycarbonylamino)-3-[2-(trifluoromethyl)phenyl]propanoic acid, Fmoc-Phe(2-CF3)-OH) (1 g, 2.196 mmol) as a starting material. A crude product obtained by the same method as in the synthesis of Compound aa060 using the obtained Compound aa063-b was purified by reverse phase column chromatography (0.1% aqueous formic acid solution/0.1% formic acid-acetonitrile solution) to give Compound aa063 ((2S)-2-[9H-fluoren-9-ylmethoxycarbonyl(methyl)amino]-3-[2-(trifluoromethyl)phenyl]propanoic acid, Fmoc-MePhe(2-CF3)-OH) (841 mg, 82% through two steps).

LCMS (ESI) m/z=470 (M+H)+

Retention time: 0.95 min (analysis condition SQDFA05)

Synthesis of Compound aa064, (2S)-3-(2-cyanophenyl)-2-[9H-fluoren-9-ylmethoxycarbonyl(methyl)amino]propanoic acid (Fmoc-MePhe(2-CN)—OH)

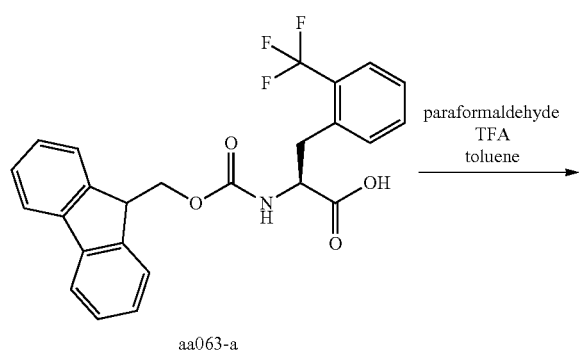

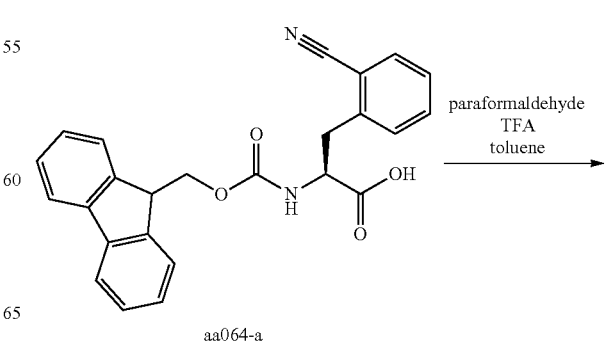

517

-continued

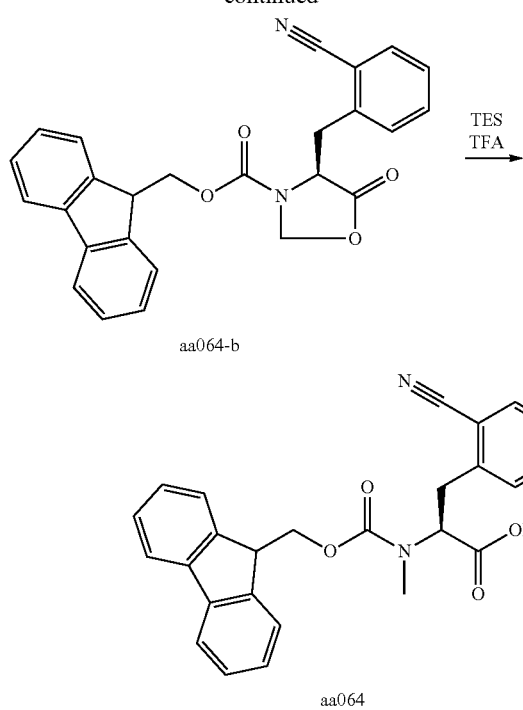

aa064-b aa064

Compound aa064-b was obtained as a crude product by the same method as in the synthesis of Compound aa060 using Compound aa064-a ((2S)-3-(2-cyanophenyl)-2-(9H-fluoren-9-ylmethoxycarbonylamino)propanoic acid, Fmoc-Phe(2-CN)—OH) (1 g, 2.425 mmol) as a starting material. A crude product obtained by the same method as in the synthesis of Compound aa060 using the obtained Compound aa064-b was purified by reverse phase column chromatography (0.1% aqueous formic acid solution/0.1% formic acid-acetonitrile solution) to give Compound aa064 ((2S)-3-(2-cyanophenyl)-2-[9H-fluoren-9-ylmethoxycarbonyl(methyl)amino]propanoic acid, Fmoc-MePhe(2-CN)—OH) (529 mg, 51% through two steps).

LCMS (ESI) m/z=427 (M+H)+

Retention time: 0.85 min (analysis condition SQDFA05)

Synthesis of Compound aa065, (2S)-2-[9H-fluoren-9-ylmethoxycarbonyl(methyl)amino]-3-pyridin-4-ylpropanoic acid (Fmoc-MeAla(4-Pyr)-OH)

518

-continued

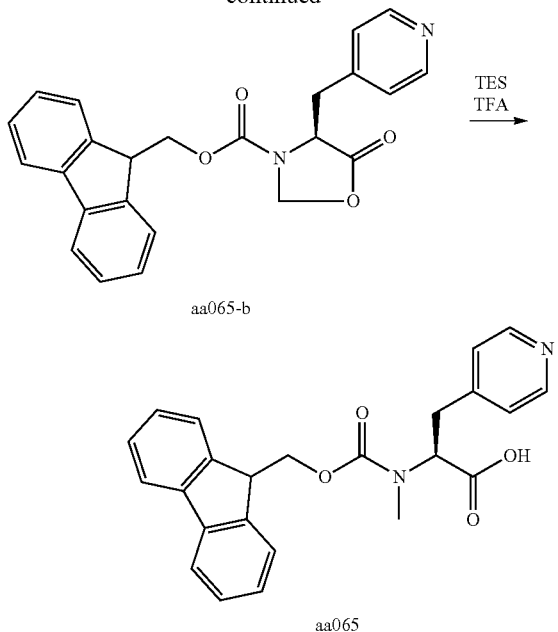

aa065-b aa065

Compound aa065-b was obtained as a crude product by the same method as in the synthesis of Compound aa060-b using Compound aa065-a ((2S)-2-[9H-fluoren-9-ylmethoxycarbonylamino]-3-pyridin-4-ylpropanoic acid, Fmoc-Ala(4-Pyr)-OH) (1.5 g, 3.86 mmol) as a starting material.

LCMS (ESI) m/z=401 (M+H)+

Retention time: 0.60 min (analysis condition SQDFA05)

A crude product obtained by the same method as in the synthesis of Compound aa060 using the total amount of Compound aa065-b obtained above was purified by reverse phase column chromatography (0.1% aqueous formic acid solution/0.1% formic acid-acetonitrile solution) to give Compound aa065 ((2S)-2-[9H-fluoren-9-ylmethoxycarbonyl(methyl)amino]-3-pyridin-4-ylpropanoic acid, Fmoc-MeAla(4-Pyr)-OH) (1.54 g, 91% through two steps).

LCMS (ESI) m/z=403 (M+H)+

Retention time: 0.51 min (analysis condition SQDFA05)

Synthesis of Compound aa066, (2S)-3-[4-(difluoromethyl)phenyl]-2-[9H-fluoren-9-ylmethoxycarbonyl(methyl)amino]propanoic acid (Fmoc-MePhe(4-CHF2)-OH)

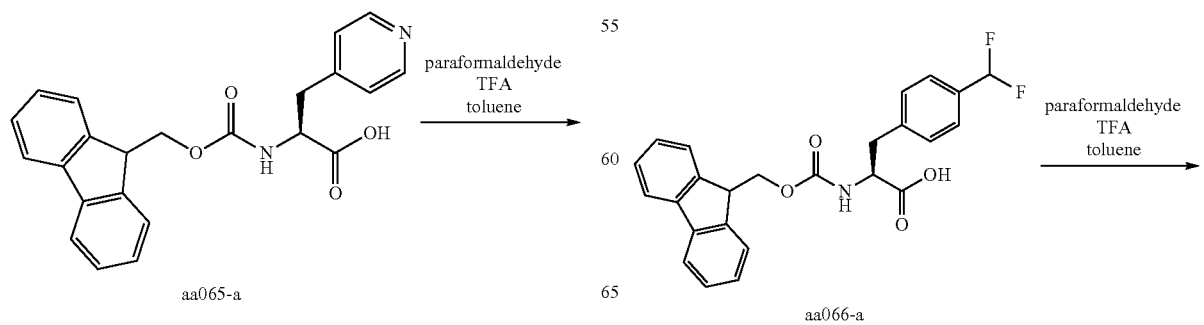

aa065-a aa066-a

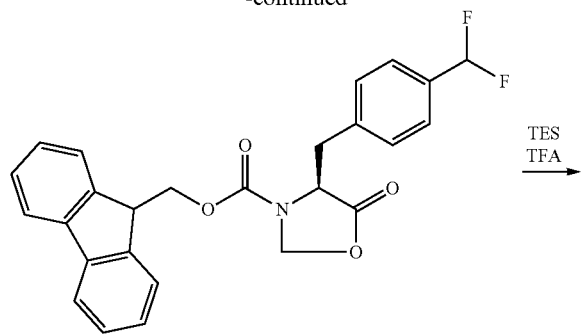

aa066-b

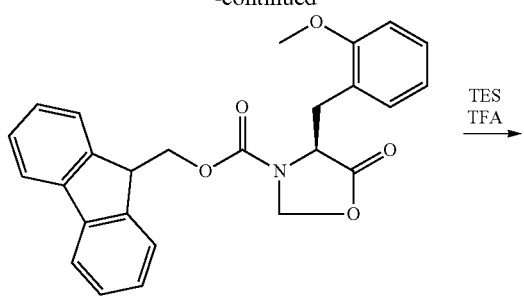

aa067-b

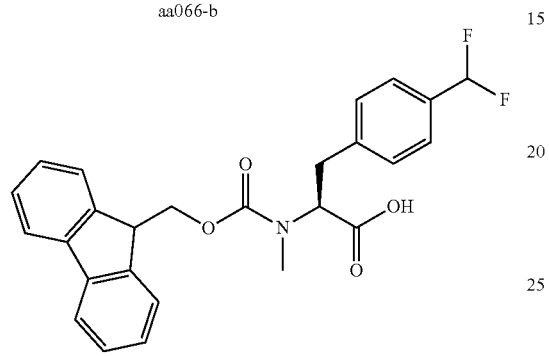

aa066

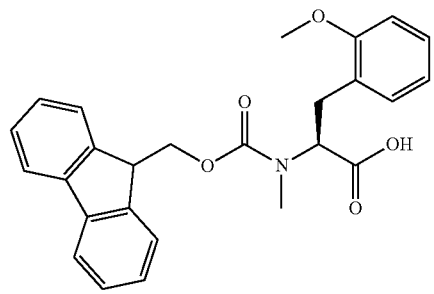

aa067

Compound aa066-b was obtained as a crude product by the same method as in the synthesis of Compound aa060-b using Compound aa066-a ((2S)-3-[4-(difluoromethyl)phenyl]-2-[9H-fluoren-9-ylmethoxycarbonylamino]propanoic acid, Fmoc-Phe(4-CHF2)-OH) (2 g, 4.57 mmol) as a starting material. A crude product obtained by the same method as in the synthesis of Compound aa060 using the obtained Compound aa066-b was purified by reverse phase column chromatography (0.1% aqueous formic acid solution/0.1% formic acid-acetonitrile solution) to give Compound aa066 ((2S)-3-[4-(difluoromethyl)phenyl]-2-[9H-fluoren-9-ylmethoxycarbonyl(methyl)amino]propanoic acid, Fmoc-MePhe(4-CHF2)-OH) (1.38 g, 67% through two steps).

LCMS (ESI) m/z=452 (M+H)+

Retention time: 0.88 min (analysis condition SQDFA05)

Synthesis of Compound aa067, (2S)-2-[9H-fluoren-9-ylmethoxycarbonyl(methyl)amino]-3-(2-methoxyphenyl)propanoic acid (Fmoc-MePhe(2-OMe)-OH)

A crude product obtained by the same method as in the synthesis of Compound aa060-b using Compound aa067-a ((2S)-2-(9H-fluoren-9-ylmethoxycarbonylamino)-3-(2-methoxyphenyl)propanoic acid, Fmoc-Phe(2-OMe)-OH) (1.39 g, 3.33 mmol) as a starting material was purified by silica gel column chromatography (ethyl acetate/hexane) to give Compound aa067-b as a mixture with a dimer.

A crude product obtained by the same method as in the synthesis of Compound aa060 using the obtained Compound aa067-b was purified by reverse phase column chromatography (0.1% aqueous formic acid solution/0.1% formic acid-acetonitrile solution) to give Compound aa067 ((2S)-2-[9H-fluoren-9-ylmethoxycarbonyl(methyl)amino]-3-(2-methoxyphenyl)propanoic acid, Fmoc-MePhe(2-OMe)-OH) (456 mg, 34% through two steps).

LCMS (ESI) m/z=432 (M+H)+

Retention time: 0.90 min (analysis condition SQDFA05)

Synthesis of Compound aa068, (2S)-2-[9H-fluoren-9-ylmethoxycarbonyl(methyl)amino]-3-pyridin-3-ylpropanoic acid (Fmoc-MeAla(3-Pyr)-OH)

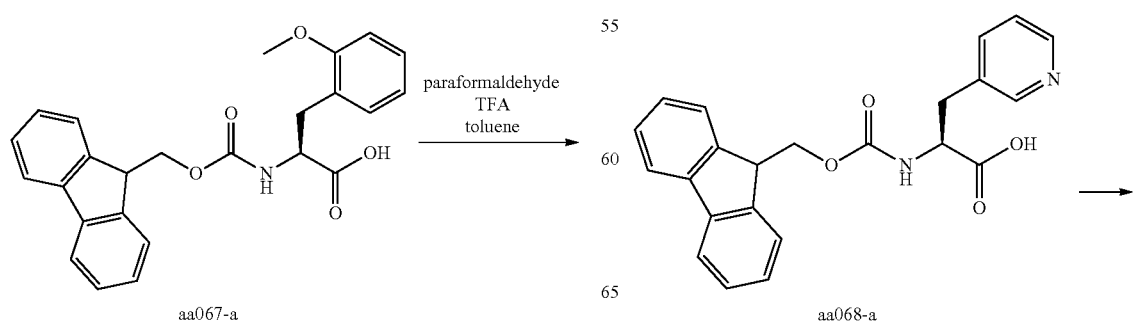

aa067-a     aa068-a

-continued

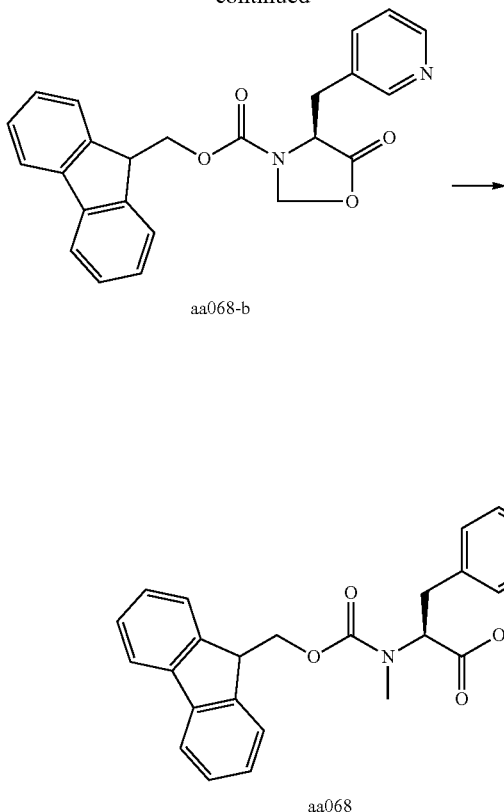

aa068-b aa068

Compound aa068-b (2.95 g, 95%) was obtained by the same method as in the synthesis of Compound aa060-b using Compound aa068-a ((2S)-2-[9H-fluoren-9-ylmethoxycarbonylamino]-3-pyridin-3-ylpropanoic acid, Fmoc-Ala(3-Pyr)-OH) (3 g, 7.72 mmol) as a starting material.

LCMS (ESI) m/z=401 (M+H)+

Retention time: 0.64 min (analysis condition SQDFA05)

A crude product obtained by the same method as in the synthesis of Compound aa060 using the obtained Compound aa068-b (2.95 g) was suspended in DCM (50 mL), a 3 mol/L aqueous sodium dihydrogenphosphate solution (45 mL, containing 1.5 mol/L sodium chloride) was added, and the mixture was stirred. After removing the aqueous layer, the organic layer was washed with a 3 mol/L aqueous sodium dihydrogenphosphate solution (45 mL, containing 1.5 mol/L sodium chloride) twice. The organic layer was dried over anhydrous magnesium sulfate and the solvent was then evaporated under reduced pressure. The resulting residue was purified by reverse phase column chromatography (water/acetonitrile) to give Compound aa068 ((2S)-2-[9H-fluoren-9-ylmethoxycarbonyl(methyl)amino]-3-pyridin-3-ylpropanoic acid, Fmoc-MeAla(3-Pyr)-OH) (2.67 g, 90%).

LCMS (ESI) m/z=403 (M+H)+

Retention time: 0.53 min (analysis condition SQDFA05)

Synthesis of Compound aa069, (2S)-3-cyclopropyloxy-2-[9H-fluoren-9-ylmethoxycarbonyl(methyl)amino]propanoic acid (Fmoc-MeSer(cPr)—OH)

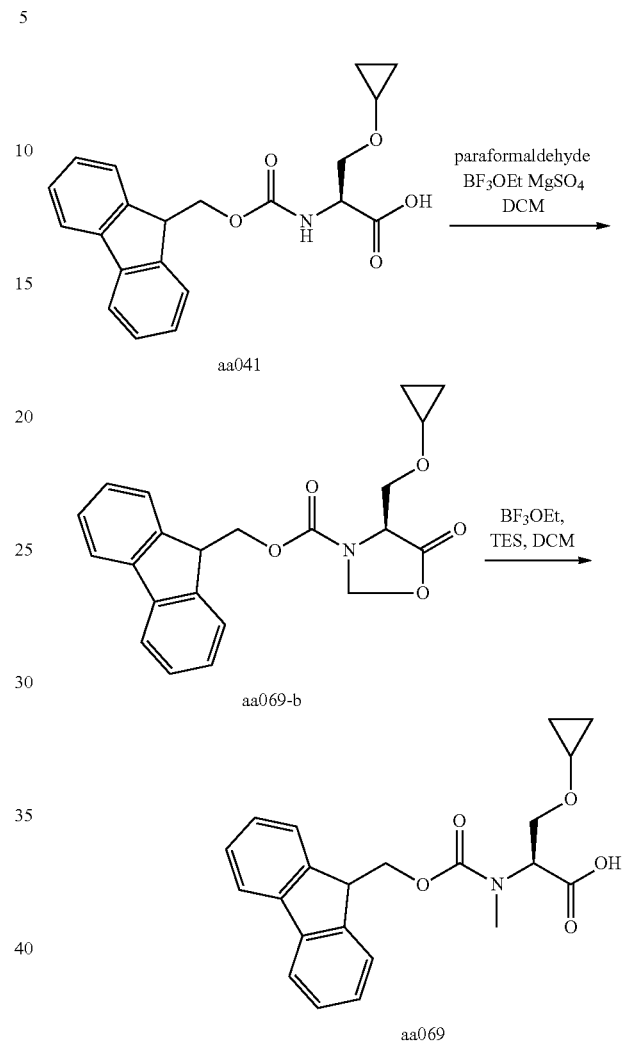

aa041 aa069-b aa069

Paraformaldehyde (1.815 g, 60.5 mmol), magnesium sulfate (2.36 g, 19.63 mmol), and boron trifluoride-diethyl ether complex (BF$_3$·OEt$_2$) (1.184 mL, 9.42 mmol) were added to a solution of Compound aa041 ((2S)-3-cyclopropyloxy-2-(9H-fluoren-9-ylmethoxycarbonylamino)propanoic acid, Fmoc-Ser(cPr)—OH) (2.89 g, 7.85 mmol) in DCM (87 mL) under a nitrogen atmosphere, and the mixture was stirred at room temperature for two hours. A saturated aqueous sodium bicarbonate solution was added to the reaction solution to separate the organic layer from the aqueous layer. The aqueous layer was extracted with DCM twice, the combined organic layers were washed with brine and dried over sodium sulfate, and the solvent was then evaporated under reduced pressure to give Compound aa069-b as a crude product (3.1 g, quant.).

LCMS (ESI) m/z=380 (M+H)+

Retention time: 0.93 min (analysis condition SQDFA05)

Triethylsilane (3.13 mL, 19.64 mmol), water (0.141 mL, 7.85 mmol), and boron trifluoride-diethyl ether complex (BF$_3$·OEt$_2$) (2.49 mL, 19.6 mmol) were added to a solution of the obtained Compound aa069-b (2.98 g, 7.85 mmol) in DCM (26.2 mL) on ice under a nitrogen atmosphere, and the mixture was stirred for two hours. A saturated aqueous ammonium chloride solution was added to the reaction solution, and the organic layer was separated. The organic layer was washed with a saturated aqueous ammonium chloride solution, then washed with brine, and concentrated under reduced pressure to give a crude product. The resulting crude product was dissolved in acetonitrile and washed with n-hexane, and the acetonitrile layer was then concentrated under reduced pressure to give Compound aa069 ((2S)-3-cyclopropyloxy-2-[9H-fluoren-9-ylmethoxycarbonyl(methyl)amino]propanoic acid, Fmoc-MeSer(cPr)—OH) (2.71 g, 90%).

LCMS (ESI) m/z=382 (M+H)+
Retention time: 0.83 min (analysis condition SQDFA05)

Synthesis of Compound aa070, (2S)-3-cyclopropyl-2-[9H-fluoren-9-ylmethoxycarbonyl(methyl)amino]propanoic acid (Fmoc-MeAla(cPr)-OH)

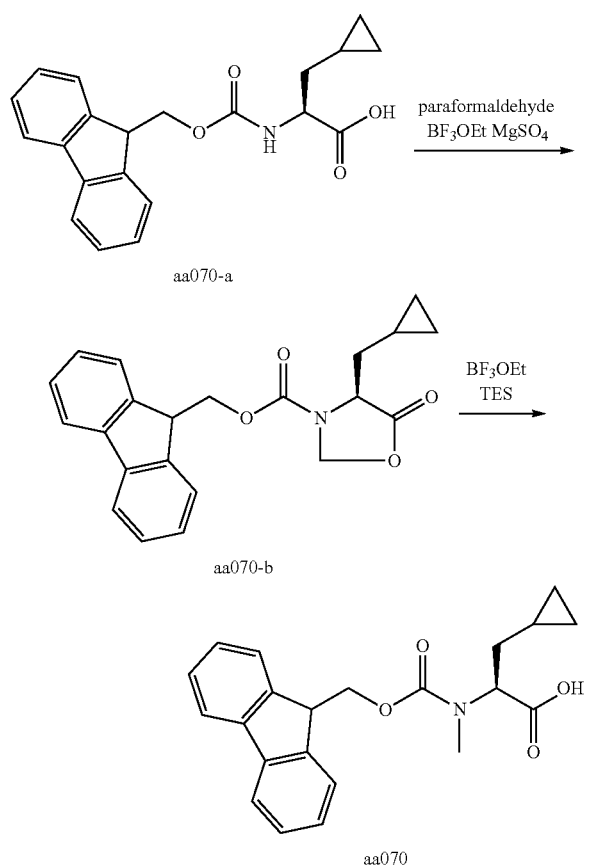

Compound aa070-b was obtained as a crude product (10.5 g) by the same method as in the synthesis of Compound aa069-b using Compound aa070-a ((2S)-3-cyclopropyl-2-[9H-fluoren-9-ylmethoxycarbonyl(methyl)amino]propanoic acid, Fmoc-Ala(cPr)—OH) (10 g, 28.5 mmol) as a starting material.

LCMS (ESI) m/z=364 (M+H)+
Retention time: 0.95 min (analysis condition SQDFA05)

A crude product obtained after reaction by the same method as in the synthesis of Compound aa069 using the obtained Compound aa070-b (10.5 g) was purified by reverse phase column chromatography (0.1% formic acid-water/0.1% formic acid-acetonitrile) to give Compound aa070 ((2S)-3-cyclopropyl-2-[9H-fluoren-9-ylmethoxycarbonyl(methyl)amino]propanoic acid, Fmoc-MeAla(cPr)—OH) (7.82 g, 75% through two steps).

LCMS (ESI) m/z=366 (M+H)+
Retention time: 0.87 min (analysis condition SQDFA05)

Synthesis of Compound aa071, (2S)-3-cyclopentyl-2-[9H-fluoren-9-ylmethoxycarbonyl(methyl)amino]propanoic acid (Fmoc-MeAla(cPent)-OH)

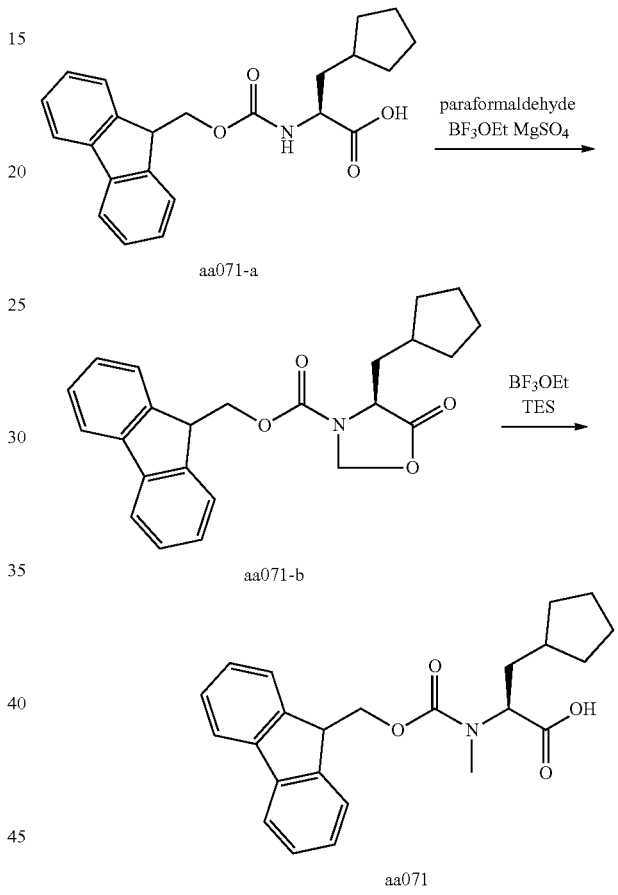

Compound aa071-b was obtained as a crude product (10.5 g) by the same method as in the synthesis of Compound aa069-b using Compound aa071-a ((2S)-3-cyclopentyl-2-[9H-fluoren-9-ylmethoxycarbonylamino]propanoic acid, Fmoc-Ala(cPent)-OH) (10 g, 26.4 mmol) as a starting material.

LCMS (ESI) m/z=392 (M+H)+
Retention time: 1.05 min (analysis condition SQDFA05)

A crude product obtained after reaction by the same method as in the synthesis of Compound aa069 using the obtained Compound aa071-b (10.5 g) was purified by reverse phase column chromatography (0.1% aqueous formic acid solution/0.1% formic acid-acetonitrile solution) to give Compound aa071 ((2S)-3-cyclopentyl-2-[9H-fluoren-9-ylmethoxycarbonyl(methyl)amino]propanoic acid, Fmoc-MeAla(cPent)-OH) (10.11 g, 96% through two steps).

LCMS (ESI) m/z=394 (M+H)+
Retention time: 0.98 min (analysis condition SQDFA05)

525

Synthesis of Compound aa072, (2S)-3-cyclobutyl-2-[9H-fluoren-9-ylmethoxycarbonyl(methyl)amino]propanoic acid (Fmoc-MeAla(cBu)-OH)

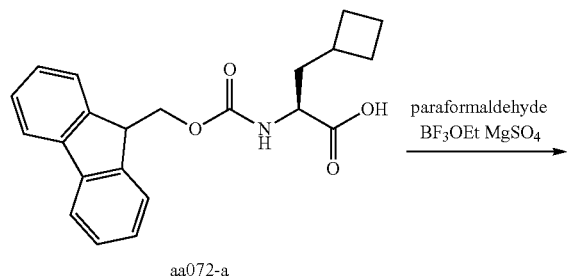

aa072-a

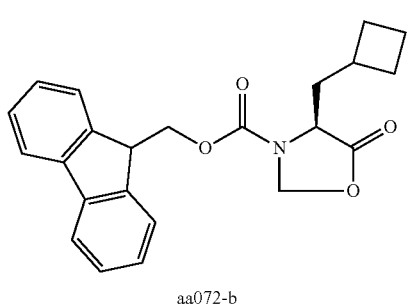

aa072-b

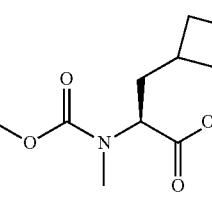

aa072

Compound aa072-b was obtained as a crude product (3.63 g) by the same method as in the synthesis of Compound aa069-b using Compound aa072-a ((2S)-3-cyclobutyl-2-[9H-fluoren-9-ylmethoxycarbonylamino]propanoic acid, Fmoc-Ala(cBu)-OH) (3.36 g, 9.19 mmol) as a starting material.

LCMS (ESI) m/z=378 (M+H)+

Retention time: 1.01 min (analysis condition SQDFA05)

A crude product obtained after reaction by the same method as in the synthesis of Compound aa069 using the obtained Compound aa072-b (3.63 g) was purified by reverse phase column chromatography (0.1% formic acid-water/0.1% formic acid-acetonitrile) to give Compound aa072 ((2S)-3-cyclobutyl-2-[9H-fluoren-9-ylmethoxycarbonyl(methyl)amino]propanoic acid, Fmoc-MeAla(cBu)-OH) (3.18 g, 91% through two steps).

LCMS (ESI) m/z=380 (M+H)+

Retention time: 0.94 min (analysis condition SQDFA05)

526

Synthesis of Compound aa073, (2S)-2-[9H-fluoren-9-ylmethoxycarbonyl(methyl)amino]-3-[3-(trifluoromethyl)phenyl]propanoic acid (Fmoc-MePhe(3-CF3)-OH)

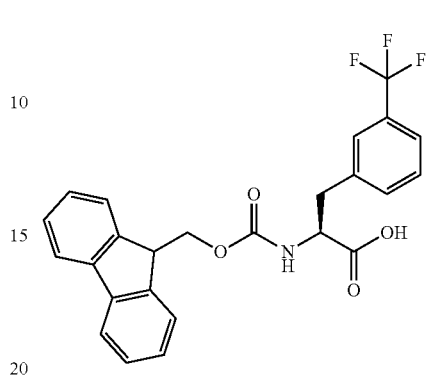

aa073-a

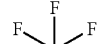

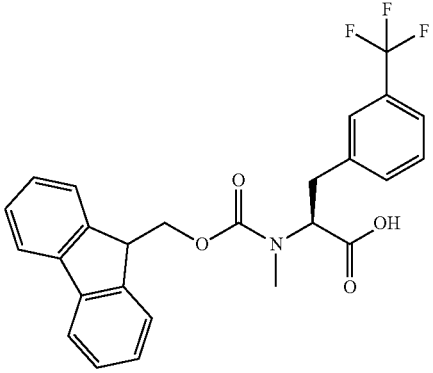

aa073

Compound aa073-b was obtained by the same method as in the synthesis of Compound aa069-b using Compound aa073-a ((2S)-2-[9H-fluoren-9-ylmethoxycarbonylamino]-3-[3-(trifluoromethyl)phenyl]propanoic acid, Fmoc-Phe(3-CF3)-OH) (2 g, 4.39 mmol) as a starting material. The obtained Compound aa073-b was reacted by the same method as in the synthesis of Compound aa069 and then purified by reverse phase column chromatography (0.1% aqueous formic acid solution/0.1% formic acid-acetonitrile solution) to give Compound aa073 ((2S)-2-[9H-fluoren-9-ylmethoxycarbonyl(methyl)amino]-3-[3-(trifluoromethyl)phenyl]propanoic acid, Fmoc-MePhe(3-CF3)-OH) (1.69 g, 82%).

LCMS (ESI) m/z=470 (M+H)+

Retention time: 0.95 min (analysis condition SQDFA05)

Synthesis of Compound aa074, (2S)-2-[9H-fluoren-9-ylmethoxycarbonyl(methyl)amino]-3-[2-(trifluoromethoxy)phenyl]propanoic acid (Fmoc-MePhe(2-OCF3)-OH)

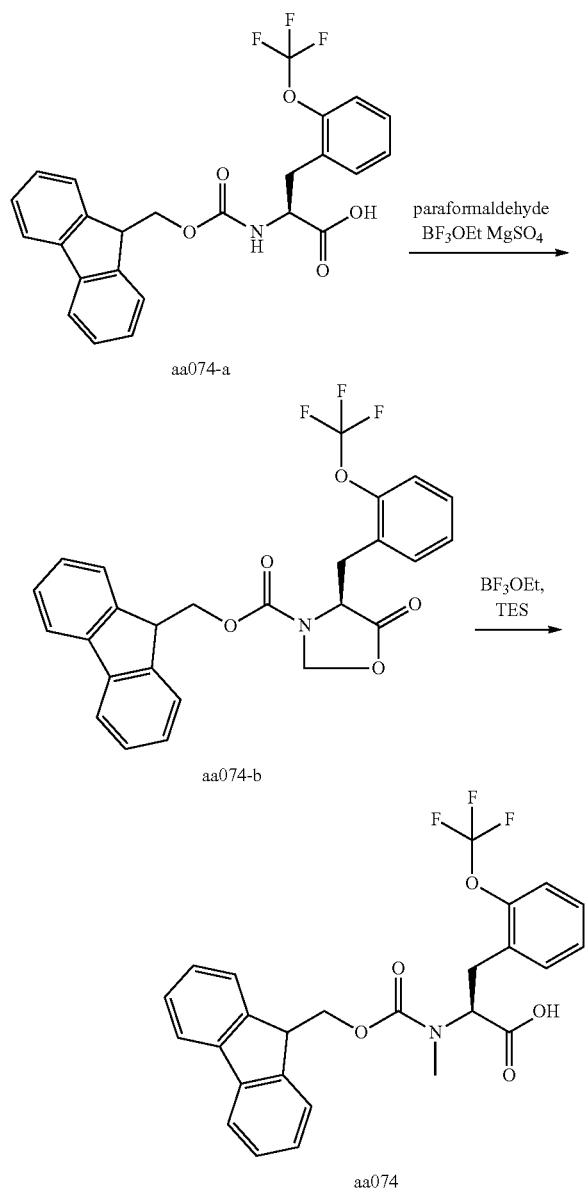

aa074-a aa074-b aa074

Compound aa074-b was obtained as a crude product by the same method as in the synthesis of Compound aa069-b using Compound aa074-a ((2S)-2-[9H-fluoren-9-ylmethoxycarbonylamino]-3-[2-(trifluoromethoxy)phenyl]propanoic acid, Fmoc-Phe(2-OCF3)-OH) (5 g, 10.61 mmol) as a starting material.

LCMS (ESI) m/z=484 (M+H)+

Retention time: 1.04 min (analysis condition SQDFA05)

Compound aa074 ((2S)-2-[9H-fluoren-9-ylmethoxycarbonyl(methyl)amino]-3-[2-(trifluoromethoxy)phenyl]propanoic acid, Fmoc-MePhe(2-OCF3)-OH) (4.77 g, 93% through two steps) was obtained by the same method as in the synthesis of Compound aa069 using the total amount of Compound aa074-b obtained above.

LCMS (ESI) m/z=486 (M+H)+

Retention time: 0.96 min (analysis condition SQDFA05)

Synthesis of Compound aa075, (2S)-2-cyclobutyl-2-[9H-fluoren-9-ylmethoxycarbonyl(methyl)amino]acetic acid (Fmoc-MeGly(cBu)-OH)

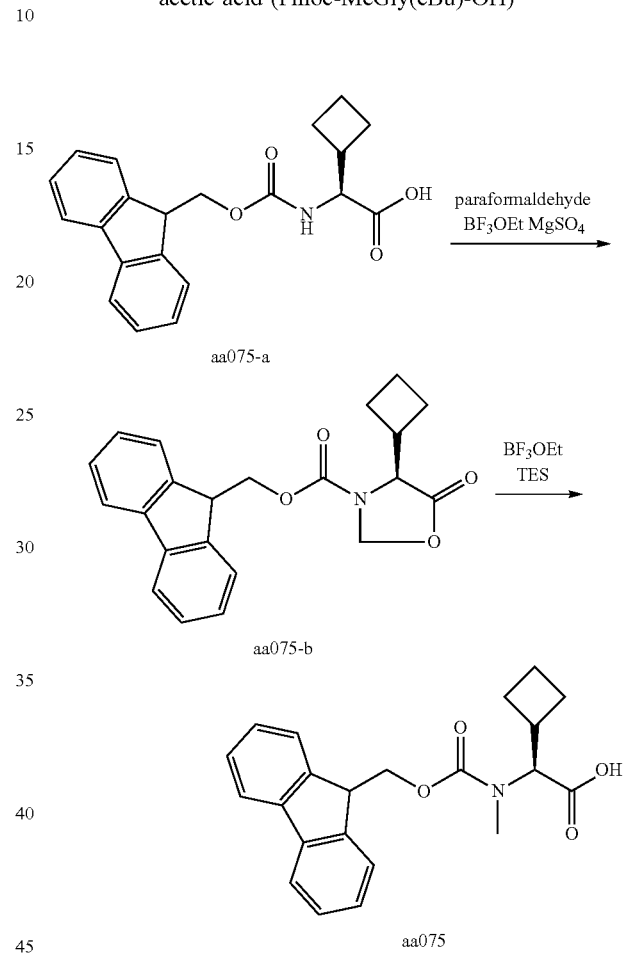

aa075-a aa075-b aa075

Compound aa075-b was obtained as a crude product by the same method as in the synthesis of Compound aa069-b using Compound aa075-a ((2S)-2-cyclobutyl-2-[9H-fluoren-9-ylmethoxycarbonylamino]acetic acid, Fmoc-Gly(cBu)-OH) (2.5 g, 7.11 mmol) as a starting material.

LCMS (ESI) m/z=364 (M+H)+

Retention time: 0.97 min (analysis condition SQDFA05)

A crude product obtained after reaction by the same method as in the synthesis of Compound aa069 using the total amount of Compound aa075-b obtained above was purified by reverse phase column chromatography (0.1% aqueous formic acid solution/0.1% formic acid-acetonitrile solution) to give Compound aa075 ((2S)-2-cyclobutyl-2-[9H-fluoren-9-ylmethoxycarbonyl(methyl)amino]acetic acid, Fmoc-MeGly(cBu)-OH) (2.32 g, 89% through two steps).

LCMS (ESI) m/z=366 (M+H)+

Retention time: 0.88 min (analysis condition SQDFA05)

529
Synthesis of Compound aa076, (2S)-2-[9H-fluoren-9-ylmethoxycarbonyl(methyl)amino]hex-5-ynoic acid (Fmoc-MeAhxy(2)-OH)

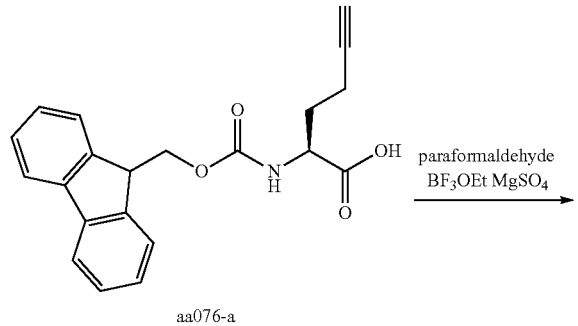

aa076-a

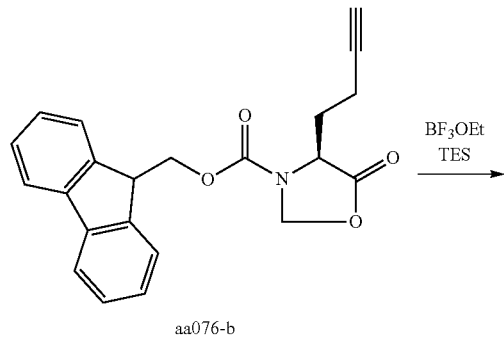

aa076-b

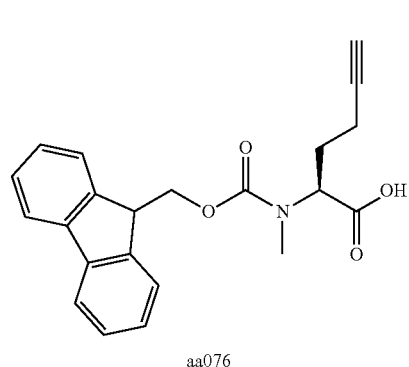

aa076

Compound aa076-b was obtained as a crude product by the same method as in the synthesis of Compound aa069-b using Compound aa076-a ((2S)-2-[9H-fluoren-9-ylmethoxycarbonylamino]hex-5-ynoic acid, Fmoc-Ahxy(2)-OH) (989 mg, 2.83 mmol) as a starting material. Compound aa076 ((2S)-2-[9H-fluoren-9-ylmethoxycarbonyl(methyl)amino]hex-5-ynoic acid, Fmoc-MeAhxy(2)-OH) (809 mg, 79% through two steps) was obtained by the same method as in the synthesis of Compound aa069 using the obtained Compound aa076-b.

LCMS (ESI) m/z=364 (M+H)+

Retention time: 0.81 min (analysis condition SQDFA05)

530
Synthesis of Compound aa077, (2S)-2-[9H-fluoren-9-ylmethoxycarbonyl(methyl)amino]-3-(2-methylphenyl)propanoic acid (Fmoc-MePhe(2-Me)-OH)

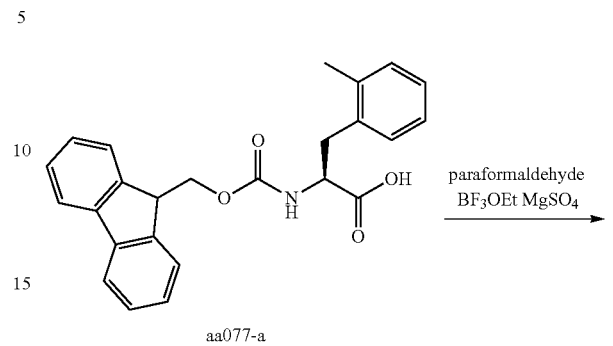

aa077-a

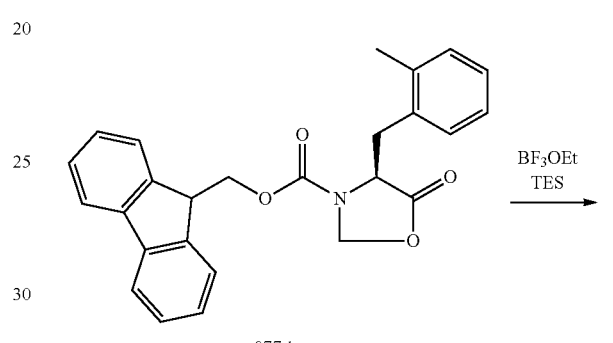

aa077-b

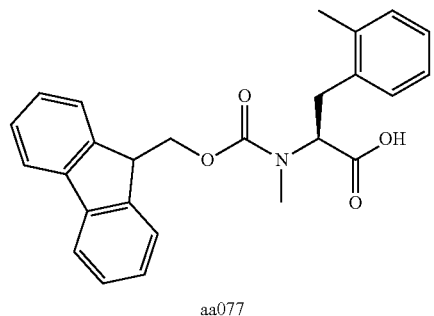

aa077

Compound aa077-a ((2S)-2-[9H-fluoren-9-ylmethoxycarbonylamino]-3-(2-methylphenyl)propanoic acid, Fmoc-Phe(2-Me)-OH) (2 g, 4.98 mmol) was used as a starting material and a reaction solution was obtained by the same method as in the synthesis of Compound aa069-b. To the resulting reaction solution was added a saturated aqueous sodium bicarbonate solution. A silica gel column (2 v/w) was charged with the reaction solution, which was then eluted with DCM to give Compound aa077-b as a crude product (1.45 g). Compound aa077 ((2S)-2-[9H-fluoren-9-ylmethoxycarbonyl(methyl)amino]-3-(2-methylphenyl)propanoic acid, Fmoc-MePhe(2-Me)-OH) (1.21 g, 58% through two steps) was obtained by the same method as in the synthesis of Compound aa069 using the obtained Compound aa077-b.

LCMS (ESI) m/z=416 (M+H)+

Retention time: 0.94 min (analysis condition SQDFA05)

Synthesis of Compound aa078, (2S)-2-[9H-fluoren-9-ylmethoxycarbonyl(methyl)amino]-4-methoxybutanoic acid (Fmoc-MeHse(Me)-OH)

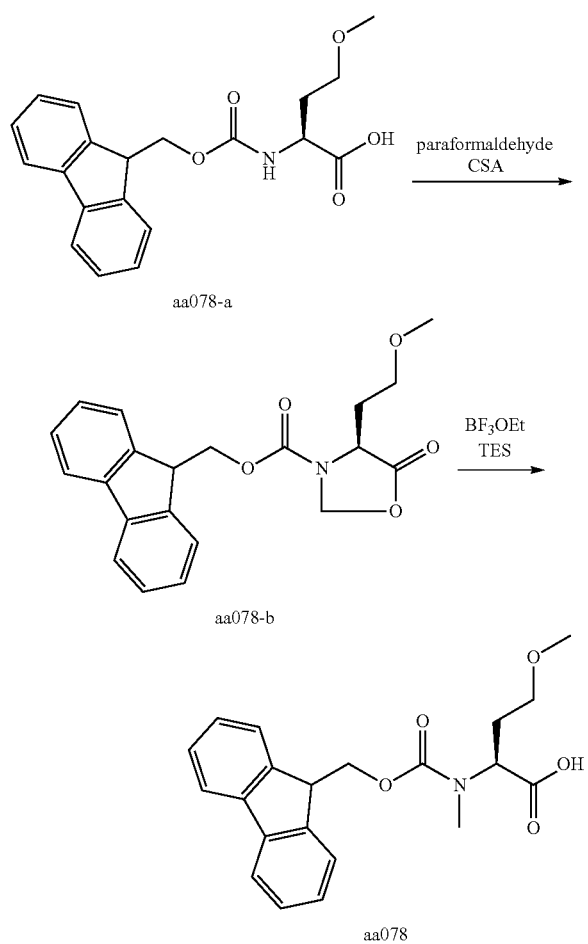

Compound aa078-a ((2S)-2-[9H-fluoren-9-ylmethoxycarbonylamino]-4-methoxybutanoic acid, Fmoc-Hse(Me)-OH) (5.0 g, 14.07 mmol), paraformaldehyde (1.27 g, 42.2 mmol), and CSA (0.163 g, 0.70 mmol) were suspended in toluene (82 mL) and stirred at 80° C. for 14 hours. The reaction solution was cooled to room temperature, after which the filtrate was diluted with ethyl acetate (100 mL) and then washed with saturated aqueous sodium bicarbonate/water (1/1) and brine/water (1/1). The organic layer was dried over anhydrous sodium sulfate, filtered, and then concentrated under reduced pressure to give Compound aa078-b as a crude product (5.1 g, 99%).

LCMS (ESI) m/z=368 (M+H)+

Retention time: 0.84 min (analysis condition SQDFA05)

To a solution of the obtained Compound aa078-b (5.12 g, 13.94 mmol) in DCM (46.5 mL) were added triethylsilane (6.68 mL, 41.8 mmol), water (0.251 mL, 13.94 mmol), and boron trifluoride-diethyl ether complex (BF₃·OEt₂) (3.53 mL, 27.9 mmol) under ice-cooling under a nitrogen atmosphere, and the mixture was stirred for two hours. To the reaction solution were added saturated aqueous ammonium chloride/water (1/1) and water (5 mL), and the organic layer was separated. The aqueous layer was extracted with DCM and the organic layer was washed with brine/water (1/1). The organic layer was dried over anhydrous sodium sulfate, filtered, and then concentrated under reduced pressure. The resulting compound was dissolved in acetonitrile, washed with n-hexane, and concentrated under reduced pressure to yield Compound aa078 ((2S)-2-[9H-fluoren-9-ylmethoxycarbonyl(methyl)amino]-4-methoxybutanoic acid, Fmoc-MeHse(Me)-OH) (4.9 g, 95%).

LCMS (ESI) m/z=370 (M+H)+

Retention time: 0.76 min (analysis condition SQDFA05)

Synthesis of Compound aa079, (2S)-2-cyclopentyl-2-[9H-fluoren-9-ylmethoxycarbonyl(methyl)amino] acetic acid (Fmoc-MeGly(cPent)-OH)

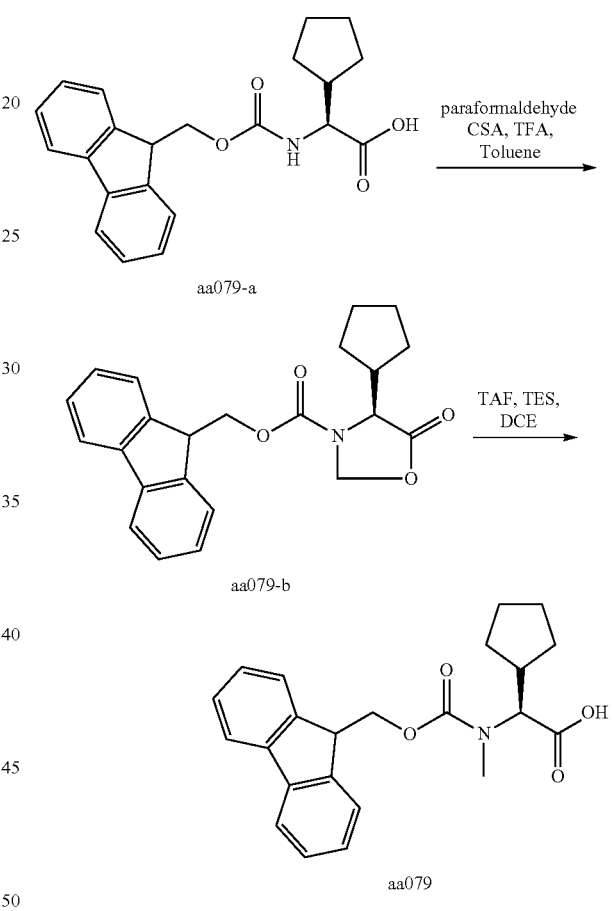

To a mixture of Compound aa079-a ((2S)-2-cyclopentyl-2-[9H-fluoren-9-ylmethoxycarbonylamino]acetic acid, Fmoc-Gly(cPent)-OH) (30.0 g, 82 mmol), paraformaldehyde (7.39 g, 246 mmol), and CSA (0.954 g, 4.10 mmol) in toluene (160 mL) was added trifluoroacetic acid (TFA) (9.0 mL), and the mixture was then stirred at 60° C. for four hours. The reaction solution was cooled to room temperature, and the solid was then removed by filtration. The filtrate was concentrated under reduced pressure, diluted with ethyl acetate (220 mL), and then sequentially washed with a saturated aqueous sodium bicarbonate solution and brine. The organic layer was dried over anhydrous sodium sulfate, filtered, and then concentrated under reduced pressure to give Compound aa079-b as a crude product. The next reaction was performed without further purification.

LCMS (ESI) m/z=378 (M+H)+

Retention time: 1.01 min (analysis condition SQDFA05)

To a mixture of the total amount of Compound aa079-b obtained above and triethylsilane (TES) (65.5 mL, 410 mmol) in dichloroethane (DCE) (90 mL) was added trifluoroacetic acid (TFA) (76 mL, 984 mmol), and the mixture was stirred at 60° C. for 16 hours. The reaction solution was cooled to room temperature and then concentrated under reduced pressure, and the resulting solid was washed with n-hexane/ethyl acetate (95/5) and dried under reduced pressure to give Compound aa079 ((2S)-2-cyclopentyl-2-[9H-fluoren-9-ylmethoxycarbonyl(methyl)amino]acetic acid, Fmoc-MeGly(cPent)-OH) (29.1 g, 93% through two steps).

LCMS (ESI) m/z=380 (M+H)+

Retention time: 0.92 min (analysis condition SQDFA05)

Synthesis of Compound aa080, (2S)-2-[9H-fluoren-9-ylmethoxycarbonyl(methyl)amino]-3-(3-fluorophenyl)propanoic acid (Fmoc-MePhe(3-F)—OH)

Compound aa080-b was obtained as a crude product (3.78 g, quant.) by the same method as in the synthesis of Compound aa078-b using Compound aa080-a ((2S)-2-(9H-fluoren-9-ylmethoxycarbonylamino)-3-(3-fluorophenyl) propanoic acid, Fmoc-Phe(3-F)—OH) (3.38 g, 8.34 mmol) as a starting material.

LCMS (ESI) m/z=418 (M+H)+

Retention time: 0.98 min (analysis condition SQDFA05)

Compound aa080 ((2S)-2-[9H-fluoren-9-ylmethoxycarbonyl(methyl)amino]-3-(3-fluorophenyl)propanoic acid, Fmoc-MePhe(3-F)—OH) (3.52 g, quant.) was obtained by the same method as in the synthesis of Compound aa078 using the obtained Compound aa080-b (3.6 g, 8.62 mmol).

LCMS (ESI) m/z=420 (M+H)+

Retention time: 0.89 min (analysis condition SQDFA05)

Synthesis of Compound aa081, (2S)-2-[9H-fluoren-9-ylmethoxycarbonyl(methyl)amino]-3-[4-(trifluoromethoxy)phenyl]propanoic acid (Fmoc-MePhe(4-OCF3)-OH)

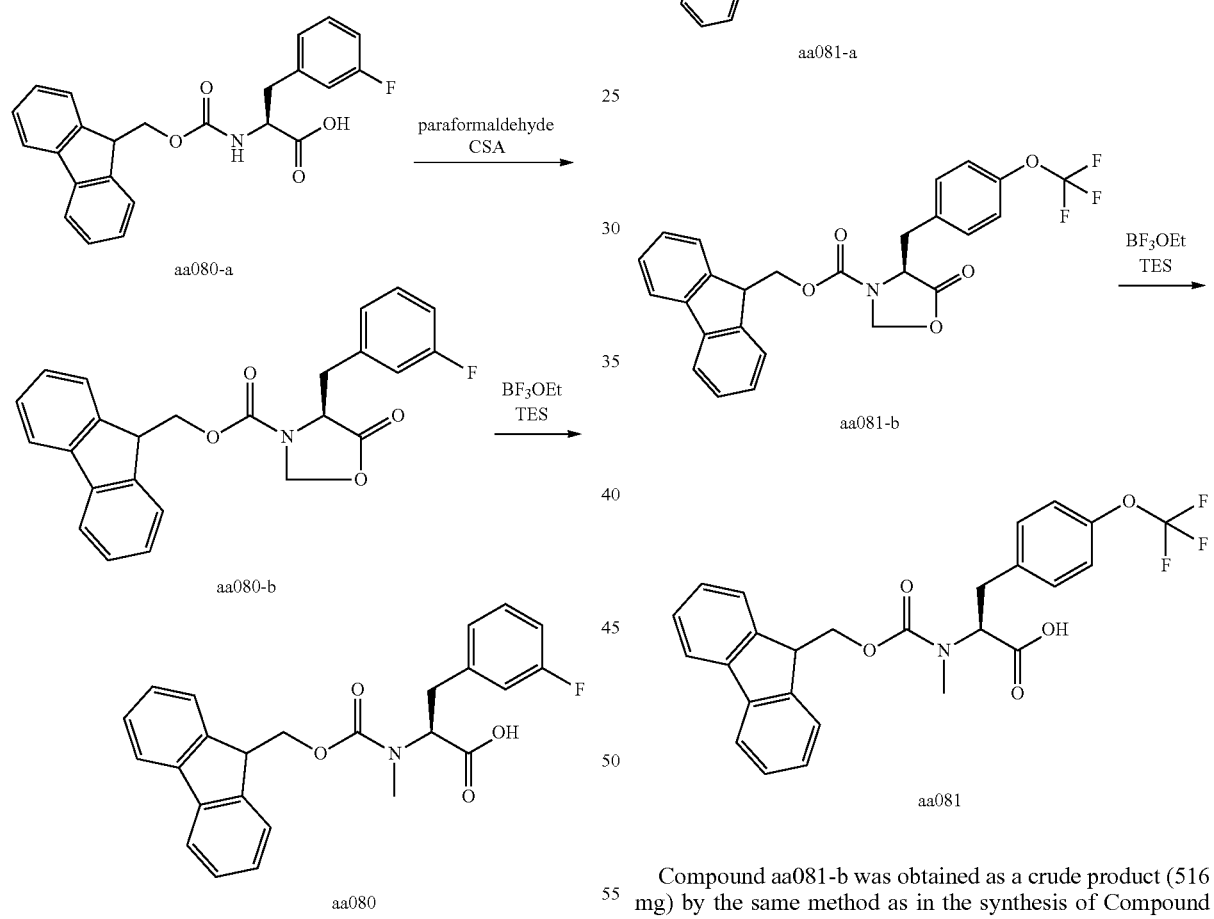

Compound aa081-b was obtained as a crude product (516 mg) by the same method as in the synthesis of Compound aa078-b using Compound aa081-a ((2S)-2-[9H-fluoren-9-ylmethoxycarbonylamino]-3-[4-(trifluoromethoxy)phenyl] propanoic acid, Fmoc-Phe(4-OCF3)-OH) (0.5 g, 1.061 mmol) as a starting material. Compound aa081 ((2S)-2-[9H-fluoren-9-ylmethoxycarbonyl(methyl)amino]-3-[4-(trifluoromethoxy)phenyl]propanoic acid, Fmoc-MePhe(4-OCF3)-OH) (462 mg, 90% through two steps) was obtained by the same method as in the synthesis of Compound aa078 using the obtained Compound aa081-b (516 mg).

LCMS (ESI) m/z=486 (M+H)+

Retention time: 0.97 min (analysis condition SQDFA05)

535
Synthesis of Compound aa082, (2S)-2-[9H-fluoren-9-ylmethoxycarbonyl(methyl)amino]-3-(4-fluorophenyl)propanoic acid (Fmoc-MePhe(4-F)—OH)

536
Synthesis of Compound aa083, (2S)-2-[9H-fluoren-9-ylmethoxycarbonyl(methyl)amino]pent-4-ynoic acid (Fmoc-MePRA-OH)

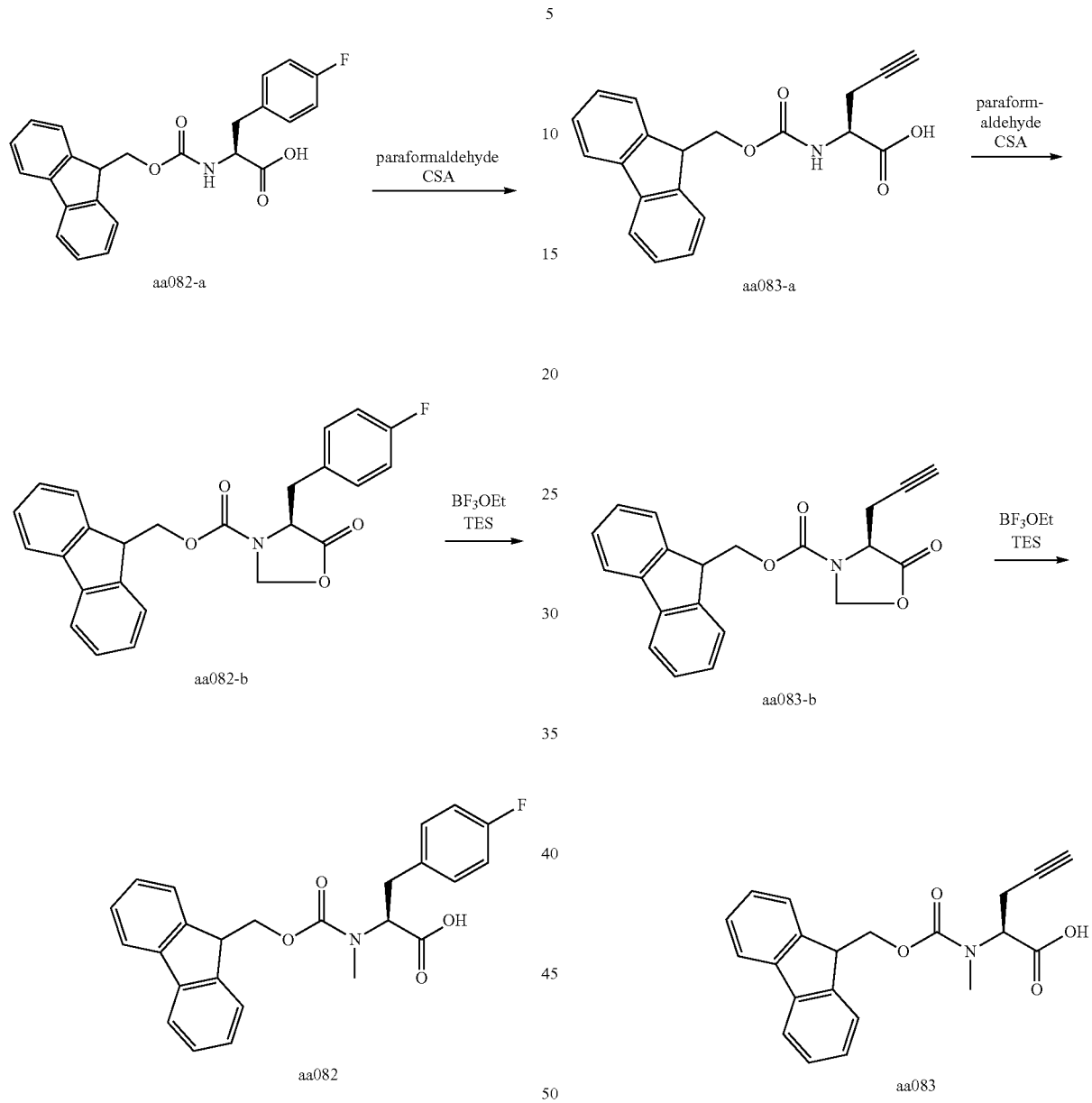

Compound aa082-b was obtained as a crude product (8.55 g) by the same method as in the synthesis of Compound aa078-b using Compound aa082-a ((2S)-2-[9H-fluoren-9-ylmethoxycarbonylamino]-3-(4-fluorophenyl)propanoic acid, Fmoc-Phe(4-F)—OH) (10.0 g, 24.67 mmol) as a starting material.

LCMS (ESI) m/z=418 (M+H)+

Retention time: 0.98 min (analysis condition SQDFA05)

Compound aa082 ((2S)-2-[9H-fluoren-9-ylmethoxycarbonyl(methyl)amino]-3-(4-fluorophenyl)propanoic acid, Fmoc-MePhe(4-F)—OH) (7.28 g, 70% through two steps) was obtained by the same method as in the synthesis of Compound aa078 using the obtained Compound aa082-b (8.55 g).

LCMS (ESI) m/z=420 (M+H)+

Retention time: 0.90 min (analysis condition SQDFA05)

Compound aa083-b (2.71 g, 87%) was obtained by the same method as in the synthesis of Compound aa078-b using Compound aa083-a ((2S)-2-[9H-fluoren-9-ylmethoxycarbonylamino]pent-4-ynoic acid, Fmoc-PRA-OH) (3 g, 8.95 mmol) as a starting material.

LCMS (ESI) m/z=348 (M+H)+

Retention time: 0.87 min (analysis condition SQDFA05)

Compound aa083 ((2S)-2-[9H-fluoren-9-ylmethoxycarbonyl(methyl)amino]pent-4-ynoic acid, Fmoc-MePRA-OH) (986 mg, 99%) was obtained by the same method as in the synthesis of Compound aa078 using the obtained Compound aa083-b (989 mg, 2.85 mmol).

LCMS (ESI) m/z=350 (M+H)+

Retention time: 0.79 min (analysis condition SQDFA05)

Synthesis of Compound aa084, (2S)-2-[9H-fluoren-9-ylmethoxycarbonyl(methyl)amino]heptanoic acid (Fmoc-MeHnl-OH)

Synthesis of Compound aa085, (2S)-2-[9H-fluoren-9-ylmethoxycarbonyl(methyl)amino]-3-(4-methylphenyl)propanoic acid (Fmoc-MePhe(4-Me)-OH)

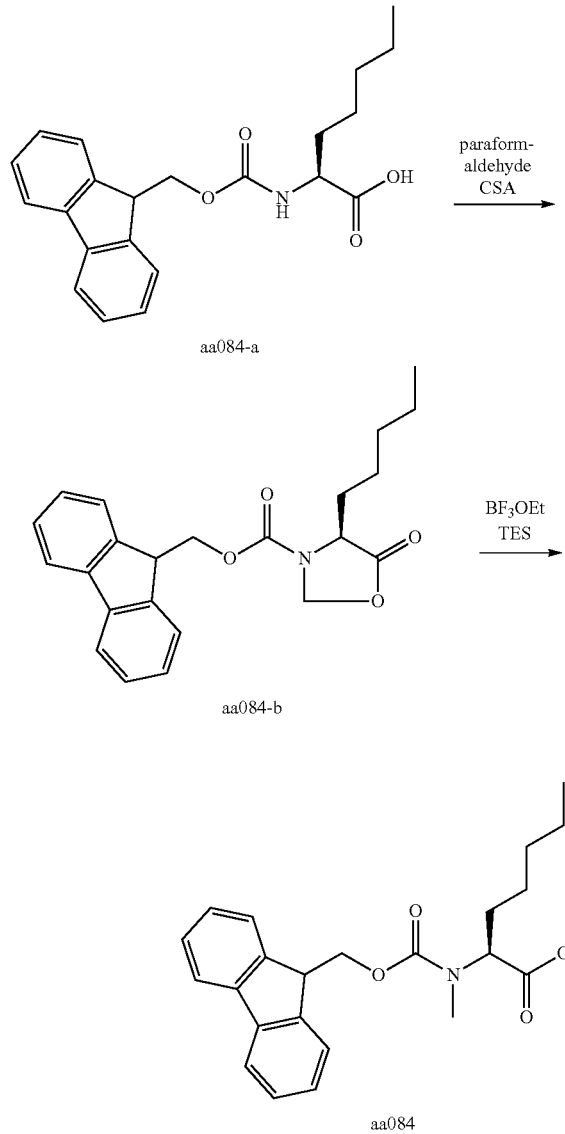

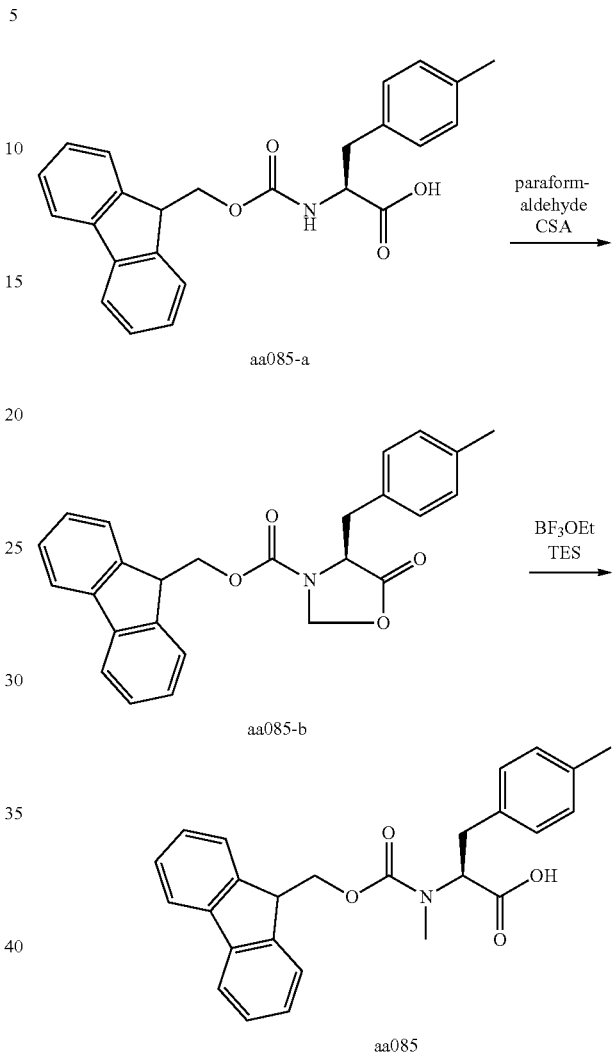

Compound aa084-b was obtained as a crude product (5.58 g) by the same method as in the synthesis of Compound aa078-b using Compound aa084-a ((2S)-2-[9H-fluoren-9-ylmethoxycarbonylamino]heptanoic acid, Fmoc-Hnl-OH) (5 g, 13.61 mmol) as a starting material.

LCMS (ESI) m/z=380 (M+H)+

Retention time: 1.05 min (analysis condition SQDFA05)

Compound aa084 ((2S)-2-[9H-fluoren-9-ylmethoxycarbonyl(methyl)amino]heptanoic acid, Fmoc-MeHnl-OH) (4.869 g, 94%) was obtained by the same method as in the synthesis of Compound aa078 using the obtained Compound aa084-b (5.16 g, 12.58 mmol).

LCMS (ESI) m/z=382 (M+H)+

Retention time: 0.97 min (analysis condition SQDFA05)

Compound aa085-b was obtained as a crude product (22.66 g) by the same method as in the synthesis of Compound aa078-b using Compound aa085-a ((2S)-2-[9H-fluoren-9-ylmethoxycarbonylamino]-3-(4-methylphenyl)propanoic acid, Fmoc-Phe(4-Me)-OH) (20 g, 49.8 mmol) as a starting material.

LCMS (ESI) m/z=414 (M+H)+

Retention time: 1.04 min (analysis condition SQDFA05)

A crude product obtained after reaction by the same method as in the synthesis of Compound aa078 using the obtained Compound aa085-b (22.66 g) was purified by reverse phase column chromatography (0.1% formic acid-water/0.1% formic acid-acetonitrile) to give Compound aa085 ((2S)-2-[9H-fluoren-9-ylmethoxycarbonyl(methyl)amino]-3-(4-methylphenyl)propanoic acid, Fmoc-MePhe(4-Me)-OH) (17.3 g, 83.5% through two steps).

LCMS (ESI) m/z=416 (M+H)+

Retention time: 2.41 min (analysis condition SQDFA3080)

539

Synthesis of Compound aa086, (2S)-3-(4-bromophenyl)-2-[9H-fluoren-9-ylmethoxycarbonyl(methyl)amino]propanoic acid (Fmoc-MePhe(4-Br)—OH)

540

Synthesis of Compound aa087, (2S)-2-[9H-fluoren-9-ylmethoxycarbonyl(methyl)amino]-3-[3-(trifluoromethoxy)phenyl]propanoic acid (Fmoc-MePhe(3-OCF3)-OH)

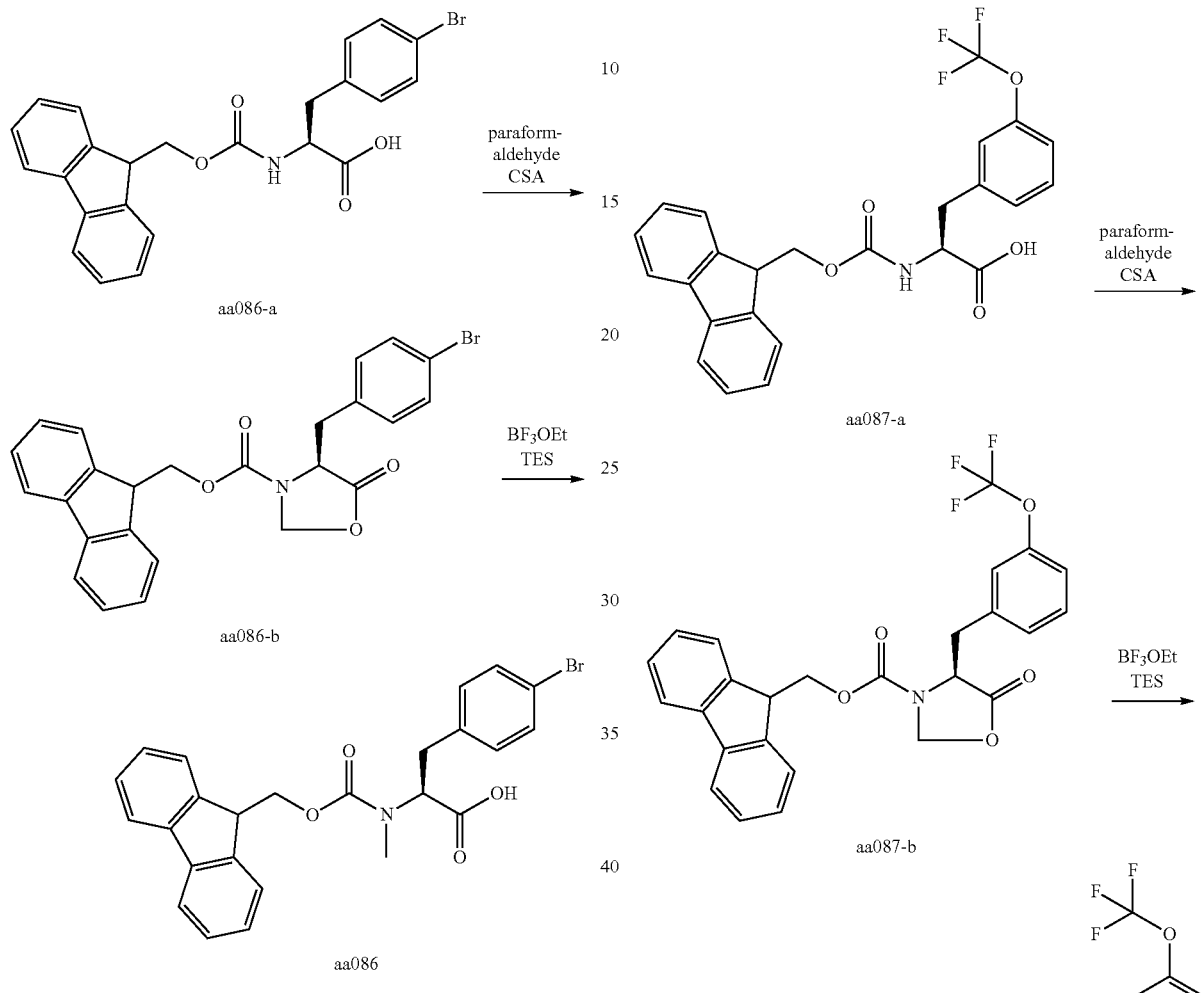

A crude product obtained by the same method as in the synthesis of Compound aa078-b using Compound aa086-a ((2S)-3-(4-bromophenyl)-2-[9H-fluoren-9-ylmethoxycarbonylamino]propanoic acid, Fmoc-Phe(4-Br)—OH) (6 g, 12.87 mmol) as a starting material was purified by reverse phase column chromatography (0.1% aqueous formic acid/0.1% formic acid-acetonitrile) to give Compound aa086-b (3.57 g, 58%).

LCMS (ESI) m/z=478 (M+H)+

Retention time: 1.05 min (analysis condition SQDFA05)

A crude product obtained by the same method as in the synthesis of Compound aa078 using the obtained Compound aa086-b (3.57 g, 7.46 mmol) was washed with acetonitrile/hexane (1/1) to give Compound aa086 ((2S)-3-(4-bromophenyl)-2-[9H-fluoren-9-ylmethoxycarbonyl(methyl)amino]propanoic acid, Fmoc-MePhe(4-Br)—OH) (3.40 g, 95%).

LCMS (ESI) m/z=480 (M+H)+

Retention time: 0.96 min (analysis condition SQDFA05)

Compound aa087-b was obtained as a crude product (5.84 g) by the same method as in the synthesis of Compound aa078-b using Compound aa087-a ((2S)-2-[9H-fluoren-9-ylmethoxycarbonylamino]-3-[3-(trifluoromethoxy)phenyl] propanoic acid, Fmoc-Phe(3-OCF3)-OH) (6.07 g, 12.87 mmol) as a starting material.

LCMS (ESI) m/z=484 (M+H)+

Retention time: 1.05 min (analysis condition SQDFA05)

Compound aa087 ((2S)-2-[9H-fluoren-9-ylmethoxycarbonyl(methyl)amino]-3-[3-(trifluoromethoxy)phenyl]propanoic acid, Fmoc-MePhe(3-OCF3)-OH) (5.66 g, 91% through two steps) was obtained by the same method as in the synthesis of Compound aa078 using the obtained Compound aa087-b (5.84 g).

LCMS (ESI) m/z=486 (M+H)+

Retention time: 0.97 min (analysis condition SQDFA05)

Synthesis of Compound aa088, 1-[9H-fluoren-9-ylmethoxycarbonyl(methyl)amino]cyclopentane-1-carboxylic acid (Fmoc-MecLeu-OH)

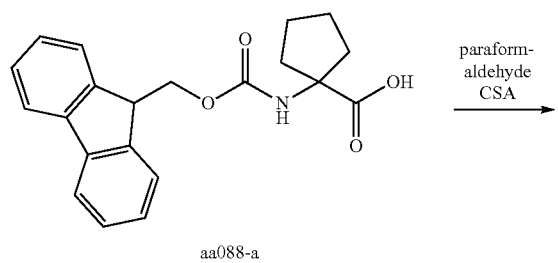

aa088-a

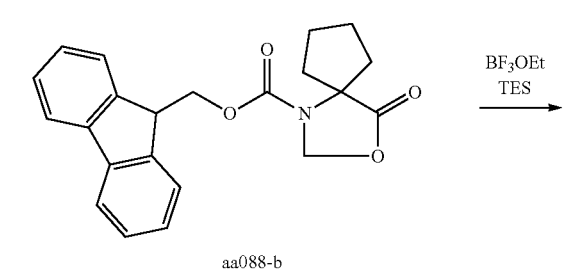

aa088-b

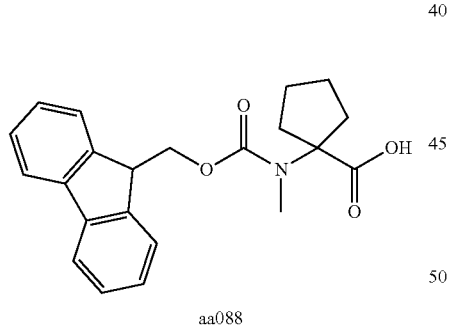

aa088

Compound aa088-b was obtained as a crude product by the same method as in the synthesis of Compound aa078-b using Compound aa088-a (1-[9H-fluoren-9-ylmethoxycarbonylamino]cyclopentane-1-carboxylic acid, Fmoc-cLeu-OH) (10 g, 28.5 mmol) as a starting material. A crude product was obtained by the same method as in the synthesis of Compound aa078 using Compound aa088-b. The resulting crude product was purified by trituration (hexane/TBME) to give Compound aa088 (1-[9H-fluoren-9-ylmethoxycarbonyl(methyl)amino]cyclopentane-1-carboxylic acid, Fmoc-MecLeu-OH) (6.82 g, 66% through two steps).

LCMS (ESI) m/z=366 (M+H)+

Retention time: 0.87 min (analysis condition SQDFA05)

Synthesis of Compound aa089, (2S)-2-cyclopropyl-2-[9H-fluoren-9-ylmethoxycarbonyl(methyl)amino]acetic acid (Fmoc-MeGly(cPr)—OH)

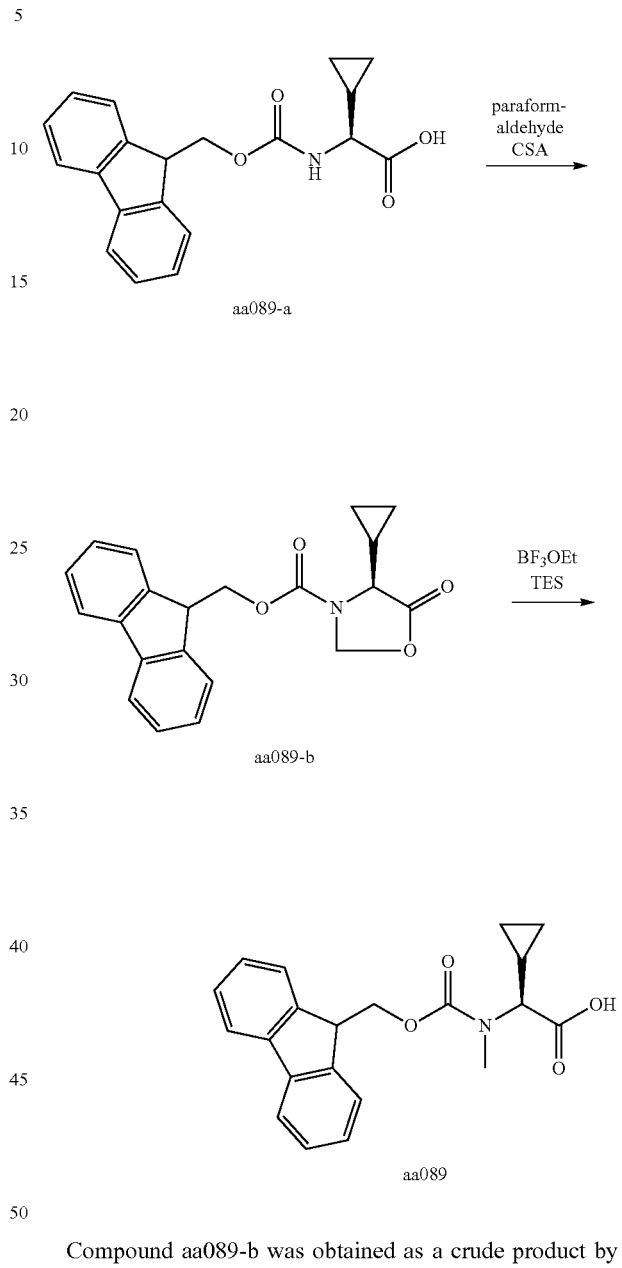

Compound aa089-b was obtained as a crude product by the same method as in the synthesis of Compound aa078-b using Compound aa089-a ((2S)-2-cyclopropyl-2-[9H-fluoren-9-ylmethoxycarbonylamino]acetic acid, Fmoc-Gly(cPr)—OH) (5 g, 14.82 mmol) as a starting material.

LCMS (ESI) m/z=350 (M+H)+

Retention time: 0.89 min (analysis condition SQDFA05)

Compound aa089 ((2S)-2-cyclopropyl-2-[9H-fluoren-9-ylmethoxycarbonyl(methyl)amino]acetic acid, Fmoc-MeGly(cPr)—OH) (5.18 g, 99% through two steps) was obtained by the same method as in the synthesis of Compound aa078 using the total amount of Compound aa089-b obtained above.

LCMS (ESI) m/z=352 (M+H)+

Retention time: 0.80 min (analysis condition SQDFA05)

543

Synthesis of Compound aa090, (2S)-2-[9H-fluoren-9-ylmethoxycarbonyl(methyl)amino]-3-[4-(trifluoromethyl)phenyl]propanoic acid (Fmoc-MePhe(4-CF3)-OH)

544

Synthesis of Compound aa091, (2S)-2-[9H-fluoren-9-ylmethoxycarbonyl(methyl)amino]-4,4,4-trifluorobutanoic acid (Fmoc-MeAbu(4-F3)-OH)

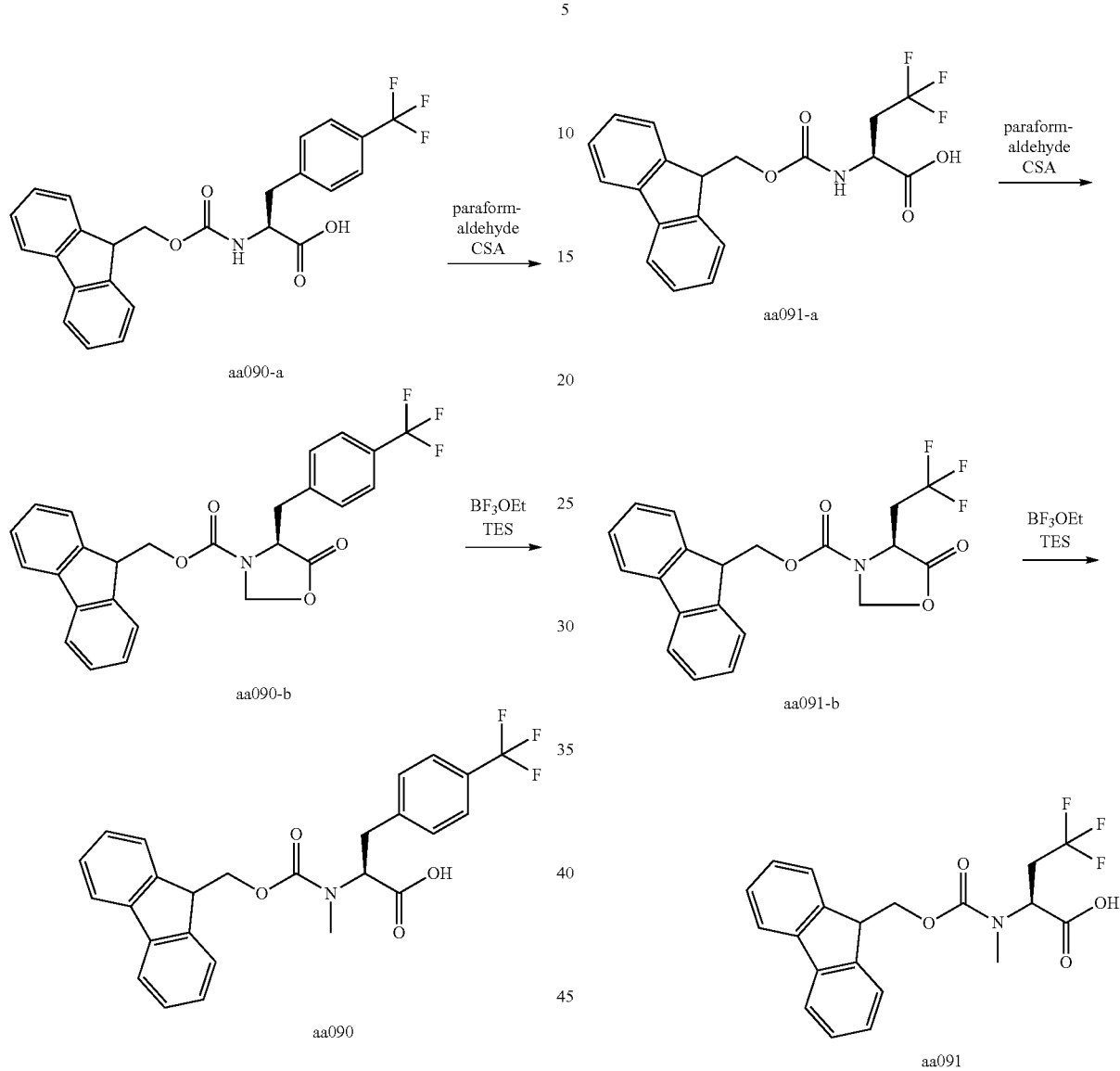

Compound aa090-b was obtained as a crude product (206.8 g) by the same method as in the synthesis of Compound aa078-b using Compound aa090-a ((2S)-2-[9H-fluoren-9-ylmethoxycarbonylamino]-3-[4-(trifluoromethyl)phenyl]propanoic acid, Fmoc-Phe(4-CF3)-OH) (200 g, 439 mmol) as a starting material.

LCMS (ESI) m/z=468.5 (M+H)+

Retention time: 3.30 min (analysis condition SMD-method_03)

Compound aa090 ((2S)-2-[9H-fluoren-9-ylmethoxycarbonyl(methyl)amino]-3-[4-(trifluoromethyl)phenyl]propanoic acid, Fmoc-MePhe(4-CF3)-OH) (195 g, 95% through two steps) was obtained by the same method as in the synthesis of Compound aa078 using the obtained Compound aa090-b (205 g).

LCMS (ESI) m/z=469.95 (M+H)+

Retention time: 2.96 min (analysis condition SMD-Method_03)

Compound aa091-b was obtained as a crude product by the same method as in the synthesis of Compound aa078-b using Compound aa091-a ((2S)-2-[9H-fluoren-9-ylmethoxycarbonylamino]-4,4,4-trifluorobutanoic acid, Fmoc-Abu(4-F3)-OH) (0.994 g, 2.62 mmol) as a starting material. A crude product obtained by the same method as in the synthesis of Compound aa078 using the obtained Compound aa091-b (4.78 g), was washed with acetonitrile and filtered to collect a solid, which was then combined with a solid obtained by washing the filtrate with hexane and then evaporating the solvent from the filtrate under reduced pressure to give Compound aa091 ((2S)-2-[9H-fluoren-9-ylmethoxycarbonyl(methyl)amino]-4,4,4-trifluorobutanoic acid, Fmoc-MeAbu(4-F3)-OH) (961 mg, 93% through two steps).

LCMS (ESI) m/z=394 (M+H)+

Retention time: 0.83 min (analysis condition SQDFA05)

Synthesis of Compound aa092, (2S)-2-[9H-fluoren-9-ylmethoxycarbonyl(methyl)amino]-4-methylsulfonylbutanoic acid (Fmoc-MeMet(O2)-OH)

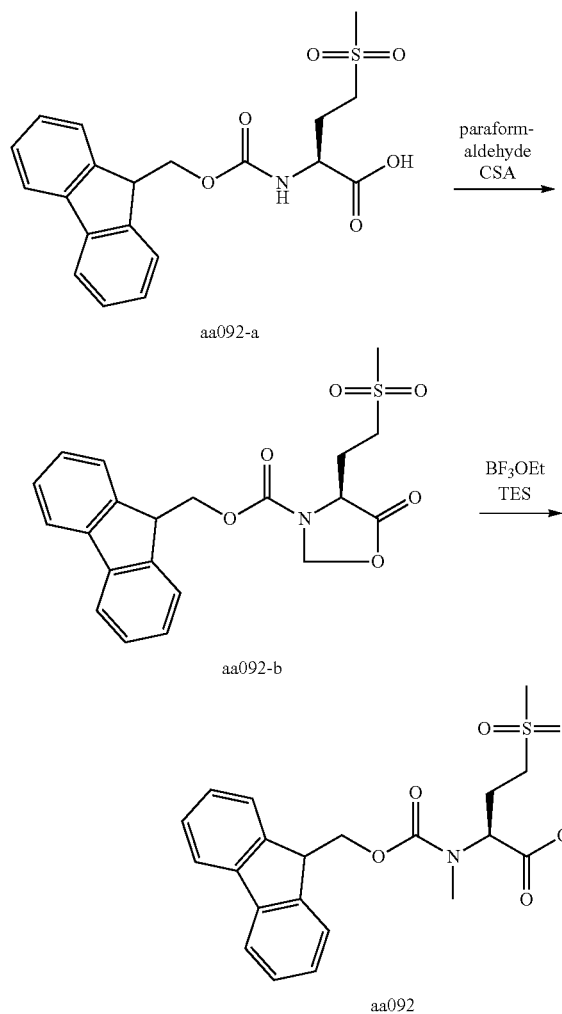

Compound aa092-a ((2S)-2-[9H-fluoren-9-ylmethoxycarbonylamino]-4-methylsulfonylbutanoic acid, Fmoc-Met(O2)-OH) (5.0 g, 12.39 mmol), paraformaldehyde (1.12 g, 37.2 mmol), and CSA (0.144 g, 0.62 mmol) were suspended in toluene (83 mL), and the mixture was stirred at 95° C. for four hours. The reaction solution was cooled to room temperature, after which the filtrate was diluted with ethyl acetate (100 mL) and then washed with saturated aqueous sodium bicarbonate/water (1/1) and brine/water (1/1). The organic layer was dried over anhydrous sodium sulfate, filtered, and then concentrated under reduced pressure to give Compound aa092-b (4.2 g) as a crude product.

LCMS (ESI) m/z=416 (M+H)+

Retention time: 0.77 min (analysis condition SQDFA05)

To a solution of the obtained Compound aa092-b (4.20 g, 10.11 mmol) in DCM (33.7 mL) were added triethylsilane (4.84 mL, 30.3 mmol), water (0.182 mL, 10.11 mmol), and boron trifluoride-diethyl ether complex (BF$_3$—OEt$_2$) (2.56 mL, 20.22 mmol) under ice-cooling under a nitrogen atmosphere, and the mixture was stirred for two hours. To the reaction solution were added saturated aqueous ammonium chloride/water (1/1) and water (3 ml), and the organic layer was separated. The aqueous layer was extracted with DCM and the organic layer was washed with brine, resulting in precipitation of a solid. The precipitated compound was washed with hexane to give Compound aa092 ((2S)-2-[9H-fluoren-9-ylmethoxycarbonyl(methyl)amino]-4-methylsulfonylbutanoic acid, Fmoc-MeMet(O2)-OH) (3.64 g, 86%).

LCMS (ESI) m/z=418 (M+H)+

Retention time: 0.68 min (analysis condition SQDFA05)

Synthesis of Compound aa093, (2S,3R)-2-[9H-fluoren-9-ylmethoxycarbonyl(methyl)amino]-3-methoxybutanoic acid (Fmoc-MeThr(Me)-OH)

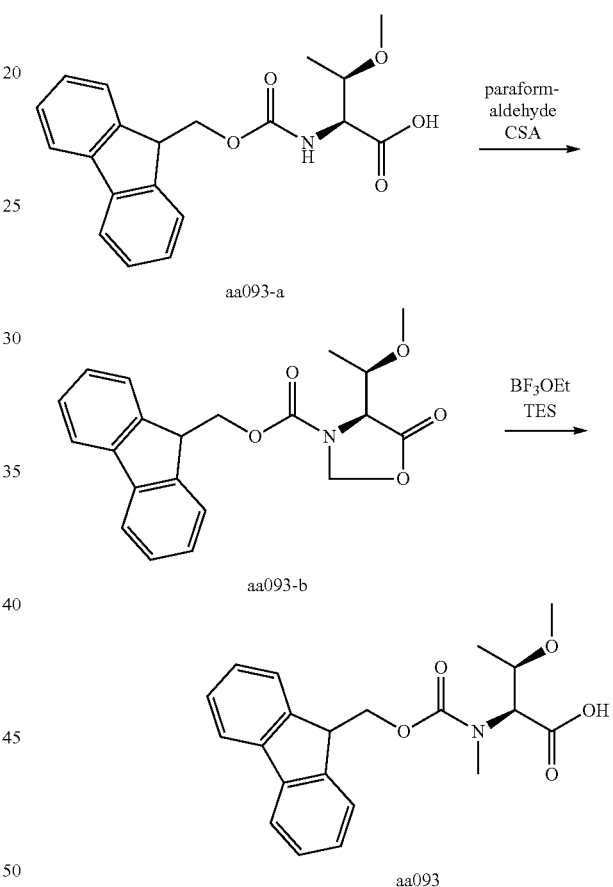

Compound aa093-b was obtained as a crude product by the same method as in the synthesis of Compound aa078-b using Compound aa093-a ((2S,3R)-2-[9H-fluoren-9-ylmethoxycarbonylamino]-3-methoxybutanoic acid, Fmoc-Thr(Me)-OH) (3 g, 8.44 mmol) as a starting material.

LCMS (ESI) m/z=368 (M+H)+

Retention time: 0.88 min (analysis condition SQDFA05)

Compound aa093 ((2S,3R)-2-[9H-fluoren-9-ylmethoxycarbonyl(methyl)amino]-3-methoxybutanoic acid, Fmoc-MeThr(Me)-OH) (2.79 g, 89% through two steps) was obtained by the same method as in the synthesis of Compound aa078 using the total amount of Compound aa093-b obtained above.

LCMS (ESI) m/z=370 (M+H)+

Retention time: 0.81 min (analysis condition SQDFA05)

547

Synthesis of Compound aa094, (2S)-3-(2-chlorophenyl)-2-[9H-fluoren-9-ylmethoxycarbonyl(methyl)amino]propanoic acid (Fmoc-MePhe(2-Cl)—OH)

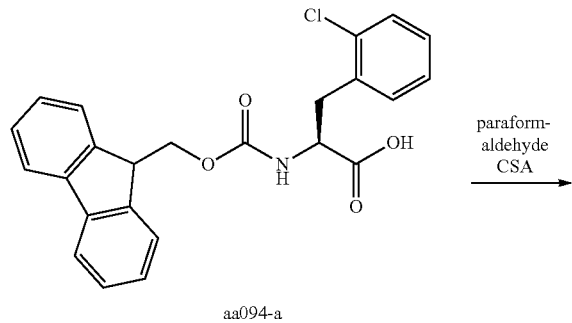
aa094-a

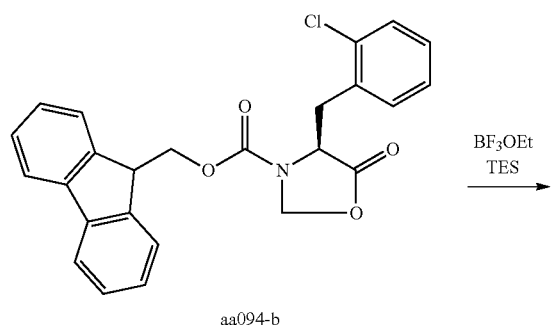
aa094-b

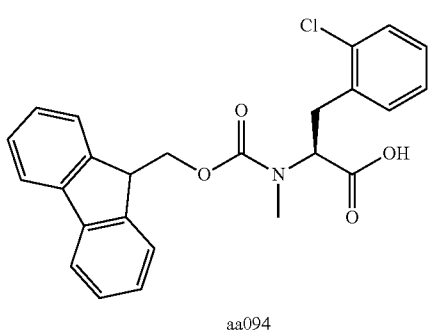
aa094

Compound aa094-b (4.2 g, 82%) was obtained by the same method as in the synthesis of Compound aa078-b using Compound aa094-a ((2S)-3-(2-chlorophenyl)-2-[9H-fluoren-9-ylmethoxycarbonylamino]propanoic acid, Fmoc-Phe(2-Cl)—OH) (5 g, 11.85 mmol) as a starting material.

LCMS (ESI) m/z=434 (M+H)+

Retention time: 1.01 min (analysis condition SQDFA05)

Compound aa094 ((2S)-3-(2-chlorophenyl)-2-[9H-fluoren-9-ylmethoxycarbonyl(methyl)amino]propanoic acid, Fmoc-MePhe(2-Cl)—OH) (3.32 g, 79%) was obtained by the same method as in the synthesis of Compound aa078 using the obtained Compound aa094-b (4.2 g).

LCMS (ESI) m/z=436 (M+H)+

Retention time: 0.94 min (analysis condition SQDFA05)

548

Synthesis of Compound aa095, (2S)-2-[9H-fluoren-9-ylmethoxycarbonyl(methyl)amino]-3-(2-fluorophenyl)propanoic acid (Fmoc-MePhe(2-F)—OH)

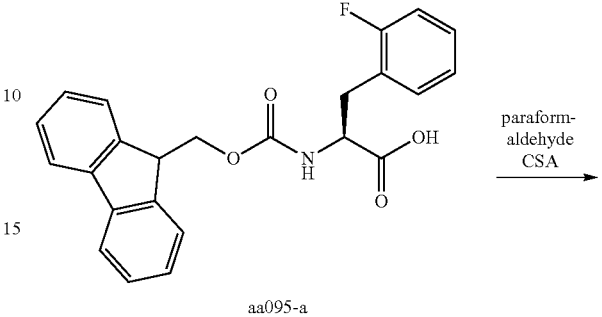
aa095-a

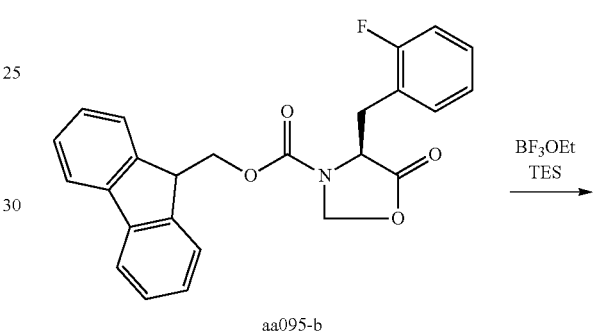
aa095-b

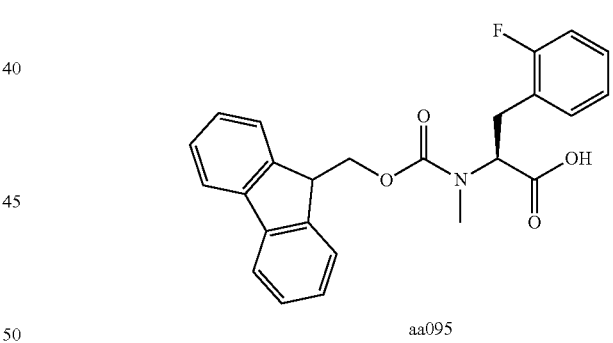
aa095

Compound aa095-b (3.21 g, quant.) was obtained by the same method as in the synthesis of Compound aa079-b using Compound aa095-a ((2S)-2-[9H-fluoren-9-ylmethoxycarbonylamino]-3-(2-fluorophenyl)propanoic acid, Fmoc-Phe(2-F)—OH) (3 g, 7.4 mmol) as a starting material.

LCMS (ESI) m/z=418 (M+H)+

Retention time: 0.97 min (analysis condition SQDFA05)

Compound aa095 ((2S)-2-[9H-fluoren-9-ylmethoxycarbonyl(methyl)amino]-3-(2-fluorophenyl)propanoic acid, Fmoc-MePhe(2-F)—OH) (2.89 g, 96%) was obtained by the same method as in the synthesis of Compound aa079 using the obtained Compound aa095-b (3 g, 7.19 mmol).

LCMS (ESI) m/z=420 (M+H)+

Retention time: 0.90 min (analysis condition SQDFA05)

549

Synthesis of Compound aa096, (2S)-2-[9H-fluoren-9-ylmethoxycarbonyl(methyl)amino]-3-(4-iodophenyl)propanoic acid (Fmoc-MePhe(4-I)—OH)

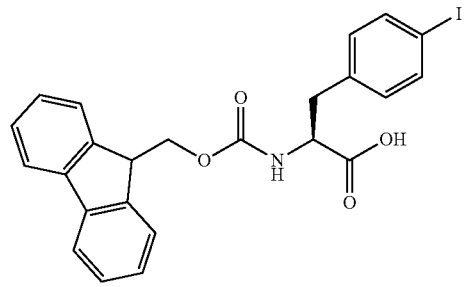

aa096-a

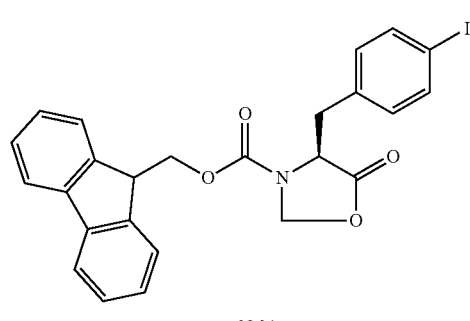

aa096-b

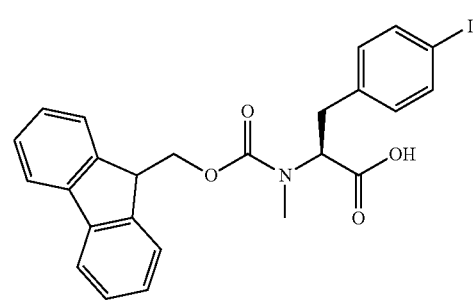

aa096

Compound aa096-b was obtained as a crude product (2.62 g) by the same method as in the synthesis of Compound aa078-b using Compound aa096-a ((2S)-2-[9H-fluoren-9-ylmethoxycarbonylamino]-3-(4-iodophenyl)propanoic acid, Fmoc-Phe(4-I)—OH) (2.36 g, 4.6 mmol) as a starting material.

LCMS (ESI) m/z=526 (M+H)+

Retention time: 1.07 min (analysis condition SQDFA05)

Compound aa096 ((2S)-2-[9H-fluoren-9-ylmethoxycarbonyl(methyl)amino]-3-(4-iodophenyl)propanoic acid, Fmoc-MePhe(4-I)—OH) (2.36 g, 97%) was obtained by the same method as in the synthesis of Compound aa078 using the obtained Compound aa096-b (2.62 g).

LCMS (ESI) m/z=528 (M+H)+

Retention time: 0.98 min (analysis condition SQDFA05)

550

Synthesis of Compound aa097, (2S)-3-(3-bromophenyl)-2-[9H-fluoren-9-ylmethoxycarbonyl(methyl)amino]propanoic acid (Fmoc-MePhe(3-Br)—OH)

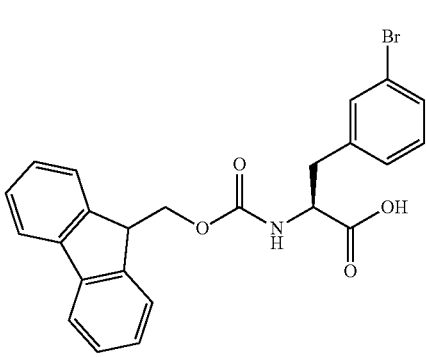

aa097-a

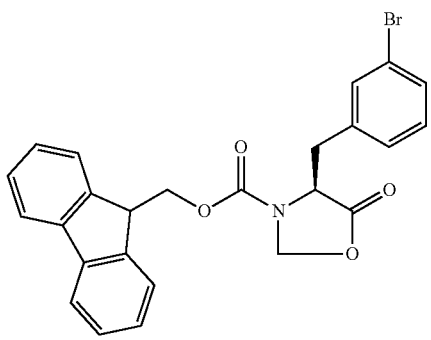

aa097-b

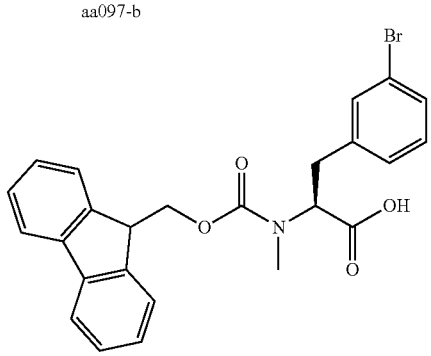

aa097

Compound aa097-b was obtained as a crude product (2.98 g) by the same method as in the synthesis of Compound aa078-b using Compound aa097-a ((2S)-3-(3-bromophenyl)-2-[9H-fluoren-9-ylmethoxycarbonylamino]propanoic acid, Fmoc-Phe(3-Br)—OH) (3 g, 6.43 mmol) as a starting material.

LCMS (ESI) m/z=478 (M+H)+

Retention time: 1.05 min (analysis condition SQDFA05)

Compound aa097 ((2S)-3-(3-bromophenyl)-2-[9H-fluoren-9-ylmethoxycarbonyl(methyl)amino]propanoic acid, Fmoc-MePhe(3-Br)—OH) (2.87 g, 92% through two steps) was obtained by the same method as in the synthesis of Compound aa078 using the obtained Compound aa097-b (2.98 g).

LCMS (ESI) m/z=480 (M+H)+

Retention time: 0.96 min (analysis condition SQDFA05)

Synthesis of Compound aa098, (2S)-2-[9H-fluoren-9-ylmethoxycarbonyl(methyl)amino]-2-methyl-3-phenylpropanoic acid (Fmoc-Me(Me)Phe-OH)

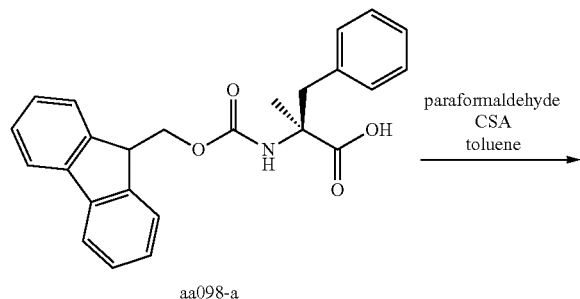

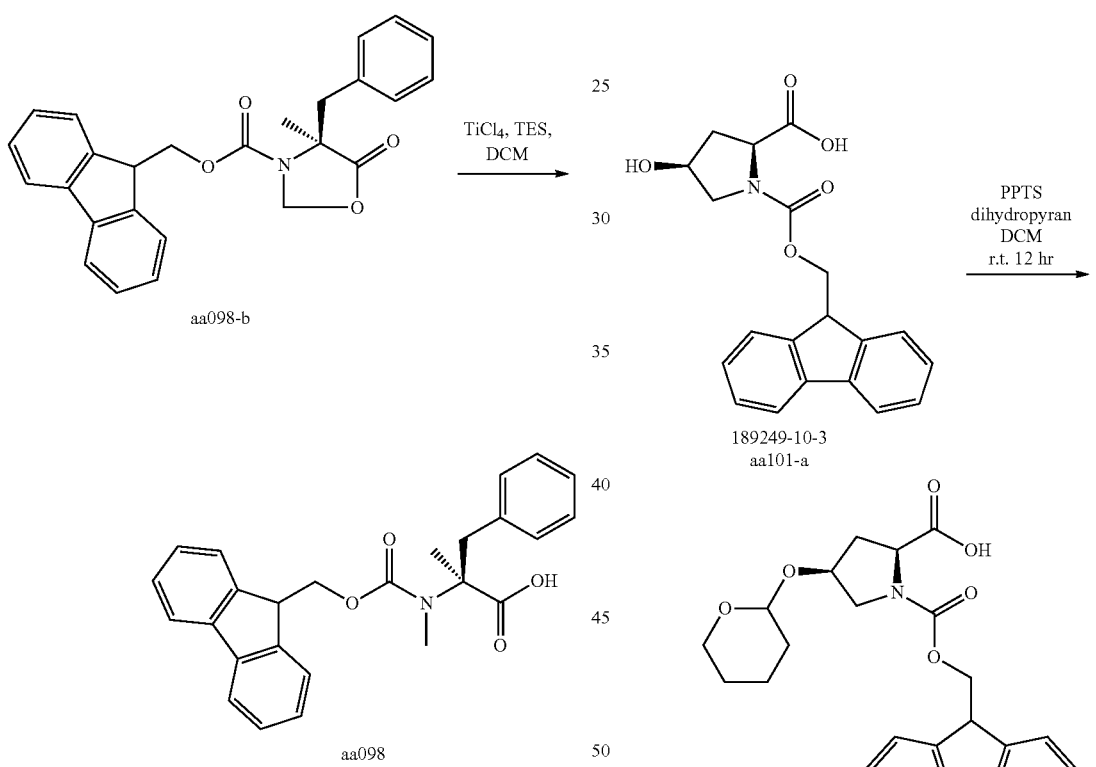

Compound aa098-a ((2S)-2-[9H-fluoren-9-ylmethoxycarbonylamino]-2-methyl-3-phenylpropanoic acid (Fmoc-(Me)Phe-OH)) (2 g, 4.98 mmol) was suspended in toluene (16.61 mL), paraformaldehyde (0.449 g, 14.95 mmol) and (1S)-(+)-10-camphorsulfonic acid (0.058 g, 0.249 mmol) were added thereto, and the mixture was then stirred at 85° C. for four hours. The reaction solution was cooled to room temperature and then diluted with ethyl acetate. The organic layer was washed with a 5% aqueous sodium carbonate solution and an 18% aqueous sodium chloride solution, then dried over anhydrous sodium sulfate, filtered, and then concentrated under reduced pressure to give Compound aa098-b (2.07 g, 100%).

LCMS (ESI) m/z=414 (M+H)+

Retention time: 1.01 min (analysis condition SQDFA05)

Compound aa098-b (520 mg, 1.258 mmol) was dissolved in dichloromethane (6.3 mL), triethylsilane (1.202 mL, 7.55 mmol) and a 1 M solution of titanium tetrachloride in dichloromethane (2.515 mL) were added, after which the mixture was stirred at 0° C. for one hour and then stirred at room temperature for one hour. To the reaction solution was added water, the mixture was filtered by a phase separator, and the filtrate was concentrated under reduced pressure. The resulting residue was purified by reverse phase column chromatography (0.1% formic acid-water/0.1% formic acid-acetonitrile) to give Compound aa098 ((2S)-2-[9H-fluoren-9-ylmethoxycarbonyl(methyl)amino]-2-methyl-3-phenylpropanoic acid, Fmoc-Me(Me)Phe-OH) (357 mg, 68%).

LCMS (ESI) m/z=416 (M+H)+

Retention time: 0.91 min (analysis condition SQDFA05)

Synthesis of Compound aa101, (2S,4S)-1-(9H-fluoren-9-ylmethoxycarbonyl)-4-(oxan-2-yloxy)pyrrolidine-2-carboxylic acid (Fmoc-cisHyp(THP)-OH)

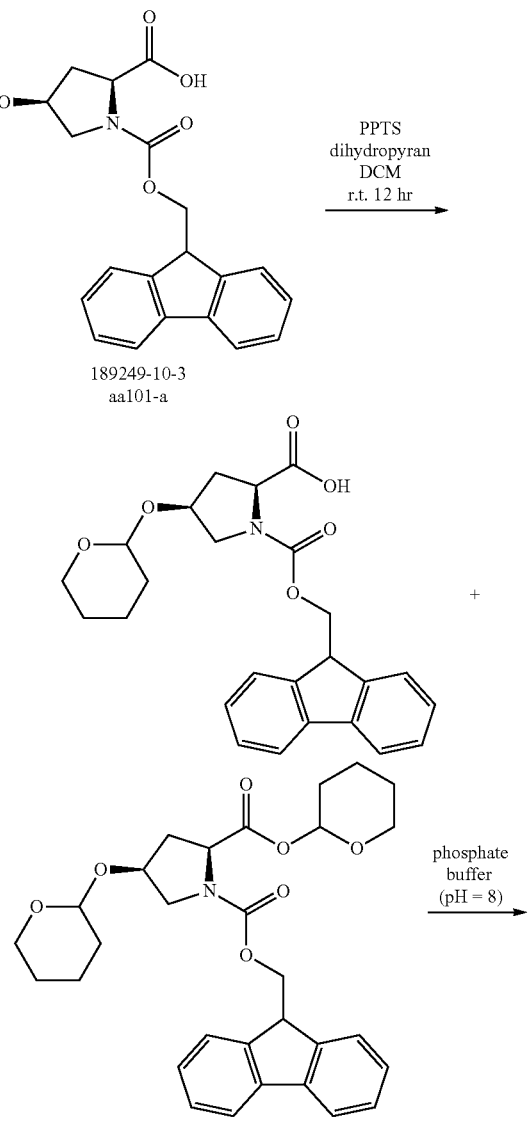

553
-continued

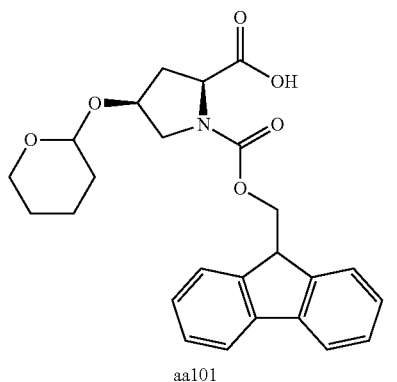

aa101

To a solution of Compound aa101-a ((2S,4S)-1-(9H-fluoren-9-ylmethoxycarbonyl)-4-hydroxypyrrolidine-2-carboxylic acid, Fmoc-cisHyp-OH) (4.18 g, 11.83 mmol) in dichloromethane (42 mL) were added 3,4-dihydropyran (2.24 g, 2.25 equivalents) and PPTS (0.3 g, 0.1 equivalents), and the mixture was stirred at room temperature for 12 hours. Water was added to the reaction solution, which was then extracted with dichloromethane. The resulting organic layer was washed with water and brine. The solvent was evaporated under reduced pressure and the resulting residue was dissolved in THF (35 mL), after which 1.0 M phosphate buffer (pH=8.0, 35 mL) was added and the mixture was stirred at 50° C. for 4 hours and 30 minutes. To the reaction solution was added ethyl acetate (35 mL), after which the organic layer and the aqueous layer were separated and the aqueous layer was extracted with ethyl acetate. The combined organic layers were washed with brine, dried over sodium sulfate, and filtered, and the solvent was then evaporated under reduced pressure. The resulting residue was dissolved in diethyl ether (50 mL), heptane (50 mL) was added, and the diethyl ether was evaporated under reduced pressure. The resulting solid was filtered to give Compound aa101 sodium salt (4.97 g). The obtained Compound aa101 sodium salt was dissolved in ethyl acetate (90 mL), a 0.05 M aqueous phosphoric acid solution (pH 2.1, 150 mL) was then added, and the mixture was stirred at room temperature for five minutes. The organic layer and the aqueous layer were separated, the aqueous layer was then extracted with ethyl acetate (90 mL), and the combined organic layers were washed with brine twice and dried over sodium sulfate. The resulting organic layer was filtered, and the solvent was then evaporated under reduced pressure to give Compound aa101 ((2S,4S)-1-(9H-fluoren-9-ylmethoxycarbonyl)-4-(oxan-2-yloxy)pyrrolidine-2-carboxylic acid, Fmoc-cisHyp(THP)-OH) (4.57 g, yield: 80%).

LCMS (ESI) m/z=460 (M+Na)+

Retention time: 0.81 min (analysis condition SQDFA05)

554

Synthesis of Compound aa102, (2S,4R)-1-(9H-fluoren-9-ylmethoxycarbonyl)-4-(oxan-2-yloxy)pyrrolidine-2-carboxylic acid (Fmoc-Hyp(THP)-OH)

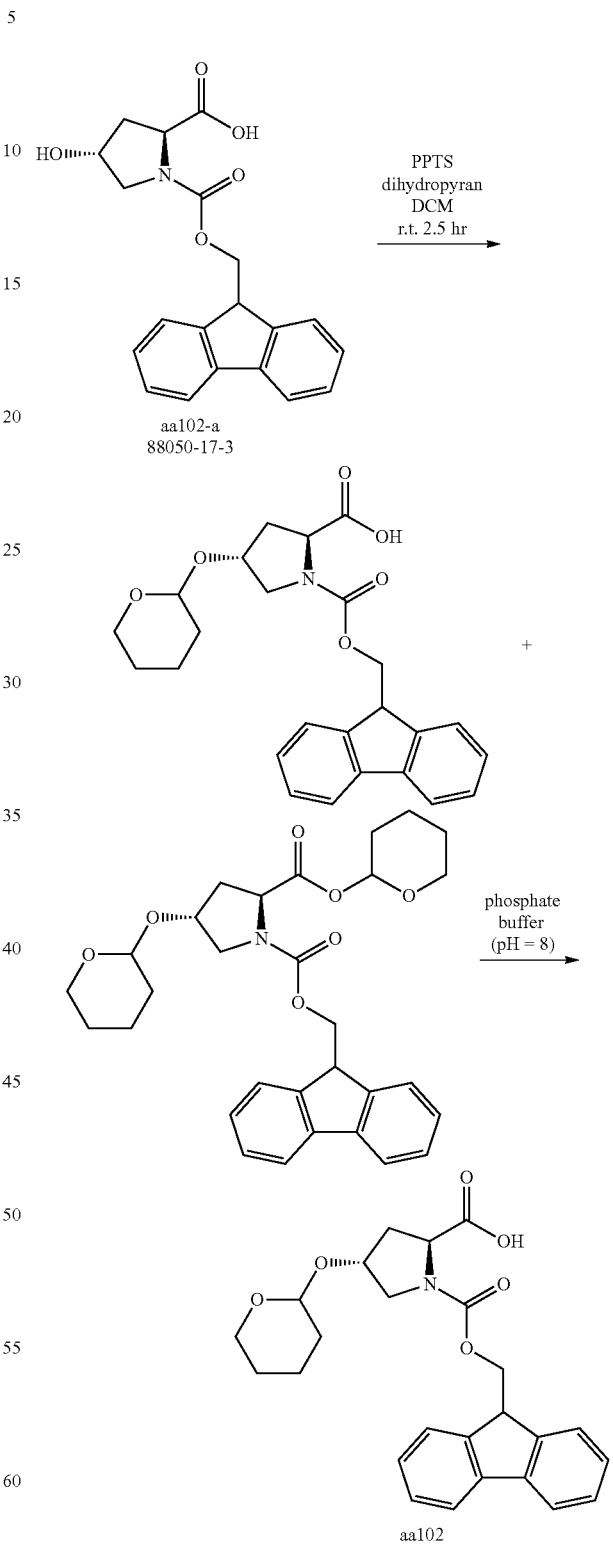

Compound aa102 ((2S,4R)-1-(9H-fluoren-9-ylmethoxycarbonyl)-4-(oxan-2-yloxy)pyrrolidine-2-carboxylic acid, Fmoc-Hyp(THP)-OH) (5.15 g, 83%) was obtained by the same method as in the synthesis of Compound aa101 using Compound aa102-a ((2S,4R)-1-(9H-fluoren-9-ylmethoxycarbonyl)-4-hydroxypyrrolidine-2-carboxylic acid, Fmoc-Hyp-OH) (5 g, 14.15 mmol) as a starting material.

LCMS (ESI) m/z=438 (M+H)+

Retention time: 0.85 min (analysis condition SQDFA05)

Synthesis of Compound aa104, (2S)-3-(3-chloro-5-iodophenyl)-2-(9H-fluoren-9-ylmethoxycarbonylamino)propanoic acid (Fmoc-Phe(3-I-5-Cl)—OH)

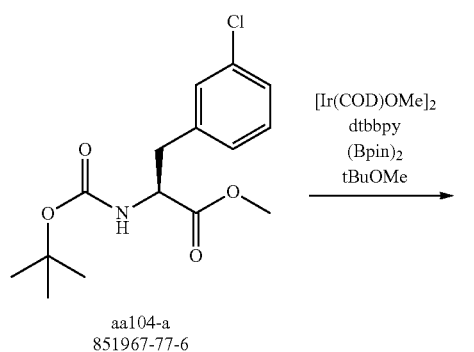

aa104-a
851967-77-6

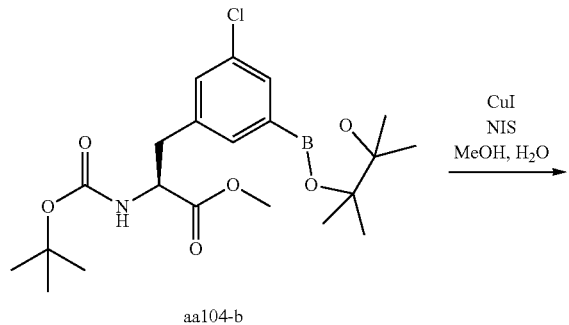

aa104-b

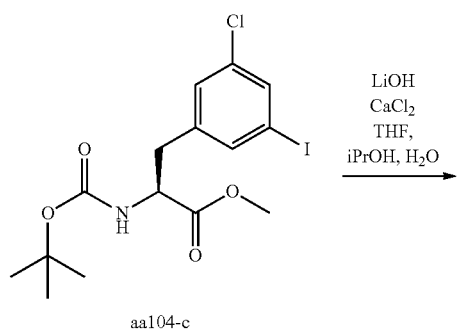

aa104-c

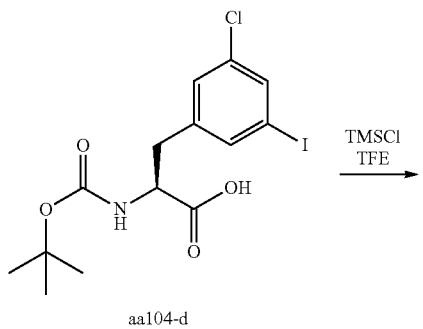

aa104-d

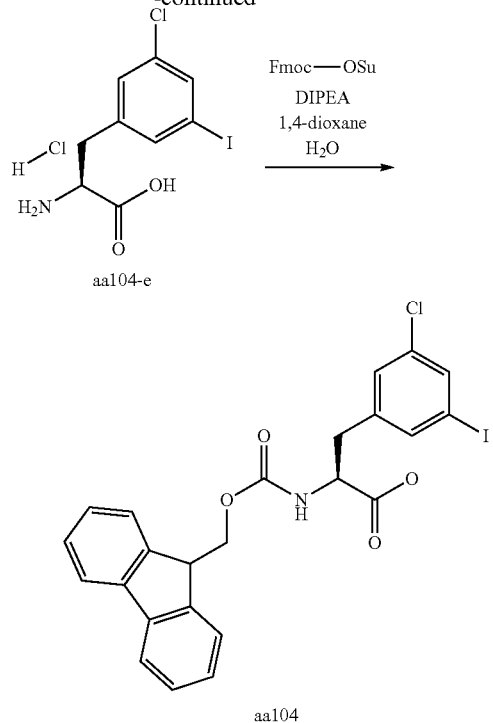

aa104-e aa104

Compound aa104-a (methyl (2S)-3-(3-chlorophenyl)-2-[(2-methylpropan-2-yl)oxycarbonylamino]propanoate) (1.05 g, 3.35 mmol) was dissolved in tert-butyl methyl ether (16.73 ml), bis(pinacolato)diboron (2.55 g, 10.04 mmol), (1,5-cyclooctadiene)(methoxy)iridium(I) dimer (0.111 g, 0.167 mmol), and 4,4'-di-tert-butyl-2,2'-bipyridine (0.090 g, 0.335 mmol) were added, and the mixture was stirred at room temperature overnight. The solvent was evaporated from the reaction solution under reduced pressure, and the resulting residue was purified by reverse phase chromatography (acetonitrile with 0.1% formic acid/distilled water with 0.1% formic acid) to give Compound aa104-b (0.920 g, 63%).

Retention time: 1.06 min (analysis condition SQDFA05)

$^1$H-NMR (varian ascend 400, 400 MHz, CDCl$_3$) δ 7.65-7.61 (m, 1H), 7.43 (bs, 1H), 7.21-7.20 (m, 1H), 5.01-4.98 (m, 1H), 4.55-4.54 (m, 1H), 3.74-3.73 (m, 3H), 3.14-3.10 (m, 1H), 3.02-2.97 (m, 1H), 1.43-1.41 (m, 12H), 1.34 (s, 9H)

Compound aa104-b (0.900 g, 2.047 mmol) was dissolved in a mixed solution of methanol (18.61 ml) and water (1.861 ml), copper(I) iodide (0.585 g, 3.07 mmol) and N-iodosuccinimide (0.691 g, 3.07 mmol) were added, and the mixture was stirred at 80° C. for two hours. The reaction solution was cooled to room temperature and then filtered through celite, and the solvent was evaporated from the resulting filtrate under reduced pressure. The concentrated residue was purified by reverse phase chromatography (acetonitrile with 0.1% formic acid/distilled water with 0.1% formic acid) to give Compound aa104-c (0.703 g, 78%).

LCMS (ESI) m/z=439.9 (M+H)+

Retention time: 0.98 min (analysis condition SQDFA05)

Calcium chloride (2.65 g, 23.88 mmol) was suspended in water (6.63 ml), lithium hydroxide monohydrate (0.267 g, 6.37 mmol) was added, and the mixture was stirred for five minutes. Isopropanol (26.5 ml), and a solution of Compound aa104-c (0.700 g, 1.592 mmol) in tetrahydrofuran (6.63 ml) were sequentially added, and the mixture was stirred at room temperature for four hours. A 20% aqueous formic acid solution was added until the pH of the reaction solution became about 3, and the reaction solution was extracted with tert-butyl methyl ether. The organic layer was washed with a saturated aqueous sodium chloride solution and dried over anhydrous sodium sulfate, and the solvent was evaporated under reduced pressure to give Compound aa104-d (679 mg, 1.595 mmol). This was mixed with another lot synthesized in the same manner, and the next reaction was performed.

LCMS (ESI) m/z=424 (M−H)−

Retention time: 0.86 min (analysis condition SQDFA05)

Compound aa104-d (1.09 g, 2.56 mmol) was dissolved in TFE (12.8 mL), TMSCl (0.485 mL, 3.84 mmol) was added, and the mixture was stirred at room temperature for one hour. The solvent was evaporated from the reaction solution under reduced pressure to give Compound aa104-e as a crude product (997 mg).

LCMS (ESI) m/z=326 (M+H)+

Retention time: 0.43 min (analysis condition SQDFA05)

Compound aa104-e (925 mg, 2.56 mmol) was suspended in water (10 ml), after which diisopropylethylamine (2.003 ml, 11.50 mmol), 1,4-dioxane (13.33 ml), and N-(9-fluorenylmethoxycarbonyloxy)succinimide (862 mg, 2.56 mmol) were sequentially added and the mixture was stirred at room temperature for one hour. To the reaction solution was added a 20% aqueous formic acid solution, and the 1,4-dioxane was evaporated under reduced pressure. Ethyl acetate was added to the concentrate, and the organic layer was extracted. The organic layer was washed with a saturated aqueous sodium chloride solution and dried over anhydrous sodium sulfate, and the solvent was evaporated under reduced pressure. The resulting residue was suspended in tert-butyl methyl ether/n-hexane (1/1) and separated by filtration to give Compound aa104 ((2S)-3-(3-chloro-5-iodophenyl)-2-(9H-fluoren-9-ylmethoxycarbonylamino)propanoic acid, Fmoc-Phe(3-I-5-Cl)—OH) (970 mg, 69%).

LCMS (ESI) m/z=570 (M+Na)+

Retention time: 0.99 min (analysis condition SQDFA05)

Synthesis of Compound aa105, (2S)-2-(9H-fluoren-9-ylmethoxycarbonylamino)-3-(2-fluoro-3-iodophenyl)propanoic acid (Fmoc-Phe(2-F-3-I)—OH)

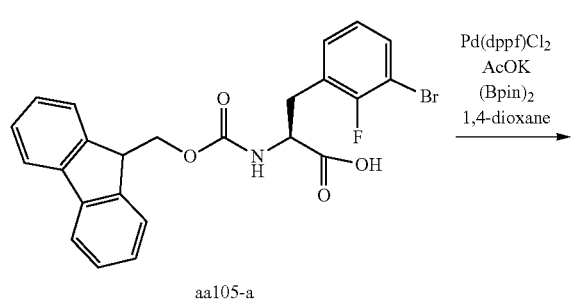

aa105-a

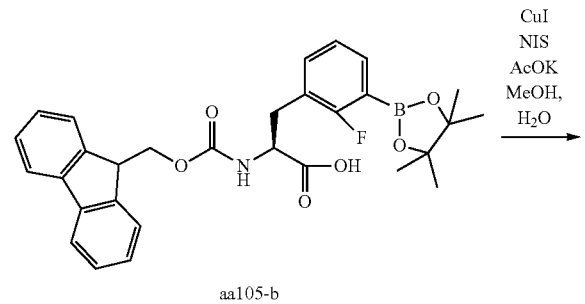

aa105-b

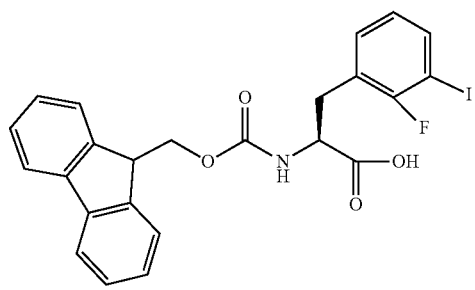

aa105

Compound aa105-a ((2S)-3-(3-bromo-2-fluorophenyl)-2-(9H-fluoren-9-ylmethoxycarbonylamino)propanoic acid, Fmoc-Phe(2-F-3-Br)—OH) (0.7 g, 1.445 mmol) was dissolved in 1,4-dioxane (14.5 mL), bis(pinacolato)diboron (1.468 g, 5.78 mmol), potassium acetate (0.397 g, 4.05 mmol), and [1,1-bis(diphenylphosphino)ferrocene]dichloropalladium(II) (0.212 g, 0.289 mmol) were added at room temperature, and the mixture was stirred at 80° C. for 5.5 hours. After 5.5 hours, bis(pinacolato)diboron (0.147 g, 0.578 mmol), potassium acetate (0.040 g, 0.405 mmol), and [1,1-bis(diphenylphosphino)ferrocene]dichloropalladium (II) (0.021 g, 0.029 mmol) were further added at room temperature, and the mixture was stirred at 80° C. for 1.5 hours. The reaction solution was filtered through celite, after which the mother liquor was concentrated under reduced pressure and the 1,4-dioxane was evaporated to give Compound aa105-b as a crude product. This was mixed with two lots synthesized in the same manner and was used for the next reaction.

The obtained Compound aa105-b (1.15 g, 2.17 mmol) was dissolved in a mixed solvent of methanol (9.75 mL) and water (1.08 mL), potassium acetate (0.425 g, 4.34 mmol), copper(I) iodide (1.16 g, 6.07 mmol), and N-iodosuccinimide (3.41 g, 15.17 mmol) were added at 0° C., and the mixture was stirred at 80° C. for two hours. Another reaction on the same scale was performed, two batches of the reaction solution were mixed and concentrated under reduced pressure to evaporate the methanol. The resulting residue was dissolved in ethyl acetate (80 mL), washed with a 7.7 to 8.3% aqueous ammonia solution (40 mL) three times, washed with a 1 M aqueous phosphoric acid solution (40 mL), and washed with a saturated sodium chloride aqueous solution (40 mL). The organic layer was dried over anhydrous sodium sulfate, filtered, and then concentrated under reduced pressure. The resulting residue was purified by reverse phase column chromatography (acetonitrile with 0.1% formic acid/distilled water with 0.1% formic acid) to give Compound aa105 ((2S)-2-(9H-fluoren-9-ylmethoxycarbonylamino)-3-(2-fluoro-3-iodophenyl)propanoic acid, Fmoc-Phe(2-F-3-I)—OH) (1.55 g, 88%).

LCMS (ESI) m/z=530 (M−H)−

Retention time: 0.90 min (analysis condition SQDFA05)

Synthesis of Compound aa106, (2S)-2-(9H-fluoren-9-ylmethoxycarbonylamino)-3-(3-fluoro-5-iodophenyl)propanoic acid (Fmoc-Phe(3-I-5-F)—OH)

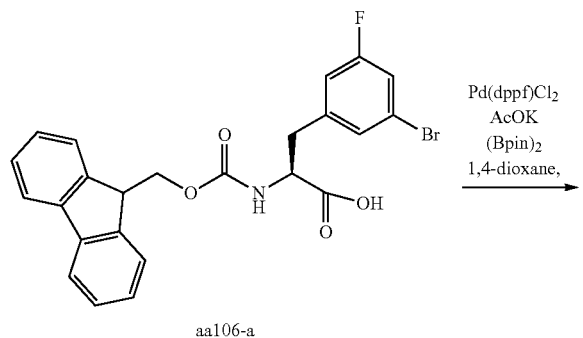

aa106-a

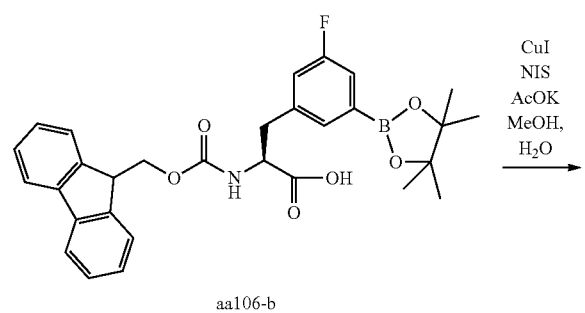

aa106-b

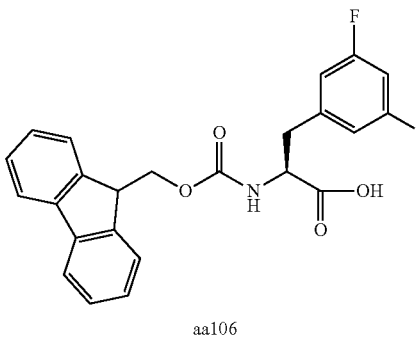

aa106

Compound aa106-b was obtained as a crude product by the same method as in the synthesis of Compound aa105-b using Compound aa106-a ((2S)-3-(3-bromo-5-fluorophenyl)-2-(9H-fluoren-9-ylmethoxycarbonylamino)propanoic acid, Fmoc-Phe(3-Br-5-F)—OH) (2.1 g, 4.335 mmol) as a starting material.

Compound aa106 ((2S)-2-(9H-fluoren-9-ylmethoxycarbonylamino)-3-(3-fluoro-5-iodophenyl)propanoic acid, Fmoc-Phe(3-I-5-F)—OH) (1.54 g, 67%) was obtained by the same method as in the synthesis of Compound aa105 using Compound aa106-b (1.152 g, 2.17 mmol).

LCMS (ESI) m/z=530 (M−H)−

Retention time: 0.97 min (analysis condition SQDFA05)

Synthesis of Compound aa109, (2S)-2-[ethyl(9H-fluoren-9-ylmethoxycarbonyl)amino]propanoic acid (Fmoc-EtAla-OH)

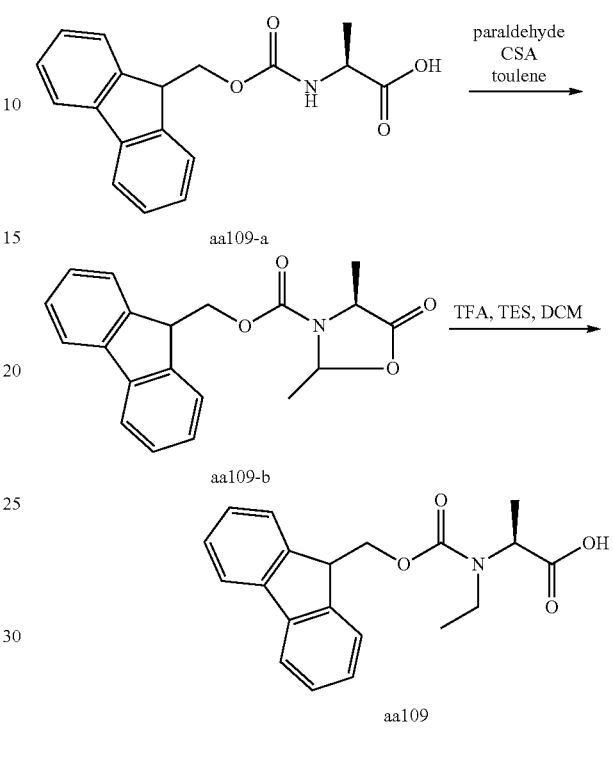

Compound aa109-a ((2S)-2-(9H-fluoren-9-ylmethoxycarbonylamino)propanoic acid, Fmoc-Ala-OH) (30 g, 96 mmol) was dissolved in toluene (321 mL), paraldehyde (19.10 mL, 145 mmol) and CSA (2.24 g, 9.64 mmol) were added, and the mixture was stirred at 80° C. for three hours. The reaction solution was cooled to room temperature, n-hexane (300 mL) and ethyl acetate (600 mL) were added, and the organic layer was washed with a saturated aqueous sodium bicarbonate solution and brine and dried over anhydrous sodium sulfate, after which the solvent was evaporated under reduced pressure. The resulting concentrate was dissolved in 20% ethyl acetate-hexane (400 mL) again, washed with a saturated aqueous sodium bicarbonate solution and brine, and dried over anhydrous sodium sulfate, and the solvent was then evaporated under reduced pressure to give Compound aa109-b (22.07 g, 68%) as a crude product.

LCMS (ESI) m/z=338 (M+H)+

Retention time: 0.90 min (analysis condition SQDFA05)

The obtained Compound aa109-b (22.04 g, 65.3 mmol) was dissolved in DCM (218 mL), TFA (150 mL, 1960 mmol) and triethylsilane (104 mL, 653 mmol) were added, and the mixture was stirred at room temperature for two hours. After concentration under reduced pressure, the concentrate was dissolved in DCM. The solution was concentrated under reduced pressure to a volume of about 200 mL, hexane (500 mL) was added, resulting in precipitation of the target compound. The target compound was collected by filtration to give Compound aa109 ((2S)-2-[ethyl(9H-fluoren-9-ylmethoxycarbonyl)amino]propanoic acid, Fmoc-EtAla-OH) (13.41 g, 61%).

LCMS (ESI) m/z=340 (M+H)+

Retention time: 0.81 min (analysis condition SQDFA05)

Synthesis of Compound aa110, (2S)-3-(4-chlorophenyl)-2-[ethyl(9H-fluoren-9-ylmethoxycarbonyl)amino]propanoic acid (Fmoc-EtPhe(4-Cl)—OH)

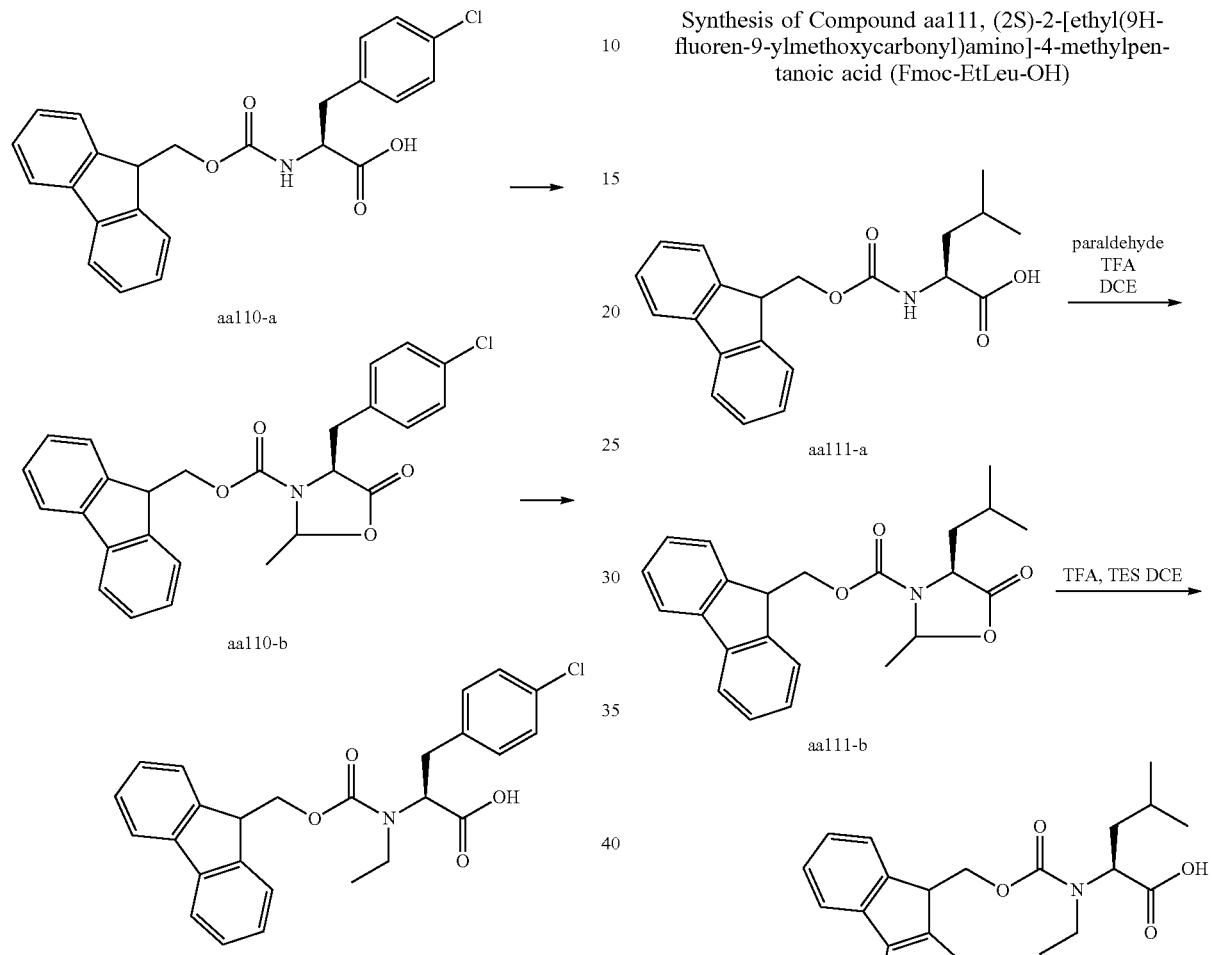

Compound aa110-a ((2S)-3-(4-chlorophenyl)-2-(9H-fluoren-9-ylmethoxycarbonylamino)propanoic acid, Fmoc-Phe(4-Cl)—OH) (3.00 g, 7.11 mmol) was dissolved in toluene (17.8 mL), paraldehyde (0.940 mL, 7.11 mmol) and CSA (0.165 g, 0.711 mmol) were added, and the mixture was stirred at 80° C. overnight. The reaction solution was cooled to room temperature, dissolved in 20% ethyl acetate-hexane (300 mL), washed twice with a saturated aqueous sodium bicarbonate solution and once with brine, and dried over anhydrous sodium sulfate, and the solvent was then evaporated under reduced pressure to give Compound aa110-b (2.63 g, 83%) as a crude product.

LCMS (ESI) m/z=448 (M+H)+

Retention time: 1.06 min (analysis condition SQDFA05)

The obtained Compound aa110-b (2.6 g, 5.8 mmol) was dissolved in DCE (19.35 mL), TFA (13.33 mL, 174 mmol) and triethylsilane (9.25 mL, 58.0 mmol) were added, and the mixture was stirred at 60° C. for six hours and then stirred at room temperature overnight. The crude product obtained by concentration under reduced pressure was purified by reverse phase column chromatography (acetonitrile with 0.1% formic acid/distilled water with 0.1% formic acid) to give Compound aa110 ((2S)-3-(4-chlorophenyl)-2-[ethyl(9H-fluoren-9-ylmethoxycarbonyl)amino]propanoic acid, Fmoc-EtPhe(4-Cl)—OH) (1.46 g, 56%).

LCMS (ESI) m/z=450 (M+H)+

Retention time: 0.98 min (analysis condition SQDFA05)

Synthesis of Compound aa111, (2S)-2-[ethyl(9H-fluoren-9-ylmethoxycarbonyl)amino]-4-methylpentanoic acid (Fmoc-EtLeu-OH)

Compound aa111-a ((2S)-2-(9H-fluoren-9-ylmethoxycarbonylamino)-4-methylpentanoic acid, Fmoc-Leu-OH) (4.95 g, 14.0 mmol, CAS No. 35661-60-0) was suspended in DCE (17.5 mL) under a nitrogen atmosphere, paraldehyde (5.61 mL, 42.0 mmol) and TFA (9.65 mL, 126 mmol) were added, and the mixture was stirred at 50° C. for six hours. The reaction mixture was cooled to room temperature and concentrated under reduced pressure, and the resulting residue was then dissolved in ethyl acetate (40 mL). The organic layer was washed with a saturated aqueous sodium bicarbonate solution (40 mL) and brine (40 mL) and dried over anhydrous sodium sulfate, and the solvent was evaporated under reduced pressure to give Compound aa111-b as a crude product.

LCMS (ESI) m/z=380 (M+H)+

Retention time: 1.02 min (analysis condition SQDFA05)

The total amount of Compound aa111-b obtained above was dissolved in DCE (35 mL), TFA (28.9 mL, 378 mmol)

and triethylsilane (20.1 mL, 126 mmol) were added, and the mixture was stirred at 60° C. for 90 minutes. The reaction solution was cooled to room temperature, concentrated under reduced pressure, and then azeotropically distilled with toluene three times. The resulting residue was purified by reverse phase column chromatography (acetonitrile with 0.1% formic acid/distilled water with 0.1% formic acid) to give Compound aa111 ((2S)-2-[ethyl(9H-fluoren-9-yl-methoxycarbonyl)amino]-4-methylpentanoic acid, Fmoc-EtLeu-OH) (3.15 g, 59% through two steps).

LCMS (ESI) m/z=382 (M+H)+
Retention time: 0.94 min (analysis condition SQDFA05)

Synthesis of Compound aa112, (2S)-3-cyclohexyl-2-[ethyl(9H-fluoren-9-ylmethoxycarbonyl)amino]propanoic acid (Fmoc-EtCha-OH)

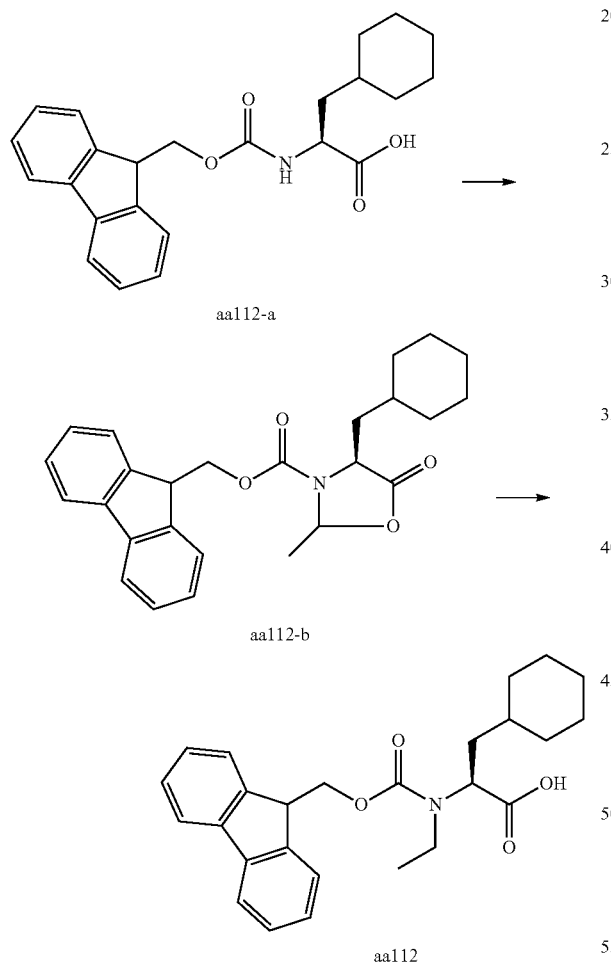

Compound aa112-b was obtained as a crude product by the same method as in the synthesis of Compound aa111-b using Compound aa112-a ((2S)-3-cyclohexyl-2-(9H-fluoren-9-ylmethoxycarbonylamino)propanoic acid, Fmoc-Cha-OH) (5.51 g, 14.0 mmol, CAS No. 135673-97-1) as a starting material.

LCMS (ESI) m/z=420 (M+H)+
Retention time: 1.12 min (analysis condition SQDFA05)
Compound aa112 ((2S)-3-cyclohexyl-2-[ethyl(9H-fluoren-9-ylmethoxycarbonyl)amino]propanoic acid, Fmoc-Et-Cha-OH) (4.78 g, 81% through two steps) was obtained by the same method as in the synthesis of Compound aa111 using the total amount of Compound aa112-b obtained above.

LCMS (ESI) m/z=422 (M+H)+
Retention time: 1.04 min (analysis condition SQDFA05)

Synthesis of Compound aa113, (2S)-2-[ethyl(9H-fluoren-9-ylmethoxycarbonyl)amino]-3-(4-methylphenyl)propanoic acid (Fmoc-EtPhe(4-Me)-OH)

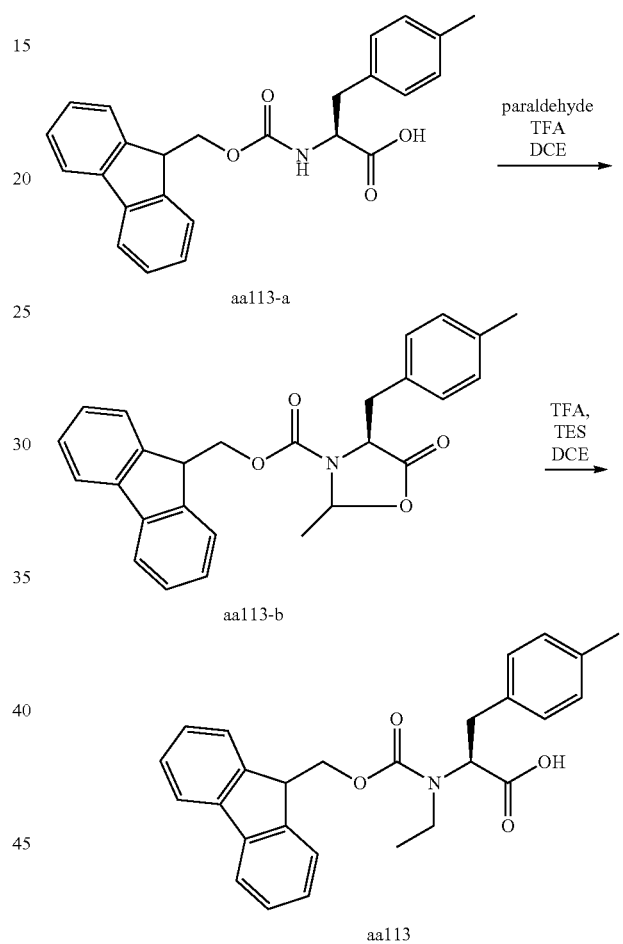

Compound aa113-a ((2S)-2-(9H-fluoren-9-ylmethoxycarbonylamino)-3-(4-methylphenyl)propanoic acid, Fmoc-Phe(4-Me)-OH) (5.62 g, 14.0 mmol, CAS No. 199006-54-7) was suspended in dichloroethane (DCE) (17.5 mL) under a nitrogen atmosphere, paraldehyde (5.61 mL, 42.0 mmol) and trifluoroacetic acid (TFA) (9.65 mL, 126 mmol) were added, and the mixture was stirred at 60° C. for six hours. The resulting reaction solution containing Compound aa113-b was used as such for the next step.

LCMS (ESI) m/z=428 (M+H)+
Retention time: 1.03 min (analysis condition SQDFA05)
To the resulting reaction solution of Compound aa113-b were added dichloroethane (DCE) (17.5 mL), trifluoroacetic acid (TFA) (19.3 mL, 252 mmol), and triethylsilane (TES) (20.1 mL, 126 mmol), and the mixture was stirred at 60° C. for 17 hours. The reaction mixture was cooled to room temperature and concentrated under reduced pressure, and the resulting residue was then dissolved in ethyl acetate (40 mL). The organic layer was washed with a saturated aqueous sodium bicarbonate solution (40 mL) and brine (40 mL) and dried over anhydrous sodium sulfate, and the solvent was evaporated under reduced pressure. The resulting residue was dissolved in acetonitrile (30 mL) and washed with hexane (15 mL) twice, and the solvent was evaporated under reduced pressure. The resulting residue was purified by reverse phase column chromatography (acetonitrile with 0.1% formic acid/distilled water with 0.1% formic acid) to give Compound aa113 ((2S)-2-[ethyl(9H-fluoren-9-ylmethoxycarbonyl)amino]-3-(4-methylphenyl)propanoic acid, Fmoc-EtPhe(4-Me)-OH) (4.4 g, 73% through two steps).

LCMS (ESI) m/z=430 (M+H)+

Retention time: 0.95 min (analysis condition SQDFA05)

Synthesis of Compound aa114, (2S)-2-[ethyl(9H-fluoren-9-ylmethoxycarbonyl)amino]-3-[4-(trifluoromethyl)phenyl]propanoic acid (Fmoc-EtPhe(4-CF3)-OH)

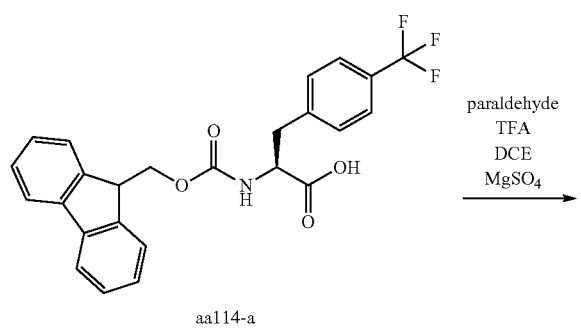

aa114-a

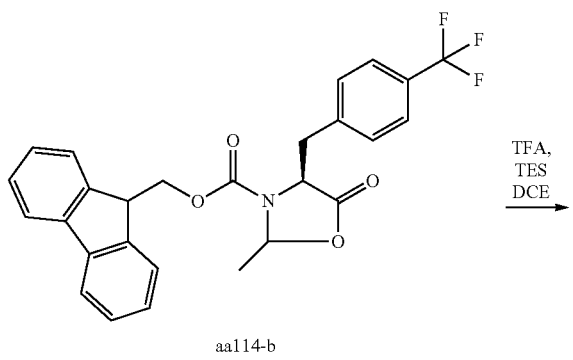

aa114-b

Compound aa114-a ((2S)-2-(9H-fluoren-9-ylmethoxycarbonylamino)-3-[4-(trifluoromethyl)phenyl]propanoic acid, Fmoc-Phe(4-CF3)-OH) (4.04 g, 8.87 mmol, CAS No. 247113-86-6) was suspended in DCE (11.1 mL) under a nitrogen atmosphere, anhydrous magnesium sulfate (4.27 g, 35.4 mmol), paraldehyde (3.55 mL, 26.6 mmol), and trifluoroacetic acid (TFA) (6.11 mL, 80 mmol) were added, and the mixture was stirred at 60° C. for three hours. Anhydrous magnesium sulfate (2.14 g, 17.7 mmol) was further added and the mixture was stirred at 60° C. for one hour. The resulting reaction solution containing Compound aa114-b was used as such for the next reaction.

LCMS (ESI) m/z=482 (M+H)+

Retention time: 1.04 min (analysis condition SQDFA05)

To the resulting reaction solution containing Compound aa114-b were added DCE (11.1 mL), TFA (12.2 mL, 159 mmol), and triethylsilane (12.7 mL, 80 mmol), and the mixture was stirred at 60° C. for 10 hours. The reaction solution was cooled to room temperature, the magnesium sulfate was filtered off, and the filtrate was then concentrated under reduced pressure. Because the intended reaction was not completed, the resulting residue was dissolved in DCE (22.2 mL), TFA (18.3 mL, 239 mmol) and triethylsilane (12.7 mL, 80 mmol) were added, and the mixture was stirred at 60° C. for eight hours. The reaction mixture was cooled to room temperature and concentrated under reduced pressure, and the resulting residue was then dissolved in ethyl acetate (40 mL). The organic layer was washed with a saturated aqueous sodium bicarbonate solution (40 mL) and brine (40 mL) and dried over anhydrous sodium sulfate, and the solvent was evaporated under reduced pressure. The resulting residue was dissolved in acetonitrile (30 mL) and washed with hexane (15 mL) twice, and the solvent was evaporated under reduced pressure. The resulting residue was purified by reverse phase column chromatography (water-acetonitrile, containing 0.1% formic acid) to give Compound aa114 ((2S)-2-[ethyl(9H-fluoren-9-ylmethoxycarbonyl)amino]-3-[4-(trifluoromethyl)phenyl]propanoic acid, Fmoc-EtPhe(4-CF3)-OH) (1.90 g, 44% through two steps).

LCMS (ESI) m/z=484 (M+H)+

Retention time: 0.97 min (analysis condition SQDFA05)

Synthesis of Compound aa116, (2S)-3-(2,6-difluorophenyl)-2-(9H-fluoren-9-ylmethoxycarbonylamino)propanoic acid (Fmoc-Phe(26-F2)-OH)

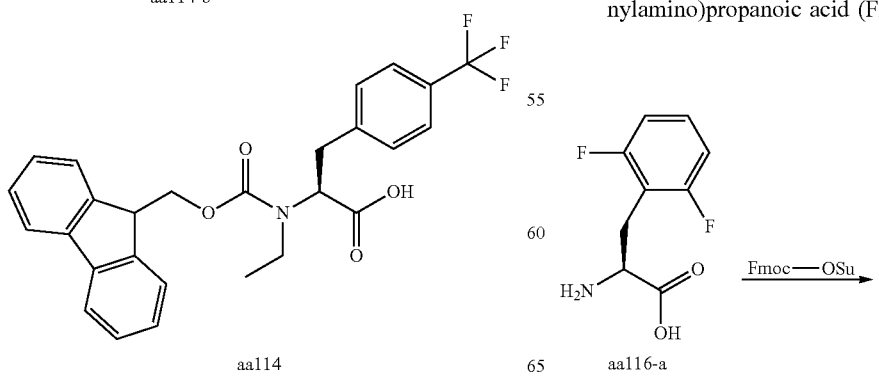

aa114 aa116-a

-continued

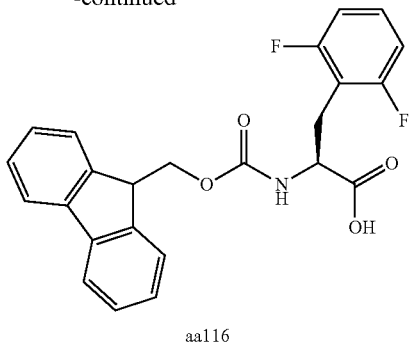

aa116

Compound aa116-a ((2S)-2-amino-3-(2,6-difluorophenyl)propanoic acid, H-Phe(26-F2)-OH) (1.00 g, 4.97 mmol) was dissolved in a mixed solvent of 1,4-dioxane (12 mL) and distilled water (9 mL), diisopropylethylamine (DIPEA) (3.03 ml, 17.4 mmol) and N-(9-fluorenylmethoxycarbonyloxy)succinimide (Fmoc-OSu) (1.761 g, 5.22 mmol) were added, and the mixture was stirred at room temperature for one hour. To the reaction solution were added a 20% aqueous formic acid solution and dimethyl sulfoxide, after which the mixture was concentrated under reduced pressure and the 1,4-dioxane was evaporated. The resulting concentrate was purified by reverse phase chromatography (acetonitrile with 0.1% formic acid/distilled water with 0.1% formic acid) to give Compound aa116 ((2S)-3-(2,6-difluorophenyl)-2-(9H-fluoren-9-ylmethoxycarbonylamino)propanoic acid, Fmoc-Phe(26-F2)-OH) (1.81 g, 86%).

LCMS (ESI) m/z=445.9 (M+Na)+
Retention time: 1.202 min (analysis condition SMD-method_04)

Synthesis of Compound aa118, (2S)-3-(2,5-difluorophenyl)-2-(9H-fluoren-9-ylmethoxycarbonylamino)propanoic acid (Fmoc-Phe(25-F2)-OH)

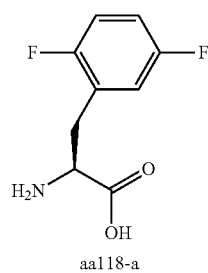

aa118-a

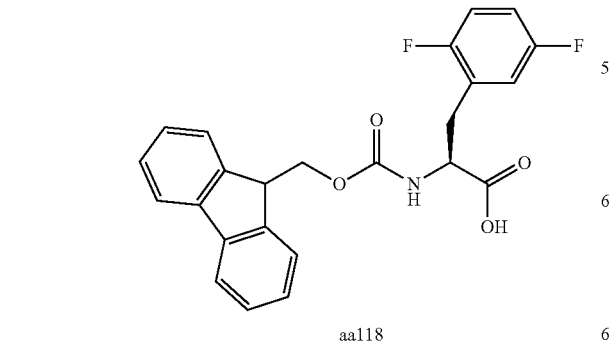

aa118

Compound aa118 ((2S)-3-(2,5-difluorophenyl)-2-(9H-fluoren-9-ylmethoxycarbonylamino)propanoic acid, Fmoc-Phe(25-F2)-OH) (2.43 g, 58%) was obtained by the same method as in the synthesis of Compound aa116 using Compound aa118-a ((2S)-2-amino-3-(2,5-difluorophenyl)propanoic acid, H-Phe(25-F2)-OH)(2 g, 9.94 mmol) as a starting material.

LCMS (ESI) m/z=424 (M+H)+
Retention time: 0.85 min (analysis condition SQDFA05)

Synthesis of Compound aa119, (2S)-2-[9H-fluoren-9-ylmethoxycarbonylamino]-3-(3-iodophenyl)-2-methylpropanoic acid (Fmoc-(Me)Phe(3-I)—OH)

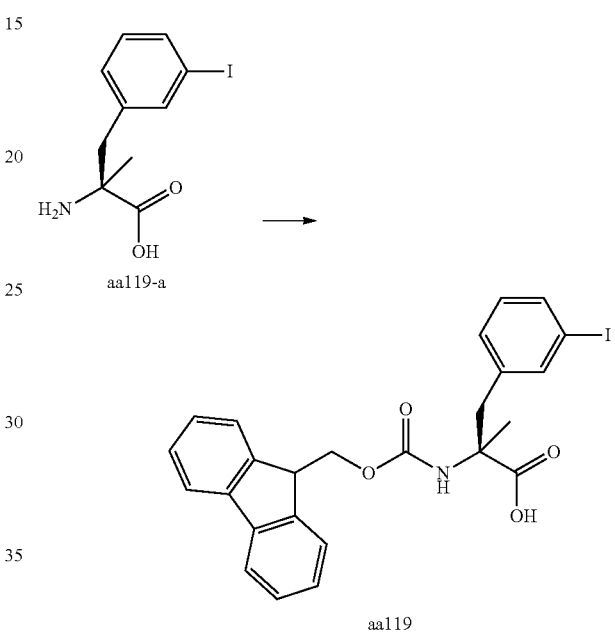

aa119

Compound aa119 ((2S)-2-[9H-fluoren-9-ylmethoxycarbonylamino]-3-(3-iodophenyl)-2-methylpropanoic acid, Fmoc-(Me)Phe(3-I)—OH) (1.1 g, 64%) was obtained by the same method as in the synthesis of Compound aa116 using Compound aa119-a ((2S)-2-amino-3-(3-iodophenyl)-2-methylpropanoic acid, H-(Me)Phe(3-T)-OH) (1 g, 3.28 mmol) as a starting material.

LCMS (ESI) m/z=528 (M+H)+
Retention time: 0.98 minute (analysis condition SQDFA05)

Synthesis of Compound aa120, (2S)-3-(3,5-dichlorophenyl)-2-(9H-fluoren-9-ylmethoxycarbonylamino)propanoic acid (Fmoc-Phe(35-Cl2)-OH)

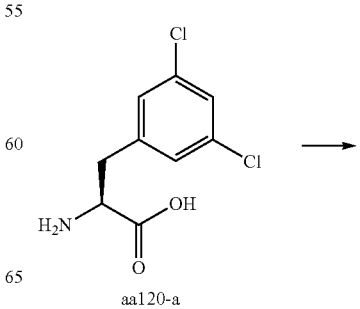

aa120-a

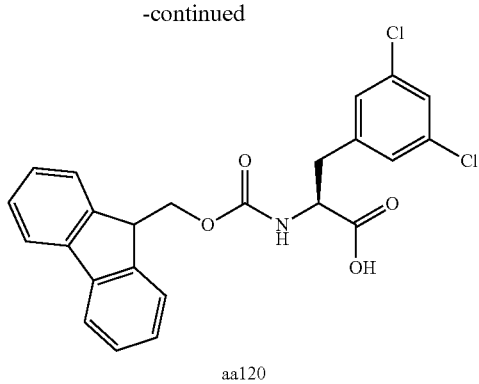

aa120

Compound aa120 ((2S)-3-(3,5-dichlorophenyl)-2-(9H-fluoren-9-ylmethoxycarbonylamino)propanoic acid, Fmoc-Phe(35-Cl2)-OH) (6.2 g, 80%) was obtained by the same method as in the synthesis of Compound aa116 using Compound aa120-a ((2S)-2-amino-3-(3,5-dichlorophenyl)propanoic acid, H-Phe(35-Cl2)-OH) (4 g, 17.09 mmol) as a starting material and using sodium carbonate instead of DIPEA.

LCMS (ESI) m/z=456 (M+H)+
Retention time: 0.94 min (analysis condition SQDFA05)

Synthesis of Compound aa121, (2S)-2-(9H-fluoren-9-ylmethoxycarbonylamino)-3-(2-fluoro-5-iodophenyl)propanoic acid (Fmoc-Phe(2-F-5-I)—OH)

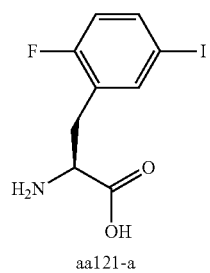

aa121-a

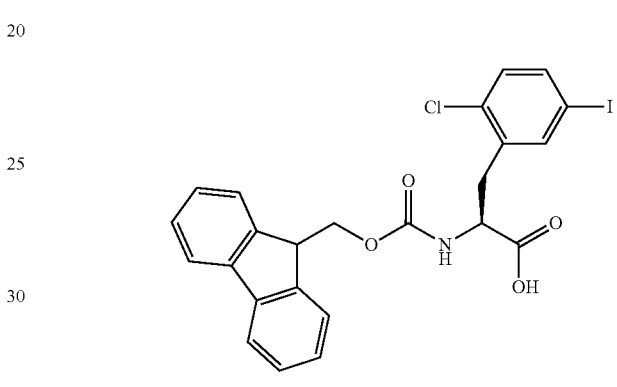

aa121

Compound aa121 ((2S)-2-(9H-fluoren-9-ylmethoxycarbonylamino)-3-(2-fluoro-5-iodophenyl)propanoic acid, Fmoc-Phe(2-F-5-I)—OH) (1.6 g, 92%) by the same method as in the synthesis of Compound aa116 using Compound aa121-a ((2S)-2-amino-3-(2-fluoro-5-iodophenyl)propanoic acid, H-Phe(2-F-5-I)—OH) (1 g, 3.24 mmol) as a starting material.

LCMS (ESI) m/z=532 (M+H)+
Retention time: 0.94 min (analysis condition SQDFA05)

Synthesis of Compound aa122, (2S)-3-(2-chloro-5-iodophenyl)-2-(9H-fluoren-9-ylmethoxycarbonylamino)propanoic acid (Fmoc-Phe(2-Cl-5-I)—OH)

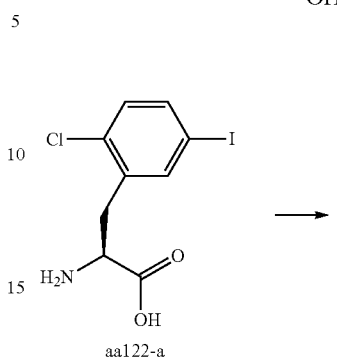

aa122-a

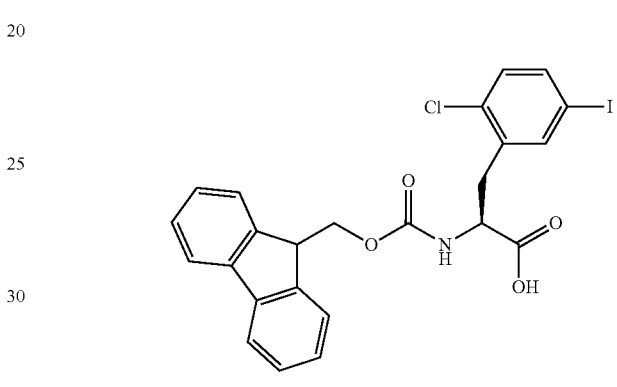

aa122

Compound aa122 ((2S)-3-(2-chloro-5-iodophenyl)-2-(9H-fluoren-9-ylmethoxycarbonylamino)propanoic acid, Fmoc-Phe(2-Cl-5-I)—OH) (0.93 g, 55%) was obtained by the same method as in the synthesis of Compound aa116 using Compound aa122-a ((2S)-2-amino-3-(2-chloro-5-iodophenyl)propanoic acid, H-Phe(2-Cl-5-I)—OH) (1 g, 3.07 mmol) as a starting material.

LCMS (ESI) m/z=546 (M−H)−
Retention time: 0.97 min (analysis condition SQDFA05)

Synthesis of Compound aa124, (2S)-3-(5-chlorothiophen-2-yl)-2-(9H-fluoren-9-ylmethoxycarbonylamino)propanoic acid (Fmoc-Ala(2-Thie-5-Cl)—OH)

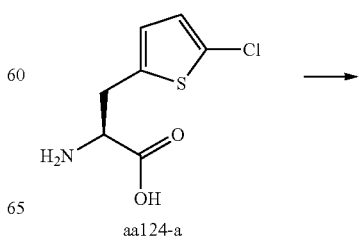

aa124-a

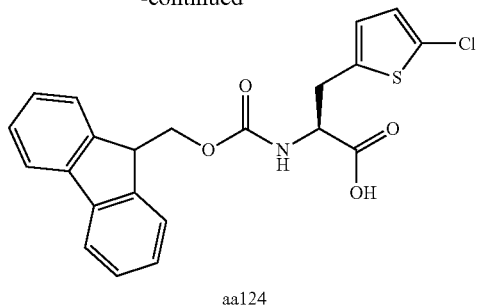

aa124

Compound aa124 ((2S)-3-(5-chlorothiophen-2-yl)-2-(9H-fluoren-9-ylmethoxycarbonylamino)propanoic acid, Fmoc-Ala(2-Thie-5-Cl)—OH) (0.87 g, 84%) was obtained by the same method as in the synthesis of Compound aa116 using Compound aa124-a ((2S)-2-amino-3-(5-chlorothiophen-2-yl)propanoic acid, H-Ala(2-Thie-5-Cl)—OH) (0.5 g, 2.431 mmol) as a starting material.

LCMS (ESI) m/z=426 (M−H)−

Retention time: 0.91 min (analysis condition SQDFA05)

Synthesis of Compound aa125, (2S)-3-(5-bromo-thiophen-2-yl)-2-(9H-fluoren-9-ylmethoxycarbo-nylamino)propanoic acid (Fmoc-Ala(2-Thie-5-Br)—OH)

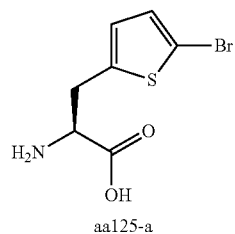

aa125-a

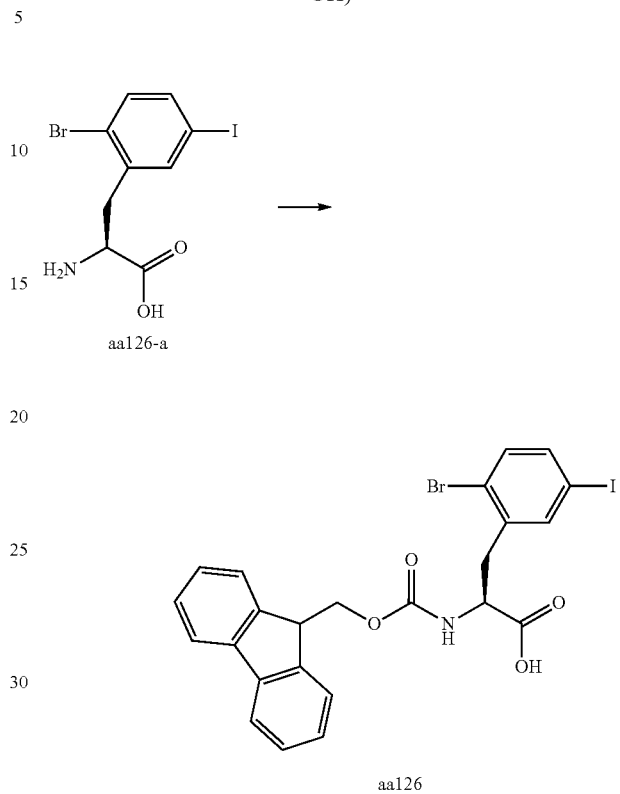

aa125

Compound aa125 ((2S)-3-(5-bromothiophen-2-yl)-2-(9H-fluoren-9-ylmethoxycarbonylamino)propanoic acid, Fmoc-Ala (2-Thie-5-Br)—OH) (0.80 g, 85%) was obtained by the same method as in the synthesis of Compound aa116 using Compound aa125-a ((2S)-2-amino-3-(5-bromothio-phen-2-yl)propanoic acid, H-Ala(2-Thie-5-Br)—OH) (0.5 g, 2 mmol) as a starting material.

LCMS (ESI) m/z=470 (M−H)−

Retention time: 0.91 min (analysis condition SQDFA05)

Synthesis of Compound aa126, (2S)-3-(2-bromo-5-iodophenyl)-2-(9H-fluoren-9-ylmethoxycarbo-nylamino)propanoic acid (Fmoc-Phe(2-Br-5-I)—OH)

aa126-a aa126

Compound aa126 ((2S)-3-(2-bromo-5-iodophenyl)-2-(9H-fluoren-9-ylmethoxycarbonylamino)propanoic acid, Fmoc-Phe(2-Br-5-I)—OH) (0.80 g, 25%) was obtained by the same method as in the synthesis of Compound aa116 using Compound aa126-a ((2S)-2-amino-3-(2-bromo-5-io-dophenyl)propanoic acid, H-Phe(2-Br-5-I)—OH) (2 g, 5.41 mmol) as a starting material.

LCMS (ESI) m/z=590 (M−H)−

Retention time: 0.96 min (analysis condition SQDFA05)

Synthesis of Compound aa127, (2S)-2-(9H-fluoren-9-ylmethoxycarbonylamino)-3-(5-iodo-2-methylphe-nyl)propanoic acid (Fmoc-Phe(2-Me-5-I)—OH)

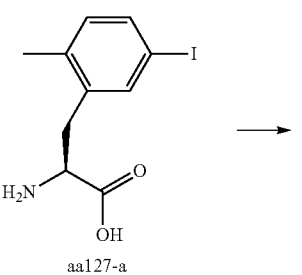

aa127-a

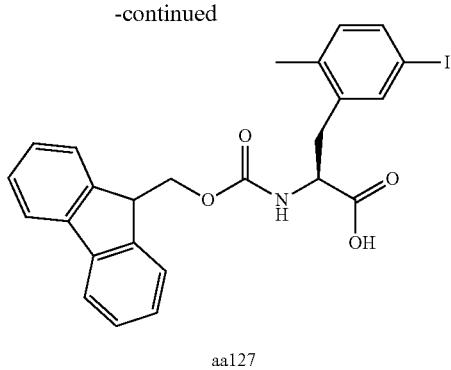

aa127

Compound aa127 ((2S)-2-(9H-fluoren-9-ylmethoxycarbonylamino)-3-(5-iodo-2-methylphenyl)propanoic acid, Fmoc-Phe(2-Me-5-I)—OH) (2.87 g, quant.) was obtained by the same method as in the synthesis of Compound aa116 using Compound aa127-a ((2S)-2-amino-3-(5-iodo-2-methylphenyl)propanoic acid, H-Phe(2-Me-5-I)—OH) (1.651 g, 5.41 mmol) as a starting material.

LCMS (ESI) m/z=526 (M−H)−
Retention time: 0.97 min (analysis condition SQDFA05)

Synthesis of Compound aa128, (2S)-3-(5-bromo-2-methylphenyl)-2-(9H-fluoren-9-ylmethoxycarbonylamino)propanoic acid (Fmoc-Phe(2-Me-5-Br)—OH)

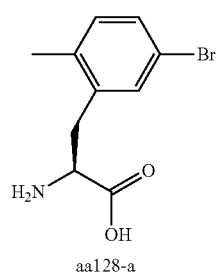

aa128-a

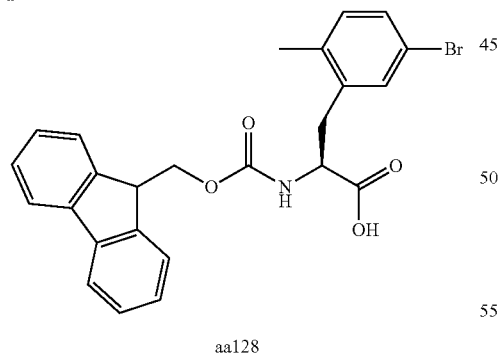

aa128

Compound aa128 ((2S)-3-(5-bromo-2-methylphenyl)-2-(9H-fluoren-9-ylmethoxycarbonylamino)propanoic acid, Fmoc-Phe(2-Me-5-Br)—OH) (2.91 g, quant.) was obtained by the same method as in the synthesis of Compound aa116 using Compound aa128-a ((2S)-2-amino-3-(5-bromo-2-methylphenyl)propanoic acid, H-Phe(2-Me-5-Br)—OH) (1.396 g, 5.41 mmol) as a starting material.

LCMS (ESI) m/z=478 (M−H)−
Retention time: 0.96 min (analysis condition SQDFA05)

Synthesis of Compound aa130, (2S)-2-[9H-fluoren-9-ylmethoxycarbonyl(methyl)amino]octanoic acid (Fmoc-MeAOC(2)-OH)

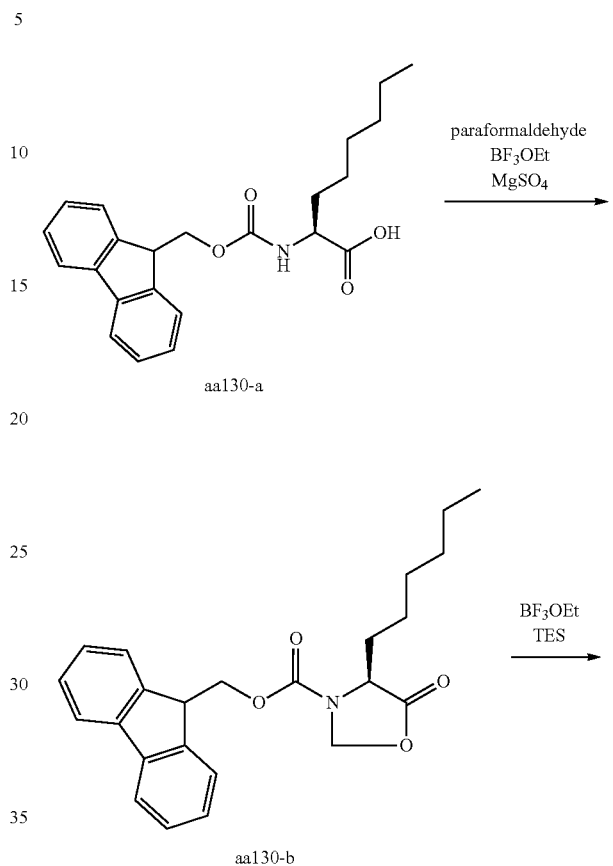

Compound aa130-b was obtained as a crude product by the same method as in the synthesis of Compound aa069-b using Compound aa130-a ((2S)-2-[9H-fluoren-9-ylmethoxycarbonylamino]octanoic acid, Fmoc-AOC(2)-OH) (6.15 g, 16.12 mmol) as a starting material. Further, Compound aa130 ((2S)-2-[9H-fluoren-9-ylmethoxycarbonyl(methyl)amino]octanoic acid, Fmoc-MeAOC(2)-OH) (6.4 g, 100% through two steps) was obtained by the same method as in the synthesis of Compound aa069 using Compound aa130-b.

LCMS (ESI) m/z=396.3 (M+H)+
Retention time: 1.00 min (analysis condition SQDFA05)

575

Synthesis of Compound aa131, (2S)-2-[9H-fluoren-9-ylmethoxycarbonyl(methyl)amino]-5-methyl-hexanoic acid (Fmoc-MeHle-OH)

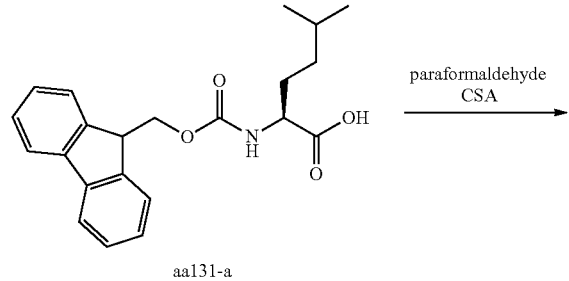

aa131-a

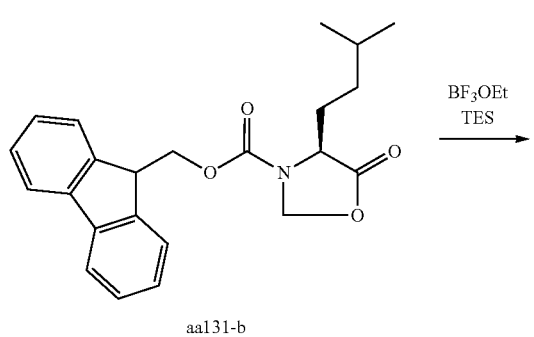

aa131-b

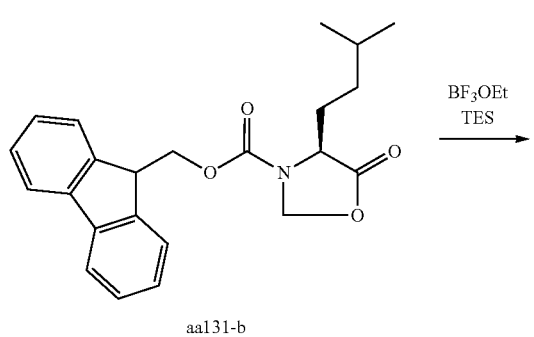

aa131

Compound aa131-b was obtained as a crude product by the same method as in the synthesis of Compound aa078-b using Compound aa131-a ((2S)-2-[9H-fluoren-9-ylmethoxycarbonylamino]-5-methylhexanoic acid, Fmoc-Hle-OH) (20 g, 54.4 mmol) as a starting material. Further, Compound aa131 ((2S)-2-[9H-fluoren-9-ylmethoxycarbonyl(methyl)amino]-5-methylhexanoic acid, Fmoc-MeHle-OH) (21.5 g, quant.) was obtained by the same method as in the synthesis of Compound aa078 using Compound aa131-b.

LCMS (ESI) m/z=382 (M+H)+

Retention time: 0.95 min (analysis condition SQDFA05)

576

Synthesis of Compound aa132, (2S)-4-[3-chloro-4-(trifluoromethyl)phenyl]-2-(9H-fluoren-9-yl-methoxycarbonylamino)butanoic acid, Fmoc-Hph(4-CF3-3-Cl)—OH

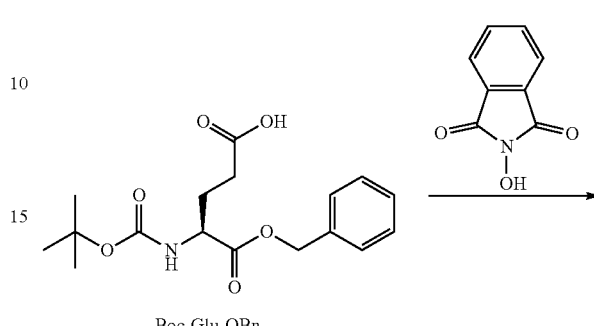

Boc-Glu-OBn

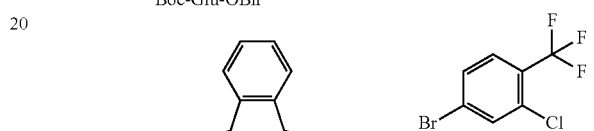

aa132-a

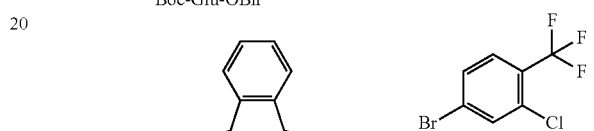

aa132-b

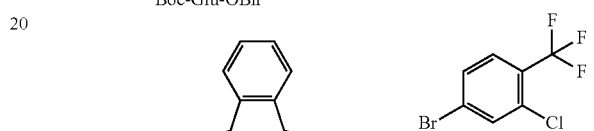

aa132

To a solution of (4S)-4-[(2-methylpropan-2-yl)oxycarbonylamino]-5-oxo-5-phenylmethoxypentanoic acid (Boc-Glu-OBn, CAS No. 30924-93-7) (200 g, 592.82 mmol), N-hydroxyphthalimide (106 g, 649.78 mmol, 1.10 equivalents), and DMAP (3.6 g, 29.47 mmol, 0.05 equivalents) in THF (2 L) was added dropwise DIC (138 mL, 1.54 equivalents) at 0° C. under a nitrogen atmosphere. The reaction solution was stirred at 25° C. for 16 hours, the solid was removed by filtration, and the solvent was evaporated from the filtrate under reduced pressure. The residue was diluted with toluene, the resulting solid was removed by filtration, and the solvent was evaporated from the filtrate under reduced pressure. The residue was purified by recrystallization (acetone/heptane) to give Compound aa132-a (1-O-benzyl 5-O-(1,3-dioxoisoindol-2-yl) (2S)-2-[(2-methylpropan-2-yl)oxycarbonylamino]pentanedioate) (230 g, 80%).

LCMS (ESI) m/z=505.2 (M+Na)+

Retention time: 0.992 min (analysis condition SMD-method_16)

Nickel bromide trihydrate (NiBr$_2$·3H$_2$O) (4 g, 0.07 equivalents) and 4,4'-di-tert-butyl-2,2'-bipyridyl (dtbbpy, CAS No. 72914-19-3) (3.9 g, 14.55 mmol, 0.07 equivalents) were added to DMA (500 mL), and the mixture was stirred at 50° C. for two hours under a nitrogen atmosphere to prepare a Ni solution.

To a mixture of Compound aa132-a (100 g, 207.3 mmol), zinc powder (70 g, 5 equivalents), and 4-bromo-2-chloro-1-(trifluoromethyl)benzene (CAS No. 467435-07-0, 160 g, 617 mmol, 3 equivalents) in DMA (500 mL) was added the Ni solution prepared above, and the mixture was stirred at 25° C. for 16 hours. To the reaction solution was added an aqueous EDTA·2Na solution (10%), and the mixture was extracted with ethyl acetate. The combined organic layers were washed with brine and then dried over anhydrous sodium sulfate, and the solvent was evaporated under reduced pressure. The resulting residue was purified by silica gel column chromatography (ethyl acetate/petroleum ether) to give Compound aa132-b (75 g, 77%).

LCMS (ESI) m/z=494 (M+Na)+

Retention time: 2.863 min (analysis condition SMD-method_17)

A solution of Compound aa132-b (75 g, 158.93 mmol) in toluene (900 mL) was cooled to 0° C., and trifluoromethanesulfonic acid (TfOH) (42 mL, 3.00 equivalents) was added dropwise. After stirring at room temperature for one hour, water (75 mL) was added. The mixture was extracted with water, and the combined aqueous layers were extracted with ethyl acetate. The combined organic layers were washed with water and dried over anhydrous sodium sulfate, and the solvent was then evaporated under reduced pressure. To the residue was added acetonitrile/water (900/900 mL), and the pH was adjusted to 7 with an aqueous sodium hydroxide solution (48%). To this solution was added Fmoc-OSu (51.2 g, 151.93 mmol, 0.95 equivalents), and the mixture was stirred at room temperature for 16 hours while maintaining the pH at 7.8-8.0. The reaction solution was filtered and the filtrate was adjusted to pH 2 with 6 mol/L aqueous hydrochloric acid. The precipitated solid was collected and dried at 50° C. to give Compound aa132 ((2S)-4-[3-chloro-4-(trifluoromethyl)phenyl]-2-(9H-fluoren-9-ylmethoxycarbonylamino)butanoic acid, Fmoc-Hph(4-CF3-3-Cl)—OH) (70 g, 87%).

LCMS (ESI) m/z=525.8 (M+Na)+

Retention time: 2.180 min (analysis condition SMD-method_21)

$^1$H-NMR (300 MHz, DMSO-d6) δ 12.70 (s, 1H), 7.91 (d, J=7.5 Hz, 2H), 7.79-7.59 (m, 5H), 7.45-7.28 (m, 5H), 4.40-4.19 (m, 3H), 3.96-3.88 (m, 1H), 2.82-2.60 (m, 2H), 2.11-1.77 (m, 2H)

Synthesis of Compound aa133, (2S)-2-(9H-fluoren-9-ylmethoxycarbonylamino)-4-[3-fluoro-4-(trifluoromethyl)phenyl]butanoic acid (Fmoc-Hph(4-CF3-3-F)—OH)

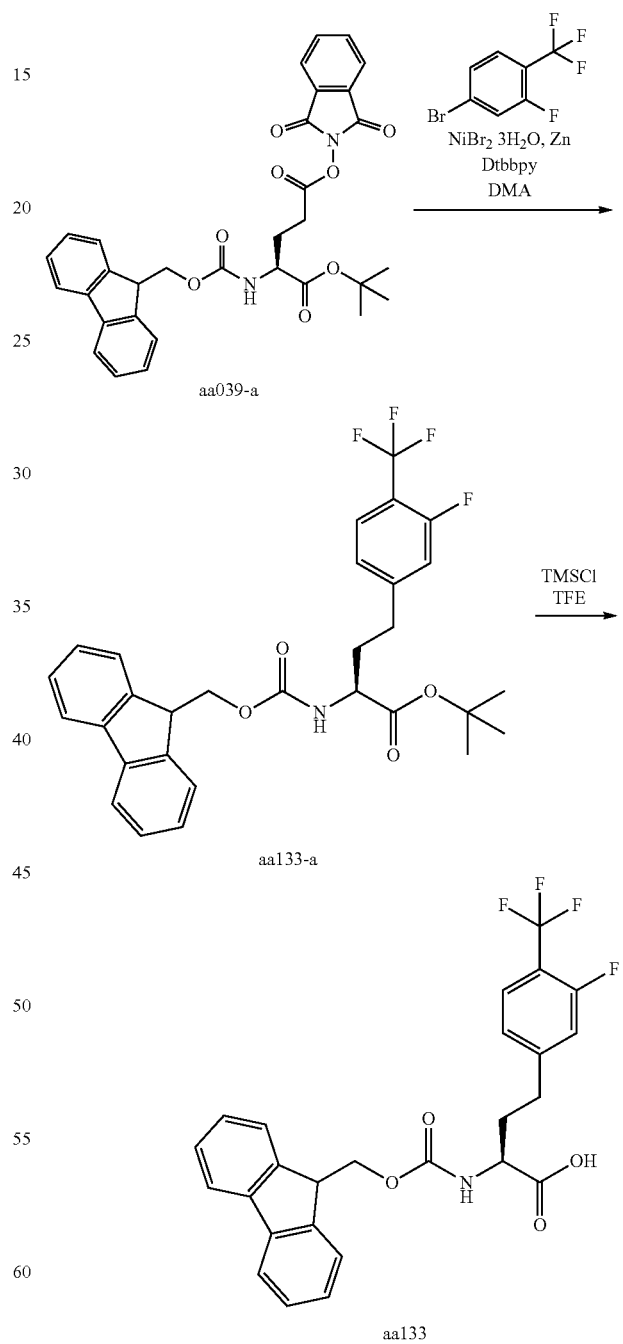

Nickel bromide trihydrate (NiBr$_2$·3H$_2$O) (71.5 g, 263 mmol, 0.3 equivalents) and 4,4'-di-tert-butyl-2,2'-bipyridyl (dtbbpy, CAS No. 72914-19-3) (70.56 g, 263 mmol, 0.3 equivalents) were added to DMA (2 L), and the mixture was stirred at 50° C. for three hours under a nitrogen atmosphere to prepare a Ni solution.

A mixture of Compound aa039-a (1-O-tert-butyl 5-O-(1,3-dioxoisoindol-2-yl) (2S)-2-(9H-fluoren-9-ylmethoxycarbonylamino)pentanedioate) (500 g, 876 mmol), which was synthesized according to the method described in this example using compound Fmoc-Glu-OtBu ((4S)-4-(9H-fluorene-9-ylmethoxycarbonylamino)-5-[(2-methylpropan-2-yl)oxy]-5-oxopentanoic acid, CAS No. 84793-07-7) as a raw material, zinc powder (287 g, 4.38 mol, 5 equivalents), and 4-bromo-2-fluoro-1-(trifluoromethyl)benzene (CAS No. 142808-15-9, 425.87 g, 1.753 mol, 2 equivalents) in DMA (2 L) was stirred at room temperature for 1 hour under a nitrogen atmosphere. To this mixture was added the Ni solution prepared above, and the mixture was stirred at room temperature for 16 hours. To the reaction solution was added an aqueous EDTA-2Na solution (4 L, 10%), and the solid was removed by filtration while washing with ethyl acetate. The filtrate was washed with brine and then dried over anhydrous sodium sulfate, and the solvent was evaporated under reduced pressure. The resulting residue was purified by silica gel column chromatography (ethyl acetate/petroleum ether) to give Compound aa133-a (230 g, 43%).

LCMS (ESI) m/z=566.2 (M+Na)+

Retention time: 1.317 min (analysis condition SMD-method_18)

A mixture of the obtained Compound aa133-a (230 g, 423 mmol) and chlorotrimethylsilane (TMSCl) (137.9 g, 1.269 mol) in trifluoroethanol (TFE) (2.3 L) was stirred at room temperature for one hour, and the precipitated solid was collected by filtration. The resulting solid was dissolved in TBME and the solvent was evaporated under reduced pressure. This operation was repeated several times to give the target Compound aa133 ((2S)-2-(9H-fluoren-9-ylmethoxycarbonylamino)-4-[3-fluoro-4-(trifluoromethyl)phenyl]butanoic acid, Fmoc-Hph(4-CF3-3-F)—OH) (190 g, 90%).

LCMS (ESI) m/z=510.2 (M+Na)+

Retention time: 1.585 min (analysis condition SMD-method_13)

$^1$H-NMR (300 MHz, DMSO-d6) δ 12.69 (s, 1H), 7.90 (d, J=7.5 Hz, 2H), 7.81-7.66 (m, 4H), 7.47-7.37 (m, 3H), 7.37-7.29 (m, 2H), 7.25 (d, J=8.1 Hz, 1H), 4.44-4.14 (m, 3H), 3.97-3.84 (m, 1H), 2.80-2.63 (m, 2H), 2.12-1.81 (m, 2H).

Synthesis of Compound aa134, (2S)-4-[3,5-difluoro-4-(trifluoromethyl)phenyl]-2-(9H-fluoren-9-ylmethoxycarbonylamino)butanoic acid, Fmoc-Hph(4-CF3-35-F2)-OH

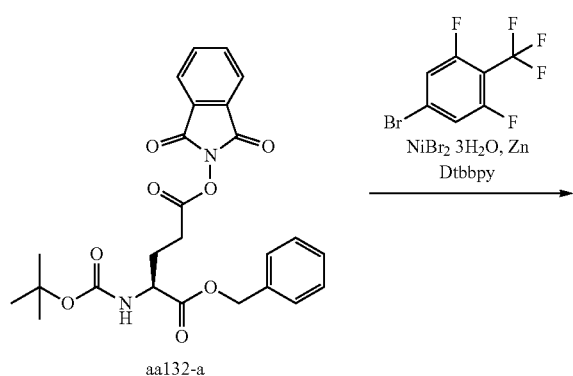

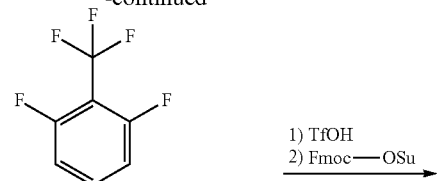

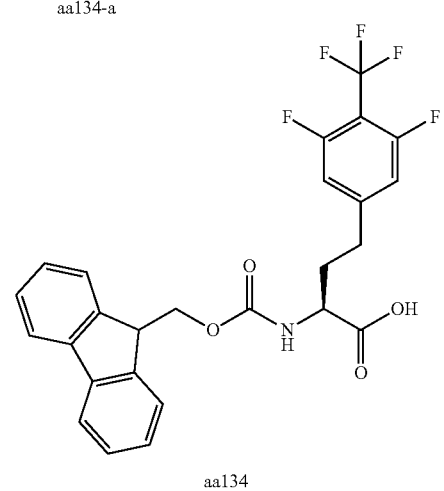

aa134-a aa134

Nickel bromide trihydrate (NiBr$_2$·3H$_2$O) (13.5 g, 49.7 mmol, 0.3 equivalents) and 4,4'-di-tert-butyl-2,2'-bipyridyl (dtbbpy, CAS No. 72914-19-3) (13.3 g, 49.7 mmol, 0.3 equivalents) were added to DMA (400 mL), and the mixture was stirred at 50° C. for three hours under a nitrogen atmosphere to prepare a Ni solution.

A mixture of Compound aa132-a (1-O-benzyl 5-O-(1,3-dioxoisoindol-2-yl) (2S)-2-[(2-methylpropan-2-yl)oxycarbonylamino]pentanedioate) (80 g, 166 mmol), zinc powder (54.2 g, 829 mmol, 5 equivalents), and 4-bromo-1,3-difluoro-2-(trifluoromethyl)benzene (CAS No. 156243-64-0, 86.6 g, 332 mmol, 2 equivalents) in DMA (400 mL) was stirred at room temperature for one hour under a nitrogen atmosphere. The above-prepared Ni solution was added, and the mixture was stirred at room temperature for 16 hours. To the reaction solution was added an aqueous EDTA-2Na solution (800 mL, 10%), and the solid was removed by filtration. The filtrate was extracted with ethyl acetate, the combined organic layers were washed with brine and then dried over anhydrous sodium sulfate, and the solvent was evaporated under reduced pressure. The resulting residue was purified by silica gel column chromatography (ethyl acetate/petroleum ether) to give Compound aa134-a (57.2 g, 69%).

LCMS (ESI) m/z=496 (M+Na)+

Retention time: 1.544 min (analysis condition SMD-method_15)

A mixture of Compound aa134-a (57.2 g, 121 mmol) in toluene (690 mL) was cooled to 0° C., and trifluoromethanesulfonic acid (TfOH) (54.4 g, 362 mmol, 3 equivalents) was added dropwise. After stirring at room temperature for one hour, water (58 mL) was added. The mixture was extracted with water, and the combined aqueous layers were extracted with ethyl acetate. The combined organic layers were washed with water and dried over anhydrous sodium sulfate, and the solvent was then evaporated under reduced pressure to give 60 g of a residue. To the residue was added acetonitrile/water (400/400 mL), and the pH was adjusted to 7 with an aqueous sodium hydroxide solution (48%). To the solution was added Fmoc-OSu (36.6 g, 108.6 mmol, 0.9 equivalents), the pH was adjusted to 8.0 with an aqueous sodium hydroxide solution (48%), and the mixture was then stirred at room temperature for 16 hours. The reaction solution was filtered while washing with acetonitrile/water (1/1) to remove the solid component. The filtrate was diluted with acetonitrile and acidified with 6 mol/L aqueous hydrochloric acid, and the precipitated solid was collected by filtration to give Compound aa134 ((2S)-4-[3,5-difluoro-4-(trifluoromethyl)phenyl]-2-(9H-fluoren-9-ylmethoxycarbonylamino)butanoic acid, Fmoc-Hph(4-CF3-35-F2)-OH) (52 g, 83%).

LCMS (ESI) m/z=528.45 (M+Na)+

Retention time: 3.538 min (analysis condition SMD-method_14)

1H-NMR (300 MHz, DMSO-d6) δ 12.69 (s, 1H), 7.90 (d, J=7.5 Hz, 2H), 7.78-7.54 (m, 3H), 7.48-7.20 (m, 6H), 4.33 (d, J=6.3 Hz, 2H), 4.24 (t, J=6.9 Hz, 1H), 3.97-3.84 (m, 1H), 2.79-2.65 (m, 2H), 2.15-2.00 (m, 1H), 2.00-1.83 (m, 1H)

Synthesis of Compound aa150 ((2S)-2-[9H-fluoren-9-ylmethoxycarbonyl(methyl)amino]-5,5,5-trifluoropentanoic acid, Fmoc-MeNva(5-F2)-OH)

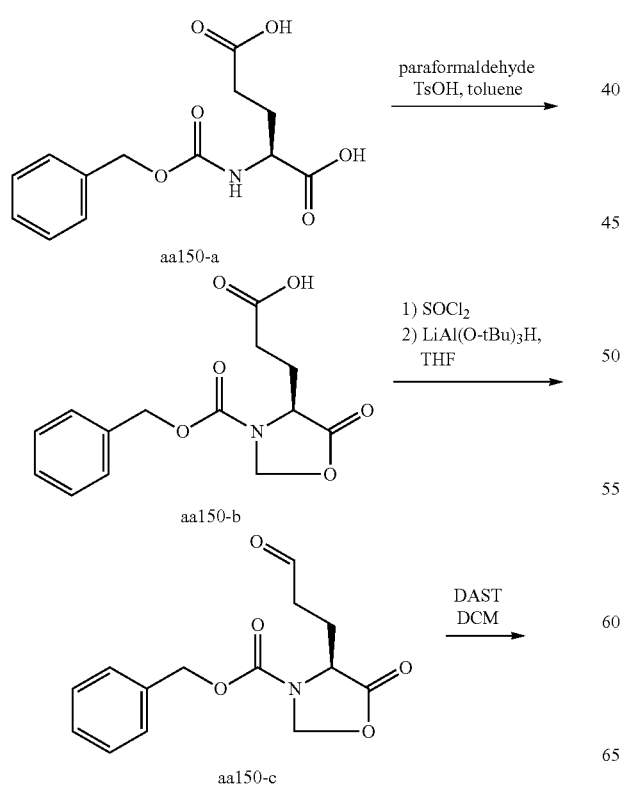

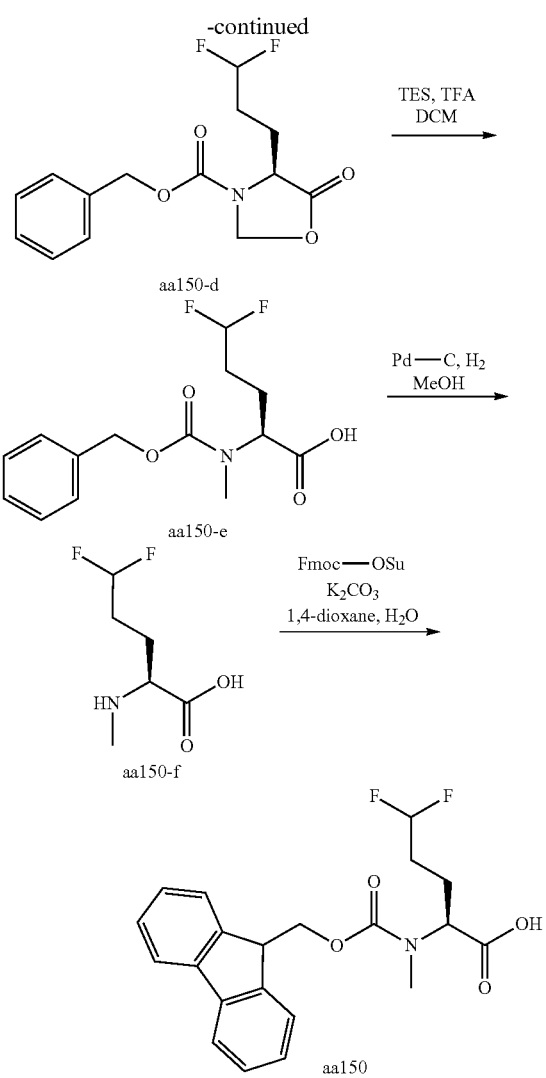

A mixture of Compound aa150-a ((2S)-2-(phenylmethoxycarbonylamino)pentanedioic acid) (50 g, 177.8 mmol), paraformaldehyde (11.87 g), and p-toluenesulfonic acid (1.84 g, 10.69 mmol) in toluene (500 mL) was stirred at 120° C. for 16 hours. The reaction solution was left to cool to room temperature, diluted with ethyl acetate, washed with brine, then dried over anhydrous sodium sulfate, and the solvent was evaporated under reduced pressure to give Compound aa150-b as a crude product (52 g, 96%). The crude product was used for the next reaction without purification.

A solution of Compound aa150-b (4 g, 13.64 mmol) in thionyl chloride (50 mL) was stirred at 85° C. for one hour, and the solvent was then evaporated under reduced pressure. The residue was dissolved in THF (20 mL) and cooled to −78° C. under a nitrogen atmosphere. A solution of lithium tri-tert-butoxyaluminum hydride (2.76 g, 10.87 mmol) in THF (20 mL) was added thereto dropwise over 2.5 hours. After stirring at −78° C. for three hours, water was added to the reaction solution, and the precipitate was removed by filtration. The filtrate was extracted with ethyl acetate, the organic layer was washed with brine, then dried over anhydrous sodium sulfate, and the solvent was evaporated under reduced pressure. The resulting residue was purified by silica gel column chromatography (ethyl acetate/petroleum ether) to give Compound aa150-c (2 g).

¹H-NMR (400 MHz, CDCl₃) δ 7.41-7.32 (m, 5H), 5.49 (br.s, 1H), 5.27-5.11 (m, 3H), 4.38-4.33 (m, 1H), 2.58-2.19 (m, 4H)

To a solution of Compound aa150-c (450 mg, 1.62 mmol) in DCM (20 mL) was added N,N-diethylaminosulfur trifluoride (DAST) (780 mg, 4.84 mmol) at 0° C. under a nitrogen atmosphere, and the mixture was stirred at room temperature for 16 hours. After adding water, the reaction solution was diluted with DCM and sequentially washed with an aqueous sodium bicarbonate solution and brine. The organic layer was dried over anhydrous sodium sulfate and the solvent was evaporated under reduced pressure. The resulting residue was purified by silica gel column chromatography (ethyl acetate/petroleum ether) to give Compound aa150-d (0.35 g, 72%). This was mixed with another lot synthesized in the same manner, and the next reaction was performed.

¹H-NMR (400 MHz, CDCl₃) δ 7.42-7.35 (m, 5H), 5.97-5.58 (m, 2H), 5.25-5.16 (m, 3H), 4.50-4.35 (m, 1H), 2.14-1.68 (m, 4H)

¹⁹F-NMR (400 MHz, CDCl₃) δ—116.562

Compound aa150-d (1 g, 3.34 mmol) and TES (12.63 g, 109 mmol) were dissolved in TFA/DCM (10/10 mL), the mixture was stirred at room temperature for four days, and the solvent was then evaporated under reduced pressure. The residue was diluted with an aqueous sodium bicarbonate solution, washed with ether, and then adjusted to pH 3 with 2 N aqueous hydrochloric acid. The organic layer was extracted with DCM, washed with brine, and then dried over anhydrous sodium sulfate, and the solvent was evaporated under reduced pressure to give Compound aa150-e (0.6 g) as a crude product. The crude product was used for the next reaction without purification.

A mixture of Compound aa150-e (0.6 g) and palladium on carbon (10%, 60 mg) in methanol (10 mL) was stirred for 16 hours under a hydrogen atmosphere at about 3 atm. The palladium on carbon was removed by filtration, and the solvent was evaporated from the filtrate under reduced pressure to give Compound aa150-f (0.23 g) as a crude product. The crude product was used for the next reaction without purification. This was mixed with another lot synthesized in the same manner, and the next reaction was performed.

To a mixture of Compound aa150-f (0.3 g, 1.79 mmol) and potassium carbonate (745 mg, 5.4 mmol) in 1,4-dioxane/water (5/5 mL) was added Fmoc-OSu (0.9 g, 1.5 equivalents), and the mixture was stirred for two hours. The reaction solution was diluted with water, washed with diethyl ether, and then adjusted to pH 3 with 2 N aqueous hydrochloric acid. The organic layers were extracted with ethyl acetate three times, combined, washed with brine, and then dried over anhydrous sodium sulfate, and the solvent was evaporated under reduced pressure. The resulting residue was purified by reverse phase column chromatography (acetonitrile with 0.05% TFA/distilled water with 0.05% TFA) to give Compound aa150 ((2S)-2-[9H-fluoren-9-ylmethoxycarbonyl(methyl)amino]-5,5,5-trifluoropentanoic acid, Fmoc-MeNva(5-F2)-OH) (0.2 g, 29%). Another lot synthesized in the same manner was also used for peptide synthesis in the present Examples.

Retention time: 3.153 min (analysis condition SMD-method_19)

¹H-NMR (300 MHz, DMSO-d6) δ 12.94 (br.s, 1H), 7.92-7.88 (d, J=7.2 Hz, 2H), 7.66-7.61 (m, 2H), 7.44-7.31 (m, 4H), 6.35-5.75 (m, 1H), 4.49-4.26 (m, 4H), 2.72 (s, 3H), 1.78-1.65 (m, 4H)

¹⁹F-NMR (300 MHz, DMSO-d6) δ–115.730

Synthesis of Compound aa151 ((2S)-3-(3,4-difluorophenyl)-2-[9H-fluoren-9-ylmethoxycarbonyl(methyl)amino]propanoic acid. Fmoc-MePhe(34-F2)-OH)

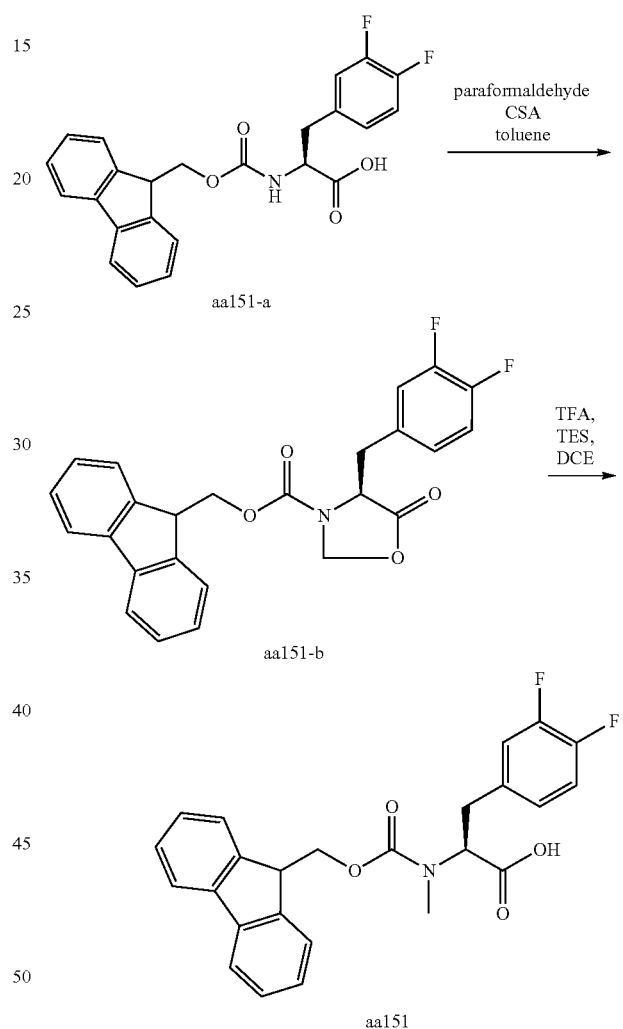

Compound aa151-b was obtained as a crude product by the same method as in the synthesis of Compound aa078-b using Compound aa151-a ((2S)-3-(3,4-difluorophenyl)-2-[9H-fluoren-9-ylmethoxycarbonyl(methyl)amino]propanoic acid, Fmoc-Phe(34-F2)-OH) (105 mg, 0.247 mmol) as a starting material. Further, Compound aa151 ((2S)-3-(3,4-difluorophenyl)-2-[9H-fluoren-9-ylmethoxycarbonyl(methyl)amino]propanoic acid, Fmoc-MePhe(34-F2)-OH) (74.4 mg, 69% through two steps) was obtained by the same method as in the synthesis of Compound aa060 using aa151-b.

LCMS (ESI) m/z=438 (M+H)+

Retention time: 0.88 min (analysis condition SQDFA05)

Synthesis of Compound aa152 ((2S)-4-(4,4-difluoropiperidin-1-yl)-2-[9H-fluoren-9-ylmethoxycarbonyl(methyl)amino]-4-oxobutanoic acid, Fmoc-MeAsn(pip-4-F2)-OH)

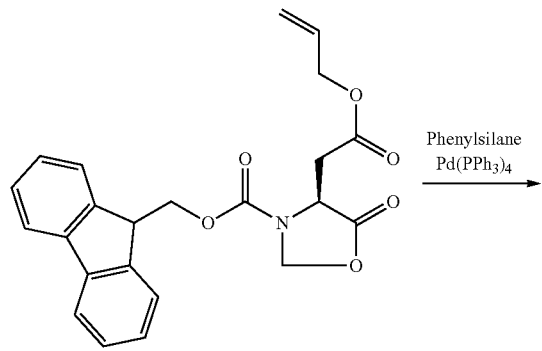

aa033-a

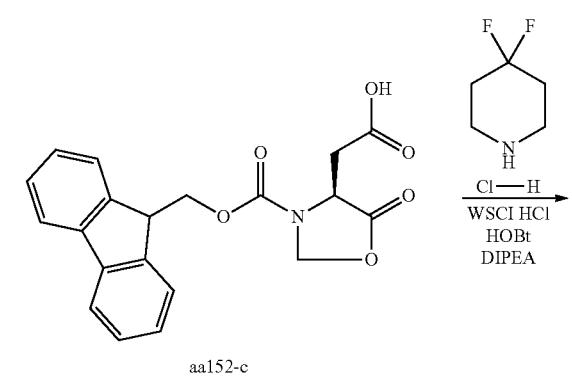

aa152-c

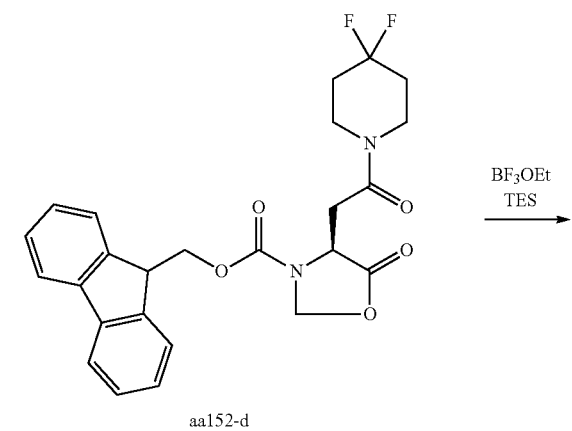

aa152-d

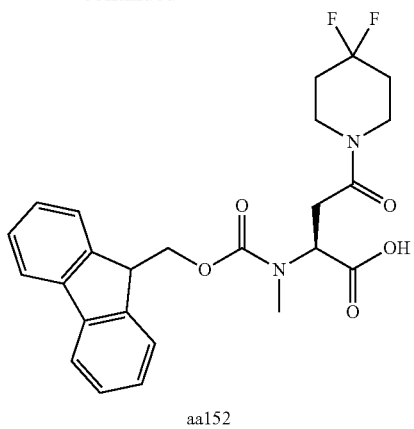

aa152

To a mixture of Compound aa033-a (9H-fluoren-9-ylmethyl (4S)-5-oxo-4-(2-oxo-2-prop-2-enoxyethyl)-1,3-oxazolidine-3-carboxylate) (10.3 g, 25.3 mmol) in DCM (25.3 mL) were added phenylsilane (2.176 ml, 17.7 mmol) and tetrakis(triphenylphosphine)palladium(0) (146 mg, 0.126 mmol), and the mixture was stirred at room temperature for 50 minutes. The reaction solution was diluted with TBME (10 v/w) and washed with a 5% aqueous sodium bicarbonate solution. The aqueous layer was adjusted to pH 4 with phosphoric acid and extracted with TBME. The resulting organic layer was washed with brine/water (1/1) and dried over anhydrous sodium sulfate, and the solvent was then evaporated under reduced pressure to give Compound aa152-c (9.12 g, 98%).

LCMS (ESI) m/z=368 (M+H)+

Retention time: 0.72 min (analysis condition SQDFA05)

Compound aa152-c (9.1 g, 24.77 mmol) and HOBt (3.68 g, 27.2 mmol) were added to a suspension of WSCI·HCl (5.7 g, 29.7 mmol) in DMF (70.8 mL) at 0° C., and the mixture was stirred at 0° C. for 30 minutes. 4,4-Difluoropiperidine hydrochloride (4.29 g, 27.2 mmol) and DIPEA (4.39 mL, 24.77 mL) were added thereto, and the mixture was stirred at 0° C. for one hour. The reaction solution was diluted with ethyl acetate and sequentially washed with 0.5 mol/L aqueous hydrochloric acid, water, saturated aqueous sodium bicarbonate/water (1/1), and brine/water (1/1). The resulting organic layer was dried over anhydrous sodium sulfate and the solvent was then evaporated under reduced pressure to give Compound aa152-d (10.87 g, 93%).

LCMS (ESI) m/z=471 (M+H)+

Retention time: 0.85 min (analysis condition SQDFA05)

The obtained Compound aa152-d (10.87 g) was reacted by the same method as in the synthesis of Compound aa069 and then purified by reverse phase column chromatography (0.1% aqueous formic acid/0.1% formic acid-acetonitrile) to give Compound aa152, (2S)-4-(4,4-difluoropiperidin-1-yl)-2-[9H-fluoren-9-ylmethoxycarbonyl(methyl)amino]-4-oxobutanoic acid (Fmoc-MeAsn(pip-4-F2)-OH) (10.6 g, 91%).

LCMS (ESI) m/z=473 (M+H)+

Retention time: 0.78 min (analysis condition SQDFA05)

Synthesis of Compound aa153 ((2S)-4-(3,3-difluoroazetidin-1-yl)-2-[9H-fluoren-9-ylmethoxycarbonyl(methyl)amino]-4-oxobutanoic acid, Fmoc-MeAsn(Aze-3-F2)-OH)

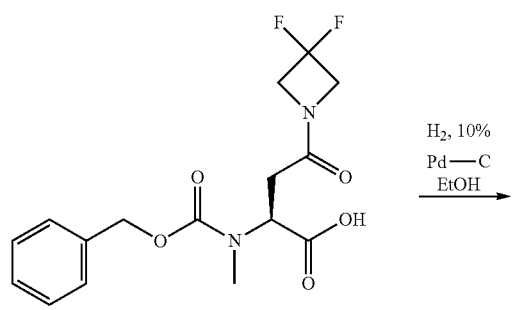

aa047-c

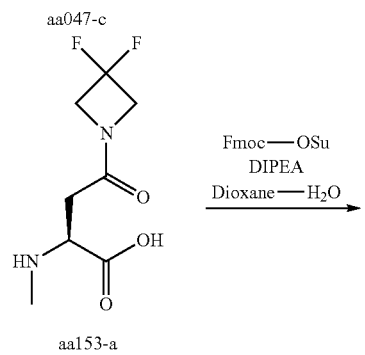

aa153-a

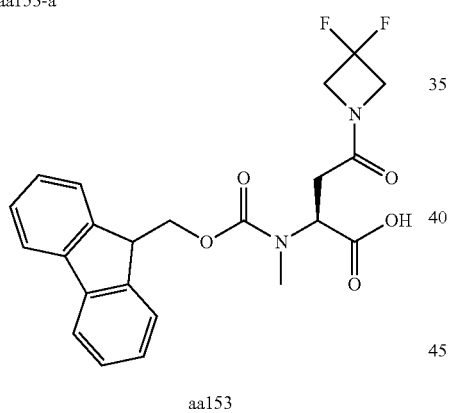

aa153

A suspension of Compound aa047-c ((2S)-4-(3,3-difluoroazetidin-1-yl)-2-[methyl(phenylmethoxycarbonyl)amino]-4-oxobutanoic acid) (500 mg, 1.403 mmol) and 10% palladium on carbon (50 w/w % water, 100 mg) in ethanol (15 mL) was stirred at room temperature for 13 hours and 15 minutes under a hydrogen atmosphere, after which the reaction mixture was filtered through celite, and the resulting filtrate was concentrated under reduced pressure to yield Compound aa153-a as a crude product (324 mg).

Compound aa153-a (324 mg) was dissolved in distilled water (5 ml), 1,4-dioxane (5 ml), diisopropylethylamine (DIPEA) (1.019 ml, 5.83 mmol), and N-(9-fluorenylmethoxycarbonyloxy)succinimide (Fmoc-OSu) (492 mg, 1.458 mmol) were added, and the mixture was stirred at room temperature for 30 minutes. To the reaction solution were added water (5 mL) and hexane/cyclopentyl methyl ether (3/1, 5 mL), and the mixture was washed with hexane/ether (3/1). To the resulting aqueous layer were added potassium hydrogen sulfate (0.79 g), ethyl acetate, and saturated aqueous potassium hydrogen sulfate (1 mL), and the mixture was extracted with ethyl acetate. The resulting organic layer was washed with brine/water (1/1) and then dried over anhydrous sodium sulfate, and the solvent was evaporated under reduced pressure to give Compound aa153, (2S)-4-(3,3-difluoroazetidin-1-yl)-2-[9H-fluoren-9-ylmethoxycarbonyl(methyl)amino]-4-oxobutanoic acid (Fmoc-MeAsn(Aze-3-F2)-OH) (660 mg, quant.).

LCMS (ESI) m/z=445 (M+H)+
Retention time: 0.72 min (analysis condition SQDFA05)

Synthesis of Compound aa154, ((2S)-2-(9H-fluoren-9-ylmethoxycarbonyl(methyl)amino)-3-(3-iodophenyl)propanoic acid, Fmoc-MePhe(3-I)—OH)

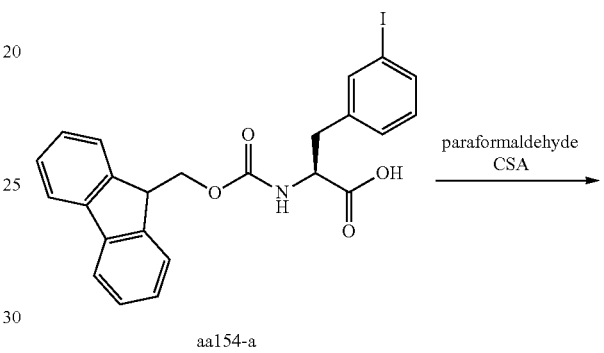

aa154-a

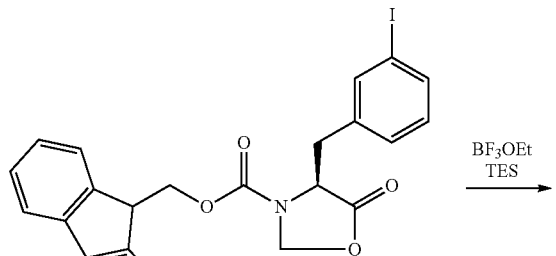

aa154-b

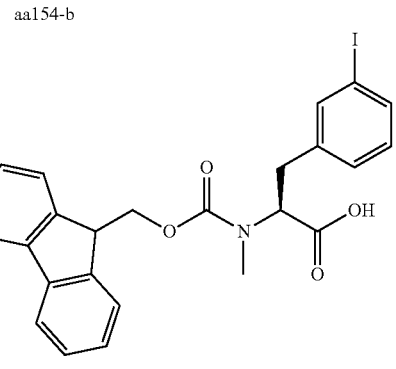

aa154

Compound aa154-b (3.11 g) was obtained as a crude product by the same method as in the synthesis of Compound aa078-b using Compound aa154-a ((2S)-2-(9H-fluoren-9-ylmethoxycarbonylamino)-3-(3-iodophenyl)propanoic acid, Fmoc-Phe(3-I)—OH) (containing one molecule of THF per molecule of amino acid, 3.29 g, 5.62 mmol) as a starting material.

LCMS (ESI) m/z=526 (M+H)+

Retention time: 1.07 min (analysis condition SQDFA05)

Compound aa154 ((2S)-2-(9H-fluoren-9-ylmethoxycarbonyl(methyl)amino)-3-(3-iodophenyl)propanoic acid (Fmoc-MePhe(3-I)—OH)) (2.924 g, 99% through two steps) was obtained by the same method as in the synthesis of Compound aa078 using the obtained Compound aa154-b.

LCMS (ESI) m/z=528 (M+H)+

Retention time: 0.98 min (analysis condition SQDFA05)

The amino acid to be loaded on the resin was synthesized according to the following scheme.

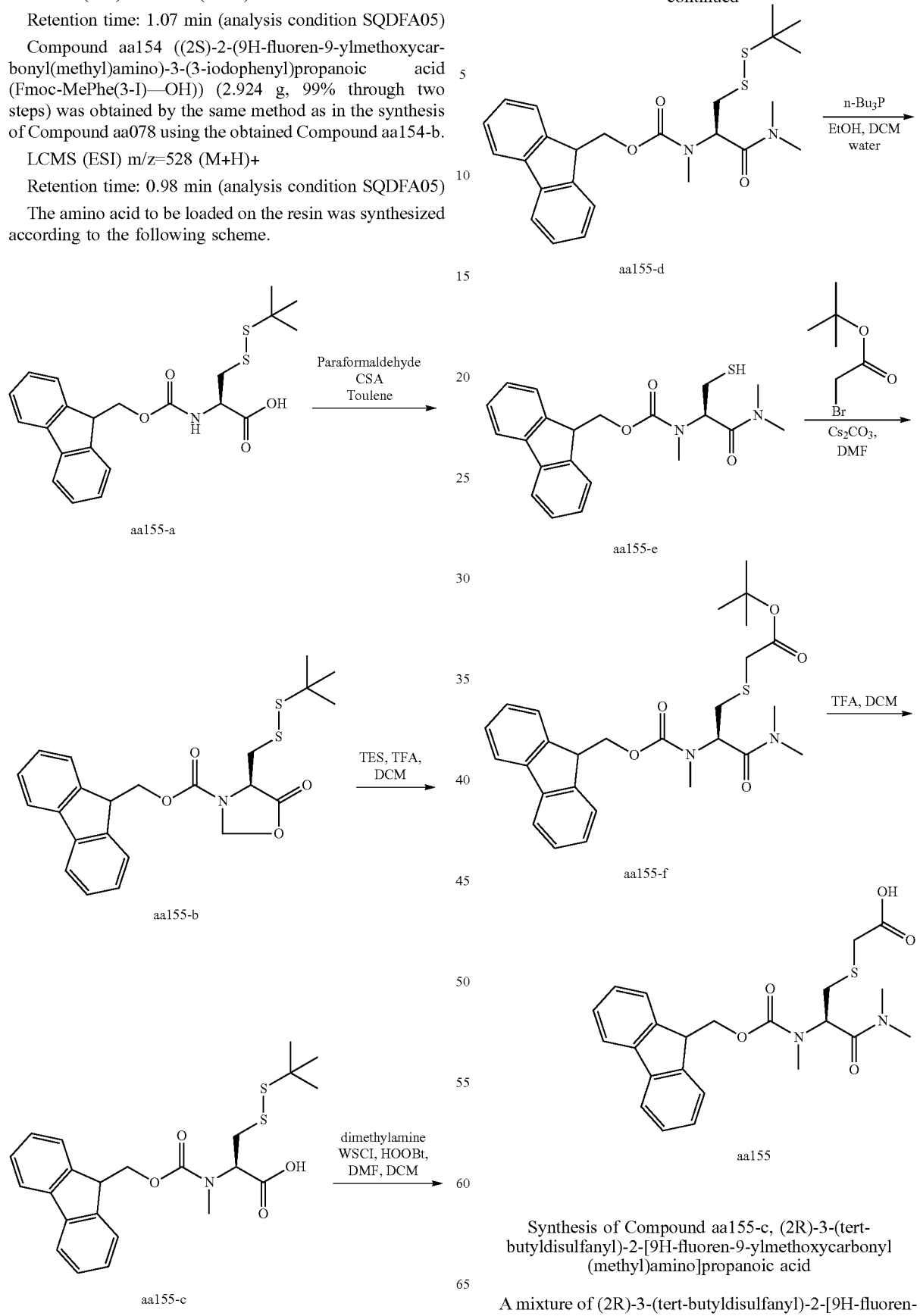

Synthesis of Compound aa155-c, (2R)-3-(tert-butyldisulfanyl)-2-[9H-fluoren-9-ylmethoxycarbonyl(methyl)amino]propanoic acid A mixture of (2R)-3-(tert-butyldisulfanyl)-2-[9H-fluoren-9-ylmethoxycarbonylamino]propanoic acid (20.0 g, 46.3 mmol), (+)-camphorsulfonic acid (752.6 mg, 3.2 mmol, 0.07 equivalents), and paraformaldehyde (13.9 g, 463.4 mmol, 10.0 equivalents) in toluene (200 mL) was stirred at room temperature for 1 hour under a nitrogen atmosphere. The reaction solution was diluted with ethyl acetate, washed with an aqueous sodium bicarbonate solution three times, and then washed with brine. The obtained organic layer was dried over anhydrous sodium sulfate and the solvent was evaporated under reduced pressure to give Compound aa155-b (9H-fluoren-9-ylmethyl(4R)-4-[(tert-butyldisulfanyl)methyl]-5-oxo-1,3-oxazolidine-3-carboxylate, 23 g) as a crude product.

LCMS (ESI) m/z=466.1 (M+Na)+

Retention time: 1.560 min (analysis condition SMD-method_20)

To a mixture of Compound aa155-b (9H-fluoren-9-ylmethyl(4R)-4-[(tert-butyldisulfanyl)methyl]-5-oxo-1,3-oxazolidine-3-carboxylate, 23 g) obtained above and triethylsilane (60.2 g, 518 mmol) in dichloromethane (120 mL) was added trifluoroacetic acid (120 mL) at room temperature under a nitrogen atmosphere, and the mixture was stirred for 40 hours. The solvent was evaporated from the reaction solution under reduced pressure, and the resulting residue was purified by reverse phase column chromatography (C18, acetonitrile/water) to give Compound aa155-c, (2R)-3-(tert-butyldisulfanyl)-2-[9H-fluoren-9-ylmethoxycarbonyl(methyl)amino] propanoic acid (13 g, 63% through two steps).

LCMS (ESI) m/z=446.1 (M+H)+

Retention time: 0.852 min (analysis condition SMD-method_30)

Synthesis of Compound aa155-d, 9H-fluoren-9-ylmethyl N-[(2R)-3-(tert-butyldisulfanyl)-1-(dimethylamino)-1-oxopropan-2-yl]-N-methylcarbamate Under a nitrogen atmosphere, Compound aa155-c ((2R)-3-(tert-butyldisulfanyl)-2-[9H-fluoren-9-ylmethoxycarbonyl(methyl)amino]propanoic acid, 13.0 g, 29.2 mmol), WSCI·HCl (6.49 g, 33.84 mmol, 1.2 equivalents), and 3,4-dihydro-3-hydroxy-4-oxo-1,2,3-benzotriazine (HOOBt) (5.23 g, 32.09 mmol, 1.1 equivalents) were added to a mixture of DMF (26 mL) and DCM (90 mL) at room temperature, and the mixture was stirred for five minutes. The obtained reaction solution was cooled to 0° C., and dimethylamine (a solution of 2 mol/L in THF, 15.60 mL, 31.2 mmol, 1.07 equivalents) was added dropwise, and the reaction solution was stirred at 0° C. for one hour. The reaction solution was diluted with ethyl acetate, washed with hydrochloric acid (1 mol/L, 130 mL) twice, then washed with water (130 mL) once, washed with an aqueous sodium bicarbonate solution (130 mL) twice, and washed with brine (130 mL) once. The obtained organic layer was dried over anhydrous sodium sulfate and the solvent was evaporated under reduced pressure. The resulting residue was purified by normal phase chromatography (petroleum ether/ethyl acetate) to give Compound aa155-d (9H-fluoren-9-ylmethyl N-[(2R)-3-(tert-butyldisulfanyl)-1-(dimethylamino)-1-oxopropan-2-yl]-N-methylcarbamate, 12.1 g, 88%).

LCMS (ESI) m/z=495.2 (M+Na)+

Retention time: 1.546 min (analysis condition SMD-method_20)

Synthesis of Compound aa155-e, 9H-fluoren-9-ylmethyl N-[(2R)-1-(dimethylamino)-1-oxo-3-sulfanylpropan-2-yl]-N-methylcarbamate Under a nitrogen atmosphere, to a mixture of Compound aa155-d (9H-fluoren-9-ylmethyl N-[(2R)-3-(tert-butyldisulfanyl)-1-(dimethylamino)-1-oxopropan-2-yl]-N-methylcarbamate, 11.7 g, 24.7 mmol) in ethanol (100 mL), DCM (150 mL), and water (25 mL), tri-n-butylphosphine (6.0 g, 29.7 mmol, 1.2 equivalents) was added dropwise at room temperature, and the mixture was stirred for three hours at room temperature. The reaction solution was extracted with dichloromethane (DCM), and the resulting organic layer was washed with brine, dried over anhydrous sodium sulfate, and the solvent was then evaporated under reduced pressure. The resulting residue was purified by normal phase chromatography (petroleum ether/ethyl acetate), and the resulting mixture was purified by reverse phase column chromatography (C18, acetonitrile/water) to give Compound aa155-e (9H-fluoren-9-ylmethyl N-[(2R)-1-(dimethylamino)-1-oxo-3-sulfanylpropan-2-yl]-N-methylcarbamate, 3.03 g, 32%).

LCMS (ESI) m/z=407.2 (M+Na)+

Retention time: 1.326 min (analysis condition SMD-method_20)

Synthesis of Compound aa155, 2-[(2R)-3-(dimethylamino)-2-[9H-fluoren-9-ylmethoxycarbonyl(methyl)amino]-3-oxopropyl]sulfanylacetic acid A mixture of Compound aa155-e (9H-fluoren-9-ylmethyl N-[(2R)-1-(dimethylamino)-1-oxo-3-sulfanylpropan-2-yl]-N-methylcarbamate, 2.80 g, 7.29 mmol) and tert-butyl bromoacetic acid (2.10 g, 10.77 mmol, 1.5 equivalents) in DMF (40 mL) was stirred at room temperature for five minutes, cesium carbonate (2.80 g, 8.59 mmol, 1.2 equivalents) was added thereto, and the mixture was stirred for one hour. The reaction solution was diluted with ethyl acetate and washed with water. The obtained organic layer was dried over anhydrous sodium sulfate, and the solvent was evaporated under reduced pressure to give Compound aa155-f (tert-butyl 2-[(2R)-3-(dimethylamino)-2-[9H-fluoren-9-ylmethoxycarbonyl(methyl)amino]-3-oxopropyl]sulfanyl acetate, 3.1 g) as a crude product. The obtained crude product was used for the next reaction without further purification.

LCMS (ESI) m/z=499.3 (M+H)+

Retention time: 1.467 min (analysis condition SMD-method_20)

Compound aa155-f (tert-butyl 2-[(2R)-3-(dimethylamino)-2-[9H-fluoren-9-ylmethoxycarbonyl(methyl)amino]-3-oxopropyl]sulfanyl acetate, 3.1 g) obtained above was dissolved in a mixture of trifluoroacetic acid (TFA) (30 mL) and dichloromethane (DCM) (30 mL), and the mixture was stirred for two hours at room temperature under a nitrogen atmosphere. The solvent was evaporated from the reaction solution under reduced pressure, and the resulting residue was purified by reverse phase column chromatography (C18, acetonitrile/water). The obtained mixture was further purified by reverse phase high-performance column chromatography (acetonitrile/water, containing TFA), and the resulting eluate was extracted with DCM. The obtained organic layer was sequentially washed with water and hydrochloric acid (1 mol/L), and the solvent was evaporated under reduced pressure to give Compound aa155 (2-[(2R)-3-(dimethylamino)-2-[9H-fluoren-9-ylmethoxycarbonyl(methyl)amino]-3-oxopropyl]sulfanylacetic acid, 1.79 g, 55% through two steps).

LCMS (ESI) m/z=443.2 (M+H)+

Retention time: 1.383 min (analysis condition SMD-method_31)

1-2. Synthesis of Amino Acid-Loaded Resins Used for Solid-Phase Peptide Synthesis by an Automated Synthesizer Amino acids listed in Table 6 were synthesized by the methods provided below, and were loaded on resins and used for peptide synthesis using a peptide synthesizer. Amino acids listed in Table 7 were purchased from commercial suppliers, and were loaded on resins and used for peptide synthesis using a peptide synthesizer. Fmoc amino acids were loaded on resins according to the method described in WO 2013/100132 or WO 2018/225864. 2-Chlorotrityl chloride resin (100-200 mesh, 1% DVB) was purchased from Watanabe Chemical Industries, Ltd. and Chem-Impex.

TABLE 6

| Compound No. | Abbreviation | Structural formula | Name |
|---|---|---|---|
| aa006 | Fmoc-MeAsp-pip | | (3S)-3-[9H-fluoren-9-ylmethoxycarbonyl(methyl)amino]-4-oxo-4-piperidin-1-ylbutanoic acid |
| aa007 | Fmoc-MeAsp-mor | | (3S)-3-[9H-fluoren-9-ylmethoxycarbonyl(methyl)amino]-4-morpholin-4-yl-4-oxobutanoic acid |
| aa008 | Fmoc-MeAsp-pyrro(3-Me2) | | (3S)-4-(3,3-dimethylpyrrolidin-1-yl)-3-[9H-fluoren-9-ylmethoxycarbonyl(methyl)amino]-4-oxobutanoic acid |
| aa009 | Fmoc-MeAsp-piz(oxe) | | (3S)-3-[9H-fluoren-9-ylmethoxycarbonyl(methyl)amino]-4-[4-(oxetan-3-yl)piperazin-1-yl]-4-oxobutanoic acid |
| aa010 | Fmoc-MeAsp-mor(26-bicyc) | | (3S)-3-[9H-fluoren-9-ylmethoxycarbonyl(methyl)amino]-4-(3-oxa-8-azabicyclo[3.2.1]octane-8-yl)-4-oxobutanoic acid |

TABLE 6-continued

| Compound No. | Abbreviation | Structural formula | Name |
|---|---|---|---|
| aa011 | Fmoc-MeAsp-NMe2 | | (3S)-4-(dimethylamino)-3-[9H-fluoren-9-ylmethoxycarbonyl(methyl)amino]-4-oxobutanoic acid |
| aa012 | Fmoc-MeAsp-aze | | (3S)-4-(azetidin-1-yl)-3-[9H-fluoren-9-ylmethoxycarbonyl(methyl)amino]-4-oxobutanoic acid |
| aa013 | Fmoc-MeAsp-pyrro | | (3S)-3-[9H-fluoren-9-ylmethoxycarbonyl(methyl)amino]-4-oxo-4-pyrrolidin-1-ylbutanoic acid |
| aa014 | Fmoc-MeAsp-pip(4-Me) | | (3S)-3-[9H-fluoren-9-ylmethoxycarbonyl(methyl)amino]-4-(4-methylpiperidin-1-yl)-4-oxobutanoic acid |
| aa015 | Fmoc-MeAsp-mor(SO2) | | (3S)-4-(1,1-dioxo-1,4-thiazinane-4-yl)-3-[9H-fluoren-9-ylmethoxycarbonyl(methyl)amino]-4-oxobutanoic acid |

TABLE 6-continued

| Compound No. | Abbreviation | Structural formula | Name |
| --- | --- | --- | --- |
| aa016 | Fmoc-Asp-piz(oxe) | | (3S)-3-(9H-fluoren-9-ylmethoxycarbonylamino)-4-[4-(oxetan-3-yl)piperazin-1-yl]-4-oxobutanoic acid |
| aa017 | Fmoc-Asp-mor(26-bicyc) | | (3S)-3-(9H-fluoren-9-ylmethoxycarbonylamino)-4-(3-oxa-8-azabicyclo[3.2.1]octane-8-yl)-4-oxobutanoic acid |
| aa018 | Fmoc-Asp-pyrro | | (3S)-3-(9H-fluoren-9-ylmethoxycarbonylamino)-4-oxo-4-pyrrolidin-1-ylbutanoic acid |
| aa019 | Fmoc-Asp-NMe2 | | (3S)-4-(dimethylamino)-3-(9H-fluoren-9-ylmethoxycarbonylamino)-4-oxobutanoic acid |
| aa020 | Fmoc-Asp-pip-tBu | | (3S)-4-(4-tert-butylpiperidin-1-yl)-3-(9H-fluoren-9-ylmethoxycarbonylamino)-4-oxobutanoic acid |
| aa021 | Fmoc-Asp-mor(SO2) | | (3S)-4-(1,1-dioxo-1,4-thiazinane-4-yl)-3-(9H-fluoren-9-ylmethoxycarbonylamino)-4-oxobutanoic acid |

TABLE 6-continued

| Compound No. | Abbreviation | Structural formula | Name |
|---|---|---|---|
| aa022 | Fmoc-Asp-mor | | (3S)-3-(9H-fluoren-9-ylmethoxycarbonylamino)-4-morpholin-4-yl-4-oxobutanoic acid |
| aa023 | Fmoc-Asp-pip(4-Me) | | (3S)-3-(9H-fluoren-9-ylmethoxycarbonylamino)-4-(4-methylpiperidin-1-yl)-4-oxobutanoic acid |
| aa024 | Fmoc-Asp-pyrro(3-Me2) | | (3S)-4-(3,3-dimethylpyrrolidin-1-yl)-3-(9H-fluoren-9-ylmethoxycarbonylamino)-4-oxobutanoic acid |
| aa025 | Fmoc-MeAsp-pip(345-F6) | | (3S)-3-[9H-fluoren-9-ylmethoxycarbonyl(methyl)amino]-4-(3,3,4,4,5,5-hexafluoropiperidin-1-yl)-4-oxobutanoic acid |
| aa026 | Fmoc-Asp-pip(345-F6) | | (3S)-3-(9H-fluoren-9-ylmethoxycarbonylamino)-4-(3,3,4,4,5,5-hexafluoropiperidin-1-yl)-4-oxobutanoic acid |

TABLE 6-continued

| Compound No. | Abbreviation | Structural formula | Name |
| --- | --- | --- | --- |
| aa027 | Fmoc-Asp-pyrro(34-F4) | | (3S)-3-(9H-fluoren-9-ylmethoxycarbonylamino)-4-oxo-4-(3,3,4,4-tetrafluoropyrrolidin-1-yl)butanoic acid |
| aa028 | Fmoc-MeAsp-pyrro(34-F4) | | (3S)-3-[9H-fluoren-9-ylmethoxycarbonyl(methyl)amino]-4-oxo-4-(3,3,4,4-tetrafluoropyrrolidin-1-yl)butanoic acid |
| aa029 | Fmoc-Asp-oxz | | (3S)-3-(9H-fluoren-9-ylmethoxycarbonylamino)-4-(1,3-oxazolidin-3-yl)-4-oxobutanoic acid |
| aa030 | Fmoc-MeAsp-oxz | | (3S)-3-[9H-fluoren-9-ylmethoxycarbonyl(methyl)amino]-4-(1,3-oxazolidin-3-yl)-4-oxobutanoic acid |
| aa031 | Fmoc-D-MeAsp-pyrro | | (3R)-3-[9H-fluoren-9-ylmethoxycarbonyl(methyl)amino]-4-oxo-4-pyrrolidin-1-ylbutanoic acid |

TABLE 6-continued

| Compound No. | Abbreviation | Structural formula | Name |
|---|---|---|---|
| aa032 | Fmoc-EtAsp-pip | | (3S)-3-[ethyl(9H-fluoren-9-ylmethoxycarbonyl)amino]-4-oxo-4-piperidin-1-ylbutanoic acid |
| aa051 | D-MeLeu-(C#CH2)-OH | | (3R)-5-methyl-3-(methylamino)hexanoic acid |
| aa052 | nPrAsp-pip | | (3S)-4-oxo-4-piperidin-1-yl-3-(propyl amino)butanoic acid |
| aa107 | Fmoc-D-Ser(NtBu-Aca)-(C#CH2)-OH | | (3S)-4-[2-(tert-butyl amino)-2-oxoethoxy]-3-(9H-fluoren-9-yl methoxycarbonyl amino) |
| aa108 | Fmoc-D-Ser(iPen)-(C#CH2)-OH | | (3S)-3-(9H-fluoren-9-yl methoxycarbonyl amino)-4-(3-methyl butoxy)butanoic acid |
| aa149 | Fmoc-Asp-pip | | (3S)-3-(9H-fluoren-9-yl methoxycarbonyl amino)-4-oxo-4-piperidin-1-yl butanoic acid |

TABLE 6-continued

| Compound No. | Abbreviation | Structural formula | Name |
| --- | --- | --- | --- |
| aa141 | Fmoc-D-Leu-(C#CH2)-OH | | (3R)-3-(9H-fluoren-9-yl methoxycarbonyl amino)-5-methyl hexanoic acid |
| aa 155 | Fmoc-MeCys (AcOH)-NMe2 | | 2-[(2R)-3-(dimethylamino)-2-[9H-fluoren-9-yl methoxycarbonyl(methyl) amino]-3-oxo-propyl] sulfanylacetic acid |

TABLE 7

| Compound No. | Abbreviation | Structural formula | Name | CAS No. |
| --- | --- | --- | --- | --- |
| aa135 | Fmoc-2-ACHxC-OH | | (1R,2R)-2-(9H-fluoren-9-ylmethoxycarbonyl amino)cyclohexane-1-carboxylic acid | 389057-34-5 |
| aa136 | Fmoc-2-ACPnC-OH | | (1R,2R)-2-(9H-fluoren-9-ylmethoxycarbonyl amino)cyclopentane-1-carboxylic acid | 359586-69-9 |
| aa137 | Fmoc-D-(Propargyl)Gly-(C#CH2)-OH | | (3R)-3-(9H-fluoren-9-ylmethoxycarbonyl amino)hex-5-ynoic acid | 332064-94-5 |

TABLE 7-continued

| Compound No. | Abbreviation | Structural formula | Name | CAS No. |
|---|---|---|---|---|
| aa138 | Fmoc-D-3-Abu-OH | | (3R)-3-(9H-fluoren-9-ylmethoxycarbonyl amino)butanoic acid | 201864-71-3 |
| aa139 | Fmoc-D-3-MeAbu-OH | | (3R)-3-[9H-fluoren-9-ylmethoxycarbonyl (methyl)amino] butanoic acid | 1460306-60-8 |
| aa140 | Fmoc-D-Gly(Allyl)-(C#CH2)-OH | | (3R)-3-(9H-fluoren-9-ylmethoxycarbonyl amino)hex-5-enoic acid | 269726-95-6 |
| aa143 | Fmoc-D-Pic(2)-(C#CH2)-OH | | (R)-2-[1-(9H-fluoren-9-ylmethoxycarbonyl) piperidin-2-yl] acetic acid | 193693-63-9 |
| aa144 | Fmoc-D-Pro-(C#CH2)-OH | | 2-[(2R)-1-(9H-fluoren-9-ylmethoxycarbonyl) pyrrolidin-2-yl] acetic acid | 193693-61-7 |
| aa145 | Fmoc-bMeAla-OH | | 3-[9H-fluoren-9-ylmethoxycarbonyl (methyl)amino] propanoic acid | 172965-84-3 |

TABLE 7-continued

| Compound No. | Abbreviation | Structural formula | Name | CAS No. |
|---|---|---|---|---|
| aa146 | Fmoc-bAla-OH | | 3-(9H-fluoren-9-ylmethoxycarbonyl amino)propanoic acid | 35737-10-1 |
| aa147 | Fmoc-D-Hph-(C#CH2)-OH | | (3R)-3-(9H-Fluoren-9-ylmethoxycarbonyl amino)-5-phenylpentanoic acid | 269398-87-0 |
| aa148 | Fmoc-3-CF3-bAla-OH | | (3S)-3-(9H-fluoren-9-ylmethoxycarbonyl amino)-4,4,4-trifluorobutanoic acid | 1310680-31-9 |

611

Synthesis of Compound aa006-resin, (3S)-3-[9H-fluoren-9-ylmethoxycarbonyl(methyl)amino]-4-oxo-4-piperidin-1-ylbutanoic acid-2-chlorotrityl resin (Fmoc-MeAsp(O-Trt(2-Cl)resin)-pip)

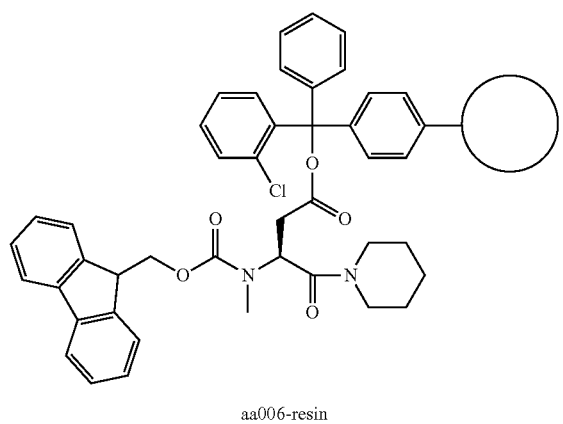 [SMILES: Cc1ccc(C(OC(=O)C[C@@H](C(=O)N2CCCCC2)N(C)C(=O)OCC2c3ccccc3-c3ccccc32)(c2ccccc2)c2ccccc2Cl)cc1]

aa006-resin

Compound aa006-resin ((3S)-3-[9H-fluoren-9-yl-methoxycarbonyl(methyl)amino]-4-oxo-4-piperidin-1-ylbutanoic acid-2-chlorotrityl resin, Fmoc-MeAsp(O-Trt(2-Cl)resin)-pip) was synthesized by the method described in WO 2018/225864.

In the present specification, when a resin is attached to a compound, the resin portion may be indicated as "○." In order to specify the point of reaction in the resin portion, the chemical structure of the reaction site may be indicated as a structure connected to "○." The above structure shows that the 2-chlorotrityl group on the resin is attached to the side chain carboxylic acid of MeAsp through an ester bond in Fmoc-MeAsp(O-Trt(2-Cl)resin)-pip (Compound aa006-resin).

Synthesis of Compound aa007-resin, (3S)-3-[9H-fluoren-9-ylmethoxycarbonyl(methyl)amino]-4-morpholin-4-yl-4-oxobutanoic acid-2-chlorotrityl resin (Fmoc-MeAsp(O-Trt(2-Cl)resin)-mor)

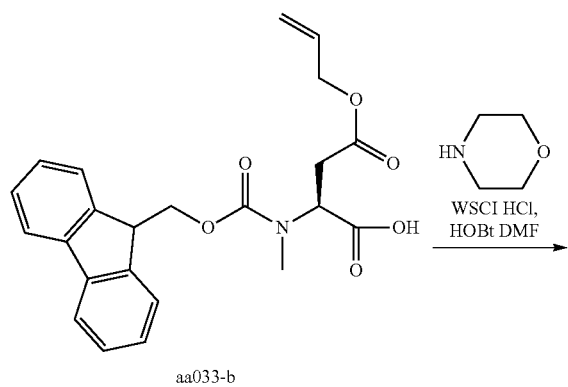

aa033-b

612

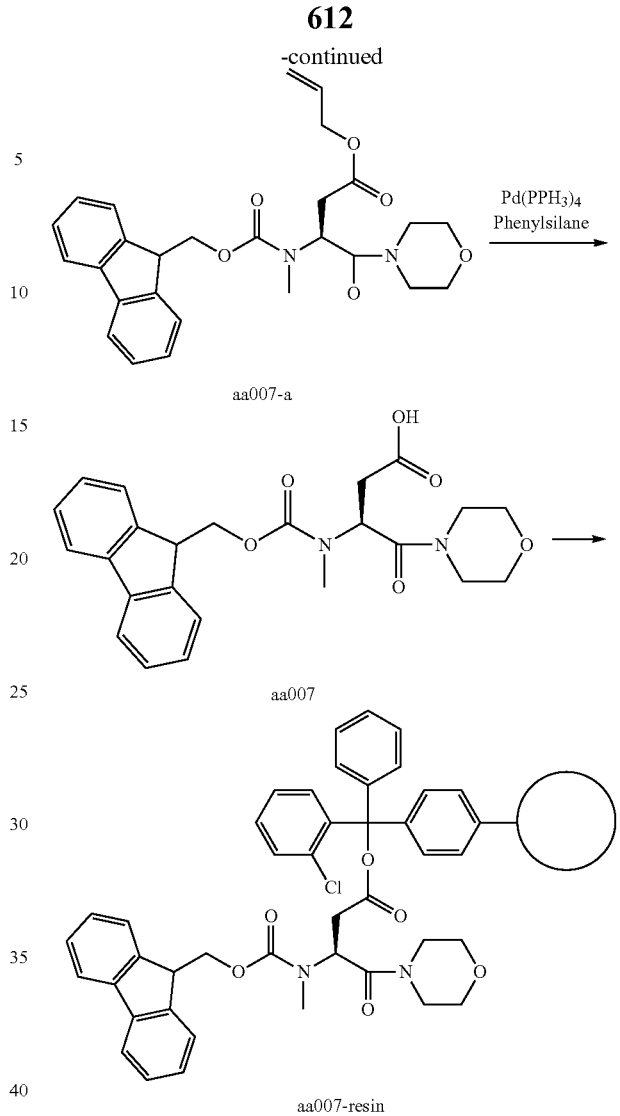

WSCI·HCl (0.506 g, 2.64 mmol) was dissolved in DMF (4.4 mL), HOBt (0.356 g, 2.64 mmol) and Compound aa033-b ((2S)-2-[9H-fluoren-9-ylmethoxycarbonyl(methyl)amino]-4-oxo-4-prop-2-enoxybutanoic acid, Fmoc-MeAsp(OAl)—OH) (0.9 g, 2.2 mmol) were added, and the mixture was stirred at 0° C. for 10 minutes. To the reaction solution was added morpholine (0.23 mL, 2.64 mmol) dropwise, and the mixture was stirred at 0° C. for one hour. Ethyl acetate (9 mL) was added to the reaction solution, which was washed with 0.5 N aqueous hydrochloric acid, water, saturated aqueous sodium bicarbonate/water (1/1), and brine/water (1/1) and dried over anhydrous sodium sulfate. The solvent was then evaporated under reduced pressure to give Compound aa007-a as a crude product (522 mg, 50%).

LCMS (ESI) m/z=479 (M+H)+

Retention time: 0.87 min (analysis condition SQDFA05)

To a solution of Compound aa007-a (446 mg, 0.932 mmol) in DCM (1.86 mL) was added tetrakis(triphenylphosphine)palladium (0) (10.8 mg, 0.0093 mmol), and phenylsilane (0.081 mL, 0.653 mmol) was further added dropwise, then the mixture was stirred at room temperature for 30 minutes. The reaction solution was diluted with TBME and a 5% aqueous sodium bicarbonate solution was added. The organic layer was removed, phosphoric acid (548 mg) was added to the aqueous layer, which was extracted with TBME. The organic layer was washed with brine and dried over anhydrous sodium sulfate, and the solvent was then evaporated under reduced pressure to give Compound aa007 ((3S)-3-[9H-fluoren-9-ylmethoxycarbonyl(methyl)amino]-4-morpholin-4-yl-4-oxobutanoic acid, Fmoc-MeAsp-mor) (321 mg, 79%).

LCMS(ESI) m/z=439 (M+H)+

Retention time: 0.69 min (analysis condition SQDFA05)

Fmoc amino acids were loaded on resins according to the method described in WO 2013/100132 or WO 2018/225864. In a reaction vessel equipped with a filter were placed 2-chlorotrityl chloride resin (1.60 mmol/g, 100-200 mesh, 1% DVB, 1 g, 1.6 mmol) and dehydrated dichloromethane (13.3 mL), and the vessel was shaken at room temperature for 10 minutes. The dichloromethane was removed by applying nitrogen pressure, after which dehydrated methanol (0.259 mL, 6.4 mmol) and diisopropylethylamine (DIPEA) (0.671 mL, 3.84 mmol) were added to a solution of Compound aa007 ((3S)-3-[9H-fluoren-9-ylmethoxycarbonyl(methyl)amino]-4-morpholin-4-yl-4-oxobutanoic acid, Fmoc-MeAsp-mor) (317 mg, 0.723 mmol) in dehydrated dichloromethane (13.3 mL), the resulting mixture was added to the reaction vessel, and the vessel was shaken for 30 minutes. The reaction solution was removed by applying nitrogen pressure, after which dehydrated methanol (1.99 mL) and diisopropylethylamine (DIPEA) (0.671 mL) were added to dehydrated dichloromethane (13.3 mL), the resulting mixture was added to the reaction vessel, and the vessel was shaken for 1 hour and 30 minutes. The reaction solution was removed by applying nitrogen pressure, after which dichloromethane was added to the reaction vessel. After shaking for 5 minutes, the reaction solution was removed by applying nitrogen pressure. This operation of washing the resin with dichloromethane was further repeated twice, and the resulting resin was dried under reduced pressure overnight to give Compound aa007-resin ((3S)-3-[9H-fluoren-9-ylmethoxycarbonyl(methyl)amino]-4-morpholin-4-yl-4-oxobutanoic acid-2-chlorotrityl resin, Fmoc-MeAsp(O-Trt(2-Cl)resin)-mor) (1.22 g, 0.37 mmol/g).

The amount of the amino acid loaded on the resin was calculated as follows. The obtained Compound aa007-resin ((3S)-3-[9H-fluoren-9-ylmethoxycarbonyl(methyl)amino]-4-morpholin-4-yl-4-oxobutanoic acid-2-chlorotrityl resin, Fmoc-MeAsp(O-Trt(2-Cl)resin)-mor) (10.4 mg) was placed in a reaction vessel, DMF (2 mL) was added, and the vessel was shaken at room temperature for one hour. DBU (40 µL) was then added and the mixture was shaken at 30° C. for 30 minutes. DMF (8 mL) was then added to the reaction mixture, and 1 mL of the solution was diluted with DMF (11.5 mL). The absorbance (294 nm) of the resulting diluted solution was measured (using Shimadzu, UV-1600PC (cell length: 1.0 cm)), and the loading amount of Compound aa007-resin was calculated to be 0.370 mmol/g.

Another lot synthesized in the same manner with a different loading amount was also used for peptide synthesis.

Synthesis of Compound aa008-resin, (3S)-4-(3,3-dimethylpyrrolidin-1-yl)-3-[9H-fluoren-9-yl-methoxycarbonyl(methyl)amino]-4-oxobutanoic acid-2-chlorotrityl resin (Fmoc-MeAsp(O-Trt(2-Cl) resin)-pyrro(3-Me2))

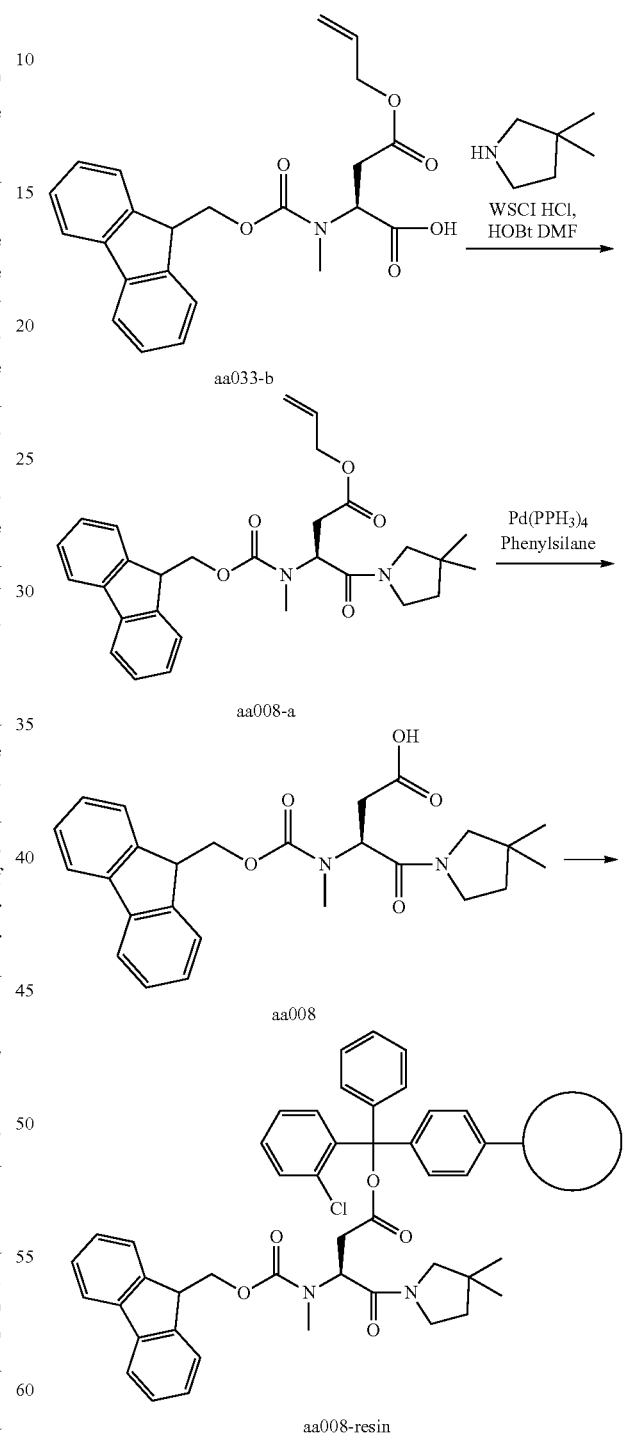

Compound aa008-a (359.6 mg, 60%) was obtained by the same method as in the synthesis of Compound aa007-a using Compound aa033-b ((2S)-2-[9H-fluoren-9-ylmethoxycarbonyl(methyl)amino]-4-oxo-4-prop-2-enoxybutanoic acid)

(0.5 g, 1.221 mmol) as a starting material and using 3,3-dimethylpyrrolidine instead of morpholine.

LCMS (ESI) m/z=491 (M+H)+

Retention time: 0.98 min (analysis condition SQDFA05)

Compound aa008 ((3S)-4-(3,3-dimethylpyrrolidin-1-yl)-3-[9H-fluoren-9-ylmethoxycarbonyl(methyl)amino]-4-oxobutanoic acid, Fmoc-MeAsp-pyrro(3-Me2)) (226.2 mg, 73%) was obtained by the same method as in the synthesis of Compound aa007 using the obtained Compound aa008-a (338 mg, 0.689 mmol).

LCMS (ESI) m/z=451 (M+H)+

Retention time: 0.84 min (analysis condition SQDFA05)

Compound aa008-resin ((3S)-4-(3,3-dimethylpyrrolidin-1-yl)-3-[9H-fluoren-9-ylmethoxycarbonyl(methyl)amino]-4-oxobutanoic acid-2-chlorotrityl resin, Fmoc-MeAsp(O-Trt(2-Cl)resin)-pyrro(3-Me2)) (731 mg, loading amount 0.455 mmol/g) was obtained by the same method as in the synthesis of Compound aa007-resin using the obtained Compound aa008 ((3S)-4-(3,3-dimethylpyrrolidin-1-yl)-3-[9H-fluoren-9-ylmethoxycarbonyl(methyl)amino]-4-oxobutanoic acid, Fmoc-MeAsp-pyrro(3-Me2)) (226 mg, 0.502 mmol).

Synthesis of Compound aa009-resin, (3S)-3-[9H-fluoren-9-ylmethoxycarbonyl(methyl)amino]-4-[4-(oxetan-3-yl)piperazin-1-yl]-4-oxobutanoic acid-2-chlorotrityl resin (Fmoc-MeAsp(O-Trt(2-Cl)resin)-piz(oxe))

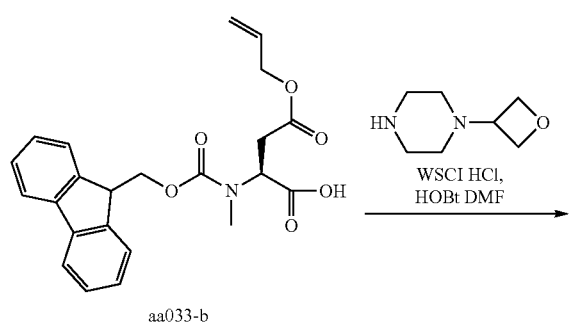

aa033-b

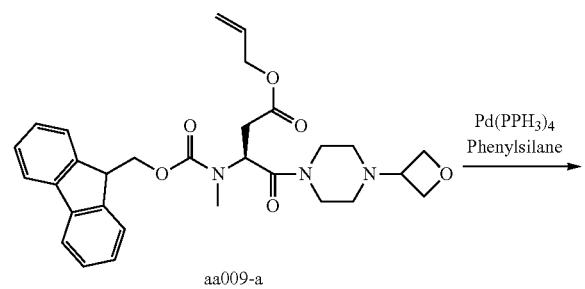

aa009-a

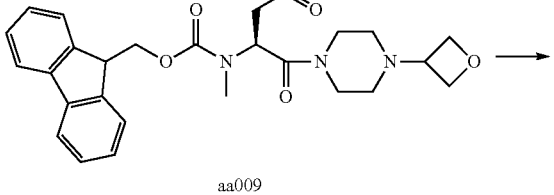

aa009

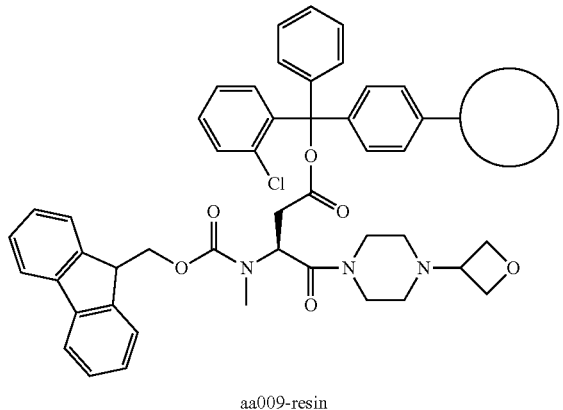

aa009-resin

Compound aa009-a (466 mg, 89%) was obtained by the same method as in the synthesis of Compound aa007-a using Compound aa033-b ((2S)-2-[9H-fluoren-9-ylmethoxycarbonyl(methyl)amino]-4-oxo-4-prop-2-enoxybutanoic acid) (0.4 g, 0.977 mmol) as a starting material and using 1-(oxetan-3-yl)piperazine instead of morpholine.

LCMS (ESI) m/z=534 (M+H)+

Retention time: 0.64 min (analysis condition SQDFA05)

A crude product obtained by the same method as in the synthesis of Compound aa007 using the obtained Compound aa009-a (466 mg, 0.873 mmol) was purified by reverse phase column chromatography (acetonitrile with 0.1% formic acid/distilled water with 0.1% formic acid) to give Compound aa009 ((3S)-3-[9H-fluoren-9-ylmethoxycarbonyl(methyl)amino]-4-[4-(oxetan-3-yl)piperazin-1-yl]-4-oxobutanoic acid, Fmoc-MeAsp-piz(oxe)) (385 mg, 89%).

LCMS (ESI) m/z=494 (M+H)+

Retention time: 0.50 min (analysis condition SQDFA05)

Compound aa009-resin ((3S)-3-[9H-fluoren-9-ylmethoxycarbonyl(methyl)amino]-4-[4-(oxetan-3-yl)piperazin-1-yl]-4-oxobutanoic acid-2-chlorotrityl resin, Fmoc-MeAsp(O-Trt(2-Cl)resin)-piz(oxe)) (1.49 g, loading amount 0.266 mmol/g) was obtained by the same method as in the synthesis of Compound aa007-resin using the obtained Compound aa009 ((3S)-3-[9H-fluoren-9-ylmethoxycarbonyl(methyl)amino]-4-[4-(oxetan-3-yl)piperazin-1-yl]-4-oxobutanoic acid, Fmoc-MeAsp-piz(oxe)) (385 mg, 0.78 mmol).

Synthesis of Compound aa010-resin, (3S)-3-[9H-fluoren-9-ylmethoxycarbonyl(methyl)amino]-4-(3-oxa-8-azabicyclo[3.2.1]octan-8-yl)-4-oxobutanoic acid-2-chlorotrityl resin (Fmoc-MeAsp(O-Trt(2-Cl)resin)-Mor(26-bicyc))

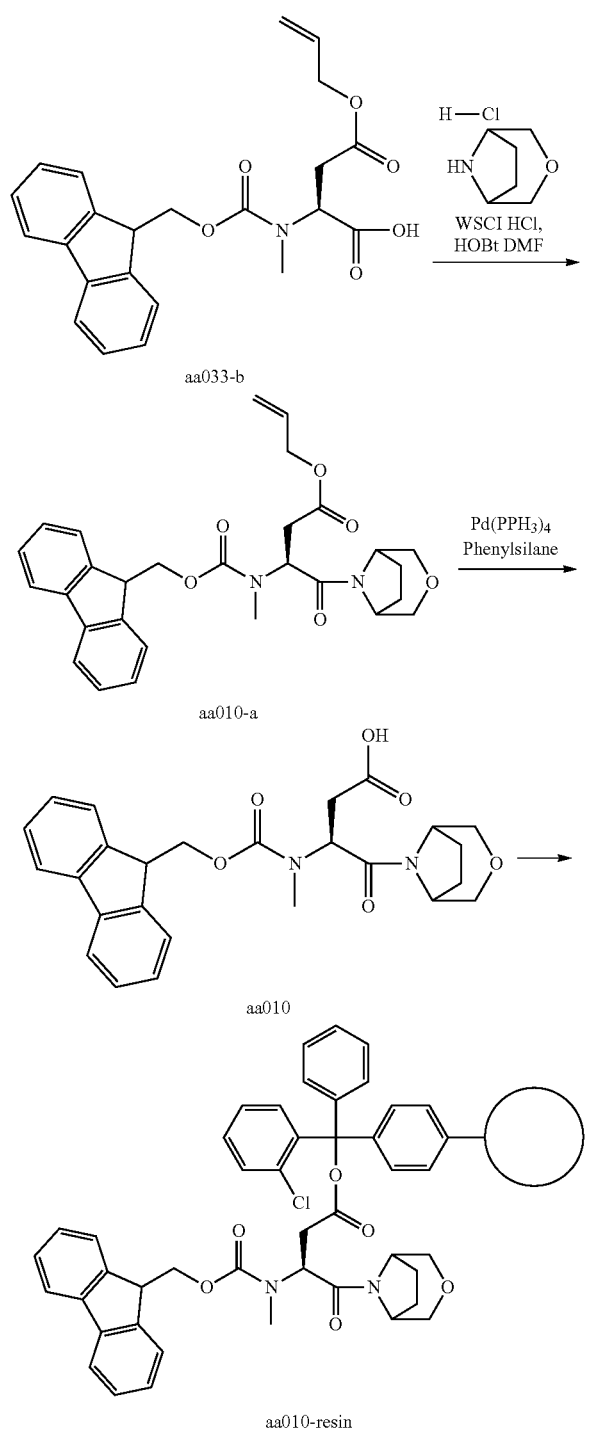

Compound aa010-a (5.8 g, 94%) was obtained by the same method as in the synthesis of Compound aa007-a using Compound aa033-b ((2S)-2-[9H-fluoren-9-ylmethoxycarbonyl(methyl)amino]-4-oxo-4-prop-2-enoxybutanoic acid) (5 g, 12.21 mmol) as a starting material and using (1R,5S)-3-oxa-8-azabicyclo[3.2.1]octane hydrochloride and one equivalent of DIPEA relative to amine, instead of morpholine.

LCMS (ESI) m/z=505 (M+H)+

Retention time: 0.87 min (analysis condition SQDFA05)

Compound aa010 ((3S)-3-[9H-fluoren-9-ylmethoxycarbonyl(methyl)amino]-4-(3-oxa-8-azabicyclo[3.2.1]octan-8-yl)-4-oxobutanoic acid, Fmoc-MeAsp-Mor(26-bicyc)) (5.1 g, 96%) was obtained by the same method as in the synthesis of Compound aa007 using the obtained Compound aa010-a (5.8 g, 11.49 mmol).

LCMS (ESI) m/z=465 (M+H)+

Retention time: 0.69 (analysis condition SQDFA05)

Compound aa010-resin ((3S)-3-[9H-fluoren-9-ylmethoxycarbonyl(methyl)amino]-4-(3-oxa-8-azabicyclo[3.2.1]octan-8-yl)-4-oxobutanoic acid-2-chlorotrityl resin, Fmoc-MeAsp(O-Trt(2-Cl)resin)-Mor(26-bicyc)) (18.3 g, loading amount 0.419 mmol/g) was obtained by the same method as in the synthesis of Compound aa007-resin using the obtained Compound aa010 ((3S)-3-[9H-fluoren-9-ylmethoxycarbonyl(methyl)amino]-4-(3-oxa-8-azabicyclo[3.2.1]octan-8-yl)-4-oxobutanoic acid, Fmoc-MeAsp-Mor(26-bicyc)) (5.1 g, 10.98 mmol).

Another lot synthesized in the same manner with a different loading amount was also used for peptide synthesis in the present Examples.

Synthesis of Compound aa011-resin, (3S)-4-(dimethylamino)-3-[9H-fluoren-9-ylmethoxycarbonyl(methyl)amino]-4-oxobutanoic acid-2-chlorotrityl resin (Fmoc-MeAsp(O-Trt(2-Cl)resin)-NMe2)

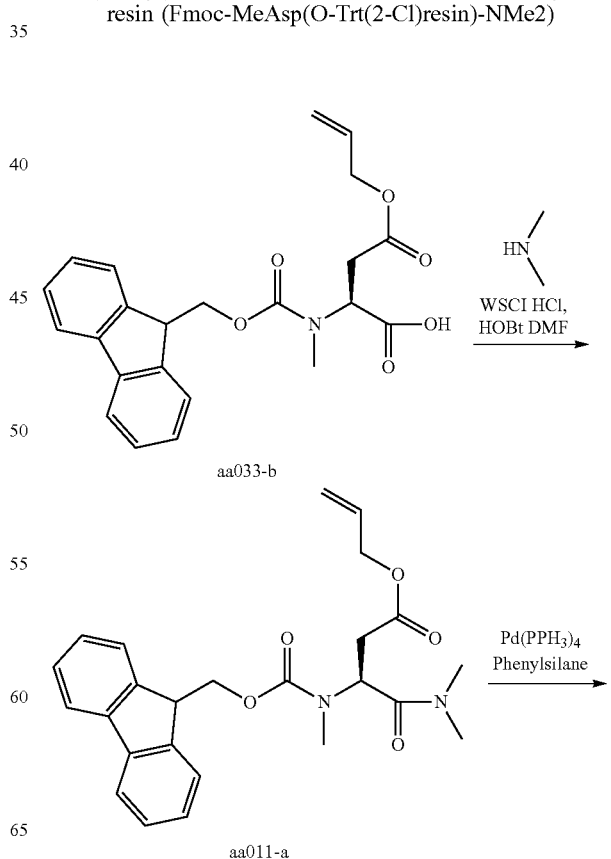

619
-continued

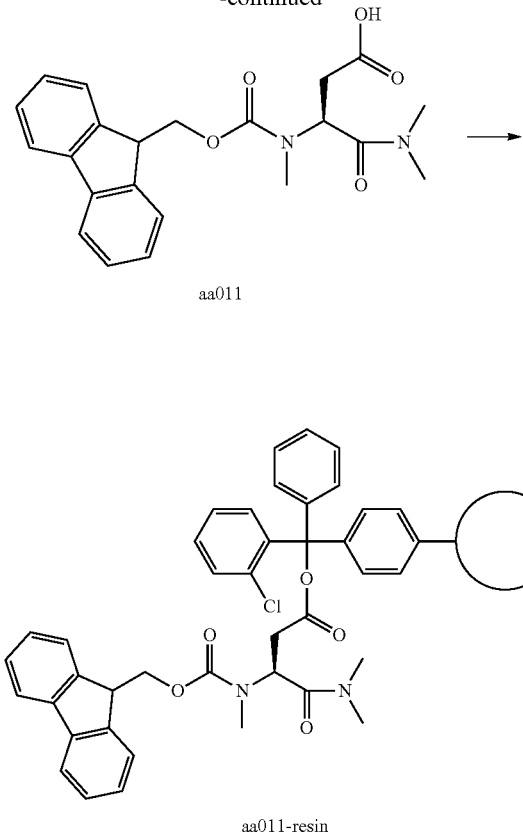

aa011 aa011-resin

Compound aa011-a (1.47 g, 92%) was obtained by the same method as in the synthesis of Compound aa007-a using Compound aa033-b ((2S)-2-[9H-fluoren-9-ylmethoxycarbonyl(methyl)amino]-4-oxo-4-prop-2-enoxybutanoic acid) (1.5 g, 3.66 mmol) as a starting material and using a solution of dimethylamine in THF (2 mol/L) instead of morpholine.

LCMS (ESI) m/z=437 (M+H)+

Retention time: 0.88 min (analysis condition SQDFA05)

Compound aa011 ((3S)-4-(dimethylamino)-3-[9H-fluoren-9-ylmethoxycarbonyl(methyl)amino]-4-oxobutanoic acid, Fmoc-MeAsp-NMe2) (1.30 g, quant.) was obtained by the same method as in the synthesis of Compound aa007 using the obtained Compound aa011-a (1.4 g, 3.21 mmol).

LCMS (ESI) m/z=397 (M+H)+

Retention time: 0.70 min (analysis condition SQDFA05)

Compound aa011-resin ((3S)-4-(dimethylamino)-3-[9H-fluoren-9-ylmethoxycarbonyl(methyl)amino]-4-oxobutanoic acid-2-chlorotrityl resin, Fmoc-MeAsp(O-Trt(2-Cl)resin)-NMe2) (4.45 g, loading amount 0.318 mmol/g) was obtained by the same method as in the synthesis of Compound aa007-resin using the obtained Compound aa011 ((3S)-4-(dimethylamino)-3-[9H-fluoren-9-ylmethoxycarbonyl(methyl)amino]-4-oxobutanoic acid, Fmoc-MeAsp-NMe2) (1.21 g, 3.05 mmol).

Another lot synthesized in the same manner with a different loading amount was also used for peptide synthesis in the present Examples.

620
Synthesis of Compound aa012-resin, (3S)-4-(azetidin-1-yl)-3-[9H-fluoren-9-ylmethoxycarbonyl(methyl)amino]-4-oxobutanoic acid-2-chlorotrityl resin (Fmoc-MeAsp(O-Trt(2-Cl)resin)-aze)

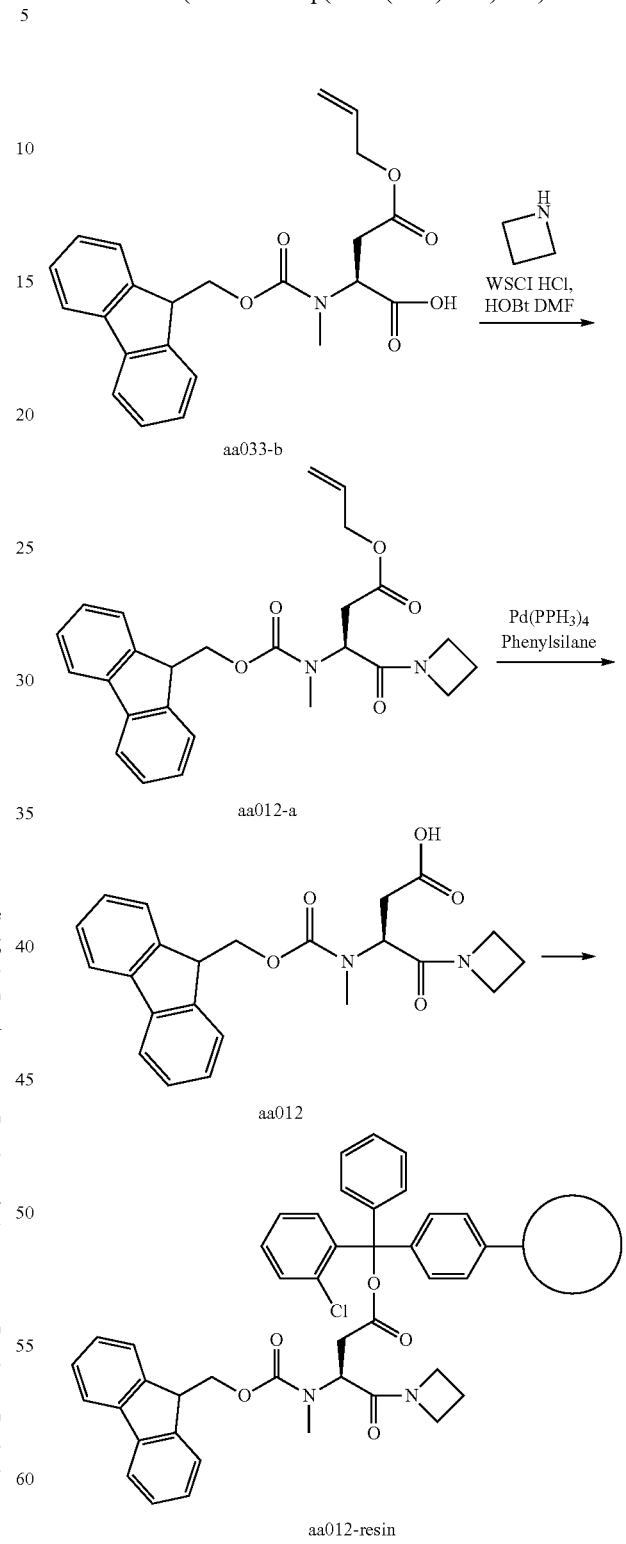

aa033-b aa012-a aa012 aa012-resin

Compound aa012-a (1.41 g, 86%) was obtained by the same method as in the synthesis of Compound aa007-a using Compound aa033-b ((2S)-2-[9H-fluoren-9-ylmethoxycarbonyl(methyl)amino]-4-oxo-4-prop-2-enoxybutanoic acid) (1.5 g, 3.66 mmol) as a starting material and using azetidine instead of morpholine.

LCMS (ESI) m/z=449 (M+H)+

Retention time: 0.86 min (analysis condition SQDFA05)

Compound aa012 ((3S)-4-(azetidin-1-yl)-3-[9H-fluoren-9-ylmethoxycarbonyl(methyl)amino]-4-oxobutanoic acid, Fmoc-MeAsp-aze) (1.14 g, 89%) was obtained by the same method as in the synthesis of Compound aa007 using the obtained Compound aa012-a (1.4 g, 3.12 mmol).

LCMS (ESI) m/z=409 (M+H)+

Retention time: 0.69 min (analysis condition SQDFA05)

Compound aa012-resin ((3S)-4-(azetidin-1-yl)-3-[9H-fluoren-9-ylmethoxycarbonyl(methyl)amino]-4-oxobutanoic acid-2-chlorotrityl resin, Fmoc-MeAsp(O-Trt(2-Cl)resin)-aze) (3.64 g, loading amount 0.2984 mmol/g) was obtained by the same method as in the synthesis of Compound aa007-resin using the obtained Compound aa012 ((3S)-4-(azetidin-1-yl)-3-[9H-fluoren-9-ylmethoxycarbonyl(methyl)amino]-4-oxobutanoic acid, Fmoc-MeAsp-aze) (1.05 g, 2.57 mmol).

Another lot synthesized in the same manner with a different loading amount was also used for peptide synthesis in the present Examples.

Synthesis of Compound aa013-resin, (3S)-3-[9H-fluoren-9-ylmethoxycarbonyl(methyl)amino]-4-oxo-4-pyrrolidin-1-ylbutanoic acid-2-chlorotrityl resin (Fmoc-MeAsp(O-Trt(2-Cl)resin)-pyrro)

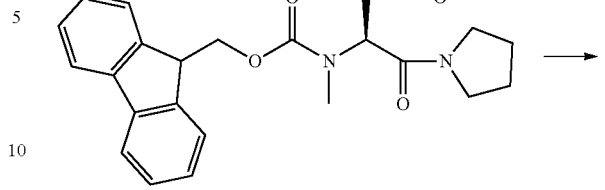

aa013

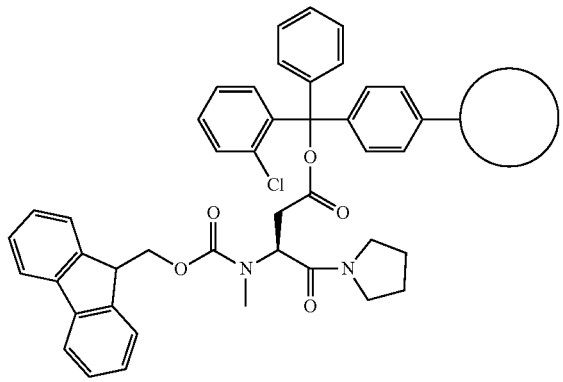

aa013-resin

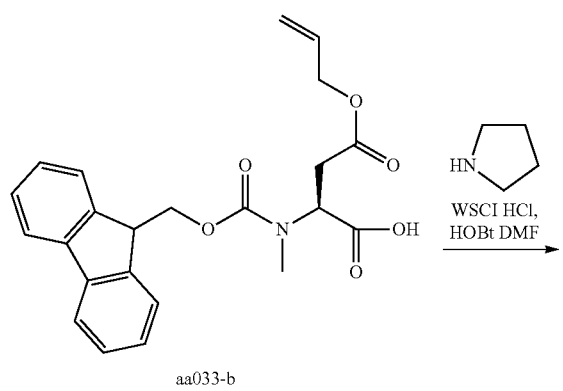

aa033-b

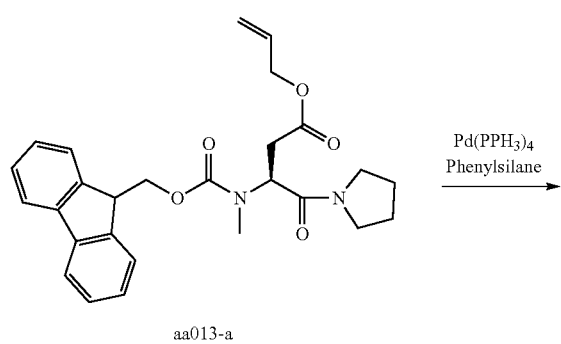

aa013-a

Compound aa013-a (30.7 g, 91%) was obtained by the same method as in the synthesis of Compound aa007-a using Compound aa033-b ((2S)-2-[9H-fluoren-9-ylmethoxycarbonyl(methyl)amino]-4-oxo-4-prop-2-enoxybutanoic acid) (30 g, 73.3 mmol) as a starting material and using pyrrolidine instead of morpholine.

LCMS (ESI) m/z=463 (M+H)+

Retention time: 0.88 min (analysis condition SQDFA05)

Compound aa013 ((3S)-3-[9H-fluoren-9-ylmethoxycarbonyl(methyl)amino]-4-oxo-4-pyrrolidin-1-ylbutanoic acid, Fmoc-MeAsp-pyrro) (26.2 g, 93%) was obtained by the same method as in the synthesis of Compound aa007 using the obtained Compound aa013-a (30.7 g, 66.4 mmol).

LCMS (ESI) m/z=423 (M+H)+

Retention time: 0.71 min (analysis condition SQDFA05)

Compound aa013-resin (9H-fluoren-9-ylmethoxycarbonyl(methyl)amino]-4-oxo-4-pyrrolidin-1-ylbutanoic acid-2-chlorotrityl resin, Fmoc-MeAsp(O-Trt(2-Cl)resin)-pyrro) (84.1 g, loading amount 0.5216 mmol/g) was obtained by the same method as in the synthesis of Compound aa007-resin using the obtained Compound aa013 ((3S)-3-[9H-fluoren-9-ylmethoxycarbonyl(methyl)amino]-4-oxo-4-pyrrolidin-1-ylbutanoic acid, Fmoc-MeAsp-pyrro) (24.6 g, 58.2 mmol).

Another lot synthesized in the same manner with a different loading amount was also used for peptide synthesis in the present Examples.

623

Synthesis of Compound aa014-resin, (3S)-3-[9H-fluoren-9-ylmethoxycarbonyl(methyl)amino]-4-(4-methylpiperidin-1-yl)-4-oxobutanoic acid-2-chlorotrityl resin (Fmoc-MeAsp(O-Trt(2-Cl)resin)-pip(4-Me))

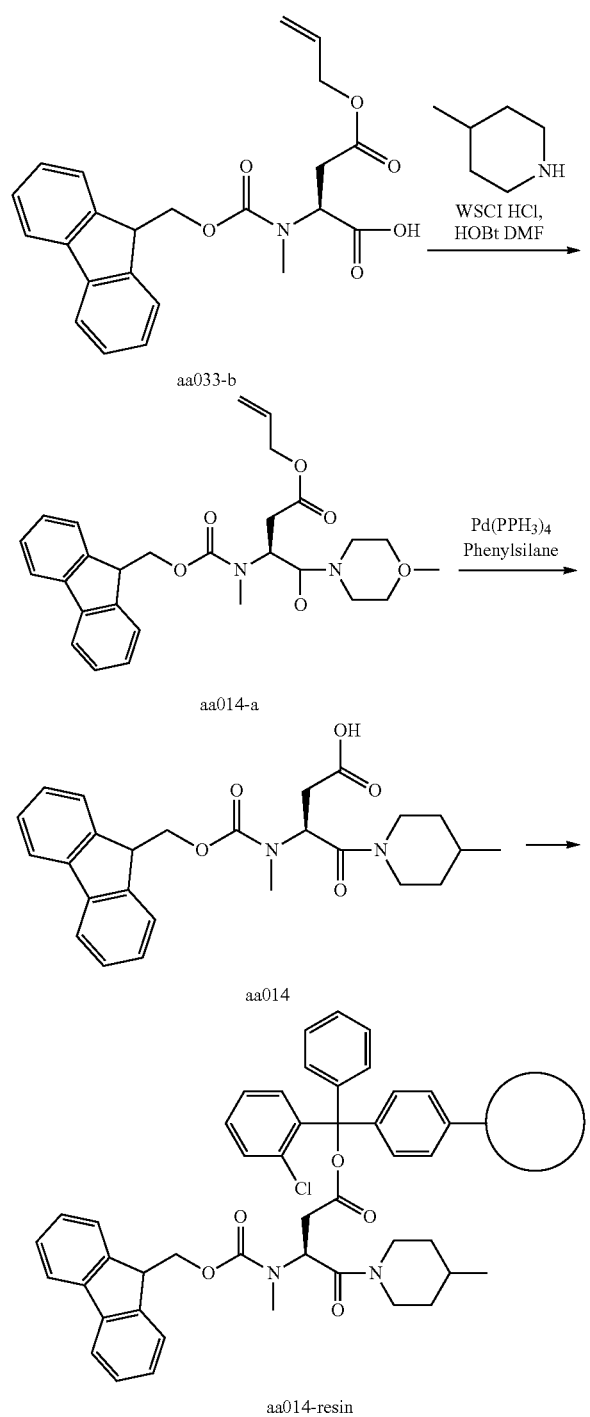

A crude product of Compound aa014-a was obtained by the same method as in the synthesis of Compound aa007-a using Compound aa033-b ((2S)-2-[9H-fluoren-9-ylmethoxycarbonyl(methyl)amino]-4-oxo-4-prop-2-enoxybutanoic acid) (0.9 g, 2.198 mmol) as a starting material and using 4-methylpiperidine instead of morpholine. The resulting crude product was purified by reverse phase column chromatography (water-acetonitrile, containing 0.1% formic acid), further dissolved in 20% ethyl acetate-hexane, then washed twice with a saturated aqueous sodium bicarbonate solution and once with a saturated aqueous sodium chloride solution, and dried over anhydrous sodium sulfate, the solvent was then evaporated under reduced pressure to give Compound aa014-a (0.587 g, 54%).

LCMS (ESI) m/z=491 (M+H)+

Retention time: 1.02 min (analysis condition SQDFA05)

Compound aa014 ((3S)-3-[9H-fluoren-9-ylmethoxycarbonyl(methyl)amino]-4-(4-methylpiperidin-1-yl)-4-oxobutanoic acid, Fmoc-MeAsp-pip(4-Me)) (376.6 mg, 77%) was obtained by the same method as in the synthesis of Compound aa007 using the obtained Compound aa014-a (535 mg, 1.09 mmol).

LCMS (ESI) m/z=451 (M+H)+

Retention time: 0.85 min (analysis condition SQDFA05)

Compound aa014-resin ((3S)-3-[9H-fluoren-9-ylmethoxycarbonyl(methyl)amino]-4-(4-methylpiperidin-1-yl)-4-oxobutanoic acid-2-chlorotrityl resin, Fmoc-MeAsp(O-Trt(2-Cl)resin)-pip(4-Me)) (1.2 g, loading amount 0.403 mmol/g) was obtained by the same method as in the synthesis of Compound aa007-resin using the obtained Compound aa014 ((3S)-3-[9H-fluoren-9-ylmethoxycarbonyl(methyl)amino]-4-(4-methylpiperidin-1-yl)-4-oxobutanoic acid, Fmoc-MeAsp-pip(4-Me)) (364 mg, 0.808 mmol).

Synthesis of Compound aa015-resin, (3S)-4-(1,1-dioxo-1,4-thiazinan-4-yl)-3-[9H-fluoren-9-ylmethoxycarbonyl(methyl)amino]-4-oxobutanoic acid-2-chlorotrityl resin (Fmoc-MeAsp(O-Trt(2-Cl)resin)-mor(SO2))

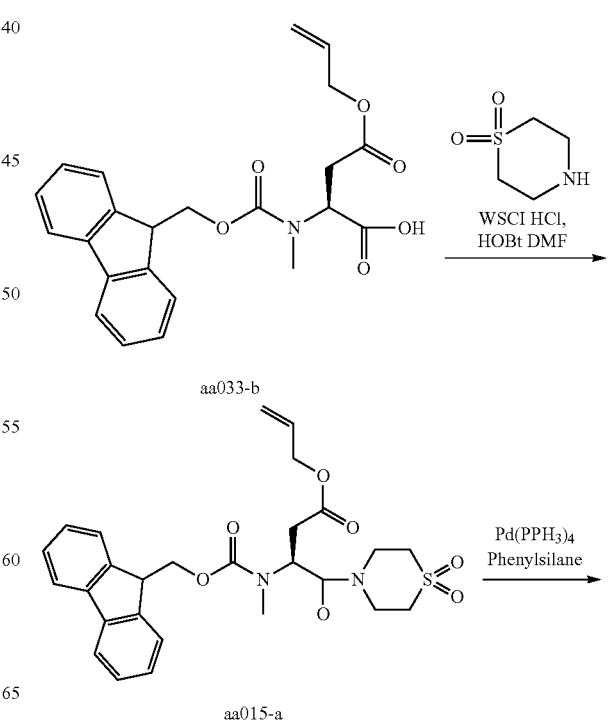

625

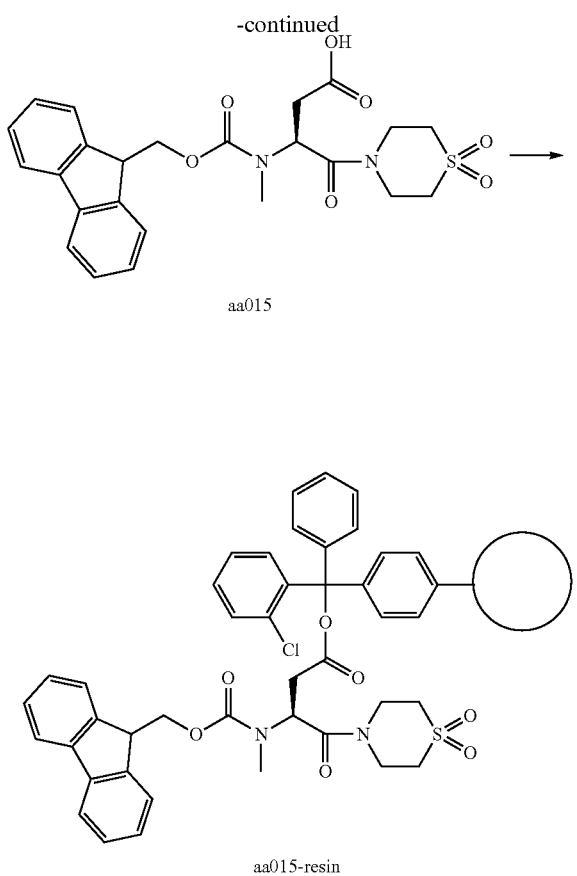

aa015 aa015-resin

Compound aa015-a (796.2 mg, 69%) was obtained by the same method as in the synthesis of Compound aa007-a using Compound aa033-b ((2S)-2-[9H-fluoren-9-ylmethoxycarbonyl(methyl)amino]-4-oxo-4-prop-2-enoxybutanoic acid) (0.9 g, 2.198 mmol) as a starting material and using 1,1-dioxido-thiomorpholine instead of morpholine.

LCMS (ESI) m/z=527 (M+H)+

Retention time: 0.84 min (analysis condition SQDFA05)

Compound aa015 ((3S)-4-(1,1-dioxo-1,4-thiazinan-4-yl)-3-[9H-fluoren-9-ylmethoxycarbonyl(methyl)amino]-4-oxobutanoic acid, Fmoc-MeAsp-mor(SO2)) (624.2 mg, 91%) was obtained by the same method as in the synthesis of Compound aa007 using the obtained Compound aa015-a (743 mg, 1.41 mmol).

LCMS (ESI) m/z=487 (M+H)+

Retention time: 0.68 min (analysis condition SQDFA05)

Compound aa015-resin ((3S)-4-(1,1-dioxo-1,4-thiazinan-4-yl)-3-[9H-fluoren-9-ylmethoxycarbonyl(methyl)amino]-4-oxobutanoic acid-2-chlorotrityl resin, Fmoc-MeAsp(O-Trt(2-Cl)resin)-mor(SO2)) (1.85 g, loading amount 0.424 mmol/g) was obtained by the same method as in the synthesis of Compound aa007-resin using the obtained Compound aa015 ((3S)-4-(1,1-dioxo-1,4-thiazinan-4-yl)-3-[9H-fluoren-9-ylmethoxycarbonyl(methyl)amino]-4-oxobutanoic acid, Fmoc-MeAsp-mor(SO2)) (606.7 mg, 1.247 mmol).

626

Synthesis of Compound aa016-resin, (3S)-3-(9H-fluoren-9-ylmethoxycarbonylamino)-4-[4-(oxetan-3-yl)piperazin-1-yl]-4-oxobutanoic acid-2-chlorotrityl resin (Fmoc-Asp(O-Trt(2-Cl)resin)-piz(oxe))

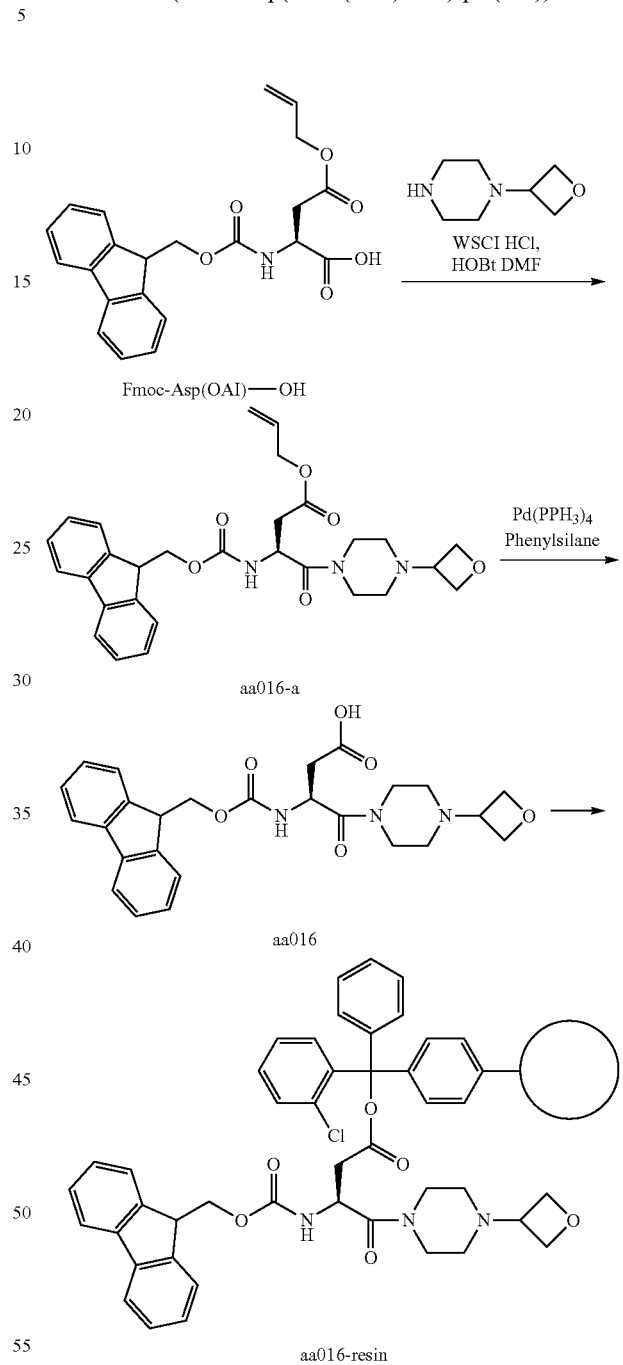

Fmoc-Asp(OAl)—OH aa016-a aa016 aa016-resin

Compound aa016-a (499 mg, 95%) was obtained by the same method as in the synthesis of Compound aa007-a using Fmoc-Asp(OAl)—OH ((2S)-2-(9H-fluoren-9-ylmethoxycarbonylamino)-4-oxo-4-prop-2-enoxybutanoic acid, CAS No. 146982-24-3) (0.4 g, 1.012 mmol) as a starting material and using 1-(oxetan-3-yl)piperazine instead of morpholine.

LCMS (ESI) m/z=520 (M+H)+

Retention time: 0.60 min (analysis condition SQDFA05)

Compound aa016 ((3S)-3-(9H-fluoren-9-ylmethoxycarbonylamino)-4-[4-(oxetan-3-yl)piperazin-1-yl]-4-oxobutanoic acid (Fmoc-Asp-piz(oxe)) (415 mg, 90%) was obtained by the same method as in the synthesis of Compound aa007 using the obtained Compound aa016-a (499 mg, 0.960 mmol).

LCMS (ESI) m/z=480 (M+H)+

Retention time: 0.49 min (analysis condition SQDFA05)

Compound aa016-resin ((3S)-3-(9H-fluoren-9-ylmethoxycarbonylamino)-4-[4-(oxetan-3-yl)piperazin-1-yl]-4-oxobutanoic acid-2-chlorotrityl resin, Fmoc-Asp(O-Trt(2-Cl)resin)-piz(oxe)) (463 mg, loading amount 0.329 mmol/g) was obtained by the same method as in the synthesis of Compound aa007-resin using the obtained Compound aa016 ((3S)-3-(9H-fluoren-9-ylmethoxycarbonylamino)-4-[4-(oxetan-3-yl)piperazin-1-yl]-4-oxobutanoic acid (Fmoc-Asp-piz(oxe)) (123 mg, 0.256 mmol).

Synthesis of Compound aa017-resin, (3S)-3-(9H-fluoren-9-ylmethoxycarbonylamino)-4-(3-oxa-8-azabicyclo[3.2.1]octan-8-yl)-4-oxobutanoic acid-2-chlorotrityl resin (Fmoc-Asp(O-Trt(2-Cl)resin)-Mor(26-bicyc))

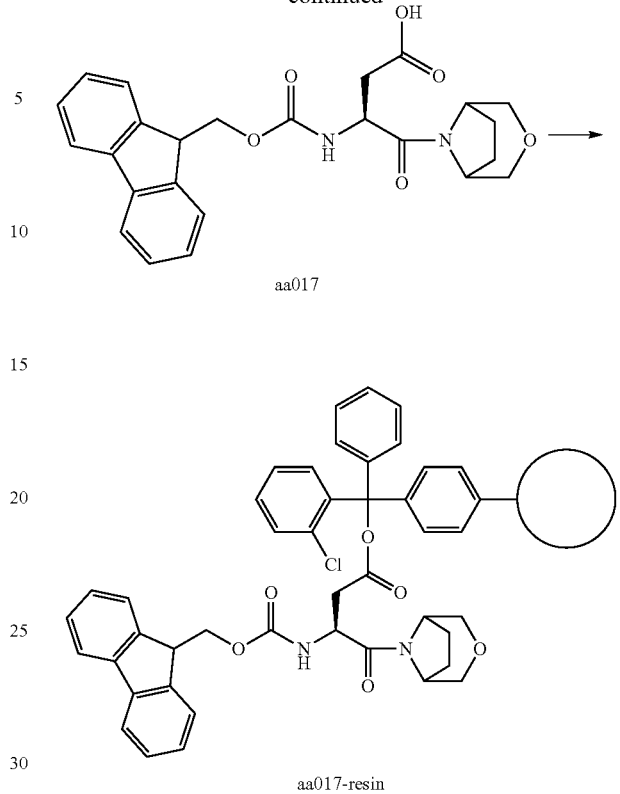

aa017

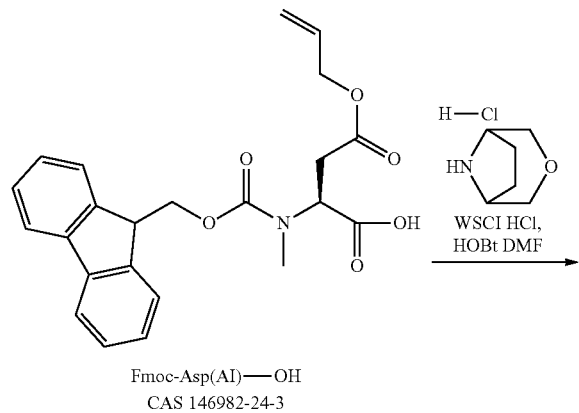

Fmoc-Asp(Al)—OH
CAS 146982-24-3

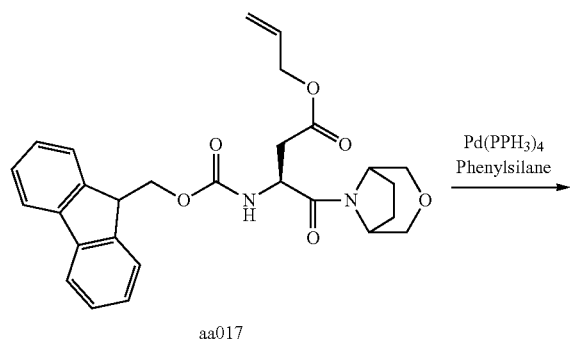

aa017

Compound aa017-a (706 mg, 95%) was obtained by the same method as in the synthesis of Compound aa007-a using Fmoc-Asp(OAl)—OH ((2S)-2-(9H-fluoren-9-ylmethoxycarbonylamino)-4-oxo-4-prop-2-enoxybutanoic acid, CAS No. 146982-24-3) (0.6 g, 1.517 mmol) as a starting material and using (1R,5S)-3-oxa-8-azabicyclo[3.2.1]octane hydrochloride and one equivalent of DIPEA relative to amine, instead of morpholine.

LCMS (ESI) m/z=491 (M+H)+

Retention time: 0.82 (analysis condition SQDFA05)

Compound aa017 ((3S)-3-(9H-fluoren-9-ylmethoxycarbonylamino)-4-(3-oxa-8-azabicyclo[3.2.1]octan-8-yl)-4-oxobutanoic acid, Fmoc-Asp-Mor(26-bicyc)) (564.5 mg, 87%) was obtained by the same method as in the synthesis of Compound aa007 using the obtained Compound aa017-a (705 mg, 1.437 mmol).

LCMS (ESI) m/z=451 (M+H)+

Retention time: 0.66 min (analysis condition SQDFA05)

Compound aa017-resin ((3S)-3-(9H-fluoren-9-ylmethoxycarbonylamino)-4-(3-oxa-8-azabicyclo[3.2.1]octan-8-yl)-4-oxobutanoic acid-2-chlorotrityl resin, Fmoc-Asp(O-Trt(2-Cl)resin)-Mor(26-bicyc)) (464 mg, loading amount 0.340 mmol/g) was obtained by the same method as in the synthesis of Compound aa007-resin using the obtained Compound aa017 ((3S)-3-(9H-fluoren-9-ylmethoxycarbonylamino)-4-(3-oxa-8-azabicyclo[3.2.1]octan-8-yl)-4-oxobutanoic acid, Fmoc-Asp-Mor(26-bicyc)) (115 mg, 0.256 mmol).

Another lot synthesized in the same manner with a different loading amount was also used for peptide synthesis in the present Examples.

Synthesis of Compound aa018-resin, (3S)-3-(9H-fluoren-9-ylmethoxycarbonylamino)-4-oxo-4-pyrrolidin-1-ylbutanoic acid-2-chlorotrityl resin (Fmoc-Asp(0-Trt(2-Cl)-resin)-pyrro)

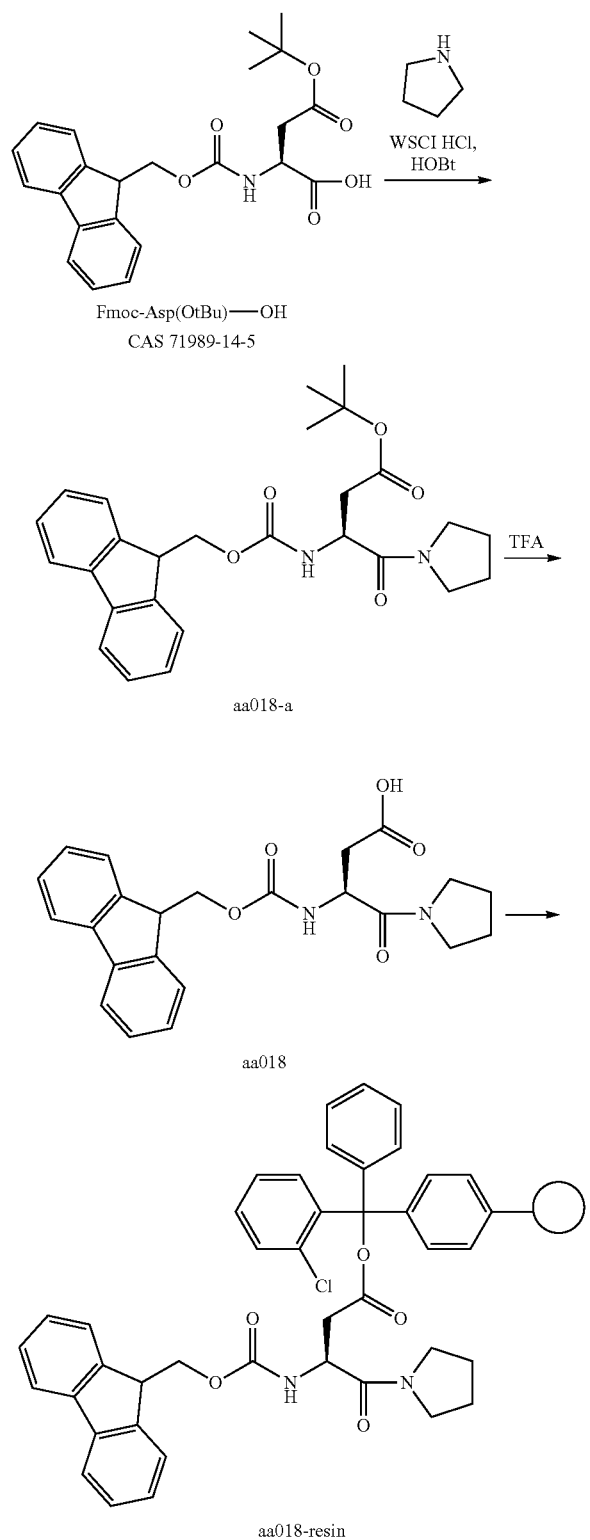

To DMF (600 mL) were sequentially added WSCI·HCl (67.1 g, 350 mmol), HOBt (43.4 g, 321 mmol), and Fmoc-Asp(OtBu)-OH (120 g, 292 mmol) at 0° C. under a nitrogen atmosphere, and the mixture was stirred at 0° C. for one hour. To this reaction solution was slowly added pyrrolidine (26.3 mL, 321 mmol), and the mixture was stirred at 0° C. for 1.5 hours. To the reaction solution were added Ethyl acetate (10 v) and 0.5 mol/L aqueous hydrochloric acid (2 v) at 0° C., and the organic layer was separated. The resulting organic layer was sequentially washed with 0.5 mol/L aqueous hydrochloric acid, water, saturated aqueous sodium bicarbonate/water (1/1), and brine/water (1/1) and dried over anhydrous sodium sulfate, and the solvent was then evaporated under reduced pressure to give Compound aa018-a as a crude product (137.1 g, quant.).

LCMS (ESI) m/z=465 (M+H)+

Retention time: 1.05 min (analysis condition SQDAA05)

To a solution of Compound aa018-a (137 g, 395 mmol) in DCM (137 mL) was slowly added TFA (271 mL) under ice-cooling such that the internal temperature did not exceed 10° C. After stirring at room temperature for one hour, diisopropyl ether (3.4 L) were added in four portions, and the precipitated solid was collected by filtration and dried to give Compound aa018 ((3S)-3-(9H-fluoren-9-ylmethoxycarbonylamino)-4-oxo-4-pyrrolidin-1-ylbutanoic acid, Fmoc-Asp-pyrro) (108.4 g, 90%).

LCMS(ESI) m/z=409 (M+H)+

Retention time: 0.83 min (analysis condition SQDAA05)

Compound aa017-resin ((3S)-3-(9H-fluoren-9-ylmethoxycarbonylamino)-4-oxo-4-pyrrolidin-1-ylbutanoic acid-2-chlorotrityl resin (Fmoc-Asp(O-Trt(2-Cl)-resin)-pyrro)) (59.79 g, loading amount 0.464 mmol/g) was obtained by the same method as in the synthesis of Compound aa007-resin using Compound aa018 ((3S)-3-(9H-fluoren-9-ylmethoxycarbonylamino)-4-oxo-4-pyrrolidin-1-ylbutanoic acid, Fmoc-Asp-pyrro) (15.91 g, 30 mmol).

Another lot synthesized in the same manner with a different loading amount was also used for peptide synthesis in the present Examples.

Synthesis of Compound aa019-resin, (3S)-4-(dimethylamino)-3-(9H-fluoren-9-ylmethoxycarbonylamino)-4-oxobutanoic acid-2-chlorotrityl resin (Fmoc-Asp(0-Trt(2-Cl)resin)-NMe2)

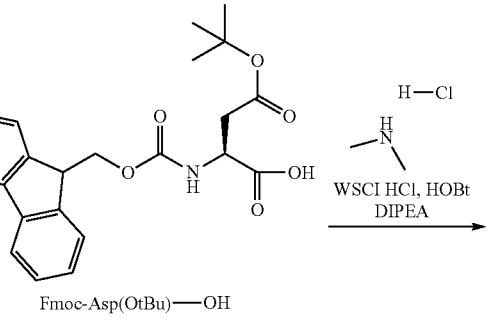

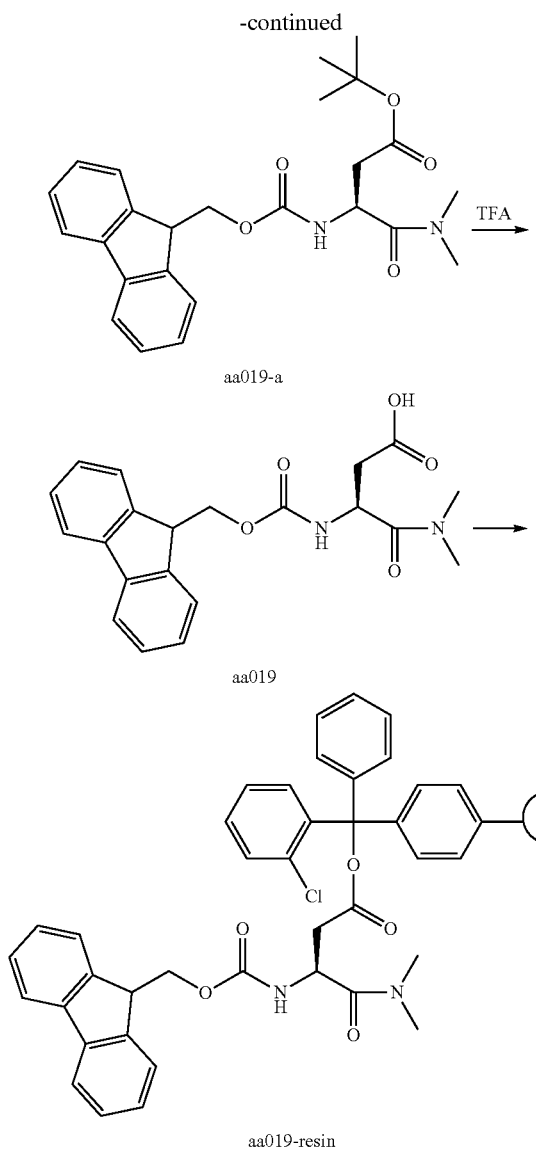

aa019-a aa019 aa019-resin

To a solution of Fmoc-Asp(OtBu)-OH (4-tert-butyl N-[(9H-fluoren-9-ylmethoxy)carbonyl]-L-aspartate, CAS No. 71989-14-5) (5 g, 12.15 mmol) and HOBt monohydrate (2.047 g, 13.37 mmol) in DMF (24.3 mL) were sequentially added dimethylamine hydrochloride (0.991 g, 12.15 mmol), WSCI·HCl (2.8 g, 14.58 mmol), and DIPEA (2.117 mL, 12.15 mmol) at 0° C. under a nitrogen atmosphere, and the mixture was stirred at 0° C. for 50 minutes. To the reaction solution were added ethyl acetate/hexane (1/1, 100 mL) and brine/water (1/1, 50 mL), and the organic layer was separated. The resulting organic layer was sequentially washed with a saturated aqueous ammonium chloride solution, water, and brine and dried over anhydrous sodium sulfate, and the solvent was then evaporated under reduced pressure. The resulting residue was purified by silica gel column chromatography (hexane/ethyl acetate) to give Compound aa019-a (5.02 g, 94%).

LCMS (ESI) m/z=439 (M+H)+

Retention time: 1.03 min (analysis condition SQDAA05)

To Compound aa019-a (5 g, 11.4 mmol) was added toluene (150 mL) and the solvent was evaporated under reduced pressure. This operation was performed three times. The residue was dissolved in DCM (5.06 mL), TFA (10.13 mL, 137 mmol) was added dropwise at 0° C. under a nitrogen atmosphere, and the mixture was stirred at room temperature for one hour. The reaction solution was cooled at 0° C., diethyl ether (10.1 mL) was added, and a 8 mol/L aqueous sodium hydroxide solution (17.1 mL) was added dropwise. A saturated aqueous sodium dihydrogenphosphate solution (7.6 mL) and water (5 mL) were further added. The solution was extracted with ethyl acetate, and the resulting organic layer was washed with saturated aqueous sodium dihydrogenphosphate/water (1/1) and dried over anhydrous sodium sulfate, after which the solvent was evaporated under reduced pressure to give Compound aa019 ((3S)-4-(dimethylamino)-3-(9H-fluoren-9-ylmethoxycarbonylamino)-4-oxobutanoic acid, Fmoc-Asp-NMe2) (2.63 g, 60%), which was used for the next reaction without further purification.

LCMS (ESI) m/z=383 (M+H)+

Retention time: 0.80 min (analysis condition SQD compound AA05)

Compound aa019-resin ((3S)-4-(dimethylamino)-3-(9H-fluoren-9-ylmethoxycarbonylamino)-4-oxobutanoic acid-2-chlorotrityl resin, Fmoc-Asp(O-Trt(2-Cl)resin)-NMe2) (9.07 g, loading amount 0.399 mmol/g) was obtained by the same method as in the synthesis of Compound aa007-resin using the obtained Compound aa019 ((3S)-4-(dimethylamino)-3-(9H-fluoren-9-ylmethoxycarbonylamino)-4-oxobutanoic acid, Fmoc-Asp-NMe2) (2.367 g, 6.19 mmol).

Another lot synthesized in the same manner with a different loading amount was also used for peptide synthesis in the present Examples.

Synthesis of Compound aa020-resin, (3S)-4-(4-tert-butylpiperidin-1-yl)-3-(9H-fluoren-9-ylmethoxycarbonylamino)-4-oxobutanoic acid-2-chlorotrityl resin (Fmoc-Asp(O-Trt(2-Cl)resin)-pip-tBu)

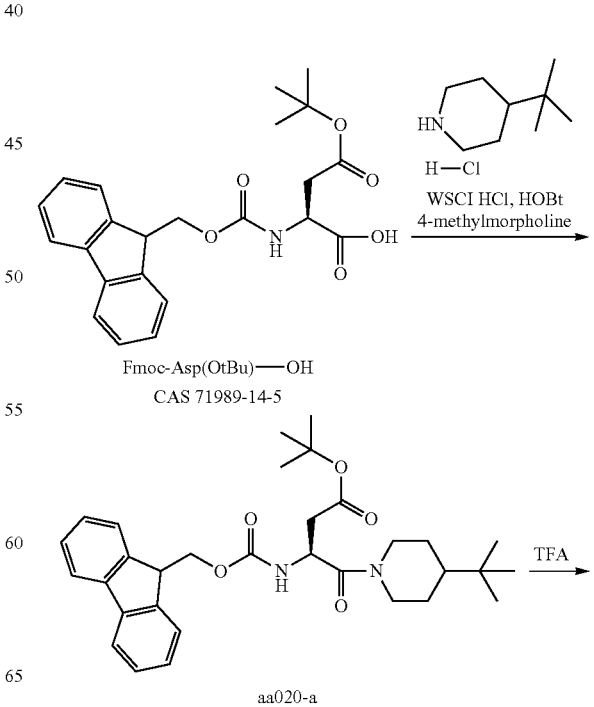

Fmoc-Asp(OtBu)—OH
CAS 71989-14-5 aa020-a


aa020

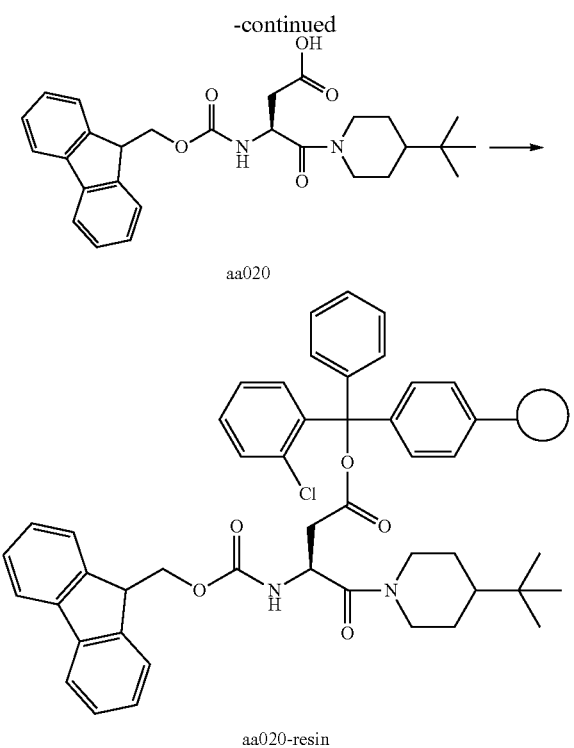

aa020-resin

Compound aa020-a (11.5 g, 93%) was obtained by the same method as in the synthesis of Compound aa019-a using Fmoc-Asp(OtBu)-OH (4-tert-butyl N-[(9H-fluoren-9-yl-methoxy)carbonyl]-L-aspartate, CAS No. 71989-14-5) (10 g, 24.3 mmol) as a starting material, using 4-(tert-butyl) piperidine hydrochloride instead of dimethylamine hydrochloride, and using 1.0 equivalent of 4-methylmorpholine relative to amine, instead of DIPEA.

LCMS (ESI) m/z=535.4 (M+H)+

Retention time: 1.19 min (analysis condition SQDAA05)

To Compound aa020-a (2 g, 3.74 mmol) was added toluene (150 mL) and the solvent was evaporated under reduced pressure. This operation was performed three times. The residue was dissolved in DCM (1.66 mL), TFA (1.66 mL, 22.44 mmol) was added dropwise at 0° C. under a nitrogen atmosphere, and the mixture was stirred at room temperature for 4 h. The reaction solution was cooled to 0° C. and triethylamine (3.13 mL, 22.4 mmol) was added dropwise. This solution was diluted with DCM (30 mL) and washed with an aqueous sodium dihydrogenphosphate solution (5%) nine times. The organic layer was dried over anhydrous sodium sulfate, and the solvent was then evaporated under reduced pressure to give Compound aa020 ((3S)-4-(4-tert-butylpiperidin-1-yl)-3-(9H-fluoren-9-yl-methoxycarbonylamino)-4-oxobutanoic acid, Fmoc-Asp-pip-tBu) (1.73 g, 96%).

LCMS (ESI) m/z=479.4 (M+H)+

Retention time: 1.02 min (analysis condition SQDAA05)

Compound aa020-resin ((3S)-4-(4-tert-butylpiperidin-1-yl)-3-(9H-fluoren-9-ylmethoxycarbonylamino)-4-oxobutanoic acid-2-chlorotrityl resin, Fmoc-Asp(O-Trt(2-Cl) resin)-pip-tBu) (5.23 g, loading amount 0.356 mmol/g) was obtained by the same method as in the synthesis of Compound aa007-resin using the obtained Compound aa020 ((3S)-4-(4-tert-butylpiperidin-1-yl)-3-(9H-fluoren-9-yl-methoxycarbonylamino)-4-oxobutanoic acid, Fmoc-Asp-pip-tBu) (1.73 g, 3.61 mmol).

Synthesis of Compound aa021-resin, (3S)-4-(1,1-dioxo-1,4-thiazinan-4-yl)-3-(9H-fluoren-9-yl-methoxycarbonylamino)-4-oxobutanoic acid-2-chlorotrityl resin (Fmoc-Asp(O-Trt(2-Cl)resin)-mor (SO2))

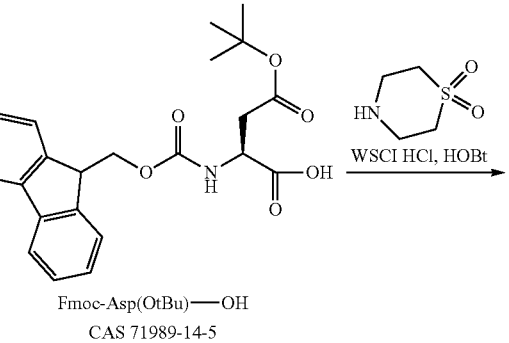

Fmoc-Asp(OtBu)—OH
CAS 71989-14-5

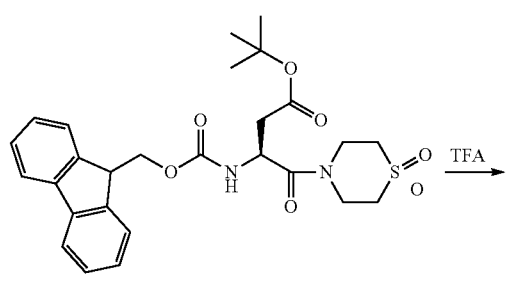

aa021-a

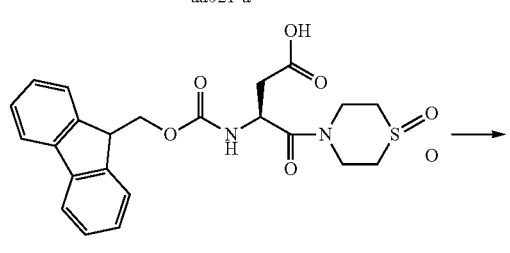

aa021

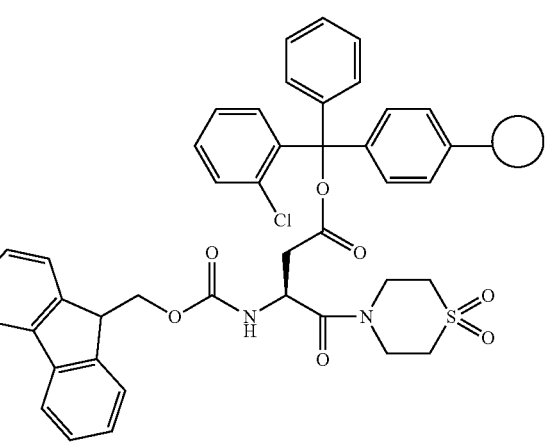

aa021-resin

Compound aa021-a (492 mg, 38%) was obtained by the same method as in the synthesis of Compound aa019-a using Fmoc-Asp(OtBu)-OH (4-tert-butyl N-[(9H-fluoren-9-yl-methoxy)carbonyl]-L-aspartate, CAS No. 71989-14-5) (1 g, 2.43 mmol) as a starting material and using 1,1-dioxido-thiomorpholine instead of dimethylamine hydrochloride and DIPEA.

LCMS (ESI) m/z=551 (M+Na)+

Retention time: 0.86 min (analysis condition SQDFA05)

Compound aa021 ((3S)-4-(1,1-dioxo-1,4-thiazinan-4-yl)-3-(9H-fluoren-9-ylmethoxycarbonylamino)-4-oxobutanoic acid, Fmoc-Asp-mor(SO2)) (356.4 mg, 95%) was obtained by the same method as in the synthesis of Compound aa020 using the obtained Compound aa021-a (420 mg, 0.795 mmol).

LCMS (ESI) m/z=473 (M+H)+

Retention time: 0.67 min (analysis condition SQDFA05)

Compound aa021-resin ((3S)-4-(1,1-dioxo-1,4-thiazinan-4-yl)-3-(9H-fluoren-9-ylmethoxycarbonylamino)-4-oxobutanoic acid-2-chlorotrityl resin, Fmoc-Asp(O-Trt(2-Cl)resin)-mor(SO2)) (1.16 g, loading amount 0.371 mmol/g) was obtained by the same method as in the synthesis of Compound aa007-resin using the obtained Compound aa021 ((3S)-4-(1,1-dioxo-1,4-thiazinan-4-yl)-3-(9H-fluoren-9-ylmethoxycarbonylamino)-4-oxobutanoic acid, Fmoc-Asp-mor(SO2)) (346 mg, 0.773 mmol).

Synthesis of Compound aa022-resin, (3S)-3-(9H-fluoren-9-ylmethoxycarbonylamino)-4-morpholin-4-yl-4-oxobutanoic acid-2-chlorotrityl resin (Fmoc-Asp(O-Trt(2-Cl)resin)-mor)

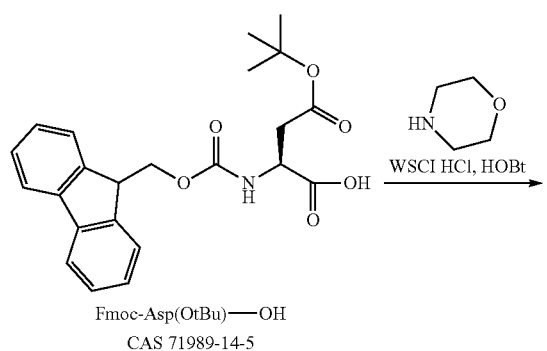

Fmoc-Asp(OtBu)—OH
CAS 71989-14-5

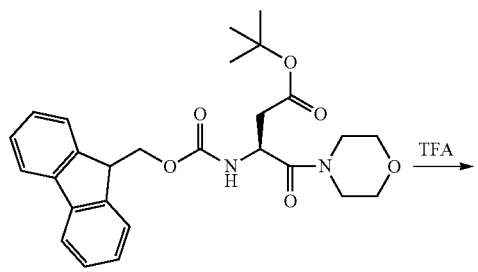

aa022-a

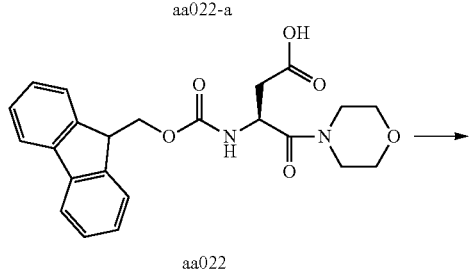

aa022

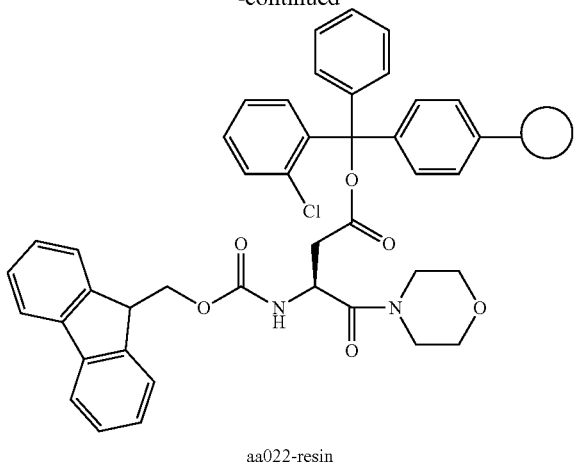

aa022-resin

Compound aa022-a (713 mg, 61%) was obtained by the same method as in the synthesis of Compound aa019-a using Fmoc-Asp(OtBu)-OH (4-tert-butyl N-[(9H-fluoren-9-ylmethoxy)carbonyl]-L-aspartate, CAS No. 71989-14-5) (1 g, 2.43 mmol) as a starting material and using morpholine instead of dimethylamine hydrochloride and DIPEA.

LCMS (ESI) m/z=481 (M+H)+

Retention time: 0.88 min (analysis condition SQDFA05)

Compound aa022 ((3S)-3-(9H-fluoren-9-ylmethoxycarbonylamino)-4-morpholin-4-yl-4-oxobutanoic acid, Fmoc-Asp-mor) (353.4 mg, 100%) was obtained by the same method as in the synthesis of Compound aa020 using the obtained Compound aa022-a (400 mg, 0.832 mmol).

LCMS (ESI) m/z=425 (M+H)+

Retention time: 0.66 min (analysis condition SQDFA05)

Compound aa022-resin, (3S)-3-(9H-fluoren-9-ylmethoxycarbonylamino)-4-morpholin-4-yl-4-oxobutanoic acid-2-chlorotrityl resin (Fmoc-Asp(O-Trt(2-Cl)resin)-mor) (1.21 g, loading amount 0.415 mmol/g) was obtained by the same method as in the synthesis of Compound aa007-resin using the obtained Compound aa022 ((3S)-3-(9H-fluoren-9-ylmethoxycarbonylamino)-4-morpholin-4-yl-4-oxobutanoic acid, Fmoc-Asp-mor) (326 mg, 0.768 mmol).

Another lot synthesized in the same manner with a different loading amount was also used for peptide synthesis in the present Examples.

Synthesis of Compound aa023-resin, (3S)-3-(9H-fluoren-9-ylmethoxycarbonylamino)-4-(4-methylpiperidin-1-yl)-4-oxobutanoic acid-2-chlorotrityl resin (Fmoc-Asp(O-Trt(2-Cl)resin)-pip(4-Me))

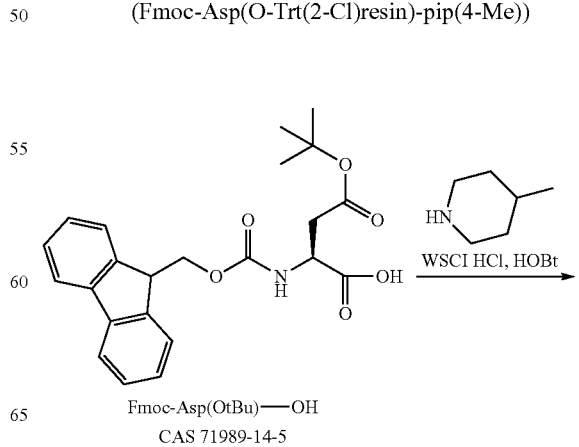

Fmoc-Asp(OtBu)—OH
CAS 71989-14-5

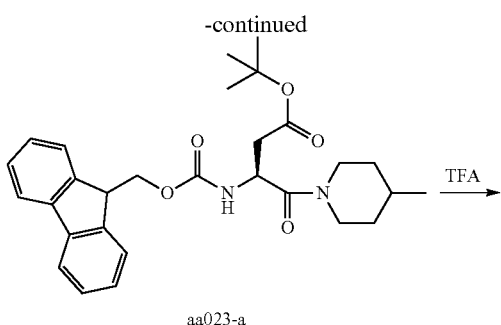

aa023-a

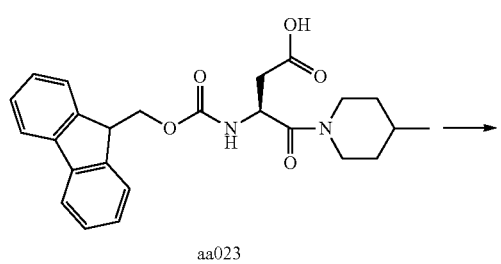

aa023

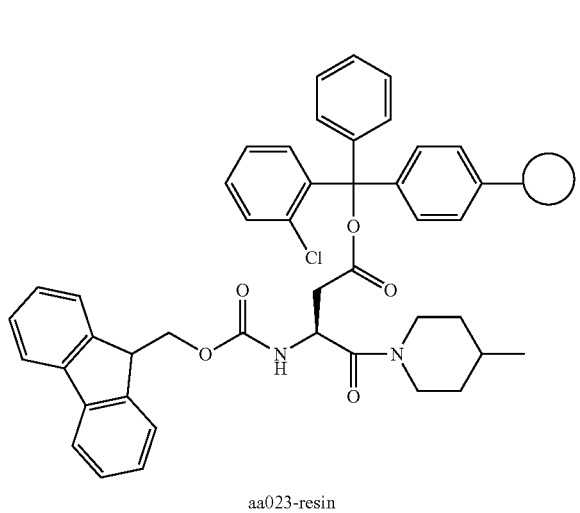

aa023-resin

A crude product of Compound aa023-a was obtained by the same method as in the synthesis of Compound aa019-a using Fmoc-Asp(OtBu)-OH (4-tert-butyl N-[(9H-fluoren-9-ylmethoxy)carbonyl]-L-aspartate, CAS No. 71989-14-5) (1 g, 2.43 mmol) as a starting material and using 4-methylpiperidine instead of dimethylamine hydrochloride and DIPEA. The resulting crude product was dissolved in 20% ethyl acetate-hexane, washed three times with a saturated aqueous sodium bicarbonate solution and once with brine, and dried over anhydrous sodium sulfate, after which the solvent was evaporated under reduced pressure to give Compound aa023-a (430 mg, 36%).

LCMS (ESI) m/z=493 (M+H)+

Retention time: 0.74 min (analysis condition SQDAA50)

Compound aa023 ((3S)-3-(9H-fluoren-9-ylmethoxycarbonylamino)-4-(4-methylpiperidin-1-yl)-4-oxobutanoic acid, Fmoc-Asp-pip(4-Me)) (326.5 mg, quant.) was obtained by the same method as in the synthesis of Compound aa020 using the obtained Compound aa023-a (359 mg, 0.728 mmol).

LCMS (ESI) m/z=437 (M+H)+

Retention time: 0.80 min (analysis condition SQDFA05)

Compound aa023-resin ((3S)-3-(9H-fluoren-9-ylmethoxycarbonylamino)-4-(4-methylpiperidin-1-yl)-4-oxobutanoic acid-2-chlorotrityl resin, Fmoc-Asp(O-Trt(2-Cl)resin)-pip(4-Me)) (1.07 g, loading amount 0.363 mmol/g) was obtained by the same method as in the synthesis of Compound aa007-resin using the obtained Compound aa023 ((3S)-3-(9H-fluoren-9-ylmethoxycarbonylamino)-4-(4-methylpiperidin-1-yl)-4-oxobutanoic acid, Fmoc-Asp-pip(4-Me)) (315 mg, 0.722 mmol).

Synthesis of Compound aa024-resin, (3S)-4-(3,3-dimethylpyrrolidin-1-yl)-3-(9H-fluoren-9-ylmethoxycarbonylamino)-4-oxobutanoic acid-2-chlorotrityl resin (Fmoc-Asp(O-Trt(2-Cl)resin)-pyrro(3-Me2))

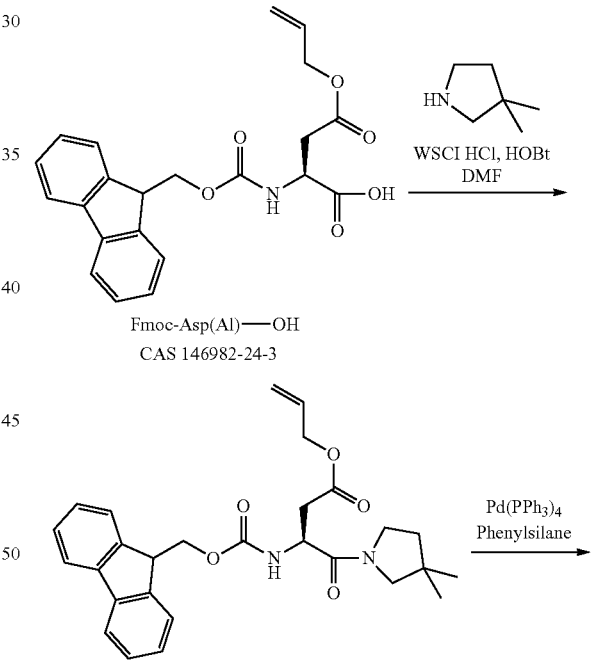

Fmoc-Asp(Al)—OH
CAS 146982-24-3 aa024-a

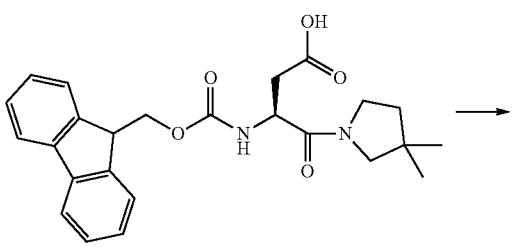

aa024

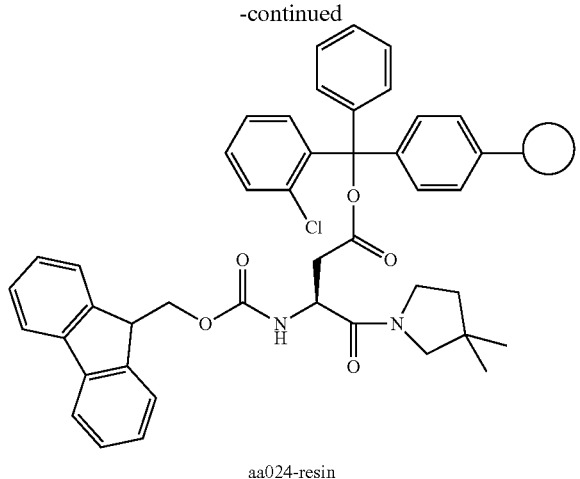

aa024-resin

Compound aa024-a (1.36 g, 56%) was obtained by the same method as in the synthesis of Compound aa007-a using Fmoc-Asp(OAl)—OH ((2S)-2-(9H-fluoren-9-ylmethoxycarbonylamino)-4-oxo-4-prop-2-enoxybutanoic acid, CAS No. 146982-24-3) (2 g, 5.06 mmol) as a starting material and using 3,3-dimethylpyrrolidine instead of morpholine.

LCMS (ESI) m/z=477 (M+H)+

Retention time: 1.322 min (analysis condition SMD-method_04)

Compound aa024 ((3S)-4-(3,3-dimethylpyrrolidin-1-yl)-3-(9H-fluoren-9-ylmethoxycarbonylamino)-4-oxobutanoic acid, Fmoc-Asp-pyrro(3-Me2)) (1.041 g, 90%) was obtained by the same method as in the synthesis of Compound aa007 using the obtained Compound aa024-a (1.269 g, 2.66 mmol).

LCMS (ESI) m/z=437 (M+H)+

Retention time: 0.81 min (analysis condition SQDFA05)

Compound aa024-resin ((3S)-4-(3,3-dimethylpyrrolidin-1-yl)-3-(9H-fluoren-9-ylmethoxycarbonylamino)-4-oxobutanoic acid-2-chlorotrityl resin, Fmoc-Asp(O-Trt(2-Cl) resin)-pyrro(3-Me2)) (4.16 g, loading amount 0.569 mmol/g) was obtained by the same method as in the synthesis of Compound aa007-resin using the obtained Compound aa024 ((3S)-4-(3,3-dimethylpyrrolidin-1-yl)-3-(9H-fluoren-9-ylmethoxycarbonylamino)-4-oxobutanoic acid, Fmoc-Asp-pyrro(3-Me2)) (1.903 g, 5.81 mmol).

Synthesis of Compound aa025-resin, (3S)-3-[9H-fluoren-9-ylmethoxycarbonyl(methyl)amino]-4-(3,3,4,4,5,5-hexafluoropiperidin-1-yl)-4-oxobutanoic acid-2-chlorotrityl resin (Fmoc-MeAsp(O-Trt(2-Cl) resin)-pip(345-F6))

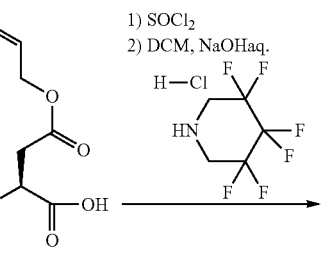

aa033-b

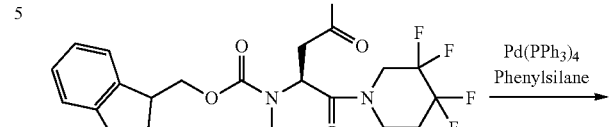

aa025-a

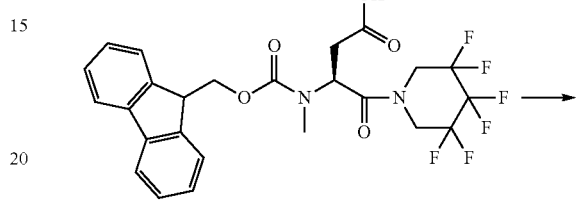

aa025

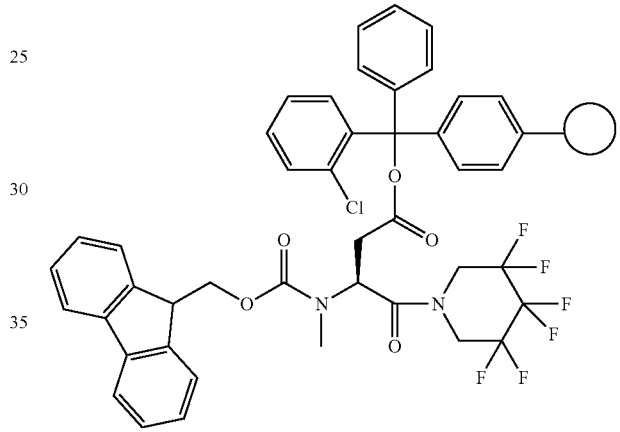

aa025-resin

To a suspension of Compound aa033-b ((2S)-2-[9H-fluoren-9-ylmethoxycarbonyl(methyl)amino]-4-oxo-4-prop-2-enoxybutanoic acid) (0.62 g, 1.57 mmol) in DCM (7.8 mL, 0.2 M) were added thionyl chloride (0.136 mL, 1.88 mmol, 1.2 equivalents) and DMF (0.00607 mL, 0.078 mmol, 5 mol %) at room temperature, and the mixture was stirred for four hours. The reaction solution was concentrated, after which the resulting solution of the crude product in DCM (3 mL) was added to a mixed suspension composed of a solution of 3,3,4,4,5,5-hexafluoropiperidine hydrochloride (300 mg, 1.31 mmol) in DCM (10 mL) and a 1 mol/L aqueous sodium hydroxide solution (13 mL) at room temperature, and the mixture was stirred for 1.5 hours. The reaction solution was extracted with TBME twice, and the resulting organic layers were washed with water, dried over sodium sulfate, and then concentrated under reduced pressure to give a crude product. The resulting crude product was purified by medium pressure reverse phase column chromatography to give Compound aa025-a (587 mg, 77%).

LCMS (ESI) m/z=585 (M+H)+

Retention time: 1.03 min (analysis condition SQDFA05)

Compound aa025 ((3S)-3-[9H-fluoren-9-ylmethoxycarbonyl(methyl)amino]-4-(3,3,4,4,5,5-hexafluoropiperidin-1-yl)-4-oxobutanoic acid, Fmoc-MeAsp-pip(345-F6)) (413 mg, 81%) was obtained by the same method as in the synthesis of Compound aa007 using the obtained Compound aa025-a (550 mg, 0.941 mmol).

LCMS (ESI) m/z=545 (M+H)+

Retention time: 0.89 min (analysis condition SQDFA05)

Compound aa025-resin ((3S)-3-[9H-fluoren-9-ylmethoxycarbonyl(methyl)amino]-4-(3,3,4,4,5,5-hexafluoropiperidin-1-yl)-4-oxobutanoic acid-2-chlorotrityl resin, Fmoc-MeAsp(O-Trt(2-Cl)resin)-pip(345-F6)) (1.17 g, loading amount 0.315 mmol/g) was obtained by the same method as in the synthesis of Compound aa007-resin using the obtained Compound aa025 ((3S)-3-[9H-fluoren-9-ylmethoxycarbonyl(methyl)amino]-4-(3,3,4,4,5,5-hexafluoropiperidin-1-yl)-4-oxobutanoic acid, Fmoc-MeAsp-pip(345-F6)) (327 mg, 0.6 mmol).

Synthesis of Compound aa026-resin, (3S)-3-(9H-fluoren-9-ylmethoxycarbonylamino)-4-(3,3,4,4,5,5-hexafluoropiperidin-1-yl)-4-oxobutanoic acid-2-chlorotrityl resin (Fmoc-Asp(O-Trt(2-Cl)resin)-pip(345-F6))

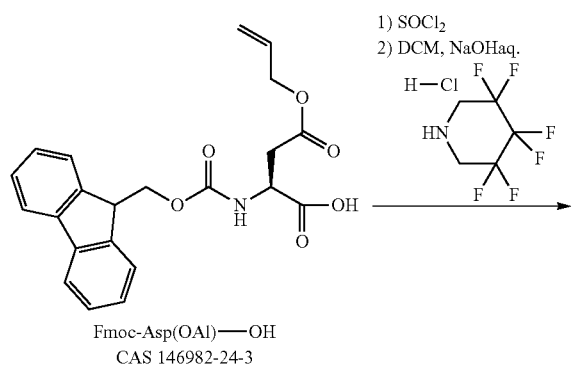

Fmoc-Asp(OAl)—OH
CAS 146982-24-3

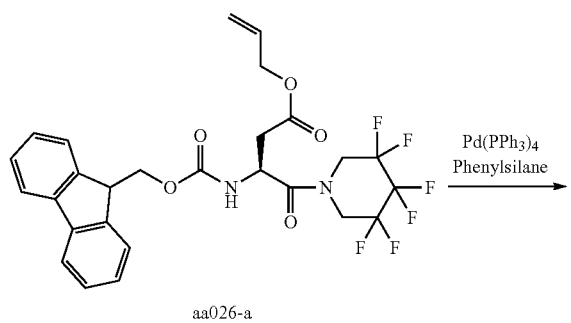

aa026-a

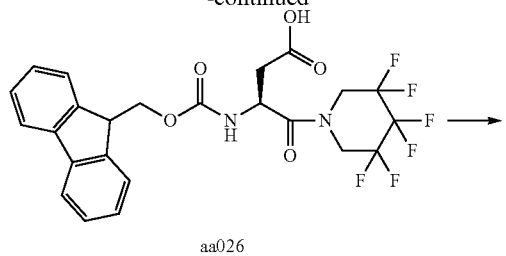

aa026

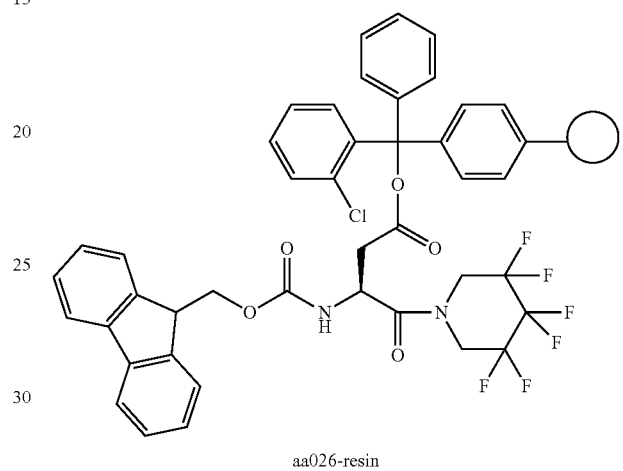

aa026-resin

Compound aa026-a (552 mg, 74%) was obtained by the same method as in the synthesis of Compound aa025-a using Fmoc-Asp(OAl)—OH ((2S)-2-(9H-fluoren-9-ylmethoxycarbonylamino)-4-oxo-4-prop-2-enoxybutanoic acid, CAS No. 146982-24-3) (649 mg, 1.568 mmol) as a starting material.

LCMS (ESI) m/z=571 (M+H)+

Retention time: 0.97 min (analysis condition SQDFA05)

Compound aa026 ((3S)-3-(9H-fluoren-9-ylmethoxycarbonylamino)-4-(3,3,4,4,5,5-hexafluoropiperidin-1-yl)-4-oxobutanoic acid, Fmoc-Asp-pip(345-F6)) (462 mg, 90%) was obtained by the same method as in the synthesis of Compound aa007 using the obtained Compound aa026-a (552 mg, 0.968 mmol).

LCMS (ESI) m/z=531 (M+H)+

Retention time: 0.84 min (analysis condition SQDFA05)

Compound aa026-resin ((3S)-3-(9H-fluoren-9-ylmethoxycarbonylamino)-4-(3,3,4,4,5,5-hexafluoropiperidin-1-yl)-4-oxobutanoic acid-2-chlorotrityl resin, Fmoc-Asp(O-Trt(2-Cl)resin)-pip(345-F6)) (1.64 g, loading amount 0.309 mmol/g) was obtained by the same method as in the synthesis of Compound aa007-resin using the obtained Compound aa026 ((3S)-3-(9H-fluoren-9-ylmethoxycarbonylamino)-4-(3,3,4,4,5,5-hexafluoropiperidin-1-yl)-4-oxobutanoic acid, Fmoc-Asp-pip(345-F6)) (446 mg, 0.84 mmol).

Synthesis of Compound aa027-resin, (3S)-3-(9H-fluoren-9-ylmethoxycarbonylamino)-4-oxo-4-(3,3,4,4-tetrafluoropyrrolidin-1-yl)butanoic acid-2-chlorotrityl resin (Fmoc-Asp(O-Trt(2-Cl)resin)-pyrro(34-F4))

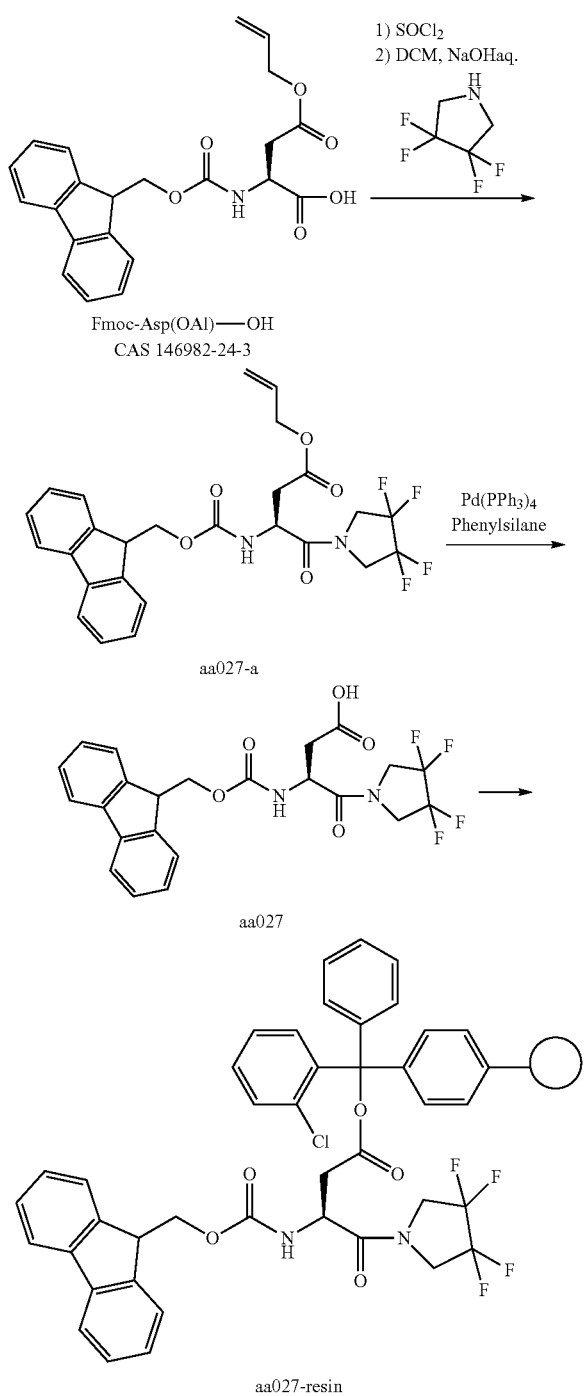

Compound aa027-a (478 mg, 91%) was obtained by the same method as in the synthesis of Compound aa025-a using Fmoc-Asp(OAl)—OH ((2S)-2-(9H-fluoren-9-ylmethoxycarbonylamino)-4-oxo-4-prop-2-enoxybutanoic acid, CAS No. 146982-24-3) (0.62 g, 1.568 mmol) as a starting material and using 3,3,4,4-tetrafluoropyrrolidine hydrochloride instead of 3,3,4,4,5,5-hexafluoropiperidine hydrochloride.

LCMS (ESI) m/z=521 (M+H)+

Retention time: 0.95 min (analysis condition SQDFA05)

Compound aa027 ((3S)-3-(9H-fluoren-9-ylmethoxycarbonylamino)-4-oxo-4-(3,3,4,4-tetrafluoropyrrolidin-1-yl)butanoic acid, Fmoc-Asp-pyrro(34-F4)) (388 mg, quant.) was obtained by the same method as in the synthesis of Compound aa007 using the obtained Compound aa027-a (416 mg, 0.799 mmol).

LCMS (ESI) m/z=481 (M+H)+

Retention time: 0.81 min (analysis condition SQDFA05)

Compound aa027-resin ((3S)-3-(9H-fluoren-9-ylmethoxycarbonylamino)-4-oxo-4-(3,3,4,4-tetrafluoropyrrolidin-1-yl)butanoic acid-2-chlorotrityl resin, Fmoc-Asp(O-Trt(2-Cl)resin)-pyrro(34-F4)) (1.74 g, loading amount 0.343 mmol/g) was obtained by the same method as in the synthesis of Compound aa007-resin using the obtained Compound aa027 ((3S)-3-(9H-fluoren-9-ylmethoxycarbonylamino)-4-oxo-4-(3,3,4,4-tetrafluoropyrrolidin-1-yl)butanoic acid, Fmoc-Asp-pyrro(34-F4)) (0.388 g, 0.808 mmol).

Synthesis of Compound aa028-resin, (3S)-3-[9H-fluoren-9-ylmethoxycarbonyl(methyl)amino]-4-oxo-4-(3,3,4,4-tetrafluoropyrrolidin-1-yl)butanoic acid-2-chlorotrityl resin (Fmoc-MeAsp(O-Trt(2-Cl)resin)-pyrro(34-F4))

-continued

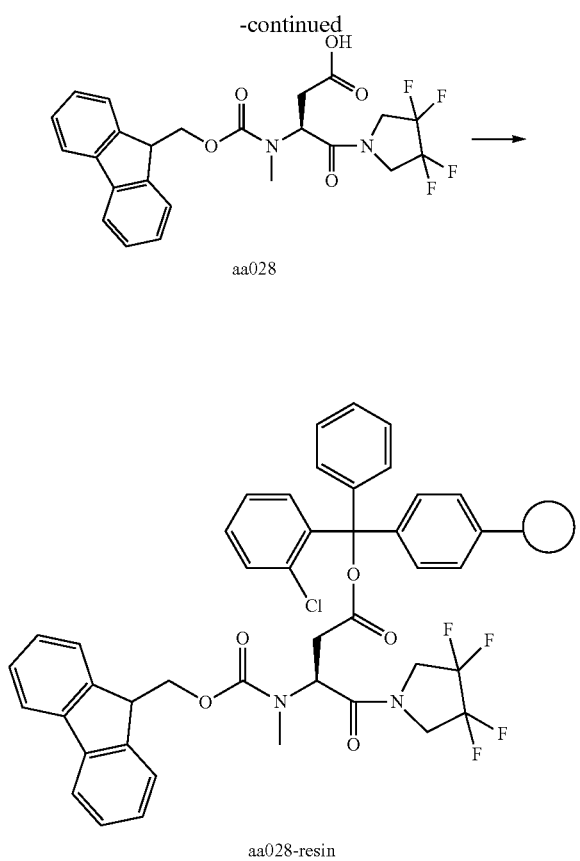

aa028 aa028-resin

Compound aa028-a (490 mg, 90%) was obtained by the same method as in the synthesis of Compound aa025-a using Compound aa033-b ((2S)-2-[9H-fluoren-9-ylmethoxycarbonyl(methyl)amino]-4-oxo-4-prop-2-enoxybutanoic acid) (0.416 mg, 1.208 mmol) as a starting material and using 3,3,4,4-tetrafluoropyrrolidine hydrochloride instead of 3,3,4,4,5,5-hexafluoropiperidine hydrochloride.

LCMS (ESI) m/z=535 (M+H)+

Retention time: 0.99 min (analysis condition SQDFA05)

Compound aa028 ((3S)-3-[9H-fluoren-9-ylmethoxycarbonyl(methyl)amino]-4-oxo-4-(3,3,4,4-tetrafluoropyrrolidin-1-yl)butanoic acid, Fmoc-MeAsp-pyrro(34-F4)) (388 mg, 97%) was obtained by the same method as in the synthesis of Compound aa007 using the obtained Compound aa028-a (450 mg, 0.842 mmol).

LCMS (ESI) m/z=495 (M+H)+

Retention time: 0.83 min (analysis condition SQDFA05)

Compound aa028-resin ((3S)-3-[9H-fluoren-9-ylmethoxycarbonyl(methyl)amino]-4-oxo-4-(3,3,4,4-tetrafluoropyrrolidin-1-yl)butanoic acid-2-chlorotrityl resin, Fmoc-MeAsp(O-Trt(2-Cl)resin)-pyrro(34-F4)) (1.88 g, loading amount 0.355 mmol/g) was obtained by the same method as in the synthesis of Compound aa007-resin using the obtained Compound aa028 ((3S)-3-[9H-fluoren-9-ylmethoxycarbonyl(methyl)amino]-4-oxo-4-(3,3,4,4-tetrafluoropyrrolidin-1-yl)butanoic acid, Fmoc-MeAsp-pyrro (34-F4)) (388 mg, 0.785 mmol).

Synthesis of Compound aa029-resin, (3S)-3-(9H-fluoren-9-ylmethoxycarbonylamino)-4-(1,3-oxazolidin-3-yl)-4-oxobutanoic acid-2-chlorotrityl resin (Fmoc-Asp(O-Trt(2-Cl)resin)-oxz)

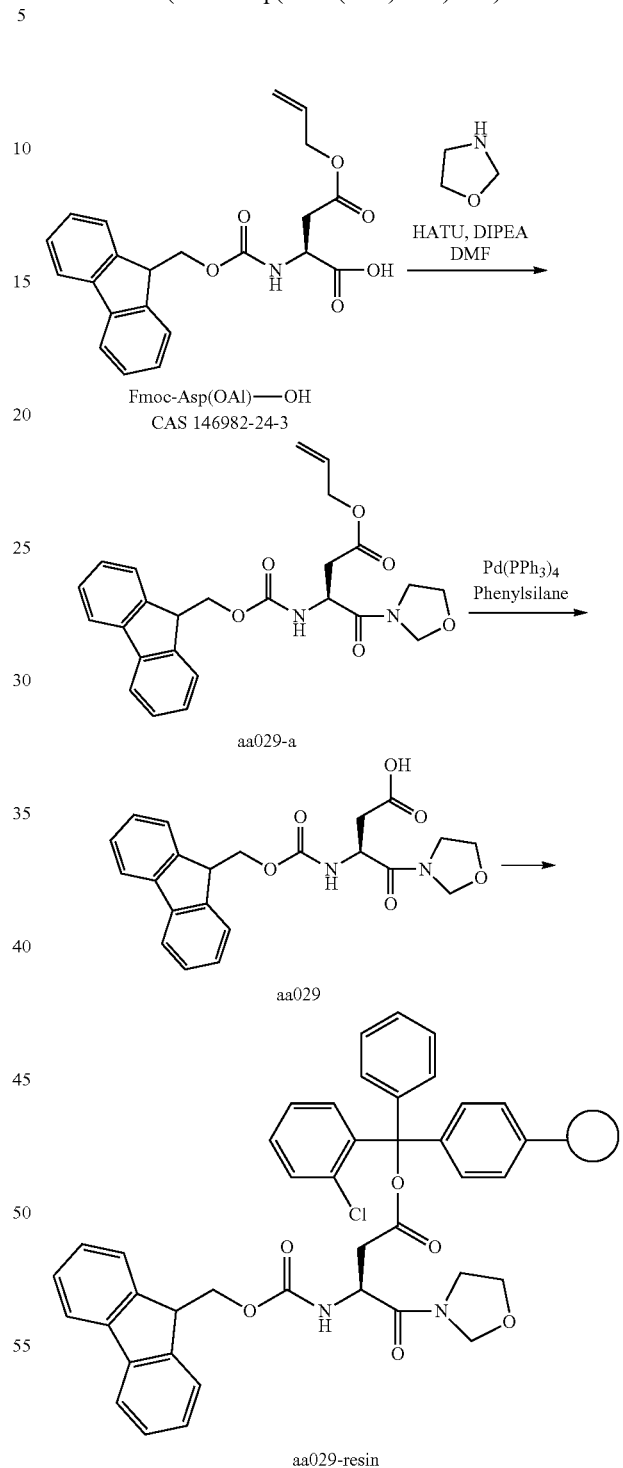

To a solution of Fmoc-Asp(OAl)—OH ((2S)-2-(9H-fluoren-9-ylmethoxycarbonylamino)-4-oxo-4-prop-2-enoxybutanoic acid, CAS No. 146982-24-3) (700 mg, 1.77 mmol) and HATU (740 mg, 1.1 equivalents) in DMF (3.5 mL, 0.5 M) was added DIPEA (229 mg, 1 equivalent), and the mixture was stirred at room temperature for 5 minutes, after which oxazolidine (155 mg, 1.2 equivalents) was added and the mixture was stirred for 15 minutes. Water was added to the reaction solution, which was then extracted with TBME and DCM. The solvent was evaporated from the resulting organic layer under reduced pressure. The resulting crude product was purified by medium pressure reverse phase column chromatography (acetonitrile with 0.1% formic acid/distilled water with 0.1% formic acid) to give Compound aa029-a (456.7 mg, 57%).

LCMS (ESI) m/z=451 (M+H)+

Retention time: 0.82 min (analysis condition SQDFA05)

Compound aa029 ((3S)-3-(9H-fluoren-9-ylmethoxycarbonylamino)-4-(1,3-oxazolidin-3-yl)-4-oxobutanoic acid, Fmoc-Asp-oxz) (426 mg, quant.) was obtained by the same method as in the synthesis of Compound aa007 using the obtained Compound aa029-a (444 mg, 0.985 mmol).

LCMS (ESI) m/z=411 (M+H)+

Retention time: 0.67 min (analysis condition SQDFA05)

Compound aa029-resin ((3S)-3-(9H-fluoren-9-ylmethoxycarbonylamino)-4-(1,3-oxazolidin-3-yl)-4-oxobutanoic acid-2-chlorotrityl resin, Fmoc-Asp(O-Trt(2-Cl)resin)-oxz) (1.99 g, loading amount 0.285 mmol/g) was obtained by the same method as in the synthesis of Compound aa007-resin using the obtained Compound aa029 ((3S)-3-(9H-fluoren-9-ylmethoxycarbonylamino)-4-(1,3-oxazolidin-3-yl)-4-oxobutanoic acid, Fmoc-Asp-oxz) (425 mg, 1.036 mmol).

Synthesis of Compound aa030-resin, (3S)-3-[9H-fluoren-9-ylmethoxycarbonyl(methyl)amino]-4-(1,3-oxazolidin-3-yl)-4-oxobutanoic acid-2-chlorotrityl resin (Fmoc-MeAsp(O-Trt(2-Cl)resin)-oxz

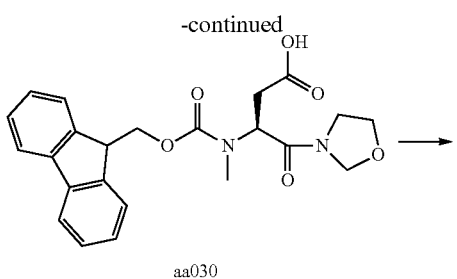

aa030

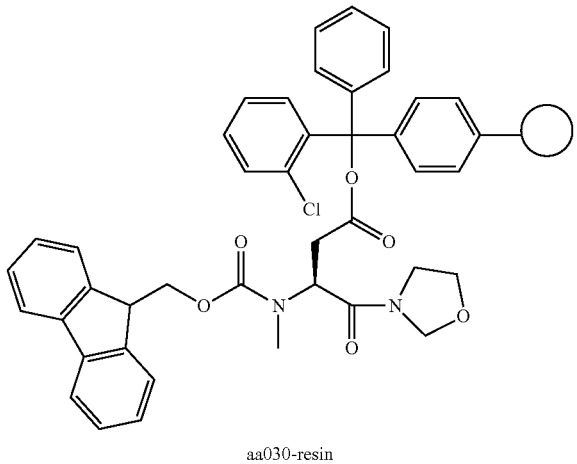

aa030-resin

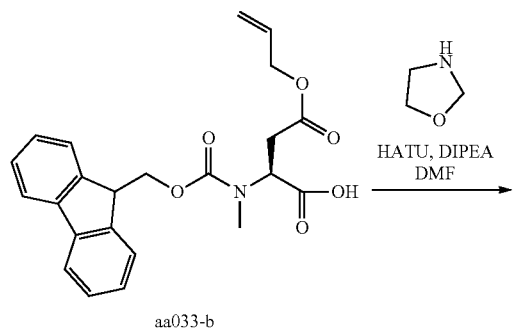

aa033-b

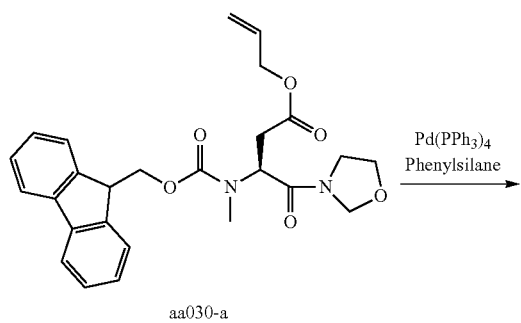

aa030-a

Compound aa030-a (164 mg, 20%) was obtained by the same method as in the synthesis of Compound aa029-a using Compound aa033-b ((2S)-2-[9H-fluoren-9-ylmethoxycarbonyl(methyl)amino]-4-oxo-4-prop-2-enoxybutanoic acid) (725 mg, 1.77 mmol) as a starting material.

LCMS (ESI) m/z=465 (M+H)+

Retention time: 0.86 min (analysis condition SQDFA05)

Compound aa030 ((3S)-3-[9H-fluoren-9-ylmethoxycarbonyl(methyl)amino]-4-(1,3-oxazolidin-3-yl)-4-oxobutanoic acid, Fmoc-MeAsp-oxz) (111 mg, 83%) was obtained by the same method as in the synthesis of Compound aa007 using the obtained Compound aa030-a (146.4 mg, 0.315 mmol). Another lot synthesized in the same manner was added thereto, and the next reaction was performed.

LCMS (ESI) m/z=425 (M+H)+

Retention time: 0.69 min (analysis condition SQDFA05)

Compound aa030-resin ((3S)-3-[9H-fluoren-9-ylmethoxycarbonyl(methyl)amino]-4-(1,3-oxazolidin-3-yl)-4-oxobutanoic acid-2-chlorotrityl resin, Fmoc-MeAsp(O-Trt(2-Cl)resin)-oxz) (1.06 g, loading amount 0.283 mmol/g) was obtained by the same method as in the synthesis of Compound aa007-resin using the obtained Compound aa030 ((3S)-3-[9H-fluoren-9-ylmethoxycarbonyl(methyl)amino]-4-(1,3-oxazolidin-3-yl)-4-oxobutanoic acid, Fmoc-MeAsp-oxz) (0.25 g, 0.589 mmol).

649

Synthesis of Compound aa031-resin, (3R)-3-[9H-fluoren-9-ylmethoxycarbonyl(methyl)amino]-4-oxo-4-pyrrolidin-1-ylbutanoic acid-2-chlorotrityl resin (Fmoc-D-MeAsp(O-Trt(2-Cl)resin)-pyrro)

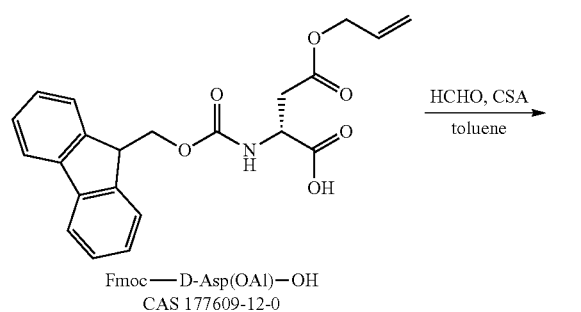

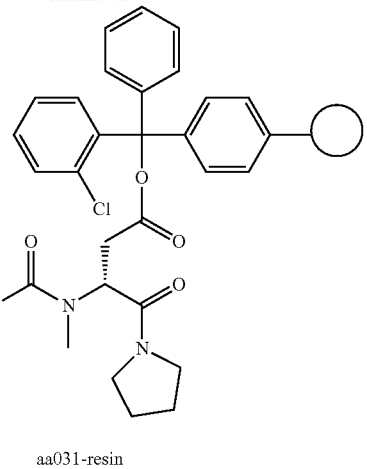

aa031-resin

Fmoc-D-Asp(OAl)—OH ((2R)-2-(9H-fluoren-9-yl-methoxycarbonylamino)-4-oxo-4-prop-2-enoxybutanoic acid) (780 mg, 1.97 mmol) was suspended in toluene (10 ml), paraformaldehyde (178 mg, 5.92 mmol) and CSA (22.9 mg, 0.10 mmol) were added, and the mixture was stirred at 85° C. for two hours. After cooling to room temperature, a saturated aqueous sodium bicarbonate solution was added and the mixture was extracted with ethyl acetate. The organic layer was washed with brine/water (1/1) and dried over anhydrous sodium sulfate, and the solvent was then evaporated under reduced pressure to give Compound aa031-a as a crude product. The next reaction was performed without further purification.

Compound aa031-a was dissolved dichloromethane (10 mL), boron trifluoride-diethyl ether complex (0.50 mL, 3.95 mmol) and triethylsilane (0.63 mL, 3.95 mmol) were added, and the mixture was stirred at room temperature for three hours. A saturated aqueous ammonium chloride solution was added to the reaction solution, and the mixture was extracted with dichloromethane. The organic layer was washed with brine and dried over anhydrous sodium sulfate, and the solvent was then evaporated under reduced pressure. The resulting concentrate was dissolved in acetonitrile and washed with hexane. The solvent was evaporated from the acetonitrile layer under reduced pressure to give Compound aa031-b (530 mg) as a crude product. The next reaction was performed without further purification.

Compound aa031-b (530 mg, 1.29 mmol) was dissolved in DMF (5 mL), HOBt-monohydrate (218 mg, 1.42 mmol) and WSCI·HCl (298 mg, 1.55 mmol) were added, and the mixture was stirred at 0° C. for 30 minutes. To the reaction solution was added pyrrolidine (0.11 ml, 1.29 mmol), and the mixture was further stirred at room temperature for 30 minutes. To the reaction solution was added a 0.5 N aqueous hydrochloric acid solution, and the mixture was extracted with ethyl acetate. The organic layer was washed with a saturated aqueous sodium bicarbonate solution and brine and dried over anhydrous sodium sulfate, and the solvent was evaporated under reduced pressure to give Compound aa031-c (550 mg, 60% over three steps).

LCMS (ESI) m/z=463 (M+H)+

Retention time: 0.89 min (analysis condition SQDFA05)

Compound aa031-c (crude, 550 mg, 1.19 mmol) was dissolved in dichloromethane (10 ml), phenylsilane (0.10 ml, 0.83 mmol) and tetrakis(triphenylphosphine)palladium (0) (13.7 mg, 0.012 mmol) were added, and the mixture was stirred at room temperature for one hour. The reaction solution was diluted with TBME and a 5% aqueous sodium bicarbonate solution (40 ml) was added. The organic layer was removed, phosphoric acid (699 mg) was added to the aqueous layer, which was extracted with TBME. The organic layer was washed with brine/water (1/1, 40 mL) and dried over anhydrous sodium sulfate, and the solvent was then evaporated under reduced pressure to give Compound aa031 ((3R)-3-[9H-fluoren-9-ylmethoxycarbonyl(methyl)amino]-4-oxo-4-pyrrolidin-1-ylbutanoic acid, Fmoc-D-MeAsp-pyrro) (334 mg, 67%).

LCMS (ESI) m/z=423 (M+H)+

Retention time: 0.71 min (analysis condition SQDFA05)

Compound aa031-resin ((3R)-3-[9H-fluoren-9-ylmethoxycarbonyl(methyl)amino]-4-oxo-4-pyrrolidin-1-ylbutanoic acid-2-chlorotrityl resin, Fmoc-D-MeAsp(O-Trt(2-Cl)resin)-pyrro) (loading amount 0.423 mmol/g) was obtained by the same method as in the synthesis of Compound aa007-resin using the obtained Compound aa031 ((3R)-3-[9H-fluoren-9-ylmethoxycarbonyl(methyl)amino]-4-oxo-4-pyrrolidin-1-ylbutanoic acid, Fmoc-D-MeAsp-pyrro) (330 mg, 0.781 mmol).

Synthesis of Compound aa032-resin, (3S)-3-[ethyl(9H-fluoren-9-ylmethoxycarbonyl)amino]-4-oxo-4-piperidin-1-ylbutanoic acid-2-chlorotrityl resin (Fmoc-EtAsp(O-Trt(2-Cl)resin)-pip)

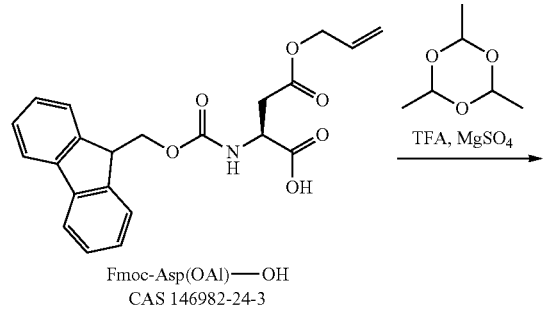

Fmoc-Asp(OAl)—OH ((2S)-2-(9H-fluoren-9-ylmethoxycarbonylamino)-4-oxo-4-prop-2-enoxybutanoic acid, CAS No. 146982-24-3) (5 g, 12.65 mmol, CAS No. 146982-24-3) was suspended in toluene (15.2 mL) under a nitrogen atmosphere, anhydrous magnesium sulfate (4.57 g, 37.9 mmol), paraldehyde (2.53 mL, 19.0 mmol), and TFA (1.94 mL, 25.3 mmol) were added, and the mixture was stirred at 70° C. for five hours. The reaction solution was left to cool to room temperature, washed twice with a mixture of water (10 v), 1 M aqueous dipotassium hydrogenphosphate (K₂HPO₄) solution (3 v), 3.5% aqueous potassium bicarbonate (KHCO₃) solution (4 v), and acetonitrile (2 v), and washed with brine/water (1/1, 5 v), and the organic layer was dried over magnesium sulfate. The resulting organic layer was filtered and then concentrated under reduced pressure to give a crude product of aa032-a, which was used for the next reaction without further purification.

LCMS (ESI) m/z=422 (M+H)+

Retention time: 0.92 min (analysis condition SQDFA05)

To a solution of the crude product containing Compound aa032-a in toluene (16 mL) were added triethylsilane (4.04 mL, 25.3 mmol) and a 1 M solution of titanium tetrachloride (TiCl₄) in toluene (25.3 mL, 25.3 mmol) under a nitrogen atmosphere, and the mixture was stirred at room temperature for 50 minutes. The reaction solution was washed with water (5 v) twice and washed with a 1 M aqueous dipotassium hydrogenphosphate (K₂HPO₄) solution (5 v). Hexane (9 v) was added to the resulting organic layer, which was extracted twice with a mixture of 3.5% aqueous potassium bicarbonate (KHCO₃) solution (4 v) and acetonitrile (2 v). The resulting aqueous layer was washed with hexane (8 v). The resulting aqueous layer was adjusted to pH 3 or lower with a 85% aqueous phosphoric acid solution and then extracted with TBME (5 v), and the resulting organic layer was washed with brine and then dried over magnesium sulfate. The resulting organic layer was filtered and then concentrated under reduced pressure to give Compound aa032-b (4.85 g, 91% through two steps).

LCMS (ESI) m/z=424 (M+H)+

Retention time: 0.85 min (analysis condition SQDFA05)

Compound aa032-c (530 mg, 89%) was obtained by the same method as in the synthesis of Compound aa007-a using Compound aa032-b (512 mg, 1.21 mmol) as a starting material and using piperidine instead of morpholine.

LCMS (ESI) m/z=491 (M+H)+

Retention time: 0.99 min (analysis condition SQDFA05)

Compound aa032 ((3S)-3-[ethyl(9H-fluoren-9-yl-methoxycarbonyl)amino]-4-oxo-4-piperidin-1-ylbutanoic acid, Fmoc-EtAsp-pip) (334 mg, 73%) was obtained by the same method as in the synthesis of Compound aa007 using the obtained Compound aa032-c (495 mg, 1.01 mmol).

LCMS (ESI) m/z=451 (M+H)+

Retention time: 0.82 min (analysis condition SQDFA05)

Compound aa032-resin ((3S)-3-[ethyl(9H-fluoren-9-yl-methoxycarbonyl)amino]-4-oxo-4-piperidin-1-ylbutanoic acid-2-chlorotrityl resin, Fmoc-EtAsp(O-Trt(2-Cl)resin)-pip) (18.3 g, loading amount 0.350 mmol/g) was obtained by the same method as in the synthesis of Compound aa007-resin using the obtained Compound aa032 ((3S)-3-[ethyl(9H-fluoren-9-ylmethoxycarbonyl)amino]-4-oxo-4-piperidin-1-ylbutanoic acid, Fmoc-EtAsp-pip) (0.33 g, 0.732 mmol).

Synthesis of Compound aa051 ((3R)-5-methyl-3-(methylamino)hexanoic acid-2-chlorotrityl resin, H-D-MeLeu-(C#CH2)-O-Trt(2-Cl)resin)

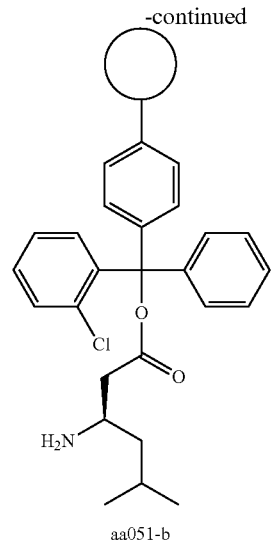

aa051-b

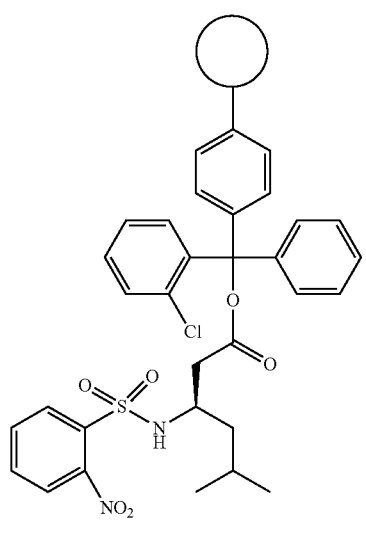

aa051-c

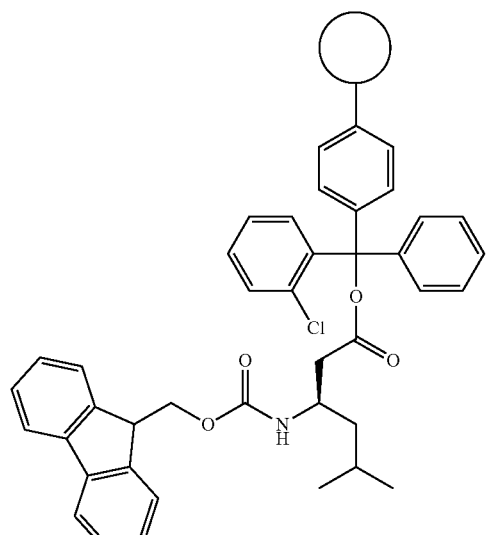

aa141-resin

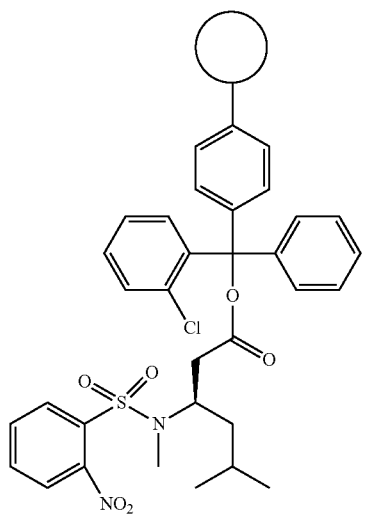

aa051-d

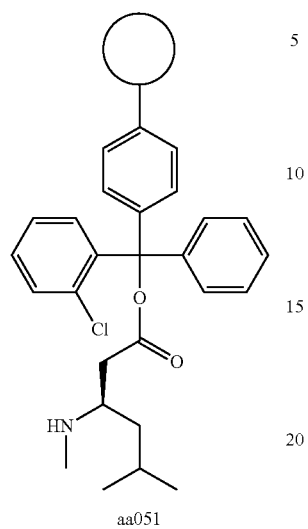

aa051

To a reaction vessel equipped with a filter were added Compound aa141-resin (100 mg, 0.0499 mmol, 0.499 mmol/g) and dehydrated DCM (1.0 mL), and the resin was swollen. The DCM was removed, and the resin was then washed with dehydrated DMF (0.7 mL) twice. An Fmoc deprotection solution (a solution (2% v/v) of diazabicycloundecene (DBU) in DMF, 0.7 mL) was added, the vessel was shaken at room temperature for 10 minutes, and the reaction solution was then removed. The resin was washed with dehydrated THF (0.7 mL) four times to give resin-loaded Compound aa051-b.

To this were added a nosyl chloride/dehydrated THF solution (using 0.35 mL out of the solution prepared at 0.88 g/7 mL; 0.20 mmol) and a collidine/THF solution (using 0.35 mL out of the solution prepared by diluting collidine (1.35 mL) to 7 mL with THF; 0.50 mmol), and the vessel was shaken at 40° C. for two hours. Next, the reaction solution was removed, and the resin was washed with dehydrated THF (0.7 mL) four times and then washed with dehydrated DCM (0.7 mL) four times to give resin-loaded Compound aa051-c.

This was swollen with dehydrated DCM (1.0 mL) and washed with dehydrated THF (0.7 mL) four times, after which a triphenylphosphine/dehydrated THF solution (66.0 mg/0.7 mL, 0.25 mmol), methanol (0.020 mL, 0.50 mmol), and diisopropyl azodicarboxylate (DIAD) (0.05 mL, 0.25 mmol) were added, and the vessel was stirred at 40° C. for 30 minutes. Next, the reaction solution was removed, and the resin was washed with dehydrated THF (0.7 mL) four times and then washed with dehydrated DCM (0.7 mL) four times to give resin-loaded Compound aa051-d.

This was swollen with dehydrated DCM (1.0 mL) and washed with dehydrated NMP (0.7 mL) four times, after which a DBU/NMP solution (using 0.35 mL out of the solution prepared by diluting DBU (0.4 mL) to 3.5 mL with dehydrated NMP) and a 1-dodecanethiol/NMP solution (using 0.35 mL out of the solution prepared by diluting 1-dodecanethiol (1.2 mL) to 3.5 mL with dehydrated NMP) were added and the vessel was shaken at 40° C. for one hour. Next, the reaction solution was removed, and the resin was washed with dehydrated NMP (0.7 mL) four times and then washed with dehydrated DCM (0.7 mL) four times to give resin-loaded Compound aa051.

A small amount of the resin-loaded Compound aa051 was cleaved from the resin with TFE/DCM (1/1), and the structure of the amino acid was confirmed by LC/MS.

LCMS (ESI) m/z=160 (M+H)+

Retention time: 0.30 min (analysis condition SQDAA05)

Synthesis of Compound aa052 ((3S)-4-oxo-4-piperidin-1-yl-3-(propylamino)butanoic acid-2-chlorotrityl resin, H-nPrAsp-O-Trt(2-Cl)resin)

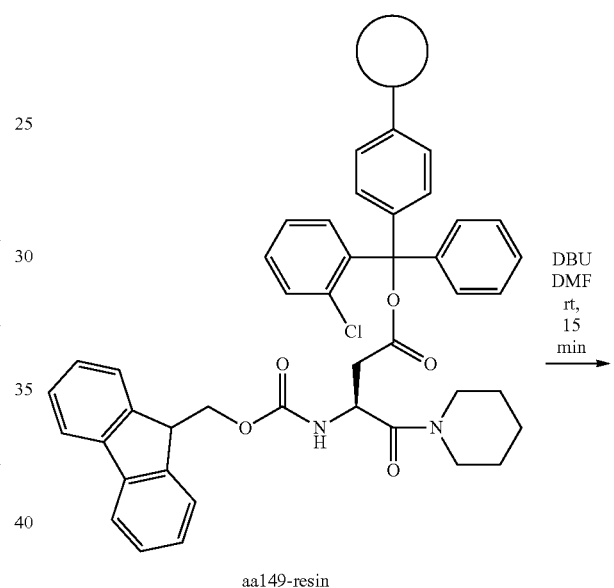

aa149-resin

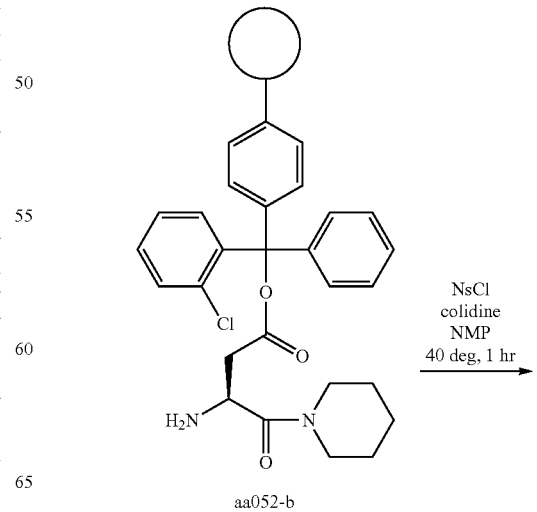

aa052-b

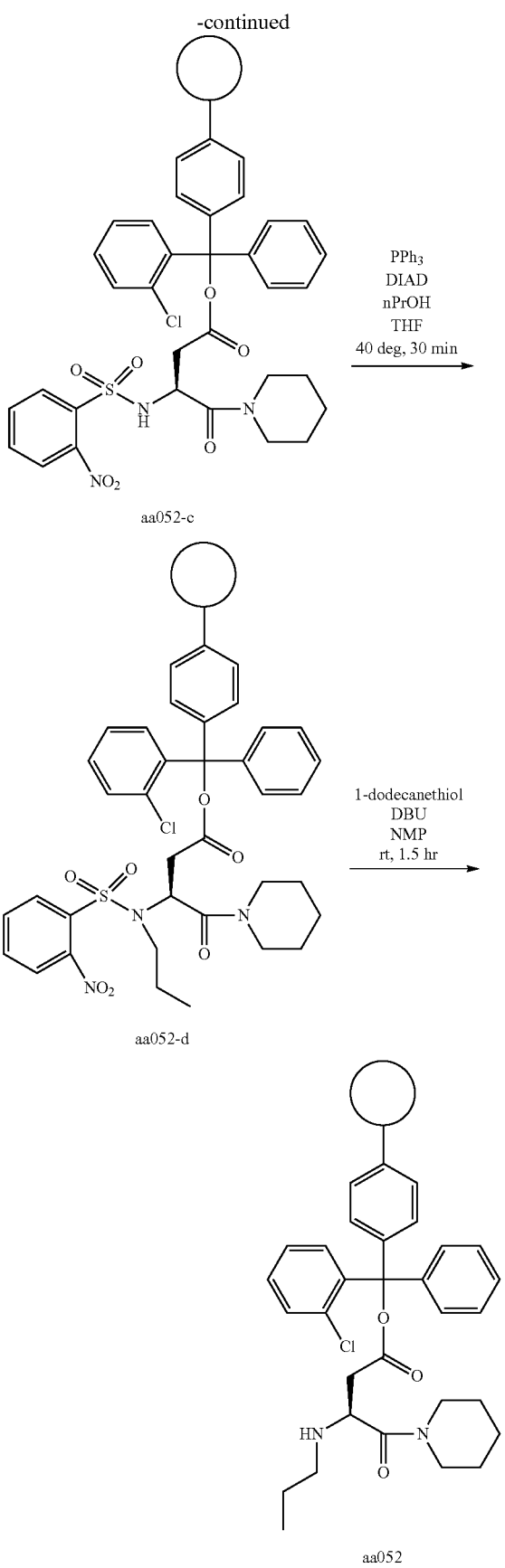

Into a reaction vessel equipped with a filter were placed Compound aa149-resin (3 g, 1.36 mmol, 0.452 mmol/g) and dehydrated DCM (30 mL), and the vessel was shaken at room temperature for 15 minutes. The DCM was removed by applying nitrogen pressure, after which dehydrated DMF (30 mL) was added and the DMF was removed by applying nitrogen pressure. This operation was performed four times. A 2% solution of DBU in DMF (18 mL) was added, the vessel was shaken at room temperature for 15 minutes, and the reaction solution was removed by applying nitrogen pressure. Dehydrated NMP (30 mL) was added and the NMP was removed by applying nitrogen pressure. This operation was performed six times to give resin-loaded Compound aa052-b.

Dehydrated NMP (30 mL) was added thereto and the NMP was removed by applying nitrogen pressure. This operation was performed six times. A solution of NsCl (1.20 g, 5.42 mmol) in dehydrated NMP (30 mL), and collidine (1.8 mL, 13.6 mmol) were added and the vessel was shaken at 40° C. for one hour, after which the reaction solution was removed by applying nitrogen pressure. Dehydrated NMP (30 mL) was added and the NMP was removed by applying nitrogen pressure. This operation was performed six times to give resin-loaded Compound aa052-c.

Dehydrated DCM (30 mL) was placed thereinto and the vessel was shaken at room temperature for 15 minutes. The DCM was removed by applying nitrogen pressure, after which dehydrated DCM (25 mL) was added and the DCM was removed by applying nitrogen pressure. This operation was performed twice. Dehydrated THF (25 mL) was added and the THF was removed by applying nitrogen pressure. This operation was performed four times. A solution of triphenylphosphine (1.78 g, 6.78 mmol), DIAD (1.34 mL, 6.78 mmol), and 1-propanol (1.02 mL, 13.6 mmol) in THF (30 mL) was added, the vessel was shaken at 40° C. for 30 minutes, and the reaction solution was removed by applying nitrogen pressure. Dehydrated THF (25 mL) was added and the THF was removed by applying nitrogen pressure. This operation was performed four times. Dehydrated DCM (25 mL) was added and the DCM was removed by applying nitrogen pressure. This operation was performed four times to give resin-loaded Compound aa052-d.

Into a reaction vessel equipped with a filter were placed resin-loaded Compound aa052-d (600 mg, 0.271 mol, 0.452 mmol/g) and dehydrated DCM (6 mL), and the vessel was shaken at room temperature for 15 minutes. The DCM was removed by applying nitrogen pressure, after which dehydrated NMP (6 mL) was added and the NMP was removed by applying nitrogen pressure. This operation was performed four times. A mixture of dehydrated NMP and DBU (9/1, 2.4 mL) and a mixture of dehydrated NMP and dodecanethiol (3/1, 3 mL) were added, the vessel was shaken at room temperature for 1.5 hours, and the reaction solution was removed by applying nitrogen pressure. Dehydrated NMP (6 mL) was added and the NMP was removed by applying nitrogen pressure. This operation was performed four times. Dehydrated DCM (6 mL) was added and the DCM was removed by applying nitrogen pressure. This operation was performed four times to give resin-loaded Compound aa052.

A small amount of the resin-loaded Compound aa052 was cleaved from the resin with TFE/DCM (1/1), and the structure of the amino acid was confirmed by LC/MS.

LCMS (ESI) m/z=243 (M+H)+

Retention time: 0.30 min (analysis condition SQDFA05)

Synthesis of Compound aa135-resin ((1R,2R)-2-(9H-fluoren-9-ylmethoxycarbonylamino)cyclohexane-1-carboxylic acid-2-chlorotrityl resin, Fmoc-2-ACHxC-O-Trt(2-Cl)resin)

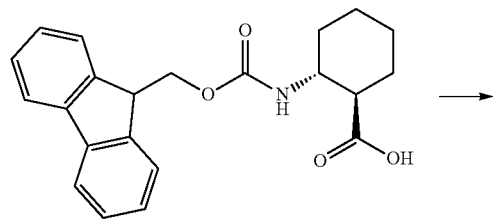

Fmoc-2-ACHxC-OH

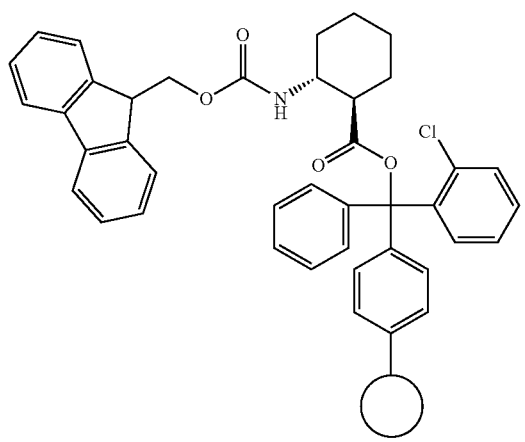

aa135-resin

Compound aa135-resin ((1R,2R)-2-(9H-fluoren-9-ylmethoxycarbonylamino)cyclohexane-1-carboxylic acid-2-chlorotrityl resin, Fmoc-2-ACHxC-O-Trt(2-Cl)resin) (4.38 g, loading amount 0.411 mmol/g) was obtained by the same method as in the synthesis of Compound aa007-resin using (1R,2R)-2-(9H-fluoren-9-ylmethoxycarbonylamino)cyclohexane-1-carboxylic acid (Fmoc-2-ACHxC-OH) purchased from a commercial supplier (1.12 g, 3.07 mmol) and 2-chlorotrityl chloride resin (1.60 mmol/g, 100-200 mesh, 1% DVB, 3.84 g, 6.14 mmol).

Synthesis of Compound aa136-resin ((1R,2R)-2-(9H-fluoren-9-ylmethoxycarbonylamino)cyclopentane-1-carboxylic acid-2-chlorotrityl resin (Fmoc-2-ACPnC-O-Trt(2-Cl)resin))

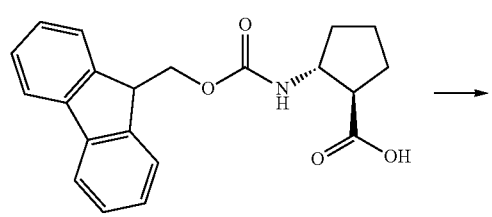

Fmoc-2-ACPnC-OH

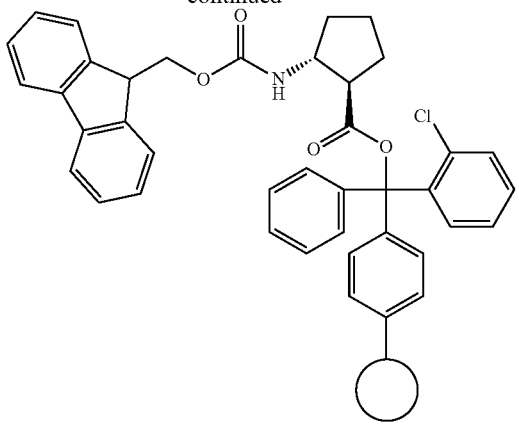

aa136-resin

Compound aa136-resin ((1R,2R)-2-(9H-fluoren-9-ylmethoxycarbonylamino)cyclopentane-1-carboxylic acid-2-chlorotrityl resin, Fmoc-2-ACPnC-O-Trt(2-Cl)resin) (1.65 g, loading amount 0.520 mmol/g) was obtained by the same method as in the synthesis of Compound aa007-resin using (1R,2R)-2-(9H-fluoren-9-ylmethoxycarbonylamino)cyclopentane-1-carboxylic acid (Fmoc-2-ACPnC-OH) purchased from a commercial supplier (0.411 g, 1.17 mmol) and 2-chlorotrityl chloride resin (1.60 mmol/g, 100-200 mesh, 1% DVB, 1.46 g, 2.34 mmol).

Synthesis of Compound aa137-resin, (3R)-3-(9H-fluoren-9-ylmethoxycarbonylamino)hex-5-ynoic acid-2-chlorotrityl resin (Fmoc-D-(Propargyl)Gly-(C#CH2)-O-Trt(2-Cl)resin)

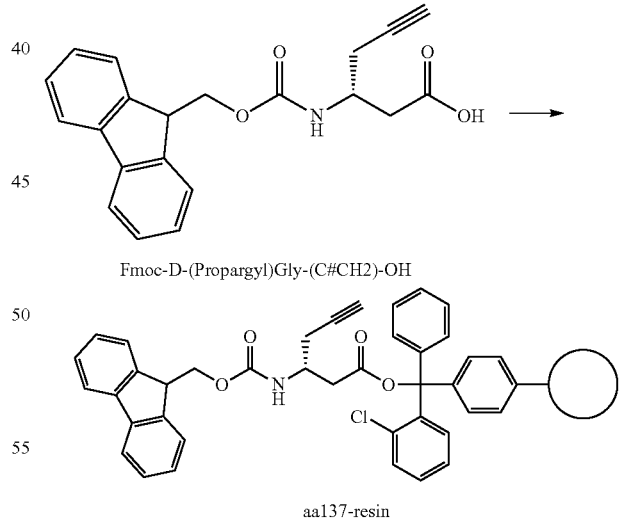

Fmoc-D-(Propargyl)Gly-(C#CH2)-OH aa137-resin

Compound aa137-resin ((3R)-3-(9H-fluoren-9-ylmethoxycarbonylamino)hex-5-ynoic acid-2-chlorotrityl resin, Fmoc-D-(Propargyl)Gly-(C#CH2)-O-Trt(2-Cl)resin) (4.18 g, loading amount 0.432 mmol/g) was obtained by the same method as in the synthesis of Compound aa007-resin using (3R)-3-(9H-fluoren-9-ylmethoxycarbonylamino)hex-5-ynoic acid (Fmoc-D-(Propargyl)Gly-(C#CH2)-OH) purchased from a commercial supplier (0.994 g, 2.85 mmol)

and 2-chlorotrityl chloride resin (1.59 mmol/g, 100-200 mesh, 1% DVB, 3.58 g, 5.69 mmol).

Synthesis of Compound aa138-resin, (3R)-3-(9H-fluoren-9-ylmethoxycarbonylamino)butanoic acid-2-chlorotrityl resin (Fmoc-D-3-Abu-O-Trt(2-Cl)resin)

Synthesis of Compound aa139-resin, (3R)-3-[9H-fluoren-9-ylmethoxycarbonyl(methyl)amino]butanoic acid-2-chlorotrityl resin (Fmoc-D-3-MeAbu-O-Trt(2-Cl)resin)

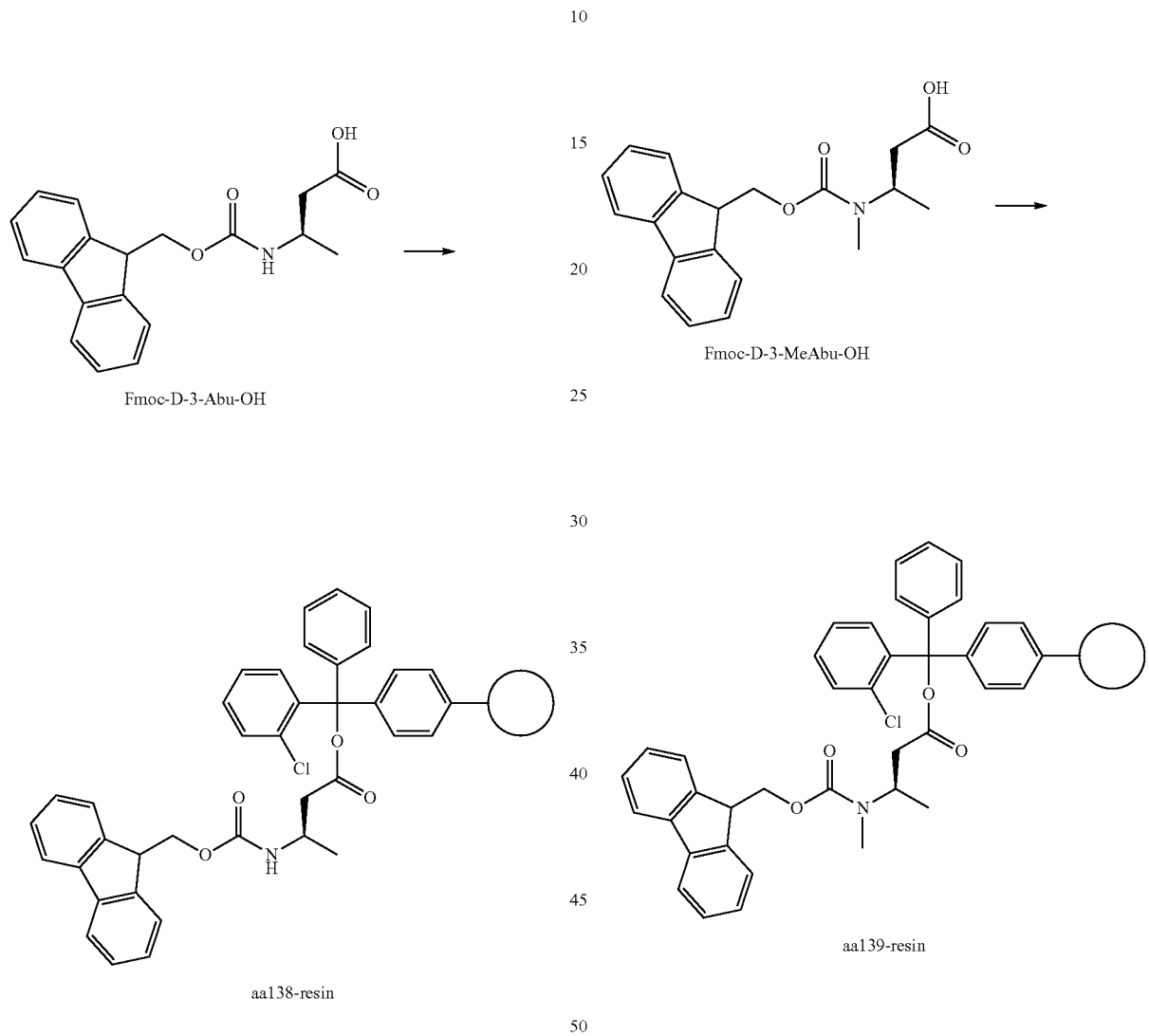

Fmoc-D-3-Abu-OH

Fmoc-D-3-MeAbu-OH aa138-resin aa139-resin

Compound aa138-resin, (3R)-3-(9H-fluoren-9-ylmethoxycarbonylamino)butanoic acid-2-chlorotrityl resin (Fmoc-D-3-Abu-O-Trt(2-Cl)resin) (33.44 g, loading amount 0.598 mmol/g) was obtained by the same method as in the synthesis of Compound aa007-resin using (3R)-3-(9H-fluoren-9-ylmethoxycarbonylamino)butanoic acid (Fmoc-D-3-Abu-OH) purchased from a commercial supplier (7.1 g, 21.82 mmol) and 2-chlorotrityl chloride resin (1.6 mmol/g, 100-200 mesh, 1% DVB, 27.25 g, 43.6 mmol).

Another lot synthesized in the same manner with a different loading amount was also used for peptide synthesis in the present Examples.

Compound aa139-resin, (3R)-3-[9H-fluoren-9-ylmethoxycarbonyl(methyl)amino]butanoic acid-2-chlorotrityl resin (Fmoc-D-3-MeAbu-O-Trt(2-Cl)resin) (58.95 g, loading amount 0.536 mmol/g) was obtained by the same method as in the synthesis of Compound aa007-resin using (3R)-3-[9H-fluoren-9-ylmethoxycarbonyl(methyl)amino]butanoic acid (Fmoc-D-3-MeAbu-OH) purchased from a commercial supplier (11.5 g, 33.9 mmol) and 2-chlorotrityl chloride resin (1.69 mmol/g, 100-200 mesh, 1% DVB, 50 g, 84.5 mmol).

Another lot synthesized in the same manner with a different loading amount was also used for peptide synthesis in the present Examples.

Synthesis of Compound aa140-resin, (3R)-3-(9H-fluoren-9-ylmethoxycarbonylamino)hex-5-enoic acid-2-chlorotrityl resin (Fmoc-D-Gly(Allyl)-(C#CH2)-O-Trt(2-Cl)resin)

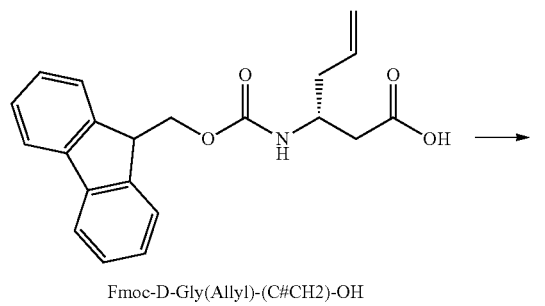

Fmoc-D-Gly(Allyl)-(C#CH2)-OH

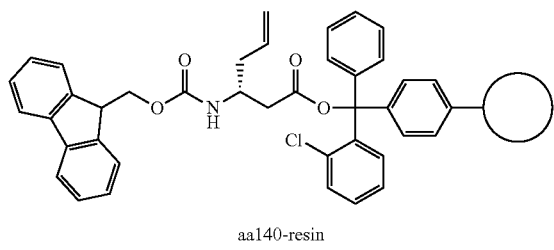

aa140-resin

Compound aa140-resin ((3R)-3-(9H-fluoren-9-ylmethoxycarbonylamino)hex-5-enoic acid-2-chlorotrityl resin, Fmoc-D-Gly(Allyl)-(C#CH2)-O-Trt(2-Cl)resin) (4.15 g, loading amount 0.420 mmol/g) was obtained by the same method as in the synthesis of Compound aa007-resin using (3R)-3-(9H-fluoren-9-ylmethoxycarbonylamino)hex-5-enoic acid (Fmoc-D-Gly(Allyl)-(C#CH2)-OH) purchased from a commercial supplier (1 g, 2.85 mmol) and 2-chlorotrityl chloride resin (1.59 mmol/g, 100-200 mesh, 1% DVB, 3.58 g, 5.69 mmol).

Synthesis of Compound aa141-resin, (3R)-3-(9H-fluoren-9-ylmethoxycarbonylamino)-5-methyl-hexanoic acid-2-chlorotrityl resin (Fmoc-D-Leu-(C#CH2)-O-Trt(2-Cl)resin)

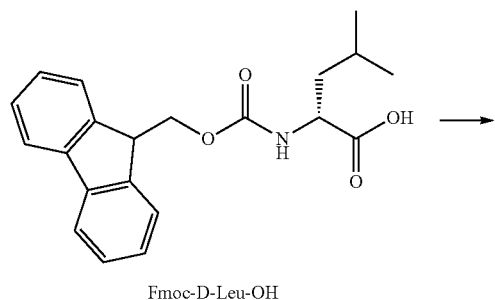

Fmoc-D-Leu-OH

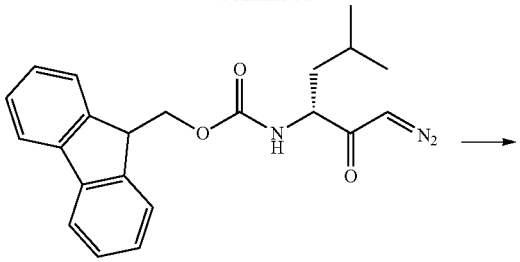

aa141-a

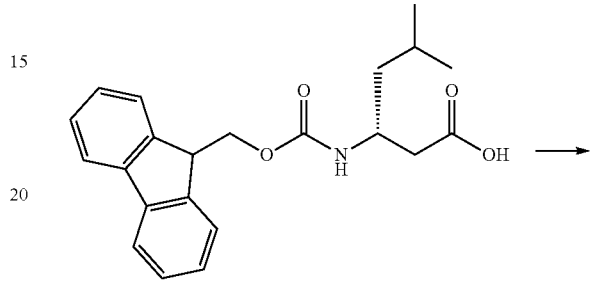

aa141
Fmoc-D-Leu-(C#CH2)-OH

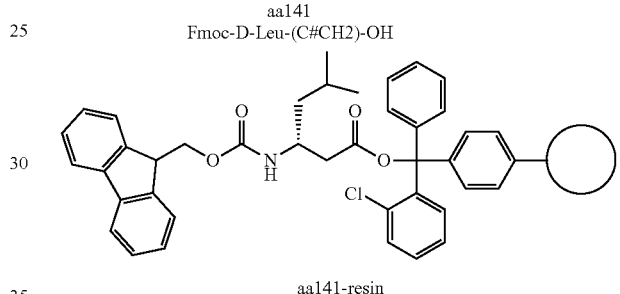

aa141-resin

To a mixture of diethyl ether (30 mL) and aqueous potassium hydroxide (50%, 12 mL) was added N-methyl-N-nitrosoacetamide (CAS No. 7417-67-6) (3.5 g, 29.5 mmol) at 0° C., and the mixture was stirred for 30 minutes. The diethyl ether layer was separated, and potassium hydroxide pellets were added to prepare a diazomethane solution. Two batches of the diazomethane solution on the same scale were further prepared and used for the next reaction.

Fmoc-D-Leu-OH (N-[(9H-fluoren-9-ylmethoxy)carbonyl]-D-leucine) (5 g, 14.15 mmol) was dissolved in toluene and the solvent was evaporated under reduced pressure. This operation was performed three times. The residue was dissolved in THF (40.4 mL) and cooled in a salt ice bath. N-Methylmorpholine (2.022 mL, 18.39 mmol) and ethyl chloroformate (1.766 mL, 18.39 mmol) were added dropwise thereto, respectively. After stirring in the salt ice bath for 20 minutes, the prepared diazomethane solution (28.3 mmol) was added at room temperature three times at 30-minutes intervals. The progress of the reaction was confirmed by LC/MS. The reaction solution was cooled to 0° C. and diluted with diethyl ether, after which a 10% aqueous citric acid solution was added and the mixture was extracted with diethyl ether. The organic layer was sequentially washed with a saturated aqueous sodium bicarbonate solution and brine and dried over anhydrous sodium sulfate, and the solvent was evaporated under reduced pressure. The residue was purified by silica gel column chromatography (hexane/ethyl acetate) to give aa141-a (5 g, 13.24 mmol).

LCMS (ESI) m/z=378.3 (M+H)+

Retention time: 0.89 min (analysis condition SQDFA05)

A solution of aa141-a (4 g, 10.59 mmol) in THF (42.4 mL) was cooled to 0° C., water (4.24 mL), silver trifluoroacetate (0.257 g, 1.165 mmol), and N-methylmorpholine (2.91 mL, 26.5 mmol) were added, and the mixture was stirred at room temperature. After confirming the completion of the reaction by LC/MS, the reaction solution was cooled to 0° C. and diluted with diethyl ether (40 mL). An aqueous citric acid solution (10%) was added to the mixture, which was extracted with ethyl acetate. The organic layer was washed with brine and then dried over anhydrous sodium sulfate, and the solvent was evaporated under reduced pressure. The resulting residue was triturated with hexane/ethyl acetate, and the solid was collected by filtration to give the target compound, aa141 ((3R)-3-(9H-fluoren-9-ylmethoxycarbonylamino)-5-methylhexanoic acid, Fmoc-D-Leu-(C#CH2)-OH) (4 g, 82%).

LCMS (ESI) m/z=368.3 (M+H)+

Retention time: 0.85 min (analysis condition SQDFA05)

Compound aa141-resin ((3R)-3-(9H-fluoren-9-ylmethoxycarbonylamino)-5-methylhexanoic acid-2-chlorotrityl resin, Fmoc-D-Leu-(C#CH2)-O-Trt(2-Cl)resin) (4.1 g, loading amount 0.349 mmol/g) was obtained by the same method as in the synthesis of Compound aa007-resin using aa141 ((3R)-3-(9H-fluoren-9-ylmethoxycarbonylamino)-5-methylhexanoic acid, Fmoc-D-Leu-(C#CH2)-OH) (1.045 g, 2.85 mmol) and 2-chlorotrityl chloride resin (1.59 mmol/g, 100-200 mesh, 1% DVB, 3.58 g, 5.69 mmol).

Synthesis of Compound aa143-resin, (R)-2-[1-(9H-fluoren-9-ylmethoxycarbonyl)piperidin-2-yl]acetic acid-2-chlorotrityl resin (Fmoc-D-Pic(2)-(C#CH2)-O-Trt(2-Cl)resin)

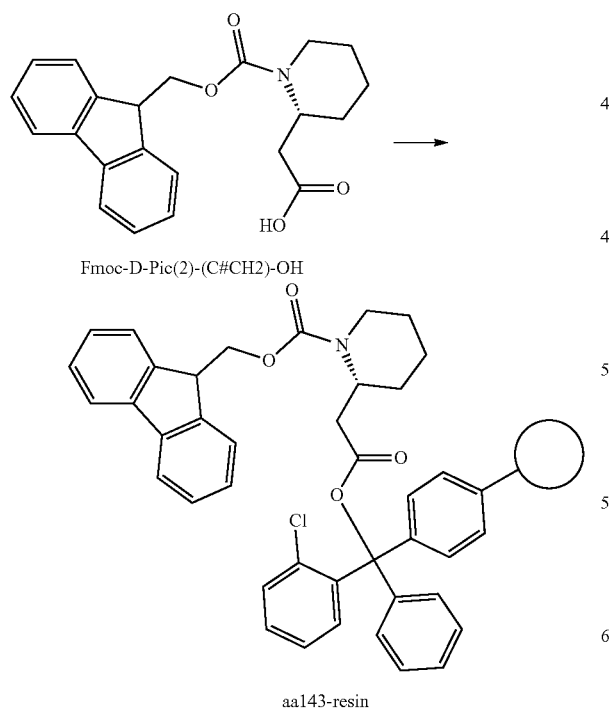

Fmoc-D-Pic(2)-(C#CH2)-OH aa143-resin

Compound aa143-resin, (R)-2-[1-(9H-fluoren-9-ylmethoxycarbonyl)piperidin-2-yl]acetic acid-2-chlorotrityl resin (Fmoc-D-Pic(2)-(C#CH2)-O-Trt(2-Cl)resin) (4.27 g, loading amount 0.347 mmol/g) was obtained by the same method as in the synthesis of Compound aa007-resin using (R)-2-[1-(9H-fluoren-9-ylmethoxycarbonyl)piperidin-2-yl] acetic acid (Fmoc-D-Pic(2)-(C#CH2)-OH) (1.01 g, 2.76 mmol) purchased from a commercial supplier and 2-chlorotrityl chloride resin (1.6 mmol/g, 100-200 mesh, 1% DVB, 3.84 g, 6.14 mmol).

Synthesis of Compound aa144-resin, 2-[(2R)-1-(9H-fluoren-9-ylmethoxycarbonyl)pyrrolidin-2-yl]acetic acid-2-chlorotrityl resin (Fmoc-D-Pro-(C#CH2)-O-Trt(2-Cl)resin)

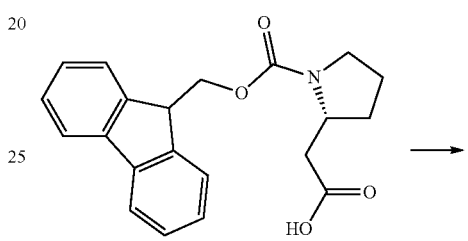

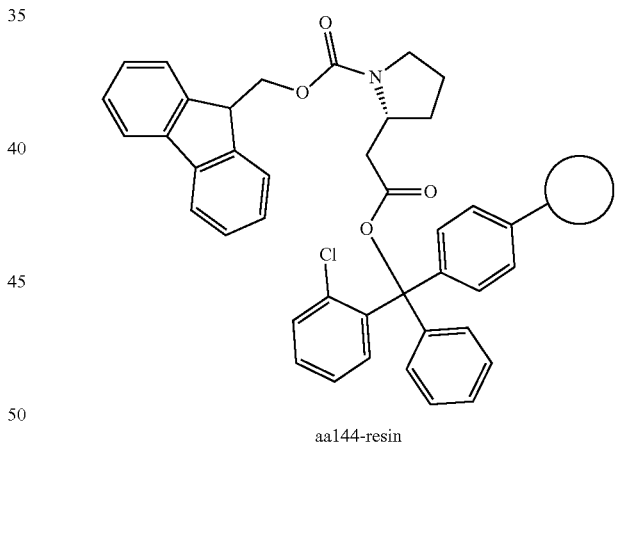

aa144-resin

Compound aa144-resin (2-[(2R)-1-(9H-fluoren-9-ylmethoxycarbonyl)pyrrolidin-2-yl]acetic acid-2-chlorotrityl resin, Fmoc-D-Pro-(C#CH2)-O-Trt(2-Cl)resin) (7.19 g, loading amount 0.377 mmol/g) was obtained by the same method as in the synthesis of Compound aa007-resin using 2-[(2R)-1-(9H-fluoren-9-ylmethoxycarbonyl)pyrrolidin-2-yl]acetic acid (Fmoc-D-Pro-(C#CH2)-OH) (1 g, 2.85 mmol) purchased from a commercial supplier and 2-chlorotrityl chloride resin (1.6 mmol/g, 100-200 mesh, 1% DVB, 7 g, 21.39 mmol).

Synthesis of Compound aa107-resin, (3S)-4-[2-(tert-butylamino)-2-oxoethoxy]-3-(9H-fluoren-9-ylmethoxycarbonylamino)butanoic acid-2-chlorotrityl resin (Fmoc-D-Ser(NtBu-Aca)-(C#CH2)-O-Trt (2-Cl)resin)

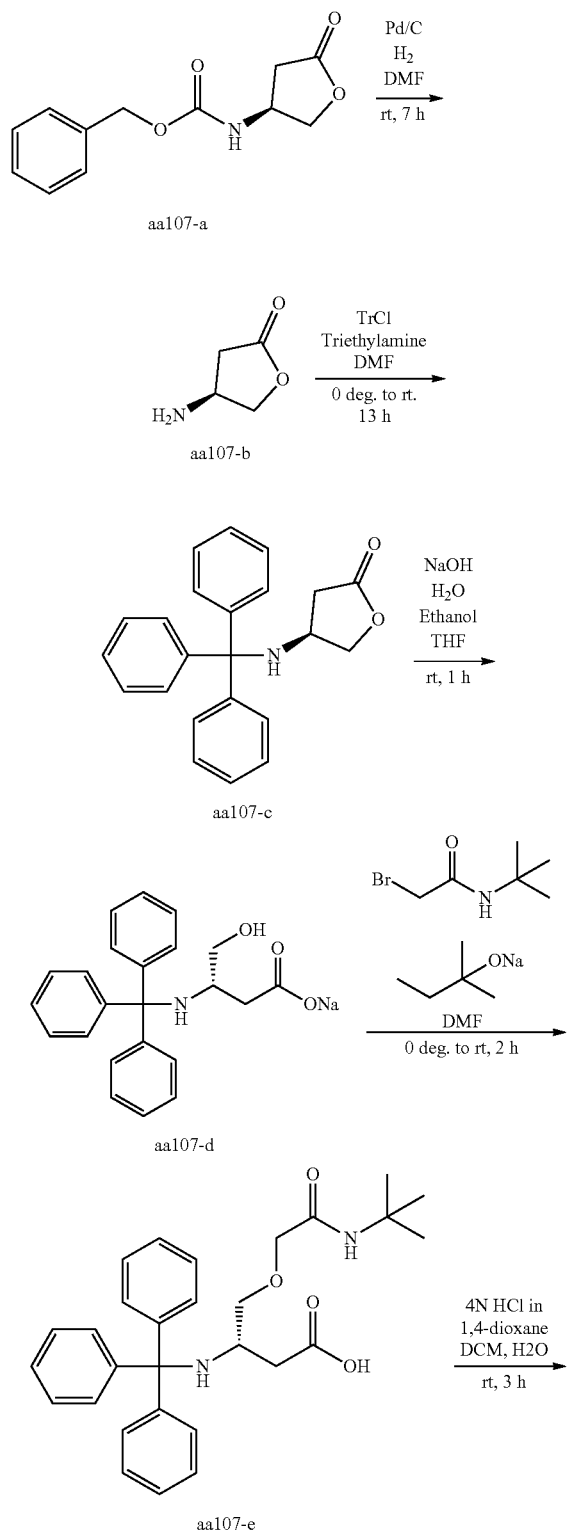

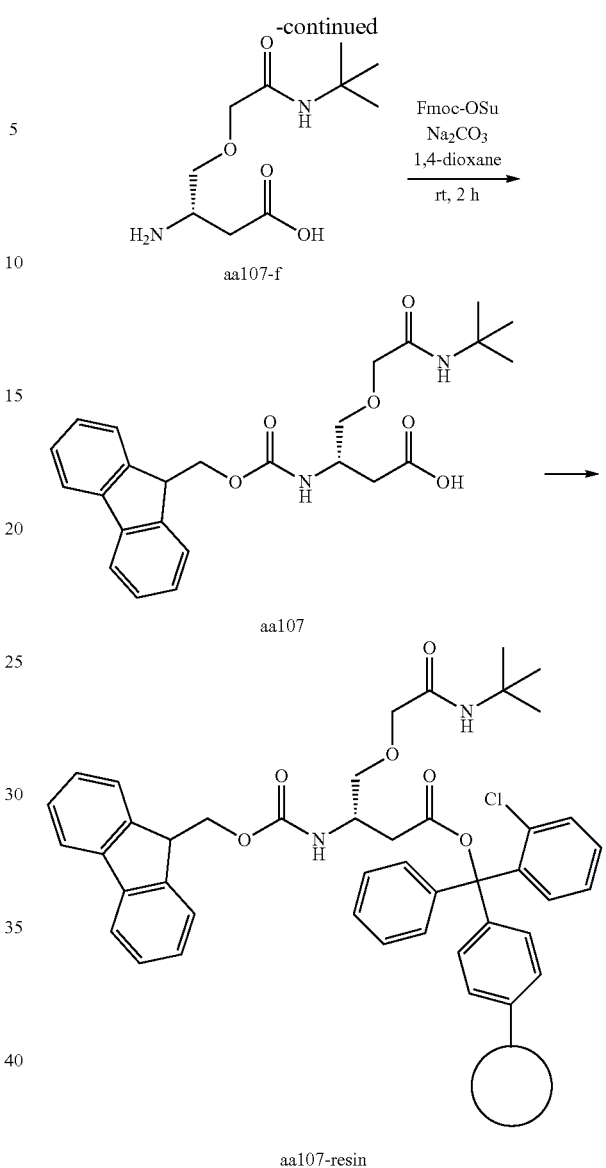

To Compound aa107-a ((S)—β-(carbobenzoxyamino)-γ-butyrolactone) (15 g, 63.8 mmol) and palladium on carbon (5 g, 30 wt %) was added DMF (180 mL) under a nitrogen atmosphere, and the atmosphere was replaced with a hydrogen atmosphere. The reaction solution was stirred at room temperature for seven hours and filtered through celite. The celite was washed with DMF (25 mL) twice and the resulting residue was concentrated to give Compound aa107-b as a crude product (6.0 g, 93%). This was used for the next reaction without further purification.

The obtained Compound aa107-b (6.0 g, 59.3 mmol) was dissolved in DMF (170 mL) and cooled to 0° C. To the reaction solution was added triethylamine (24.8 mL, 178 mmol), after which a solution of trityl chloride (TrCl) (18.2 g, 65.3 mmol) in DMF (130 mL) was slowly added dropwise over 20 minutes. The reaction solution was warmed to room temperature and stirred at room temperature for 13 h. The reaction solution was concentrated under reduced pressure and the resulting residue was purified by silica gel column chromatography (n-hexane/ethyl acetate) to give Compound aa107-c (17 g, 83%).

LCMS (ESI) m/z=366 (M+Na)+

Retention time: 0.65 min (analysis condition SQDAA50)

The obtained Compound aa107-c (20.8 g, 60.6 mmol) and sodium hydroxide (2.66 g, 66.6 mmol) were dissolved in a water/ethanol/THF solution (1.14 L, 1/5/5), the mixture was stirred at room temperature for one hour, and the reaction solution was concentrated under reduced pressure to give Compound aa107-d (23.9 g, quant.).

LCMS (ESI) m/z=384 (M+Na)+

Retention time: 0.47 min (analysis condition SQDAA50)

The obtained Compound aa107-d (6 g, 15.7 mmol) was dissolved in DMF (50 mL) and cooled to 0° C. A solution of sodium tert-pentoxide (46.9 mmol) in toluene (14.8 mL) was added thereto, and the mixture was warmed to room temperature and stirred for 30 minutes. Next, a solution of 2-bromo-N-(tert-butyl)acetamide (CAS No. 57120-58-8) (4.56 g, 23.5 mmol) in DMF (15 mL) was added at 0° C. The reaction solution was warmed to room temperature and stirred for five hours. The reaction solution was concentrated under reduced pressure, and the resulting residue was purified by reverse phase column chromatography (10 mM aqueous ammonium acetate (AA)/methanol) to give Compound aa107-e (5.9 g, 79%).

LCMS (ESI) m/z=497 (M+Na)+

Retention time: 0.60 min (analysis condition SQDAA50)

The obtained Compound aa107-e (5.0 g, 10.5 mmol) was dissolved in DCM/water (140 mL, 5/2), and 4 N aqueous hydrochloric acid/1,4-dioxane (42.1 mL, 169 mmol) was added. The reaction solution was stirred at room temperature for one hour, water (40 mL) was then added, and the mixture was washed with n-hexane (100 mL) twice. The resulting aqueous solution containing Compound aa107-f was used as such for the next reaction.

LCMS (ESI) m/z=233 (M+H)+

Retention time: 0.27 min (analysis condition SQDFA05)

To the above aqueous solution of Compound aa107-f (ca. 90 mL) were added sodium carbonate (27.8 g, 263 mmol) and a solution of Fmoc-OSu (4.25 g, 12.6 mmol) in 1,4-dioxane (75 mL). The reaction solution was stirred at room temperature for two hours, after which TBME (300 mL) and 2 N aqueous hydrochloric acid (150 mL) were added. The organic layer was concentrated under reduced pressure, and the resulting residue was then purified by reverse phase column chromatography (acetonitrile with 0.1% formic acid/distilled water with 0.1% formic acid) to give Compound aa107 ((3S)-4-[2-(tert-butylamino)-2-oxoethoxy]-3-(9H-fluoren-9-ylmethoxycarbonylamino)butanoic acid, Fmoc-D-Ser(NtBu-Aca)-(C#CH2)-OH) (2.3 g, 48.2% through two steps).

LCMS (ESI) m/z=455 (M+H)+

Retention time: 0.75 min (analysis condition SQDFA05)

Compound aa107-resin ((3S)-4-[2-(tert-butylamino)-2-oxoethoxy]-3-(9H-fluoren-9-ylmethoxycarbonylamino)butanoic acid-2-chlorotrityl resin, Fmoc-D-Ser(NtBu-Aca)-(C#CH2)-O-Trt(2-Cl)resin) (4 g, loading amount 0.279 mmol/g) was obtained by the same method as in the synthesis of Compound aa007-resin using Compound aa107 ((3S)-4-[2-(tert-butylamino)-2-oxoethoxy]-3-(9H-fluoren-9-ylmethoxycarbonylamino)butanoic acid, Fmoc-D-Ser(NtBu-Aca)-(C#CH2)-OH) (1 g, 2.2 mmol) and 2-chlorotrityl chloride resin (1.6 mmol/g, 100-200 mesh, 1% DVB, 3.43 g, 5.5 mmol).

Synthesis of Compound aa108-resin, (3S)-3-(9H-fluoren-9-ylmethoxycarbonylamino)-4-(3-methylbutoxy)butanoic acid-2-chlorotrityl resin (Fmoc-D-Ser(iPen)-(C#CH2)-O-Trt(2-Cl)resin)

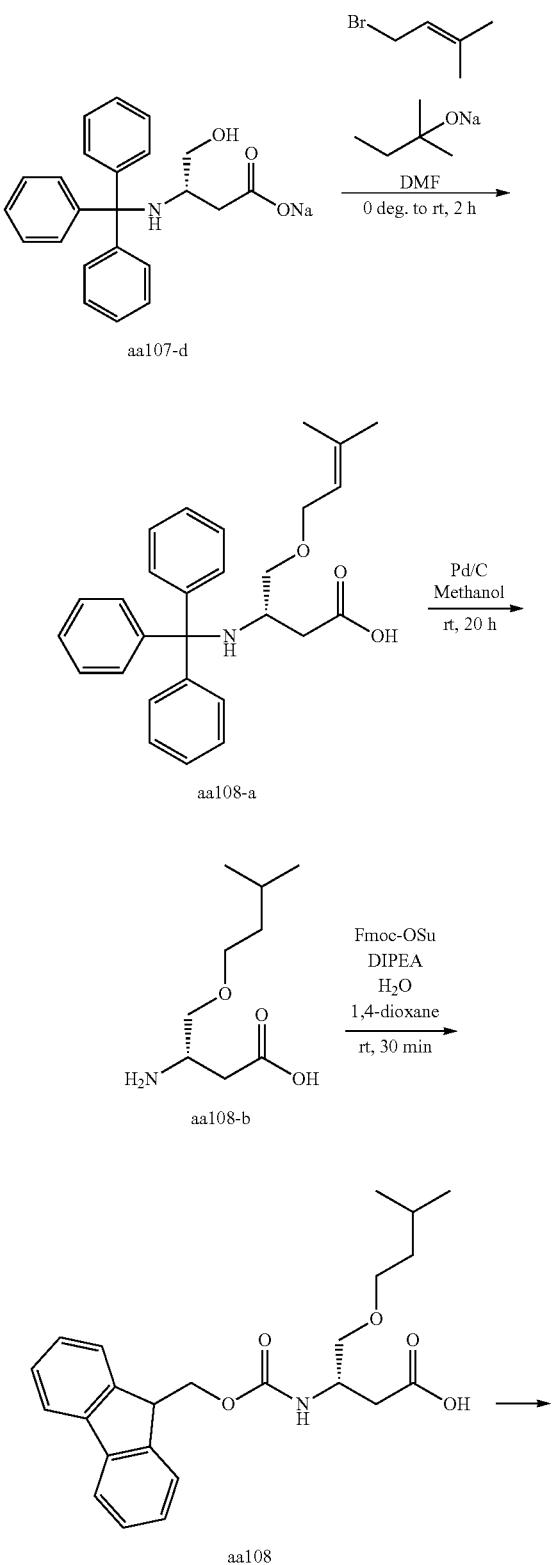

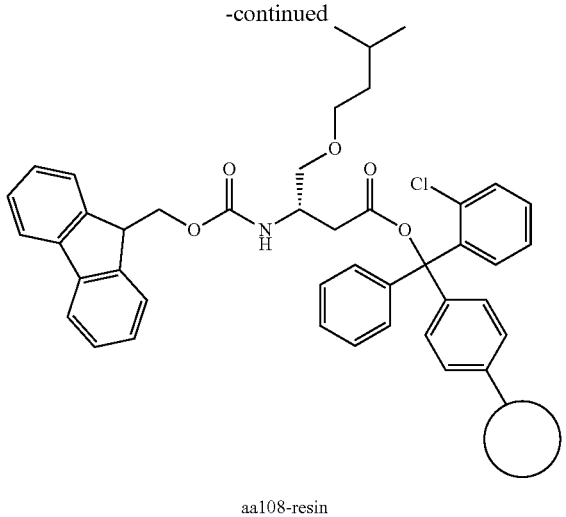

aa108-resin

Compound aa107-d (6 g, 15.7 mmol) was dissolved in DMF (103 mL) and cooled to 0° C. To the reaction solution was added a solution of sodium tert-pentoxide (46.9 mmol) in toluene (14.1 mL), and the mixture was warmed to room temperature and stirred for 30 minutes. Next, 1-bromo-3-methyl-2-butene (2.71 mL, 23.5 mmol) was added at 0° C. The reaction solution was warmed to room temperature and stirred for four hours. 1-Bromo-3-methyl-2-butene (0.9 mL, 7.8 mmol) was further added and the mixture was stirred for four hours. Thereafter, the reaction solution was concentrated under reduced pressure, and the resulting residue was purified by reverse phase column chromatography (10 mM aqueous ammonium acetate/methanol) to give Compound aa108-a (3.4 g, 50.6%).

LCMS (ESI) m/z=428 (M−H)−

Retention time: 0.59 min (analysis condition SQDFA50)

Compound aa108-a (3.6 g, 8.38 mmol) and palladium on carbon (360 mg, 10 wt %) were mixed in methanol (41.9 mL), and then the mixture was stirred at room temperature for 20 hours under hydrogen atmosphere. To the reaction solution were added formic acid and DMSO, and the mixture was decanted with hexane (100 mL) and then concentrated under reduced pressure. The residue was purified by reverse phase column chromatography (acetonitrile with 0.1% formic acid/distilled water with 0.1% formic acid) to give Compound aa108-b (600 mg, 38%).

LCMS (ESI) m/z=190 (M+H)+

Retention time: 0.15 min (analysis condition SQDFA50)

The obtained Compound aa108-b (600 mg, 3.17 mmol) was dissolved in water (3.6 mL), DIPEA (2.49 mL, 14.3 mmol) was added, and Fmoc-OSu (1.07 g, 3.17 mmol) was added as a solution in 1,4-dioxane (4.75 mL). The reaction solution was stirred at room temperature for 30 minutes, water (4 mL) was then added, and the mixture was extracted with hexane/ether (3 mL, 3/1) twice. Potassium hydrogen sulfate (KHSO$_4$) (1.62 g, 14.3 mmol) was added to the aqueous layer, which was extracted with ethyl acetate (20 mL) twice. The combined organic layers were washed with brine/water (1/1, 15 mL) twice, dried over anhydrous sodium sulfate, and then filtered, and the filtrate was concentrated under reduced pressure to give Compound aa108 ((3S)-3-(9H-fluoren-9-ylmethoxycarbonylamino)-4-(3-methylbutoxy)butanoic acid, Fmoc-D-Ser(iPen)-(C#CH2)-OH) (1.2 g, 92%).

LCMS (ESI) m/z=412 (M+H)+

Retention time: 0.91 min (analysis condition SQDFA05)

Compound aa108-resin ((3S)-3-(9H-fluoren-9-yl-methoxycarbonylamino)-4-(3-methylbutoxy)butanoic acid-2-chlorotrityl resin, Fmoc-D-Ser(iPen)-(C#CH2)-O-Trt(2-Cl)resin) (434 mg, loading amount 0.415 mmol/g) was obtained by the same method as in the synthesis of Compound aa007-resin using Compound aa108 ((3S)-3-(9H-fluoren-9-ylmethoxycarbonylamino)-4-(3-methylbutoxy) butanoic acid, Fmoc-D-Ser(iPen)-(C#CH2)-OH) (0.1 g, 0.243 mmol) and 2-chlorotrityl chloride resin (1.6 mmol/g, 100-200 mesh, 1% DVB, 0.380 g, 0.61 mmol).

Synthesis of Compound aa145-resin, 3-[9H-fluoren-9-ylmethoxycarbonyl(methyl)amino]propanoic acid-2-chlorotrityl resin (Fmoc-bMeAla-O-Trt(2-Cl) resin)

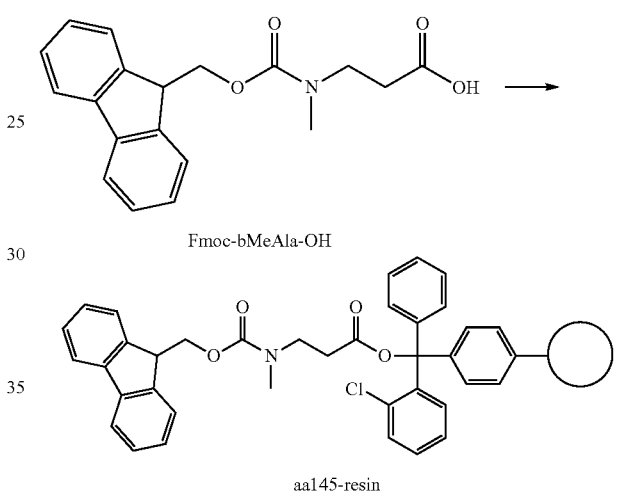

Fmoc-bMeAla-OH aa145-resin

Compound aa145-resin (3-[9H-fluoren-9-ylmethoxycarbonyl(methyl)amino]propanoic acid-2-chlorotrityl resin, Fmoc-bMeAla-O-Trt(2-Cl)resin) (4.34 g, loading amount 0.449 mmol/g) was obtained by the same method as in the synthesis of Compound aa007-resin using 3-[9H-fluoren-9-ylmethoxycarbonyl(methyl)amino]propanoic acid (Fmoc-bMeAla-OH) (1 g, 3.07 mmol) purchased from a commercial supplier and 2-chlorotrityl chloride resin (1.6 mmol/g, 100-200 mesh, 1% DVB, 3.84 g, 6.15 mmol).

Synthesis of Compound aa146-resin, 3-(9H-fluoren-9-ylmethoxycarbonylamino)propanoic acid-2-chlorotrityl resin (Fmoc-bAla-O-Trt(2-Cl)resin)

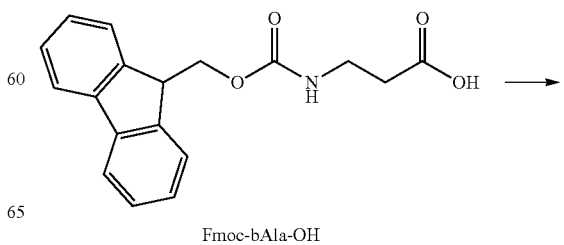

Fmoc-bAla-OH

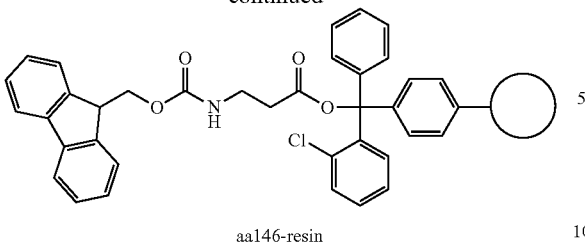

aa146-resin

Compound aa146-resin (3-(9H-fluoren-9-ylmethoxycarbonylamino)propanoic acid-2-chlorotrityl resin, Fmoc-bAla-O-Trt(2-Cl)resin) (37.86 g, loading amount 0.528 mmol/g) was obtained by the same method as in the synthesis of Compound aa007-resin using 3-(9H-fluoren-9-ylmethoxycarbonylamino)propanoic acid (Fmoc-bAla-OH) (8 g, 25.7 mmol) purchased from a commercial supplier and 2-chlorotrityl chloride resin (1.6 mmol/g, 100-200 mesh, 1% DVB, 32.1 g, 51.4 mmol).

Synthesis of Compound aa147-resin, (3R)-3-(9H-fluoren-9-ylmethoxycarbonylamino)-5-phenylpentanoic acid-2-chlorotrityl resin (Fmoc-D-Hph-(C#CH2)-O-Trt(2-Cl)resin)

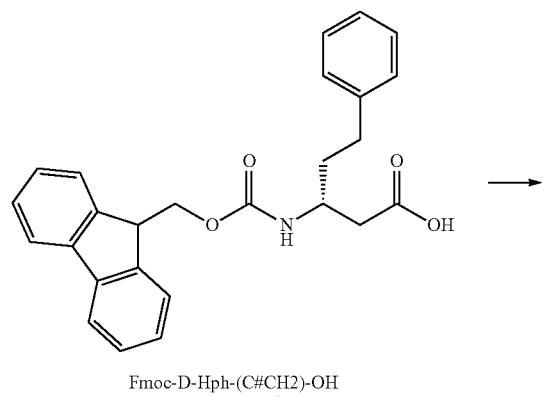

Fmoc-D-Hph-(C#CH2)-OH

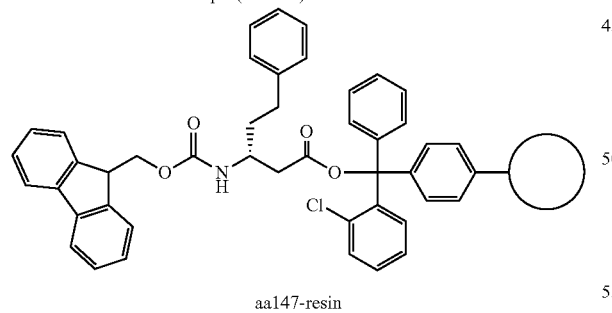

aa147-resin

Compound aa147-resin ((3R)-3-(9H-fluoren-9-ylmethoxycarbonylamino)-5-phenylpentanoic acid-2-chlorotrityl resin, Fmoc-D-Hph-(C#CH2)-O-Trt(2-Cl)resin) (3.61 g, loading amount 0.415 mmol/g) was obtained by the same method as in the synthesis of Compound aa007-resin using (3R)-3-(9H-fluoren-9-ylmethoxycarbonylamino)-5-phenylpentanoic acid (Fmoc-D-Hph-(C#CH2)-OH) (1 g, 2.41 mmol) purchased from a commercial supplier and 2-chlorotrityl chloride resin (1.6 mmol/g, 100-200 mesh, 1% DVB, 3.03 g, 4.82 mmol).

Synthesis of Compound aa148-resin, (3S)-3-(9H-fluoren-9-ylmethoxycarbonylamino)-4,4,4-trifluorobutanoic acid-2-chlorotrityl resin (Fmoc-3-CF3-bAla-(C#CH2)-O-Trt(2-Cl)resin)

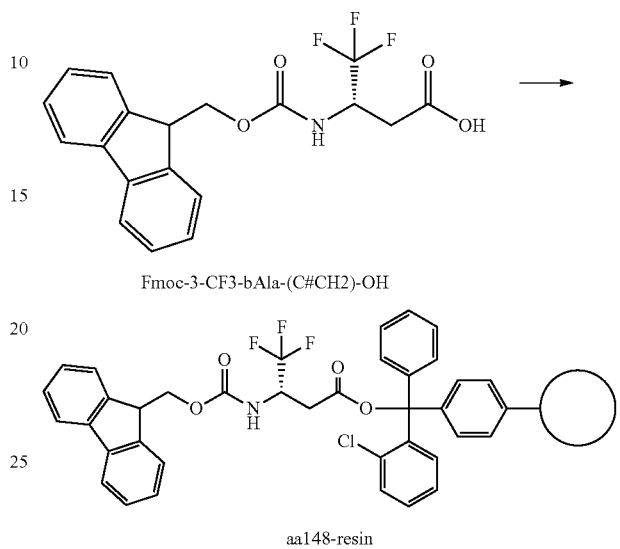

Fmoc-3-CF3-bAla-(C#CH2)-OH aa148-resin

Compound aa148-resin, (3S)-3-(9H-fluoren-9-ylmethoxycarbonylamino)-4,4,4-trifluorobutanoic acid-2-chlorotrityl resin (Fmoc-3-CF3-bAla-(C#CH2)-O-Trt(2-Cl) resin) (2.19 g, loading amount 0.399 mmol/g) was obtained by the same method as in the synthesis of Compound aa007-resin using (3S)-3-(9H-fluoren-9-ylmethoxycarbonylamino)-4,4,4-trifluorobutanoic acid (Fmoc-3-CF3-bAla-(C#CH2)-OH) (0.569 mg, 1.5 mmol) purchased from a commercial supplier and 2-chlorotrityl chloride resin (1.59 mmol/g, 100-200 mesh, 1% DVB, 1.89 g, 3 mmol).

Synthesis of Compound aa149-resin, (3S)-3-(9H-fluoren-9-ylmethoxycarbonylamino)-4-oxo-4-piperidin-1-ylbutanoic acid-2-chlorotrityl resin (Fmoc-Asp(O-Trt(2-Cl)resin)-pip)

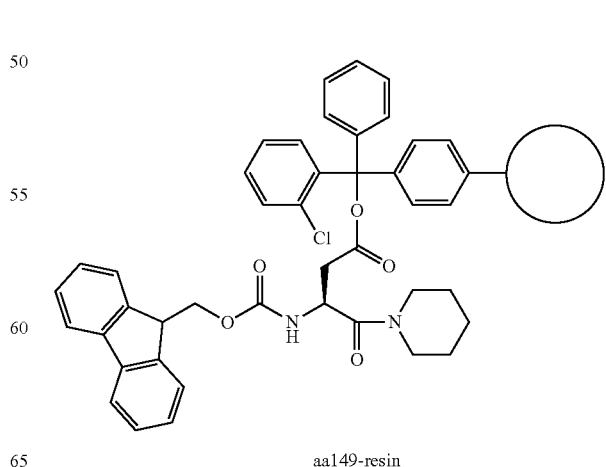

aa149-resin

Compound aa149-resin, (3S)-3-(9H-fluoren-9-yl-methoxycarbonylamino)-4-oxo-4-piperidin-1-ylbutanoic acid-2-chlorotrityl resin (Fmoc-Asp(O-Trt(2-Cl)resin)-pip) was synthesized by the method described in WO 2013/100132 or WO 2018/225864.

Synthesis of Compound aa155-resin, 2-[(2R)-3-(dimethylamino)-2-[9H-fluoren-9-ylmethoxycarbonyl(methyl)amino]-3-oxopropyl]sulfanylacetic acid-2-chlorotrityl resin The amino acid was loaded onto the resin according to the following scheme.

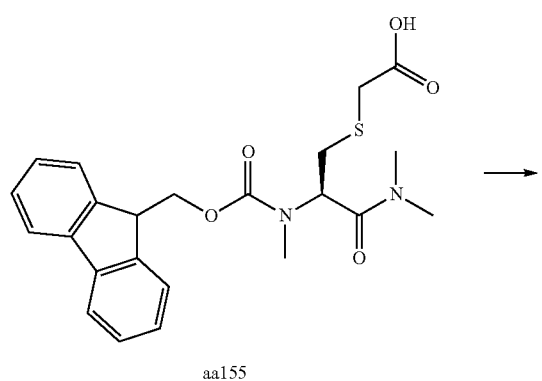

aa155

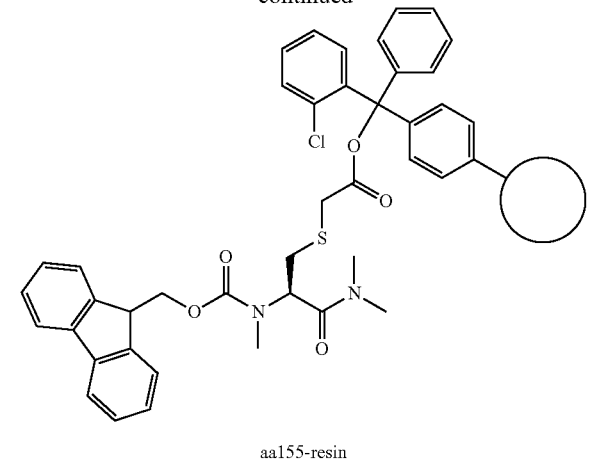

aa155-resin

Compound aa155-resin, 2-[(2R)-3-(dimethylamino)-2-[9H-fluoren-9-ylmethoxycarbonyl(methyl)amino]-3-oxopropyl]sulfanylacetic acid-2-chlorotrityl resin (1.54 g, loading amount 0.336 mmol/g) was obtained by the same method as in the synthesis of Compound aa007-resin using Compound aa155 (2-[(2R)-3-(dimethylamino)-2-[9H-fluoren-9-ylmethoxycarbonyl(methyl)amino]-3-oxopropyl]sulfanylacetic acid) (0.46 g, 1.04 mmol) and 2-chlorotrityl chloride resin (1.6 mmol/g, 100-200 mesh, 1% DVB, 1.3 g, 2.08 mmol).

1-3. Peptide Solid-Phase Synthesis by an Automated Synthesizer

Cyclic peptide compounds (Compounds 1-762, 764-845, 847-1027, 1029-1146, 1148-1410, 1412-2020, 2111, 2143-2151, and 2172-2179) (Table 24) were synthesized by the method described in WO 2013/100132 or WO 2018/225864. Peptides were synthesized by the Fmoc method detailed below using a peptide synthesizer (Multipep RS; manufactured by Intavis). The detailed operational procedure was according to the manual appended to the synthesizer. The relationship between formal names, structures, and abbreviations of the respective amino acid residues constituting cyclic peptides described in Table 24 will be understood from Tables 2 to 7 above and Table 8 below.

TABLE 8

| Abbreviation | Amino acid structural formula | Name |
| --- | --- | --- |
| MeGln(Aze-3-F2) | | (2S)-5-(3,3-difluoroazetidin-1-yl)-2-(methylamino)-5-oxo-pentanoic acid |
| (MeOMeallyl)Gly | | 2-[[(E)-4-methoxybut-2-enyl]amino]acetic acid |
| (DMAOEt)Gly | | 2-[2-[2-(dimethylamino)-2-oxo-ethoxy]ethylamino]acetic acid |

TABLE 8-continued

| Abbreviation | Amino acid structural formula | Name |
|---|---|---|
| (HOtBuOEt)Gly | | 2-[2-(2-hydroxy-2-methyl-propoxy)ethylamino]acetic acid |
| (HOtBuallyl)Gly | | 2-[[(E)-5-hydroxy-5-methyl-hex-2-enyl]amino]acetic acid |
| (Me2NCOnPr)Gly | | 2-[4-(dimethylamino)-4-oxo-butyl]amino]acetic acid |
| (5-OH-nPent)Gly | | 2-(5-hydroxypentylamino)acetic acid |
| (HOEtallyl)Gly | | 2-[[(E)-5-hydroxypent-2-enyl]amino]acetic acid |
| (DMFallyl)Gly | | 2-[[(E)-4-(dimethylamino)-4-oxo-but-2-enyl]amino]acetic acid |
| (HOiPrallyl)Gly | | 2-[[(E)-4-hydroxy-4-methyl-pent-2-enyl]amino]acetic acid |
| Hph(24-F2) | | (2S)-2-amino-4-(2,4-difluorophenyl)butanoic acid |
| (HOEt)Gly | | 2-(2-hydroxyethylamino)acetic acid |
| (3-pyr-Me)Gly | | 2-(3-pyridylmethylamino)acetic acid |
| (4-pyr-Me)Gly | | 2-(4-pyridylmethylamino)acetic acid |

TABLE 8-continued

| Abbreviation | Amino acid structural formula | Name |
|---|---|---|
| (3-pyr-Et)Gly | | 2-[2-(3-pyridyl)ethylamino]acetic acid |
| (4-pyr-Et)Gly | | 2-[2-(4-pyridyl)ethylamino]acetic acid |
| (Et(2-F3)OEt)Gly | | 2-[2-(2,2,2-trifluoroethoxy)ethylamino]acetic acid |
| (MeOEtOEt)Gly | | 2-[2-(2-methoxyethoxy)ethylamino]acetic acid |
| (Et(2-F2)OEt)Gly | | 2-[2-(2,2-difluoroethoxy)ethylamino]acetic acid |
| (pip(4-F2)Et)Gly | | 2-[2-(4,4-difluoro-1-piperidyl)ethylamino]acetic acid |

TABLE 8-continued

| Abbreviation | Amino acid structural formula | Name |
| --- | --- | --- |
| MeAbu(BocAze) | | (2S)-4-(1-tert-butoxycarbonylazetidin-3-yl)-2-(methylamino)butanoic acid |
| Hph(2-F-4-Cl) | | (2S)-2-amino-4-(4-chloro-2-fluoro-phenyl)butanoic acid |
| MeAbu(BocAzedene) | | (2S)-4-(1-tert-butoxycarbonylazetidin-3-ylidene)-2-(methylamino)butanoic acid |
| MeAbu(THP) | | (2S)-2-(methylamino)-4-tetrahydropyran-4-yl-butanoic acid |
| MeAbu(THPdene) | | (2S)-2-(methylamino)-4-tetrahydropyran-4-ylidene-butanoic acid |

TABLE 8-continued

| Abbreviation | Amino acid structural formula | Name |
|---|---|---|
| (OxecBu)Gly | | 2-(2-oxaspiro[3.3]heptan-6-ylamino)acetic acid |
| (OxeMe)Gly | | 2-(oxetan-3-ylmethylamino)acetic acid |
| (F2cBucBu)Gly | | 2-[(2,2-difluorospiro[3.3]heptan-6-yl)amino]acetic acid |
| (Ph-4-Cl)Gly | | 2-(4-chloroanilino)acetic acid |
| (Ph-3-Cl)Gly | | 2-(3-chloroanilino)acetic acid |
| (3-Thienyl)Gly | | 2-(3-thienylamino)acetic acid |
| Hyp(2-EtOH) | | (2S,4R)-4-(2-hydroxyethoxy)pyrrolidine-2-carboxylic acid |
| cisHyp(2-EtOH) | | (2S,4S)-4-(2-hydroxyethoxy)pyrrolidine-2-carboxylic acid |

TABLE 8-continued

| Abbreviation | Amino acid structural formula | Name |
| --- | --- | --- |
| Hph(2-F-5-Cl) | | (2S)-2-amino-4-(5-chloro-2-fluorophenyl)butanoic acid |
| PhGly | | 2-anilinoacetic acid |
| Hyp(3-thie-Me) | | (2S,4R)-4-(3-thienylmethoxy)pyrrolidine-2-carboxylic acid |
| Ser(Ph) | | (2S)-2-amino-3-phenoxy-propanoic acid |
| Pro(4S-Tri) | | (2S,4S)-4-(triazol-1-yl)pyrrolidine-2-carboxylic acid |
| Pro(4R-Tri) | | (2S,4R)-4-(triazol-1-yl)pyrrolidine-2-carboxylic acid |
| cisPro(4-pip-4-F2) | | (2S,4S)-4-(4,4-difluoro-1-piperidyl)pyrrolidine-2-carboxylic acid |
| Hyp(Et(2-F2)) | | (2S,4R)-4-(2,2-difluoroethoxy)pyrrolidine-2-carboxylic acid |
| cisHyp(Et(2-F2)) | | (2S,4S)-4-(2,2-difluoroethoxy)pyrrolidine-2-carboxylic acid |

TABLE 8-continued

| Abbreviation | Amino acid structural formula | Name |
|---|---|---|
| cisHyp(3-Me-Pyr) | | (2S,4S)-4-(3-pyridylmethoxy)pyrrolidine-2-carboxylic acid |
| Hyp(3-Me-Pyr) | | (2S,4R)-4-(3-pyridylmethoxy)pyrrolidine-2-carboxylic acid |
| MeAla(3-Pyr-4-CN) | | (2S)-3-(6-cyano-3-pyridyl)-2-(methylamino)propanoic acid |
| MeTyr(3-F) | | (2S)-3-(3-fluoro-4-hydroxy-phenyl)-2-(methylamino)propanoic acid |
| cisHyp(Bzl(4-OCHF2)) | | (2S,4S)-4-[[4-(difluoromethoxy)phenyl]methoxy]pyrrolidine-2-carboxylic acid |
| cisHyp(Bzl(4-Me)) | | (2S,4S)-4-(p-tolylmethoxy)pyrrolidine-2-carboxylic acid |
| cisHyp(Bzl(3-OMe)) | | (2S,4S)-4-[(3-methoxyphenyl)methoxy]pyrrolidine-2-carboxylic acid |
| cisHyp(Bzl(3-Me)) | | (2S,4S)-4-(m-tolylmethoxy)pyrrolidine-2-carboxylic acid |
| cisHyp(Bzl(2-Me)) | | (2S,4S)-4-(o-tolylmethoxy)pyrrolidine-2-carboxylic acid |

TABLE 8-continued

| Abbreviation | Amino acid structural formula | Name |
|---|---|---|
| Hyp(Bzl(4-OCHF2)) | | (2S,4R)-4-[4-(difluoromethoxy)phenyl]methoxy]pyrrolidine-2-carboxylic acid |
| Hyp(Bzl(4-Me)) | | (2S,4R)-4-(p-tolylmethoxy)pyrrolidine-2-carboxylic acid |
| Hph(245-F3) | | (2S)-2-amino-4-(2,4,5-trifluorophenyl)butanoic acid |
| Hyp(Bzl(3-OMe)) | | (2S,4R)-4-[(3-methoxyphenyl)methoxy]pyrrolidine-2-carboxylic acid |
| Hyp(Bzl(3-Me)) | | (2S,4R)-4-(m-tolylmethoxy)pyrrolidine-2-carboxylic acid |
| Hyp(Bzl(2-Me)) | | (2S,4R)-4-(o-tolylmethoxy)pyrrolidine-2-carboxylic acid |
| Hyp(Bzl(4-Cl)) | | (2S,4R)-4-[(4-chlorophenyl)methoxy]pyrrolidine-2-carboxylic acid |
| Hyp(Bzl(3-Cl)) | | (2S,4R)-4-[(3-chlorophenyl)methoxy]pyrrolidine-2-carboxylic acid |

TABLE 8-continued

| Abbreviation | Amino acid structural formula | Name |
| --- | --- | --- |
| cisHyp(Bzl(4-Cl)) | | (2S,4S)-4-[(4-chlorophenyl)methoxy]pyrrolidine-2-carboxylic acid |
| cisHyp(Bzl(3-Cl)) | | (2S,4S)-4-[(3-chlorophenyl)methoxy]pyrrolidine-2-carboxylic acid |
| cisHyp(Bzl(2-Cl)) | | (2S,4S)-4-[(2-chlorophenyl)methoxy]pyrrolidine-2-carboxylic acid |
| Hyp(Bzl(2-Cl)) | | (2S,4R)-4-[(2-chlorophenyl)methoxy]pyrrolidine-2-carboxylic acid |
| cisHyp(Et) | | (2S,4S)-4-ethoxypyrrolidine-2-carboxylic acid |
| Hph(F5) | | (2S)-2-amino-4-(2,3,4,5,6-pentafluorophenyl)butanoic acid |
| Hyp(Bzl) | | (2S,4R)-4-benzyloxypyrrolidine-2-carboxylic acid |
| cisHyp | | (2S,4S)-4-hydroxypyrrolidine-2-carboxylic acid |
| Hyp | | (2S,4R)-4-hydroxypyrrolidine-2-carboxylic acid |

TABLE 8-continued

| Abbreviation | Amino acid structural formula | Name |
| --- | --- | --- |
| Ser(tBuOH) | 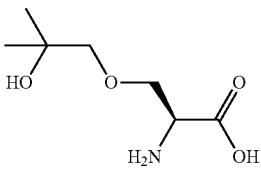 | (2S)-2-amino-3-(2-hydroxy-2-methyl-propoxy)propanoic acid |
| Ser(Bn-2-Cl) | 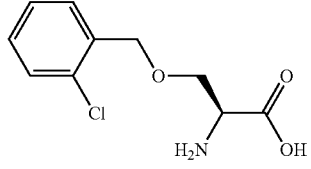 [SMILES: N[C@@H](COCc1ccccc1Cl)C(=O)O] | (2S)-2-amino-3-[(2-chlorophenyl)methoxy]propanoic acid |
| Ser(Bn-3-Cl) | 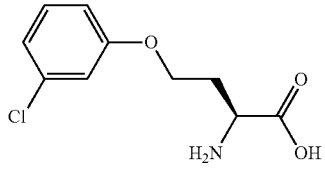 | (2S)-2-amino-3-[(3-chlorophenyl)methoxy]propanoic acid |
| Ser(Ph-4-Cl) | 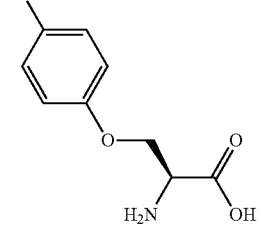 | (2S)-2-amino-3-(4-chlorophenoxy)propanoic acid |
| Hse(Ph-4-CF3) | 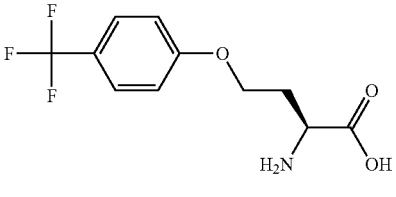 [SMILES: N[C@@H](CCOc1ccc(C(F)(F)F)cc1)C(=O)O] | (2S)-2-amino-4-[4-(trifluoromethyl)phenoxy]butanoic acid |
| Hse(Ph-34-Cl2) | 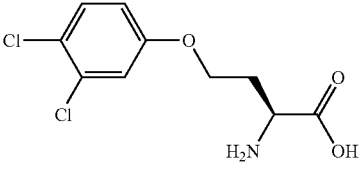 [SMILES: N[C@@H](CCOc1ccc(Cl)c(Cl)c1)C(=O)O] | (2S)-2-amino-4-(3,4-dichlorophenoxy)butanoic acid |
| Hse(Ph-4-Cl) | 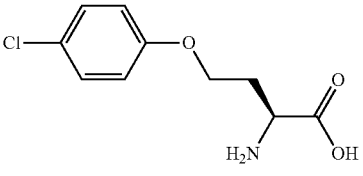 [SMILES: N[C@@H](CCOc1ccc(Cl)cc1)C(=O)O] | (2S)-2-amino-4-(4-chlorophenoxy)butanoic acid |

TABLE 8-continued

| Abbreviation | Amino acid structural formula | Name |
|---|---|---|
| Hph(4-CF3-2-F) | | (2S)-2-amino-4-[2-fluoro-4-(trifluoromethyl)phenyl]butanoic acid |
| Ser(Bn-4-Cl) | | (2S)-2-amino-3-[(4-chlorophenyl)methoxy]propanoic acid |
| Phe3(4-CF3) | | (2S)-2-amino-5-[4-(trifluoromethyl)phenyl]pentanoic acid |
| Hph(34-Cl2-5-OtBu) | | (2S)-2-amino-4-(3-tert-butoxy-4,5-dichloro-phenyl)butanoic acid |
| Hph(34-Cl2-5-OnBu) | | (2S)-2-amino-4-(3-butoxy-4,5-dichloro-phenyl)butanoic acid |
| Hph(34-Cl2-5-OiPr) | | (2S)-2-amino-4-(3,4-dichloro-5-isopropoxy-phenyl)butanoic acid |

TABLE 8-continued

| Abbreviation | Amino acid structural formula | Name |
|---|---|---|
| Hph(34-Cl2-5-CN) | | (2S)-2-amino-4-(3,4-dichloro-5-cyano-phenyl)butanoic acid |
| Hph(34-Cl2-5-OMe) | | (2S)-2-amino-4-(3,4-dichloro-5-methoxy-phenyl)butanoic acid |
| Hph(345-Cl3) | | (2S)-2-amino-4-(3,4,5-trichlorophenyl)butanoic acid |
| Abu(7-Quino) | | (2S)-2-amino-4-(7-quinolyl)butanoic acid |
| Hph(3-F-4-CHF2) | | (2S)-2-amino-4-[4-(difluoromethyl)-3-fluoro-phenyl]butanoic acid |
| MeAsp-pip(4-F2) | | (3S)-4-(4,4-difluoro-1-piperidyl)-3-(methylamino)-4-oxo-butanoic acid |

TABLE 8-continued

| Abbreviation | Amino acid structural formula | Name |
| --- | --- | --- |
| Hph(4-SO2Me) | | (2S)-2-amino-4-(4-methylsulfonylphenyl)butanoic acid |
| Abu(2-Pyr-4-CF3) | | (2S)-2-amino-4-[5-(trifluoromethyl)-2-pyridyl]butanoic acid |
| Abu(3-Pyr-4-CHF2) | | (2S)-2-amino-4-[6-(difluoromethyl)-3-pyridyl]butanoic acid |
| Abu(5-Bzfr) | | (2S)-2-amino-4-(benzofuran-5-yl)butanoic acid |
| Abu(3-Pyr-4-OMe) | | (2S)-2-amino-4-(6-methoxy-3-pyridyl)butanoic acid |

TABLE 8-continued

| Abbreviation | Amino acid structural formula | Name |
| --- | --- | --- |
| Abu(1-Me-5-Indo) | | (2S)-2-amino-4-(1-methylindol-5-yl)butanoic acid |
| Abu(1-Me-6-Indo) | | (2S)-2-amino-4-(1-methylindol-6-yl)butanoic acid |
| Abu(6-Quino) | | (2S)-2-amino-4-(6-quinolyl)butanoic acid |
| Hph(3-F-4-OCF3) | | (2S)-2-amino-4-[3-fluoro-4-(trifluoromethoxy)phenyl]butanoic acid |
| Hph(3-Cl-4-OCF3) | | (2S)-2-amino-4-[3-chloro-4-(trifluoromethoxy)phenyl]butanoic acid |

TABLE 8-continued

| Abbreviation | Amino acid structural formula | Name |
|---|---|---|
| MeAsp-pip(3-F2) | 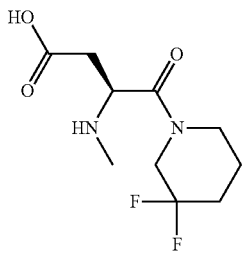 [SMILES: CN[C@@H](CC(=O)O)C(=O)N1CCCC(F)(F)C1] | (3S)-4-(3,3-difluoro-1-piperidyl)-3-(methylamino)-4-oxo-butanoic acid |
| Abu(34-Cate(CF2)) | 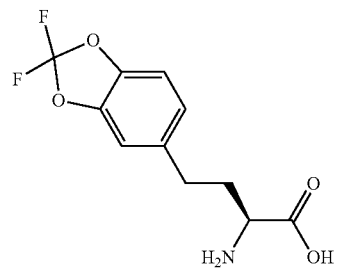 [SMILES: N[C@@H](CCc1ccc2c(c1)OC(F)(F)O2)C(=O)O] | (2S)-2-amino-4-(2,2-difluoro-1,3-benzodioxol-5-yl)butanoic acid |
| Abu(3-Pyr-4-CF3) | 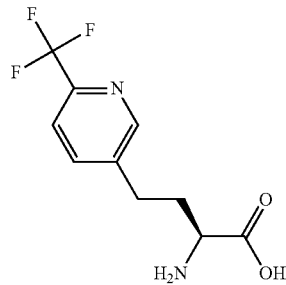 [SMILES: N[C@@H](CCc1ccc(C(F)(F)F)nc1)C(=O)O] | (2S)-2-amino-4-[6-(trifluoromethyl)-3-pyridyl]butanoic acid |
| Hph(3-OMe-4-CF3) | 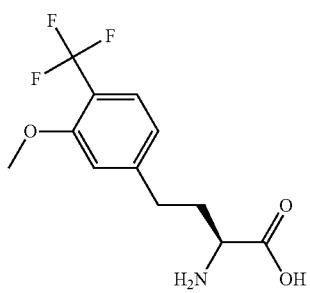 [SMILES: COc1cc(CC[C@H](N)C(=O)O)ccc1C(F)(F)F] | (2S)-2-amino-4-[3-methoxy-4-(trifluoromethyl)phenyl]butanoic acid |
| Hph(3-CN-4-CF3) | 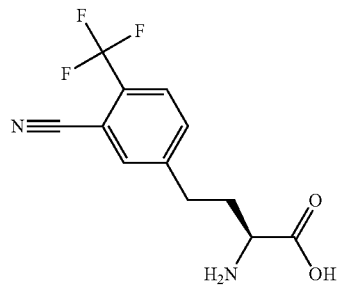 [SMILES: N#Cc1cc(CC[C@H](N)C(=O)O)ccc1C(F)(F)F] | (2S)-2-amino-4-[3-cyano-4-(trifluoromethyl)phenyl]butanoic acid |

TABLE 8-continued

| Abbreviation | Amino acid structural formula | Name |
| --- | --- | --- |
| Hph(3-F-4-OCHF2) | | (2S)-2-amino-4-[4-(difluoromethoxy)-3-fluoro-phenyl]butanoic acid |
| Phe(3-C#C) | | (2S)-2-amino-3-(3-ethynylphenyl)propanoic acid |
| Phe(3-Cl-4-F) | | (2S)-2-amino-3-(3-chloro-4-fluoro-phenyl)propanoic acid |
| Hph(3-CF3) | | (2S)-2-amino-4-[3-(trifluoromethyl)phenyl]butanoic acid |
| 1-ACPrC | | 1-aminocyclopropanecarboxylic acid |
| cHex | | 1-aminocyclohexanecarboxylic acid |
| Hph(246-F3) | | (2S)-2-amino-4-(2,4,6-trifluorophenyl)butanoic acid |
| EtPhe(2-Cl) | | (2S)-3-(2-chlorophenyl)-2-(ethylamino)propanoic acid |

TABLE 8-continued

| Abbreviation | Amino acid structural formula | Name |
| --- | --- | --- |
| MeAsn(mor) | | (2S)-2-(methylamino)-4-morpholino-4-oxo-butanoic acid |
| MeAsn(pyrro) | | (2S)-2-(methylamino)-4-oxo-4-pyrrolidin-1-yl-butanoic acid |
| MeAsn(pip) | | (2S)-2-(methylamino)-4-oxo-4-(1-piperidyl)butanoic acid |
| MeAsn(Aze) | | (2S)-4-(azetidin-1-yl)-2-(methylamino)-4-oxo-butanoic acid |
| MeAsn(Me2) | | (2S)-4-(dimethylamino)-2-(methylamino)-4-oxo-butanoic acid |
| MeGln(mor) | | (2S)-2-(methylamino)-5-morpholino-5-oxo-pentanoic acid |
| MeGln(pyrro) | | (2S)-2-(methylamino)-5-oxo-5-pyrrolidin-1-yl-pentanoic acid |

TABLE 8-continued

| Abbreviation | Amino acid structural formula | Name |
|---|---|---|
| MeGln(pip) | | (2S)-2-(methylamino)-5-oxo-5-(1-piperidyl)pentanoic acid |
| MeGln(Aze) | | (2S)-5-(azetidin-1-yl)-2-(methylamino)-5-oxo-pentanoic acid |
| Hph(2-F-6-Cl) | | (2S)-2-amino-4-(2-chloro-6-fluoro-phenyl)butanoic acid |
| MeSer(tBuOH) | | (2S)-3-(2-hydroxy-2-methyl-propoxy)-2-(methylamino)propanoic acid |

The peptide synthesis method by the Fmoc method (the basic peptide synthesis method) is described in detail in the following 1-3-1 to 1-3-5.

1-3-1. Peptide Elongation Reaction by the Fmoc Method from the N-Terminus of an Amino Acid Peptide compounds were synthesized by a solid-phase synthesis method using Fmoc-protected amino acids on a peptide synthesizer (Multipep RS or Multipep RSi) manufactured by Intavis. Specific procedures for the operation were performed according to the instructions attached to the synthesizer.

Fmoc-protected amino acids (0.3-0.6 mol/L) constituting the target peptide, and HOAt, oxyma, or HOOBt (0.375 mol/L) serving as a carboxyl group activator were dissolved in NMP or NMP/DMF (1/1) to prepare Solution 1. When the Fmoc-protected amino acids were poorly soluble in the above-mentioned solvents, DMSO was added at 20% to 30% (v/v) to prepare Solution 1. When using, for example, Fmoc-MeSer(tBuOTHP)-OH, Fmoc-Ser(tBuOTHP)-OH, Fmoc-MeSer(THP)-OH, Fmoc-Thr(THP)-OH, Fmoc-Ser(THP)-OH, Fmoc-cisHyp(THP)-OH (Compound aa101), or Fmoc-Hyp(THP)-OH (Compound aa102) as an Fmoc-protected amino acid having a THP protecting group on the side chain, oxyma was used as the carboxyl group activator to prepare Solution 1, and Molecular Sieves 4A 1/8 (Wako Pure Chemical Industries) or Molecular Sieves 4A 1/16 (Wako Pure Chemical Industries) were added thereto, and the solution was used for peptide synthesis. N,N'-Diisopropylcarbodiimide (DIC) (10% v/v) and N,N-dimethylformamide (DMF) were mixed to prepare Solution 2.

2-Chlorotritylresin (100 mg) to which was attached the carboxylic acid at the side chain of an aspartic acid with the N-terminus protected by Fmoc group or the main chain carboxylic acid site of an amino acid with the N-terminus protected by Fmoc group was added to a solid-phase reaction vessel and the vessel was placed into the peptide synthesizer. Dichloromethane (DCM) (0.8 mL) was added to this resin (100 mg), and the resin was swollen by allowing to stand for one hour. Subsequently, the solution was removed from the frit. Solution 1 and Solution 2 were placed in the peptide synthesizer, and automated synthesis by the peptide synthesizer was started.

A solution of diazabicycloundecene (DBU) in DMF (2% v/v, 0.7 mL) was added to a resin-containing solid-phase reaction vessel to deprotect the N-terminal Fmoc group at room temperature. For deprotection of the first residue, the reaction was carried out for 4.5 minutes, and for deprotection of the second or subsequent residue, the reaction was carried out for 10 minutes, after which the solution was removed from the frit. DMF (0.7 mL) was added thereto, and after allowing to stand for 5 minutes, the solution was removed from the frit. Repeating this resin washing step three more times gave the resin onto which was attached the amino acid or peptide having an amino group at the N-terminus by removing the Fmoc group.

Next, Solution 1 (0.3 mL) and Solution 2 (0.36 mL) were mixed in a mixing vial of the synthesizer, and then added to the above-mentioned deprotected resin, and the solid-phase reaction vessel was warmed to 40° C. For sequences that elongated poorly, and such, the vessel was warmed to reach 60° C. as necessary. Condensation reaction between the amino group on the resin and the Fmoc-protected amino acid was carried out for 2.5 hours. For sequences that elongated poorly, and such, the reaction was carried out for 20 hours. After the reaction, the solution was removed from the frit. When the elongation efficiency was low, this condensation reaction with the Fmoc-protected amino acid was further repeated once or twice. Next, the resin was washed three times with DMF (0.7 mL). This Fmoc amino acid condensation reaction following the Fmoc deprotection reaction was defined as one cycle, and by repeating this cycle, the peptide was elongated on the resin surface. After completion of the peptide elongation, a solution of diazabicycloundecene (DBU) in DMF (2% v/v, 0.7 mL) was added to the resin, this was allowed to react for 15 minutes to carry out the Fmoc deprotection reaction, and then the solution was removed from the frit. The resulting resin was washed four times with DMF (0.7 mL), and four times with DCM (0.7 mL).

1-3-2. Cleavage of the Elongated Peptide from the Resin

To the resin obtained by methods described in WO2013/100132 and WO2018/225864, or by the above-mentioned method, 2,2,2-trifluoroethanol (TFE)/DCM (1/1, v/v, 2 mL) containing 0.75% (v/v) DIPEA was added, followed by the reaction at room temperature for two hours. Then, the reaction to cleave the peptide chain from the resin was carried out. After the reaction, the solution in the tube was recovered from the frit. The operation of adding 2,2,2-trifluoroethanol (TFE)/DCM (1/1, v/v, 1 mL) to the remaining resin and recovering the solution from the frit was performed twice. All the resulting cleavage solutions were combined, DMF (4 mL) or 1,2-dichloroethane (4 mL) were mixed therein, and then the solvent was evaporated under reduced pressure by a high throughput centrifugal evaporator (HT-12) manufactured by Genevac.

1-3-3. Method of Cyclizing the Cleaved Peptide

The residue obtained by the above-mentioned method was dissolved in a mixture of DMF (4 mL) and DCM (4 mL). To the mixture were added a solution of (1-cyano-2-ethoxy-2-oxoethylideneaminooxy)dimethylamino-mopholino-carbeniumhexafluorophosphate (COMU) in DMF (0.5 M, 1.5 equivalents) or a solution of O-(7-aza-1H-benzotriazol-1-yl)-N,N,N,N,-tetramethyluroniumhexafluorophosphate (HATU) in DMF (0.5 M, 1.5 equivalents), and DIPEA (1.8 equivalents), and by stirring this mixture at room temperature for two hours, a cyclocondensation reaction between the N-terminal amino group and the C-terminal carboxyl group was carried out. The number of equivalents was calculated based on the value obtained by multiplying the amount of resin used (normally 100 mg) to the amino acid loading rate (mmol/g) of the resin used as a raw material. After confirming the production of the target cyclic peptide by LC/MS measurement (SQ Detector 2, manufactured by Waters), the solvent was evaporated from the reaction solution under reduced pressure by a high throughput centrifugal evaporator (HT-12) manufactured by Genevac.

1-3-4. Deprotection of the Protecting Group for the Side Chain Functional Group Possessed by the Cyclic Peptide For the sequences synthesized using an Fmoc-protected amino acid having a THP-protected hydroxyl group on the side chain, for example, Fmoc-MeSer(tBuOTHP)-OH, Fmoc-Ser(tBuOTHP)-OH, Fmoc-MeSer(THP)-OH, Fmoc-Thr(THP)-OH, Fmoc-Ser(THP)-OH, Fmoc-D-MeSer(THP)-OH (Compound aa054), Fmoc-cisHyp(THP)-OH (Compound aa101), or Fmoc-Hyp(THP)-OH (Compound aa102), 4 mL of a solution of tetramethylammonium hydrogensulfate (0.05 M) in 1,1,1,3,3,3-hexafluoroisopropyl alcohol (HFIP) (containing 2% (v/v) triisopropylsilane (TIPS) and 1% (v/v) 1,2-dichloroethane) was added to the above-obtained residue, and the residue was dissolved, after which the THP protecting group was deprotected by allowing to stand at room temperature for four hours. After confirming the completion of the reaction by LC/MS (SQ Detector 2 manufactured by Waters), diisopropylethylamine (DIPEA) (70 μL) was added and the solvent was evaporated under reduced pressure by a high throughput centrifugal evaporator (HT-12) manufactured by Genevac. In this deprotection reaction, another fluoroalcohol such as 2,2,2-trifluoroethanol (TFE) may also be used instead of HFIP.

For the sequences synthesized using Fmoc-MeAsp (OAl)—OH, cyclic peptides were dissolved in DMF (0.5 M), tetrakis(triphenylphosphine)palladium (0) (0.01-0.05 equivalents relative to the peptide) and phenylsilane (0.7 equivalents relative to the peptide) were added at room temperature under a nitrogen atmosphere, and the allyl group was deprotected by stirring for 30 minutes. Production of the target cyclic peptide was confirmed by LC/MS measurements (SQ Detector 2 manufactured by Waters), and then the solvent was evaporated from the reaction solution under reduced pressure by a high throughput centrifugal evaporator (HT-12) manufactured by Genevac.

1-3-5. Method of Purifying the Cyclic Peptides

DMF or DMSO was added to the residue obtained by the above-mentioned method, insoluble substances were removed by filtration, and then purification by preparative HPLC was carried out to give the target cyclic peptide. Waters Auto Purification System was used for the purification instrument, YMC-Actus Triart C18 (internal diameter of 20 mm, length of 100 mm) or YMC-Actus Triart Phenyl (internal diameter of 20 mm, length of 100 mm) was used as the column, and methanol-aqueous ammonium acetate solution (50 mmol/L) or acetonitrile-water containing 0.1% formic acid was used as the mobile phase.

Synthesis of Compound 1

The target Compound 1 (16.6 mg, 23%) was obtained using Compound aa006-resin ((3S)-3-[9H-fluoren-9-yl-methoxycarbonyl(methyl)amino]-4-oxo-4-piperidin-1-ylbutanoic acid-2-chlorotrityl resin, Fmoc-MeAsp(O-Trt(2-Cl) resin)-pip) (0.478 mmol/g, 100 mg, 0.0478 mmol) as a raw material, and using Fmoc-MeChg-OH, Fmoc-cLeu-OH, Fmoc-Pro-OH, Fmoc-Hph(4-CF3-3-Cl)—OH, Fmoc-MeGly-OH, Fmoc-MeCha-OH, Fmoc-MeGly-OH, Fmoc-MeGly-OH, Fmoc-Cha-OH, and Fmoc-MeLeu-OH, by performing the above-described peptide elongation reaction by the Fmoc method, cleavage of the elongated peptide from the resin, cyclization of the cleaved peptide (using O-(7-aza-1H-benzotriazol-1-yl)-N,N,N,N,-tetramethyluroniumhexafluorophosphate (HATU) as the cyclizing agent), and purification of the cyclic peptide.

Compound 1 ((3S,9S,18S,21S,25S,28S,34S)-3-[2-[3-chloro-4-(trifluoromethyl)phenyl]ethyl]-28-cyclohexyl-9,18-bis(cyclohexylmethyl)-21-isobutyl-7,10,13,16,22,26,29-heptamethyl-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone)

Compounds 2 to 762, Compounds 764 to 845, Compounds 847 to 1027, Compounds 1029 to 1135, Compounds 2007 to 2020, and Compound 2111 were produced based on the method for producing Compound 1. Compounds 1373 to 1376 were produced by performing an additional deprotection reaction to the cyclic peptide compounds produced based on the method for producing Compound 1. Compounds 1450 to 1460 were produced by a method based on the method for producing Compound 1 which additionally includes repeating the step of condensing an αα-disubstituted amino acid with an N-alkyl amino acid multiple times.

Synthesis of Compound 1355

The target Compound 1355 (9.75 mg, 24%) was obtained using Compound aa010-resin, (3S)-3-[9H-fluoren-9-yl-methoxycarbonyl(methyl)amino]-4-(3-oxa-8-azabicyclo[3.2.1]octan-8-yl)-4-oxobutanoic acid-2-chlorotrityl resin (Fmoc-MeAsp(O-Trt(2-Cl)resin)-Mor(26-bicyc)) (0.279 mmol/g, 100 mg, 0.0279 mmol) as a raw material, and using Fmoc-MeGly(cPent)-OH, Fmoc-cLeu-OH, Fmoc-Pro-OH, Fmoc-Hph(4-CF3-35-F2)-OH, Fmoc-MeGly-OH, Fmoc-MeSer(nPr)—OH, Fmoc-Aze(2)-OH, Fmoc-MeAla-OH, Fmoc-Ile-OH, and Fmoc-MeLeu-OH, by performing the above-described peptide elongation reaction by the Fmoc method, cleavage of the elongated peptide from the resin, cyclization of the cleaved peptide (using (1-cyano-2-ethoxy-2-oxoethylideneaminooxy)dimethylamino-mopholino-carbeniumhexafluorophosphate (COMU) as the cyclizing agent), and purification of the cyclic peptide.

Compound 1355 ((5S,8S,11S,15S,18S,23aS,29S,35S,37aS)-15-(3-oxa-8-azabicyclo[3.2.1]octane-8-carbonyl)-8-((S)-sec-butyl)-18-cyclopentyl-29-(3,5-difluoro-4-(trifluoromethyl)phenethyl)-11-isobutyl-5,6,12,16,19,33,36-heptamethyl-35-(propoxymethyl)docosahydro-2H,4H-spiro[azeto[2,1-u]pyrrolo[2,1-i][1,4,7,10,13,16,19,22,25,28,31]undecaazacyclotetratriacontine-21,1'-cyclopentan]-4,7,10,13,17,20,23,28,31,34,37(14H,22H)-undecaone)

Compound 1

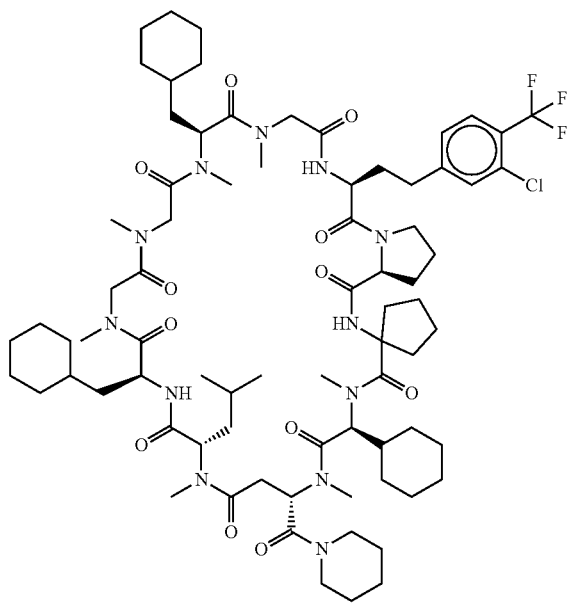

LCMS (ESI) m/z=1480.1 (M–H)–
Retention time: 2.155 min (analysis condition SSC-FA-03)

Compound 1355

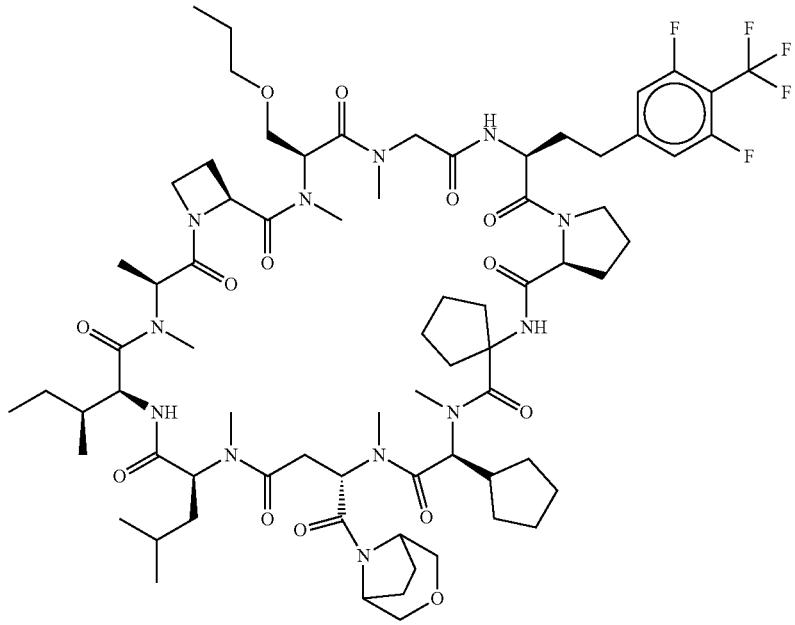

LCMS (ESI) m/z=1457.9 (M−H)−

Retention time: 7.425 min (analysis condition SSC-A-AF-01)

Compounds 1136 to 1146, Compounds 1148 to 1354, and Compounds 1356 to 1372 were produced based on the method for producing Compound 1355. Compounds 1869 to 2006 were produced by a method based on the method for producing Compound 1355 which additionally includes the step of condensing a sequence comprising an αα-disubstituted amino acid and/or N-alkyl amino acid by heating at 40° C. to 60° C.

Synthesis of Compound 1471

The target Compound 1471 (12.68 mg, 19%) was obtained using Compound aa138-resin, (3R)-3-(9H-fluoren-9-ylmethoxycarbonylamino)butanoic acid-2-chlorotrityl resin (Fmoc-D-3-Abu-O-Trt(2-Cl)resin) (0.494 mmol/g, 100 mg, 0.0494 mmol) as a raw material, and using Fmoc-MeGly(cPent)-OH, Fmoc-cLeu-OH, Fmoc-Pro-OH, Fmoc-Hph(4-CF3-3-Cl)—OH, Fmoc-MeGly-OH, Fmoc-MePhe(4-Me)-OH, Fmoc-MeGly-OH, Fmoc-MeGly-OH, Fmoc-Ile-OH, and Fmoc-MeLeu-OH, by performing the above-described peptide elongation reaction by the Fmoc method (for the elongation with Fmoc-cLeu-OH, Oxyma was used as the condensing agent, and after the reaction, disposal of the solution from the frit was followed by further condensation reaction with Fmoc-cLeu-OH which was repeated twice. Furthermore, the unreacted amino groups were capped using Z-Gly-OH (CAS No. 1138-80-3), HOAt and DIC as condensing agents, and DMF as solvent. The treatment step for unreacted amino groups is also called a removal step by glycine capping), cleavage of the elongated peptide from the resin, cyclization of the cleaved peptide (using O-(7-aza-1H-benzotriazol-1-yl)-N,N,N,N,-tetramethyluroniumhexafluorophosphate (HATU) as the cyclizing agent), and purification of the cyclic peptide.

Compound 1471 ((3S,9S,18S,21S,25R,28S,34S)-3-[2-[3-chloro-4-(trifluoromethyl)phenyl]ethyl]-28-cyclopentyl-21-isobutyl-7,10,13,16,22,25,29-heptamethyl-18-[(1S)-1-methylpropyl]-9-(p-tolylmethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone)

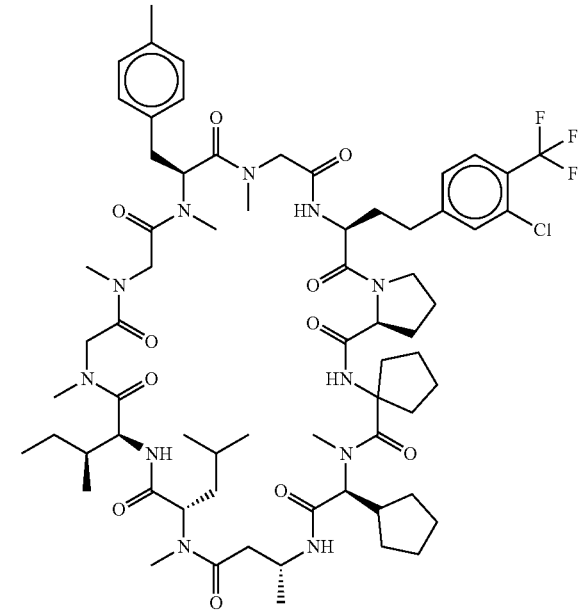

Compound 1471

LCMS (ESI) m/z=1322.9 (M−H)−
Retention time: 2.149 min (analysis condition SSC-AF-00)

Based on the method for producing Compound 1471, Compounds 1377 to 1410, Compounds 1412 to 1449, Compounds 1461 to 1470, and Compounds 1472 to 1643 were produced by a method based on the method for producing Compound 1471 which additionally includes performing the step of condensing a sequence comprising an αα-disubstituted amino acid and/or N-alkyl amino acid by repeating the step multiple times or by heating at 40° C. to 60° C., or by combining the repetition and heating.

Synthesis of Compound 1805

The target Compound 1805 (25.53 mg, 38%) was obtained by using Compound aa006-resin ((3S)-3-[9H-fluoren-9-ylmethoxycarbonyl(methyl)amino]-4-oxo-4-piperidin-1-ylbutanoic acid-2-chlorotrityl resin, Fmoc-MeAsp(O-Trt(2-Cl)resin)-pip) (0.478 mmol/g, 100 mg, 0.0478 mmol) as a raw material, and using Fmoc-MeChg-OH, Fmoc-cLeu-OH, Fmoc-Pro-OH, Fmoc-Hph(4-CF3-3-Cl)—OH, Fmoc-MeGly-OH, Fmoc-MeSer(nPr)—OH, Fmoc-MeGly-OH, Fmoc-MeGly-OH, Fmoc-Ile-OH, and Fmoc-MeLeu-OH, by performing the above-described peptide elongation reaction by the Fmoc method (Fmoc-MeChg-OH was subjected to a condensation reaction using Oxyma as the condensing agent at 50° C. for ten hours, and Fmoc-cLeu-OH was subjected to a condensation reaction using Oxyma as the condensing agent at 60° C. for 16 hours), cleavage of the elongated peptide from the resin, cyclization of the cleaved peptide (using (1-cyano-2-ethoxy-2-oxoethylideneaminooxy)dimethylamino-mopholino-carbeniumhexafluorophosphate (COMU) as the cyclizing agent), and purification of the cyclic peptide.

Compound 1805 ((3S,9S,18S,21S,25S,28S,34S)-3-[2-[3-chloro-4-(trifluoromethyl)phenyl]ethyl]-28-cyclohexyl-21-isobutyl-7,10,13,16,22,26,29-heptamethyl-18-[(1S)-1-methylpropyl]-25-(piperidine-1-carbonyl)-9-(propoxymethyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone)

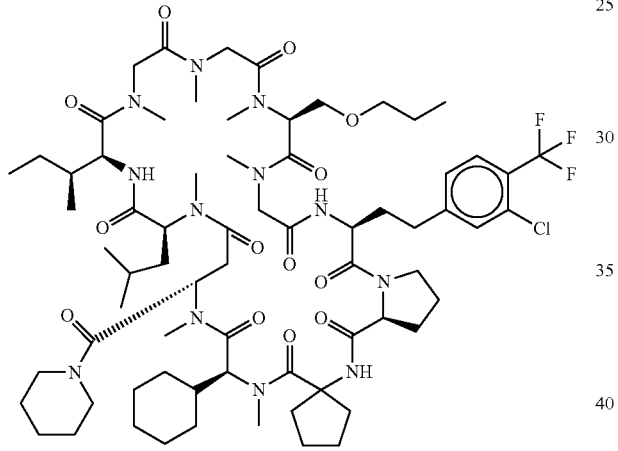

Compound 1805

LCMS (ESI) m/z=1415.9 (M−H)−

Retention time: 1.923 min (analysis condition SSC-FA-03)

Synthesis of Compound 2172 and Compound 2173

Compound 2172 and Compound 2173 were synthesized using Compound aa155-resin (2-[(2R)-3-(dimethylamino)-2-[(9H-fluoren-9-ylmethoxycarbonyl(methyl)amino]-3-oxopropyl]sulfanylacetic acid-2-chlorotrityl resin, Fmoc-MeGly(cPent)-OH), Fmoc-MeIle-OH, Fmoc-cLeu-OH, Fmoc-Pro-OH, Fmoc-Hph(4-CF3-3-Cl)—OH, Fmoc-MeGly-OH, Fmoc-MeCha-OH, Fmoc-MePhe(4-Me)-OH, and Fmoc-Ile-OH as raw materials, and using, by a method similar to the synthesis of any one of Compounds 1 to 762, Compounds 764 to 1027, Compounds 1029 to 1410, Compounds 1412 to 2020, and Compound 2111, and the target Compound 2172 (1.31 mg, 3%) and Compound 2173 (1.42 mg, 3%) were obtained.

Compound 2172 ((3S,9S,18S,24R,27S,33S)-18-[(2S)-butan-2-yl]-3-[2-[3-chloro-4-(trifluoromethyl)phenyl]ethyl]-9-(cyclohexylmethyl)-27-cyclopentyl-N,N,7,10,13,16,25,28-octamethyl-2,5,8,11,14,17,20,26,29,32-decaoxospiro[22-thia-1,4,7,10,13,16,19,25,28,31-decazabicyclo[31.3.0]hexatriacontane-30,1'-cyclopentane]-24-carboxamide)

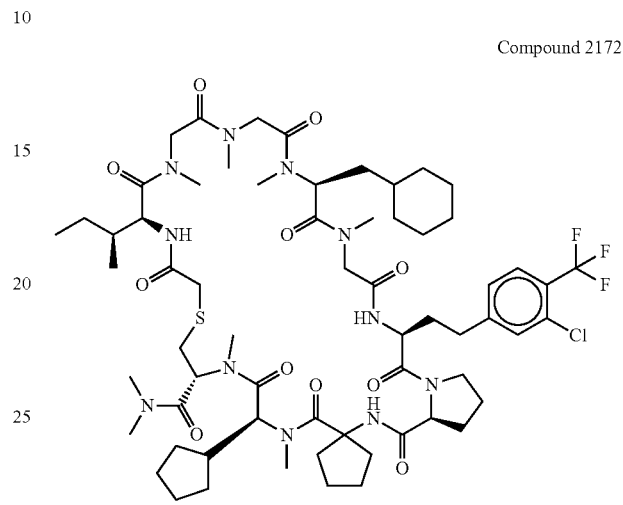

Compound 2172

LCMS (ESI) m/z=1307.1 (M+H)+

Retention time: 1.48 min (analysis condition SQDFA05long)

Compound 2173 ((3S,9S,18S,24R,27S,33S)-18,27-bis[(2S)-butan-2-yl]-3-[2-[3-chloro-4-(trifluoromethyl)phenyl]ethyl]-N,N,7,10,13,16,25,28-octamethyl-9-[(4-methylphenyl)methyl]-2,5,8,11,14,17,20,26,29,32-decaoxospiro[22-thia-1,4,7,10,13,16,19,25,28,31-decazabicyclo[31.3.0]hexatriacontane-30,1'-cyclopentane]-24-carboxamide)

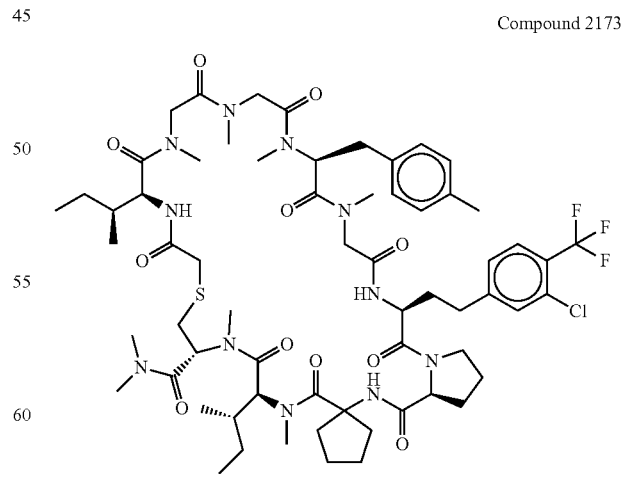

Compound 2173

LCMS (ESI) m/z=1303.1 (M+H)+

Retention time: 1.16 min (analysis condition SQDFA05long)

Synthesis of Compound 2174 ((3S,9S,12S,17S,20S, 23S,29R,32S,38S)-20-[(2S)-butan-2-yl]-32-cyclopentyl-3-[2-[3-fluoro-4-(trifluoromethyl)phenyl] ethyl]-N,N,7,10,17,18,24,30,33-nonamethyl-23-(2-methylpropyl)-2,5,8,11,16,19,22,25,31,34,37-undecaoxo-9-(propoxymethyl)spiro[27-thia-1,4,7,10,15,18,21,24,30,33,36-undecazatricyclo[36.3.0.012,15]hentetracontane-35,1'-cyclopentane]-29-carboxamide)

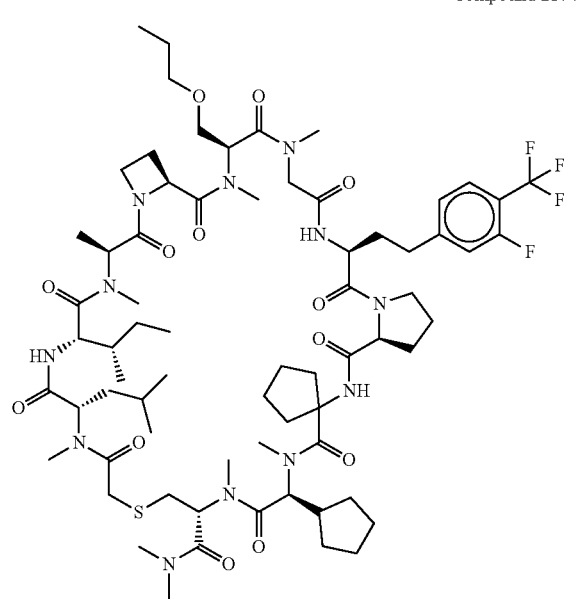

Compound 2174

The peptide chain was elongated by the common peptide elongation method described herein, using Compound aa155-resin (2-[(2R)-3-(dimethylamino)-2-[9H-fluoren-9-ylmethoxycarbonyl(methyl)amino]-3-oxopropyl]sulfanylacetic acid-2-chlorotrityl resin) as a raw material, and using Fmoc-MeGly(cPent)-OH, Fmoc-cLeu-OH, Fmoc-Pro-OH, Fmoc-Hph(4-CF3-3-F)—OH, Fmoc-MeGly-OH, Fmoc-MeSer(nPr)—OH, Fmoc-Aze(2)-OH, Fmoc-MeAla-OH, and Fmoc-Tle-OH in that order. The following operation was carried out while leaving the Fmoc group at the N terminus.

The resin was sequentially washed with DMF (four times with 0.7 mL), DCM (twice with 0.7 mL), and toluene (twice with 0.7 mL). A solution of diazabicycloundecene (DBU) in toluene (2% v/v, 0.7 mL) was added thereto, the solution was allowed to react for ten minutes, and then Fmoc group deprotection was performed. After removing the solution from the frit, the resin was sequentially washed with toluene (twice with 0.7 mL) and DCM (twice with 0.7 mL)

To the above-obtained resin was added a solution of Fmoc-MeLeu-OH (49 mg, 0.134 mmol, 4 equivalents), [ethylcyano(hydroxyimino)acetate-02]tri-1-pyrrolidinylphosphonium hexafluorophosphoric acid (PyOxym) (70.6 mg, 0.134 mmol, 4 equivalents), and DIPEA (0.035 mL, 0.2 mmol, 6 equivalents) in DCM (0.7 mL), and this was allowed to stand at room temperature for three hours. After removing the solution from the frit, the resin was washed with DCM (three times with 0.7 mL), and further washed with DMF (three times with 0.7 mL). To the obtained resin was added a solution of diazabicycloundecene (DBU) in DMF (2% v/v, 0.7 mL), this was allowed to react for 15 minutes to deprotect Fmoc group, and then the solution was removed from the frit. The obtained resin was washed with DMF (four times with 0.7 mL), and then with DCM (four times with 1.25 mL).

On the resin obtained by the above-mentioned method, 2,2,2-trifluoroethanol (TFE)/DCM (1/1, v/v, 2 mL) containing 0.75% DIPEA was added, and this was shaken at room temperature for two hours to carry out the reaction to cleave the peptide chain from the resin. After the reaction, the solution in the tube was recovered from the frit. The operation of adding 2,2,2-trifluoroethanol (TFE)/DCM (1/1, v/v, 1 mL) to the remaining resin and recovering the solution from the frit was performed twice. All the obtained cleavage solutions were combined, DMF (4 mL) was added, and the solvent was evaporated under reduced pressure by a high throughput centrifugal evaporator (HT-12) manufactured by Genevac.

The residue obtained by the above-mentioned method was dissolved in a mixture of DMF (4 mL) and DCM (4 mL), a solution of (1-cyano-2-ethoxy-2-oxoethylideneaminooxy) dimethylamino-mopholino-carbeniumhexafluorophosphate (COMU) in DMF (0.5 M, 0.1 mL), and DIPEA (0.015 mL) were added thereto, and a cyclocondensation reaction between the N-terminal amino group and the side chain carboxylic acid was carried out by stirring at room temperature for two hours. After confirming the production of the target cyclic peptide by LC/MS measurement (SQ Detector 2, manufactured by Waters), the solvent was evaporated from the reaction solution under reduced pressure by a high throughput centrifugal evaporator (HT-12) manufactured by Genevac.

DMF was added to the residue obtained by the above-mentioned method, insoluble substances were removed by filtration, and then purification by preparative-HPLC (on a Waters Auto Purification System, YMC-Actus Triart Phenyl (internal diameter of 20 mm, length of 100 mm) was used as the column, and methanol-aqueous ammonium acetate solution (50 mmol/L) was used as the mobile phase) gave the target Compound 2174 (5.55 mg, 12%).

LCMS (ESI) m/z=1420.3 (M+H)+

Retention time: 1.10 min (analysis condition SQDFA05long)

Synthesis of Compounds 2175 to 2179

Compounds 2175 to 2179 were synthesized by a method similar to the synthesis of Compound 2174, using Compound aa155-resin (2-[(2R)-3-(dimethylamino)-2-[9H-fluoren-9-ylmethoxycarbonyl(methyl)amino]-3-oxopropyl]sulfanylacetic acid-2-chlorotrityl resin) as a raw material, and using Fmoc-MeGly(cPent)-OH, Fmoc-MeIle-OH, Fmoc-cLeu-OH, Fmoc-Pro-OH, Fmoc-Hyp(Et)-OH, Fmoc-Hph (4-CF3-3-Cl)—OH, Fmoc-Hph(4-CF3-3-F)—OH, Fmoc-Hph(4-CF3-35-F2)-OH, Fmoc-MeGly-OH, Fmoc-MeCha-OH, Fmoc-MePhe(4-Me)-OH, Fmoc-Aze(2)-OH, Fmoc-MeAla-OH, Fmoc-Ile-OH, and Fmoc-MeLeu-OH as Fmoc amino acids.

721

Compound 2175 ((3S,9S,18S,21S,27R,30S,36S)-18-[(2S)-butan-2-yl]-3-[2-[3-chloro-4-(trifluoromethyl)phenyl]ethyl]-9-(cyclohexylmethyl)-30-cyclopentyl-N,N,7,10,13,16,22,28,31-nonamethyl-21-(2-methylpropyl)-2,5,8,11,14,17,20,23,29,32,35-undecaoxospiro[25-thia-1,4,7,10,13,16,19,22,28,31,34-undecazabicyclo[34.3.0]nonatriacontane-33,1'-cyclopentane]-27-carboxamide)

722

Compound 2176 ((3S,9S,12S,17S,20S,23S,29R,32S,38S,40R)-20-[(2S)-butan-2-yl]-9-(cyclohexylmethyl)-32-cyclopentyl-3-[2-[3,5-difluoro-4-(trifluoromethyl)phenyl]ethyl]-40-ethoxy-N,N,7,10,17,18,24,30,33-nonamethyl-23-(2-methylpropyl)-2,5,8,11,16,19,22,25,31,34,37-undecaoxospiro[27-thia-1,4,7,10,15,18,21,24,30,33,36-undecazatricyclo[36.3.0.01²,¹⁵]hentetracontane-35,1'-cyclopentane]-29-carboxamide)

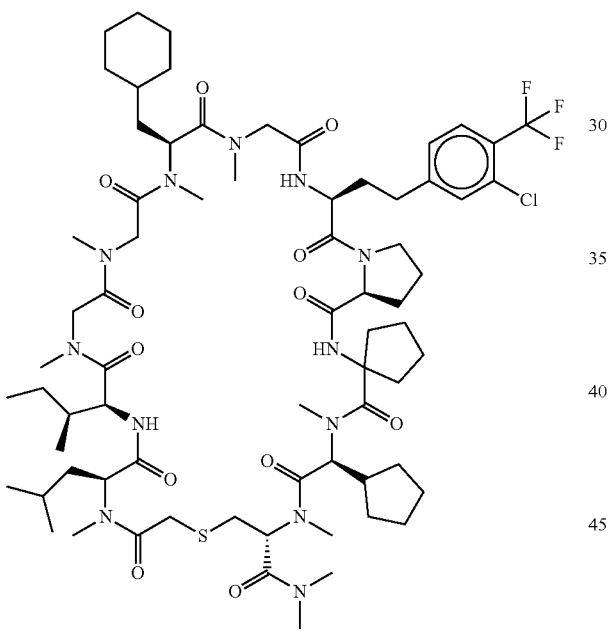

Compound 2175

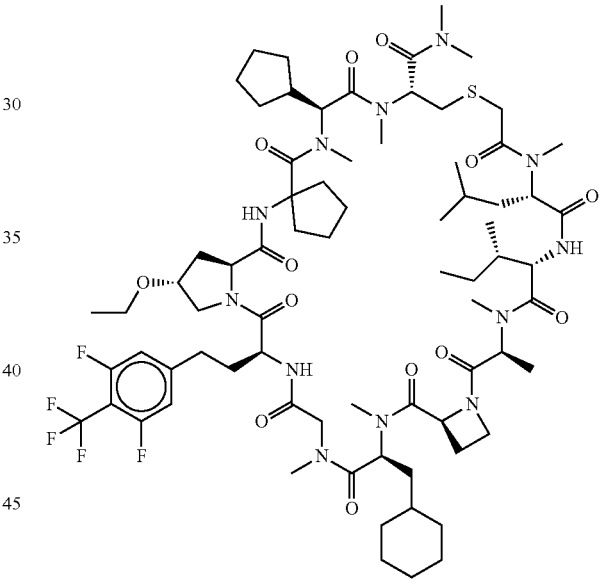

Compound 2176

LCMS (ESI) m/z=1434.3 (M+H)+

Retention time: 1.64 min (analysis condition SQDFA05long)

LCMS (ESI) m/z=1506.4 (M+H)+

Retention time: 1.88 min (analysis condition SQDFA05long)

Compound 2177 ((3S,9S,12S,17S,20S,23S,29R,32S,38S)-20-[(2S)-butan-2-yl]-3-[2-[3-chloro-4-(trifluoromethyl)phenyl]ethyl]-32-cyclopentyl-N,N,7,10,17,18,24,30,33-nonamethyl-9-[(4-methylphenyl)methyl]-23-(2-methylpropyl)-2,5,8,11,16,19,22,25,31,34,37-undecaoxospiro[27-thia-1,4,7,10,15,18,21,24,30,33,36-undecazatricyclo[36.3.0.0 12,15]hentetracontane-35,1'-cyclopentane]-29-carboxamide)

Compound 2178 ((3S,9S,18S,21S,27R,30S,36S)-18,30-bis[(2S)-butan-2-yl]-3-[2-[3-chloro-4-(trifluoromethyl)phenyl]ethyl]-N,N,7,10,13,16,22,28,31-nonamethyl-9-[(4-methylphenyl)methyl]-21-(2-methylpropyl)-2,5,8,11,14,17,20,23,29,32,35-undecaoxospiro[25-thia-1,4,7,10,13,16,19,22,28,31,34-undecazabicyclo[34.3.0]nonatriacontane-33,1'-cyclopentane]-27-carboxamide)

Compound 2177

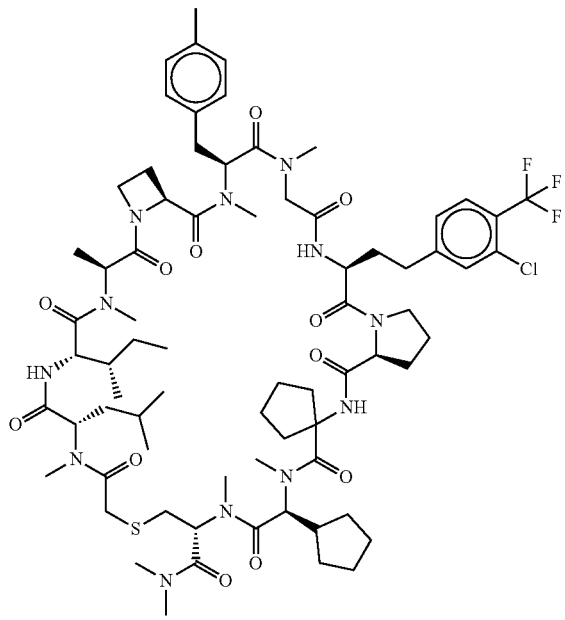

Compound 2178

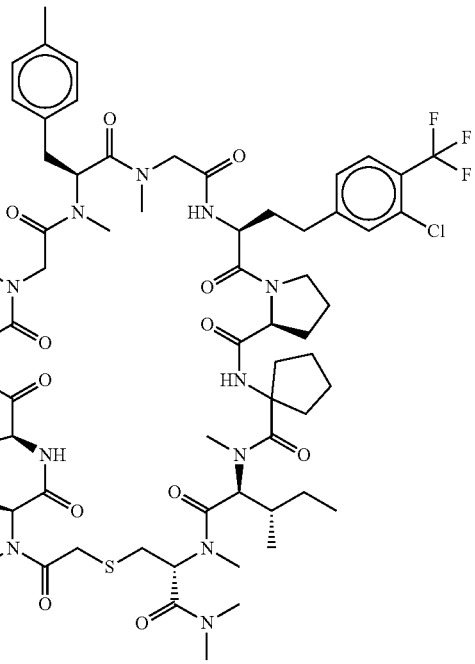

LCMS (ESI) m/z=1468.3 (M+H)+

Retention time: 1.55 min (analysis condition SQDFA05long)

LCMS (ESI) m/z=1430.3 (M+H)+

Retention time: 1.43 min (analysis condition SQDFA05long)

Compound 2179 ((3S,9S,12S,17S,20S,23S,29R,32S,38S)-20-[(2S)-butan-2-yl]-9,32-dicyclopentyl-3-[2-[3-fluoro-4-(trifluoromethyl)phenyl]ethyl]-N,N,7,10,17,18,24,30,33-nonamethyl-23-(2-methylpropyl)-2,5,8,11,16,19,22,25,31,34,37-undecaoxospiro[27-thia-1,4,7,10,15,18,21,24,30,33,36-undecazatricyclo[36.3.0.012,15]hentetracontane-35,1'-cyclopentane]-29-carboxamide)

Copmound 2179

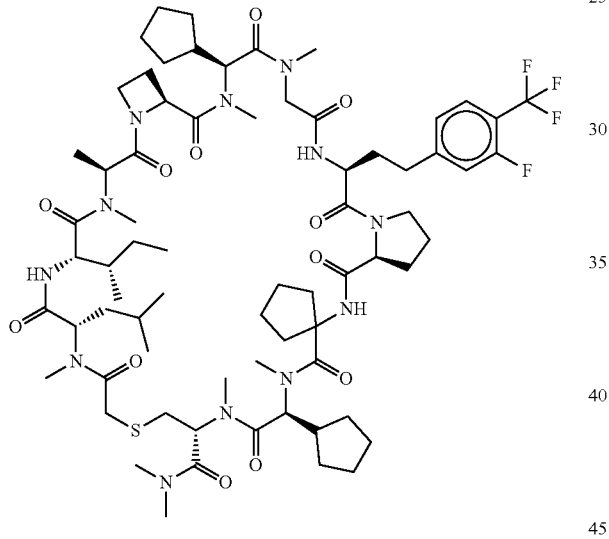

LCMS (ESI) m/z=1416.3 (M+H)+

Retention time: 1.17 min (analysis condition SQDFA05long)

The mass spectral values and the liquid chromatography retention times of cyclic peptide compounds described in Examples are described in Table 22.

1-4. Cyclic Peptide Synthesis by Peptide Modification
1-4-1. Peptide Synthesis Through N-Methylation of TFA Amides on Resins Synthesis of Compound 2159 ((5S,8S,11S,15R,18S, 23aS,29S,35S,37aS)-8,11-di((S)-sec-butyl)-29-(3-chloro-4-(trifluoromethyl)phenethyl)-35-(cyclohexylmethyl)-18-isopropyl-5,6,12,15,16,19,21,21,22,33, 36-undecamethyltetracosahydro-2H-azeto[2,1-u] pyrrolo[2,1-i][1,4,7,10,13,16,19,22,25,28,31] undecaazacyclotetratriacontyne-4,7,10,13,17,20,23, 28,31,34,37(14H)-undecone)

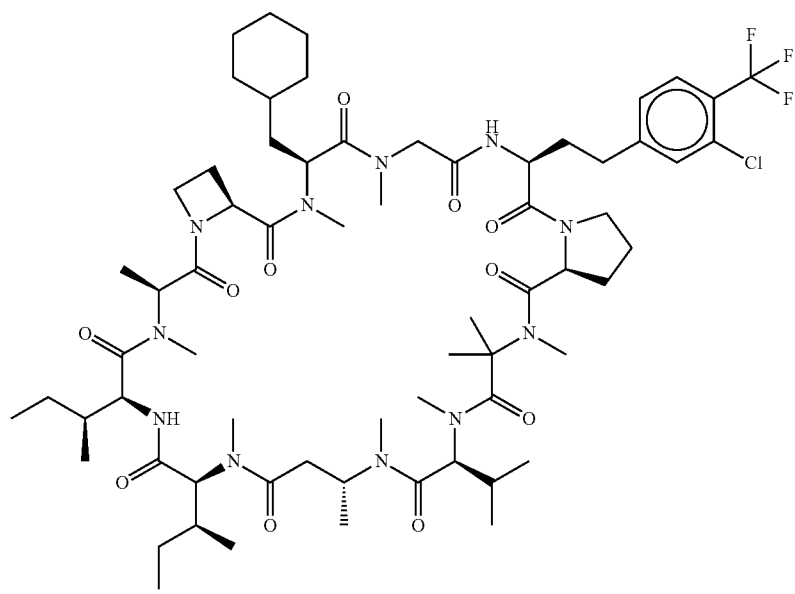

Compound 2159

Compound 2159 was synthesized according to the following scheme.

-continued

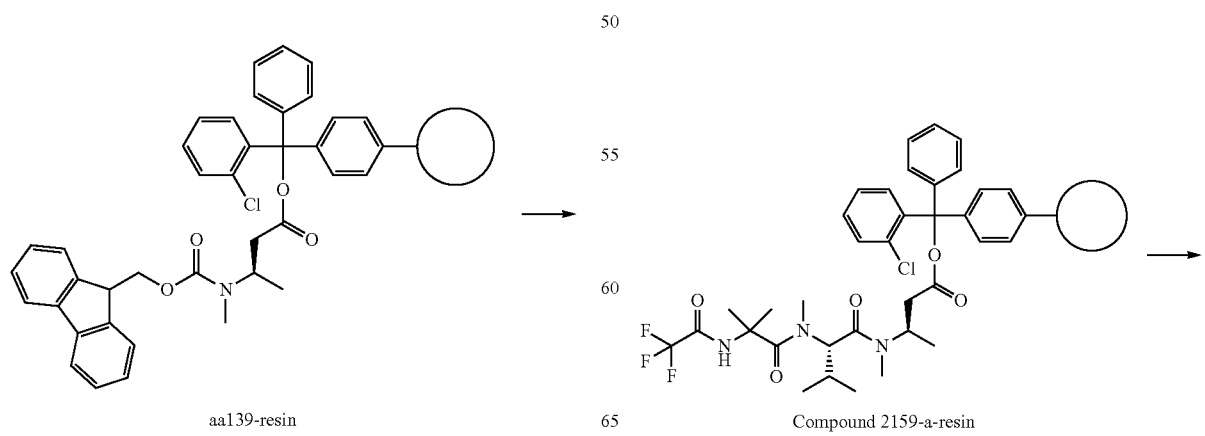

aa139-resin        Compound 2159-a-resin

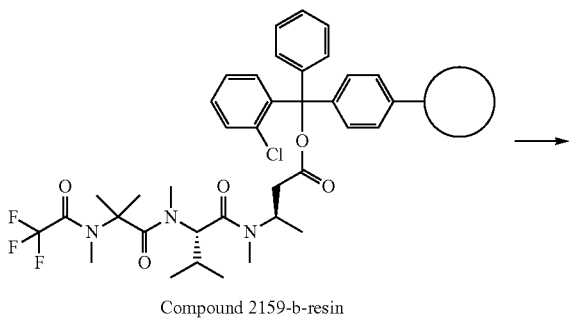

Compound 2159-b-resin

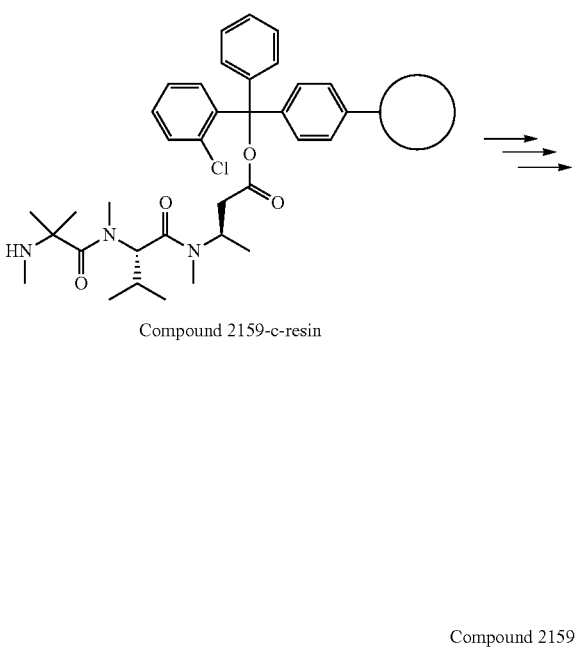

Compound 2159-c-resin

Compound 2159

To a solution of 2-amino-2-methylpropanoic acid (H-Aib-OH, CAS No. 62-57-7) (2.5 g, 24.24 mmol) and DIPEA (4.66 mL, 26.7 mmol) in methanol (12.12 mL) was added ethyl trifluoroacetate (3.76 mL, 31.5 mmol), and the mixture was stirred at 60° C. for 20 hours. The reaction solution was cooled to room temperature, and the solvent was evaporated under reduced pressure. To the resulting residue was added 1 mol/L aqueous hydrochloric acid, and the mixture was extracted with ethyl acetate. The organic layer was washed with brine and then dried over anhydrous sodium sulfate, and the solvent was evaporated under reduced pressure. The resulting residue was purified by reverse phase column chromatography (acetonitrile with 0.1% formic acid/distilled water with 0.1% formic acid) to give 2-methyl-2-(2,2,2-trifluoroacetamido)propanoic acid (TFA-Aib-OH) (2.2 g, 46%).

LCMS (ESI) m/z=198 (M−H)−

Retention time: 0.40 min (analysis condition SQDFA05)

Compound 2159-a-resin was obtained by elongating Fmoc-MeVal-OH using the basic peptide elongation method described in the present Examples in a reaction vessel equipped with a filter, and then elongating TFA-Aib-OH (2-methyl-2-(2,2,2-trifluoroacetamido)propanoic acid) obtained by the above formulation, with Compound aa139-resin ((3R)-3-[9H-fluoren-9-ylmethoxycarbonyl(methyl)amino]butanoic acid-2-chlorotrityl resin, Fmoc-D-3-MeAbu-O-Trt(2-Cl)resin) (100 mg, 0.343 mmol/g, 0.0343 mmol) used as a raw material.

The obtained Compound 2159-a-resin was swollen with DCM (1 mL) and then washed with DMF (1 mL) four times. A solution of phosphazene base $P_1$-tBu (38 μL, 0.150 mmol) in DMF (180 μL) and a solution of methyl iodide (62 μL, 1 mmol) in DMF (180 μL) were added, and the vessel was shaken at 40° C. for 30 minutes under sealed conditions. After removing the reaction solution, the resin was washed with DMF (1 mL) four times and further washed with DCM (1 mL) four times to give Compound 2159-b-resin. The obtained resin was partially cleaved with TFE/DCM (1/1) and analyzed by LC/MS to confirm the progress of the reaction.

LCMS (ESI) m/z=424 (M−H)−

Retention time: 0.57 min (analysis condition SQDFA05)

Sodium borohydride ($NaBH_4$) (758 mg, 20 mmol) was placed in a flask, pumped up, and then, under a nitrogen atmosphere, dissolved in triglyme (10 mL) to provide Solution A. The above-obtained Compound 2159-b-resin was swollen with DCM (1 mL) and then washed with THE (0.7 mL) four times. To the resin were added THE (0.5 mL), methanol (0.25 mL), and Solution A (0.25 mL), and the flask was shaken at room temperature for 40 minutes in an open system. After removing the reaction solution, methanol (0.7 mL) was added, and after one minute, the solution was discarded. This resin-washing operation was repeated four times. Further, the resin was similarly washed with DCM (0.7 mL) four times to give Compound 2159-c-resin. The obtained resin was partially cleaved with TFE/DCM (1/1) and analyzed by LC/MS to confirm the progress of the reaction.

LCMS (ESI) m/z=330 (M+H)+

Retention time: 0.33 min (analysis condition SQDFA05)

Subsequent peptide elongation, cyclization, and purification steps were conducted according to the basic route to give Compound 2159 ((5S,8S,11S,15R,18S,23aS,29S,35S,37aS)-8,11-di((S)-sec-butyl)-29-(3-chloro-4-(trifluoromethyl)phenethyl)-35-(cyclohexylmethyl)-18-isopropyl-5,6,12,15,16,19,21,21,22,33,36-undecamethyltetracosahydro-2H-azeto[2,1-u]pyrrolo[2,1-i][1,4,7,10,13,16,19,22,25,28,31]undecaazacyclotetratriacontyne-4,7,10,13,17,20,23,28,31,34,37(14H)-undecone) (4.1 mg, 9%). The LC/MS data are as described in Table 22.

Compounds 2152-2158 and Compound 2160 were synthesized by the same method as in the synthesis of Compound 2159. The LC/MS data are as described in Table 22.

1-4-2. Peptide Modification by Alkylation of OH

Synthesis of Compound 2116 ((3S,9S,18S,21S,25R,
28S,34S,36R)-36-benzyloxy-9-(cyclohexylmethyl)-
3-[2-[3-fluoro-4-(trifluoromethyl)phenyl]ethyl]-21,
28-diisobutyl-7,10,13,16,22,25,29-heptamethyl-18-
[(1S)-1-methylpropyl]spiro[1,4,7,10,13,16,19,22,26,
29,32-undecazabicyclo[32.3.0]heptatriacontane-31,
1'-cyclopentane]-2,5,8,11,14,17,20,23,27,30,33-
undecone)

Compound 2116

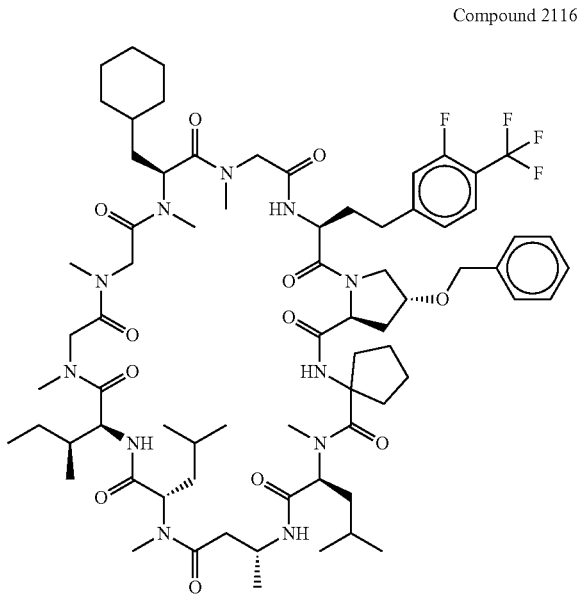

In a glass screw cap vial were mixed Compound 1483 ((3S,9S,18S,21S,25R,28S,34S,36R)-9-(cyclohexylmethyl)-3-[2-[3-fluoro-4-(trifluoromethyl)phenyl]ethyl]-36-hydroxy-21,28-diisobutyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone) synthesized by the basic peptide synthesis described in the present Examples (5 mg, 3.83 μmol), silver(I) oxide (26.6 mg, 0.115 mmol), and benzyl bromide (19.7 mg, 0.115 mmol), 1,4-dioxane (0.05 mol/L, 77 μL) was added, the vial was capped, and reaction was performed at 60° C. overnight. The reaction solution was filtered, and the filtrate was then purified by reverse phase medium pressure column chromatography (acetonitrile/water, containing 0.3% formic acid) to give Compound 2116 ((3S,9S,18S,21S,25R,28S,34S,36R)-36-benzyloxy-9-(cyclohexylmethyl)-3-[2-[3-fluoro-4-(trifluoromethyl)phenyl]ethyl]-21,28-diisobutyl-7,10,13,16,22,25,29-heptamethyl-18-[(1S)-1-methylpropyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone) (3.7 mg, 70%). The LC/MS data are as described in Table 22.

Synthesis of Compounds 2118, 2125, 2128, 2130, 2131, 2133, 2134, 2138, and 2139

Compounds 2118, 2125, 2128, 2130, 2131, 2133, 2134, 2138, and 2139 were synthesized by the same method as in the synthesis of Compound 2116 using Compound 875 ((3S,9S,18S,21S,25S,28S,34S,36R)-9-(cyclohexylmethyl)-3-[2-[3-fluoro-4-(trifluoromethyl)phenyl]ethyl]-36-hydroxy-21,28-diisobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'cyclopentane]-2,5,8,11,14,17,20,23,27,30,33-undecone) synthesized by the basic peptide elongation method described in the present Examples, as a raw material, and using alkylating agents provided in the following table. Purification was conducted by reverse phase medium pressure column chromatography or preparative HPLC. The following table describes target compound peptides, alkylating agents used for reactions, amounts (mg) of Compound 875 used as a raw material, and yield amounts (mg) and yield percentages (%) of the target compounds. The LC/MS data are as described in Table 22.

TABLE 9

| Target compound | Alkylating agent | Raw material mg | Target compound mg | Yield % |
|---|---|---|---|---|
| Compound 2138 | 2-chlorobenzyl bromide | 5.4 | 3 | 50 |
| Compound 2118 | ethyl iodide | 10.8 | 7 | 63 |
| Compound 2134 | 3-chlorobenzyl bromide | 5.4 | 2 | 35 |
| Compound 2133 | 4-chlorobenzyl bromide | 5.4 | 1.9 | 32 |
| Compound 2139 | 2-methylbenzyl bromide | 5.4 | 3.1 | 54 |
| Compound 2125 | 3-methylbenzyl bromide | 5.4 | 2.3 | 39 |
| Compound 2131 | 3-methoxybenzyl bromide | 5.4 | 2 | 34 |
| Compound 2130 | 4-methylbenzyl bromide | 5.4 | 2.9 | 50 |
| Compound 2128 | 4-(difluoromethoxy)benzyl bromide | 5.4 | 2.3 | 38 |

Synthesis of Compounds 2132, 2126, 2129, 2127, 2137, 2141, 2136, 2140, and 2135

Compounds 2132, 2126, 2129, 2127, 2137, 2141, 2136, 2140, and 2135 were synthesized by the same method as in the synthesis of Compound 2116 using Compound 544 ((3S,9S,18S,21S,25S,28S,34S,36S)-9-(cyclohexylmethyl)-3-[2-[3-fluoro-4-(trifluoromethyl)phenyl]ethyl]-36-hydroxy-21,28-diisobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone) synthesized by the basic peptide elongation method described in the present Examples, as a raw material, and using alkylating agents provided in the following table. Purification was conducted by reverse phase medium pressure column chromatography or preparative HPLC. The following table describes target compound peptides, alkylating agents used for reactions, amounts (mg) of Compound 544 used as a raw material, and yield amounts (mg) and yield percentages (%) of the target compounds. The LC/MS data are as described in Table 22.

TABLE 10

| Target compound | Alkylating agent | Raw material mg | Target compound mg | Yield % |
|---|---|---|---|---|
| Compound 2132 | 2-chlorobenzyl bromide | 5.4 | 0.7 | 11 |
| Compound 2126 | 3-chlorobenzyl bromide | 5.4 | 0.3 | 6 |
| Compound 2129 | 4-chlorobenzyl bromide | 5.4 | 0.7 | 11 |
| Compound 2127 | ethyl iodide | 10.8 | 2.6 | 23 |
| Compound 2137 | 2-methylbenzyl bromide | 5.4 | 2.4 | 41 |
| Compound 2141 | 3-methylbenzyl bromide | 5.4 | 2.5 | 42 |
| Compound 2136 | 3-methoxybenzyl bromide | 5.4 | 1.7 | 29 |
| Compound 2140 | 4-methylbenzyl bromide | 5.4 | 1.7 | 29 |
| Compound 2135 | 4-(difluoromethoxy)benzyl bromide | 5.4 | 2 | 32 |

Synthesis of Compounds 2043, 2044, and 2045

A precursor peptide shown below (Compound 2044-a) (230 mg, 0.188 mmol, 39%) was synthesized by the basic peptide synthesis method described in the present Examples, using Compound aa006-resin ((3S)-3-[9H-fluoren-9-yl-methoxycarbonyl(methyl)amino]-4-oxo-4-piperidin-1-ylbutanoic acid-2-chlorotrityl resin, Fmoc-MeAsp(O-Trt(2-Cl)resin)-pip) (0.3 mmol/g, 1.6 g, 0.48 mmol) as a raw material.

Compound 2044-a

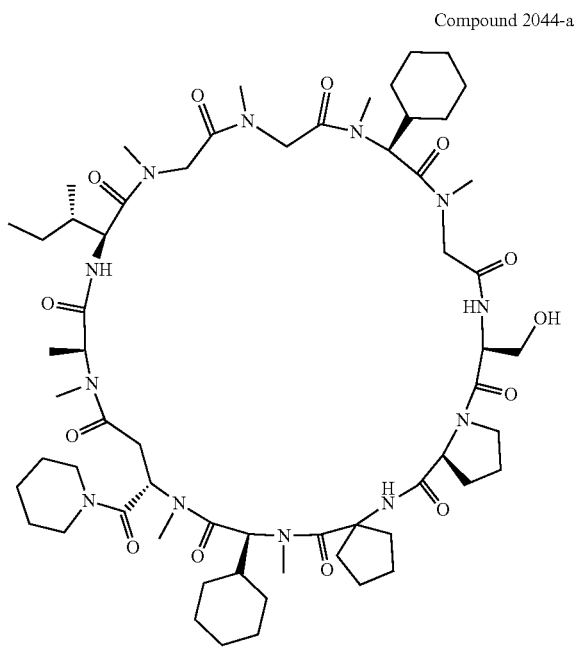

LCMS (ESI) m/z=1224 (M+H)+

Retention time: 0.82 min (analysis condition SQDFA05)

Compounds 2043, 2044, and 2045 were synthesized by the same method as in the synthesis of Compound 2116 using Compound 2044-a as a raw material, and using alkylating agents provided in the following table. Purification was conducted by reverse phase medium pressure column chromatography or preparative HPLC. The following table describes target compound peptides, alkylating agents used for reactions, amounts (mg) of raw material Compound 2044-a, and yield amounts (mg) and yield percentages (%) of the target compounds. The LC/MS data are as described in Table 22.

TABLE 11

| Target compound | Alkylating agent | Raw material mg | Target compound mg | Yield % |
|---|---|---|---|---|
| Compound 2044 | 4-chlorobenzyl bromide | 20 | 8.2 | 37 |
| Compound 2045 | 3-chlorobenzyl bromide | 9.9 | 6 | 55 |
| Compound 2043 | 2-chlorobenzyl bromide | 9.9 | 1 | 9 |

Synthesis of Compound 2117 ((3S,9S,18S,21S,25S,28S,34S,36S)-3-[2-[3-chloro-4-(trifluoromethyl)phenyl]ethyl]-28-cyclohexyl-9-(cyclohexylmethyl)-36-(2-hydroxyethoxy)-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone)

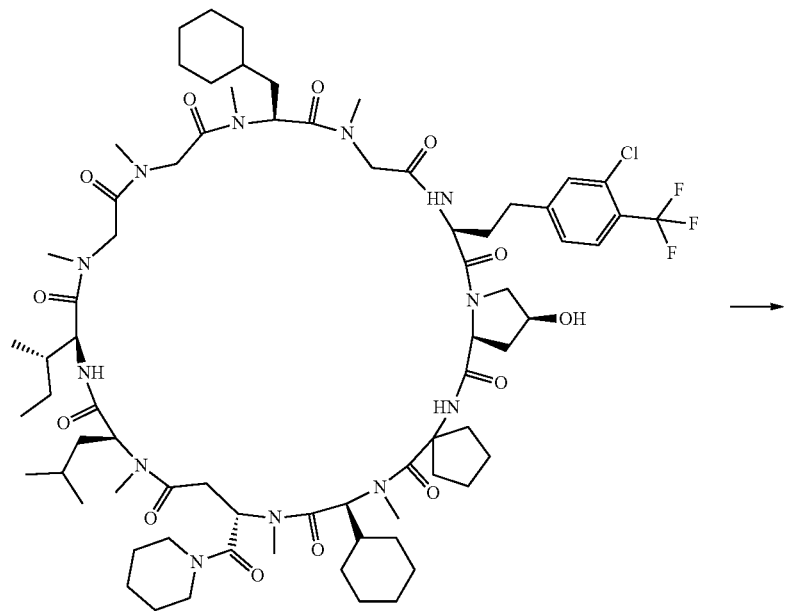

Compound 1374

-continued

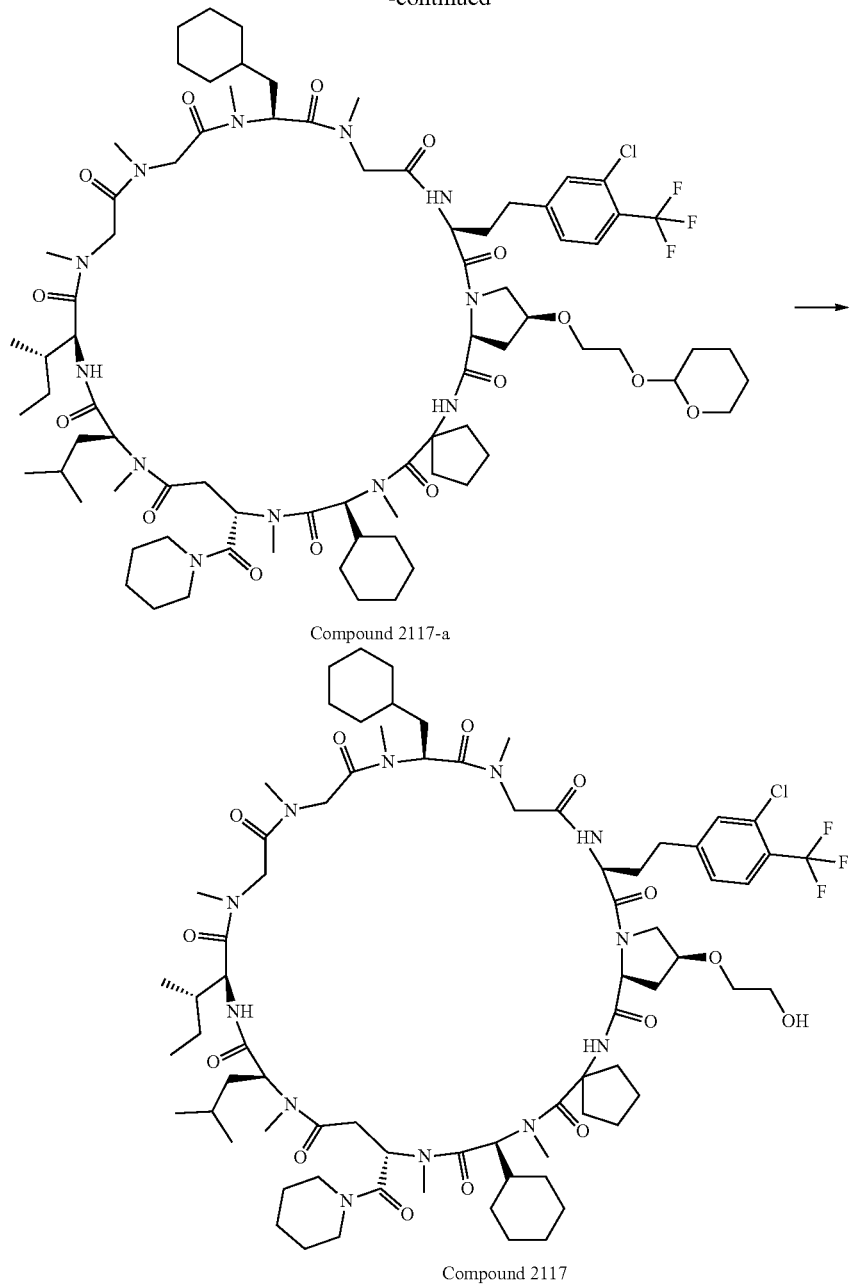

Compound 2117-a

Compound 2117

To Compound 1374 ((3S,9S,18S,21S,25S,28S,34S,36S)-3-[2-[3-chloro-4-(trifluoromethyl)phenyl]ethyl]-28-cyclohexyl-9-(cyclohexylmethyl)-36-hydroxy-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone) (5 mg, 3.43 μmol) as a raw material were added 2-(2-bromoethoxy)tetrahydro-2H-pyran (14.3 mg, 0.0686 mmol) and tetrabutylammonium bromide (3.32 mg, 10.29 μmol), after which dichloromethane (0.04 mol/L, 86 μL) and a 5 mol/L aqueous sodium hydroxide solution (27.4 μL) were added and the mixture was reacted at room temperature for five days. The reaction solution was purified by reverse phase medium pressure column chromatography (acetonitrile/water, containing 0.3% formic acid) to give Compound 2117-a (3.3 mg, 61%).

LCMS (ESI) m/z=1586 (M+H)+

Retention time: 0.85 min (analysis condition SQDFA50)

Compound 2117-a (3.3 mg, 2.08 μmol) was subjected to deprotection of the THP protecting group according to the basic peptide elongation method described in the present Examples, and was then purified to give Compound 2117 ((3S,9S,18S,21S,25S,28S,34S,36S)-3-[2-[3-chloro-4-(trifluoromethyl)phenyl]ethyl]-28-cyclohexyl-9-(cyclohexylmethyl)-36-(2-hydroxyethoxy)-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone) (1.59 mg, 54%). The LC/MS data are as described in Table 22.

Synthesis of Compound 2122 ((3S,9S,18S,21S,25S, 28S,34S,36R)-3-[2-[3-chloro-4-(trifluoromethyl) phenyl]ethyl]-28-cyclohexyl-9-(cyclohexylmethyl)-36-(2-hydroxyethoxy)-21-isobutyl-7,10,13,16,22,26, 29-heptamethyl-18-[(1S)-1-methylpropyl]-25-(piperidine-1-carbonyl)spiro[1,4,7,10,13,16,19,22, 26,29,32-undecazabicyclo[32.3.0]heptatriacontane-31,1'-cyclopentane]-2,5,8,11,14,17,20,23,27,30,33-undecone)
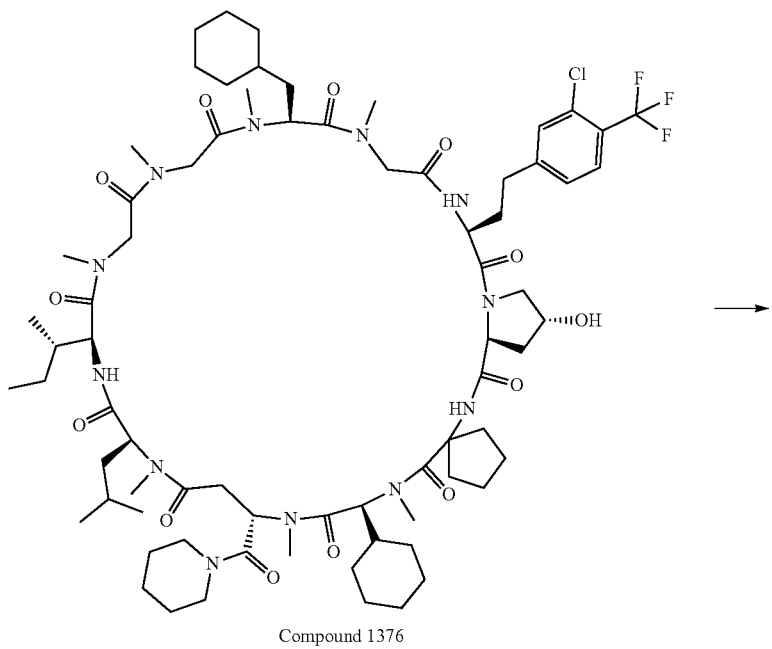
Compound 1376
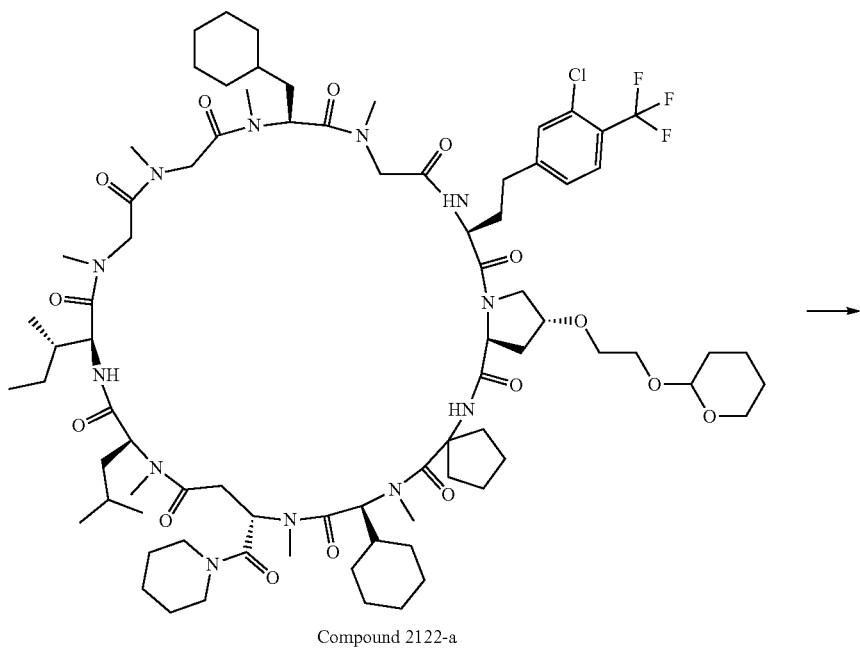
Compound 2122-a -continued

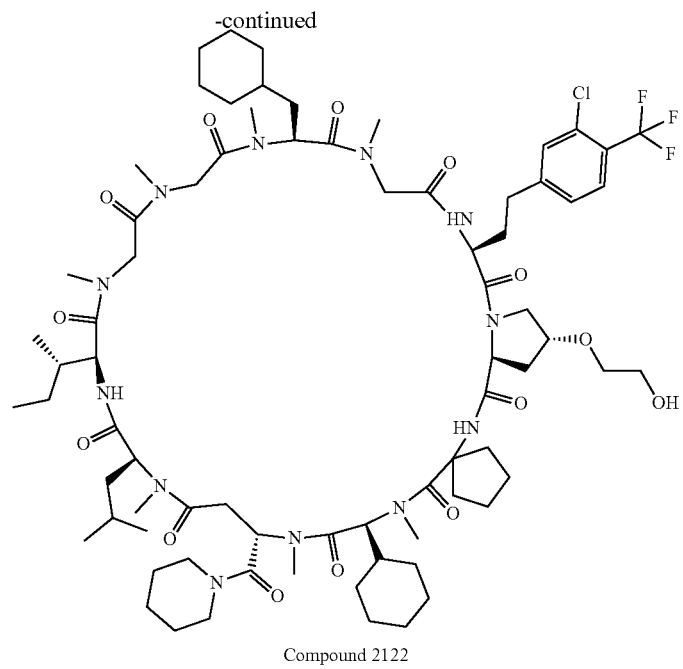

Compound 2122

Compound 2122-a (3.1 mg, 57%) was obtained by the same method as in the synthesis of Compound 1374-a using Compound 1376 ((3S,9S,18S,21S,25S,28S,34S,36R)-3-[2-[3-chloro-4-(trifluoromethyl)phenyl]ethyl]-28-cyclohexyl-9-(cyclohexylmethyl)-36-hydroxy-21-isobutyl-7,10,13,16, 22,26,29-heptamethyl-18-[(1S)-1-methylpropyl]-25-(piperidine-1-carbonyl)spiro[1,4,7,10,13,16,19,22,26,29, 32-undecazabicyclo[32.3.0]heptatriacontane-31,1'-cyclopentane]-2,5,8,11,14,17,20,23,27,30,33-undecone) (5 mg, 3.43 μmol) as a raw material.

LCMS (ESI) m/z=1585.9 (M+H)+

Retention time: 0.95 min (analysis condition SQDFA50)

Compound 2122-a (3.1 mg) was subjected to deprotection of the THP protecting group according to the basic peptide elongation method described in the present Examples, and was then purified to give Compound 2122 ((3S,9S,18S,21S, 25S,28S,34S,36R)-3-[2-[3-chloro-4-(trifluoromethyl)phenyl]ethyl]-28-cyclohexyl-9-(cyclohexylmethyl)-36-(2-hydroxyethoxy)-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone) (1.3 mg, 44%). The LC/MS data are as described in Table 22.

Synthesis of Compounds 2121, 2119, 2124, 2120, and 2123

Compounds 2121, 2119, and 2124 were synthesized by the same method as in the synthesis of Compound 2117-a using Compound 1376 ((3S,9S,18S,21S,25S,28S,34S,36R)-3-[2-[3-chloro-4-(trifluoromethyl)phenyl]ethyl]-28-cyclohexyl-9-(cyclohexylmethyl)-36-hydroxy-21-isobutyl-7,10, 13,16,22,26,29-heptamethyl-18-[(1S)-1-methylpropyl]-25-(piperidine-1-carbonyl)spiro[1,4,7,10,13,16,19,22,26,29, 32-undecazabicyclo[32.3.0]heptatriacontane-31,1'-cyclopentane]-2,5,8,11,14,17,20,23,27,30,33-undecone) as a raw material. Purification was conducted by reverse phase medium pressure column chromatography or preparative HPLC. The following table describes target compound peptides, alkylating agents used for reactions, amounts (mg) of Compound 1376 used as a raw material, and yield amounts (mg) and yield percentages (%) of the target compounds. The LC/MS data are as described in Table 22.

TABLE 12

| Target compound | Alkylating agent | Raw material mg | Target compound mg | Yield % |
|---|---|---|---|---|
| Compound 2124 | 3-bromomethylthiophene | 5 | 2.1 | 39 |
| Compound 2121 | 3-(chloromethyl)pyridine | 15 | 0.67 | 4 |
| Compound 2119 | 2,2-difluoroethyl triflate | 5 | 4.27 | 82 |

Compounds 2120 and 2123 were synthesized by the same method as in the synthesis of Compound 2117-a using Compound 1374 ((3S,9S,18S,21S,25S,28S,34S,36S)-3-[2-[3-chloro-4-(trifluoromethyl)phenyl]ethyl]-28-cyclohexyl-9-(cyclohexylmethyl)-36-hydroxy-21-isobutyl-7,10,13,16,22,26,29-heptamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone) as a raw material. Purification was conducted by reverse phase medium pressure column chromatography or preparative HPLC. The following table describes target compound peptides, alkylating agents used for reactions, amounts (mg) of Compound 1374 used as a raw material, and yield amounts (mg) and yield percentages (%) of the target compounds. The LC/MS data are as described in Table 22.

TABLE 13

| Target compound | Alkylating agent | Raw material mg | Target compound mg | Yield % |
|---|---|---|---|---|
| Compound 2120 | 3-(chloromethyl)pyridine | 15 | 1.3 | 8 |
| Compound 2123 | 2,2-difluoroethyl triflate | 5 | 5 | 96 |

1-4-3. Peptide Modification by Reductive Coupling Reaction

Synthesis of Compound 2085 ((5S,8S,11S,15S,18S,23aS,29S,35S,37aS)-8-((S)-sec-butyl)-35-(cyclohexylmethyl)-18-cyclopentyl-29-(4-(difluoromethyl)-3-fluorophenethyl)-11-isobutyl-5,6,12,16,19,33,36-heptamethyl-15-(piperidin-1-carbonyl)docosahydro-2H,4H-spiro[azeto[2,1-u]pyrrolo[2,1-i][1,4,7,10,13,16,19,22,25,28,31]undecazacyclotetratriacontyne-21,1'-cyclopentane]-4,7,10,13,17,20,23,28,31,34,37(14H,22H)-undecone)

Compound 2085 was synthesized according to the following scheme.

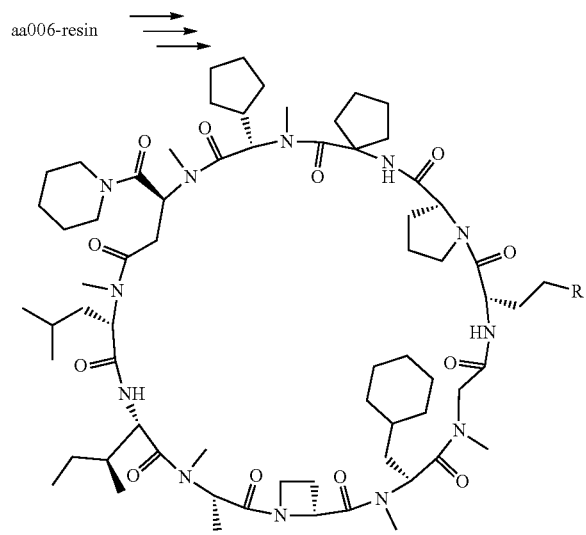

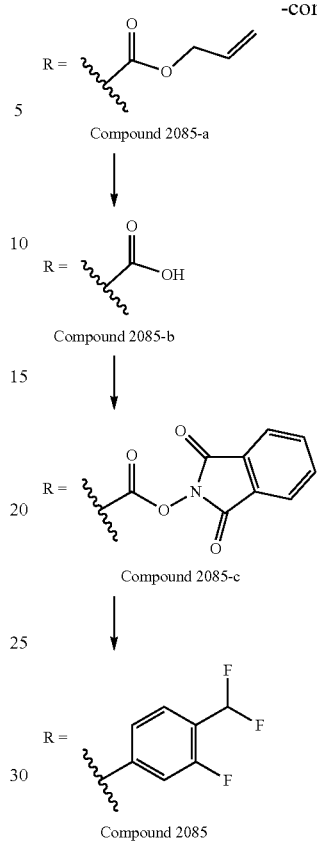

Compound 2085

Compound 2085-a (772 mg, 0.531 mmol, 77%) was obtained by the basic peptide synthesis method described in the present Examples, using Compound aa006-resin ((3S)-3-[9H-fluoren-9-ylmethoxycarbonyl(methyl)amino]-4-oxo-4-piperidin-1-ylbutanoic acid-2-chlorotrityl resin, Fmoc-MeAsp(O-Trt(2-Cl)resin)-pip) (0.531 mmol/g, 1.3 g, 0.69 mmol) as a raw material.
LCMS (ESI) m/z=1360 (M+H)+
Retention time: 1.01 min (analysis condition SQDFA05)
Compound 2085-a (772 mg, 0.568 mmol) and tetrakis(triphenylphosphine)palladium(0) (6.56 mg, 5.68 μmol) were mixed, DCM (1.2 ml) and phenylsilane (49 μl, 0.398 mmol) were added under a nitrogen atmosphere, and the mixture was stirred at room temperature for 30 minutes. The reaction mixture was purified by reverse phase column chromatography (acetonitrile with 0.1% formic acid/distilled water with 0.1% formic acid) to give Compound 2085-b (255 mg, 34%).
LCMS (ESI) m/z=1320 (M+H)+
Retention time: 0.87 min (analysis condition SQDFA05)
Compound 2085-b (255 mg, 0.193 mmol), N-hydroxyphthalimide (40.9 mg, 0.25 mmol), and 1-ethyl-3-(3-dimethylaminopropyl)carbodiimide hydrochloride (WSCI·HCl) (74.1 mg, 0.386 mmol) were dissolved in DCM (2 ml), and the reaction solution was stirred at room temperature for 2 hours and 15 minutes. The reaction mixture was diluted with DCM and washed with water twice. The organic layer was dried over sodium sulfate and then concentrated under reduced pressure to give Compound 2085-c as a crude product (299 mg, quant.).
LCMS (ESI) m/z=1465 (M+H)+
Retention time: 1.00 min (analysis condition SQDFA05)

Nickel bromide trihydrate (NiBr$_2$·3H$_2$O) (2.79 mg, 10.24 μmol) and 4,4'-di-tert-butyl-2,2'-bipyridyl (2.75 mg, 1.052 μmol) were dissolved in DMA (60 μL) under a nitrogen atmosphere to prepare a Ni solution.

To a mixture of Compound 2085-c (15.0 mg, 10.24 μmol), zinc powder (10 mg, 0.154 mmol), and 4-bromo-1-(difluoromethyl)-2-fluorobenzene (12.0 mg, 51.2 μmol) was added DMA (60 μL) under a nitrogen atmosphere, after which the above-prepared Ni solution was added and the mixture was stirred at room temperature for 16 hours. The reaction solution was then purified by reverse phase column chromatography (acetonitrile with 0.1% formic acid/distilled water with 0.1% formic acid), and the fractions were lyophilized to give Compound 2085 ((5S,8S,11S,15S,18S,23aS,29S,35S,37aS)-8-((S)-sec-butyl)-35-(cyclohexylmethyl)-18-cyclopentyl-29-(4-(difluoromethyl)-3-fluorophenethyl)-11-isobutyl-5,6,12,16,19,33,36-heptamethyl-15-(piperidin-1-carbonyl)docosahydro-2H,4H-spiro[azeto[2,1-u]pyrrolo[2,1-i][1,4,7,10,13,16,19,22,25,28,31]undecazacyclotetratriacontyne-21,1'-cyclopentane]-4,7,10,13,17,20,23,28,31,34,37(14H,22H)-undecone) (6.2 mg, 42.7%). The LC/MS data are as described in Table 22.

Synthesis of Compounds 2077, 2076, 2072, 2080, 2078, 2074, 2057, 2067, 2070, 2065, 2064, 2084, 2063, 2060, and 2069

Compounds 2077, 2076, 2072, 2080, 2078, 2074, 2057, 2067, 2070, 2065, 2064, 2084, 2063, 2060, and 2069 were obtained by the same synthesis method as in Compound 2085 using Compound 2085-c (15 mg) and using aryl bromides provided below (5 equivalents relative to the raw material peptide). The following table describes target compound peptides, aryl bromides used for reactions, and yield amounts (mg) and yield percentages (%) of the target compounds. The LC/MS data are as described in Table 22.

TABLE 14

| Target compound | Aryl bromide | Target compound mg | Yield % |
|---|---|---|---|
| Compound 2077 | 7-bromoquinoline | 7.6 | 53 |
| Compound 2076 | 4-bromo-1-(difluoromethoxy)-2-fluorobenzene | 6.3 | 43 |
| Compound 2072 | 5-bromo-2-(trifluoromethyl)benzonitrile | 4.6 | 31 |
| Compound 2080 | 4-bromo-2-methoxy-1-(trifluoromethyl)benzene | 5.2 | 35 |
| Compound 2078 | 5-bromo-2-(trifluoromethyl)pyridine | 3.8 | 26 |
| Compound 2074 | 5-bromo-2,2-difluoro-1,3-benzodioxole | 5.8 | 40 |
| Compound 2057 | 4-bromo-2-chloro-1-(trifluoromethoxy)benzene | 1.4 | 9 |
| Compound 2067 | 4-bromo-2-fluoro-1-(trifluoromethoxy)benzene | 4.7 | 31 |

TABLE 14-continued

| Target compound | Aryl bromide | Target compound mg | Yield % |
|---|---|---|---|
| Compound 2070 | 6-bromoquinoline | 6 | 42 |
| Compound 2065 | 6-bromo-1-methyl-1H-indole | 4.6 | 32 |
| Compound 2064 | 5-bromo-1-methyl-1H-indole | 4.4 | 30 |
| Compound 2084 | 5-bromo-2-methoxypyridine | 5.8 | 41 |
| Compound 2063 | 5-bromobenzofuran | 3.8 | 27 |
| Compound 2060 | 5-bromo-2-(difluoromethyl)pyridine | 5.5 | 38 |
| Compound 2069 | 2-bromo-5-(trifluoromethyl)pyridine | 3.8 | 26 |

Synthesis of Compound 2058 ((3S,9S,18S,21S,25S,28S,34S)-28-cyclohexyl-9-(cyclohexylmethyl)-21-isobutyl-7,10,13,16,22,26,29-heptamethyl-18-[(1S)-1-methyl]propyl]-3-[2-(4-methylsulfonylphenyl)ethyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone)

Compound 2058 was synthesized according to the following scheme.

aa006-resin

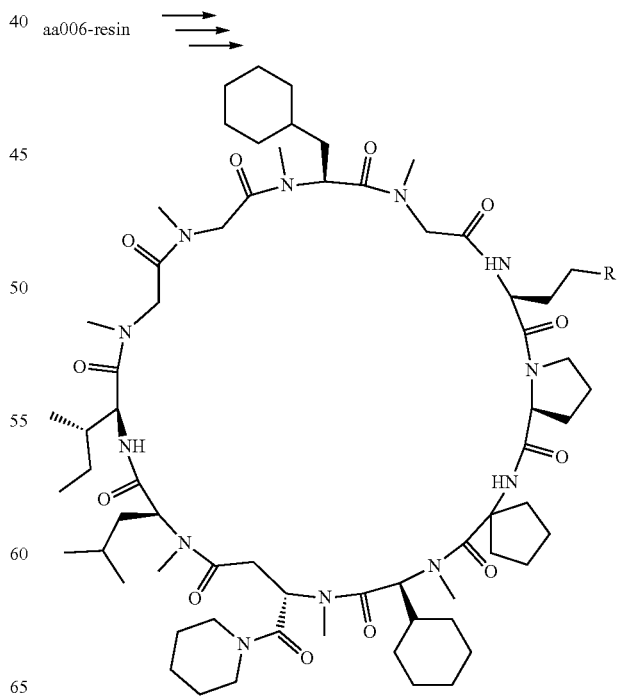

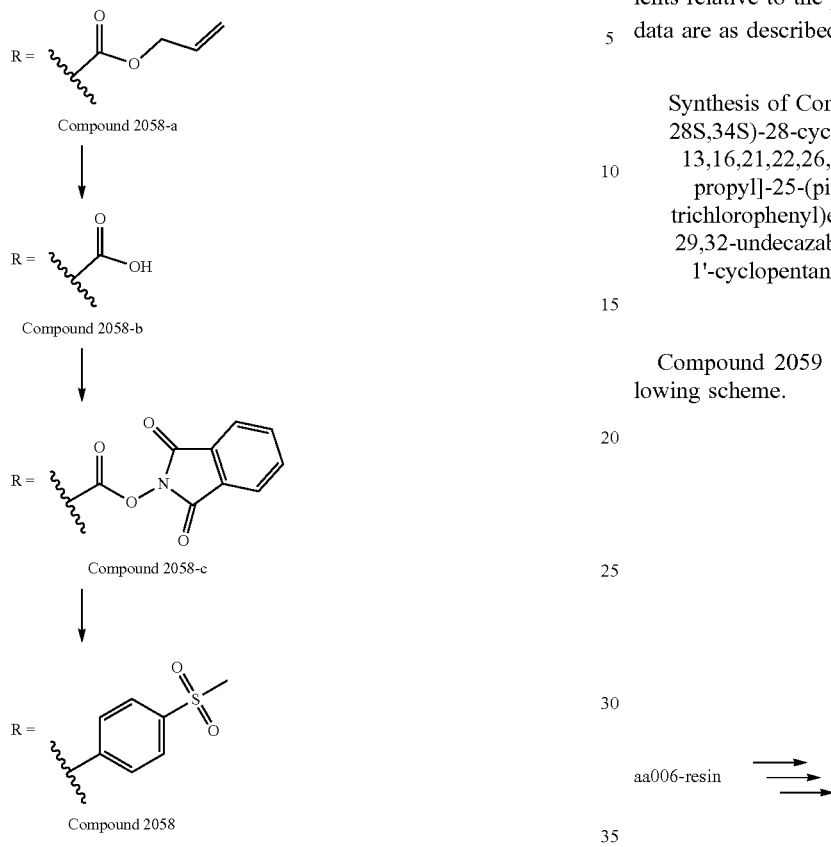

Compound 2058-a was obtained by peptide synthesis according to the basic peptide synthesis method described in the present Examples, using Compound aa006-resin ((3S)-3-[9H-fluoren-9-ylmethoxycarbonyl(methyl)amino]-4-oxo-4-piperidin-1-ylbutanoic acid-2-chlorotrityl resin, Fmoc-MeAsp(O-Trt(2-Cl)resin)-pip) as a raw material. Further, Compound 2058-b was obtained by the same method as in the synthesis of Compound 2085-b. Further, Compound 2058-c (299 mg, 0.206 mmol) was obtained by the same method as in the synthesis of Compound 2085-c.

LCMS (ESI) m/z=1453 (M+H)+

Retention time: 1.03 min (analysis condition SQDFA05)

Compound 2058 ((3S,9S,18S,21S,25S,28S,34S)-28-cyclohexyl-9-(cyclohexylmethyl)-21-isobutyl-7,10,13,16,22,26,29-heptamethyl-18-[(1S)-1-methylpropyl]-3-[2-(4-methylsulfonylphenyl)ethyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone) (4.1 mg, 28%) was obtained by the same method as in the synthesis of Compound 2085 using Compound 2058-c (15 mg, 10.32 μmol) as a raw material and using 1-bromo-4-(methylsulfonyl)benzene (5 equivalents relative to the peptide) as an aryl halide. The LC/MS data are as described in Table 22.

Synthesis of Compound 2059 ((3S,9S,18S,21S,25S,28S,34S)-28-cyclohexyl-9-(cyclohexylmethyl)-7,10,13,16,21,22,26,29-octamethyl-18-[(1S)-1-methylpropyl]-25-(piperidine-1-carbonyl)-3-[2-(3,4,5-trichlorophenyl)ethyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone)

Compound 2059 was synthesized according to the following scheme.

aa006-resin →→→

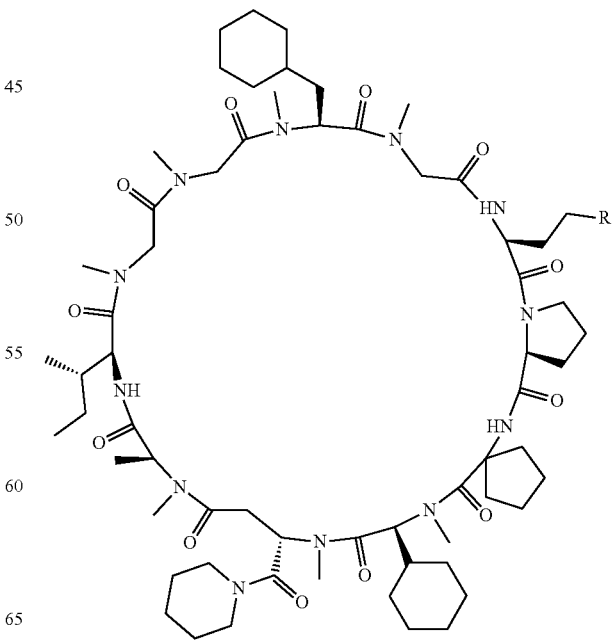

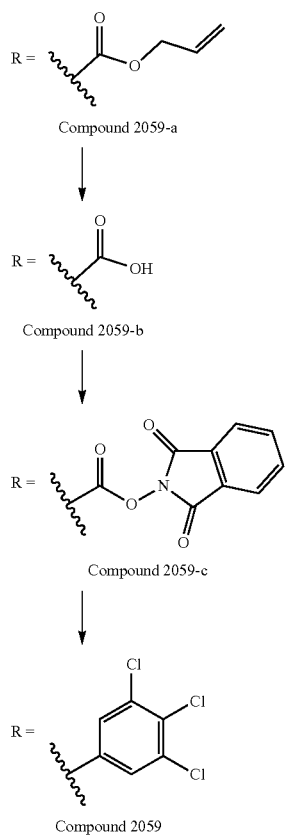

Compound 2059-a

Compound 2059-b

Compound 2059-c

Compound 2059

Compound 2059-a was obtained by peptide synthesis according to the basic peptide synthesis method described in the present Examples, using Compound aa006-resin ((3S)-3-[9H-fluoren-9-ylmethoxycarbonyl(methyl)amino]-4-oxo-4-piperidin-1-ylbutanoic acid-2-chlorotrityl resin, Fmoc-MeAsp(O-Trt(2-Cl)resin)-pip) (0.437 mmol/g, 3 g, 1.311 mmol) as a raw material. Further, Compound 2059-b was obtained by the same method as in the synthesis of Compound 2085-b. Further, Compound 2059-c (388 mg, 0.275 mmol, 21%) was obtained by the same method as in the synthesis of Compound 2085-c.

LCMS (ESI) m/z=1411 (M+H)+

Retention time: 0.95 min (analysis condition SQDFA05)

Compound 2059 ((3S,9S,18S,21S,25S,28S,34S)-28-cyclohexyl-9-(cyclohexylmethyl)-7,10,13,16,21,22,26,29-octamethyl-18-[(1S)-1-methylpropyl]-25-(piperidine-1-carbonyl)-3-[2-(3,4,5-trichlorophenyl)ethyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone) (6.6 mg, 47%) was obtained by the same method as in the synthesis of Compound 2085 using Compound 2059-c (15 mg) as a raw material and using 5-bromo-1,2,3-trichlorobenzene (10 equivalents relative to the peptide) as an aryl halide. The LC/MS data are as described in Table 22.

Synthesis of Compounds 2081, 2075, 2062, 2066, and 2082

Compounds 2081, 2075, 2062, 2066, and 2082 were obtained by the same synthesis method as in Compound 2059 using Compound 2059-c (15 mg) as a raw material and using aryl halides provided below (10 equivalents relative to the raw material peptide). The following table describes target compound peptides, aryl halides used for reactions, and yield amounts (mg) and yield percentages (%) of the target compounds. The LC/MS data are as described in Table 22.

TABLE 15

| Target compound | Aryl halide | Yield mg | Yield % |
| --- | --- | --- | --- |
| Compound 2081 | 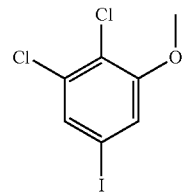<br>Compound 2081-a | 6.9 | 47 |
| Compound 2075 | 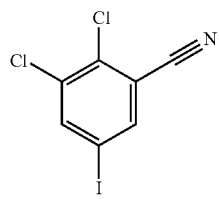 [SMILES: N#Cc1cc(I)cc(Cl)c1Cl]<br>Compound 2075-a | 0.7 | 5 |
| Compound 2062 | 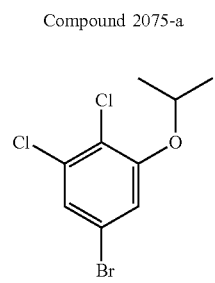<br>Compound 2062-a | 9.4 | 60 |

TABLE 15-continued

| Target compound | Aryl halide | Yield mg | Yield % |
|---|---|---|---|
| Compound 2066 | 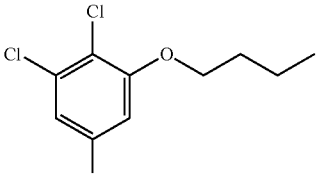<br>Compound 2066-a | 3.3 | 21 |
| Compound 2082 | 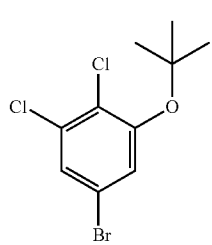<br>Compound 2082-a | 8.3 | 53 |

Synthesis of Compound 2068 ((3S,9S,18S,21S,25S,28S,34S)-9-(cyclohexylmethyl)-28-isopropyl-7,10,13,16,21,22,26,29-octamethyl-18-[(1S)-1-methyl]propyl]-25-(piperidine-1-carbonyl)-3-[2-(3,4,5-trichlorophenyl)ethyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone)

Compound 2068 was synthesized according to the following scheme.

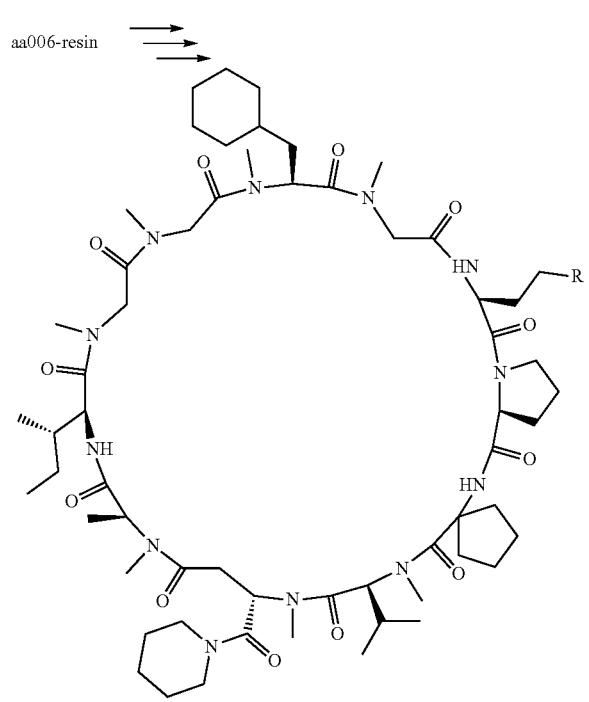

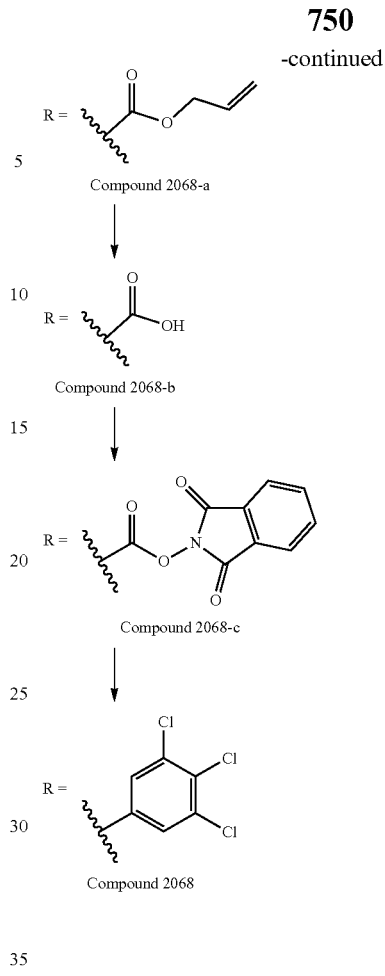

Compound 2068-a was obtained by peptide synthesis according to the basic peptide synthesis method described in the present Examples, using Compound aa006-resin ((3S)-3-[19H-fluoren-9-ylmethoxycarbonyl(methyl)amino]-4-oxo-4-piperidin-1-ylbutanoic acid-2-chlorotrityl resin, Fmoc-MeAsp(O-Trt(2-Cl)resin)-pip) (0.437 mmol/g, 4.1 g, 1.79 mmol) as a raw material. Further, Compound 2068-b was obtained by the same method as in the synthesis of Compound 2085-b. Further, Compound 2068-c (553 mg, 0.403 mmol, 23%) was obtained by the same method as in the synthesis of Compound 2085-c.

LCMS (ESI) m/z=1371 (M+H)+

Retention time: 0.86 min (analysis condition SQDFA05)

Nickel bromide trihydrate (5.97 mg, 0.022 mmol) and 4,4'-di-tert-butyl-2,2'-bipyridyl (5.87 mg, 0.022 mmol) were dissolved in DMA (110 μL) under a nitrogen atmosphere to prepare a Ni solution.

To Compound 2068-c (15.0 mg, 10.94 μmol), zinc powder (10.7 mg, 0.164 mmol), and 5-bromo-1,2,3-trichlorobenzene (28.5 mg, 109 μmol) was added DMA (55 μL) under a nitrogen atmosphere, after which the above-prepared Ni solution was added and the mixture was stirred at room temperature for five hours. The precipitate was filtered off, and the solvent was then evaporated under reduced pressure. n-Hexane/TFE/water=1/1/1 was added and the precipitate was filtered off, after which the n-hexane layer was removed and the solvent was evaporated under reduced pressure. The reaction solution was then purified by reverse phase column chromatography (acetonitrile with 0.1% formic acid/distilled water with 0.1% formic acid) to give Compound 2068 ((3S,9S,18S,21S,25S,28S,34S)-9-(cyclohexylmethyl)-28-isopropyl-7,10,13,16,21,22,26,29-octamethyl-18-[(1S)-1-methylpropyl]-25-(piperidine-1-carbonyl)-

3-[2-(3,4,5-trichlorophenyl)ethyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone) (5.0 mg, 33%). The LC/MS data are as described in Table 22.

Synthesis of Compounds 2061, 2071, 2079, 2083, and 2073

Compounds 2061, 2071, 2079, 2083, and 2073 were obtained by the same synthesis method as in Compound 2068 using Compound 2068-c (15 mg) as a raw material and using aryl halides provided below (10 equivalents relative to the raw material peptide). The following table describes target compound peptides, aryl halides used for reactions, and yield amounts (mg) and yield percentages (%) of the target compounds. The LC/MS data are as described in Table 22.

TABLE 16

| Target compound | Aryl halide | Yield mg | Yield % |
|---|---|---|---|
| Compound 2061 | Compound 2081-a | 6.8 | 46 |
| Compound 2071 | Compound 2075-a | 2.5 | 17 |
| Compound 2079 | Compound 2062-a | 1.1 | 7 |
| Compound 2083 | Compound 2066-a | 7.2 | 47 |

TABLE 16-continued

| Target compound | Aryl halide | Yield mg | Yield % |
|---|---|---|---|
| Compound 2073 | Compound 2082-a | 9.2 | 60 |

Aryl halides used for synthesizing Compounds 2081, 2075, 2062, 2066, 2082, 2061, 2071, 2079, 2083, and 2073 were synthesized as follows.

Synthesis of Compound 2081-a
(1,2-dichloro-5-iodo-3-methoxybenzene)

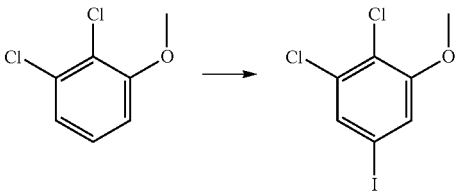

To a solution of 2,3-dichloroanisole (1.0 g, 5.65 mmol) in TBME (28.2 mL) were added bis(pinacolato)diboron (B$_2$pin$_2$) (2.15 g, 8.48 mmol) and (1,5-cyclooctadiene)(methoxy)iridium(I) (dimer) ([Ir(COD)(OMe)]$_2$) (0.187 g, 0.282 mmol), and the mixture was stirred at room temperature for two hours under a nitrogen atmosphere. The solvent was evaporated under reduced pressure, DMF (50 mL) was added, copper(I) iodide (CuI) (1.61 g, 8.47 mmol) was further added, and the mixture was stirred at 80° C. for four hours in air. After cooling to room temperature, n-hexane/ethyl acetate=1/1 (100 mL) was added and the mixture was sequentially washed with 100 mL each of a saturated aqueous ammonium chloride solution, a saturated aqueous sodium thiosulfate solution, a saturated aqueous sodium bicarbonate solution, and 50% saline. This was dried over anhydrous sodium sulfate and filtered off, after which the solvent was evaporated under reduced pressure. The resulting residue was purified by reverse phase column chromatography (acetonitrile with 0.1% formic acid/distilled water with 0.1% formic acid). The fractions were collected, concentrated, then dissolved in n-hexane/ethyl acetate=1/1, and washed with a saturated aqueous sodium bicarbonate solution. This was dried over anhydrous sodium sulfate and filtered off, after which the solvent was evaporated under reduced pressure to give Compound 2081-a (1,2-dichloro-5-iodo-3-methoxybenzene) (514 mg, 30%).

Retention time: 1.01 min (analysis condition SQDFA05)
$^1$H-NMR (DMSO-D$_6$) δ: 7.60 (1H, d, J=1.9 Hz), 7.45 (1H, d, J=1.9 Hz), 3.90 (3H, s).

Synthesis of Compound 2075-a (2,3-dichloro-5-iodobenzonitrile)

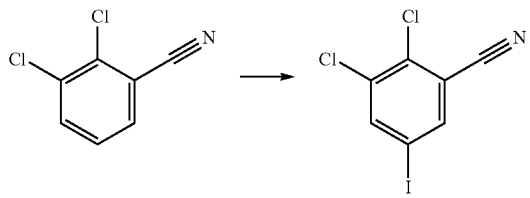 [SMILES: N#Cc1cccc(Cl)c1Cl ; N#Cc1cc(I)cc(Cl)c1Cl]

To a solution of 2,3-dichlorobenzonitrile (500 mg, 2.91 mmol) in THF (14.5 mL) were added bis(pinacolato)diboron (B$_2$pin$_2$) (1.11 g, 4.36 mmol) and (1,5-cyclooctadiene)(methoxy)iridium(I) (dimer) ([Tr(COD)(OMe)]) (96 mg, 0.145 mmol), and the mixture was stirred at 60° C. for one hour under a nitrogen atmosphere. The solvent was evaporated under reduced pressure, DMF (30 mL) was added, copper(I) iodide (CuI) (830 mg, 4.36 mmol) and N-iodosuccinimide (NIS) (981 mg, 4.36 mmol) were further added, and the mixture was stirred at 80° C. for six hours in air. After cooling to room temperature, n-hexane/ethyl acetate=1/1 (30 mL) was added and the mixture was sequentially washed with 60 mL each of a saturated aqueous ammonium chloride solution, a saturated aqueous sodium bicarbonate solution, and 50% saline. This was dried over anhydrous sodium sulfate and filtered off, after which the solvent was evaporated under reduced pressure. The resulting residue was purified by reverse phase column chromatography (acetonitrile with 0.1% formic acid/distilled water with 0.1% formic acid). The fractions were collected, concentrated, then dissolved in n-hexane/ethyl acetate=1/1, and washed with a saturated aqueous sodium bicarbonate solution. This was dried over anhydrous sodium sulfate and filtered off, after which the solvent was evaporated under reduced pressure to give Compound 2075-a (2,3-dichloro-5-iodobenzonitrile) (535 mg, 62%).

Retention time: 0.91 min (analysis condition SQDFA05)
$^1$H-NMR (DMSO-D$_6$) δ: 8.42 (1H, d, J=1.9 Hz), 8.39 (1H, d, J=1.9 Hz).

Synthesis of Compound 2062-a (5-bromo-1,2-dichloro-3-propan-2-yloxybenzene)

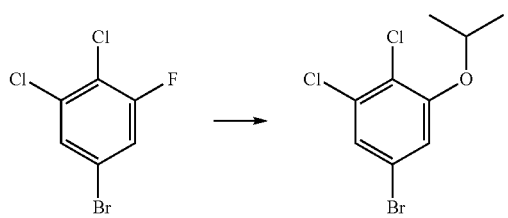

A solution of 5-bromo-1,2-dichloro-3-fluorobenzene (200 mg, 0.820 mmol) and 2-propanol (246 mg, 4.10 mmol) in DMF (1.0 mL) was cooled to 0° C. under ice-cooling, and sodium hydride (NaH) (60%, oil, 65.6 mg, 1.64 mmol) was added. The mixture was stirred at 60° C. for one hour and then cooled to 0° C., and sodium hydride (NaH) (60%, oil, 10.0 mg, 0.250 mmol) was added. The mixture was stirred at 60° C. for 30 minutes and then cooled to room temperature, a saturated aqueous ammonium chloride solution was added, and the mixture was extracted with ethyl acetate/n-hexane=1/1. This was dried over anhydrous sodium sulfate and filtered off, and the solvent was evaporated under reduced pressure to give Compound 2062-a (5-bromo-1,2-dichloro-3-propan-2-yloxybenzene) (211 mg, 91%).

Retention time: 1.11 min (analysis condition SQDFA05)
$^1$H-NMR (CDCl$_3$) δ: 7.22 (1H, d, J=2.1 Hz), 6.97 (1H, dd, J=2.1, 0.5 Hz), 4.58-4.51 (1H, m), 1.39 (6H, d, J=6.2 Hz).

Synthesis of Compound 2066-a (5-bromo-1-butoxy-2,3-dichlorobenzene)

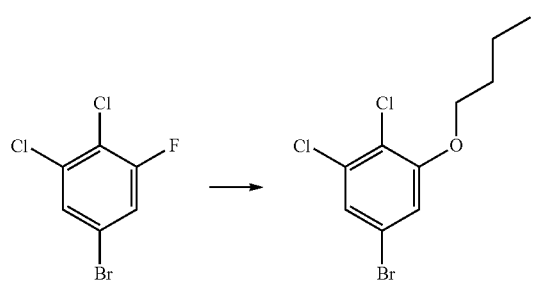

Compound 2066-a (5-bromo-1-butoxy-2,3-dichlorobenzene) (211 mg, 86%) was obtained by the same synthesis method as in Compound 2062-a using 5-bromo-1,2-dichloro-3-fluorobenzene and n-butanol.

Retention time: 1.19 min (analysis condition SQDFA05)
$^1$H-NMR (CDCl$_3$) δ: 7.22 (1H, d, J=2.1 Hz), 6.95 (1H, d, J=2.1 Hz), 4.01 (2H, t, J=6.4 Hz), 1.86-1.79 (2H, m), 1.57-1.48 (2H, m), 0.99 (3H, t, J=7.4 Hz).

Synthesis of Compound 2082-a (5-bromo-1,2-dichloro-3-[(2-methylpropan-2-yl)oxy]benzene)

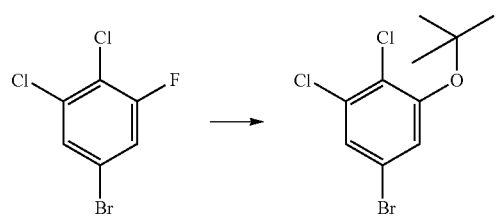

A solution of 5-bromo-1,2-dichloro-3-fluorobenzene (200 mg, 0.820 mmol) and tert-butanol (304 mg, 4.10 mmol) in DMF (1.0 mL) was cooled to 0° C. under ice-cooling, and sodium hydride (NaH) (60%, oil, 49.2 mg, 1.23 mmol) was added. The mixture was stirred at 60° C. for 1.5 hours and then cooled to 0° C. under ice-cooling, and sodium hydride (NaH) (60%, oil, 49.2 mg, 1.23 mmol) was added. The mixture was stirred at 60° C. for 30 minutes and then cooled to room temperature, and water (100 μL) was added. The reaction solution was then purified by reverse phase column chromatography (acetonitrile with 0.1% formic acid/distilled water with 0.1% formic acid), and the fractions were lyophilized to give Compound 2082-a (5-bromo-1,2-dichloro-3-[(2-methylpropan-2-yl)oxy]benzene) (127 mg, 52%).

Retention time: 1.15 min (analysis condition SQDFA05)
$^1$H-NMR (CDCl$_3$) δ: 7.34 (1H, d, J=2.1 Hz), 7.18 (1H, d, J=2.1 Hz), 1.44 (9H, s).

1-4-4. Peptide Modification by Sonogashira Coupling Reaction
Synthesis of Compound 2142 ((3S,9S,12S,18S,27S,30S,34S)-9-butyl-18-[(4-chlorophenyl)methyl]-12-[(3-ethinylphenyl)methyl]-3,30-diisobutyl-1,6,6,7,16,19,22,25,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone)
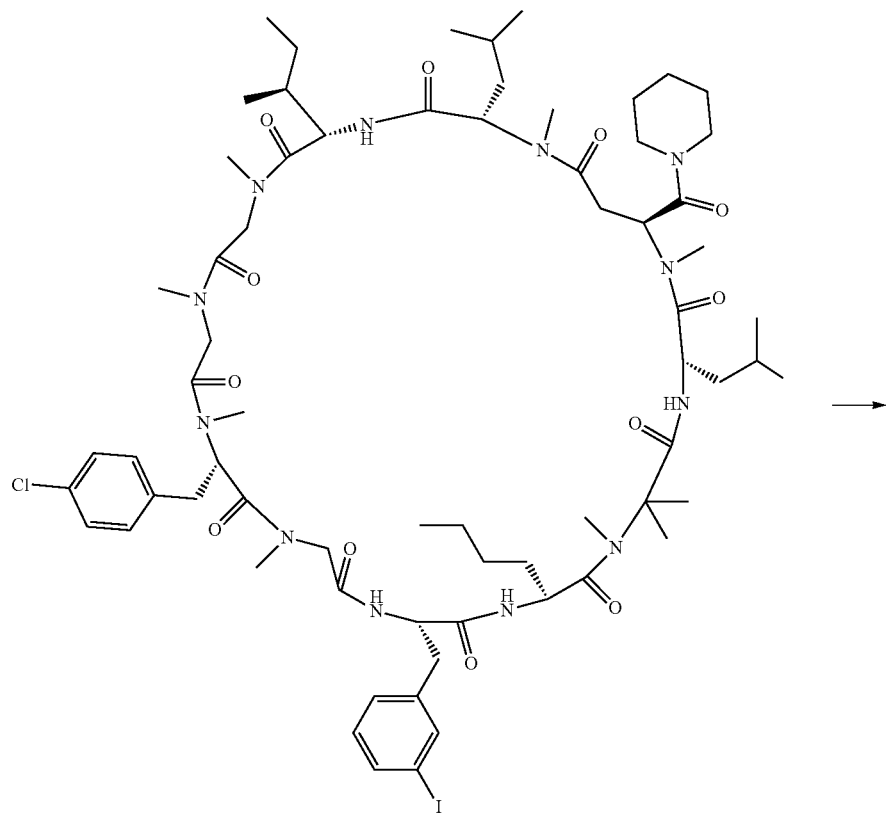
Compound 2142-a -continued

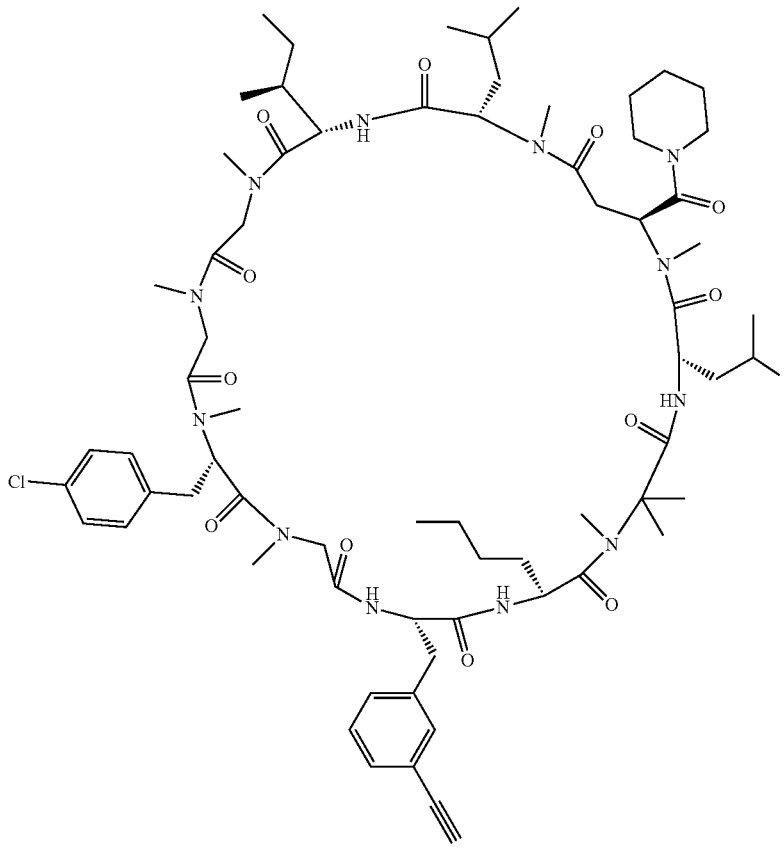

Compound 2142

Compound 2142-a (123.7 mg, 49%) was obtained by peptide synthesis according to the basic peptide synthesis method described in the present Examples, using Compound aa006-resin ((3S)-3-[9H-fluoren-9-ylmethoxycarbonyl (methyl)amino]-4-oxo-4-piperidin-1-ylbutanoic acid-2-chlorotrityl resin, Fmoc-MeAsp(O-Trt(2-Cl)resin)-pip) (400 mg, 0.436 mmol/g, 0.1744 mmol) as a raw material.

LCMS (ESI) m/z=1443.6 (M+H)+

Retention time: 1.06 min (analysis condition SQDFA05)

To a mixture of Compound 2142-a (30 mg, 0.021 mmol), bis(triphenylphosphine)palladium(II) dichloride (7.3 mg, 0.5 equivalents), and copper(I) iodide (4 mg, 1 equivalent) in DMF (208 μl) were added triethylamine (0.145 mL, 50 equivalents) and trimethylsilylacetylene (35.2 μL, 12 equivalents), and the mixture was stirred at room temperature for 30 minutes. Half of the reaction solution was purified by reverse phase column chromatography (acetonitrile with 0.1% formic acid/distilled water with 0.1% formic acid). To the resulting fractions were added potassium carbonate (6 equivalents relative to the raw material peptide) and water (6 equivalents relative to the raw material peptide), and the mixture was concentrated under reduced pressure. To the residue were added methanol (500 µL) and water (50 µL). After confirming that the trimethylsilyl group was deprotected, the resulting reaction solution was concentrated under reduced pressure. The residue was dissolved in DMSO (1 mL) and then purified by reverse phase column chromatography (acetonitrile with 0.1% formic acid/distilled water with 0.1% formic acid), and the fractions containing the target compound were lyophilized. The residue was dissolved in DMSO (1 mL) and then concentrated under reduced pressure again to give Compound 2142 ((3S,9S,12S,18S,27S,30S,34S)-9-butyl-18-[(4-chlorophenyl)methyl]-12-[(3-ethinylphenyl)methyl]-3,30-diisobutyl-1,6,6,7,16,19,22,25,31-nonamethyl-27-[(1S)-1-methylpropyl]-34-(piperidine-1-carbonyl)-1,4,7,10,13,16,19,22,25,28,31-undecazacyclotetratriacontane-2,5,8,11,14,17,20,23,26,29,32-undecone) (1.6 mg, 6%). The LC/MS data are as described in Table 22.

1-4-5. Peptide Modification by Click Chemistry

Synthesis of Compound 2113 ((3S,9S,18S,21S,25S,28S,34S,36R)-3-[2-[3-chloro-4-(trifluoromethyl)phenyl]ethyl]-9-(cyclopentylmethyl)-21-isobutyl-28-isopropyl-7,10,13,16,22,26,29-heptamethyl-18-[(1S)-1-methylpropyl]-25-(piperidine-1-carbonyl)-36-(triazol-1-yl)spiro[1,4,7,10,13,16,19,22,26,29,32-undecazabicyclo[32.3.0]heptatriacontane-31,1'-cyclopentane]-2,5,8,11,14,17,20,23,27,30,33-undecone)

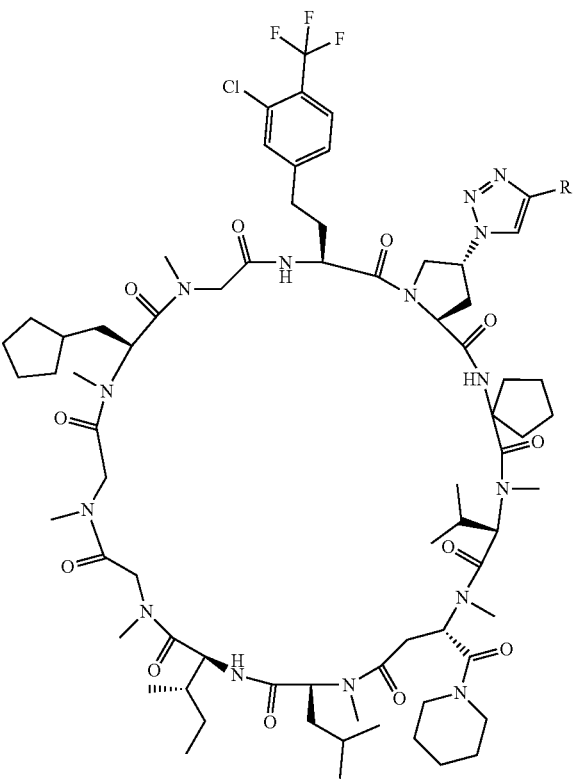

Compound 2113-b (R = trimethylsilyl group)
Compound 2113 (R = H)

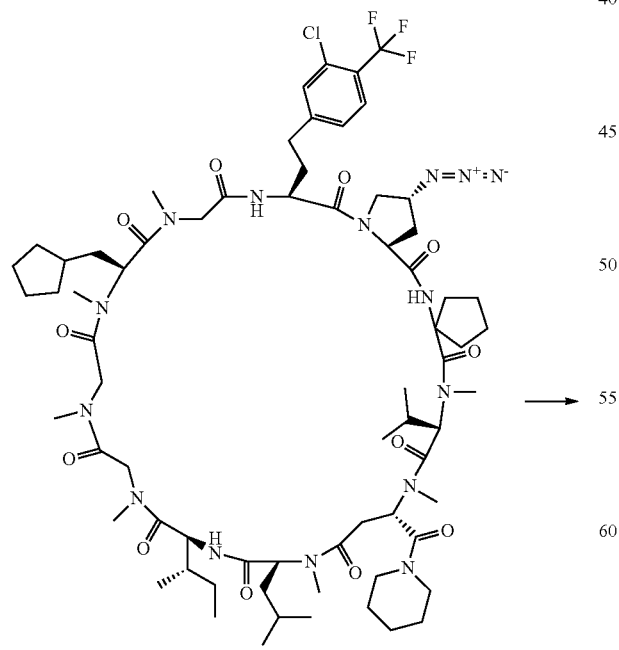

Compound 2113-a

Compound 2113-a (5.4 mg, 10%) was obtained by peptide synthesis according to the basic peptide synthesis method described in the present Examples, using Compound aa006- resin ((3S)-3-[9H-fluoren-9-ylmethoxycarbonyl(methyl) amino]-4-oxo-4-piperidin-1-ylbutanoic acid-2-chlorotrityl resin, Fmoc-MeAsp(O-Trt(2-Cl)resin)-pip) (100 mg, 0.37 mmol/g, 0.037 mmol) as a raw material and using (2S,4R)-4-azido-1-Fmoc-pyrrolidine-2-carboxylic acid (Fmoc-L-Pro (4-N3)-OH(2S,4R), CAS No. 702679-55-8) as an Fmoc amino acid.

LCMS (ESI) m/z=1428.97 (M+H)+

Retention time: 1.05 min (analysis condition SQDFA05)

To Compound 2113-a (5.4 mg, 3.8 µmol) were added copper(I) iodide (3 mg, 15.75 µmol), acetonitrile (0.5 mL), DIPEA (50 µL, 286 µmol), and trimethylsilylacetylene (50 µL, 0.361 mmol) under a nitrogen atmosphere, and the mixture was stirred at room temperature for 16 hours. The reaction mixture was filtered through celite, washed with acetonitrile, and then concentrated under reduced pressure. The resulting crude product was purified by reverse phase column chromatography (acetonitrile with 0.1% formic acid/distilled water with 0.1% formic acid) to give Compound 2113-b (6.4 mg, quant.).

LCMS (ESI) m/z=1527.06 (M+H)+

Retention time: 1.10 min (analysis condition SQDFA05)

Compound 2113-b (6.4 mg) was dissolved in 1,4-dioxane (1 mL), and a solution of tetrabutylammonium fluoride (TBAF) in THF (1 M, 0.5 mL, 0.5 mmol) was added. The reaction mixture was stirred at room temperature for 162 hours and then concentrated under reduced pressure. The resulting crude product was purified by reverse phase column chromatography (acetonitrile with 0.1% formic acid/distilled water with 0.1% formic acid) to give Compound 2113 ((3S,9S,18S,21S,25S,28S,34S,36R)-3-[2-[3-chloro-4-(trifluoromethyl)phenyl]ethyl]-9-(cyclopentylmethyl)-21-isobutyl-28-isopropyl-7,10,13,16,22,26,29-heptamethyl-18-[(1S)-1-methylpropyl]-25-(piperidine-1-carbonyl)-36-(triazol-1-yl)spiro[1,4,7,10,13,16,19,22,26,29,32-undecazabicyclo[32.3.0]heptatriacontane-31,1'-cyclopentane]-2,5,8,11,14,17,20,23,27,30,33-undecone) (4.6 mg, 84% through two steps). The LC/MS data are as described in Table 22.

Synthesis of Compound 2115 ((3S,9S,18S,21S,25S, 28S,34S,36S)-3-[2-[3-chloro-4-(trifluoromethyl) phenyl]ethyl]-9-(cyclopentylmethyl)-21-isobutyl-28-isopropyl-7,10,13,16,22,26,29-heptamethyl-18-[(1S)-1-methylpropyl]-25-(piperidine-1-carbonyl)-36-(triazol-1-yl)spiro[1,4,7,10,13,16,19,22,26,29,32-undecazabicyclo[32.3.0]heptatriacontane-31,1'-cyclopentane]-2,5,8,11,14,17,20,23,27,30,33-undecone)

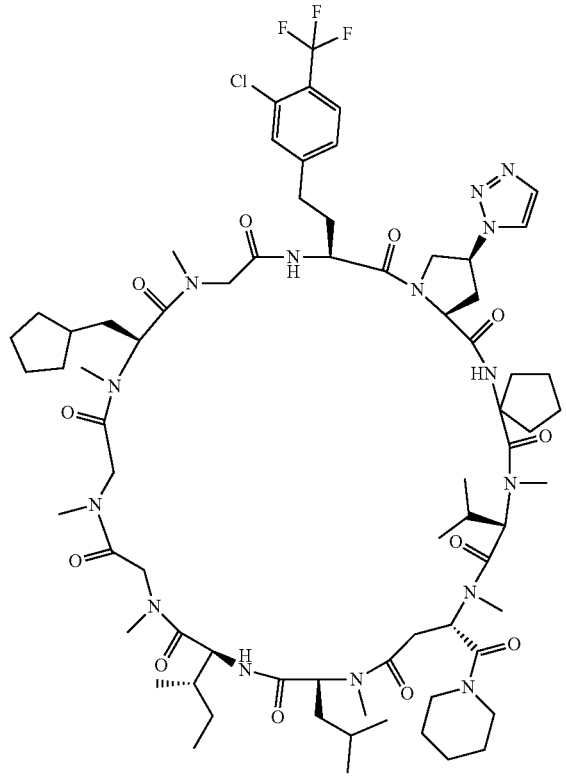

Compound 2115

Compound 2115 ((3S,9S,18S,21S,25S,28S,34S,36S)-3-[2-[3-chloro-4-(trifluoromethyl)phenyl]ethyl]-9-(cyclopentylmethyl)-21-isobutyl-28-isopropyl-7,10,13,16,22,26,29-heptamethyl-18-[(1S)-1-methylpropyl]-25-(piperidine-1-carbonyl)-36-(triazol-1-yl)spiro[1,4,7,10,13,16,19,22,26,29,32-undecazabicyclo[32.3.0]heptatriacontane-31,1'-cyclopentane]-2,5,8,11,14,17,20,23,27,30,33-undecone) (8.0 mg) was obtained by the same method as in the synthesis of Compound 2113 using Compound aa006-resin ((3S)-3-[9H-fluoren-9-ylmethoxycarbonyl(methyl)amino]-4-oxo-4-piperidin-1-ylbutanoic acid-2-chlorotrityl resin, Fmoc-MeAsp(O-Trt(2-Cl)resin)-pip) as a starting material for peptide synthesis according to the basic peptide synthesis method described in the present Examples, and using (2S, 4S)-4-azido-1-Fmoc-pyrrolidine-2-carboxylic acid (Fmoc-L-Pro(4-N3)-OH(2S,4S), CAS No. 263847-08-1) as an Fmoc amino acid. The LC/MS data are as described in Table 22.

1-4-6. Peptide Modification by Suzuki Coupling
Synthesis of Compound 2096 ((3S,9S,18S,21S,25S, 28S,31S,34S)-31-benzyl-9-[(4-chlorophenyl) methyl]-3-[2-[2-fluoro-4-(trifluoromethyl)phenyl] ethyl]-28-isobutyl-7,10,13,16,21,22,29,32-octamethyl-18-[(1S)-1-methylpropyl]-25-(pyrrolidine-1-carbonyl)-1,4,7,10,13,16,19,22,26,29, 32-undecazabicyclo[32.3.0]heptatriacontane-2,5,8, 11,14,17,20,23,27,30,33-undecone)
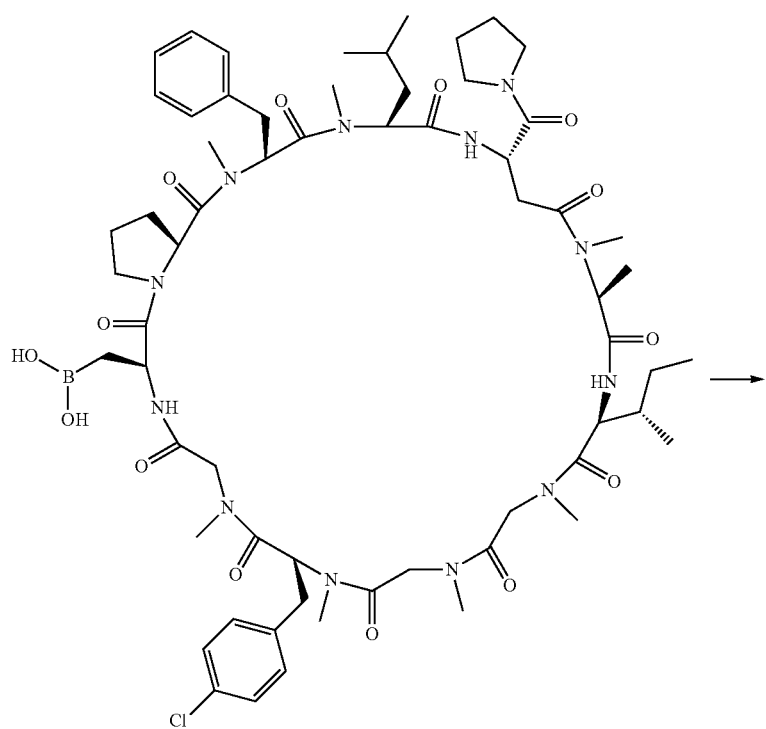
Compound 2096-a

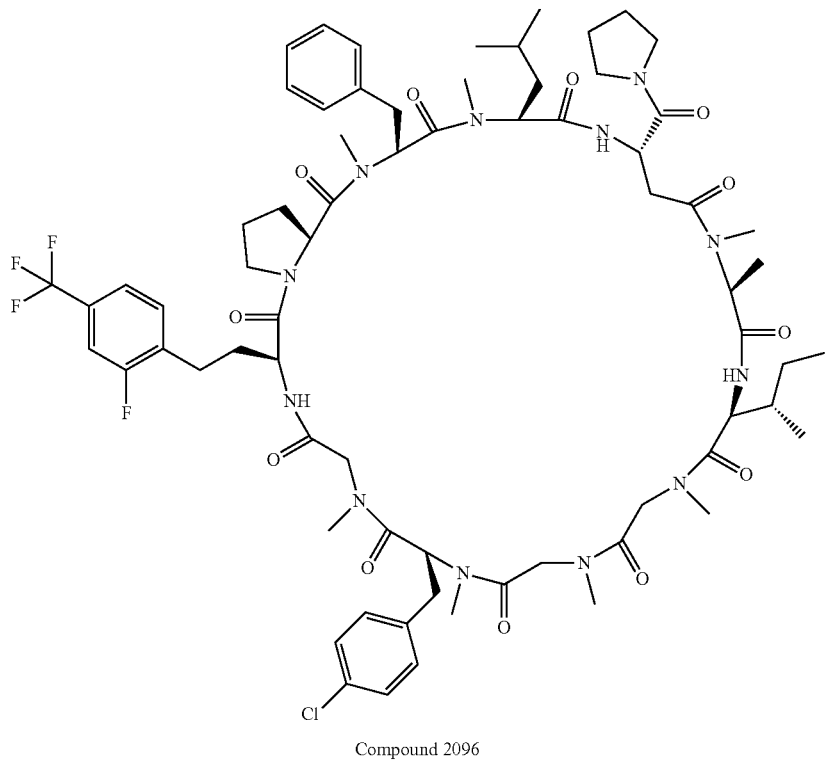

Compound 2096

Compound 2096-a (157 mg) was obtained by peptide synthesis according to the basic peptide synthesis method described in the present Examples, using Compound aa018-resin ((3S)-3-(9H-fluoren-9-ylmethoxycarbonylamino)-4-oxo-4-pyrrolidin-1-ylbutanoic acid-2-chlorotrityl resin (Fmoc-Asp(O-Trt(2-Cl)-resin)-pyrro)) as a raw material.

LCMS (ESI) m/z=1273.3 (M−H)−

Retention time: 0.74 min (analysis condition SQDFA05)

To a mixed solution of Compound 2096-a (15 mg, 0.012 mmol), thallium carbonate (55.1 mg, 0.118 mmol), and RuPhos Pd G4 (CAS No. 1599466-85-9, 30 mg, 0.035 mmol) in water/THF (1/10, 0.235 mL) was added 1-(bromomethyl)-2-fluoro-4-(trifluoromethyl)benzene (24.2 mg, 0.094 mmol) under a nitrogen atmosphere, and the mixture was then stirred at 70° C. for 18 hours. The reaction solution was filtered through celite and then purified by reverse phase column chromatography (C18, methanol/10 mM aqueous ammonium acetate and 0.3% formic acid/acetonitrile/water) to give Compound 2096 ((3S,9S,18S,21S,25S,28S,31S,34S)-31-benzyl-9-[(4-chlorophenyl)methyl]-3-[2-[2-fluoro-4-(trifluoromethyl)phenyl]ethyl]-28-isobutyl-7,10,13,16,21,22,29,32-octamethyl-18-[(1S)-1-methylpropyl]-25-(pyrrolidine-1-carbonyl)-1,4,7,10,13,16,19,22,26,29,32-undecazabicyclo[32.3.0]heptatriacontane-2,5,8,11,14,17,20,23,27,30,33-undecone) (14.1 mg, 71%). The LC/MS data are as described in Table 22.

Synthesis of Compounds 2093, 2091, 2087, 2094, 2086, 2089, 2092, 2090, 2088, and 2095

Compound 2093-a (312 mg) was obtained by peptide synthesis according to the basic peptide synthesis method described in the present Examples, using Compound aa138-resin ((3R)-3-(9H-fluoren-9-ylmethoxycarbonylamino)butanoic acid-2-chlorotrityl resin, Fmoc-D-3-Abu-O-Trt(2-Cl) resin) as a raw material.

LCMS (ESI) m/z=1188.4 (M−H)− (detected as dehydrated form)

Retention time: 2.84 min (analysis condition SQDFA30long50deg)

Compound 2093-a

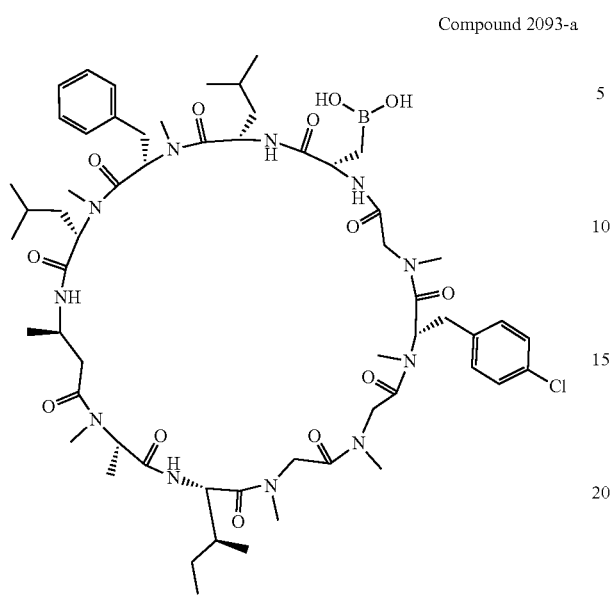

Compound 2093, 2091, 2087, 2094, 2086, 2089, 2092, 2090, 2088, and 2095 were obtained by the same synthesis method as in Compound 2096 using Compound 2093-a as a raw material and using a benzyl bromide provided below (8 equivalents relative to the raw material peptide). The following table describes target compound peptides, benzyl bromides used for reactions, and yield amounts (mg) and yield percentages (%) of the target compounds. The LC/MS data are as described in Table 22.

TABLE 17

| Target compound | Benzyl bromide | Yield mg | Yield % |
|---|---|---|---|
| Compound 2093 | 1-(bromomethyl)-3-fluoro-4-(trifluoromethyl)benzene | 5.6 | 34 |
| Compound 2091 | 1-(bromomethyl)-2,3,4,5,6,-pentafluorobenzene | 9 | 54 |
| Compound 2087 | 1-(bromomethyl)-2,4,5-trifluorobenzene | 5.3 | 33 |
| Compound 2094 | 2-(bromomethyl)-4-chloro-1-fluorobenzene | 5.8 | 35 |
| Compound 2086 | 1-(bromomethyl)-4-chloro-2-fluorobenzene | 2.6 | 16 |
| Compound 2089 | 1-(bromomethyl)-2,4-difluorobenzene | 1.7 | 11 |
| Compound 2092 | 2-(bromomethyl)-1-chloro-3-fluorobenzene | 0.7 | 4.6 |
| Compound 2090 | 2-(bromomethyl)-1,3,5-trifluorobenzene | 7 | 43 |
| Compound 2088 | 4-(bromomethyl)-2-chloro-1-(trifluoromethyl)benzene | 3.8 | 22 |
| Compound 2095 | 1-(bromomethyl)-3-(trifluoromethyl)benzene | 1.4 | 8.8 |

1-4-6. Peptide Modification by Chan-Lam-Evans Coupling

The following table shows structural formulas of 2,4,6-triarylboroxane-pyridine complexes used for reactions corresponding to target compounds. These 2,4,6-triarylboroxane-pyridine complexes were synthesized with reference to J. Org. Chem. 2004, 69, 5087-5092.

| Target compound | 2,4,6-triarylboroxane-pyridine complex |
|---|---|
| Compound 2040 Compound 2042 | 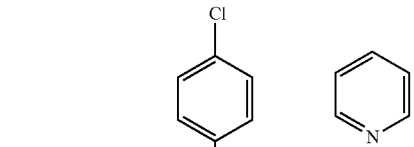 |
| Compound 2039 | 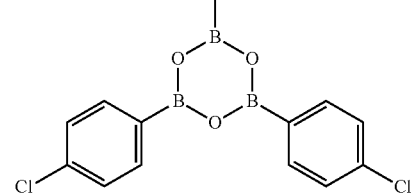 |
| Compound 2041 | 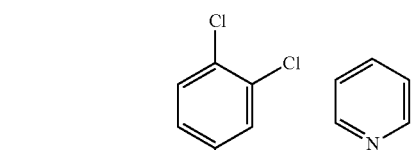 |
| Compound 2114 | 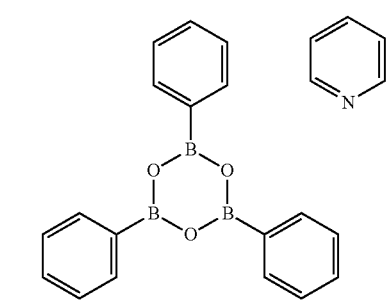 [SMILES: c1ccc(B2OB(c3ccccc3)OB(c3ccccc3)O2)cc1 ; c1ccncc1] |

Synthesis of Compound 2040 ((3S,9S,18S,21S,25S, 28S,34S),-3-[2-(4-chlorophenoxy)ethyl]-28-cyclohexyl-9-(cyclohexylmethyl)-7,10,13,16,21,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone)
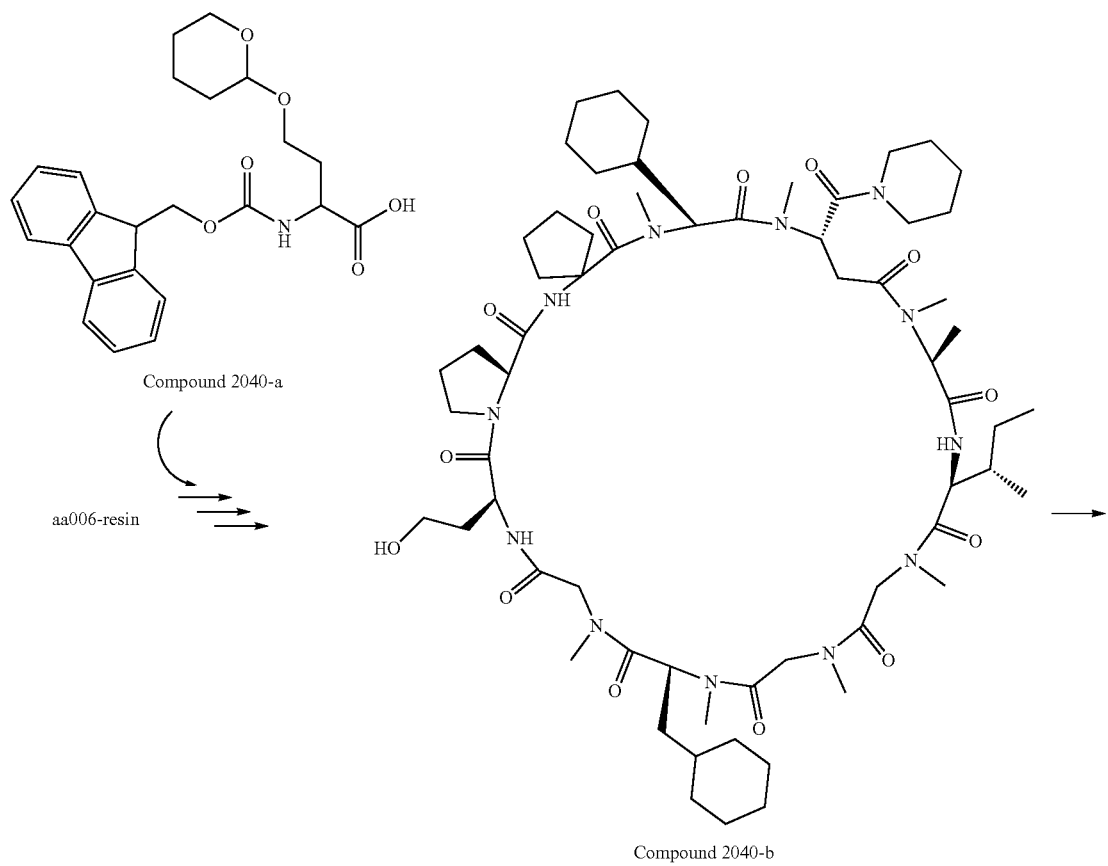

-continued

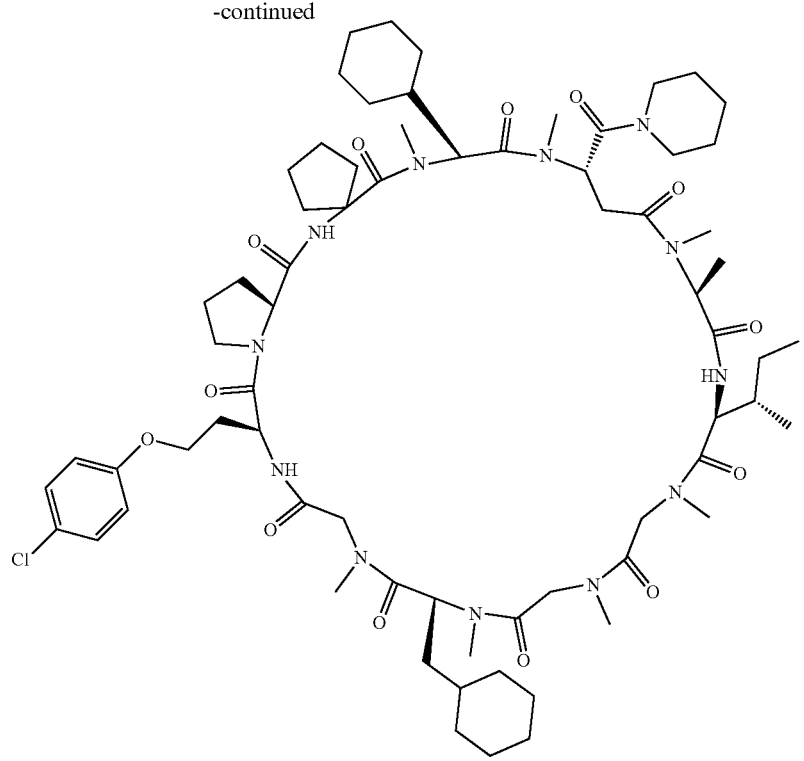

Compound 2040

To a mixture of 2-(9H-fluoren-9-ylmethoxycarbonylamino)-4-hydroxybutanoic acid (Fmoc-Hse-OH) (2.56 g, 7.5 mmol) in THE (15 mL) were added PPTS (94 mg, 0.375 mmol) and 3,4-dihydropyran (4.75 mL, 52.5 mmol), and the mixture was stirred at 50° C. for 16 hours. Ethyl acetate was added to the reaction solution, which was washed with brine three times. The organic layer was dried over anhydrous sodium sulfate, and the solvent was then evaporated under reduced pressure to give a mixture of Compound 2040-a with a compound having a carboxylic acid converted to THP. The resulting crude product was used for the next reaction without further purification.

The total amount of the crude product obtained above was dissolved in THE (30 mL), an aqueous disodium hydrogenphosphate solution (1 M, 30 mL) was added, and the mixture was stirred at 50° C. for four hours. The reaction solution was extracted with ethyl acetate, the organic layer was washed with brine and then dried over anhydrous sodium sulfate, and the solvent was evaporated under reduced pressure to give Compound 2040-a (3.6 g, quant.). The resulting crude product was used for the next reaction without further purification.

LCMS (ESI) m/z=448 (M+Na)+

Retention time: 0.82 min (analysis condition SQDFA05)

Compound 2040-b (410 mg) was obtained by peptide synthesis according to the basic peptide synthesis method described in the present Examples, using Compound aa006-resin ((3S)-3-[9H-fluoren-9-ylmethoxycarbonyl(methyl)amino]-4-oxo-4-piperidin-1-ylbutanoic acid-2-chlorotrityl resin, Fmoc-MeAsp(O-Trt(2-Cl)resin)-pip) (1.6 g) as a raw material and using the above-obtained Compound 2040-a as an Fmoc amino acid.

LCMS (ESI) m/z=1238.1 (M−H)−

Retention time: 0.81 min (analysis condition SQDFA05)

To a solution of Compound 2040-b (15 mg, 0.012 mmol) in 1,2-dichloroethane (225 µL, 0.05 mol/L) were added DIPEA (8 equivalents), copper(II) acetate (4 equivalents), 2,4,6-triarylboroxane-pyridine complex (1.7 equivalents), and molecular sieves 4A (3.3 w/w), and the mixture was then reacted at room temperature overnight under an oxygen atmosphere. The reaction solution was concentrated and then partially purified by reverse phase column chromatography (C18, methanol/10 mM aqueous ammonium acetate solution). The resulting residue was purified by preparative HPLC to give Compound 2040 ((3S,9S,18S,21S,25S,28S,34S)-3-[2-(4-chlorophenoxy)ethyl]-28-cyclohexyl-9-(cyclohexylmethyl)-7,10,13,16,21,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone) (3.3 mg, 22%). The LC/MS data are as described in Table 22.

Synthesis of Compound 2039 ((3S,9S,18S,21S,25S, 28S,34S)-28-cyclohexyl-9-(cyclohexylmethyl)-3-[2-(3,4-dichlorophenoxy)ethyl]-7,10,13,16,21,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone)

Synthesis of Compound 2041 ((3S,9S,18S,21S,25S, 28S,34S)-28-cyclohexyl-9-(cyclohexylmethyl)-7,10, 13,16,21,22,26,29-octamethyl-18-[(1S)-1-methylpropyl]-25-(piperidine-1-carbonyl)-3-[2-[4-(trifluoromethyl)phenoxy]ethyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone)

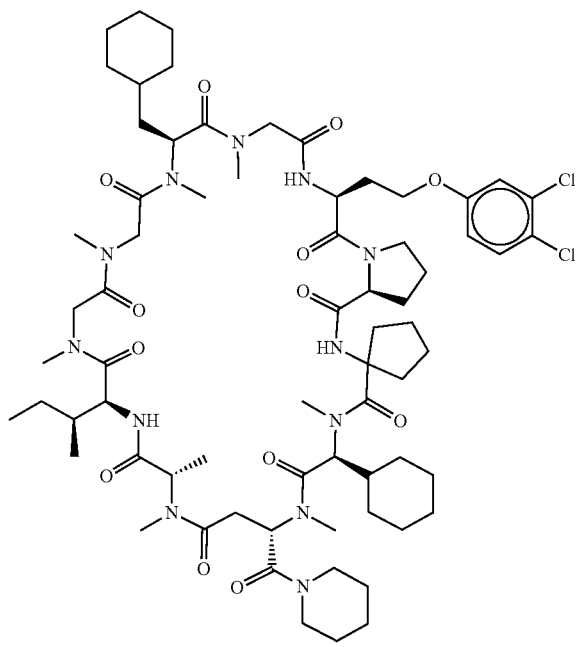

Compound 2039

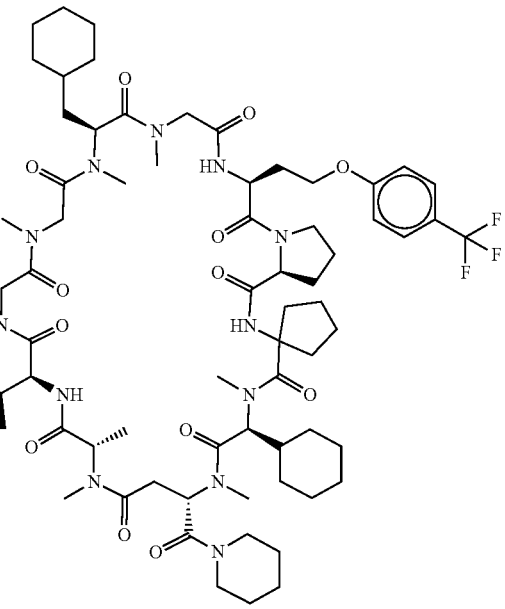

Compound 2041

Compound 2039 ((3S,9S,18S,21S,25S,28S,34S)-28-cyclohexyl-9-(cyclohexylmethyl)-3-[2-(3,4-dichlorophenoxy)ethyl]-7,10,13,16,21,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone) (1.3 mg, 7.5%) was obtained by the same method as in the synthesis of Compound 2040 using Compound 2040-b (15 mg, 0.012 mmol) as a raw material. The LC/MS data are as described in Table 22.

Compound 2041 ((3S,9S,18S,21S,25S,28S,34S)-28-cyclohexyl-9-(cyclohexylmethyl)-7,10,13,16,21,22,26,29-octamethyl-18-[(1S)-1-methylpropyl]-25-(piperidine-1-carbonyl)-3-[2-[4-(trifluoromethyl)phenoxy]ethyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone) (2.1 mg, 13%) was obtained by the same method as in the synthesis of Compound 2040 using Compound 2040-b (15 mg, 0.012 mmol) as a raw material. The LC/MS data are as described in Table 22.

Synthesis of Compound 2042 ((3S,9S,18S,21S,25S, 28S,34S)-3-[(4-chlorophenoxy)methyl]-28-cyclohexyl-9-(cyclohexylmethyl)-7,10,13,16,21,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone)
aa006-resin →→→ 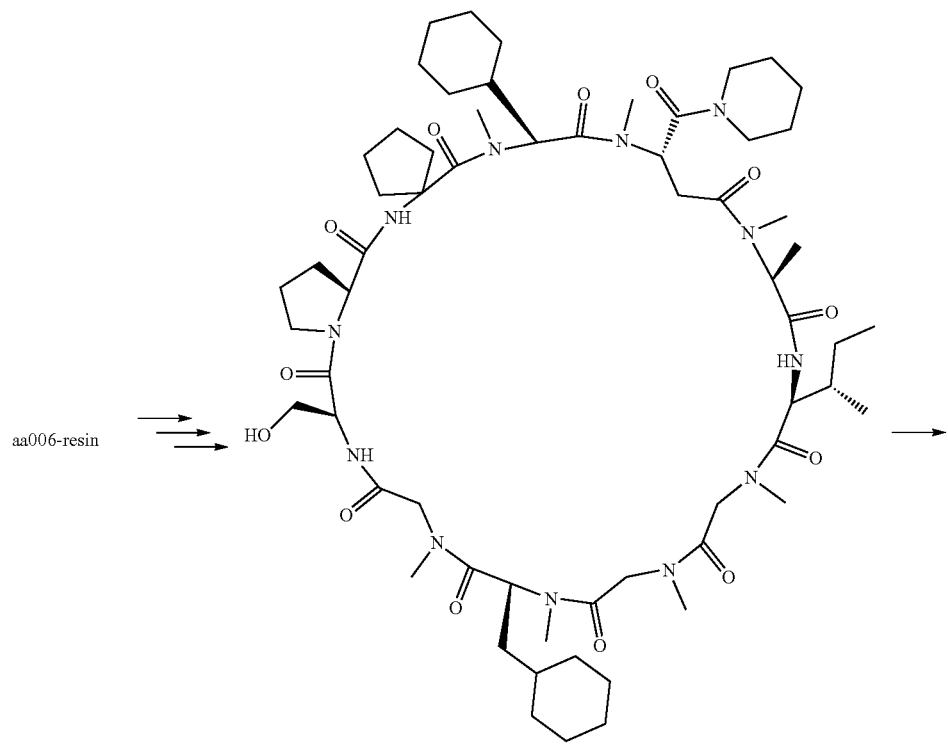 →
Compound 2042-a

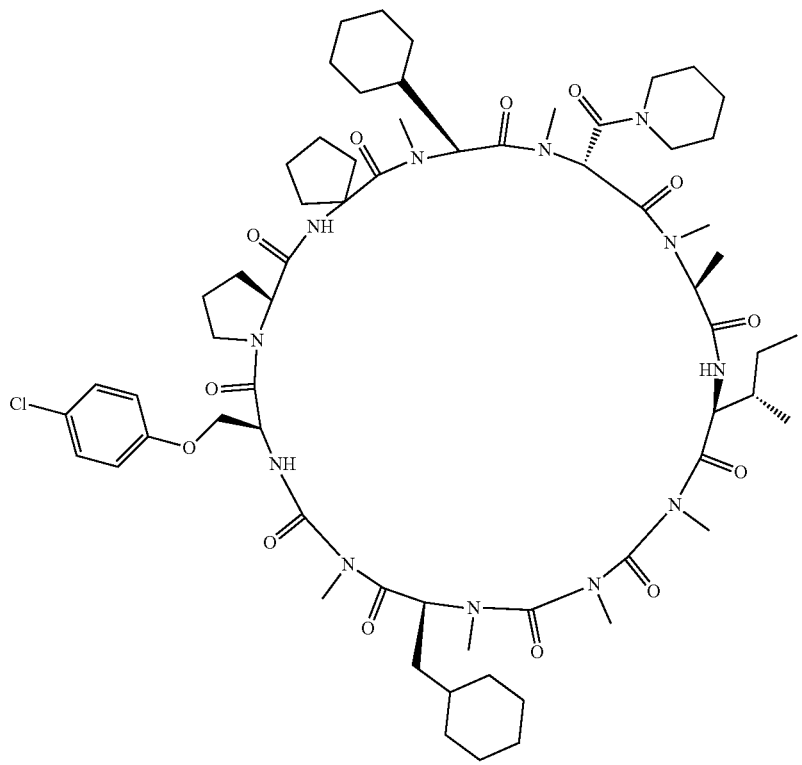

Compound 2042

Compound 2042-a (230 mg) was obtained by peptide synthesis according to the basic peptide synthesis method described in the present Examples, using Compound aa006-resin ((3S)-3-[9H-fluoren-9-ylmethoxycarbonyl(methyl)amino]-4-oxo-4-piperidin-1-ylbutanoic acid-2-chlorotrityl resin, Fmoc-MeAsp(O-Trt(2-Cl)resin)-pip) (1.6 g) as a raw material.

LCMS (ESI) m/z=1224.1 (M+H)+

Retention time: 0.82 min (analysis condition SQDFA05)

Compound 2042 ((3S,9S,18S,21S,25S,28S,34S)-3-[(4-chlorophenoxy)methyl]-28-cyclohexyl-9-(cyclohexylmethyl)-7,10,13,16,21,22,26,29-octamethyl-18-[(1S)-1-methylpropyl]-25-(piperidine-1-carbonyl)spiro[1,4,7,10,13,16,19,22,26,29,32-undecazabicyclo[32.3.0]heptatriacontane-31,1'-cyclopentane]-2,5,8,11,14,17,20,23,27,30,33-undecone) (2.56 mg, 16%) was obtained by the same method as in the synthesis of Compound 2040 using Compound 2042-a (15 mg, 12 μmol) as a raw material. The LC/MS data are as described in Table 22.

Synthesis of Compound 2114 ((6S,9S,13S,16S,22S, 25S,31S,34S)-25-[(3-iodophenyl)methyl]-9,16-diisobutyl-4,10,14,19,19,20,29,32-octamethyl-6-[(1S)-1-methylpropyl]-22-(phenoxymethyl)-13-(piperidine-1-carbonyl)-31-(p-tolylmethyl)-1,4,7,10,14,17,20,23,26,29,32-undecazabicyclo[32.2.0]hexatriacontane-2,5,8,11,15,18,21,24,27,30,33-undecone)

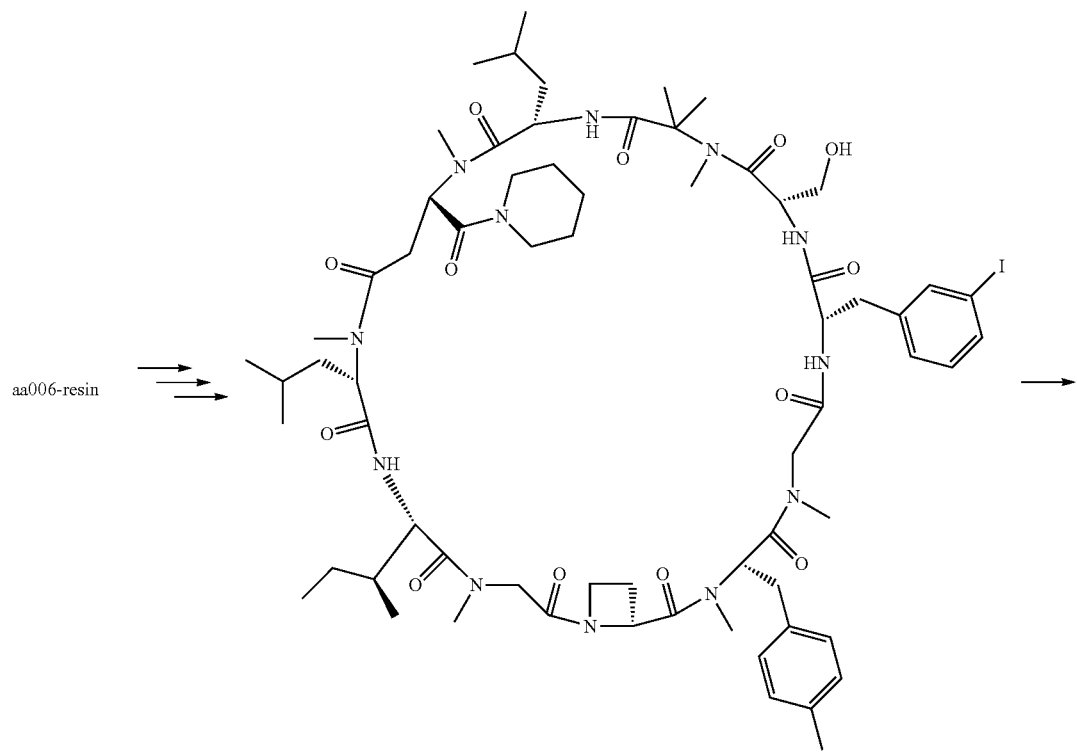

Compound 2114-a

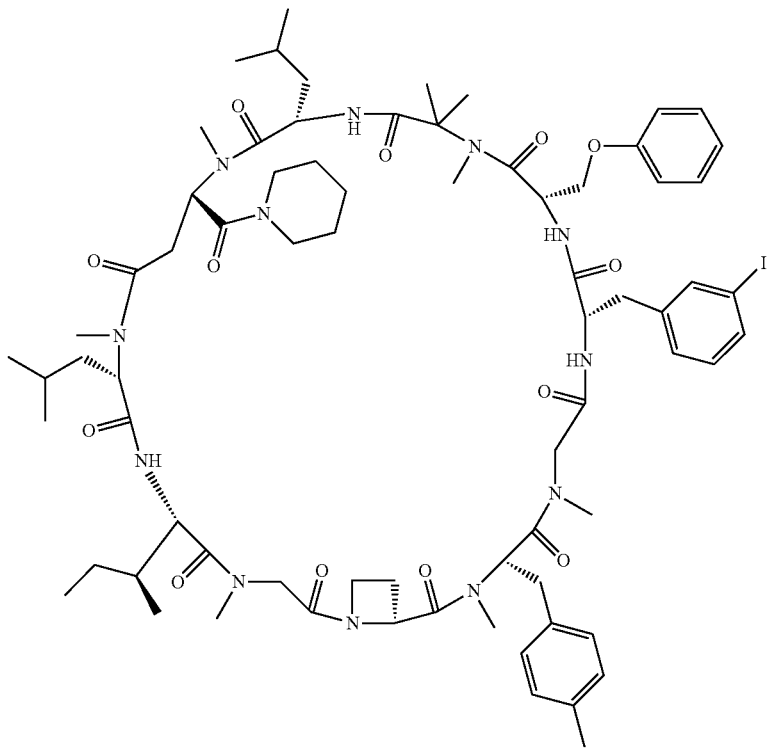

Compound 2114

Compound 2114-a (60 mg, 36%) was obtained by peptide synthesis according to the basic peptide synthesis method described in the present Examples, using Compound aa006-resin ((3S)-3-[9H-fluoren-9-ylmethoxycarbonyl(methyl)amino]-4-oxo-4-piperidin-1-ylbutanoic acid-2-chlorotrityl resin, Fmoc-MeAsp(O-Trt(2-Cl)resin)-pip) (0.4 g, 0.3 mmol/g, 0.12 mmol) as a raw material.

LCMS (ESI) m/z=1409.6 (M+H)+

Retention time: 0.92 min (analysis condition SQDFA05)

Compound 2114 ((6S,9S,13S,16S,22S,25S,31S,34S)-25-[(3-iodophenyl)methyl]-9,16-diisobutyl-4,10,14,19,19,20,29,32-octamethyl-6-[(1S)-1-methylpropyl]-22-(phenoxymethyl)-13-(piperidine-1-carbonyl)-31-(p-tolylmethyl)-1,4,7,10,14,17,20,23,26,29,32-undecazabicyclo[32.2.0]hexatriacontane-2,5,8,11,15,18,21,24,27,30,33-undecone) (1.53 mg, 29%) was obtained by the same method as in the synthesis of Compound 2040 using Compound 2114-a (5 mg, 3.55 μmol) as a raw material. The LC/MS data are as described in Table 22.

1-4-7. Peptide Synthesis Through N-Alkylation by Mitsunobu Reaction on Resins

Synthesis of Compound 2161 ((8S,11S,17S,26S, 29S,33S,36S)-8-[(2-chlorophenyl)methyl]-11-[2-[3-chloro-4-(trifluoromethyl)phenyl]ethyl]-17-(cyclohexylmethyl)-9-ethyl-36-isopropyl-15,18,21,24,29, 30,34,37-octamethyl-26-[(1S)-1-methylpropyl]-33-(piperidine-1-carbonyl)-6,9,12,15,18,21,24,27,30,34, 37-undecazaspiro[4.33]octatriacontane-7,10,13,16, 19,22,25,28,31,35,38-undecone)

Compound 2161 was synthesized according to the following route.

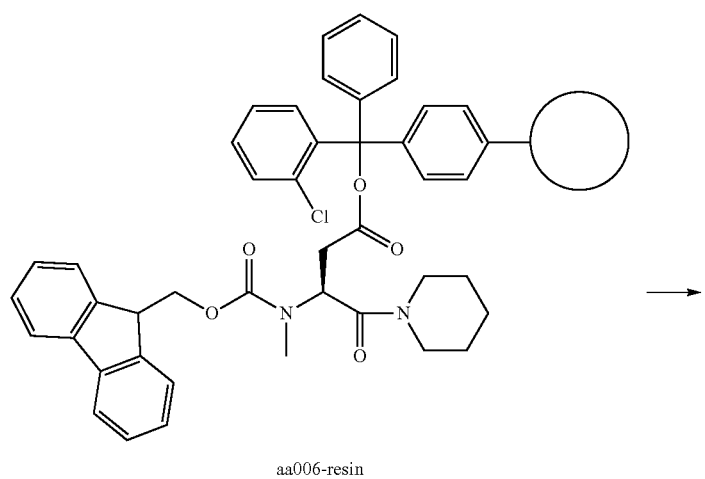

aa006-resin

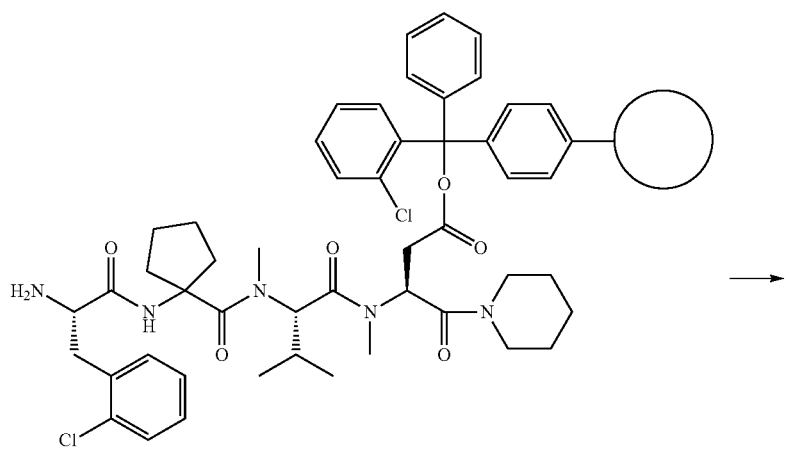

Compound 2161-a-resin

-continued
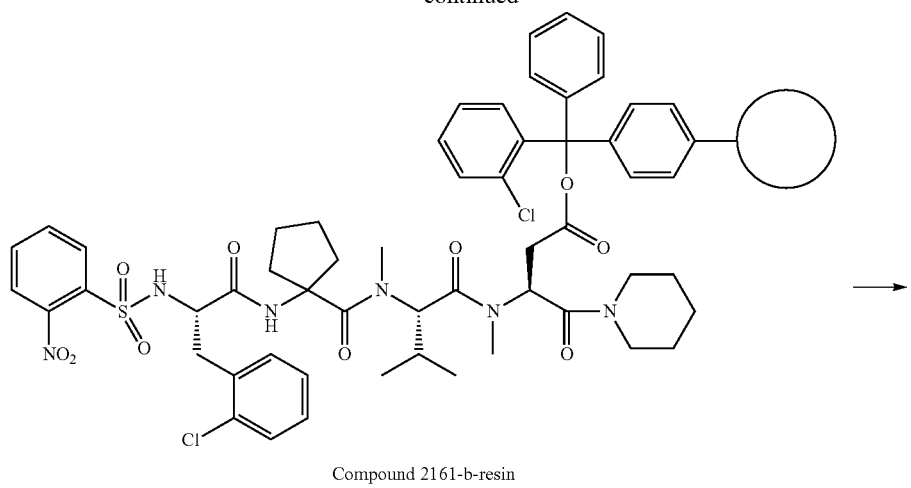
Compound 2161-b-resin
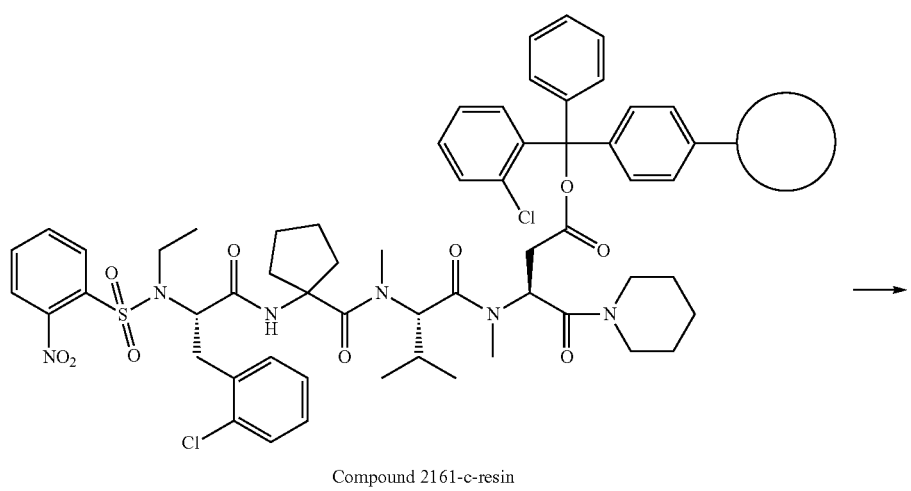
Compound 2161-c-resin
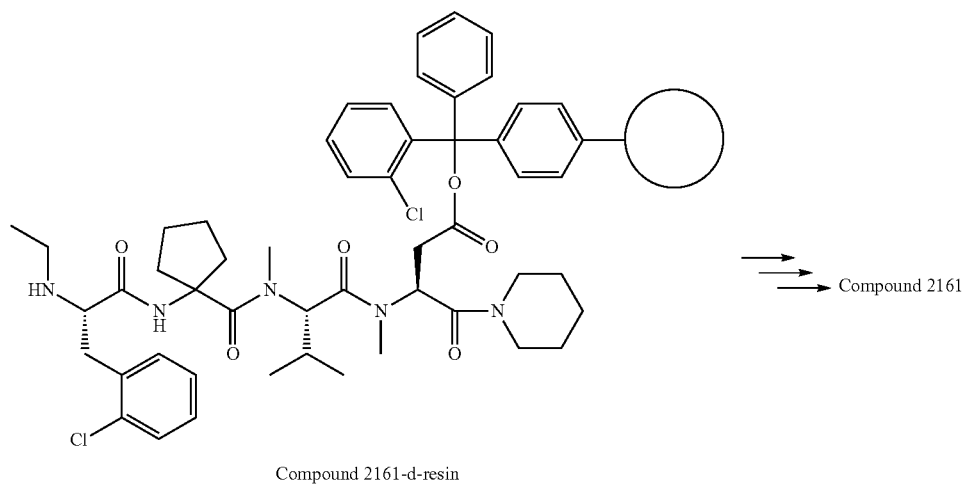
Compound 2161-d-resin
→→ Compound 2161

-continued

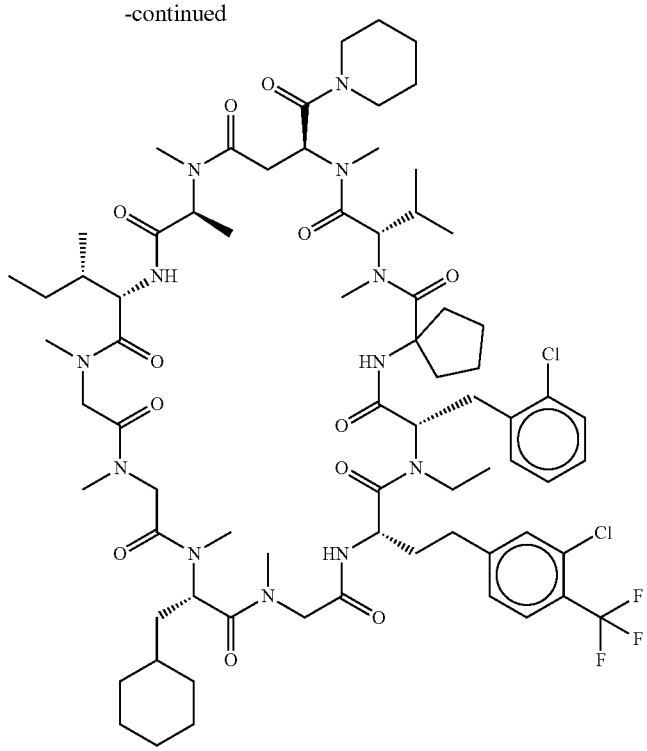

Compound 2161

Compound 2161-a-resin was obtained by peptide synthesis according to the basic peptide synthesis method described in the present Examples, using Compound aa006-resin ((3S)-3-[9H-fluoren-9-ylmethoxycarbonyl(methyl)amino]-4-oxo-4-piperidin-1-ylbutanoic acid-2-chlorotrityl resin, Fmoc-MeAsp(O-Trt(2-Cl)resin)-pip) (100 mg, 0.462 mmol/g, 0.0462 mmol) as a raw material.

To the above-obtained Compound 2161-a-resin were added a nosyl chloride/THF solution (0.2 mmol, 0.35 mL) and a collidine/THF solution (0.5 mmol, 0.35 mL), and the mixture was shaken at 40° C. for two hours. Thereafter, the resin was washed with THF (0.7 mL) four times and then washed with DCM (0.7 mL) four times to give Compound 2161-b-resin. The obtained resin was partially cleaved with TFE/DCM (1/1) and analyzed by LC/MS to confirm the progress of the reaction.

LCMS (ESI) m/z=805 (M+H)+

Retention time: 0.79 min (analysis condition SQDFA05)

The above-obtained Compound 2161-b-resin was swollen with DCM (1.0 mL) and washed with THF (0.7 mL) four times, after which a triphenylphosphine/THF solution (66.0 mg/0.7 mL, 0.25 mmol), ethanol (0.024 mL, 0.41 mmol), and diisopropyl azodicarboxylate (DIAD) (0.05 mL, 0.26 mmol) were added and the mixture was shaken at 40° C. for 30 minutes. Thereafter, the resin was washed with THF (0.7 mL) four times and then washed with DCM (0.7 mL) four times to give Compound 2161-c-resin. The obtained resin was partially cleaved with TFE/DCM (1/1) and analyzed by LC/MS to confirm the progress of the reaction.

LCMS (ESI) m/z=833 (M+H)+

Retention time: 0.88 min (analysis condition SQDFA05)

The above-obtained Compound 2161-c-resin was swollen with DCM (1.0 mL) and washed with NMP (0.7 mL) four times, after which a DBU/NMP solution (36 µL/314 µL) and a 1-dodecanethiol/NMP solution (89 µL/261 µL) were added and the mixture was shaken at 40° C. for one hour. Thereafter, the resin was washed with NMP (0.7 mL) four times and then washed with DCM (0.7 mL) four times to give Compound 2161-d-resin. The obtained resin was partially cleaved with TFE/DCM (1/1) and analyzed by LC/MS to confirm the progress of the reaction.

LCMS (ESI) m/z=648 (M+H)+

Retention time: 0.51 min (analysis condition SQDFA05)

Peptide chain elongation and cyclic peptide synthesis were conducted according to the basic route using the above-obtained Compound 2161-d-resin to give Compound 2161 ((8S,11S,17S,26S,29S,33S,36S)-8-[(2-chlorophenyl)methyl]-11-[2-[3-chloro-4-(trifluoromethyl)phenyl]ethyl]-17-(cyclohexylmethyl)-9-ethyl-36-isopropyl-15,18,21,24,29,30,34,37-octamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone) (5.5 mg, 8%). The LC/MS data are as described in Table 22.

Synthesis of Compounds 2162-2167

Compounds 2162-2167 were synthesized in the same manner as in the synthesis of Compound 2161. The LC/MS data are as described in Table 22.

Synthesis of Compounds 2168-2171

Compounds 2168-2171 were synthesized according to the basic scheme provided below in the same manner as in the synthesis of Compound 2161 using methanol (0.019 mL, 0.47 mmol) instead of ethanol in Mitsunobu reaction.

789
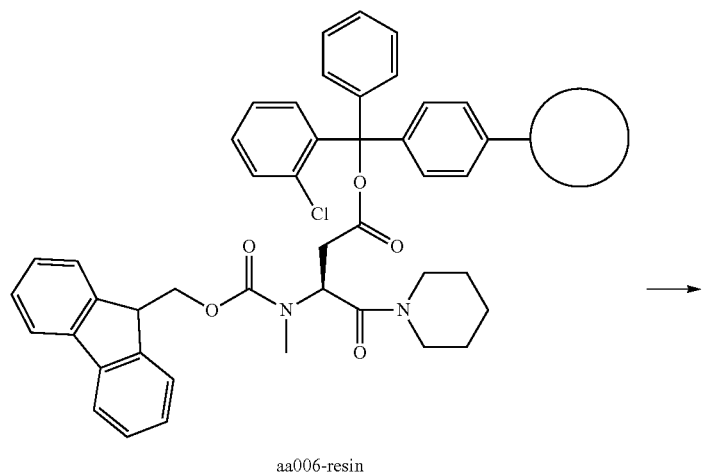
aa006-resin
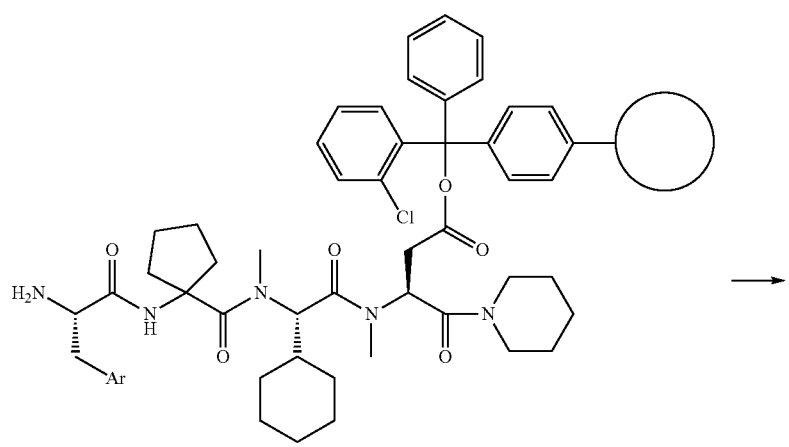
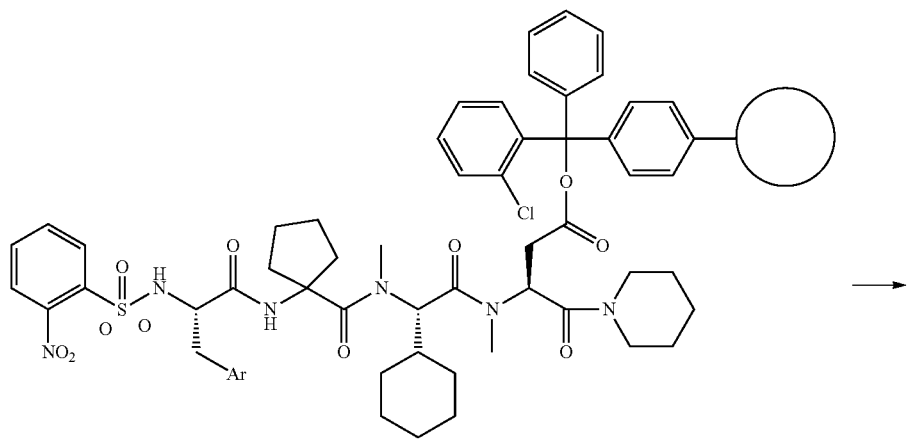
790

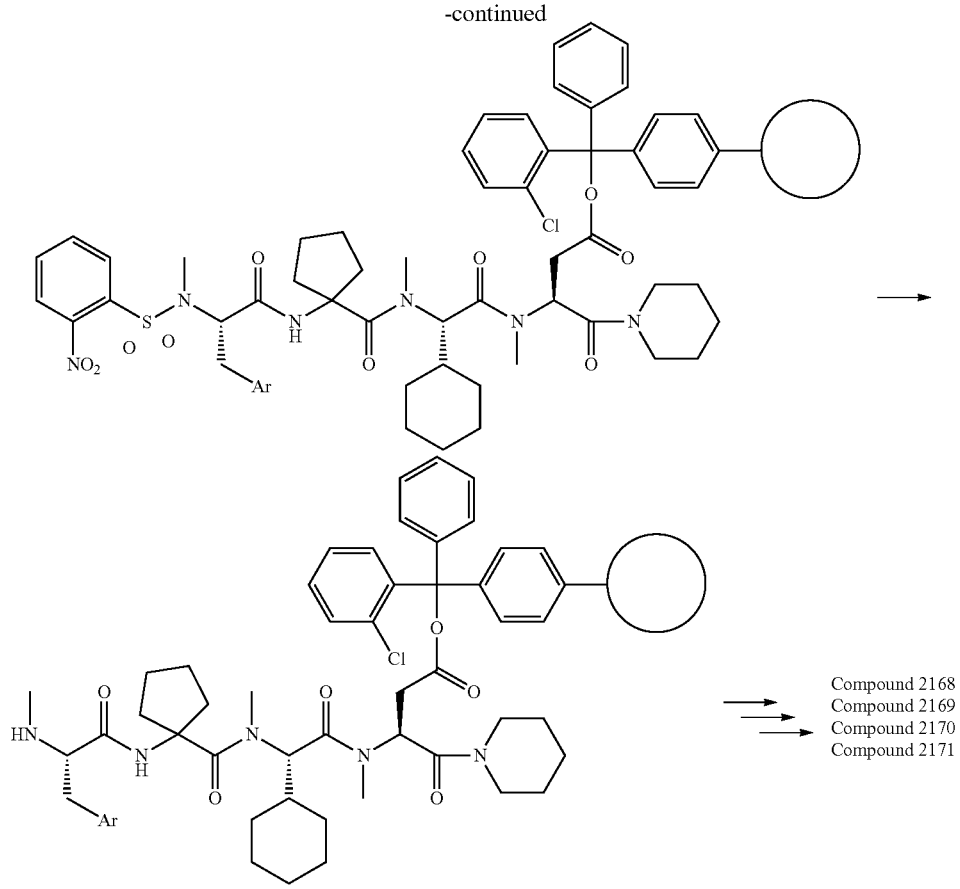
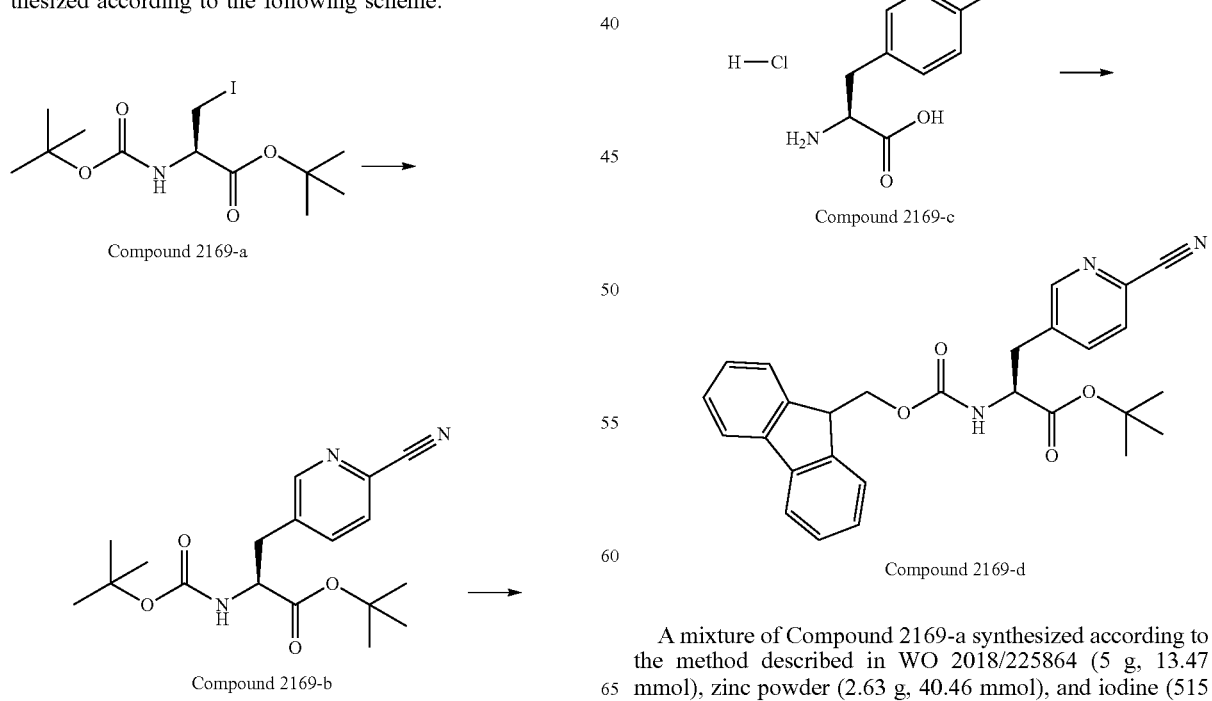
The Fmoc amino acid having a pyridine ring on the side chain, as used for synthesizing Compound 2169, was synthesized according to the following scheme.
A mixture of Compound 2169-a synthesized according to the method described in WO 2018/225864 (5 g, 13.47 mmol), zinc powder (2.63 g, 40.46 mmol), and iodine (515 mg, 2.03 mmol) in DMF (15 mL) was stirred at room temperature for two hours under a nitrogen atmosphere. To the solution were added 5-bromopyridine-2-carbonitrile (3.19 g, 17.43 mmol), tris(dibenzylideneacetone)(chloroform)dipalladium (0), (350 mg, 0.34 mmol), and 2-dicyclohexylphosphino-2',4',6'-triisopropylbiphenyl (Xphos) (321 mg, 0.67 mmol) were added, and the mixture was stirred at 50° C. for three hours. The reaction solution was purified by silica gel column chromatography (ethyl acetate/petroleum ether) to give Compound 2169-b (2.5 g, 53%). This was mixed with another lot synthesized in the same manner and was used for the next reaction.

LCMS (ESI) m/z=348 (M+H)+

Retention time: 1.508 min (analysis condition SMD-method23)

A solution of Compound 2169-b (12 g, 34.54 mmol) in dichloromethane (100 mL) was stirred at 25° C. for two hours while bubbling with hydrochloric acid gas. The precipitated solid was collected by filtration to give Compound 2169-c as a crude product (7.83 g, 100%). This was used for the next reaction without further purification.

To a solution of Compound 2169-c (2.4 g, 10.54 mmol) and potassium carbonate (3.77 g, 27.28 mmol) in water (34 mL) was added a solution of Fmoc-OSu (3.06 g, 10.54 mmol) in 1,4-dioxane (34 mL), and the mixture was stirred at 0° C. for one hour. The reaction solution was diluted with water and washed with diethyl ether three times. The resulting aqueous layer was adjusted to a pH range of 5 to 6 and extracted with ethyl acetate. The organic layer was dried over anhydrous sodium sulfate, and the solvent was then evaporated under reduced pressure. The resulting residue was purified by silica gel column chromatography (dichloromethane/methanol) to give Compound 2169-d (1 g, 23%).

LCMS (ESI) m/z=414.2 (M+H)+

Retention time: 2.737 min (analysis condition SMD-method_22)

Compound 2170 was synthesized using, as an Fmoc amino acid, 9H-fluoren-9-ylmethoxycarbonylamino-3-[3-fluoro-4-[(2-methylpropan-2-yl)oxy]phenyl]propanoic acid (Fmoc-Tyr(3-F, tBu)-OH) synthesized as described in WO 2018/225864. The phenol tBu group was deprotected by adding 2 mL of a 0.1 M tetramethylammonium bisulfate/1,1,1,3,3,3-hexafluoroisopropyl alcohol (HFIP) solution containing 2% triisopropylsilane (TIPS) to the residue after cyclization reaction, and allowing to stand at room temperature for 24 hours.

1-4-8. Peptide Synthesis Through Amination on Resins

Synthesis of Compound 2035 ((11S,17S,26S,29S,33S,36S)-11-[2-[3-chloro-4-(trifluoromethyl)phenyl]ethyl]-36-cyclohexyl-17-(cyclohexylmethyl)-9-(2,2-difluorospiro[3.3]heptan-6-yl)-29-isobutyl-15,18,21,24,30,34,37-heptamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone)

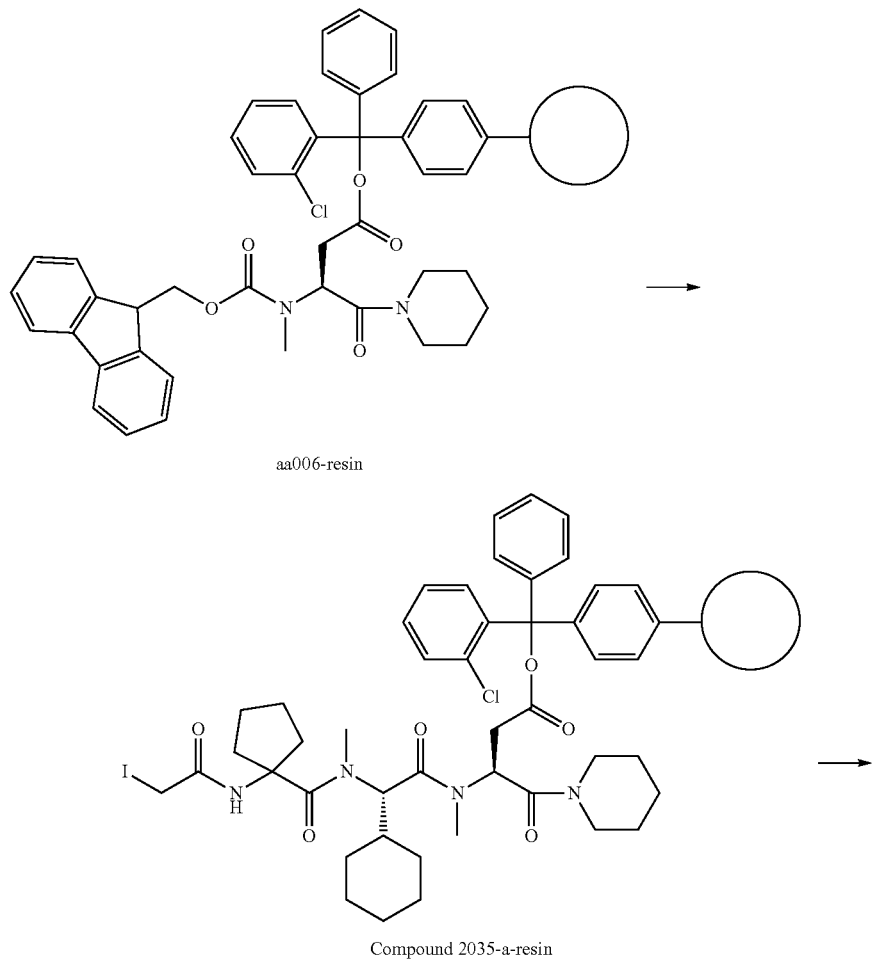

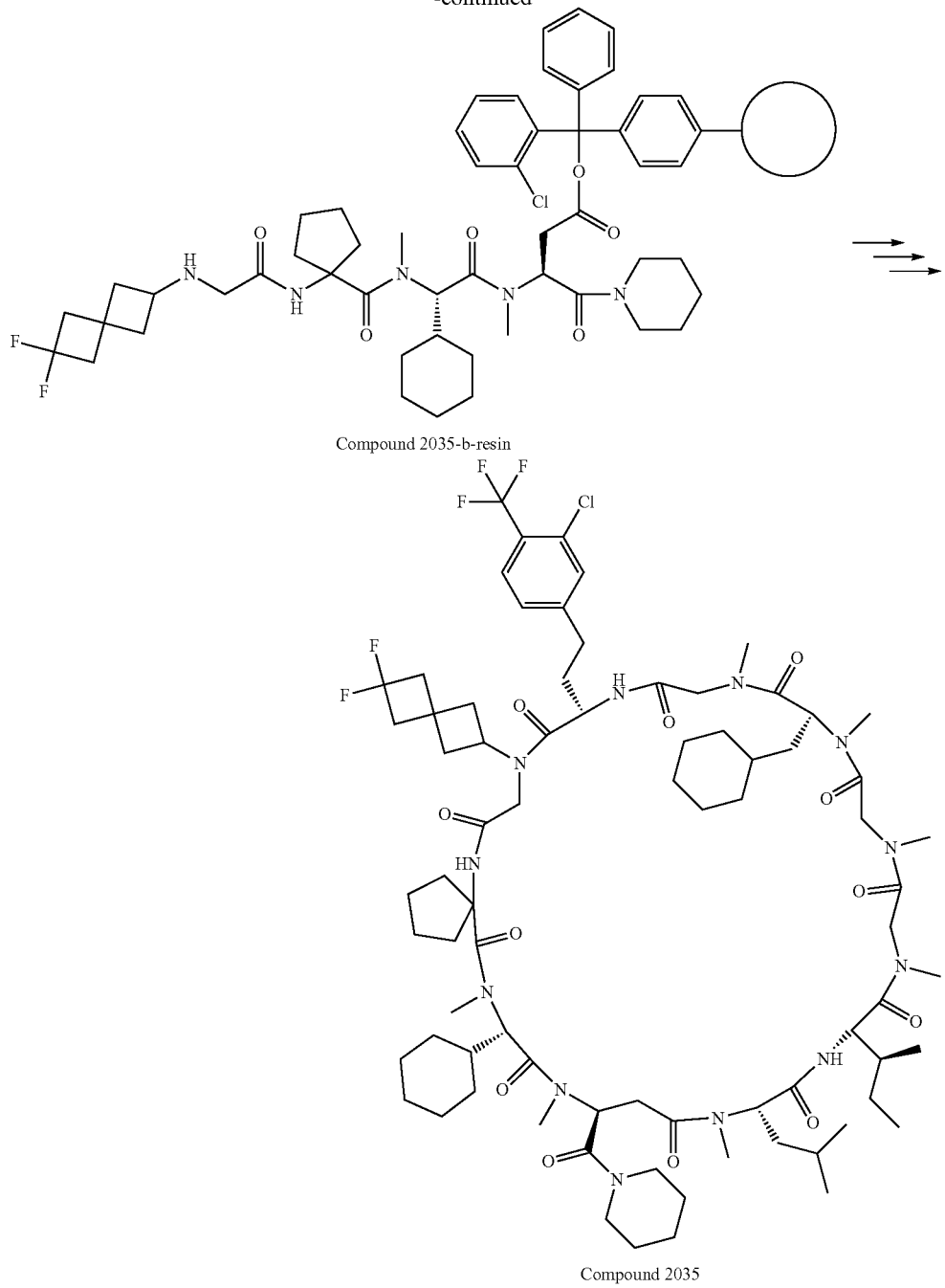

Compound 2035-b-resin

Compound 2035

Fmoc-MeChg-OH and then Fmoc-cLeu-OH were elongated and the Fmoc group was deprotected by peptide synthesis according to the basic peptide synthesis method described in the present Examples, using Compound aa006-resin ((3S)-3-[9H-fluoren-9-ylmethoxycarbonyl(methyl)amino]-4-oxo-4-piperidin-1-ylbutanoic acid-2-chlorotrityl resin, Fmoc-MeAsp(O-Trt(2-Cl)resin)-pip) (100 mg, 0.437 mmol/g, 0.0437 mmol) as a raw material, after which Compound 2035-a-resin with the peptide N-terminus iodinated on the resin was obtained using a mixture composed of a solution of iodoacetic acid (0.6 mol/L, 0.3 mL) in NMP/DMF (1/1) and a solution of diisopropylcarbodiimide (DIC) in N,N-dimethylformamide (DMF) (10% v/v, 0.36 mL). Further, this was reacted with 6,6-difluorospiro[3.3]heptan-2-amine hydrochloride in the presence of DIPEA to give Compound 2035-b-resin. Subsequent peptide chain elongation and cyclic peptide synthesis were conducted according to the basic route to give Compound 2035 ((11S,17S,26S,29S,33S,36S)-11-[2-[3-chloro-4-(trifluoromethyl)phenyl]ethyl]-36-cyclohexyl-17-(cyclohexylmethyl)-9-(2,2-difluorospiro[3.3]heptan-6-yl)-29-isobutyl-15,18,21,24,30,34,37-heptamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone) (4.12 mg, 6%). The LC/MS data are as described in Table 22.

Synthesis of Compounds 2031, 2030, 2022, 2021, 2036, 2025, 2024, 2029, 2032, 2033, 2026, 2023, 2028, 2027, and 2034

Tripeptide-loaded resins were synthesized by the same method as in the synthesis of Compound 2035, iodoacetic acids were then condensed and aminated, and peptide chain elongation and cyclic peptide synthesis were further conducted according to the basic route to synthesize Compounds 2031, 2030, 2022, 2021, 2036, 2025, 2024, 2029, 2032, 2033, 2026, 2023, 2028, 2027, and 2034. The following table describes target compound peptides, amines used for reactions, and yield amounts (mg) of the target compounds. The LC/MS data are as described in Table 22.

TABLE 19

| Peptide | Amine | Yield mg |
| --- | --- | --- |
| Compound 2031 | 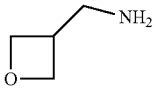 | 5.09 |
| Compound 2030 | 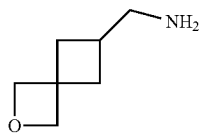 | 2.76 |
| Compound 2022 | 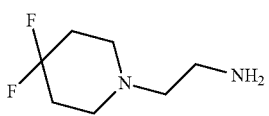 | 10.32 |
| Compound 2021 | 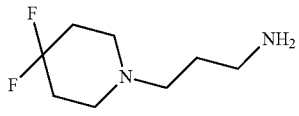 [SMILES: NCCCN1CCC(F)(F)CC1] | 8.99 |
| Compound 2036 | 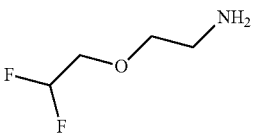 | 5.06 |
| Compound 2025 | 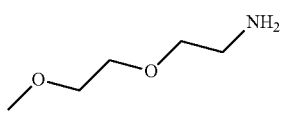 | 8.11 |
| Compound 2024 | 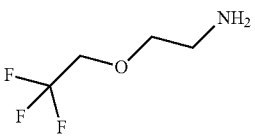 | 2.99 |
| Compound 2029 | 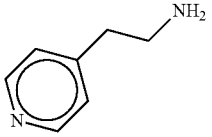 | 18.06 |
| Compound 2032 | 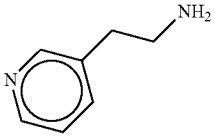 | 16.68 |
| Compound 2033 | 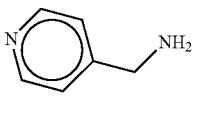 | 9.24 |
| Compound 2026 | 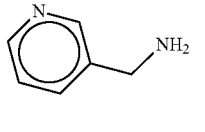 | 14.51 |
| Compound 2023 | 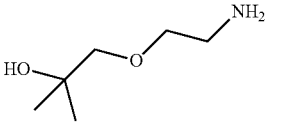 | 3.39 |
| Compound 2028 | 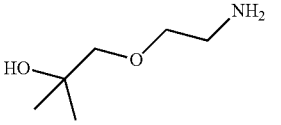 | 4.78 |
| Compound 2027 | 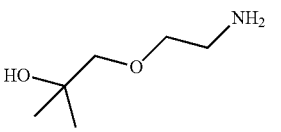 | 5.34 |
| Compound 2034 | 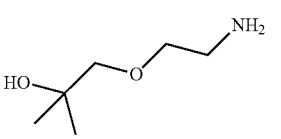 | 4.99 |

Synthesis of Compound 2037 (((11S,17S,26S,29S, 33S,36S)-11-[2-[3-chloro-4-(trifluoromethyl)phenyl] ethyl]-36-cyclohexyl-17-(cyclohexylmethyl)-9-(2-hydroxyethyl)-29-isobutyl-15,18,21,24,30,34,37-heptamethyl-26-[(1S)-1-methylpropyl]-33-(piperidine-1-carbonyl)-6,9,12,15,18,21,24,27,30,34, 37-undecazaspiro[4.33]octatriacontane-7,10,13,16, 19,22,25,28,31,35,38-undecone) and Compound 2038 (2-[2-[(11S,17S,26S,29S,33S,36S)-11-[2-[3-chloro-4-(trifluoromethyl)phenyl]ethyl]-36-cyclohexyl-17-(cyclohexylmethyl)-29-isobutyl-15,18,21, 24,30,34,37-heptamethyl-26-[(1S)-1-methylpropyl]-7,10,13,16,19,22,25,28,31,35,38-undecaoxo-33-(piperidine-1-carbonyl)-6,9,12,15,18,21,24,27,30,34, 37-undecazaspiro[4.33]octatriacontan-9-yl]ethoxy]-N,N-dimethyl-acetamide)

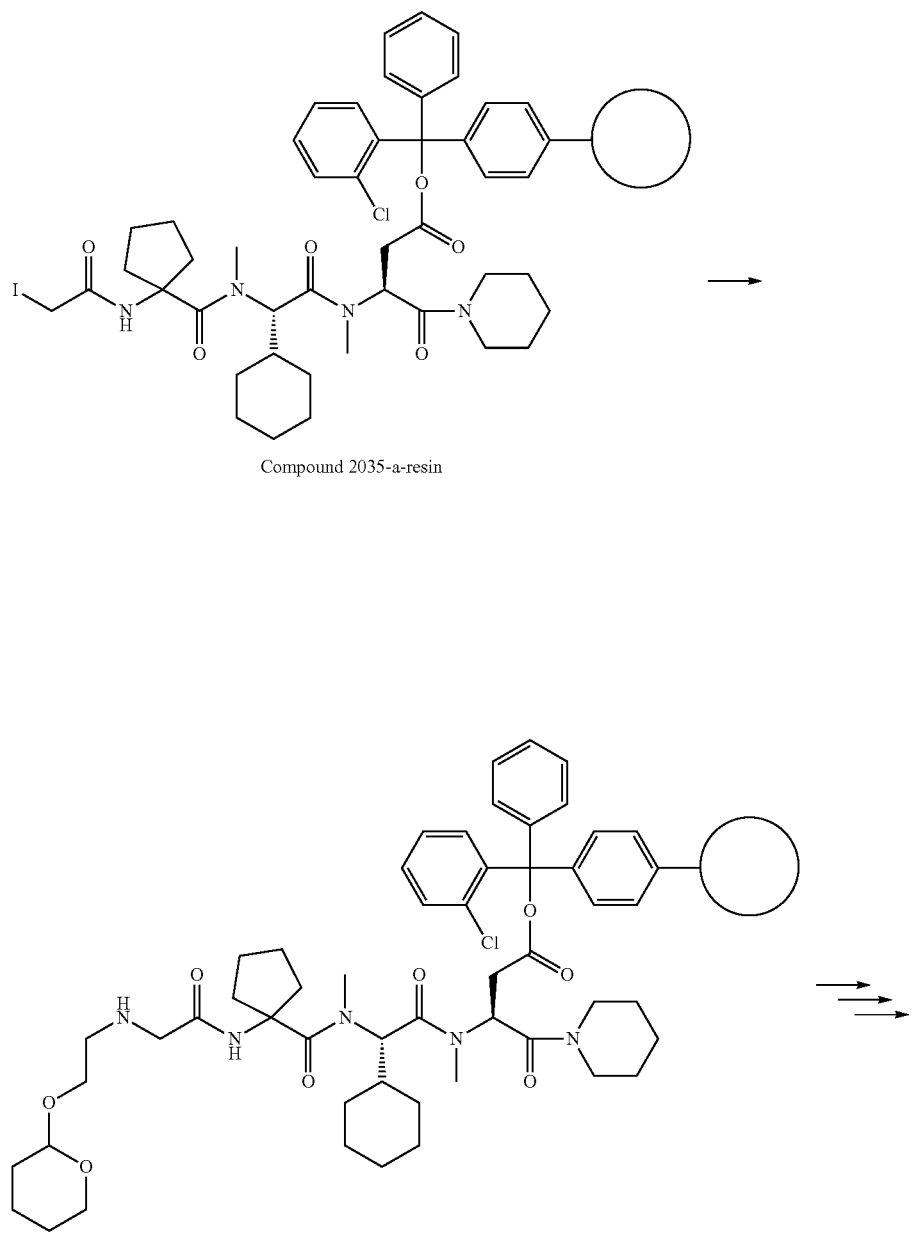

Compound 2035-a-resin

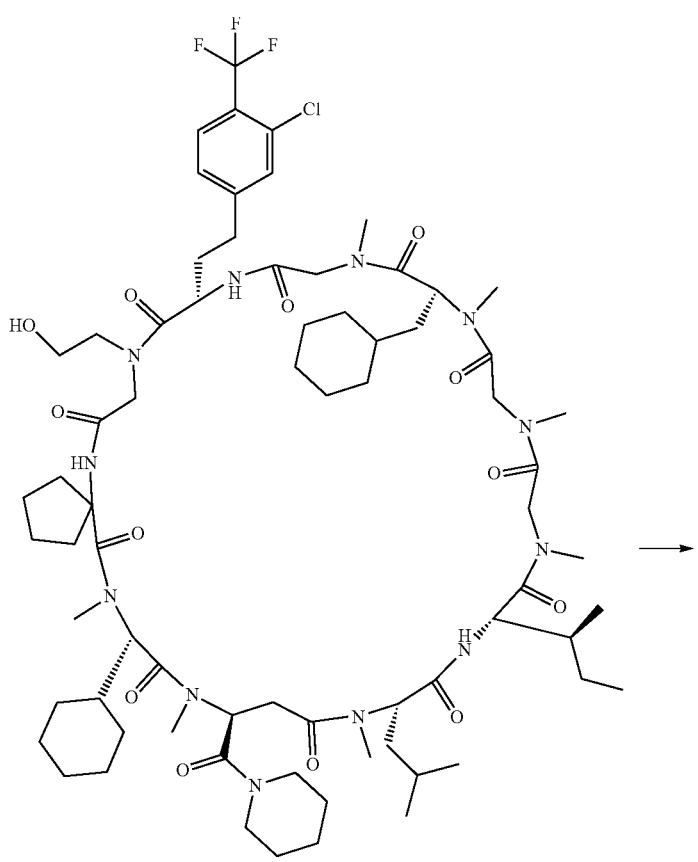
Compound 2037

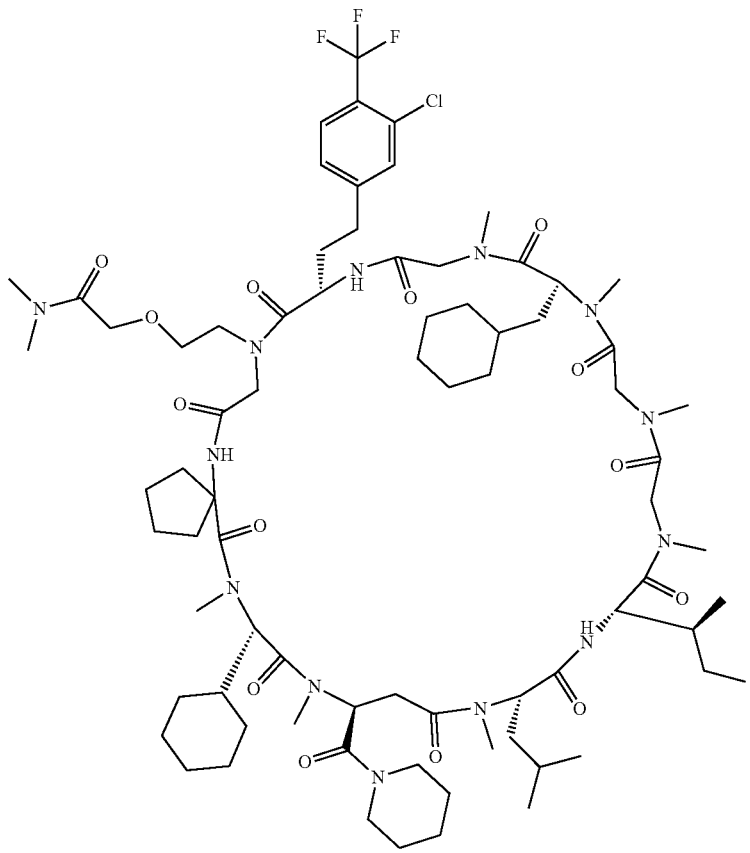

Compound 2038

Compound 2037 ((11S,17S,26S,29S,33S,36S)-11-[2-[3-chloro-4-(trifluoromethyl)phenyl]ethyl]-36-cyclohexyl-17-(cyclohexylmethyl)-9-(2-hydroxyethyl)-29-isobutyl-15,18,21,24,30,34,37-heptamethyl-26-[1(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone) was obtained by the same method as in the synthesis of Compound 2035 using Compound 2035-a-resin and using 2-(2-aminoethoxy)oxane as an amine, and by conducting peptide chain elongation, and cyclic peptide synthesis including THP deprotection, according to the basic route. The LC/MS data are described in Table 22.

Compound 2038 (2-[2-[(11S,17S,26S,29S,33S,36S)-11-[2-[3-chloro-4-(Trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-7,10,13,16,19,22,25,28,31,35,38-undecaoxo-33-(piperidine-1-carbonyl)-6,9,12,15,18,21,24,27,30,34,37-undecazaspiro[4.33]octatriacontan-9-yl]ethoxy]-N,N-dimethylacetamide) (4.7 mg, 89%) was obtained by the same method as in the synthesis of Compound 2116 using Compound 2037 (5 mg, 3.46 µmol), silver oxide (24.0 mg, 0.104 mmol), and 2-bromo-N,N-dimethylacetamide (17.2 mg, 0.104 mmol). The LC/MS data are described in Table 22.

1-4-9. Peptide Modification by Amidation of Carboxylic Acids
Synthesis of Compound 2108 (3-[(3S,6S,9S,13S,16S,22S,25S,31S,34S)-25-[2-[3-chloro-4-(trifluoromethyl)phenyl]ethyl]-31-(cyclohexylmethyl)-16-cyclopentyl-9-isobutyl-3,4,10,14,17,23,29,32-octamethyl-6-[(1S)-1-methylpropyl]-13-(morpholine-4-carbonyl)-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-22-yl]-N,N-dimethyl-propanamide)
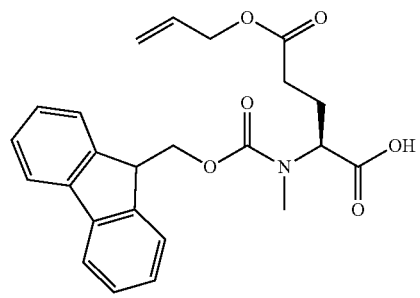
Compound 2108-a
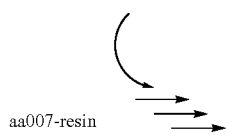
aa007-resin
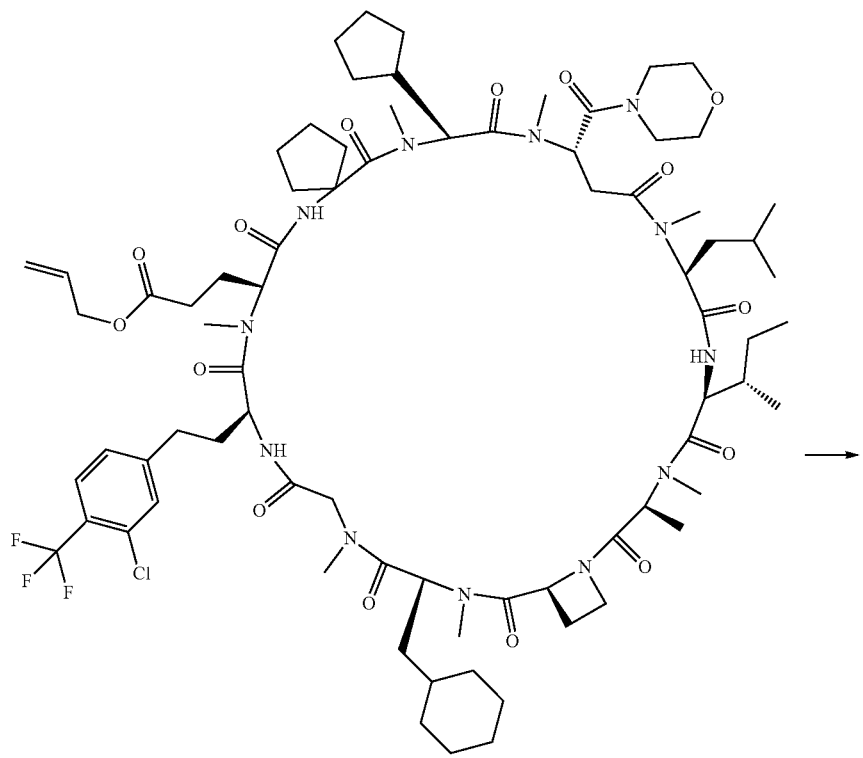
Compound 2108-b

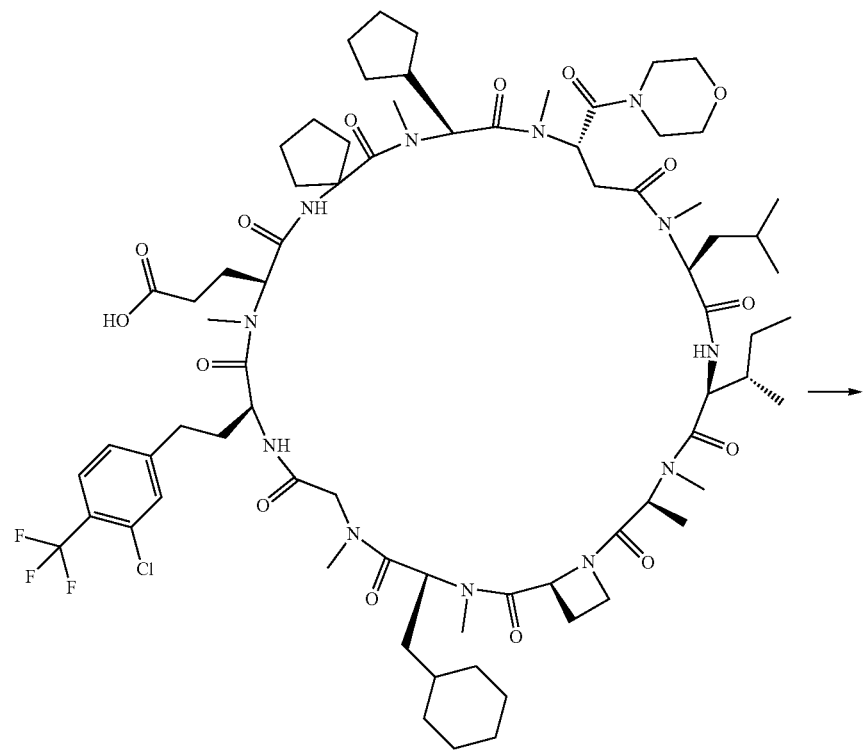
Compound 2108-c

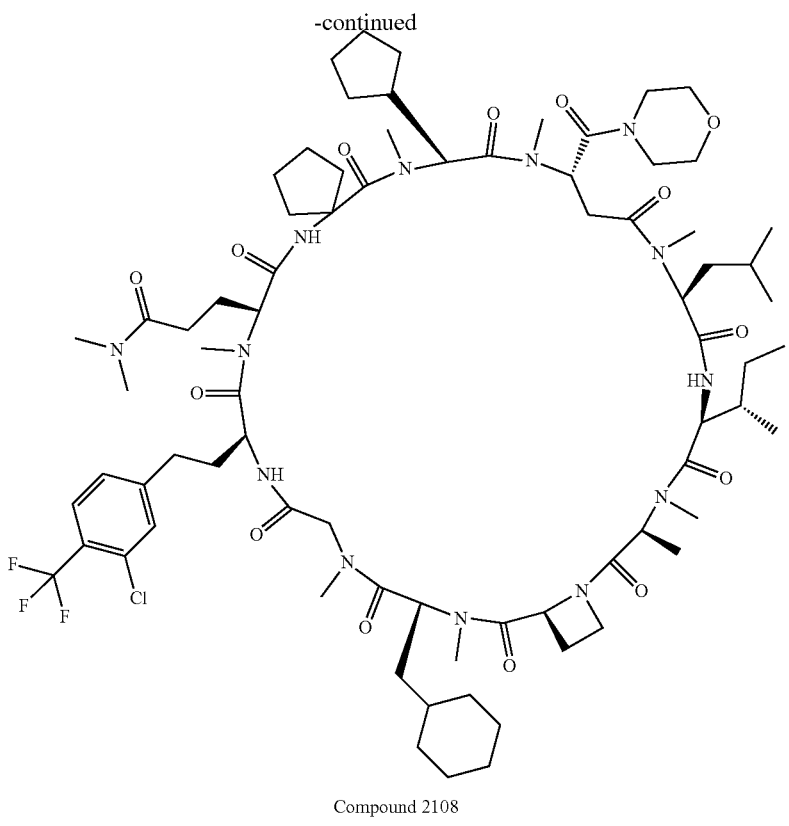

Compound 2108

Compound 2108-a ((2S)-2-[9H-fluoren-9-ylmethoxycarbonyl(methyl)amino]-5-oxo-5-prop-2-enoxypentanoic acid) was obtained as a crude product (2.179 g, 96%) by the same method as in the synthesis of Compound aa078-b using (2S)-2-(9H-fluoren-9-ylmethoxycarbonylamino)-5-oxo-5-prop-2-enoxypentanoic acid (Fmoc-Glu(OAl)—OH) (2.197 g, 5.37 mmol) as a starting material.

LCMS (ESI) m/z=424 (M+H)+

Retention time: 0.84 min (analysis condition SQDFA05)

Compound 2108-b was obtained as a crude product by peptide synthesis according to the basic peptide synthesis method described in the present Examples, using Compound aa007-resin ((3S)-3-[9H-fluoren-9-ylmethoxycarbonyl(methyl)amino]-4-morpholin-4-yl-4-oxobutanoic acid-2-chlorotrityl resin, Fmoc-MeAsp(O-Trt(2-Cl)resin)-mor) (0.424 mmol/g, 600 mg, 0.254 mmol) as a starting material and using Compound 2108-a ((2S)-2-[9H-fluoren-9-ylmethoxycarbonyl(methyl)amino]-5-oxo-5-prop-2-enoxypentanoic acid) as a reagent.

The total amount of Compound 2108-b obtained above (0.254 mmol) was dissolved in dichloromethane (2.5 mL), tetrakistriphenylphosphinepalladium (14.7 mg, 0.05 equiv.) and phenylsilane (22 μL, 0.7 equiv.) were added, and the mixture was stirred at room temperature for 75 minutes. Tetrakistriphenylphosphinepalladium (14.7 mg, 0.05 equiv.) and phenylsilane (22 μL, 0.7 equiv.) were added to the reaction solution, and the mixture was stirred for 90 minutes to give a reaction solution containing Compound 2108-c. A solution of HATU (193 mg, 2 equiv.) in dimethylformamide (2.5 mL), and diisopropylethylamine (0.11 mL, 2.4 equiv.) were added thereto, and the mixture was stirred for 15 minutes. This reaction solution (Reaction Solution A) was divided into six portions, one of which was used for the subsequent reaction.

Dimethylamine (0.11 mL, 5 equiv., 2.0 M tetrahydrofuran solution) was added to Reaction Solution A (0.0424 mmol), and the mixture was stirred at room temperature for 30 minutes. The reaction solution was concentrated under reduced pressure, and the resulting residue was purified by preparative HPLC to give Compound 2108 (3-[(3S,6S,9S,13S,16S,22S,25S,31S,34S)-25-[2-[3-chloro-4-(trifluoromethyl)phenyl]ethyl]-31-(cyclohexylmethyl)-16-cyclopentyl-9-isobutyl-3,4,10,14,17,23,29,32-octamethyl-6-[(1S)-1-methylpropyl]-13-(morpholine-4-carbonyl)-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-22-yl]-N,N-dimethyl-propanamide) (3.6 mg, 5.6%). The LC/MS data are described in Table 22.

Synthesis of Compounds 2098, 2103, 2112, 2104, and 2107

Compound 2098, 2103, 2112, 2104, or 2107 was obtained by adding an amine (5 equiv. relative to the peptide) shown in the following table instead of dimethylamine to one of the six divided portions of Reaction Solution A as obtained in the synthesis of Compound 2108, by the same method as in the synthesis of Compound 2108. The following table describes target compound peptides, amines used for reactions, and yield amounts (mg) and yield percentages (%) of the target compounds. The LC/MS data are described in Table 22.

TABLE 20

| Peptide | Amine | Yield mg | Yield % |
|---|---|---|---|
| Compound 2098 | 3,3-difluoroazetidine-hydrochloride | 2.7 | 4 |
| Compound 2103 | azetidine | 3.6 | 5.5 |
| Compound 2112 | piperidine | 3.8 | 5.7 |
| Compound 2104 | pyrrolidine | 2.5 | 3.8 |
| Compound 2107 | morpholine | 4.5 | 6.8 |

Synthesis of Compound 2106 ((3S,6S,9S,13S,16S, 22S,25S,31S,34S)-25-[2-[3-chloro-4-(trifluoromethyl)phenyl]ethyl]-31-(cyclohexylmethyl)-16-cyclopentyl-22-[2-(dimethylamino)-2-oxo-ethyl]-9-isobutyl-N,N,3,4,10,14,17,23,29,32-decamethyl-6-[(1S)-1-methylpropyl]-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide)

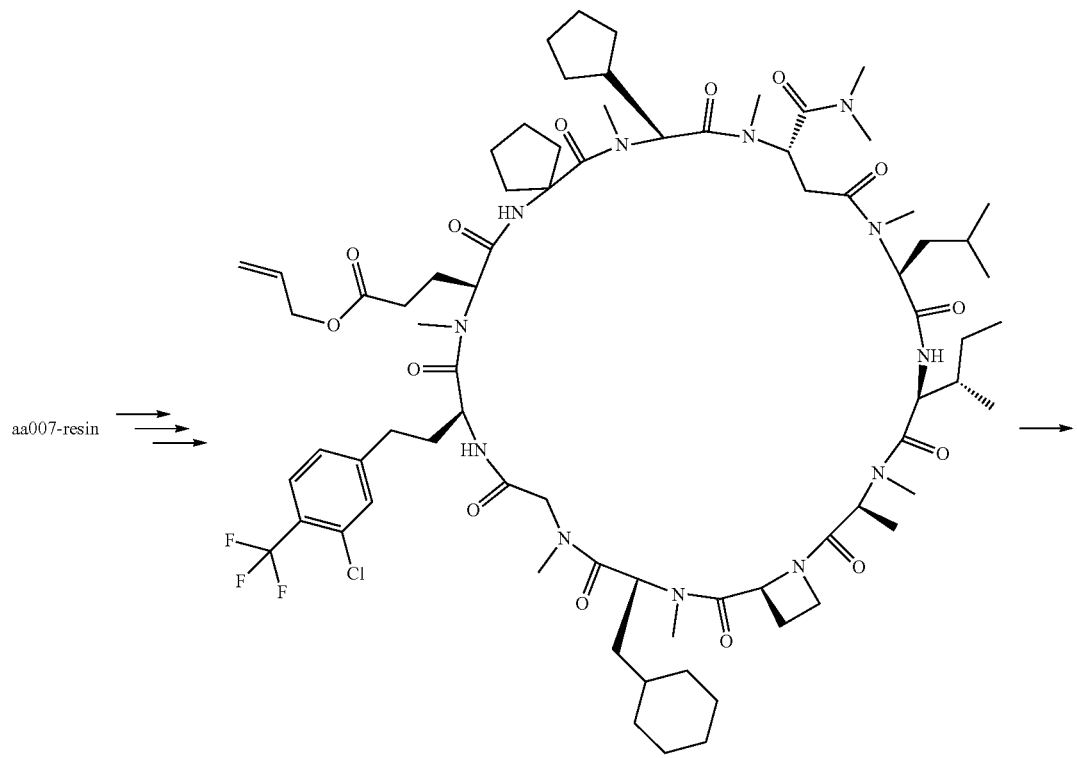

Compound 2106-a

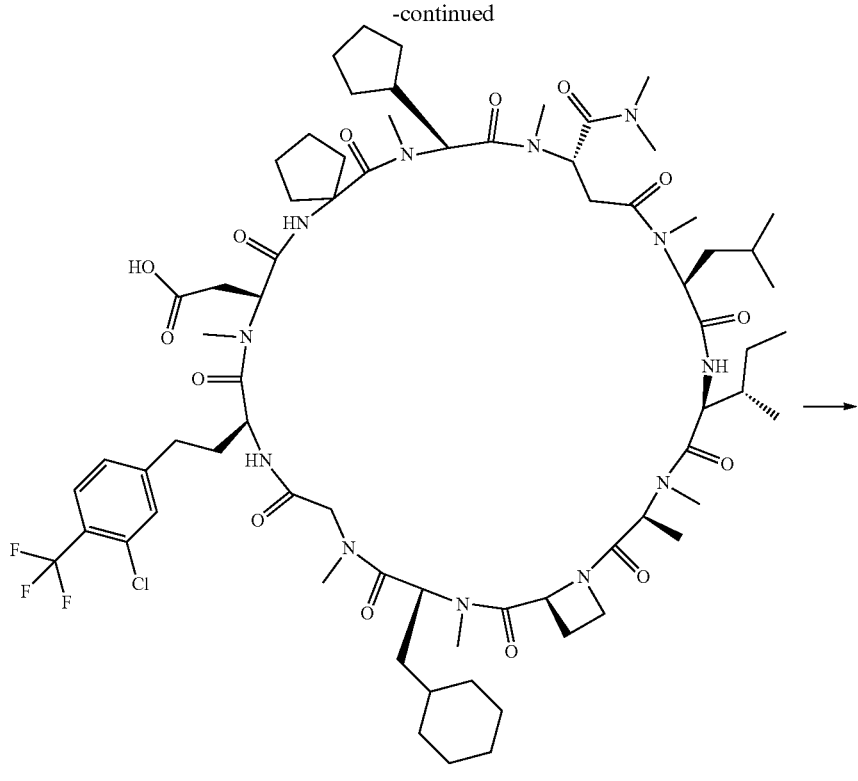
Compound 2106-b
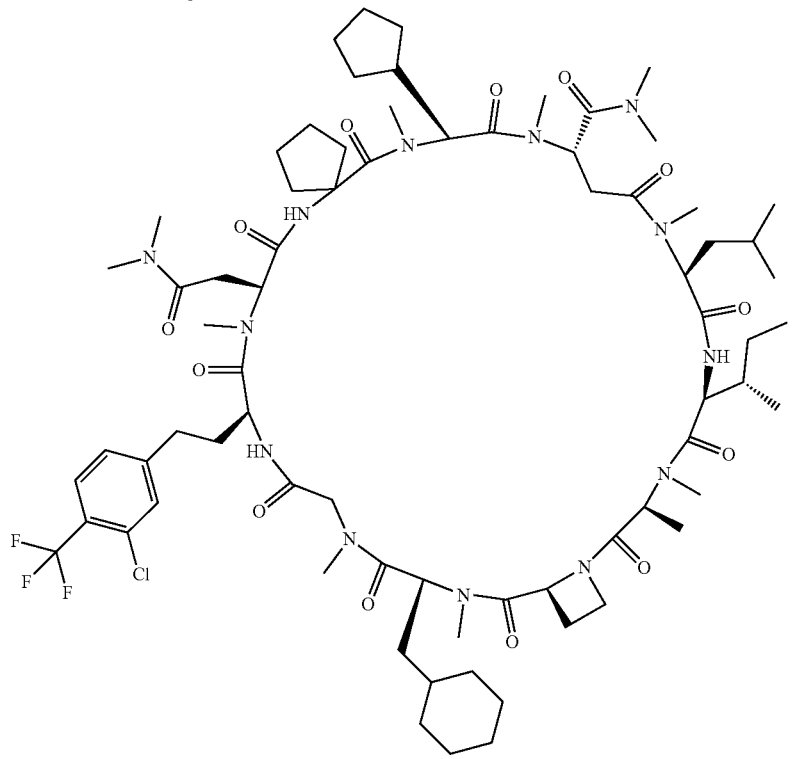
Compound 2106
Compound 2106-a was obtained as a crude product by peptide synthesis according to the basic peptide synthesis method described in the present Examples, using Compound aa011-resin ((3S)-4-(dimethylamino)-3-[9H-fluoren-9-yl-methoxycarbonyl(methyl)amino]-4-oxobutanoic acid-2-chlorotrityl resin, Fmoc-MeAsp(O-Trt(2-Cl)resin)-NMe2) (600 mg, 0.371 mmol/g, 0.223 mmol) as a starting material and using Compound 2108-a ((2S)-2-[9H-fluoren-9-yl-methoxycarbonyl(methyl)amino]-5-oxo-5-prop-2-enoxy-pentanoic acid) as a reagent.

The total amount of Compound 2106-a obtained above (0.223 mmol) was dissolved in dichloromethane (2.5 mL), tetrakis(triphenylphosphine)palladium(0) (14.7 mg, 0.05 equiv.) and phenylsilane (22 µL, 0.7 equiv.) were added thereto, and the mixture was stirred at room temperature for one hour. Tetrakis(triphenylphosphine)palladium (0) (14.7 mg, 0.05 equiv.) and phenylsilane (22 µL, 0.7 equiv.) were added to the reaction solution, and the mixture was stirred for two hours to give a reaction solution containing Compound 2106-b. A solution of HATU (193 mg, 2 equiv.) in dimethylformamide (2.5 mL) and diisopropylethylamine (0.11 mL, 2.4 equiv.) were added to the reaction solution, and the mixture was stirred for 15 minutes. This reaction solution (Reaction Solution B) was divided into six portions, one of which was used for the subsequent reaction.

Dimethylamine (0.11 mL, 5 equiv., 2.0 M tetrahydrofuran solution) was added to Reaction Solution B (0.037 mmol), and the mixture was stirred at room temperature for two hours. The reaction solution was concentrated under reduced pressure, and the resulting residue was purified by preparative HPLC to give Compound 2106 ((3S,6S,9S,13S,16S, 22S,25S,31S,34S)-25-[2-[3-chloro-4-(trifluoromethyl)phe-nyl]ethyl]-31-(cyclohexylmethyl)-16-cyclopentyl-22-[2-(dimethylamino)-2-oxo-ethyl]-9-isobutyl-N,N,3,4,10,14,17, 23,29,32-decamethyl-6-[(1S)-1-methylpropyl]-2,5,8,11,15, 18,21,24,27,30,33-undecaoxo-spiro[1,4,7,10,14,17,20,23, 26,29,32-undecazabicyclo[32.2.0]hexatriacontane-19,1'-cyclopentane]-13-carboxamide) (6.6 mg, 12%). The LC/MS data are described in Table 22.

Synthesis of Compounds 2102, 2105, 2097, and 2109

Compound 2102, 2105, 2097, or 2109 was obtained by adding an amine (5 equiv. relative to the peptide) shown in the following table instead of dimethylamine to one of the six divided portions of Reaction Solution B as obtained in the synthesis of Compound 2106, by the same method as in the synthesis of Compound 2106. The following table describes target compound peptides, amines used for reactions, and yield amounts (mg) and yield percentages (%) of the target compounds. The LC/MS data are described in Table 22.

TABLE 21

| Target compound | Amine | Yield mg | Yield % |
|---|---|---|---|
| Compound 2102 | azetidine | 6.3 | 11 |
| Compound 2105 | piperidine | 5.6 | 10 |
| Compound 2097 | pyrrolidine | 4.4 | 8 |
| Compound 2109 | morpholine | 9.2 | 16 |

Synthesis of Compound 2110 (3-[(3S,6S,9S,13S, 16S,19S,22S,25S,31S,34S)-22-butyl-25-[(3-iodo-phenyl)methyl]-9,16-diisobutyl-31-r[(4-methoxy-phenyl)methyl]-3,4,10,14,20,29,32-heptamethyl-6-[(1S)-1-methylpropyl]-2,5,8,11,15,18,21,24,27,30, 33-undecaoxo-13-(piperidine-1-carbonyl)-1,4,7,10, 14,17,20,23,26,29,32-undecazabicyclo[32.2.0] hexatriacontan-19-yl]-N,N-dimethyl-propanamide)

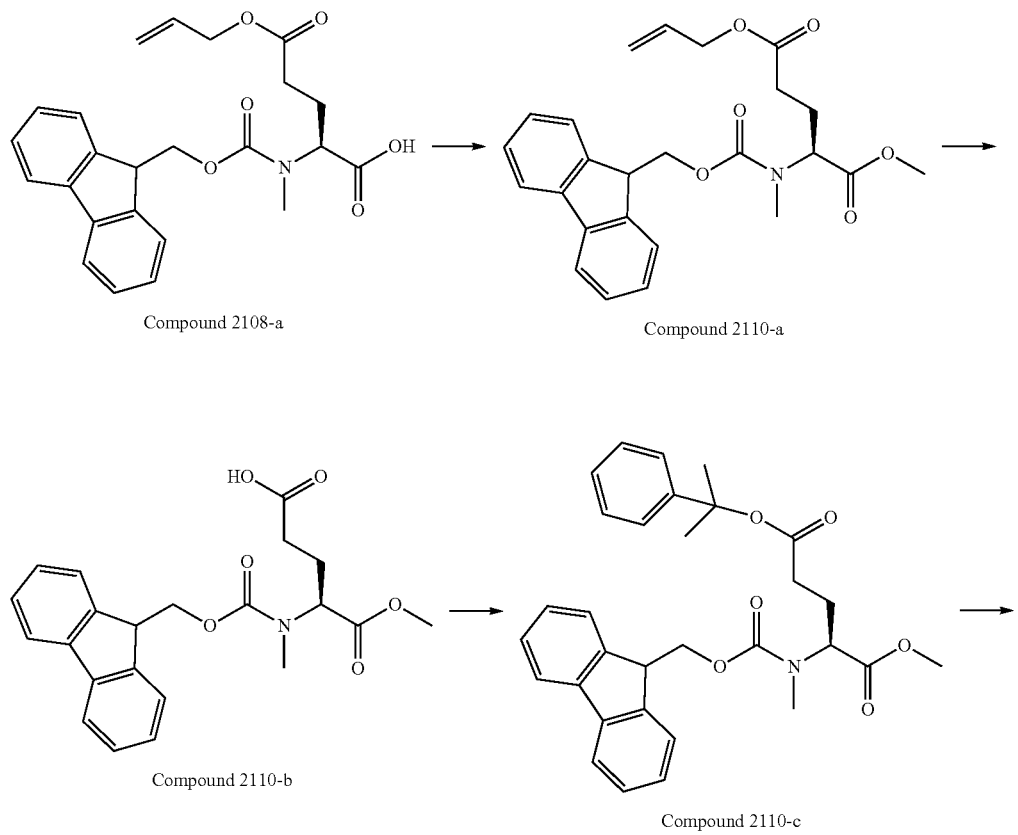

Compound 2108-a

Compound 2110-a

Compound 2110-b

Compound 2110-c

-continued
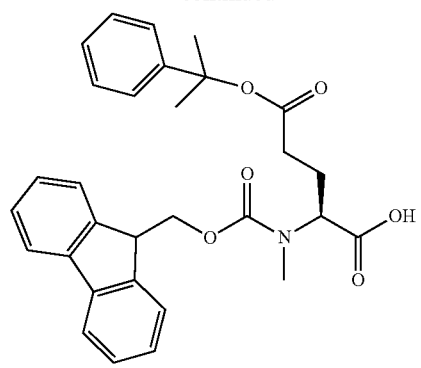
Compound 2110-d
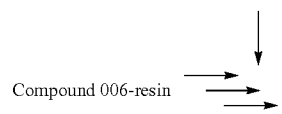
Compound 006-resin →→
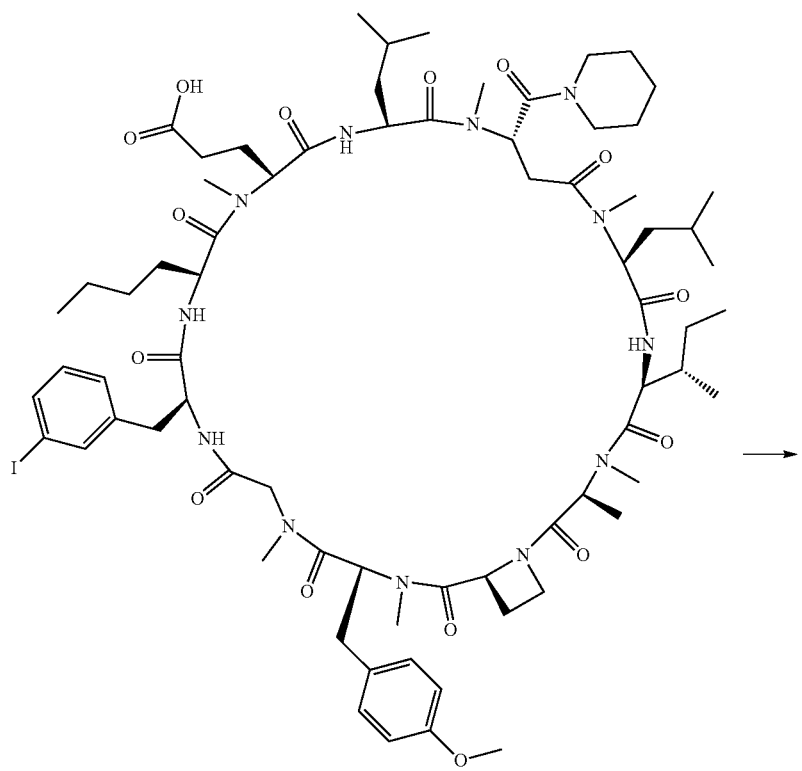
Compound 2110-e -continued

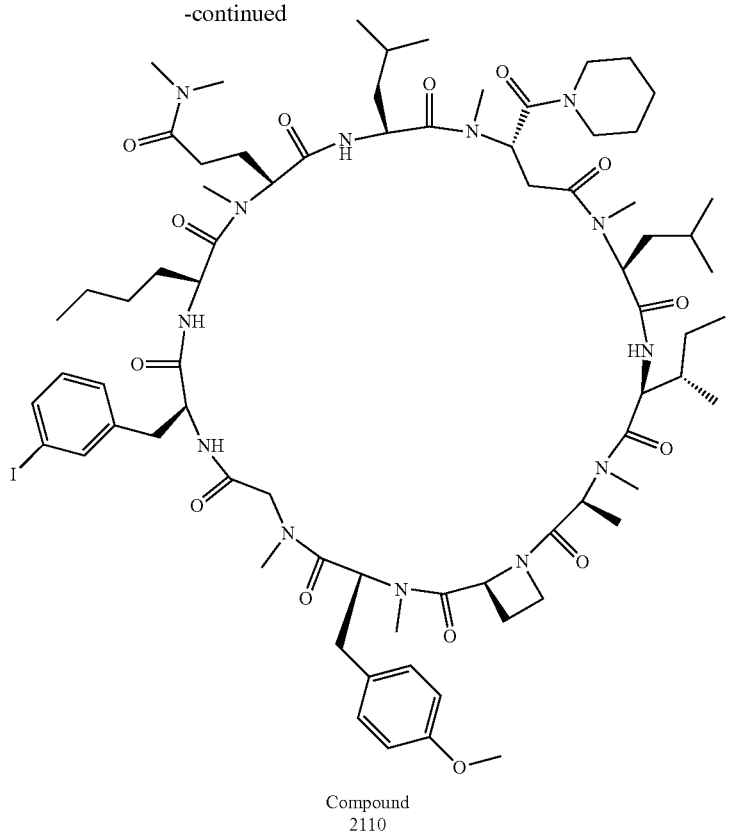

Compound 2110

A solution of Compound 2108-a (10.34 g, 24.42 mmol), WSCI·HCl (6.09 g, 31.7 mmol), and HOAt (4.32 g, 31.7 mmol) in DCM (116 mL) was stirred at room temperature for 15 minutes, methanol (1.038 mL, 25.6 mmol) and DIPEA (5.53 mL, 31.7 mmol) were added thereto, and the mixture was stirred for 90 minutes. The reaction solution was diluted with dichloromethane and sequentially washed with saturated aqueous ammonium chloride/water (1/1) and brine. The organic layer was dried over anhydrous sodium sulfate, and the solvent was then evaporated under reduced pressure to give Compound 2110-a as a crude product (10.93 g). This was mixed with another lot synthesized by the same method and was used for the next reaction.

LCMS (ESI) m/z=438 (M+H)+

Retention time: 1.338 min (analysis condition SMD-method_04)

Tetrakis(triphenylphosphine)palladium(0) (0.19 g, 0.164 mmol) and phenylsilane (2.359 mL, 19.18 mmol) were added to a solution of Compound 2110-a (11.99 g, 27.4 mmol) in DCM (54.8 mL) at 0° C. under a nitrogen atmosphere, and the mixture was stirred at room temperature overnight. The reaction solution was diluted with TBME and washed with a 5% aqueous sodium carbonate solution and water. The aqueous layer was acidified with phosphoric acid (11.25 mL, 164 mmol) and extracted with ethyl acetate. The resulting organic layer was washed with brine and dried over anhydrous sodium sulfate, and the solvent was then evaporated under reduced pressure to give Compound 2110-b (9.56 g, 95%).

LCMS (ESI) m/z=420 (M+Na)+

Retention time: 1.069 min (analysis condition SMD-method_04)

A solution of 2-phenylpropan-2-yl 2,2,2-trichloroacetimidate (13.5 g, 48.1 mmol) in DCM/cyclohexane (1/1, 32.8 mL) was added to a solution of Compound 2110-b (9.56 g, 24.05 mmol) in DCM (16.04 mL) at room temperature, and the mixture was stirred overnight. The reaction solution was filtered through celite, and the solvent was evaporated from the filtrate under reduced pressure to give Compound 2110-c as a crude product (17.29 g). This was used for the next reaction without further purification.

A solution of Compound 2110-c (17.29 g) in THF (100 mL) and 2-propanol (401 mL) was added to a suspension of calcium chloride (40 g, 361 mmol) and lithium hydroxide monohydrate (4.04 g, 96 mmol) in water (100 mL) at room temperature, and the mixture was stirred overnight. The solid in the reaction solution was removed by filtration, and the filtrate was concentrated under reduced pressure. Water was added to the residue, and the mixture was extracted with ethyl acetate. The organic layer was sequentially washed with a 0.1 M aqueous phosphoric acid solution and brine and dried over anhydrous sodium sulfate, and the solvent was evaporated under reduced pressure. The resulting residue was diluted with TBME/hexane (1/1) and extracted with 5% aqueous sodium carbonate/water/methanol (15/12/4). The resulting aqueous layer was washed with TBME/hexane (1/1) and extracted with ethyl acetate. The resulting organic layer was sequentially washed with a 0.2 M aqueous phosphoric acid solution and brine and dried over anhydrous sodium sulfate, and the solvent was evaporated under reduced pressure to give Compound 2110-d (9.68 g, 80%).

LCMS (ESI) m/z=524 (M+Na)+

Retention time: 1.365 min (analysis condition SMD-method_04)

Compound 2110-e (25 mg, 40%) was obtained by peptide synthesis according to the basic peptide synthesis method described in the present Examples, using Compound aa006-resin ((3S)-3-[9H-fluoren-9-ylmethoxycarbonyl(methyl)amino]-4-oxo-4-piperidin-1-ylbutanoic acid-2-chlorotrityl resin, Fmoc-MeAsp(O-Trt(2-Cl)resin)-pip) (100 mg, 0.411 mmol/g, 0.0411 mmol) as a raw material and using the above-obtained Compound 2110-d as a reagent. The Pis group was deprotected under the same conditions as in the deprotection of the THP group.

LCMS (ESI) m/z=1510 (M+H)+

Retention time: 0.71 min (analysis condition SQDAA50)

Compound 2110-e (15 mg, 0.0099 mmol) was dissolved in tetrahydrofuran (0.2 ml). Sodium bicarbonate (4.17 mg, 0.050 mmol), 3-(diethoxyphosphoryloxy)-1,2,3-benzotriazin-4(3H)-one (DEPBT) (14.87 mg, 0.050 mmol), and Dimethylamine (2 mol/L, a THE solution, 0.025 ml, 0.050 mmol) were added, and the mixture was then stirred at room temperature for four hours. The reaction solution was concentrated, and the resulting residue was then purified by preparative HPLC to give Compound 2110 (3-[(3S,6S,9S,13S,16S,19S,22S,25S,31S,34S)-22-butyl-25-[(3-iodophenyl)methyl]-9,16-diisobutyl-31-[(4-methoxyphenyl)methyl]-3,4,10,14,20,29,32-heptamethyl-6-[(1S)-1-methylpropyl]-2,5,8,11,15,18,21,24,27,30,33-undecaoxo-13-(piperidine-1-carbonyl)-1,4,7,10,14,17,20,23,26,29,32-undecazabicyclo[32.2.0]hexatriacontan-19-yl]-N,N-dimethyl-propanamide) (5.07 mg, 33%). The LC/MS data are described in Table 22.

Synthesis of Compound 2100 (3-[(3S,6S,9S,12S,18S,27S,30S,34S)-9-butyl-12-[(3-iodophenyl)methyl]-3,30-diisobutyl-1,7,16,19,22,25,31-heptamethyl-27-[(1S)-1-methylpropyl]-2,5,8,11,14,17,20,23,26,29,32-undecaoxo-34-(piperidine-1-carbonyl)-18-(p-tolylmethyl)-1,4,7,10,13,16,19,22,25,28,31-undecazacyclotetratriacont-6-yl]-N,N-dimethyl-propanamide)

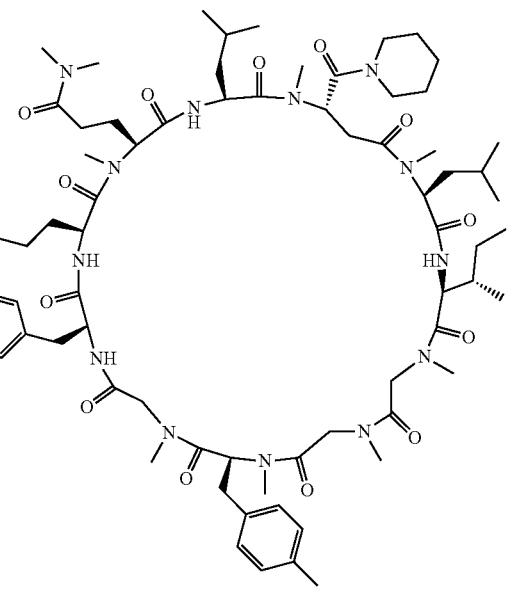

Compound 2100

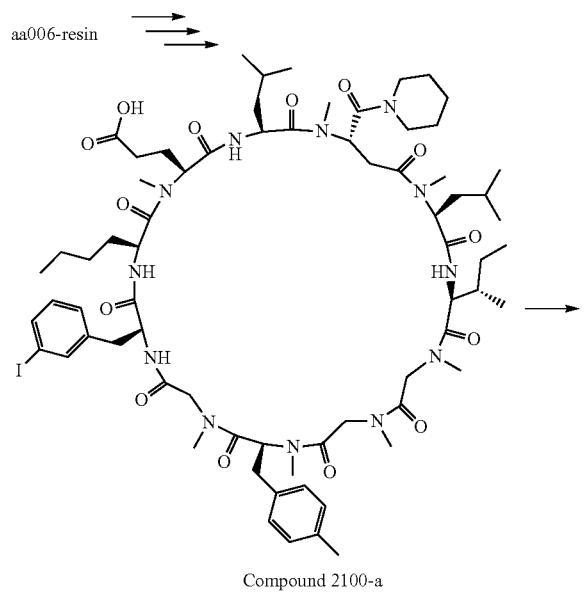

Compound 2100-a

Compound 2100-a (27.5 mg, 46%) was obtained by peptide synthesis according to the basic peptide synthesis method described in the present Examples, using Compound aa006-resin ((3S)-3-[9H-fluoren-9-ylmethoxycarbonyl(methyl)amino]-4-oxo-4-piperidin-1-ylbutanoic acid-2-chlorotrityl resin, Fmoc-MeAsp(O-Trt(2-Cl)resin)-pip) (100 mg, 0.411 mmol/g, 0.0411 mmol) as a raw material and using Compound 2110-d as a reagent. The Pis group was deprotected under the same conditions as in the deprotection of the THP group.

LCMS (ESI) m/z=1468 (M+H)+

Retention time: 0.73 min (analysis condition SQDAA50)

Compound 2100 (3-[(3S,6S,9S,12S,18S,27S,30S,34S)-9-butyl-12-[(3-iodophenyl)methyl]-3,30-diisobutyl-1,7,16,19,22,25,31-heptamethyl-27-[(1S)-1-methylpropyl]-2,5,8,11,14,17,20,23,26,29,32-undecaoxo-34-(piperidine-1-carbonyl)-18-(p-tolylmethyl)-1,4,7,10,13,16,19,22,25,28,31-undecazacyclotetratriacont-6-yl]-N,N-dimethyl-propanamide) (6.44 mg, 43%) was obtained by the same method as in the synthesis of Compound 2110 using Compound 2100-a. The LC/MS data are described in Table 22.

Synthesis of Compound 2101 ((3S,9S,12S,18S,27S,30S,34S)-34-(4,4-difluoropiperidine-1-carbonyl)-12-[(3-iodophenyl)methyl]-3,30-diisobutyl-9-[(4-methoxyphenyl)methyl]-1,6,6,7,16,19,22,25,31-nonamethyl-27-[(1S)-1-methylpropyl]-18-(p-tolylmethyl)-1,4,7,10,13,16,19,22,25,28,31-undecazacyclotetratriacontane-2,5,8,11,14,17,20,23,26,29,32-undecone)
5
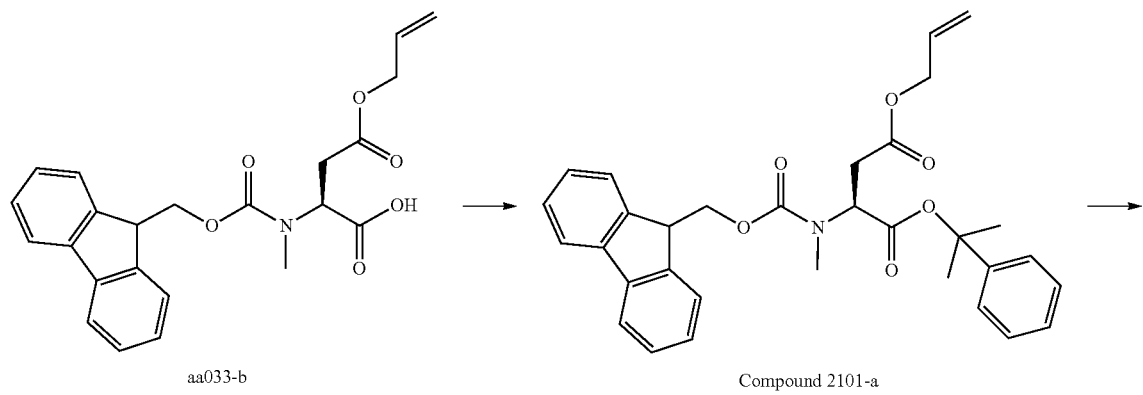
aa033-b    Compound 2101-a
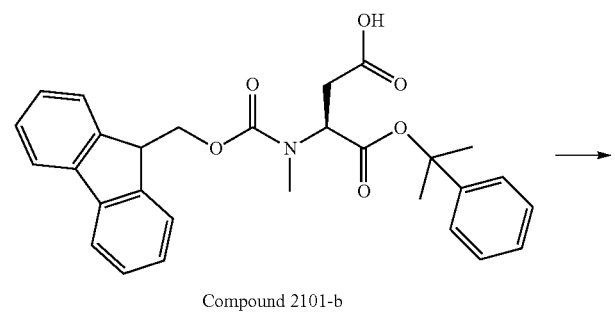
Compound 2101-b
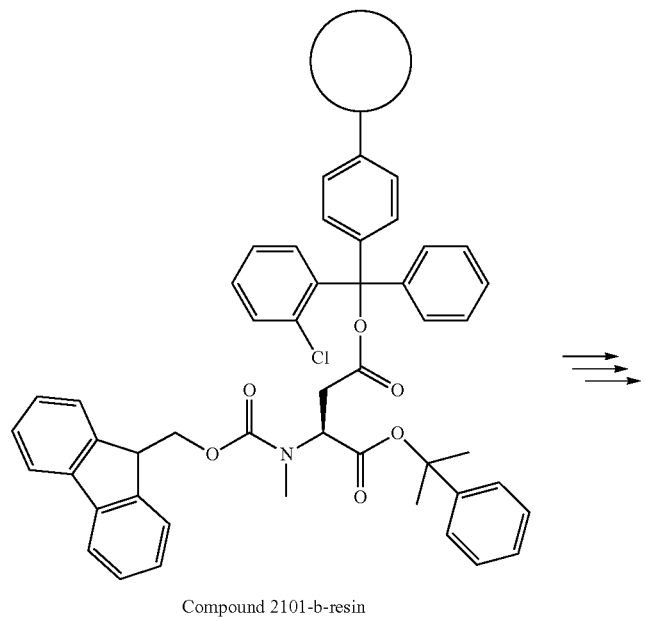
Compound 2101-b-resin

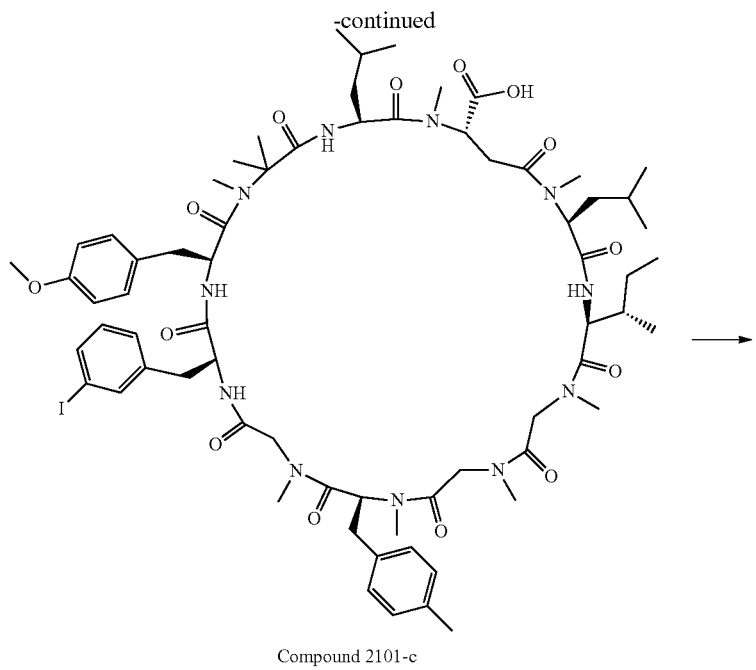

Compound 2101-c

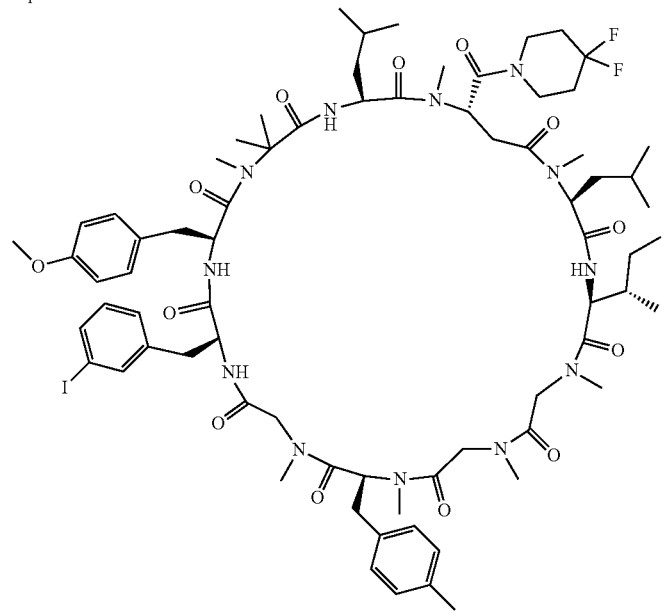

Compound 2101

2-Phenylpropan-2-yl 2,2,2-trichloroacetimidate (2.74 g, 9.77 mmol) was added as a DCM solution to a solution of aa033-b (2 g, 4.88 mmol) in DCM (15 mL), and the mixture was stirred at room temperature for two hours. The solvent was evaporated from the reaction solution under reduced pressure, and the resulting residue was purified by reverse phase column chromatography to give Compound 2101-a (2.10 g, 81%).

LCMS (ESI) m/z=550.3 (M+Na)+

Retention time: 0.76 mi (analysis condition SQDAA50)

Tetrakis(triphenylphosphine)palladium(0) (0.046 g, 0.04 mmol) and phenylsilane (0.343 mL, 2.79 mmol) were added to a solution of Compound 2101-a (2.1 g, 3.98 mmol) in DCM (15 mL) at room temperature under a nitrogen atmosphere, and the mixture was stirred for one hour. The reaction solution was diluted with MTBE and a 5% aqueous sodium bicarbonate solution, the solvent was evaporated under reduced pressure, and the resulting residue was purified by reverse phase column chromatography to give Compound 2101-b (1.67 g, 86%).

LCMS (ESI) m/z=510 (M+Na)+

Retention time: 0.94 mi (analysis condition SQDFA05)

Compound 2101-b-resin (3.6 g 0.377 mmol/g) was obtained by the same method as in the synthesis of Compound aa007-resin using the obtained Compound 2101-b (1.17 g, 2.4 mmol).

Compound 2101-c (38 mg, 24%) was obtained by peptide synthesis according to the basic peptide synthesis method described in the present Examples, using Compound 2101-b-resin (300 mg, 0.377 mmol/g, 0.1131 mmol) as a raw material. The Pis group was deprotected under the same conditions as in the deprotection of the THP group.

LCMS (ESI) m/z=1421 (M+H)+

Retention time: 0.64 min (analysis condition SQDAA50)

Compound 2101 ((3S,9S,12S,18S,27S,30S,34S)-34-(4,4-difluoropiperidine-1-carbonyl)-12-[(3-iodophenyl)methyl]-3,30-diisobutyl-9-[(4-methoxyphenyl)methyl]-1,6,6,7,16,19,22,25,31-nonamethyl-27-[(1S)-1-methylpropyl]-18-(p-tolylmethyl)-1,4,7,10,13,16,19,22,25,28,31-undecazacyclotetratriacontane-2,5,8,11,14,17,20,23,26,29,32-undecone) (6.77 mg, 42%) was obtained by the same method as in the synthesis of Compound 2110 using Compound 2101-c (15 mg, 10.56 µmol) and using 4,4-difluoropiperidine hydrochloride instead of dimethylamine. The LC/MS data are described in Table 22.

Synthesis of Compound 2099 ((3S,9S,12S,18S,27S,30S,34S)-34-(3,3-difluoropiperidine-1-carbonyl)-12-[(3-iodophenyl)methyl]-3,30-diisobutyl-9-[(4-methoxyphenyl)methyl]-1,6,6,7,16,19,22,25,31-nonamethyl-27-[(1S)-1-methylpropyl]-18-(p-tolylmethyl)-1,4,7,10,13,16,19,22,25,28,31-undecazacyclotetratriacontane-2,5,8,11,14,17,20,23,26,29,32-undecone)

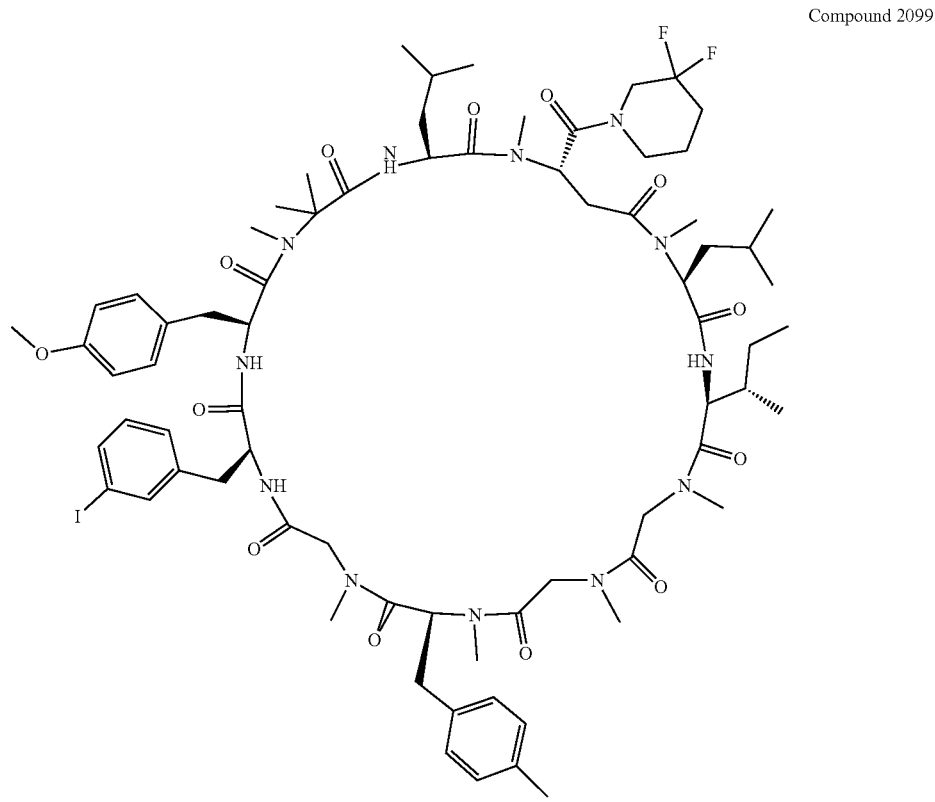 [SMILES: CC[C@H](C)[C@@H]1NC(=O)[C@H](CC(C)C)N(C)C(=O)C[C@@H](C(=O)N2CCCC(F)(F)C2)N(C)C(=O)[C@H](CC(C)C)NC(=O)C(C)(C)N(C)C(=O)[C@H](Cc2ccc(OC)cc2)NC(=O)[C@H](Cc2cccc(I)c2)NC(=O)CN(C)C2OC2(C)[C@H](Cc2ccc(C)cc2)N(C)C(=O)CN(C)C(=O)CN(C)C1=O]

Compound 2099

Compound 2099 ((3S,9S,12S,18S,27S,30S,34S)-34-(3,3-difluoropiperidine-1-carbonyl)-12-[(3-iodophenyl)methyl]-3,30-diisobutyl-9-[(4-methoxyphenyl)methyl]-1,6,6,7,16,19,22,25,31-nonamethyl-27-[(1S)-1-methylpropyl]-18-(p-tolylmethyl)-1,4,7,10,13,16,19,22,25,28,31-undecazacyclotetratriacontane-2,5,8,11,14,17,20,23,26,29,32-undecone) (5.24 mg, 33%) was obtained by the same method as in the synthesis of Compound 2110 using Compound 2101-c (15 mg, 10.56 µmol) and using 3,3-difluoropiperidine hydrochloride instead of dimethylamine. The LC/MS data are described in Table 22.

1-4-10. Peptide Modification by Olefin Metathesis Reaction

Synthesis of Compound 2053 ((8S,11S,17S,26S, 29S,33S,36S)-11-[2-[3-chloro-4-(trifluoromethyl) phenyl]ethyl]-36-cyclohexyl-17-(cyclohexylmethyl)- 29-isobutyl-9,15,18,21,24,30,34,37-octamethyl-26- [(1S)-1-methylpropyl]-33-(piperidine-1-carbonyl)-8- (2-tetrahydropyran-4-ylideneethyl)-6,9,12,15,18,21, 24,27,30,34,37-undecazaspiro[4.33]octatriacontane- 7,10,13,16,19,22,25,28,31,35,38-undecone)

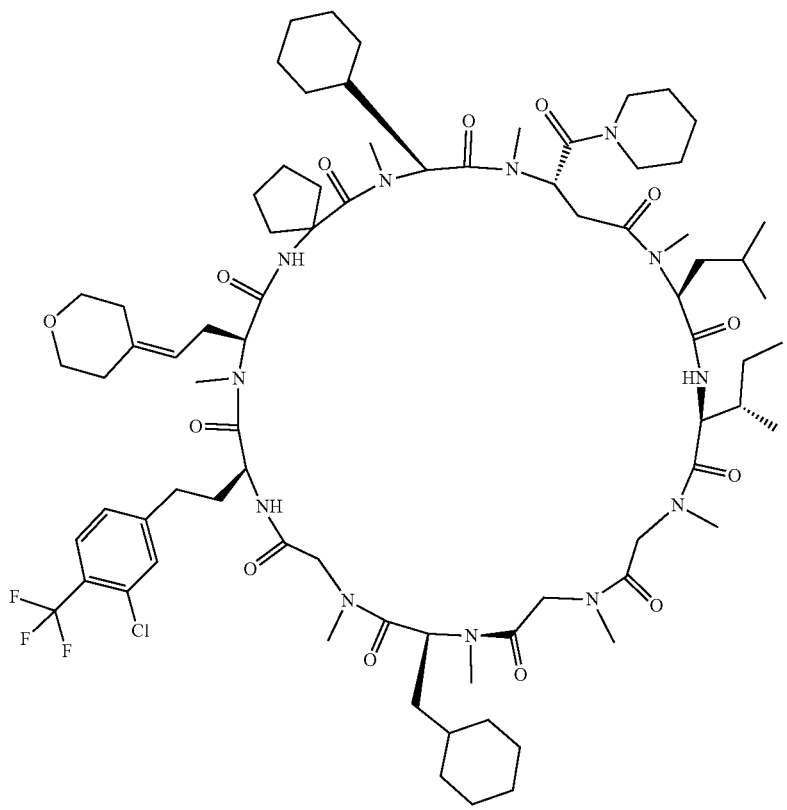

Compound 2053

A solution of Compound 1449 (9 mg, 6.18 µmol), Grubbs catalyst 2nd generation (2.6 mg), and 4-methylenetetrahydro-2H-pyran (20 µL) in 1,2-dichloroethane (1 mL) was stirred at 60° C. for six hours under a nitrogen atmosphere. 4-Methylenetetrahydro-2H-pyran (50 µL) was further added and the mixture was stirred at the same temperature for 2 hours and 45 minutes. Grubbs catalyst 2nd generation (2.6 mg) was further added and the mixture was stirred at the same temperature for 12 hours. The reaction mixture was cooled to room temperature and concentrated under reduced pressure. The resulting crude product was purified by reverse phase column chromatography (acetonitrile with 0.1% formic acid/distilled water with 0.1% formic acid) to give Compound 2053 ((8S,11S,17S,26S,29S,33S,36S)-11- [2-[3-chloro-4-(trifluoromethyl)phenyl]ethyl]-36-cyclohexyl-17-(cyclohexylmethyl)-29-isobutyl-9,15,18,21,24,30, 34,37-octamethyl-26-[(1S)-1-methylpropyl]-33- (piperidine-1-carbonyl)-8-(2-tetrahydropyran-4- ylideneethyl)-6,9,12,15,18,21,24,27,30,34,37- undecazaspiro[4.33]octatriacontane-7,10,13,16,19,22,25, 28,31,35,38-undecone) (5.0 mg, 60%). The LC/MS data are described in Table 22.

Synthesis of Compound 2048 ((8S,11S,17S,26S, 29S,33S,36S)-11-[2-[3-chloro-4-(trifluoromethyl) phenyl]ethyl]-36-cyclohexyl-17-(cyclohexylmethyl)- 29-isobutyl-9,15,18,21,24,30,34,37-octamethyl-26- [(1S)-1-methylpropyl]-33-(piperidine-1-carbonyl)-8- (2-tetrahydropyran-4-ylethyl)-6,9,12,15,18,21,24,27, 30,34,37-undecazaspiro[4.33]octatriacontane-7,10, 13,16,19,22,25,28,31,35,38-undecone)

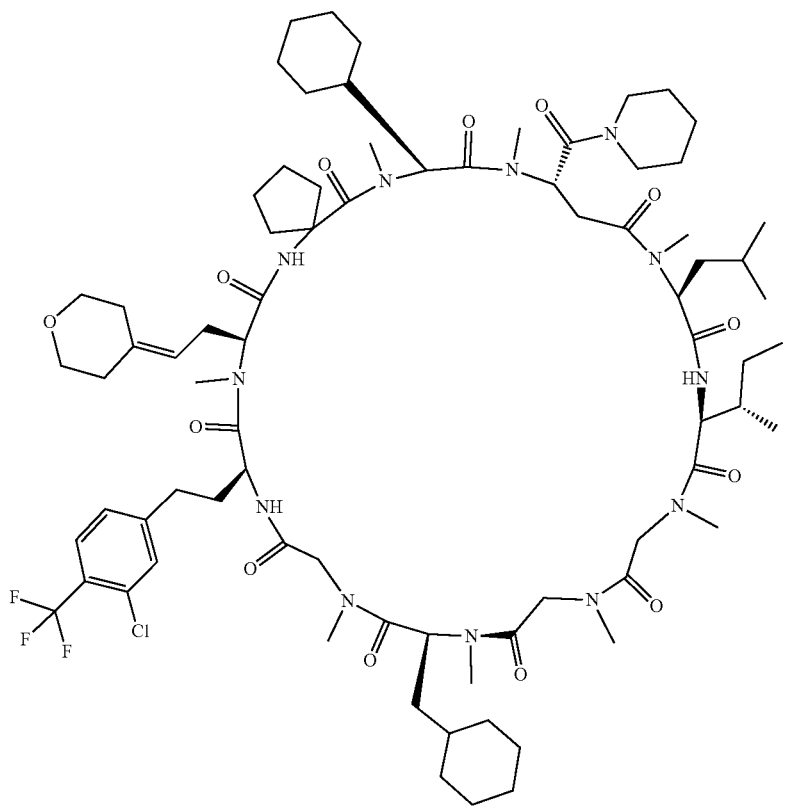

Compound 2048

A mixture of Compound 2053 (7.8 mg, 5.11 μmol) and platinum(IV) oxide (1.2 mg, 5.11 μmol) in ethanol (1 mL) was stirred at room temperature for 10 hours under a hydrogen atmosphere, after which platinum(IV) oxide (1.2 mg, 5.11 μmol) was further added and the mixture was stirred at the same temperature for about 17 hours. The reaction mixture was filtered through celite and concentrated under reduced pressure. The resulting residue was purified by reverse phase column chromatography (10 mM aqueous ammonium acetate solution/methanol) to give Compound 2048 ((8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-9,15,18,21,24,30,34,37-octamethyl-26-[(1S)-1-methylpropyl]-33-(piperidine-1-carbonyl)-8-(2-tetrahydropyran-4-ylethyl)-6,9,12,15,18,21,24,27,30, 34,37-undecazaspiro[4.33]octatriacontane-7,10,13,16,19, 22,25,28,31,35,38-undecone) (7.8 mg, 99%). The LC/MS data are described in Table 22.

Synthesis of Compound 2050 (tert-butyl 3-[2-[(8S, 11S,17S,26S,29S,33S,36S)-11-[2-[3-chloro-4-(trifluoromethyl)phenyl]ethyl]-36-cyclohexyl-17-(cyclohexylmethyl)-29-isobutyl-9,15,18,21,24,30,34,37-octamethyl-26-[(1S)-1-methylpropyl]-7,10,13,16,19,22,25,28,31,35,38-undecaoxo-33-(piperidine-1-carbonyl)-6,9,12,15,18,21,24,27,30,34,37-undecazaspiro[4.33]octatriacontan-8-yl]ethylidene]azetidine-1-carboxylate)

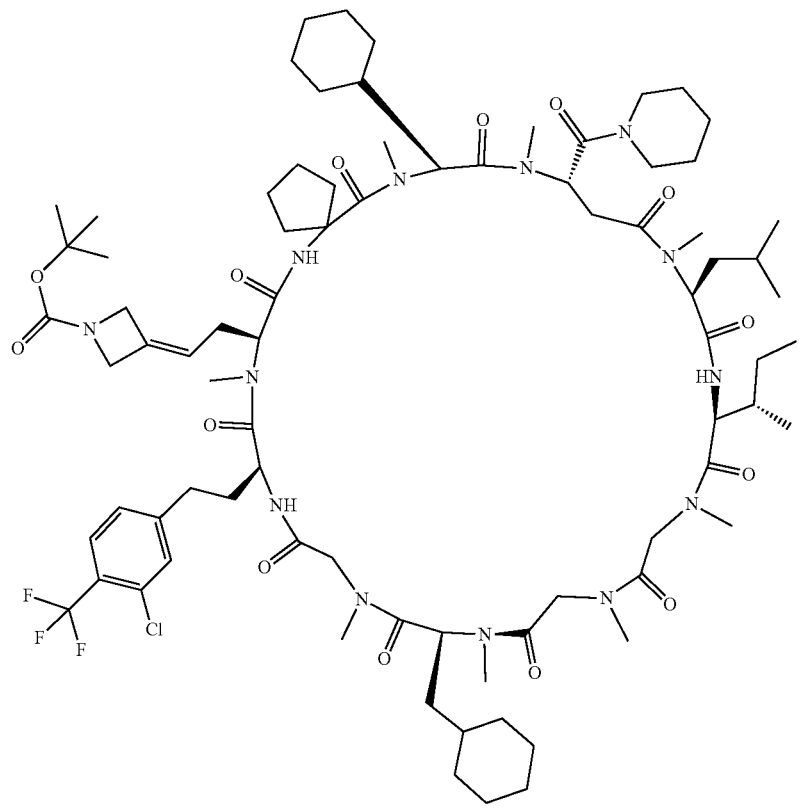

Compound 2050

Under a nitrogen atmosphere, a solution of Compound 1449 (9 mg, 6.18 μmol), Hoveyda-Grubbs catalyst 2nd generation (3.9 mg), and 1-tert-butoxycarbonyl-3-methyleneazetidine (20 μL) in dichloroethane (1 mL) was stirred at 60° C. for 2 hours and 30 minutes and then stirred at 75° C. Hoveyda-Grubbs catalyst 2nd generation (3.9 mg) and 1-tert-butoxycarbonyl-3-methylene-azetidine (20 μL) were further added and the mixture was stirred at 80° C. for 14 hours, after which Hoveyda-Grubbs catalyst 2nd generation (3.9 mg) was further added and the mixture was stirred at the same temperature for about 10 hours. The reaction mixture was cooled to room temperature and concentrated under reduced pressure, and the resulting residue was purified by preparative HPLC to give Compound 2050 (tert-butyl 3-[2-[(8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-9,15,18,21,24,30,34,37-octamethyl-26-[(1S)-1-methylpropyl]-7,10,13,16,19,22,25,28,31,35,38-undecaoxo-33-(piperidine-1-carbonyl)-6,9,12,15,18,21,24,27,30,34,37-undecazaspiro[4.33]octatriacontan-8-yl]ethylidene]azetidine-1-carboxylate) (0.65 mg, 6.6%). The LC/MS data are described in Table 22.

Synthesis of Compound 2056 (tert-butyl 3-[2-[(8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-9,15,18,21,24,30,34,37-octamethyl-26-[(1S)-1-methylpropyl]-7,10,13,16,19,22,25,28,31,35,38-undecaoxo-33-(piperidine-1-carbonyl)-6,9,12,15,18,21,24,27,30,34,37-undecazaspiro[4.33]octatriacontan-8-yl]ethyl]azetidine-1-carboxylate)

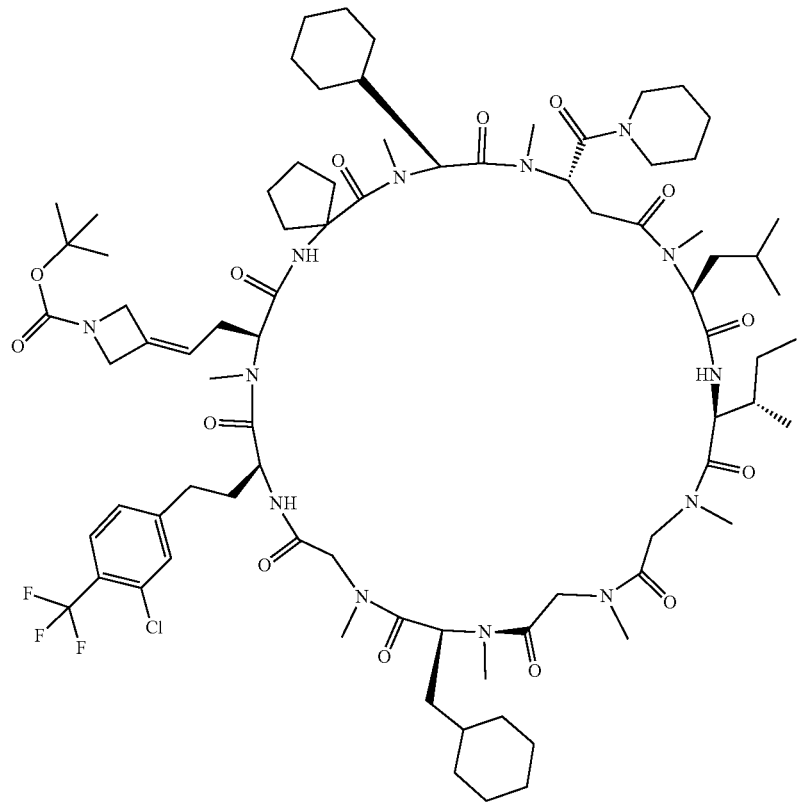

Compound 2056

A mixture of Compound 2050 (1.6 mg, 1 µmol) and platinum(IV) oxide (1 mg, 4.4 µmol) in ethanol (1 mL) was stirred at room temperature for three hours under a hydrogen atmosphere. The reaction mixture was filtered through celite and concentrated under reduced pressure. The resulting residue was purified by reverse phase column chromatography (10 mM aqueous ammonium acetate solution/methanol) to give Compound 2056 (tert-butyl 3-[2-[(8S,11S,17S,26S,29S,33S,36S)-11-[2-[3-chloro-4-(trifluoromethyl)phenyl]ethyl]-36-cyclohexyl-17-(cyclohexylmethyl)-29-isobutyl-9,15,18,21,24,30,34,37-octamethyl-26-[(1S)-1-methylpropyl]-7,10,13,16,19,22,25,28,31,35,38-undecaoxo-33-(piperidine-1-carbonyl)-6,9,12,15,18,21,24,27,30,34,37-undecazaspiro[4.33]octatriacontan-8-yl]ethyl]azetidine-1-carboxylate) (1.2 mg, 75%). The LC/MS data are described in Table 22.

Synthesis of Compound 2046 ((11S,17S,26S,29S, 33S,36S)-11-[2-[3-chloro-4-(trifluoromethyl)phenyl] ethyl]-36-cyclohexyl-17-(cyclohexylmethyl)-9-(5-hydroxypent-2-enyl)-29-isobutyl-15,18,21,24,30,34, 37-heptamethyl-26-[(1S)-1-methylpropyl]-33-(piperidine-1-carbonyl)-6,9,12,15,18,21,24,27,30,34, 37-undecazaspiro[4.33]octatriacontane-7,10,13,16, 19,22,25,28,31,35,38-undecone)

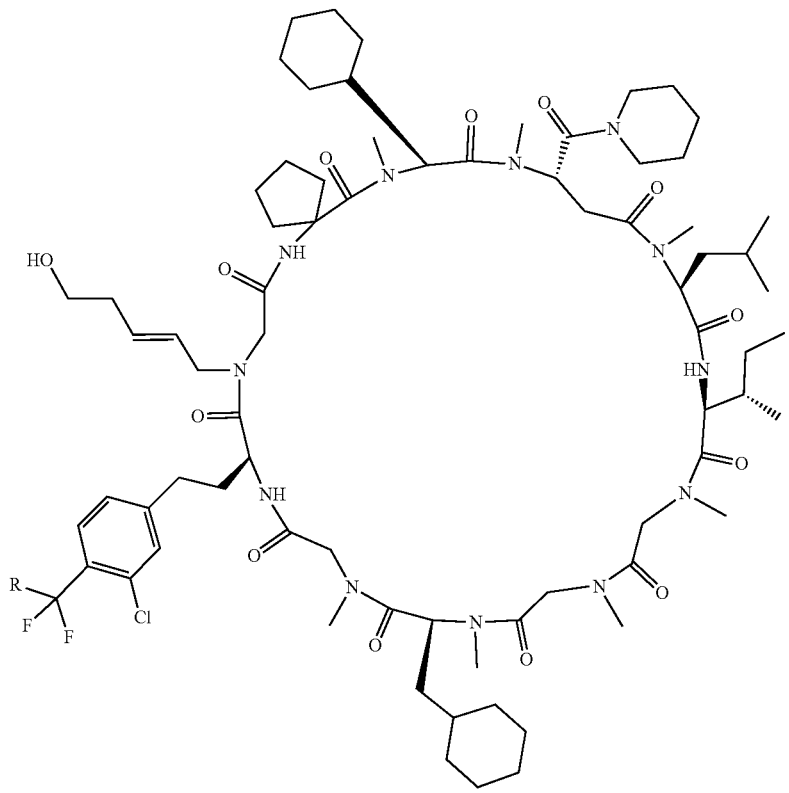

Compound 2046

Compound 899 (40 mg, 0.028 μmol) was dissolved in 1,2-dichloroethane (0.66 mL), Stewart-Grubbs catalyst (CAS No. 927429-61-6, 24 mg, 0.042 mmol) and homoallyl alcohol (20 μL, 8 equiv.) were added, and the mixture was stirred at room temperature for 16 hours. Homoallyl alcohol (20 μL, 8 equiv.) was further added and the mixture was stirred for two hours, after which Stewart-Grubbs catalyst (CAS No. 927429-61-6, 12 mg, 0.021 mmol) was added and the mixture was further stirred for two hours. The reaction solution was concentrated under reduced pressure, and the resulting residue was purified by reverse phase column chromatography (acetonitrile with 0.1% formic acid/distilled water with 0.1% formic acid) to give Compound 2046 ((11S,17S,26S,29S,33S,36S)-11-[2-[3-chloro-4-(trifluoromethyl)phenyl]ethyl]-36-cyclohexyl-17-(cyclohexylmethyl)-9-(5-hydroxypent-2-enyl)-29-isobutyl-15,18,21,24,30,34, 37-heptamethyl-26-[(1S)-1-methylpropyl]-33-(piperidine-1-carbonyl)-6,9,12,15,18,21,24,27,30,34,37-undecazaspiro [4.33]octatriacontane-7,10,13,16,19,22,25,28,31,35,38-undecone) (12.3 mg, 30%). The LC/MS data are described in Table 22.

Synthesis of Compound 2049 ((11S,17S,26S,29S,33S,36S)-11-[2-[3-chloro-4-(trifluoromethyl)phenyl]ethyl]-36-cyclohexyl-17-(cyclohexylmethyl)-9-(5-hydroxypentyl)-29-isobutyl-15,18,21,24,30,34,37-heptamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone)

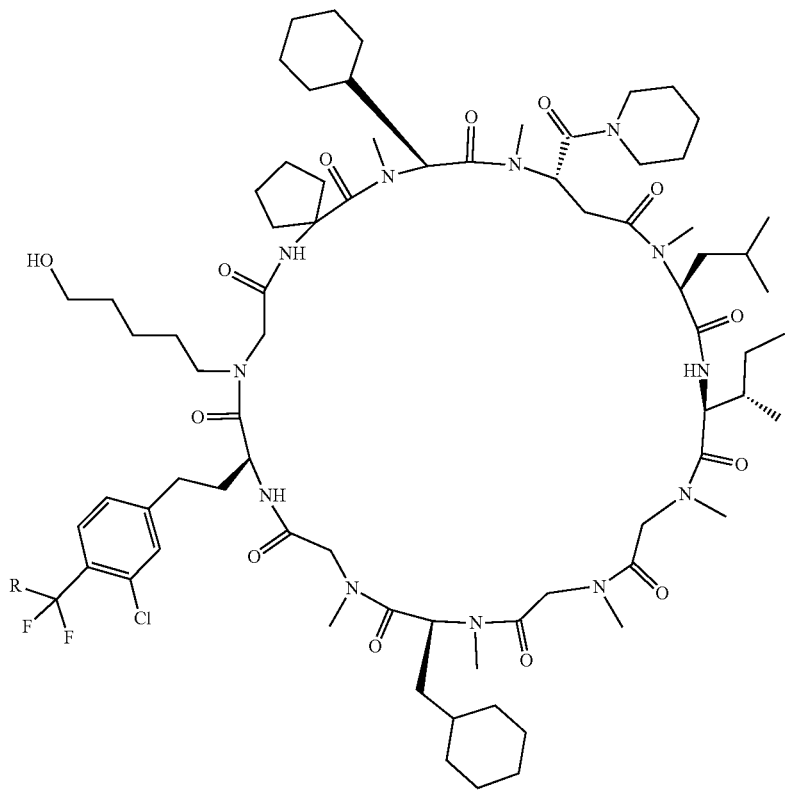

Compound 2049

Platinum(IV) oxide (3.7 mg, 16 μmol) was added to a solution of Compound 2046 (3.0 mg, 2.02 μmol) in ethanol (1.0 mL), the atmosphere in the reaction vessel was replaced with hydrogen, and the mixture was stirred at room temperature for three hours. The reaction solution was filtered through celite, and the filtrate was concentrated under reduced pressure. The resulting residue was purified by reverse phase column chromatography to give Compound 2049 ((11S,17S,26S,29S,33S,36S)-11-[2-[3-chloro-4-(trifluoromethyl)phenyl]ethyl]-36-cyclohexyl-17-(cyclohexylmethyl)-9-(5-hydroxypentyl)-29-isobutyl-15,18,21,24,30,34,37-heptamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone) (2.6 mg, 87%). The LC/MS data are described in Table 22.

Synthesis of Compound 2047 ((11S,17S,26S,29S, 33S,36S)-11-[2-[3-chloro-4-(trifluoromethyl)phenyl] ethyl]-36-cyclohexyl-17-(cyclohexylmethyl)-9-(4-hydroxy-4-methyl-pent-2-enyl)-29-isobutyl-15,18, 21,24,30,34,37-heptamethyl-26-[(1S)-1-methylpropyl]-33-(piperidine-1-carbonyl)-6,9,12,15, 18,21,24,27,30,34,37-undecazaspiro[4.33] octatriacontane-7,10,13,16,19,22,25,28,31,35,38-undecone)

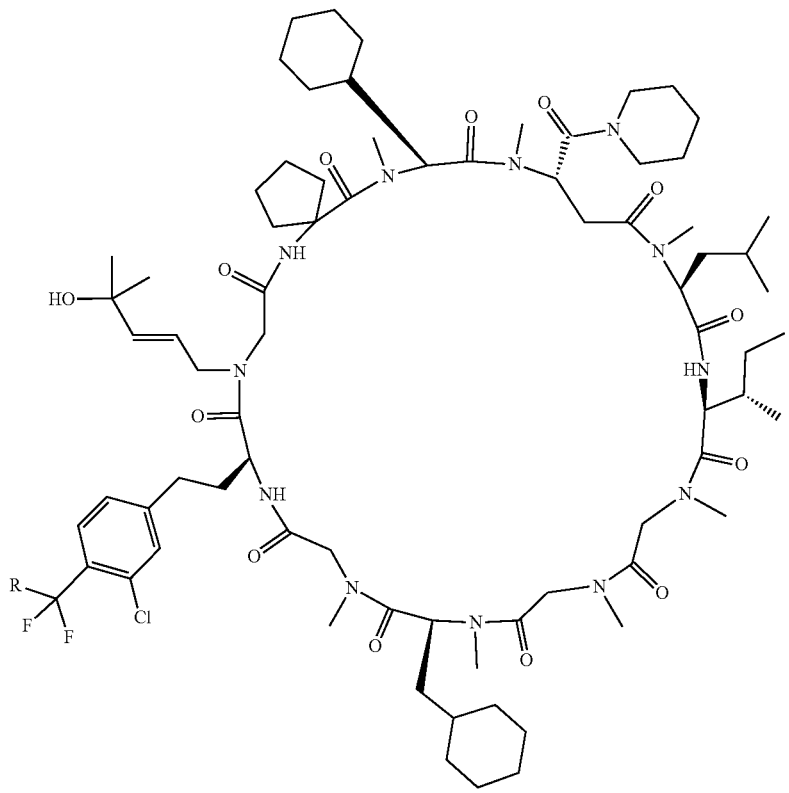

Compound 2047

Compound 899 (20 mg, 14 µmol) was dissolved in dichloroethane (0.33 mL), Stewart-Grubbs catalyst (CAS No. 927429-61-6, 12 mg, 21 µmol) and 2-methyl-3-buten-2-ol (12 µL, 8 equiv.) were added, and the mixture was stirred at room temperature for 16 hours. 2-Methyl-3-buten-2-ol (12 µL, 8 equiv.) was further added and the mixture was stirred for 45 minutes, after which Stewart-Grubbs catalyst (CAS No. 927429-61-6, 6.0 mg, 0.8 equiv.) was added and the mixture was stirred for three hours. The reaction solution was concentrated under reduced pressure, and the resulting residue was purified by reverse phase column chromatography (acetonitrile with 0.1% formic acid/distilled water with 0.1% formic acid) to give a crude product. The crude product was purified by preparative HPLC to give Compound 2047 ((11S,17S,26S,29S,33S,36S)-11-[2-[3-chloro-4-(trifluoromethyl)phenyl]ethyl]-36-cyclohexyl-17-(cyclohexylmethyl)-9-(4-hydroxy-4-methyl-pent-2-enyl)-29-isobutyl-15,18,21,24,30,34,37-heptamethyl-26-1[(1S)-1-methylpropyl]-33-(piperidine-1-carbonyl)-6,9,12,15,18,21, 24,27,30,34,37-undecazaspiro[4.33]octatriacontane-7,10, 13,16,19,22,25,28,31,35,38-undecone) (1.4 mg, 7%). The LC/MS data are described in Table 22.

Synthesis of Compound 2054 (4-[(11S,17S,26S,29S,33S,36S)-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-7,10,13,16,19,22,25,28,31,35,38-undecaoxo-33-(piperidine-1-carbonyl)-6,9,12,15,18,21,24,27,30,34,37-undecazaspiro[4.33]octatriacontan-9-yl]-N,N-dimethyl-but-2-enamide)

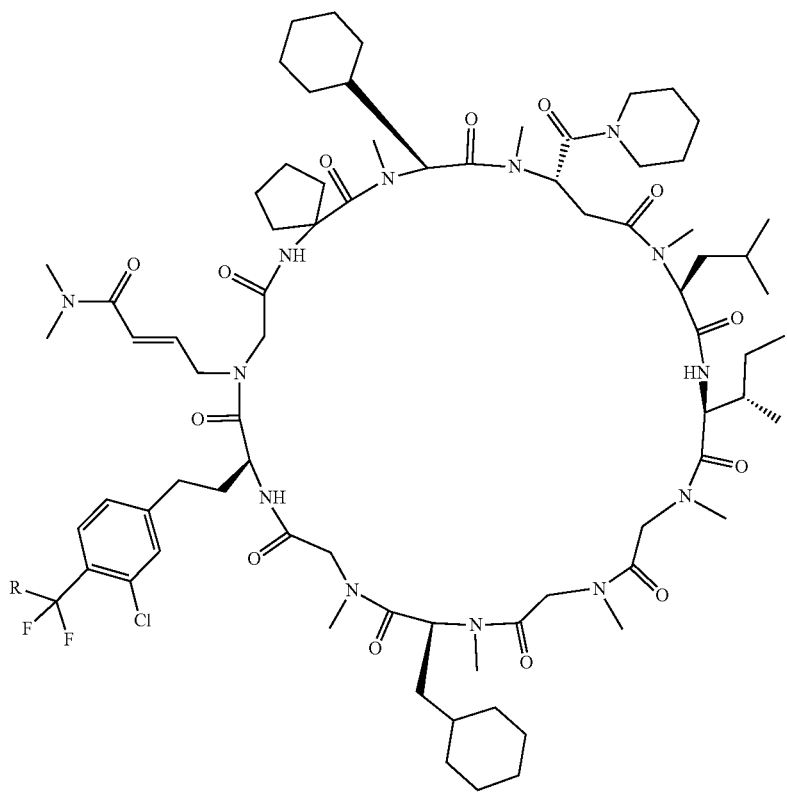

Compound 2054

Compound 2054 (4-[(11S,17S,26S,29S,33S,36S)-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-7,10,13,16,19,22,25,28,31,35,38-undecaoxo-33-(piperidine-1-carbonyl)-6,9,12,15,18,21,24,27,30,34,37-undecazaspiro[4.33]octatriacontan-9-yl]-N,N-dimethyl-but-2-enamide) (1.4 mg, 6%) was obtained by the same synthesis method as in the synthesis of Compound 2047 using Compound 899 (20 mg, 14 μmol) as a starting material and using N,N-dimethylacrylamide (16 equiv.) instead of 2-methyl-3-buten-2-ol. The LC/MS data are described in Table 22.

Synthesis of Compound 2052 (4-[(11S,17S,26S,29S,33S,36S)-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-7,10,13,16,19,22,25,28,31,35,38-undecaoxo-33-(piperidine-1-carbonyl)-6,9,12,15,18,21,24,27,30,34,37-undecazaspiro[4.33]octatriacontan-9-yl]-N,N-dimethyl-butanamide)

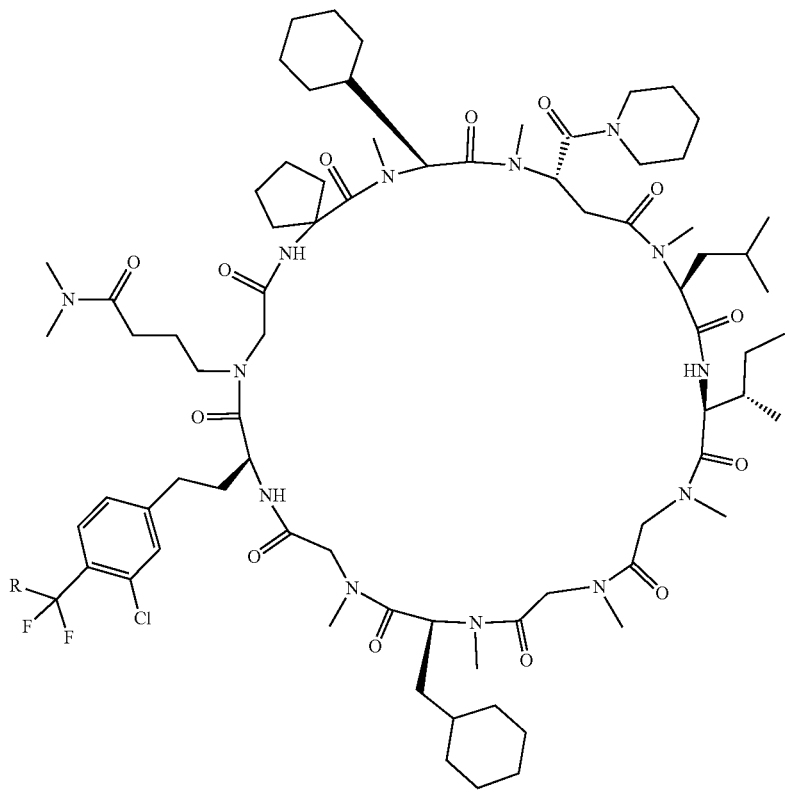

Compound 2052

Platinum(IV) oxide (4.7 mg, 10 equiv.) was added to a solution of Compound 2054 (3.1 mg, 2.08 μmol) in ethanol (1.0 mL), the atmosphere in the reaction vessel was replaced with hydrogen, and the mixture was stirred at room temperature for three hours. The reaction solution was filtered through celite, and the filtrate was concentrated under reduced pressure. The resulting residue was purified by reverse phase column chromatography and then further purified by preparative HPLC to give Compound 2052 (4-[(11S,17S,26S,29S,33S,36S)-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-7,10,13,16,19,22,25,28,31,35,38-undecaoxo-33-(piperidine-1-carbonyl)-6,9,12,15,18,21,24,27,30,34,37-undecazaspiro[4.33]octatriacontan-9-yl]-N,N-dimethyl-butanamide) (1.4 mg, 45%). The LC/MS data are described in Table 22.

Synthesis of Compound 2051 ((11S,17S,26S,29S, 33S,36S)-11-[2-[3-chloro-4-(trifluoromethyl)phenyl] ethyl]-36-cyclohexyl-17-(cyclohexylmethyl)-29-isobutyl-9-[(E)-4-methoxybut-2-enyl]-15,18,21,24, 30,34,37-heptamethyl-26-[(1S)-1-methylpropyl]-33-(piperidine-1-carbonyl)-6,9,12,15,18,21,24,27,30,34, 37-undecazaspiro[4.33]octatriacontane-7,10,13,16, 19,22,25,28,31,35,38-undecone)

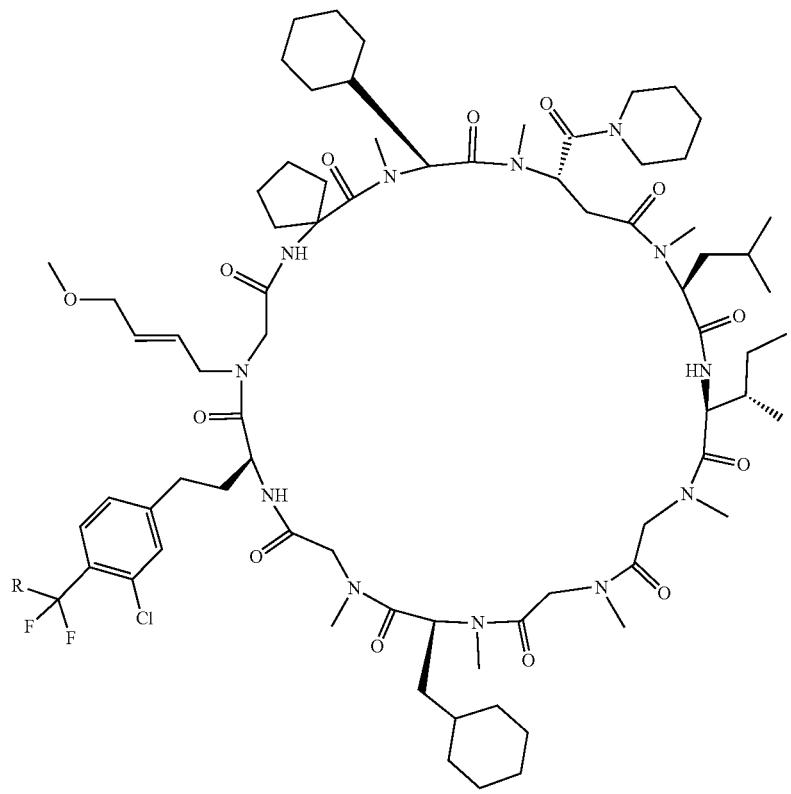

Compound 2051

Compound 899 (50 mg, 35 μmol) was dissolved in 1,2-dichloroethane (0.69 mL), Stewart-Grubbs catalyst (CAS No. 927429-61-6, 29.7 mg, 1.5 equiv.) and allyl methyl ether (52 μL, 16 equiv.) were added, and the mixture was stirred at room temperature for two hours. Stewart-Grubbs catalyst (CAS No. 927429-61-6, 29.7 mg, 1.5 equiv.) and allyl methyl ether (52 μL, 16 equiv.) were further added, the mixture was stirred for two hours, and the reaction solution was then concentrated under reduced pressure. The resulting residue was purified by reverse phase column chromatography and then further purified by preparative HPLC to give Compound 2051 ((11S,17S,26S,29S, 33S,36S)-11-[2-[3-chloro-4-(trifluoromethyl)phenyl]ethyl]-36-cyclohexyl-17-(cyclohexylmethyl)-29-isobutyl-9-[(E)-4-methoxybut-2-enyl]-15,18,21,24,30,34,37-heptamethyl-26-[(1S)-1-methylpropyl]-33-(piperidine-1-carbonyl)-6,9, 12,15,18,21,24,27,30,34,37-undecazaspiro[4.33] octatriacontane-7,10,13,16,19,22,25,28,31,35,38-undecone) (7.4 mg, 14%). The LC/MS data are described in Table 22.

Synthesis of Compound 2055 ((3S,9S,18S,21S,25S, 28S,34S)-28-cyclohexyl-9-(cyclohexylmethyl)-7,10, 13,16,21,22,26,29-octamethyl-18-[(1S)-1-methylpropyl]-25-(piperidine-1-carbonyl)-3-[3-[4-(trifluoromethyl)phenyl]propyl]spiro[1,4,7,10,13,16, 19,22,26,29,32-undecazabicyclo[32.3.0] heptatriacontane-31,1'-cyclopentane]-2,5,8,11,14,17, 20,23,27,30,33-undecone)

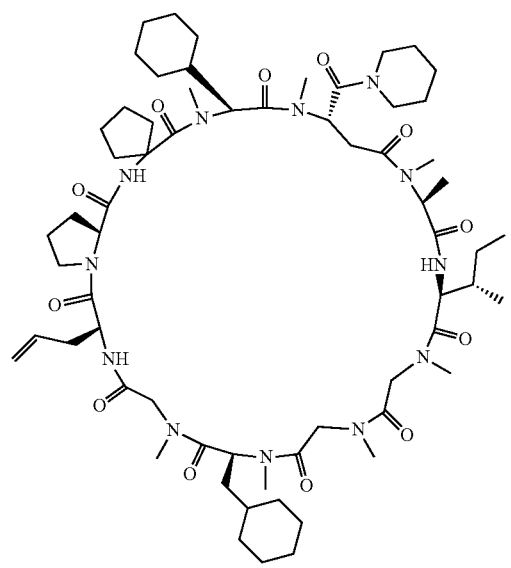

Compound 2055-a

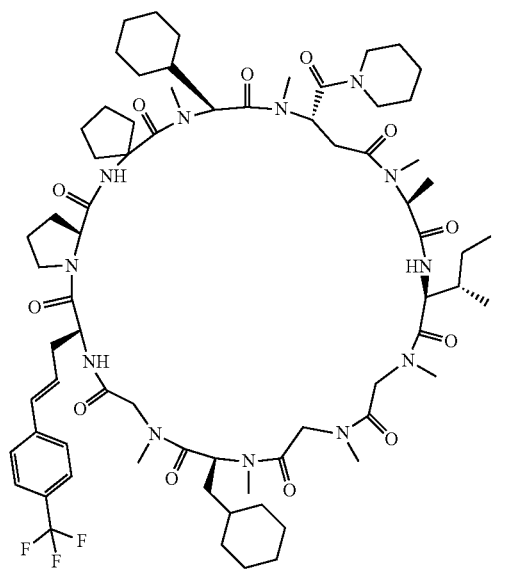

Compound 2055-b

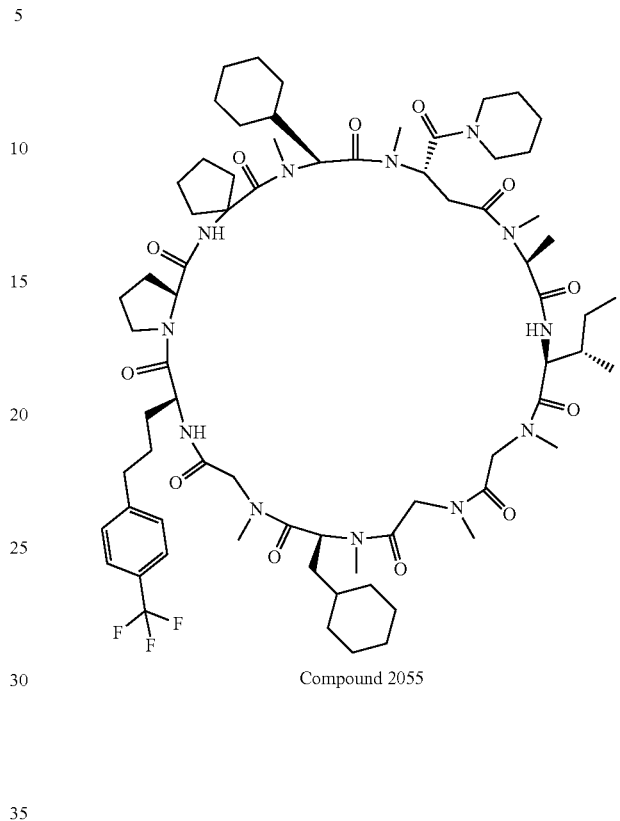

Compound 2055

Compound 2055-a (490 mg, 83%) was obtained by peptide synthesis according to the basic peptide synthesis method described in the present Examples, using Compound aa006-resin ((3S)-3-[9H-fluoren-9-ylmethoxycarbonyl (methyl)amino]-4-oxo-4-piperidin-1-ylbutanoic acid-2-chlorotrityl resin, Fmoc-MeAsp(O-Trt(2-Cl)resin)-pip) (1.6 g, 0.3 mmol/g, 0.48 mmol) as a raw material.

LCMS (ESI) m/z=1234 (M+H)+

Retention time: 0.93 min (analysis condition SQDFA05)

Compound 2055-b was obtained as a crude product by the same method as in Compound 2046 using Compound 2055-a (20 mg, 16 μmol) as a raw material and using 1-(trifluoromethyl)-4-vinylbenzene instead of homoallyl alcohol. The obtained compound 2055-b was dissolved in methanol (3 mL), palladium on carbon (10%) (60 mg) was added, and the mixture was then stirred at room temperature overnight under a hydrogen atmosphere. The reaction solution was concentrated, and the resulting residue was purified by reverse phase column chromatography (10 mM aqueous ammonium acetate solution/water) and then further purified by preparative HPLC to give Compound 2055 ((3S,9S,18S, 21S,25S,28S,34S)-28-cyclohexyl-9-(cyclohexylmethyl)-7, 10,13,16,21,22,26,29-octamethyl-18-[(1S)-1-methylpropyl]-25-(piperidine-1-carbonyl)-3-[3-[4-(trifluoromethyl) phenyl]propyl]spiro[1,4,7,10,13,16,19,22,26,29,32-undecazabicyclo[32.3.0]heptatriacontane-31,1'-cyclopentane]-2,5,8,11,14,17,20,23,27,30,33-undecone) (1.92 mg, 8.6%). The LC/MS data are described in Table 22.

Synthesis of Compound 1411 ((1S,7S,10S,14S,17S, 26S,32S)-32-[(3-iodophenyl)methyl]-7,14-di-isobutyl-3,4,4,9,13,19,22,25,28-nonamethyl-17-[(1S)-1-methylpropyl]-10-(piperidine-1-carbonyl)-3, 6,9,13,16,19,22,25,28,31,34-undecazabicyclo [24.8.6]tetracontane-2,5,8,12,15,18,21,24,27,30,33-undecone)
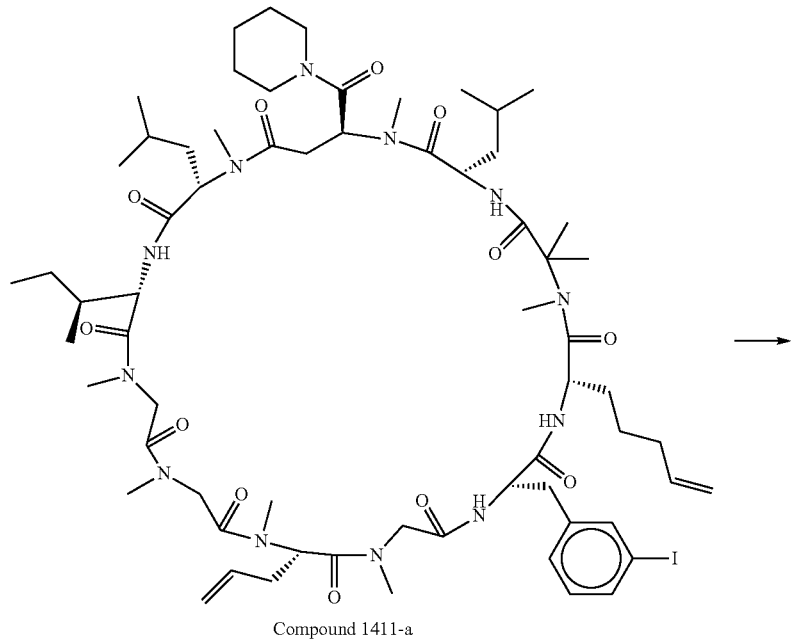
Compound 1411-a
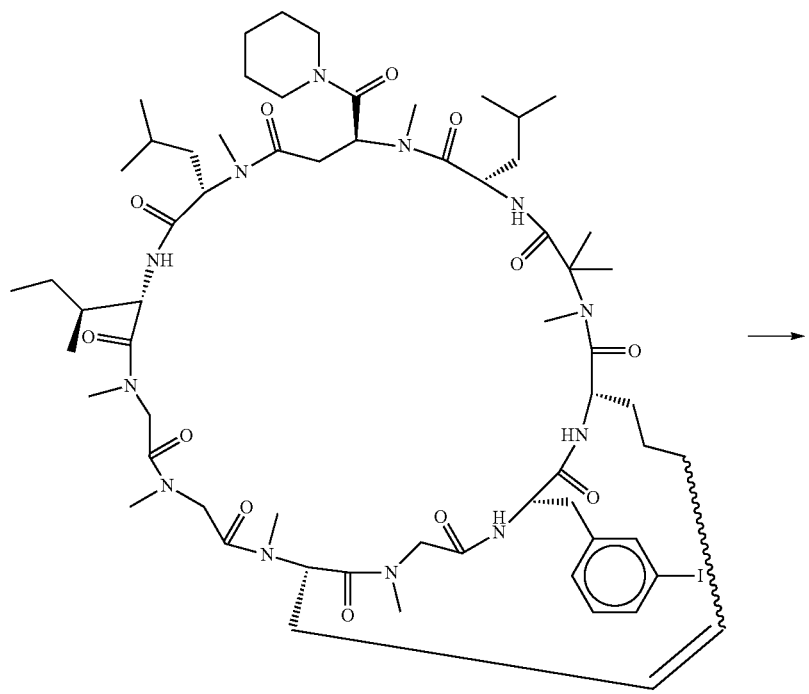
Compound 1411-b

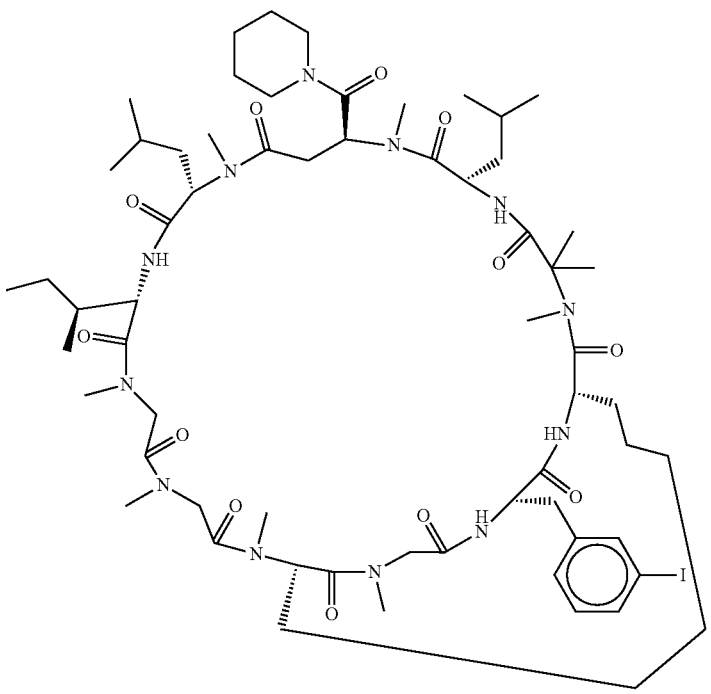

Compound 1411

Compound 1411-a (56.1 mg, 31%) was obtained by peptide synthesis according to the basic peptide synthesis method described in the present Examples, using Compound aa006-resin ((3S)-3-[9H-fluoren-9-ylmethoxycarbonyl (methyl)amino]-4-oxo-4-piperidin-1-ylbutanoic acid-2-chlorotrityl resin, Fmoc-MeAsp (O-Trt(2-Cl)resin)-pip) (0.3 g, 0.436 mmol/g, 0.131 mmol) as a raw material.

LCMS (ESI) m/z=1372 (M+H)+

Retention time: 0.97 min (analysis condition SQDFA05)

Stewart-Grubbs catalyst (CAS No. 927429-61-6, 3.6 mg, 6.3 μmol) was added to a solution of Compound 1411-a (28.7 mg, 21 μmol) in 1,2-dichloroethane (3 mL), and the mixture was stirred at a temperature between 45° C. and 50° C. for five hours. The reaction solution was concentrated under reduced pressure, and the resulting residue was purified by reverse phase column chromatography to give Compound 1411-b (23 mg, 82%).

LCMS (ESI) m/z=1344 (M+H)+

Retention time: 0.90 min (analysis condition SQDFA05)

Platinum(IV) oxide (4 mg, 18 μmol) was added to a solution of Compound 1411-b (20.2 mg, 15 μmol) in ethanol (1.5 mL), the atmosphere in the reaction vessel was replaced with hydrogen, and the mixture was stirred at room temperature for 90 minutes. The reaction solution was filtered through celite, the filtrate was concentrated under reduced pressure, and the resulting residue was purified by reverse phase column chromatography to give Compound 1411 ((1S,7S,10S,14S,17S,26S,32S)-32-[(3-iodophenyl)methyl]-7,14-diisobutyl-3,4,4,9,13,19,22,25,28-nonamethyl-17-[(1S)-1-methylpropyl]-10-(piperidine-1-carbonyl)-3,6,9,13, 16,19,22,25,28,31,34-undecazabicyclo[24.8.6]tetracontane-2,5,8,12,15,18,21,24,27,30,33-undecone) (14 mg, 69%). The LC/MS data are described in Table 22.

1-5. Cyclic Peptide Synthesis Using Fmoc-Protected Dipeptides as Reagents

Synthesis of Compound 2144-b (2-(N-[(2S)-4-[3-chloro-4-(trifluoromethyl)phenyl]-2-(9H-fluoren-9-ylmethoxycarbonylamino)butanoyl]anilino)acetic acid)

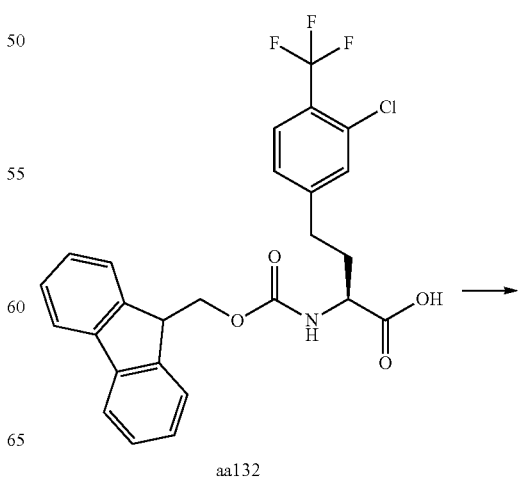

aa132

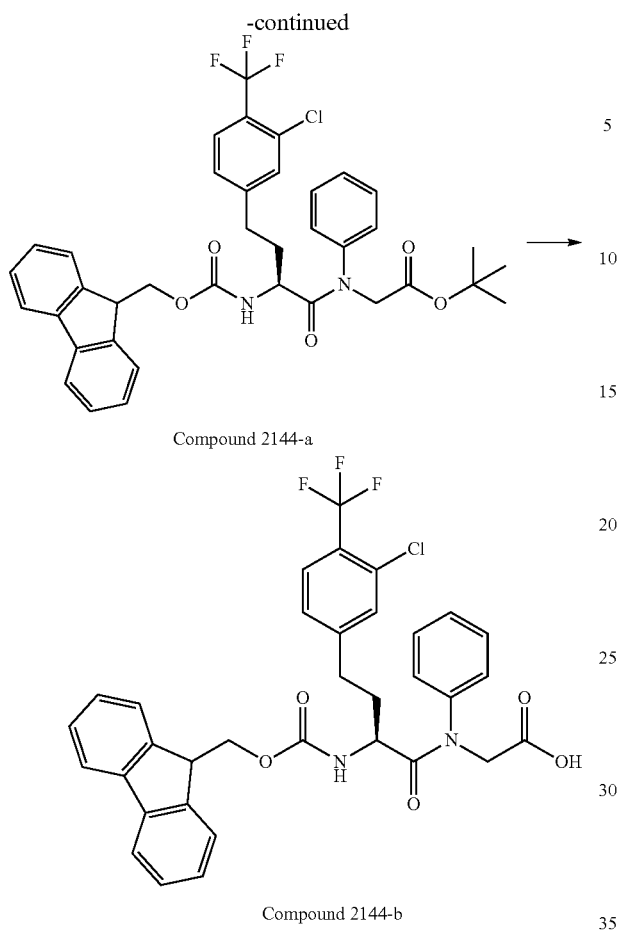

Compound 2144-a

Compound 2144-b

Thionyl chloride (4.32 mL, 59.5 mmol) and DMF (154 µL, 1.985 mmol) were added to a solution of Compound aa132 (10 g, 19.85 mmol) in DCM (397 mL), and the mixture was stirred at room temperature for four days. The solvent was evaporated from the reaction solution under reduced pressure to give an acid chloride (10.95 g), which was used as it is for the next reaction.

A solution of tert-butyl 2-anilinoacetate (1.8 g, 8.68 mmol) in DCM (25 mL) was added to a solution of the above-obtained acid chloride (4.76 g, 9.12 mmol) in DCM (65 mL) at 0° C., and the mixture was stirred at room temperature for four hours. Methanol (1.8 mL) and a saturated aqueous ammonium chloride solution were added, and the mixture was extracted with DCM. The resulting organic layer was washed with a saturated aqueous ammonium chloride solution and dried over anhydrous sodium sulfate, and the solvent was then evaporated under reduced pressure. The resulting residue was purified by reverse phase column chromatography (acetonitrile with 0.1% formic acid/distilled water with 0.1% formic acid) to give Compound 2144-a (4.27 g, 71%).

LCMS (ESI) m/z=693.2 (M+H)+

Retention time: 1.18 min (analysis condition SQDFA05)

TMSCl (2.307 mL, 18.18 mmol) was added to a solution of Compound 2144-a (4.2 g, 6.06 mmol) in TFE (30.3 mL) at room temperature, and the mixture was stirred. After confirming by LC/MS that the reaction was completed, the reaction solution was concentrated under reduced pressure, and the resulting residue was purified by reverse phase column chromatography (acetonitrile with 0.1% formic acid/distilled water with 0.1% formic acid) to give Compound 2144-b (2-(N-[(2S)-4-[3-chloro-4-(trifluoromethyl)phenyl]-2-(9H-fluoren-9-ylmethoxycarbonylamino)butanoyl]anilino)acetic acid) (3.795 g, 98%).

LCMS (ESI) m/z=637.2 (M+H)+

Retention time: 1.01 min (analysis condition SQDFA05)

Synthesis of Compound 2146-b (2-(4-chloro-N-[(2S)-4-[3-chloro-4-(trifluoromethyl)phenyl]-2-(9H-fluoren-9-ylmethoxycarbonylamino)butanoyl]anilino)acetic acid)

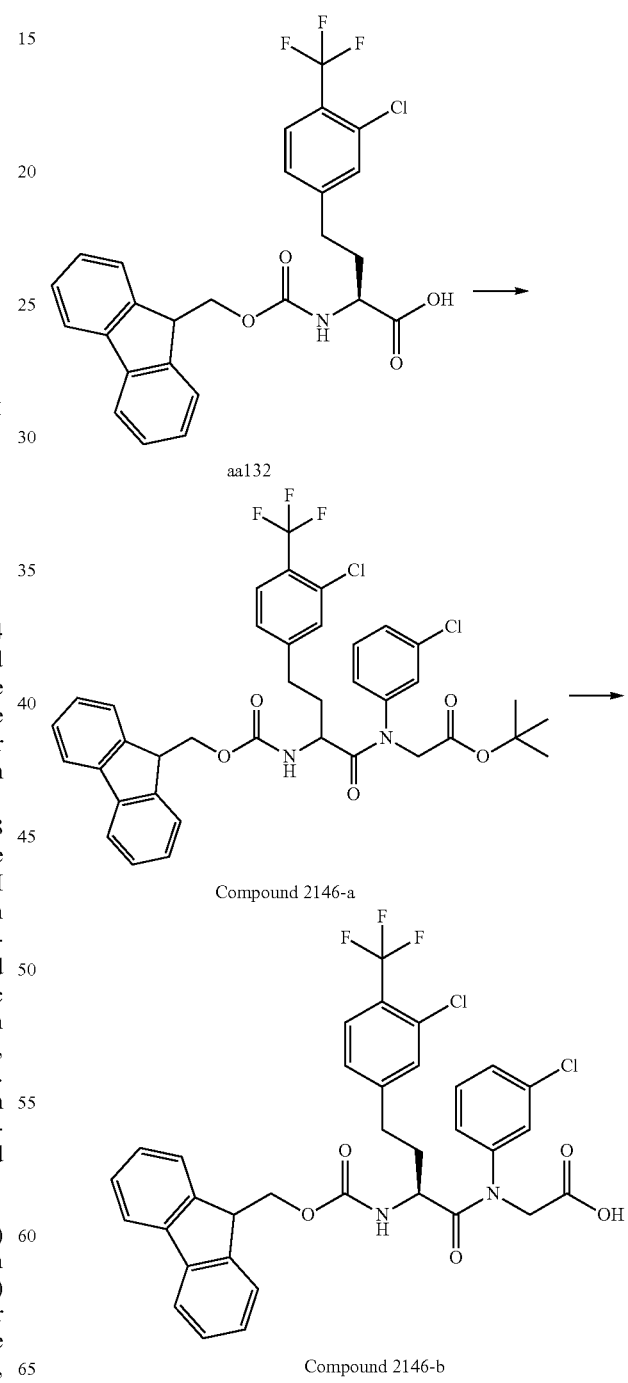

aa132

Compound 2146-a

Compound 2146-b

Compound 2146-b (2-(4-chloro-N-[(2S)-4-[3-chloro-4-(trifluoromethyl)phenyl]-2-(9H-fluoren-9-ylmethoxycarbonylamino)butanoyl]anilino)acetic acid) (3.9 g, 97%) was obtained in the same manner as in the synthesis of Compound 2144-b using tert-butyl 2-(3-chloroanilino)acetate instead of N-phenylglycine tert-butyl 2-anilinoacetate.

LCMS (ESI) m/z=671.2 (M+H)+

Retention time: 1.05 min (analysis condition SQDFA05)

Synthesis of Compound 2147-b (2-(4-chloro-N-[(2S)-4-[3-chloro-4-(trifluoromethyl)phenyl]-2-(9H-fluoren-9-ylmethoxycarbonylamino)butanoyl]anilino)acetic acid)

-continued

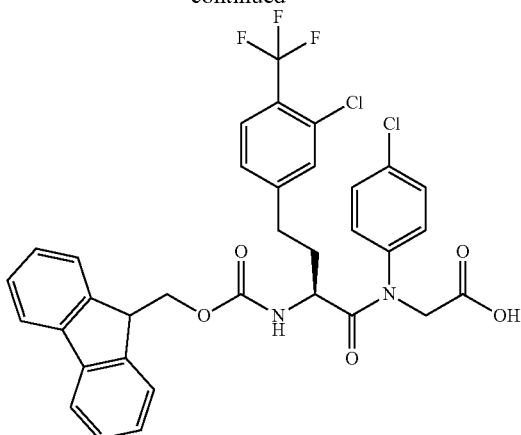

Compound 2147-b

Compound 2147-b (2-(4-chloro-N-[(2S)-4-[3-chloro-4-(trifluoromethyl)phenyl]-2-(9H-fluoren-9-ylmethoxycarbonylamino)butanoyl]anilino)acetic acid) (3.21 g, 94%) was obtained in the same manner as in the synthesis of Compound 2144-b using tert-butyl 2-(4-chloroanilino)acetate instead of N-phenylglycine tert-butyl 2-anilinoacetate.

LCMS (ESI) m/z=671 (M+H)+

Retention time: 1.06 min (analysis condition SQDFA05)

Synthesis of Compound 2149-b (2-[[(2S)-4-[3-chloro-4-(trifluoromethyl)phenyl]-2-(9H-fluoren-9-ylmethoxycarbonylamino)butanoyl]-thiophen-3-ylamino]acetic acid)

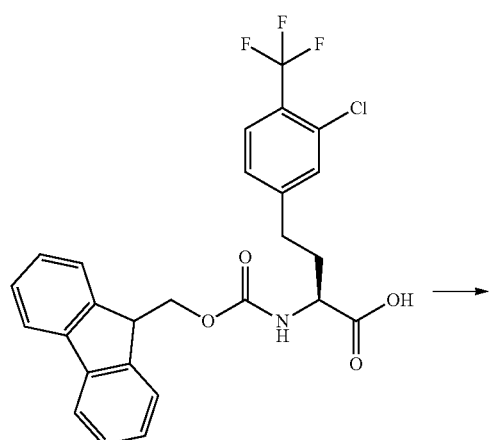

aa132

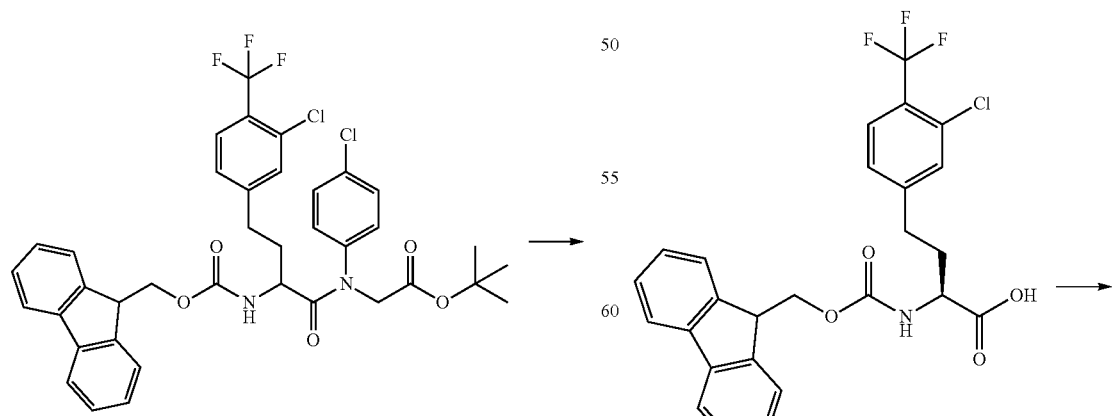

Compound 2147-a aa132

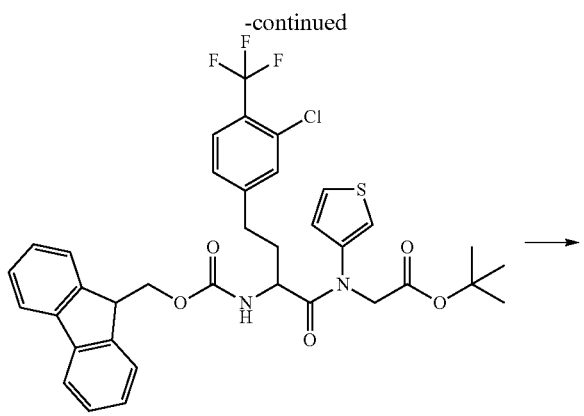

Compound 2149-a

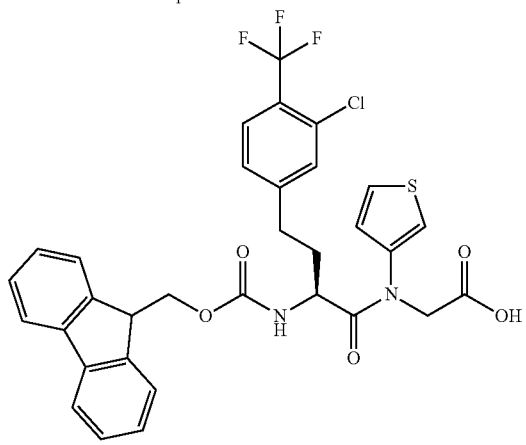

Compound 2149-b

Compound 2149-b (2-[[(2S)-4-[3-chloro-4-(trifluoromethyl)phenyl]-2-(9H-fluoren-9-ylmethoxycarbonylamino)butanoyl]-thiophen-3-ylamino]acetic acid) (4.3 g, quant.) was obtained in the same manner as in the synthesis of Compound 2144-b using tert-butyl 2-(thiophen-3-ylamino)acetate instead of N-phenylglycine tert-butyl 2-anilinoacetate.

LCMS (ESI) m/z=643 (M+H)+

Retention time: 1.00 min (analysis condition SQDFA05)

Synthesis of Compounds 2143-2151

Compounds 2143-2151 were obtained by peptide synthesis according to the basic peptide synthesis method described in the present Examples, using Compound 2144-b, 2146-b, 2147-b, and 2149-b as reagents. The LC/MS data are described in Table 22.

Synthesis of Compound 2180 ((11S,17S,26S,29S,33S,36S)-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-9-[2-(4-methylpiperazin-1-yl)ethyl]-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone)

Compound 2180 was synthesized according to the following scheme.

aa006-resin

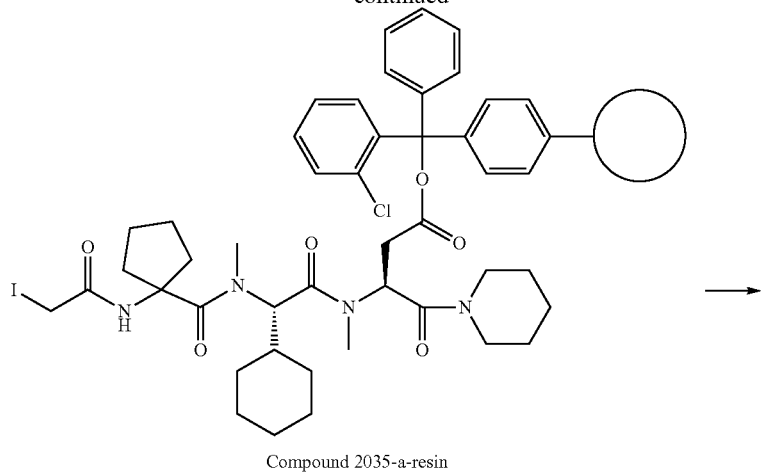
Compound 2035-a-resin
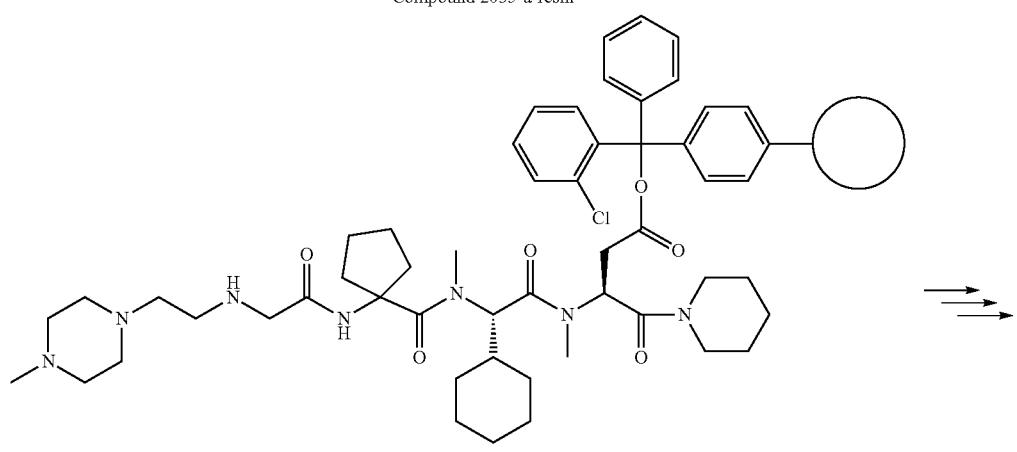
Compound 2180-a-resin
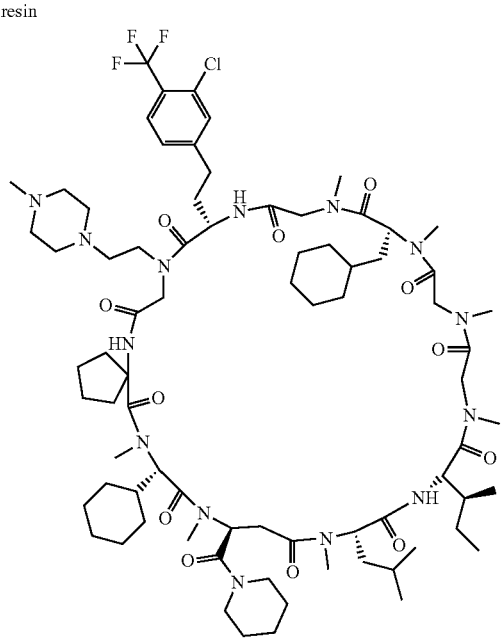
Compound 2180
Compound aa006-resin ((3S)-3-[19H-fluoren-9-yl-methoxycarbonyl(methyl)amino]-4-oxo-4-piperidin-1-ylbutanoic acid-2-chlorotrityl resin, Fmoc-MeAsp(O-Trt(2-Cl) resin)-pip) (100 mg, 0.411 mmol/g, 0.0411 mmol) was used as a raw material, and by subjecting the obtained Compound 2035-a-resin to reaction with 2-(4-methylpiperazin-1-yl)

ethanamine hydrochloride (CAS: 401817-30-9) (0.45 mol/L solution in N-methylpyrrolidone, 0.3 mL) in the presence of DIPEA, iodine was substituted with an amino group to give Compound 2180-a-resin. Subsequent peptide chain elongation and cyclic peptide synthesis were performed according to the basic peptide synthesis method to obtain Compound 2180 ((11S,17S,26S,29S,33S,36S)-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-9-[2-(4-methylpiperazin-1-yl)ethyl]-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone) (6.4 mg, 9%).

LCMS (ESI) m/z=1528.3 (M+H)+

Retention time: 0.82 min (analysis condition SQDFA05)

Synthesis of Compound 2181 ((3S,6S,9S,13S,16S,31S,34S)-25-[2-[3-chloro-4-(trifluoromethyl)phenyl]ethyl]-23-[2-[2-(dimethylamino)ethoxy]ethyl]-9-isobutyl-N,N,3,4,10,14,17,29,32-nonamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide)

Compound 2181 was synthesized according to the following scheme.

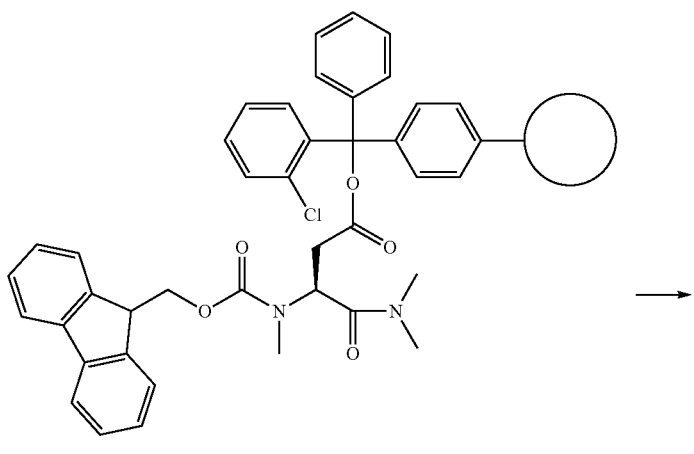

aa011-resin

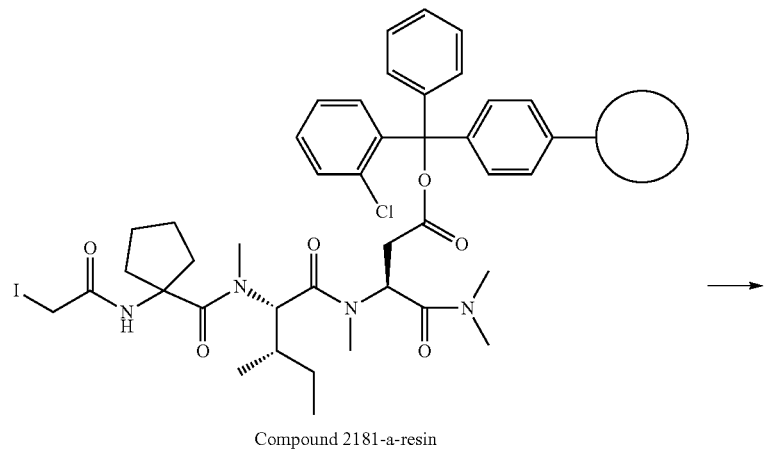

Compound 2181-a-resin

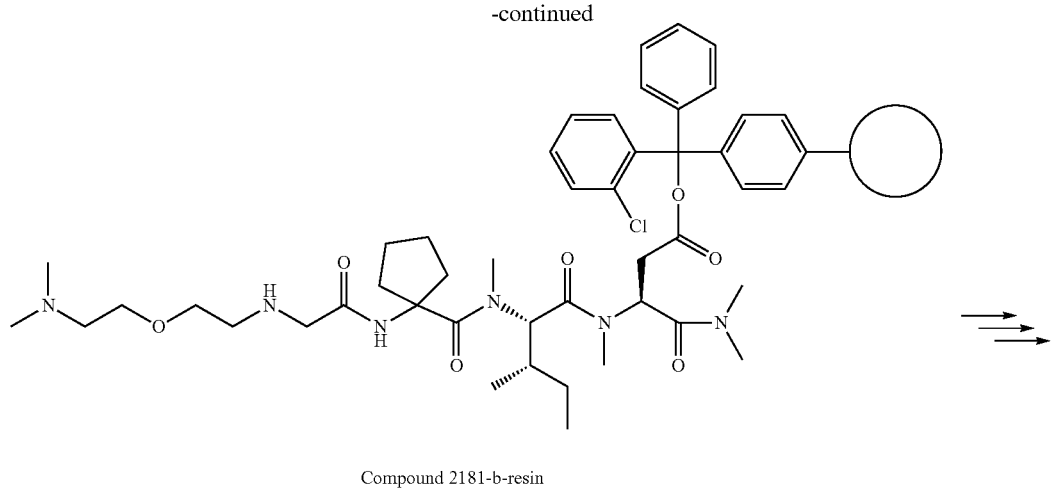

Compound 2181-b-resin

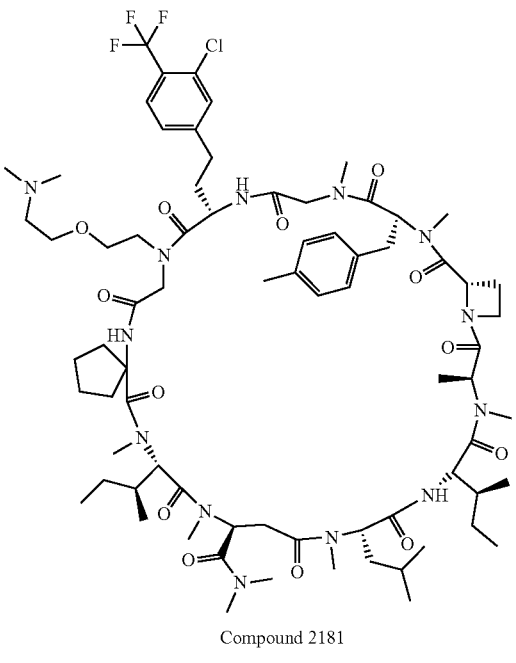

Compound 2181

Peptide synthesis according to the basic peptide synthesis method described in the present Example was performed using Compound aa011-resin ((3S)-4-(dimethylamino)-3-[9H-fluoren-9-ylmethoxycarbonyl(methyl)amino]-4-oxobutanoic acid-2-chlorotrityl resin, Fmoc-MeAsp (O-Trt(2-Cl)resin)-NMe2) (100 mg, 0.456 mmol/g, 0.0456 mmol) as a raw material. Elongation with Fmoc-MeIle-OH and then with Fmoc-cLeu-OH, and deprotection of the Fmoc group were followed by condensation between the amino groups on the resin and iodoacetic acid in a mixture of a solution of iodoacetic acid (0.6 mol/L, 0.3 mL) in NMP/DMF (1/1) and a solution of diisopropylcarbodiimide (DIC) in N,N-dimethylformamide (DMF) (10% v/v, 0.36 mL) to obtain Compound 2181-a-resin in which the N-terminus of the peptide on the resin was iodinated. By further allowing 2-(2-aminoethoxy)-N,N-dimethylethanamine (CAS: 85322-63-0) (0.45 mol/L solution in N-methylpyrrolidone, 0.3 mL) to react in the presence of DIPEA, iodine was substituted with an amino group to obtain Compound 2181-b-resin. Subsequent peptide chain elongation and cyclic peptide synthesis were performed according to the basic peptide synthesis method to give Compound 2181 ((3S,6S,9S,13S,16S,31S,34S)-25-[2-[3-chloro-4-(trifluoromethyl)phenyl]ethyl]-23-[2-[2-(dimethylamino)ethoxy]ethyl]-9-isobutyl-N,N,3,4,10,14,17,29,32-nonamethyl-6,16-bis[(1S)-1-methylpropyl]-2,5,8,11,15,18,21,24,27,30,33-undecaoxo-31-(p-tolylmethyl)spiro[1,4,7,10,14,17,20,23,26,29,32-undecazabicyclo[32.2.0]hexatriacontane-19,1'-cyclopentane]-13-carboxamide) (1.7 mg, 2.5%).

LCMS (ESI) m/z=1485.2 (M+H)+

Retention time: 0.77 min (analysis condition SQDFA05)

Synthesis of Compound 2182 ((3S,6S,9S,13S,16S, 25S,31S,34S)-23-[2-(azetidin-3-yl)ethyl]-31-(cyclohexylmethyl)-16-cyclopentyl-25-[2-[3-fluoro-4-(trifluoromethyl)phenyl]ethyl]-9-isobutyl-N,N,3,4,10,14, 17,29,32-nonamethyl-6-[(1S)-1-methylpropyl]-2,5,8, 11,15,18,21,24,27,30,33-undecaoxo-spiro[1,4,7,10, 14,17,20,23,26,29,32-undecazabicyclo[32.2.0] hexatriacontane-19,1'-cyclopentane]-13-carboxamide)
Compound 2182 was synthesized according to the following scheme.
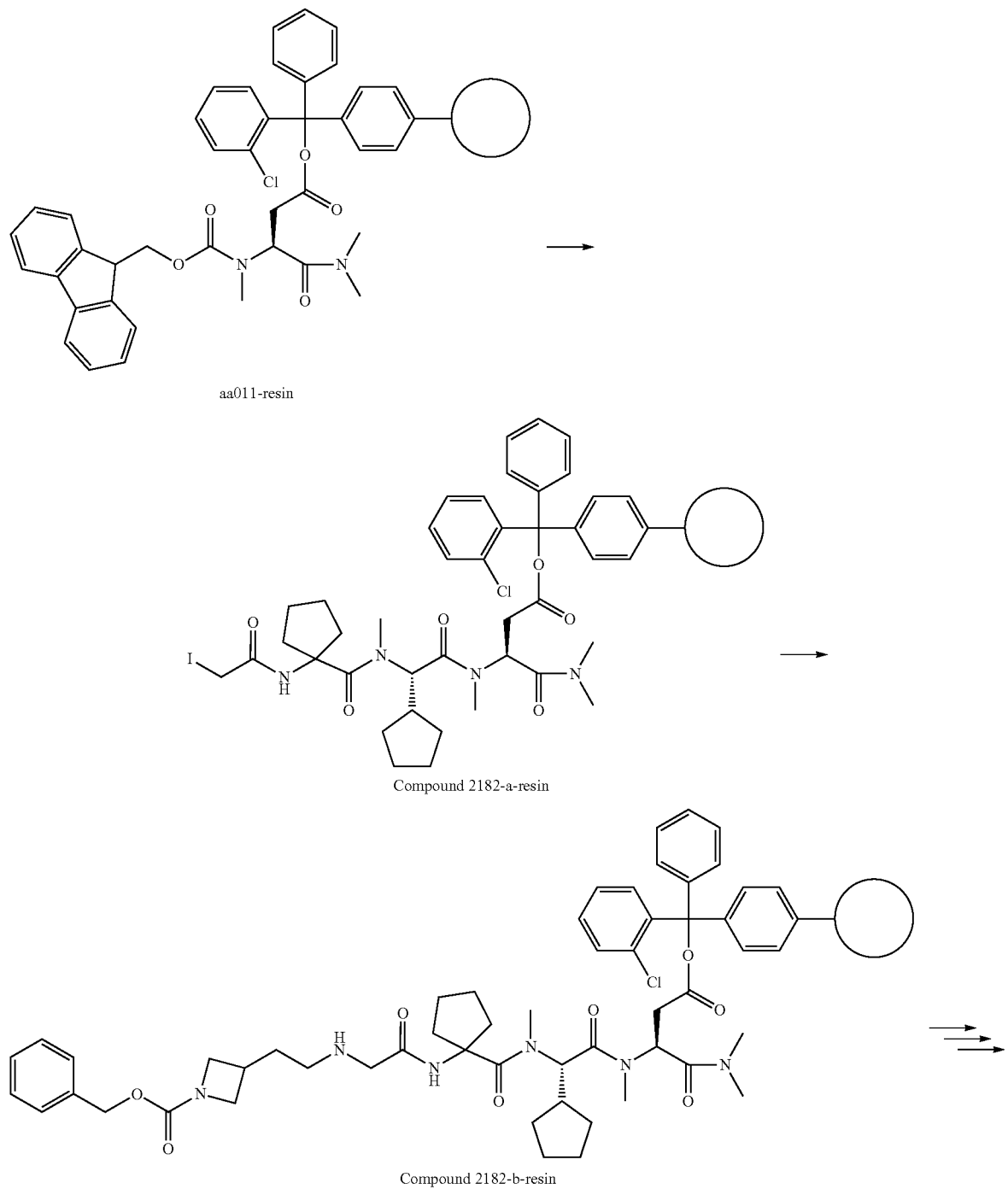

-continued

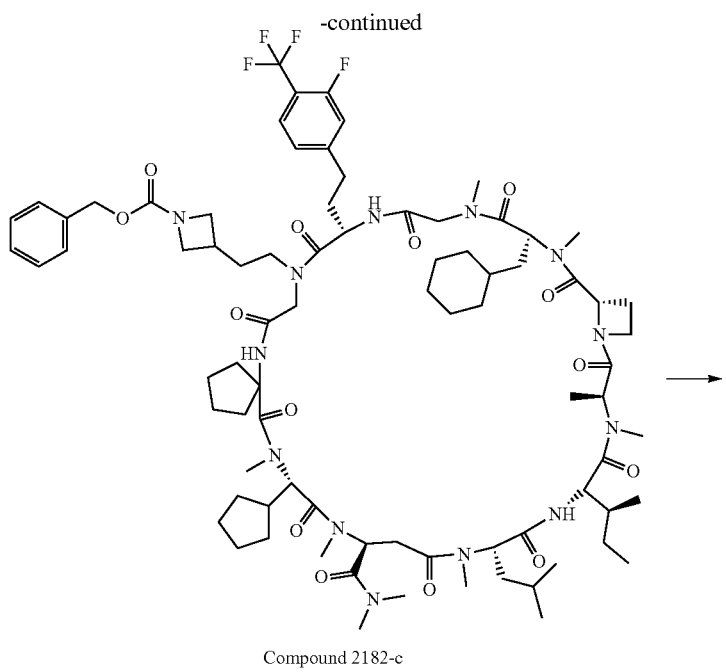

Compound 2182-c

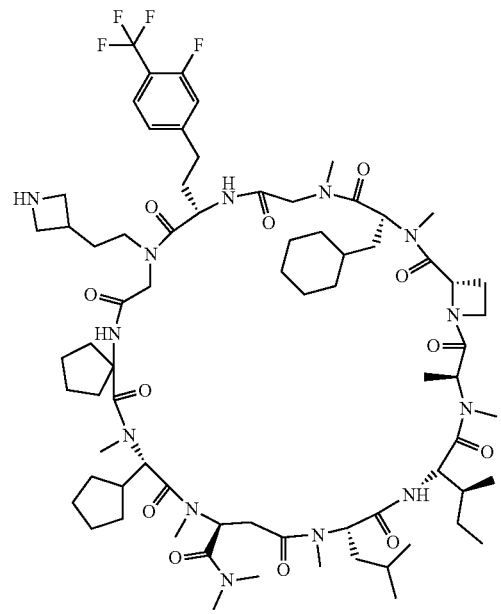

Compound 2182

Peptide synthesis according to the basic peptide synthesis method described in the present Example was performed using Compound aa011-resin ((3S)-4-(dimethylamino)-3-[9H-fluoren-9-ylmethoxycarbonyl(methyl)amino]-4-oxobutanoic acid-2-chlorotrityl resin, Fmoc-MeAsp (O-Trt(2-Cl) resin)-NMe2) (100 mg, 0.456 mmol/g, 0.0456 mmol) as a raw material. Elongation with Fmoc-MeGly(cPent)-OH (aa079) and then with Fmoc-cLeu-OH, and deprotection of the Fmoc group were followed by condensation between the amino groups on the resin and iodoacetic acid in a mixture of a solution of iodoacetic acid (0.6 mol/L, 0.3 mL) in NMP/DMF (1/1) and a solution of diisopropylcarbodiimide (DIC) in N,N-dimethylformamide (DMF) (10% v/v, 0.36 mL) to obtain Compound 2182-a-resin in which the N-terminus of the peptide on the resin was iodinated. By further allowing 1-azetidine carboxylic acid, 3-(2-aminoethyl)-phenylmethylester (CAS: 1420898-03-8) (0.45 mol/L solution in N-methylpyrrolidone, 0.3 mL) to react in the presence of DIPEA, Compound 2182-b-resin was obtained. Subsequent peptide chain elongation and cyclic peptide synthesis were performed according to the basic peptide synthesis method to give Compound 2182-c (6 mg, 2.5%). Compound 2182-c (6 mg) was dissolved in acetic acid (1 mL), and 10 wt % palladium-activated carbon (5.0 mg) was added thereto. Upon purging the reaction vessel with hydrogen, this mixture was stirred at room temperature for one hour. With additional 10 wt % palladium-activated carbon (5.0 mg), the mixture was stirred under a hydrogen atmosphere at room temperature for another two hours. The reaction solution was filtered through celite, the solids were washed with ethanol, and then the filtrate was concentrated under reduced pressure to obtain a crude product. The crude product was purified by fractionation HPLC to obtain Compound 2182 ((3S,6S,9S,13S,16S,25S,31S,34S)-23-[2-(azetidin-3-yl)ethyl]-31-(cyclohexylmethyl)-16-cyclopentyl-25-[2-[3-fluoro-4-(trifluoromethyl)phenyl]ethyl]-9-isobutyl-N,N,3,4,10,14,17,29,32-nonamethyl-6-[(1S)-1-methylpropyl]-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide) (1.25 mg, 23%).

LCMS (ESI) m/z=1441.2 (M+H)+

Retention time: 2.42 min (analysis condition SQDFA05long)

Synthesis of Compound 2183 ((3S,6S,9S,13S,16S,25S,31S,34S)-25-[2-[3-chloro-4-(trifluoromethyl)phenyl]ethyl]-31-(cyclohexylmethyl)-16-cyclopentyl-9-isobutyl-N,N,3,4,10,14,17,29,32-nonamethyl-23-[2-[2-(methylamino)ethoxy]ethyl]-6-[(1S)-1-methylpropyl]-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide)

Compound 2183 was synthesized according to the following scheme.

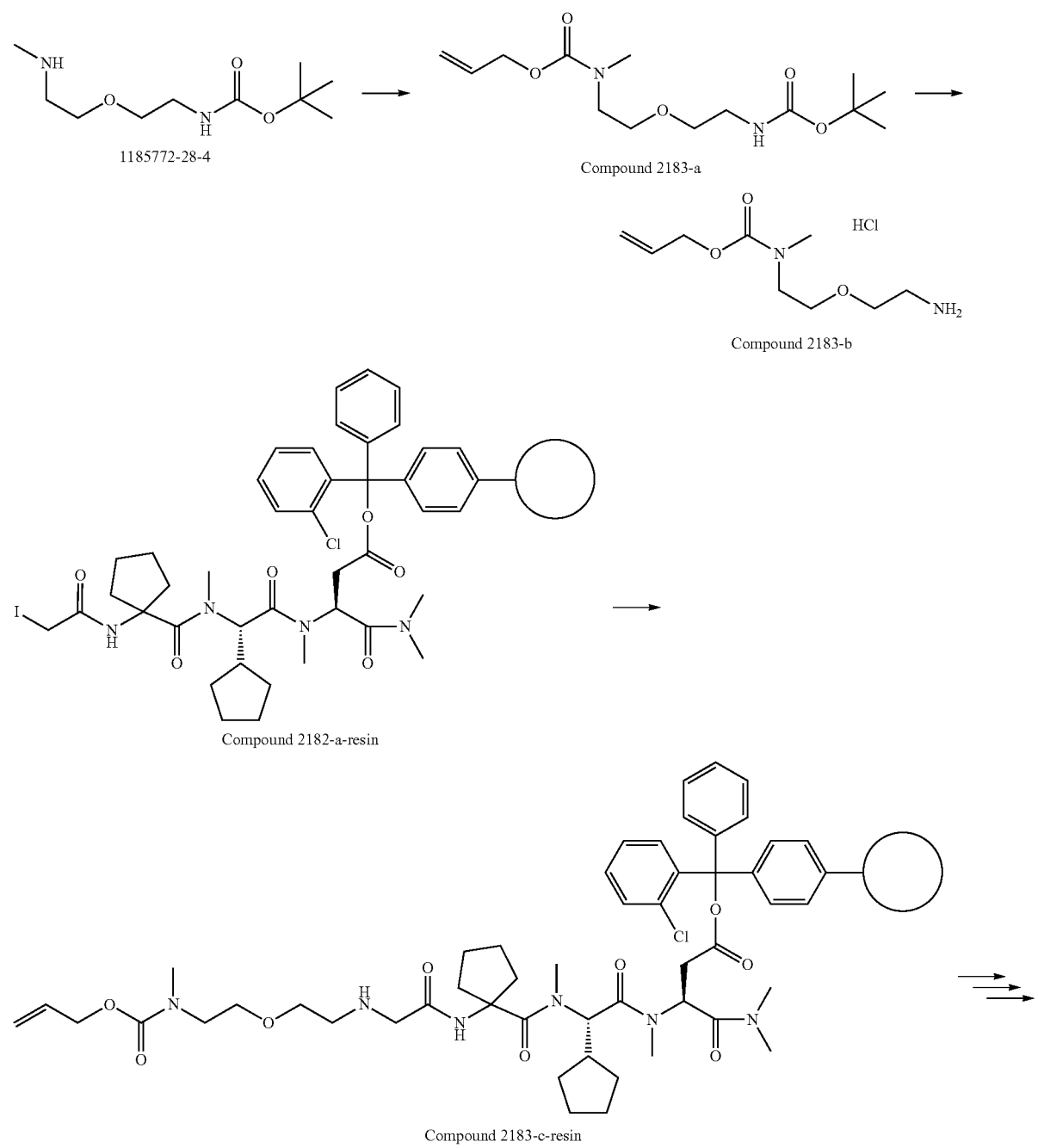

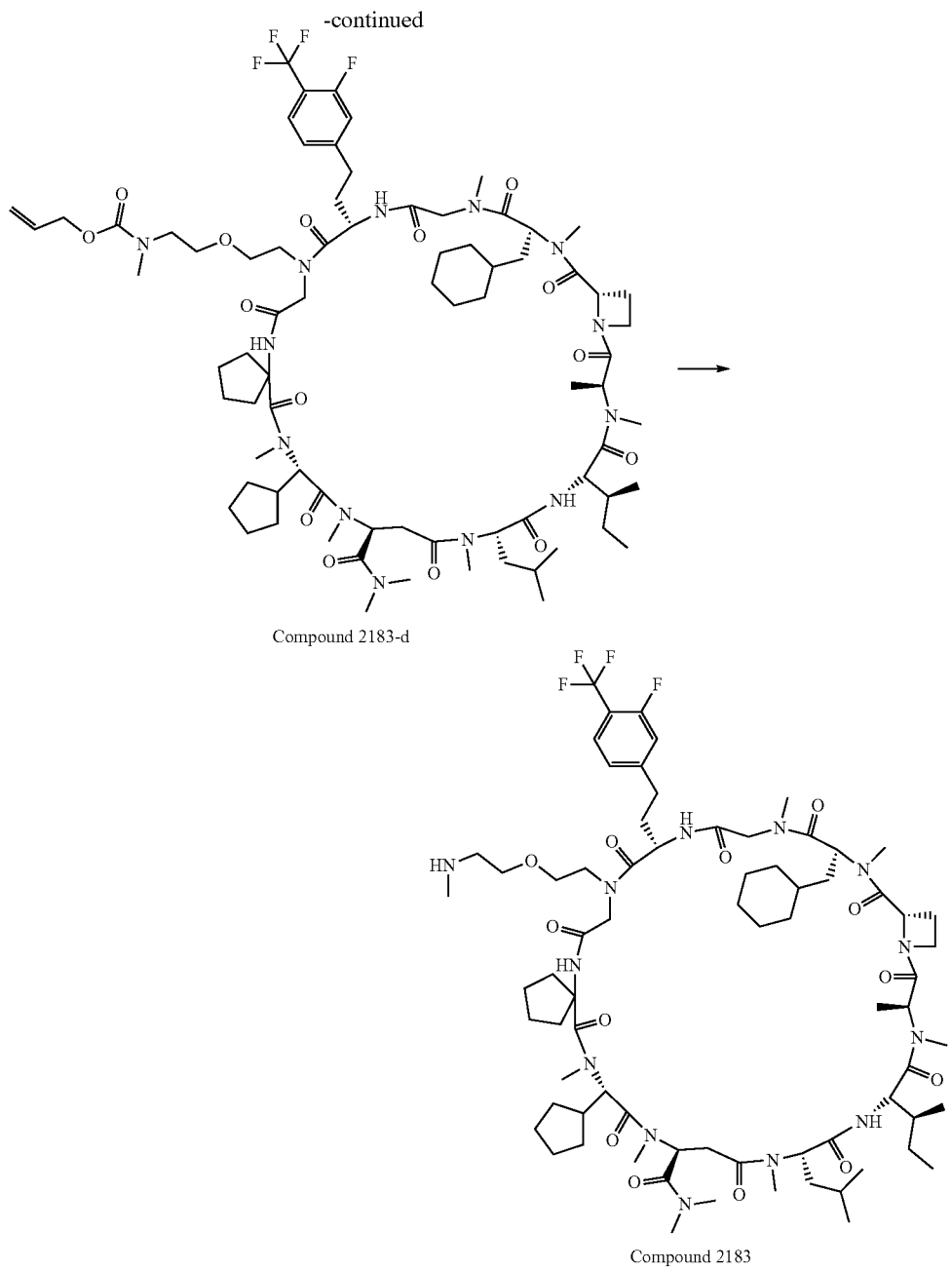

Compound 2183-d

Compound 2183

Carbamic acid, N-[2-[2-(methylamino)ethoxy]ethyl]-,1,1-dimethylethylester (CAS: 1185772-28-4) (2.00 g, 9.16 mmol) was dissolved in a mixture of THF (3 mL) and water (2 mL), and cooled to 0° C. Aqueous sodium carbonate solution (2 mol/L, 4.58 mL, 1 equivalent) and allyl chloroformate (Alloc-Cl) (0.883 g, 0.8 equivalents) were added thereto, and then aqueous sodium carbonate solution (2 mol/L, 2.29 mL, 0.5 equivalents) was added, and the mixture was stirred at room temperature for 45 minutes. The reaction solution was diluted with water, and extracted twice with MTBE. The organic phases were combined, the mixture was washed with brine and dried over sodium sulfate, and the solvent was evaporated under reduced pressure. The obtained residue was purified by silica gel column chromatography (hexane/ethyl acetate) to obtain Compound 2183-a (1.79 g, 64.6%).

LCMS (ESI) m/z=303.18 (M+H)+(analysis condition SQDFA05)

$^1$H-NMR (DMSO-D$_6$) δ: 6.79-6.67 (1H, m), 6.00-5.83 (1H, m), 5.31-5.22 (1H, m), 5.20-5.13 (1H, m), 4.53-4.48 (1H, m), 3.49 (2H, t, J=5.6 Hz), 3.40-3.32 (4H, m), 3.05 (2H, q, J=5.8 Hz),2.91-2.82 (3H, m), 1.37 (9H, s).

To the above-obtained Compound 2183-a (0.9 g, 2.98 mmol) was added a hydrogen chloride, 1,4-dioxane solution (4 mol/L, 6.61 mL, 8.5 equivalents), and the mixture was allowed to react at room temperature for six hours. The reaction solution was concentrated to obtain Compound 2183-b (1.08 g).

LCMS (ESI) m/z=203.06 (M+H)+(analysis condition SQDFA05)

$^1$H-NMR (DMSO-D$_6$) δ: 7.89 (3H, bs), 5.92 (1H, ddd, J=16.2, 10.7, 5.2 Hz), 5.31-5.23 (1H, m), 5.21-5.16 (1H, m), 4.53-4.49 (2H, m), 3.62-3.51 (4H, m), 3.44-3.37 (2H, m), 3.00-2.92 (2H, m), 2.92-2.84 (3H, m).

Compound 2182-a-resin was allowed to react with carbamic acid, N-[2-(2-aminoethoxy)ethyl]-N-methyl-,2-propan-1-ylester hydrochloride (Compound 2183-b) (0.45 mol/L solution in N-methyl pyrrolidone, 0.3 mL) in the presence of DIPEA to obtain Compound 2183-c-resin. Subsequent peptide chain elongation and cyclic peptide synthesis were carried out according to the basic peptide synthesis method to obtain Compound 2183-d (6.59 mg).

Compound 2183-d (6.59 mg) was dissolved in tetrahydrofuran (1 mL) under a nitrogen atmosphere, and a solution of zinc chloride in tetrahydrofuran (0.5 M, 84 μL), tetramethyldisiloxane (30 μL), and tetrakistriphenylphosphine palladium (2.4 mg) were added. The reaction vessel was shaken at room temperature for three hours. The reaction solution was concentrated under reduced pressure to obtain a crude product. The crude product was purified by fractionation HPLC to obtain Compound 2183 ((3S,6S,9S,13S,16S,25S,31S,34S)-25-[2-[3-chloro-4-(trifluoromethyl)phenyl]ethyl]-31-(cyclohexylmethyl)-16-cyclopentyl-9-isobutyl-N,N,3,4,10,14,17,29,32-nonamethyl-23-[2-[2-(methylamino)ethoxy]ethyl]-6-[(1S)-1-methylpropyl]-2,5,8,11,15,18,21,24,27,30,33-undecaoxo-spiro[1,4,7,10,14,17,20,23,26,29,32-undecazabicyclo[32.2.0]hexatriacontane-19,1'-cyclopentane]-13-carboxamide) (1.18 mg, 19%).

LCMS (ESI) m/z=1475.2 (M+H)+

Retention time: 2.55 min (analysis condition SQDFA05long)

Synthesis of Compound 2184 ((11S,17S,26S,29S,33S,36S)-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-9-(2-piperazin-1-ylethyl)-33-(piperidine-1-carbonyl)-6,9,12,15,18,21,24,27,30,34,37-undecazaspiro[4.33]octatriacontane-7,10,13,16,19,22,25,28,31,35,38-undecone)

Compound 2184 was synthesized according to the following scheme.

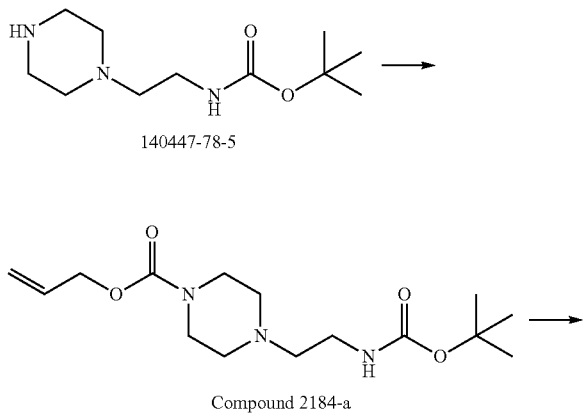

140447-78-5

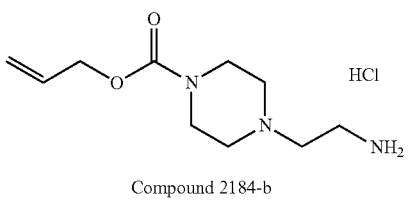

Compound 2184-a

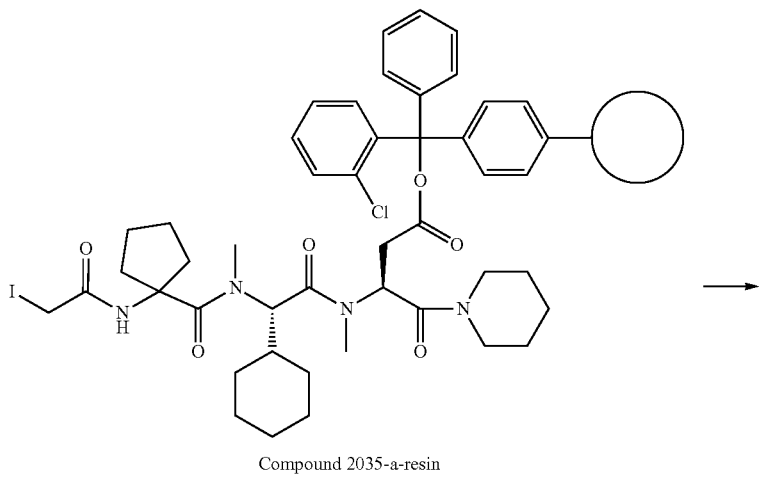

Compound 2184-b

Compound 2035-a-resin

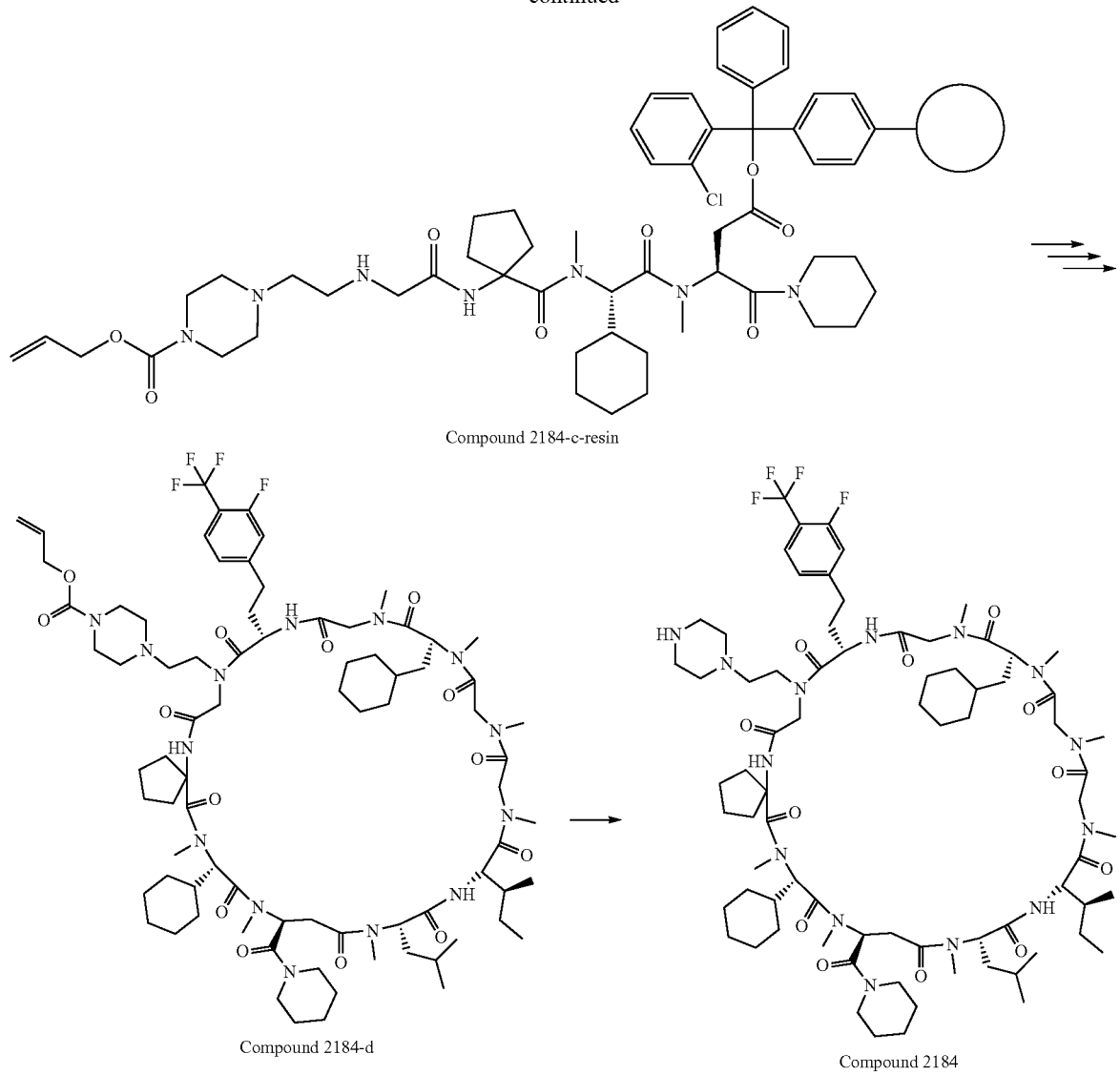

Compound 2184-c-resin

Compound 2184-d

Compound 2184

Carbamic acid, N-[2-(1-piperazinyl)ethyl]-,1,1-dimethyl-ethylester (CAS: 140447-78-5) (4.84 g, 21.11 mmol) was dissolved in a mixture of THF (3 mL) and water (2 mL), and cooled to 0° C. Aqueous sodium carbonate solution (2 mol/L, 10.55 mL, 1 equivalent) and allyl chloroformate (Alloc-Cl) (2.035 g, 0.8 equivalents) were added thereto, and then aqueous sodium carbonate solution (2 mol/L, 5.28 mL, 0.5 equivalents) was added, and the mixture was stirred at room temperature for three hours. The reaction solution was diluted with water, and extracted twice with MTBE. The organic phases were combined, the mixture was washed with brine and dried over sodium sulfate, and the solvent was evaporated under reduced pressure. The obtained residue was purified by silica gel column chromatography (hexane/ethyl acetate) to obtain Compound 2184-a (4.46 g, 84%).

LCMS (ESI) m/z=314.19 (M+H)+

Retention time: 0.85 min (analysis condition SQDAA05)

To the above-obtained Compound 2184-a (1 g, 3.19 mmol) was added a hydrogen chloride, 1,4-dioxane solution (4 mol/L, 6.78 mL, 8.5 equivalents), and the mixture was allowed to react at room temperature overnight. The reaction solution was concentrated to obtain Compound 2184-b (884.1 mg).

LCMS (ESI) m/z=214.10 (M+H)+(analysis condition SQDAA05)

$^1$H-NMR (DMSO-D$_6$) δ: 8.40 (3H, bs), 5.94 (1H, ddd, J=17.2, 10.5, 5.3 Hz), 5.31 (1H, dq, J=17.2, 1.6 Hz), 5.22 (1H, dq, J=10.5, 1.4 Hz), 4.60-4.55 (2H, m), 4.20-3.00 (12H, m).

Compound 2035-a-resin (100 mg, 0.0462 mmol) was allowed to react with Compound 2184-b (0.45 mol/L solution in N-methyl pyrrolidone, 0.3 mL) in the presence of DIPEA to obtain Compound 2184-c-resin. Subsequent peptide chain elongation and cyclic peptide synthesis were carried out according to the basic peptide synthesis method to obtain Compound 2184-d as a crude product.

To Compound 2184-d in THF (0.25 mL), phenylsilane (3.5 mg, 0.32 mmol) and tetrakistriphenylphosphine palladium (14.5 mg, 0.013 mmol) were sequentially added, and the mixture was allowed to react at room temperature for 8 hours and 30 minutes. The obtained reaction solution was purified by reverse phase HPLC to obtain Compound 2184 ((11S,17S,26S,29S,33S,36S)-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-9-(2-piperazin-1-ylethyl)-33-(piperidine-1-carbonyl)-6,9,12,15,18,21,24,27,30,34,37-undecazaspiro[4.33]octatriacontane-7,10,13,16,19,22,25,28,31,35,38-undecone) (2.6 mg, 4.2%).

LCMS (ESI) m/z=1511.7 (M–H)–
Retention time: 0.80 min (analysis condition SQDAA05)

Synthesis of Compound 2185 ((11S,17S,26S,29S, 33S,36S)-9-[2-(2-aminoethoxy)ethyl]-11-[2-[3-chloro-4-(trifluoromethyl)phenyl]ethyl]-36-cyclohexyl-17-(cyclohexylmethyl)-29-isobutyl-15,18,21, 24,30,34,37-heptamethyl-26-[(1S)-1-methylpropyl]-33-(piperidine-1-carbonyl)-6,9,12,15,18,21,24,27,30, 34,37-undecazaspiro[4.33]octatriacontane-7,10,13, 16,19,22,25,28,31,35,38-undecone)

Compound 2185 was synthesized according to the following scheme.

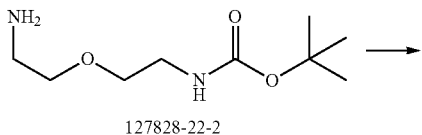
127828-22-2

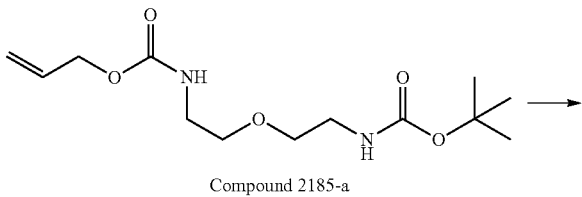
Compound 2185-a

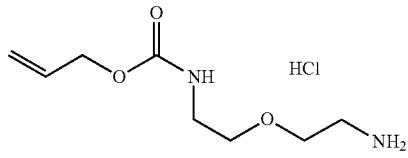
Compound 2185-b

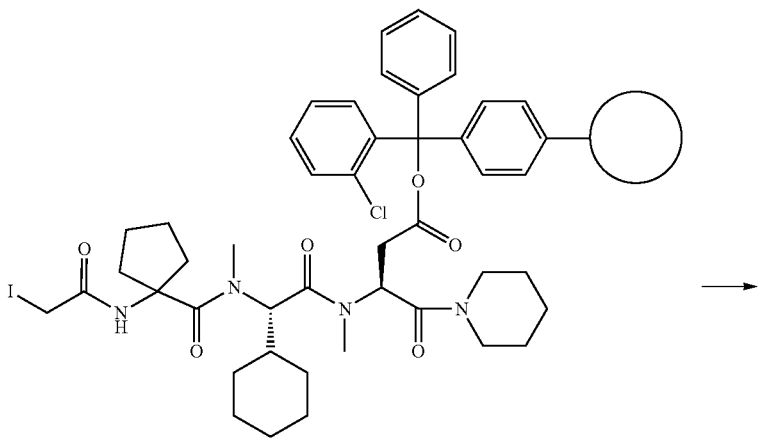
Compound 2035-a-resin

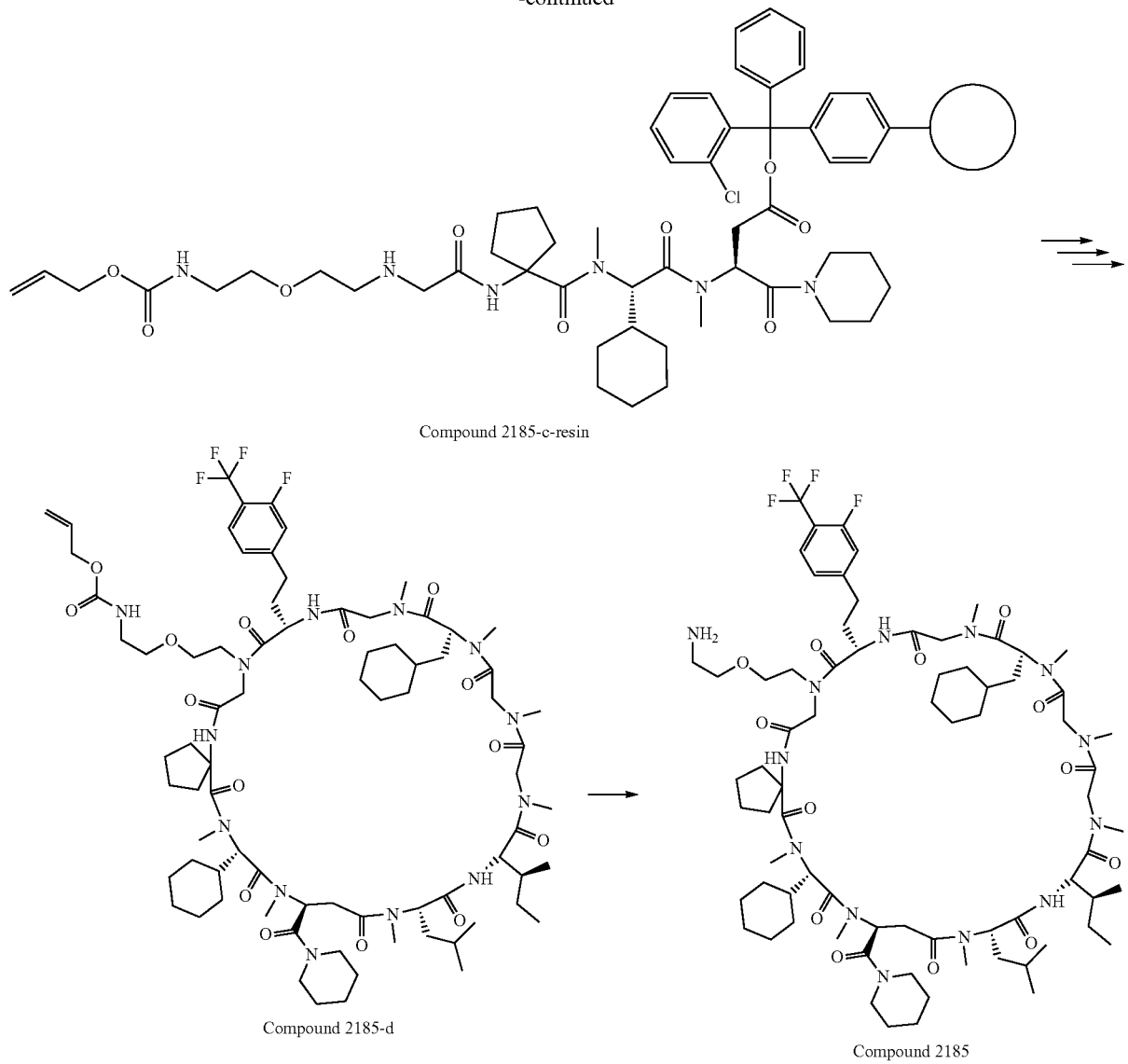

Compound 2185-c-resin

Compound 2185-d

Compound 2185

Carbamic acid, N-[2-(2-aminoethoxy)ethyl]-,1,1-dimethylethylester (CAS: 127828-22-2) (2 g, 9.79 mmol) was dissolved in a mixture of THF (3 mL) and water (2 mL), and cooled to 0° C. Aqueous sodium carbonate solution (2 mol/L, 4.9 mL, 1 equivalent) and allyl chloroformate (Alloc-Cl) (0.828 mL, 7.83 mmol, 0.8 equivalents) were added thereto at 0° C., and then aqueous sodium carbonate solution (2 mol/L, 2.448 mL, 0.5 equivalents) was added, and the mixture was stirred at room temperature. 2.5 hours later, the reaction solution was diluted with water, and extracted twice with MTBE. The organic phases were combined, the mixture was washed with brine and then dried over sodium sulfate, and the solvent was evaporated under reduced pressure. The obtained residue was purified by silica gel column chromatography (hexane/ethyl acetate) to obtain Compound 2185-a (1.5 g, 66%).

LCMS (ESI) m/z=289.13 (M+H)+

Retention time: 0.62 min (analysis condition SQDFA05)

To the above-obtained Compound 2185-a (1.5 g, 5.2 mmol) was added a hydrogen chloride, 1,4-dioxane solution (4 mol/L, 11.05 mL, 8.5 equivalents), and the mixture was stirred at room temperature for six hours. The solvent was evaporated from the reaction solution under reduced pressure to obtain Compound 2185-b (1.35 g).

LCMS (ESI) m/z=189.03 (M+H)+(analysis condition SQDFA05)

$^1$H-NMR (DMSO-D$_6$) δ: 7.96 (3H, bs), 7.32-7.20 (1H, m), 5.91 (1H, ddd, J=17.2, 10.6, 5.3 Hz), 5.33-5.24 (1H, m), 5.20-5.15 (1H, m), 4.53-4.44 (2H, m), 3.65-3.52 (2H, m), 3.63 (2H, t, J=5.7 Hz), 3.19 (2H, q, J=5.7 Hz), 3.03-2.90 (2H, m).

Compound 2035-a-resin (100 mg, 0.0462 mmol) was allowed to react with Compound 2185-b (0.45 mol/L solution in N-methyl pyrrolidone, 0.3 mL) in the presence of DIPEA to obtain Compound 2185-c-resin. Subsequent peptide chain elongation and cyclic peptide synthesis were carried out according to the basic peptide synthesis method to obtain Compound 2185-d (6.66 mg).

Compound 2185-d (6.66 mg) was dissolved in tetrahydrofuran (1 mL) under a nitrogen atmosphere, and a solution of zinc chloride in tetrahydrofuran (0.5 mol/L, 84 μL), tetramethyldisiloxane (30 μL), and tetrakistriphenylphosphine palladium (2.4 mg) were added thereto, and the mixture was stirred at room temperature for three hours. The reaction solution was concentrated under reduced pressure to obtain a crude product. The crude product was purified by fractionation HPLC to obtain Compound 2185 ((11S,17S,26S,29S,33S,36S)-9-[2-(2-aminoethoxy)ethyl]-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone) (1.51 mg, 24%).

LCMS (ESI) m/z=1489.2 (M+H)+
Retention time: 2.73 min (analysis condition SQDFA05long)

Synthesis of Compound 2186 ((11S,17S,26S,29S,33S,36S)-9-(4-aminobutyl)-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone)

Compound 2186 was synthesized according to the following scheme.

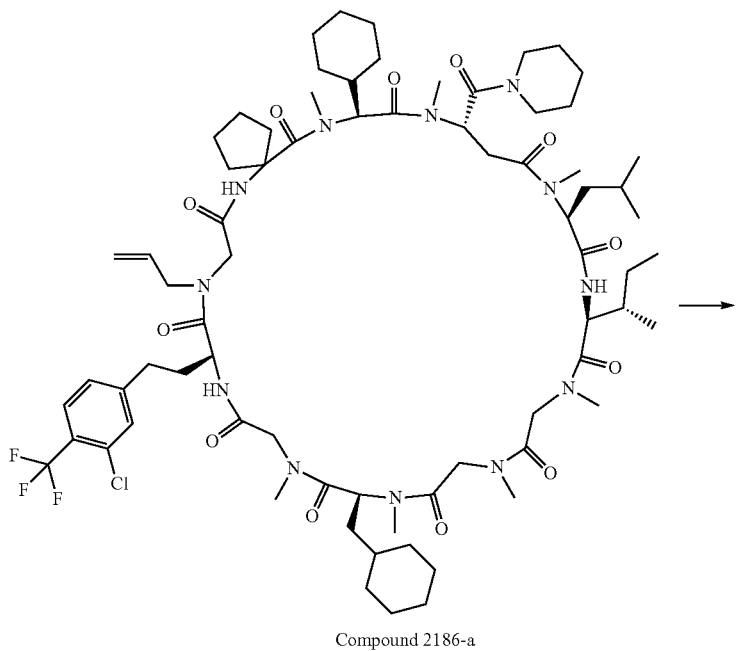

Compound 2186-a

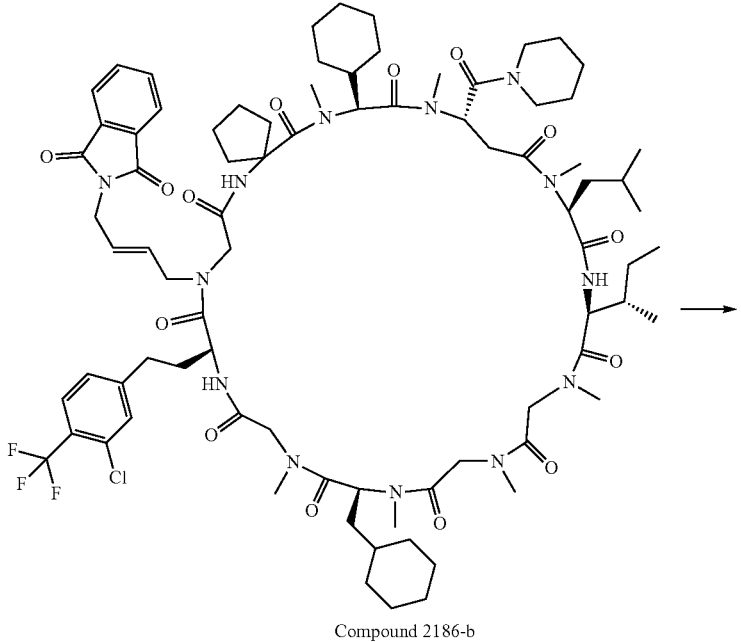

Compound 2186-b

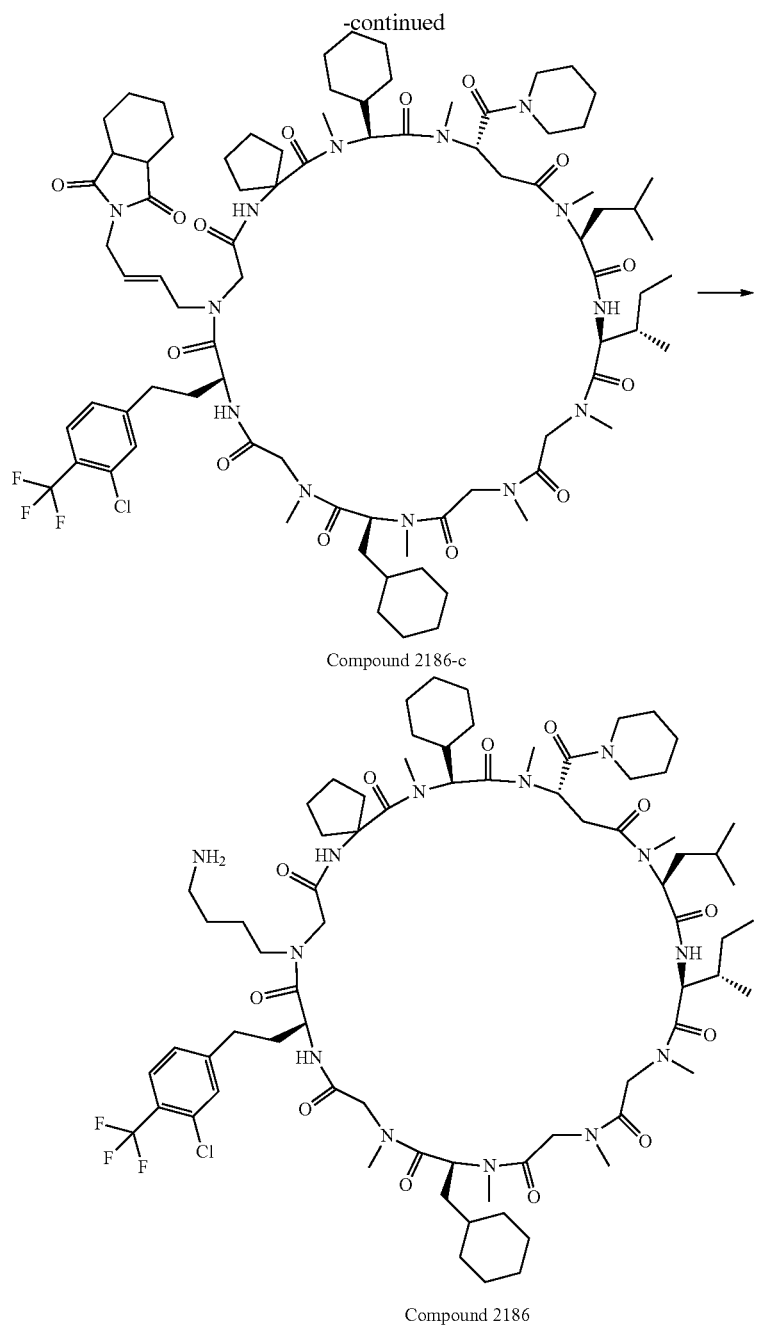

Compound 2186-c

Compound 2186

The target Compound 2186-a (1.282 g, 0.893 mmol, 52%) was obtained using Compound aa006-resin ((3S)-3-[9H-fluoren-9-ylmethoxycarbonyl(methyl)amino]-4-oxo-4-piperidin-1-ylbutanoic acid-2-chlorotrityl resin, Fmoc-MeAsp (O-Trt(2-Cl)resin)-pip) (0.411 mmol/g, 4.2 g, 1.726 mmol) as a starting material, and using Fmoc-MeChg-OH, Fmoc-cLeu-OH, Fmoc-AllylGly-OH, Fmoc-Hph(4-CF3-3-Cl)—OH, Fmoc-MeGly-OH, Fmoc-MeCha-OH, Fmoc-MeGly-OH, Fmoc-MeGly-OH, Fmoc-Ile-OH, and Fmoc-MeLeu-OH by performing the above-described peptide elongation reaction by the Fmoc method, cleavage of the elongated peptide from the resin, cyclization of the cleaved peptide (using (1-cyano-2-ethoxy-2-oxoethylideneaminooxy)dimethylamino-mopholino-carbeniumhexafluorophosphate (COMU) as the cyclizing agent), and purification of the cyclic peptide (reverse phase medium pressure column chromatography, $C_{18}$, methanol/10 mM aqueous ammonium acetate solution)).

LCMS (ESI) m/z=1440.13 (M–H)–

Retention time: 0.88 min (analysis condition SQDAA50)

Compound 2186-a (50.0 mg, 0.35 mmol) was dissolved in dichloroethane (0.69 mL), Stewart-Grubbs catalyst (29.7 mg, 1.5 equivalents) and N-allylphthalimide (51.9 mg, 8 equivalents) were added thereto, and the mixture was stirred at room temperature for two hours. Stewart-Grubbs catalyst (30 mg, 1.5 equivalents) and N-allylphthalimide (104 mg, 16 equivalents) were further added and the mixture was stirred for three hours, then the reaction solution was concentrated under reduced pressure, and the obtained residue was purified by reverse phase medium pressure column chromatography (acetonitrile with 0.1% formic acid/water with 0.1% formic acid) to obtain Compound 2186-b (2.0 mg, 3.6%).

Compound 2186-b (2.0 mg, 1.249 µmol) was dissolved in ethanol (1.0 mL), and platinum (IV) oxide (3.9 mg, 14 equivalents) was added thereto. The reaction vessel was purged with hydrogen, and the mixture was stirred at room temperature for 30 min. The reaction solution was filtered through celite, solids were washed with ethanol, and then the filtrate was concentrated under reduced pressure to obtain Compound 2186-c. The next reaction was carried out without further purification. The obtained Compound 2186-c was dissolved in ethanol (1.0 mL), hydrazine-hydrate (0.03 mL) was added, and the mixture was stirred at 80° C. for 24 hours. The solvent was evaporated from the reaction solution under reduced pressure to obtain Compound 2186 as a crude product. The crude product was mixed with the crude product of Compound 2186 obtained using Compound 2186-a (0.7 mg) by performing olefin metathesis reaction, reduction by platinum oxide, and further treatment with hydrazine-hydrate similarly, and reverse phase HPLC purification was performed to obtain Compound 2186 ((11S,17S,26S,29S,33S,36S)-9-(4-aminobutyl)-11-[2-[3-chloro-4-(trifluoromethyl)phenyl]ethyl]-36-cyclohexyl-17-(cyclohexylmethyl)-29-isobutyl-15,18,21,24,30,34,37-heptamethyl-26-[(1S)-1-methylpropyl]-33-(piperidine-1-carbonyl)-6,9,12,15,18,21,24,27,30,34,37-undecazaspiro[4.33]octatriacontane-7,10,13,16,19,22,25,28,31,35,38-undecone) (0.48 mg, 1%).

LCMS (ESI) m/z=1473.3 (M+H)+

Retention time: 2.77 min (analysis condition SQDFA05long)

TABLE 22

| Compound No. | Analytical condition | Retention time (min) | MS Found(m/z) | MS polarity |
|---|---|---|---|---|
| 1 | SSC-FA-03 | 2.155 | 1480.1 | (M − H)− |
| 2 | SSC-TFA-07 | 1.575 | 1318.8 | (M + H)+ |
| 3 | SSC-FA-03 | 1.948 | 1520.8 | (M − H)− |
| 4 | SSC-FA-03 | 1.788 | 1383.9 | (M − H)− |
| 5 | SSC-A-AF-01 | 7.456 | 1436.0 | (M + H)+ |
| 6 | SSC-AF-00 | 2.247 | 1584.9 | (M − H)− |
| 7 | SSC-FA-03 | 1.823 | 1414.0 | (M − H)− |
| 8 | SSC-AF-00 | 2.225 | 1341.0 | (M − H)− |
| 9 | SSC-FA-03 | 1.688 | 1414.0 | (M − H)− |
| 10 | SSC-FA-03 | 2.165 | 1572.8 | (M − H)− |
| 11 | SSC-A-FA-01 | 5.059 | 1425.7 | (M − H)− |
| 12 | SSC-TFA-07 | 1.416 | 1401.7 | (M + H)+ |
| 13 | SSC-AF-00 | 2.160 | 1470.0 | (M − H)− |
| 14 | SSC-TFA-07 | 1.415 | 1288.7 | (M + H)+ |
| 15 | SSC-TFA-07 | 1.408 | 1441.7 | (M + H)+ |
| 16 | SSC-FA-03 | 1.708 | 1404.0 | (M − H)− |
| 17 | SSC-FA-03 | 1.827 | 1427.8 | (M − H)− |
| 18 | SSC-TFA-07 | 1.337 | 1238.7 | (M + H)+ |
| 19 | SSC-AF-00 | 2.084 | 1224.6 | (M − H)− |
| 20 | SSC-FA-03 | 1.748 | 1429.9 | (M − H)− |
| 21 | SSC-TFA-07 | 1.296 | 1379.6 | (M + H)+ |
| 22 | SSC-TFA-07 | 1.577 | 1332.7 | (M + H)+ |
| 23 | SSC-FA-03 | 2.037 | 1440.0 | (M − H)− |
| 24 | SSC-AF-00 | 2.112 | 1373.9 | (M − H)− |
| 25 | SSC-AA-20 | 2.107 | 1330.8 | (M − H)− |
| 26 | SSC-A-FA-01 | 6.444 | 1574.7 | (M + H)+ |
| 27 | SSC-AF-00 | 2.209 | 1481.9 | (M − H)− |
| 28 | SSC-TFA-07 | 1.295 | 1210.8 | (M + H)+ |
| 29 | SSC-AA-20 | 2.103 | 1389.7 | (M − H)− |
| 30 | SSC-TFA-07 | 1.599 | 1441.8 | (M + H)+ |
| 31 | SSC-TFA-07 | 1.480 | 1258.9 | (M + H)+ |
| 32 | SSC-AF-00 | 2.060 | 1367.9 | (M − H)− |
| 33 | SSC-A-FA-02 | 6.625 | 1412.7 | (M + H)+ |
| 34 | SSC-A-FA-02 | 6.601 | 1454.6 | (M − H)− |
| 35 | SSC-AF-00 | 2.153 | 1411.9 | (M − H)− |
| 36 | SSC-FA-03 | 1.727 | 1504.8 | (M − H)− |
| 37 | SSC-TFA-07 | 1.615 | 1453.8 | (M + H)+ |
| 38 | SSC-TFA-07 | 1.627 | 1356.7 | (M + H)+ |
| 39 | SSC-A-FA-01 | 6.352 | 1434.6 | (M + H)+ |
| 40 | SSC-AF-00 | 2.156 | 1441.8 | (M − H)− |
| 41 | SSC-A-AF-01 | 7.864 | 1536.8 | (M − H)− |
| 42 | SSC-FA-03 | 1.881 | 1340.5 | (M − H)− |
| 43 | SSC-FA-03 | 2.056 | 1494.0 | (M − H)− |
| 44 | SSC-FA-03 | 1.749 | 1418.0 | (M − H)− |
| 45 | SSC-FA-03 | 1.953 | 1453.9 | (M − H)− |
| 46 | SSC-TFA-07 | 1.403 | 1372.0 | (M + H)+ |
| 47 | SSC-AF-00 | 2.053 | 1433.9 | (M − H)− |
| 48 | SSC-A-AF-02 | 8.379 | 1475.8 | (M − H)− |
| 49 | SSC-AF-00 | 2.168 | 1339.0 | (M − H)− |
| 50 | SSC-TFA-07 | 1.404 | 1405.7 | (M + H)+ |
| 51 | SSC-TFA-07 | 1.475 | 1322.7 | (M + H)+ |
| 52 | SSC-AF-00 | 2.165 | 1490.0 | (M − H)− |
| 53 | SSC-TFA-07 | 1.335 | 1444.9 | (M + H)+ |
| 54 | SSC-A-FA-01 | 5.477 | 1503.7 | (M − H)− |
| 55 | SSC-A-AF-01 | 7.507 | 1448.1 | (M − H)− |
| 56 | SSC-AF-00 | 2.199 | 1411.9 | (M − H)− |
| 57 | SSC-TFA-07 | 1.532 | 1320.7 | (M + H)+ |
| 58 | SSC-AF-00 | 2.221 | 1452.0 | (M − H)− |
| 59 | SSC-TFA-07 | 1.545 | 1316.7 | (M + H)+ |
| 60 | SSC-AF-00 | 2.204 | 1426.0 | (M − H)− |
| 61 | SSC-TFA-07 | 1.528 | 1292.7 | (M + H)+ |
| 62 | SSC-A-AF-02 | 7.791 | 1414.6 | (M + H)+ |
| 63 | SSC-AF-00 | 2.223 | 1504.8 | (M − H)− |
| 64 | SSC-AF-00 | 2.340 | 1383.0 | (M − H)− |
| 65 | SSC-TFA-07 | 1.439 | 1366.5 | (M + H)+ |
| 66 | SSC-A-FA-02 | 6.275 | 1438.7 | (M + H)+ |
| 67 | SSC-FA-03 | 1.788 | 1381.8 | (M − H)− |
| 68 | SSC-AF-00 | 2.223 | 1437.8 | (M − H)− |
| 69 | SSC-AF-00 | 2.165 | 1421.9 | (M − H)− |
| 70 | SSC-TFA-07 | 1.588 | 1445.7 | (M + H)+ |
| 71 | SSC-AF-00 | 2.083 | 1332.4 | (M − H)− |
| 72 | SSC-FA-03 | 1.877 | 1363.7 | (M − H)− |
| 73 | SSC-FA-03 | 1.884 | 1485.7 | (M − H)− |
| 74 | SSC-A-FA-02 | 6.389 | 1376.8 | (M + H)+ |
| 75 | SSC-TFA-07 | 1.407 | 1262.6 | (M + H)+ |
| 76 | SSC-TFA-07 | 1.524 | 1316.7 | (M + H)+ |
| 77 | SSC-AF-00 | 2.164 | 1284.7 | (M − H)− |
| 78 | SSC-FA-03 | 1.844 | 1435.9 | (M − H)− |
| 79 | SSC-FA-03 | 1.909 | 1314.8 | (M − H)− |
| 80 | SSC-AF-00 | 2.153 | 1427.9 | (M − H)− |
| 81 | SSC-TFA-07 | 1.545 | 1318.7 | (M + H)+ |
| 82 | SSC-FA-03 | 1.899 | 1328.4 | (M + H)+ |
| 83 | SSC-TFA-07 | 1.453 | 1320.8 | (M + H)+ |
| 84 | SSC-AF-00 | 2.244 | 1451.8 | (M − H)− |
| 85 | SSC-A-FA-02 | 6.600 | 1444.6 | (M + H)+ |
| 86 | SSC-AF-00 | 2.189 | 1514.1 | (M − H)− |
| 87 | SSC-AF-00 | 2.276 | 1480.0 | (M − H)− |
| 88 | SSC-TFA-07 | 1.463 | 1290.7 | (M + H)+ |
| 89 | SSC-AF-00 | 2.180 | 1581.9 | (M − H)− |
| 90 | SSC-AF-00 | 2.292 | 1517.8 | (M + H)+ |
| 91 | SSC-FA-03 | 1.785 | 1413.9 | (M − H)− |
| 92 | SSC-AF-00 | 2.203 | 1490.0 | (M − H)− |
| 93 | SSC-AF-00 | 2.033 | 1234.7 | (M − H)− |
| 94 | SSC-FA-03 | 1.928 | 1475.8 | (M − H)− |
| 95 | SSC-FA-03 | 2.059 | 1493.8 | (M − H)− |
| 96 | SSC-TFA-07 | 1.424 | 1389.8 | (M + H)+ |
| 97 | SSC-FA-03 | 1.833 | 1480.8 | (M − H)− |
| 98 | SSC-FA-03 | 1.808 | 1272.9 | (M − H)− |
| 99 | SSC-A-FA-02 | 6.297 | 1434.7 | (M − H)− |
| 100 | SSC-TFA-07 | 1.465 | 1411.6 | (M + H)+ |
| 101 | SSC-TFA-07 | 1.407 | 1274.6 | (M + H)+ |
| 102 | SSC-AF-00 | 2.140 | 1388.0 | (M − H)− |
| 103 | SSC-FA-03 | 1.939 | 1441.7 | (M − H)− |
| 104 | SSC-A-FA-01 | 5.293 | 1532.7 | (M − H)− |
| 105 | SSC-A-AF-01 | 8.051 | 1590.9 | (M + H)+ |
| 106 | SSC-TFA-07 | 1.577 | 1427.7 | (M + H)+ |
| 107 | SSC-A-FA-02 | 6.531 | 1366.6 | (M + H)+ |
| 108 | SSC-TFA-07 | 1.476 | 1367.7 | (M + H)+ |
| 109 | SSC-FA-03 | 1.756 | 1232.5 | (M − H)− |
| 110 | SSC-FA-03 | 1.919 | 1458.5 | (M − H)− |
| 111 | SSC-FA-03 | 2.101 | 1587.8 | (M − H)− |
| 112 | SSC-TFA-07 | 1.459 | 1345.7 | (M + H)+ |
| 113 | SSC-TFA-07 | 1.616 | 1356.7 | (M + H)+ |

TABLE 22-continued

| Compound No. | Analytical condition | Retention time (min) | MS Found(m/z) | MS polarity |
|---|---|---|---|---|
| 114 | SSC-AF-00 | 2.140 | 1274.7 | (M − H)− |
| 115 | SSC-FA-03 | 1.868 | 1383.7 | (M − H)− |
| 116 | SSC-TFA-07 | 1.589 | 1318.7 | (M + H)+ |
| 117 | SSC-FA-03 | 1.853 | 1320.9 | (M − H)− |
| 118 | SSC-FA-03 | 2.035 | 1457.6 | (M − H)− |
| 119 | SSC-TFA-07 | 1.549 | 1310.8 | (M + H)+ |
| 120 | SSC-FA-03 | 1.892 | 1479.7 | (M − H)− |
| 121 | SSC-AF-00 | 2.120 | 1316.6 | (M − H)− |
| 122 | SSC-TFA-07 | 1.547 | 1316.7 | (M + H)+ |
| 123 | SSC-TFA-07 | 1.645 | 1332.7 | (M + H)+ |
| 124 | SSC-TFA-07 | 1.589 | 1364.6 | (M + H)+ |
| 125 | SSC-AF-00 | 2.192 | 1513.9 | (M − H)− |
| 126 | SSC-FA-03 | 1.788 | 1399.9 | (M − H)− |
| 127 | SSC-AF-00 | 2.141 | 1409.8 | (M − H)− |
| 128 | SSC-A-FA-01 | 5.245 | 1409.8 | (M − H)− |
| 129 | SSC-A-FA-01 | 5.524 | 1483.0 | (M − H)− |
| 130 | SSC-A-AF-01 | 7.763 | 1496.7 | (M + H)+ |
| 131 | SSC-TFA-07 | 1.492 | 1387.7 | (M + H)+ |
| 132 | SSC-A-FA-02 | 6.548 | 1464.6 | (M + H)+ |
| 133 | SSC-AF-00 | 2.127 | 1274.7 | (M + H)+ |
| 134 | SSC-FA-03 | 1.717 | 1367.6 | (M − H)− |
| 135 | SSC-AF-00 | 2.163 | 1383.9 | (M − H)− |
| 136 | SSC-TFA-07 | 1.515 | 1425.6 | (M + H)+ |
| 137 | SSC-FA-03 | 2.113 | 1454.0 | (M − H)− |
| 138 | SSC-A-AF-02 | 8.124 | 1454.6 | (M + H)+ |
| 139 | SSC-TFA-07 | 1.481 | 1397.8 | (M + H)+ |
| 140 | SSC-AF-00 | 2.113 | 1441.8 | (M − H)− |
| 141 | SSC-FA-03 | 1.843 | 1441.8 | (M − H)− |
| 142 | SSC-TFA-07 | 1.533 | 1314.8 | (M + H)+ |
| 143 | SSC-FA-03 | 2.095 | 1587.9 | (M − H)− |
| 144 | SSC-A-AF-01 | 7.877 | 1437.8 | (M − H)− |
| 145 | SSC-FA-03 | 1.904 | 1475.7 | (M − H)− |
| 146 | SSC-FA-03 | 1.795 | 1310.4 | (M − H)− |
| 147 | SSC-AF-00 | 2.289 | 1530.0 | (M + H)+ |
| 148 | SSC-FA-03 | 1.949 | 1427.9 | (M − H)− |
| 149 | SSC-TFA-07 | 1.455 | 1278.7 | (M + H)+ |
| 150 | SSC-FA-03 | 1.873 | 1412.0 | (M − H)− |
| 151 | SSC-FA-03 | 1.889 | 1306.7 | (M − H)− |
| 152 | SSC-AF-00 | 2.093 | 1403.8 | (M − H)− |
| 153 | SSC-TFA-07 | 1.349 | 1226.7 | (M + H)+ |
| 154 | SSC-A-FA-01 | 4.451 | 1470.6 | (M + H)+ |
| 155 | SSC-A-FA-01 | 5.567 | 1423.8 | (M − H)− |
| 156 | SSC-AF-00 | 2.148 | 1373.9 | (M − H)− |
| 157 | SSC-AF-00 | 2.175 | 1424.0 | (M − H)− |
| 158 | SSC-TFA-07 | 1.493 | 1360.6 | (M + H)+ |
| 159 | SSC-FA-03 | 1.847 | 1401.9 | (M − H)− |
| 160 | SSC-AF-00 | 2.233 | 1429.5 | (M + H)+ |
| 161 | SSC-AF-00 | 2.171 | 1555.7 | (M − H)− |
| 162 | SSC-AF-00 | 2.091 | 1463.9 | (M − H)− |
| 163 | SSC-A-FA-01 | 5.444 | 1455.8 | (M − H)− |
| 164 | SSC-AF-00 | 2.193 | 1424.0 | (M − H)− |
| 165 | SSC-TFA-07 | 1.468 | 1320.8 | (M + H)+ |
| 166 | SSC-AF-00 | 2.211 | 1462.0 | (M − H)− |
| 167 | SSC-TFA-07 | 1.425 | 1319.8 | (M + H)+ |
| 168 | SSC-FA-03 | 2.059 | 1537.6 | (M − H)− |
| 169 | SSC-AF-00 | 2.184 | 1503.9 | (M − H)− |
| 170 | SSC-AA-20 | 2.055 | 1244.6 | (M − H)− |
| 171 | SSC-FA-03 | 1.953 | 1457.9 | (M − H)− |
| 172 | SSC-FA-03 | 1.933 | 1437.9 | (M − H)− |
| 173 | SSC-AF-00 | 2.108 | 1555.9 | (M − H)− |
| 174 | SSC-FA-03 | 1.755 | 1475.9 | (M − H)− |
| 175 | SSC-AF-00 | 2.077 | 1389.6 | (M + H)+ |
| 176 | SSC-AF-00 | 2.109 | 1455.8 | (M − H)− |
| 177 | SSC-AF-00 | 2.179 | 1466.8 | (M − H)− |
| 178 | SSC-TFA-07 | 1.497 | 1304.8 | (M + H)+ |
| 179 | SSC-FA-03 | 2.097 | 1509.9 | (M − H)− |
| 180 | SSC-TFA-07 | 1.488 | 1498.8 | (M + H)+ |
| 181 | SSC-TFA-07 | 1.453 | 1314.7 | (M + H)+ |
| 182 | SSC-AF-00 | 2.161 | 1423.8 | (M − H)− |
| 183 | SSC-TFA-07 | 1.489 | 1302.7 | (M + H)+ |
| 184 | SSC-TFA-07 | 1.269 | 1361.8 | (M + H)+ |
| 185 | SSC-TFA-07 | 1.525 | 1316.7 | (M + H)+ |
| 186 | SSC-FA-03 | 1.887 | 1328.4 | (M − H)− |
| 187 | SSC-FA-03 | 1.911 | 1385.9 | (M − H)− |
| 188 | SSC-FA-03 | 1.817 | 1497.8 | (M − H)− |
| 189 | SSC-TFA-07 | 1.544 | 1354.7 | (M + H)+ |
| 190 | SSC-A-AF-01 | 7.563 | 1466.6 | (M − H)− |
| 191 | SSC-AF-00 | 2.135 | 1386.0 | (M − H)− |
| 192 | SSC-FA-03 | 1.991 | 1435.9 | (M − H)− |
| 193 | SSC-A-FA-01 | 5.300 | 1367.9 | (M − H)− |
| 194 | SSC-FA-03 | 1.837 | 1312.5 | (M + H)+ |
| 195 | SSC-FA-03 | 1.811 | 1383.9 | (M − H)− |
| 196 | SSC-TFA-07 | 1.380 | 1262.7 | (M + H)+ |
| 197 | SSC-TFA-07 | 1.469 | 1399.8 | (M + H)+ |
| 198 | SSC-A-FA-02 | 6.440 | 1368.7 | (M + H)+ |
| 199 | SSC-TFA-07 | 1.440 | 1419.9 | (M + H)+ |
| 200 | SSC-FA-03 | 2.148 | 1467.8 | (M − H)− |
| 201 | SSC-AF-00 | 2.105 | 1410.0 | (M − H)− |
| 202 | SSC-AF-00 | 2.165 | 1367.7 | (M − H)− |
| 203 | SSC-A-FA-02 | 6.648 | 1456.6 | (M + H)+ |
| 204 | SSC-TFA-07 | 1.532 | 1316.7 | (M + H)+ |
| 205 | SSC-FA-03 | 2.016 | 1413.9 | (M − H)− |
| 206 | SSC-FA-03 | 1.836 | 1298.5 | (M − H)− |
| 207 | SSC-TFA-07 | 1.403 | 1330.6 | (M + H)+ |
| 208 | SSC-AF-00 | 2.156 | 1469.7 | (M − H)− |
| 209 | SSC-A-AF-01 | 7.703 | 1489.9 | (M + H)+ |
| 210 | SSC-TFA-07 | 1.543 | 1304.7 | (M + H)+ |
| 211 | SSC-TFA-07 | 1.445 | 1286.7 | (M + H)+ |
| 212 | SSC-TFA-07 | 1.432 | 1276.7 | (M + H)+ |
| 213 | SSC-TFA-07 | 1.604 | 1318.7 | (M + H)+ |
| 214 | SSC-TFA-07 | 1.453 | 1322.9 | (M + H)+ |
| 215 | SSC-A-FA-01 | 5.729 | 1410.0 | (M − H)− |
| 216 | SSC-FA-03 | 1.985 | 1505.8 | (M − H)− |
| 217 | SSC-TFA-07 | 1.632 | 1334.7 | (M + H)+ |
| 218 | SSC-FA-03 | 1.879 | 1494.9 | (M − H)− |
| 219 | SSC-AF-00 | 2.105 | 1232.8 | (M + H)+ |
| 220 | SSC-TFA-07 | 1.487 | 1387.7 | (M + H)+ |
| 221 | SSC-TFA-07 | 1.505 | 1399.7 | (M + H)+ |
| 222 | SSC-A-FA-01 | 6.188 | 1548.7 | (M + H)+ |
| 223 | SSC-TFA-07 | 1.479 | 1292.7 | (M + H)+ |
| 224 | SSC-AA-20 | 2.103 | 1389.7 | (M − H)− |
| 225 | SSC-AF-00 | 2.200 | 1438.0 | (M − H)− |
| 226 | SSC-FA-03 | 2.073 | 1467.8 | (M − H)− |
| 227 | SSC-TFA-07 | 1.397 | 1282.7 | (M + H)+ |
| 228 | SSC-AF-00 | 2.136 | 1427.8 | (M − H)− |
| 229 | SSC-TFA-07 | 1.424 | 1413.7 | (M + H)+ |
| 230 | SSC-TFA-07 | 1.499 | 1302.6 | (M + H)+ |
| 231 | SSC-TFA-07 | 1.524 | 1302.8 | (M + H)+ |
| 232 | SSC-AF-00 | 2.144 | 1407.9 | (M − H)− |
| 233 | SSC-TFA-07 | 1.353 | 1492.8 | (M + H)+ |
| 234 | SSC-AF-00 | 2.144 | 1397.6 | (M − H)− |
| 235 | SSC-FA-03 | 1.708 | 1435.7 | (M − H)− |
| 236 | SSC-AF-00 | 2.132 | 1400.0 | (M − H)− |
| 237 | SSC-AF-00 | 2.264 | 1366.9 | (M − H)− |
| 238 | SSC-TFA-07 | 1.399 | 1323.7 | (M + H)+ |
| 239 | SSC-FA-03 | 1.887 | 1527.8 | (M − H)− |
| 240 | SSC-AF-00 | 2.152 | 1508.8 | (M − H)− |
| 241 | SSC-A-FA-02 | 6.756 | 1364.7 | (M − H)− |
| 242 | SSC-TFA-07 | 1.472 | 1290.7 | (M + H)+ |
| 243 | SSC-FA-03 | 1.543 | 1472.8 | (M − H)− |
| 244 | SSC-FA-03 | 1.719 | 1360.7 | (M − H)− |
| 245 | SSC-AF-00 | 2.096 | 1513.9 | (M − H)− |
| 246 | SSC-FA-03 | 1.875 | 1383.8 | (M − H)− |
| 247 | SSC-FA-03 | 1.857 | 1485.8 | (M − H)− |
| 248 | SSC-TFA-07 | 1.439 | 1288.6 | (M + H)+ |
| 249 | SSC-FA-03 | 2.119 | 1465.9 | (M − H)− |
| 250 | SSC-FA-03 | 2.155 | 1485.9 | (M − H)− |
| 251 | SSC-AF-00 | 2.177 | 1523.0 | (M + H)+ |
| 252 | SSC-TFA-07 | 1.353 | 1362.7 | (M + H)+ |
| 253 | SSC-AF-00 | 2.163 | 1467.5 | (M − H)− |
| 254 | SSC-AF-00 | 2.101 | 1441.9 | (M − H)− |
| 255 | SSC-AF-00 | 2.345 | 1543.8 | (M + H)+ |
| 256 | SSC-FA-03 | 1.793 | 1399.7 | (M + H)+ |
| 257 | SSC-TFA-07 | 1.484 | 1334.8 | (M + H)+ |
| 258 | SSC-AF-00 | 2.124 | 1296.7 | (M − H)− |
| 259 | SSC-AF-00 | 2.228 | 1533.9 | (M − H)− |
| 260 | SSC-TFA-07 | 1.472 | 1346.8 | (M + H)+ |
| 261 | SSC-TFA-07 | 1.489 | 1302.8 | (M + H)+ |
| 262 | SSC-TFA-07 | 1.489 | 1274.8 | (M + H)+ |
| 263 | SSC-A-AF-01 | 7.788 | 1453.9 | (M − H)− |
| 264 | SSC-TFA-07 | 1.405 | 1276.7 | (M + H)+ |
| 265 | SSC-TFA-07 | 1.405 | 1299.8 | (M + H)+ |
| 266 | SSC-TFA-07 | 1.377 | 1343.7 | (M + H)+ |
| 267 | SSC-FA-03 | 1.991 | 1299.0 | (M − H)− |

TABLE 22-continued

| Compound No. | Analytical condition | Retention time (min) | MS Found(m/z) | MS polarity |
|---|---|---|---|---|
| 268 | SSC-TFA-07 | 1.423 | 1276.7 | (M + H)+ |
| 269 | SSC-A-FA-02 | 6.321 | 1430.6 | (M + H)+ |
| 270 | SSC-AF-00 | 2.216 | 1449.8 | (M − H)− |
| 271 | SSC-TFA-07 | 1.441 | 1322.8 | (M + H)+ |
| 272 | SSC-FA-03 | 1.839 | 1501.8 | (M − H)− |
| 273 | SSC-TFA-07 | 1.471 | 1314.7 | (M + H)+ |
| 274 | SSC-AF-00 | 2.152 | 1399.5 | (M − H)− |
| 275 | SSC-TFA-07 | 1.447 | 1278.7 | (M + H)+ |
| 276 | SSC-AF-00 | 2.097 | 1503.8 | (M − H)− |
| 277 | SSC-FA-03 | 2.051 | 1413.8 | (M − H)− |
| 278 | SSC-FA-03 | 1.804 | 1408.7 | (M − H)− |
| 279 | SSC-A-FA-01 | 5.560 | 1434.0 | (M − H)− |
| 280 | SSC-AF-00 | 2.143 | 1409.6 | (M − H)− |
| 281 | SSC-TFA-07 | 1.575 | 1427.6 | (M + H)+ |
| 282 | SSC-FA-03 | 2.008 | 1456.0 | (M − H)− |
| 283 | SSC-AF-00 | 2.156 | 1489.9 | (M − H)− |
| 284 | SSC-AF-00 | 2.107 | 1395.9 | (M − H)− |
| 285 | SSC-TFA-07 | 1.588 | 1330.6 | (M + H)+ |
| 286 | SSC-TFA-07 | 1.443 | 1286.9 | (M + H)+ |
| 287 | SSC-TFA-07 | 1.571 | 1401.7 | (M + H)+ |
| 288 | SSC-AF-00 | 2.097 | 1395.9 | (M − H)− |
| 289 | SSC-FA-03 | 1.705 | 1372.0 | (M − H)− |
| 290 | SSC-TFA-07 | 1.503 | 1302.6 | (M + H)+ |
| 291 | SSC-FA-03 | 1.815 | 1302.5 | (M + H)+ |
| 292 | SSC-FA-03 | 1.871 | 1329.6 | (M − H)− |
| 293 | SSC-AF-00 | 2.171 | 1409.9 | (M − H)− |
| 294 | SSC-AF-00 | 2.229 | 1428.0 | (M − H)− |
| 295 | SSC-TFA-07 | 1.471 | 1443.7 | (M + H)+ |
| 296 | SSC-A-FA-02 | 7.016 | 1474.9 | (M − H)− |
| 297 | SSC-AF-00 | 2.301 | 1493.7 | (M − H)− |
| 298 | SSC-TFA-07 | 1.512 | 1385.8 | (M + H)+ |
| 299 | SSC-TFA-07 | 1.471 | 1320.8 | (M + H)+ |
| 300 | SSC-FA-03 | 1.885 | 1444.3 | (M − H)− |
| 301 | SSC-A-FA-01 | 6.227 | 1450.6 | (M + H)+ |
| 302 | SSC-AF-00 | 2.095 | 1425.9 | (M − H)− |
| 303 | SSC-A-FA-01 | 5.293 | 1419.8 | (M − H)− |
| 304 | SSC-AF-00 | 2.164 | 1481.7 | (M − H)− |
| 305 | SSC-TFA-07 | 1.571 | 1318.8 | (M + H)+ |
| 306 | SSC-TFA-07 | 1.373 | 1461.7 | (M + H)+ |
| 307 | SSC-AF-00 | 2.171 | 1397.5 | (M − H)− |
| 308 | SSC-A-FA-01 | 5.464 | 1407.8 | (M − H)− |
| 309 | SSC-FA-03 | 1.932 | 1427.5 | (M − H)− |
| 310 | SSC-AF-00 | 2.147 | 1342.4 | (M − H)− |
| 311 | SSC-TFA-07 | 1.592 | 1415.8 | (M + H)+ |
| 312 | SSC-TFA-07 | 1.445 | 1375.7 | (M + H)+ |
| 313 | SSC-FA-03 | 1.773 | 1381.6 | (M − H)− |
| 314 | SSC-FA-03 | 1.821 | 1371.9 | (M − H)− |
| 315 | SSC-TFA-07 | 1.449 | 1302.9 | (M + H)+ |
| 316 | SSC-AF-00 | 2.040 | 1359.9 | (M − H)− |
| 317 | SSC-FA-03 | 1.871 | 1415.5 | (M − H)− |
| 318 | SSC-TFA-07 | 1.479 | 1425.7 | (M + H)+ |
| 319 | SSC-A-FA-01 | 6.677 | 1468.6 | (M + H)+ |
| 320 | SSC-AF-00 | 2.177 | 1478.0 | (M − H)− |
| 321 | SSC-TFA-07 | 1.633 | 1441.7 | (M + H)+ |
| 322 | SSC-TFA-07 | 1.444 | 1350.8 | (M + H)+ |
| 323 | SSC-TFA-07 | 1.339 | 1260.7 | (M + H)+ |
| 324 | SSC-TFA-07 | 1.636 | 1407.7 | (M + H)+ |
| 325 | SSC-TFA-07 | 1.404 | 1359.7 | (M + H)+ |
| 326 | SSC-FA-03 | 1.867 | 1437.7 | (M − H)− |
| 327 | SSC-AF-00 | 2.136 | 1409.9 | (M − H)− |
| 328 | SSC-AF-00 | 2.139 | 1439.8 | (M − H)− |
| 329 | SSC-TFA-07 | 1.587 | 1348.7 | (M + H)+ |
| 330 | SSC-FA-03 | 1.999 | 1481.4 | (M − H)− |
| 331 | SSC-A-FA-01 | 4.375 | 1452.6 | (M − H)− |
| 332 | SSC-TFA-07 | 1.465 | 1320.8 | (M + H)+ |
| 333 | SSC-AF-00 | 2.171 | 1300.5 | (M − H)− |
| 334 | SSC-FA-03 | 1.825 | 1396.0 | (M − H)− |
| 335 | SSC-FA-03 | 1.884 | 1481.9 | (M − H)− |
| 336 | SSC-AF-00 | 2.215 | 1516.0 | (M − H)− |
| 337 | SSC-TFA-07 | 1.457 | 1288.7 | (M + H)+ |
| 338 | SSC-AF-00 | 2.279 | 1545.1 | (M − H)− |
| 339 | SSC-FA-03 | 1.848 | 1431.8 | (M − H)− |
| 340 | SSC-FA-03 | 2.008 | 1486.0 | (M − H)− |
| 341 | SSC-FA-03 | 1.747 | 1274.9 | (M − H)− |
| 342 | SSC-A-AF-01 | 7.544 | 1407.8 | (M − H)− |
| 343 | SSC-A-FA-01 | 5.341 | 1440.0 | (M − H)− |
| 344 | SSC-A-FA-01 | 6.165 | 1464.6 | (M + H)+ |
| 345 | SSC-A-FA-02 | 7.005 | 1466.7 | (M − H)− |
| 346 | SSC-FA-03 | 1.988 | 1435.8 | (M − H)− |
| 347 | SSC-TFA-07 | 1.476 | 1316.6 | (M + H)+ |
| 348 | SSC-A-AF-01 | 7.915 | 1430.6 | (M − H)− |
| 349 | SSC-AF-00 | 2.224 | 1424.0 | (M − H)− |
| 350 | SSC-AF-00 | 2.160 | 1437.8 | (M − H)− |
| 351 | SSC-TFA-07 | 1.415 | 1308.6 | (M + H)+ |
| 352 | SSC-FA-03 | 1.889 | 1427.7 | (M − H)− |
| 353 | SSC-FA-03 | 1.852 | 1473.9 | (M − H)− |
| 354 | SSC-FA-03 | 1.845 | 1322.9 | (M − H)− |
| 355 | SSC-AF-00 | 2.135 | 1470.8 | (M − H)− |
| 356 | SSC-AF-00 | 2.203 | 1425.8 | (M − H)− |
| 357 | SSC-TFA-07 | 1.399 | 1323.6 | (M + H)+ |
| 358 | SSC-AF-00 | 2.173 | 1423.8 | (M − H)− |
| 359 | SSC-A-FA-02 | 6.141 | 1358.7 | (M − H)− |
| 360 | SSC-TFA-07 | 1.421 | 1359.6 | (M + H)+ |
| 361 | SSC-FA-03 | 1.651 | 1204.8 | (M − H)− |
| 362 | SSC-A-FA-01 | 6.135 | 1452.6 | (M + H)+ |
| 363 | SSC-A-AF-01 | 7.219 | 1405.9 | (M − H)− |
| 364 | SSC-TFA-07 | 1.505 | 1306.8 | (M + H)+ |
| 365 | SSC-A-AF-02 | 8.011 | 1464.7 | (M + H)+ |
| 366 | SSC-FA-03 | 1.927 | 1331.0 | (M − H)− |
| 367 | SSC-FA-03 | 1.817 | 1453.5 | (M − H)− |
| 368 | SSC-FA-03 | 1.896 | 1411.6 | (M − H)− |
| 369 | SSC-FA-03 | 1.691 | 1258.5 | (M − H)− |
| 370 | SSC-FA-03 | 1.915 | 1514.0 | (M − H)− |
| 371 | SSC-A-FA-01 | 6.021 | 1420.6 | (M + H)+ |
| 372 | SSC-TFA-07 | 1.364 | 1391.9 | (M + H)+ |
| 373 | SSC-TFA-07 | 1.281 | 1348.8 | (M + H)+ |
| 374 | SSC-A-FA-02 | 6.708 | 1464.6 | (M − H)− |
| 375 | SSC-A-AF-02 | 7.887 | 1374.6 | (M + H)+ |
| 376 | SSC-AF-00 | 2.172 | 1523.8 | (M − H)− |
| 377 | SSC-A-FA-02 | 6.900 | 1468.7 | (M − H)− |
| 378 | SSC-FA-03 | 1.827 | 1395.9 | (M − H)− |
| 379 | SSC-AF-00 | 2.132 | 1516.9 | (M − H)− |
| 380 | SSC-AF-00 | 2.172 | 1371.8 | (M − H)− |
| 381 | SSC-AF-00 | 2.092 | 1413.9 | (M − H)− |
| 382 | SSC-AF-00 | 2.049 | 1341.6 | (M − H)− |
| 383 | SSC-TFA-07 | 1.499 | 1312.7 | (M + H)+ |
| 384 | SSC-AF-00 | 2.155 | 1482.8 | (M − H)− |
| 385 | SSC-FA-03 | 1.955 | 1489.8 | (M − H)− |
| 386 | SSC-FA-03 | 1.863 | 1310.6 | (M − H)− |
| 387 | SSC-FA-03 | 1.912 | 1481.9 | (M − H)− |
| 388 | SSC-AF-00 | 2.147 | 1463.9 | (M − H)− |
| 389 | SSC-FA-03 | 1.560 | 1520.9 | (M − H)− |
| 390 | SSC-FA-03 | 1.808 | 1438.1 | (M − H)− |
| 391 | SSC-AF-00 | 2.205 | 1438.0 | (M − H)− |
| 392 | SSC-AF-00 | 2.283 | 1482.0 | (M − H)− |
| 393 | SSC-AF-00 | 2.169 | 1411.9 | (M − H)− |
| 394 | SSC-AF-00 | 2.156 | 1414.0 | (M − H)− |
| 395 | SSC-TFA-07 | 1.523 | 1304.7 | (M + H)+ |
| 396 | SSC-FA-03 | 1.647 | 1230.4 | (M − H)− |
| 397 | SSC-AF-00 | 2.140 | 1427.9 | (M − H)− |
| 398 | SSC-AA-20 | 2.108 | 1349.8 | (M − H)− |
| 399 | SSC-TFA-07 | 1.568 | 1439.7 | (M + H)+ |
| 400 | SSC-A-FA-01 | 5.539 | 1433.8 | (M − H)− |
| 401 | SSC-A-AF-02 | 8.128 | 1462.6 | (M + H)+ |
| 402 | SSC-TFA-07 | 1.484 | 1288.7 | (M + H)+ |
| 403 | SSC-AF-00 | 2.113 | 1443.8 | (M − H)− |
| 404 | SSC-FA-03 | 1.856 | 1335.0 | (M − H)− |
| 405 | SSC-TFA-07 | 1.563 | 1318.7 | (M + H)+ |
| 406 | SSC-TFA-07 | 1.393 | 1322.8 | (M + H)+ |
| 407 | SSC-TFA-07 | 1.401 | 1318.8 | (M + H)+ |
| 408 | SSC-FA-03 | 1.739 | 1428.0 | (M − H)− |
| 409 | SSC-AF-00 | 2.196 | 1424.1 | (M − H)− |
| 410 | SSC-FA-03 | 1.805 | 1447.9 | (M − H)− |
| 411 | SSC-AF-00 | 2.215 | 1437.9 | (M − H)− |
| 412 | SSC-AF-00 | 2.128 | 1272.9 | (M − H)− |
| 413 | SSC-FA-03 | 1.704 | 1218.8 | (M − H)− |
| 414 | SSC-TFA-07 | 1.475 | 1270.8 | (M + H)+ |
| 415 | SSC-FA-03 | 1.919 | 1427.9 | (M − H)− |
| 416 | SSC-AF-00 | 2.208 | 1340.4 | (M − H)− |
| 417 | SSC-AF-00 | 2.160 | 1385.9 | (M − H)− |
| 418 | SSC-TFA-07 | 1.449 | 1344.6 | (M + H)+ |
| 419 | SSC-FA-03 | 1.777 | 1475.8 | (M − H)− |
| 420 | SSC-AF-00 | 2.168 | 1328.5 | (M − H)− |
| 421 | SSC-TFA-07 | 1.497 | 1399.8 | (M + H)+ |

TABLE 22-continued

| Compound No. | Analytical condition | Retention time (min) | MS Found(m/z) | MS polarity |
|---|---|---|---|---|
| 422 | SSC-AF-00 | 2.120 | 1541.8 | (M − H)− |
| 423 | SSC-TFA-07 | 1.504 | 1457.7 | (M + H)+ |
| 424 | SSC-A-FA-02 | 6.431 | 1379.1 | (M − H)+ |
| 425 | SSC-FA-03 | 2.051 | 1489.8 | (M − H)− |
| 426 | SSC-FA-03 | 1.853 | 1415.7 | (M − H)− |
| 427 | SSC-FA-03 | 1.811 | 1387.9 | (M − H)− |
| 428 | SSC-AF-00 | 2.296 | 1516.1 | (M − H)− |
| 429 | SSC-AF-00 | 2.112 | 1260.5 | (M + H)+ |
| 430 | SSC-A-FA-02 | 6.889 | 1476.6 | (M − H)− |
| 431 | SSC-AF-00 | 2.217 | 1383.7 | (M − H)− |
| 432 | SSC-A-AF-02 | 8.151 | 1422.8 | (M − H)− |
| 433 | SSC-AF-00 | 2.205 | 1489.0 | (M − H)− |
| 434 | SSC-FA-03 | 1.833 | 1425.9 | (M − H)− |
| 435 | SSC-TFA-07 | 1.851 | 1514.0 | (M + H)+ |
| 436 | SSC-AF-00 | 2.161 | 1300.8 | (M − H)− |
| 437 | SSC-FA-03 | 1.891 | 1411.9 | (M − H)− |
| 438 | SSC-TFA-07 | 1.529 | 1401.8 | (M + H)+ |
| 439 | SSC-TFA-07 | 1.525 | 1304.7 | (M + H)+ |
| 440 | SSC-FA-03 | 1.947 | 1422.7 | (M − H)− |
| 441 | SSC-FA-03 | 1.827 | 1478.5 | (M − H)− |
| 442 | SSC-AF-00 | 2.140 | 1481.9 | (M − H)− |
| 443 | SSC-FA-03 | 2.117 | 1442.0 | (M + H)+ |
| 444 | SSC-AF-00 | 2.141 | 1494.8 | (M − H)− |
| 445 | SSC-FA-03 | 1.740 | 1445.4 | (M + H)+ |
| 446 | SSC-AF-00 | 2.113 | 1383.9 | (M − H)− |
| 447 | SSC-AF-00 | 2.152 | 1397.6 | (M + H)+ |
| 448 | SSC-TFA-07 | 1.373 | 1349.7 | (M + H)+ |
| 449 | SSC-FA-03 | 2.101 | 1490.0 | (M − H)− |
| 450 | SSC-AF-00 | 2.127 | 1413.5 | (M − H)− |
| 451 | SSC-AF-00 | 2.171 | 1411.9 | (M − H)− |
| 452 | SSC-FA-03 | 1.911 | 1423.9 | (M − H)− |
| 453 | SSC-AF-00 | 2.163 | 1411.9 | (M − H)− |
| 454 | SSC-FA-03 | 1.801 | 1288.7 | (M − H)− |
| 455 | SSC-TFA-07 | 1.540 | 1328.7 | (M + H)+ |
| 456 | SSC-TFA-07 | 1.485 | 1316.7 | (M + H)+ |
| 457 | SSC-TFA-07 | 1.401 | 1415.6 | (M + H)+ |
| 458 | SSC-AF-00 | 2.079 | 1350.0 | (M − H)− |
| 459 | SSC-FA-03 | 1.852 | 1497.8 | (M − H)− |
| 460 | SSC-FA-03 | 1.583 | 1476.9 | (M − H)− |
| 461 | SSC-AF-00 | 2.160 | 1452.0 | (M − H)− |
| 462 | SSC-A-AF-02 | 7.828 | 1428.6 | (M + H)+ |
| 463 | SSC-FA-03 | 1.939 | 1509.0 | (M − H)− |
| 464 | SSC-AF-00 | 2.159 | 1340.7 | (M − H)− |
| 465 | SSC-TFA-07 | 1.485 | 1314.6 | (M + H)+ |
| 466 | SSC-A-FA-02 | 6.693 | 1478.6 | (M + H)+ |
| 467 | SSC-TFA-07 | 1.298 | 1357.6 | (M + H)+ |
| 468 | SSC-TFA-07 | 1.452 | 1373.7 | (M + H)+ |
| 469 | SSC-FA-03 | 1.913 | 1467.6 | (M − H)− |
| 470 | SSC-AF-00 | 2.191 | 1430.0 | (M − H)− |
| 471 | SSC-TFA-07 | 1.477 | 1354.7 | (M + H)+ |
| 472 | SSC-FA-03 | 2.063 | 1488.1 | (M − H)− |
| 473 | SSC-AA-20 | 2.161 | 1419.7 | (M − H)− |
| 474 | SSC-TFA-07 | 1.496 | 1314.7 | (M + H)+ |
| 475 | SSC-A-FA-02 | 6.823 | 1416.7 | (M + H)+ |
| 476 | SSC-TFA-07 | 1.559 | 1427.8 | (M + H)+ |
| 477 | SSC-FA-03 | 1.681 | 1532.8 | (M + H)+ |
| 478 | SSC-FA-03 | 2.093 | 1468.1 | (M − H)− |
| 479 | SSC-FA-03 | 2.249 | 1601.0 | (M + H)+ |
| 480 | SSC-AF-00 | 2.193 | 1517.1 | (M − H)− |
| 481 | SSC-FA-03 | 1.877 | 1346.9 | (M − H)− |
| 482 | SSC-FA-03 | 1.833 | 1280.9 | (M − H)− |
| 483 | SSC-AF-00 | 2.197 | 1521.8 | (M − H)− |
| 484 | SSC-AF-00 | 2.145 | 1427.8 | (M − H)− |
| 485 | SSC-FA-03 | 2.045 | 1470.1 | (M − H)− |
| 486 | SSC-A-FA-01 | 6.473 | 1478.7 | (M + H)+ |
| 487 | SSC-AF-00 | 2.092 | 1373.9 | (M − H)− |
| 488 | SSC-TFA-07 | 1.521 | 1316.8 | (M + H)+ |
| 489 | SSC-AF-00 | 2.043 | 1295.5 | (M − H)− |
| 490 | SSC-TFA-07 | 1.429 | 1300.6 | (M + H)+ |
| 491 | SSC-FA-03 | 1.884 | 1382.1 | (M − H)− |
| 492 | SSC-AF-00 | 2.172 | 1439.9 | (M − H)− |
| 493 | SSC-FA-03 | 1.889 | 1495.0 | (M − H)− |
| 494 | SSC-A-FA-02 | 6.515 | 1376.6 | (M − H)− |
| 495 | SSC-FA-03 | 2.001 | 1425.8 | (M − H)− |
| 496 | SSC-AF-00 | 2.163 | 1455.9 | (M − H)− |
| 497 | SSC-AF-00 | 2.144 | 1427.9 | (M − H)− |
| 498 | SSC-FA-03 | 2.076 | 1571.7 | (M − H)− |
| 499 | SSC-TFA-07 | 1.321 | 1343.7 | (M + H)+ |
| 500 | SSC-AF-00 | 2.239 | 1510.8 | (M − H)− |
| 501 | SSC-AF-00 | 2.197 | 1328.5 | (M − H)− |
| 502 | SSC-TFA-07 | 1.307 | 1451.8 | (M + H)+ |
| 503 | SSC-A-FA-02 | 6.264 | 1418.6 | (M + H)+ |
| 504 | SSC-TFA-07 | 1.521 | 1304.8 | (M + H)+ |
| 505 | SSC-A-AF-02 | 8.020 | 1452.6 | (M − H)− |
| 506 | SSC-A-FA-01 | 5.477 | 1447.7 | (M + H)+ |
| 507 | SSC-AF-00 | 2.048 | 1345.5 | (M − H)− |
| 508 | SSC-TFA-07 | 1.421 | 1373.6 | (M + H)+ |
| 509 | SSC-A-FA-01 | 5.879 | 1501.7 | (M − H)− |
| 510 | SSC-A-FA-02 | 6.465 | 1373.1 | (M − H)− |
| 511 | SSC-TFA-07 | 1.356 | 1248.7 | (M + H)+ |
| 512 | SSC-TFA-07 | 1.531 | 1362.6 | (M + H)+ |
| 513 | SSC-AA-20 | 2.085 | 1488.7 | (M + H)+ |
| 514 | SSC-FA-03 | 2.116 | 1487.9 | (M − H)− |
| 515 | SSC-FA-03 | 1.853 | 1423.9 | (M − H)− |
| 516 | SSC-FA-03 | 2.004 | 1286.9 | (M − H)− |
| 517 | SSC-TFA-07 | 1.279 | 1454.7 | (M + H)+ |
| 518 | SSC-AF-00 | 2.212 | 1496.0 | (M − H)− |
| 519 | SSC-FA-03 | 1.549 | 1422.8 | (M − H)− |
| 520 | SSC-TFA-07 | 1.459 | 1276.7 | (M + H)+ |
| 521 | SSC-TFA-07 | 1.375 | 1284.7 | (M + H)+ |
| 522 | SSC-TFA-07 | 1.420 | 1359.7 | (M + H)+ |
| 523 | SSC-FA-03 | 2.113 | 1491.9 | (M − H)− |
| 524 | SSC-FA-03 | 1.993 | 1437.9 | (M − H)− |
| 525 | SSC-A-AF-02 | 8.091 | 1406.6 | (M − H)− |
| 526 | SSC-AF-00 | 2.159 | 1411.8 | (M − H)− |
| 527 | SSC-FA-03 | 2.204 | 1515.9 | (M − H)− |
| 528 | SSC-FA-03 | 2.001 | 1366.9 | (M − H)− |
| 529 | SSC-AF-00 | 2.140 | 1318.5 | (M − H)− |
| 530 | SSC-TFA-07 | 1.513 | 1359.7 | (M + H)+ |
| 531 | SSC-AF-00 | 2.164 | 1362.9 | (M − H)− |
| 532 | SSC-AF-00 | 2.167 | 1397.9 | (M − H)− |
| 533 | SSC-TFA-07 | 1.463 | 1385.6 | (M + H)+ |
| 534 | SSC-FA-03 | 1.917 | 1411.7 | (M − H)− |
| 535 | SSC-AF-00 | 2.195 | 1441.9 | (M − H)− |
| 536 | SSC-TFA-07 | 1.500 | 1411.8 | (M + H)+ |
| 537 | SSC-AF-00 | 2.209 | 1329.0 | (M − H)− |
| 538 | SSC-AF-00 | 2.113 | 1324.9 | (M − H)− |
| 539 | SSC-FA-03 | 1.895 | 1314.5 | (M − H)− |
| 540 | SSC-TFA-07 | 1.427 | 1256.7 | (M + H)+ |
| 541 | SSC-A-FA-02 | 6.353 | 1434.7 | (M − H)− |
| 542 | SSC-TFA-07 | 1.555 | 1316.7 | (M + H)+ |
| 543 | SSC-FA-03 | 2.103 | 1453.9 | (M − H)− |
| 544 | SSC-TFA-07 | 1.445 | 1415.7 | (M + H)+ |
| 545 | SSC-FA-03 | 1.812 | 1529.9 | (M − H)− |
| 546 | SSC-TFA-07 | 1.501 | 1336.9 | (M + H)+ |
| 547 | SSC-A-FA-02 | 6.729 | 1448.7 | (M − H)− |
| 548 | SSC-AF-00 | 2.153 | 1399.6 | (M − H)− |
| 549 | SSC-AF-00 | 2.147 | 1326.7 | (M − H)− |
| 550 | SSC-TFA-07 | 1.451 | 1288.7 | (M + H)+ |
| 551 | SSC-FA-03 | 1.984 | 1422.0 | (M − H)− |
| 552 | SSC-AF-00 | 2.256 | 1466.0 | (M − H)− |
| 553 | SSC-AF-00 | 2.183 | 1409.9 | (M − H)− |
| 554 | SSC-FA-03 | 1.869 | 1381.9 | (M − H)− |
| 555 | SSC-AF-00 | 2.052 | 1356.0 | (M − H)− |
| 556 | SSC-AF-00 | 2.143 | 1473.5 | (M − H)− |
| 557 | SSC-FA-03 | 1.496 | 1432.8 | (M − H)− |
| 558 | SSC-TFA-07 | 1.637 | 1441.8 | (M + H)+ |
| 559 | SSC-FA-03 | 1.859 | 1407.9 | (M − H)− |
| 560 | SSC-TFA-07 | 1.336 | 1258.7 | (M + H)+ |
| 561 | SSC-TFA-07 | 1.504 | 1399.7 | (M + H)+ |
| 562 | SSC-FA-03 | 2.024 | 1437.9 | (M − H)− |
| 563 | SSC-AF-00 | 2.192 | 1435.6 | (M − H)− |
| 564 | SSC-TFA-07 | 1.365 | 1309.6 | (M + H)+ |
| 565 | SSC-TFA-07 | 1.412 | 1300.7 | (M + H)+ |
| 566 | SSC-AF-00 | 2.193 | 1396.7 | (M − H)− |
| 567 | SSC-FA-03 | 1.800 | 1402.0 | (M − H)− |
| 568 | SSC-FA-03 | 1.837 | 1385.9 | (M − H)− |
| 569 | SSC-TFA-07 | 1.509 | 1316.6 | (M + H)+ |
| 570 | SSC-TFA-07 | 1.520 | 1328.5 | (M + H)+ |
| 571 | SSC-A-FA-01 | 5.515 | 1425.7 | (M + H)+ |
| 572 | SSC-AF-00 | 2.261 | 1465.6 | (M − H)− |
| 573 | SSC-A-FA-02 | 6.337 | 1396.6 | (M + H)+ |
| 574 | SSC-A-FA-02 | 6.388 | 1452.6 | (M + H)+ |
| 575 | SSC-FA-03 | 1.847 | 1385.9 | (M − H)− |

TABLE 22-continued

| Compound No. | Analytical condition | Retention time (min) | MS Found(m/z) | MS polarity |
|---|---|---|---|---|
| 576 | SSC-AF-00 | 2.116 | 1220.5 | (M − H)− |
| 577 | SSC-TFA-07 | 1.644 | 1455.8 | (M + H)+ |
| 578 | SSC-TFA-07 | 1.540 | 1338.8 | (M + H)+ |
| 579 | SSC-A-FA-02 | 6.495 | 1430.6 | (M + H)+ |
| 580 | SSC-TFA-07 | 1.491 | 1314.7 | (M + H)+ |
| 581 | SSC-TFA-07 | 1.439 | 1274.6 | (M + H)+ |
| 582 | SSC-TFA-07 | 1.307 | 1417.8 | (M + H)+ |
| 583 | SSC-TFA-07 | 1.664 | 1368.8 | (M + H)+ |
| 584 | SSC-AF-00 | 2.133 | 1324.5 | (M − H)− |
| 585 | SSC-AF-00 | 2.179 | 1441.9 | (M − H)− |
| 586 | SSC-TFA-07 | 1.572 | 1318.7 | (M + H)+ |
| 587 | SSC-AF-00 | 2.147 | 1416.9 | (M − H)− |
| 588 | SSC-TFA-07 | 1.496 | 1288.7 | (M + H)+ |
| 589 | SSC-FA-03 | 1.799 | 1499.9 | (M − H)− |
| 590 | SSC-AF-00 | 2.229 | 1499.0 | (M − H)− |
| 591 | SSC-FA-03 | 1.967 | 1399.9 | (M − H)− |
| 592 | SSC-FA-03 | 2.153 | 1534.9 | (M − H)− |
| 593 | SSC-TFA-07 | 1.581 | 1330.7 | (M + H)+ |
| 594 | SSC-A-FA-02 | 6.632 | 1461.0 | (M + H)+ |
| 595 | SSC-AF-00 | 2.205 | 1342.7 | (M + H)+ |
| 596 | SSC-AF-00 | 2.173 | 1469.9 | (M − H)− |
| 597 | SSC-FA-03 | 1.824 | 1328.5 | (M − H)− |
| 598 | SSC-AF-00 | 2.181 | 1336.9 | (M − H)− |
| 599 | SSC-TFA-07 | 1.440 | 1397.8 | (M + H)+ |
| 600 | SSC-TFA-07 | 1.587 | 1415.8 | (M + H)+ |
| 601 | SSC-AF-00 | 2.179 | 1272.5 | (M − H)− |
| 602 | SSC-AF-00 | 2.152 | 1302.7 | (M + H)+ |
| 603 | SSC-FA-03 | 1.940 | 1427.9 | (M − H)− |
| 604 | SSC-FA-03 | 1.655 | 1427.7 | (M − H)− |
| 605 | SSC-FA-03 | 1.852 | 1360.9 | (M − H)− |
| 606 | SSC-A-AF-01 | 7.861 | 1470.7 | (M + H)+ |
| 607 | SSC-FA-03 | 1.825 | 1373.6 | (M − H)− |
| 608 | SSC-TFA-07 | 1.503 | 1304.7 | (M + H)+ |
| 609 | SSC-AA-20 | 2.107 | 1389.5 | (M − H)− |
| 610 | SSC-TFA-07 | 1.485 | 1411.7 | (M + H)+ |
| 611 | SSC-A-FA-02 | 6.413 | 1428.6 | (M + H)+ |
| 612 | SSC-TFA-07 | 1.217 | 1301.6 | (M + H)+ |
| 613 | SSC-TFA-07 | 1.297 | 1324.0 | (M + H)+ |
| 614 | SSC-AF-00 | 2.267 | 1547.0 | (M − H)− |
| 615 | SSC-TFA-07 | 1.597 | 1342.8 | (M + H)+ |
| 616 | SSC-FA-03 | 1.971 | 1489.8 | (M − H)− |
| 617 | SSC-AF-00 | 2.172 | 1496.0 | (M − H)− |
| 618 | SSC-FA-03 | 1.793 | 1313.6 | (M − H)− |
| 619 | SSC-FA-03 | 1.884 | 1441.9 | (M − H)− |
| 620 | SSC-TFA-07 | 1.511 | 1389.7 | (M + H)+ |
| 621 | SSC-AF-00 | 2.121 | 1246.8 | (M − H)− |
| 622 | SSC-A-AF-01 | 7.701 | 1472.0 | (M + H)+ |
| 623 | SSC-FA-03 | 1.833 | 1387.9 | (M − H)− |
| 624 | SSC-AF-00 | 2.131 | 1401.7 | (M − H)− |
| 625 | SSC-AF-00 | 2.081 | 1315.6 | (M − H)− |
| 626 | SSC-A-FA-02 | 6.673 | 1396.6 | (M + H)+ |
| 627 | SSC-AF-00 | 2.200 | 1425.9 | (M − H)− |
| 628 | SSC-A-FA-02 | 6.727 | 1393.1 | (M − H)− |
| 629 | SSC-TFA-07 | 1.608 | 1344.7 | (M + H)+ |
| 630 | SSC-AF-00 | 2.163 | 1501.8 | (M − H)− |
| 631 | SSC-AF-00 | 2.148 | 1449.9 | (M − H)− |
| 632 | SSC-AA-20 | 2.149 | 1332.7 | (M + H)+ |
| 633 | SSC-FA-03 | 1.873 | 1310.1 | (M − H)− |
| 634 | SSC-AA-20 | 2.128 | 1475.6 | (M − H)− |
| 635 | SSC-TFA-07 | 1.304 | 1423.7 | (M + H)+ |
| 636 | SSC-FA-03 | 1.824 | 1413.9 | (M − H)− |
| 637 | SSC-TFA-07 | 1.479 | 1463.5 | (M + H)+ |
| 638 | SSC-FA-03 | 1.851 | 1486.0 | (M − H)− |
| 639 | SSC-AF-00 | 2.179 | 1441.9 | (M − H)− |
| 640 | SSC-A-FA-01 | 6.267 | 1462.6 | (M + H)+ |
| 641 | SSC-TFA-07 | 1.413 | 1264.7 | (M + H)+ |
| 642 | SSC-TFA-07 | 1.615 | 1453.7 | (M + H)+ |
| 643 | SSC-AF-00 | 2.321 | 1495.6 | (M − H)− |
| 644 | SSC-TFA-07 | 1.489 | 1304.7 | (M + H)+ |
| 645 | SSC-TFA-07 | 1.440 | 1326.7 | (M + H)+ |
| 646 | SSC-TFA-07 | 1.329 | 1355.9 | (M + H)+ |
| 647 | SSC-FA-03 | 1.912 | 1451.9 | (M − H)− |
| 648 | SSC-FA-03 | 1.832 | 1334.5 | (M − H)− |
| 649 | SSC-TFA-07 | 1.460 | 1276.8 | (M + H)+ |
| 650 | SSC-AF-00 | 2.201 | 1441.9 | (M − H)− |
| 651 | SSC-FA-03 | 1.701 | 1244.5 | (M − H)− |
| 652 | SSC-A-FA-01 | 6.589 | 1476.6 | (M + H)+ |
| 653 | SSC-AF-00 | 2.151 | 1465.9 | (M + H)+ |
| 654 | SSC-TFA-07 | 1.339 | 1292.7 | (M + H)+ |
| 655 | SSC-A-FA-01 | 3.989 | 1442.7 | (M + H)+ |
| 656 | SSC-AF-00 | 2.253 | 1531.1 | (M − H)− |
| 657 | SSC-TFA-07 | 1.404 | 1375.6 | (M + H)+ |
| 658 | SSC-TFA-07 | 1.424 | 1288.7 | (M + H)+ |
| 659 | SSC-AF-00 | 2.077 | 1295.8 | (M − H)− |
| 660 | SSC-A-FA-01 | 4.956 | 1383.6 | (M + H)+ |
| 661 | SSC-AF-00 | 2.248 | 1470.0 | (M − H)− |
| 662 | SSC-AF-00 | 2.225 | 1455.9 | (M − H)− |
| 663 | SSC-TFA-07 | 1.483 | 1302.8 | (M + H)+ |
| 664 | SSC-TFA-07 | 1.243 | 1230.8 | (M + H)+ |
| 665 | SSC-AF-00 | 2.147 | 1288.7 | (M − H)− |
| 666 | SSC-FA-03 | 1.857 | 1300.6 | (M − H)− |
| 667 | SSC-FA-03 | 1.996 | 1439.8 | (M − H)− |
| 668 | SSC-A-FA-01 | 6.295 | 1442.6 | (M + H)+ |
| 669 | SSC-TFA-07 | 1.495 | 1338.6 | (M + H)+ |
| 670 | SSC-TFA-07 | 1.437 | 1369.7 | (M + H)+ |
| 671 | SSC-FA-03 | 1.800 | 1308.5 | (M + H)+ |
| 672 | SSC-FA-03 | 1.963 | 1438.0 | (M − H)− |
| 673 | SSC-A-AF-02 | 8.123 | 1450.7 | (M + H)+ |
| 674 | SSC-AF-00 | 2.135 | 1396.1 | (M − H)− |
| 675 | SSC-TFA-07 | 1.479 | 1415.8 | (M + H)+ |
| 676 | SSC-TFA-07 | 1.665 | 1483.7 | (M + H)+ |
| 677 | SSC-FA-03 | 1.864 | 1398.0 | (M − H)− |
| 678 | SSC-FA-03 | 1.865 | 1431.6 | (M − H)− |
| 679 | SSC-A-FA-01 | 5.848 | 1494.7 | (M + H)+ |
| 680 | SSC-AF-00 | 2.124 | 1453.8 | (M − H)− |
| 681 | SSC-FA-03 | 1.824 | 1422.0 | (M − H)− |
| 682 | SSC-AF-00 | 2.171 | 1504.6 | (M − H)− |
| 683 | SSC-FA-03 | 1.840 | 1501.9 | (M − H)− |
| 684 | SSC-AF-00 | 2.069 | 1385.5 | (M − H)− |
| 685 | SSC-FA-03 | 1.668 | 1299.6 | (M − H)− |
| 686 | SSC-TFA-07 | 1.584 | 1318.8 | (M + H)+ |
| 687 | SSC-TFA-07 | 1.479 | 1338.8 | (M + H)+ |
| 688 | SSC-FA-03 | 2.045 | 1471.9 | (M − H)− |
| 689 | SSC-FA-03 | 2.015 | 1437.8 | (M − H)− |
| 690 | SSC-FA-03 | 1.925 | 1415.9 | (M − H)− |
| 691 | SSC-FA-03 | 1.989 | 1415.8 | (M − H)− |
| 692 | SSC-FA-03 | 2.217 | 1485.9 | (M − H)− |
| 693 | SSC-AF-00 | 2.083 | 1419.5 | (M + H)+ |
| 694 | SSC-FA-03 | 1.933 | 1304.6 | (M + H)+ |
| 695 | SSC-A-FA-02 | 6.256 | 1422.7 | (M − H)− |
| 696 | SSC-AF-00 | 2.247 | 1517.8 | (M − H)− |
| 697 | SSC-TFA-07 | 1.360 | 1248.6 | (M + H)+ |
| 698 | SSC-A-FA-02 | 6.627 | 1461.0 | (M − H)− |
| 699 | SSC-AF-00 | 2.255 | 1467.6 | (M − H)− |
| 700 | SSC-FA-03 | 1.904 | 1423.6 | (M − H)− |
| 701 | SSC-AF-00 | 2.187 | 1465.8 | (M − H)− |
| 702 | SSC-FA-03 | 1.851 | 1401.7 | (M − H)− |
| 703 | SSC-AF-00 | 2.180 | 1514.0 | (M + H)+ |
| 704 | SSC-A-FA-02 | 6.629 | 1400.7 | (M − H)− |
| 705 | SSC-TFA-07 | 1.548 | 1306.7 | (M + H)+ |
| 706 | SSC-FA-03 | 1.911 | 1489.6 | (M − H)− |
| 707 | SSC-TFA-07 | 1.483 | 1302.7 | (M + H)+ |
| 708 | SSC-TFA-07 | 1.520 | 1304.7 | (M + H)+ |
| 709 | SSC-TFA-07 | 1.531 | 1439.7 | (M + H)+ |
| 710 | SSC-TFA-07 | 1.411 | 1420.7 | (M + H)+ |
| 711 | SSC-AF-00 | 2.189 | 1466.0 | (M − H)− |
| 712 | SSC-TFA-07 | 1.493 | 1387.7 | (M + H)+ |
| 713 | SSC-A-FA-02 | 6.597 | 1408.6 | (M + H)+ |
| 714 | SSC-TFA-07 | 1.375 | 1262.6 | (M + H)+ |
| 715 | SSC-AF-00 | 2.073 | 1355.6 | (M − H)− |
| 716 | SSC-FA-03 | 1.964 | 1421.8 | (M − H)− |
| 717 | SSC-AF-00 | 2.137 | 1404.9 | (M − H)− |
| 718 | SSC-FA-03 | 1.995 | 1455.5 | (M − H)− |
| 719 | SSC-A-AF-01 | 8.037 | 1558.9 | (M − H)− |
| 720 | SSC-FA-03 | 1.865 | 1340.7 | (M − H)− |
| 721 | SSC-FA-03 | 1.785 | 1451.9 | (M − H)− |
| 722 | SSC-FA-03 | 2.163 | 1454.0 | (M − H)− |
| 723 | SSC-TFA-07 | 1.544 | 1330.7 | (M + H)+ |
| 724 | SSC-A-FA-02 | 6.811 | 1424.7 | (M + H)+ |
| 725 | SSC-AF-00 | 2.211 | 1500.0 | (M − H)− |
| 726 | SSC-A-FA-01 | 5.923 | 1437.9 | (M − H)− |
| 727 | SSC-AF-00 | 2.275 | 1557.1 | (M − H)− |
| 728 | SSC-FA-03 | 2.157 | 1453.9 | (M − H)− |
| 729 | SSC-AF-00 | 2.211 | 1437.8 | (M − H)− |

TABLE 22-continued

| Compound No. | Analytical condition | Retention time (min) | MS Found(m/z) | MS polarity |
|---|---|---|---|---|
| 730 | SSC-FA-03 | 2.199 | 1469.9 | (M − H)− |
| 731 | SSC-A-AF-02 | 8.049 | 1452.7 | (M + H)+ |
| 732 | SSC-FA-03 | 1.920 | 1455.7 | (M − H)+ |
| 733 | SSC-TFA-07 | 1.579 | 1439.6 | (M + H)+ |
| 734 | SSC-AF-00 | 2.152 | 1464.0 | (M − H)− |
| 735 | SSC-AF-00 | 2.059 | 1427.7 | (M − H)− |
| 736 | SSC-FA-03 | 1.765 | 1347.5 | (M + H)+ |
| 737 | SSC-AF-00 | 2.281 | 1442.0 | (M − H)− |
| 738 | SSC-A-FA-02 | 6.660 | 1368.7 | (M + H)+ |
| 739 | SSC-TFA-07 | 1.388 | 1387.8 | (M + H)+ |
| 740 | SSC-TFA-07 | 1.484 | 1322.6 | (M + H)+ |
| 741 | SSC-AF-00 | 2.191 | 1414.0 | (M − H)− |
| 742 | SSC-TFA-07 | 1.441 | 1334.7 | (M + H)+ |
| 743 | SSC-A-FA-02 | 6.651 | 1461.1 | (M − H)− |
| 744 | SSC-FA-03 | 1.813 | 1416.0 | (M − H)− |
| 745 | SSC-AF-00 | 2.161 | 1409.5 | (M − H)− |
| 746 | SSC-AF-00 | 2.205 | 1286.9 | (M − H)− |
| 747 | SSC-TFA-07 | 1.577 | 1330.6 | (M + H)+ |
| 748 | SSC-FA-03 | 1.943 | 1427.7 | (M − H)− |
| 749 | SSC-FA-03 | 1.884 | 1360.5 | (M − H)− |
| 750 | SSC-A-FA-02 | 6.584 | 1428.5 | (M + H)+ |
| 751 | SSC-TFA-07 | 1.404 | 1306.7 | (M + H)+ |
| 752 | SSC-TFA-07 | 1.501 | 1419.6 | (M + H)+ |
| 753 | SSC-FA-03 | 1.968 | 1348.5 | (M − H)− |
| 754 | SSC-AF-00 | 2.191 | 1511.9 | (M − H)− |
| 755 | SSC-FA-03 | 1.937 | 1453.8 | (M − H)− |
| 756 | SSC-AF-00 | 2.179 | 1427.9 | (M − H)− |
| 757 | SSC-FA-03 | 1.751 | 1517.0 | (M − H)− |
| 758 | SSC-TFA-07 | 1.361 | 1357.6 | (M + H)+ |
| 759 | SSC-AF-00 | 2.140 | 1442.0 | (M − H)− |
| 760 | SSC-AF-00 | 2.179 | 1399.9 | (M − H)− |
| 761 | SSC-A-FA-01 | 6.021 | 1520.7 | (M + H)+ |
| 762 | SSC-TFA-07 | 1.592 | 1429.8 | (M + H)+ |
| 764 | SSC-TFA-07 | 1.415 | 1322.9 | (M + H)+ |
| 765 | SSC-AF-00 | 2.147 | 1441.6 | (M − H)− |
| 766 | SSC-FA-03 | 1.865 | 1421.6 | (M − H)− |
| 767 | SSC-TFA-07 | 1.375 | 1309.7 | (M + H)+ |
| 768 | SSC-A-AF-01 | 7.712 | 1423.8 | (M − H)− |
| 769 | SSC-TFA-07 | 1.409 | 1397.7 | (M + H)+ |
| 770 | SSC-FA-03 | 1.877 | 1548.9 | (M + H)+ |
| 771 | SSC-TFA-07 | 1.473 | 1314.7 | (M + H)+ |
| 772 | SSC-TFA-07 | 1.515 | 1346.8 | (M + H)+ |
| 773 | SSC-AF-00 | 2.159 | 1260.9 | (M − H)− |
| 774 | SSC-FA-03 | 1.872 | 1467.7 | (M − H)− |
| 775 | SSC-A-FA-02 | 6.701 | 1420.7 | (M − H)− |
| 776 | SSC-FA-03 | 1.868 | 1314.9 | (M − H)− |
| 777 | SSC-A-FA-02 | 6.740 | 1491.9 | (M + H)+ |
| 778 | SSC-FA-03 | 2.020 | 1425.8 | (M − H)− |
| 779 | SSC-TFA-07 | 1.401 | 1421.8 | (M + H)+ |
| 780 | SSC-A-FA-01 | 5.719 | 1638.9 | (M + H)+ |
| 781 | SSC-FA-03 | 1.888 | 1501.6 | (M − H)− |
| 782 | SSC-TFA-07 | 1.435 | 1352.6 | (M + H)+ |
| 783 | SSC-FA-03 | 2.005 | 1505.6 | (M − H)− |
| 784 | SSC-FA-03 | 1.775 | 1395.8 | (M − H)− |
| 785 | SSC-A-FA-02 | 6.371 | 1464.6 | (M + H)+ |
| 786 | SSC-AF-00 | 2.220 | 1531.0 | (M − H)− |
| 787 | SSC-TFA-07 | 1.513 | 1413.7 | (M + H)+ |
| 788 | SSC-TFA-07 | 1.368 | 1260.7 | (M + H)+ |
| 789 | SSC-FA-03 | 2.068 | 1515.9 | (M − H)− |
| 790 | SSC-FA-03 | 1.823 | 1426.0 | (M − H)− |
| 791 | SSC-FA-03 | 1.924 | 1537.4 | (M + H)+ |
| 792 | SSC-AF-00 | 2.161 | 1429.9 | (M − H)− |
| 793 | SSC-A-FA-01 | 5.032 | 1456.7 | (M + H)+ |
| 794 | SSC-FA-03 | 2.153 | 1483.9 | (M − H)− |
| 795 | SSC-FA-03 | 1.815 | 1324.5 | (M − H)− |
| 796 | SSC-FA-03 | 2.139 | 1520.1 | (M − H)− |
| 797 | SSC-TFA-07 | 1.459 | 1320.7 | (M + H)+ |
| 798 | SSC-FA-03 | 2.189 | 1370.6 | (M − H)− |
| 799 | SSC-AF-00 | 2.109 | 1397.8 | (M − H)− |
| 800 | SSC-TFA-07 | 1.456 | 1320.8 | (M + H)+ |
| 801 | SSC-TFA-07 | 1.643 | 1346.7 | (M + H)+ |
| 802 | SSC-TFA-07 | 1.379 | 1266.6 | (M + H)+ |
| 803 | SSC-AF-00 | 2.211 | 1468.0 | (M − H)− |
| 804 | SSC-TFA-07 | 1.395 | 1371.7 | (M + H)+ |
| 805 | SSC-FA-03 | 1.817 | 1442.8 | (M − H)− |
| 806 | SSC-A-FA-01 | 5.865 | 1439.9 | (M + H)+ |
| 807 | SSC-AF-00 | 2.167 | 1412.0 | (M − H)− |
| 808 | SSC-TFA-07 | 1.368 | 1391.8 | (M + H)+ |
| 809 | SSC-AF-00 | 2.281 | 1483.8 | (M − H)− |
| 810 | SSC-AF-00 | 2.160 | 1385.5 | (M − H)− |
| 811 | SSC-TFA-07 | 1.460 | 1288.7 | (M + H)+ |
| 812 | SSC-AF-00 | 2.272 | 1514.1 | (M − H)− |
| 813 | SSC-FA-03 | 2.088 | 1571.7 | (M − H)− |
| 814 | SSC-AF-00 | 2.091 | 1459.7 | (M − H)− |
| 815 | SSC-TFA-07 | 1.455 | 1288.7 | (M + H)+ |
| 816 | SSC-A-FA-02 | 6.792 | 1476.6 | (M + H)+ |
| 817 | SSC-A-FA-01 | 4.897 | 1524.7 | (M + H)+ |
| 818 | SSC-AF-00 | 2.135 | 1528.9 | (M − H)− |
| 819 | SSC-AF-00 | 2.233 | 1587.7 | (M − H)− |
| 820 | SSC-AF-00 | 2.207 | 1441.8 | (M − H)− |
| 821 | SSC-FA-03 | 1.945 | 1439.9 | (M − H)− |
| 822 | SSC-AF-00 | 2.152 | 1445.9 | (M − H)− |
| 823 | SSC-FA-03 | 1.961 | 1423.8 | (M − H)− |
| 824 | SSC-TFA-07 | 1.455 | 1290.6 | (M + H)+ |
| 825 | SSC-FA-03 | 1.939 | 1363.6 | (M − H)− |
| 826 | SSC-AF-00 | 2.136 | 1494.9 | (M − H)− |
| 827 | SSC-AF-00 | 2.049 | 1401.6 | (M − H)− |
| 828 | SSC-A-AF-01 | 7.365 | 1355.6 | (M + H)+ |
| 829 | SSC-FA-03 | 1.747 | 1367.9 | (M − H)− |
| 830 | SSC-AF-00 | 2.133 | 1298.6 | (M − H)− |
| 831 | SSC-FA-03 | 1.875 | 1286.5 | (M − H)− |
| 832 | SSC-TFA-07 | 1.451 | 1278.7 | (M + H)+ |
| 833 | SSC-A-FA-02 | 6.701 | 1440.7 | (M − H)− |
| 834 | SSC-FA-03 | 2.081 | 1312.9 | (M − H)− |
| 835 | SSC-FA-03 | 1.935 | 1439.8 | (M − H)− |
| 836 | SSC-FA-03 | 1.787 | 1413.7 | (M − H)− |
| 837 | SSC-TFA-07 | 1.477 | 1290.6 | (M + H)+ |
| 838 | SSC-FA-03 | 2.008 | 1505.6 | (M − H)− |
| 839 | SSC-AF-00 | 2.165 | 1274.8 | (M + H)+ |
| 840 | SSC-A-FA-01 | 5.016 | 1394.0 | (M − H)− |
| 841 | SSC-TFA-07 | 1.419 | 1317.7 | (M + H)+ |
| 842 | SSC-TFA-07 | 1.396 | 1250.7 | (M + H)+ |
| 843 | SSC-TFA-07 | 1.555 | 1328.9 | (M + H)+ |
| 844 | SSC-AF-00 | 2.105 | 1272.7 | (M − H)− |
| 845 | SSC-TFA-07 | 1.497 | 1316.7 | (M + H)+ |
| 847 | SSC-TFA-07 | 1.519 | 1312.9 | (M + H)+ |
| 848 | SSC-FA-03 | 2.136 | 1456.0 | (M − H)− |
| 849 | SSC-FA-03 | 2.104 | 1466.1 | (M − H)− |
| 850 | SSC-FA-03 | 1.809 | 1401.9 | (M − H)− |
| 851 | SSC-TFA-07 | 1.501 | 1332.6 | (M + H)+ |
| 852 | SSC-TFA-07 | 1.645 | 1374.7 | (M + H)+ |
| 853 | SSC-AF-00 | 2.077 | 1415.7 | (M − H)− |
| 854 | SSC-FA-03 | 2.063 | 1475.8 | (M − H)− |
| 855 | SSC-FA-03 | 2.113 | 1515.6 | (M − H)− |
| 856 | SSC-FA-03 | 1.736 | 1438.5 | (M − H)− |
| 857 | SSC-TFA-07 | 1.469 | 1302.7 | (M + H)+ |
| 858 | SSC-TFA-07 | 1.527 | 1376.8 | (M + H)+ |
| 859 | SSC-AF-00 | 2.165 | 1326.6 | (M − H)− |
| 860 | SSC-AF-00 | 2.033 | 1299.6 | (M − H)− |
| 861 | SSC-AF-00 | 2.169 | 1451.7 | (M − H)− |
| 862 | SSC-FA-03 | 1.715 | 1373.5 | (M − H)− |
| 863 | SSC-A-FA-01 | 6.205 | 1444.7 | (M + H)+ |
| 864 | SSC-TFA-07 | 1.560 | 1348.7 | (M + H)+ |
| 865 | SSC-AA-20 | 2.064 | 1292.7 | (M + H)+ |
| 866 | SSC-A-AF-01 | 7.561 | 1421.8 | (M − H)− |
| 867 | SSC-TFA-07 | 1.401 | 1420.7 | (M + H)+ |
| 868 | SSC-FA-03 | 1.880 | 1410.1 | (M − H)− |
| 869 | SSC-A-FA-02 | 6.093 | 1348.6 | (M + H)+ |
| 870 | SSC-TFA-07 | 1.439 | 1342.8 | (M + H)+ |
| 871 | SSC-AF-00 | 2.053 | 1410.0 | (M − H)− |
| 872 | SSC-FA-03 | 2.127 | 1472.0 | (M − H)− |
| 873 | SSC-AF-00 | 2.195 | 1340.9 | (M − H)− |
| 874 | SSC-TFA-07 | 1.431 | 1302.7 | (M + H)+ |
| 875 | SSC-TFA-07 | 1.425 | 1415.7 | (M + H)+ |
| 876 | SSC-FA-03 | 2.055 | 1517.7 | (M − H)− |
| 877 | SSC-AF-00 | 2.195 | 1425.9 | (M − H)− |
| 878 | SSC-TFA-07 | 1.443 | 1419.7 | (M + H)+ |
| 879 | SSC-TFA-07 | 1.400 | 1274.7 | (M + H)+ |
| 880 | SSC-FA-03 | 1.909 | 1413.8 | (M − H)− |
| 881 | SSC-FA-03 | 1.924 | 1493.8 | (M − H)− |
| 882 | SSC-FA-03 | 1.817 | 1487.9 | (M − H)− |
| 883 | SSC-AF-00 | 2.151 | 1292.8 | (M + H)+ |
| 884 | SSC-AA-20 | 2.132 | 1449.6 | (M + H)+ |
| 885 | SSC-AF-00 | 2.172 | 1427.8 | (M − H)− |

TABLE 22-continued

| Compound No. | Analytical condition | Retention time (min) | MS Found(m/z) | MS polarity |
|---|---|---|---|---|
| 886 | SSC-TFA-07 | 1.627 | 1334.7 | (M + H)+ |
| 887 | SSC-AF-00 | 2.223 | 1535.0 | (M − H)− |
| 888 | SSC-TFA-07 | 1.389 | 1323.7 | (M + H)+ |
| 889 | SSC-TFA-07 | 1.360 | 1458.8 | (M + H)+ |
| 890 | SSC-AF-00 | 2.153 | 1439.9 | (M − H)− |
| 891 | SSC-A-FA-02 | 6.420 | 1338.6 | (M − H)− |
| 892 | SSC-TFA-07 | 1.567 | 1320.8 | (M + H)+ |
| 893 | SSC-TFA-07 | 1.468 | 1333.8 | (M + H)+ |
| 894 | SSC-AF-00 | 2.211 | 1495.7 | (M − H)− |
| 895 | SSC-AF-00 | 2.187 | 1445.8 | (M − H)− |
| 896 | SSC-A-AF-01 | 7.573 | 1422.0 | (M − H)− |
| 897 | SSC-AF-00 | 2.173 | 1346.7 | (M + H)+ |
| 898 | SSC-A-FA-02 | 6.677 | 1418.7 | (M − H)− |
| 899 | SSC-A-FA-02 | 6.756 | 1439.9 | (M − H)− |
| 900 | SSC-A-AF-01 | 7.679 | 1456.7 | (M + H)+ |
| 901 | SSC-TFA-07 | 1.540 | 1316.6 | (M + H)+ |
| 902 | SSC-TFA-07 | 1.388 | 1272.7 | (M + H)+ |
| 903 | SSC-FA-03 | 1.729 | 1315.6 | (M − H)− |
| 904 | SSC-TFA-07 | 1.551 | 1318.7 | (M + H)+ |
| 905 | SSC-TFA-07 | 1.512 | 1304.8 | (M + H)+ |
| 906 | SSC-FA-03 | 1.861 | 1427.7 | (M − H)− |
| 907 | SSC-A-AF-01 | 7.649 | 1408.6 | (M + H)+ |
| 908 | SSC-FA-03 | 2.101 | 1489.8 | (M − H)− |
| 909 | SSC-AF-00 | 2.109 | 1298.6 | (M − H)− |
| 910 | SSC-AF-00 | 2.200 | 1532.7 | (M − H)− |
| 911 | SSC-TFA-07 | 1.551 | 1413.7 | (M + H)+ |
| 912 | SSC-FA-03 | 2.017 | 1487.5 | (M + H)+ |
| 913 | SSC-TFA-07 | 1.427 | 1334.6 | (M + H)+ |
| 914 | SSC-FA-03 | 1.588 | 1476.8 | (M − H)− |
| 915 | SSC-AF-00 | 2.051 | 1369.7 | (M − H)− |
| 916 | SSC-TFA-07 | 1.417 | 1345.8 | (M + H)+ |
| 917 | SSC-AF-00 | 2.200 | 1399.8 | (M − H)− |
| 918 | SSC-AF-00 | 2.075 | 1394.1 | (M − H)− |
| 919 | SSC-AF-00 | 2.048 | 1281.8 | (M − H)− |
| 920 | SSC-AF-00 | 2.193 | 1494.1 | (M − H)− |
| 921 | SSC-A-FA-01 | 5.544 | 1435.8 | (M − H)− |
| 922 | SSC-AF-00 | 2.156 | 1324.7 | (M − H)− |
| 923 | SSC-TFA-07 | 1.429 | 1300.7 | (M + H)+ |
| 924 | SSC-TFA-07 | 1.536 | 1316.6 | (M + H)+ |
| 925 | SSC-TFA-07 | 1.409 | 1395.7 | (M + H)+ |
| 926 | SSC-FA-03 | 1.856 | 1453.9 | (M − H)− |
| 927 | SSC-TFA-07 | 1.493 | 1336.9 | (M + H)+ |
| 928 | SSC-A-FA-02 | 6.937 | 1421.0 | (M − H)− |
| 929 | SSC-FA-03 | 1.856 | 1387.8 | (M − H)− |
| 930 | SSC-AF-00 | 2.061 | 1262.5 | (M + H)+ |
| 931 | SSC-FA-03 | 1.951 | 1473.9 | (M − H)− |
| 932 | SSC-A-FA-02 | 6.813 | 1464.7 | (M + H)+ |
| 933 | SSC-FA-03 | 1.905 | 1337.0 | (M − H)− |
| 934 | SSC-FA-03 | 2.075 | 1537.7 | (M − H)− |
| 935 | SSC-TFA-07 | 1.415 | 1420.6 | (M + H)+ |
| 936 | SSC-AF-00 | 2.148 | 1397.5 | (M − H)− |
| 937 | SSC-TFA-07 | 1.540 | 1316.6 | (M + H)+ |
| 938 | SSC-FA-03 | 1.701 | 1446.0 | (M − H)− |
| 939 | SSC-FA-03 | 1.949 | 1387.8 | (M − H)− |
| 940 | SSC-AF-00 | 2.347 | 1514.1 | (M − H)− |
| 941 | SSC-FA-03 | 1.963 | 1441.8 | (M − H)− |
| 942 | SSC-FA-03 | 1.633 | 1474.8 | (M − H)− |
| 943 | SSC-FA-03 | 1.785 | 1469.5 | (M − H)− |
| 944 | SSC-TFA-07 | 1.467 | 1292.7 | (M + H)+ |
| 945 | SSC-AF-00 | 2.167 | 1439.7 | (M − H)− |
| 946 | SSC-AF-00 | 2.124 | 1407.9 | (M − H)− |
| 947 | SSC-A-FA-02 | 6.931 | 1414.7 | (M + H)+ |
| 948 | SSC-AF-00 | 2.152 | 1397.9 | (M − H)− |
| 949 | SSC-A-FA-02 | 6.668 | 1454.5 | (M − H)− |
| 950 | SSC-FA-03 | 2.104 | 1552.9 | (M − H)− |
| 951 | SSC-A-FA-02 | 6.720 | 1408.7 | (M − H)− |
| 952 | SSC-TFA-07 | 1.472 | 1300.7 | (M + H)+ |
| 953 | SSC-AF-00 | 2.175 | 1359.6 | (M + H)+ |
| 954 | SSC-FA-03 | 1.868 | 1329.6 | (M − H)− |
| 955 | SSC-TFA-07 | 1.465 | 1419.7 | (M + H)+ |
| 956 | SSC-TFA-07 | 2.105 | 1306.7 | (M + H)+ |
| 957 | SSC-FA-03 | 1.780 | 1381.9 | (M − H)− |
| 958 | SSC-AF-00 | 2.161 | 1471.8 | (M − H)− |
| 959 | SSC-FA-03 | 2.021 | 1438.0 | (M − H)− |
| 960 | SSC-AF-00 | 2.283 | 1529.7 | (M + H)+ |
| 961 | SSC-AF-00 | 2.143 | 1484.6 | (M − H)− |
| 962 | SSC-A-FA-02 | 6.436 | 1352.6 | (M + H)+ |
| 963 | SSC-FA-03 | 1.999 | 1455.7 | (M − H)− |
| 964 | SSC-AF-00 | 2.195 | 1409.5 | (M − H)− |
| 965 | SSC-A-FA-01 | 5.088 | 1422.0 | (M − H)− |
| 966 | SSC-TFA-07 | 1.544 | 1328.7 | (M + H)+ |
| 967 | SSC-TFA-07 | 1.457 | 1278.8 | (M + H)+ |
| 968 | SSC-TFA-07 | 1.565 | 1427.7 | (M + H)+ |
| 969 | SSC-TFA-07 | 1.528 | 1389.8 | (M + H)+ |
| 970 | SSC-TFA-07 | 1.636 | 1332.7 | (M + H)+ |
| 971 | SSC-FA-03 | 1.881 | 1470.4 | (M − H)− |
| 972 | SSC-AF-00 | 2.183 | 1362.9 | (M − H)− |
| 973 | SSC-FA-03 | 1.899 | 1479.6 | (M − H)− |
| 974 | SSC-FA-03 | 1.731 | 1429.8 | (M − H)− |
| 975 | SSC-TFA-07 | 1.372 | 1309.6 | (M + H)+ |
| 976 | SSC-FA-03 | 1.711 | 1295.7 | (M − H)− |
| 977 | SSC-FA-03 | 1.923 | 1423.6 | (M − H)− |
| 978 | SSC-TFA-07 | 1.419 | 1294.8 | (M + H)+ |
| 979 | SSC-AF-00 | 2.108 | 1274.4 | (M − H)− |
| 980 | SSC-TFA-07 | 1.449 | 1385.7 | (M + H)+ |
| 981 | SSC-FA-03 | 1.812 | 1529.7 | (M − H)− |
| 982 | SSC-FA-03 | 1.784 | 1466.7 | (M − H)− |
| 983 | SSC-FA-03 | 2.175 | 1480.0 | (M − H)− |
| 984 | SSC-A-FA-01 | 6.952 | 1588.8 | (M + H)+ |
| 985 | SSC-TFA-07 | 1.441 | 1276.7 | (M + H)+ |
| 986 | SSC-AF-00 | 2.223 | 1440.0 | (M − H)− |
| 987 | SSC-FA-03 | 1.745 | 1398.1 | (M − H)− |
| 988 | SSC-TFA-07 | 1.581 | 1453.8 | (M + H)+ |
| 989 | SSC-TFA-07 | 1.329 | 1391.8 | (M + H)+ |
| 990 | SSC-FA-03 | 1.817 | 1326.4 | (M − H)− |
| 991 | SSC-TFA-07 | 1.584 | 1344.7 | (M + H)+ |
| 992 | SSC-TFA-07 | 1.705 | 1376.7 | (M + H)+ |
| 993 | SSC-AF-00 | 2.117 | 1359.9 | (M − H)− |
| 994 | SSC-TFA-07 | 1.476 | 1368.6 | (M + H)+ |
| 995 | SSC-AF-00 | 2.184 | 1425.6 | (M − H)− |
| 996 | SSC-TFA-07 | 1.520 | 1340.7 | (M + H)+ |
| 997 | SSC-FA-03 | 2.023 | 1521.5 | (M − H)− |
| 998 | SSC-TFA-07 | 1.653 | 1556.9 | (M + H)+ |
| 999 | SSC-FA-03 | 1.841 | 1383.6 | (M − H)− |
| 1000 | SSC-AF-00 | 2.157 | 1489.8 | (M − H)− |
| 1001 | SSC-FA-03 | 1.791 | 1475.9 | (M − H)− |
| 1002 | SSC-FA-03 | 1.800 | 1439.6 | (M − H)− |
| 1003 | SSC-A-FA-02 | 6.353 | 1416.6 | (M + H)+ |
| 1004 | SSC-FA-03 | 1.813 | 1292.9 | (M − H)− |
| 1005 | SSC-FA-03 | 2.143 | 1455.9 | (M − H)− |
| 1006 | SSC-A-FA-02 | 6.283 | 1446.6 | (M − H)− |
| 1007 | SSC-AF-00 | 2.279 | 1348.6 | (M − H)− |
| 1008 | SSC-AF-00 | 2.137 | 1444.0 | (M − H)− |
| 1009 | SSC-FA-03 | 2.075 | 1509.8 | (M − H)− |
| 1010 | SSC-FA-03 | 1.879 | 1399.8 | (M − H)− |
| 1011 | SSC-AF-00 | 2.057 | 1307.9 | (M − H)− |
| 1012 | SSC-AF-00 | 2.168 | 1463.0 | (M − H)− |
| 1013 | SSC-TFA-07 | 1.363 | 1272.8 | (M + H)+ |
| 1014 | SSC-TFA-07 | 1.541 | 1348.6 | (M + H)+ |
| 1015 | SSC-AF-00 | 2.183 | 1481.9 | (M − H)− |
| 1016 | SSC-FA-03 | 2.263 | 1541.8 | (M − H)− |
| 1017 | SSC-FA-03 | 1.724 | 1391.9 | (M − H)− |
| 1018 | SSC-TFA-07 | 1.432 | 1344.6 | (M + H)+ |
| 1019 | SSC-TFA-07 | 1.481 | 1316.7 | (M + H)+ |
| 1020 | SSC-TFA-07 | 1.491 | 1302.7 | (M + H)+ |
| 1021 | SSC-AF-00 | 2.156 | 1328.7 | (M + H)+ |
| 1022 | SSC-AF-00 | 2.220 | 1454.0 | (M − H)− |
| 1023 | SSC-AF-00 | 2.195 | 1363.0 | (M − H)− |
| 1024 | SSC-AF-00 | 2.075 | 1368.0 | (M − H)− |
| 1025 | SSC-FA-03 | 1.845 | 1492.9 | (M − H)− |
| 1026 | SSC-FA-03 | 2.020 | 1443.8 | (M − H)− |
| 1027 | SSC-FA-03 | 1.808 | 1372.0 | (M − H)− |
| 1029 | SSC-AF-00 | 2.129 | 1412.1 | (M − H)− |
| 1030 | SSC-AF-00 | 2.084 | 1440.1 | (M − H)− |
| 1031 | SSC-TFA-07 | 1.439 | 1278.8 | (M + H)+ |
| 1032 | SSC-AF-00 | 2.245 | 1332.6 | (M + H)+ |
| 1033 | SSC-TFA-07 | 1.604 | 1332.7 | (M + H)+ |
| 1034 | SSC-FA-03 | 1.741 | 1371.9 | (M − H)− |
| 1035 | SSC-AF-00 | 2.209 | 1521.6 | (M − H)− |
| 1036 | SSC-AF-00 | 2.179 | 1423.9 | (M − H)− |
| 1037 | SSC-FA-03 | 1.952 | 1427.8 | (M − H)− |
| 1038 | SSC-TFA-07 | 1.517 | 1304.7 | (M + H)+ |
| 1039 | SSC-A-FA-01 | 6.327 | 1616.8 | (M + H)+ |
| 1040 | SSC-AF-00 | 2.161 | 1410.0 | (M − H)− |

TABLE 22-continued

| Compound No. | Analytical condition | Retention time (min) | MS Found(m/z) | MS polarity |
|---|---|---|---|---|
| 1041 | SSC-FA-03 | 1.801 | 1401.9 | (M − H)− |
| 1042 | SSC-A-AF-01 | 7.533 | 1421.8 | (M − H)− |
| 1043 | SSC-AF-00 | 2.117 | 1317.8 | (M + H)+ |
| 1044 | SSC-AF-00 | 2.231 | 1537.6 | (M − H)− |
| 1045 | SSC-AF-00 | 2.260 | 1441.8 | (M − H)− |
| 1046 | SSC-FA-03 | 1.916 | 1326.9 | (M − H)− |
| 1047 | SSC-FA-03 | 1.904 | 1423.7 | (M − H)− |
| 1048 | SSC-TFA-07 | 1.339 | 1389.9 | (M + H)+ |
| 1049 | SSC-A-AF-02 | 7.935 | 1456.6 | (M + H)+ |
| 1050 | SSC-TFA-07 | 1.536 | 1316.7 | (M + H)+ |
| 1051 | SSC-TFA-07 | 1.453 | 1373.7 | (M + H)+ |
| 1052 | SSC-FA-03 | 2.075 | 1571.8 | (M − H)− |
| 1053 | SSC-FA-03 | 2.221 | 1542.0 | (M − H)− |
| 1054 | SSC-AF-00 | 2.107 | 1306.7 | (M + H)+ |
| 1055 | SSC-AF-00 | 2.137 | 1309.7 | (M − H)− |
| 1056 | SSC-AF-00 | 2.129 | 1272.9 | (M − H)− |
| 1057 | SSC-FA-03 | 1.869 | 1479.9 | (M − H)− |
| 1058 | SSC-AF-00 | 2.183 | 1525.5 | (M − H)− |
| 1059 | SSC-A-FA-01 | 5.319 | 1419.7 | (M − H)− |
| 1060 | SSC-FA-03 | 1.897 | 1451.9 | (M − H)− |
| 1061 | SSC-TFA-07 | 1.459 | 1427.7 | (M + H)+ |
| 1062 | SSC-A-AF-01 | 7.752 | 1454.6 | (M + H)+ |
| 1063 | SSC-AF-00 | 2.229 | 1509.8 | (M − H)− |
| 1064 | SSC-AF-00 | 2.169 | 1411.9 | (M − H)− |
| 1065 | SSC-AF-00 | 2.176 | 1314.5 | (M − H)− |
| 1066 | SSC-FA-03 | 1.765 | 1258.5 | (M − H)− |
| 1067 | SSC-TFA-07 | 1.364 | 1270.8 | (M + H)+ |
| 1068 | SSC-TFA-07 | 1.563 | 1320.7 | (M + H)+ |
| 1069 | SSC-TFA-07 | 1.473 | 1334.6 | (M + H)+ |
| 1070 | SSC-A-AF-01 | 7.624 | 1425.9 | (M − H)− |
| 1071 | SSC-FA-03 | 1.613 | 1476.8 | (M − H)− |
| 1072 | SSC-AF-00 | 2.125 | 1401.7 | (M − H)− |
| 1073 | SSC-AF-00 | 2.191 | 1425.9 | (M − H)− |
| 1074 | SSC-A-FA-02 | 6.265 | 1402.6 | (M + H)+ |
| 1075 | SSC-AF-00 | 2.137 | 1316.9 | (M − H)− |
| 1076 | SSC-TFA-07 | 1.536 | 1308.7 | (M + H)+ |
| 1077 | SSC-FA-03 | 1.847 | 1310.5 | (M − H)− |
| 1078 | SSC-FA-03 | 1.923 | 1522.8 | (M − H)− |
| 1079 | SSC-TFA-07 | 1.527 | 1356.9 | (M + H)+ |
| 1080 | SSC-A-AF-01 | 7.272 | 1410.0 | (M − H)− |
| 1081 | SSC-FA-03 | 1.516 | 1492.6 | (M − H)− |
| 1082 | SSC-TFA-07 | 1.555 | 1328.7 | (M + H)+ |
| 1083 | SSC-FA-03 | 1.875 | 1306.9 | (M − H)− |
| 1084 | SSC-TFA-07 | 1.411 | 1306.7 | (M + H)+ |
| 1085 | SSC-TFA-07 | 1.391 | 1391.8 | (M + H)+ |
| 1086 | SSC-AA-20 | 2.083 | 1290.4 | (M − H)− |
| 1087 | SSC-FA-03 | 1.739 | 1518.9 | (M − H)− |
| 1088 | SSC-FA-03 | 1.880 | 1294.5 | (M − H)− |
| 1089 | SSC-AF-00 | 2.185 | 1468.0 | (M − H)− |
| 1090 | SSC-TFA-07 | 1.355 | 1228.8 | (M + H)+ |
| 1091 | SSC-FA-03 | 1.860 | 1422.1 | (M − H)− |
| 1092 | SSC-TFA-07 | 1.373 | 1455.7 | (M + H)+ |
| 1093 | SSC-FA-03 | 2.097 | 1457.8 | (M − H)− |
| 1094 | SSC-FA-03 | 1.800 | 1449.7 | (M − H)− |
| 1095 | SSC-TFA-07 | 1.577 | 1318.8 | (M + H)+ |
| 1096 | SSC-AF-00 | 2.328 | 1544.0 | (M + H)+ |
| 1097 | SSC-TFA-07 | 1.429 | 1254.8 | (M + H)+ |
| 1098 | SSC-AF-00 | 2.060 | 1398.0 | (M − H)− |
| 1099 | SSC-AF-00 | 2.131 | 1407.6 | (M − H)− |
| 1100 | SSC-FA-03 | 1.883 | 1486.0 | (M − H)− |
| 1101 | SSC-FA-03 | 1.879 | 1415.9 | (M − H)− |
| 1102 | SSC-TFA-07 | 1.604 | 1372.7 | (M + H)+ |
| 1103 | SSC-FA-03 | 1.909 | 1397.9 | (M − H)− |
| 1104 | SSC-A-AF-01 | 7.524 | 1480.6 | (M + H)+ |
| 1105 | SSC-TFA-07 | 1.485 | 1340.6 | (M + H)+ |
| 1106 | SSC-AF-00 | 2.171 | 1411.9 | (M − H)− |
| 1107 | SSC-TFA-07 | 1.495 | 1314.7 | (M + H)+ |
| 1108 | SSC-A-FA-01 | 5.573 | 1510.7 | (M + H)+ |
| 1109 | SSC-AF-00 | 2.161 | 1399.9 | (M − H)− |
| 1110 | SSC-TFA-07 | 1.527 | 1348.6 | (M + H)+ |
| 1111 | SSC-TFA-07 | 1.424 | 1262.7 | (M + H)+ |
| 1112 | SSC-AF-00 | 2.157 | 1454.1 | (M − H)− |
| 1113 | SSC-AF-00 | 2.301 | 1481.8 | (M − H)− |
| 1114 | SSC-AF-00 | 2.200 | 1437.9 | (M − H)− |
| 1115 | SSC-AF-00 | 2.293 | 1485.8 | (M + H)+ |
| 1116 | SSC-FA-03 | 1.749 | 1515.8 | (M − H)− |
| 1117 | SSC-A-FA-01 | 5.455 | 1397.6 | (M + H)+ |
| 1118 | SSC-FA-03 | 1.989 | 1397.5 | (M − H)− |
| 1119 | SSC-TFA-07 | 1.463 | 1449.7 | (M + H)+ |
| 1120 | SSC-A-FA-01 | 5.471 | 1421.8 | (M − H)− |
| 1121 | SSC-FA-03 | 1.825 | 1383.6 | (M − H)− |
| 1122 | SSC-AF-00 | 2.193 | 1402.7 | (M − H)− |
| 1123 | SSC-FA-03 | 1.929 | 1490.0 | (M − H)− |
| 1124 | SSC-TFA-07 | 1.453 | 1373.7 | (M + H)+ |
| 1125 | SSC-AF-00 | 2.144 | 1407.9 | (M − H)− |
| 1126 | SSC-TFA-07 | 1.539 | 1340.6 | (M + H)+ |
| 1127 | SSC-FA-03 | 1.940 | 1524.0 | (M − H)− |
| 1128 | SSC-TFA-07 | 1.529 | 1413.7 | (M + H)+ |
| 1129 | SSC-FA-03 | 2.043 | 1565.5 | (M − H)− |
| 1130 | SSC-AF-00 | 2.168 | 1387.9 | (M − H)− |
| 1131 | SSC-A-AF-01 | 7.592 | 1395.7 | (M − H)− |
| 1132 | SSC-FA-03 | 1.993 | 1425.8 | (M − H)− |
| 1133 | SSC-AF-00 | 2.157 | 1346.7 | (M + H)+ |
| 1134 | SSC-AF-00 | 2.240 | 1452.0 | (M − H)− |
| 1135 | SSC-FA-03 | 1.444 | 1488.8 | (M − H)− |
| 1136 | SSC-FA-03 | 1.953 | 1483.9 | (M − H)− |
| 1137 | SSC-A-FA-01 | 5.269 | 1439.6 | (M − H)− |
| 1138 | SSC-FA-03 | 2.125 | 1427.9 | (M − H)− |
| 1139 | SSC-A-AF-01 | 7.524 | 1557.7 | (M − H)− |
| 1140 | SSC-A-FA-01 | 4.973 | 1427.7 | (M + H)+ |
| 1141 | SSC-A-FA-01 | 5.353 | 1419.7 | (M − H)− |
| 1142 | SSC-A-FA-01 | 5.333 | 1439.8 | (M − H)− |
| 1143 | SSC-A-FA-01 | 5.688 | 1470.1 | (M − H)− |
| 1144 | SSC-A-FA-01 | 5.969 | 1470.1 | (M − H)− |
| 1145 | SSC-A-AF-01 | 7.457 | 1437.8 | (M − H)− |
| 1146 | SSC-A-FA-01 | 5.632 | 1487.8 | (M − H)− |
| 1148 | SSC-A-AF-01 | 7.523 | 1433.8 | (M − H)− |
| 1149 | SSC-A-FA-01 | 5.876 | 1499.6 | (M + H)+ |
| 1150 | SSC-FA-03 | 2.049 | 1454.0 | (M − H)− |
| 1151 | SSC-A-FA-01 | 5.496 | 1517.8 | (M − H)− |
| 1152 | SSC-A-AF-01 | 7.393 | 1417.6 | (M − H)− |
| 1153 | SSC-FA-03 | 1.961 | 1336.5 | (M − H)− |
| 1154 | SSC-A-AF-01 | 7.671 | 1469.9 | (M − H)− |
| 1155 | SSC-AF-00 | 2.105 | 1513.4 | (M − H)− |
| 1156 | SSC-FA-03 | 1.977 | 1471.7 | (M + H)+ |
| 1157 | SSC-FA-03 | 2.037 | 1428.0 | (M − H)− |
| 1158 | SSC-A-AF-01 | 7.832 | 1467.9 | (M − H)− |
| 1159 | SSC-A-AF-01 | 7.680 | 1501.7 | (M − H)− |
| 1160 | SSC-A-FA-01 | 5.996 | 1450.0 | (M − H)− |
| 1161 | SSC-FA-03 | 1.984 | 1425.9 | (M − H)− |
| 1162 | SSC-A-FA-01 | 5.751 | 1458.1 | (M − H)− |
| 1163 | SSC-A-AF-01 | 7.803 | 1447.9 | (M − H)− |
| 1164 | SSC-A-AF-01 | 7.359 | 1382.0 | (M − H)− |
| 1165 | SSC-A-FA-01 | 5.871 | 1413.9 | (M − H)− |
| 1166 | SSC-A-FA-01 | 5.811 | 1450.0 | (M − H)− |
| 1167 | SSC-A-FA-01 | 5.355 | 1455.8 | (M − H)− |
| 1168 | SSC-FA-03 | 1.980 | 1457.9 | (M − H)− |
| 1169 | SSC-AF-00 | 2.061 | 1419.9 | (M − H)− |
| 1170 | SSC-A-FA-01 | 5.619 | 1414.0 | (M − H)− |
| 1171 | SSC-A-AF-01 | 7.760 | 1453.8 | (M − H)− |
| 1172 | SSC-FA-03 | 2.005 | 1413.7 | (M − H)− |
| 1173 | SSC-A-AF-01 | 7.568 | 1453.7 | (M + H)+ |
| 1174 | SSC-AF-00 | 2.140 | 1386.0 | (M − H)− |
| 1175 | SSC-A-AF-01 | 7.673 | 1504.0 | (M − H)− |
| 1176 | SSC-A-AF-01 | 7.804 | 1465.8 | (M − H)− |
| 1177 | SSC-AF-00 | 2.035 | 1405.5 | (M − H)− |
| 1178 | SSC-FA-03 | 1.801 | 1427.9 | (M − H)− |
| 1179 | SSC-A-FA-01 | 6.292 | 1505.6 | (M + H)+ |
| 1180 | SSC-FA-03 | 1.896 | 1427.9 | (M − H)− |
| 1181 | SSC-AF-00 | 2.084 | 1483.0 | (M − H)− |
| 1182 | SSC-A-FA-01 | 5.596 | 1565.7 | (M − H)− |
| 1183 | SSC-A-AF-01 | 7.759 | 1515.6 | (M + H)+ |
| 1184 | SSC-FA-03 | 1.736 | 1389.8 | (M − H)− |
| 1185 | SSC-FA-03 | 2.019 | 1354.6 | (M − H)− |
| 1186 | SSC-AF-00 | 2.239 | 1453.9 | (M − H)− |
| 1187 | SSC-FA-03 | 1.635 | 1345.7 | (M − H)− |
| 1188 | SSC-FA-03 | 1.771 | 1399.8 | (M − H)− |
| 1189 | SSC-A-AF-01 | 7.953 | 1455.8 | (M − H)− |
| 1190 | SSC-A-AF-01 | 7.725 | 1501.8 | (M − H)− |
| 1191 | SSC-AF-00 | 2.101 | 1456.9 | (M − H)− |
| 1192 | SSC-A-FA-01 | 6.016 | 1450.0 | (M − H)− |
| 1193 | SSC-A-AF-01 | 7.640 | 1469.8 | (M − H)− |
| 1194 | SSC-A-FA-01 | 6.040 | 1477.9 | (M − H)− |
| 1195 | SSC-FA-03 | 1.763 | 1401.5 | (M − H)− |

TABLE 22-continued

| Compound No. | Analytical condition | Retention time (min) | MS Found(m/z) | MS polarity |
|---|---|---|---|---|
| 1196 | SSC-A-FA-01 | 5.849 | 1549.9 | (M − H)− |
| 1197 | SSC-A-FA-01 | 5.459 | 1422.0 | (M − H)− |
| 1198 | SSC-A-AF-01 | 7.805 | 1437.8 | (M − H)− |
| 1199 | SSC-A-FA-01 | 5.912 | 1449.8 | (M − H)− |
| 1200 | SSC-FA-03 | 1.781 | 1415.5 | (M + H)+ |
| 1201 | SSC-A-FA-01 | 5.771 | 1458.1 | (M − H)− |
| 1202 | SSC-AF-00 | 2.189 | 1455.6 | (M − H)− |
| 1203 | SSC-FA-03 | 2.121 | 1454.0 | (M − H)− |
| 1204 | SSC-A-FA-01 | 6.067 | 1467.9 | (M − H)− |
| 1205 | SSC-A-FA-01 | 5.767 | 1410.1 | (M − H)− |
| 1206 | SSC-A-AF-01 | 7.420 | 1573.7 | (M − H)− |
| 1207 | SSC-FA-03 | 2.064 | 1497.9 | (M − H)− |
| 1208 | SSC-A-AF-01 | 7.500 | 1439.6 | (M − H)− |
| 1209 | SSC-A-FA-01 | 5.433 | 1466.1 | (M − H)− |
| 1210 | SSC-A-AF-01 | 7.595 | 1534.0 | (M − H)− |
| 1211 | SSC-FA-03 | 1.887 | 1385.9 | (M − H)− |
| 1212 | SSC-FA-03 | 1.771 | 1423.5 | (M + H)+ |
| 1213 | SSC-AF-00 | 2.108 | 1335.0 | (M − H)− |
| 1214 | SSC-FA-03 | 1.809 | 1439.8 | (M − H)− |
| 1215 | SSC-A-FA-01 | 5.611 | 1504.1 | (M − H)− |
| 1216 | SSC-FA-03 | 1.849 | 1399.4 | (M − H)− |
| 1217 | SSC-A-AF-01 | 7.496 | 1437.7 | (M + H)+ |
| 1218 | SSC-FA-03 | 1.948 | 1362.6 | (M − H)− |
| 1219 | SSC-AF-00 | 2.119 | 1473.8 | (M − H)− |
| 1220 | SSC-A-FA-01 | 5.807 | 1469.6 | (M + H)+ |
| 1221 | SSC-AF-00 | 2.115 | 1308.5 | (M − H)− |
| 1222 | SSC-AF-00 | 2.113 | 1308.7 | (M − H)− |
| 1223 | SSC-A-AF-01 | 7.413 | 1425.8 | (M − H)− |
| 1224 | SSC-A-FA-01 | 5.505 | 1466.0 | (M − H)− |
| 1225 | SSC-FA-03 | 1.799 | 1306.9 | (M − H)− |
| 1226 | SSC-FA-03 | 1.891 | 1455.9 | (M + H)+ |
| 1227 | SSC-FA-03 | 2.128 | 1454.0 | (M − H)− |
| 1228 | SSC-A-AF-01 | 7.584 | 1454.0 | (M − H)− |
| 1229 | SSC-FA-03 | 2.159 | 1547.8 | (M − H)− |
| 1230 | SSC-AF-00 | 2.075 | 1433.8 | (M − H)− |
| 1231 | SSC-A-FA-01 | 5.629 | 1441.7 | (M + H)+ |
| 1232 | SSC-A-AF-01 | 7.825 | 1448.0 | (M − H)− |
| 1233 | SSC-A-AF-01 | 7.552 | 1503.7 | (M − H)− |
| 1234 | SSC-A-FA-01 | 5.547 | 1517.8 | (M − H)− |
| 1235 | SSC-AF-00 | 2.152 | 1453.9 | (M − H)− |
| 1236 | SSC-A-FA-01 | 5.704 | 1501.8 | (M − H)− |
| 1237 | SSC-A-AF-01 | 7.513 | 1440.0 | (M − H)− |
| 1238 | SSC-FA-03 | 1.759 | 1475.7 | (M − H)− |
| 1239 | SSC-FA-03 | 1.735 | 1294.6 | (M − H)− |
| 1240 | SSC-FA-03 | 1.597 | 1388.6 | (M − H)− |
| 1241 | SSC-A-AF-01 | 7.871 | 1455.6 | (M − H)− |
| 1242 | SSC-A-FA-01 | 5.708 | 1523.7 | (M − H)− |
| 1243 | SSC-FA-03 | 1.995 | 1413.9 | (M − H)− |
| 1244 | SSC-A-FA-01 | 5.623 | 1516.0 | (M − H)− |
| 1245 | SSC-A-FA-01 | 5.728 | 1495.5 | (M − H)− |
| 1246 | SSC-AF-00 | 2.047 | 1431.8 | (M − H)− |
| 1247 | SSC-AF-00 | 2.125 | 1387.4 | (M − H)− |
| 1248 | SSC-A-FA-01 | 5.768 | 1464.0 | (M + H)+ |
| 1249 | SSC-AF-00 | 2.044 | 1453.9 | (M − H)− |
| 1250 | SSC-A-FA-01 | 5.671 | 1500.1 | (M − H)− |
| 1251 | SSC-A-FA-01 | 5.504 | 1481.8 | (M − H)− |
| 1252 | SSC-A-FA-01 | 5.383 | 1396.0 | (M − H)− |
| 1253 | SSC-A-FA-01 | 5.845 | 1414.1 | (M − H)− |
| 1254 | SSC-A-AF-01 | 7.511 | 1525.5 | (M − H)− |
| 1255 | SSC-FA-03 | 2.147 | 1453.8 | (M − H)− |
| 1256 | SSC-FA-03 | 1.660 | 1345.7 | (M − H)− |
| 1257 | SSC-FA-03 | 1.857 | 1427.8 | (M − H)− |
| 1258 | SSC-FA-03 | 1.849 | 1483.8 | (M − H)− |
| 1259 | SSC-A-FA-01 | 5.759 | 1499.6 | (M + H)+ |
| 1260 | SSC-A-FA-01 | 5.477 | 1567.9 | (M − H)− |
| 1261 | SSC-A-FA-01 | 5.271 | 1550.1 | (M − H)− |
| 1262 | SSC-A-AF-01 | 7.683 | 1424.0 | (M − H)− |
| 1263 | SSC-AF-00 | 2.123 | 1489.6 | (M − H)− |
| 1264 | SSC-A-FA-01 | 5.695 | 1432.1 | (M − H)− |
| 1265 | SSC-FA-03 | 2.044 | 1507.7 | (M − H)− |
| 1266 | SSC-A-AF-01 | 7.741 | 1455.9 | (M + H)+ |
| 1267 | SSC-A-AF-01 | 7.871 | 1455.9 | (M − H)− |
| 1268 | SSC-FA-03 | 1.655 | 1345.7 | (M − H)− |
| 1269 | SSC-A-AF-01 | 7.455 | 1431.8 | (M − H)− |
| 1270 | SSC-A-AF-01 | 7.739 | 1447.8 | (M − H)− |
| 1271 | SSC-A-FA-01 | 5.608 | 1560.0 | (M − H)− |
| 1272 | SSC-A-FA-01 | 5.901 | 1468.0 | (M − H)− |
| 1273 | SSC-FA-03 | 1.960 | 1414.0 | (M − H)− |
| 1274 | SSC-AF-00 | 2.204 | 1425.8 | (M − H)− |
| 1275 | SSC-A-FA-01 | 5.880 | 1426.1 | (M − H)− |
| 1276 | SSC-AF-00 | 2.192 | 1440.0 | (M − H)− |
| 1277 | SSC-AF-00 | 2.135 | 1401.6 | (M − H)− |
| 1278 | SSC-A-AF-01 | 7.327 | 1461.5 | (M − H)− |
| 1279 | SSC-FA-03 | 1.817 | 1449.9 | (M − H)− |
| 1280 | SSC-AF-00 | 2.203 | 1425.6 | (M − H)− |
| 1281 | SSC-A-FA-01 | 6.031 | 1490.0 | (M − H)− |
| 1282 | SSC-A-AF-01 | 7.433 | 1419.9 | (M − H)− |
| 1283 | SSC-A-FA-01 | 5.857 | 1460.0 | (M − H)− |
| 1284 | SSC-FA-03 | 1.616 | 1496.8 | (M − H)− |
| 1285 | SSC-A-FA-01 | 5.607 | 1463.8 | (M − H)− |
| 1286 | SSC-AF-00 | 2.145 | 1459.6 | (M − H)− |
| 1287 | SSC-A-FA-01 | 5.337 | 1409.5 | (M + H)+ |
| 1288 | SSC-FA-03 | 1.876 | 1499.9 | (M − H)− |
| 1289 | SSC-A-AF-01 | 7.719 | 1503.7 | (M + H)+ |
| 1290 | SSC-A-AF-01 | 7.801 | 1488.1 | (M − H)− |
| 1291 | SSC-FA-03 | 2.011 | 1439.8 | (M − H)− |
| 1292 | SSC-A-FA-01 | 5.412 | 1396.0 | (M − H)− |
| 1293 | SSC-A-FA-01 | 5.055 | 1491.9 | (M + H)+ |
| 1294 | SSC-FA-03 | 1.456 | 1468.8 | (M − H)− |
| 1295 | SSC-A-AF-01 | 7.777 | 1462.1 | (M − H)− |
| 1296 | SSC-A-FA-01 | 5.695 | 1455.9 | (M − H)− |
| 1297 | SSC-A-FA-01 | 5.351 | 1576.0 | (M − H)− |
| 1298 | SSC-AF-00 | 2.095 | 1485.7 | (M − H)− |
| 1299 | SSC-A-FA-01 | 5.024 | 1441.8 | (M − H)− |
| 1300 | SSC-FA-03 | 1.745 | 1258.8 | (M − H)− |
| 1301 | SSC-A-FA-01 | 5.500 | 1507.6 | (M + H)+ |
| 1302 | SSC-FA-03 | 2.048 | 1428.0 | (M − H)− |
| 1303 | SSC-A-AF-01 | 7.389 | 1551.9 | (M − H)− |
| 1304 | SSC-AF-00 | 2.033 | 1405.7 | (M − H)− |
| 1305 | SSC-AF-00 | 2.088 | 1333.6 | (M − H)− |
| 1306 | SSC-A-FA-01 | 5.596 | 1458.0 | (M − H)− |
| 1307 | SSC-FA-03 | 1.875 | 1322.5 | (M − H)− |
| 1308 | SSC-A-AF-01 | 7.648 | 1456.0 | (M − H)− |
| 1309 | SSC-A-FA-01 | 4.709 | 1411.9 | (M − H)− |
| 1310 | SSC-A-AF-01 | 7.676 | 1489.7 | (M + H)+ |
| 1311 | SSC-A-FA-01 | 5.421 | 1539.7 | (M − H)− |
| 1312 | SSC-A-AF-01 | 7.629 | 1517.9 | (M − H)− |
| 1313 | SSC-FA-03 | 1.787 | 1415.8 | (M − H)− |
| 1314 | SSC-AF-00 | 2.147 | 1399.9 | (M − H)− |
| 1315 | SSC-AF-00 | 2.208 | 1425.8 | (M − H)− |
| 1316 | SSC-AF-00 | 2.163 | 1399.9 | (M − H)− |
| 1317 | SSC-A-FA-01 | 5.619 | 1499.6 | (M + H)+ |
| 1318 | SSC-AF-00 | 2.124 | 1355.7 | (M − H)− |
| 1319 | SSC-A-FA-01 | 5.979 | 1501.7 | (M − H)− |
| 1320 | SSC-A-AF-01 | 7.676 | 1501.8 | (M + H)+ |
| 1321 | SSC-FA-03 | 1.956 | 1468.0 | (M − H)− |
| 1322 | SSC-A-FA-01 | 5.521 | 1463.9 | (M − H)− |
| 1323 | SSC-AF-00 | 2.195 | 1439.9 | (M − H)− |
| 1324 | SSC-A-AF-01 | 7.652 | 1410.0 | (M − H)− |
| 1325 | SSC-A-FA-01 | 5.819 | 1447.9 | (M − H)− |
| 1326 | SSC-A-FA-01 | 5.428 | 1455.8 | (M − H)− |
| 1327 | SSC-AF-00 | 2.064 | 1407.8 | (M − H)− |
| 1328 | SSC-AF-00 | 2.117 | 1324.5 | (M + H)+ |
| 1329 | SSC-FA-03 | 1.792 | 1413.5 | (M − H)− |
| 1330 | SSC-A-FA-01 | 5.368 | 1547.6 | (M − H)− |
| 1331 | SSC-AF-00 | 2.116 | 1334.5 | (M − H)− |
| 1332 | SSC-FA-03 | 1.908 | 1340.5 | (M − H)− |
| 1333 | SSC-AF-00 | 2.163 | 1441.8 | (M − H)− |
| 1334 | SSC-AF-00 | 2.147 | 1411.8 | (M − H)− |
| 1335 | SSC-A-AF-01 | 7.671 | 1531.8 | (M − H)− |
| 1336 | SSC-A-AF-01 | 7.255 | 1428.0 | (M − H)− |
| 1337 | SSC-A-FA-02 | 6.216 | 1481.7 | (M + H)+ |
| 1338 | SSC-A-FA-01 | 5.437 | 1469.9 | (M − H)− |
| 1339 | SSC-A-FA-01 | 5.604 | 1503.9 | (M − H)− |
| 1340 | SSC-A-FA-01 | 5.424 | 1408.0 | (M − H)− |
| 1341 | SSC-A-FA-01 | 6.053 | 1514.0 | (M − H)− |
| 1342 | SSC-A-AF-01 | 7.621 | 1414.1 | (M − H)− |
| 1343 | SSC-A-FA-01 | 5.456 | 1490.0 | (M − H)− |
| 1344 | SSC-FA-03 | 1.691 | 1419.7 | (M − H)− |
| 1345 | SSC-FA-03 | 2.153 | 1454.0 | (M − H)− |
| 1346 | SSC-A-FA-01 | 5.835 | 1449.9 | (M − H)− |
| 1347 | SSC-FA-03 | 2.111 | 1453.8 | (M − H)− |
| 1348 | SSC-A-FA-01 | 5.337 | 1543.6 | (M + H)+ |
| 1349 | SSC-FA-03 | 1.755 | 1463.5 | (M + H)+ |

TABLE 22-continued

| Compound No. | Analytical condition | Retention time (min) | MS Found(m/z) | MS polarity |
|---|---|---|---|---|
| 1350 | SSC-AF-00 | 2.072 | 1445.9 | (M − H)− |
| 1351 | SSC-A-FA-01 | 5.725 | 1450.0 | (M − H)− |
| 1352 | SSC-FA-03 | 1.920 | 1475.3 | (M − H)− |
| 1353 | SSC-AF-00 | 2.163 | 1412.0 | (M − H)− |
| 1354 | SSC-AF-00 | 2.216 | 1426.0 | (M − H)− |
| 1355 | SSC-A-AF-01 | 7.425 | 1457.9 | (M − H)− |
| 1356 | SSC-A-AF-01 | 7.568 | 1503.7 | (M − H)− |
| 1357 | SSC-A-FA-01 | 6.156 | 1487.8 | (M − H)− |
| 1358 | SSC-AF-00 | 2.095 | 1449.8 | (M − H)− |
| 1359 | SSC-A-FA-01 | 5.357 | 1467.9 | (M − H)− |
| 1360 | SSC-A-AF-01 | 7.449 | 1473.6 | (M − H)− |
| 1361 | SSC-FA-03 | 1.813 | 1457.8 | (M − H)− |
| 1362 | SSC-A-FA-01 | 5.183 | 1506.0 | (M − H)− |
| 1363 | SSC-A-AF-01 | 7.851 | 1460.0 | (M − H)− |
| 1364 | SSC-A-FA-01 | 5.587 | 1520.0 | (M − H)− |
| 1365 | SSC-A-FA-01 | 5.475 | 1422.0 | (M − H)− |
| 1366 | SSC-A-FA-02 | 6.213 | 1459.7 | (M + H)+ |
| 1367 | SSC-A-FA-01 | 5.889 | 1458.1 | (M − H)− |
| 1368 | SSC-A-AF-01 | 7.532 | 1478.0 | (M − H)− |
| 1369 | SSC-A-FA-01 | 5.992 | 1495.8 | (M − H)− |
| 1370 | SSC-A-FA-01 | 5.833 | 1457.7 | (M + H)+ |
| 1371 | SSC-A-FA-01 | 5.392 | 1517.9 | (M + H)+ |
| 1372 | SSC-FA-03 | 1.871 | 1405.7 | (M − H)− |
| 1373 | SSC-TFA-07 | 1.352 | 1322.8 | (M + H)+ |
| 1374 | SSC-A-AF-01 | 8.067 | 1457.7 | (M + H)+ |
| 1375 | SSC-TFA-07 | 1.348 | 1322.7 | (M + H)+ |
| 1376 | SSC-AF-00 | 2.192 | 1455.9 | (M − H)− |
| 1377 | SSC-FA-03 | 1.755 | 1284.4 | (M − H)− |
| 1378 | SSC-AF-00 | 2.161 | 1290.9 | (M − H)− |
| 1379 | SSC-FA-03 | 2.015 | 1340.5 | (M − H)− |
| 1380 | SSC-FA-03 | 1.821 | 1264.5 | (M − H)− |
| 1381 | SSC-FA-03 | 1.829 | 1286.9 | (M − H)− |
| 1382 | SSC-AF-00 | 2.132 | 1300.5 | (M + H)+ |
| 1383 | SSC-FA-03 | 1.863 | 1352.5 | (M − H)− |
| 1384 | SSC-AF-00 | 2.185 | 1330.6 | (M + H)+ |
| 1385 | SSC-FA-03 | 1.845 | 1342.4 | (M + H)+ |
| 1386 | SSC-FA-03 | 1.875 | 1326.7 | (M − H)− |
| 1387 | SSC-FA-03 | 1.816 | 1276.5 | (M − H)− |
| 1388 | SSC-AF-00 | 2.144 | 1314.6 | (M − H)− |
| 1389 | SSC-AF-00 | 2.217 | 1320.9 | (M − H)− |
| 1390 | SSC-FA-03 | 1.905 | 1278.9 | (M − H)− |
| 1391 | SSC-AF-00 | 2.160 | 1290.9 | (M − H)− |
| 1392 | SSC-AF-00 | 2.072 | 1340.4 | (M + H)+ |
| 1393 | SSC-AF-00 | 2.173 | 1382.4 | (M − H)− |
| 1394 | SSC-AF-00 | 2.188 | 1340.9 | (M − H)− |
| 1395 | SSC-FA-03 | 1.969 | 1394.9 | (M − H)− |
| 1396 | SSC-FA-03 | 1.905 | 1368.8 | (M − H)− |
| 1397 | SSC-FA-03 | 1.792 | 1328.6 | (M + H)+ |
| 1398 | SSC-FA-03 | 1.763 | 1272.8 | (M − H)− |
| 1399 | SSC-AF-00 | 2.120 | 1352.8 | (M − H)− |
| 1400 | SSC-FA-03 | 2.071 | 1333.0 | (M − H)− |
| 1401 | SSC-FA-03 | 2.001 | 1394.4 | (M − H)− |
| 1402 | SSC-AF-00 | 2.124 | 1298.9 | (M − H)− |
| 1403 | SSC-AF-00 | 2.133 | 1380.8 | (M − H)− |
| 1404 | SSC-AF-00 | 2.133 | 1393.8 | (M − H)− |
| 1405 | SSC-FA-03 | 1.904 | 1426.0 | (M + H)+ |
| 1406 | SSC-FA-03 | 1.787 | 1360.3 | (M − H)− |
| 1407 | SSC-TFA-07 | 1.359 | 1337.8 | (M + H)+ |
| 1408 | SSC-FA-03 | 1.797 | 1368.8 | (M − H)− |
| 1409 | SSC-TFA-07 | 1.376 | 1463.7 | (M + H)+ |
| 1410 | SSC-TFA-07 | 1.348 | 1415.7 | (M + H)+ |
| 1411 | SSC-FA-03 | 1.672 | 1345.6 | (M + H)+ |
| 1412 | SSC-TFA-07 | 1.304 | 1333.8 | (M + H)+ |
| 1413 | SSC-FA-03 | 1.903 | 1411.8 | (M − H)− |
| 1414 | SSC-AF-00 | 2.113 | 1451.7 | (M − H)− |
| 1415 | SSC-AF-00 | 2.143 | 1419.4 | (M − H)− |
| 1416 | SSC-AF-00 | 2.180 | 1413.9 | (M − H)− |
| 1417 | SSC-AF-00 | 2.168 | 1479.6 | (M + H)+ |
| 1418 | SSC-AF-00 | 2.137 | 1356.8 | (M − H)− |
| 1419 | SSC-FA-03 | 1.985 | 1479.7 | (M − H)− |
| 1420 | SSC-FA-03 | 1.904 | 1425.9 | (M − H)− |
| 1421 | SSC-FA-03 | 1.847 | 1439.8 | (M − H)− |
| 1422 | SSC-FA-03 | 1.889 | 1453.8 | (M − H)− |
| 1423 | SSC-AF-00 | 2.152 | 1401.5 | (M + H)+ |
| 1424 | SSC-TFA-07 | 1.468 | 1411.7 | (M + H)+ |
| 1425 | SSC-FA-03 | 1.767 | 1469.9 | (M − H)− |
| 1426 | SSC-FA-03 | 1.793 | 1423.3 | (M − H)− |
| 1427 | SSC-FA-03 | 1.715 | 1372.3 | (M − H)− |
| 1428 | SSC-AF-00 | 2.105 | 1449.8 | (M − H)− |
| 1429 | SSC-AF-00 | 2.135 | 1465.8 | (M − H)− |
| 1430 | SSC-TFA-07 | 1.425 | 1477.7 | (M + H)+ |
| 1431 | SSC-TFA-07 | 1.339 | 1413.6 | (M + H)+ |
| 1432 | SSC-TFA-07 | 1.572 | 1427.7 | (M + H)+ |
| 1433 | SSC-AF-00 | 2.176 | 1489.9 | (M − H)− |
| 1434 | SSC-AF-00 | 2.301 | 1515.9 | (M − H)− |
| 1435 | SSC-FA-03 | 2.109 | 1441.6 | (M − H)− |
| 1436 | SSC-AF-00 | 2.333 | 1513.9 | (M − H)− |
| 1437 | SSC-FA-03 | 2.192 | 1499.9 | (M − H)− |
| 1438 | SSC-FA-03 | 2.000 | 1427.9 | (M − H)− |
| 1439 | SSC-FA-03 | 2.059 | 1428.0 | (M − H)− |
| 1440 | SSC-AF-00 | 2.315 | 1499.9 | (M − H)− |
| 1441 | SSC-FA-03 | 2.076 | 1454.0 | (M − H)− |
| 1442 | SSC-AF-00 | 2.263 | 1489.8 | (M − H)− |
| 1443 | SSC-FA-03 | 2.272 | 1525.7 | (M − H)− |
| 1444 | SSC-FA-03 | 1.881 | 1429.9 | (M − H)− |
| 1445 | SSC-FA-03 | 2.032 | 1456.0 | (M − H)− |
| 1446 | SSC-AF-00 | 2.268 | 1489.9 | (M − H)− |
| 1447 | SSC-AF-00 | 2.217 | 1441.6 | (M + H)+ |
| 1448 | SSC-AF-00 | 2.189 | 1443.8 | (M − H)− |
| 1449 | SSC-FA-03 | 2.140 | 1453.8 | (M − H)− |
| 1450 | SSC-TFA-07 | 1.500 | 1487.9 | (M + H)+ |
| 1451 | SSC-AF-00 | 2.087 | 1318.7 | (M + H)+ |
| 1452 | SSC-TFA-07 | 1.479 | 1290.8 | (M + H)+ |
| 1453 | SSC-TFA-07 | 1.403 | 1411.8 | (M + H)+ |
| 1454 | SSC-TFA-07 | 1.481 | 1385.9 | (M + H)+ |
| 1455 | SSC-TFA-07 | 1.360 | 1385.8 | (M + H)+ |
| 1456 | SSC-TFA-07 | 1.447 | 1413.8 | (M + H)+ |
| 1457 | SSC-AF-00 | 2.148 | 1290.7 | (M + H)+ |
| 1458 | SSC-TFA-07 | 1.468 | 1385.9 | (M + H)+ |
| 1459 | SSC-TFA-07 | 1.521 | 1304.7 | (M + H)+ |
| 1460 | SSC-AF-00 | 2.088 | 1328.7 | (M + H)+ |
| 1461 | SSC-AF-00 | 2.176 | 1306.9 | (M − H)− |
| 1462 | SSC-FA-03 | 1.760 | 1292.5 | (M − H)− |
| 1463 | SSC-FA-03 | 1.788 | 1346.4 | (M − H)− |
| 1464 | SSC-AF-00 | 2.151 | 1398.5 | (M + H)+ |
| 1465 | SSC-FA-03 | 1.892 | 1294.6 | (M − H)− |
| 1466 | SSC-FA-03 | 1.741 | 1266.6 | (M − H)− |
| 1467 | SSC-TFA-07 | 1.491 | 1399.8 | (M + H)+ |
| 1468 | SSC-AF-00 | 2.223 | 1402.9 | (M − H)− |
| 1469 | SSC-TFA-07 | 1.399 | 1260.8 | (M + H)+ |
| 1470 | SSC-AF-00 | 2.144 | 1360.8 | (M − H)− |
| 1471 | SSC-AF-00 | 2.149 | 1322.9 | (M − H)− |
| 1472 | SSC-TFA-07 | 1.485 | 1384.7 | (M + H)+ |
| 1473 | SSC-AF-00 | 2.161 | 1384.9 | (M − H)− |
| 1474 | SSC-TFA-07 | 1.453 | 1274.8 | (M + H)+ |
| 1475 | SSC-FA-03 | 1.916 | 1402.8 | (M − H)− |
| 1476 | SSC-TFA-07 | 1.439 | 1372.7 | (M + H)+ |
| 1477 | SSC-FA-03 | 1.993 | 1340.9 | (M − H)− |
| 1478 | SSC-AF-00 | 2.123 | 1272.5 | (M − H)− |
| 1479 | SSC-FA-03 | 1.939 | 1310.5 | (M − H)− |
| 1480 | SSC-TFA-07 | 1.536 | 1510.9 | (M + H)+ |
| 1481 | SSC-FA-03 | 1.839 | 1284.9 | (M − H)− |
| 1482 | SSC-FA-03 | 2.025 | 1416.8 | (M − H)− |
| 1483 | SSC-TFA-07 | 1.404 | 1304.9 | (M + H)+ |
| 1484 | SSC-TFA-07 | 1.471 | 1372.7 | (M + H)+ |
| 1485 | SSC-FA-03 | 1.763 | 1280.9 | (M − H)− |
| 1486 | SSC-AF-00 | 2.081 | 1320.8 | (M − H)− |
| 1487 | SSC-AF-00 | 2.183 | 1348.9 | (M − H)− |
| 1488 | SSC-FA-03 | 1.899 | 1360.9 | (M − H)− |
| 1489 | SSC-TFA-07 | 1.447 | 1371.8 | (M + H)+ |
| 1490 | SSC-TFA-07 | 1.484 | 1288.8 | (M + H)+ |
| 1491 | SSC-FA-03 | 1.851 | 1298.9 | (M − H)− |
| 1492 | SSC-AF-00 | 2.172 | 1425.7 | (M + H)+ |
| 1493 | SSC-AF-00 | 2.115 | 1274.7 | (M + H)+ |
| 1494 | SSC-FA-03 | 1.885 | 1320.5 | (M − H)− |
| 1495 | SSC-TFA-07 | 1.515 | 1413.8 | (M + H)+ |
| 1496 | SSC-FA-03 | 1.883 | 1388.4 | (M − H)− |
| 1497 | SSC-FA-03 | 1.899 | 1374.4 | (M − H)− |
| 1498 | SSC-FA-03 | 1.873 | 1308.5 | (M − H)− |
| 1499 | SSC-AF-00 | 2.205 | 1326.9 | (M − H)− |
| 1500 | SSC-FA-03 | 1.883 | 1334.9 | (M − H)− |
| 1501 | SSC-AF-00 | 2.137 | 1398.0 | (M − H)− |
| 1502 | SSC-TFA-07 | 1.491 | 1476.9 | (M + H)+ |
| 1503 | SSC-TFA-07 | 1.529 | 1304.8 | (M + H)+ |

TABLE 22-continued

| Compound No. | Analytical condition | Retention time (min) | MS Found(m/z) | MS polarity |
|---|---|---|---|---|
| 1504 | SSC-FA-03 | 1.984 | 1362.6 | (M − H)− |
| 1505 | SSC-TFA-07 | 1.560 | 1386.7 | (M + H)+ |
| 1506 | SSC-FA-03 | 1.796 | 1258.5 | (M − H)+ |
| 1507 | SSC-AF-00 | 2.183 | 1360.5 | (M − H)− |
| 1508 | SSC-FA-03 | 1.895 | 1362.4 | (M − H)− |
| 1509 | SSC-AF-00 | 2.140 | 1324.7 | (M + H)+ |
| 1510 | SSC-FA-03 | 1.955 | 1312.9 | (M − H)− |
| 1511 | SSC-TFA-07 | 1.495 | 1278.8 | (M + H)+ |
| 1512 | SSC-FA-03 | 1.787 | 1360.3 | (M − H)− |
| 1513 | SSC-TFA-07 | 1.537 | 1425.8 | (M + H)+ |
| 1514 | SSC-AF-00 | 2.109 | 1306.4 | (M − H)− |
| 1515 | SSC-TFA-07 | 1.396 | 1298.8 | (M + H)+ |
| 1516 | SSC-AF-00 | 2.115 | 1370.9 | (M − H)− |
| 1517 | SSC-AF-00 | 2.225 | 1348.9 | (M − H)− |
| 1518 | SSC-AF-00 | 2.147 | 1288.8 | (M + H)+ |
| 1519 | SSC-TFA-07 | 1.475 | 1372.7 | (M + H)+ |
| 1520 | SSC-AF-00 | 2.172 | 1350.4 | (M + H)+ |
| 1521 | SSC-AF-00 | 2.223 | 1336.9 | (M − H)− |
| 1522 | SSC-FA-03 | 1.936 | 1372.4 | (M − H)− |
| 1523 | SSC-FA-03 | 1.784 | 1334.4 | (M − H)− |
| 1524 | SSC-AF-00 | 2.149 | 1376.8 | (M − H)− |
| 1525 | SSC-AF-00 | 2.136 | 1306.9 | (M − H)− |
| 1526 | SSC-AF-00 | 2.067 | 1302.8 | (M + H)+ |
| 1527 | SSC-TFA-07 | 1.536 | 1314.8 | (M + H)+ |
| 1528 | SSC-TFA-07 | 1.464 | 1449.8 | (M + H)+ |
| 1529 | SSC-TFA-07 | 1.404 | 1304.8 | (M + H)+ |
| 1530 | SSC-AF-00 | 2.263 | 1329.0 | (M − H)− |
| 1531 | SSC-FA-03 | 2.080 | 1340.5 | (M − H)− |
| 1532 | SSC-AF-00 | 2.113 | 1451.9 | (M − H)− |
| 1533 | SSC-AF-00 | 2.077 | 1270.7 | (M + H)+ |
| 1534 | SSC-AF-00 | 2.132 | 1274.7 | (M + H)+ |
| 1535 | SSC-AF-00 | 2.199 | 1286.5 | (M − H)− |
| 1536 | SSC-AF-00 | 2.164 | 1320.9 | (M − H)− |
| 1537 | SSC-FA-03 | 1.907 | 1348.9 | (M − H)− |
| 1538 | SSC-TFA-07 | 1.492 | 1407.8 | (M + H)+ |
| 1539 | SSC-FA-03 | 1.975 | 1299.0 | (M − H)− |
| 1540 | SSC-FA-03 | 1.861 | 1332.5 | (M − H)− |
| 1541 | SSC-TFA-07 | 1.477 | 1469.8 | (M + H)+ |
| 1542 | SSC-AF-00 | 2.224 | 1390.4 | (M − H)− |
| 1543 | SSC-AF-00 | 2.176 | 1298.9 | (M − H)− |
| 1544 | SSC-FA-03 | 1.931 | 1300.5 | (M − H)− |
| 1545 | SSC-AF-00 | 2.128 | 1274.7 | (M + H)+ |
| 1546 | SSC-TFA-07 | 1.431 | 1358.7 | (M + H)+ |
| 1547 | SSC-TFA-07 | 1.428 | 1298.7 | (M + H)+ |
| 1548 | SSC-TFA-07 | 1.632 | 1358.7 | (M + H)+ |
| 1549 | SSC-TFA-07 | 1.444 | 1312.7 | (M + H)+ |
| 1550 | SSC-TFA-07 | 1.444 | 1312.6 | (M + H)+ |
| 1551 | SSC-AF-00 | 2.079 | 1326.4 | (M − H)− |
| 1552 | SSC-TFA-07 | 1.727 | 1495.8 | (M + H)+ |
| 1553 | SSC-TFA-07 | 1.556 | 1453.8 | (M + H)+ |
| 1554 | SSC-TFA-07 | 1.699 | 1467.7 | (M + H)+ |
| 1555 | SSC-TFA-07 | 1.499 | 1463.7 | (M + H)+ |
| 1556 | SSC-TFA-07 | 1.405 | 1302.6 | (M + H)+ |
| 1557 | SSC-TFA-07 | 1.443 | 1413.7 | (M + H)+ |
| 1558 | SSC-TFA-07 | 1.657 | 1469.7 | (M + H)+ |
| 1559 | SSC-AF-00 | 2.203 | 1473.9 | (M − H)− |
| 1560 | SSC-TFA-07 | 1.587 | 1344.7 | (M + H)+ |
| 1561 | SSC-TFA-07 | 1.689 | 1503.7 | (M + H)+ |
| 1562 | SSC-TFA-07 | 1.425 | 1385.6 | (M + H)+ |
| 1563 | SSC-TFA-07 | 1.493 | 1382.6 | (M + H)+ |
| 1564 | SSC-TFA-07 | 1.476 | 1302.7 | (M + H)+ |
| 1565 | SSC-AF-00 | 2.140 | 1366.8 | (M − H)− |
| 1566 | SSC-AF-00 | 2.211 | 1451.8 | (M − H)− |
| 1567 | SSC-TFA-07 | 1.473 | 1366.6 | (M + H)+ |
| 1568 | SSC-TFA-07 | 1.525 | 1316.7 | (M + H)+ |
| 1569 | SSC-AF-00 | 2.208 | 1440.0 | (M − H)− |
| 1570 | SSC-AF-00 | 2.100 | 1310.5 | (M − H)− |
| 1571 | SSC-TFA-07 | 1.417 | 1316.6 | (M + H)+ |
| 1572 | SSC-TFA-07 | 1.484 | 1366.6 | (M + H)+ |
| 1573 | SSC-TFA-07 | 1.480 | 1368.6 | (M + H)+ |
| 1574 | SSC-TFA-07 | 1.760 | 1509.8 | (M + H)+ |
| 1575 | SSC-TFA-07 | 1.461 | 1352.7 | (M + H)+ |
| 1576 | SSC-TFA-07 | 1.473 | 1473.6 | (M + H)+ |
| 1577 | SSC-AF-00 | 2.279 | 1482.0 | (M − H)− |
| 1578 | SSC-TFA-07 | 1.391 | 1274.6 | (M + H)+ |
| 1579 | SSC-TFA-07 | 1.493 | 1463.7 | (M + H)+ |
| 1580 | SSC-TFA-07 | 1.624 | 1467.8 | (M + H)+ |
| 1581 | SSC-AF-00 | 2.301 | 1397.0 | (M − H)− |
| 1582 | SSC-TFA-07 | 1.447 | 1334.5 | (M + H)+ |
| 1583 | SSC-TFA-07 | 1.445 | 1413.7 | (M + H)+ |
| 1584 | SSC-AF-00 | 2.131 | 1407.9 | (M − H)− |
| 1585 | SSC-TFA-07 | 1.403 | 1302.6 | (M + H)+ |
| 1586 | SSC-AF-00 | 2.201 | 1340.4 | (M − H)− |
| 1587 | SSC-TFA-07 | 1.452 | 1362.5 | (M + H)+ |
| 1588 | SSC-TFA-07 | 1.425 | 1425.7 | (M + H)+ |
| 1589 | SSC-TFA-07 | 1.472 | 1348.6 | (M + H)+ |
| 1590 | SSC-TFA-07 | 1.459 | 1376.5 | (M + H)+ |
| 1591 | SSC-TFA-07 | 1.424 | 1318.6 | (M + H)+ |
| 1592 | SSC-AF-00 | 2.233 | 1454.0 | (M − H)− |
| 1593 | SSC-AF-00 | 2.204 | 1328.5 | (M − H)− |
| 1594 | SSC-AF-00 | 2.124 | 1409.5 | (M + H)+ |
| 1595 | SSC-TFA-07 | 1.587 | 1441.7 | (M + H)+ |
| 1596 | SSC-AF-00 | 2.252 | 1468.0 | (M − H)− |
| 1597 | SSC-TFA-07 | 1.473 | 1376.5 | (M + H)+ |
| 1598 | SSC-AF-00 | 2.101 | 1393.8 | (M − H)− |
| 1599 | SSC-TFA-07 | 1.425 | 1316.7 | (M + H)+ |
| 1600 | SSC-TFA-07 | 1.740 | 1495.8 | (M + H)+ |
| 1601 | SSC-AF-00 | 2.221 | 1454.0 | (M − H)− |
| 1602 | SSC-TFA-07 | 1.400 | 1302.6 | (M + H)+ |
| 1603 | SSC-AF-00 | 2.259 | 1480.1 | (M − H)− |
| 1604 | SSC-TFA-07 | 1.416 | 1298.7 | (M + H)+ |
| 1605 | SSC-TFA-07 | 1.393 | 1314.6 | (M + H)+ |
| 1606 | SSC-TFA-07 | 1.395 | 1284.6 | (M + H)+ |
| 1607 | SSC-TFA-07 | 1.433 | 1288.6 | (M + H)+ |
| 1608 | SSC-AF-00 | 2.131 | 1407.5 | (M − H)− |
| 1609 | SSC-TFA-07 | 1.491 | 1445.7 | (M + H)+ |
| 1610 | SSC-TFA-07 | 1.427 | 1316.7 | (M + H)+ |
| 1611 | SSC-AF-00 | 2.136 | 1427.7 | (M − H)− |
| 1612 | SSC-TFA-07 | 1.609 | 1356.7 | (M + H)+ |
| 1613 | SSC-TFA-07 | 1.453 | 1352.6 | (M + H)+ |
| 1614 | SSC-TFA-07 | 1.416 | 1298.7 | (M + H)+ |
| 1615 | SSC-TFA-07 | 1.445 | 1332.5 | (M + H)+ |
| 1616 | SSC-TFA-07 | 1.557 | 1427.6 | (M + H)+ |
| 1617 | SSC-TFA-07 | 1.467 | 1366.5 | (M + H)+ |
| 1618 | SSC-AF-00 | 2.281 | 1382.9 | (M − H)− |
| 1619 | SSC-TFA-07 | 1.617 | 1358.6 | (M + H)+ |
| 1620 | SSC-TFA-07 | 1.447 | 1352.6 | (M + H)+ |
| 1621 | SSC-TFA-07 | 1.463 | 1332.6 | (M + H)+ |
| 1622 | SSC-AF-00 | 2.221 | 1452.0 | (M − H)− |
| 1623 | SSC-TFA-07 | 1.443 | 1318.6 | (M + H)+ |
| 1624 | SSC-TFA-07 | 1.700 | 1517.8 | (M + H)+ |
| 1625 | SSC-TFA-07 | 1.441 | 1362.5 | (M + H)+ |
| 1626 | SSC-AF-00 | 2.128 | 1407.9 | (M − H)− |
| 1627 | SSC-TFA-07 | 1.431 | 1298.7 | (M + H)+ |
| 1628 | SSC-AF-00 | 2.244 | 1390.9 | (M − H)− |
| 1629 | SSC-TFA-07 | 1.481 | 1463.8 | (M + H)+ |
| 1630 | SSC-AF-00 | 2.155 | 1477.7 | (M − H)− |
| 1631 | SSC-AF-00 | 2.104 | 1411.8 | (M − H)− |
| 1632 | SSC-TFA-07 | 1.428 | 1298.7 | (M + H)+ |
| 1633 | SSC-TFA-07 | 1.487 | 1382.6 | (M + H)+ |
| 1634 | SSC-AF-00 | 2.100 | 1310.5 | (M − H)− |
| 1635 | SSC-TFA-07 | 1.469 | 1368.6 | (M + H)+ |
| 1636 | SSC-TFA-07 | 1.469 | 1429.6 | (M + H)+ |
| 1637 | SSC-TFA-07 | 1.500 | 1382.6 | (M + H)+ |
| 1638 | SSC-AF-00 | 2.143 | 1397.8 | (M − H)− |
| 1639 | SSC-TFA-07 | 1.513 | 1413.7 | (M + H)+ |
| 1640 | SSC-TFA-07 | 1.519 | 1479.8 | (M + H)+ |
| 1641 | SSC-TFA-07 | 1.511 | 1479.7 | (M + H)+ |
| 1642 | SSC-TFA-07 | 1.663 | 1467.8 | (M + H)+ |
| 1643 | SSC-TFA-07 | 1.496 | 1473.7 | (M + H)+ |
| 1644 | SSC-FA-03 | 2.124 | 1454.0 | (M − H)− |
| 1645 | SSC-AF-00 | 2.101 | 1433.8 | (M − H)− |
| 1646 | SSC-FA-03 | 1.849 | 1401.5 | (M − H)− |
| 1647 | SSC-AF-00 | 2.120 | 1421.9 | (M − H)− |
| 1648 | SSC-AF-00 | 2.136 | 1315.0 | (M − H)− |
| 1649 | SSC-AF-00 | 2.131 | 1421.9 | (M − H)− |
| 1650 | SSC-AF-00 | 2.216 | 1440.0 | (M − H)− |
| 1651 | SSC-FA-03 | 2.100 | 1453.8 | (M − H)− |
| 1652 | SSC-FA-03 | 1.947 | 1399.8 | (M − H)− |
| 1653 | SSC-AF-00 | 2.029 | 1393.8 | (M − H)− |
| 1654 | SSC-AF-00 | 2.200 | 1328.7 | (M − H)− |
| 1655 | SSC-FA-03 | 1.755 | 1272.8 | (M − H)− |
| 1656 | SSC-AF-00 | 2.137 | 1411.9 | (M − H)− |
| 1657 | SSC-FA-03 | 1.988 | 1439.9 | (M − H)− |

TABLE 22-continued

| Compound No. | Analytical condition | Retention time (min) | MS Found(m/z) | MS polarity |
|---|---|---|---|---|
| 1658 | SSC-AF-00 | 2.121 | 1433.5 | (M − H)− |
| 1659 | SSC-FA-03 | 1.844 | 1385.8 | (M − H)− |
| 1660 | SSC-AF-00 | 2.167 | 1461.8 | (M − H)− |
| 1661 | SSC-AF-00 | 2.139 | 1336.5 | (M − H)− |
| 1662 | SSC-FA-03 | 1.885 | 1400.0 | (M − H)− |
| 1663 | SSC-FA-03 | 2.127 | 1465.9 | (M − H)− |
| 1664 | SSC-FA-03 | 1.759 | 1399.8 | (M − H)− |
| 1665 | SSC-FA-03 | 1.821 | 1411.7 | (M − H)− |
| 1666 | SSC-AF-00 | 2.117 | 1383.9 | (M − H)− |
| 1667 | SSC-FA-03 | 2.084 | 1312.4 | (M + H)+ |
| 1668 | SSC-AF-00 | 2.232 | 1455.8 | (M − H)− |
| 1669 | SSC-FA-03 | 1.956 | 1411.9 | (M − H)− |
| 1670 | SSC-AF-00 | 2.105 | 1397.8 | (M − H)− |
| 1671 | SSC-AF-00 | 2.225 | 1439.8 | (M − H)− |
| 1672 | SSC-FA-03 | 1.920 | 1412.0 | (M − H)− |
| 1673 | SSC-FA-03 | 2.000 | 1376.9 | (M − H)− |
| 1674 | SSC-FA-03 | 1.731 | 1343.6 | (M − H)− |
| 1675 | SSC-FA-03 | 1.959 | 1425.8 | (M − H)− |
| 1676 | SSC-AF-00 | 2.165 | 1408.0 | (M − H)− |
| 1677 | SSC-AF-00 | 2.075 | 1369.9 | (M − H)− |
| 1678 | SSC-AF-00 | 2.160 | 1411.9 | (M − H)− |
| 1679 | SSC-AF-00 | 2.152 | 1437.8 | (M − H)− |
| 1680 | SSC-FA-03 | 1.956 | 1413.9 | (M − H)− |
| 1681 | SSC-AF-00 | 2.100 | 1357.9 | (M − H)− |
| 1682 | SSC-FA-03 | 1.957 | 1350.9 | (M − H)− |
| 1683 | SSC-FA-03 | 1.736 | 1280.9 | (M − H)− |
| 1684 | SSC-FA-03 | 1.831 | 1385.8 | (M − H)− |
| 1685 | SSC-FA-03 | 1.831 | 1433.8 | (M − H)− |
| 1686 | SSC-AF-00 | 2.159 | 1399.9 | (M − H)− |
| 1687 | SSC-FA-03 | 1.771 | 1373.9 | (M − H)− |
| 1688 | SSC-FA-03 | 1.852 | 1287.0 | (M − H)− |
| 1689 | SSC-AF-00 | 2.196 | 1425.9 | (M − H)− |
| 1690 | SSC-AF-00 | 2.179 | 1454.0 | (M − H)− |
| 1691 | SSC-FA-03 | 1.755 | 1254.4 | (M − H)− |
| 1692 | SSC-FA-03 | 2.107 | 1454.0 | (M − H)− |
| 1693 | SSC-AF-00 | 2.171 | 1490.8 | (M − H)− |
| 1694 | SSC-FA-03 | 1.904 | 1336.9 | (M − H)− |
| 1695 | SSC-FA-03 | 1.881 | 1397.8 | (M − H)− |
| 1696 | SSC-FA-03 | 1.937 | 1399.5 | (M + H)+ |
| 1697 | SSC-FA-03 | 2.021 | 1440.0 | (M − H)− |
| 1698 | SSC-FA-03 | 1.775 | 1395.7 | (M − H)− |
| 1699 | SSC-AF-00 | 2.087 | 1371.9 | (M − H)− |
| 1700 | SSC-AF-00 | 2.192 | 1461.6 | (M − H)− |
| 1701 | SSC-AF-00 | 2.180 | 1465.9 | (M − H)− |
| 1702 | SSC-AF-00 | 2.089 | 1298.4 | (M − H)− |
| 1703 | SSC-FA-03 | 1.491 | 1476.8 | (M − H)− |
| 1704 | SSC-FA-03 | 1.908 | 1451.8 | (M − H)− |
| 1705 | SSC-FA-03 | 2.009 | 1439.9 | (M − H)− |
| 1706 | SSC-FA-03 | 2.065 | 1354.8 | (M − H)− |
| 1707 | SSC-FA-03 | 2.044 | 1453.8 | (M − H)− |
| 1708 | SSC-AF-00 | 2.224 | 1439.8 | (M − H)− |
| 1709 | SSC-AF-00 | 2.152 | 1399.6 | (M − H)− |
| 1710 | SSC-FA-03 | 1.811 | 1411.8 | (M − H)− |
| 1711 | SSC-AF-00 | 2.097 | 1386.0 | (M − H)− |
| 1712 | SSC-FA-03 | 1.853 | 1385.9 | (M − H)− |
| 1713 | SSC-AF-00 | 2.169 | 1413.9 | (M − H)− |
| 1714 | SSC-AF-00 | 2.181 | 1362.6 | (M − H)− |
| 1715 | SSC-AF-00 | 2.123 | 1383.9 | (M − H)− |
| 1716 | SSC-AF-00 | 2.132 | 1397.7 | (M − H)− |
| 1717 | SSC-AF-00 | 2.187 | 1354.8 | (M − H)− |
| 1718 | SSC-AF-00 | 2.104 | 1465.0 | (M − H)− |
| 1719 | SSC-AF-00 | 2.201 | 1427.9 | (M − H)− |
| 1720 | SSC-FA-03 | 1.833 | 1383.7 | (M − H)− |
| 1721 | SSC-AF-00 | 1.701 | 1359.5 | (M − H)− |
| 1722 | SSC-AF-00 | 2.235 | 1440.0 | (M − H)− |
| 1723 | SSC-AF-00 | 2.232 | 1440.0 | (M − H)− |
| 1724 | SSC-FA-03 | 1.811 | 1391.9 | (M − H)− |
| 1725 | SSC-AF-00 | 2.111 | 1421.8 | (M − H)− |
| 1726 | SSC-FA-03 | 2.004 | 1452.0 | (M − H)− |
| 1727 | SSC-AF-00 | 2.164 | 1447.7 | (M − H)− |
| 1728 | SSC-FA-03 | 1.808 | 1385.9 | (M − H)− |
| 1729 | SSC-AF-00 | 2.149 | 1399.9 | (M − H)− |
| 1730 | SSC-AF-00 | 2.083 | 1292.5 | (M − H)− |
| 1731 | SSC-AF-00 | 2.139 | 1413.9 | (M − H)− |
| 1732 | SSC-FA-03 | 1.711 | 1284.4 | (M − H)− |
| 1733 | SSC-FA-03 | 2.021 | 1342.7 | (M − H)− |
| 1734 | SSC-FA-03 | 1.832 | 1487.5 | (M − H)− |
| 1735 | SSC-AF-00 | 2.269 | 1454.0 | (M − H)− |
| 1736 | SSC-FA-03 | 2.052 | 1455.8 | (M − H)− |
| 1737 | SSC-AF-00 | 2.101 | 1371.8 | (M − H)− |
| 1738 | SSC-AF-00 | 2.117 | 1399.8 | (M − H)− |
| 1739 | SSC-FA-03 | 1.901 | 1412.0 | (M − H)− |
| 1740 | SSC-AF-00 | 2.240 | 1439.8 | (M − H)− |
| 1741 | SSC-AF-00 | 2.133 | 1385.9 | (M − H)− |
| 1742 | SSC-AF-00 | 2.129 | 1298.9 | (M − H)− |
| 1743 | SSC-FA-03 | 1.871 | 1371.6 | (M − H)− |
| 1744 | SSC-FA-03 | 2.020 | 1465.9 | (M − H)− |
| 1745 | SSC-AF-00 | 2.151 | 1507.0 | (M − H)− |
| 1746 | SSC-FA-03 | 2.087 | 1451.8 | (M − H)− |
| 1747 | SSC-FA-03 | 1.951 | 1362.9 | (M − H)− |
| 1748 | SSC-FA-03 | 1.865 | 1444.0 | (M − H)− |
| 1749 | SSC-FA-03 | 1.745 | 1393.8 | (M − H)− |
| 1750 | SSC-AF-00 | 2.141 | 1362.6 | (M − H)− |
| 1751 | SSC-FA-03 | 1.873 | 1401.5 | (M + H)+ |
| 1752 | SSC-FA-03 | 1.764 | 1357.8 | (M − H)− |
| 1753 | SSC-FA-03 | 1.787 | 1377.6 | (M − H)− |
| 1754 | SSC-FA-03 | 1.972 | 1425.9 | (M − H)− |
| 1755 | SSC-AF-00 | 2.084 | 1383.9 | (M − H)− |
| 1756 | SSC-AF-00 | 2.076 | 1419.9 | (M − H)− |
| 1757 | SSC-FA-03 | 1.937 | 1425.8 | (M − H)− |
| 1758 | SSC-FA-03 | 1.731 | 1413.9 | (M − H)− |
| 1759 | SSC-FA-03 | 2.056 | 1452.0 | (M − H)− |
| 1760 | SSC-AF-00 | 2.148 | 1397.9 | (M − H)− |
| 1761 | SSC-AF-00 | 2.077 | 1419.9 | (M − H)− |
| 1762 | SSC-AF-00 | 2.081 | 1407.7 | (M − H)− |
| 1763 | SSC-FA-03 | 1.920 | 1441.5 | (M − H)− |
| 1764 | SSC-FA-03 | 1.889 | 1439.9 | (M − H)− |
| 1765 | SSC-AF-00 | 2.135 | 1499.7 | (M − H)− |
| 1766 | SSC-AF-00 | 2.211 | 1453.9 | (M − H)− |
| 1767 | SSC-AF-00 | 2.169 | 1412.0 | (M − H)− |
| 1768 | SSC-FA-03 | 1.751 | 1399.8 | (M − H)− |
| 1769 | SSC-AF-00 | 2.079 | 1407.8 | (M − H)− |
| 1770 | SSC-AF-00 | 2.196 | 1411.9 | (M − H)− |
| 1771 | SSC-FA-03 | 1.919 | 1429.8 | (M − H)− |
| 1772 | SSC-AF-00 | 2.152 | 1459.6 | (M − H)− |
| 1773 | SSC-AF-00 | 2.165 | 1300.5 | (M − H)− |
| 1774 | SSC-AF-00 | 2.113 | 1310.9 | (M − H)− |
| 1775 | SSC-AF-00 | 2.183 | 1412.0 | (M − H)− |
| 1776 | SSC-FA-03 | 2.048 | 1453.8 | (M − H)− |
| 1777 | SSC-AF-00 | 2.125 | 1411.8 | (M − H)− |
| 1778 | SSC-FA-03 | 1.737 | 1268.4 | (M + H)+ |
| 1779 | SSC-FA-03 | 1.761 | 1393.8 | (M − H)− |
| 1780 | SSC-FA-03 | 1.812 | 1383.9 | (M − H)− |
| 1781 | SSC-FA-03 | 1.899 | 1425.8 | (M − H)− |
| 1782 | SSC-AF-00 | 2.135 | 1436.0 | (M − H)− |
| 1783 | SSC-AF-00 | 2.133 | 1282.5 | (M + H)+ |
| 1784 | SSC-FA-03 | 1.923 | 1300.6 | (M − H)− |
| 1785 | SSC-AF-00 | 2.136 | 1459.8 | (M − H)− |
| 1786 | SSC-FA-03 | 2.016 | 1453.9 | (M − H)− |
| 1787 | SSC-FA-03 | 2.020 | 1451.8 | (M − H)− |
| 1788 | SSC-FA-03 | 1.741 | 1399.5 | (M − H)− |
| 1789 | SSC-AF-00 | 2.183 | 1346.9 | (M − H)− |
| 1790 | SSC-FA-03 | 1.807 | 1407.8 | (M − H)− |
| 1791 | SSC-AF-00 | 2.157 | 1411.9 | (M − H)− |
| 1792 | SSC-AF-00 | 2.100 | 1324.5 | (M − H)− |
| 1793 | SSC-FA-03 | 1.912 | 1350.6 | (M − H)− |
| 1794 | SSC-FA-03 | 1.845 | 1411.9 | (M − H)− |
| 1795 | SSC-AF-00 | 2.188 | 1474.0 | (M − H)− |
| 1796 | SSC-FA-03 | 1.971 | 1423.9 | (M − H)− |
| 1797 | SSC-AF-00 | 2.132 | 1447.7 | (M − H)− |
| 1798 | SSC-FA-03 | 2.017 | 1425.9 | (M − H)− |
| 1799 | SSC-AF-00 | 2.161 | 1413.9 | (M − H)− |
| 1800 | SSC-AF-00 | 2.168 | 1328.5 | (M − H)− |
| 1801 | SSC-FA-03 | 1.836 | 1322.9 | (M − H)− |
| 1802 | SSC-FA-03 | 1.952 | 1397.6 | (M − H)− |
| 1803 | SSC-AF-00 | 2.120 | 1385.9 | (M − H)− |
| 1804 | SSC-AF-00 | 2.157 | 1447.9 | (M − H)− |
| 1805 | SSC-FA-03 | 1.923 | 1415.9 | (M − H)− |
| 1806 | SSC-FA-03 | 1.801 | 1391.8 | (M − H)− |
| 1807 | SSC-FA-03 | 2.015 | 1425.9 | (M − H)− |
| 1808 | SSC-FA-03 | 1.880 | 1301.0 | (M − H)− |
| 1809 | SSC-FA-03 | 1.856 | 1336.9 | (M − H)− |
| 1810 | SSC-AF-00 | 2.116 | 1460.8 | (M − H)− |
| 1811 | SSC-AF-00 | 2.172 | 1439.8 | (M − H)− |

TABLE 22-continued

| Compound No. | Analytical condition | Retention time (min) | MS Found(m/z) | MS polarity |
|---|---|---|---|---|
| 1812 | SSC-AF-00 | 2.079 | 1359.5 | (M − H)− |
| 1813 | SSC-AF-00 | 2.228 | 1368.9 | (M − H)− |
| 1814 | SSC-AF-00 | 2.131 | 1399.9 | (M − H)− |
| 1815 | SSC-FA-03 | 1.940 | 1413.8 | (M − H)− |
| 1816 | SSC-AF-00 | 2.105 | 1409.7 | (M − H)− |
| 1817 | SSC-AF-00 | 2.179 | 1411.7 | (M − H)− |
| 1818 | SSC-AF-00 | 2.124 | 1411.8 | (M − H)− |
| 1819 | SSC-FA-03 | 1.936 | 1439.7 | (M − H)− |
| 1820 | SSC-AF-00 | 2.251 | 1465.8 | (M − H)− |
| 1821 | SSC-AF-00 | 2.205 | 1425.9 | (M − H)− |
| 1822 | SSC-FA-03 | 1.885 | 1424.0 | (M − H)− |
| 1823 | SSC-FA-03 | 1.972 | 1426.0 | (M − H)− |
| 1824 | SSC-FA-03 | 2.063 | 1451.9 | (M − H)− |
| 1825 | SSC-FA-03 | 1.843 | 1397.5 | (M − H)− |
| 1826 | SSC-AF-00 | 2.231 | 1439.8 | (M − H)− |
| 1827 | SSC-FA-03 | 1.809 | 1383.9 | (M − H)− |
| 1828 | SSC-AF-00 | 2.111 | 1434.0 | (M − H)− |
| 1829 | SSC-FA-03 | 1.900 | 1385.9 | (M − H)− |
| 1830 | SSC-FA-03 | 1.992 | 1414.0 | (M − H)− |
| 1831 | SSC-FA-03 | 1.935 | 1441.9 | (M − H)− |
| 1832 | SSC-FA-03 | 1.955 | 1399.9 | (M − H)− |
| 1833 | SSC-AF-00 | 2.212 | 1439.9 | (M − H)− |
| 1834 | SSC-FA-03 | 1.627 | 1448.8 | (M − H)− |
| 1835 | SSC-AF-00 | 2.236 | 1451.9 | (M − H)− |
| 1836 | SSC-FA-03 | 1.779 | 1381.6 | (M − H)− |
| 1837 | SSC-FA-03 | 1.760 | 1399.5 | (M − H)− |
| 1838 | SSC-FA-03 | 2.095 | 1465.6 | (M − H)− |
| 1839 | SSC-AF-00 | 2.121 | 1403.9 | (M − H)− |
| 1840 | SSC-AF-00 | 2.101 | 1445.9 | (M − H)− |
| 1841 | SSC-AF-00 | 2.136 | 1425.8 | (M − H)− |
| 1842 | SSC-AF-00 | 2.085 | 1407.9 | (M − H)− |
| 1843 | SSC-AF-00 | 2.163 | 1425.9 | (M − H)− |
| 1844 | SSC-AF-00 | 2.091 | 1365.9 | (M − H)− |
| 1845 | SSC-AF-00 | 2.176 | 1411.9 | (M − H)− |
| 1846 | SSC-AF-00 | 2.196 | 1413.6 | (M − H)− |
| 1847 | SSC-FA-03 | 1.800 | 1399.8 | (M − H)− |
| 1848 | SSC-AF-00 | 2.071 | 1387.9 | (M − H)− |
| 1849 | SSC-AF-00 | 2.201 | 1407.8 | (M − H)− |
| 1850 | SSC-FA-03 | 1.904 | 1433.7 | (M − H)− |
| 1851 | SSC-FA-03 | 1.948 | 1360.9 | (M − H)− |
| 1852 | SSC-AF-00 | 2.137 | 1460.0 | (M − H)− |
| 1853 | SSC-AF-00 | 2.099 | 1409.5 | (M − H)− |
| 1854 | SSC-FA-03 | 1.911 | 1399.5 | (M − H)− |
| 1855 | SSC-FA-03 | 1.957 | 1455.8 | (M − H)− |
| 1856 | SSC-AF-00 | 2.148 | 1336.6 | (M − H)− |
| 1857 | SSC-FA-03 | 1.877 | 1429.7 | (M + H)+ |
| 1858 | SSC-AF-00 | 2.131 | 1399.9 | (M − H)− |
| 1859 | SSC-FA-03 | 1.985 | 1439.8 | (M − H)− |
| 1860 | SSC-AF-00 | 2.223 | 1451.8 | (M − H)− |
| 1861 | SSC-AF-00 | 2.259 | 1454.0 | (M − H)− |
| 1862 | SSC-FA-03 | 1.980 | 1424.0 | (M − H)− |
| 1863 | SSC-FA-03 | 1.953 | 1425.8 | (M − H)− |
| 1864 | SSC-AF-00 | 2.187 | 1451.5 | (M − H)− |
| 1865 | SSC-AF-00 | 2.097 | 1373.9 | (M − H)− |
| 1866 | SSC-FA-03 | 1.737 | 1420.0 | (M − H)− |
| 1867 | SSC-AF-00 | 2.024 | 1367.8 | (M − H)− |
| 1868 | SSC-AF-00 | 2.172 | 1437.8 | (M − H)− |
| 1869 | SSC-FA-03 | 1.871 | 1475.8 | (M − H)− |
| 1870 | SSC-AF-00 | 2.140 | 1410.0 | (M − H)− |
| 1871 | SSC-AF-00 | 2.101 | 1435.7 | (M − H)− |
| 1872 | SSC-FA-03 | 1.817 | 1449.6 | (M − H)− |
| 1873 | SSC-A-FA-01 | 6.407 | 1549.7 | (M − H)− |
| 1874 | SSC-A-AF-01 | 8.385 | 1427.0 | (M − H)− |
| 1875 | SSC-AF-00 | 2.139 | 1428.0 | (M − H)− |
| 1876 | SSC-A-FA-01 | 6.835 | 1531.7 | (M + H)+ |
| 1877 | SSC-FA-03 | 1.836 | 1425.6 | (M − H)− |
| 1878 | SSC-A-FA-01 | 5.625 | 1467.7 | (M + H)+ |
| 1879 | SSC-FA-03 | 1.924 | 1465.6 | (M − H)− |
| 1880 | SSC-AF-00 | 2.231 | 1490.0 | (M − H)− |
| 1881 | SSC-FA-03 | 1.537 | 1491.0 | (M − H)− |
| 1882 | SSC-A-AF-01 | 7.781 | 1546.1 | (M − H)− |
| 1883 | SSC-A-FA-01 | 6.135 | 1364.6 | (M + H)+ |
| 1884 | SSC-AF-00 | 2.092 | 1475.7 | (M − H)− |
| 1885 | SSC-A-AF-01 | 7.835 | 1487.7 | (M − H)− |
| 1886 | SSC-FA-03 | 1.516 | 1486.8 | (M − H)− |
| 1887 | SSC-A-FA-01 | 6.040 | 1473.7 | (M + H)+ |
| 1888 | SSC-A-FA-01 | 6.519 | 1598.0 | (M − H)− |
| 1889 | SSC-A-FA-01 | 5.489 | 1431.6 | (M + H)+ |
| 1890 | SSC-AF-00 | 2.101 | 1459.7 | (M − H)− |
| 1891 | SSC-A-AF-01 | 8.248 | 1380.6 | (M − H)− |
| 1892 | SSC-AF-00 | 2.144 | 1490.8 | (M − H)− |
| 1893 | SSC-A-FA-01 | 5.875 | 1509.7 | (M + H)+ |
| 1894 | SSC-FA-03 | 1.919 | 1411.8 | (M − H)− |
| 1895 | SSC-A-FA-01 | 6.648 | 1513.8 | (M − H)− |
| 1896 | SSC-AF-00 | 2.049 | 1389.9 | (M − H)− |
| 1897 | SSC-AF-00 | 2.061 | 1460.8 | (M − H)− |
| 1898 | SSC-FA-03 | 1.879 | 1459.8 | (M − H)− |
| 1899 | SSC-A-AF-01 | 8.316 | 1432.5 | (M − H)− |
| 1900 | SSC-FA-03 | 1.807 | 1443.6 | (M − H)− |
| 1901 | SSC-AF-00 | 2.169 | 1440.0 | (M − H)− |
| 1902 | SSC-A-FA-01 | 6.504 | 1555.9 | (M − H)− |
| 1903 | SSC-A-FA-01 | 5.531 | 1461.6 | (M + H)+ |
| 1904 | SSC-AF-00 | 2.080 | 1421.7 | (M − H)− |
| 1905 | SSC-FA-03 | 1.801 | 1405.8 | (M − H)− |
| 1906 | SSC-AF-00 | 2.156 | 1439.8 | (M − H)− |
| 1907 | SSC-FA-03 | 1.956 | 1463.9 | (M − H)− |
| 1908 | SSC-FA-03 | 1.877 | 1427.8 | (M − H)− |
| 1909 | SSC-A-AF-01 | 7.932 | 1471.6 | (M − H)− |
| 1910 | SSC-A-FA-01 | 6.503 | 1597.8 | (M − H)− |
| 1911 | SSC-FA-03 | 1.779 | 1466.8 | (M − H)− |
| 1912 | SSC-A-FA-01 | 6.449 | 1378.7 | (M + H)+ |
| 1913 | SSC-AF-00 | 2.131 | 1476.8 | (M − H)− |
| 1914 | SSC-A-FA-01 | 5.473 | 1450.0 | (M − H)− |
| 1915 | SSC-FA-03 | 1.841 | 1413.6 | (M − H)− |
| 1916 | SSC-FA-03 | 1.868 | 1439.8 | (M − H)− |
| 1917 | SSC-FA-03 | 1.500 | 1436.9 | (M − H)− |
| 1918 | SSC-A-AF-01 | 8.237 | 1436.6 | (M + H)+ |
| 1919 | SSC-A-FA-01 | 6.120 | 1392.6 | (M + H)+ |
| 1920 | SSC-A-FA-01 | 5.977 | 1515.6 | (M + H)+ |
| 1921 | SSC-FA-03 | 1.852 | 1470.8 | (M − H)− |
| 1922 | SSC-A-FA-01 | 5.559 | 1459.9 | (M − H)− |
| 1923 | SSC-FA-03 | 1.849 | 1427.8 | (M − H)− |
| 1924 | SSC-FA-03 | 1.965 | 1485.8 | (M − H)− |
| 1925 | SSC-FA-03 | 1.912 | 1411.8 | (M − H)− |
| 1926 | SSC-AF-00 | 2.191 | 1526.0 | (M − H)− |
| 1927 | SSC-A-FA-01 | 5.764 | 1497.1 | (M − H)− |
| 1928 | SSC-FA-03 | 1.923 | 1453.6 | (M − H)− |
| 1929 | SSC-FA-03 | 1.745 | 1373.9 | (M − H)− |
| 1930 | SSC-AF-00 | 2.139 | 1522.0 | (M − H)− |
| 1931 | SSC-FA-03 | 1.831 | 1383.9 | (M − H)− |
| 1932 | SSC-FA-03 | 1.904 | 1529.8 | (M − H)− |
| 1933 | SSC-FA-03 | 1.924 | 1453.8 | (M − H)− |
| 1934 | SSC-FA-03 | 1.796 | 1401.9 | (M − H)− |
| 1935 | SSC-A-AF-01 | 7.776 | 1501.9 | (M − H)− |
| 1936 | SSC-FA-03 | 1.913 | 1454.0 | (M − H)− |
| 1937 | SSC-AF-00 | 2.104 | 1479.0 | (M − H)− |
| 1938 | SSC-AF-00 | 2.169 | 1441.8 | (M − H)− |
| 1939 | SSC-AF-00 | 2.141 | 1391.6 | (M − H)− |
| 1940 | SSC-AF-00 | 2.163 | 1434.2 | (M − H)− |
| 1941 | SSC-AF-00 | 2.135 | 1373.6 | (M − H)− |
| 1942 | SSC-A-FA-01 | 6.349 | 1525.6 | (M + H)+ |
| 1943 | SSC-A-FA-01 | 6.147 | 1507.5 | (M − H)− |
| 1944 | SSC-A-FA-01 | 5.992 | 1557.6 | (M + H)+ |
| 1945 | SSC-A-FA-01 | 6.043 | 1515.6 | (M + H)+ |
| 1946 | SSC-AF-00 | 2.117 | 1462.8 | (M − H)− |
| 1947 | SSC-FA-03 | 1.851 | 1408.2 | (M − H)− |
| 1948 | SSC-FA-03 | 1.847 | 1503.9 | (M − H)− |
| 1949 | SSC-FA-03 | 1.733 | 1403.5 | (M − H)− |
| 1950 | SSC-A-AF-02 | 7.981 | 1399.8 | (M − H)− |
| 1951 | SSC-A-AF-01 | 7.521 | 1501.9 | (M − H)− |
| 1952 | SSC-A-FA-01 | 6.000 | 1492.0 | (M − H)− |
| 1953 | SSC-A-AF-01 | 7.695 | 1555.9 | (M − H)− |
| 1954 | SSC-FA-03 | 1.836 | 1427.8 | (M − H)− |
| 1955 | SSC-AF-00 | 2.204 | 1546.8 | (M − H)− |
| 1956 | SSC-FA-03 | 1.741 | 1415.8 | (M − H)− |
| 1957 | SSC-FA-03 | 1.908 | 1452.0 | (M − H)− |
| 1958 | SSC-AF-00 | 2.145 | 1397.6 | (M − H)− |
| 1959 | SSC-A-AF-01 | 7.092 | 1454.7 | (M − H)− |
| 1960 | SSC-A-FA-01 | 5.577 | 1465.6 | (M − H)− |
| 1961 | SSC-A-FA-01 | 4.977 | 1359.6 | (M + H)+ |
| 1962 | SSC-FA-03 | 1.501 | 1472.9 | (M − H)− |
| 1963 | SSC-AF-00 | 2.123 | 1448.0 | (M − H)− |
| 1964 | SSC-A-FA-01 | 6.416 | 1549.6 | (M − H)− |
| 1965 | SSC-FA-03 | 1.860 | 1426.1 | (M − H)− |

TABLE 22-continued

| Compound No. | Analytical condition | Retention time (min) | MS Found(m/z) | MS polarity |
|---|---|---|---|---|
| 1966 | SSC-FA-03 | 1.760 | 1418.0 | (M − H)− |
| 1967 | SSC-A-FA-01 | 5.724 | 1360.5 | (M − H)− |
| 1968 | SSC-AF-00 | 2.148 | 1358.0 | (M − H)− |
| 1969 | SSC-FA-03 | 1.895 | 1411.8 | (M − H)− |
| 1970 | SSC-A-AF-01 | 8.021 | 1556.1 | (M − H)− |
| 1971 | SSC-AF-00 | 2.109 | 1429.7 | (M − H)− |
| 1972 | SSC-AF-00 | 2.107 | 1489.9 | (M − H)− |
| 1973 | SSC-AF-00 | 2.045 | 1432.7 | (M − H)− |
| 1974 | SSC-A-AF-01 | 8.269 | 1392.7 | (M − H)− |
| 1975 | SSC-AF-00 | 2.128 | 1397.6 | (M − H)− |
| 1976 | SSC-FA-03 | 1.905 | 1454.0 | (M − H)− |
| 1977 | SSC-FA-03 | 1.941 | 1512.0 | (M − H)− |
| 1978 | SSC-AF-00 | 2.131 | 1487.9 | (M − H)− |
| 1979 | SSC-AF-00 | 2.131 | 1415.8 | (M − H)− |
| 1980 | SSC-FA-03 | 1.871 | 1542.8 | (M − H)− |
| 1981 | SSC-A-FA-01 | 5.297 | 1456.6 | (M + H)+ |
| 1982 | SSC-FA-03 | 1.548 | 1464.8 | (M − H)− |
| 1983 | SSC-FA-03 | 1.873 | 1515.9 | (M − H)− |
| 1984 | SSC-AF-00 | 2.116 | 1473.7 | (M − H)− |
| 1985 | SSC-AF-00 | 2.085 | 1486.9 | (M − H)− |
| 1986 | SSC-A-FA-01 | 5.824 | 1505.6 | (M + H)+ |
| 1987 | SSC-A-FA-01 | 6.361 | 1545.7 | (M + H)+ |
| 1988 | SSC-AF-00 | 2.160 | 1423.8 | (M − H)− |
| 1989 | SSC-A-FA-01 | 6.744 | 1512.1 | (M − H)− |
| 1990 | SSC-FA-03 | 1.896 | 1485.6 | (M − H)− |
| 1991 | SSC-A-AF-01 | 7.800 | 1501.7 | (M − H)− |
| 1992 | SSC-A-FA-01 | 6.268 | 1527.6 | (M + H)+ |
| 1993 | SSC-FA-03 | 1.841 | 1501.9 | (M − H)− |
| 1994 | SSC-FA-03 | 1.840 | 1461.8 | (M − H)− |
| 1995 | SSC-A-AF-01 | 8.312 | 1379.0 | (M − H)− |
| 1996 | SSC-AF-00 | 2.148 | 1427.8 | (M − H)− |
| 1997 | SSC-A-AF-01 | 7.956 | 1469.6 | (M − H)− |
| 1998 | SSC-AF-00 | 2.115 | 1413.9 | (M − H)− |
| 1999 | SSC-FA-03 | 1.789 | 1399.5 | (M − H)− |
| 2000 | SSC-A-FA-01 | 5.895 | 1509.5 | (M + H)+ |
| 2001 | SSC-FA-03 | 1.908 | 1411.8 | (M − H)− |
| 2002 | SSC-A-AF-01 | 7.488 | 1496.8 | (M − H)− |
| 2003 | SSC-A-AF-01 | 7.715 | 1362.6 | (M − H)− |
| 2004 | SSC-FA-03 | 1.835 | 1419.9 | (M − H)− |
| 2005 | SSC-FA-03 | 1.775 | 1387.6 | (M − H)− |
| 2006 | SSC-FA-03 | 1.808 | 1401.6 | (M − H)− |
| 2007 | SSC-A-FA-02 | 6.119 | 1465.7 | (M + H)+ |
| 2008 | SSC-A-FA-02 | 5.992 | 1443.7 | (M + H)+ |
| 2009 | SSC-FA-03 | 1.867 | 1298.5 | (M − H)− |
| 2010 | SSC-AF-00 | 2.117 | 1272.9 | (M − H)− |
| 2011 | SSC-A-FA-02 | 5.859 | 1463.5 | (M − H)− |
| 2012 | SSC-AF-00 | 2.199 | 1300.9 | (M − H)− |
| 2013 | SSC-FA-03 | 1.796 | 1284.5 | (M − H)− |
| 2014 | SSC-FA-03 | 2.105 | 1300.5 | (M − H)− |
| 2015 | SSC-FA-03 | 2.127 | 1368.7 | (M − H)− |
| 2016 | SSC-FA-03 | 2.021 | 1344.9 | (M − H)− |
| 2017 | SSC-FA-03 | 2.012 | 1328.9 | (M − H)− |
| 2018 | SSC-AF-00 | 2.241 | 1328.6 | (M − H)− |
| 2019 | SSC-FA-03 | 2.019 | 1362.9 | (M − H)− |
| 2020 | SSC-A-FA-02 | 5.791 | 1457.6 | (M − H)− |
| 2021 | SSC-A-AF-01 | 8.403 | 1560.9 | (M − H)− |
| 2022 | SSC-A-AF-01 | 8.377 | 1546.9 | (M − H)− |
| 2023 | SSC-A-AF-01 | 7.795 | 1487.9 | (M − H)− |
| 2024 | SSC-A-FA-01 | 7.003 | 1526.0 | (M − H)− |
| 2025 | SSC-A-FA-01 | 6.751 | 1501.8 | (M − H)− |
| 2026 | SSC-A-AF-01 | 8.057 | 1491.0 | (M − H)− |
| 2027 | SSC-A-FA-01 | 5.683 | 1396.6 | (M + H)+ |
| 2028 | SSC-A-FA-01 | 5.761 | 1477.8 | (M − H)− |
| 2029 | SSC-A-AF-01 | 8.036 | 1504.9 | (M − H)− |
| 2030 | SSC-AF-00 | 2.200 | 1495.9 | (M − H)− |
| 2031 | SSC-FA-03 | 1.979 | 1469.8 | (M − H)− |
| 2032 | SSC-A-AF-01 | 8.084 | 1504.9 | (M − H)− |
| 2033 | SSC-A-AF-01 | 7.992 | 1491.0 | (M − H)− |
| 2034 | SSC-A-FA-01 | 5.313 | 1485.8 | (M + H)+ |
| 2035 | SSC-FA-03 | 2.117 | 1529.9 | (M − H)− |
| 2036 | SSC-A-FA-01 | 6.809 | 1508.0 | (M − H)− |
| 2037 | SSC-A-FA-01 | 6.308 | 1443.9 | (M − H)− |
| 2038 | SSC-A-FA-01 | 6.261 | 1528.8 | (M − H)− |
| 2039 | SSC-A-AF-01 | 7.985 | 1381.7 | (M + H)+ |
| 2040 | SSC-A-AF-01 | 7.727 | 1345.6 | (M − H)− |
| 2041 | SSC-A-AF-01 | 7.716 | 1381.8 | (M + H)+ |
| 2042 | SSC-A-AF-01 | 7.679 | 1333.7 | (M + H)+ |
| 2043 | SSC-A-AF-01 | 7.745 | 1347.7 | (M + H)+ |
| 2044 | SSC-A-AF-01 | 7.796 | 1347.7 | (M + H)+ |
| 2045 | SSC-A-FA-01 | 5.783 | 1347.7 | (M + H)+ |
| 2046 | SSC-A-FA-01 | 6.255 | 1483.8 | (M − H)− |
| 2047 | SSC-A-AF-01 | 8.128 | 1499.8 | (M − H)− |
| 2048 | SSC-AF-00 | 2.244 | 1525.9 | (M − H)− |
| 2049 | SSC-A-FA-01 | 6.192 | 1486.1 | (M − H)− |
| 2050 | SQDAA05 | 0.89 | 1595.3 | (M − H)− |
| 2051 | SSC-A-FA-01 | 8.191 | 1485.7 | (M + H)+ |
| 2052 | SSC-A-FA-01 | 6.256 | 1514.7 | (M + H)+ |
| 2053 | SSC-AF-00 | 2.245 | 1524.1 | (M − H)− |
| 2054 | SSC-A-AF-01 | 8.000 | 1511.1 | (M − H)− |
| 2055 | SSC-A-AF-01 | 7.879 | 1379.8 | (M + H)+ |
| 2056 | SQDFA50 | 1.10 | 1597.5 | (M − H)− |
| 2057 | SSC-AF-00 | 2.235 | 1467.7 | (M − H)− |
| 2058 | SSC-AF-00 | 2.009 | 1416.1 | (M − H)− |
| 2059 | SSC-AF-00 | 2.267 | 1397.7 | (M − H)− |
| 2060 | SSC-FA-03 | 1.748 | 1401.0 | (M − H)− |
| 2061 | SSC-AF-00 | 2.119 | 1353.6 | (M − H)− |
| 2062 | SSC-FA-03 | 2.067 | 1421.6 | (M − H)− |
| 2063 | SSC-AF-00 | 2.155 | 1389.6 | (M − H)− |
| 2064 | SSC-FA-03 | 1.881 | 1403.1 | (M − H)− |
| 2065 | SSC-FA-03 | 1.908 | 1403.2 | (M − H)− |
| 2066 | SSC-FA-03 | 2.188 | 1435.6 | (M − H)− |
| 2067 | SSC-FA-03 | 2.003 | 1451.7 | (M − H)− |
| 2068 | SSC-FA-03 | 1.893 | 1357.7 | (M − H)− |
| 2069 | SSC-AF-00 | 2.140 | 1419.0 | (M − H)− |
| 2070 | SSC-AF-00 | 2.077 | 1401.2 | (M − H)− |
| 2071 | SSC-FA-03 | 1.756 | 1350.5 | (M + H)+ |
| 2072 | SSC-AF-00 | 2.131 | 1443.0 | (M − H)− |
| 2073 | SSC-FA-03 | 1.957 | 1395.7 | (M − H)− |
| 2074 | SSC-FA-03 | 1.977 | 1430.0 | (M − H)− |
| 2075 | SSC-FA-03 | 1.885 | 1388.8 | (M − H)− |
| 2076 | SSC-FA-03 | 1.881 | 1434.0 | (M − H)− |
| 2077 | SSC-AF-00 | 2.091 | 1403.1 | (M + H)+ |
| 2078 | SSC-AF-00 | 2.111 | 1418.6 | (M − H)− |
| 2079 | SSC-FA-03 | 1.927 | 1381.8 | (M − H)− |
| 2080 | SSC-AF-00 | 2.169 | 1448.0 | (M − H)− |
| 2081 | SSC-AF-00 | 2.193 | 1393.8 | (M − H)− |
| 2082 | SSC-AF-00 | 2.277 | 1437.6 | (M + H)+ |
| 2083 | SSC-FA-03 | 2.037 | 1395.8 | (M − H)− |
| 2084 | SSC-FA-03 | 1.755 | 1381.0 | (M − H)− |
| 2085 | SSC-AF-00 | 2.143 | 1419.7 | (M − H)− |
| 2086 | SQDFA05 | 1.04 | 1306.7 | (M + H)+ |
| 2087 | SQDFA05 | 1.01 | 1308.7 | (M + H)+ |
| 2088 | SQDFA05 | 1.07 | 1356.7 | (M + H)+ |
| 2089 | SQDFA05 | 1.00 | 1290.7 | (M + H)+ |
| 2090 | SQDFA05 | 1.00 | 1308.7 | (M + H)+ |
| 2091 | SQDFA05 | 1.04 | 1344.7 | (M + H)+ |
| 2092 | SQDFA05 | 1.02 | 1306.7 | (M + H)+ |
| 2093 | SQDFA05 | 1.04 | 1340.6 | (M + H)+ |
| 2094 | SQDFA05 | 1.03 | 1306.7 | (M + H)+ |
| 2095 | SQDFA05 | 1.04 | 1322.7 | (M + H)+ |
| 2096 | SSC-TFA-07 | 1.363 | 1407.7 | (M + H)+ |
| 2097 | SSC-A-FA-01 | 5.915 | 1497.1 | (M − H)− |
| 2098 | SSC-A-FA-01 | 5.805 | 1576.8 | (M + H)+ |
| 2099 | SSC-A-AF-01 | 7.441 | 1521.8 | (M − H)− |
| 2100 | SSC-A-FA-01 | 5.575 | 1494.6 | (M + H)+ |
| 2101 | SSC-A-FA-01 | 5.523 | 1523.6 | (M + H)+ |
| 2102 | SSC-A-FA-01 | 5.717 | 1484.7 | (M + H)+ |
| 2103 | SSC-A-FA-01 | 5.472 | 1540.9 | (M + H)+ |
| 2104 | SSC-A-AF-01 | 7.816 | 1553.0 | (M − H)− |
| 2105 | SSC-A-AF-01 | 8.048 | 1510.9 | (M − H)− |
| 2106 | SSC-A-AF-01 | 7.720 | 1472.7 | (M + H)+ |
| 2107 | SSC-A-FA-01 | 5.476 | 1570.7 | (M + H)+ |
| 2108 | SSC-A-FA-01 | 5.508 | 1528.7 | (M + H)+ |
| 2109 | SSC-A-FA-01 | 5.720 | 1513.1 | (M − H)− |
| 2110 | SSC-A-FA-01 | 5.288 | 1535.1 | (M − H)− |
| 2111 | SSC-A-FA-01 | 5.409 | 1512.8 | (M − H)− |
| 2112 | SSC-A-FA-01 | 5.979 | 1568.7 | (M + H)+ |
| 2113 | SSC-AF-00 | 2.089 | 1452.9 | (M − H)− |
| 2114 | SSC-FA-03 | 1.861 | 1483.8 | (M − H)− |
| 2115 | SSC-AF-00 | 2.080 | 1452.9 | (M − H)− |
| 2116 | SSC-TFA-07 | 1.576 | 1394.8 | (M + H)+ |
| 2117 | SSC-FA-03 | 1.961 | 1500.0 | (M − H)− |
| 2118 | SSC-TFA-07 | 1.527 | 1443.8 | (M + H)+ |
| 2119 | SSC-FA-03 | 2.023 | 1520.0 | (M − H)− |

TABLE 22-continued

| Compound No. | Analytical condition | Retention time (min) | MS Found(m/z) | MS polarity |
| --- | --- | --- | --- | --- |
| 2120 | SSC-FA-03 | 1.819 | 1546.9 | (M − H)− |
| 2121 | SSC-AF-00 | 2.199 | 1547.0 | (M − H)− |
| 2122 | SSC-FA-03 | 1.927 | 1499.9 | (M − H)− |
| 2123 | SSC-FA-03 | 2.116 | 1519.9 | (M − H)− |
| 2124 | SSC-FA-03 | 2.105 | 1552.0 | (M − H)− |
| 2125 | SSC-TFA-07 | 1.640 | 1519.8 | (M + H)+ |
| 2126 | SSC-TFA-07 | 1.704 | 1539.8 | (M + H)+ |
| 2127 | SSC-TFA-07 | 1.580 | 1443.8 | (M + H)+ |
| 2128 | SSC-TFA-07 | 1.581 | 1571.9 | (M + H)+ |
| 2129 | SSC-TFA-07 | 1.700 | 1539.9 | (M + H)+ |
| 2130 | SSC-TFA-07 | 1.640 | 1519.9 | (M + H)+ |
| 2131 | SSC-TFA-07 | 1.588 | 1535.9 | (M + H)+ |
| 2132 | SSC-TFA-07 | 1.696 | 1539.9 | (M + H)+ |
| 2133 | SSC-TFA-07 | 1.640 | 1540.0 | (M + H)+ |
| 2134 | SSC-TFA-07 | 1.640 | 1539.7 | (M + H)+ |
| 2135 | SSC-TFA-07 | 1.611 | 1571.9 | (M + H)+ |
| 2136 | SSC-TFA-07 | 1.637 | 1535.9 | (M + H)+ |
| 2137 | SSC-TFA-07 | 1.692 | 1519.8 | (M + H)+ |
| 2138 | SSC-TFA-07 | 1.635 | 1540.0 | (M + H)+ |
| 2139 | SSC-TFA-07 | 1.632 | 1519.9 | (M + H)+ |
| 2140 | SSC-TFA-07 | 1.700 | 1519.9 | (M + H)+ |
| 2141 | SSC-TFA-07 | 1.704 | 1519.9 | (M + H)+ |
| 2142 | SSC-AF-00 | 2.084 | 1339.6 | (M − H)− |
| 2143 | SSC-AF-00 | 2.133 | 1308.4 | (M − H)− |
| 2144 | SSC-AF-00 | 2.069 | 1379.5 | (M + H)+ |
| 2145 | SSC-FA-03 | 1.812 | 1296.5 | (M − H)− |
| 2146 | SSC-FA-03 | 1.861 | 1411.5 | (M − H)− |
| 2147 | SSC-FA-03 | 1.873 | 1411.5 | (M − H)− |
| 2148 | SSC-FA-03 | 1.752 | 1280.5 | (M − H)− |
| 2149 | SSC-FA-03 | 1.893 | 1411.7 | (M − H)− |
| 2150 | SSC-FA-03 | 1.851 | 1395.5 | (M + H)+ |
| 2151 | SSC-FA-03 | 1.911 | 1405.9 | (M − H)− |
| 2152 | SSC-A-FA-01 | 5.337 | 1302.6 | (M + H)+ |
| 2153 | SSC-A-AF-01 | 7.408 | 1288.7 | (M − H)− |
| 2154 | SSC-A-FA-01 | 4.595 | 1262.5 | (M + H)+ |
| 2155 | SSC-A-AF-01 | 7.603 | 1314.9 | (M − H)− |
| 2156 | SSC-A-FA-01 | 5.383 | 1300.7 | (M − H)− |
| 2157 | SSC-A-AF-01 | 7.243 | 1286.9 | (M − H)− |
| 2158 | SSC-A-FA-01 | 5.564 | 1316.6 | (M + H)+ |
| 2159 | SSC-A-AF-01 | 7.513 | 1318.6 | (M + H)+ |
| 2160 | SSC-A-FA-01 | 5.204 | 1290.6 | (M + H)+ |
| 2161 | SSC-A-FA-02 | 6.656 | 1469.9 | (M − H)− |
| 2162 | SSC-A-FA-02 | 6.215 | 1455.6 | (M − H)− |
| 2163 | SSC-A-AF-02 | 8.011 | 1477.9 | (M − H)− |
| 2164 | SSC-A-FA-02 | 6.060 | 1429.8 | (M − H)− |
| 2165 | SSC-A-AF-02 | 8.325 | 1519.9 | (M − H)− |
| 2166 | SSC-A-FA-02 | 6.292 | 1479.6 | (M + H)+ |
| 2167 | SSC-A-FA-02 | 6.045 | 1471.8 | (M − H)− |
| 2168 | SSC-AF-00 | 2.245 | 1471.9 | (M − H)− |
| 2169 | SSC-FA-03 | 2.100 | 1529.6 | (M − H)− |
| 2170 | SSC-AF-00 | 2.192 | 1537.9 | (M − H)− |
| 2171 | SSC-AF-00 | 2.287 | 1533.7 | (M − H)− |
| 2172 | SQDFA05long | 1.480 | 1307.1 | (M + H)+ |
| 2173 | SQDFA05long | 1.160 | 1303.1 | (M + H)+ |
| 2174 | SQDFA05long | 1.100 | 1420.3 | (M + H)+ |
| 2175 | SQDFA05long | 1.640 | 1434.3 | (M + H)+ |
| 2176 | SQDFA05long | 1.880 | 1506.4 | (M + H)+ |
| 2177 | SQDFA05long | 1.550 | 1468.3 | (M + H)+ |
| 2178 | SQDFA05long | 1.430 | 1430.3 | (M + H)+ |
| 2179 | SQDFA05long | 1.170 | 1416.3 | (M + H)+ |
| 2180 | SQDFA05 | 0.820 | 1528.3 | (M + H)+ |
| 2181 | SQDFA05 | 0.770 | 1485.2 | (M + H)+ |
| 2182 | SQDFA05long | 2.420 | 1441.2 | (M + H)+ |
| 2183 | SQDFA05long | 2.550 | 1475.2 | (M + H)+ |
| 2184 | SQDAA50 | 0.800 | 1511.7 | (M − H)− |
| 2185 | SQDFA05long | 2.730 | 1489.2 | (M + H)+ |
| 2186 | SQDFA05long | 2.770 | 1473.3 | (M + H)+ |

Example 2: Pharmacological Test Example

Protein-Protein Interaction Inhibition Between Kras and SOS1 (KrasG12D-SOS PPI) Using AlphaScreen Protein-protein interaction inhibition (PPI) between Kras and SOS1 was measured by energy transfer from nickel-conjugated donor beads to streptavidin-conjugated acceptor beads using biotin-tagged human Kras expressed in E. coli and loaded with GDP after purification and His-tagged human SOS1 enzyme. This measurement utilizes the phenomenon in which donor beads are irradiated with light at 680 nm, such that energy is transferred to acceptor beads through singlet oxygen and light at 520-620 nm is detected from the acceptor beads. The 50% inhibitory concentration (IC50 value) was calculated from the inhibition rate relative to the test substance-free control group.

IC50 values of the test compounds are shown in the following table. The cyclic peptide compounds of the present invention were shown to inhibit the protein-protein interaction between Kras and SOS1. Inhibition of binding between K-ras and SOS1 is known to inhibit signaling downstream of Kras. Accordingly, the compounds of the present invention are also suggested to have cell growth inhibitory activity.

TABLE 23

| Compound No. | KRAS G12D-SOS PPI IC50 (μM) |
| --- | --- |
| 1 | 0.0059 |
| 2 | 0.015 |
| 3 | 0.31 |
| 4 | 0.013 |
| 5 | 0.00099 |
| 6 | 0.013 |
| 7 | 0.018 |
| 8 | 0.075 |
| 9 | 0.0015 |
| 10 | 0.018 |
| 11 | 0.0015 |
| 12 | 0.24 |
| 13 | 0.038 |
| 14 | 0.11 |
| 15 | 0.0033 |
| 16 | 0.00070 |
| 17 | 0.030 |
| 18 | 0.23 |
| 19 | 0.050 |
| 20 | 0.00076 |
| 21 | 0.25 |
| 22 | 0.11 |
| 23 | 0.0027 |
| 24 | 0.025 |
| 25 | 0.15 |
| 26 | 0.0043 |
| 27 | 0.0033 |
| 28 | 0.16 |
| 29 | 0.32 |
| 30 | 0.0046 |
| 31 | 0.38 |
| 32 | 0.020 |
| 33 | 0.0069 |
| 34 | 0.074 |
| 35 | 0.0021 |
| 36 | 0.0047 |
| 37 | 0.017 |
| 38 | 0.16 |
| 39 | 0.011 |
| 40 | 0.00096 |
| 41 | 0.011 |
| 42 | 0.19 |
| 43 | 0.031 |
| 44 | 0.0011 |
| 45 | 0.084 |
| 46 | 0.12 |
| 47 | 0.0015 |
| 48 | 0.00097 |
| 49 | 0.012 |
| 50 | 0.028 |
| 51 | 0.090 |
| 52 | 0.00066 |
| 53 | 0.12 |

TABLE 23-continued

| Compound No. | KRAS G12D-SOS PPI IC50 (μM) |
|---|---|
| 54 | 0.0019 |
| 55 | 0.00077 |
| 56 | 0.0023 |
| 57 | 0.016 |
| 58 | 0.028 |
| 59 | 0.036 |
| 60 | 0.0079 |
| 61 | 0.016 |
| 62 | 0.0038 |
| 63 | 0.0037 |
| 64 | 0.13 |
| 65 | 0.24 |
| 66 | 0.0036 |
| 67 | 0.0083 |
| 68 | 0.00058 |
| 69 | 0.0088 |
| 70 | 0.16 |
| 71 | 0.15 |
| 72 | 0.00047 |
| 73 | 0.00033 |
| 74 | 0.0072 |
| 75 | 0.094 |
| 76 | 0.19 |
| 77 | 0.10 |
| 78 | 0.0016 |
| 79 | 0.0093 |
| 80 | 0.0028 |
| 81 | 0.014 |
| 82 | 0.14 |
| 83 | 0.11 |
| 84 | 0.073 |
| 85 | 0.015 |
| 86 | 0.0090 |
| 87 | 0.045 |
| 88 | 0.018 |
| 89 | 0.0019 |
| 90 | 0.0050 |
| 91 | 0.0015 |
| 92 | 0.0055 |
| 93 | 0.0069 |
| 94 | 0.0033 |
| 95 | 0.011 |
| 96 | 0.22 |
| 97 | 0.040 |
| 98 | 0.068 |
| 99 | 0.0029 |
| 100 | 0.0074 |
| 101 | 0.16 |
| 102 | 0.011 |
| 103 | 0.022 |
| 104 | 0.028 |
| 105 | 0.0053 |
| 106 | 0.0089 |
| 107 | 0.0040 |
| 108 | 0.0050 |
| 109 | 0.040 |
| 110 | 0.0038 |
| 111 | 0.10 |
| 112 | 0.073 |
| 113 | 0.28 |
| 114 | 0.020 |
| 115 | 0.0060 |
| 116 | 0.14 |
| 117 | 0.021 |
| 118 | 0.0019 |
| 119 | 0.039 |
| 120 | 0.00055 |
| 121 | 0.0054 |
| 122 | 0.0086 |
| 123 | 0.17 |
| 124 | 0.14 |
| 125 | 0.0028 |
| 126 | 0.00050 |
| 127 | 0.00043 |
| 128 | 0.0016 |
| 129 | 0.011 |
| 130 | 0.010 |
| 131 | 0.0033 |
| 132 | 0.00096 |
| 133 | 0.023 |
| 134 | 0.00061 |
| 135 | 0.038 |
| 136 | 0.0077 |
| 137 | 0.00076 |
| 138 | 0.044 |
| 139 | 0.0084 |
| 140 | 0.00081 |
| 141 | 0.032 |
| 142 | 0.038 |
| 143 | 0.068 |
| 144 | 0.0011 |
| 145 | 0.025 |
| 146 | 0.0040 |
| 147 | 0.0067 |
| 148 | 0.0018 |
| 149 | 0.051 |
| 150 | 0.0013 |
| 151 | 0.0050 |
| 152 | 0.11 |
| 153 | 0.060 |
| 154 | 0.0048 |
| 155 | 0.0016 |
| 156 | 0.00098 |
| 157 | 0.0075 |
| 158 | 0.010 |
| 159 | 0.0024 |
| 160 | 0.0010 |
| 161 | 0.00082 |
| 162 | 0.23 |
| 163 | 0.0061 |
| 164 | 0.0022 |
| 165 | 0.041 |
| 166 | 0.021 |
| 167 | 0.058 |
| 168 | 0.029 |
| 169 | 0.016 |
| 170 | 0.35 |
| 171 | 0.014 |
| 172 | 0.0040 |
| 173 | 0.00056 |
| 174 | 0.057 |
| 175 | 0.012 |
| 176 | 0.0014 |
| 177 | 0.045 |
| 178 | 0.022 |
| 179 | 0.042 |
| 180 | 0.011 |
| 181 | 0.13 |
| 182 | 0.00098 |
| 183 | 0.026 |
| 184 | 0.32 |
| 185 | 0.17 |
| 186 | 0.048 |
| 187 | 0.0032 |
| 188 | 0.0061 |
| 189 | 0.11 |
| 190 | 0.15 |
| 191 | 0.0034 |
| 192 | 0.022 |
| 193 | 0.42 |
| 194 | 0.027 |
| 195 | 0.0095 |
| 196 | 0.013 |
| 197 | 0.0068 |
| 198 | 0.0085 |
| 199 | 0.036 |
| 200 | 0.013 |
| 201 | 0.00058 |
| 202 | 0.039 |
| 203 | 0.031 |
| 204 | 0.18 |
| 205 | 0.00049 |

TABLE 23-continued

| Compound No. | KRAS G12D-SOS PPI IC50 (μM) |
|---|---|
| 206 | 0.11 |
| 207 | 0.0030 |
| 208 | 0.12 |
| 209 | 0.0016 |
| 210 | 0.080 |
| 211 | 0.043 |
| 212 | 0.042 |
| 213 | 0.048 |
| 214 | 0.28 |
| 215 | 0.029 |
| 216 | 0.0080 |
| 217 | 0.066 |
| 218 | 0.0019 |
| 219 | 0.073 |
| 220 | 0.0031 |
| 221 | 0.0028 |
| 222 | 0.020 |
| 223 | 0.018 |
| 224 | 0.23 |
| 225 | 0.015 |
| 226 | 0.0035 |
| 227 | 0.082 |
| 228 | 0.024 |
| 229 | 0.0067 |
| 230 | 0.039 |
| 231 | 0.12 |
| 232 | 0.020 |
| 233 | 0.066 |
| 234 | 0.0021 |
| 235 | 0.011 |
| 236 | 0.0085 |
| 237 | 0.042 |
| 238 | 0.012 |
| 239 | 0.00077 |
| 240 | 0.14 |
| 241 | 0.018 |
| 242 | 0.027 |
| 243 | 0.00043 |
| 244 | 0.14 |
| 245 | 0.00037 |
| 246 | 0.00030 |
| 247 | 0.0070 |
| 248 | 0.031 |
| 249 | 0.0016 |
| 250 | 0.0098 |
| 251 | 0.0038 |
| 252 | 0.055 |
| 253 | 0.00099 |
| 254 | 0.015 |
| 255 | 0.0078 |
| 256 | 0.00098 |
| 257 | 0.097 |
| 258 | 0.036 |
| 259 | 0.021 |
| 260 | 0.050 |
| 261 | 0.052 |
| 262 | 0.043 |
| 263 | 0.0029 |
| 264 | 0.0045 |
| 265 | 0.28 |
| 266 | 0.0046 |
| 267 | 0.13 |
| 268 | 0.018 |
| 269 | 0.0034 |
| 270 | 0.00067 |
| 271 | 0.065 |
| 272 | 0.00052 |
| 273 | 0.036 |
| 274 | 0.00082 |
| 275 | 0.046 |
| 276 | 0.00076 |
| 277 | 0.0051 |
| 278 | 0.025 |
| 279 | 0.00099 |
| 280 | 0.024 |
| 281 | 0.0078 |
| 282 | 0.094 |
| 283 | 0.0068 |
| 284 | 0.071 |
| 285 | 0.052 |
| 286 | 0.096 |
| 287 | 0.0051 |
| 288 | 0.0017 |
| 289 | 0.00030 |
| 290 | 0.16 |
| 291 | 0.055 |
| 292 | 0.00045 |
| 293 | 0.12 |
| 294 | 0.0014 |
| 295 | 0.068 |
| 296 | 0.055 |
| 297 | 0.049 |
| 298 | 0.021 |
| 299 | 0.13 |
| 300 | 0.0095 |
| 301 | 0.00074 |
| 302 | 0.00068 |
| 303 | 0.00068 |
| 304 | 0.087 |
| 305 | 0.17 |
| 306 | 0.044 |
| 307 | 0.0044 |
| 308 | 0.00093 |
| 309 | 0.00075 |
| 310 | 0.096 |
| 311 | 0.0059 |
| 312 | 0.0010 |
| 313 | 0.0042 |
| 314 | 0.0026 |
| 315 | 0.12 |
| 316 | 0.0033 |
| 317 | 0.030 |
| 318 | 0.019 |
| 319 | 0.0082 |
| 320 | 0.0099 |
| 321 | 0.011 |
| 322 | 0.031 |
| 323 | 0.14 |
| 324 | 0.38 |
| 325 | 0.014 |
| 326 | 0.00070 |
| 327 | 0.00047 |
| 328 | 0.094 |
| 329 | 0.040 |
| 330 | 0.080 |
| 331 | 0.030 |
| 332 | 0.21 |
| 333 | 0.11 |
| 334 | IC00050 |
| 335 | 0.067 |
| 336 | 0.093 |
| 337 | 0.016 |
| 338 | 0.22 |
| 339 | 0.00038 |
| 340 | 0.0047 |
| 341 | 0.0029 |
| 342 | 0.00095 |
| 343 | 0.00087 |
| 344 | 0.00083 |
| 345 | 0.058 |
| 346 | 0.011 |
| 347 | 0.027 |
| 348 | 0.0060 |
| 349 | 0.19 |
| 350 | 0.064 |
| 351 | 0.28 |
| 352 | 0.0055 |
| 353 | 0.00069 |
| 354 | 0.0016 |
| 355 | 0.053 |
| 356 | 0.00092 |
| 357 | 0.022 |

TABLE 23-continued

| Compound No. | KRAS G12D-SOS PPI IC50 (µM) |
|---|---|
| 358 | 0.033 |
| 359 | 0.0032 |
| 360 | 0.0028 |
| 361 | 0.34 |
| 362 | 0.00066 |
| 363 | 0.00065 |
| 364 | 0.0097 |
| 365 | 0.038 |
| 366 | 0.0040 |
| 367 | 0.00060 |
| 368 | 0.0027 |
| 369 | 0.35 |
| 370 | 0.00035 |
| 371 | 0.0013 |
| 372 | 0.13 |
| 373 | 0.33 |
| 374 | 0.0065 |
| 375 | 0.012 |
| 376 | 0.044 |
| 377 | 0.024 |
| 378 | 0.00068 |
| 379 | 0.013 |
| 380 | 0.0056 |
| 381 | 0.0016 |
| 382 | 0.035 |
| 383 | 0.26 |
| 384 | 0.0010 |
| 385 | 0.0047 |
| 386 | 0.010 |
| 387 | 0.0042 |
| 388 | 0.00050 |
| 389 | 0.045 |
| 390 | 0.00077 |
| 391 | 0.00040 |
| 392 | 0.012 |
| 393 | 0.0053 |
| 394 | 0.013 |
| 395 | 0.047 |
| 396 | 0.22 |
| 397 | 0.0023 |
| 398 | 0.12 |
| 399 | 0.0089 |
| 400 | 0.00085 |
| 401 | 0.0036 |
| 402 | 0.026 |
| 403 | 0.0011 |
| 404 | 0.0048 |
| 405 | 0.27 |
| 406 | 0.25 |
| 407 | 0.039 |
| 408 | 0.011 |
| 409 | 0.0024 |
| 410 | 0.00048 |
| 411 | 0.00062 |
| 412 | 0.12 |
| 413 | 0.050 |
| 414 | 0.11 |
| 415 | 0.0015 |
| 416 | 0.054 |
| 417 | 0.015 |
| 418 | 0.017 |
| 419 | 0.0024 |
| 420 | 0.0034 |
| 421 | 0.010 |
| 422 | 0.00087 |
| 423 | 0.064 |
| 424 | 0.011 |
| 425 | 0.00057 |
| 426 | 0.0087 |
| 427 | 0.00071 |
| 428 | 0.0091 |
| 429 | 0.099 |
| 430 | 0.039 |
| 431 | 0.25 |
| 432 | 0.0045 |
| 433 | 0.0022 |
| 434 | 0.00052 |
| 435 | 0.25 |
| 436 | 0.16 |
| 437 | 0.00047 |
| 438 | 0.0060 |
| 439 | 0.052 |
| 440 | 0.0029 |
| 441 | 0.00073 |
| 442 | 0.070 |
| 443 | 0.030 |
| 444 | 0.018 |
| 445 | 0.00067 |
| 446 | 0.0018 |
| 447 | 0.014 |
| 448 | 0.091 |
| 449 | 0.030 |
| 450 | 0.0066 |
| 451 | 0.010 |
| 452 | 0.080 |
| 453 | 0.017 |
| 454 | 0.0027 |
| 455 | 0.059 |
| 456 | 0.034 |
| 457 | 0.069 |
| 458 | 0.0059 |
| 459 | 0.0095 |
| 460 | 0.0010 |
| 461 | 0.0012 |
| 462 | 0.012 |
| 463 | 0.0044 |
| 464 | 0.13 |
| 465 | 0.055 |
| 466 | 0.0031 |
| 467 | 0.20 |
| 468 | 0.0025 |
| 469 | 0.0036 |
| 470 | 0.0022 |
| 471 | 0.058 |
| 472 | 0.14 |
| 473 | 0.41 |
| 474 | 0.28 |
| 475 | 0.051 |
| 476 | 0.0041 |
| 477 | 0.0043 |
| 478 | 0.0030 |
| 479 | 0.30 |
| 480 | 0.0014 |
| 481 | 0.0020 |
| 482 | 0.17 |
| 483 | 0.017 |
| 484 | 0.11 |
| 485 | 0.16 |
| 486 | IC0048 |
| 487 | 0.0059 |
| 488 | 0.029 |
| 489 | 0.0081 |
| 490 | 0.24 |
| 491 | 0.00035 |
| 492 | 0.012 |
| 493 | 0.30 |
| 494 | 0.0086 |
| 495 | 0.0032 |
| 496 | 0.010 |
| 497 | 0.0043 |
| 498 | 0.049 |
| 499 | 0.085 |
| 500 | 0.0048 |
| 501 | 0.16 |
| 502 | 0.047 |
| 503 | 0.0071 |
| 504 | 0.053 |
| 505 | 0.086 |
| 506 | 0.00068 |
| 507 | 0.00048 |
| 508 | 0.012 |
| 509 | 0.0013 |

TABLE 23-continued

| Compound No. | KRAS G12D-SOS PPI IC50 (μM) |
|---|---|
| 510 | 0.0040 |
| 511 | 0.090 |
| 512 | 0.15 |
| 513 | 0.046 |
| 514 | 0.014 |
| 515 | 0.00055 |
| 516 | 0.062 |
| 517 | 0.028 |
| 518 | 0.00067 |
| 519 | 0.0020 |
| 520 | 0.017 |
| 521 | 0.071 |
| 522 | 0.0053 |
| 523 | 0.0058 |
| 524 | 0.082 |
| 525 | 0.0023 |
| 526 | 0.0066 |
| 527 | 0.038 |
| 528 | 0.020 |
| 529 | 0.0082 |
| 530 | 0.14 |
| 531 | 0.0016 |
| 532 | 0.00048 |
| 533 | 0.0085 |
| 534 | 0.013 |
| 535 | 0.00065 |
| 536 | 0.23 |
| 537 | 0.082 |
| 538 | 0.11 |
| 539 | 0.19 |
| 540 | 0.15 |
| 541 | 0.0043 |
| 542 | 0.061 |
| 543 | 0.00056 |
| 544 | 0.0022 |
| 545 | 0.0011 |
| 546 | 0.13 |
| 547 | 0.0010 |
| 548 | 0.0016 |
| 549 | 0.0040 |
| 550 | 0.11 |
| 551 | 0.00052 |
| 552 | 0.00063 |
| 553 | 0.027 |
| 554 | 0.0053 |
| 555 | 0.0026 |
| 556 | 0.030 |
| 557 | 0.0044 |
| 558 | 0.0018 |
| 559 | 0.0017 |
| 560 | 0.11 |
| 561 | 0.0034 |
| 562 | 0.00056 |
| 563 | 0.0011 |
| 564 | 0.0096 |
| 565 | 0.055 |
| 566 | 0.16 |
| 567 | 0.0015 |
| 568 | 0.0080 |
| 569 | 0.073 |
| 570 | 0.027 |
| 571 | 0.00083 |
| 572 | 0.039 |
| 573 | 0.010 |
| 574 | 0.0086 |
| 575 | 0.00056 |
| 576 | 0.23 |
| 577 | 0.021 |
| 578 | 0.12 |
| 579 | 0.017 |
| 580 | 0.066 |
| 581 | 0.032 |
| 582 | 0.024 |
| 583 | 0.37 |
| 584 | 0.031 |
| 585 | 0.094 |
| 586 | 0.16 |
| 587 | 0.0012 |
| 588 | 0.36 |
| 589 | 0.00049 |
| 590 | 0.0014 |
| 591 | 0.0021 |
| 592 | 0.026 |
| 593 | 0.034 |
| 594 | 0.00054 |
| 595 | 0.29 |
| 596 | 0.034 |
| 597 | 0.011 |
| 598 | 0.30 |
| 599 | 0.012 |
| 600 | 0.0045 |
| 601 | 0.087 |
| 602 | 0.28 |
| 603 | 0.00089 |
| 604 | 0.016 |
| 605 | 0.0090 |
| 606 | 0.0083 |
| 607 | 0.22 |
| 608 | 0.0059 |
| 609 | 0.11 |
| 610 | 0.15 |
| 611 | 0.0033 |
| 612 | 0.12 |
| 613 | 0.50 |
| 614 | 0.024 |
| 615 | 0.22 |
| 616 | 0.0039 |
| 617 | 0.11 |
| 618 | 0.0024 |
| 619 | 0.019 |
| 620 | 0.011 |
| 621 | 0.059 |
| 622 | 0.0017 |
| 623 | 0.0018 |
| 624 | 0.16 |
| 625 | 0.070 |
| 626 | 0.0024 |
| 627 | 0.013 |
| 628 | 0.020 |
| 629 | 0.010 |
| 630 | 0.0017 |
| 631 | 0.0010 |
| 632 | 0.073 |
| 633 | 0.12 |
| 634 | 0.26 |
| 635 | 0.19 |
| 636 | 0.0011 |
| 637 | 0.026 |
| 638 | 0.045 |
| 639 | 0.014 |
| 640 | 0.00086 |
| 641 | 0.018 |
| 642 | 0.054 |
| 643 | 0.027 |
| 644 | 0.017 |
| 645 | 0.058 |
| 646 | 0.12 |
| 647 | 0.00058 |
| 648 | 0.0032 |
| 649 | 0.36 |
| 650 | 0.00060 |
| 651 | 0.086 |
| 652 | 0.0043 |
| 653 | 0.044 |
| 654 | 0.11 |
| 655 | 0.0049 |
| 656 | 0.017 |
| 657 | 0.31 |
| 658 | 0.15 |
| 659 | 0.13 |
| 660 | 0.21 |
| 661 | 0.013 |

TABLE 23-continued

| Compound No. | KRAS G12D-SOS PPI IC50 (μM) |
|---|---|
| 662 | 0.0032 |
| 663 | 0.016 |
| 664 | 0.025 |
| 665 | 0.037 |
| 666 | 0.025 |
| 667 | 0.0051 |
| 668 | 0.0019 |
| 669 | 0.22 |
| 670 | 0.0051 |
| 671 | 0.052 |
| 672 | 0.0025 |
| 673 | 0.011 |
| 674 | 0.0056 |
| 675 | 0.059 |
| 676 | 0.031 |
| 677 | 0.0041 |
| 678 | 0.0017 |
| 679 | 0.037 |
| 680 | 0.0099 |
| 681 | 0.0059 |
| 682 | 0.020 |
| 683 | 0.00061 |
| 684 | 0.0019 |
| 685 | 0.13 |
| 686 | 0.17 |
| 687 | 0.016 |
| 688 | 0.0023 |
| 689 | 0.0021 |
| 690 | 0.0018 |
| 691 | 0.0071 |
| 692 | 0.0069 |
| 693 | 0.0016 |
| 694 | 0.014 |
| 695 | 0.0023 |
| 696 | 0.040 |
| 697 | 0.012 |
| 698 | 0.023 |
| 699 | 0.00083 |
| 700 | 0.0050 |
| 701 | 0.00069 |
| 702 | 0.13 |
| 703 | 0.0085 |
| 704 | 0.013 |
| 705 | 0.36 |
| 706 | 0.066 |
| 707 | 0.014 |
| 708 | 0.011 |
| 709 | 0.041 |
| 710 | 0.0044 |
| 711 | 0.035 |
| 712 | 0.0027 |
| 713 | 0.0040 |
| 714 | IC0023 |
| 715 | 0.0061 |
| 716 | 0.0011 |
| 717 | 0.00086 |
| 718 | 0.039 |
| 719 | 0.0059 |
| 720 | 0.039 |
| 721 | 0.0015 |
| 722 | 0.42 |
| 723 | 0.017 |
| 724 | 0.024 |
| 725 | 0.0078 |
| 726 | 0.0013 |
| 727 | 0.0069 |
| 728 | 0.016 |
| 729 | 0.043 |
| 730 | 0.012 |
| 731 | 0.0035 |
| 732 | 0.0014 |
| 733 | 0.051 |
| 734 | 0.0022 |
| 735 | 0.00044 |
| 736 | 0.037 |
| 737 | 0.11 |

TABLE 23-continued

| Compound No. | KRAS G12D-SOS PPI IC50 (μM) |
|---|---|
| 738 | 0.015 |
| 739 | 0.036 |
| 740 | 0.011 |
| 741 | 0.086 |
| 742 | 0.017 |
| 743 | 0.040 |
| 744 | 0.0075 |
| 745 | 0.029 |
| 746 | 0.13 |
| 747 | 0.011 |
| 748 | 0.13 |
| 749 | 0.0028 |
| 750 | 0.028 |
| 751 | 0.082 |
| 752 | 0.20 |
| 753 | 0.035 |
| 754 | 0.024 |
| 755 | 0.0056 |
| 756 | 0.00058 |
| 757 | 0.0037 |
| 758 | 0.14 |
| 759 | 0.16 |
| 760 | 0.0052 |
| 761 | 0.00057 |
| 762 | 0.0055 |
| 764 | 0.083 |
| 765 | 0.050 |
| 766 | 0.13 |
| 767 | 0.024 |
| 768 | 0.0011 |
| 769 | 0.052 |
| 770 | 0.020 |
| 771 | 0.025 |
| 772 | 0.15 |
| 773 | 0.14 |
| 774 | 0.00055 |
| 775 | 0.0046 |
| 776 | 0.0073 |
| 777 | 0.33 |
| 778 | 0.00070 |
| 779 | 0.16 |
| 780 | 0.021 |
| 781 | 0.060 |
| 782 | 0.021 |
| 783 | 0.0098 |
| 784 | 0.0040 |
| 785 | 0.0035 |
| 786 | 0.0060 |
| 787 | 0.0029 |
| 788 | 0.013 |
| 789 | 0.00061 |
| 790 | 0.0025 |
| 791 | IC.32 |
| 792 | 0.0035 |
| 793 | 0.024 |
| 794 | 0.011 |
| 795 | 0.072 |
| 796 | 0.0093 |
| 797 | 0.019 |
| 798 | 0.059 |
| 799 | 0.0014 |
| 800 | 0.086 |
| 801 | 0.45 |
| 802 | 0.39 |
| 803 | 0.30 |
| 804 | 0.00099 |
| 805 | 0.038 |
| 806 | 0.0011 |
| 807 | 0.00074 |
| 808 | 0.099 |
| 809 | 0.047 |
| 810 | 0.049 |
| 811 | 0.059 |
| 812 | 0.036 |
| 813 | 0.069 |
| 814 | 0.00041 |

TABLE 23-continued

| Compound No. | KRAS G12D-SOS PPI IC50 (μM) |
|---|---|
| 815 | 0.026 |
| 816 | 0.0039 |
| 817 | 0.015 |
| 818 | 0.0012 |
| 819 | 0.053 |
| 820 | 0.00073 |
| 821 | 0.012 |
| 822 | 0.15 |
| 823 | 0.016 |
| 824 | 0.0056 |
| 825 | 0.00035 |
| 826 | 0.11 |
| 827 | 0.0028 |
| 828 | 0.040 |
| 829 | 0.0023 |
| 830 | 0.28 |
| 831 | 0.18 |
| 832 | 0.12 |
| 833 | 0.0091 |
| 834 | 0.057 |
| 835 | 0.00054 |
| 836 | 0.00066 |
| 837 | 0.0060 |
| 838 | 0.010 |
| 839 | 0.22 |
| 840 | 0.0012 |
| 841 | 0.024 |
| 842 | 0.043 |
| 843 | 0.049 |
| 844 | 0.028 |
| 845 | 0.0082 |
| 847 | 0.054 |
| 848 | 0.016 |
| 849 | 0.0019 |
| 850 | 0.024 |
| 851 | 0.027 |
| 852 | 0.19 |
| 853 | 0.00062 |
| 854 | 0.011 |
| 855 | 0.0084 |
| 856 | 0.014 |
| 857 | 0.017 |
| 858 | 0.33 |
| 859 | 0.064 |
| 860 | 0.21 |
| 861 | 0.0045 |
| 862 | 0.0027 |
| 863 | 0.0025 |
| 864 | 0.073 |
| 865 | 0.055 |
| 866 | 0.0012 |
| 867 | 0.0034 |
| 868 | 0.0029 |
| 869 | 0.0098 |
| 870 | 0.015 |
| 871 | 0.00078 |
| 872 | 0.0019 |
| 873 | 0.051 |
| 874 | 0.025 |
| 875 | 0.0031 |
| 876 | 0.018 |
| 877 | 0.0025 |
| 878 | 0.32 |
| 879 | 0.036 |
| 880 | 0.0029 |
| 881 | 0.00056 |
| 882 | 0.00047 |
| 883 | 0.049 |
| 884 | 0.063 |
| 885 | 0.0019 |
| 886 | 0.10 |
| 887 | 0.0062 |
| 888 | 0.0039 |
| 889 | 0.070 |
| 890 | 0.00047 |
| 891 | 0.0096 |
| 892 | 0.068 |
| 893 | 0.021 |
| 894 | 0.011 |
| 895 | 0.0084 |
| 896 | 0.0011 |
| 897 | 0.15 |
| 898 | 0.012 |
| 899 | 0.0019 |
| 900 | 0.00084 |
| 901 | 0.035 |
| 902 | 0.14 |
| 903 | 0.024 |
| 904 | 0.0073 |
| 905 | 0.18 |
| 906 | 0.0027 |
| 907 | 0.0014 |
| 908 | 0.039 |
| 909 | 0.020 |
| 910 | 0.0043 |
| 911 | 0.0045 |
| 912 | 0.012 |
| 913 | 0.053 |
| 914 | 0.0011 |
| 915 | 0.040 |
| 916 | 0.042 |
| 917 | 0.0020 |
| 918 | 0.00089 |
| 919 | 0.052 |
| 920 | 0.015 |
| 921 | 0.0011 |
| 922 | 0.23 |
| 923 | 0.23 |
| 924 | 0.13 |
| 925 | 0.36 |
| 926 | 0.00099 |
| 927 | 0.023 |
| 928 | 0.027 |
| 929 | 0.0041 |
| 930 | 0.039 |
| 931 | 0.27 |
| 932 | 0.0054 |
| 933 | 0.083 |
| 934 | 0.034 |
| 935 | 0.0060 |
| 936 | 0.0011 |
| 937 | 0.25 |
| 938 | 0.00069 |
| 939 | 0.0080 |
| 940 | 0.15 |
| 941 | 0.0033 |
| 942 | 0.0010 |
| 943 | 0.00083 |
| 944 | 0.018 |
| 945 | 0.0098 |
| 946 | 0.0075 |
| 947 | 0.075 |
| 948 | 0.0031 |
| 949 | 0.0013 |
| 950 | 0.0090 |
| 951 | 0.0079 |
| 952 | 0.12 |
| 953 | 0.18 |
| 954 | 0.0019 |
| 955 | 0.026 |
| 956 | 0.080 |
| 957 | 0.00044 |
| 958 | 0.0021 |
| 959 | 0.0014 |
| 960 | 0.0079 |
| 961 | 0.012 |
| 962 | 0.0078 |
| 963 | 0.013 |
| 964 | 0.011 |
| 965 | 0.00086 |
| 966 | 0.11 |
| 967 | 0.058 |

TABLE 23-continued

| Compound No. | KRAS G12D-SOS PPI IC50 (μM) |
|---|---|
| 968 | 0.0031 |
| 969 | 0.0020 |
| 970 | 0.25 |
| 971 | 0.016 |
| 972 | 0.33 |
| 973 | 0.0028 |
| 974 | 0.00091 |
| 975 | 0.022 |
| 976 | 0.18 |
| 977 | 0.00033 |
| 978 | 0.17 |
| 979 | 0.037 |
| 980 | 0.0038 |
| 981 | 0.00037 |
| 982 | 0.048 |
| 983 | 0.0018 |
| 984 | 0.025 |
| 985 | 0.042 |
| 986 | 0.025 |
| 987 | 0.00096 |
| 988 | 0.012 |
| 989 | 0.034 |
| 990 | 0.083 |
| 991 | 0.076 |
| 992 | 0.18 |
| 993 | 0.016 |
| 994 | 0.011 |
| 995 | 0.0057 |
| 996 | 0.090 |
| 997 | 0.024 |
| 998 | 0.017 |
| 999 | 0.0017 |
| 1000 | 0.0026 |
| 1001 | 0.00044 |
| 1002 | 0.0021 |
| 1003 | 0.0084 |
| 1004 | 0.013 |
| 1005 | 0.0035 |
| 1006 | 0.0063 |
| 1007 | 0.013 |
| 1008 | 0.00076 |
| 1009 | 0.043 |
| 1010 | 0.0043 |
| 1011 | 0.038 |
| 1012 | 0.0012 |
| 1013 | 0.031 |
| 1014 | 0.013 |
| 1015 | 0.018 |
| 1016 | 0.024 |
| 1017 | 0.00088 |
| 1018 | 0.011 |
| 1019 | 0.014 |
| 1020 | 0.051 |
| 1021 | 0.24 |
| 1022 | 0.00042 |
| 1023 | 0.020 |
| 1024 | 0.0019 |
| 1025 | 0.0043 |
| 1026 | 0.00079 |
| 1027 | 0.0082 |
| 1029 | 0.0014 |
| 1030 | 0.0017 |
| 1031 | 0.32 |
| 1032 | 0.060 |
| 1033 | 0.36 |
| 1034 | 0.0017 |
| 1035 | 0.011 |
| 1036 | 0.0077 |
| 1037 | 0.00066 |
| 1038 | 0.018 |
| 1039 | 0.045 |
| 1040 | 0.014 |
| 1041 | 0.0016 |
| 1042 | 0.00072 |
| 1043 | 0.060 |
| 1044 | 0.055 |

TABLE 23-continued

| Compound No. | KRAS G12D-SOS PPI IC50 (μM) |
|---|---|
| 1045 | 0.0067 |
| 1046 | 0.0046 |
| 1047 | 0.0063 |
| 1048 | 0.018 |
| 1049 | 0.0037 |
| 1050 | 0.049 |
| 1051 | 0.0029 |
| 1052 | 0.11 |
| 1053 | 0.0067 |
| 1054 | 0.12 |
| 1055 | 0.0022 |
| 1056 | 0.018 |
| 1057 | 0.0012 |
| 1058 | 0.014 |
| 1059 | 0.00064 |
| 1060 | 0.00065 |
| 1061 | 0.014 |
| 1062 | 0.00092 |
| 1063 | 0.043 |
| 1064 | 0.0043 |
| 1065 | 0.070 |
| 1066 | 0.024 |
| 1067 | 0.29 |
| 1068 | 0.12 |
| 1069 | 0.017 |
| 1070 | 0.00091 |
| 1071 | 0.0013 |
| 1072 | 0.0012 |
| 1073 | 0.0021 |
| 1074 | 0.011 |
| 1075 | 0.14 |
| 1076 | 0.019 |
| 1077 | 0.034 |
| 1078 | 0.19 |
| 1079 | 0.015 |
| 1080 | 0.0010 |
| 1081 | 0.025 |
| 1082 | 0.27 |
| 1083 | 0.019 |
| 1084 | 0.053 |
| 1085 | 0.050 |
| 1086 | 0.18 |
| 1087 | 0.015 |
| 1088 | 0.17 |
| 1089 | 0.0016 |
| 1090 | 0.088 |
| 1091 | 0.0010 |
| 1092 | 0.041 |
| 1093 | 0.00073 |
| 1094 | 0.0022 |
| 1095 | 0.046 |
| 1096 | 0.0026 |
| 1097 | 0.23 |
| 1098 | 0.0056 |
| 1099 | 0.00092 |
| 1100 | 0.0063 |
| 1101 | 0.0090 |
| 1102 | 0.16 |
| 1103 | 0.016 |
| 1104 | 0.011 |
| 1105 | 0.021 |
| 1106 | 0.035 |
| 1107 | 0.093 |
| 1108 | 0.011 |
| 1109 | 0.023 |
| 1110 | 0.13 |
| 1111 | 0.041 |
| 1112 | 0.0060 |
| 1113 | 0.41 |
| 1114 | 0.011 |
| 1115 | 0.0025 |
| 1116 | 0.00044 |
| 1117 | 0.0022 |
| 1118 | 0.20 |
| 1119 | 0.18 |
| 1120 | 0.0025 |

TABLE 23-continued

| Compound No. | KRAS G12D-SOS PPI IC50 (μM) |
|---|---|
| 1121 | 0.0014 |
| 1122 | 0.067 |
| 1123 | 0.18 |
| 1124 | 0.0070 |
| 1125 | 0.0025 |
| 1126 | 0.25 |
| 1127 | 0.26 |
| 1128 | 0.0021 |
| 1129 | 0.15 |
| 1130 | 0.0044 |
| 1131 | 0.013 |
| 1132 | 0.0013 |
| 1133 | 0.056 |
| 1134 | 0.0060 |
| 1135 | 0.0058 |
| 1136 | 0.070 |
| 1137 | 0.0046 |
| 1138 | 0.067 |
| 1139 | 0.00059 |
| 1140 | 0.0020 |
| 1141 | 0.00097 |
| 1142 | 0.0065 |
| 1143 | 0.00073 |
| 1144 | 0.00049 |
| 1145 | 0.0011 |
| 1146 | 0.0019 |
| 1148 | 0.0012 |
| 1149 | 0.00062 |
| 1150 | 0.00052 |
| 1151 | 0.0052 |
| 1152 | 0.0012 |
| 1153 | 0.0025 |
| 1154 | 0.0024 |
| 1155 | 0.17 |
| 1156 | 0.14 |
| 1157 | 0.0016 |
| 1158 | 0.00052 |
| 1159 | 0.0028 |
| 1160 | 0.00042 |
| 1161 | 0.060 |
| 1162 | 0.00057 |
| 1163 | 0.00046 |
| 1164 | 0.0014 |
| 1165 | 0.00073 |
| 1166 | 0.00047 |
| 1167 | 0.0087 |
| 1168 | 0.10 |
| 1169 | 0.053 |
| 1170 | 0.00054 |
| 1171 | 0.00099 |
| 1172 | 0.0068 |
| 1173 | 0.00074 |
| 1174 | 0.062 |
| 1175 | 0.00079 |
| 1176 | 0.00080 |
| 1177 | 0.012 |
| 1178 | 0.0010 |
| 1179 | 0.00052 |
| 1180 | 0.00050 |
| 1181 | 0.0060 |
| 1182 | 0.00056 |
| 1183 | 0.00073 |
| 1184 | 0.13 |
| 1185 | 0.011 |
| 1186 | 0.0086 |
| 1187 | 0.099 |
| 1188 | 0.033 |
| 1189 | 0.00074 |
| 1190 | 0.00083 |
| 1191 | 0.0067 |
| 1192 | 0.00039 |
| 1193 | 0.0021 |
| 1194 | 0.00052 |
| 1195 | 0.038 |
| 1196 | 0.00048 |
| 1197 | 0.00060 |
| 1198 | 0.0012 |
| 1199 | 0.00070 |
| 1200 | 0.045 |
| 1201 | 0.00053 |
| 1202 | 0.24 |
| 1203 | 0.0021 |
| 1204 | 0.00044 |
| 1205 | 0.0028 |
| 1206 | 0.00057 |
| 1207 | 0.0027 |
| 1208 | 0.00069 |
| 1209 | 0.00085 |
| 1210 | 0.00074 |
| 1211 | 0.031 |
| 1212 | 0.12 |
| 1213 | 0.017 |
| 1214 | 0.077 |
| 1215 | 0.0018 |
| 1216 | 0.12 |
| 1217 | 0.0010 |
| 1218 | 0.0049 |
| 1219 | 0.016 |
| 1220 | 0.00064 |
| 1221 | 0.038 |
| 1222 | 0.025 |
| 1223 | 0.0012 |
| 1224 | 0.00067 |
| 1225 | 0.034 |
| 1226 | 0.015 |
| 1227 | 0.0013 |
| 1228 | 0.00059 |
| 1229 | 0.046 |
| 1230 | 0.098 |
| 1231 | 0.00059 |
| 1232 | 0.00047 |
| 1233 | 0.0025 |
| 1234 | 0.0045 |
| 1235 | 0.0055 |
| 1236 | 0.0073 |
| 1237 | 0.00086 |
| 1238 | 0.0099 |
| 1239 | 0.18 |
| 1240 | 0.29 |
| 1241 | 0.00050 |
| 1242 | 0.00052 |
| 1243 | 0.027 |
| 1244 | 0.00063 |
| 1245 | 0.00054 |
| 1246 | 0.055 |
| 1247 | 0.0048 |
| 1248 | 0.00067 |
| 1249 | 0.033 |
| 1250 | IC 0.00063 |
| 1251 | 0.0026 |
| 1252 | 0.0025 |
| 1253 | 0.00081 |
| 1254 | 0.00054 |
| 1255 | 0.0014 |
| 1256 | 0.0091 |
| 1257 | 0.0065 |
| 1258 | 0.026 |
| 1259 | 0.00049 |
| 1260 | 0.00054 |
| 1261 | 0.00065 |
| 1262 | 0.0013 |
| 1263 | 0.0027 |
| 1264 | 0.00054 |
| 1265 | 0.28 |
| 1266 | 0.0012 |
| 1267 | 0.00036 |
| 1268 | 0.019 |
| 1269 | 0.0010 |
| 1270 | 0.00061 |
| 1271 | 0.00049 |
| 1272 | 0.0020 |
| 1273 | 0.0072 |

TABLE 23-continued

| Compound No. | KRAS G12D-SOS PPI IC50 (μM) |
|---|---|
| 1274 | 0.0038 |
| 1275 | 0.00065 |
| 1276 | 0.017 |
| 1277 | 0.0067 |
| 1278 | 0.00065 |
| 1279 | 0.016 |
| 1280 | 0.074 |
| 1281 | 0.00042 |
| 1282 | 0.00081 |
| 1283 | 0.00063 |
| 1284 | 0.00069 |
| 1285 | 0.00053 |
| 1286 | 0.024 |
| 1287 | 0.0011 |
| 1288 | 0.031 |
| 1289 | 0.00067 |
| 1290 | 0.00063 |
| 1291 | 0.0054 |
| 1292 | 0.0020 |
| 1293 | 0.00096 |
| 1294 | 0.050 |
| 1295 | 0.00050 |
| 1296 | 0.00059 |
| 1297 | 0.00051 |
| 1298 | 0.028 |
| 1299 | 0.0036 |
| 1300 | 0.094 |
| 1301 | 0.00067 |
| 1302 | 0.00075 |
| 1303 | 0.00072 |
| 1304 | 0.085 |
| 1305 | 0.24 |
| 1306 | 0.00050 |
| 1307 | 0.0027 |
| 1308 | 0.00065 |
| 1309 | 0.00085 |
| 1310 | 0.00087 |
| 1311 | 0.00051 |
| 1312 | 0.00074 |
| 1313 | 0.065 |
| 1314 | 0.090 |
| 1315 | 0.0010 |
| 1316 | 0.0032 |
| 1317 | 0.00057 |
| 1318 | 0.078 |
| 1319 | 0.00082 |
| 1320 | 0.0014 |
| 1321 | 0.00055 |
| 1322 | 0.00082 |
| 1323 | 0.0043 |
| 1324 | 0.0012 |
| 1325 | 0.00096 |
| 1326 | 0.0051 |
| 1327 | 0.072 |
| 1328 | 0.22 |
| 1329 | 0.0017 |
| 1330 | 0.00062 |
| 1331 | 0.0011 |
| 1332 | 0.023 |
| 1333 | 0.00048 |
| 1334 | 0.0030 |
| 1335 | 0.00049 |
| 1336 | 0.00066 |
| 1337 | 0.00055 |
| 1338 | 0.017 |
| 1339 | 0.00057 |
| 1340 | 0.0012 |
| 1341 | 0.00082 |
| 1342 | 0.00053 |
| 1343 | 0.00061 |
| 1344 | 0.19 |
| 1345 | 0.040 |
| 1346 | 0.00060 |
| 1347 | 0.0013 |
| 1348 | 0.00062 |
| 1349 | 0.15 |
| 1350 | 0.017 |
| 1351 | 0.00082 |
| 1352 | 0.11 |
| 1353 | 0.011 |
| 1354 | 0.0077 |
| 1355 | 0.0032 |
| 1356 | 0.0011 |
| 1357 | 0.00052 |
| 1358 | 0.019 |
| 1359 | 0.0062 |
| 1360 | 0.00097 |
| 1361 | 0.024 |
| 1362 | 0.00081 |
| 1363 | 0.00057 |
| 1364 | 0.0012 |
| 1365 | 0.0012 |
| 1366 | 0.00063 |
| 1367 | 0.00065 |
| 1368 | 0.00067 |
| 1369 | 0.00055 |
| 1370 | 0.00060 |
| 1371 | 0.0016 |
| 1372 | 0.017 |
| 1373 | 0.0077 |
| 1374 | 0.00054 |
| 1375 | 0.0093 |
| 1376 | 0.00071 |
| 1377 | 0.0058 |
| 1378 | 0.38 |
| 1379 | 0.064 |
| 1380 | 0.016 |
| 1381 | 0.15 |
| 1382 | 0.23 |
| 1383 | 0.13 |
| 1384 | 0.23 |
| 1385 | 0.20 |
| 1386 | 0.0100 |
| 1387 | 0.014 |
| 1388 | 0.010 |
| 1389 | 0.24 |
| 1390 | 0.28 |
| 1391 | 0.065 |
| 1392 | 0.028 |
| 1393 | 0.38 |
| 1394 | 0.13 |
| 1395 | 0.27 |
| 1396 | 0.016 |
| 1397 | 0.0064 |
| 1398 | 0.0066 |
| 1399 | 0.070 |
| 1400 | 0.21 |
| 1401 | 0.12 |
| 1402 | 0.057 |
| 1403 | 0.032 |
| 1404 | 0.017 |
| 1405 | 0.082 |
| 1406 | 0.16 |
| 1407 | 0.17 |
| 1408 | 0.16 |
| 1409 | 0.17 |
| 1410 | 0.27 |
| 1411 | 0.082 |
| 1412 | 0.31 |
| 1413 | 0.19 |
| 1414 | 0.038 |
| 1415 | 0.034 |
| 1416 | 0.097 |
| 1417 | 0.029 |
| 1418 | 0.11 |
| 1419 | 0.046 |
| 1420 | 0.089 |
| 1421 | 0.032 |
| 1422 | 0.016 |
| 1423 | 0.19 |
| 1424 | 0.20 |
| 1425 | 0.019 |

TABLE 23-continued

| Compound No. | KRAS G12D-SOS PPI IC50 (μM) |
|---|---|
| 1426 | 0.048 |
| 1427 | 0.25 |
| 1428 | 0.042 |
| 1429 | 0.044 |
| 1430 | 0.40 |
| 1431 | 0.22 |
| 1432 | 0.26 |
| 1433 | 0.029 |
| 1434 | 0.15 |
| 1435 | 0.0074 |
| 1436 | 0.039 |
| 1437 | 0.081 |
| 1438 | 0.036 |
| 1439 | 0.0037 |
| 1440 | 0.016 |
| 1441 | 0.0064 |
| 1442 | 0.28 |
| 1443 | 0.023 |
| 1444 | 0.0088 |
| 1445 | 0.25 |
| 1446 | 0.15 |
| 1447 | 0.10 |
| 1448 | 0.0011 |
| 1449 | 0.014 |
| 1450 | 0.22 |
| 1451 | 0.020 |
| 1452 | 0.038 |
| 1453 | 0.11 |
| 1454 | 0.011 |
| 1455 | 0.030 |
| 1456 | 0.012 |
| 1457 | 0.011 |
| 1458 | 0.0072 |
| 1459 | 0.29 |
| 1460 | 0.13 |
| 1461 | 0.037 |
| 1462 | 0.00079 |
| 1463 | 0.00068 |
| 1464 | 0.19 |
| 1465 | 0.051 |
| 1466 | 0.0010 |
| 1467 | 0.12 |
| 1468 | 0.090 |
| 1469 | 0.23 |
| 1470 | 0.21 |
| 1471 | 0.0017 |
| 1472 | 0.067 |
| 1473 | 0.39 |
| 1474 | 0.24 |
| 1475 | 0.0027 |
| 1476 | 0.046 |
| 1477 | 0.028 |
| 1478 | 0.0030 |
| 1479 | 0.12 |
| 1480 | 0.0089 |
| 1481 | 0.0050 |
| 1482 | 0.088 |
| 1483 | 0.034 |
| 1484 | 0.19 |
| 1485 | 0.00084 |
| 1486 | 0.00050 |
| 1487 | 0.34 |
| 1488 | 0.26 |
| 1489 | 0.018 |
| 1490 | 0.32 |
| 1491 | 0.0037 |
| 1492 | 0.24 |
| 1493 | 0.10 |
| 1494 | 0.14 |
| 1495 | 0.12 |
| 1496 | 0.0020 |
| 1497 | 0.025 |
| 1498 | 0.0017 |
| 1499 | 0.019 |
| 1500 | 0.0039 |
| 1501 | 0.014 |
| 1502 | 0.024 |
| 1503 | 0.016 |
| 1504 | 0.057 |
| 1505 | 0.22 |
| 1506 | 0.0029 |
| 1507 | 0.024 |
| 1508 | 0.0013 |
| 1509 | 0.023 |
| 1510 | 0.11 |
| 1511 | 0.19 |
| 1512 | 0.0012 |
| 1513 | 0.27 |
| 1514 | 0.0010 |
| 1515 | 0.077 |
| 1516 | 0.34 |
| 1517 | 0.049 |
| 1518 | 0.37 |
| 1519 | 0.12 |
| 1520 | 0.059 |
| 1521 | 0.11 |
| 1522 | 0.090 |
| 1523 | 0.00075 |
| 1524 | 0.0019 |
| 1525 | 0.10 |
| 1526 | 0.10 |
| 1527 | 0.19 |
| 1528 | 0.041 |
| 1529 | 0.011 |
| 1530 | 0.13 |
| 1531 | 0.23 |
| 1532 | 0.0048 |
| 1533 | 0.068 |
| 1534 | 0.062 |
| 1535 | 0.041 |
| 1536 | 0.021 |
| 1537 | 0.0039 |
| 1538 | 0.11 |
| 1539 | 0.054 |
| 1540 | 0.23 |
| 1541 | 0.0040 |
| 1542 | 0.17 |
| 1543 | 0.16 |
| 1544 | 0.0056 |
| 1545 | 0.042 |
| 1546 | 0.040 |
| 1547 | 0.022 |
| 1548 | 0.14 |
| 1549 | 0.0036 |
| 1550 | 0.019 |
| 1551 | 0.0049 |
| 1552 | 0.061 |
| 1553 | 0.012 |
| 1554 | 0.20 |
| 1555 | 0.0061 |
| 1556 | 0.017 |
| 1557 | 0.0057 |
| 1558 | 0.071 |
| 1559 | 0.028 |
| 1560 | 0.16 |
| 1561 | 0.033 |
| 1562 | 0.0048 |
| 1563 | 0.0062 |
| 1564 | 0.038 |
| 1565 | 0.014 |
| 1566 | 0.020 |
| 1567 | 0.033 |
| 1568 | 0.094 |
| 1569 | 0.016 |
| 1570 | 0.0043 |
| 1571 | 0.0048 |
| 1572 | 0.0098 |
| 1573 | 0.057 |
| 1574 | 0.035 |
| 1575 | 0.045 |
| 1576 | 0.0051 |
| 1577 | 0.050 |

TABLE 23-continued

| Compound No. | KRAS G12D-SOS PPI IC50 (μM) |
|---|---|
| 1578 | 0.028 |
| 1579 | 0.0082 |
| 1580 | 0.011 |
| 1581 | 0.23 |
| 1582 | 0.035 |
| 1583 | 0.012 |
| 1584 | 0.0095 |
| 1585 | 0.043 |
| 1586 | 0.059 |
| 1587 | 0.031 |
| 1588 | 0.0041 |
| 1589 | 0.039 |
| 1590 | 0.0032 |
| 1591 | 0.097 |
| 1592 | 0.21 |
| 1593 | 0.14 |
| 1594 | 0.0032 |
| 1595 | 0.015 |
| 1596 | 0.023 |
| 1597 | 0.011 |
| 1598 | 0.0092 |
| 1599 | 0.017 |
| 1600 | 0.31 |
| 1601 | 0.022 |
| 1602 | 0.0063 |
| 1603 | 0.094 |
| 1604 | 0.0058 |
| 1605 | 0.012 |
| 1606 | 0.015 |
| 1607 | 0.028 |
| 1608 | 0.0058 |
| 1609 | 0.0053 |
| 1610 | 0.0067 |
| 1611 | 0.0032 |
| 1612 | 0.39 |
| 1613 | 0.11 |
| 1614 | 0.051 |
| 1615 | 0.040 |
| 1616 | 0.012 |
| 1617 | 0.0027 |
| 1618 | 0.29 |
| 1619 | 0.36 |
| 1620 | 0.0054 |
| 1621 | 0.0072 |
| 1622 | 0.13 |
| 1623 | 0.054 |
| 1624 | 0.092 |
| 1625 | 0.0072 |
| 1626 | 0.0044 |
| 1627 | 0.015 |
| 1628 | 0.067 |
| 1629 | 0.0025 |
| 1630 | 0.0062 |
| 1631 | 0.0050 |
| 1632 | 0.0029 |
| 1633 | 0.050 |
| 1634 | 0.013 |
| 1635 | 0.14 |
| 1636 | 0.011 |
| 1637 | 0.017 |
| 1638 | 0.0073 |
| 1639 | 0.0058 |
| 1640 | 0.0066 |
| 1641 | 0.0083 |
| 1642 | 0.058 |
| 1643 | 0.0072 |
| 1644 | 0.0031 |
| 1645 | 0.0010 |
| 1646 | 0.0046 |
| 1647 | 0.0030 |
| 1648 | 0.010 |
| 1649 | 0.00042 |
| 1650 | 0.0026 |
| 1651 | 0.0049 |
| 1652 | 0.0031 |
| 1653 | 0.00089 |
| 1654 | 0.022 |
| 1655 | 0.085 |
| 1656 | 0.0014 |
| 1657 | 0.0028 |
| 1658 | 0.00055 |
| 1659 | 0.00038 |
| 1660 | 0.016 |
| 1661 | 0.0027 |
| 1662 | 0.00065 |
| 1663 | 0.0016 |
| 1664 | 0.0088 |
| 1665 | 0.019 |
| 1666 | 0.0011 |
| 1667 | 0.013 |
| 1668 | 0.00085 |
| 1669 | 0.0018 |
| 1670 | 0.0010 |
| 1671 | 0.0011 |
| 1672 | 0.0043 |
| 1673 | 0.0054 |
| 1674 | 0.058 |
| 1675 | 0.0012 |
| 1676 | 0.0016 |
| 1677 | 0.0086 |
| 1678 | 0.026 |
| 1679 | 0.00085 |
| 1680 | 0.00061 |
| 1681 | 0.0031 |
| 1682 | 0.0024 |
| 1683 | 0.052 |
| 1684 | 0.0043 |
| 1685 | 0.00060 |
| 1686 | 0.0015 |
| 1687 | 0.0042 |
| 1688 | 0.024 |
| 1689 | 0.0011 |
| 1690 | 0.097 |
| 1691 | 0.12 |
| 1692 | 0.0035 |
| 1693 | 0.0017 |
| 1694 | 0.00055 |
| 1695 | 0.0080 |
| 1696 | 0.00057 |
| 1697 | 0.11 |
| 1698 | 0.0012 |
| 1699 | 0.0011 |
| 1700 | 0.00066 |
| 1701 | 0.00075 |
| 1702 | 0.031 |
| 1703 | 0.00041 |
| 1704 | 0.0060 |
| 1705 | 0.0098 |
| 1706 | 0.14 |
| 1707 | 0.18 |
| 1708 | 0.010 |
| 1709 | 0.010 |
| 1710 | 0.33 |
| 1711 | 0.00078 |
| 1712 | 0.0098 |
| 1713 | 0.00049 |
| 1714 | 0.0023 |
| 1715 | 0.0024 |
| 1716 | 0.0079 |
| 1717 | 0.0033 |
| 1718 | 0.00080 |
| 1719 | 0.018 |
| 1720 | 0.00058 |
| 1721 | 0.022 |
| 1722 | 0.0028 |
| 1723 | 0.0036 |
| 1724 | 0.016 |
| 1725 | 0.023 |
| 1726 | 0.00068 |
| 1727 | 0.0012 |
| 1728 | 0.0012 |
| 1729 | 0.00044 |

TABLE 23-continued

| Compound No. | KRAS G12D-SOS PPI IC50 (μM) |
|---|---|
| 1730 | 0.035 |
| 1731 | 0.0019 |
| 1732 | 0.0055 |
| 1733 | 0.13 |
| 1734 | 0.071 |
| 1735 | 0.0011 |
| 1736 | 0.0043 |
| 1737 | 0.0083 |
| 1738 | 0.011 |
| 1739 | 0.0047 |
| 1740 | 0.00079 |
| 1741 | 0.0038 |
| 1742 | 0.020 |
| 1743 | 0.0013 |
| 1744 | 0.0040 |
| 1745 | 0.0013 |
| 1746 | 0.00089 |
| 1747 | 0.016 |
| 1748 | 0.00061 |
| 1749 | 0.00074 |
| 1750 | 0.0013 |
| 1751 | 0.0073 |
| 1752 | 0.017 |
| 1753 | 0.0025 |
| 1754 | 0.067 |
| 1755 | 0.0079 |
| 1756 | 0.00054 |
| 1757 | 0.00043 |
| 1758 | 0.0012 |
| 1759 | 0.0027 |
| 1760 | 0.032 |
| 1761 | 0.00041 |
| 1762 | 0.00037 |
| 1763 | 0.0045 |
| 1764 | 0.0032 |
| 1765 | 0.074 |
| 1766 | 0.0036 |
| 1767 | 0.0072 |
| 1768 | 0.14 |
| 1769 | 0.011 |
| 1770 | 0.00071 |
| 1771 | 0.078 |
| 1772 | 0.00075 |
| 1773 | 0.051 |
| 1774 | 0.00084 |
| 1775 | 0.0040 |
| 1776 | 0.024 |
| 1777 | 0.00063 |
| 1778 | 0.0073 |
| 1779 | 0.00052 |
| 1780 | 0.12 |
| 1781 | 0.049 |
| 1782 | 0.0022 |
| 1783 | 0.052 |
| 1784 | 0.011 |
| 1785 | 0.00045 |
| 1786 | 0.00072 |
| 1787 | 0.0011 |
| 1788 | 0.0043 |
| 1789 | 0.0065 |
| 1790 | 0.00070 |
| 1791 | 0.0030 |
| 1792 | 0.00092 |
| 1793 | 0.0019 |
| 1794 | 0.040 |
| 1795 | 0.00099 |
| 1796 | 0.00076 |
| 1797 | 0.0037 |
| 1798 | 0.0010 |
| 1799 | 0.015 |
| 1800 | 0.011 |
| 1801 | 0.0029 |
| 1802 | 0.021 |
| 1803 | 0.0053 |
| 1804 | 0.00051 |
| 1805 | 0.00092 |
| 1806 | 0.014 |
| 1807 | 0.00089 |
| 1808 | 0.047 |
| 1809 | 0.0014 |
| 1810 | 0.00065 |
| 1811 | 0.056 |
| 1812 | 0.00056 |
| 1813 | 0.036 |
| 1814 | 0.17 |
| 1815 | 0.0025 |
| 1816 | 0.012 |
| 1817 | 0.0014 |
| 1818 | 0.00040 |
| 1819 | 0.0038 |
| 1820 | 0.014 |
| 1821 | 0.00099 |
| 1822 | 0.050 |
| 1823 | 0.059 |
| 1824 | 0.00075 |
| 1825 | 0.0034 |
| 1826 | 0.099 |
| 1827 | 0.0066 |
| 1828 | 0.0027 |
| 1829 | 0.0015 |
| 1830 | 0.0016 |
| 1831 | 0.071 |
| 1832 | 0.0010 |
| 1833 | 0.0075 |
| 1834 | 0.00081 |
| 1835 | 0.0011 |
| 1836 | 0.00047 |
| 1837 | 0.0020 |
| 1838 | 0.0026 |
| 1839 | 0.055 |
| 1840 | 0.0012 |
| 1841 | 0.0044 |
| 1842 | 0.00066 |
| 1843 | 0.00084 |
| 1844 | 0.017 |
| 1845 | 0.00084 |
| 1846 | 0.0011 |
| 1847 | 0.00063 |
| 1848 | 0.0014 |
| 1849 | 0.23 |
| 1850 | 0.00060 |
| 1851 | 0.0025 |
| 1852 | 0.00094 |
| 1853 | 0.0089 |
| 1854 | 0.0055 |
| 1855 | 0.34 |
| 1856 | 0.0054 |
| 1857 | 0.019 |
| 1858 | 0.0011 |
| 1859 | 0.015 |
| 1860 | 0.011 |
| 1861 | 0.0013 |
| 1862 | 0.0020 |
| 1863 | 0.010 |
| 1864 | 0.048 |
| 1865 | 0.00043 |
| 1866 | 0.0028 |
| 1867 | 0.00073 |
| 1868 | 0.10 |
| 1869 | 0.00076 |
| 1870 | 0.00074 |
| 1871 | 0.00048 |
| 1872 | 0.00065 |
| 1873 | 0.033 |
| 1874 | 0.40 |
| 1875 | 0.00042 |
| 1876 | 0.098 |
| 1877 | 0.00086 |
| 1878 | 0.0088 |
| 1879 | 0.00066 |
| 1880 | 0.013 |
| 1881 | 0.0014 |

TABLE 23-continued

| Compound No. | KRAS G12D-SOS PPI IC50 (μM) |
|---|---|
| 1882 | 0.0097 |
| 1883 | 0.065 |
| 1884 | 0.00041 |
| 1885 | 0.032 |
| 1886 | 0.00093 |
| 1887 | 0.18 |
| 1888 | 0.053 |
| 1889 | 0.098 |
| 1890 | 0.00055 |
| 1891 | 0.23 |
| 1892 | 0.0015 |
| 1893 | 0.014 |
| 1894 | 0.00055 |
| 1895 | 0.36 |
| 1896 | 0.00049 |
| 1897 | 0.0099 |
| 1898 | 0.00093 |
| 1899 | 0.22 |
| 1900 | 0.00099 |
| 1901 | 0.00056 |
| 1902 | 0.054 |
| 1903 | 0.0040 |
| 1904 | 0.00057 |
| 1905 | 0.00033 |
| 1906 | 0.00055 |
| 1907 | 0.0013 |
| 1908 | 0.00065 |
| 1909 | 0.11 |
| 1910 | 0.060 |
| 1911 | 0.00067 |
| 1912 | 0.027 |
| 1913 | 0.0011 |
| 1914 | 0.0077 |
| 1915 | 0.00038 |
| 1916 | 0.00099 |
| 1917 | 0.028 |
| 1918 | 0.28 |
| 1919 | 0.21 |
| 1920 | 0.021 |
| 1921 | 0.00083 |
| 1922 | 0.0031 |
| 1923 | 0.00089 |
| 1924 | 0.0051 |
| 1925 | 0.00055 |
| 1926 | 0.021 |
| 1927 | 0.0033 |
| 1928 | 0.00050 |
| 1929 | 0.00061 |
| 1930 | 0.0036 |
| 1931 | 0.00056 |
| 1932 | 0.0011 |
| 1933 | 0.00059 |
| 1934 | 0.0010 |
| 1935 | 0.011 |
| 1936 | 0.00068 |
| 1937 | 0.0031 |
| 1938 | 0.00076 |
| 1939 | 0.00071 |
| 1940 | 0.0016 |
| 1941 | 0.0015 |
| 1942 | 0.29 |
| 1943 | 0.0080 |
| 1944 | 0.045 |
| 1945 | 0.018 |
| 1946 | 0.0015 |
| 1947 | 0.0012 |
| 1948 | 0.00054 |
| 1949 | 0.00060 |
| 1950 | 0.0028 |
| 1951 | 0.0099 |
| 1952 | 0.0081 |
| 1953 | 0.051 |
| 1954 | 0.0023 |
| 1955 | 0.0015 |
| 1956 | 0.00076 |
| 1957 | 0.0012 |
| 1958 | 0.00045 |
| 1959 | 0.0052 |
| 1960 | 0.056 |
| 1961 | 0.0018 |
| 1962 | 0.0014 |
| 1963 | 0.00063 |
| 1964 | 0.036 |
| 1965 | 0.00055 |
| 1966 | 0.00092 |
| 1967 | 0.077 |
| 1968 | 0.0012 |
| 1969 | 0.00061 |
| 1970 | 0.052 |
| 1971 | 0.0011 |
| 1972 | 0.00037 |
| 1973 | 0.0071 |
| 1974 | 0.045 |
| 1975 | 0.00051 |
| 1976 | 0.0015 |
| 1977 | 0.00047 |
| 1978 | 0.00051 |
| 1979 | 0.00064 |
| 1980 | 0.0015 |
| 1981 | 0.0051 |
| 1982 | 0.047 |
| 1983 | 0.00068 |
| 1984 | 0.00038 |
| 1985 | 0.00070 |
| 1986 | 0.011 |
| 1987 | 0.015 |
| 1988 | 0.00069 |
| 1989 | 0.46 |
| 1990 | 0.00043 |
| 1991 | 0.0092 |
| 1992 | 0.28 |
| 1993 | 0.00064 |
| 1994 | 0.00058 |
| 1995 | 0.34 |
| 1996 | 0.00064 |
| 1997 | 0.22 |
| 1998 | 0.00075 |
| 1999 | 0.00082 |
| 2000 | 0.015 |
| 2001 | 0.00048 |
| 2002 | 0.0030 |
| 2003 | 0.0086 |
| 2004 | 0.00033 |
| 2005 | 0.00064 |
| 2006 | 0.00062 |
| 2007 | 0.23 |
| 2008 | 0.14 |
| 2009 | 0.082 |
| 2010 | 0.22 |
| 2011 | 0.017 |
| 2012 | 0.20 |
| 2013 | 0.15 |
| 2014 | 0.34 |
| 2015 | 0.26 |
| 2016 | 0.27 |
| 2017 | 0.35 |
| 2018 | 0.32 |
| 2019 | 0.11 |
| 2020 | 0.27 |
| 2021 | 0.0028 |
| 2022 | 0.0038 |
| 2023 | 0.0017 |
| 2024 | 0.0043 |
| 2025 | 0.0014 |
| 2026 | 0.0013 |
| 2027 | 0.11 |
| 2028 | 0.011 |
| 2029 | 0.00083 |
| 2030 | 0.0023 |
| 2031 | 0.00082 |
| 2032 | 0.0012 |
| 2033 | 0.00065 |

TABLE 23-continued

| Compound No. | KRAS G12D-SOS PPI IC50 (μM) |
|---|---|
| 2034 | 0.0020 |
| 2035 | 0.024 |
| 2036 | 0.0011 |
| 2037 | 0.00058 |
| 2038 | 0.0083 |
| 2039 | 0.018 |
| 2040 | 0.15 |
| 2041 | 0.11 |
| 2042 | 0.070 |
| 2043 | 0.012 |
| 2044 | 0.0079 |
| 2045 | 0.015 |
| 2046 | 0.0037 |
| 2047 | 0.0057 |
| 2048 | 0.0035 |
| 2049 | 0.0040 |
| 2050 | 0.051 |
| 2051 | 0.0025 |
| 2052 | 0.0049 |
| 2053 | 0.010 |
| 2054 | 0.0041 |
| 2055 | 0.027 |
| 2056 | 0.013 |
| 2057 | 0.0011 |
| 2058 | 0.38 |
| 2059 | 0.00096 |
| 2060 | 0.11 |
| 2061 | 0.021 |
| 2062 | 0.0069 |
| 2063 | 0.0088 |
| 2064 | 0.012 |
| 2065 | 0.016 |
| 2066 | 0.063 |
| 2067 | 0.00084 |
| 2068 | 0.0017 |
| 2069 | 0.078 |
| 2070 | 0.018 |
| 2071 | 0.0092 |
| 2072 | 0.00042 |
| 2073 | 0.012 |
| 2074 | 0.0027 |
| 2075 | 0.0011 |
| 2076 | 0.0025 |
| 2077 | 0.047 |
| 2078 | 0.011 |
| 2079 | 0.017 |
| 2080 | 0.00033 |
| 2081 | 0.0020 |
| 2082 | 0.041 |
| 2083 | 0.052 |
| 2084 | 0.13 |
| 2085 | 0.0029 |
| 2086 | 0.10 |
| 2087 | 0.13 |
| 2088 | 0.030 |
| 2089 | 0.30 |
| 2090 | 0.38 |
| 2091 | 0.27 |
| 2092 | 0.35 |
| 2093 | 0.037 |
| 2094 | 0.20 |
| 2095 | 0.24 |
| 2096 | 0.019 |
| 2097 | 0.00057 |
| 2098 | 0.0080 |
| 2099 | 0.025 |
| 2100 | 0.015 |
| 2101 | 0.053 |
| 2102 | 0.00092 |
| 2103 | 0.0083 |
| 2104 | 0.010 |
| 2105 | 0.0026 |
| 2106 | 0.0020 |
| 2107 | 0.0048 |
| 2108 | 0.0079 |
| 2109 | 0.0018 |
| 2110 | 0.0098 |
| 2111 | 0.0082 |
| 2112 | 0.011 |
| 2113 | 0.00047 |
| 2114 | 0.11 |
| 2115 | 0.0011 |
| 2116 | 0.11 |
| 2117 | 0.00041 |
| 2118 | 0.0032 |
| 2119 | 0.00039 |
| 2120 | 0.0010 |
| 2121 | 0.00056 |
| 2122 | 0.00046 |
| 2123 | 0.0015 |
| 2124 | 0.00091 |
| 2125 | 0.016 |
| 2126 | 0.037 |
| 2127 | 0.0045 |
| 2128 | 0.015 |
| 2129 | 0.046 |
| 2130 | 0.010 |
| 2131 | 0.0098 |
| 2132 | 0.091 |
| 2133 | 0.012 |
| 2134 | 0.0098 |
| 2135 | 0.088 |
| 2136 | 0.039 |
| 2137 | 0.069 |
| 2138 | 0.0086 |
| 2139 | 0.023 |
| 2140 | 0.032 |
| 2141 | 0.072 |
| 2142 | 0.044 |
| 2143 | 0.041 |
| 2144 | 0.0069 |
| 2145 | 0.022 |
| 2146 | 0.0051 |
| 2147 | 0.0080 |
| 2148 | 0.063 |
| 2149 | 0.0040 |
| 2150 | 0.0057 |
| 2151 | 0.0025 |
| 2152 | 0.071 |
| 2153 | 0.0069 |
| 2154 | 0.033 |
| 2155 | 0.028 |
| 2156 | 0.0045 |
| 2157 | 0.0069 |
| 2158 | 0.089 |
| 2159 | 0.0035 |
| 2160 | 0.0038 |
| 2161 | 0.48 |
| 2162 | 0.20 |
| 2163 | 0.073 |
| 2164 | 0.30 |
| 2165 | 0.22 |
| 2166 | 0.33 |
| 2167 | 0.38 |
| 2168 | 0.0013 |
| 2169 | 0.0061 |
| 2170 | 0.069 |
| 2171 | 0.12 |
| 2172 | 0.014 |
| 2173 | 0.0060 |
| 2174 | 0.87 |
| 2175 | 0.18 |
| 2176 | 0.12 |
| 2177 | 0.25 |
| 2178 | 0.16 |
| 2179 | 0.54 |
| 2180 | 0.00093 |
| 2181 | 0.0055 |
| 2182 | 0.0036 |
| 2183 | 0.0019 |
| 2184 | 0.0079 |

TABLE 23-continued

| Compound No. | KRAS G12D-SOS PPI IC50 (µM) |
|---|---|
| 2185 | 0.0024 |
| 2186 | 0.0075 |

Measurement of AsPC-1 Cell Growth Inhibition (AsPC-1 CGI)

Test compounds were serially diluted with dimethyl sulfoxide, and 200 nL was then dispensed to a U-bottom 96-well plate using Labcyte Echo. Human pancreatic cancer cell line AsPC-1 was suspended in RPMI-1640 medium supplemented with 15% fetal bovine serum to prepare a cell suspension at 1000 cells/100 µL. The cell suspension was dispensed to a plate containing a test compound at 100 µL per well and incubated at 37° C. in a 5% carbon dioxide gas incubator. 96 hours later, 80 µL of CellTiter-Glo (Promega) was added to each well and fluorescence was measured. The cell growth inhibition (CGI) of the test compound was calculated as 50% growth inhibitory concentration (IC50 value) from the growth inhibition rate when the test compound was added relative to the test compound-free control. IC50 values (µM) of the test compounds were classified in that range and the results are shown below.

Cyclic peptide compounds of Compound Nos. 5, 9, 16, 20, 27, 33, 40, 47, 54, 55, 66, 120, 132, 134, 144, 150, 176, 209, 245, 253, 270, 276, 279, 289, 301, 302, 303, 308, 316, 334, 342, 343, 344, 362, 363, 370, 371, 374, 378, 381, 390, 391, 400, 404, 415, 422, 432, 466, 481, 506, 509, 515, 529, 545, 547, 555, 567, 571, 574, 587, 589, 594, 626, 630, 640, 668, 678, 690, 693, 695, 713, 717, 721, 731, 734, 775, 799, 806, 816, 835, 836, 840, 863, 866, 871, 882, 896, 907, 926, 938, 965, 973, 974, 981, 987, 999, 1017, 1042, 1059, 1070, 1080, 1091, 1099, 1116, 1117, 1120, 1132, 1139, 1141, 1143, 1144, 1148, 1149, 1151, 1152, 1158, 1160, 1162, 1163, 1165, 1166, 1170, 1173, 1175, 1179, 1182, 1183, 1190, 1192, 1194, 1196, 1199, 1201, 1204, 1205, 1206, 1208, 1209, 1210, 1215, 1217, 1220, 1224, 1231, 1232, 1234, 1237, 1241, 1242, 1244, 1245, 1248, 1250, 1259, 1260, 1261, 1264, 1267, 1269, 1270, 1271, 1272, 1281, 1282, 1283, 1285, 1289, 1290, 1293, 1295, 1296, 1297, 1301, 1303, 1306, 1308, 1310, 1311, 1312, 1317, 1319, 1320, 1322, 1324, 1325, 1330, 1333, 1335, 1336, 1337, 1339, 1341, 1342, 1343, 1346, 1348, 1351, 1356, 1357, 1360, 1362, 1363, 1364, 1365, 1366, 1367, 1368, 1369, 1370, 1371, 1645, 1649, 1659, 1661, 1662, 1750, 1756, 1772, 1777, 1779, 1787, 1792, 1793, 1809, 1818, 1836, 1842, 1843, 1858, 1865, 1875, 1886, 1894, 1898, 1962, 1977, 1979, 1985, 1990, 2001, and 2080 showed an IC50 value which is 0.02 (µM) or lower.

Cyclic peptide compounds of Compound Nos. 44, 48, 49, 56, 73, 79, 89, 127, 128, 155, 173, 182, 201, 236, 243, 263, 272, 311, 313, 339, 340, 366, 386, 388, 403, 410, 441, 469, 531, 558, 563, 622, 647, 684, 694, 726, 768, 774, 776, 778, 790, 807, 814, 818, 827, 868, 885, 890, 900, 918, 921, 958, 959, 977, 1000, 1001, 1002, 1008, 1029, 1030, 1046, 1060, 1062, 1073, 1093, 1098, 1137, 1142, 1146, 1154, 1159, 1164, 1171, 1193, 1197, 1198, 1223, 1228, 1236, 1251, 1253, 1254, 1275, 1278, 1287, 1292, 1299, 1326, 1340, 1355, 1658, 1675, 1679, 1685, 1694, 1700, 1701, 1722, 1726, 1727, 1729, 1757, 1761, 1762, 1790, 1821, 1840, 1850, 1851, 1852, 1870, 1871, 1872, 1884, 1890, 1904, 1905, 1907, 1925, 1930, 1936, 1938, 1948, 1950, 1958, 1972, 1978, 1983, 1984, 1996, 2004, 2067, 2072, and 2119 showed an IC50 value which is higher than 0.02 (µM) and is 0.05 (µM) or lower.

Cyclic peptide compounds of Compound Nos. 11, 68, 88, 126, 137, 160, 161, 163, 239, 246, 274, 292, 326, 327, 353, 385, 408, 409, 411, 420, 425, 434, 437, 438, 453, 486, 518, 532, 535, 543, 551, 562, 608, 616, 650, 652, 662, 674, 677, 683, 699, 701, 708, 712, 735, 783, 820, 825, 837, 845, 859, 881, 904, 909, 912, 948, 1023, 1037, 1047, 1112, 1150, 1176, 1178, 1180, 1189, 1233, 1309, 1321, 1331, 1338, 1359, 1374, 1463, 1475, 1496, 1512, 1524, 1537, 1549, 1550, 1551, 1563, 1570, 1571, 1572, 1590, 1597, 1604, 1610, 1617, 1620, 1621, 1629, 1634, 1637, 1653, 1654, 1668, 1671, 1680, 1689, 1696, 1714, 1717, 1720, 1728, 1735, 1740, 1746, 1748, 1770, 1784, 1785, 1786, 1795, 1798, 1800, 1801, 1804, 1805, 1807, 1812, 1824, 1835, 1861, 1869, 1879, 1881, 1892, 1901, 1906, 1908, 1911, 1915, 1923, 1932, 1933, 1941, 1947, 1963, 1965, 1966, 1968, 1969, 1975, 1988, 1993, 1994, 2005, 2006, 2057, 2063, 2074, 2076, 2118, 2121, and 2122 showed an IC50 value which is higher than 0.05 (µM) and is 0.1 (µM) or lower.

Cyclic peptide compounds of Compound Nos. 2, 15, 23, 30, 35, 36, 37, 39, 52, 58, 60, 64, 72, 78, 80, 81, 86, 90, 94, 100, 106, 108, 110, 119, 121, 122, 131, 136, 140, 147, 157, 164, 168, 207, 211, 212, 216, 220, 221, 223, 225, 229, 238, 249, 250, 256, 264, 273, 285, 287, 288, 294, 300, 309, 319, 321, 328, 337, 341, 348, 354, 356, 360, 364, 367, 384, 387, 393, 395, 397, 399, 416, 428, 439, 445, 446, 449, 455, 456, 461, 470, 476, 478, 480, 488, 491, 496, 497, 520, 523, 526, 544, 548, 552, 559, 561, 568, 572, 575, 580, 599, 600, 606, 618, 620, 629, 631, 644, 663, 667, 672, 676, 680, 689, 700, 714, 732, 740, 747, 749, 755, 756, 757, 762, 771, 787, 789, 798, 804, 809, 811, 815, 824, 838, 849, 853, 854, 872, 873, 877, 880, 888, 893, 901, 910, 911, 916, 920, 929, 930, 943, 944, 957, 960, 961, 968, 971, 980, 983, 985, 988, 995, 997, 1005, 1012, 1014, 1018, 1019, 1022, 1026, 1035, 1036, 1038, 1040, 1051, 1055, 1057, 1064, 1066, 1069, 1071, 1072, 1109, 1114, 1115, 1124, 1128, 1130, 1140, 1145, 1153, 1167, 1172, 1181, 1203, 1207, 1213, 1218, 1227, 1235, 1252, 1255, 1262, 1266, 1273, 1284, 1291, 1302, 1315, 1323, 1329, 1332, 1334, 1347, 1353, 1376, 1439, 1454, 1457, 1458, 1462, 1466, 1471, 1477, 1481, 1482, 1485, 1486, 1497, 1498, 1499, 1500, 1501, 1504, 1508, 1514, 1523, 1544, 1555, 1557, 1561, 1564, 1565, 1567, 1569, 1576, 1579, 1583, 1584, 1588, 1589, 1594, 1596, 1598, 1599, 1601, 1602, 1605, 1607, 1608, 1609, 1611, 1615, 1616, 1625, 1626, 1630, 1631, 1632, 1633, 1636, 1638, 1639, 1640, 1641, 1643, 1646, 1648, 1650, 1652, 1656, 1657, 1663, 1669, 1670, 1672, 1673, 1682, 1684, 1686, 1693, 1699, 1704, 1705, 1709, 1711, 1712, 1713, 1716, 1731, 1737, 1738, 1739, 1744, 1749, 1751, 1758, 1763, 1764, 1766, 1767, 1773, 1774, 1789, 1791, 1796, 1797, 1803, 1817, 1825, 1828, 1829, 1830, 1832, 1833, 1838, 1845, 1846, 1847, 1854, 1859, 1860, 1863, 1866, 1867, 1877, 1896, 1900, 1913, 1916, 1921, 1924, 1926, 1928, 1929, 1931, 1934, 1939, 1940, 1949, 1954, 1955, 1956, 1957, 1971, 1976, 1980, 1998, 1999, 2031, 2059, 2064, 2065, 2077, 2078, 2084, 2085, 2097, 2102, 2117, 2120, 2123, 2124, 2131, 2138, 2139, and 2168 showed an IC50 value which is higher than 0.1 (µM) and is 0.5 (µM) or lower.

Cyclic peptide compounds of Compound Nos. 1, 4, 6, 7, 10, 12, 13, 14, 17, 22, 24, 32, 43, 45, 57, 59, 61, 63, 67, 69, 71, 75, 76, 83, 87, 91, 92, 93, 95, 97, 102, 103, 109, 111, 114, 115, 116, 117, 118, 123, 124, 125, 133, 135, 139, 141, 142, 143, 145, 146, 148, 149, 151, 156, 158, 159, 162, 165, 166, 169, 171, 172, 174, 175, 177, 178, 179, 180, 183, 185, 186, 187, 188, 191, 192, 194, 195, 196, 197, 200, 202, 204, 205, 208, 210, 213, 217, 218, 226, 228, 230, 231, 232, 234, 235, 237, 247, 248, 251, 254, 255, 257, 259, 262, 265, 266, 268, 275, 277, 278, 280, 281, 283, 284, 295, 297, 298, 304, 305, 307, 312, 314, 317, 318, 320, 325, 329, 330, 332, 335, 336, 346, 347, 352, 357, 358, 368, 376, 379, 380, 382, 389, 392, 394, 402, 405, 407, 417, 418, 419, 421, 423, 426, 427, 433, 440, 442, 443, 444, 447, 450, 451, 454, 457, 458, 459, 460, 463, 468, 471, 477, 483, 484, 485, 487, 489, 492, 495, 498, 500, 501, 504, 507, 508, 511, 514, 516, 519, 522, 524, 527, 528, 533, 534, 538, 540, 542, 549, 553, 554, 556, 557, 564, 565, 569, 570, 577, 581, 584, 585, 586, 590, 591, 592, 593, 596, 597, 598, 603, 604, 605, 614, 619, 623, 627, 635, 636, 638, 641, 643, 645, 648, 653, 656, 661, 664, 665, 666, 670, 681, 682, 687, 688, 691, 692, 696, 697, 703, 705, 706, 707, 709, 710, 711, 715, 716, 718, 720, 722, 723, 725, 727, 728, 729, 730, 736, 741, 742, 744, 745, 753, 754, 760, 765, 766, 767, 769, 770, 772, 781, 782, 784, 786, 788, 792, 794, 796, 797, 800, 801, 803, 805, 810, 812, 813, 819, 821, 822, 823, 829, 841, 842, 844, 848, 850, 851, 855, 856, 857, 858, 861, 862, 864, 867, 874, 875, 876, 879, 883, 887, 892, 894, 895, 897, 903, 905, 906, 908, 913, 914, 915, 917, 933, 934, 935, 936, 939, 940, 941, 942, 945, 946, 950, 954, 955, 956, 963, 964, 967, 969, 970, 975, 979, 982, 986, 991, 993, 994, 998, 1004, 1007, 1009, 1010, 1011, 1015, 1016, 1020, 1021, 1024, 1025, 1027, 1033, 1034, 1041, 1043, 1044, 1045, 1050, 1053, 1054, 1056, 1058, 1061, 1063, 1068, 1076, 1077, 1079, 1081, 1083, 1084, 1087, 1089, 1094, 1095, 1096, 1100, 1101, 1103, 1105, 1106, 1110, 1111, 1121, 1123, 1125, 1129, 1133, 1134, 1135, 1138, 1157, 1169, 1174, 1177, 1185, 1186, 1187, 1188, 1191, 1195, 1200, 1202, 1211, 1214, 1216, 1219, 1221, 1222, 1225, 1226, 1229, 1230, 1238, 1239, 1243, 1246, 1247, 1249, 1256, 1257, 1258, 1263, 1268, 1274, 1276, 1277, 1279, 1286, 1288, 1294, 1298, 1300, 1304, 1305, 1307, 1313, 1314, 1316, 1318, 1327, 1328, 1345, 1350, 1354, 1358, 1361, 1372, 1377, 1380, 1386, 1387, 1388, 1392, 1396, 1397, 1398, 1403, 1404, 1411, 1414, 1415, 1417, 1419, 1421, 1422, 1424, 1425, 1426, 1428, 1429, 1432, 1433, 1435, 1436, 1438, 1440, 1441, 1443, 1444, 1448, 1449, 1451, 1452, 1453, 1455, 1456, 1459, 1460, 1461, 1465, 1467, 1469, 1472, 1474, 1476, 1478, 1480, 1483, 1484, 1489, 1490, 1491, 1493, 1495, 1502, 1503, 1506, 1507, 1509, 1511, 1515, 1517, 1518, 1519, 1520, 1526, 1527, 1528, 1529, 1532, 1533, 1534, 1535, 1536, 1539, 1541, 1545, 1546, 1547, 1553, 1556, 1559, 1562, 1566, 1573, 1574, 1575, 1578, 1580, 1582, 1585, 1587, 1591, 1595, 1606, 1613, 1614, 1623, 1627, 1635, 1644, 1647, 1651, 1660, 1664, 1665, 1666, 1667, 1674, 1676, 1677, 1678, 1681, 1687, 1688, 1690, 1692, 1695, 1697, 1698, 1702, 1703, 1706, 1707, 1708, 1715, 1718, 1719, 1721, 1723, 1724, 1725, 1730, 1732, 1733, 1736, 1741, 1742, 1743, 1745, 1747, 1752, 1753, 1754, 1755, 1759, 1760, 1768, 1769, 1771, 1775, 1776, 1778, 1780, 1782, 1788, 1799, 1802, 1806, 1808, 1810, 1811, 1813, 1815, 1816, 1819, 1820, 1822, 1823, 1826, 1827, 1831, 1834, 1837, 1841, 1844, 1848, 1849, 1853, 1855, 1856, 1857, 1862, 1864, 1880, 1897, 1917, 1937, 1946, 1973, 1982, 2030, 2035, 2058, 2060, 2061, 2062, 2066, 2068, 2069, 2070, 2071, 2073, 2075, 2079, 2081, 2082, 2083, 2113, 2115, 2116, 2125, 2127, 2128, 2129, 2130, 2132, 2135, 2136, 2137, 2140, 2141, 2142, 2143, 2144, 2145, 2146, 2147, 2149, 2150, 2151, 2169, 2172, 2173, 2174, 2175, 2176, 2177, 2178, and 2179 showed an IC50 value which is higher than 0.5 (μM).
TABLE 24
| Compound No. | Structural formula |
|---|---|
| 1 | 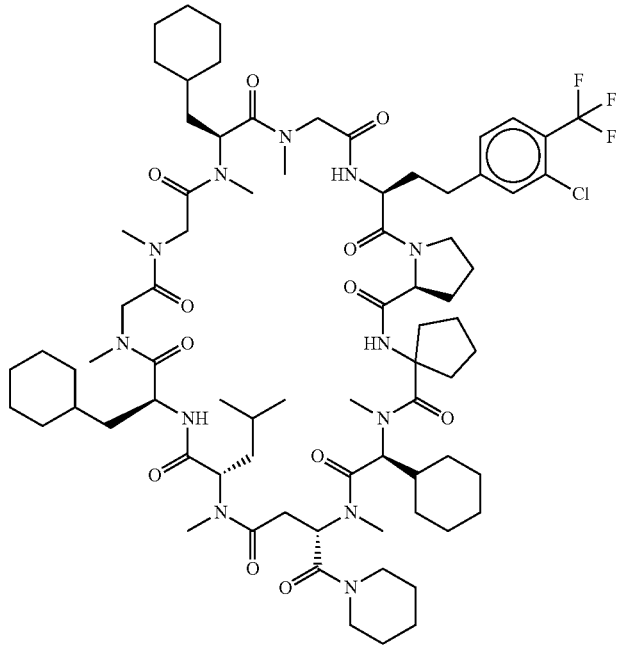 |

TABLE 24-continued
| Compound No. | Structural formula |
|---|---|
| 2 | 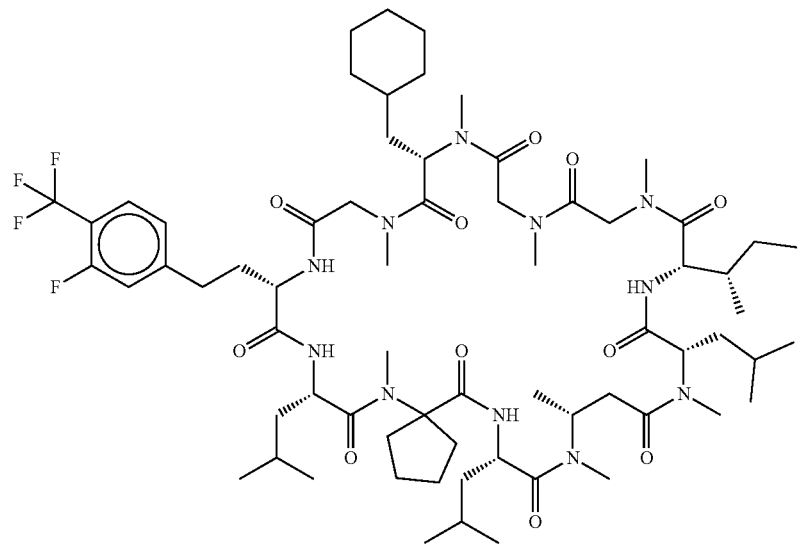 |
| 3 | 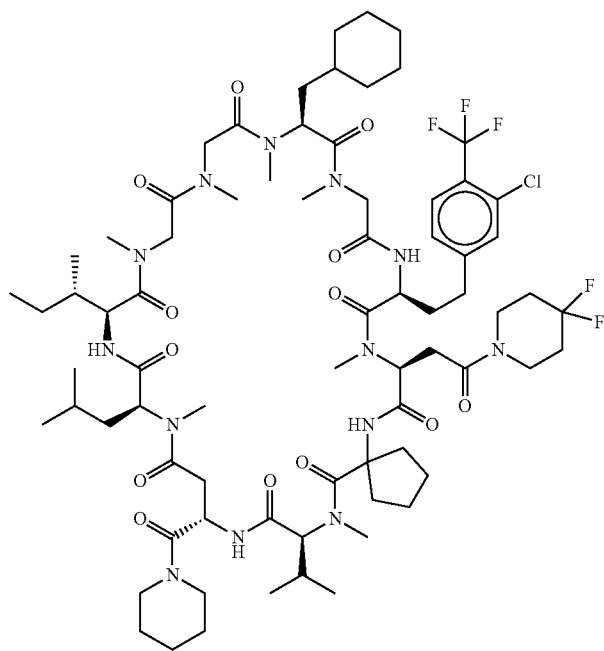 |

TABLE 24-continued
| Compound No. | Structural formula |
|---|---|
| 4 | 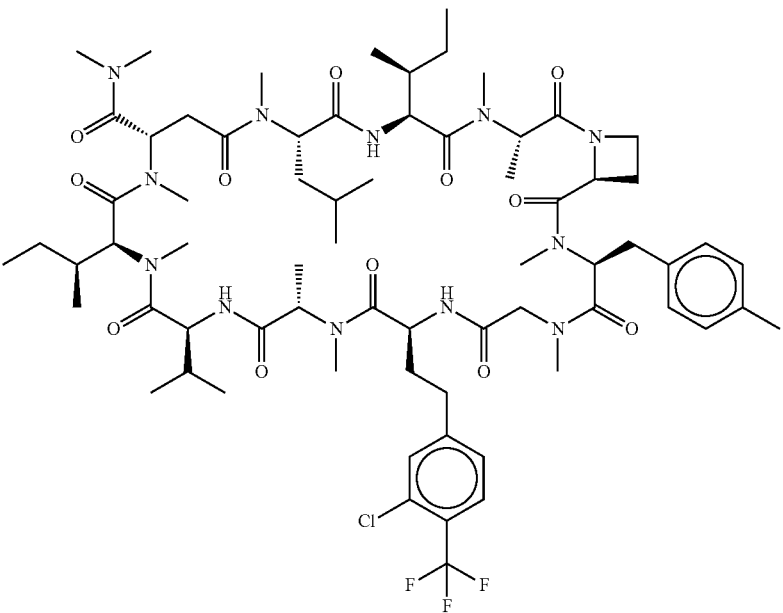 |
| 5 | 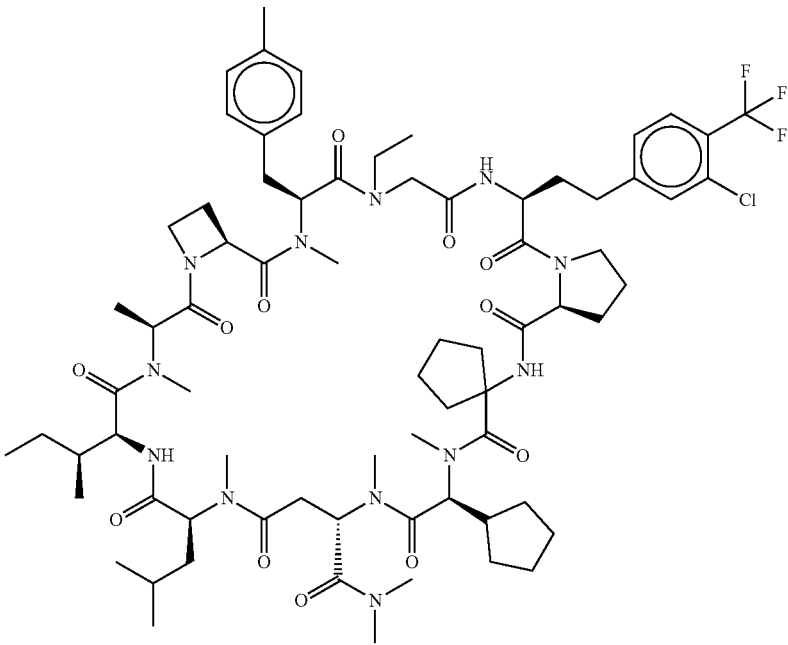 |

TABLE 24-continued
| Compound No. | Structural formula |
|---|---|
| 6 | 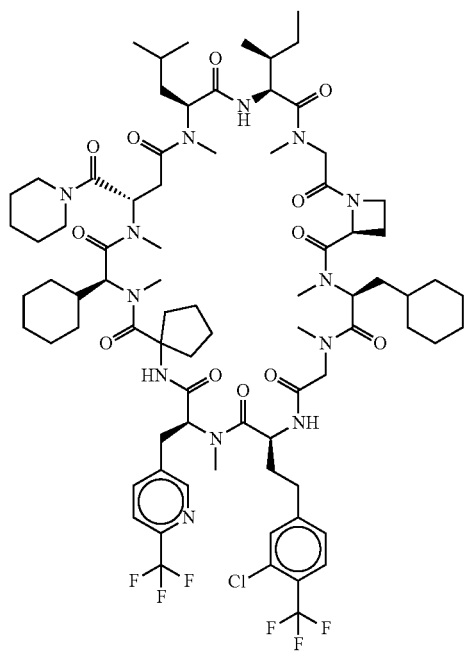 |
| 7 | 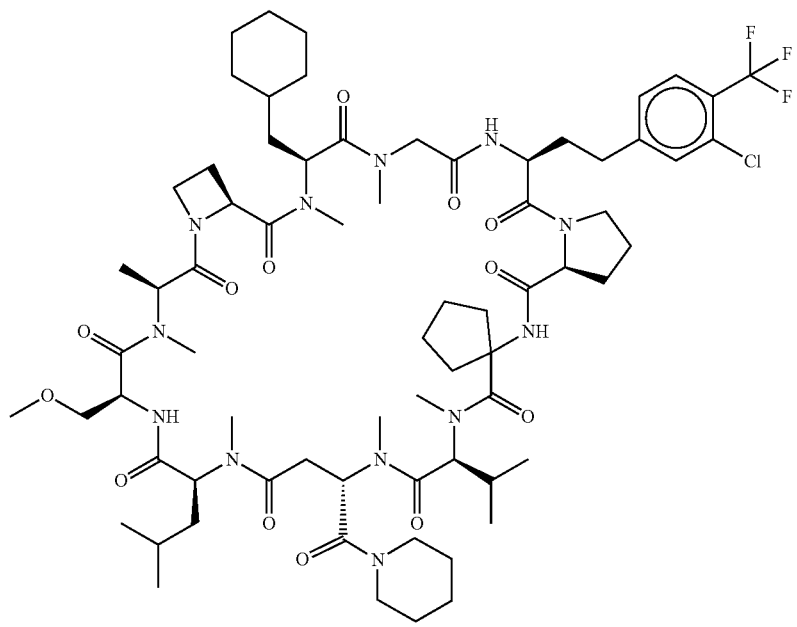 |

TABLE 24-continued
| Compound No. | Structural formula |
|---|---|
| 8 | 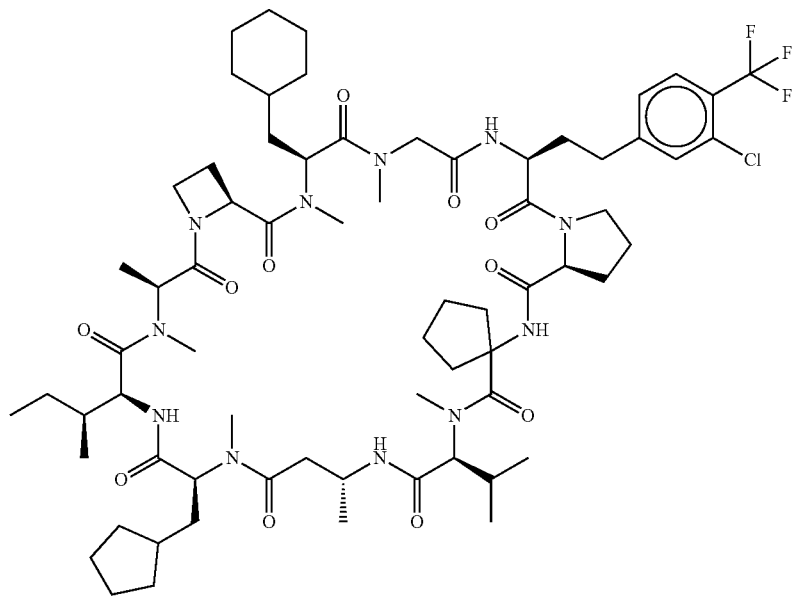 |
| 9 | 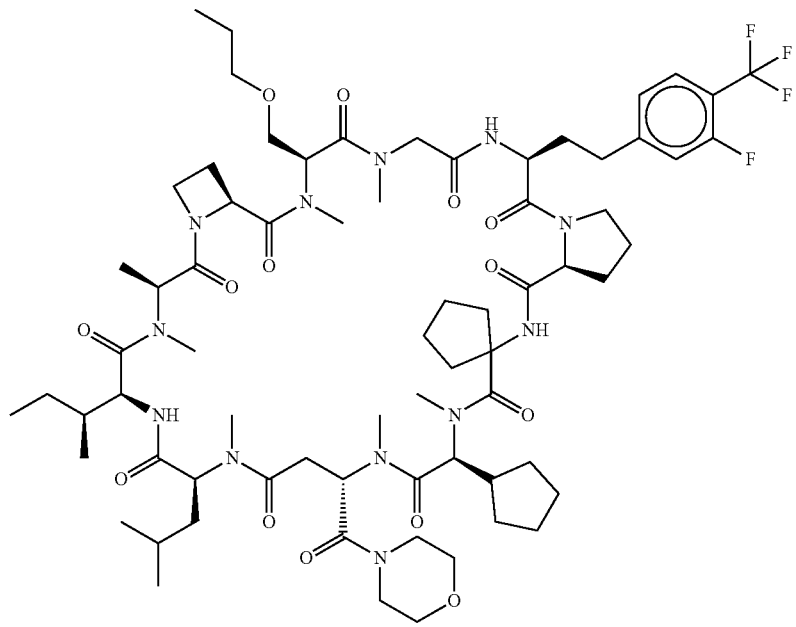 |

TABLE 24-continued
| Compound No. | Structural formula |
|---|---|
| 10 | 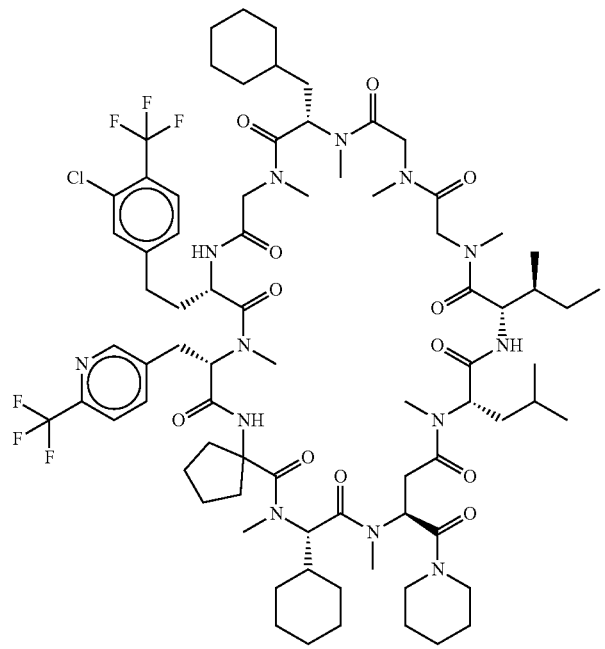 |
| 11 | 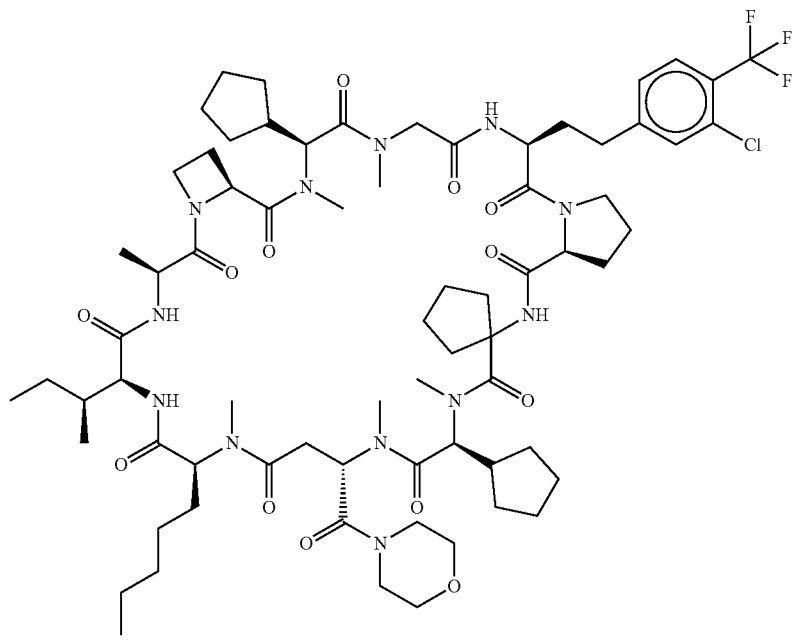 |

TABLE 24-continued
| Compound No. | Structural formula |
|---|---|
| 12 | 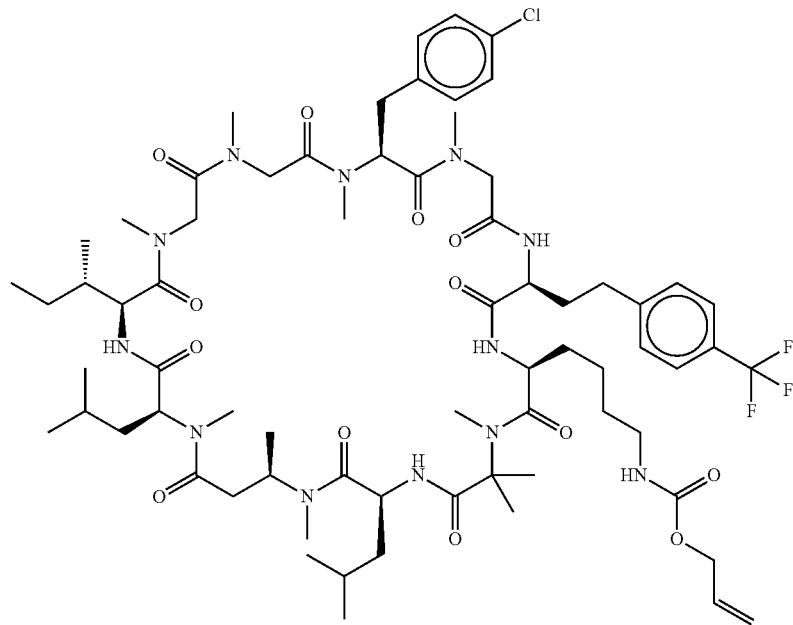 |
| 13 | 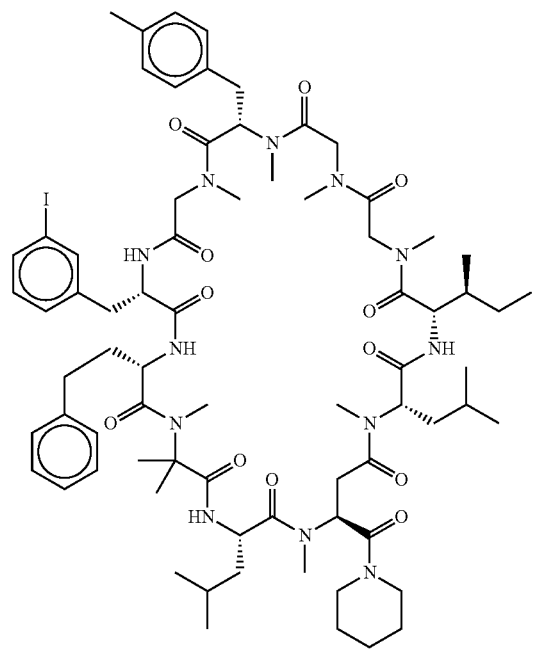 |

TABLE 24-continued
| Compound No. | Structural formula |
|---|---|
| 14 | 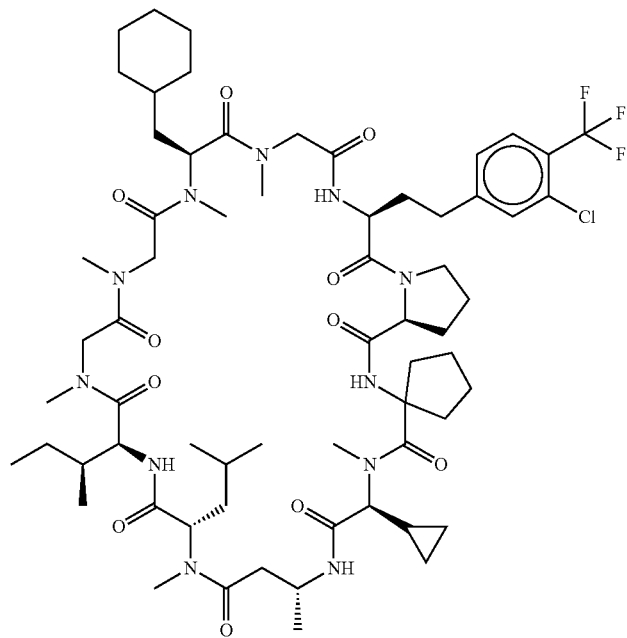 |
| 15 | 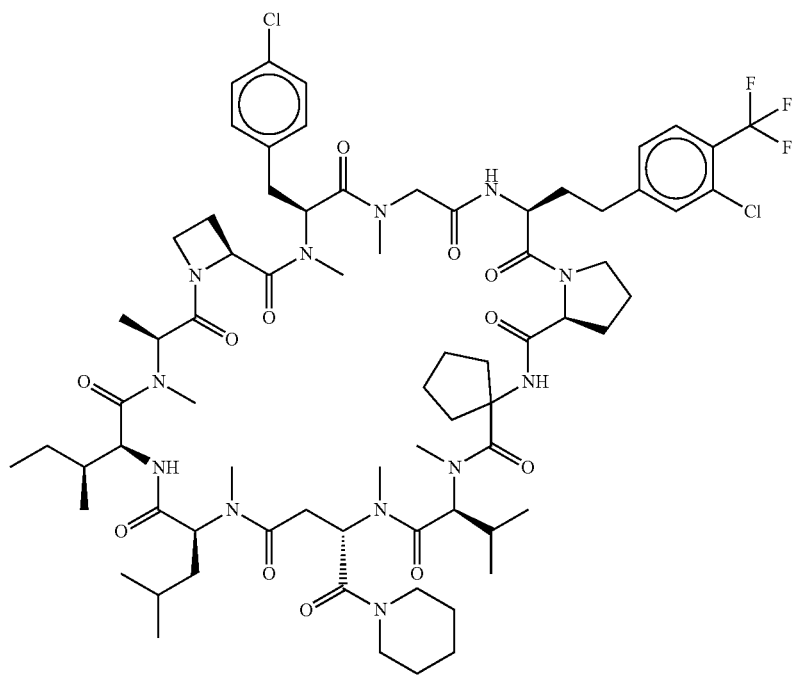 |

TABLE 24-continued
| Compound No. | Structural formula |
|---|---|
| 16 | 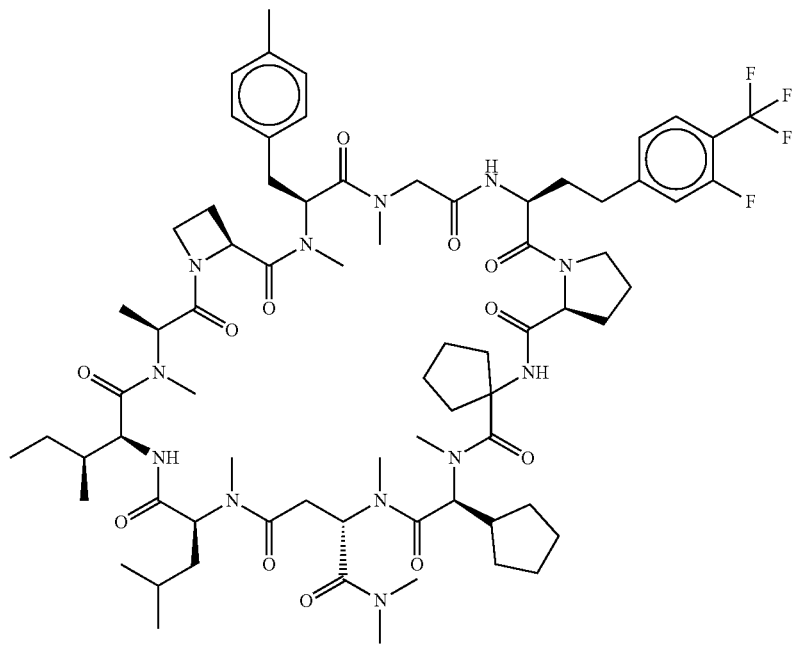 |
| 17 | 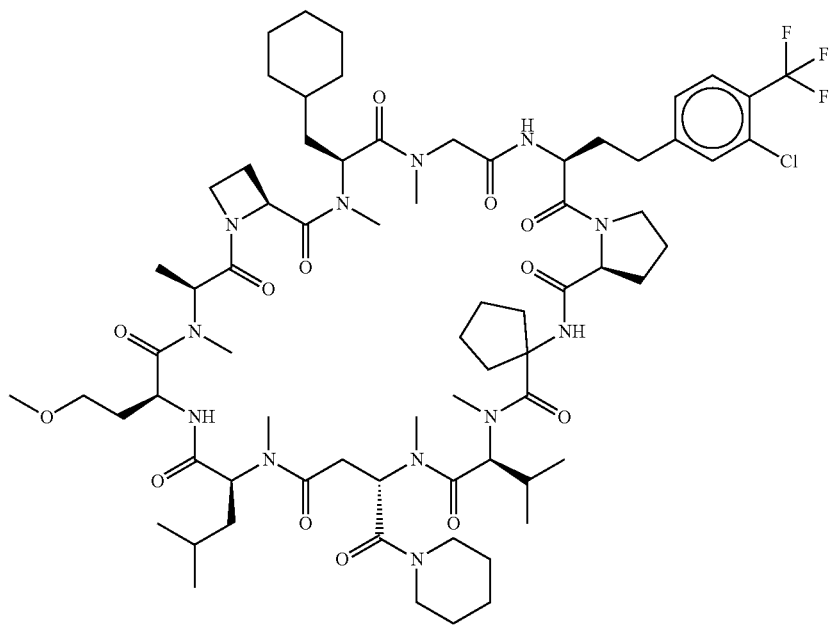 |

TABLE 24-continued
| Compound No. | Structural formula |
|---|---|
| 18 | 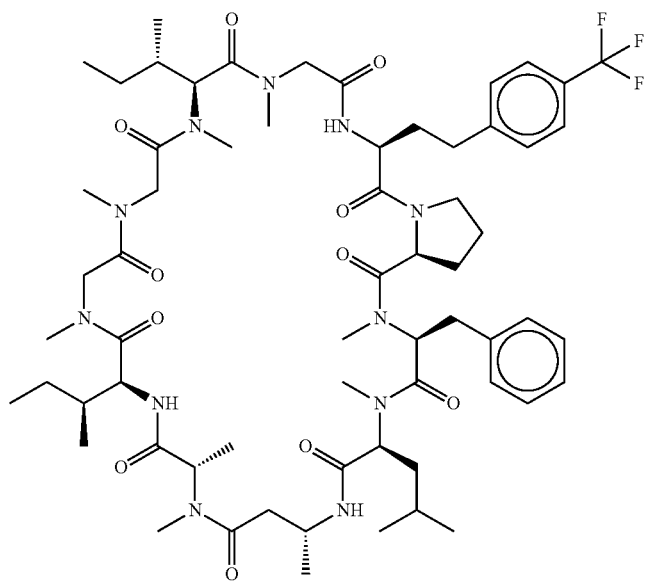 |
| 19 | 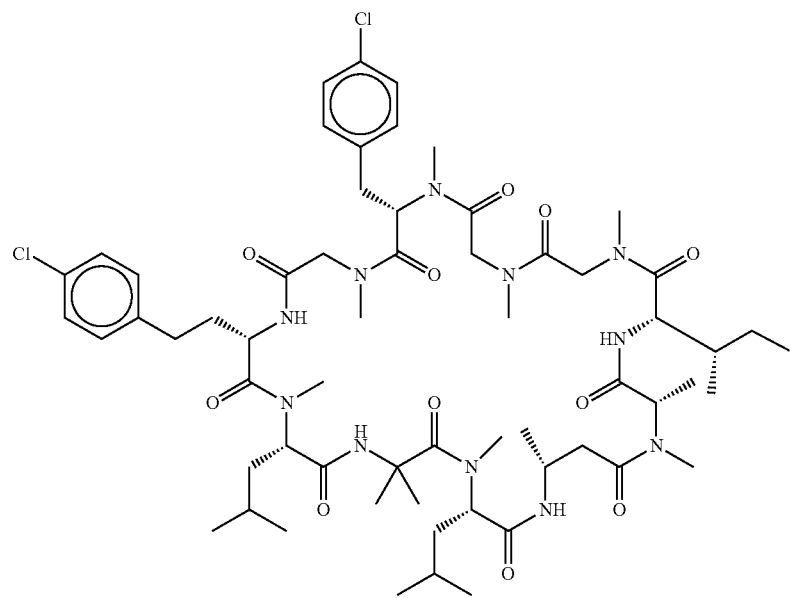 |

TABLE 24-continued
| Compound No. | Structural formula |
|---|---|
| 20 | 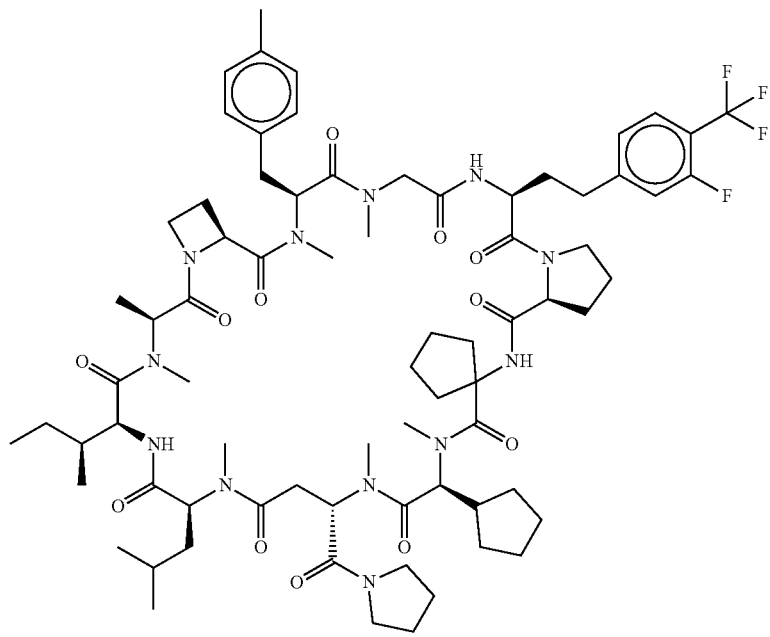 |
| 21 | 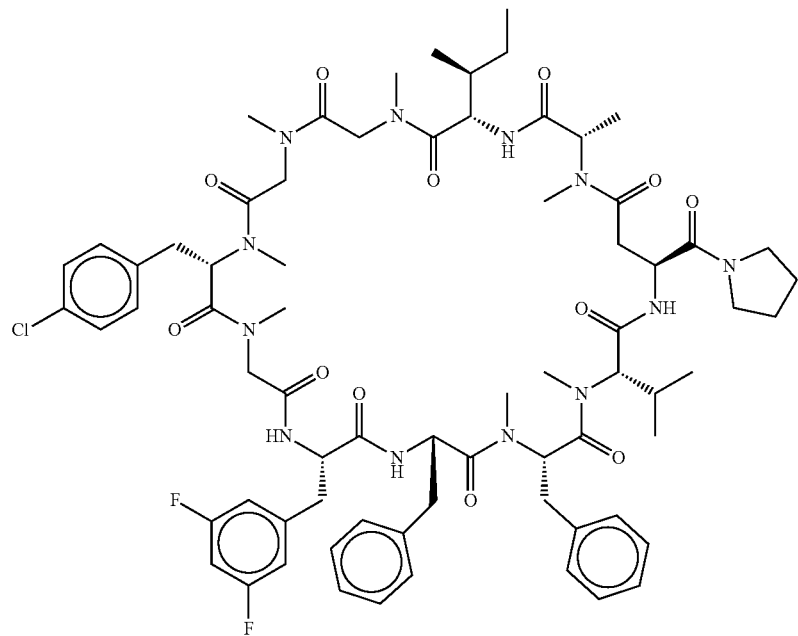 |

TABLE 24-continued
| Compound No. | Structural formula |
|---|---|
| 22 | 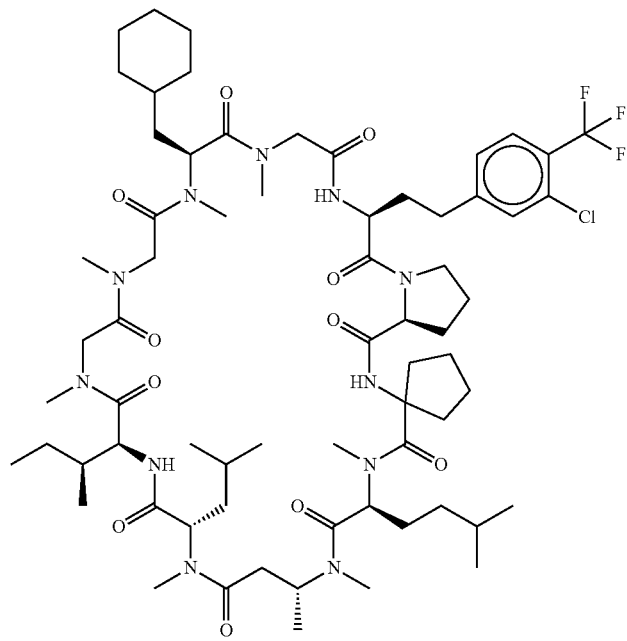 |
| 23 | 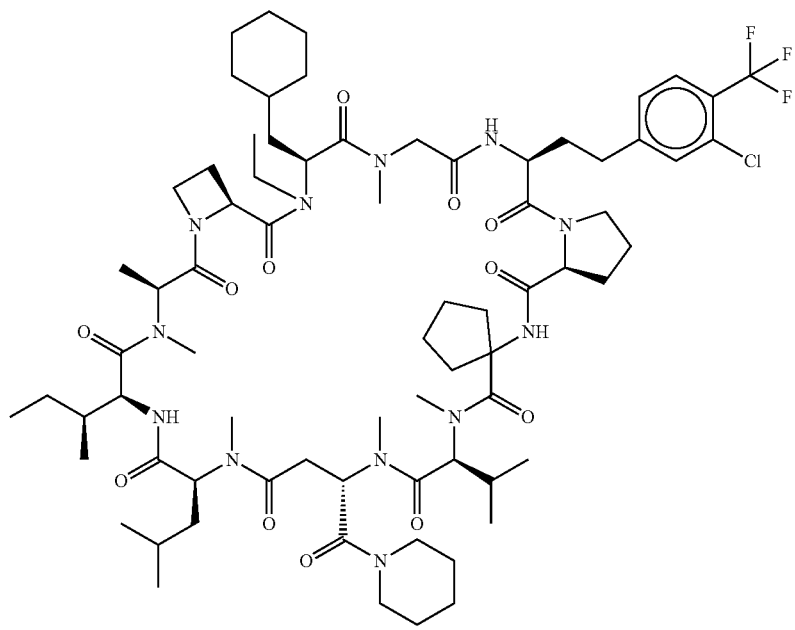 |

TABLE 24-continued
| Compound No. | Structural formula |
|---|---|
| 24 | 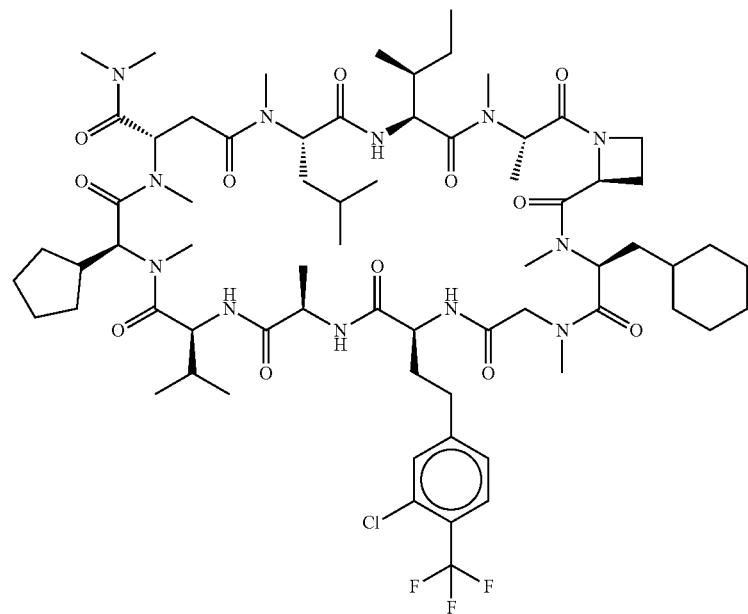 |
| 25 | 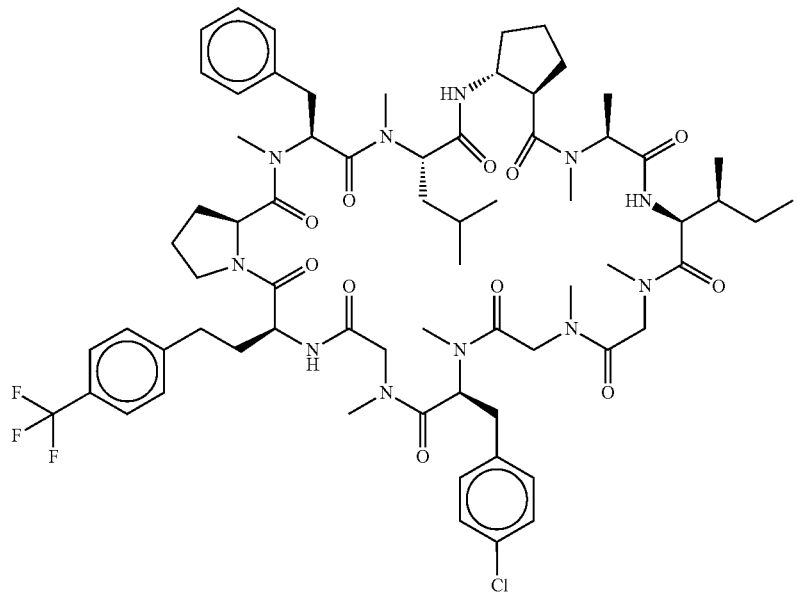 |

TABLE 24-continued
| Compound No. | Structural formula |
|---|---|
| 26 | 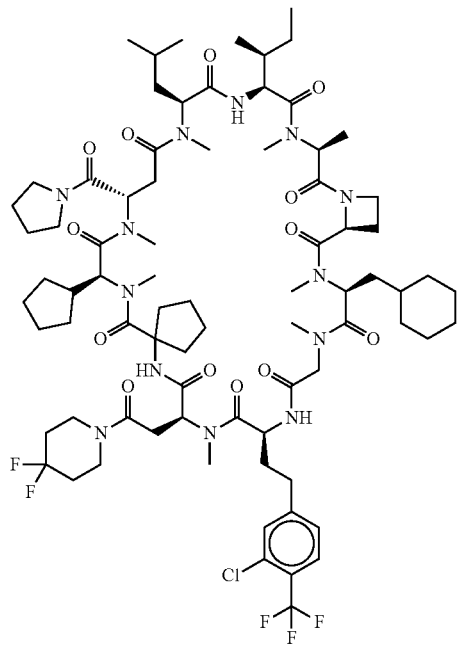 |
| 27 | 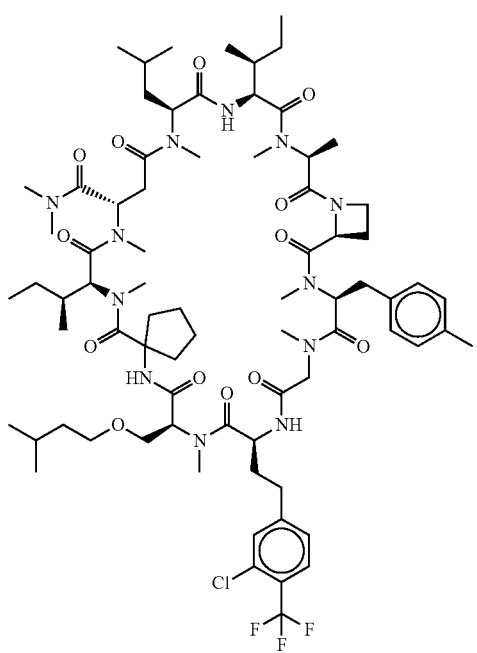 |

TABLE 24-continued
| Compound No. | Structural formula |
|---|---|
| 28 | 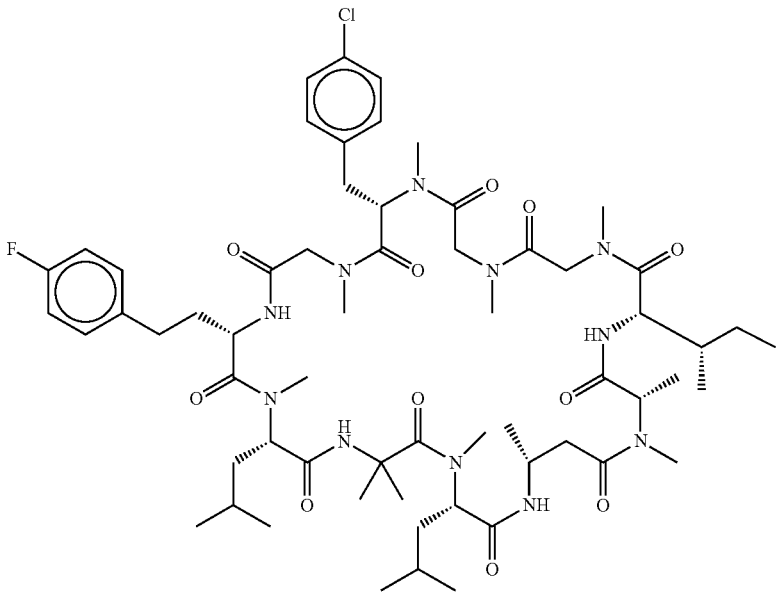 |
| 29 | 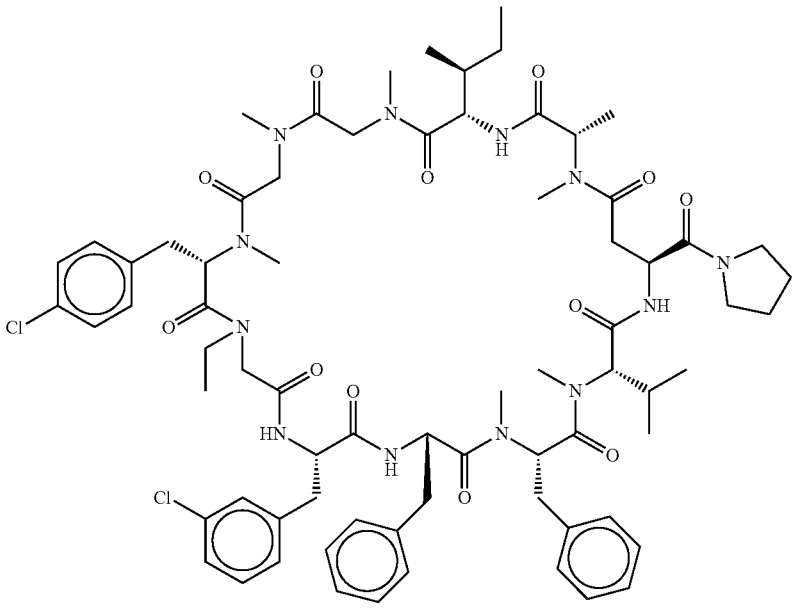 |

TABLE 24-continued
| Compound No. | Structural formula |
|---|---|
| 30 | 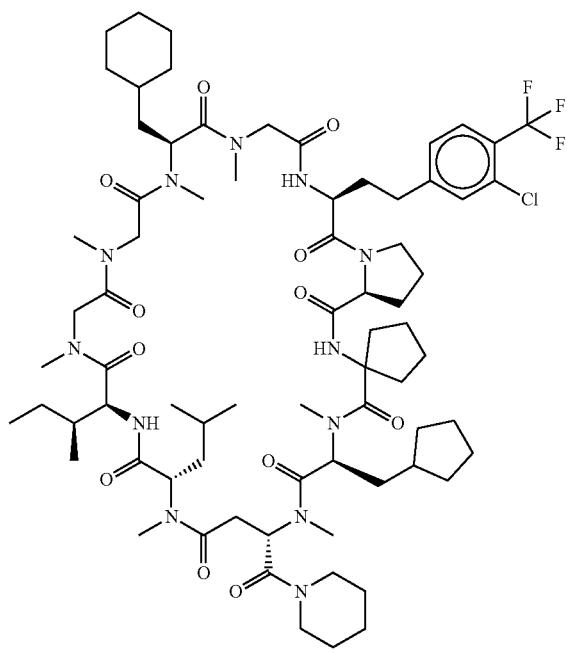 |
| 31 | 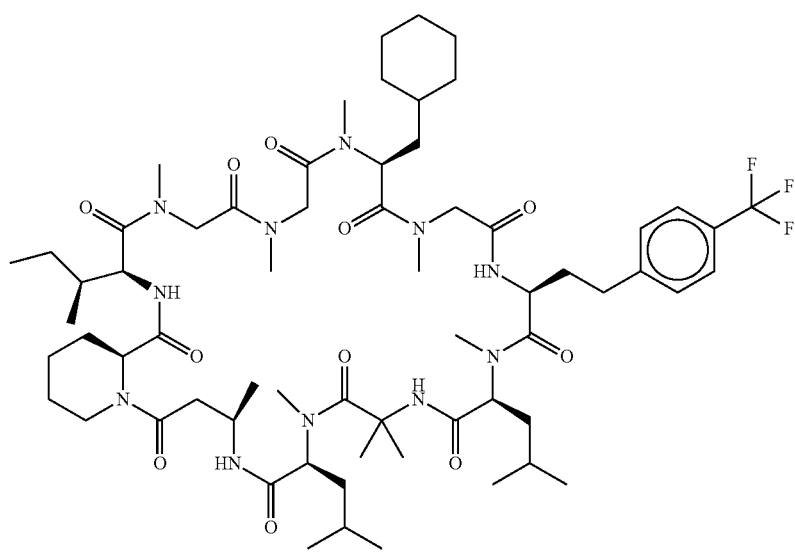 |

TABLE 24-continued
| Compound No. | Structural formula |
|---|---|
| 32 | 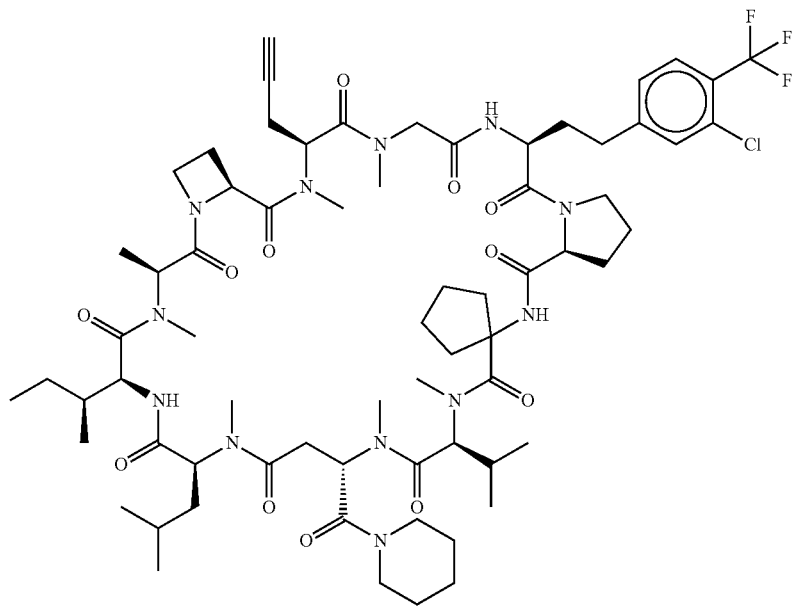 |
| 33 | 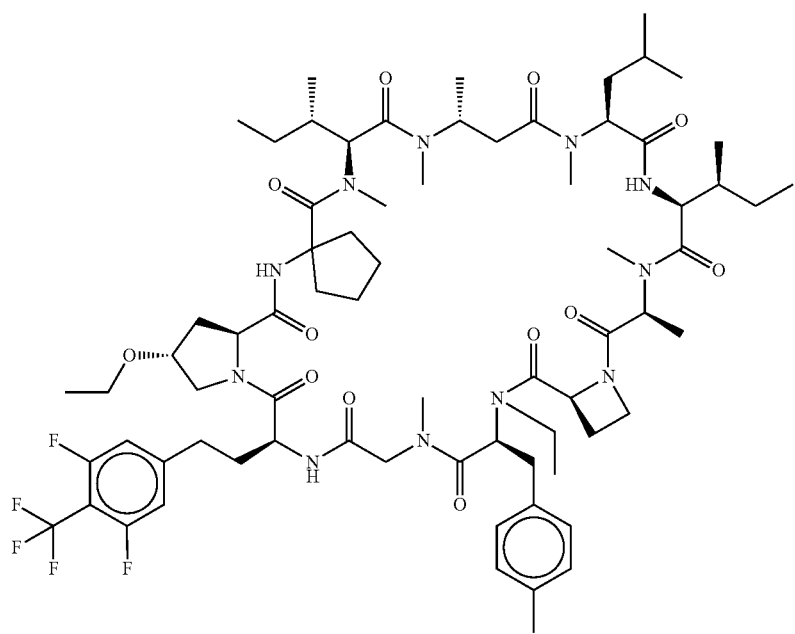 |

| Compound No. | Structural formula |
|---|---|
| 34 | 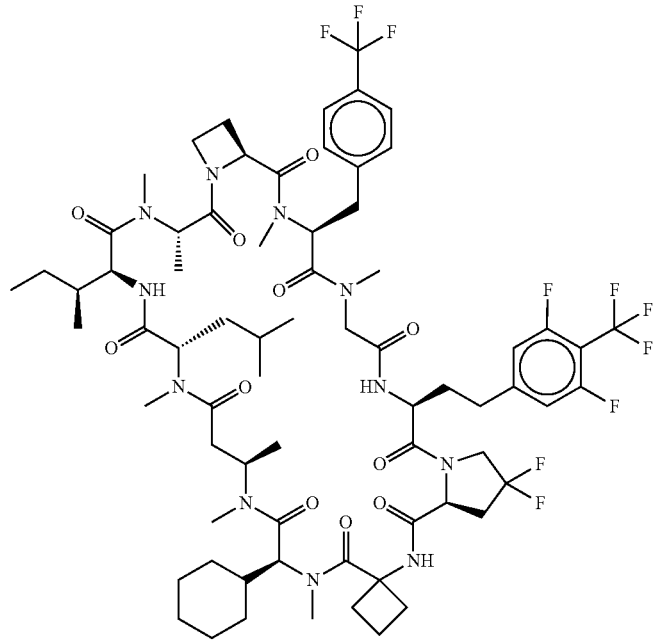 |
| 35 | 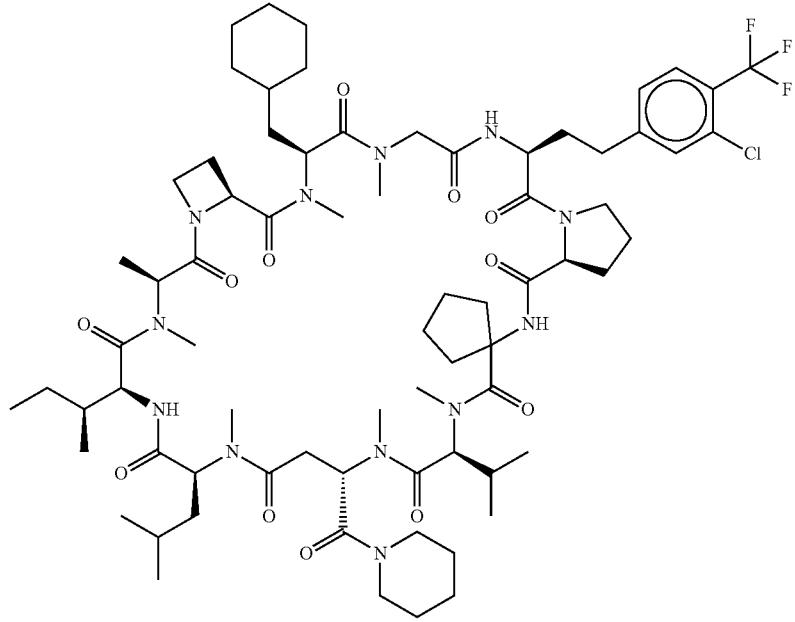 |

TABLE 24-continued
| Compound No. | Structural formula |
|---|---|
| 36 | 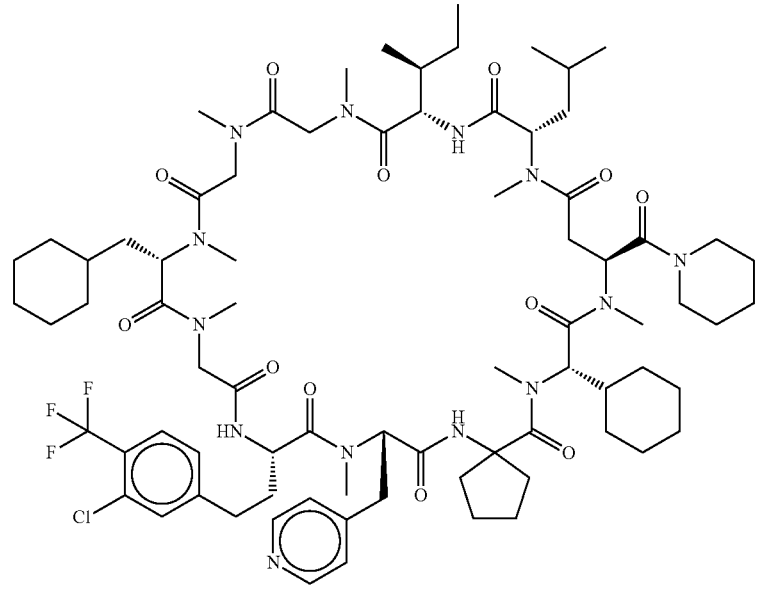 |
| 37 | 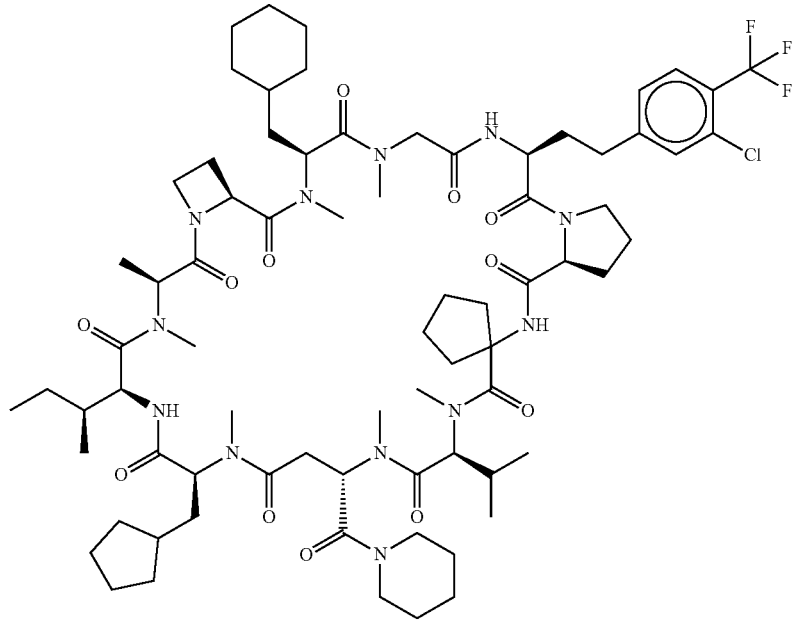 |

TABLE 24-continued
| Compound No. | Structural formula |
| --- | --- |
| 38 | 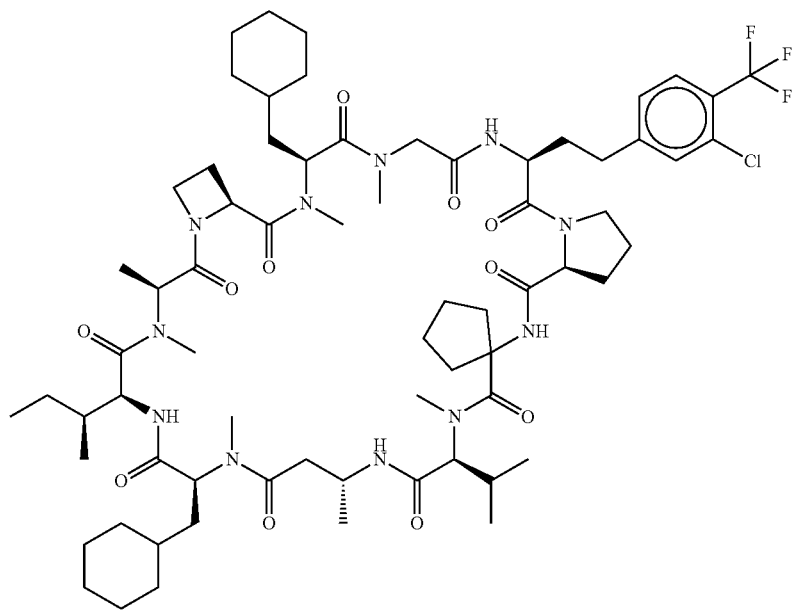 |
| 39 | 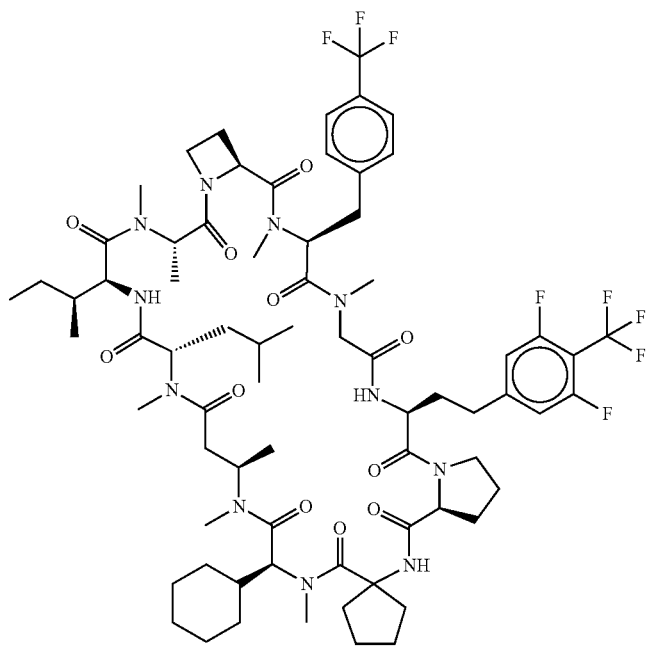 |

TABLE 24-continued
| Compound No. | Structural formula |
|---|---|
| 40 | 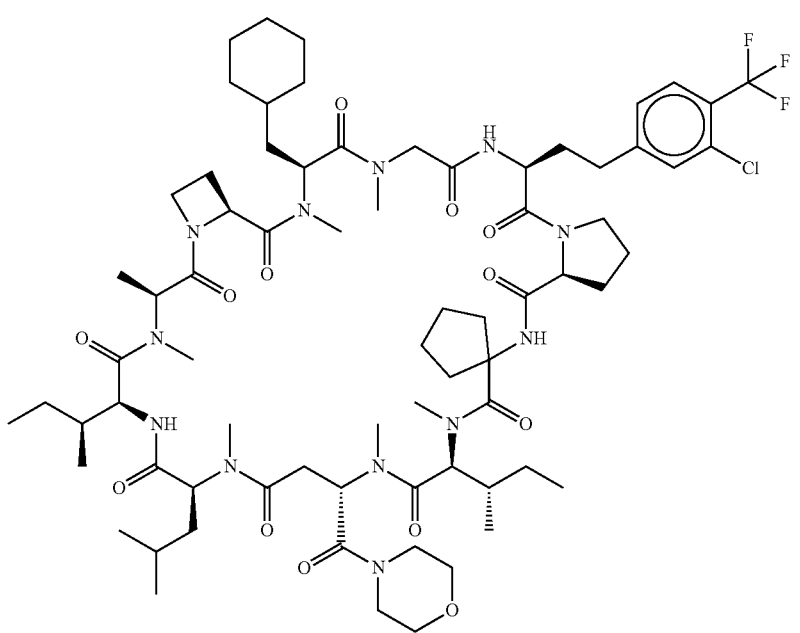 |
| 41 | 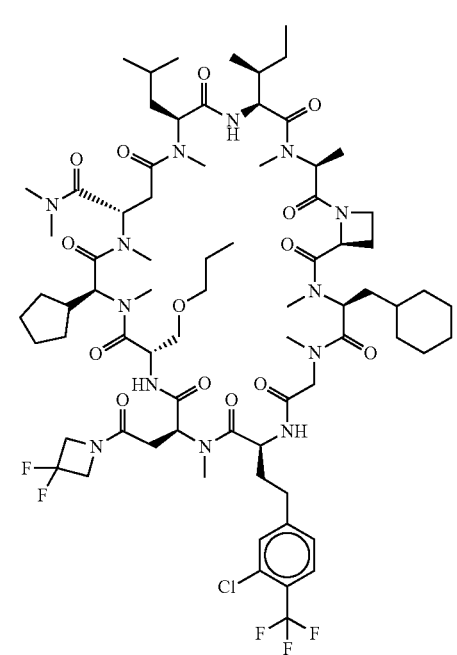 |

TABLE 24-continued
| Compound No. | Structural formula |
|---|---|
| 42 | 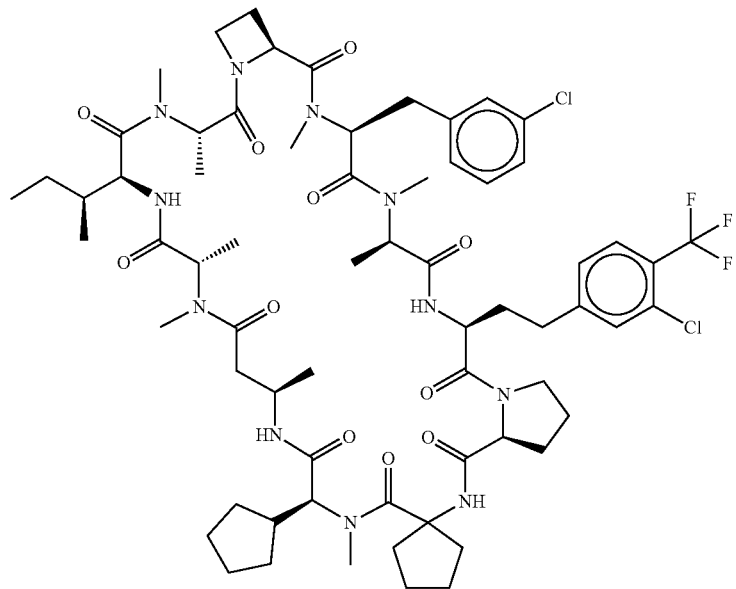 |
| 43 | 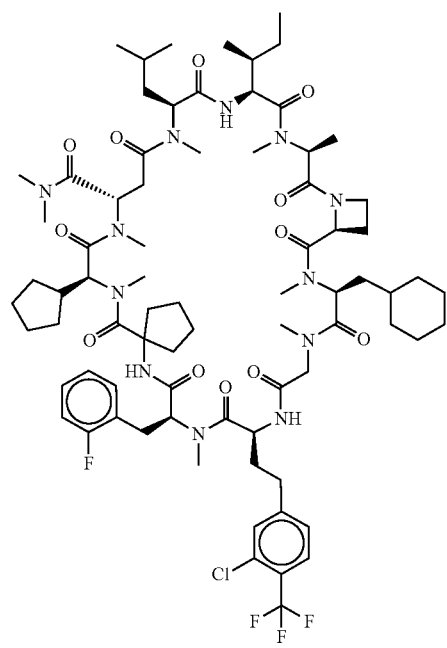 |

TABLE 24-continued
| Compound No. | Structural formula |
|---|---|
| 44 | 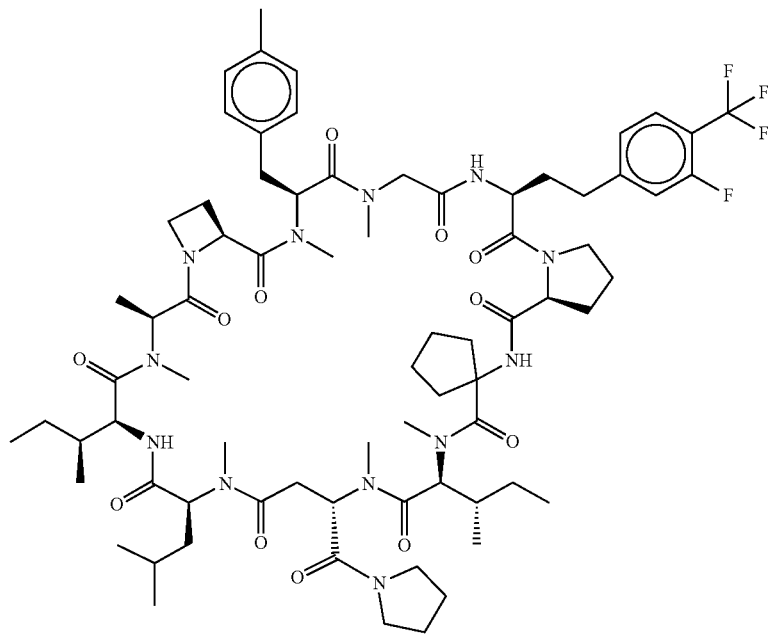 |
| 45 | 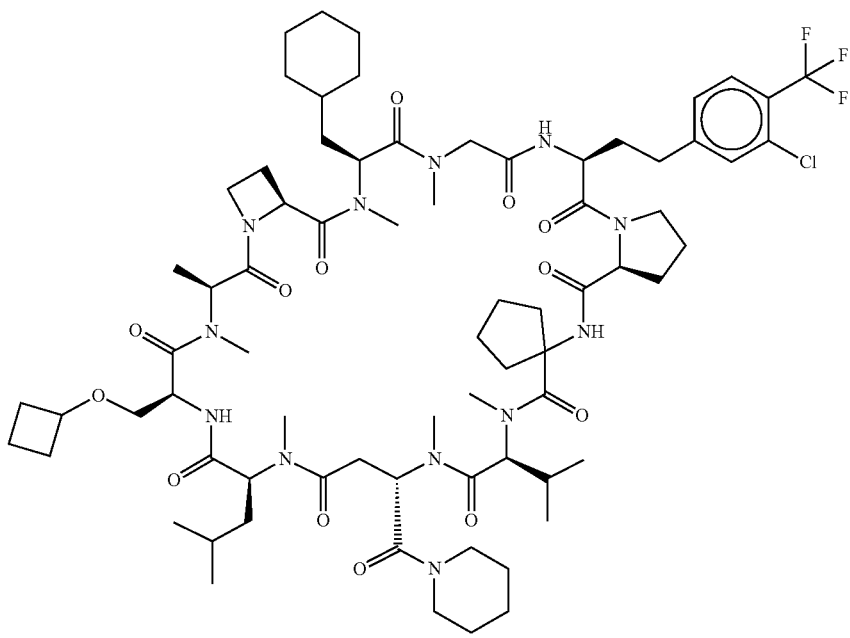 |

TABLE 24-continued
| Compound No. | Structural formula |
|---|---|
| 46 | 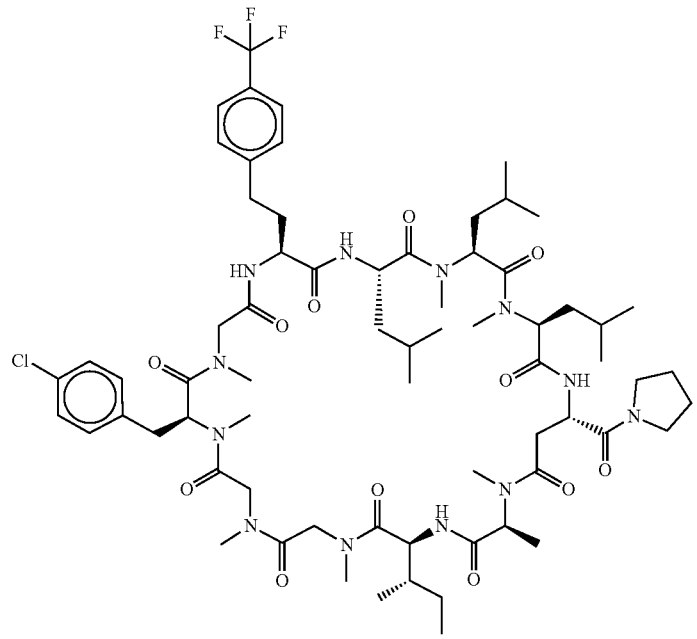 |
| 47 | 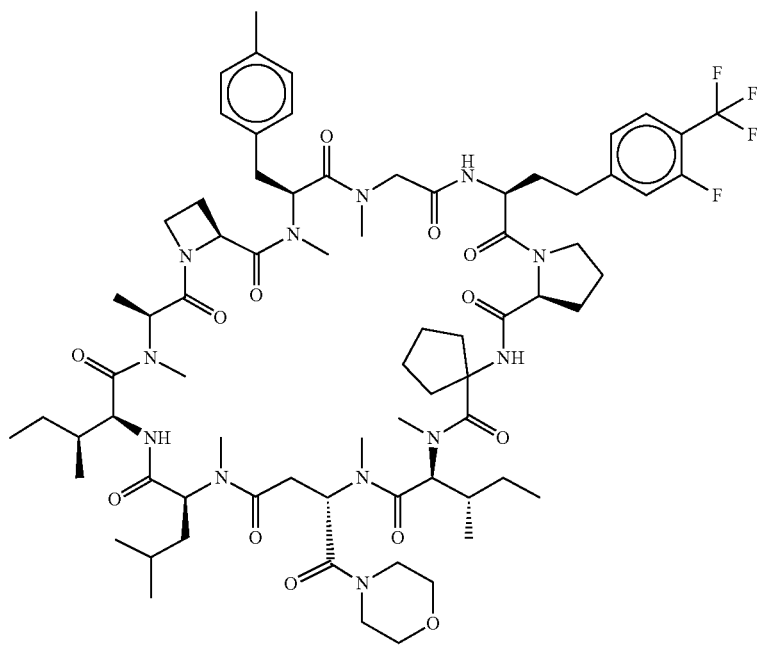 |

TABLE 24-continued
| Compound No. | Structural formula |
|---|---|
| 48 | 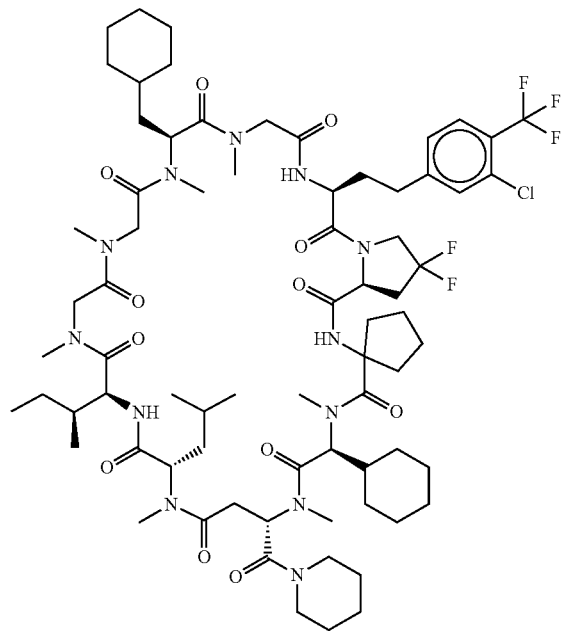 |
| 49 | 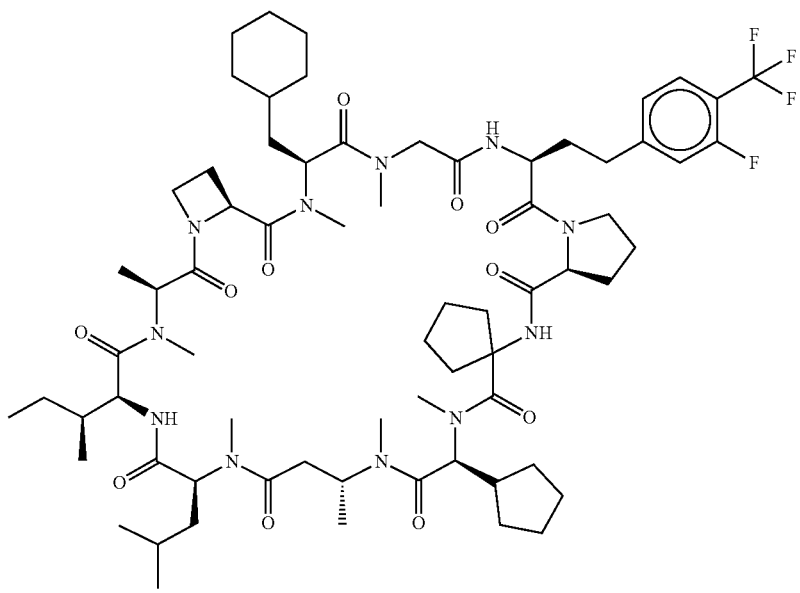 |

TABLE 24-continued
| Compound No. | Structural formula |
|---|---|
| 50 | 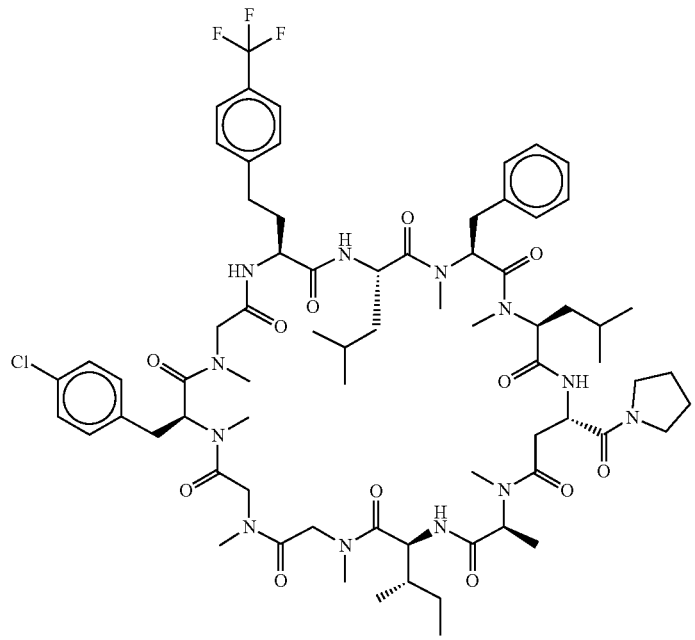 |
| 51 | 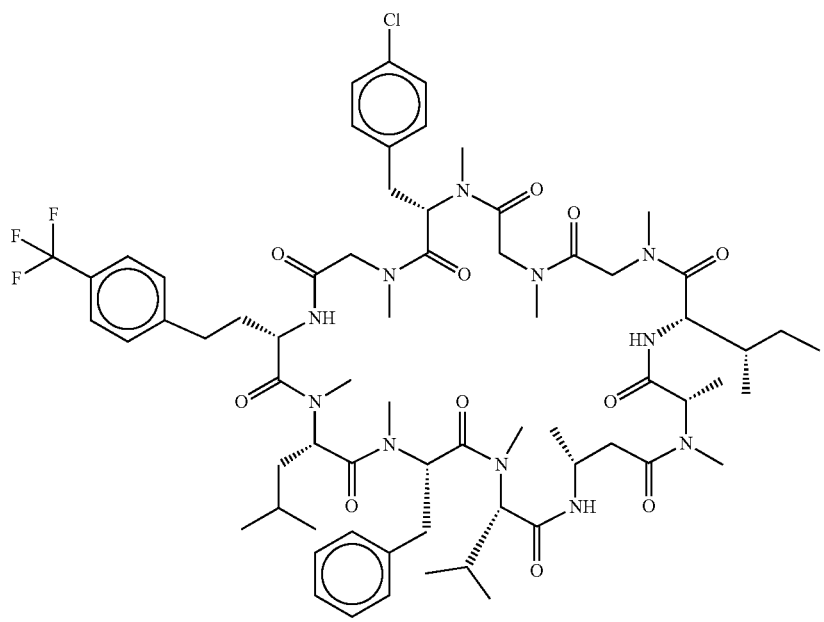 |

TABLE 24-continued
| Compound No. | Structural formula |
|---|---|
| 52 | 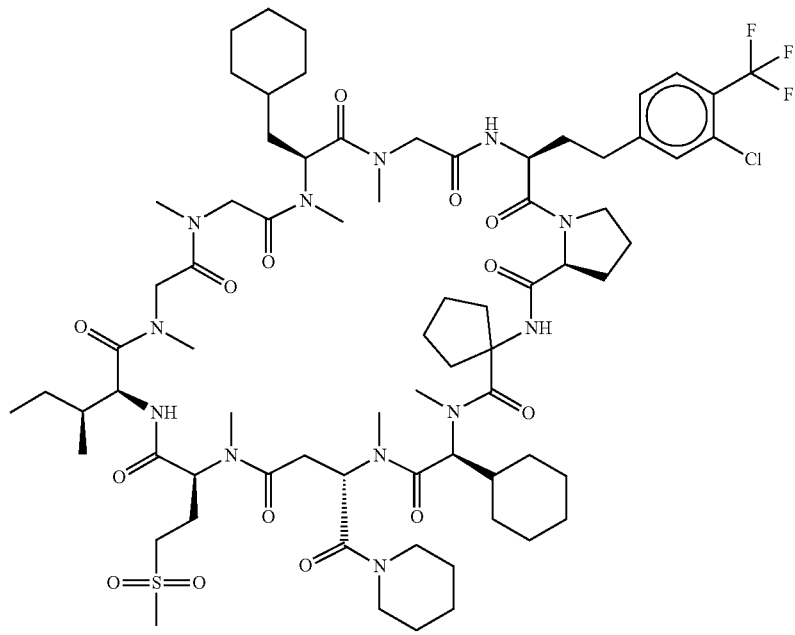 |
| 53 | 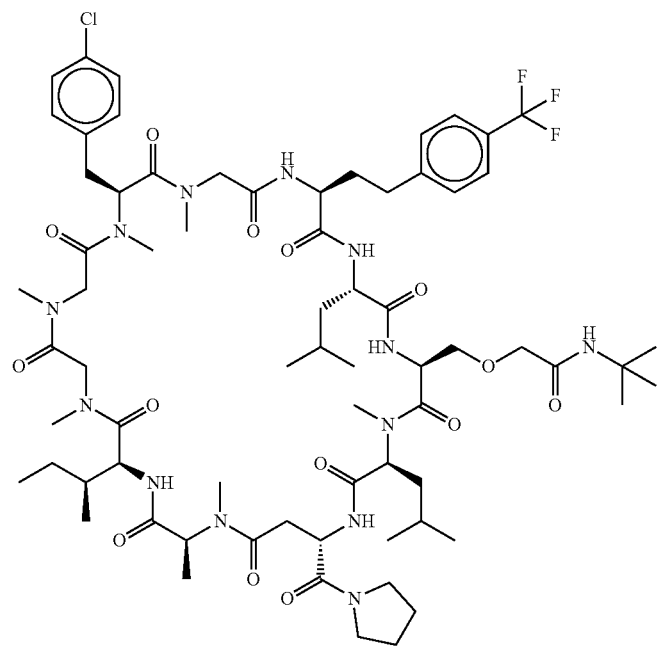 |

TABLE 24-continued
| Compound No. | Structural formula |
|---|---|
| 54 | 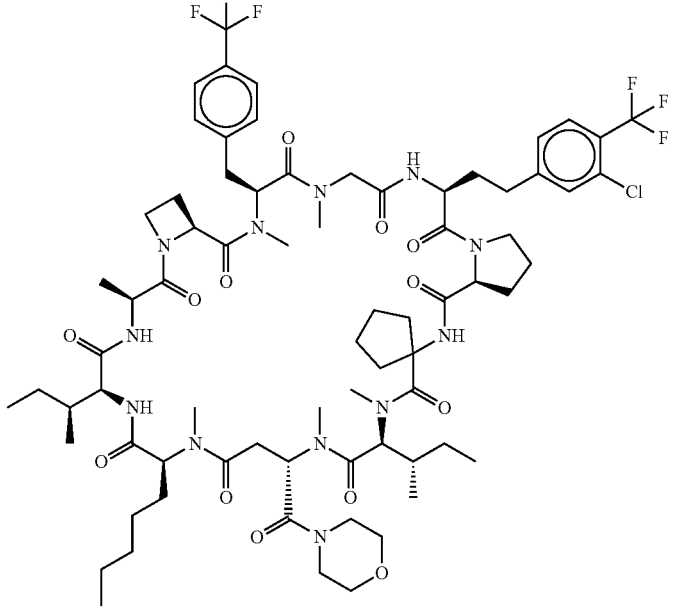 |
| 55 | 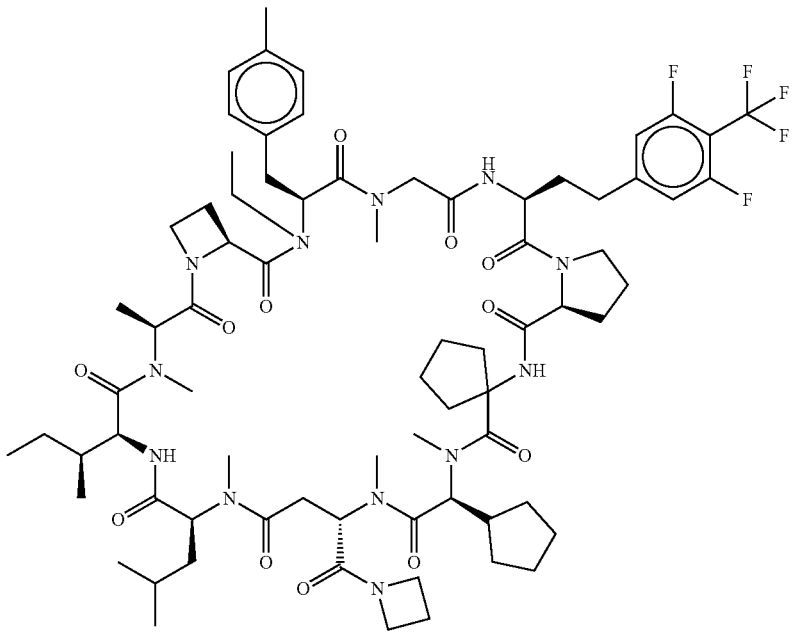 |

TABLE 24-continued
| Compound No. | Structural formula |
|---|---|
| 56 | 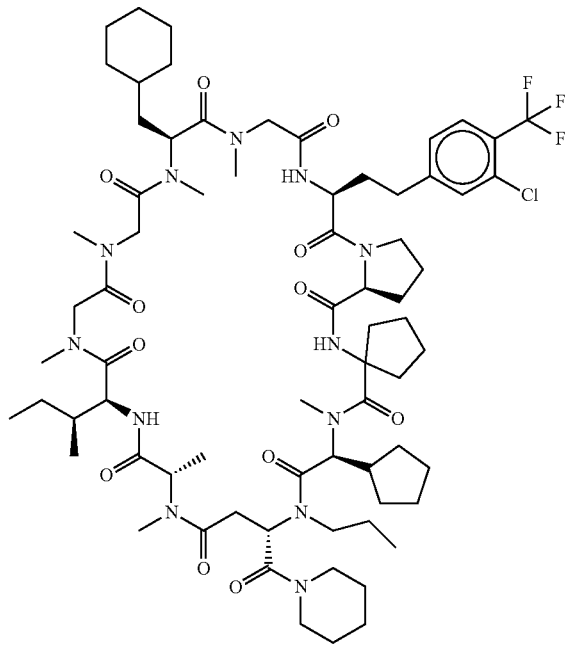 |
| 57 | 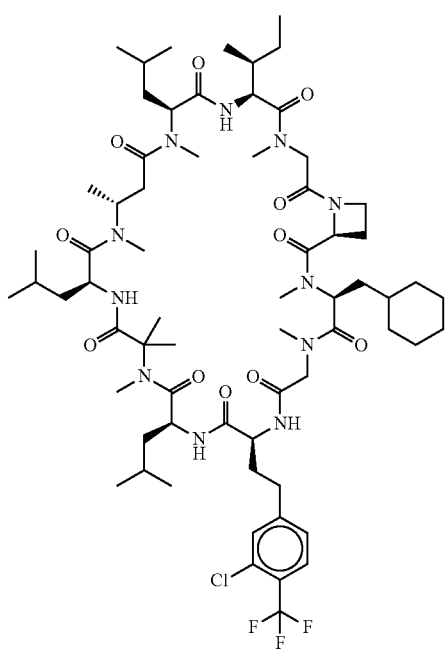 |

TABLE 24-continued
| Compound No. | Structural formula |
|---|---|
| 58 | 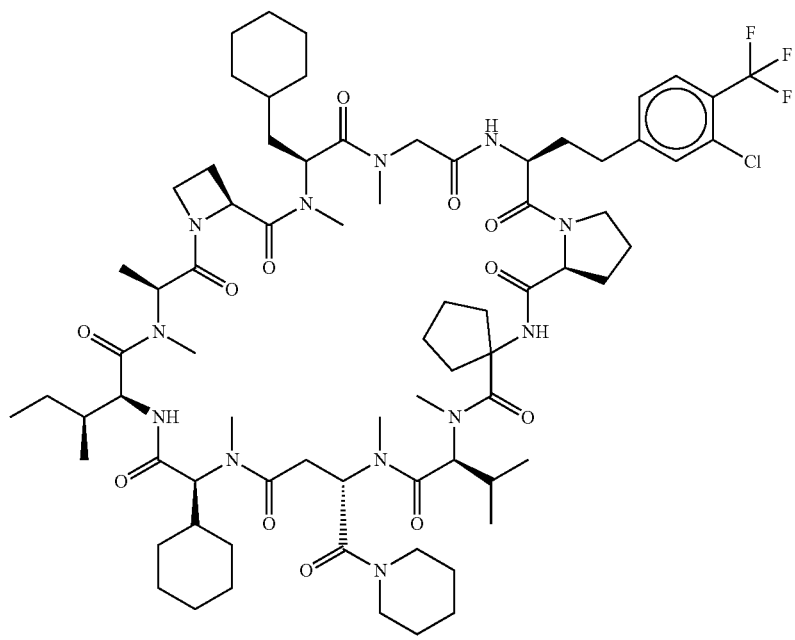 |
| 59 | 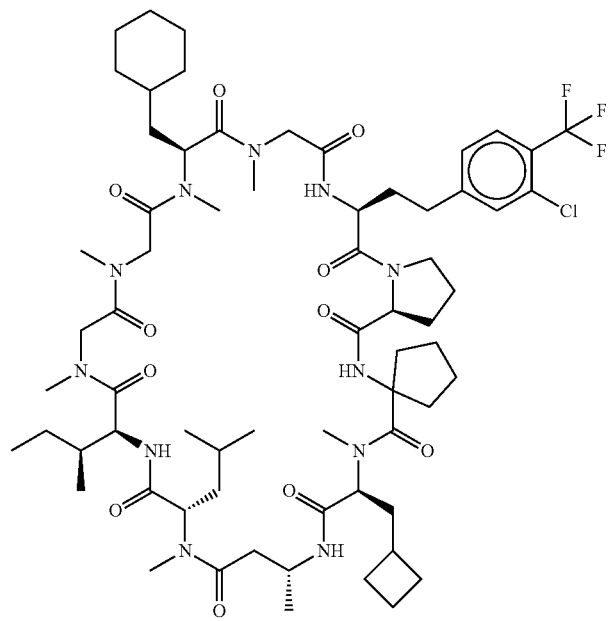 |

TABLE 24-continued
| Compound No. | Structural formula |
|---|---|
| 60 | 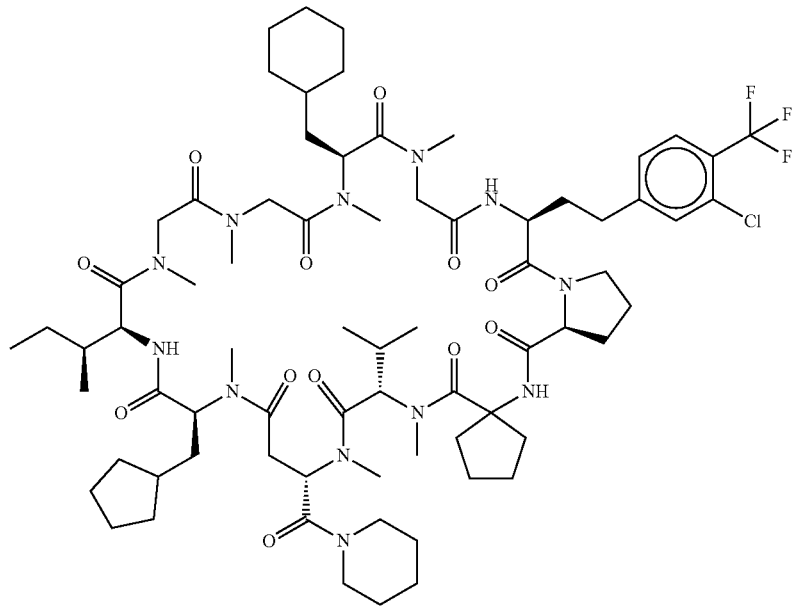 |
| 61 | 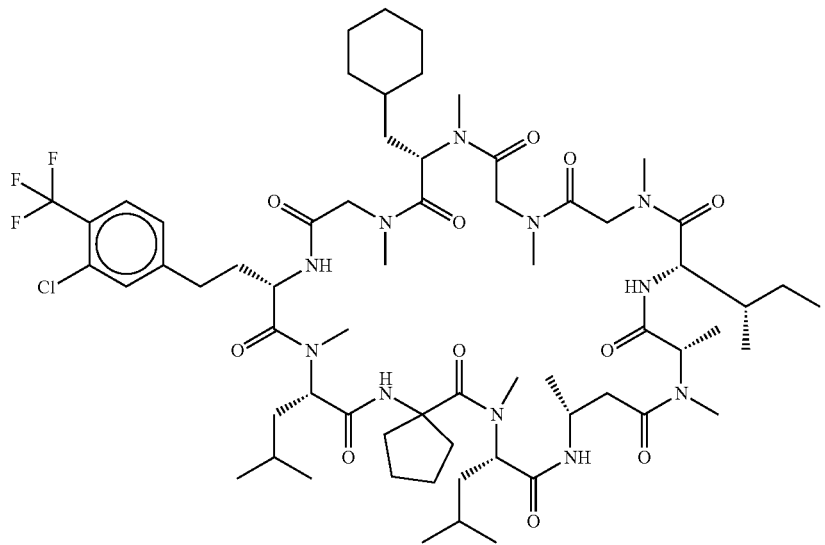 |

TABLE 24-continued
| Compound No. | Structural formula |
|---|---|
| 62 | 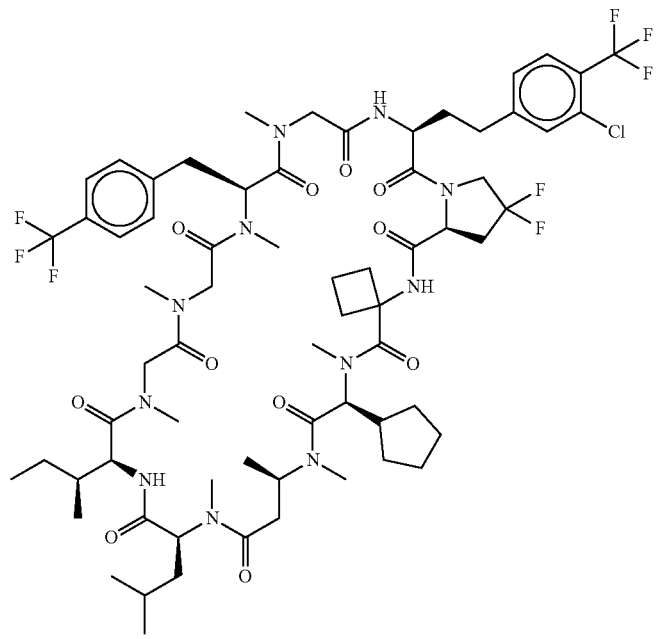 |
| 63 | 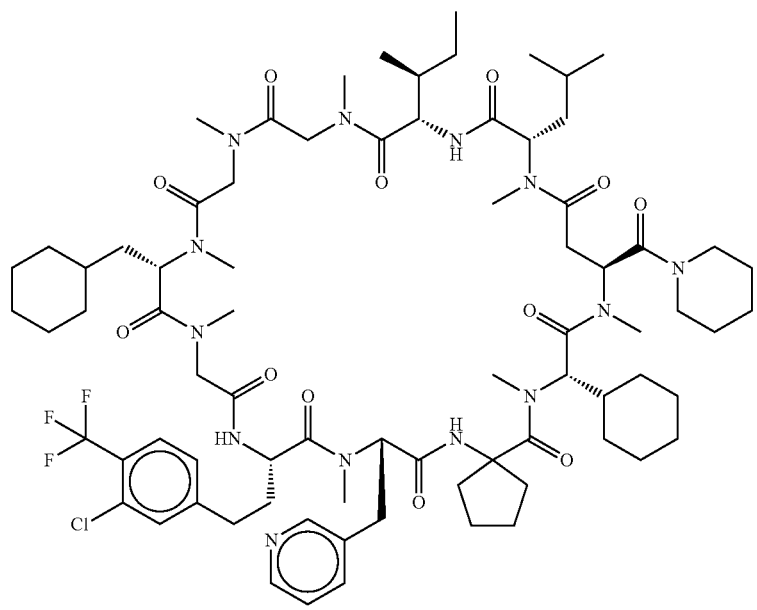 |

TABLE 24-continued
| Compound No. | Structural formula |
|---|---|
| 64 | 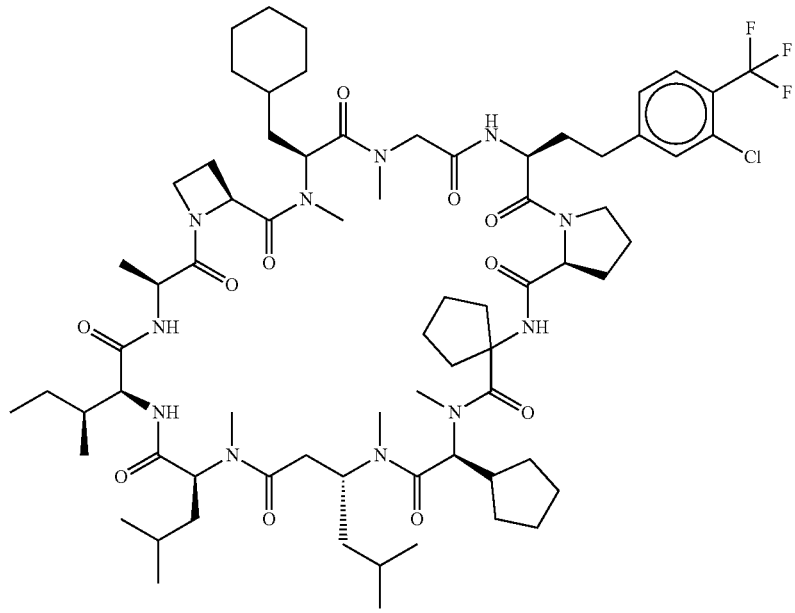 |
| 65 | 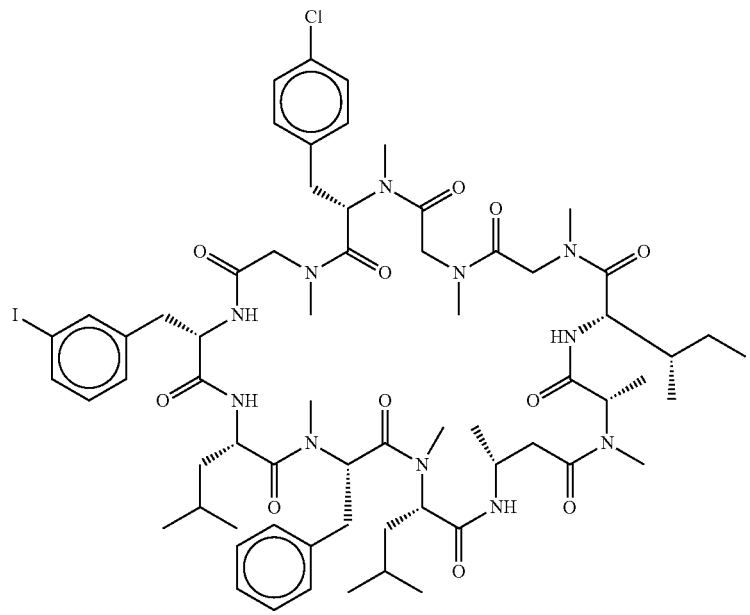 |

TABLE 24-continued
| Compound No. | Structural formula |
|---|---|
| 66 | 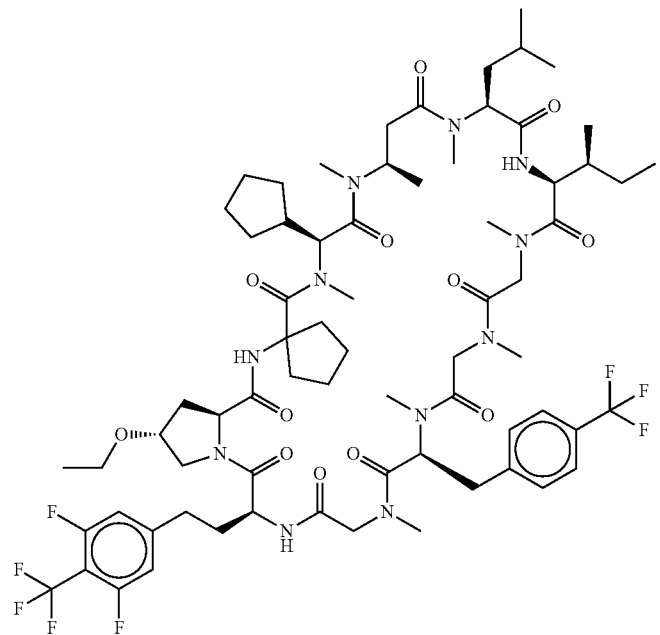 |
| 67 | 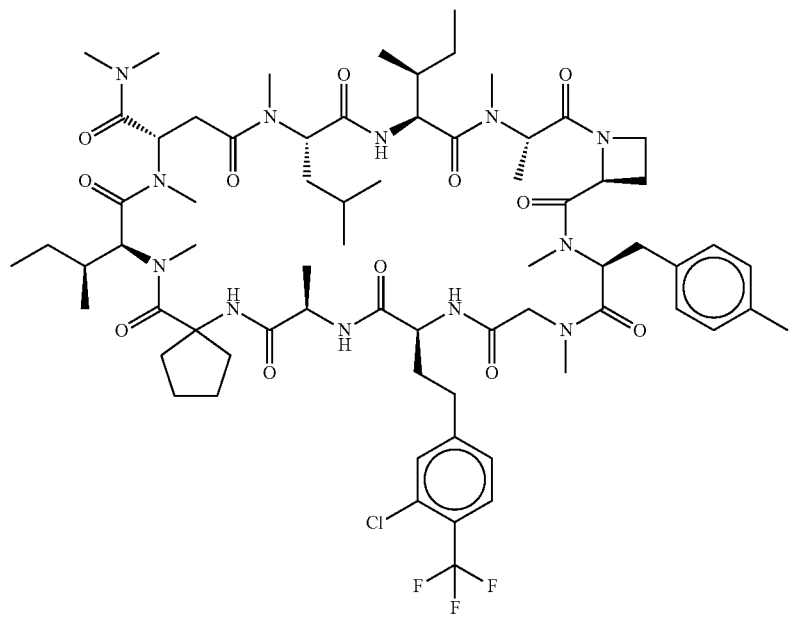 |

TABLE 24-continued
| Compound No. | Structural formula |
|---|---|
| 68 | 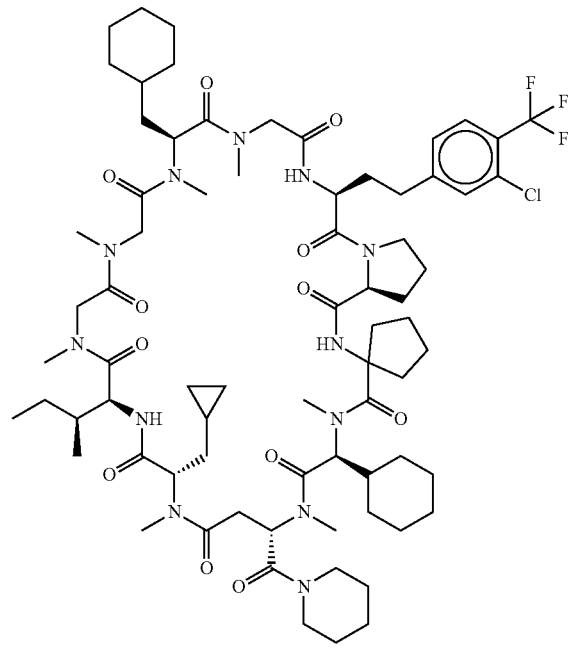 |
| 69 | 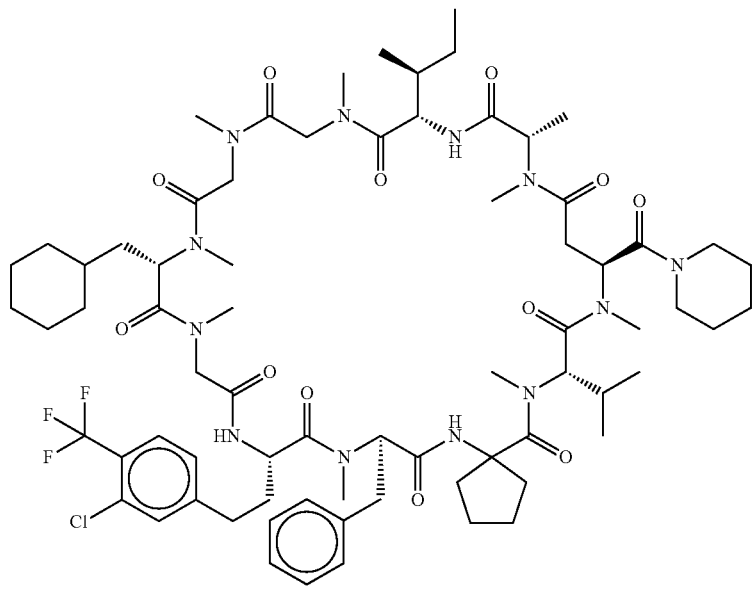 |

TABLE 24-continued
| Compound No. | Structural formula |
|---|---|
| 70 | 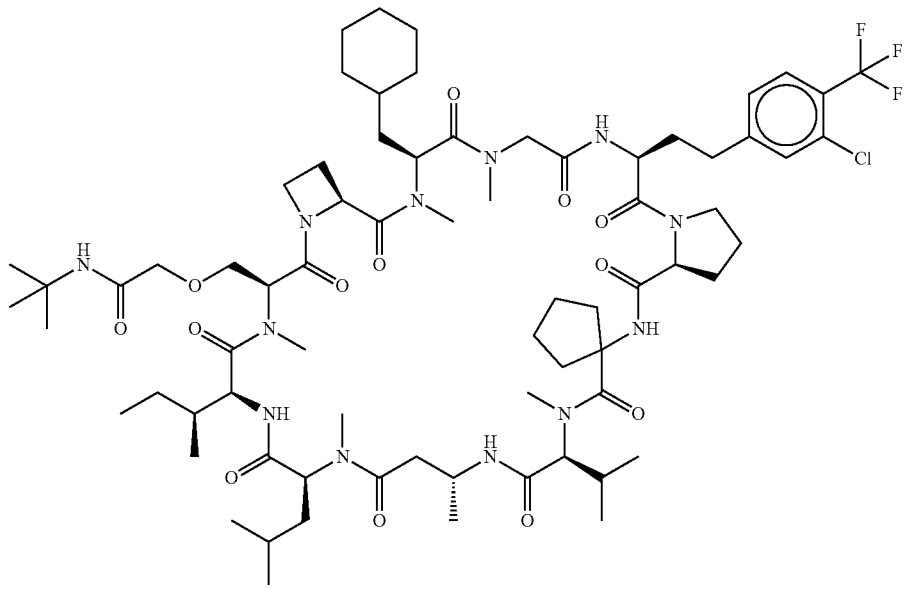 |
| 71 | 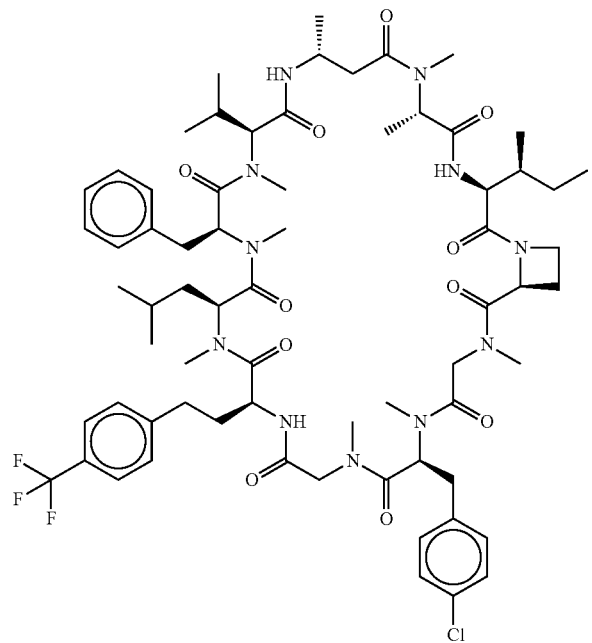 |

TABLE 24-continued
| Compound No. | Structural formula |
|---|---|
| 72 | 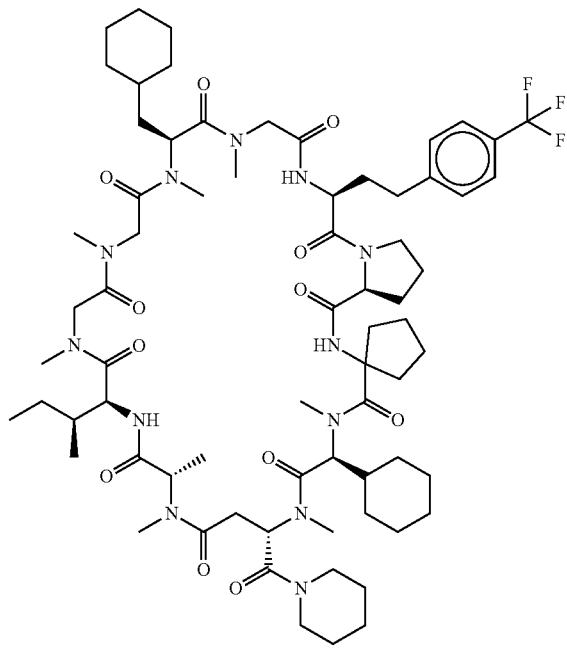 |
| 73 | 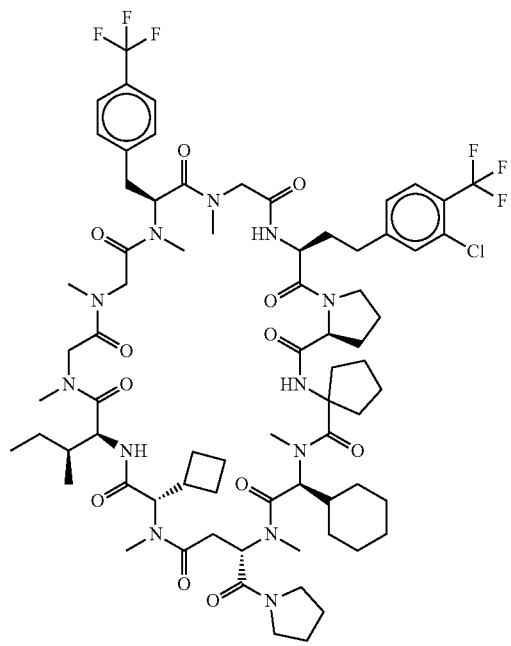 |

TABLE 24-continued
| Compound No. | Structural formula |
|---|---|
| 74 | 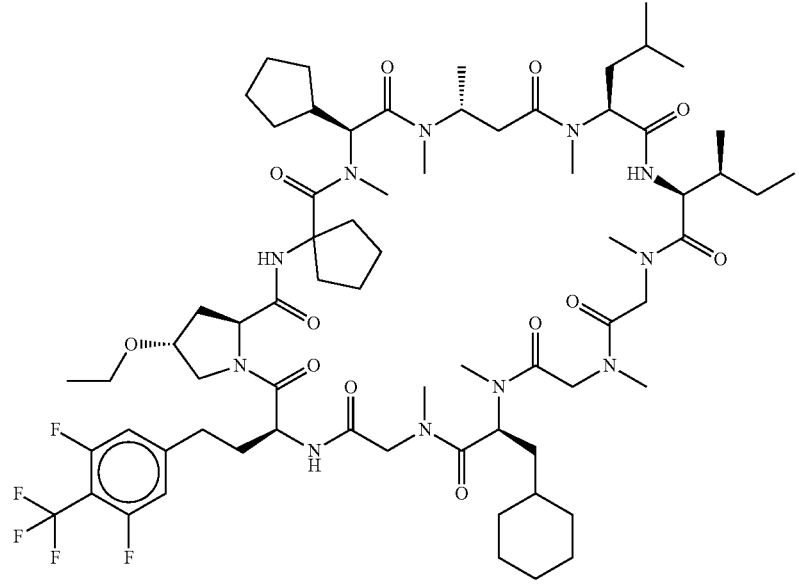 |
| 75 | 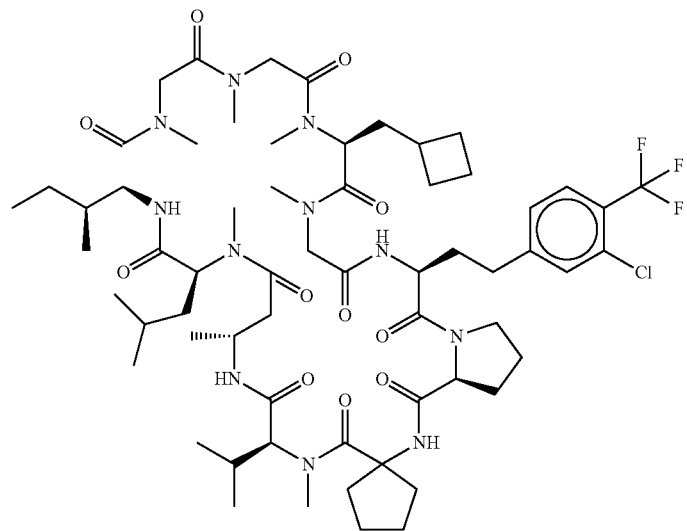 |

TABLE 24-continued
| Compound No. | Structural formula |
|---|---|
| 76 | 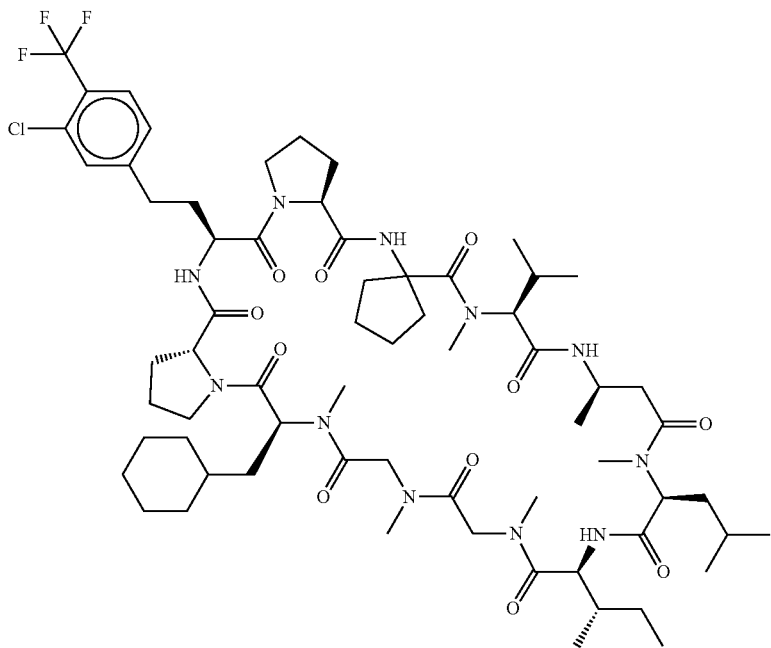 |
| 77 | 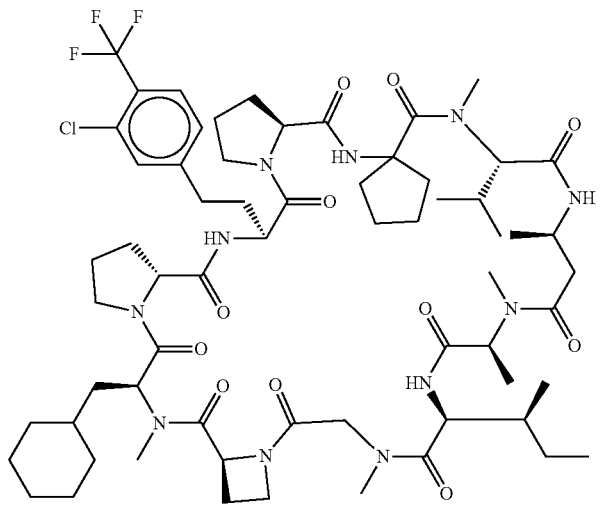 |

TABLE 24-continued
| Compound No. | Structural formula |
|---|---|
| 78 | 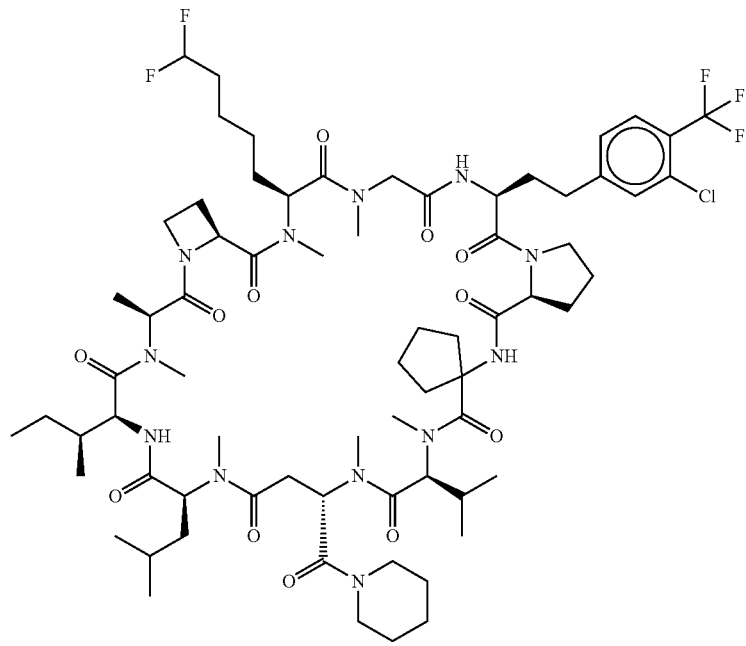 |
| 79 | 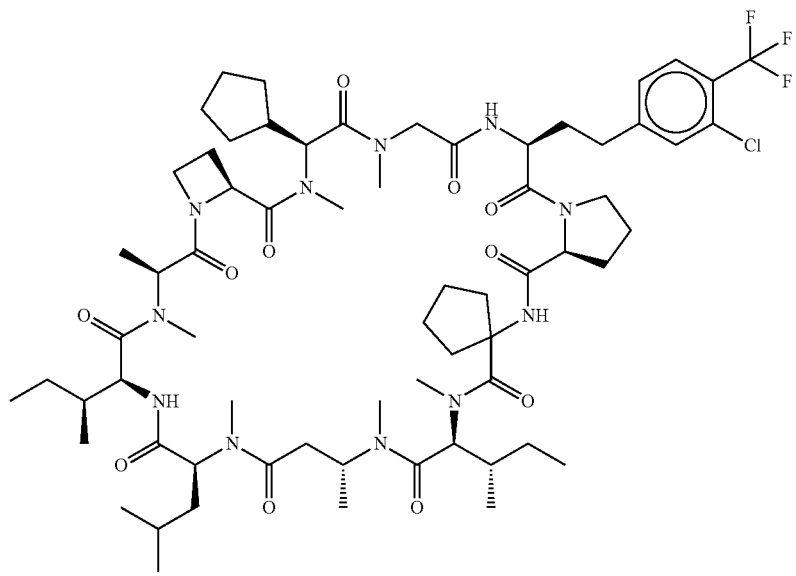 |

TABLE 24-continued
| Compound No. | Structural formula |
|---|---|
| 80 | 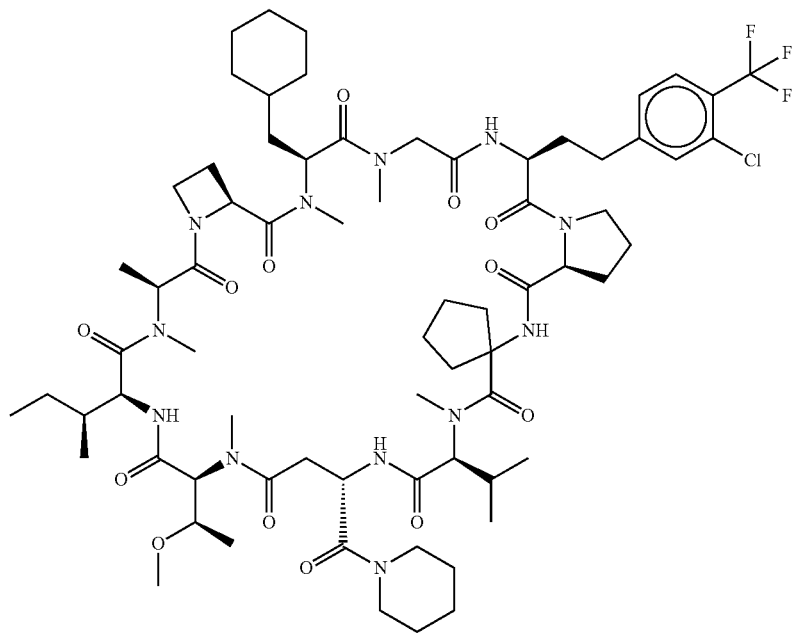 |
| 81 | 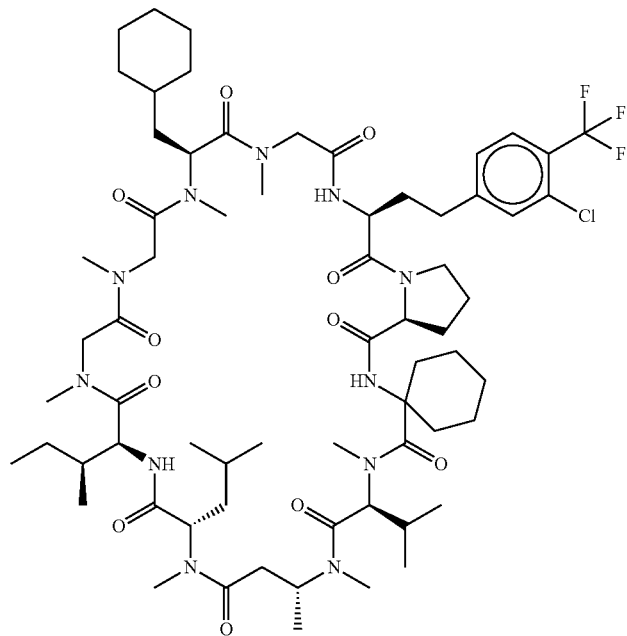 |

TABLE 24-continued
| Compound No. | Structural formula |
|---|---|
| 82 | 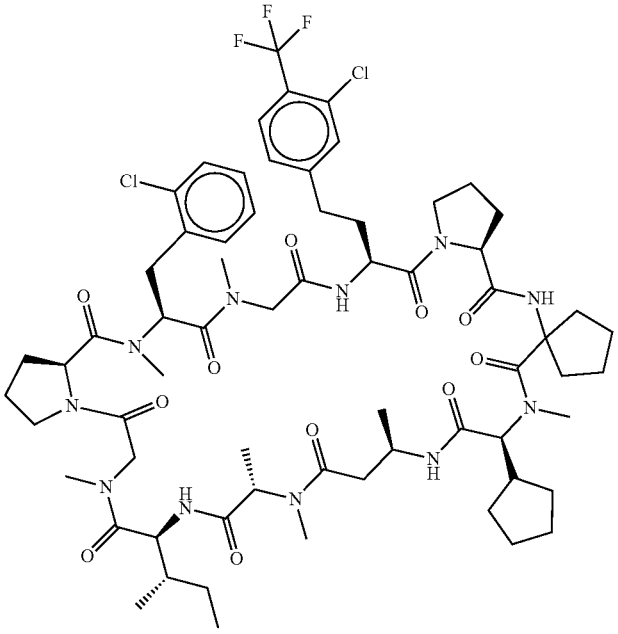 |
| 83 | 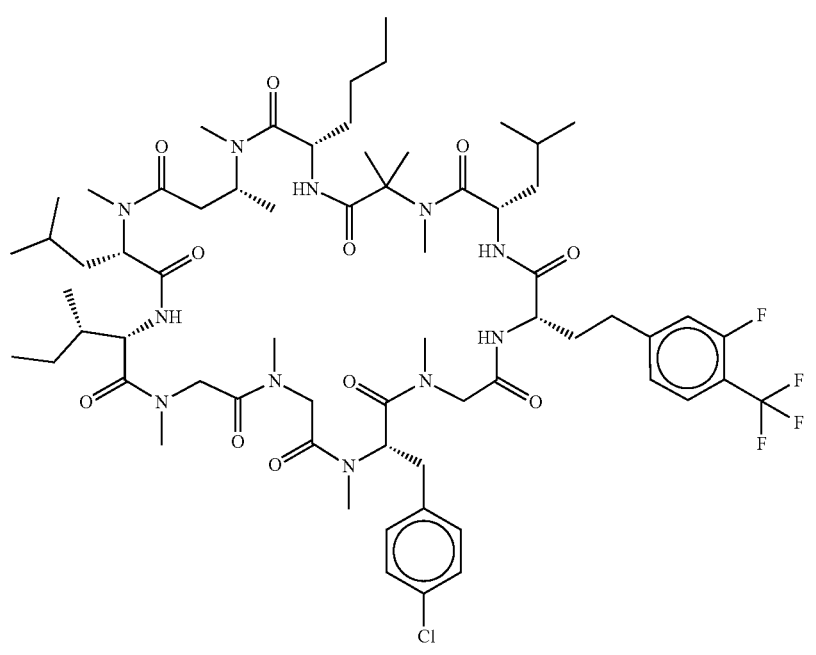 |

TABLE 24-continued
| Compound No. | Structural formula |
|---|---|
| 84 | 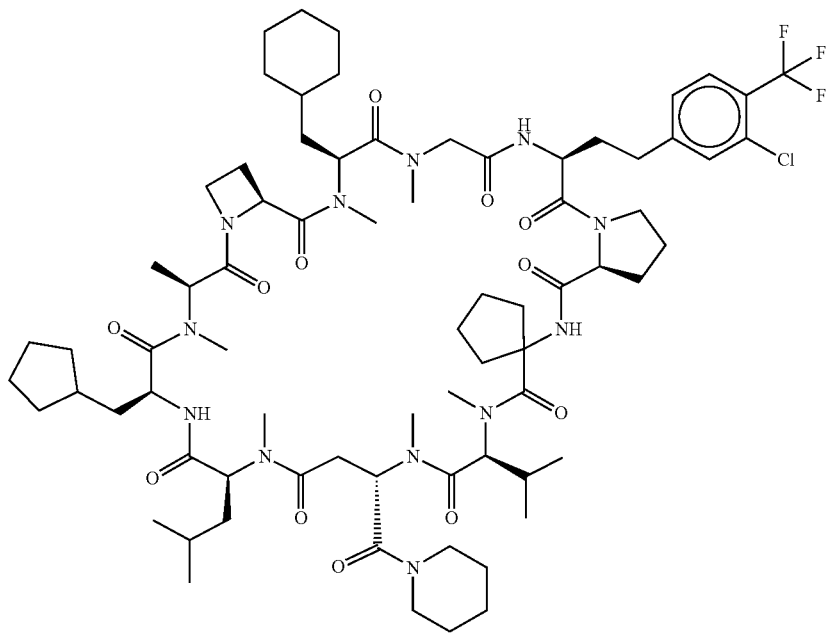 |
| 85 | 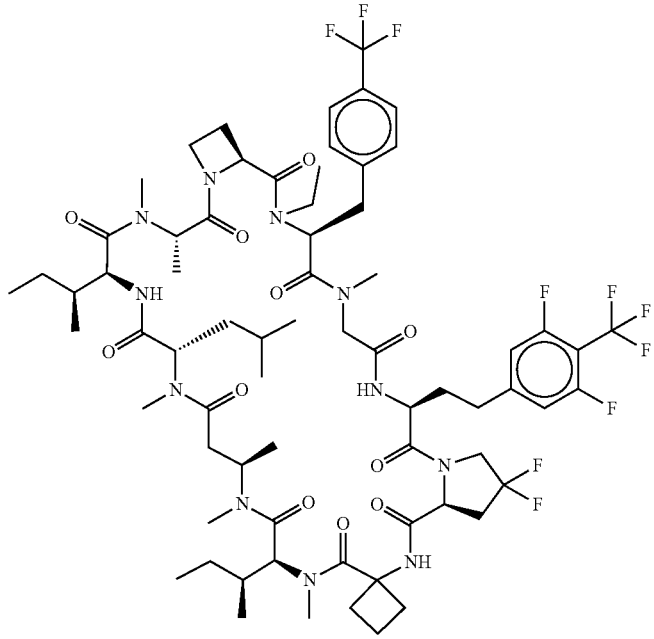 |

TABLE 24-continued
| Compound No. | Structural formula |
|---|---|
| 86 | 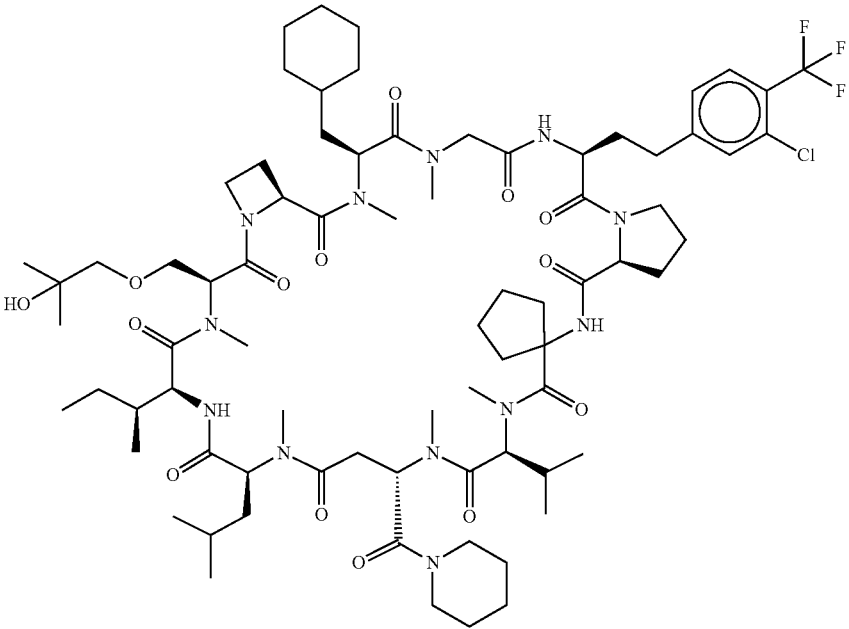 |
| 87 | 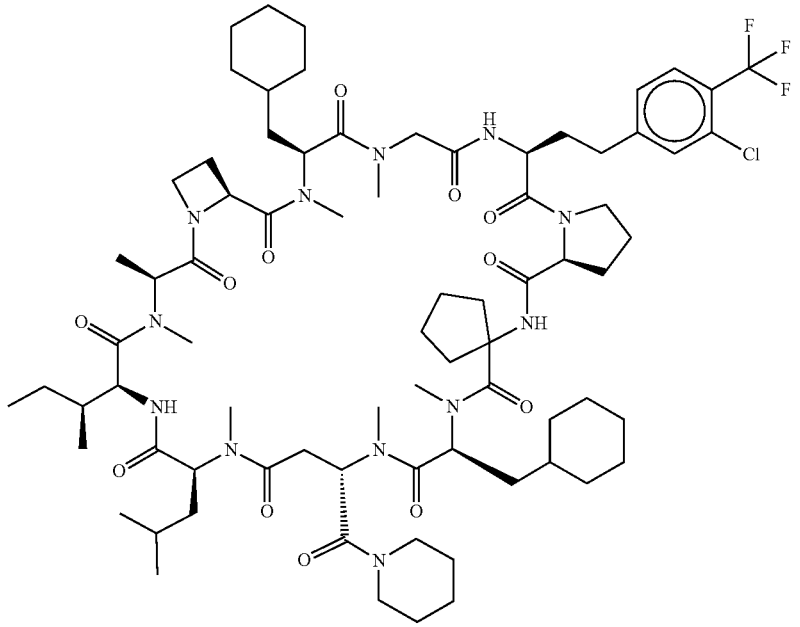 |

TABLE 24-continued
| Compound No. | Structural formula |
|---|---|
| 88 | 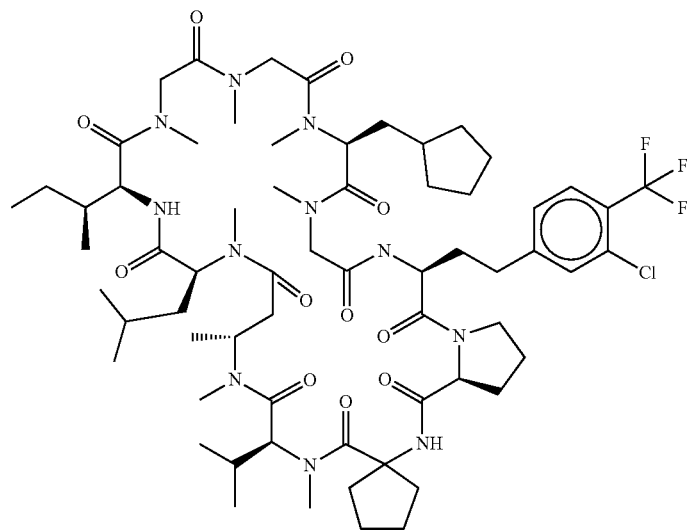 |
| 89 | 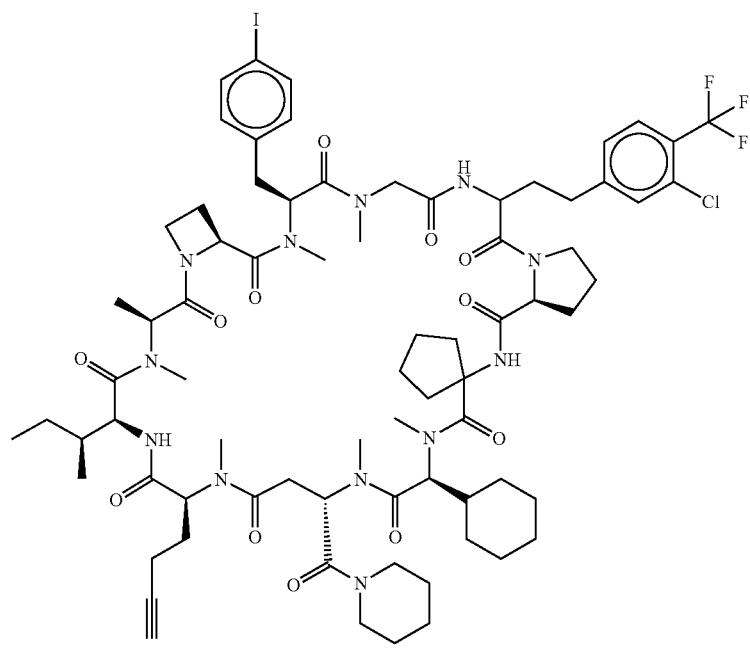 |

TABLE 24-continued
| Compound No. | Structural formula |
|---|---|
| 90 | 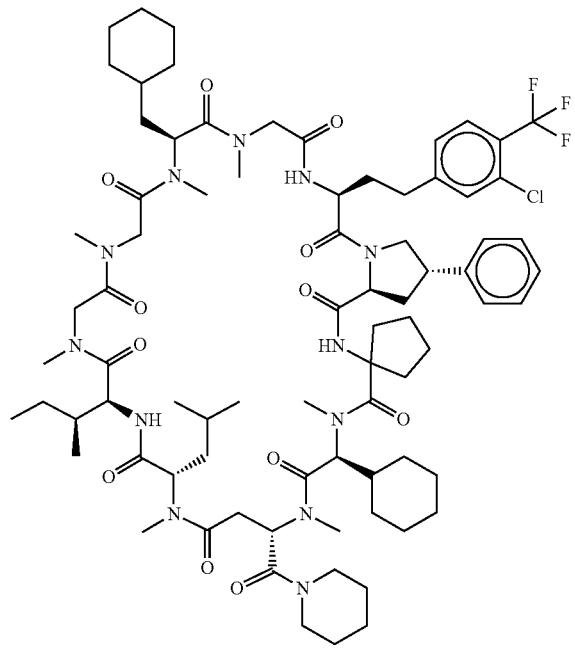 |
| 91 | 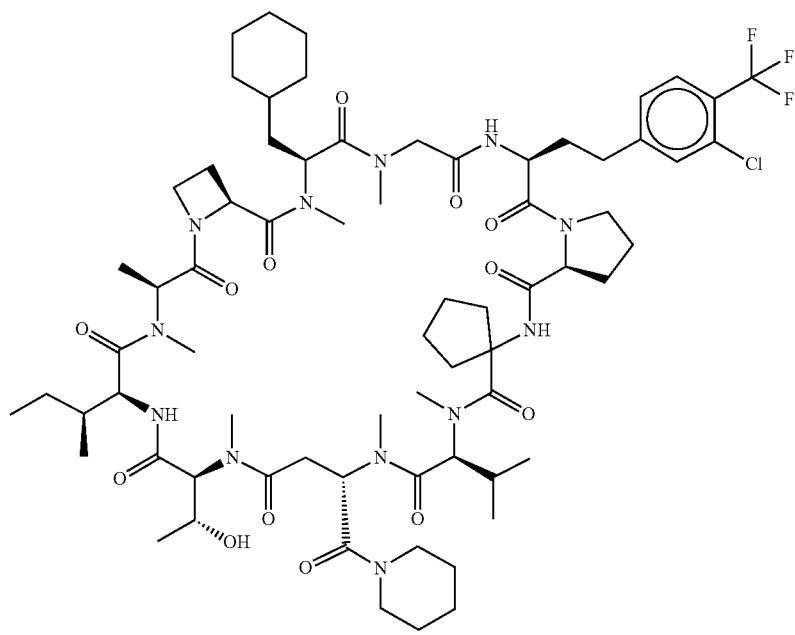 |

TABLE 24-continued
| Compound No. | Structural formula |
|---|---|
| 92 | 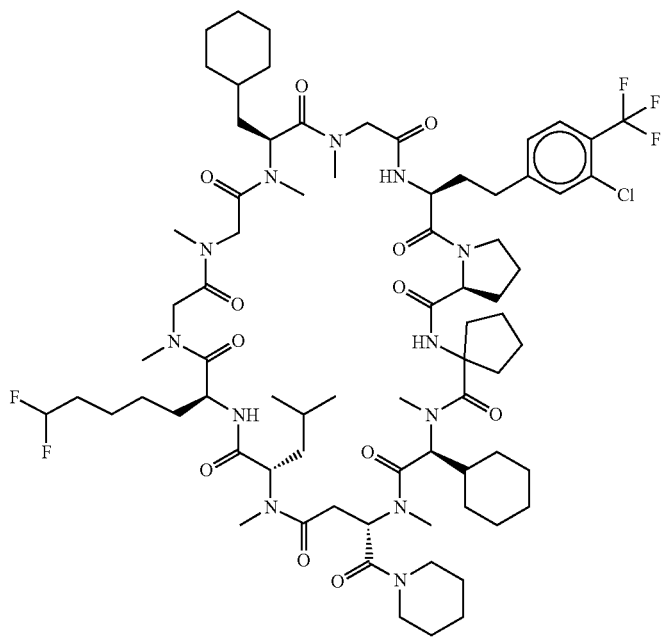 |
| 93 | 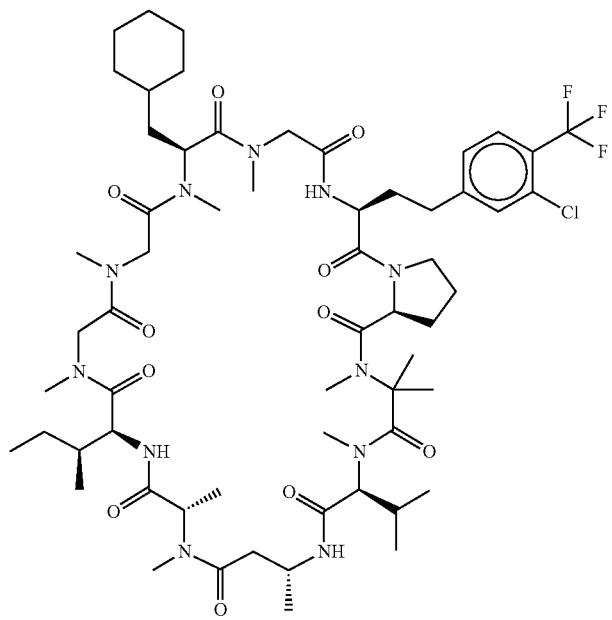 |

TABLE 24-continued
| Compound No. | Structural formula |
|---|---|
| 94 | 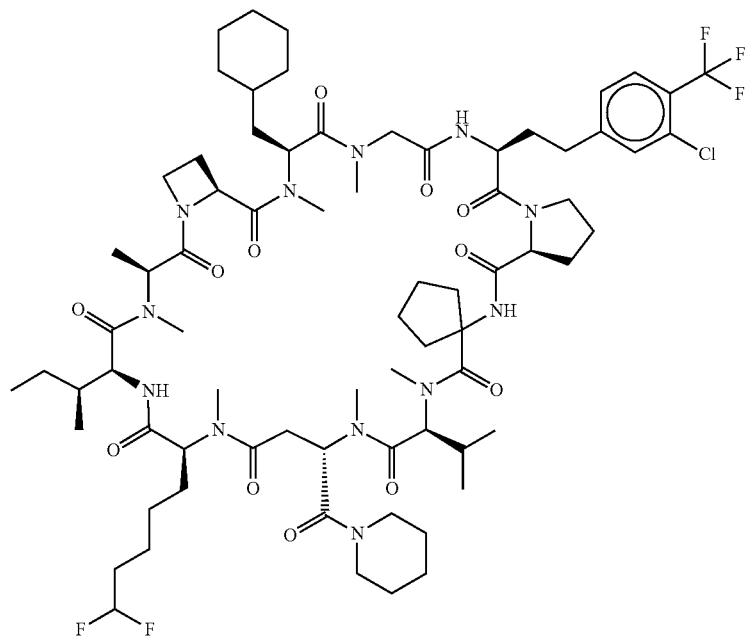 |
| 95 | 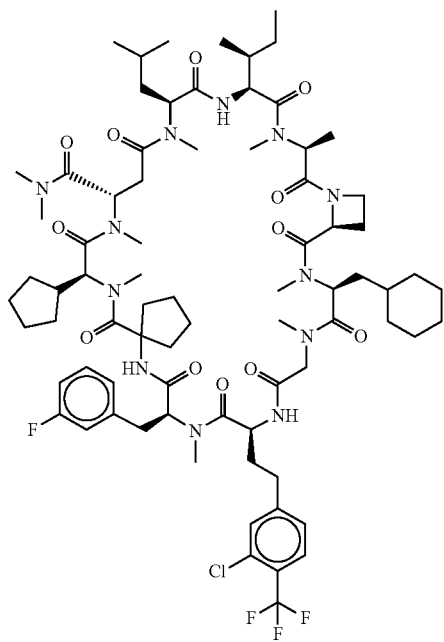 |

TABLE 24-continued
| Compound No. | Structural formula |
|---|---|
| 96 | 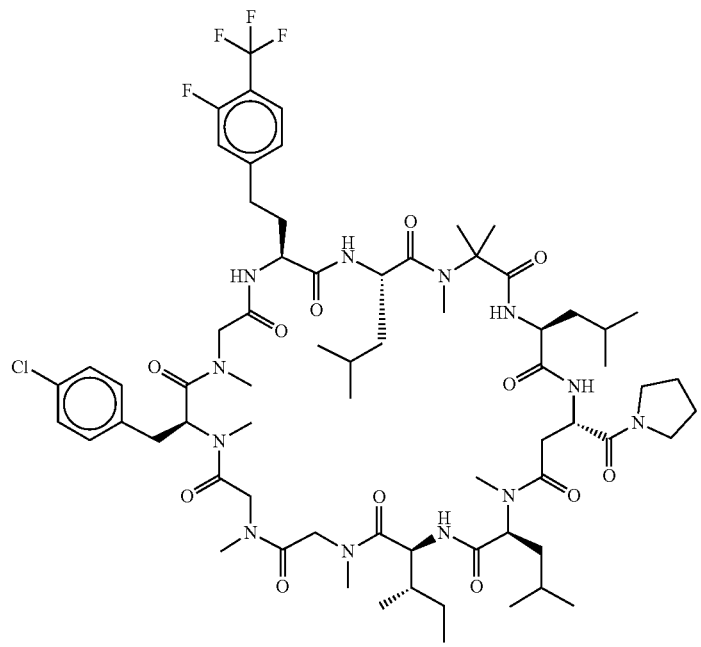 |
| 97 | 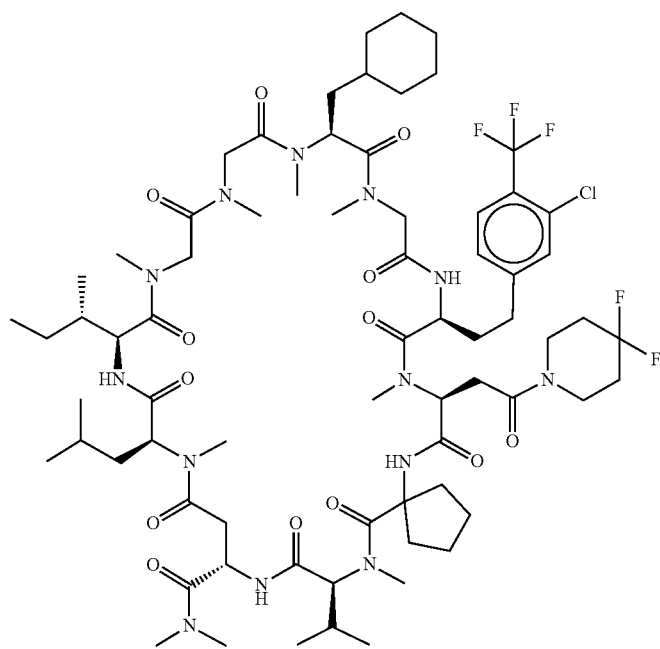 |

TABLE 24-continued
| Compound No. | Structural formula |
|---|---|
| 98 | 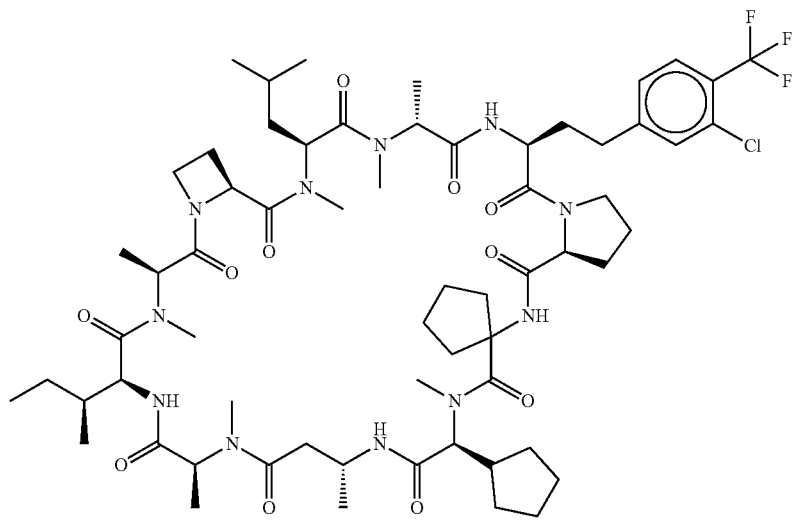 |
| 99 | 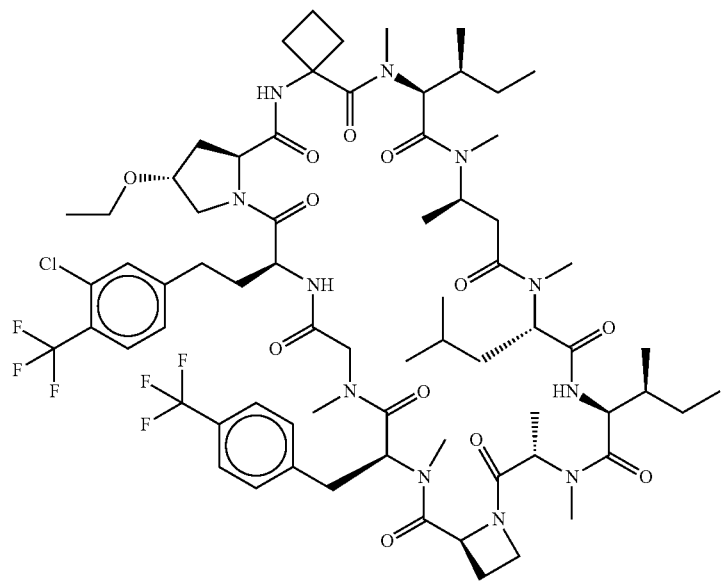 |

TABLE 24-continued
| Compound No. | Structural formula |
|---|---|
| 100 | 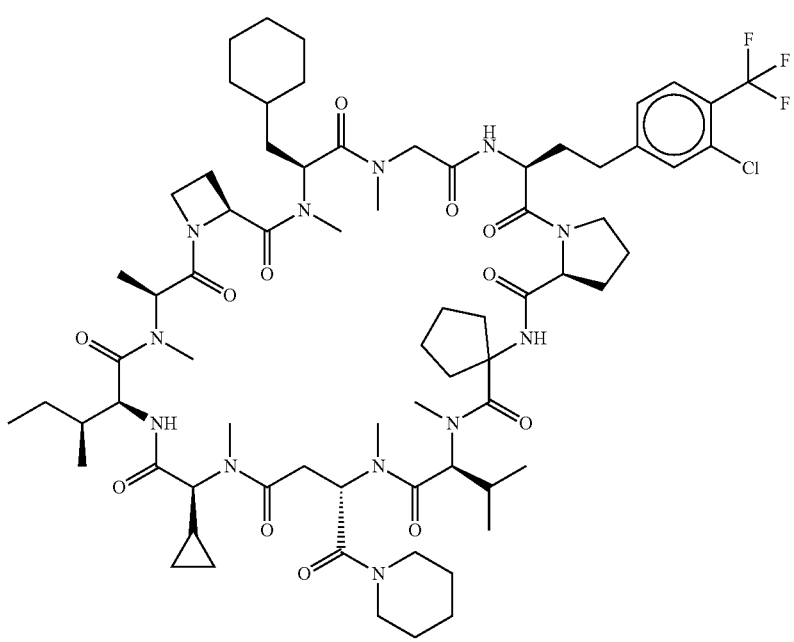 |
| 101 | 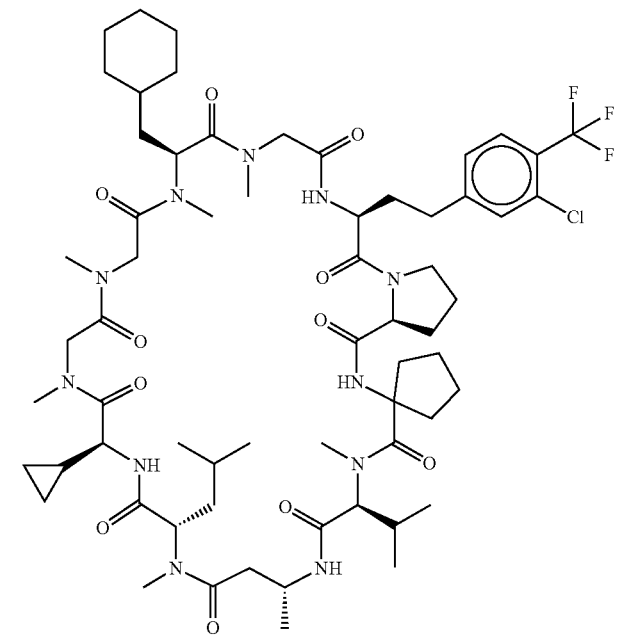 |

TABLE 24-continued
| Compound No. | Structural formula |
|---|---|
| 102 | 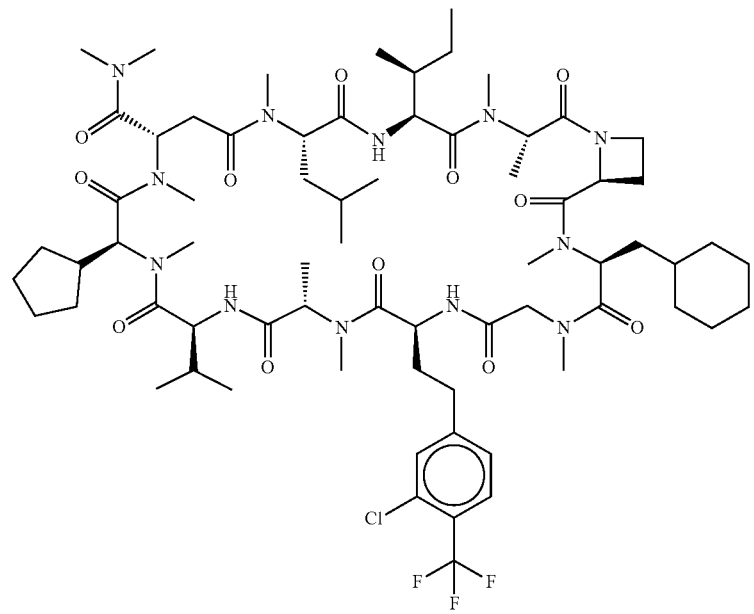 |
| 103 | 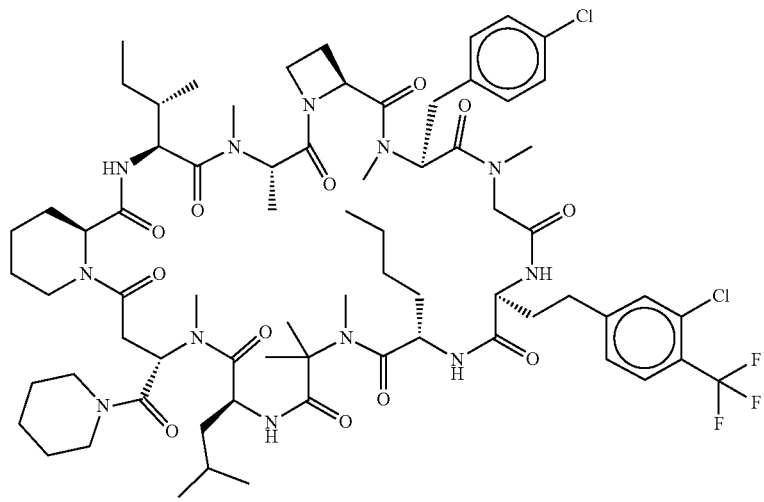 |

TABLE 24-continued
| Compound No. | Structural formula |
|---|---|
| 104 | 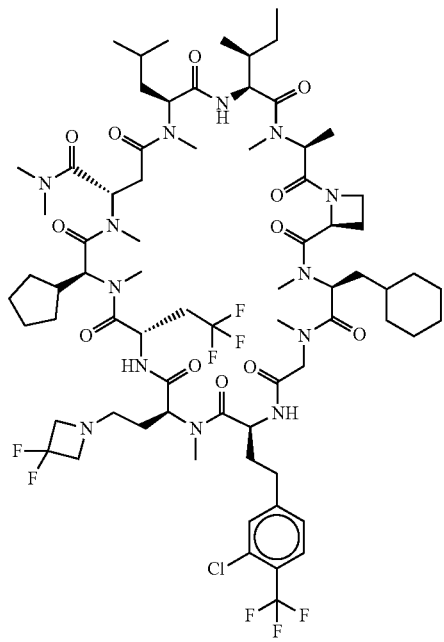 |
| 105 | 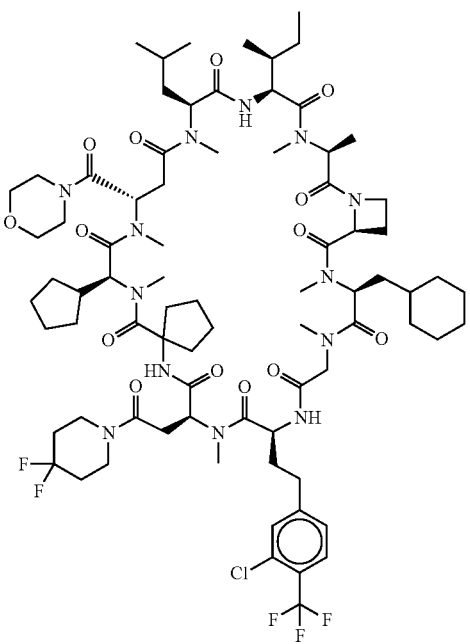 |

TABLE 24-continued
| Compound No. | Structural formula |
|---|---|
| 106 | 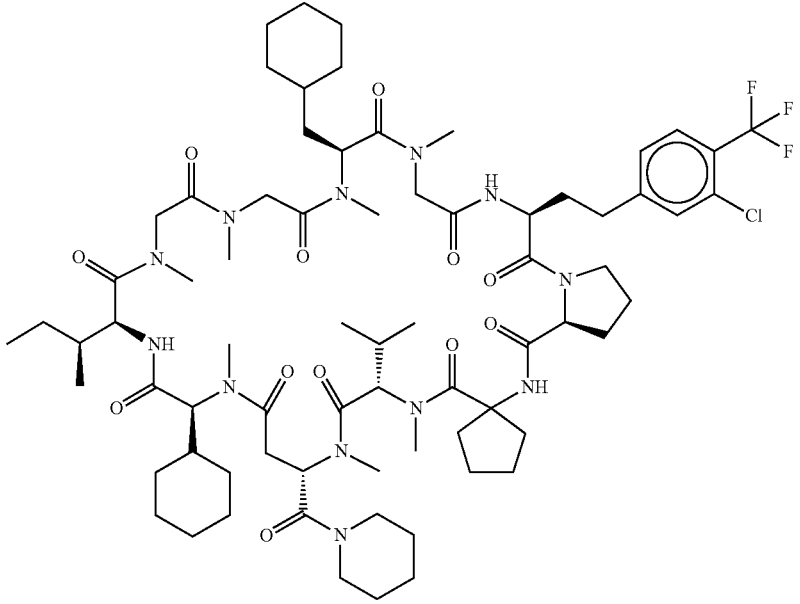 |
| 107 | 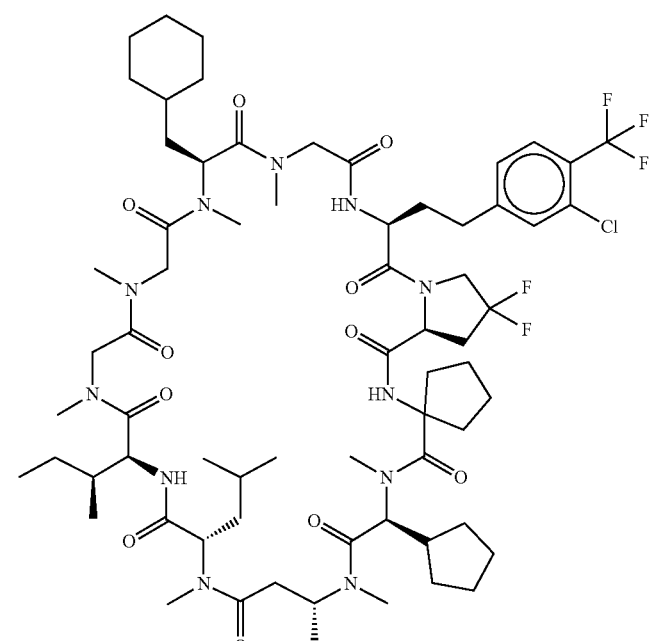 |

TABLE 24-continued
| Compound No. | Structural formula |
|---|---|
| 108 | 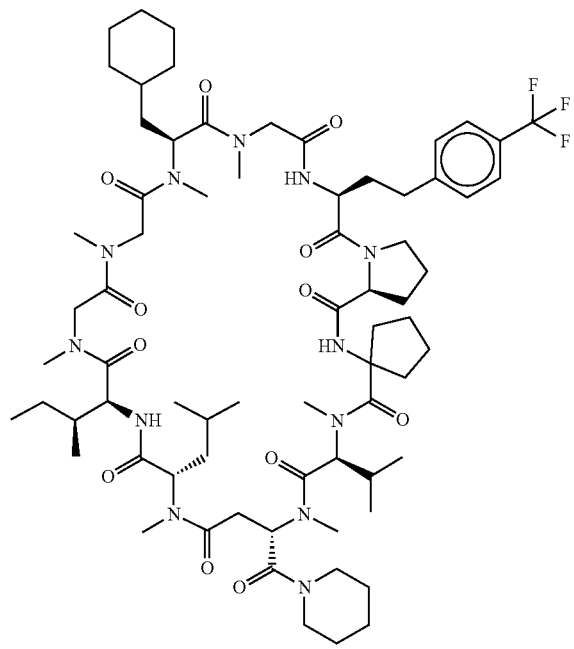 |
| 109 | 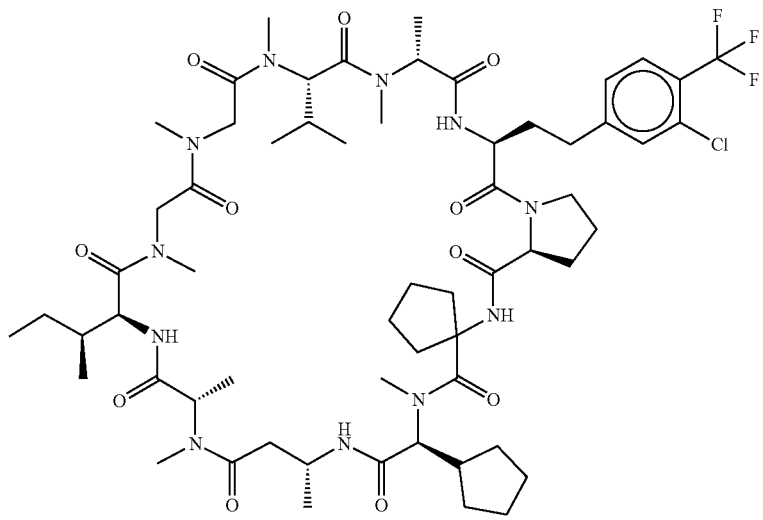 |

TABLE 24-continued
| Compound No. | Structural formula |
|---|---|
| 110 | 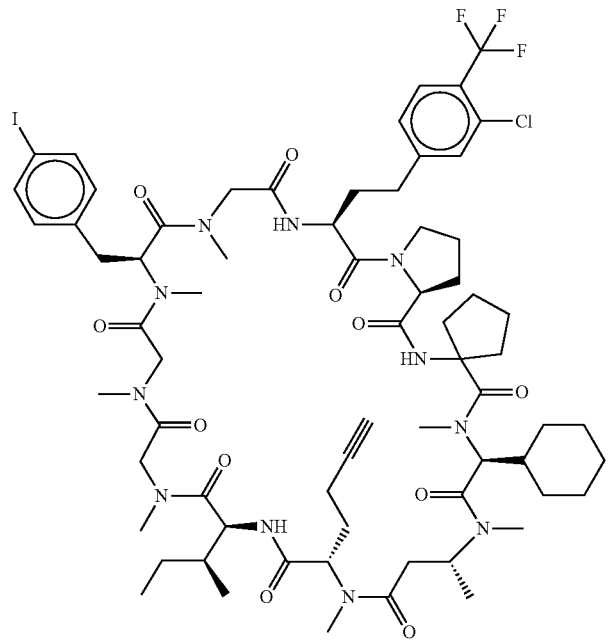 |
| 111 | 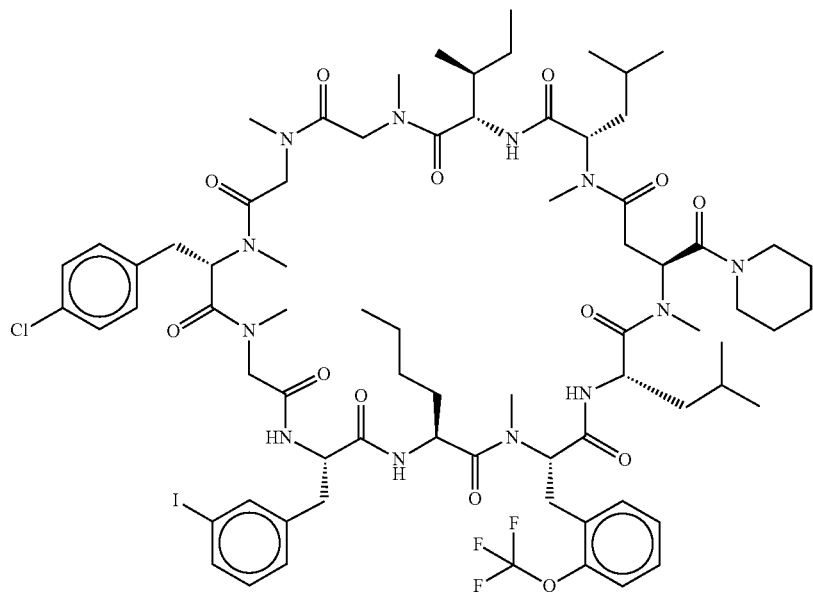 |

TABLE 24-continued
| Compound No. | Structural formula |
|---|---|
| 112 | 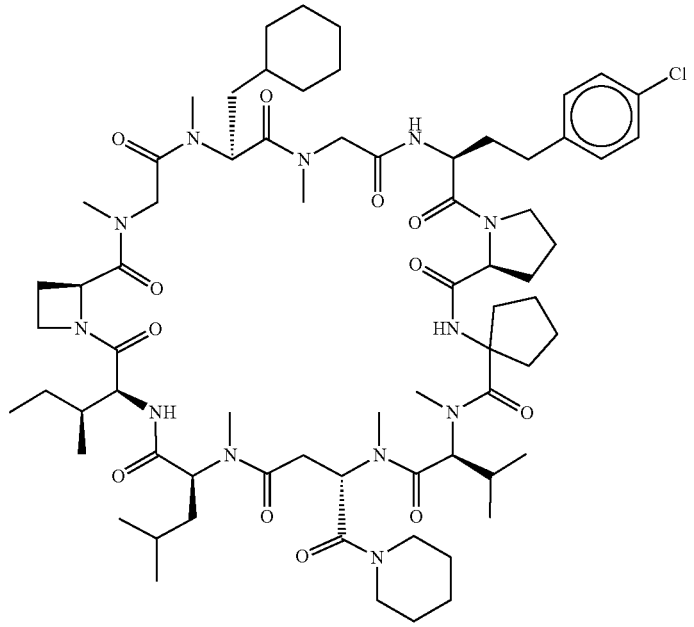 |
| 113 | 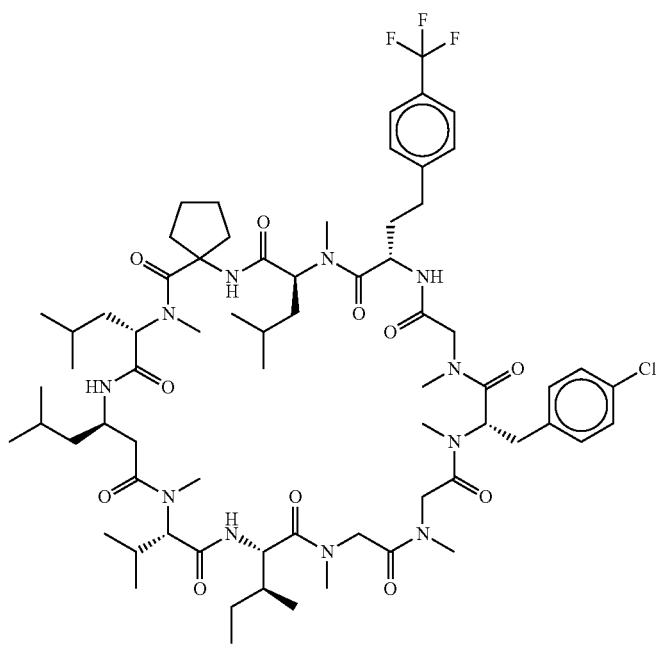 |

TABLE 24-continued
| Compound No. | Structural formula |
|---|---|
| 114 | 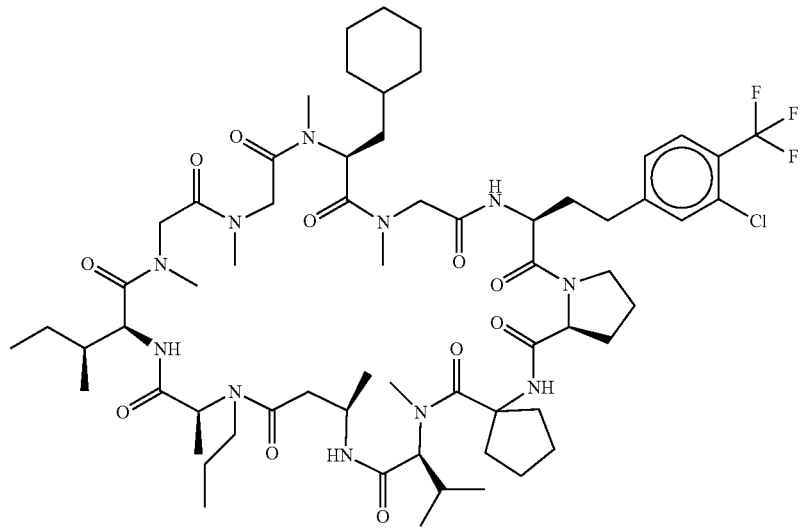 |
| 115 | 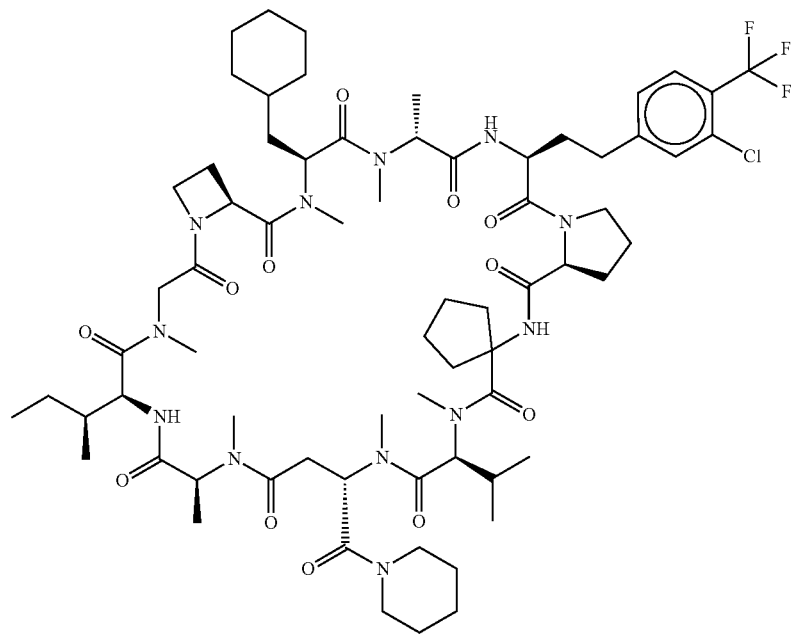 |

TABLE 24-continued
| Compound No. | Structural formula |
|---|---|
| 116 | 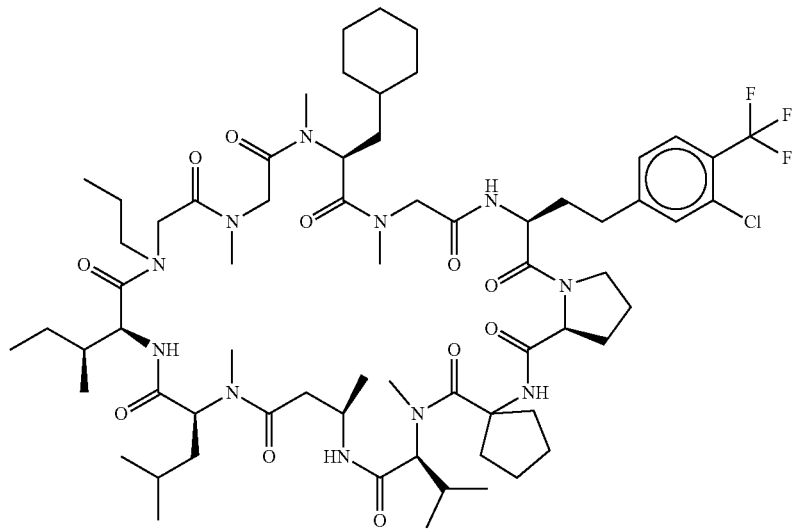 |
| 117 | 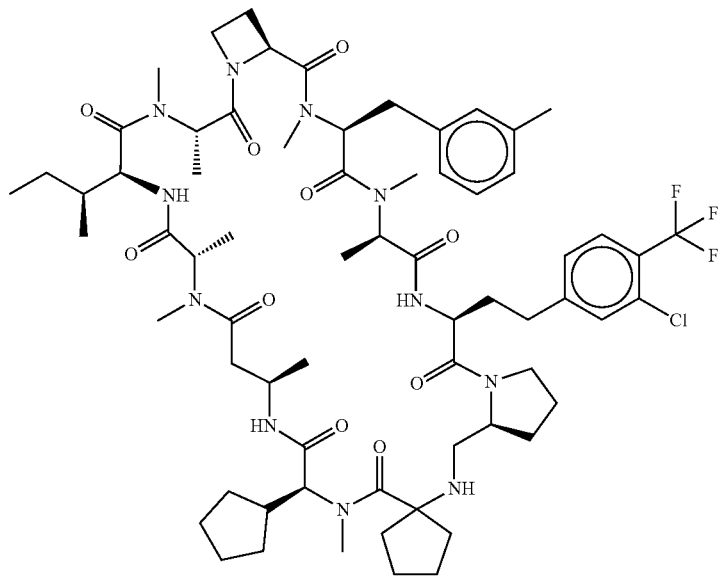 |

TABLE 24-continued
| Compound No. | Structural formula |
|---|---|
| 118 | 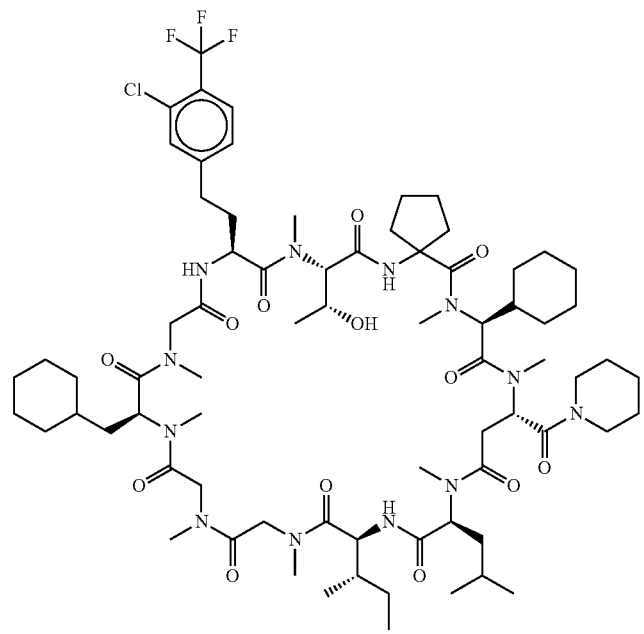 |
| 119 | 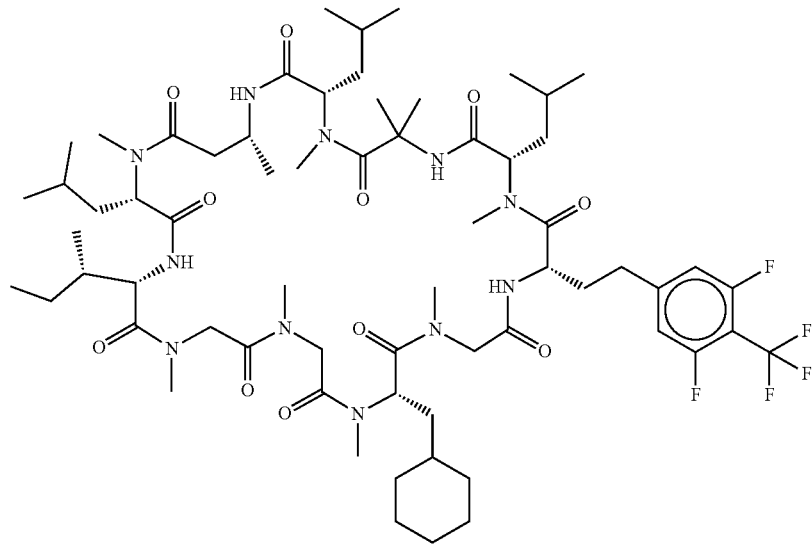 |

TABLE 24-continued
| Compound No. | Structural formula |
|---|---|
| 120 | 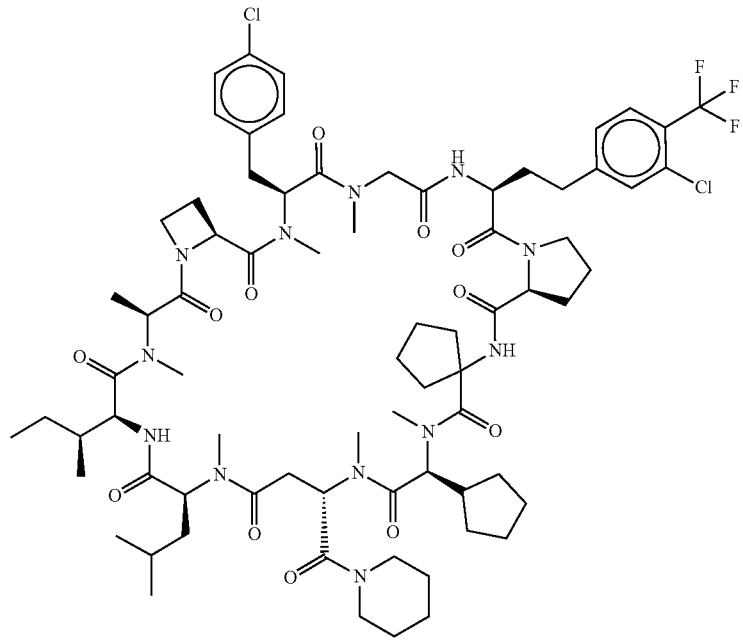 |
| 121 | 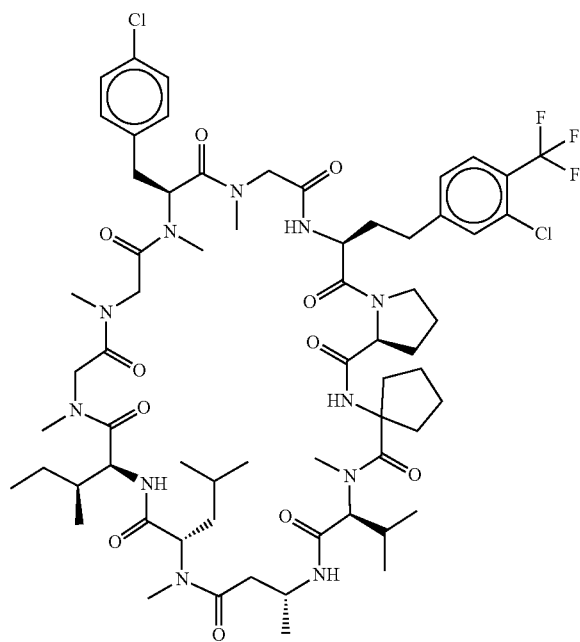 |

TABLE 24-continued
| Compound No. | Structural formula |
|---|---|
| 122 | 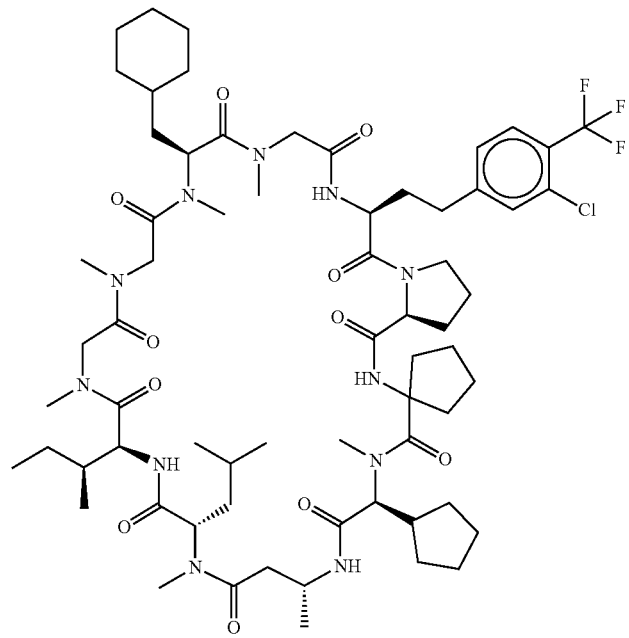 |
| 123 | 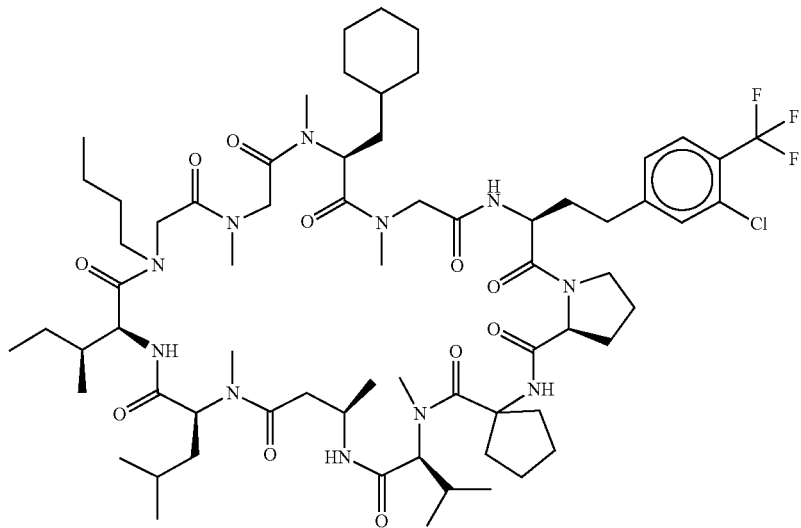 |

TABLE 24-continued
| Compound No. | Structural formula |
|---|---|
| 124 | 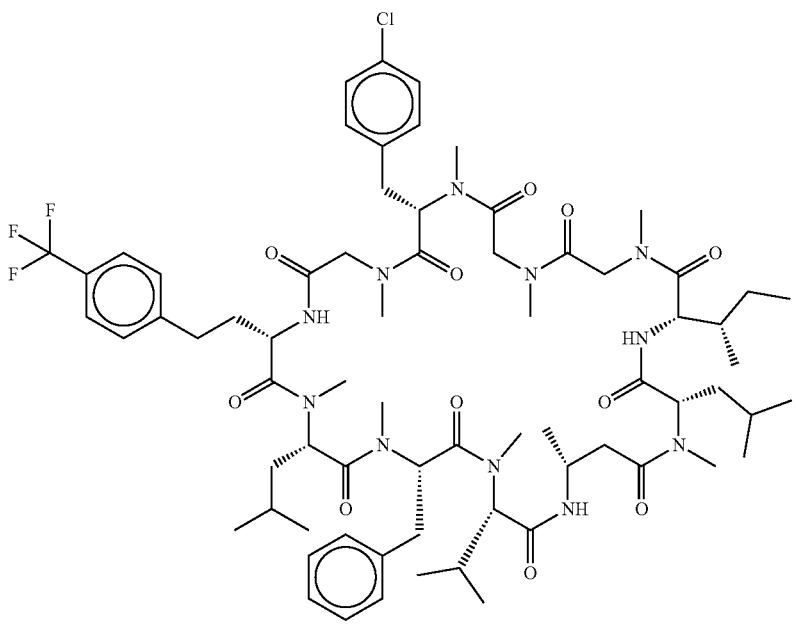 |
| 125 | 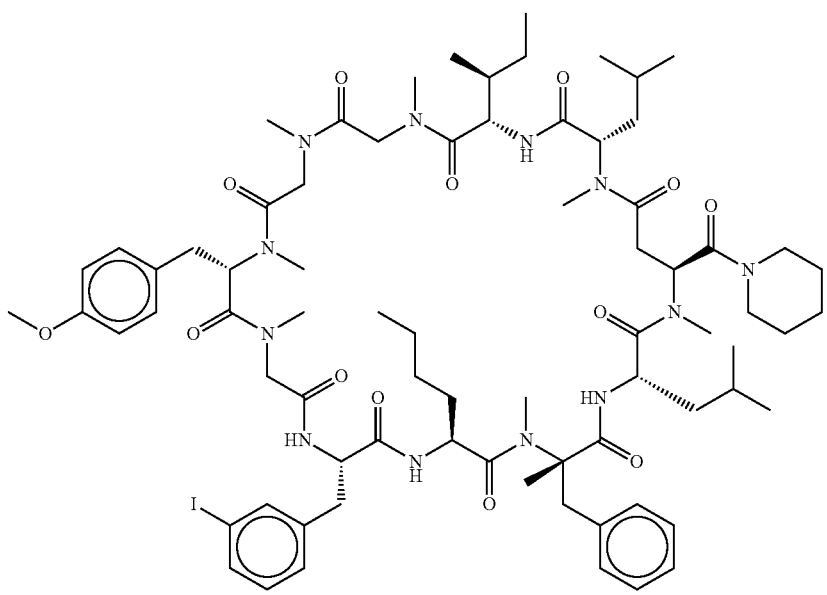 |

TABLE 24-continued
| Compound No. | Structural formula |
| --- | --- |
| 126 | 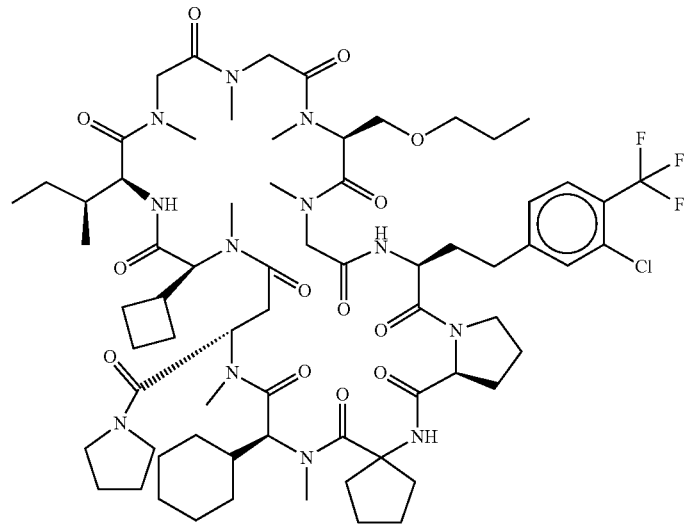 |
| 127 | 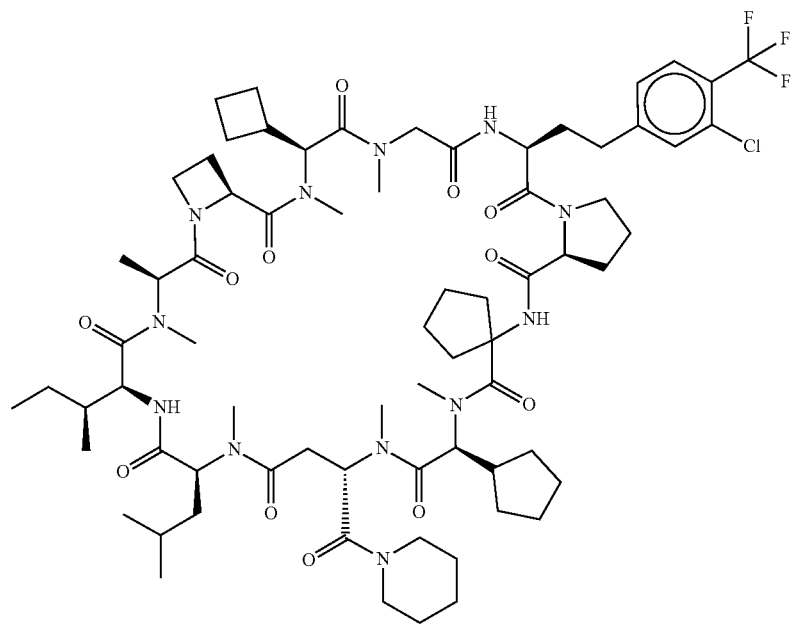 |

TABLE 24-continued
| Compound No. | Structural formula |
|---|---|
| 128 | 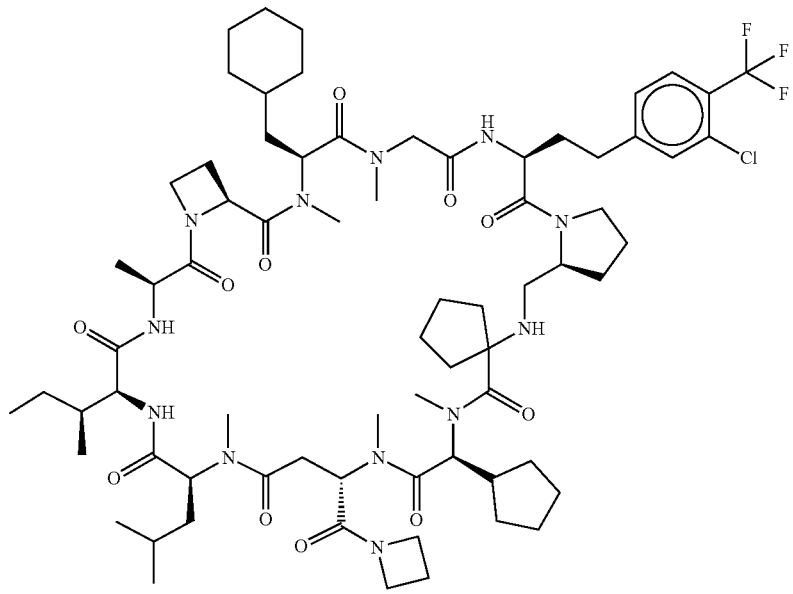 |
| 129 | 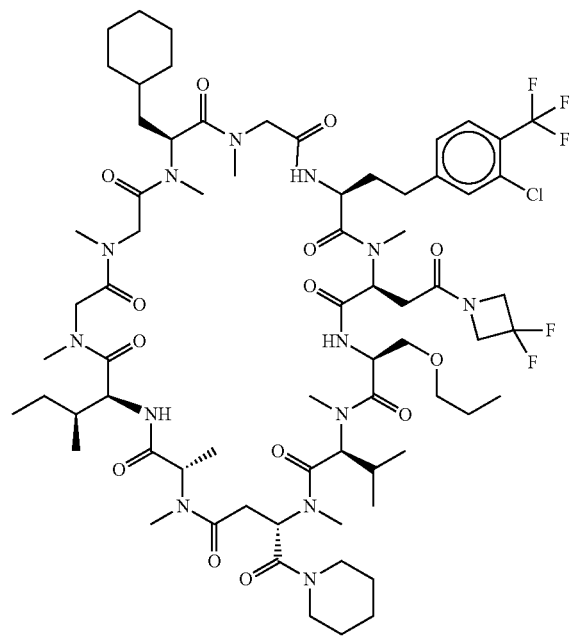 |

TABLE 24-continued
| Compound No. | Structural formula |
|---|---|
| 130 | 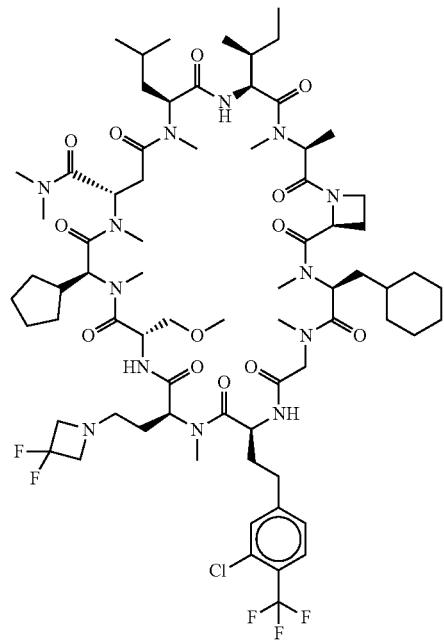 |
| 131 | 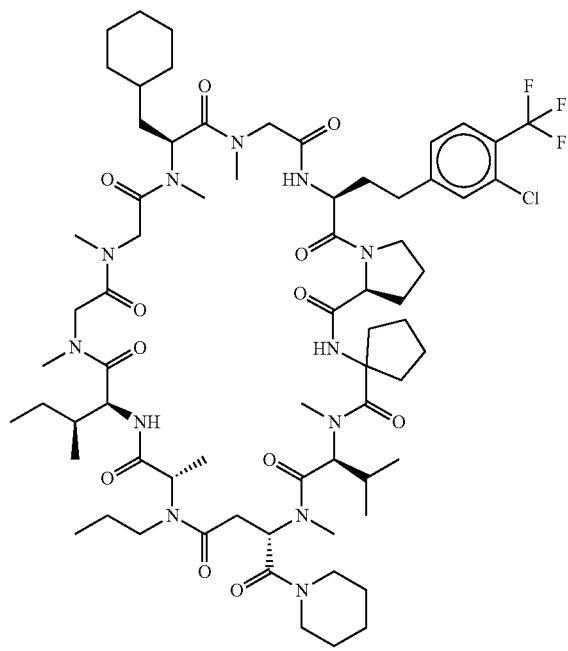 |

TABLE 24-continued
| Compound No. | Structural formula |
|---|---|
| 132 | 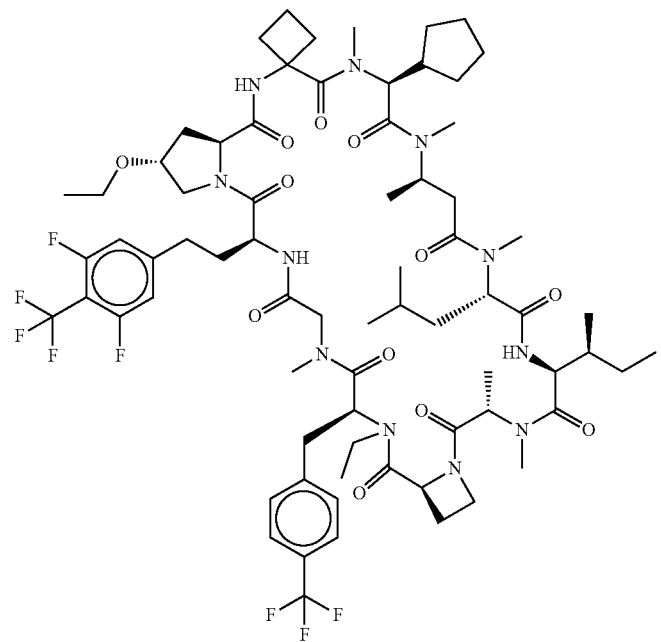 |
| 133 | 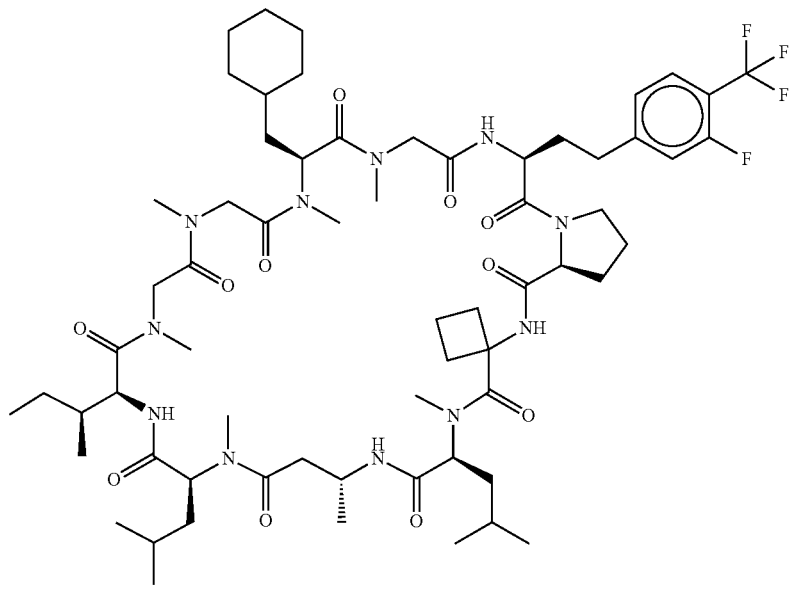 |

TABLE 24-continued
| Compound No. | Structural formula |
|---|---|
| 134 | 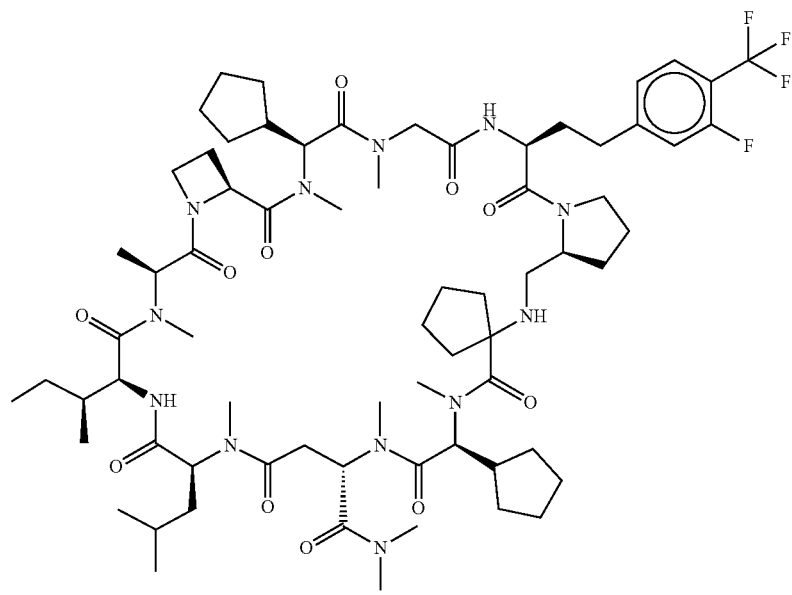 |
| 135 | 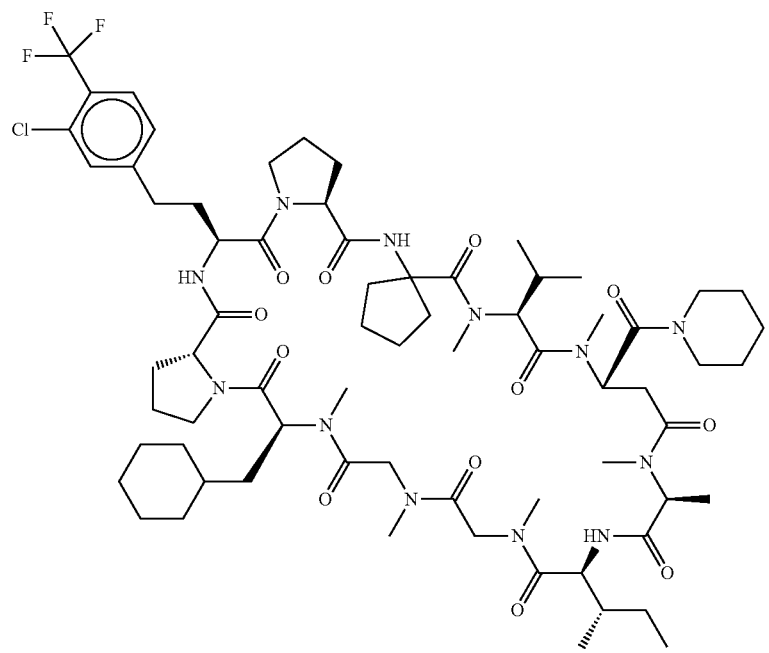 |

TABLE 24-continued
| Compound No. | Structural formula |
|---|---|
| 136 | 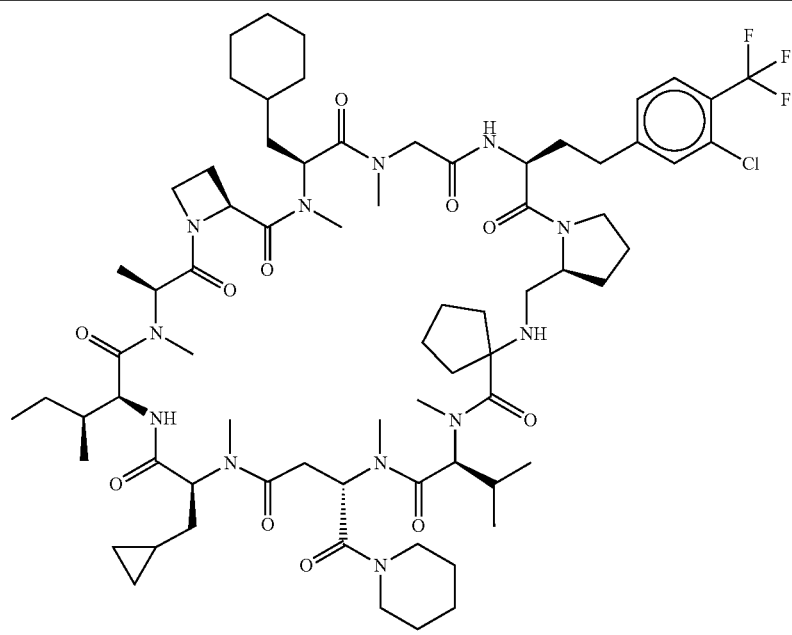 |
| 137 | 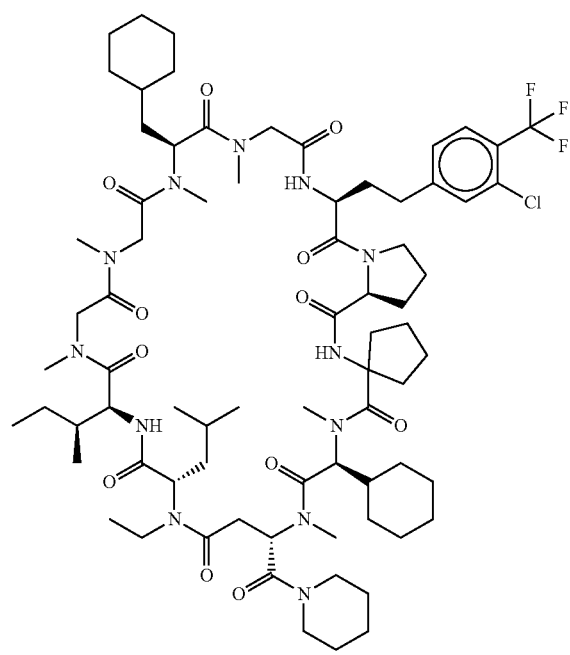 |

TABLE 24-continued
| Compound No. | Structural formula |
|---|---|
| 138 | 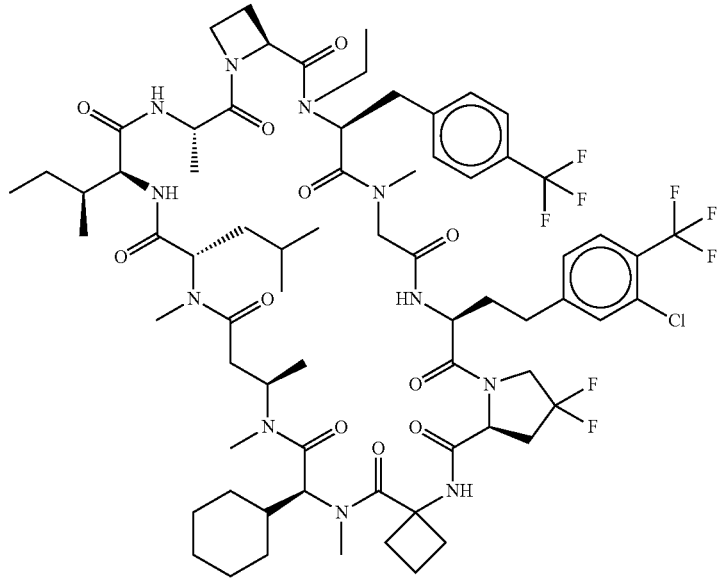 |
| 139 | 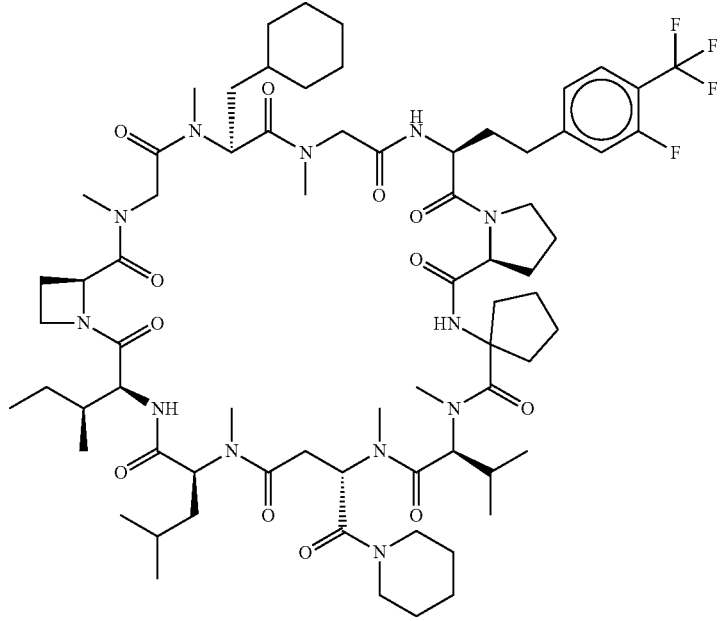 |

TABLE 24-continued
| Compound No. | Structural formula |
|---|---|
| 140 | 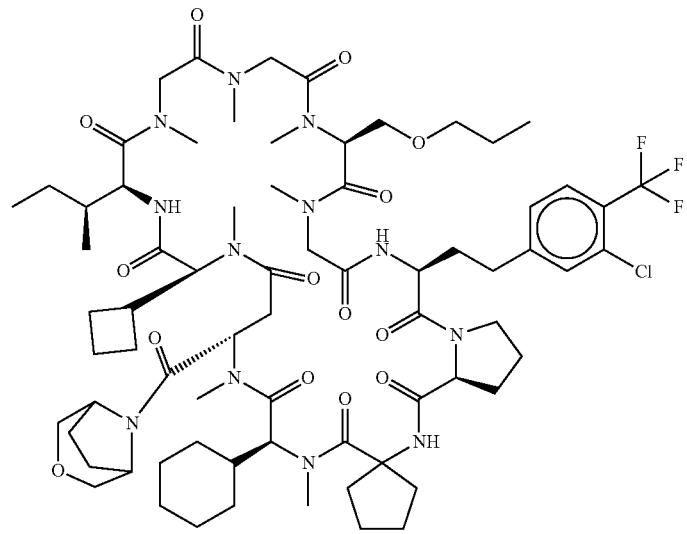 |
| 141 | 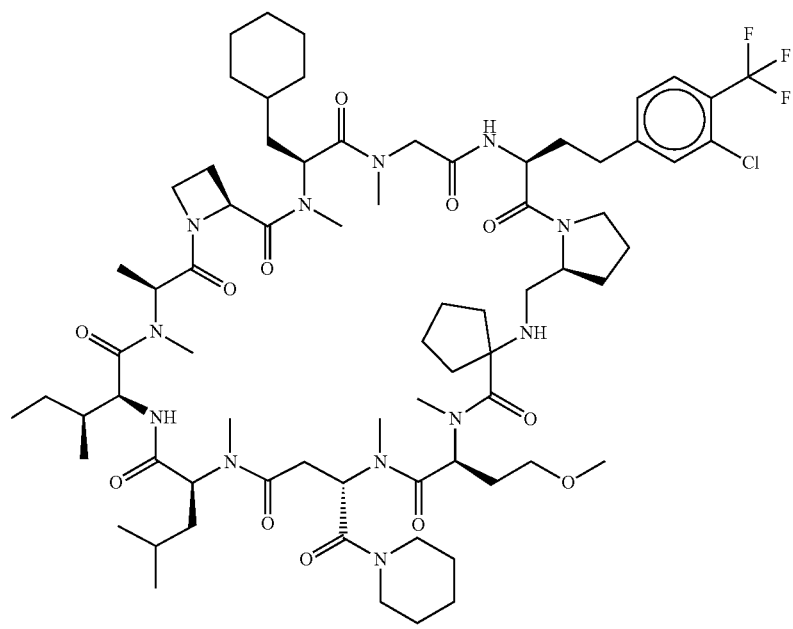 |

TABLE 24-continued
| Compound No. | Structural formula |
|---|---|
| 142 | 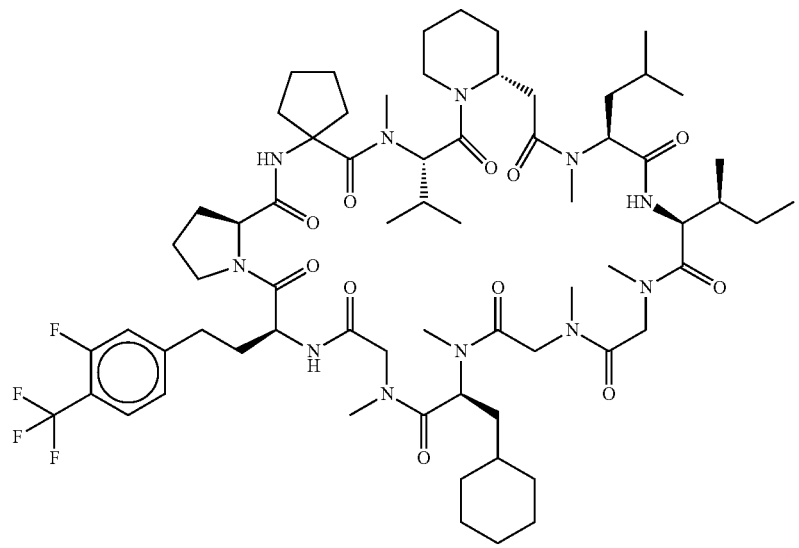 |
| 143 | 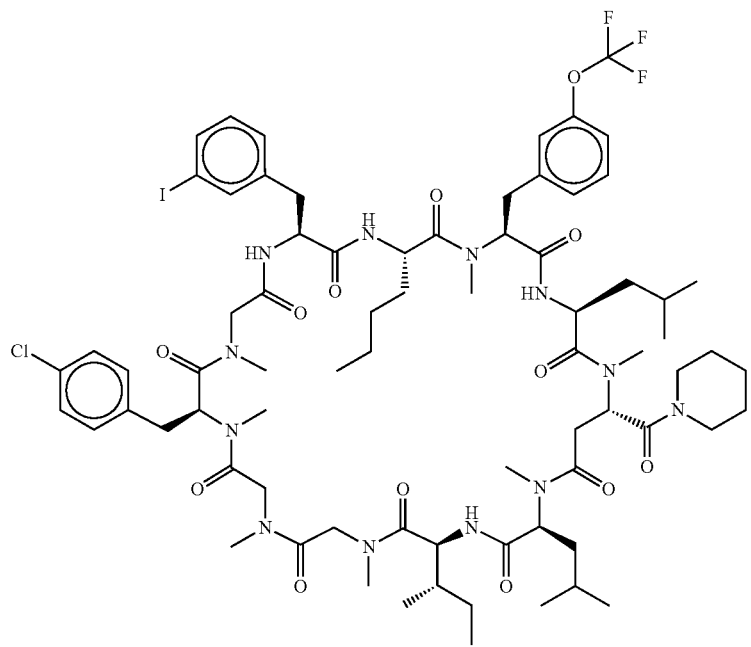 |

TABLE 24-continued
| Compound No. | Structural formula |
|---|---|
| 144 | 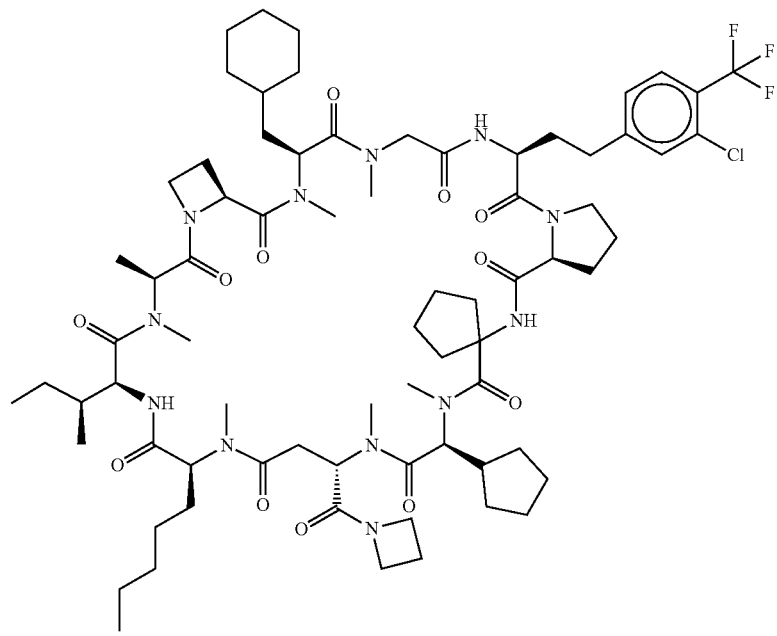 |
| 145 | 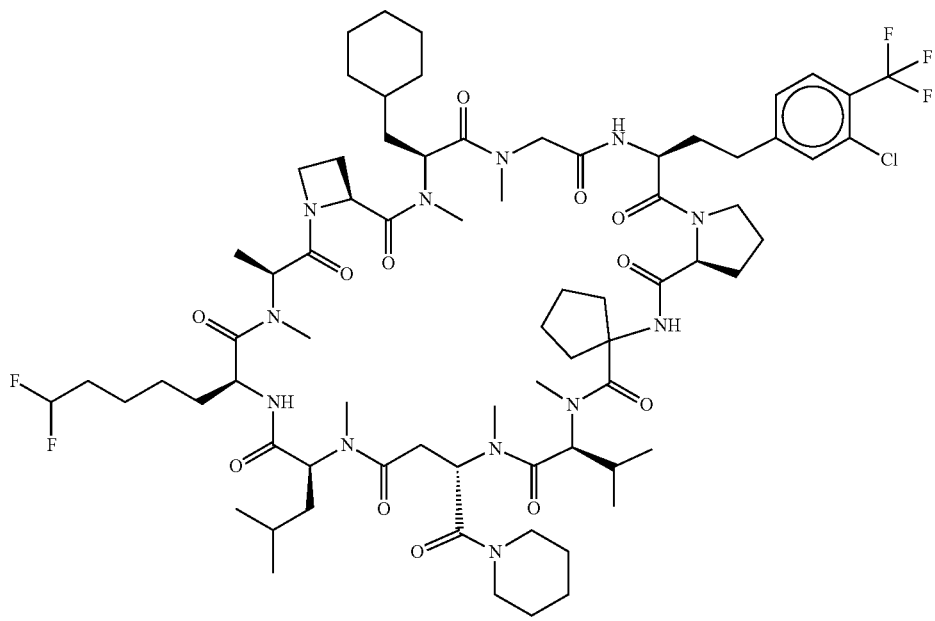 |

TABLE 24-continued

| Compound No. | Structural formula |
|---|---|
| 146 | |
| 147 | |

TABLE 24-continued
| Compound No. | Structural formula |
| --- | --- |
| 148 | 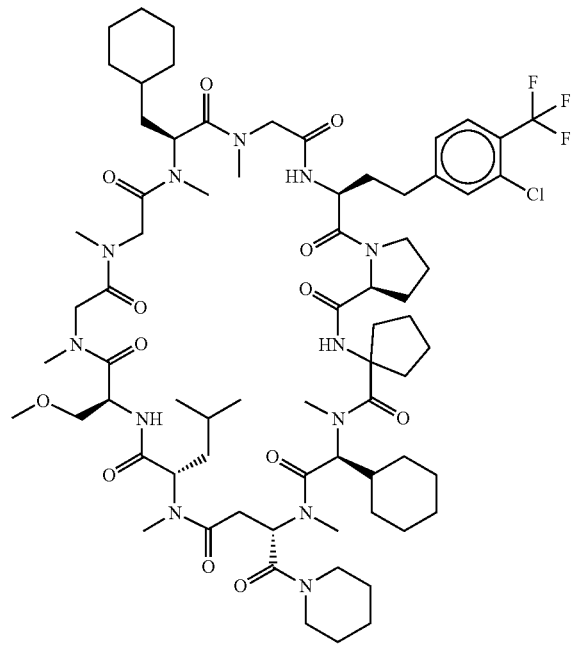 |
| 149 | 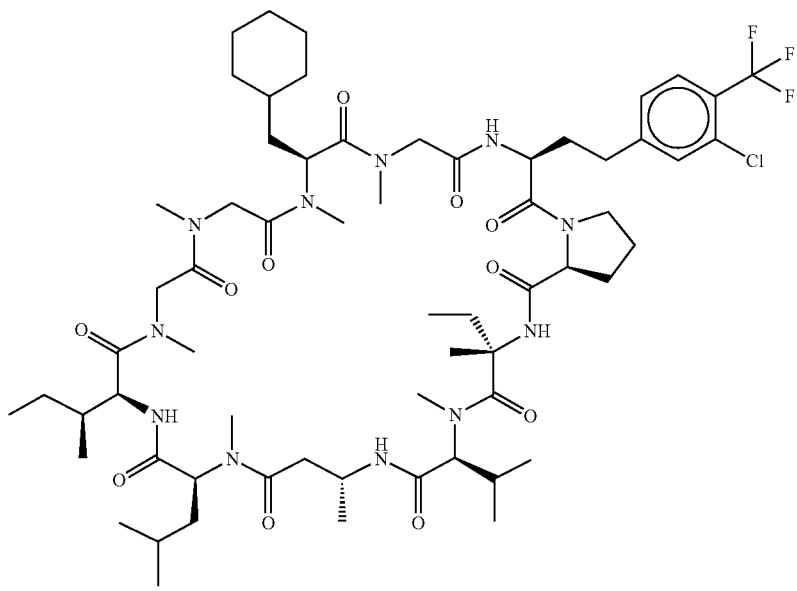 |

TABLE 24-continued
| Compound No. | Structural formula |
|---|---|
| 150 | 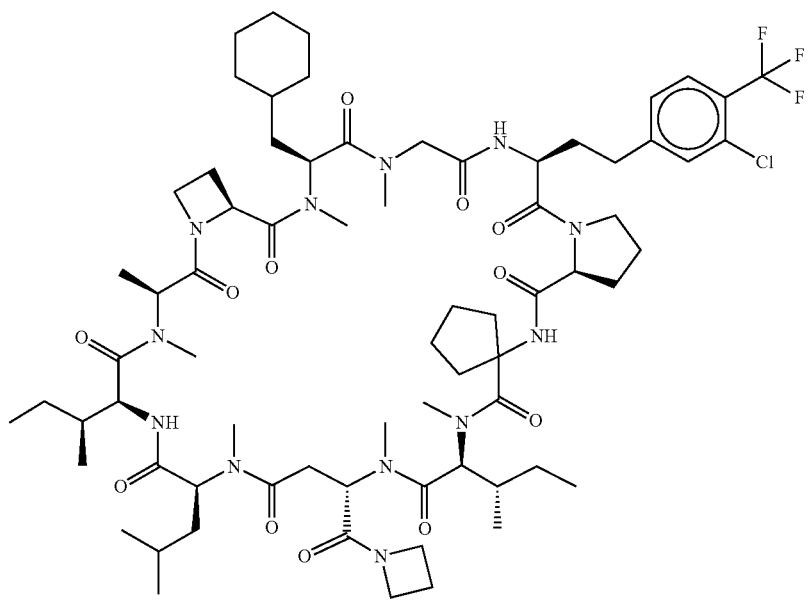 |
| 151 | 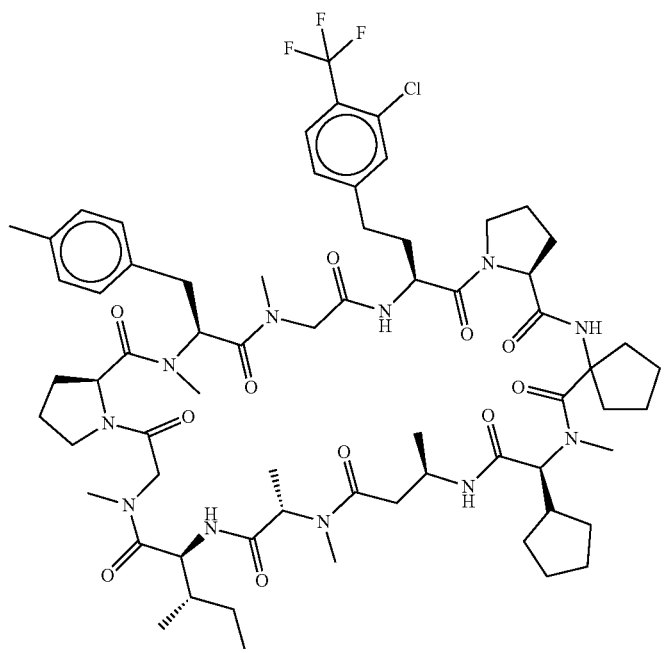 |

TABLE 24-continued
| Compound No. | Structural formula |
|---|---|
| 152 | 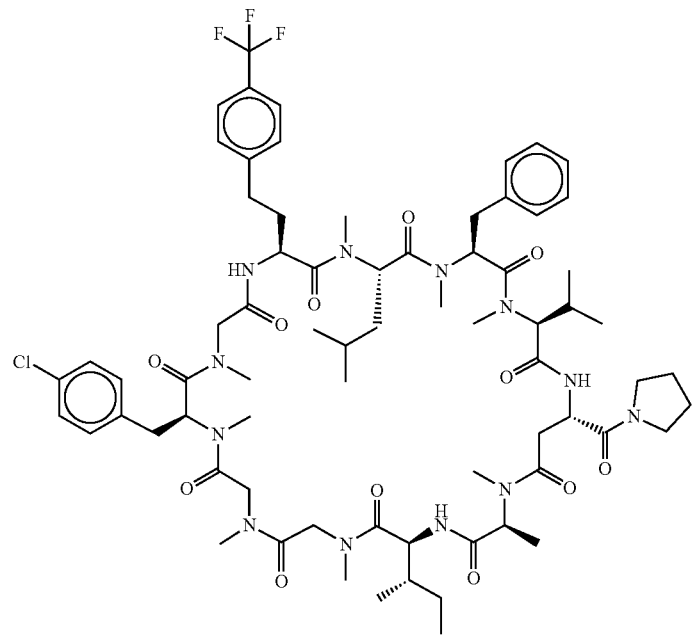 |
| 153 | 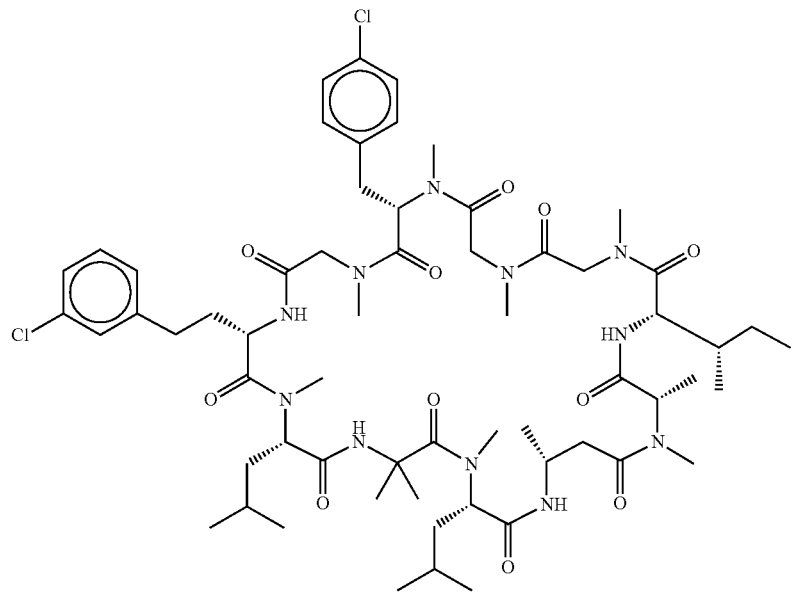 |

TABLE 24-continued
| Compound No. | Structural formula |
|---|---|
| 154 | 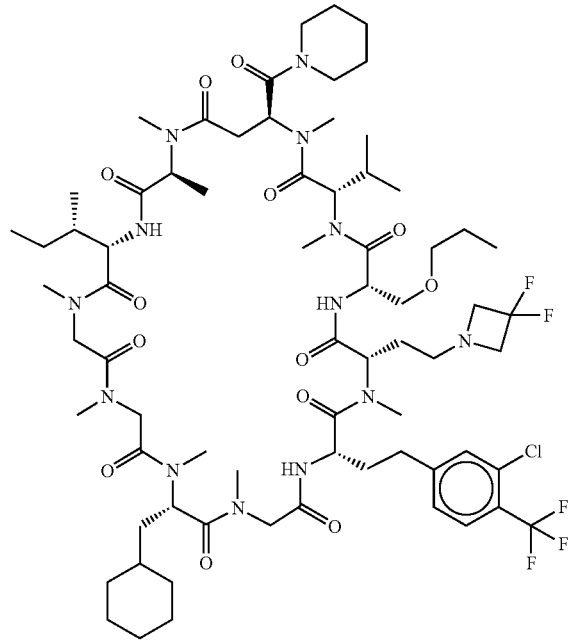 |
| 155 | 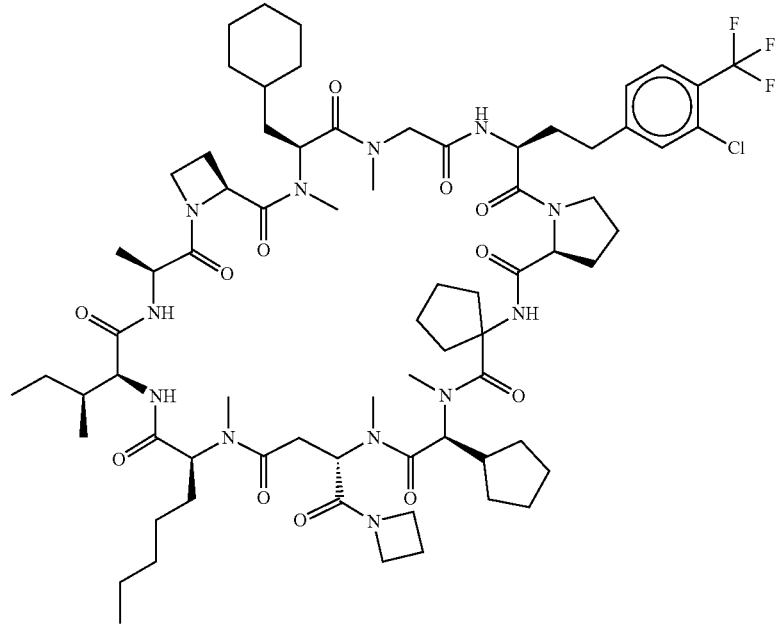 |

TABLE 24-continued
| Compound No. | Structural formula |
|---|---|
| 156 | 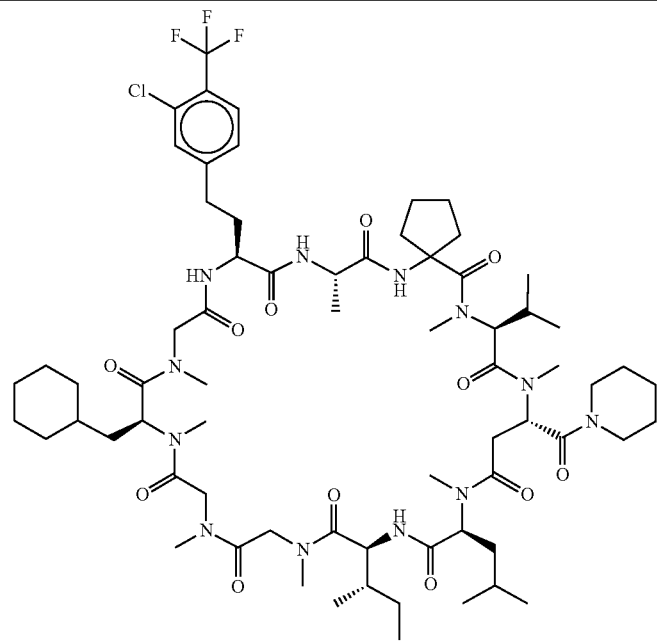 |
| 157 | 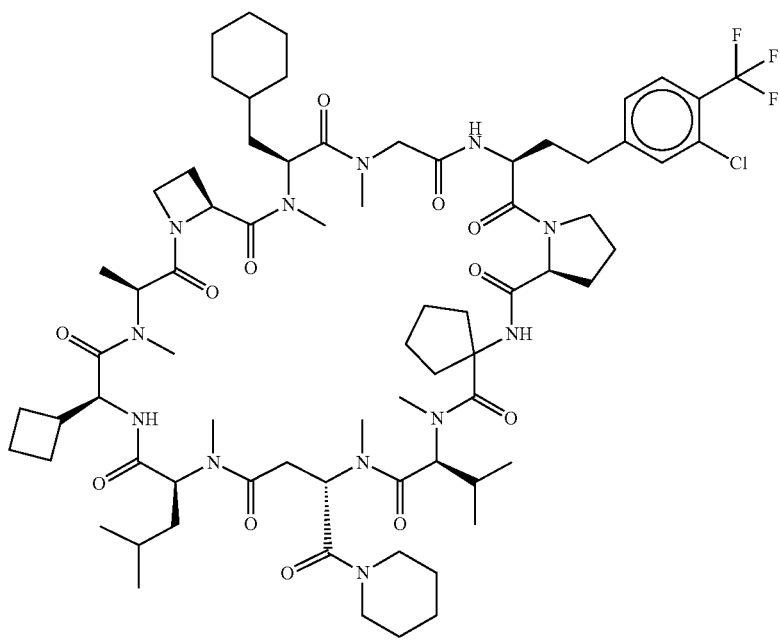 |

TABLE 24-continued
| Compound No. | Structural formula |
|---|---|
| 158 | 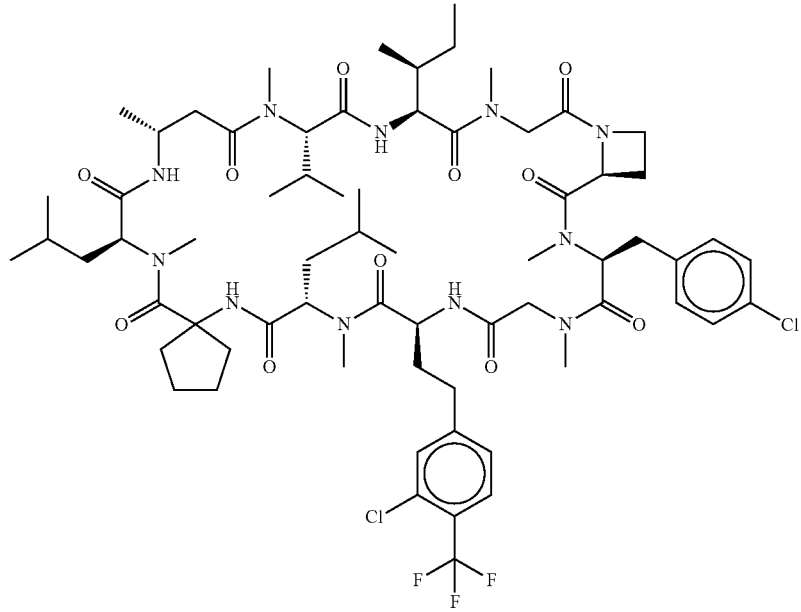 |
| 159 | 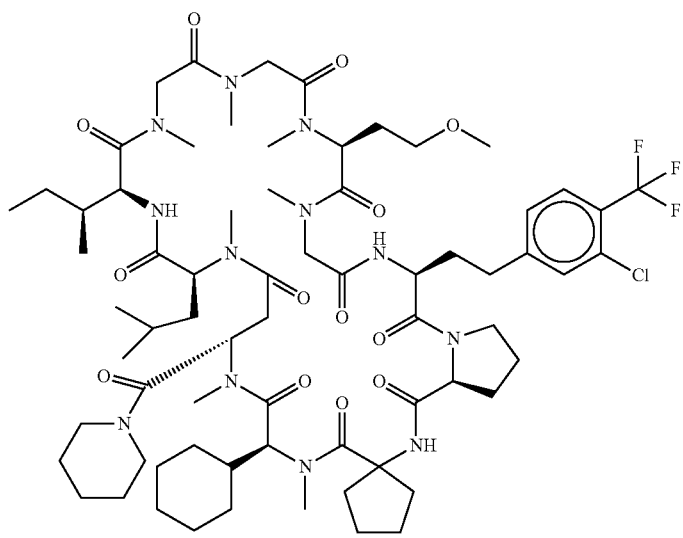 |

TABLE 24-continued
| Compound No. | Structural formula |
|---|---|
| 160 | 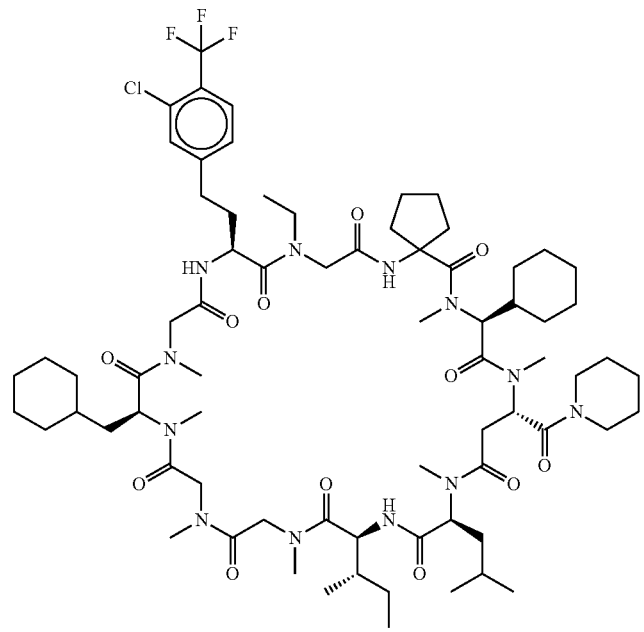 |
| 161 | 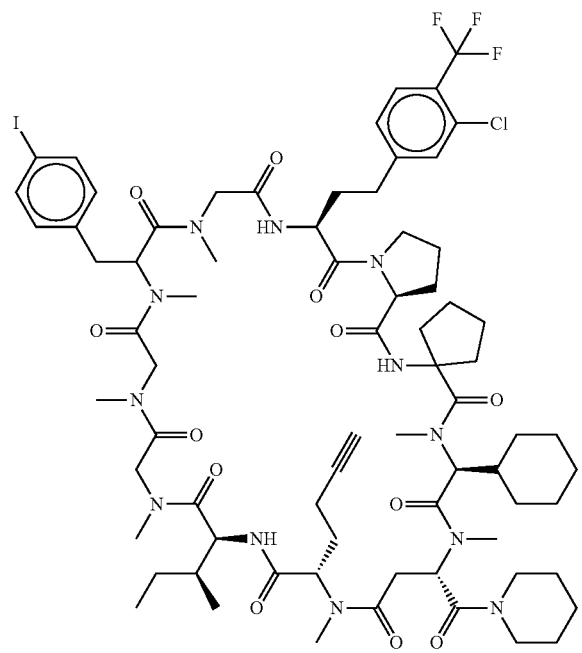 |

TABLE 24-continued
| Compound No. | Structural formula |
|---|---|
| 162 | 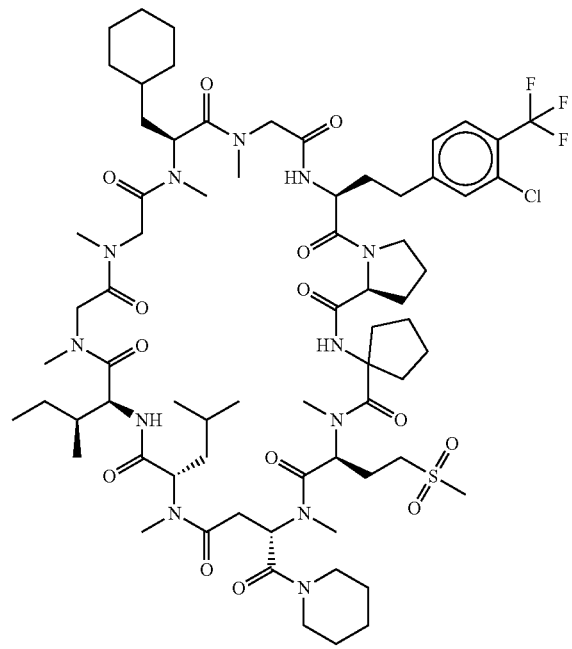 |
| 163 | 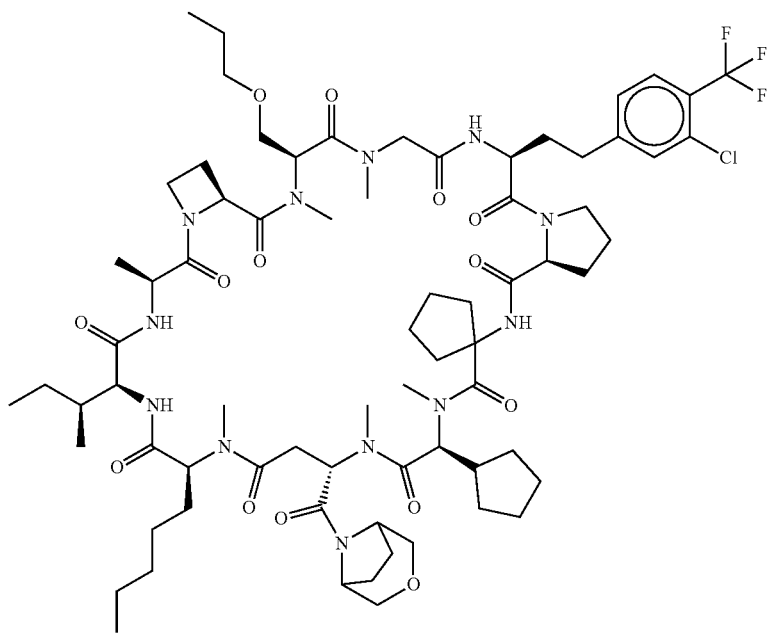 |

TABLE 24-continued
| Compound No. | Structural formula |
|---|---|
| 164 | 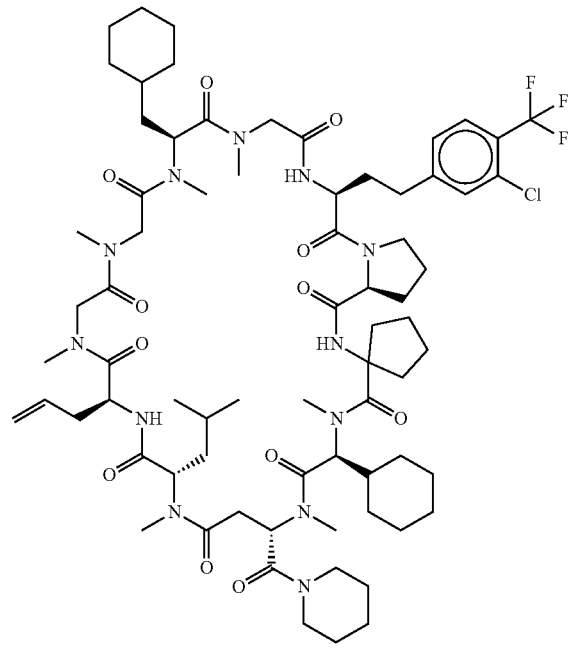 |
| 165 | 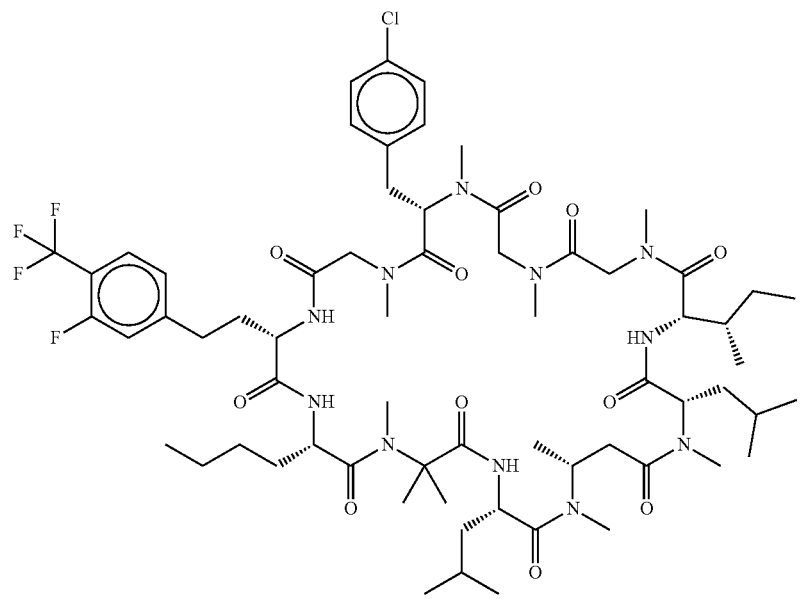 |

TABLE 24-continued
| Compound No. | Structural formula |
|---|---|
| 166 | 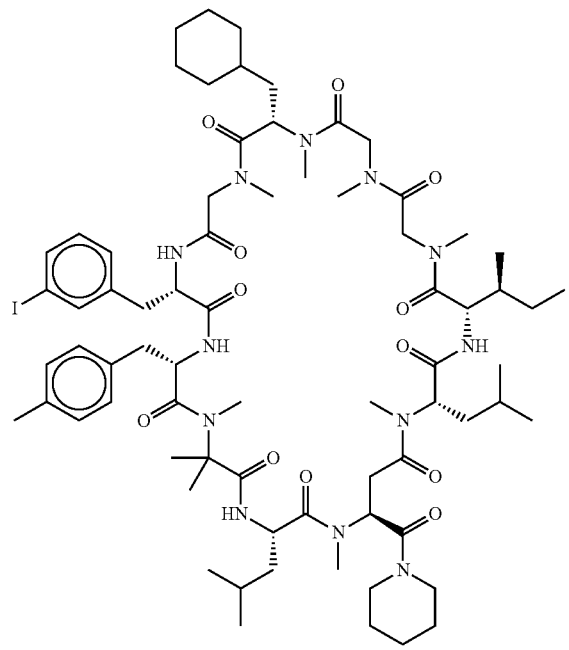 |
| 167 | 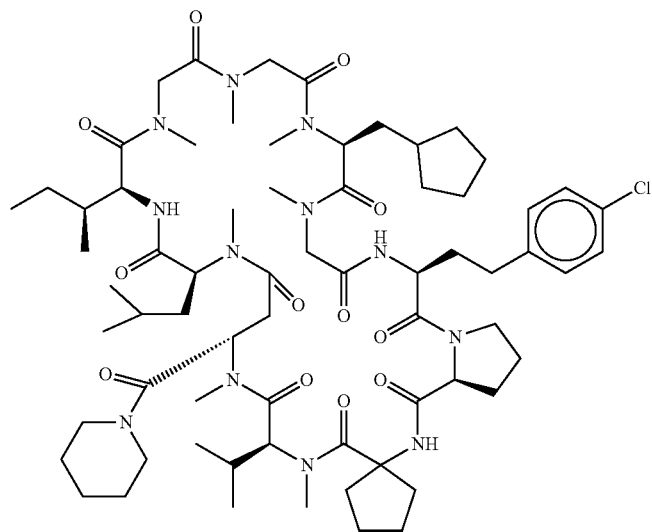 |

TABLE 24-continued
| Compound No. | Structural formula |
|---|---|
| 168 | 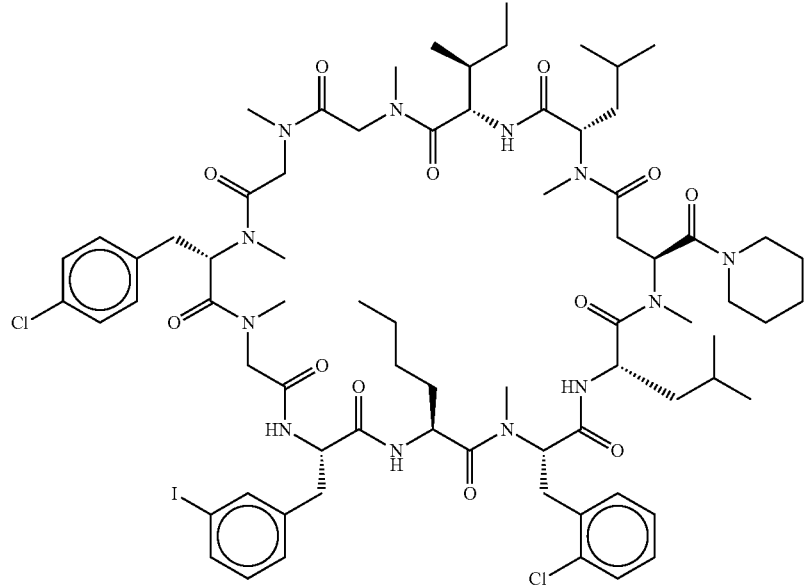 |
| 169 | 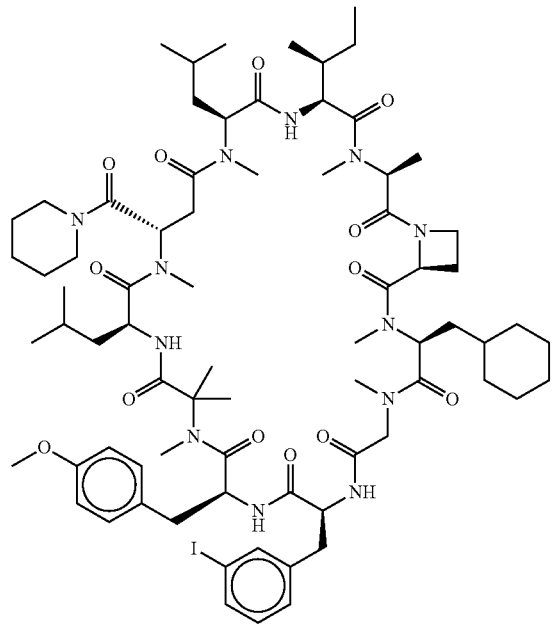 |

TABLE 24-continued
| Compound No. | Structural formula |
|---|---|
| 170 | 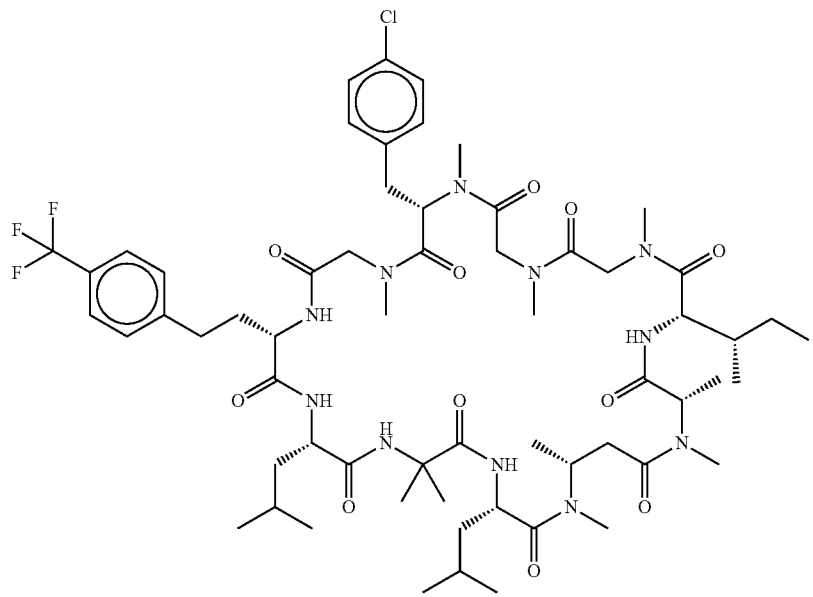 |
| 171 | 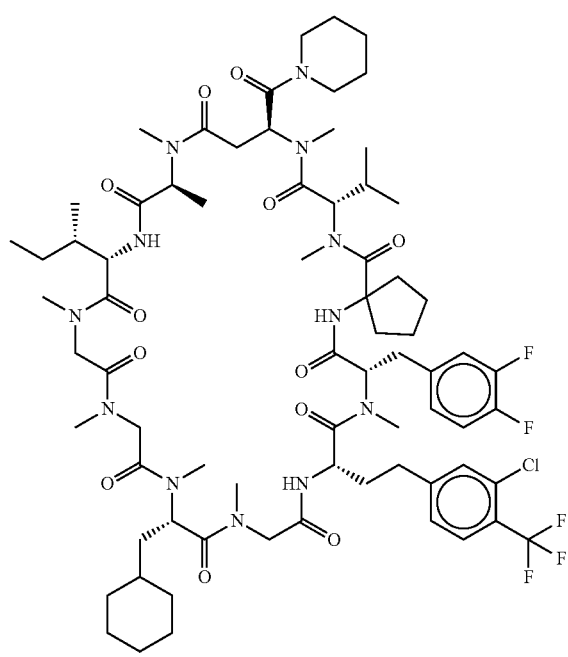 |

TABLE 24-continued
| Compound No. | Structural formula |
|---|---|
| 172 | 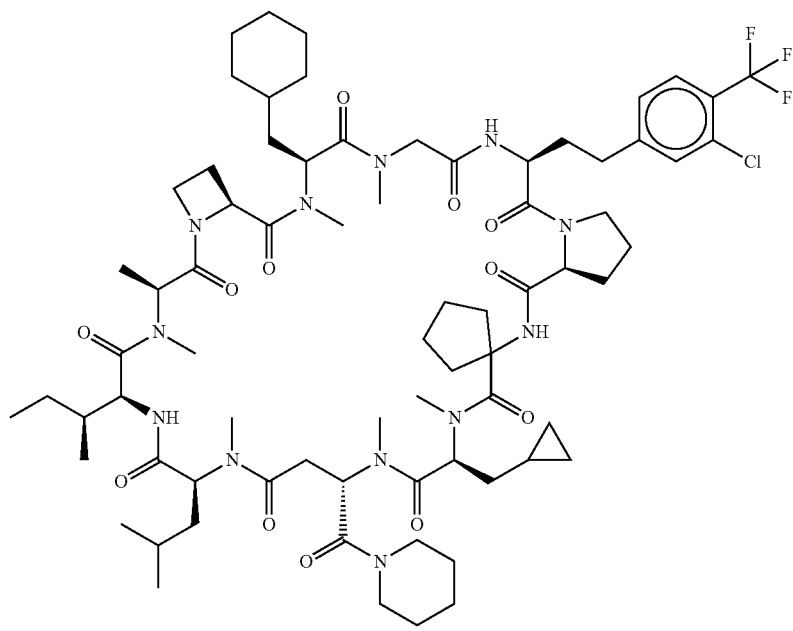 |
| 173 | 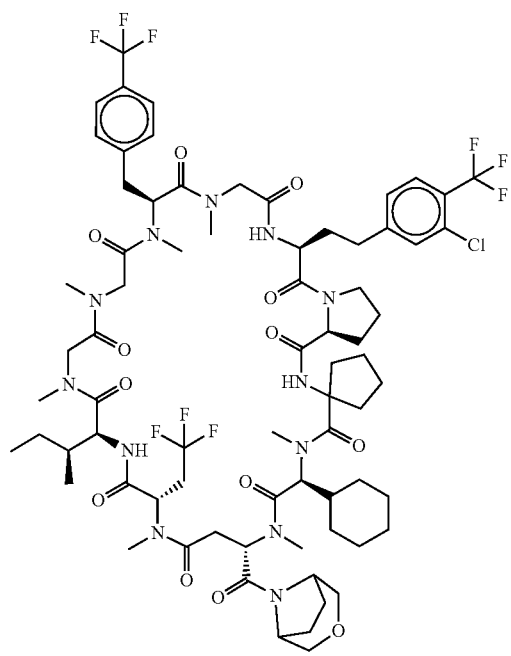 |

TABLE 24-continued
| Compound No. | Structural formula |
|---|---|
| 174 | 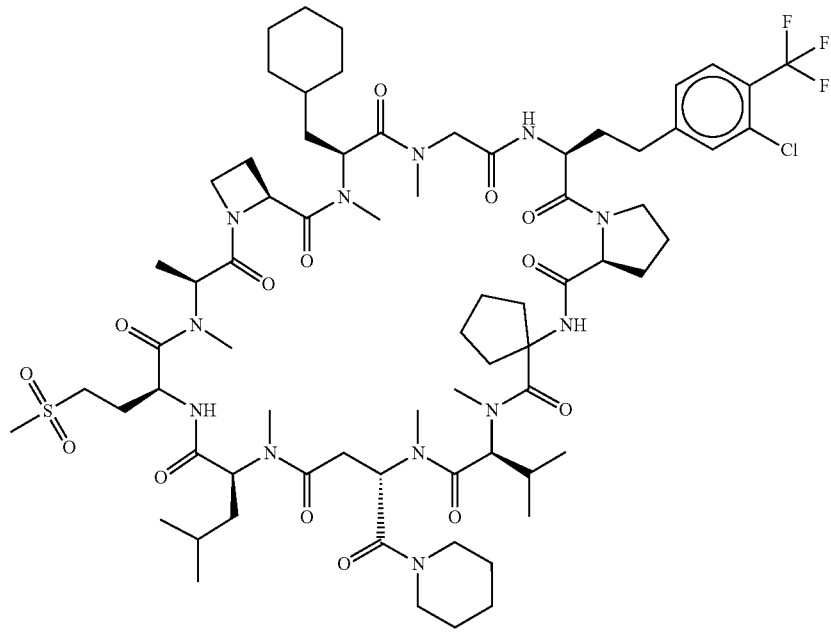 |
| 175 | 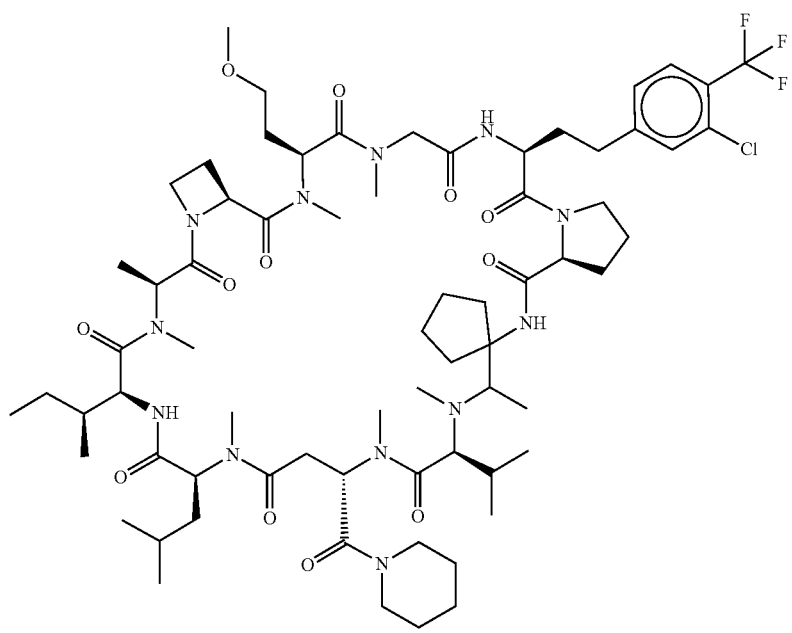 |

TABLE 24-continued
| Compound No. | Structural formula |
|---|---|
| 176 | 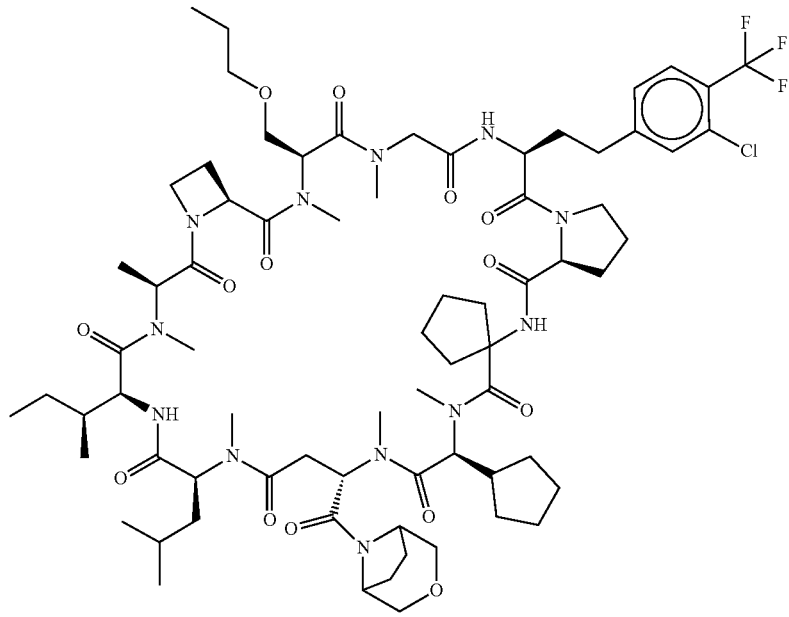 |
| 177 | 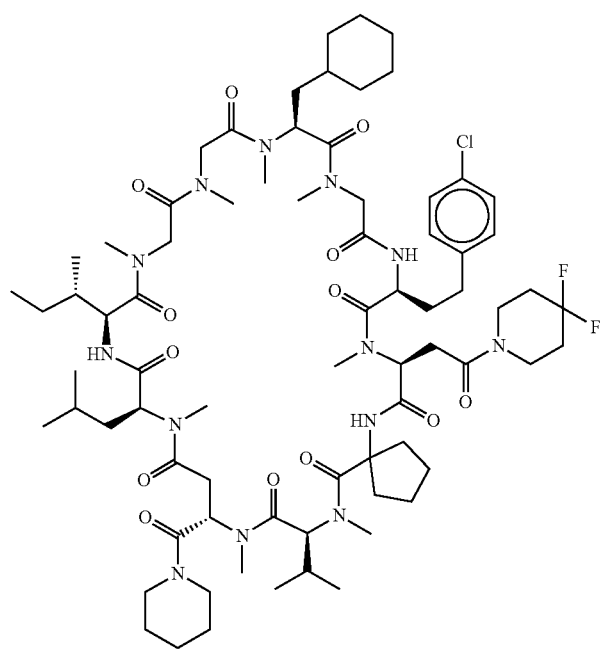 |

TABLE 24-continued
| Compound No. | Structural formula |
|---|---|
| 178 | 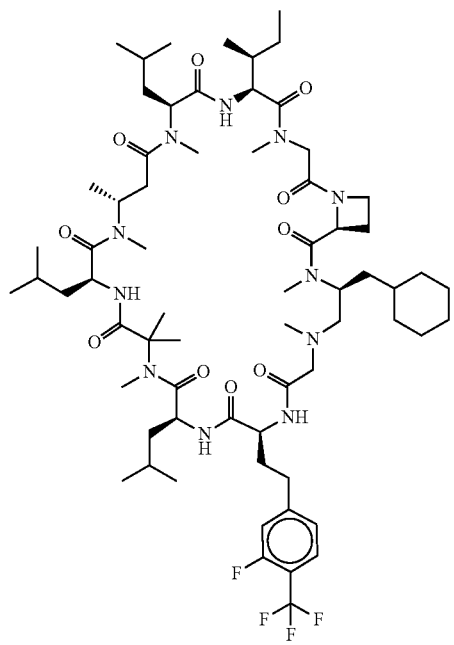 |
| 179 | 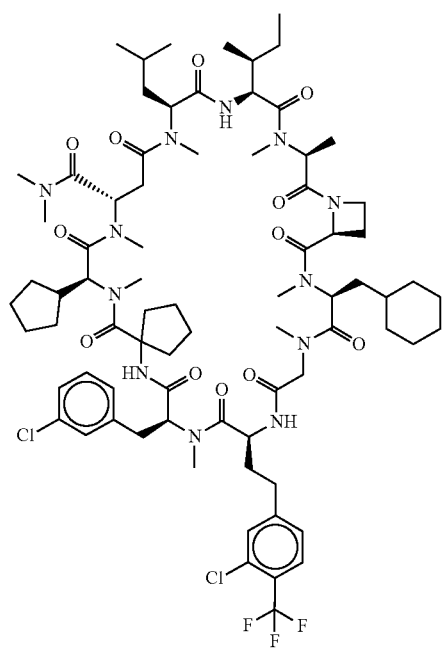 |

TABLE 24-continued
| Compound No. | Structural formula |
|---|---|
| 180 | 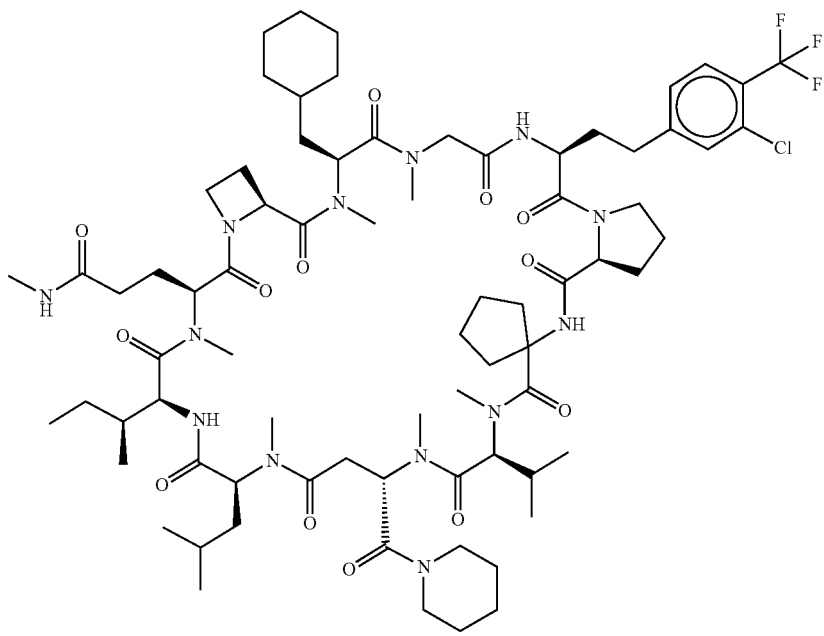 |
| 181 | 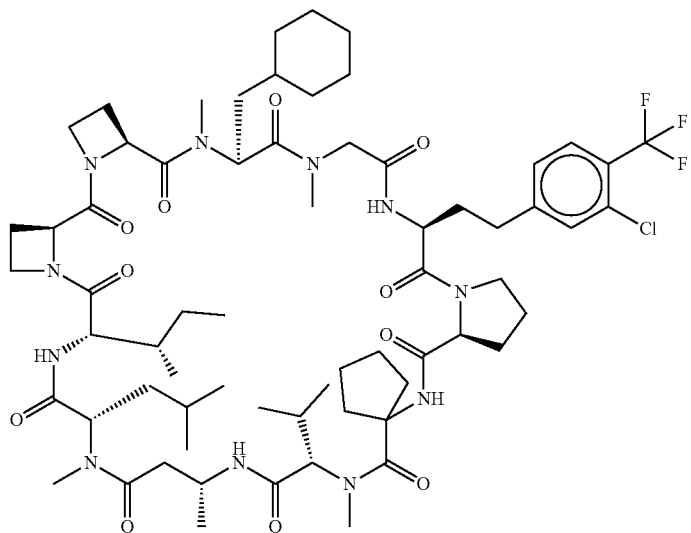 |

TABLE 24-continued
| Compound No. | Structural formula |
|---|---|
| 182 | 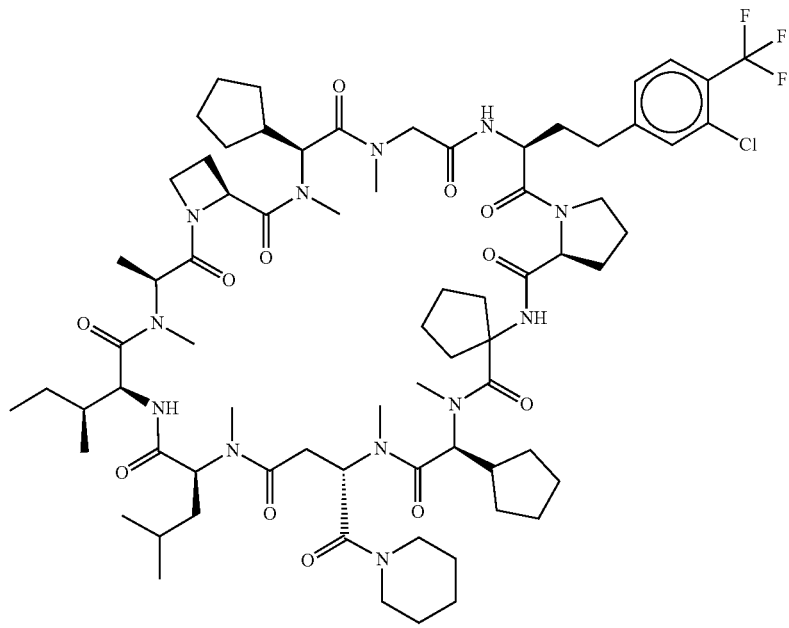 |
| 183 | 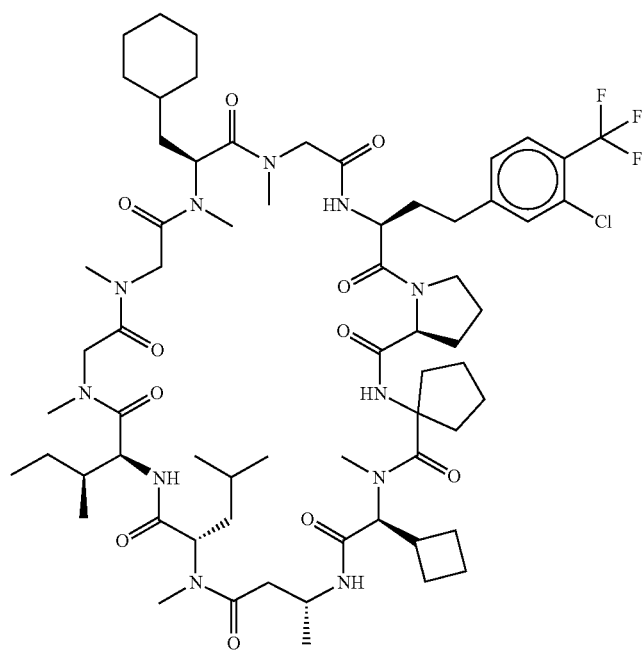 |

TABLE 24-continued
| Compound No. | Structural formula |
|---|---|
| 184 | 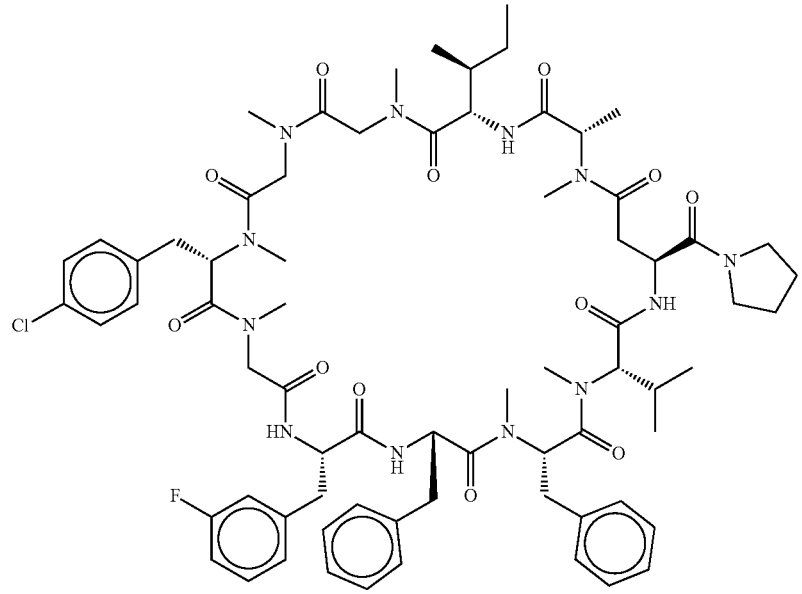 |
| 185 | 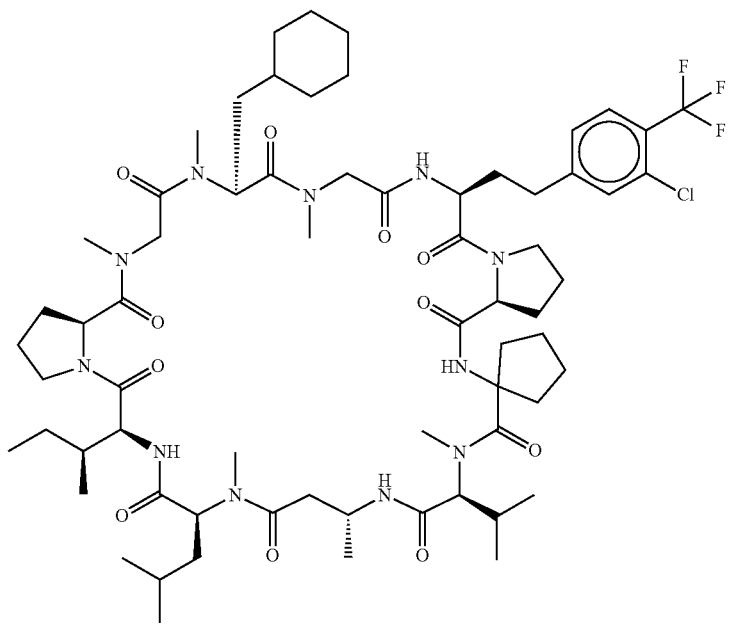 |

TABLE 24-continued
| Compound No. | Structural formula |
|---|---|
| 186 | 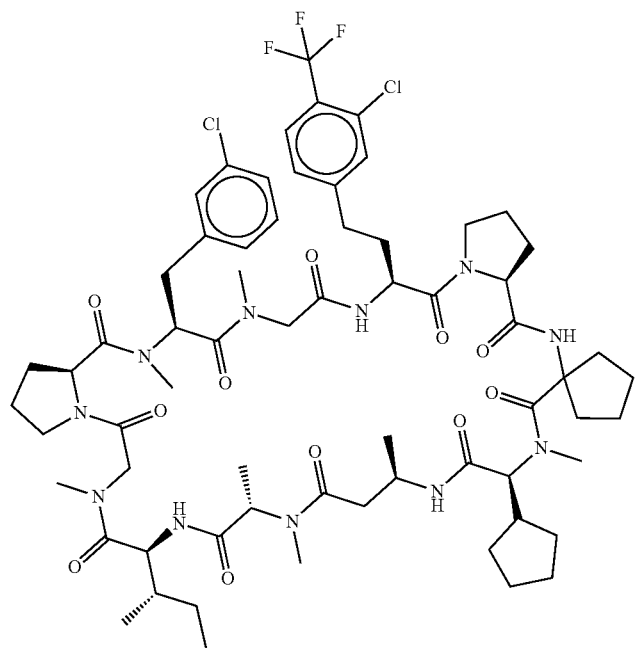 |
| 187 | 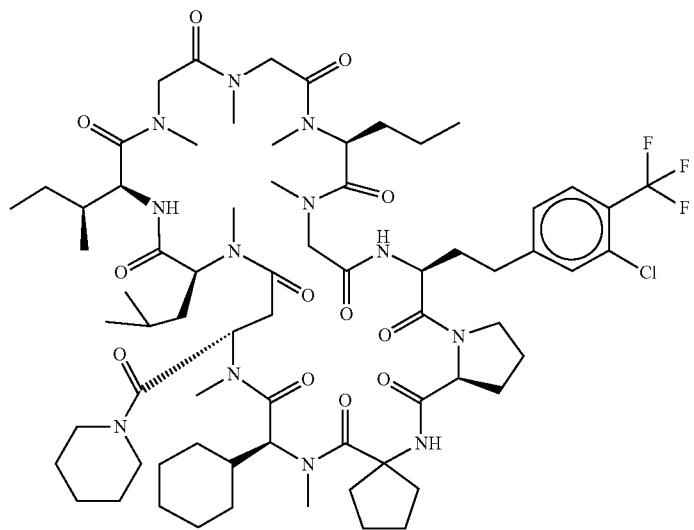 |

TABLE 24-continued
| Compound No. | Structural formula |
|---|---|
| 188 | 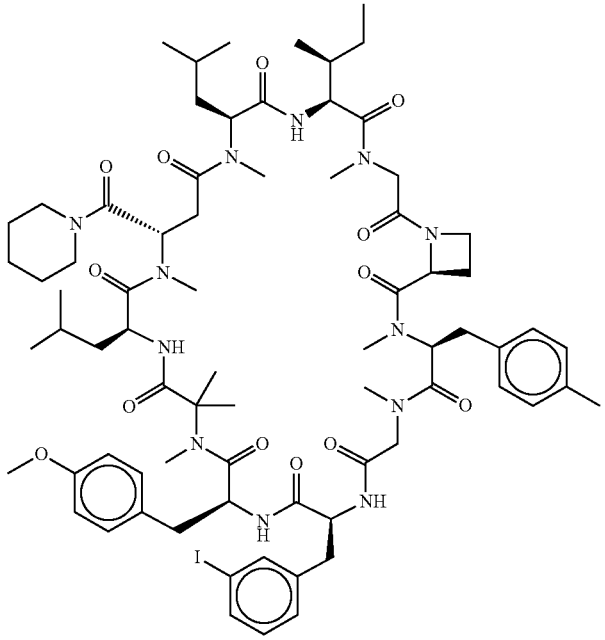 |
| 189 | 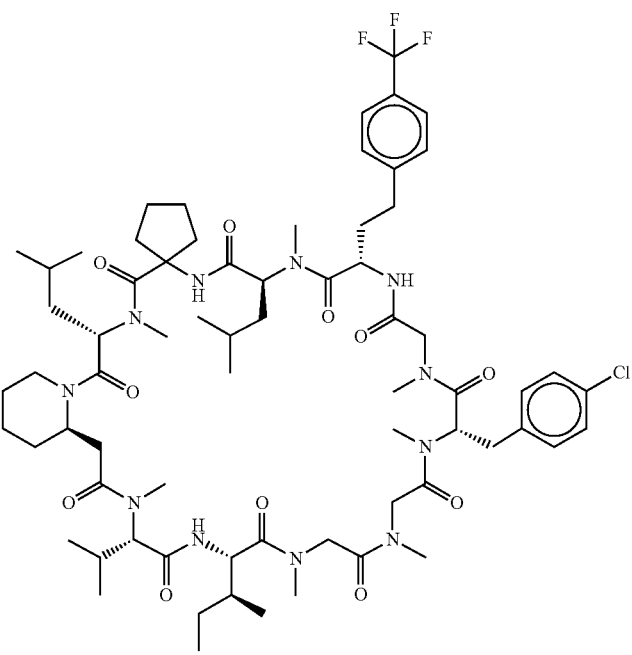 |

TABLE 24-continued
| Compound No. | Structural formula |
|---|---|
| 190 | 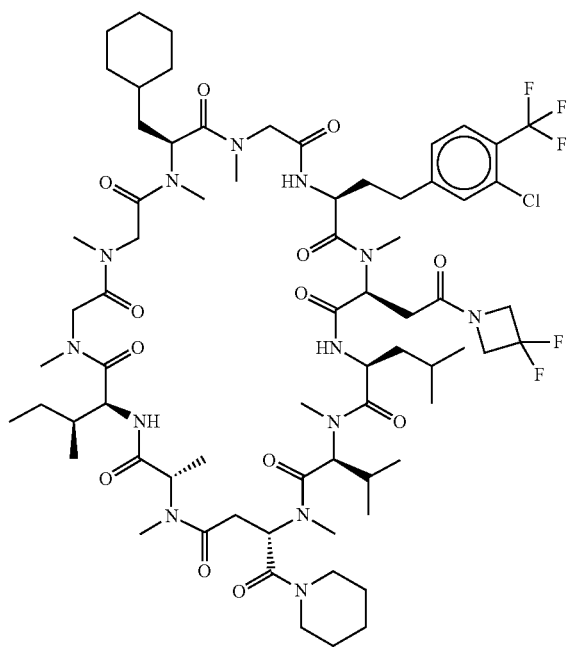 |
| 191 | 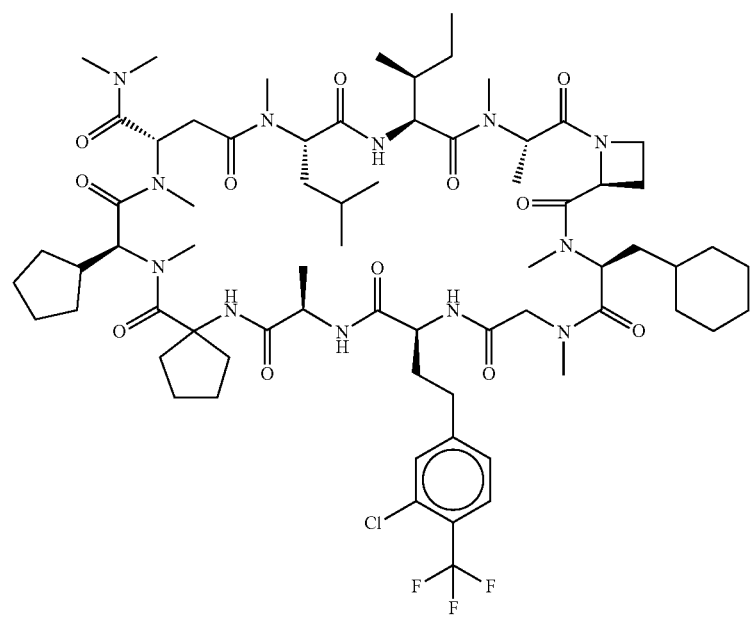 |

TABLE 24-continued
| Compound No. | Structural formula |
|---|---|
| 192 | 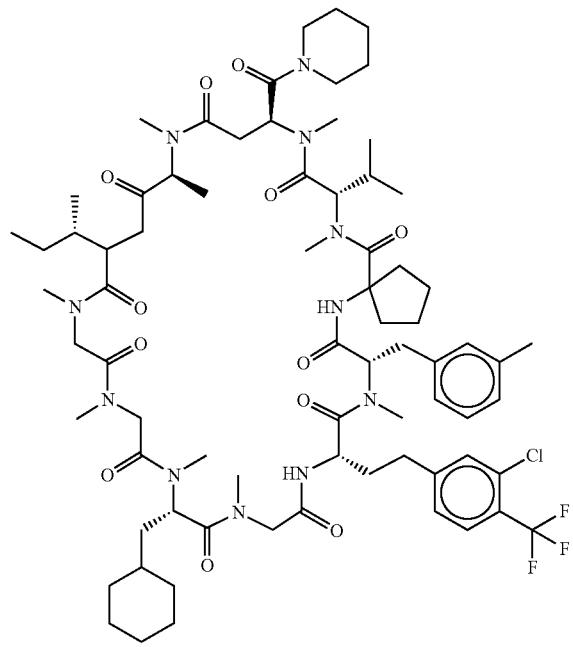 |
| 193 | 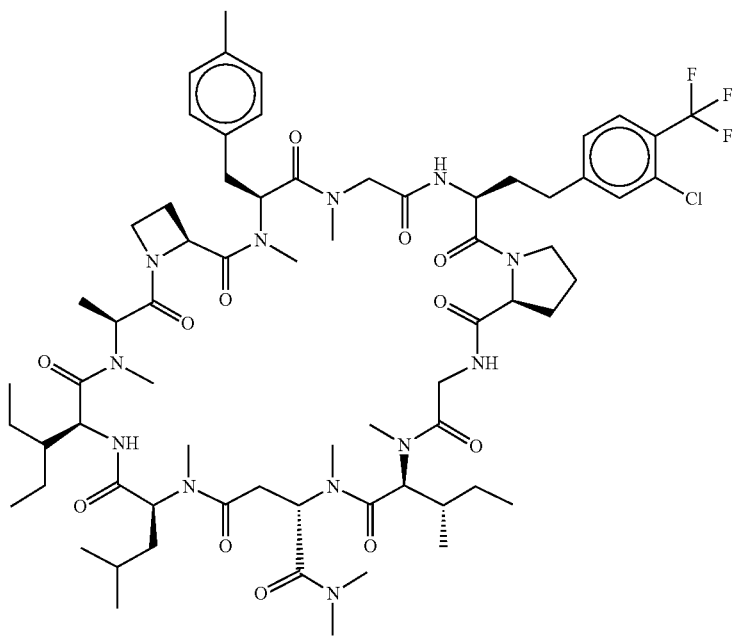 |

TABLE 24-continued
| Compound No. | Structural formula |
|---|---|
| 194 | 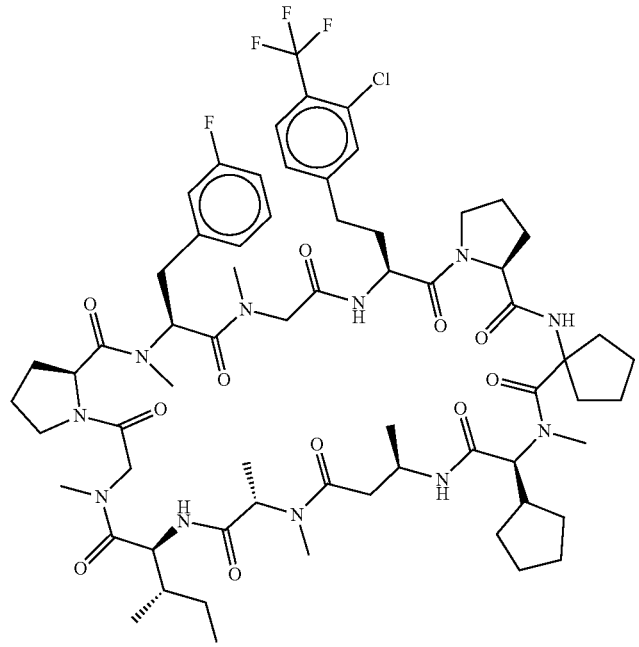 |
| 195 | 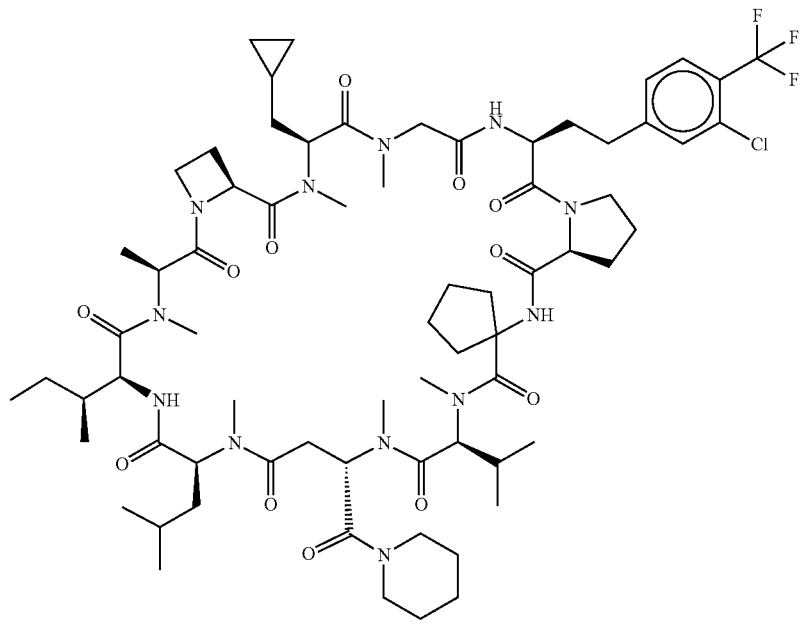 |

TABLE 24-continued
| Compound No. | Structural formula |
|---|---|
| 196 | 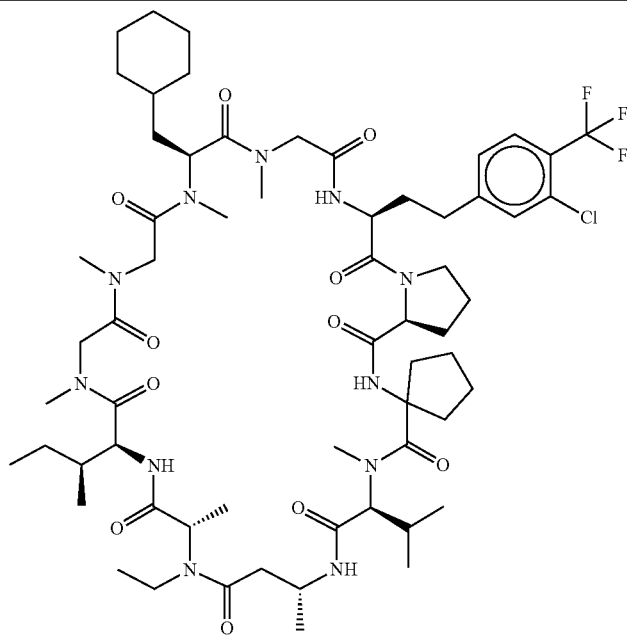 |
| 197 | 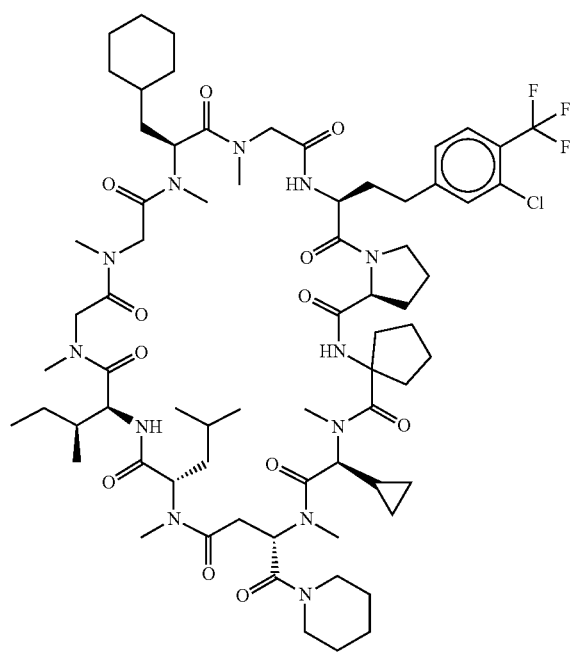 |

TABLE 24-continued
| Compound No. | Structural formula |
|---|---|
| 198 | 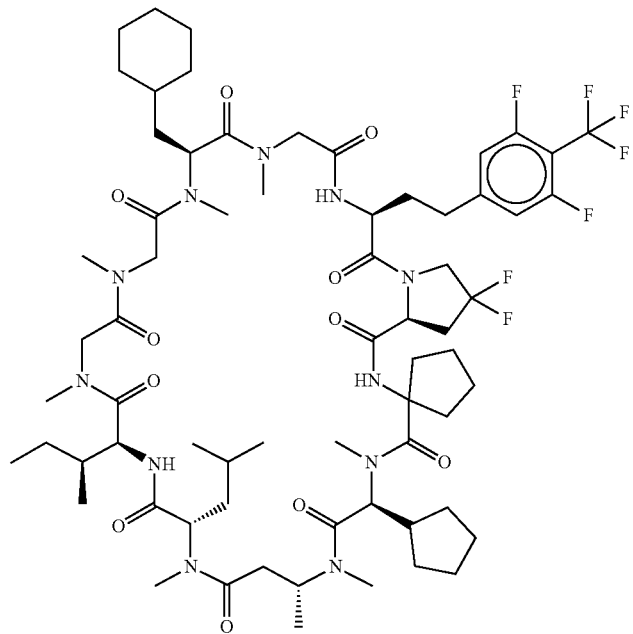 |
| 199 | 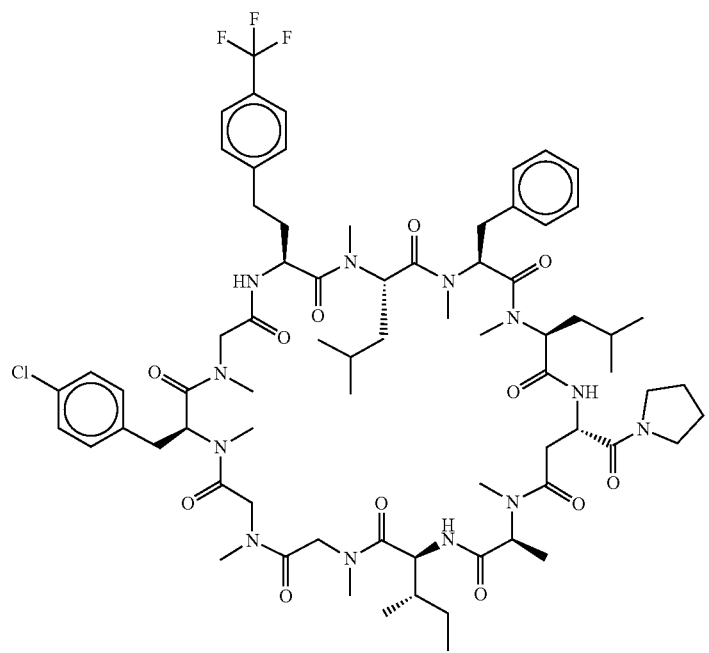 |

TABLE 24-continued
| Compound No. | Structural formula |
|---|---|
| 200 | 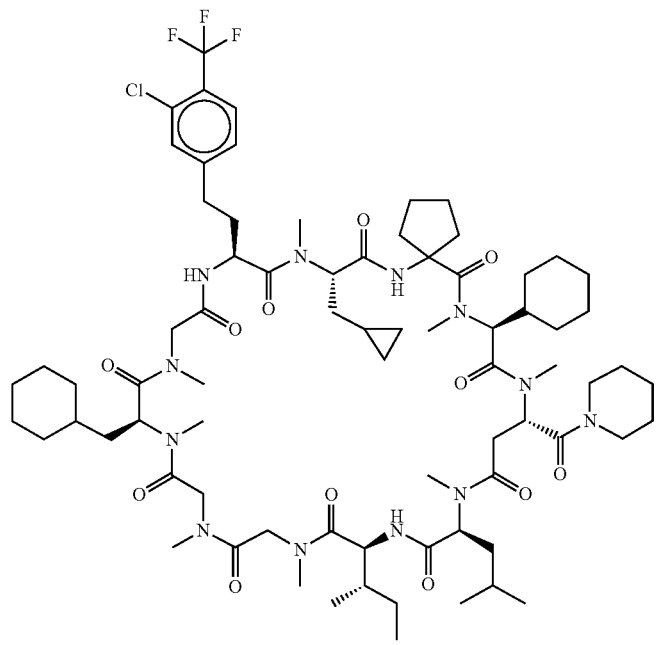 |
| 201 | 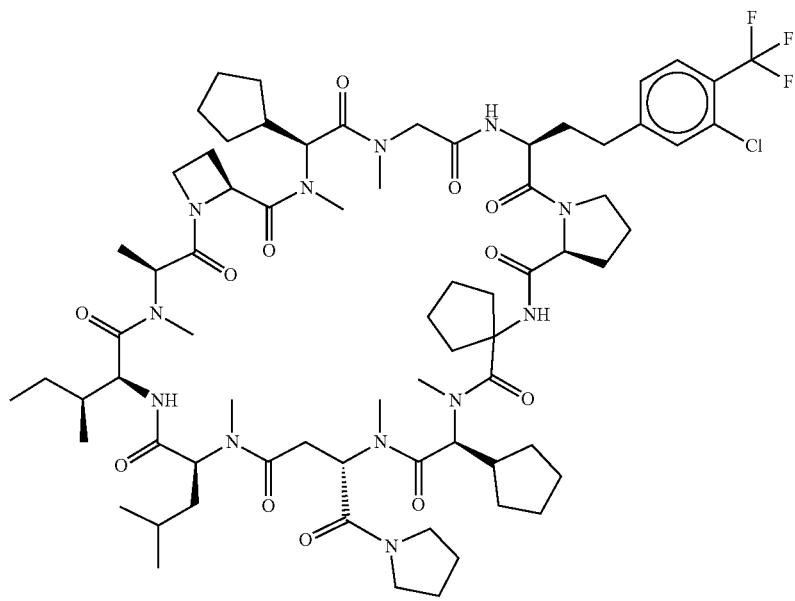 |

TABLE 24-continued
| Compound No. | Structural formula |
|---|---|
| 202 | 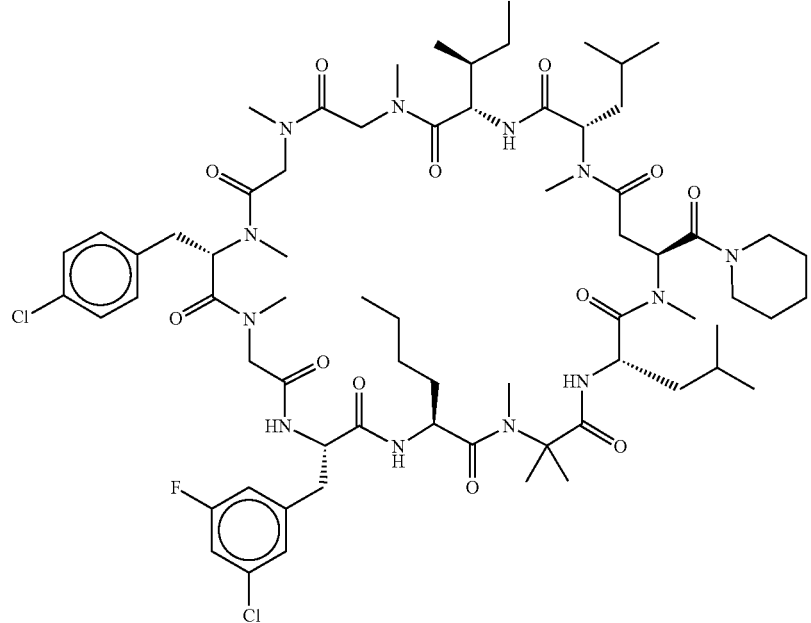 |
| 203 | 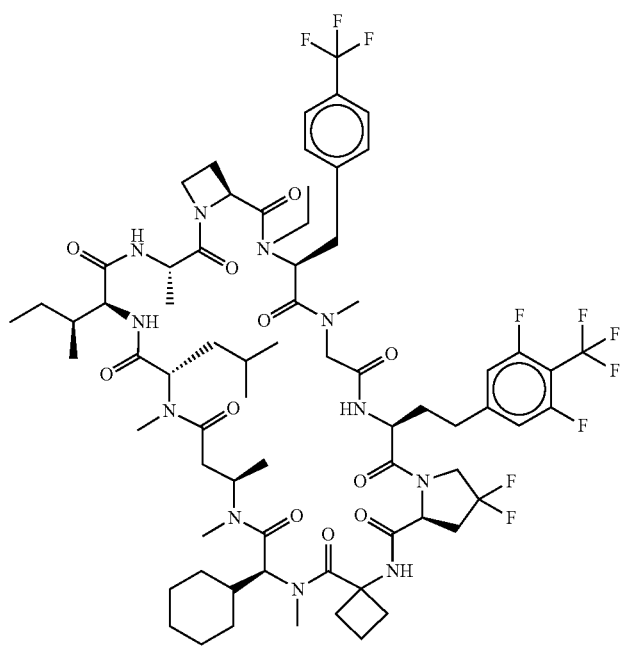 |

TABLE 24-continued
| Compound No. | Structural formula |
|---|---|
| 204 | 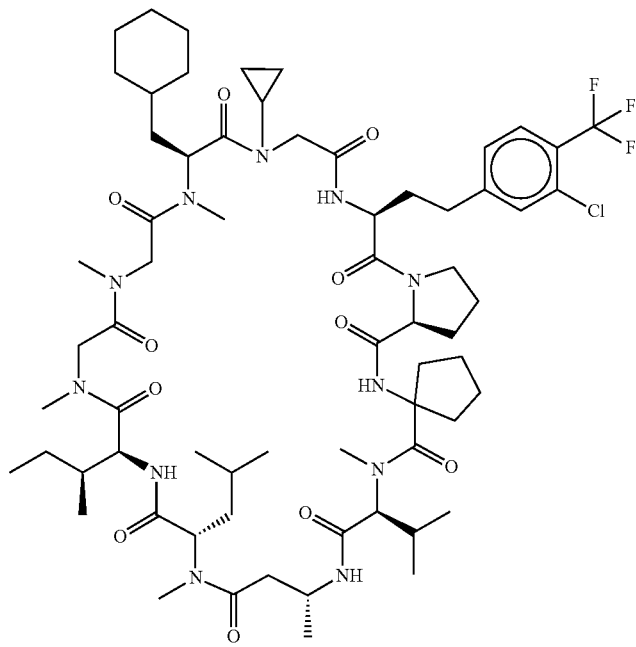 |
| 205 | 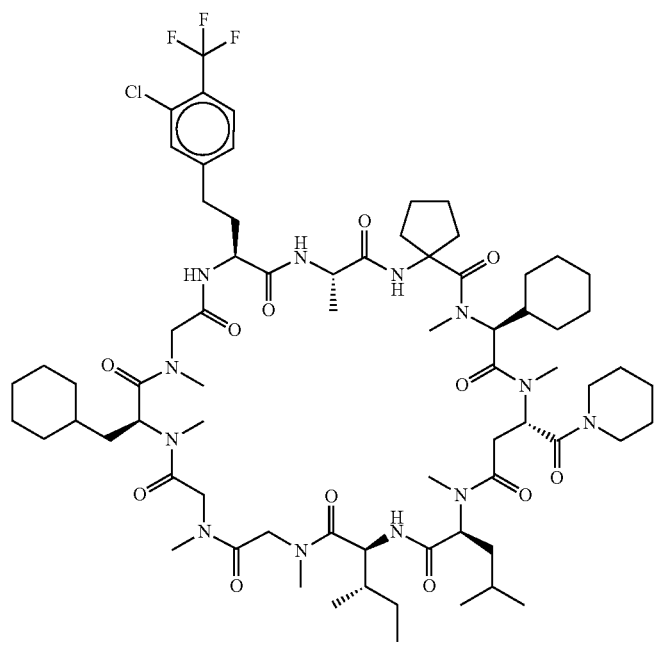 |

TABLE 24-continued
| Compound No. | Structural formula |
|---|---|
| 206 | 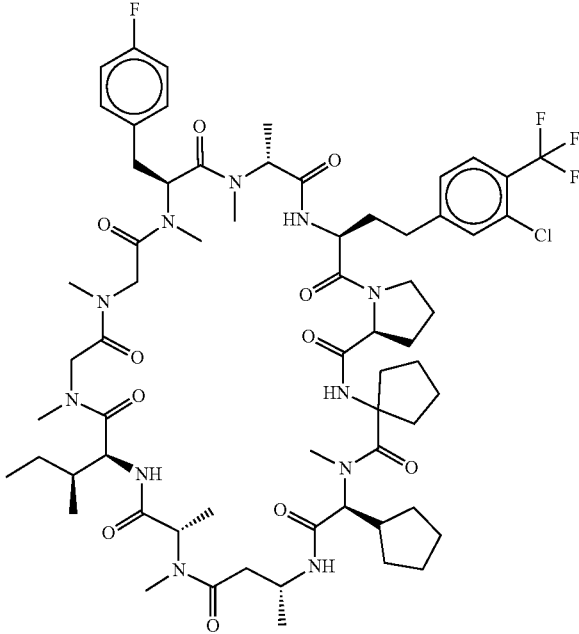 |
| 207 | 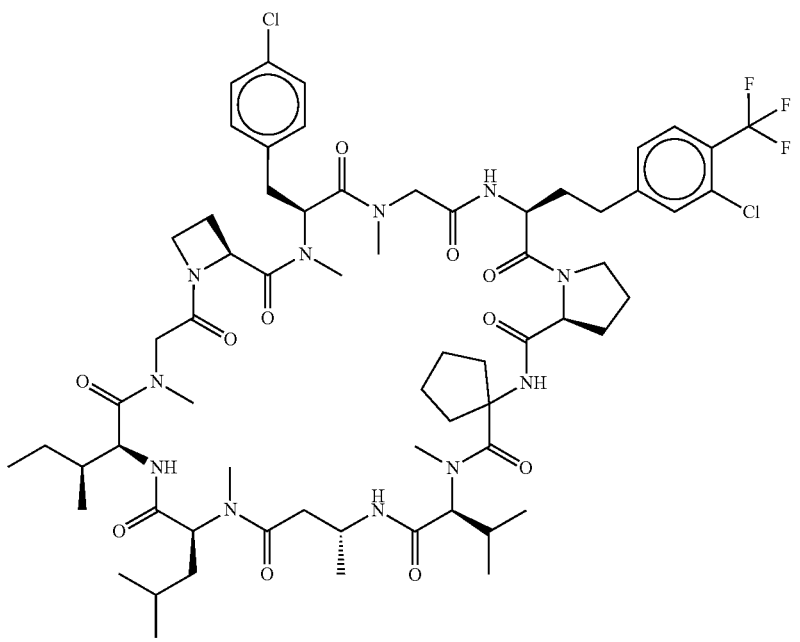 |

TABLE 24-continued
| Compound No. | Structural formula |
|---|---|
| 208 | 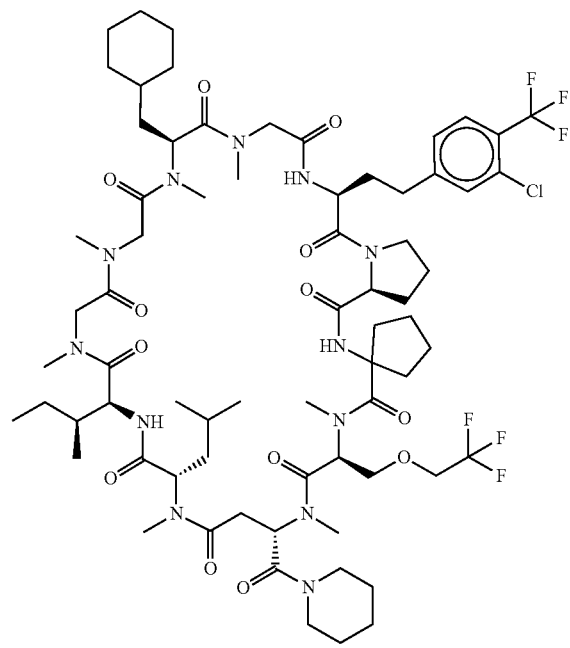 |
| 209 | 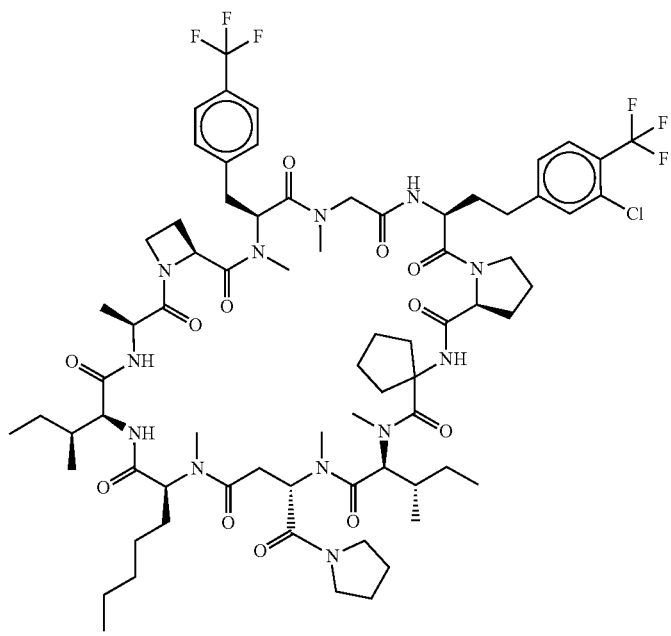 |

TABLE 24-continued
| Compound No. | Structural formula |
|---|---|
| 210 | 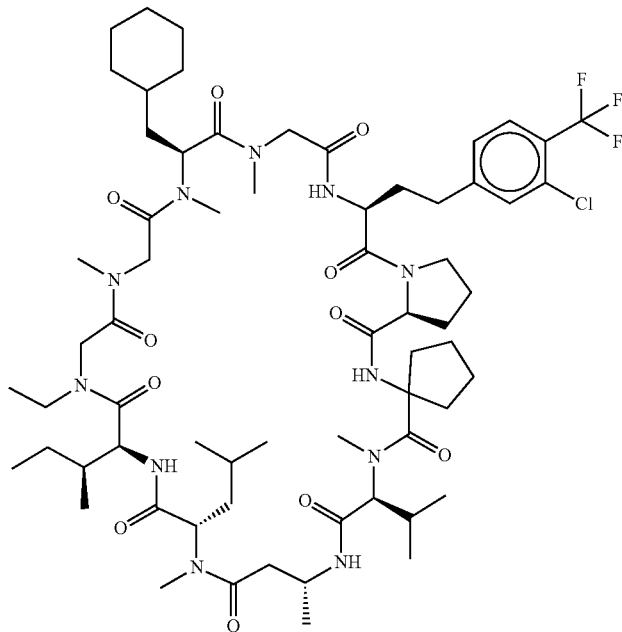 |
| 211 | 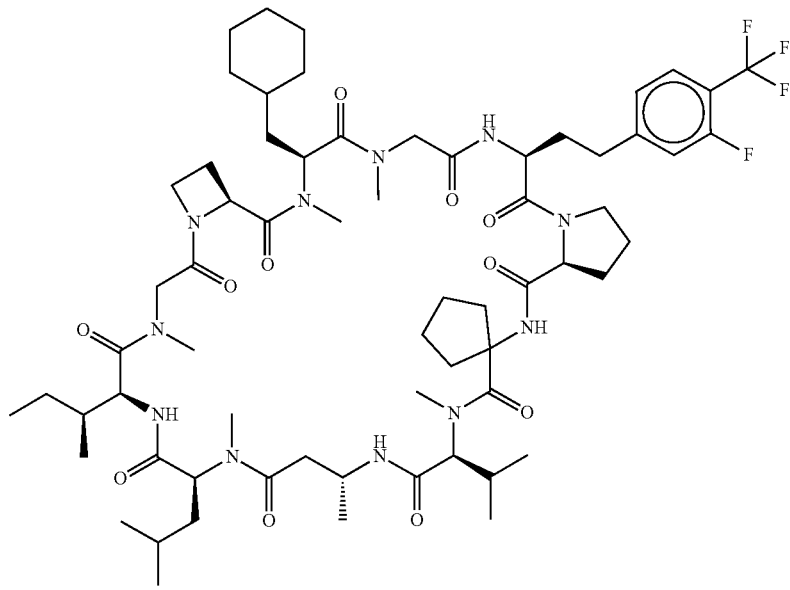 |

| Compound No. | Structural formula |
|---|---|
| 212 | 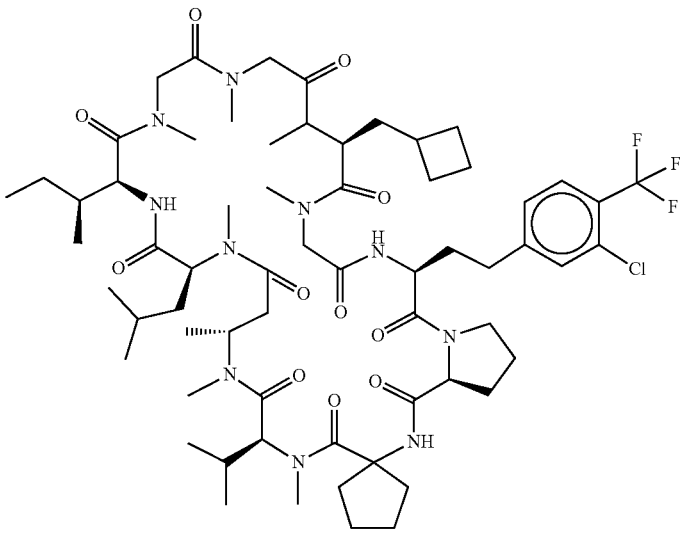 |
| 213 | 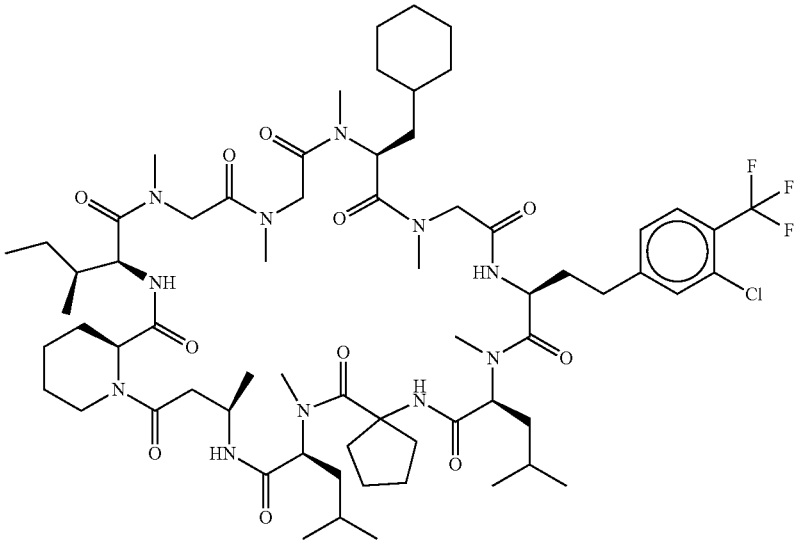 |

TABLE 24-continued
| Compound No. | Structural formula |
|---|---|
| 214 | 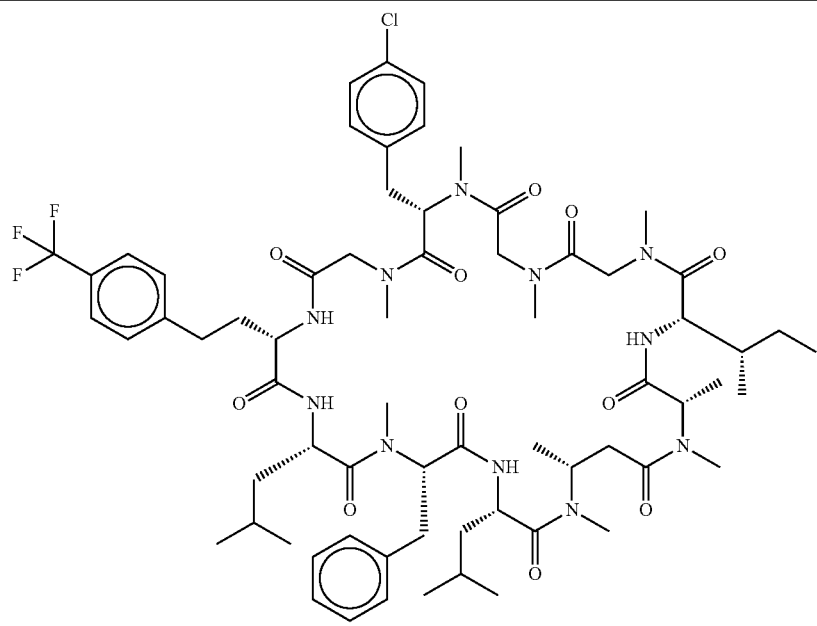 |
| 215 | 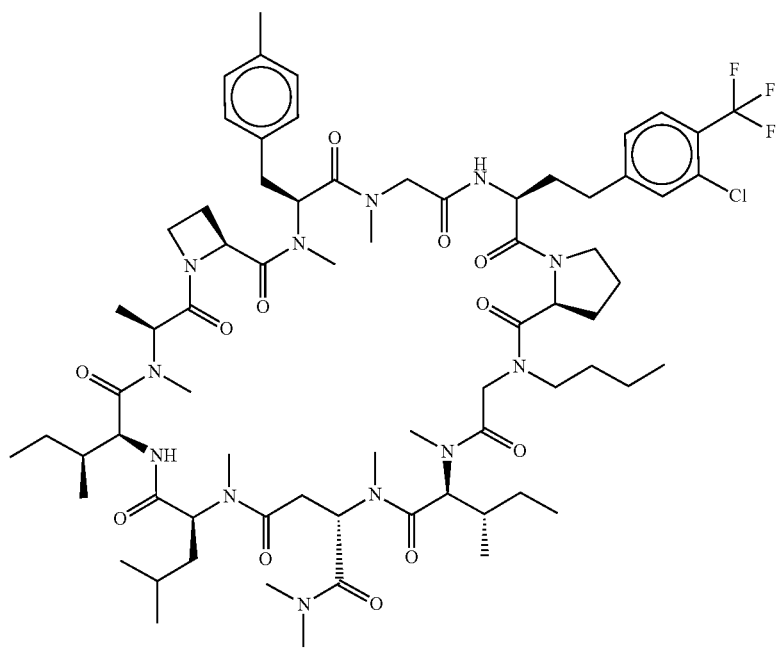 |

TABLE 24-continued
| Compound No. | Structural formula |
|---|---|
| 216 | 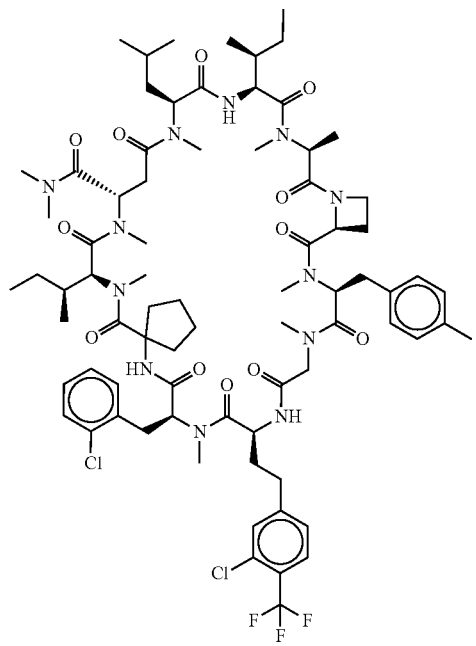 |
| 217 | 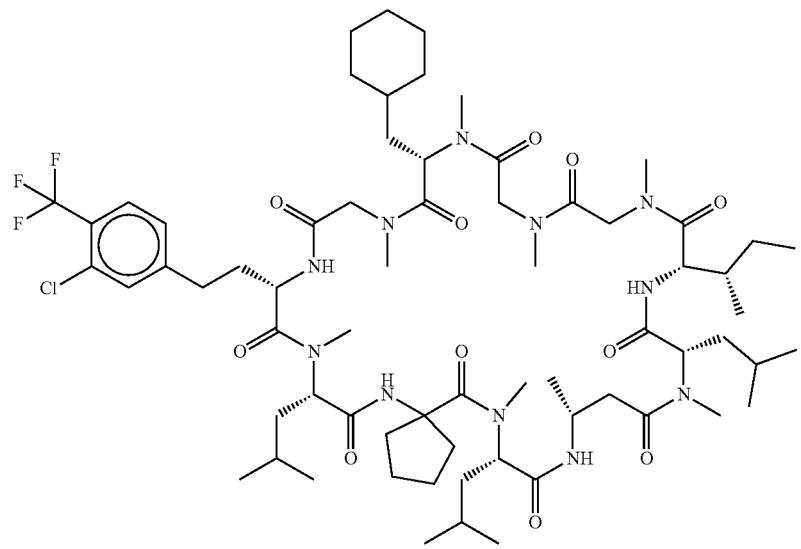 |

TABLE 24-continued
| Compound No. | Structural formula |
|---|---|
| 218 | 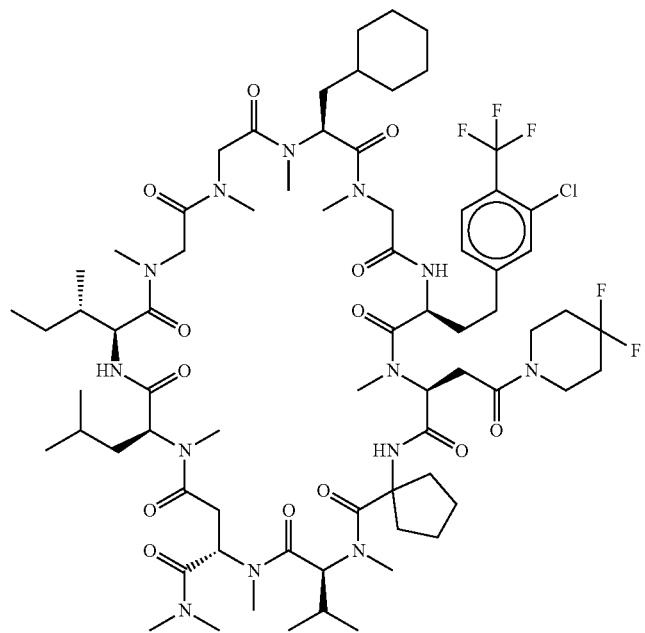 |
| 219 | 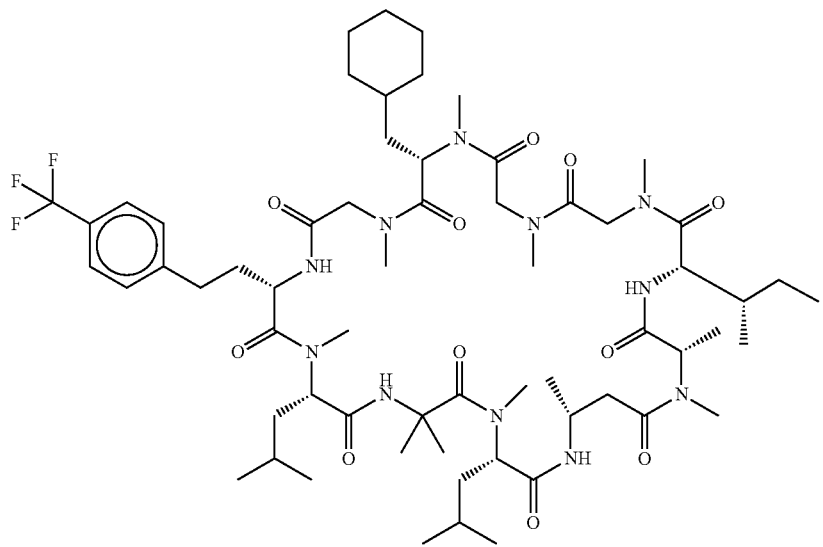 |

TABLE 24-continued
| Compound No. | Structural formula |
|---|---|
| 220 | 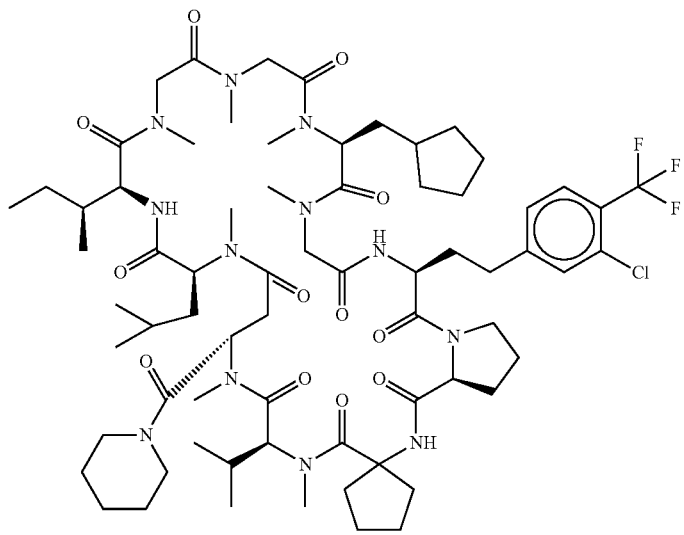 |
| 221 | 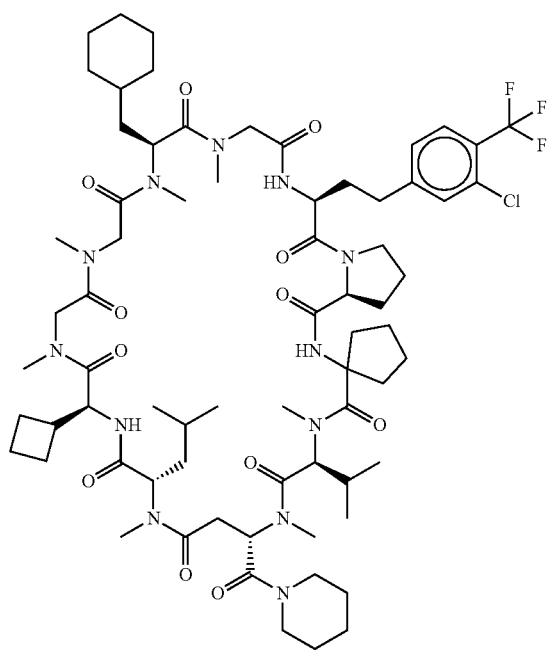 |

TABLE 24-continued
| Compound No. | Structural formula |
| --- | --- |
| 222 | 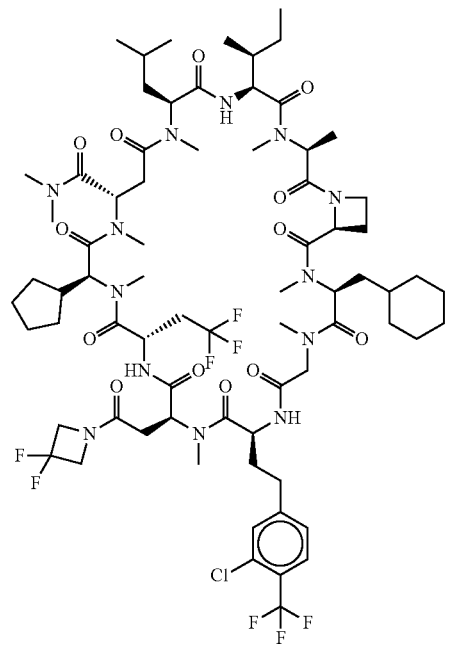 |
| 223 | 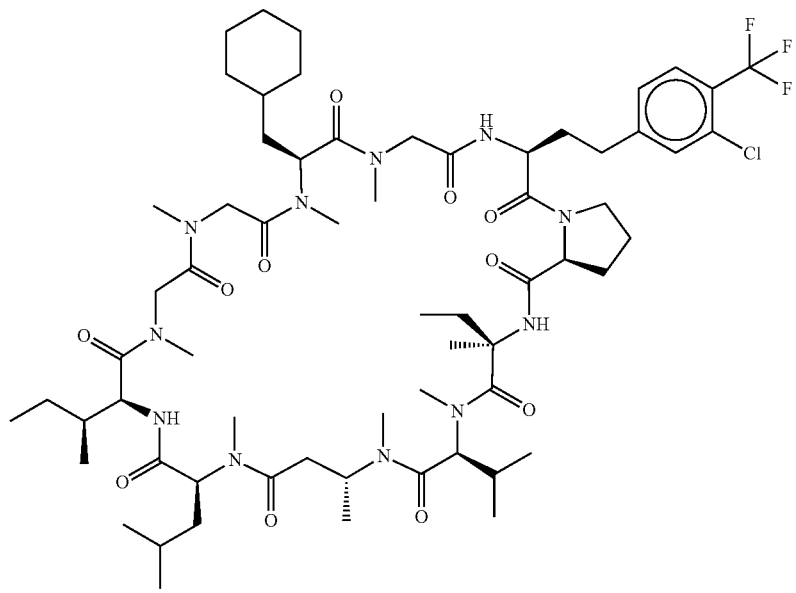 |

TABLE 24-continued
| Compound No. | Structural formula |
|---|---|
| 224 | 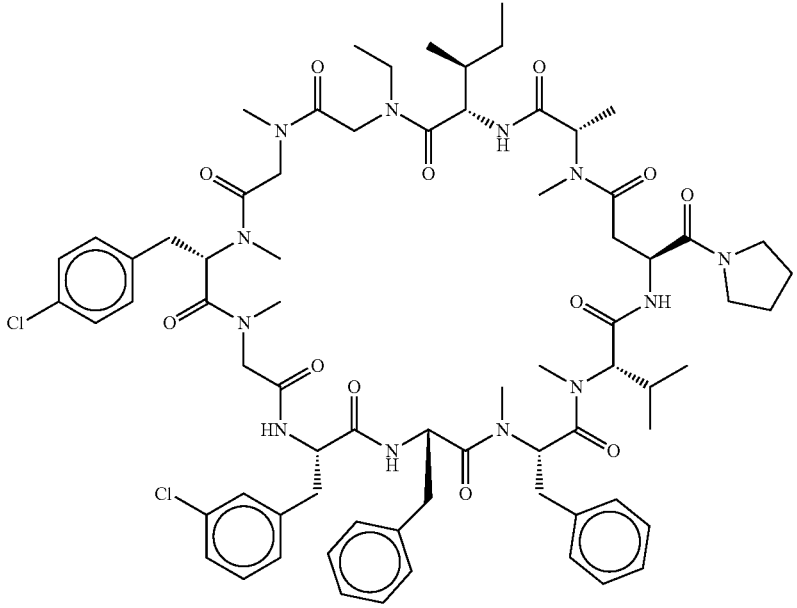 |
| 225 | 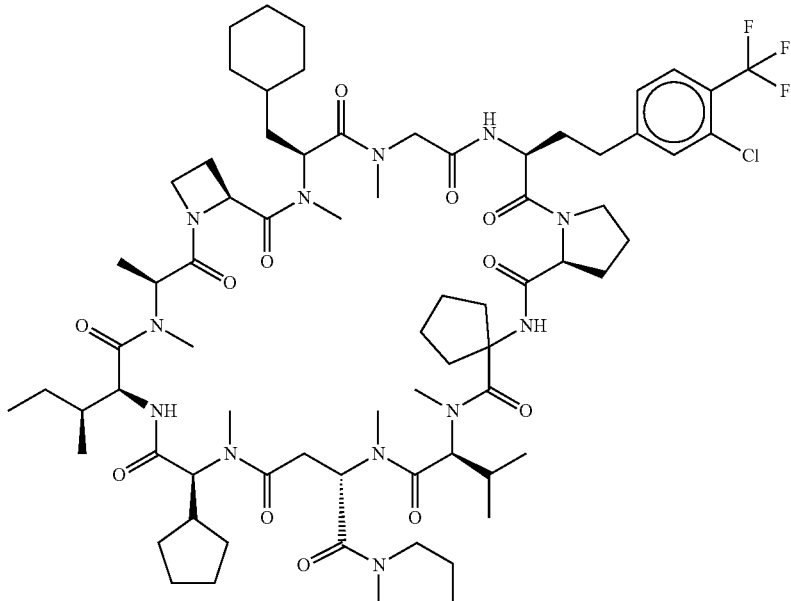 |

TABLE 24-continued
| Compound No. | Structural formula |
|---|---|
| 226 | 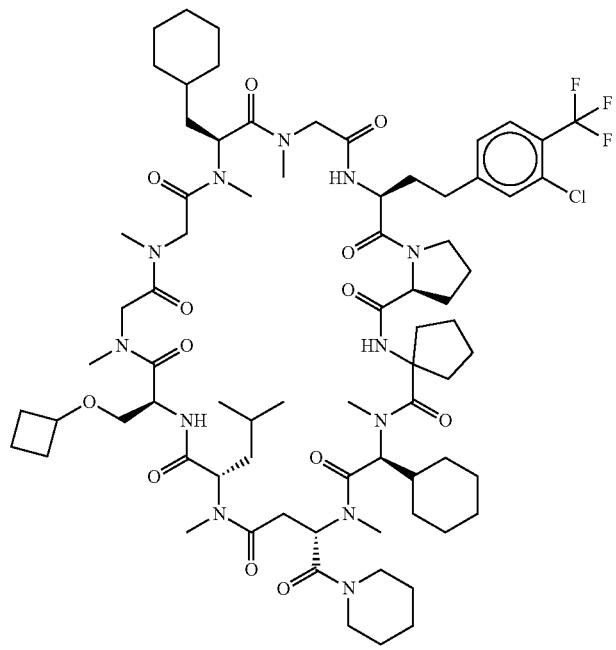 |
| 227 | 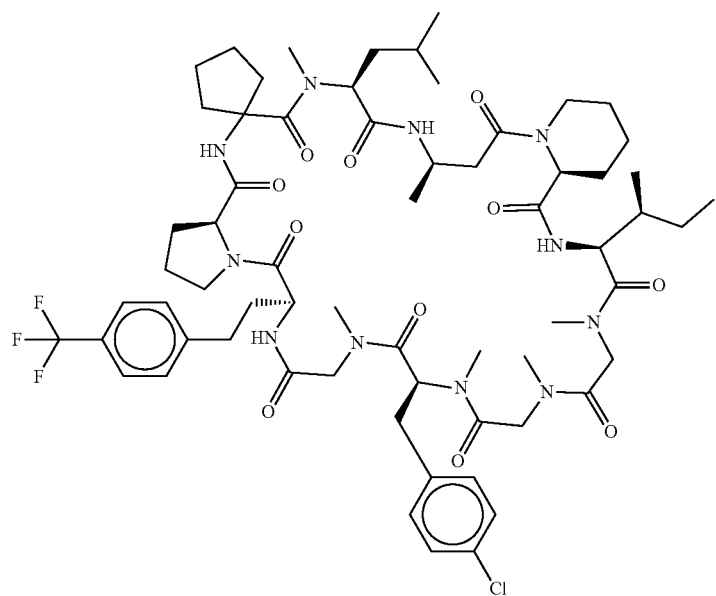 |

TABLE 24-continued
| Compound No. | Structural formula |
|---|---|
| 228 | 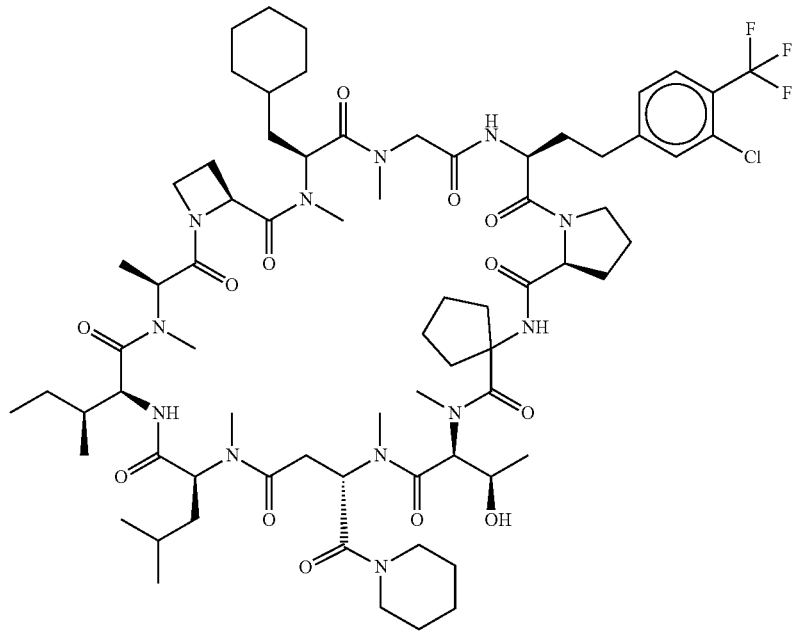 |
| 229 | 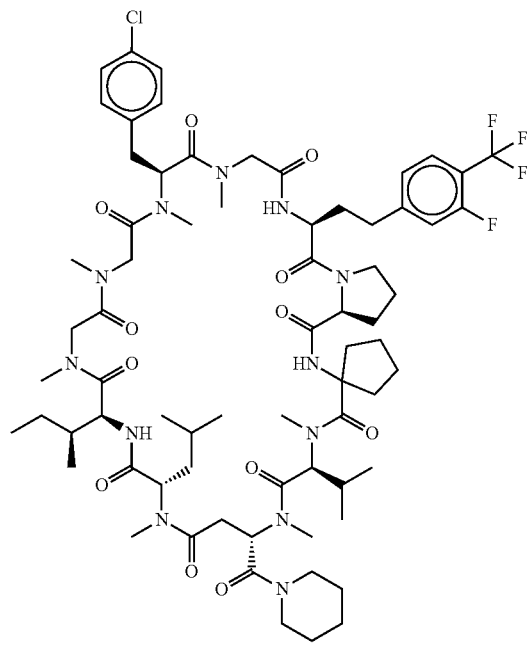 |

TABLE 24-continued
| Compound No. | Structural formula |
|---|---|
| 230 | 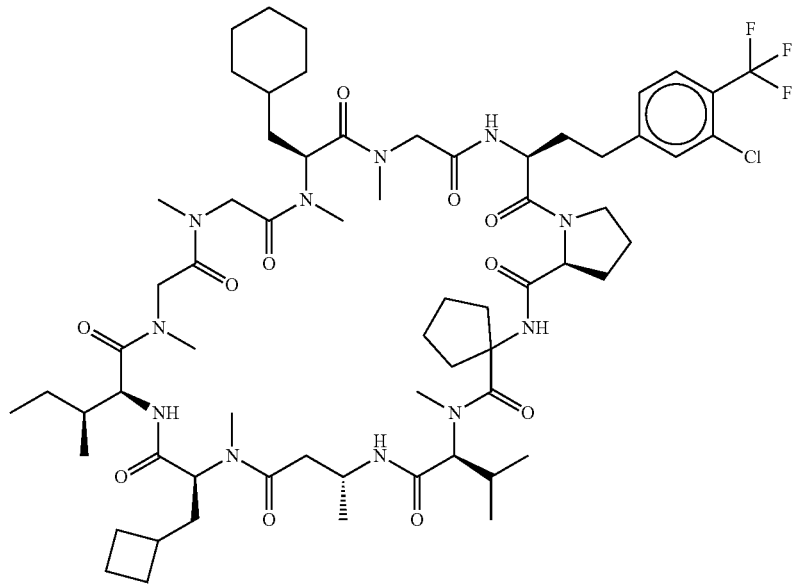 |
| 231 | 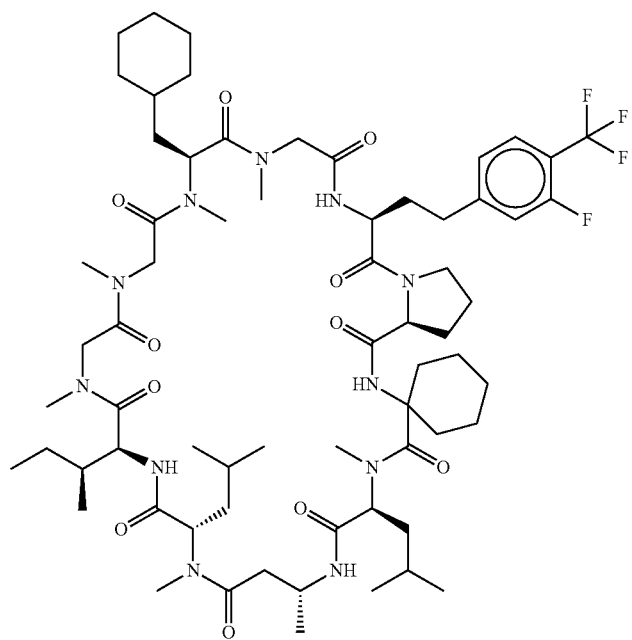 |

TABLE 24-continued
| Compound No. | Structural formula |
|---|---|
| 232 | 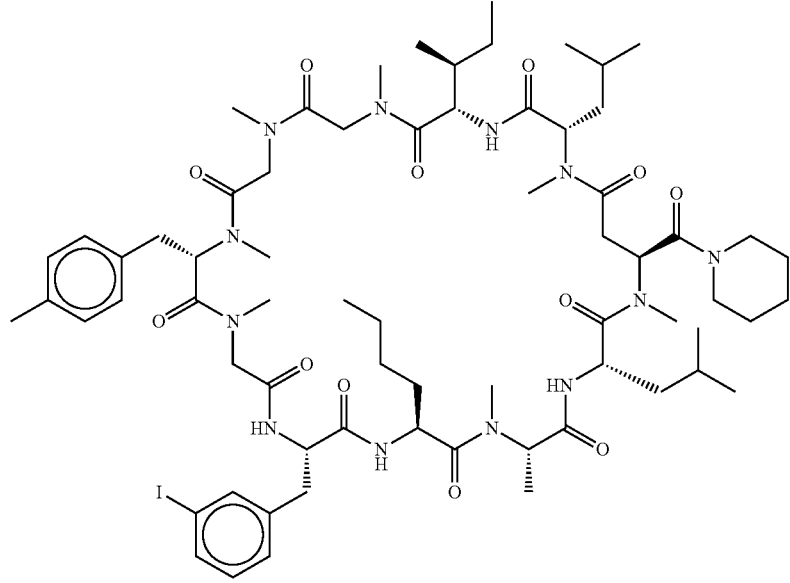 |
| 233 | 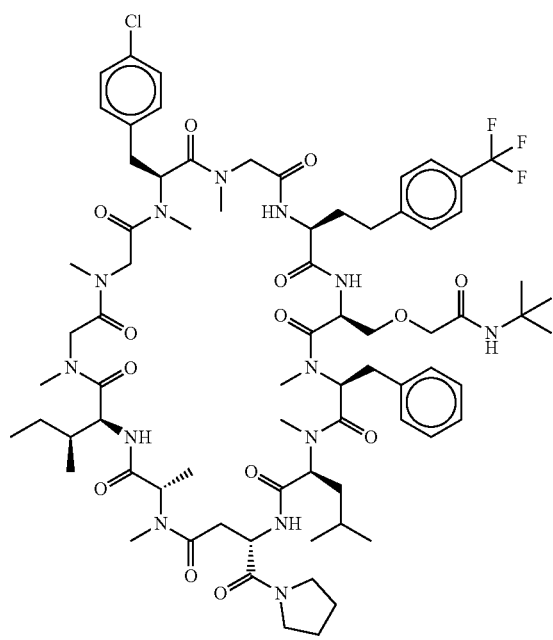 |

TABLE 24-continued
| Compound No. | Structural formula |
| --- | --- |
| 234 | 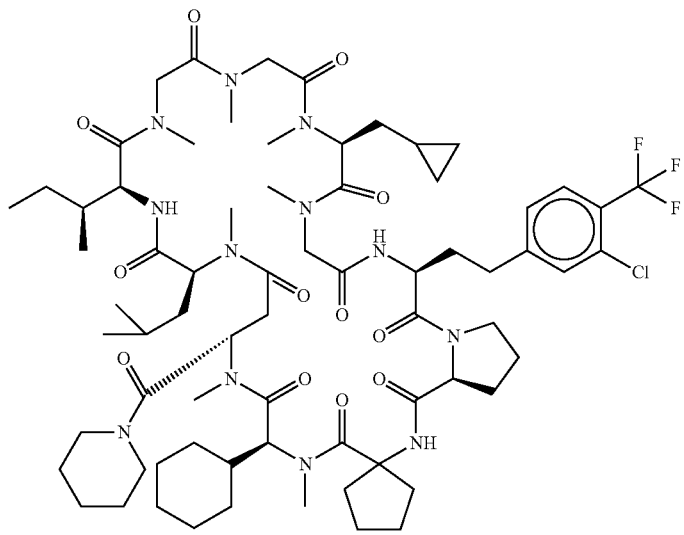 |
| 235 | 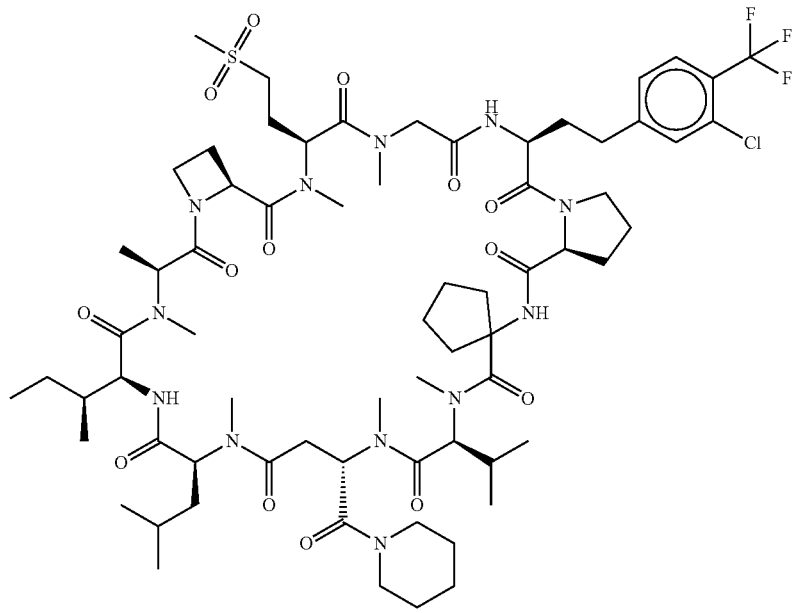 |

TABLE 24-continued
| Compound No. | Structural formula |
|---|---|
| 236 | 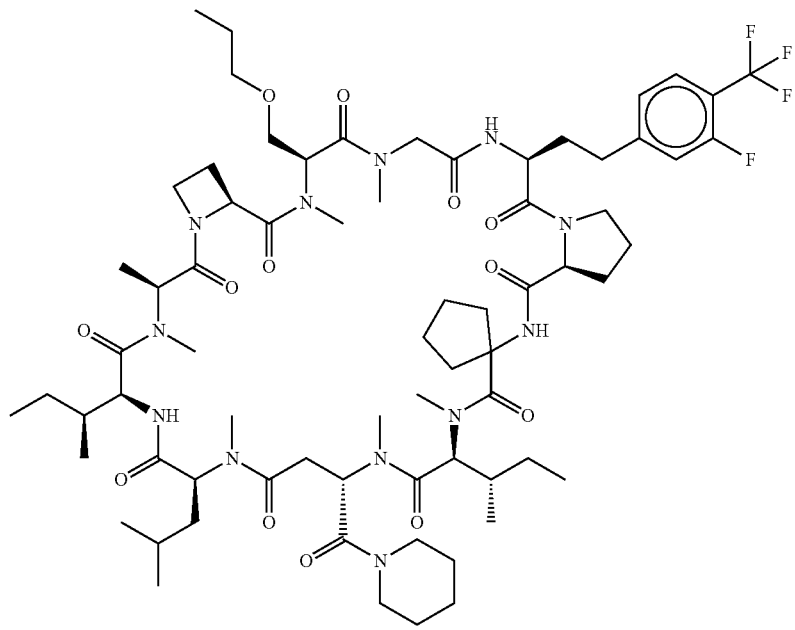 |
| 237 | 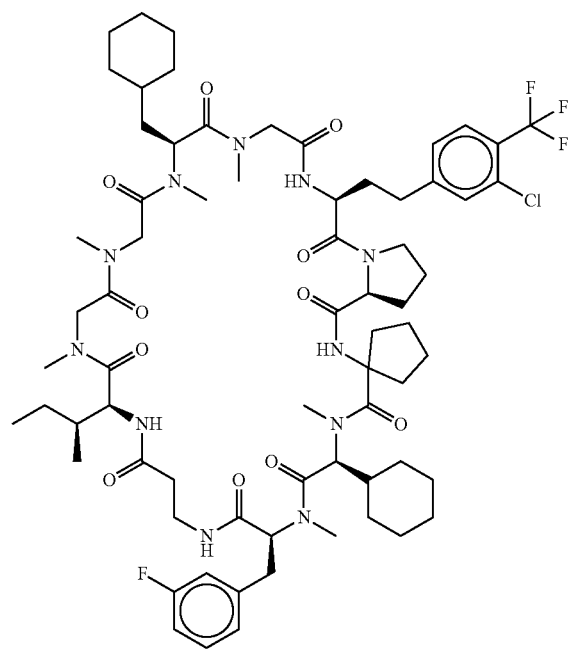 |

TABLE 24-continued
| Compound No. | Structural formula |
|---|---|
| 238 | 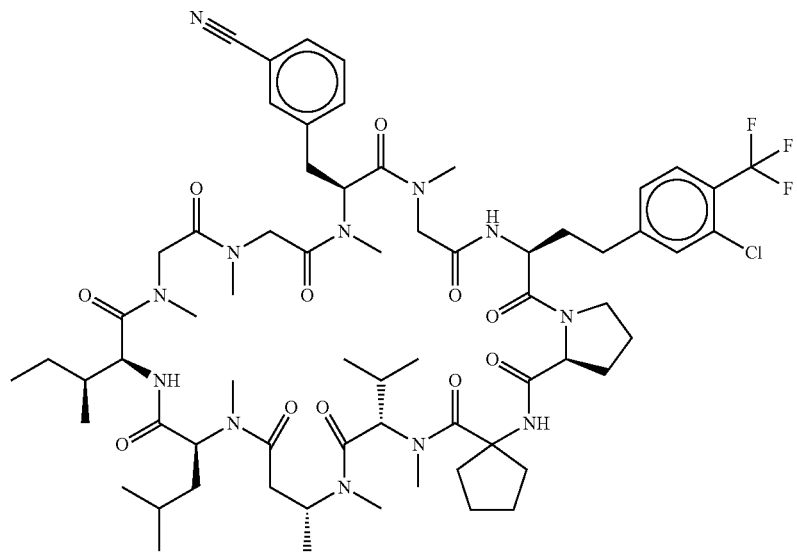 |
| 239 | 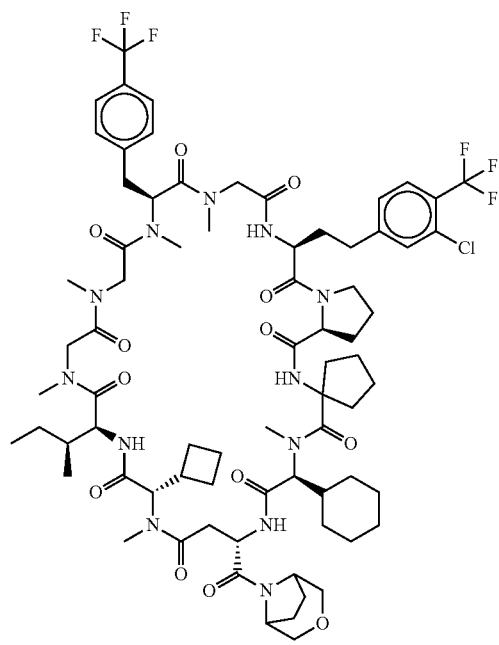 |

TABLE 24-continued
| Compound No. | Structural formula |
|---|---|
| 240 | 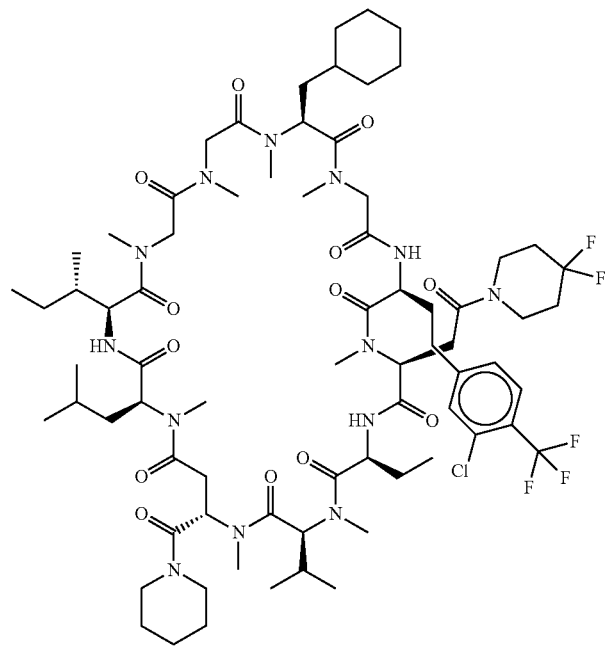 |
| 241 | 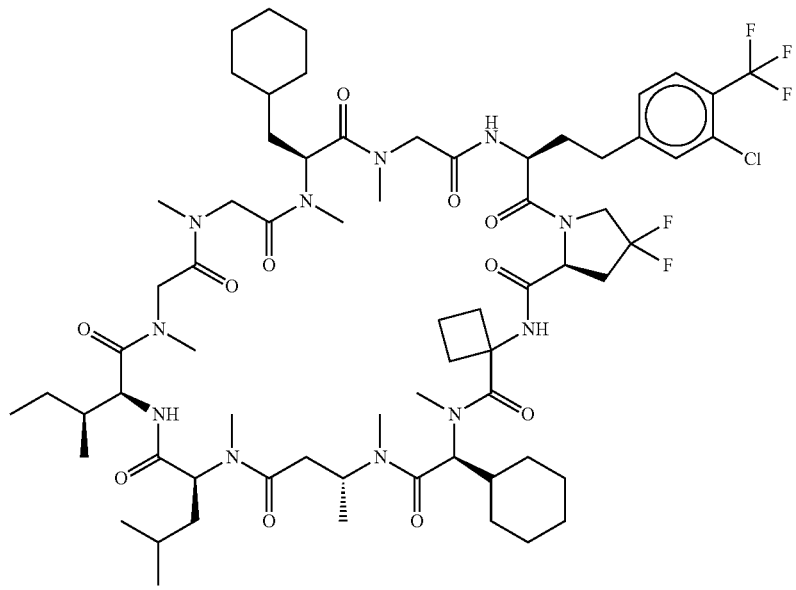 |

TABLE 24-continued
| Compound No. | Structural formula |
|---|---|
| 242 | 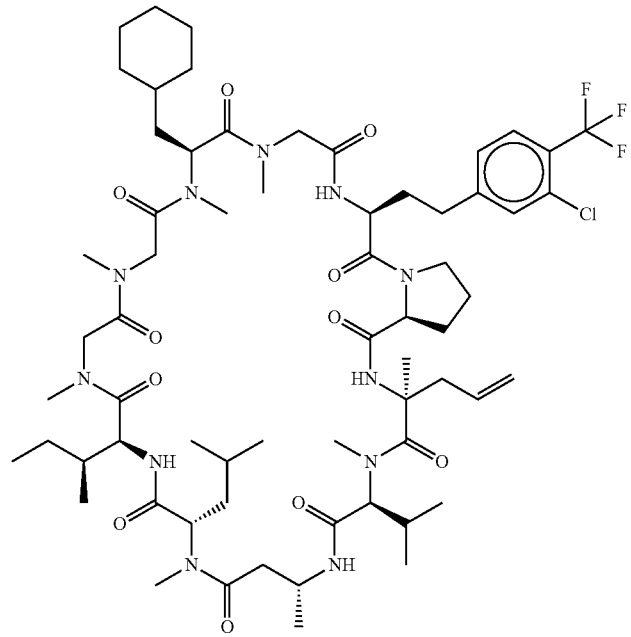 |
| 243 | 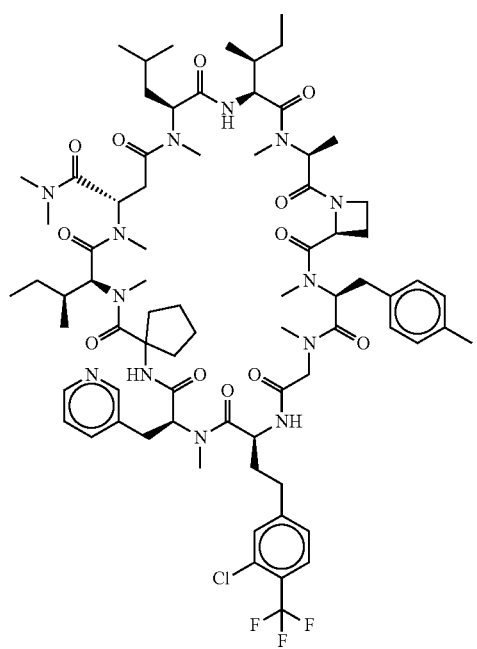 |

TABLE 24-continued
| Compound No. | Structural formula |
|---|---|
| 244 | 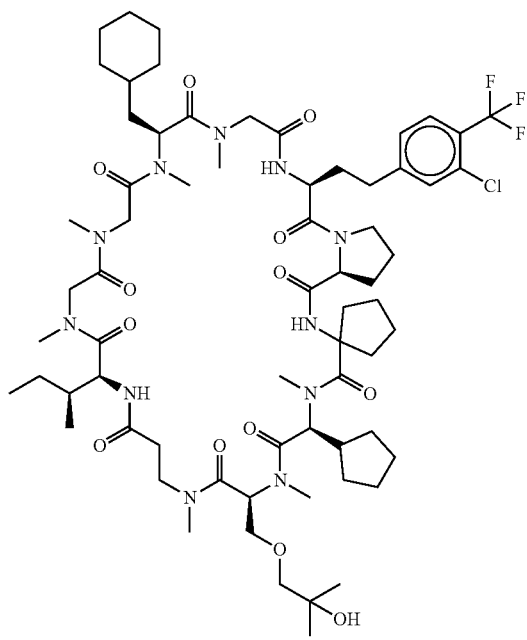 |
| 245 | 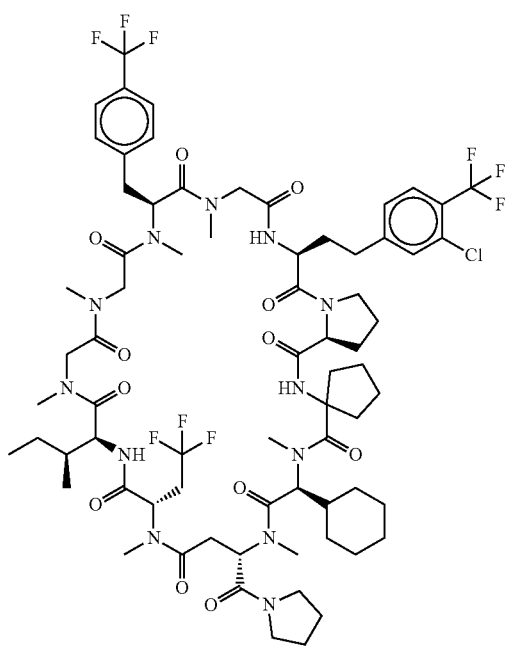 |

TABLE 24-continued
| Compound No. | Structural formula |
|---|---|
| 246 | 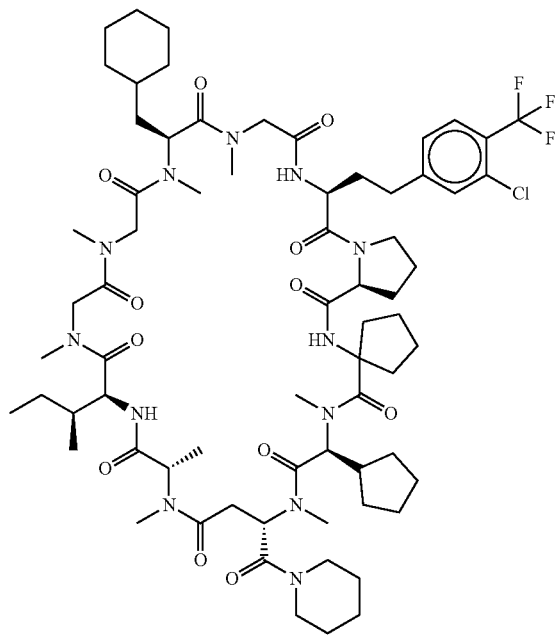 |
| 247 | 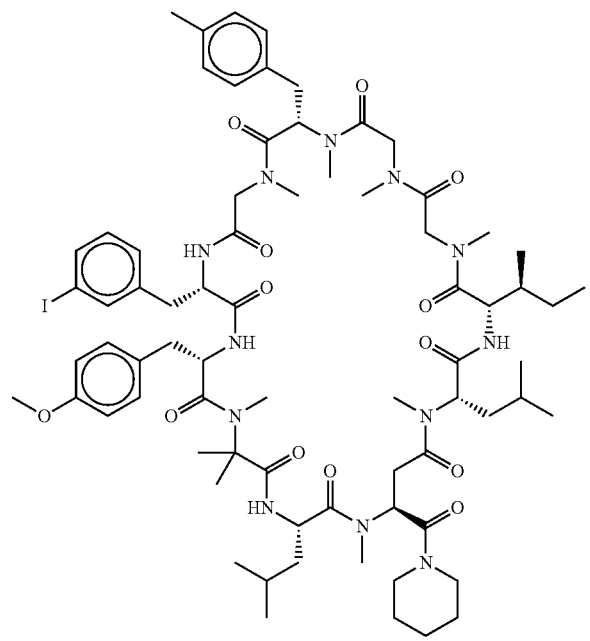 |

TABLE 24-continued
| Compound No. | Structural formula |
|---|---|
| 248 | 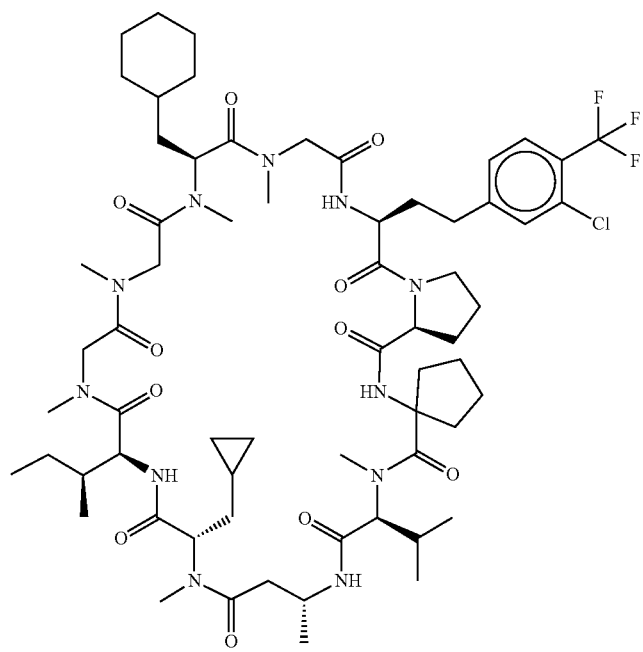 |
| 249 | 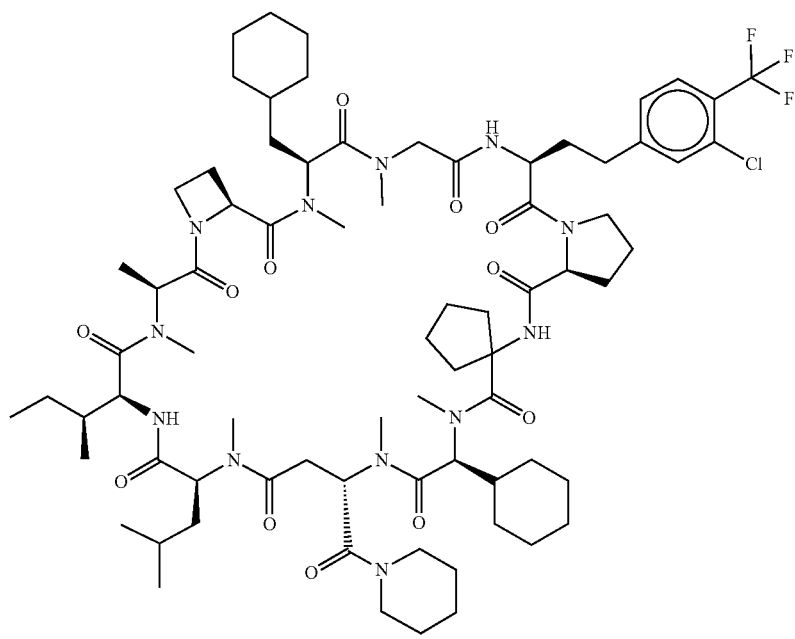 |

TABLE 24-continued
| Compound No. | Structural formula |
|---|---|
| 250 | 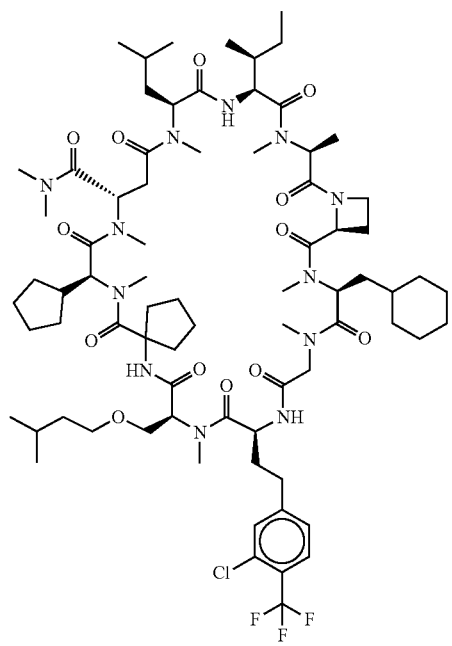 |
| 251 | 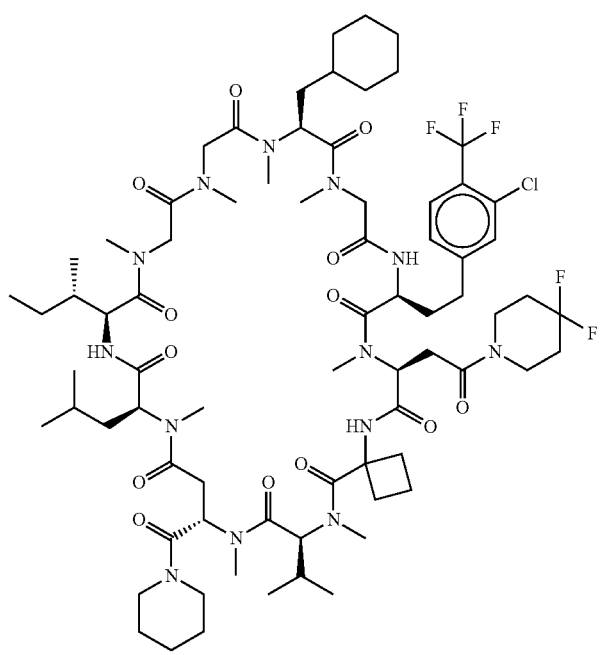 |

TABLE 24-continued
| Compound No. | Structural formula |
| --- | --- |
| 252 | 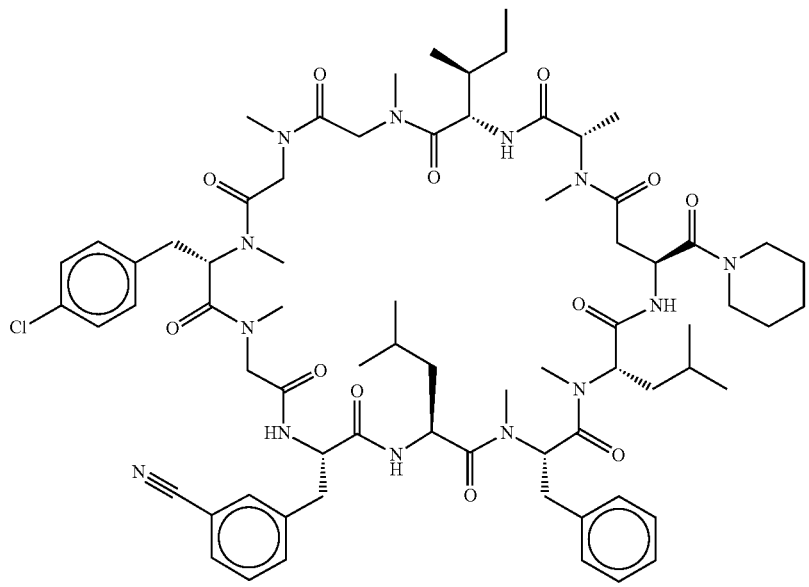 |
| 253 | 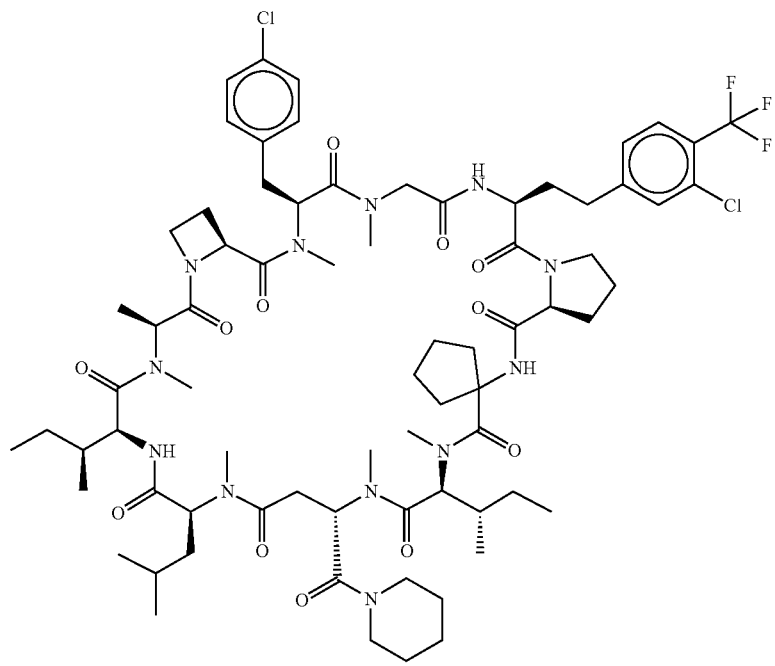 |

TABLE 24-continued
| Compound No. | Structural formula |
|---|---|
| 254 | 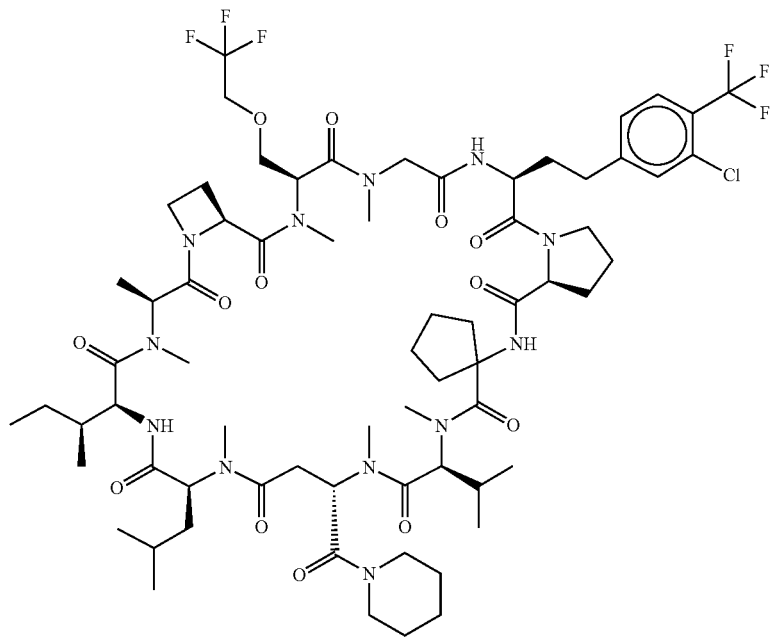 |
| 255 | 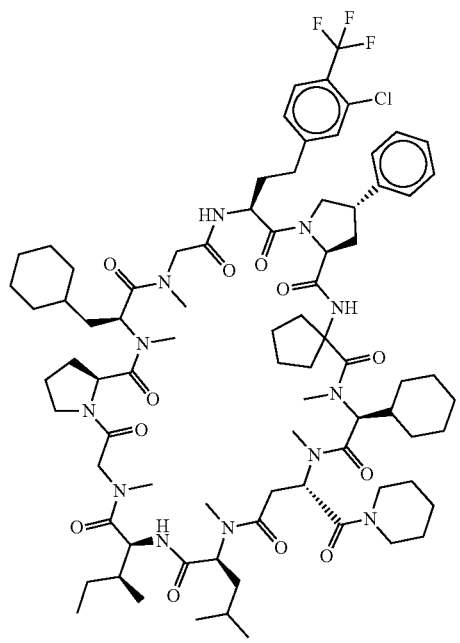 |

TABLE 24-continued
| Compound No. | Structural formula |
|---|---|
| 256 | 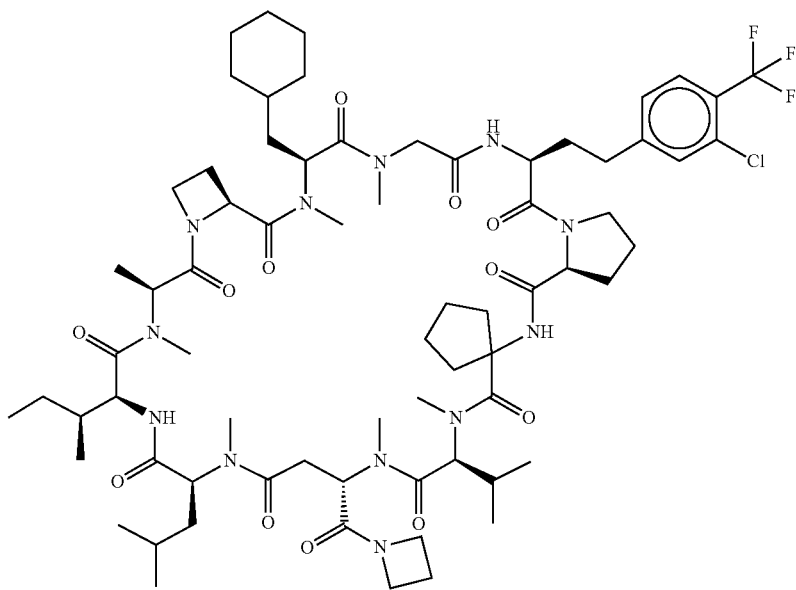 |
| 257 | 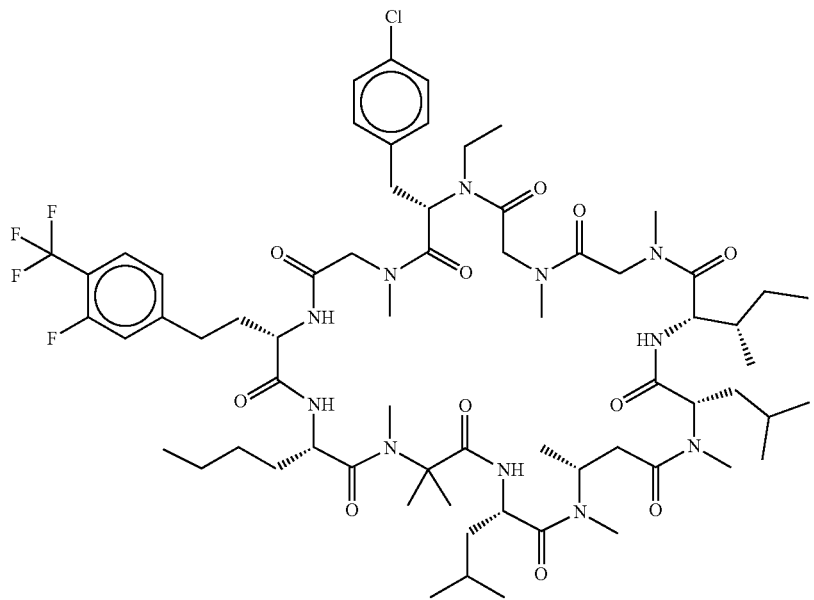 |

TABLE 24-continued
| Compound No. | Structural formula |
|---|---|
| 258 | 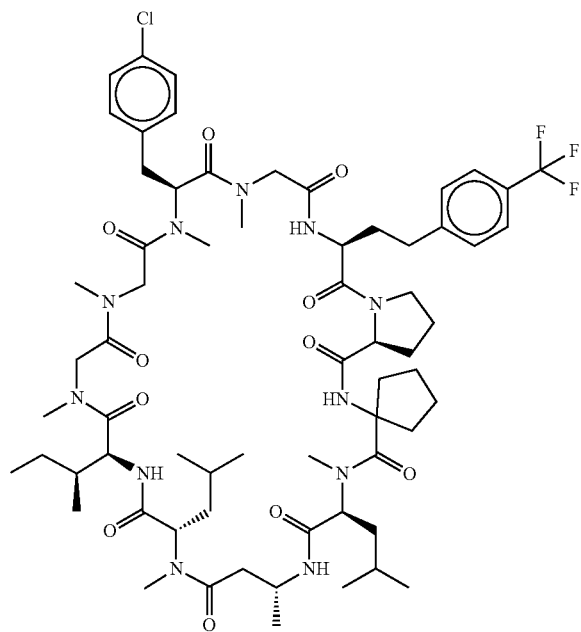 |
| 259 | 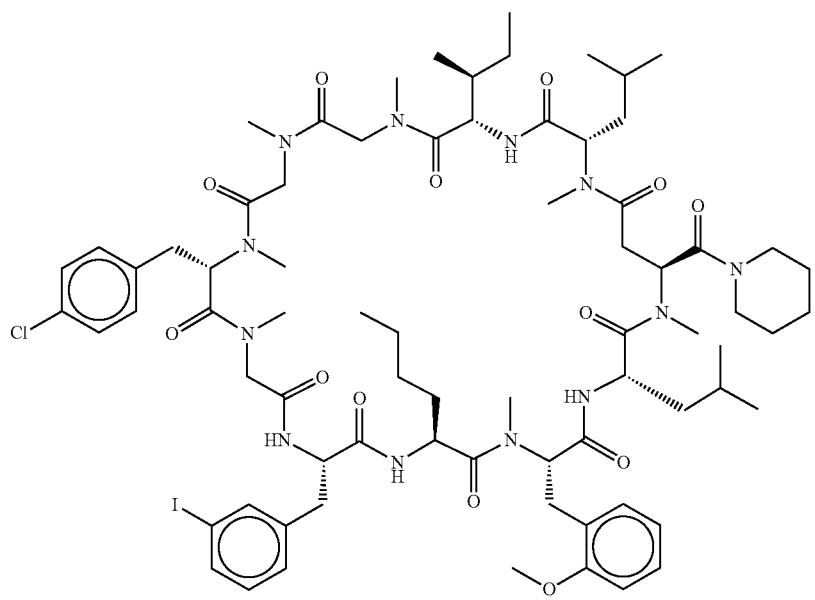 |

TABLE 24-continued
| Compound No. | Structural formula |
|---|---|
| 260 | 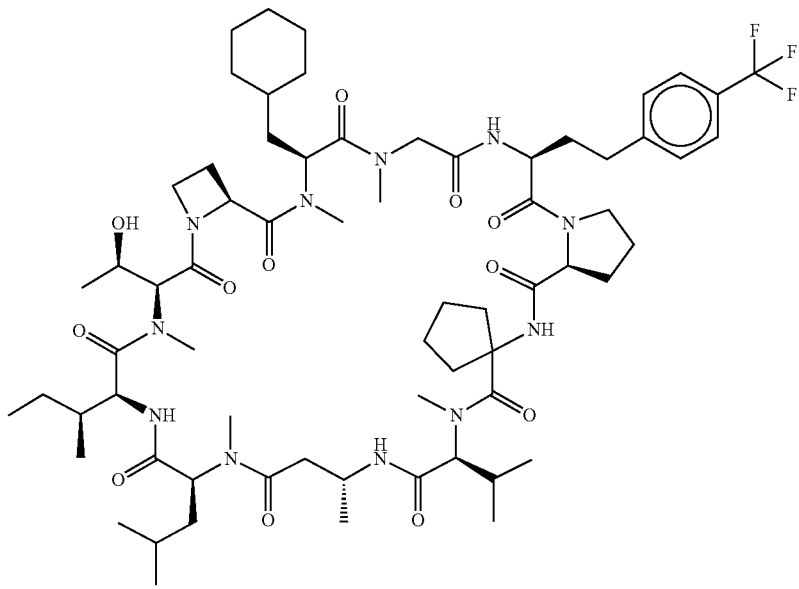 |
| 261 | 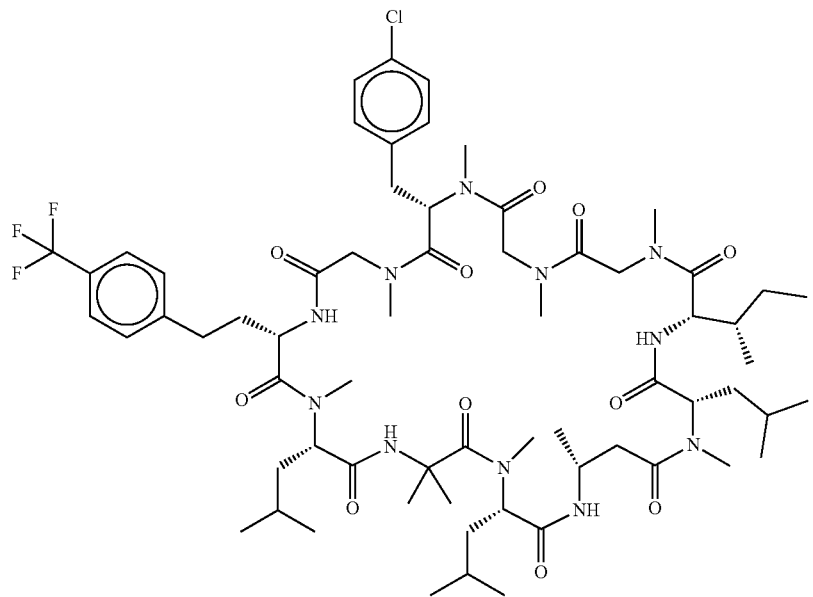 |

TABLE 24-continued
| Compound No. | Structural formula |
| --- | --- |
| 262 | 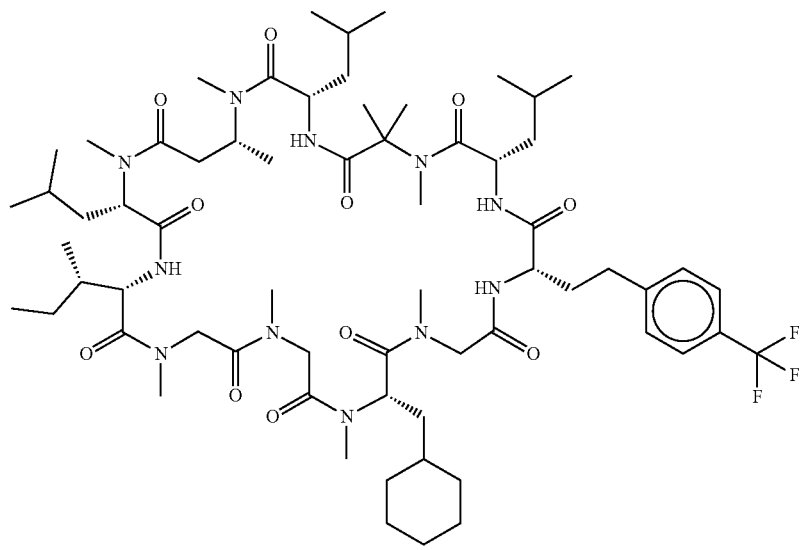 |
| 263 | 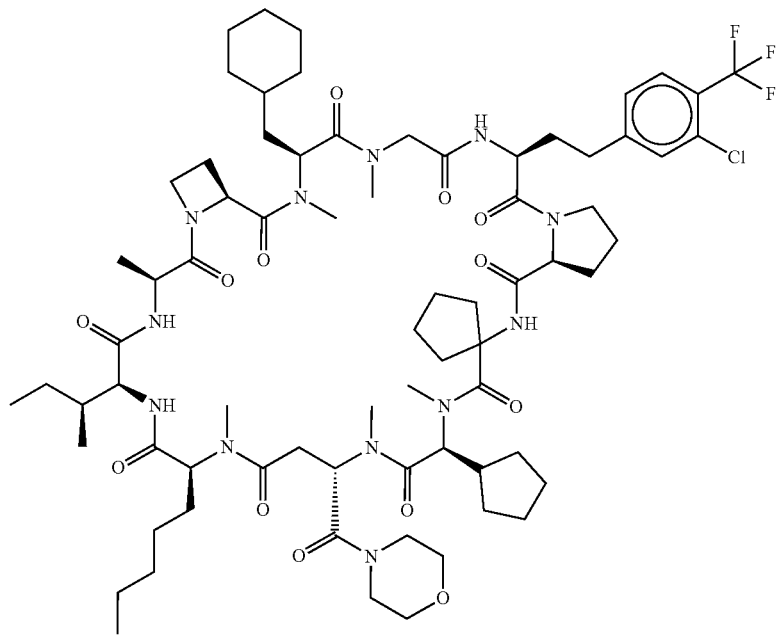 |

TABLE 24-continued
| Compound No. | Structural formula |
|---|---|
| 264 | 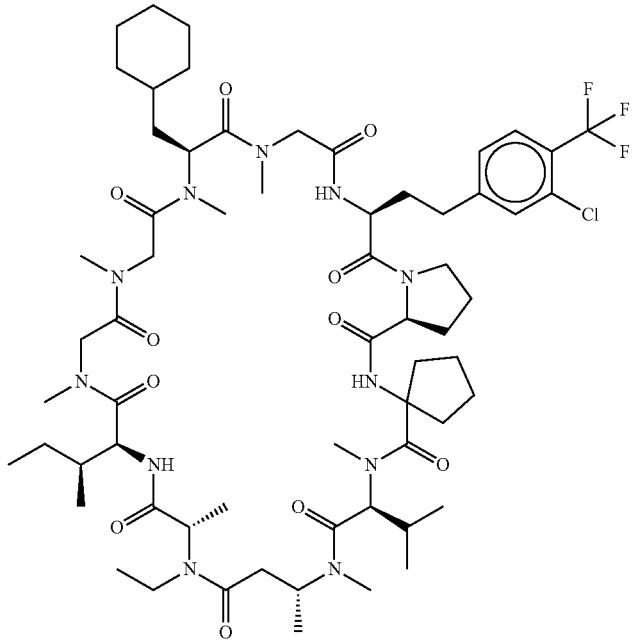 |
| 265 | 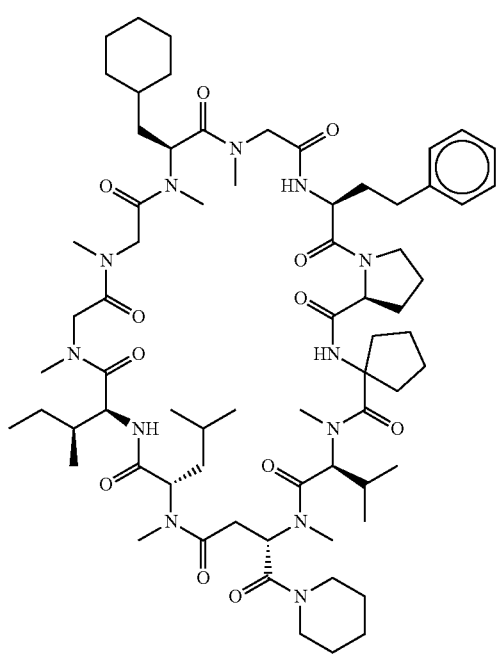 |

TABLE 24-continued
| Compound No. | Structural formula |
|---|---|
| 266 | 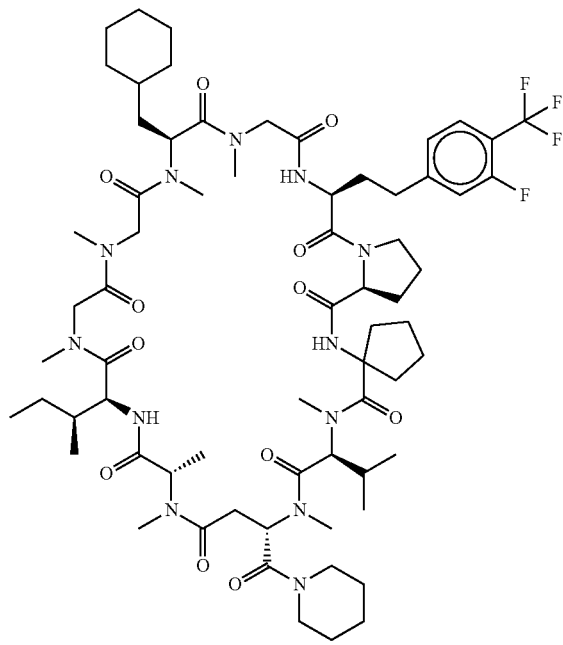 |
| 267 | 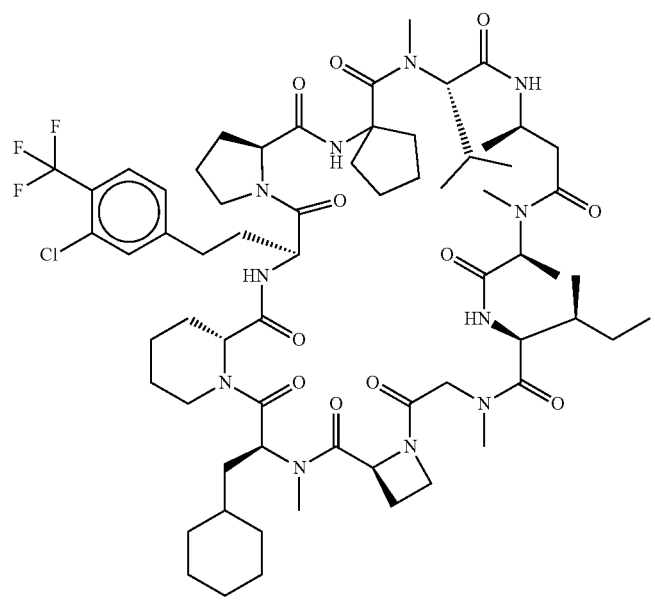 |

TABLE 24-continued
| Compound No. | Structural formula |
|---|---|
| 268 | 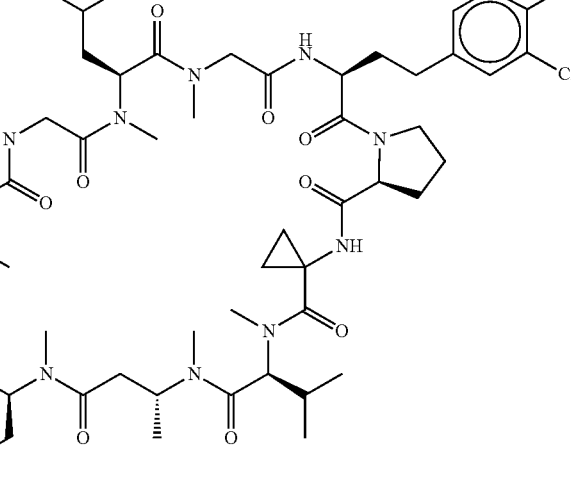 |
| 269 | 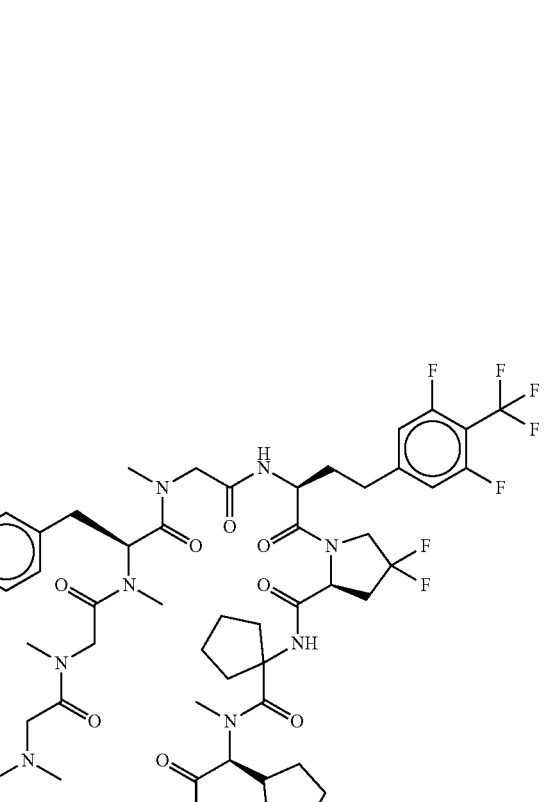 |

TABLE 24-continued
| Compound No. | Structural formula |
|---|---|
| 270 | 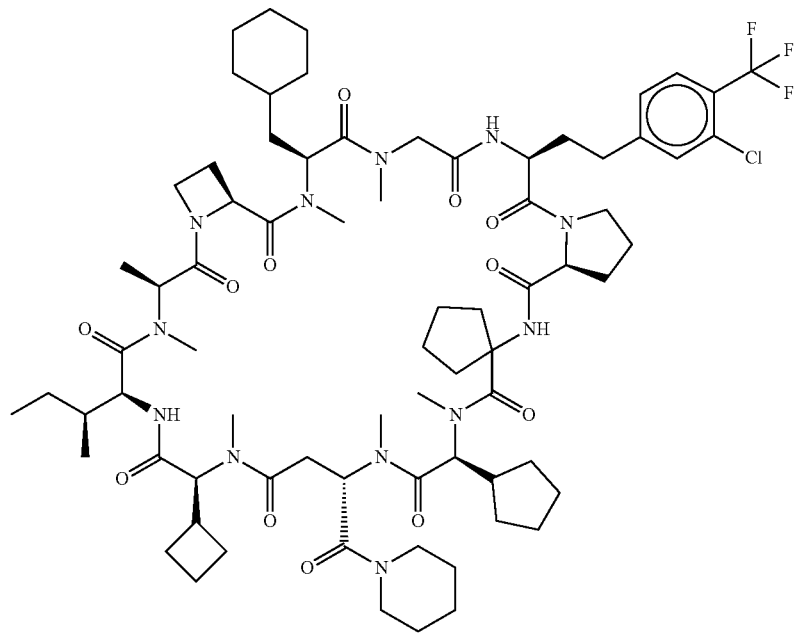 |
| 271 | 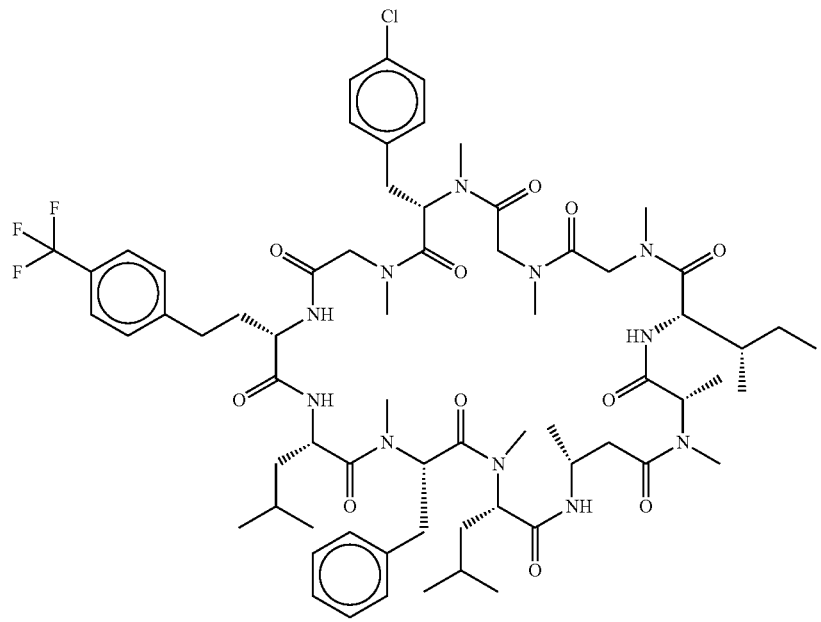 |

TABLE 24-continued
| Compound No. | Structural formula |
|---|---|
| 272 | 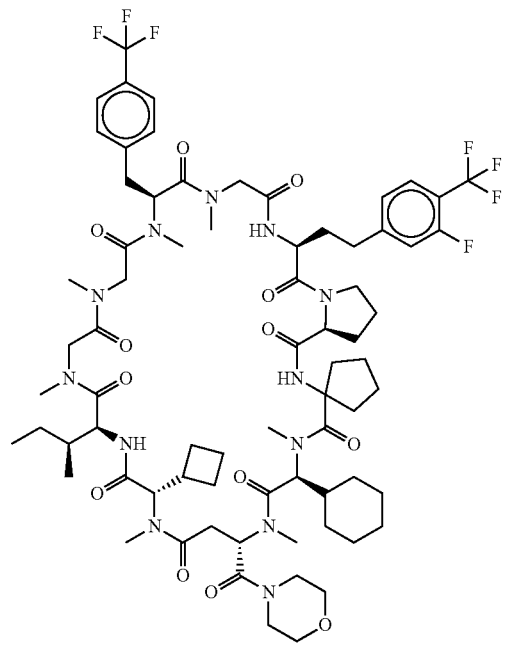 |
| 273 | 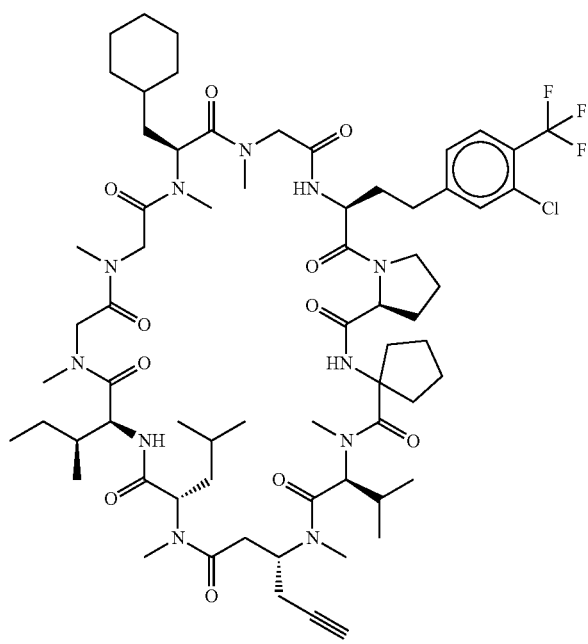 |

TABLE 24-continued
| Compound No. | Structural formula |
|---|---|
| 274 | 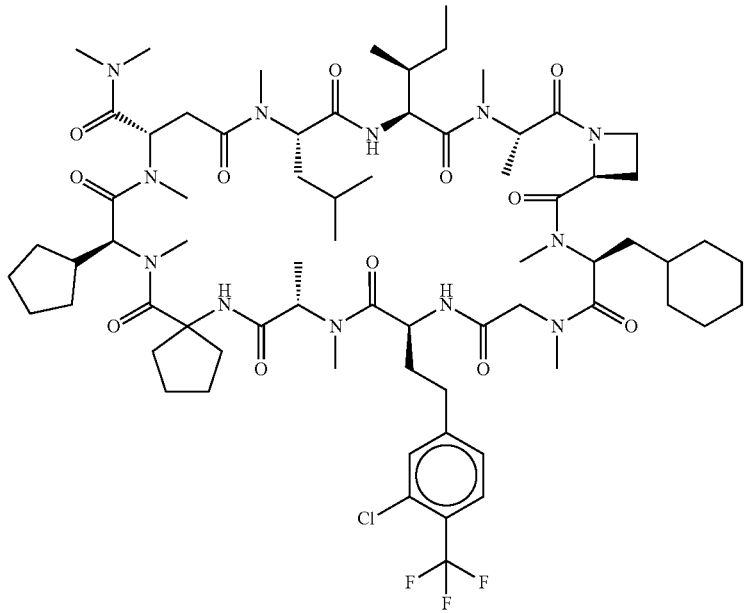 |
| 275 | 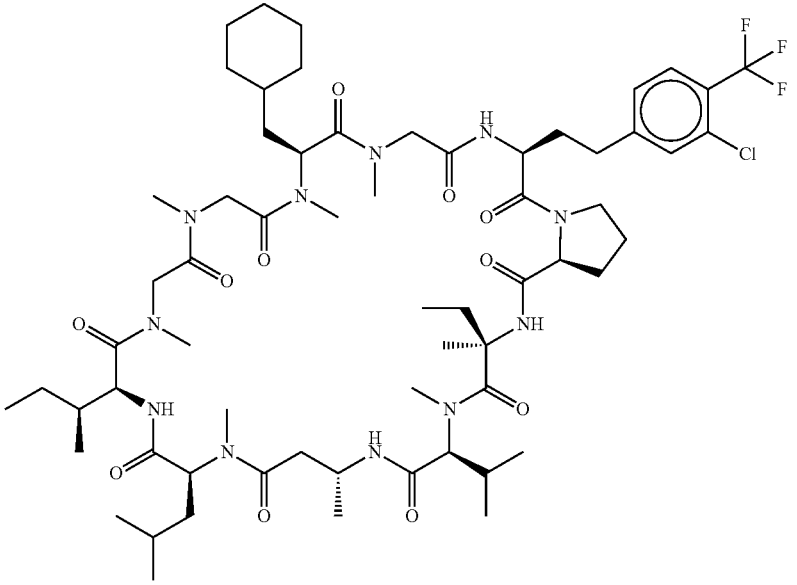 |

TABLE 24-continued
| Compound No. | Structural formula |
|---|---|
| 276 | 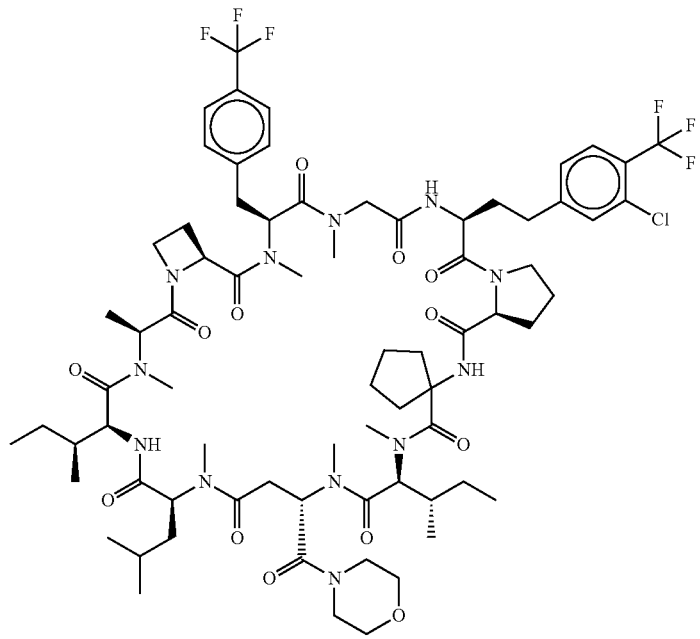 |
| 277 | 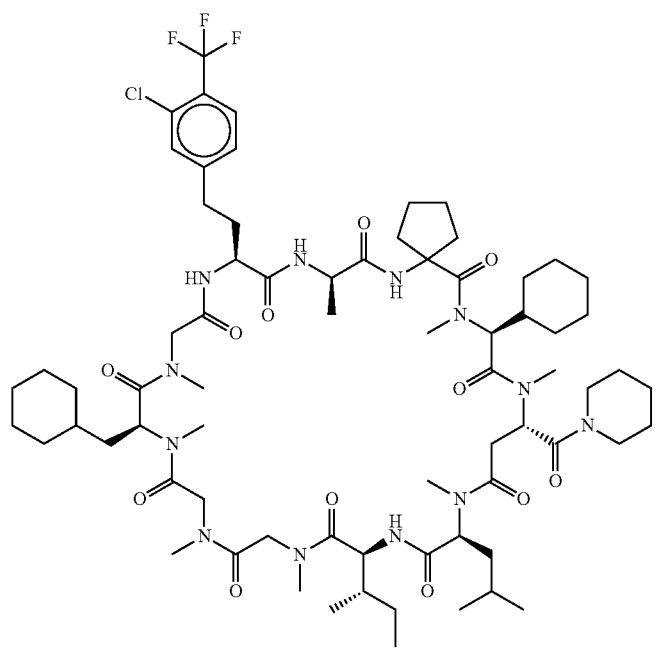 |

TABLE 24-continued
| Compound No. | Structural formula |
|---|---|
| 278 | 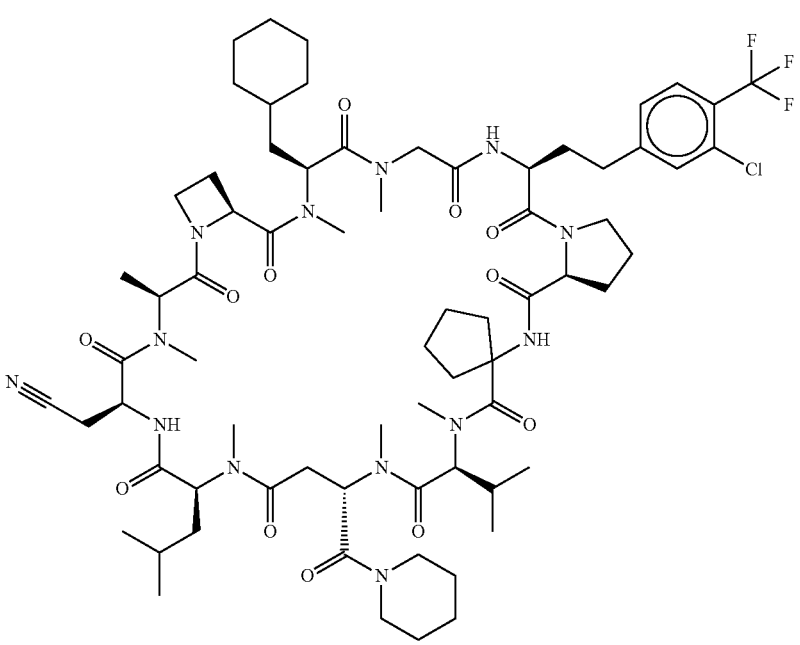 |
| 279 | 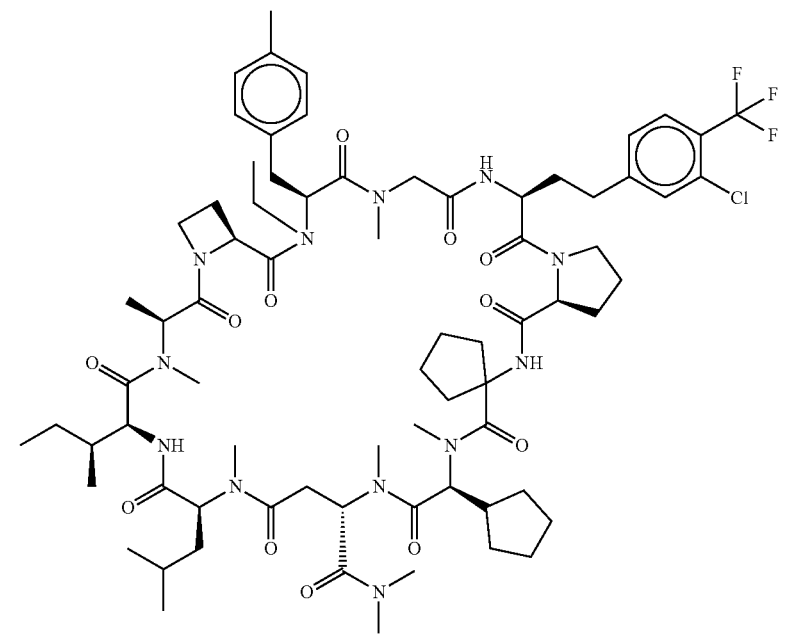 |

TABLE 24-continued
| Compound No. | Structural formula |
|---|---|
| 280 | 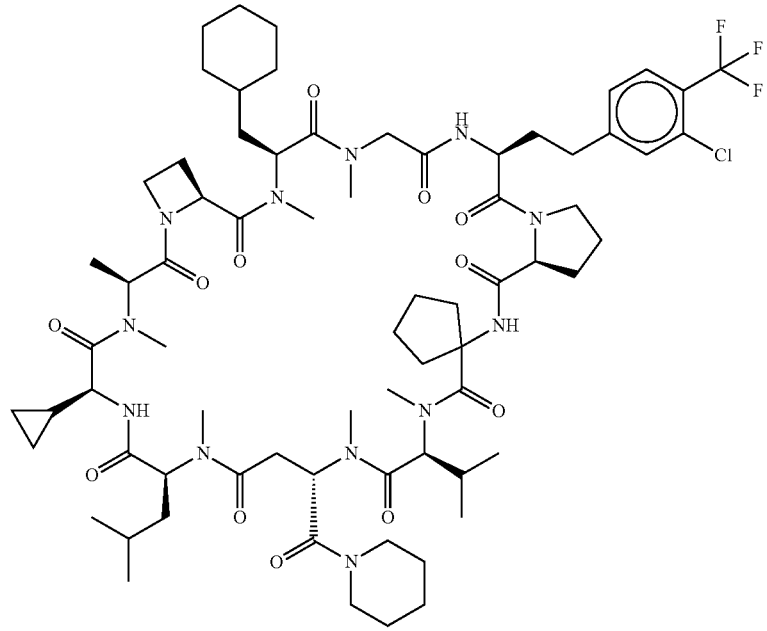 |
| 281 | 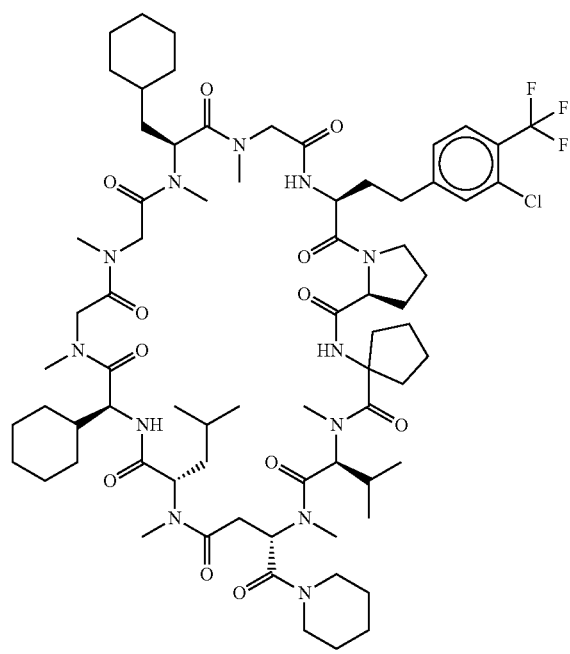 |

TABLE 24-continued
| Compound No. | Structural formula |
|---|---|
| 282 | 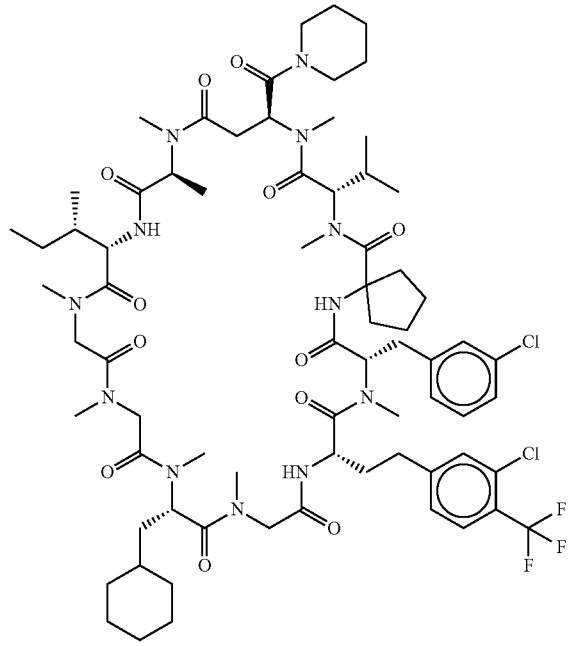 |
| 283 | 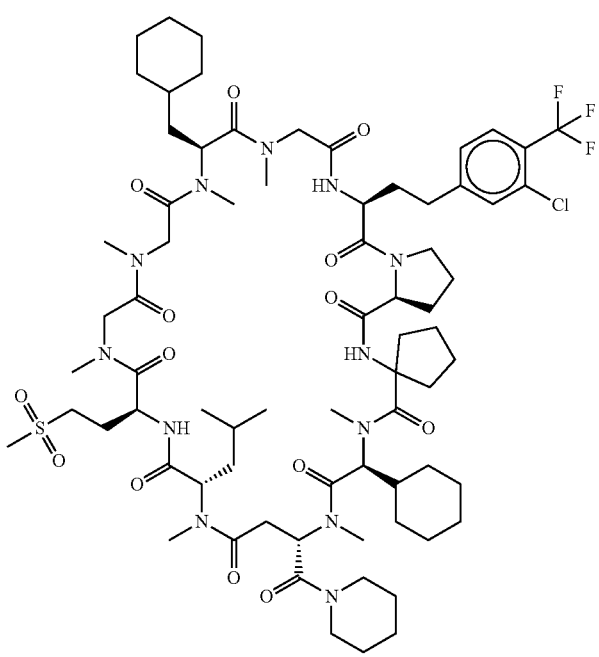 |

TABLE 24-continued
| Compound No. | Structural formula |
|---|---|
| 284 | 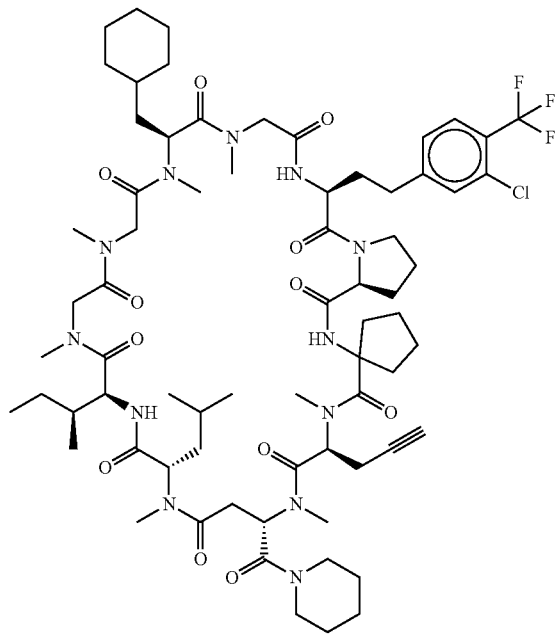 |
| 285 | 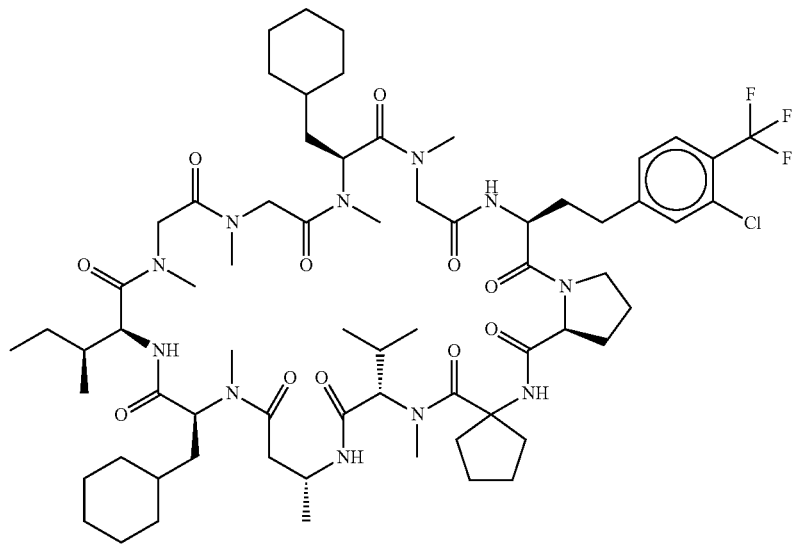 |

TABLE 24-continued
| Compound No. | Structural formula |
|---|---|
| 286 | 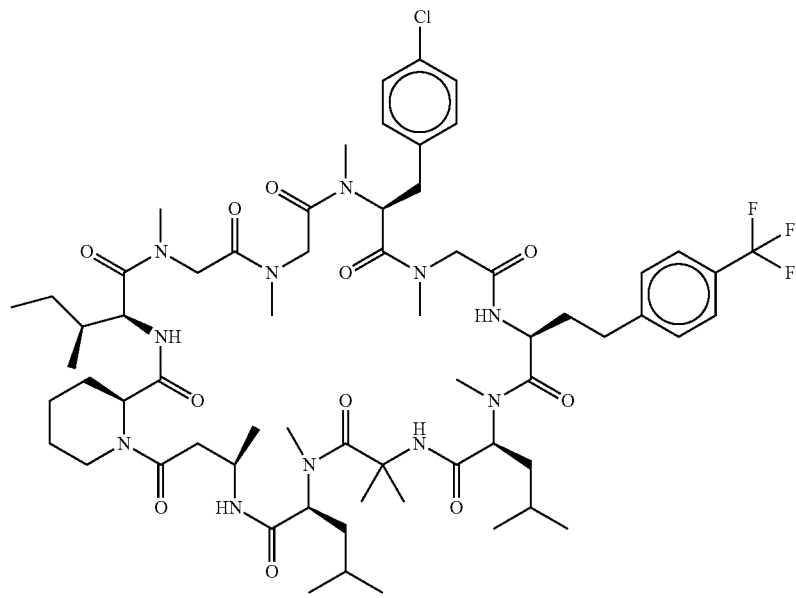 |
| 287 | 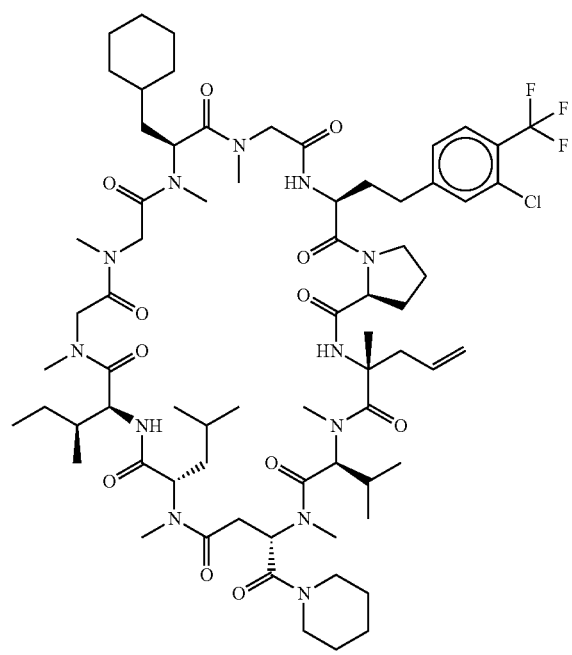 |

TABLE 24-continued
| Compound No. | Structural formula |
|---|---|
| 288 | 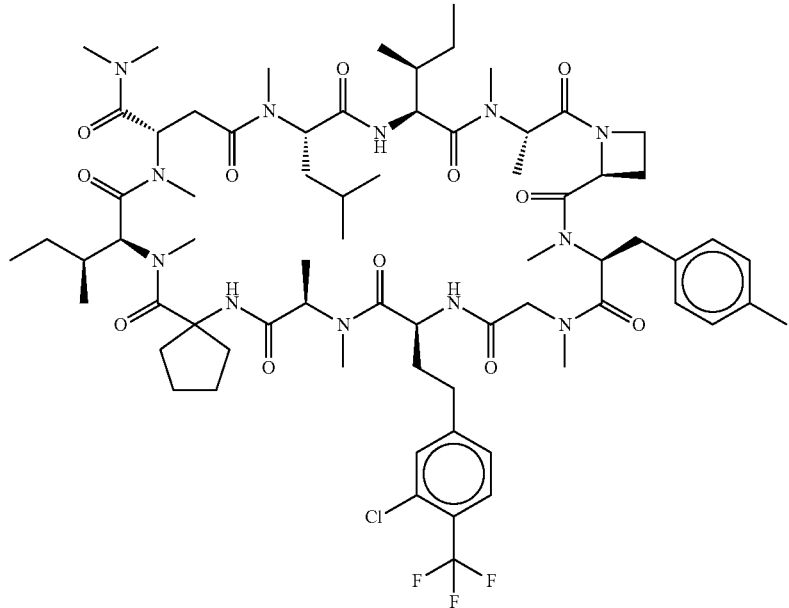 |
| 289 | 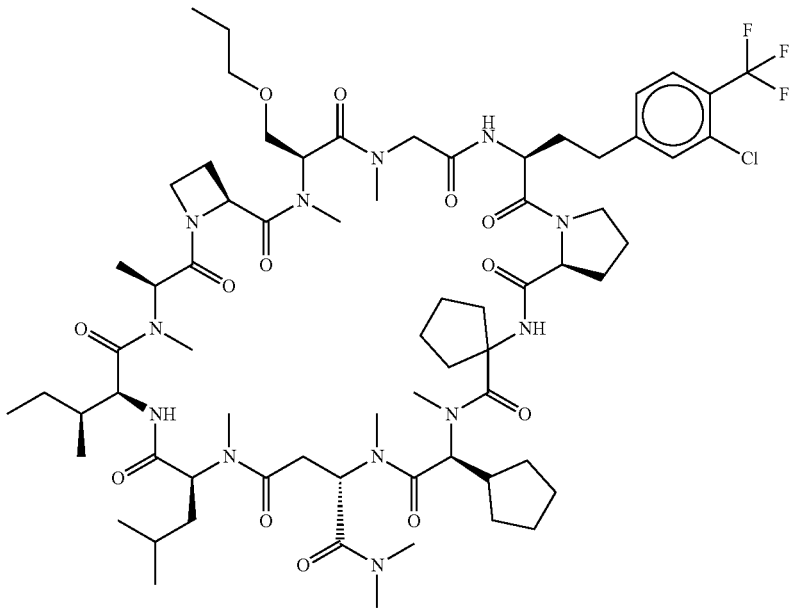 |

TABLE 24-continued
| Compound No. | Structural formula |
|---|---|
| 290 | 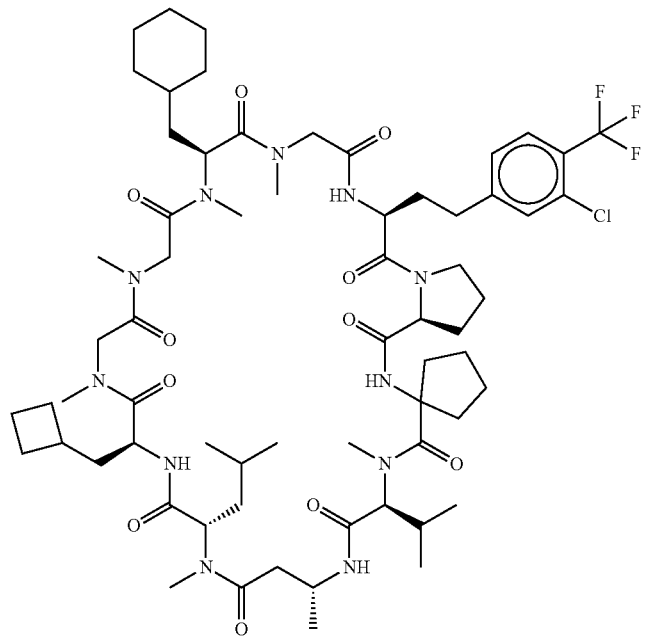 |
| 291 | 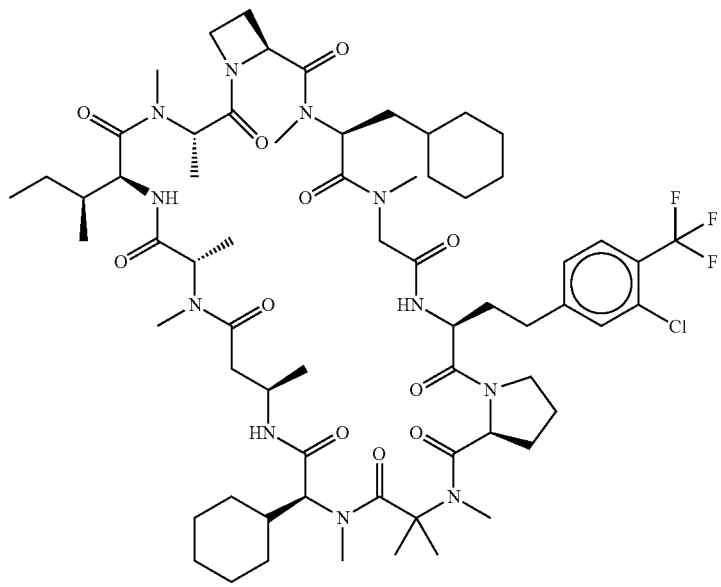 |

TABLE 24-continued
| Compound No. | Structural formula |
|---|---|
| 292 | 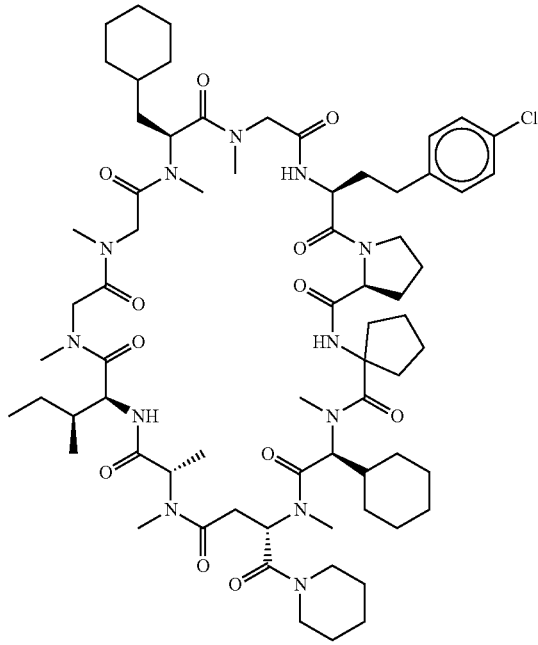 |
| 293 | 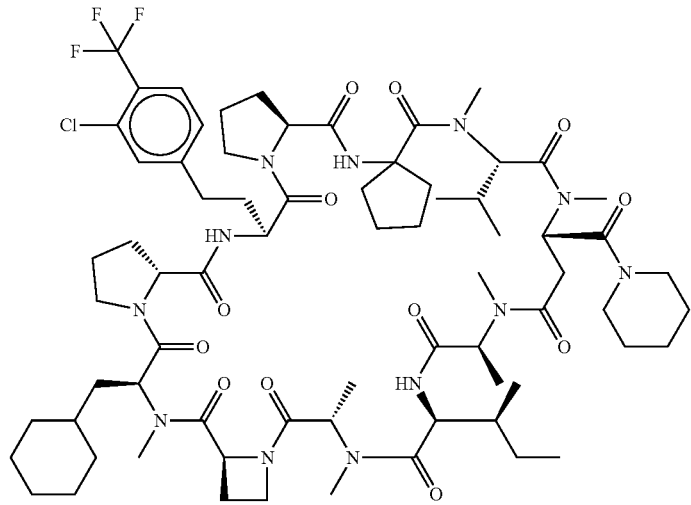 |

TABLE 24-continued
| Compound No. | Structural formula |
|---|---|
| 294 | 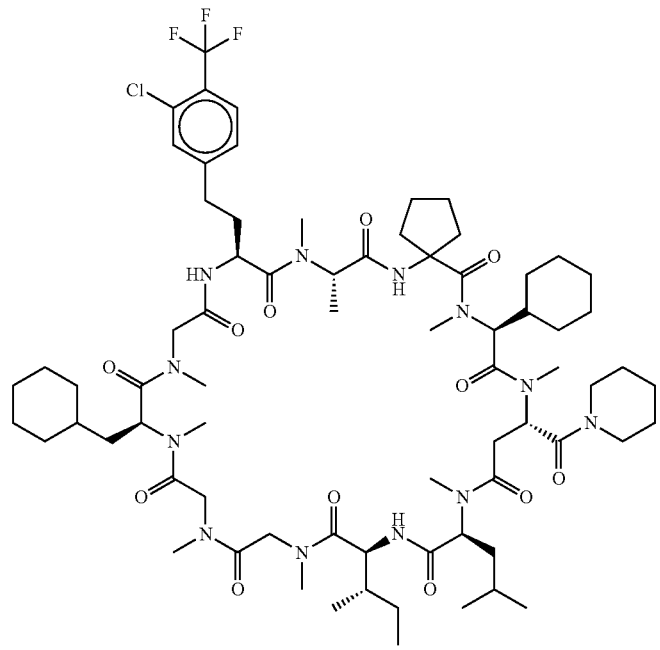 |
| 295 | 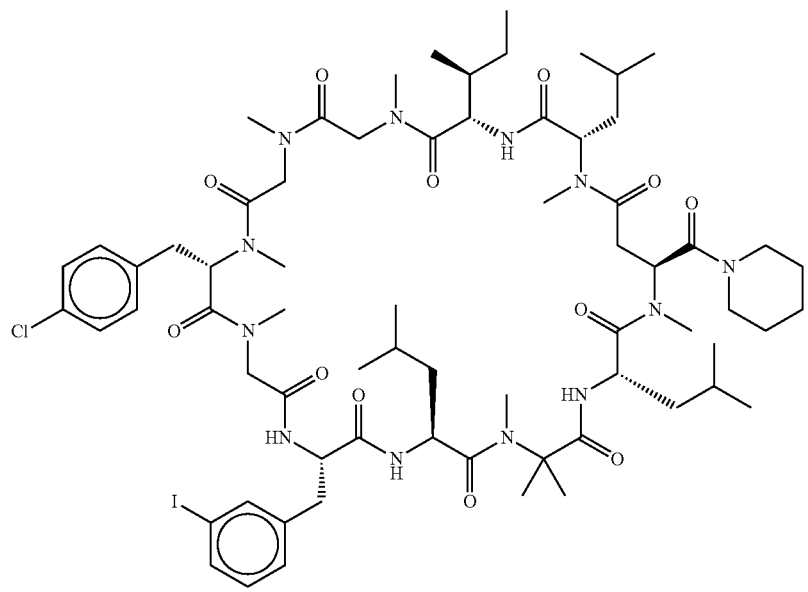 |

TABLE 24-continued
| Compound No. | Structural formula |
|---|---|
| 296 | 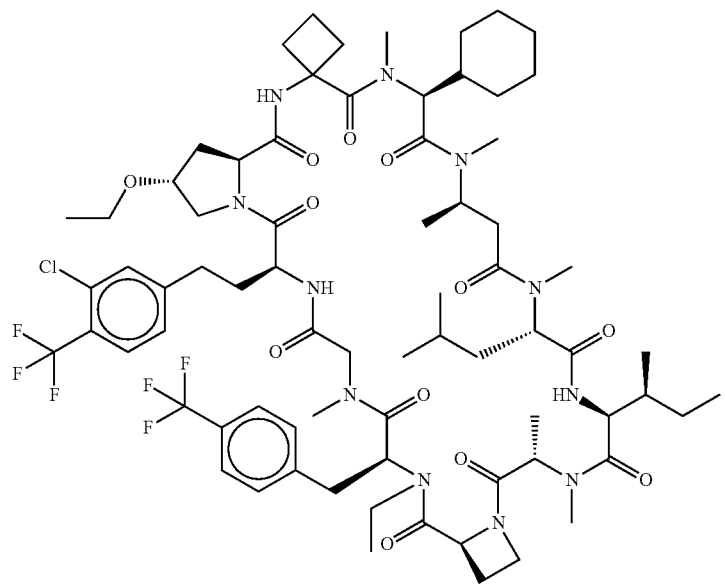 |
| 297 | 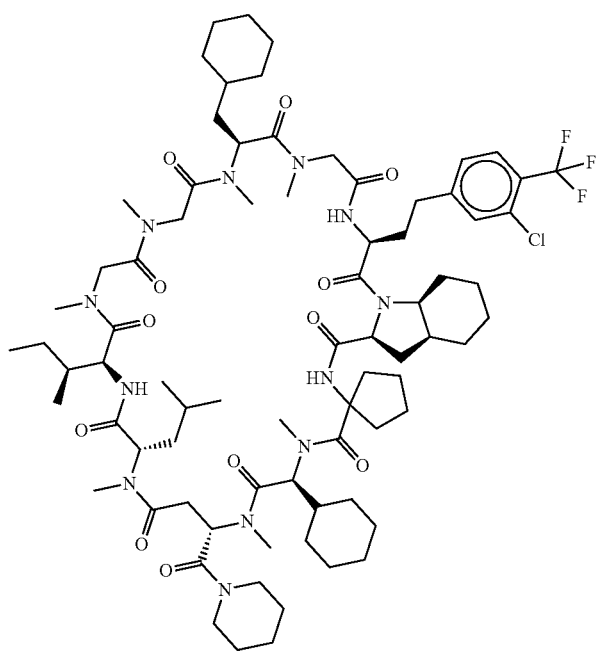 |

TABLE 24-continued
| Compound No. | Structural formula |
|---|---|
| 298 | 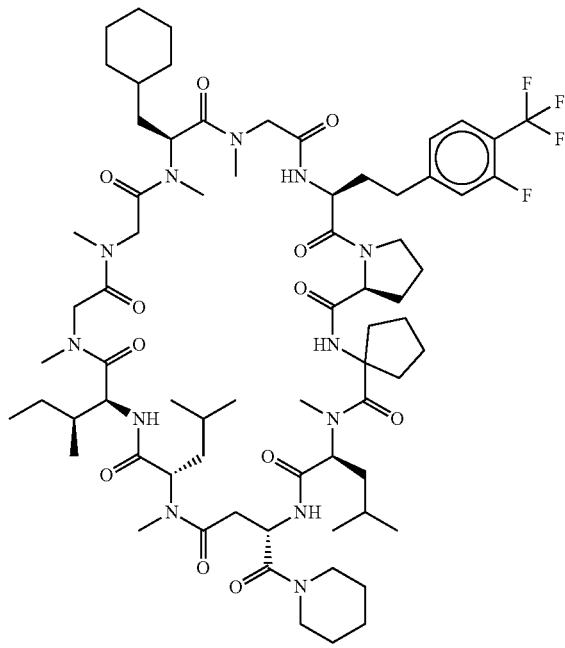 |
| 299 | 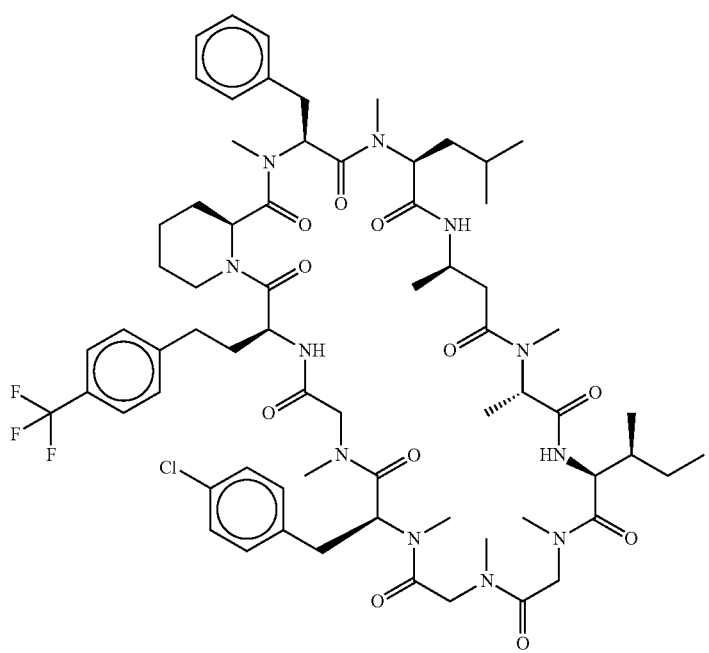 |

TABLE 24-continued
| Compound No. | Structural formula |
|---|---|
| 300 | 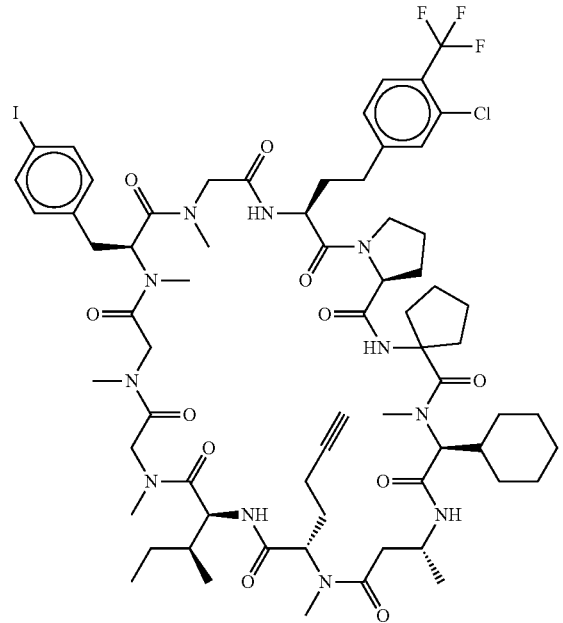 |
| 301 | 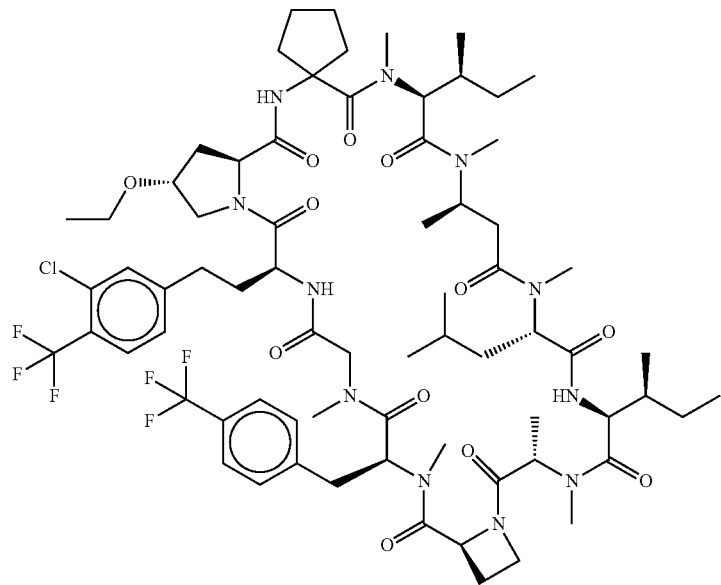 |

TABLE 24-continued
| Compound No. | Structural formula |
|---|---|
| 302 | 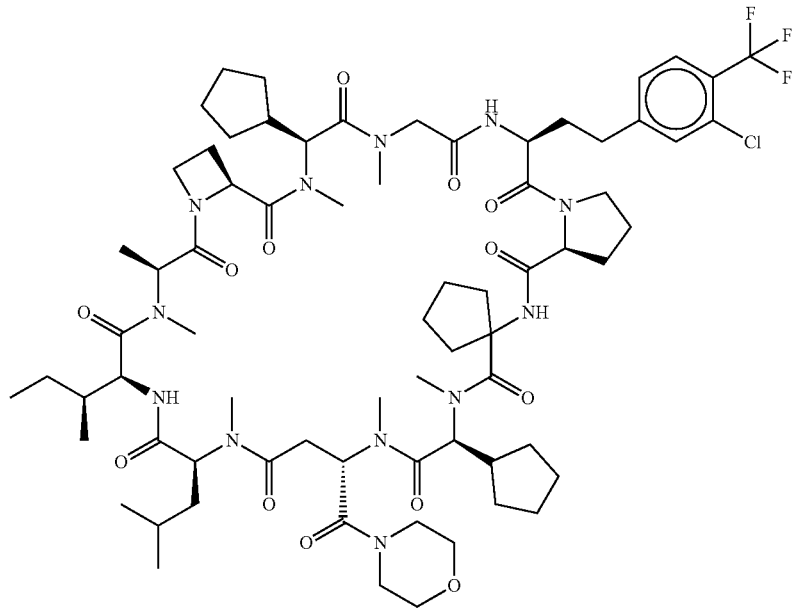 |
| 303 | 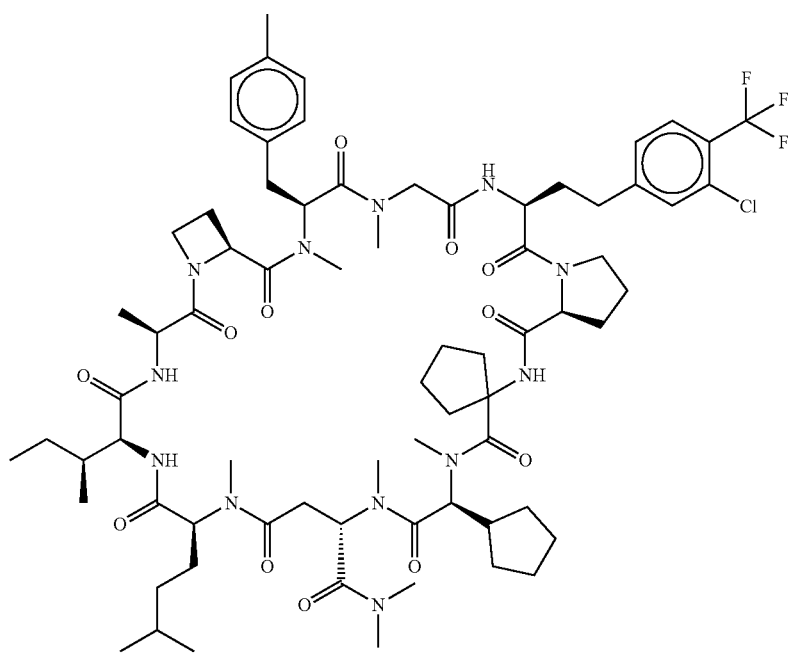 |

TABLE 24-continued
| Compound No. | Structural formula |
|---|---|
| 304 | 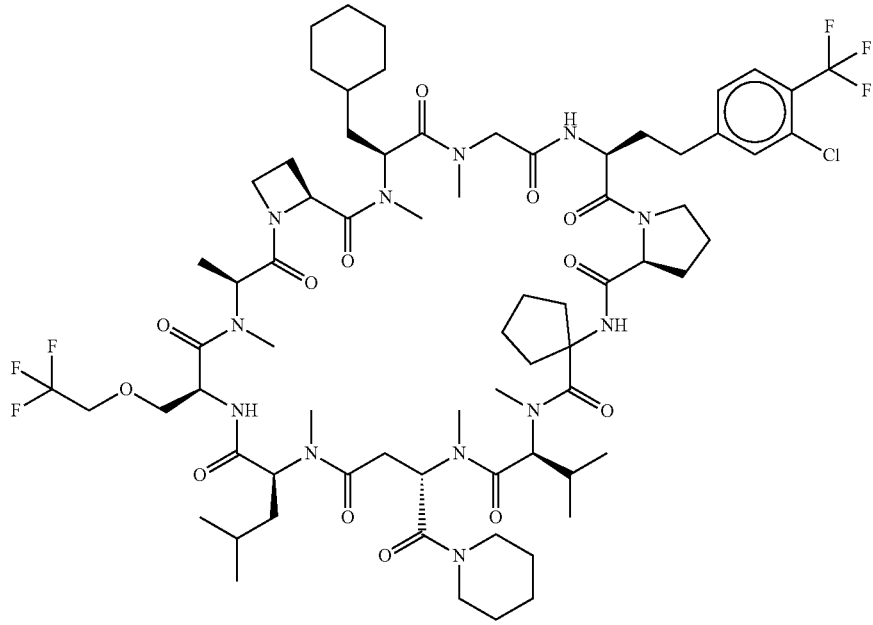 |
| 305 | 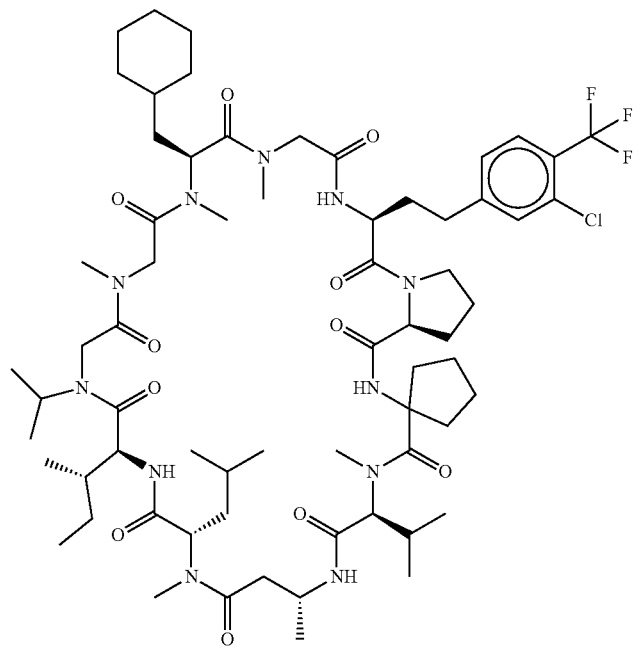 |

TABLE 24-continued
| Compound No. | Structural formula |
|---|---|
| 306 | 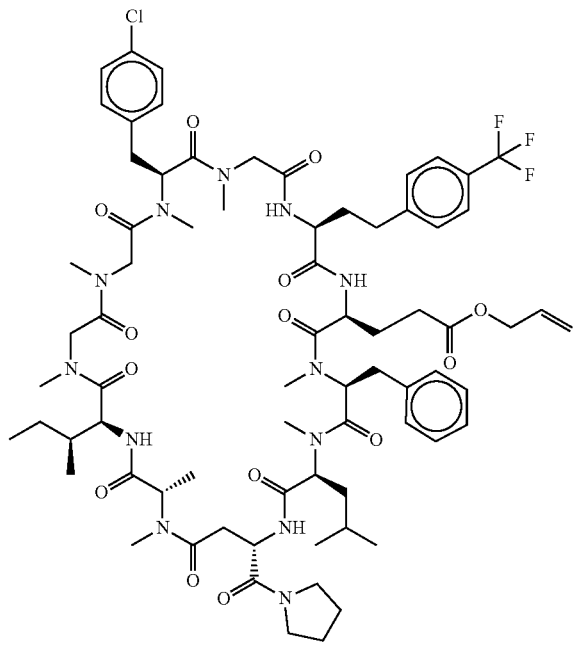 |
| 307 | 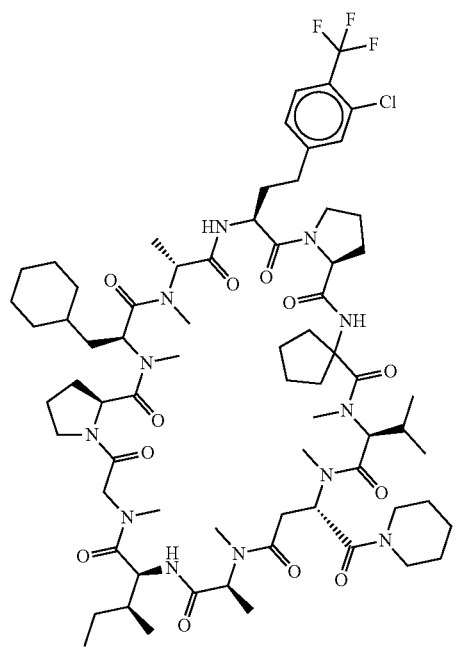 |

TABLE 24-continued
| Compound No. | Structural formula |
|---|---|
| 308 | 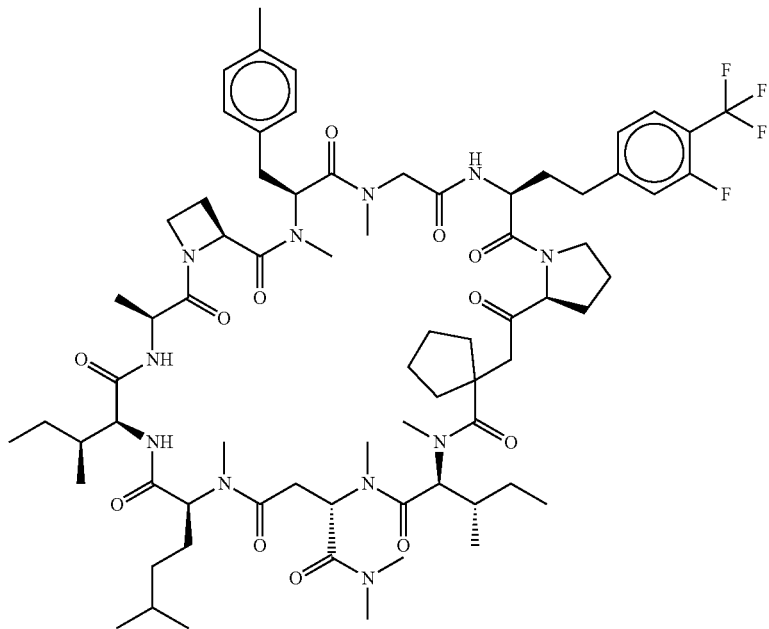 |
| 309 | 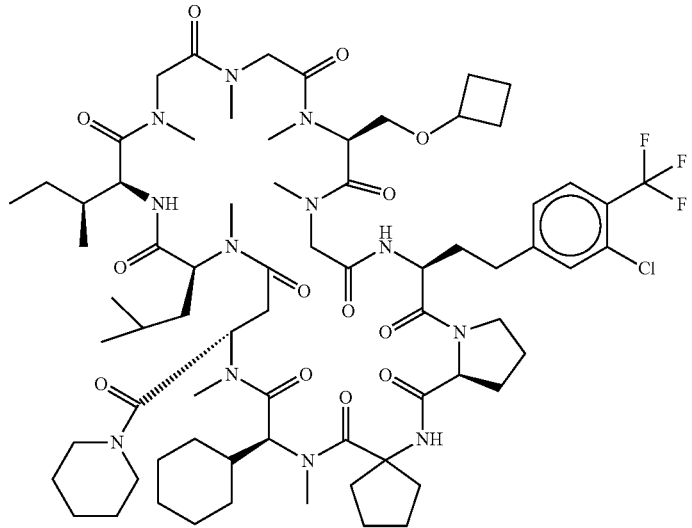 |

TABLE 24-continued
| Compound No. | Structural formula |
|---|---|
| 310 | 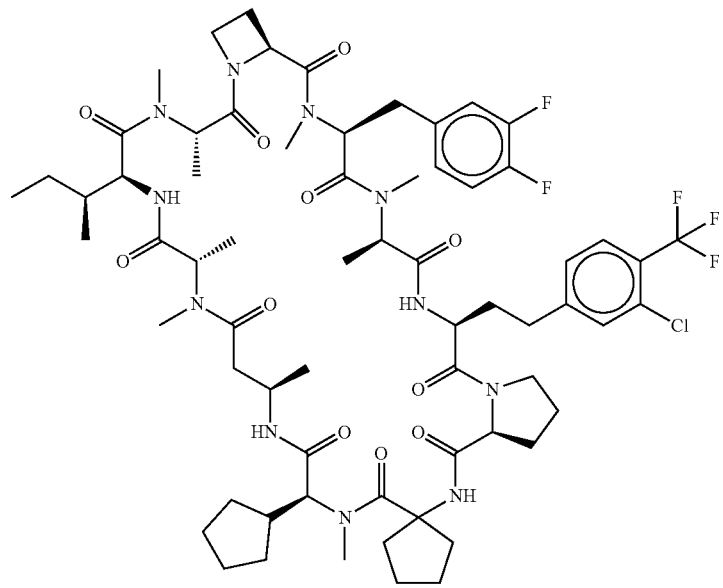 |
| 311 | 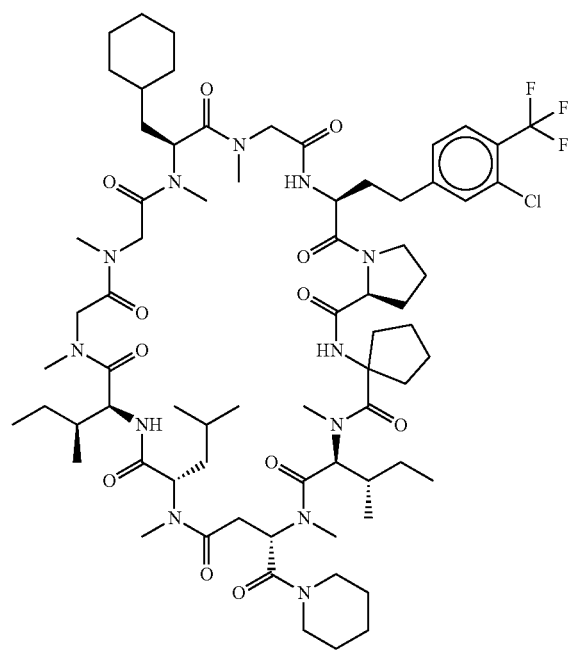 |

TABLE 24-continued
| Compound No. | Structural formula |
|---|---|
| 312 | 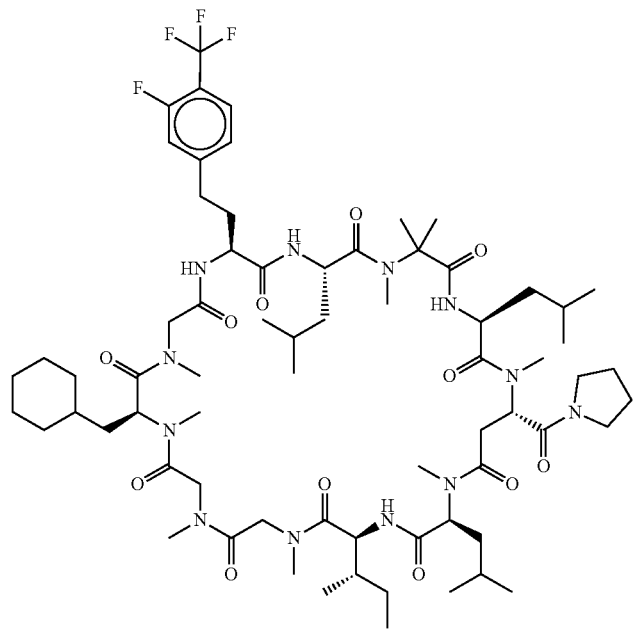 |
| 313 | 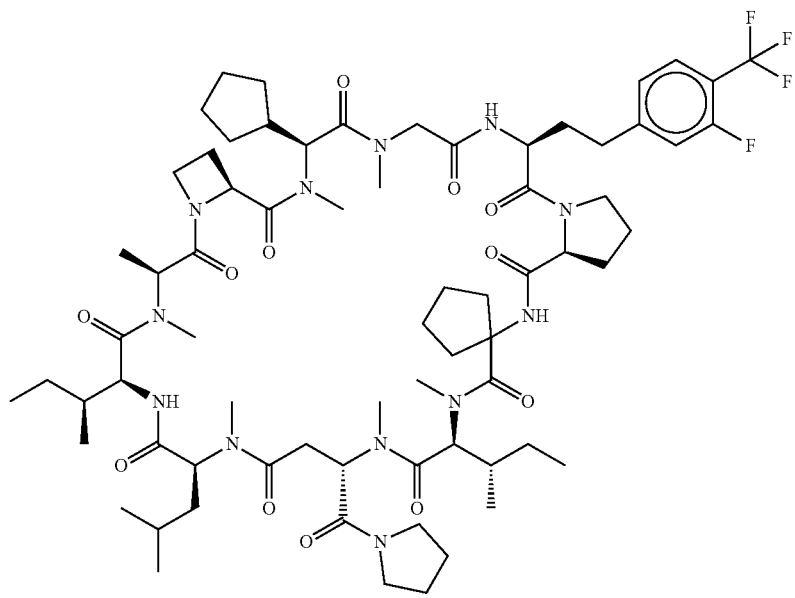 |

TABLE 24-continued
| Compound No. | Structural formula |
|---|---|
| 314 | 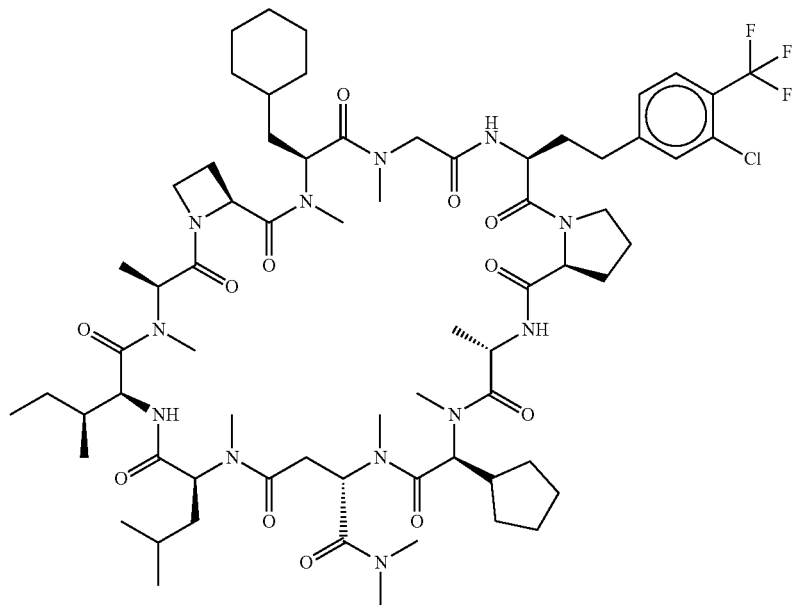 |
| 315 | 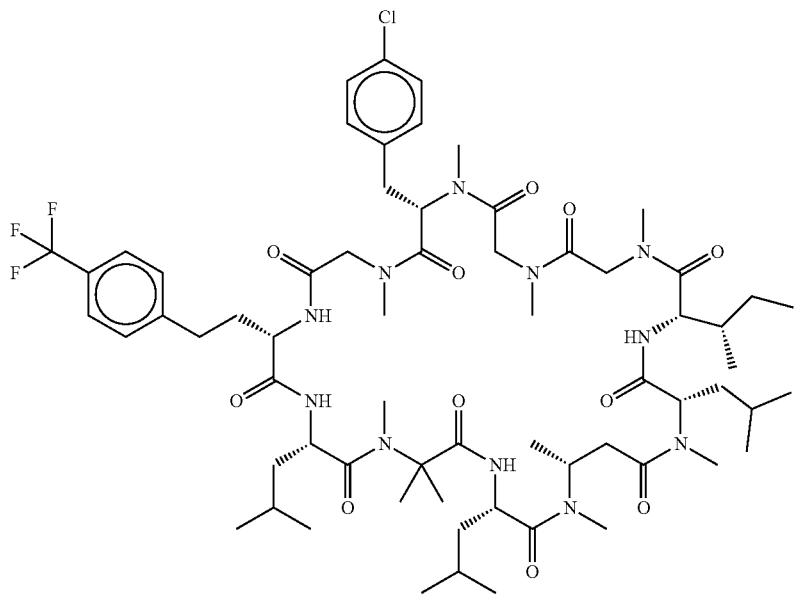 |

TABLE 24-continued
| Compound No. | Structural formula |
|---|---|
| 316 | 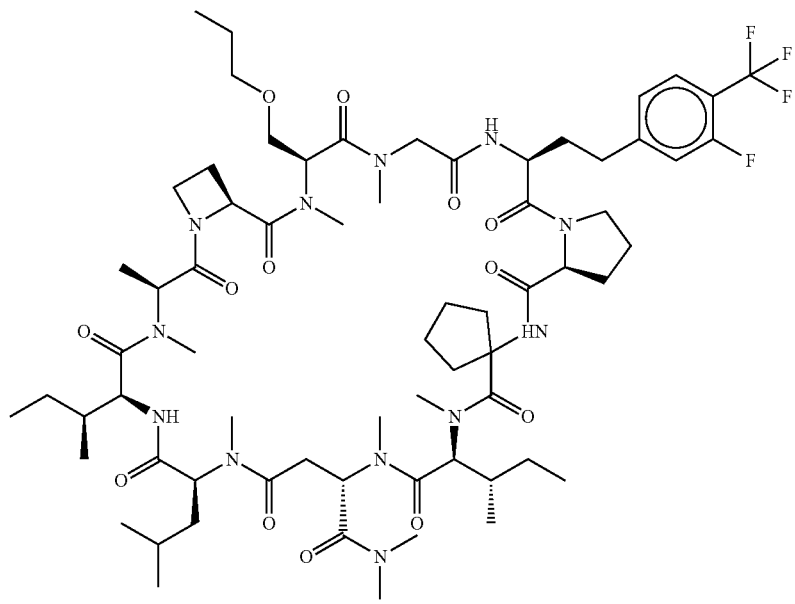 |
| 317 | 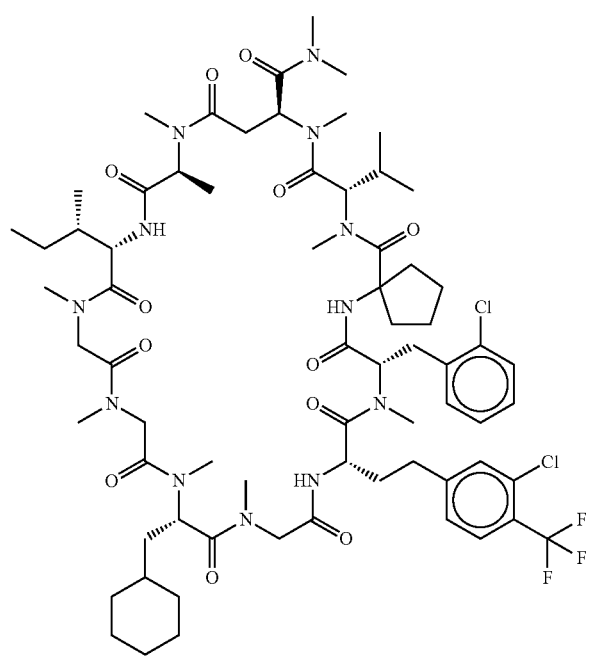 |

TABLE 24-continued
| Compound No. | Structural formula |
|---|---|
| 318 | 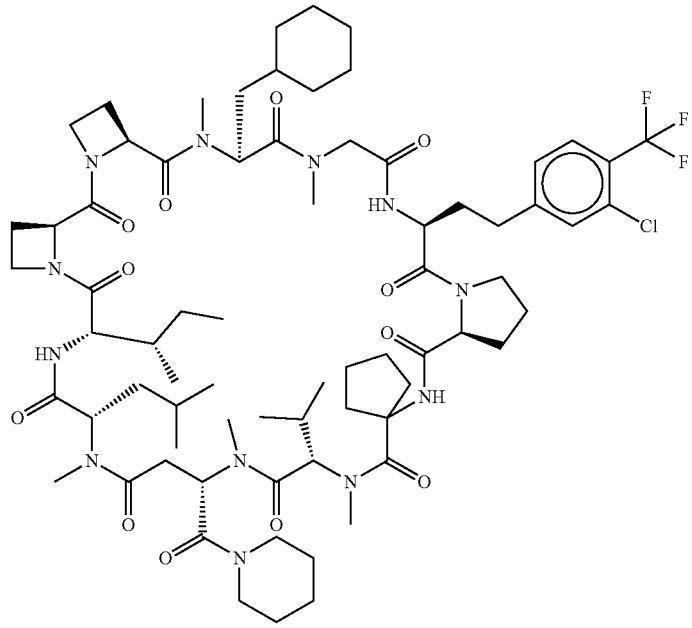 |
| 319 | 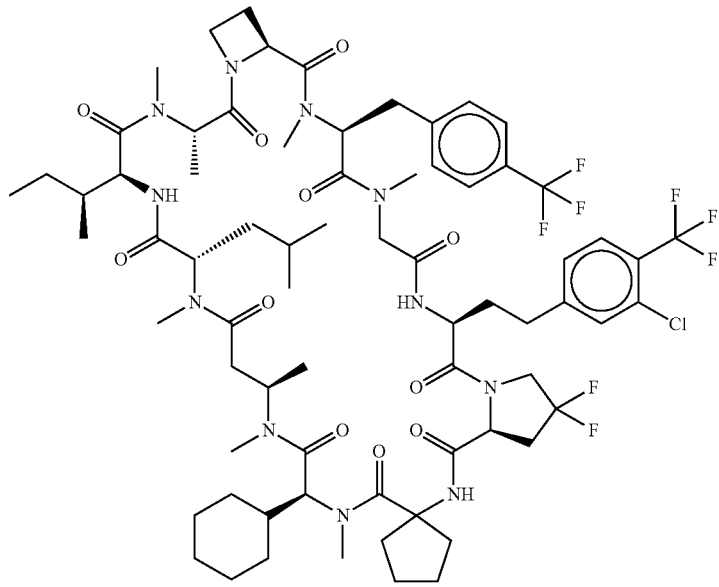 |

TABLE 24-continued
| Compound No. | Structural formula |
|---|---|
| 320 | 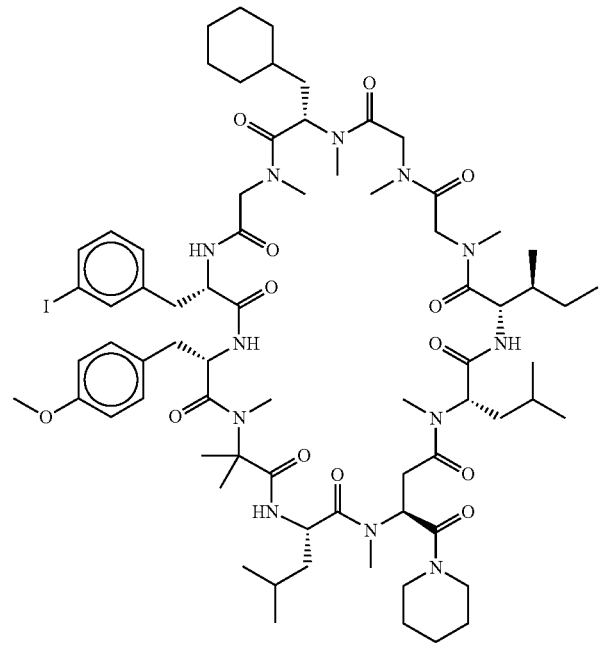 |
| 321 | 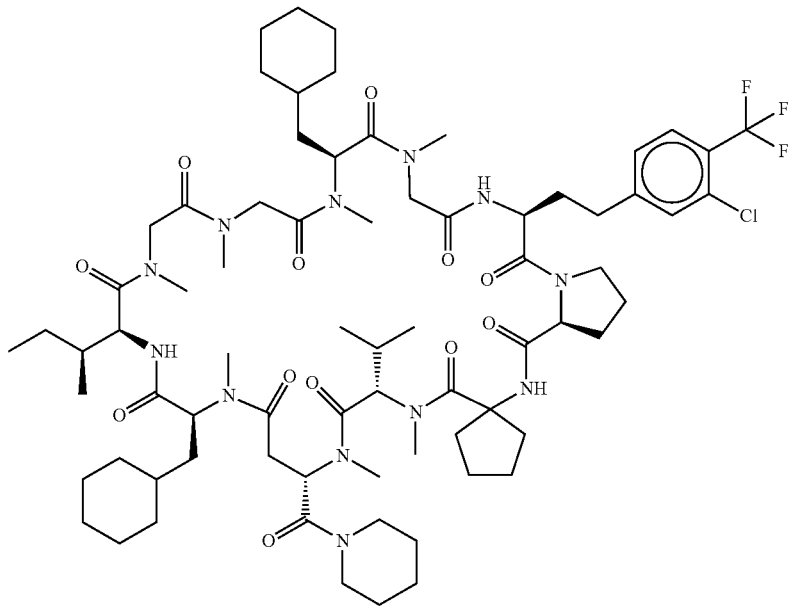 |

TABLE 24-continued
| Compound No. | Structural formula |
|---|---|
| 322 | 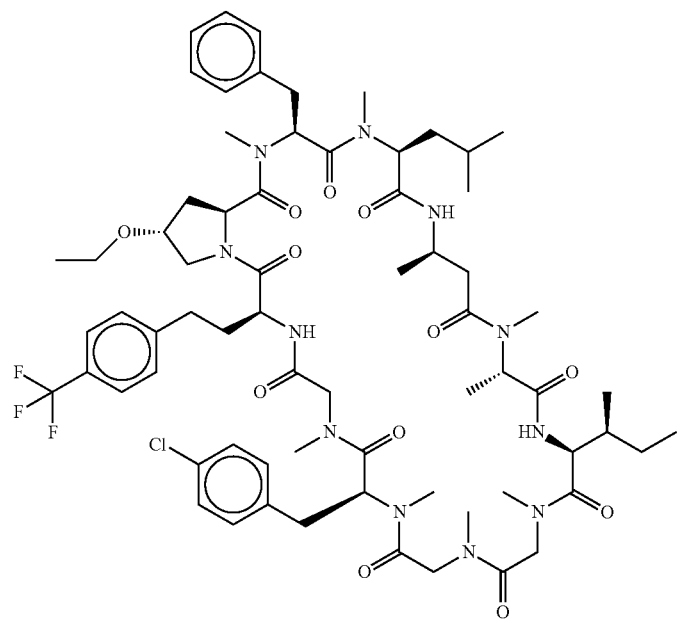 |
| 323 | 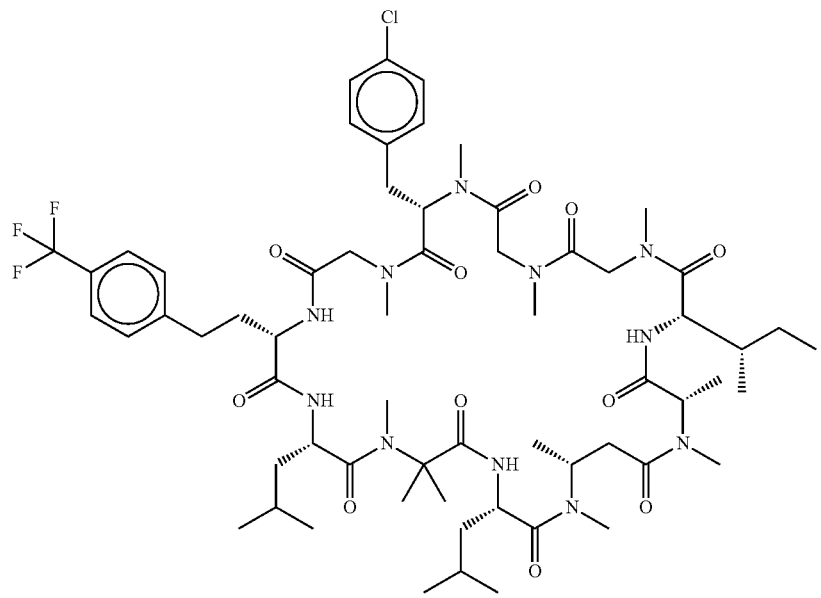 |

TABLE 24-continued
| Compound No. | Structural formula |
|---|---|
| 324 | 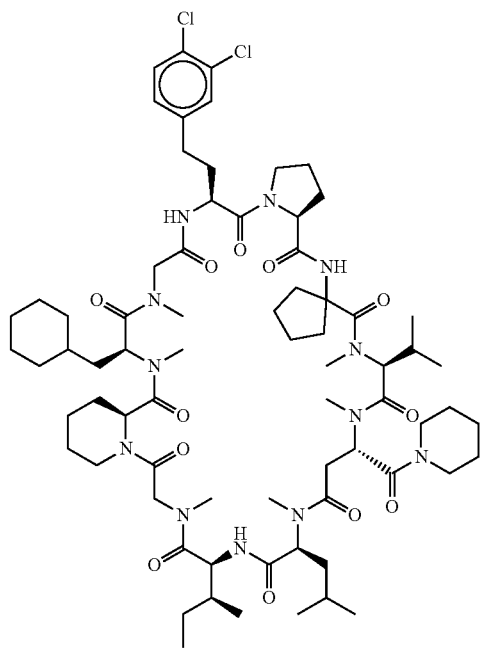 |
| 325 | 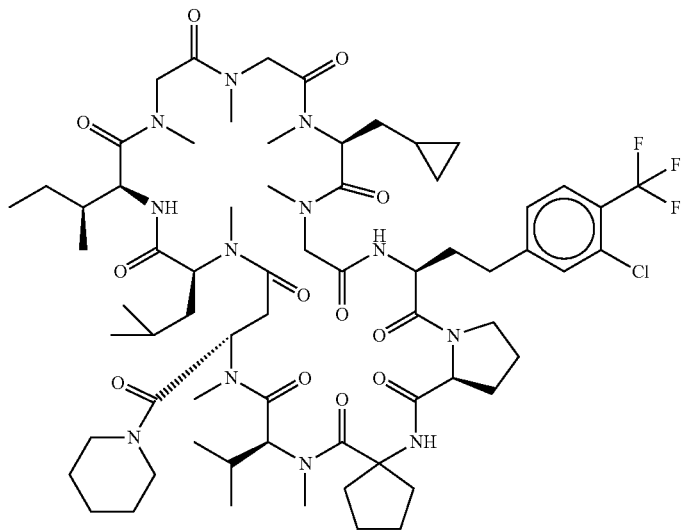 |

TABLE 24-continued
| Compound No. | Structural formula |
|---|---|
| 326 | 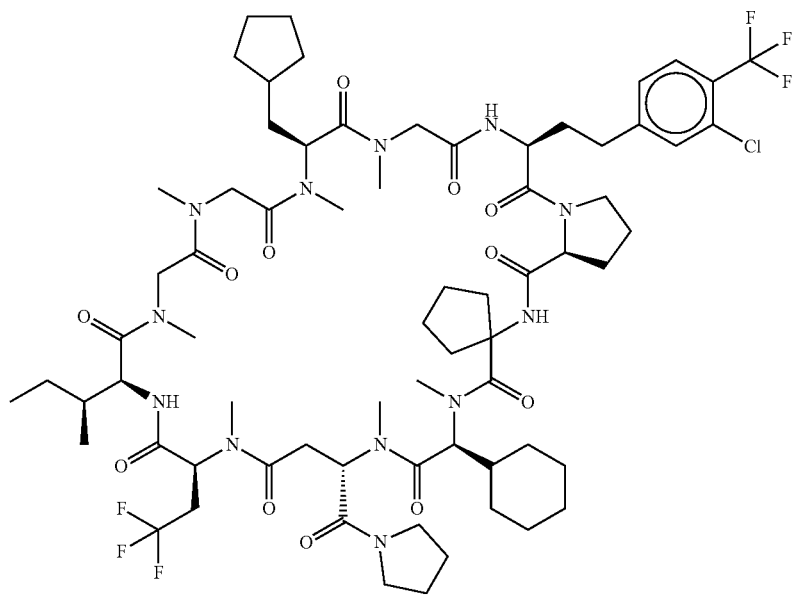 |
| 327 | 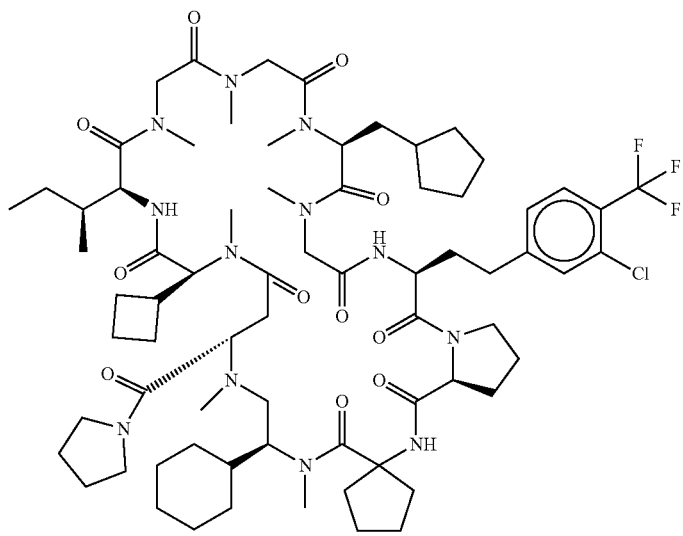 |

TABLE 24-continued
| Compound No. | Structural formula |
|---|---|
| 328 | 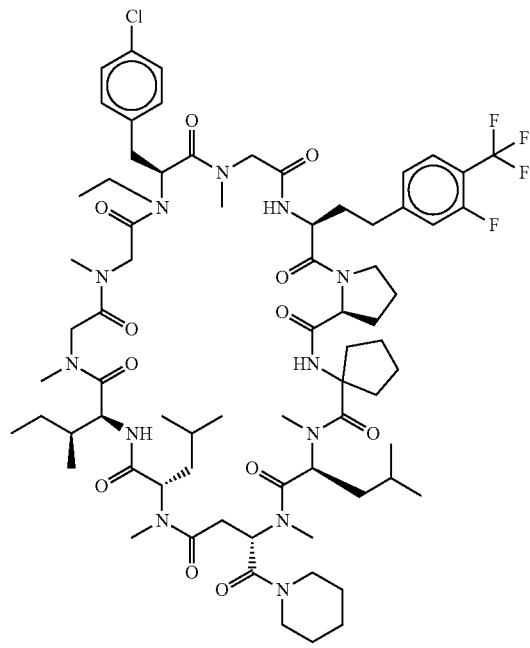 |
| 329 | 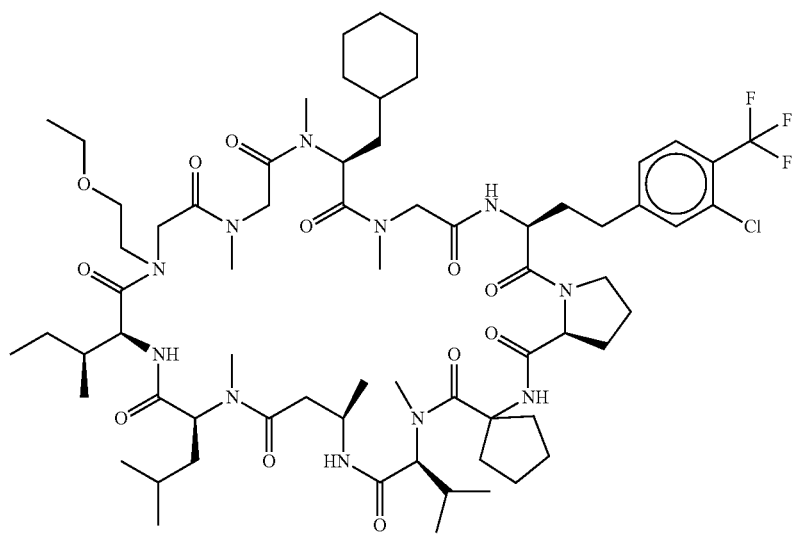 |

TABLE 24-continued
| Compound No. | Structural formula |
|---|---|
| 330 | 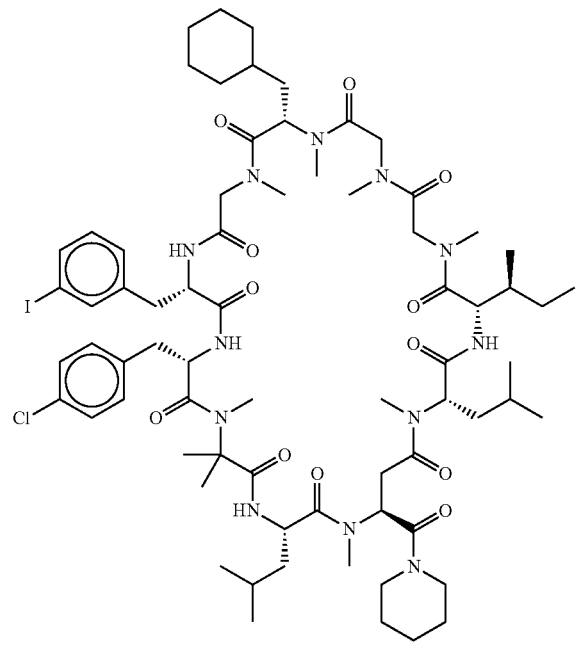 |
| 331 | 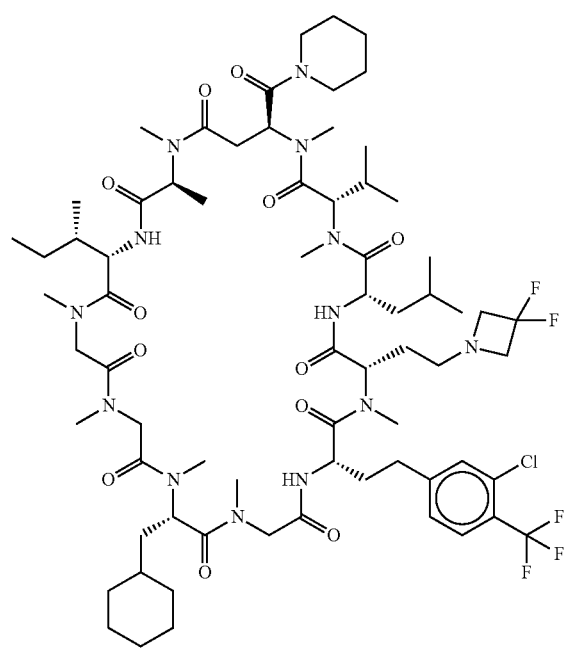 |

TABLE 24-continued
| Compound No. | Structural formula |
|---|---|
| 332 | 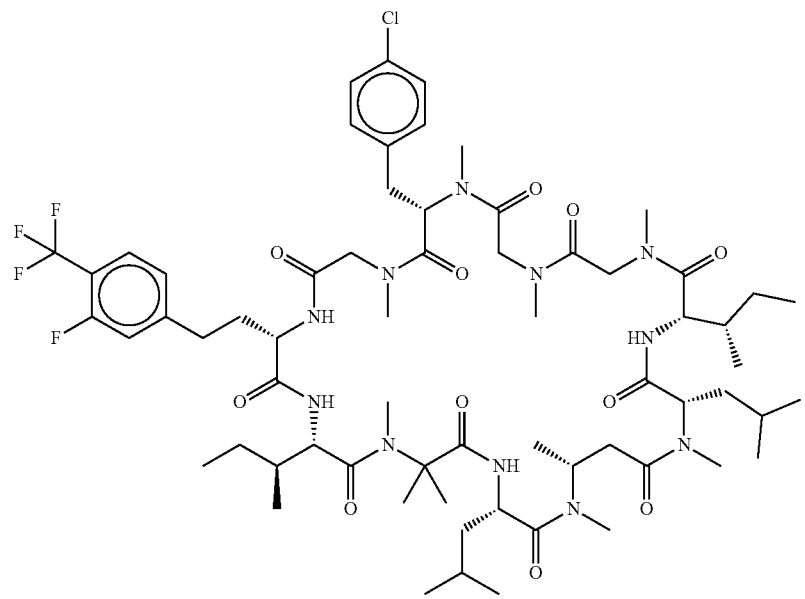 |
| 333 | 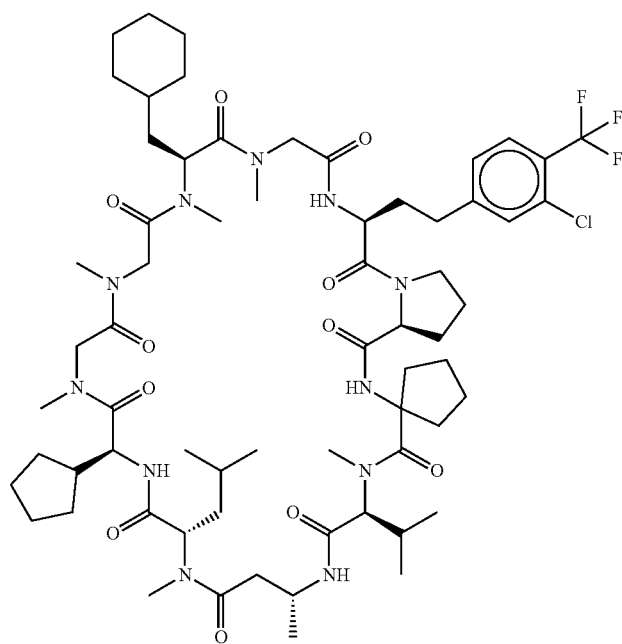 |

TABLE 24-continued
| Compound No. | Structural formula |
| --- | --- |
| 334 | 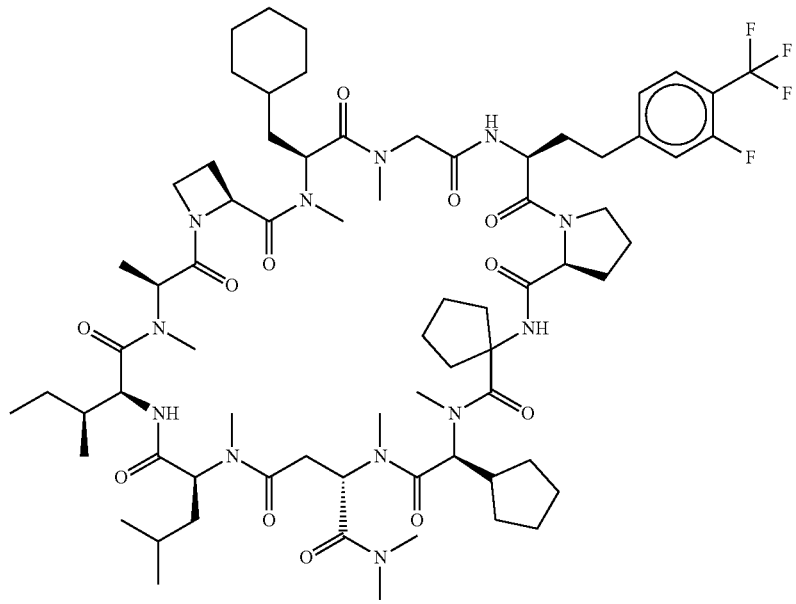 |
| 335 | 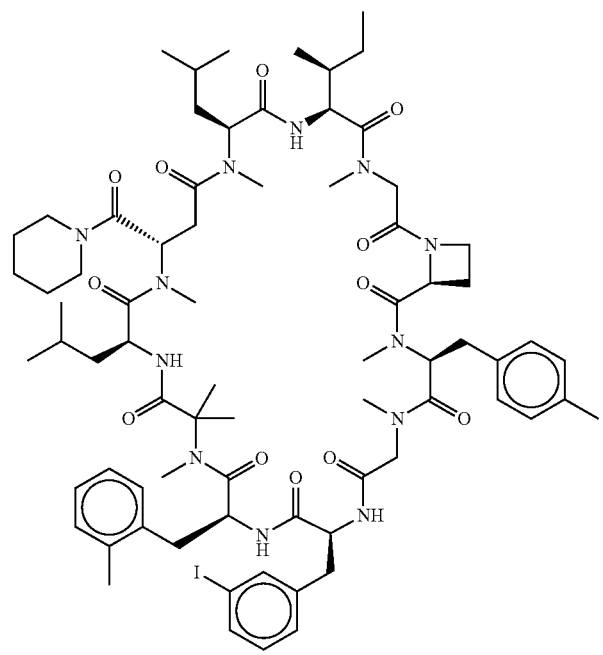 |

TABLE 24-continued
| Compound No. | Structural formula |
|---|---|
| 336 | 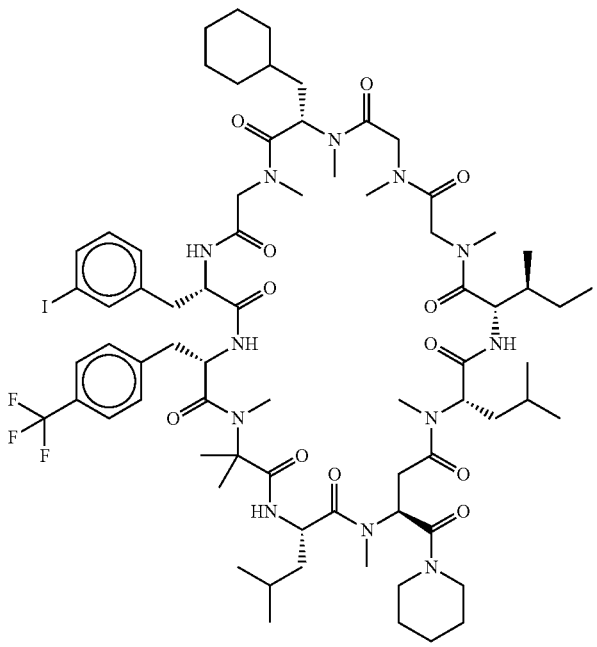 |
| 337 | 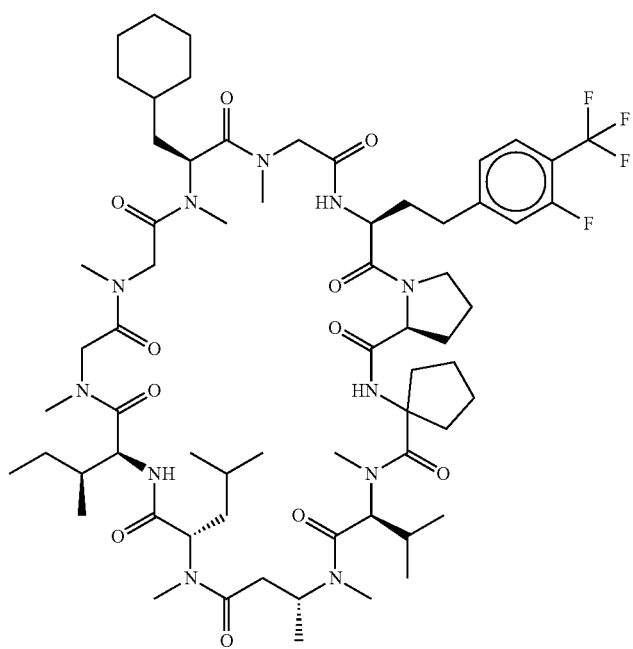 |

TABLE 24-continued
| Compound No. | Structural formula |
|---|---|
| 338 | 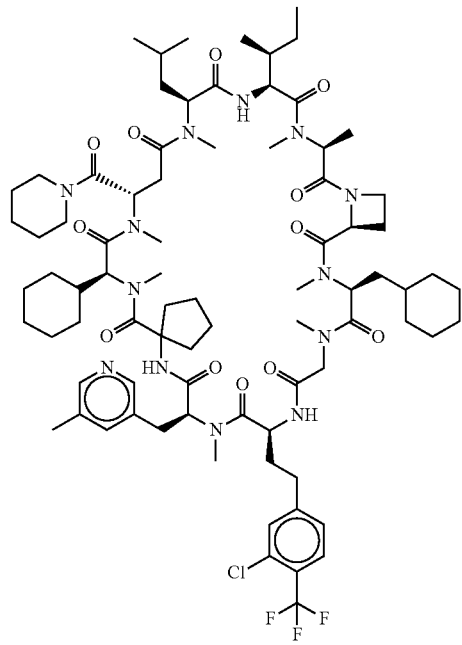 |
| 339 | 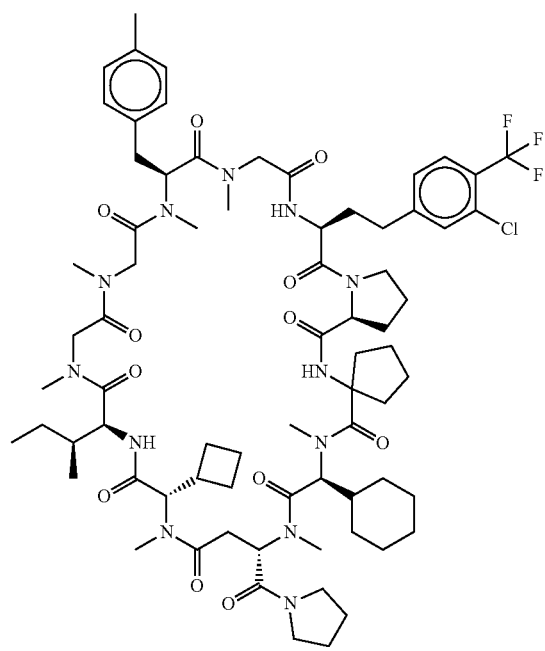 |

TABLE 24-continued
| Compound No. | Structural formula |
|---|---|
| 340 | 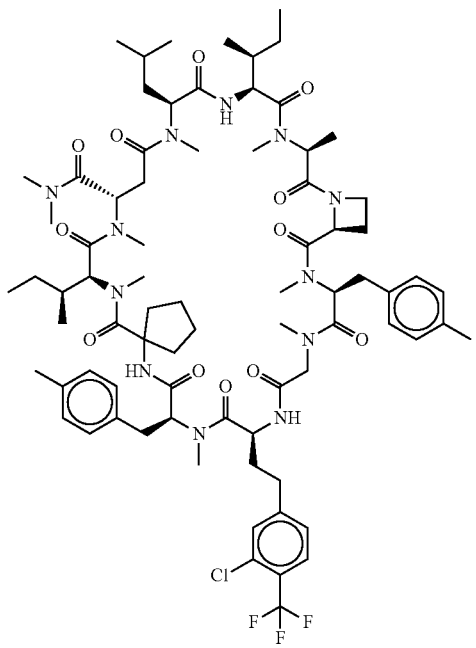 |
| 341 | 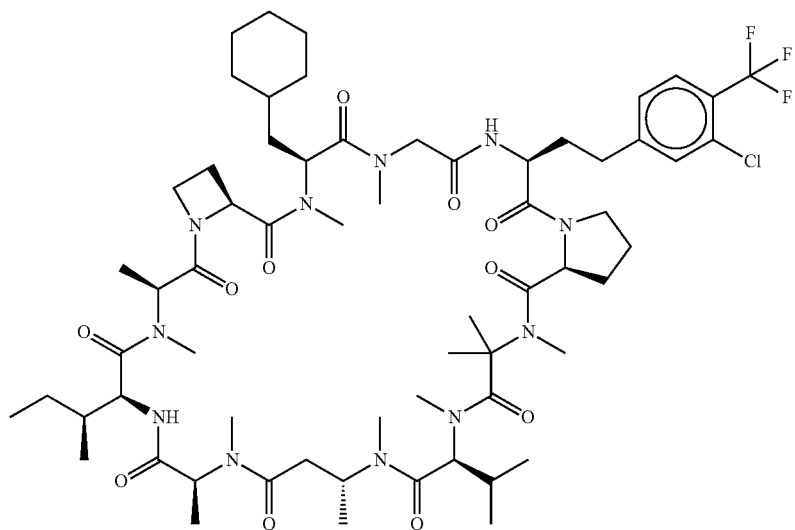 |

TABLE 24-continued
| Compound No. | Structural formula |
|---|---|
| 342 | 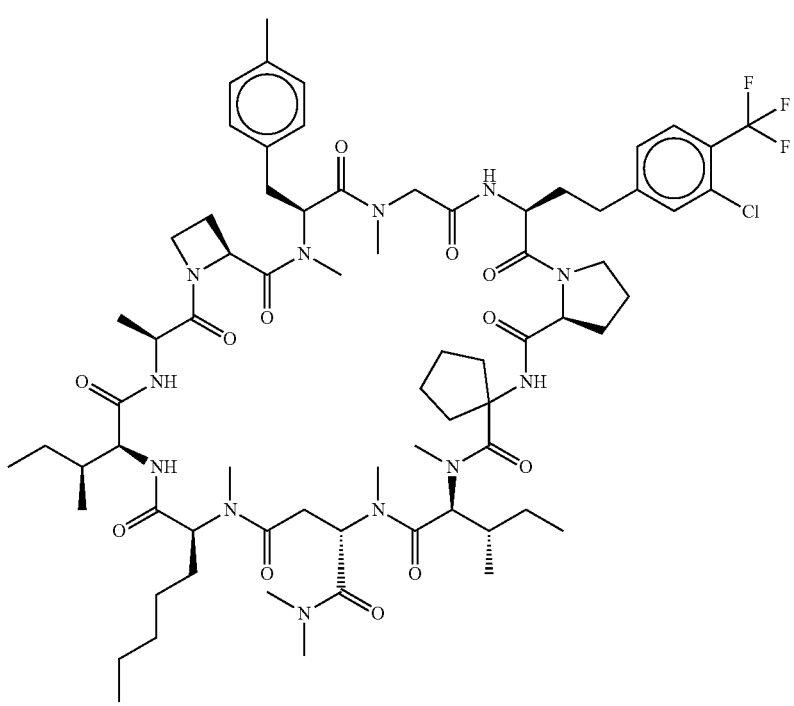 |
| 343 | 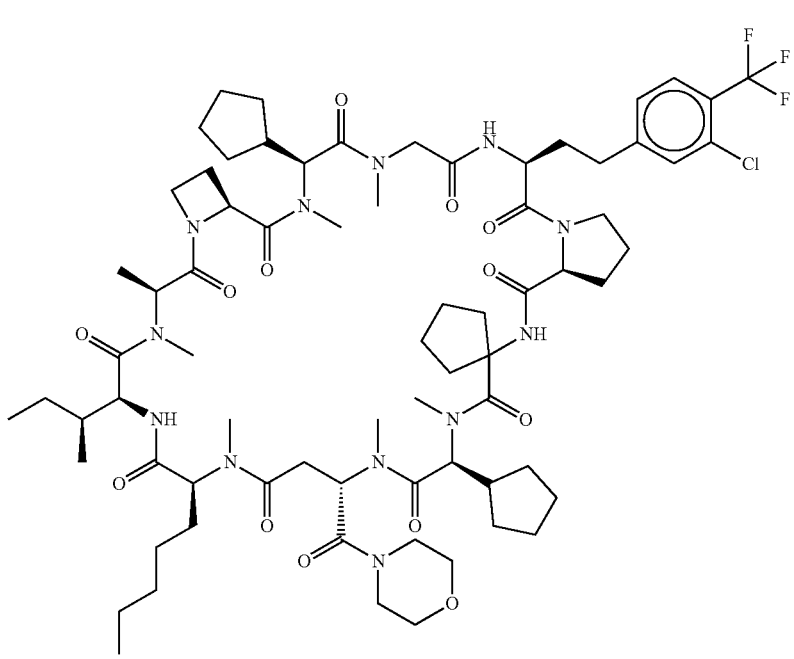 |

TABLE 24-continued
| Compound No. | Structural formula |
|---|---|
| 344 | 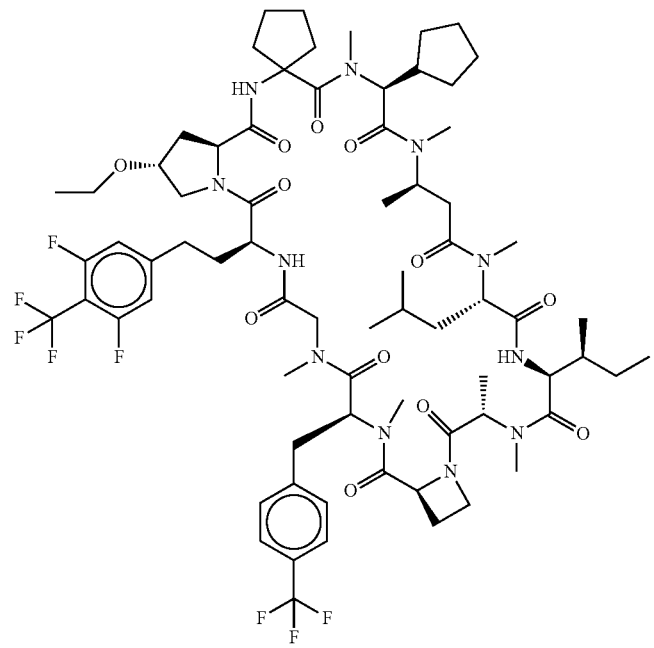 |
| 345 | 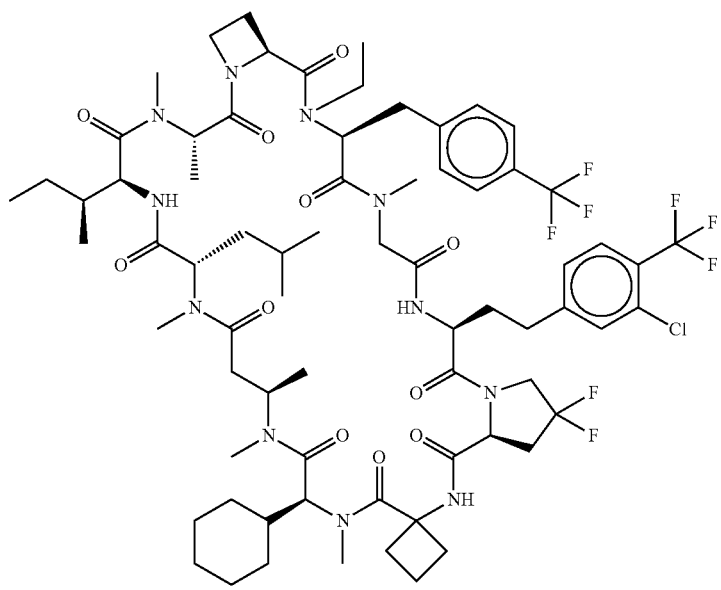 |

TABLE 24-continued
| Compound No. | Structural formula |
|---|---|
| 346 | 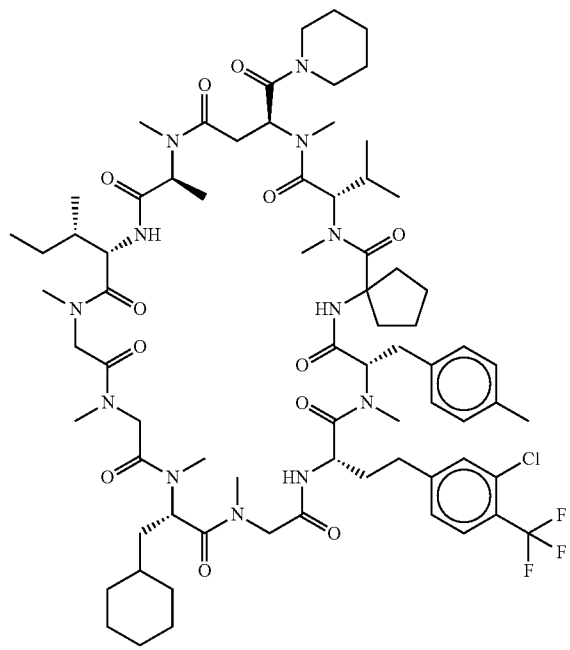 |
| 347 | 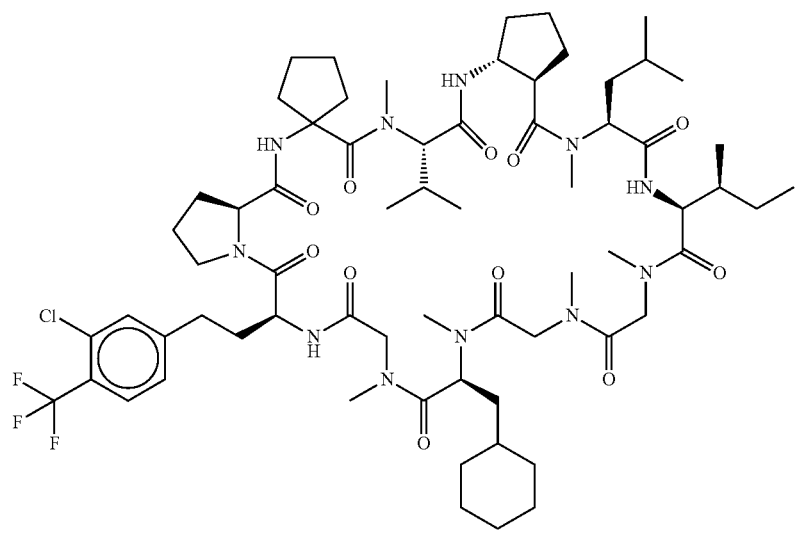 |

TABLE 24-continued
| Compound No. | Structural formula |
|---|---|
| 348 | 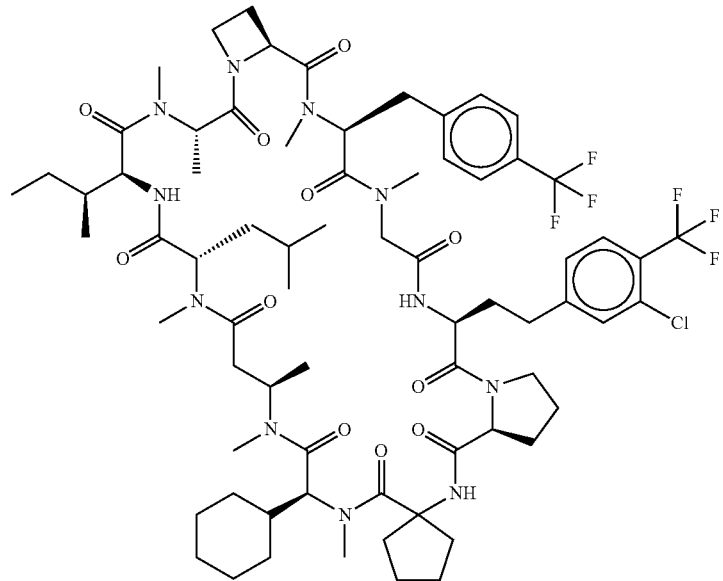 |
| 349 | 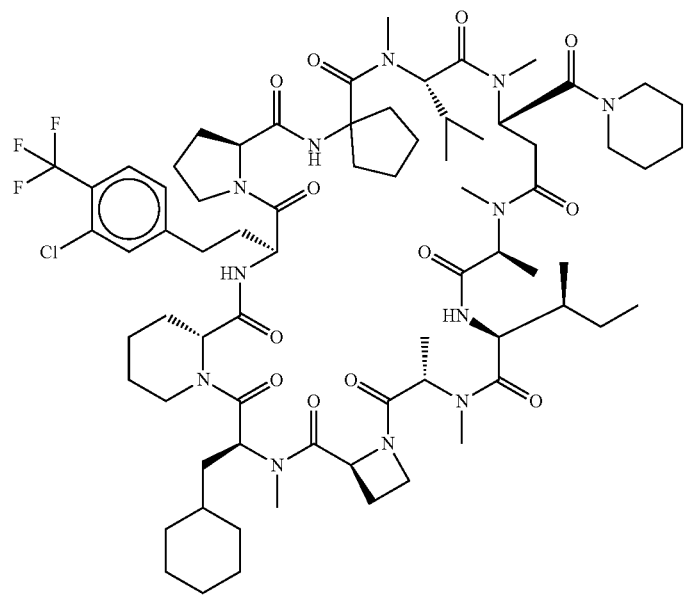 |

TABLE 24-continued
| Compound No. | Structural formula |
|---|---|
| 350 | 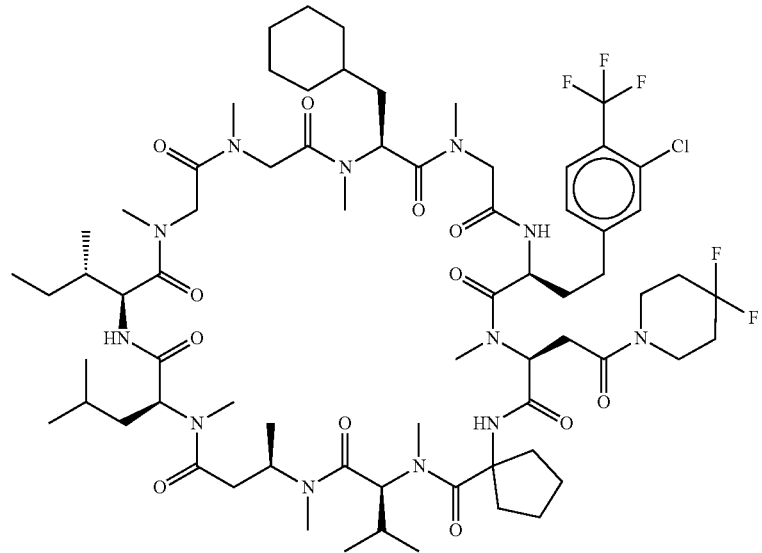 |
| 351 | 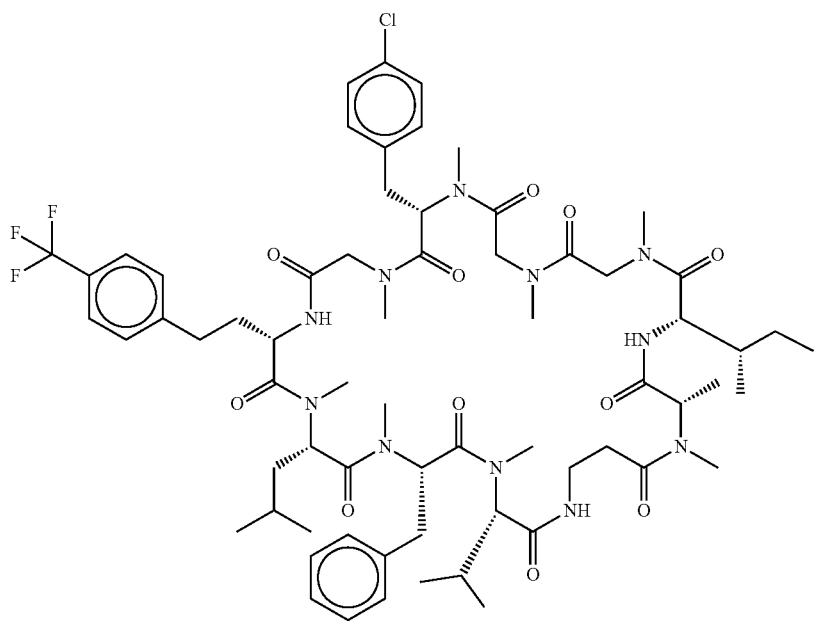 |

TABLE 24-continued
| Compound No. | Structural formula |
|---|---|
| 352 | 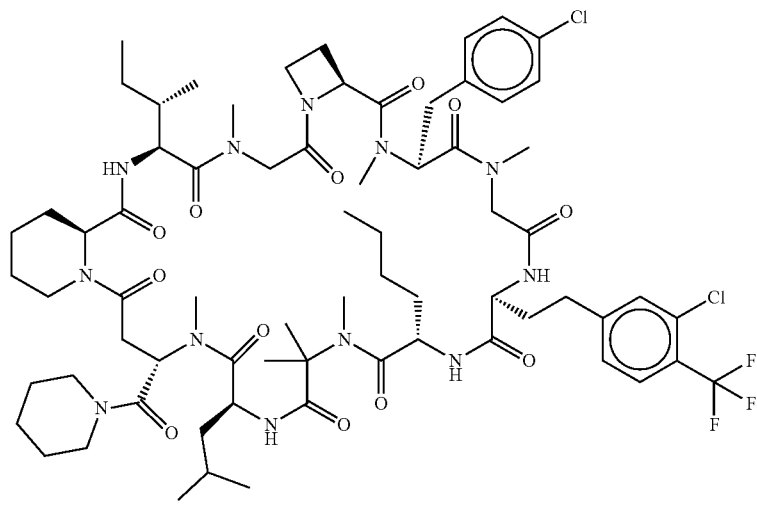 |
| 353 | 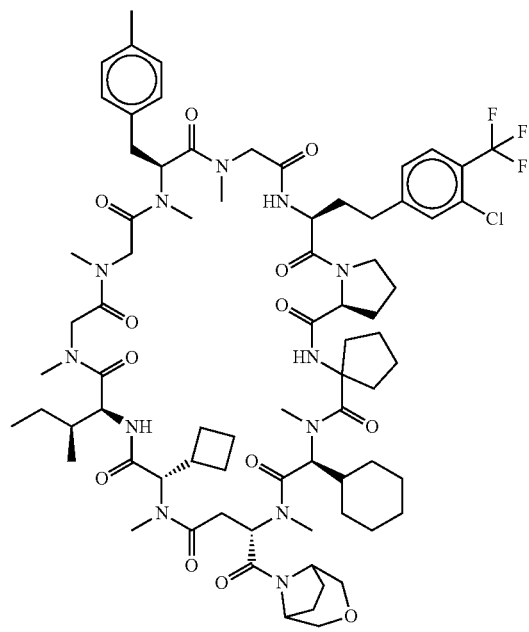 |

TABLE 24-continued
| Compound No. | Structural formula |
|---|---|
| 354 | 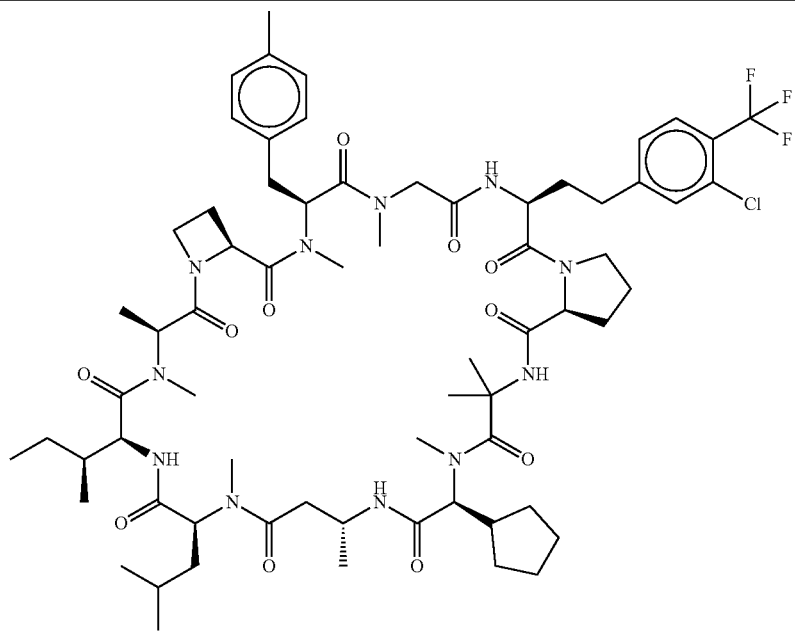 |
| 355 | 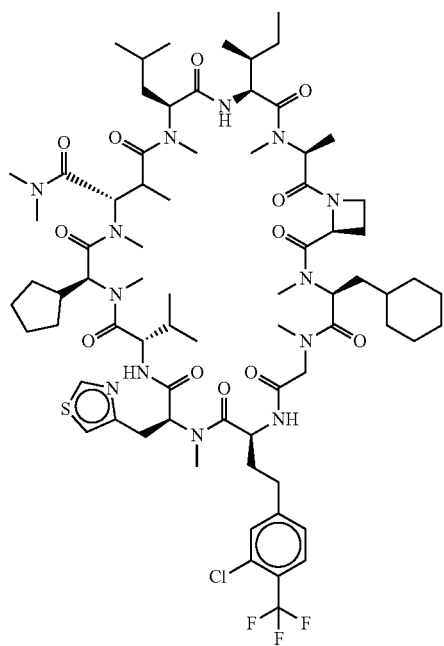 |

TABLE 24-continued
| Compound No. | Structural formula |
|---|---|
| 356 | 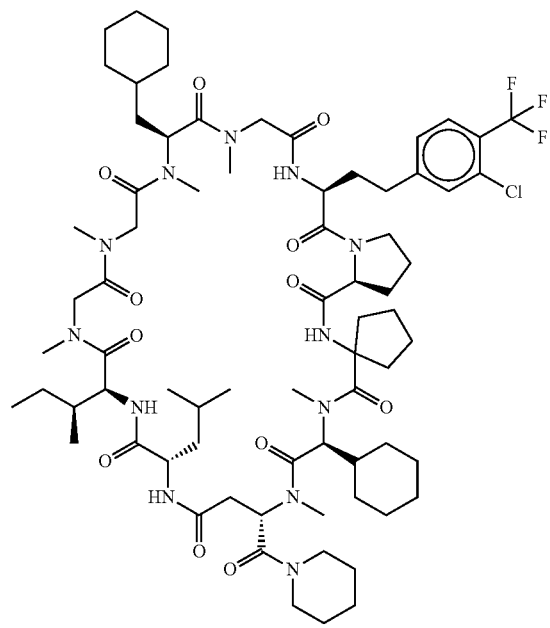 |
| 357 | 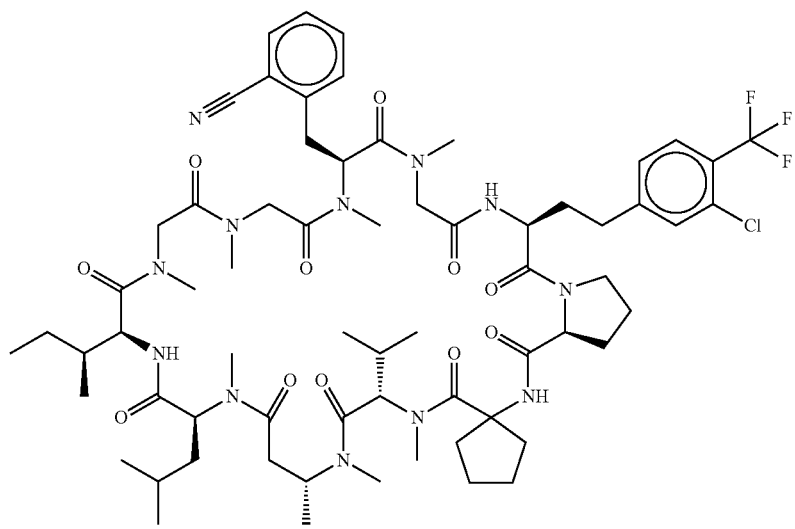 |

TABLE 24-continued
| Compound No. | Structural formula |
|---|---|
| 358 | 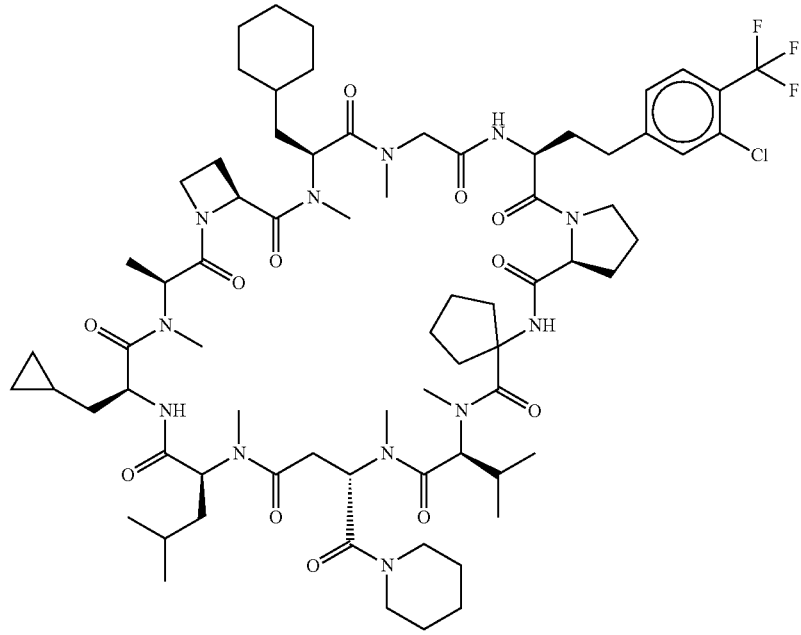 |
| 359 | 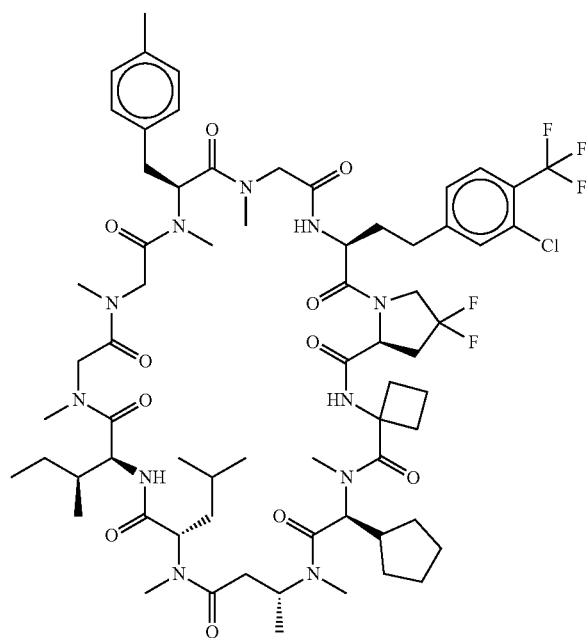 |

TABLE 24-continued
| Compound No. | Structural formula |
|---|---|
| 360 | 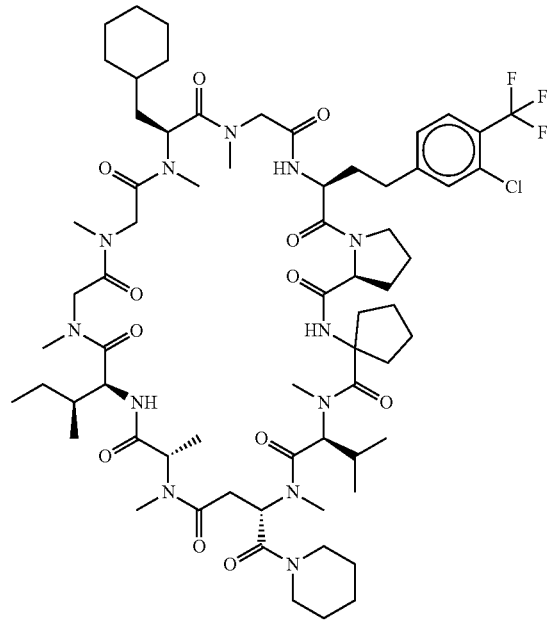 |
| 361 | 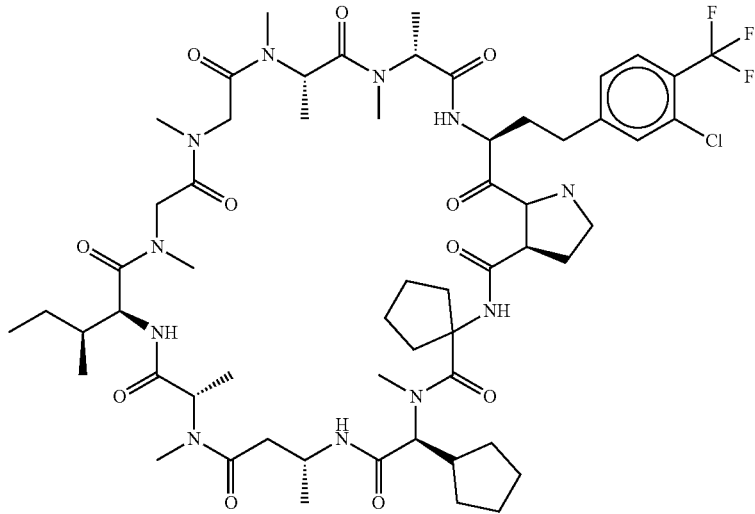 |

TABLE 24-continued
| Compound No. | Structural formula |
|---|---|
| 362 | 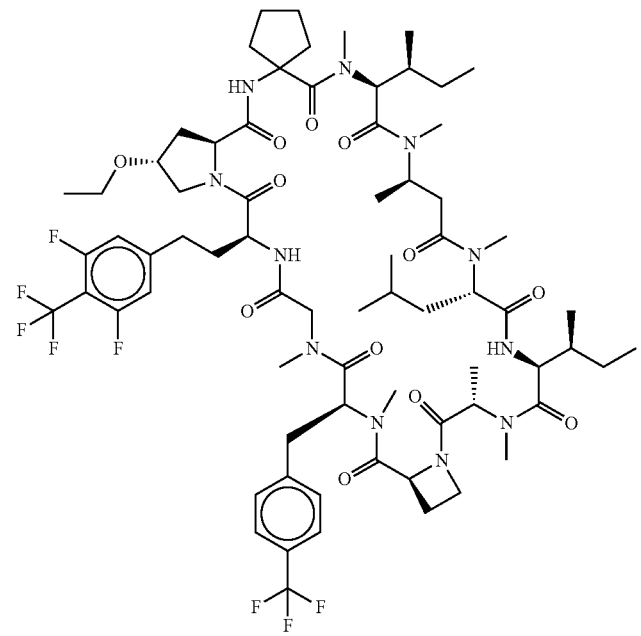 |
| 363 | 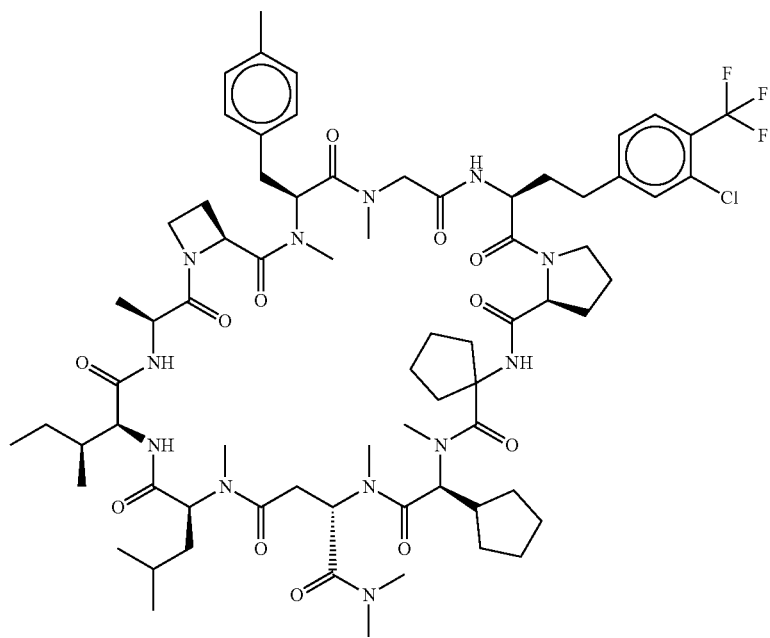 |

TABLE 24-continued
| Compound No. | Structural formula |
|---|---|
| 364 | 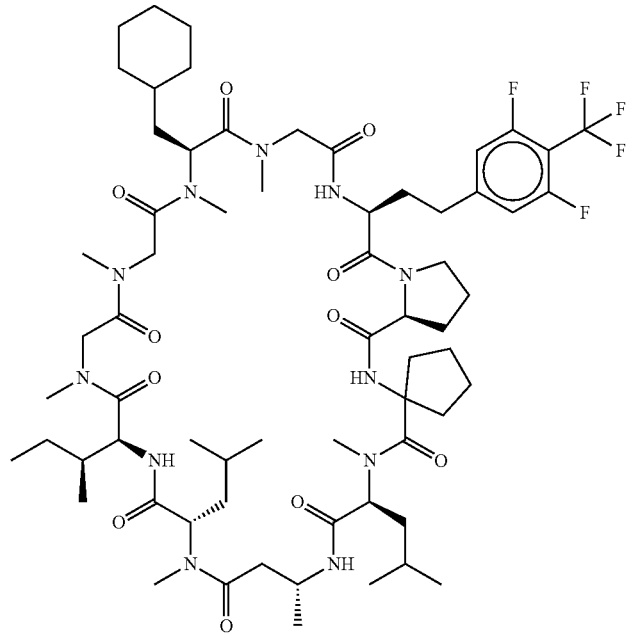 |
| 365 | 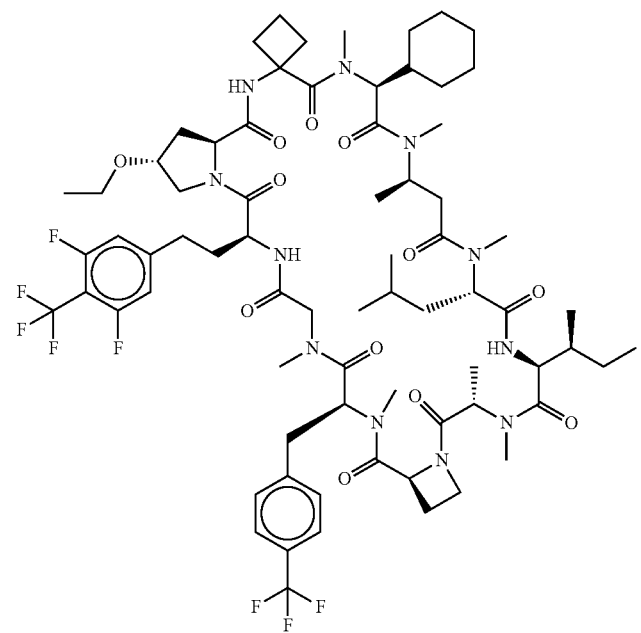 |

TABLE 24-continued
| Compound No. | Structural formula |
|---|---|
| 366 | 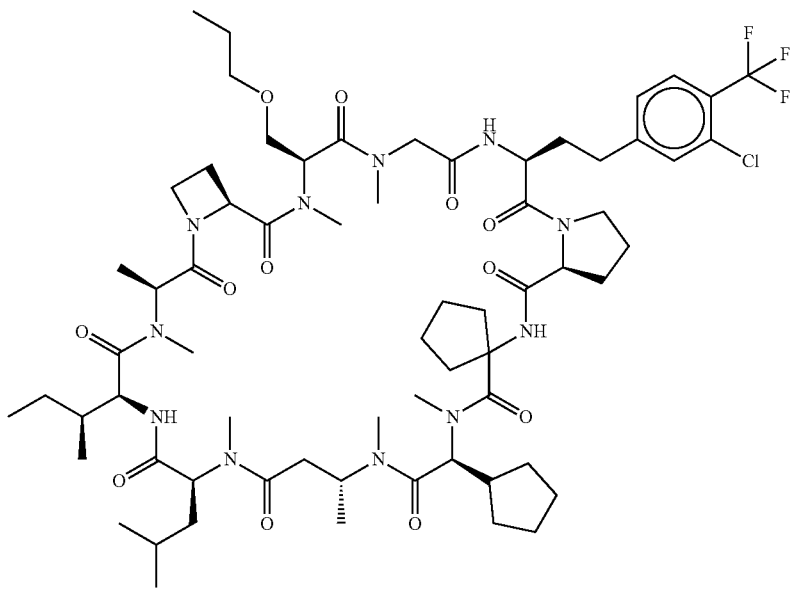 |
| 367 | 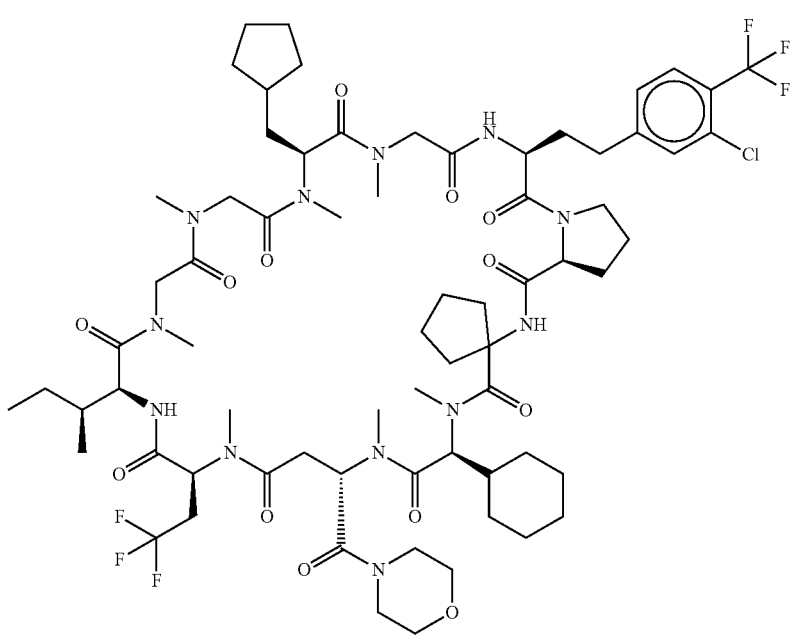 |

TABLE 24-continued
| Compound No. | Structural formula |
|---|---|
| 368 | 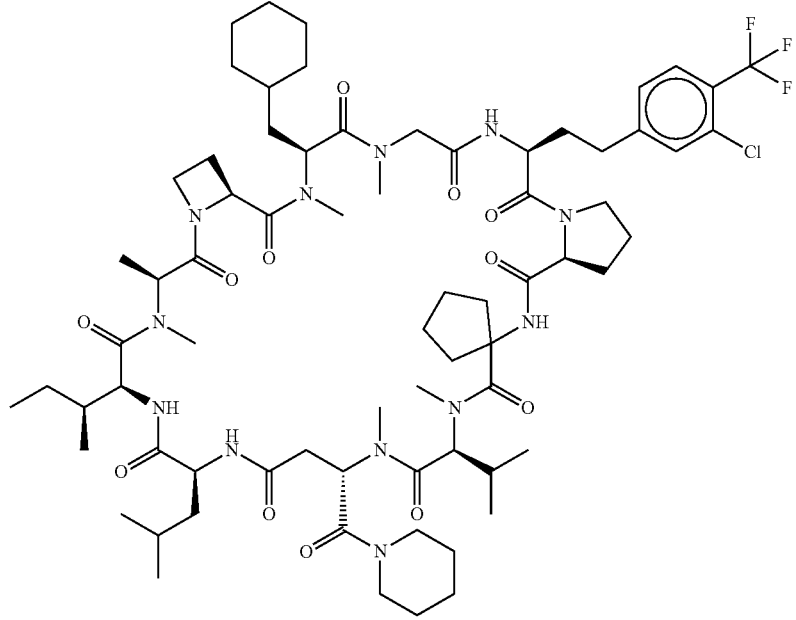 |
| 369 | 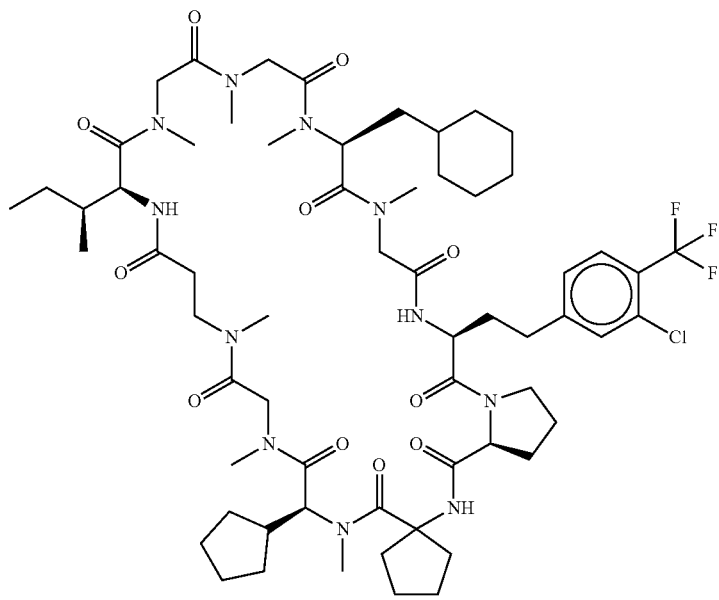 |

TABLE 24-continued
| Compound No. | Structural formula |
|---|---|
| 370 | 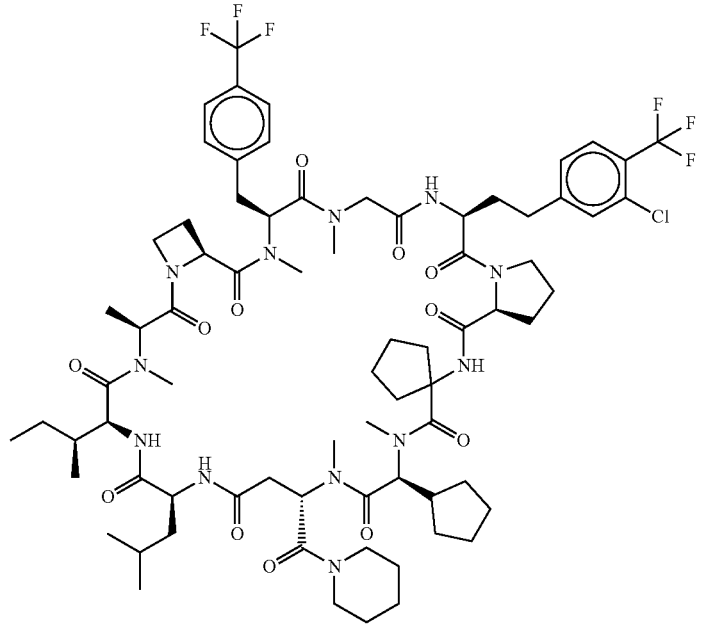 |
| 371 | 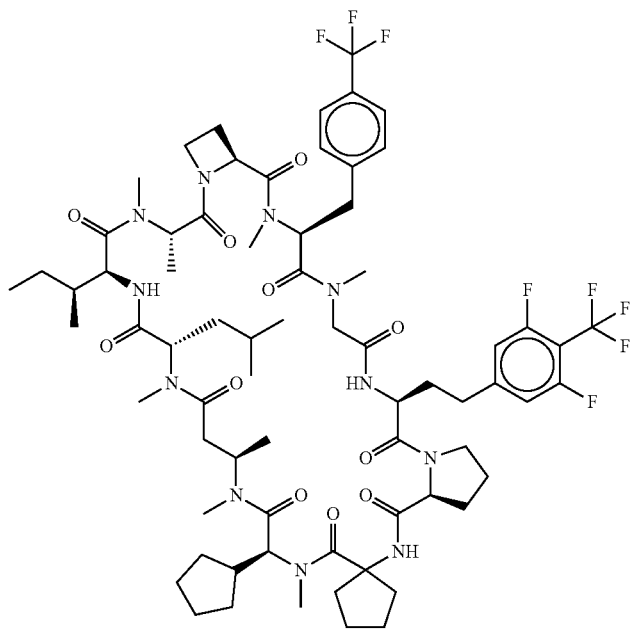 |

TABLE 24-continued
| Compound No. | Structural formula |
|---|---|
| 372 | 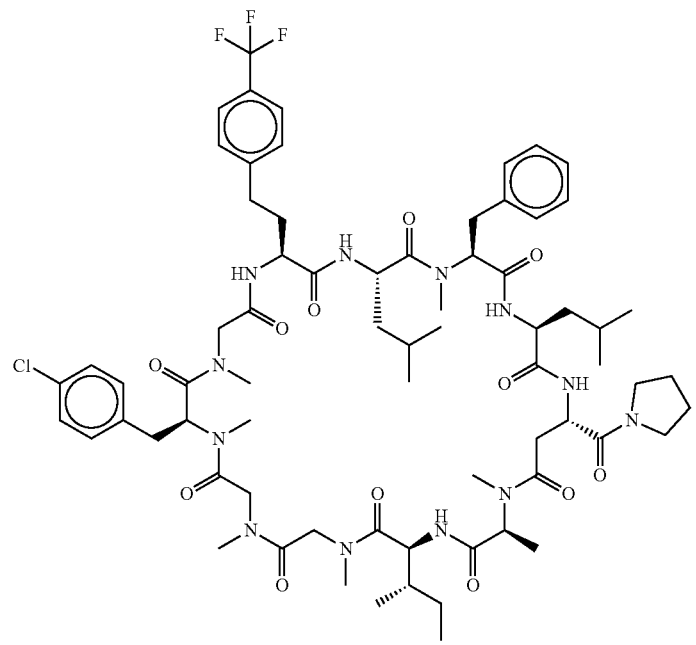 |
| 373 | 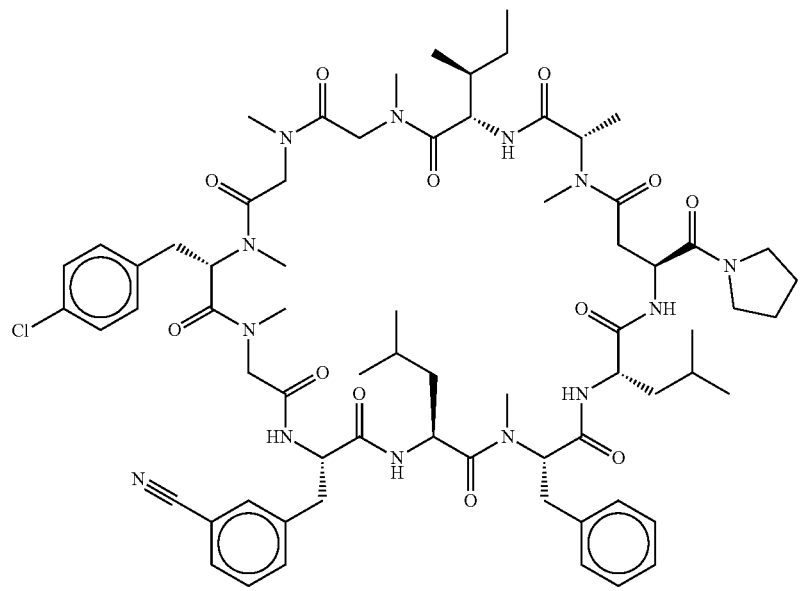 |

TABLE 24-continued
| Compound No. | Structural formula |
|---|---|
| 374 | 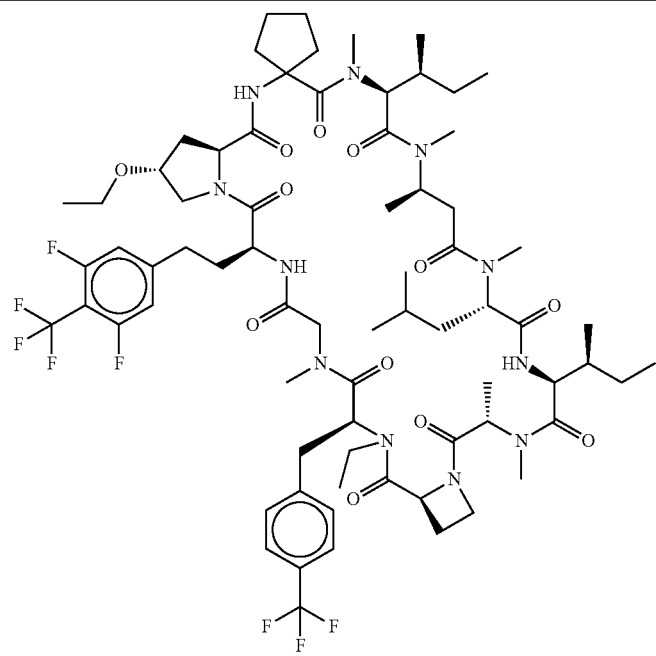 |
| 375 | 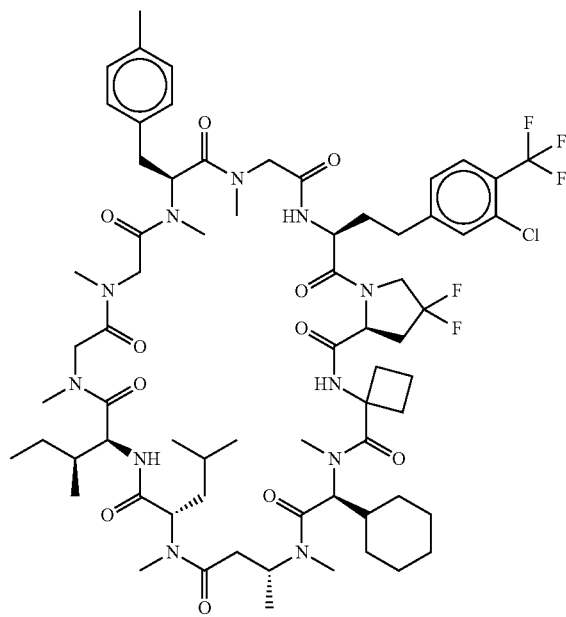 |

TABLE 24-continued
| Compound No. | Structural formula |
|---|---|
| 376 | 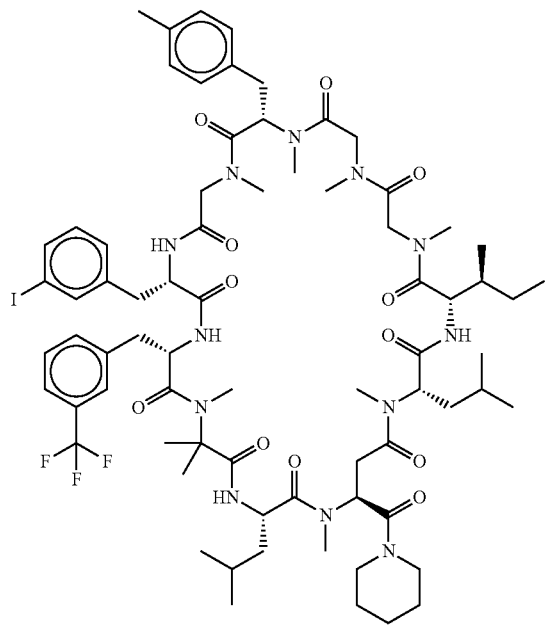 |
| 377 | 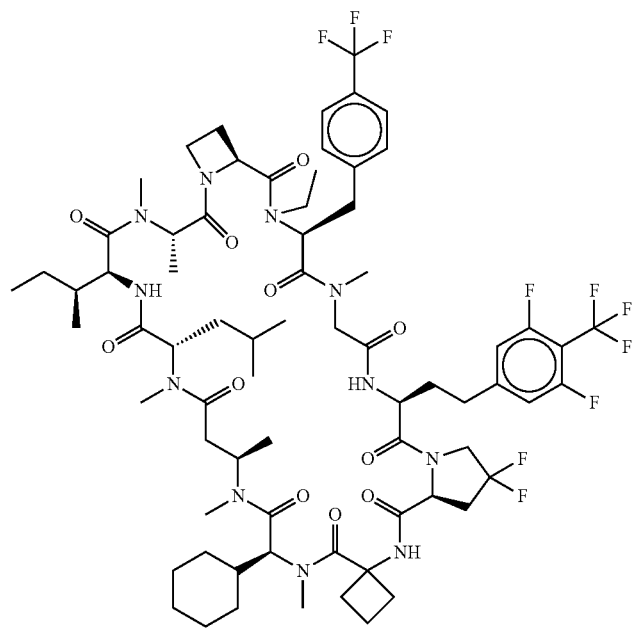 |

TABLE 24-continued
| Compound No. | Structural formula |
|---|---|
| 378 | 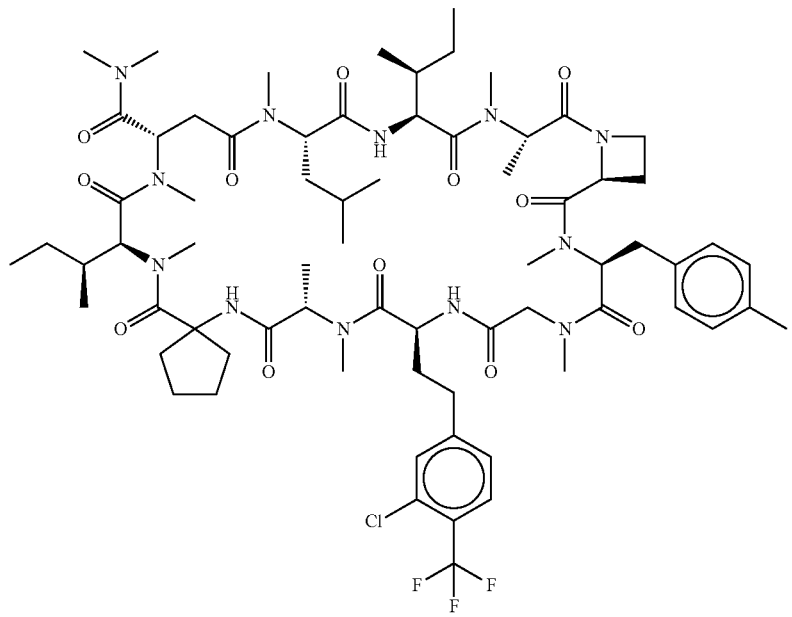 |
| 379 | 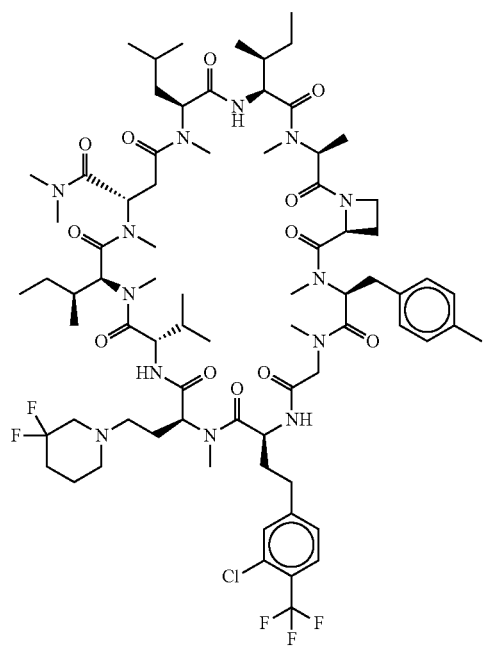 |

TABLE 24-continued
| Compound No. | Structural formula |
| --- | --- |
| 380 | 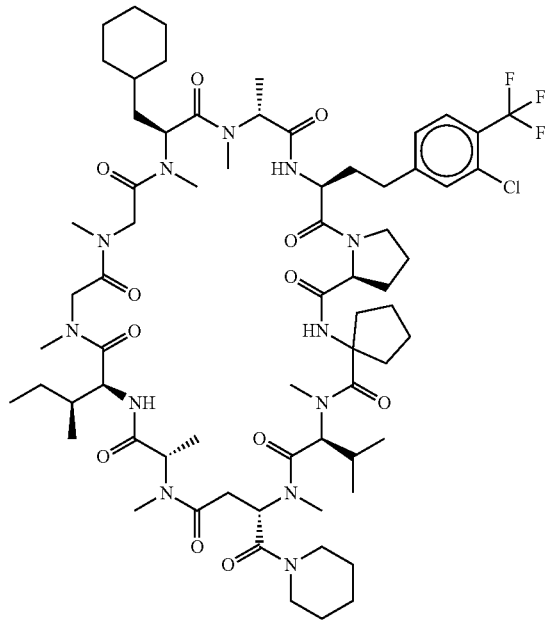 |
| 381 | 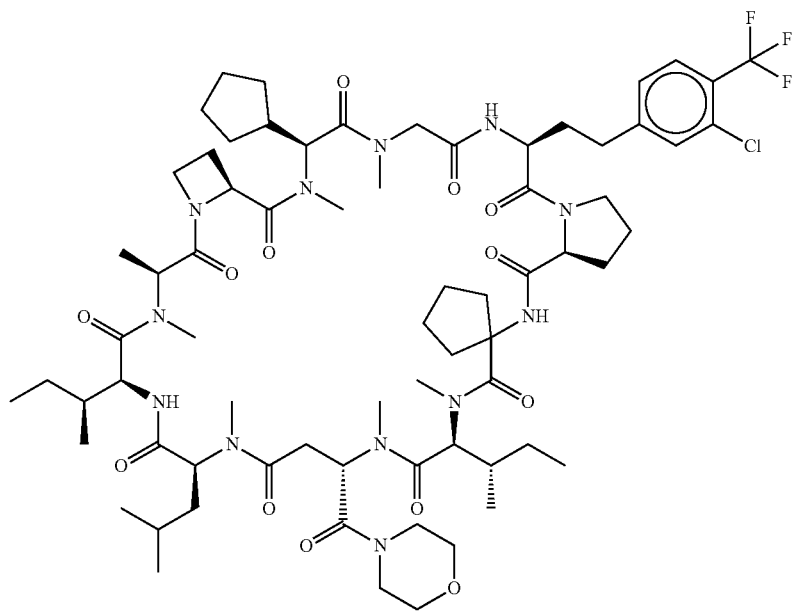 |

TABLE 24-continued
| Compound No. | Structural formula |
| --- | --- |
| 382 | 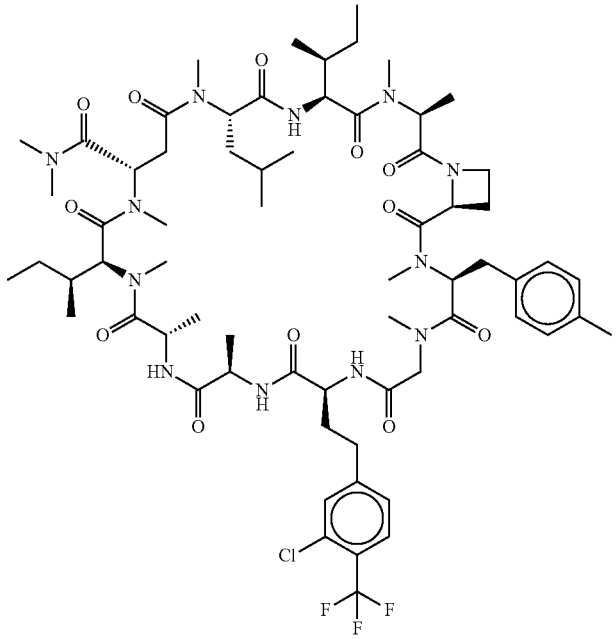 |
| 383 | 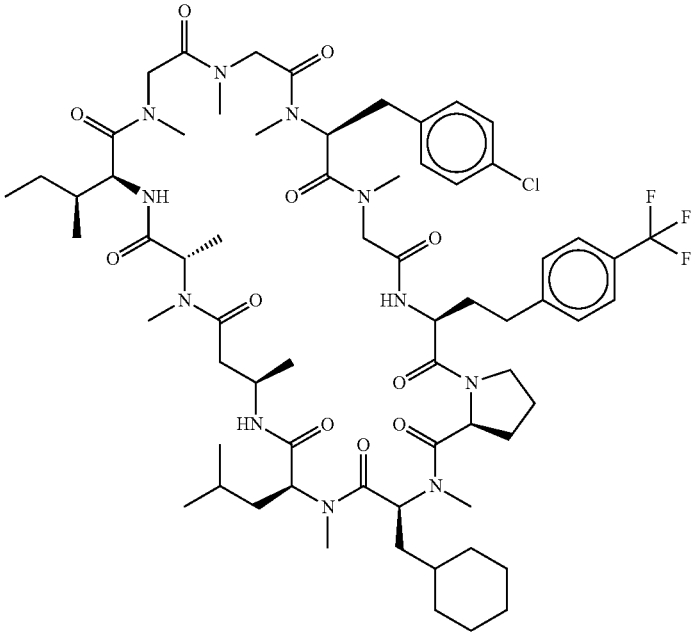 |

TABLE 24-continued
| Compound No. | Structural formula |
|---|---|
| 384 | 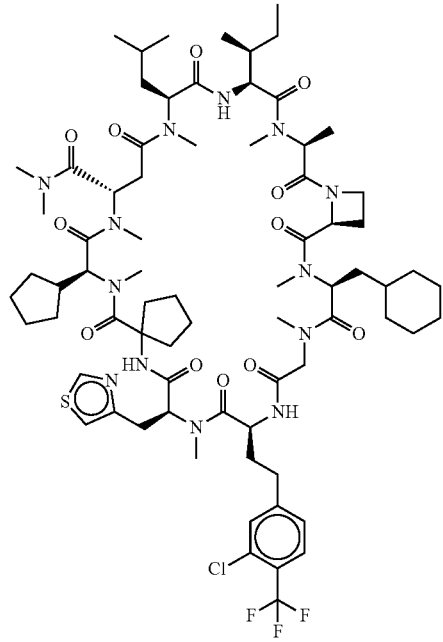 |
| 385 | 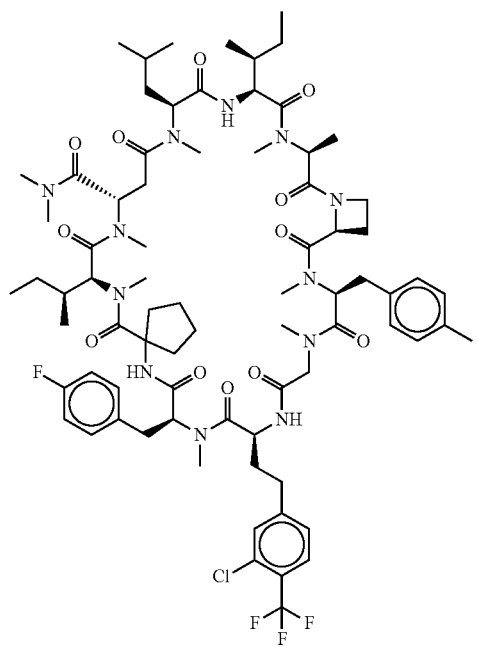 |

TABLE 24-continued
| Compound No. | Structural formula |
|---|---|
| 386 | 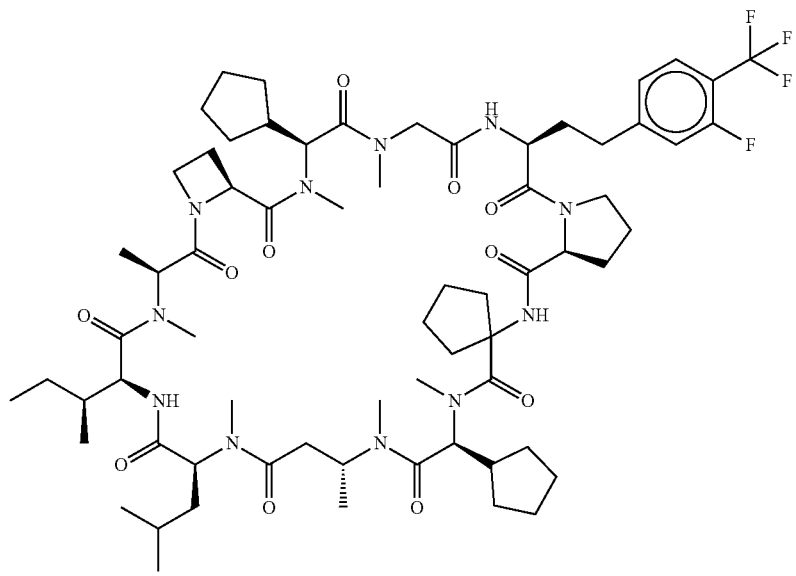 |
| 387 | 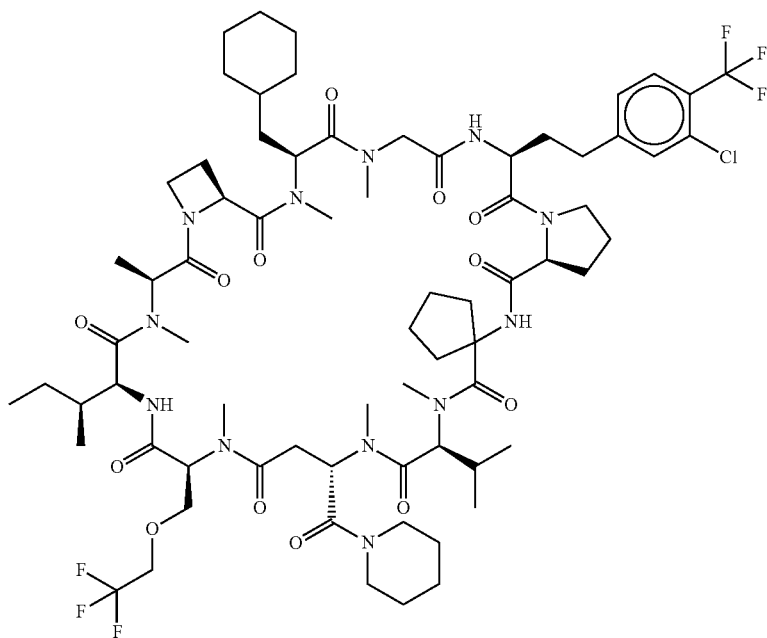 |

TABLE 24-continued
| Compound No. | Structural formula |
|---|---|
| 388 | 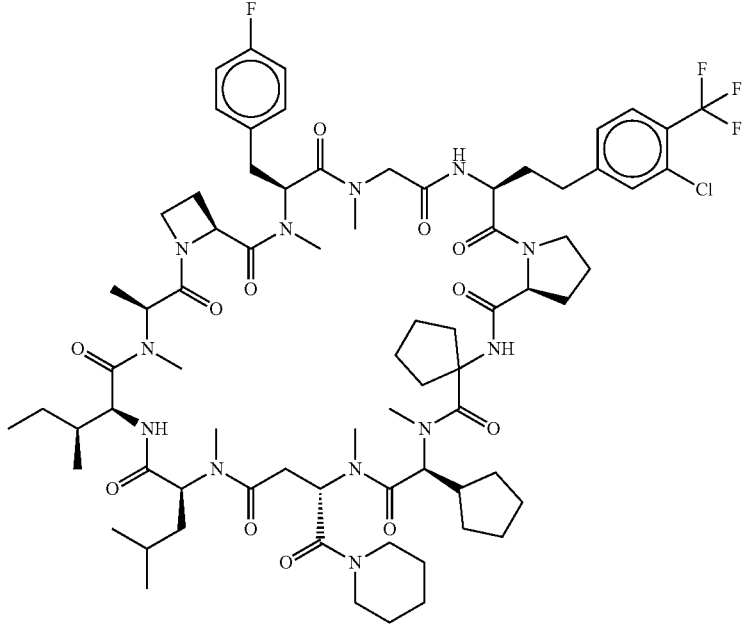 |
| 389 | 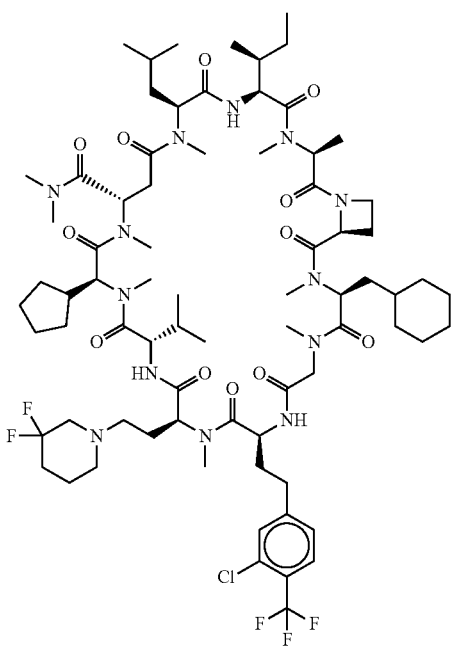 |

TABLE 24-continued
| Compound No. | Structural formula |
|---|---|
| 390 | 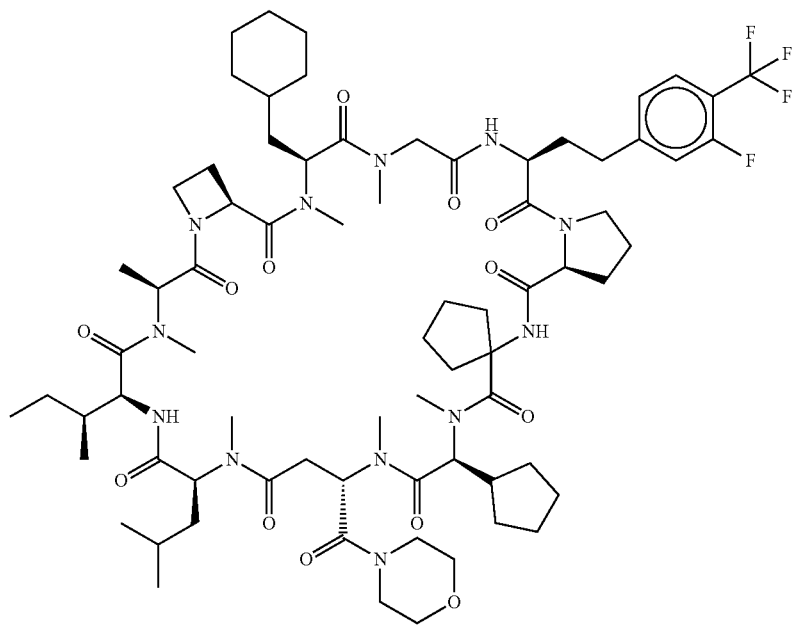 |
| 391 | 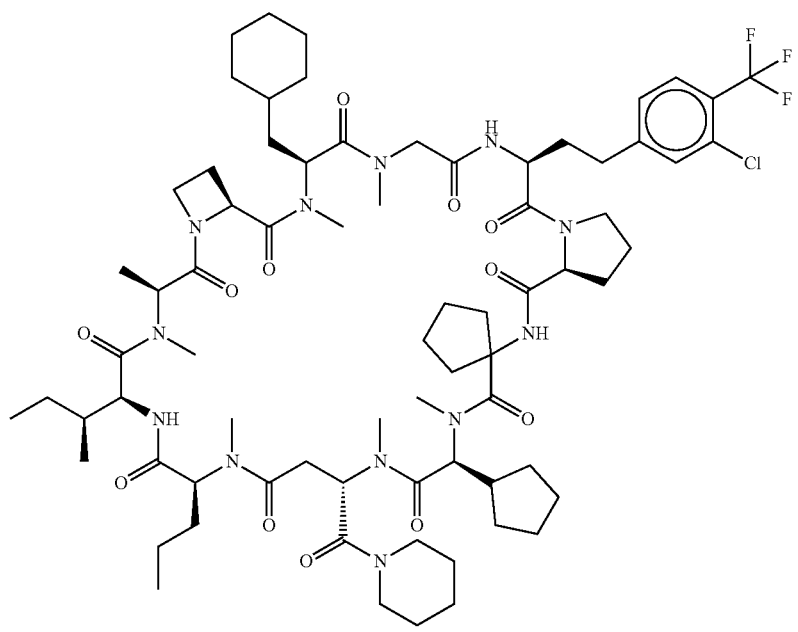 |

TABLE 24-continued
| Compound No. | Structural formula |
|---|---|
| 392 | 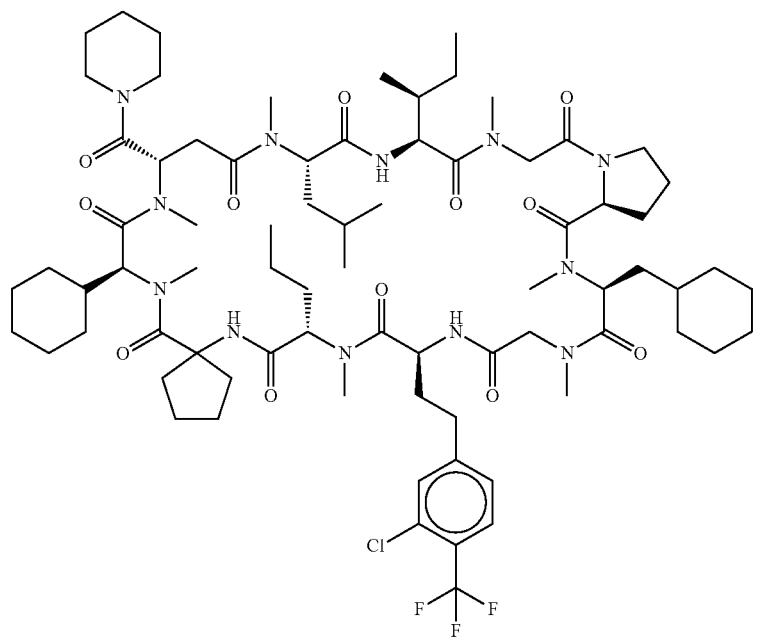 |
| 393 | 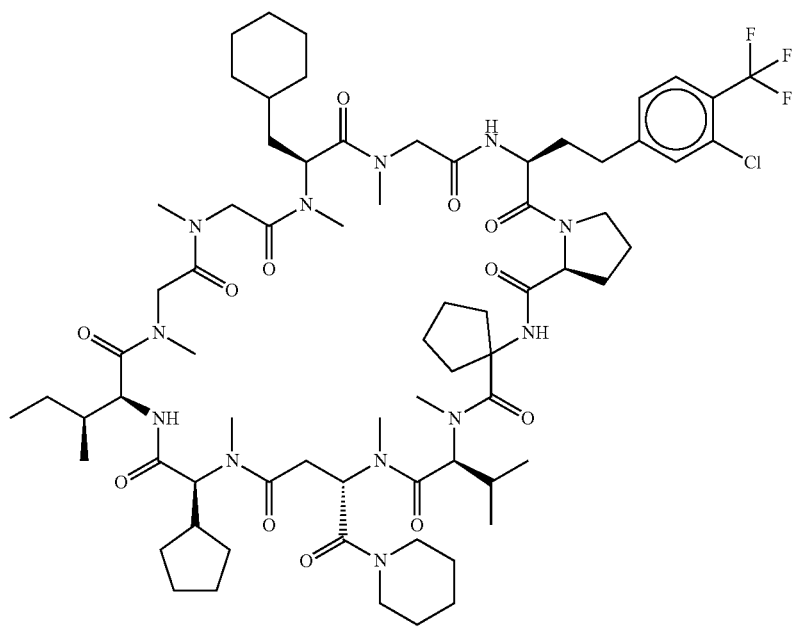 |

TABLE 24-continued
| Compound No. | Structural formula |
|---|---|
| 394 | 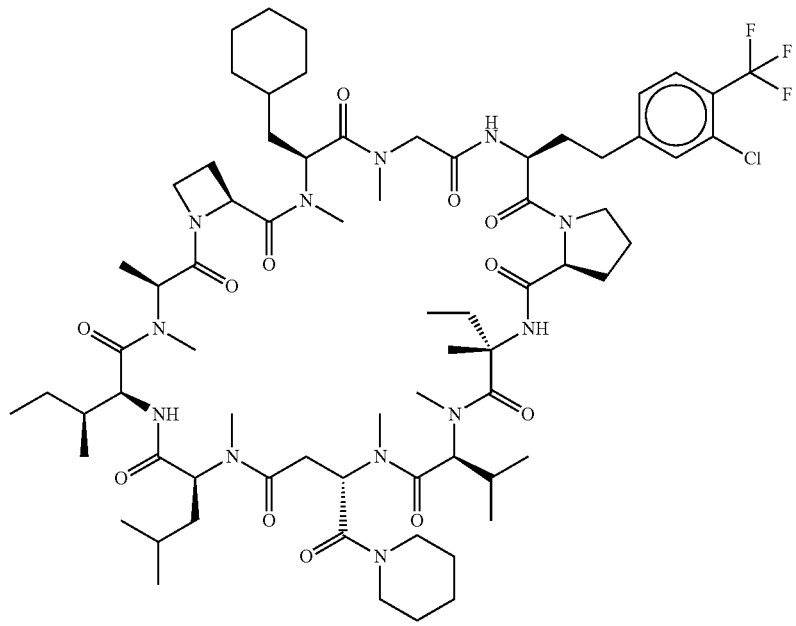 |
| 395 | 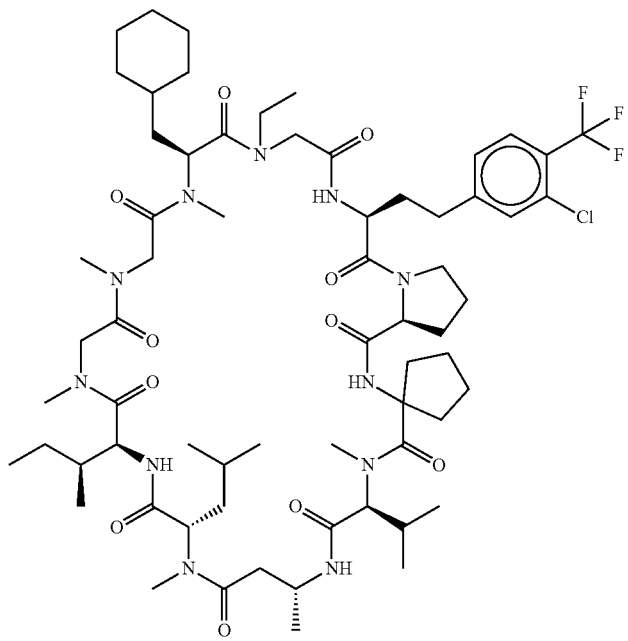 |

TABLE 24-continued
| Compound No. | Structural formula |
|---|---|
| 396 | 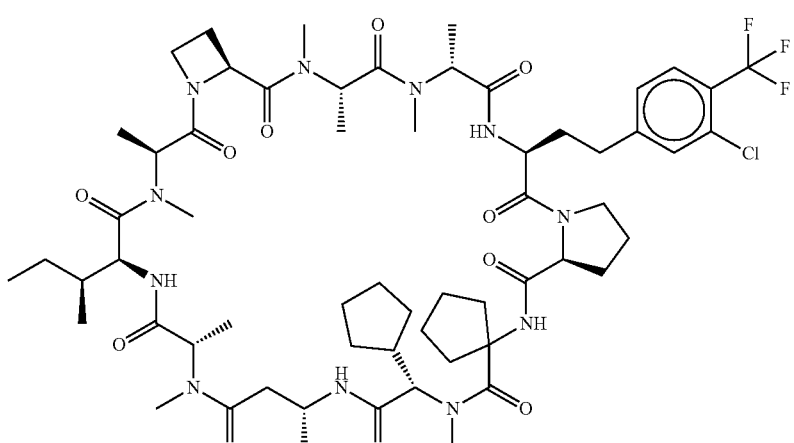 |
| 397 | 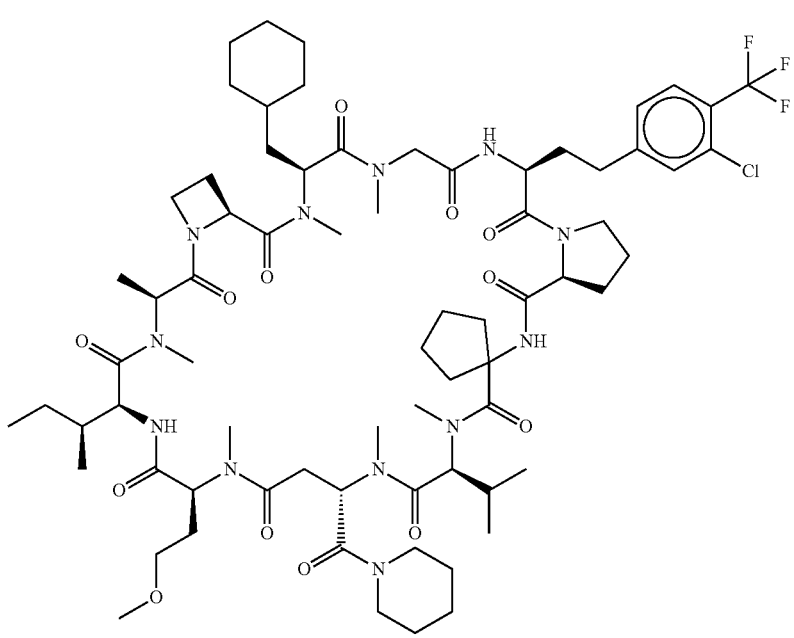 |

TABLE 24-continued
| Compound No. | Structural formula |
|---|---|
| 398 | 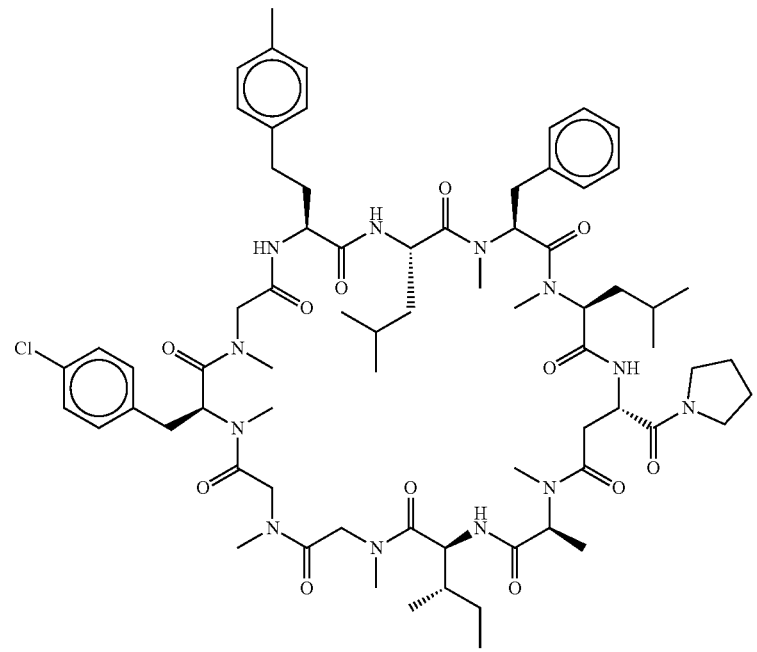 |
| 399 | 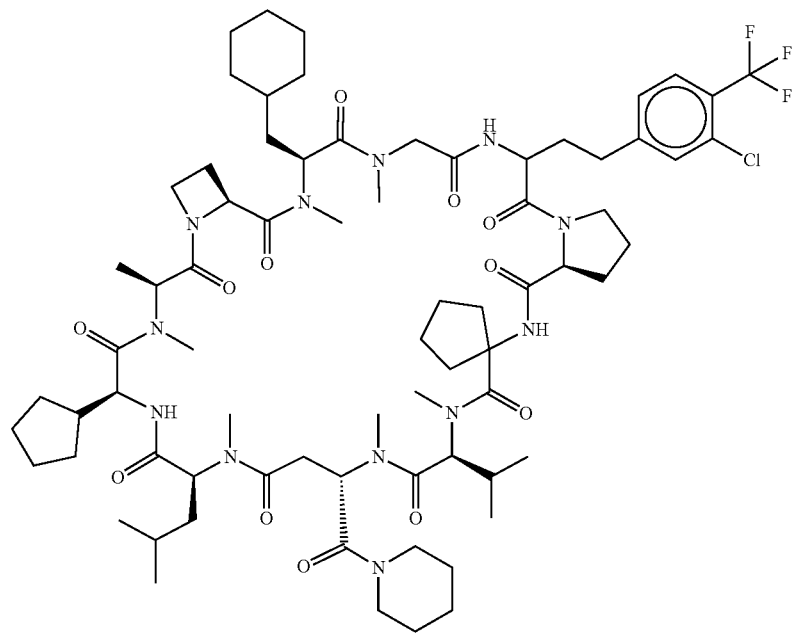 |

TABLE 24-continued
| Compound No. | Structural formula |
|---|---|
| 400 | 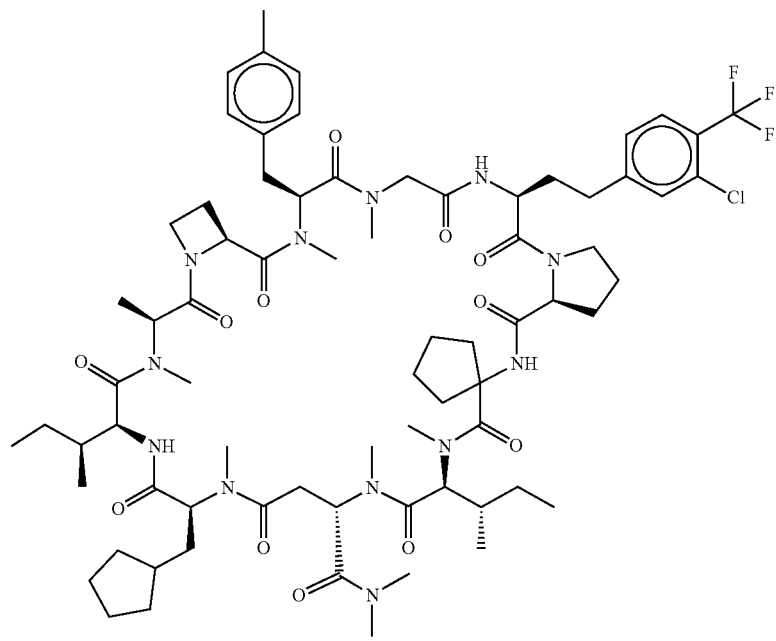 |
| 401 | 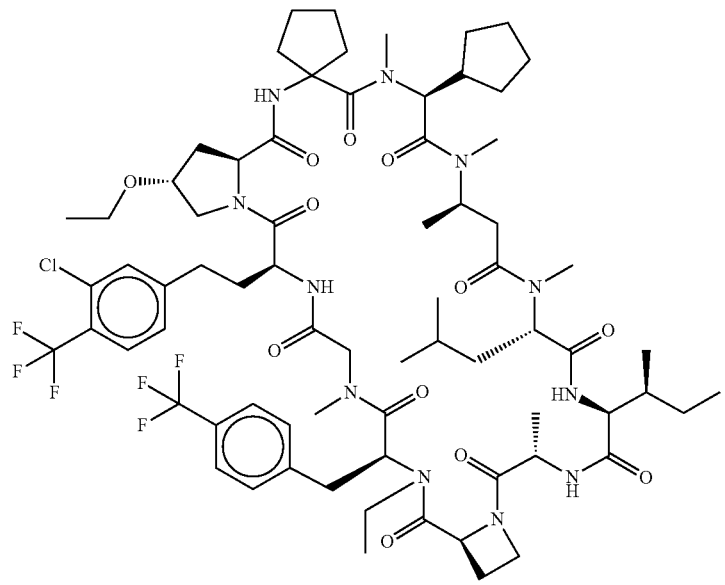 |

TABLE 24-continued
| Compound No. | Structural formula |
|---|---|
| 402 | 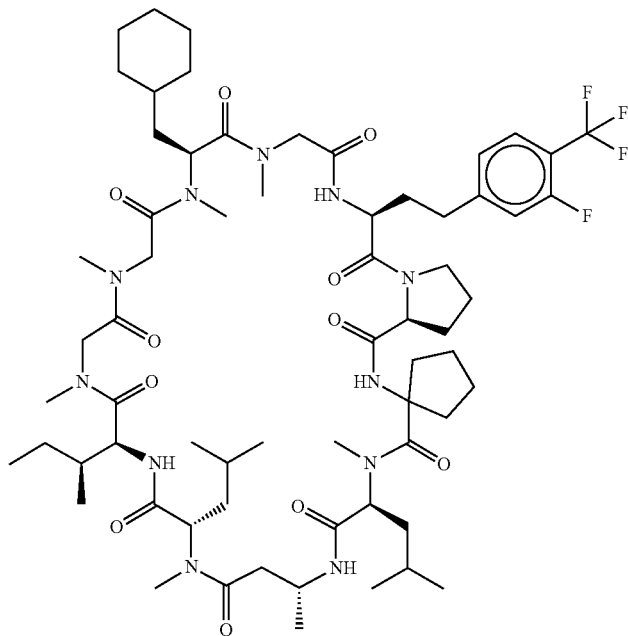 |
| 403 | 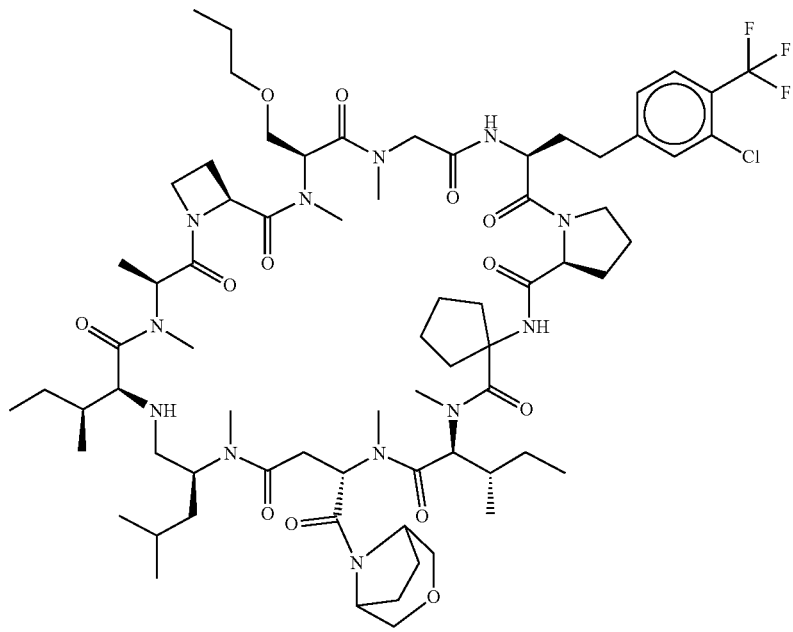 |

TABLE 24-continued
| Compound No. | Structural formula |
|---|---|
| 404 | 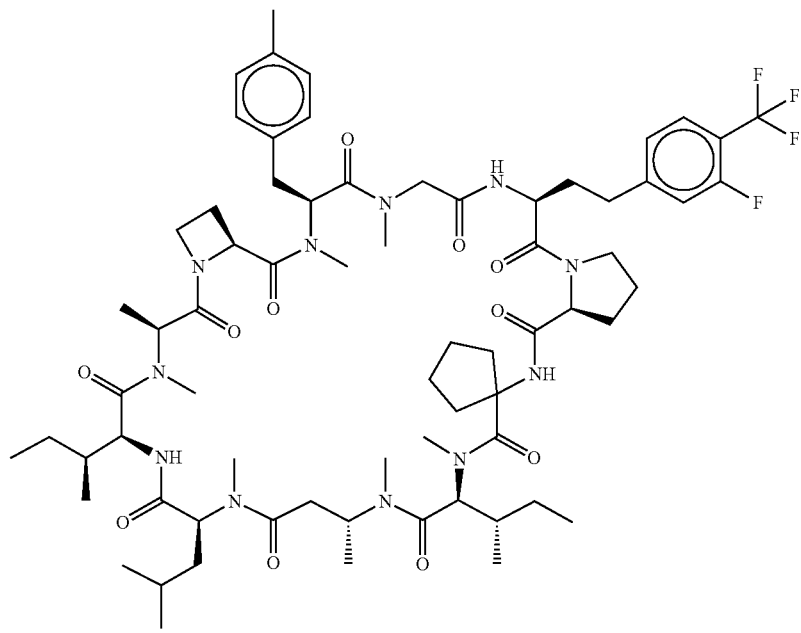 |
| 405 | 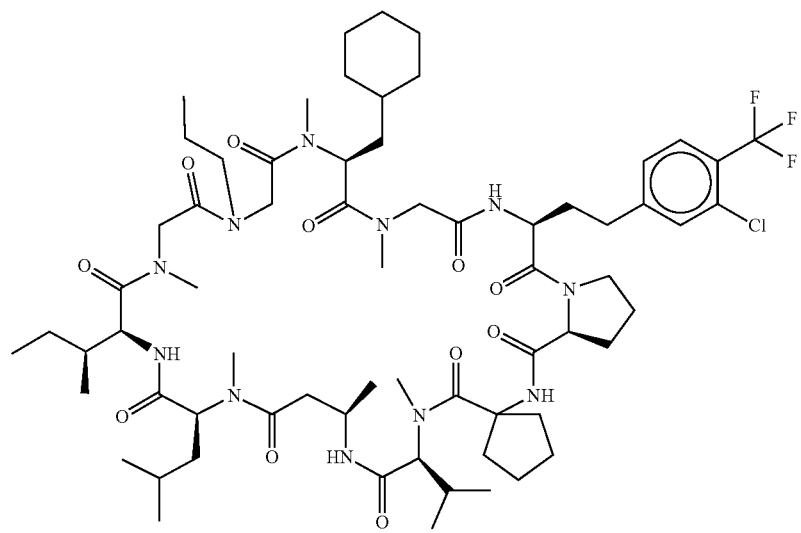 |

TABLE 24-continued
| Compound No. | Structural formula |
|---|---|
| 406 | 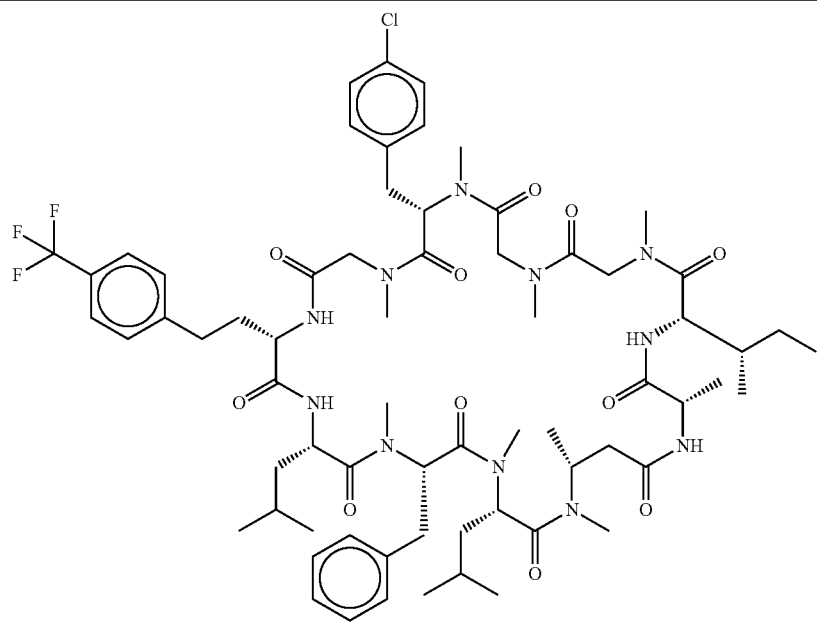 |
| 407 | 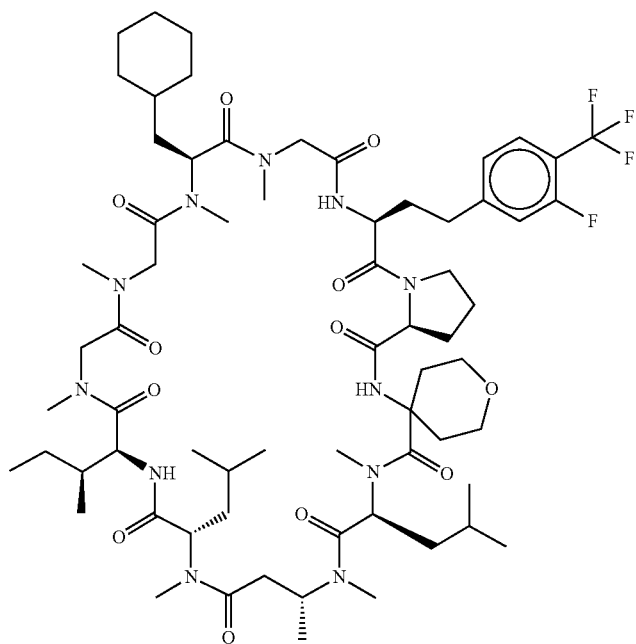 |

TABLE 24-continued
| Compound No. | Structural formula |
|---|---|
| 408 | 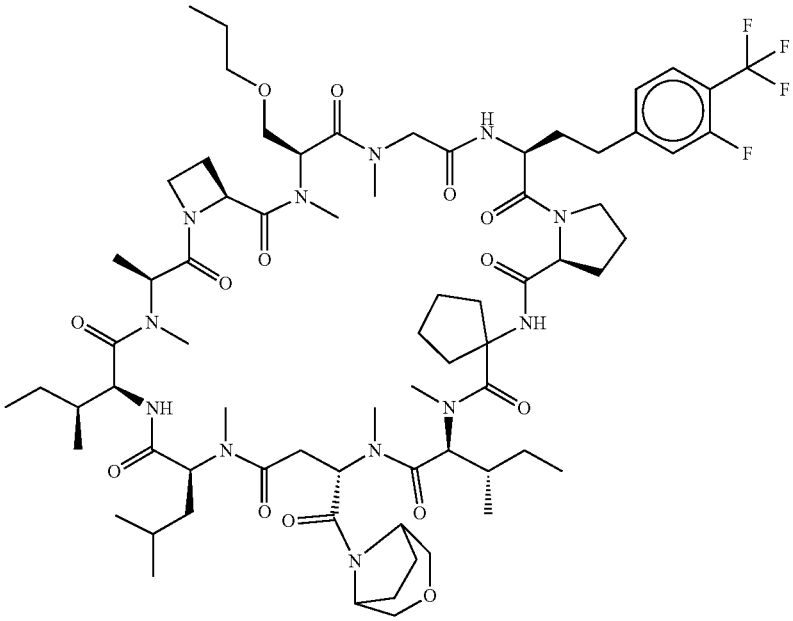 |
| 409 | 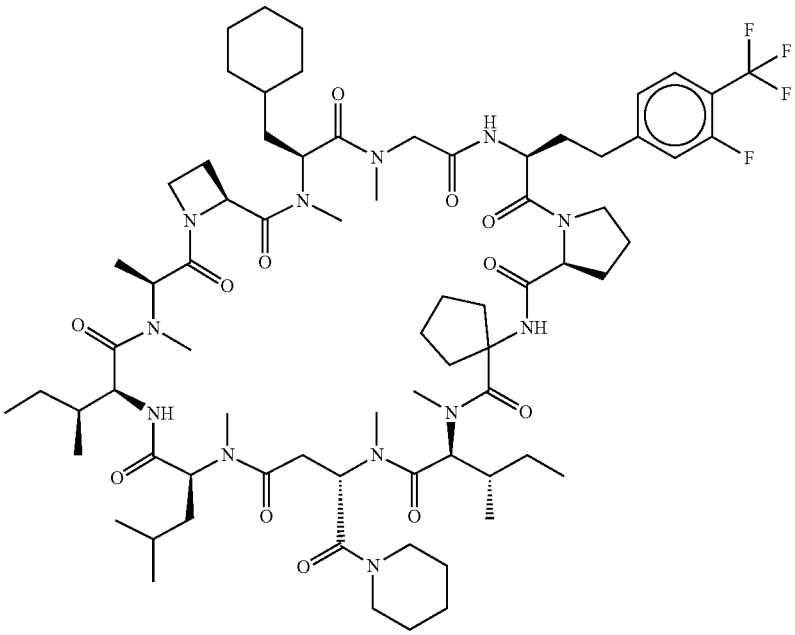 |

TABLE 24-continued
| Compound No. | Structural formula |
|---|---|
| 410 | 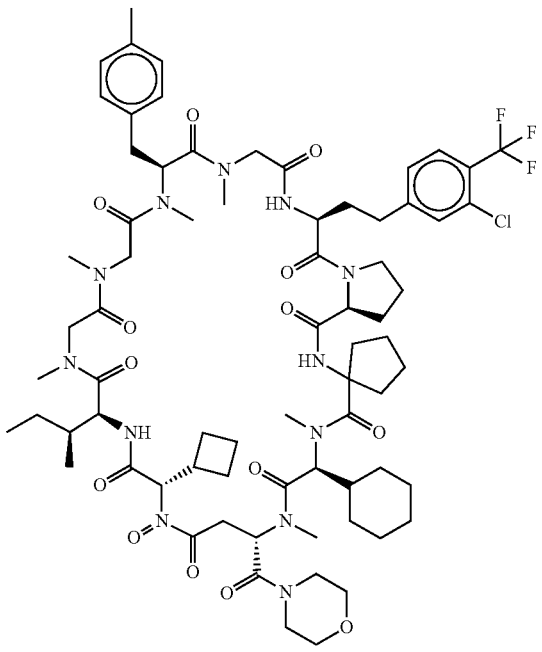 |
| 411 | 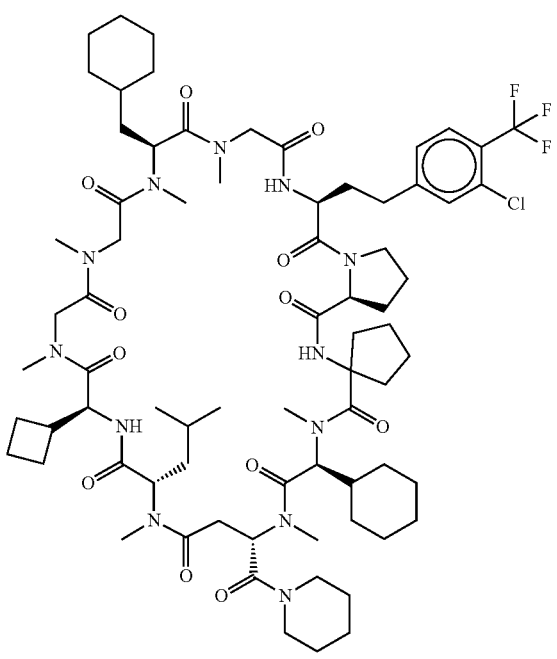 |

TABLE 24-continued
| Compound No. | Structural formula |
| --- | --- |
| 412 | 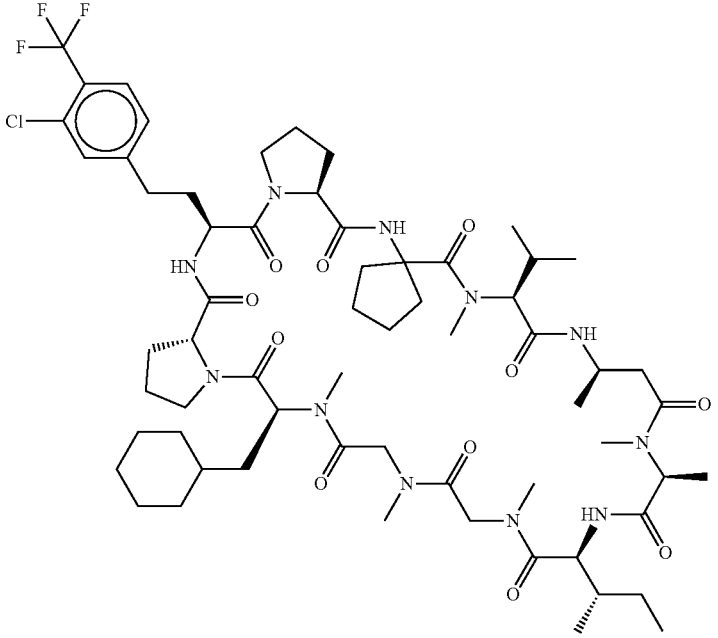 |
| 413 | 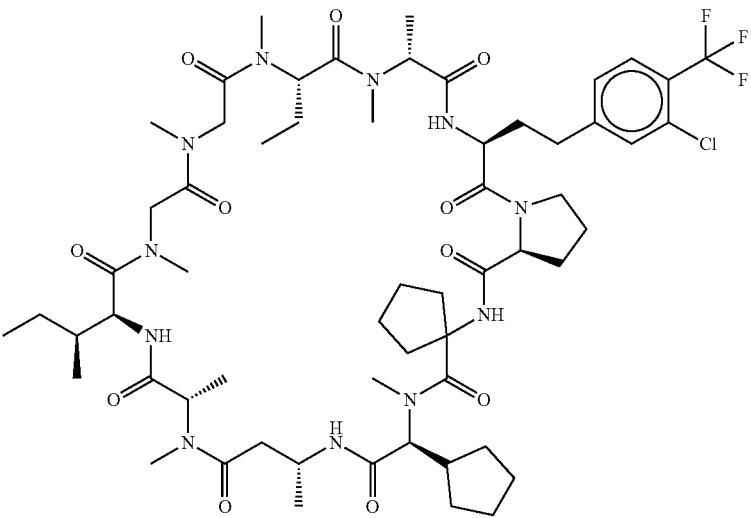 |

TABLE 24-continued
| Compound No. | Structural formula |
|---|---|
| 414 | 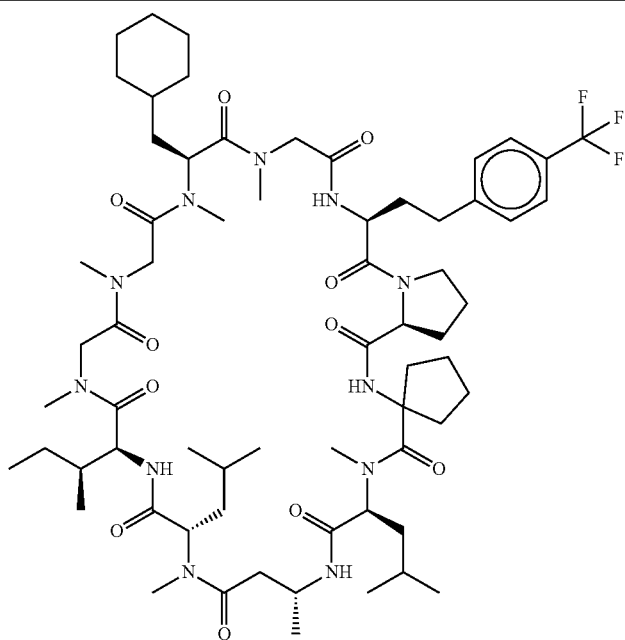 |
| 415 | 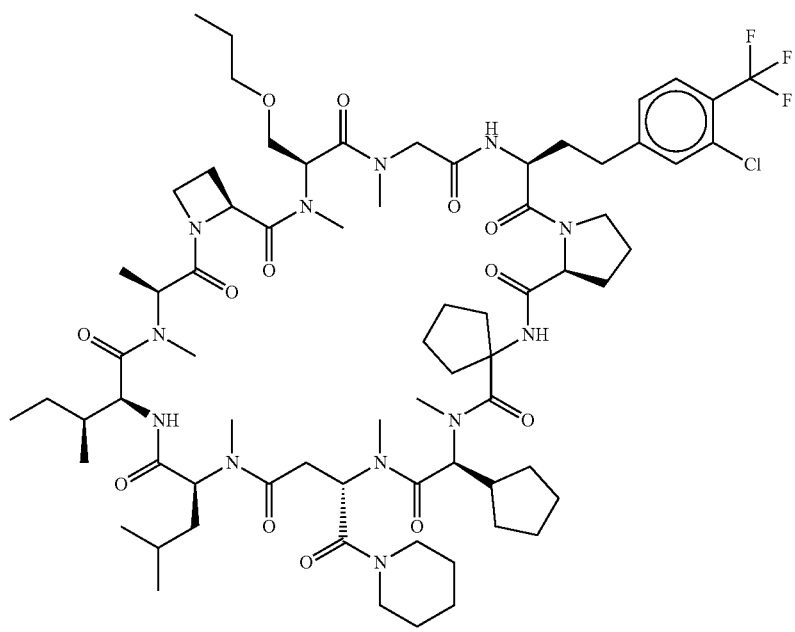 |

TABLE 24-continued
| Compound No. | Structural formula |
|---|---|
| 416 | 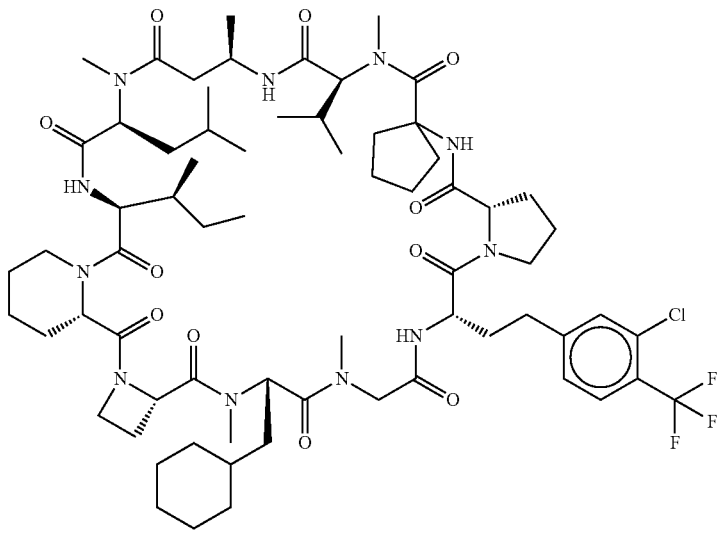 |
| 417 | 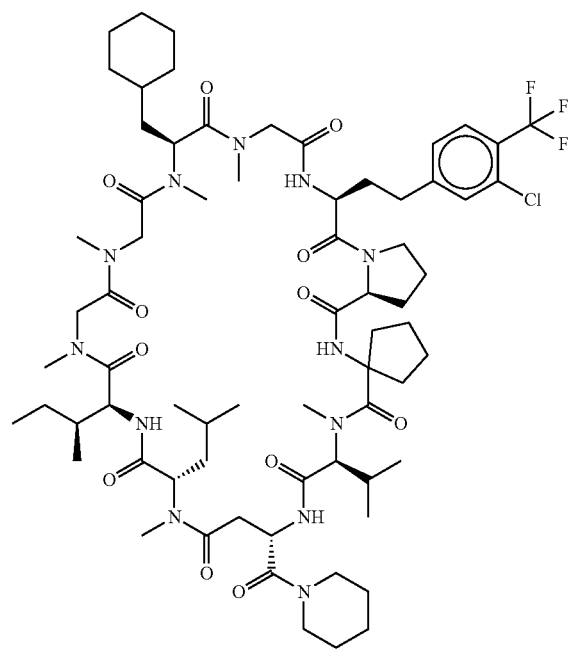 |

TABLE 24-continued
| Compound No. | Structural formula |
|---|---|
| 418 | 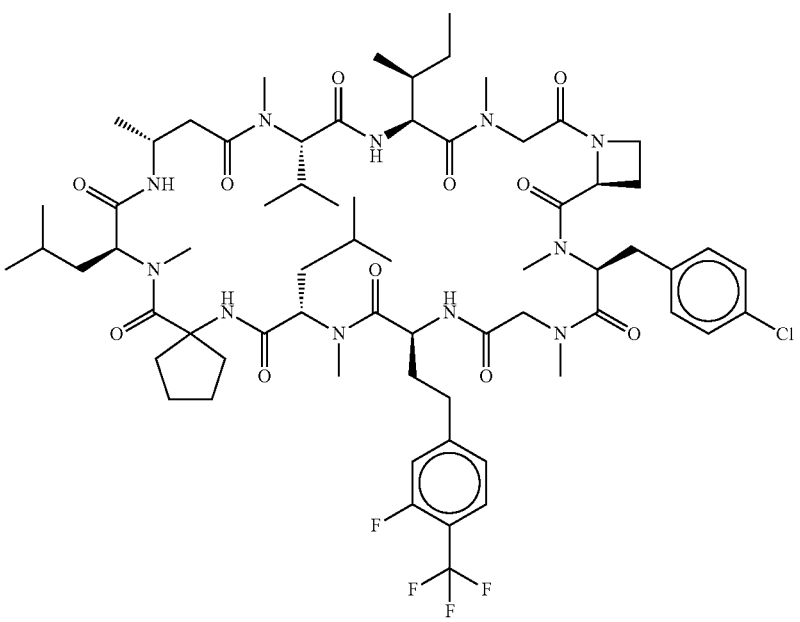 |
| 419 | 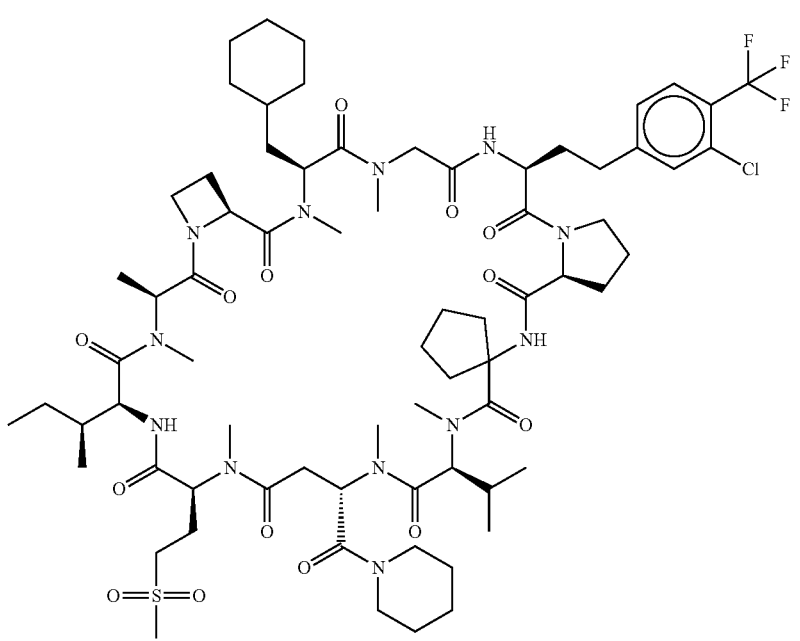 |

TABLE 24-continued
| Compound No. | Structural formula |
|---|---|
| 420 | 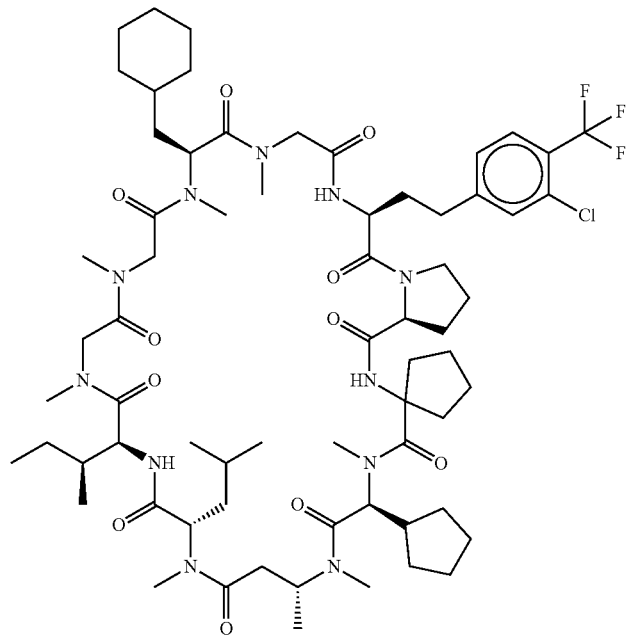 |
| 421 | 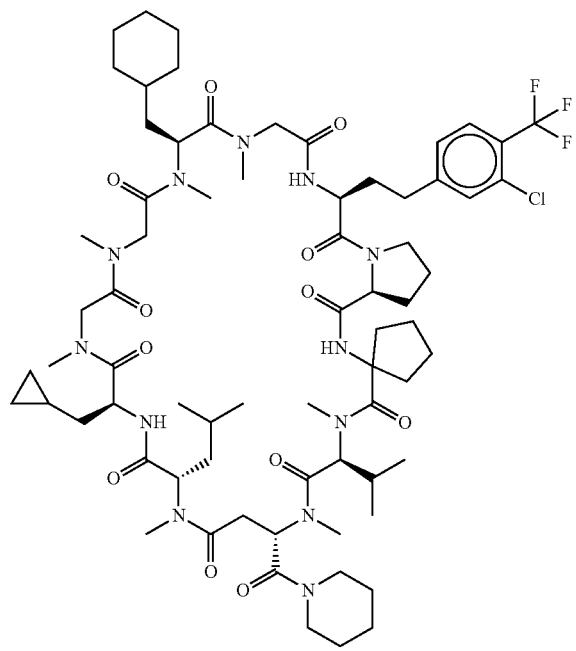 |

TABLE 24-continued
| Compound No. | Structural formula |
|---|---|
| 422 | 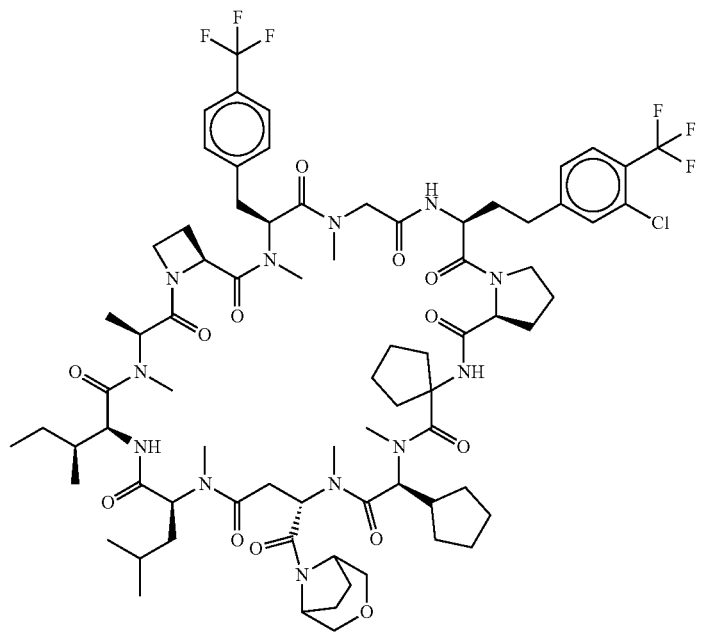 |
| 423 | 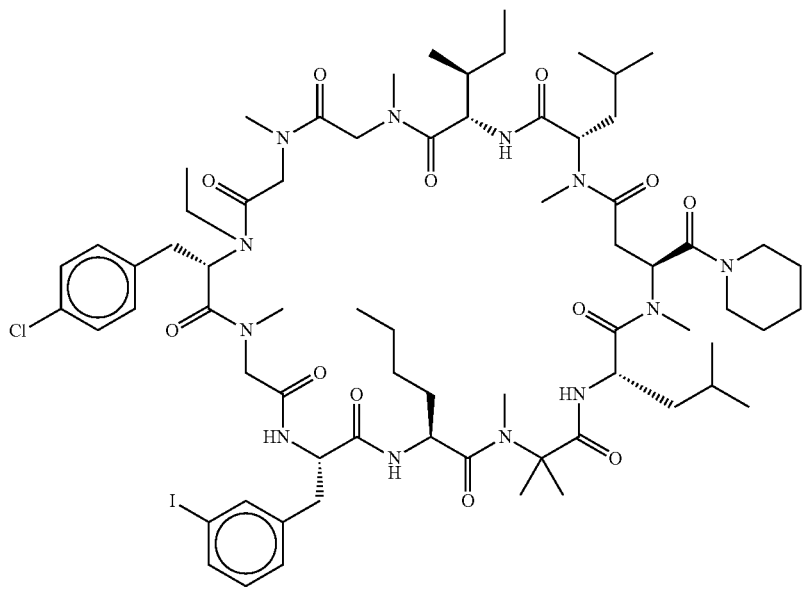 |

TABLE 24-continued
| Compound No. | Structural formula |
|---|---|
| 424 | 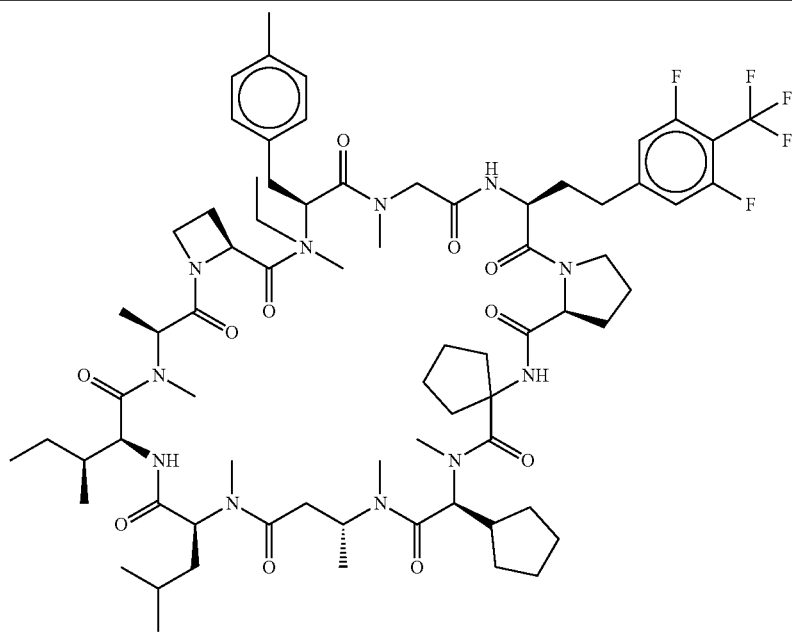 |
| 425 | 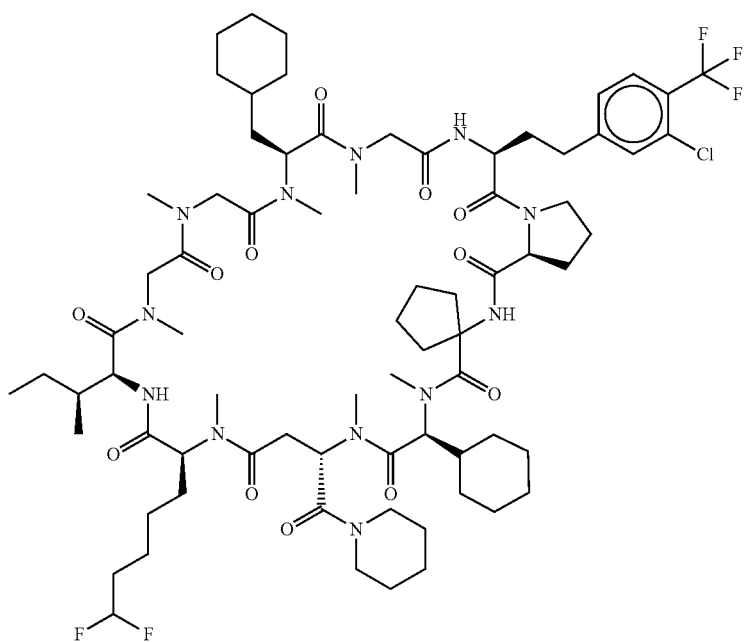 |

TABLE 24-continued
| Compound No. | Structural formula |
|---|---|
| 426 | 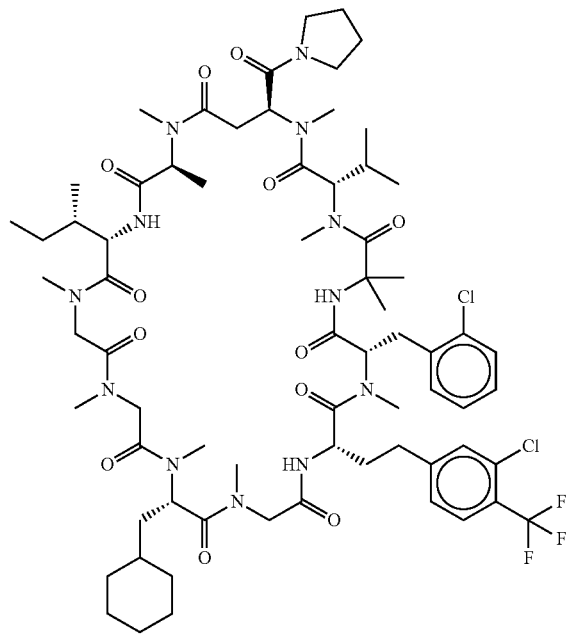 |
| 427 | 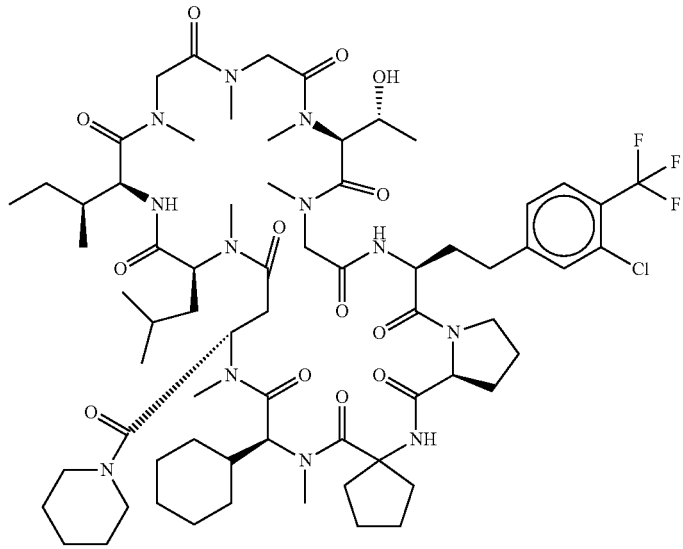 |

TABLE 24-continued
| Compound No. | Structural formula |
|---|---|
| 428 | 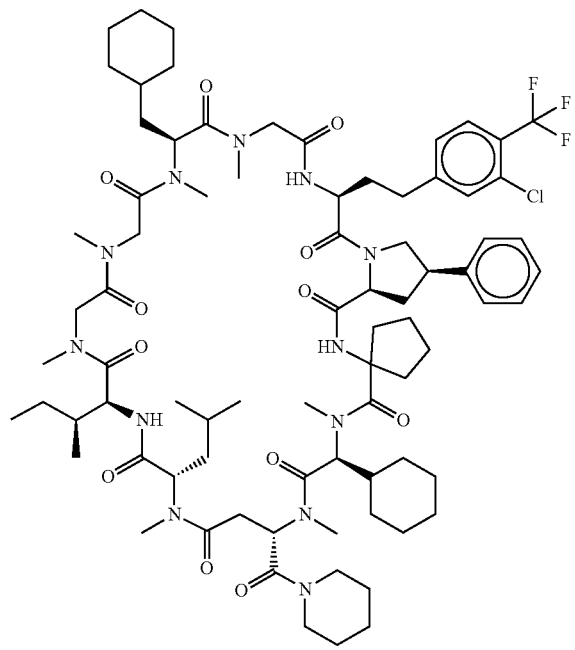 |
| 429 | 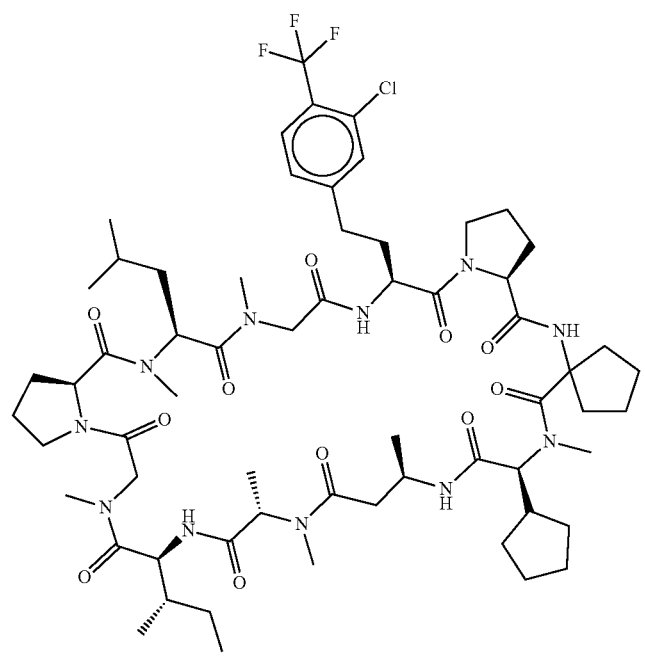 |

TABLE 24-continued
| Compound No. | Structural formula |
|---|---|
| 430 | 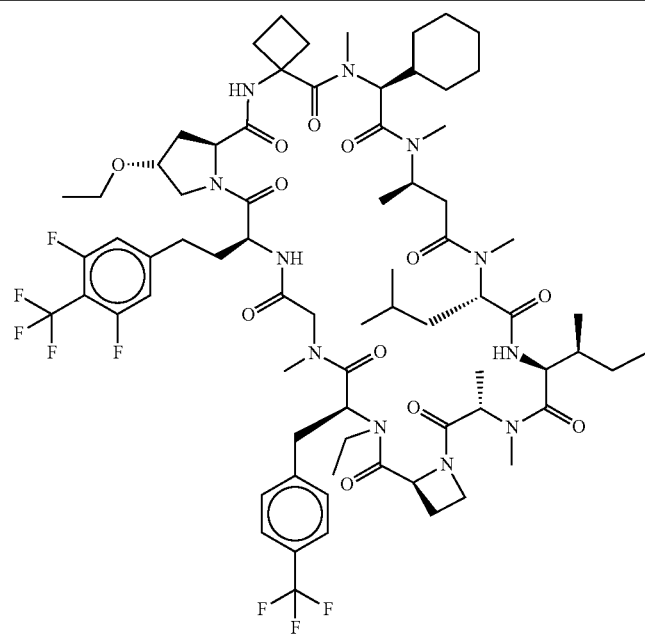 |
| 431 | 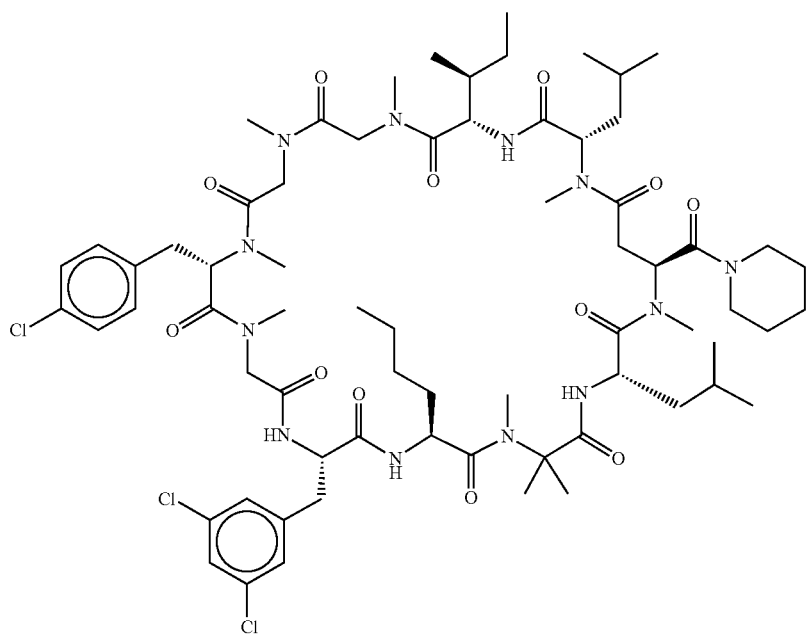 |

TABLE 24-continued

| Compound No. | Structural formula |
|---|---|
| 432 | |
| 433 | |

TABLE 24-continued
| Compound No. | Structural formula |
|---|---|
| 434 | 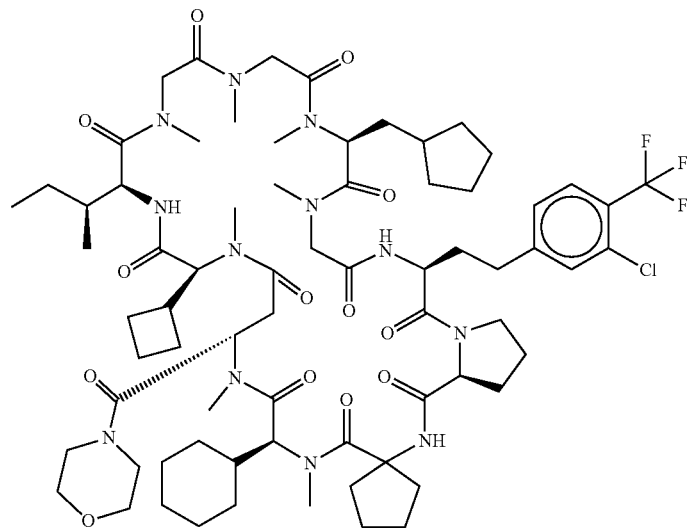 |
| 435 | 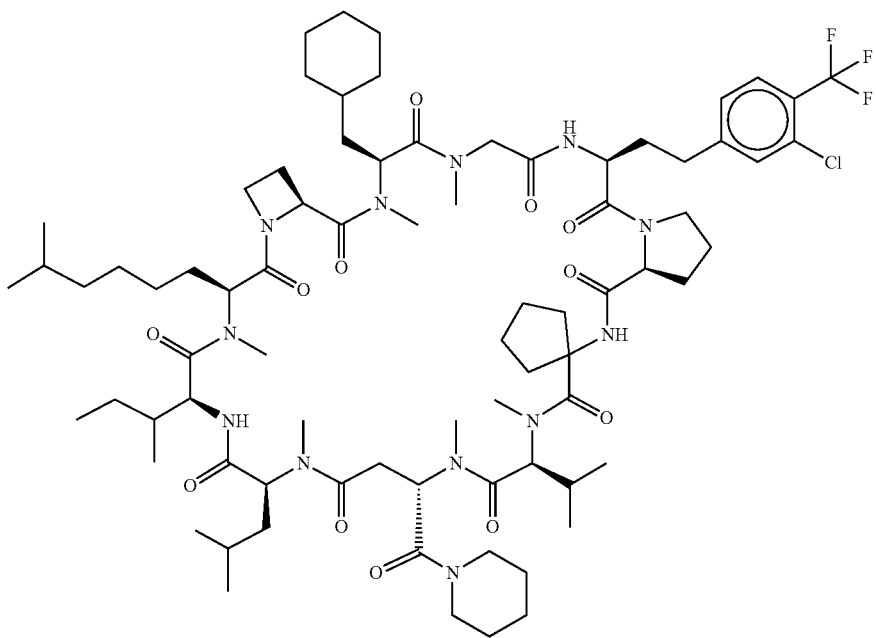 |

TABLE 24-continued
| Compound No. | Structural formula |
|---|---|
| 436 | 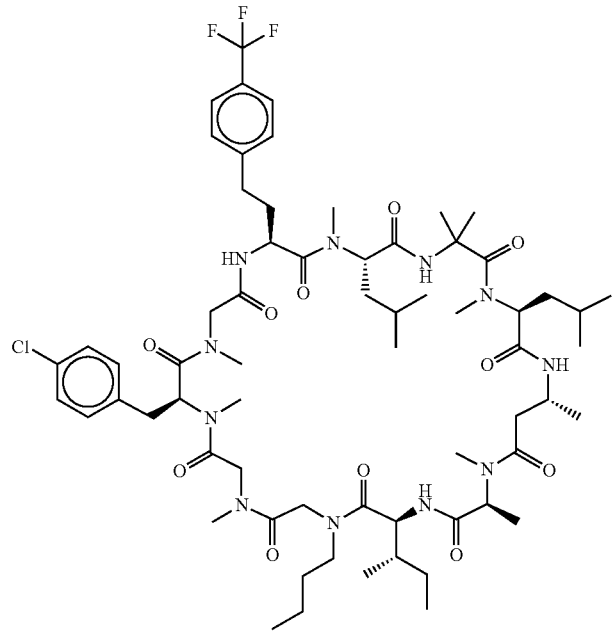 |
| 437 | 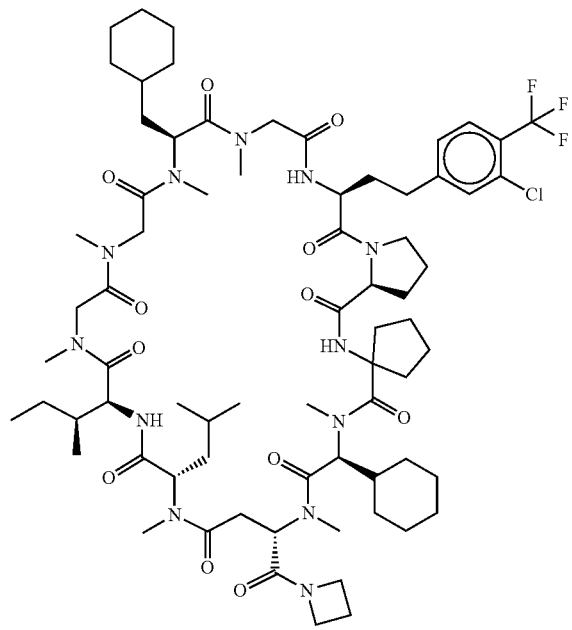 |

TABLE 24-continued
| Compound No. | Structural formula |
|---|---|
| 438 | 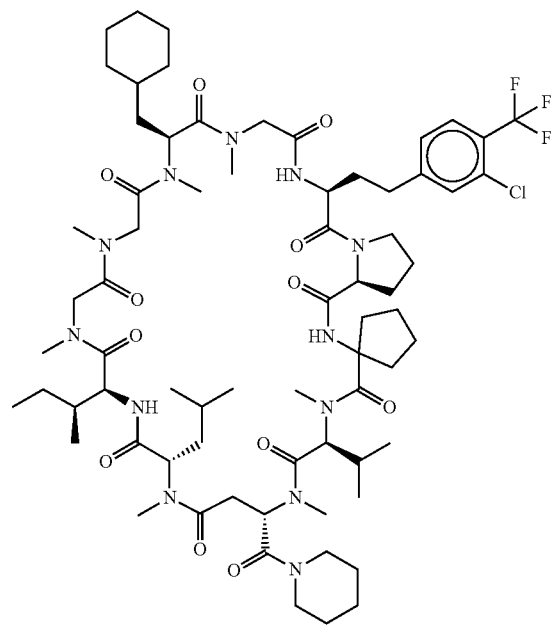 |
| 439 | 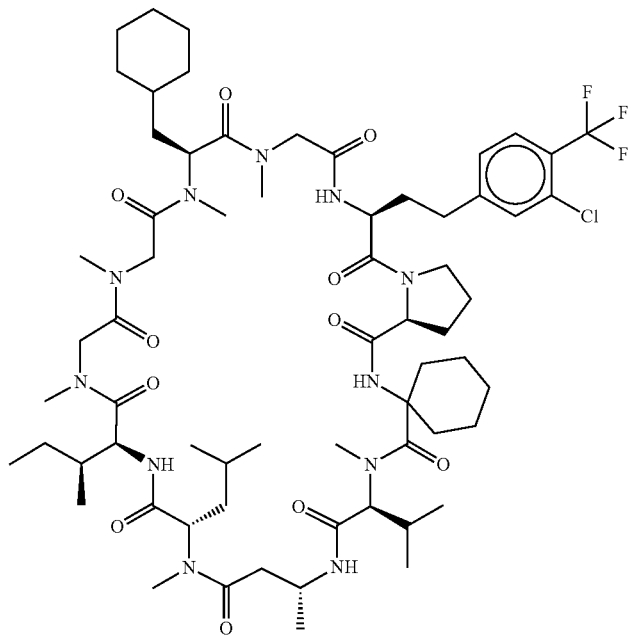 |

TABLE 24-continued

| Compound No. | Structural formula |
|---|---|
| 440 | |
| 441 | |

TABLE 24-continued
| Compound No. | Structural formula |
|---|---|
| 442 | 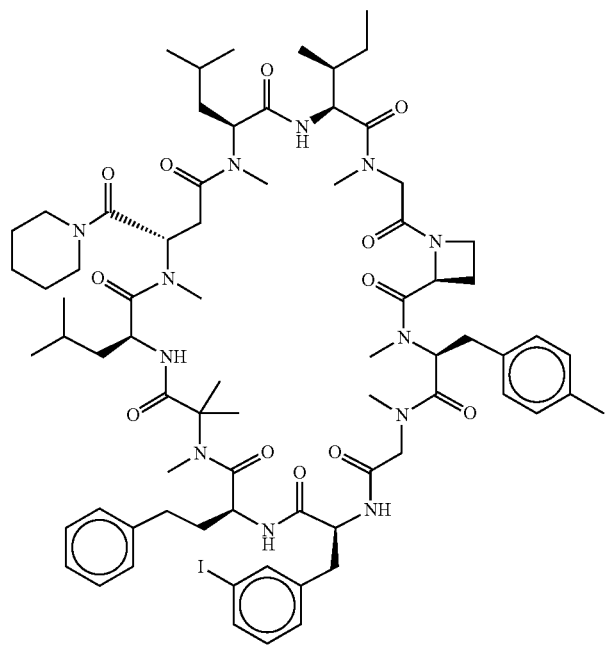 |
| 443 | 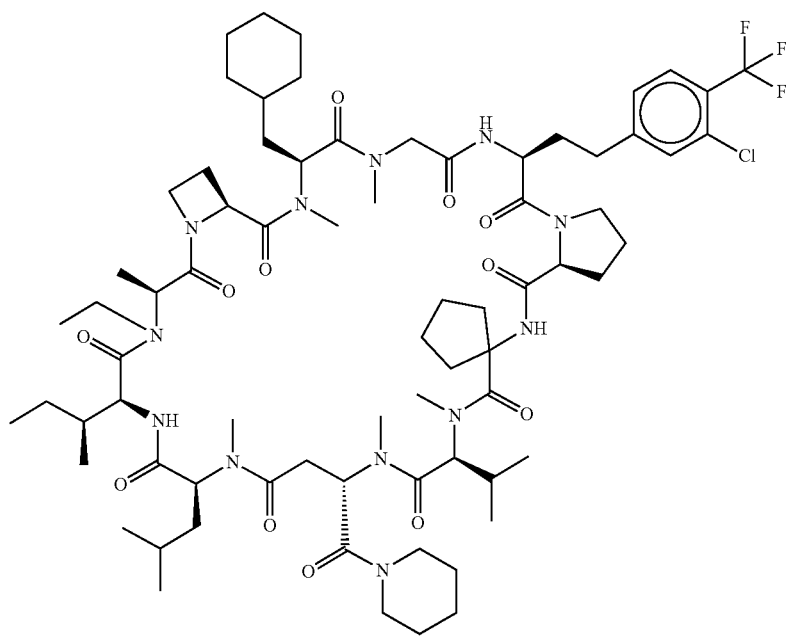 |

TABLE 24-continued
| Compound No. | Structural formula |
|---|---|
| 444 | 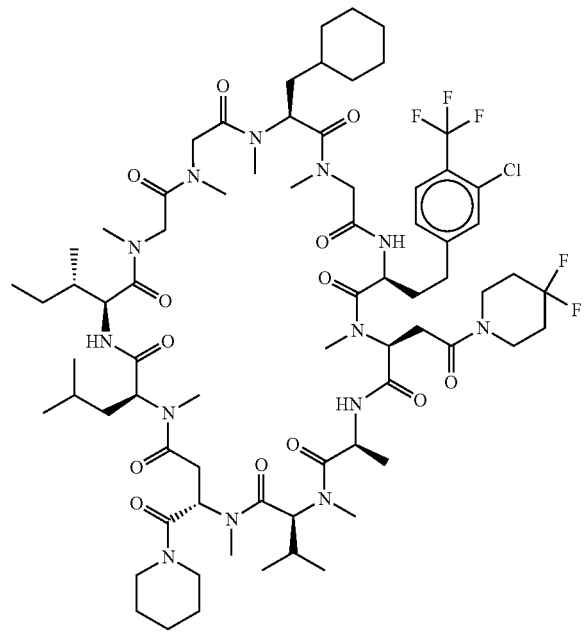 |
| 445 | 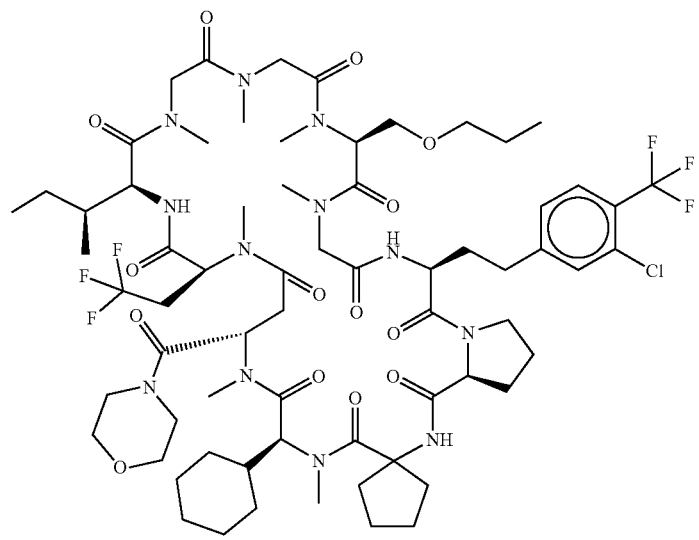 |

TABLE 24-continued
| Compound No. | Structural formula |
|---|---|
| 446 | 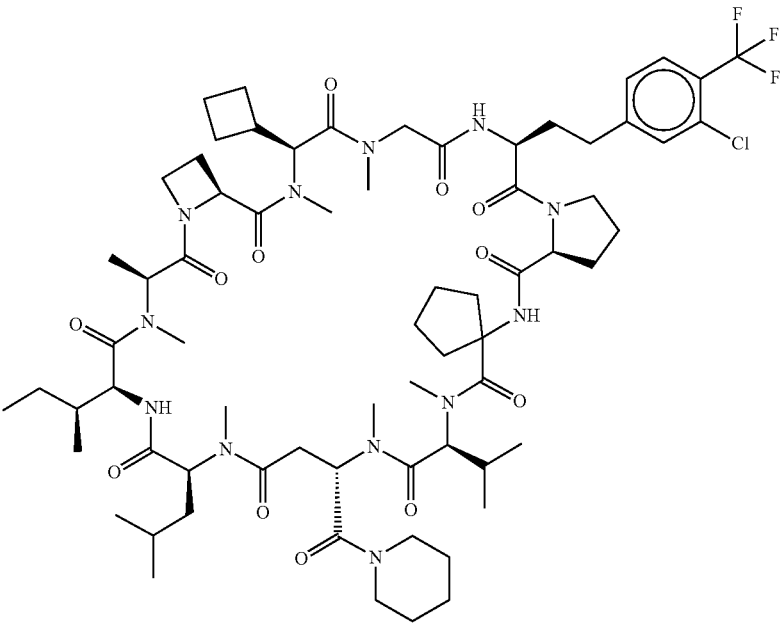 |
| 447 | 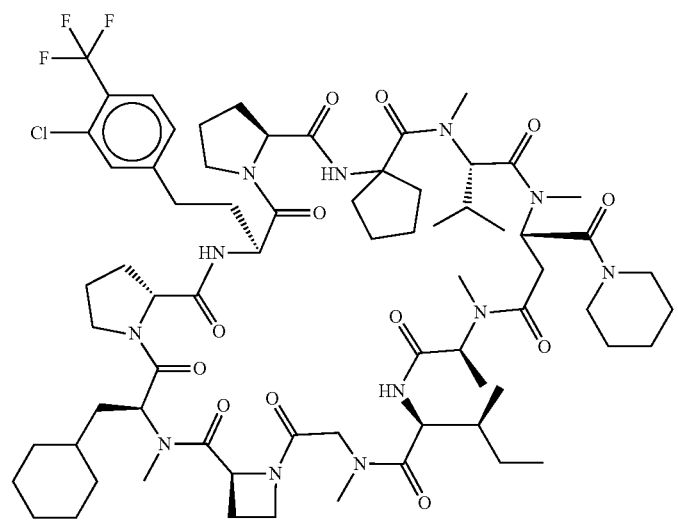 |

TABLE 24-continued
| Compound No. | Structural formula |
|---|---|
| 448 | 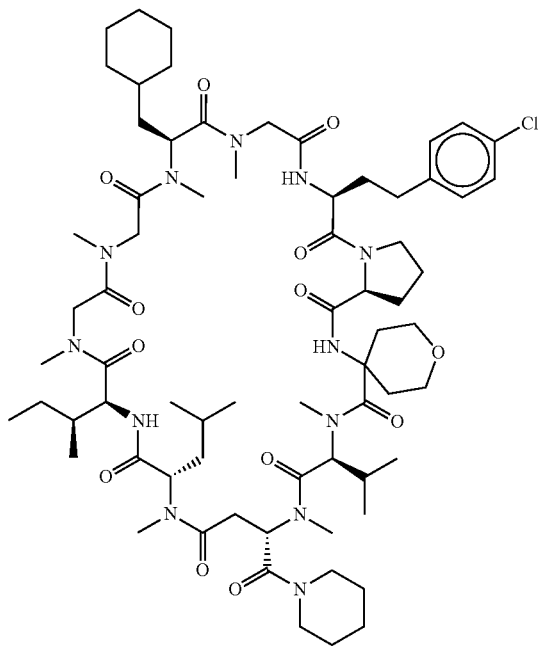 |
| 449 | 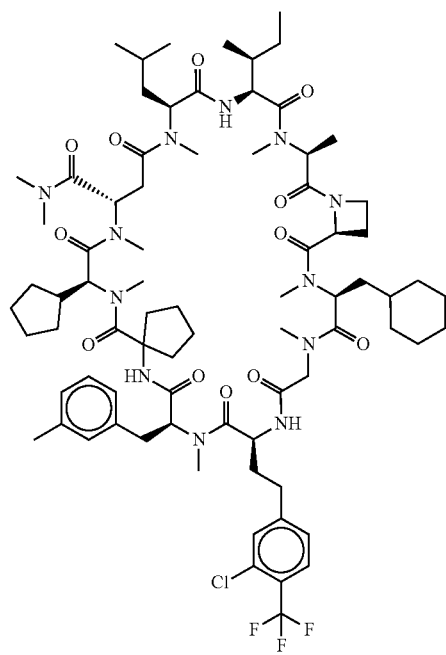 |

TABLE 24-continued
| Compound No. | Structural formula |
|---|---|
| 450 | 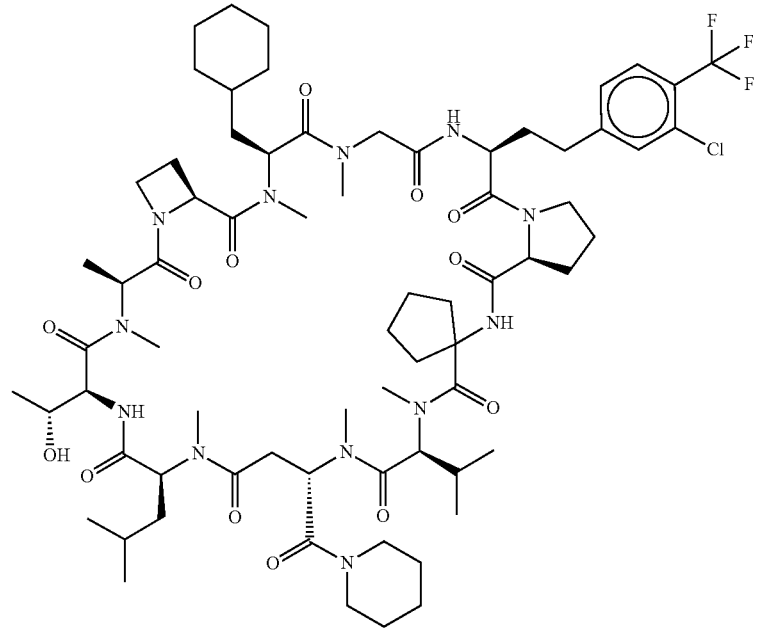 |
| 451 | 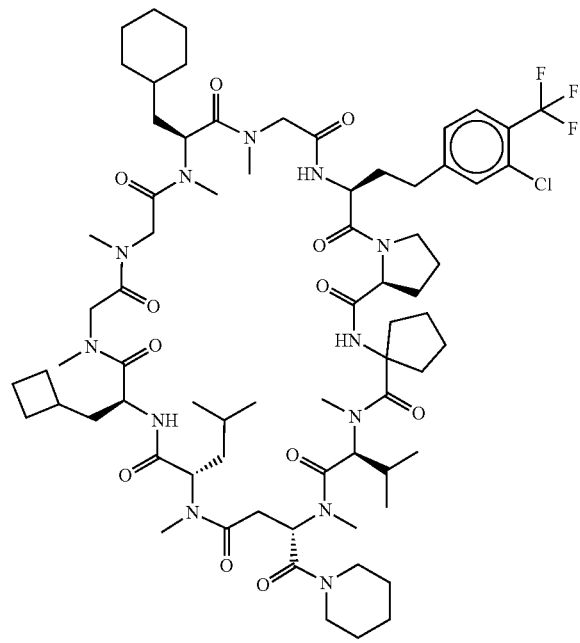 |

TABLE 24-continued
| Compound No. | Structural formula |
|---|---|
| 452 | 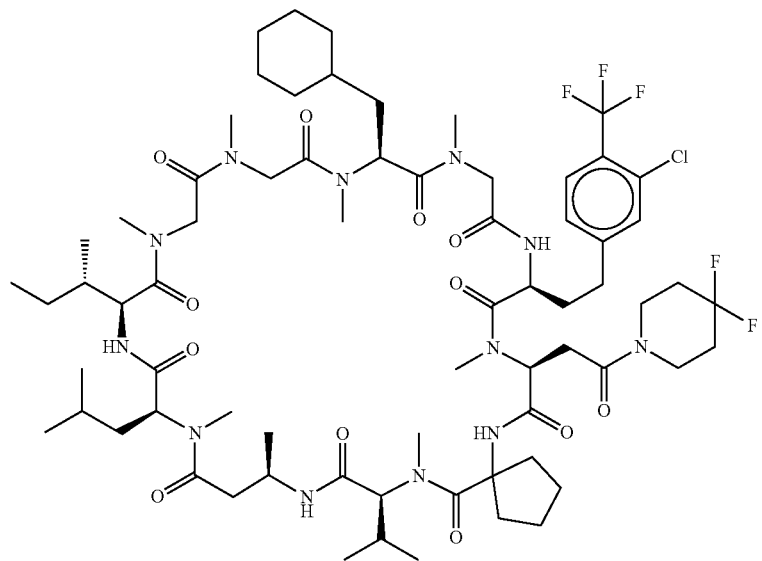 |
| 453 | 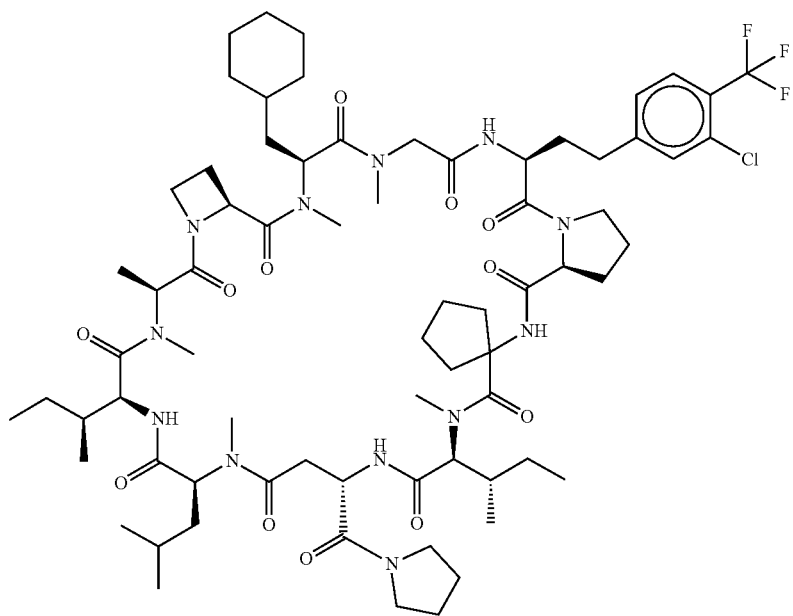 |

TABLE 24-continued
| Compound No. | Structural formula |
|---|---|
| 454 | 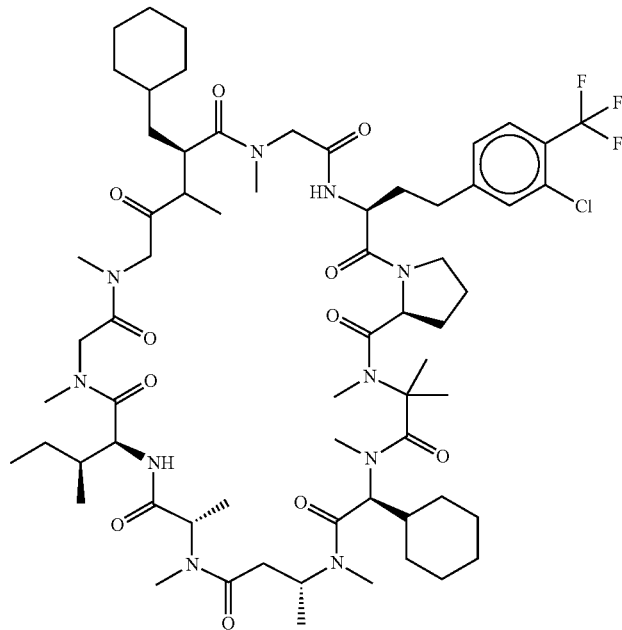 |
| 455 | 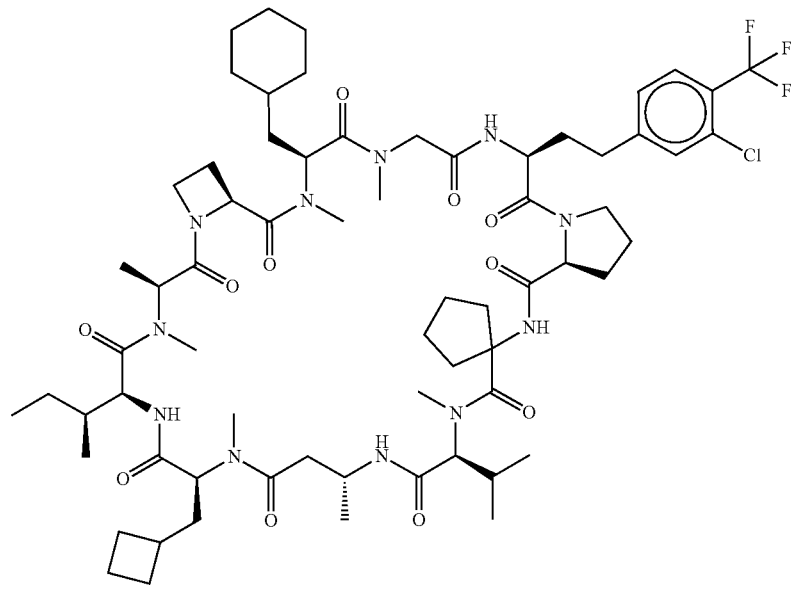 |

TABLE 24-continued
| Compound No. | Structural formula |
| --- | --- |
| 456 | 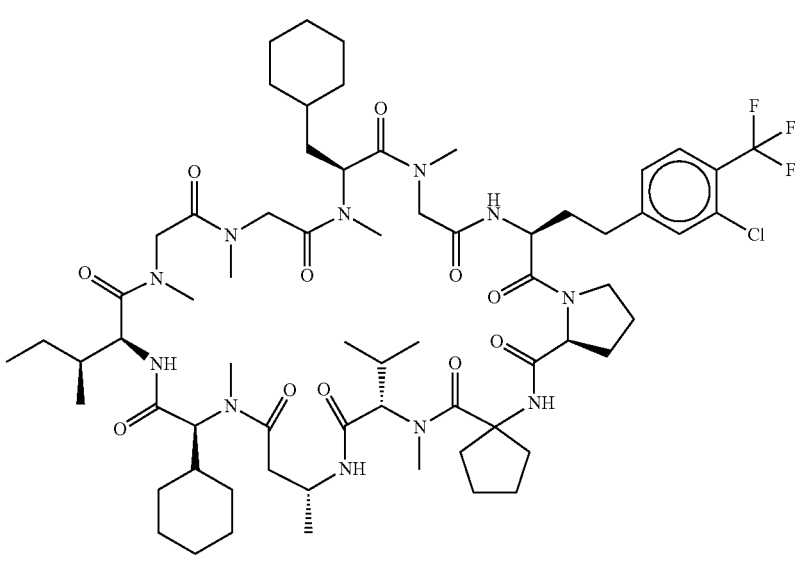 |
| 457 | 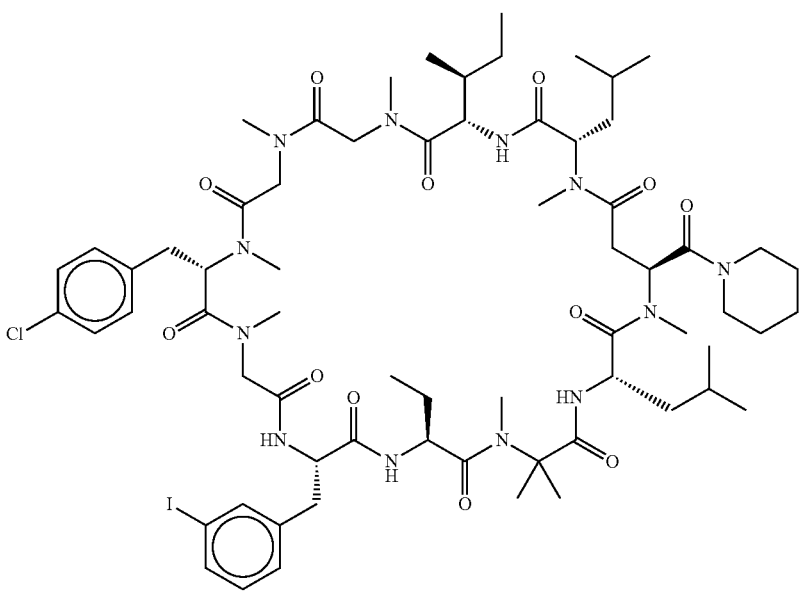 |

TABLE 24-continued
| Compound No. | Structural formula |
|---|---|
| 458 | 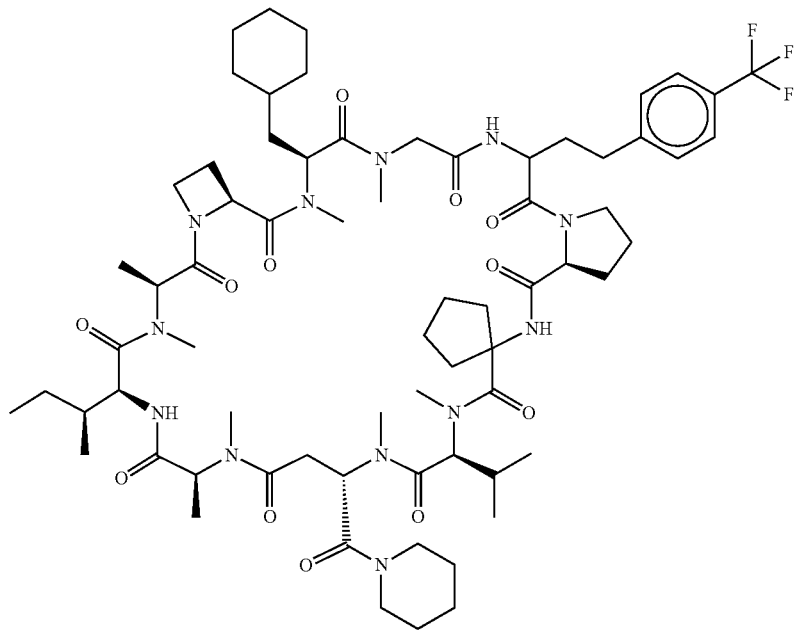 |
| 459 | 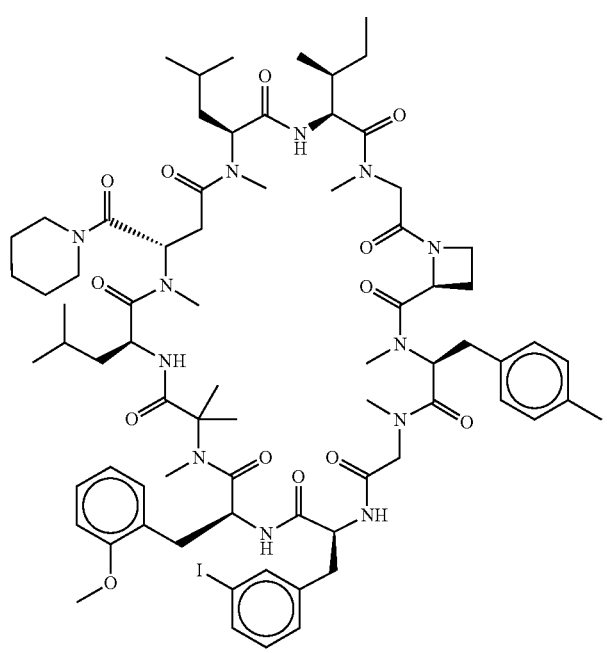 |

TABLE 24-continued
| Compound No. | Structural formula |
|---|---|
| 460 | 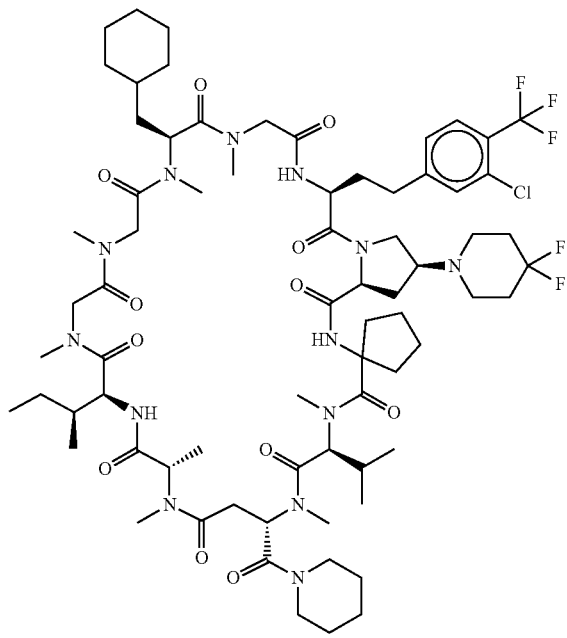 |
| 461 | 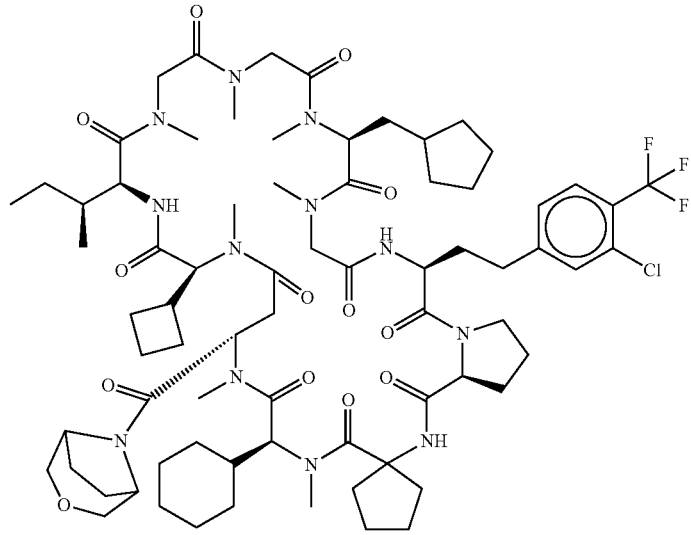 |

TABLE 24-continued
| Compound No. | Structural formula |
|---|---|
| 462 | 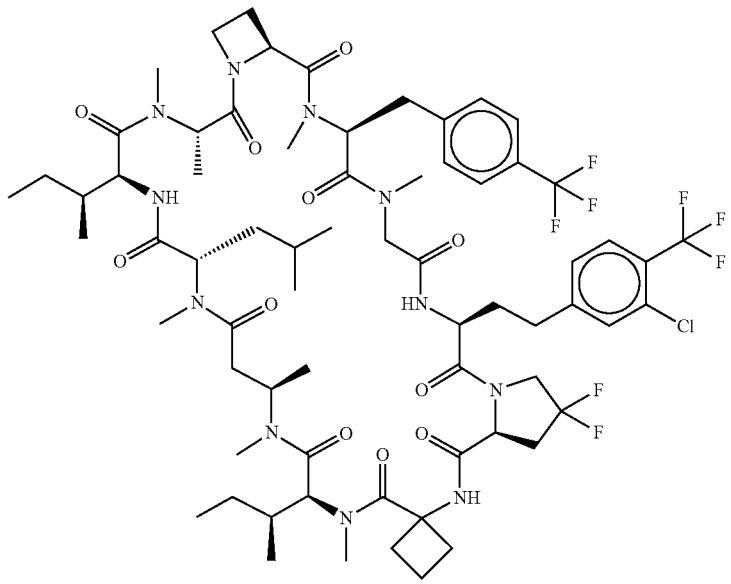 |
| 463 | 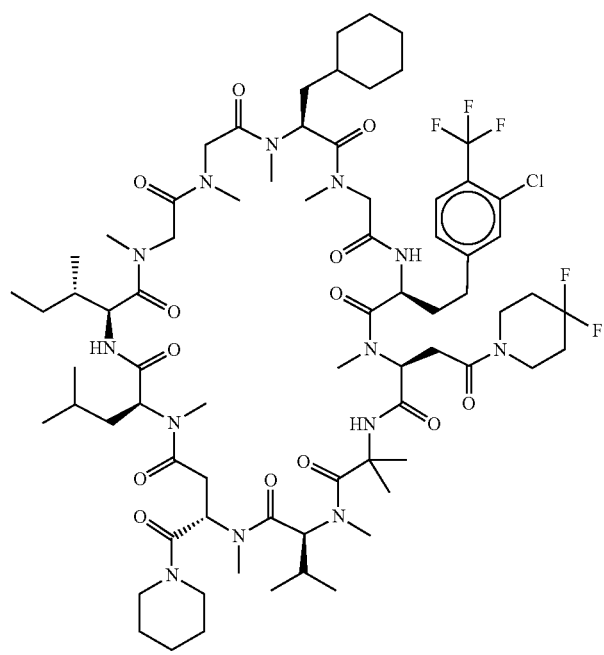 |

TABLE 24-continued
| Compound No. | Structural formula |
|---|---|
| 464 | 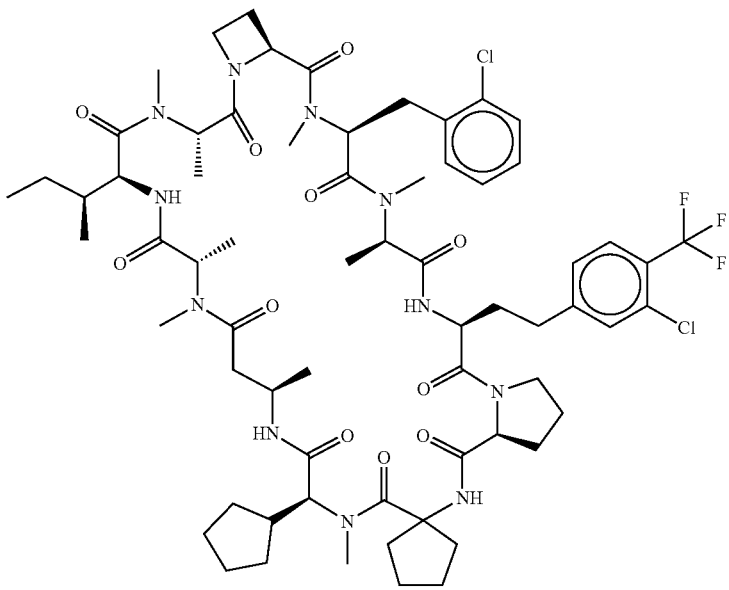 |
| 465 | 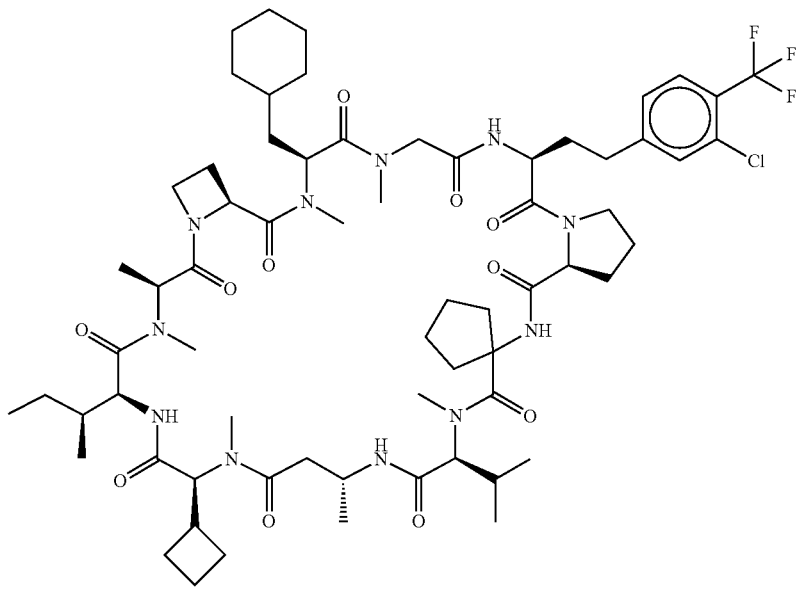 |

TABLE 24-continued
| Compound No. | Structural formula |
|---|---|
| 466 | 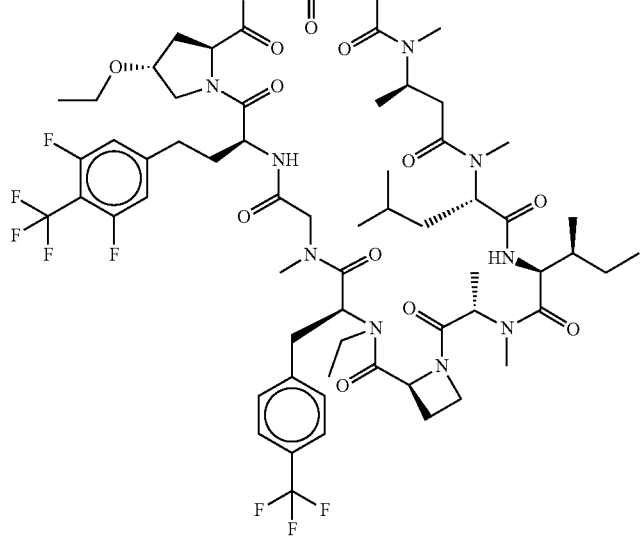 |
| 467 | 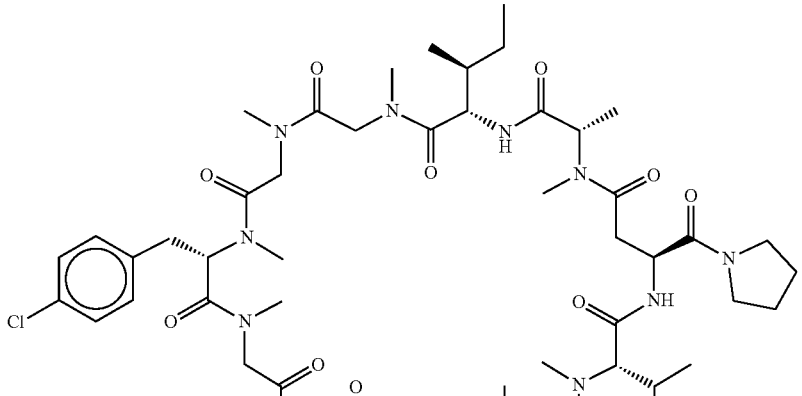 |

TABLE 24-continued
| Compound No. | Structural formula |
|---|---|
| 468 | 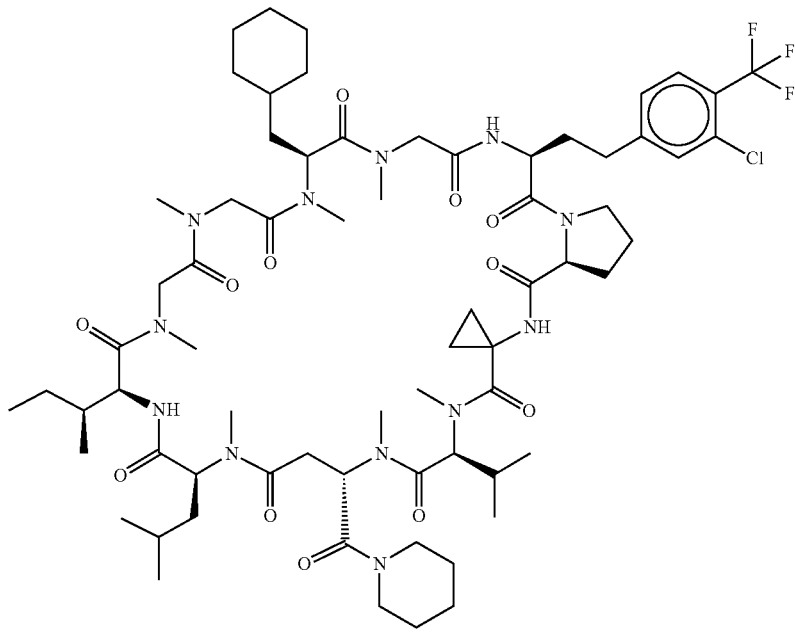 |
| 469 | 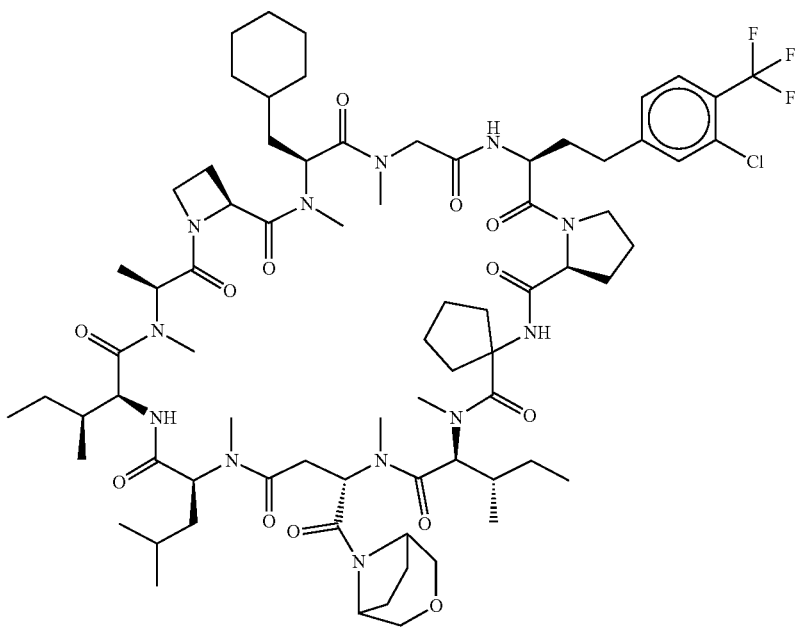 |

TABLE 24-continued
| Compound No. | Structural formula |
|---|---|
| 470 | 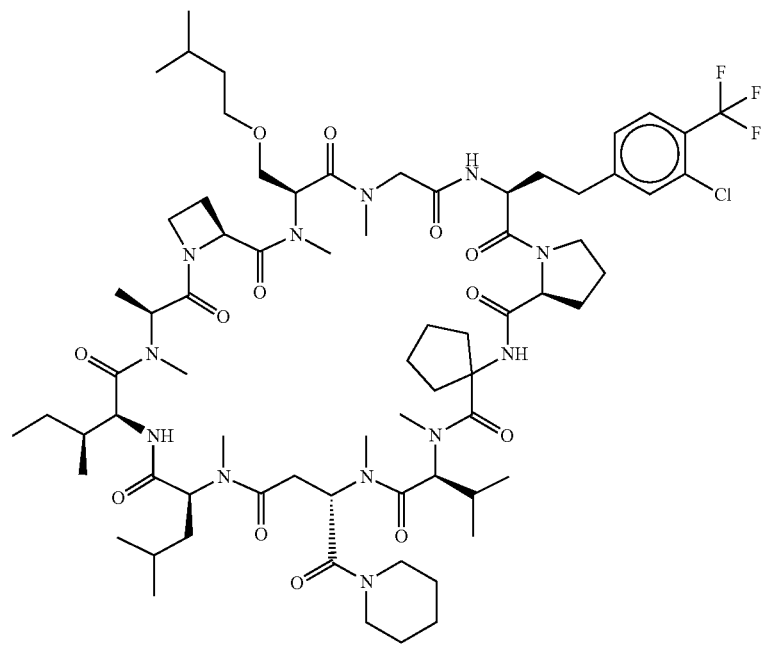 |
| 471 | 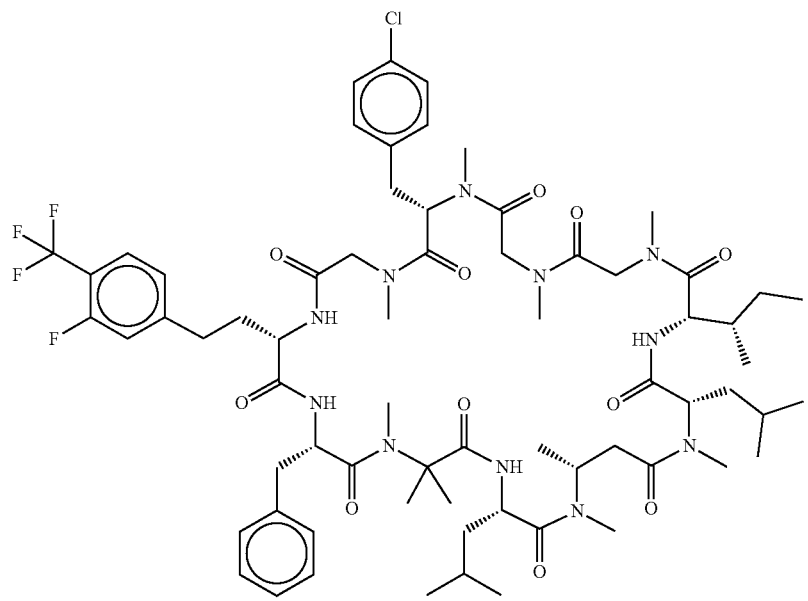 |

TABLE 24-continued
| Compound No. | Structural formula |
|---|---|
| 472 | 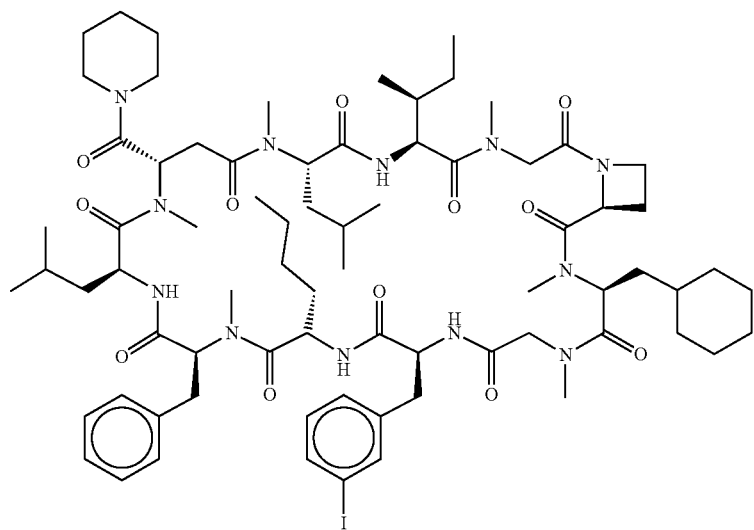 |
| 473 | 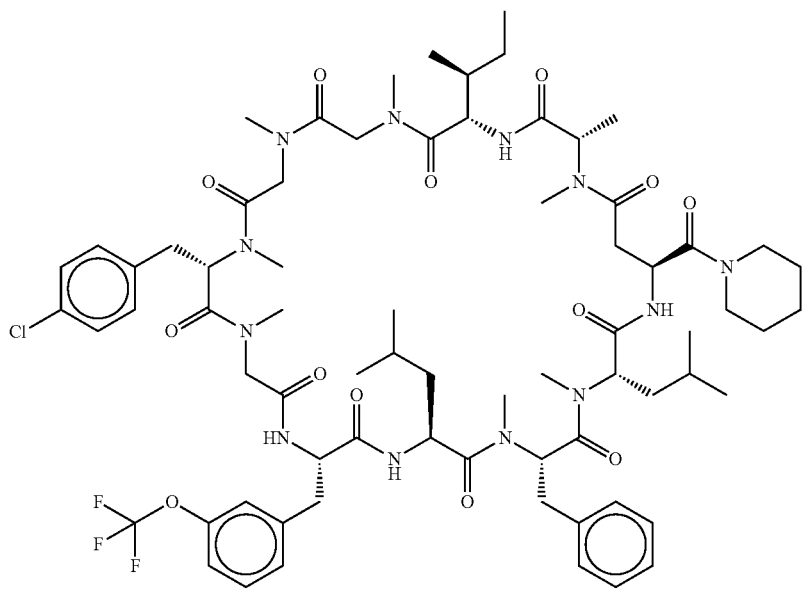 |

TABLE 24-continued
| Compound No. | Structural formula |
| --- | --- |
| 474 | 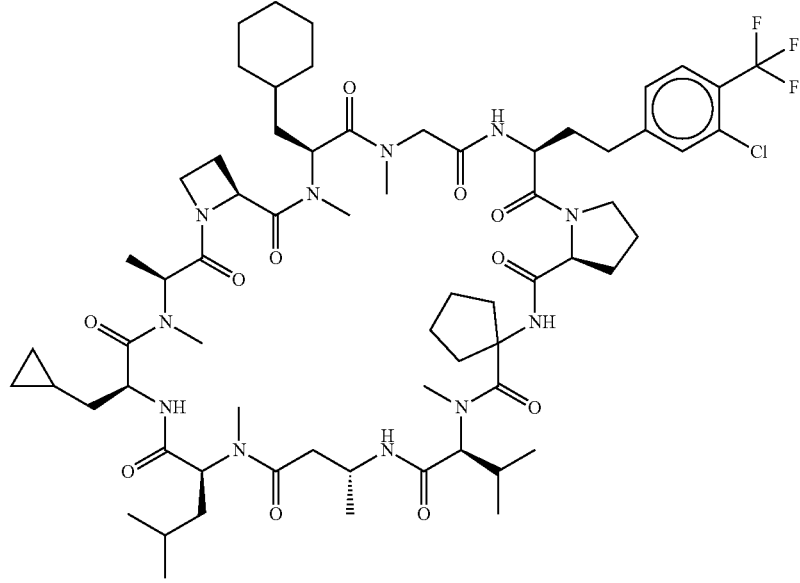 |
| 475 | 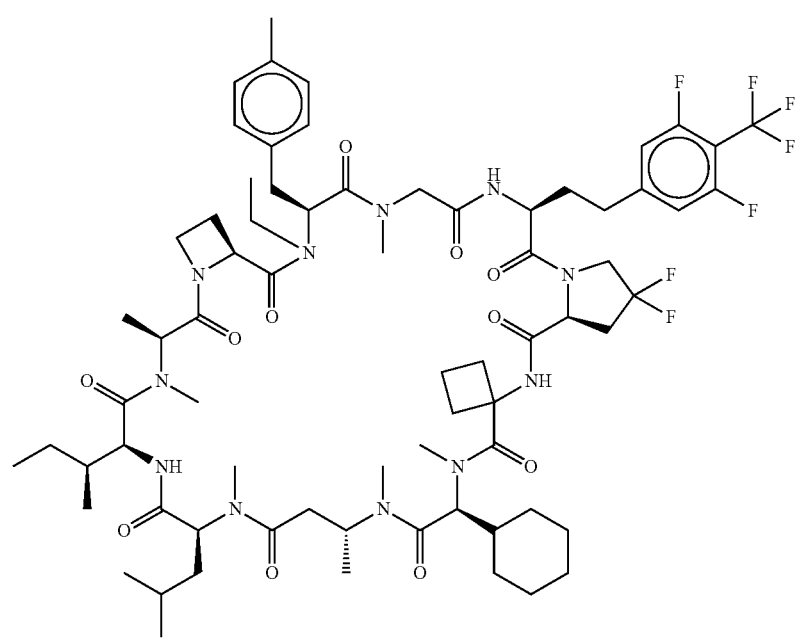 |

TABLE 24-continued
| Compound No. | Structural formula |
|---|---|
| 476 | 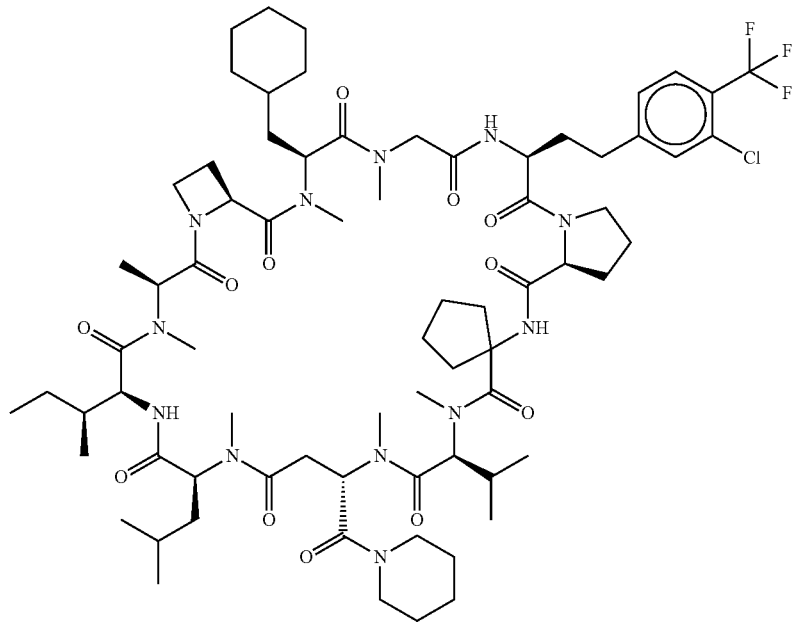 |
| 477 | 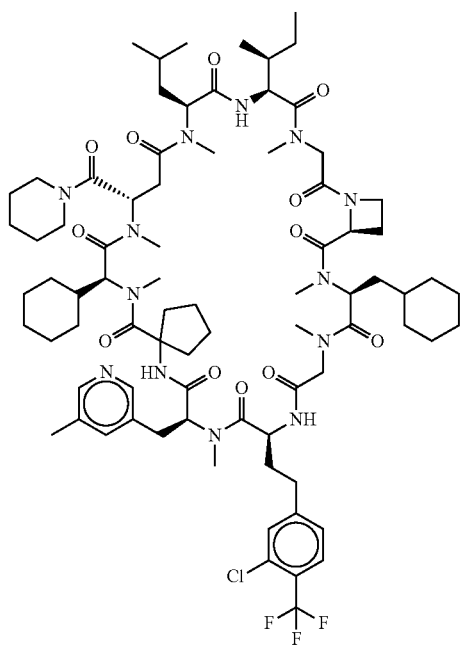 |

TABLE 24-continued
| Compound No. | Structural formula |
|---|---|
| 478 | 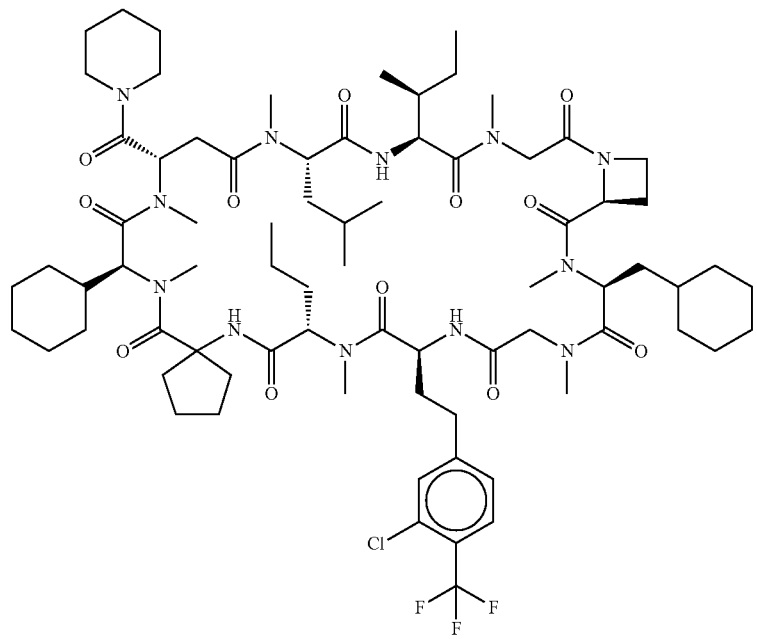 |
| 479 | 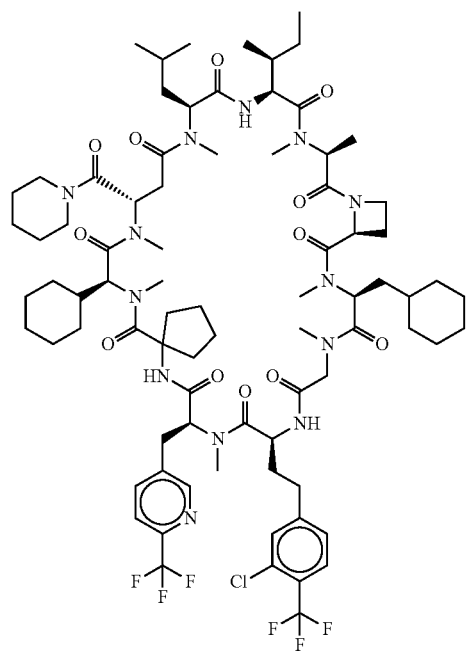 |

| Compound No. | Structural formula |
|---|---|
| 480 | 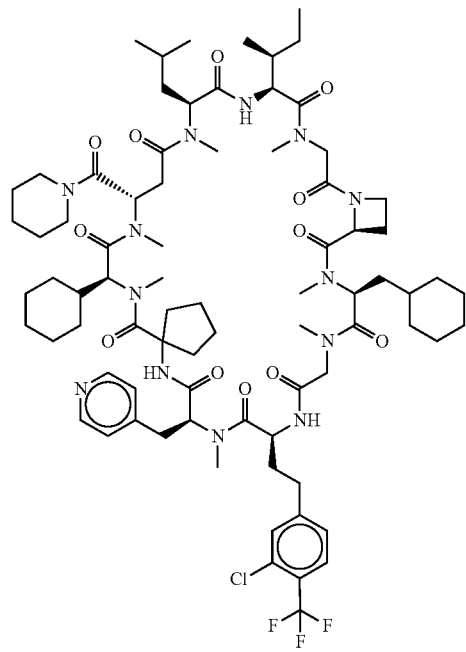 |
| 481 | 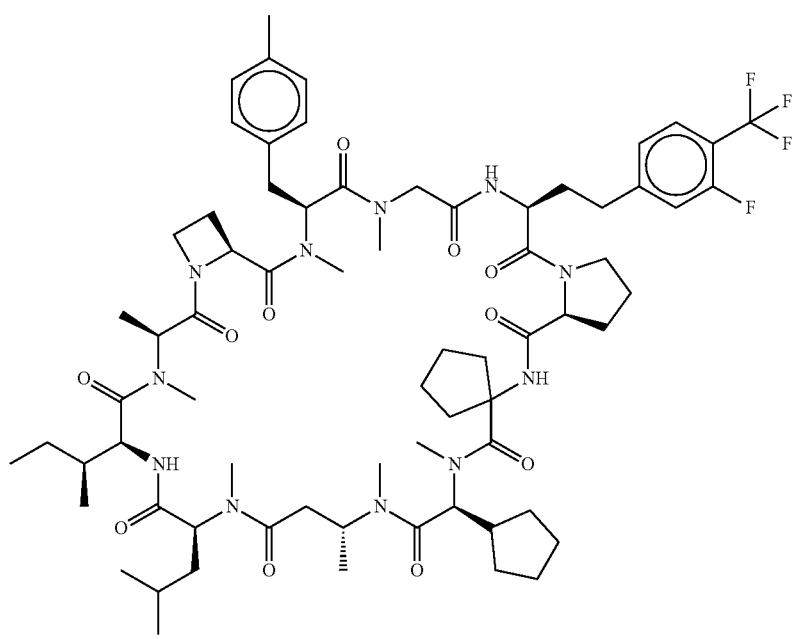 |

TABLE 24-continued
| Compound No. | Structural formula |
|---|---|
| 482 | 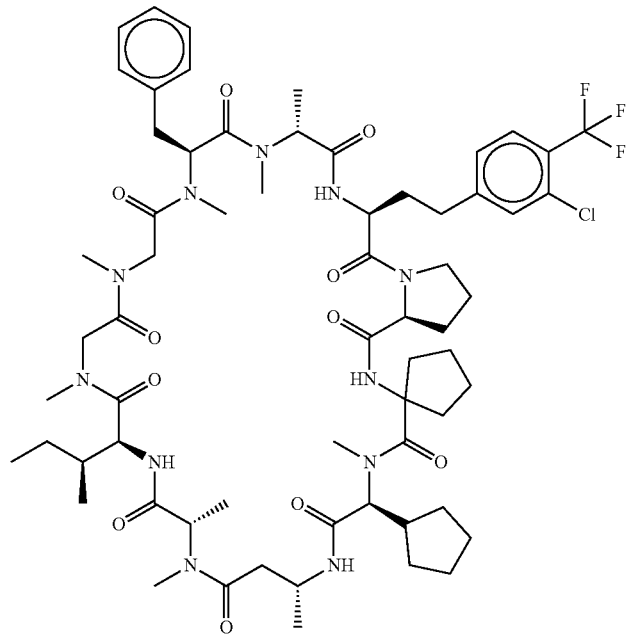 |
| 483 | 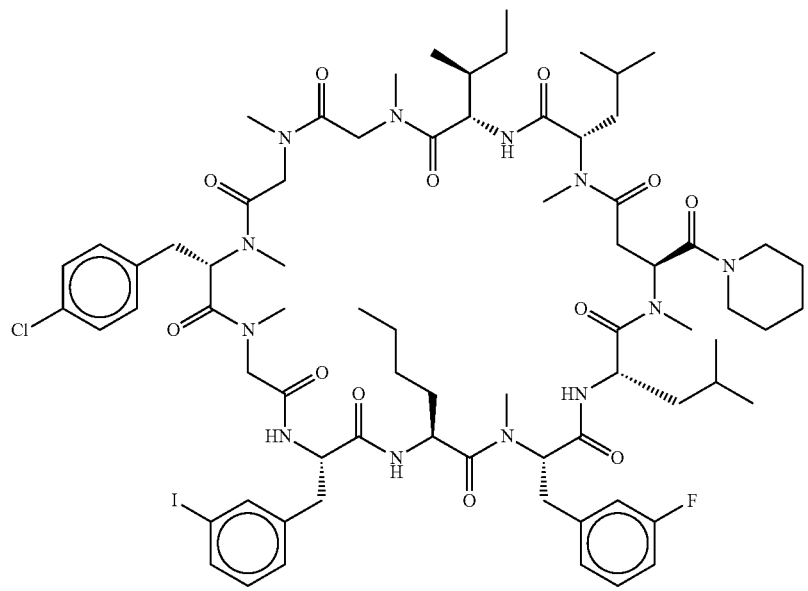 |

TABLE 24-continued
| Compound No. | Structural formula |
|---|---|
| 484 | 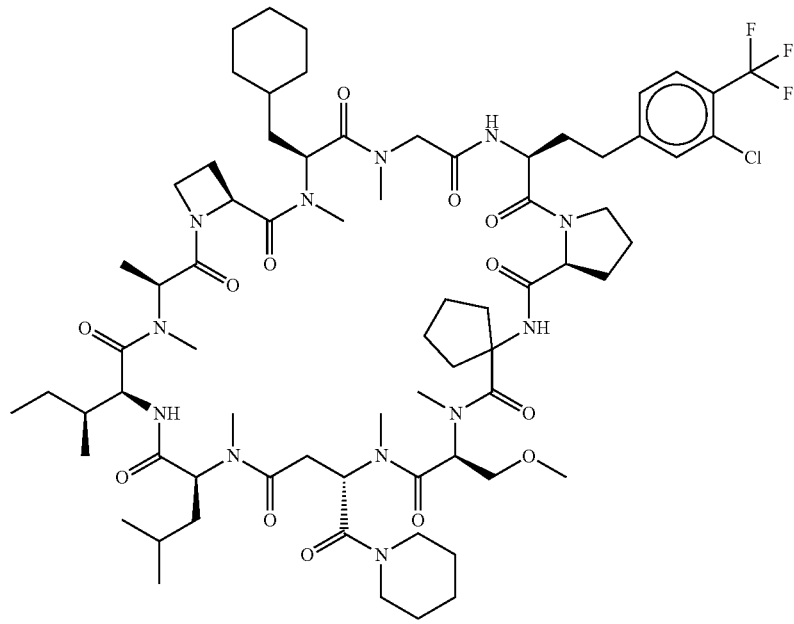 |
| 485 | 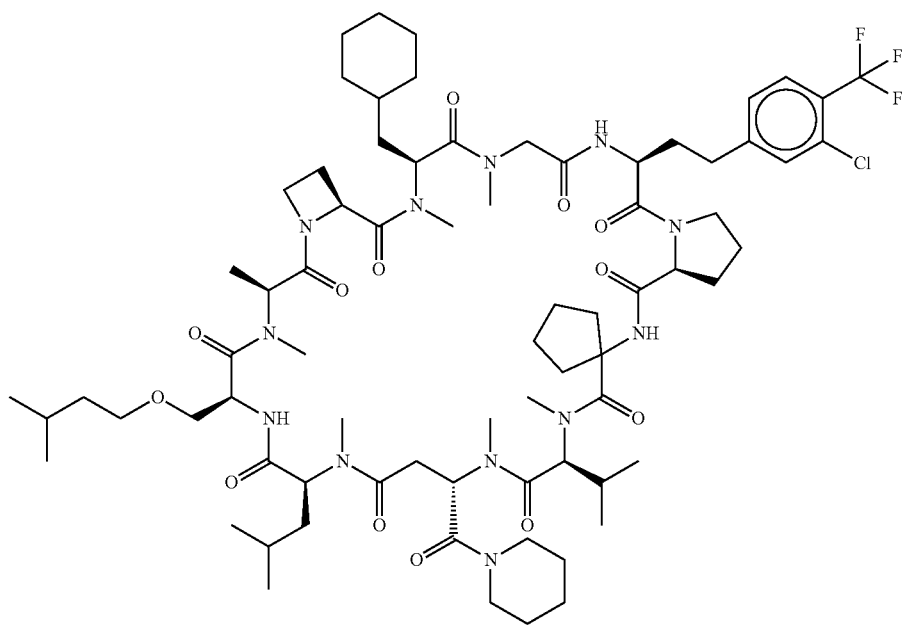 |

TABLE 24-continued
| Compound No. | Structural formula |
|---|---|
| 486 | 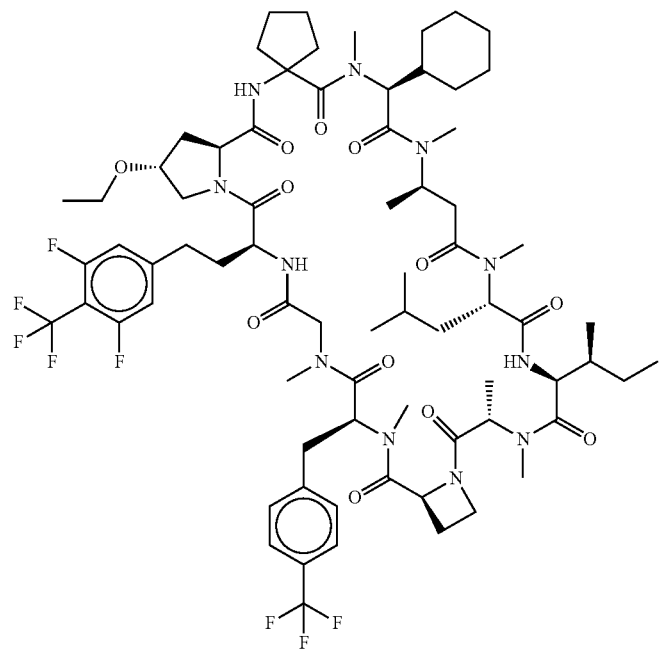 |
| 487 | 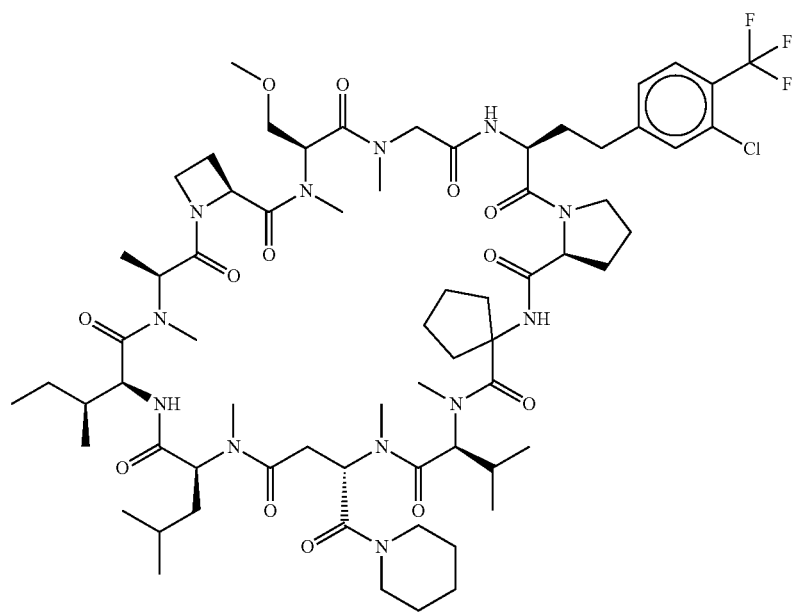 |

TABLE 24-continued
| Compound No. | Structural formula |
|---|---|
| 488 | 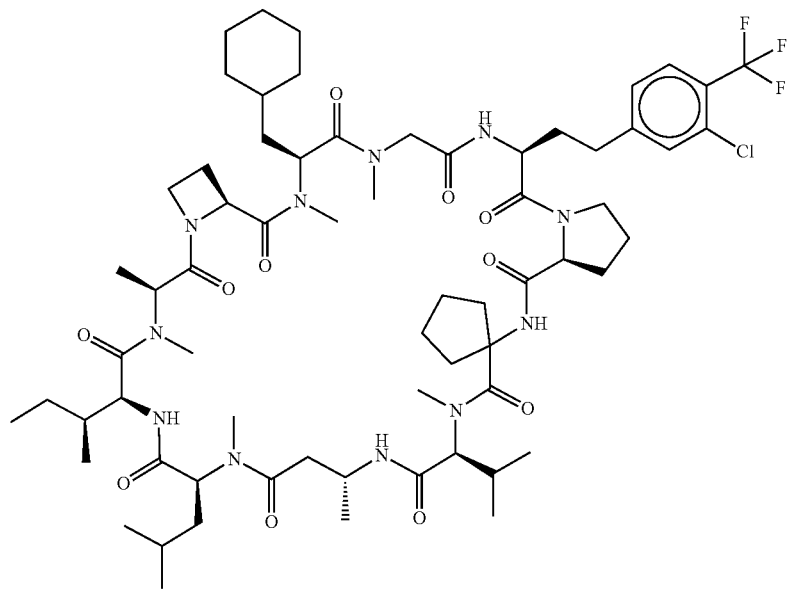 |
| 489 | 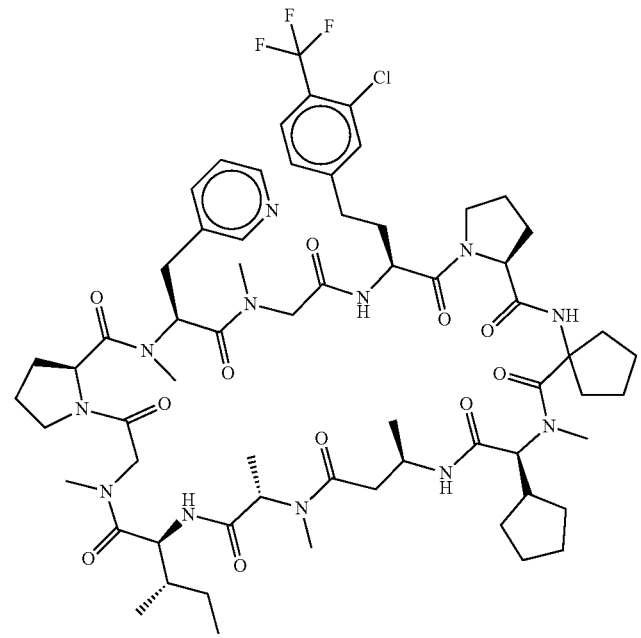 |

TABLE 24-continued
| Compound No. | Structural formula |
|---|---|
| 490 | 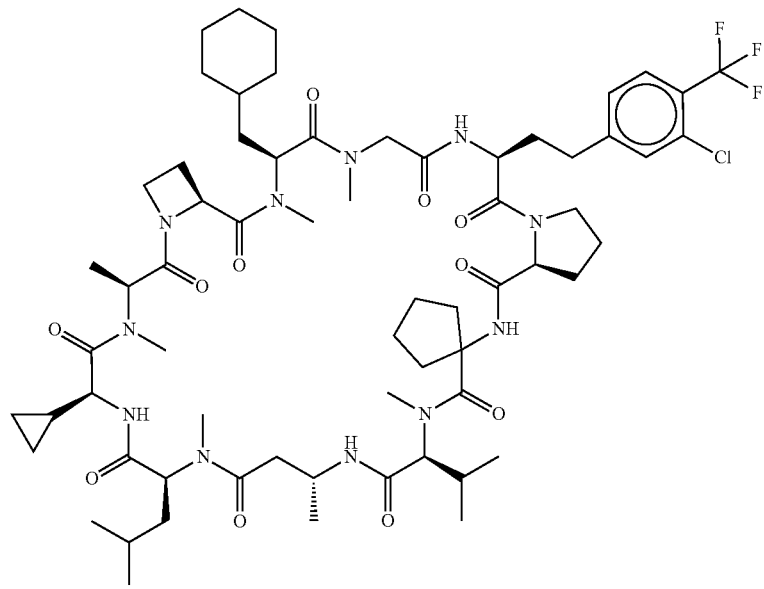 |
| 491 | 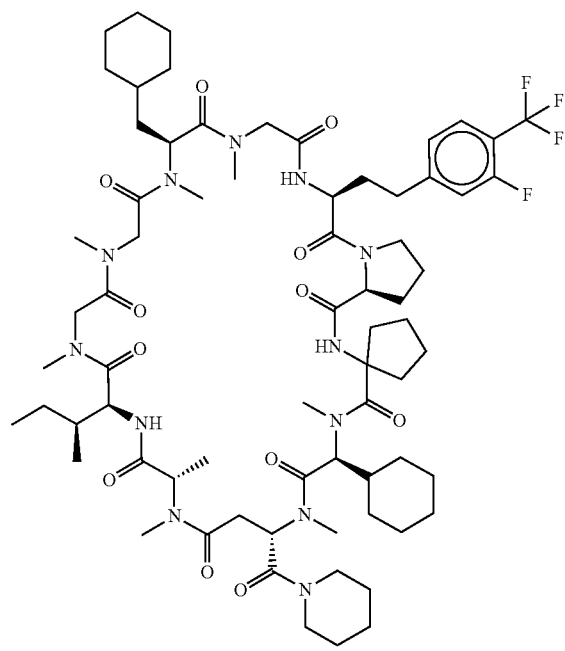 |

TABLE 24-continued
| Compound No. | Structural formula |
|---|---|
| 492 | 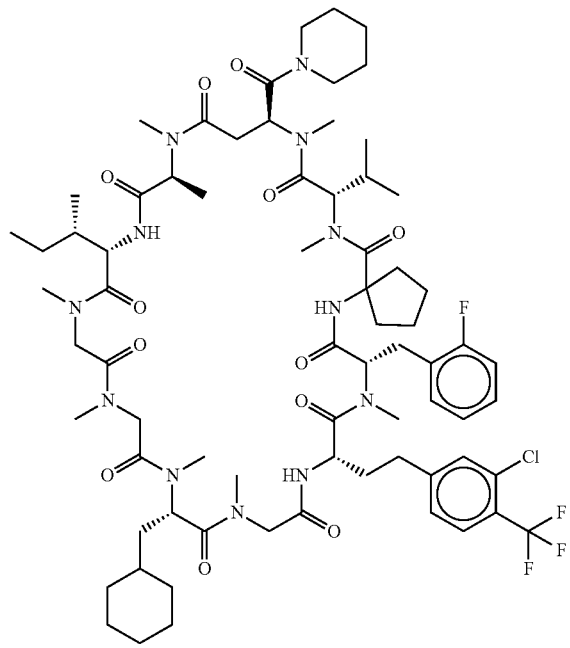 |
| 493 | 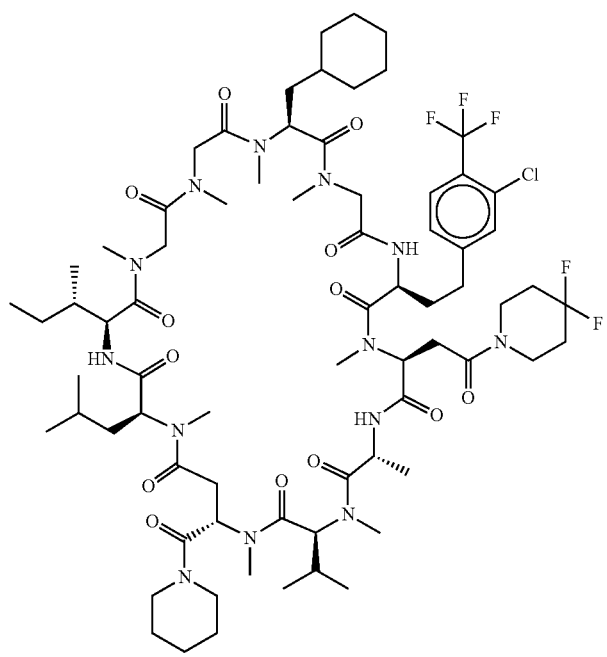 |

TABLE 24-continued
| Compound No. | Structural formula |
|---|---|
| 494 | 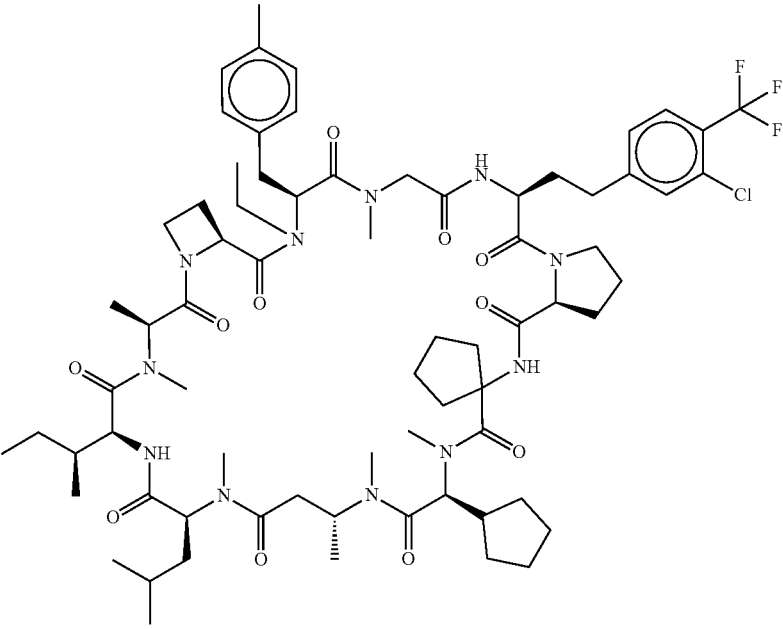 |
| 495 | 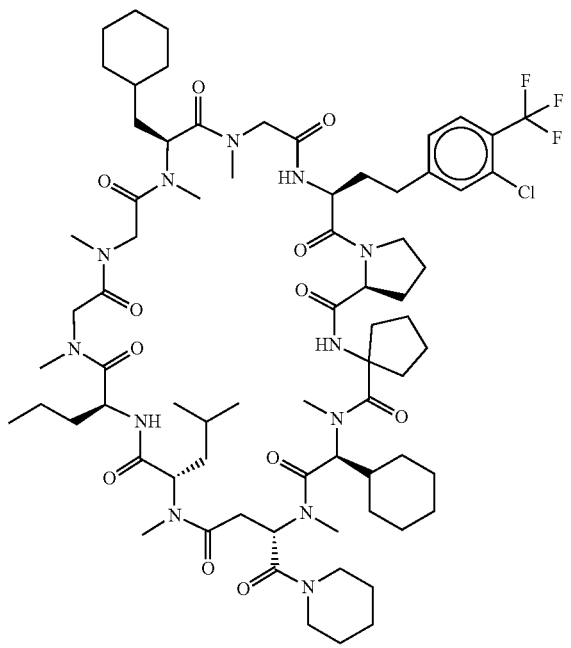 |

TABLE 24-continued
| Compound No. | Structural formula |
|---|---|
| 496 | 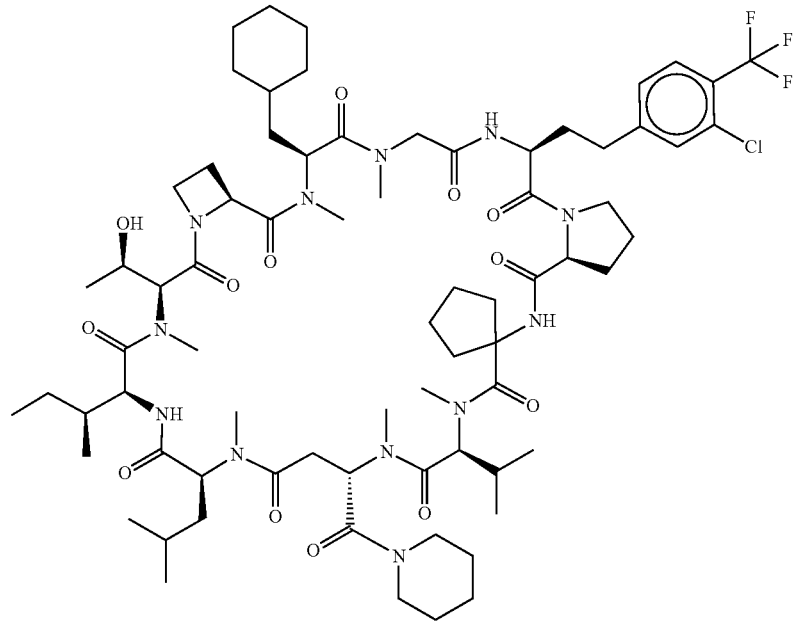 |
| 497 | 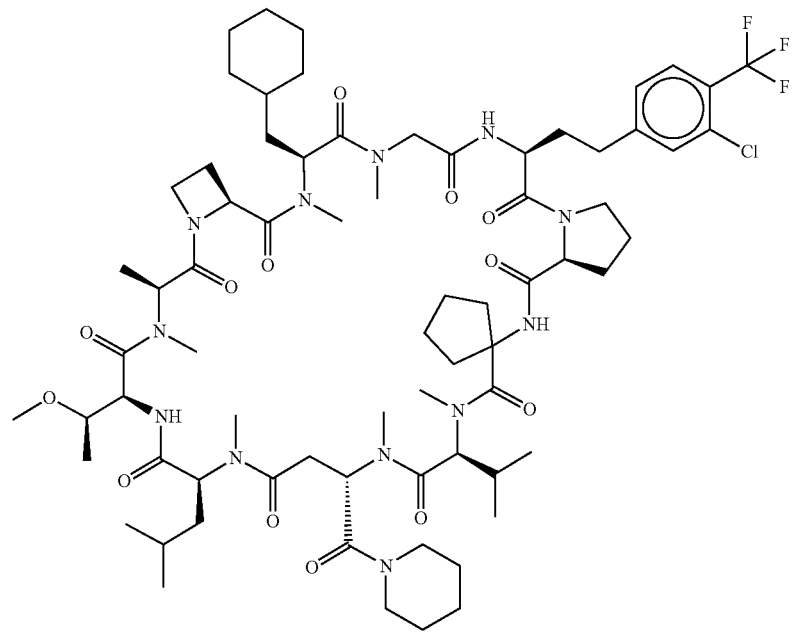 |

TABLE 24-continued
| Compound No. | Structural formula |
|---|---|
| 498 | 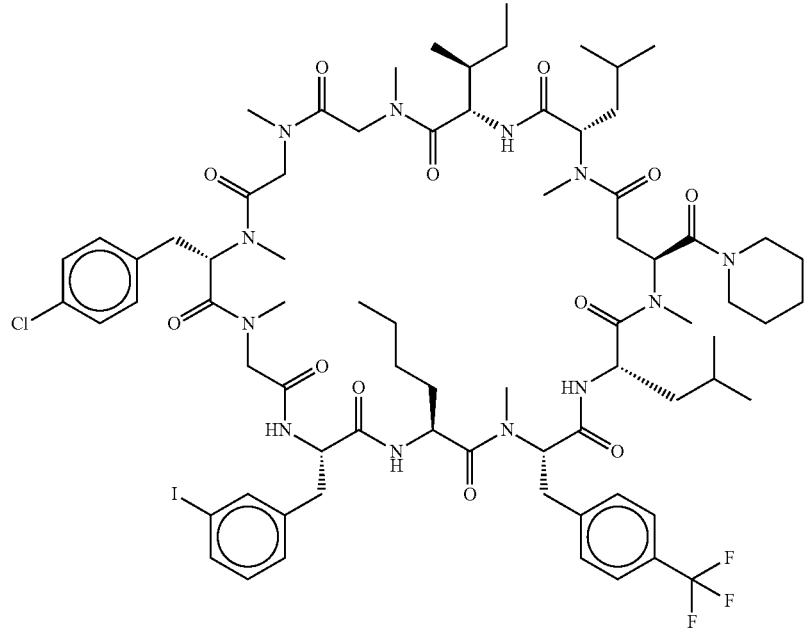 |
| 499 | 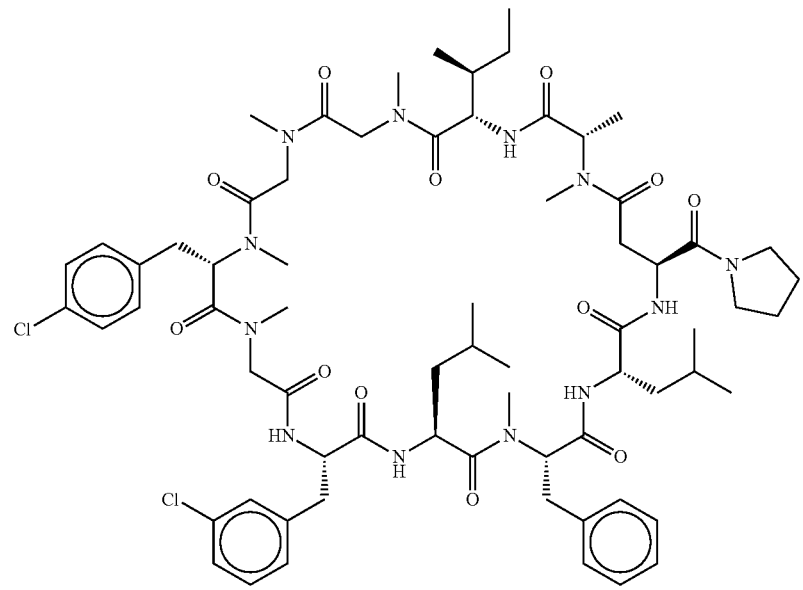 |

TABLE 24-continued
| Compound No. | Structural formula |
|---|---|
| 500 | 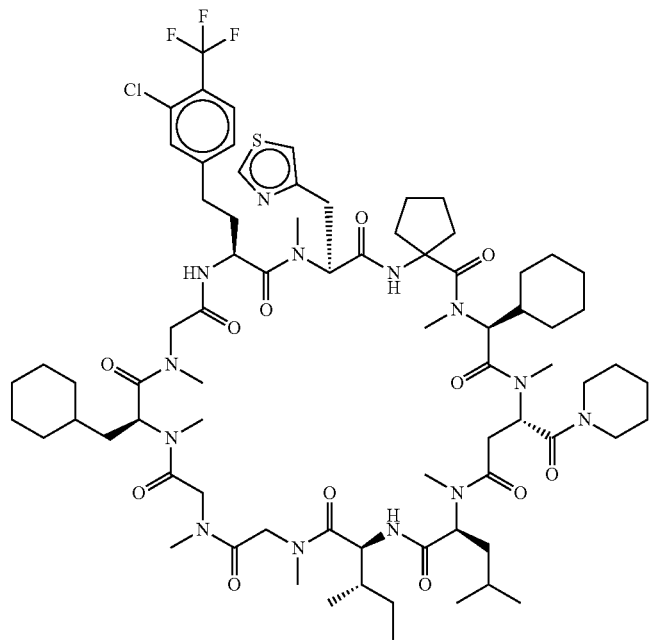 |
| 501 | 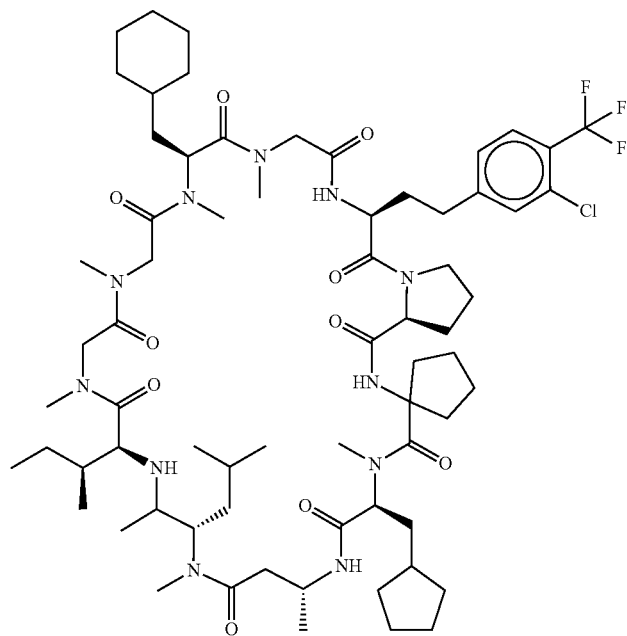 |

TABLE 24-continued
| Compound No. | Structural formula |
|---|---|
| 502 | 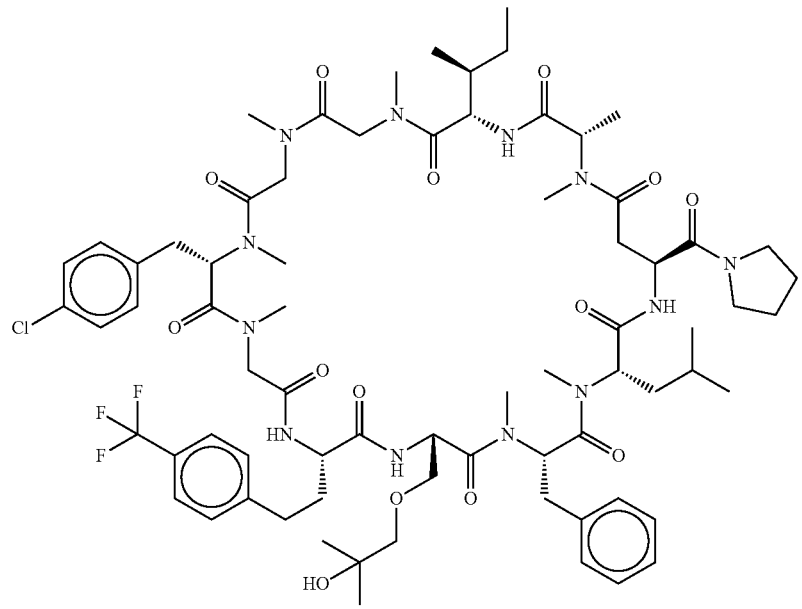 |
| 503 | 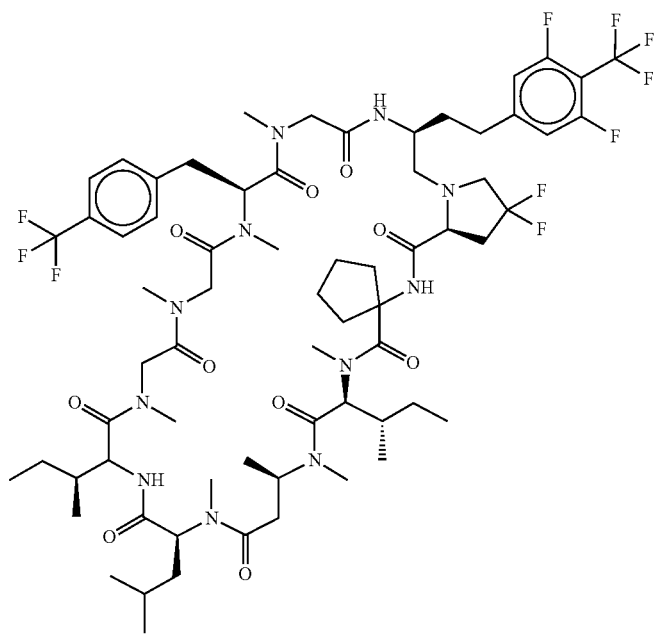 |

TABLE 24-continued
| Compound No. | Structural formula |
|---|---|
| 504 | 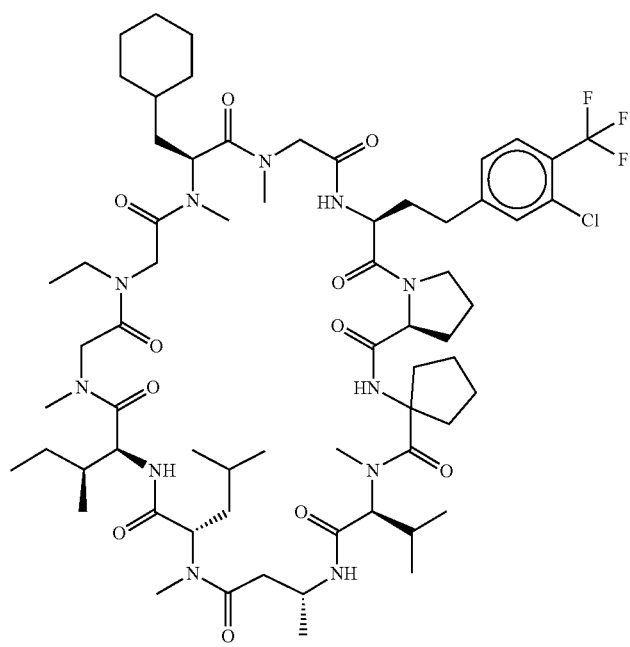 |
| 505 | 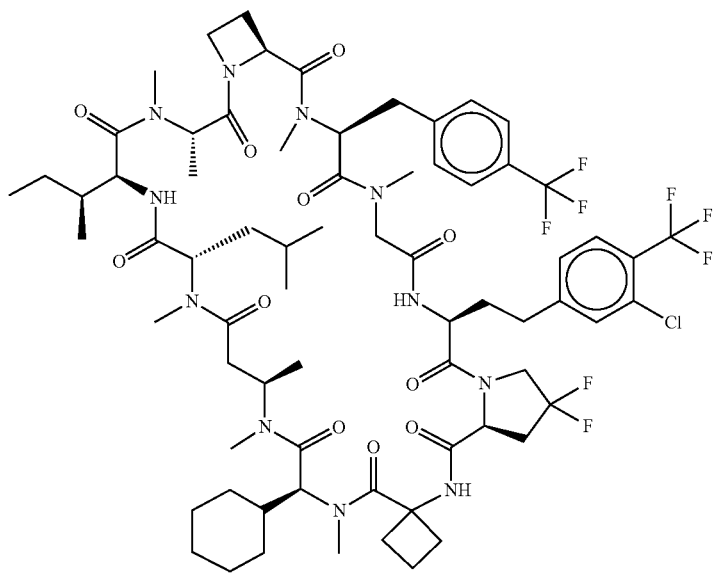 |

TABLE 24-continued
| Compound No. | Structural formula |
|---|---|
| 506 | 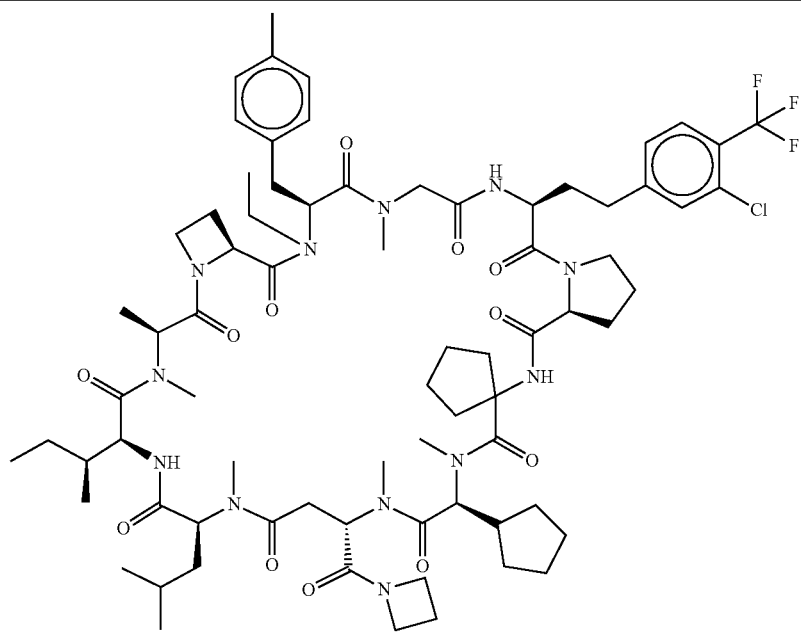 |
| 507 | 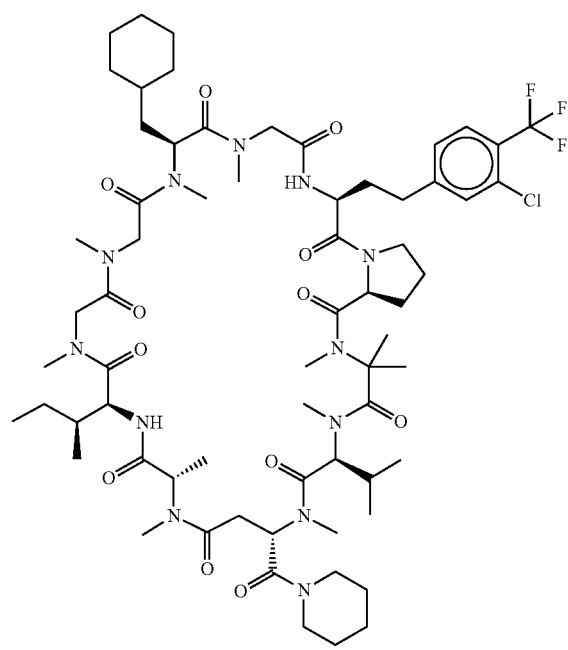 |

TABLE 24-continued
| Compound No. | Structural formula |
|---|---|
| 508 | 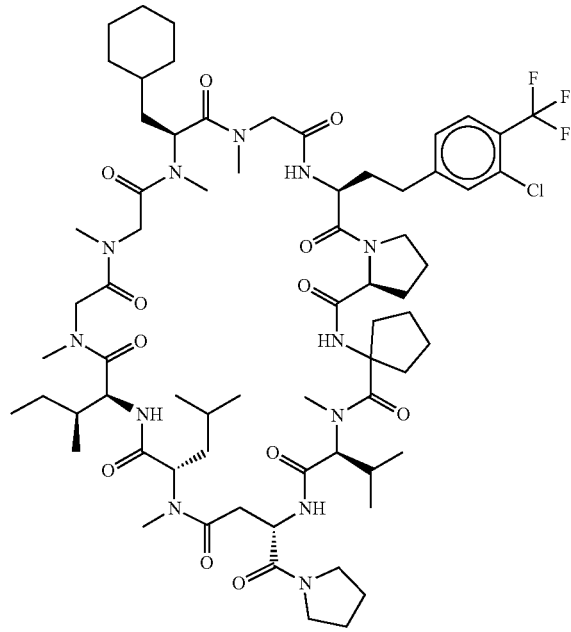 |
| 509 | 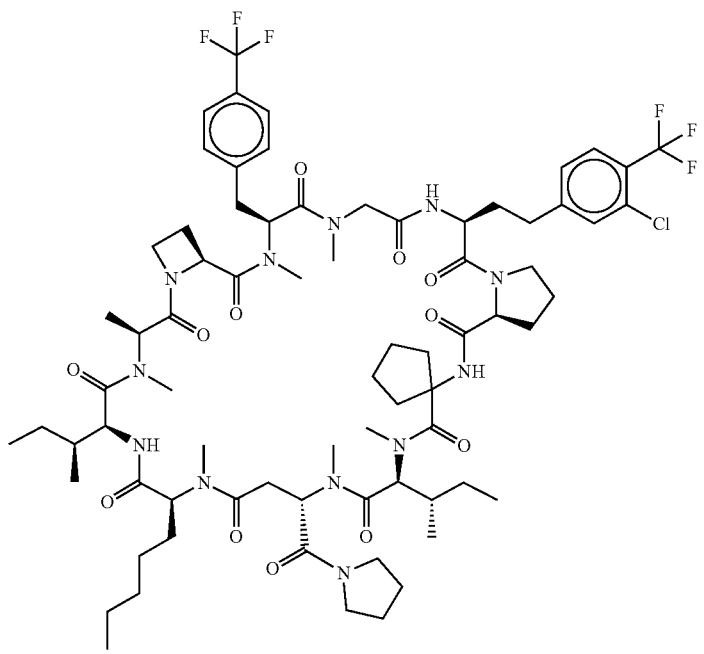 |

TABLE 24-continued
| Compound No. | Structural formula |
| --- | --- |
| 510 | 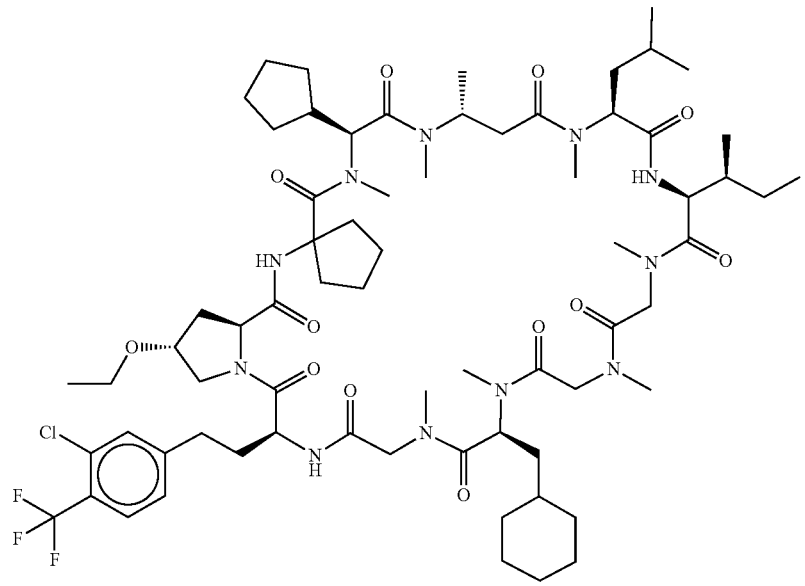 |
| 511 | 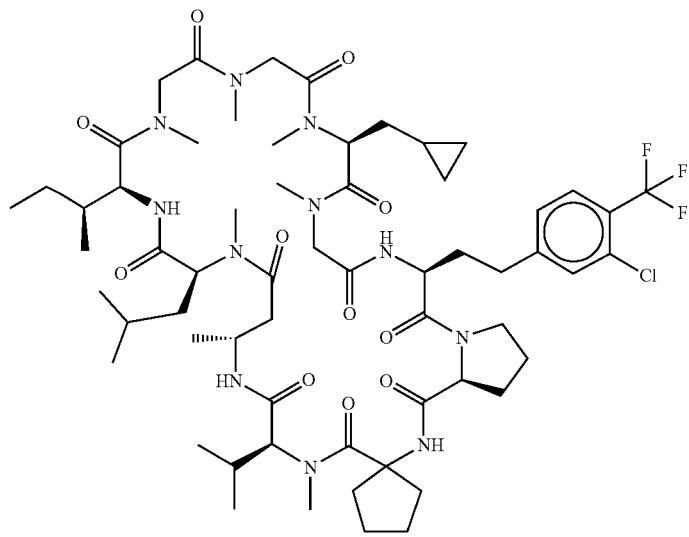 |

TABLE 24-continued
| Compound No. | Structural formula |
|---|---|
| 512 | 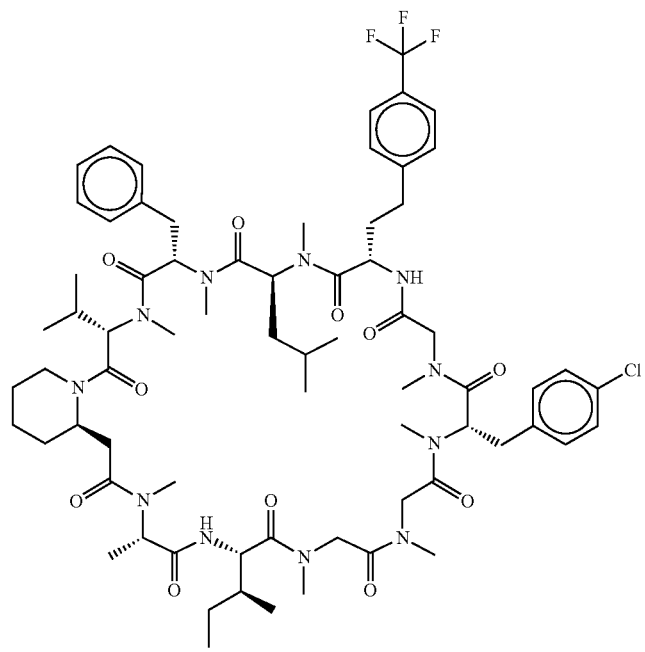 |
| 513 | 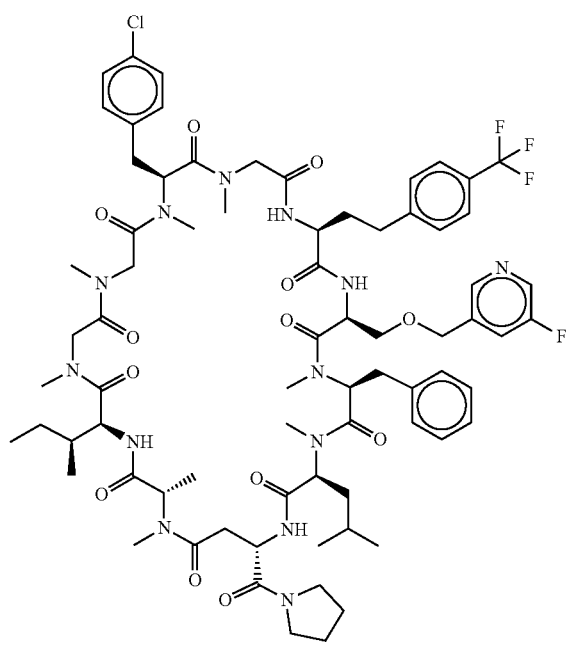 |

TABLE 24-continued
| Compound No. | Structural formula |
|---|---|
| 514 | 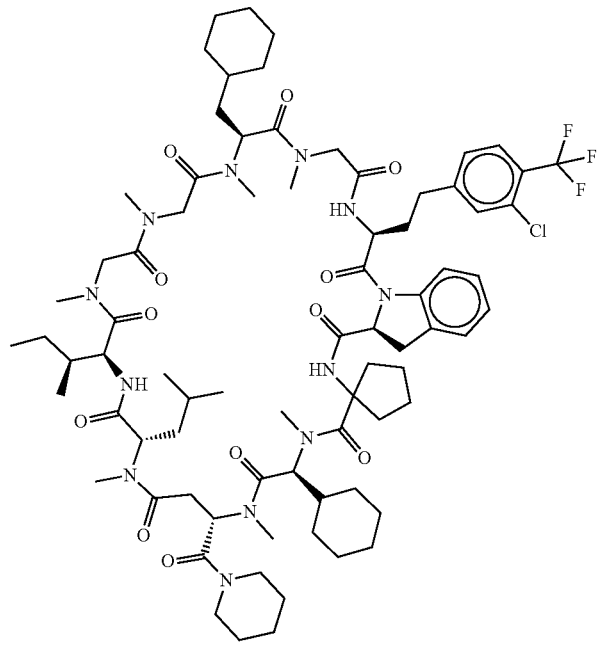 |
| 515 | 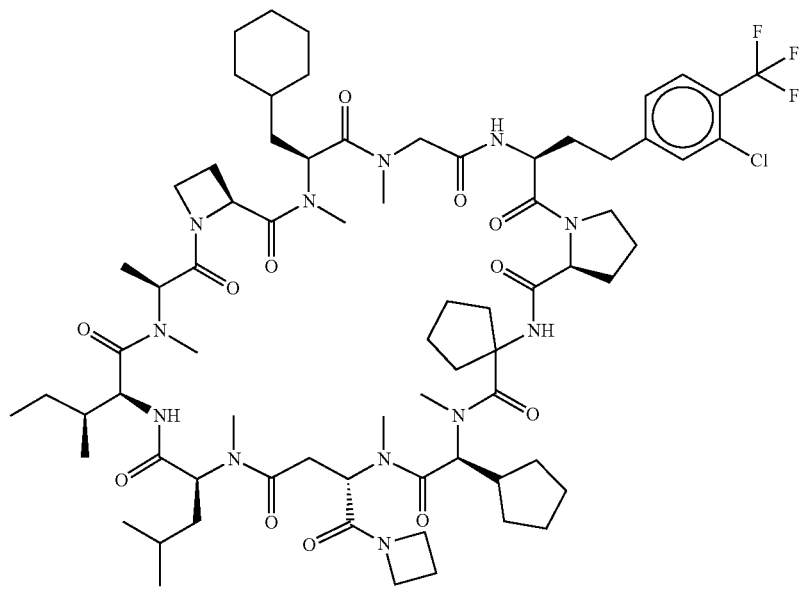 |

TABLE 24-continued
| Compound No. | Structural formula |
| --- | --- |
| 516 | 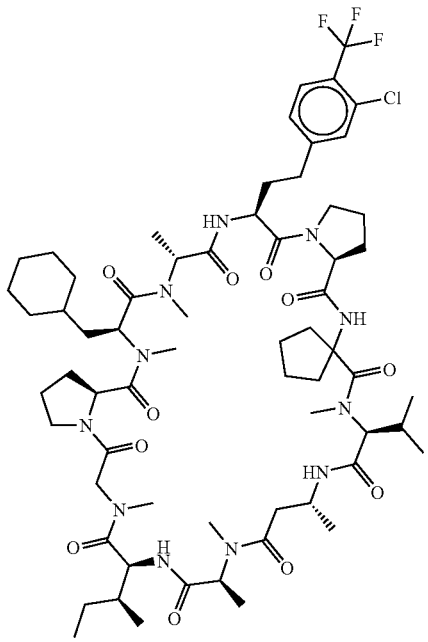 |
| 517 | 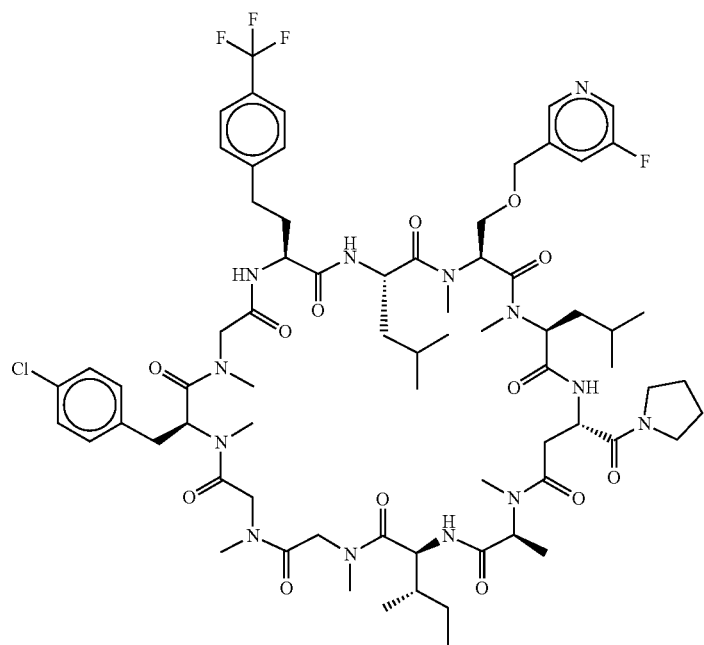 |

TABLE 24-continued
| Compound No. | Structural formula |
|---|---|
| 518 | 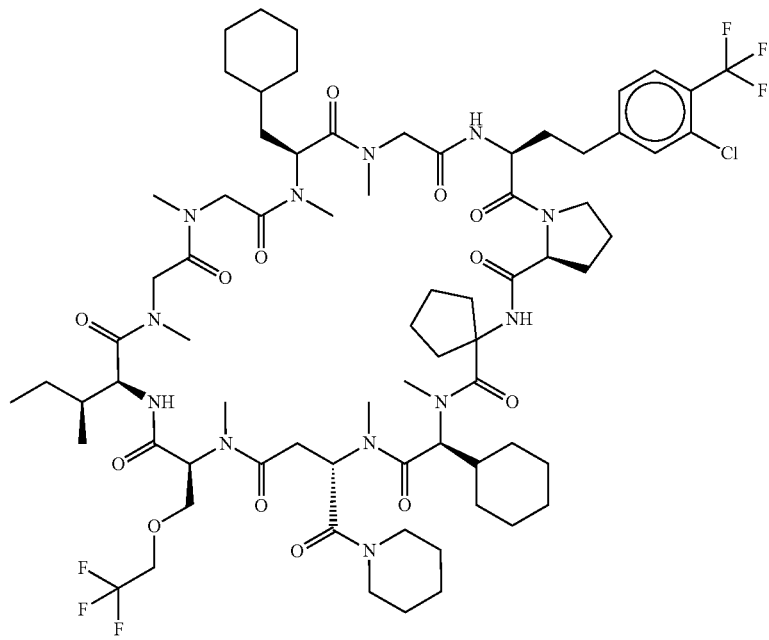 |
| 519 | 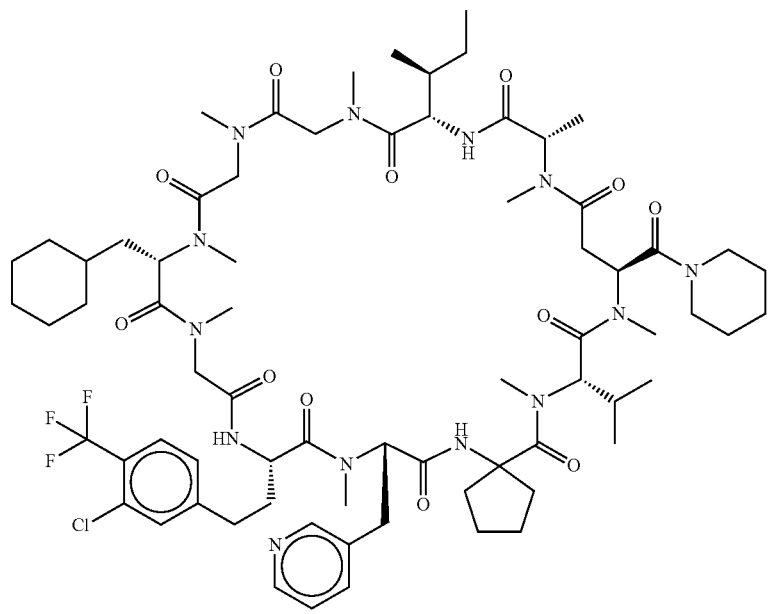 |

TABLE 24-continued
| Compound No. | Structural formula |
|---|---|
| 520 | 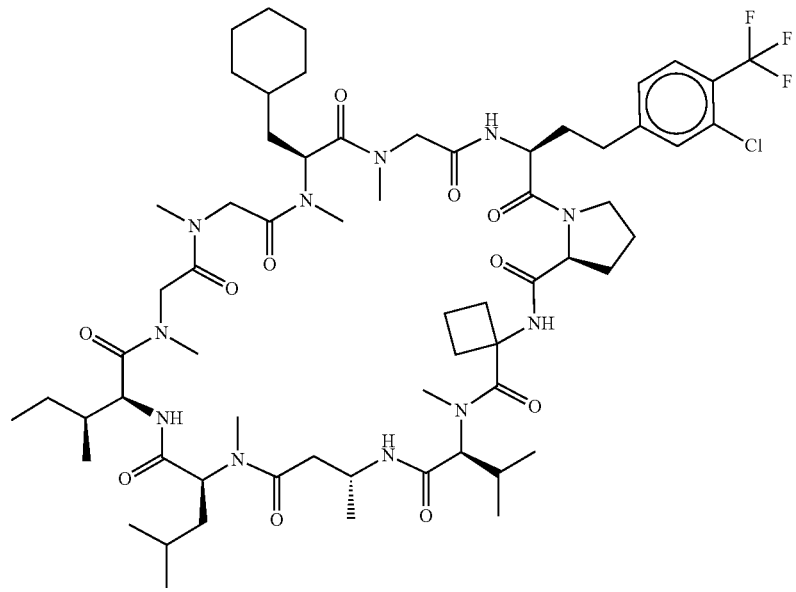 |
| 521 | 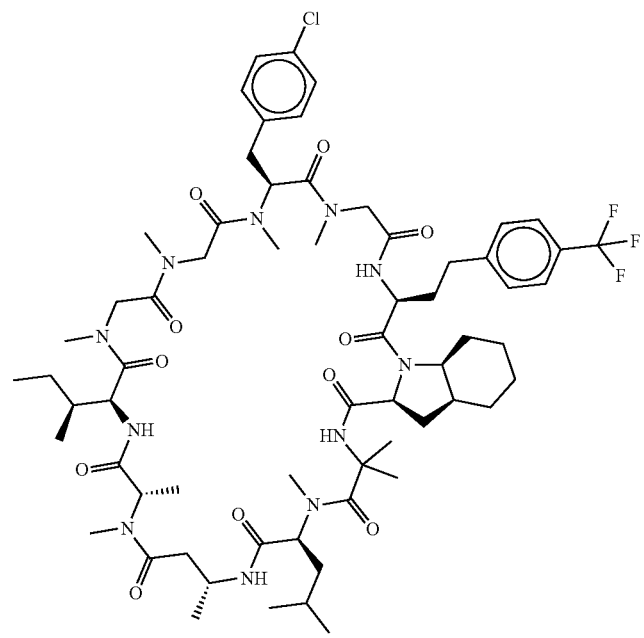 |

TABLE 24-continued
| Compound No. | Structural formula |
|---|---|
| 522 | 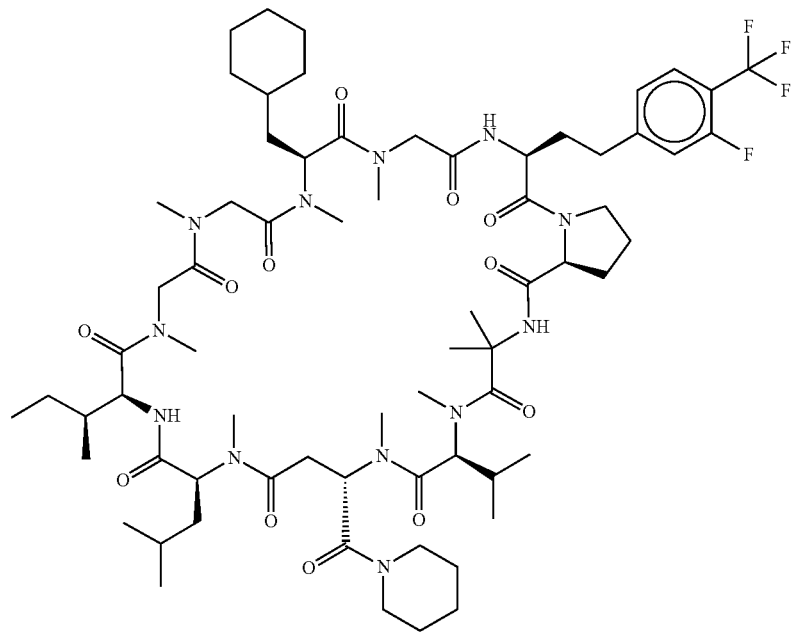 |
| 523 | 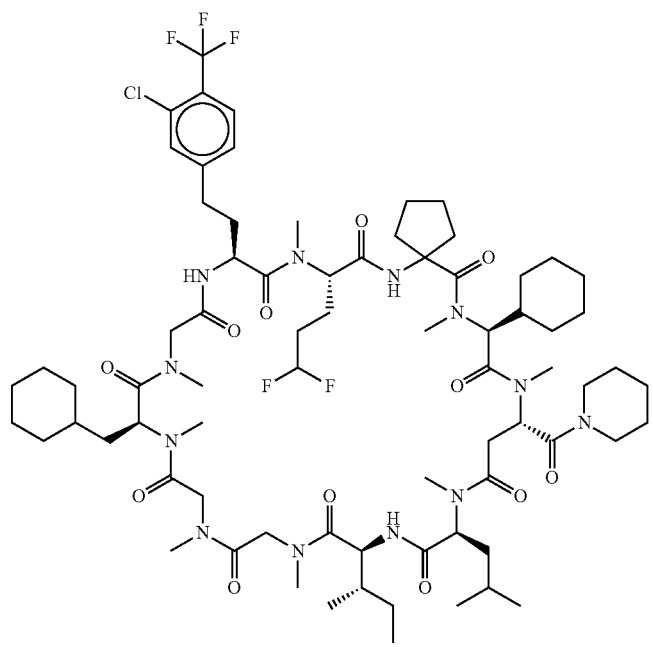 |

TABLE 24-continued
| Compound No. | Structural formula |
|---|---|
| 524 | 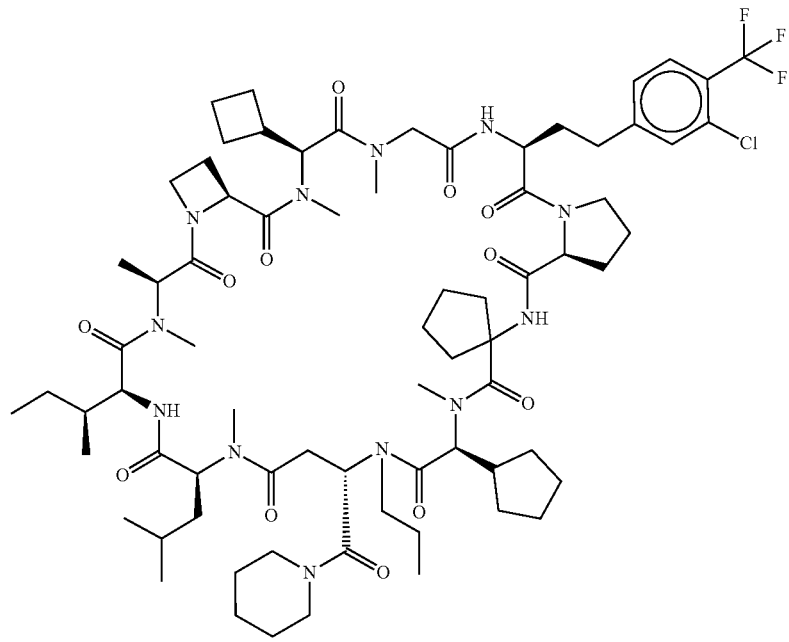 |
| 525 | 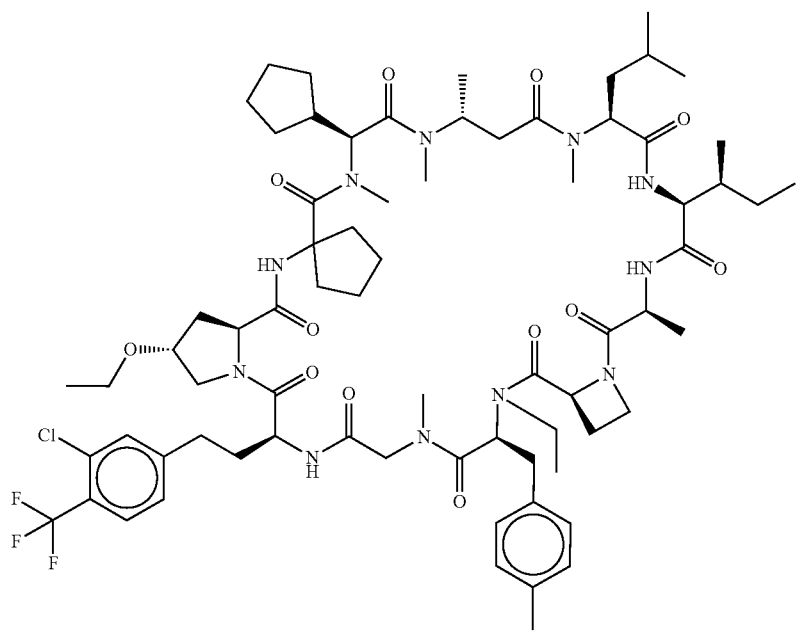 |

TABLE 24-continued
| Compound No. | Structural formula |
|---|---|
| 526 | 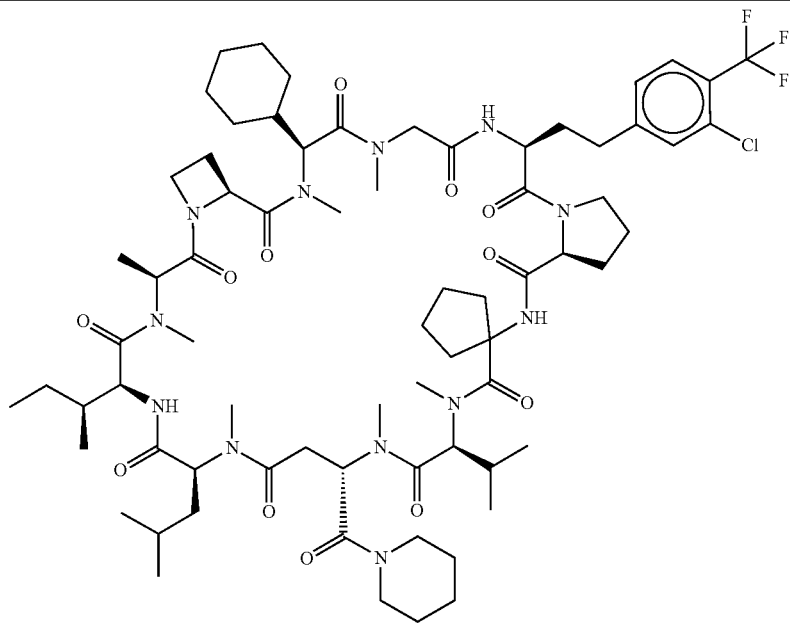 |
| 527 | 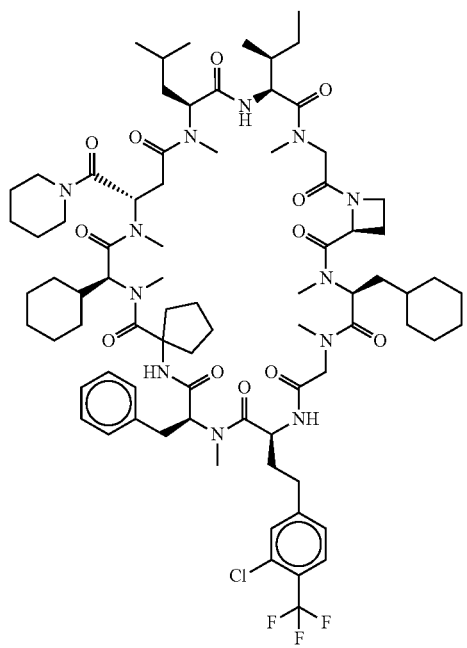 |

TABLE 24-continued
| Compound No. | Structural formula |
|---|---|
| 528 | 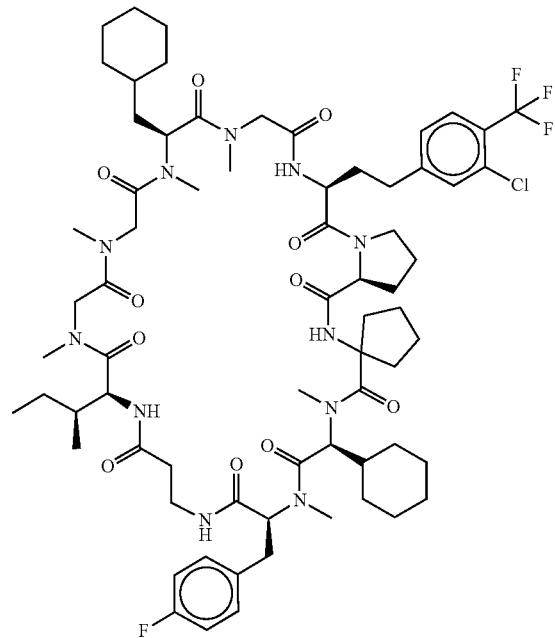 |
| 529 | 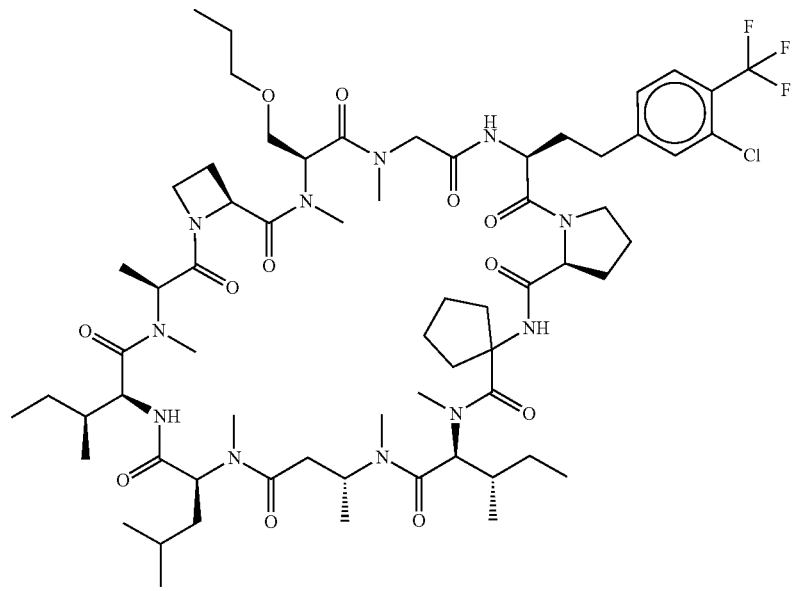 |

TABLE 24-continued
| Compound No. | Structural formula |
|---|---|
| 530 | 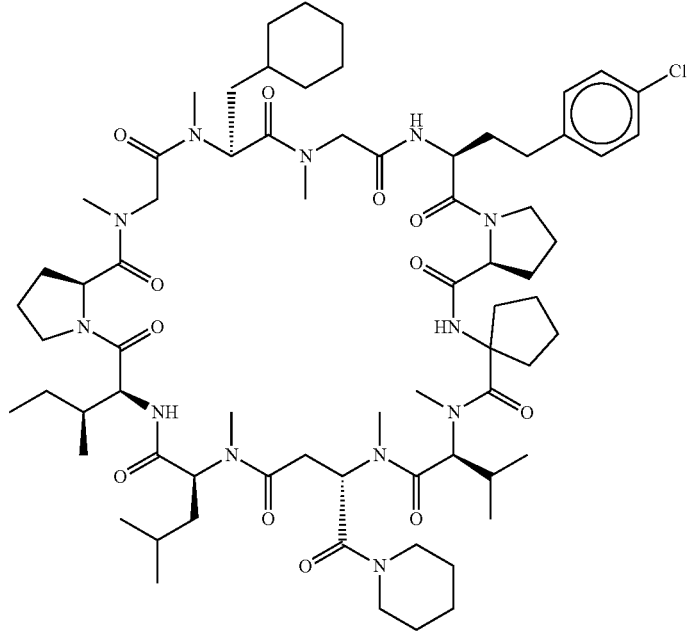 |
| 531 | 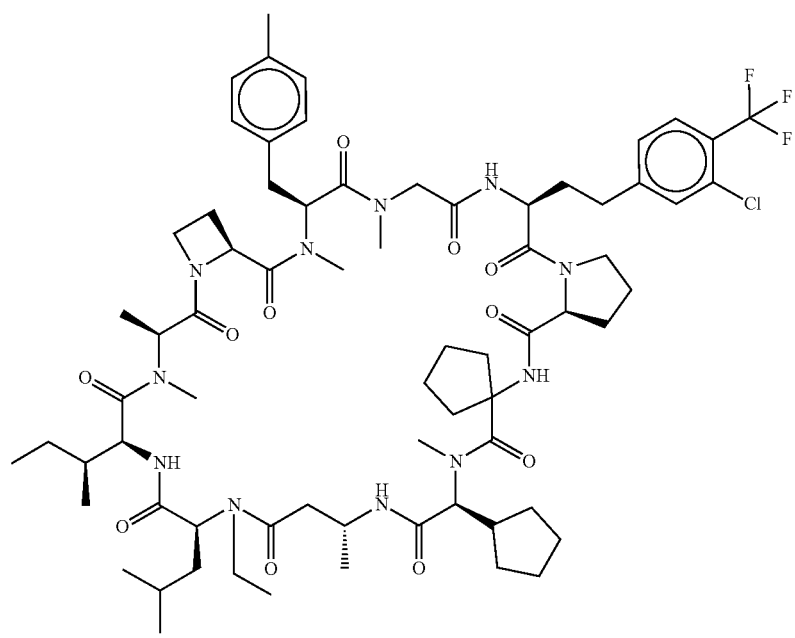 |

TABLE 24-continued
| Compound No. | Structural formula |
|---|---|
| 532 | 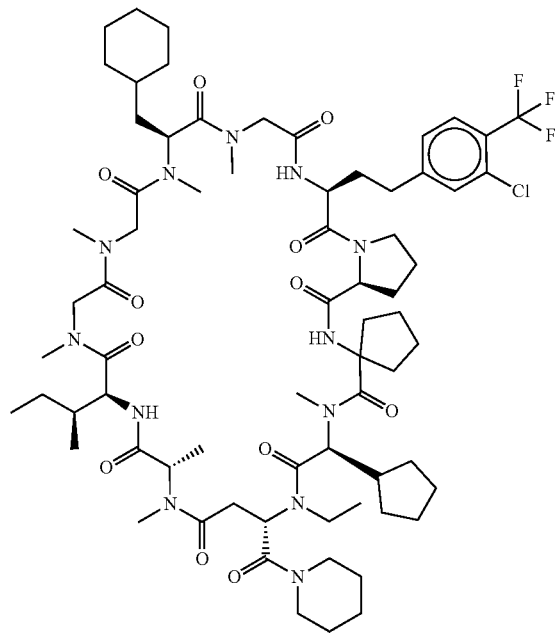 |
| 533 | 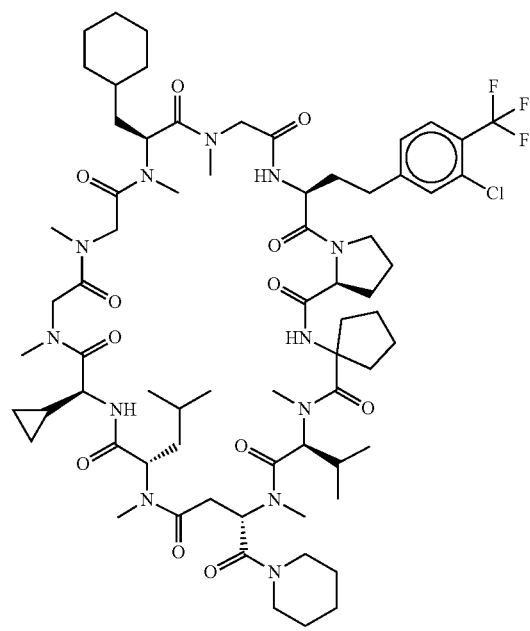 |

TABLE 24-continued
| Compound No. | Structural formula |
|---|---|
| 534 | 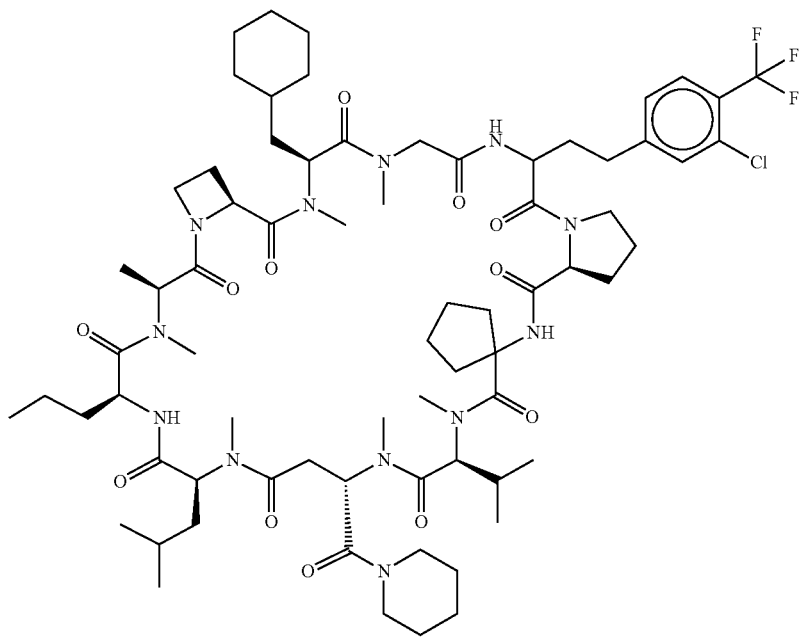 |
| 535 | 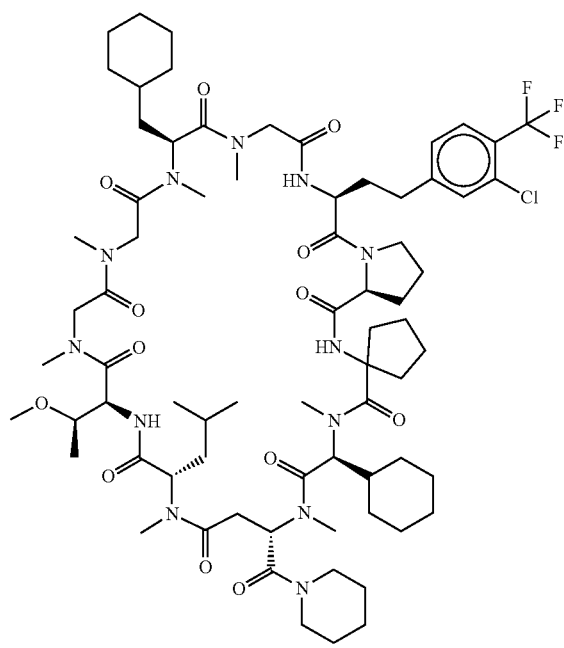 |

TABLE 24-continued
| Compound No. | Structural formula |
|---|---|
| 536 | 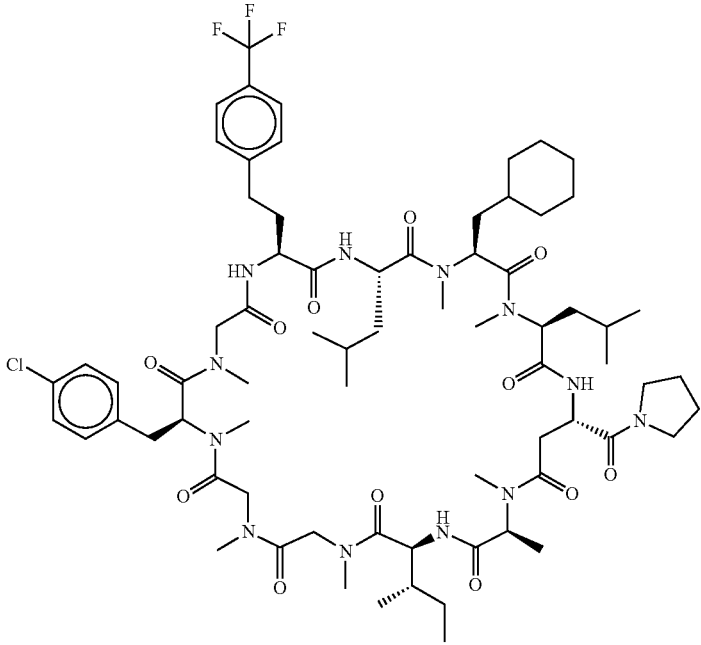 |
| 537 | 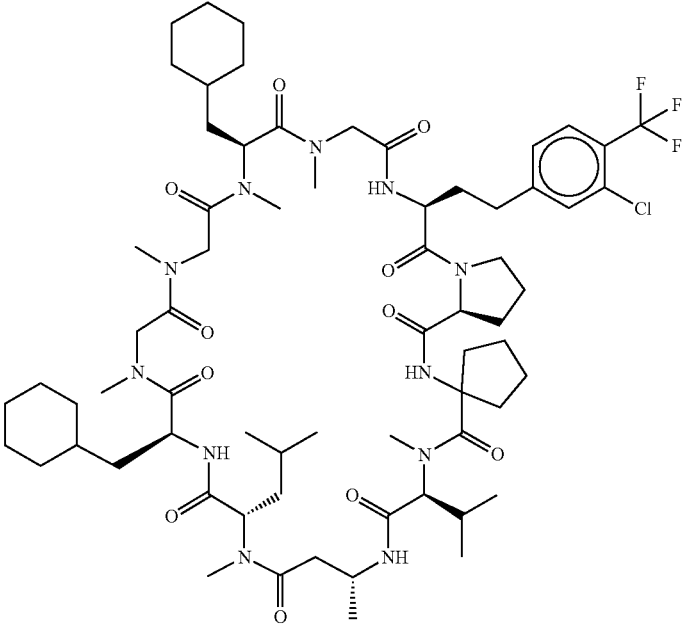 |

TABLE 24-continued
| Compound No. | Structural formula |
|---|---|
| 538 | 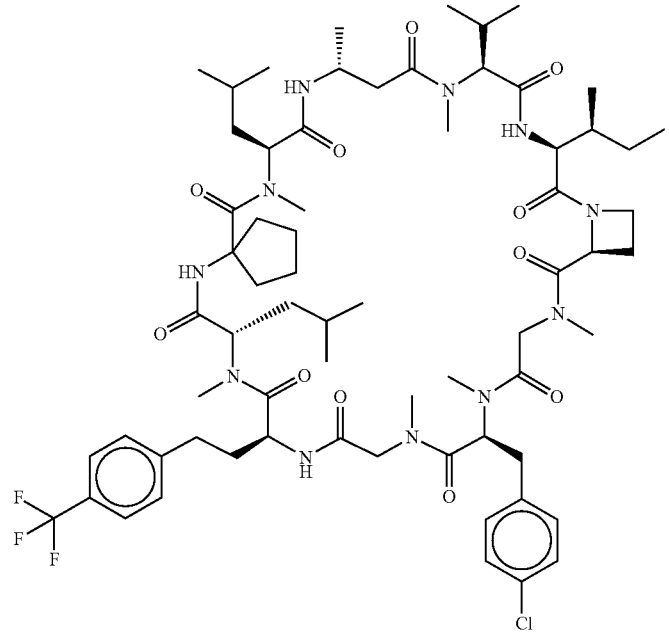 |
| 539 | 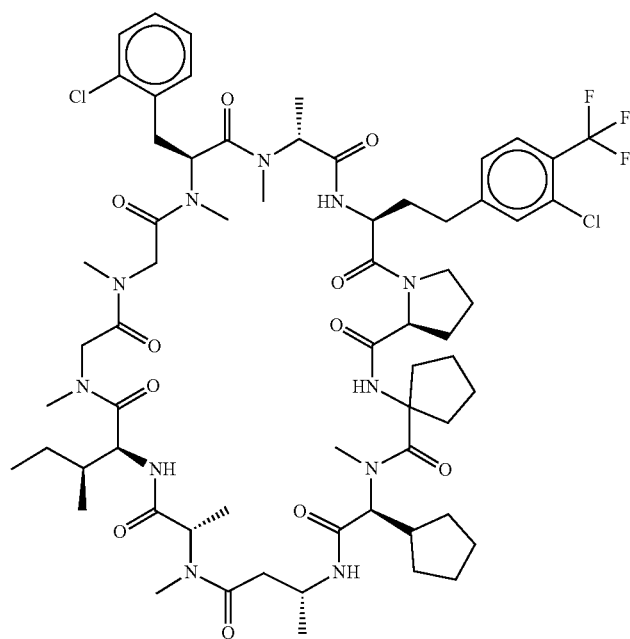 |

TABLE 24-continued
| Compound No. | Structural formula |
|---|---|
| 540 | 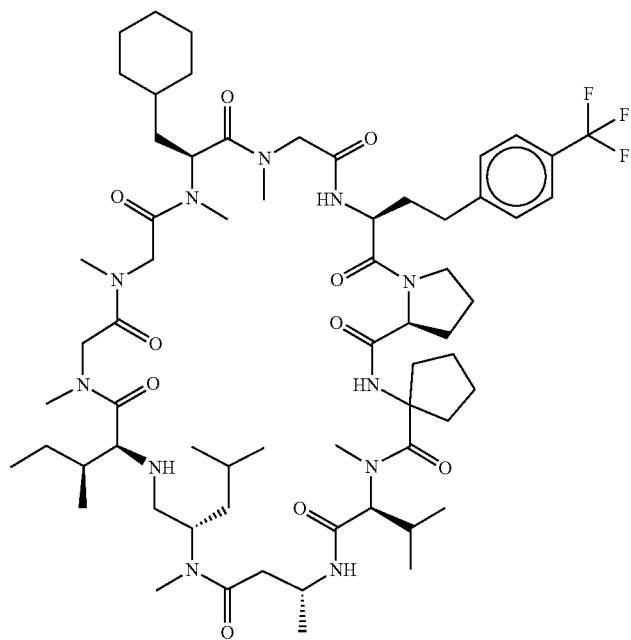 |
| 541 | 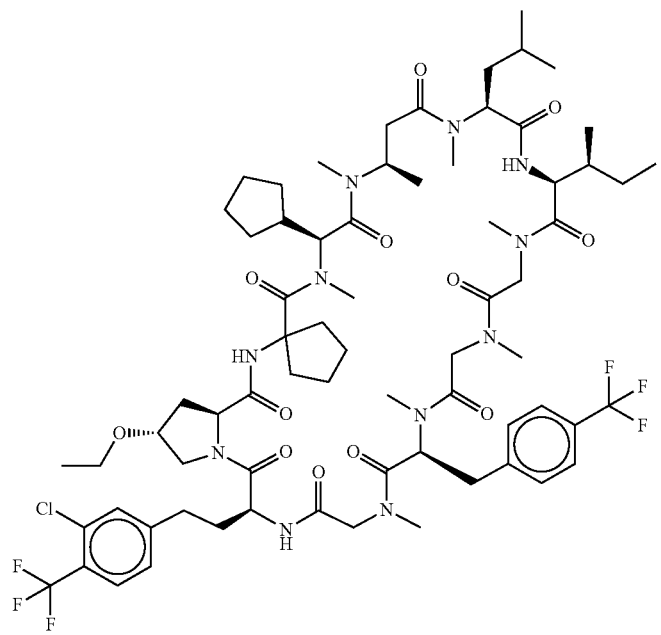 |

TABLE 24-continued
| Compound No. | Structural formula |
|---|---|
| 542 | 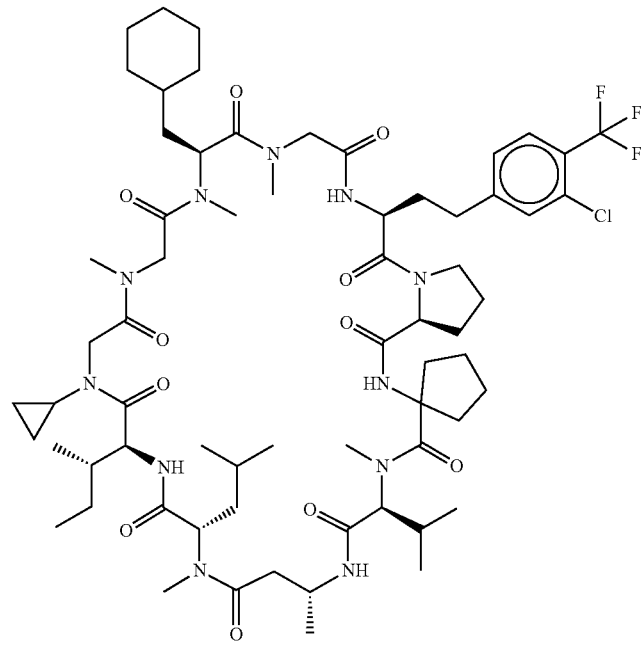 |
| 543 | 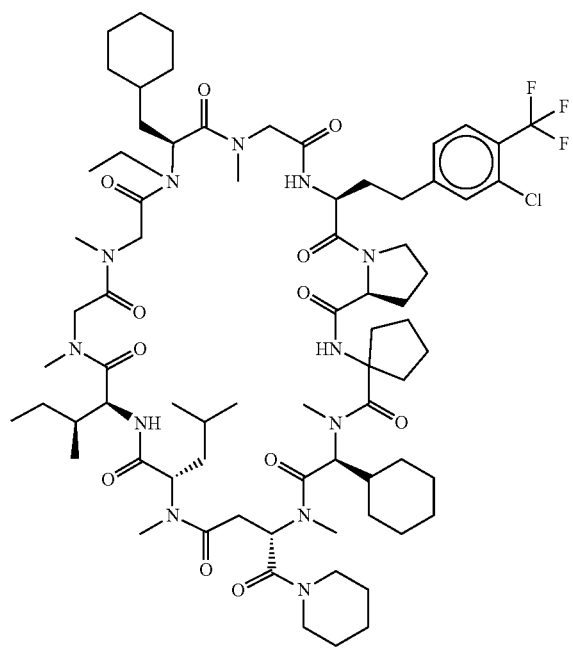 |

TABLE 24-continued
| Compound No. | Structural formula |
|---|---|
| 544 | 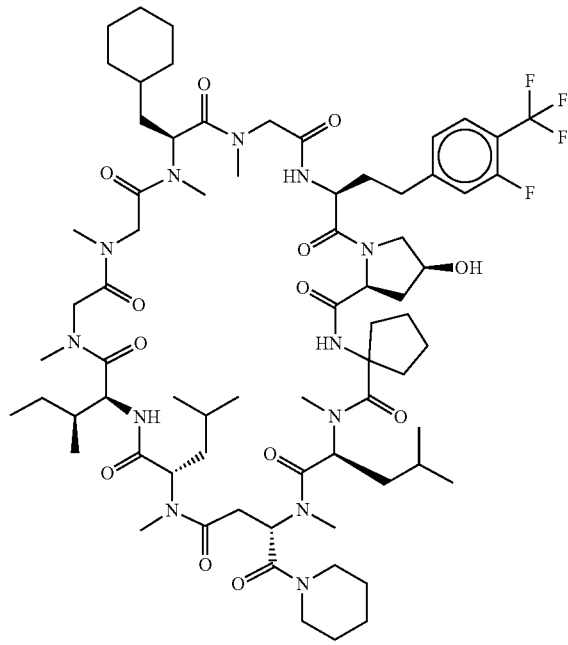 |
| 545 | 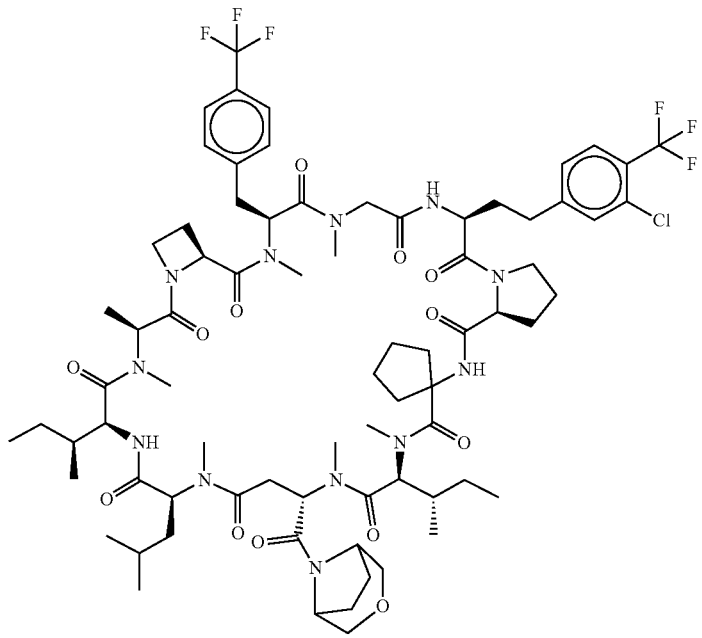 |

TABLE 24-continued
| Compound No. | Structural formula |
|---|---|
| 546 | 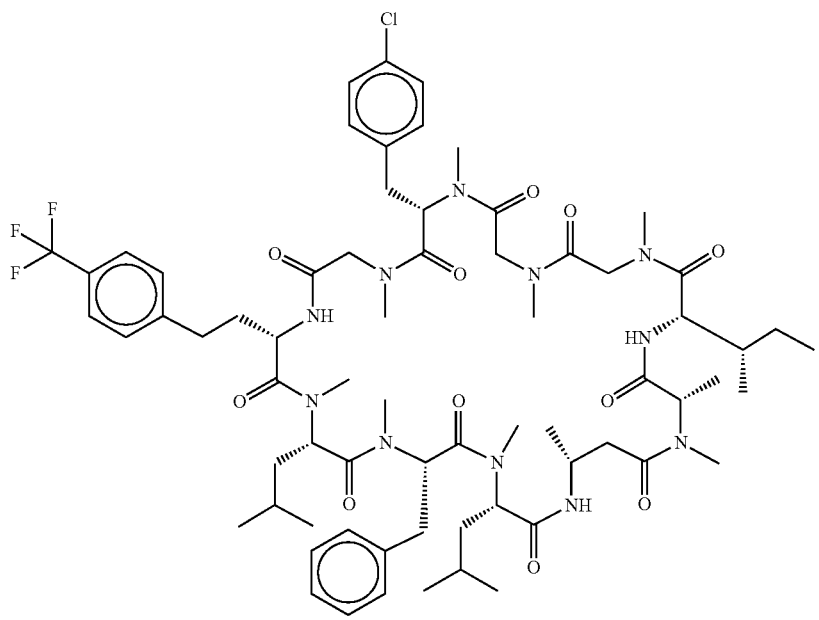 |
| 547 | 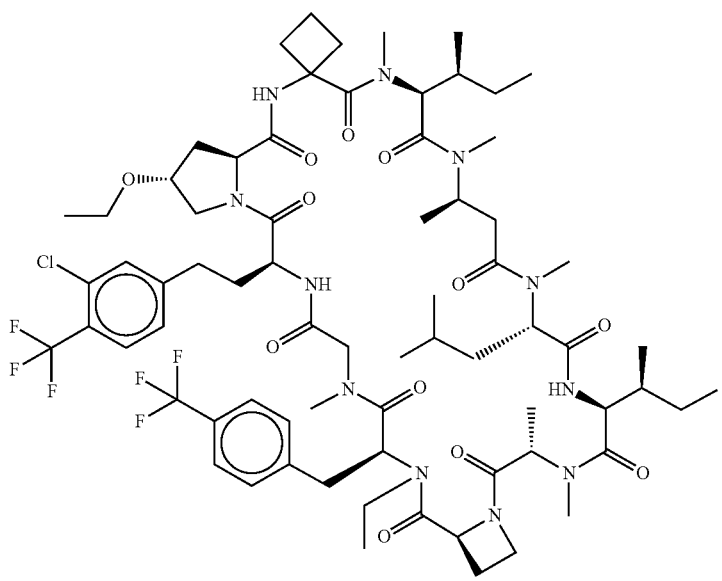 |

TABLE 24-continued
| Compound No. | Structural formula |
|---|---|
| 548 | 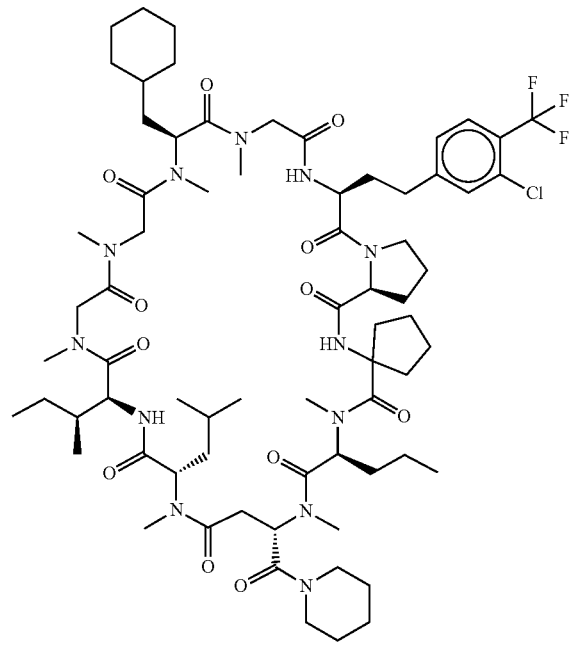 |
| 549 | 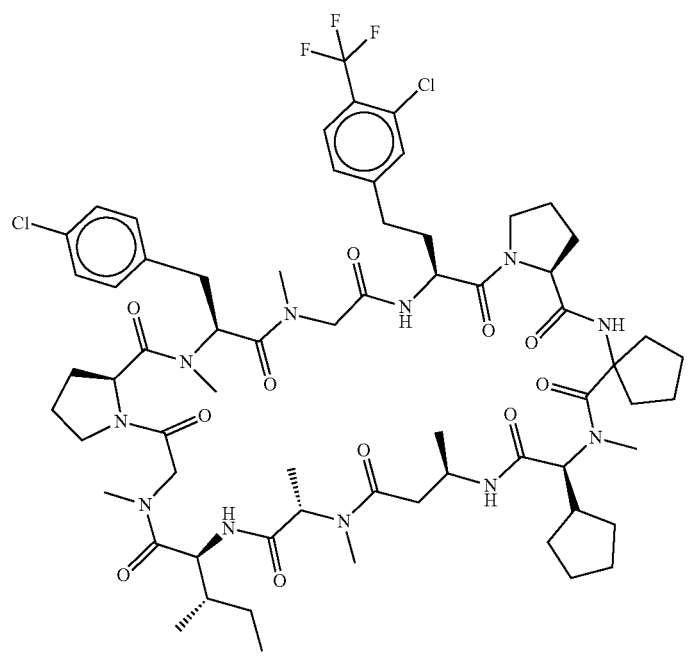 |

TABLE 24-continued
| Compound No. | Structural formula |
|---|---|
| 550 | 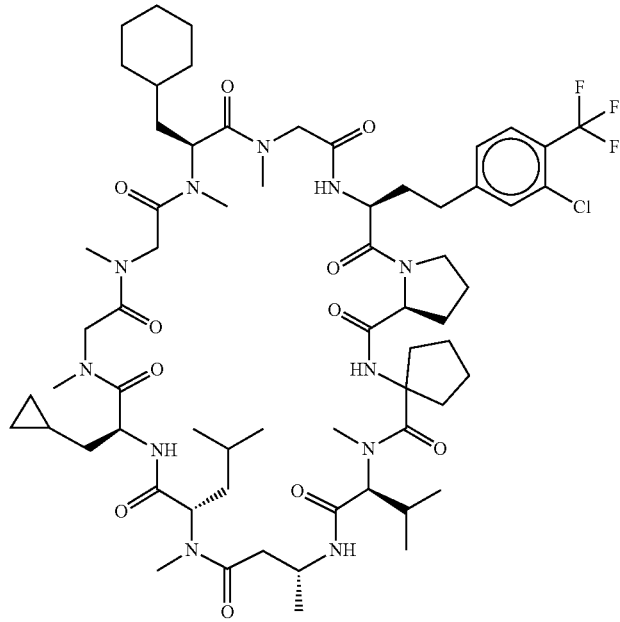 |
| 551 | 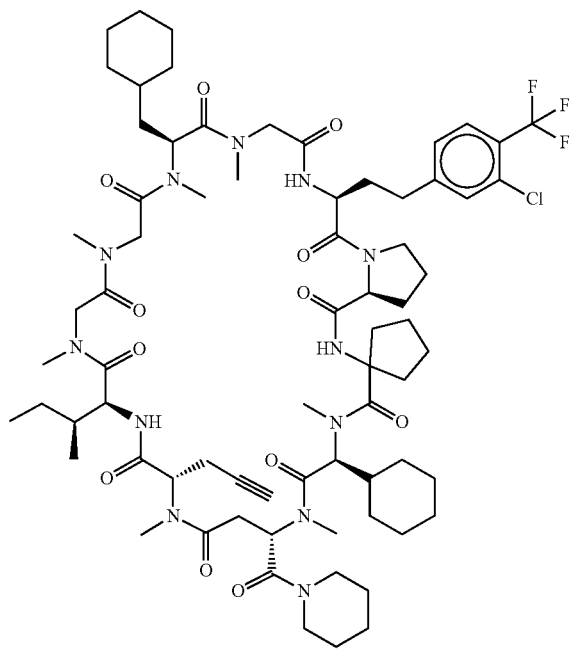 |

TABLE 24-continued
| Compound No. | Structural formula |
|---|---|
| 552 | 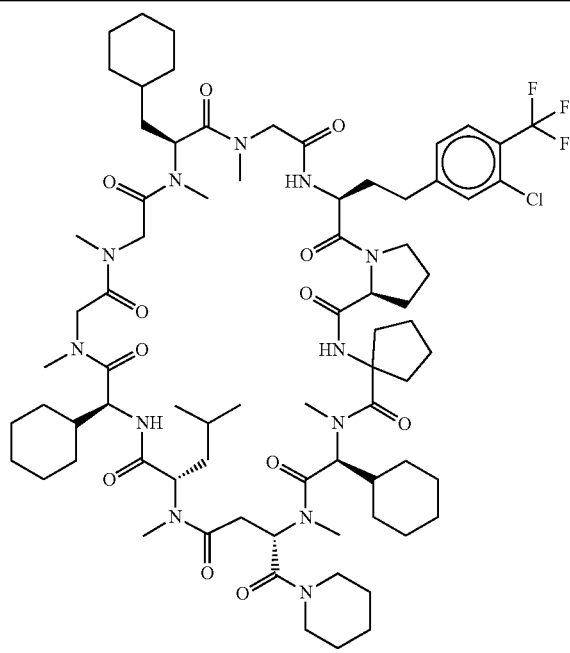 |
| 553 | 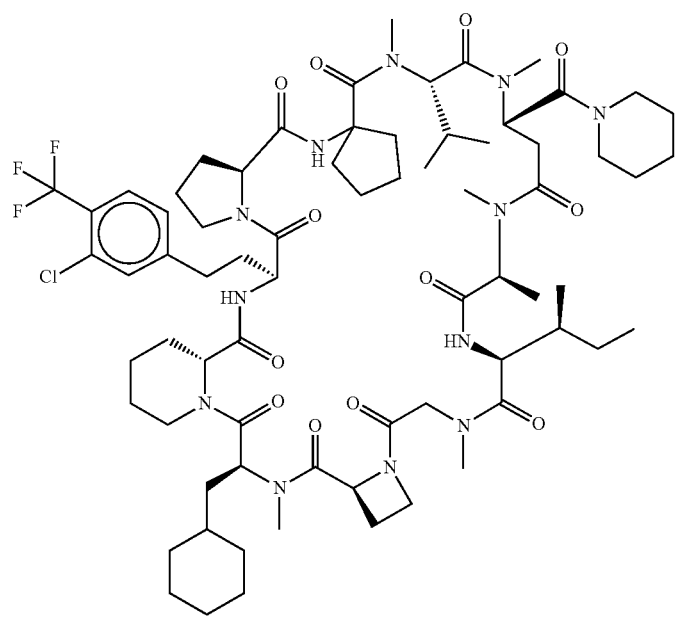 |

TABLE 24-continued
| Compound No. | Structural formula |
|---|---|
| 554 | 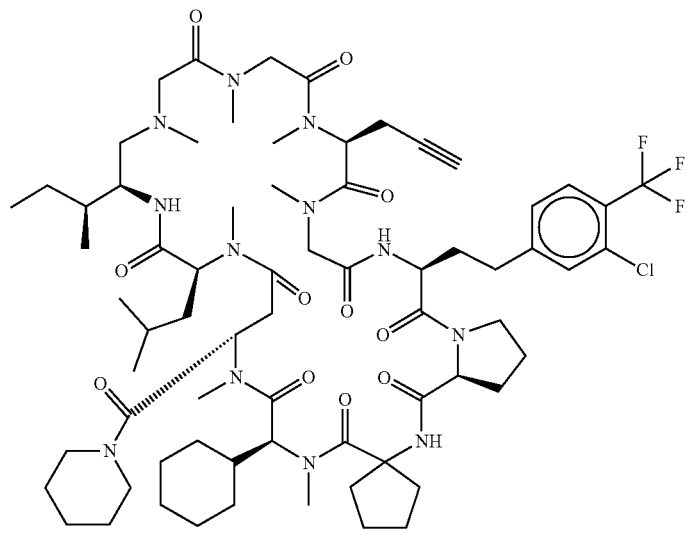 |
| 555 | 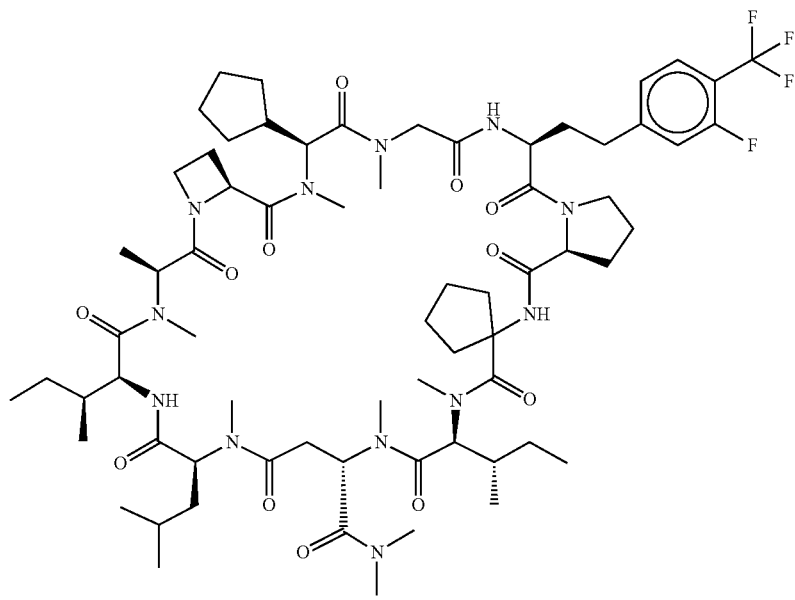 |

TABLE 24-continued
| Compound No. | Structural formula |
|---|---|
| 556 | 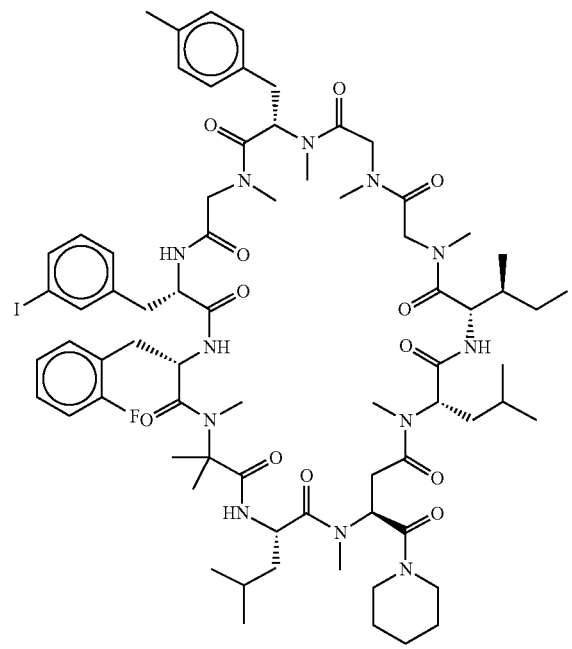 |
| 557 | 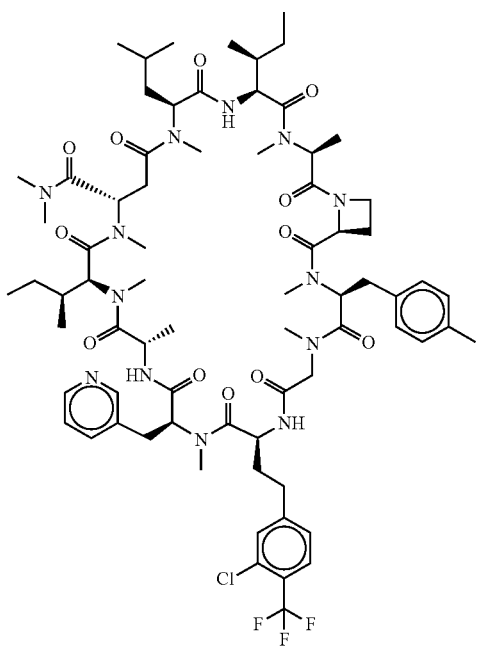 |

TABLE 24-continued
| Compound No. | Structural formula |
|---|---|
| 558 | 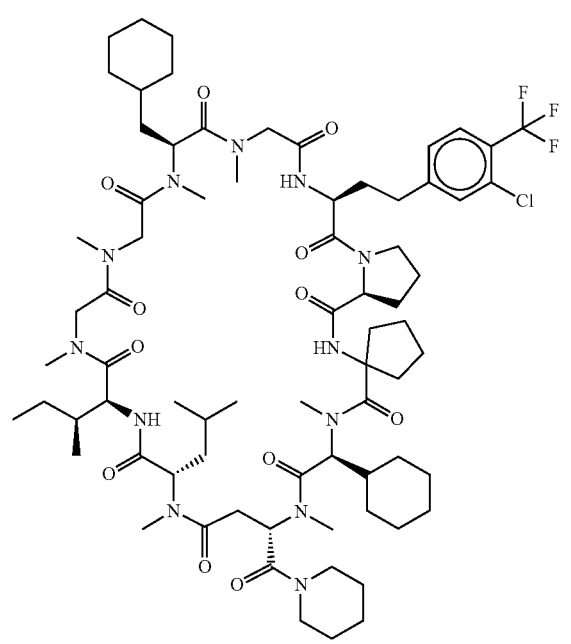 |
| 559 | 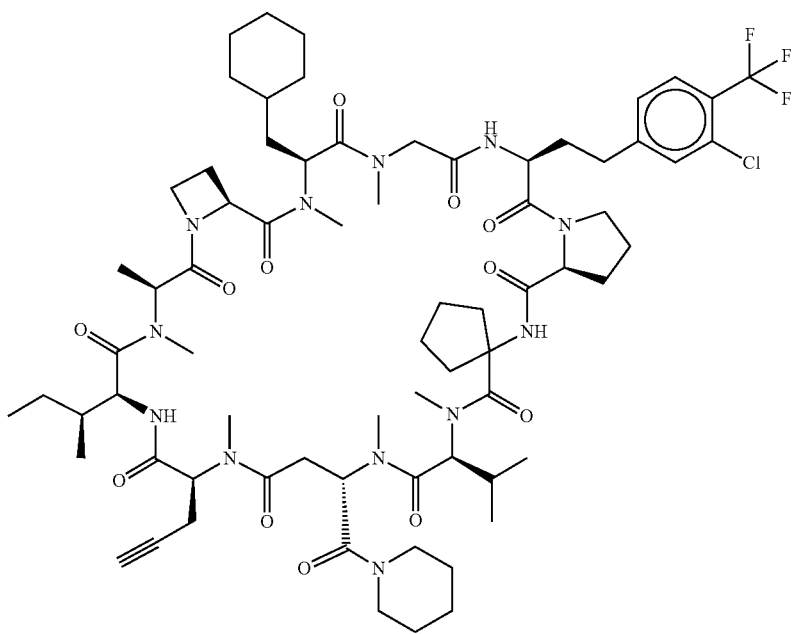 |

TABLE 24-continued
| Compound No. | Structural formula |
|---|---|
| 560 | 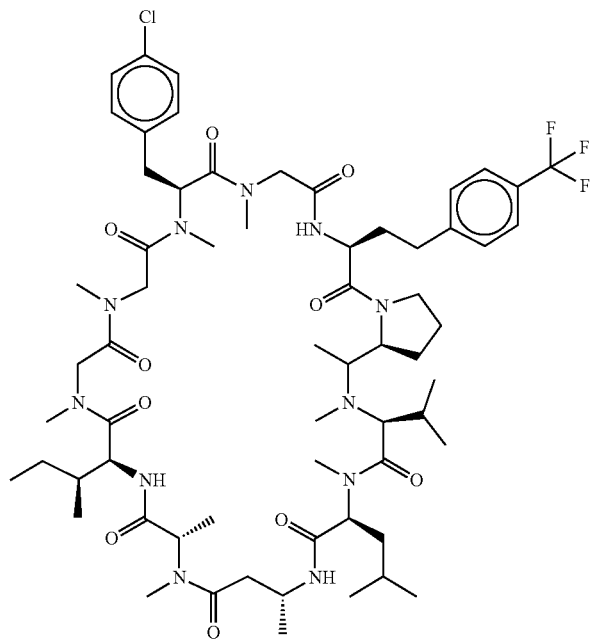 |
| 561 | 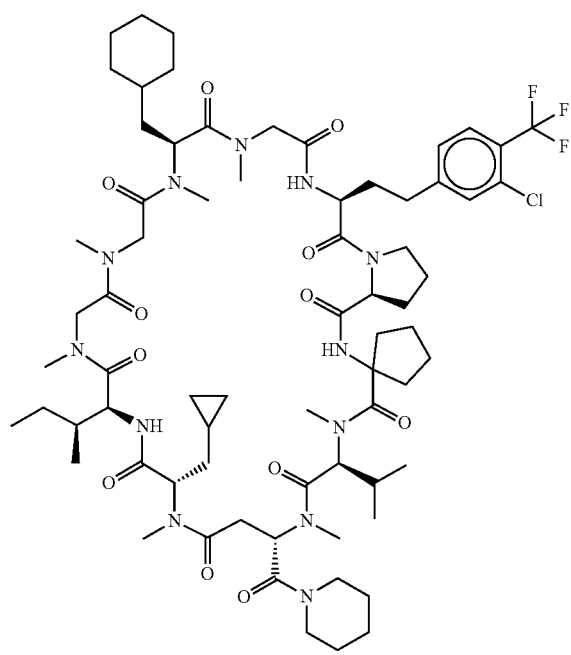 |

TABLE 24-continued
| Compound No. | Structural formula |
|---|---|
| 562 | 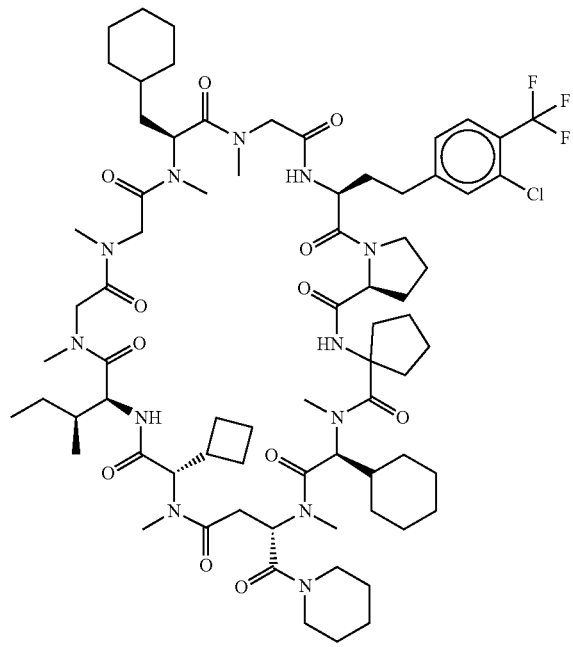 |
| 563 | 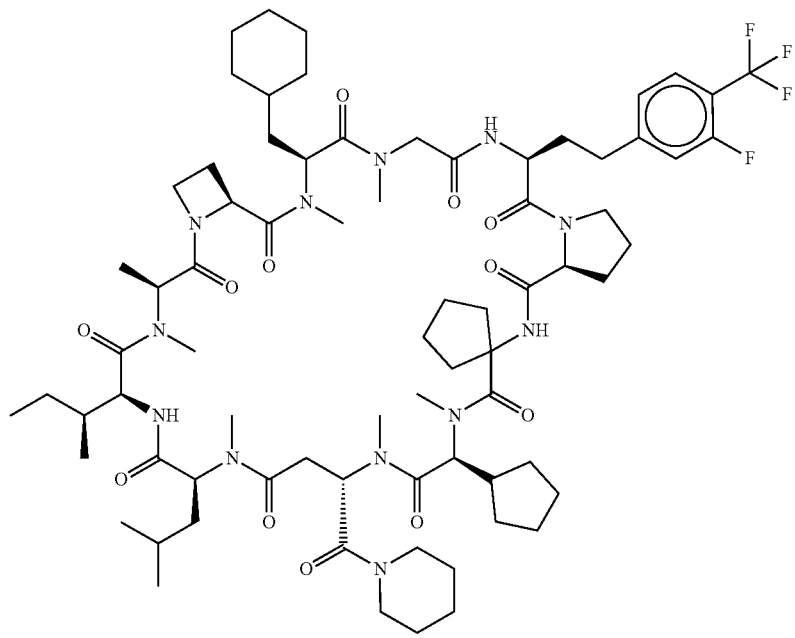 |

TABLE 24-continued
| Compound No. | Structural formula |
|---|---|
| 564 | 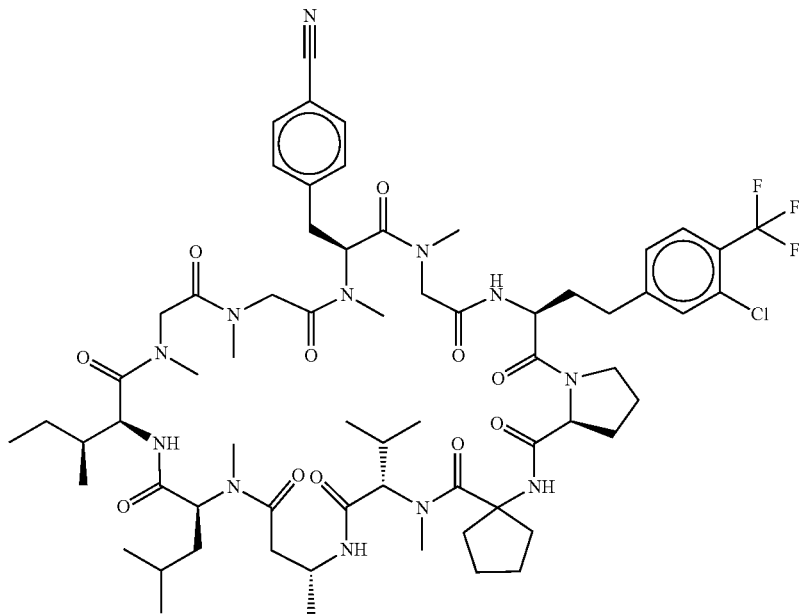 |
| 565 | 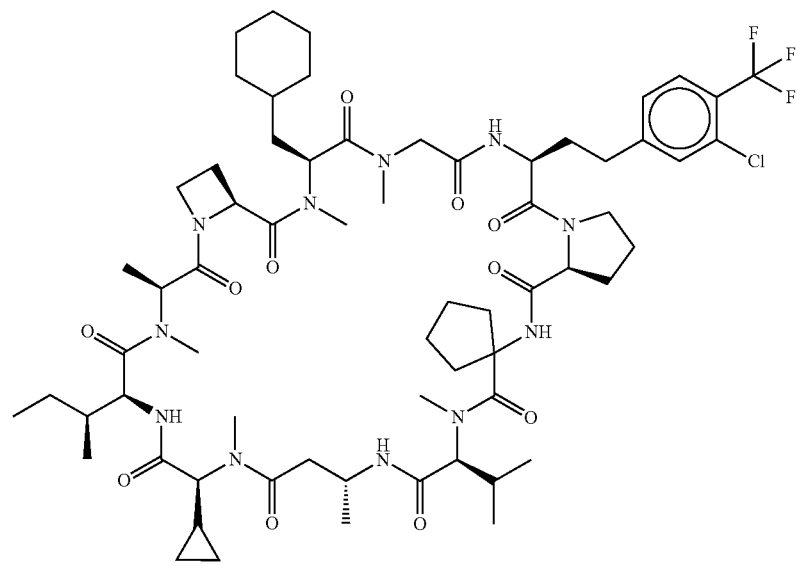 |

TABLE 24-continued
| Compound No. | Structural formula |
|---|---|
| 566 | 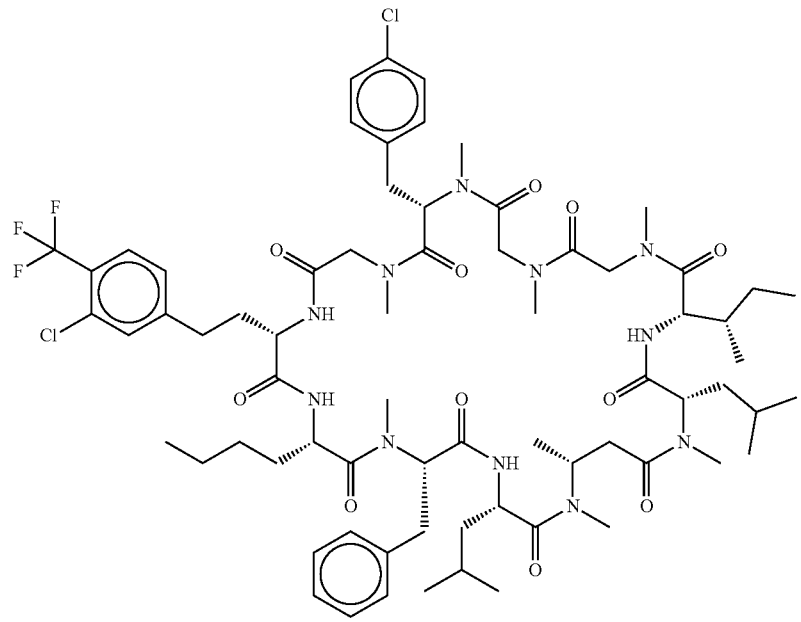 |
| 567 | 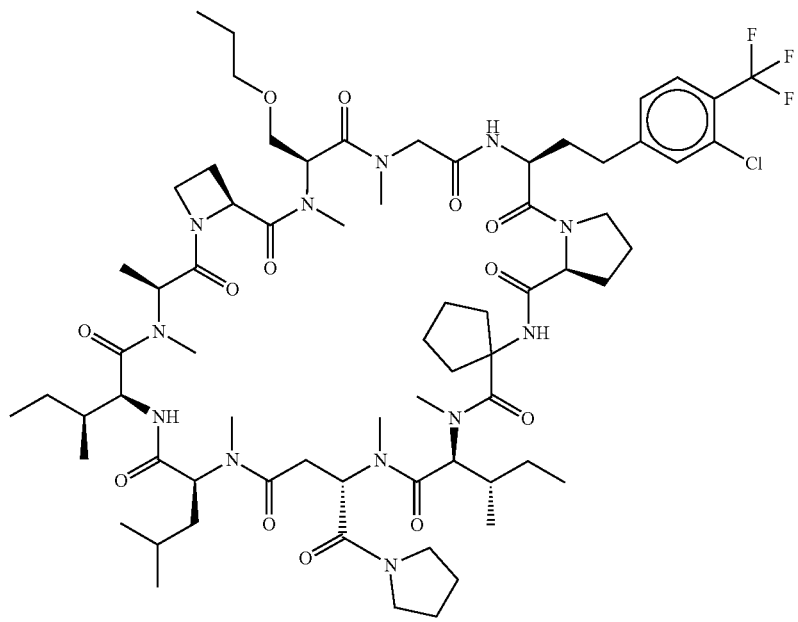 |

TABLE 24-continued
| Compound No. | Structural formula |
|---|---|
| 568 | 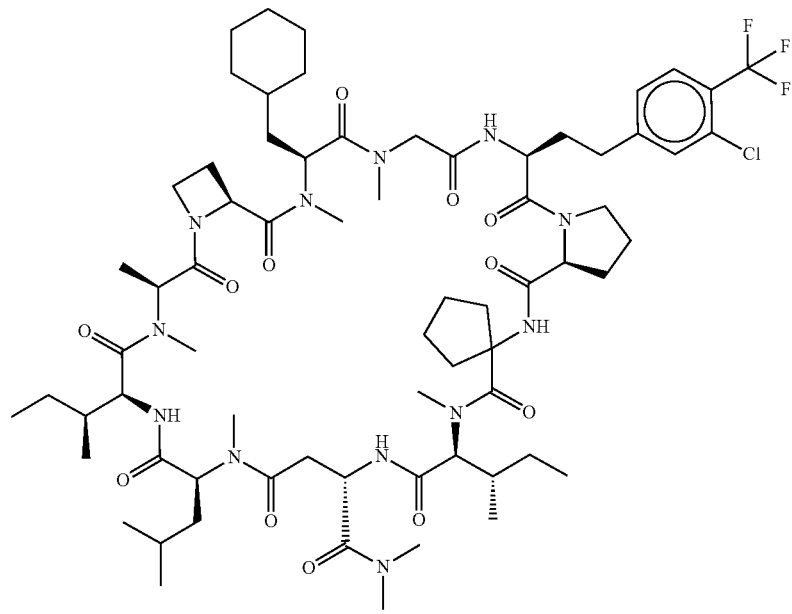 |
| 569 | 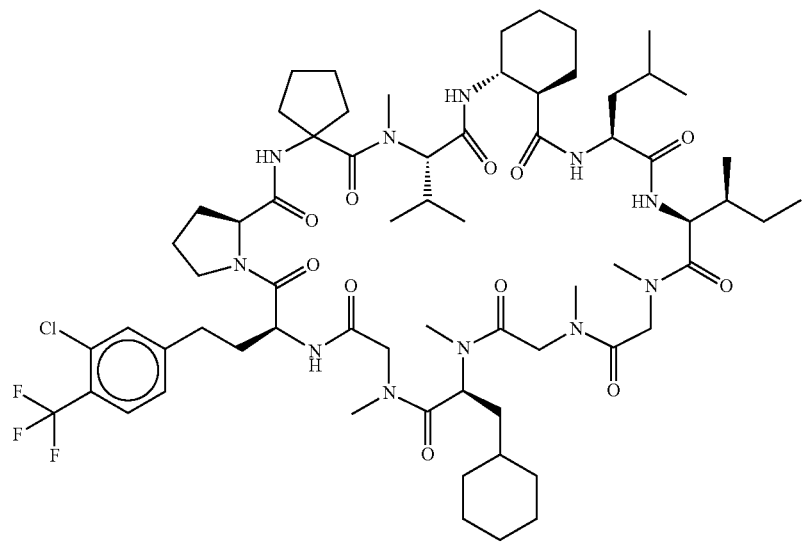 |

TABLE 24-continued
| Compound No. | Structural formula |
|---|---|
| 570 | 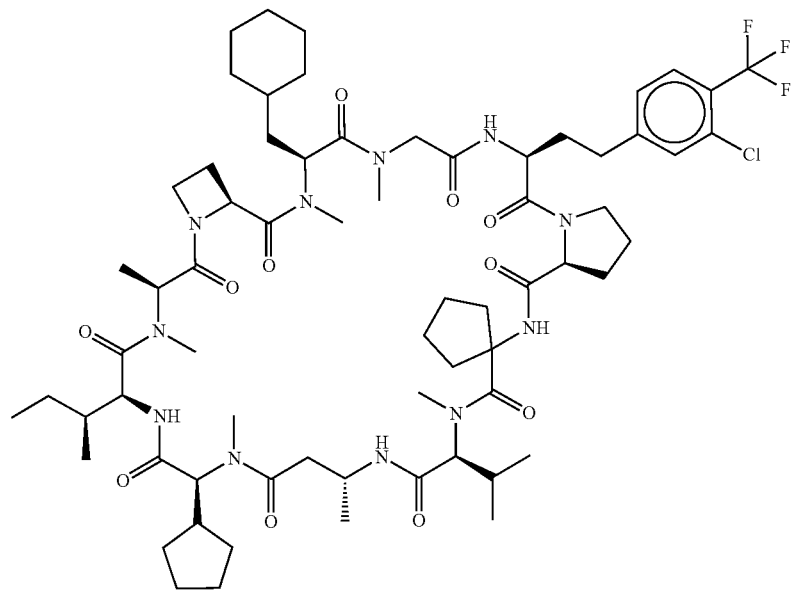 |
| 571 | 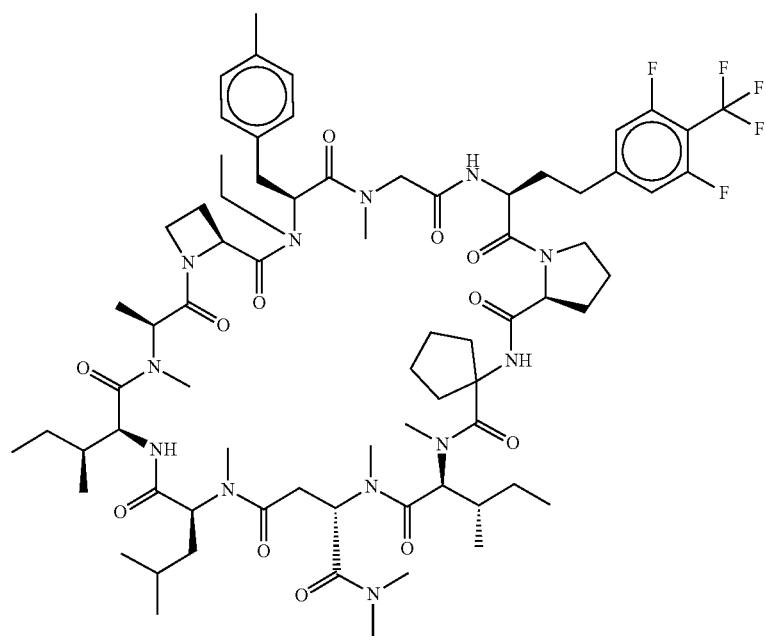 |

TABLE 24-continued
| Compound No. | Structural formula |
|---|---|
| 572 | 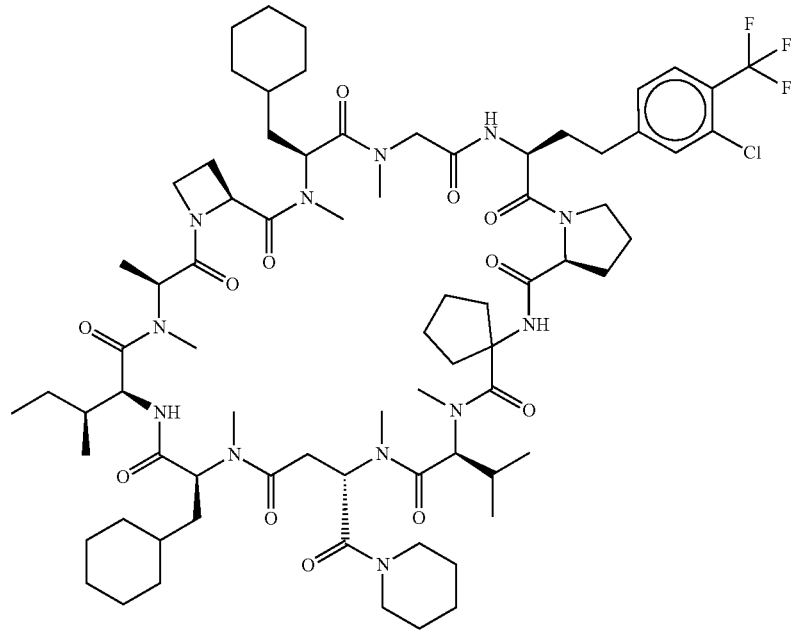 |
| 573 | 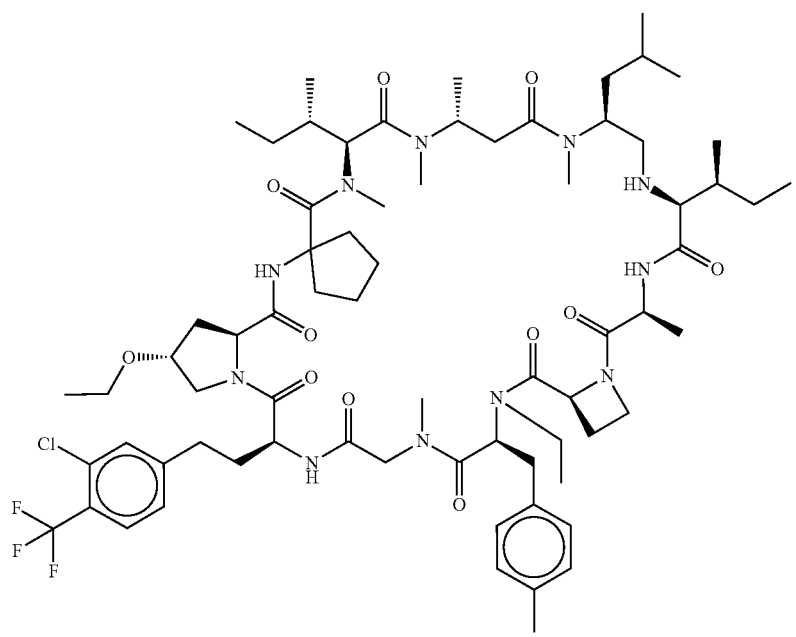 |

TABLE 24-continued
| Compound No. | Structural formula |
|---|---|
| 574 | 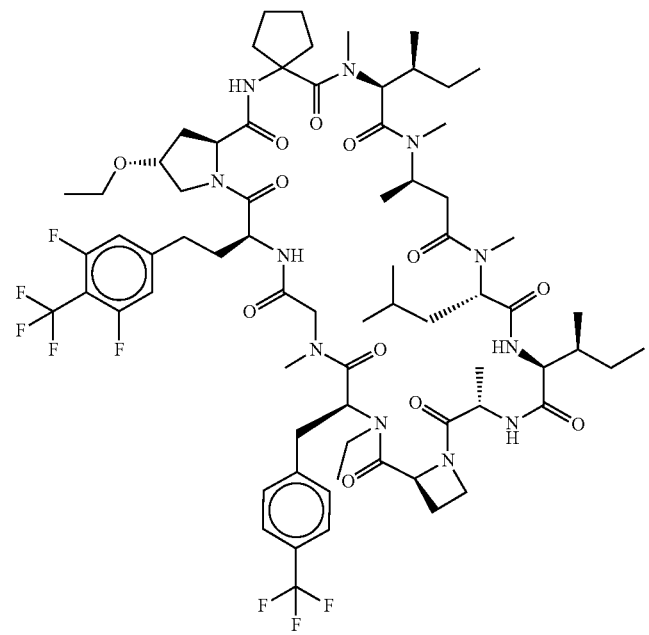 |
| 575 | 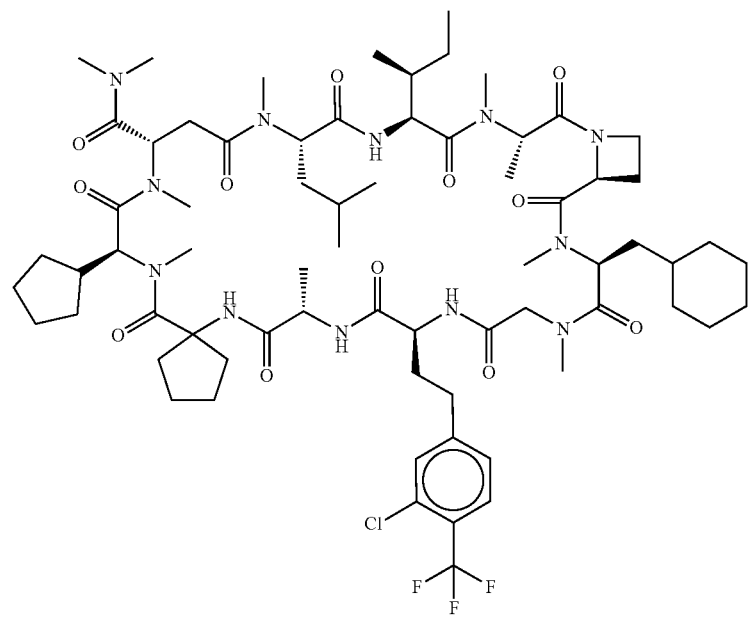 |

TABLE 24-continued
| Compound No. | Structural formula |
|---|---|
| 576 | 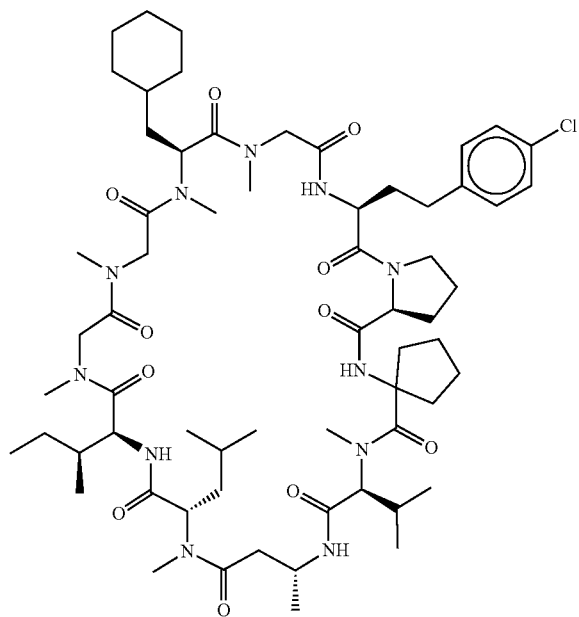 |
| 577 | 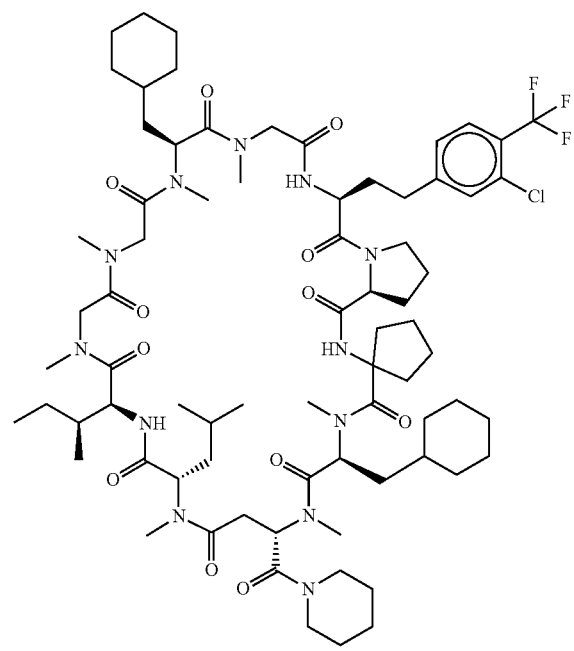 |

TABLE 24-continued
| Compound No. | Structural formula |
|---|---|
| 578 | 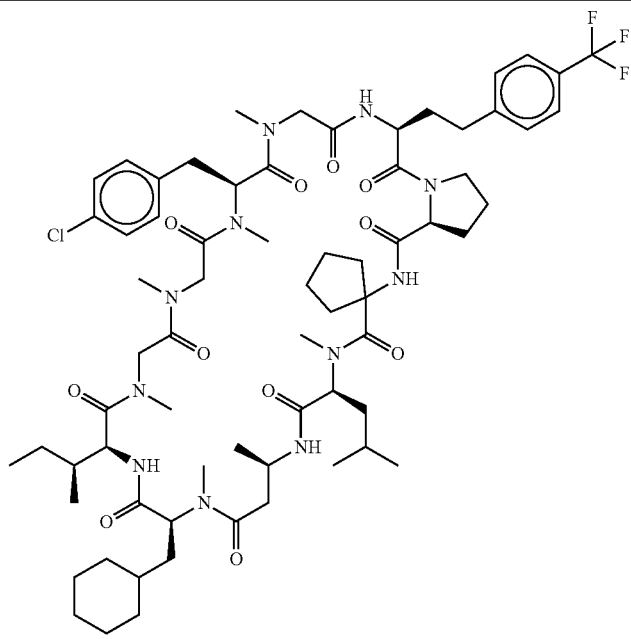 |
| 579 | 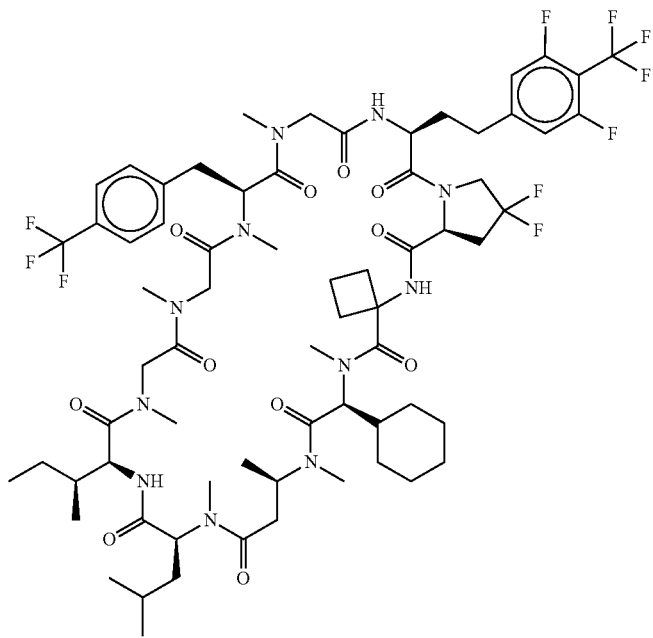 |

TABLE 24-continued
| Compound No. | Structural formula |
|---|---|
| 580 | 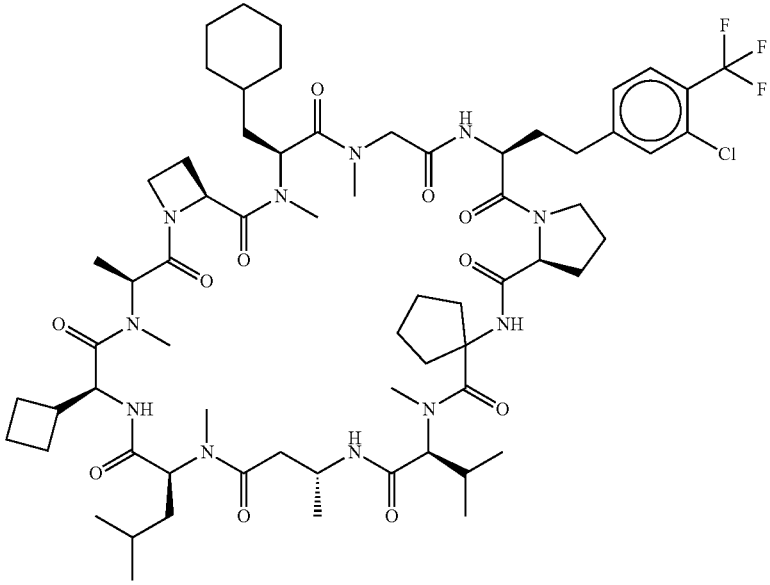 |
| 581 | 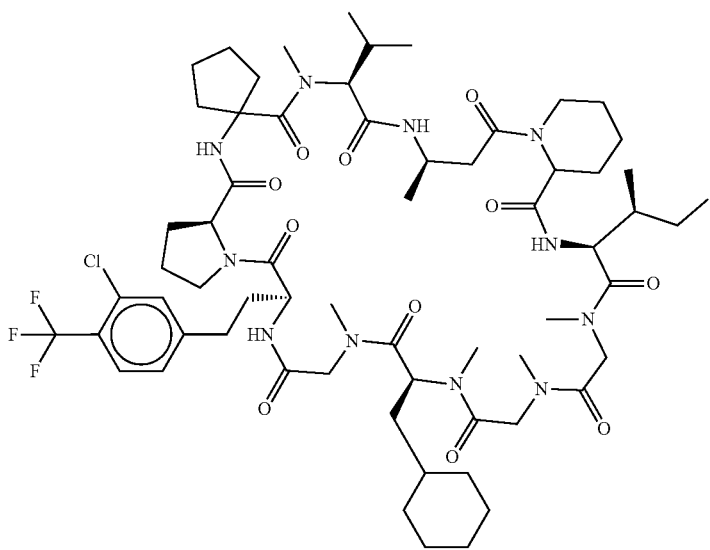 |

TABLE 24-continued
| Compound No. | Structural formula |
|---|---|
| 582 | 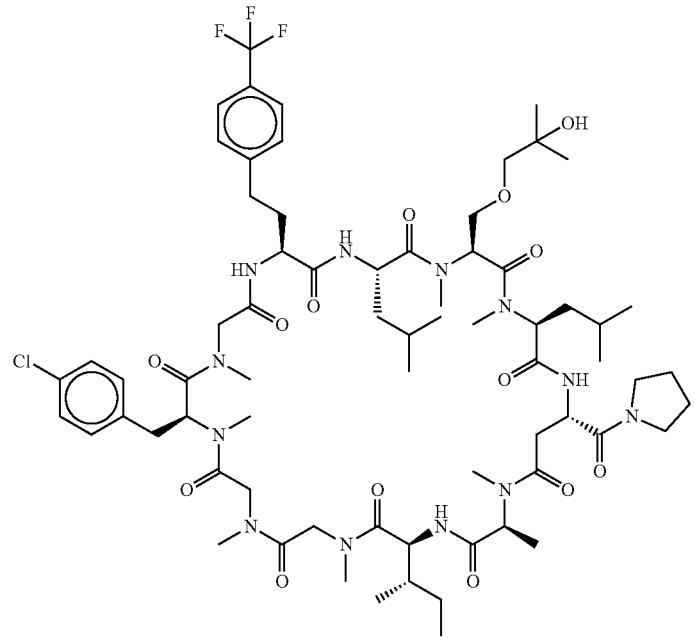 |
| 583 | 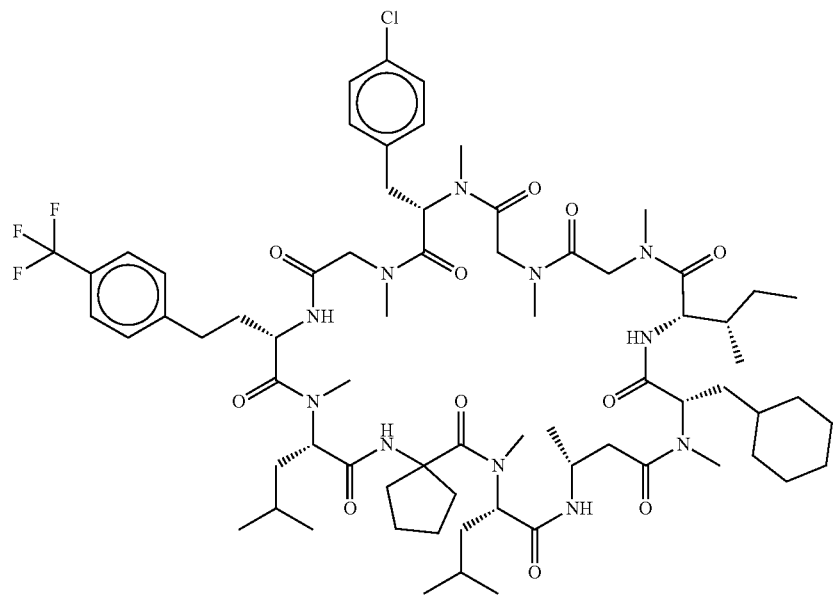 |

TABLE 24-continued
| Compound No. | Structural formula |
|---|---|
| 584 | 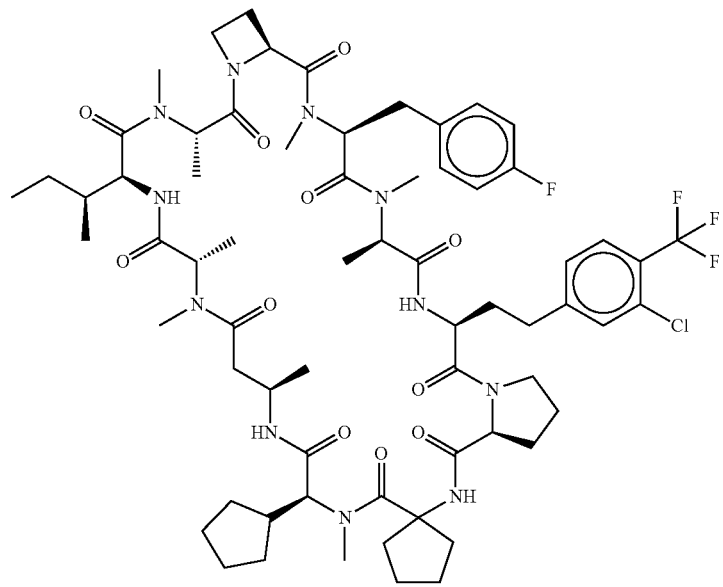 |
| 585 | 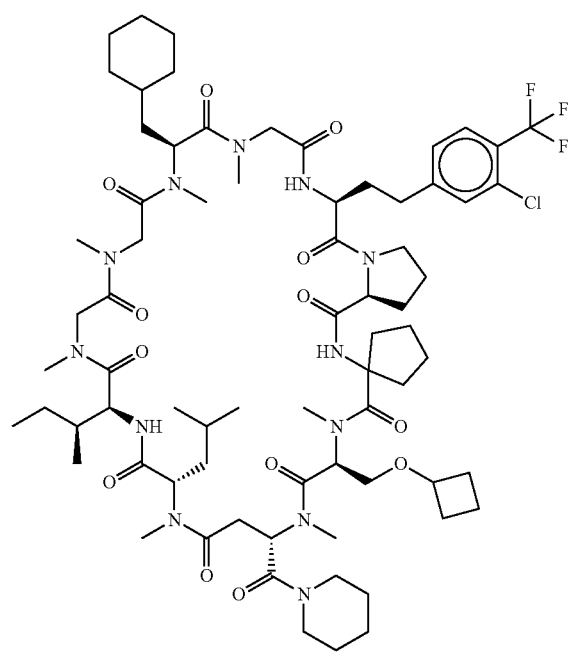 |

TABLE 24-continued
| Compound No. | Structural formula |
|---|---|
| 586 | 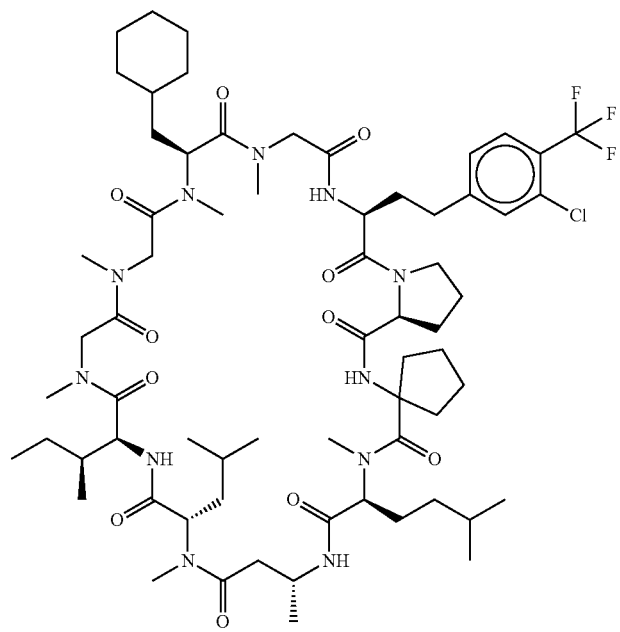 |
| 587 | 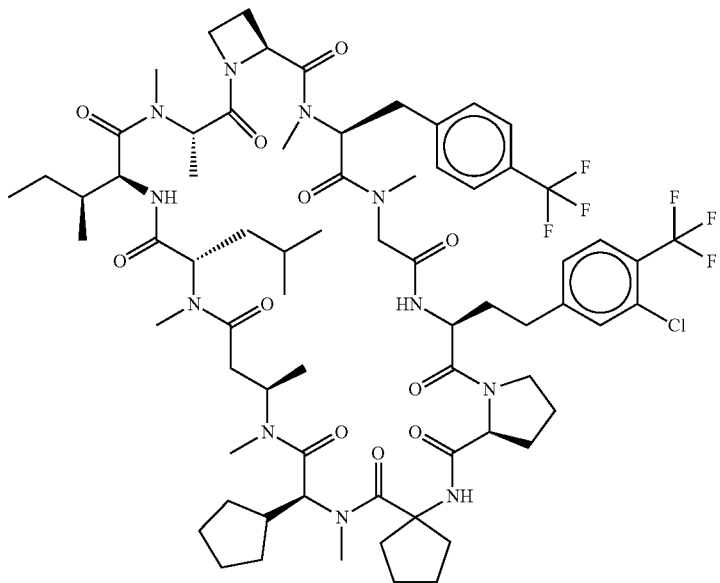 |

TABLE 24-continued
| Compound No. | Structural formula |
|---|---|
| 588 | 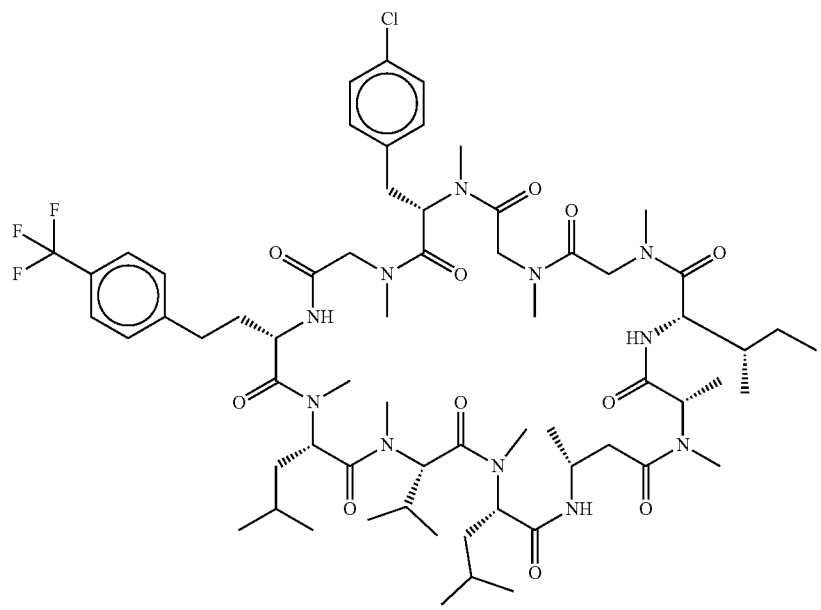 |
| 589 | 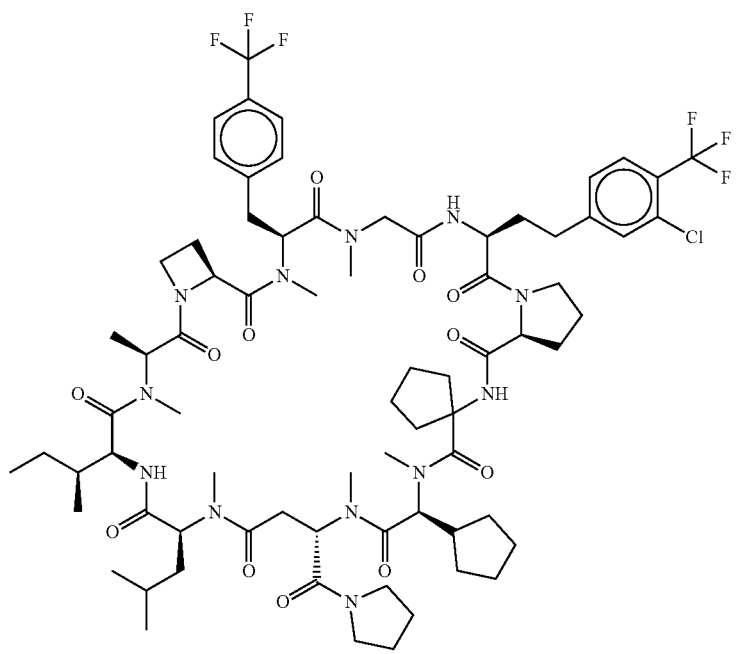 |

TABLE 24-continued
| Compound No. | Structural formula |
|---|---|
| 590 | 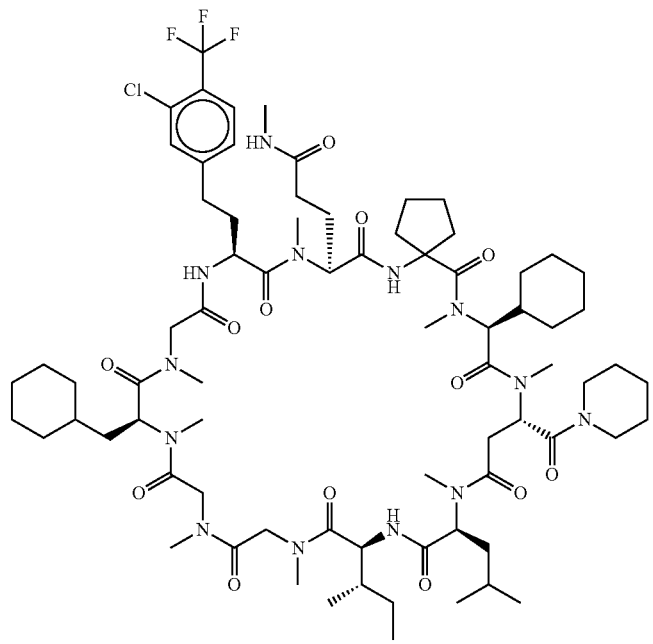 |
| 591 | 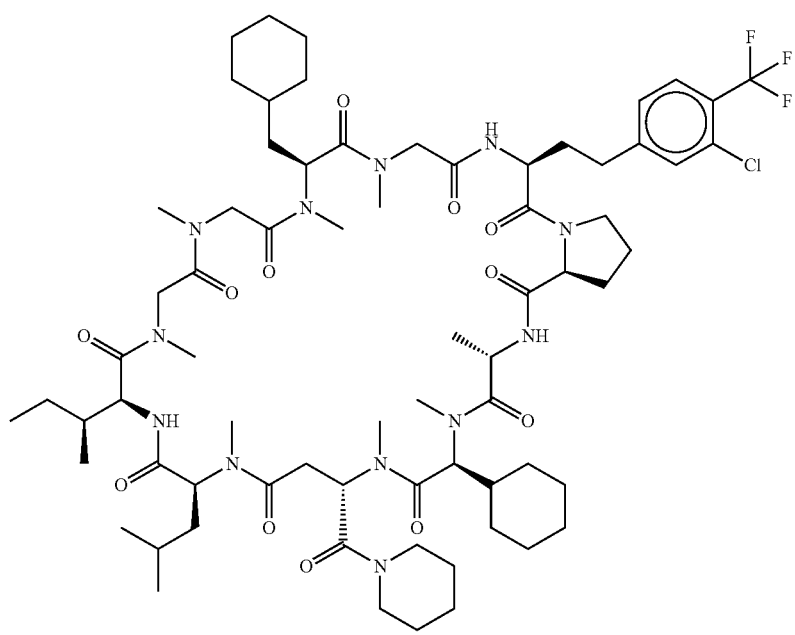 |

| Compound No. | Structural formula |
|---|---|
| 592 | 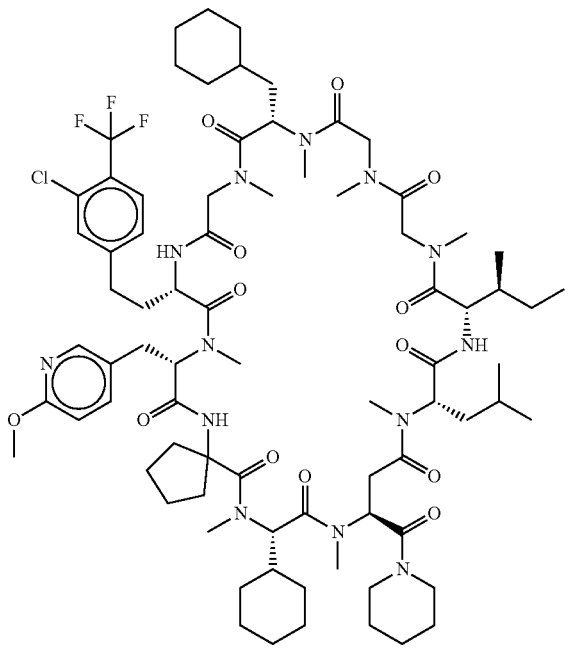 |
| 593 | 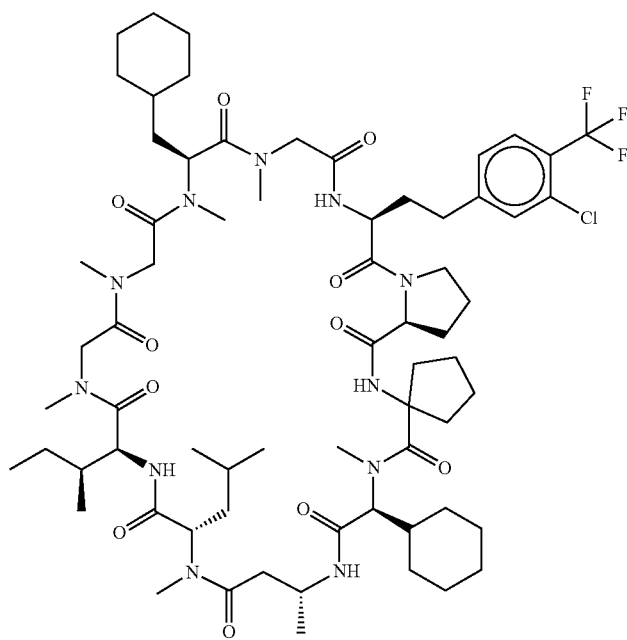 |

TABLE 24-continued
| Compound No. | Structural formula |
|---|---|
| 594 | 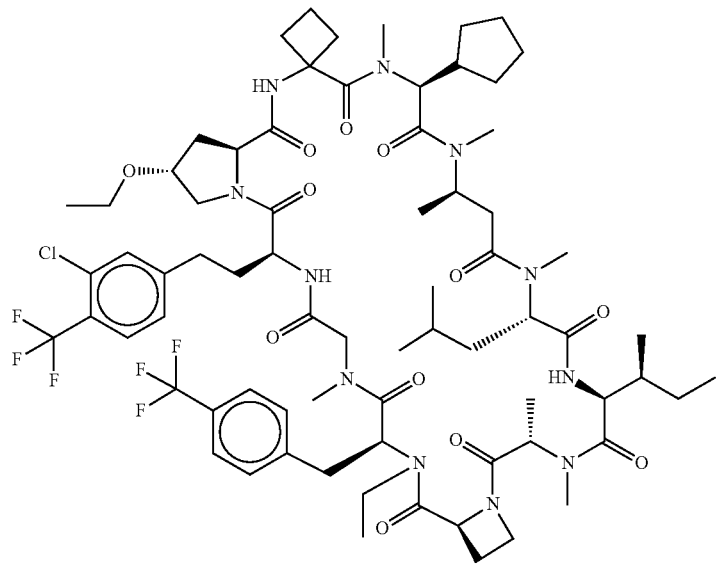 |
| 595 | 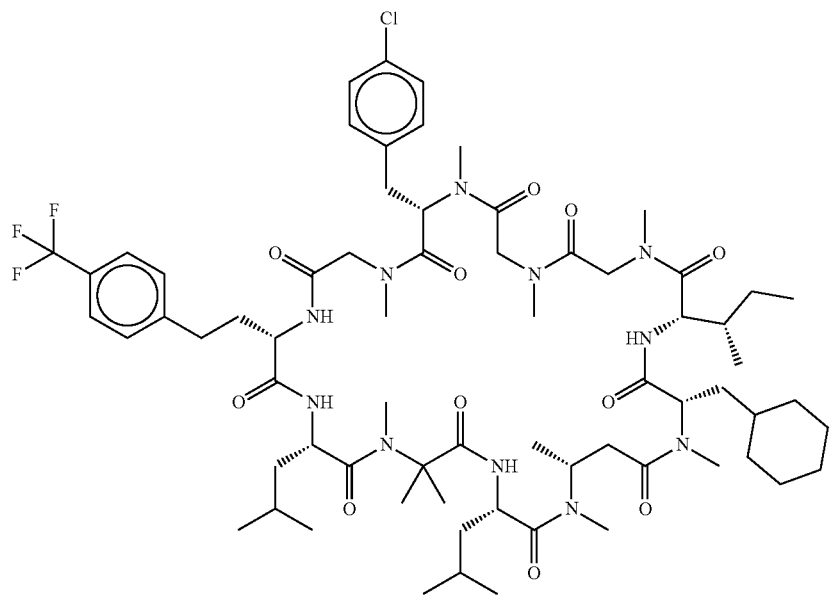 |

TABLE 24-continued
| Compound No. | Structural formula |
|---|---|
| 596 | 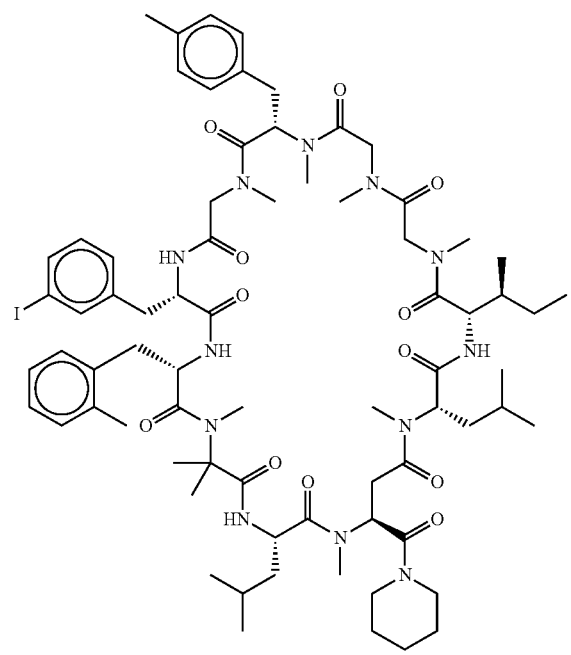 |
| 597 | 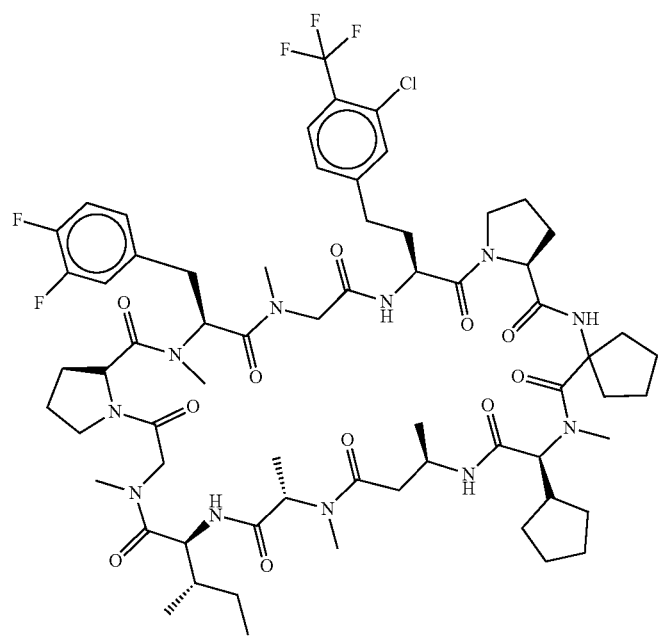 |

TABLE 24-continued
| Compound No. | Structural formula |
|---|---|
| 598 | 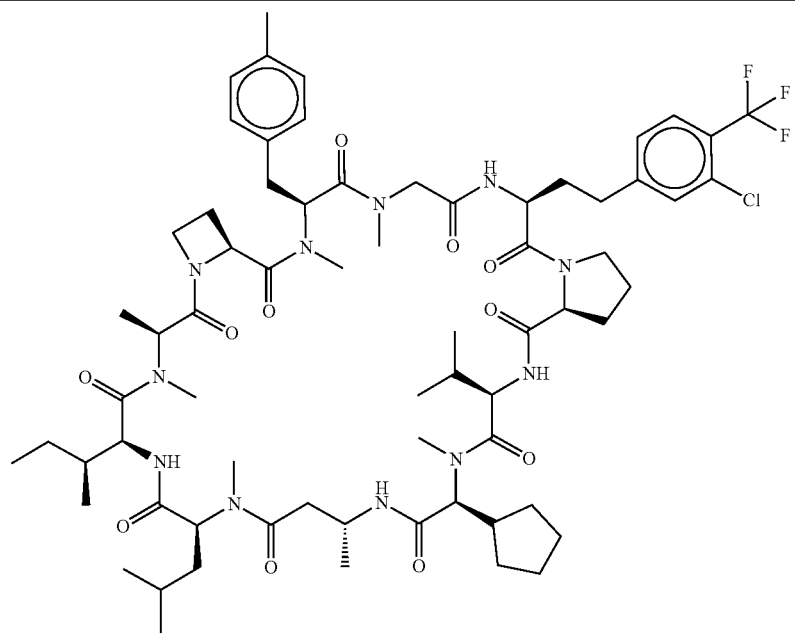 |
| 599 | 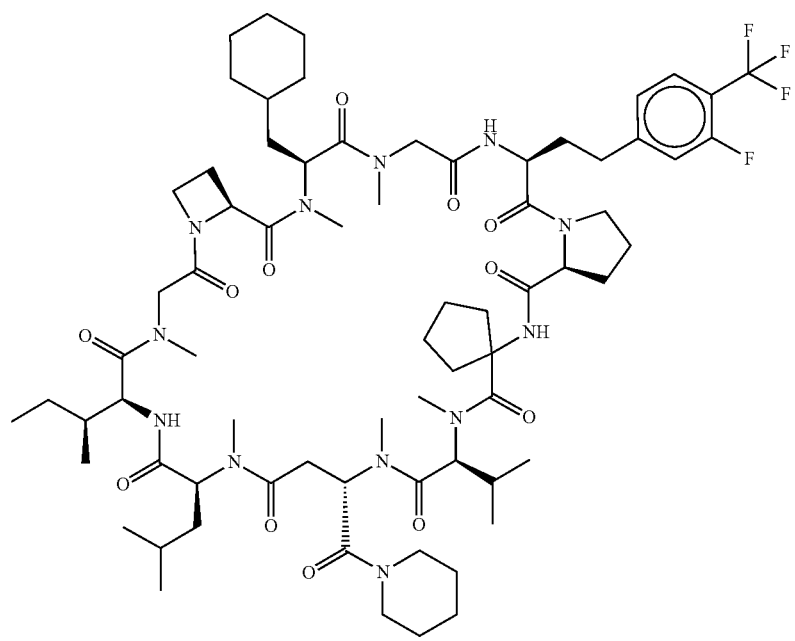 |

TABLE 24-continued
| Compound No. | Structural formula |
|---|---|
| 600 | 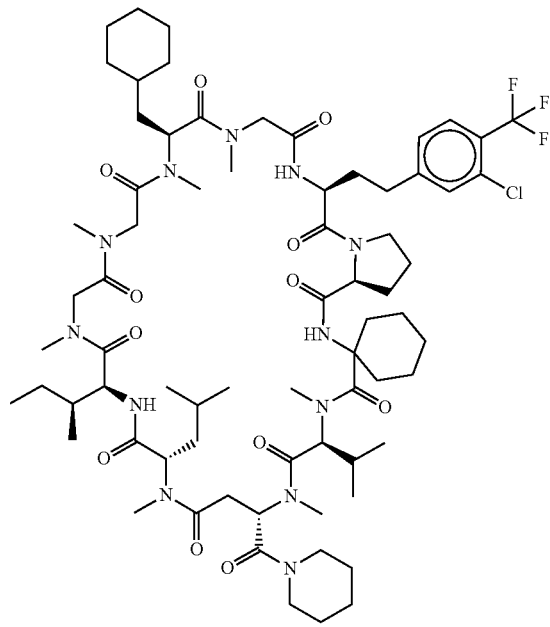 |
| 601 | 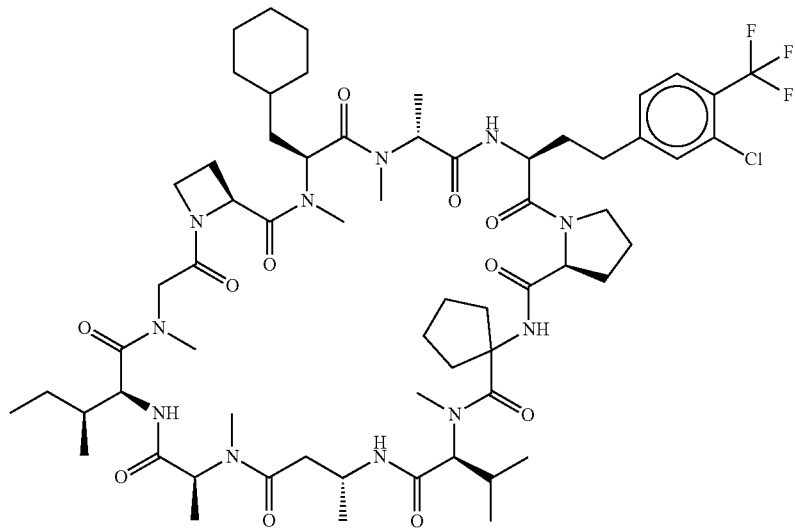 |

TABLE 24-continued
| Compound No. | Structural formula |
|---|---|
| 602 | 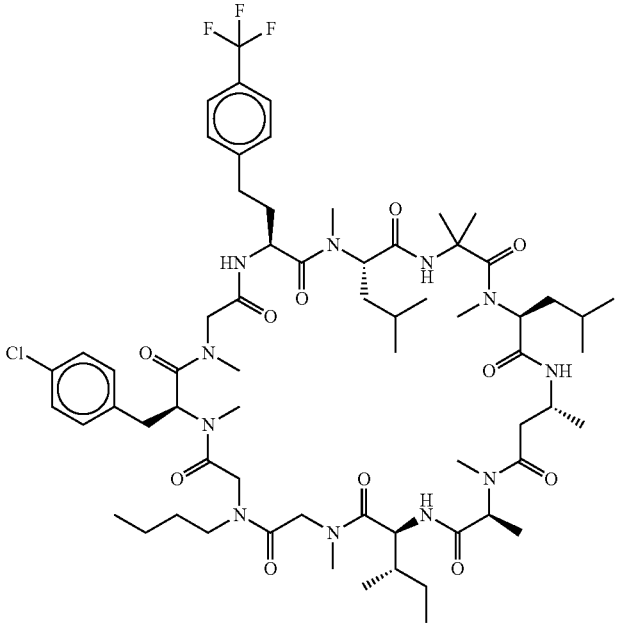 |
| 603 | 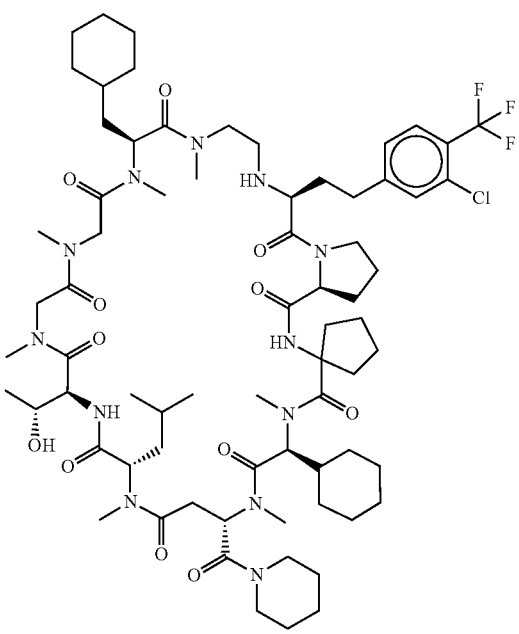 |

TABLE 24-continued
| Compound No. | Structural formula |
|---|---|
| 604 | 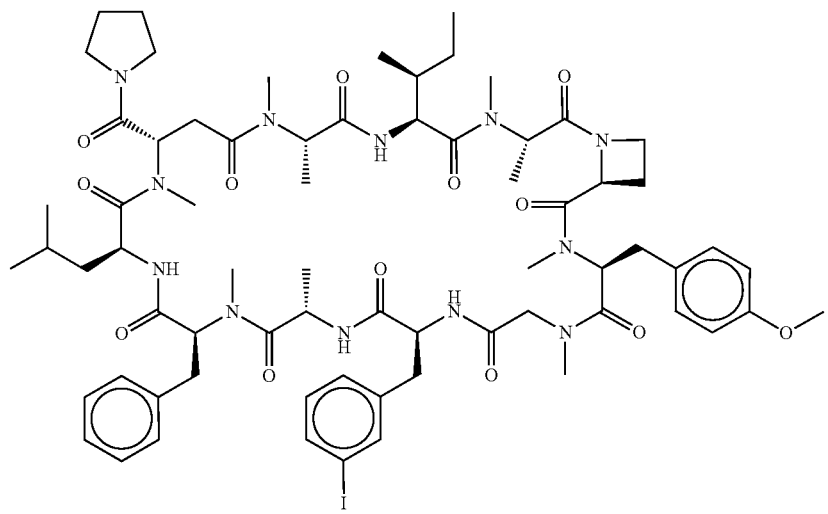 |
| 605 | 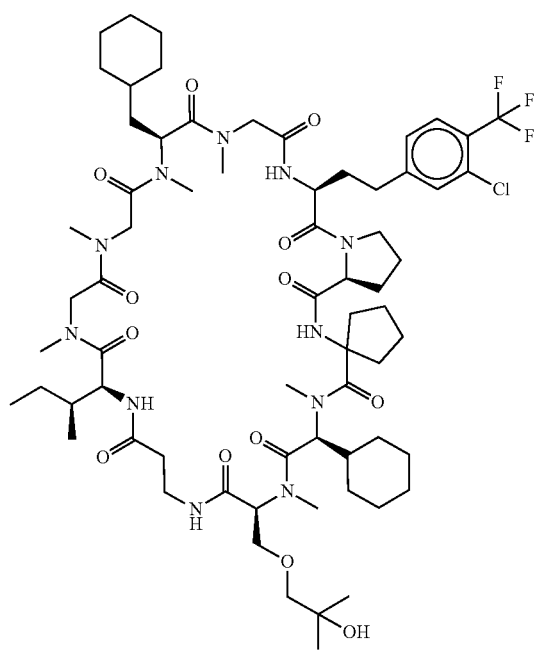 |

TABLE 24-continued
| Compound No. | Structural formula |
|---|---|
| 606 | 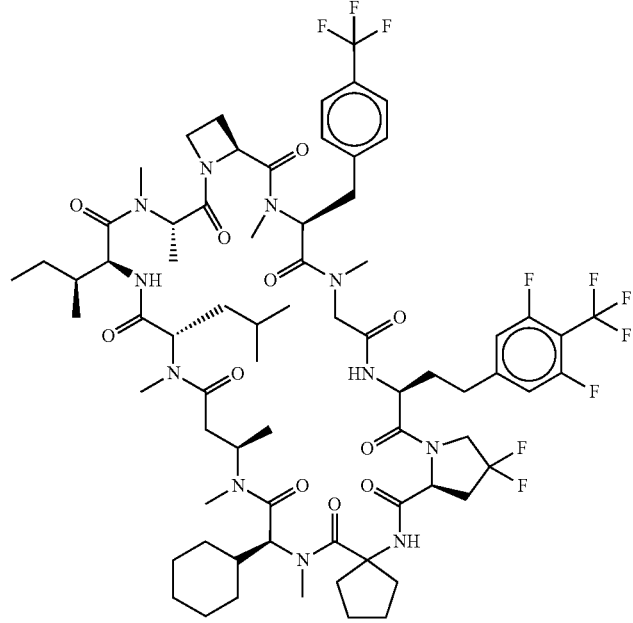 |
| 607 | 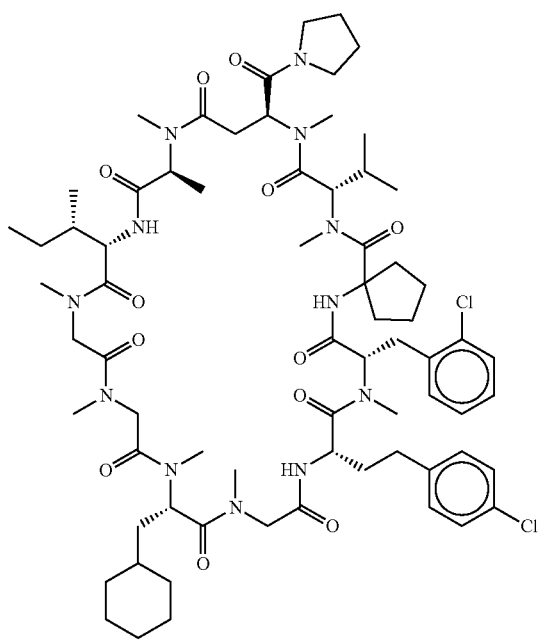 |

TABLE 24-continued
| Compound No. | Structural formula |
|---|---|
| 608 | 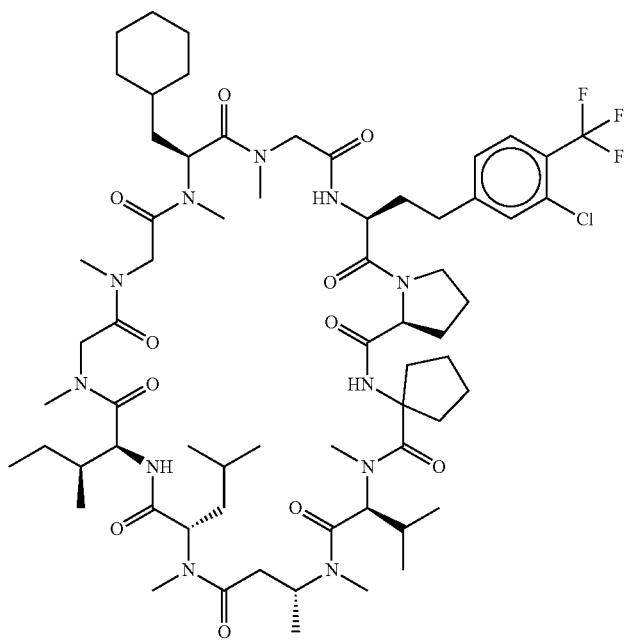 |
| 609 | 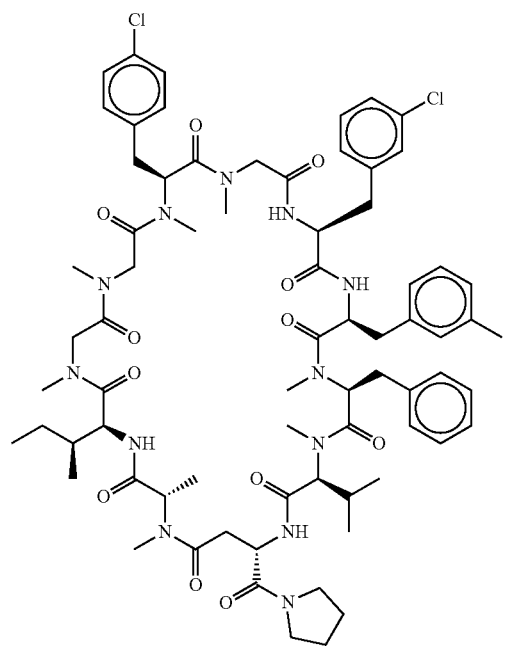 |

TABLE 24-continued
| Compound No. | Structural formula |
|---|---|
| 610 | 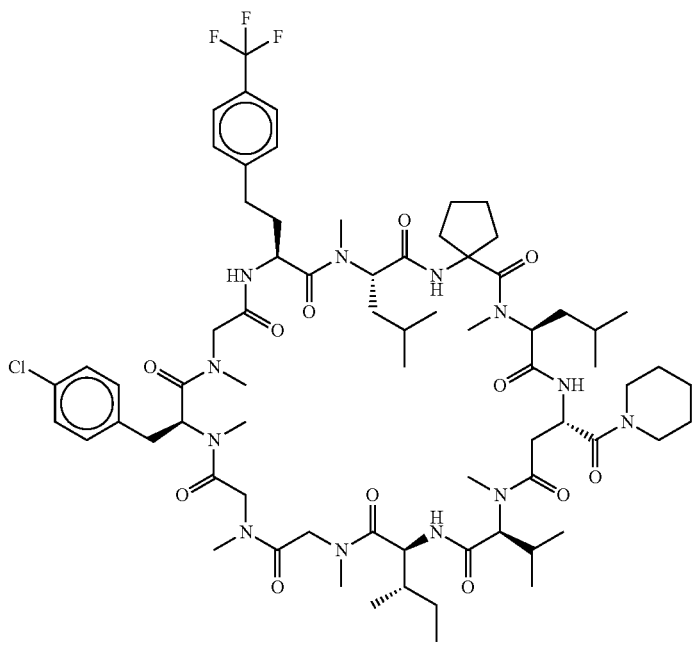 |
| 611 | 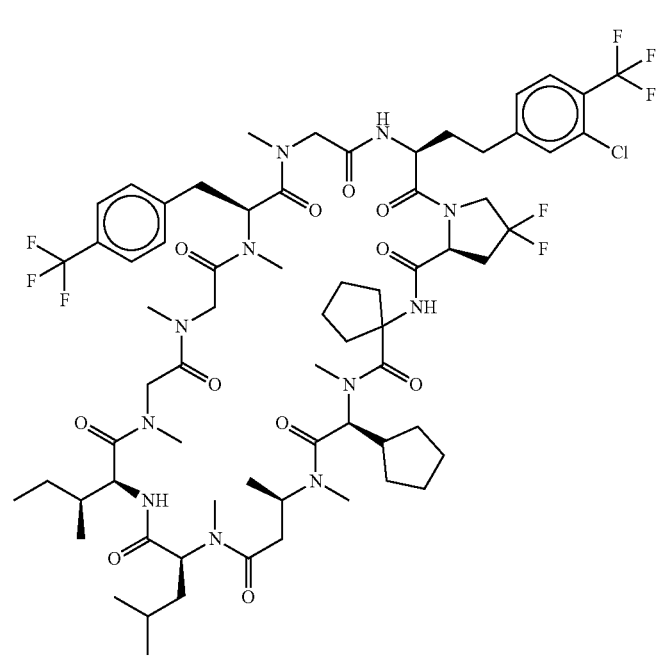 |

TABLE 24-continued
| Compound No. | Structural formula |
|---|---|
| 612 | 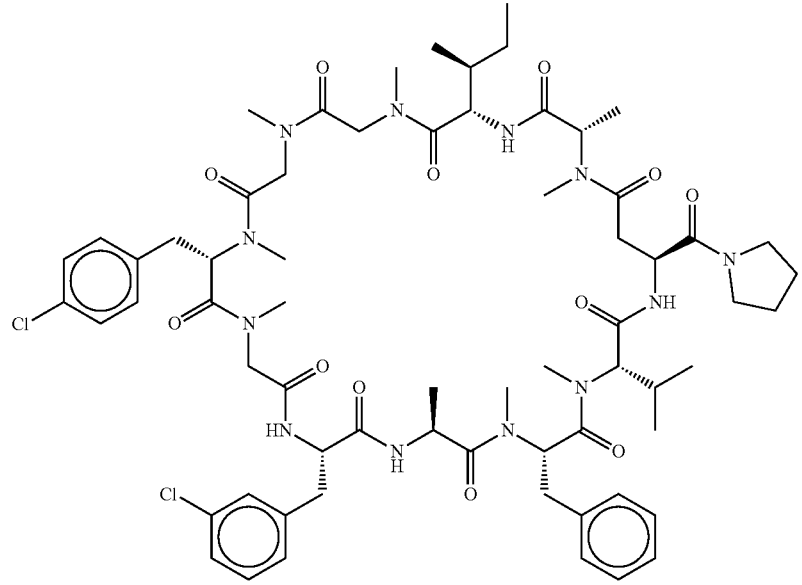 |
| 613 | 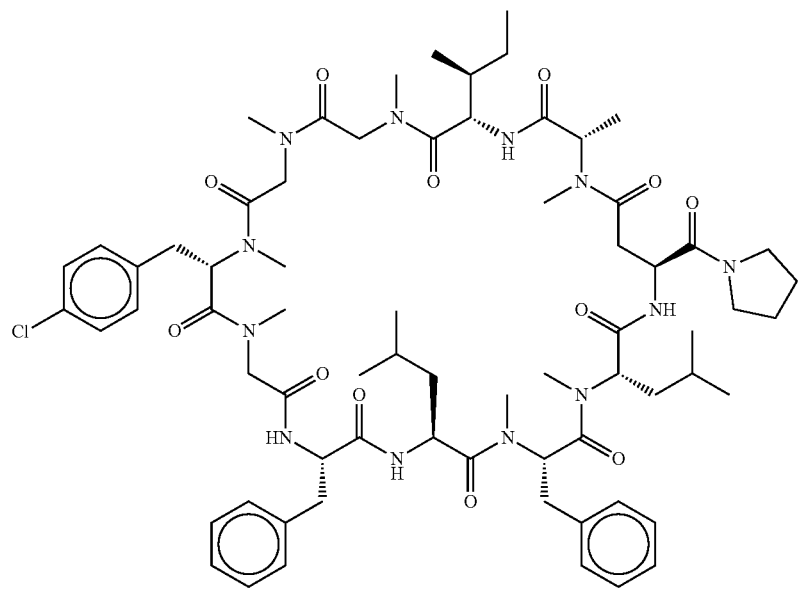 |

TABLE 24-continued
| Compound No. | Structural formula |
|---|---|
| 614 | 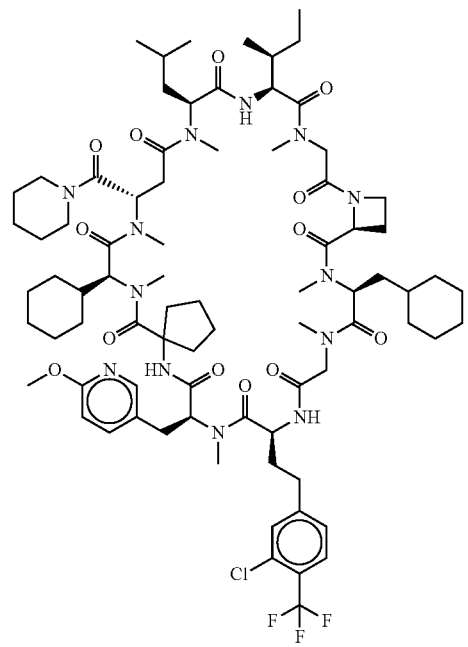 |
| 615 | 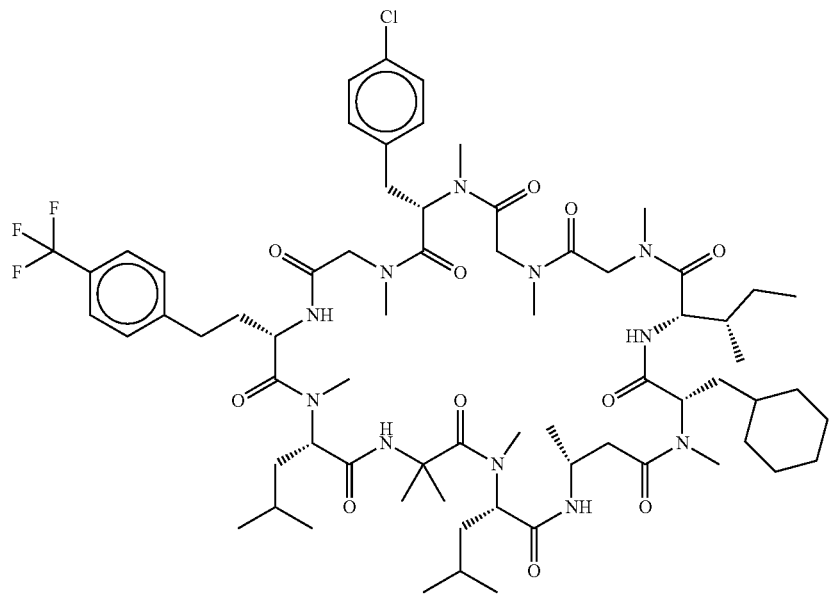 |

TABLE 24-continued
| Compound No. | Structural formula |
|---|---|
| 616 | 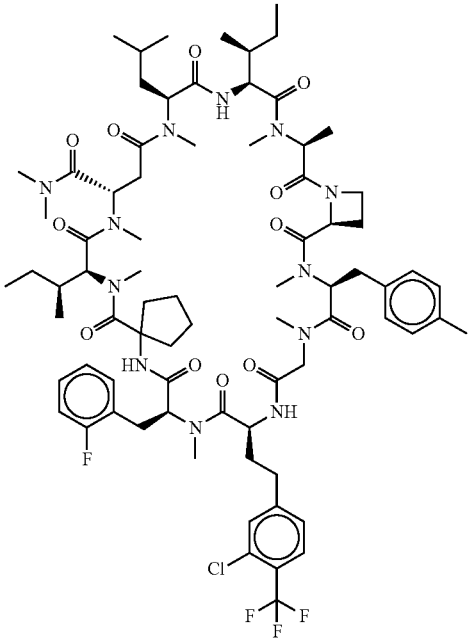 |
| 617 | 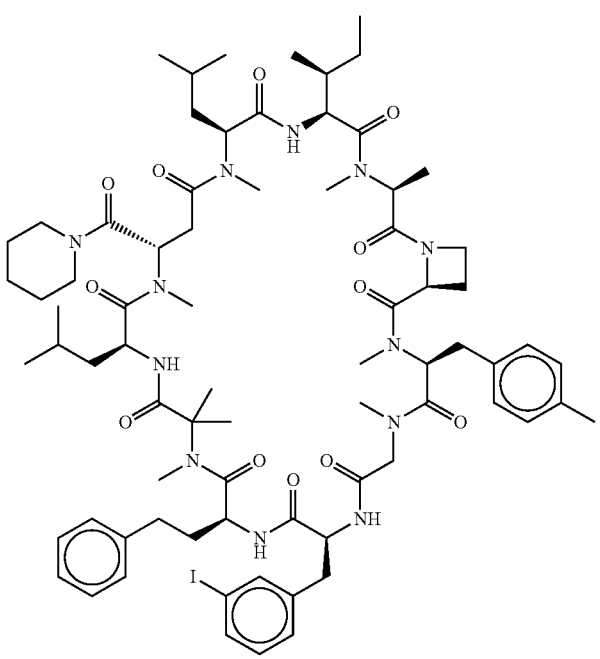 |

TABLE 24-continued
| Compound No. | Structural formula |
|---|---|
| 618 | 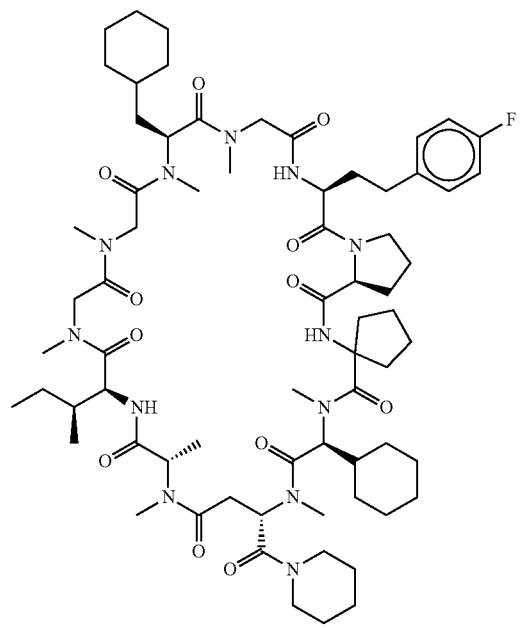 |
| 619 | 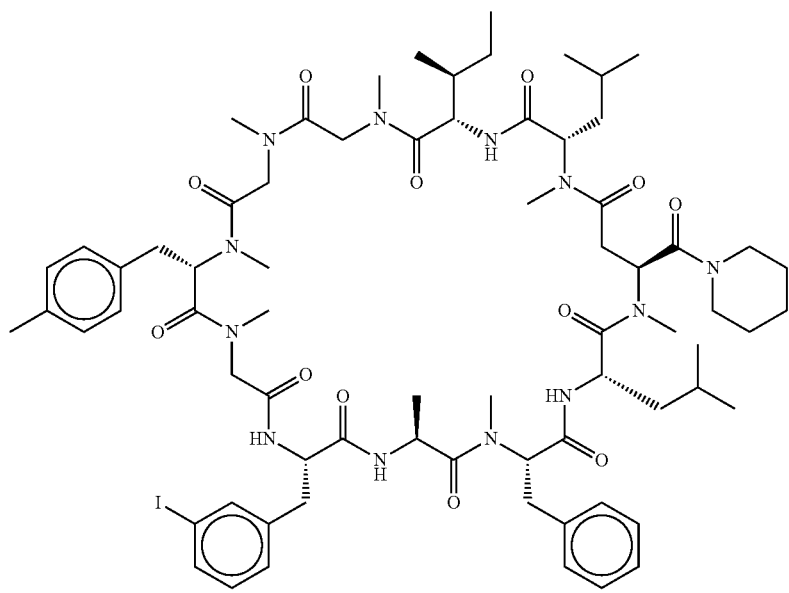 |

TABLE 24-continued
| Compound No. | Structural formula |
|---|---|
| 620 | 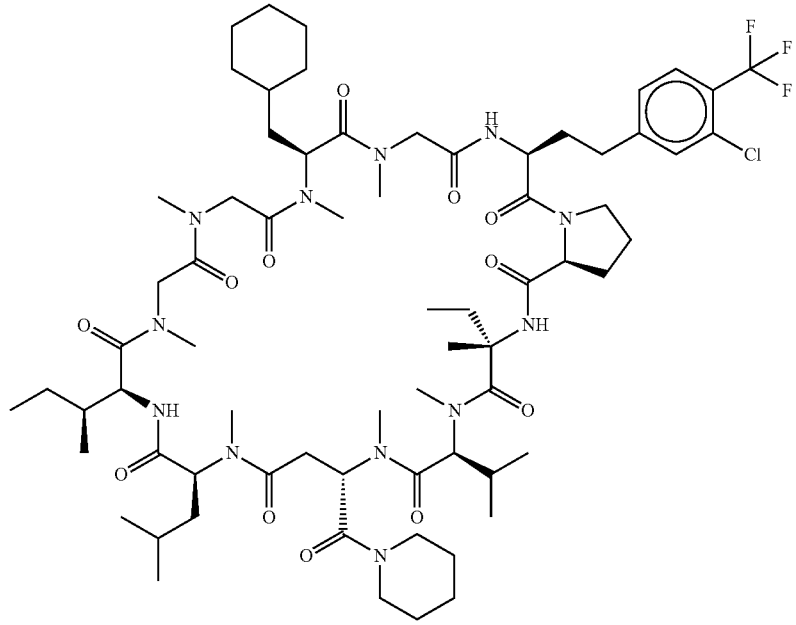 |
| 621 | 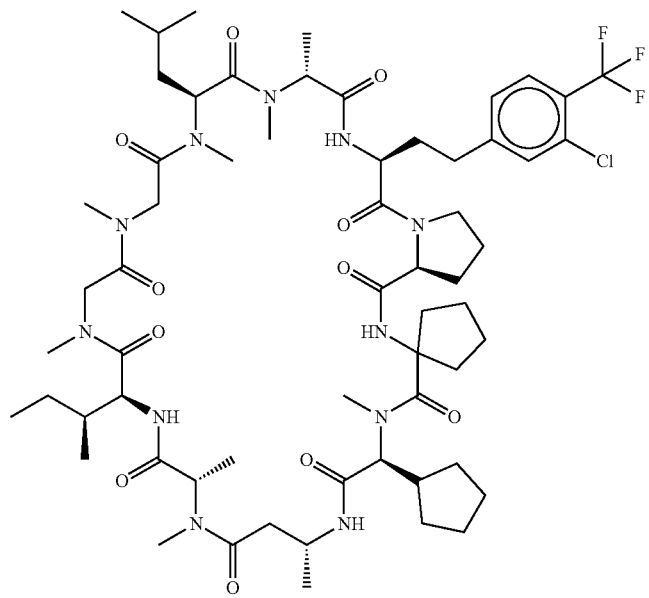 |

TABLE 24-continued
| Compound No. | Structural formula |
|---|---|
| 622 | 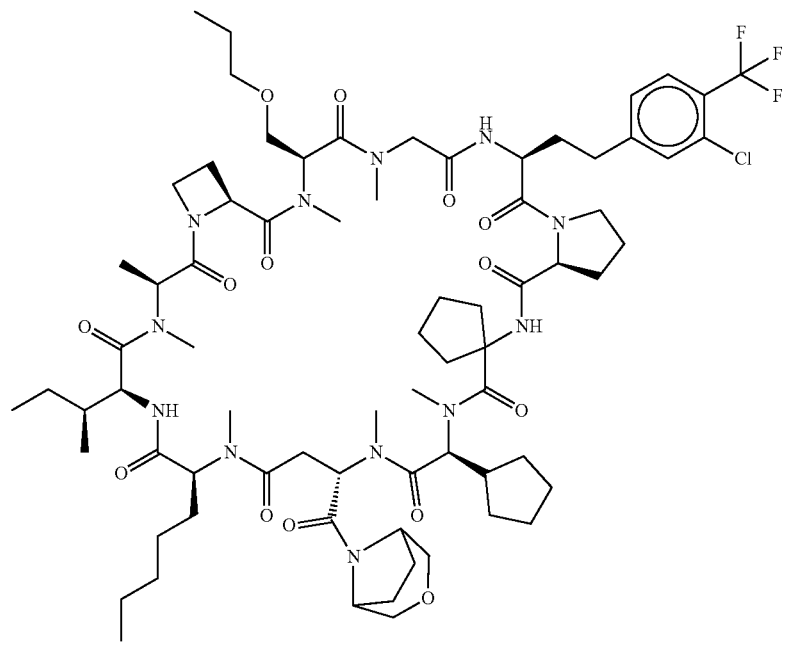 |
| 623 | 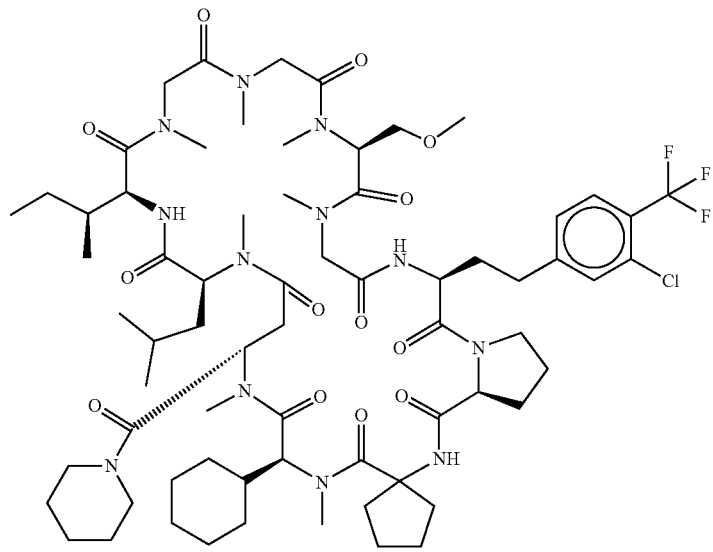 |

TABLE 24-continued
| Compound No. | Structural formula |
|---|---|
| 624 | 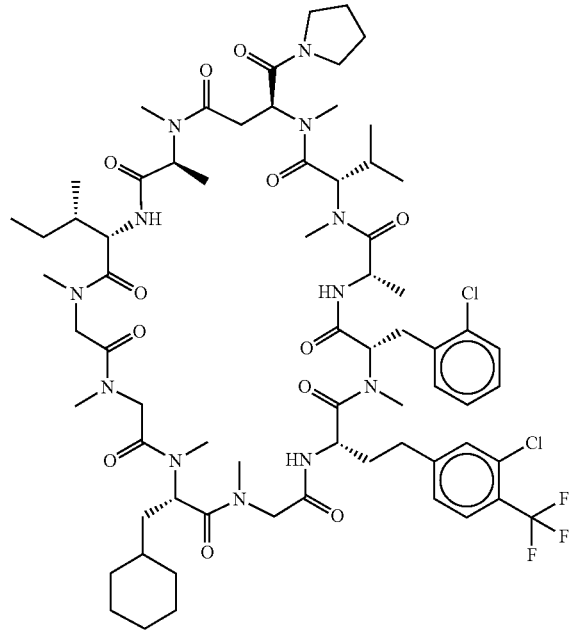 |
| 625 | 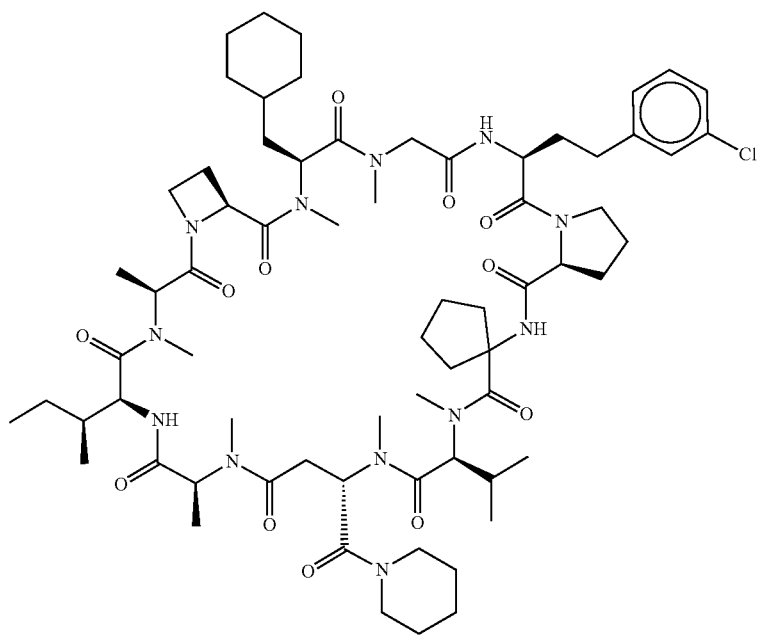 |

TABLE 24-continued
| Compound No. | Structural formula |
|---|---|
| 626 | 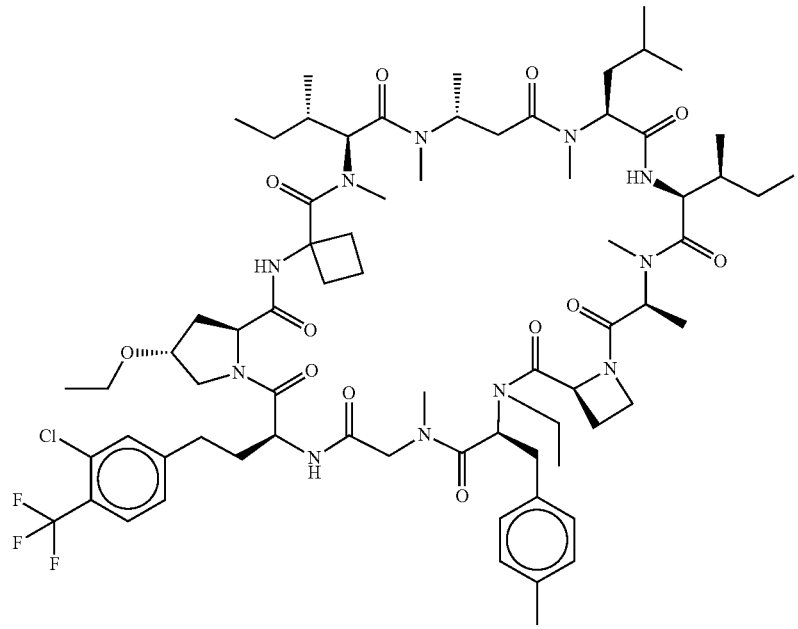 |
| 627 | 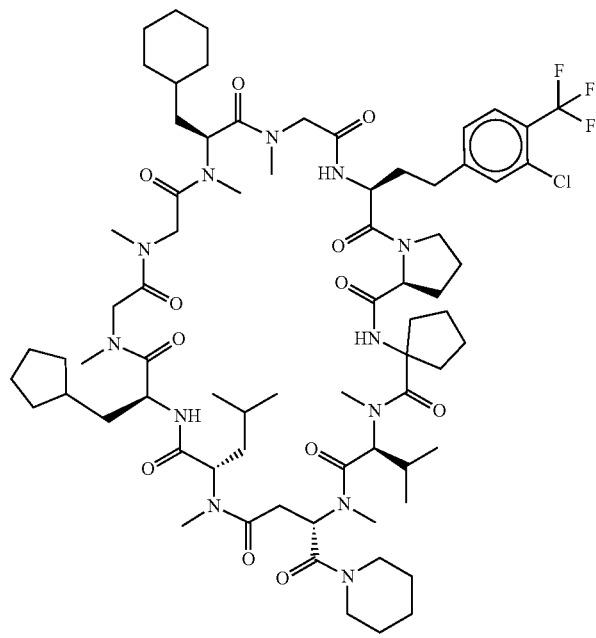 |

TABLE 24-continued
| Compound No. | Structural formula |
|---|---|
| 628 | 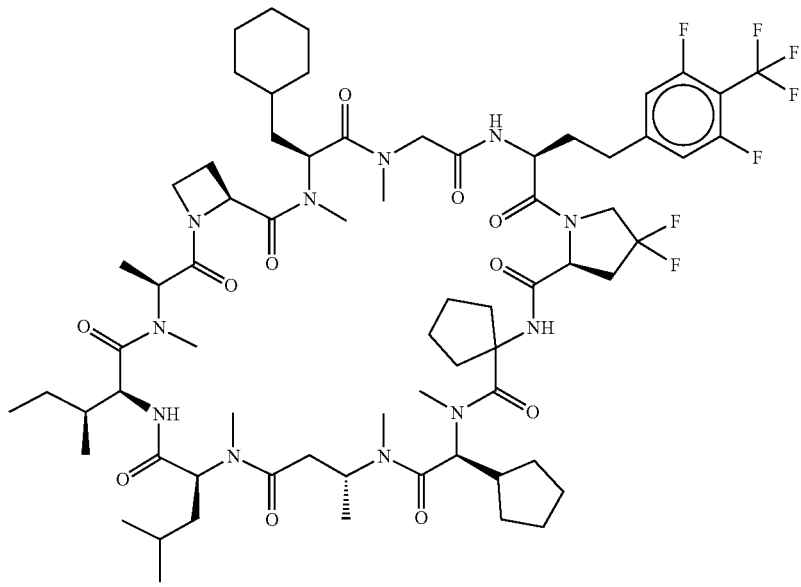 |
| 629 | 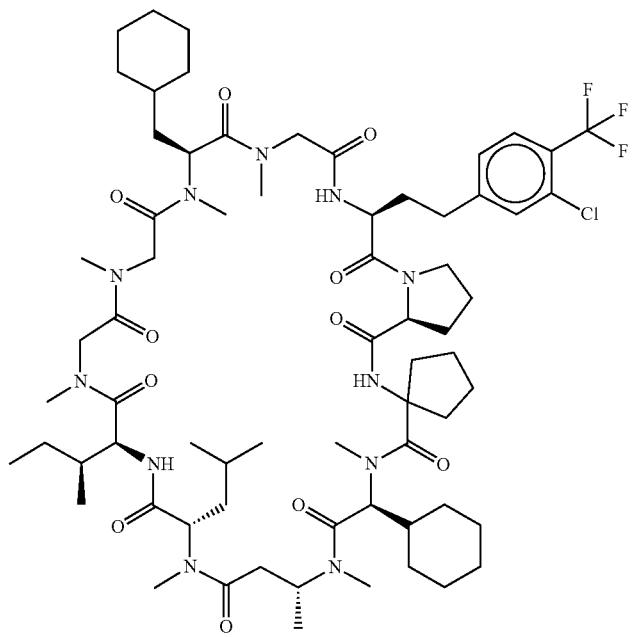 |

TABLE 24-continued
| Compound No. | Structural formula |
|---|---|
| 630 | 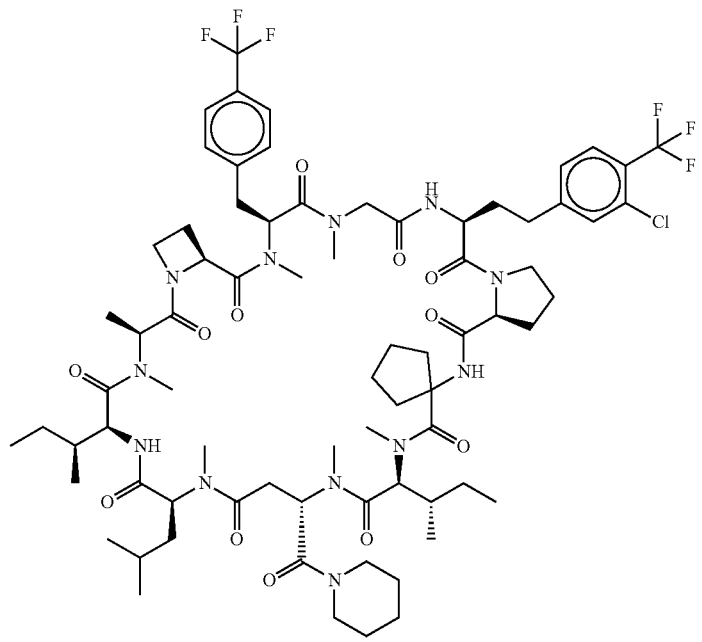 |
| 631 | 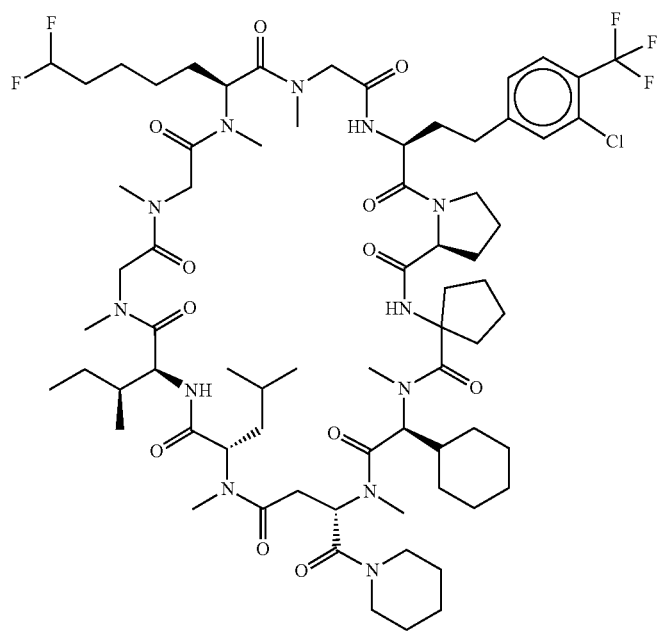 |

| Compound No. | Structural formula |
|---|---|
| 632 | 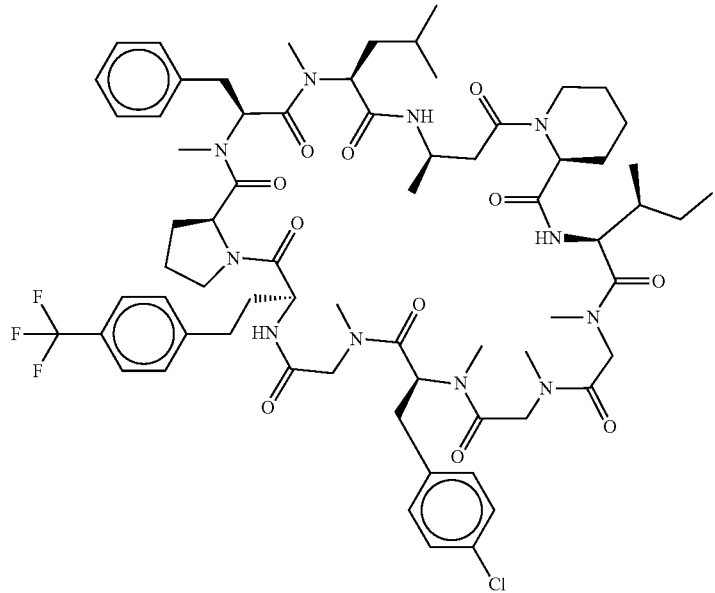 |
| 633 | 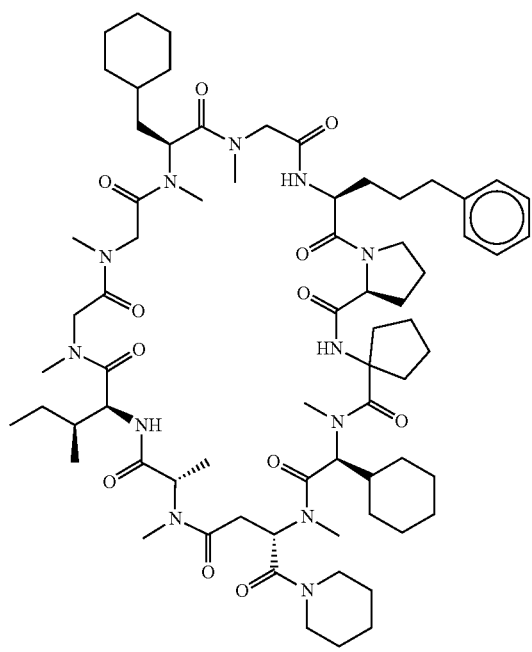 |

TABLE 24-continued
| Compound No. | Structural formula |
|---|---|
| 634 | 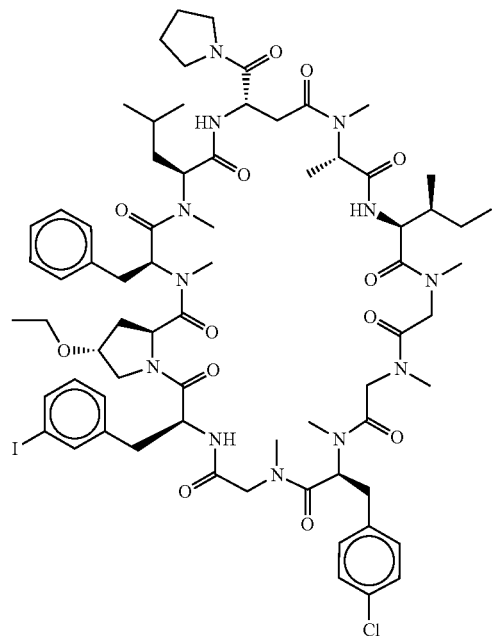 |
| 635 | 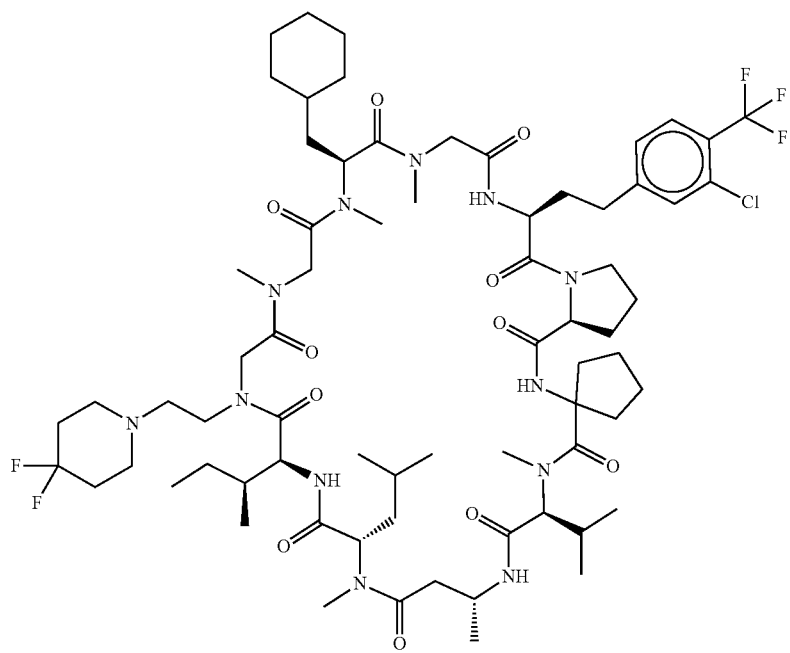 |

TABLE 24-continued
| Compound No. | Structural formula |
|---|---|
| 636 | 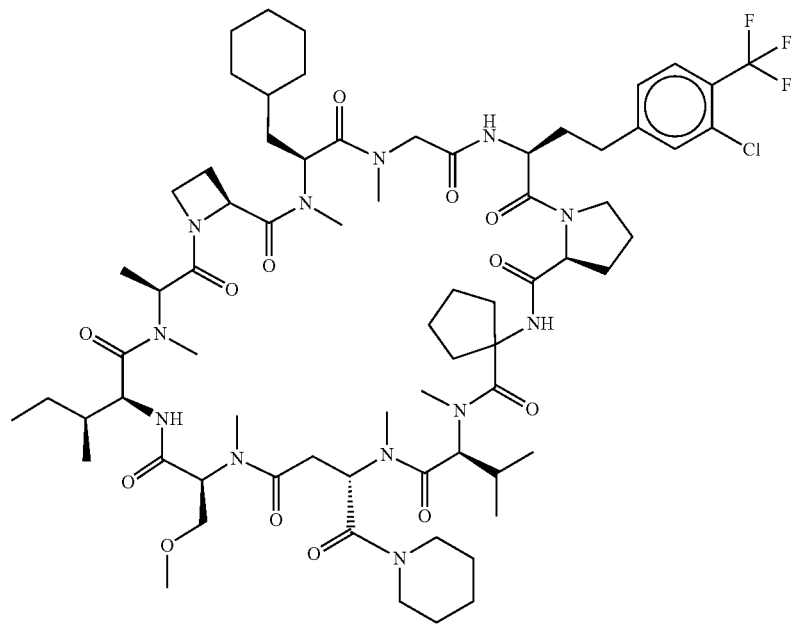 |
| 637 | 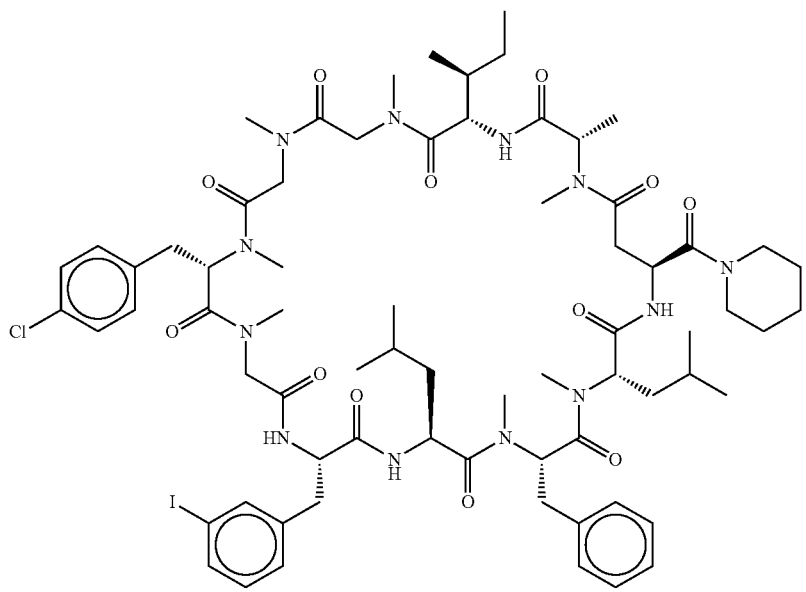 |

TABLE 24-continued
| Compound No. | Structural formula |
|---|---|
| 638 | 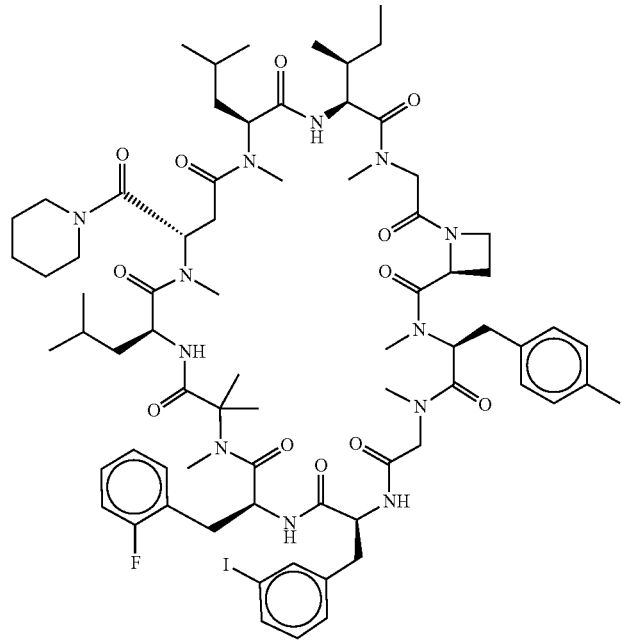 |
| 639 | 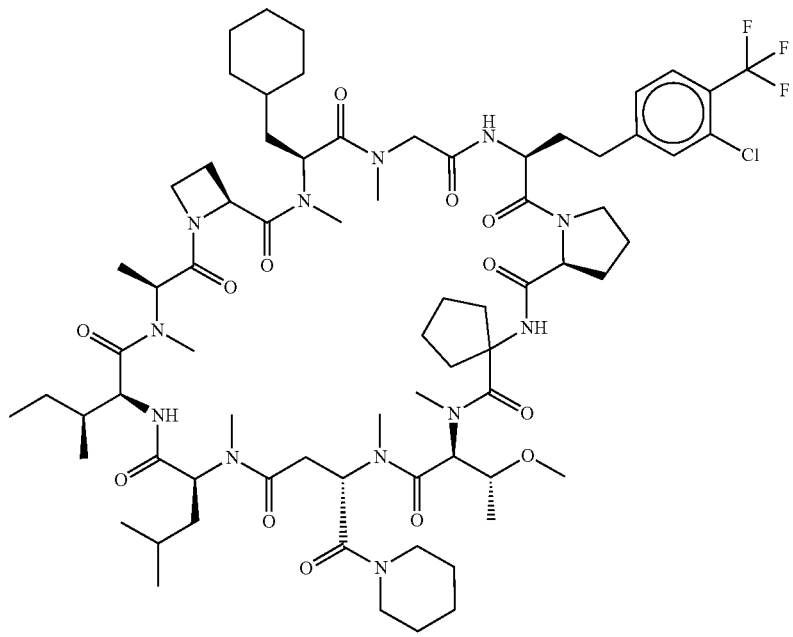 |

TABLE 24-continued
| Compound No. | Structural formula |
|---|---|
| 640 | 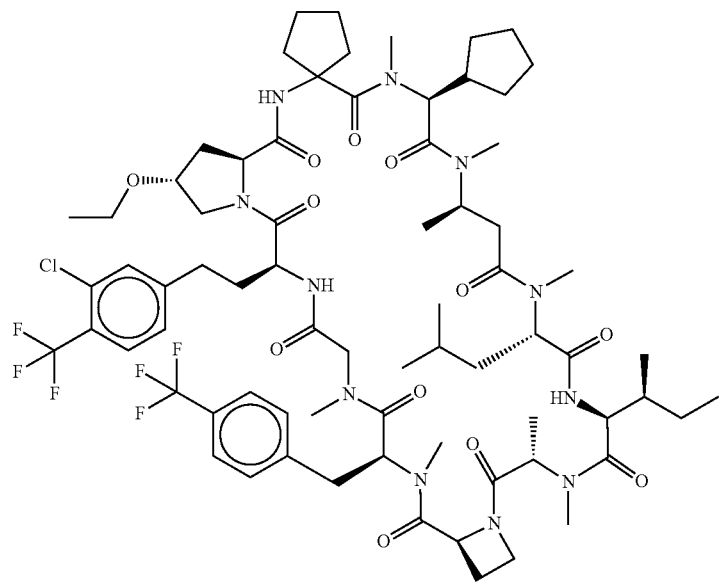 |
| 641 | 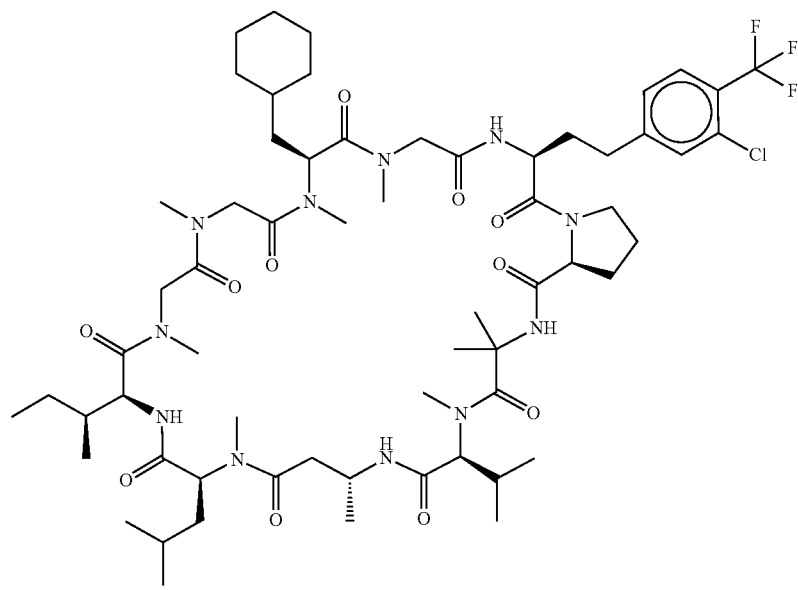 |

TABLE 24-continued
| Compound No. | Structural formula |
|---|---|
| 642 | 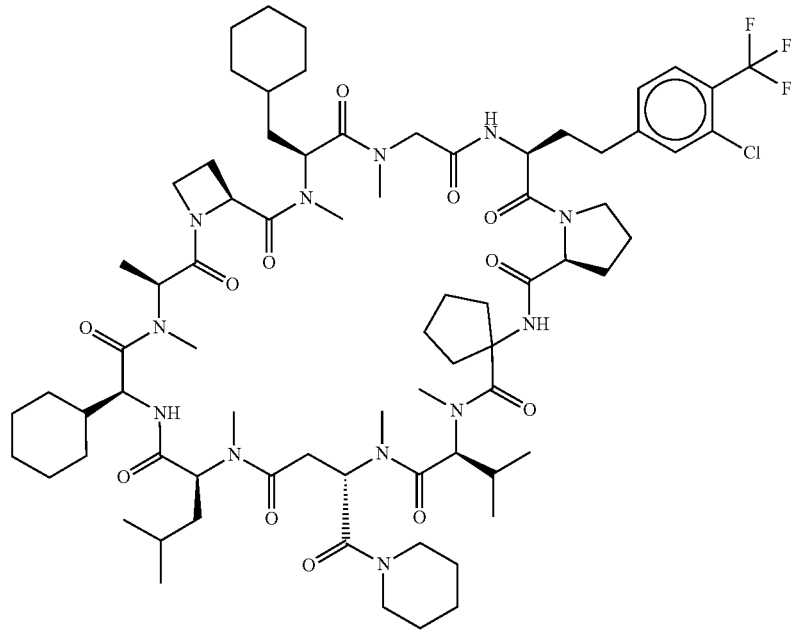 |
| 643 | 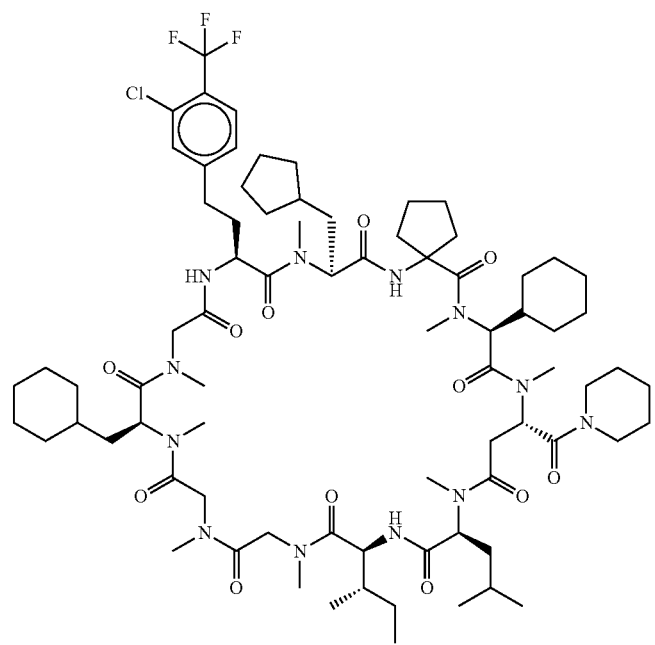 |

TABLE 24-continued
| Compound No. | Structural formula |
|---|---|
| 644 | 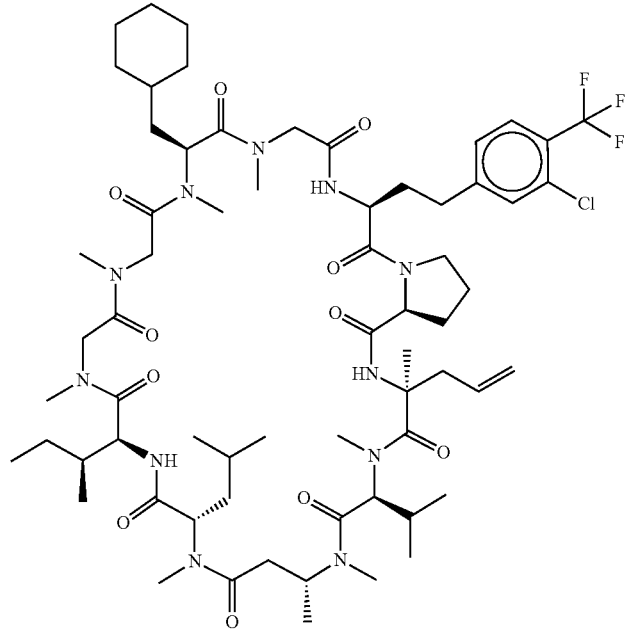 |
| 645 | 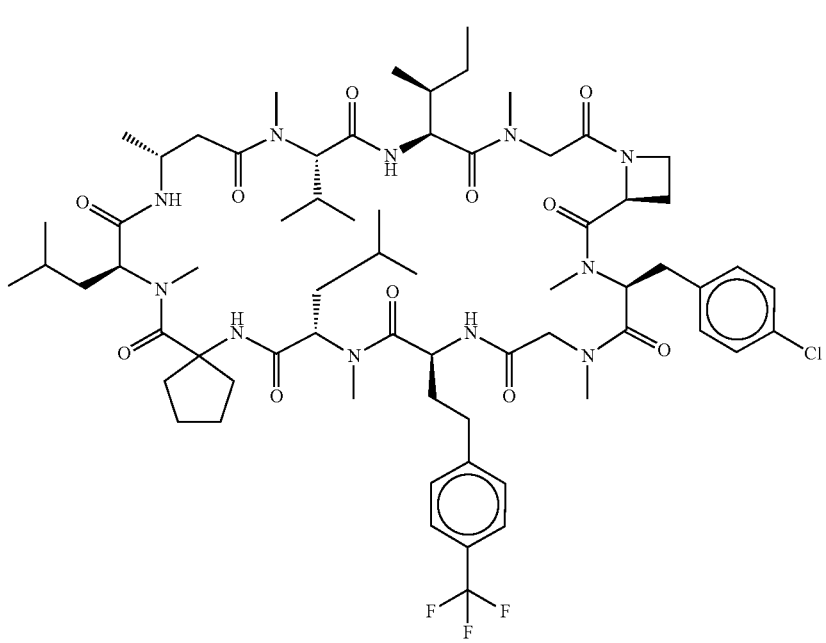 |

TABLE 24-continued
| Compound No. | Structural formula |
|---|---|
| 646 | 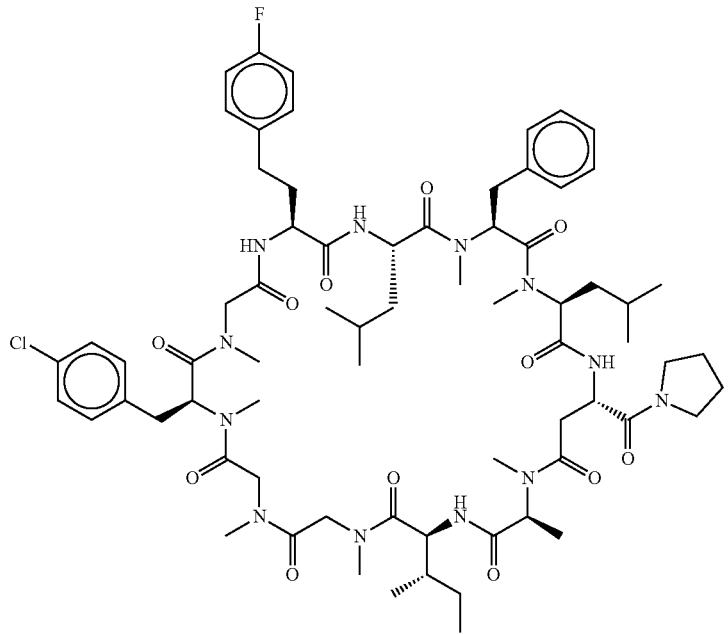 |
| 647 | 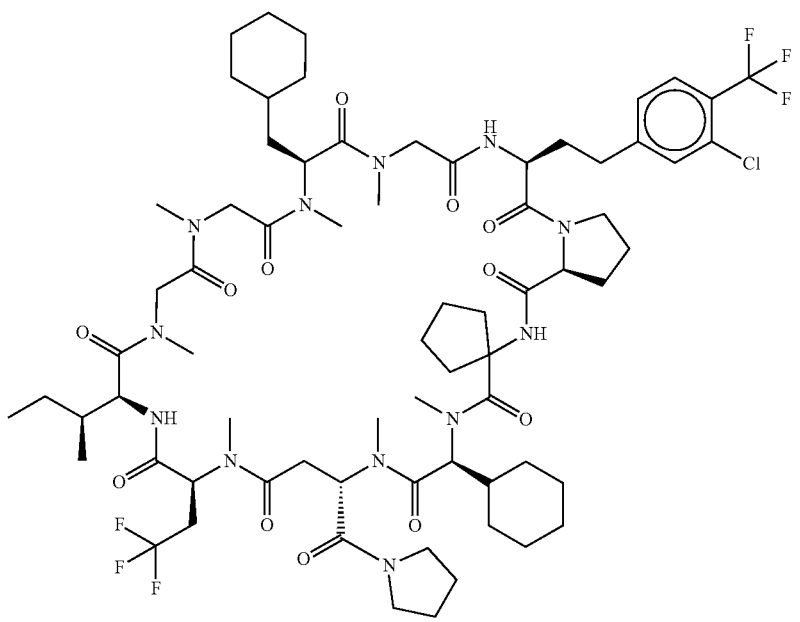 |

TABLE 24-continued
| Compound No. | Structural formula |
|---|---|
| 648 | 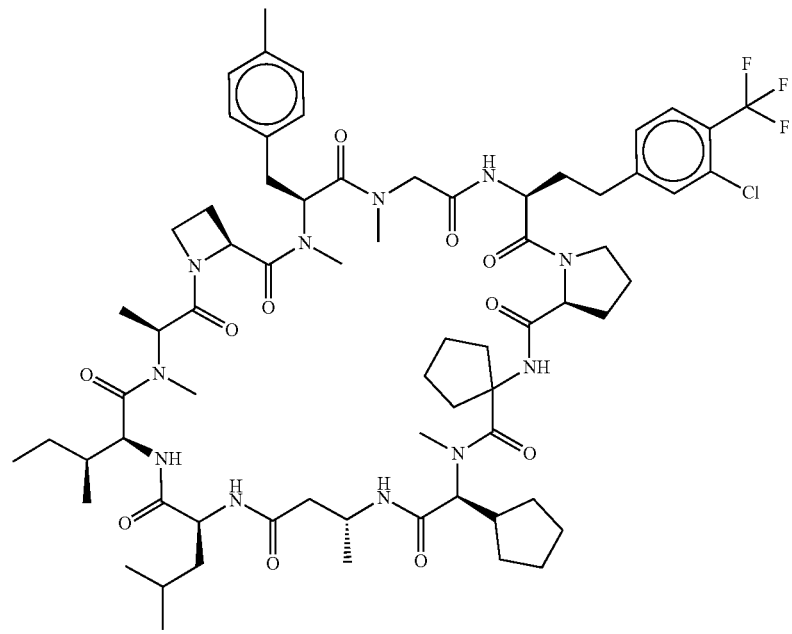 |
| 649 | 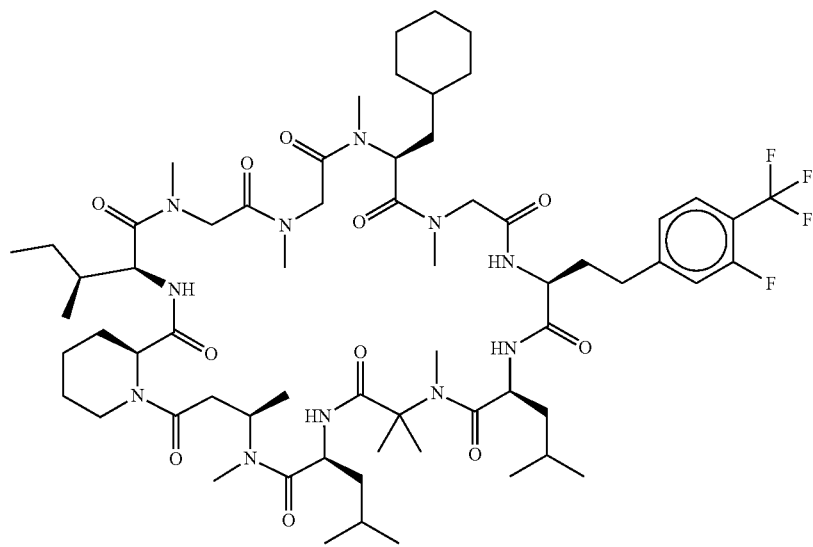 |

TABLE 24-continued
| Compound No. | Structural formula |
|---|---|
| 650 | 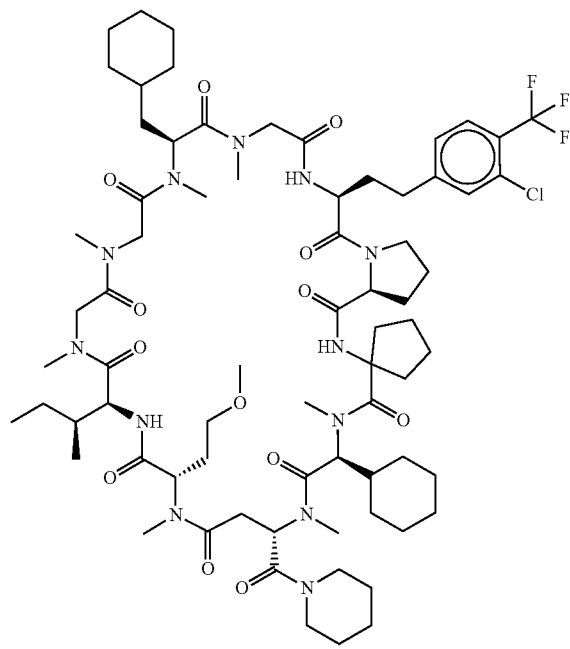 |
| 651 | 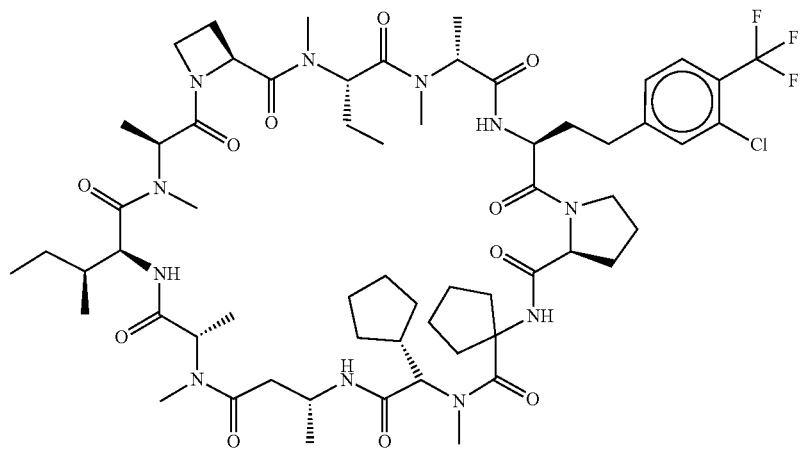 |

TABLE 24-continued
| Compound No. | Structural formula |
|---|---|
| 652 | 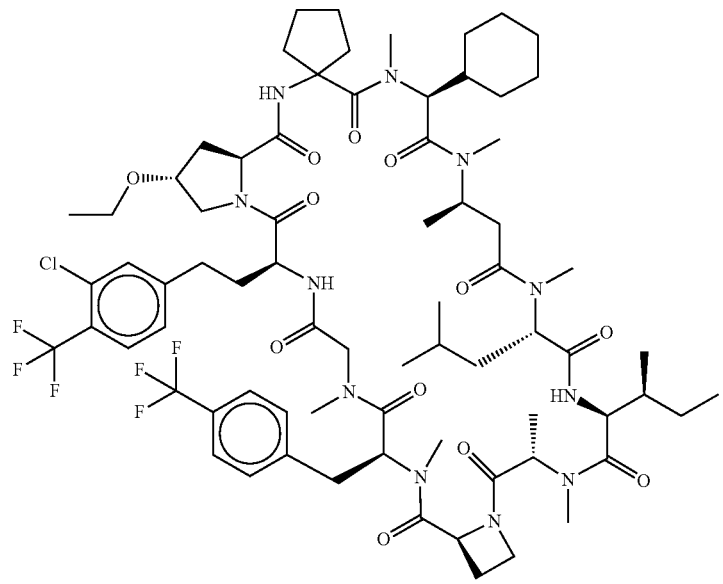 |
| 653 | 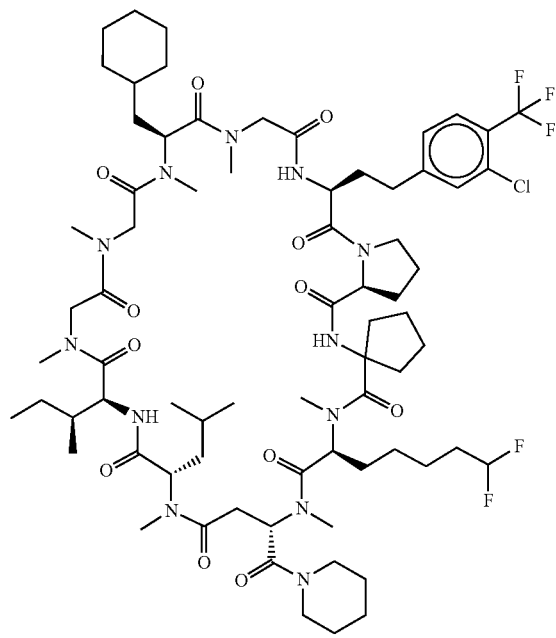 |

TABLE 24-continued
| Compound No. | Structural formula |
|---|---|
| 654 | 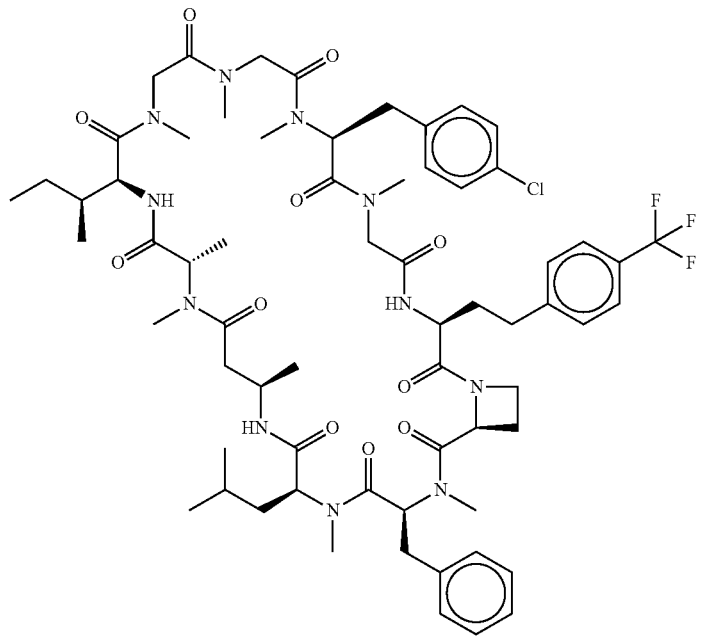 |
| 655 | 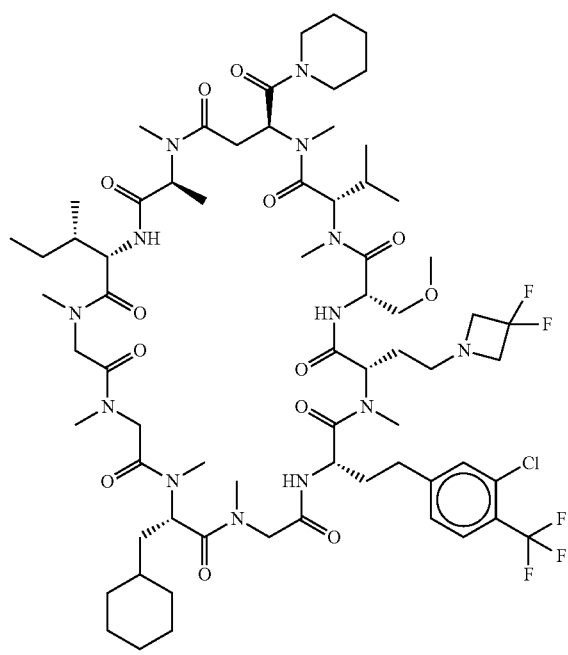 |

TABLE 24-continued
| Compound No. | Structural formula |
|---|---|
| 656 | 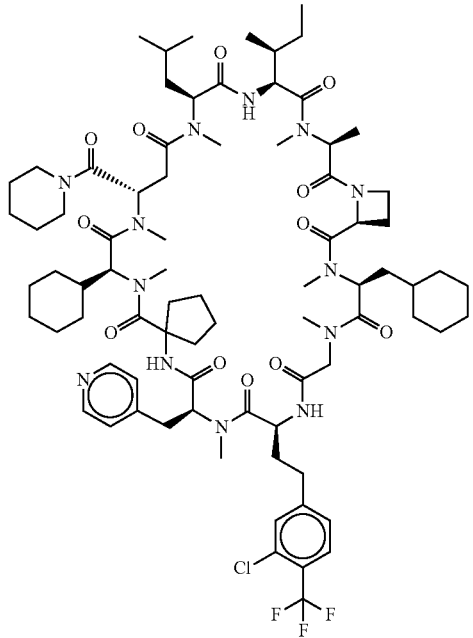 |
| 657 | 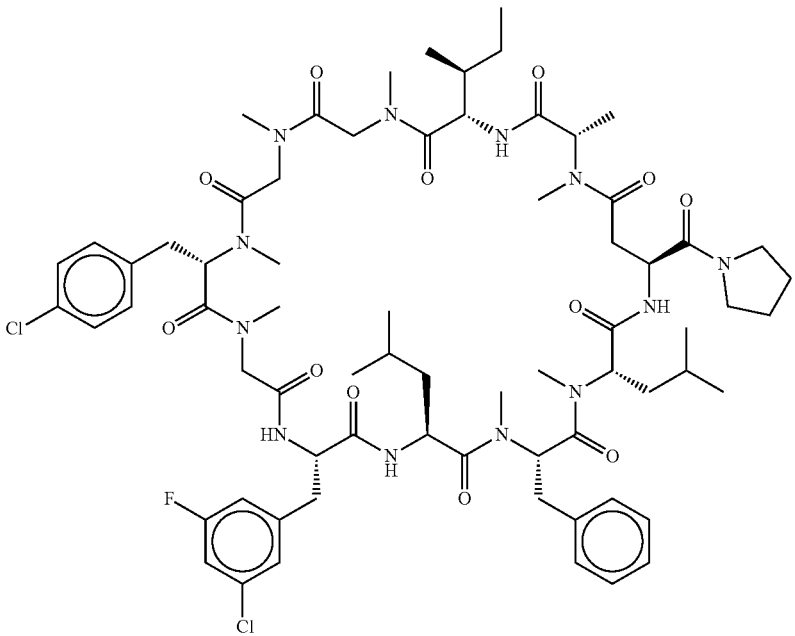 |

TABLE 24-continued
| Compound No. | Structural formula |
|---|---|
| 658 | 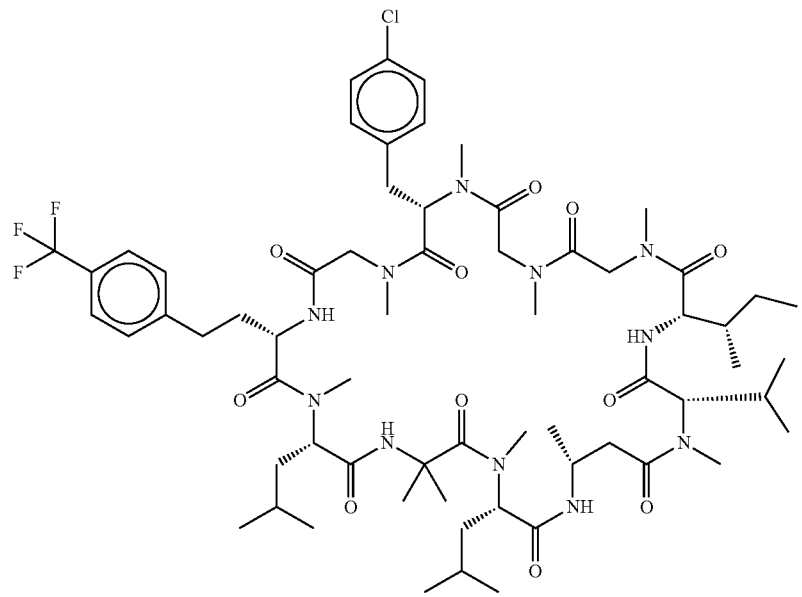 |
| 659 | 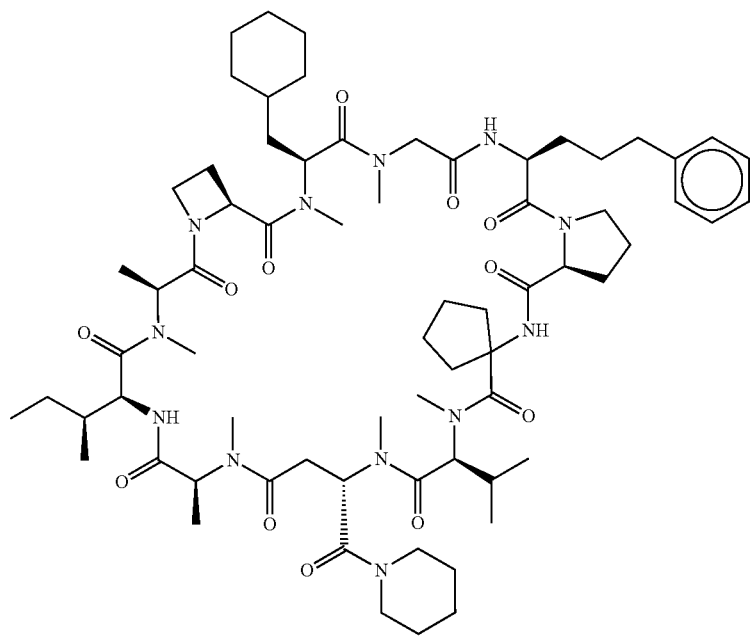 |

TABLE 24-continued
| Compound No. | Structural formula |
|---|---|
| 660 | 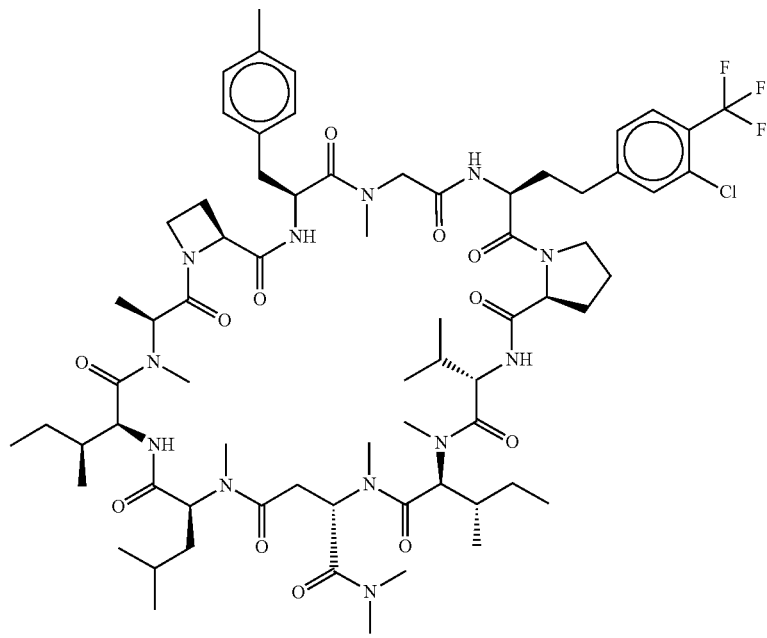 |
| 661 | 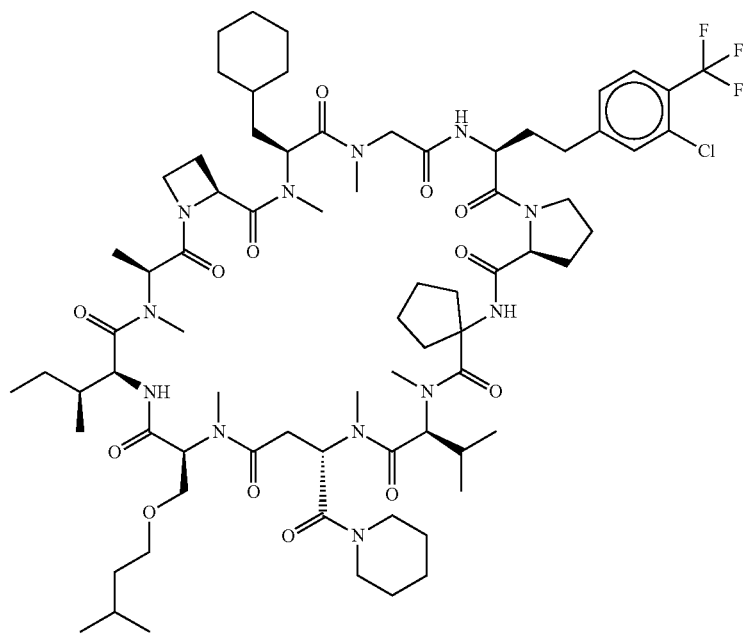 |

TABLE 24-continued
| Compound No. | Structural formula |
|---|---|
| 662 | 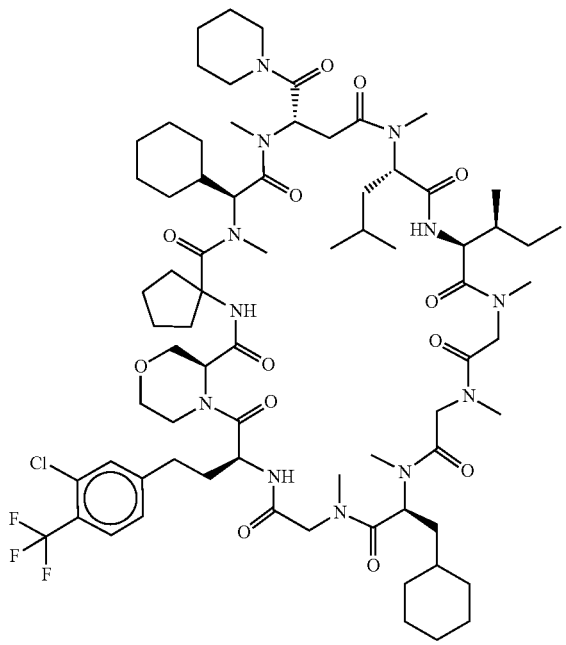 |
| 663 | 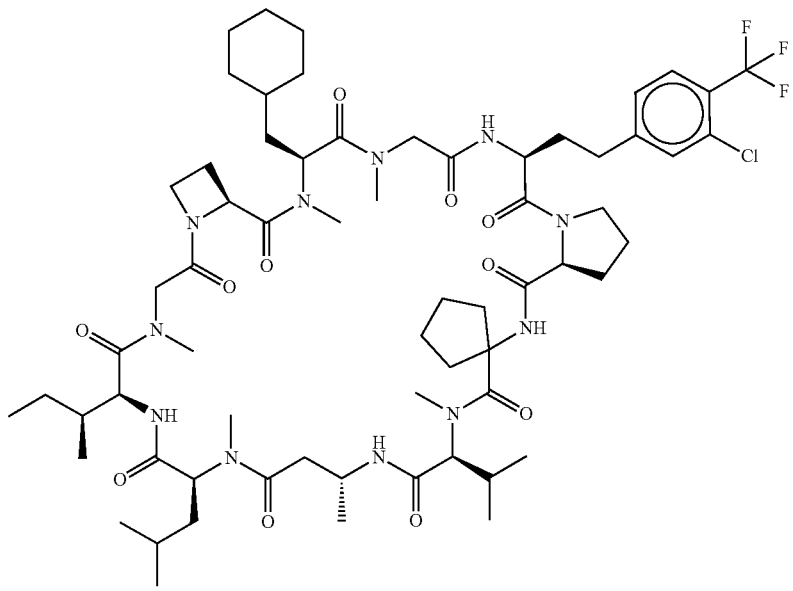 |

TABLE 24-continued
| Compound No. | Structural formula |
|---|---|
| 664 | 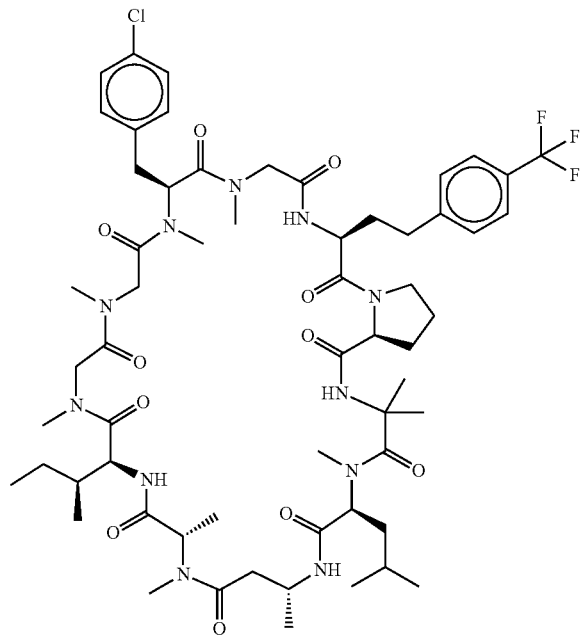 |
| 665 | 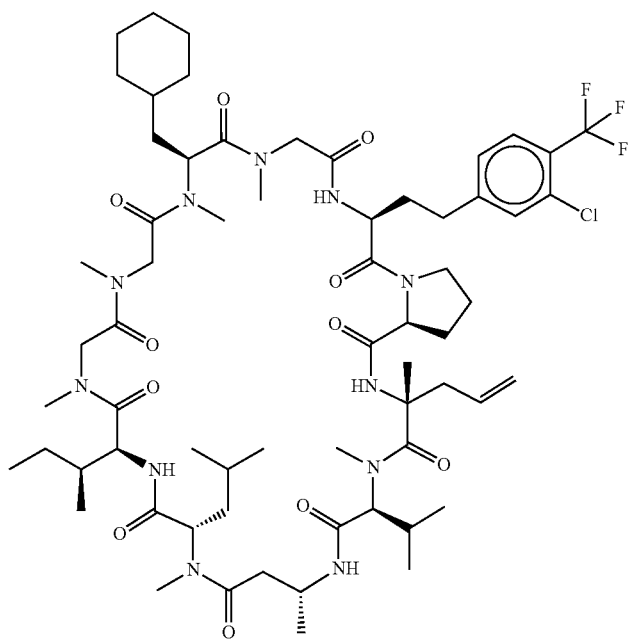 |

TABLE 24-continued
| Compound No. | Structural formula |
|---|---|
| 666 | 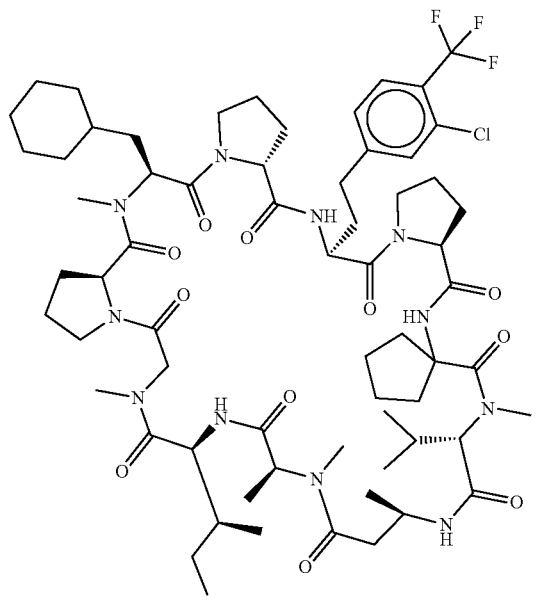 |
| 667 | 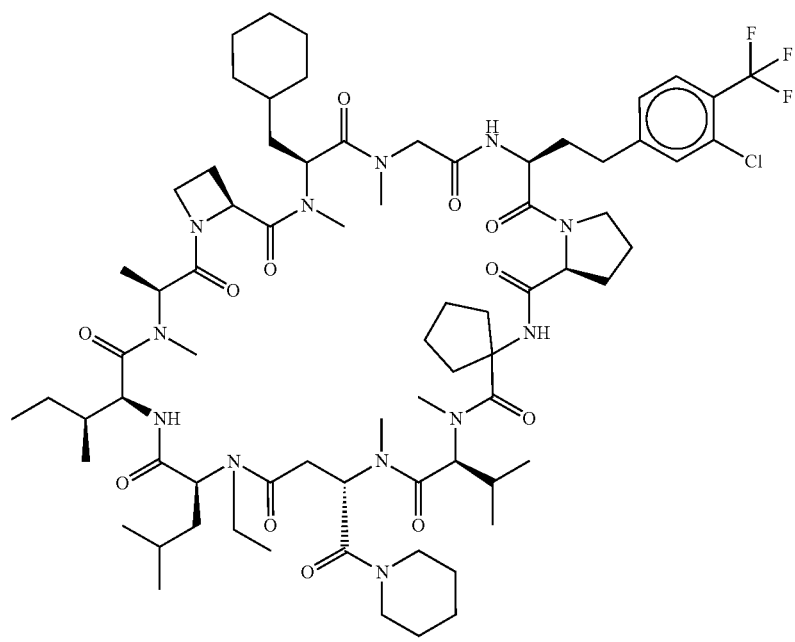 |

TABLE 24-continued
| Compound No. | Structural formula |
|---|---|
| 668 | 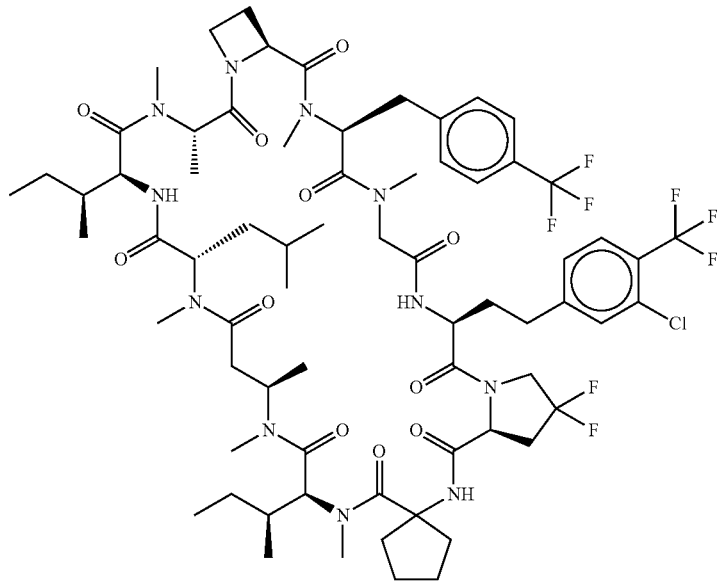 |
| 669 | 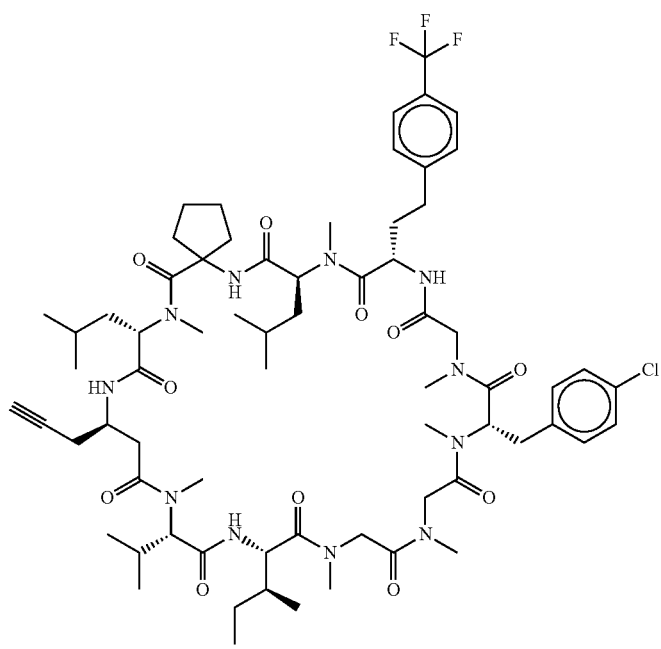 |

TABLE 24-continued
| Compound No. | Structural formula |
|---|---|
| 670 | 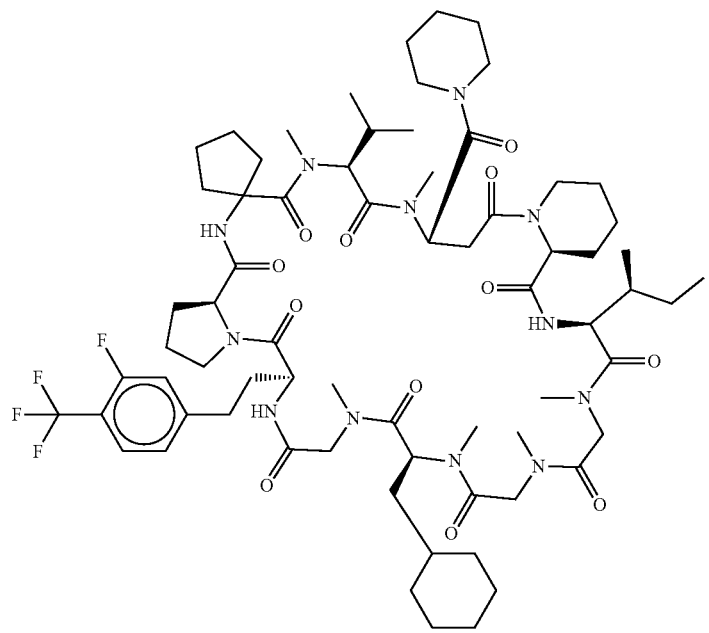 |
| 671 | 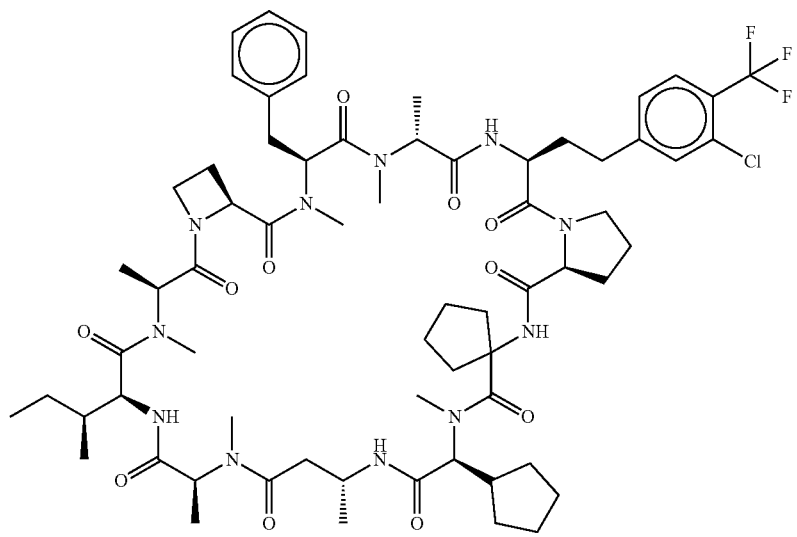 |

TABLE 24-continued
| Compound No. | Structural formula |
|---|---|
| 672 | 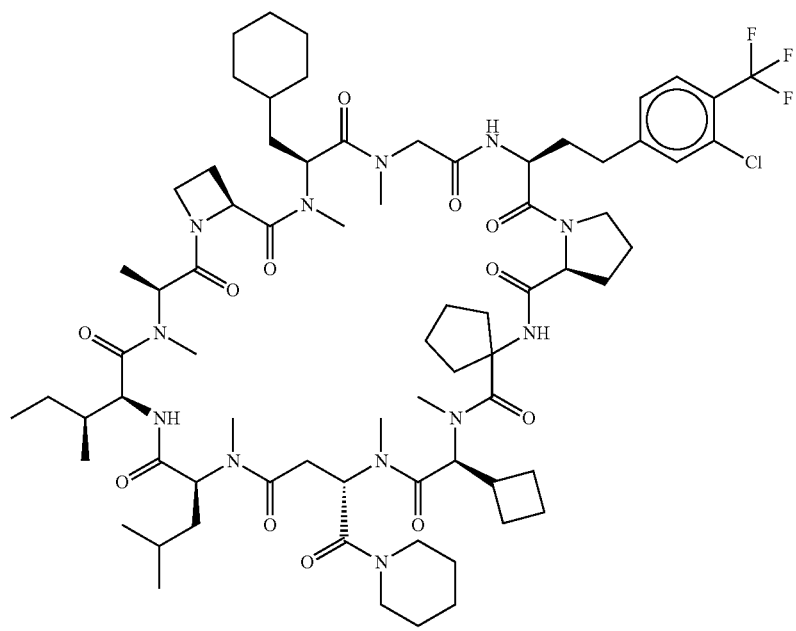 |
| 673 | 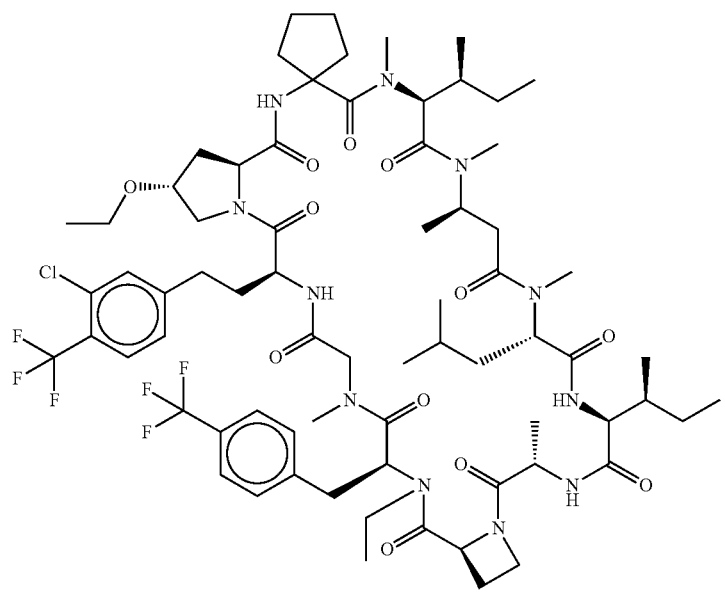 |

TABLE 24-continued
| Compound No. | Structural formula |
|---|---|
| 674 | 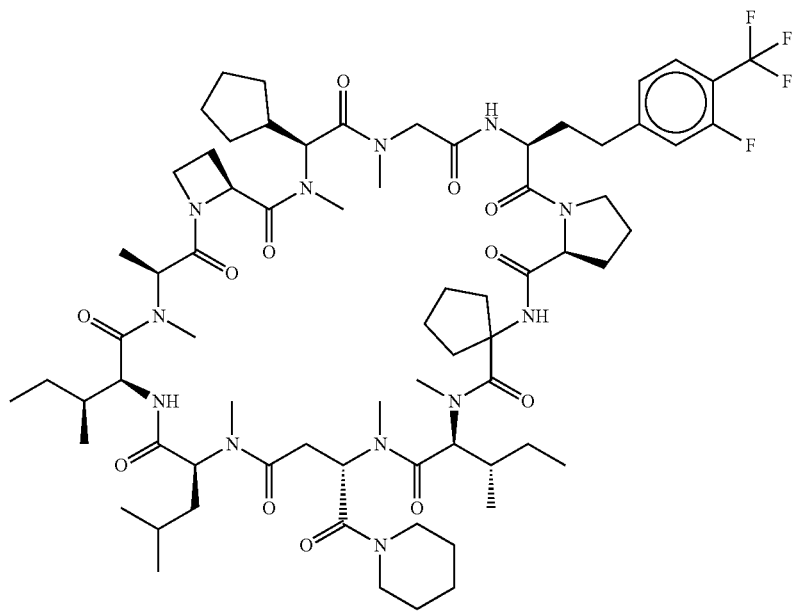 |
| 675 | 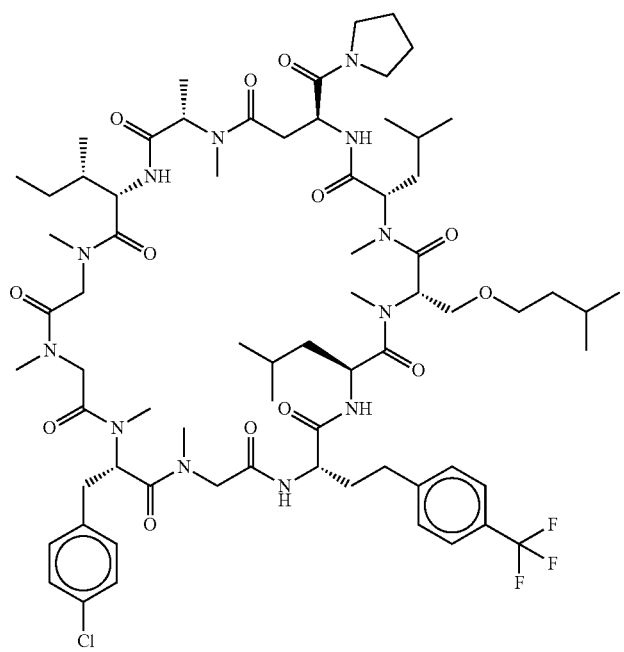 |

TABLE 24-continued
| Compound No. | Structural formula |
|---|---|
| 676 | 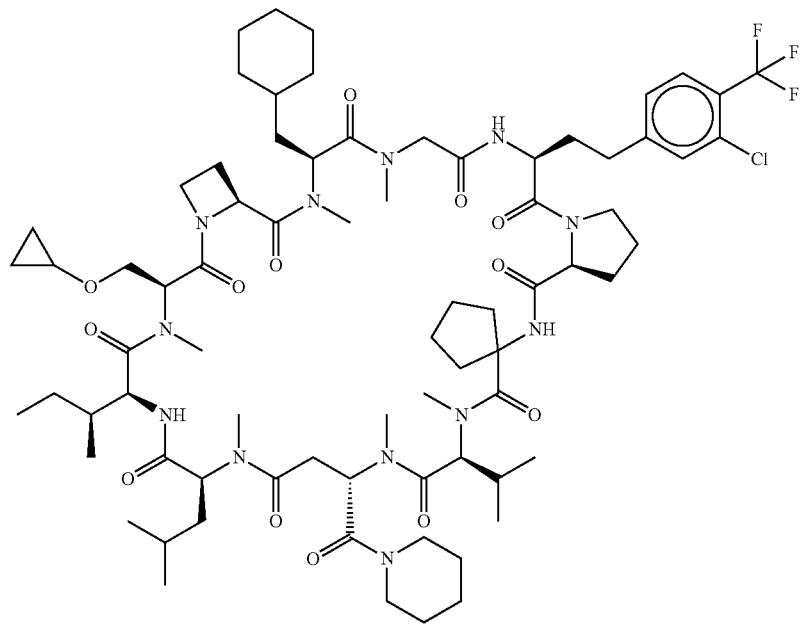 |
| 677 | 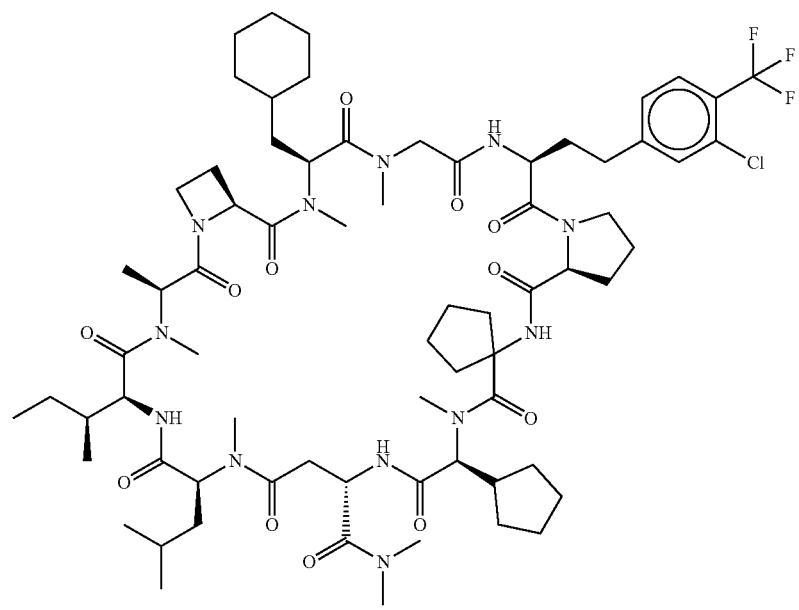 |

TABLE 24-continued
| Compound No. | Structural formula |
|---|---|
| 678 | 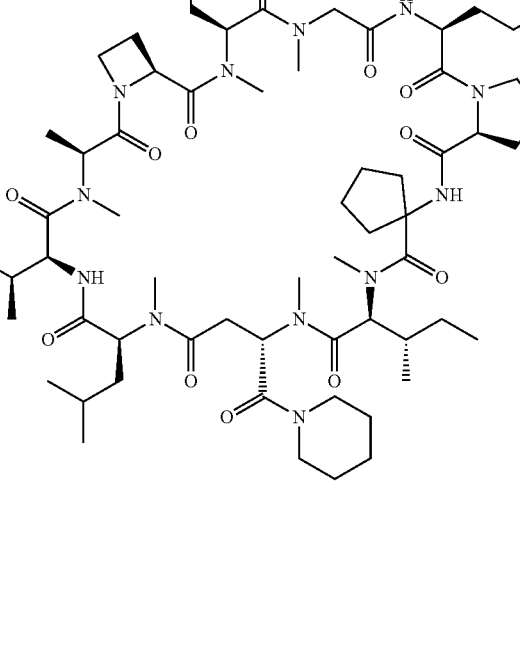 |
| 679 | 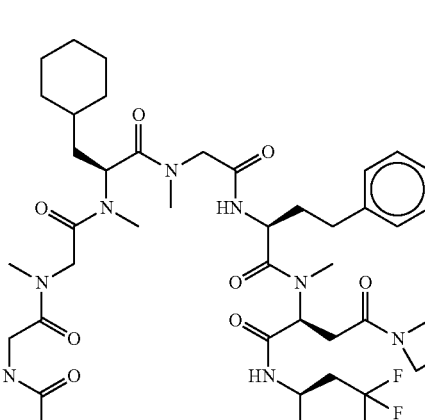 |

TABLE 24-continued
| Compound No. | Structural formula |
|---|---|
| 680 | 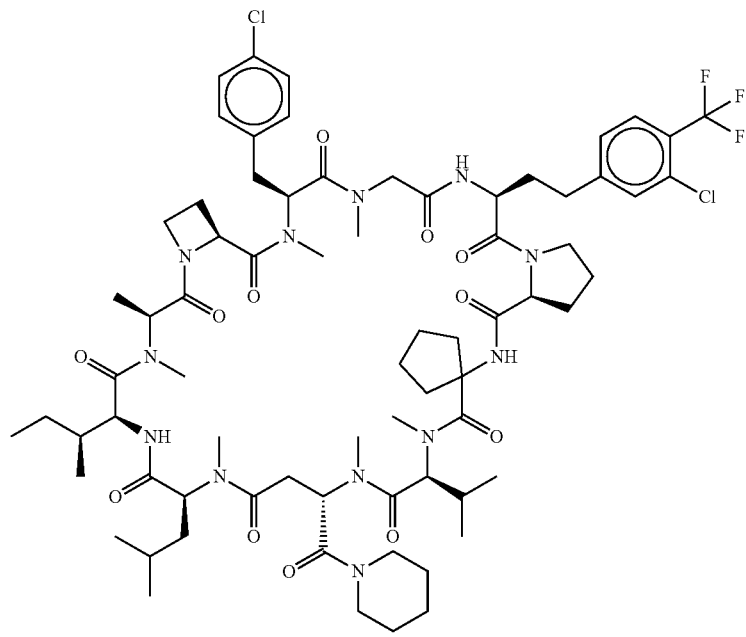 |
| 681 | 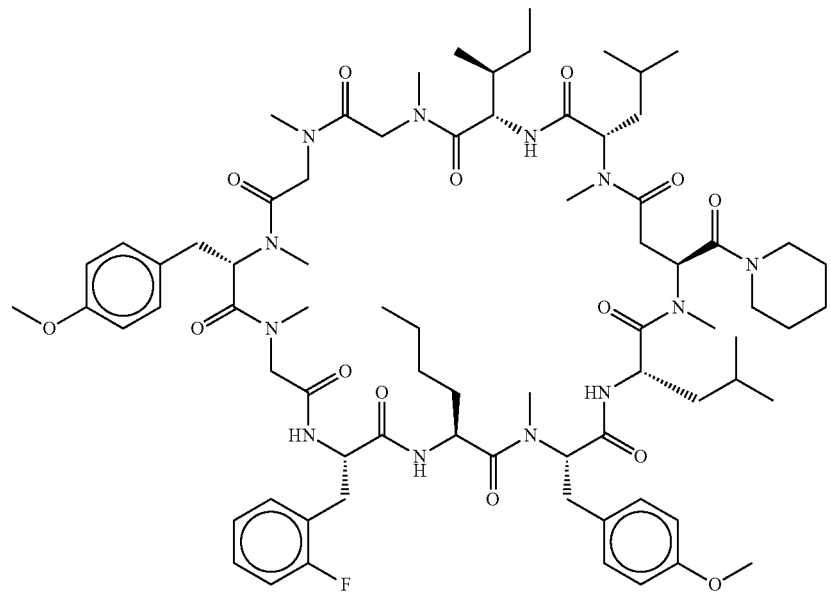 |

TABLE 24-continued
| Compound No. | Structural formula |
|---|---|
| 682 | 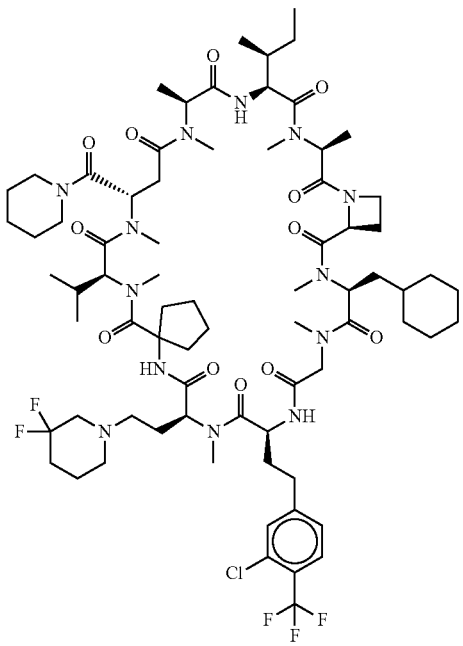 |
| 683 | 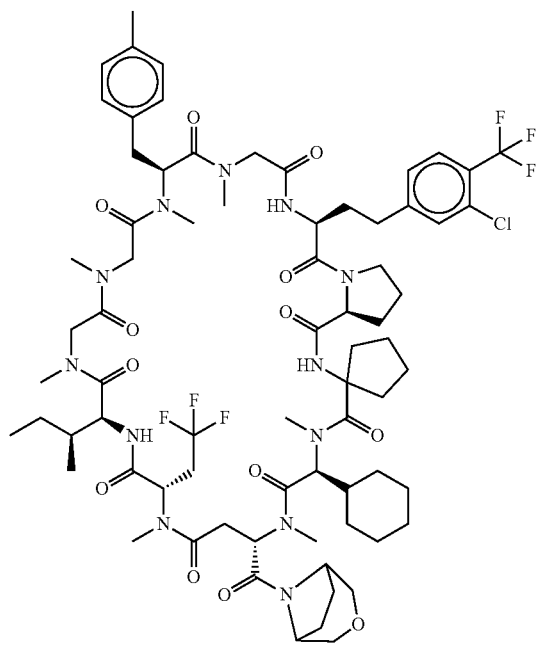 |

TABLE 24-continued
| Compound No. | Structural formula |
|---|---|
| 684 | 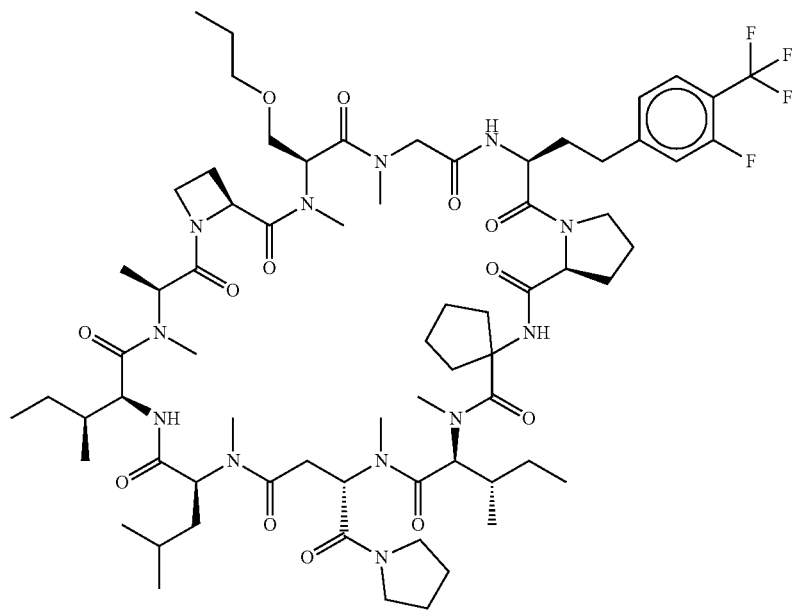 |
| 685 | 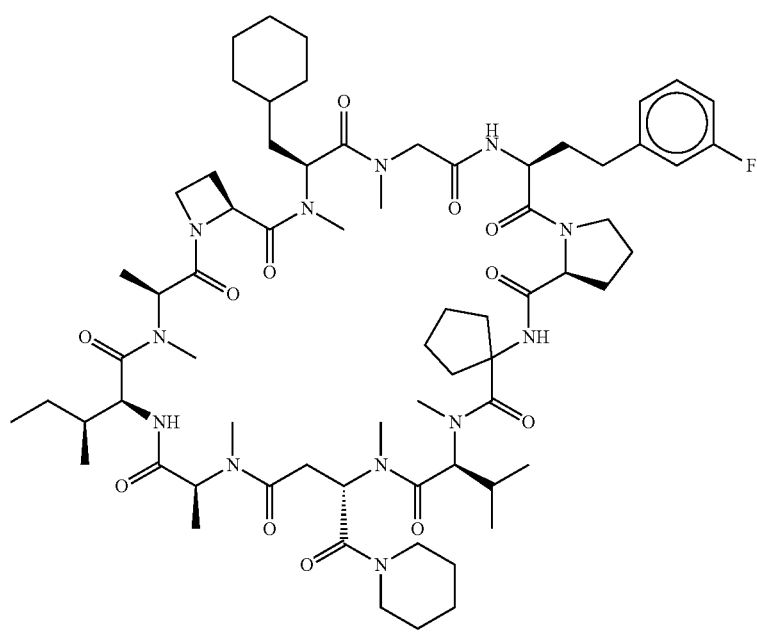 |

TABLE 24-continued
| Compound No. | Structural formula |
|---|---|
| 686 | 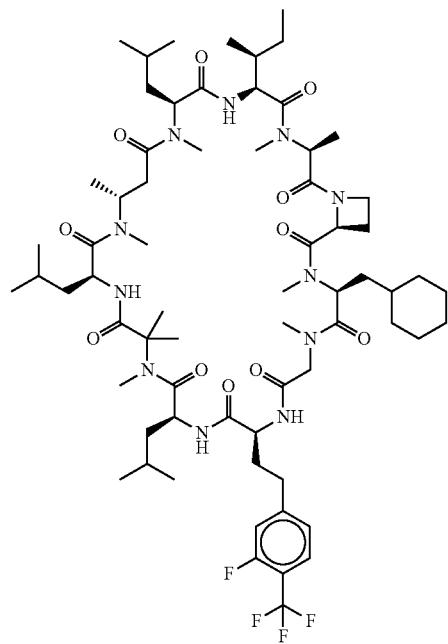 |
| 687 | 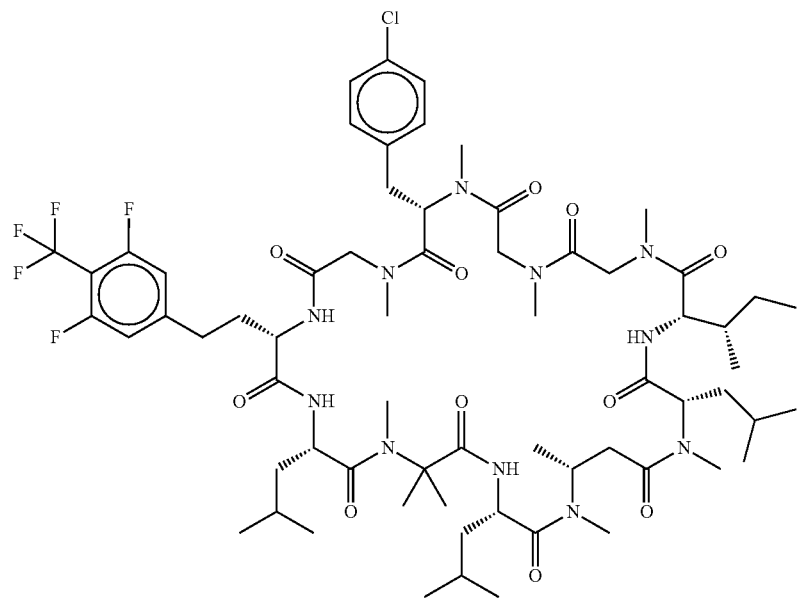 |

TABLE 24-continued
| Compound No. | Structural formula |
|---|---|
| 688 | 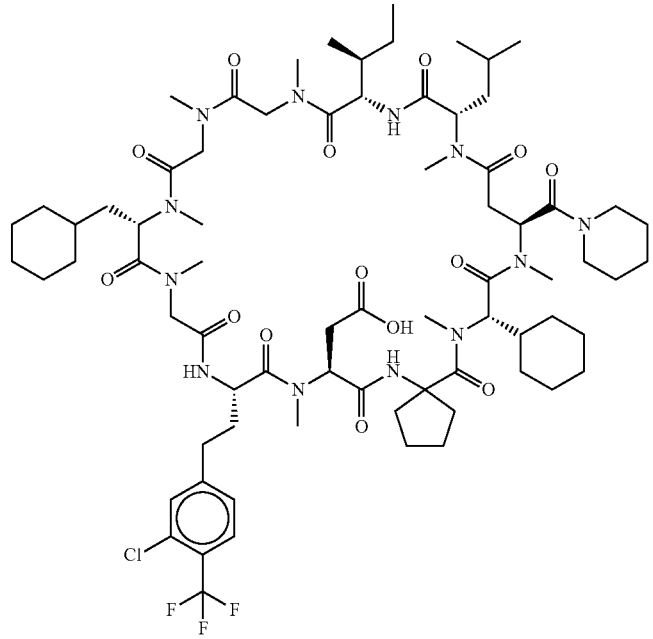 |
| 689 | 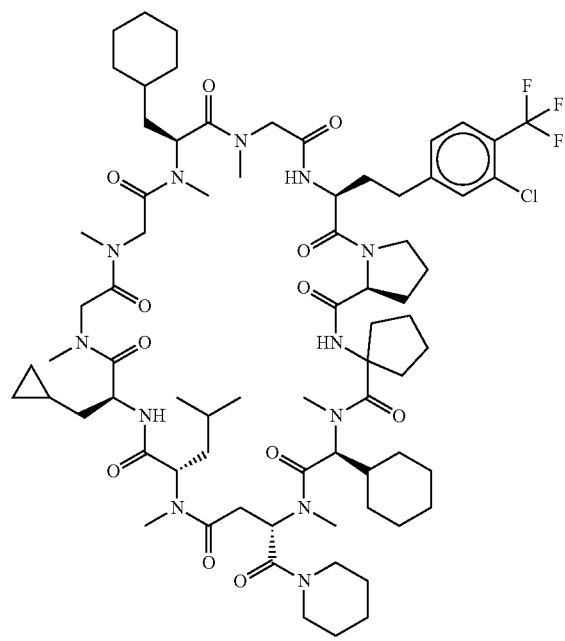 |

TABLE 24-continued
| Compound No. | Structural formula |
|---|---|
| 690 | 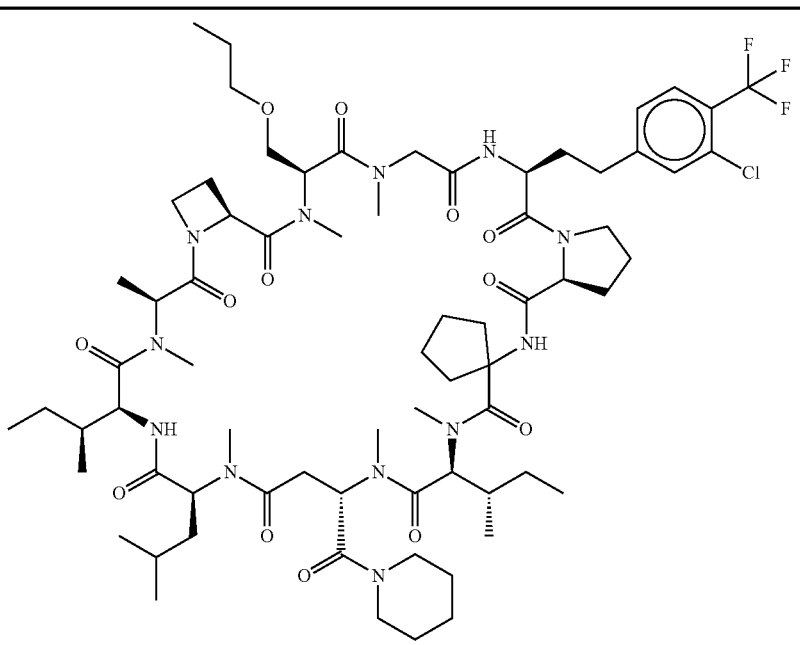 |
| 691 | 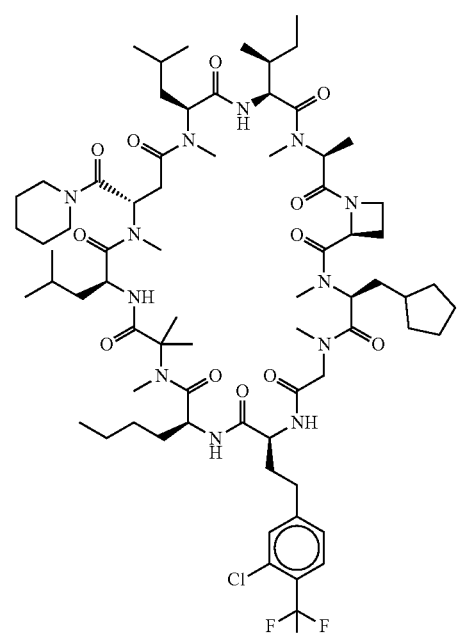 |

TABLE 24-continued
| Compound No. | Structural formula |
|---|---|
| 692 | 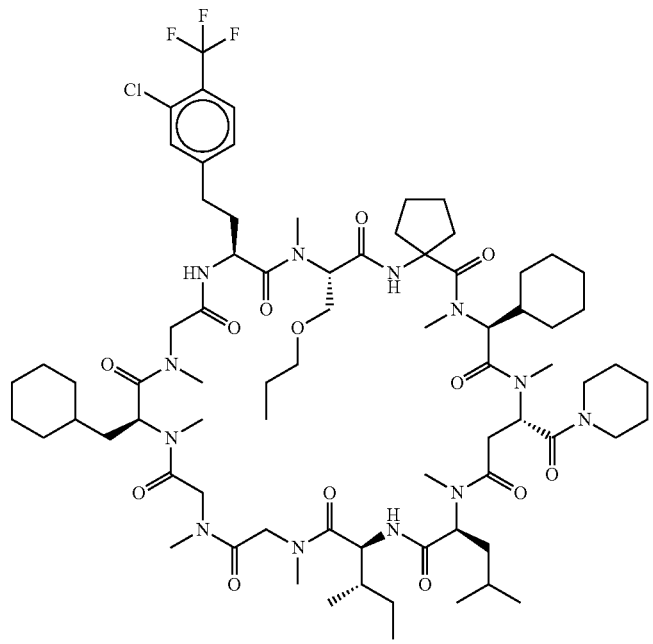 |
| 693 | 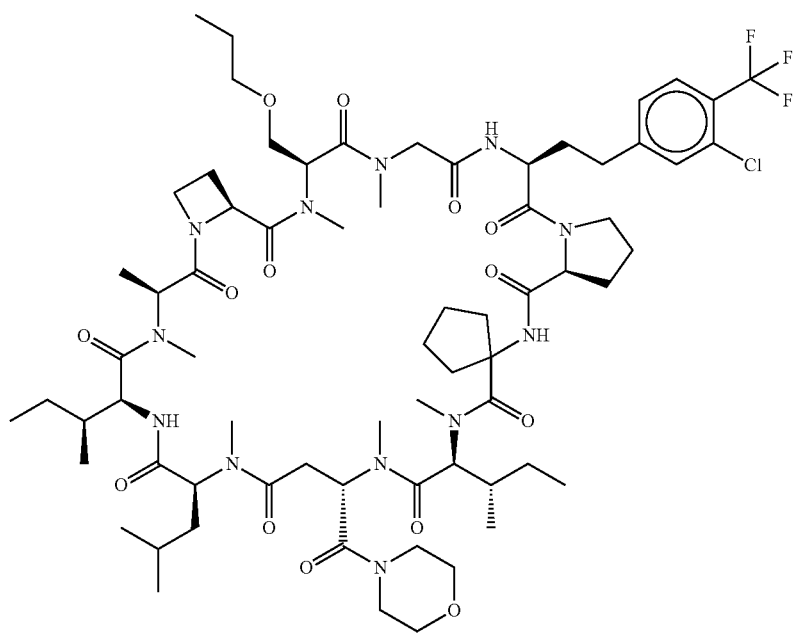 |

TABLE 24-continued
| Compound No. | Structural formula |
|---|---|
| 694 | 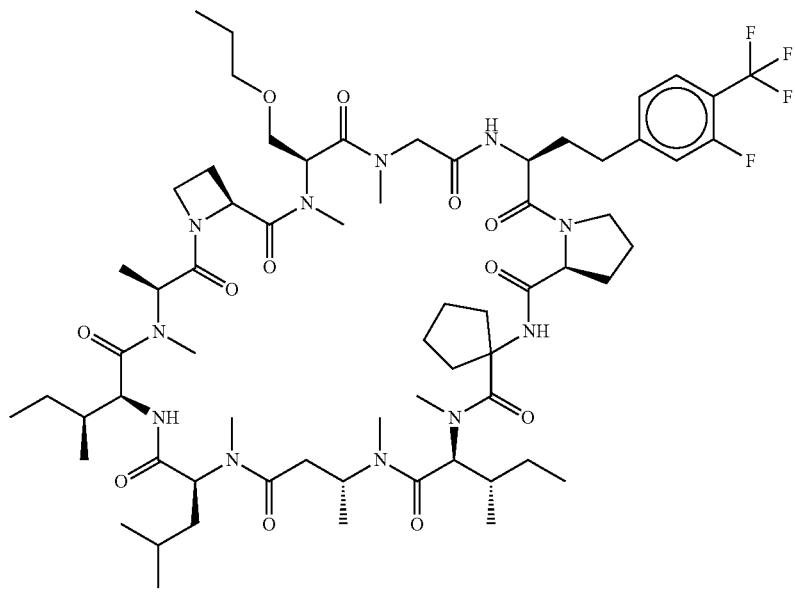 |
| 695 | 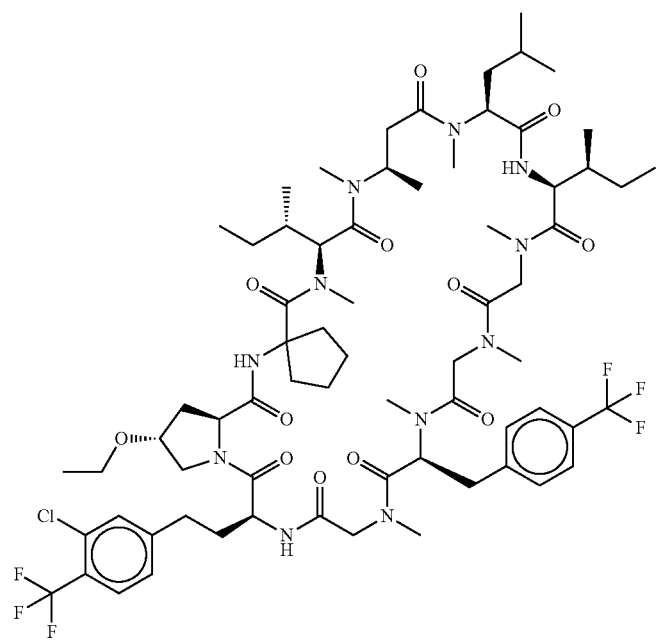 |

TABLE 24-continued
| Compound No. | Structural formula |
|---|---|
| 696 | 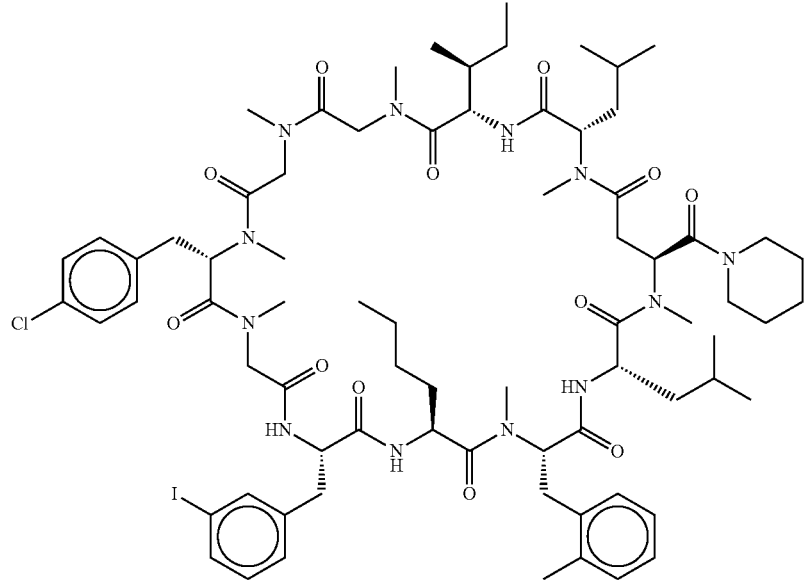 |
| 697 | 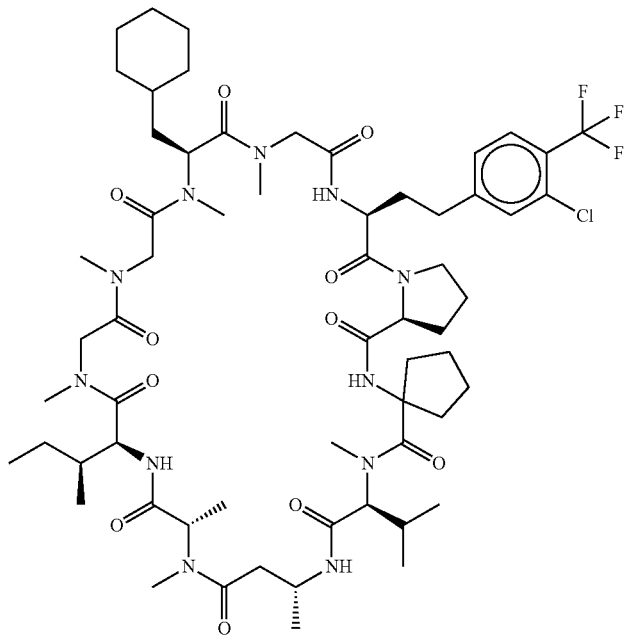 |

TABLE 24-continued
| Compound No. | Structural formula |
|---|---|
| 698 | 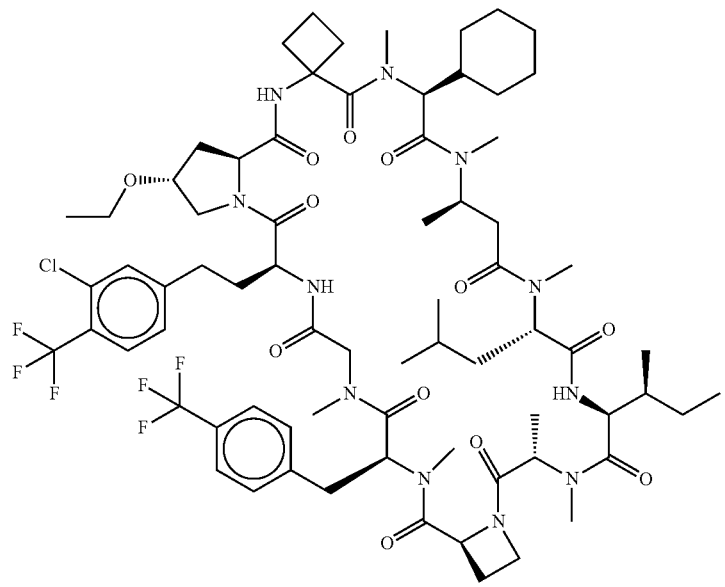 |
| 699 | 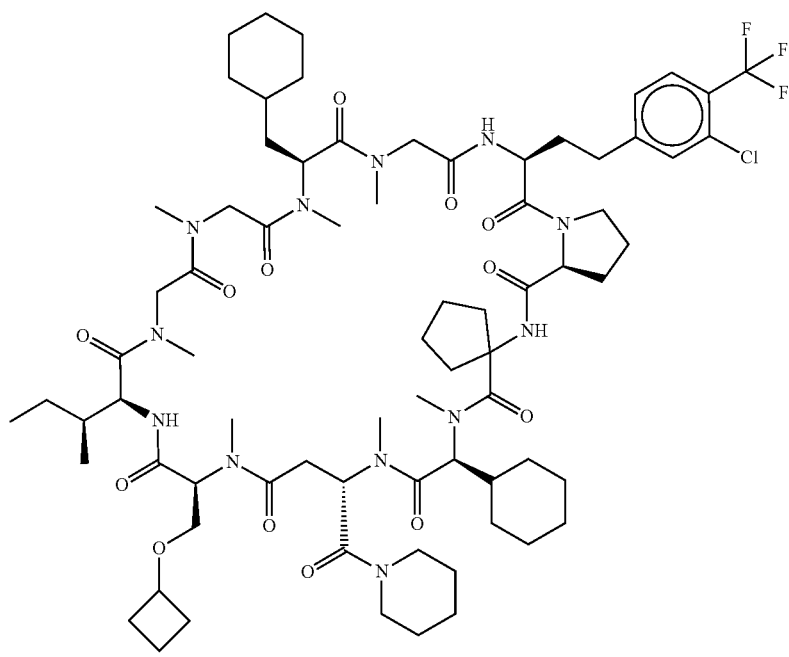 |

TABLE 24-continued
| Compound No. | Structural formula |
|---|---|
| 700 | 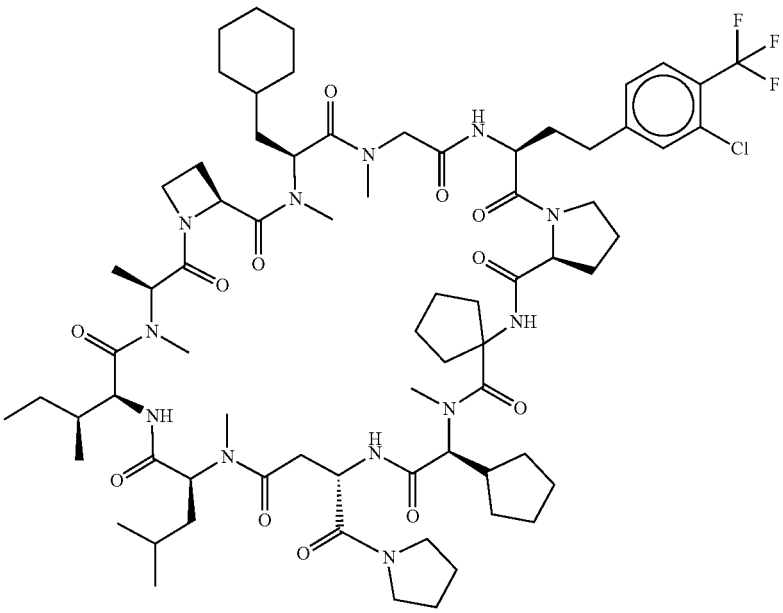 |
| 701 | 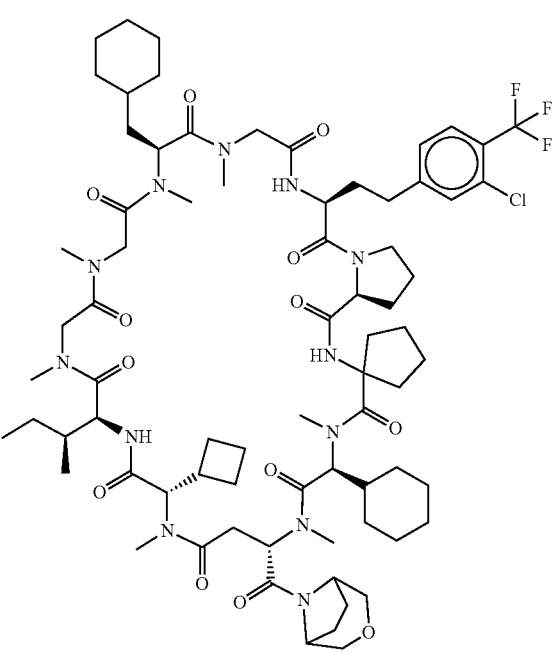 |

TABLE 24-continued
| Compound No. | Structural formula |
|---|---|
| 702 | 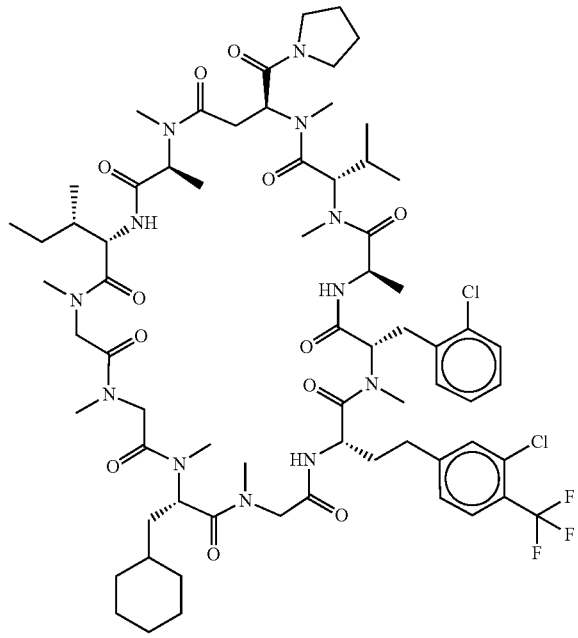 |
| 703 | 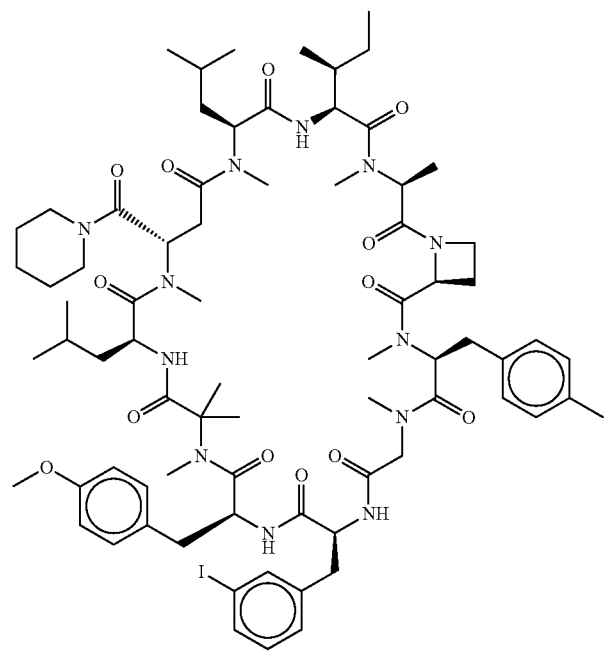 |

TABLE 24-continued
| Compound No. | Structural formula |
|---|---|
| 704 | 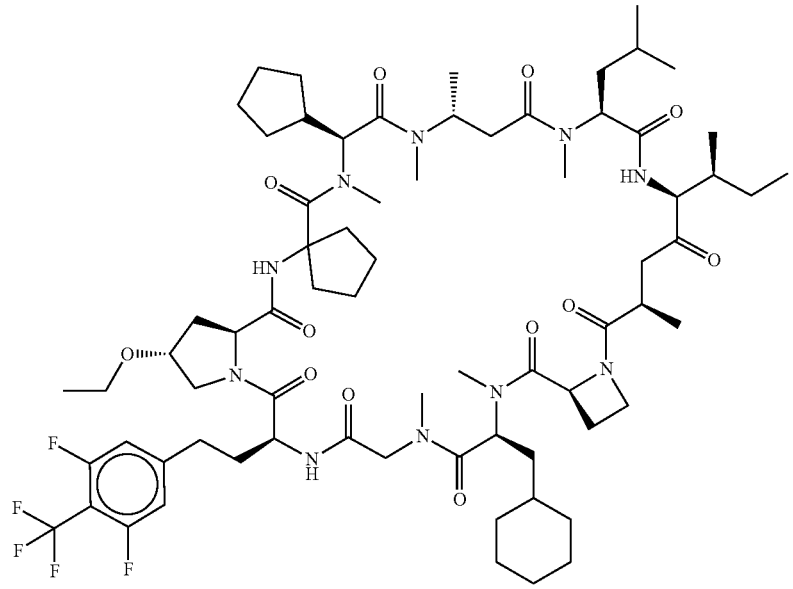 |
| 705 | 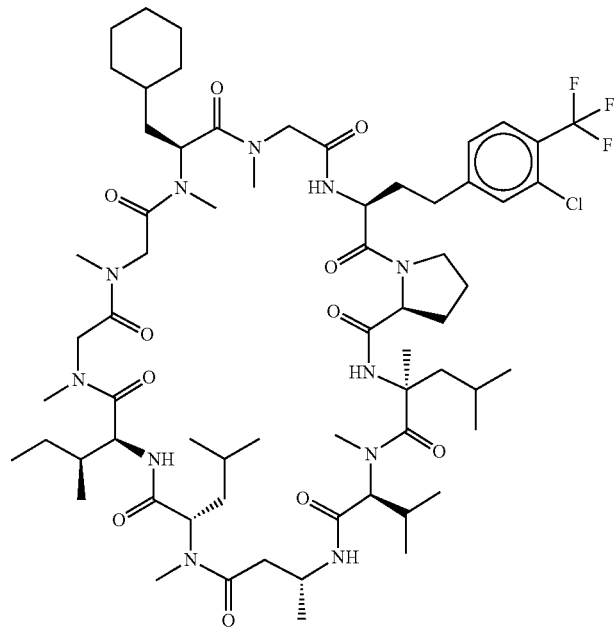 |

TABLE 24-continued
| Compound No. | Structural formula |
|---|---|
| 706 | 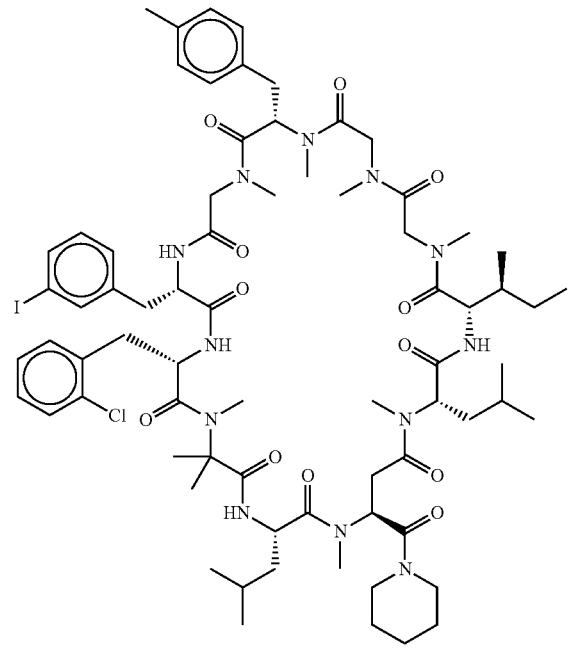 |
| 707 | 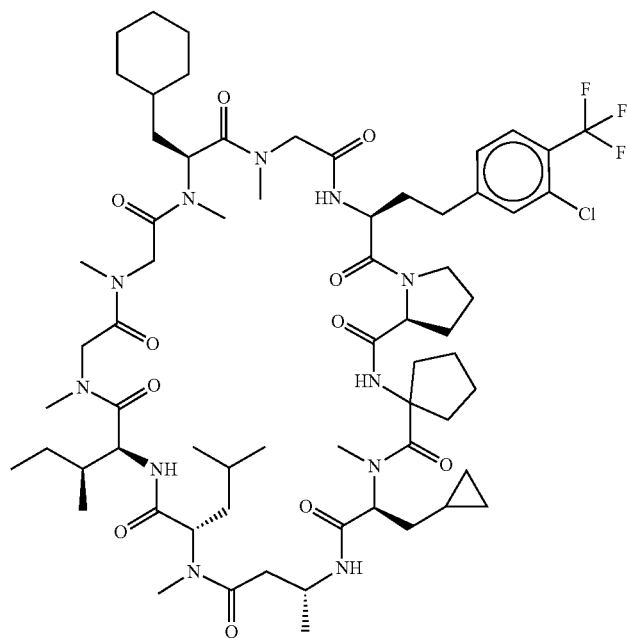 |

TABLE 24-continued
| Compound No. | Structural formula |
|---|---|
| 708 | 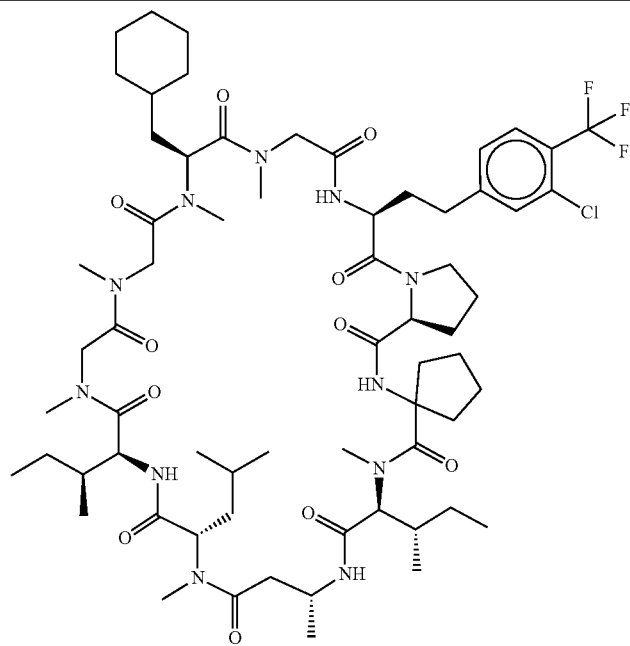 |
| 709 | 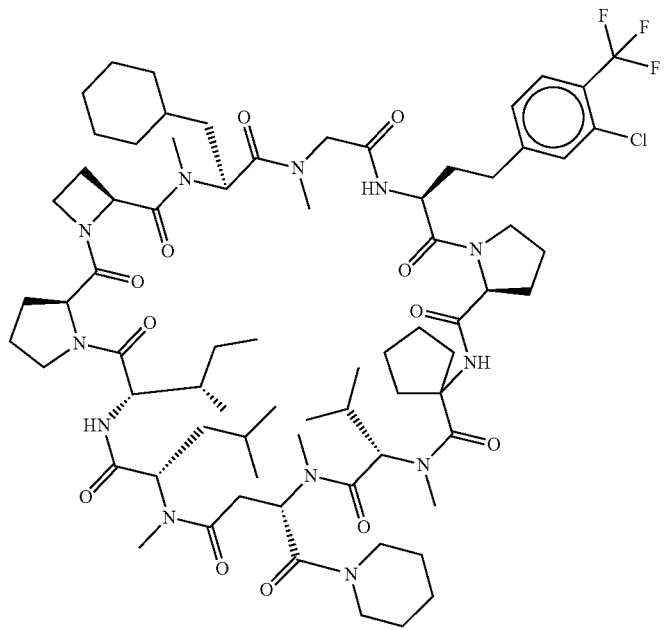 |

TABLE 24-continued
| Compound No. | Structural formula |
|---|---|
| 710 | 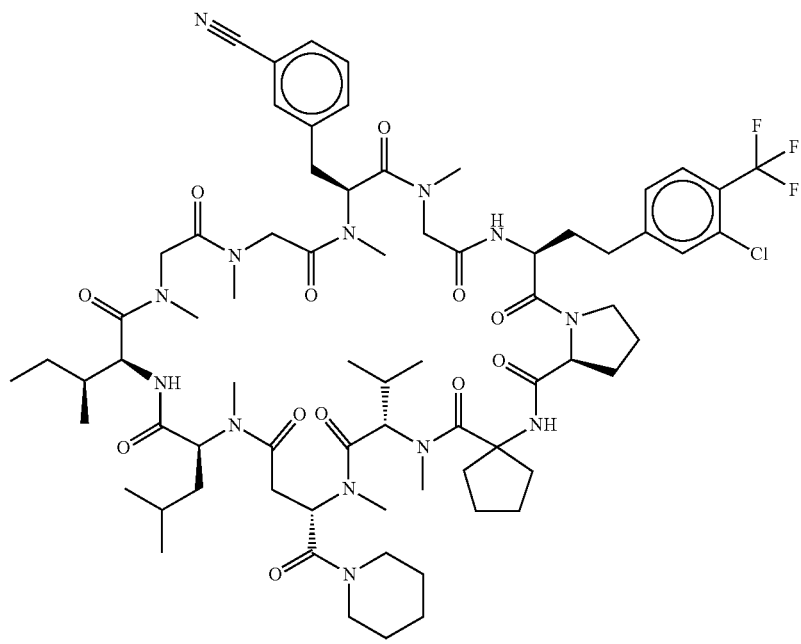 |
| 711 | 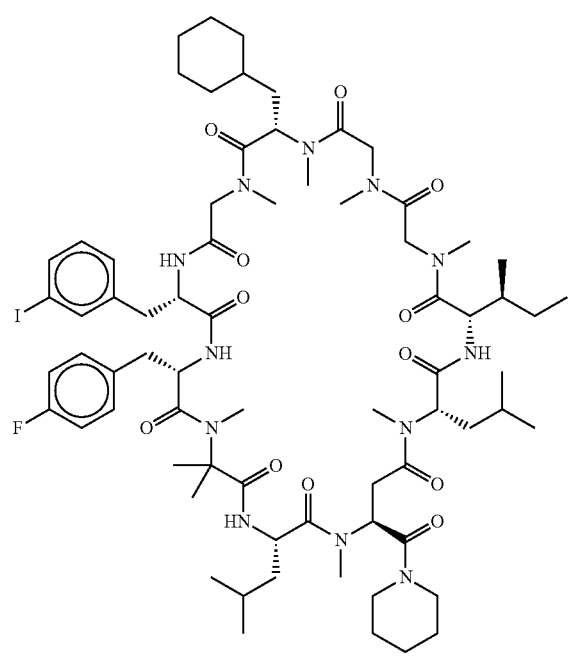 |

TABLE 24-continued
| Compound No. | Structural formula |
|---|---|
| 712 | 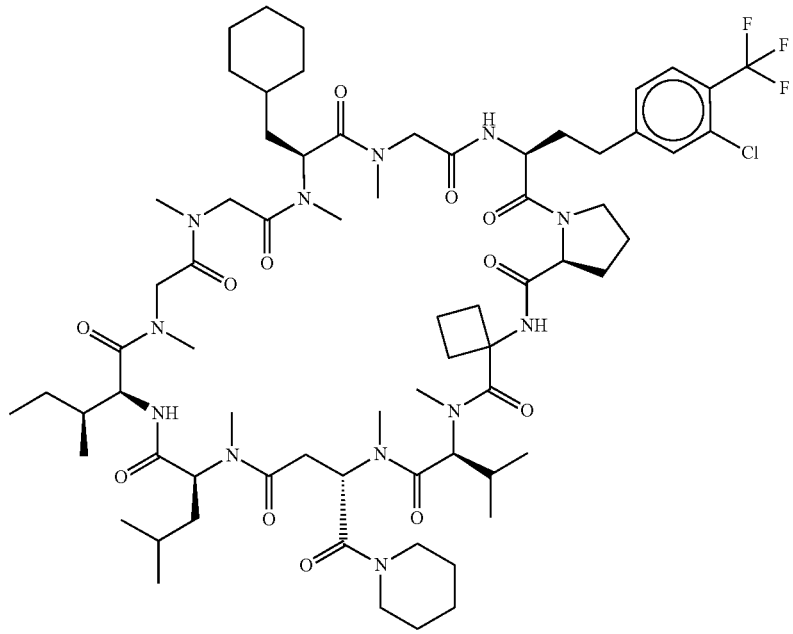 |
| 713 | 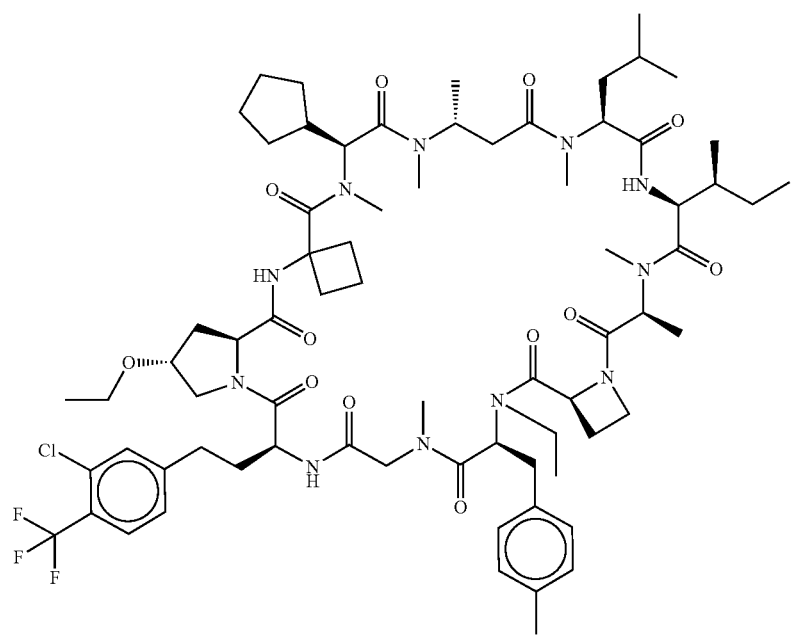 |

TABLE 24-continued
| Compound No. | Structural formula |
|---|---|
| 714 | 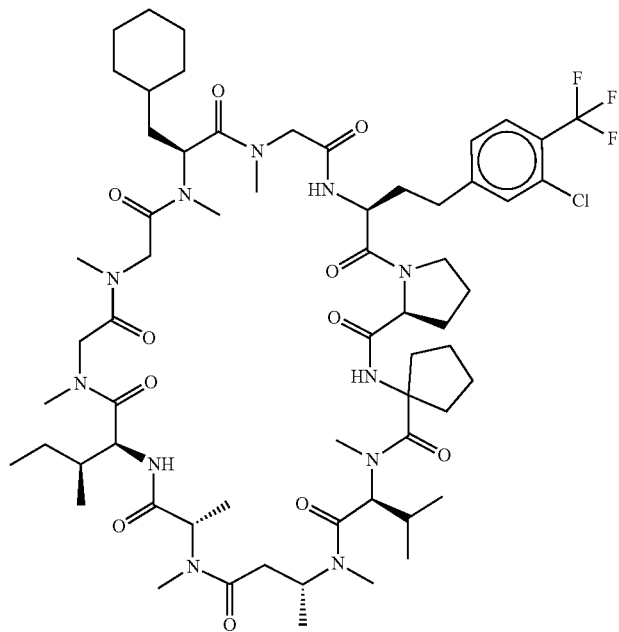 |
| 715 | 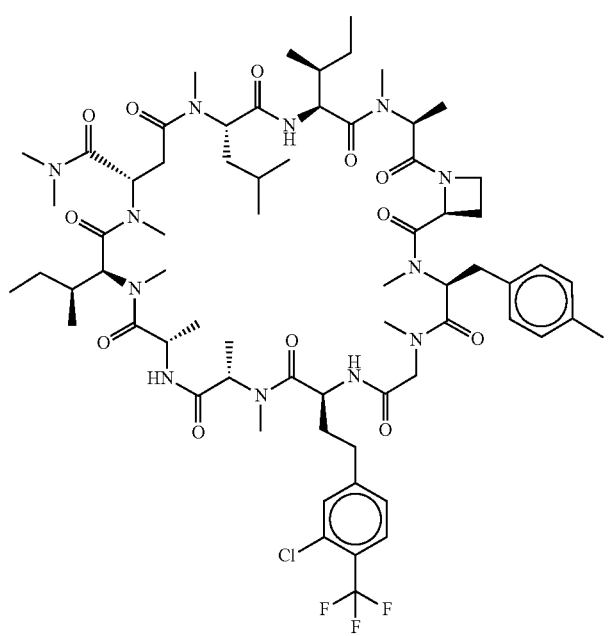 |

TABLE 24-continued
| Compound No. | Structural formula |
|---|---|
| 716 | 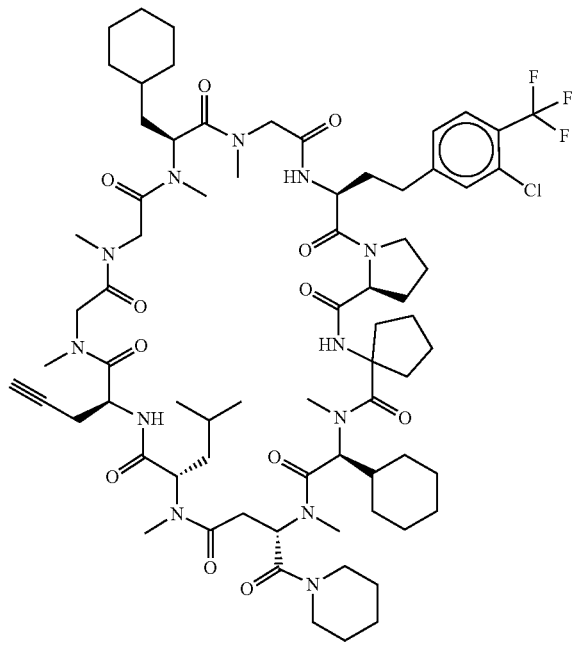 |
| 717 | 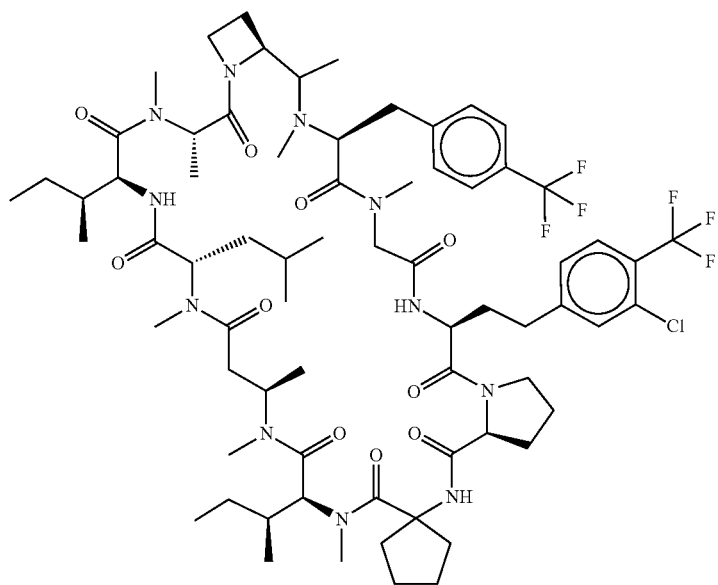 |

TABLE 24-continued
| Compound No. | Structural formula |
|---|---|
| 718 | 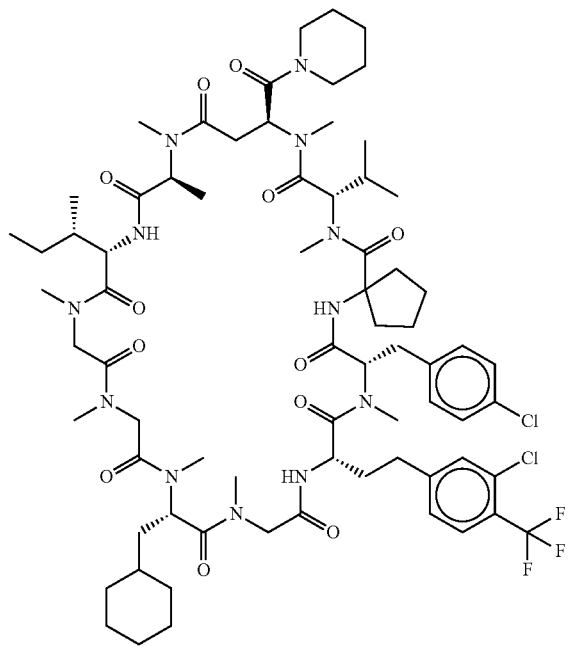 |
| 719 | 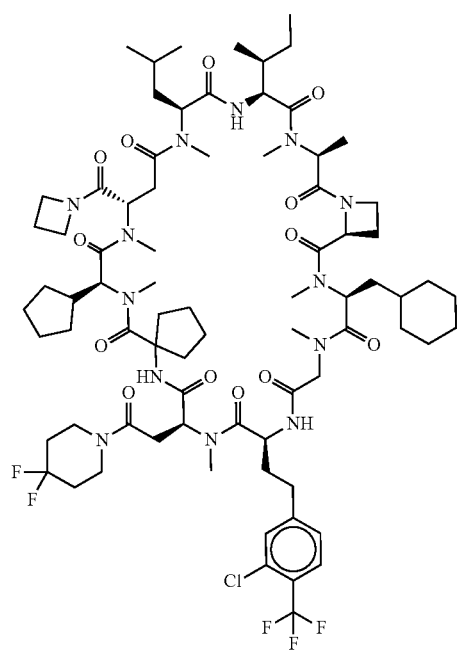 |

TABLE 24-continued
| Compound No. | Structural formula |
|---|---|
| 720 | 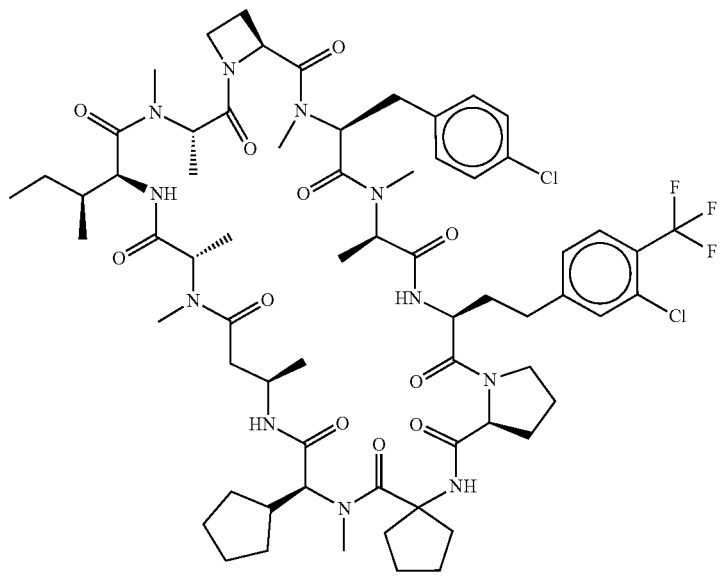 |
| 721 | 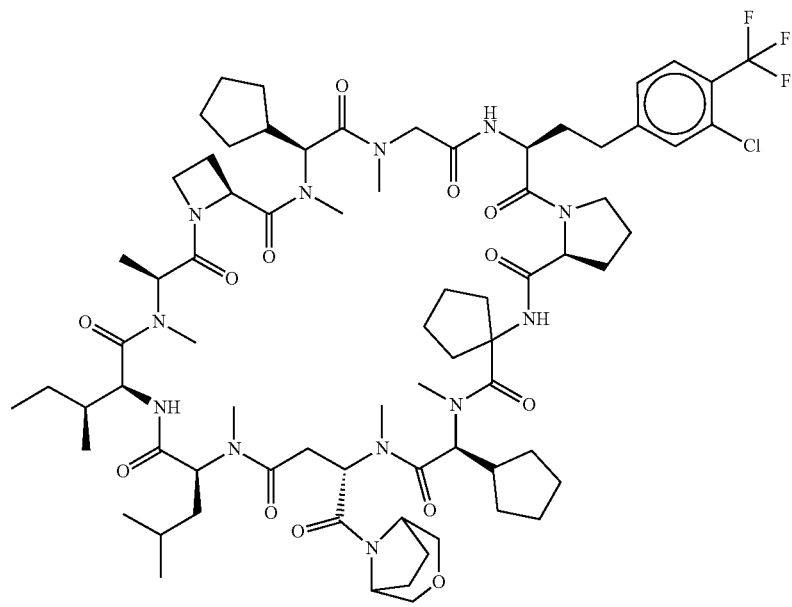 |

TABLE 24-continued
| Compound No. | Structural formula |
|---|---|
| 722 | 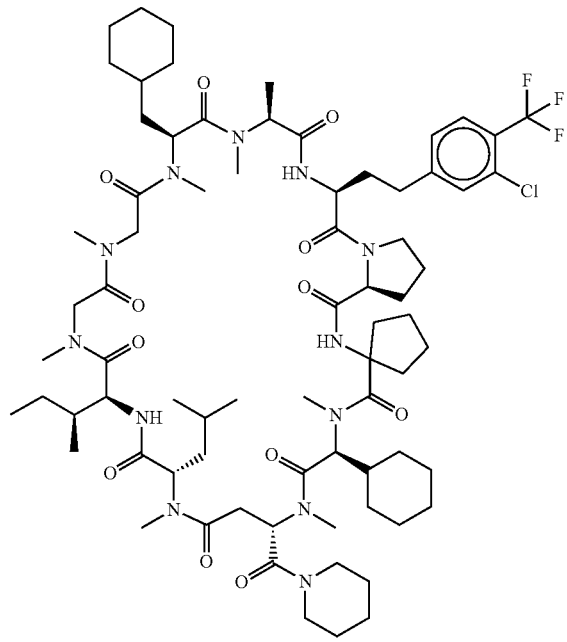 |
| 723 | 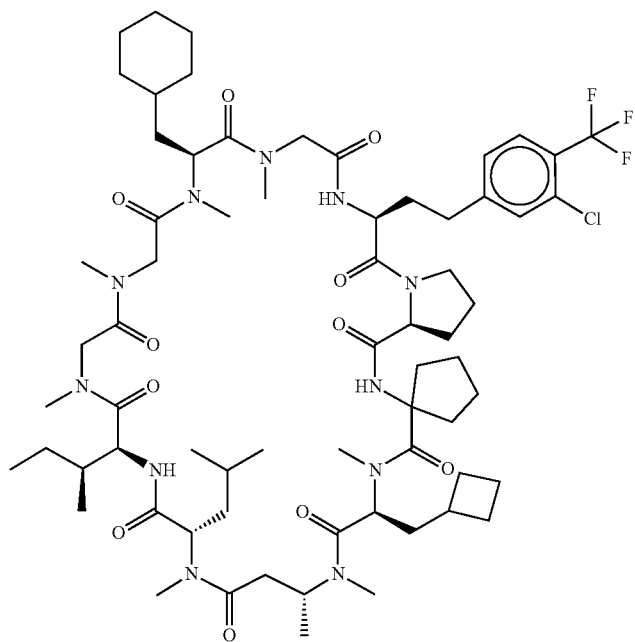 |

TABLE 24-continued
| Compound No. | Structural formula |
|---|---|
| 724 | 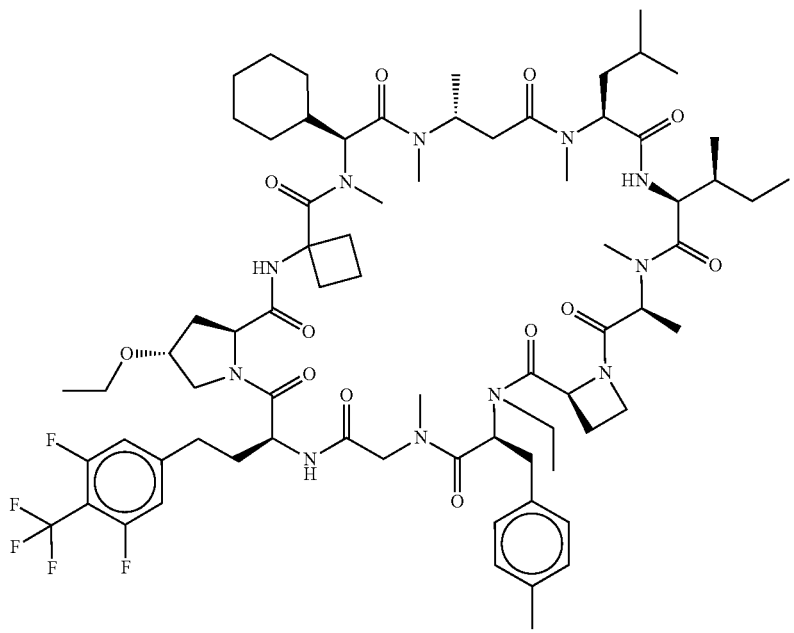 |
| 725 | 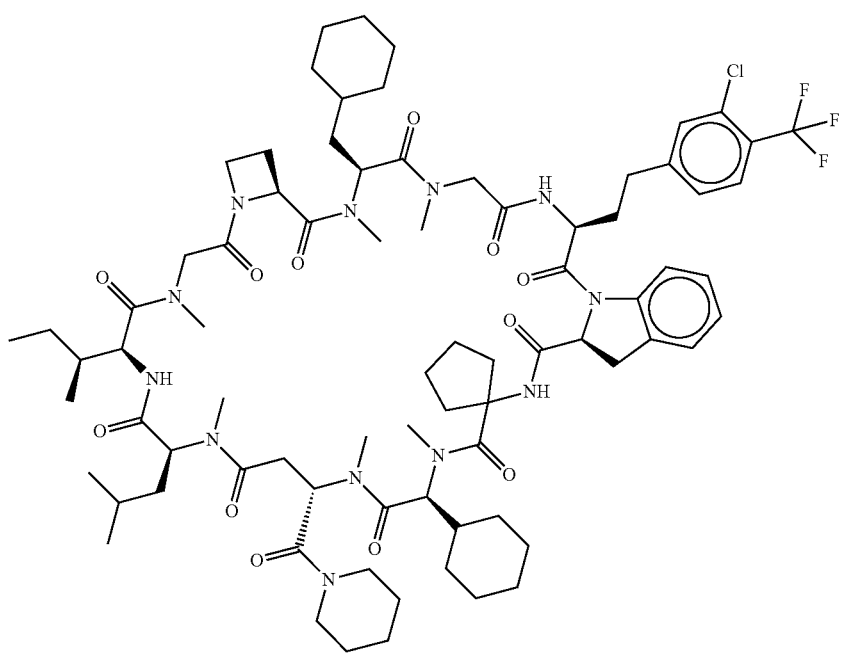 |

TABLE 24-continued
| Compound No. | Structural formula |
|---|---|
| 726 | 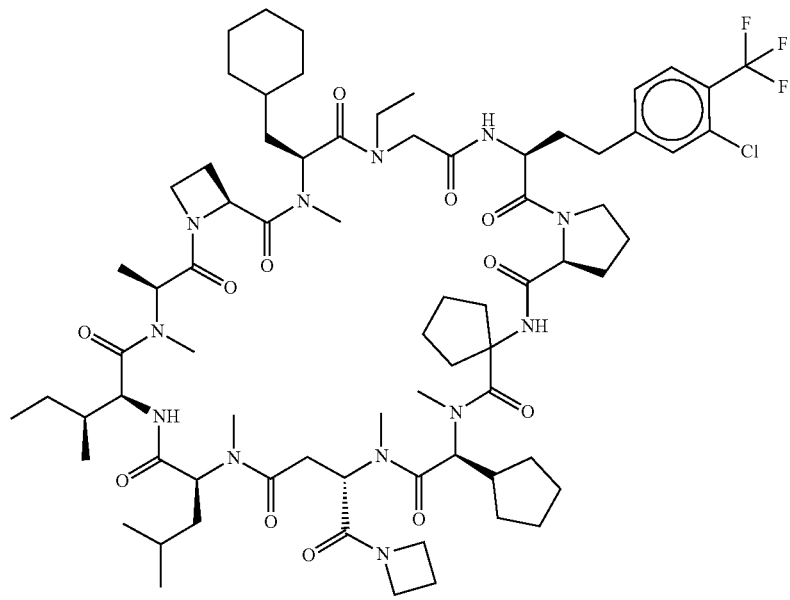 |
| 727 | 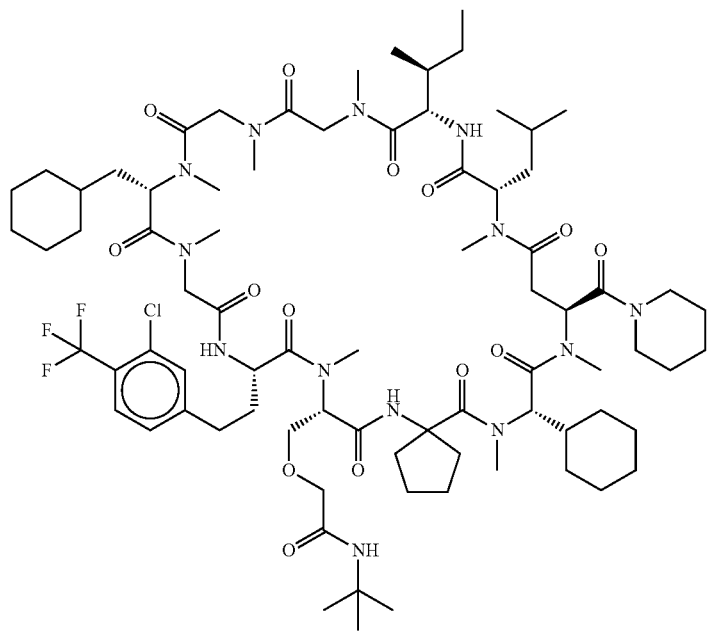 |

TABLE 24-continued
| Compound No. | Structural formula |
|---|---|
| 728 | 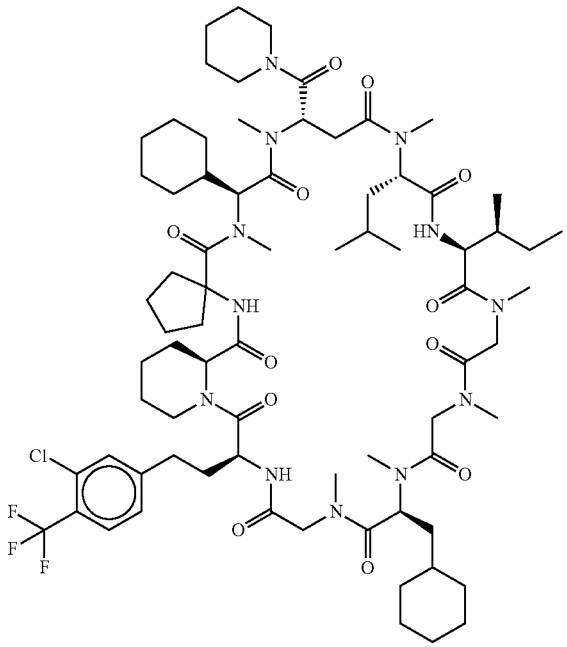 |
| 729 | 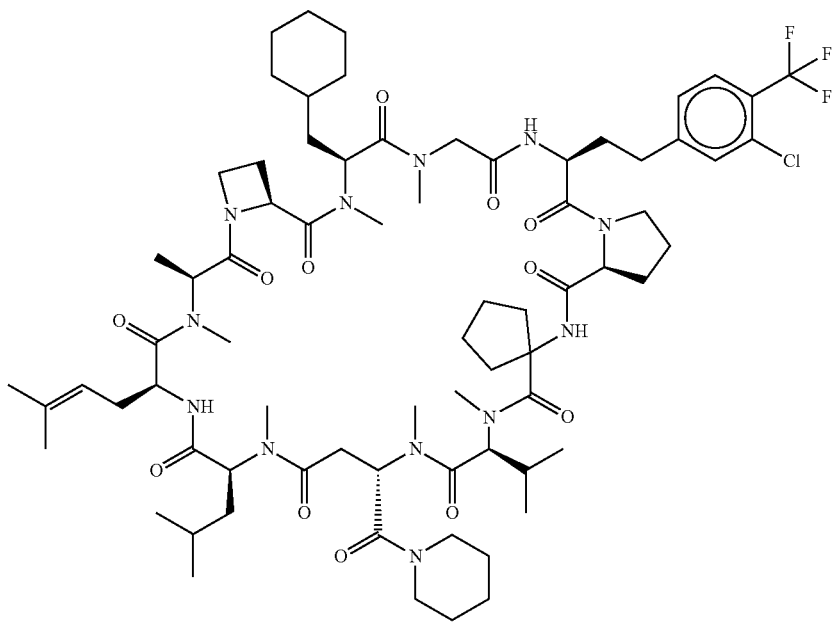 |

TABLE 24-continued
| Compound No. | Structural formula |
| --- | --- |
| 730 | 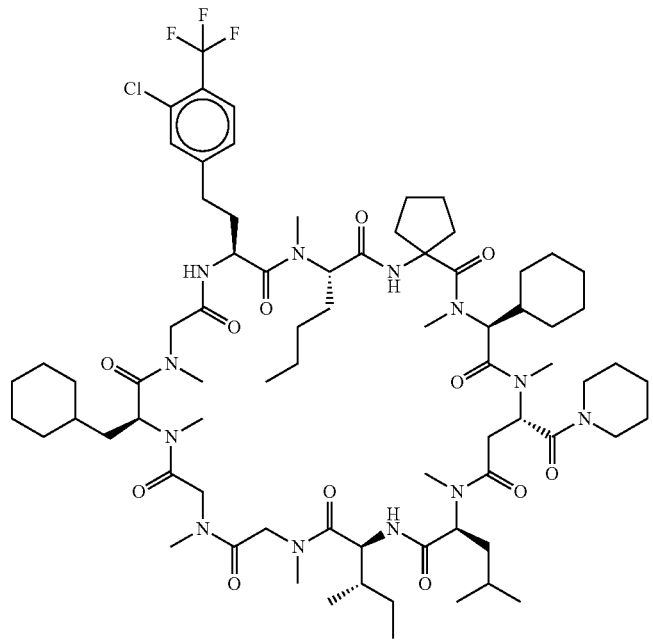 |
| 731 | 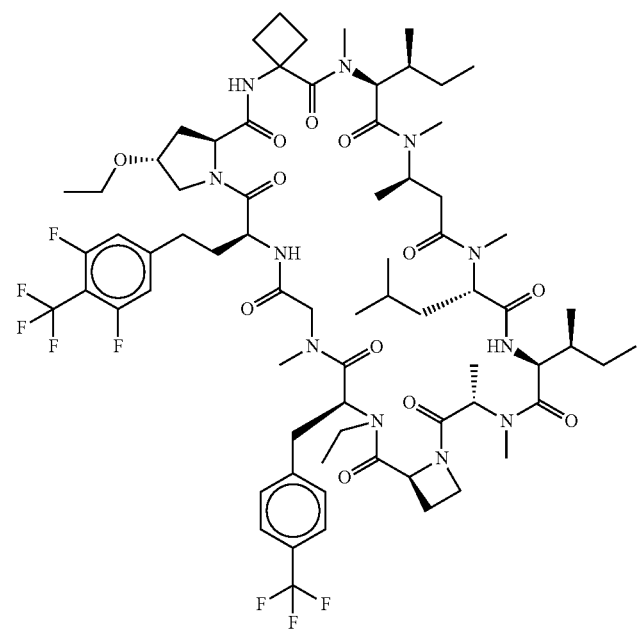 |

TABLE 24-continued
| Compound No. | Structural formula |
|---|---|
| 732 | 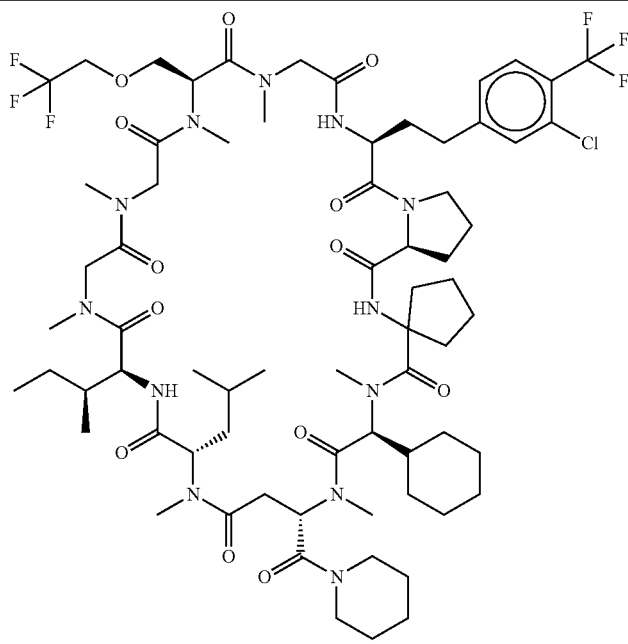 |
| 733 | 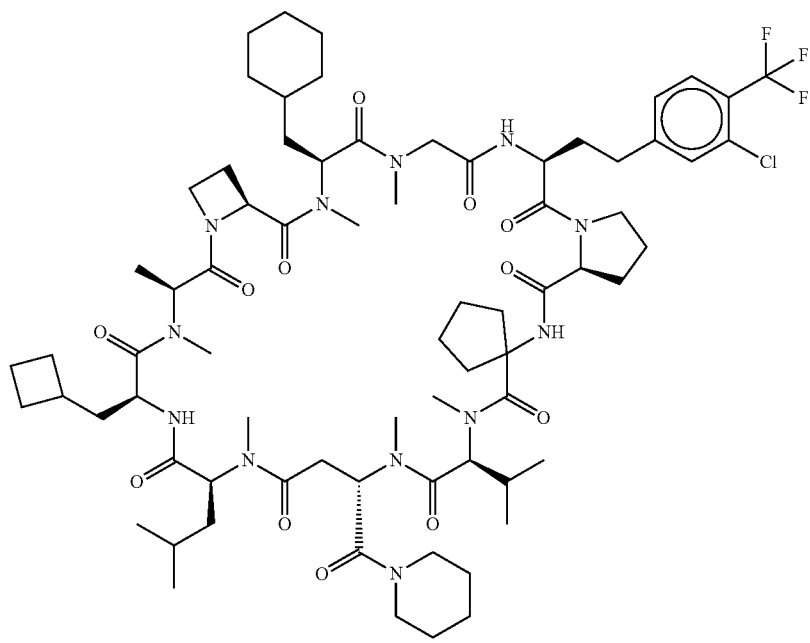 |

TABLE 24-continued
| Compound No. | Structural formula |
|---|---|
| 734 | 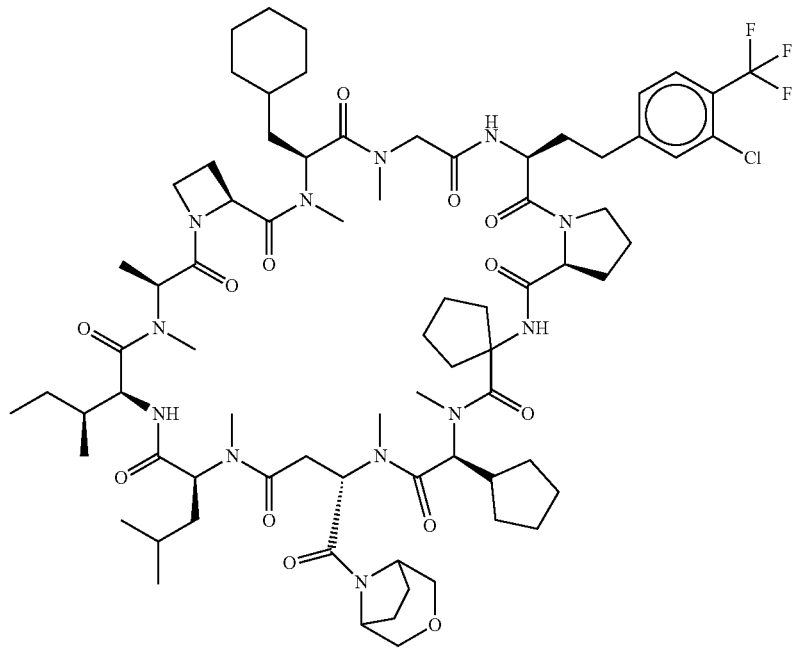 |
| 735 | 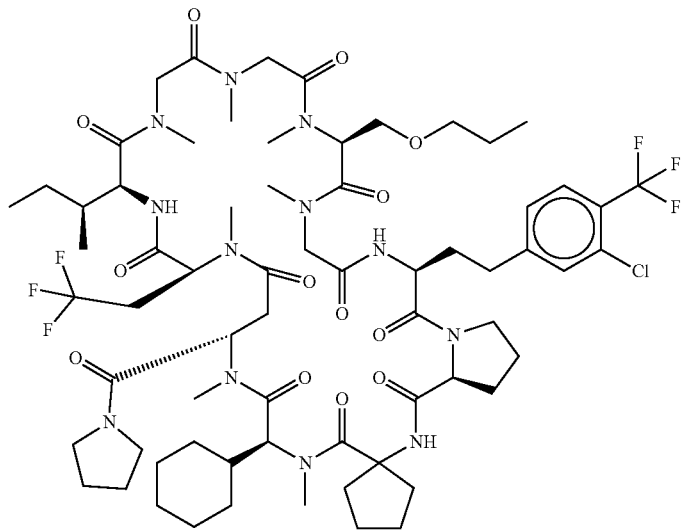 |

TABLE 24-continued
| Compound No. | Structural formula |
|---|---|
| 736 | 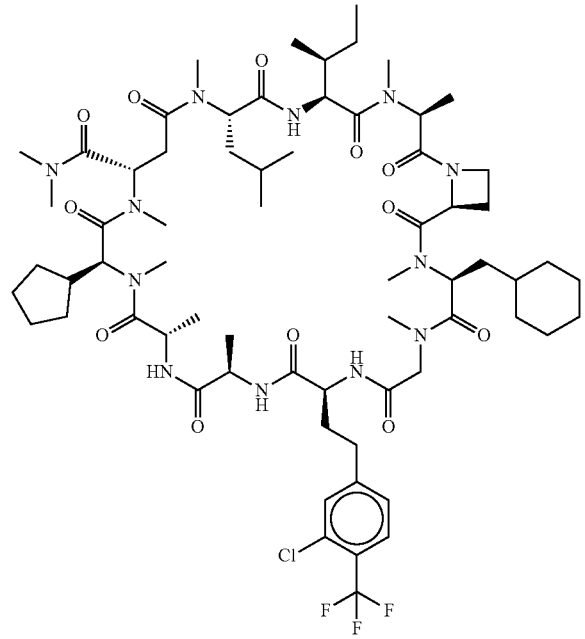 |
| 737 | 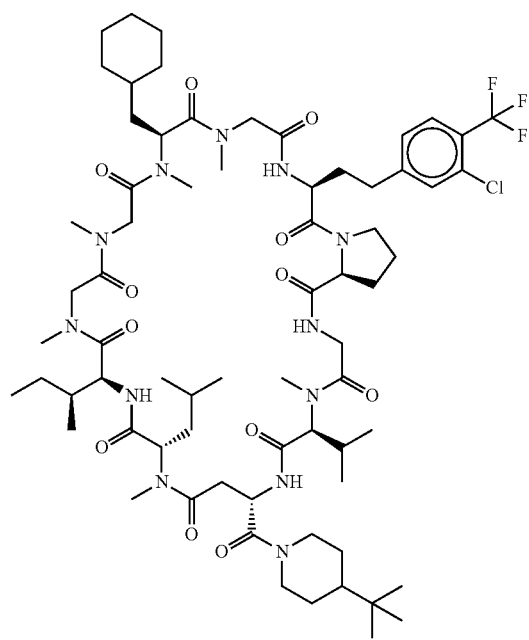 |

TABLE 24-continued
| Compound No. | Structural formula |
| --- | --- |
| 738 | 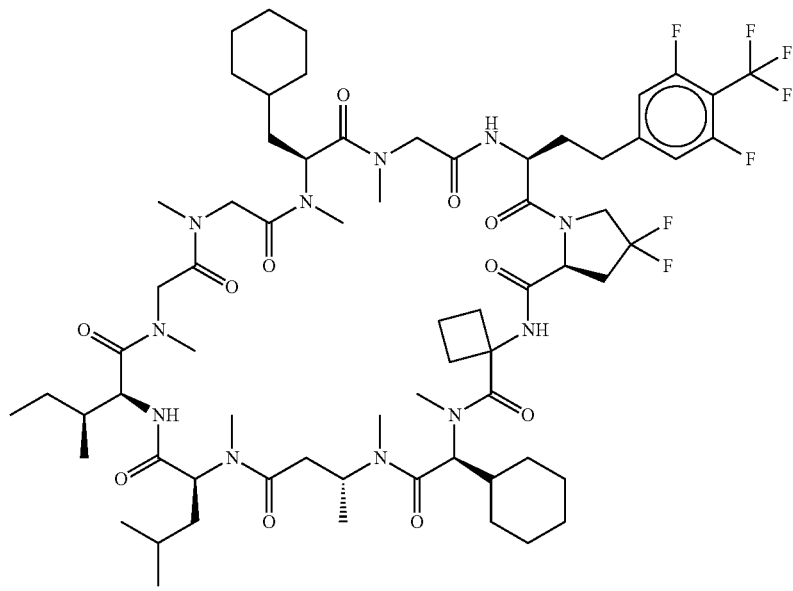 |
| 739 | 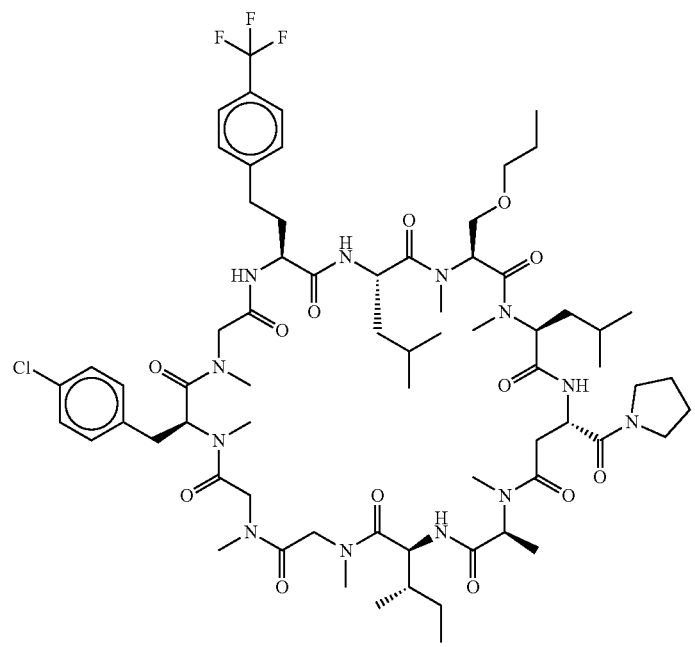 |

TABLE 24-continued
| Compound No. | Structural formula |
|---|---|
| 740 | 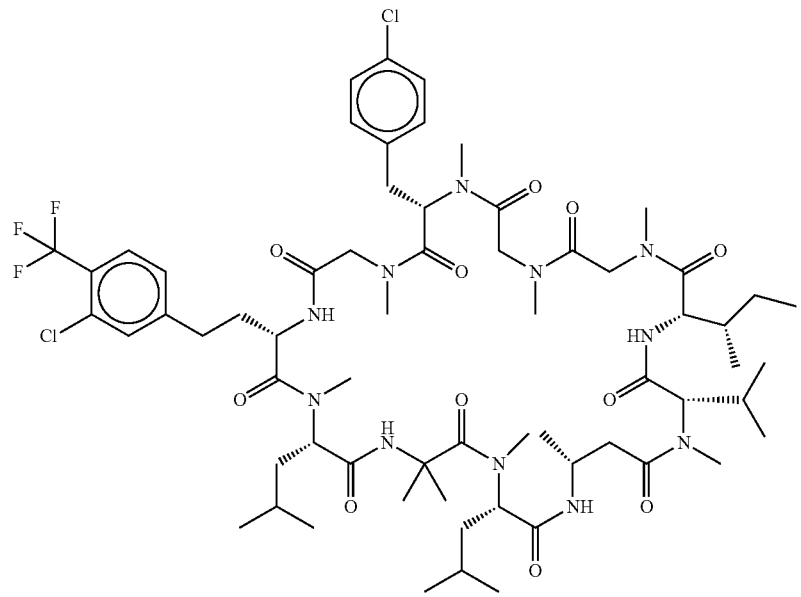 |
| 741 | 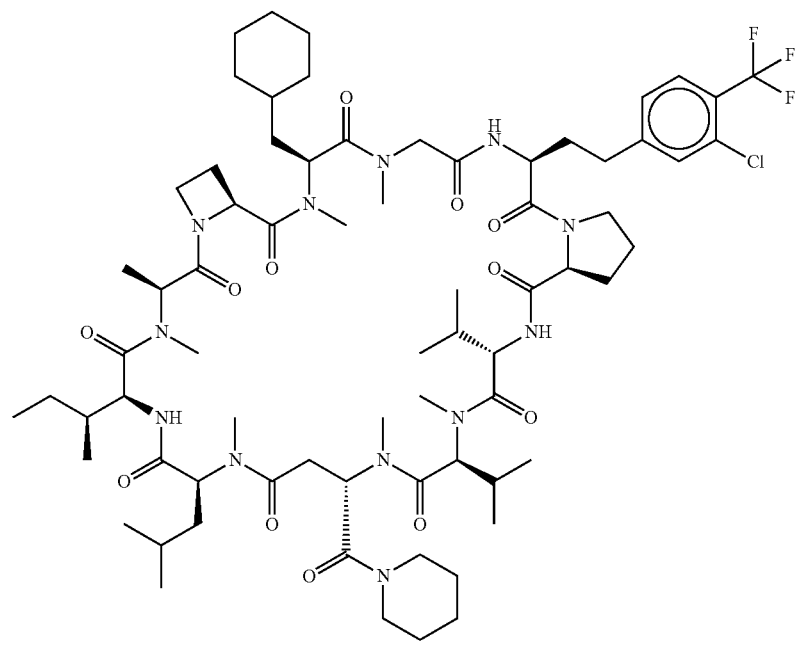 |

TABLE 24-continued
| Compound No. | Structural formula |
| --- | --- |
| 742 | 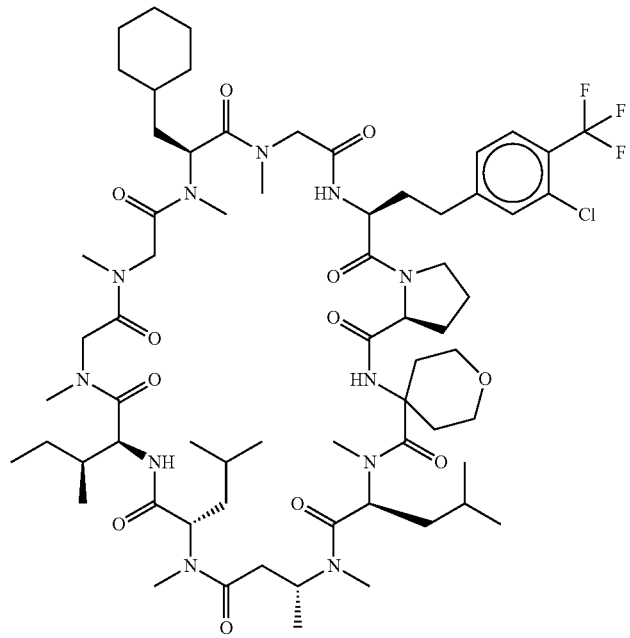 |
| 743 | 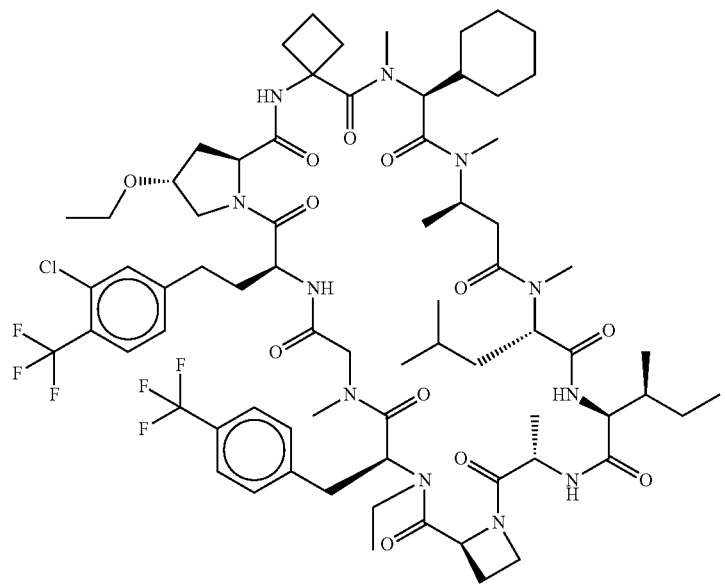 |

TABLE 24-continued
| Compound No. | Structural formula |
| --- | --- |
| 744 | 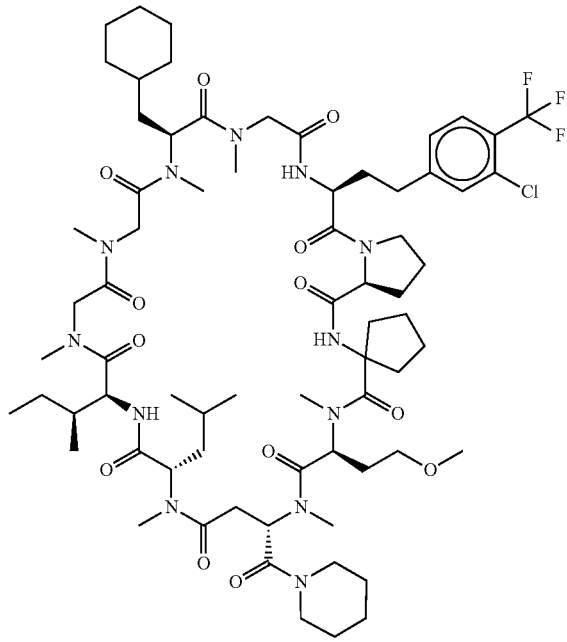 |
| 745 | 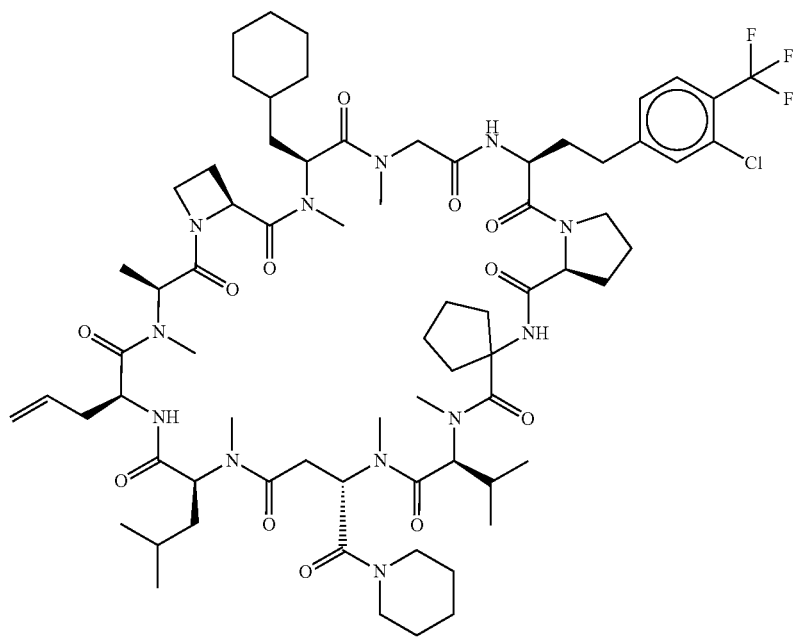 |

TABLE 24-continued
| Compound No. | Structural formula |
|---|---|
| 746 | 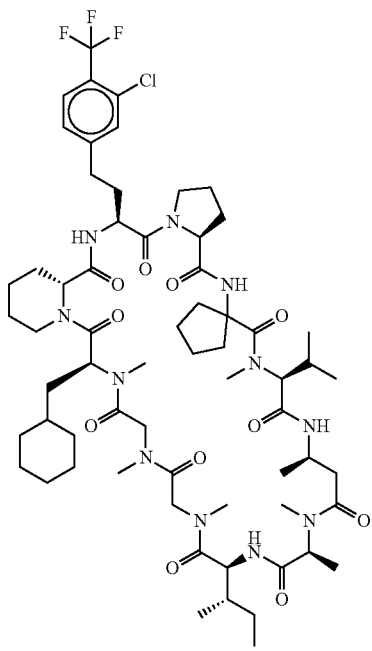 |
| 747 | 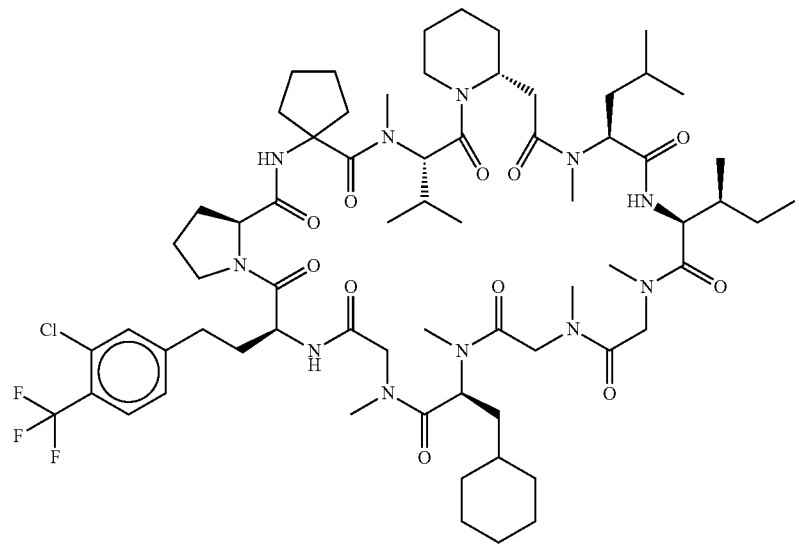 |

TABLE 24-continued
| Compound No. | Structural formula |
|---|---|
| 748 | 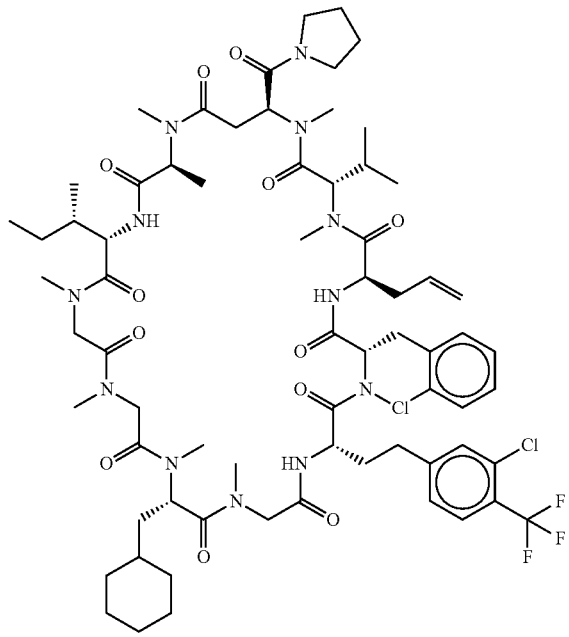 |
| 749 | 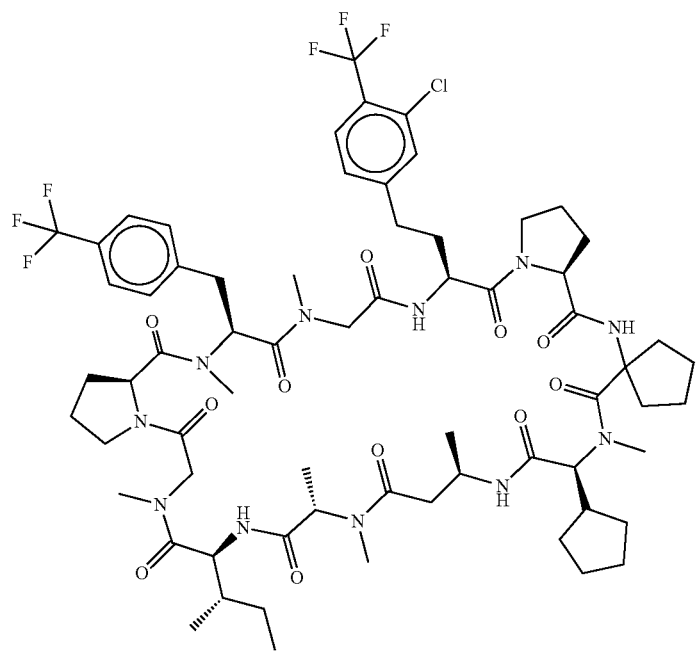 |

TABLE 24-continued
| Compound No. | Structural formula |
|---|---|
| 750 | 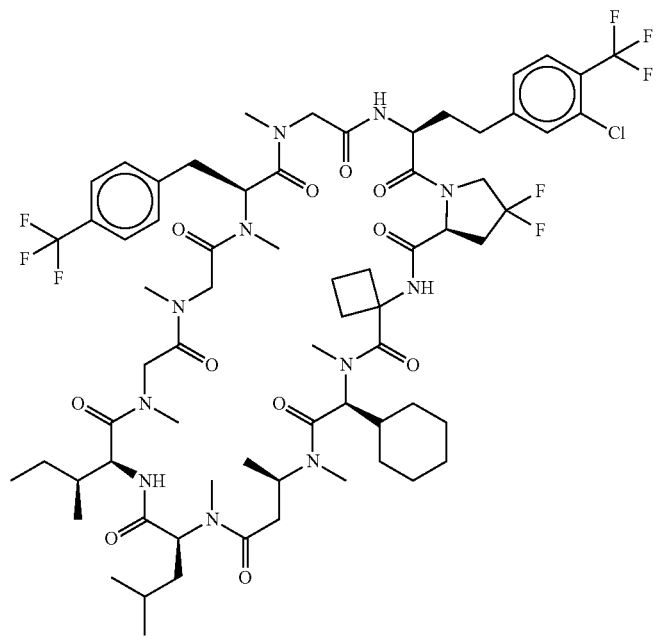 |
| 751 | 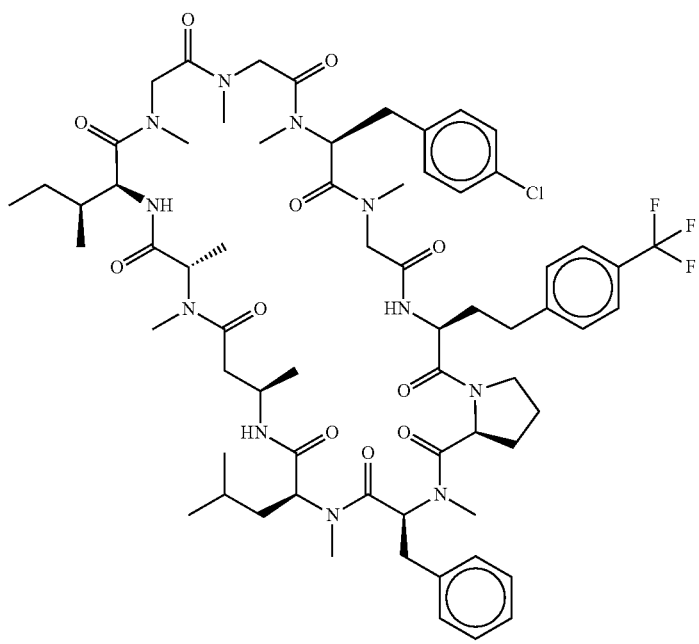 |

TABLE 24-continued
| Compound No. | Structural formula |
|---|---|
| 752 | 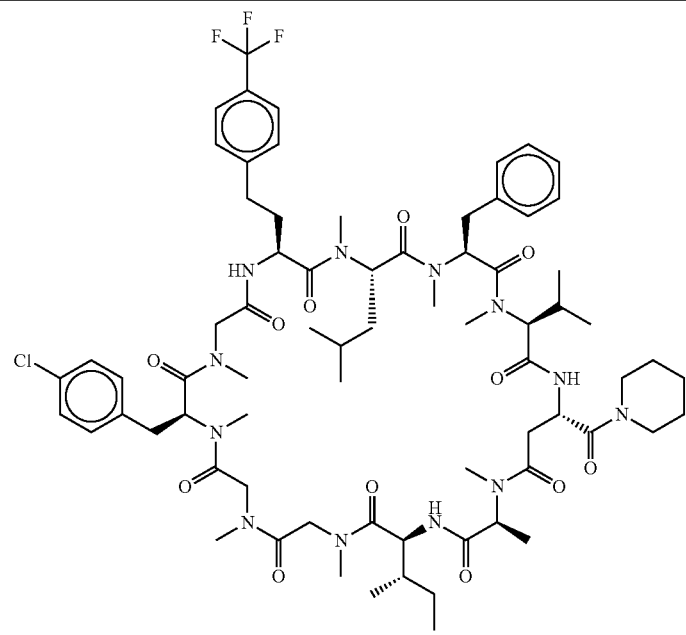 |
| 753 | 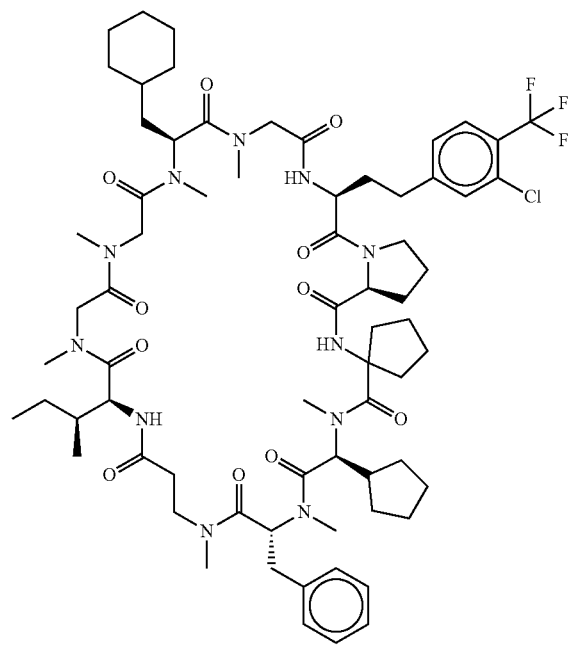 |

TABLE 24-continued
| Compound No. | Structural formula |
|---|---|
| 754 | 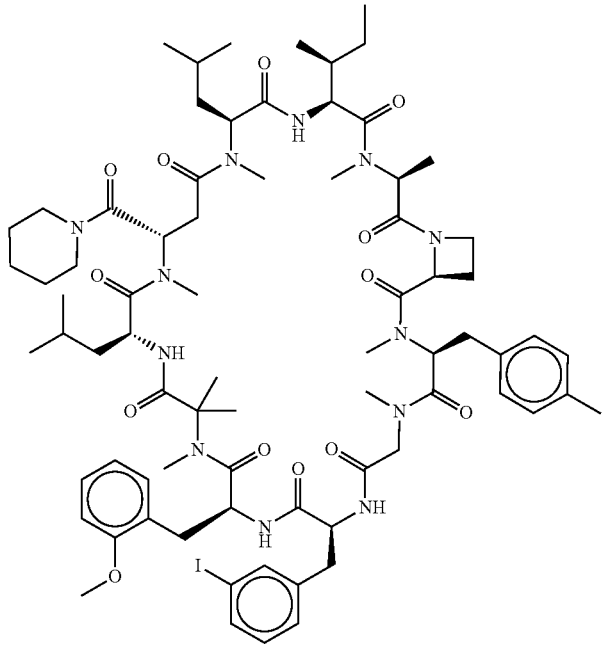 |
| 755 | 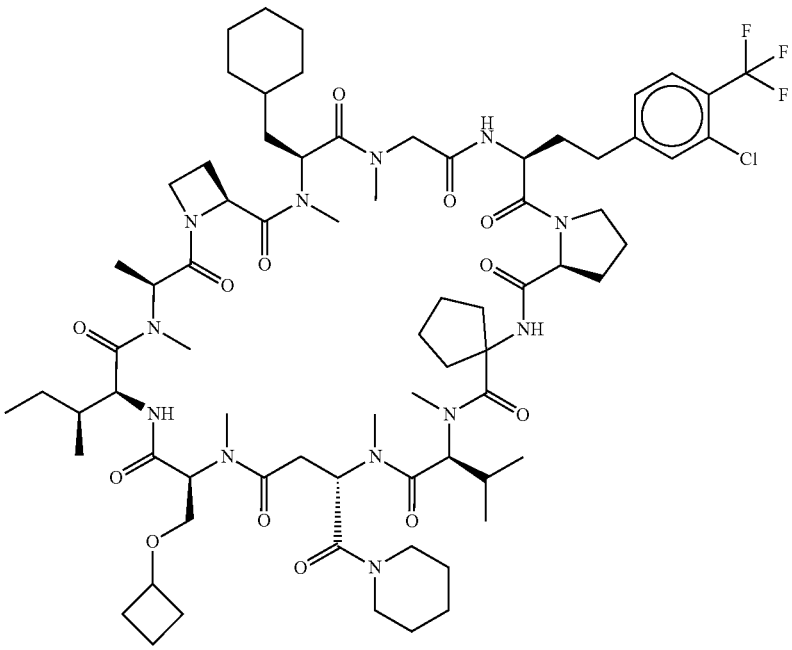 |

TABLE 24-continued
| Compound No. | Structural formula |
|---|---|
| 756 | 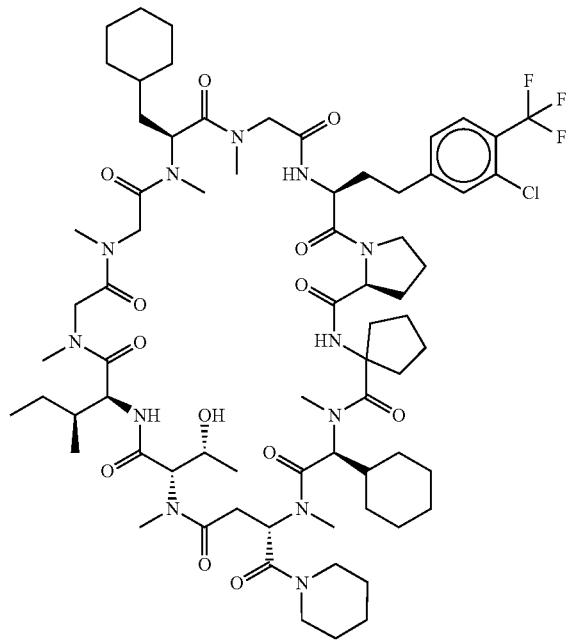 |
| 757 | 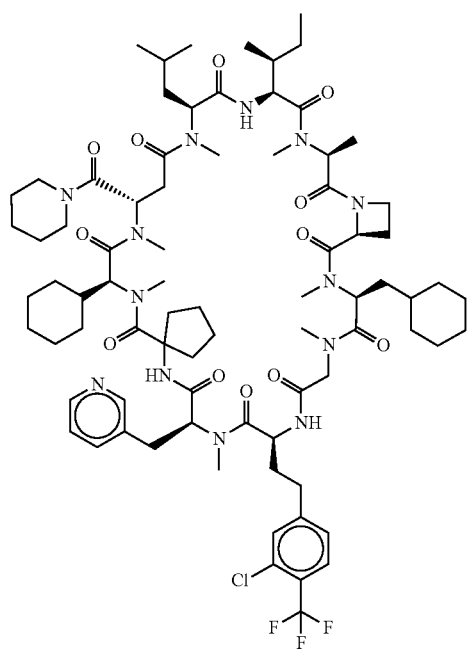 |

TABLE 24-continued
| Compound No. | Structural formula |
|---|---|
| 758 | 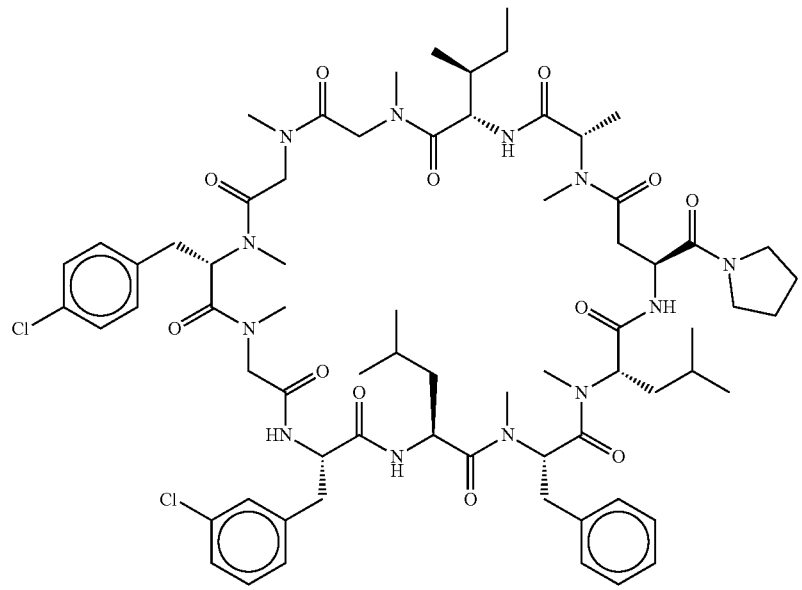 |
| 759 | 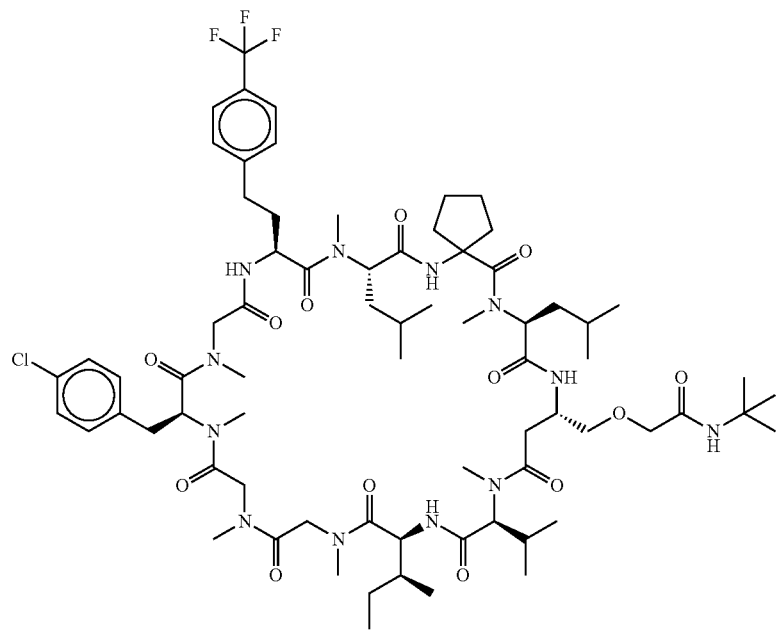 |

TABLE 24-continued
| Compound No. | Structural formula |
|---|---|
| 760 | 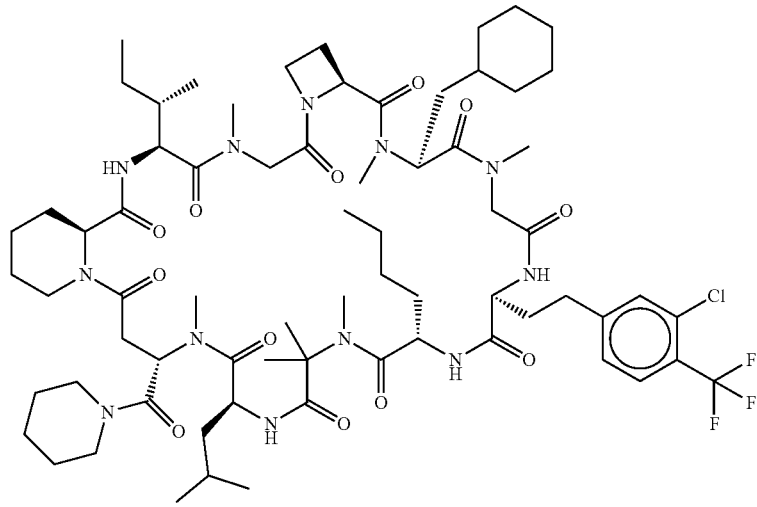 |
| 761 | 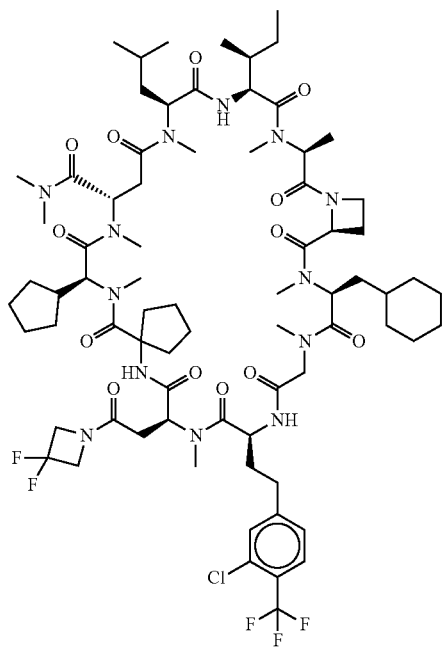 |

TABLE 24-continued
| Compound No. | Structural formula |
|---|---|
| 762 | 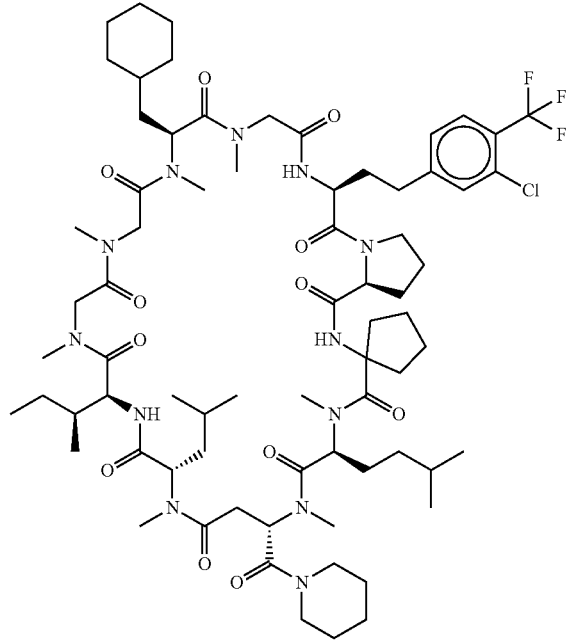 |
| 764 | 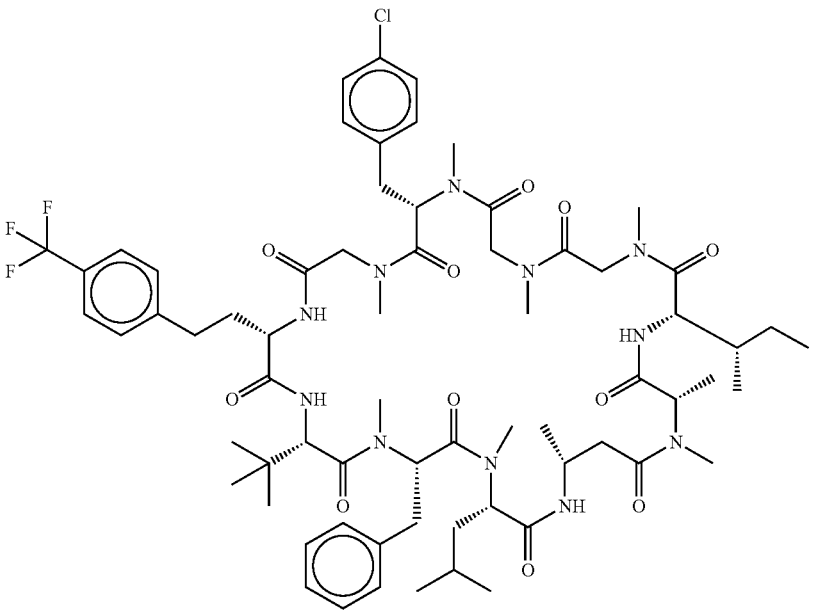 |

TABLE 24-continued

| Compound No. | Structural formula |
|---|---|
| 765 | |
| 766 | |

TABLE 24-continued
| Compound No. | Structural formula |
|---|---|
| 767 | 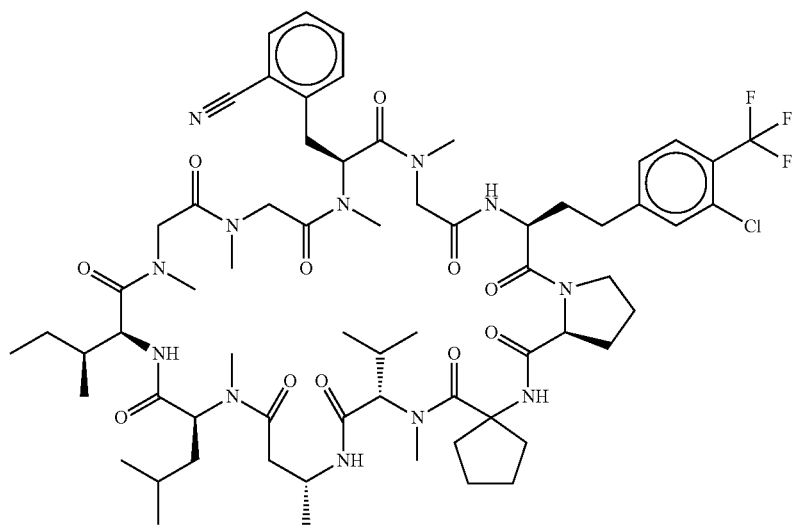 |
| 768 | 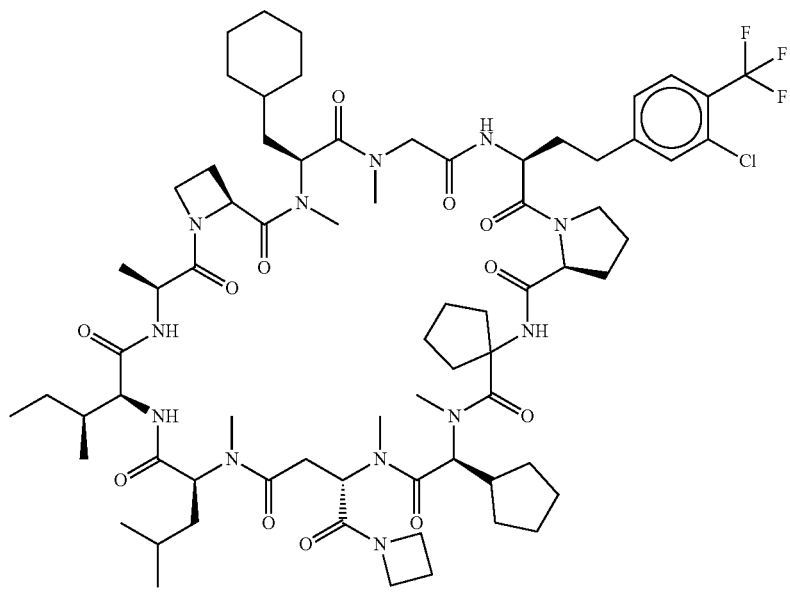 |

TABLE 24-continued
| Compound No. | Structural formula |
|---|---|
| 769 | 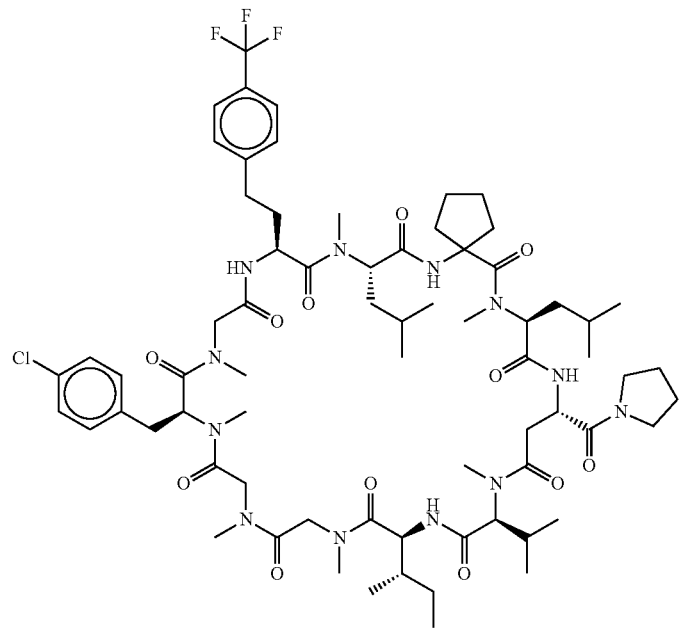 |
| 770 | 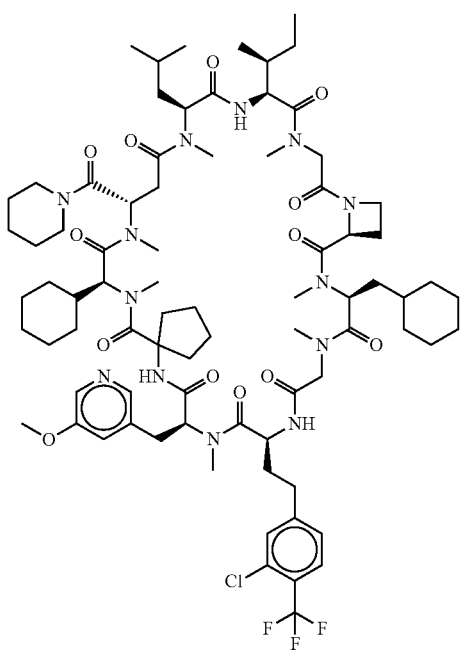 |

TABLE 24-continued
| Compound No. | Structural formula |
|---|---|
| 771 | 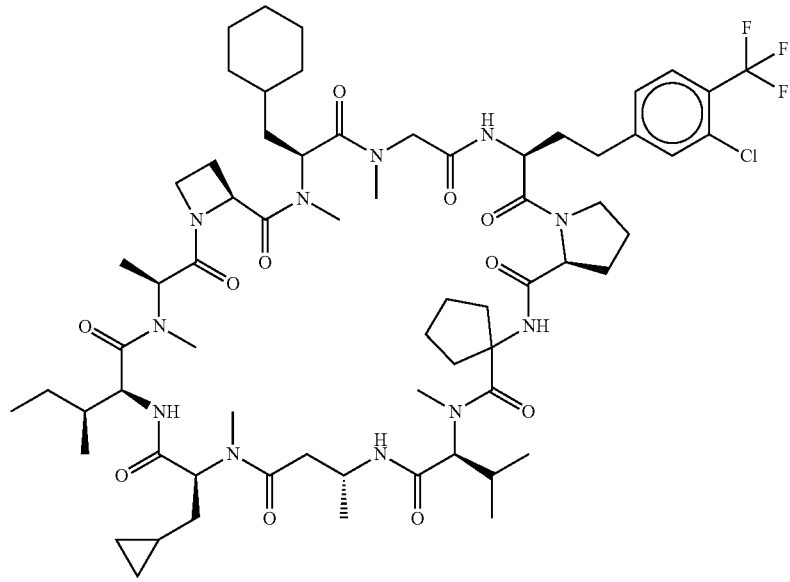 |
| 772 | 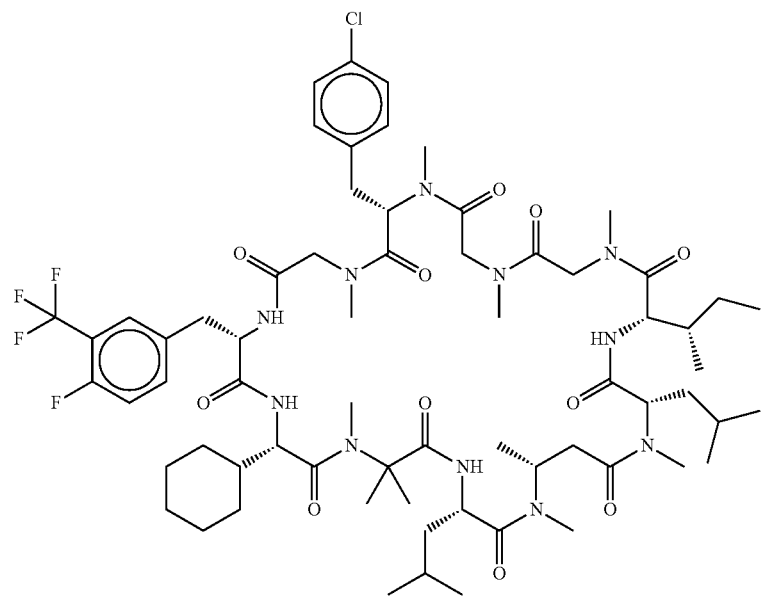 |

TABLE 24-continued
| Compound No. | Structural formula |
|---|---|
| 773 | 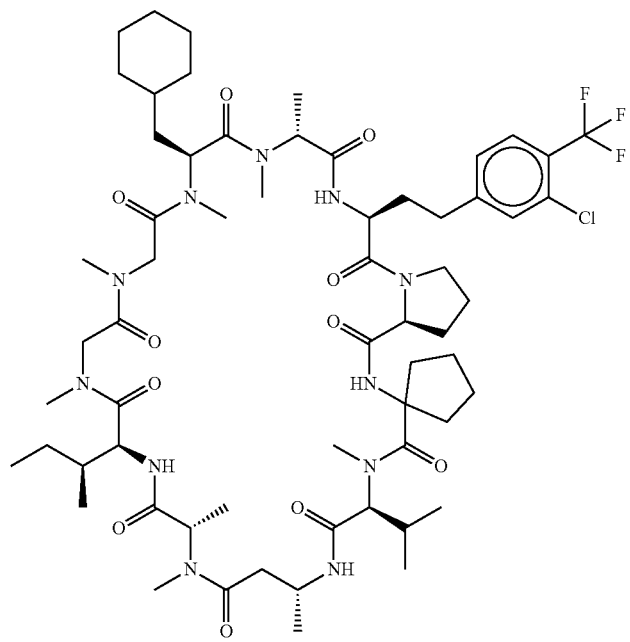 |
| 774 | 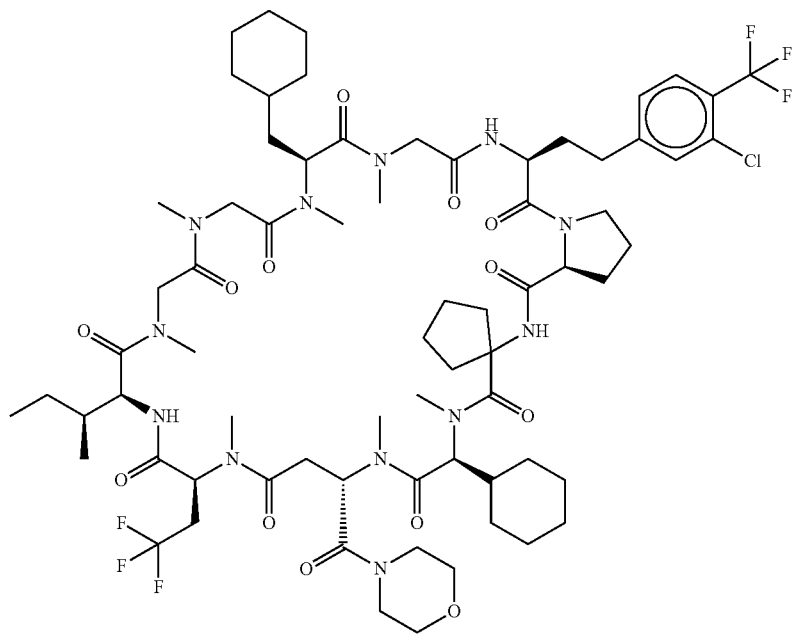 |

TABLE 24-continued
| Compound No. | Structural formula |
|---|---|
| 775 | 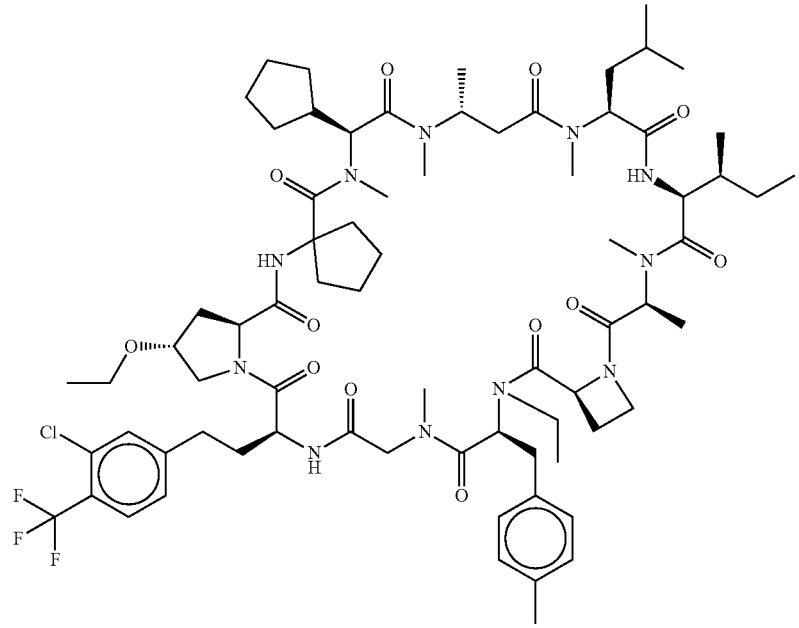 |
| 776 | 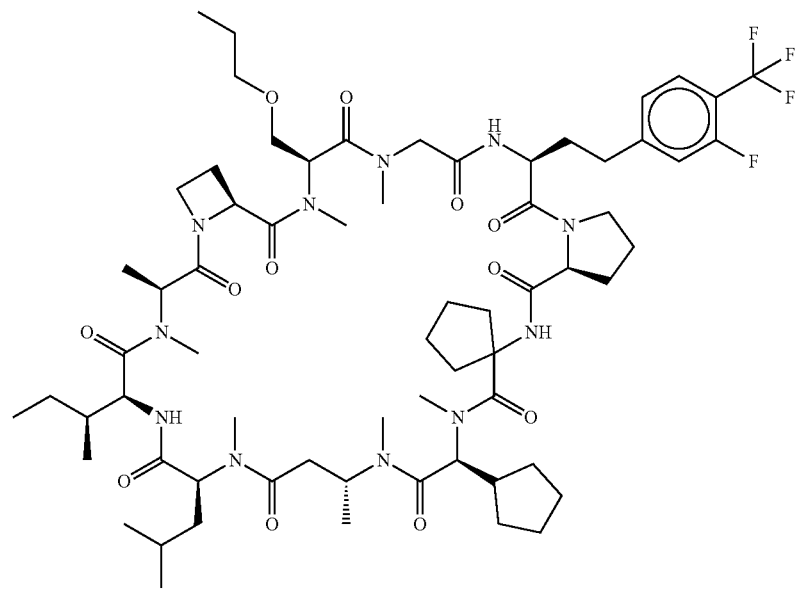 |

TABLE 24-continued
| Compound No. | Structural formula |
|---|---|
| 777 | 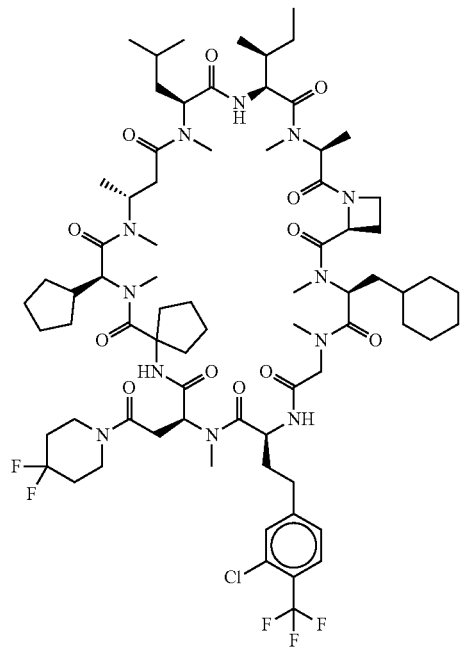 |
| 778 | 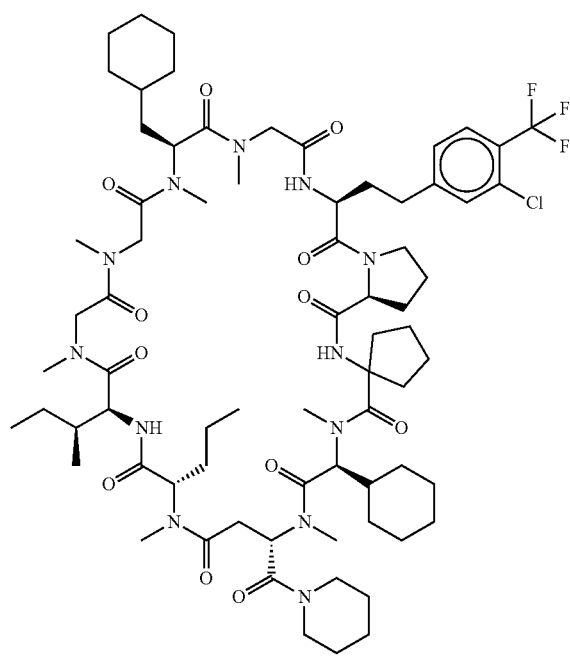 |

TABLE 24-continued
| Compound No. | Structural formula |
|---|---|
| 779 | 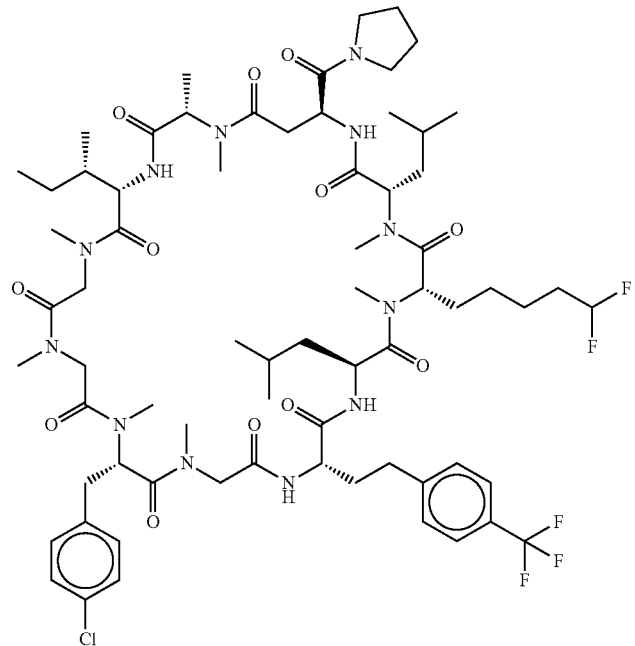 |
| 780 | 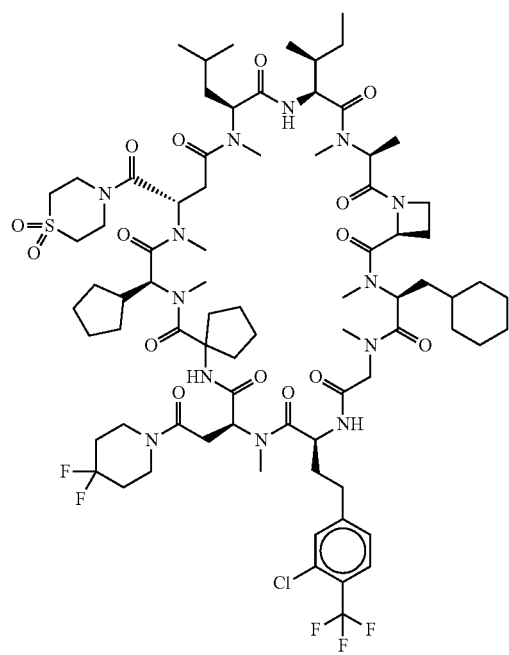 |

TABLE 24-continued
| Compound No. | Structural formula |
|---|---|
| 781 | 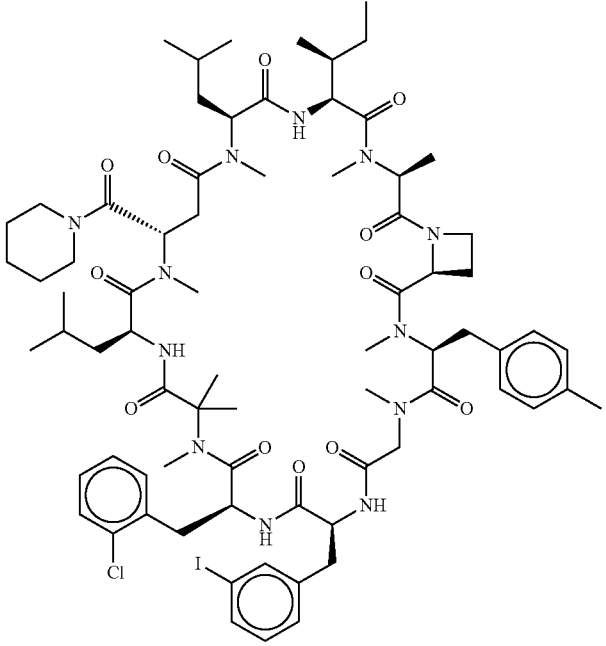 |
| 782 | 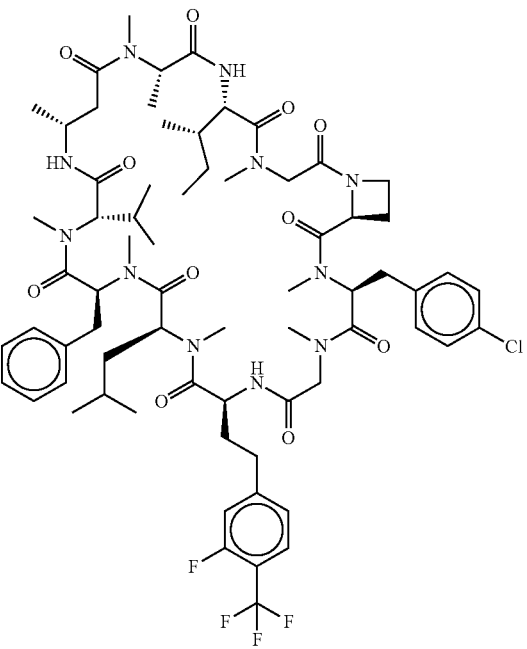 |

TABLE 24-continued
| Compound No. | Structural formula |
|---|---|
| 783 | 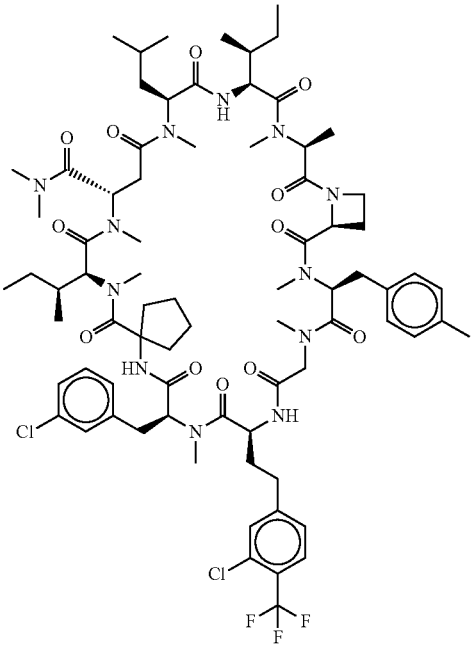 |
| 784 | 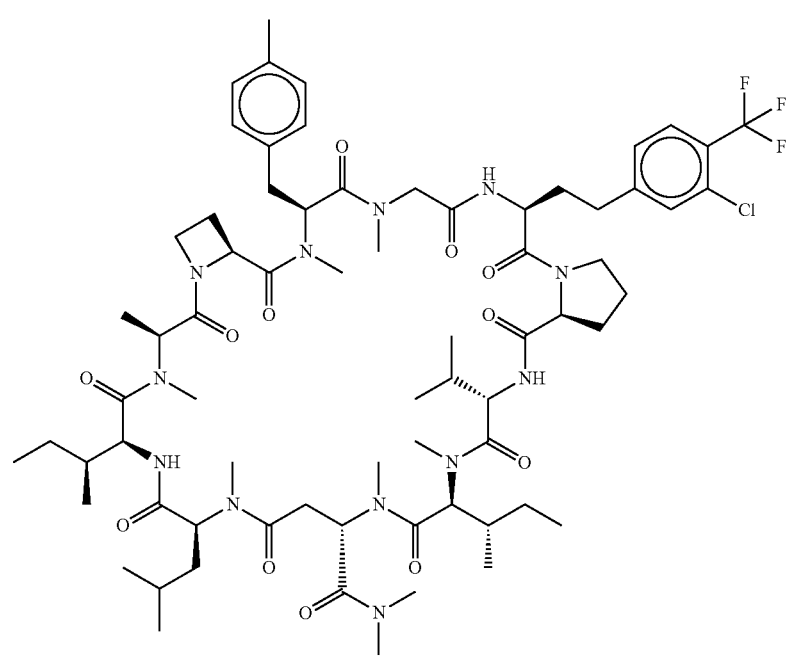 |

TABLE 24-continued
| Compound No. | Structural formula |
|---|---|
| 785 | 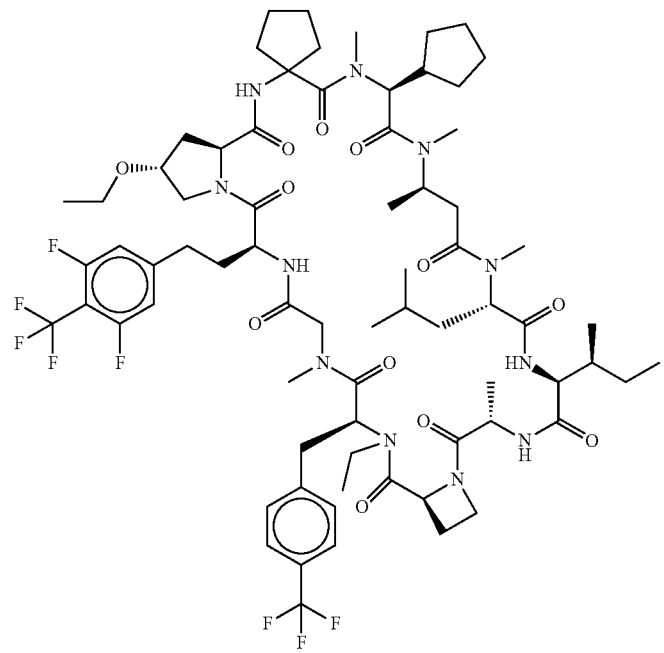 |
| 786 | 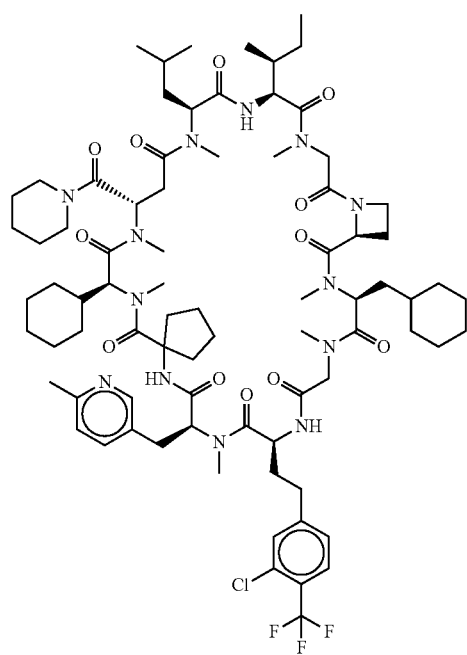 |

TABLE 24-continued
| Compound No. | Structural formula |
|---|---|
| 787 | 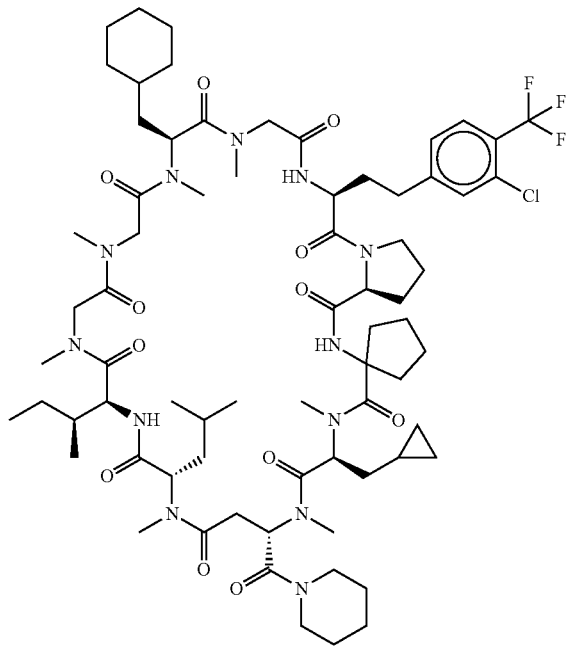 |
| 788 | 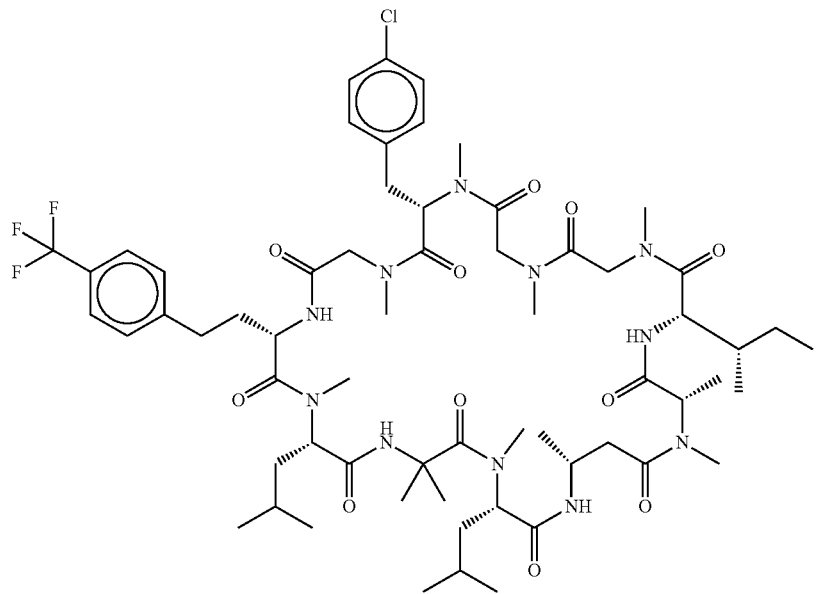 |

TABLE 24-continued
| Compound No. | Structural formula |
|---|---|
| 789 | 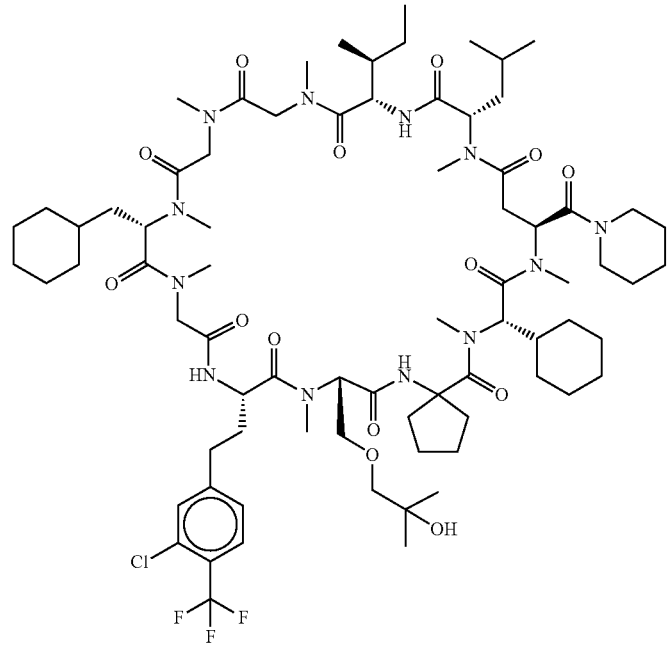 |
| 790 | 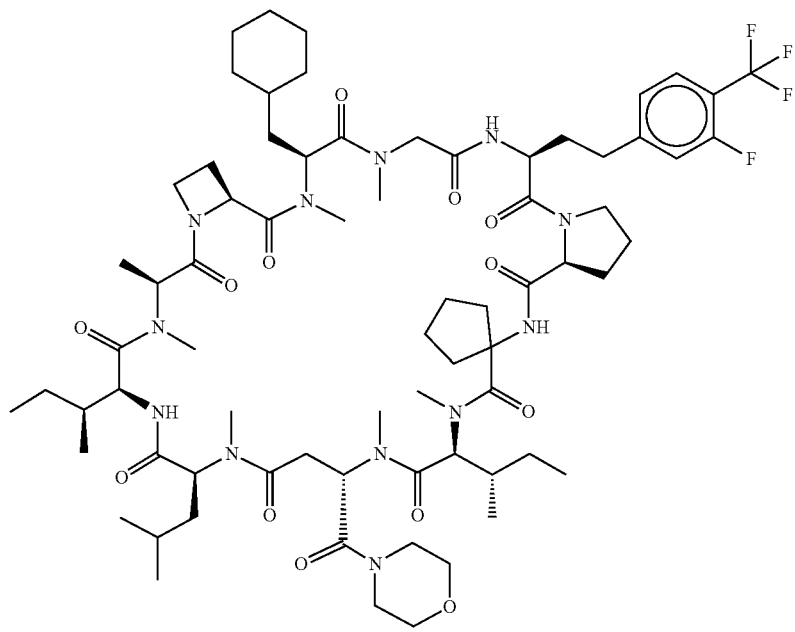 |

TABLE 24-continued
| Compound No. | Structural formula |
|---|---|
| 791 | 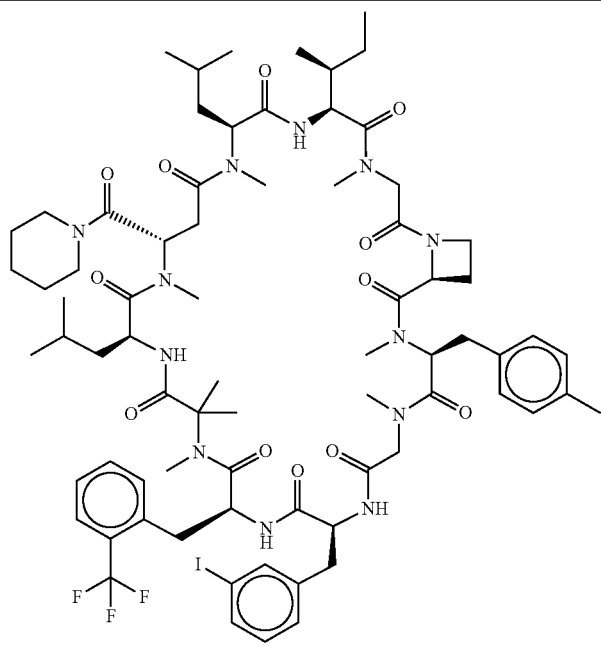 |
| 792 | 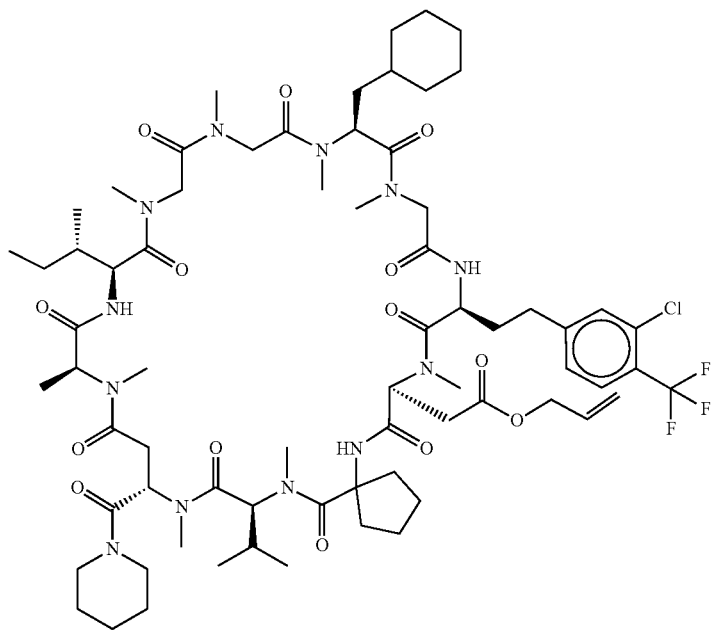 |

TABLE 24-continued
| Compound No. | Structural formula |
|---|---|
| 793 | 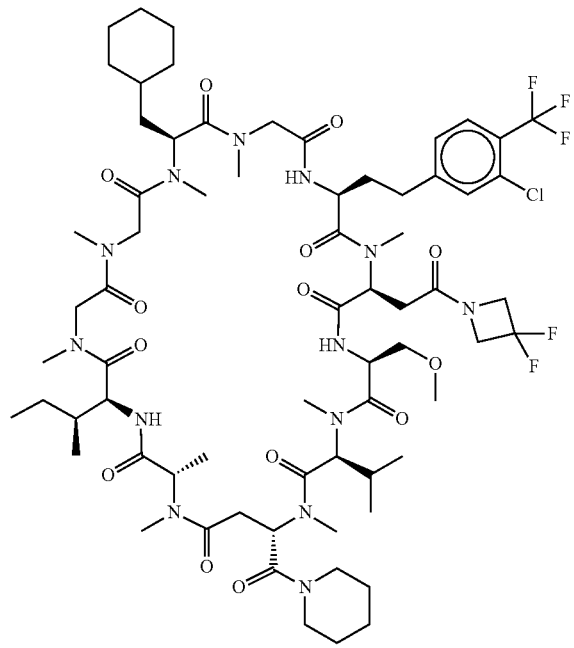 |
| 794 | 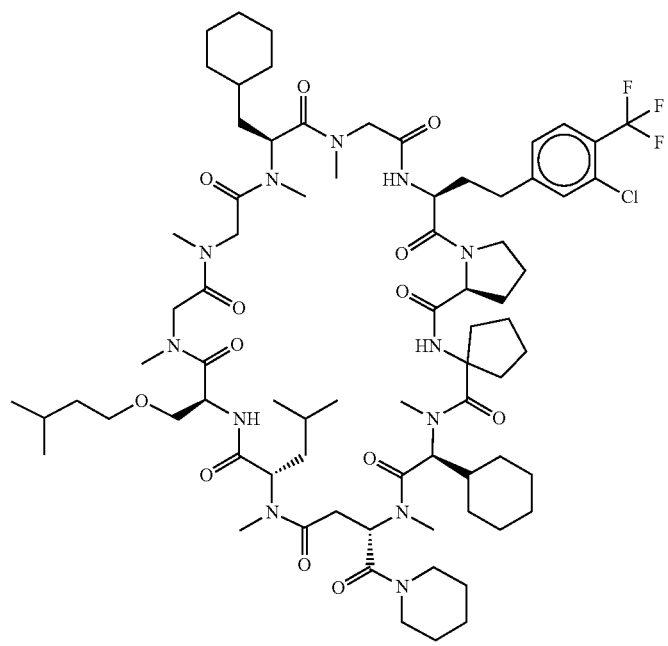 |

TABLE 24-continued
| Compound No. | Structural formula |
|---|---|
| 795 | 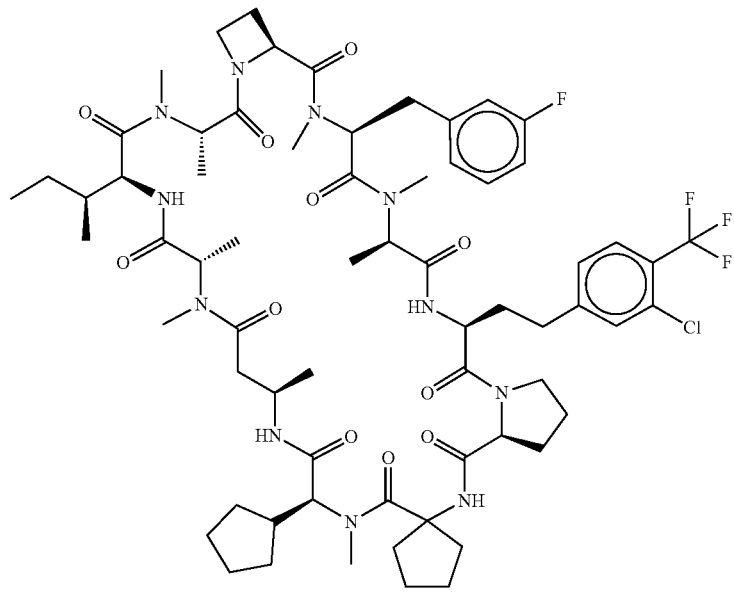 |
| 796 | 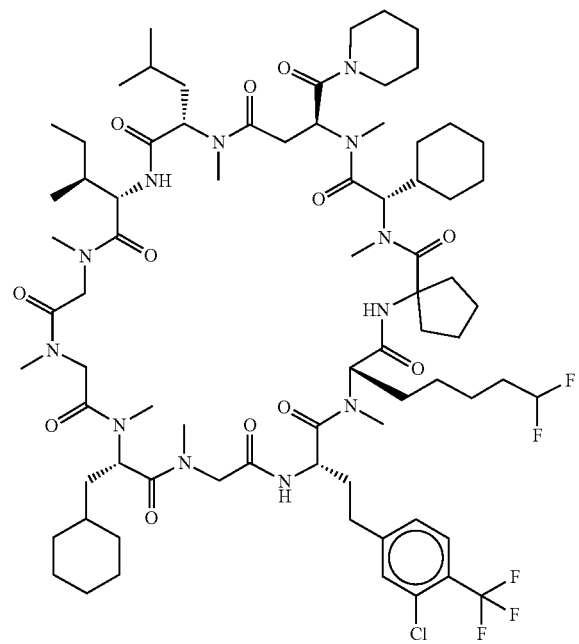 |

TABLE 24-continued
| Compound No. | Structural formula |
|---|---|
| 797 | 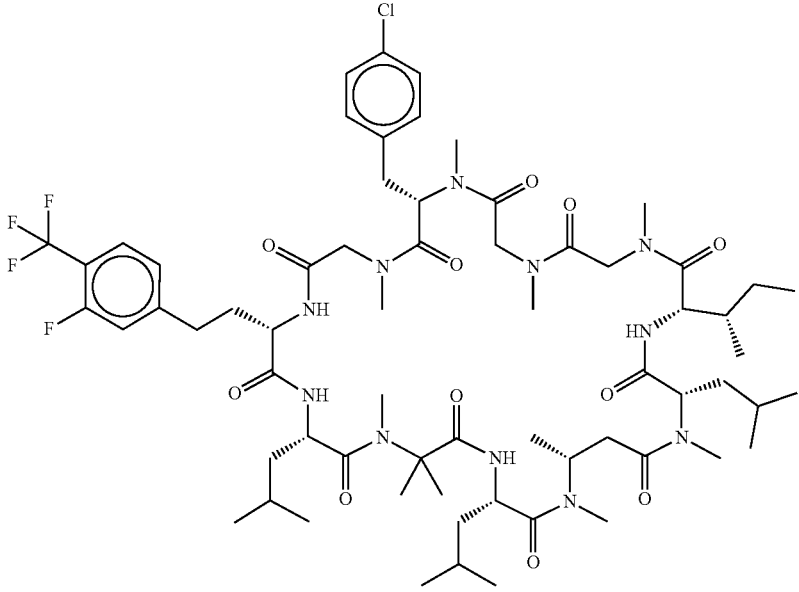 |
| 798 | 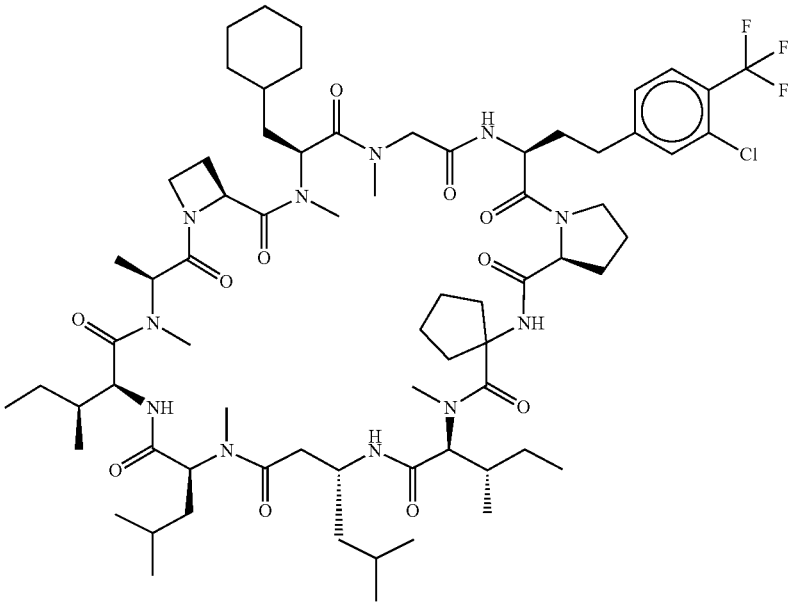 |

TABLE 24-continued
| Compound No. | Structural formula |
|---|---|
| 799 | 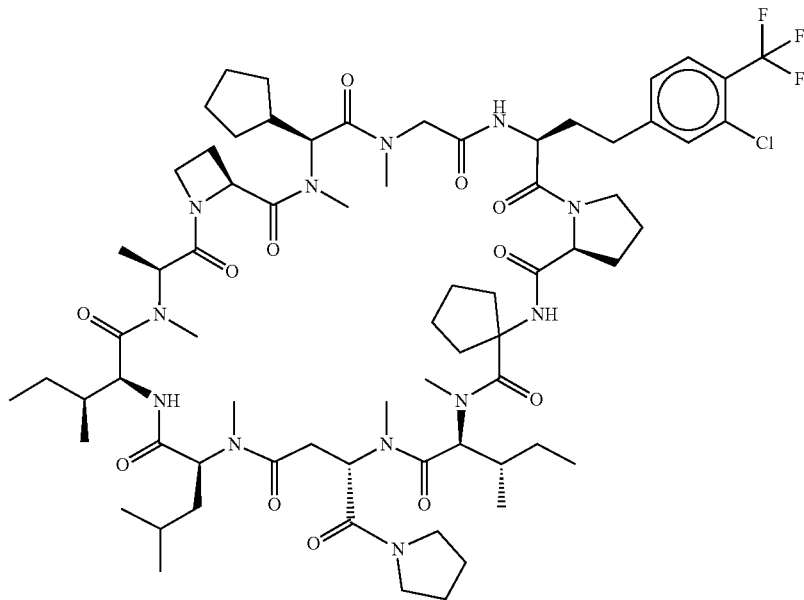 |
| 800 | 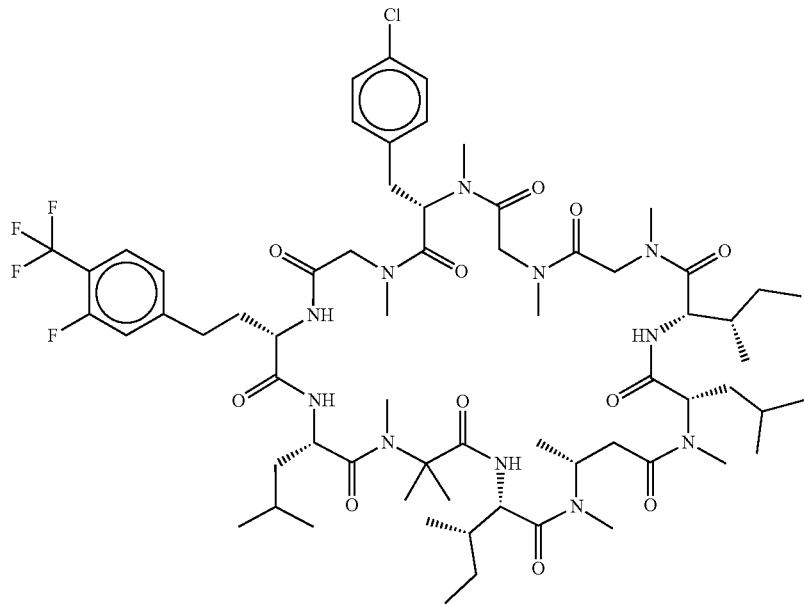 |

TABLE 24-continued
| Compound No. | Structural formula |
|---|---|
| 801 | 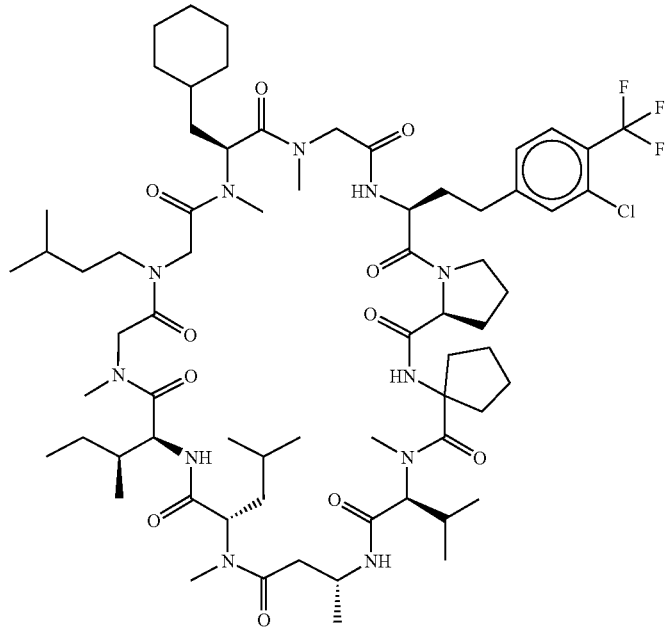 |
| 802 | 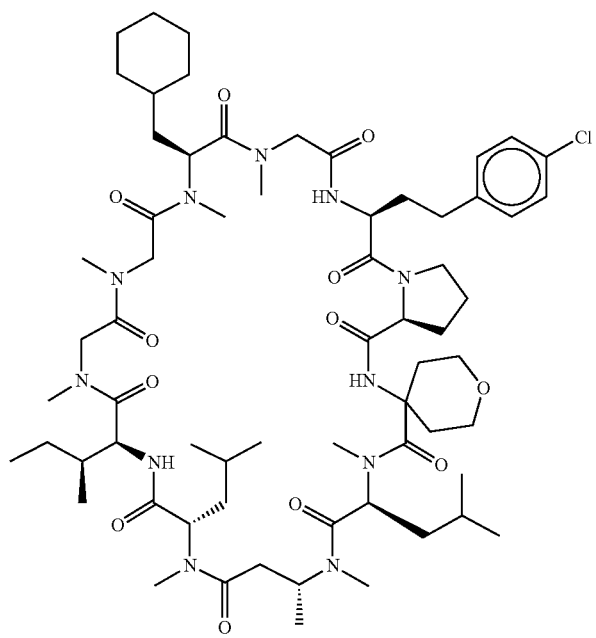 |

TABLE 24-continued
| Compound No. | Structural formula |
|---|---|
| 803 | 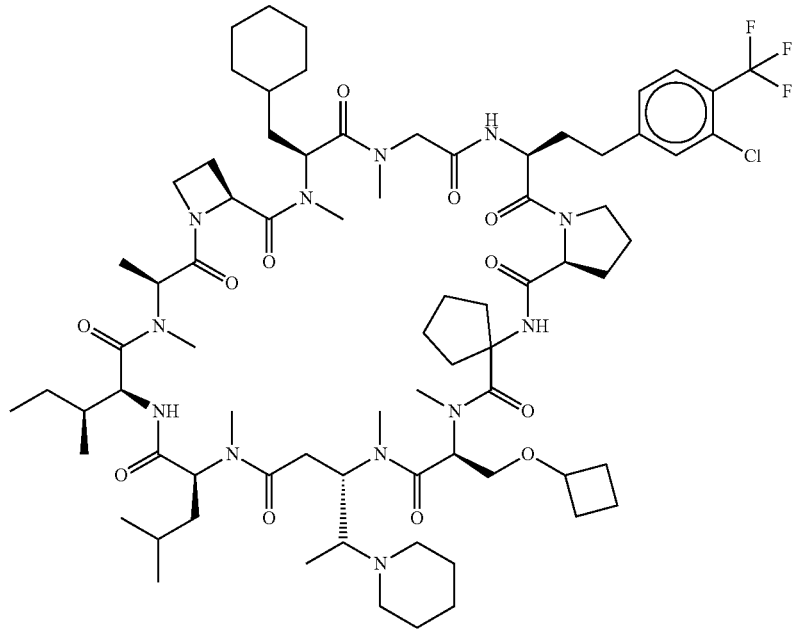 |
| 804 | 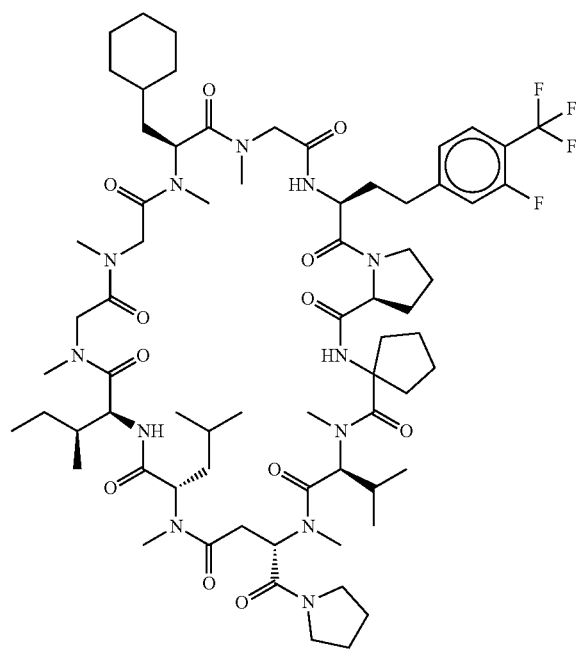 |

TABLE 24-continued
| Compound No. | Structural formula |
|---|---|
| 805 | 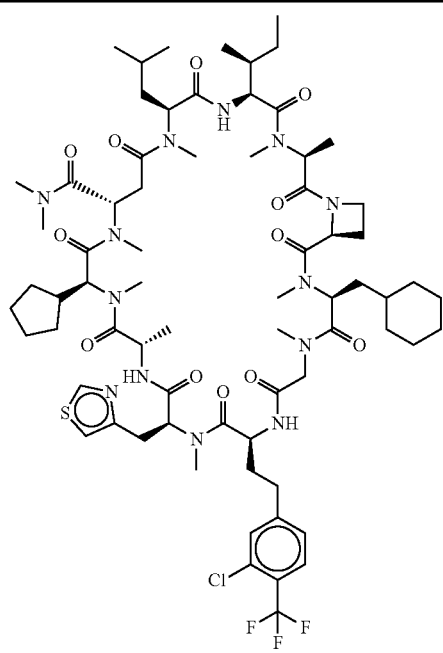 |
| 806 | 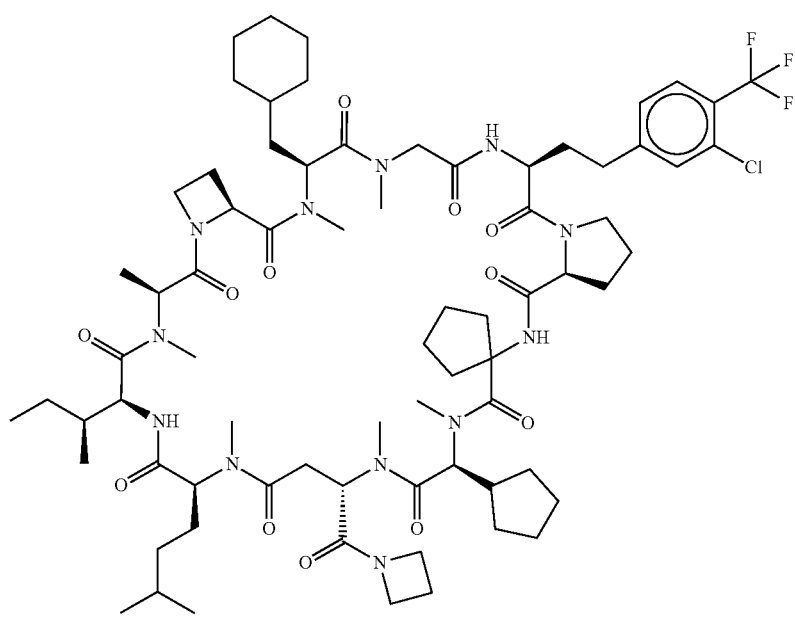 |

TABLE 24-continued
| Compound No. | Structural formula |
|---|---|
| 807 | 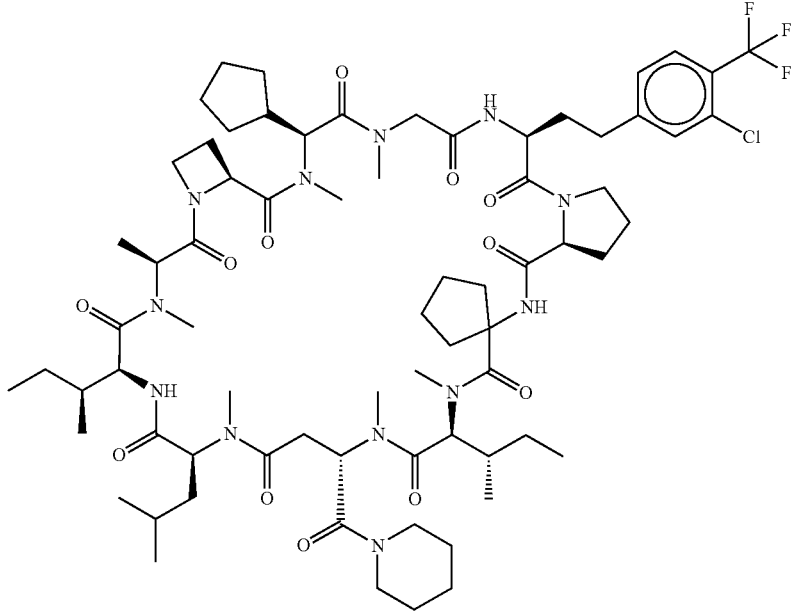 |
| 808 | 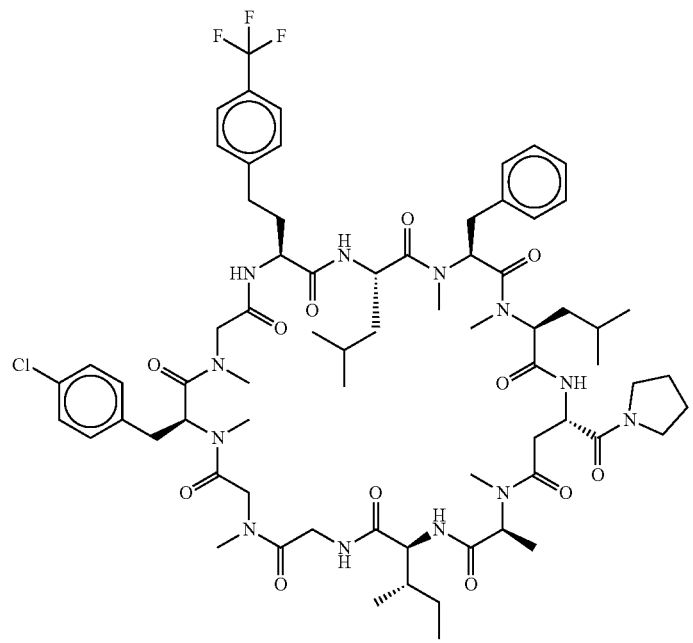 |

TABLE 24-continued
| Compound No. | Structural formula |
|---|---|
| 809 | 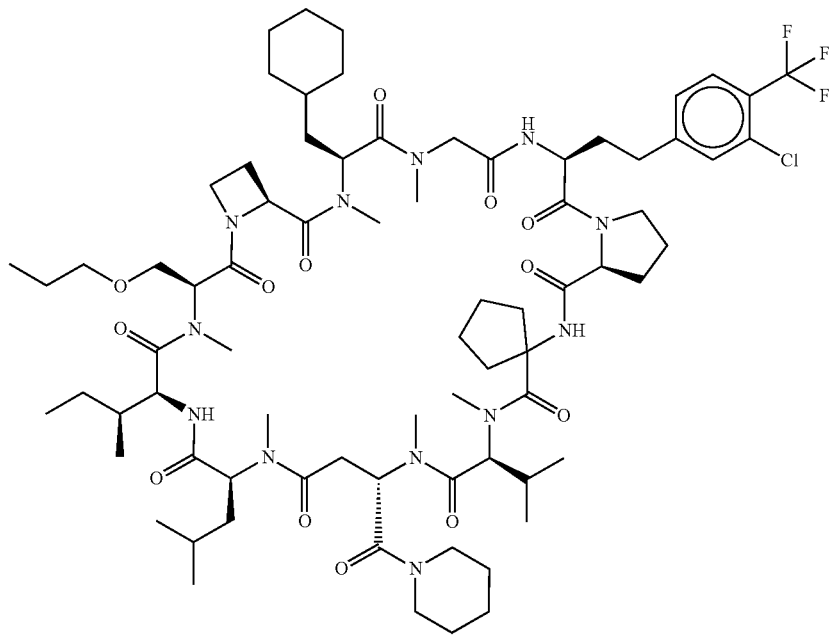 |
| 810 | 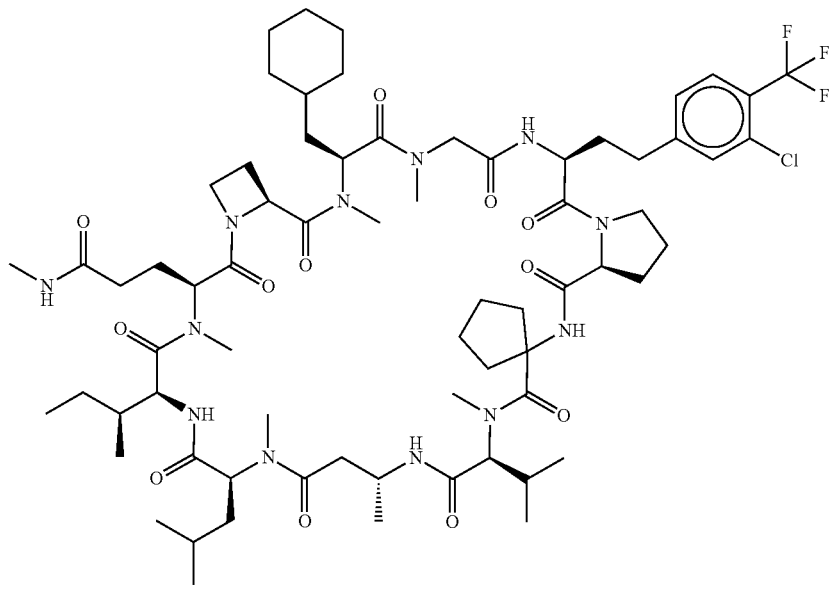 |

TABLE 24-continued
| Compound No. | Structural formula |
|---|---|
| 811 | 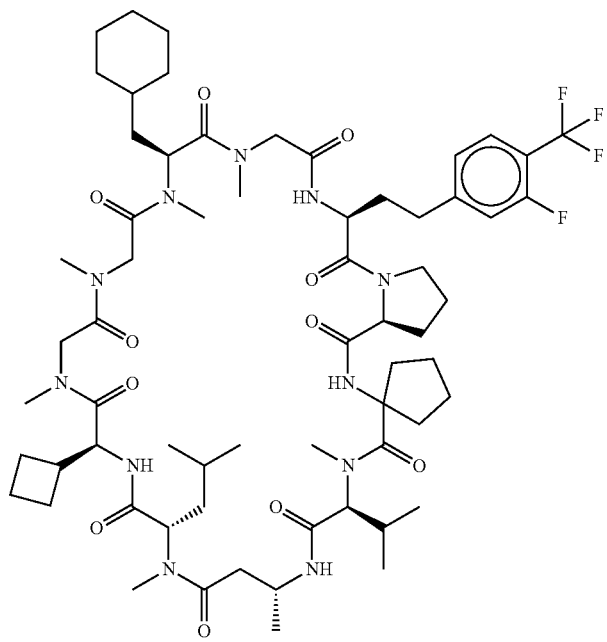 |
| 812 | 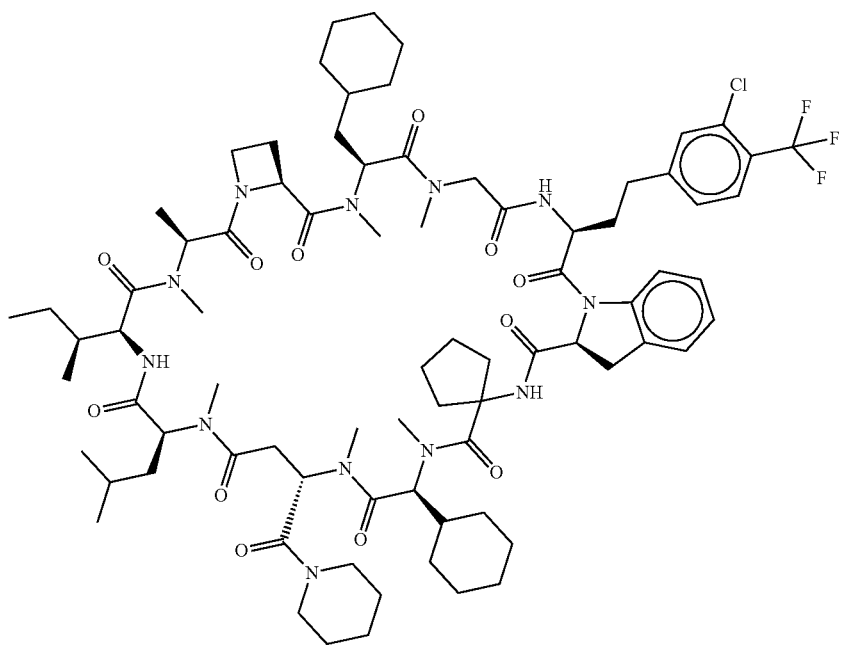 |

TABLE 24-continued
| Compound No. | Structural formula |
|---|---|
| 813 | 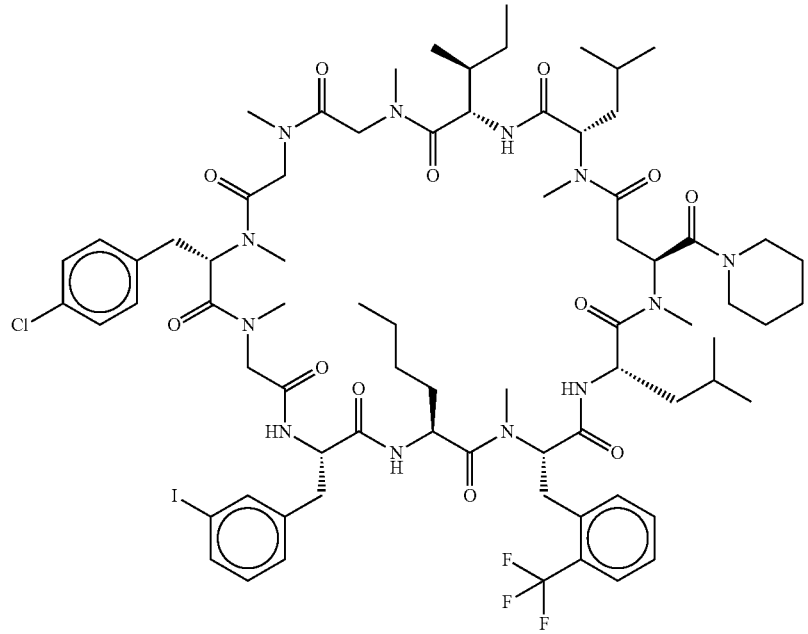 |
| 814 | 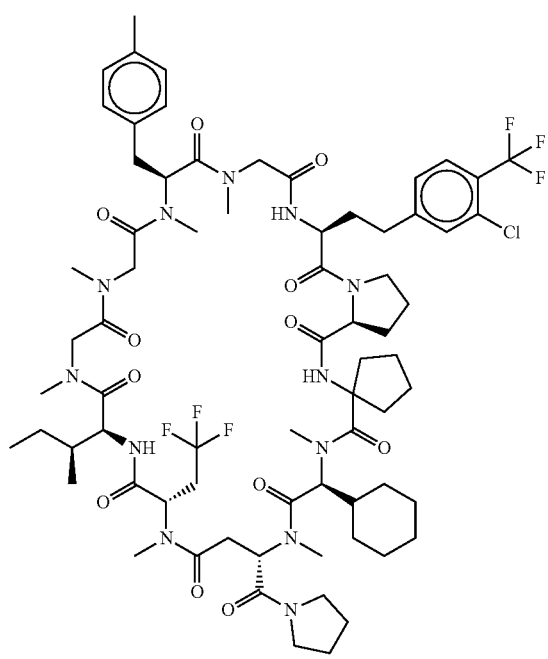 |

TABLE 24-continued
| Compound No. | Structural formula |
|---|---|
| 815 | 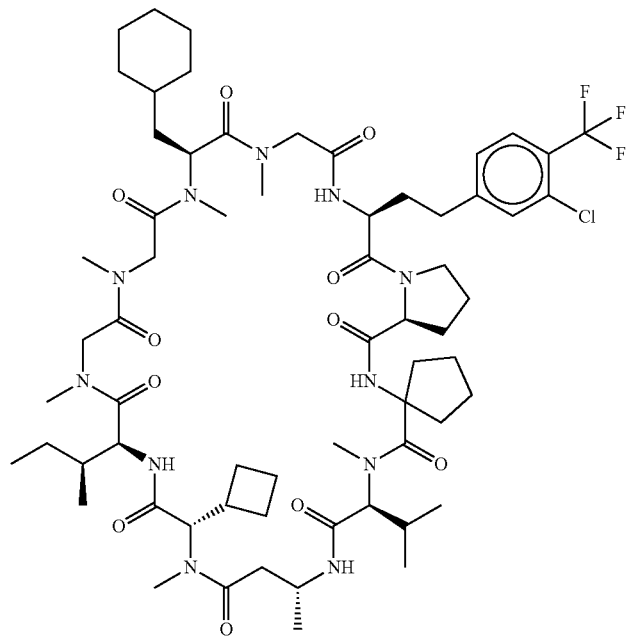 |
| 816 | 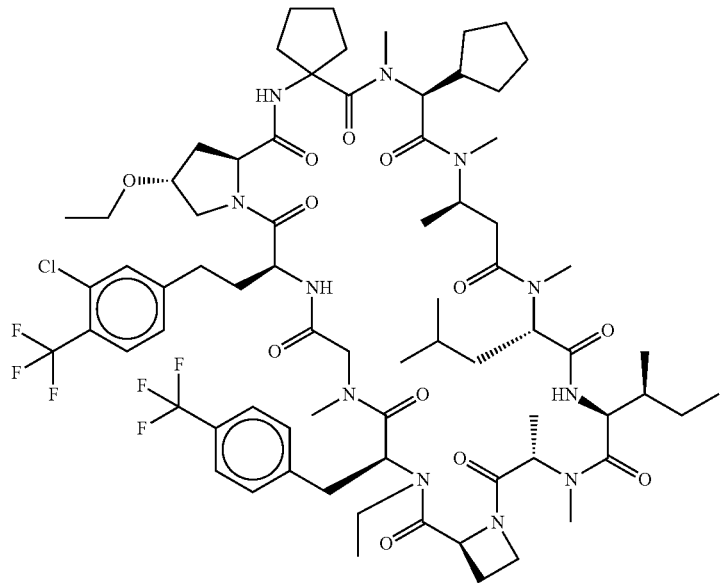 |

TABLE 24-continued
| Compound No. | Structural formula |
|---|---|
| 817 | 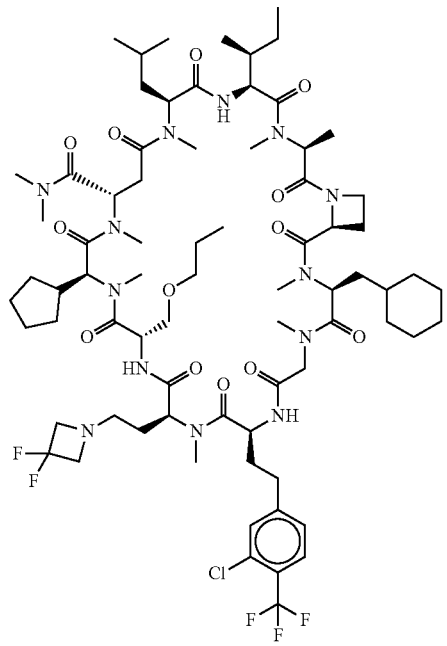 |
| 818 | 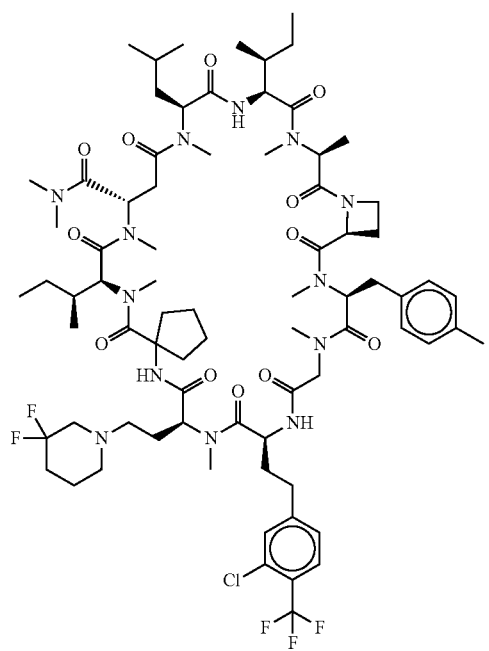 |

TABLE 24-continued
| Compound No. | Structural formula |
|---|---|
| 819 | 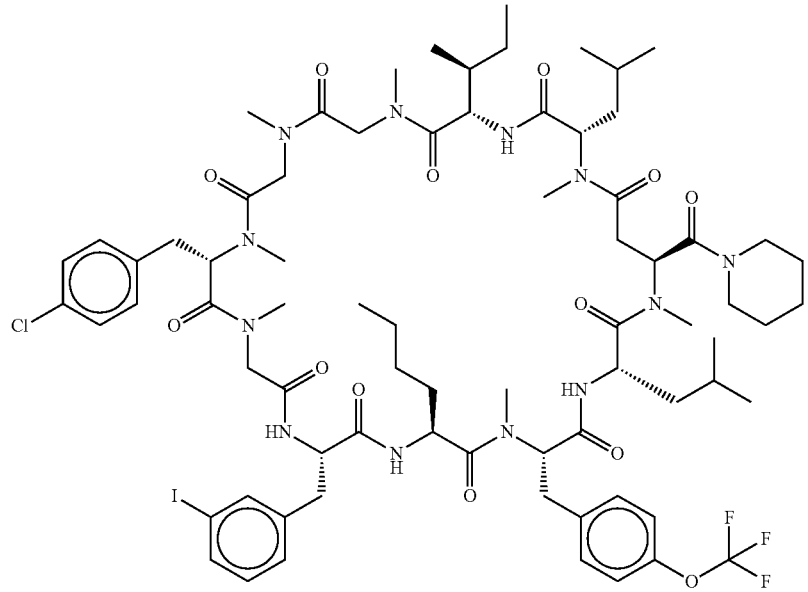 |
| 820 | 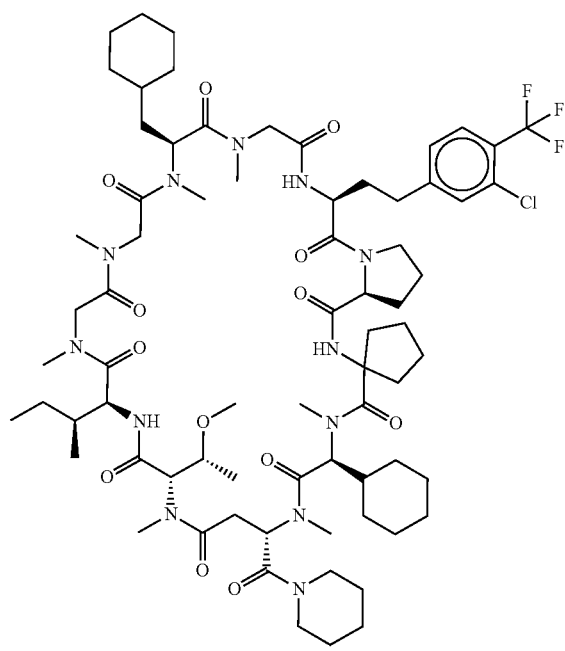 |

TABLE 24-continued
| Compound No. | Structural formula |
|---|---|
| 821 | 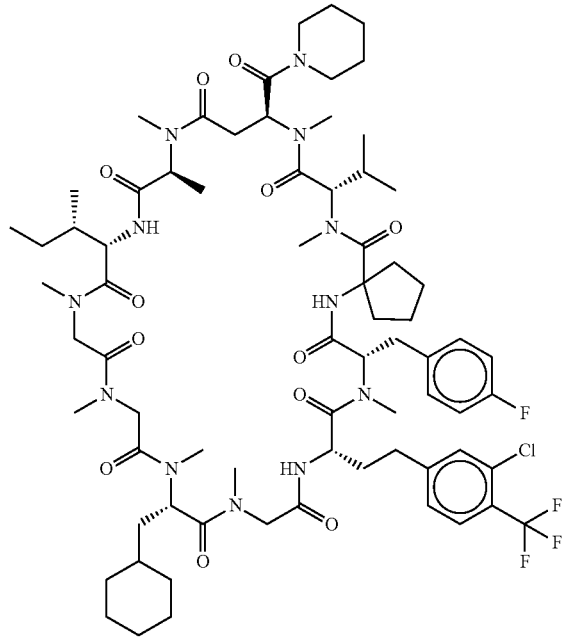 |
| 822 | 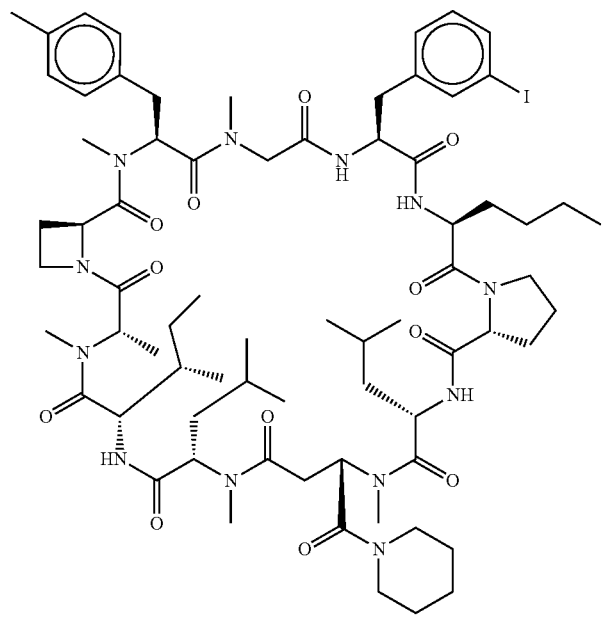 |

TABLE 24-continued
| Compound No. | Structural formula |
|---|---|
| 823 | 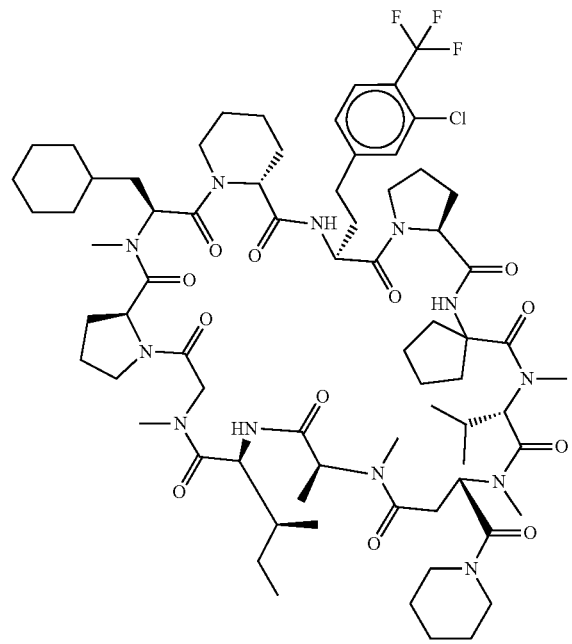 |
| 824 | 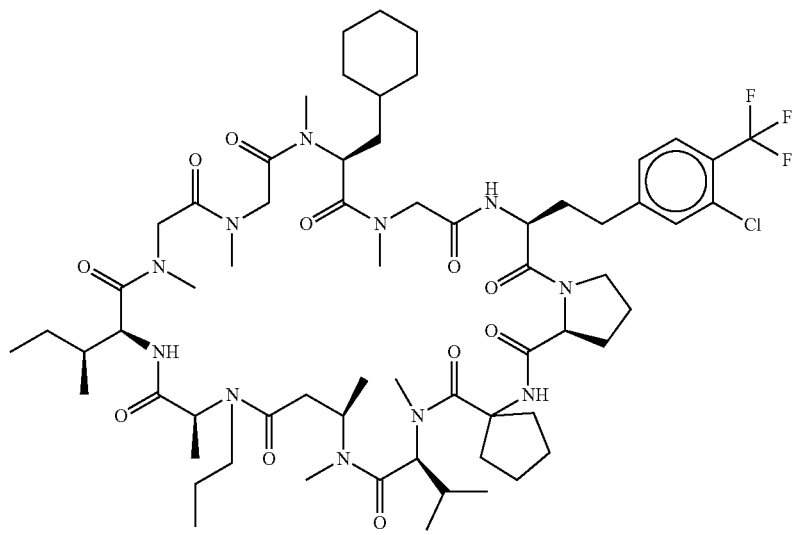 |

TABLE 24-continued
| Compound No. | Structural formula |
| --- | --- |
| 825 | 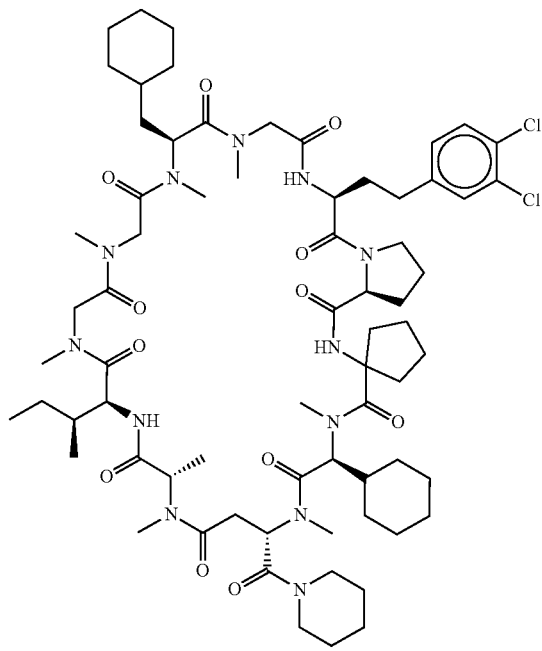 |
| 826 | 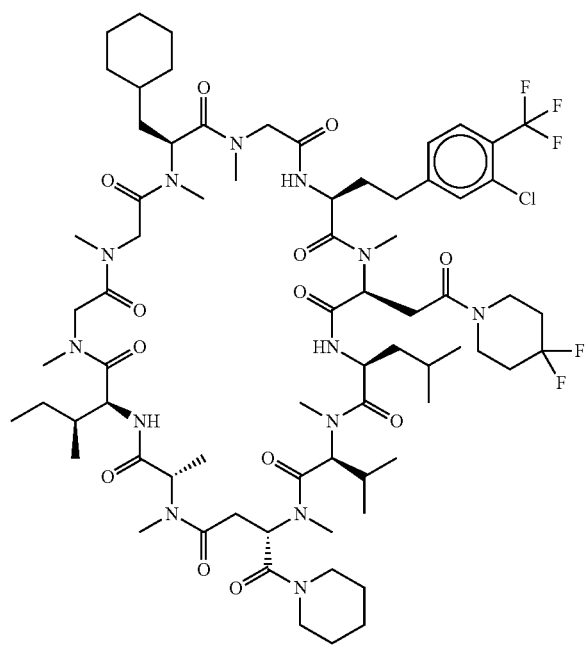 |

TABLE 24-continued
| Compound No. | Structural formula |
|---|---|
| 827 | 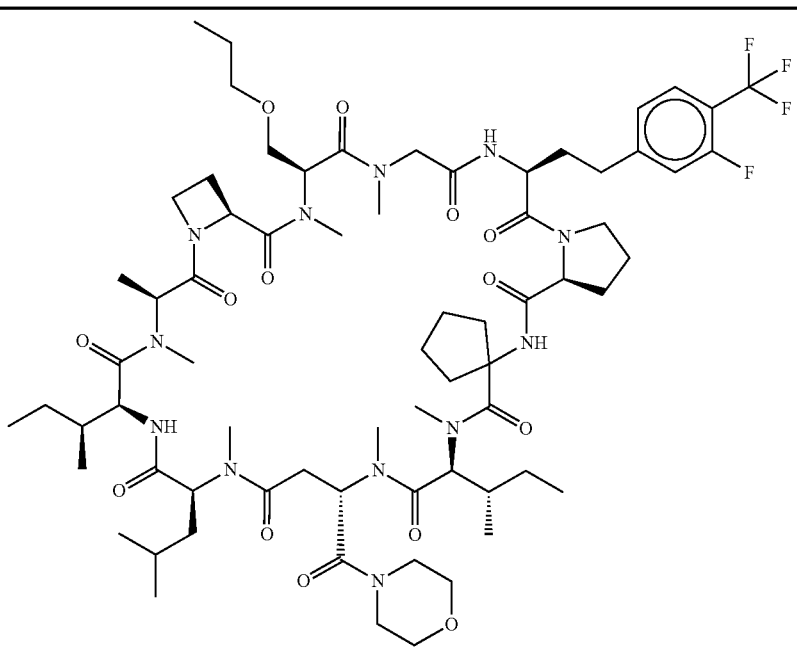 |
| 828 | 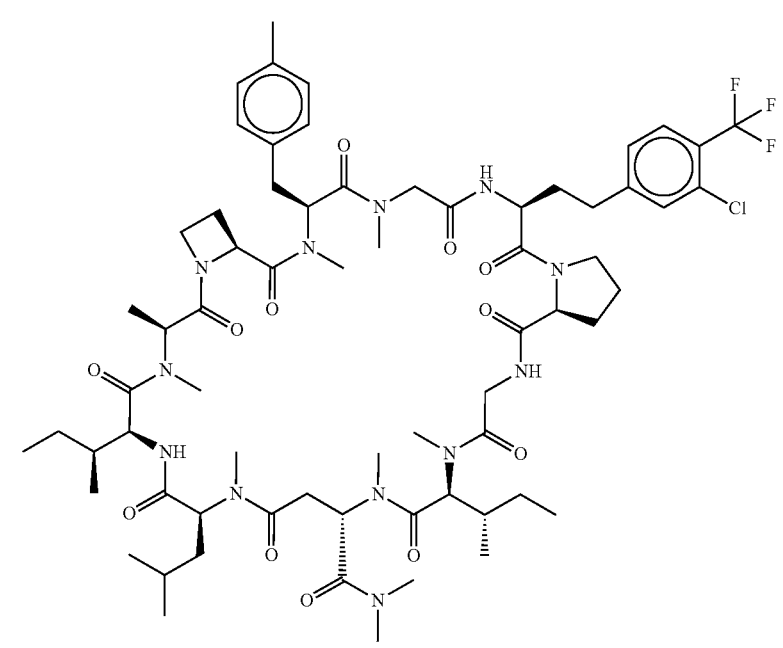 |

TABLE 24-continued
| Compound No. | Structural formula |
|---|---|
| 829 | 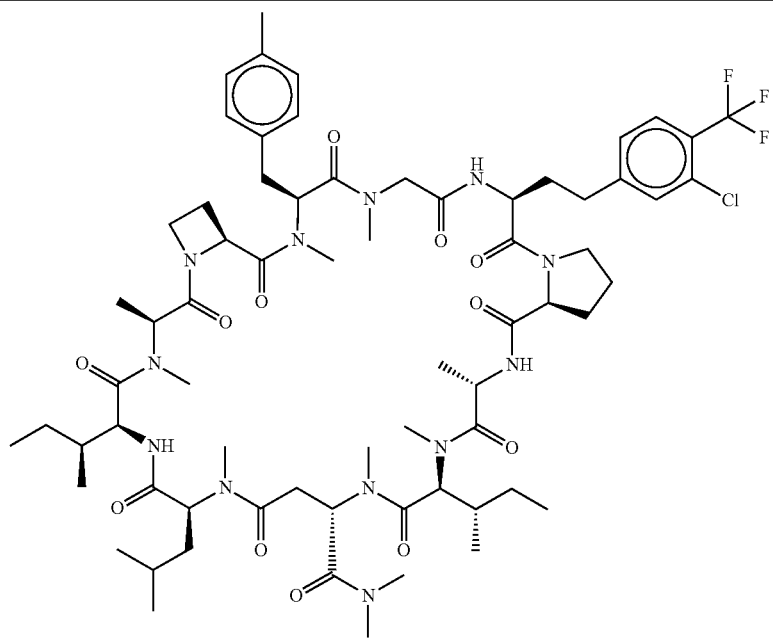 |
| 830 | 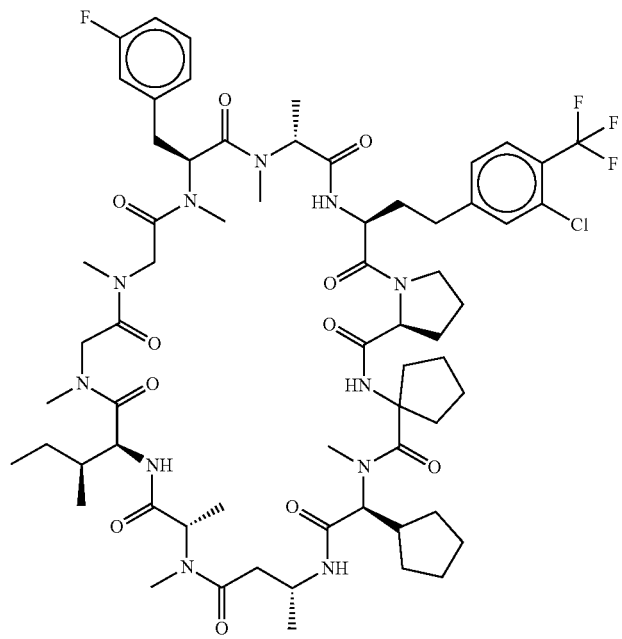 |

TABLE 24-continued
| Compound No. | Structural formula |
| --- | --- |
| 831 | 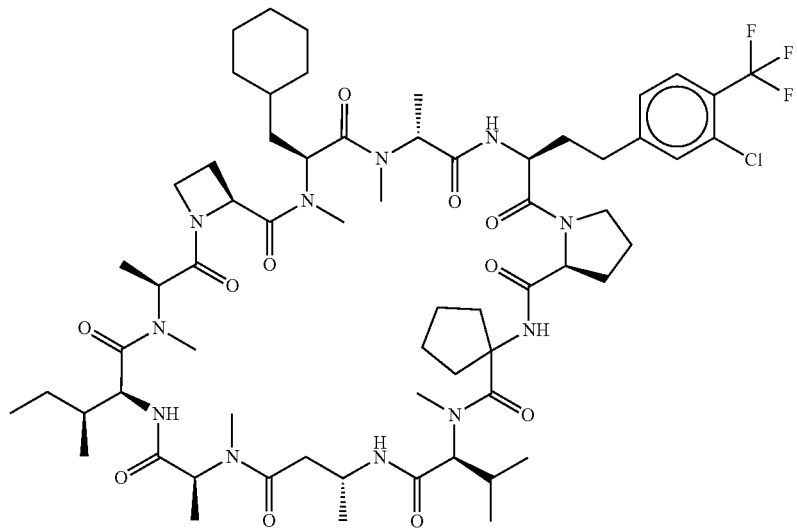 |
| 832 | 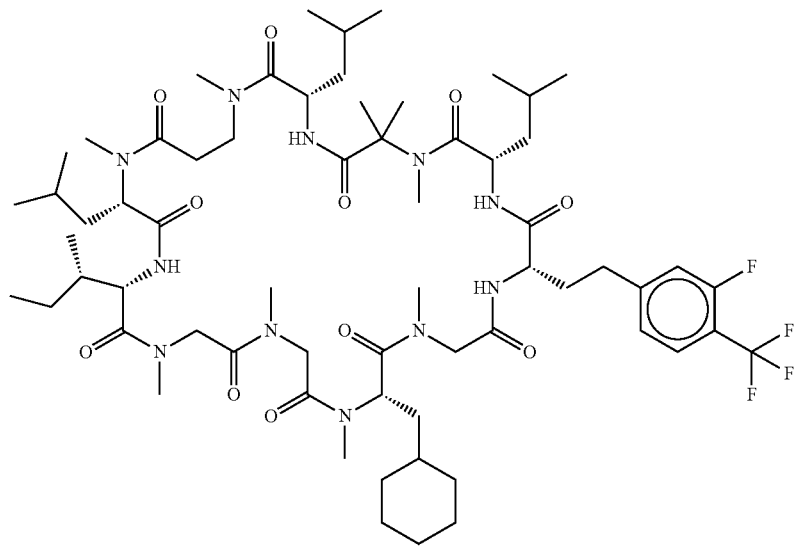 |

TABLE 24-continued
| Compound No. | Structural formula |
|---|---|
| 833 | 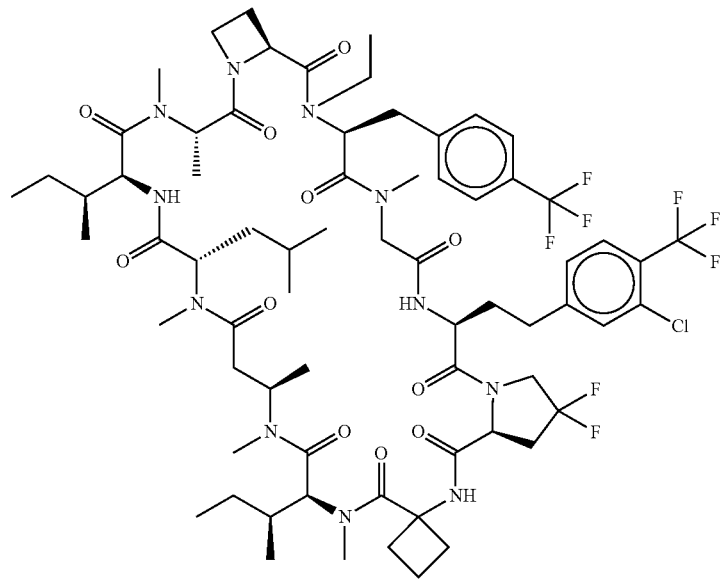 |
| 834 | 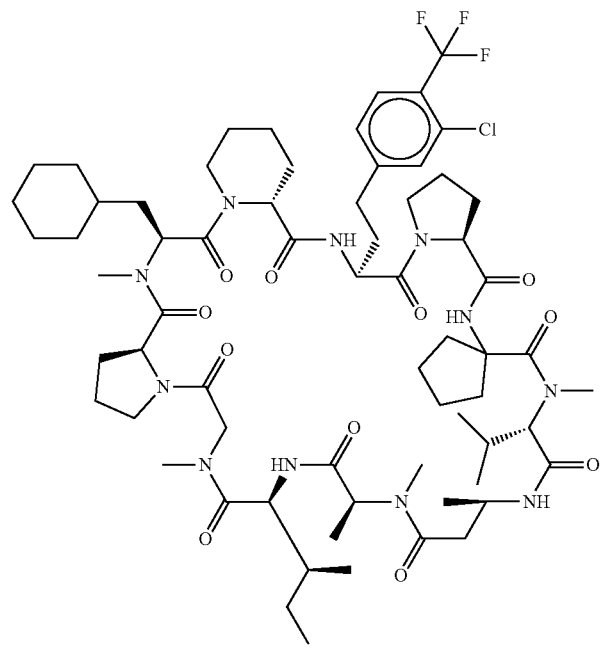 |

TABLE 24-continued
| Compound No. | Structural formula |
|---|---|
| 835 | 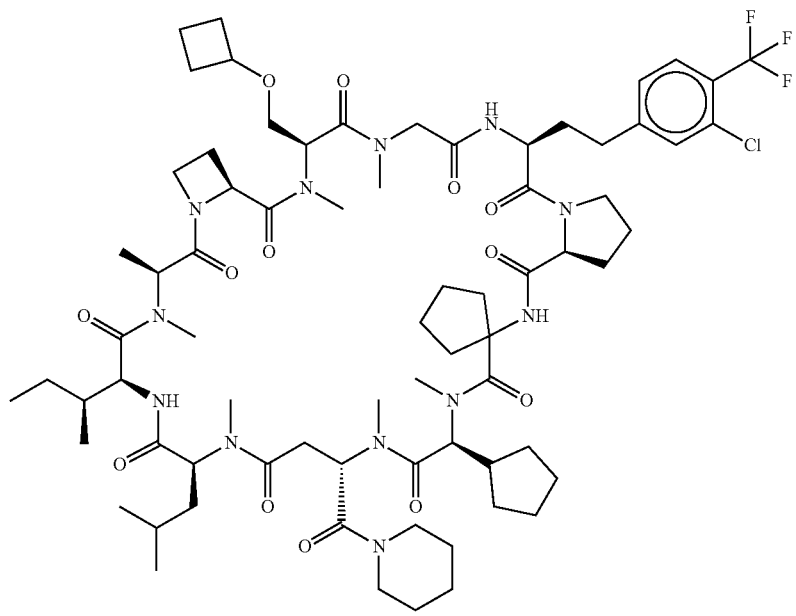 |
| 836 | 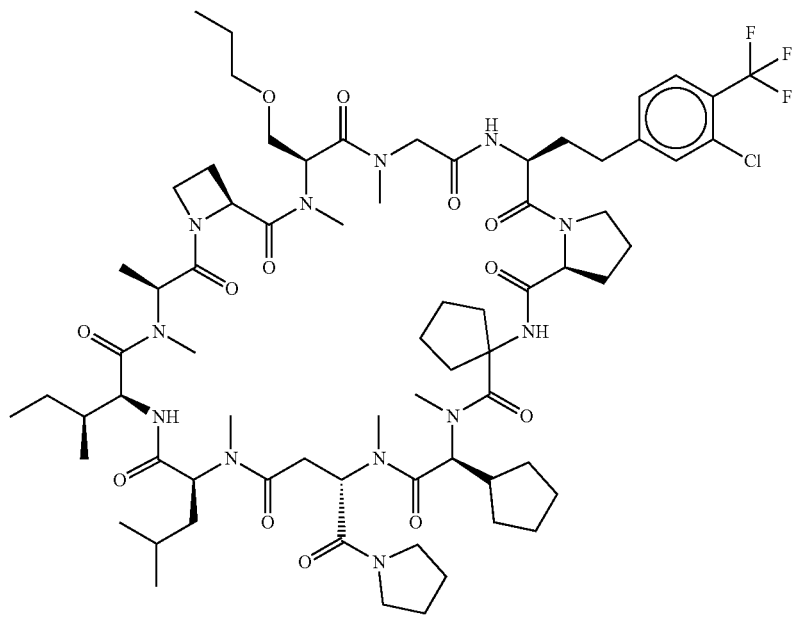 |

TABLE 24-continued
| Compound No. | Structural formula |
|---|---|
| 837 | 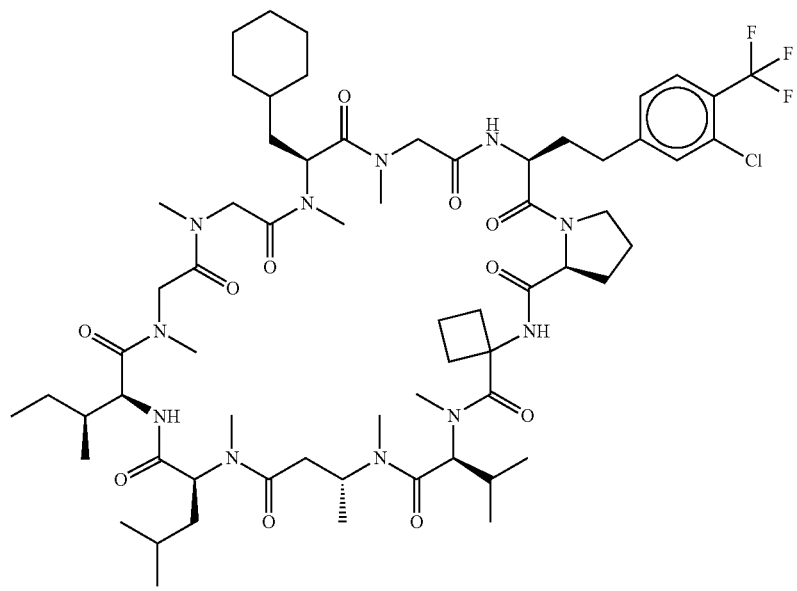 |
| 838 | 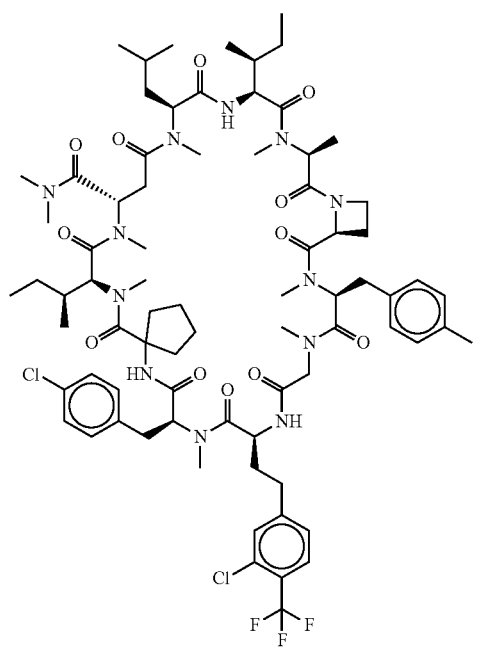 |

TABLE 24-continued
| Compound No. | Structural formula |
|---|---|
| 839 | 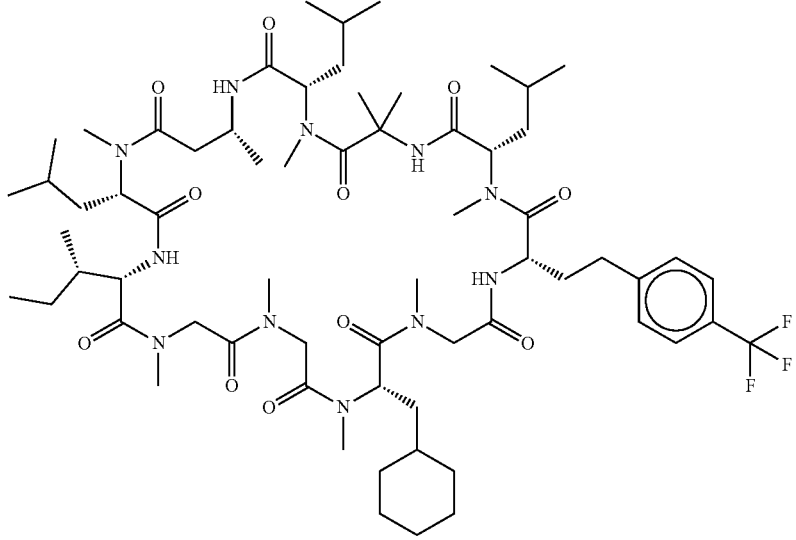 |
| 840 | 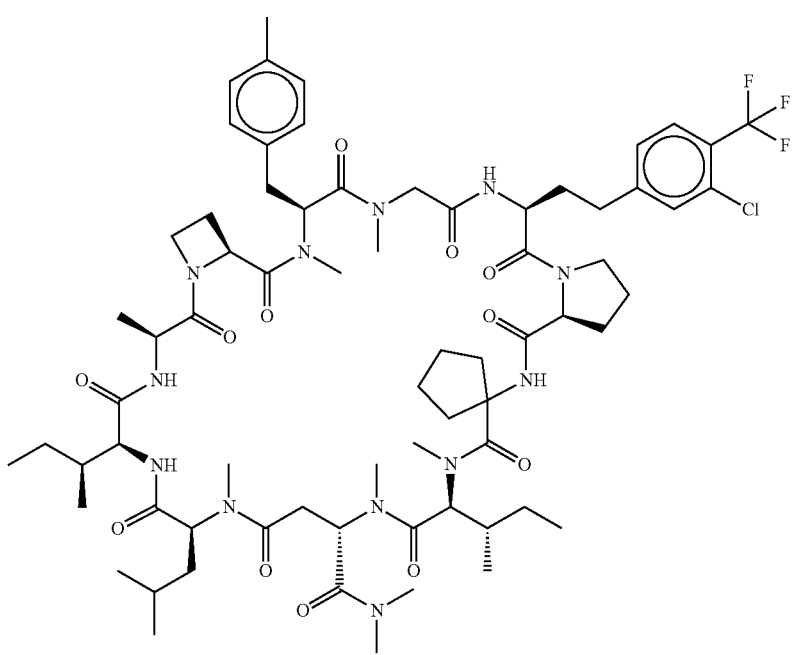 |

TABLE 24-continued
| Compound No. | Structural formula |
|---|---|
| 841 | 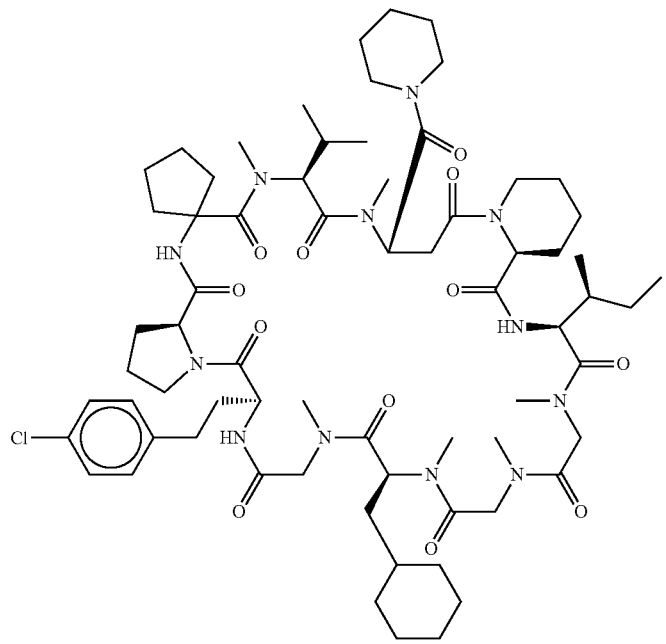 |
| 842 | 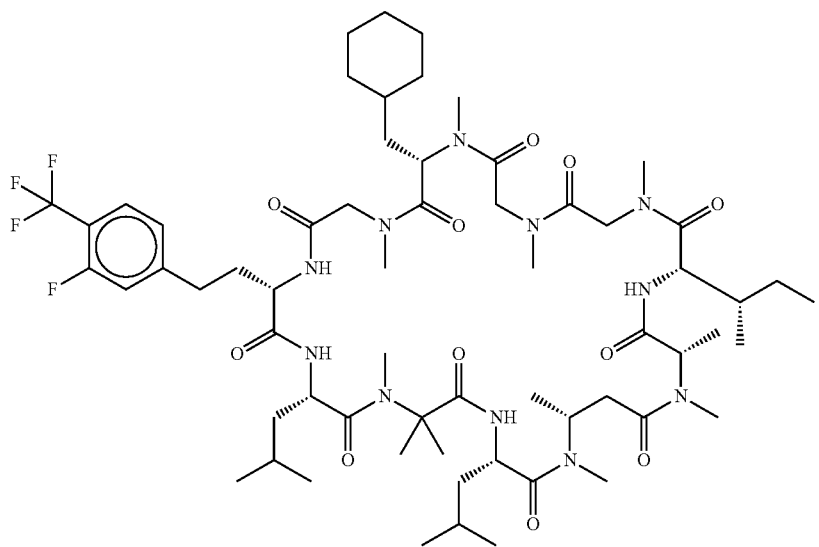 |

TABLE 24-continued
| Compound No. | Structural formula |
|---|---|
| 843 | 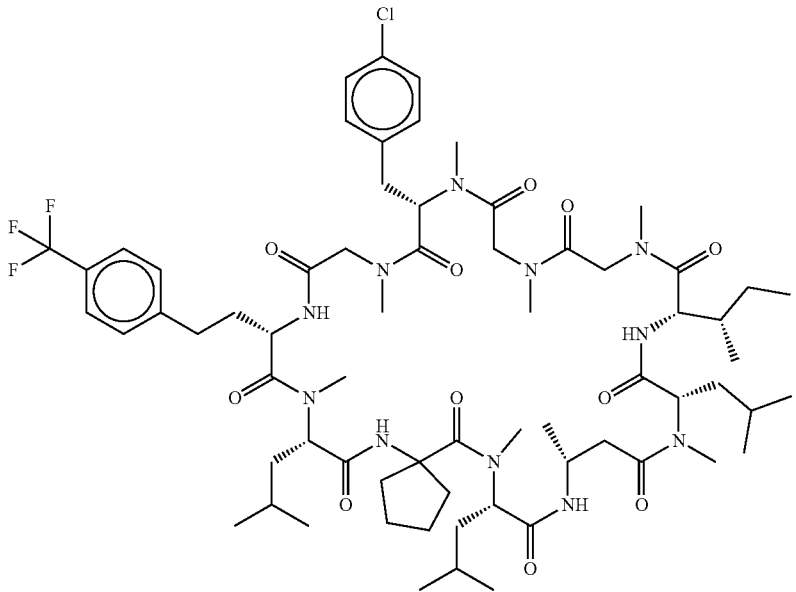 |
| 844 | 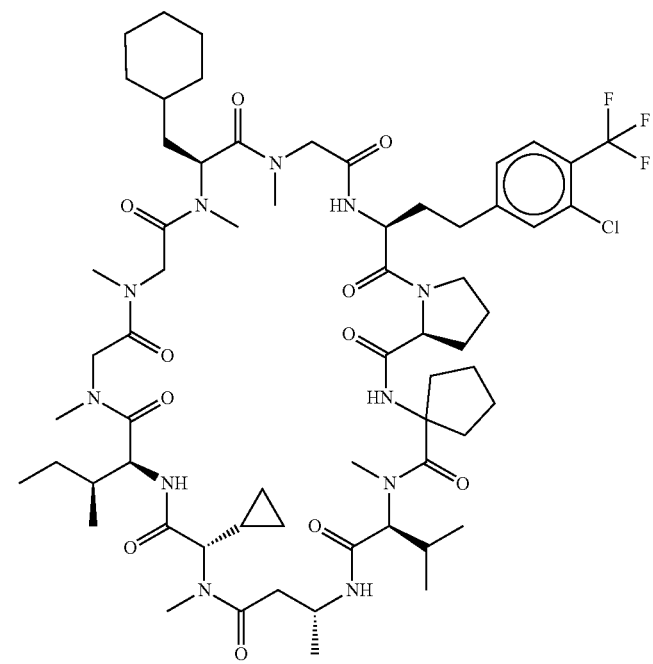 |

TABLE 24-continued
| Compound No. | Structural formula |
|---|---|
| 845 | 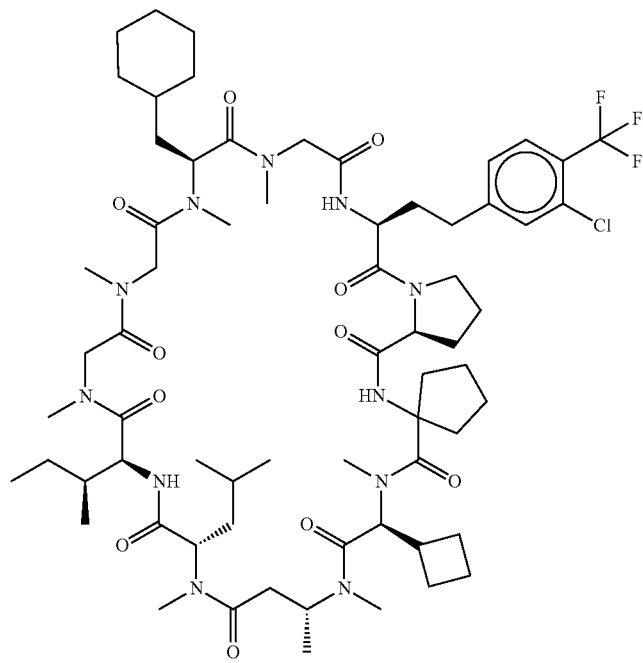 |
| 847 | 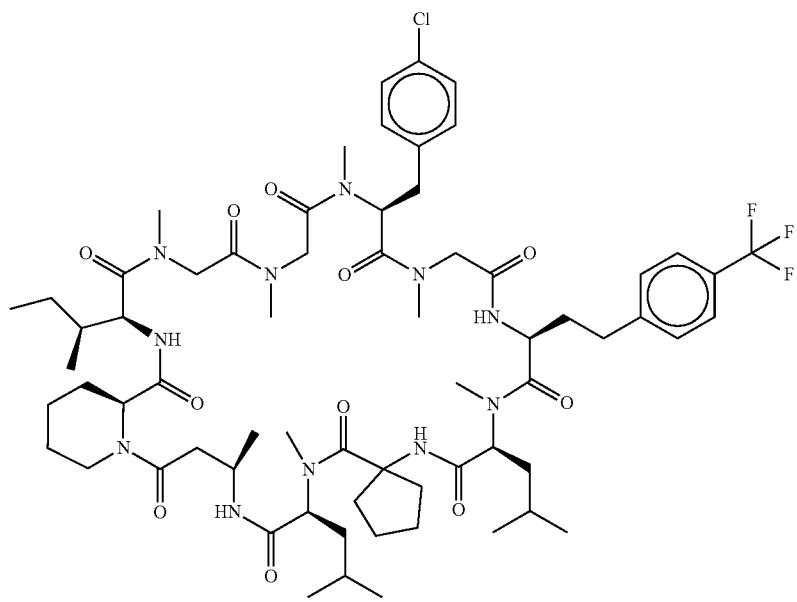 |

TABLE 24-continued
| Compound No. | Structural formula |
|---|---|
| 848 | 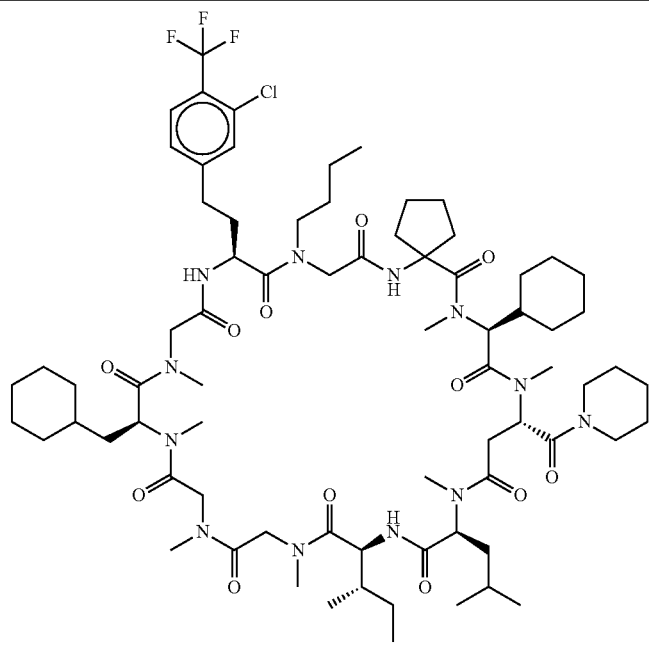 |
| 849 | 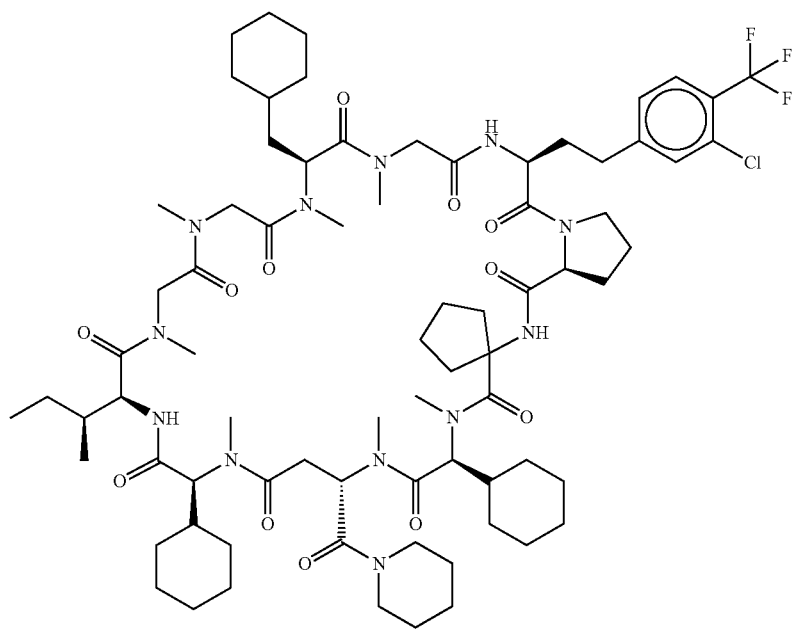 |

TABLE 24-continued
| Compound No. | Structural formula |
|---|---|
| 850 | 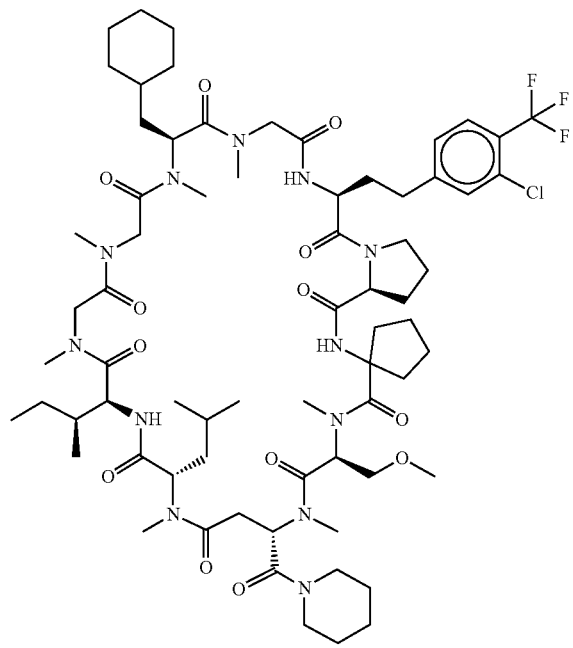 |
| 851 | 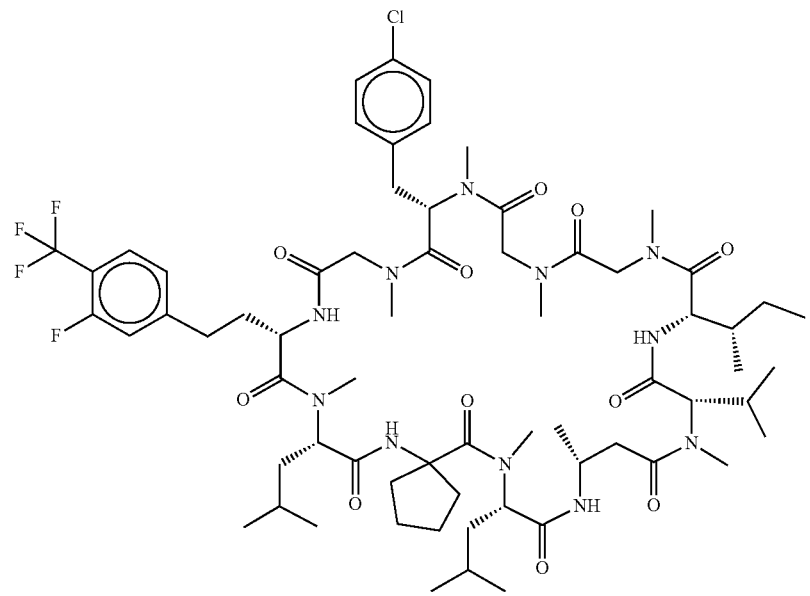 |

TABLE 24-continued
| Compound No. | Structural formula |
|---|---|
| 852 | 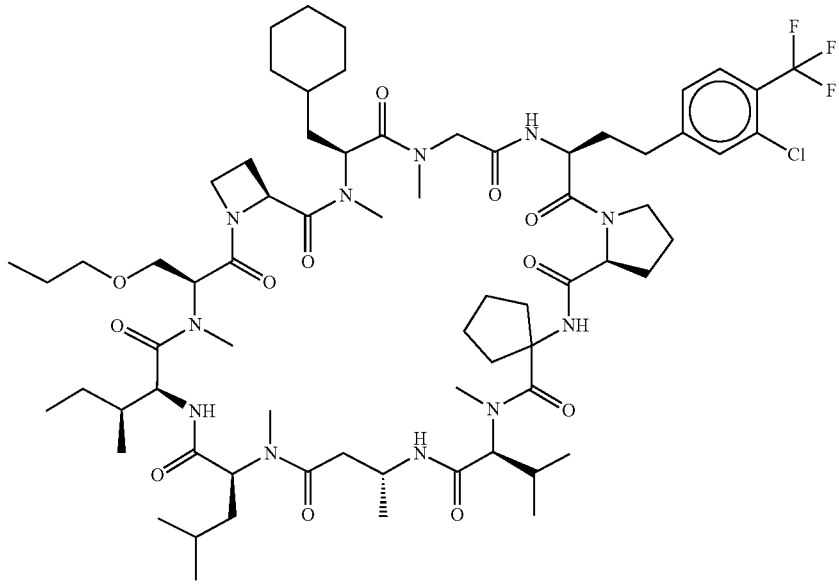 |
| 853 | 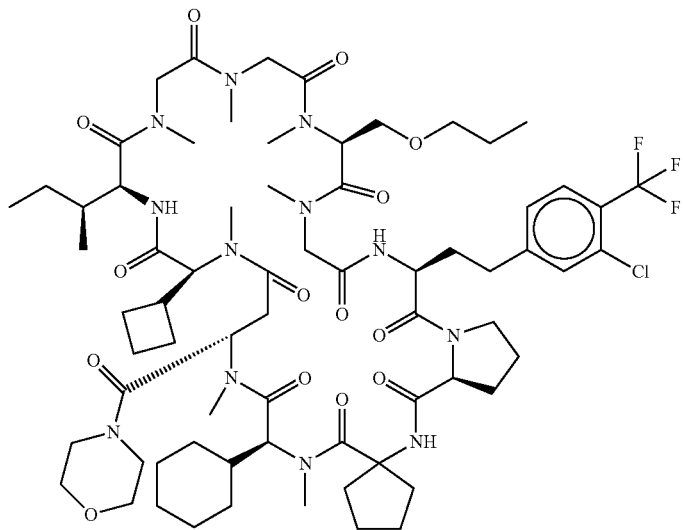 |

TABLE 24-continued
| Compound No. | Structural formula |
|---|---|
| 854 | 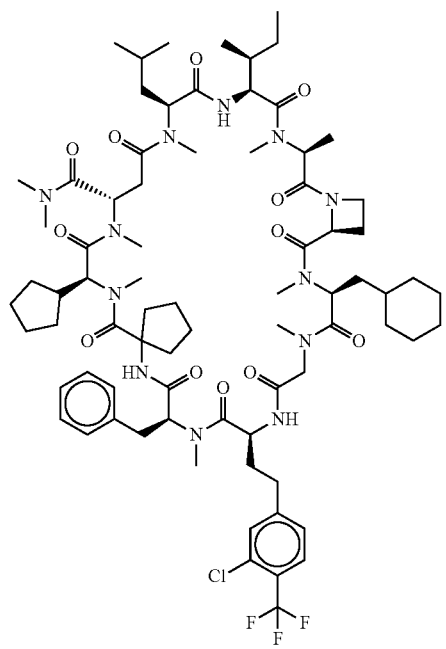 |
| 855 | 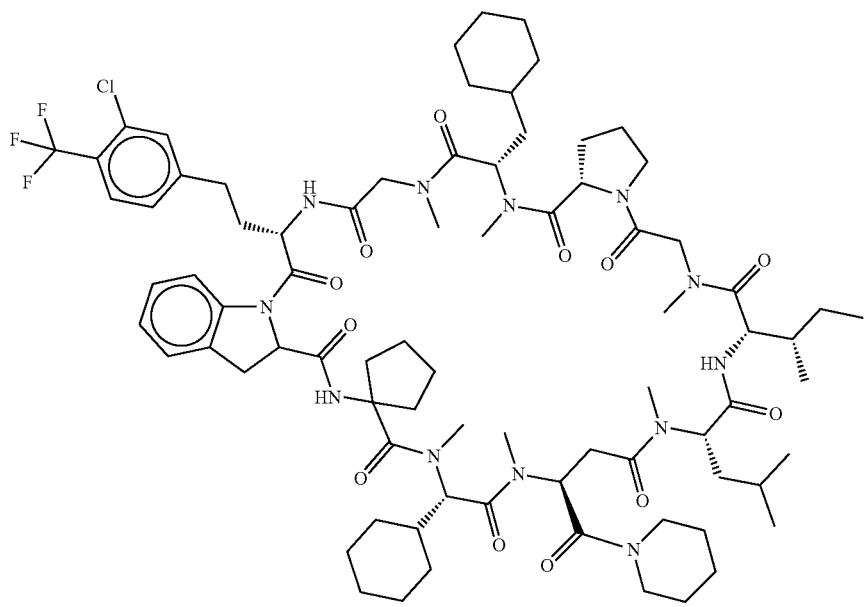 |

TABLE 24-continued
| Compound No. | Structural formula |
|---|---|
| 856 | 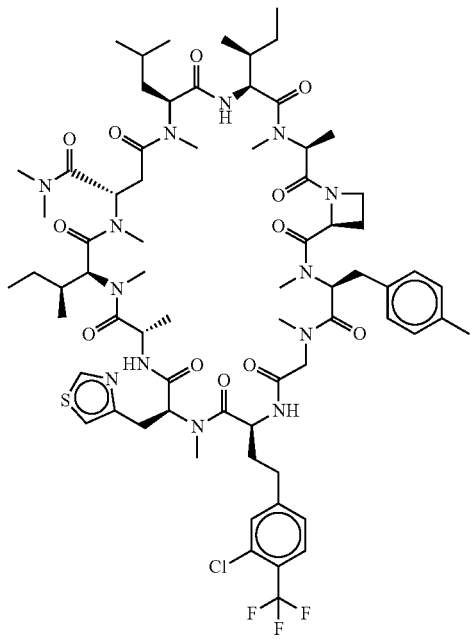 |
| 857 | 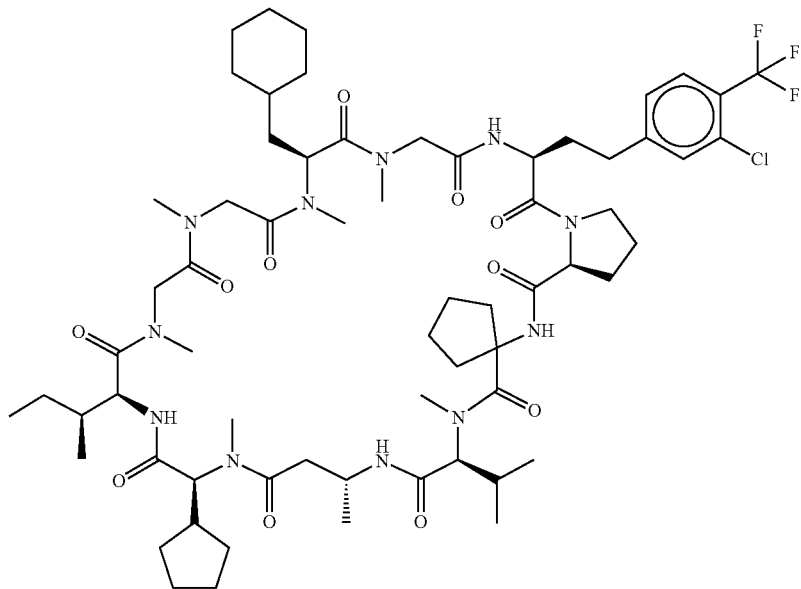 |

TABLE 24-continued
| Compound No. | Structural formula |
|---|---|
| 858 | 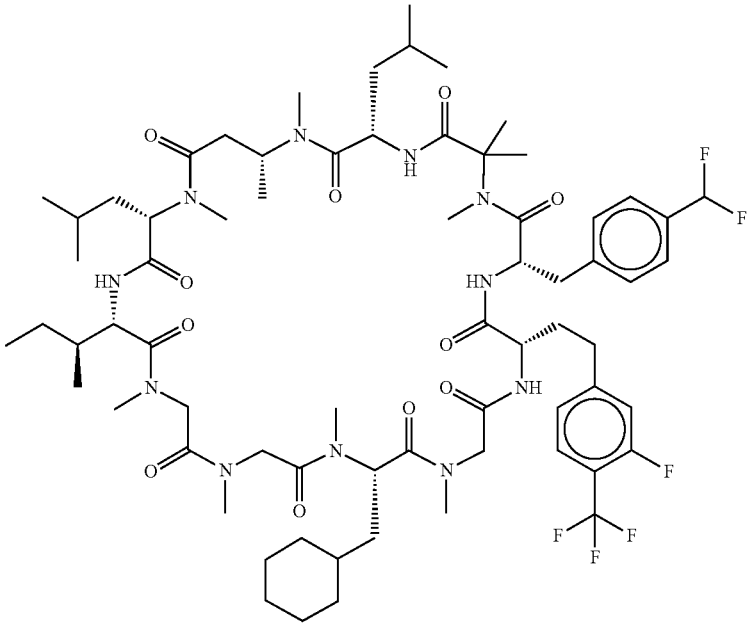 |
| 859 | 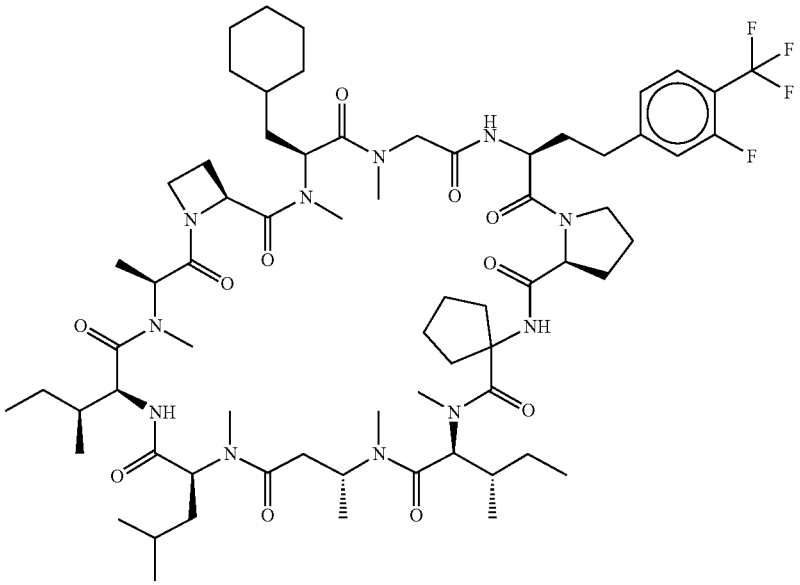 |

TABLE 24-continued
| Compound No. | Structural formula |
|---|---|
| 860 | 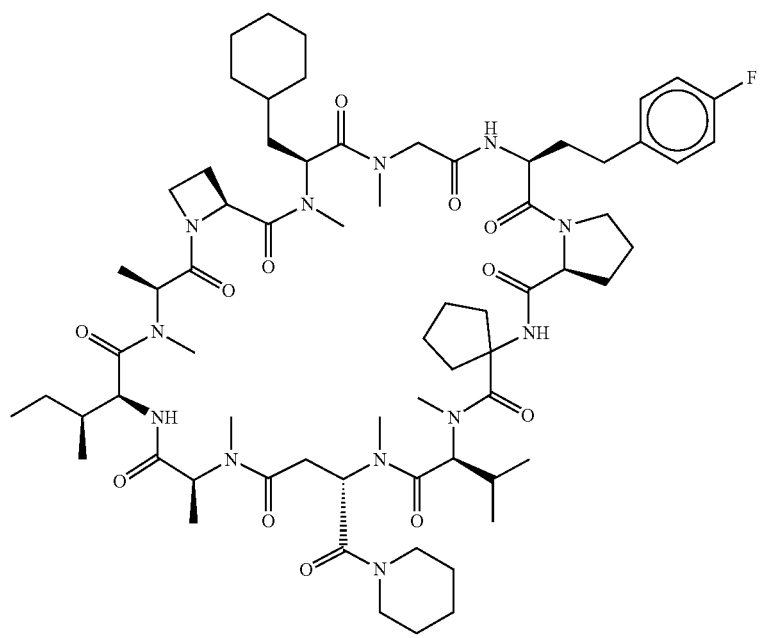 |
| 861 | 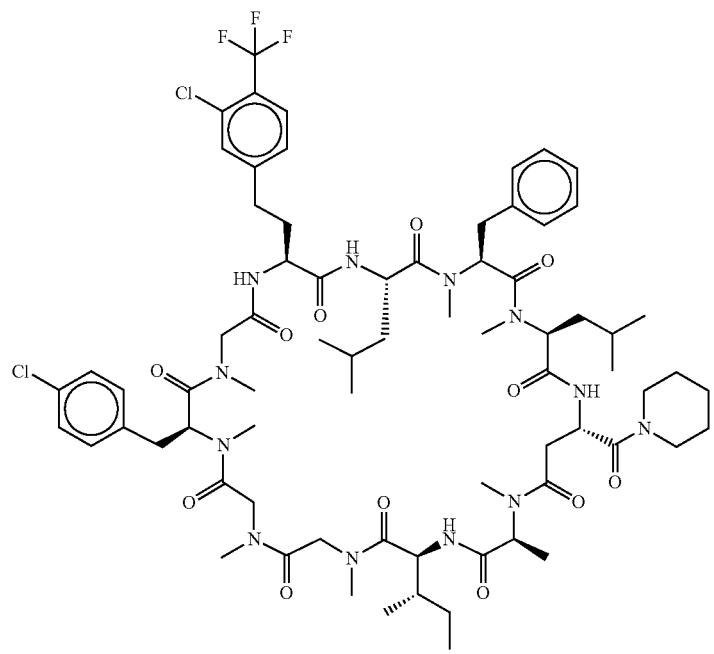 |

TABLE 24-continued
| Compound No. | Structural formula |
|---|---|
| 862 | 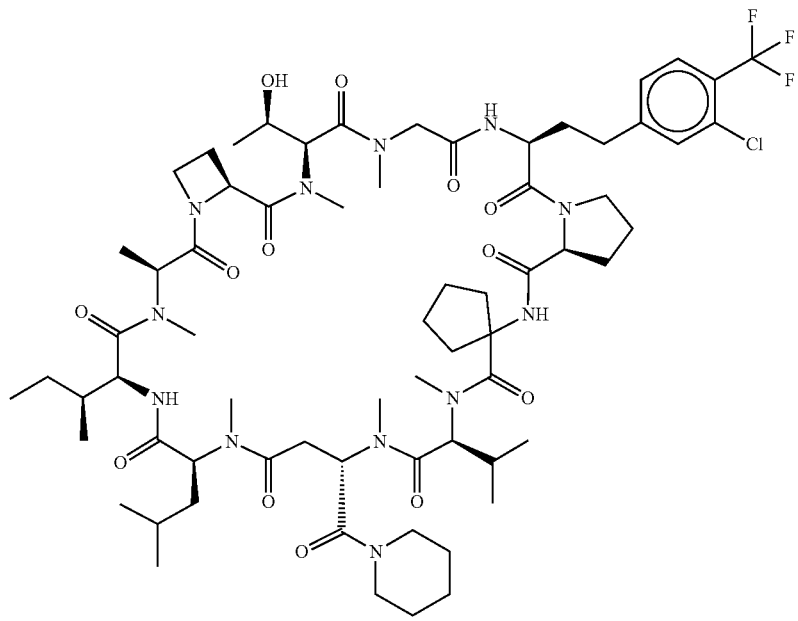 |
| 863 | 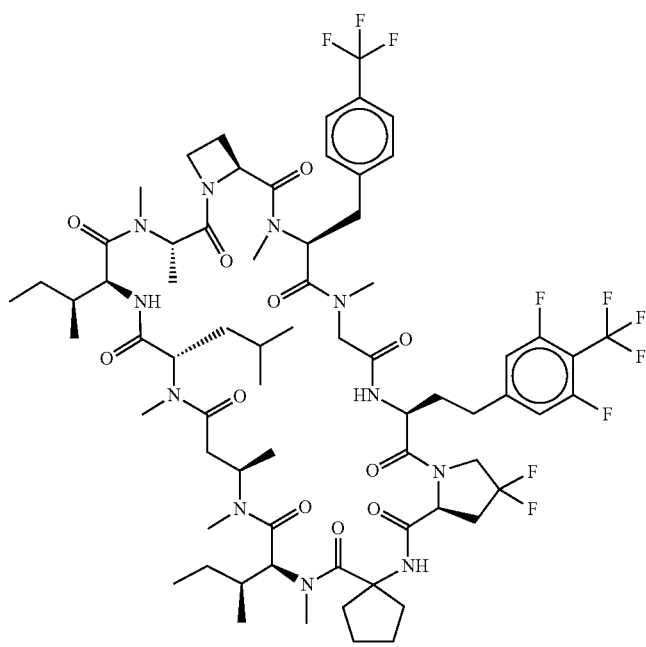 |

TABLE 24-continued
| Compound No. | Structural formula |
|---|---|
| 864 | 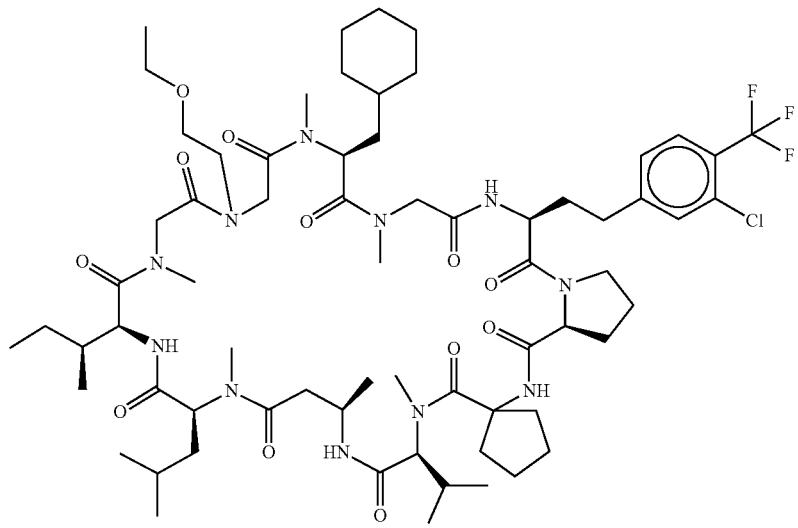 |
| 865 | 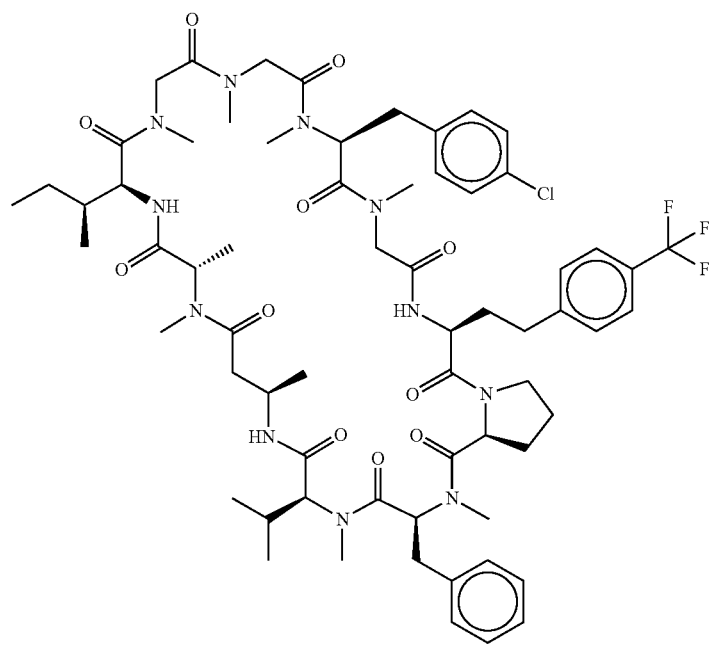 |

TABLE 24-continued
| Compound No. | Structural formula |
|---|---|
| 866 | 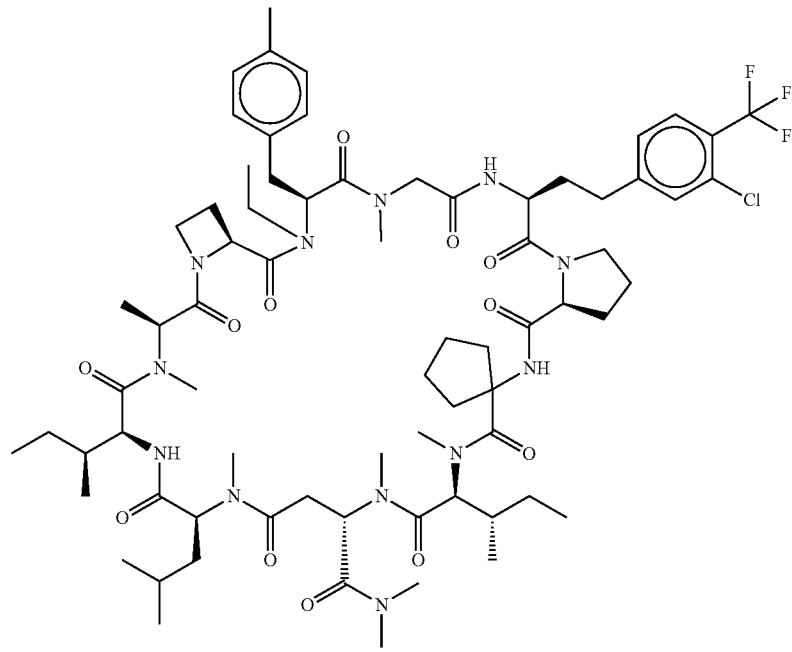 |
| 867 | 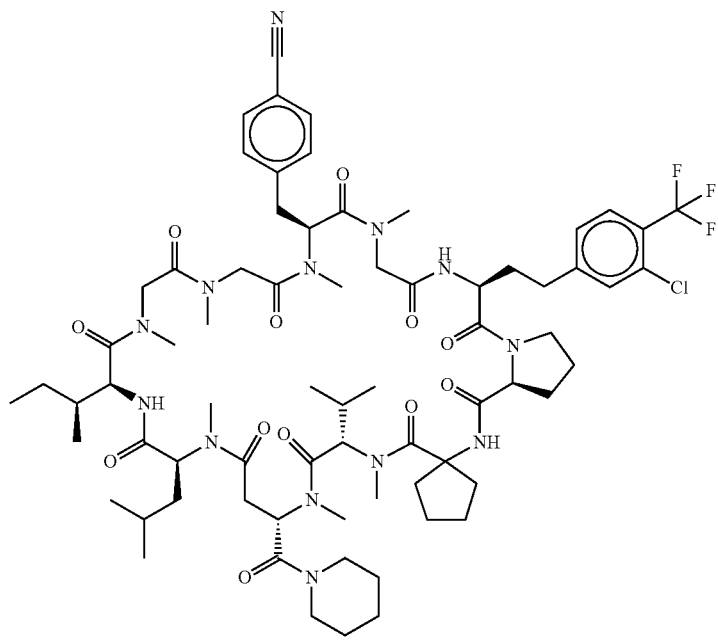 |

TABLE 24-continued
| Compound No. | Structural formula |
|---|---|
| 868 | 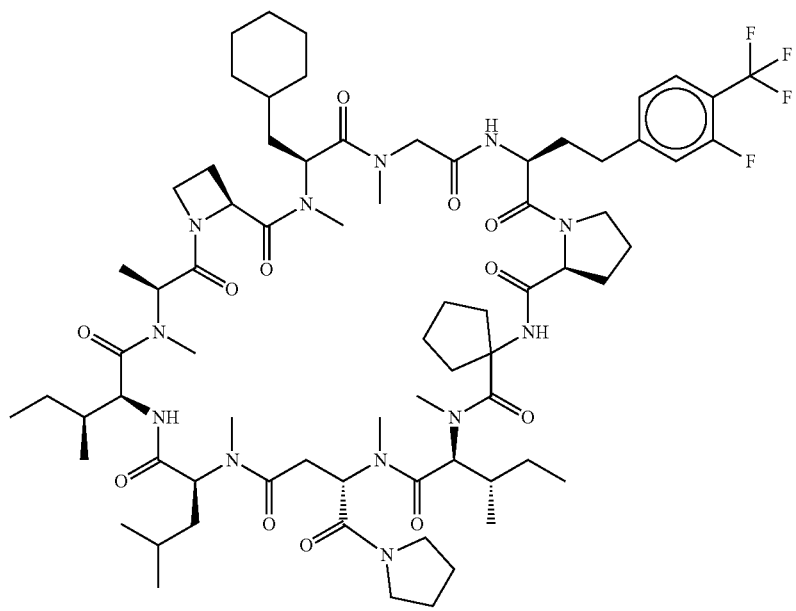 |
| 869 | 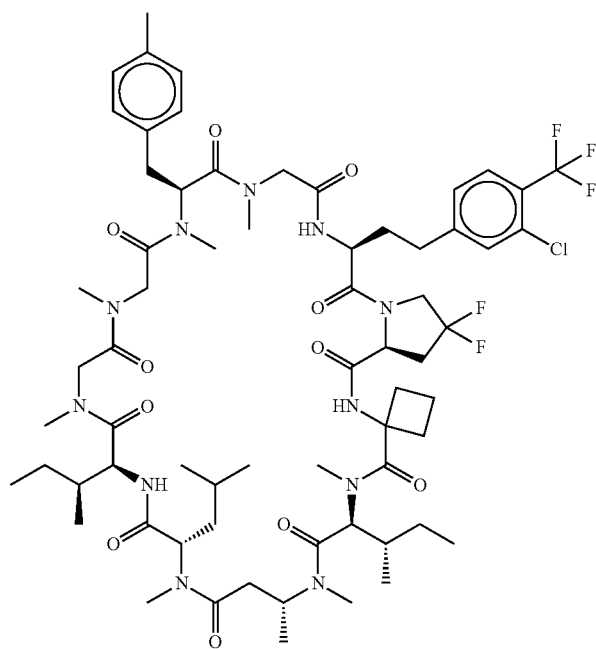 |

TABLE 24-continued
| Compound No. | Structural formula |
|---|---|
| 870 | 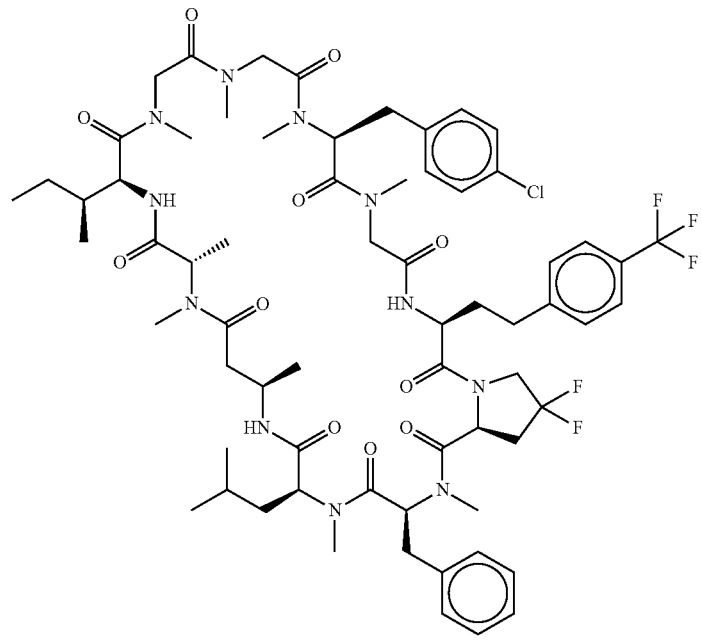 |
| 871 | 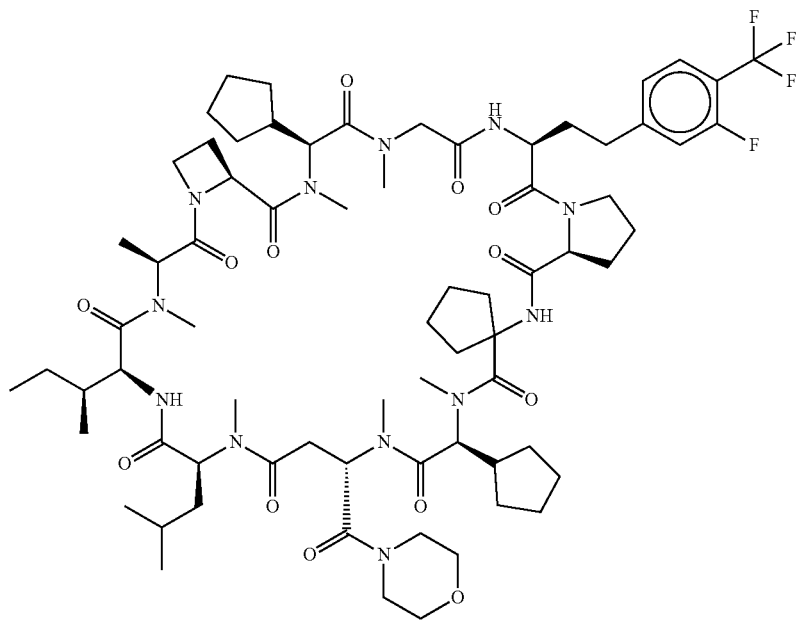 |

TABLE 24-continued
| Compound No. | Structural formula |
|---|---|
| 872 | 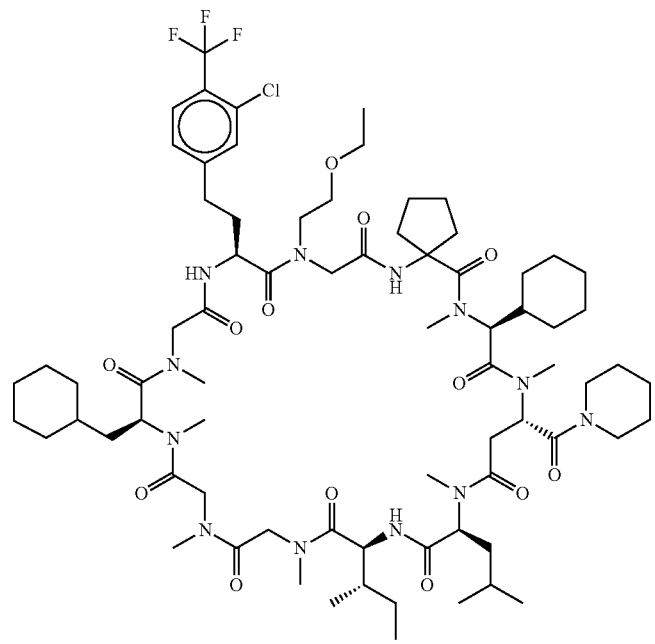 |
| 873 | 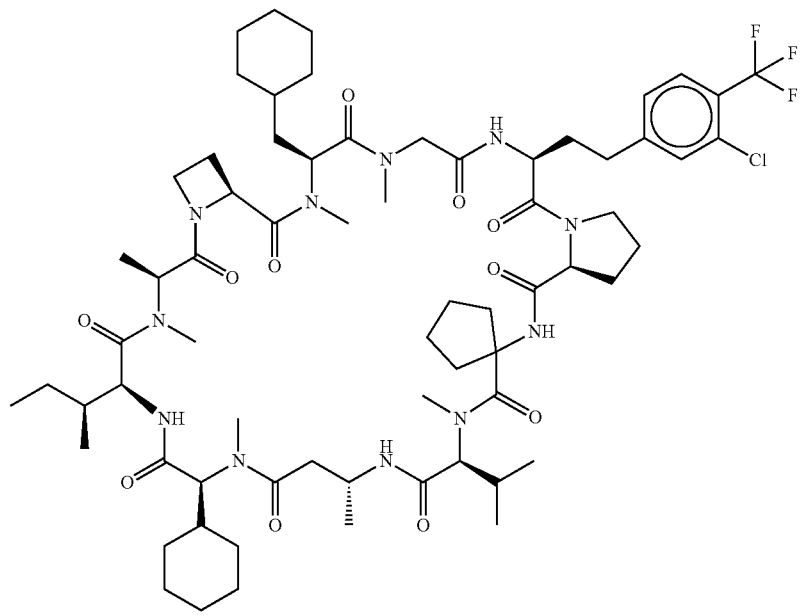 |

TABLE 24-continued
| Compound No. | Structural formula |
|---|---|
| 874 | 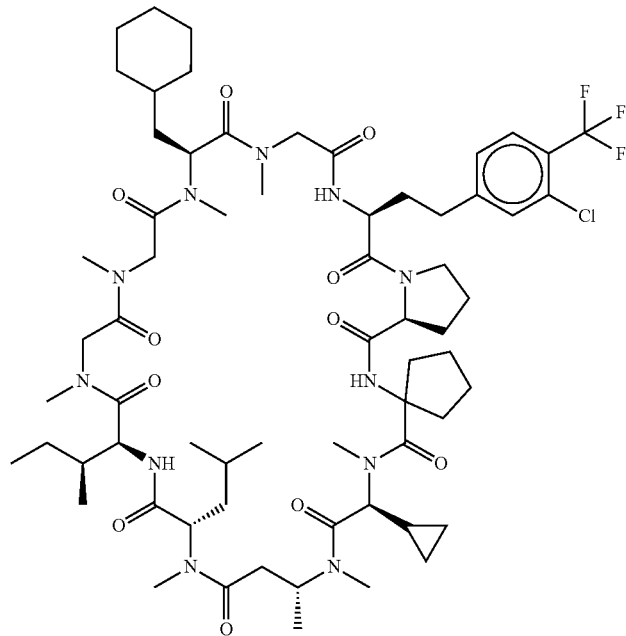 |
| 875 | 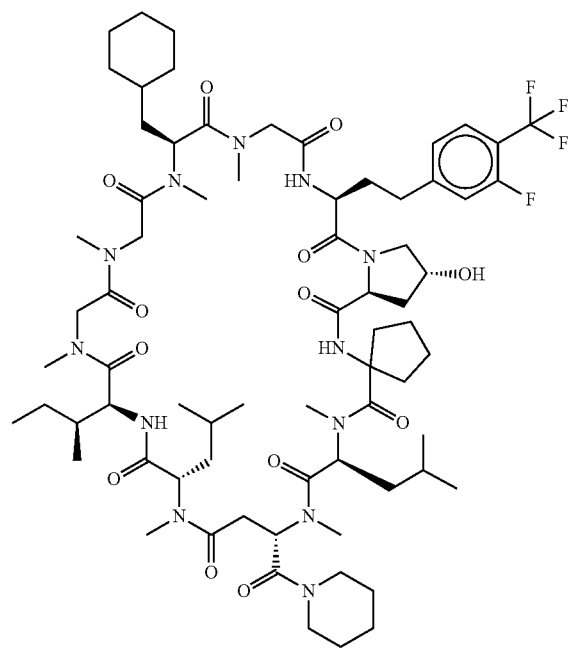 |

TABLE 24-continued
| Compound No. | Structural formula |
|---|---|
| 876 | 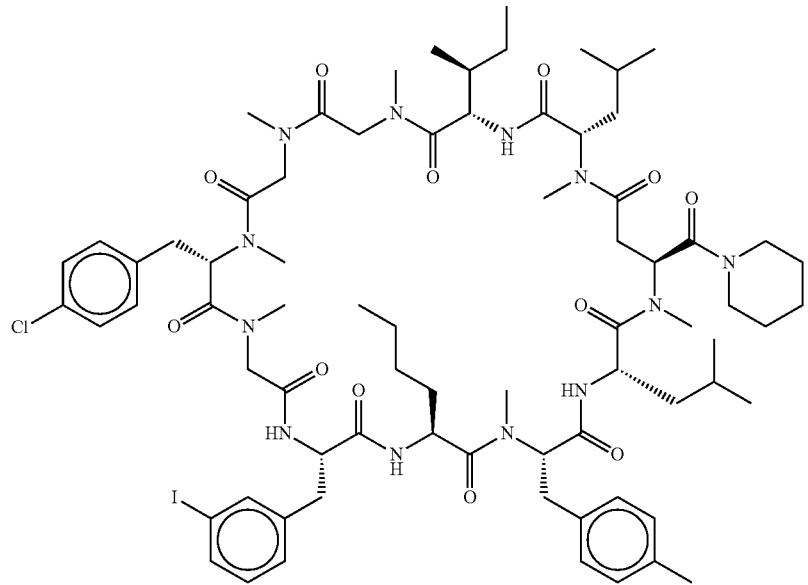 |
| 877 | 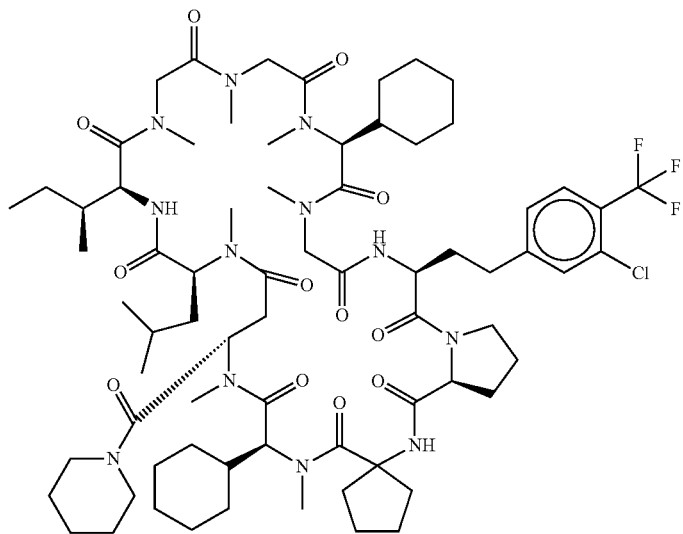 |

TABLE 24-continued
| Compound No. | Structural formula |
|---|---|
| 878 | 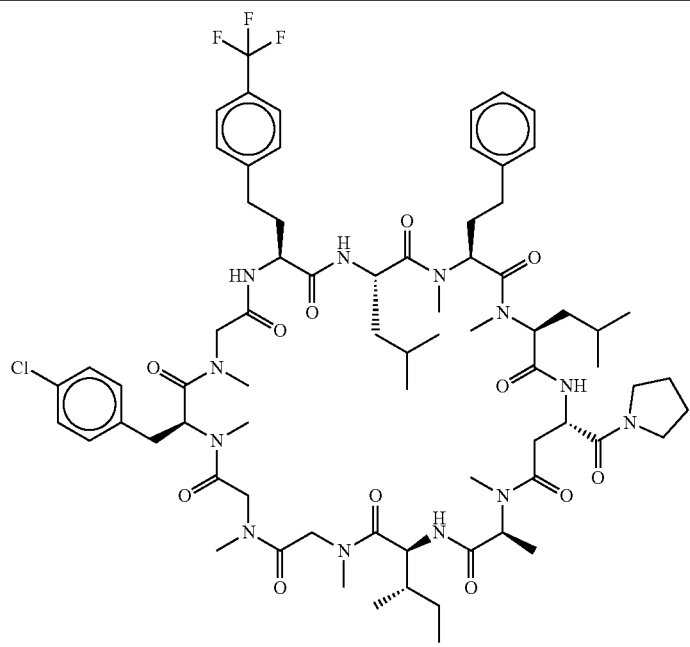 |
| 879 | 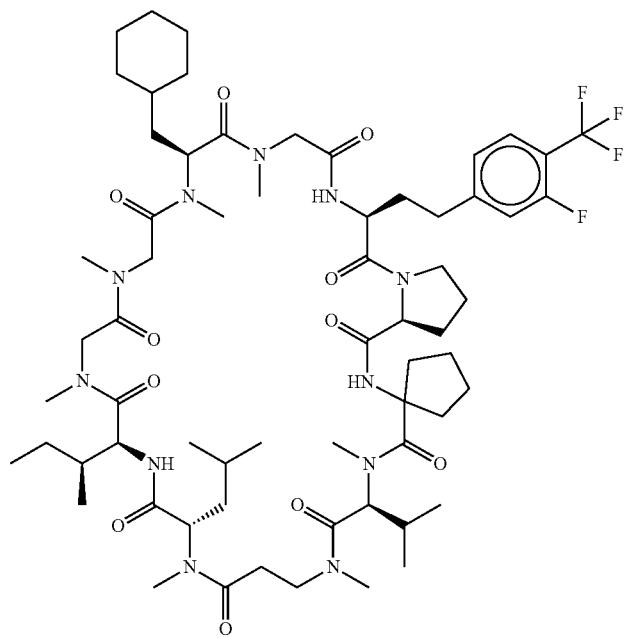 |

TABLE 24-continued
| Compound No. | Structural formula |
|---|---|
| 880 | 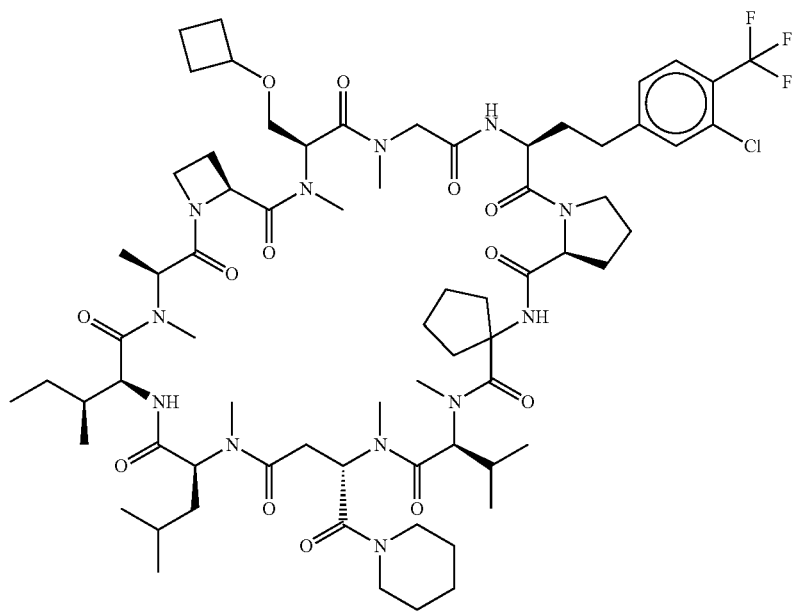 |
| 881 | 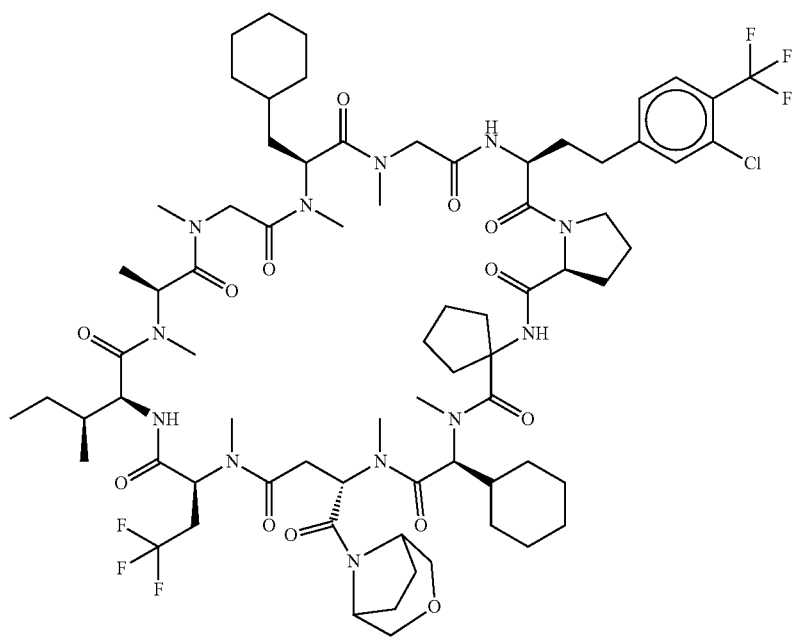 |

TABLE 24-continued
| Compound No. | Structural formula |
|---|---|
| 882 | 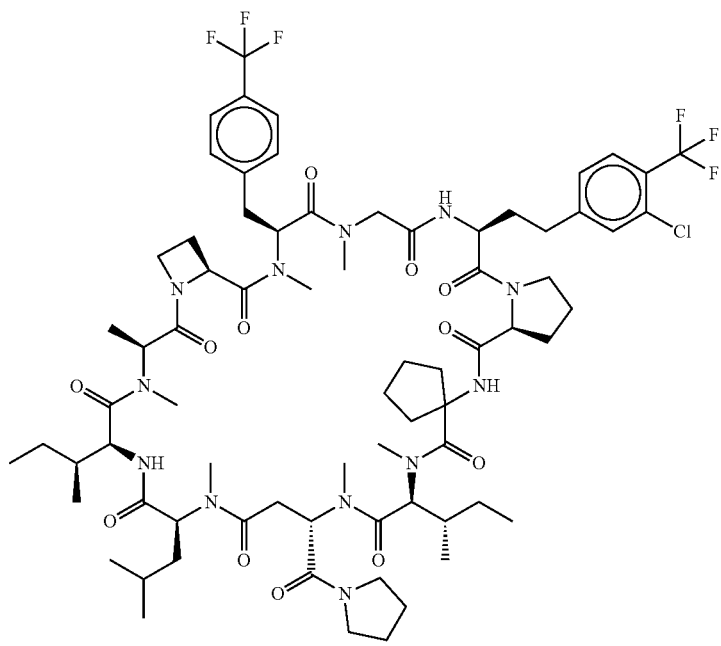 |
| 883 | 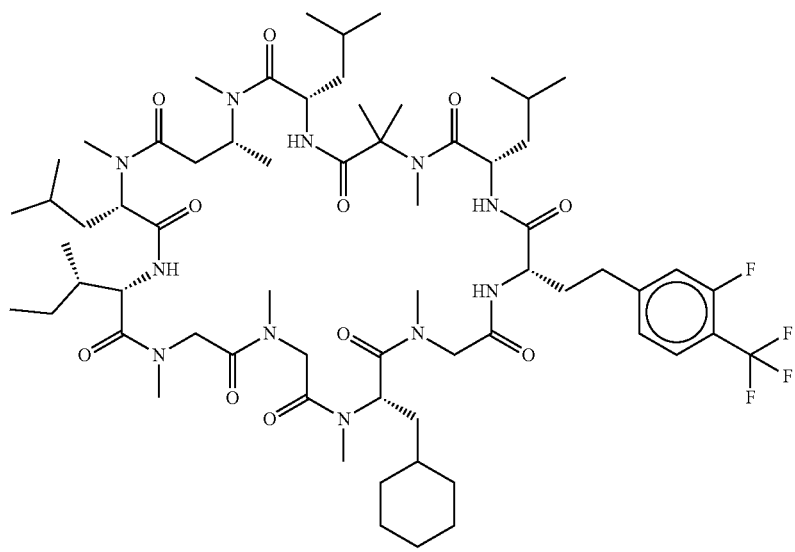 |

TABLE 24-continued
| Compound No. | Structural formula |
|---|---|
| 884 | 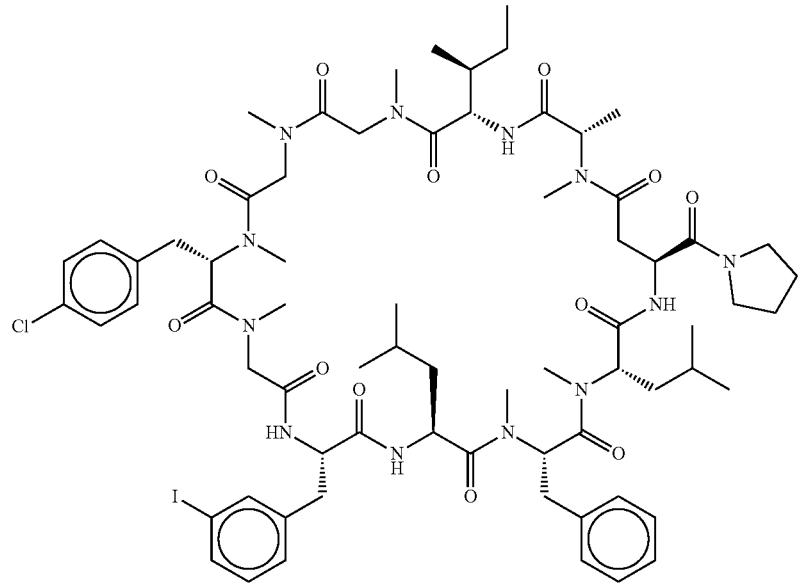 |
| 885 | 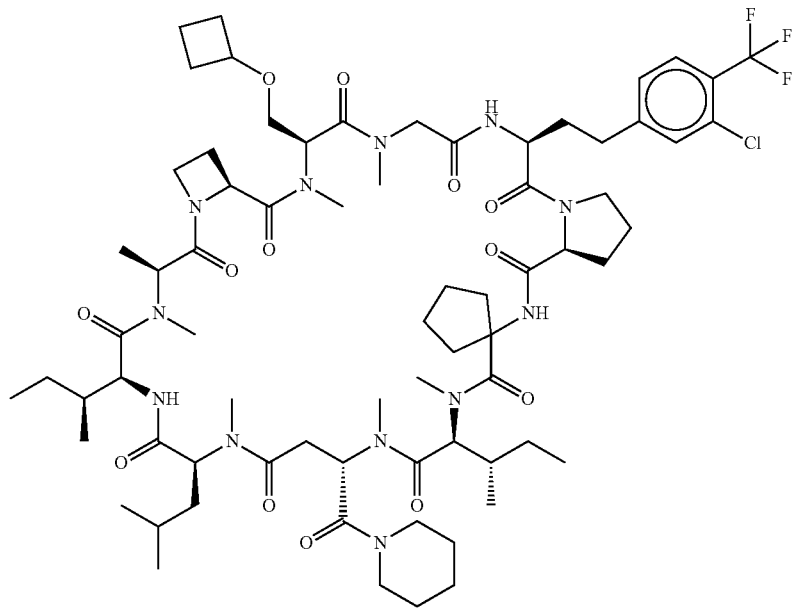 |

… TABLE 24-continued
| Compound No. | Structural formula |
|---|---|
| 886 | 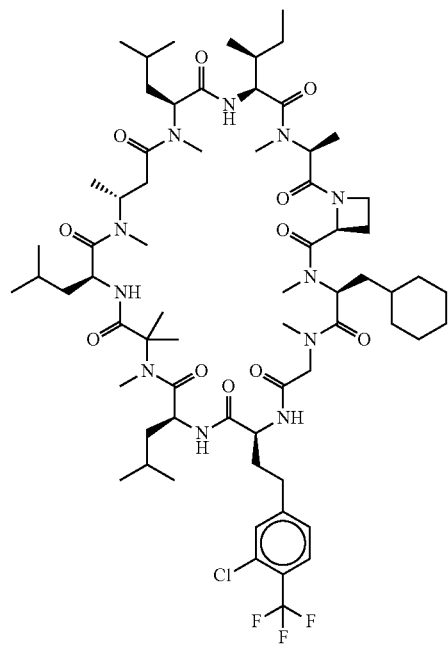 |
| 887 | 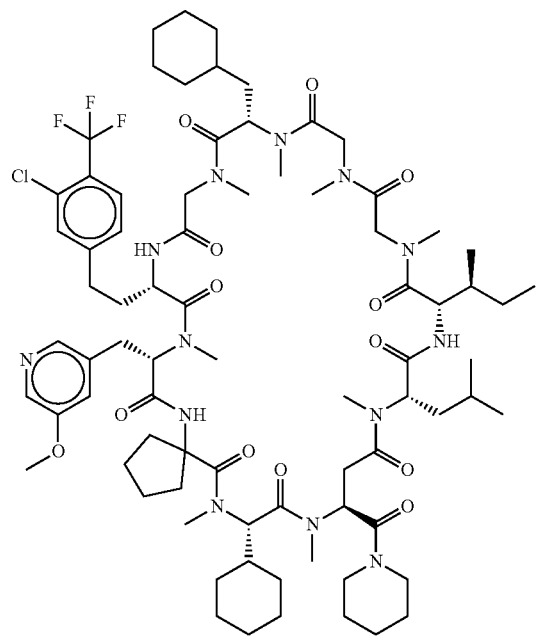 |

TABLE 24-continued
| Compound No. | Structural formula |
|---|---|
| 888 | 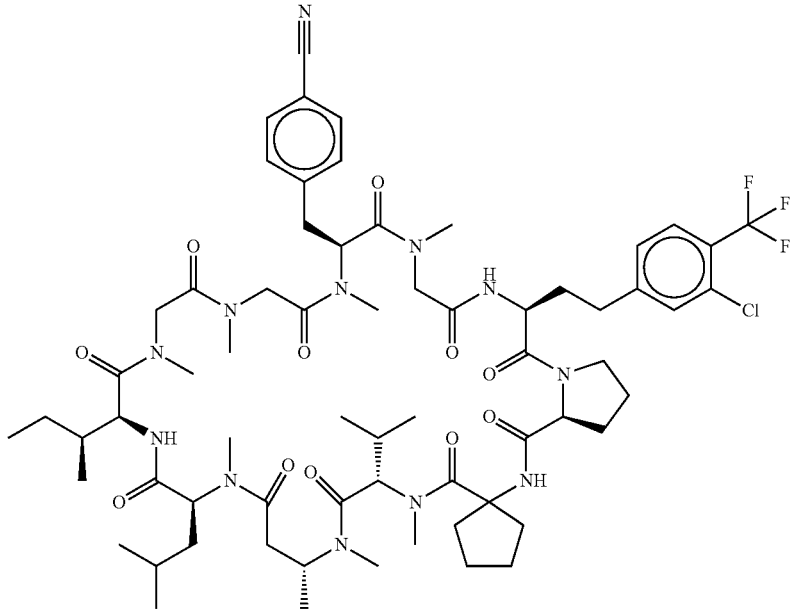 |
| 889 | 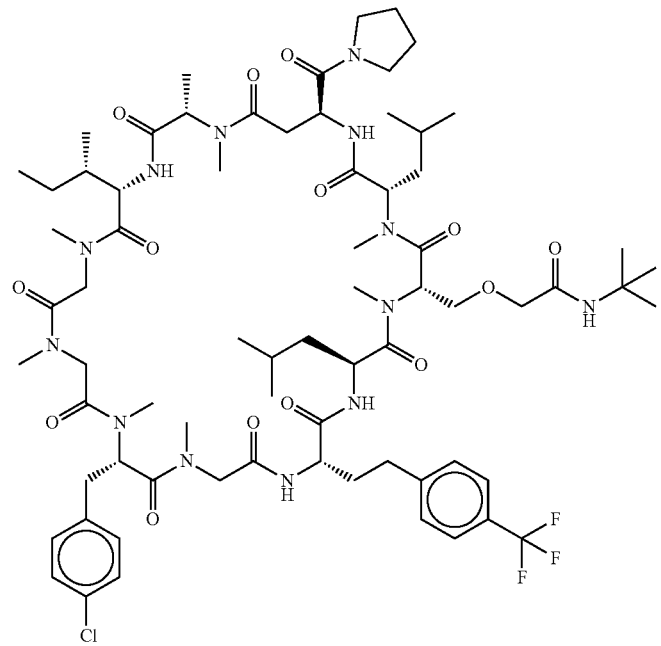 |

TABLE 24-continued
| Compound No. | Structural formula |
|---|---|
| 890 | 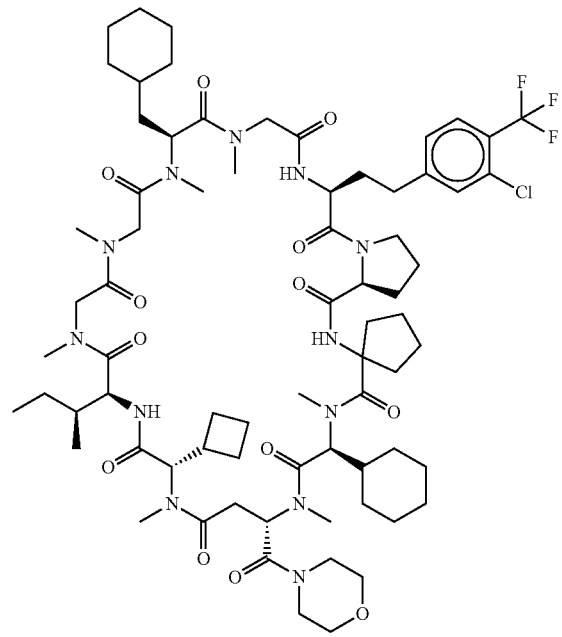 |
| 891 | 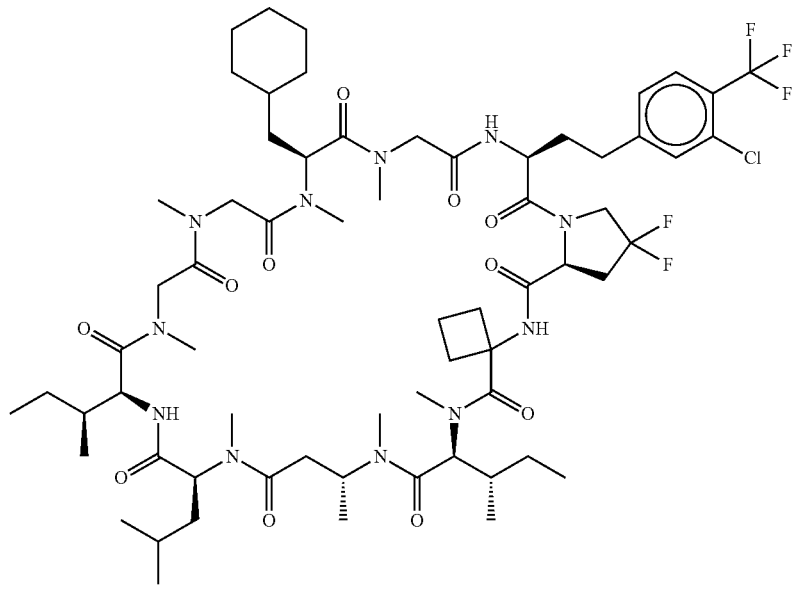 |

TABLE 24-continued
| Compound No. | Structural formula |
|---|---|
| 892 | 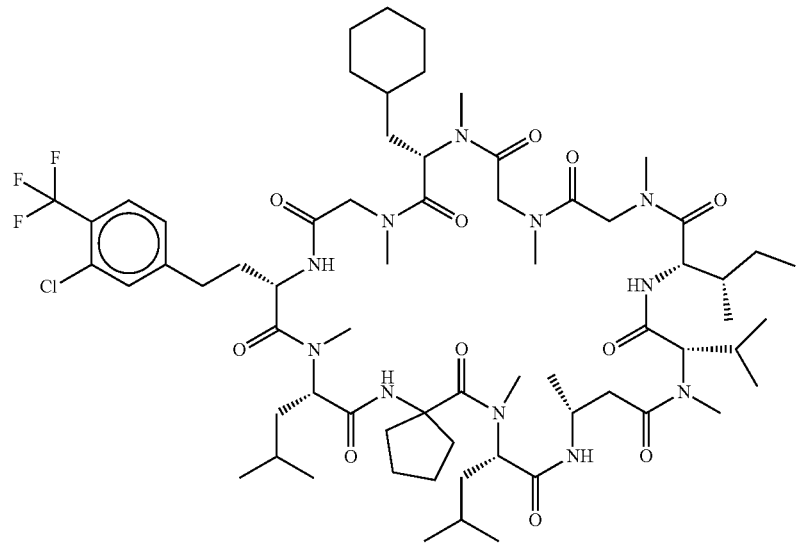 |
| 893 | 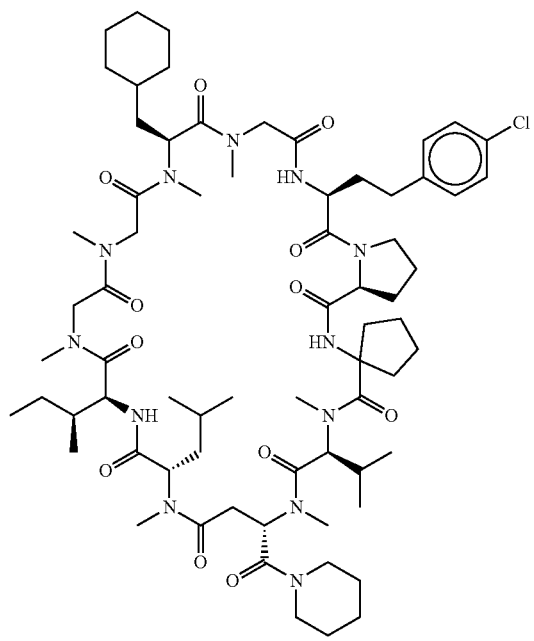 |

TABLE 24-continued
| Compound No. | Structural formula |
|---|---|
| 894 | 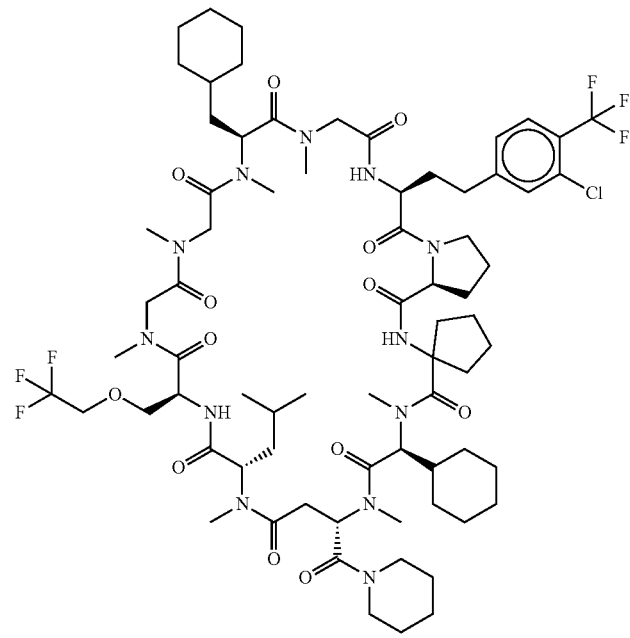 |
| 895 | 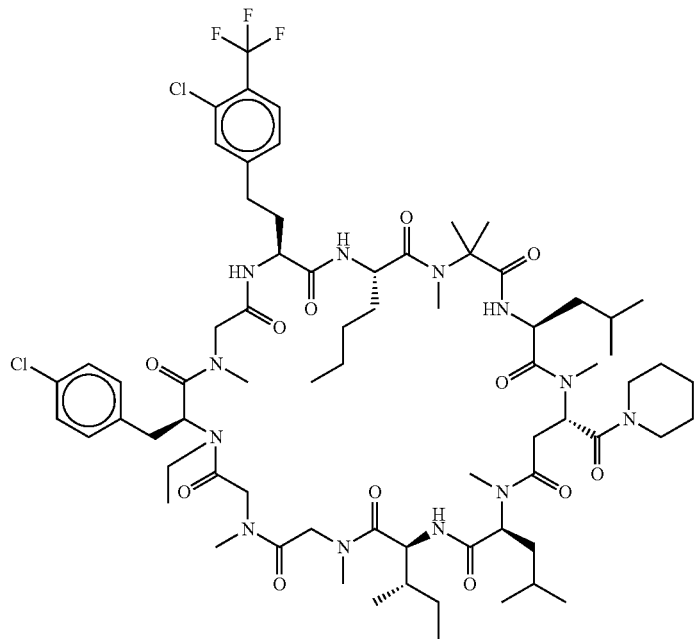 |

TABLE 24-continued
| Compound No. | Structural formula |
|---|---|
| 896 | 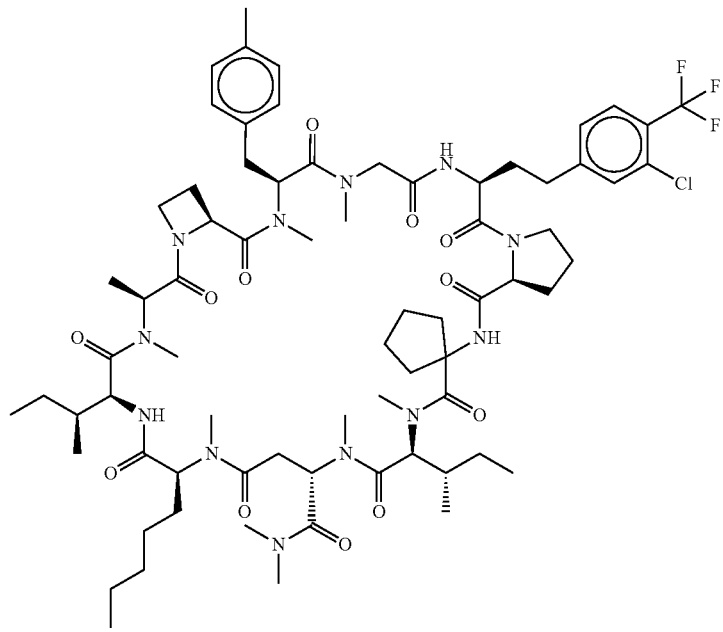 |
| 897 | 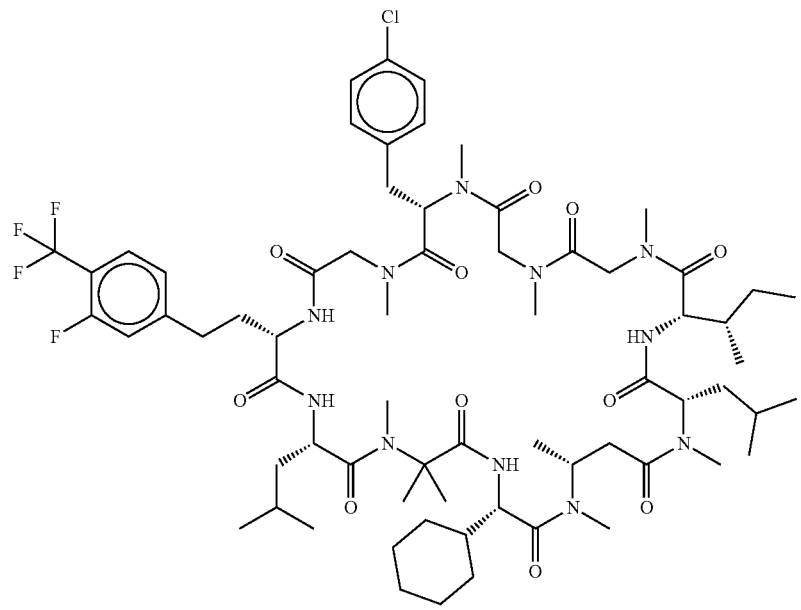 |

TABLE 24-continued
| Compound No. | Structural formula |
|---|---|
| 898 | 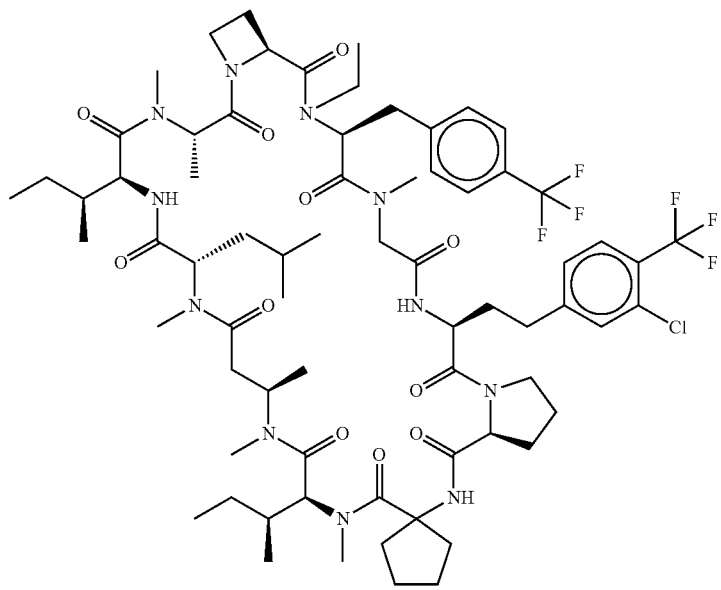 |
| 899 | 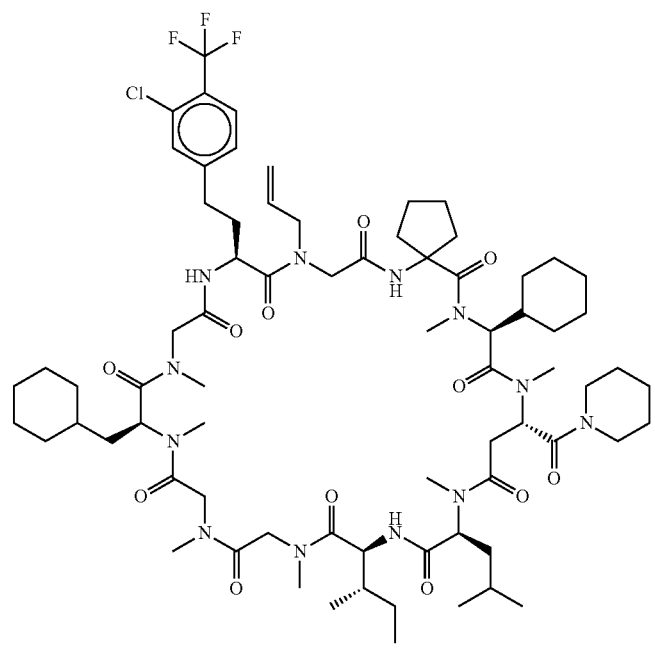 |

TABLE 24-continued
| Compound No. | Structural formula |
|---|---|
| 900 | 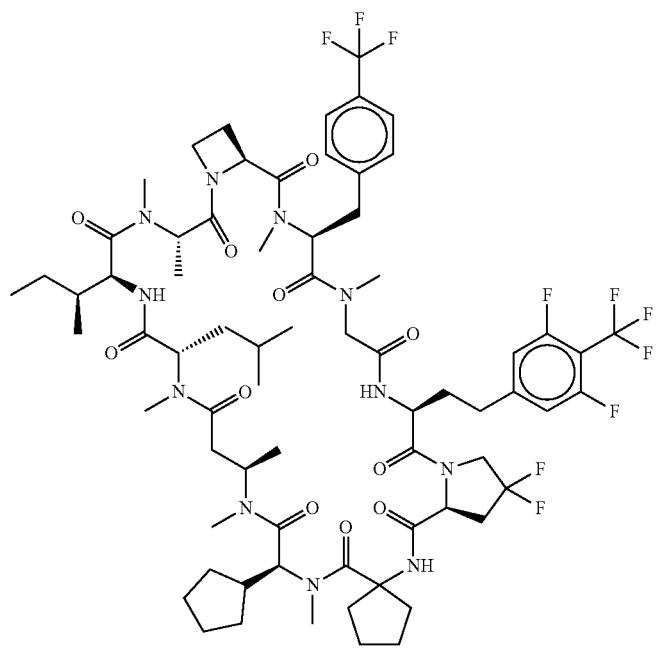 |
| 901 | 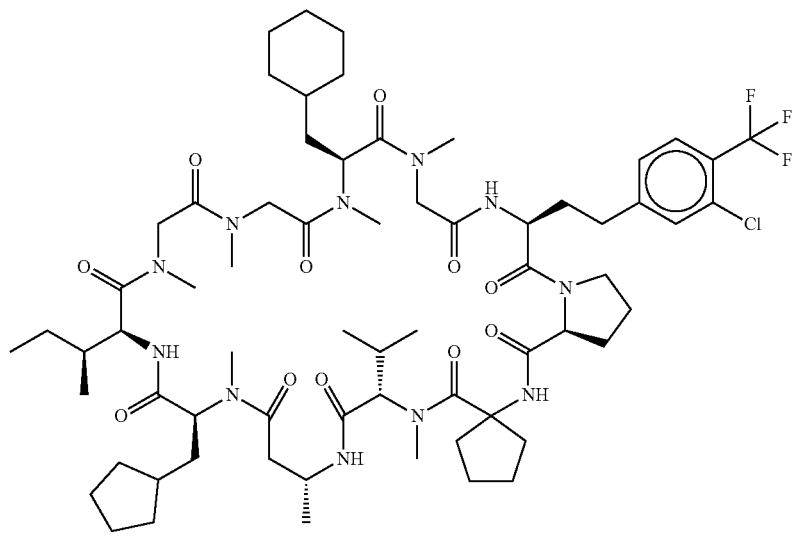 |

TABLE 24-continued
| Compound No. | Structural formula |
|---|---|
| 902 | 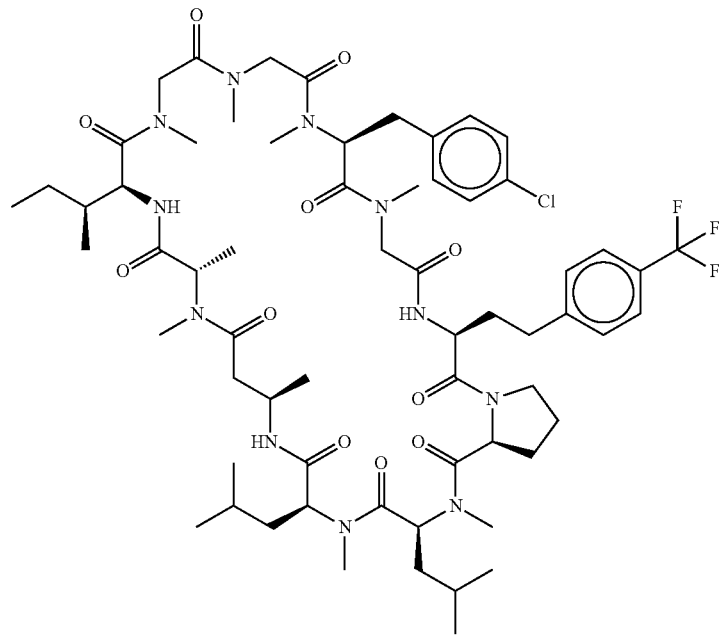 |
| 903 | 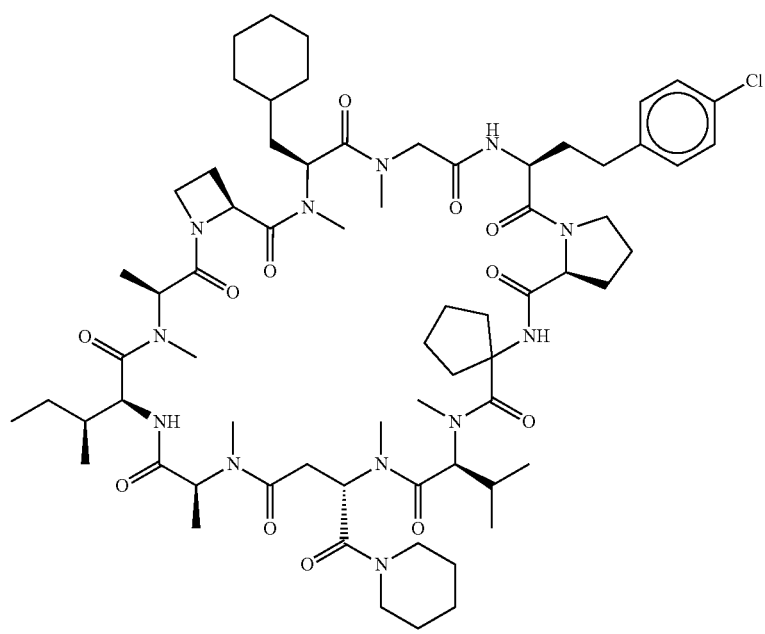 |

TABLE 24-continued
| Compound No. | Structural formula |
|---|---|
| 904 | 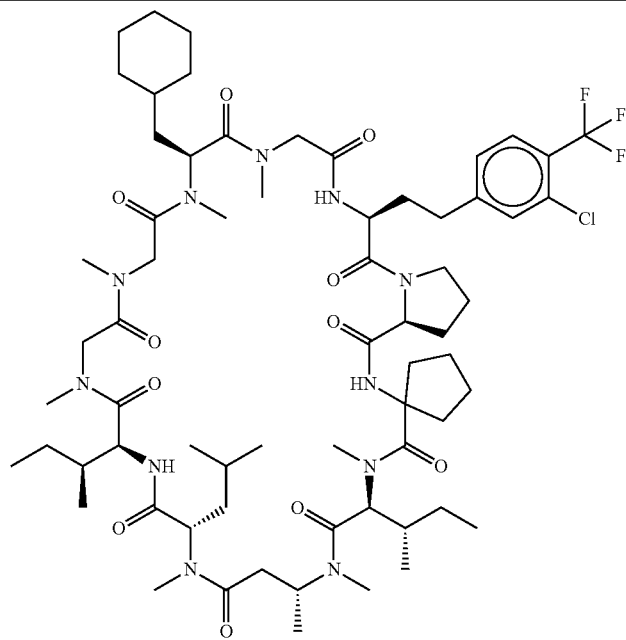 |
| 905 | 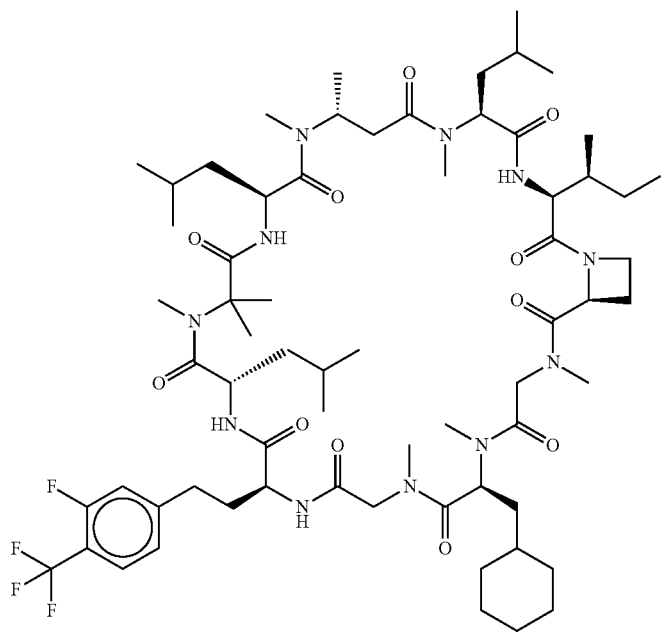 |

TABLE 24-continued
| Compound No. | Structural formula |
|---|---|
| 906 | 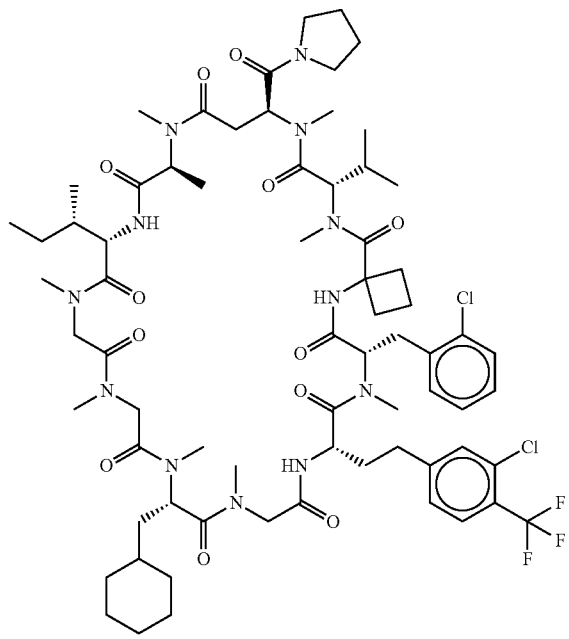 |
| 907 | 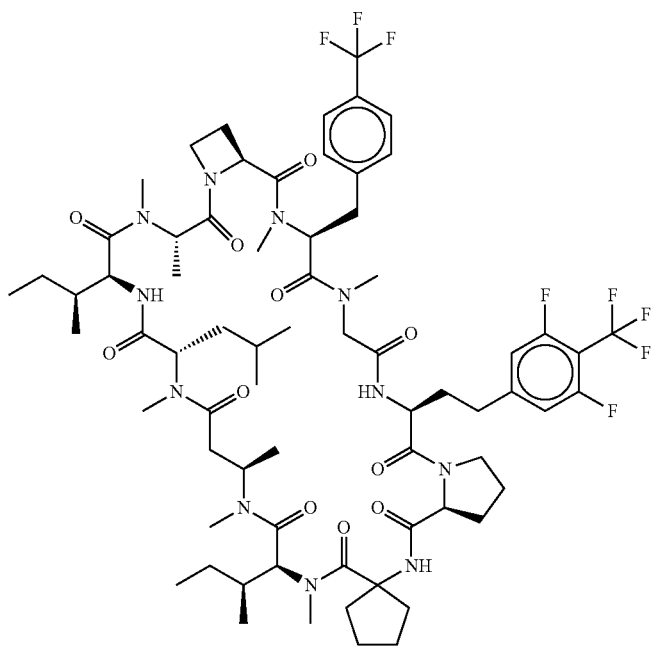 |

TABLE 24-continued
| Compound No. | Structural formula |
|---|---|
| 908 | 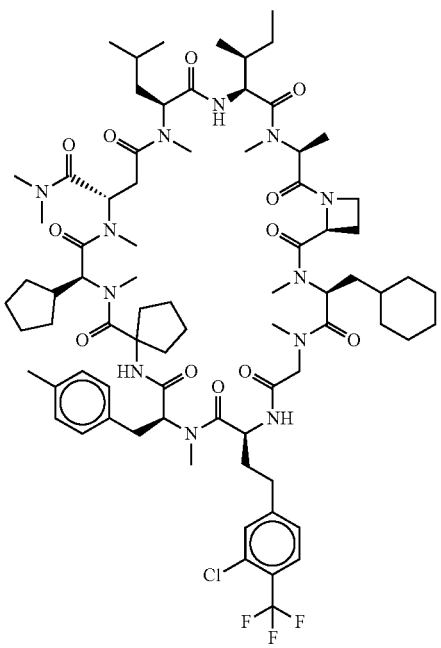 |
| 909 | 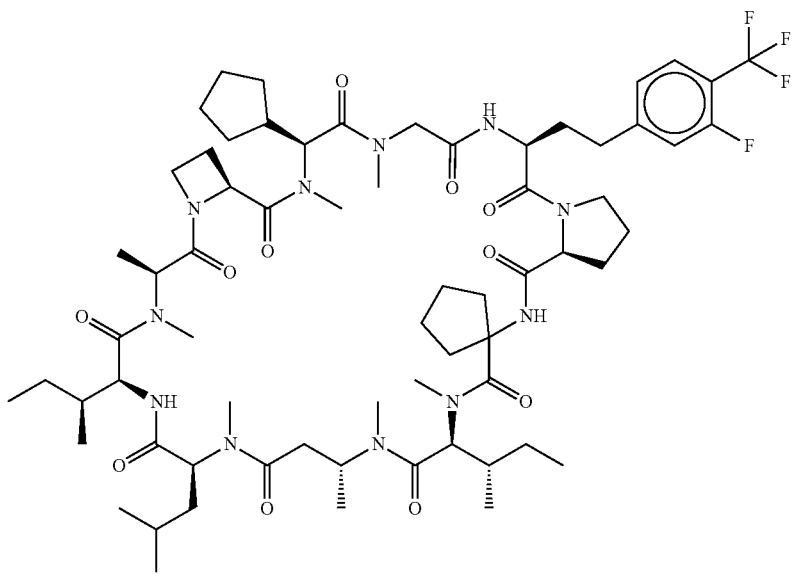 |

TABLE 24-continued
| Compound No. | Structural formula |
|---|---|
| 910 | 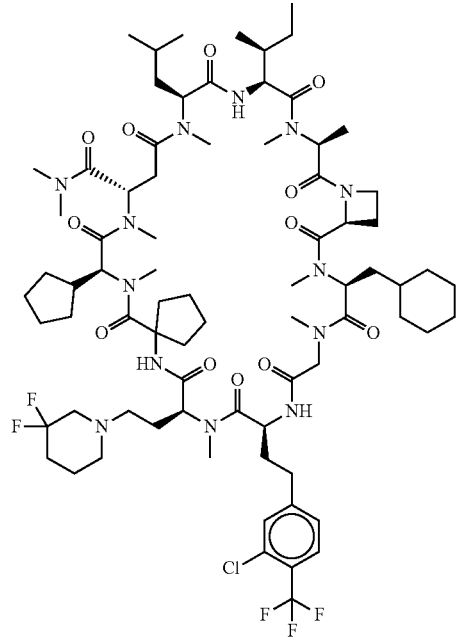 |
| 911 | 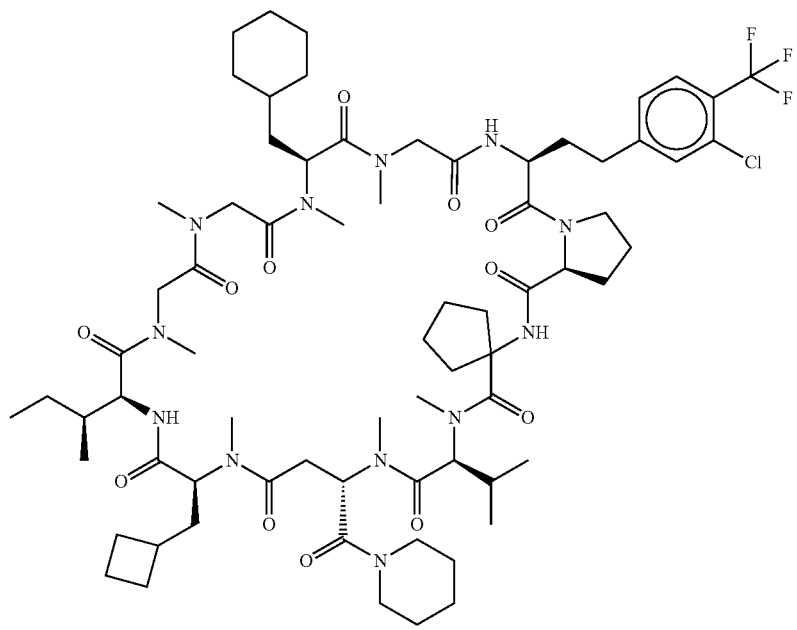 |

TABLE 24-continued
| Compound No. | Structural formula |
|---|---|
| 912 | 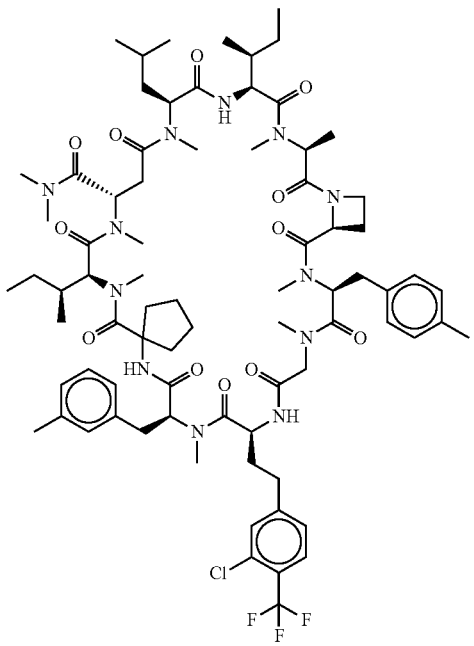 |
| 913 | 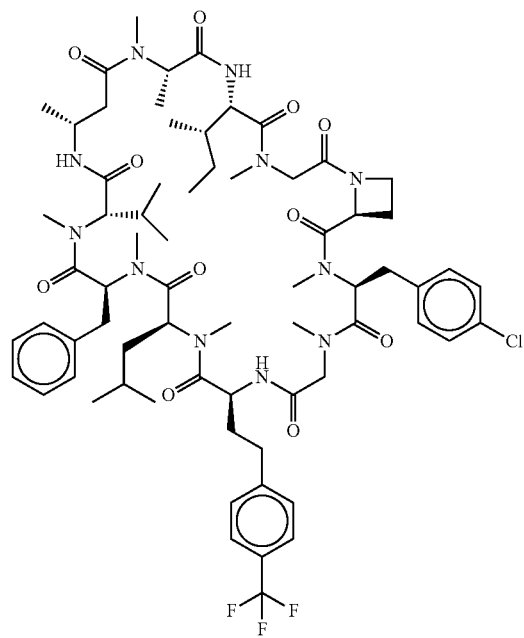 |

TABLE 24-continued
| Compound No. | Structural formula |
|---|---|
| 914 | 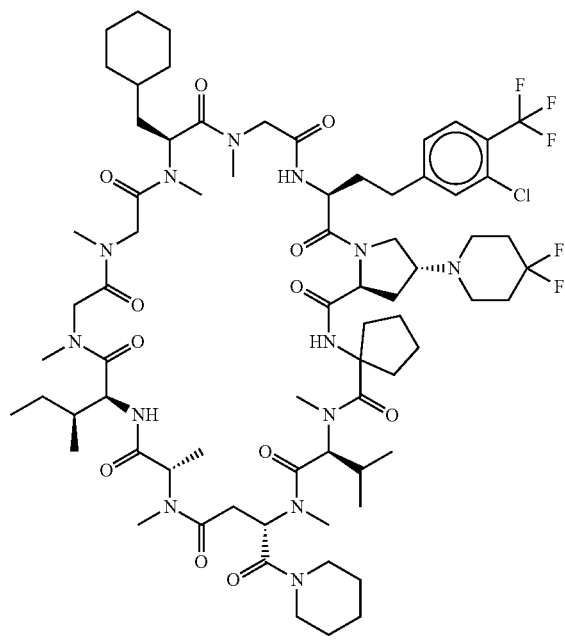 |
| 915 | 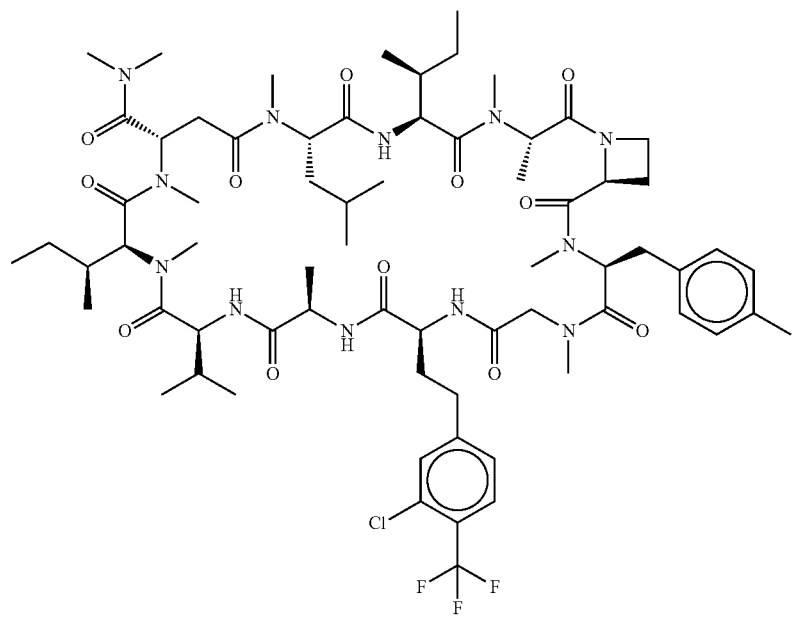 |

TABLE 24-continued
| Compound No. | Structural formula |
|---|---|
| 916 | 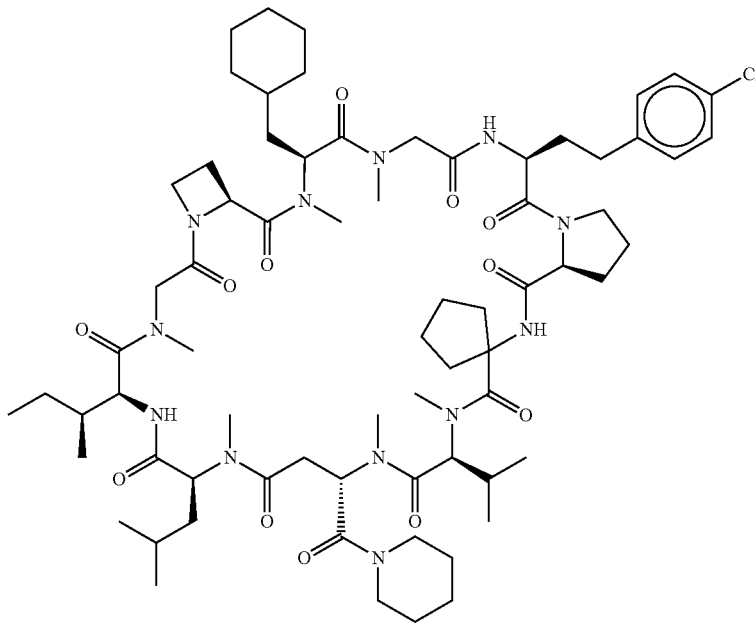 |
| 917 | 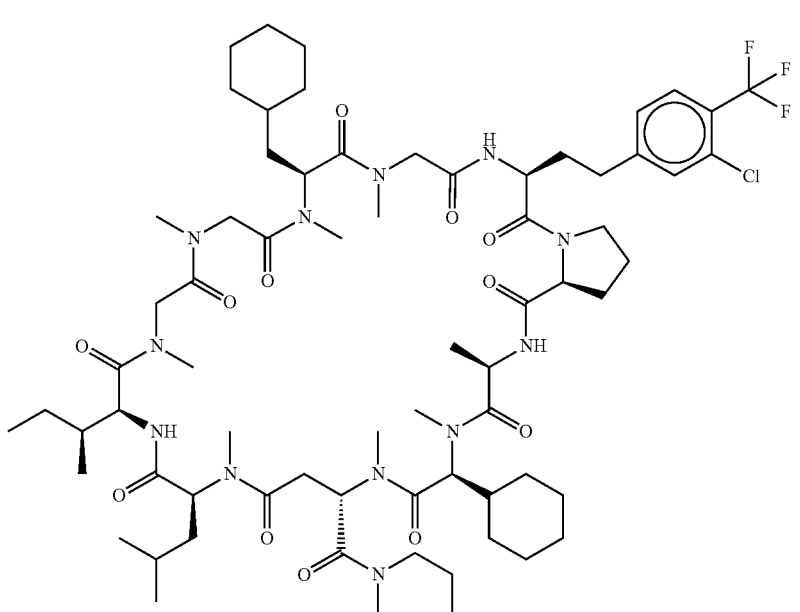 |

TABLE 24-continued
| Compound No. | Structural formula |
|---|---|
| 918 | 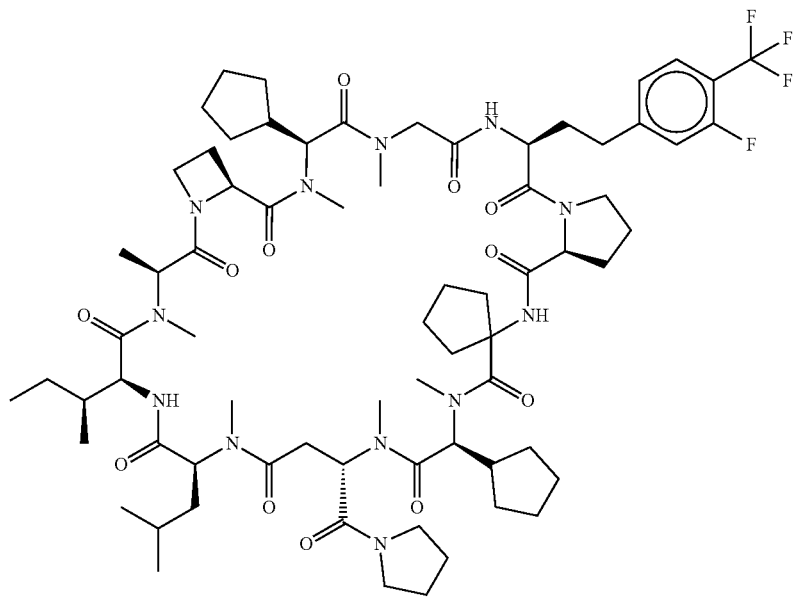 |
| 919 | 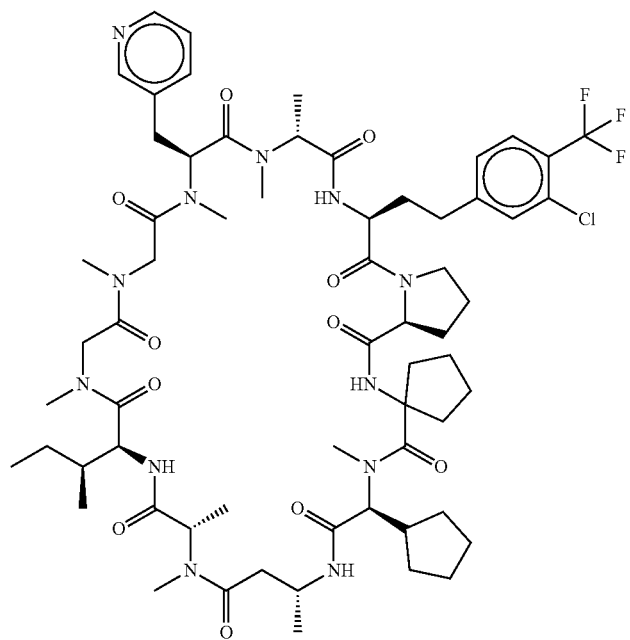 |

TABLE 24-continued
| Compound No. | Structural formula |
|---|---|
| 920 | 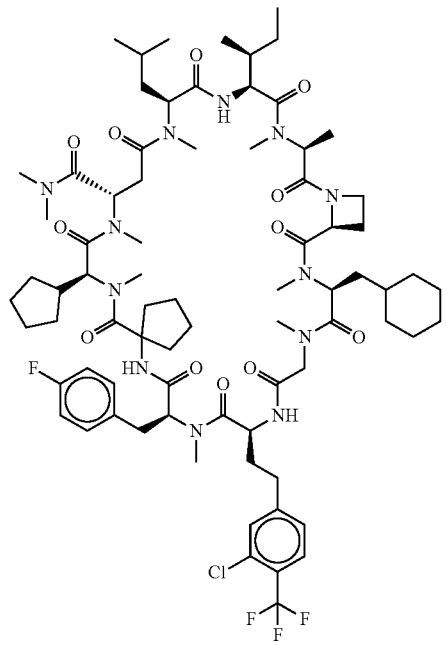 |
| 921 | 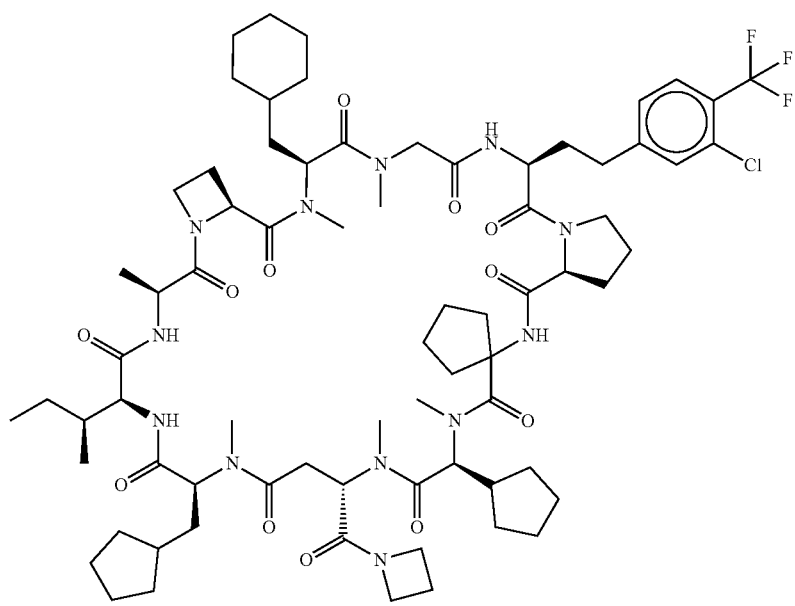 |

TABLE 24-continued
| Compound No. | Structural formula |
|---|---|
| 922 | 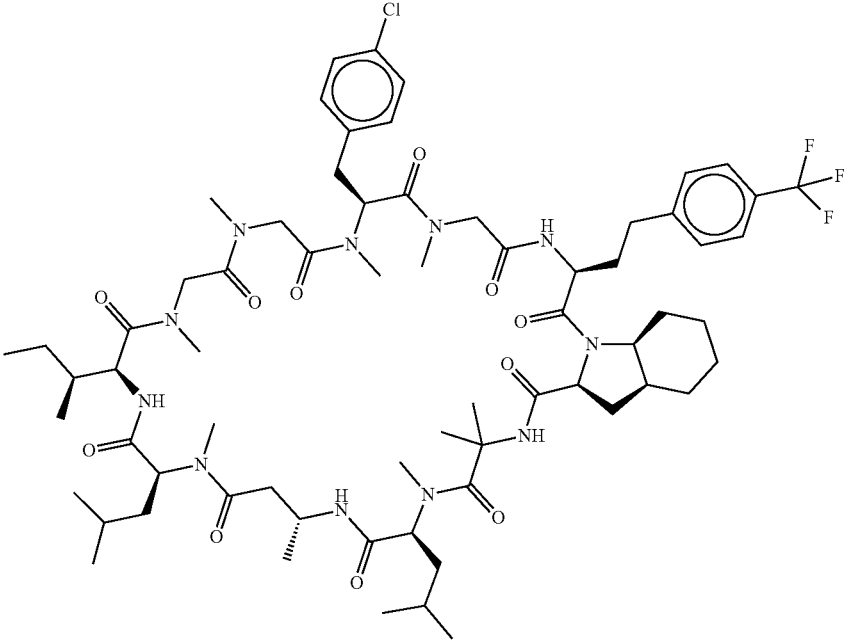 |
| 923 | 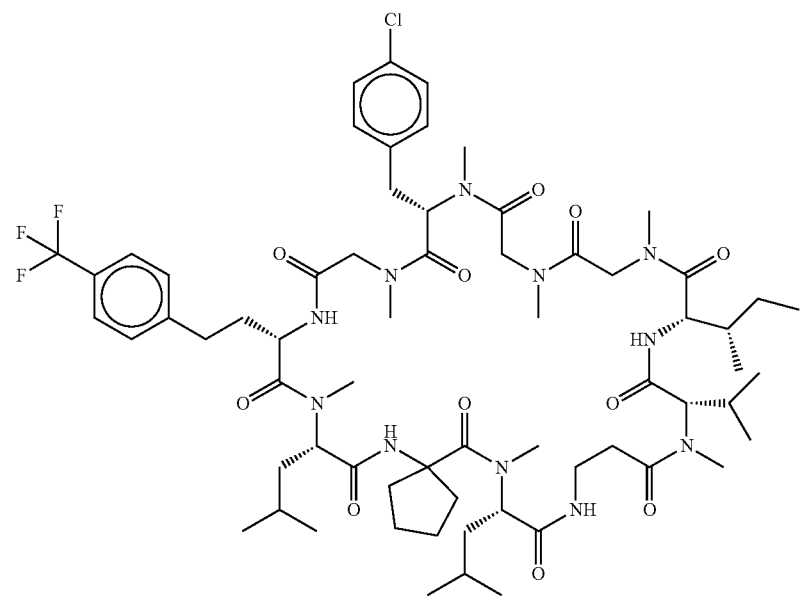 |

TABLE 24-continued
| Compound No. | Structural formula |
|---|---|
| 924 | 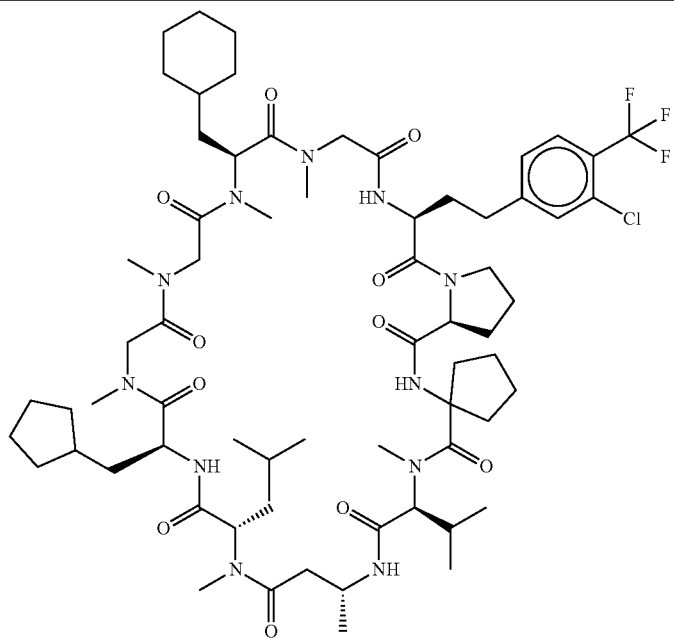 |
| 925 | 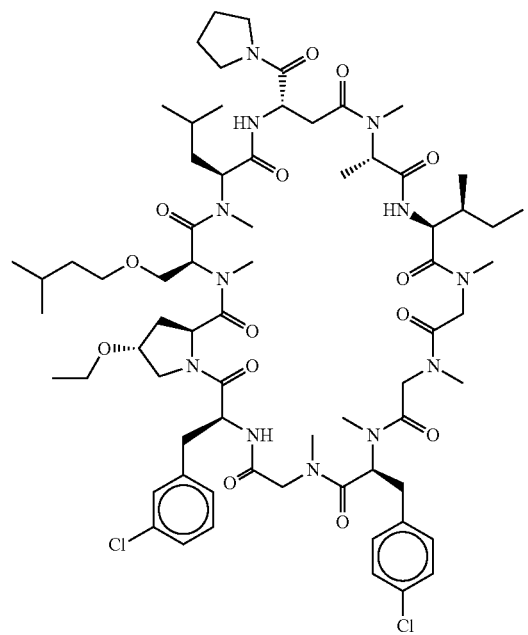 |

TABLE 24-continued
| Compound No. | Structural formula |
|---|---|
| 926 | 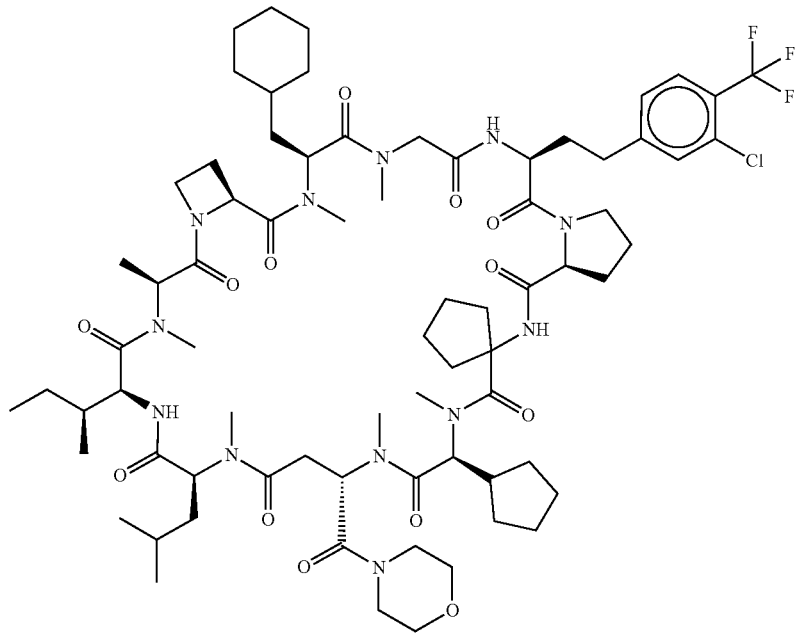 |
| 927 | 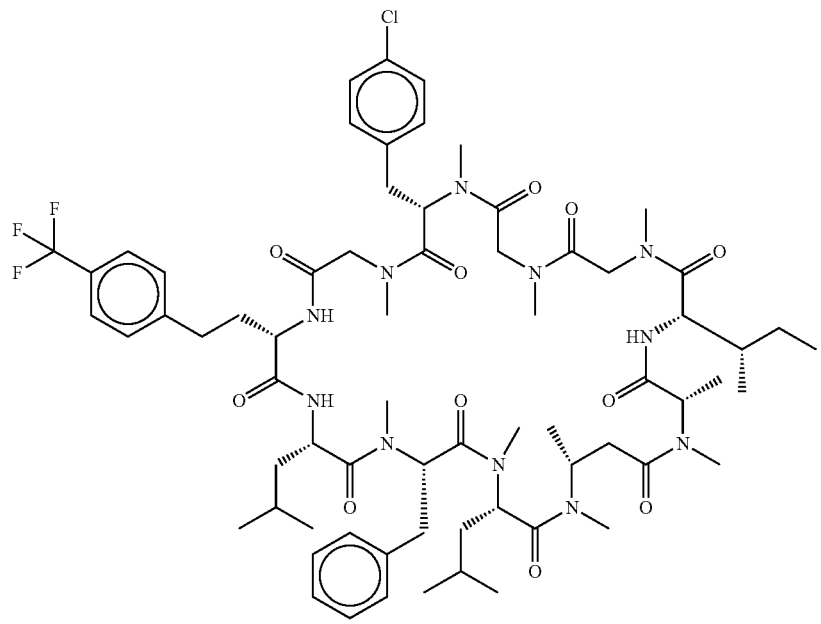 |

TABLE 24-continued
| Compound No. | Structural formula |
|---|---|
| 928 | 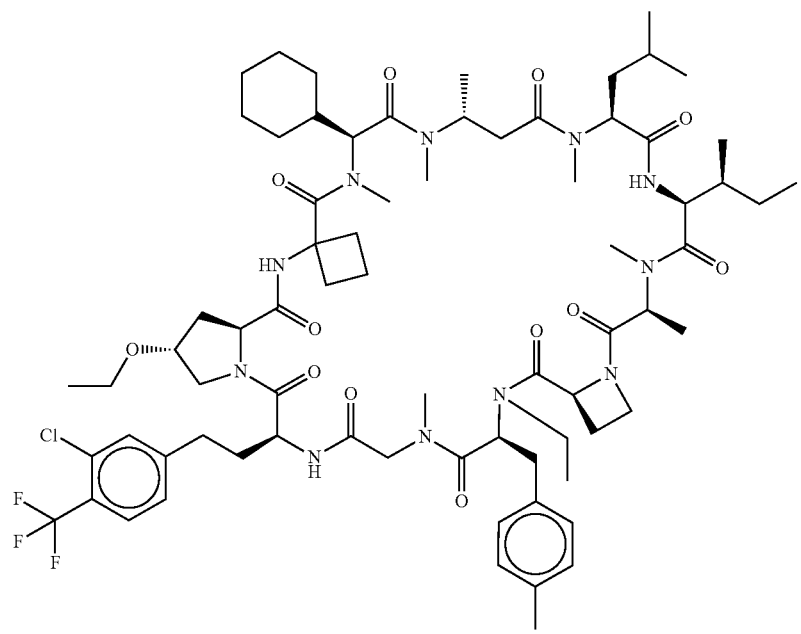 |
| 929 | 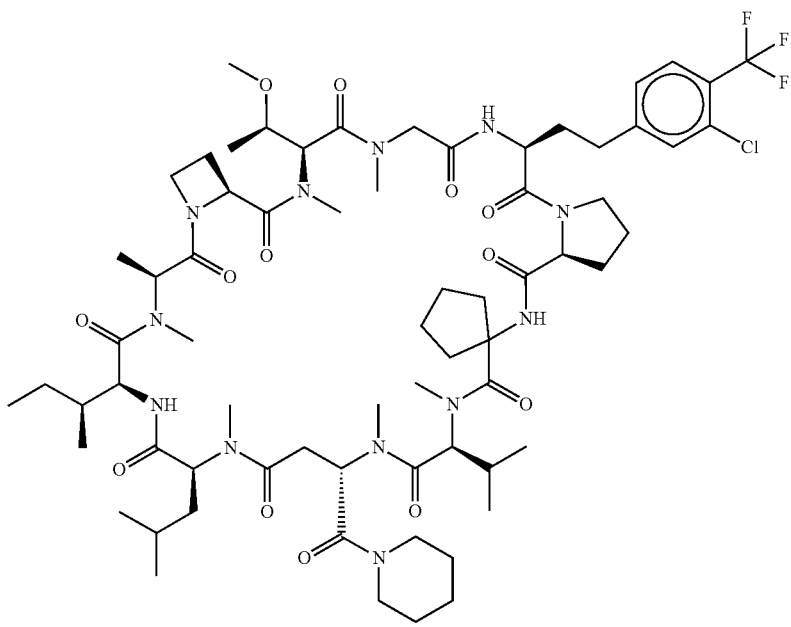 |

TABLE 24-continued
| Compound No. | Structural formula |
|---|---|
| 930 | 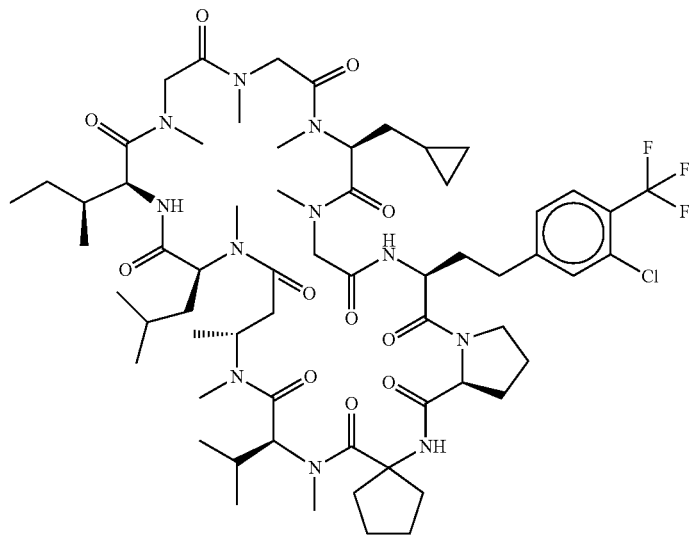 |
| 931 | 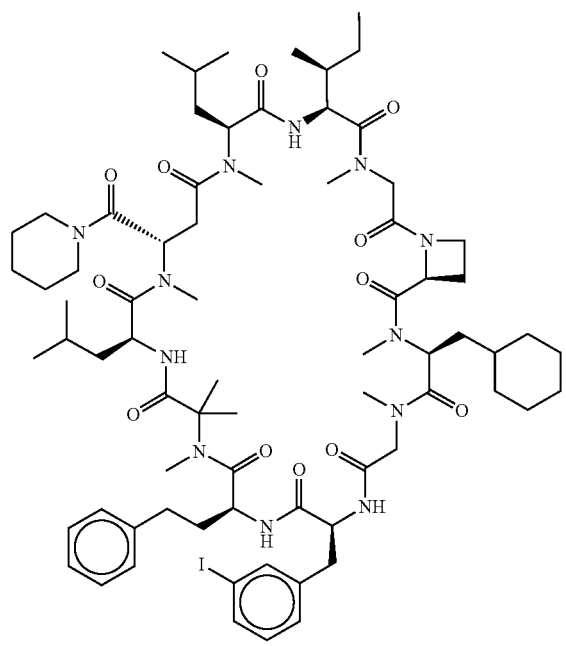 |

TABLE 24-continued
| Compound No. | Structural formula |
|---|---|
| 932 | 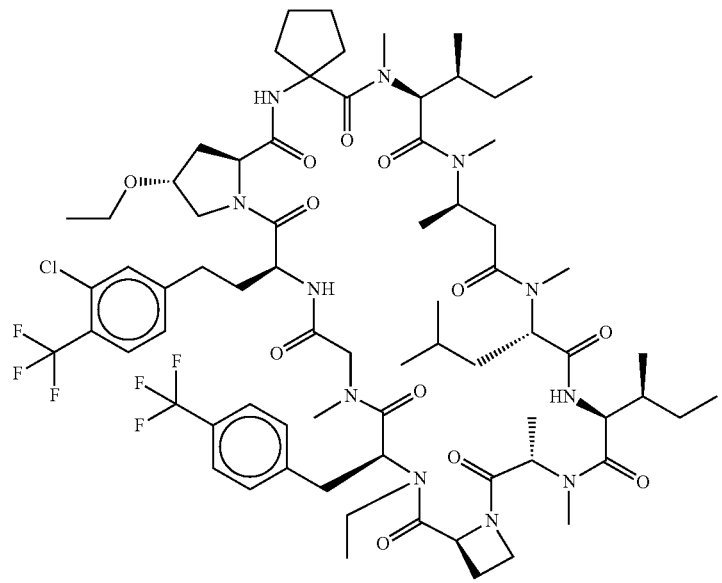 |
| 933 | 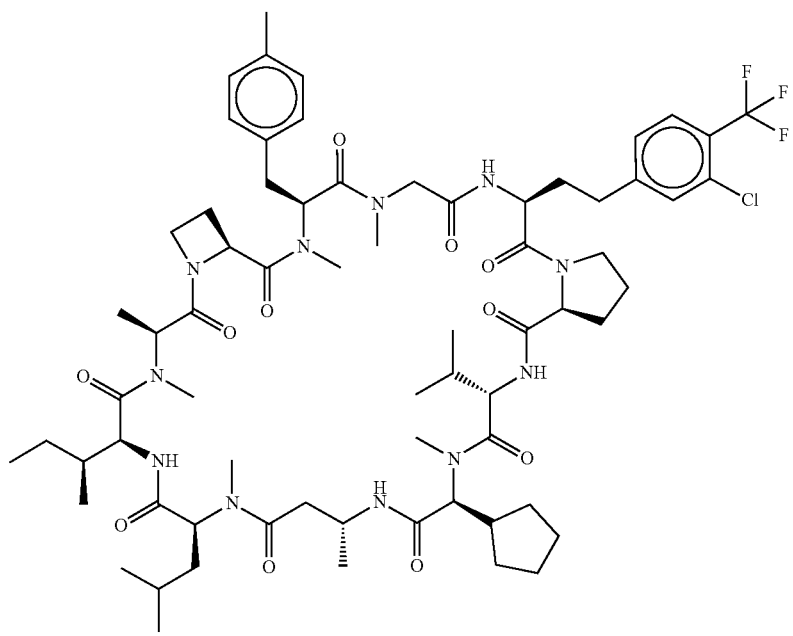 |

TABLE 24-continued
| Compound No. | Structural formula |
|---|---|
| 934 | 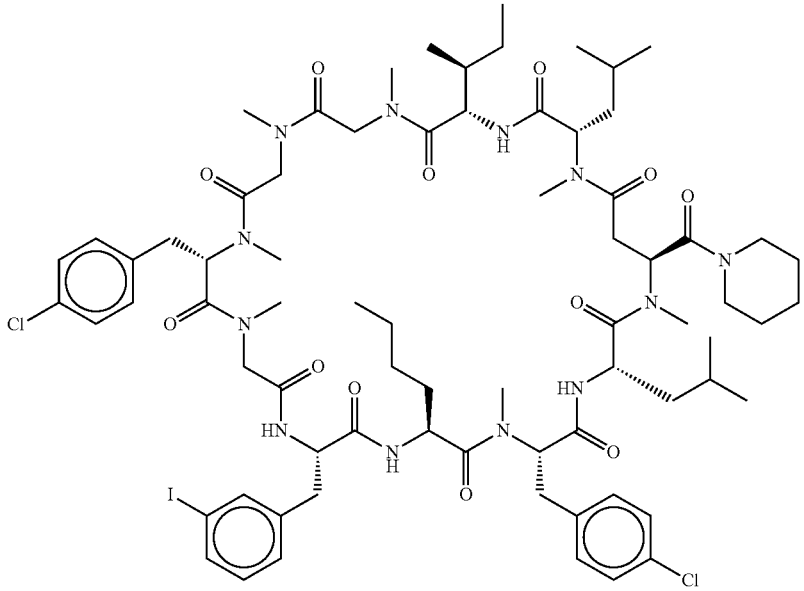 |
| 935 | 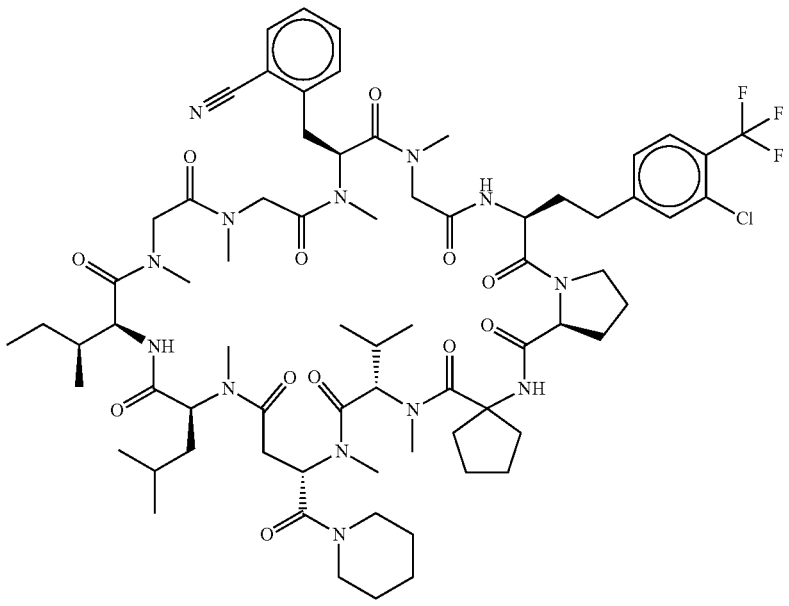 |

TABLE 24-continued
| Compound No. | Structural formula |
|---|---|
| 936 | 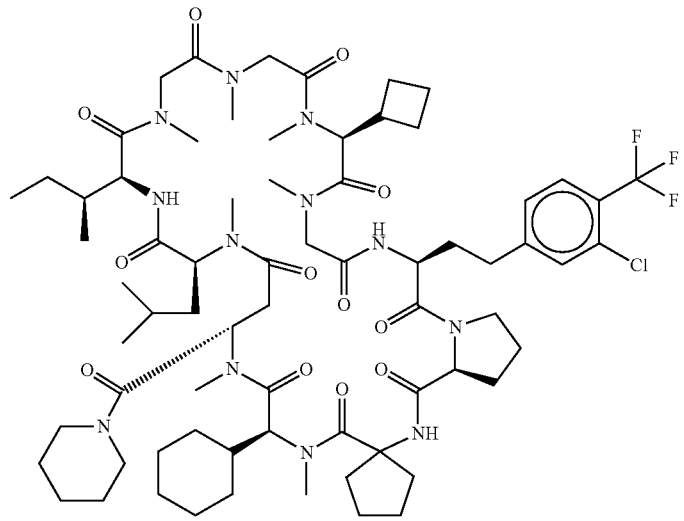 |
| 937 | 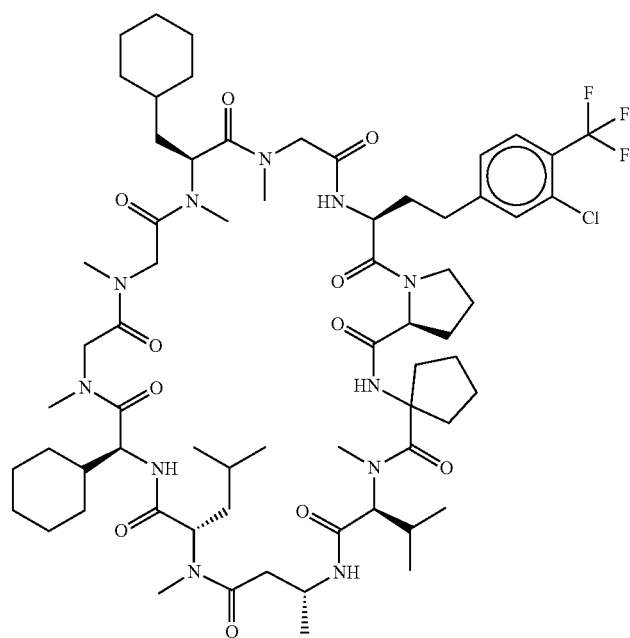 |

TABLE 24-continued
| Compound No. | Structural formula |
|---|---|
| 938 | 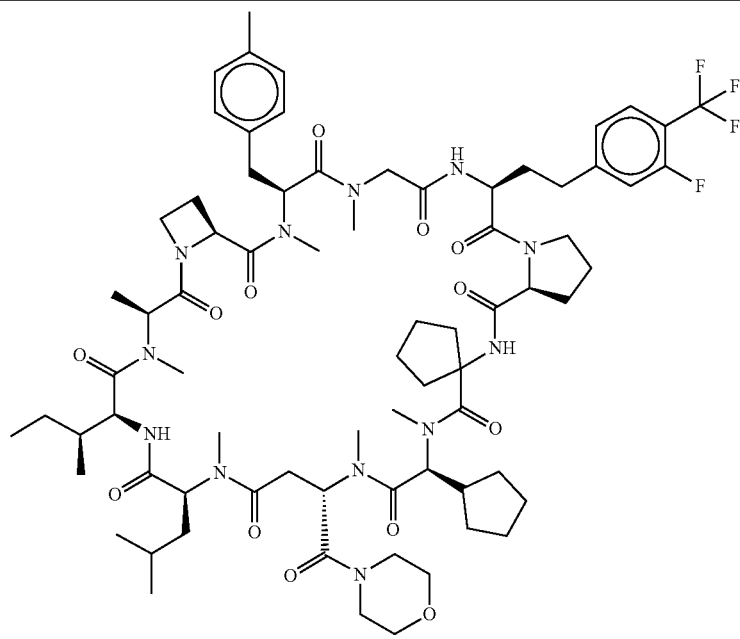 |
| 939 | 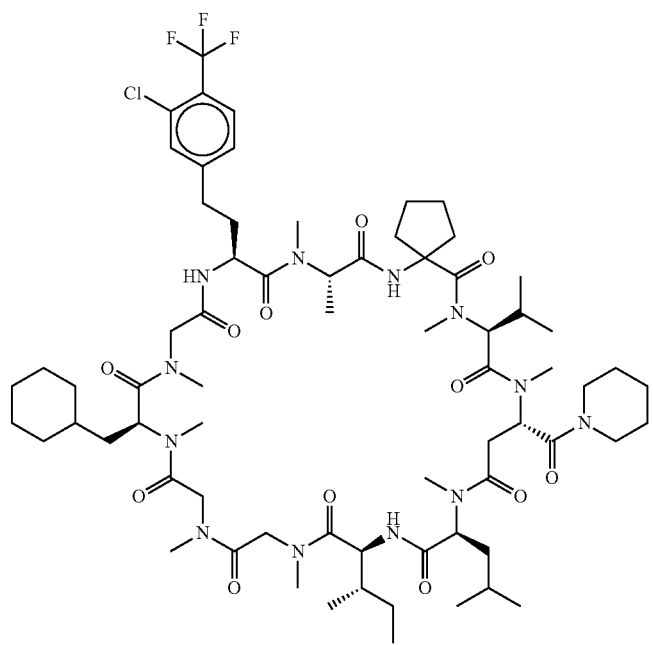 |

TABLE 24-continued
| Compound No. | Structural formula |
| --- | --- |
| 940 | 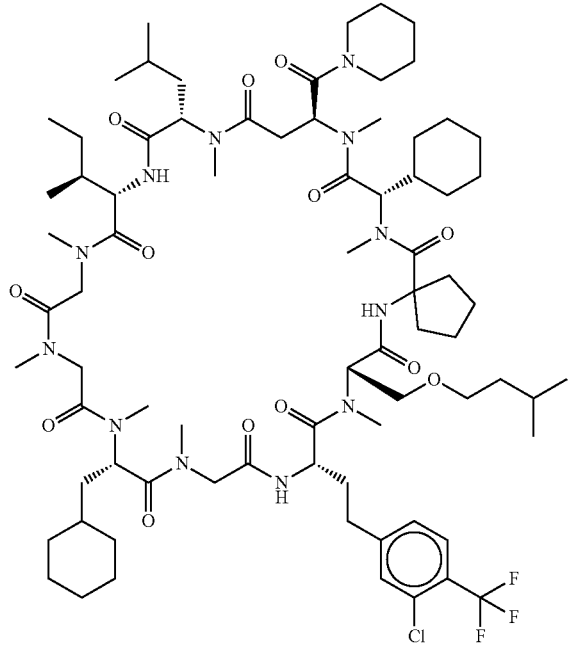 |
| 941 | 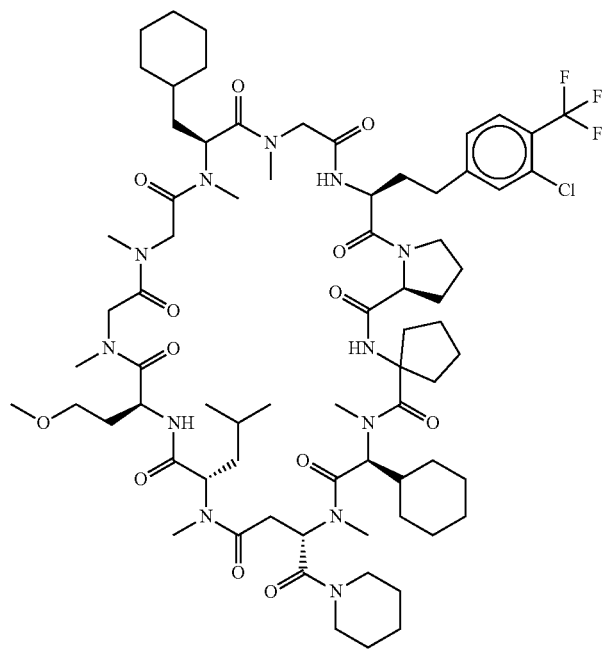 |

TABLE 24-continued
| Compound No. | Structural formula |
|---|---|
| 942 | 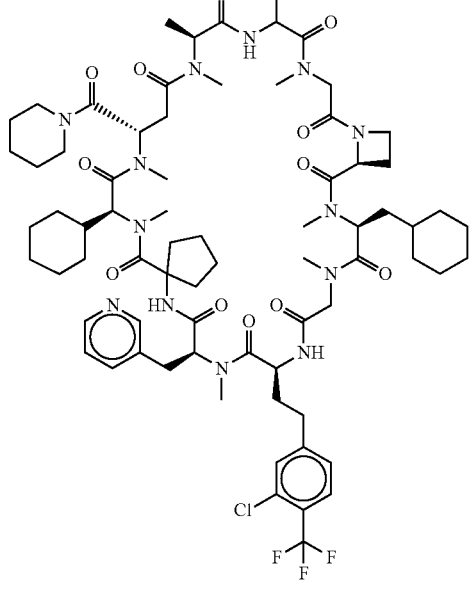 |
| 943 | 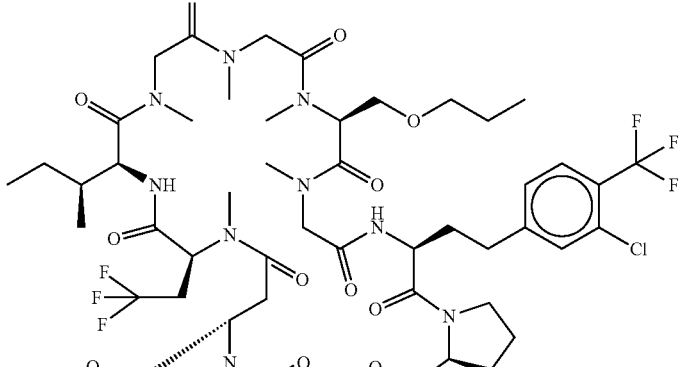 |

TABLE 24-continued
| Compound No. | Structural formula |
|---|---|
| 944 | 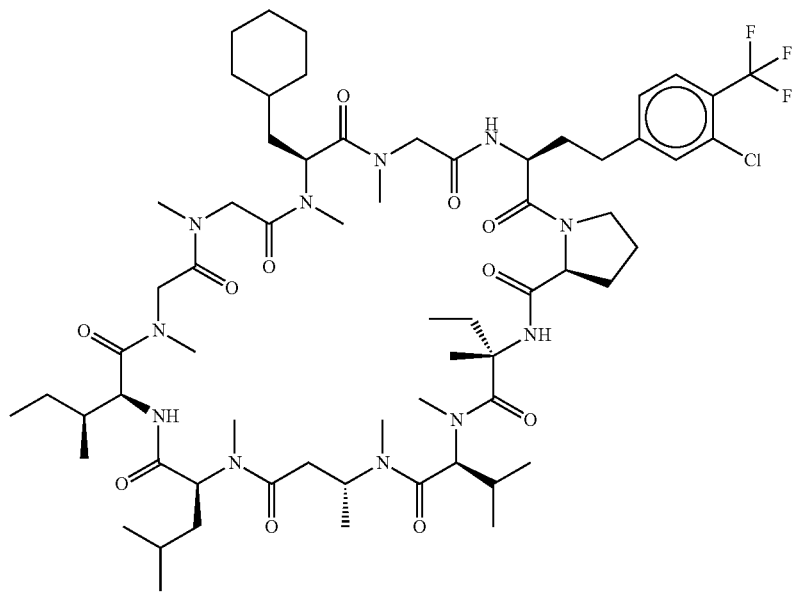 |
| 945 | 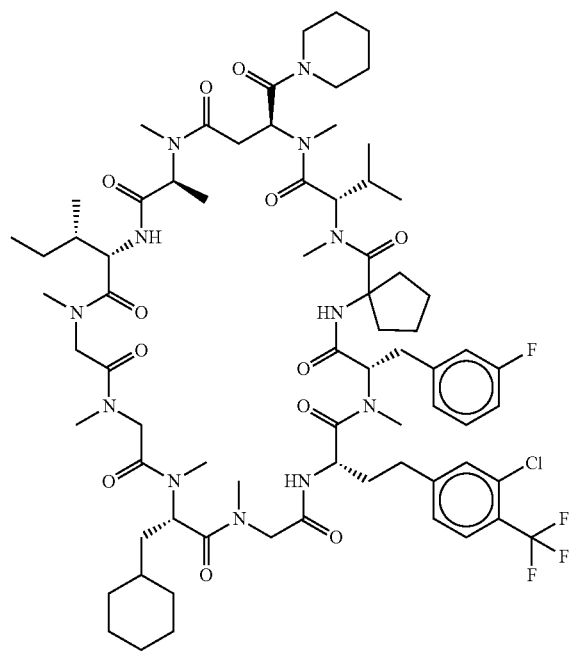 |

TABLE 24-continued
| Compound No. | Structural formula |
|---|---|
| 946 | 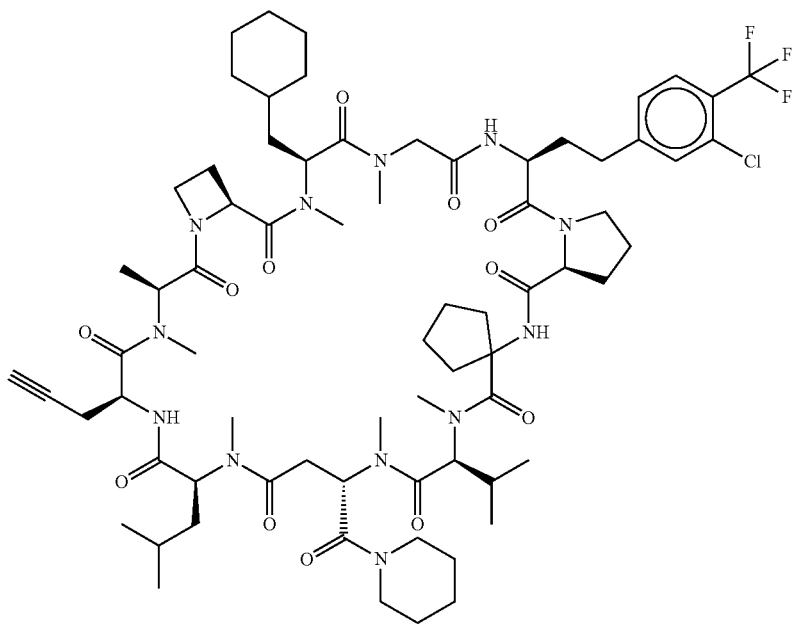 |
| 947 | 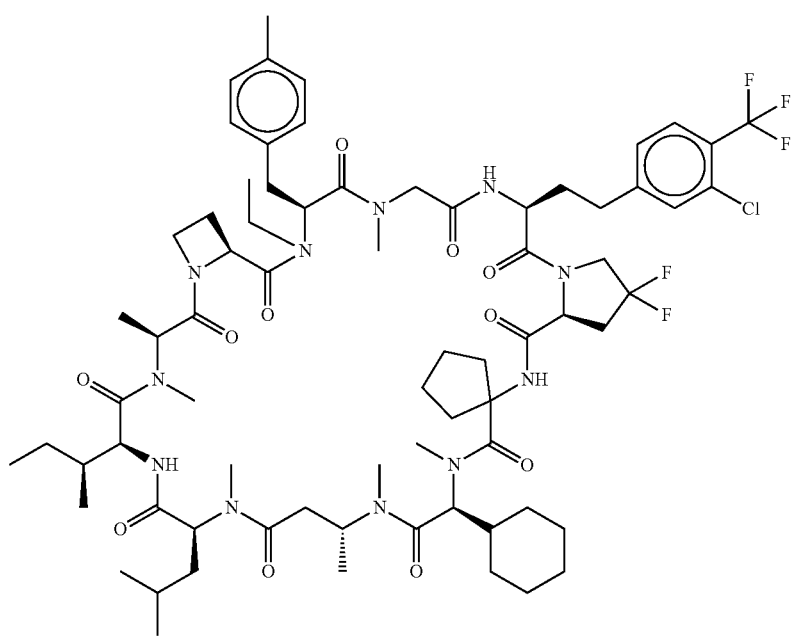 |

TABLE 24-continued
| Compound No. | Structural formula |
| --- | --- |
| 948 | 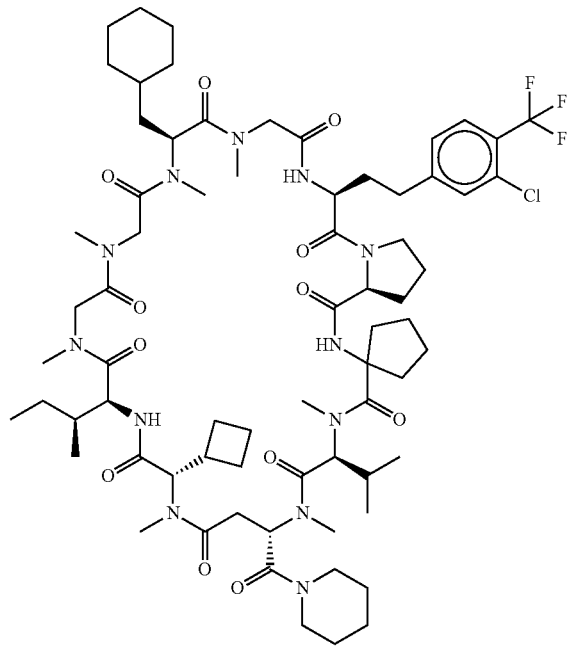 |
| 949 | 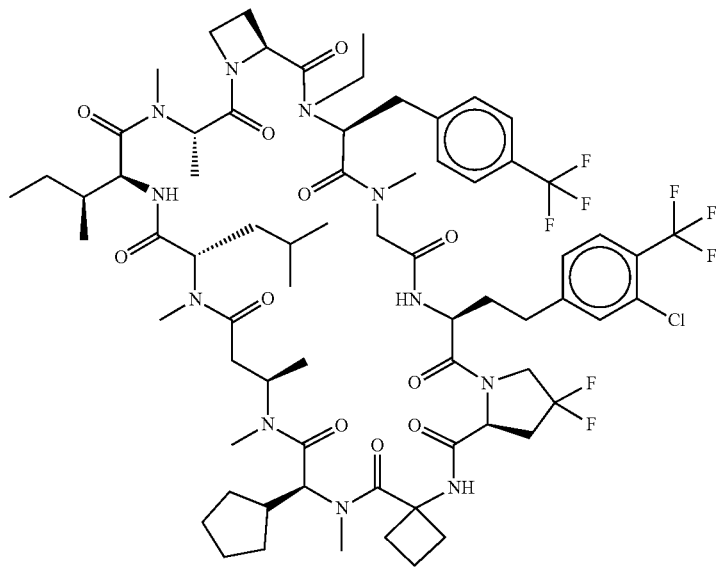 |

TABLE 24-continued
| Compound No. | Structural formula |
|---|---|
| 950 | 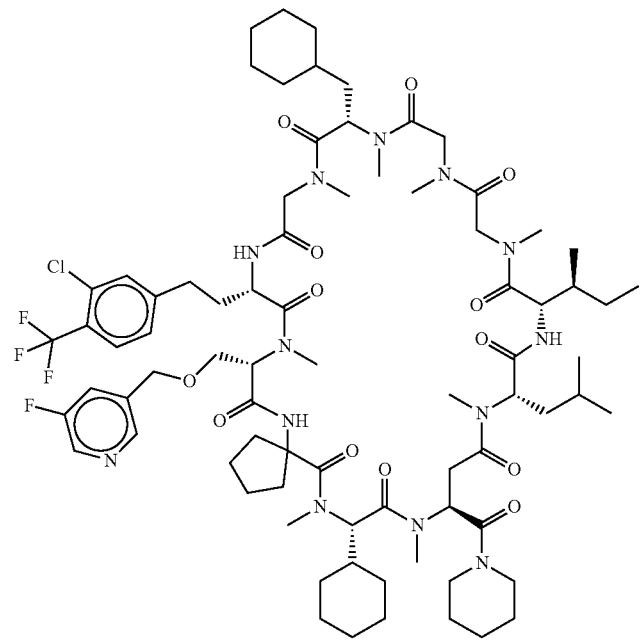 |
| 951 | 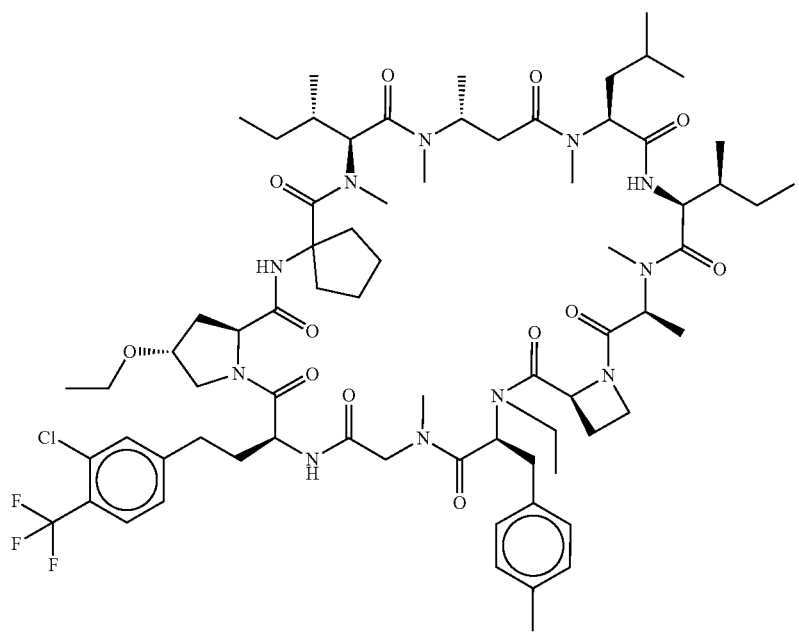 |

TABLE 24-continued
| Compound No. | Structural formula |
|---|---|
| 952 | 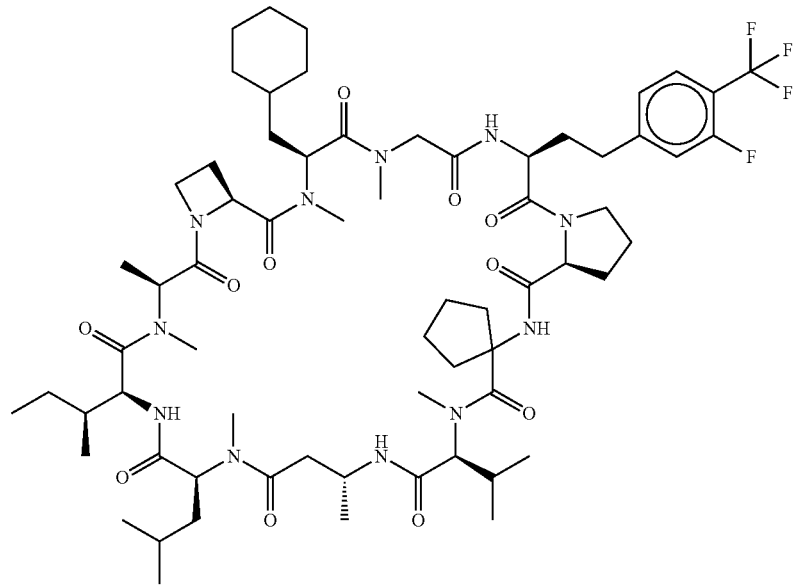 |
| 953 | 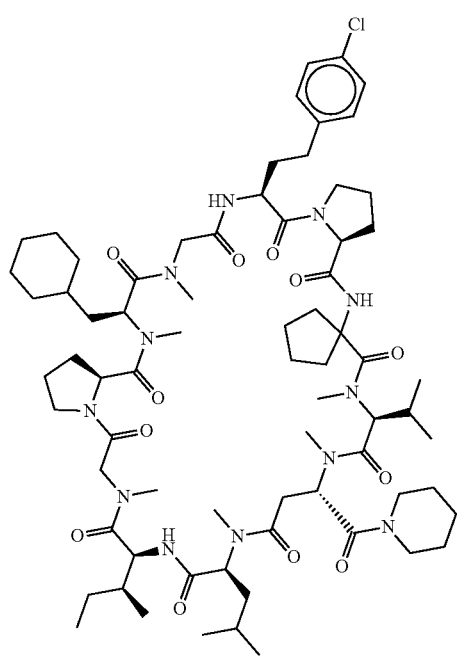 |

TABLE 24-continued
| Compound No. | Structural formula |
|---|---|
| 954 | 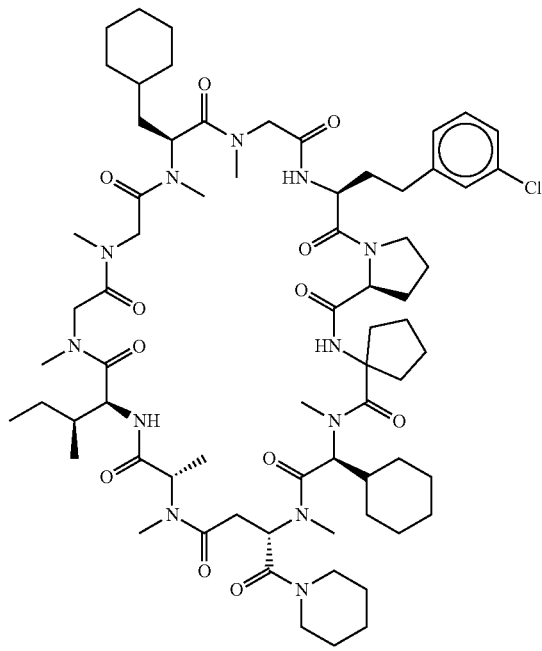 |
| 955 | 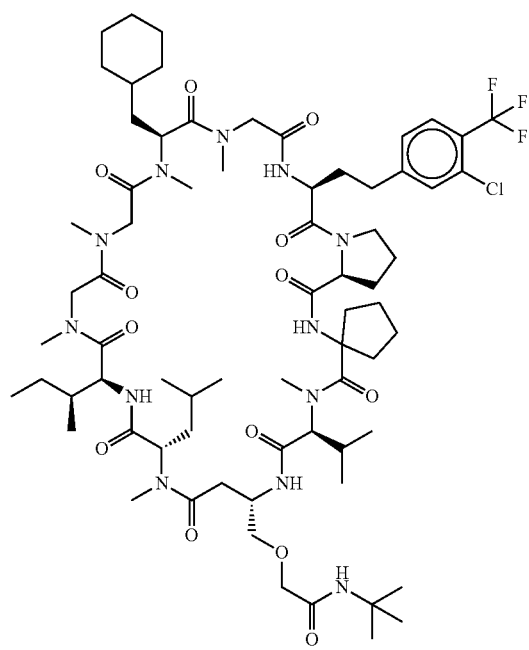 |

TABLE 24-continued
| Compound No. | Structural formula |
|---|---|
| 956 | 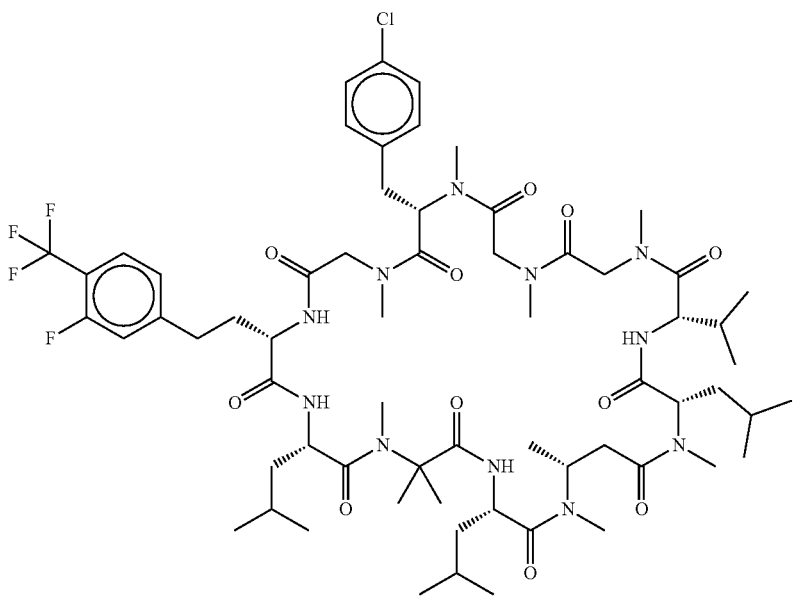 |
| 957 | 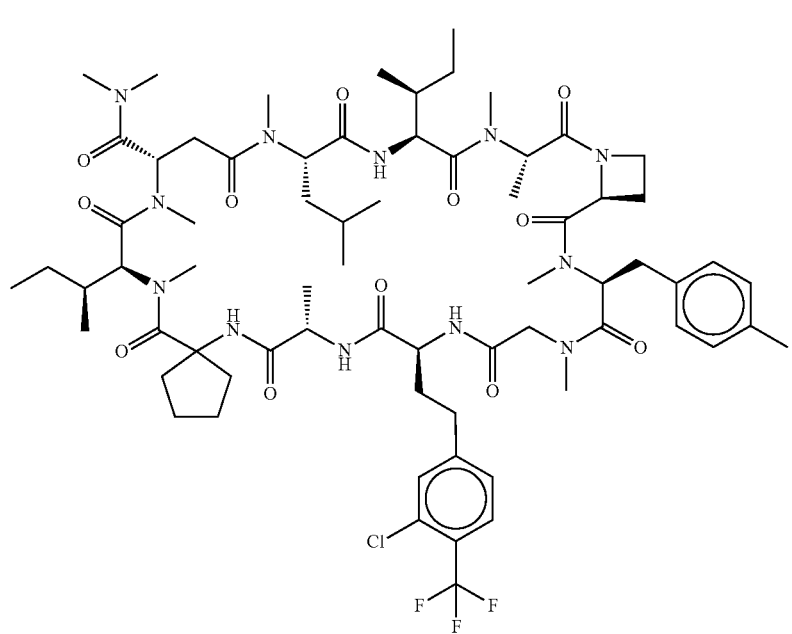 |

TABLE 24-continued
| Compound No. | Structural formula |
|---|---|
| 958 | 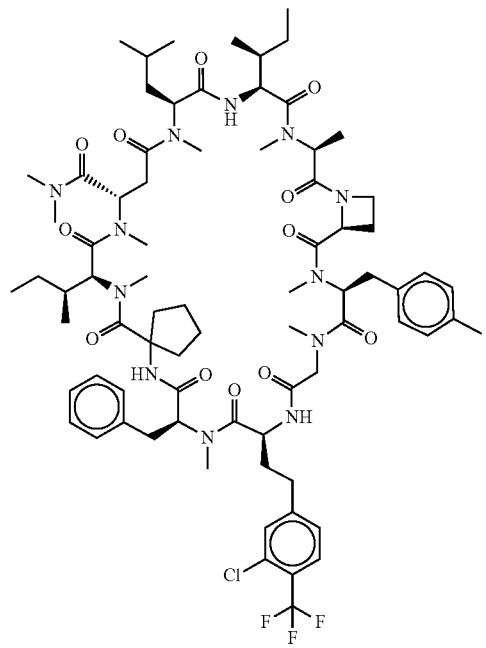 |
| 959 | 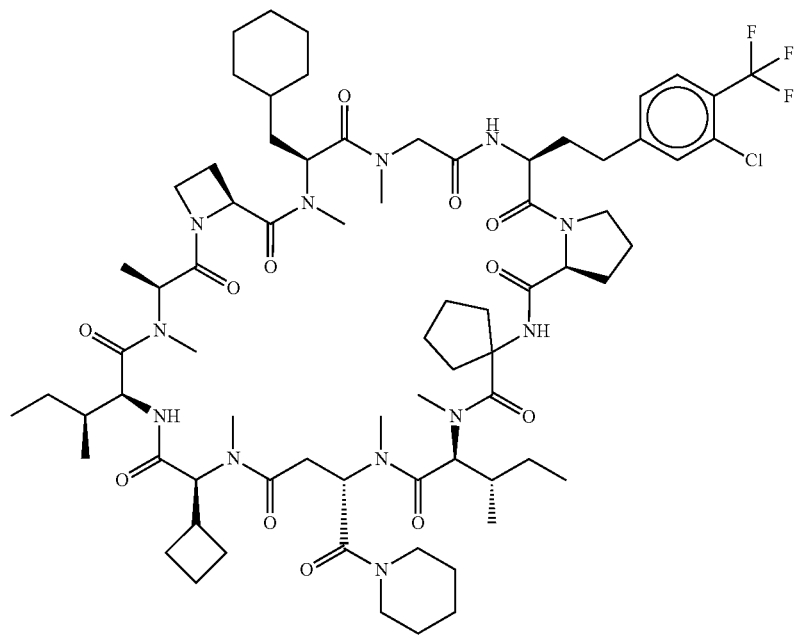 |

TABLE 24-continued
| Compound No. | Structural formula |
|---|---|
| 960 | 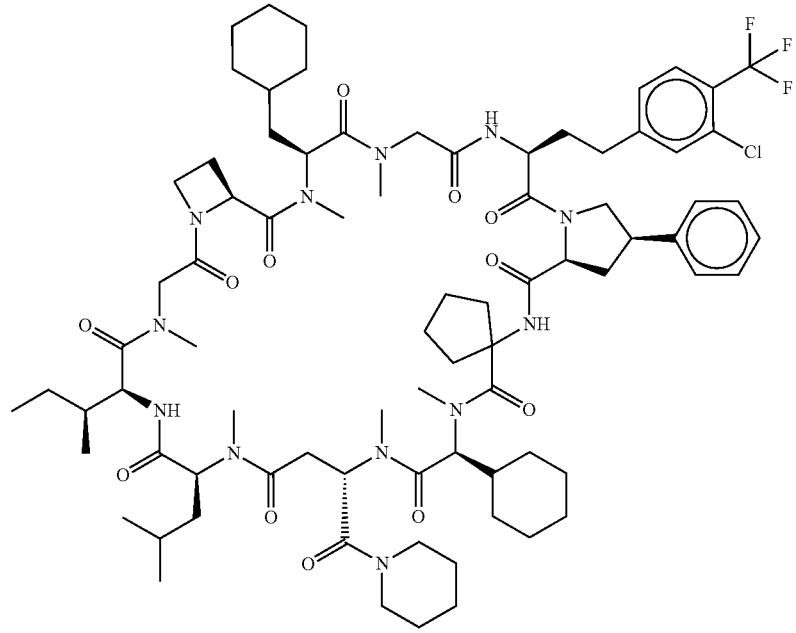 |
| 961 | 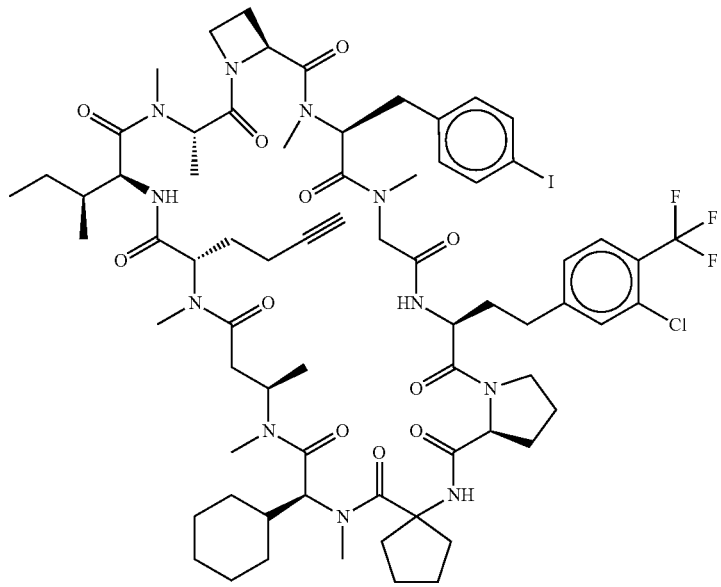 |

TABLE 24-continued
| Compound No. | Structural formula |
|---|---|
| 962 | 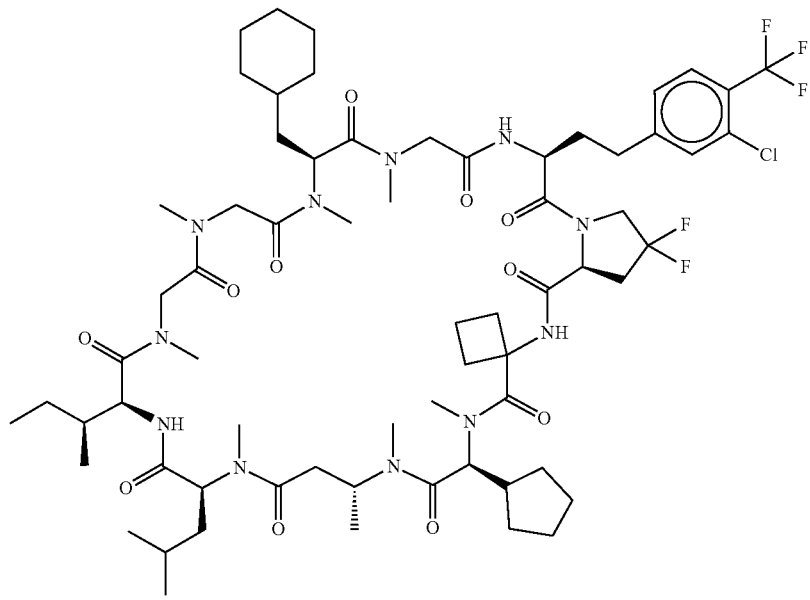 |
| 963 | 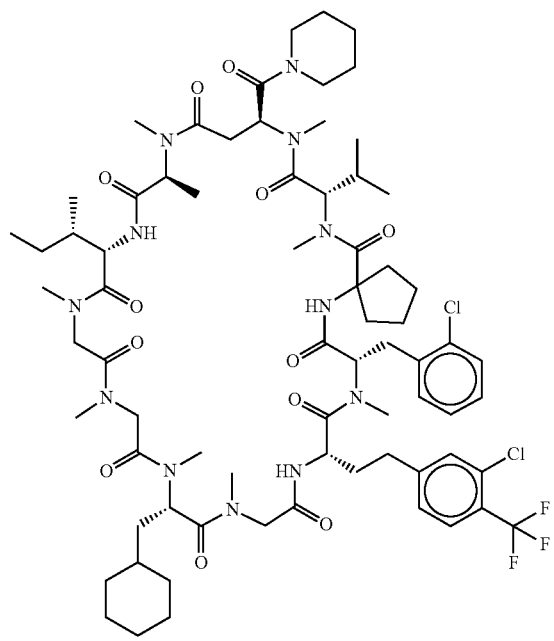 |

TABLE 24-continued
| Compound No. | Structural formula |
|---|---|
| 964 | 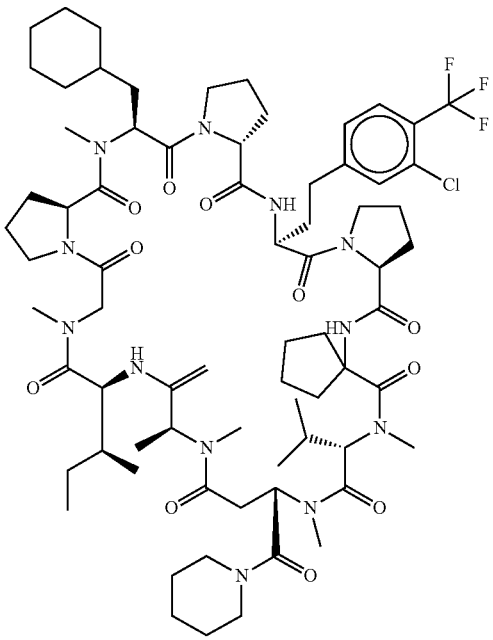 |
| 965 | 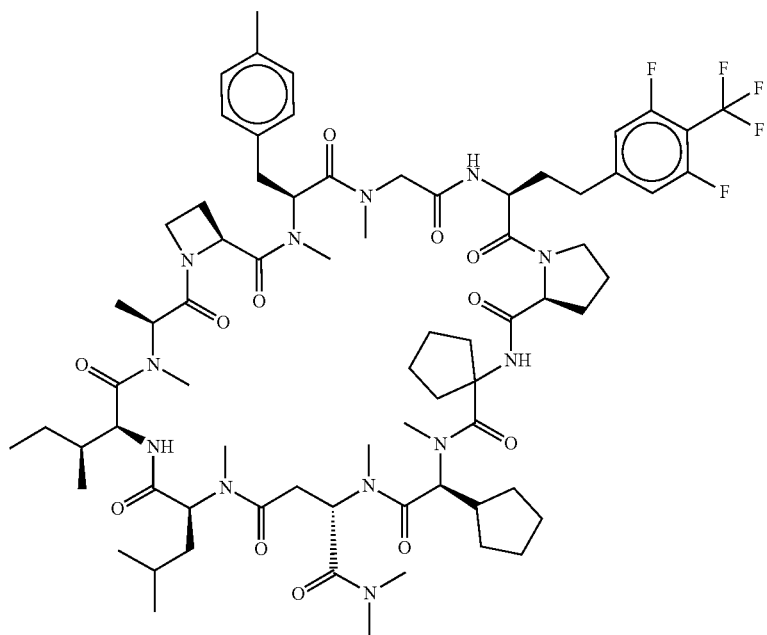 |

TABLE 24-continued
| Compound No. | Structural formula |
|---|---|
| 966 | 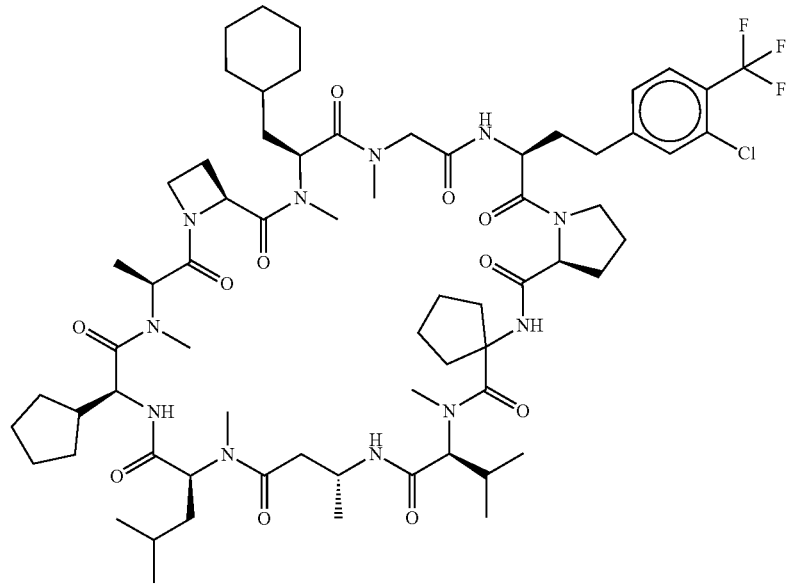 |
| 967 | 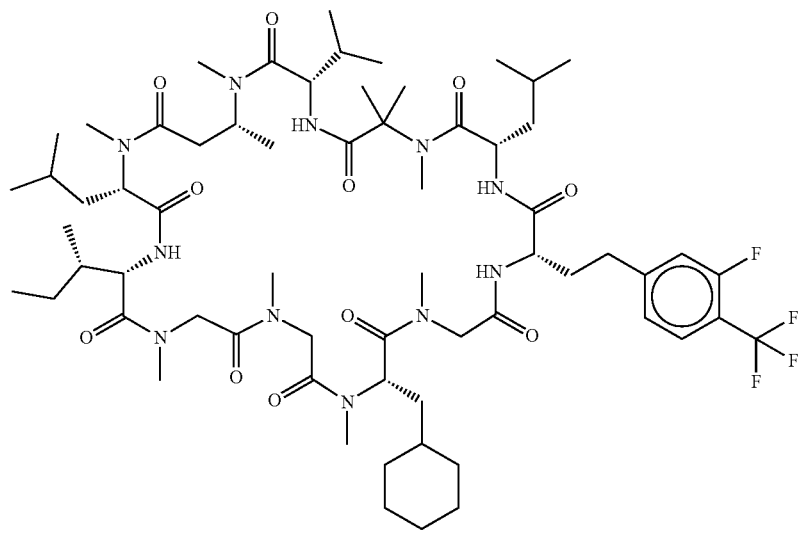 |

TABLE 24-continued
| Compound No. | Structural formula |
|---|---|
| 968 | 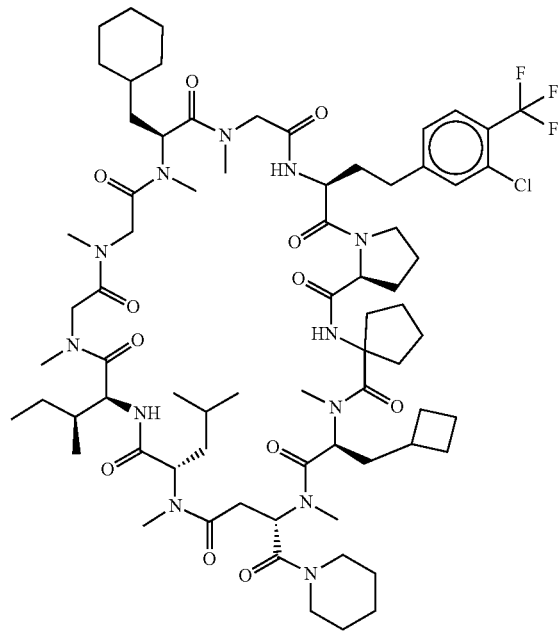 |
| 969 | 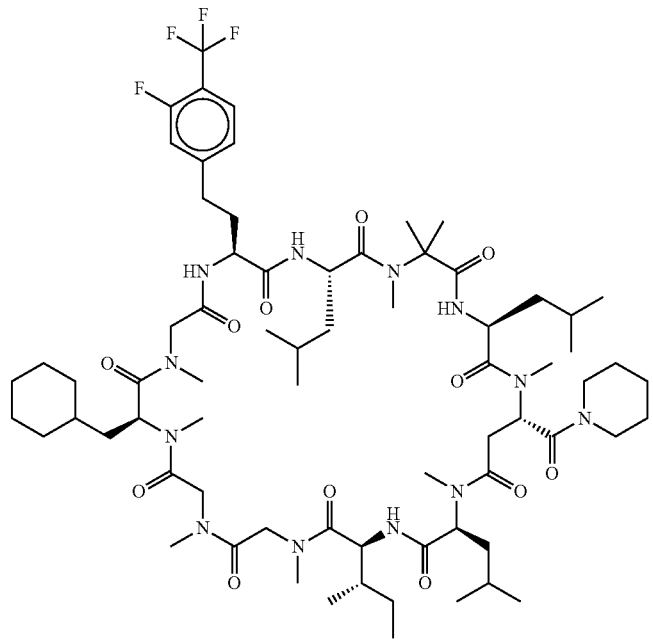 |

TABLE 24-continued
| Compound No. | Structural formula |
|---|---|
| 970 | 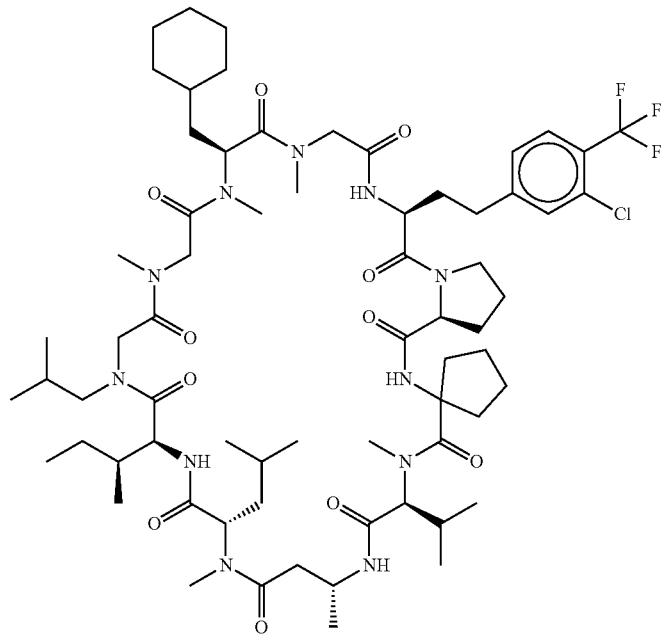 |
| 971 | 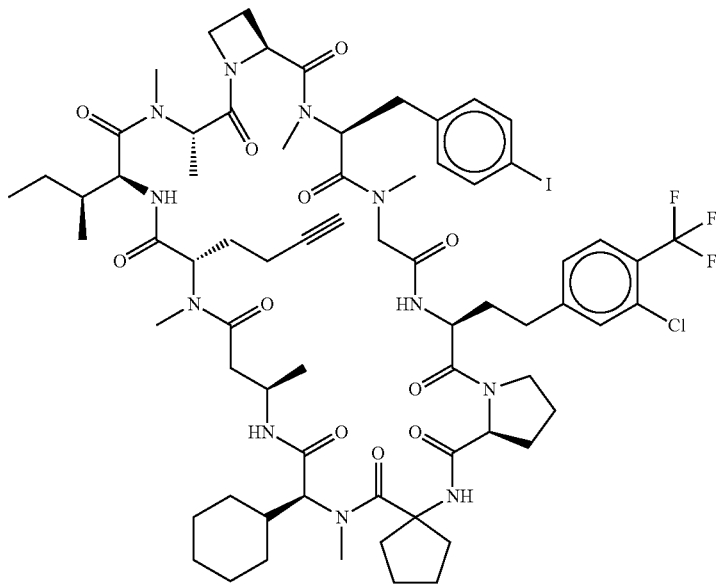 |

TABLE 24-continued
| Compound No. | Structural formula |
|---|---|
| 972 | 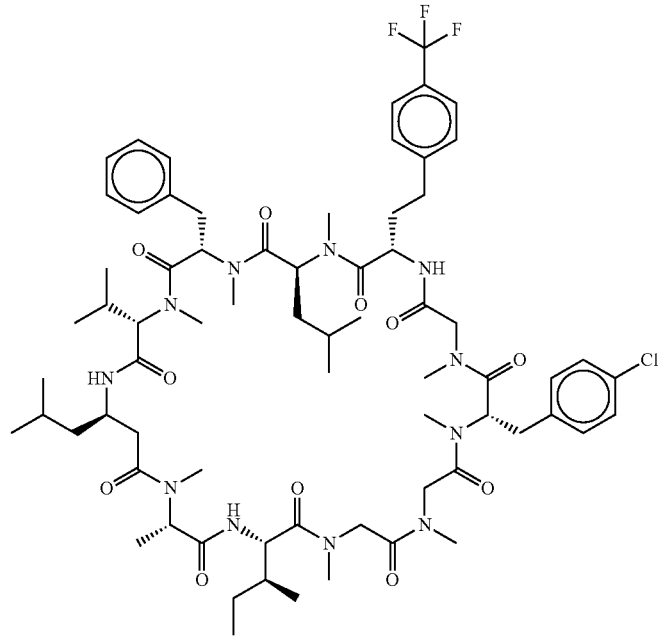 |
| 973 | 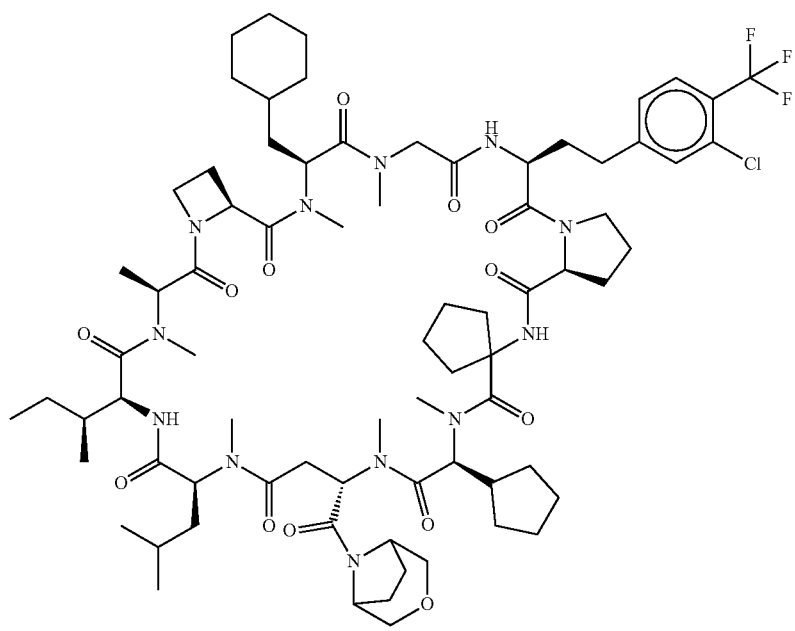 |

TABLE 24-continued
| Compound No. | Structural formula |
|---|---|
| 974 | 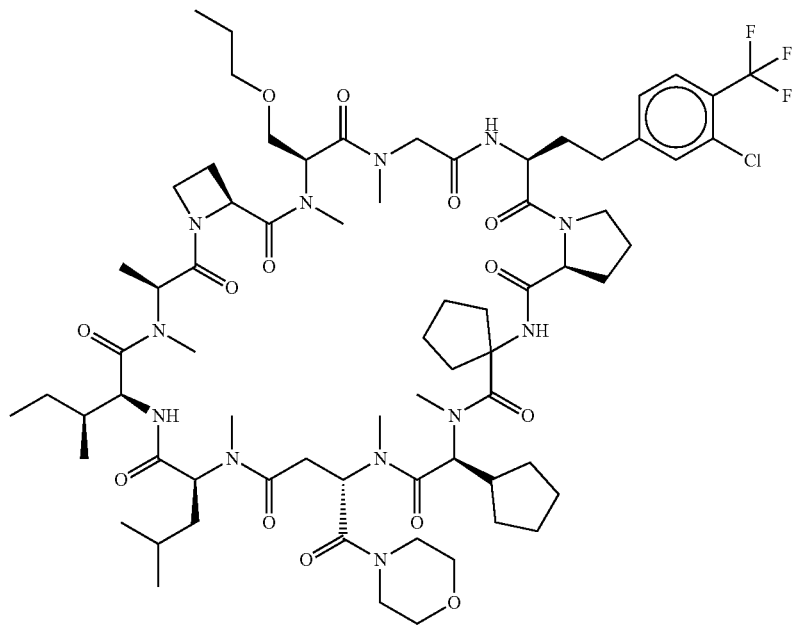 |
| 975 | 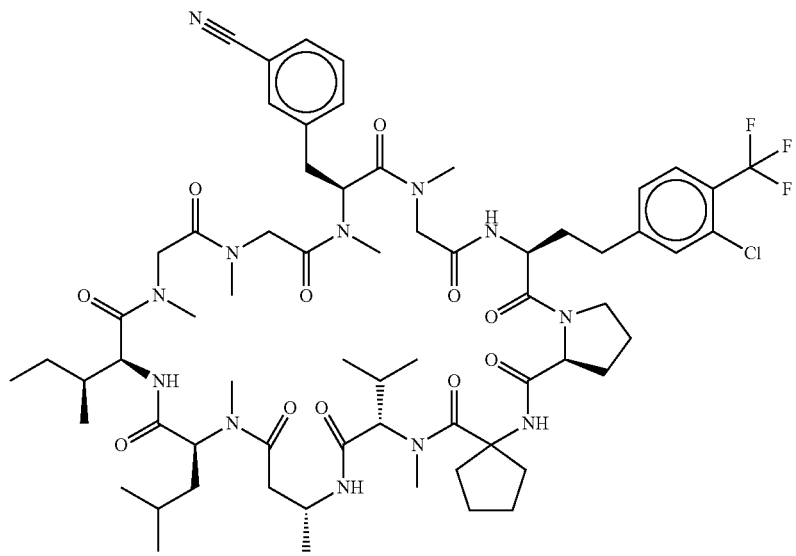 |

TABLE 24-continued
| Compound No. | Structural formula |
|---|---|
| 976 | 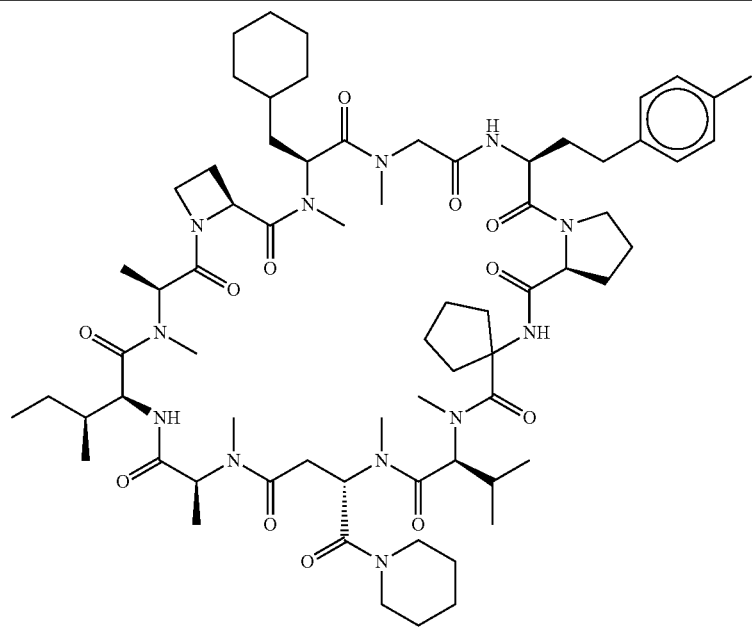 |
| 977 | 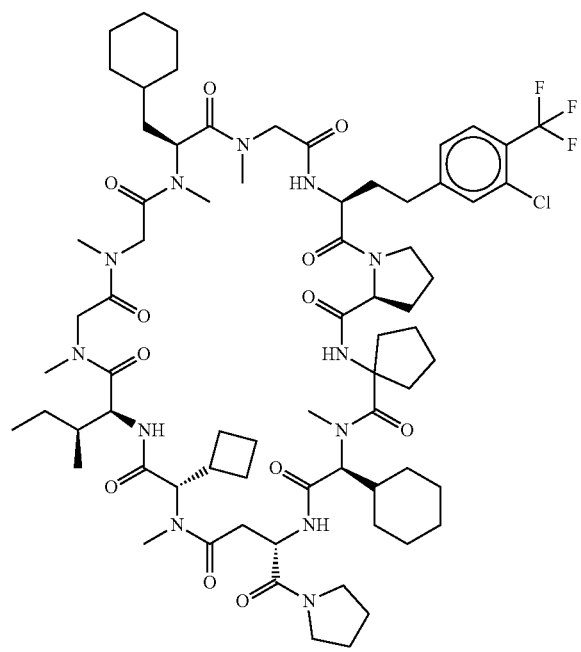 |

TABLE 24-continued
| Compound No. | Structural formula |
|---|---|
| 978 | 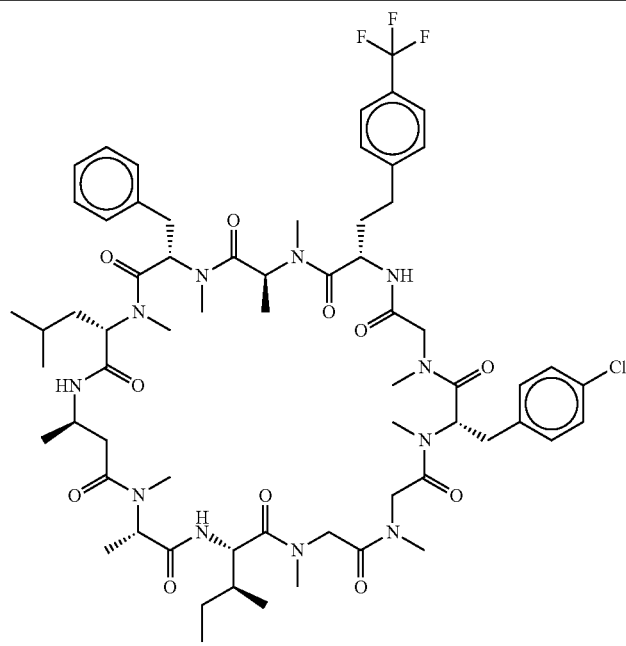 |
| 979 | 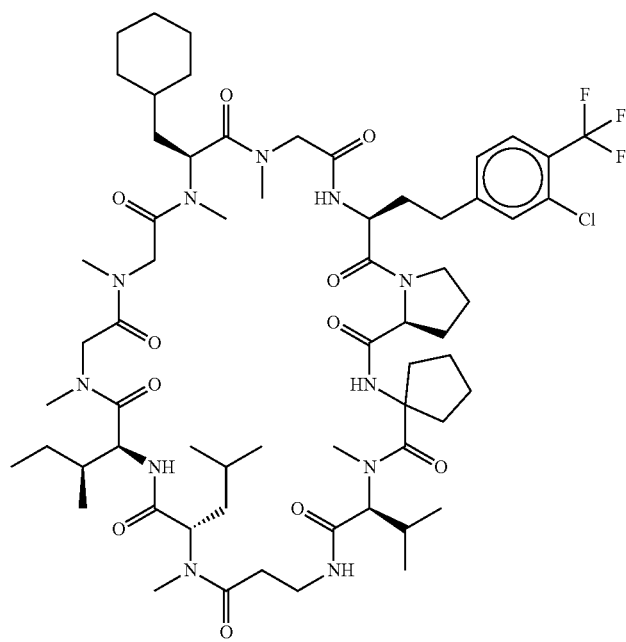 |

TABLE 24-continued
| Compound No. | Structural formula |
|---|---|
| 980 | 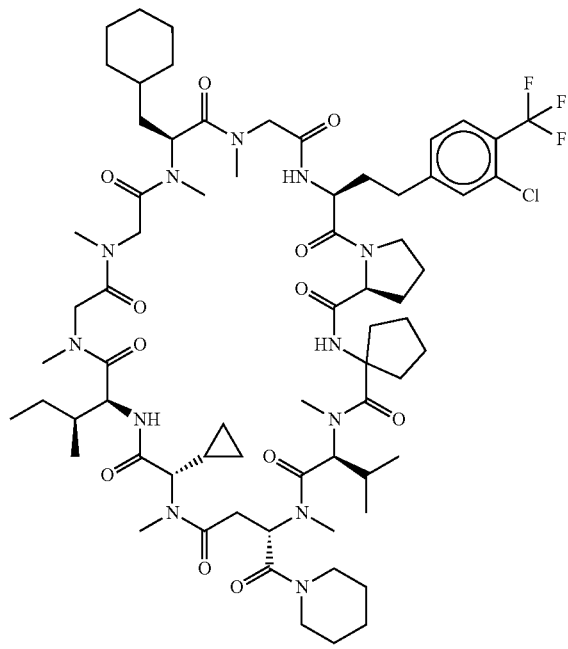 |
| 981 | 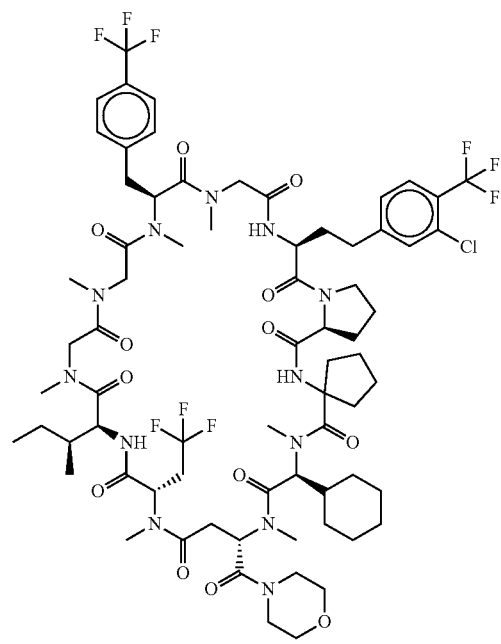 |

TABLE 24-continued
| Compound No. | Structural formula |
|---|---|
| 982 | 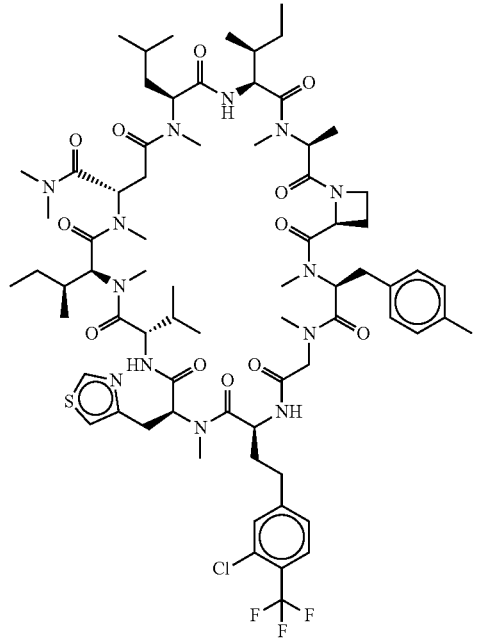 |
| 983 | 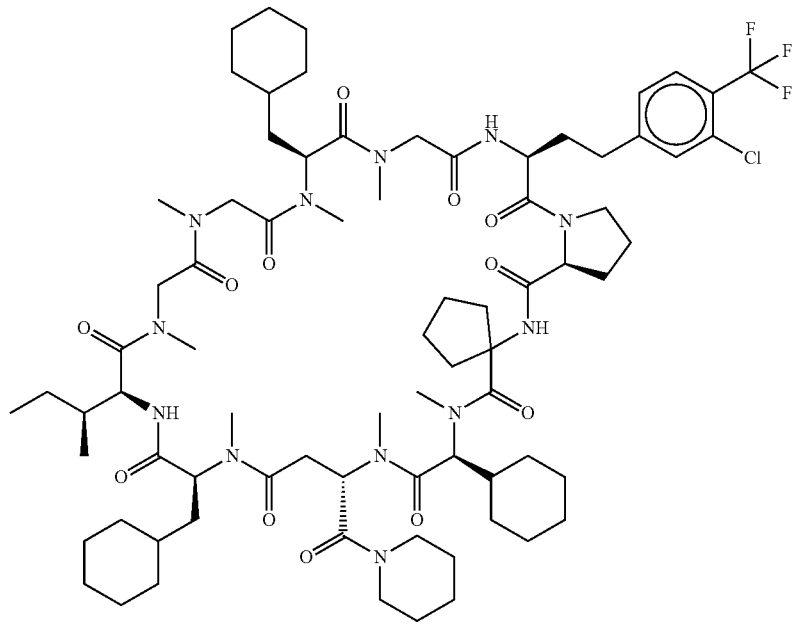 |

TABLE 24-continued
| Compound No. | Structural formula |
|---|---|
| 984 | 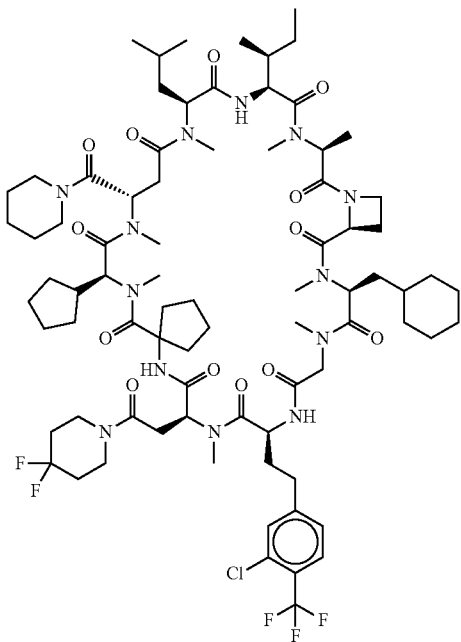 |
| 985 | 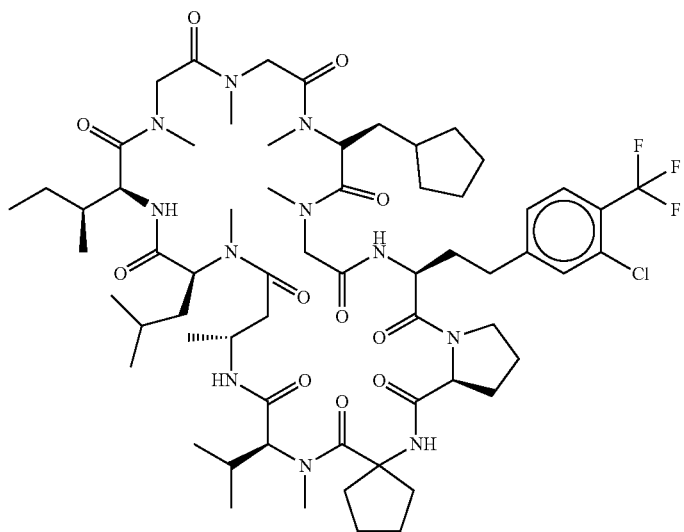 |

TABLE 24-continued
| Compound No. | Structural formula |
|---|---|
| 986 | 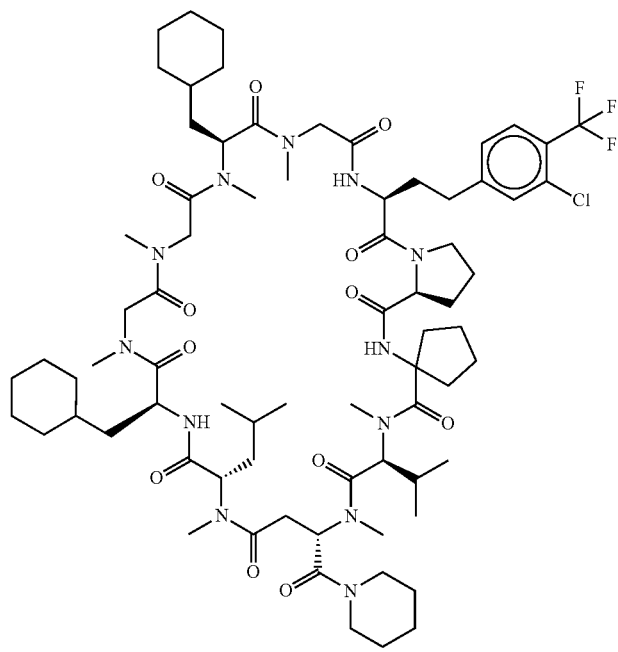 |
| 987 | 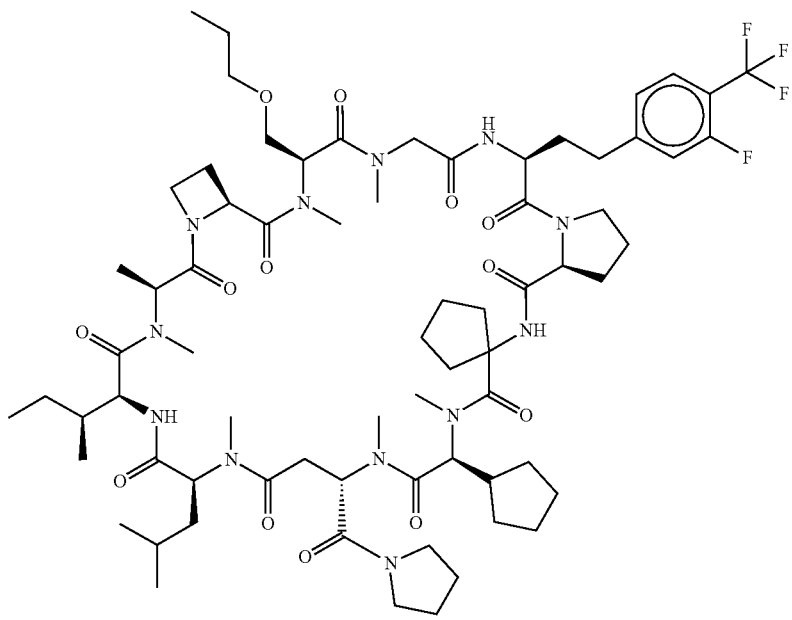 |

TABLE 24-continued
| Compound No. | Structural formula |
|---|---|
| 988 | 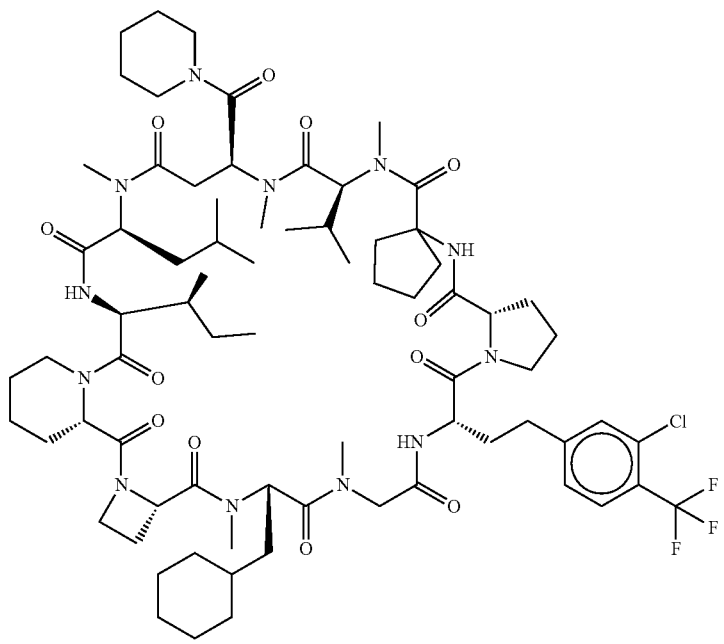 |
| 989 | 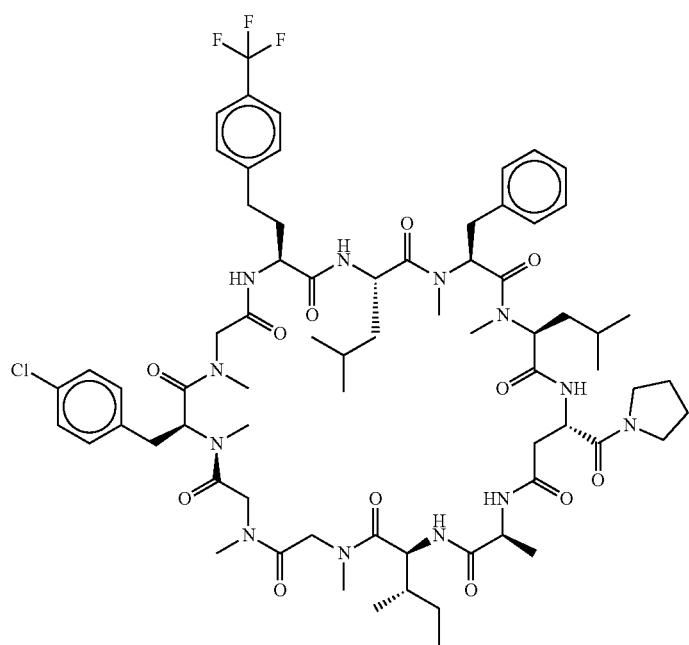 |

TABLE 24-continued
| Compound No. | Structural formula |
|---|---|
| 990 | 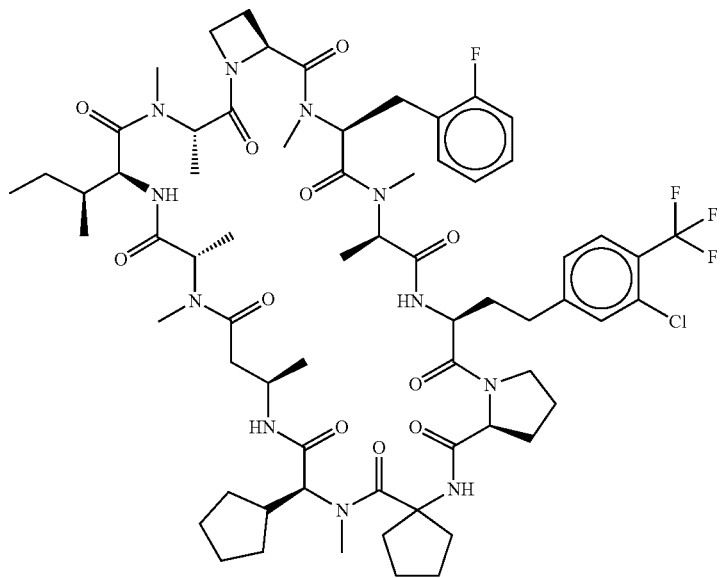 |
| 991 | 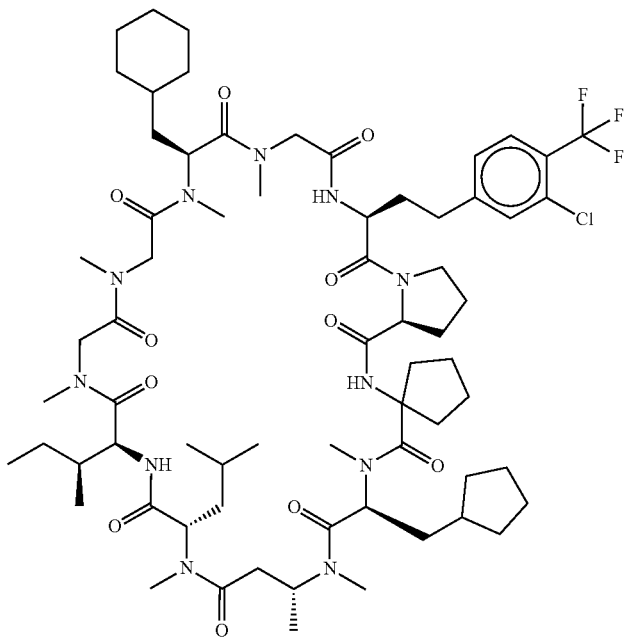 |

TABLE 24-continued
| Compound No. | Structural formula |
|---|---|
| 992 | 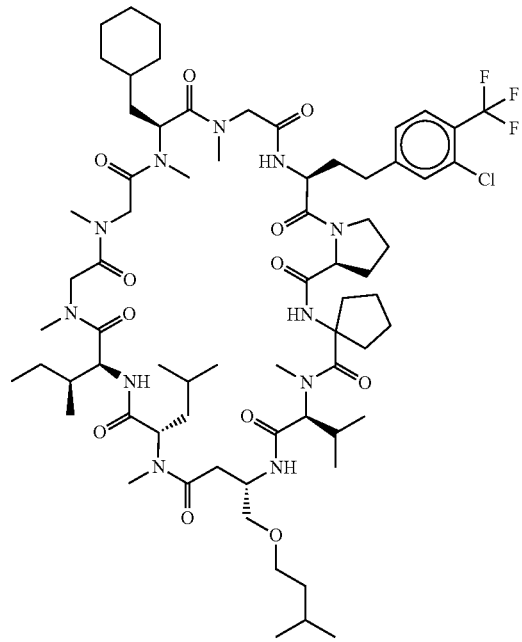 |
| 993 | 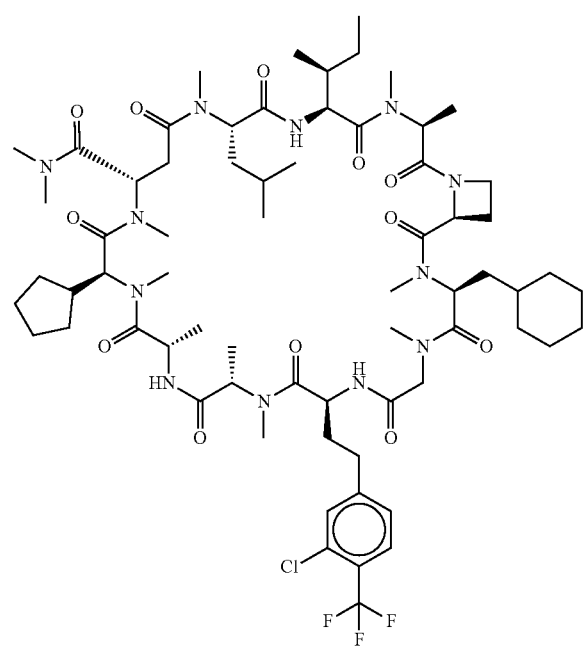 |

TABLE 24-continued
| Compound No. | Structural formula |
|---|---|
| 994 | 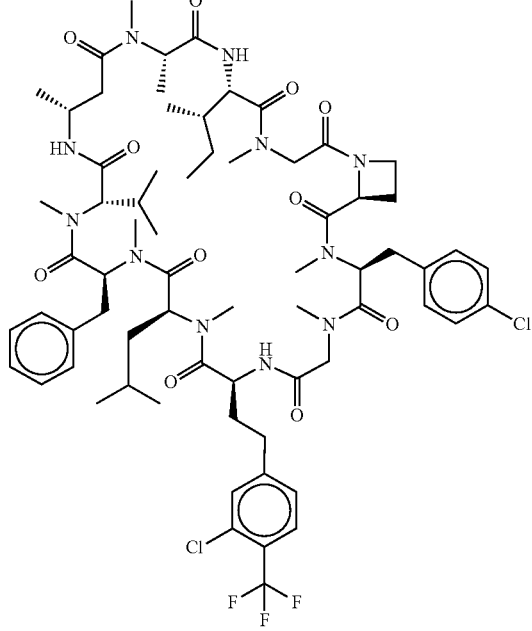 |
| 995 | 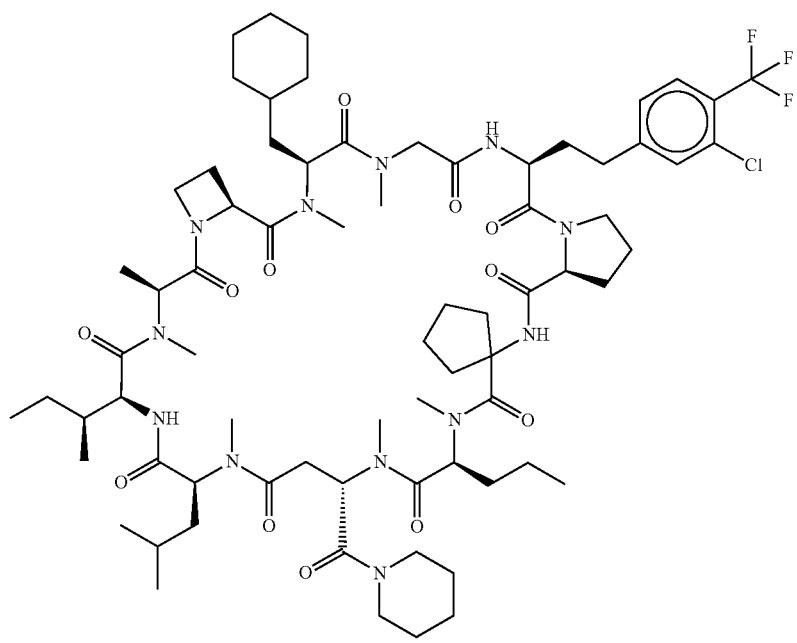 |

TABLE 24-continued
| Compound No. | Structural formula |
|---|---|
| 996 | 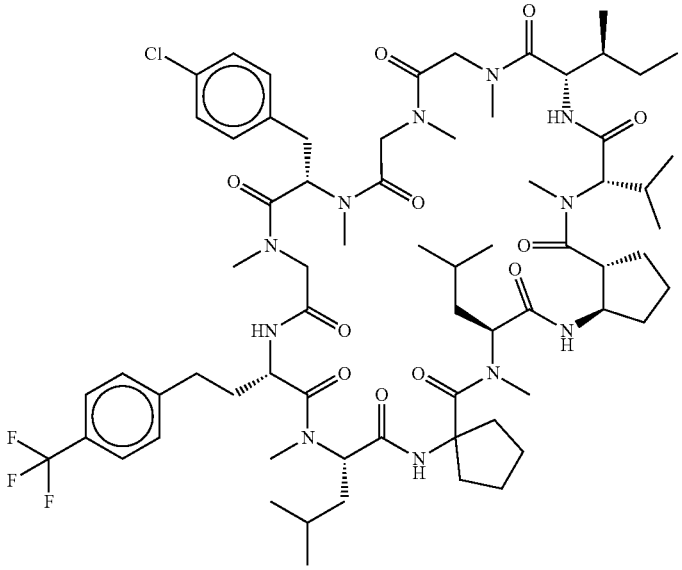 |
| 997 | 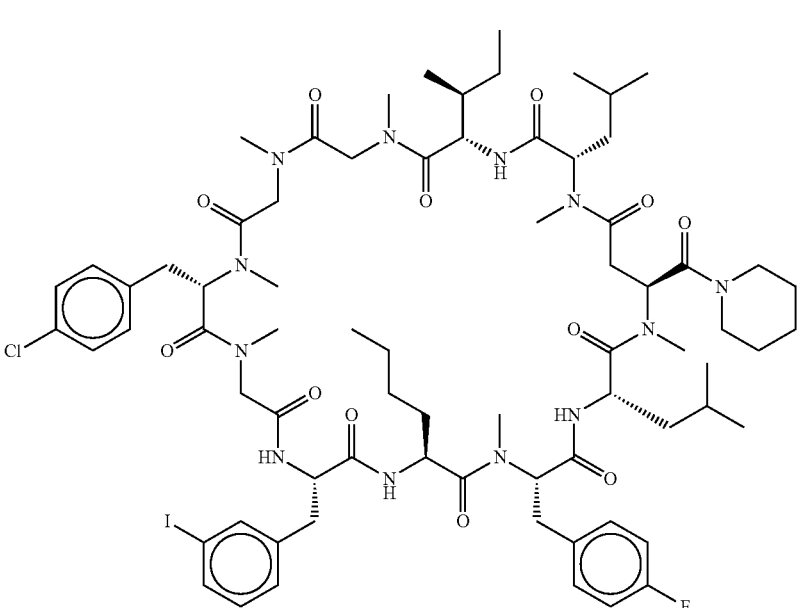 |

TABLE 24-continued
| Compound No. | Structural formula |
|---|---|
| 998 | 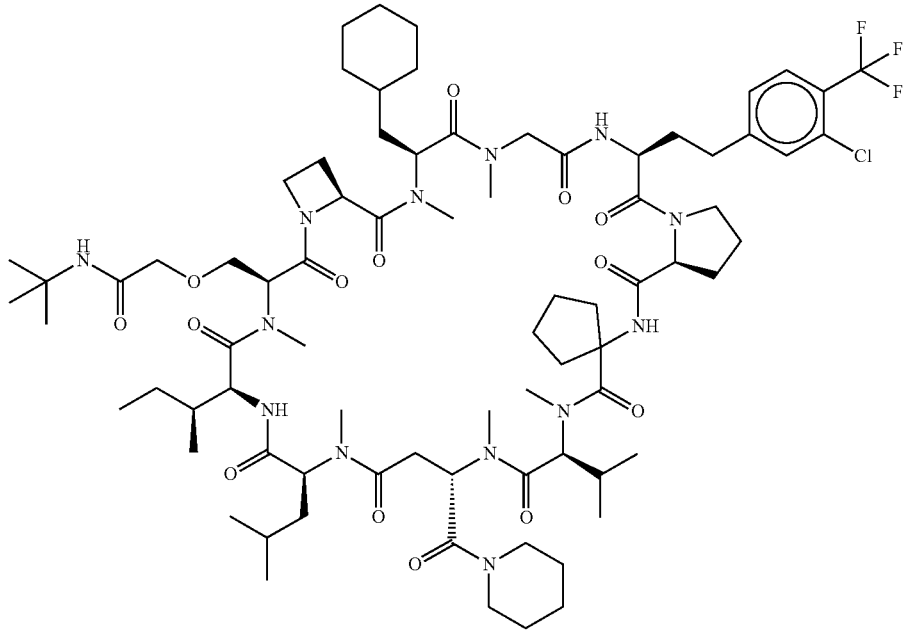 |
| 999 | 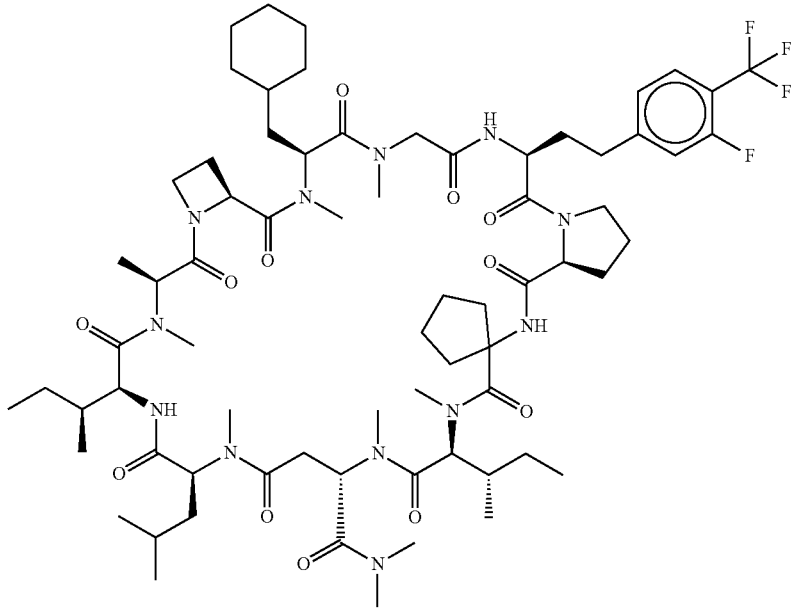 |

TABLE 24-continued
| Compound No. | Structural formula |
|---|---|
| 1000 | 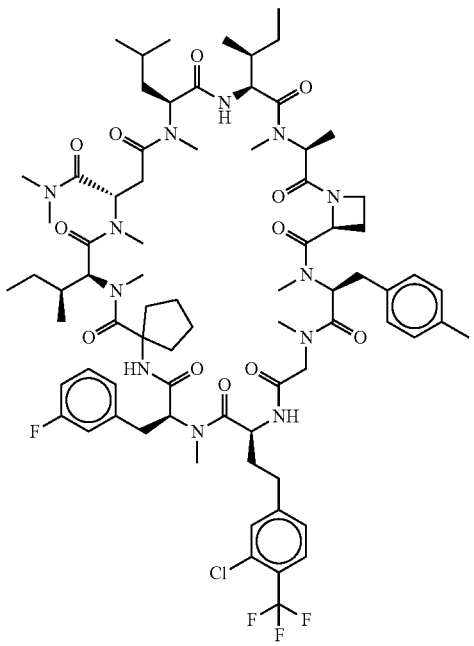 |
| 1001 | 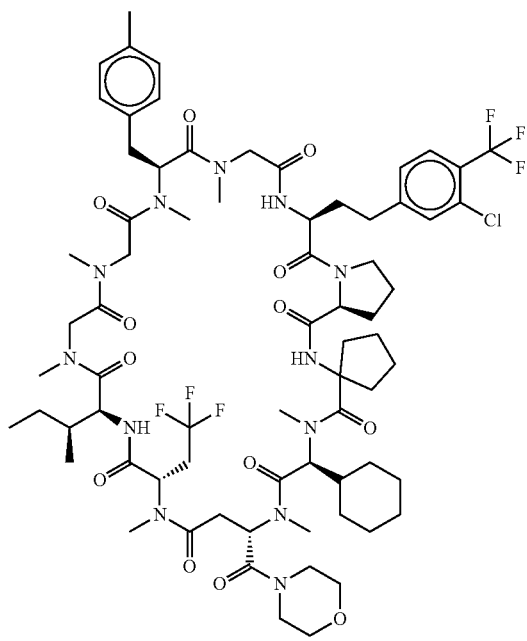 |

TABLE 24-continued
| Compound No. | Structural formula |
|---|---|
| 1002 | 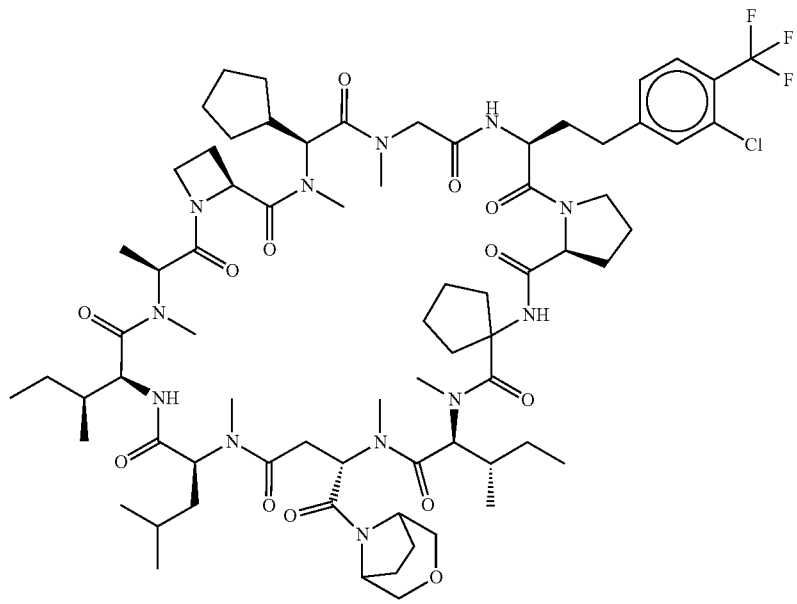 |
| 1003 | 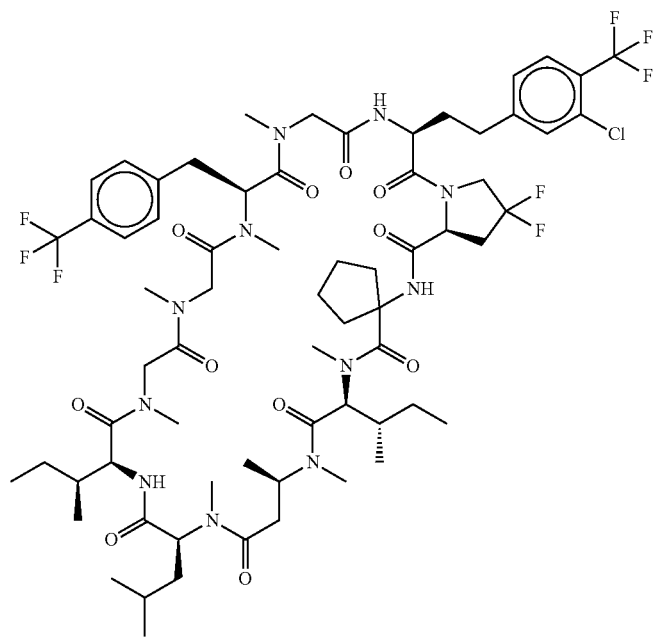 |

TABLE 24-continued
| Compound No. | Structural formula |
|---|---|
| 1004 | 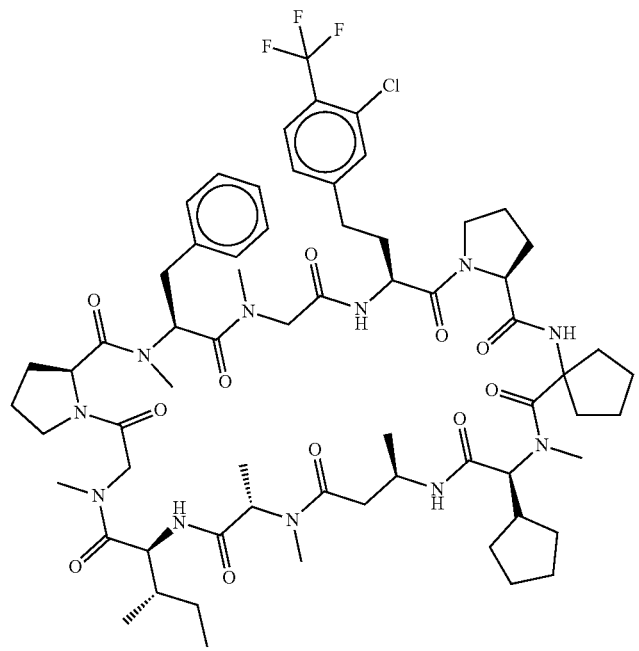 |
| 1005 | 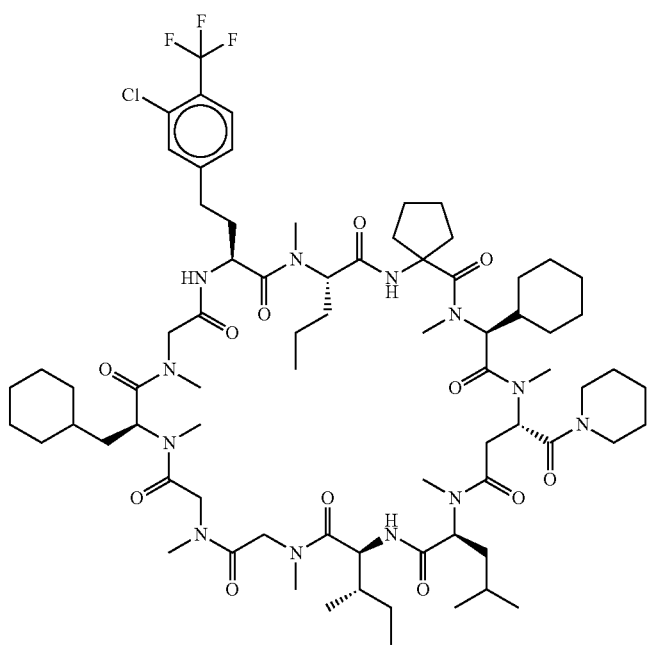 |

TABLE 24-continued
| Compound No. | Structural formula |
|---|---|
| 1006 | 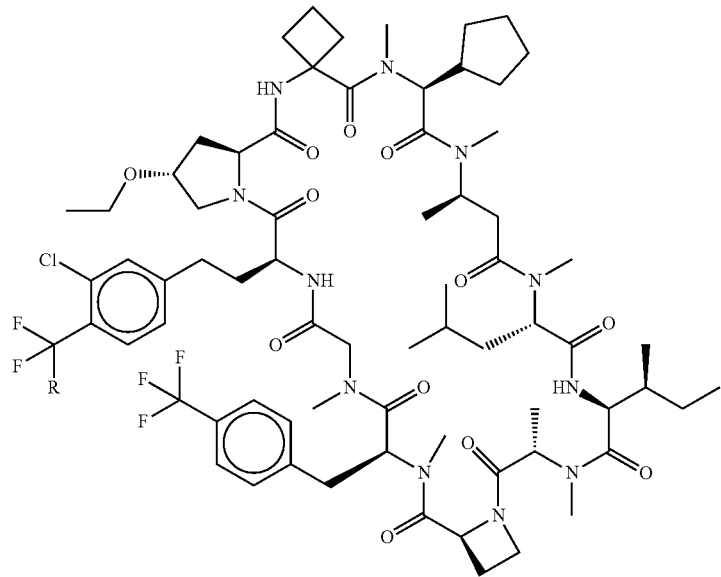 |
| 1007 | 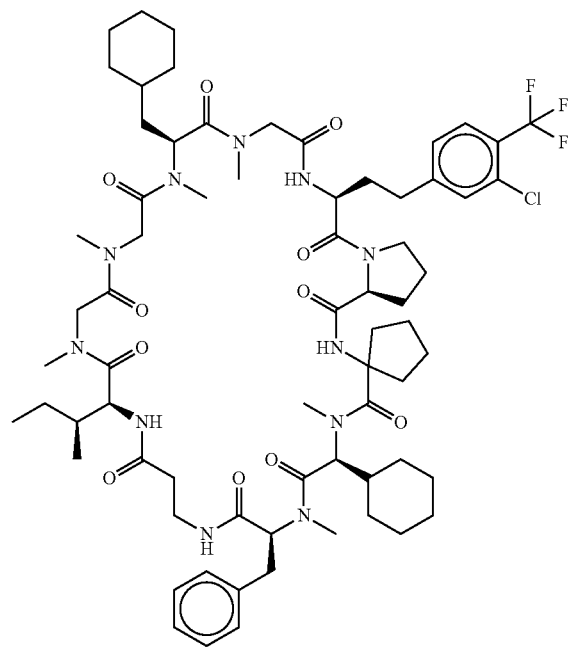 |

TABLE 24-continued
| Compound No. | Structural formula |
| --- | --- |
| 1008 | 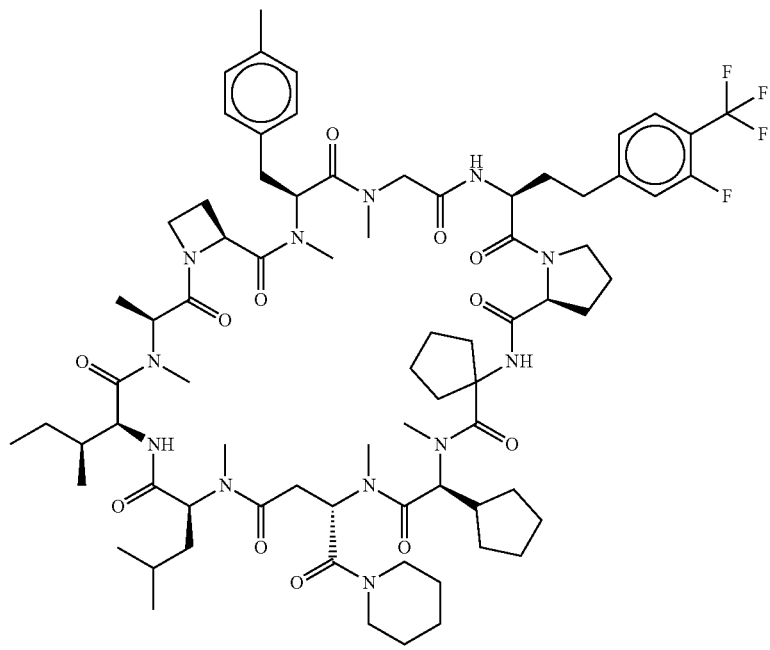 |
| 1009 | 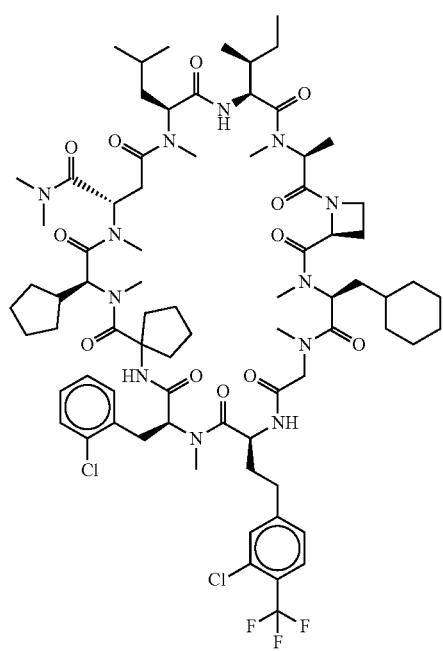 |

TABLE 24-continued
| Compound No. | Structural formula |
|---|---|
| 1010 | 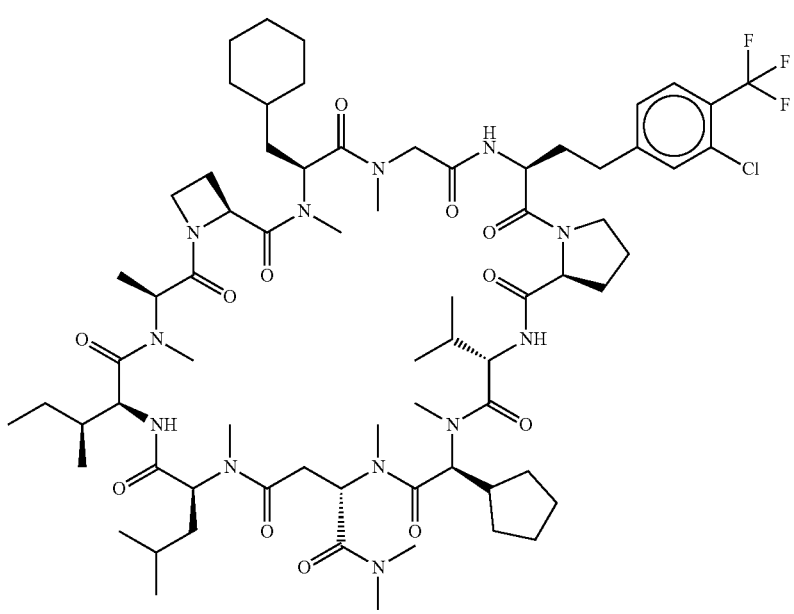 |
| 1011 | 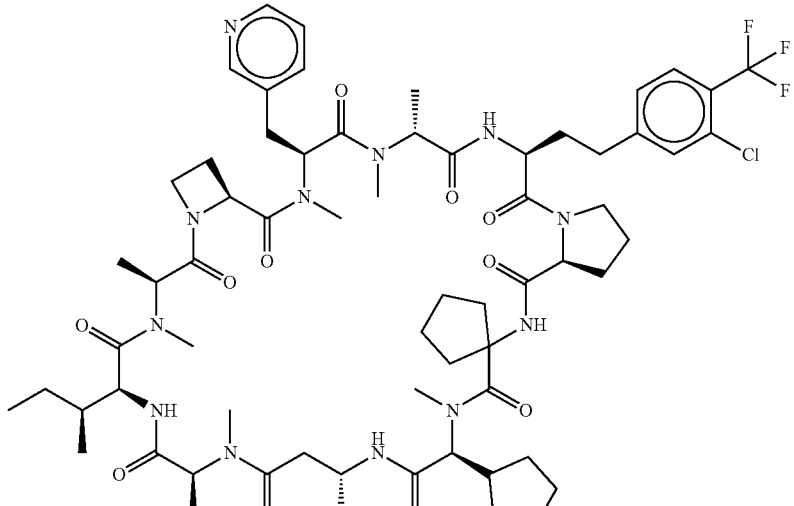 |

TABLE 24-continued
| Compound No. | Structural formula |
|---|---|
| 1012 | 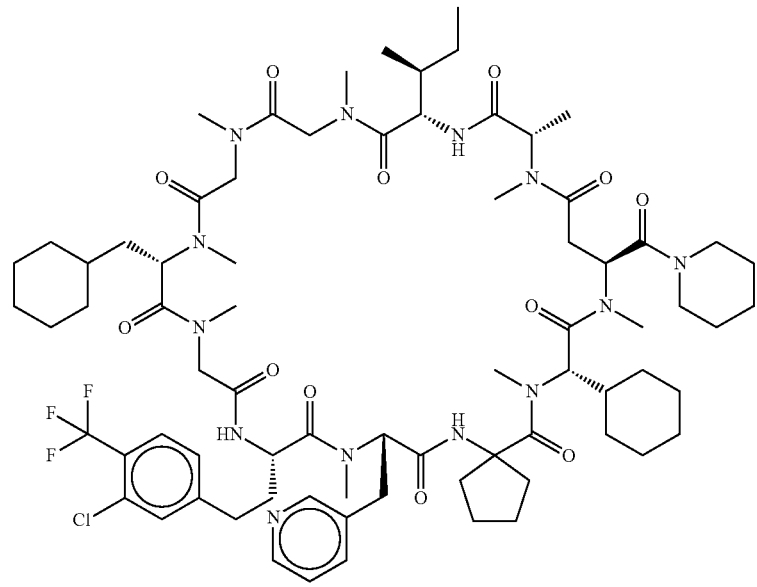 |
| 1013 | 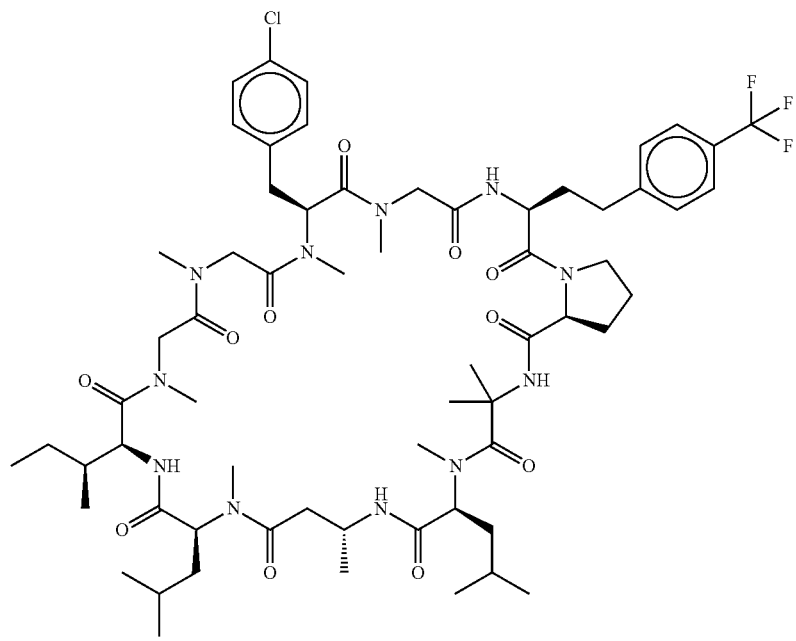 |

TABLE 24-continued

| Compound No. | Structural formula |
|---|---|
| 1014 | |
| 1015 | |

TABLE 24-continued
| Compound No. | Structural formula |
|---|---|
| 1016 | 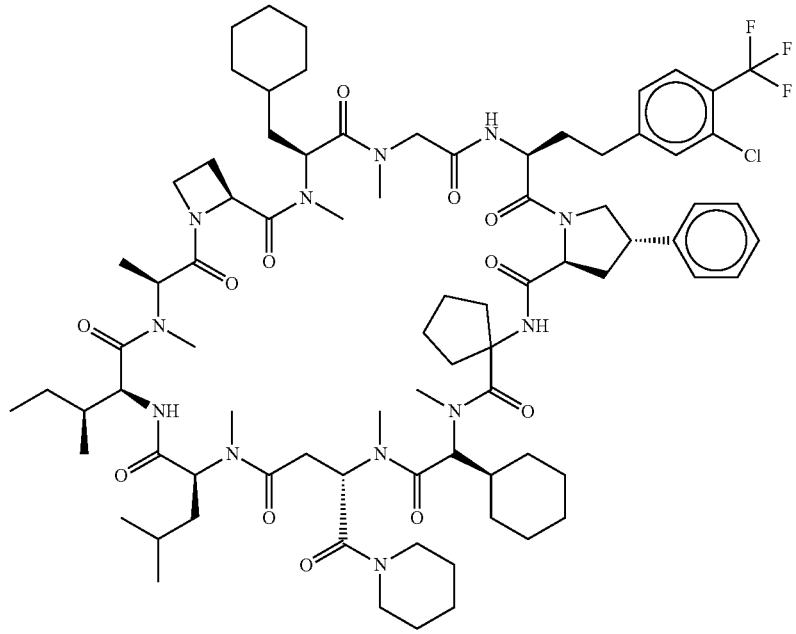 |
| 1017 | 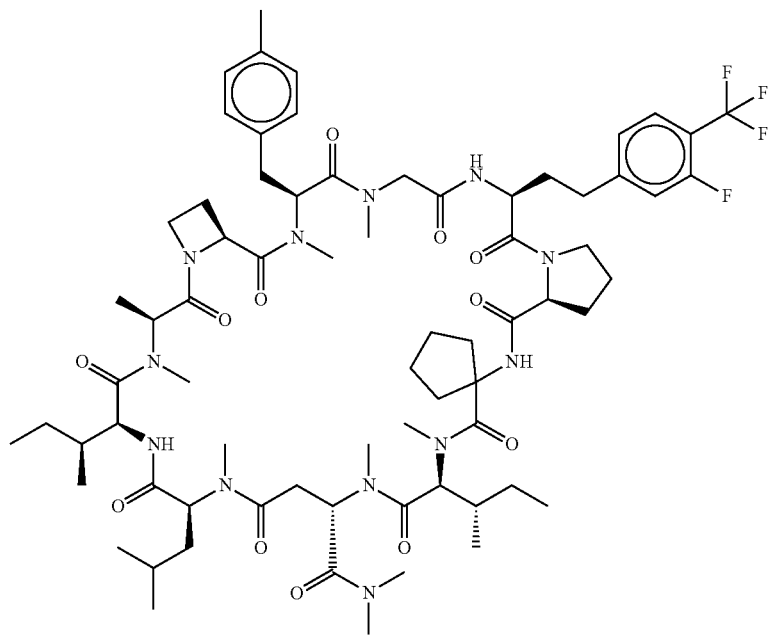 |

TABLE 24-continued
| Compound No. | Structural formula |
|---|---|
| 1018 | 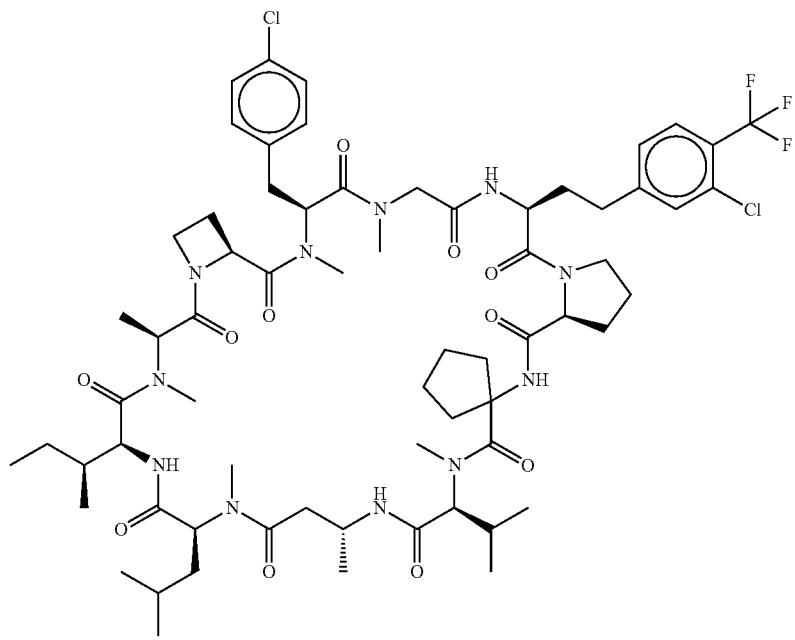 |
| 1019 | 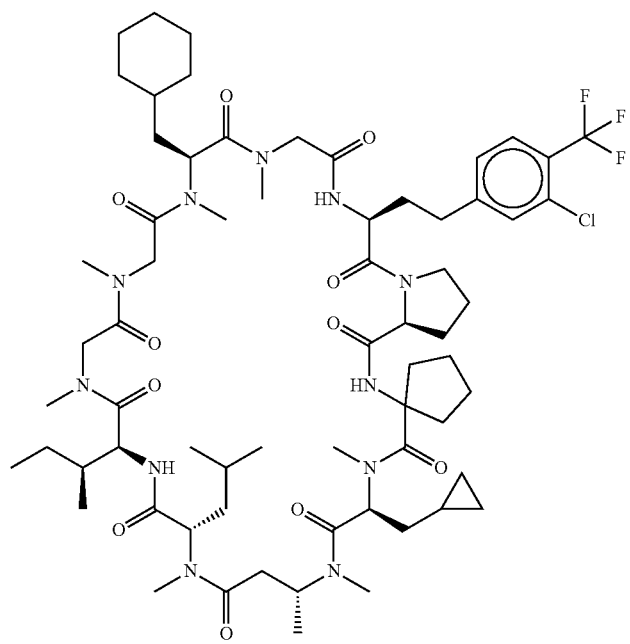 |

TABLE 24-continued
| Compound No. | Structural formula |
|---|---|
| 1020 | 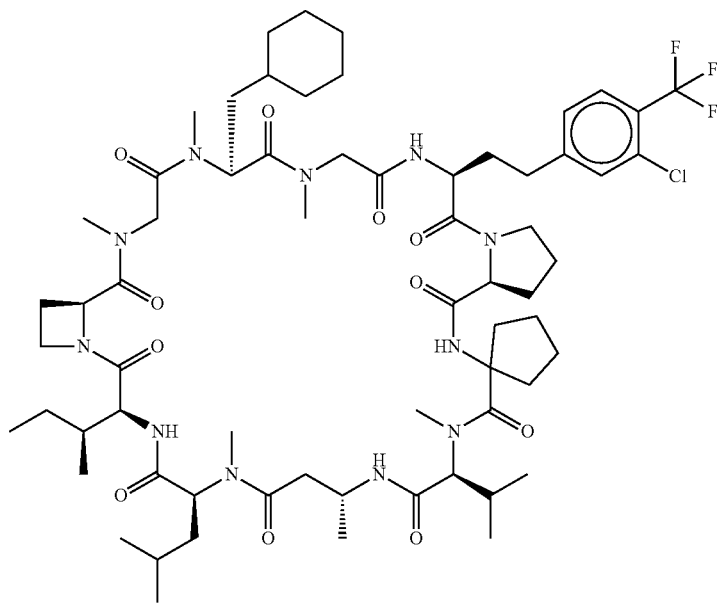 |
| 1021 | 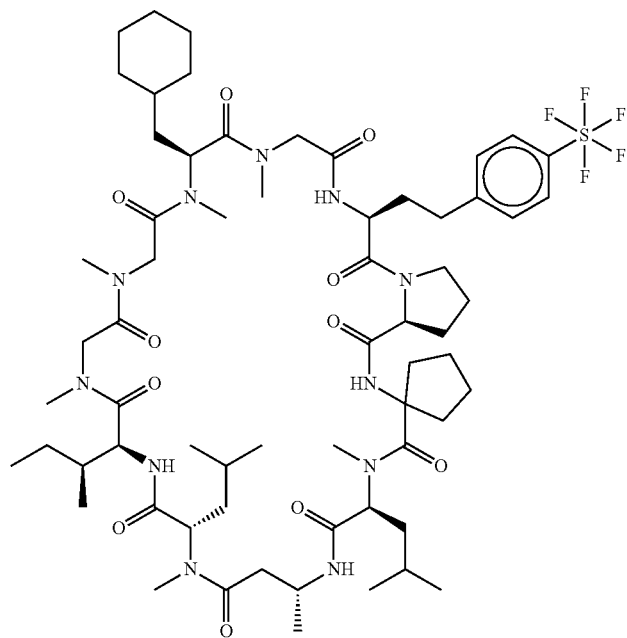 |

TABLE 24-continued
| Compound No. | Structural formula |
|---|---|
| 1022 | 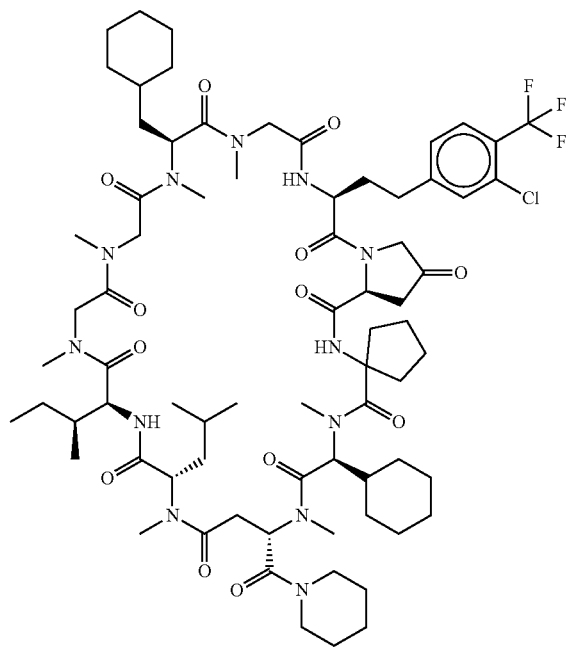 |
| 1023 | 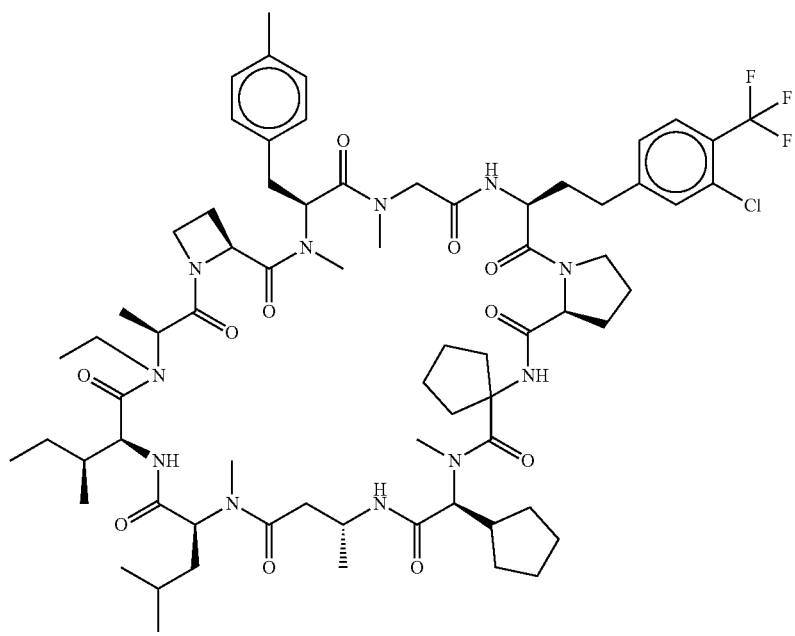 |

TABLE 24-continued
| Compound No. | Structural formula |
|---|---|
| 1024 | 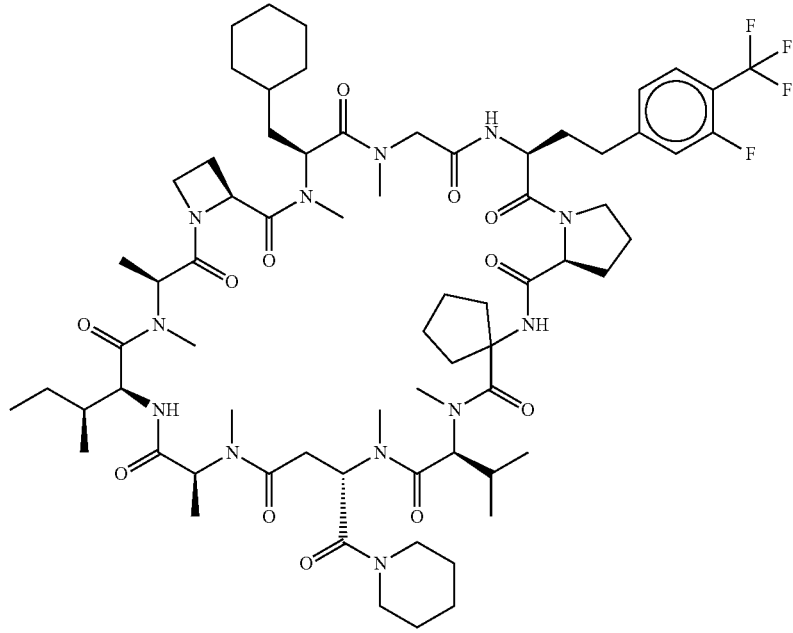 |
| 1025 | 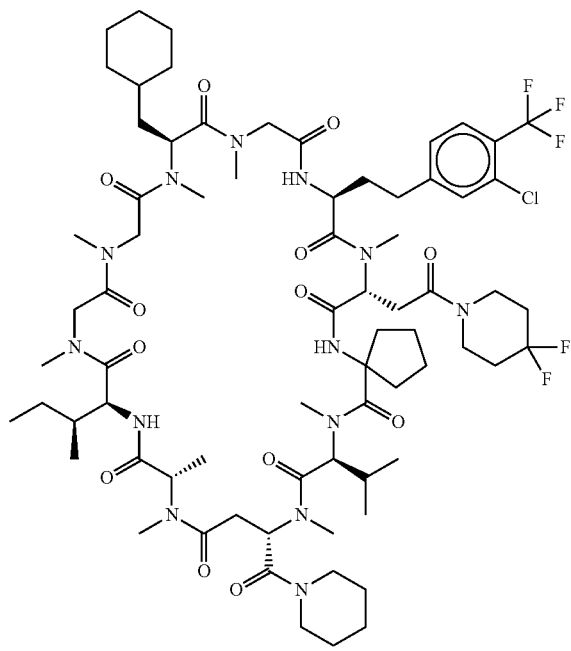 |

TABLE 24-continued
| Compound No. | Structural formula |
|---|---|
| 1026 | 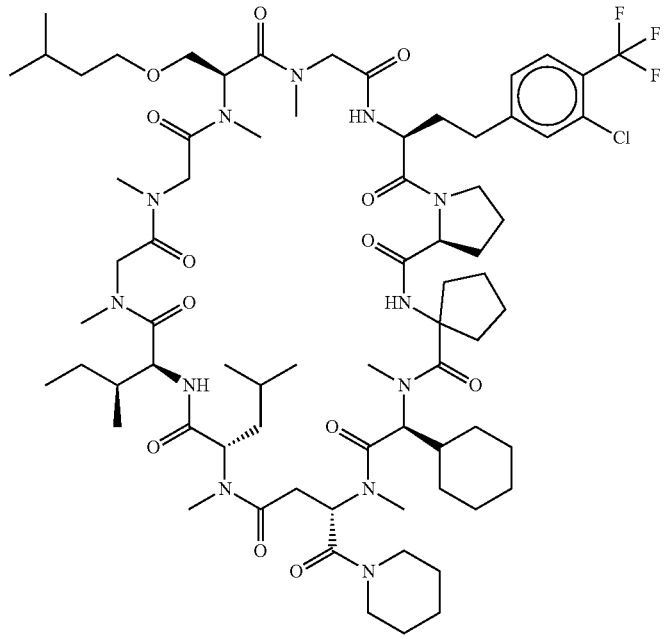 |
| 1027 | 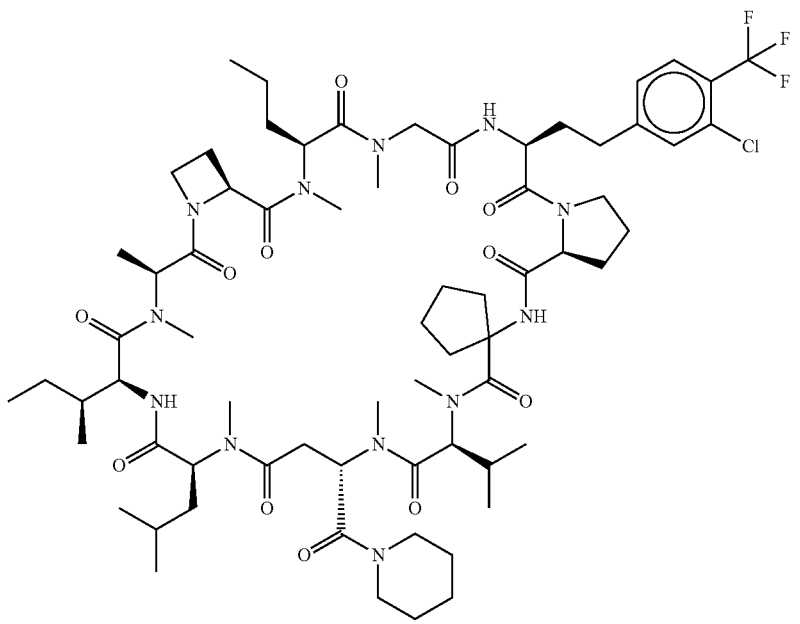 |

TABLE 24-continued
| Compound No. | Structural formula |
|---|---|
| 1029 | 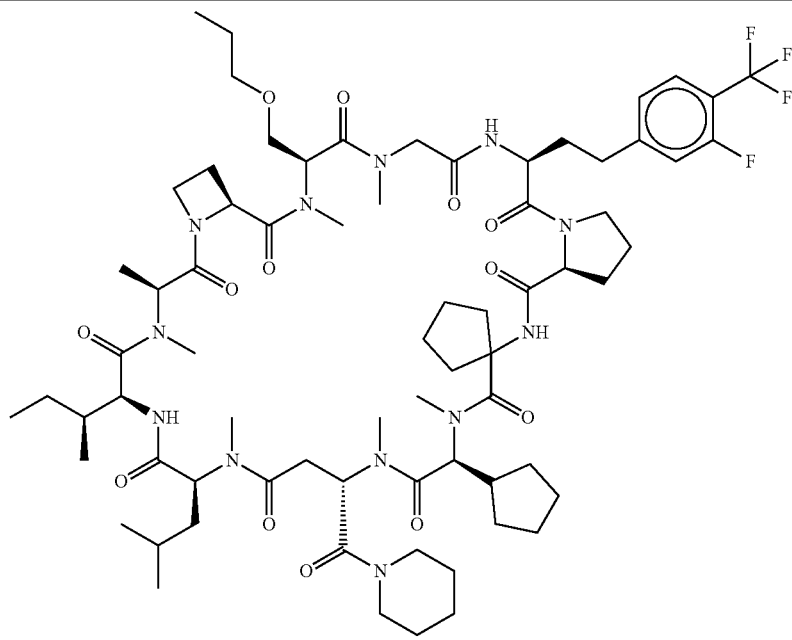 |
| 1030 | 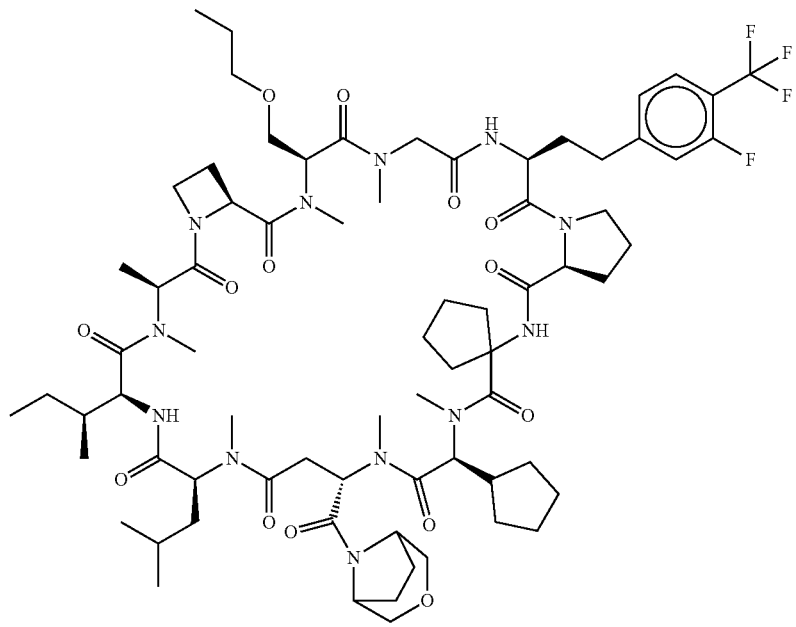 |

TABLE 24-continued

| Compound No. | Structural formula |
|---|---|
| 1031 | |
| 1032 | |

TABLE 24-continued
| Compound No. | Structural formula |
|---|---|
| 1033 | 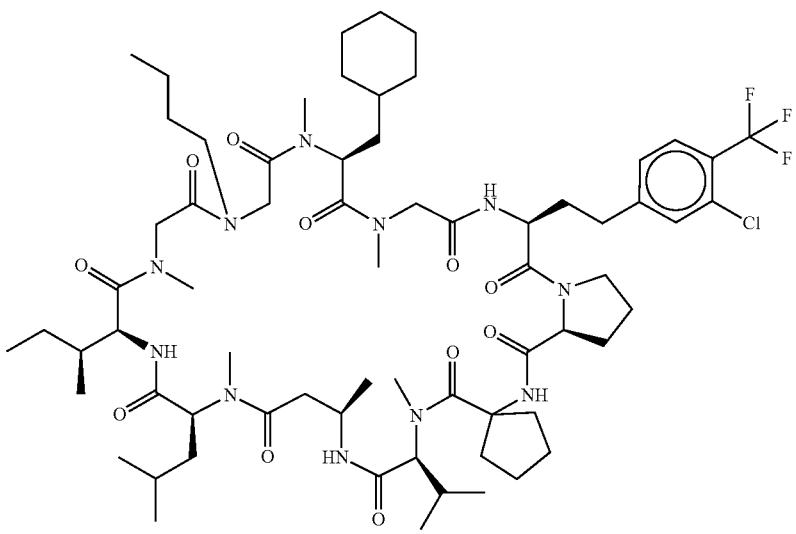 |
| 1034 | 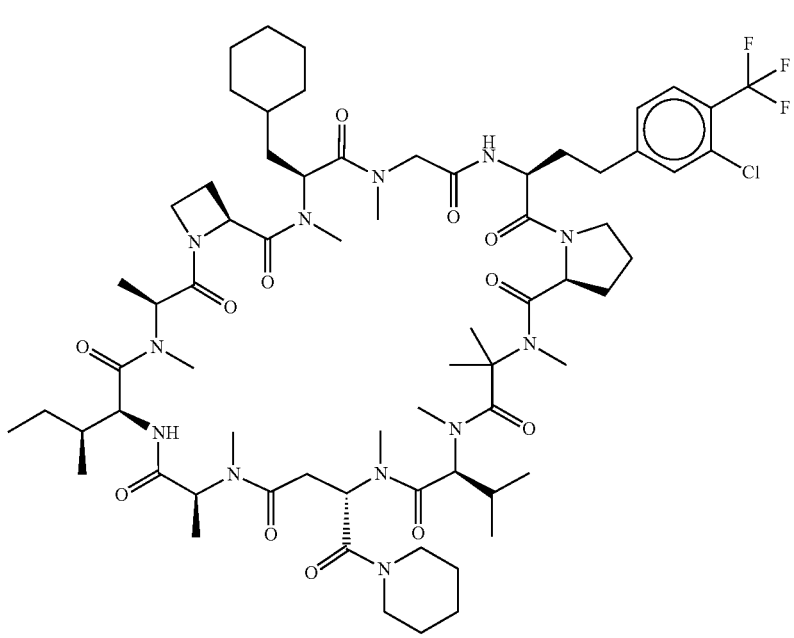 |

TABLE 24-continued
| Compound No. | Structural formula |
|---|---|
| 1035 | 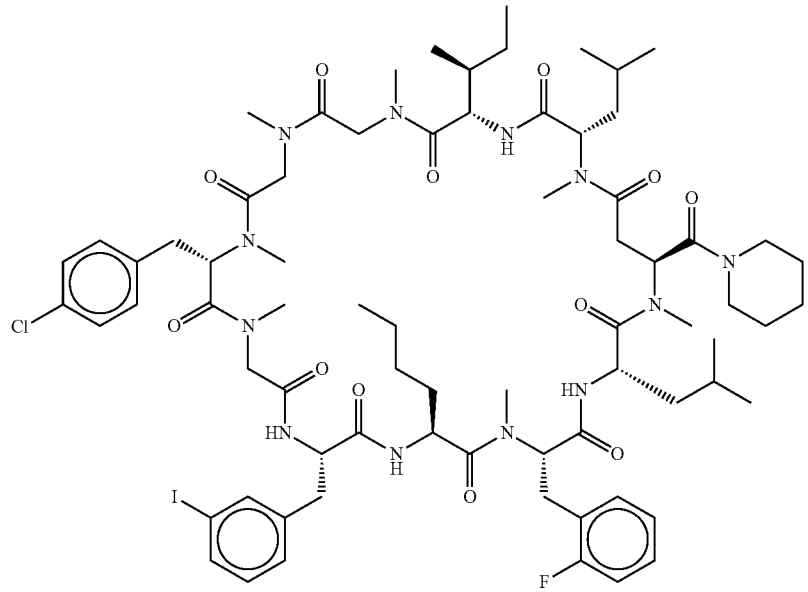 |
| 1036 | 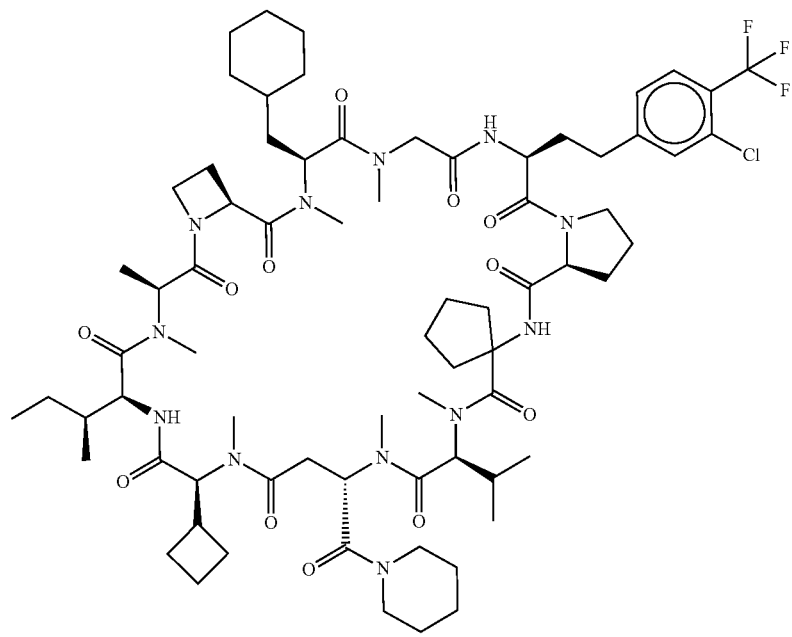 |

1981
TABLE 24-continued
| Compound No. | Structural formula |
|---|---|
| 1037 | 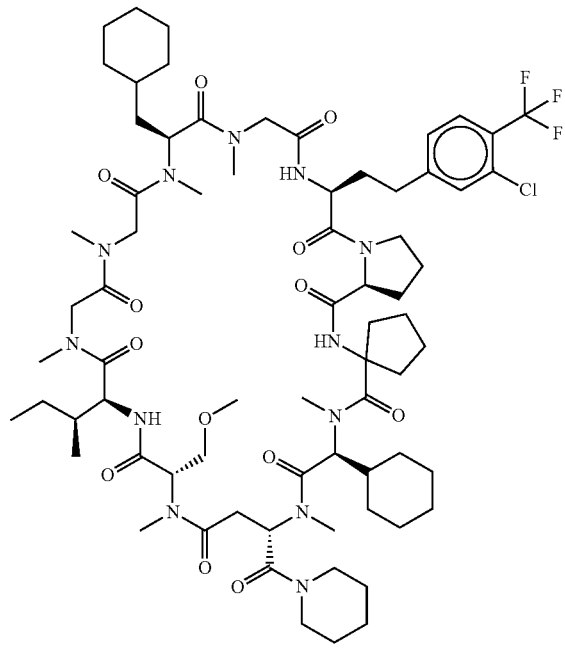 |
| 1038 | 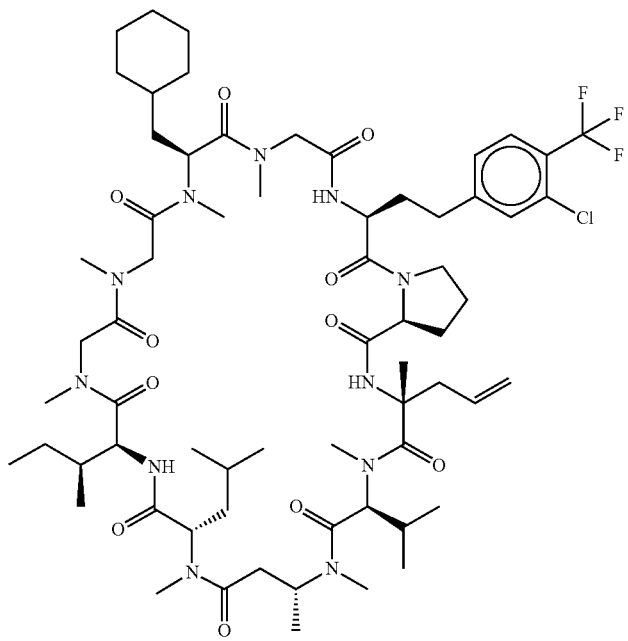 |

TABLE 24-continued
| Compound No. | Structural formula |
|---|---|
| 1039 | 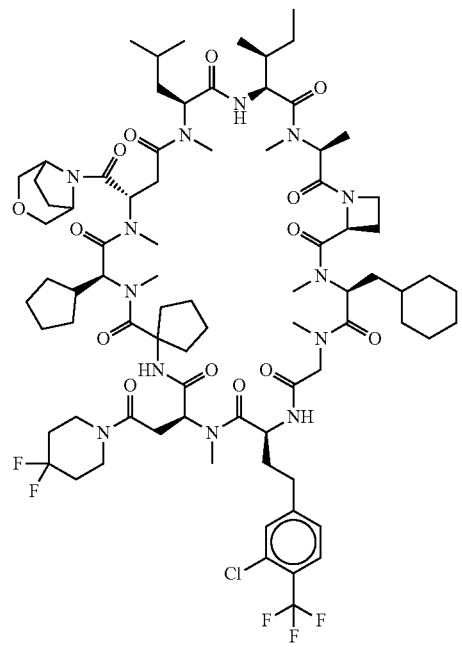 |
| 1040 | 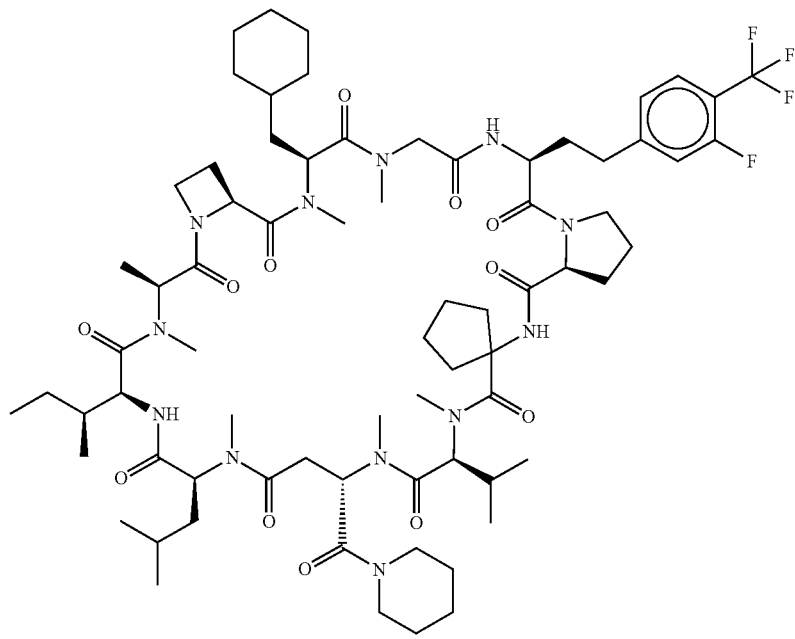 |

TABLE 24-continued
| Compound No. | Structural formula |
|---|---|
| 1041 | 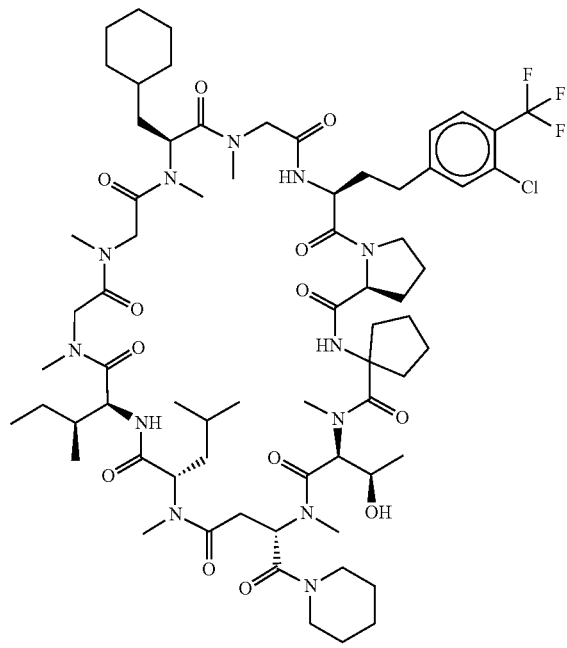 |
| 1042 | 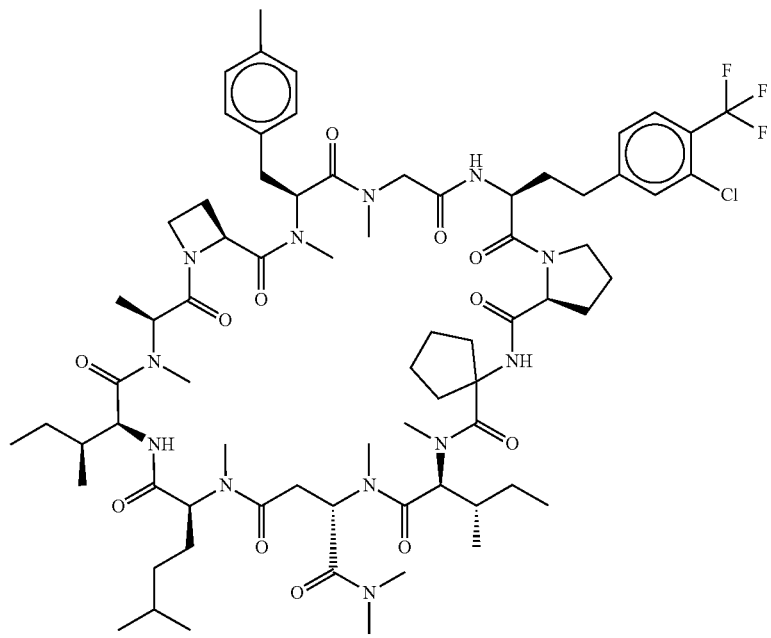 |

TABLE 24-continued
| Compound No. | Structural formula |
|---|---|
| 1043 | 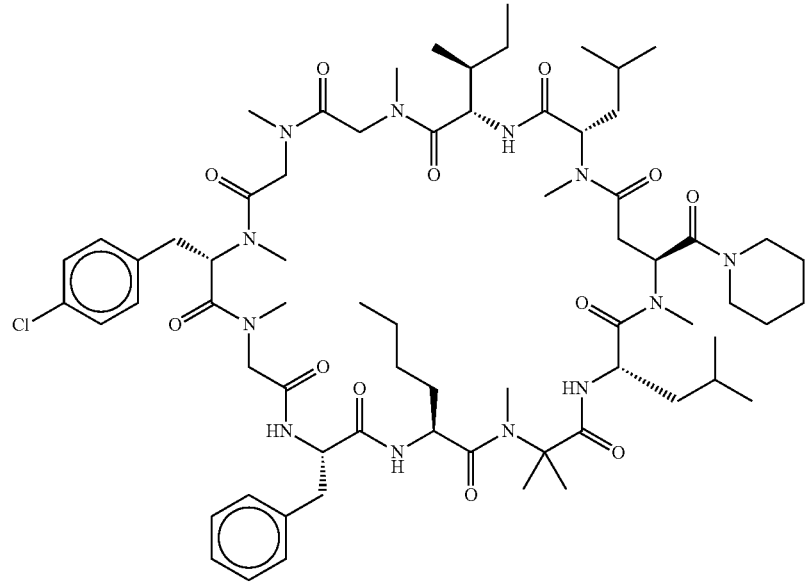 |
| 1044 | 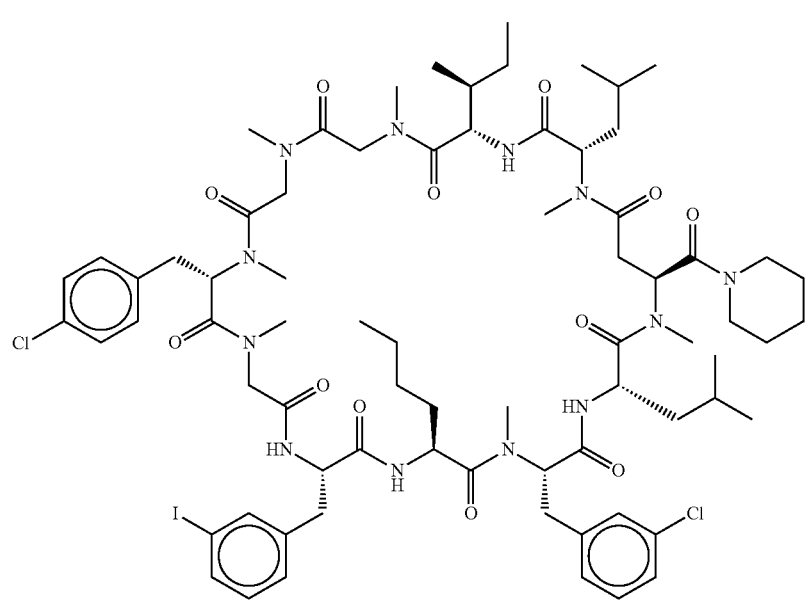 |

TABLE 24-continued
| Compound No. | Structural formula |
|---|---|
| 1045 | 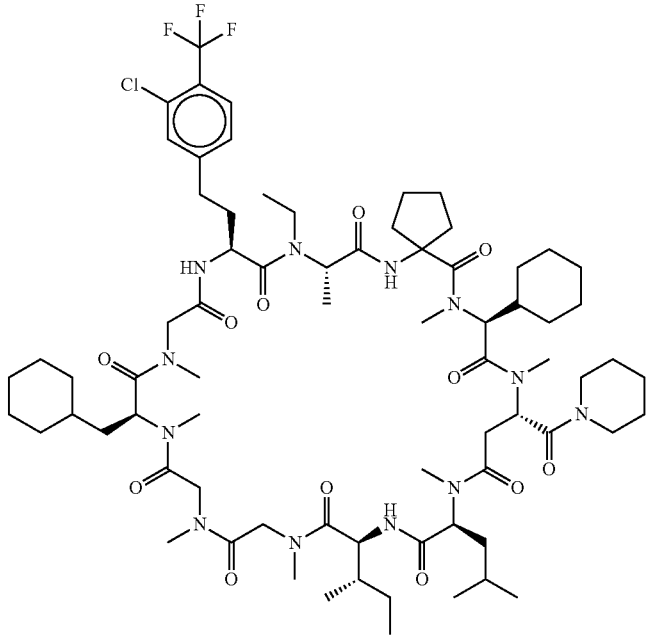 |
| 1046 | 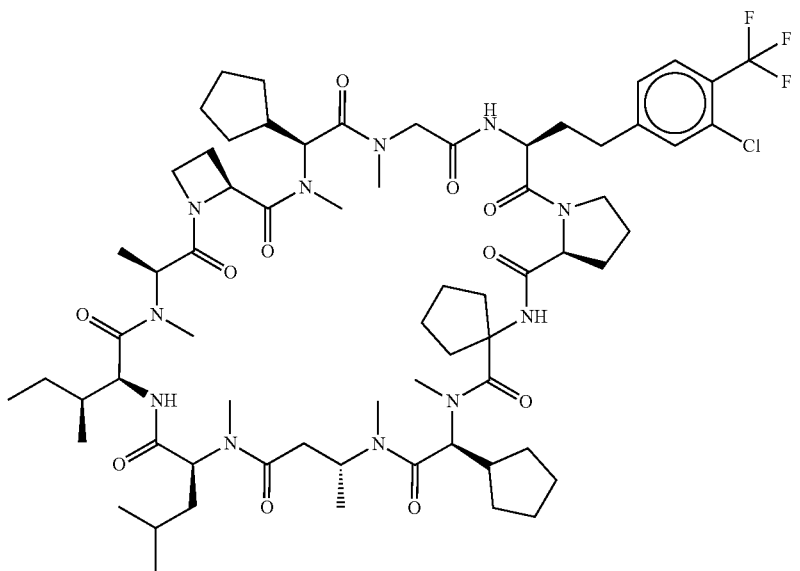 |

TABLE 24-continued
| Compound No. | Structural formula |
|---|---|
| 1047 | 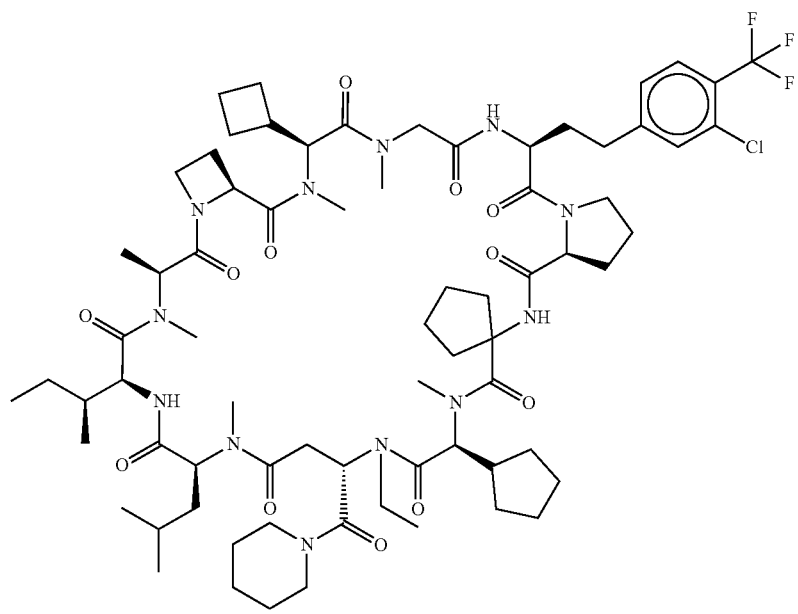 |
| 1048 | 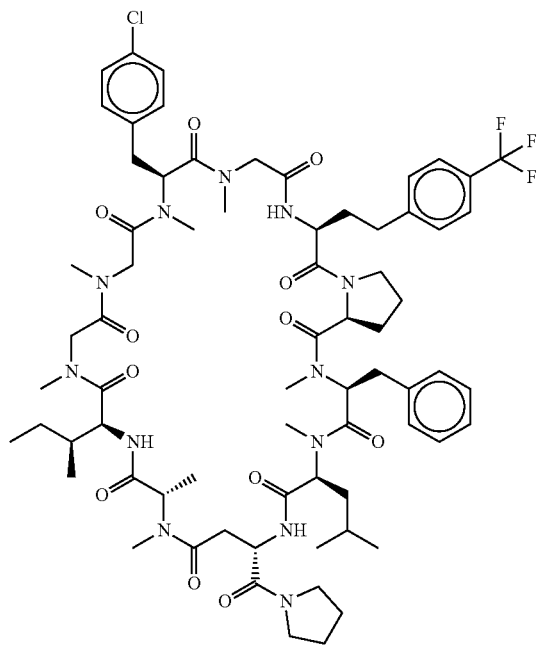 |

TABLE 24-continued
| Compound No. | Structural formula |
|---|---|
| 1049 | 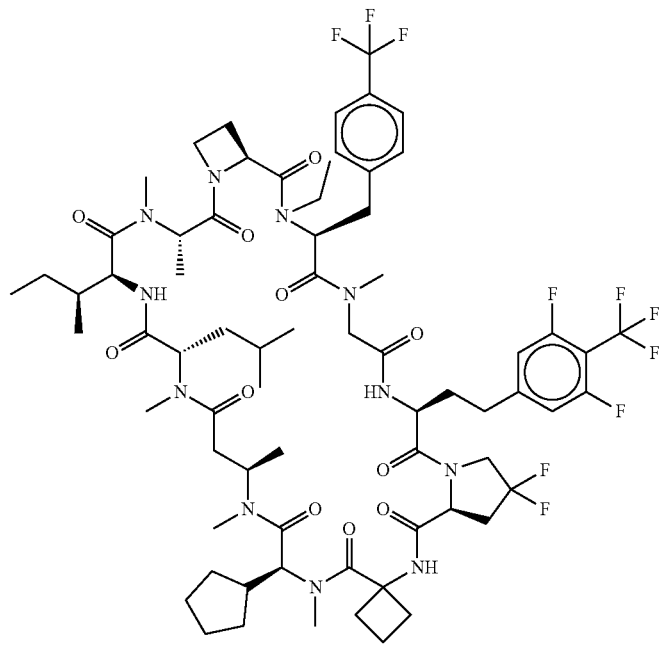 |
| 1050 | 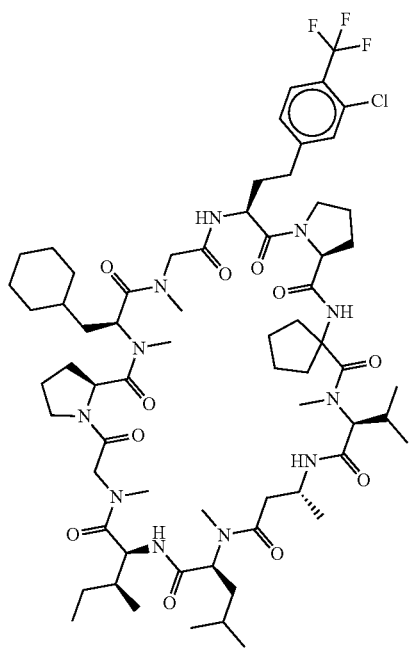 |

TABLE 24-continued
| Compound No. | Structural formula |
|---|---|
| 1051 | 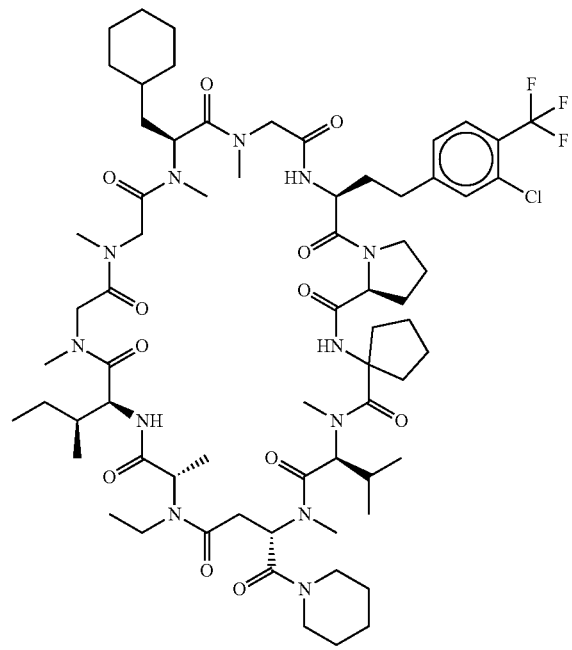 |
| 1052 | 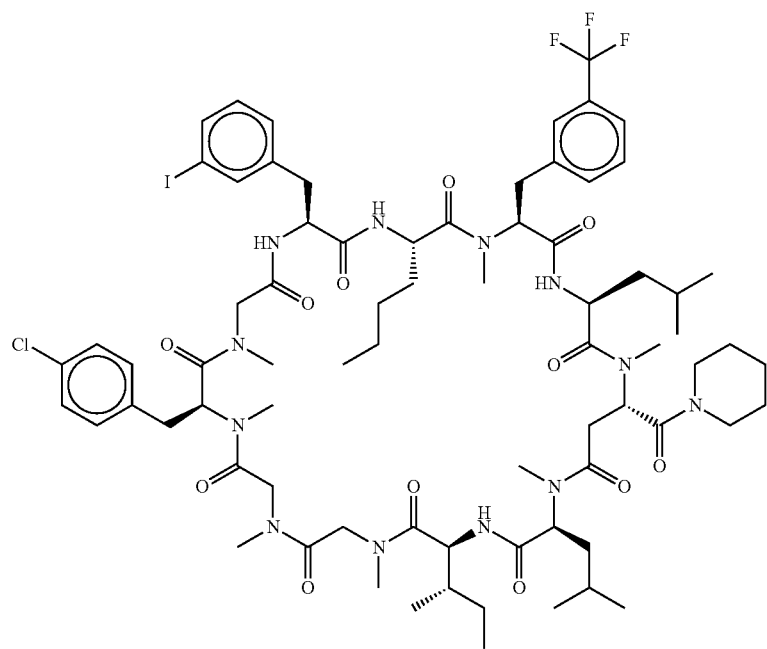 |

TABLE 24-continued
| Compound No. | Structural formula |
|---|---|
| 1053 | 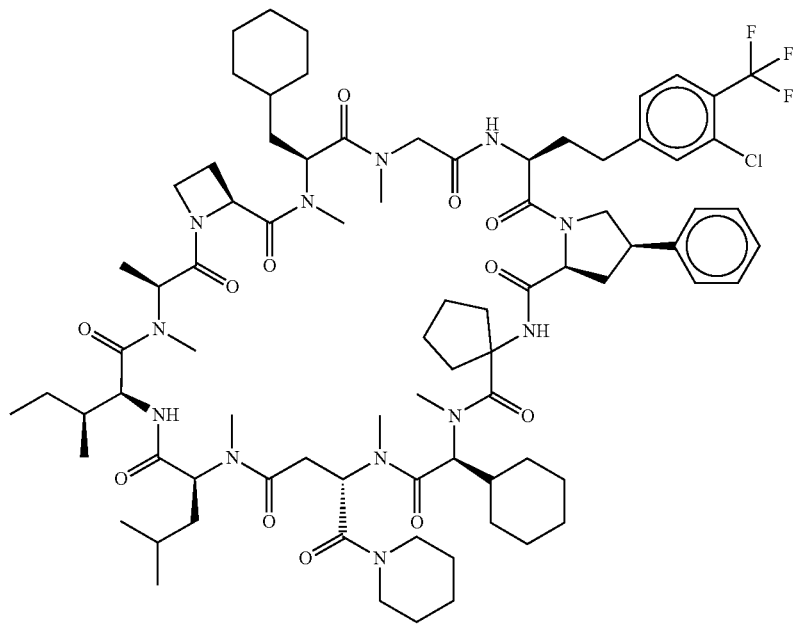 |
| 1054 | 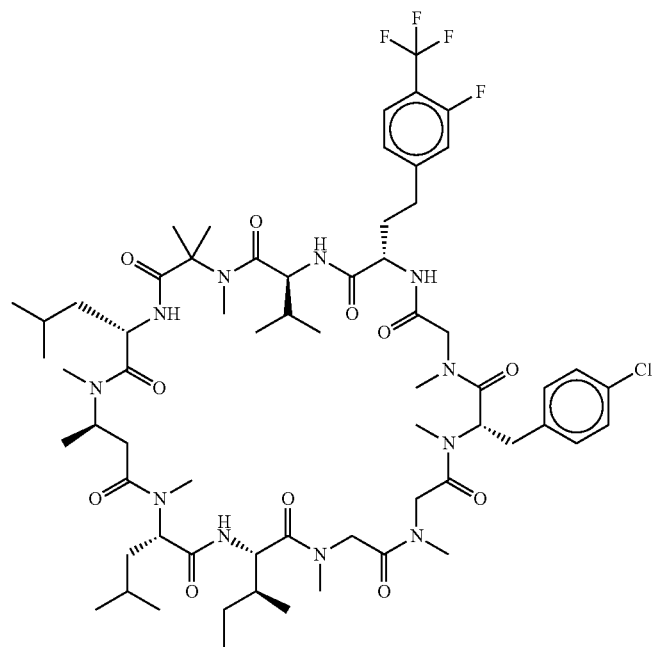 |

TABLE 24-continued
| Compound No. | Structural formula |
|---|---|
| 1055 | 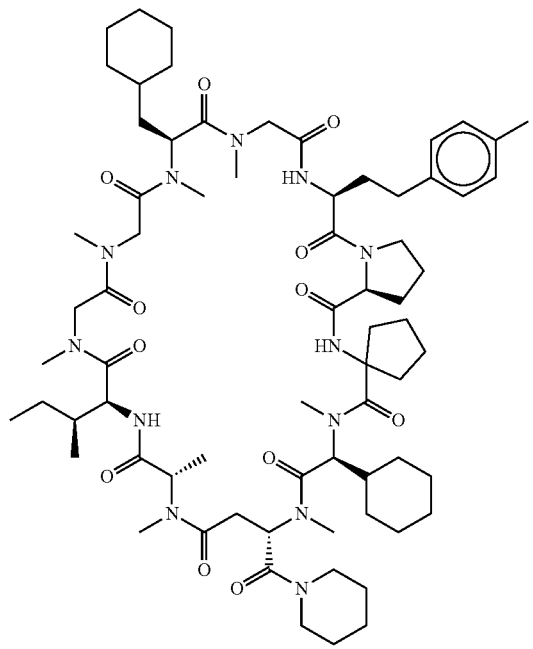 |
| 1056 | 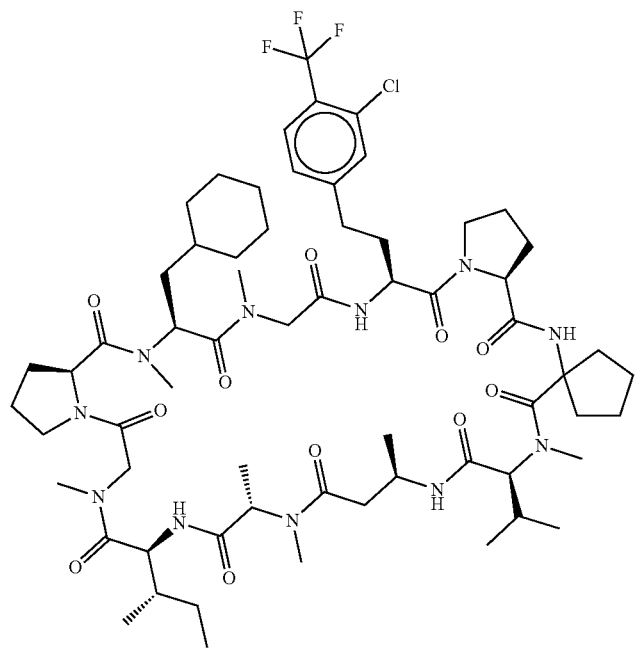 |

TABLE 24-continued
| Compound No. | Structural formula |
|---|---|
| 1057 | 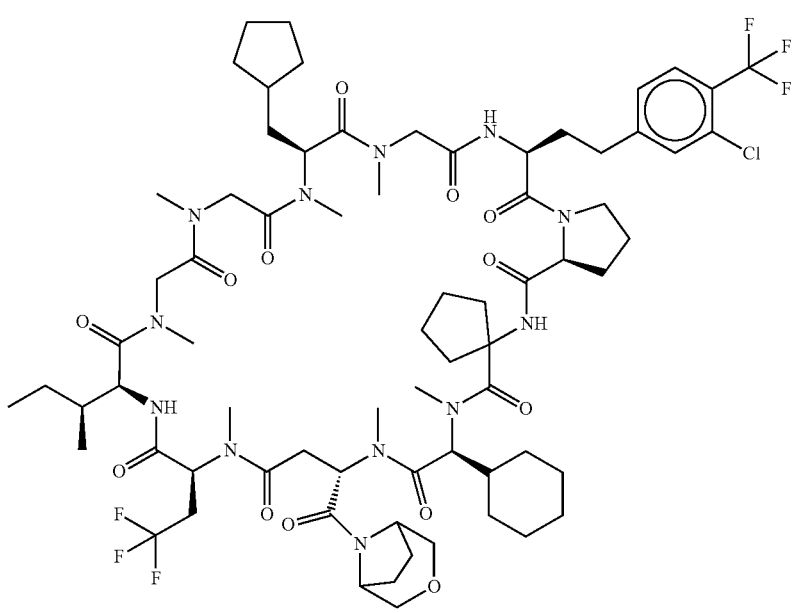 |
| 1058 | 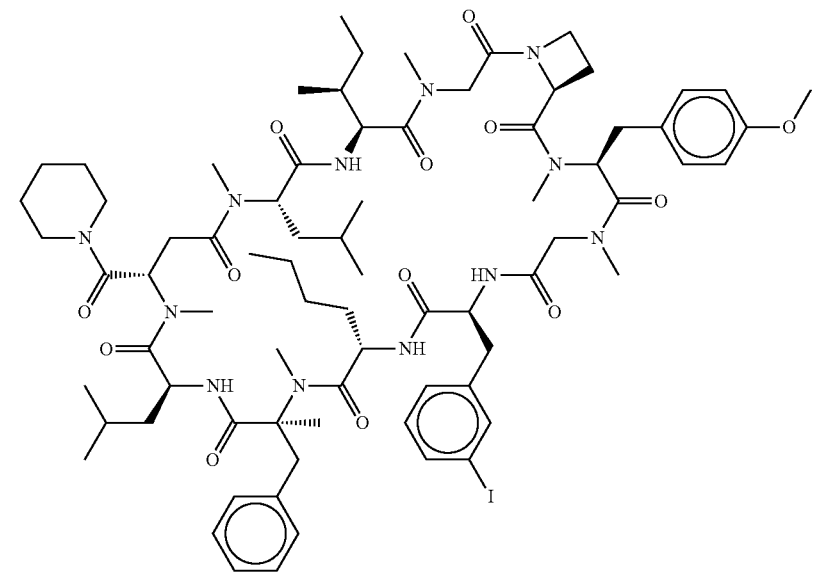 |

TABLE 24-continued
| Compound No. | Structural formula |
|---|---|
| 1059 | 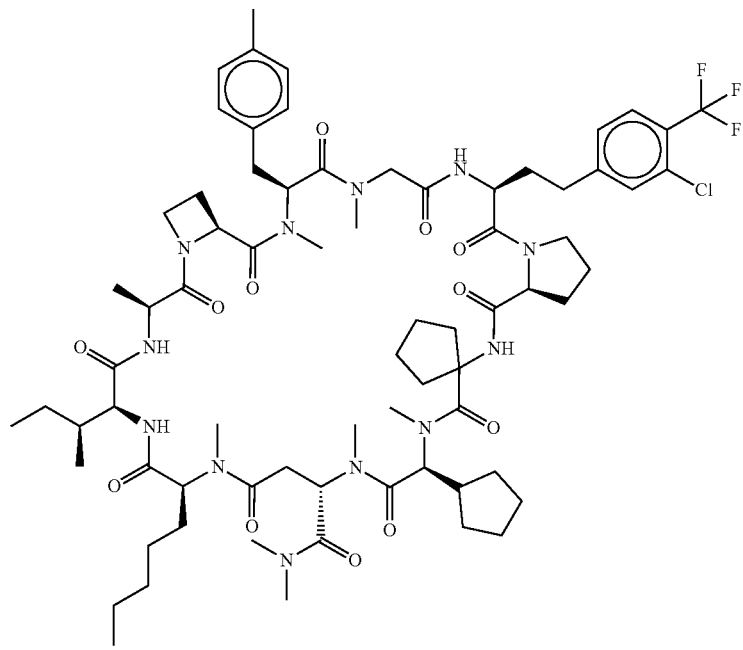 |
| 1060 | 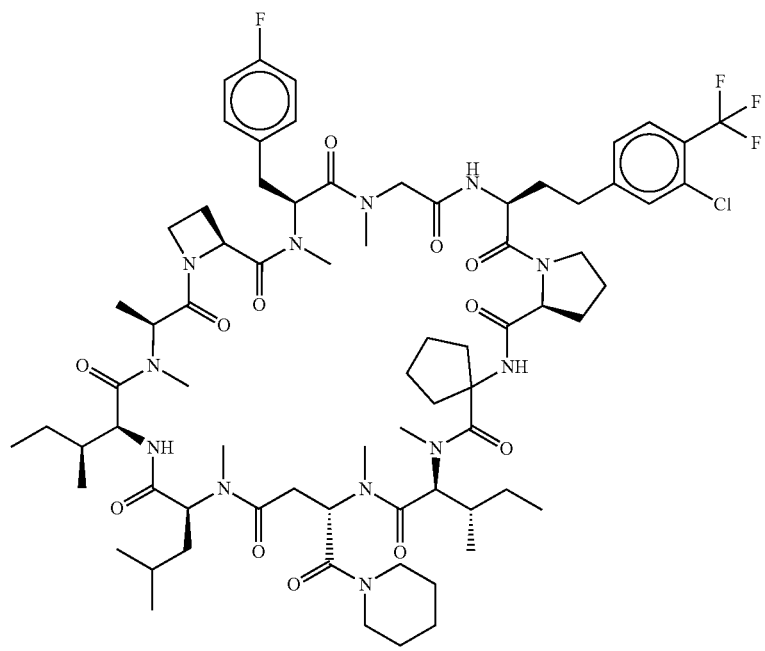 |

TABLE 24-continued
| Compound No. | Structural formula |
|---|---|
| 1061 | 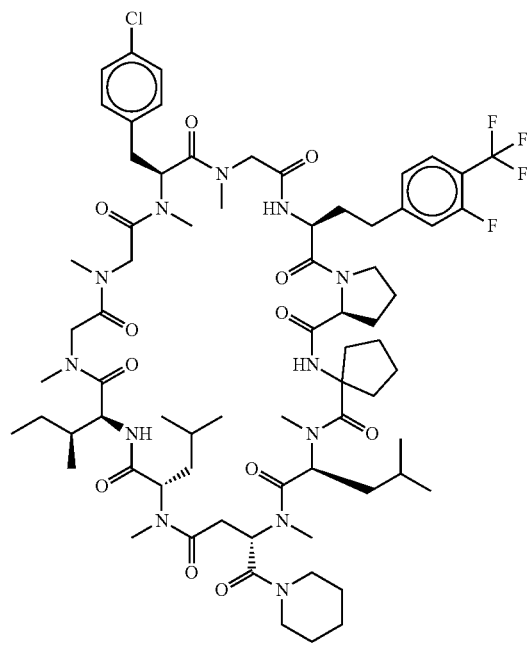 |
| 1062 | 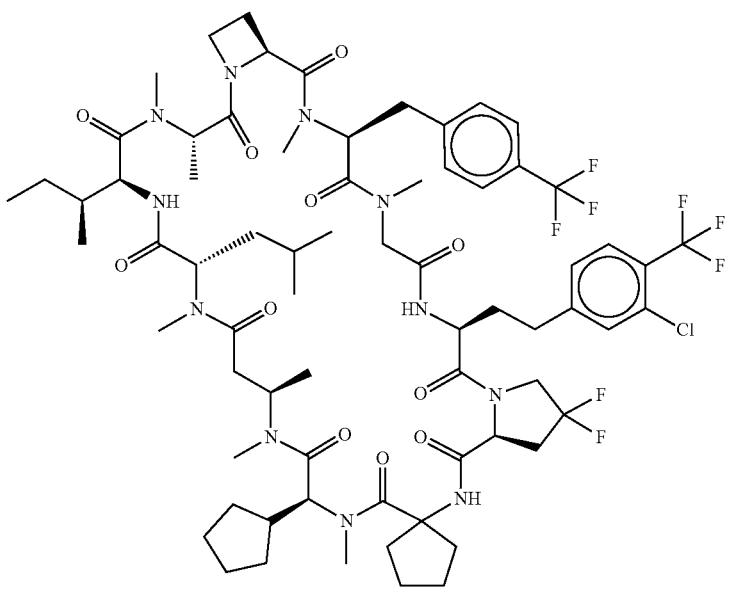 |

TABLE 24-continued
| Compound No. | Structural formula |
|---|---|
| 1063 | 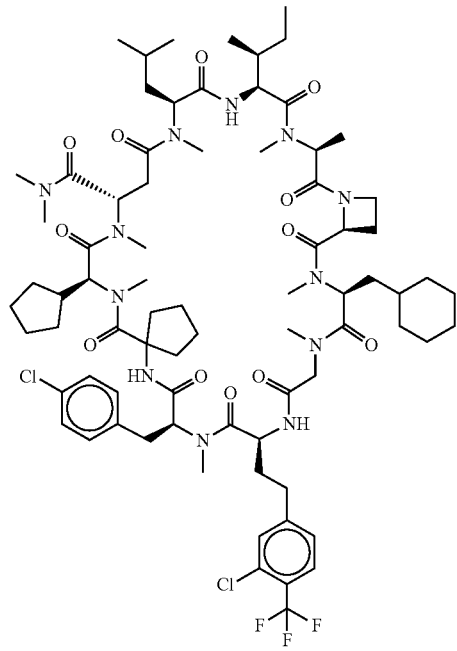 |
| 1064 | 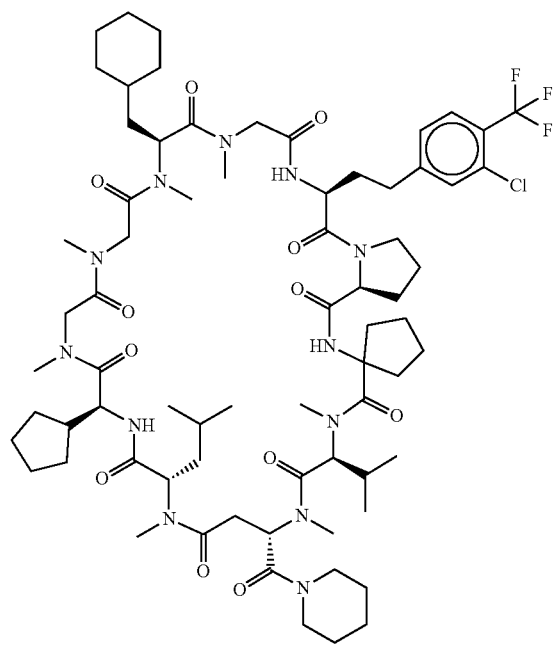 |

TABLE 24-continued
| Compound No. | Structural formula |
|---|---|
| 1065 | 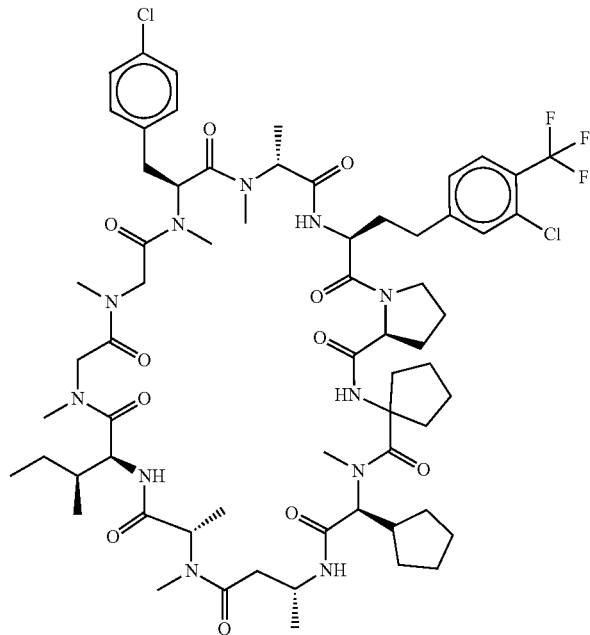 |
| 1066 | 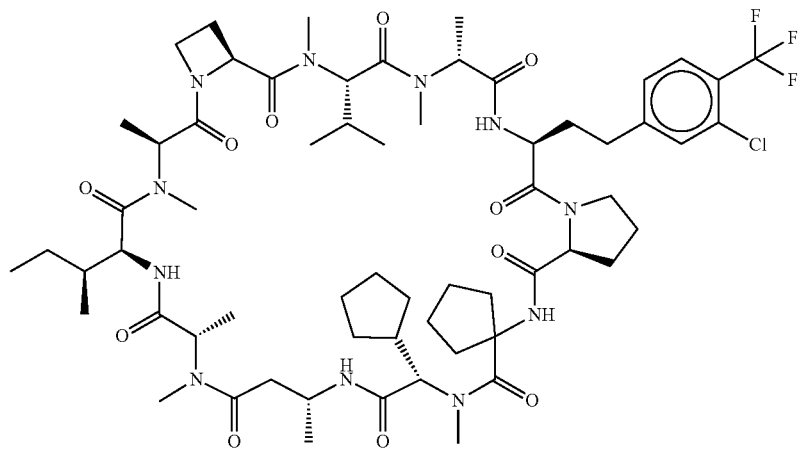 |

TABLE 24-continued
| Compound No. | Structural formula |
|---|---|
| 1067 | 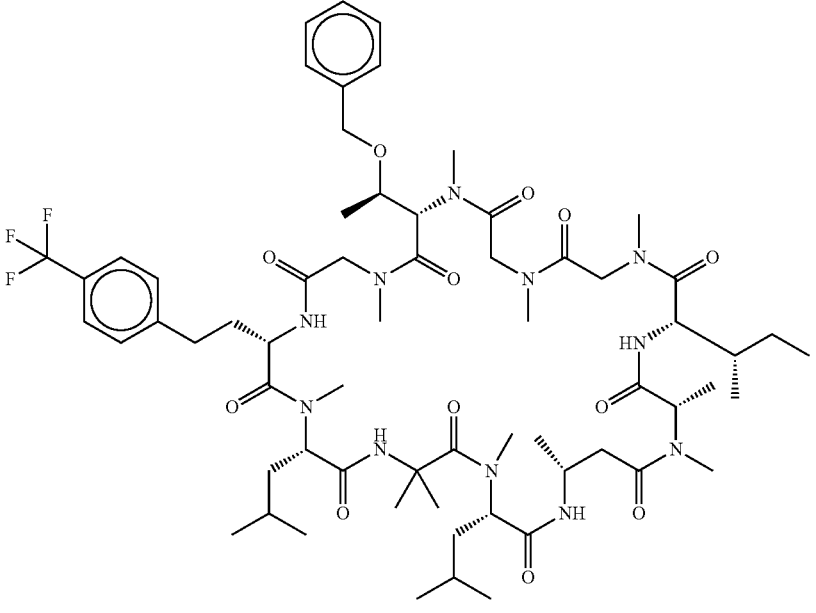 |
| 1068 | 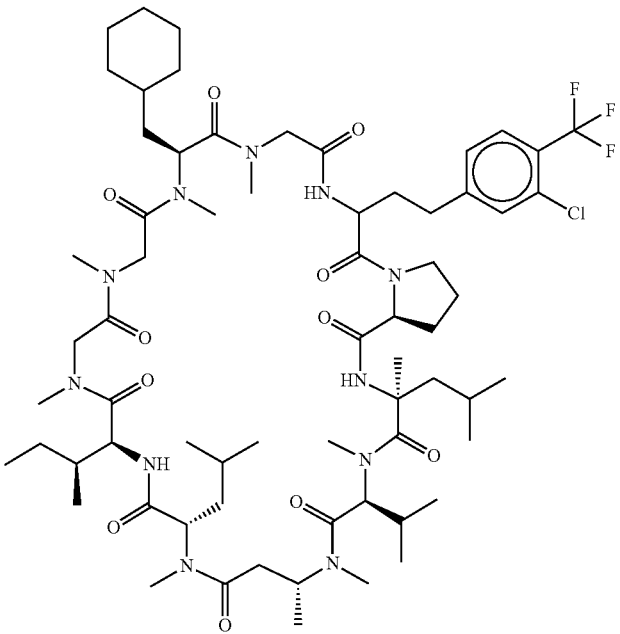 |

2013 US 12,371,454 B2 2014
TABLE 24-continued
| Compound No. | Structural formula |
|---|---|
| 1069 | 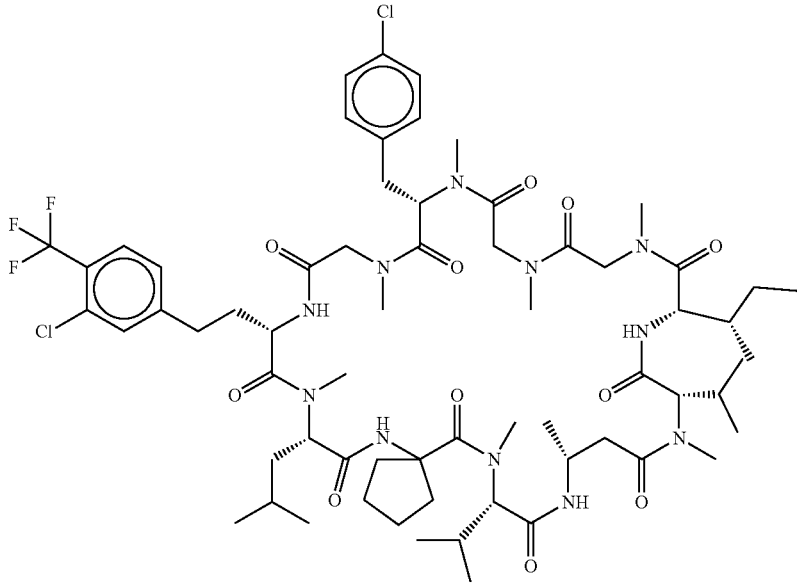 |
| 1070 | 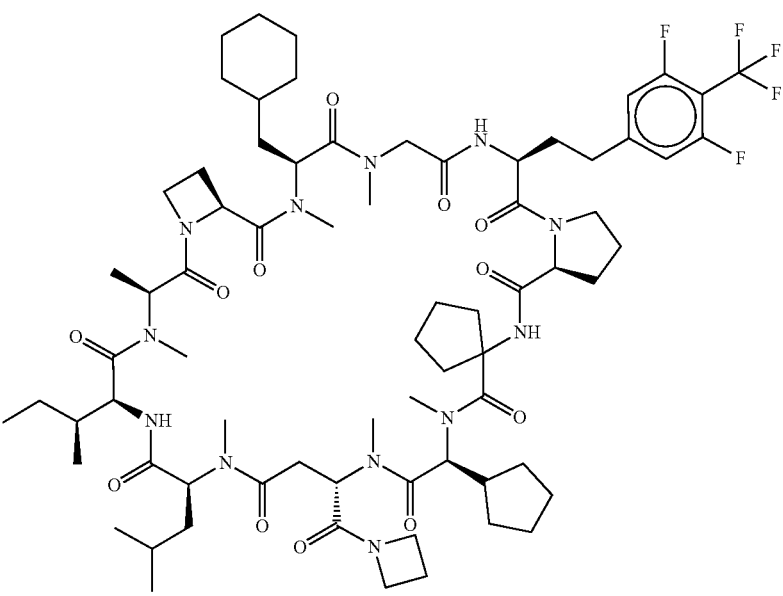 |

TABLE 24-continued
| Compound No. | Structural formula |
|---|---|
| 1071 | 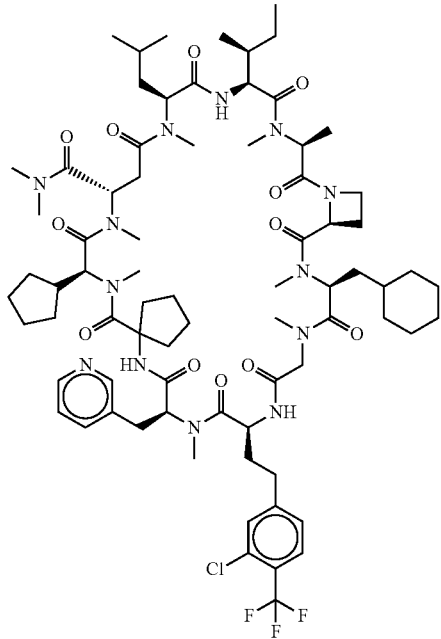 |
| 1072 | 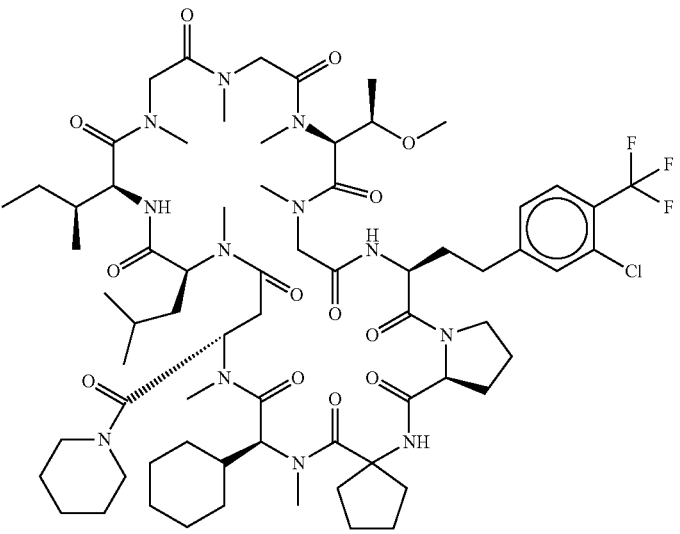 |

TABLE 24-continued
| Compound No. | Structural formula |
|---|---|
| 1073 | 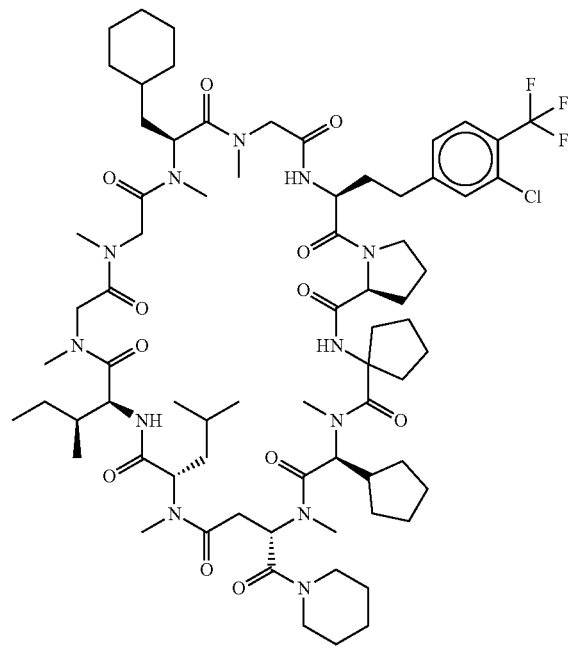 |
| 1074 | 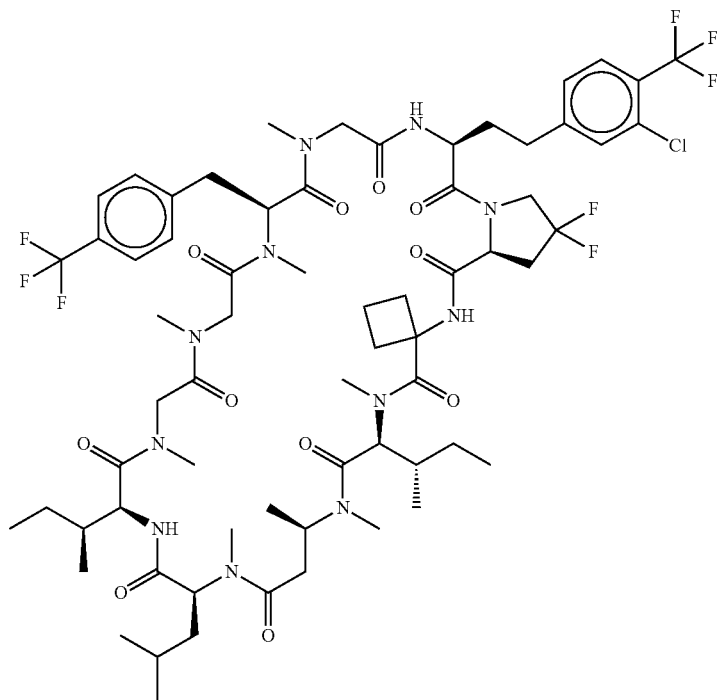 |

TABLE 24-continued
| Compound No. | Structural formula |
|---|---|
| 1075 | 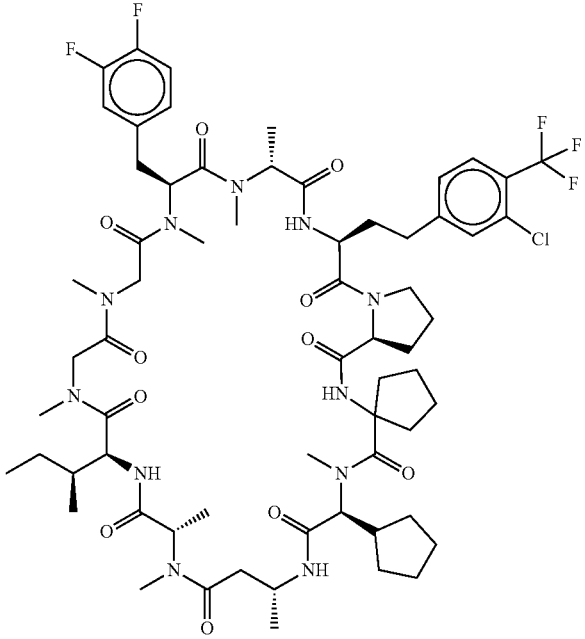 |
| 1076 | 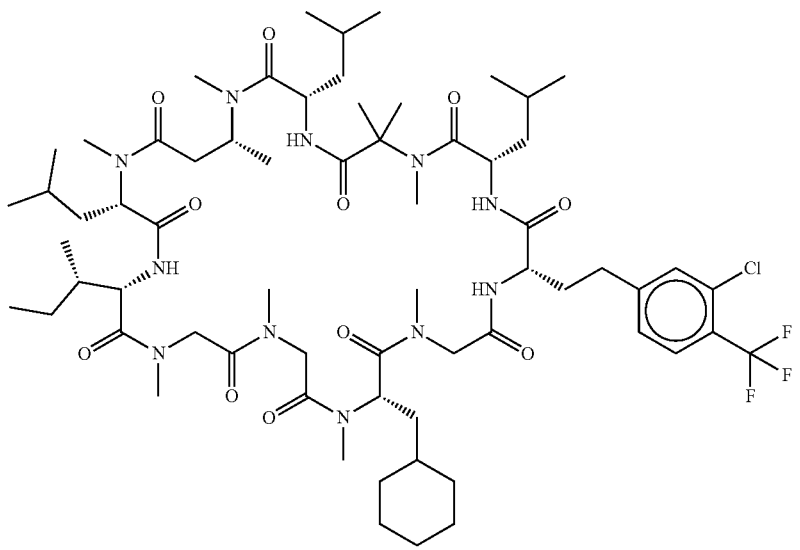 |

TABLE 24-continued
| Compound No. | Structural formula |
|---|---|
| 1077 | 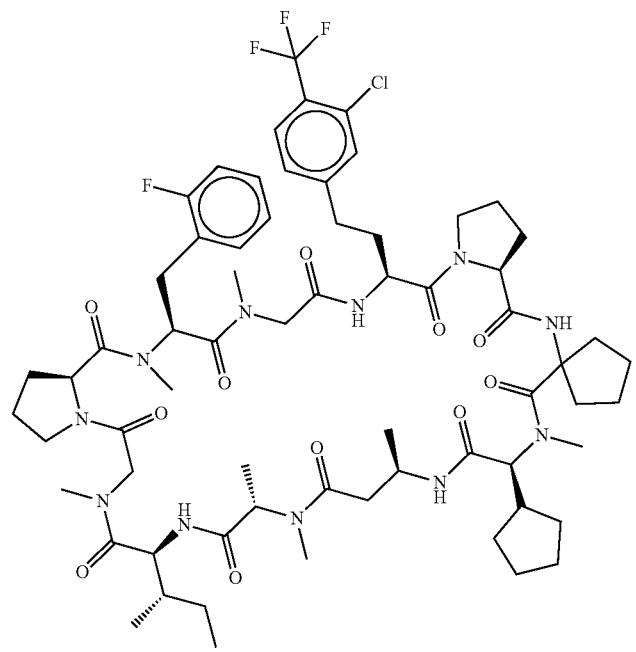 |
| 1078 | 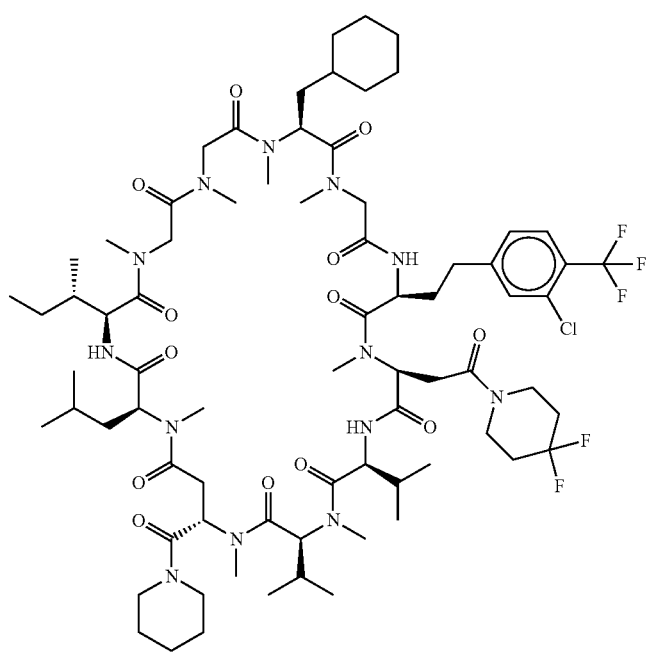 |

TABLE 24-continued
| Compound No. | Structural formula |
|---|---|
| 1079 | 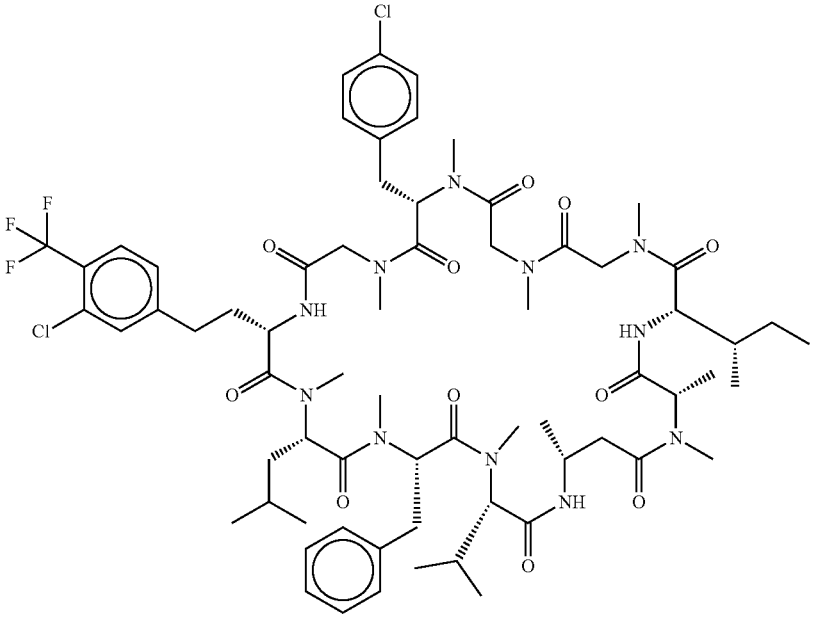 |
| 1080 | 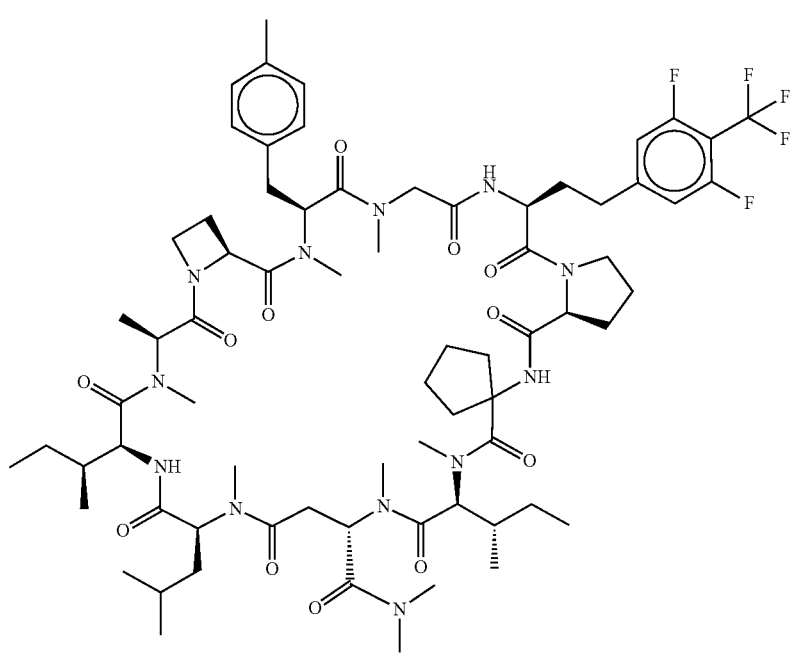 |

TABLE 24-continued
| Compound No. | Structural formula |
|---|---|
| 1081 | 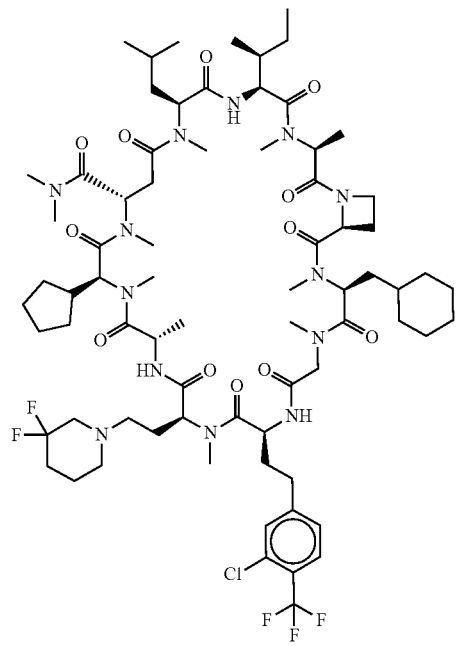 |
| 1082 | 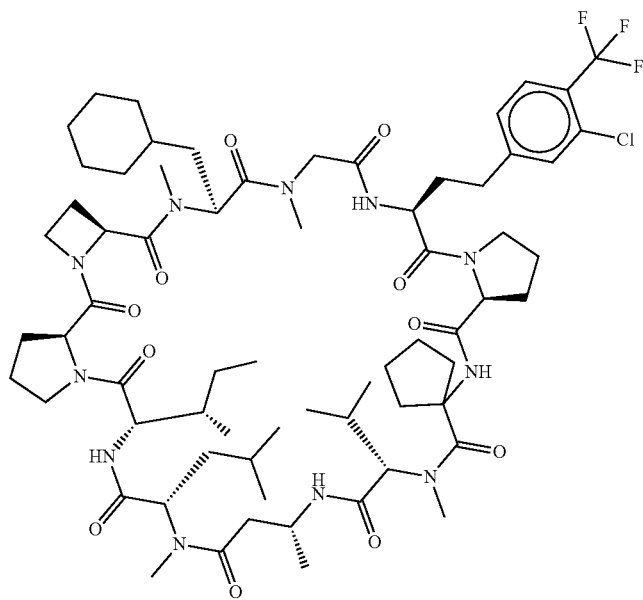 |

TABLE 24-continued
| Compound No. | Structural formula |
|---|---|
| 1083 | 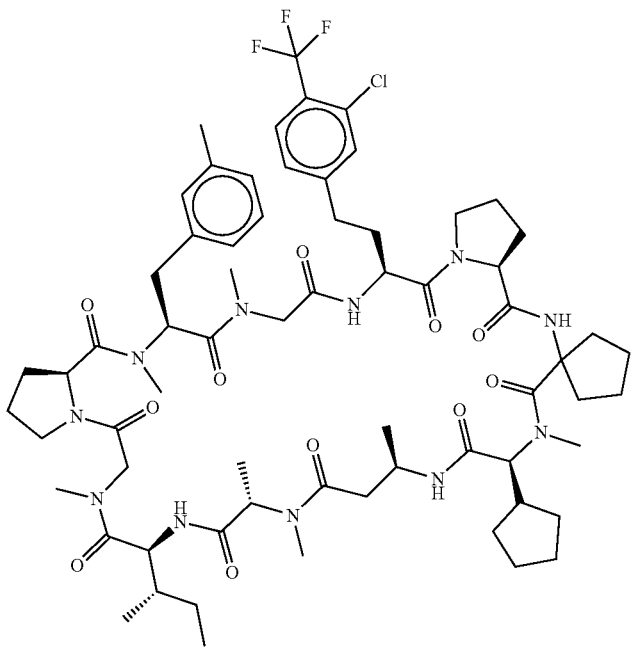 |
| 1084 | 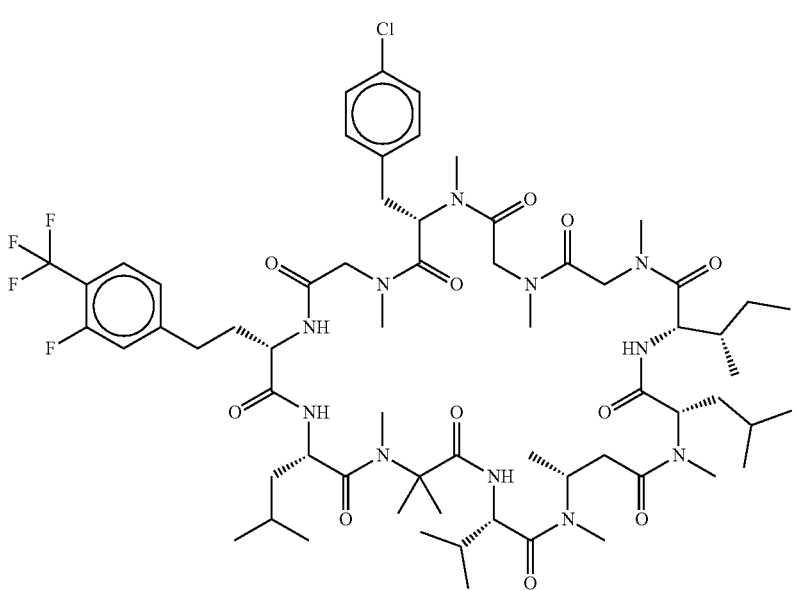 |

TABLE 24-continued
| Compound No. | Structural formula |
|---|---|
| 1085 | 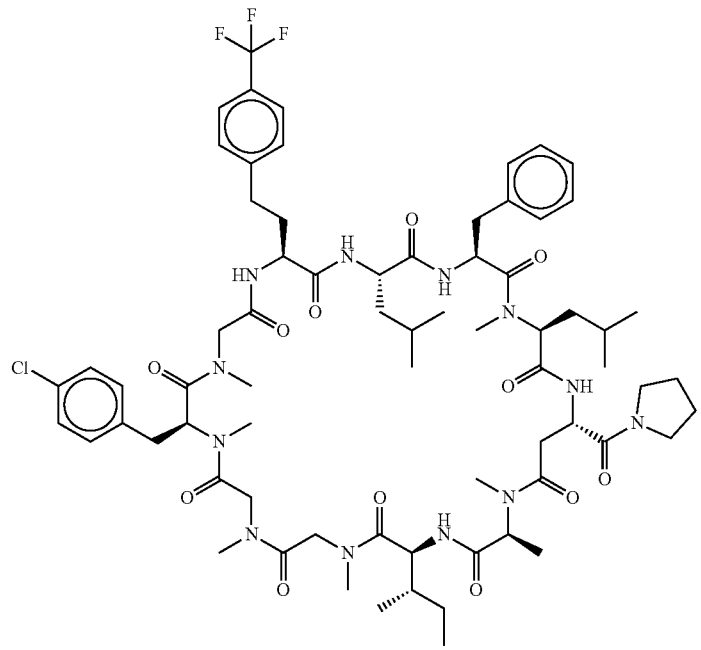 |
| 1086 | 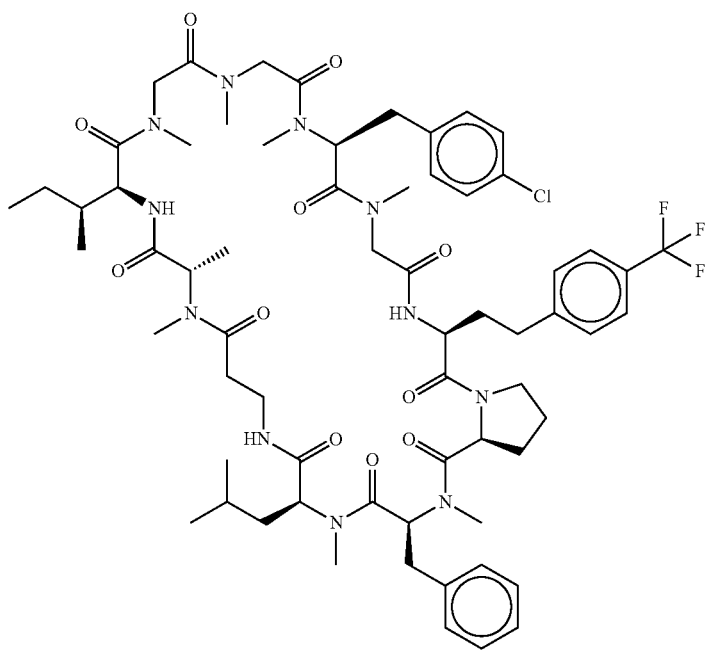 |

TABLE 24-continued
| Compound No. | Structural formula |
|---|---|
| 1087 | 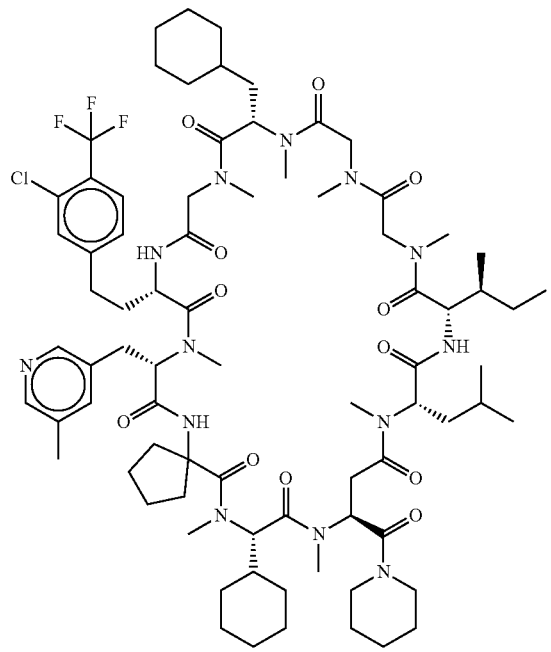 |
| 1088 | 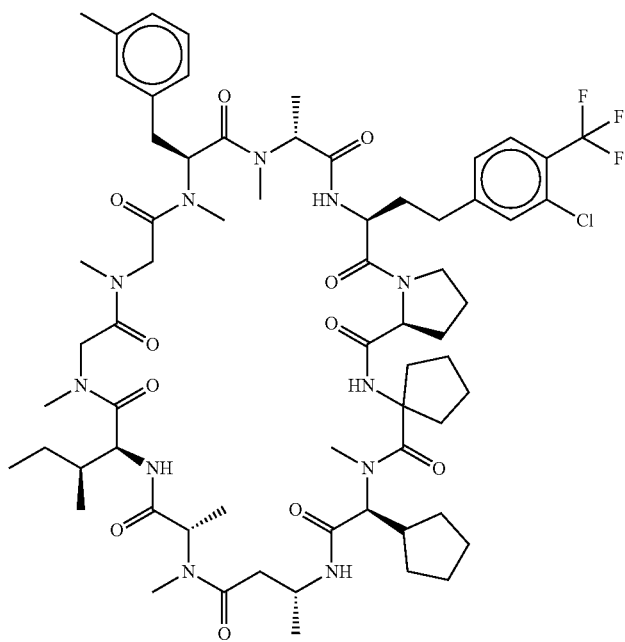 |

TABLE 24-continued
| Compound No. | Structural formula |
|---|---|
| 1089 | 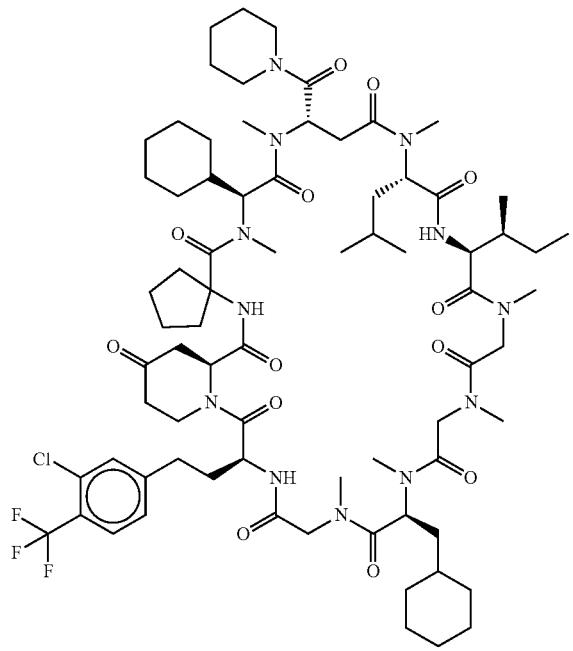 |
| 1090 | 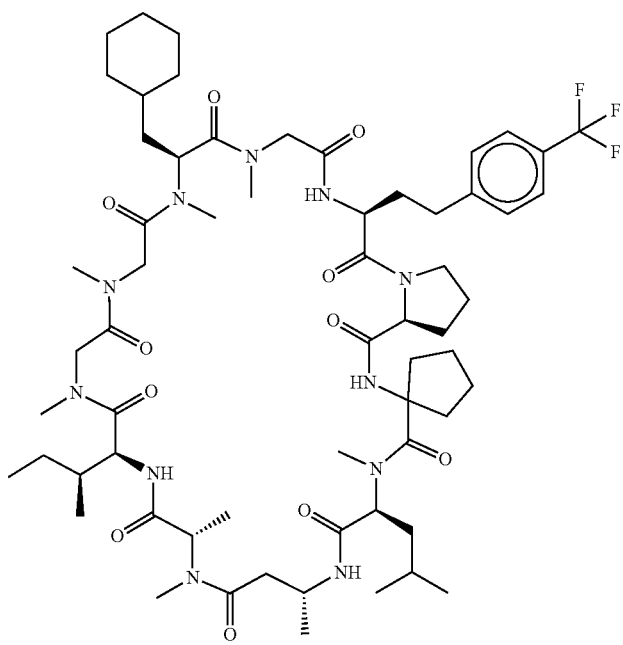 |

TABLE 24-continued
| Compound No. | Structural formula |
|---|---|
| 1091 | 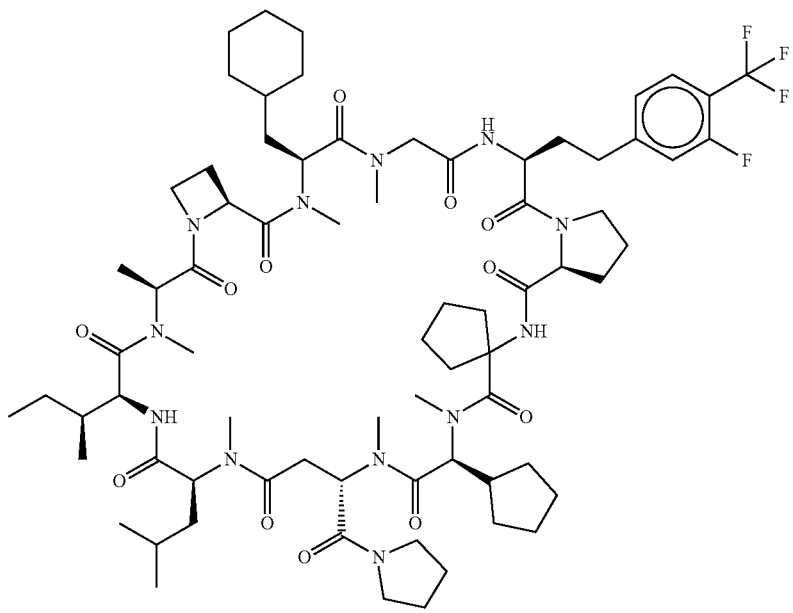 |
| 1092 | 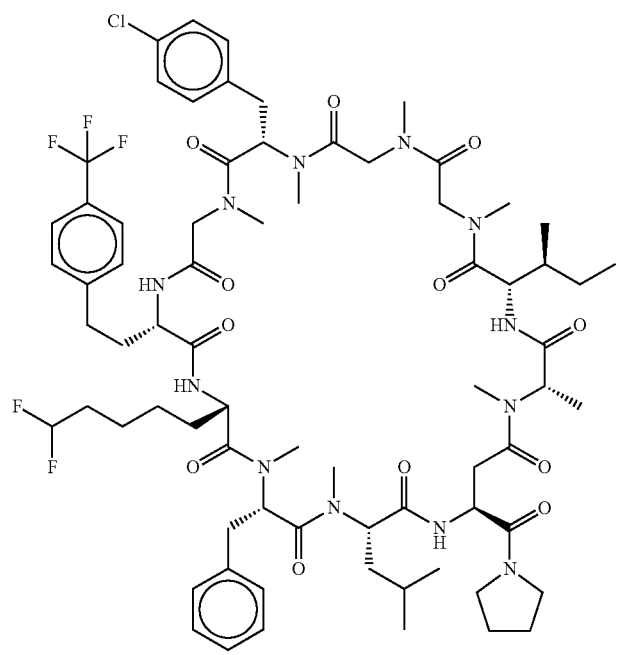 |

TABLE 24-continued
| Compound No. | Structural formula |
|---|---|
| 1093 | 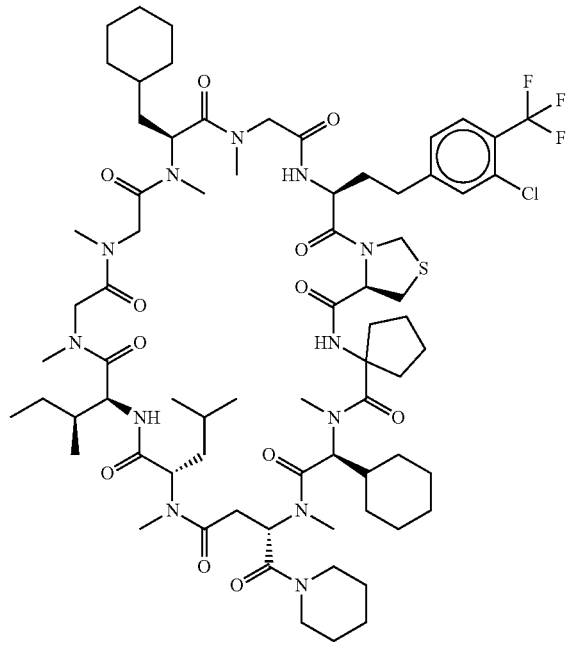 |
| 1094 | 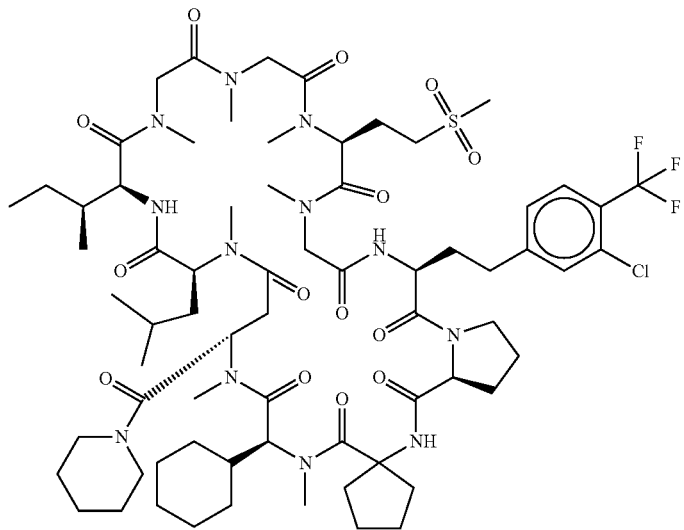 |

TABLE 24-continued
| Compound No. | Structural formula |
|---|---|
| 1095 | 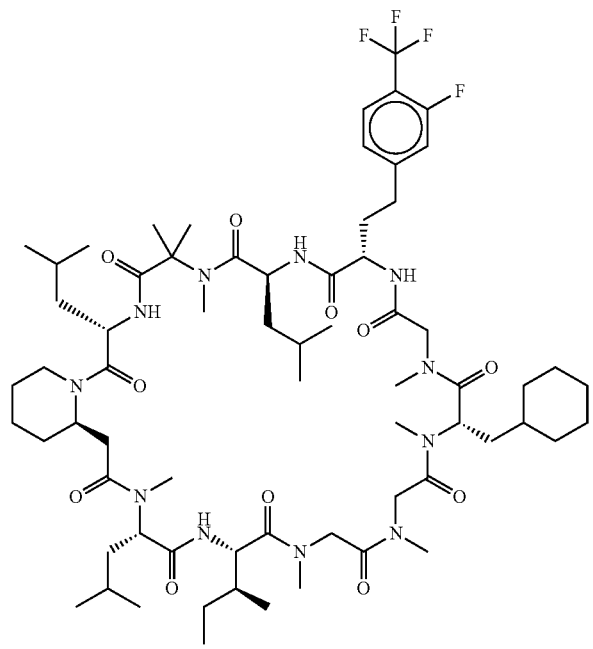 |
| 1096 | 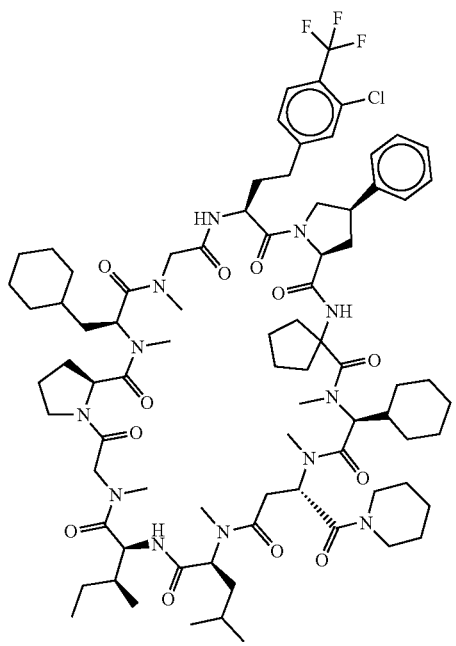 |

TABLE 24-continued
| Compound No. | Structural formula |
|---|---|
| 1097 | 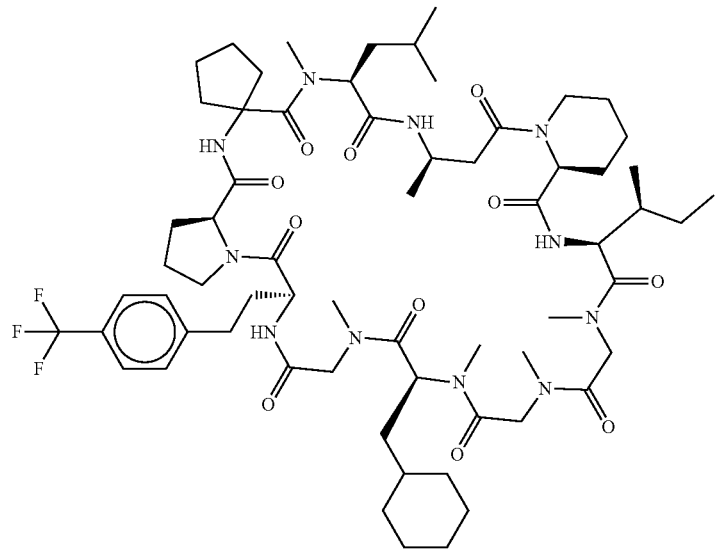 |
| 1098 | 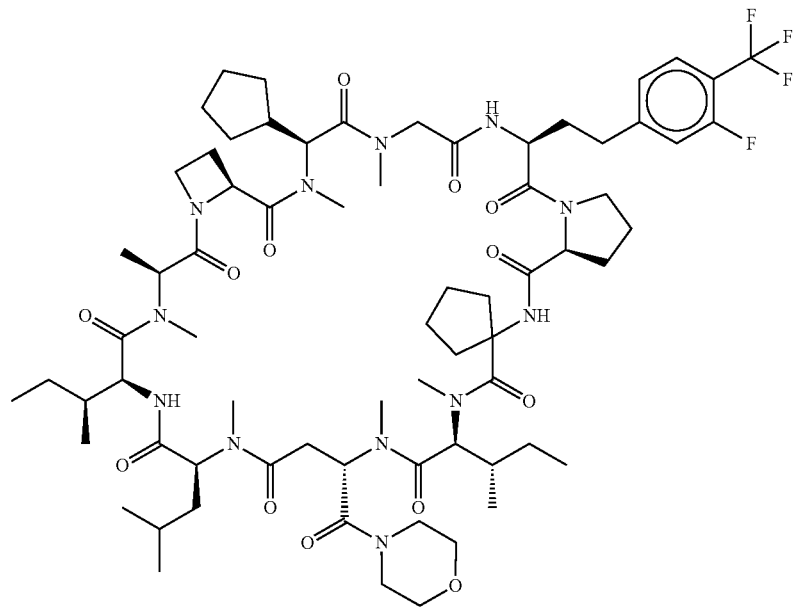 |

TABLE 24-continued
| Compound No. | Structural formula |
|---|---|
| 1099 | 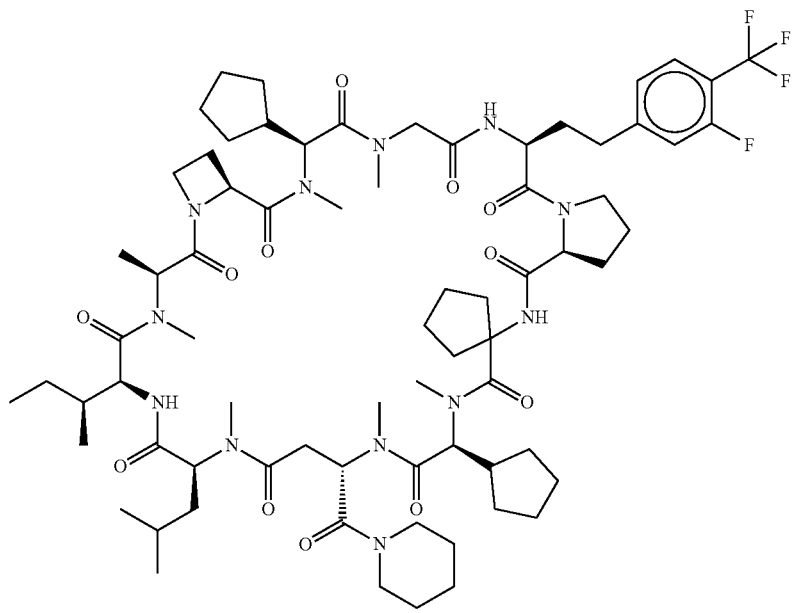 |
| 1100 | 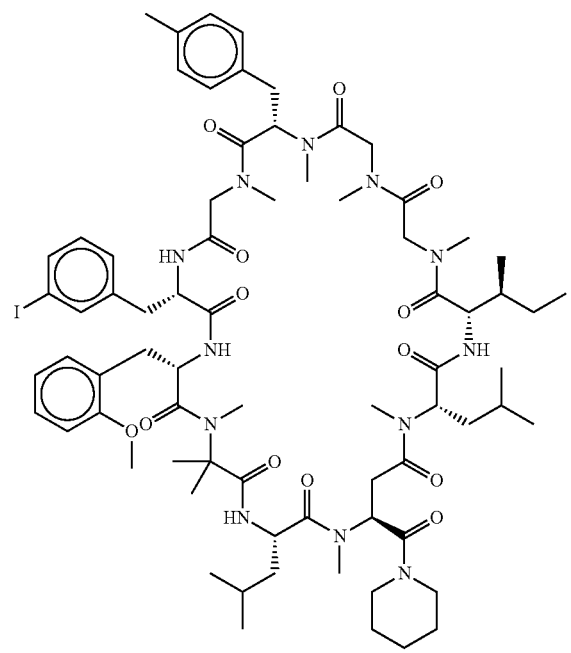 |

TABLE 24-continued
| Compound No. | Structural formula |
|---|---|
| 1101 | 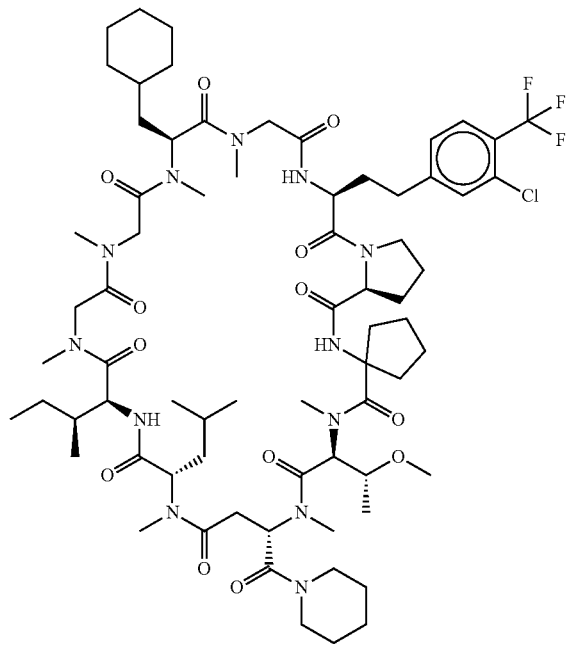 |
| 1102 | 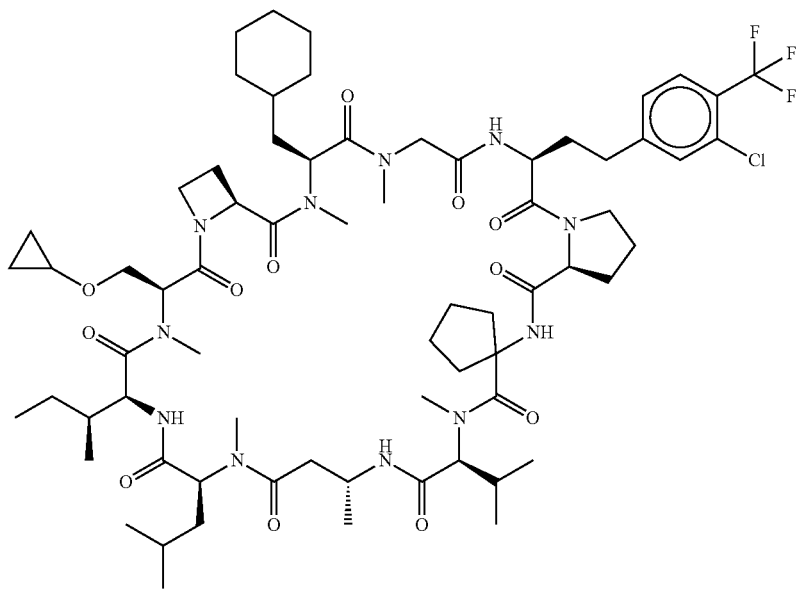 |

TABLE 24-continued
| Compound No. | Structural formula |
|---|---|
| 1103 | 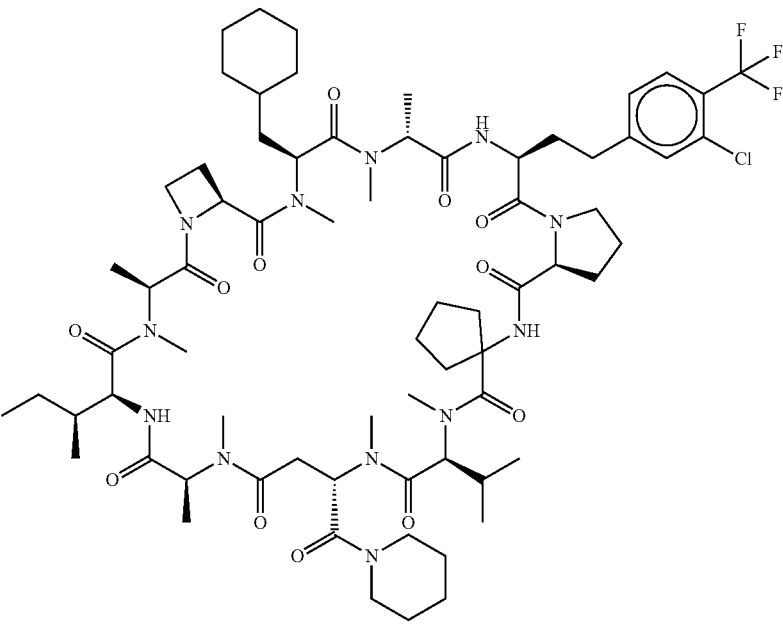 |
| 1104 | 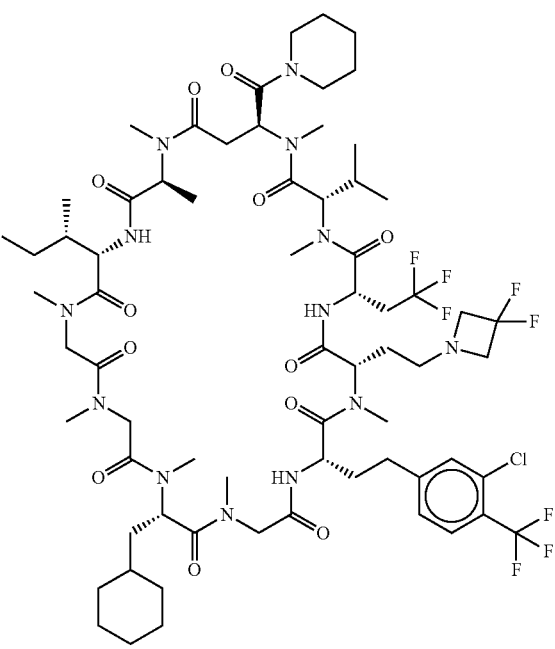 |

TABLE 24-continued
| Compound No. | Structural formula |
|---|---|
| 1105 | 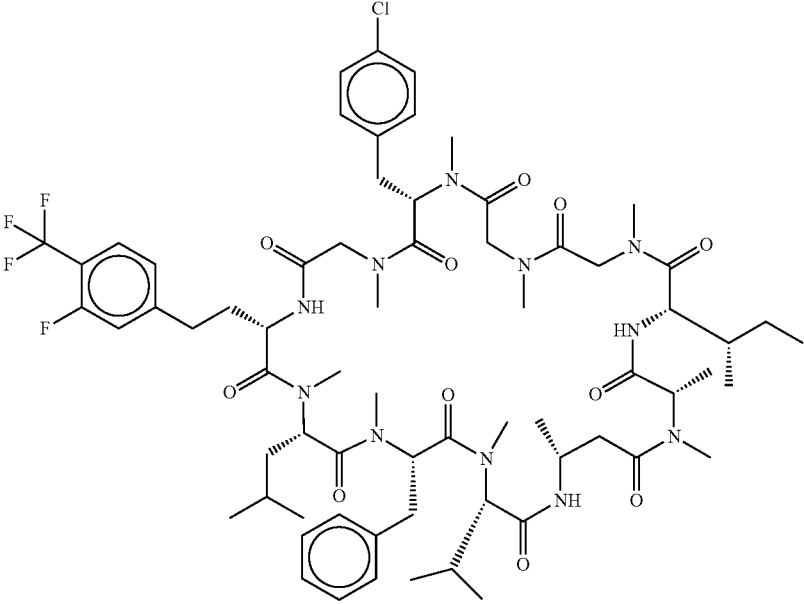 |
| 1106 | 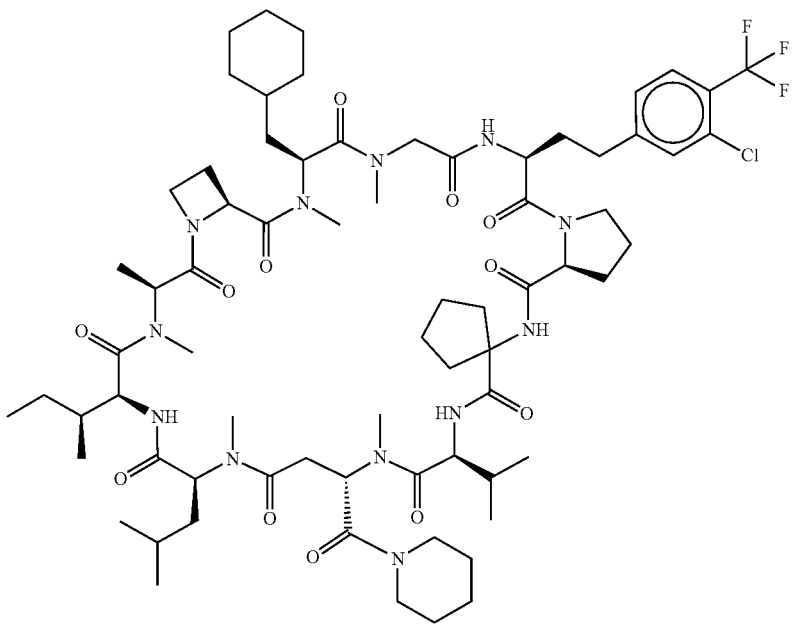 |

TABLE 24-continued
| Compound No. | Structural formula |
|---|---|
| 1107 | 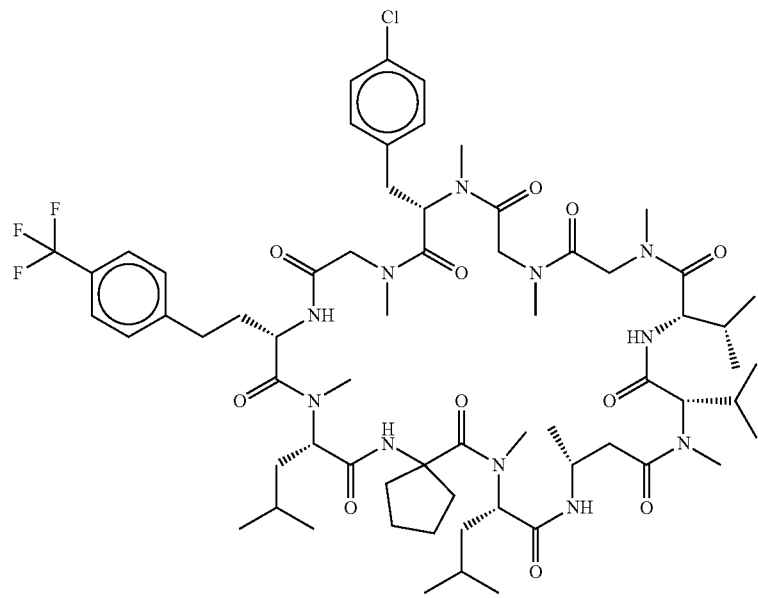 |
| 1108 | 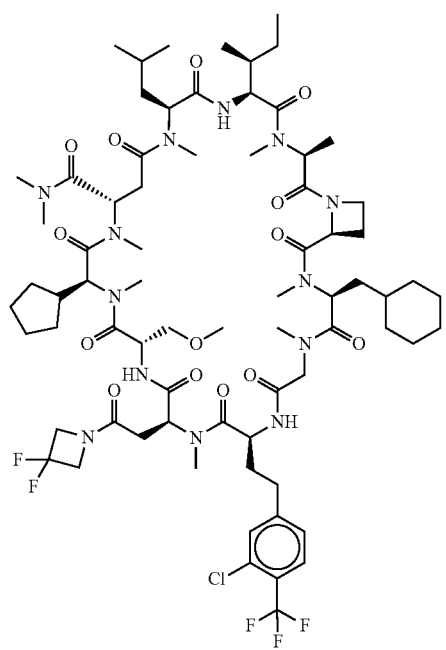 |

TABLE 24-continued
| Compound No. | Structural formula |
|---|---|
| 1109 | 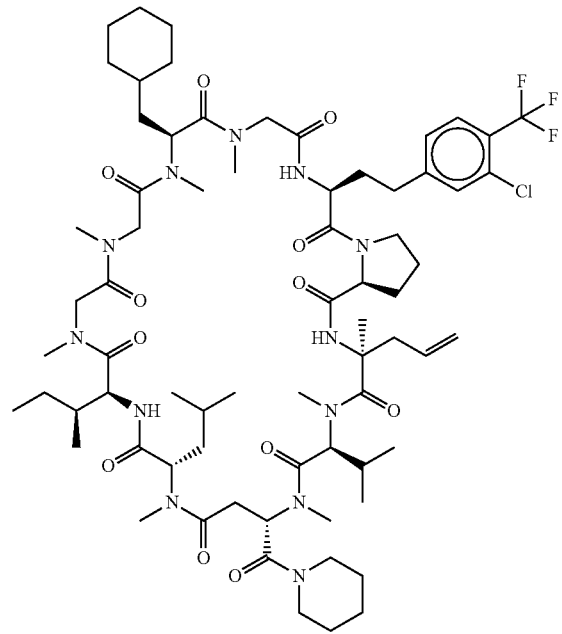 |
| 1110 | 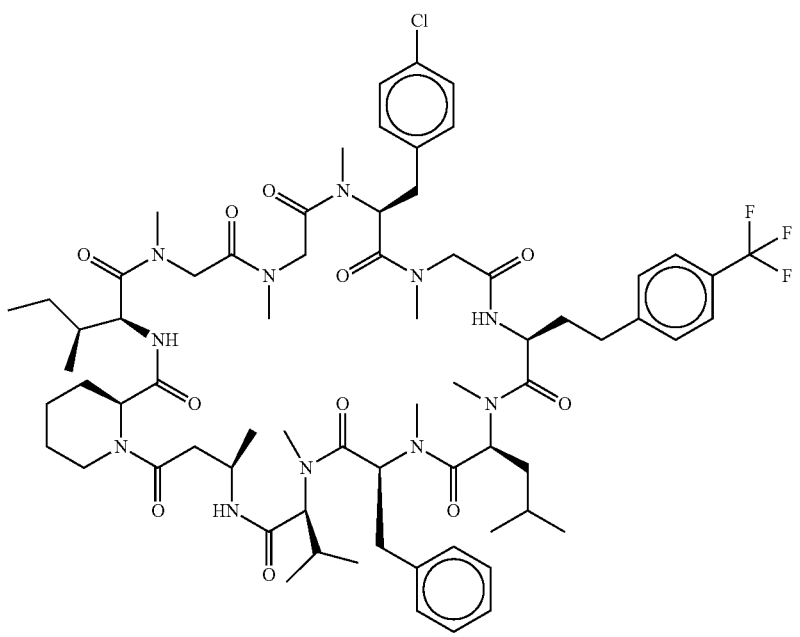 |

TABLE 24-continued
| Compound No. | Structural formula |
|---|---|
| 1111 | 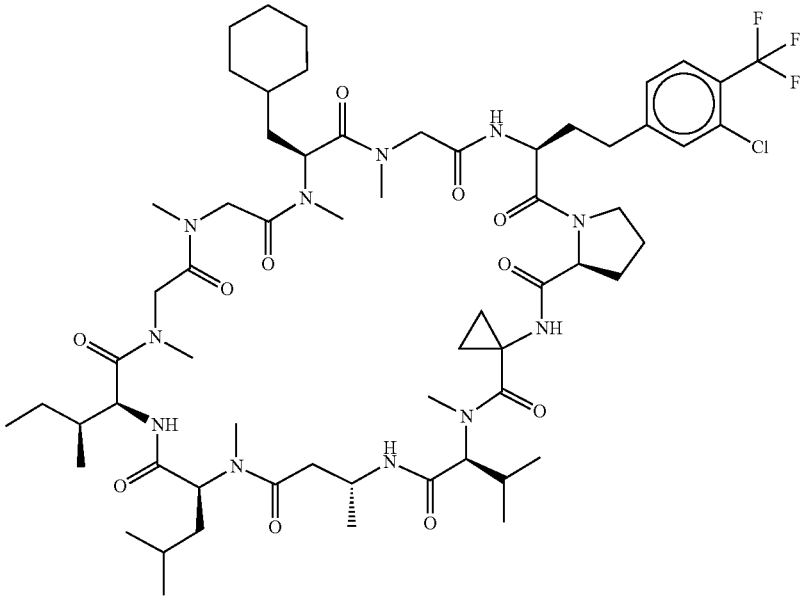 |
| 1112 | 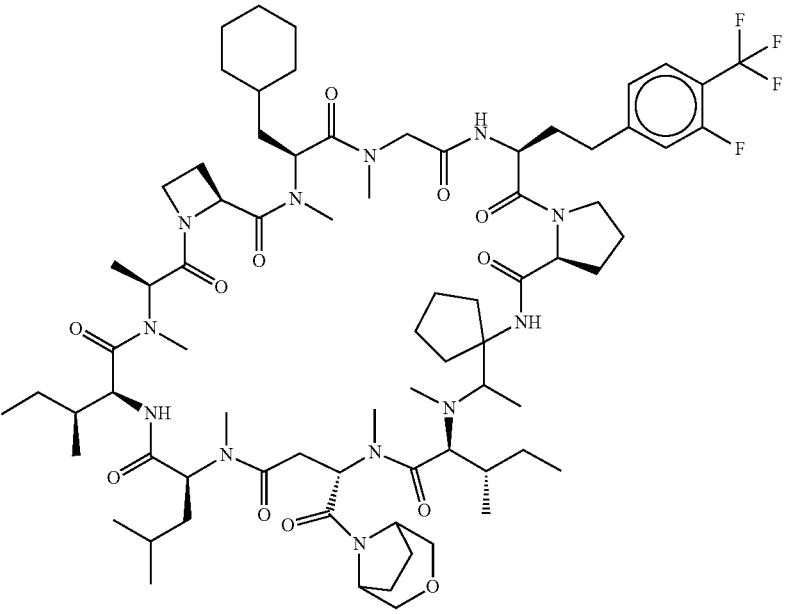 |

TABLE 24-continued
| Compound No. | Structural formula |
|---|---|
| 1113 | 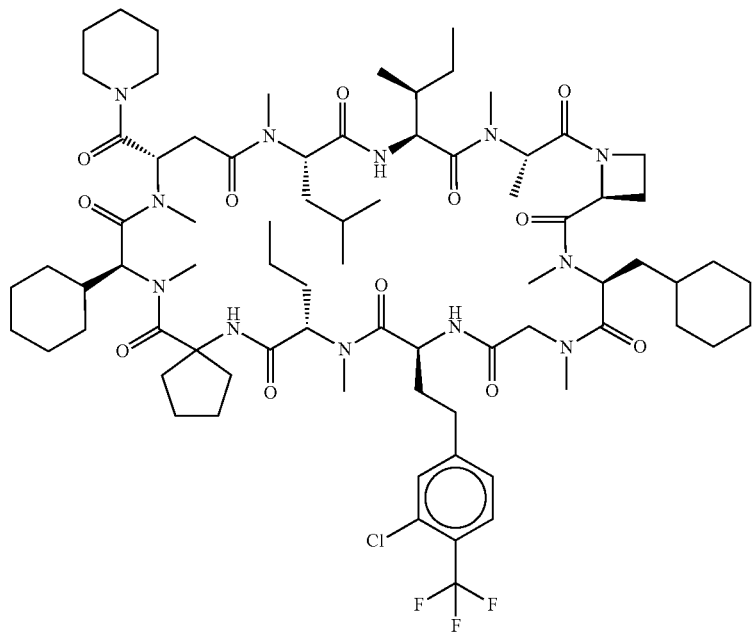 |
| 1114 | 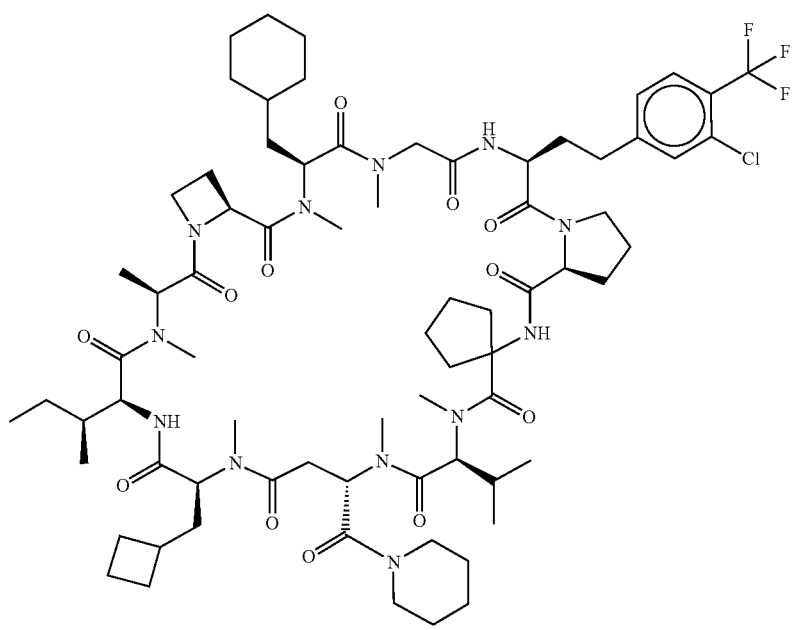 |

TABLE 24-continued
| Compound No. | Structural formula |
|---|---|
| 1115 | 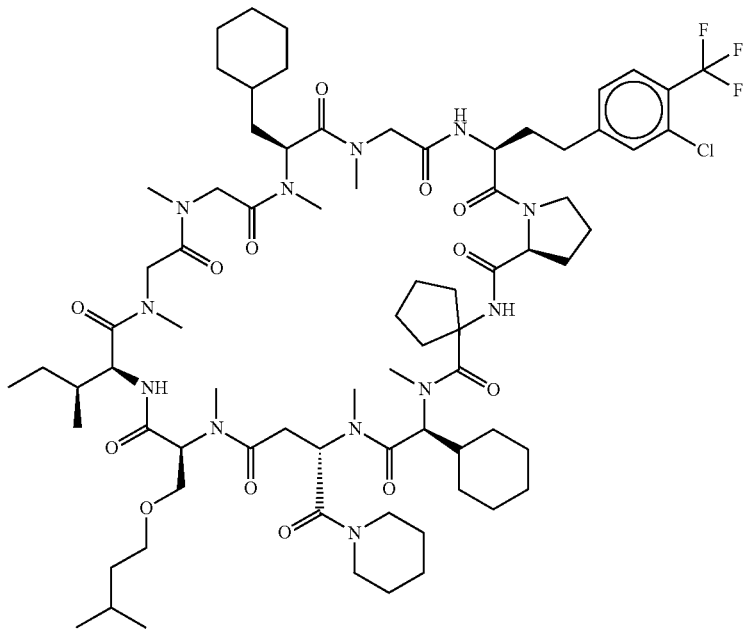 |
| 1116 | 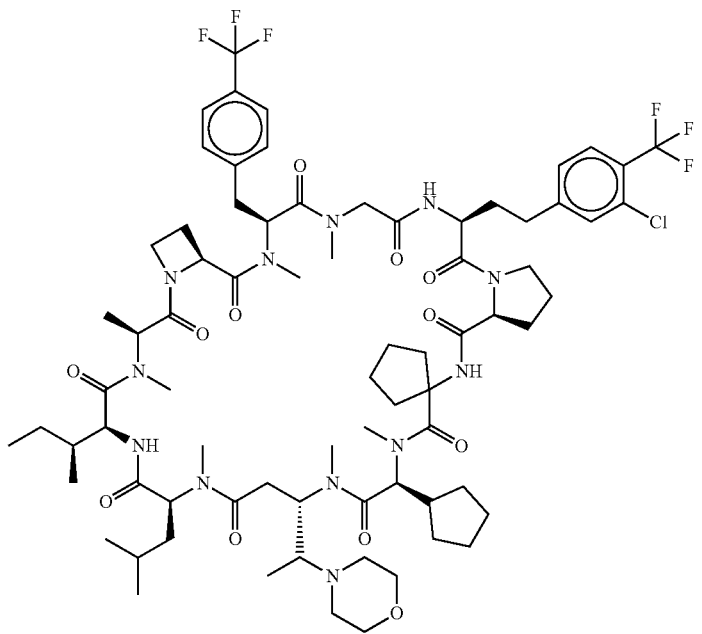 |

TABLE 24-continued
| Compound No. | Structural formula |
|---|---|
| 1117 | 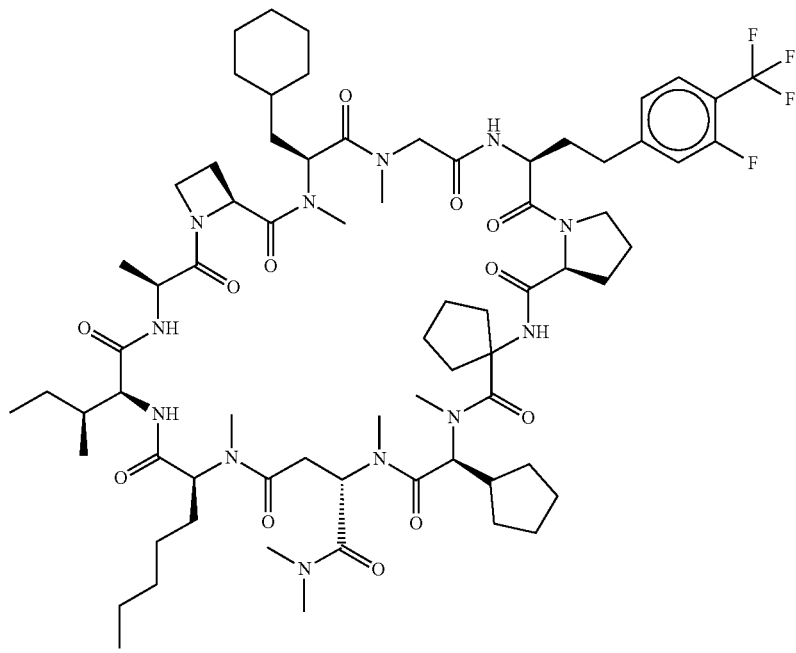 |
| 1118 | 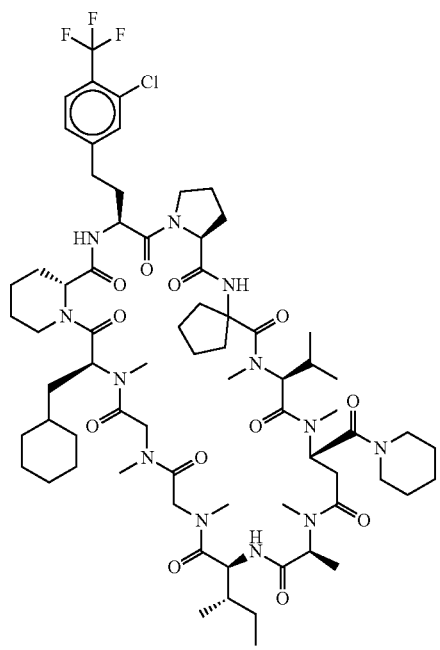 |

TABLE 24-continued
| Compound No. | Structural formula |
|---|---|
| 1119 | 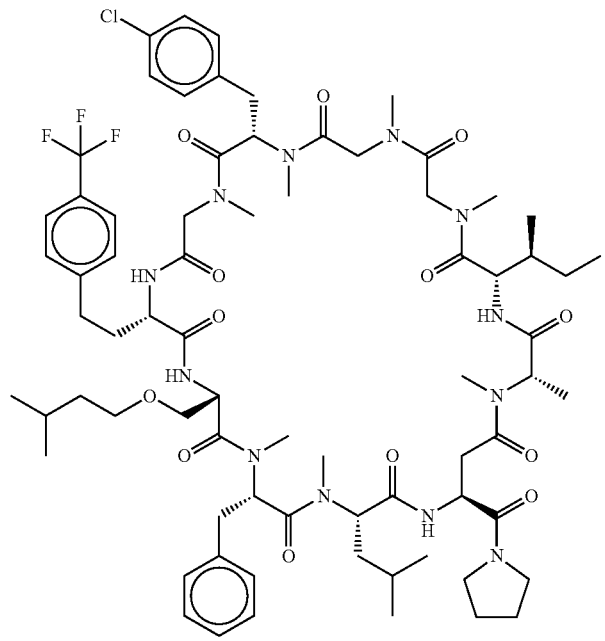 |
| 1120 | 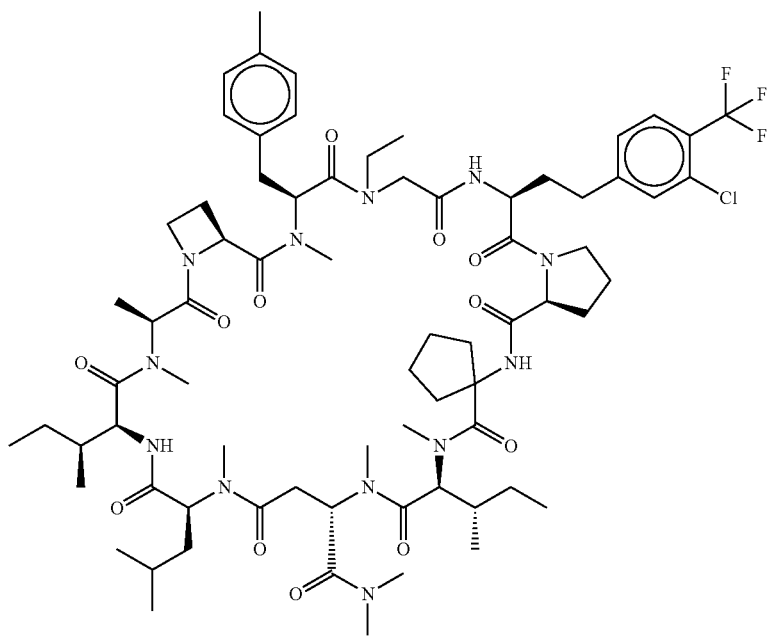 |

TABLE 24-continued
| Compound No. | Structural formula |
|---|---|
| 1121 | 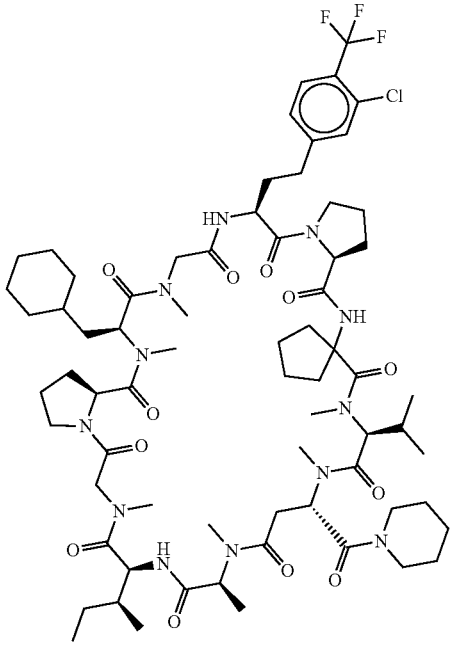 |
| 1122 | 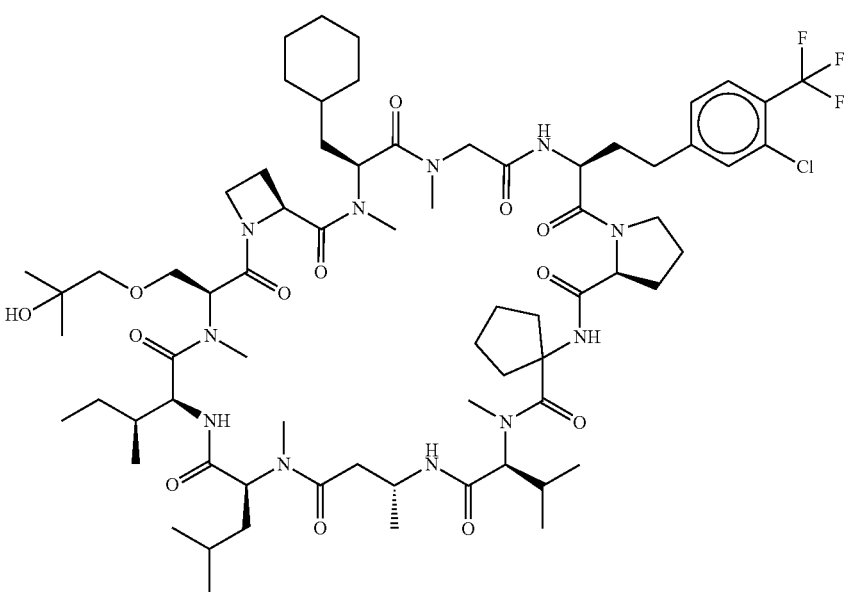 |

TABLE 24-continued
| Compound No. | Structural formula |
|---|---|
| 1123 | 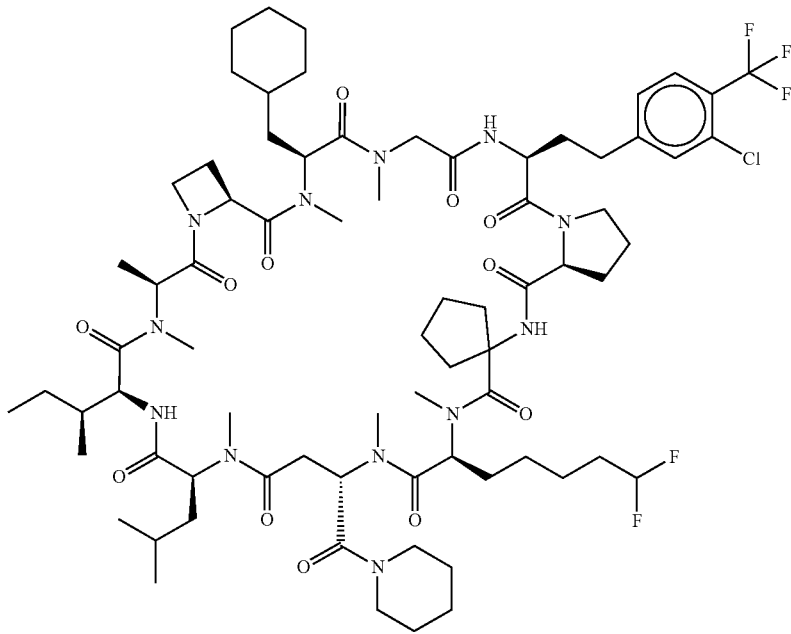 |
| 1124 | 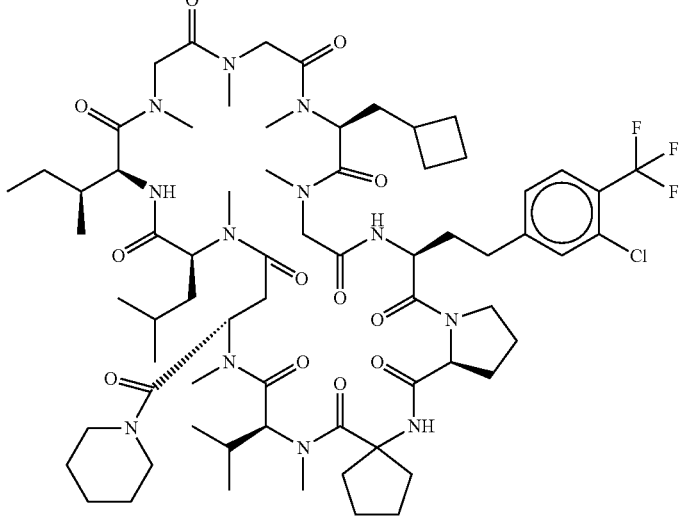 |

TABLE 24-continued
| Compound No. | Structural formula |
|---|---|
| 1125 | 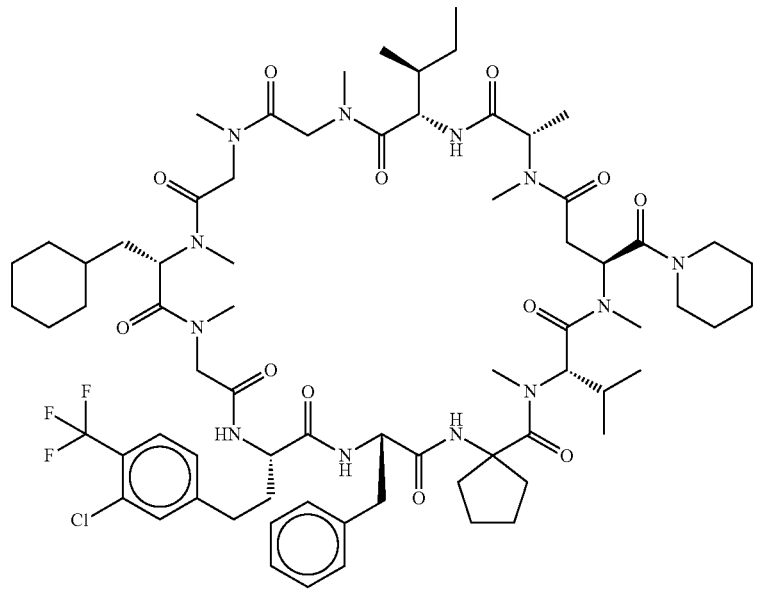 |
| 1126 | 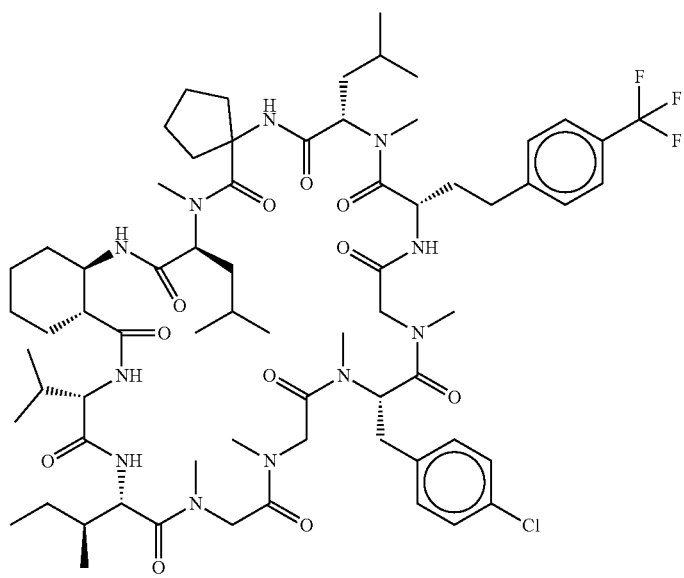 |

TABLE 24-continued
| Compound No. | Structural formula |
|---|---|
| 1127 | 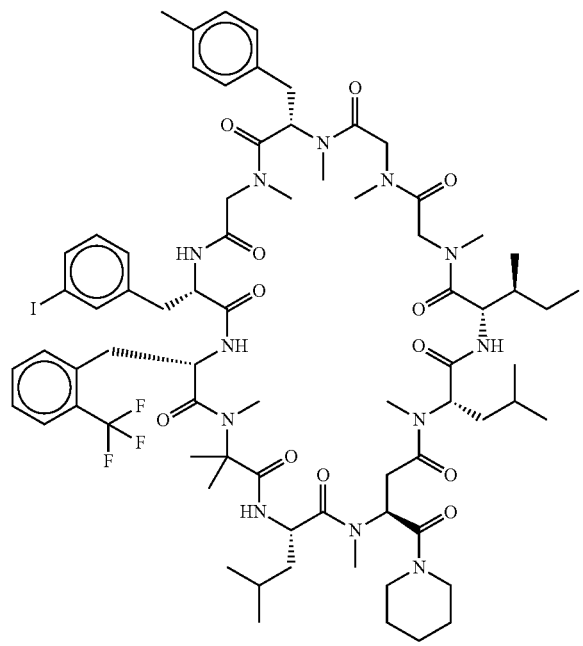 |
| 1128 | 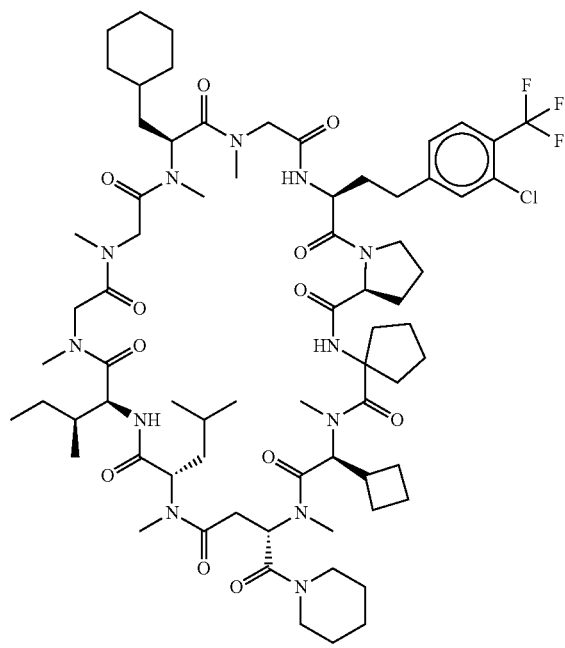 |

TABLE 24-continued
| Compound No. | Structural formula |
|---|---|
| 1129 | 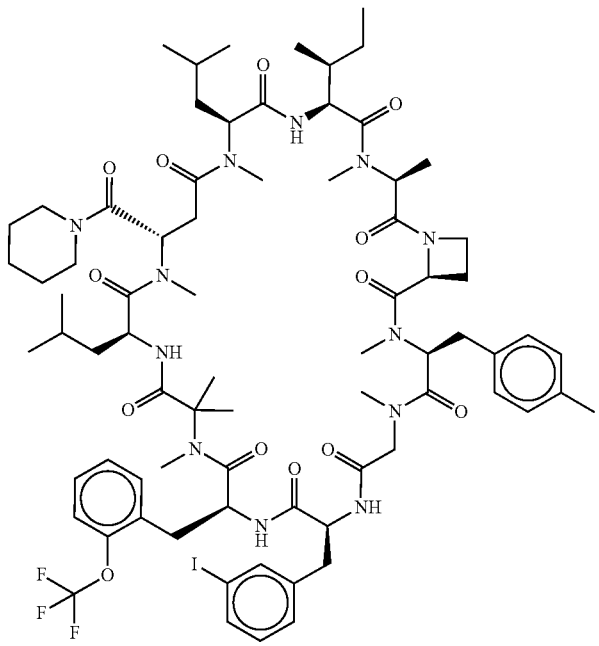 |
| 1130 | 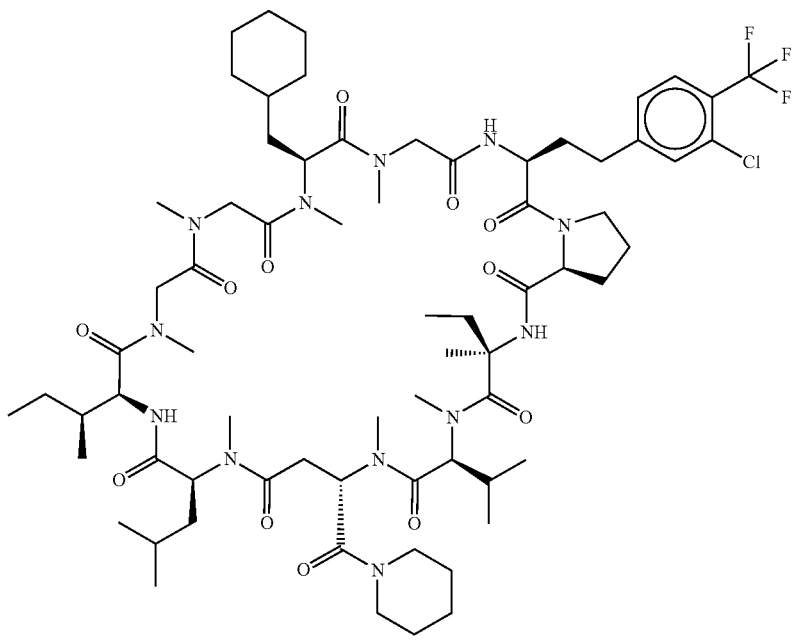 |

TABLE 24-continued
| Compound No. | Structural formula |
|---|---|
| 1131 | 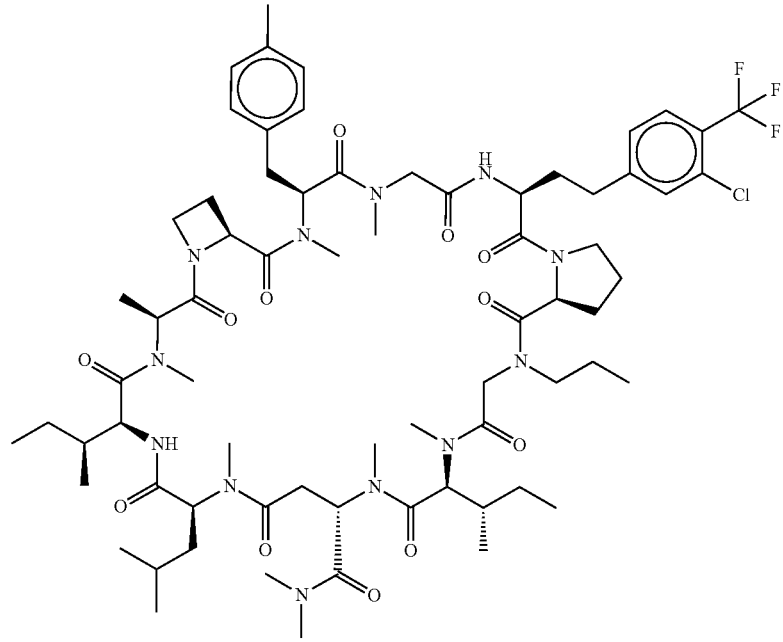 |
| 1132 | 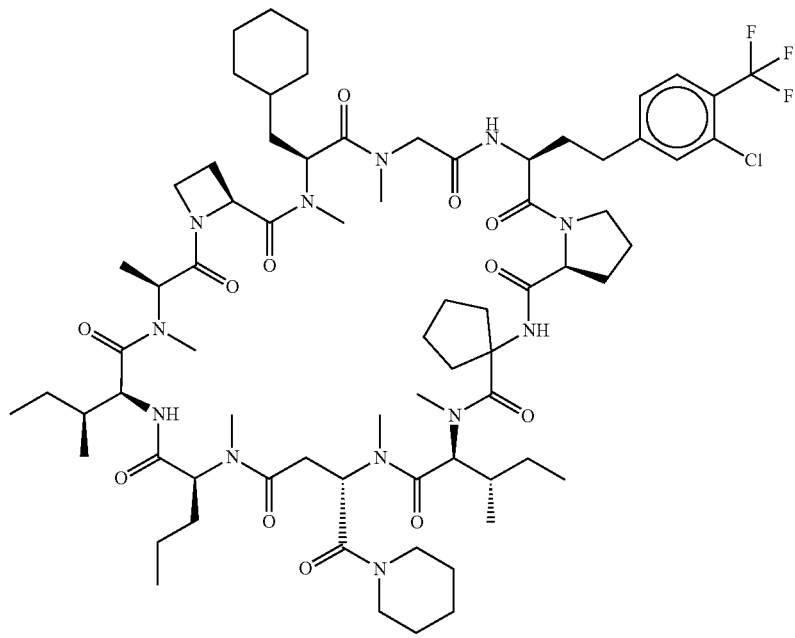 |

TABLE 24-continued
| Compound No. | Structural formula |
|---|---|
| 1133 | 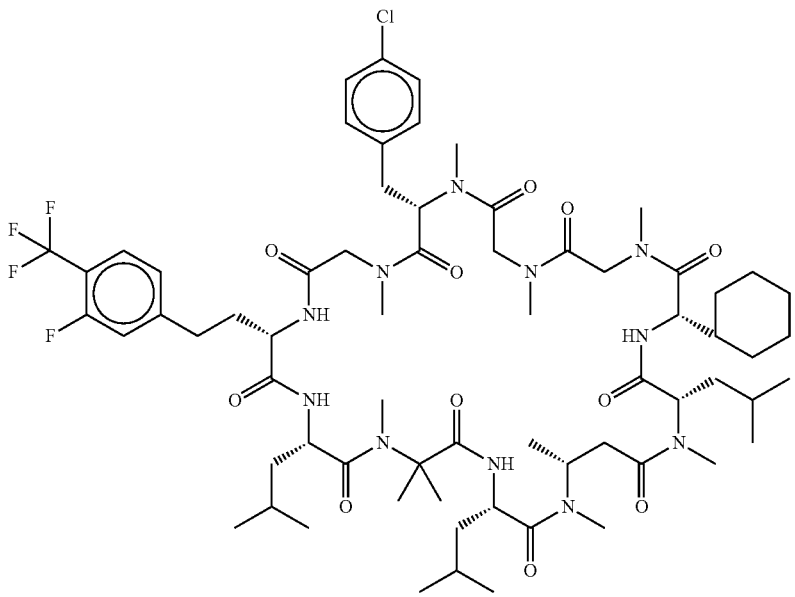 |
| 1134 | 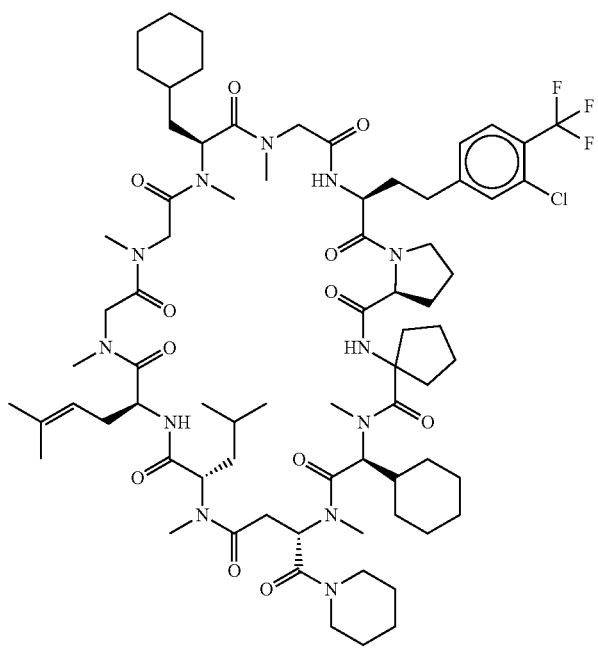 |

TABLE 24-continued
| Compound No. | Structural formula |
|---|---|
| 1135 | 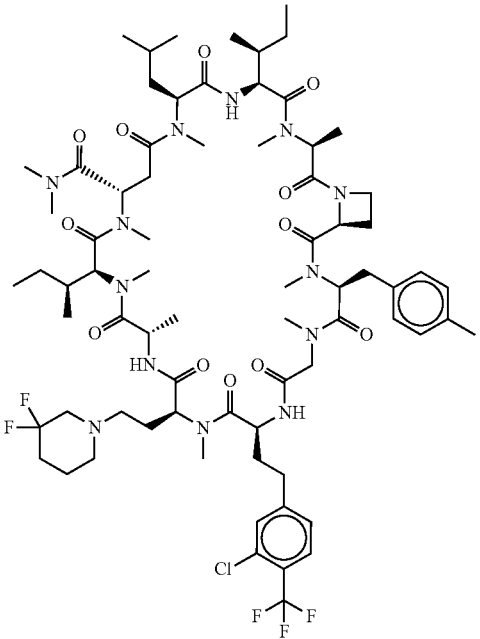 |
| 1136 | 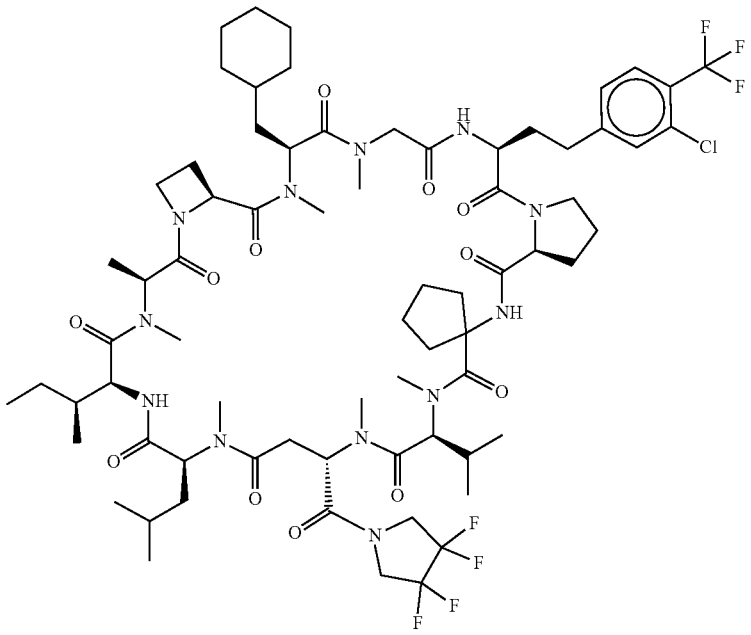 |

TABLE 24-continued
| Compound No. | Structural formula |
|---|---|
| 1137 | 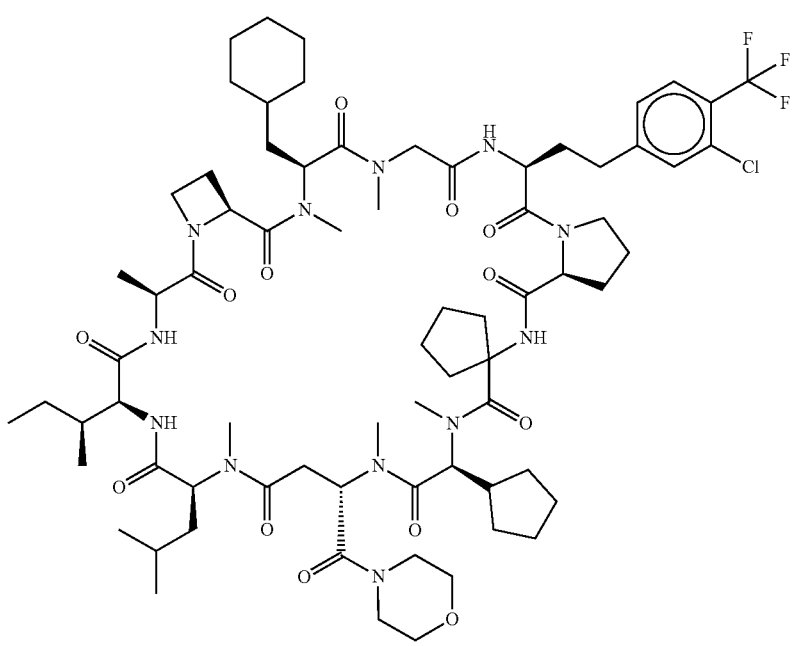 |
| 1138 | 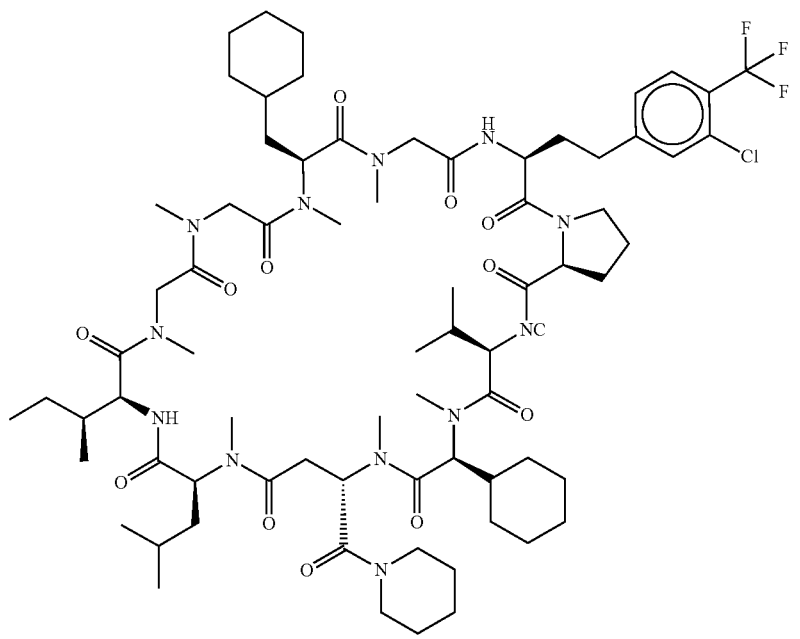 |

TABLE 24-continued
| Compound No. | Structural formula |
|---|---|
| 1139 | 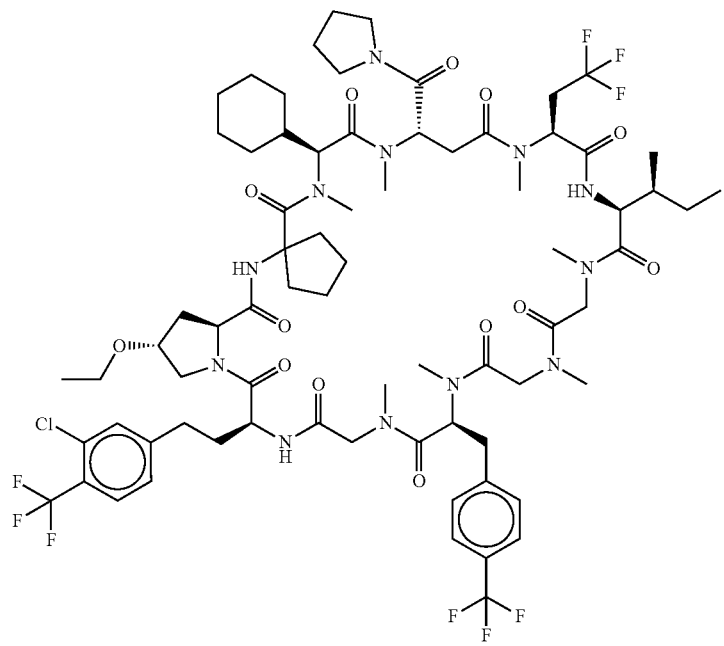 |
| 1140 | 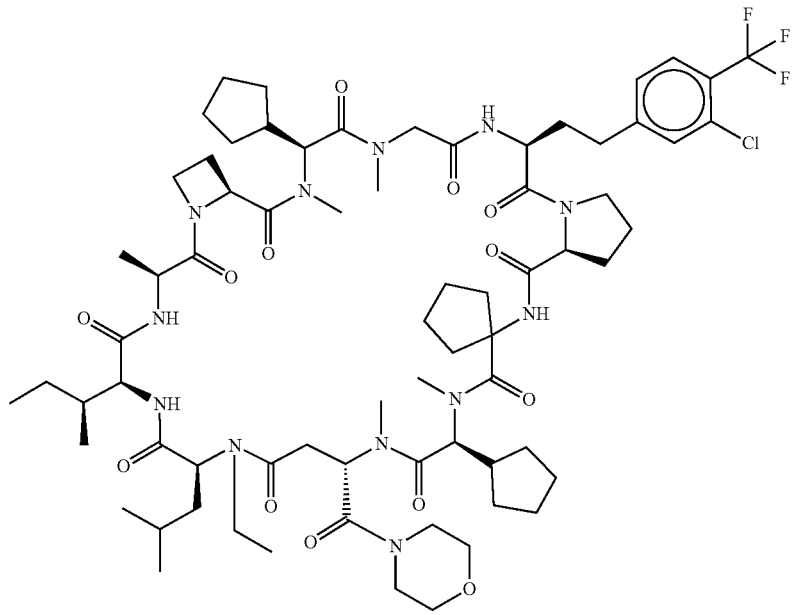 |

TABLE 24-continued

| Compound No. | Structural formula |
|---|---|
| 1141 | |
| 1142 | |

TABLE 24-continued
| Compound No. | Structural formula |
|---|---|
| 1143 | 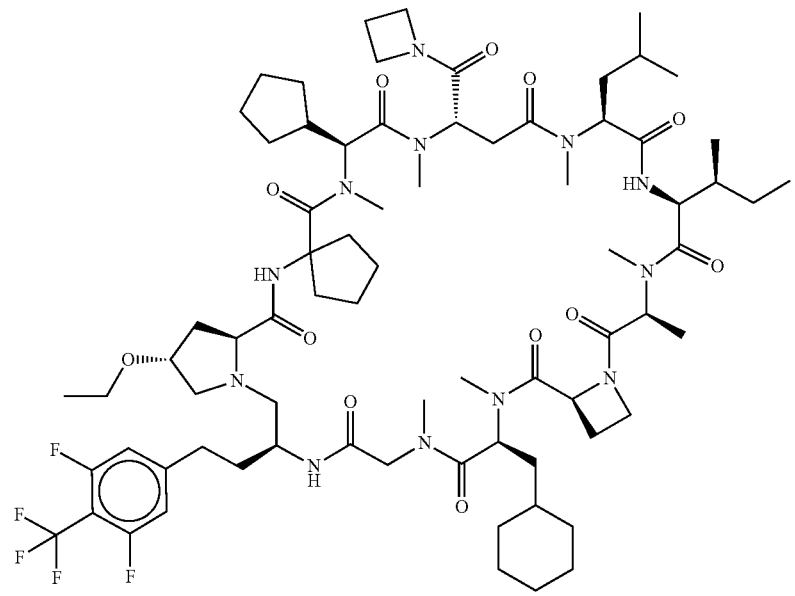 |
| 1144 | 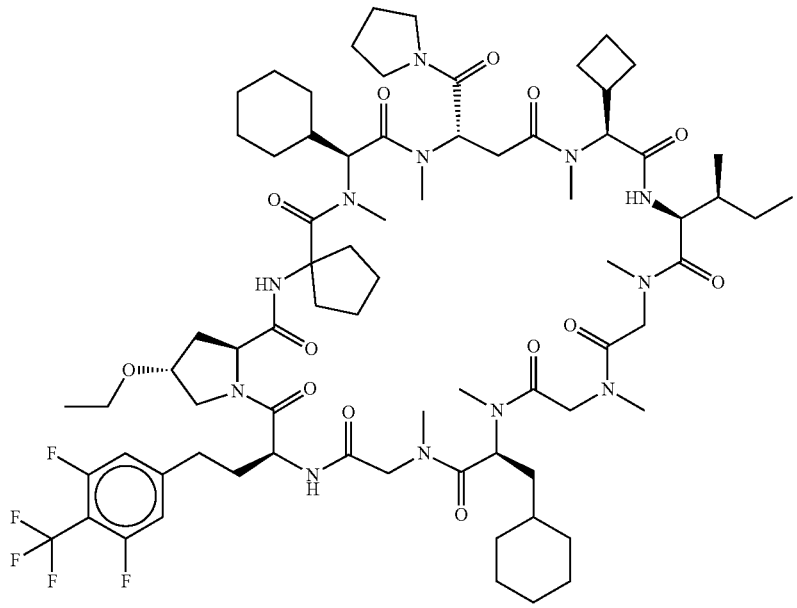 |

TABLE 24-continued
| Compound No. | Structural formula |
|---|---|
| 1145 | 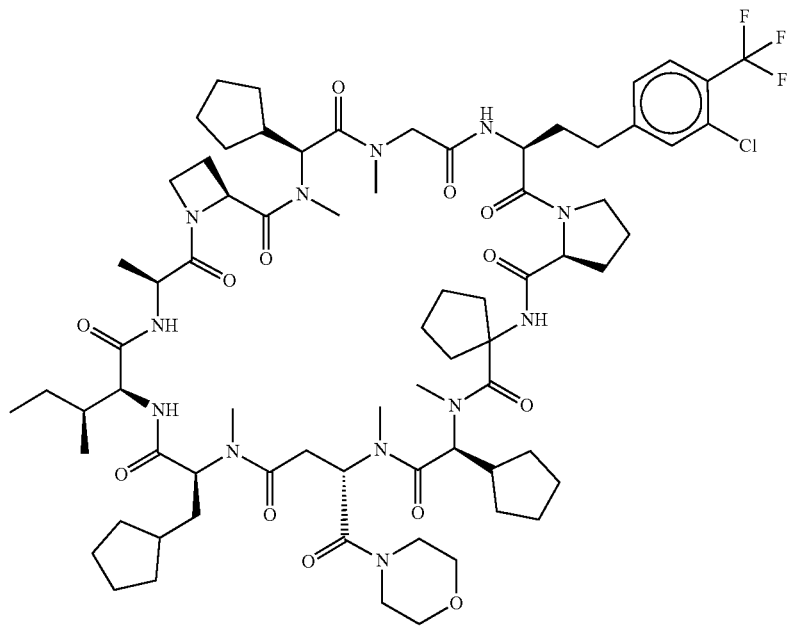 |
| 1146 | 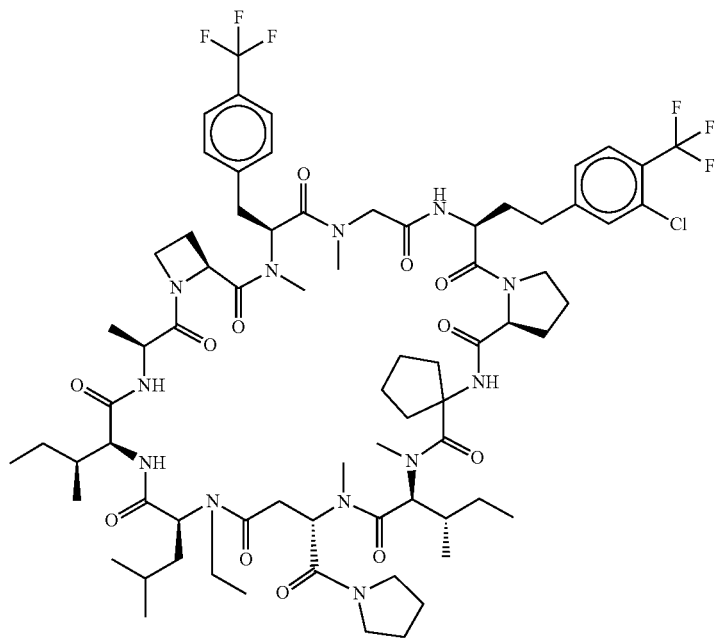 |

TABLE 24-continued

| Compound No. | Structural formula |
|---|---|
| 1148 | |
| 1149 | |

TABLE 24-continued
| Compound No. | Structural formula |
|---|---|
| 1150 | 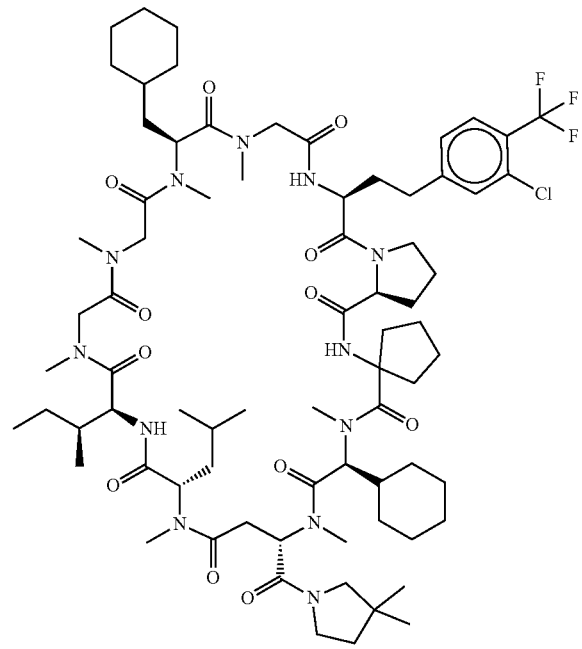 |
| 1151 | 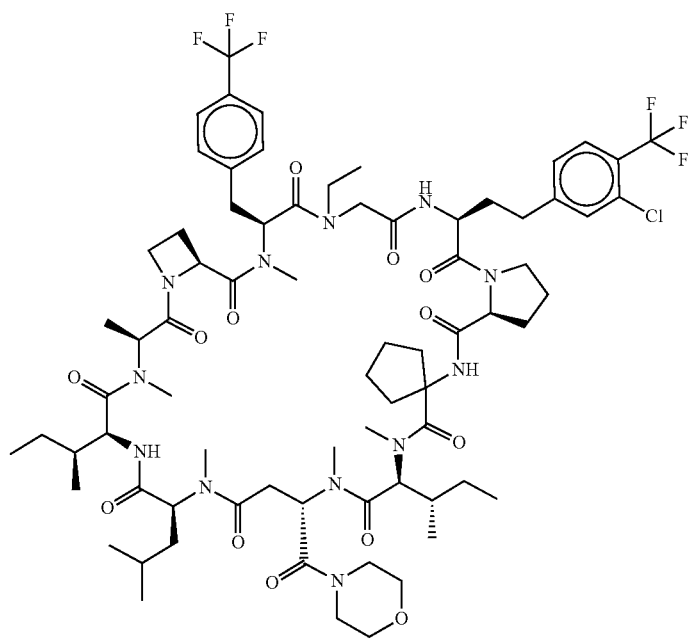 |

TABLE 24-continued
| Compound No. | Structural formula |
|---|---|
| 1152 | 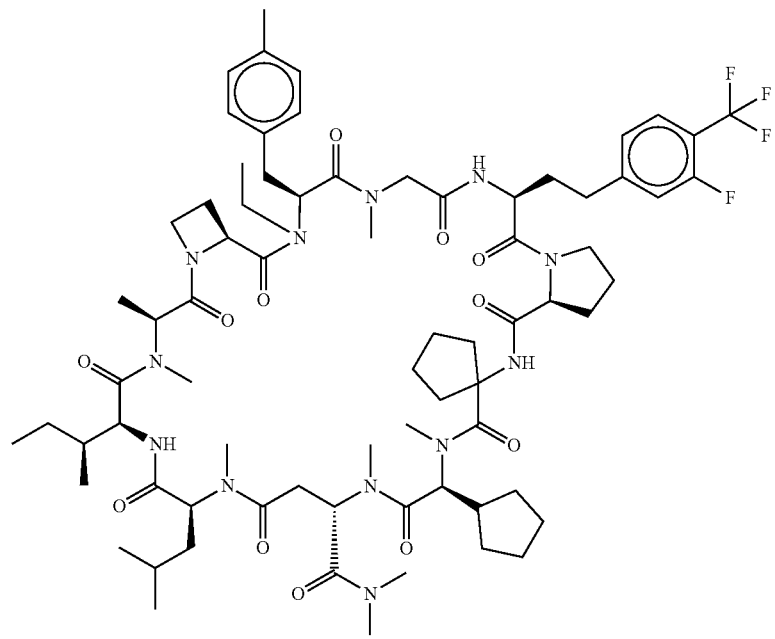 |
| 1153 | 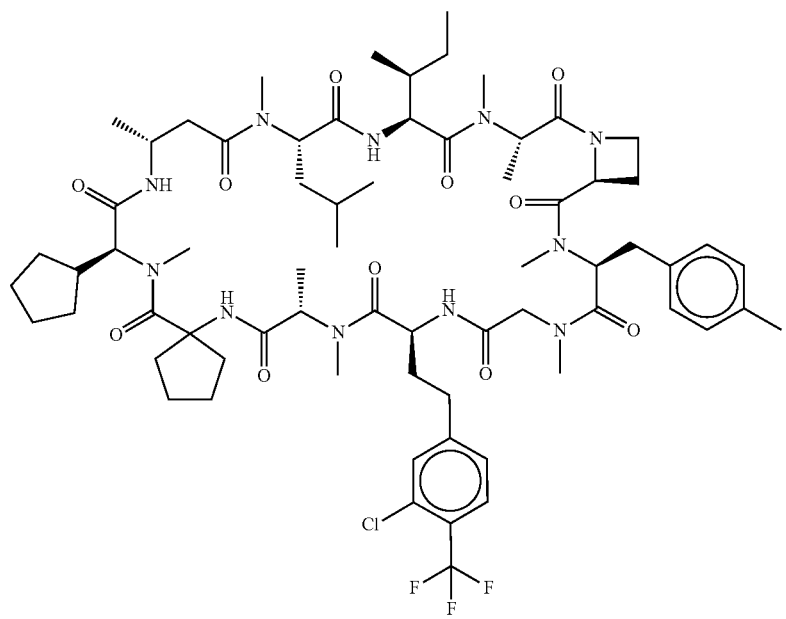 |

TABLE 24-continued
| Compound No. | Structural formula |
|---|---|
| 1154 | 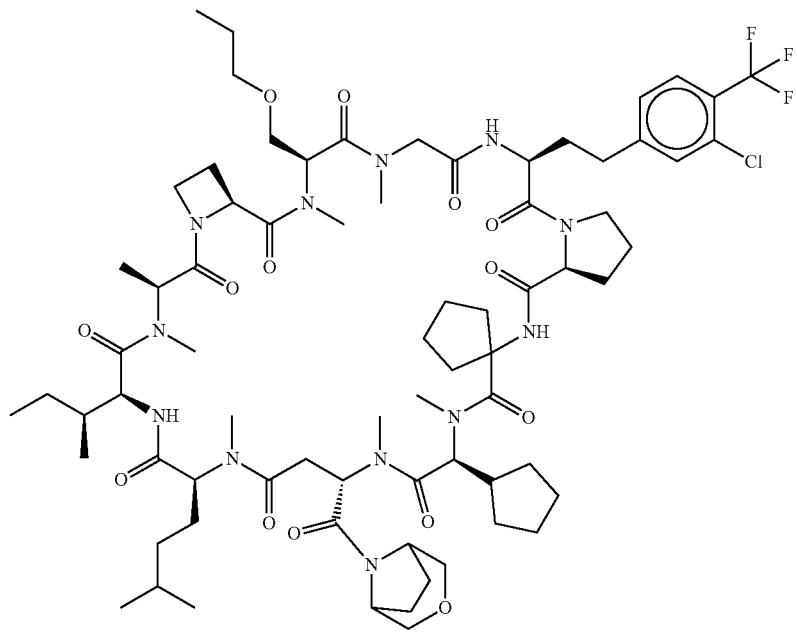 |
| 1155 | 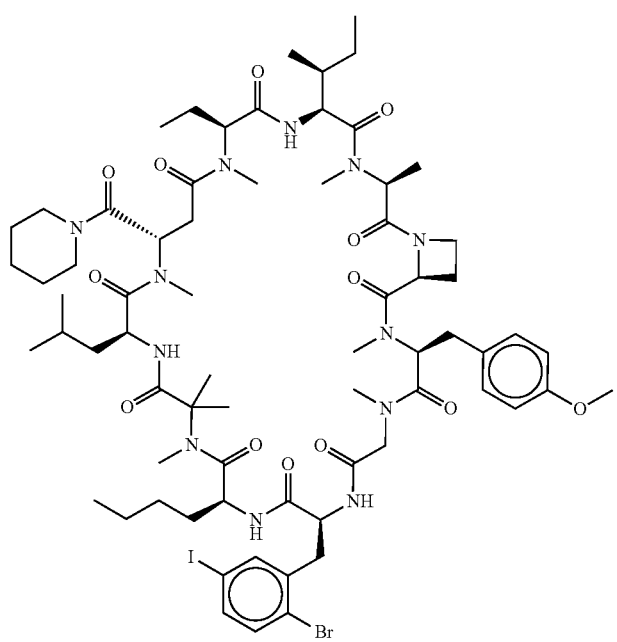 |

TABLE 24-continued
| Compound No. | Structural formula |
|---|---|
| 1156 | 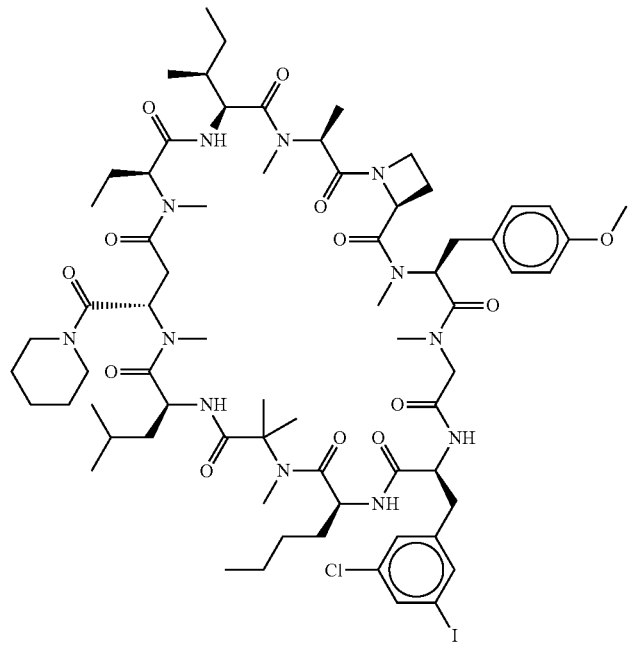 |
| 1157 | 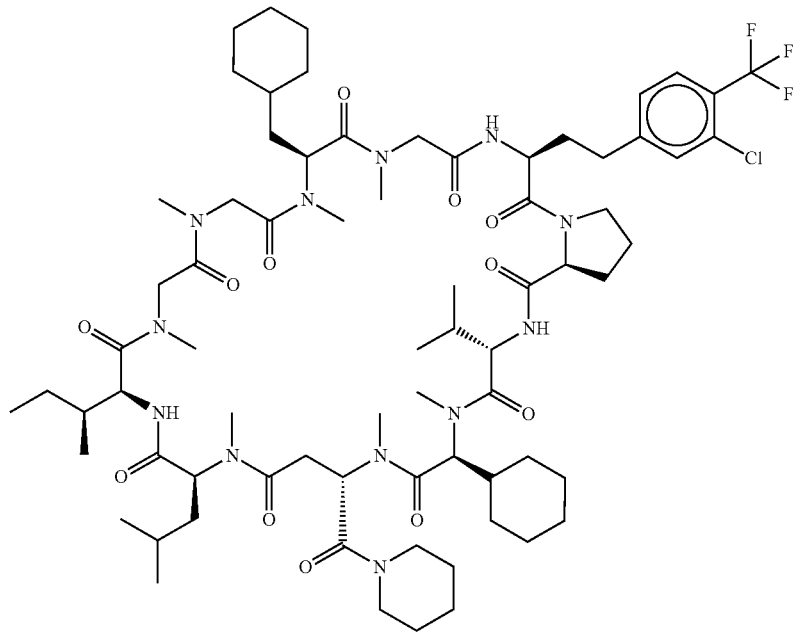 |

TABLE 24-continued
| Compound No. | Structural formula |
|---|---|
| 1158 | 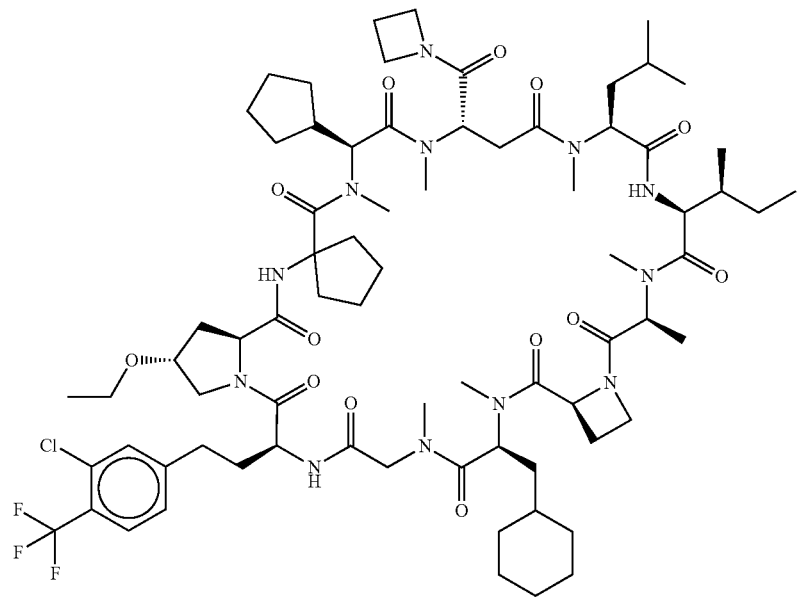 |
| 1159 | 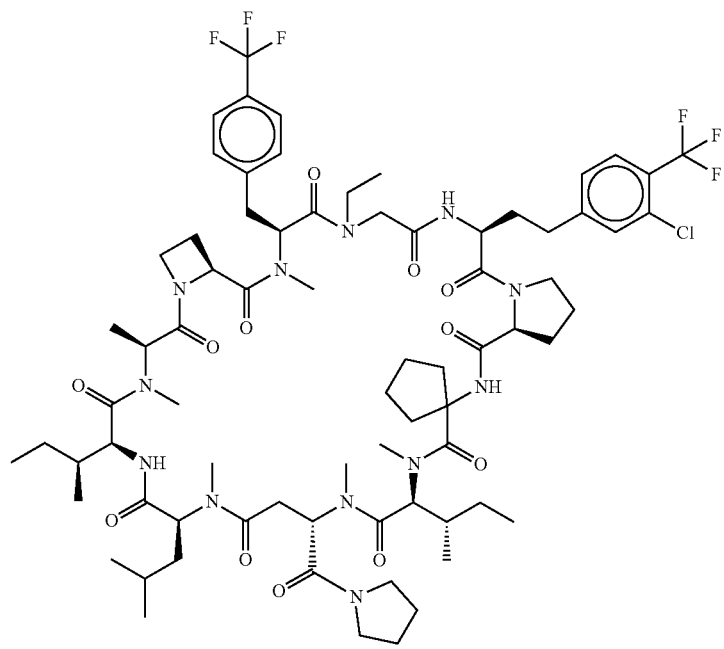 |

TABLE 24-continued
| Compound No. | Structural formula |
|---|---|
| 1160 | 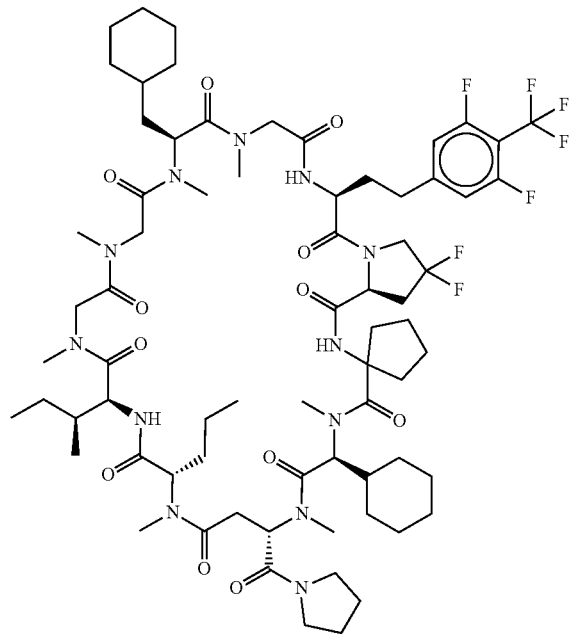 |
| 1161 | 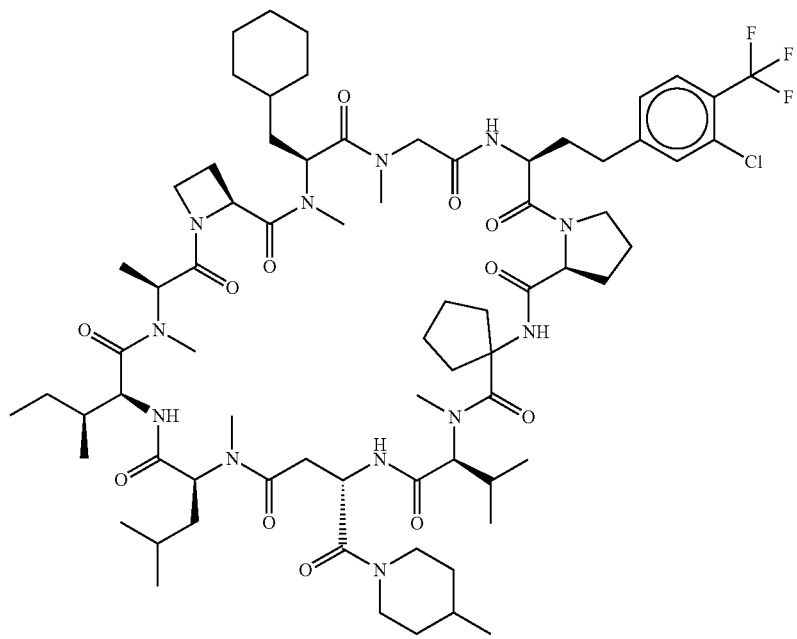 |

TABLE 24-continued
| Compound No. | Structural formula |
|---|---|
| 1162 | 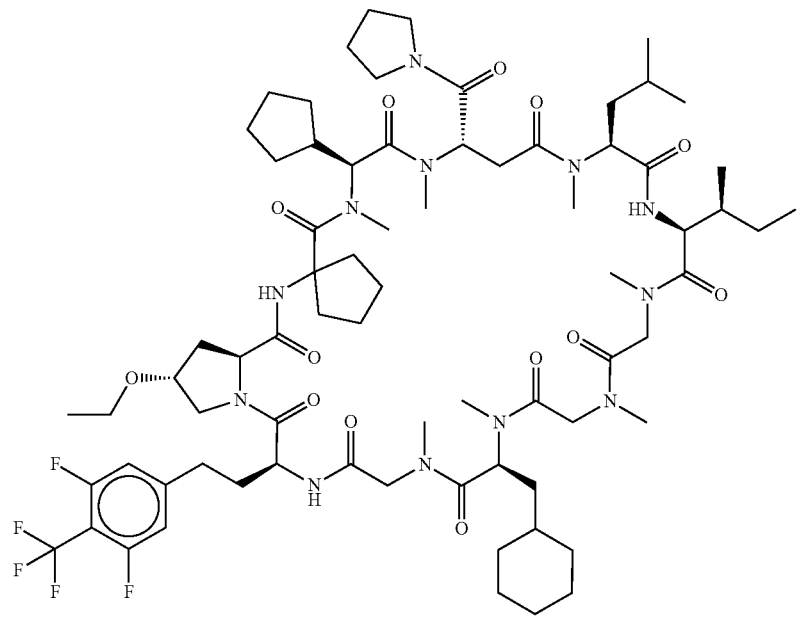 |
| 1163 | 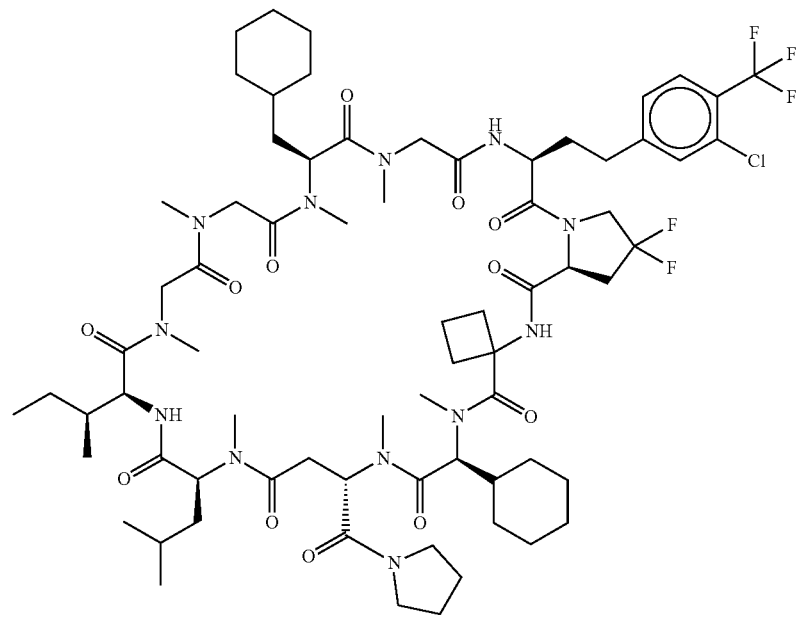 |

TABLE 24-continued
| Compound No. | Structural formula |
|---|---|
| 1164 | 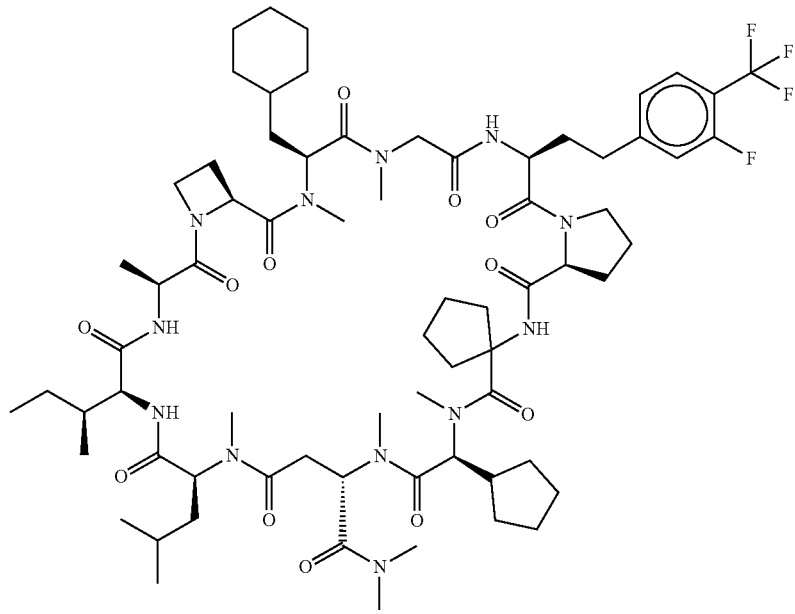 |
| 1165 | 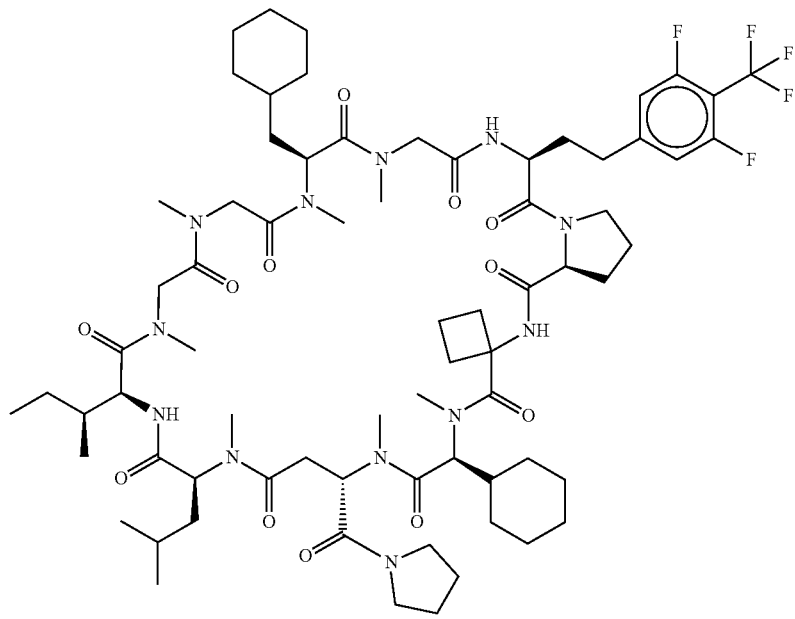 |

TABLE 24-continued
| Compound No. | Structural formula |
|---|---|
| 1166 | 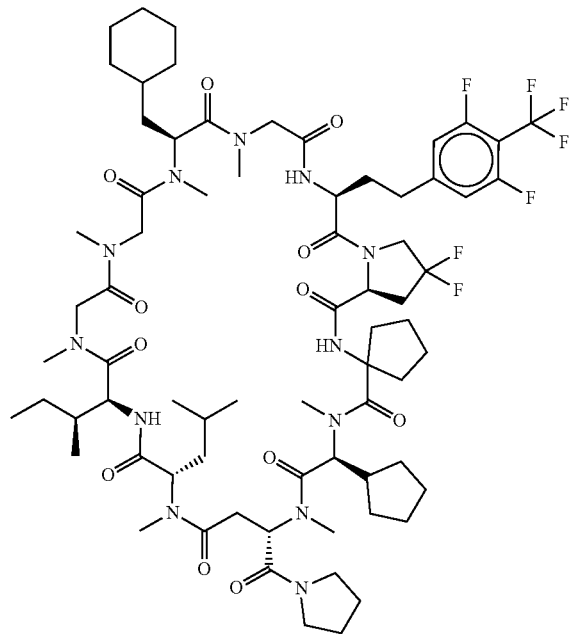 |
| 1167 | 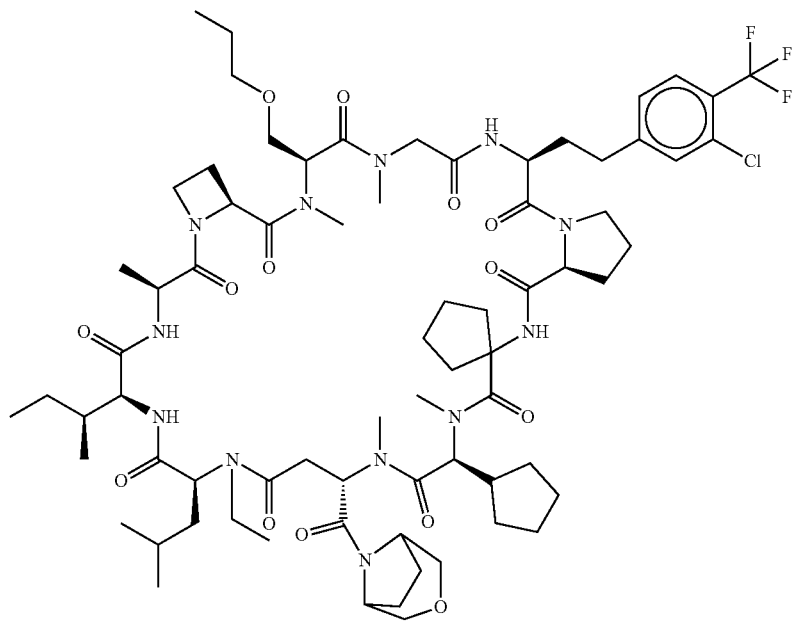 |

TABLE 24-continued
| Compound No. | Structural formula |
|---|---|
| 1168 | 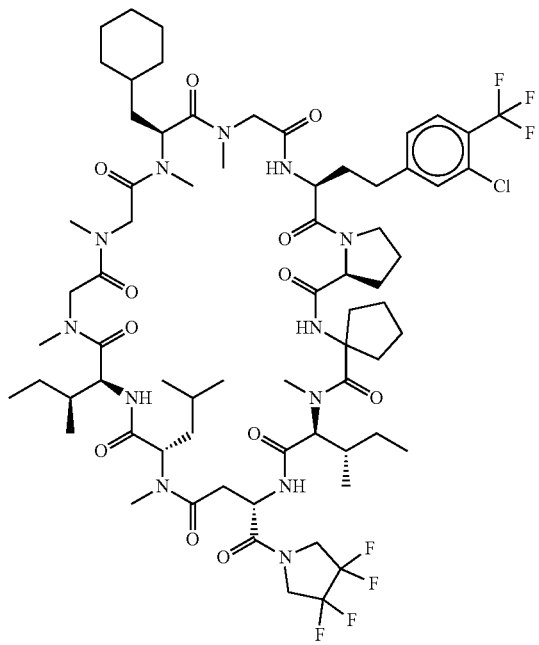 |
| 1169 | 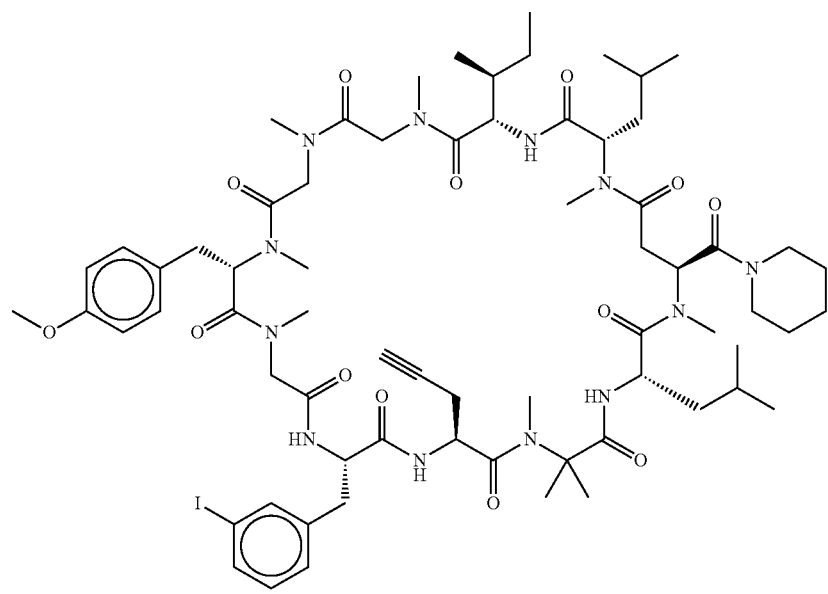 |

TABLE 24-continued
| Compound No. | Structural formula |
|---|---|
| 1170 | 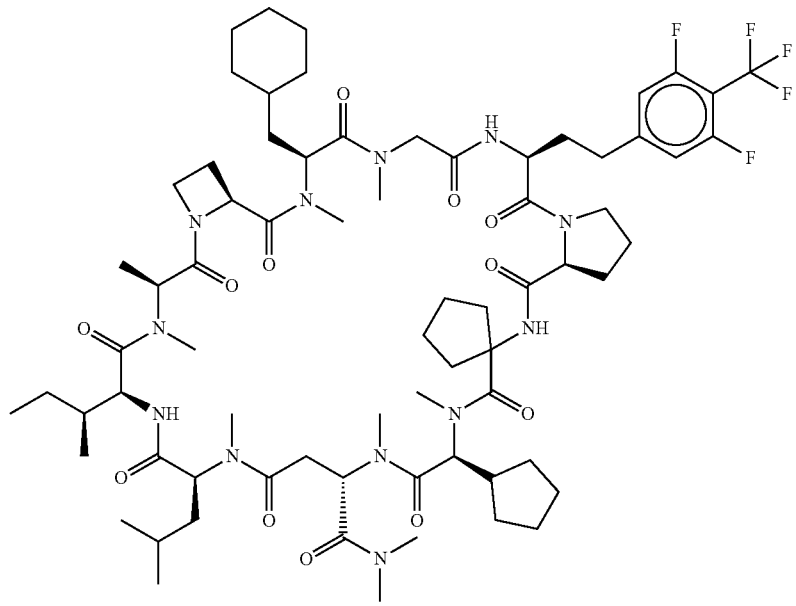 |
| 1171 | 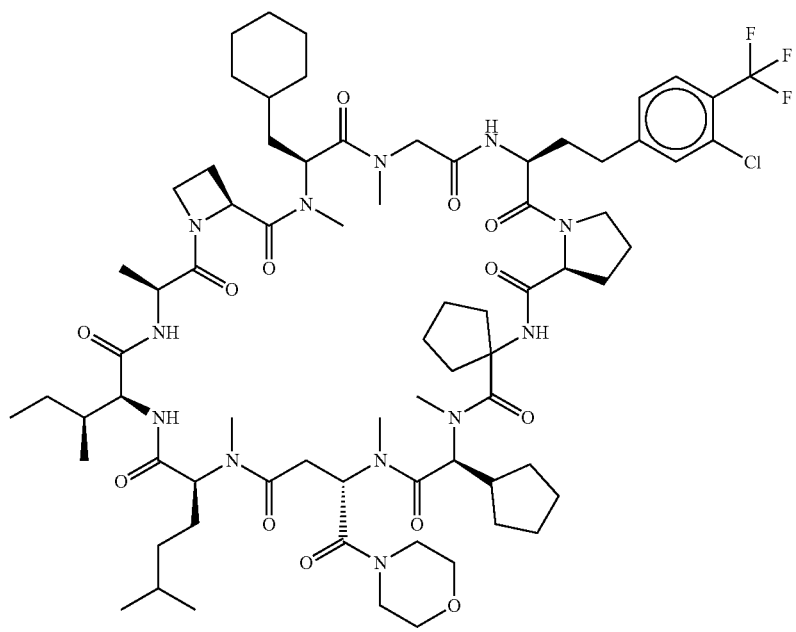 |

TABLE 24-continued
| Compound No. | Structural formula |
|---|---|
| 1172 | 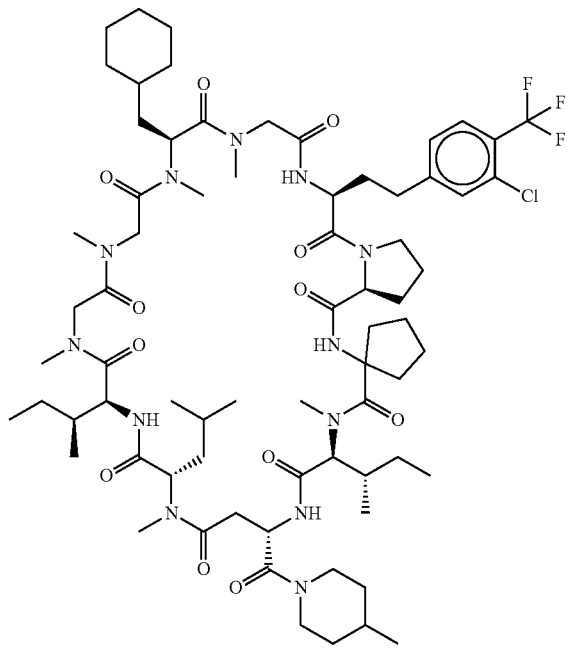 |
| 1173 | 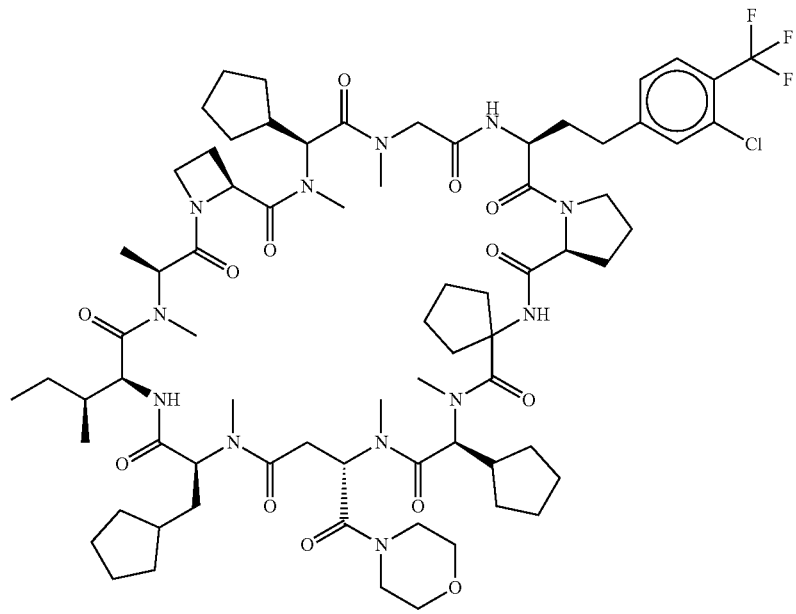 |

TABLE 24-continued
| Compound No. | Structural formula |
|---|---|
| 1174 | 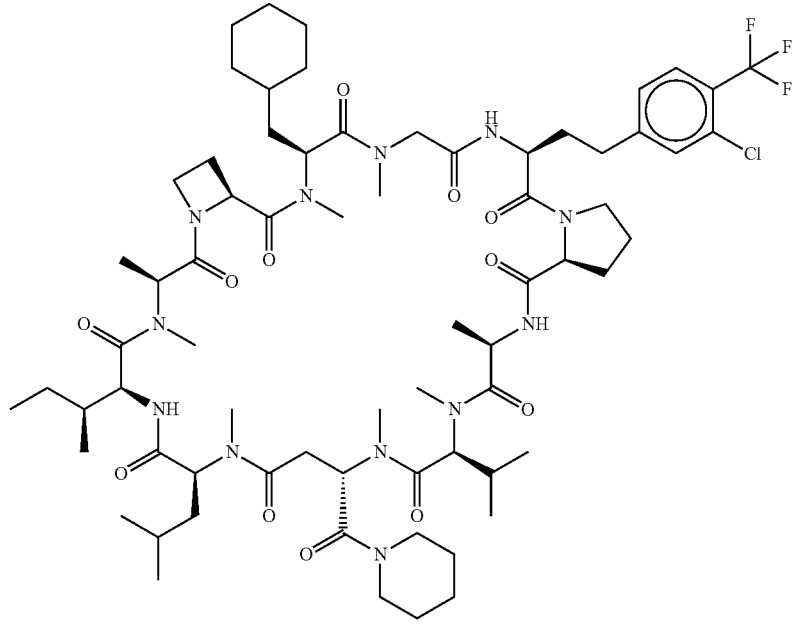 |
| 1175 | 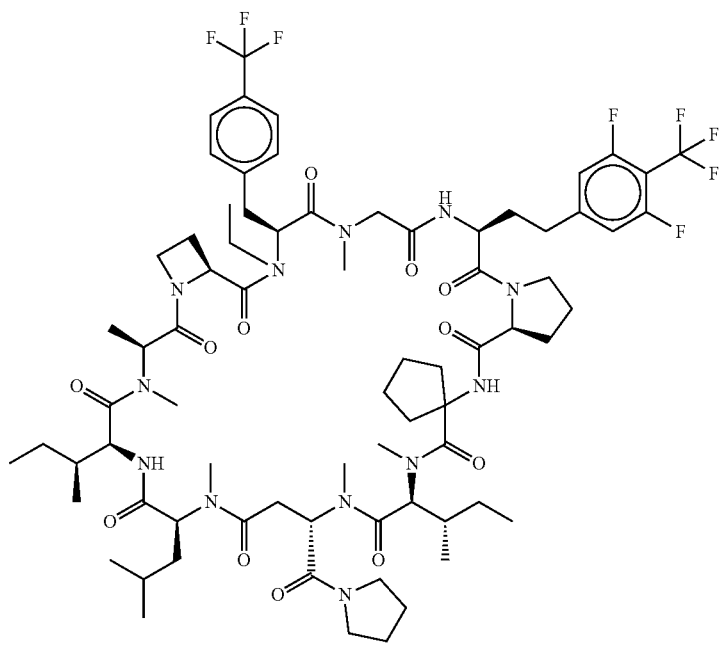 |

TABLE 24-continued
| Compound No. | Structural formula |
| --- | --- |
| 1176 | 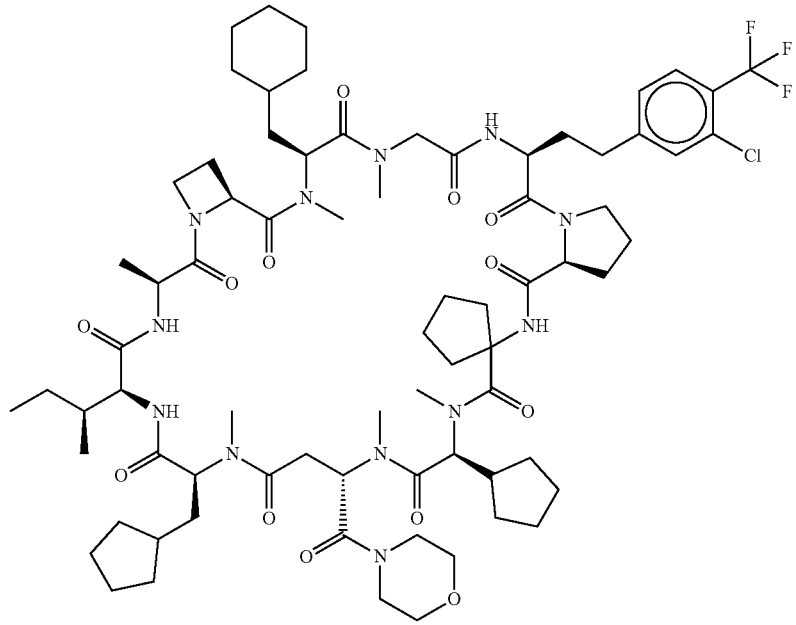 |
| 1177 | 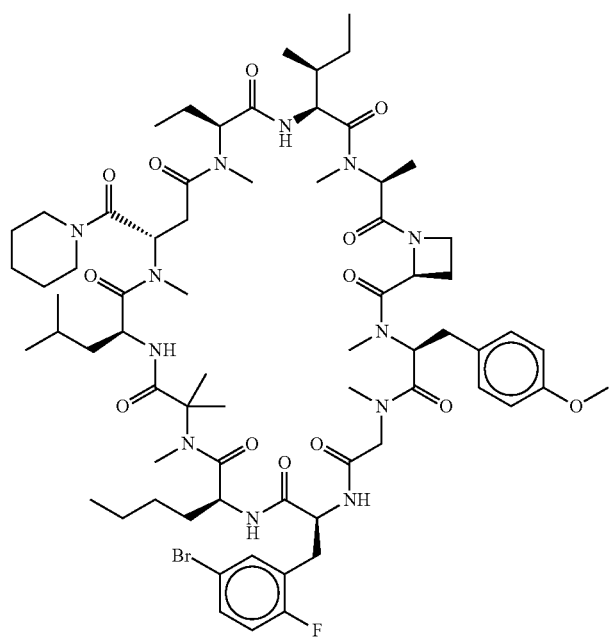 |

TABLE 24-continued
| Compound No. | Structural formula |
|---|---|
| 1178 | 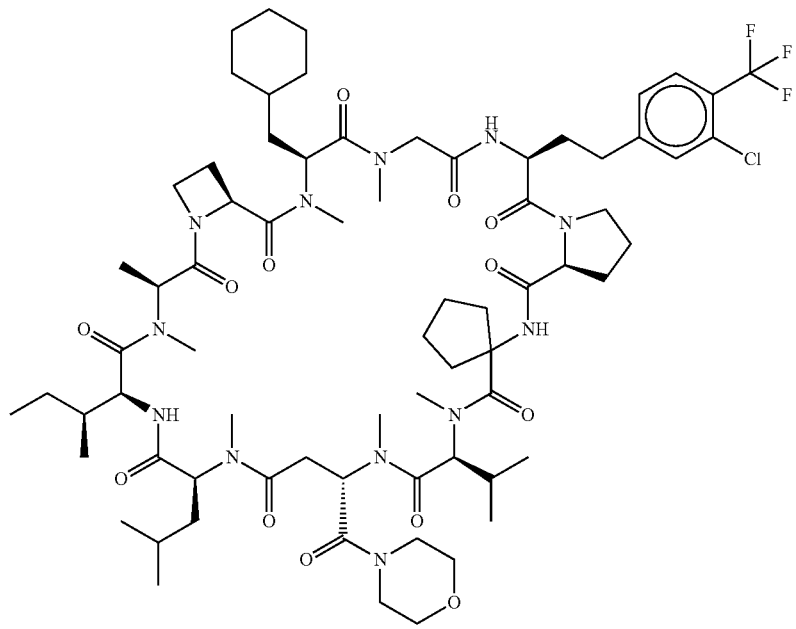 |
| 1179 | 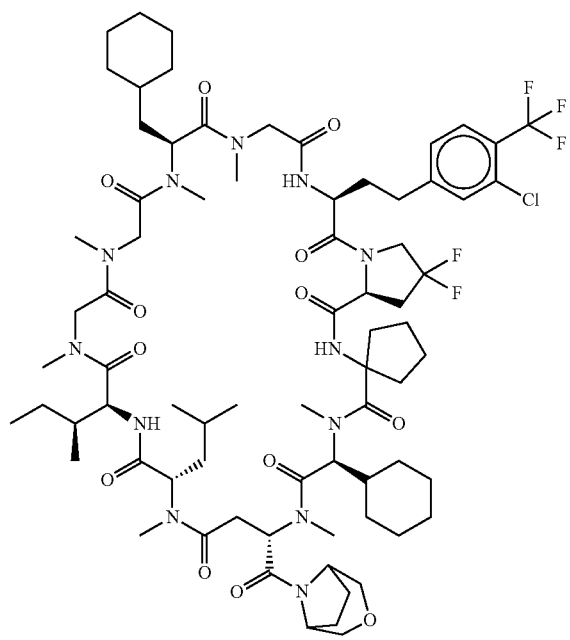 |

TABLE 24-continued
| Compound No. | Structural formula |
|---|---|
| 1180 | 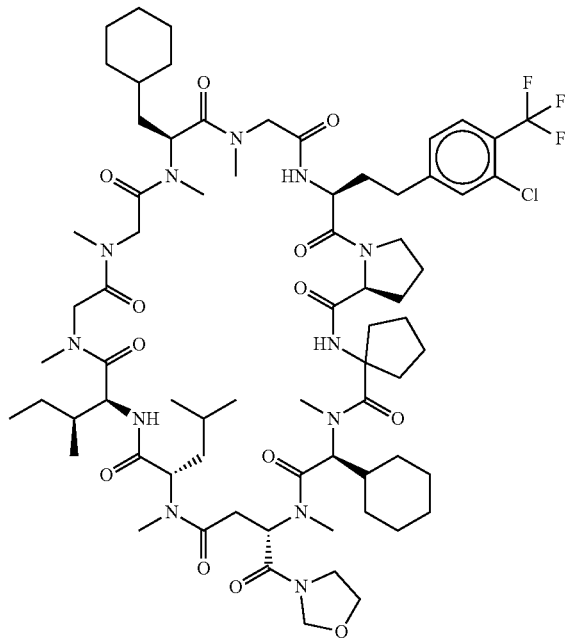 |
| 1181 | 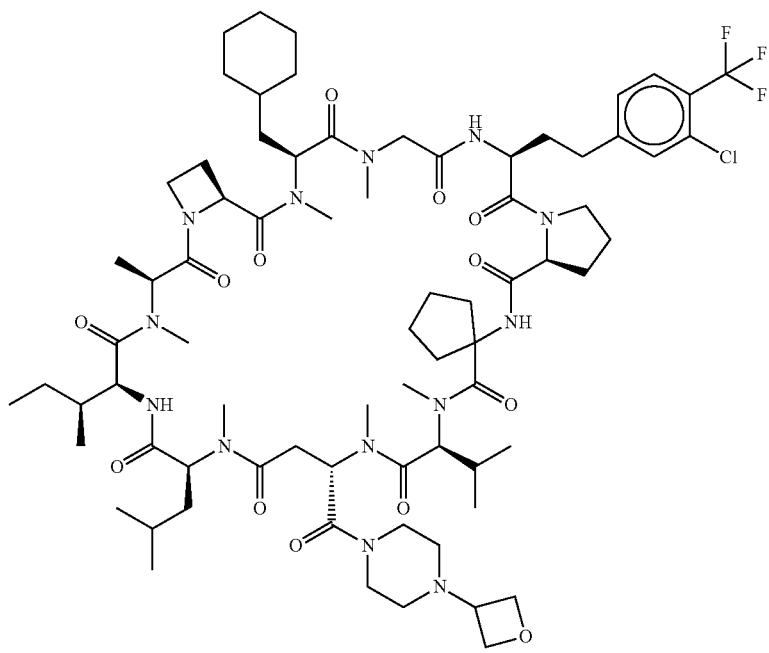 |

TABLE 24-continued
| Compound No. | Structural formula |
|---|---|
| 1182 | 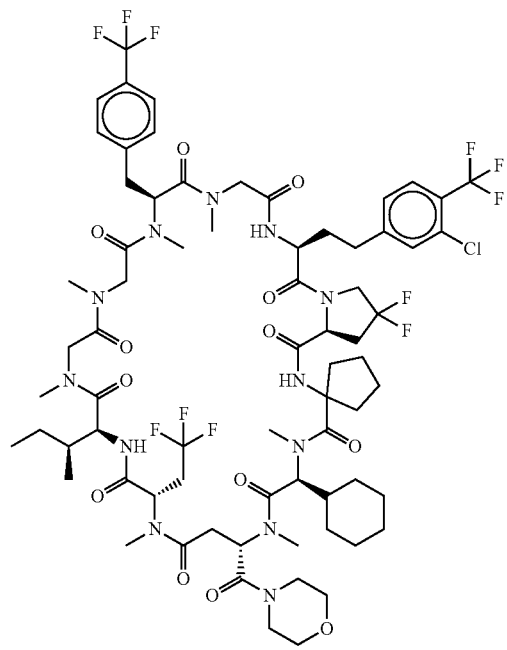 |
| 1183 | 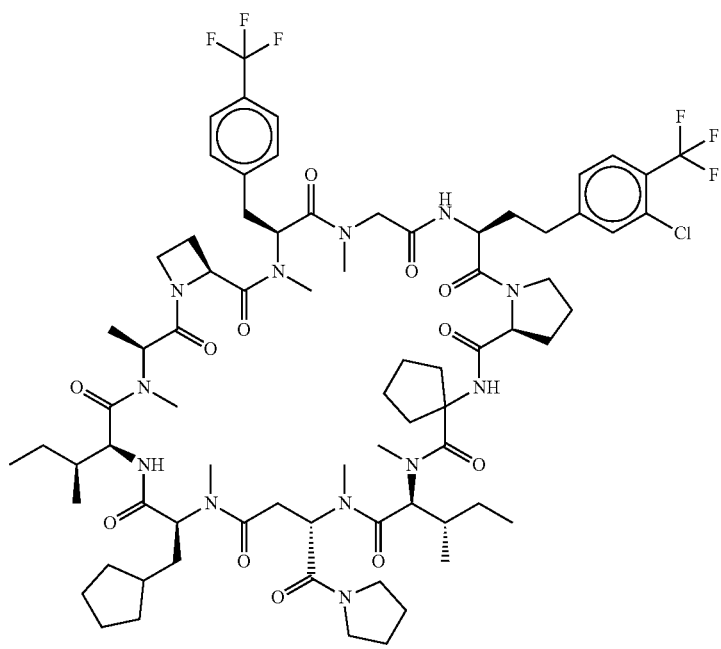 |

TABLE 24-continued
| Compound No. | Structural formula |
|---|---|
| 1184 | 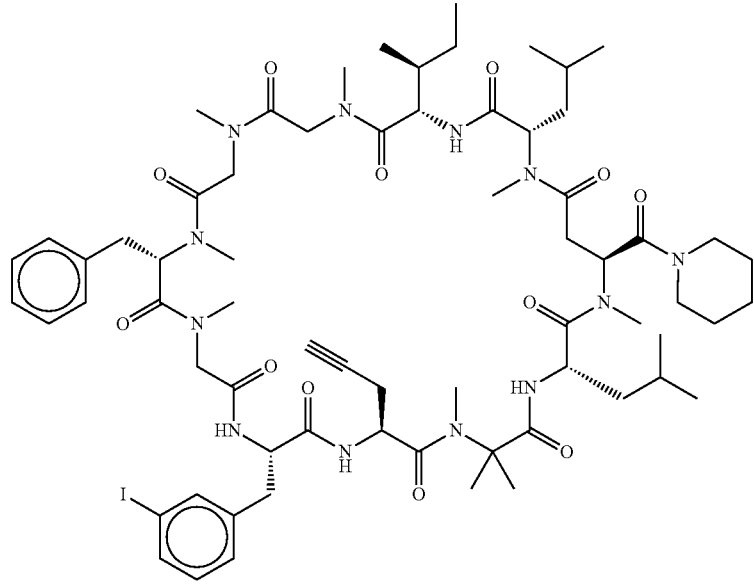 |
| 1185 | 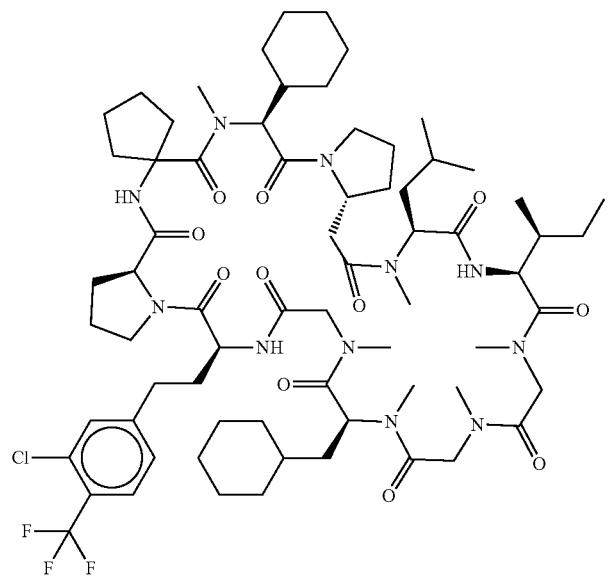 |

TABLE 24-continued
| Compound No. | Structural formula |
|---|---|
| 1186 | 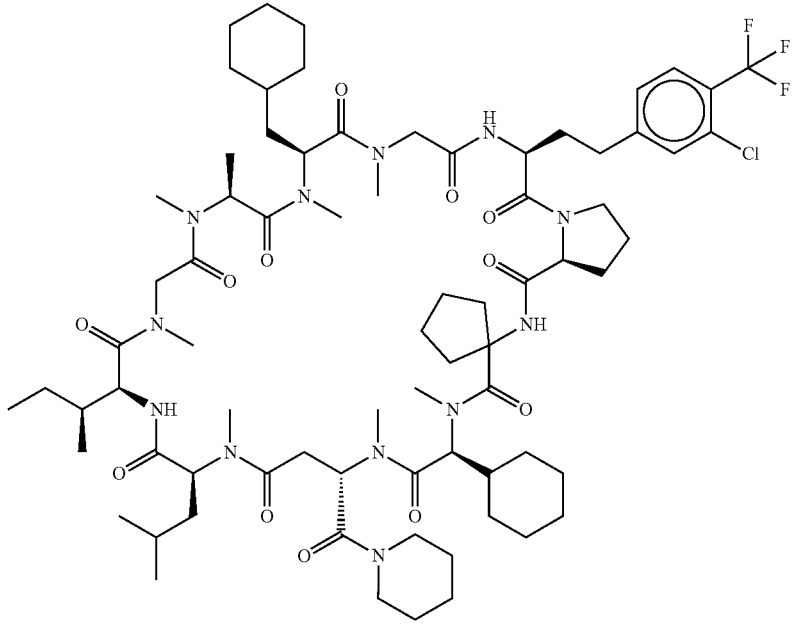 |
| 1187 | 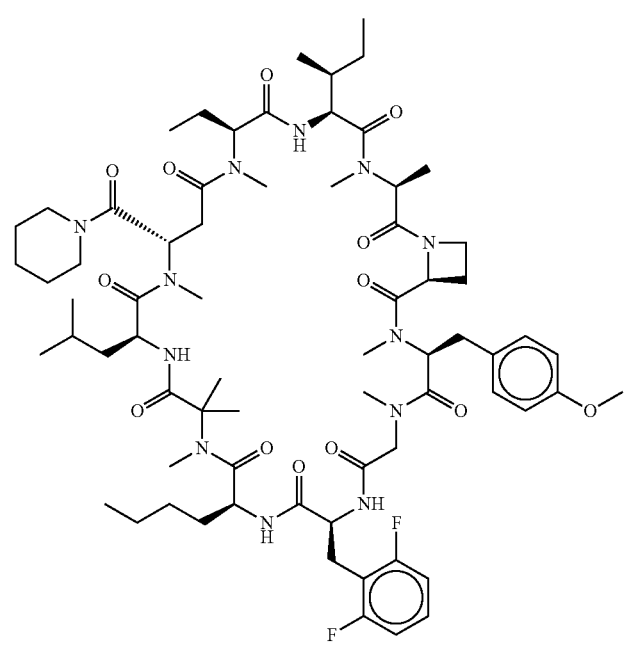 |

TABLE 24-continued
| Compound No. | Structural formula |
|---|---|
| 1188 | 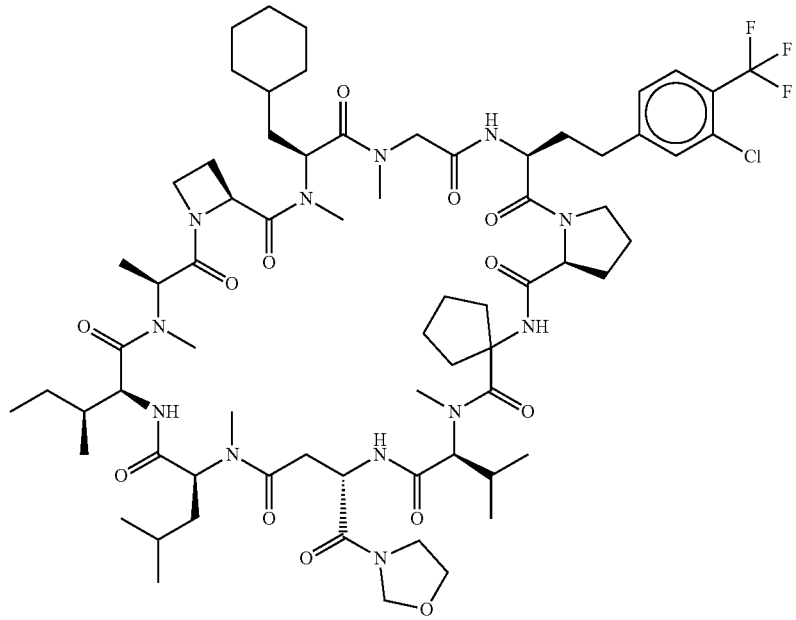 |
| 1189 | 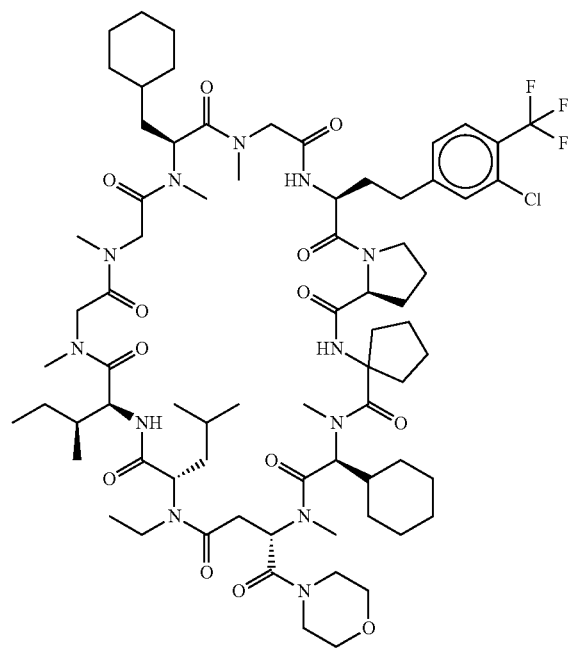 |

TABLE 24-continued
| Compound No. | Structural formula |
|---|---|
| 1190 | 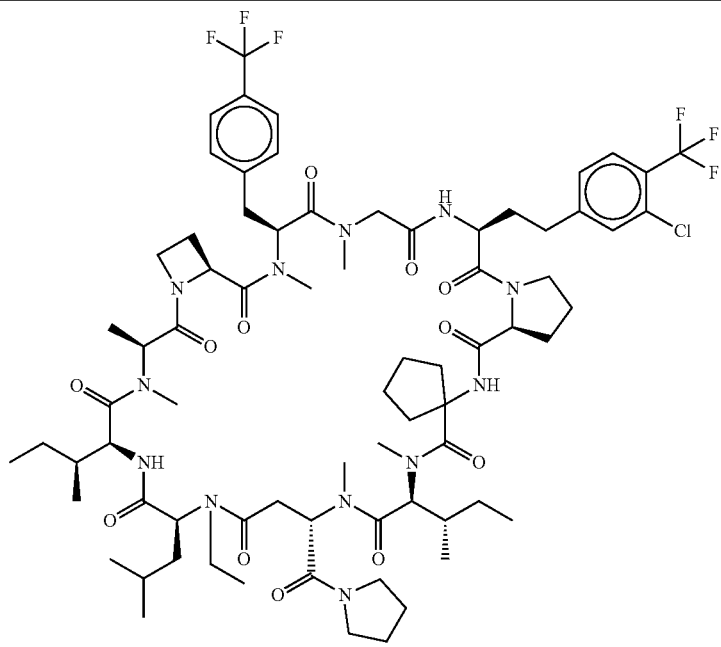 |
| 1191 | 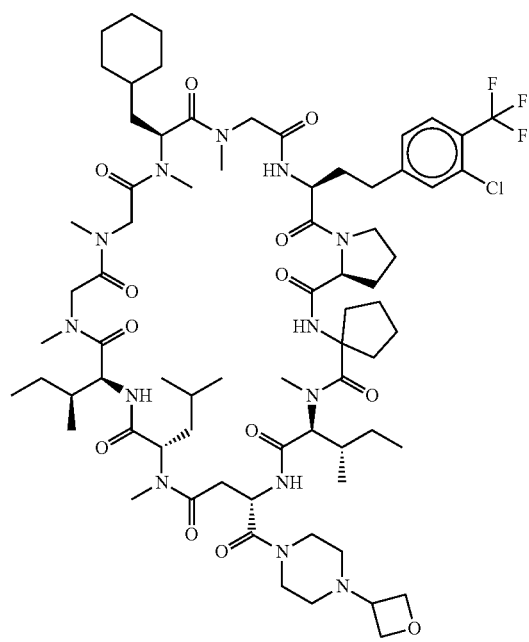 |

TABLE 24-continued
| Compound No. | Structural formula |
|---|---|
| 1192 | 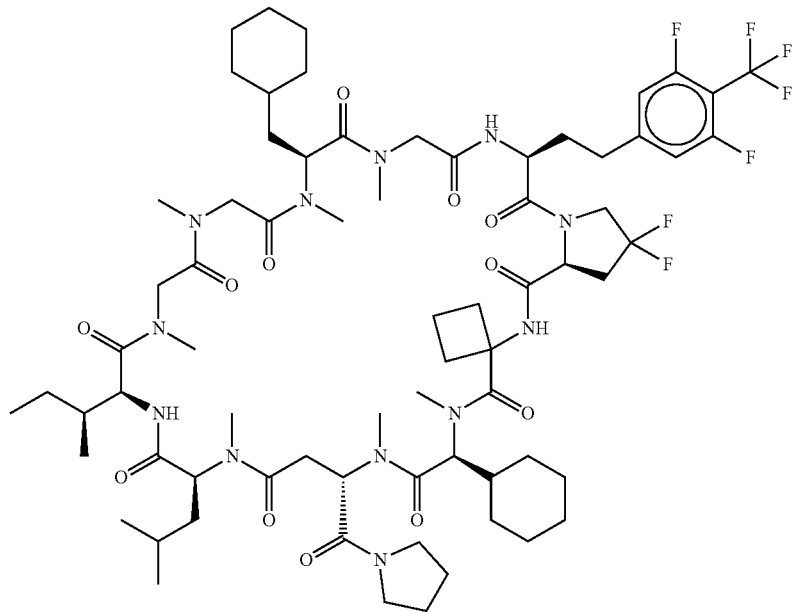 |
| 1193 | 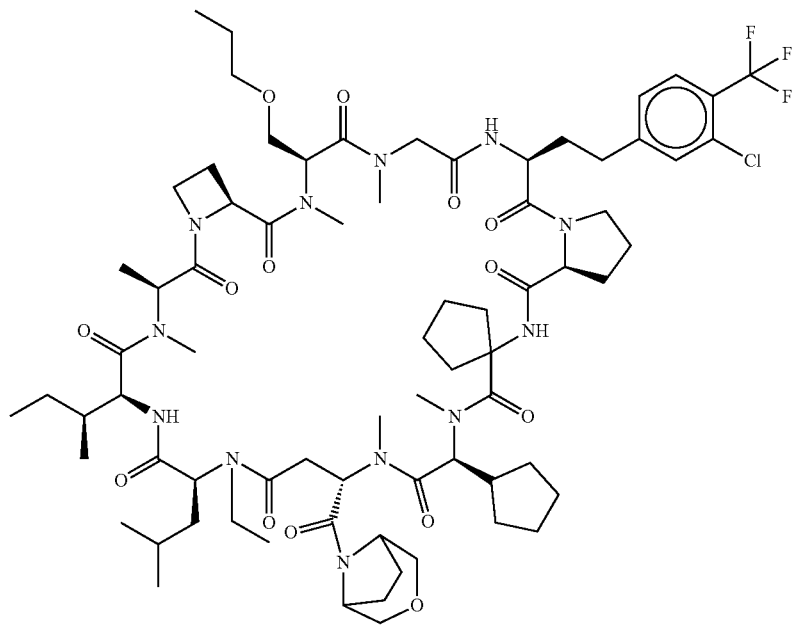 |

TABLE 24-continued
| Compound No. | Structural formula |
|---|---|
| 1194 | 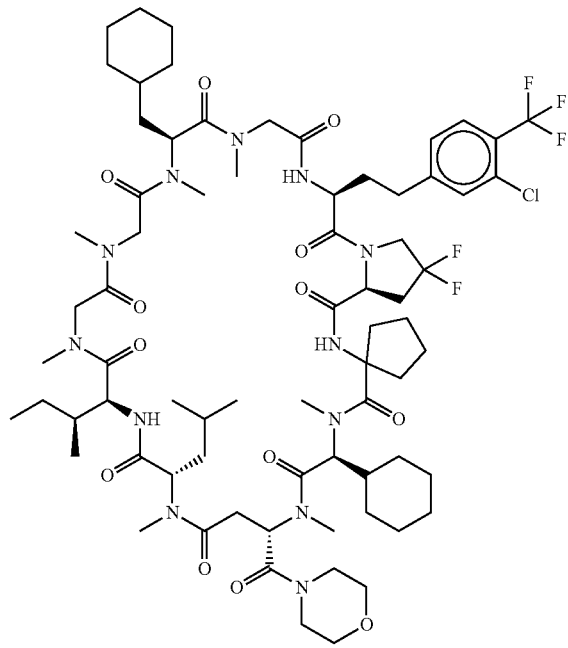 |
| 1195 | 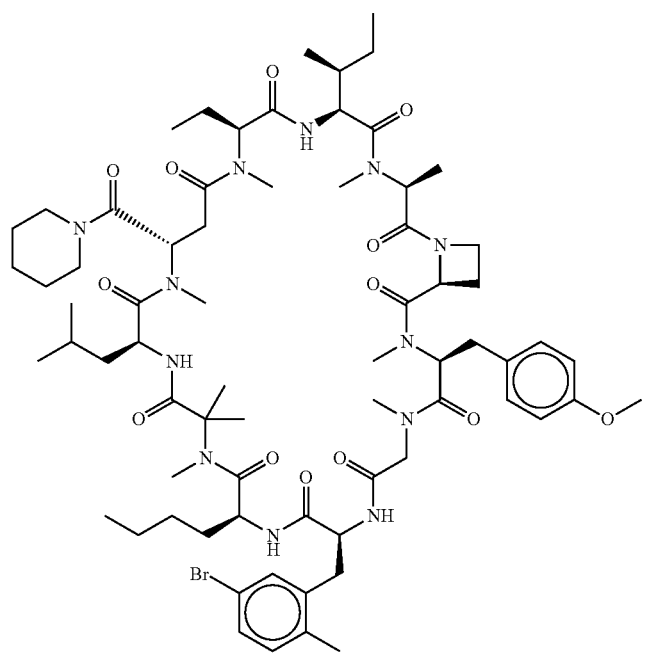 |

TABLE 24-continued
| Compound No. | Structural formula |
|---|---|
| 1196 | 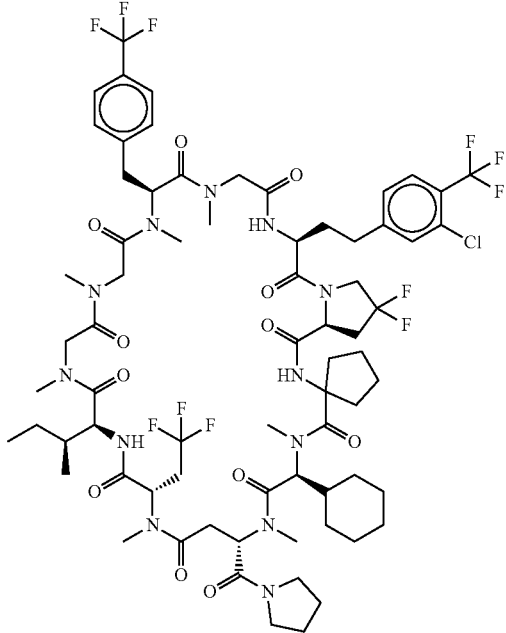 |
| 1197 | 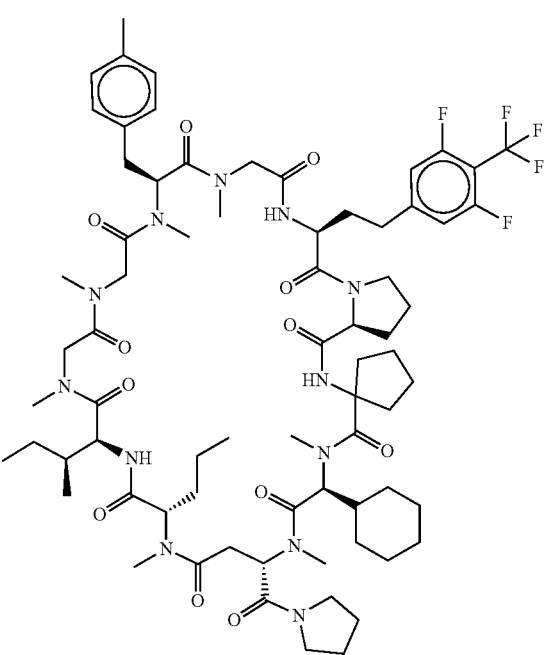 |

TABLE 24-continued
| Compound No. | Structural formula |
|---|---|
| 1198 | 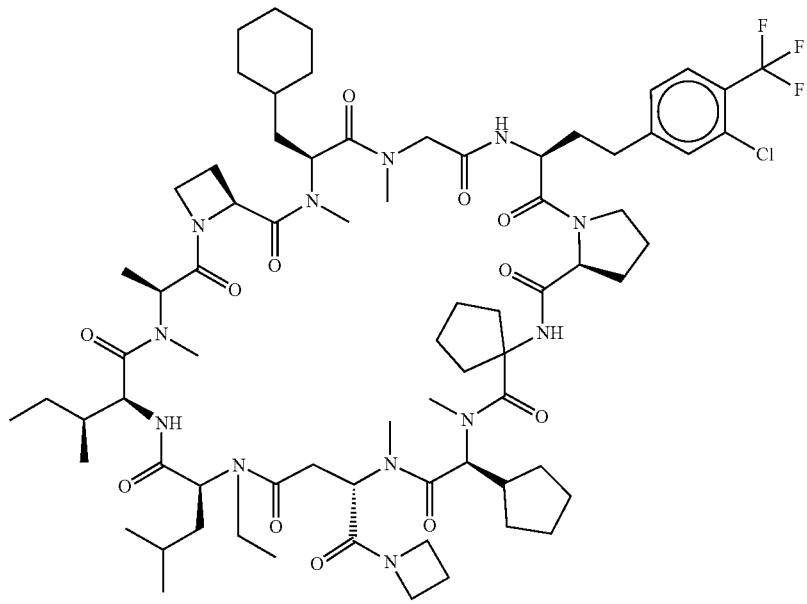 |
| 1199 | 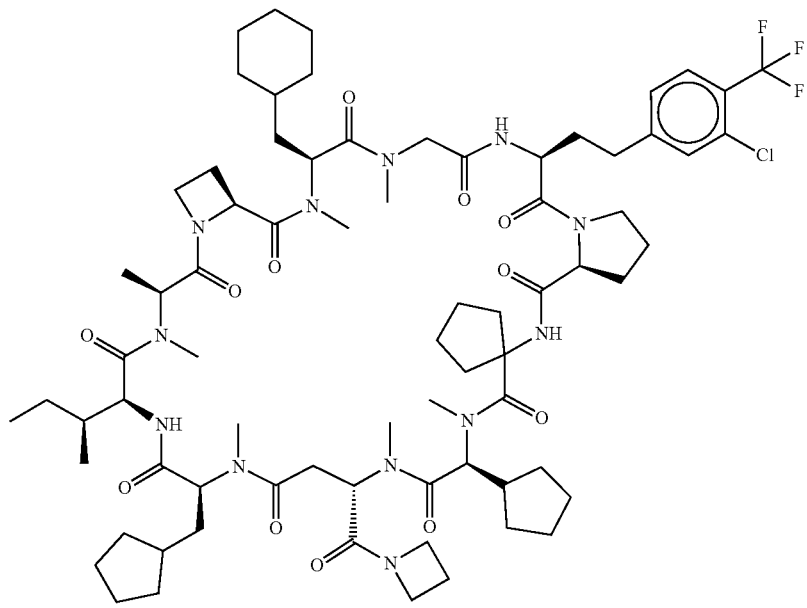 |

TABLE 24-continued

| Compound No. | Structural formula |
|---|---|
| 1200 | |
| 1201 | |

TABLE 24-continued
| Compound No. | Structural formula |
|---|---|
| 1202 | 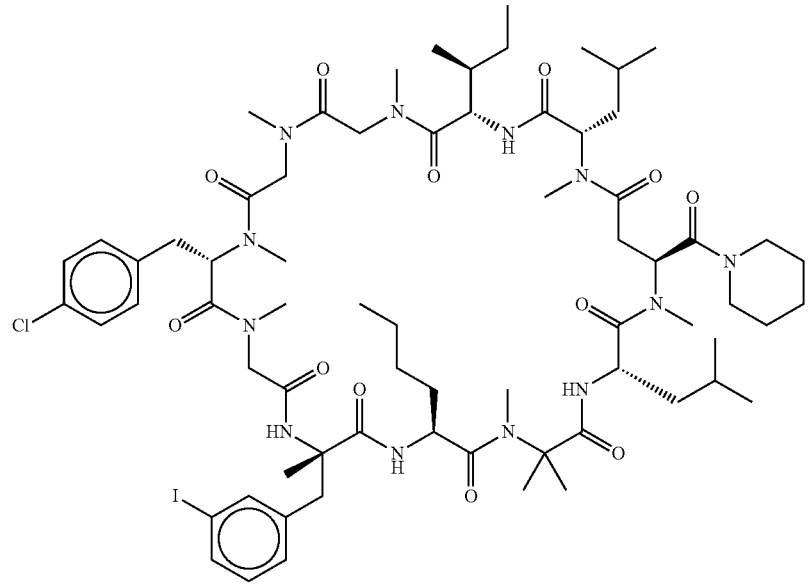 |
| 1203 | 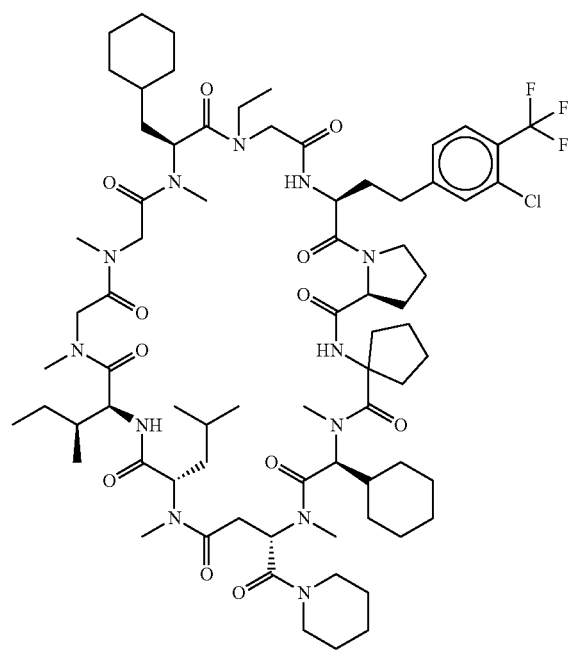 |

TABLE 24-continued
| Compound No. | Structural formula |
|---|---|
| 1204 | 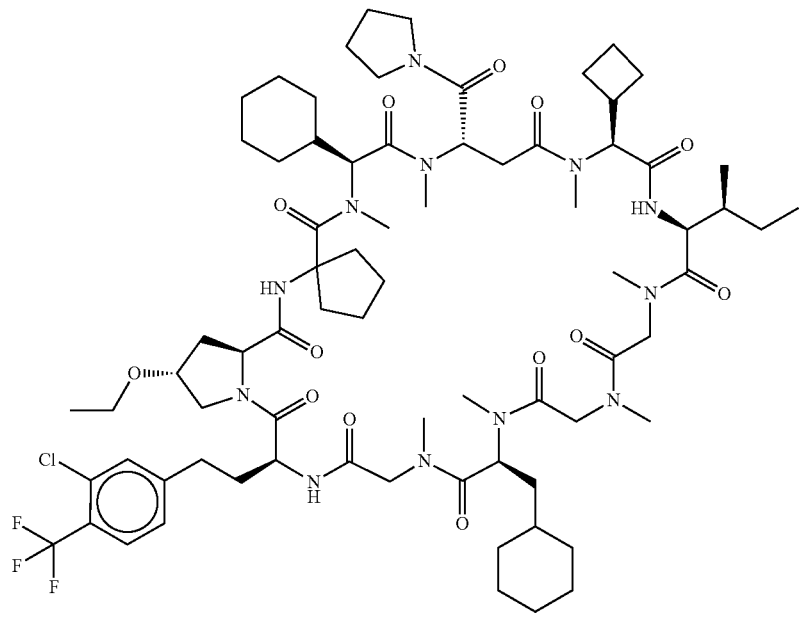 |
| 1205 | 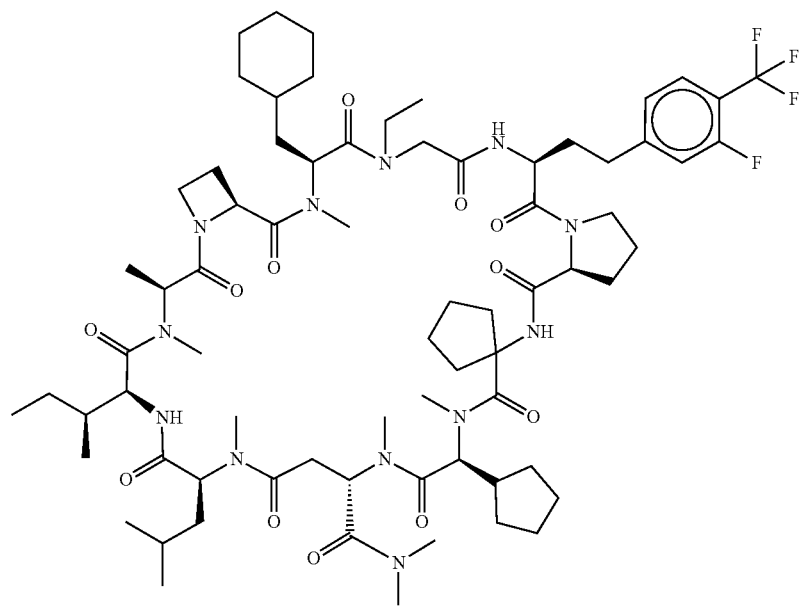 |

TABLE 24-continued
| Compound No. | Structural formula |
| --- | --- |
| 1206 | 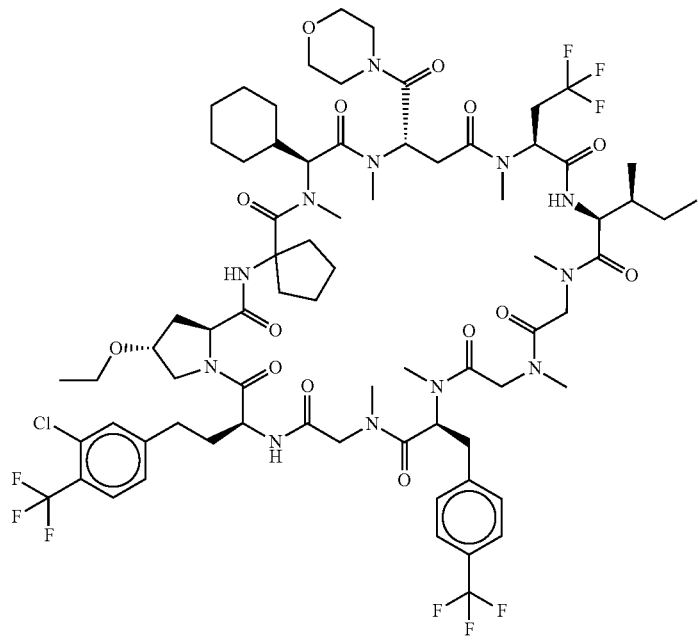 |
| 1207 | 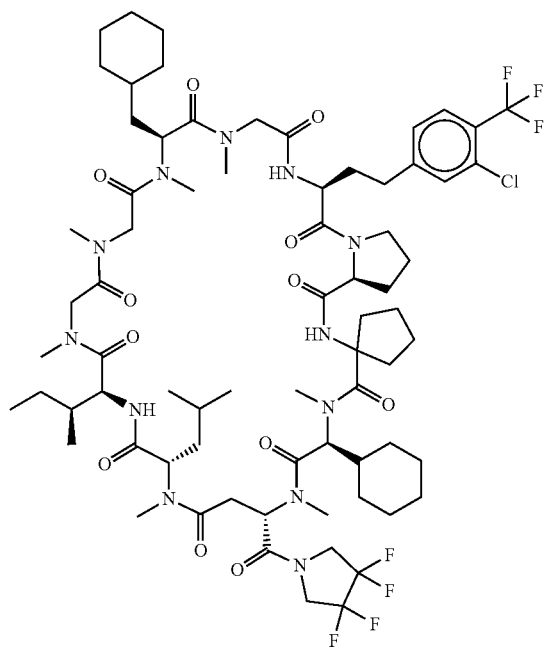 |

TABLE 24-continued
| Compound No. | Structural formula |
|---|---|
| 1208 | 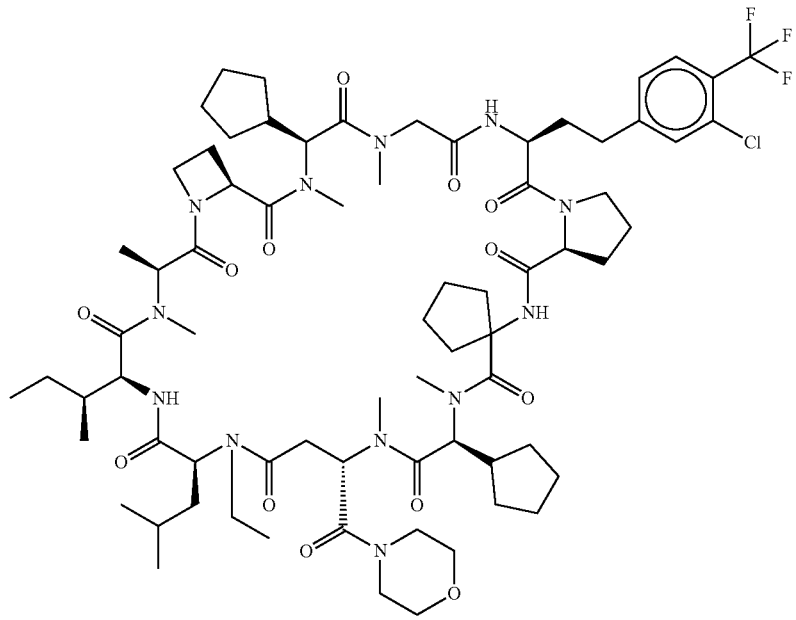 |
| 1209 | 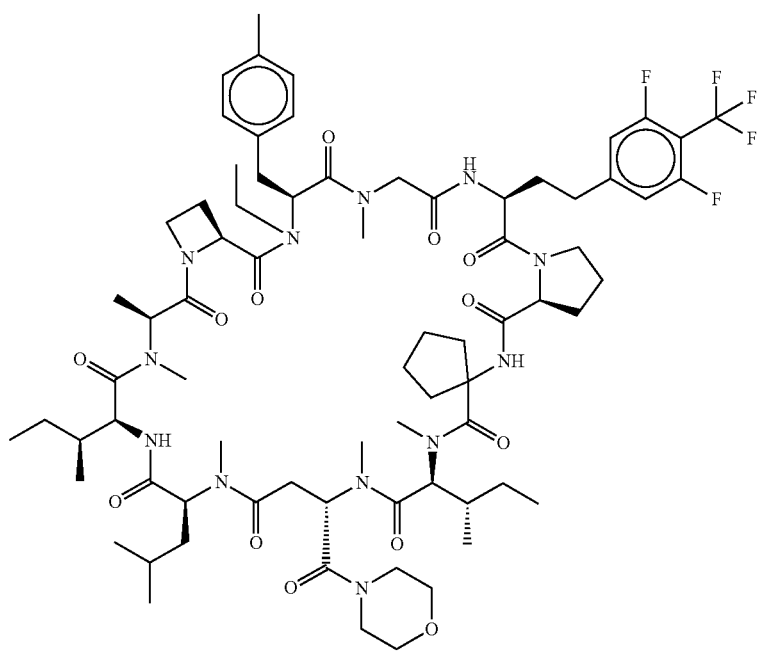 |

TABLE 24-continued
| Compound No. | Structural formula |
|---|---|
| 1210 | 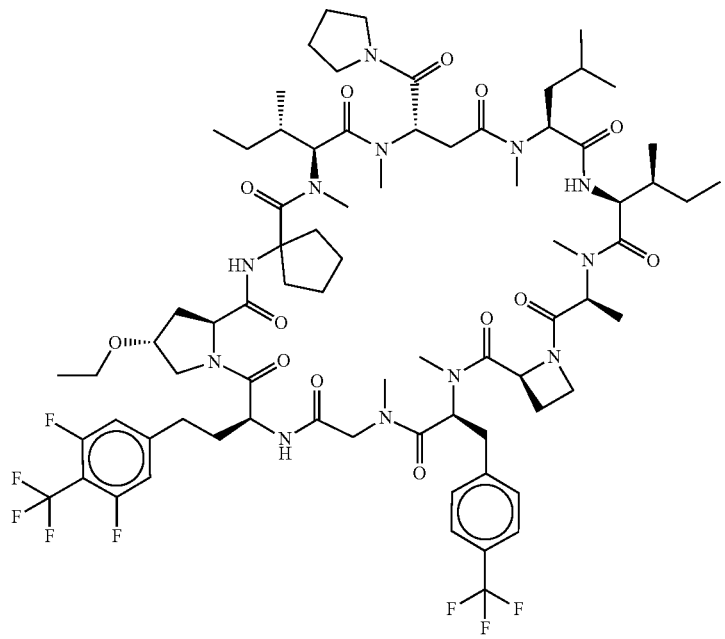 |
| 1211 | 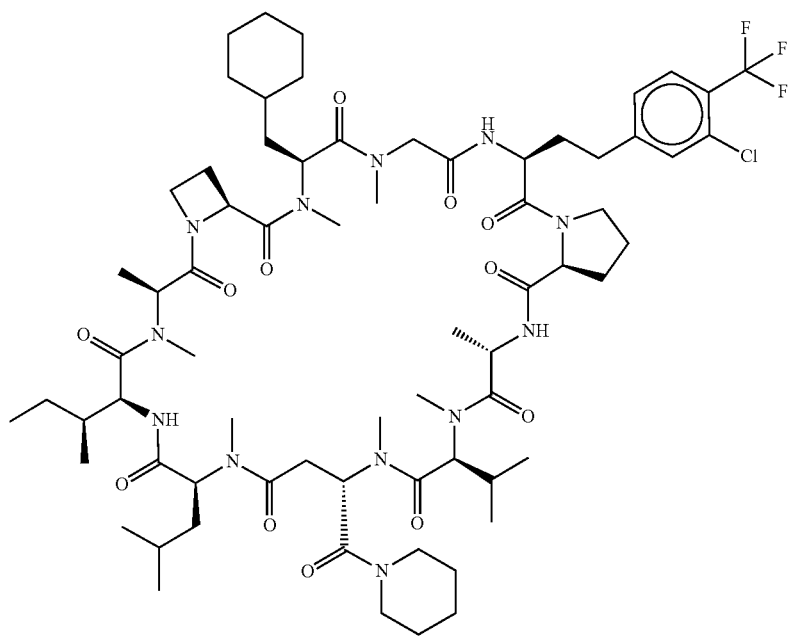 |

TABLE 24-continued
| Compound No. | Structural formula |
|---|---|
| 1212 | 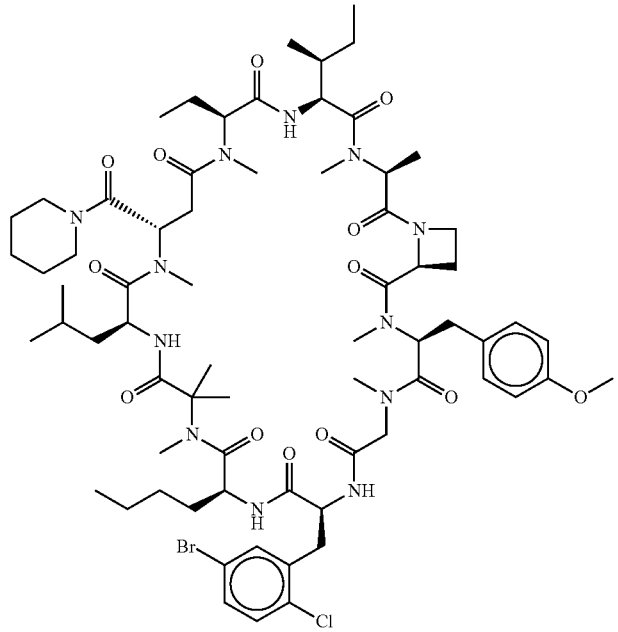 |
| 1213 | 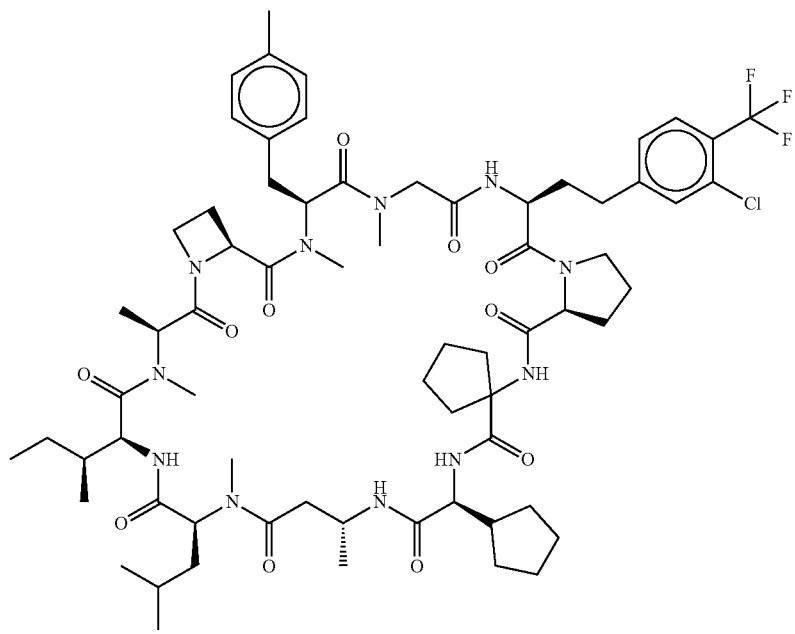 |

TABLE 24-continued
| Compound No. | Structural formula |
|---|---|
| 1214 | 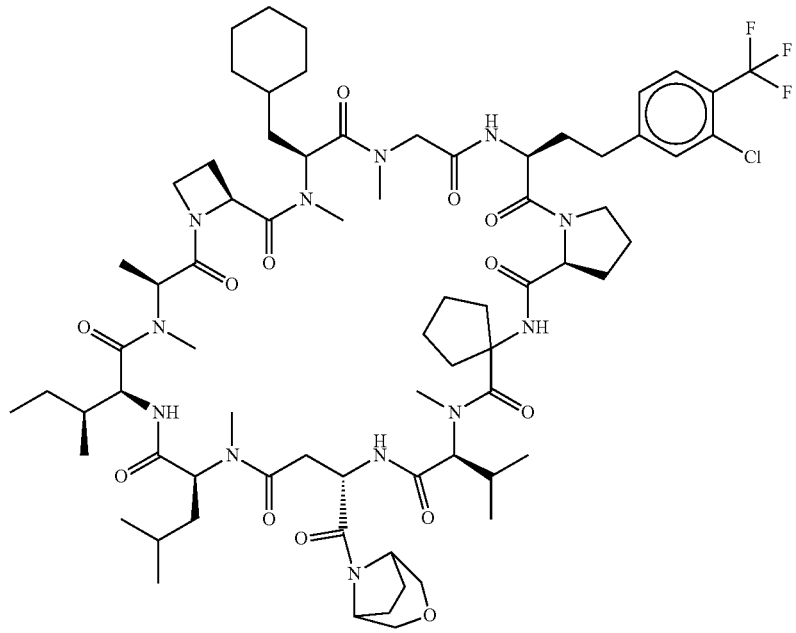 |
| 1215 | 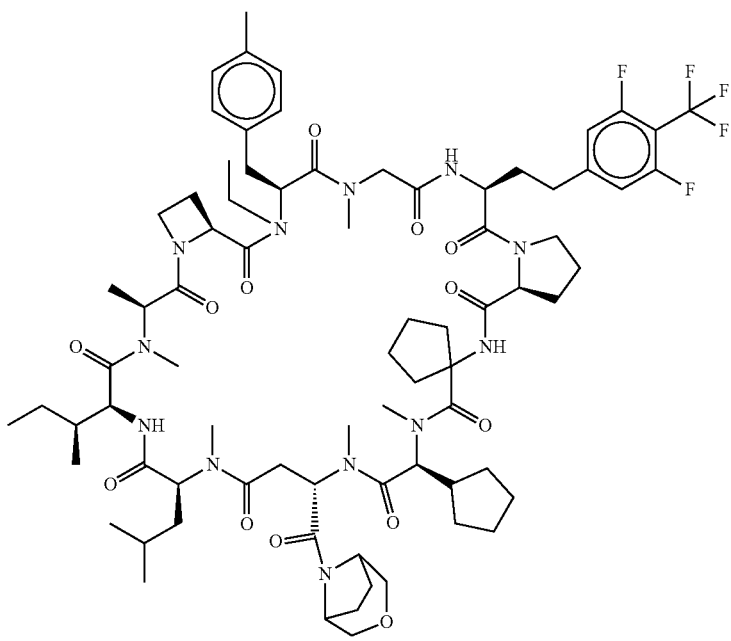 |

TABLE 24-continued
| Compound No. | Structural formula |
|---|---|
| 1216 | 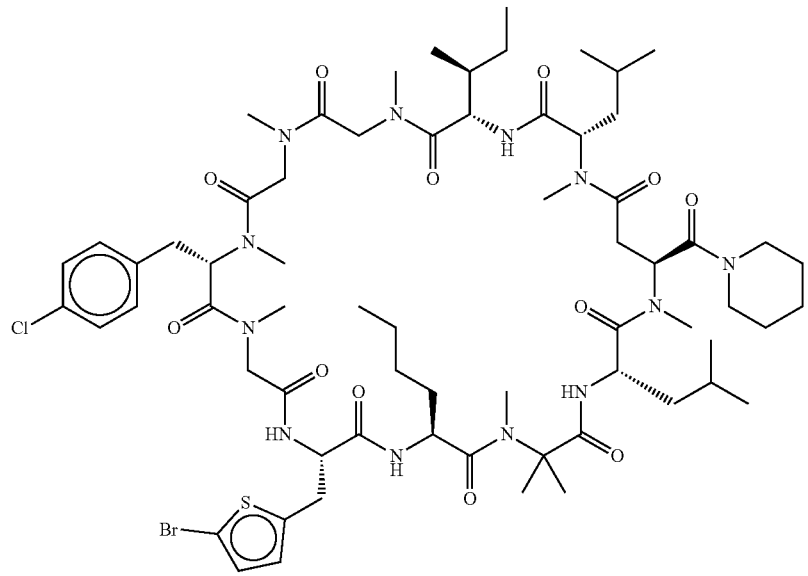 |
| 1217 | 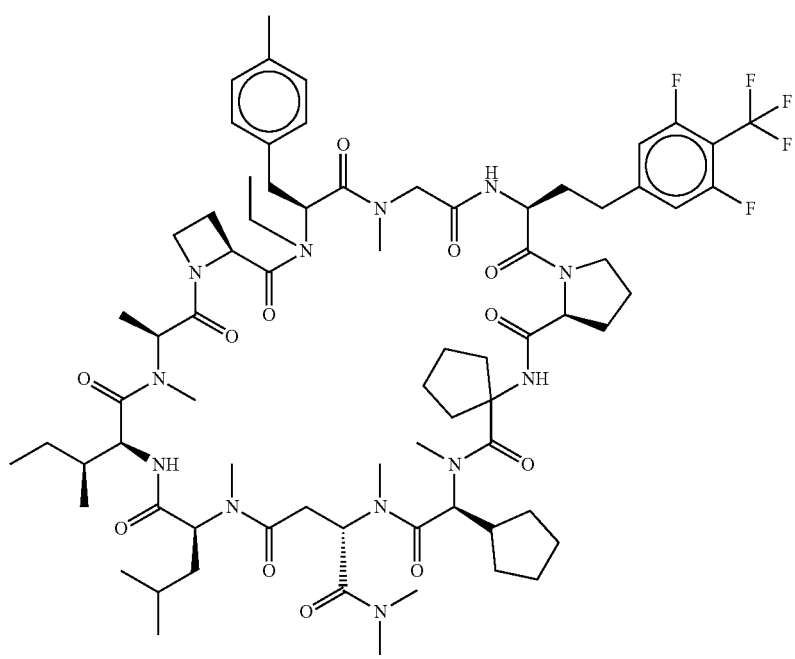 |

TABLE 24-continued
| Compound No. | Structural formula |
|---|---|
| 1218 | 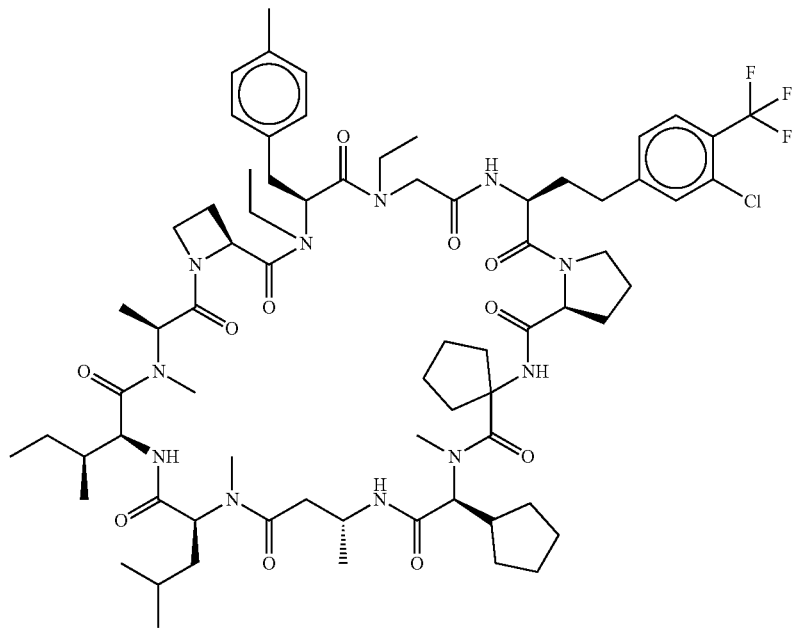 |
| 1219 | 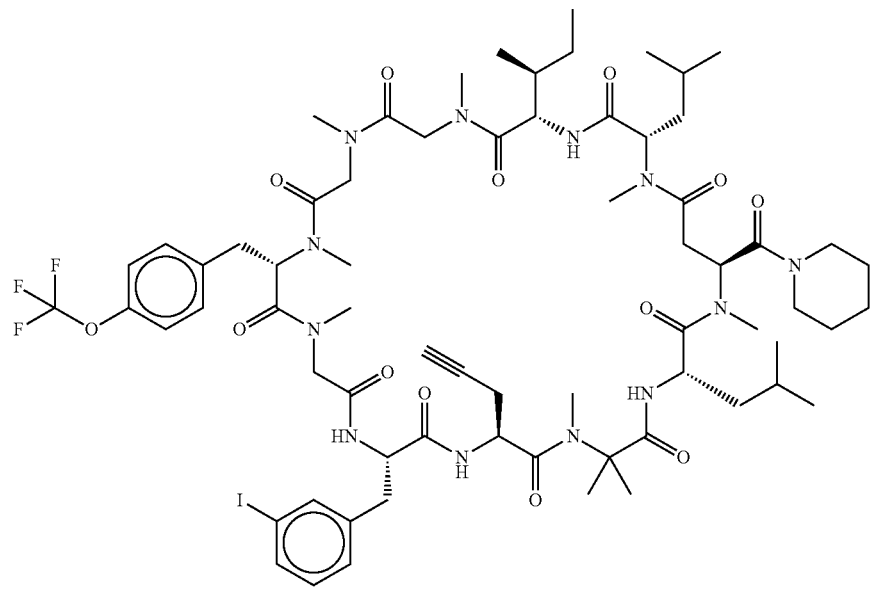 |

TABLE 24-continued
| Compound No. | Structural formula |
|---|---|
| 1220 | 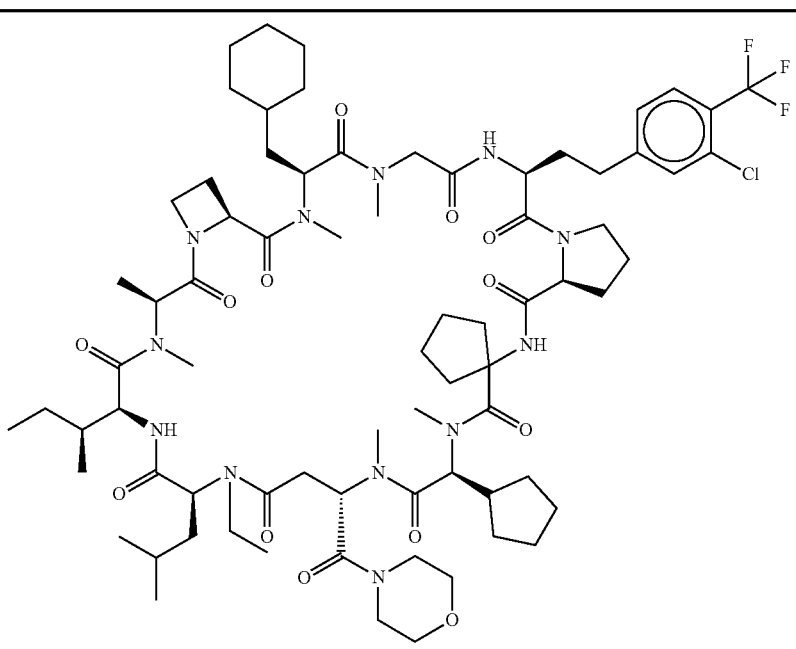 |
| 1221 | 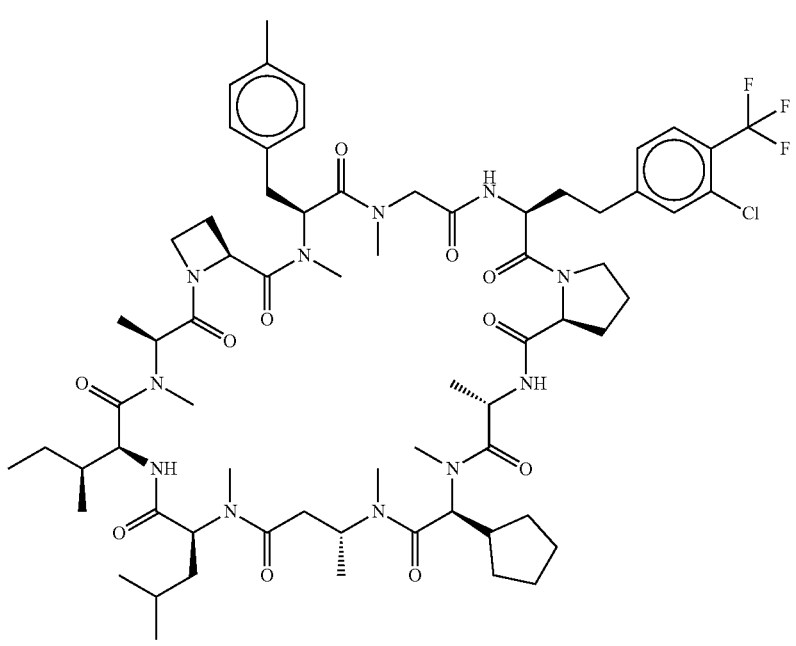 |

TABLE 24-continued
| Compound No. | Structural formula |
|---|---|
| 1222 | 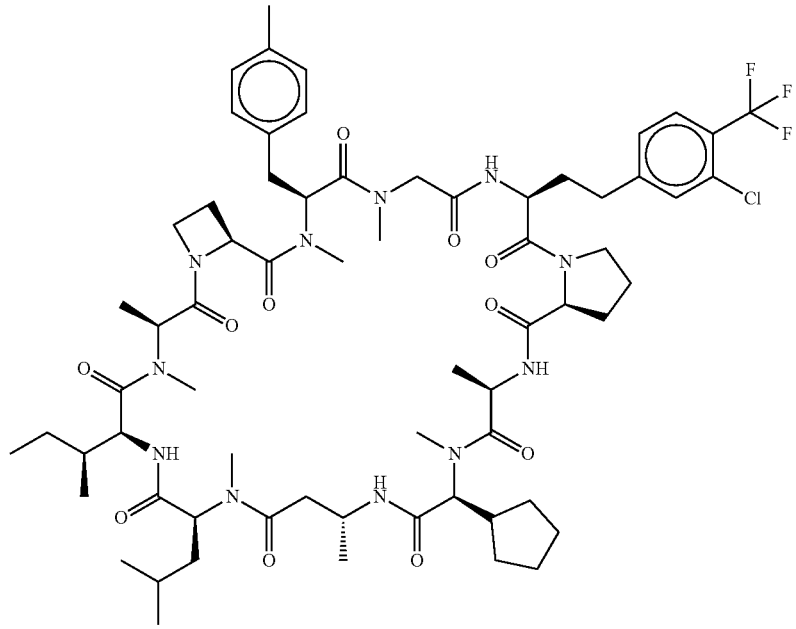 |
| 1223 | 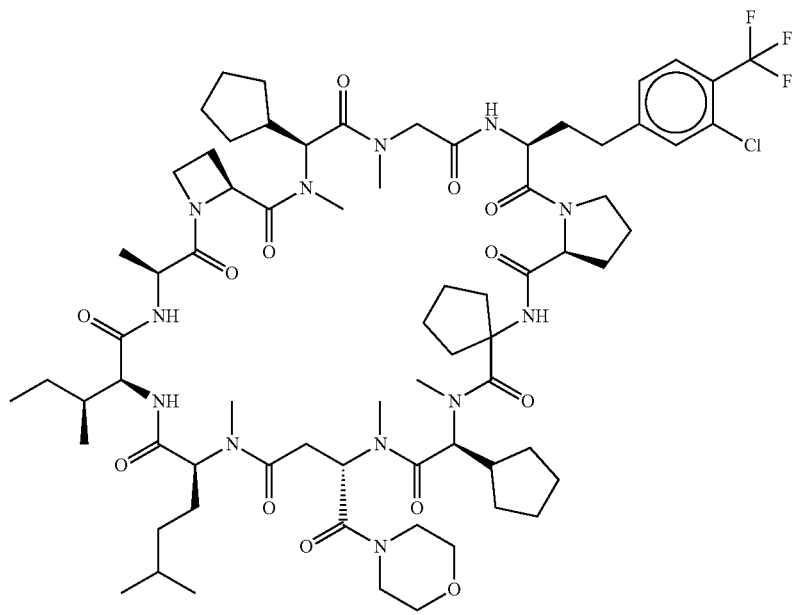 |

TABLE 24-continued

| Compound No. | Structural formula |
| --- | --- |
| 1224 | |
| 1225 | |

TABLE 24-continued
| Compound No. | Structural formula |
|---|---|
| 1226 | 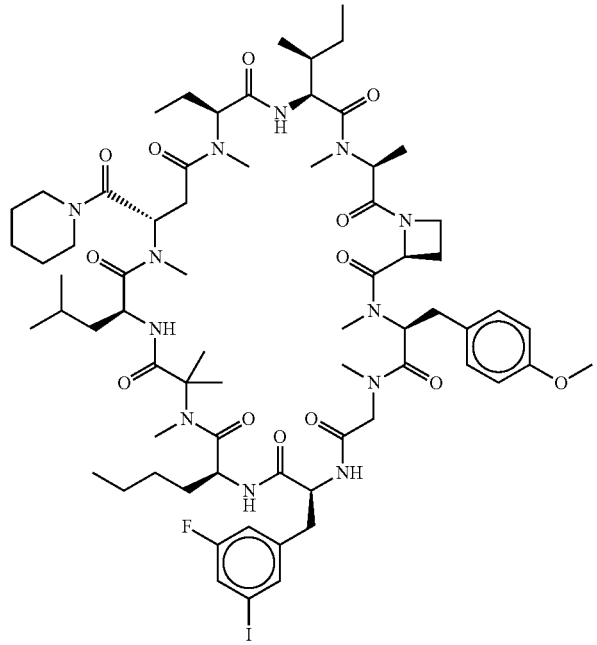 |
| 1227 | 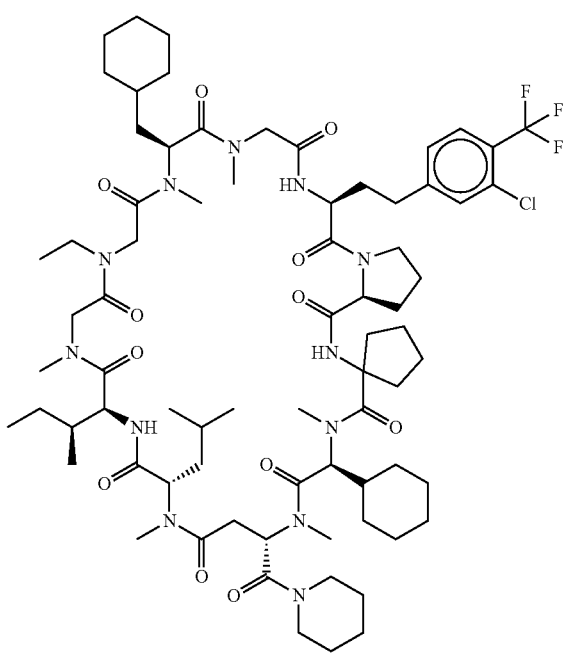 |

TABLE 24-continued
| Compound No. | Structural formula |
|---|---|
| 1228 | 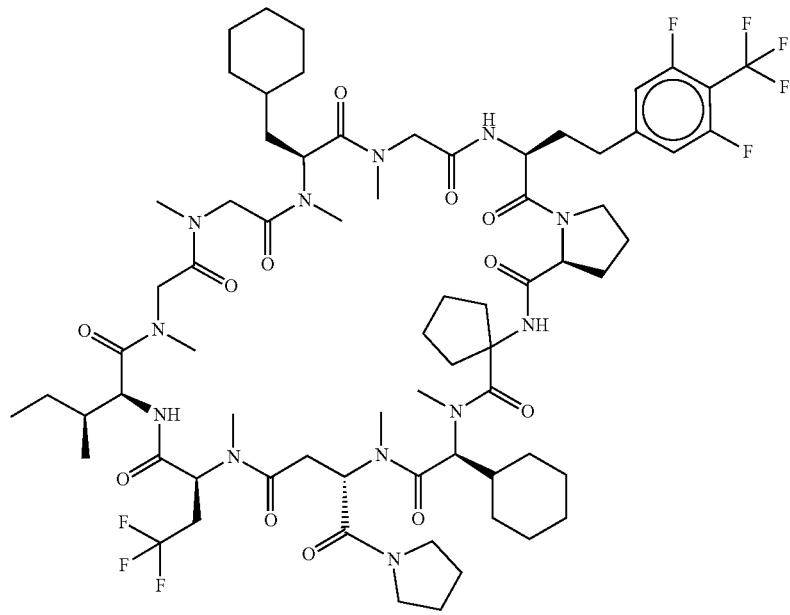 |
| 1229 | 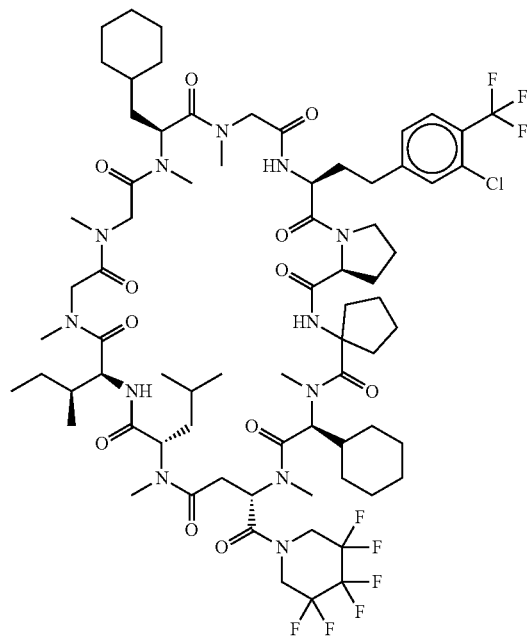 |

TABLE 24-continued
| Compound No. | Structural formula |
|---|---|
| 1230 | 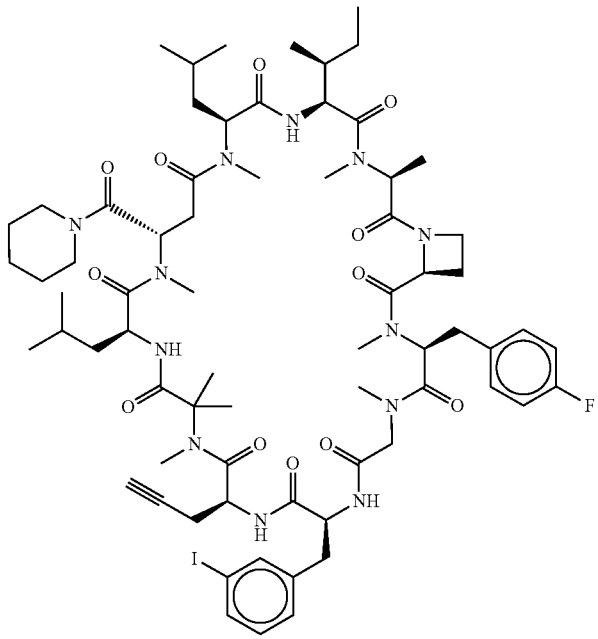 |
| 1231 | 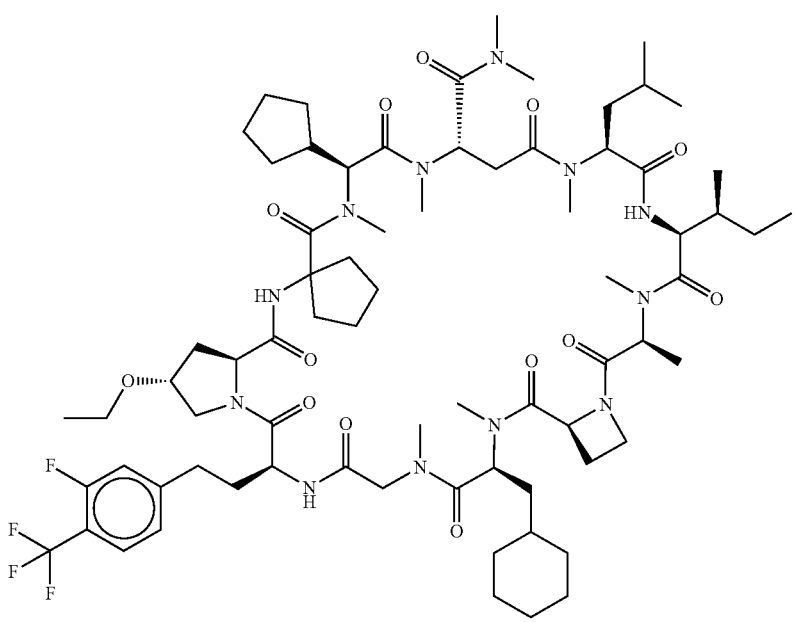 |

TABLE 24-continued
| Compound No. | Structural formula |
|---|---|
| 1232 | 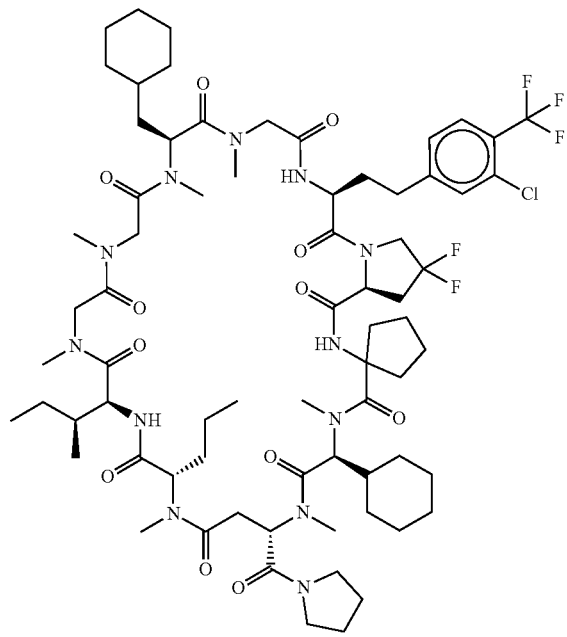 |
| 1233 | 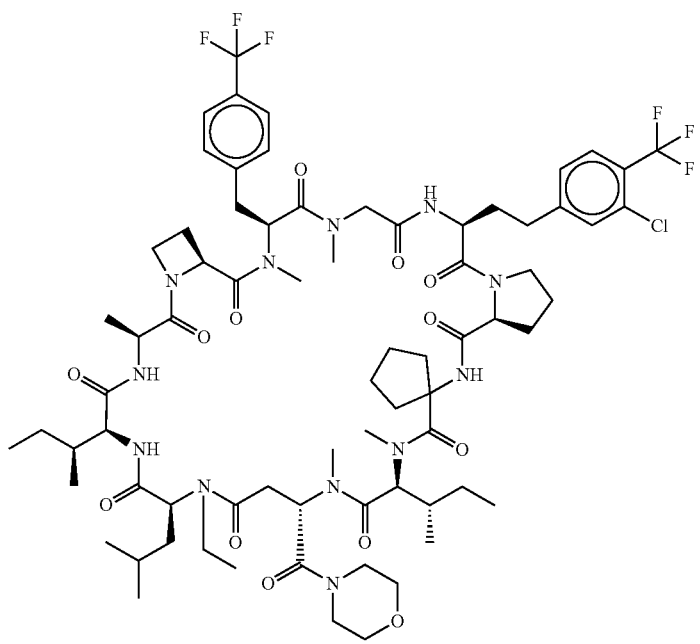 |

TABLE 24-continued
| Compound No. | Structural formula |
|---|---|
| 1234 | 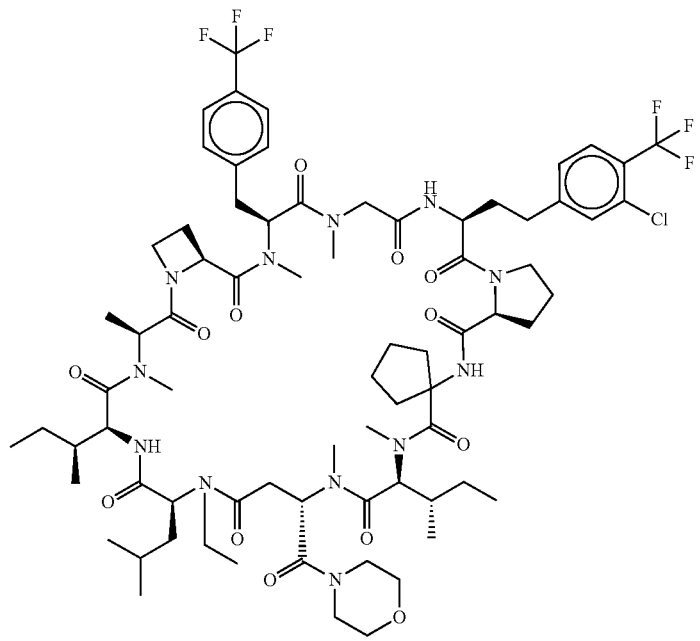 |
| 1235 | 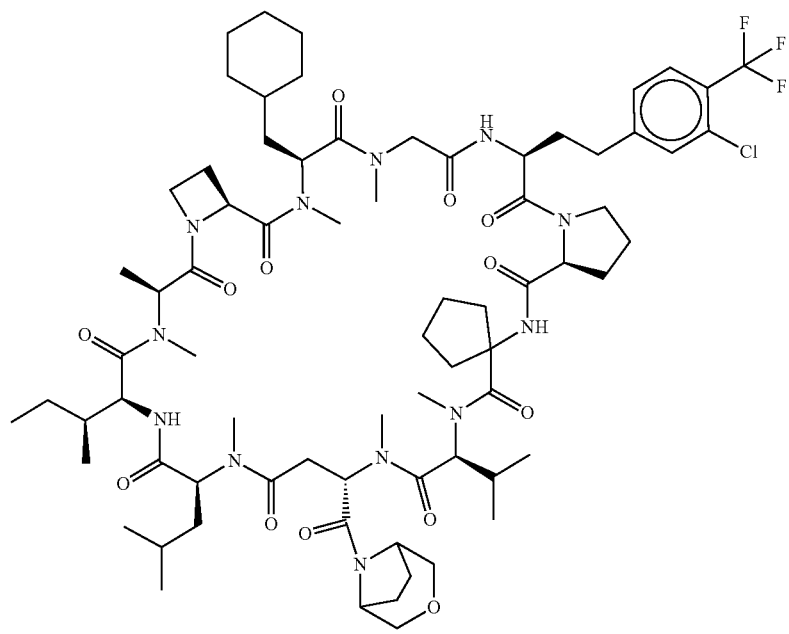 |

TABLE 24-continued
| Compound No. | Structural formula |
|---|---|
| 1236 | 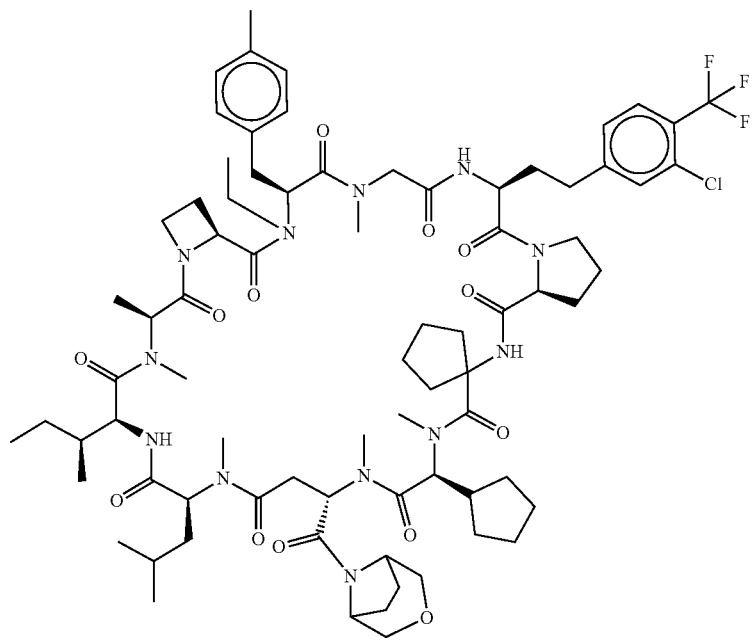 |
| 1237 | 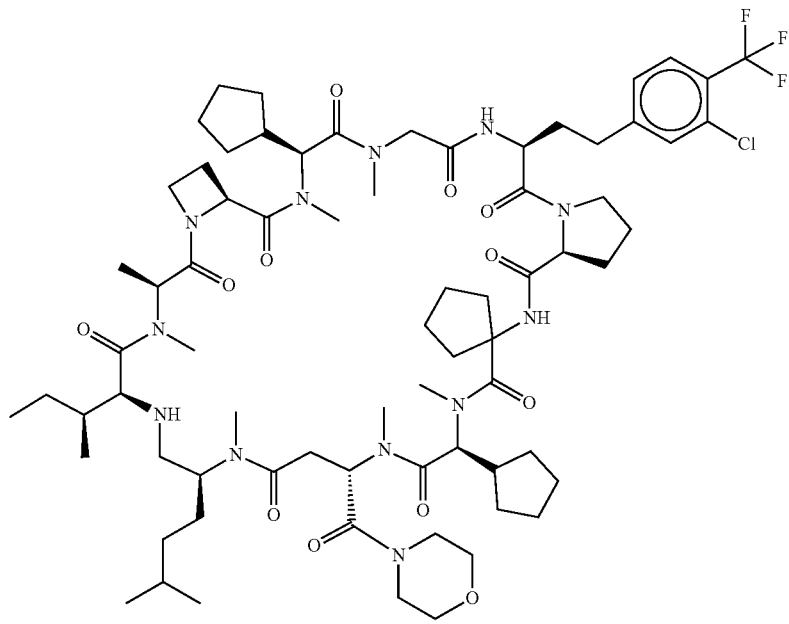 |

TABLE 24-continued
| Compound No. | Structural formula |
|---|---|
| 1238 | 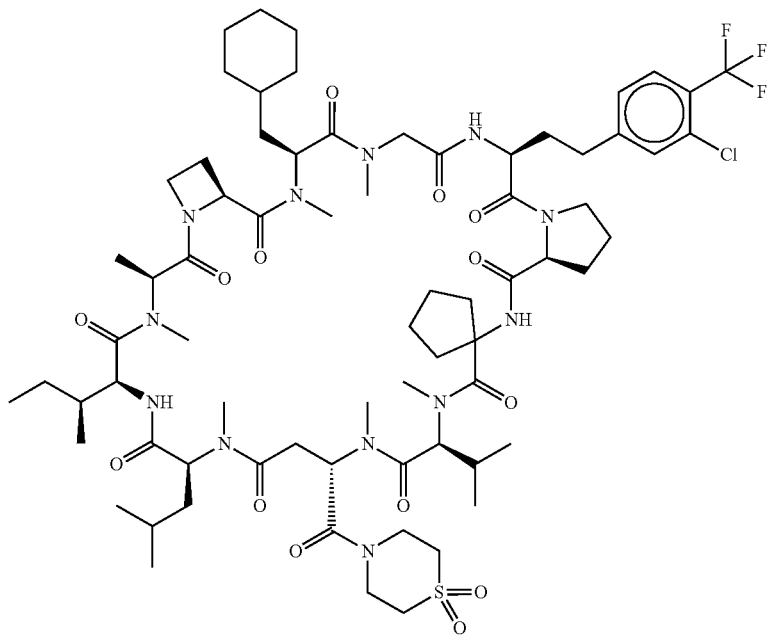 |
| 1239 | 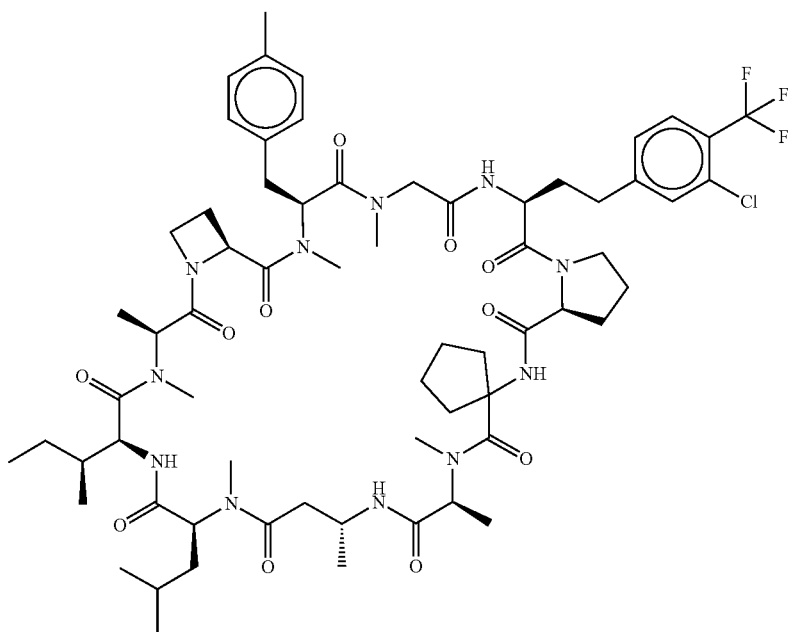 |

TABLE 24-continued
| Compound No. | Structural formula |
|---|---|
| 1240 | 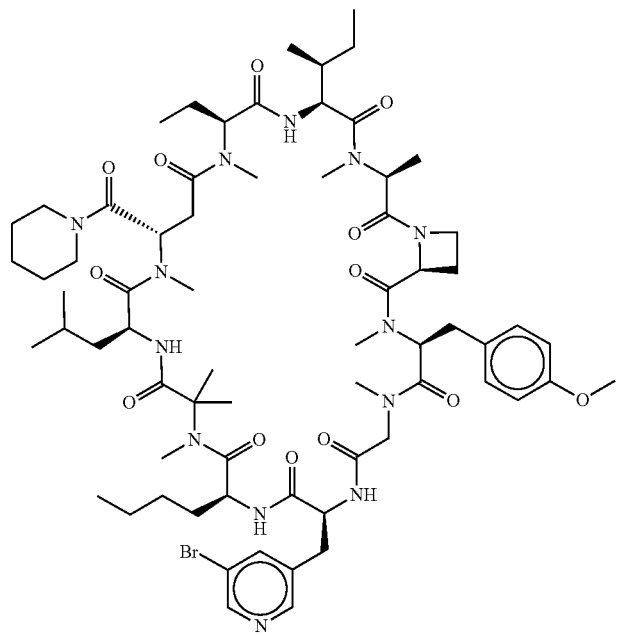 |
| 1241 | 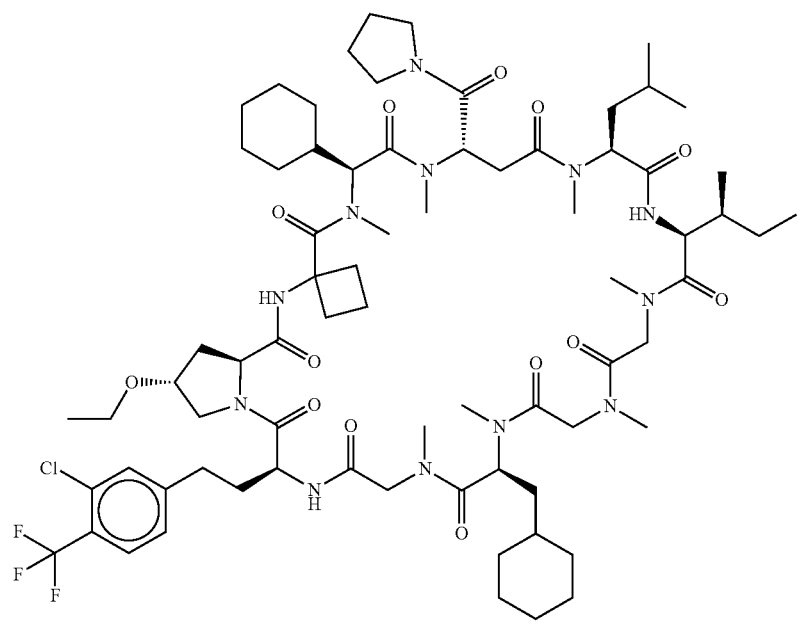 |

TABLE 24-continued
| Compound No. | Structural formula |
|---|---|
| 1242 | 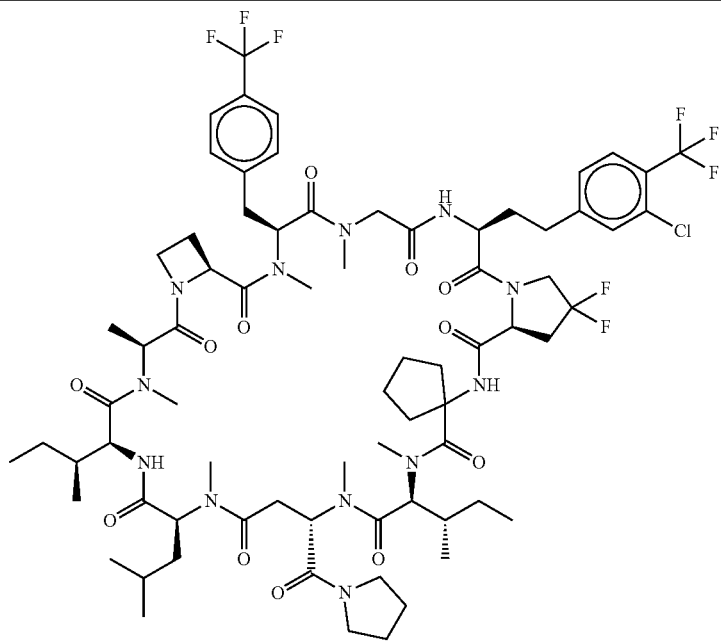 |
| 1243 | 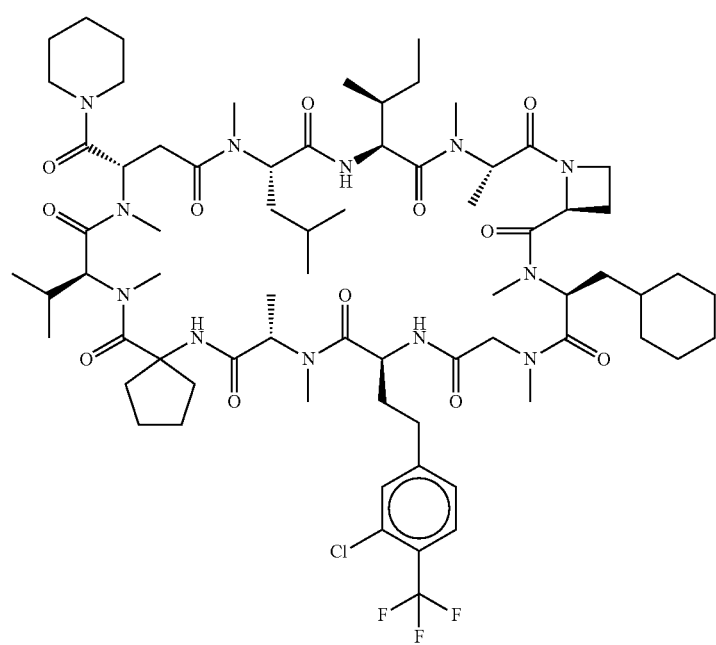 |

TABLE 24-continued
| Compound No. | Structural formula |
|---|---|
| 1244 | 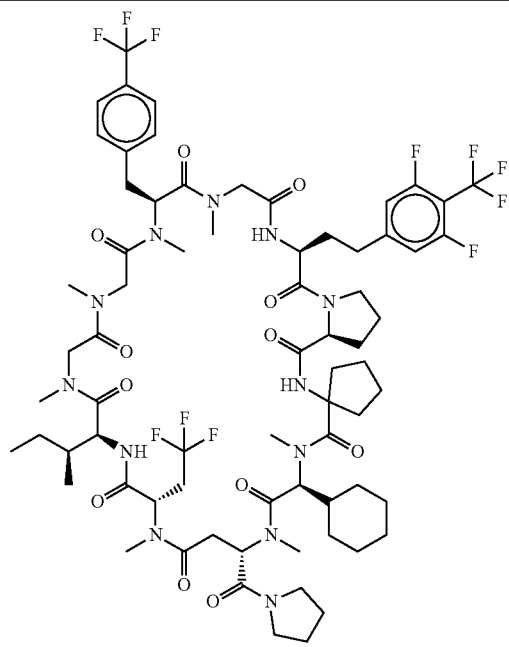 |
| 1245 | 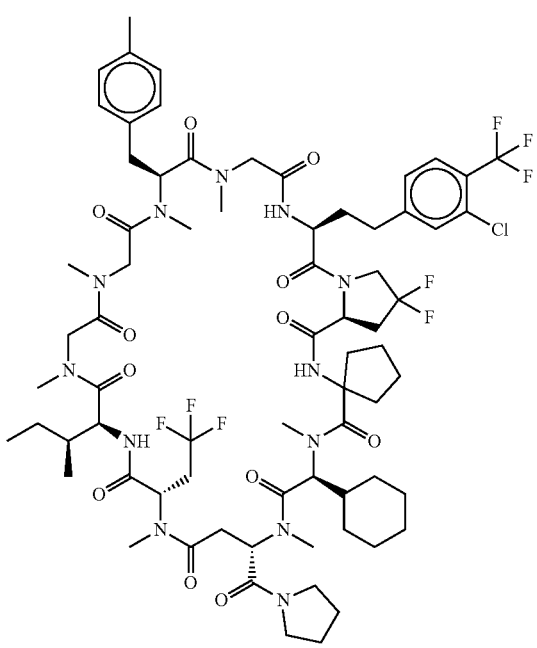 |

TABLE 24-continued
| Compound No. | Structural formula |
|---|---|
| 1246 | 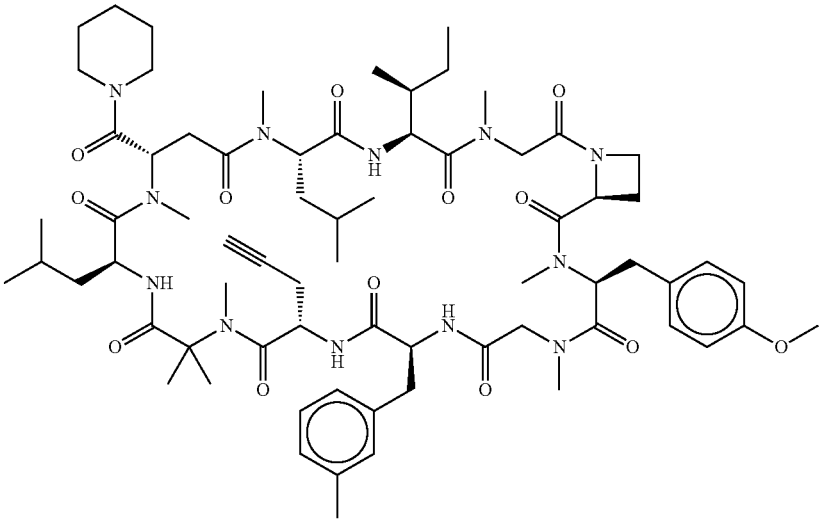 |
| 1247 | 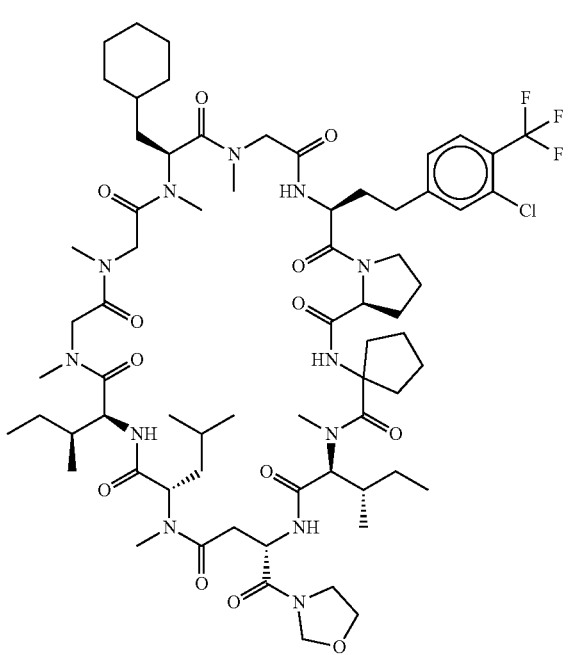 |

TABLE 24-continued
| Compound No. | Structural formula |
|---|---|
| 1248 | 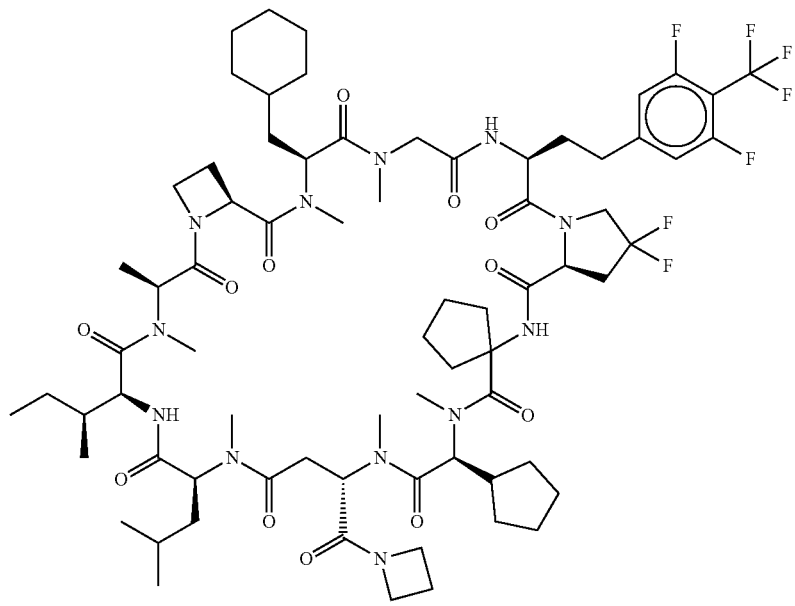 |
| 1249 | 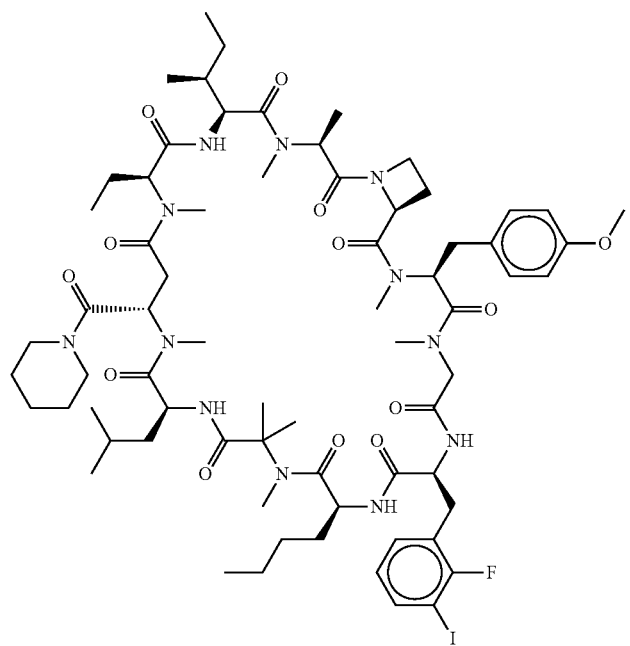 |

TABLE 24-continued
| Compound No. | Structural formula |
|---|---|
| 1250 | 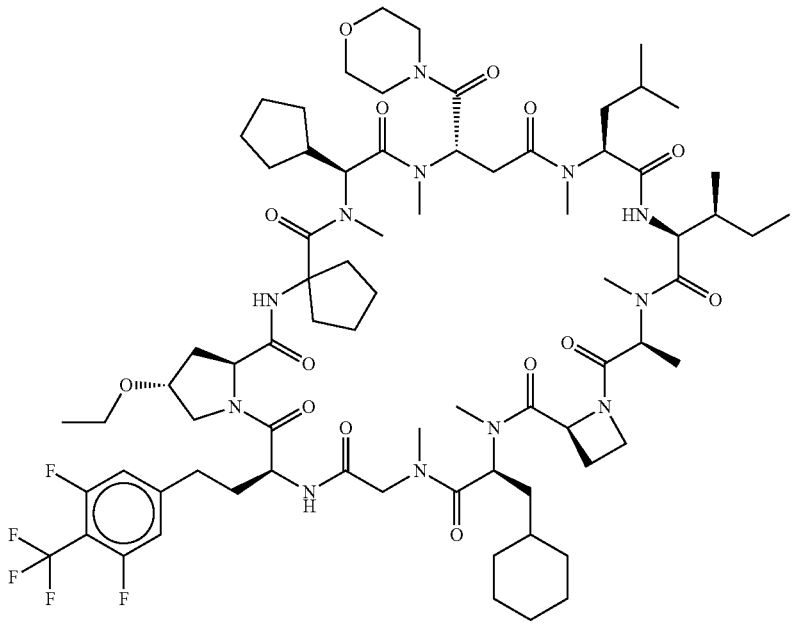 |
| 1251 | 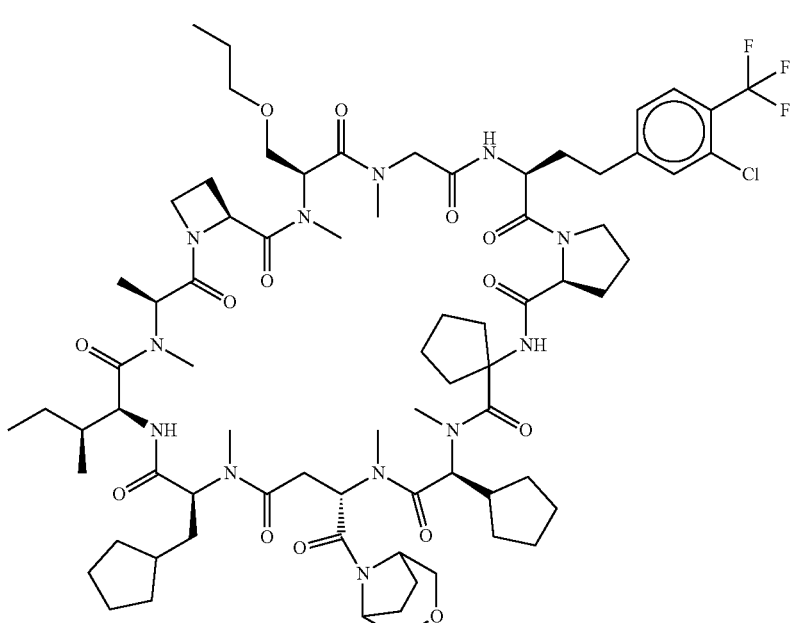 |

TABLE 24-continued
| Compound No. | Structural formula |
|---|---|
| 1252 | 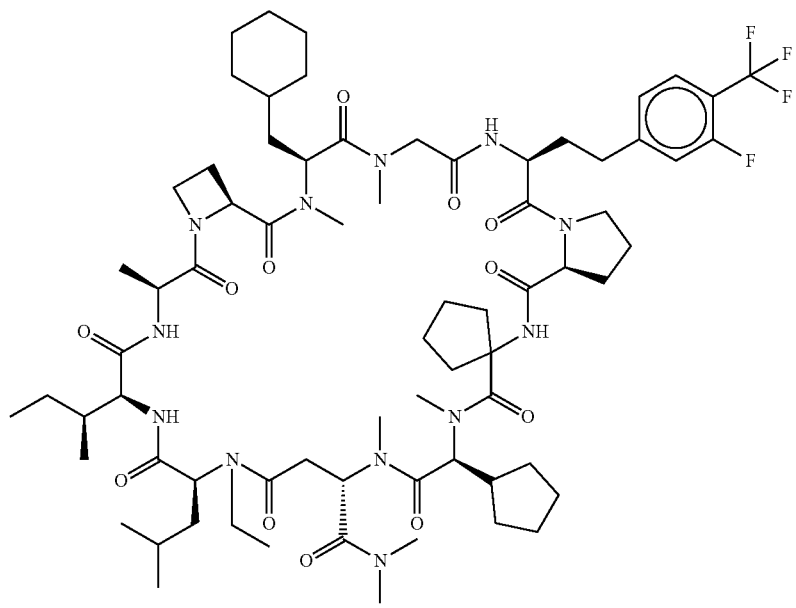 |
| 1253 | 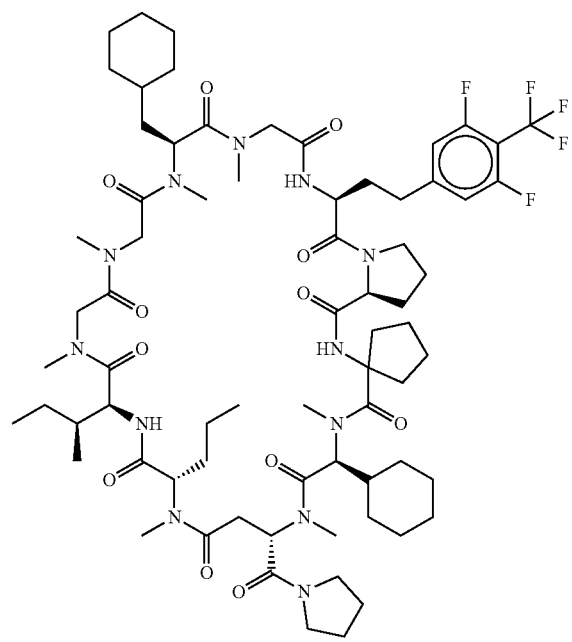 |

TABLE 24-continued

| Compound No. | Structural formula |
|---|---|
| 1254 | |
| 1255 | |

TABLE 24-continued
| Compound No. | Structural formula |
| --- | --- |
| 1256 | 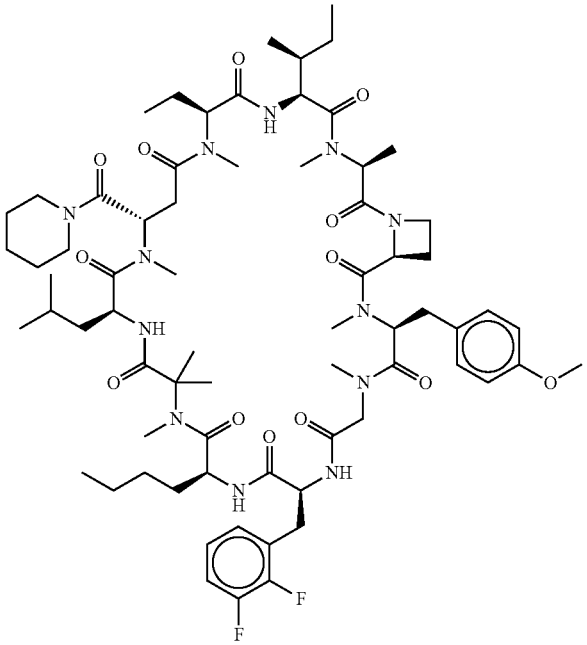 |
| 1257 | 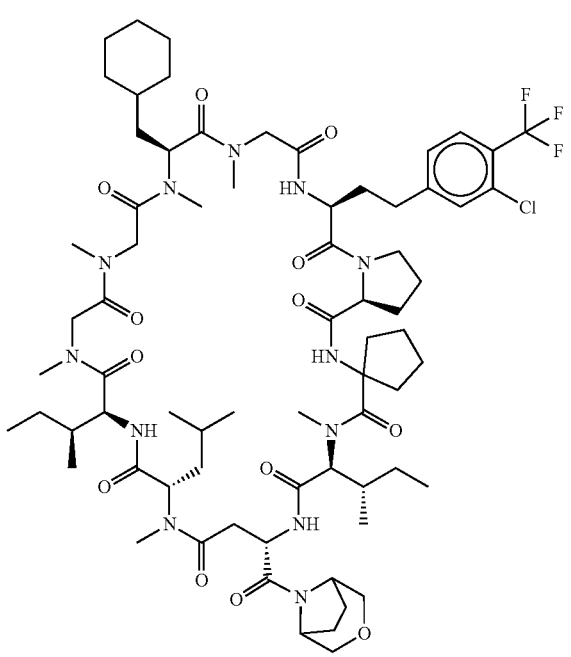 |

TABLE 24-continued
| Compound No. | Structural formula |
|---|---|
| 1258 | 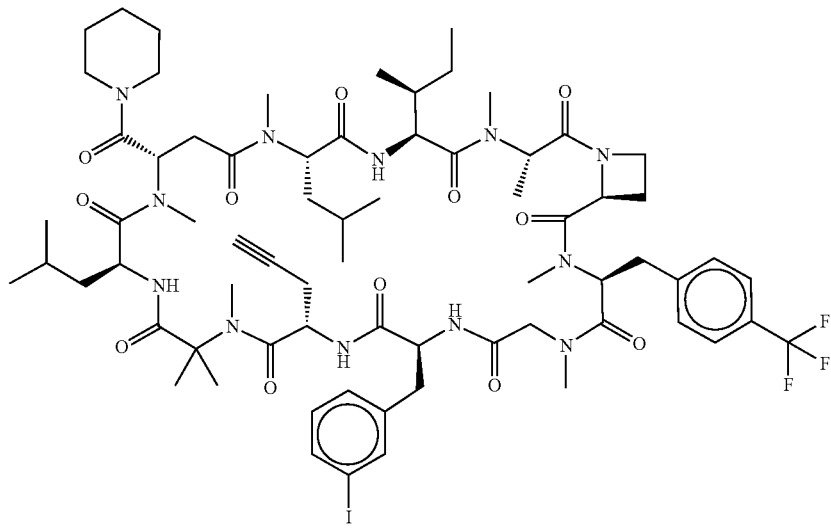 |
| 1259 | 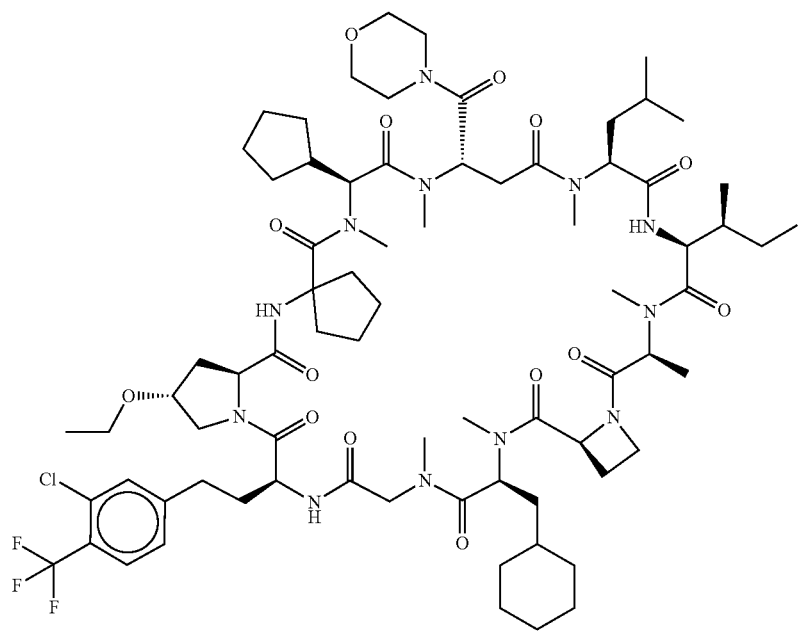 |

TABLE 24-continued
| Compound No. | Structural formula |
|---|---|
| 1260 | 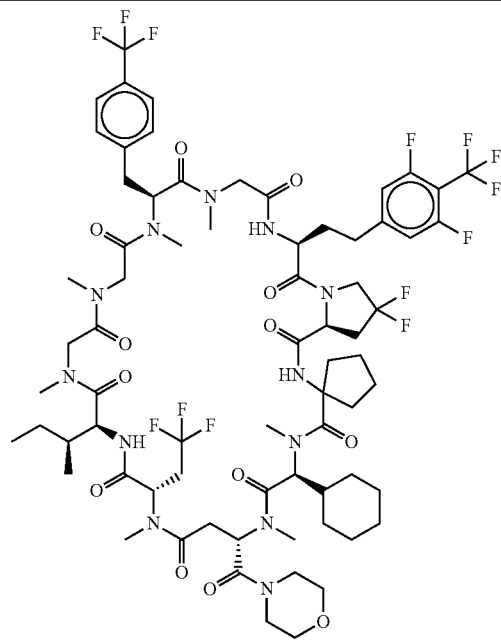 |
| 1261 | 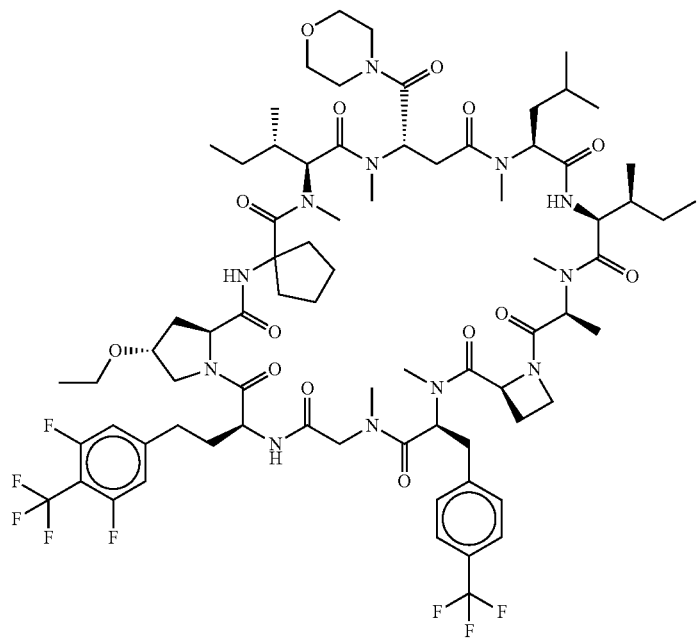 |

TABLE 24-continued
| Compound No. | Structural formula |
|---|---|
| 1262 | 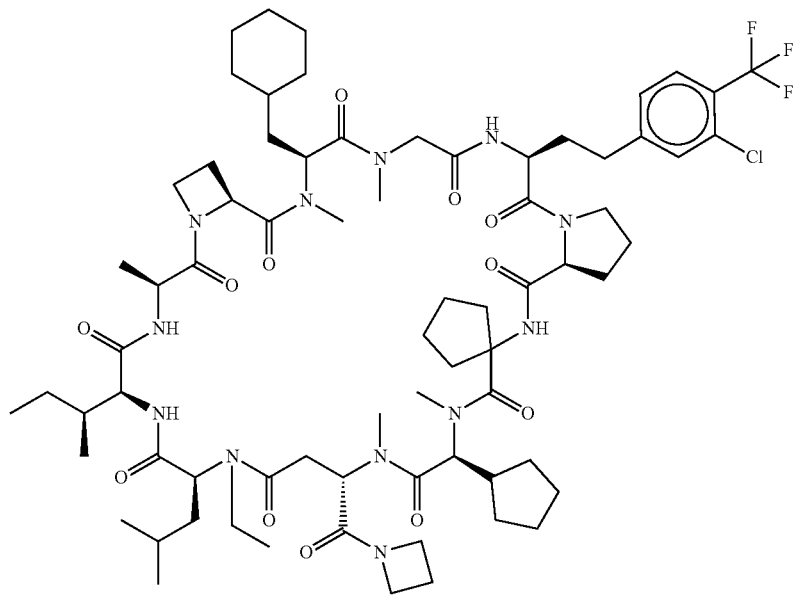 |
| 1263 | 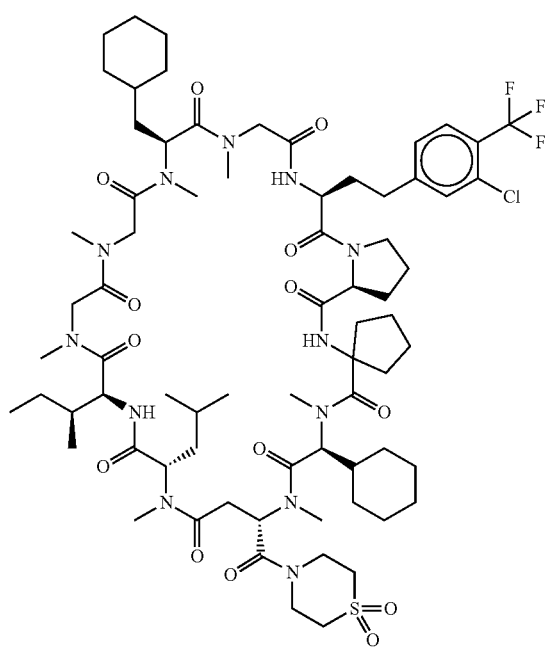 |

TABLE 24-continued
| Compound No. | Structural formula |
|---|---|
| 1264 | 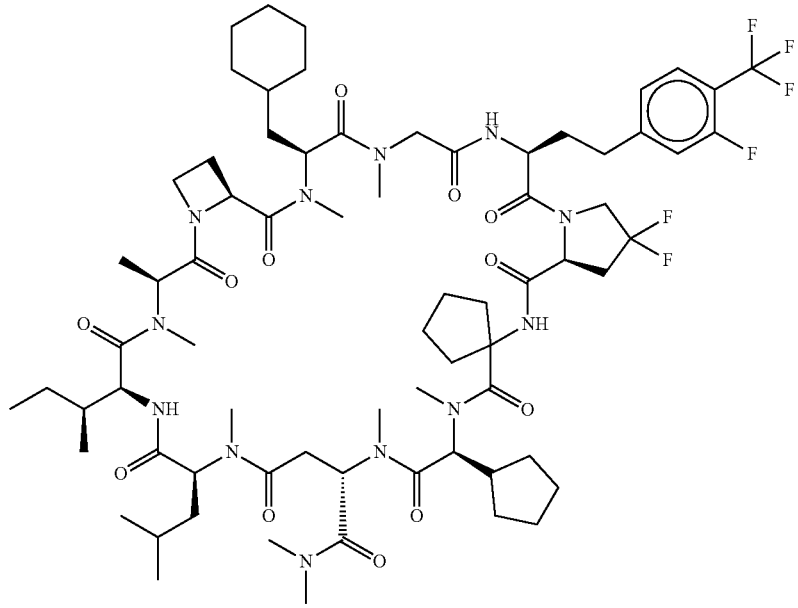 |
| 1265 | 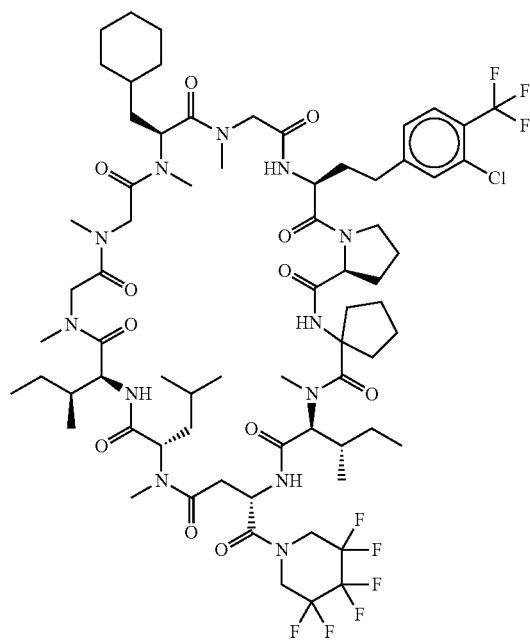 |

TABLE 24-continued
| Compound No. | Structural formula |
|---|---|
| 1266 | 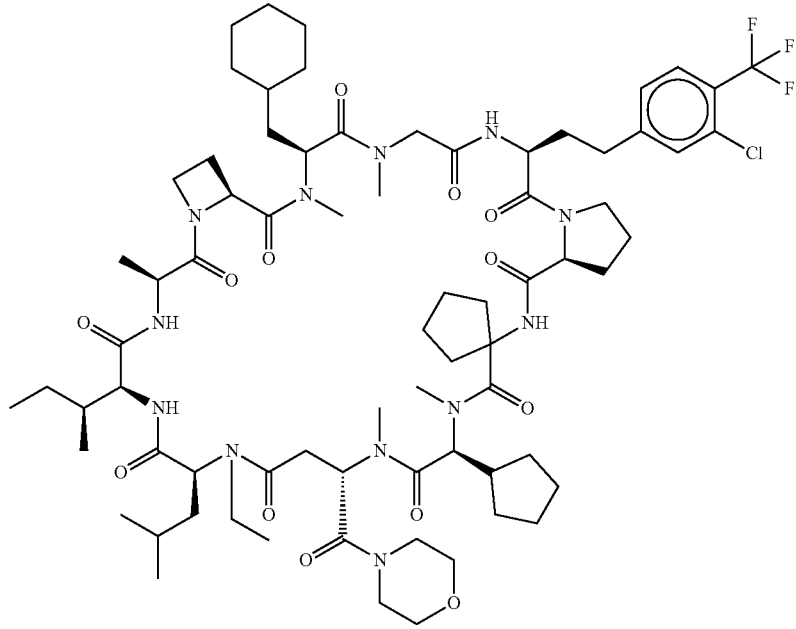 |
| 1267 | 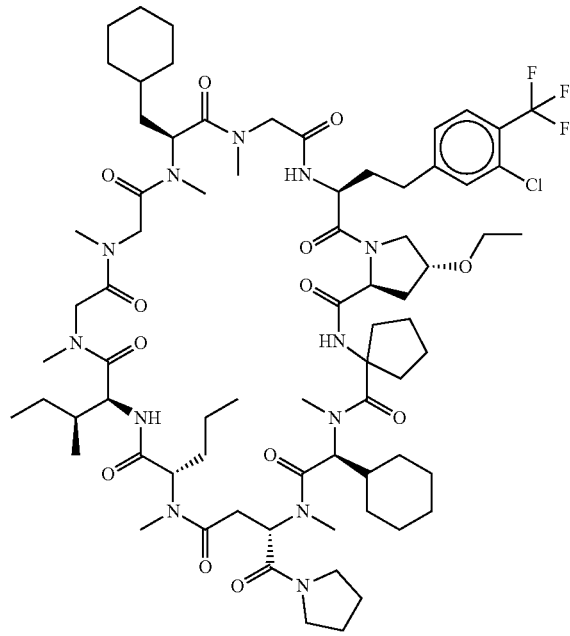 |

TABLE 24-continued
| Compound No. | Structural formula |
|---|---|
| 1268 | 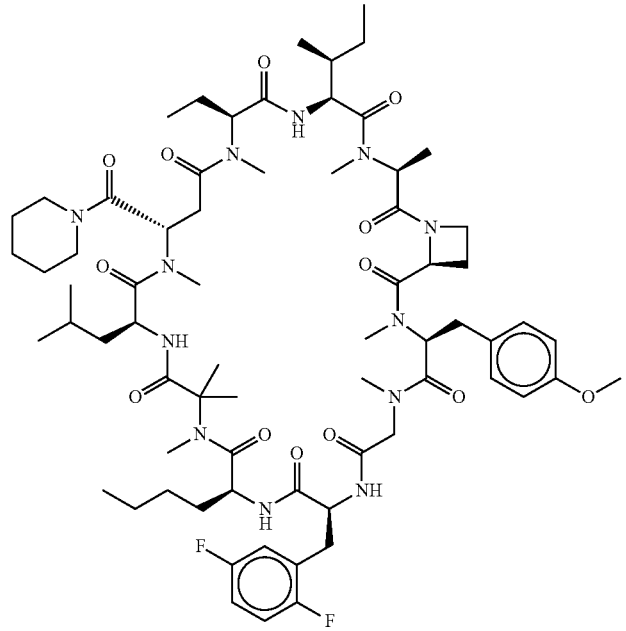 |
| 1269 | 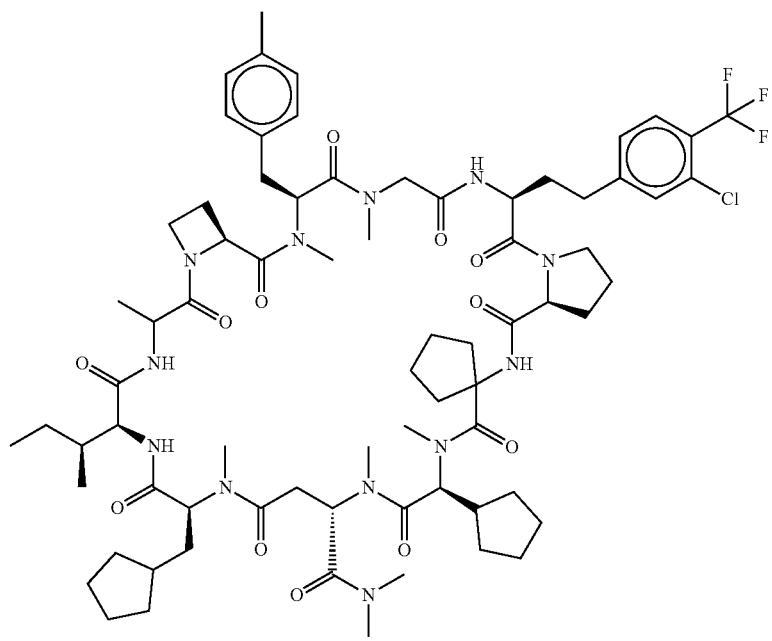 |

TABLE 24-continued
| Compound No. | Structural formula |
|---|---|
| 1270 | 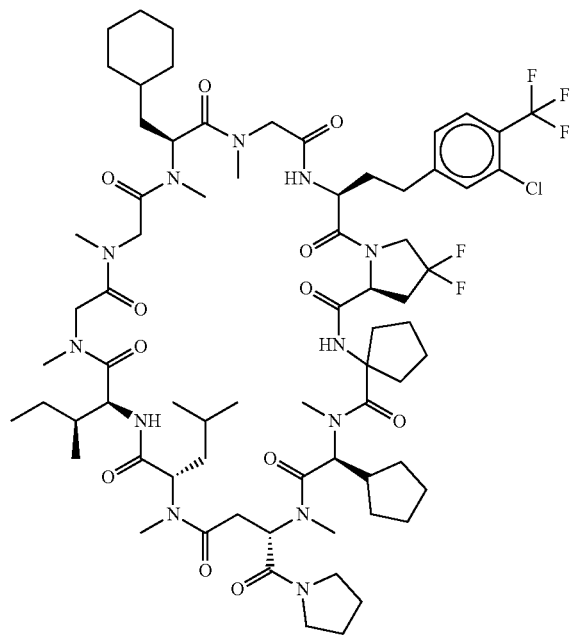 |
| 1271 | 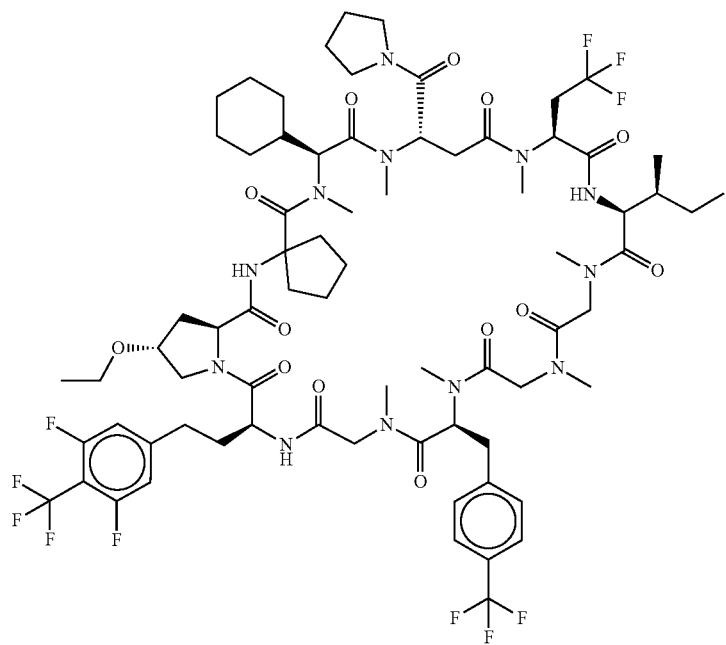 |

TABLE 24-continued
| Compound No. | Structural formula |
|---|---|
| 1272 | 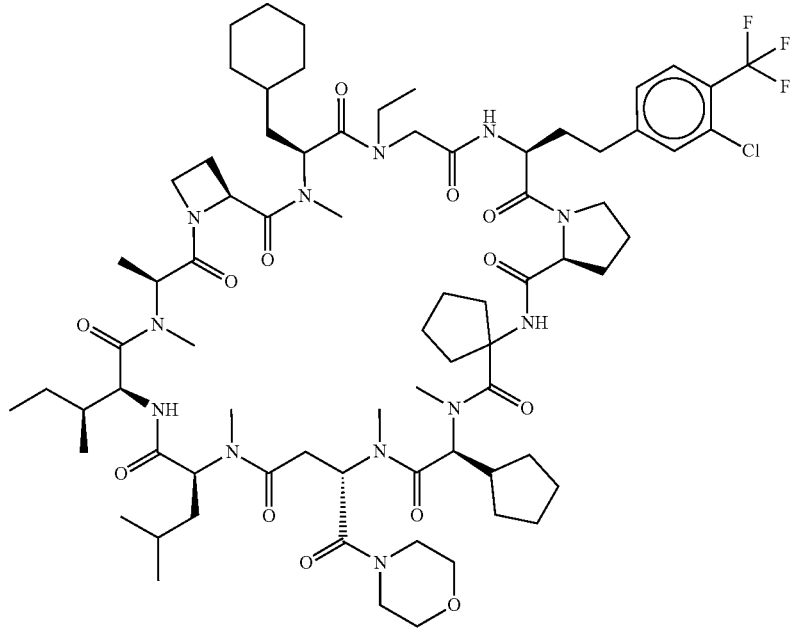 |
| 1273 | 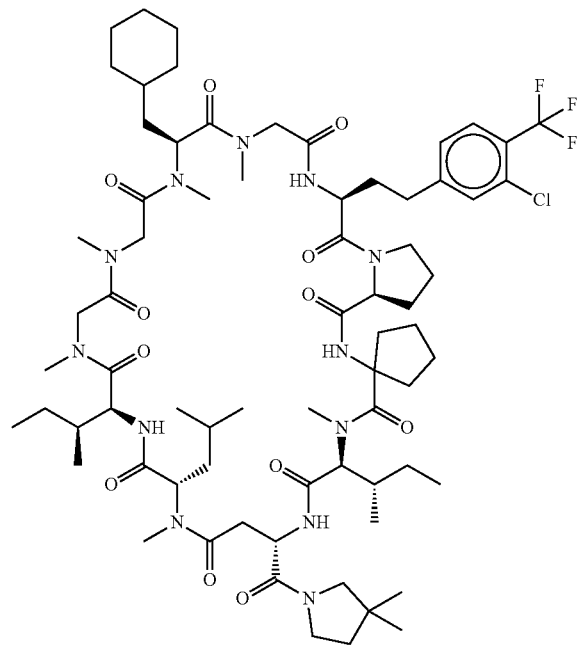 |

TABLE 24-continued
| Compound No. | Structural formula |
|---|---|
| 1274 | 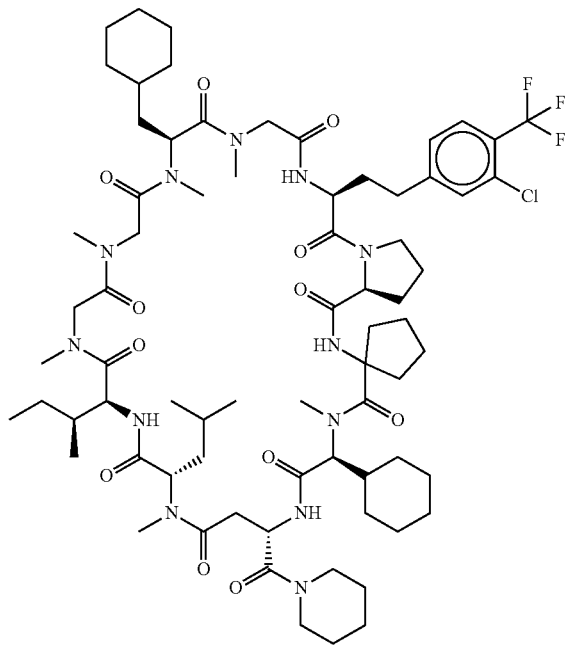 |
| 1275 | 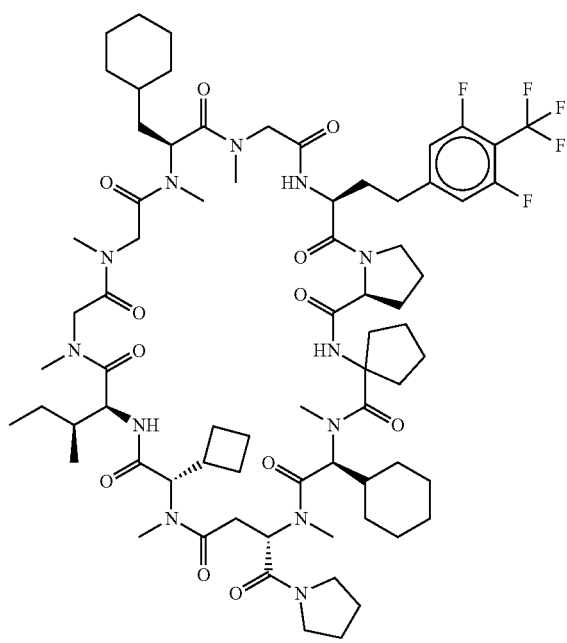 |

TABLE 24-continued
| Compound No. | Structural formula |
|---|---|
| 1276 | 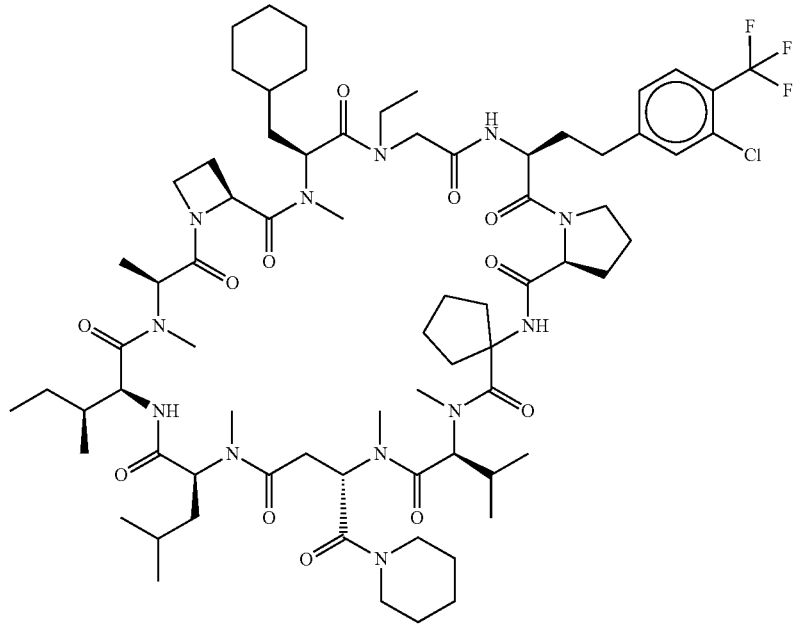 |
| 1277 | 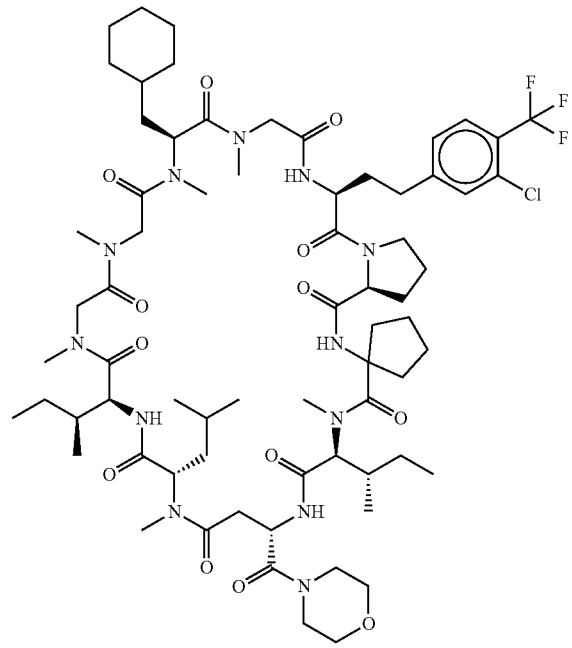 |

TABLE 24-continued
| Compound No. | Structural formula |
|---|---|
| 1278 | 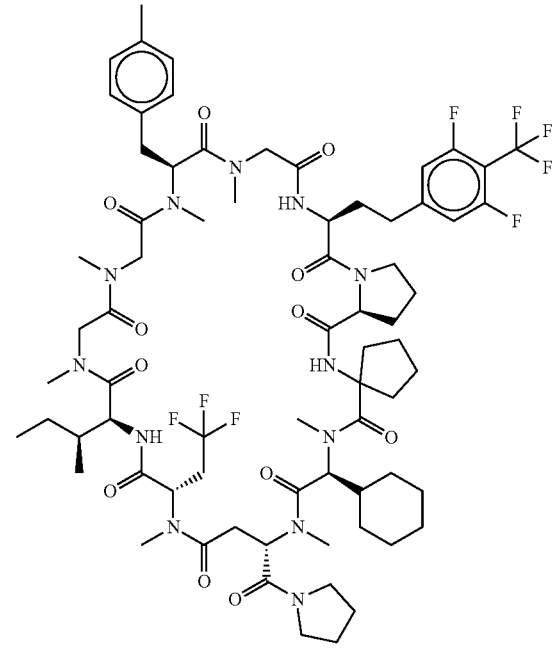 |
| 1279 | 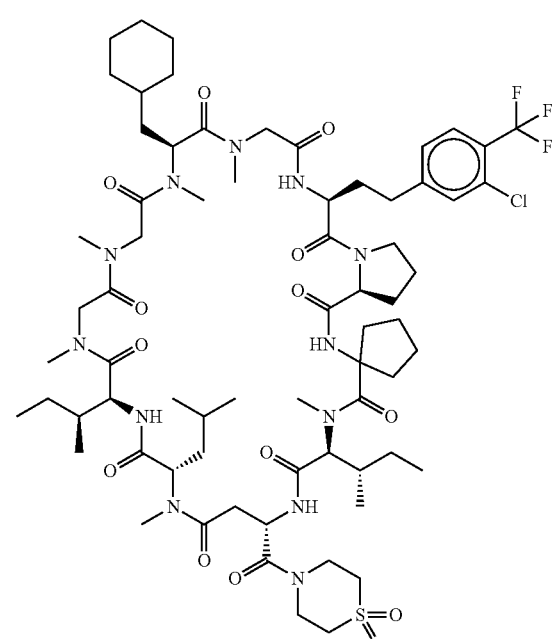 |

TABLE 24-continued
| Compound No. | Structural formula |
|---|---|
| 1280 | 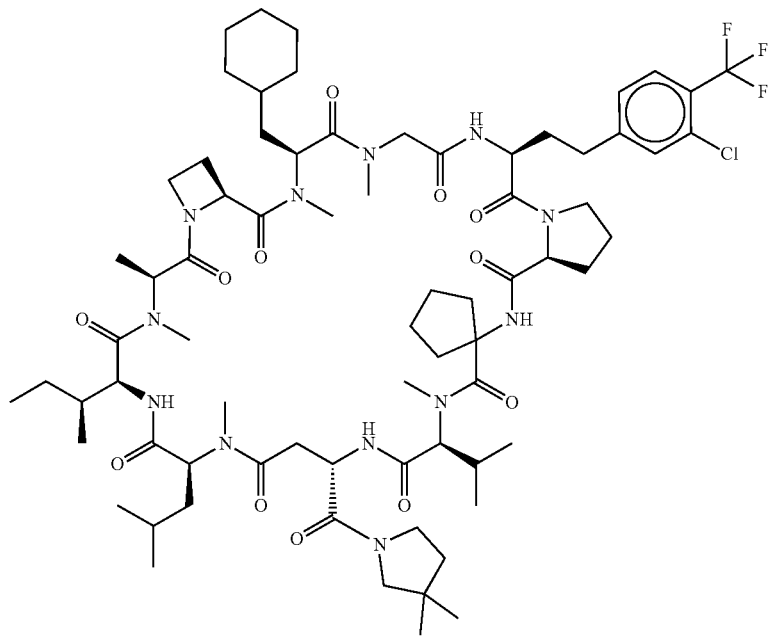 |
| 1281 | 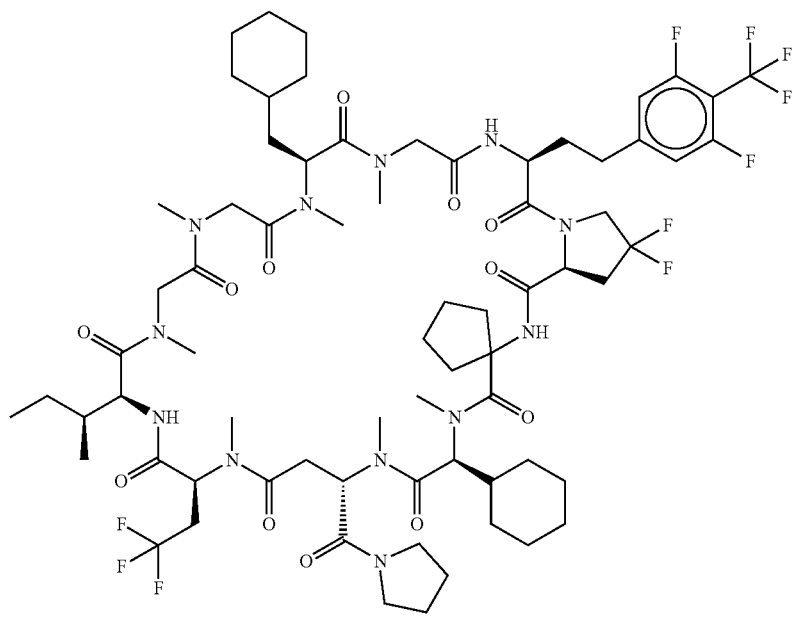 |

TABLE 24-continued
| Compound No. | Structural formula |
|---|---|
| 1282 | 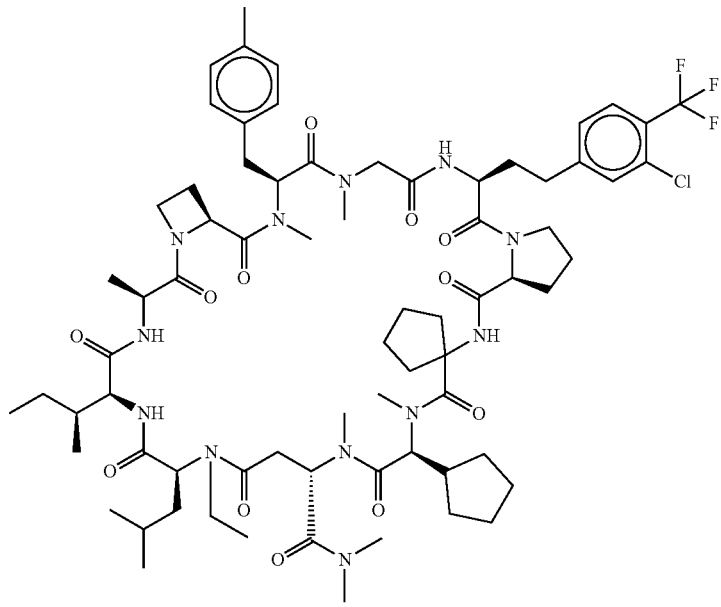 |
| 1283 | 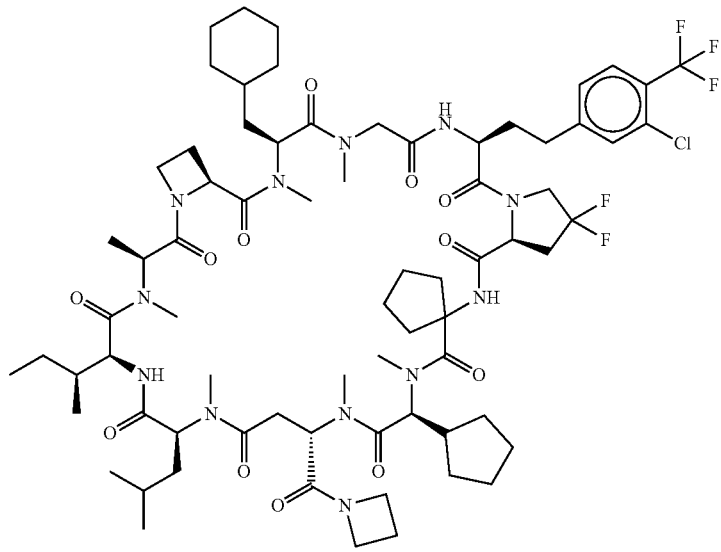 |

TABLE 24-continued
| Compound No. | Structural formula |
|---|---|
| 1284 | 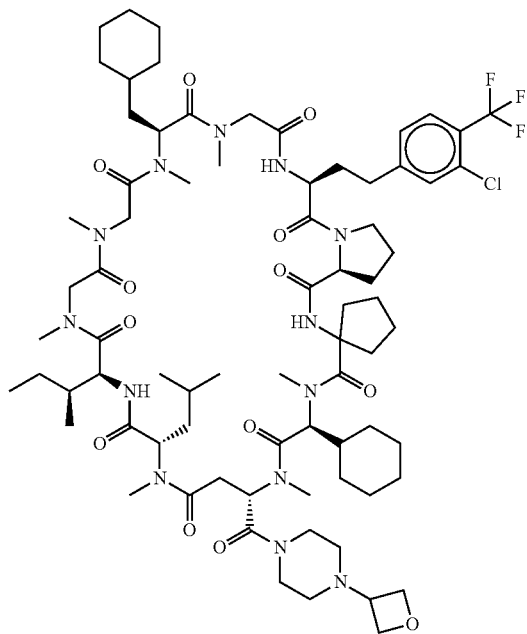 |
| 1285 | 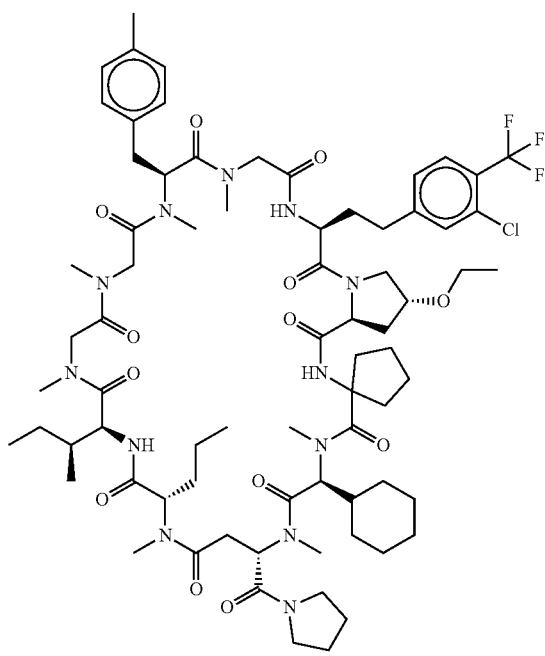 |

TABLE 24-continued
| Compound No. | Structural formula |
|---|---|
| 1286 | 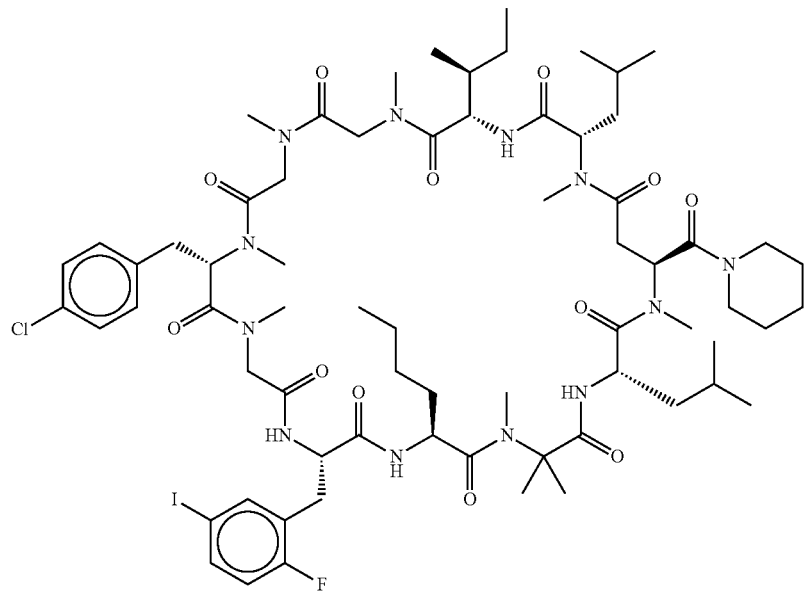 |
| 1287 | 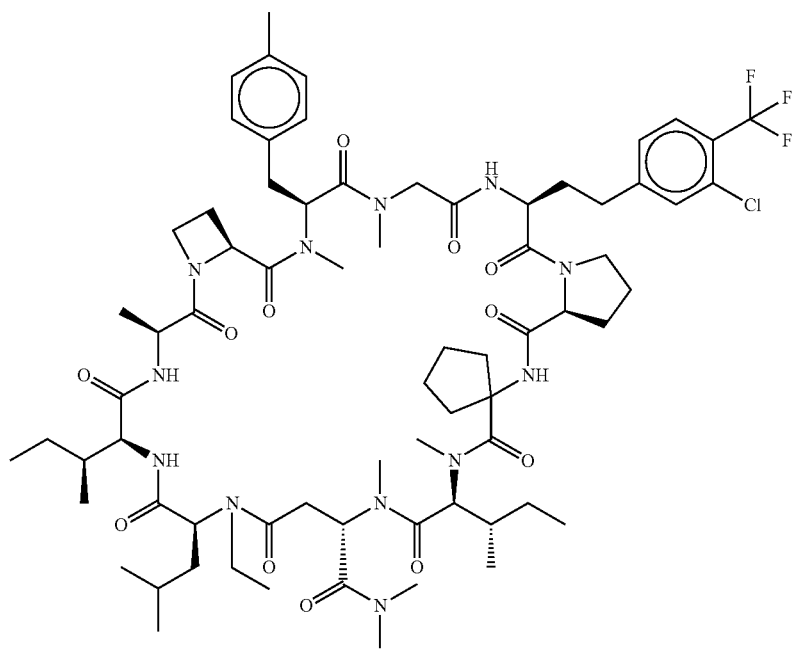 |

TABLE 24-continued
| Compound No. | Structural formula |
|---|---|
| 1288 | 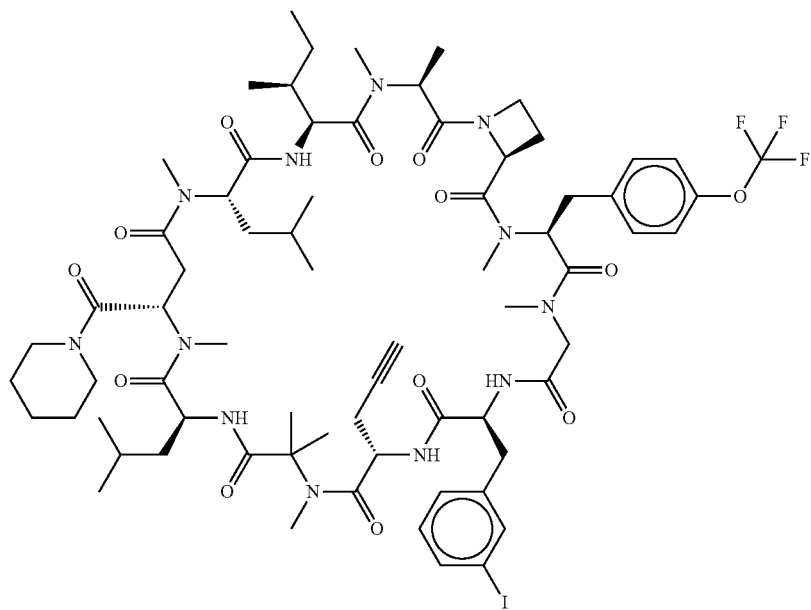 |
| 1289 | 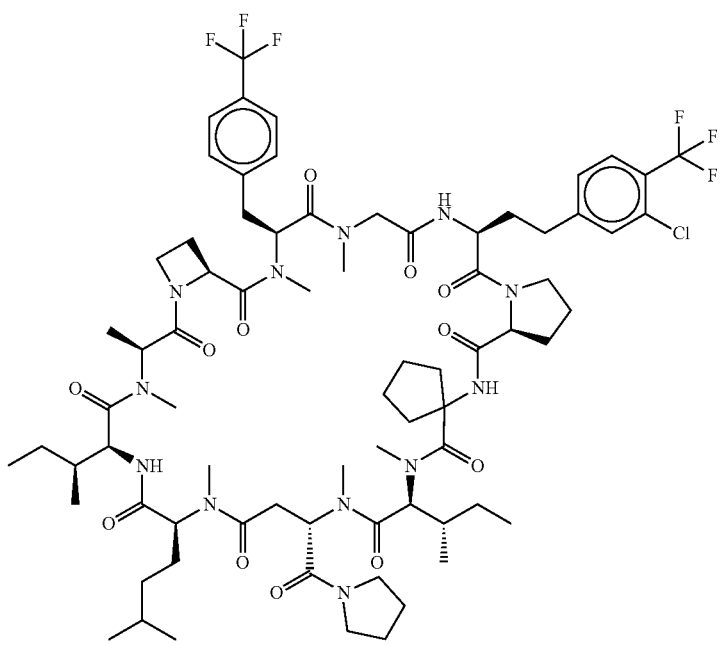 |

TABLE 24-continued
| Compound No. | Structural formula |
|---|---|
| 1290 | 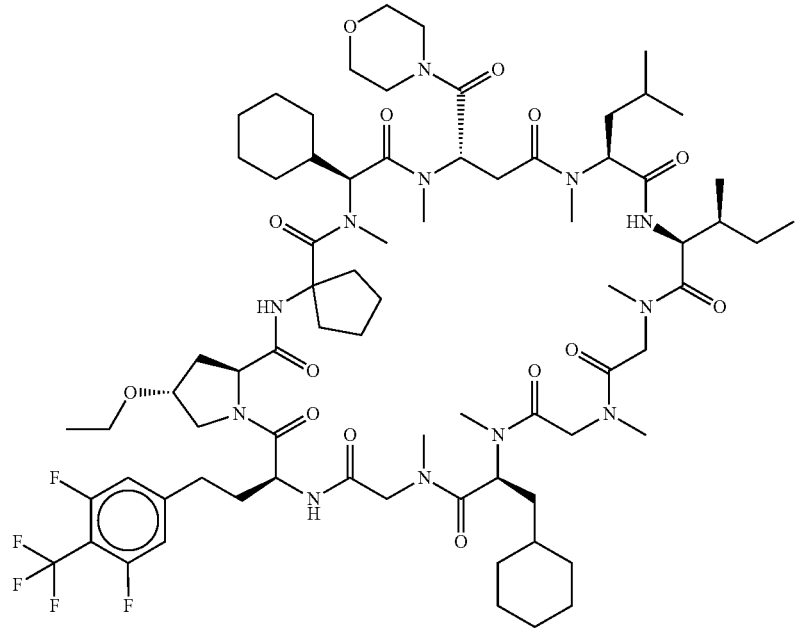 |
| 1291 | 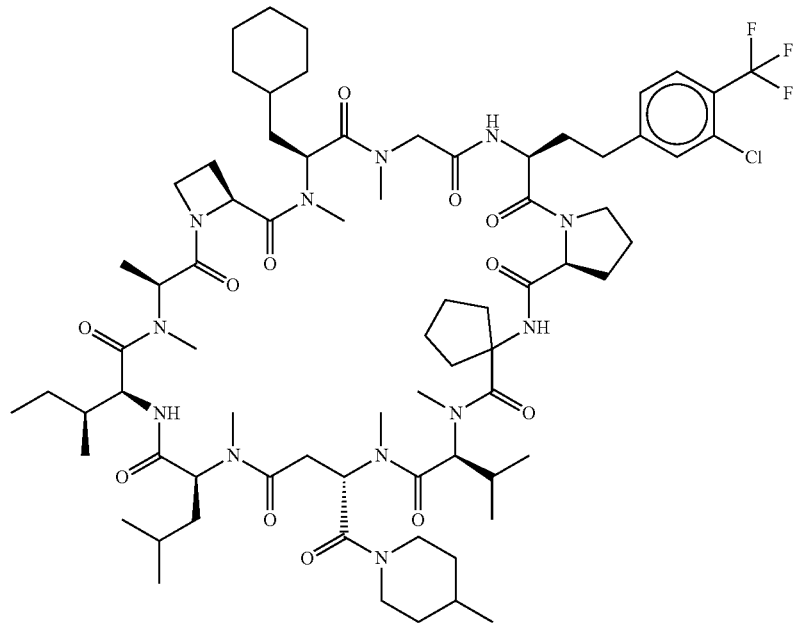 |

TABLE 24-continued
| Compound No. | Structural formula |
|---|---|
| 1292 | 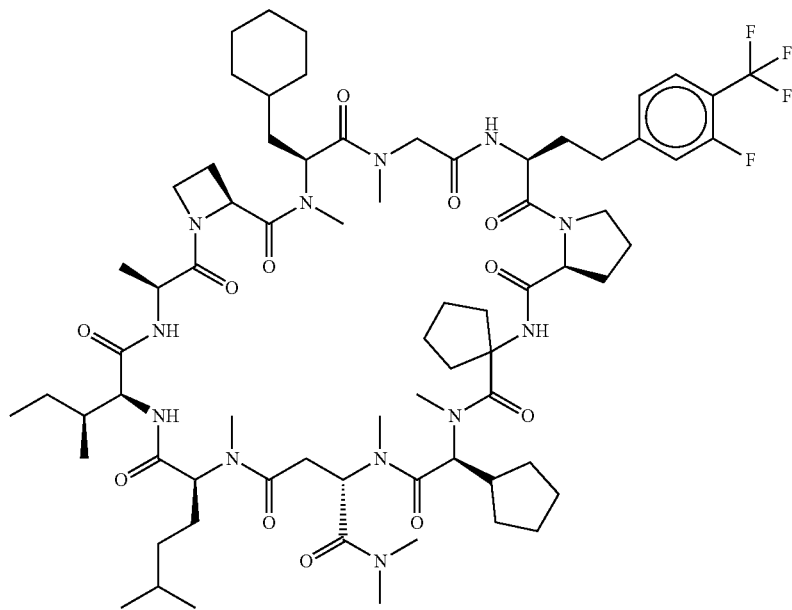 |
| 1293 | 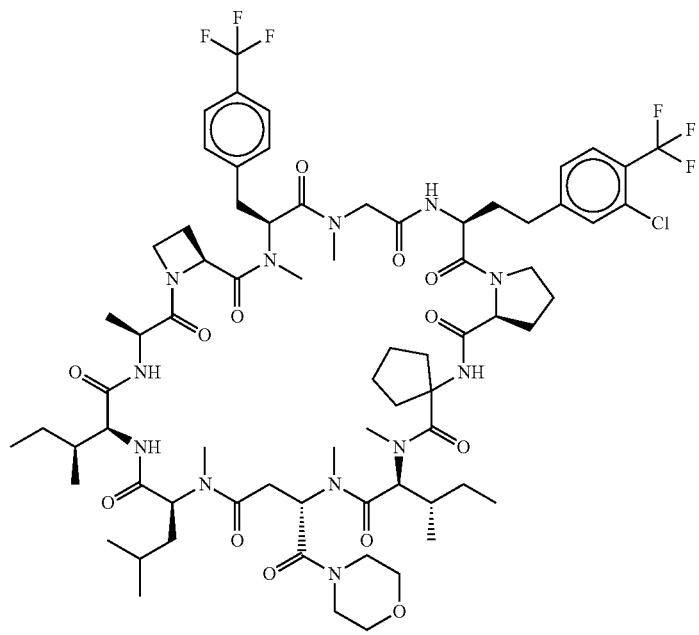 |

TABLE 24-continued
| Compound No. | Structural formula |
|---|---|
| 1294 | 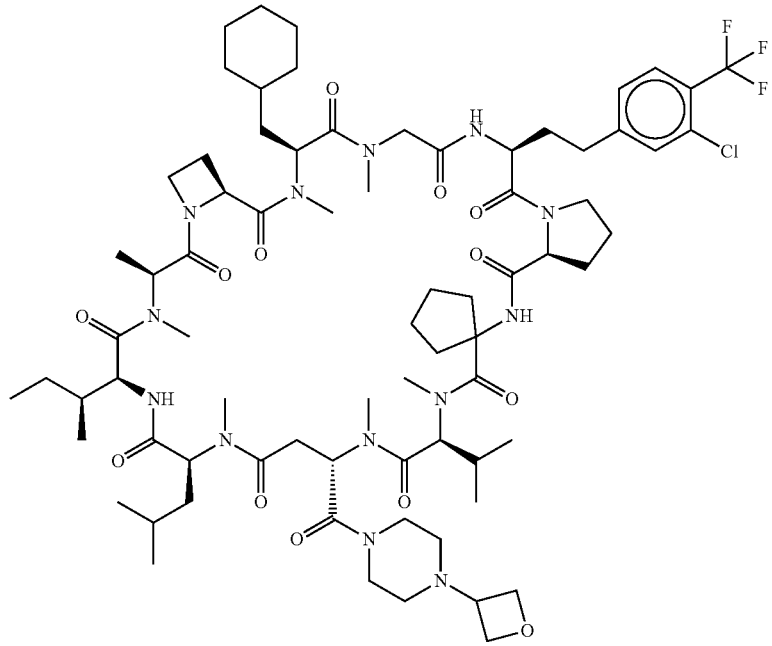 |
| 1295 | 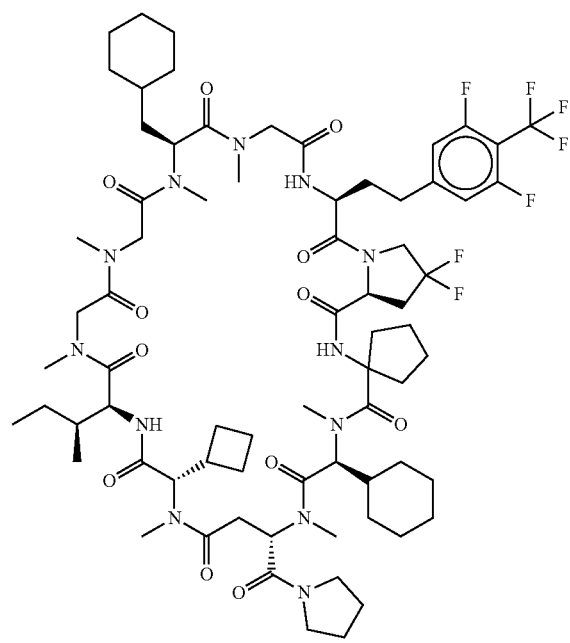 |

TABLE 24-continued
| Compound No. | Structural formula |
|---|---|
| 1296 | 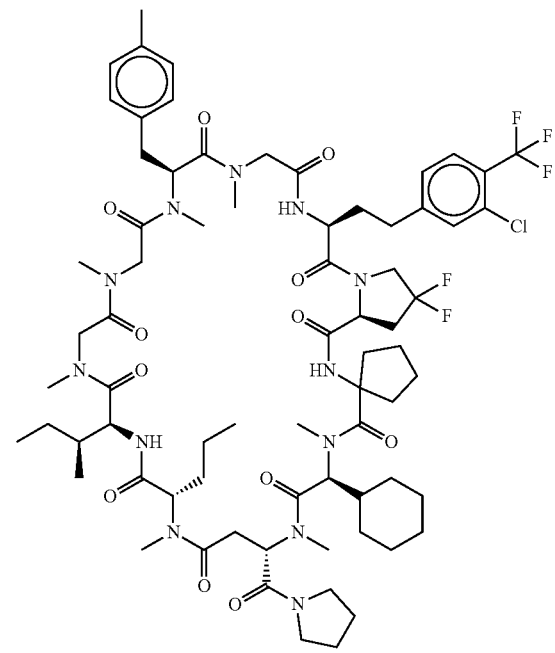 |
| 1297 | 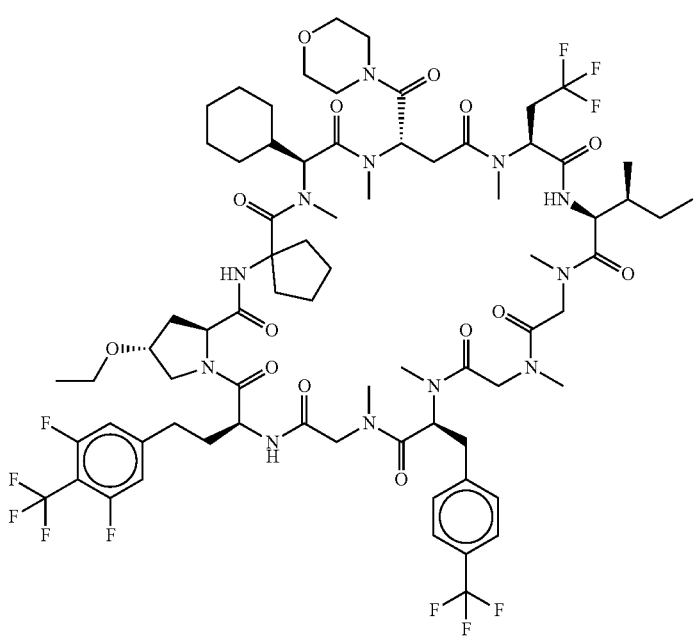 |

TABLE 24-continued
| Compound No. | Structural formula |
|---|---|
| 1298 | 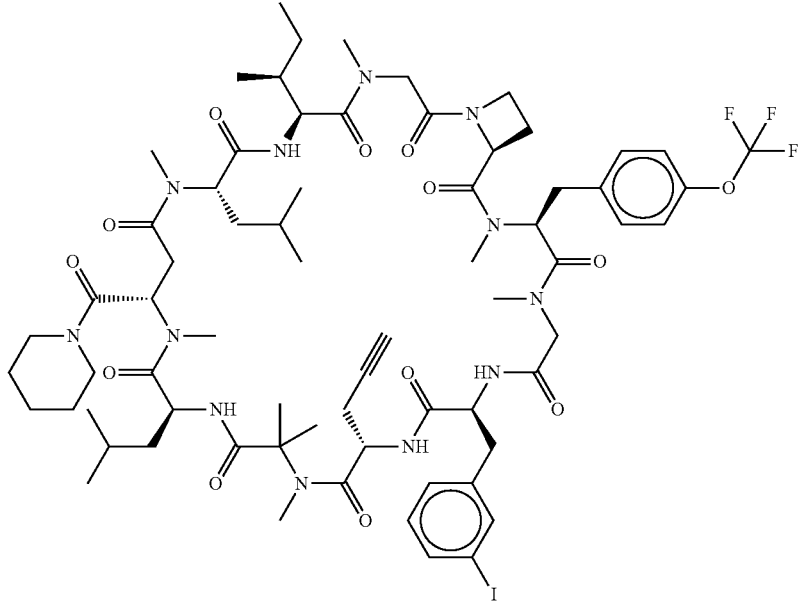 |
| 1299 | 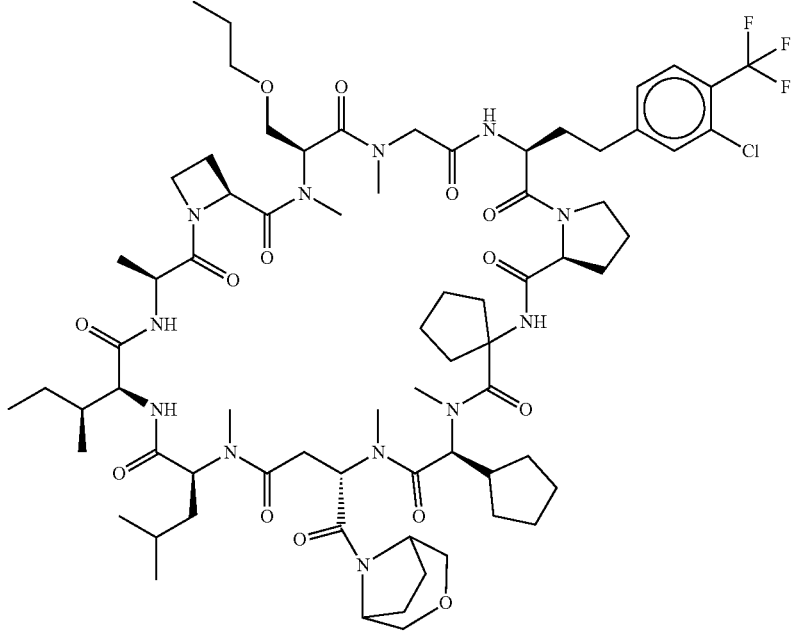 |

TABLE 24-continued
| Compound No. | Structural formula |
|---|---|
| 1300 | 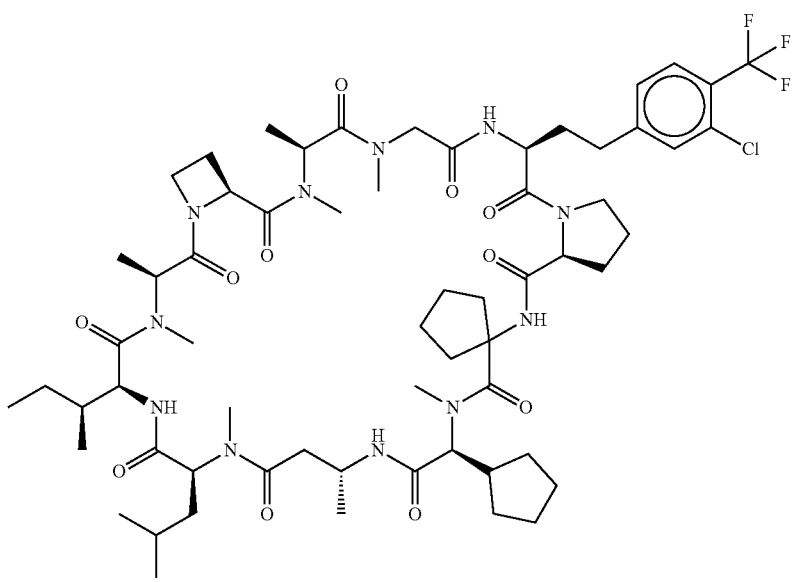 |
| 1301 | 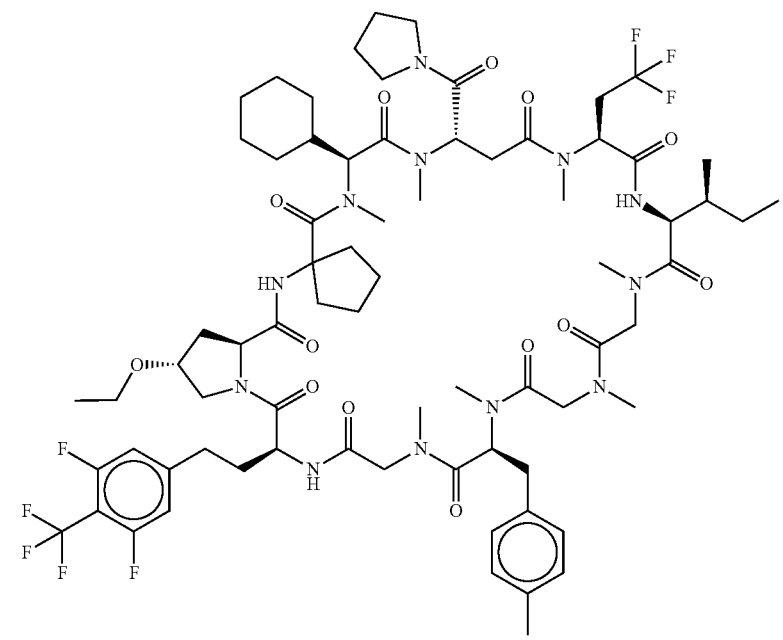 |

TABLE 24-continued
| Compound No. | Structural formula |
|---|---|
| 1302 | 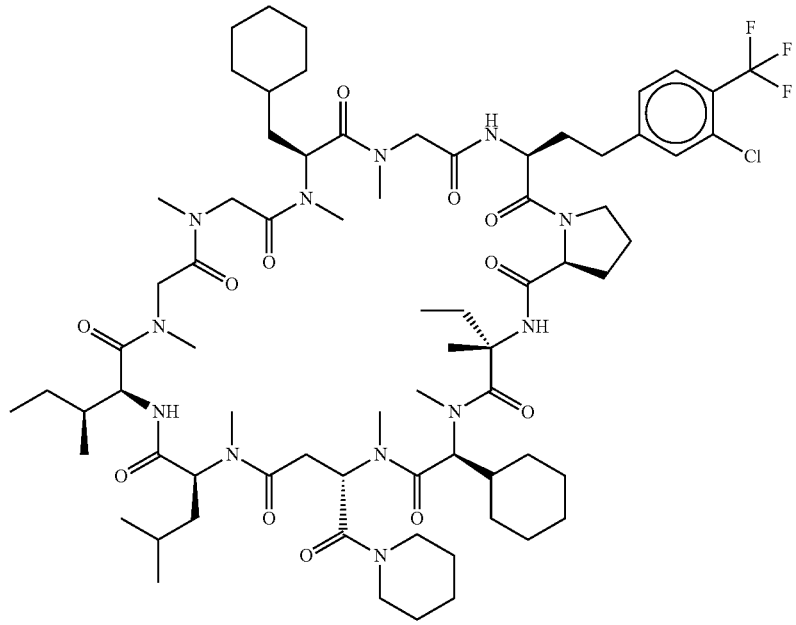 |
| 1303 | 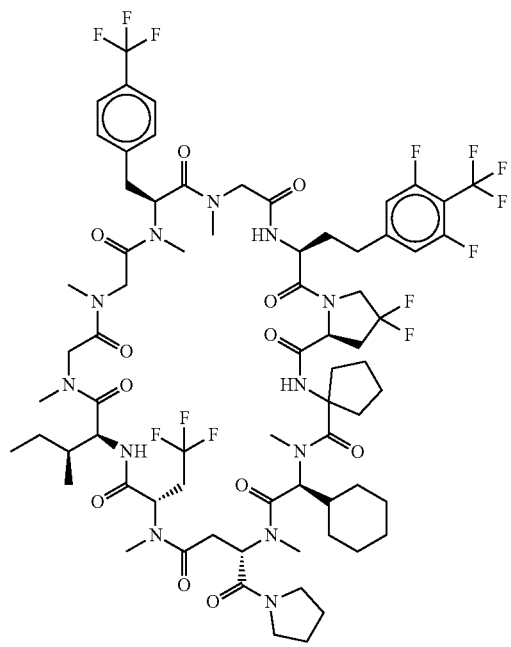 |

TABLE 24-continued
| Compound No. | Structural formula |
|---|---|
| 1304 | 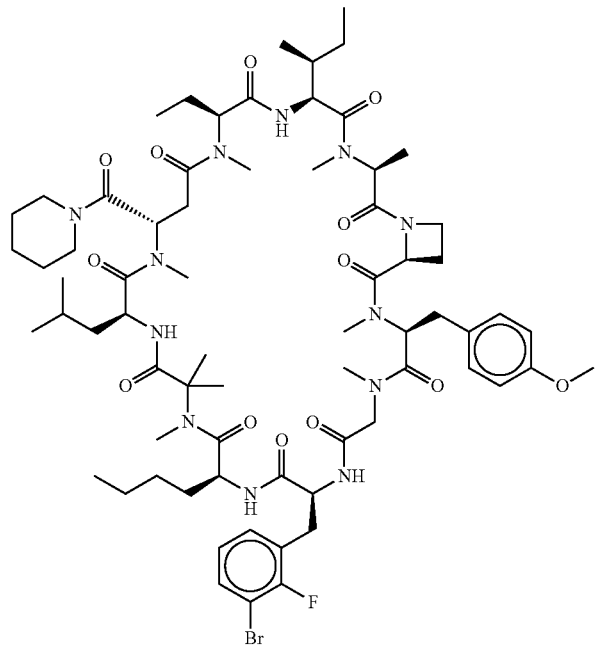 |
| 1305 | 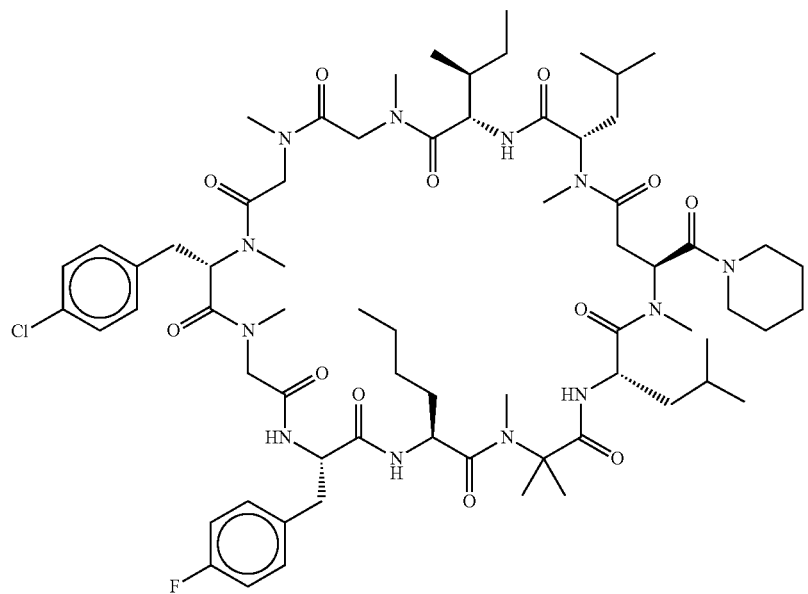 |

TABLE 24-continued
| Compound No. | Structural formula |
|---|---|
| 1306 | 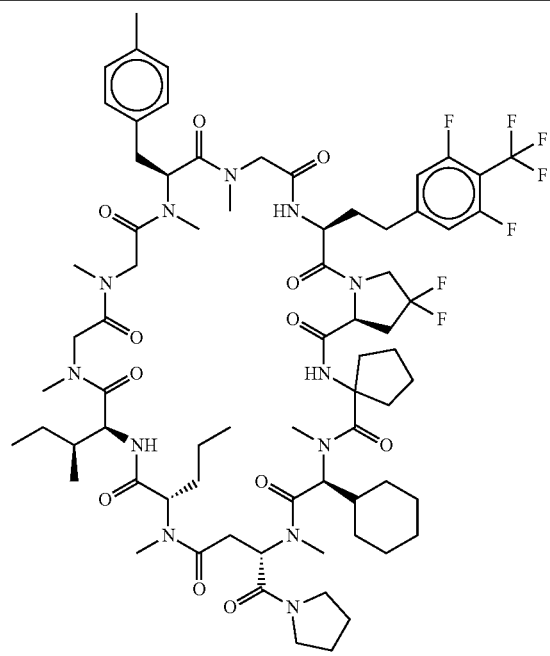 |
| 1307 | 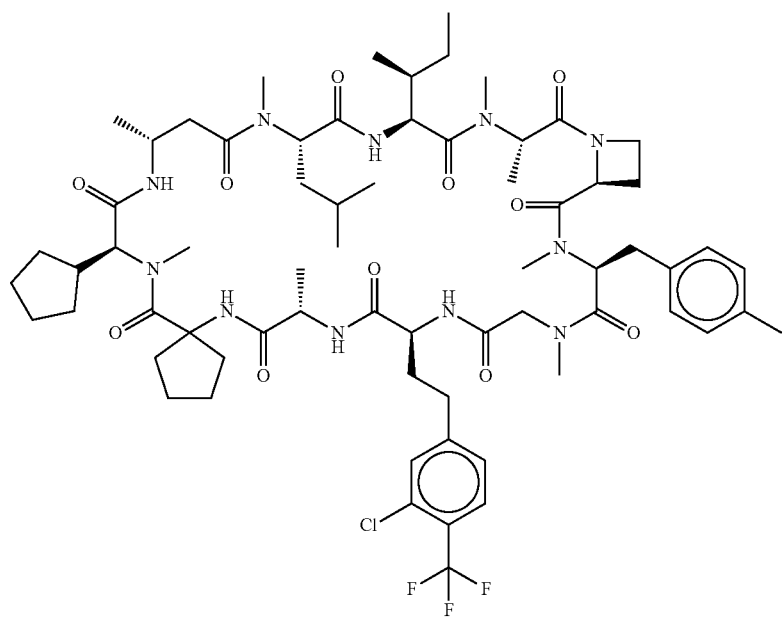 |

TABLE 24-continued
| Compound No. | Structural formula |
|---|---|
| 1308 | 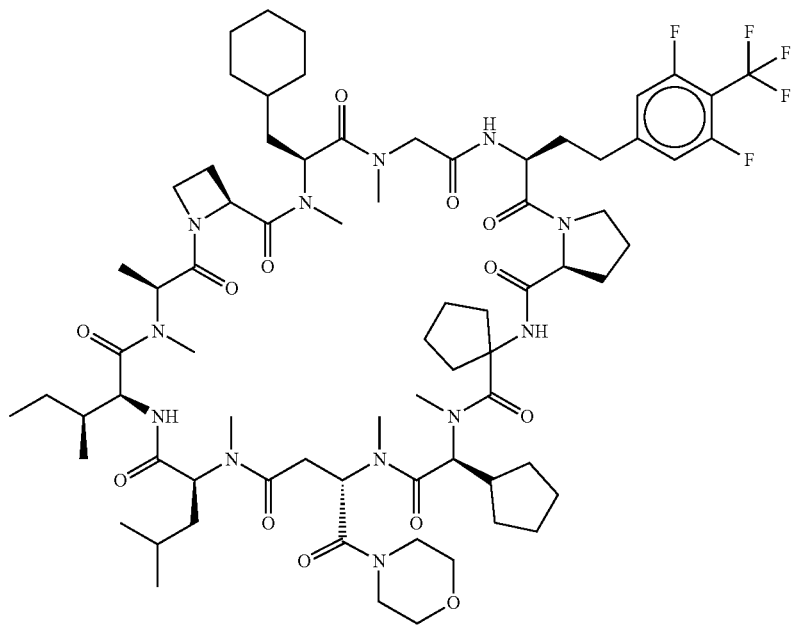 |
| 1309 | 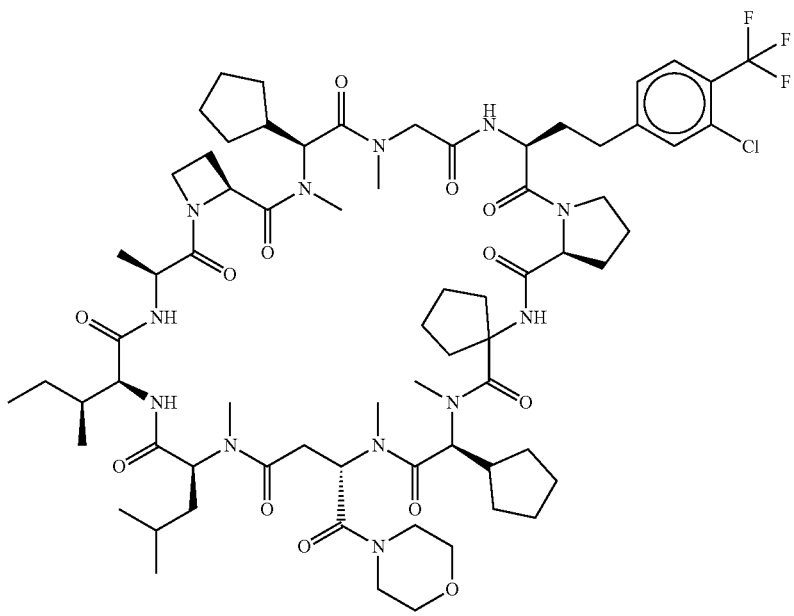 |

TABLE 24-continued
| Compound No. | Structural formula |
|---|---|
| 1310 | 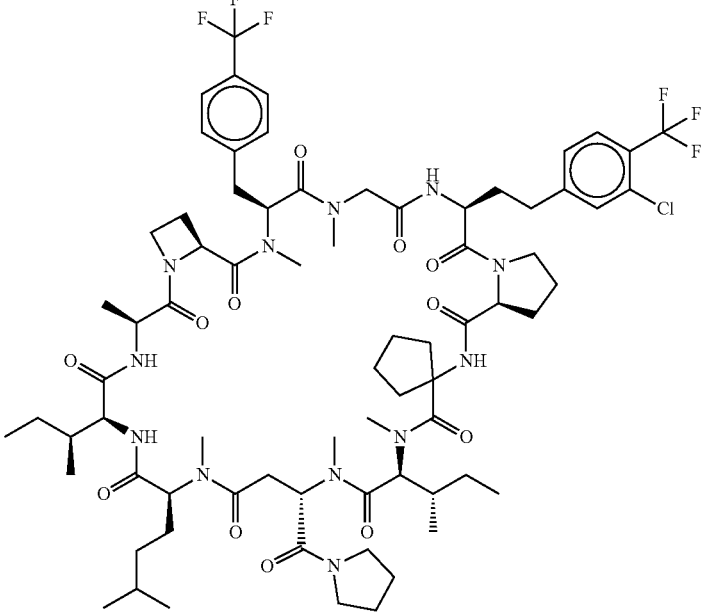 |
| 1311 | 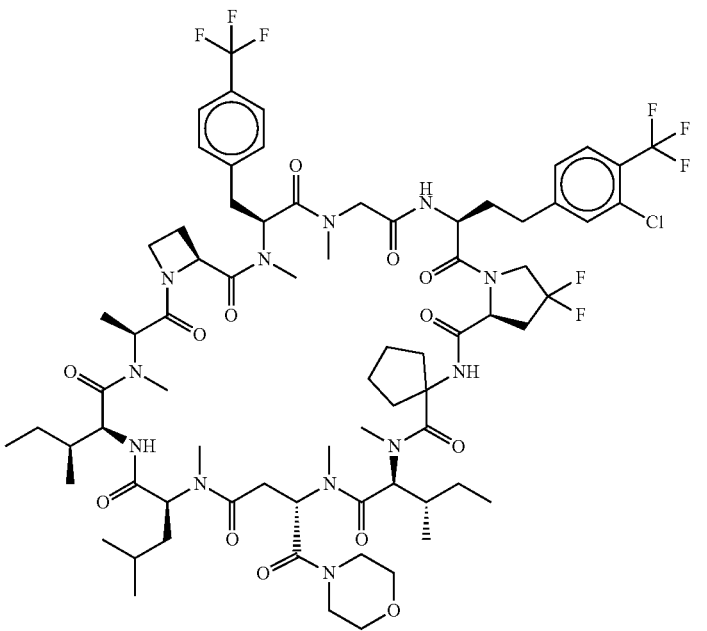 |

TABLE 24-continued
| Compound No. | Structural formula |
|---|---|
| 1312 | 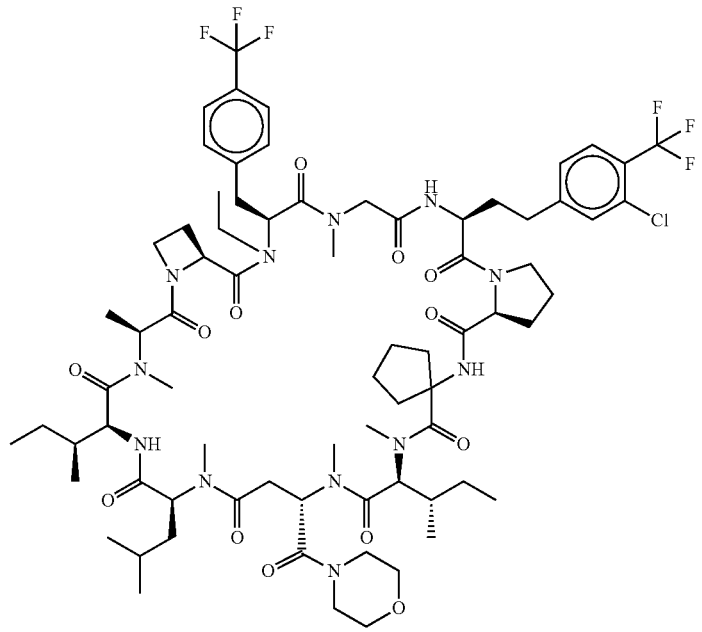 |
| 1313 | 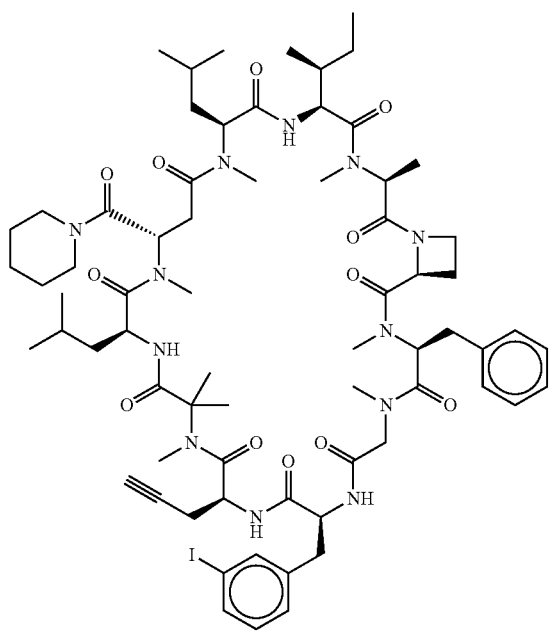 |

TABLE 24-continued
| Compound No. | Structural formula |
|---|---|
| 1314 | 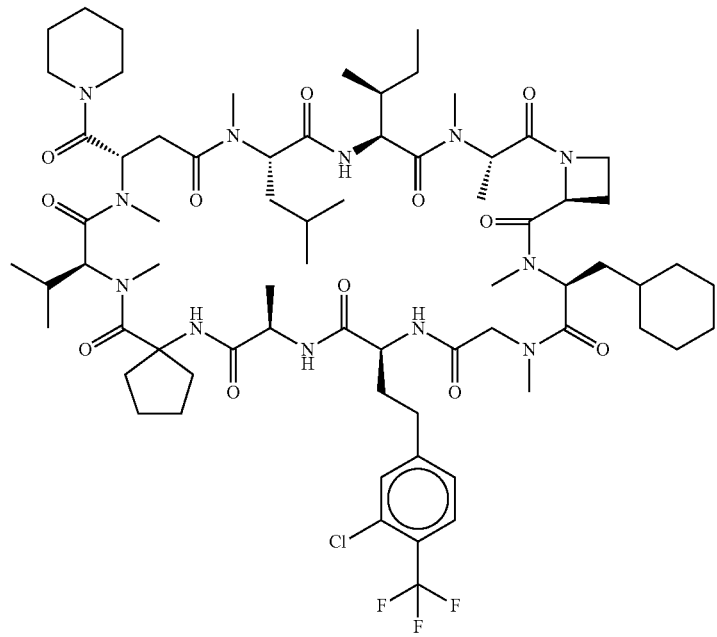 |
| 1315 | 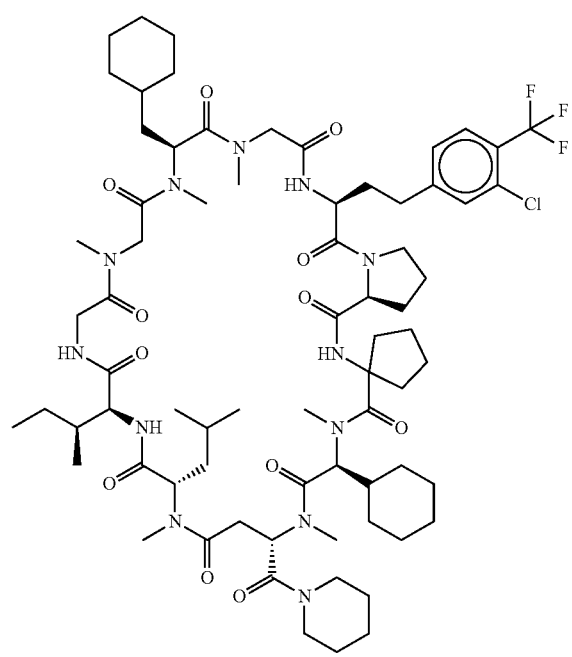 |

TABLE 24-continued
| Compound No. | Structural formula |
|---|---|
| 1316 | 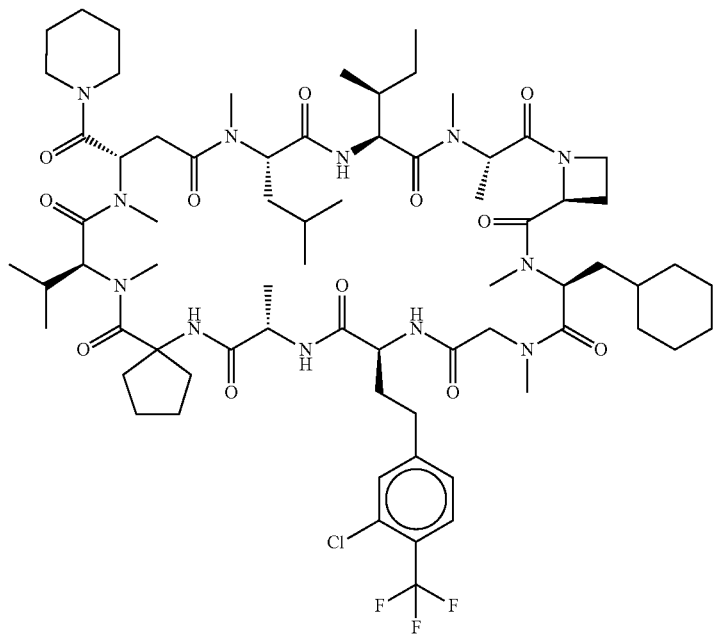 |
| 1317 | 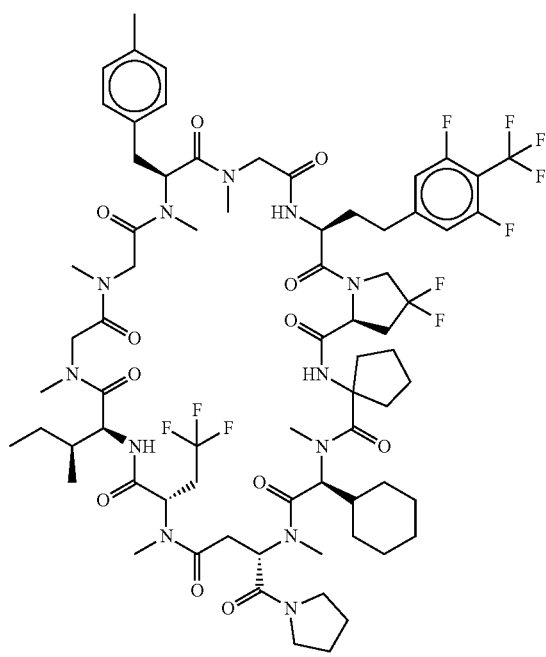 |

TABLE 24-continued
| Compound No. | Structural formula |
|---|---|
| 1318 | 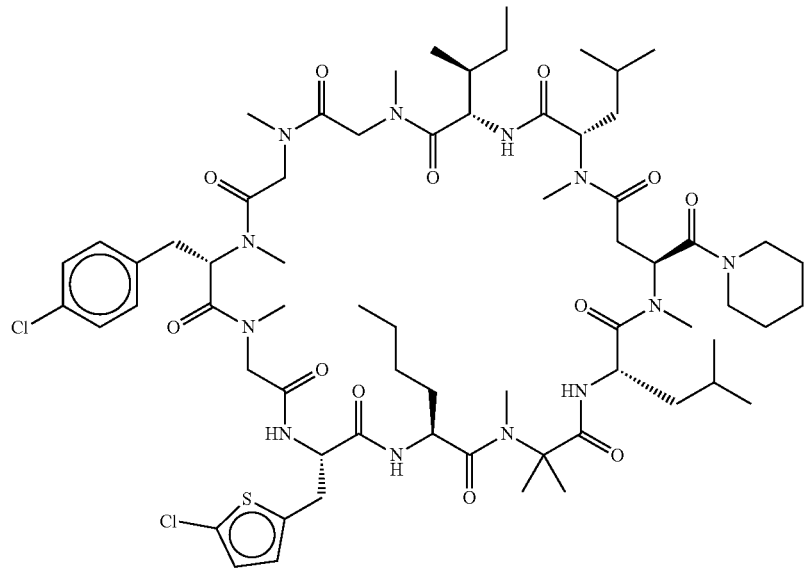 |
| 1319 | 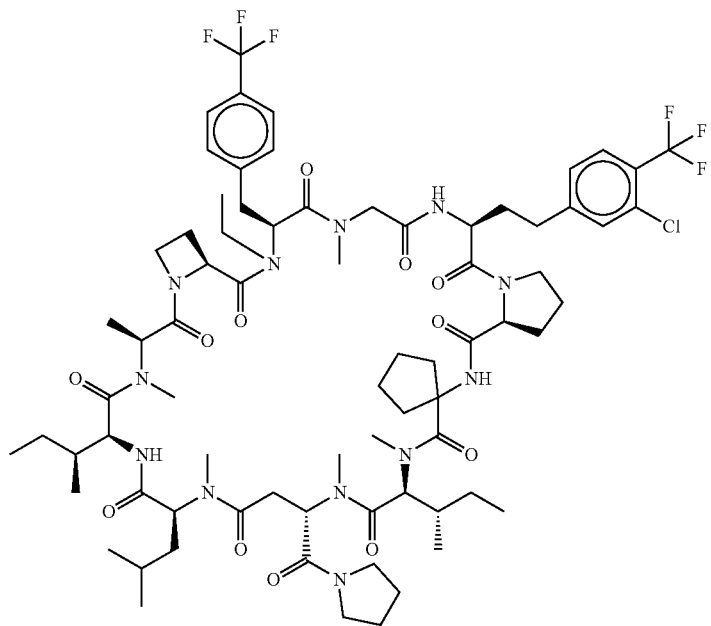 |

TABLE 24-continued
| Compound No. | Structural formula |
|---|---|
| 1320 | 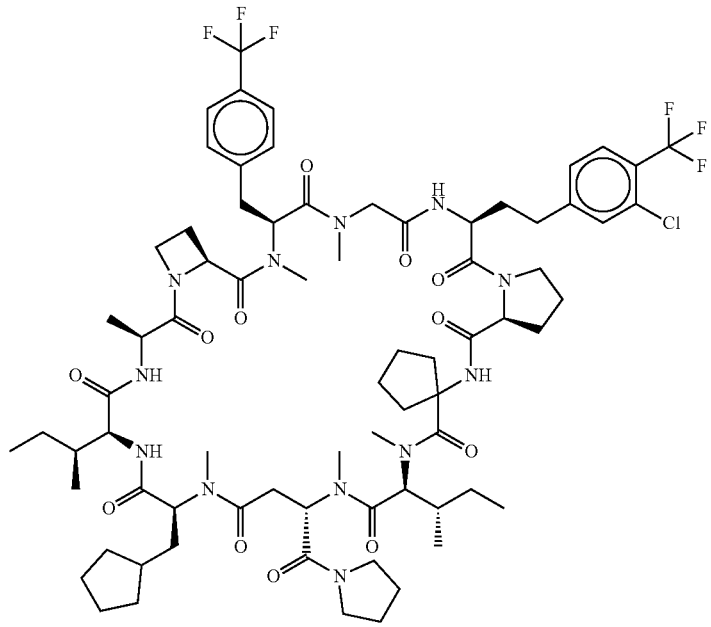 |
| 1321 | 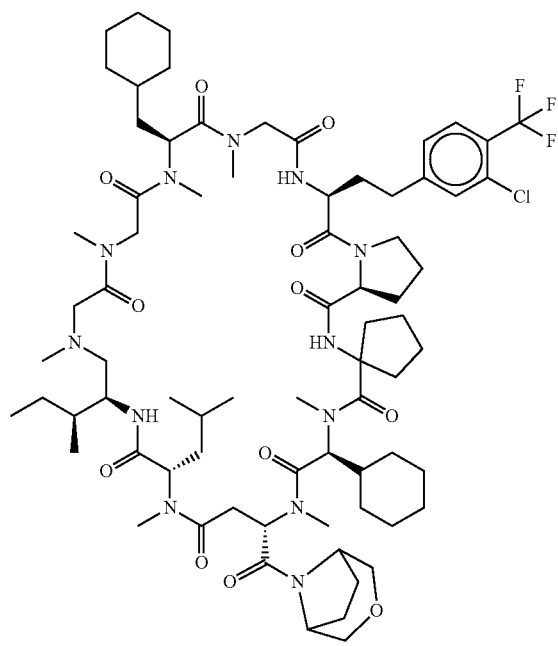 |

TABLE 24-continued
| Compound No. | Structural formula |
|---|---|
| 1322 | 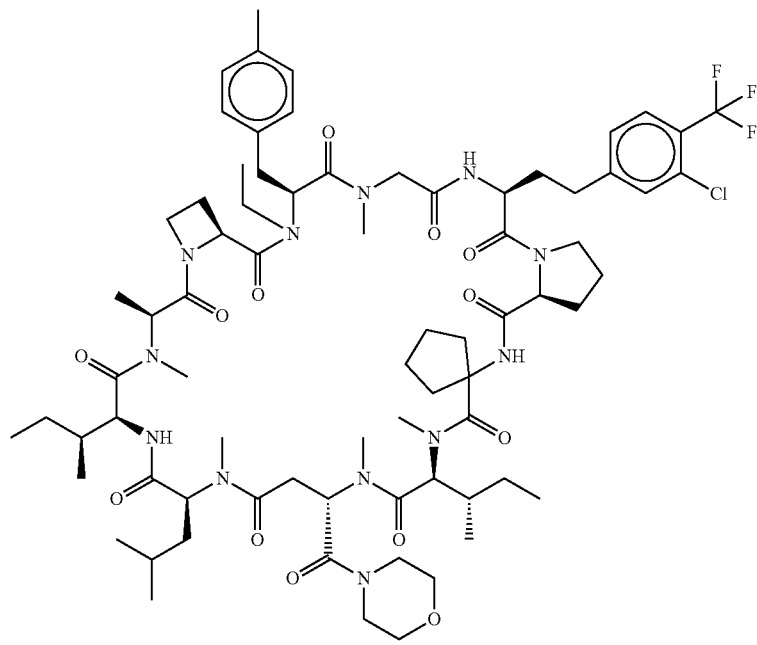 |
| 1323 | 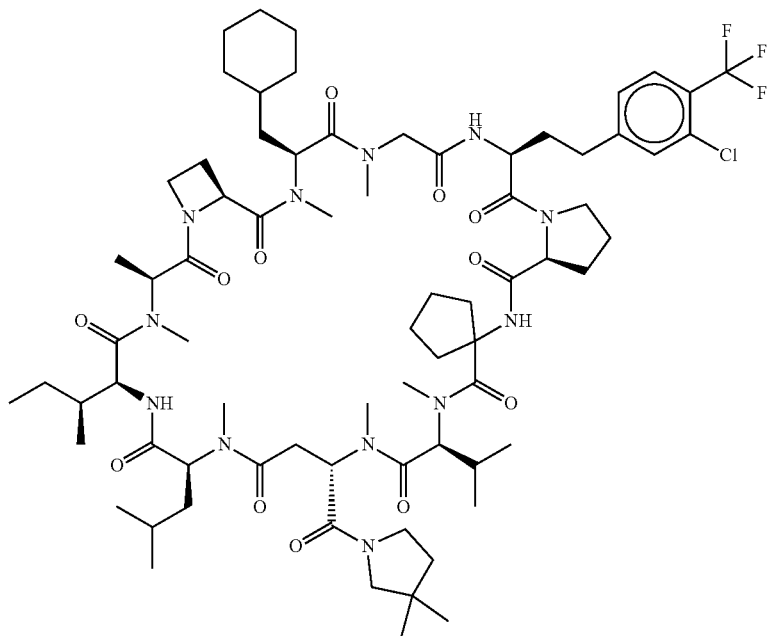 |

TABLE 24-continued
| Compound No. | Structural formula |
|---|---|
| 1324 | 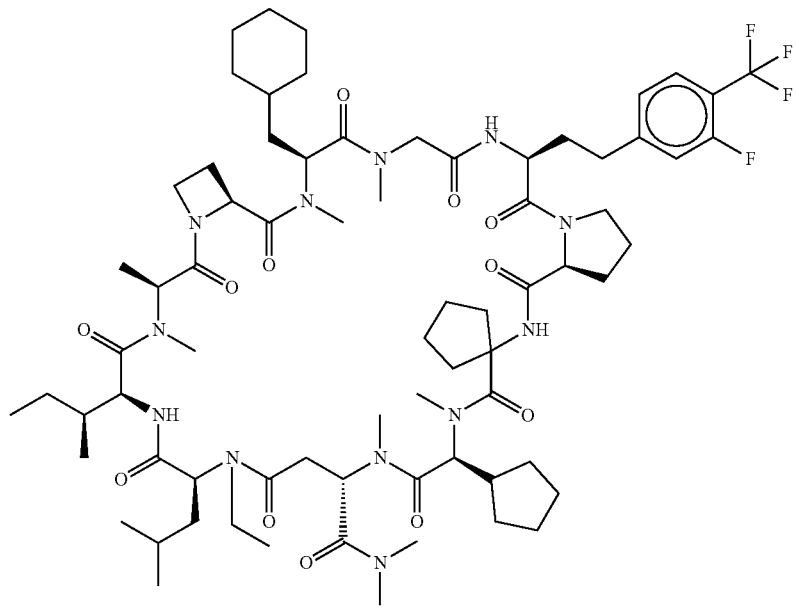 |
| 1325 | 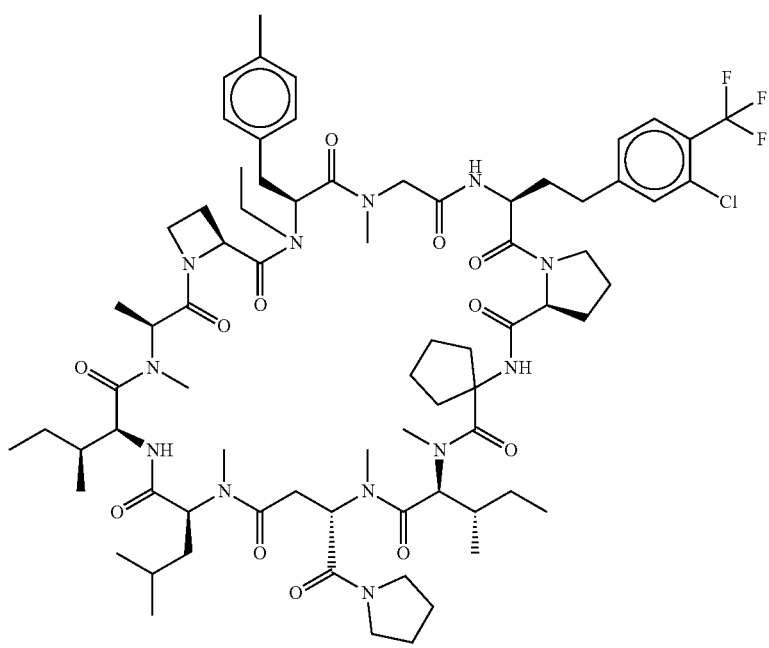 |

TABLE 24-continued
| Compound No. | Structural formula |
| --- | --- |
| 1326 | 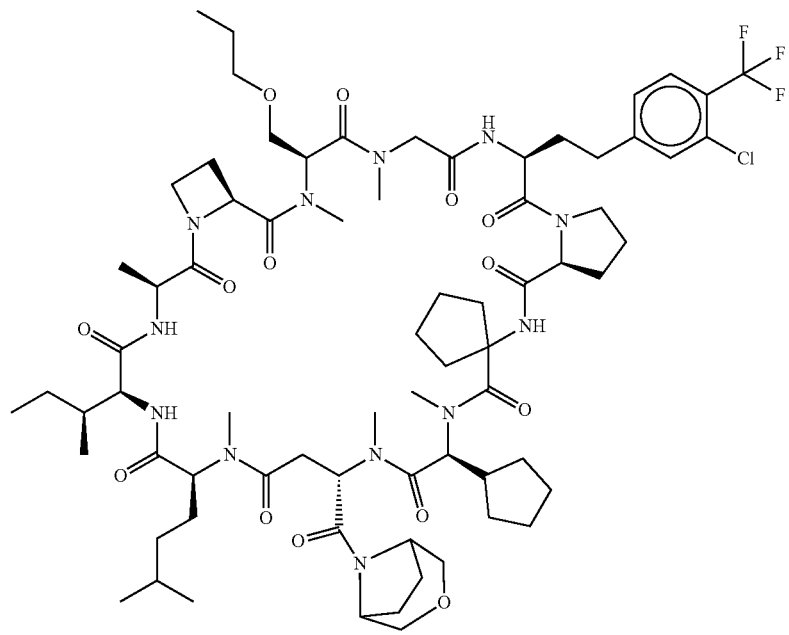 |
| 1327 | 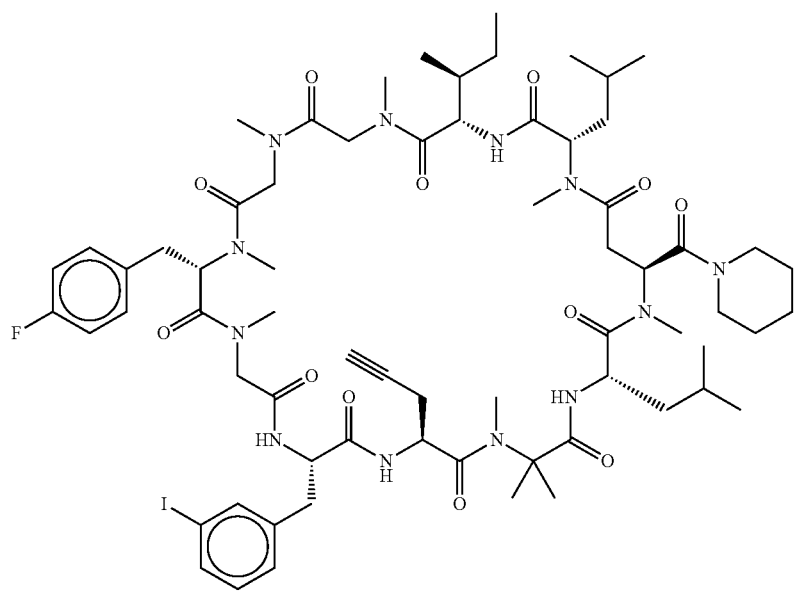 |

TABLE 24-continued
| Compound No. | Structural formula |
|---|---|
| 1328 | 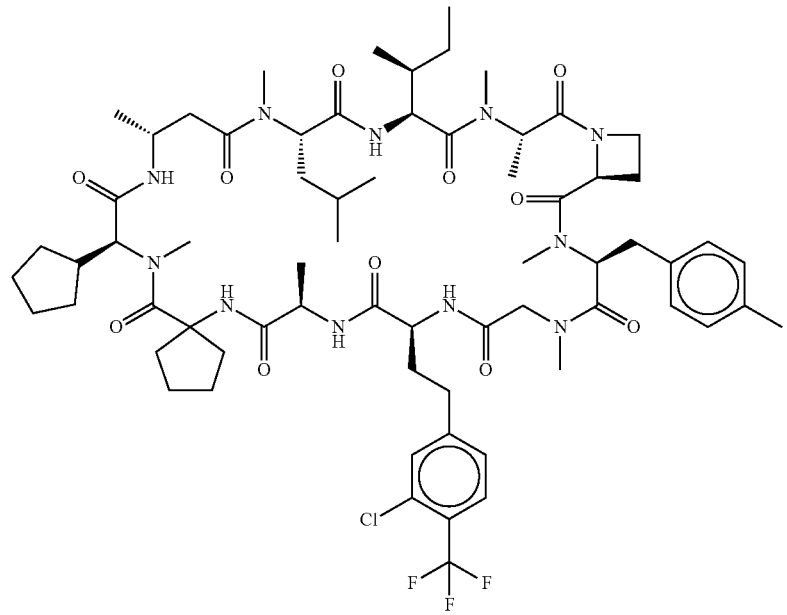 |
| 1329 | 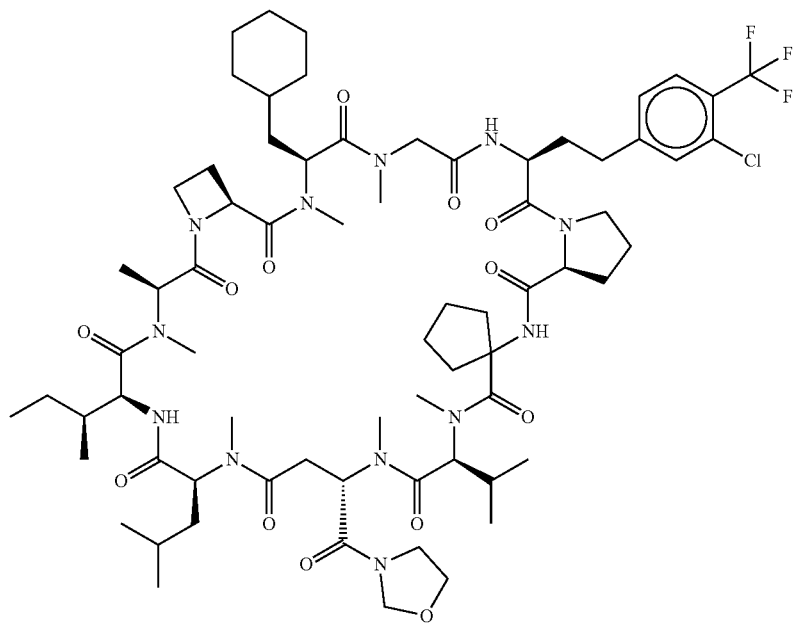 |

TABLE 24-continued
| Compound No. | Structural formula |
|---|---|
| 1330 | 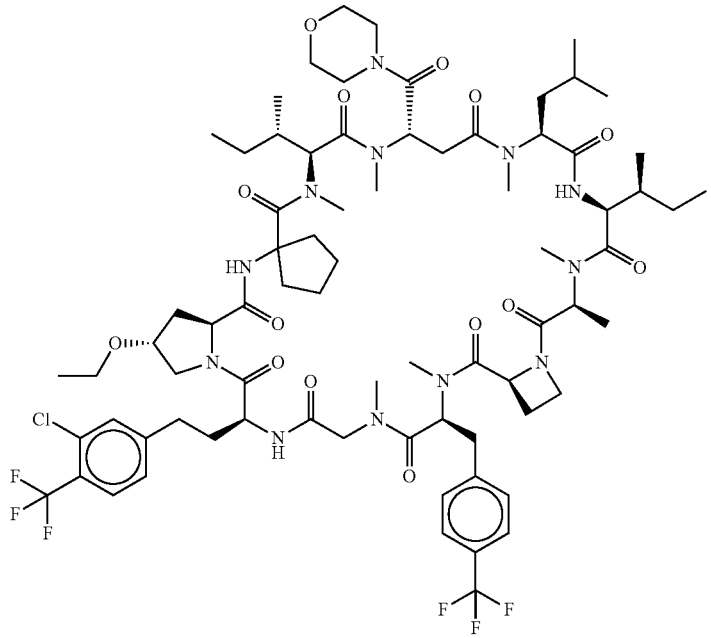 |
| 1331 | 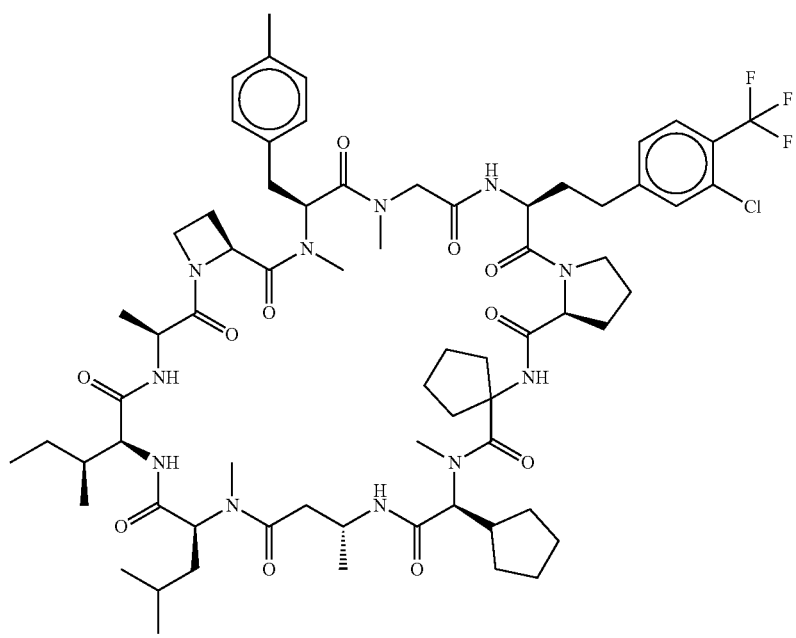 |

TABLE 24-continued
| Compound No. | Structural formula |
|---|---|
| 1332 | 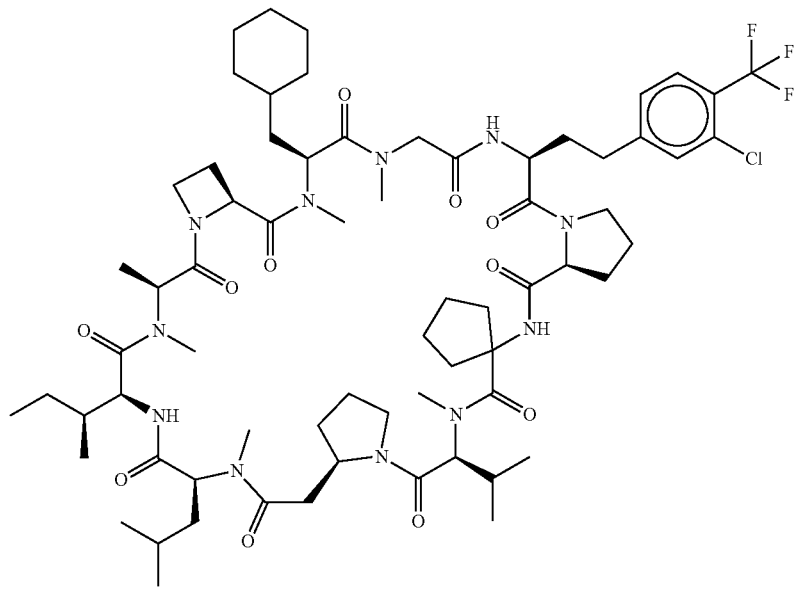 |
| 1333 | 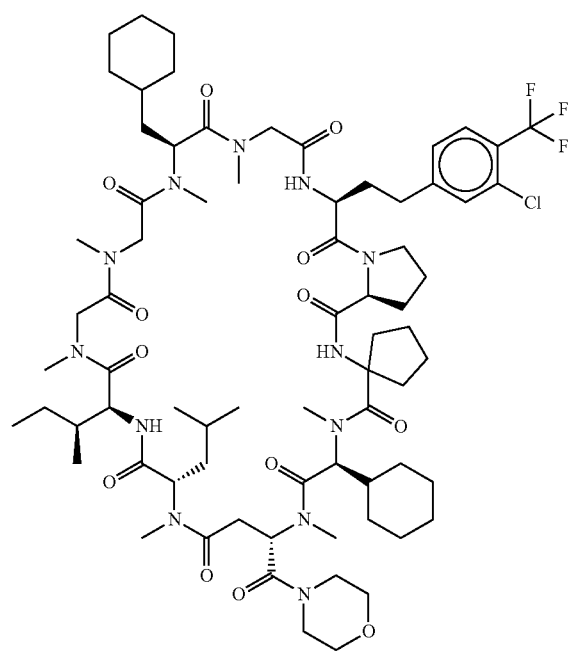 |

TABLE 24-continued
| Compound No. | Structural formula |
|---|---|
| 1334 | 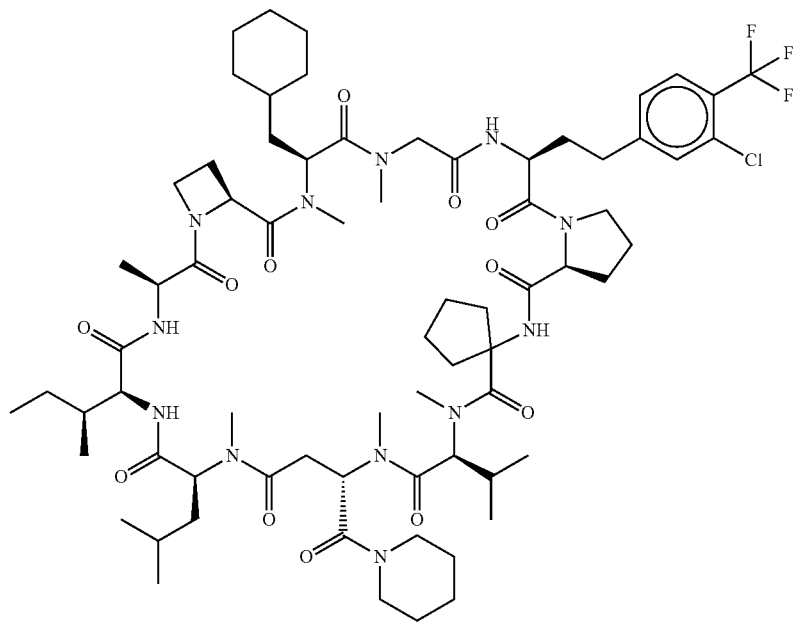 |
| 1335 | 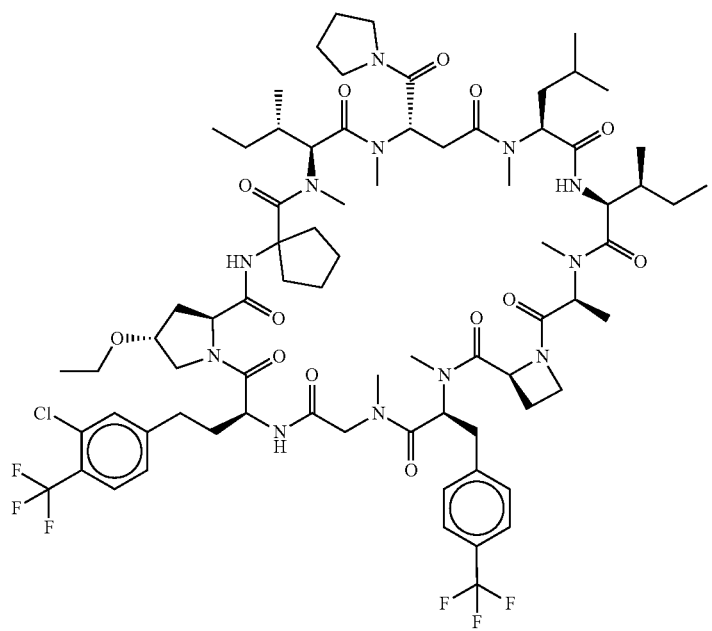 |

TABLE 24-continued
| Compound No. | Structural formula |
|---|---|
| 1336 | 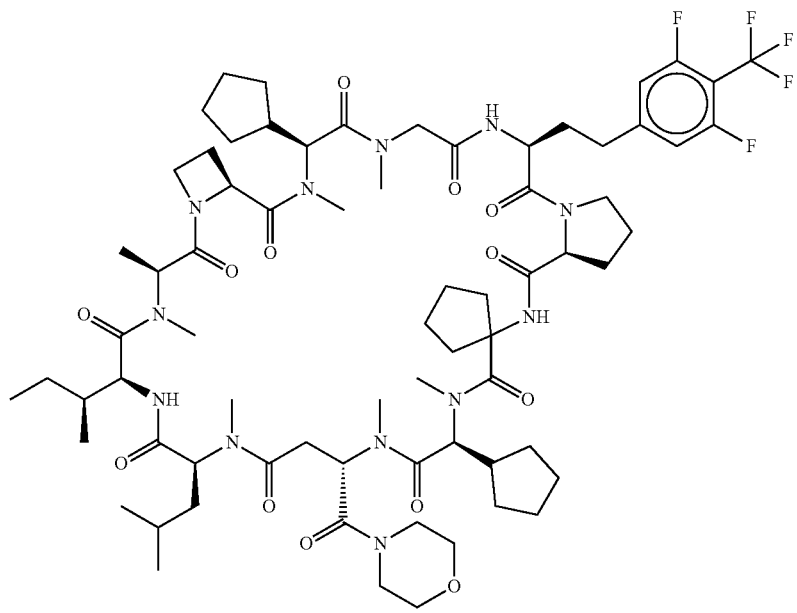 |
| 1337 | 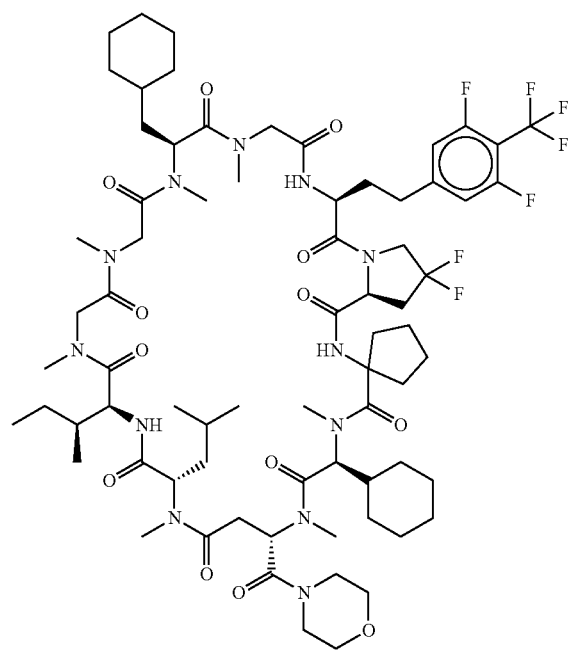 |

TABLE 24-continued
| Compound No. | Structural formula |
|---|---|
| 1338 | 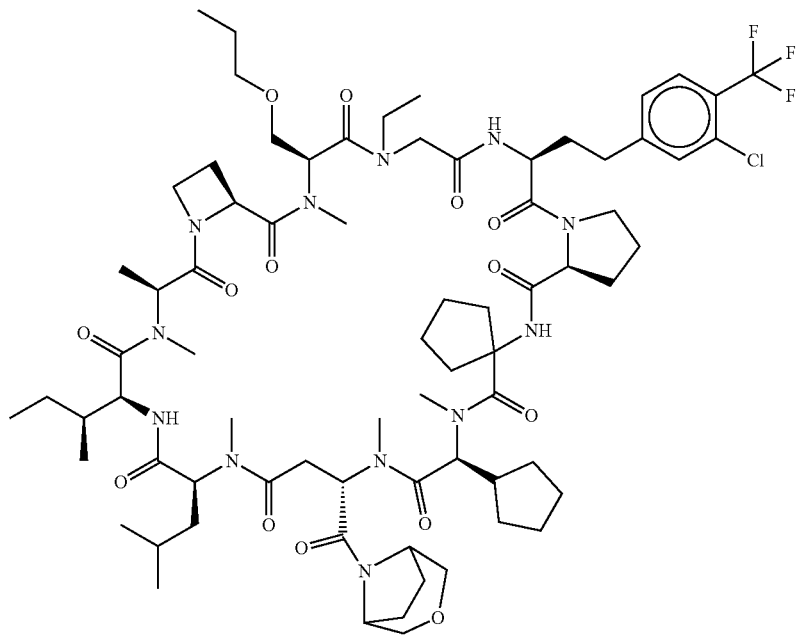 |
| 1339 | 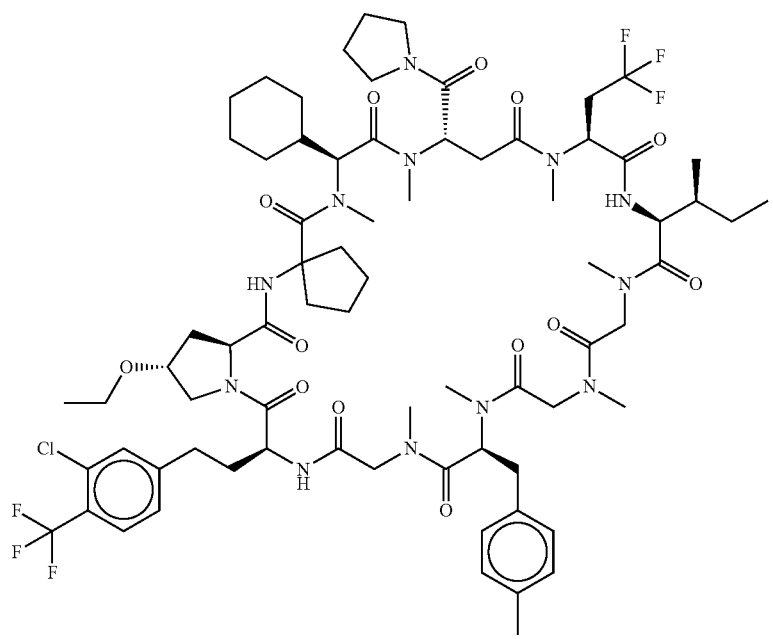 |

TABLE 24-continued
| Compound No. | Structural formula |
|---|---|
| 1340 | 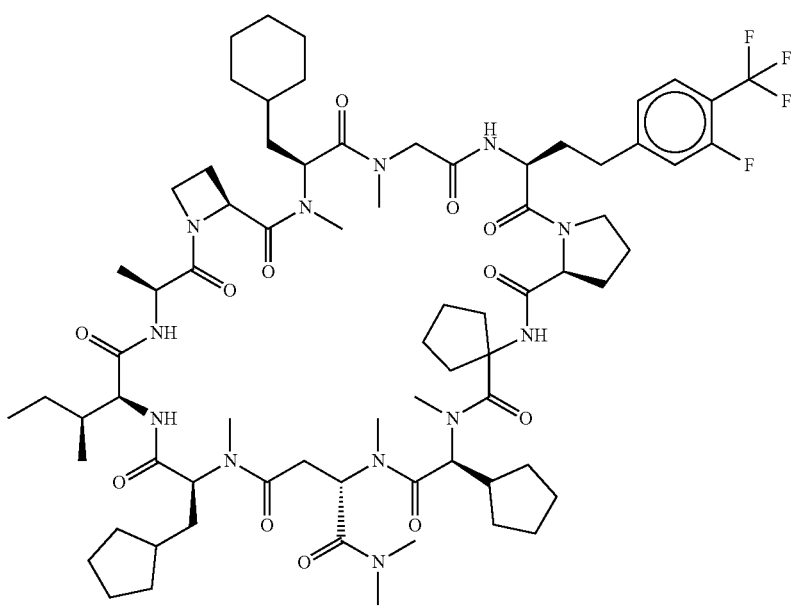 |
| 1341 | 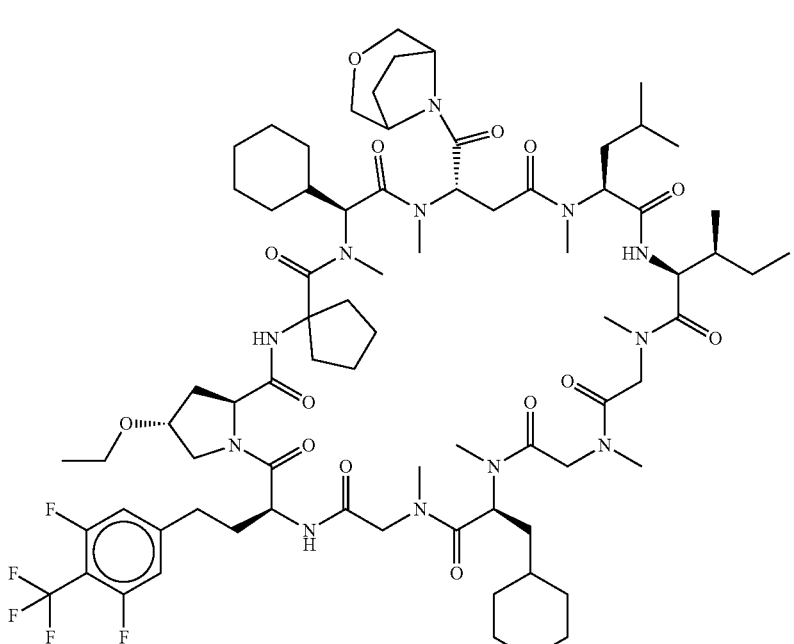 |

TABLE 24-continued
| Compound No. | Structural formula |
|---|---|
| 1342 | 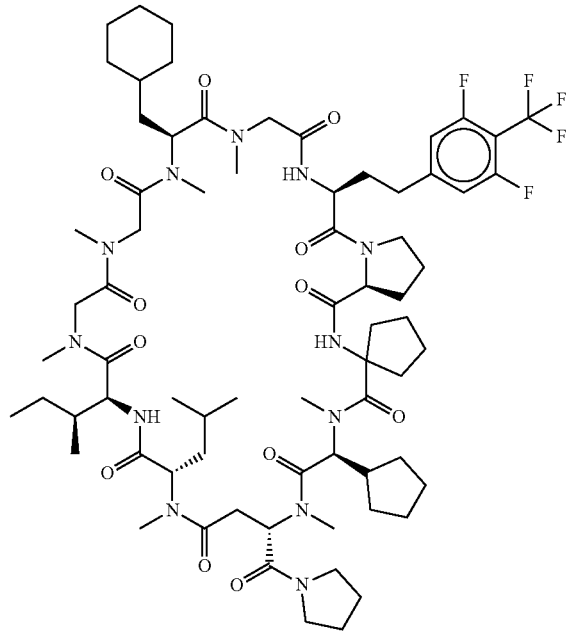 |
| 1343 | 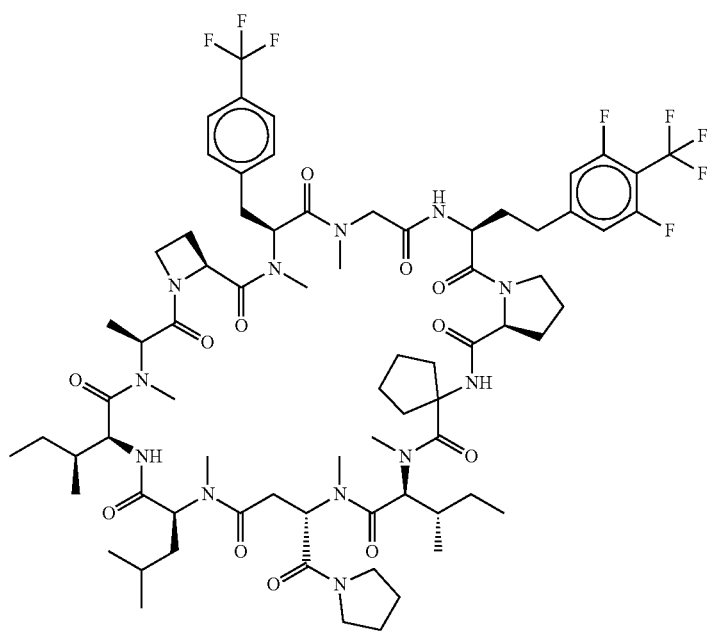 |

TABLE 24-continued
| Compound No. | Structural formula |
|---|---|
| 1344 | 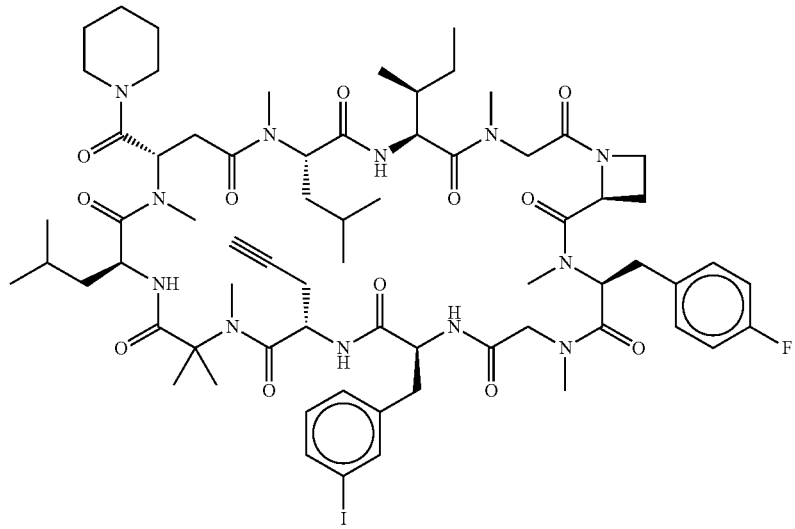 |
| 1345 | 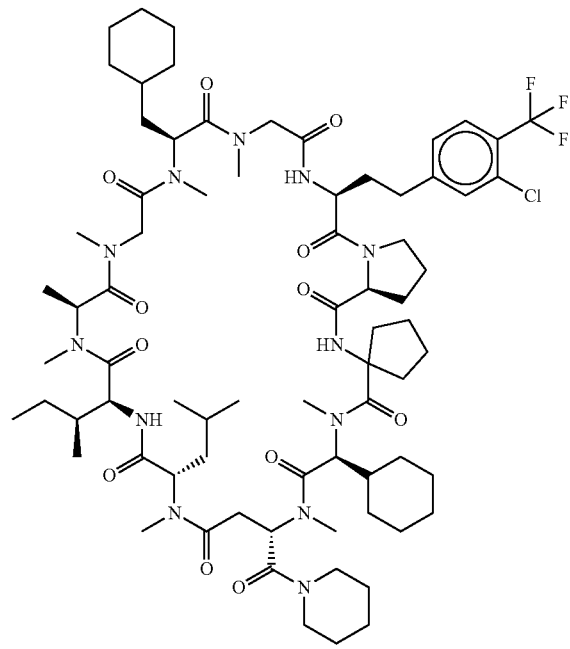 |

TABLE 24-continued
| Compound No. | Structural formula |
|---|---|
| 1346 | 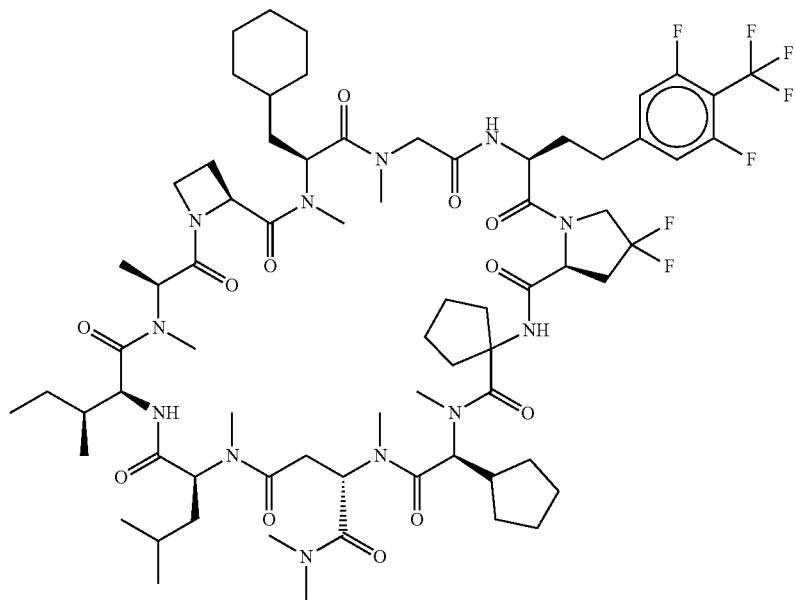 |
| 1347 | 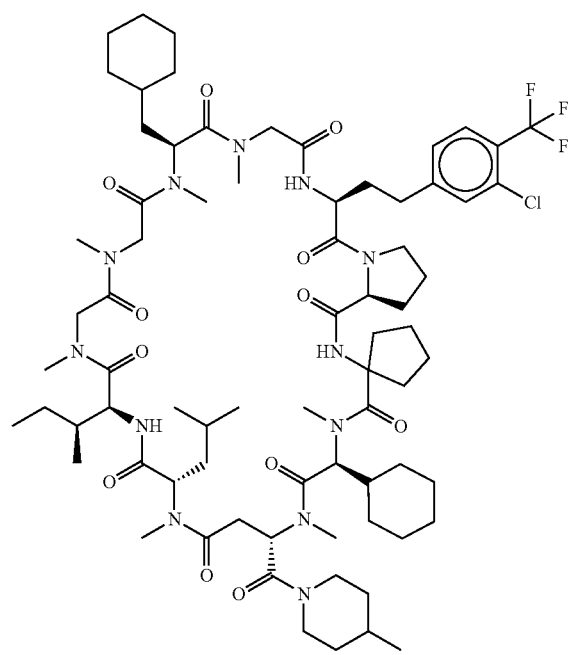 |

TABLE 24-continued
| Compound No. | Structural formula |
|---|---|
| 1348 | 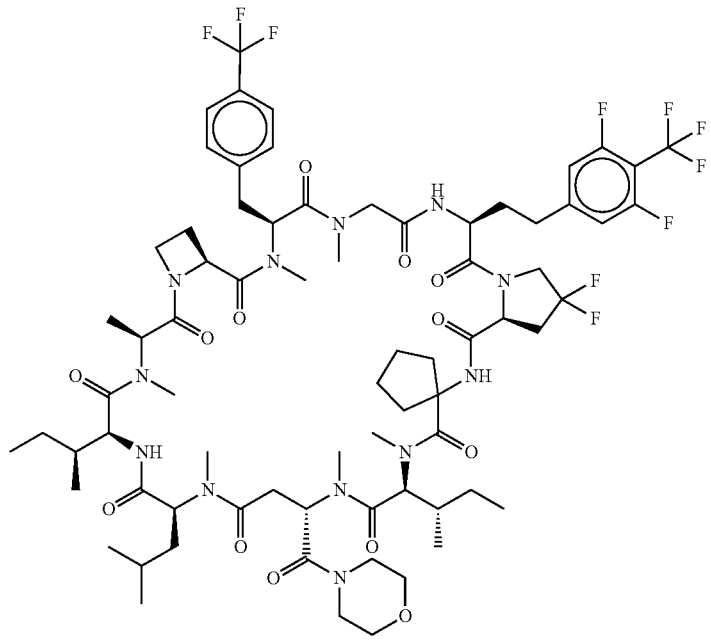 |
| 1349 | 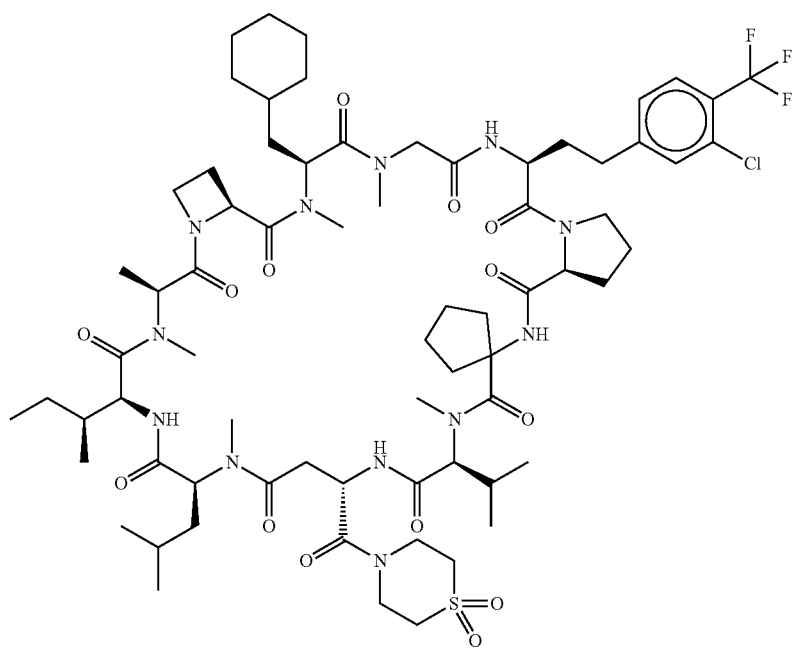 |

TABLE 24-continued
| Compound No. | Structural formula |
|---|---|
| 1350 | 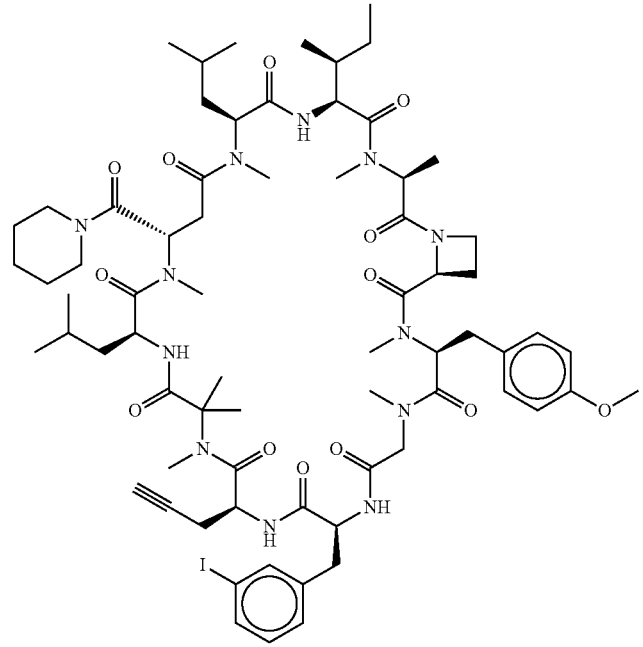 |
| 1351 | 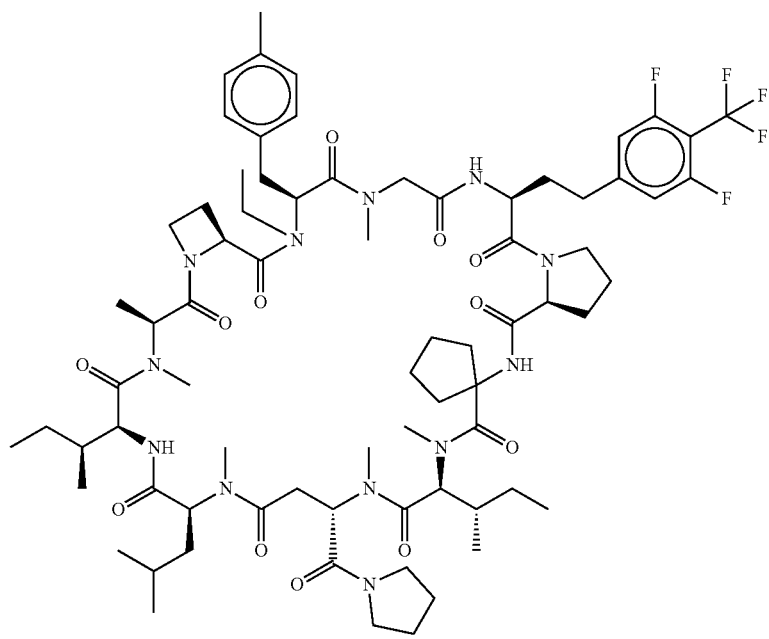 |

TABLE 24-continued
| Compound No. | Structural formula |
|---|---|
| 1352 | 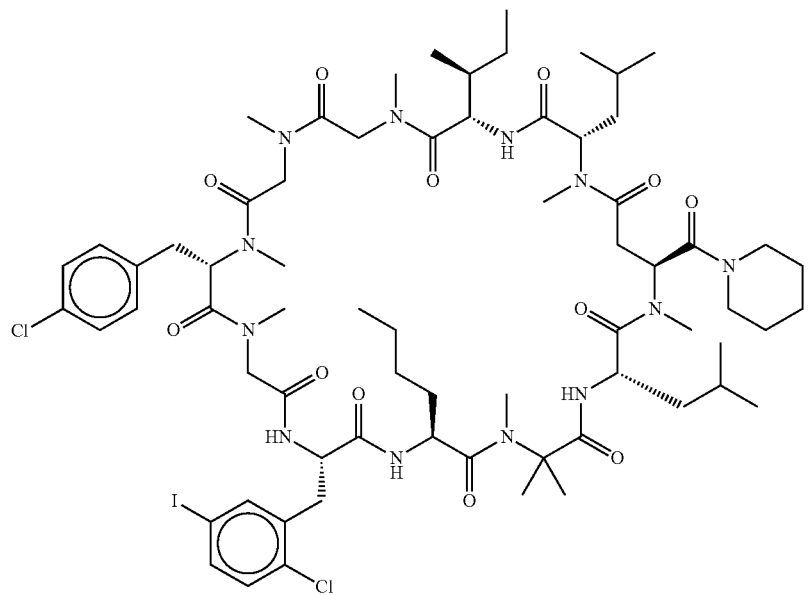 |
| 1353 | 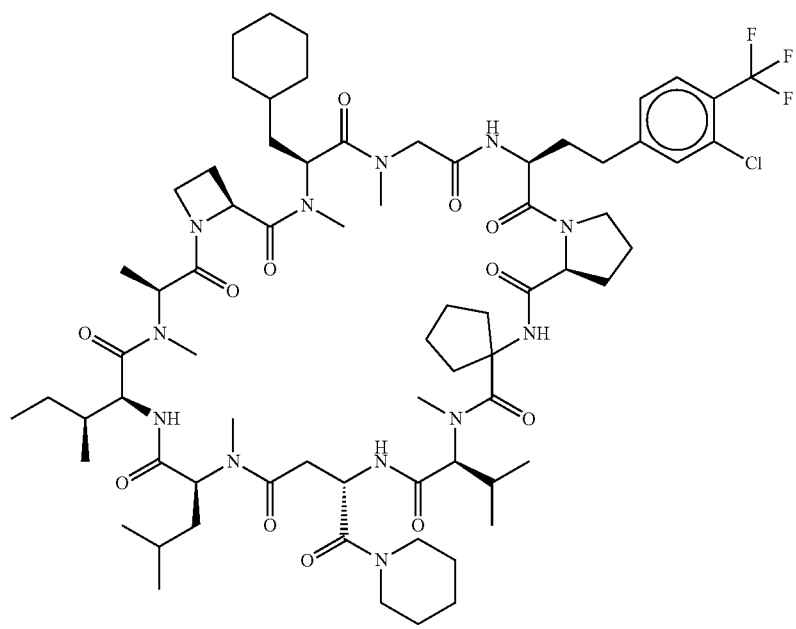 |

TABLE 24-continued
| Compound No. | Structural formula |
|---|---|
| 1354 | 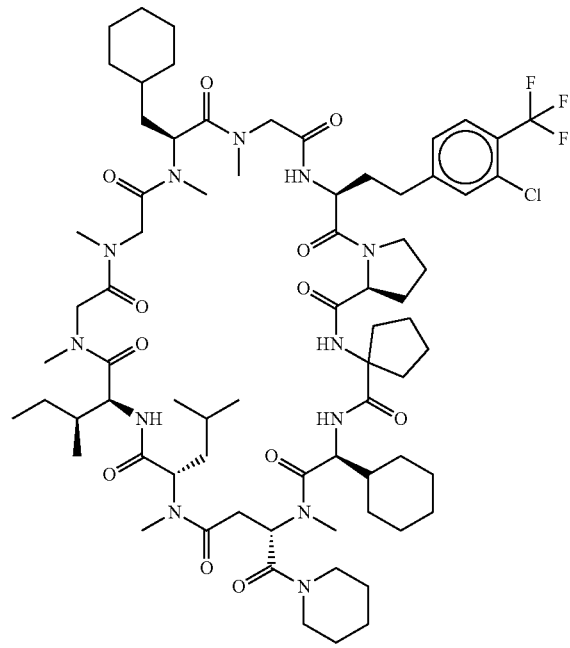 |
| 1355 | 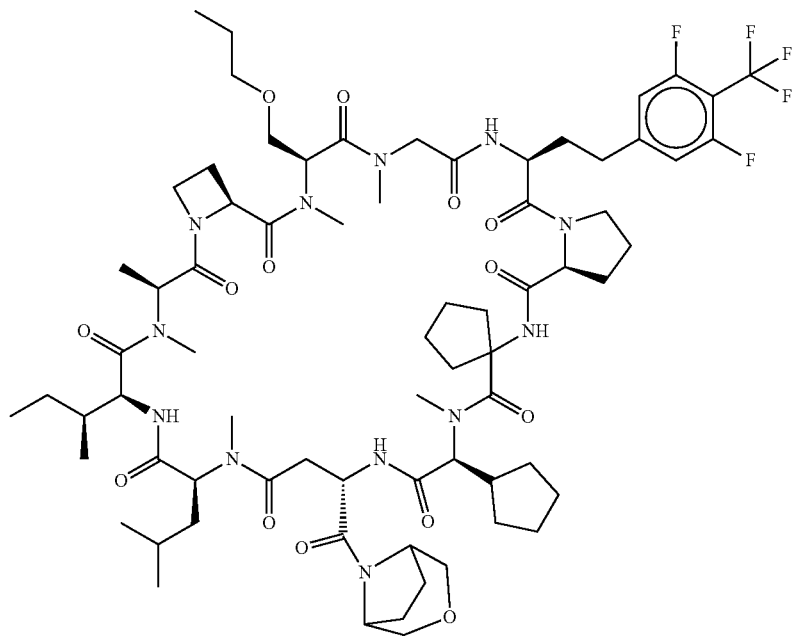 |

TABLE 24-continued
| Compound No. | Structural formula |
|---|---|
| 1356 | 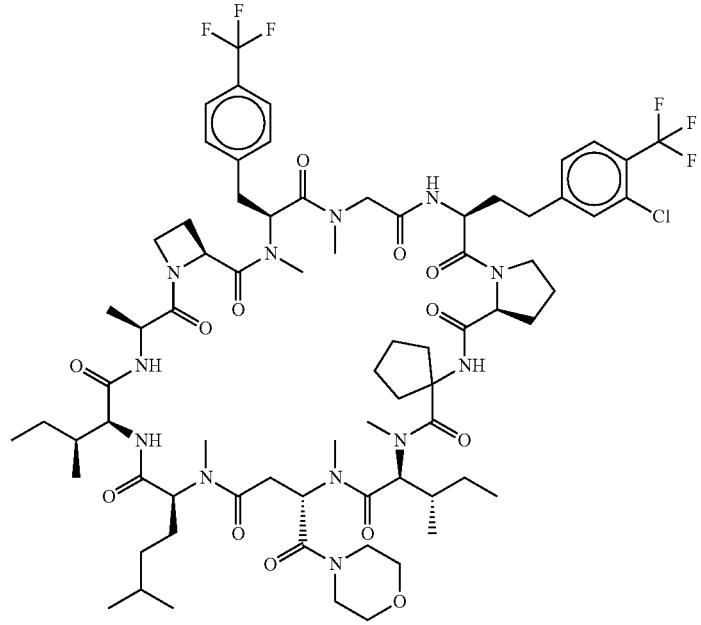 |
| 1357 | 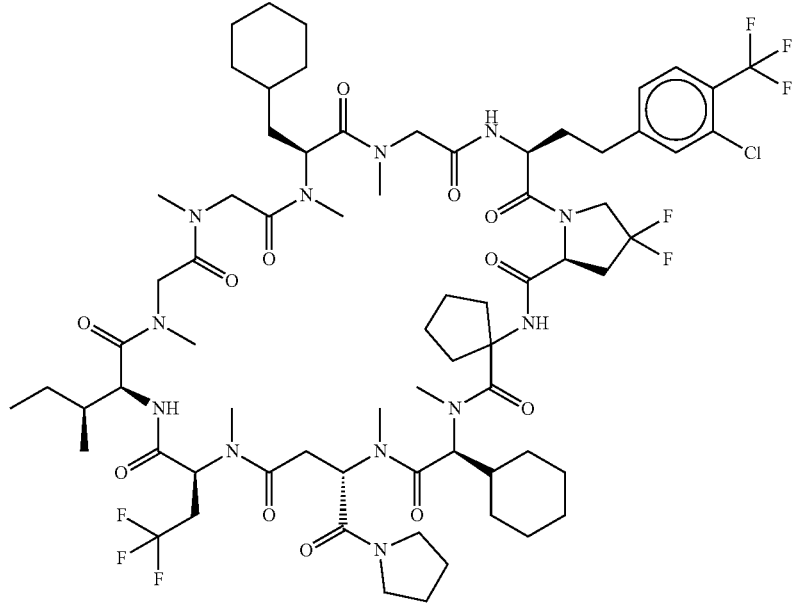 |

TABLE 24-continued
| Compound No. | Structural formula |
|---|---|
| 1358 | 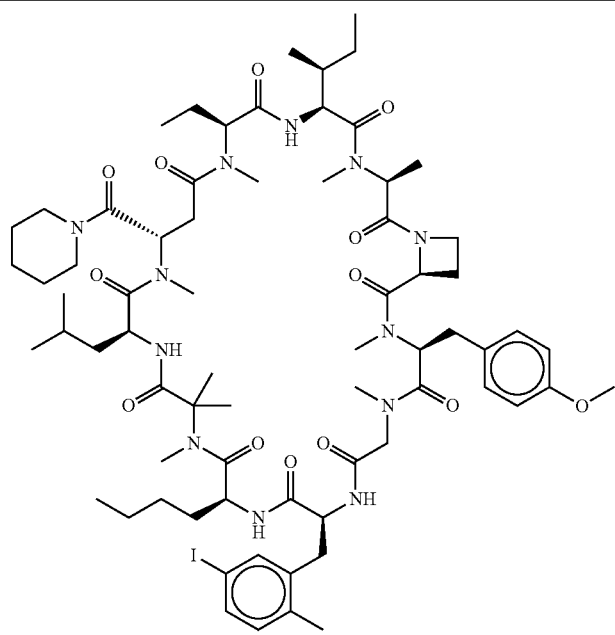 |
| 1359 | 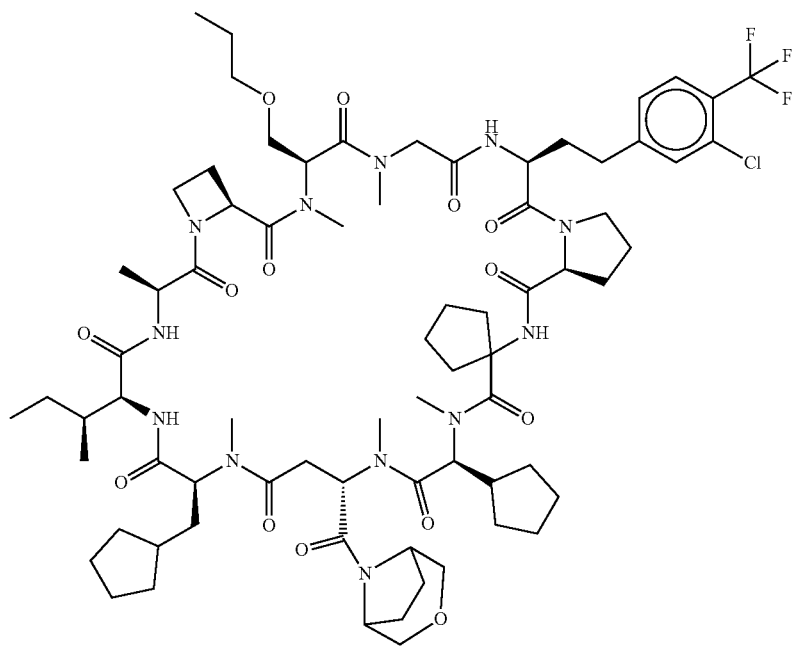 |

TABLE 24-continued
| Compound No. | Structural formula |
|---|---|
| 1360 | 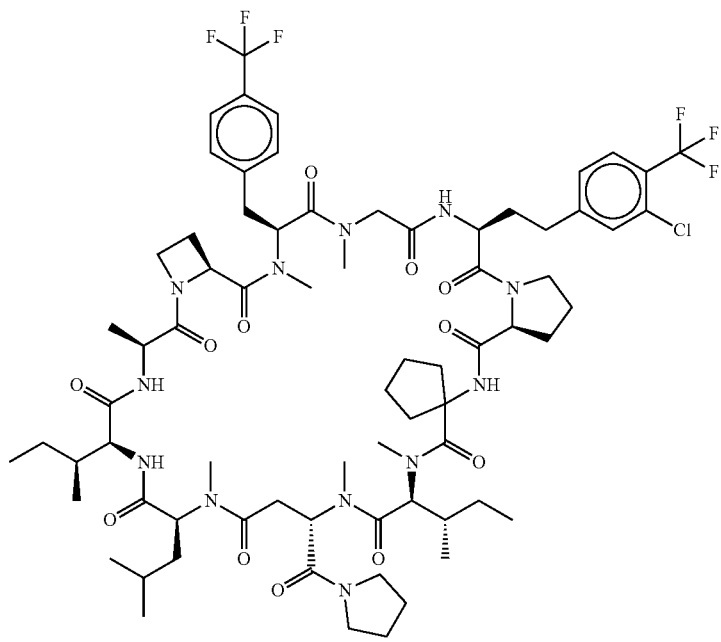 |
| 1361 | 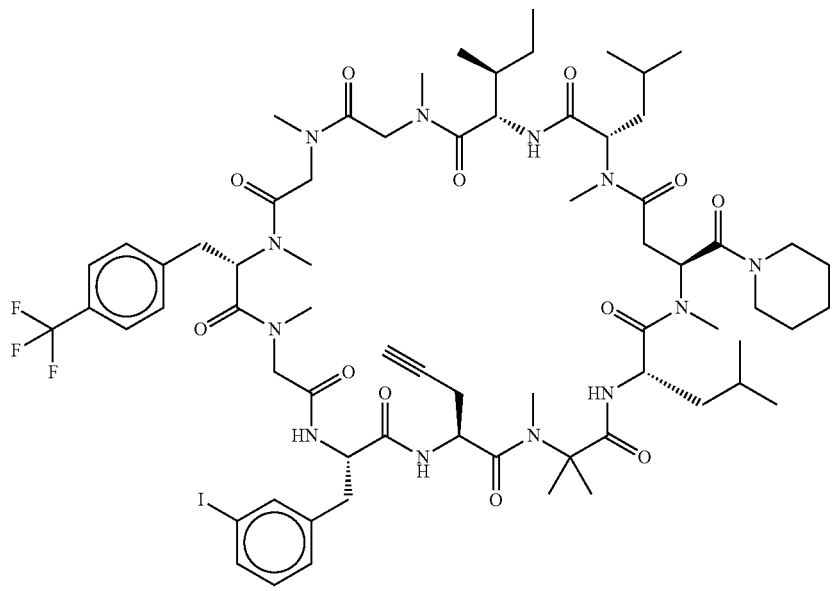 |

TABLE 24-continued
| Compound No. | Structural formula |
|---|---|
| 1362 | 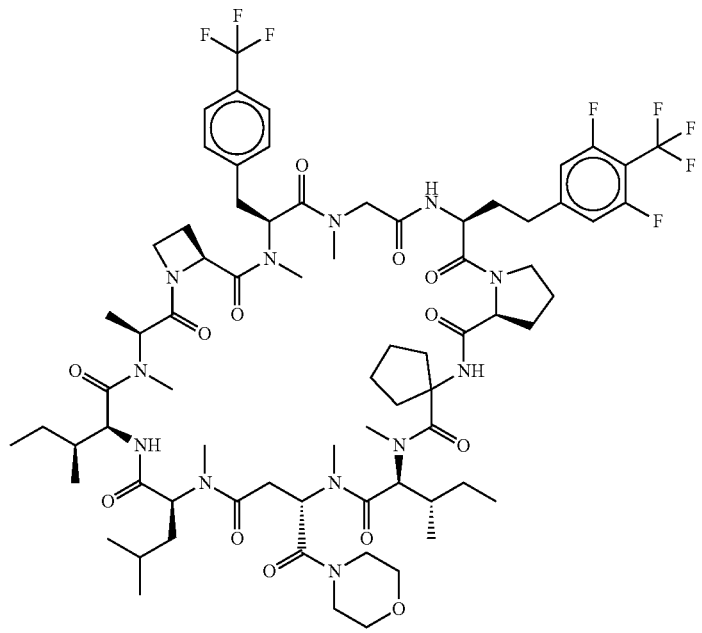 |
| 1363 | 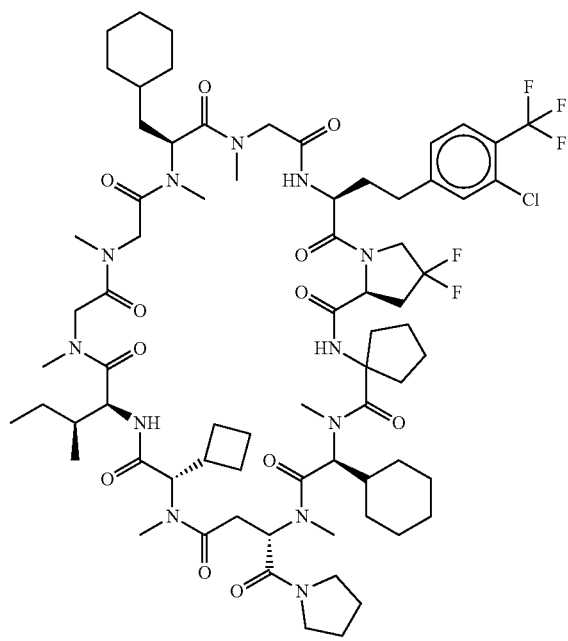 |

TABLE 24-continued
| Compound No. | Structural formula |
| --- | --- |
| 1364 | 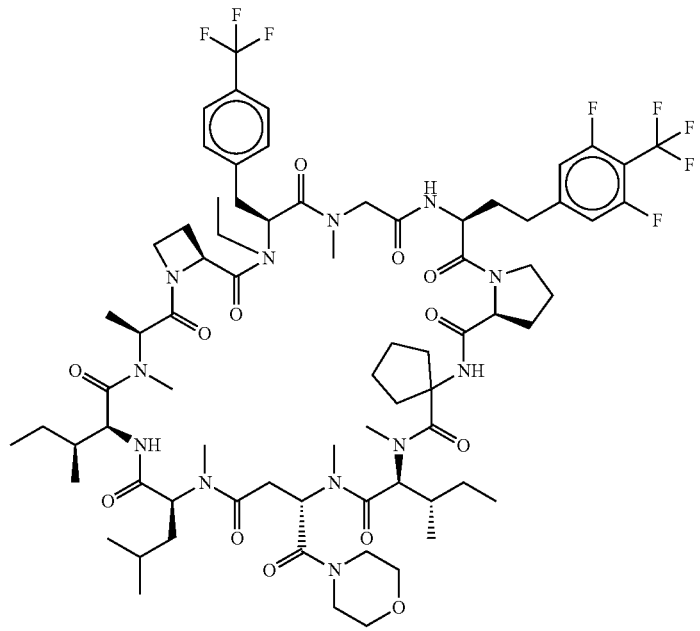 |
| 1365 | 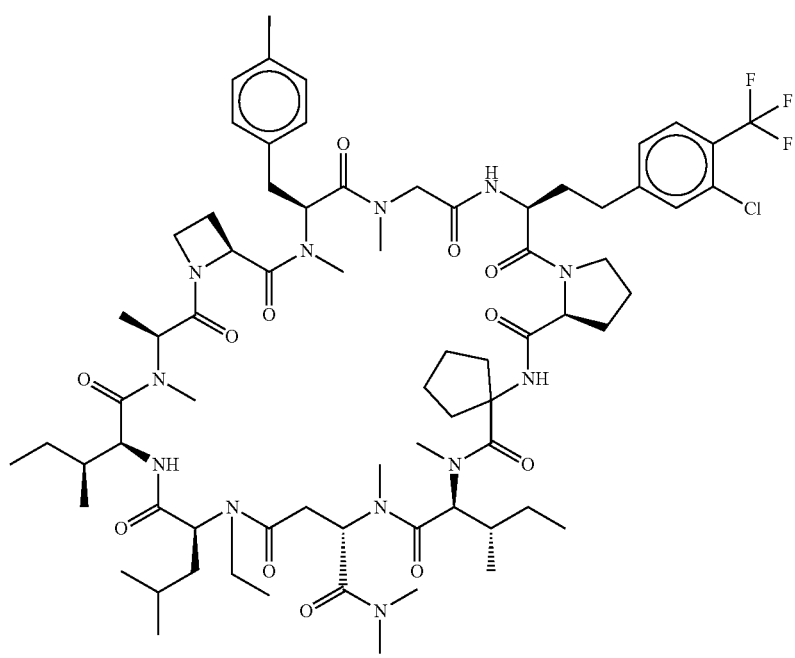 |

TABLE 24-continued

| Compound No. | Structural formula |
|---|---|
| 1366 | |
| 1367 | |

TABLE 24-continued
| Compound No. | Structural formula |
|---|---|
| 1368 | 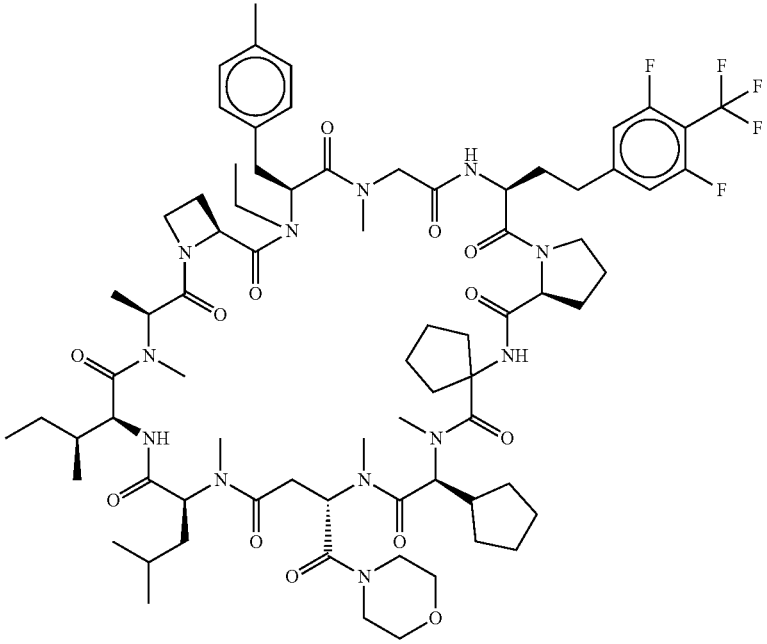 |
| 1369 | 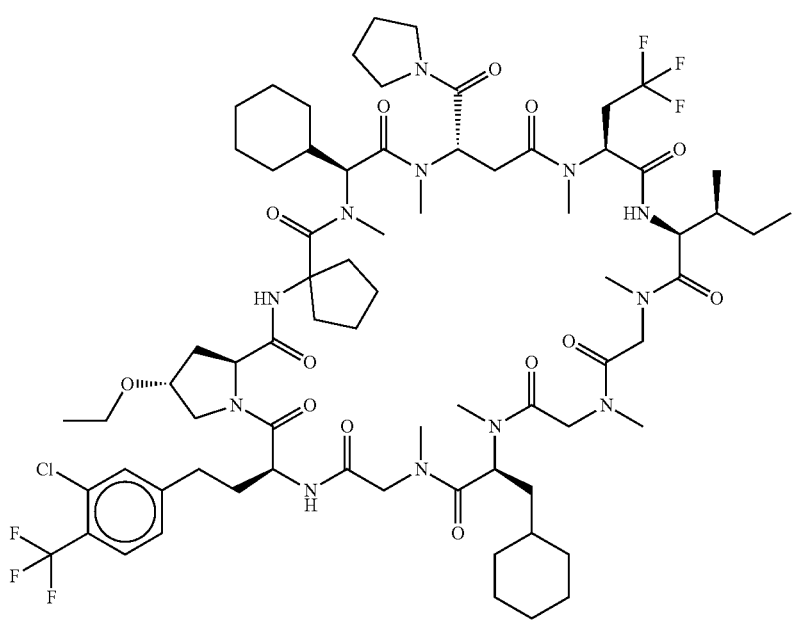 |

TABLE 24-continued
| Compound No. | Structural formula |
|---|---|
| 1370 | 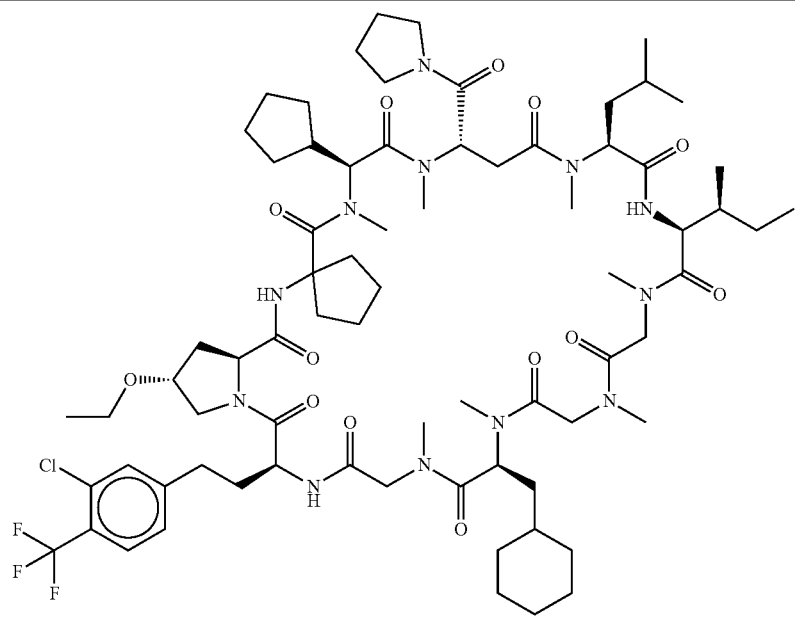 |
| 1371 | 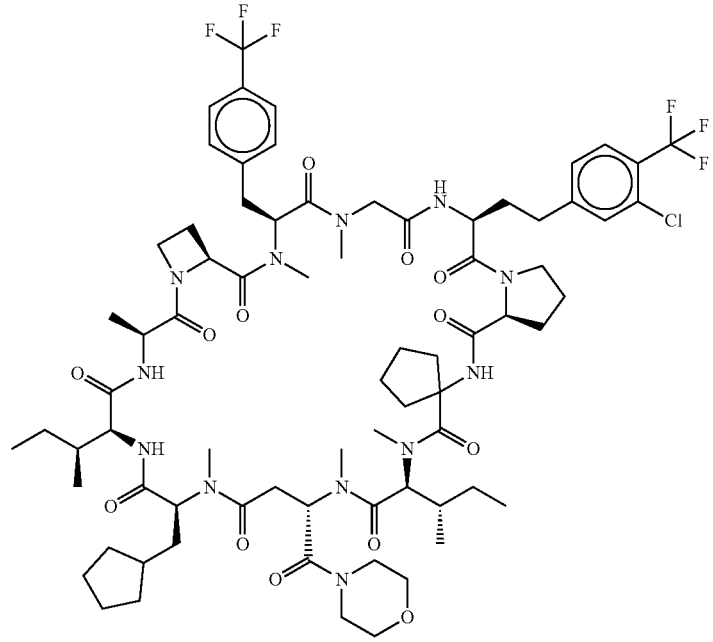 |

TABLE 24-continued
| Compound No. | Structural formula |
|---|---|
| 1372 | 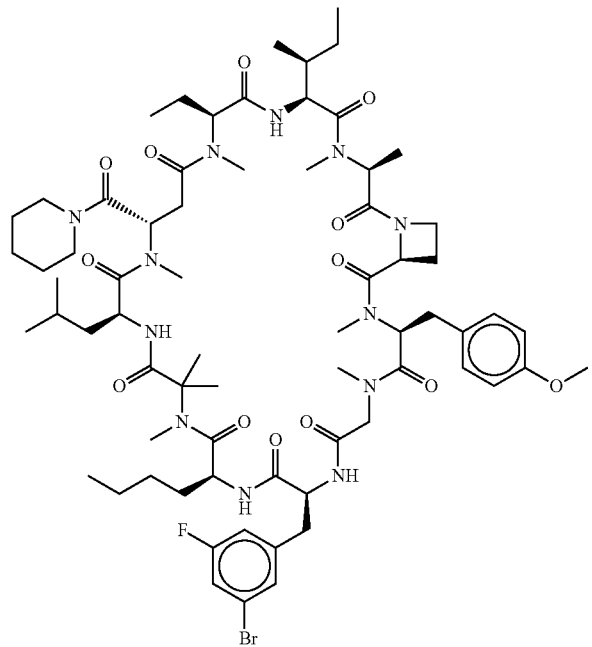 |
| 1373 | 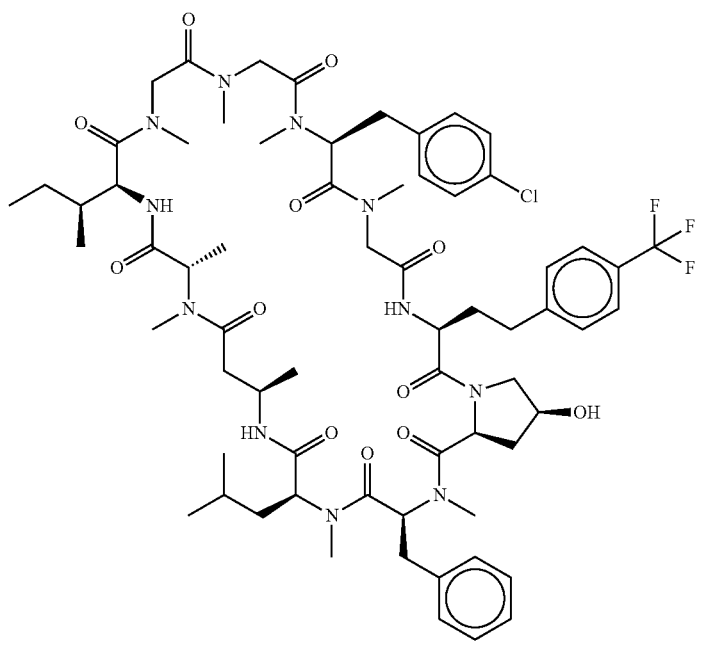 |

TABLE 24-continued
| Compound No. | Structural formula |
|---|---|
| 1374 | 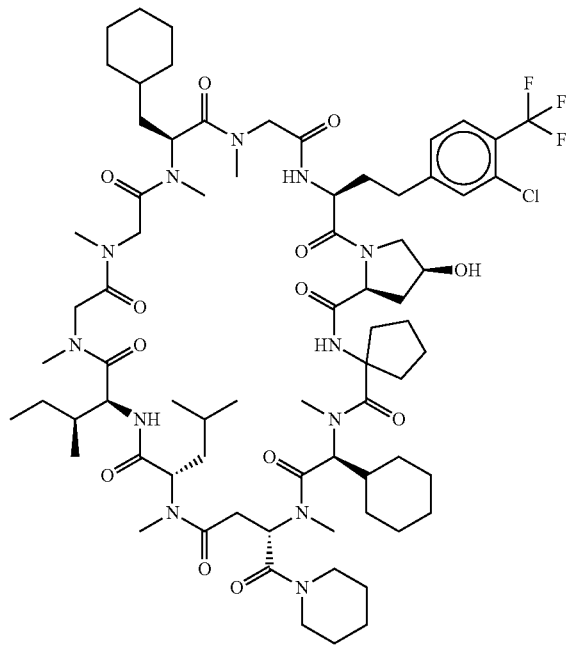 |
| 1375 | 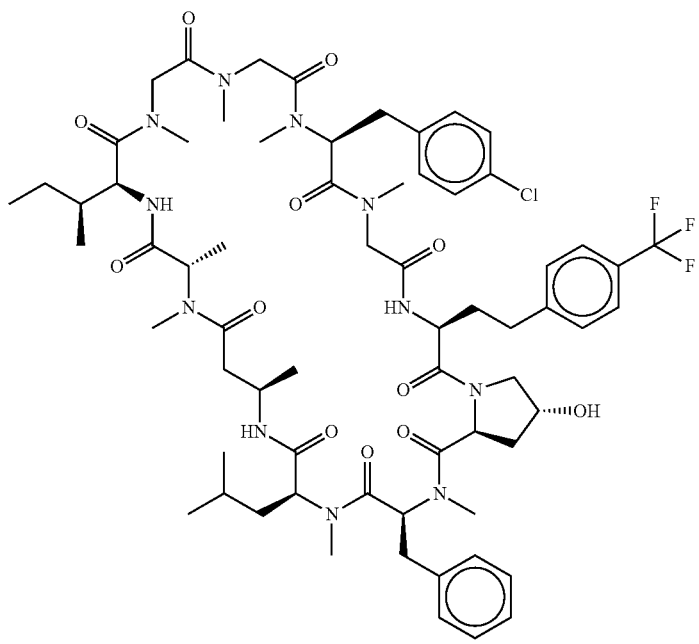 |

TABLE 24-continued
| Compound No. | Structural formula |
|---|---|
| 1376 | 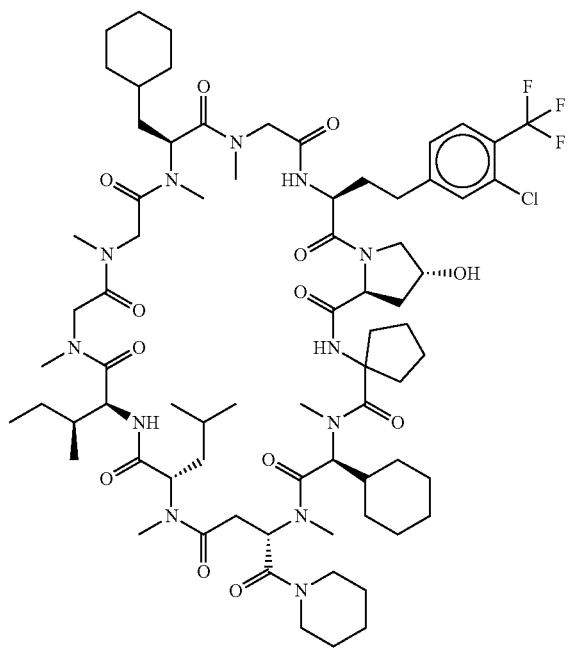 |
| 1377 | 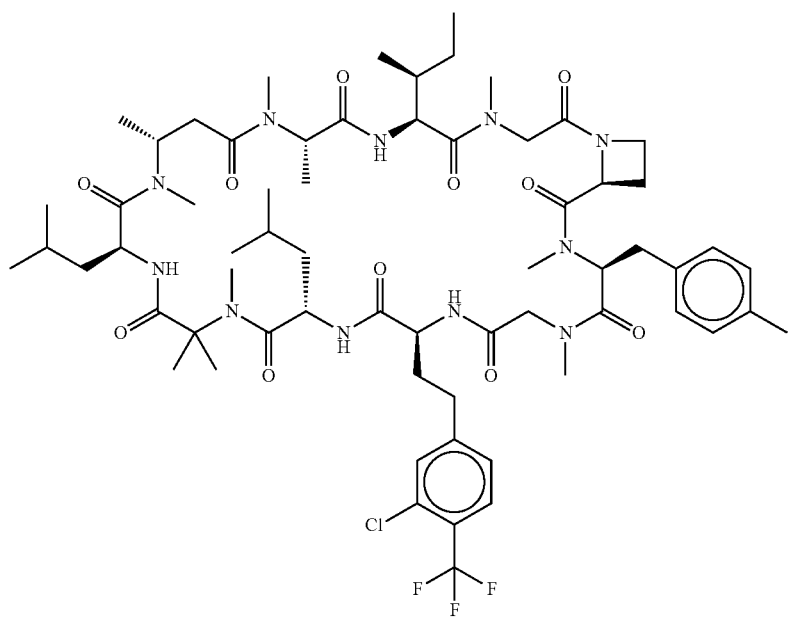 |

TABLE 24-continued
| Compound No. | Structural formula |
|---|---|
| 1378 | 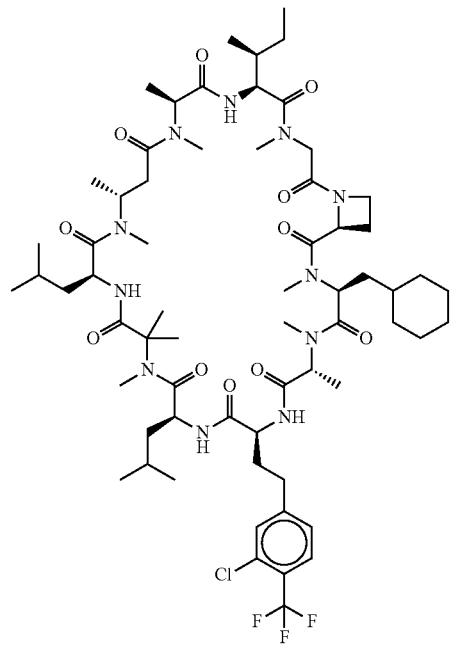 |
| 1379 | 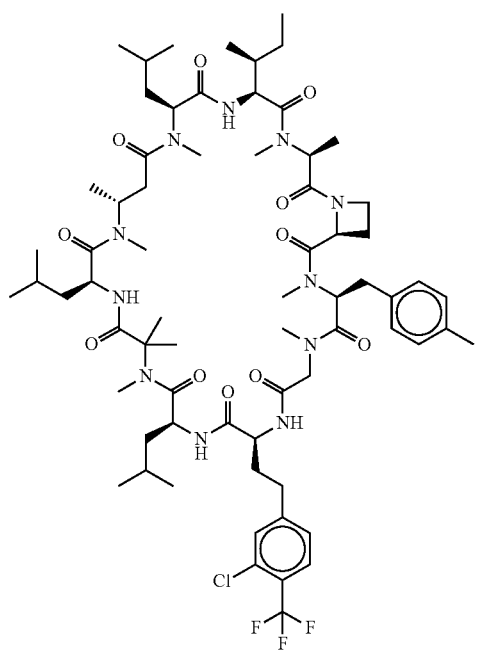 |

TABLE 24-continued
| Compound No. | Structural formula |
|---|---|
| 1380 | 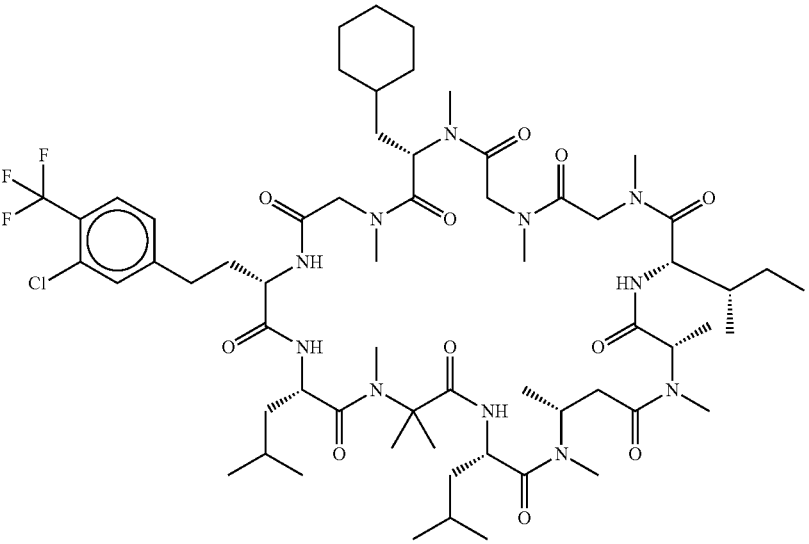 |
| 1381 | 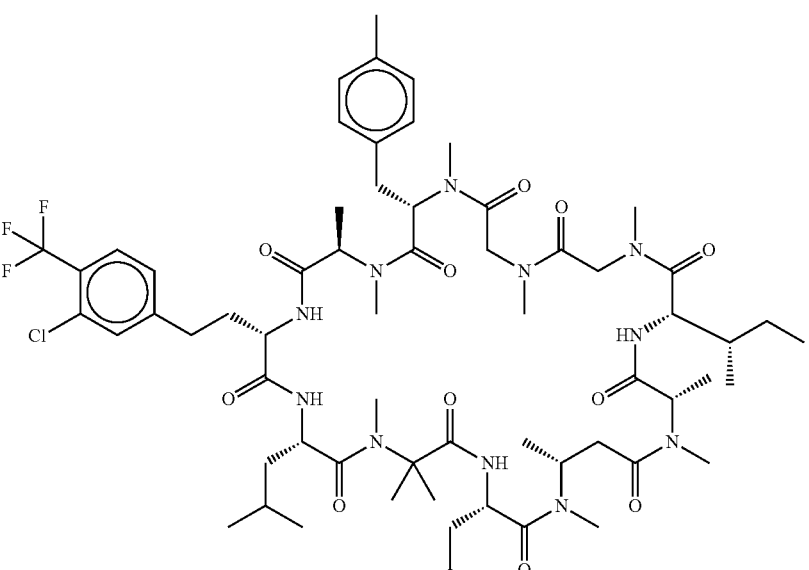 |

TABLE 24-continued
| Compound No. | Structural formula |
|---|---|
| 1382 | 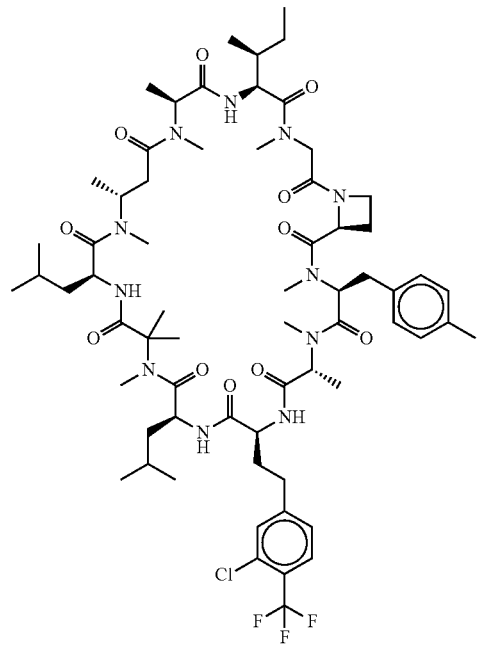 |
| 1383 | 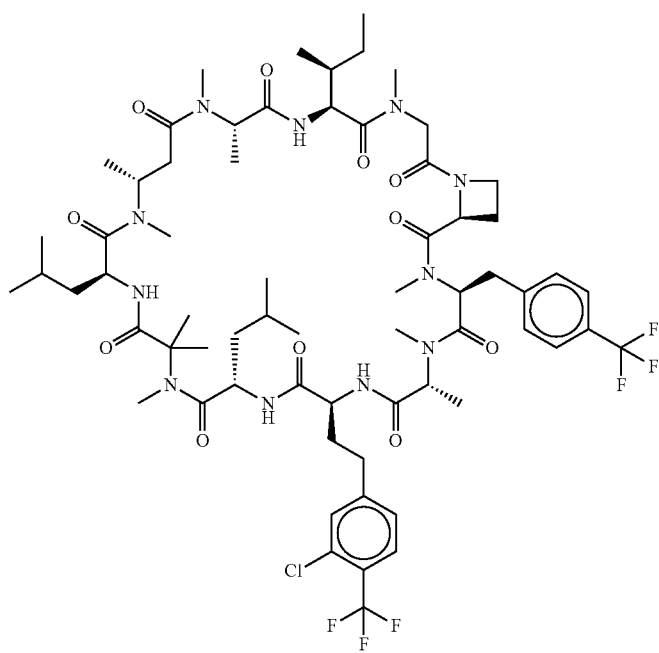 |

TABLE 24-continued
| Compound No. | Structural formula |
|---|---|
| 1384 | 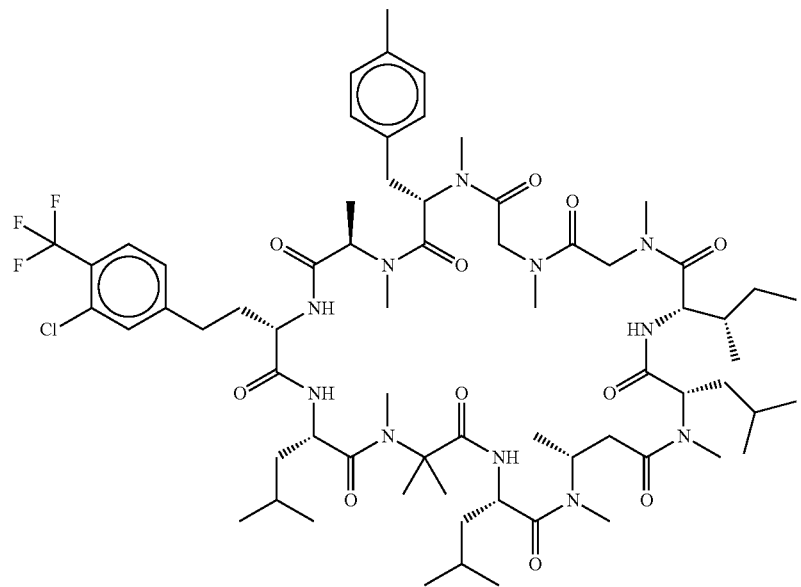 |
| 1385 | 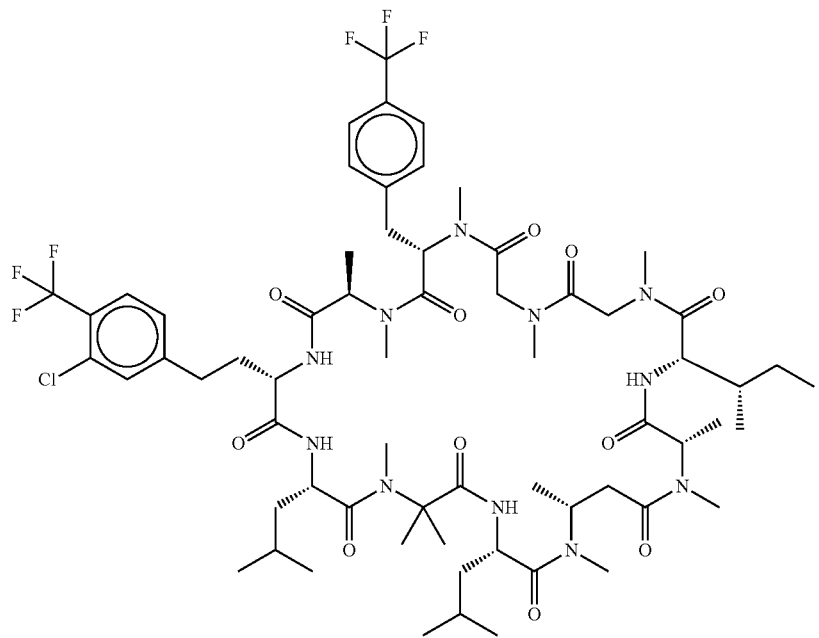 |

TABLE 24-continued
| Compound No. | Structural formula |
|---|---|
| 1386 | 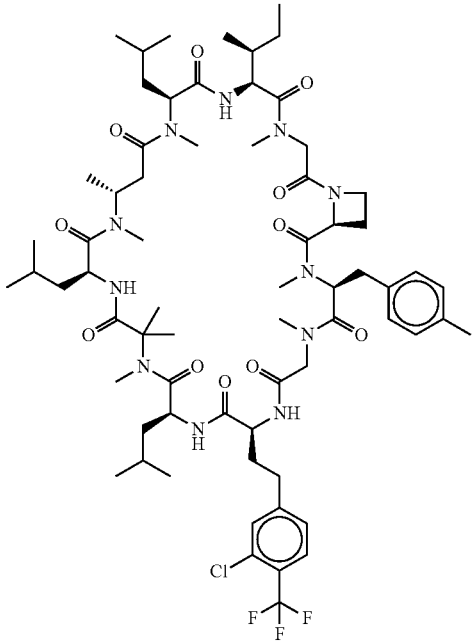 |
| 1387 | 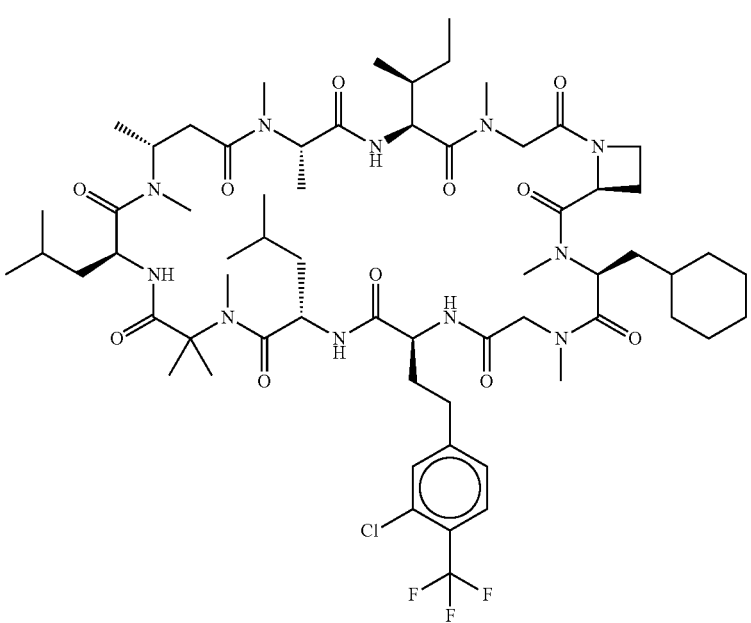 |

TABLE 24-continued
| Compound No. | Structural formula |
|---|---|
| 1388 | 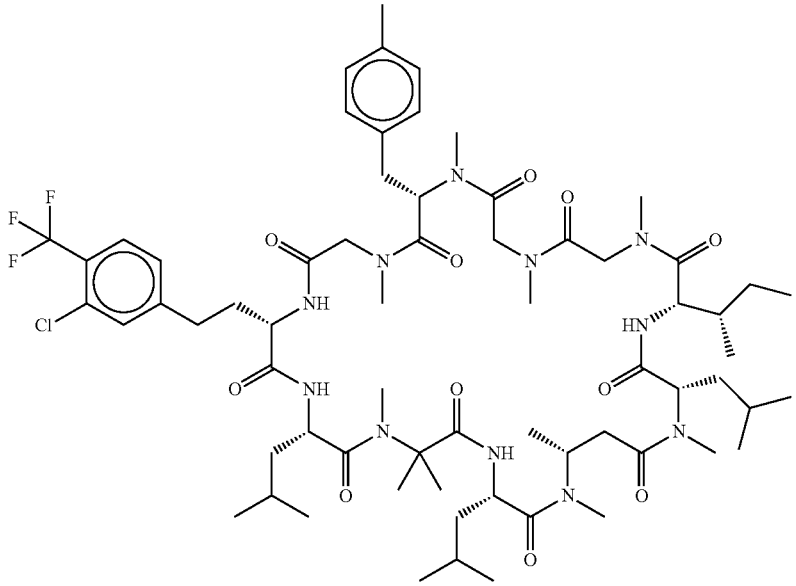 |
| 1389 | 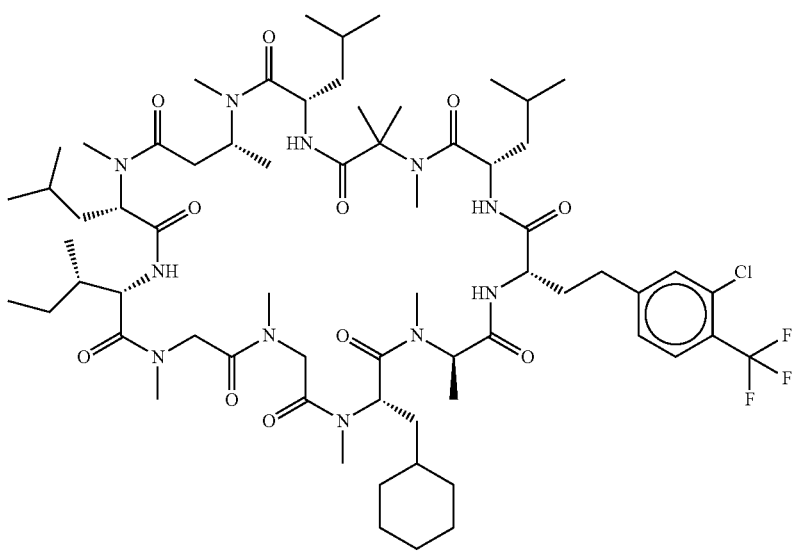 |

TABLE 24-continued
| Compound No. | Structural formula |
|---|---|
| 1390 | 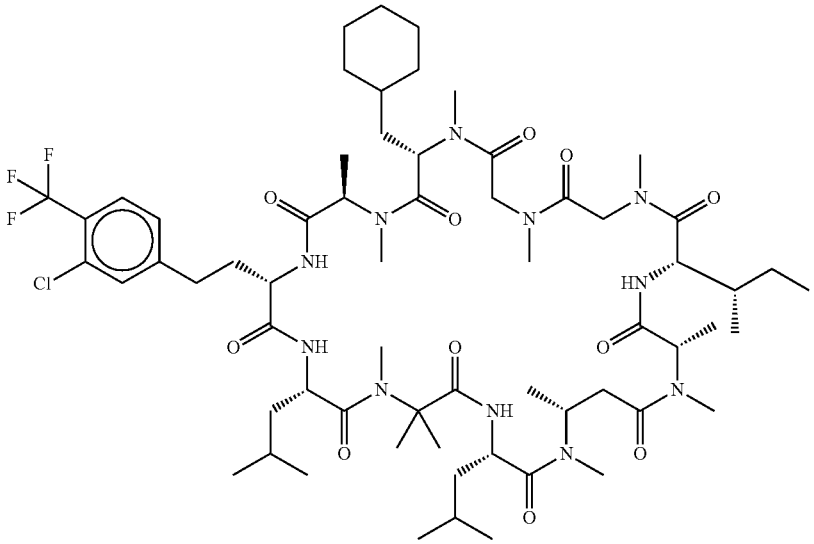 |
| 1391 | 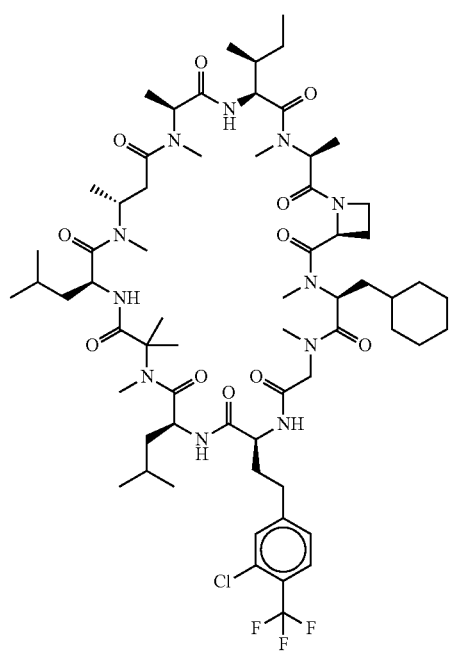 |

| Compound No. | Structural formula |
| --- | --- |
| 1392 | 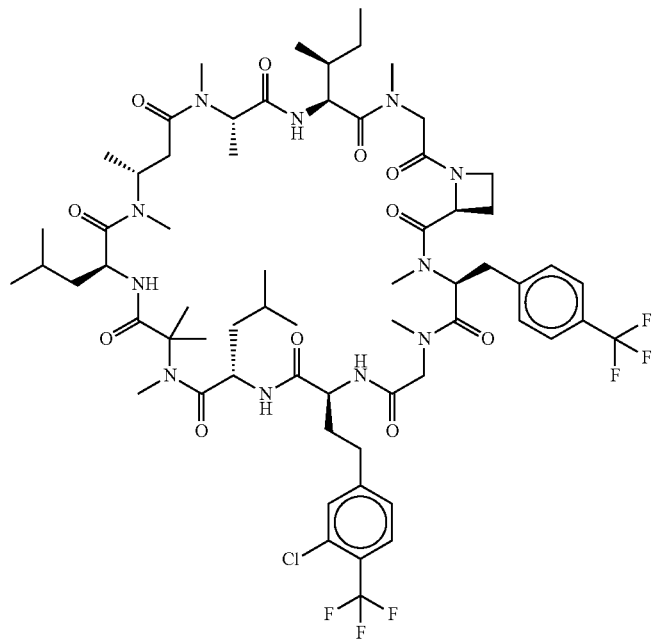 |
| 1393 | 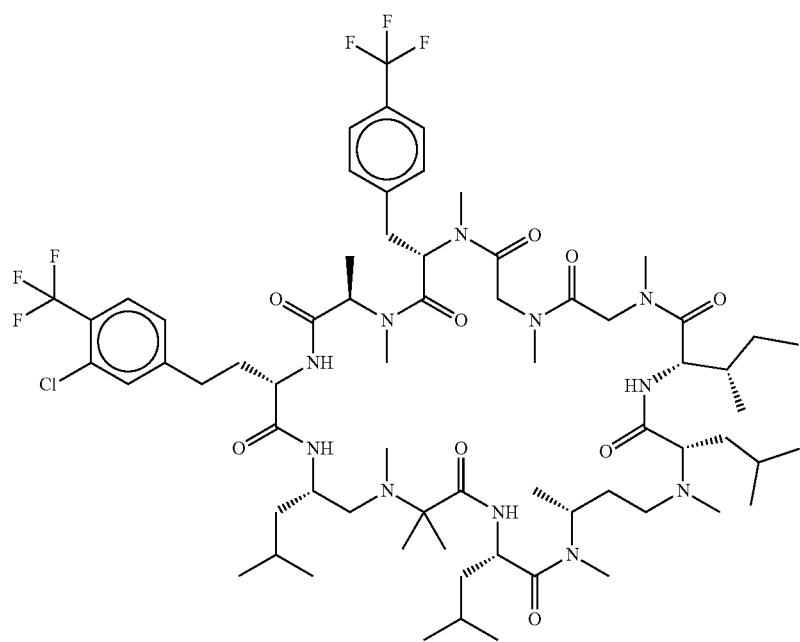 |

TABLE 24-continued
| Compound No. | Structural formula |
|---|---|
| 1394 | 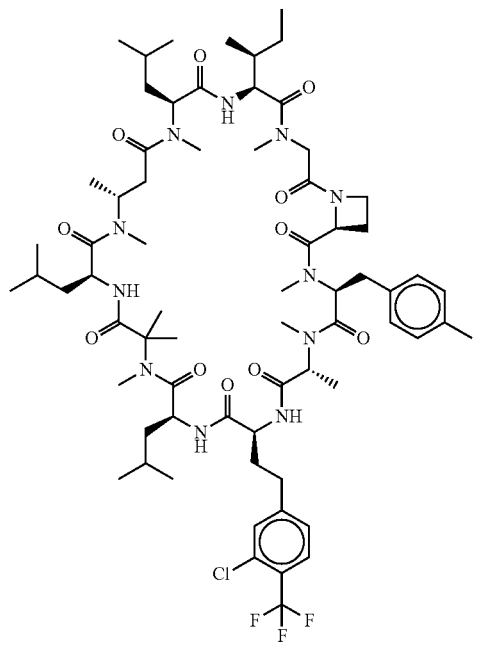 |
| 1395 | 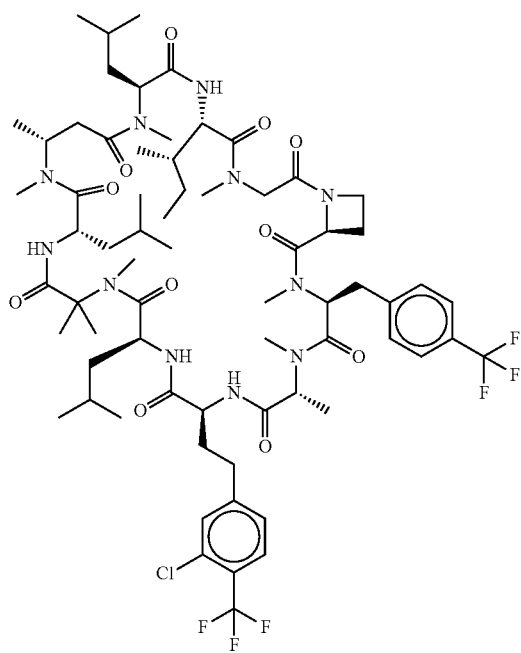 |

TABLE 24-continued
| Compound No. | Structural formula |
|---|---|
| 1396 | 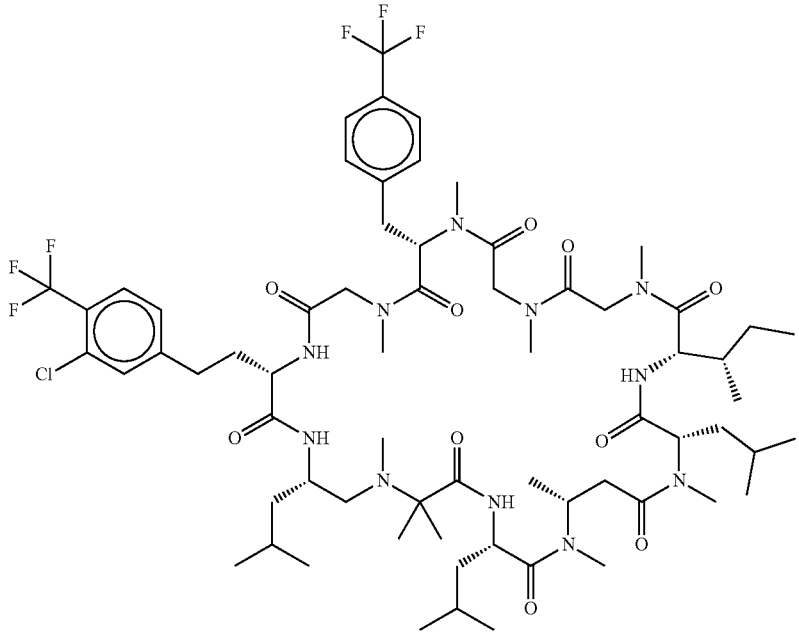 |
| 1397 | 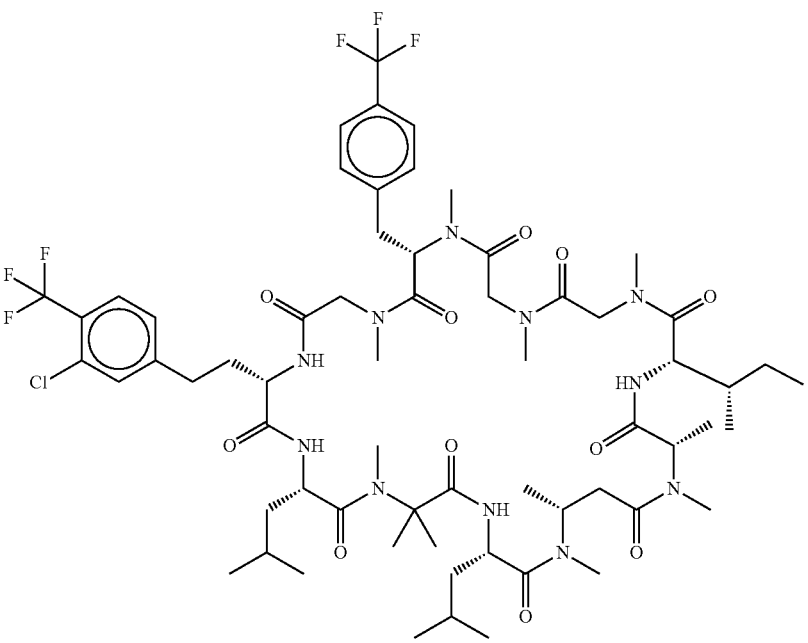 |

TABLE 24-continued
| Compound No. | Structural formula |
|---|---|
| 1398 | 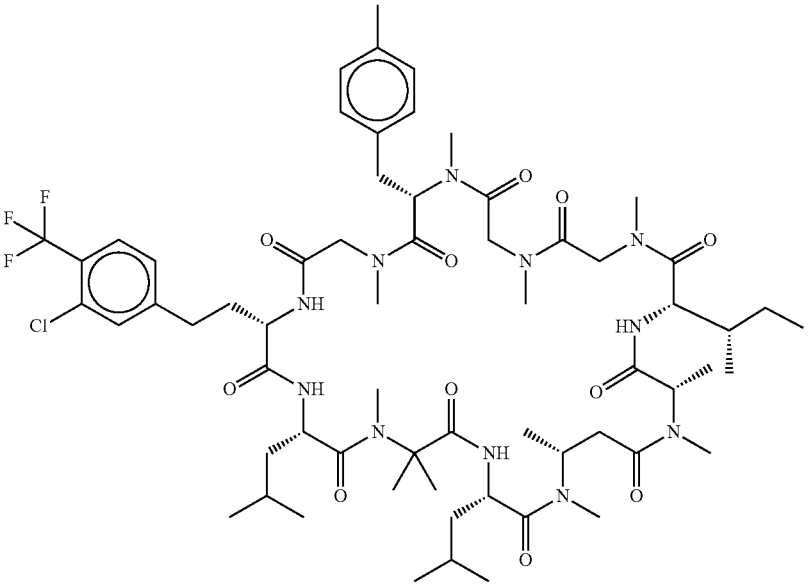 |
| 1399 | 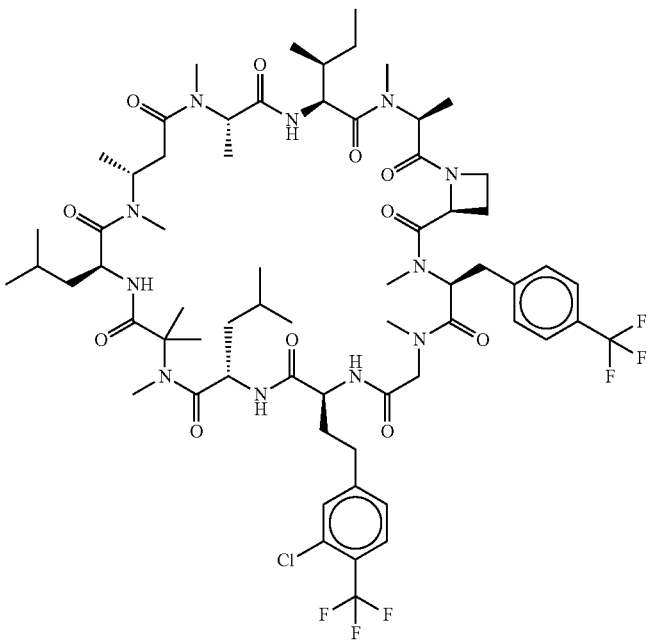 |

TABLE 24-continued
| Compound No. | Structural formula |
|---|---|
| 1400 | 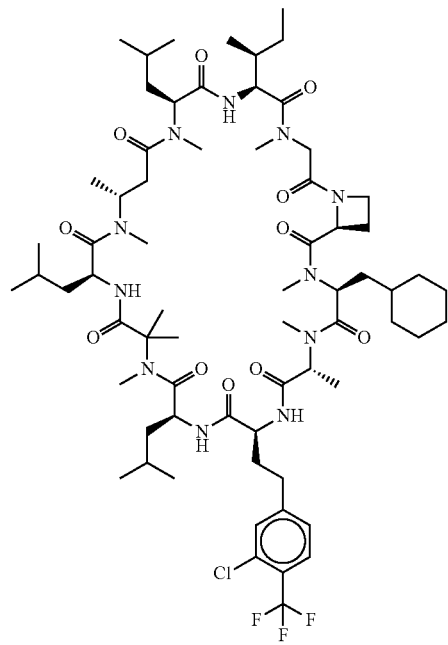 |
| 1401 | 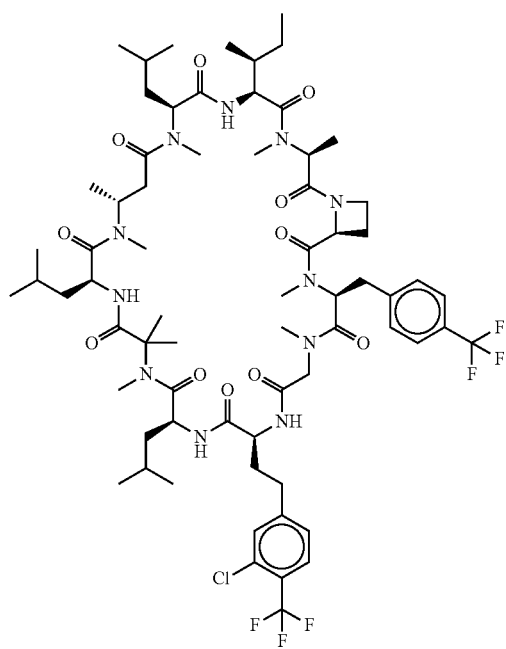 |

TABLE 24-continued
| Compound No. | Structural formula |
|---|---|
| 1402 | 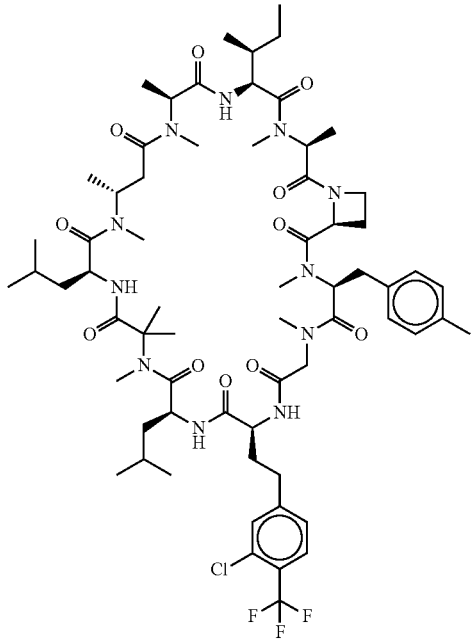 |
| 1403 | 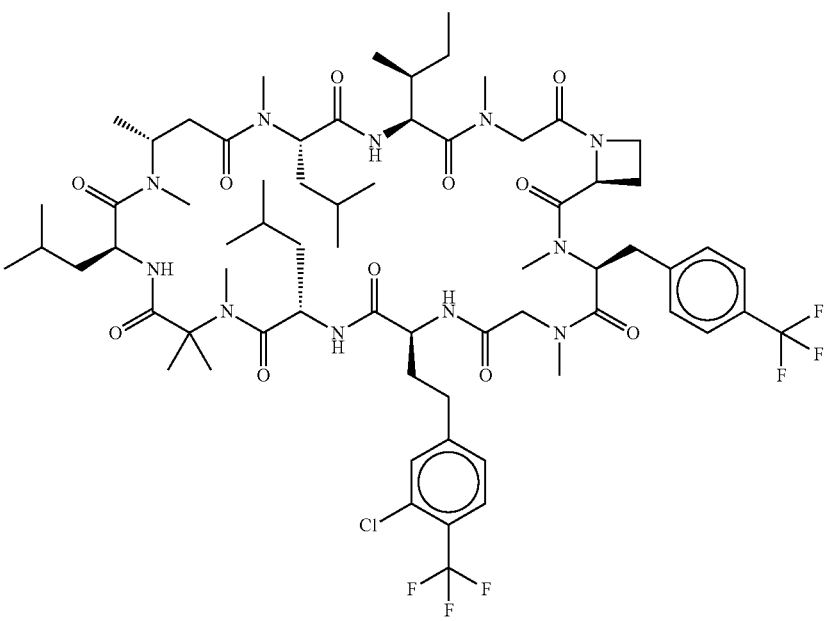 |

TABLE 24-continued
| Compound No. | Structural formula |
|---|---|
| 1404 | 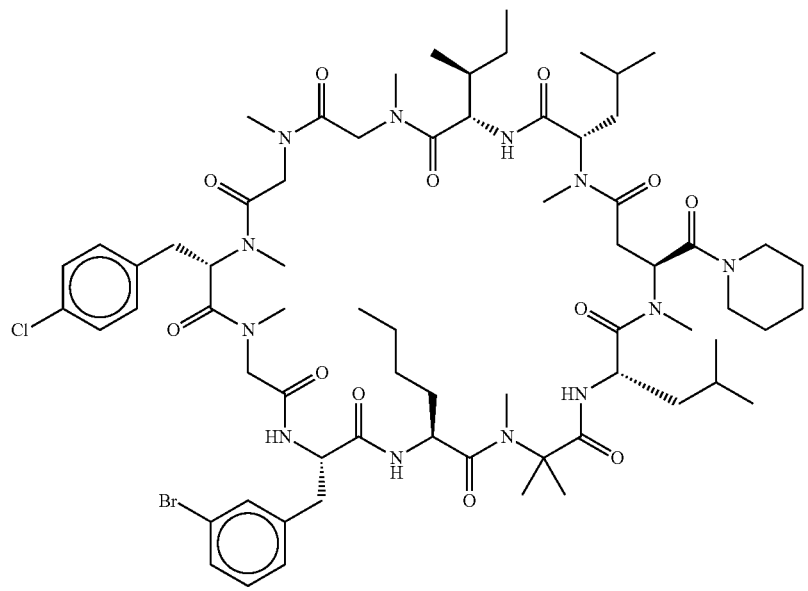 |
| 1405 | 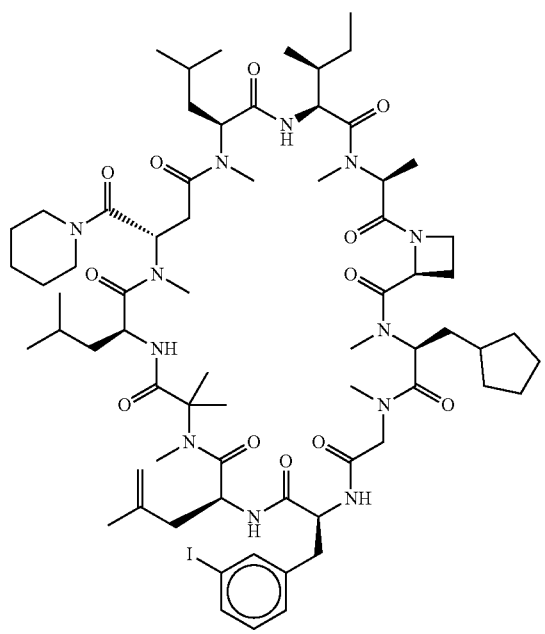 |

TABLE 24-continued
| Compound No. | Structural formula |
|---|---|
| 1406 | 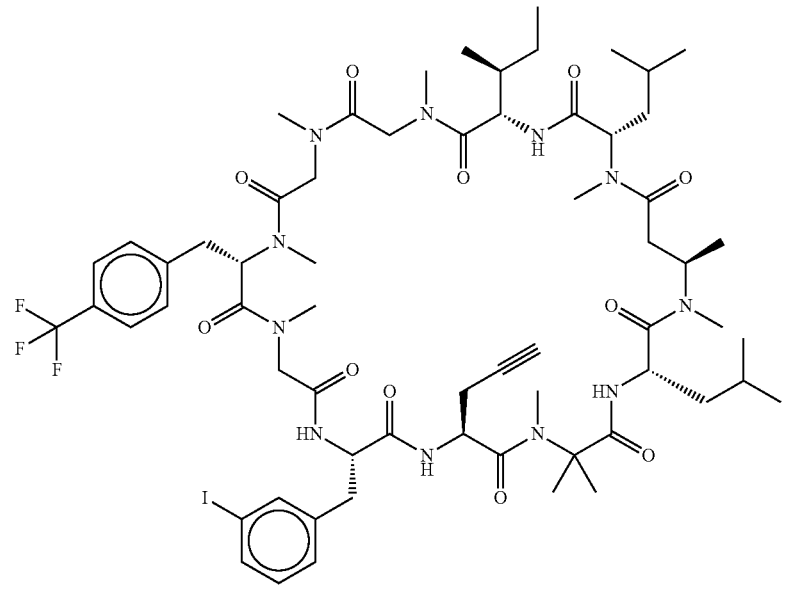 |
| 1407 | 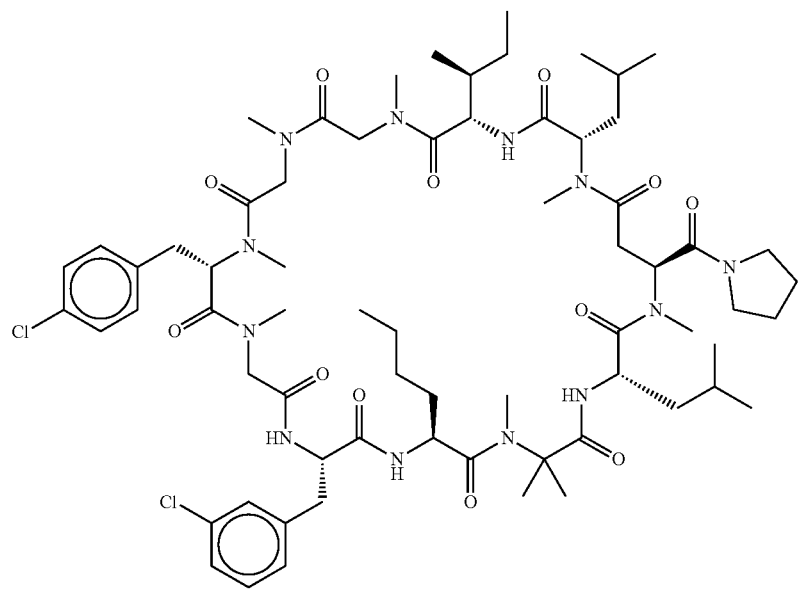 |

TABLE 24-continued
| Compound No. | Structural formula |
|---|---|
| 1408 | 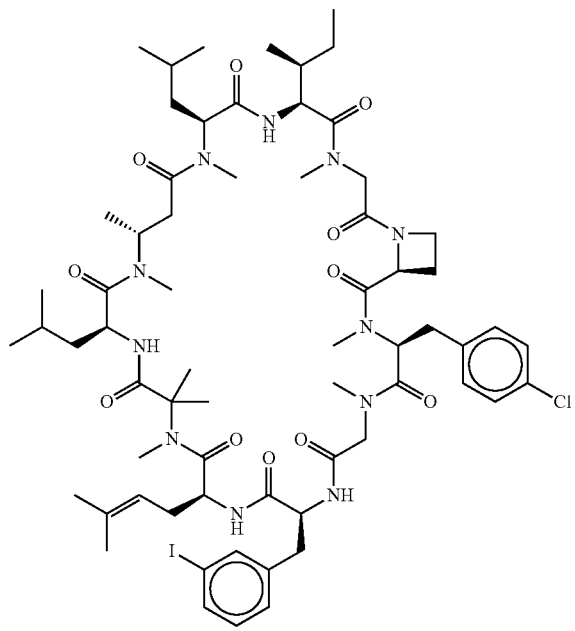 |
| 1409 | 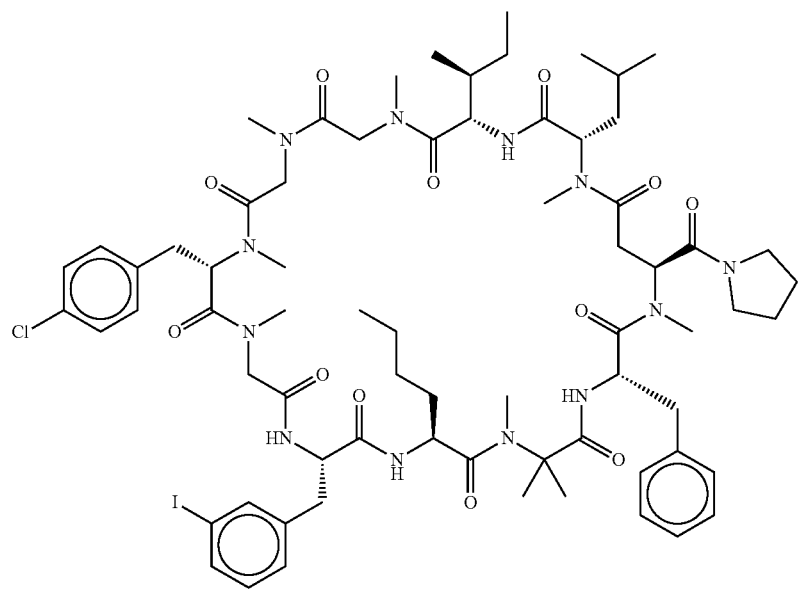 |

TABLE 24-continued
| Compound No. | Structural formula |
| --- | --- |
| 1410 | 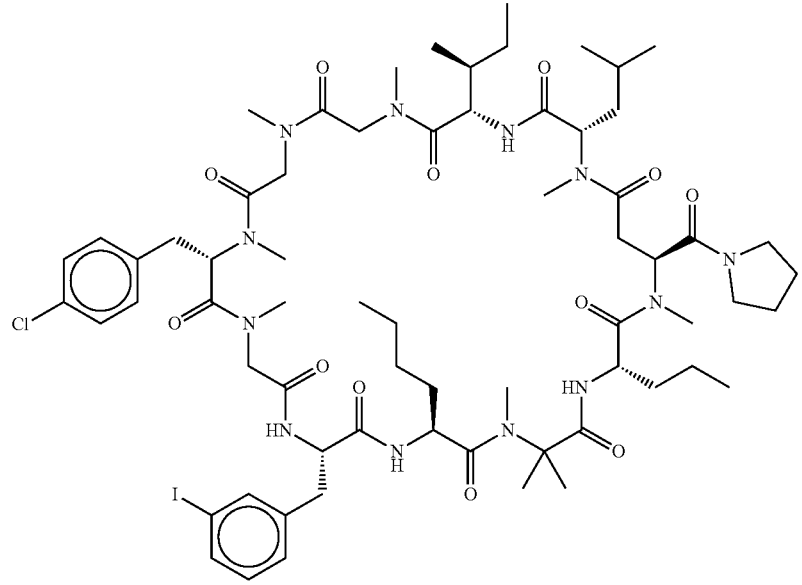 |
| 1411 | 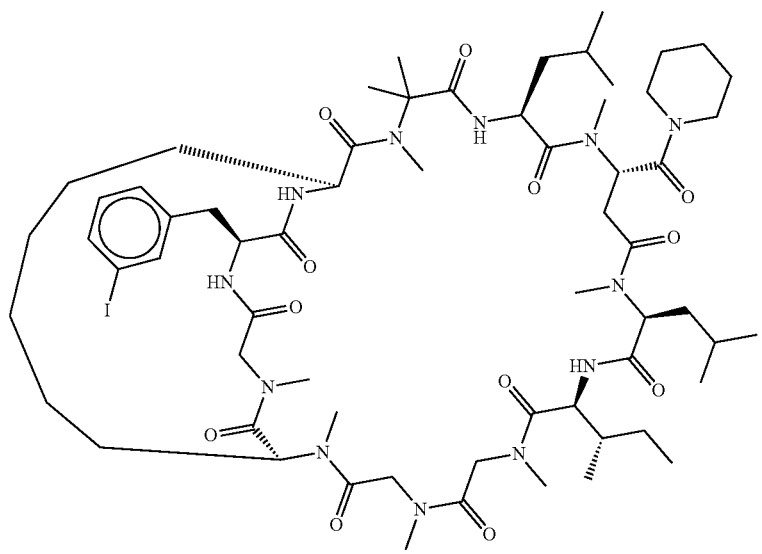 |

TABLE 24-continued
| Compound No. | Structural formula |
|---|---|
| 1412 | 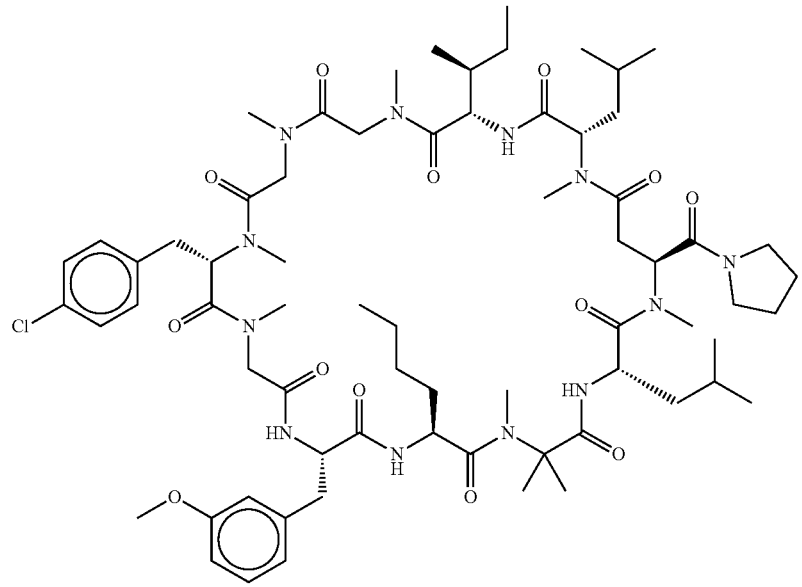 |
| 1413 | 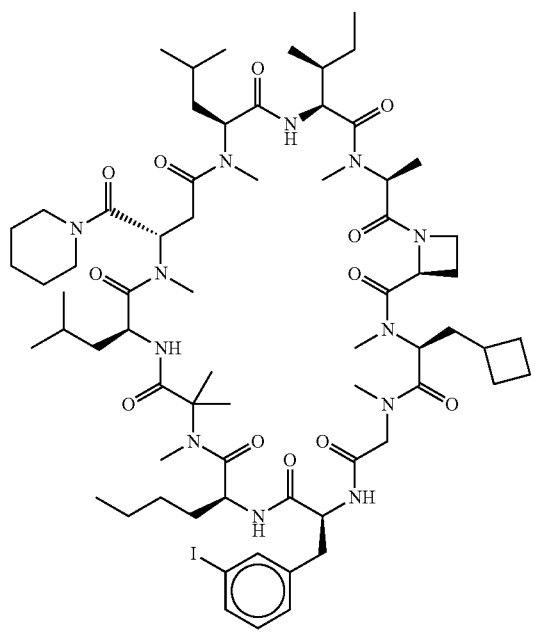 |

TABLE 24-continued
| Compound No. | Structural formula |
|---|---|
| 1414 | 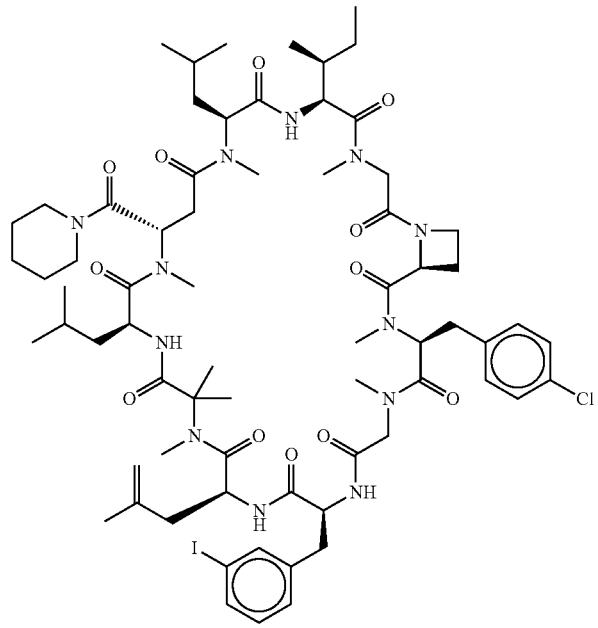 |
| 1415 | 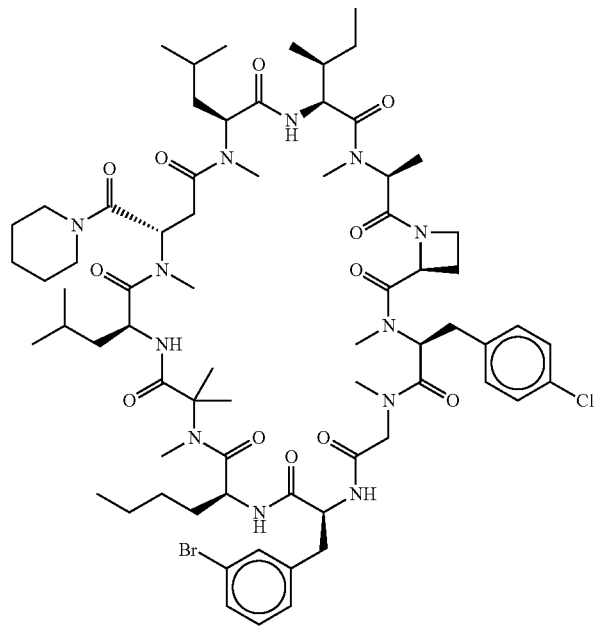 |

TABLE 24-continued
| Compound No. | Structural formula |
|---|---|
| 1416 | 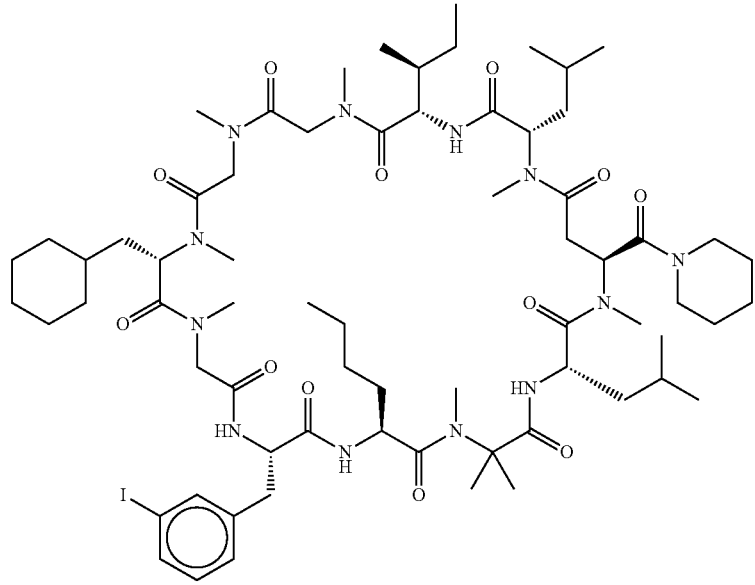 |
| 1417 | 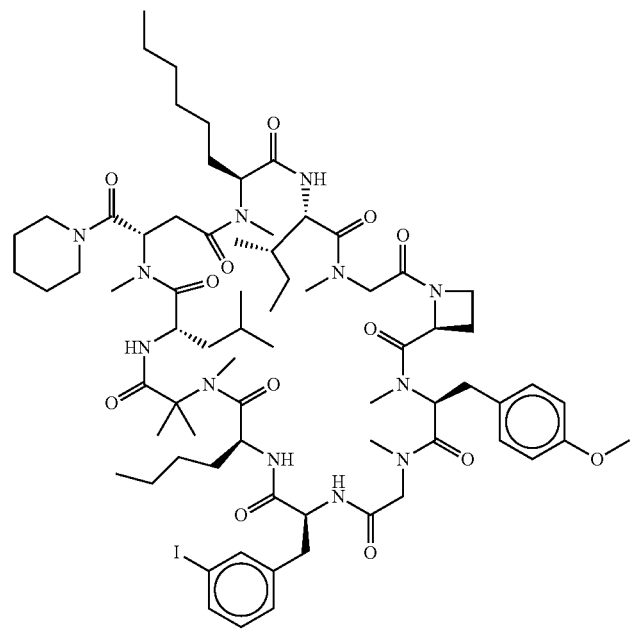 |

TABLE 24-continued
| Compound No. | Structural formula |
|---|---|
| 1418 | 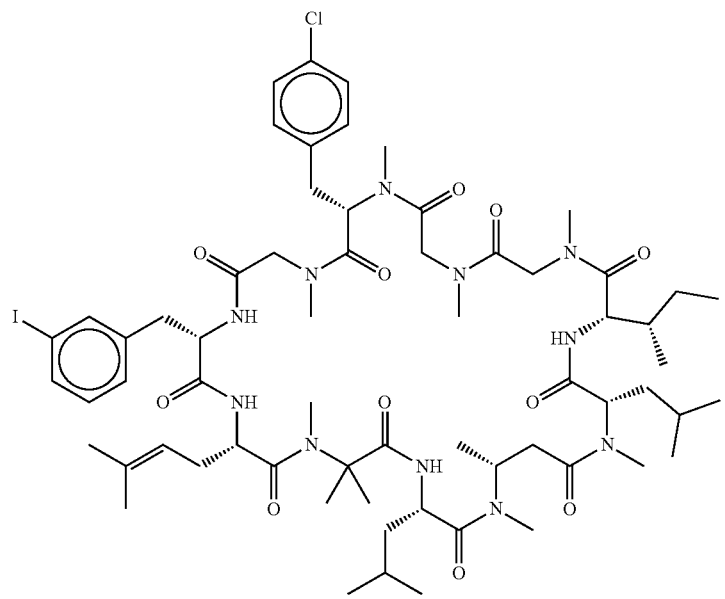 |
| 1419 | 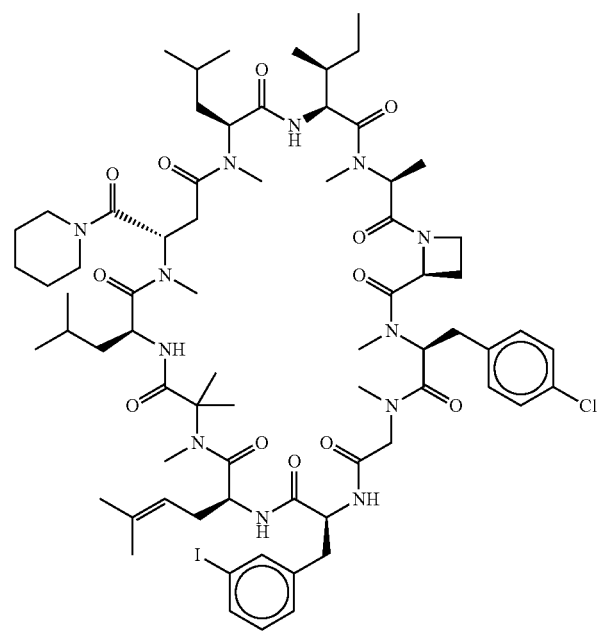 |

TABLE 24-continued
| Compound No. | Structural formula |
| --- | --- |
| 1420 | 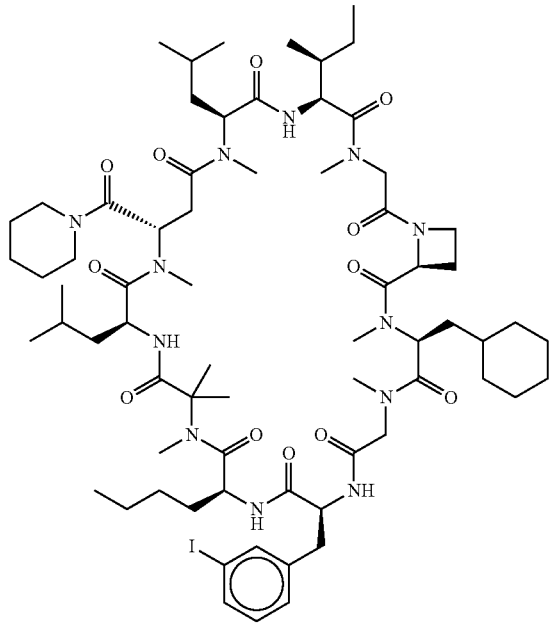 |
| 1421 | 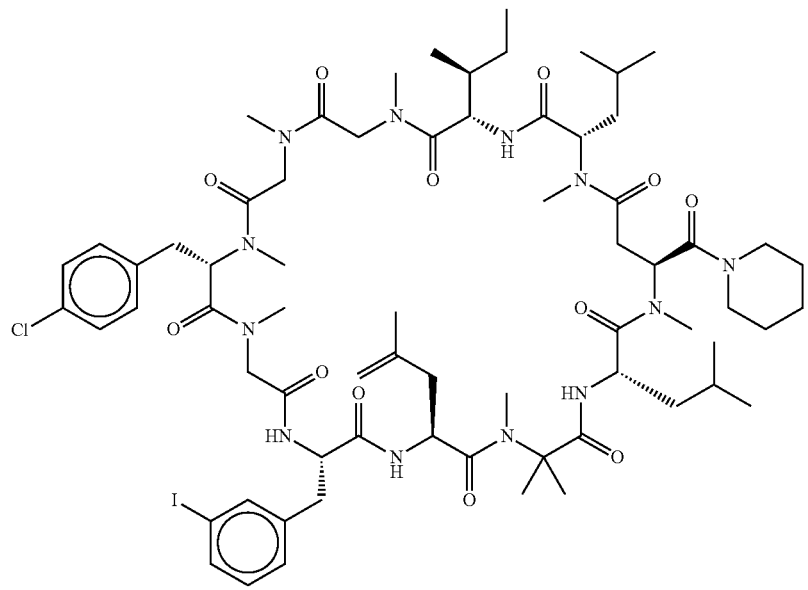 |

TABLE 24-continued
| Compound No. | Structural formula |
|---|---|
| 1422 | 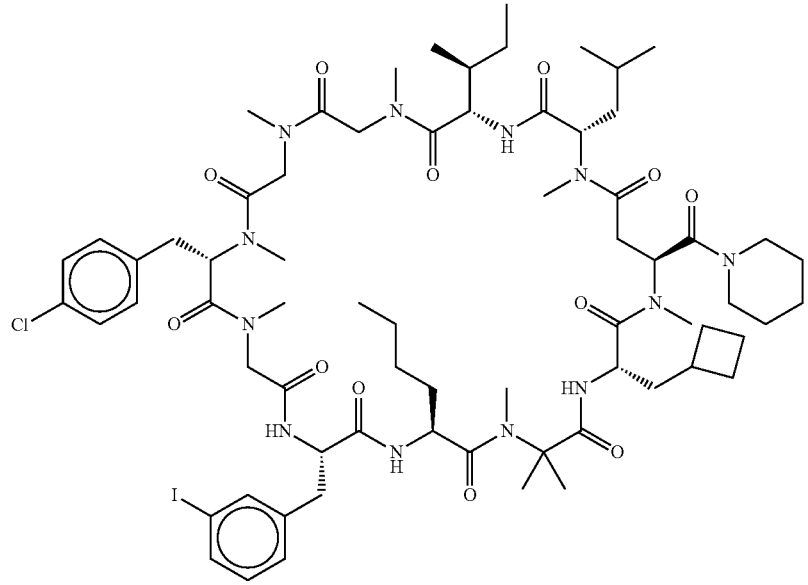 |
| 1423 | 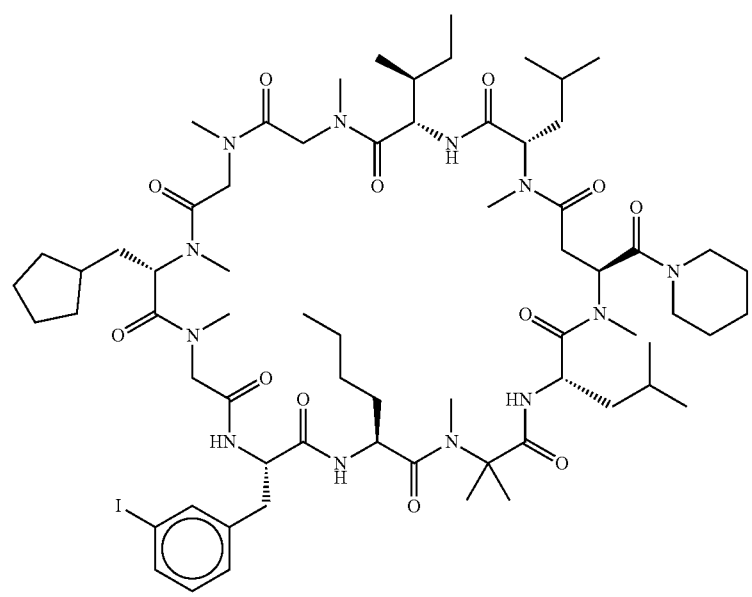 |

TABLE 24-continued
| Compound No. | Structural formula |
|---|---|
| 1424 | 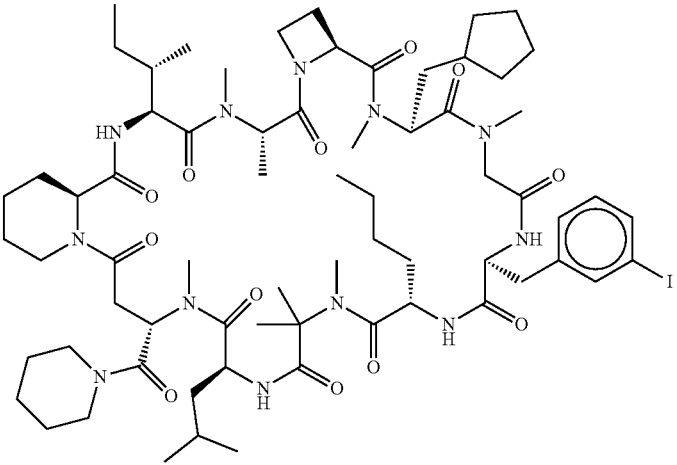 |
| 1425 | 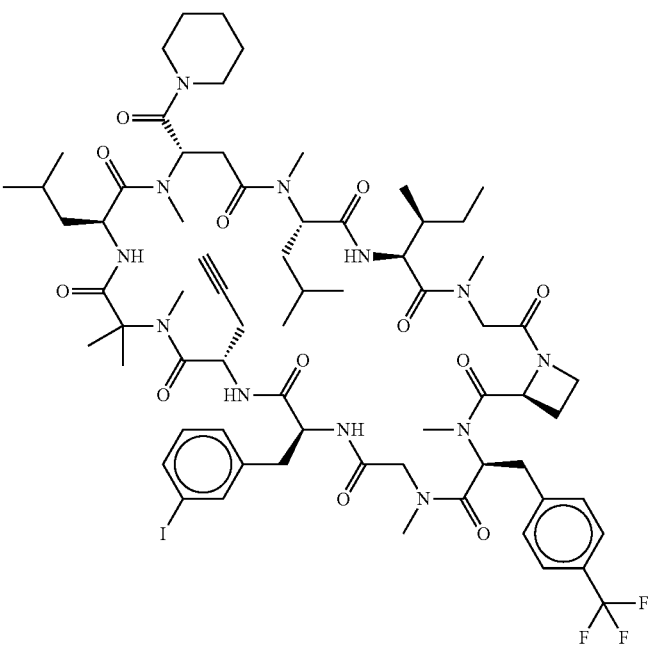 |

TABLE 24-continued
| Compound No. | Structural formula |
|---|---|
| 1426 | 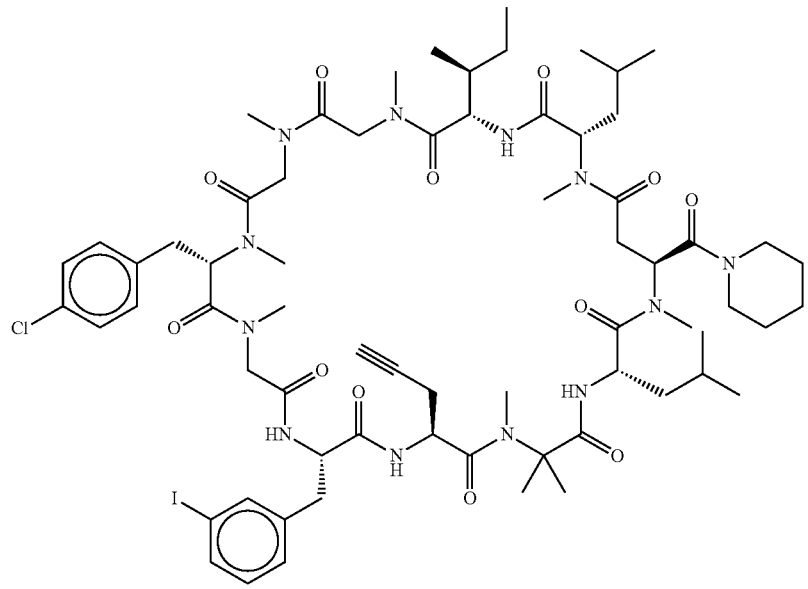 |
| 1427 | 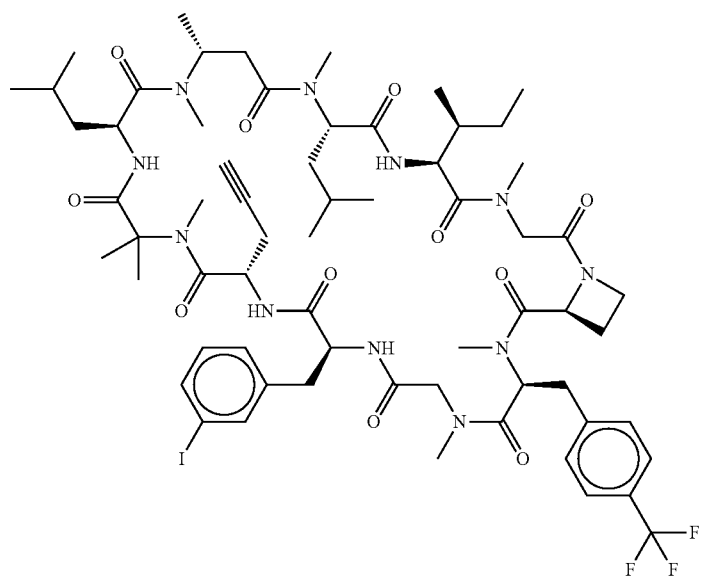 |

TABLE 24-continued
| Compound No. | Structural formula |
|---|---|
| 1428 | 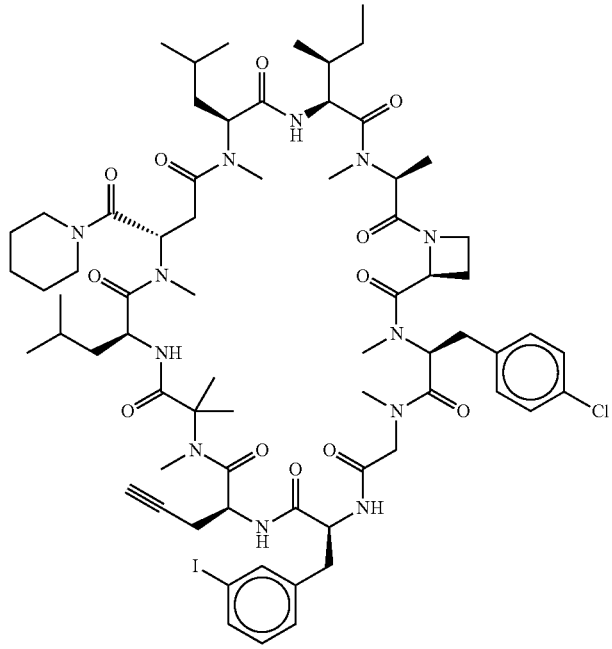 |
| 1429 | 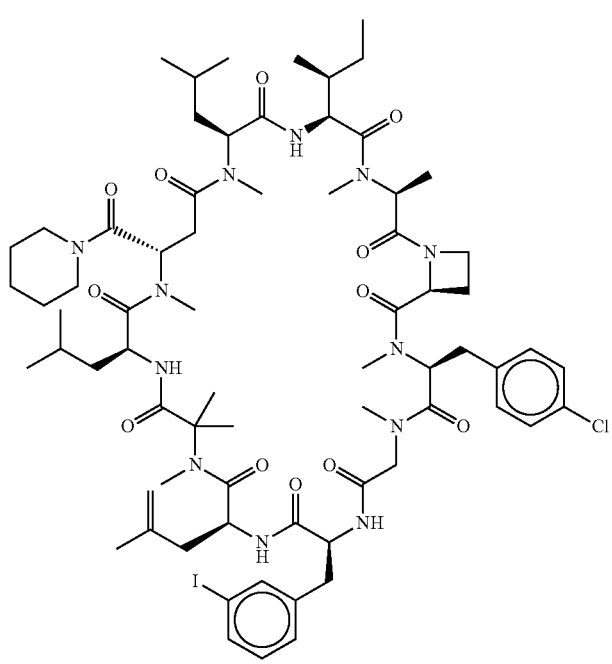 |

TABLE 24-continued
| Compound No. | Structural formula |
|---|---|
| 1430 | 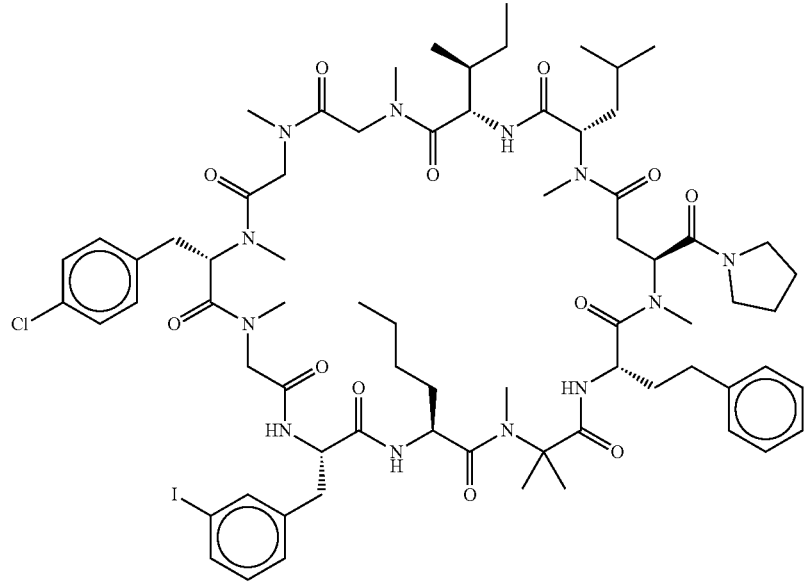 |
| 1431 | 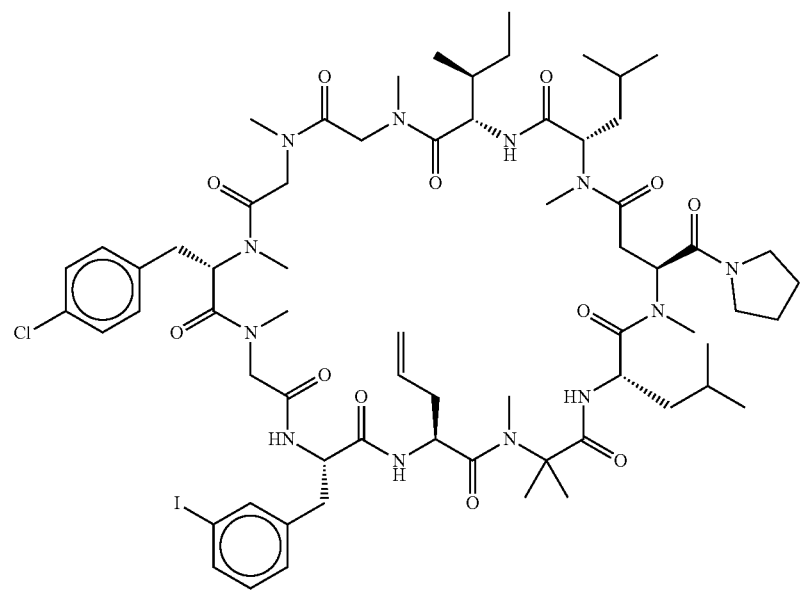 |

TABLE 24-continued
| Compound No. | Structural formula |
|---|---|
| 1432 | 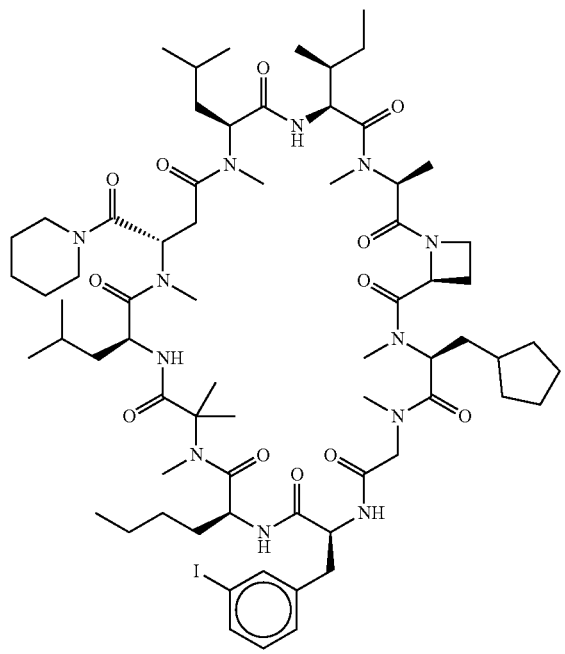 |
| 1433 | 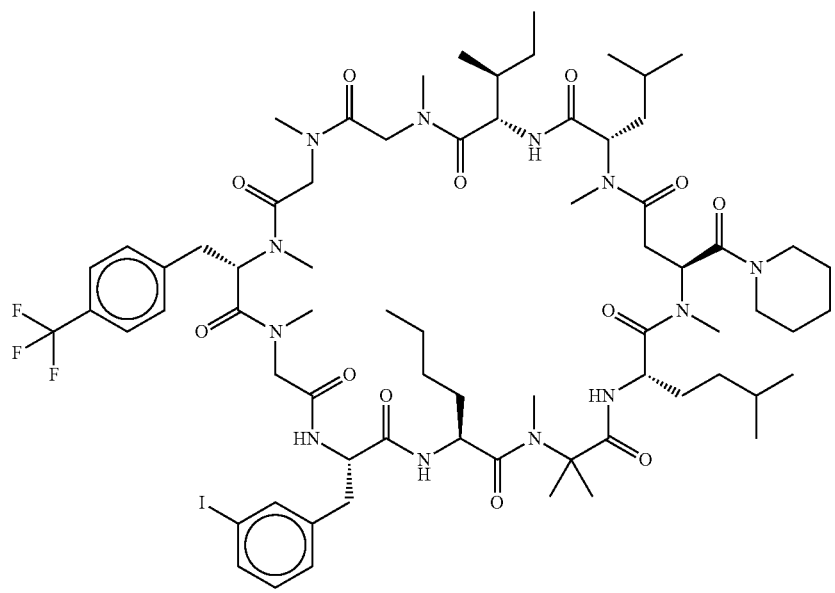 |

TABLE 24-continued
| Compound No. | Structural formula |
|---|---|
| 1434 | 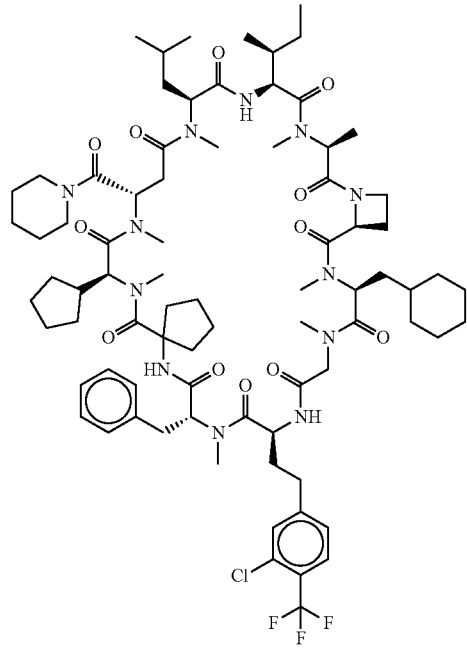 |
| 1435 | 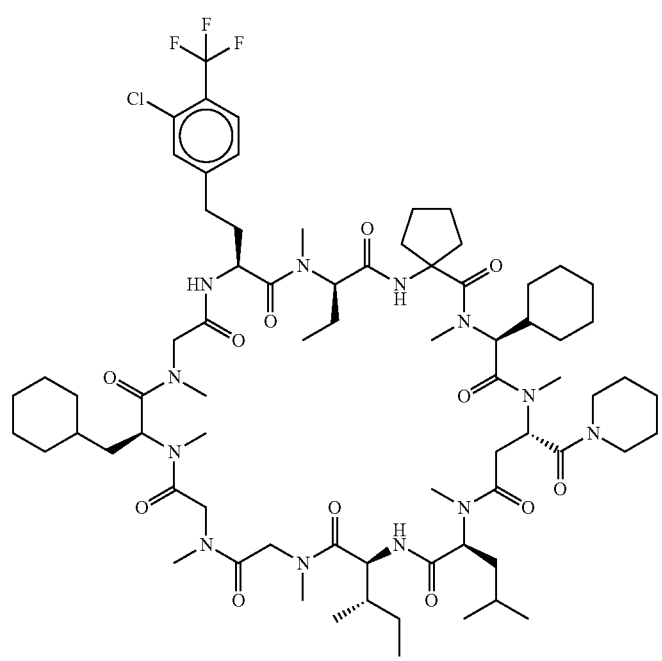 |

TABLE 24-continued
| Compound No. | Structural formula |
|---|---|
| 1436 | 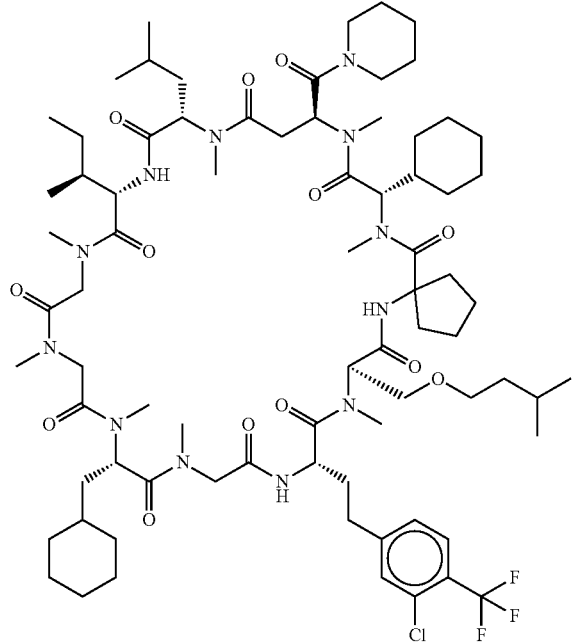 |
| 1437 | 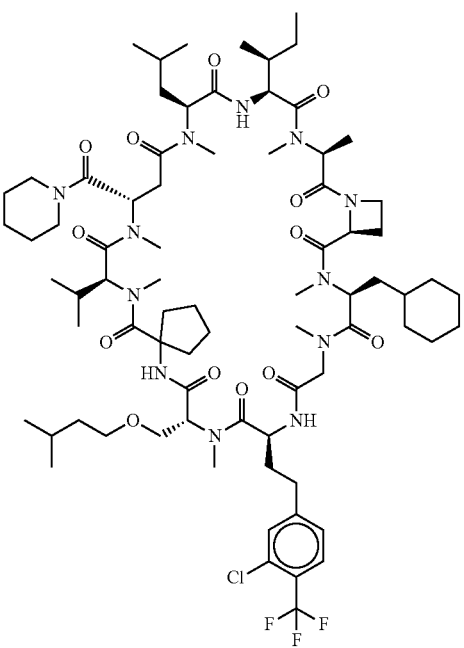 |

TABLE 24-continued
| Compound No. | Structural formula |
|---|---|
| 1438 | 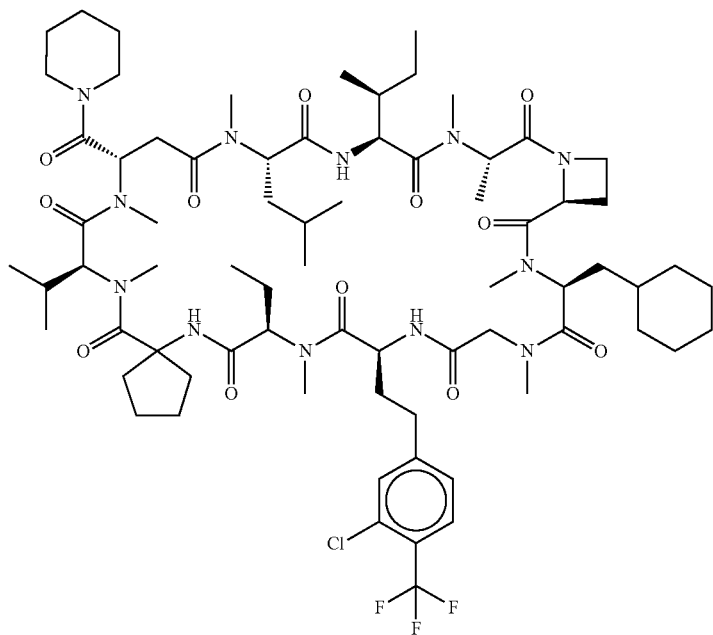 |
| 1439 | 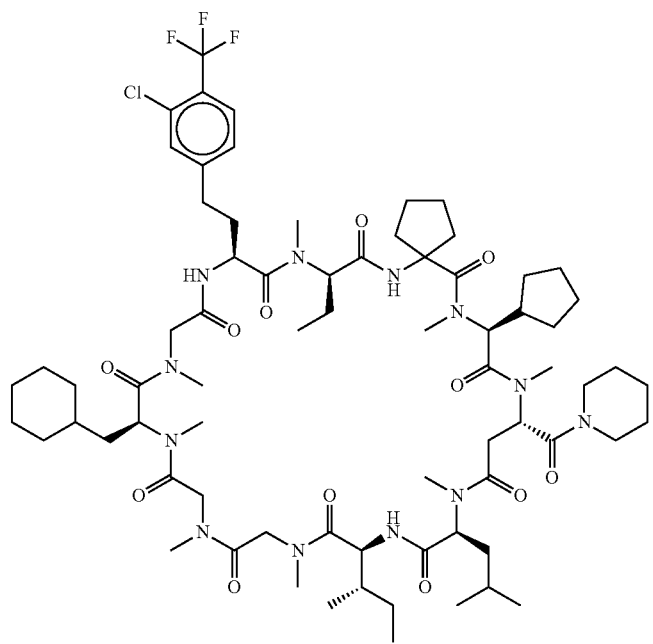 |

TABLE 24-continued
| Compound No. | Structural formula |
| --- | --- |
| 1440 | 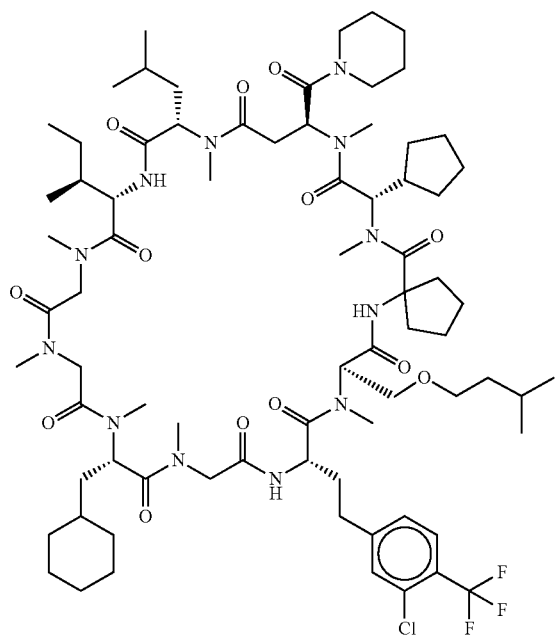 |
| 1441 | 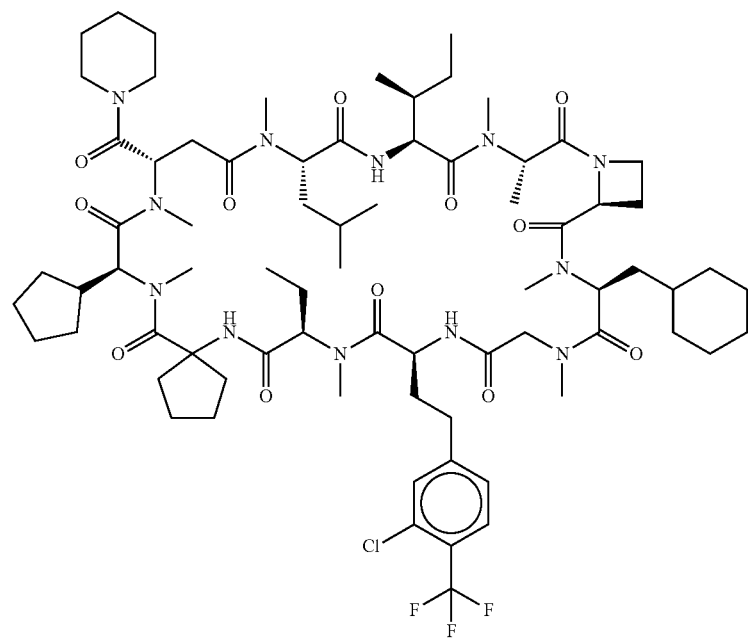 |

TABLE 24-continued
| Compound No. | Structural formula |
|---|---|
| 1442 | 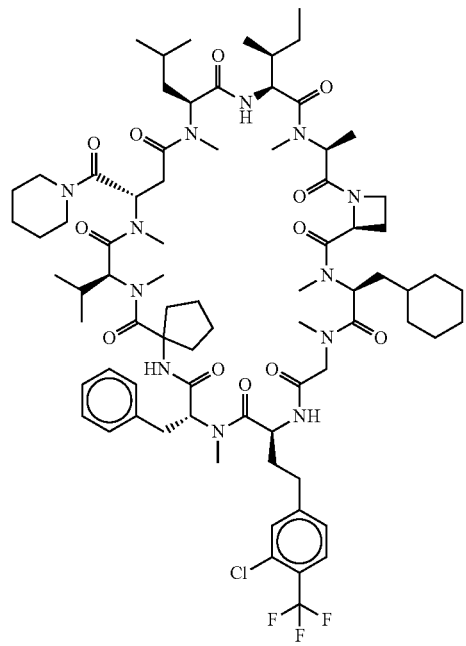 |
| 1443 | 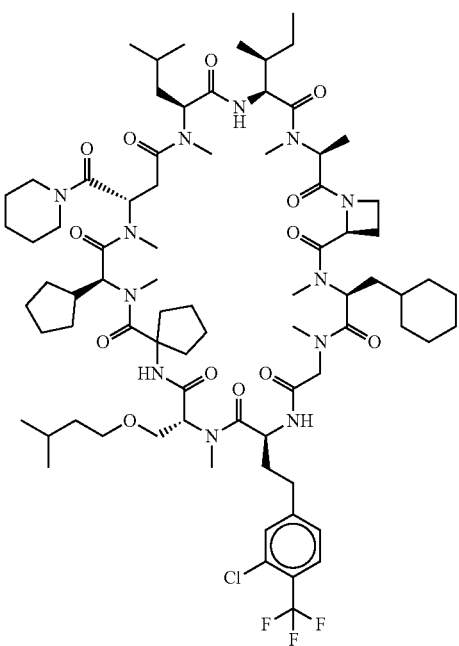 |

TABLE 24-continued
| Compound No. | Structural formula |
|---|---|
| 1444 | 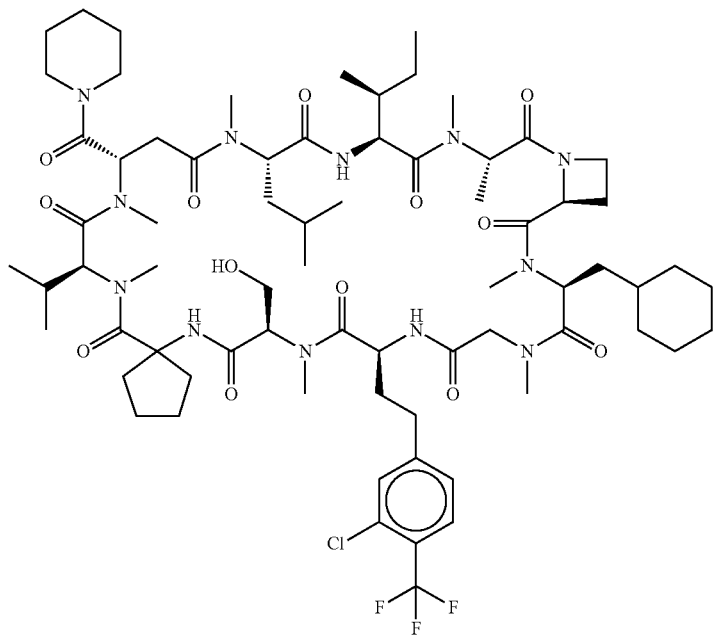 |
| 1445 | 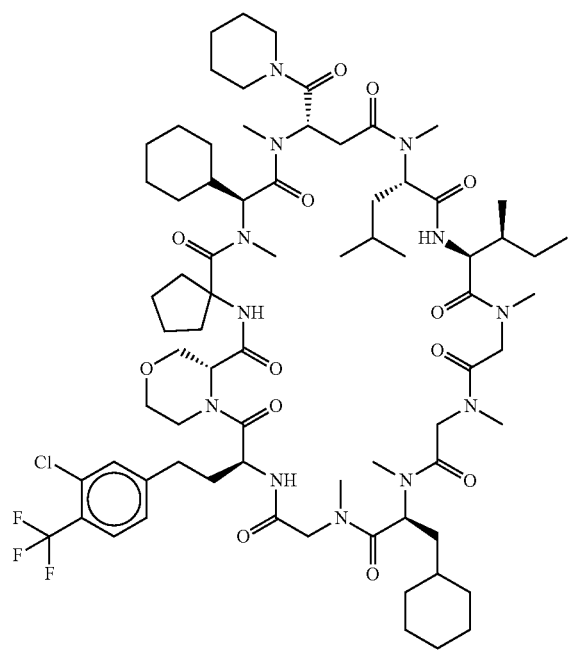 |

TABLE 24-continued
| Compound No. | Structural formula |
|---|---|
| 1446 | 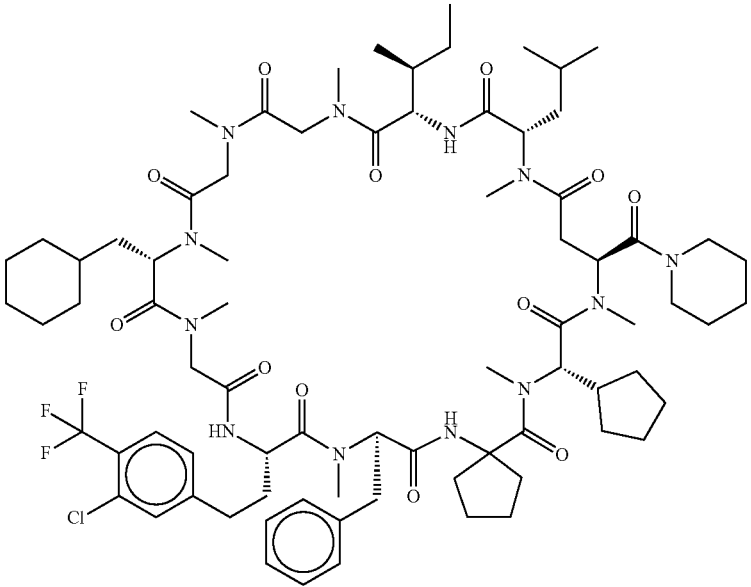 |
| 1447 | 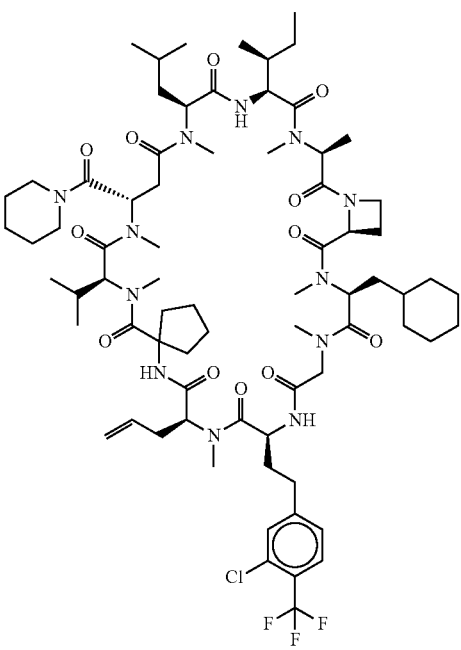 |

TABLE 24-continued
| Compound No. | Structural formula |
|---|---|
| 1448 | 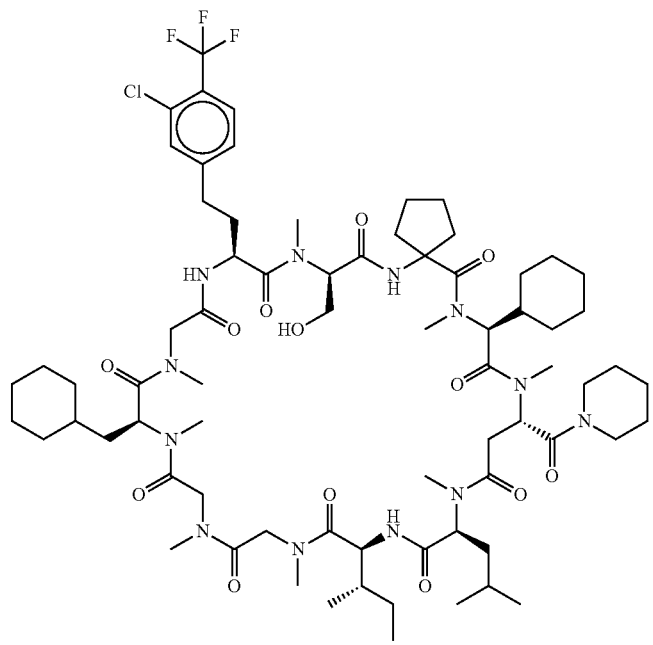 |
| 1449 | 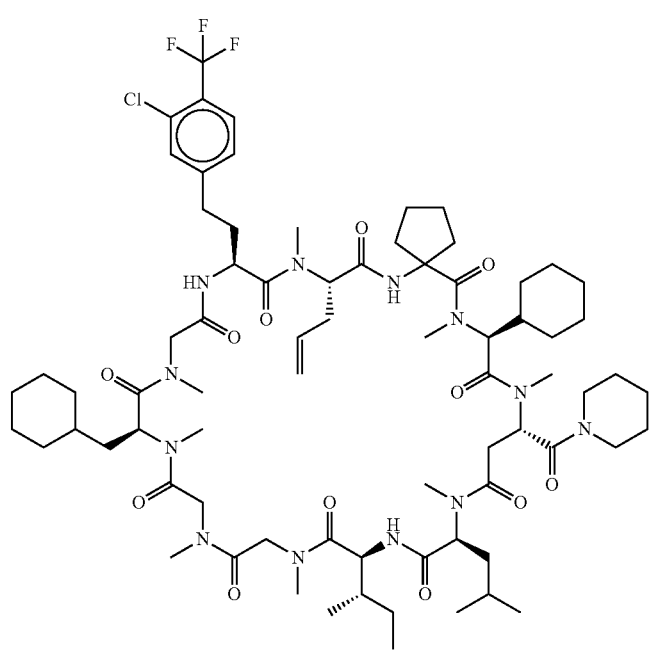 |

TABLE 24-continued
| Compound No. | Structural formula |
|---|---|
| 1450 | 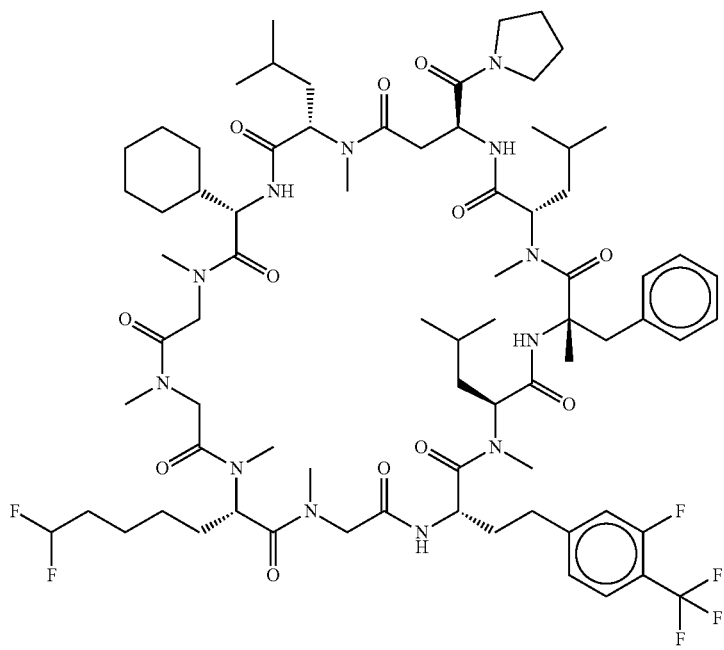 |
| 1451 | 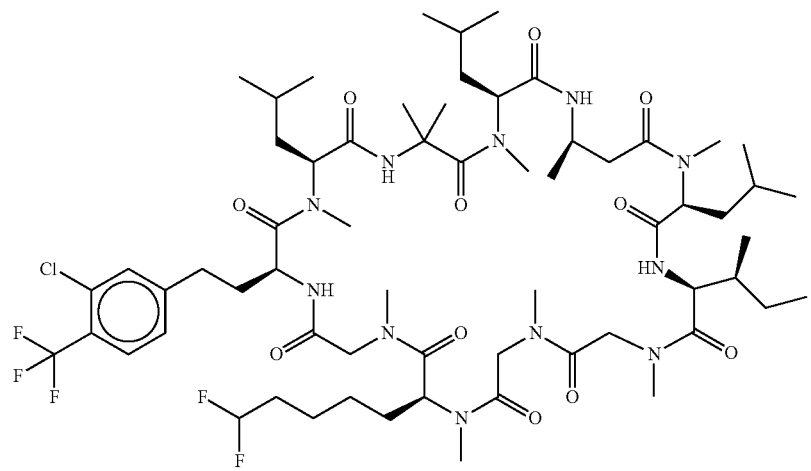 |

TABLE 24-continued
| Compound No. | Structural formula |
|---|---|
| 1452 | 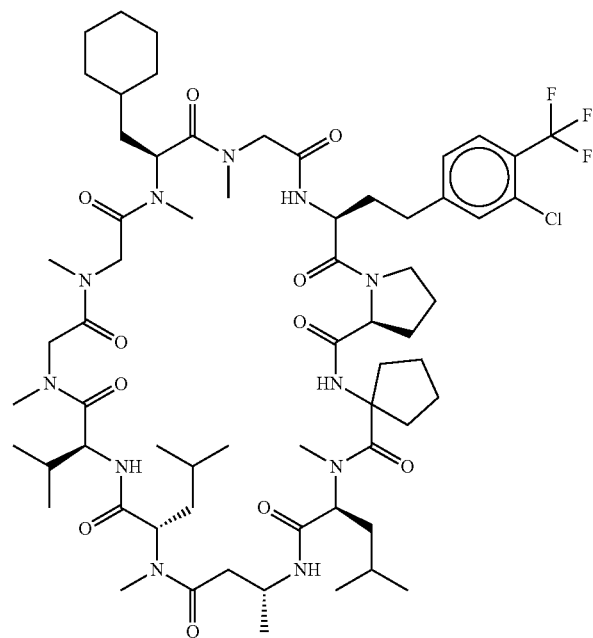 |
| 1453 | 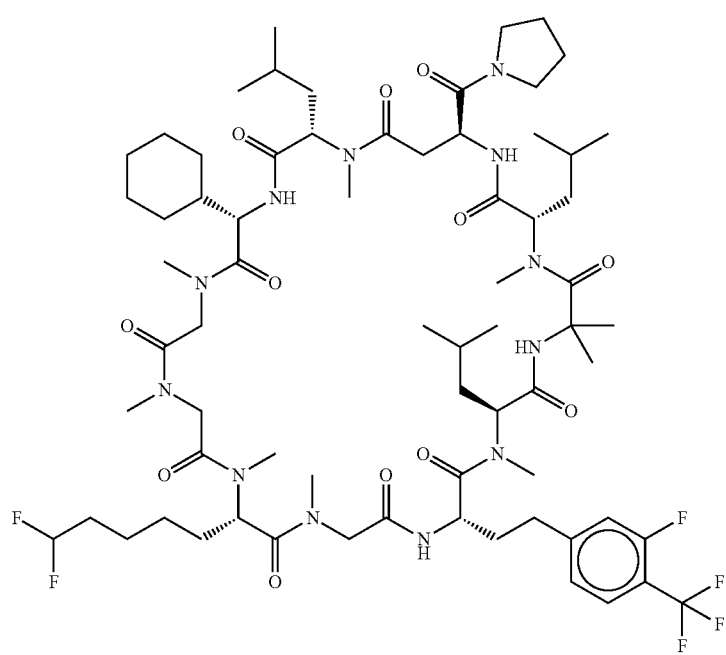 |

TABLE 24-continued
| Compound No. | Structural formula |
|---|---|
| 1454 | 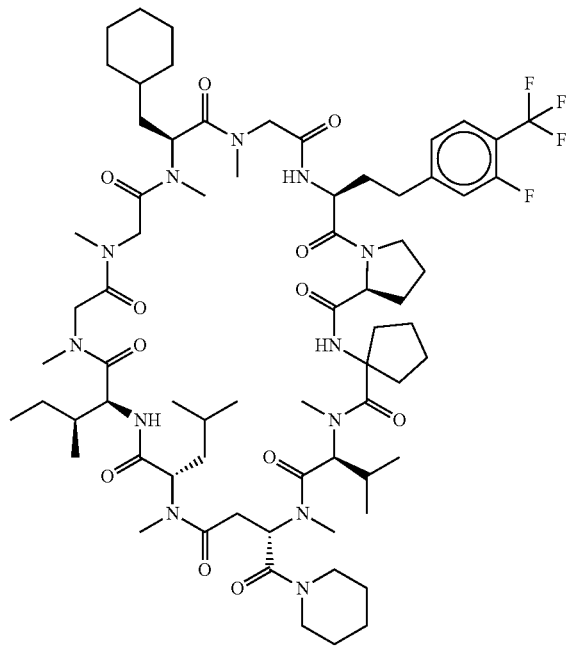 |
| 1455 | 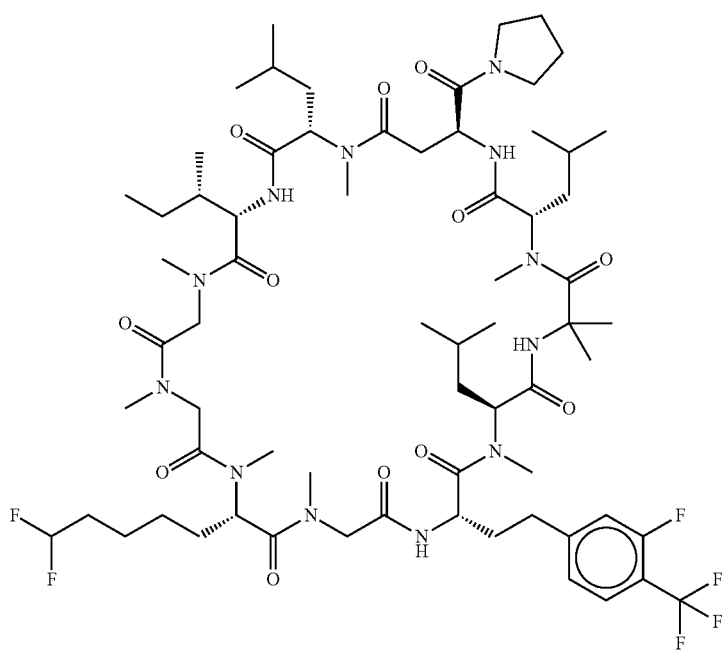 |

TABLE 24-continued
| Compound No. | Structural formula |
|---|---|
| 1456 | 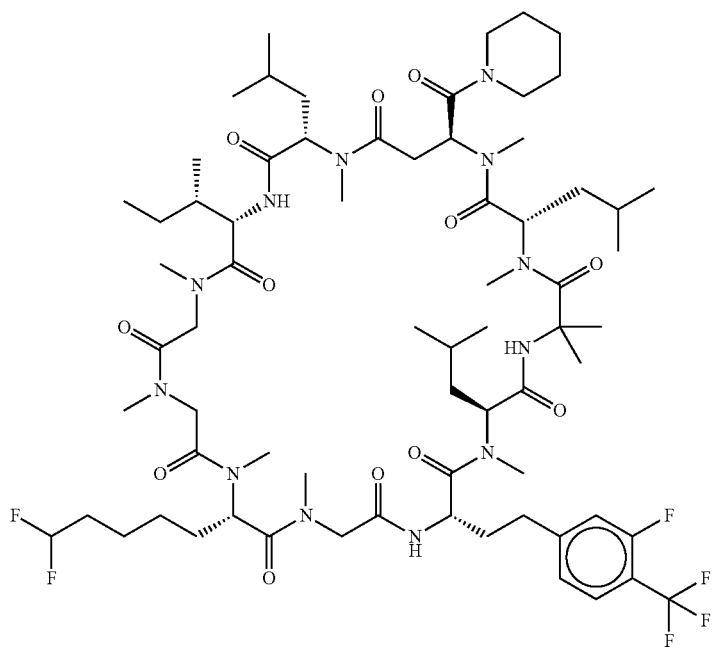 |
| 1457 | 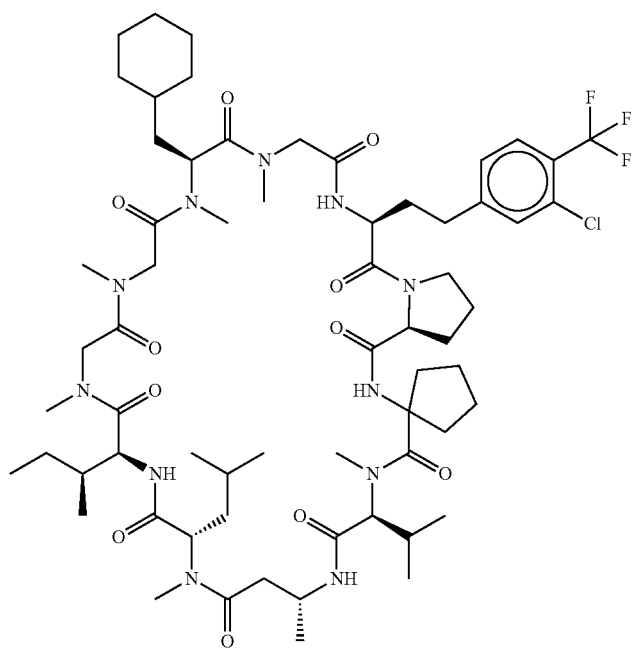 |

TABLE 24-continued
| Compound No. | Structural formula |
|---|---|
| 1458 | 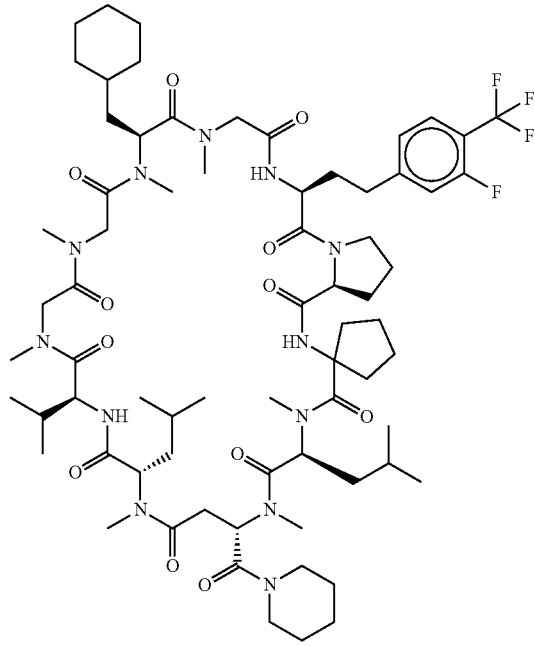 |
| 1459 | 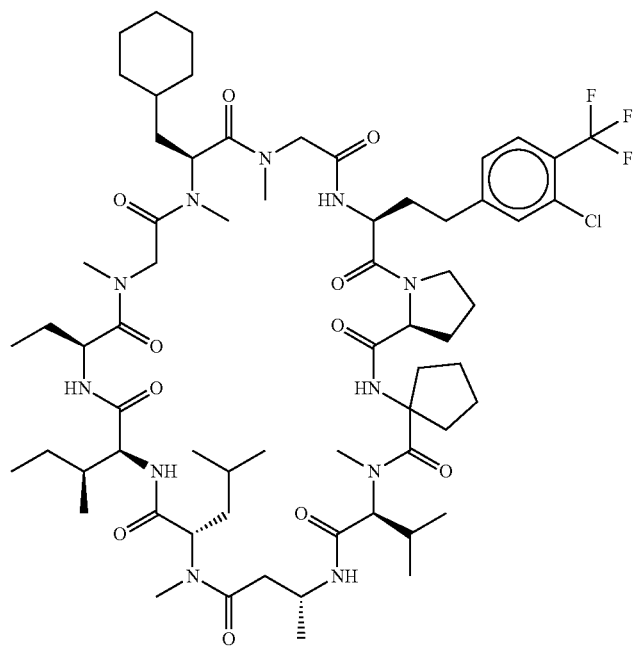 |

TABLE 24-continued
| Compound No. | Structural formula |
|---|---|
| 1460 | 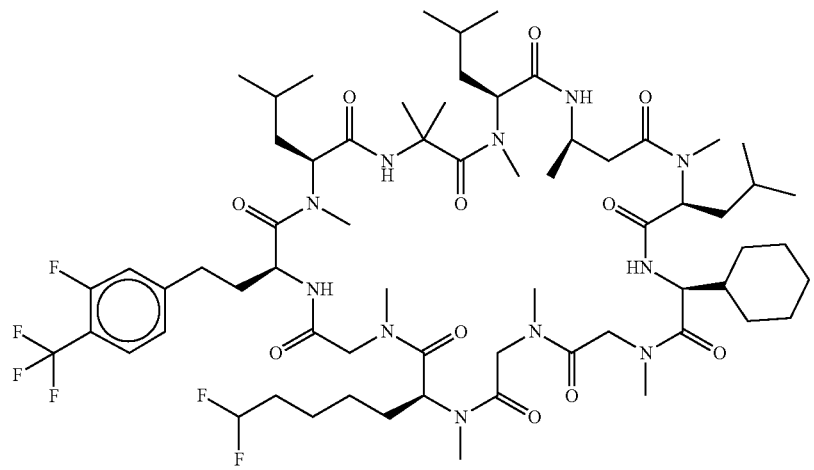 |
| 1461 | 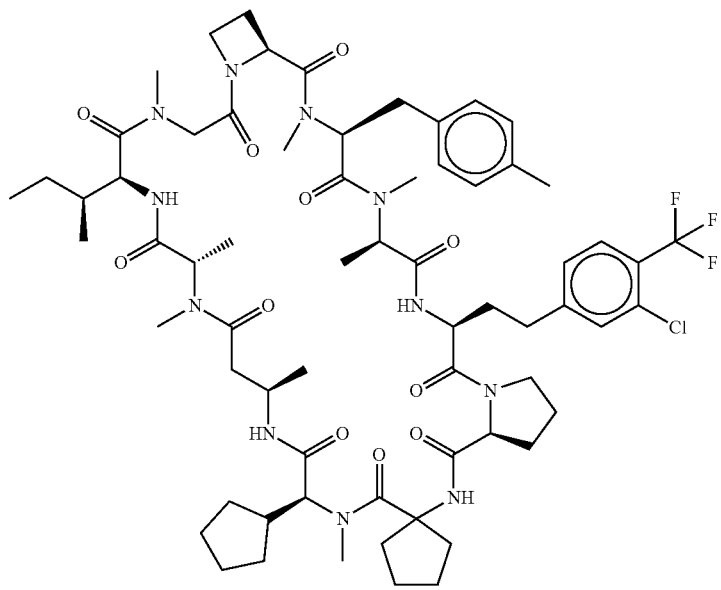 |

TABLE 24-continued
| Compound No. | Structural formula |
| --- | --- |
| 1462 | 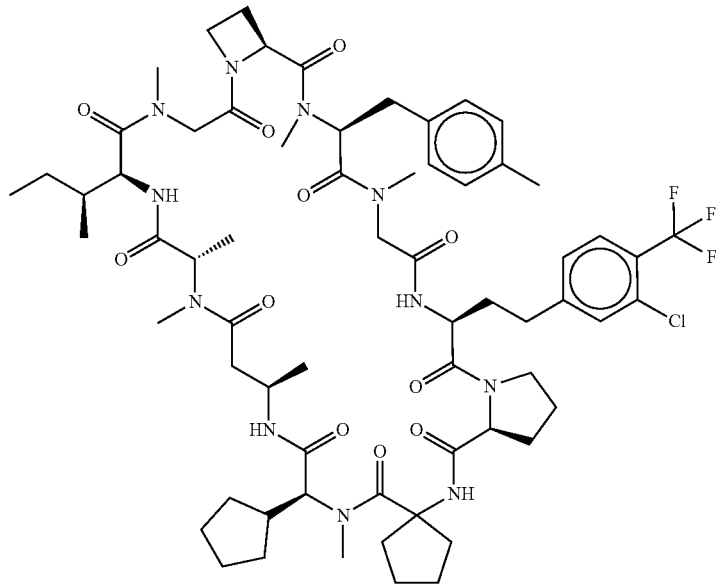 |
| 1463 | 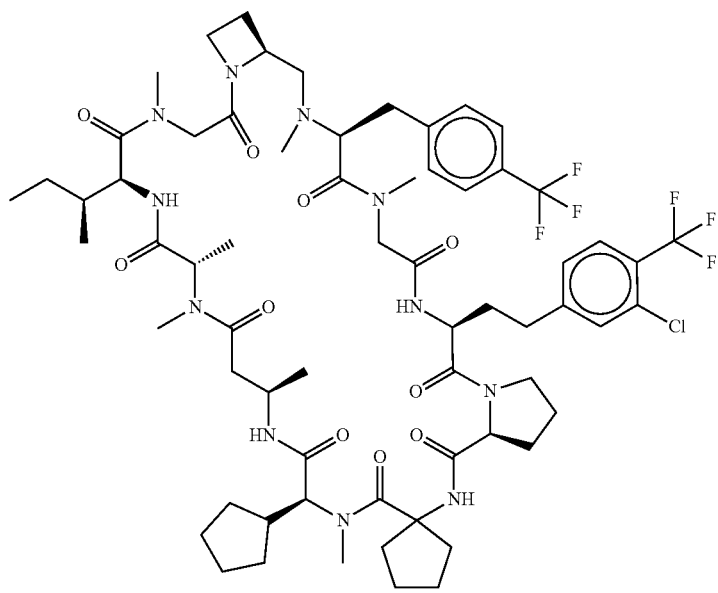 |

| Compound No. | Structural formula |
|---|---|
| 1464 | 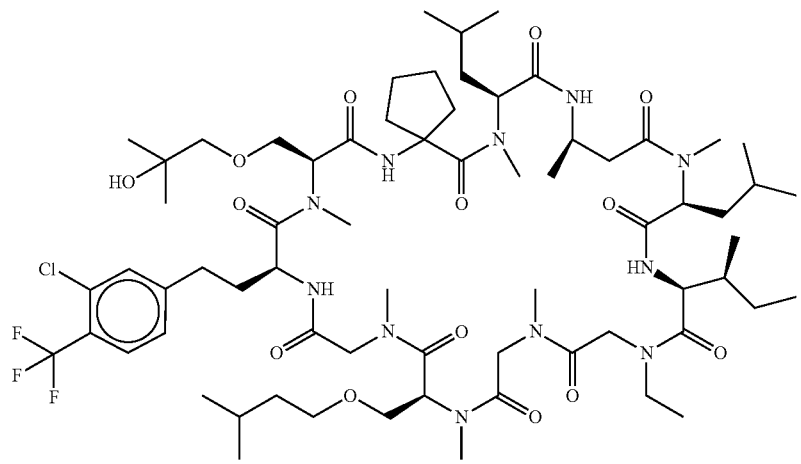 |
| 1465 | 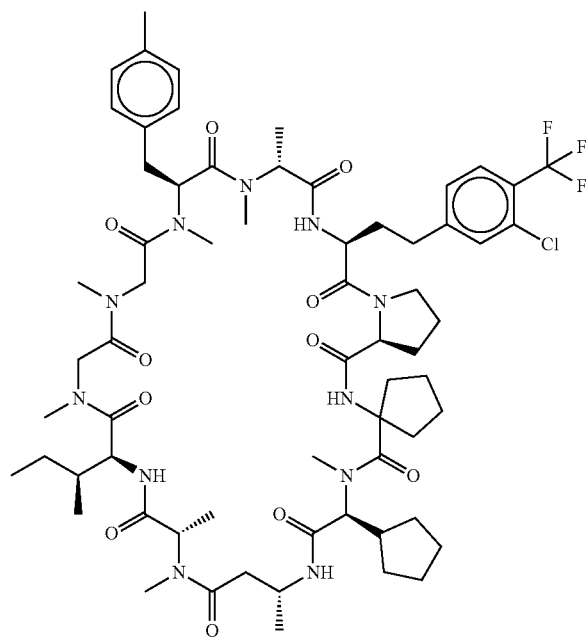 |

TABLE 24-continued
| Compound No. | Structural formula |
|---|---|
| 1466 | 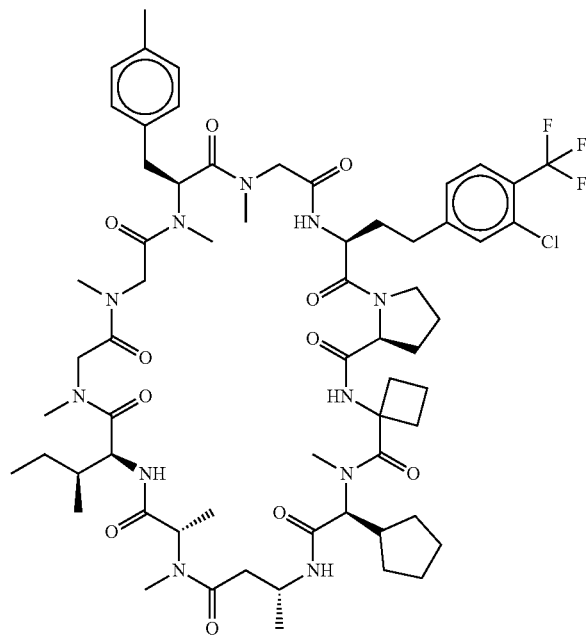 |
| 1467 | 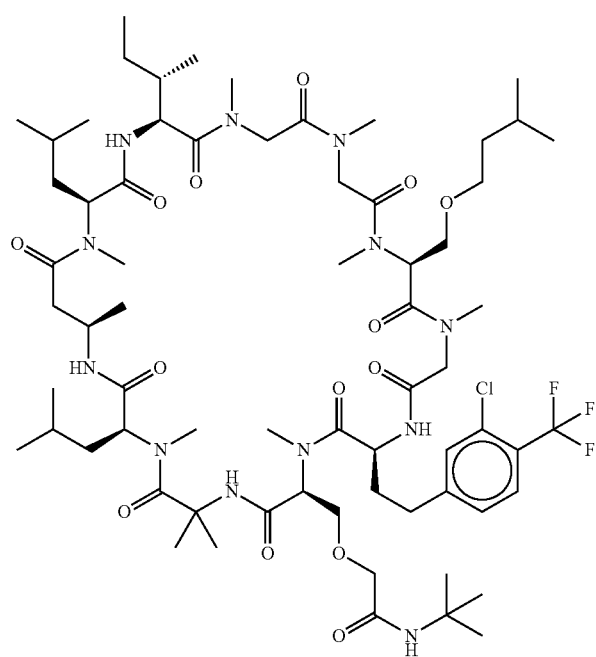 |

TABLE 24-continued
| Compound No. | Structural formula |
|---|---|
| 1468 | 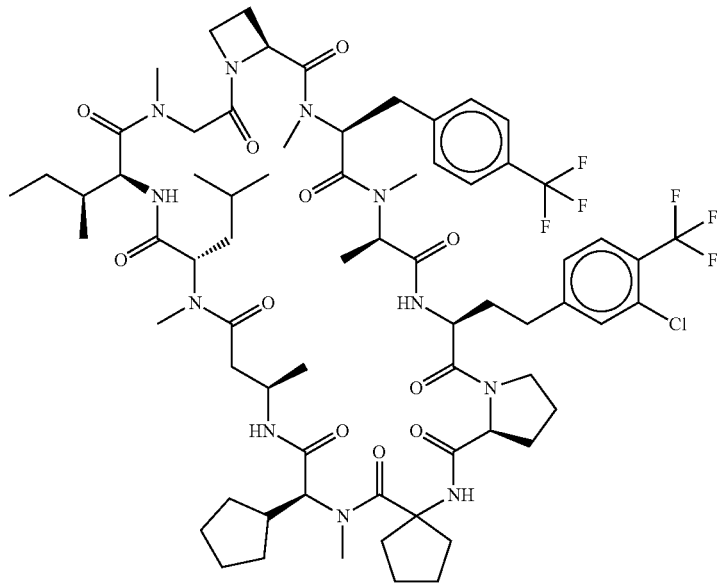 |
| 1469 | 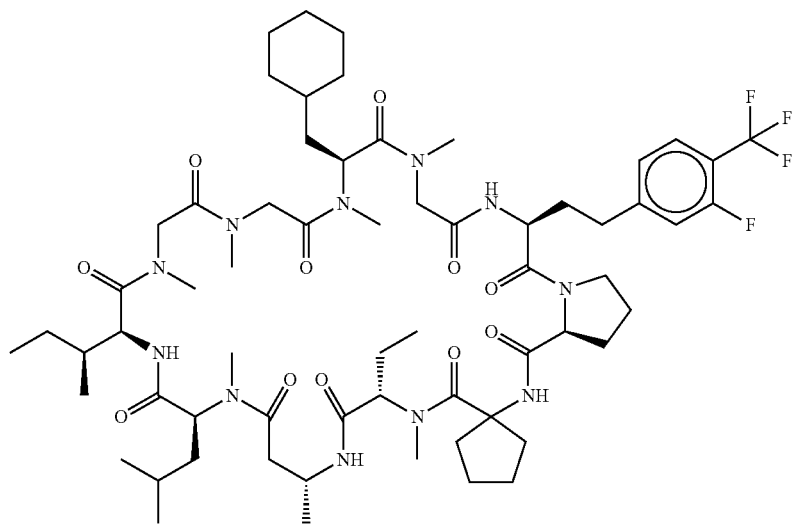 |

TABLE 24-continued
| Compound No. | Structural formula |
|---|---|
| 1470 | 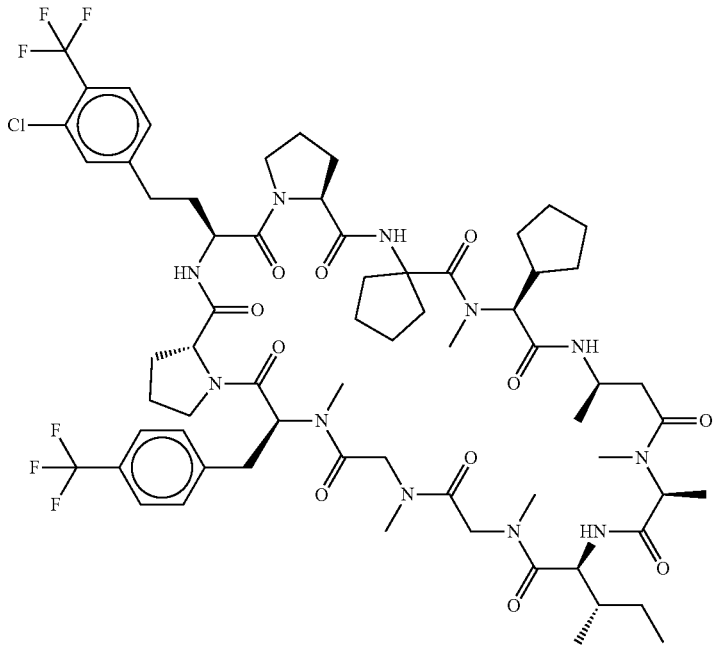 |
| 1471 | 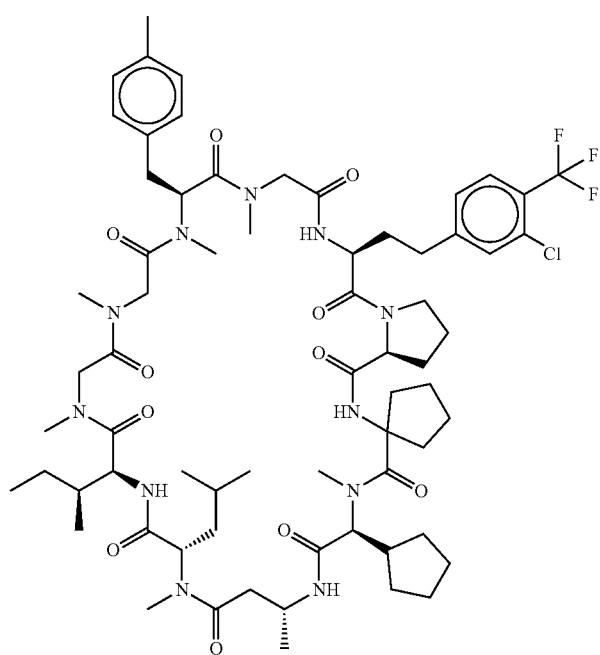 |

TABLE 24-continued
| Compound No. | Structural formula |
|---|---|
| 1472 | 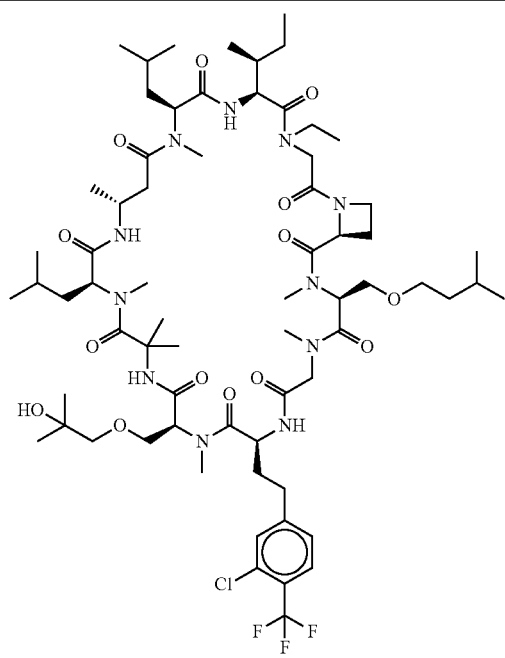 |
| 1473 | 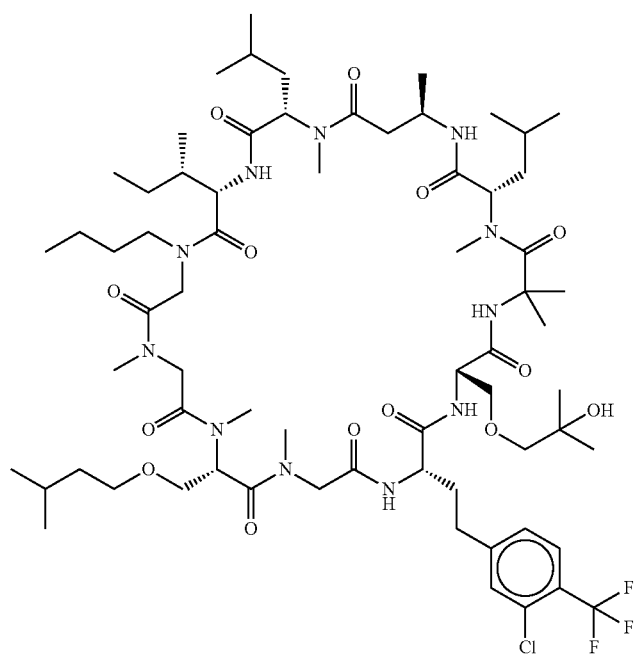 |

US 12,371,454 B2
2417                                                                                           2418
TABLE 24-continued
| Compound No. | Structural formula |
|---|---|
| 1474 | 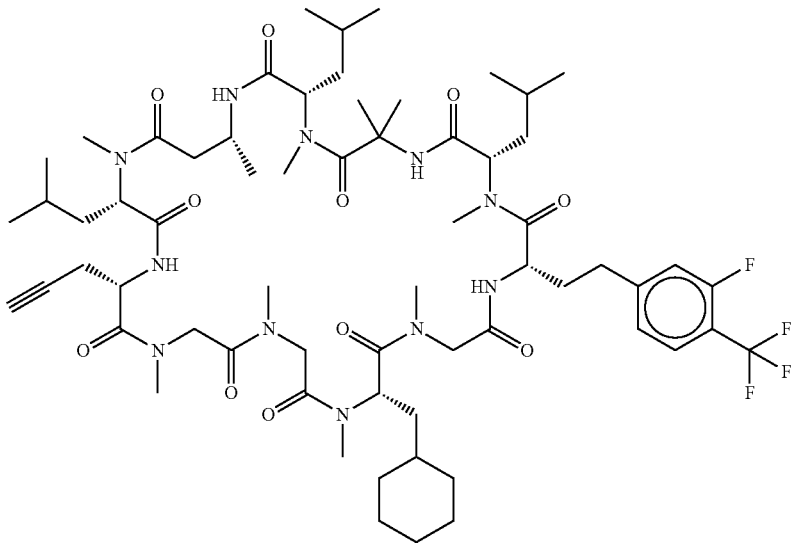 |
| 1475 | 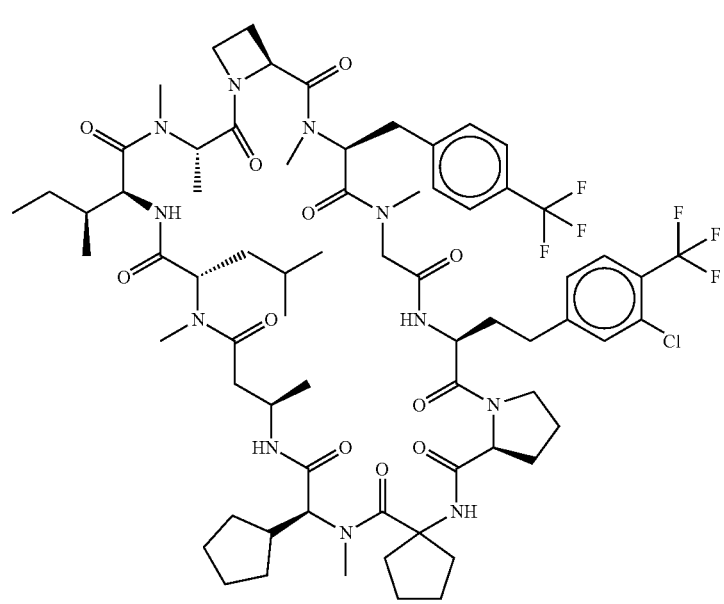 |
| 1476 | 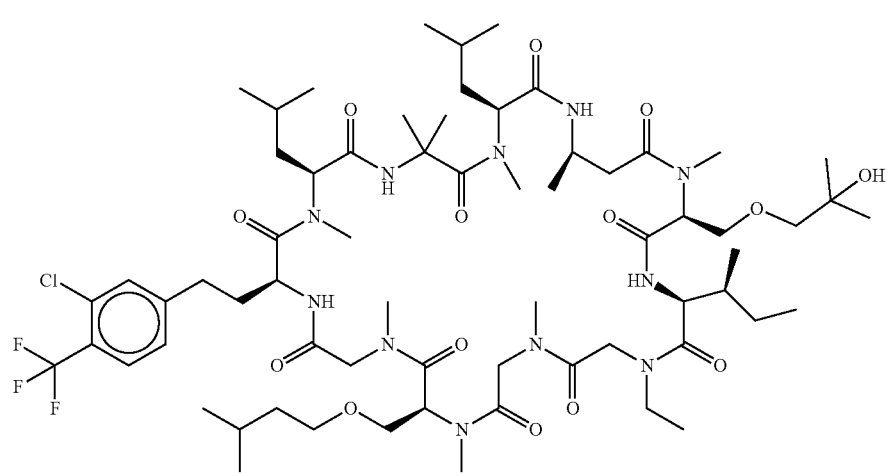 |

TABLE 24-continued
| Compound No. | Structural formula |
|---|---|
| 1477 | 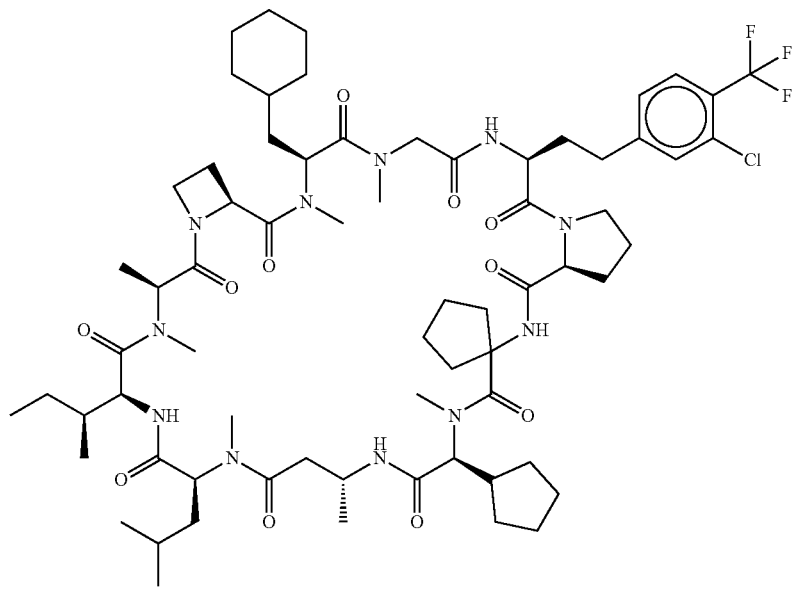 |
| 1478 | 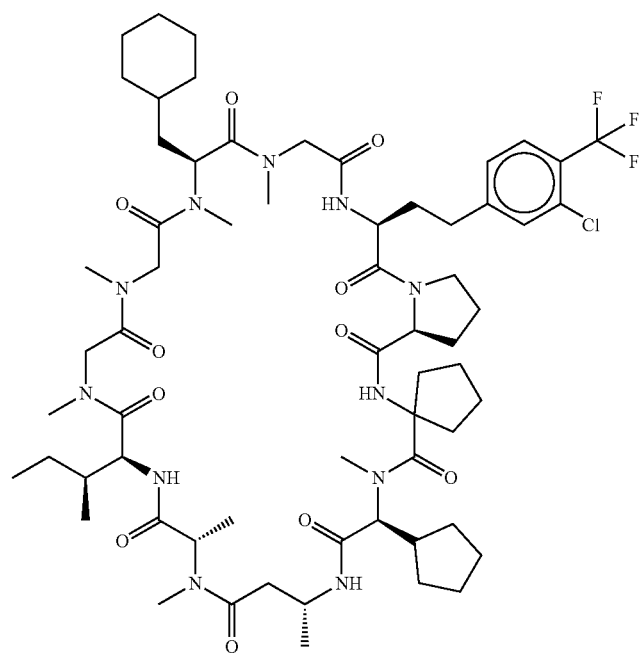 |

TABLE 24-continued
| Compound No. | Structural formula |
|---|---|
| 1479 | 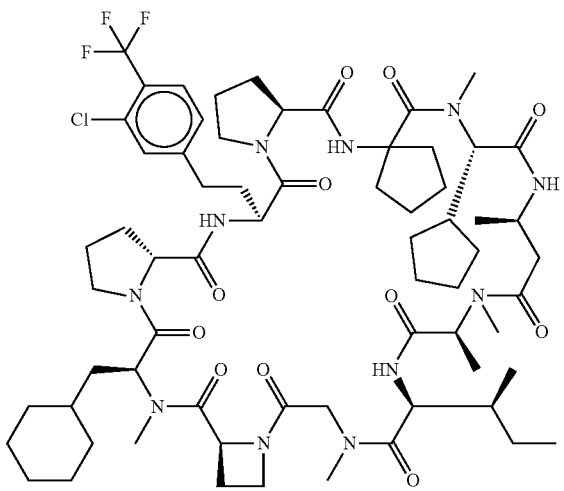 |
| 1480 | 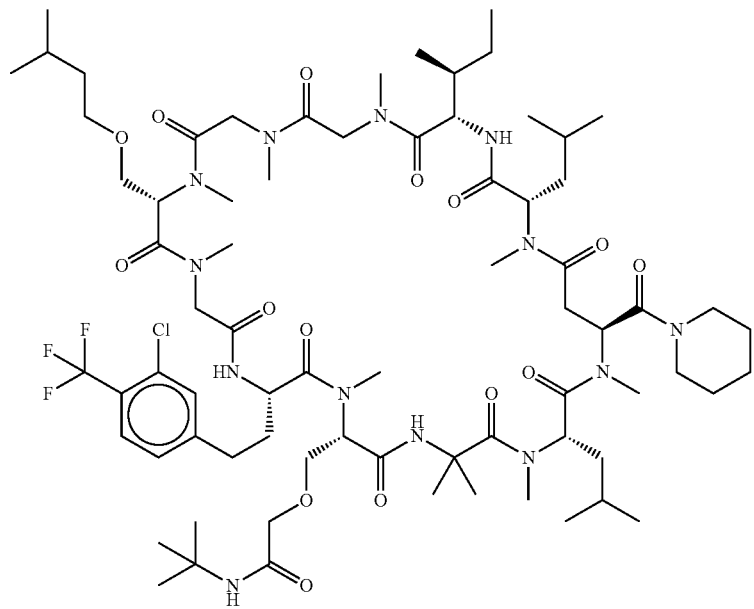 |

TABLE 24-continued
| Compound No. | Structural formula |
|---|---|
| 1481 | 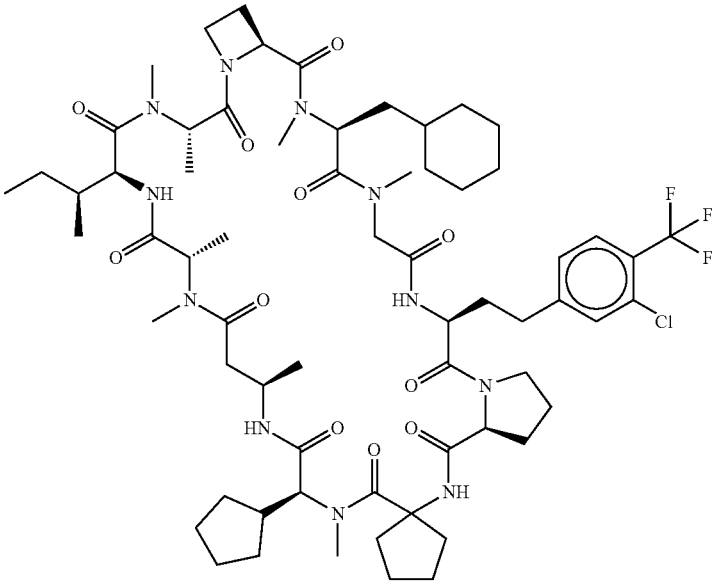 |
| 1482 | 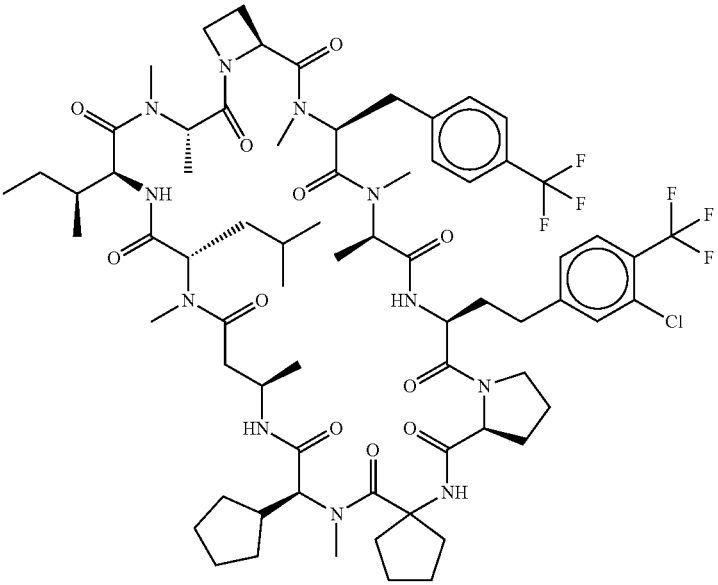 |

TABLE 24-continued
| Compound No. | Structural formula |
|---|---|
| 1483 | 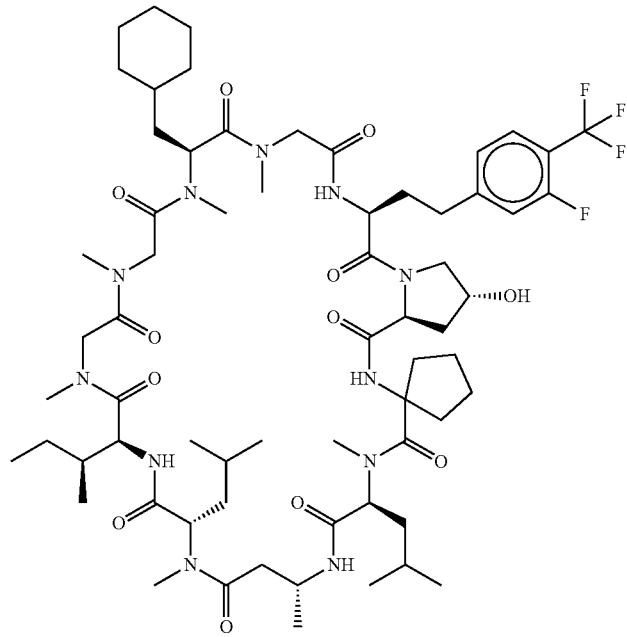 |
| 1484 | 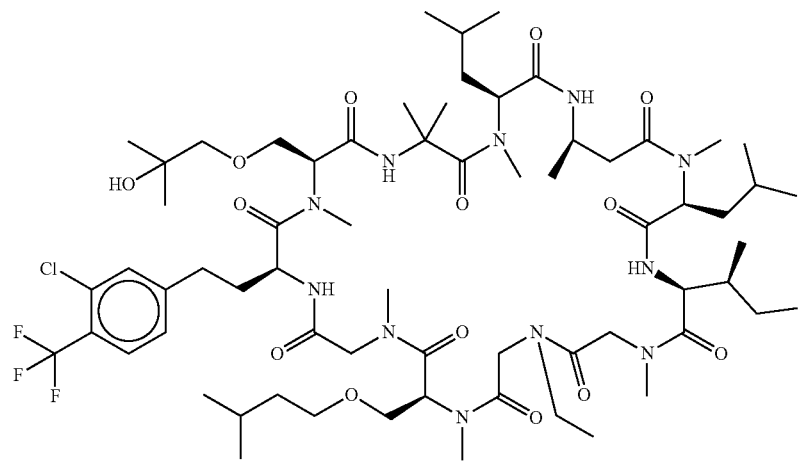 |

TABLE 24-continued
| Compound No. | Structural formula |
|---|---|
| 1485 | 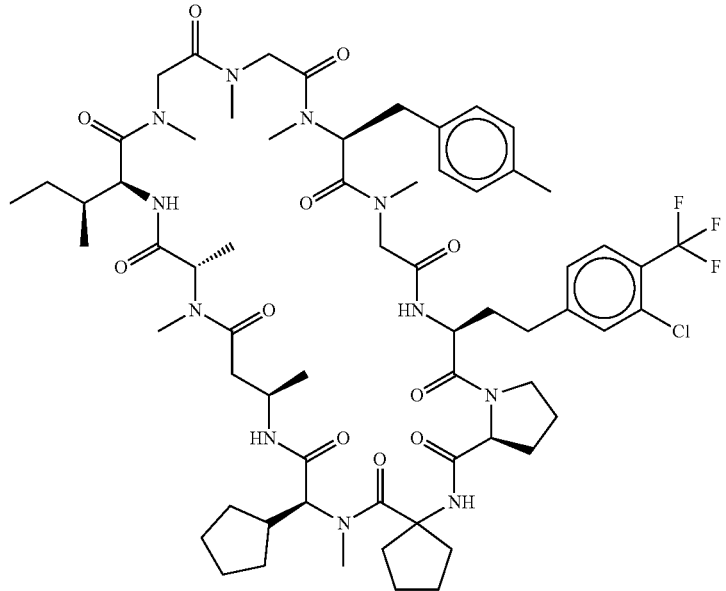 |
| 1486 | 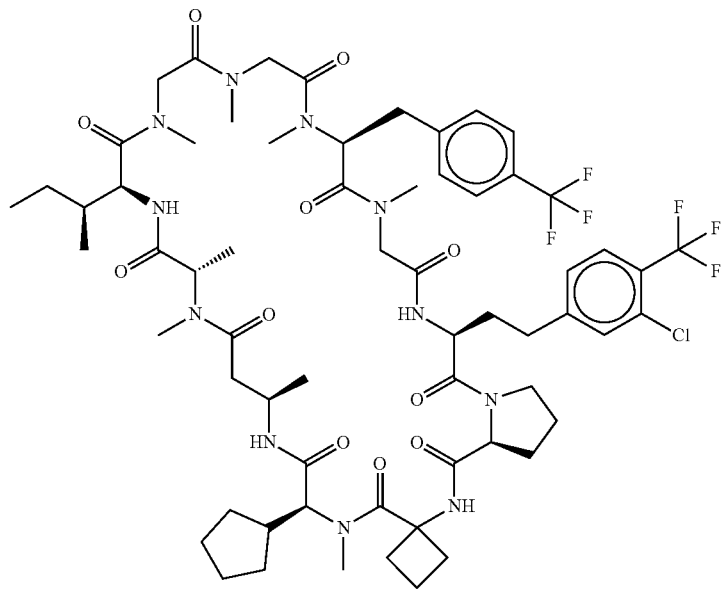 |

TABLE 24-continued
| Compound No. | Structural formula |
|---|---|
| 1487 | 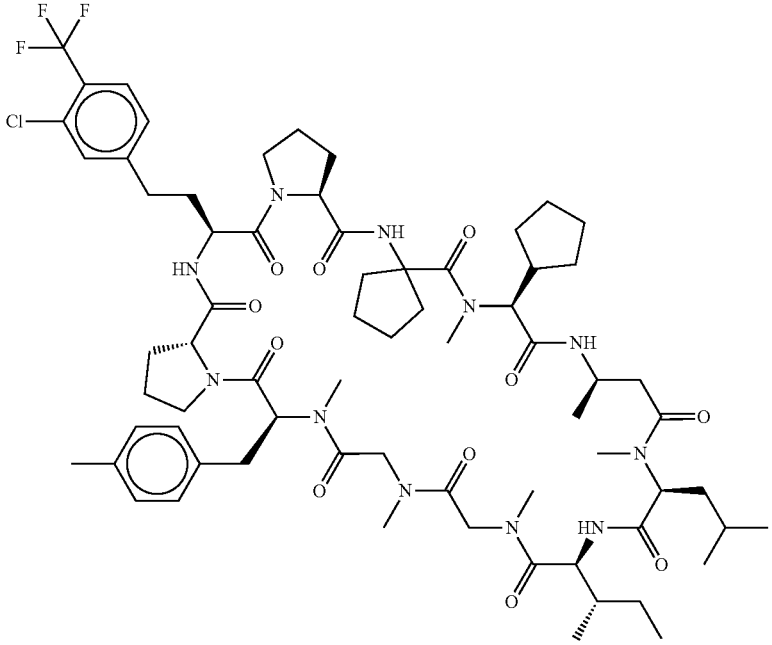 |
| 1488 | 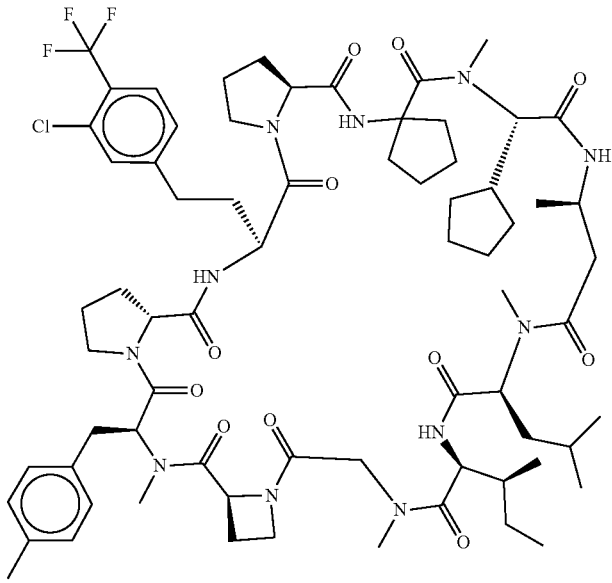 |

TABLE 24-continued
| Compound No. | Structural formula |
| --- | --- |
| 1489 | 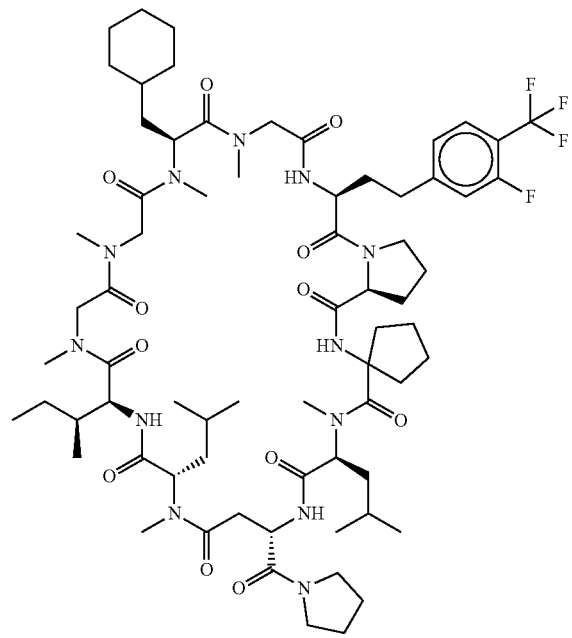 |
| 1490 | 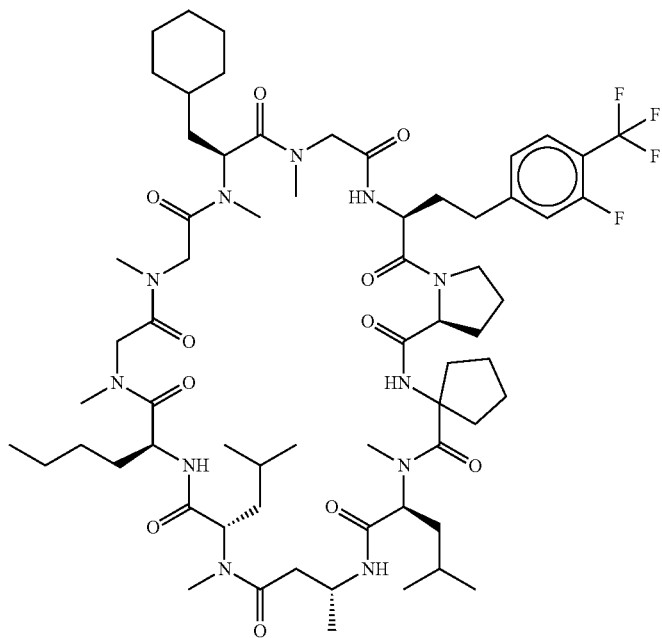 |

TABLE 24-continued
| Compound No. | Structural formula |
|---|---|
| 1491 | 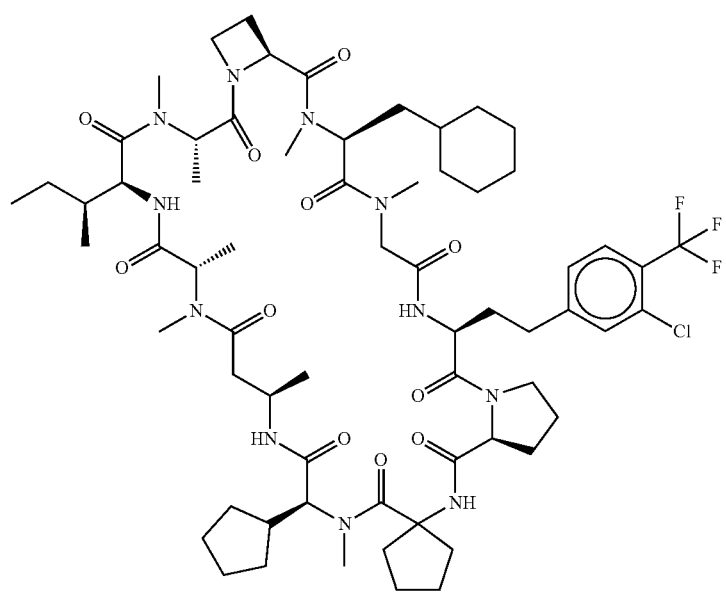 |
| 1492 | 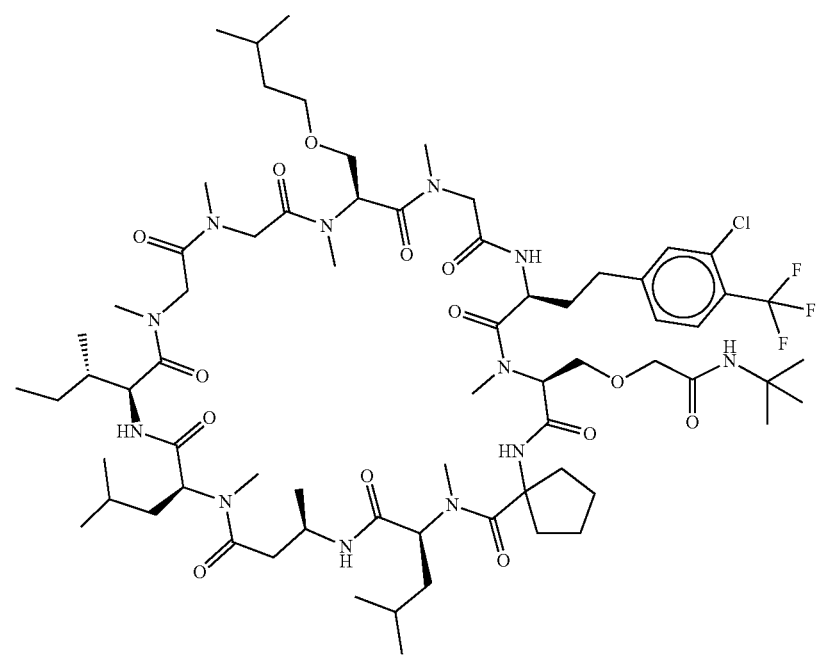 |

TABLE 24-continued
| Compound No. | Structural formula |
|---|---|
| 1493 | 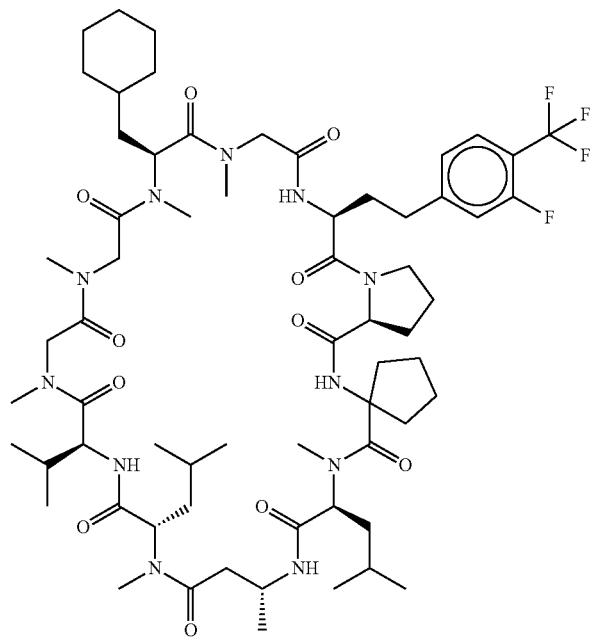 |
| 1494 | 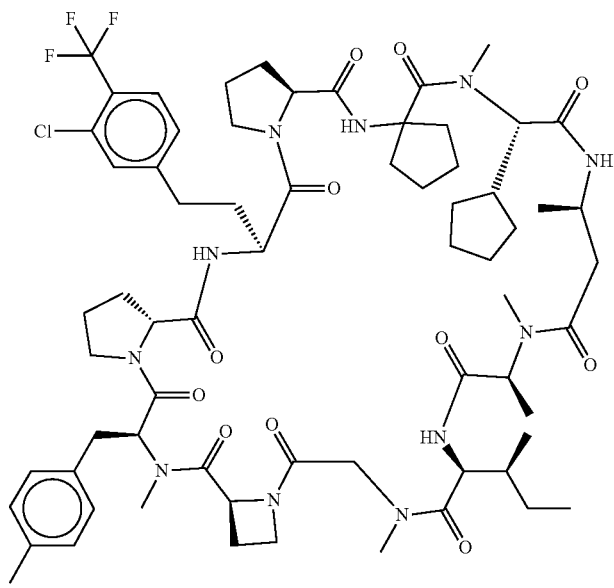 |

TABLE 24-continued
| Compound No. | Structural formula |
| --- | --- |
| 1495 | 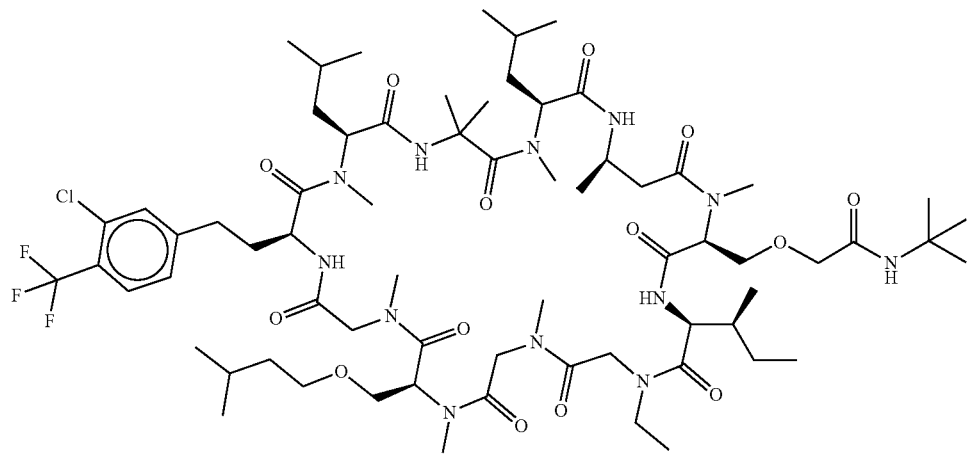 |
| 1496 | 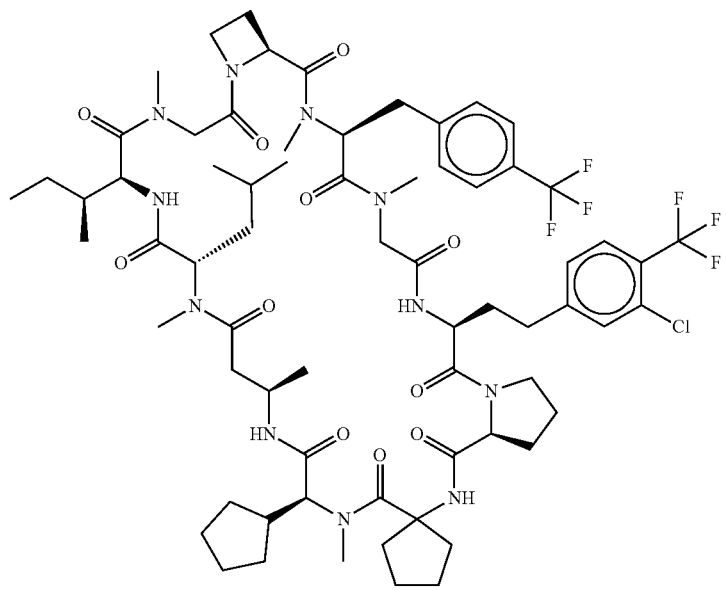 |

TABLE 24-continued
| Compound No. | Structural formula |
| --- | --- |
| 1497 | 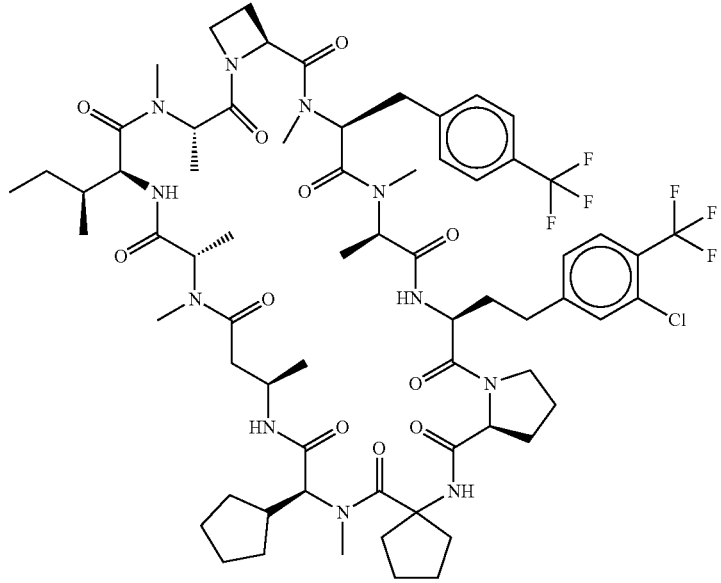 |
| 1498 | 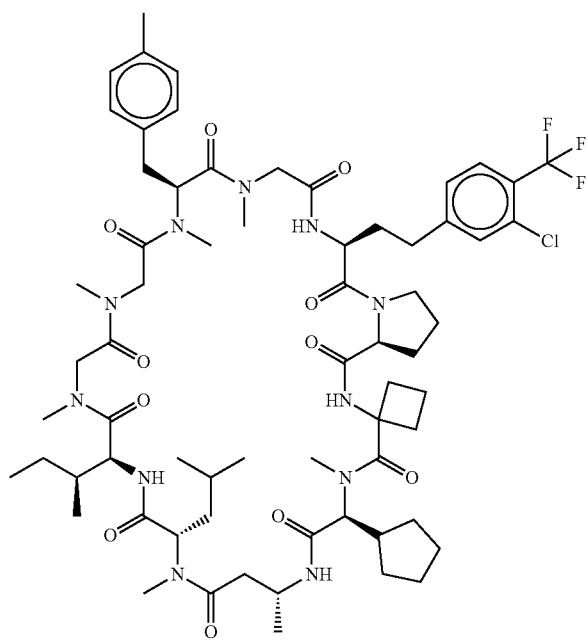 |

TABLE 24-continued
| Compound No. | Structural formula |
|---|---|
| 1499 | 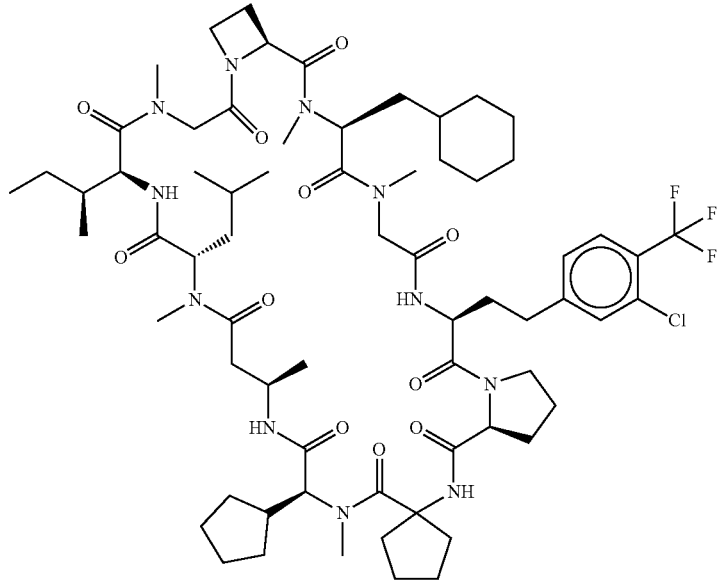 |
| 1500 | 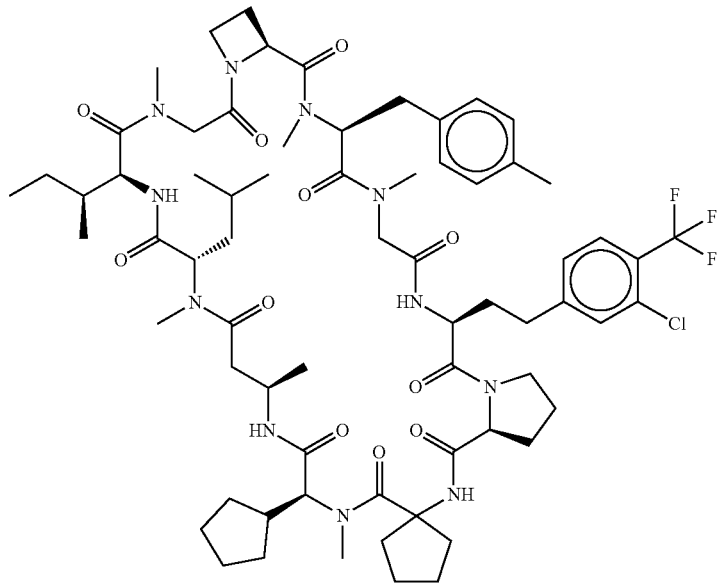 |

TABLE 24-continued
| Compound No. | Structural formula |
|---|---|
| 1501 | 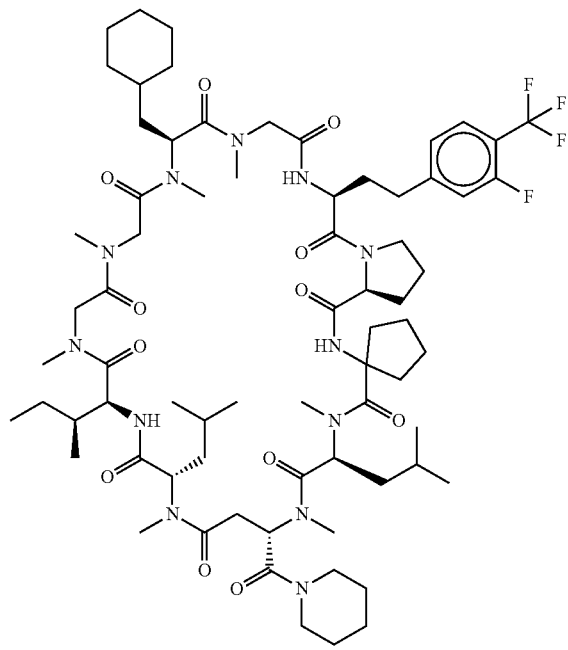 |
| 1502 | 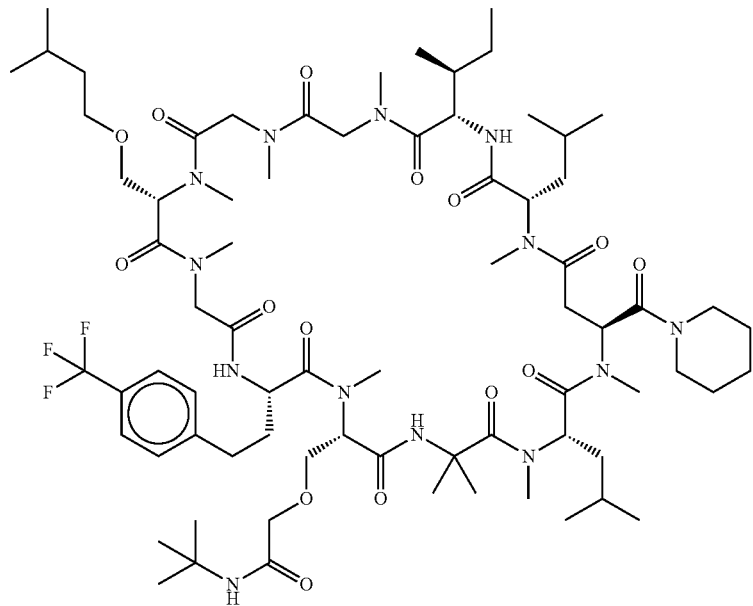 |

TABLE 24-continued
| Compound No. | Structural formula |
|---|---|
| 1503 | 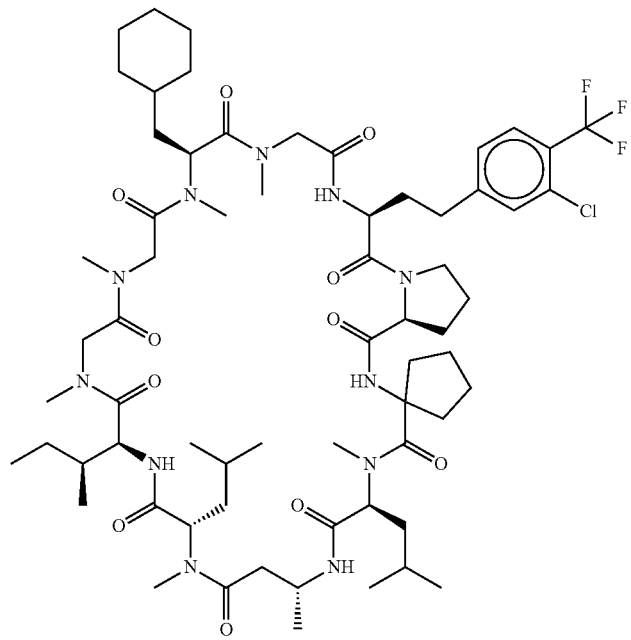 |
| 1504 | 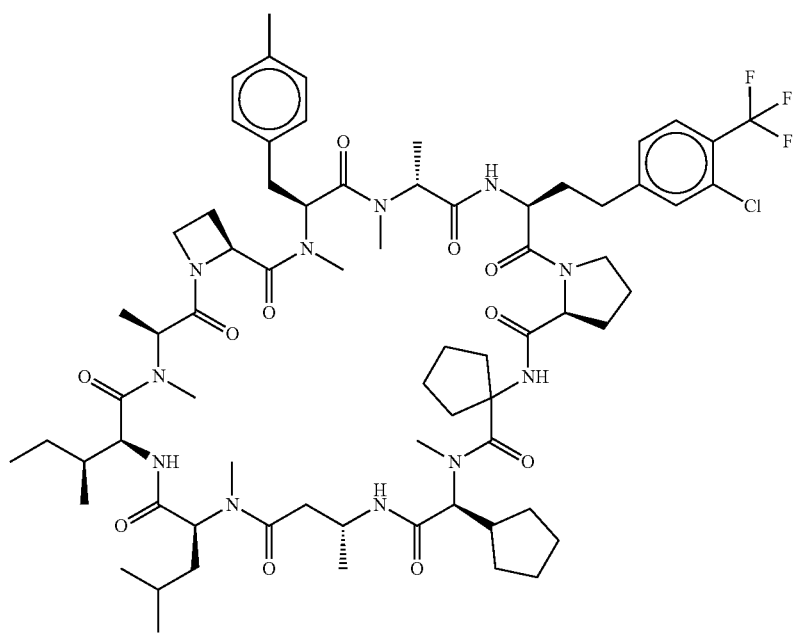 |

TABLE 24-continued
| Compound No. | Structural formula |
| --- | --- |
| 1505 | 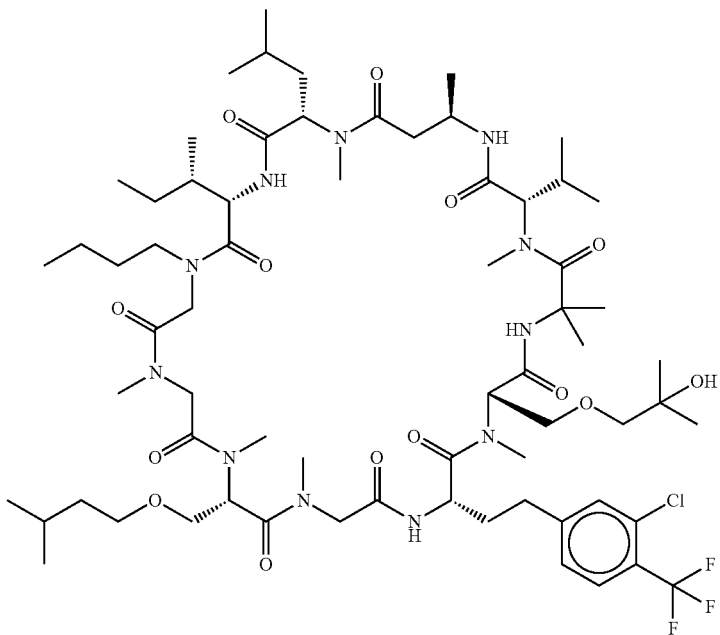 |
| 1506 | 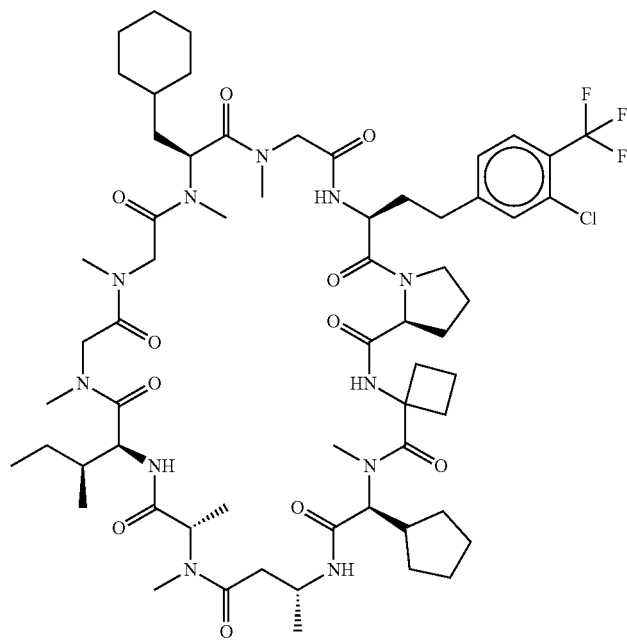 |

TABLE 24-continued
| Compound No. | Structural formula |
|---|---|
| 1507 | 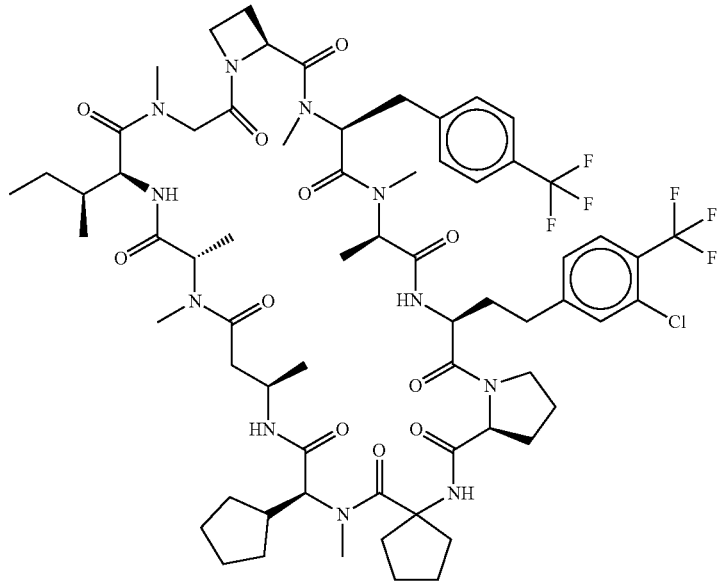 |
| 1508 | 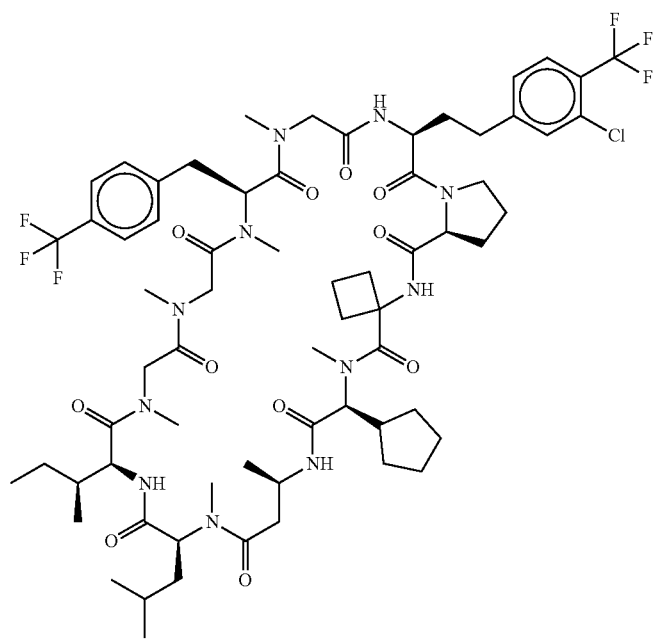 |

TABLE 24-continued
| Compound No. | Structural formula |
|---|---|
| 1509 | 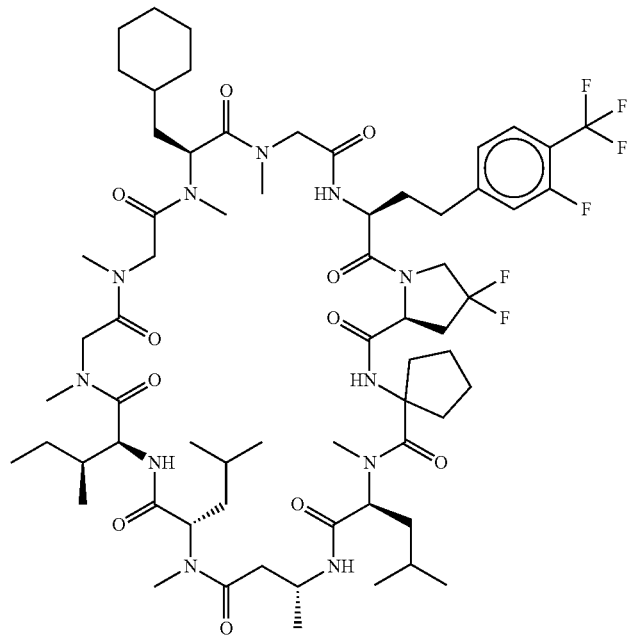 |
| 1510 | 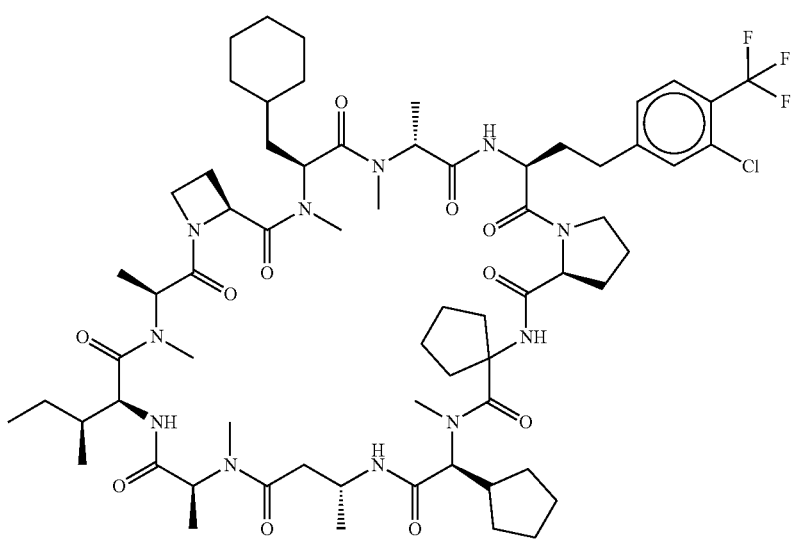 |

TABLE 24-continued
| Compound No. | Structural formula |
|---|---|
| 1511 | 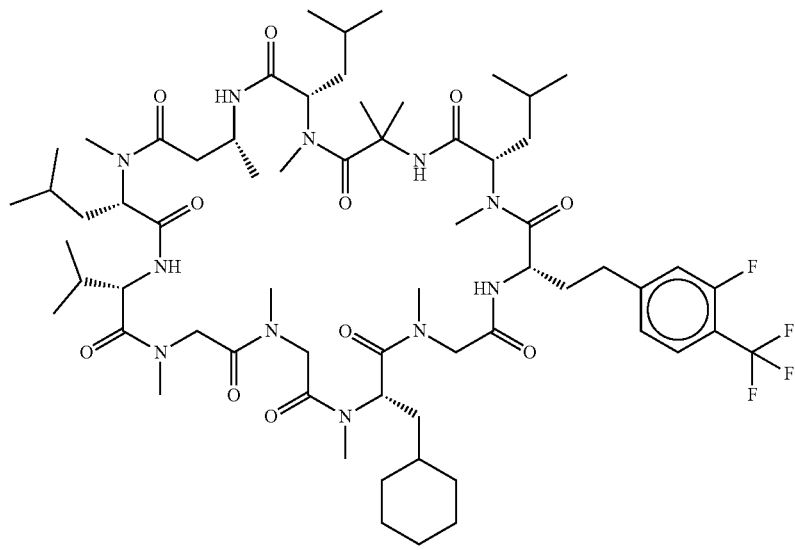 |
| 1512 | 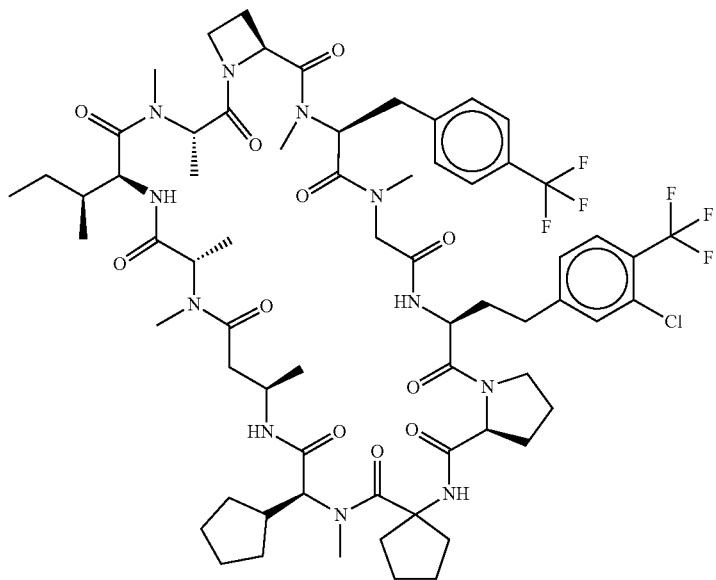 |

TABLE 24-continued
| Compound No. | Structural formula |
|---|---|
| 1513 | 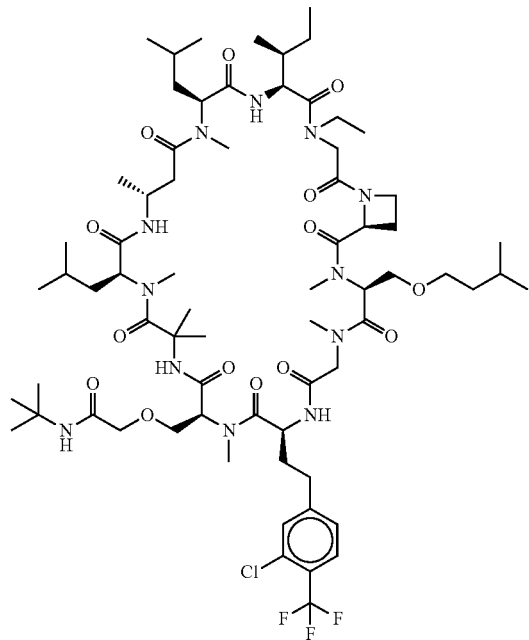 |
| 1514 | 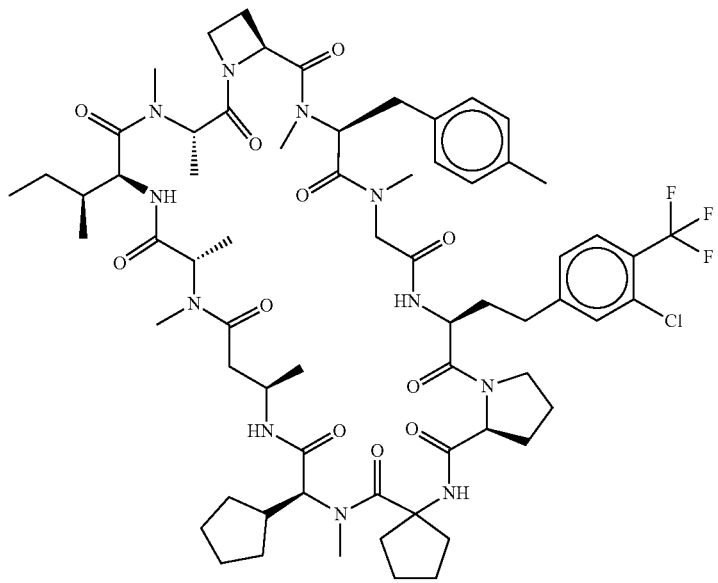 |

TABLE 24-continued
| Compound No. | Structural formula |
|---|---|
| 1515 | 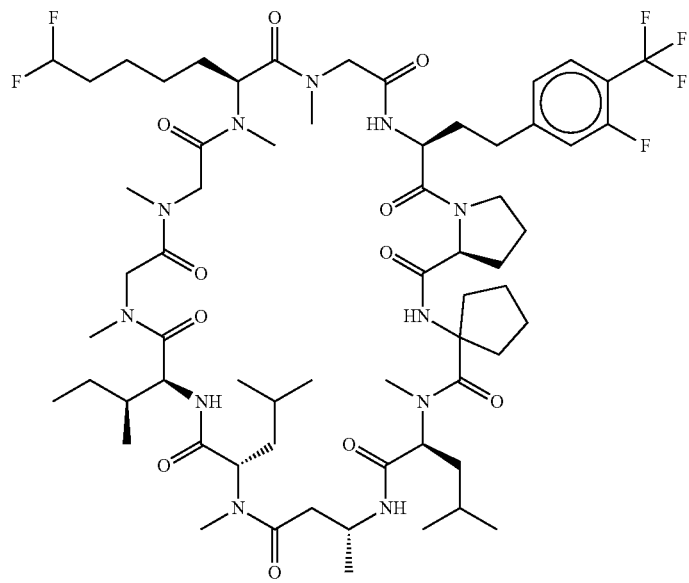 |
| 1516 | 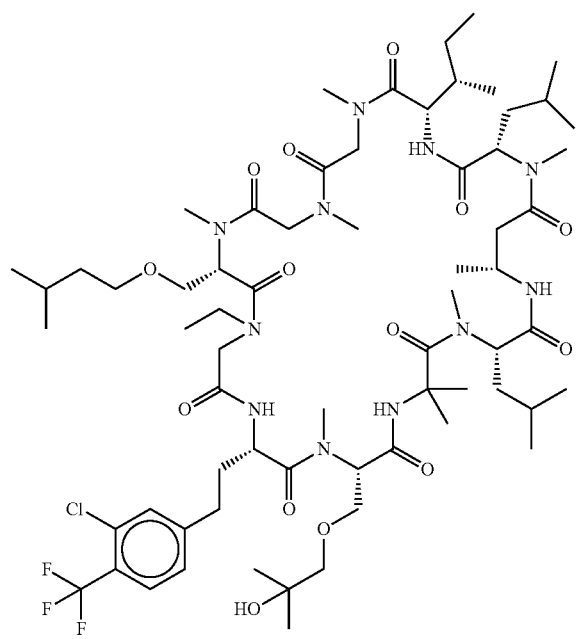 |

TABLE 24-continued
| Compound No. | Structural formula |
|---|---|
| 1517 | 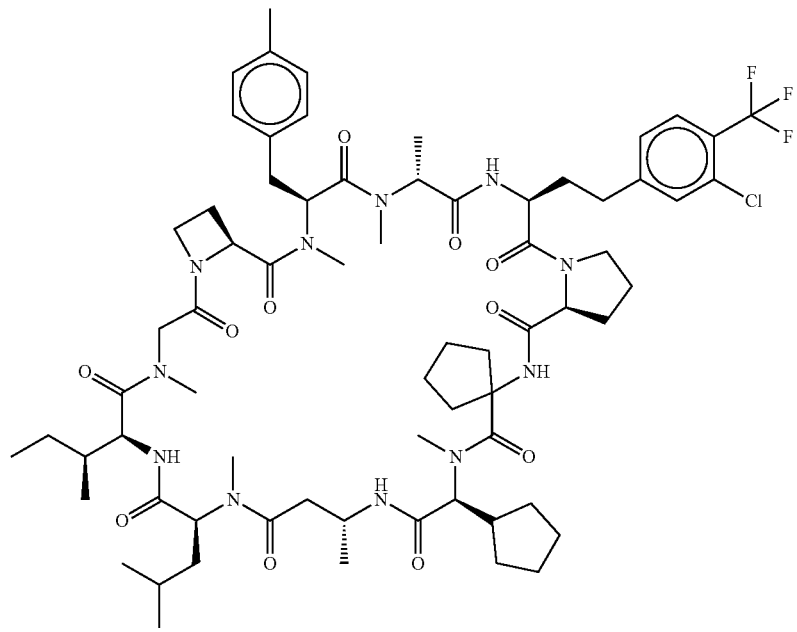 |
| 1518 | 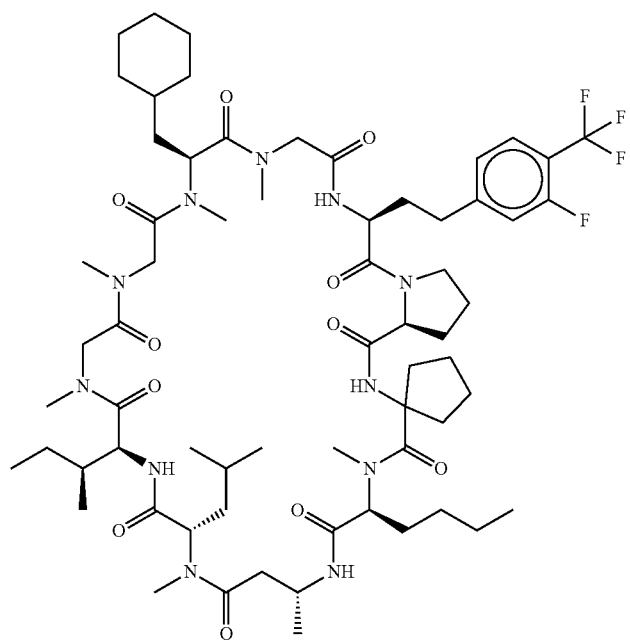 |

TABLE 24-continued
| Compound No. | Structural formula |
|---|---|
| 1519 | 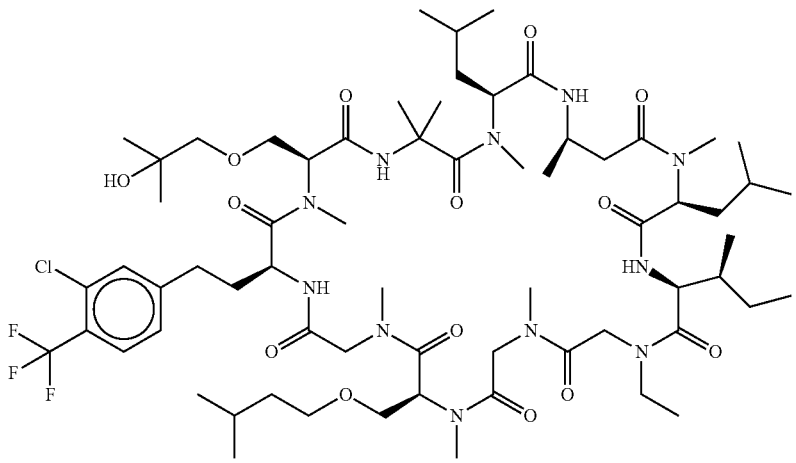 |
| 1520 | 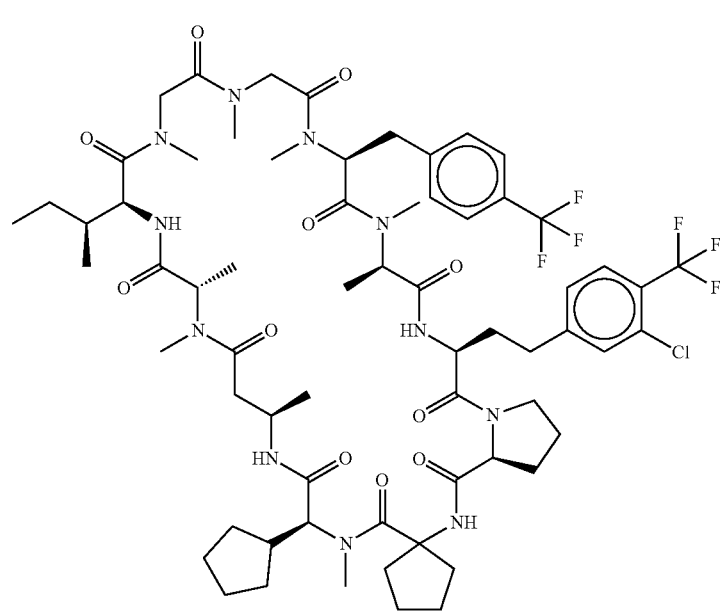 |

TABLE 24-continued
| Compound No. | Structural formula |
|---|---|
| 1521 | 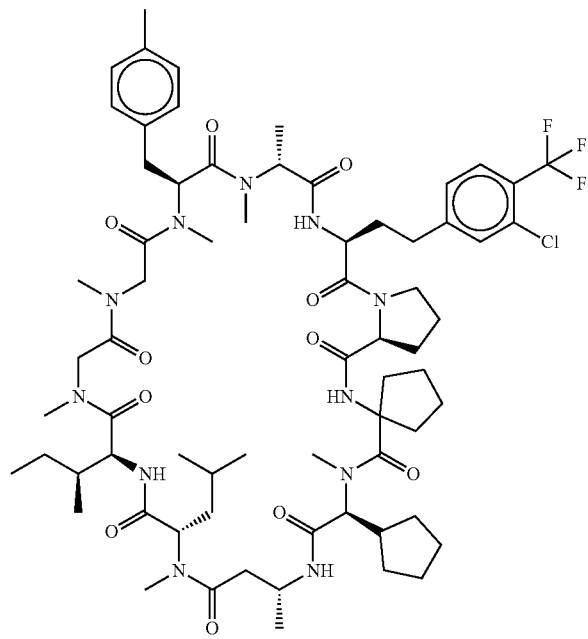 |
| 1522 | 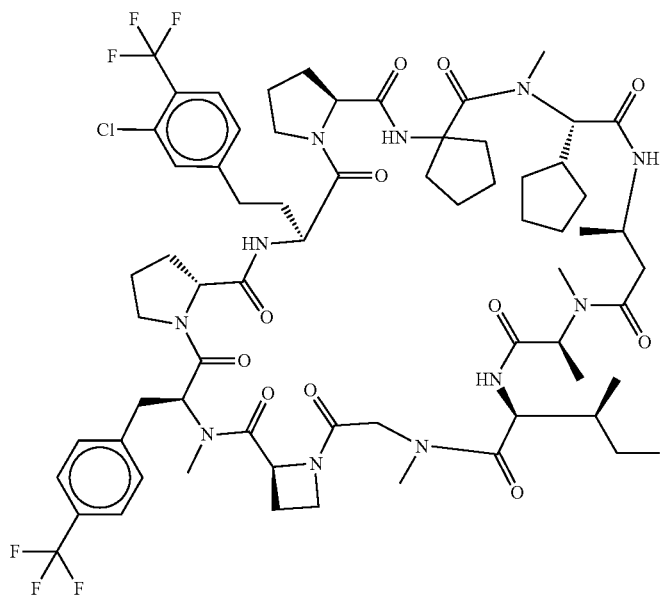 |

TABLE 24-continued
| Compound No. | Structural formula |
|---|---|
| 1523 | 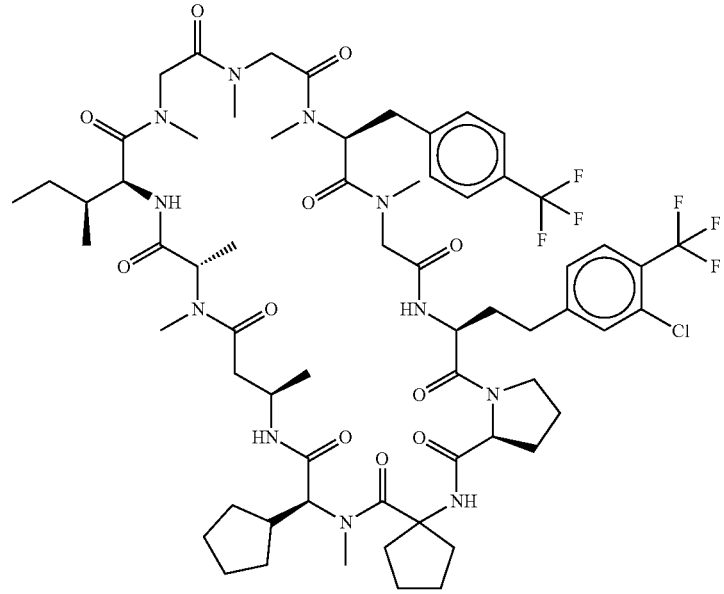 |
| 1524 | 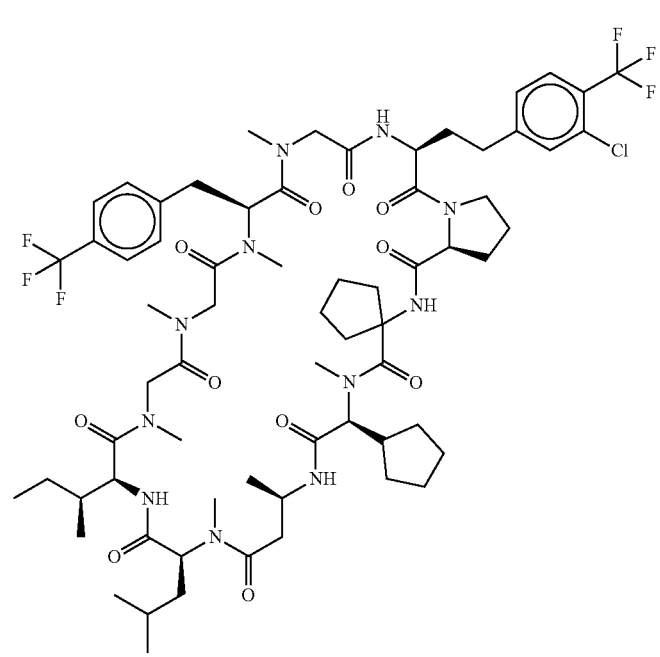 |

TABLE 24-continued
| Compound No. | Structural formula |
|---|---|
| 1525 | 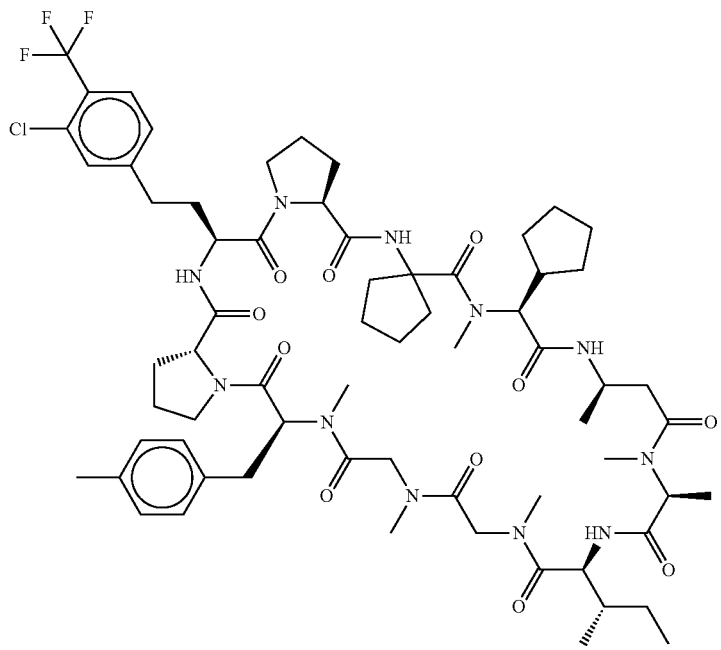 |
| 1526 | 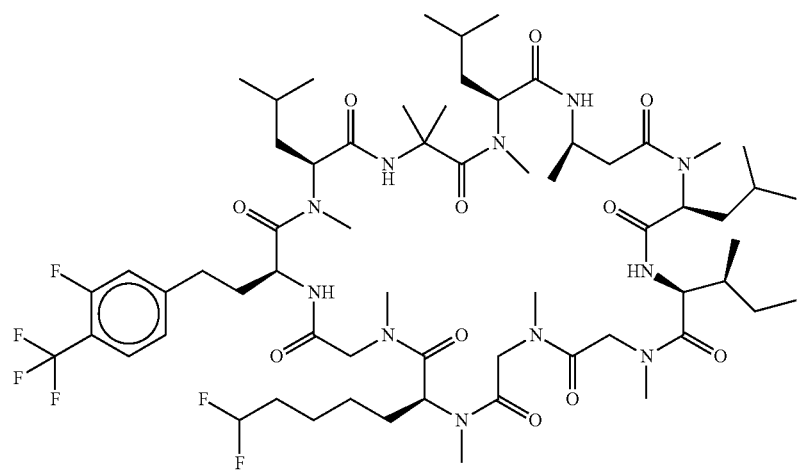 |

TABLE 24-continued
| Compound No. | Structural formula |
|---|---|
| 1527 | 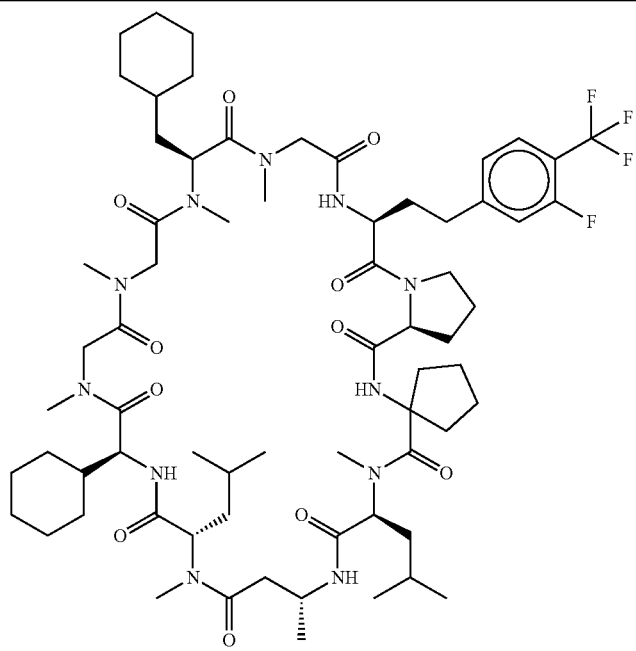 |
| 1528 | 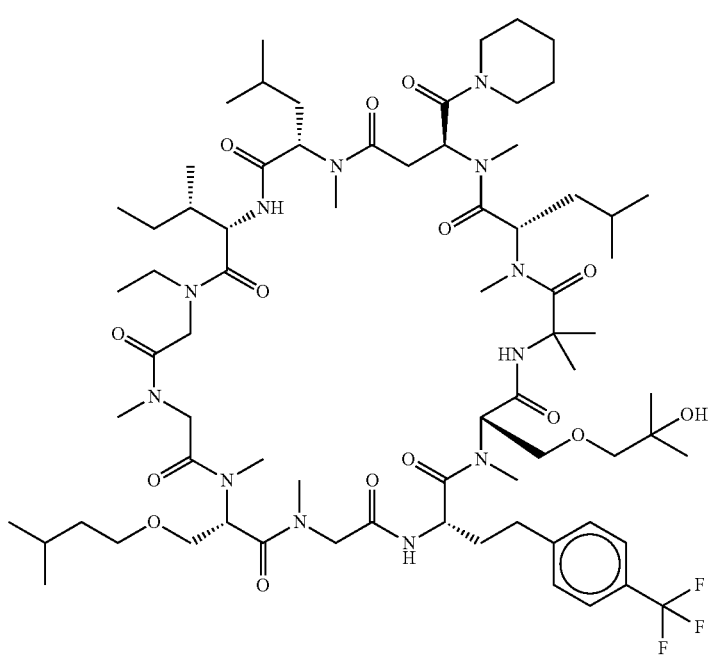 |

TABLE 24-continued
| Compound No. | Structural formula |
|---|---|
| 1529 | 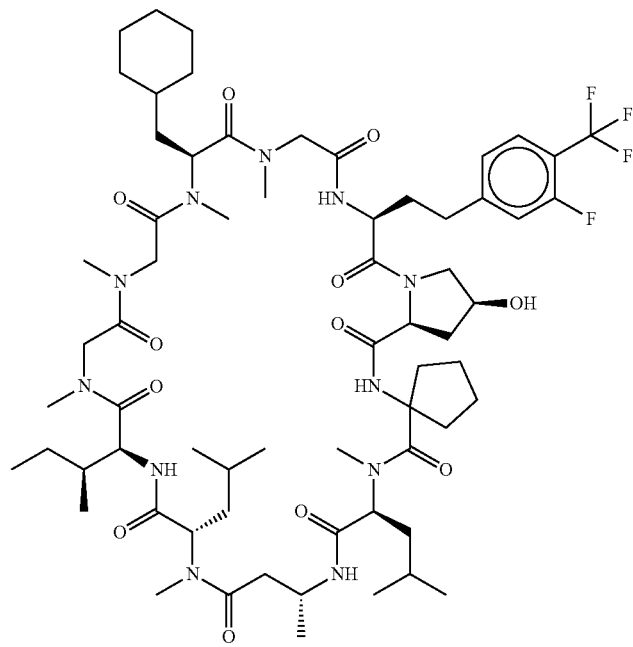 |
| 1530 | 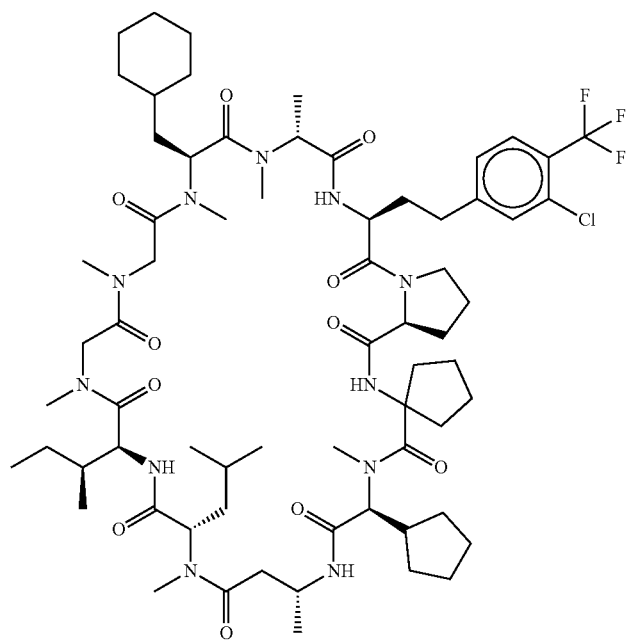 |

TABLE 24-continued
| Compound No. | Structural formula |
|---|---|
| 1531 | 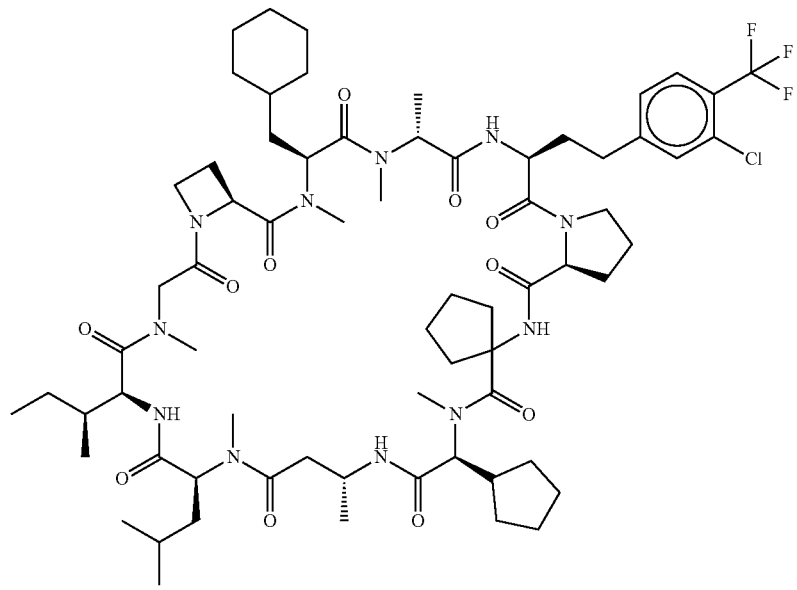 |
| 1532 | 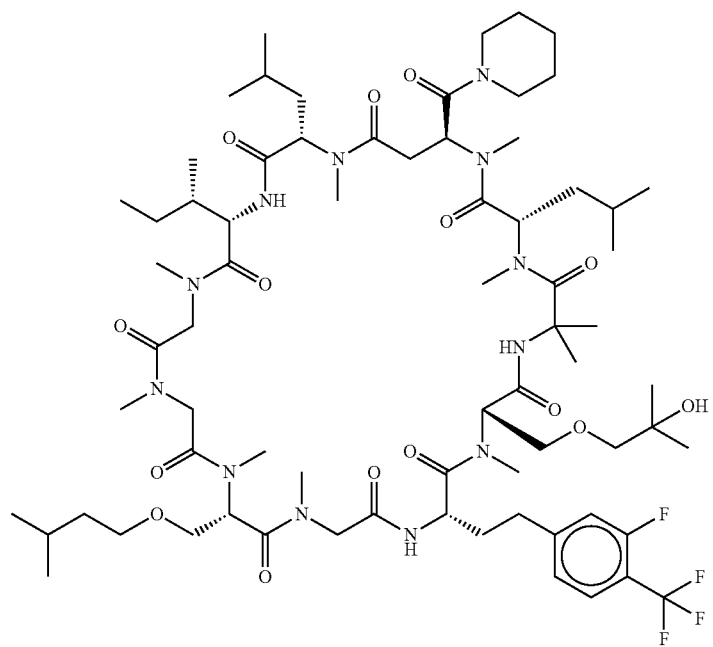 |

TABLE 24-continued
| Compound No. | Structural formula |
|---|---|
| 1533 | 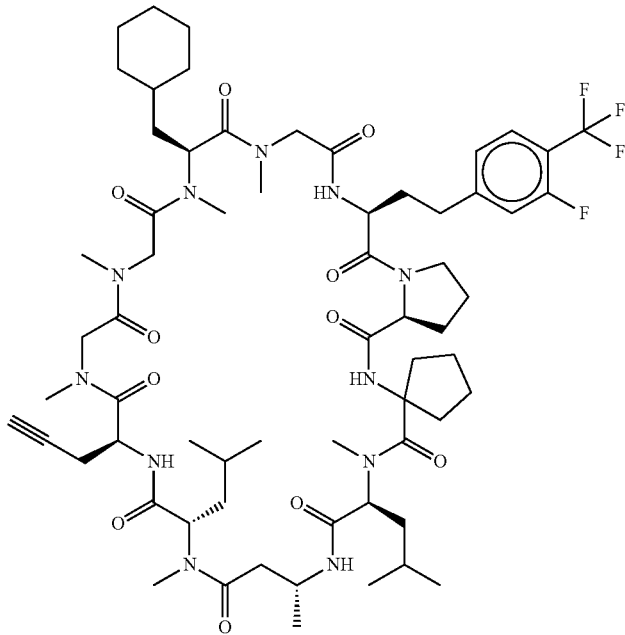 |
| 1534 | 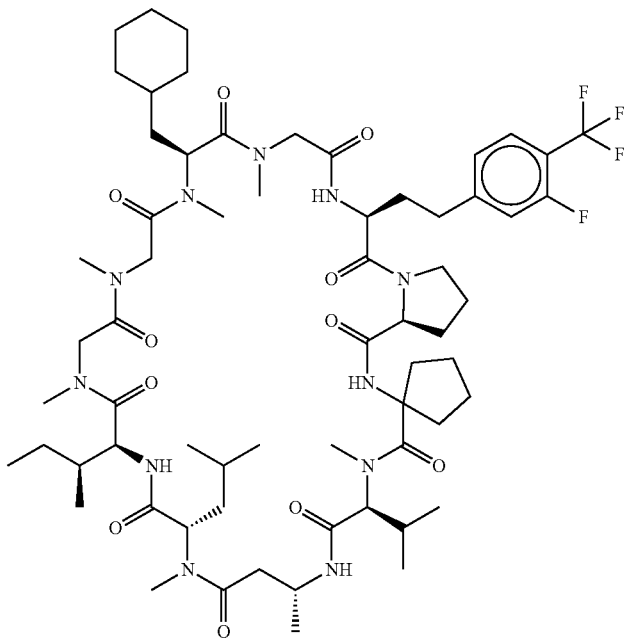 |

TABLE 24-continued
| Compound No. | Structural formula |
|---|---|
| 1535 | 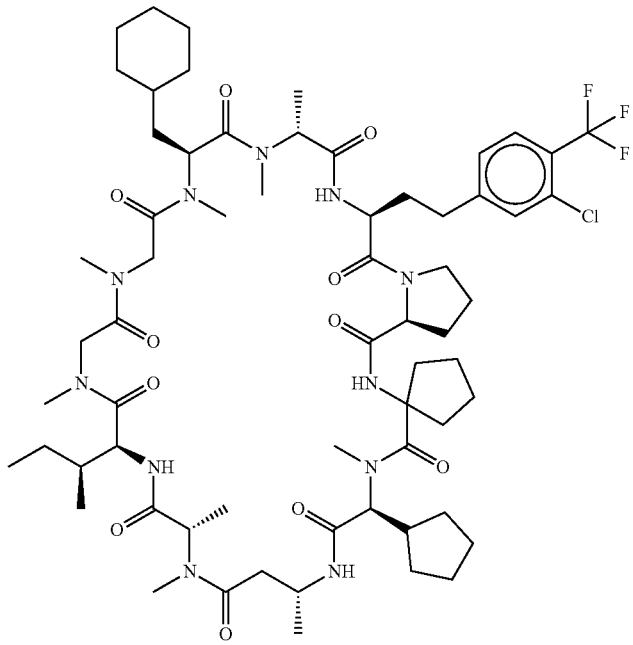 |
| 1536 | 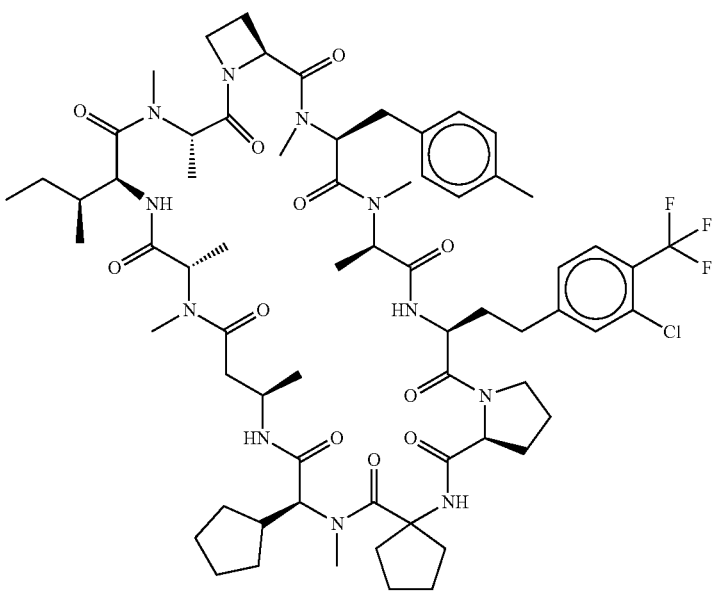 |

| Compound No. | Structural formula |
|---|---|
| 1537 | 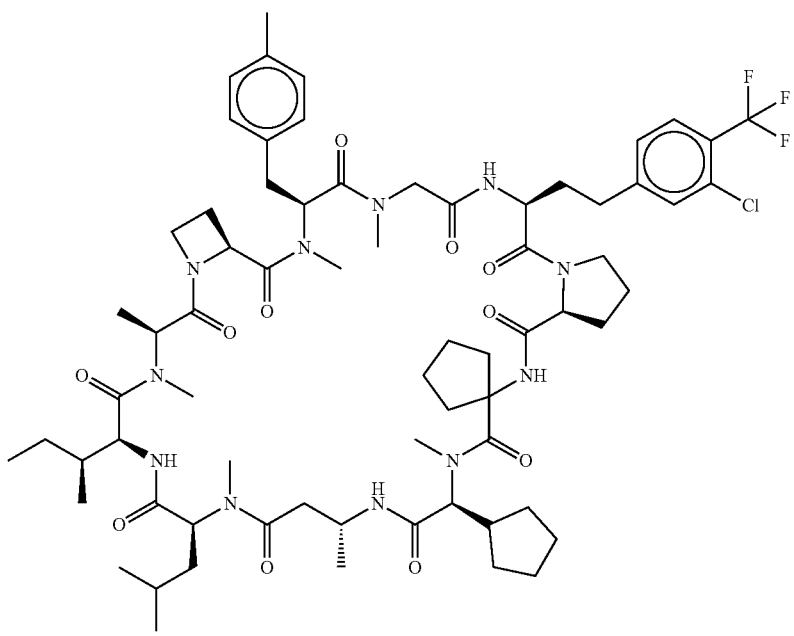 |
| 1538 | 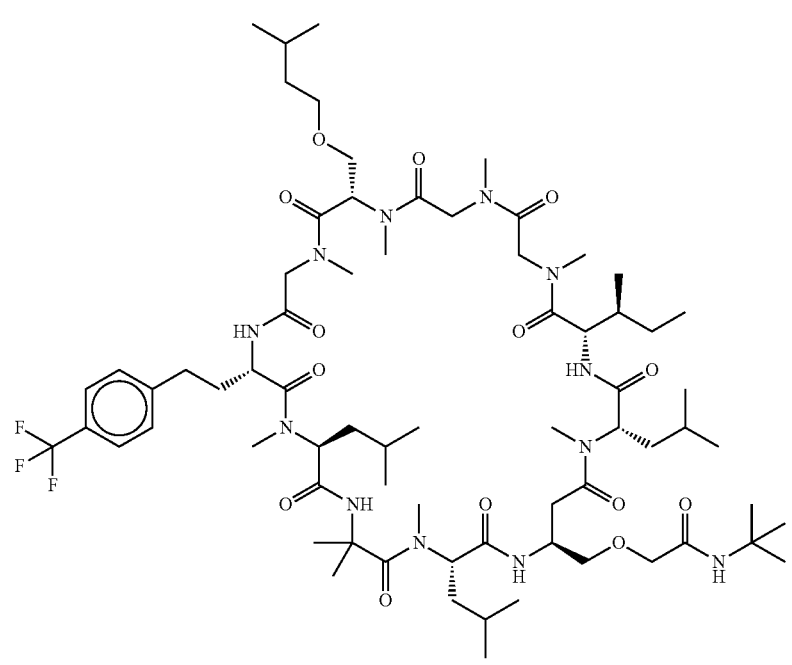 |

TABLE 24-continued
| Compound No. | Structural formula |
|---|---|
| 1539 | 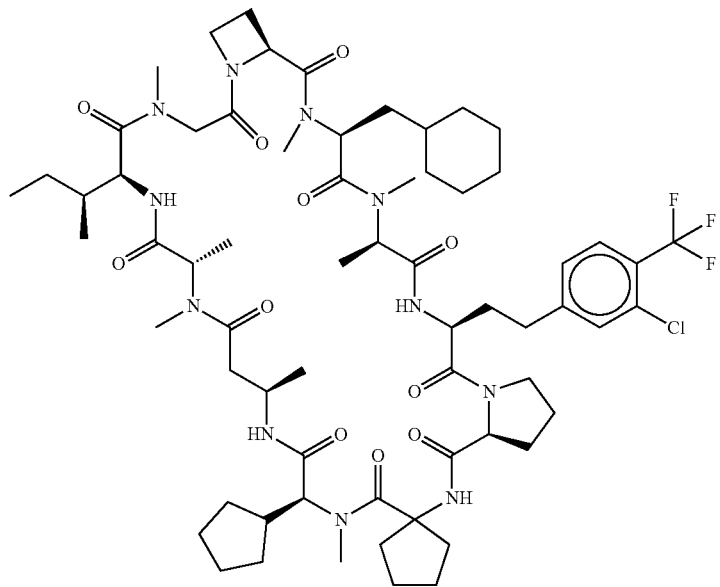 |
| 1540 | 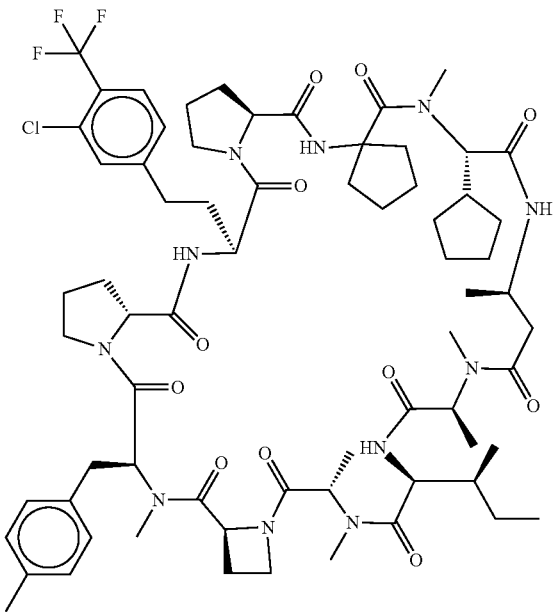 |

TABLE 24-continued
| Compound No. | Structural formula |
| --- | --- |
| 1541 | 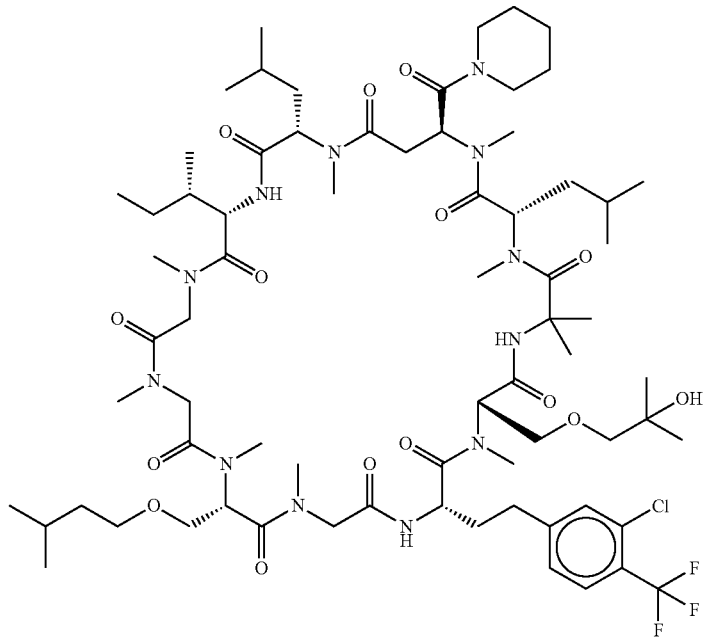 |
| 1542 | 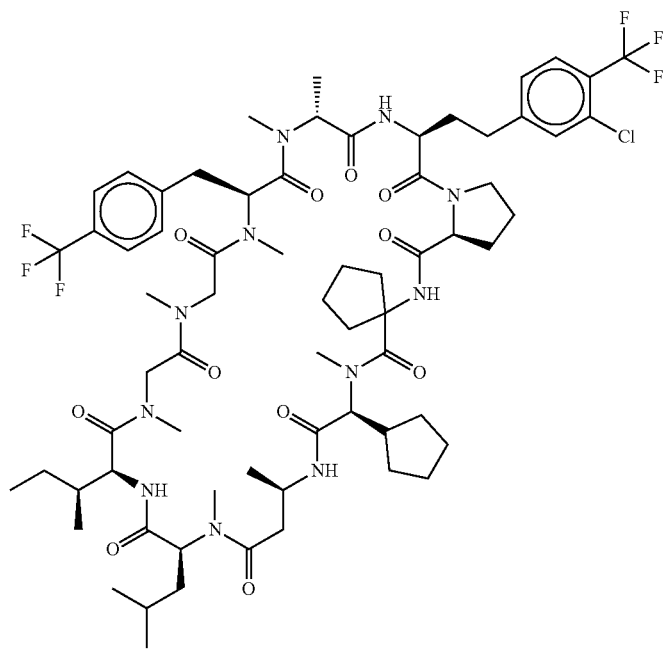 |

TABLE 24-continued
| Compound No. | Structural formula |
|---|---|
| 1543 | 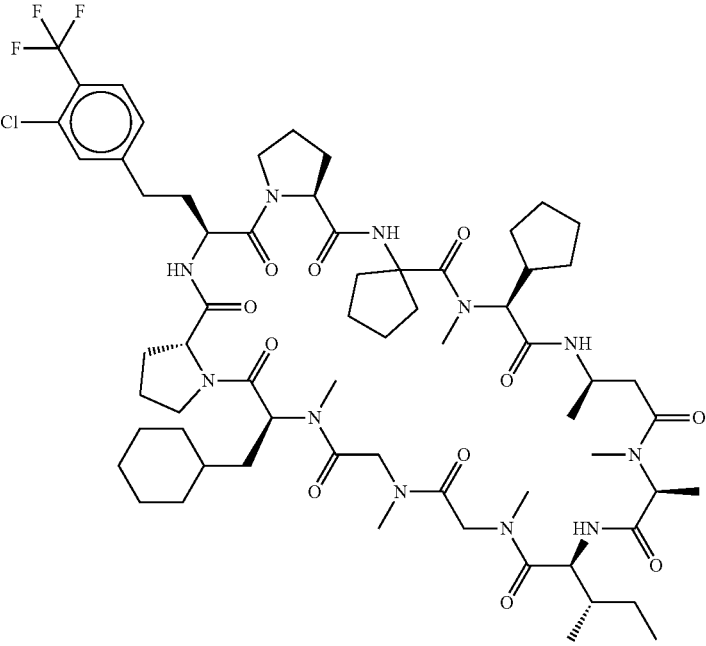 |
| 1544 | 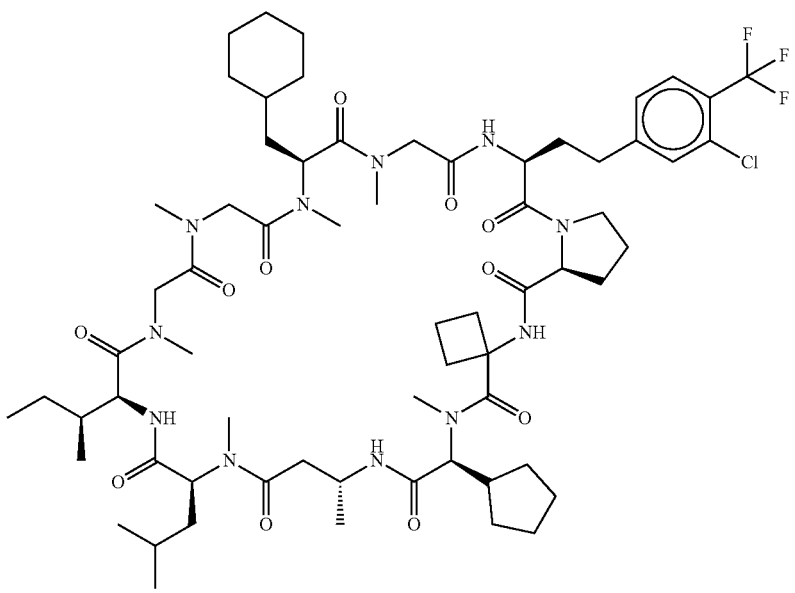 |

TABLE 24-continued
| Compound No. | Structural formula |
|---|---|
| 1545 | 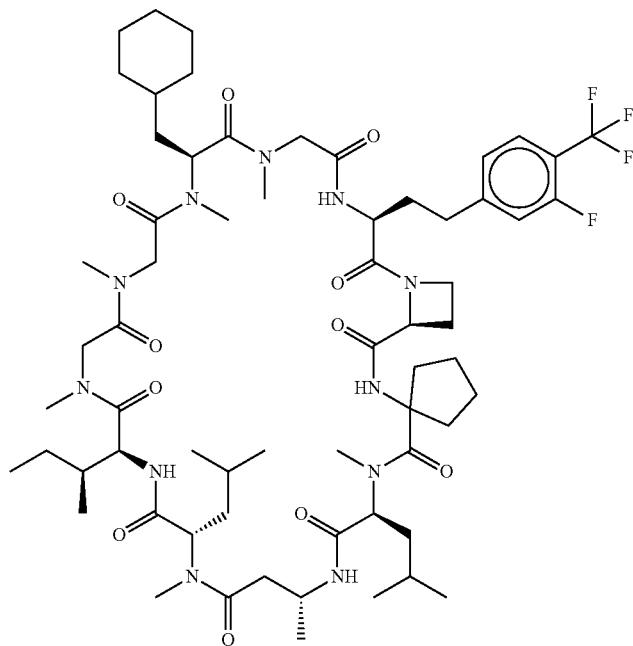 |
| 1546 | 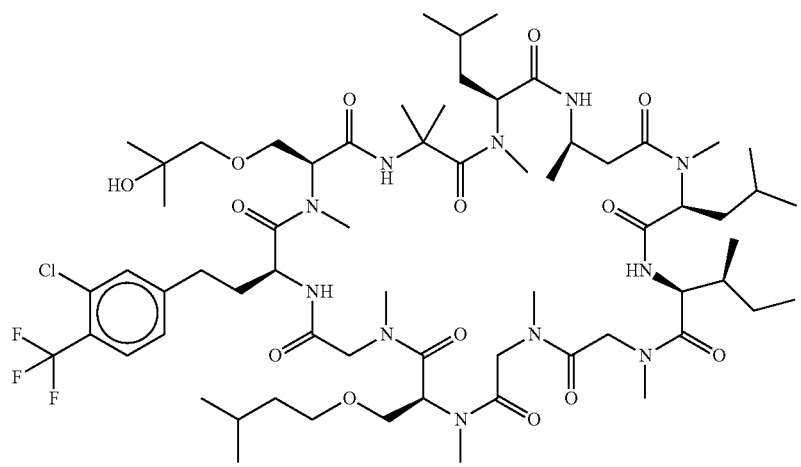 |

TABLE 24-continued
| Compound No. | Structural formula |
|---|---|
| 1547 | 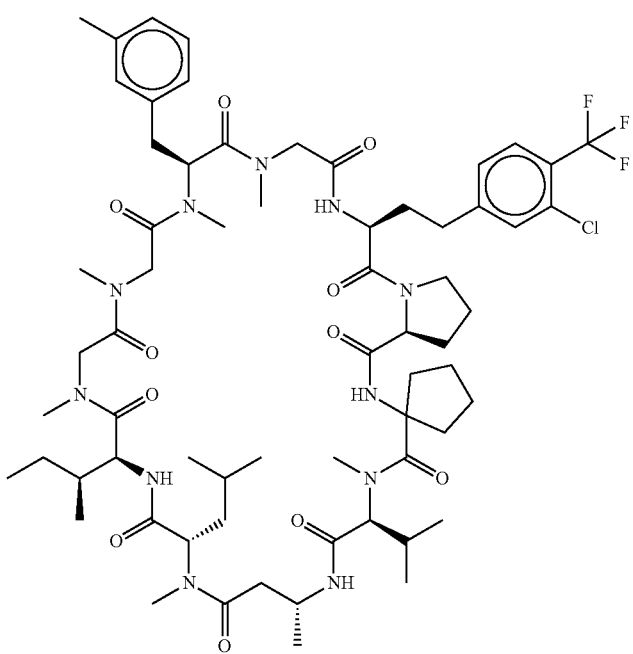 |
| 1548 | 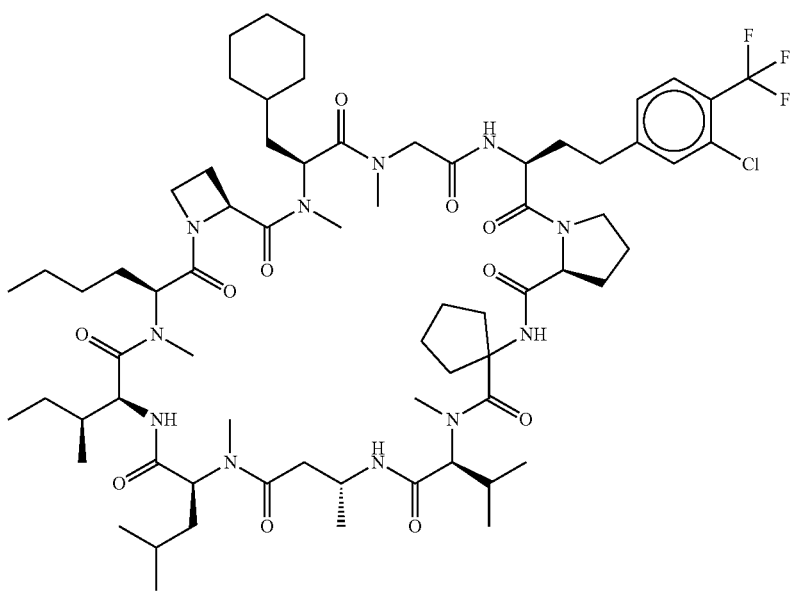 |

TABLE 24-continued
| Compound No. | Structural formula |
|---|---|
| 1549 | 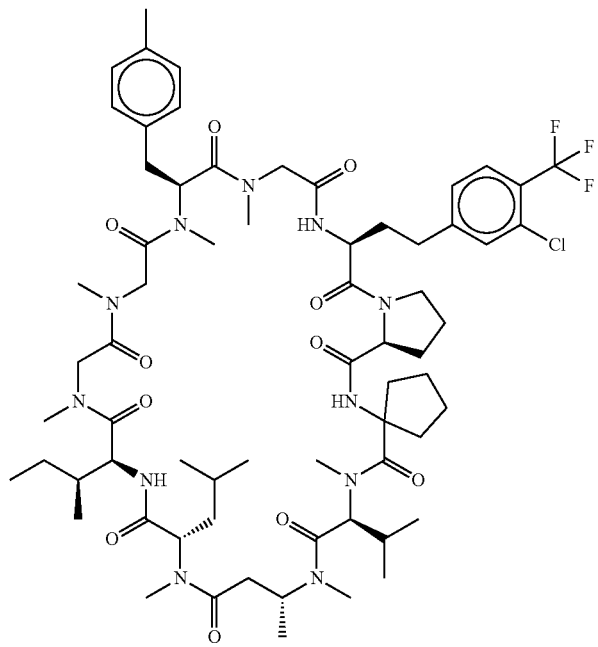 |
| 1550 | 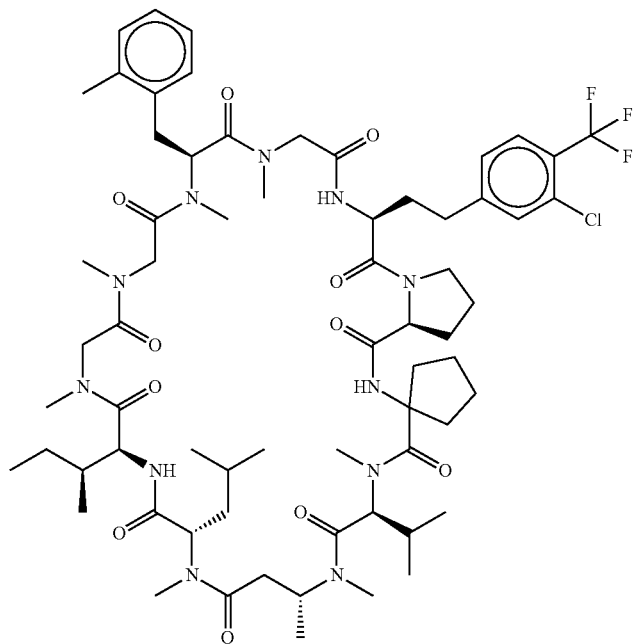 |

TABLE 24-continued
| Compound No. | Structural formula |
| --- | --- |
| 1551 | 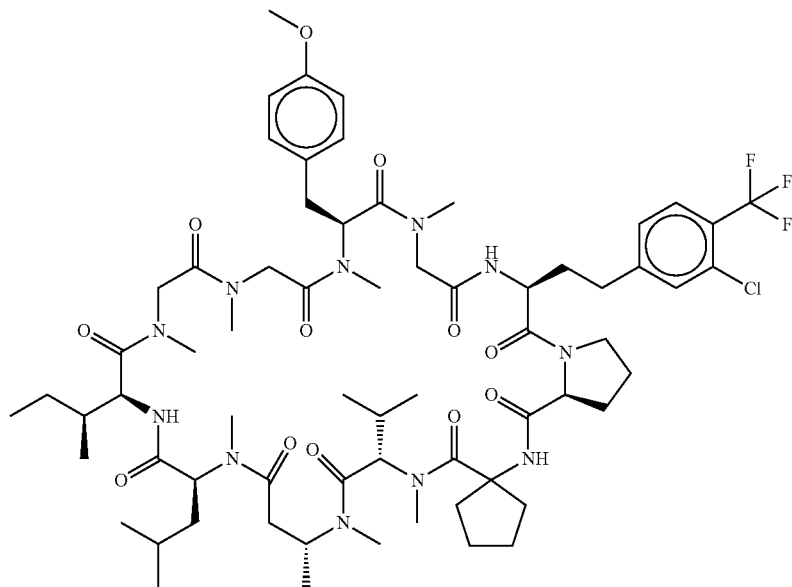 |
| 1552 | 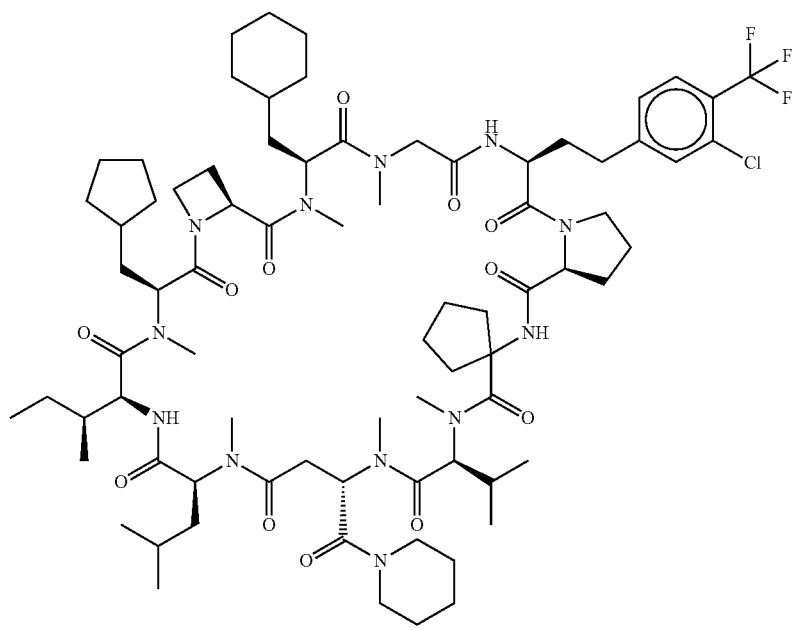 |

TABLE 24-continued
| Compound No. | Structural formula |
|---|---|
| 1553 | 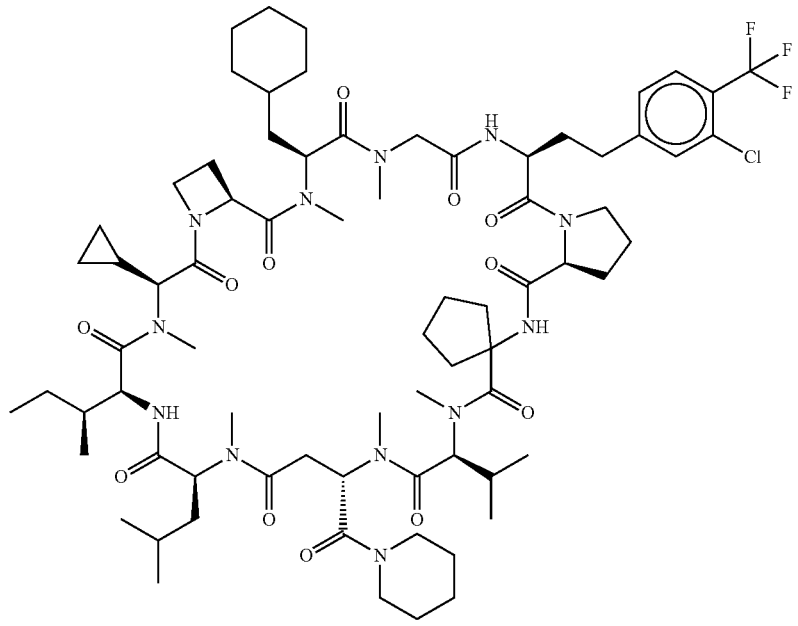 |
| 1554 | 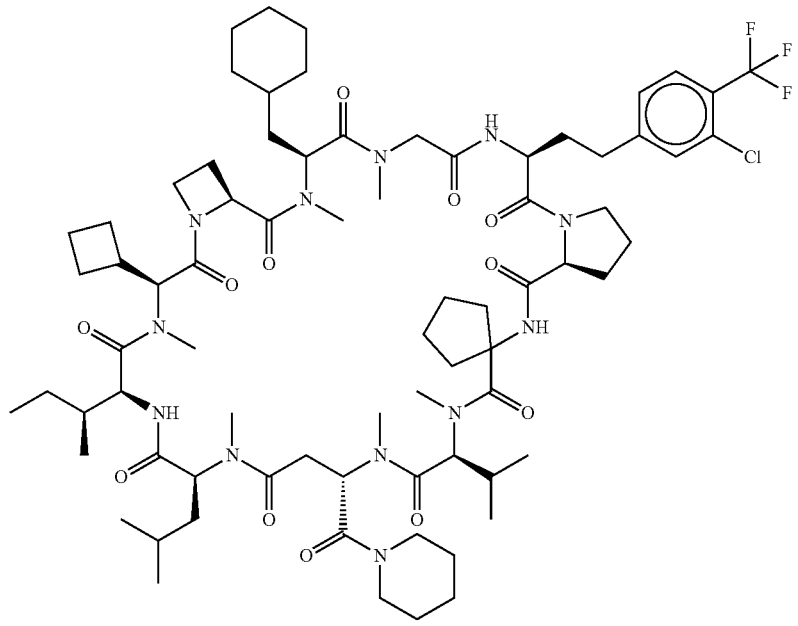 |

TABLE 24-continued
| Compound No. | Structural formula |
|---|---|
| 1555 | 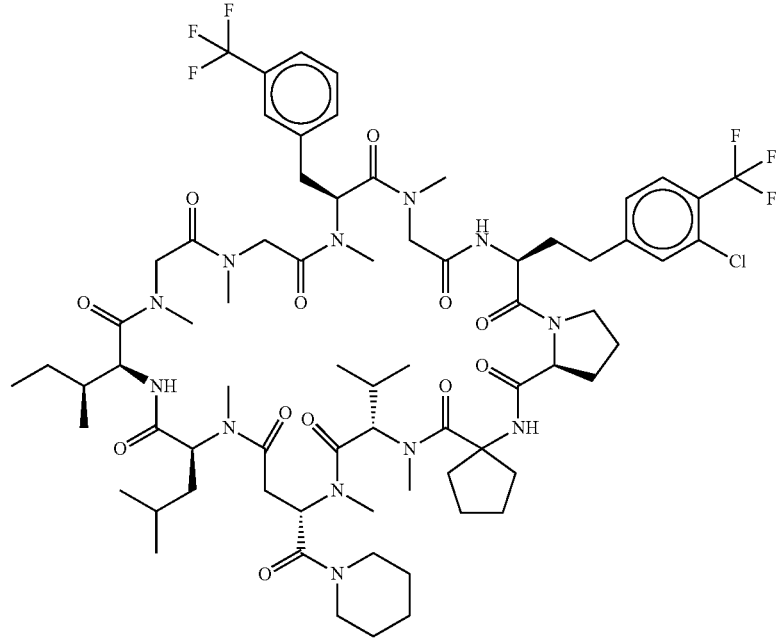 |
| 1556 | 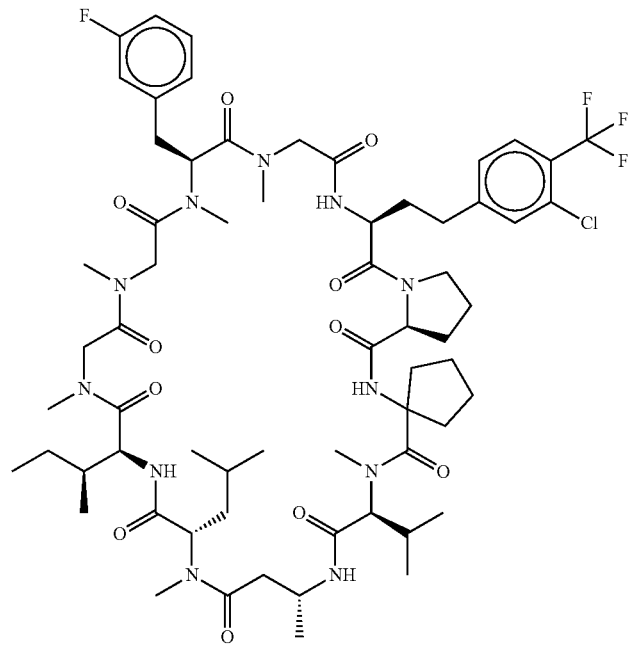 |

TABLE 24-continued
| Compound No. | Structural formula |
|---|---|
| 1557 | 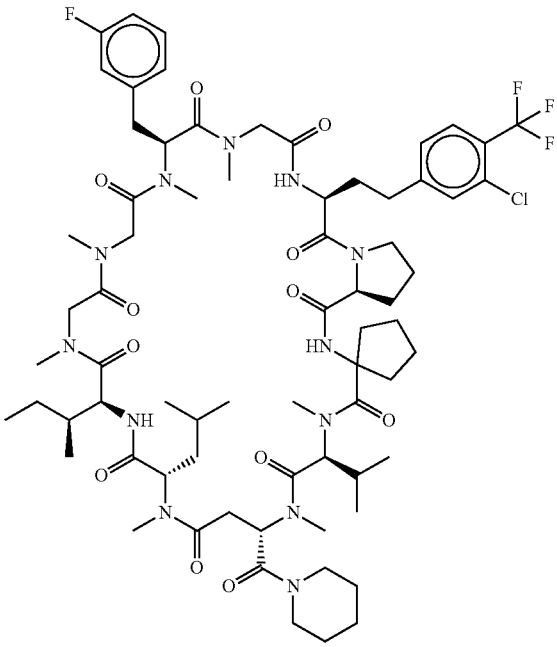 |
| 1558 | 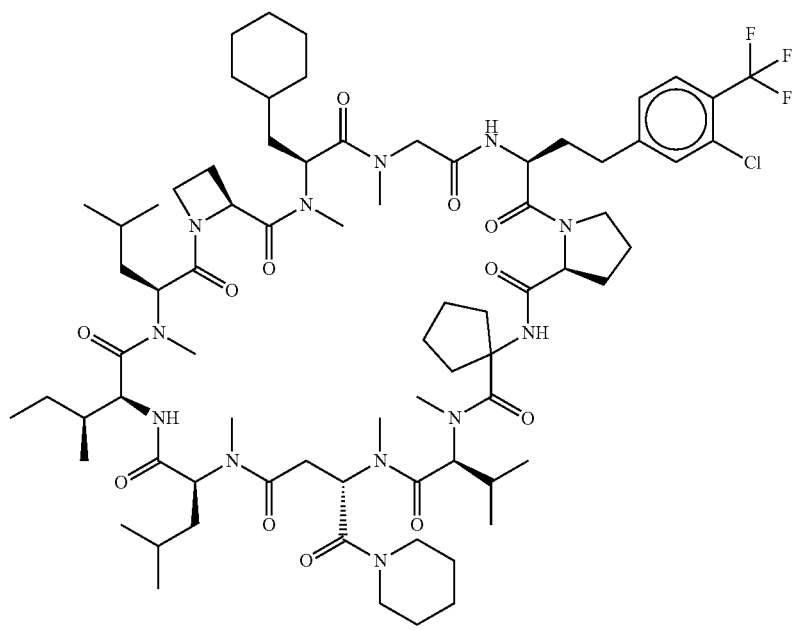 |

TABLE 24-continued
| Compound No. | Structural formula |
|---|---|
| 1559 | 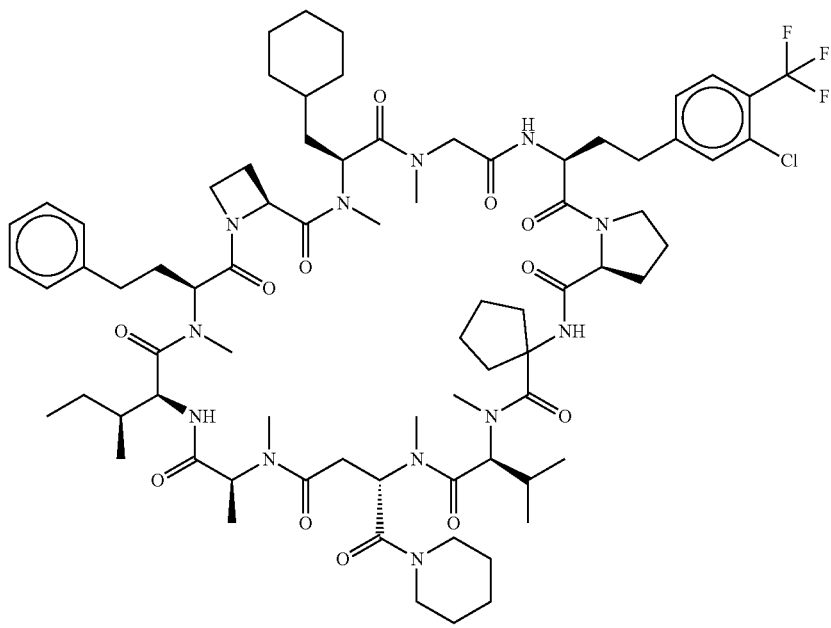 |
| 1560 | 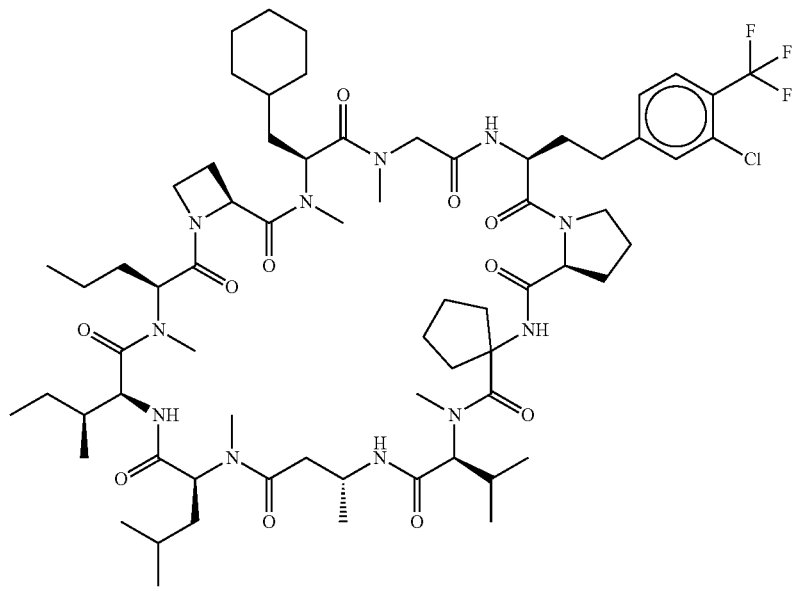 |

TABLE 24-continued
| Compound No. | Structural formula |
| --- | --- |
| 1561 | 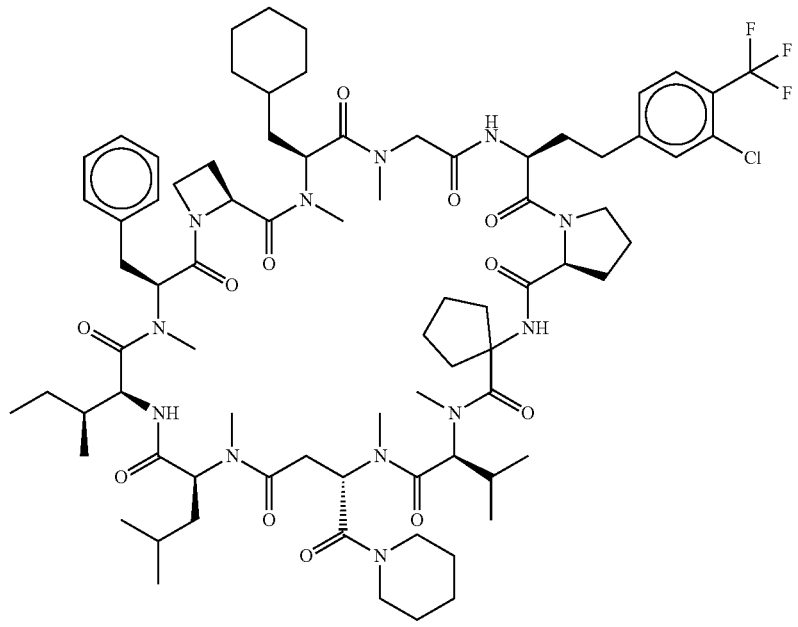 |
| 1562 | 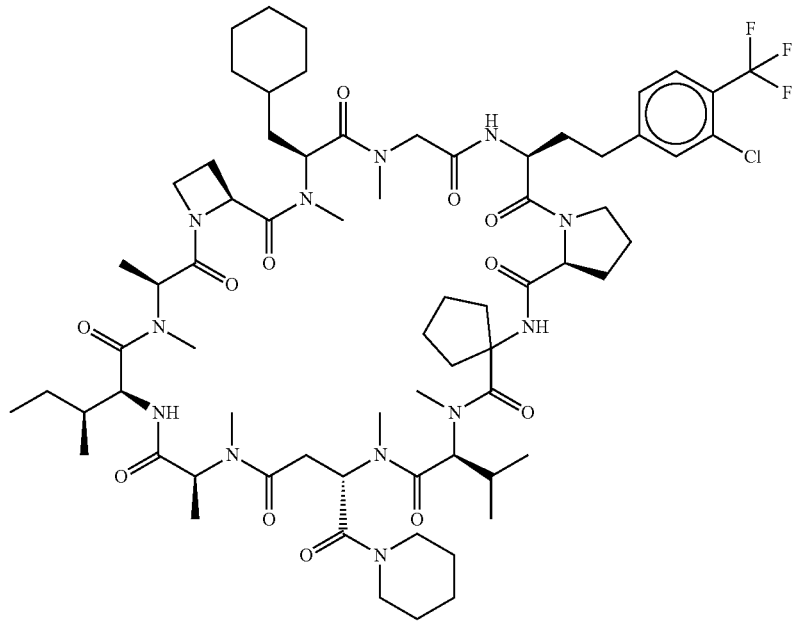 |

TABLE 24-continued

| Compound No. | Structural formula |
| --- | --- |
| 1563 | |
| 1564 | |

TABLE 24-continued
| Compound No. | Structural formula |
|---|---|
| 1565 | 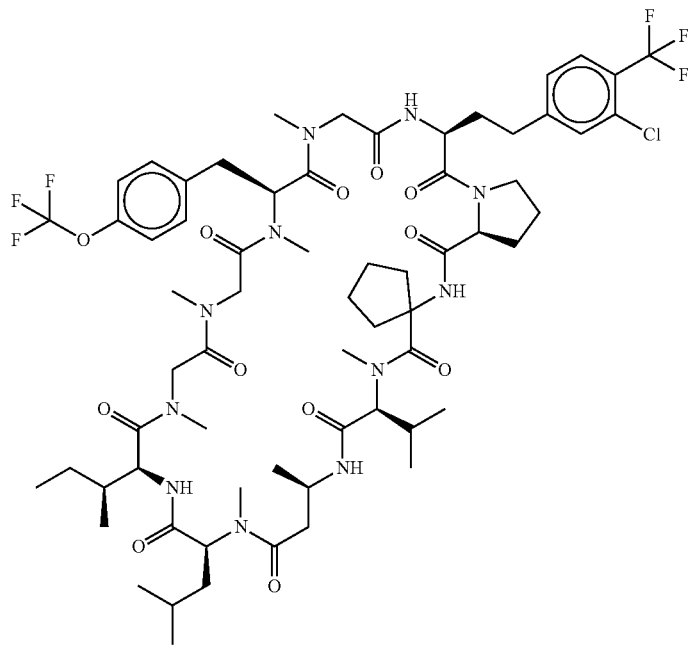 |
| 1566 | 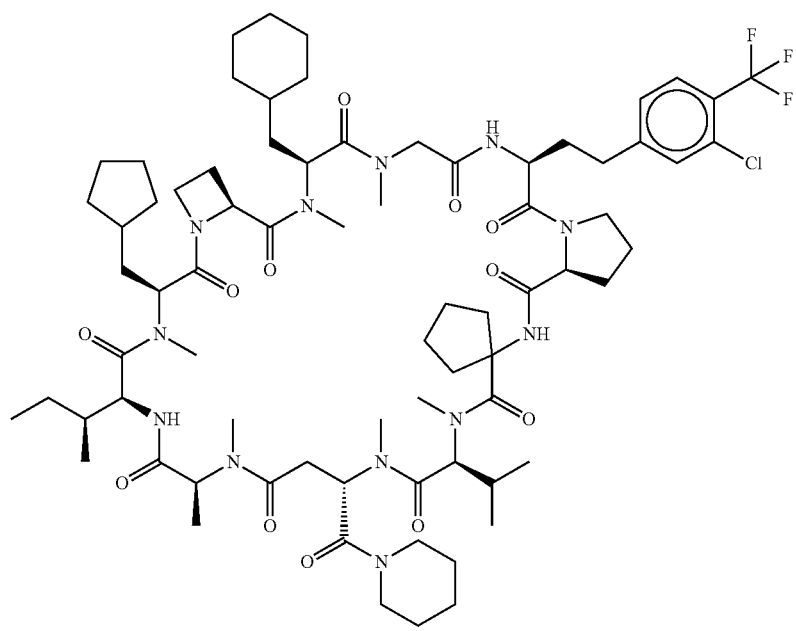 |

TABLE 24-continued
| Compound No. | Structural formula |
|---|---|
| 1567 | 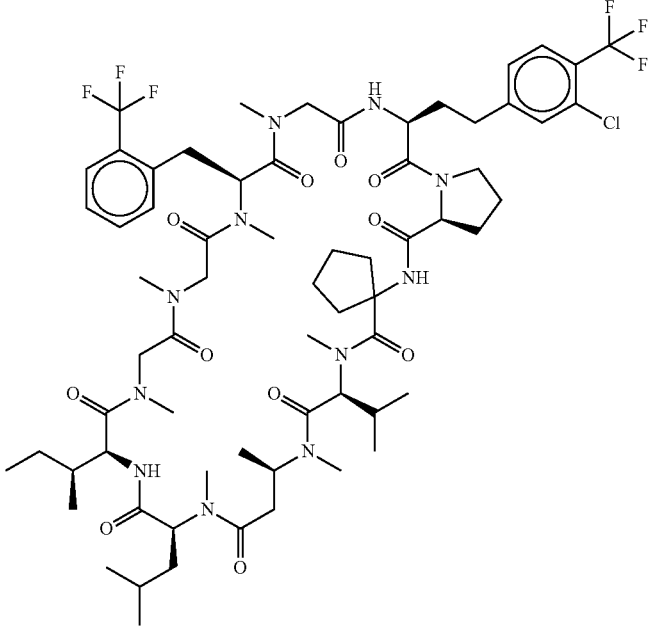 |
| 1568 | 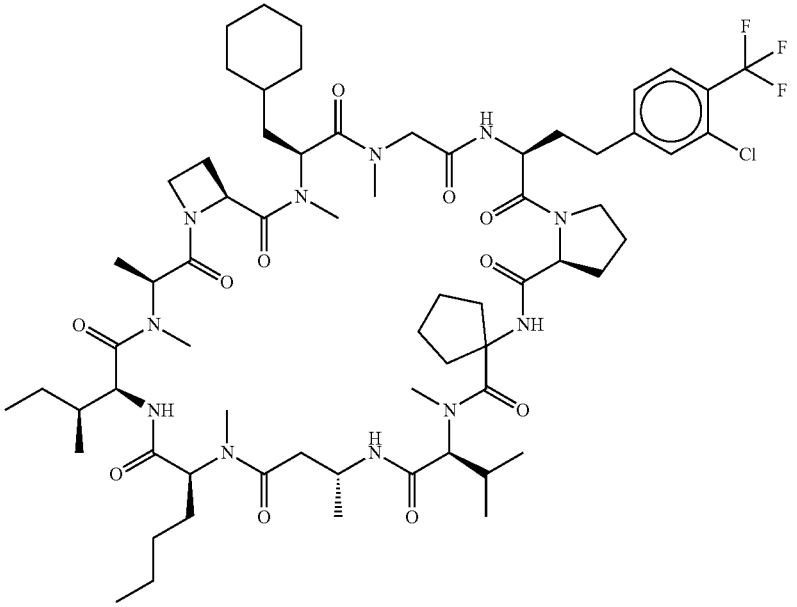 |

TABLE 24-continued
| Compound No. | Structural formula |
|---|---|
| 1569 | 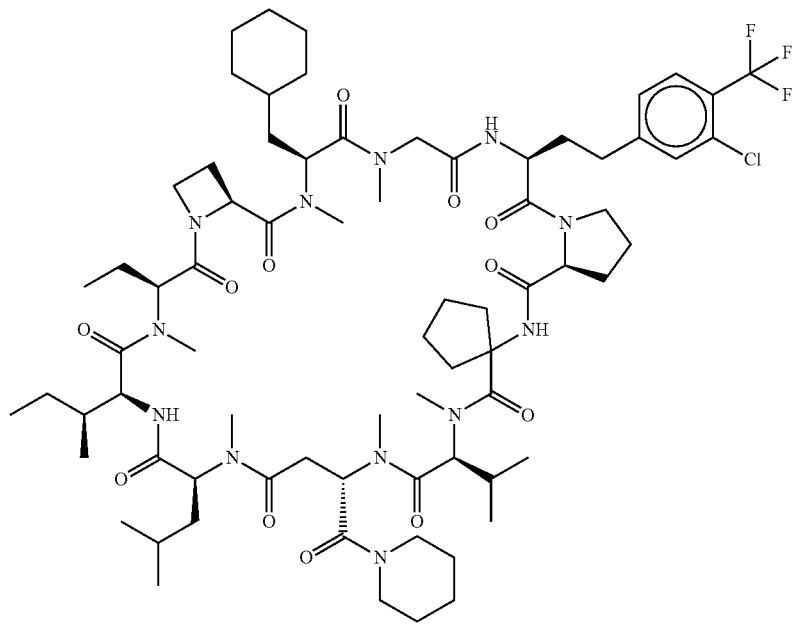 |
| 1570 | 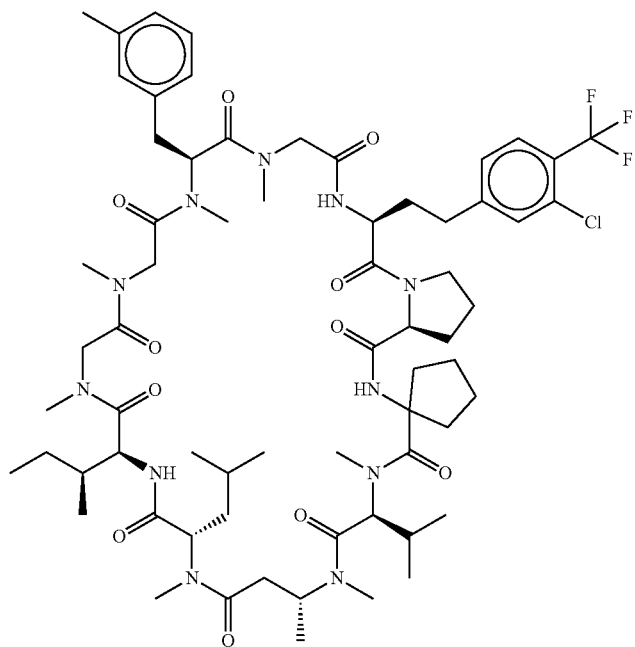 |

TABLE 24-continued
| Compound No. | Structural formula |
|---|---|
| 1571 | 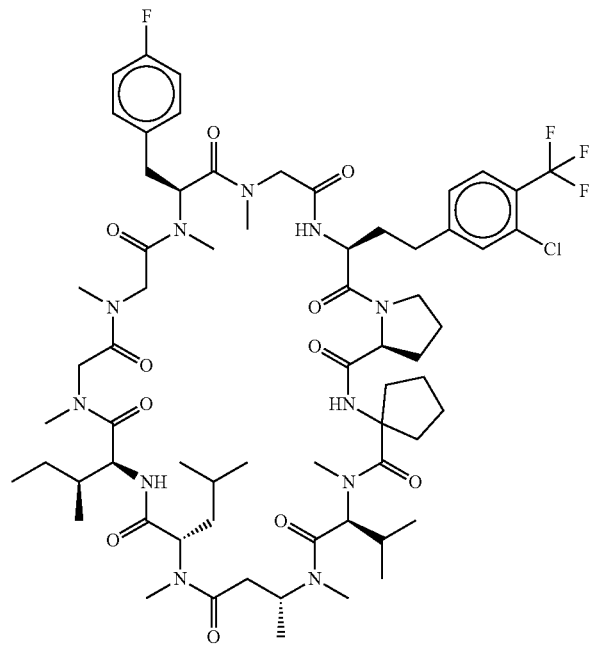 |
| 1572 | 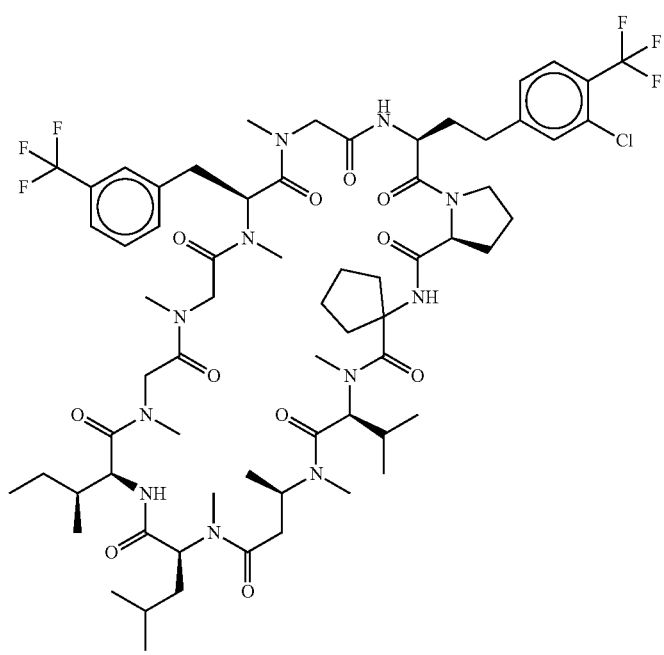 |

TABLE 24-continued
| Compound No. | Structural formula |
|---|---|
| 1573 | 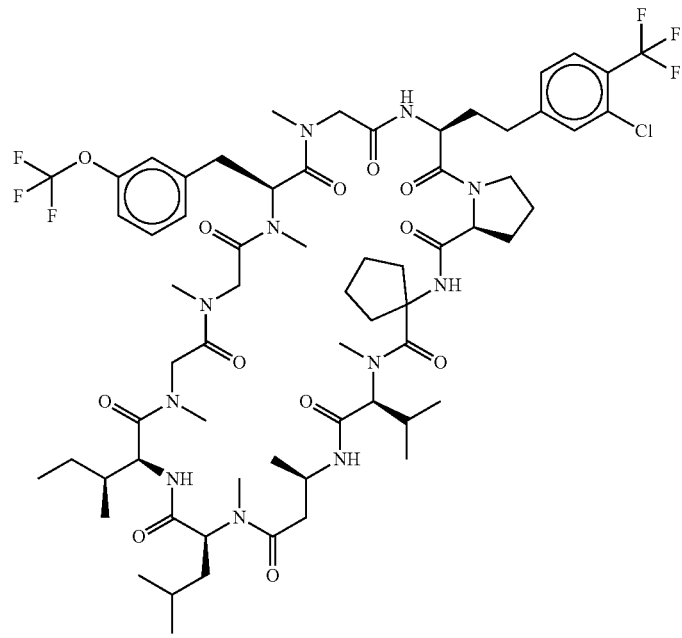 |
| 1574 | 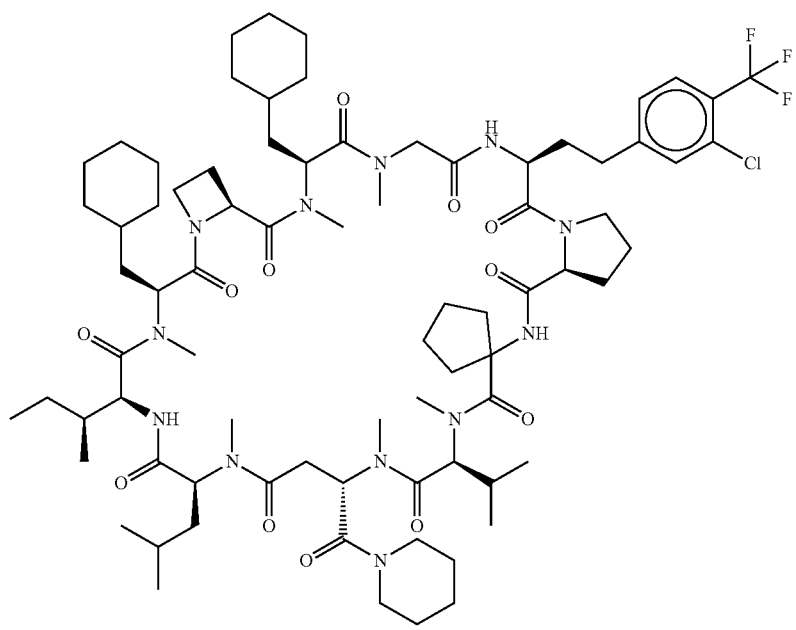 |

TABLE 24-continued

| Compound No. | Structural formula |
|---|---|
| 1575 | |
| 1576 | |

TABLE 24-continued
| Compound No. | Structural formula |
|---|---|
| 1577 | 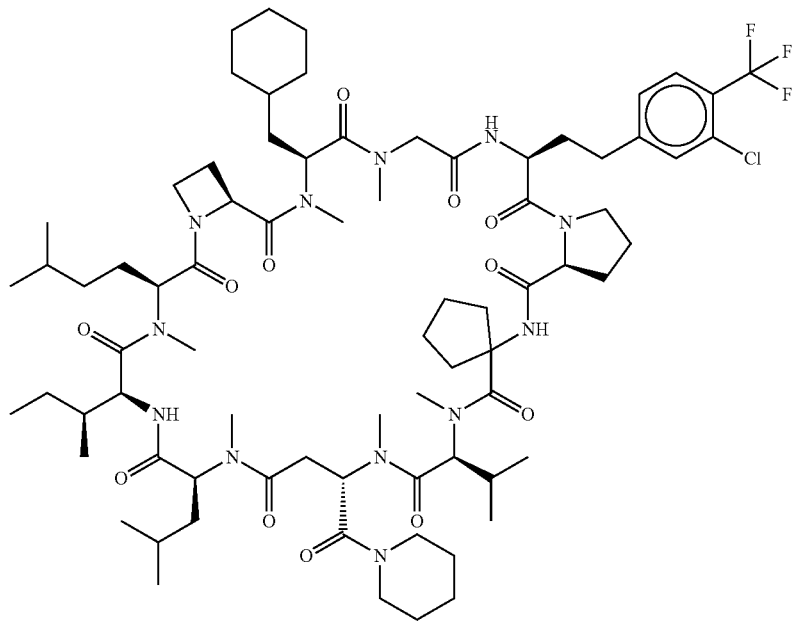 |
| 1578 | 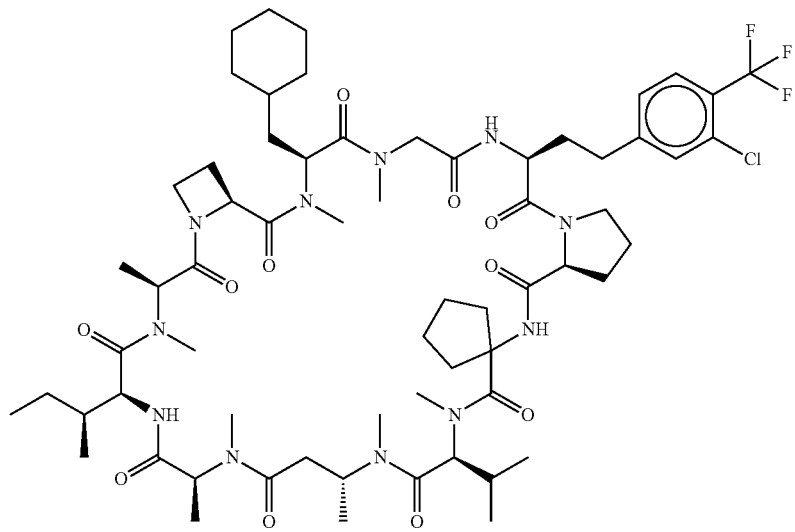 |

TABLE 24-continued
| Compound No. | Structural formula |
|---|---|
| 1579 | 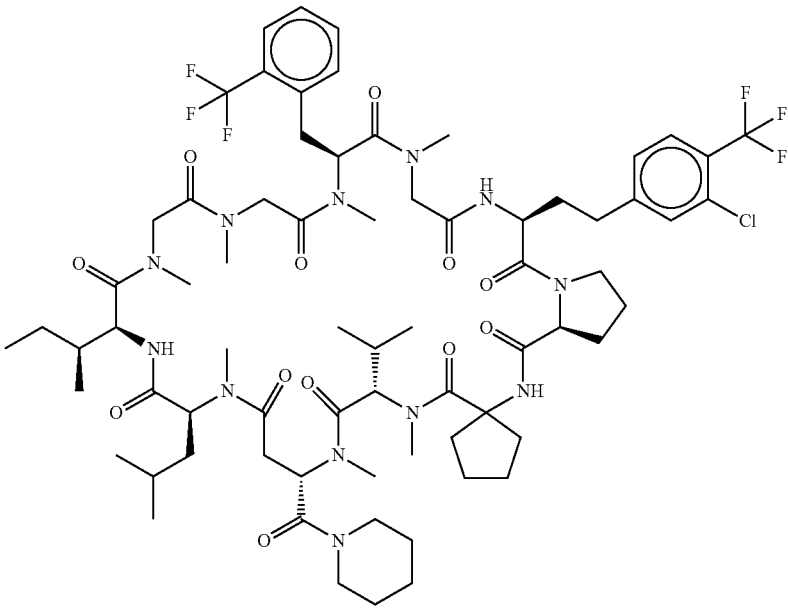 |
| 1580 | 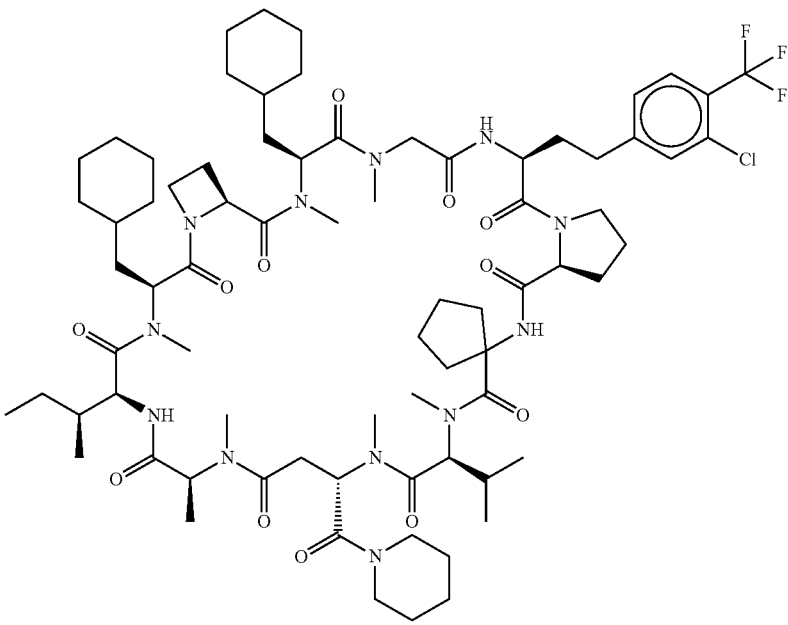 |

TABLE 24-continued
| Compound No. | Structural formula |
|---|---|
| 1581 | 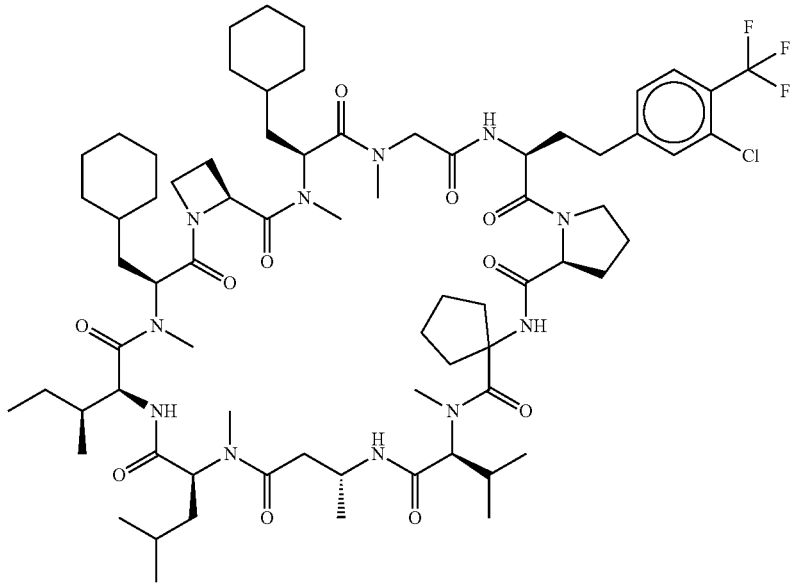 |
| 1582 | 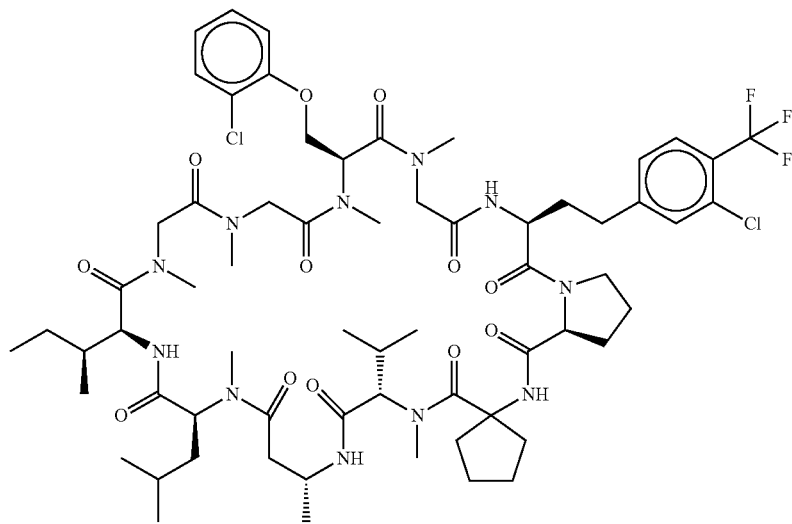 |

TABLE 24-continued
| Compound No. | Structural formula |
|---|---|
| 1583 | 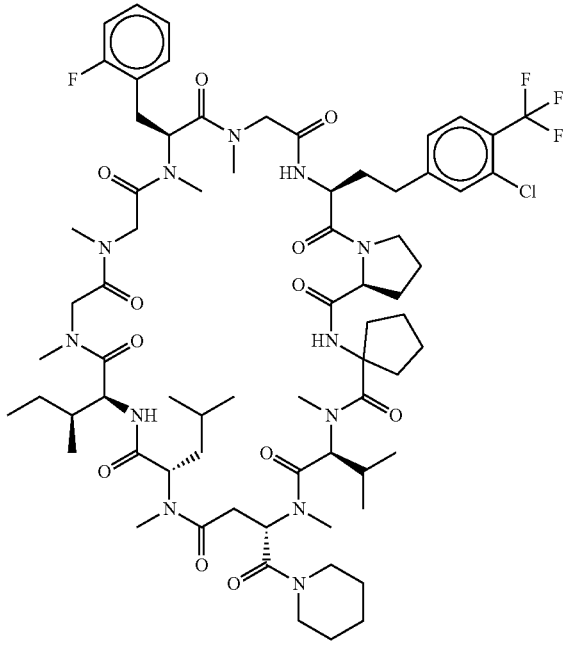 |
| 1584 | 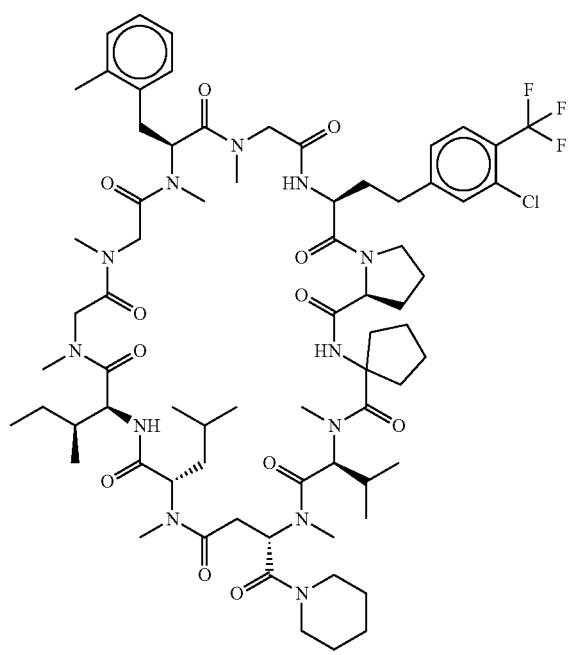 |

TABLE 24-continued
| Compound No. | Structural formula |
|---|---|
| 1585 | 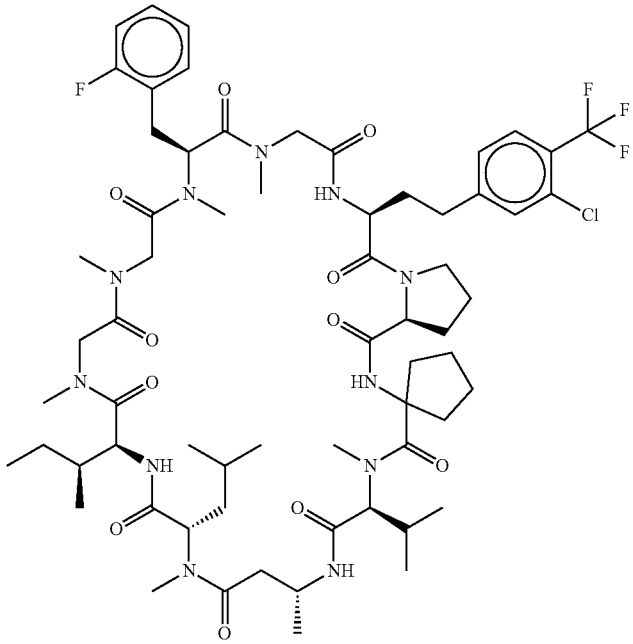 |
| 1586 | 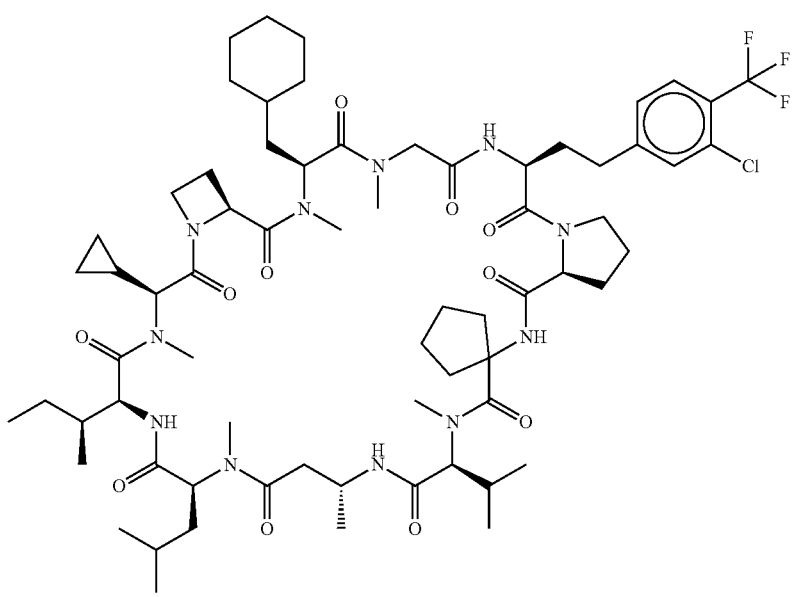 |

TABLE 24-continued
| Compound No. | Structural formula |
|---|---|
| 1587 | 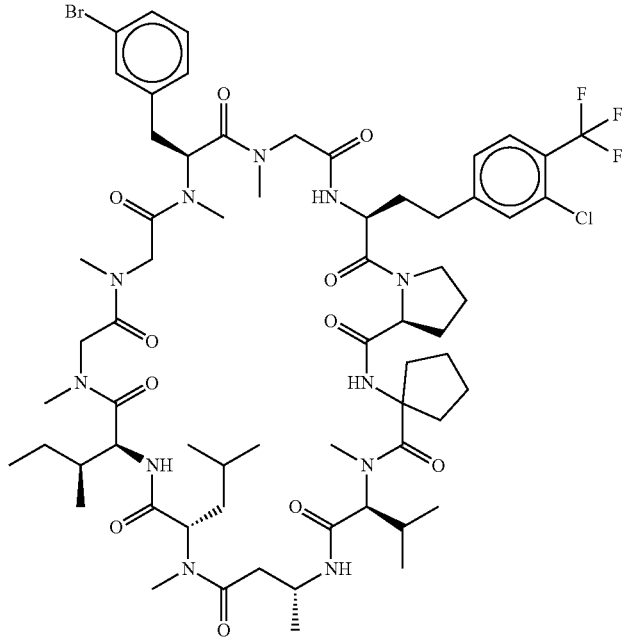 |
| 1588 | 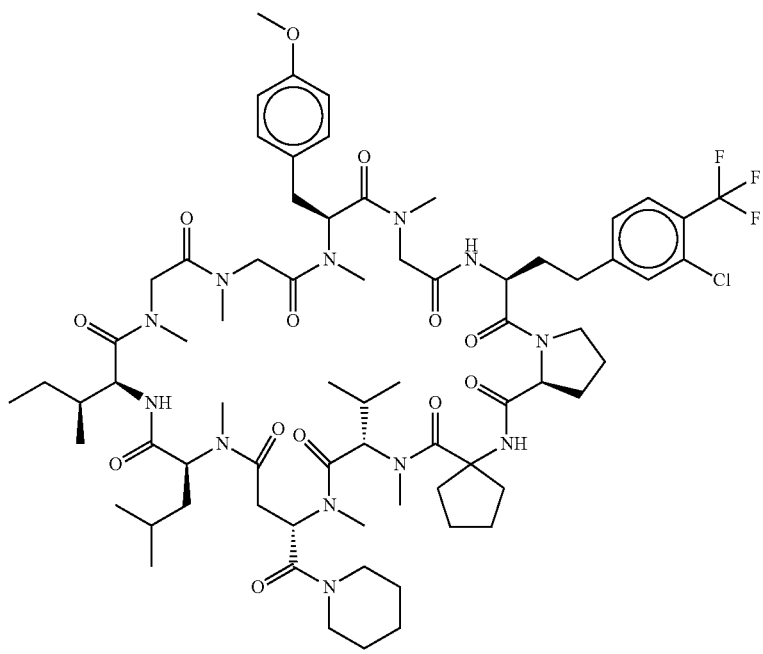 |

TABLE 24-continued
| Compound No. | Structural formula |
|---|---|
| 1589 | 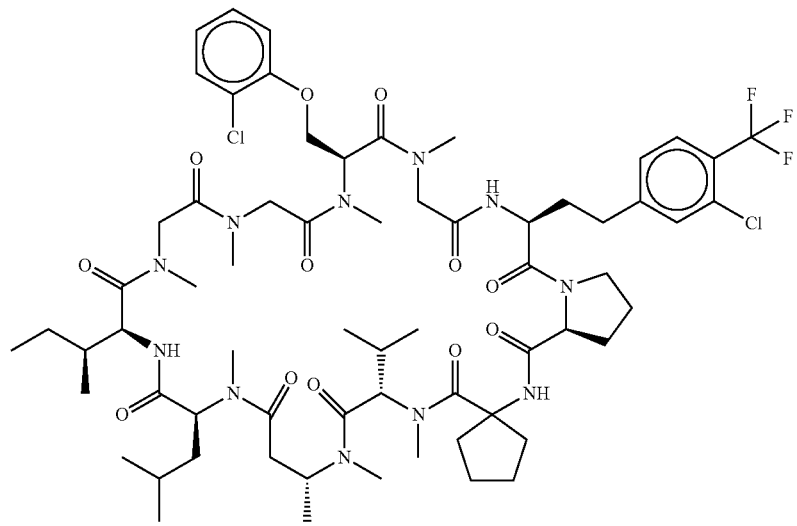 |
| 1590 | 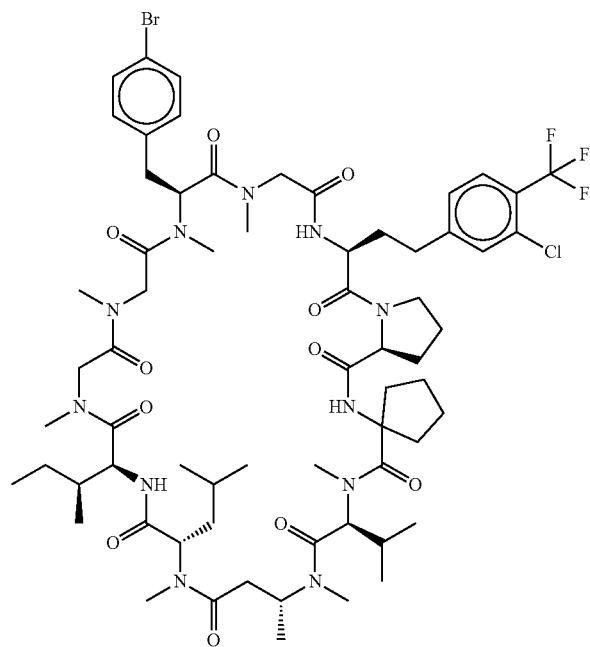 |

TABLE 24-continued
| Compound No. | Structural formula |
|---|---|
| 1591 | 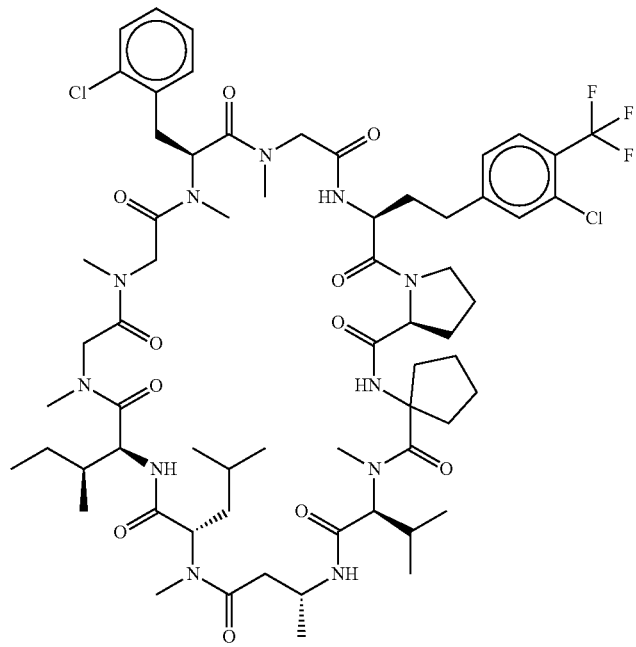 |
| 1592 | 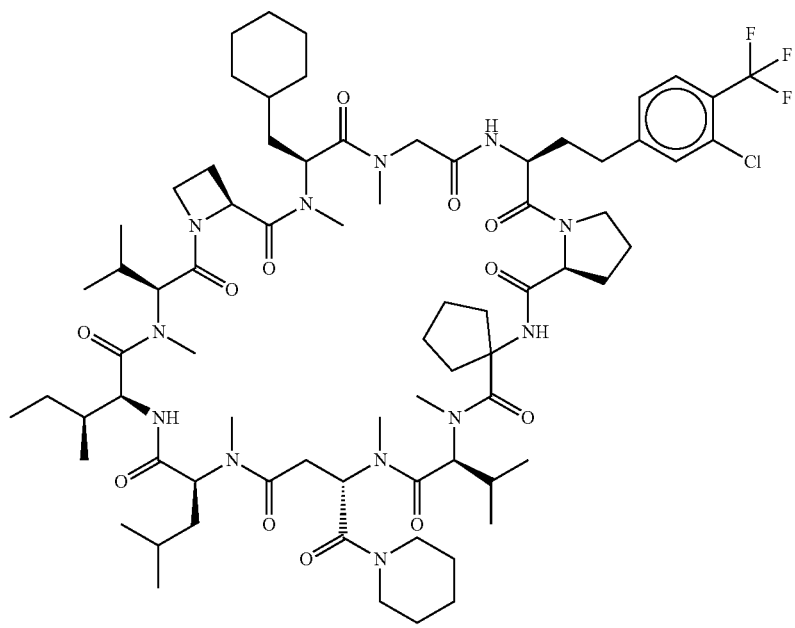 |

TABLE 24-continued
| Compound No. | Structural formula |
|---|---|
| 1593 | 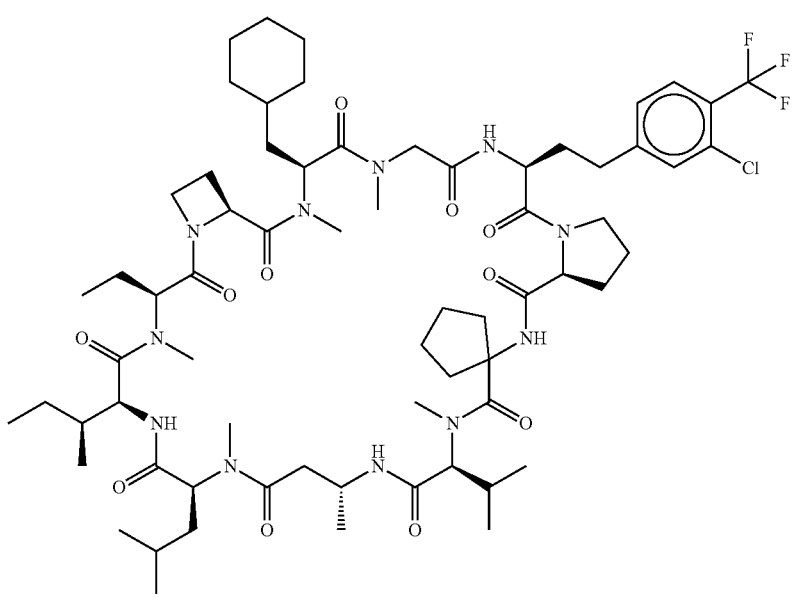 |
| 1594 | 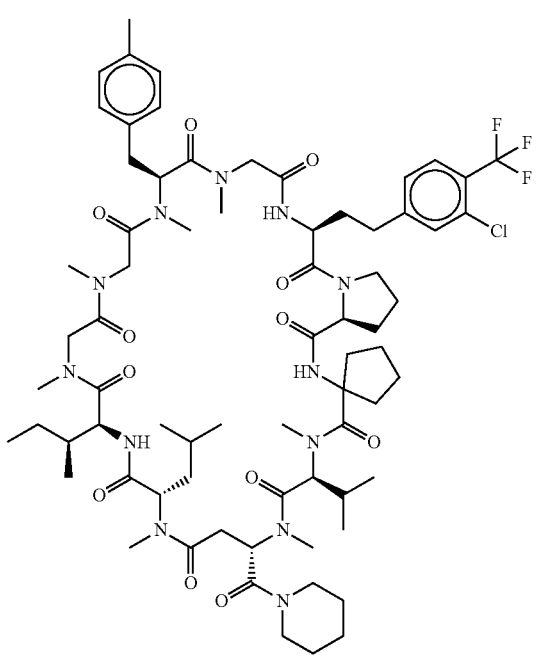 |

TABLE 24-continued
| Compound No. | Structural formula |
|---|---|
| 1595 | 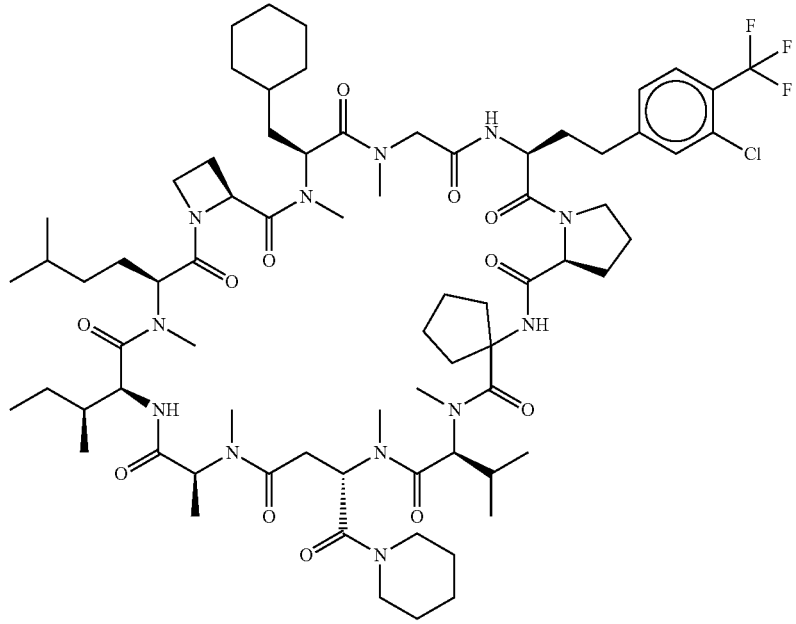 |
| 1596 | 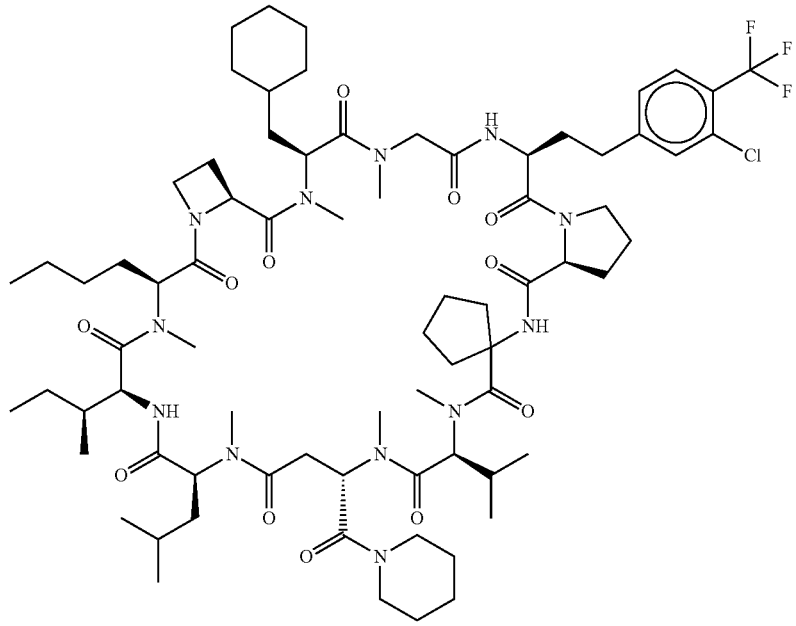 |

TABLE 24-continued
| Compound No. | Structural formula |
| --- | --- |
| 1597 | 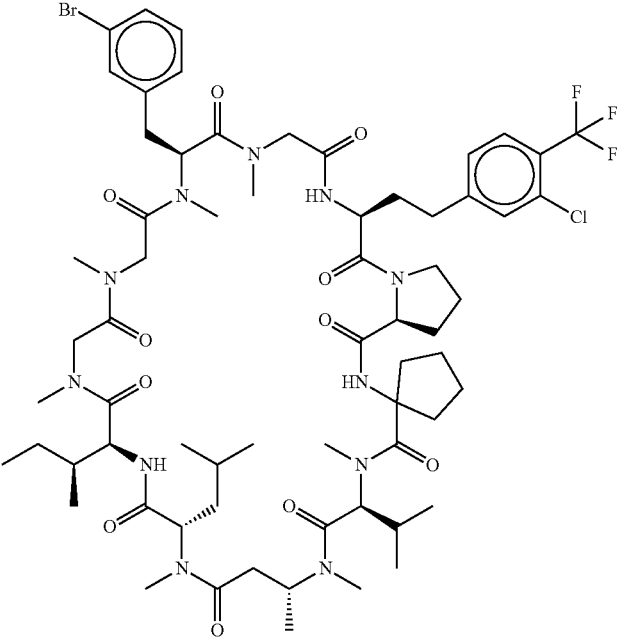 |
| 1598 | 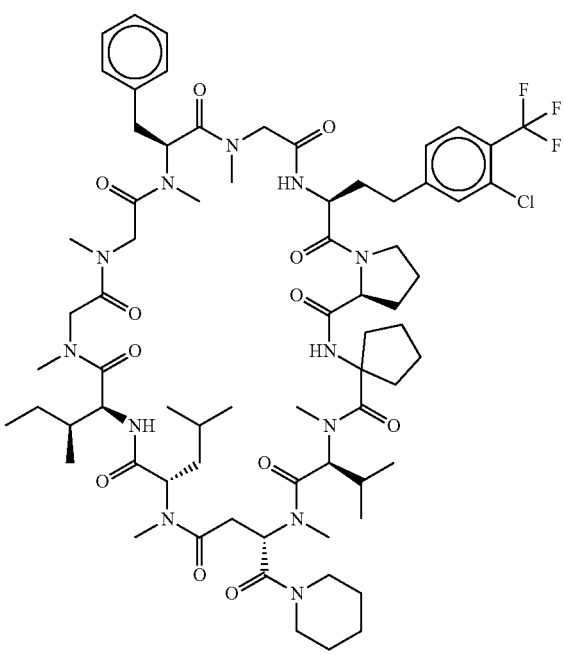 |

TABLE 24-continued
| Compound No. | Structural formula |
|---|---|
| 1599 | 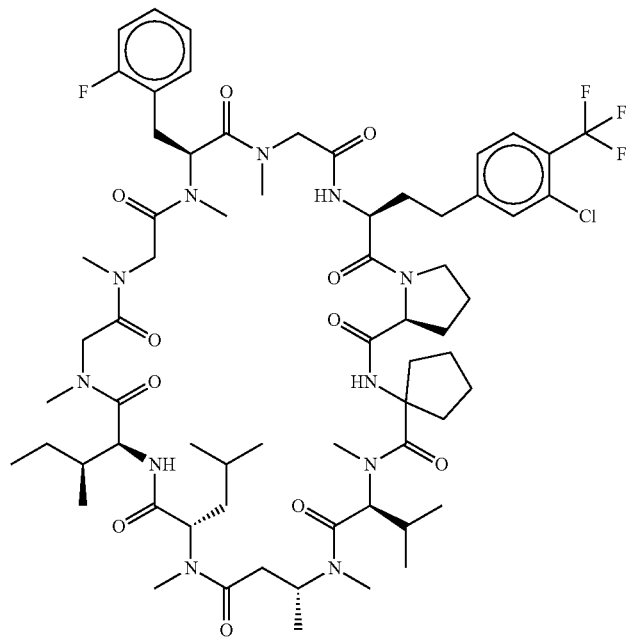 |
| 1600 | 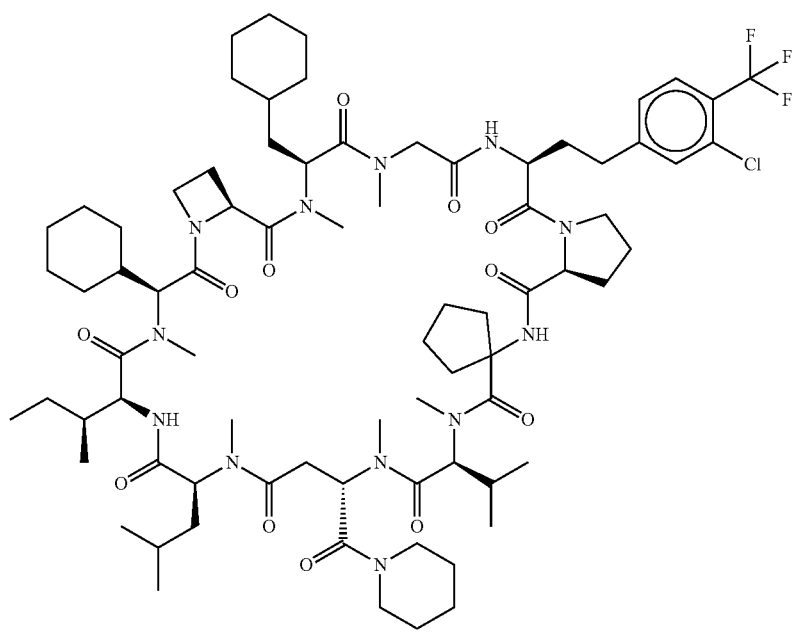 |

TABLE 24-continued
| Compound No. | Structural formula |
|---|---|
| 1601 | 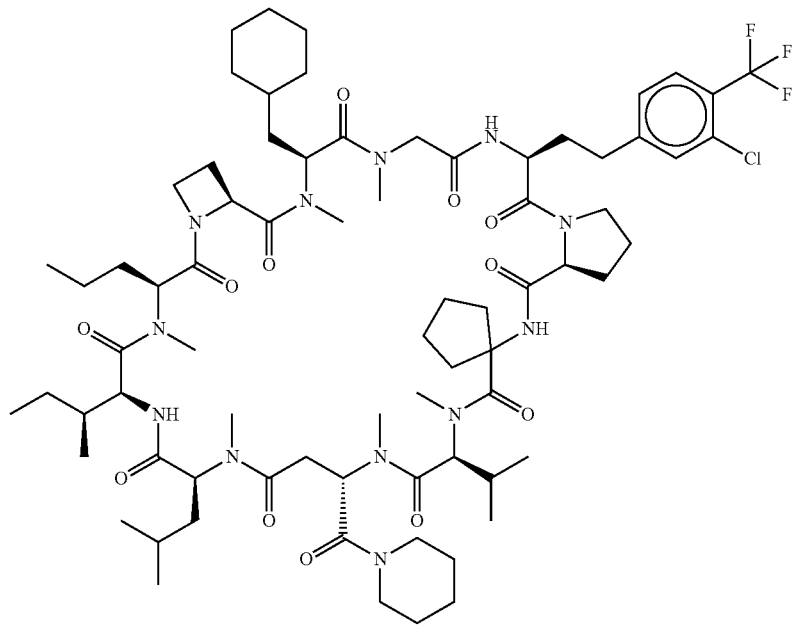 |
| 1602 | 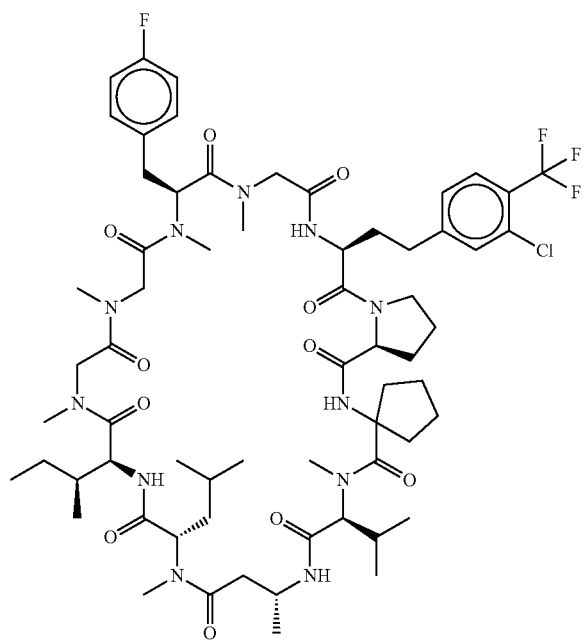 |

TABLE 24-continued
| Compound No. | Structural formula |
|---|---|
| 1603 | 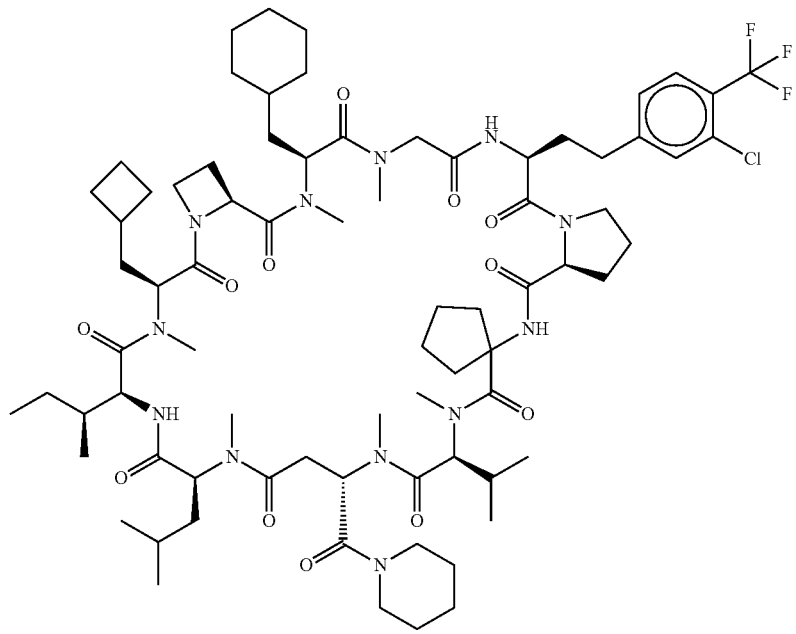 |
| 1604 | 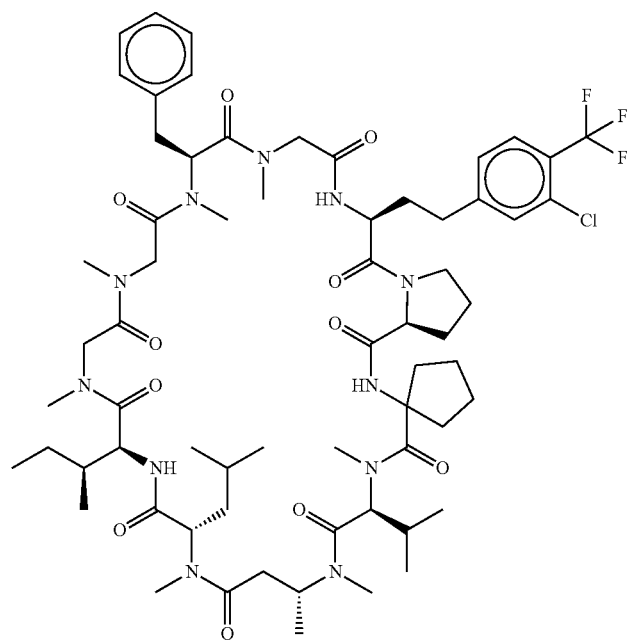 |

TABLE 24-continued
| Compound No. | Structural formula |
|---|---|
| 1605 | 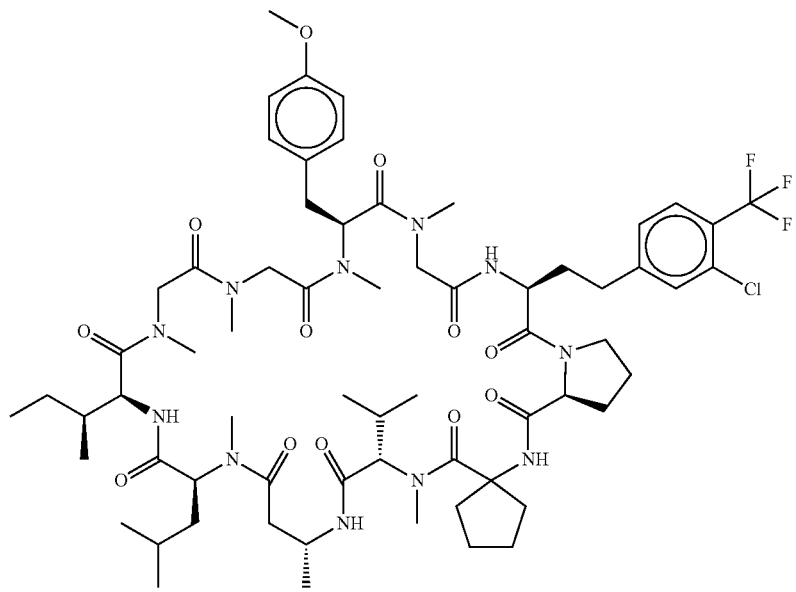 |
| 1606 | 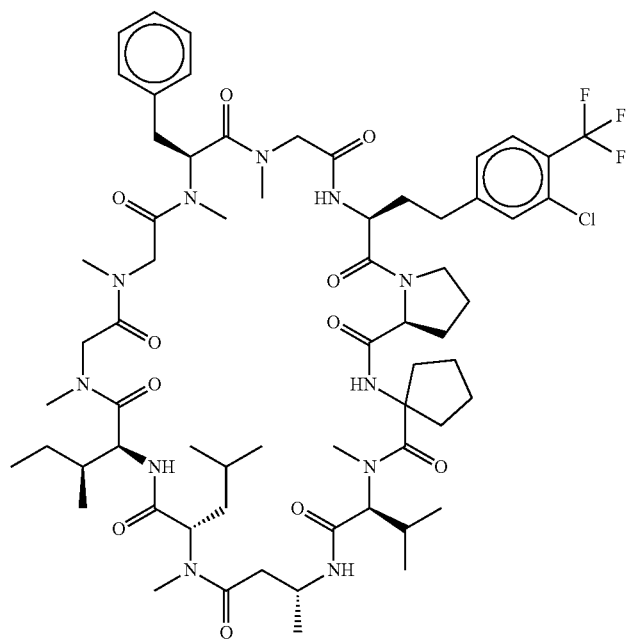 |

TABLE 24-continued
| Compound No. | Structural formula |
|---|---|
| 1607 | 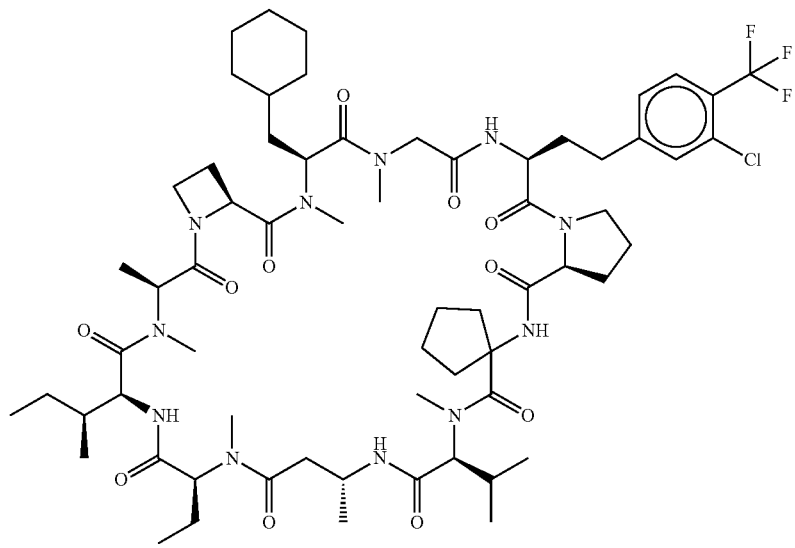 |
| 1608 | 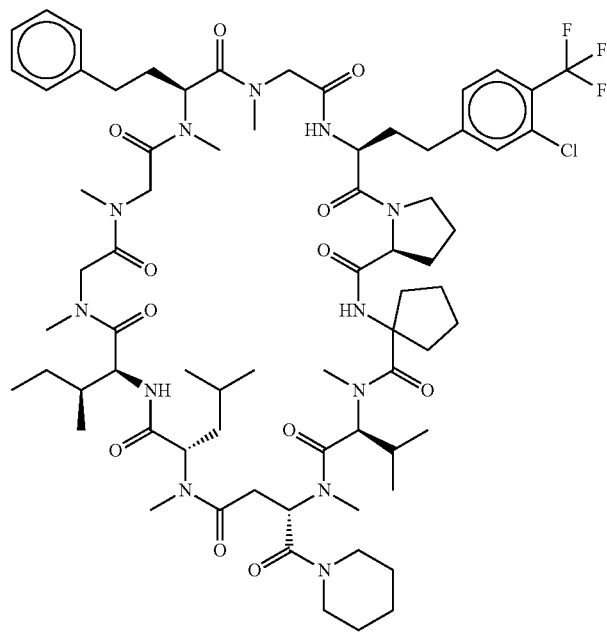 |

TABLE 24-continued
| Compound No. | Structural formula |
|---|---|
| 1609 | 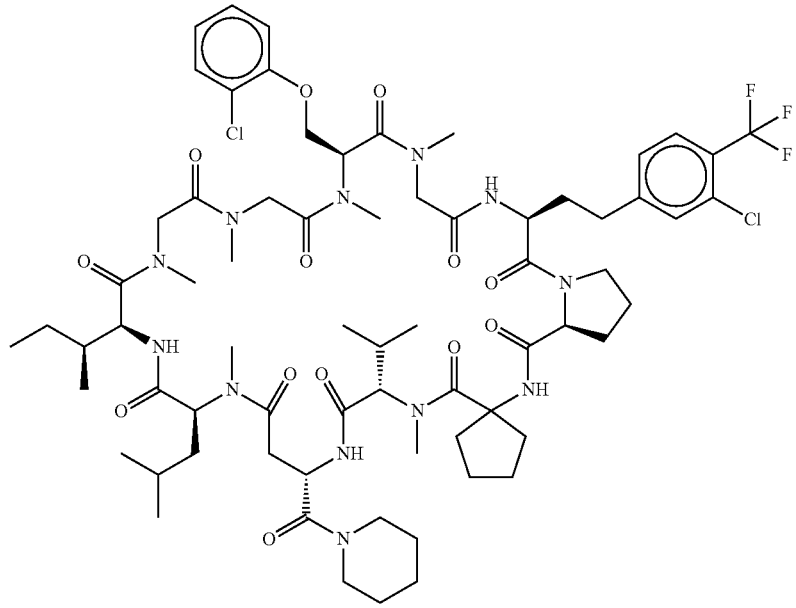 |
| 1610 | 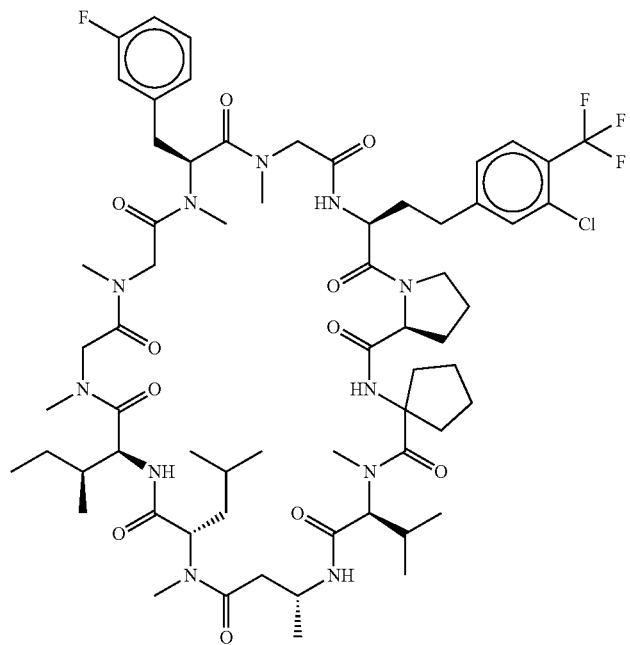 |

TABLE 24-continued
| Compound No. | Structural formula |
| --- | --- |
| 1611 | 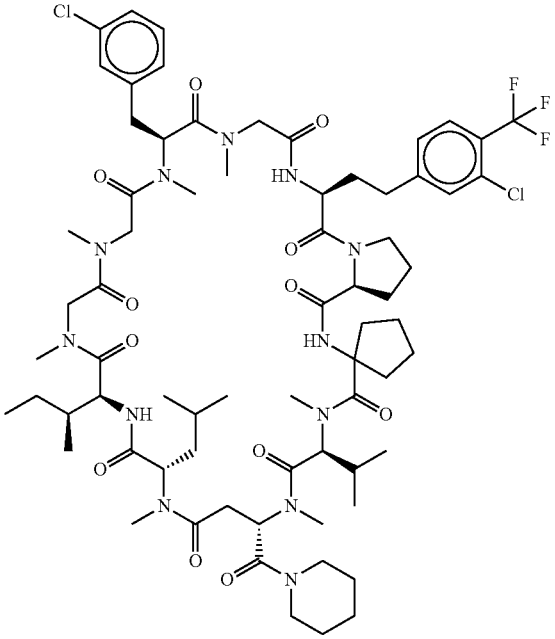 |
| 1612 | 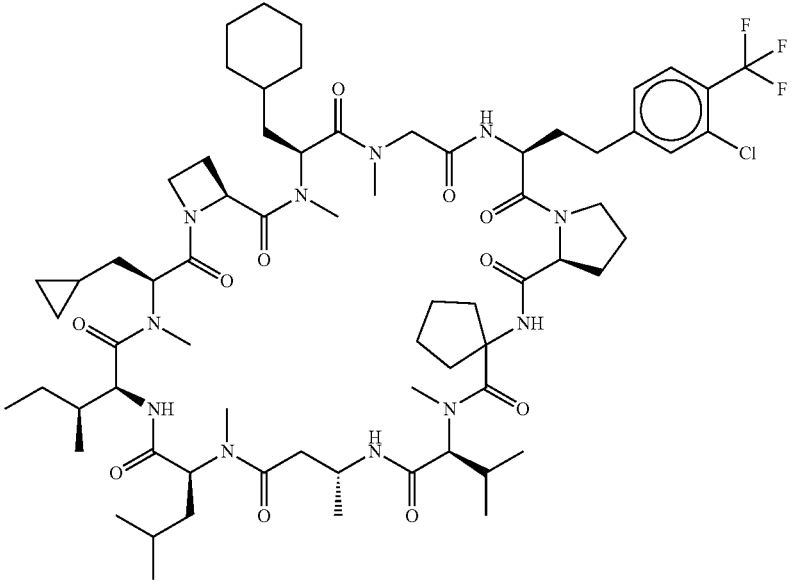 |

TABLE 24-continued
| Compound No. | Structural formula |
|---|---|
| 1613 | 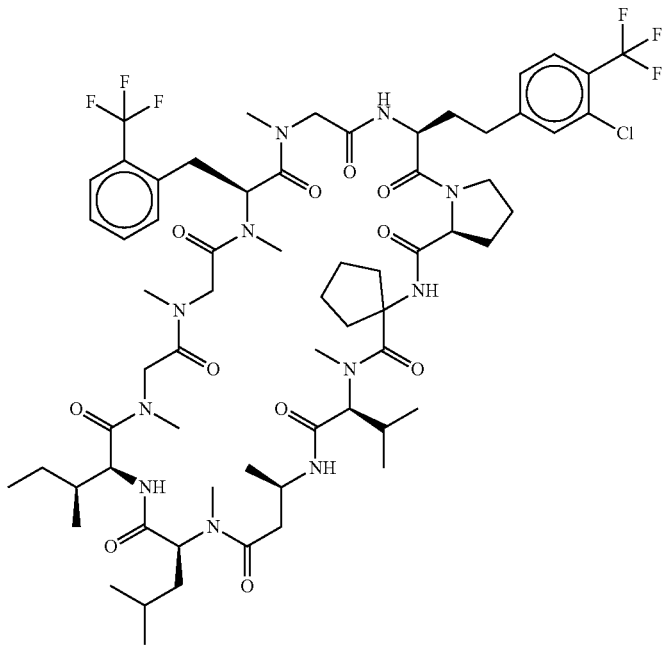 |
| 1614 | 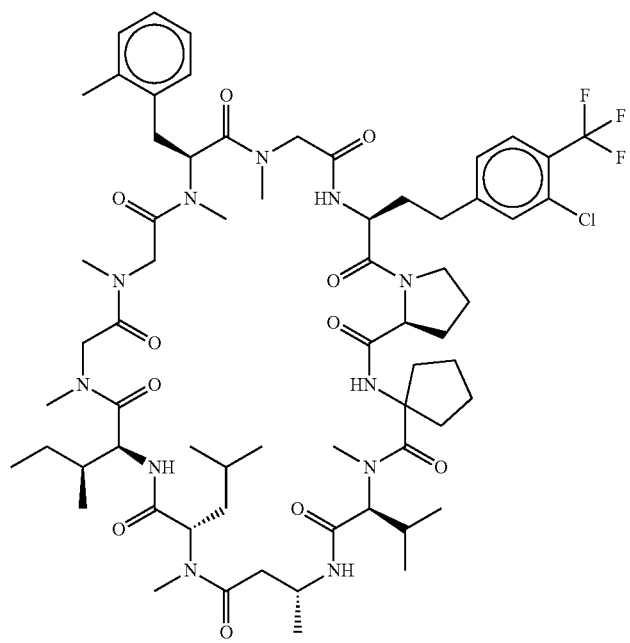 |

TABLE 24-continued
| Compound No. | Structural formula |
|---|---|
| 1615 | 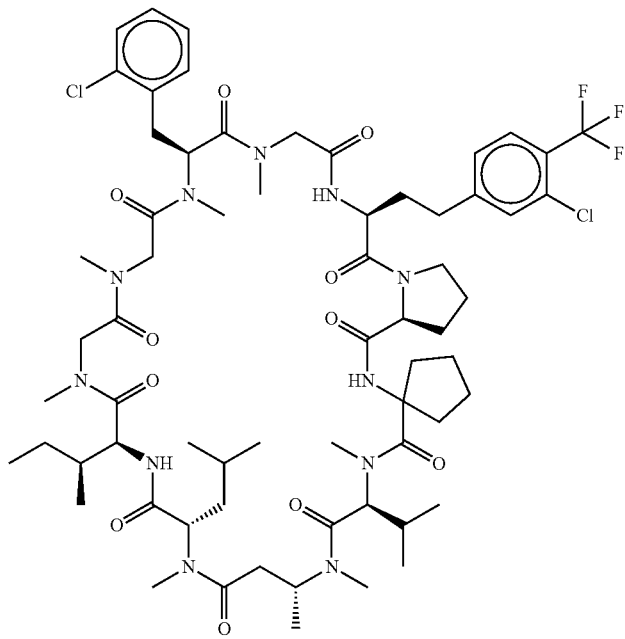 |
| 1616 | 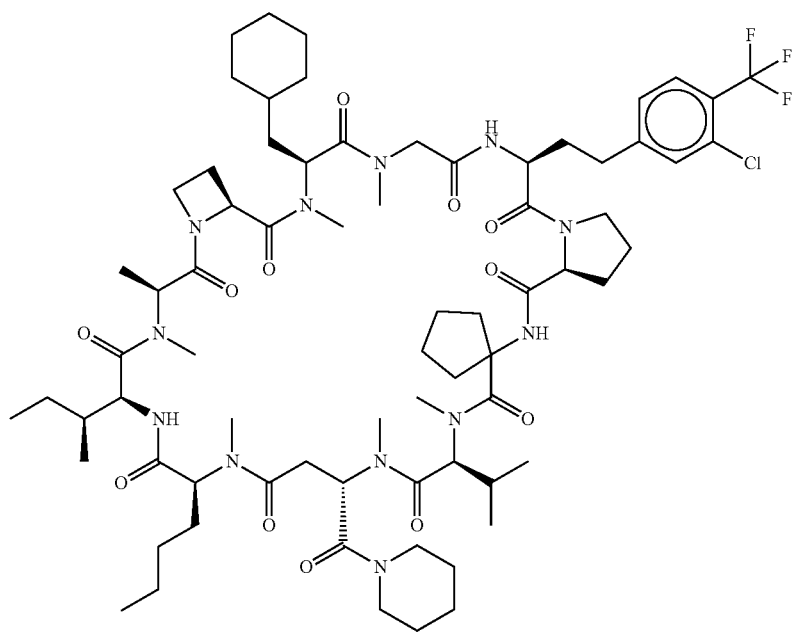 |

TABLE 24-continued
| Compound No. | Structural formula |
|---|---|
| 1617 | 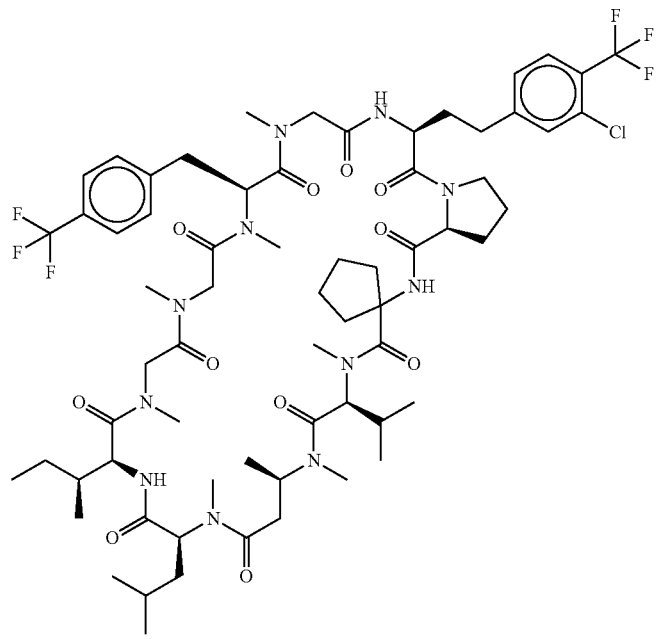 |
| 1618 | 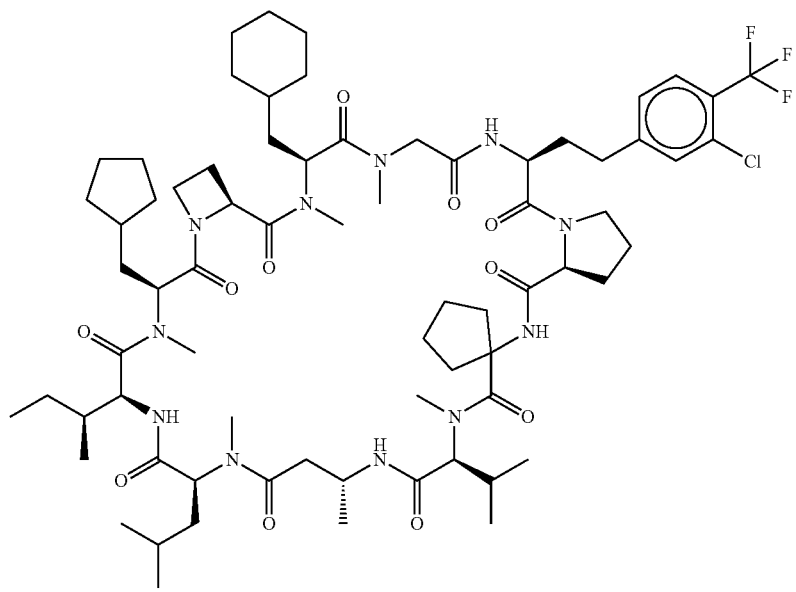 |

TABLE 24-continued
| Compound No. | Structural formula |
|---|---|
| 1619 | 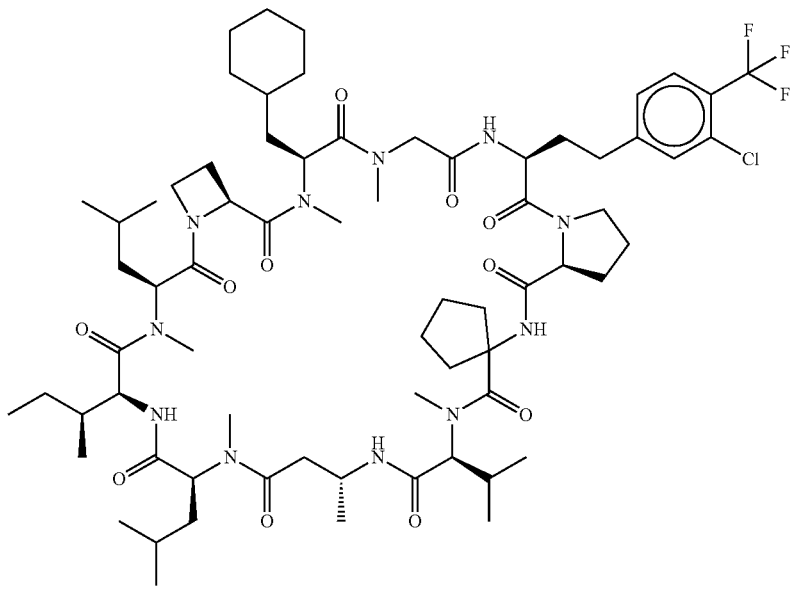 |
| 1620 | 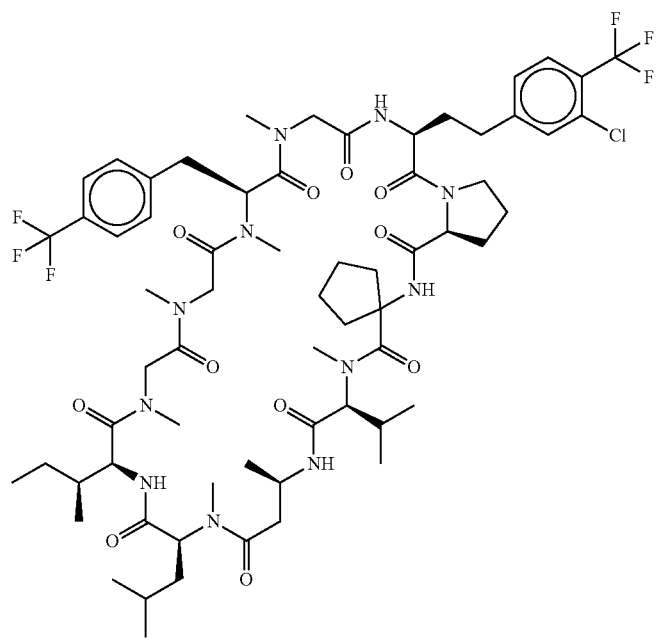 |

TABLE 24-continued
| Compound No. | Structural formula |
|---|---|
| 1621 | 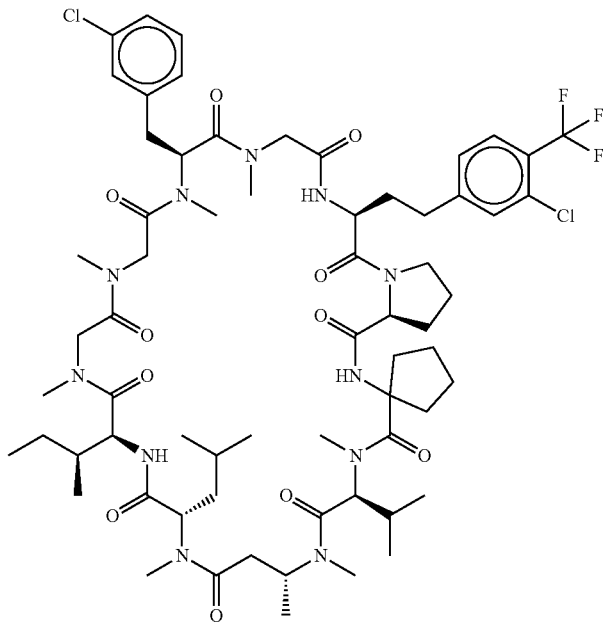 |
| 1622 | 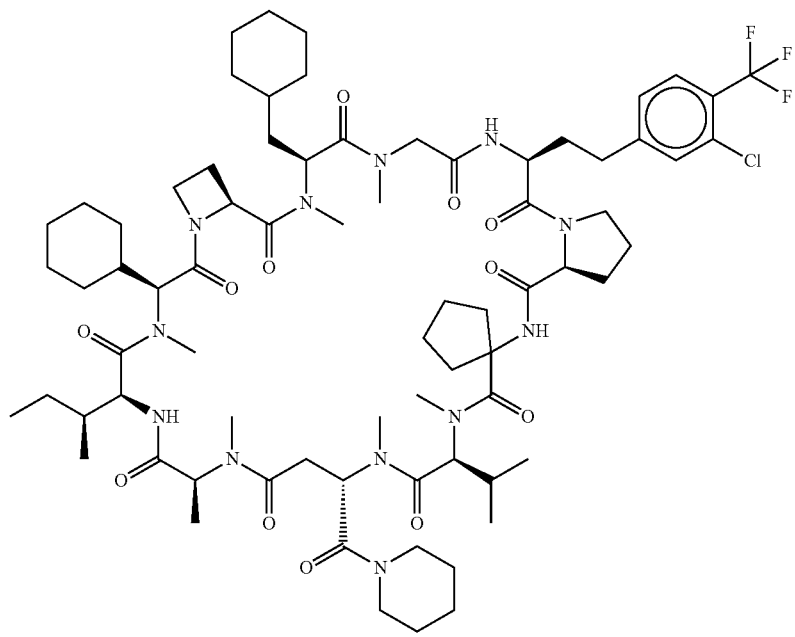 |

TABLE 24-continued

| Compound No. | Structural formula |
|---|---|
| 1623 | |
| 1624 | |

TABLE 24-continued
| Compound No. | Structural formula |
|---|---|
| 1625 | 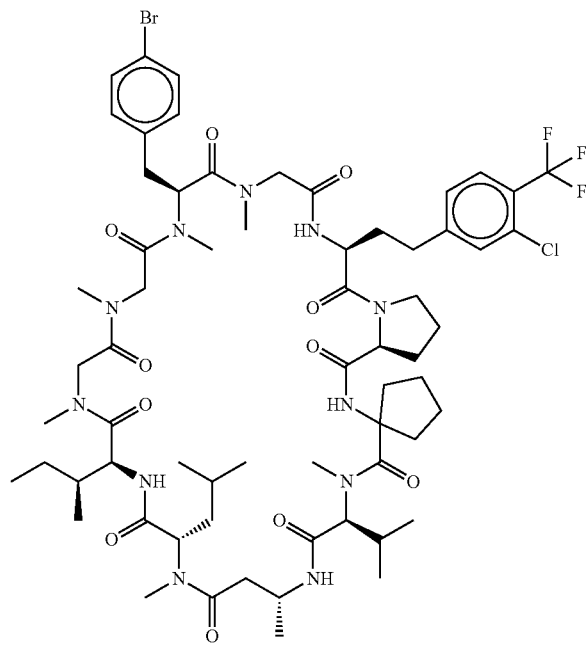 |
| 1626 | 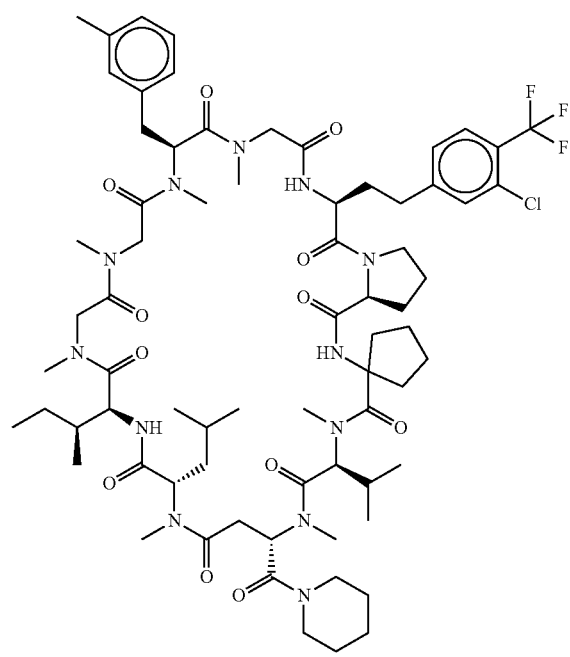 |

//
TABLE 24-continued
| Compound No. | Structural formula |
|---|---|
| 1627 | 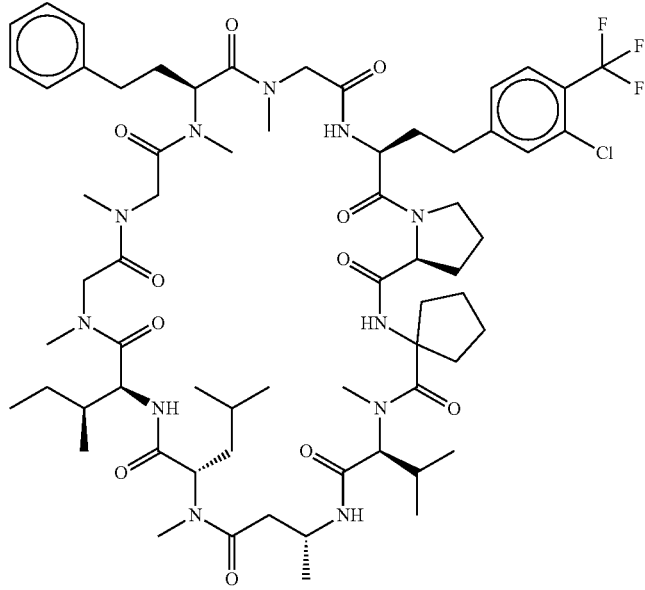 |
| 1628 | 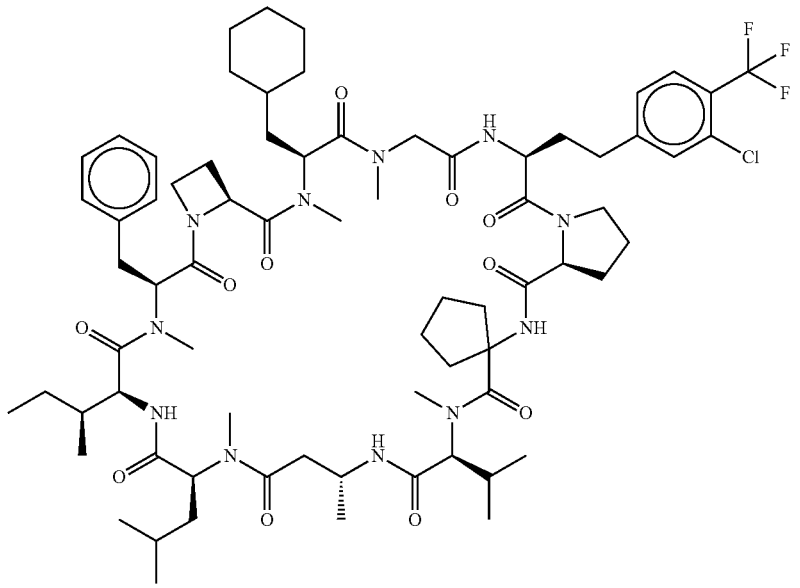 |

TABLE 24-continued
| Compound No. | Structural formula |
|---|---|
| 1629 | 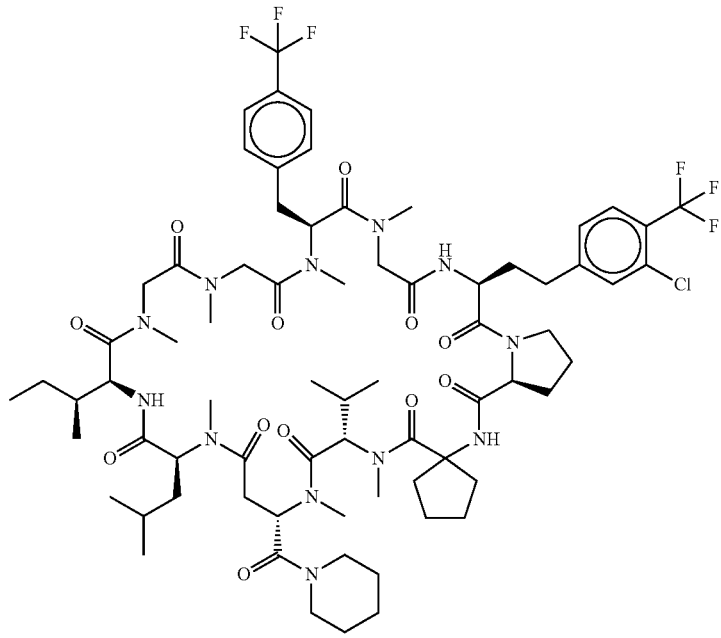 |
| 1630 | 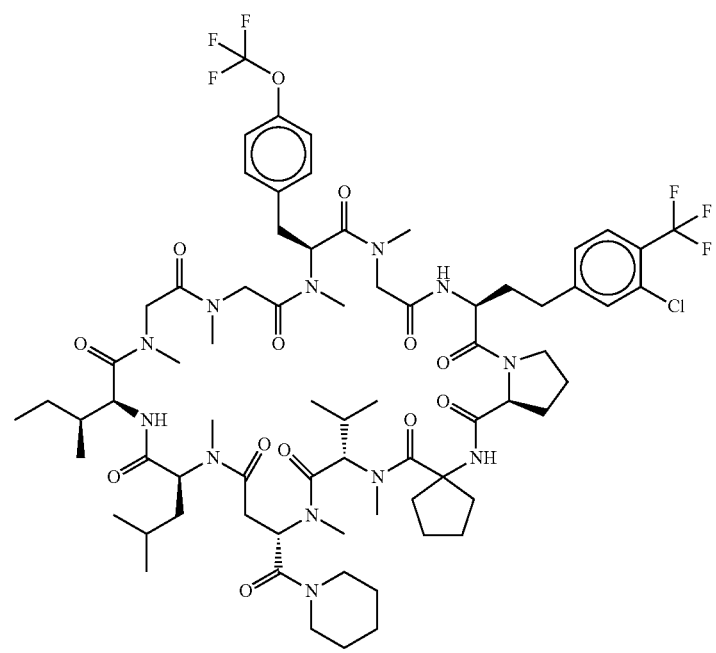 |

TABLE 24-continued
| Compound No. | Structural formula |
|---|---|
| 1631 | 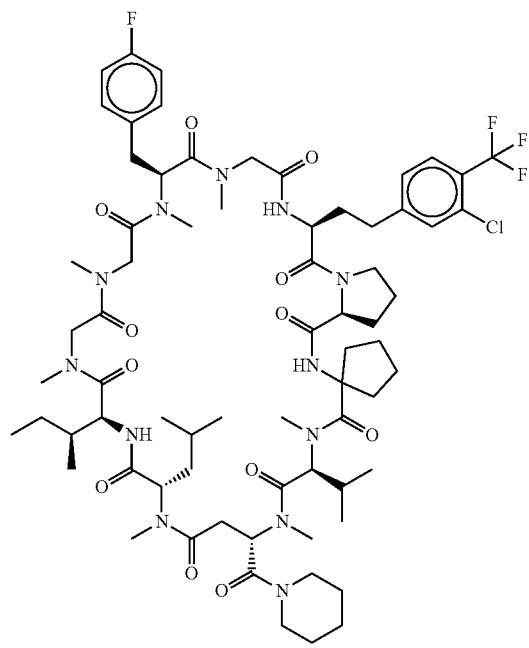 |
| 1632 | 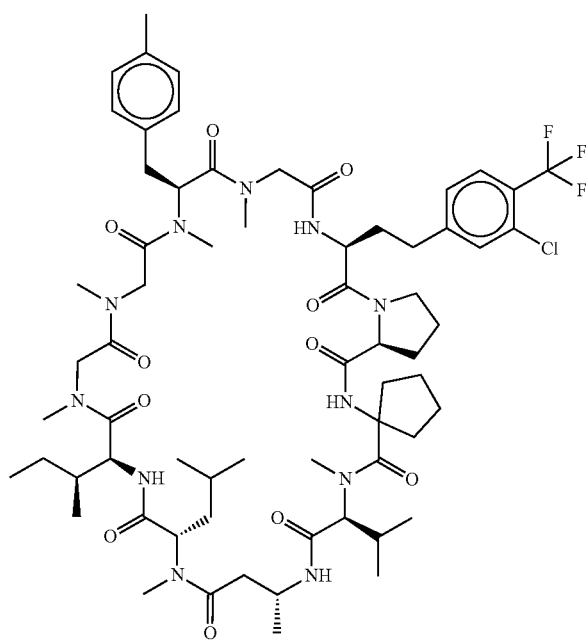 |

TABLE 24-continued
| Compound No. | Structural formula |
|---|---|
| 1633 | 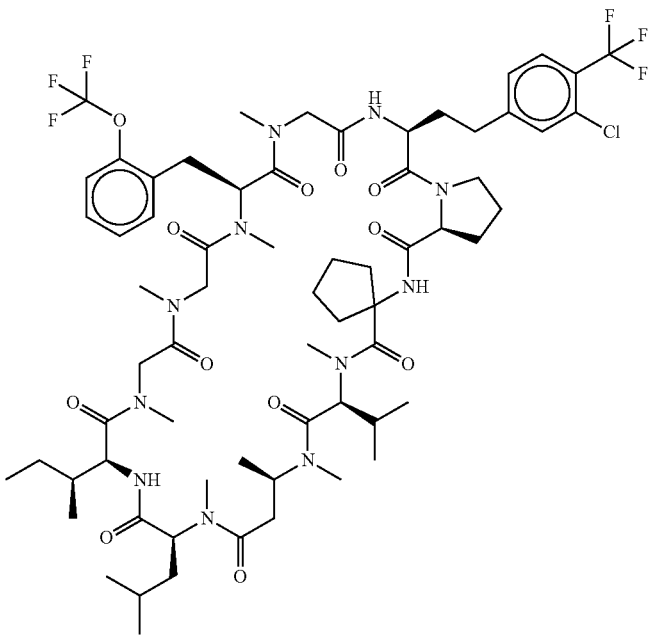 |
| 1634 | 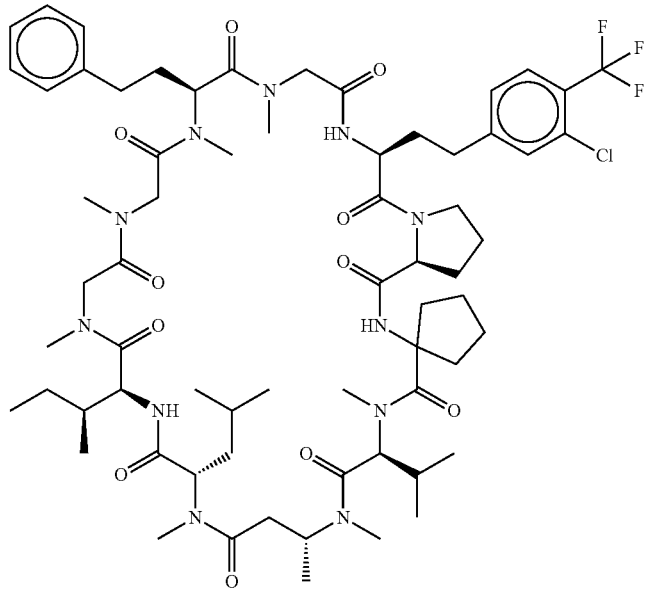 |

TABLE 24-continued
| Compound No. | Structural formula |
|---|---|
| 1635 | 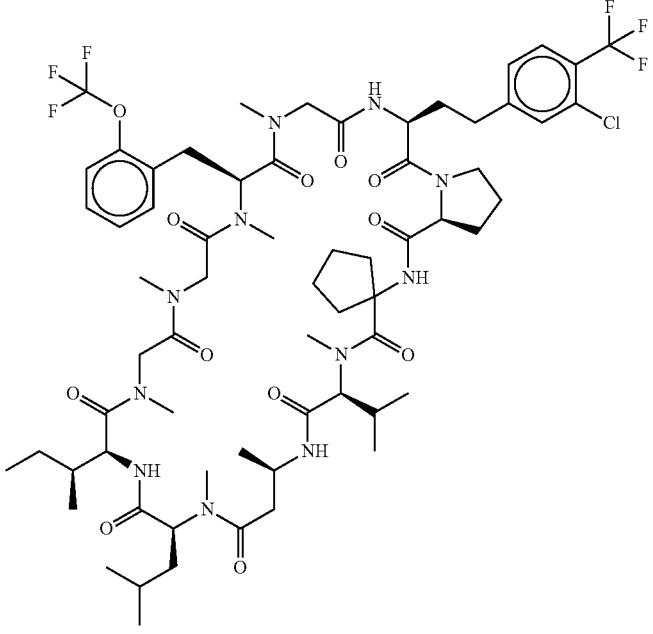 |
| 1636 | 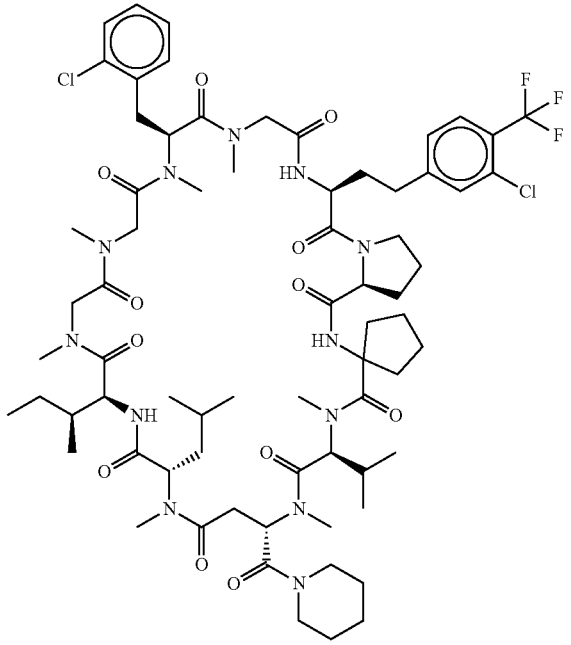 |

TABLE 24-continued
| Compound No. | Structural formula |
|---|---|
| 1637 | 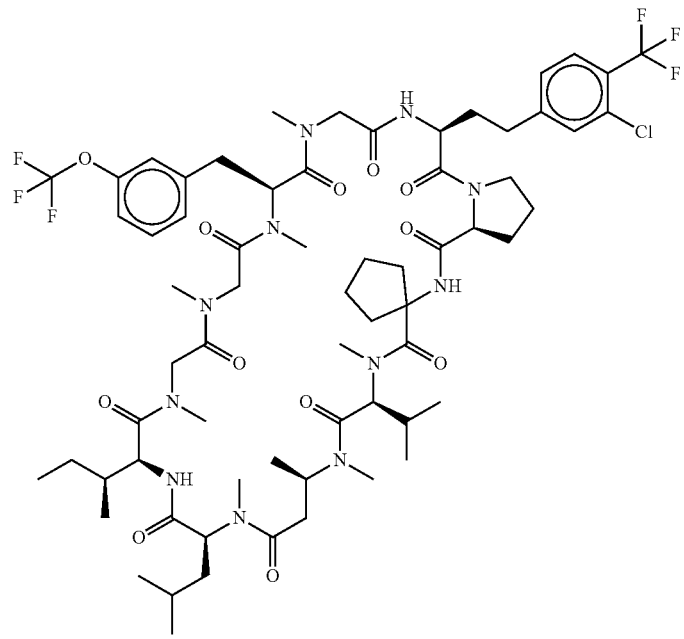 |
| 1638 | 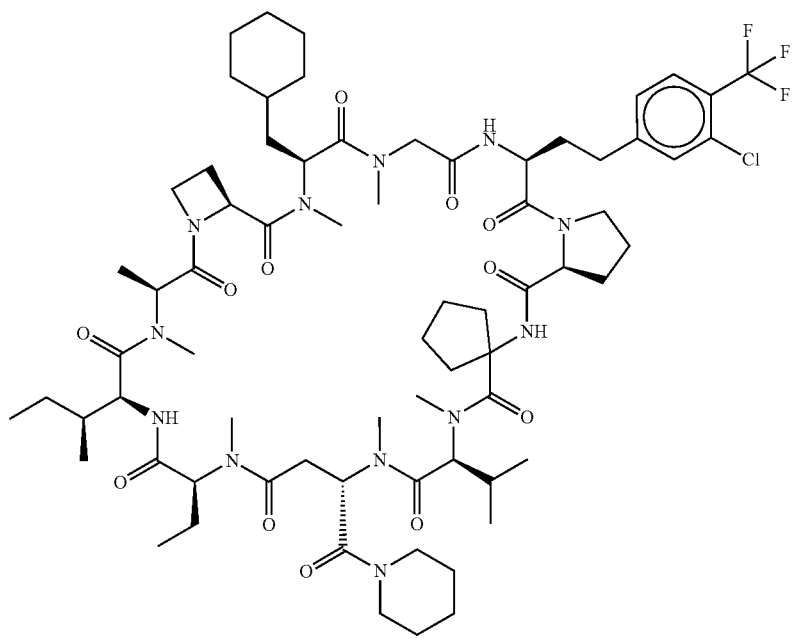 |

TABLE 24-continued
| Compound No. | Structural formula |
|---|---|
| 1639 | 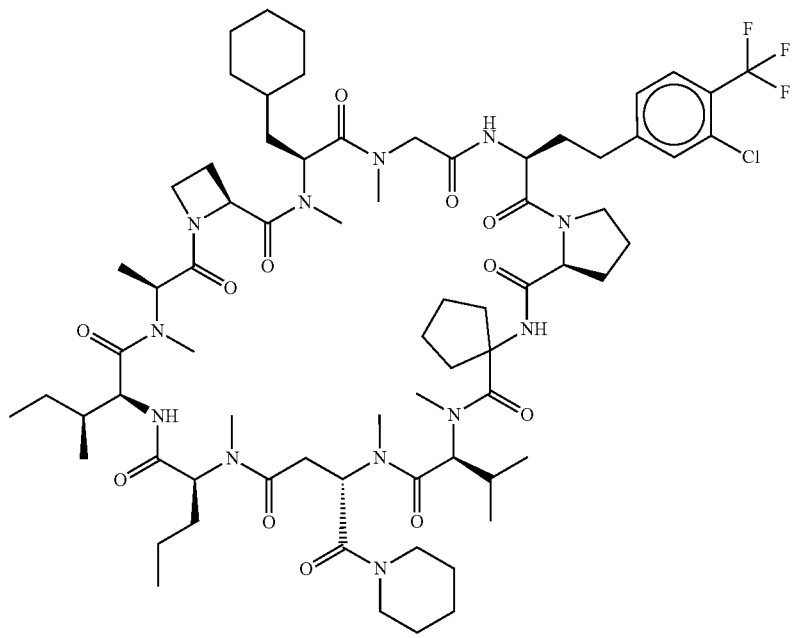 |
| 1640 | 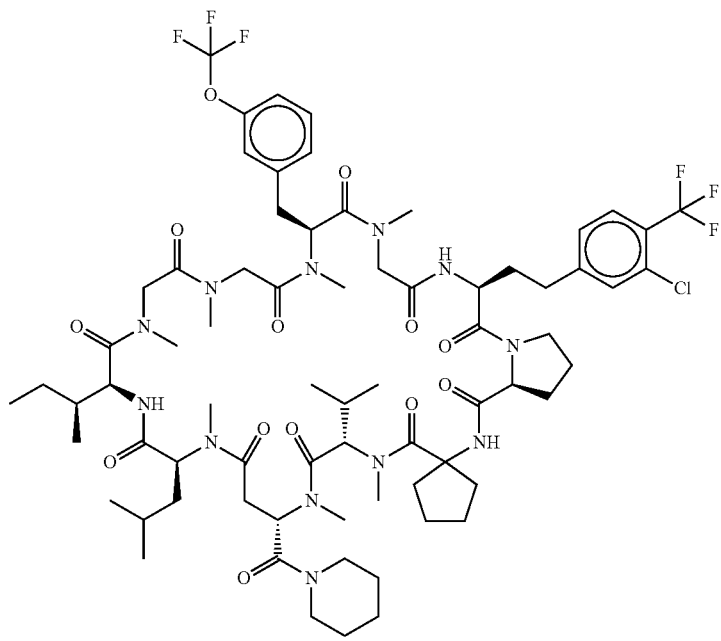 |

TABLE 24-continued
| Compound No. | Structural formula |
|---|---|
| 1641 | 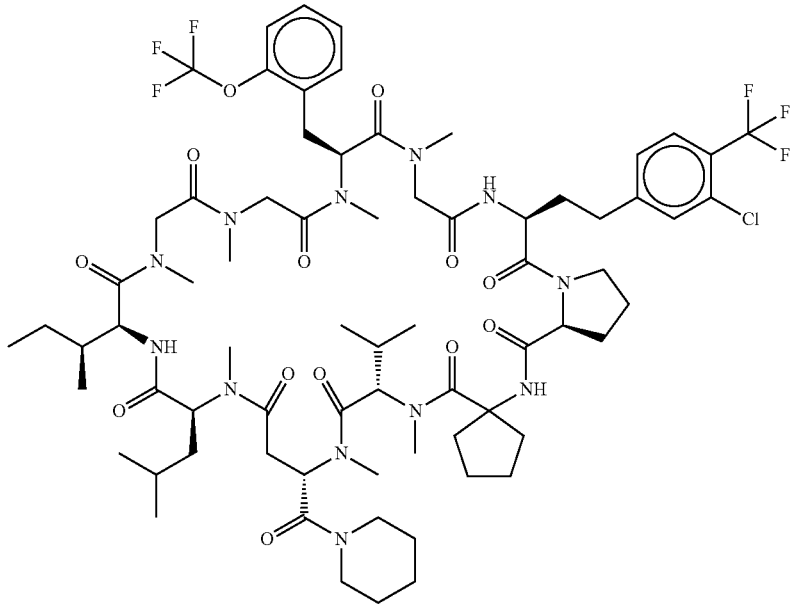 |
| 1642 | 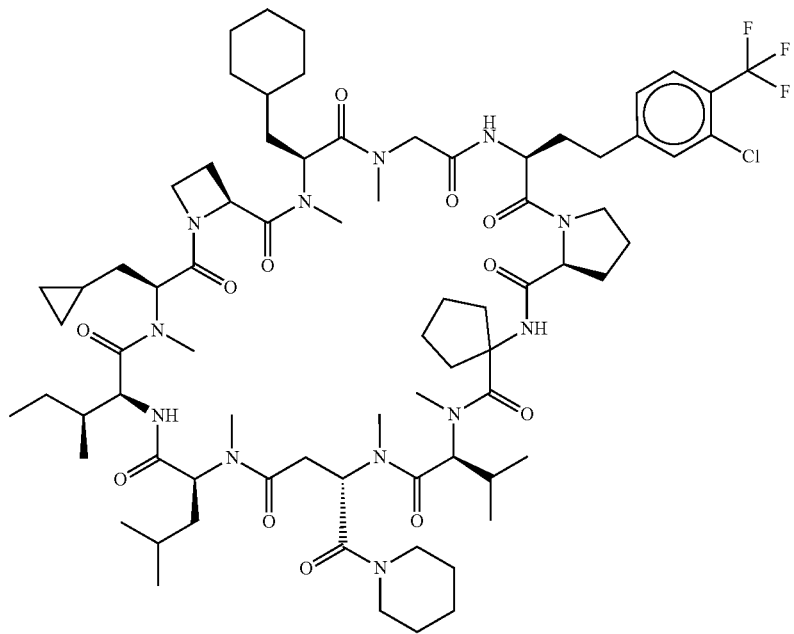 |

TABLE 24-continued
| Compound No. | Structural formula |
|---|---|
| 1643 | 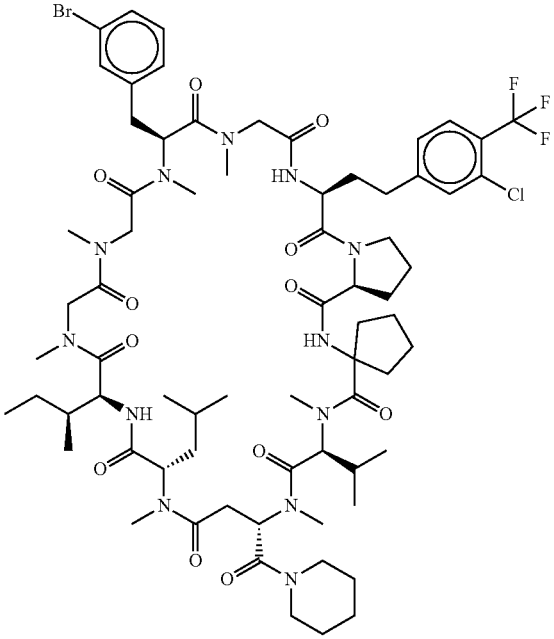 |
| 1644 | 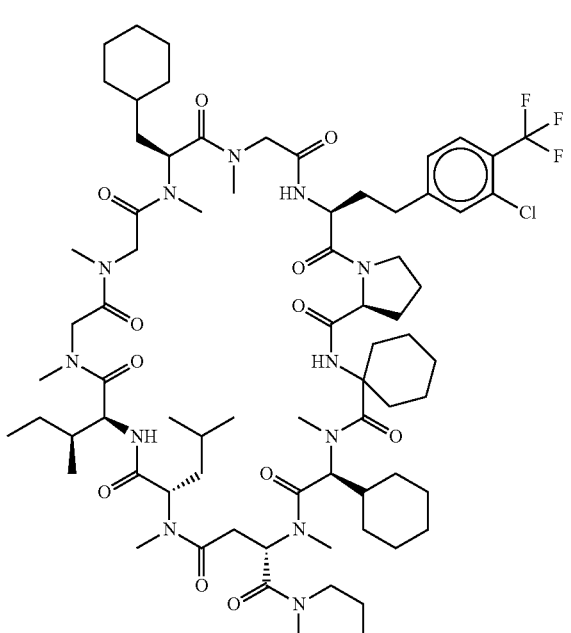 |

TABLE 24-continued
| Compound No. | Structural formula |
|---|---|
| 1645 | 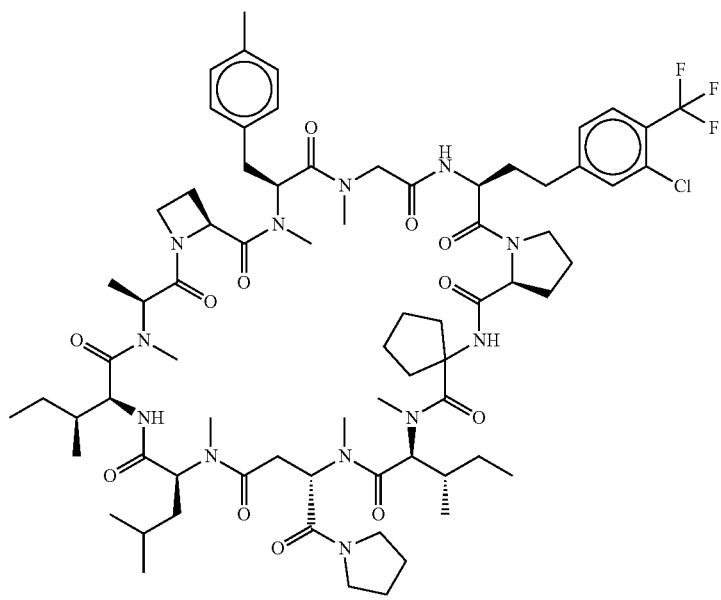 |
| 1646 | 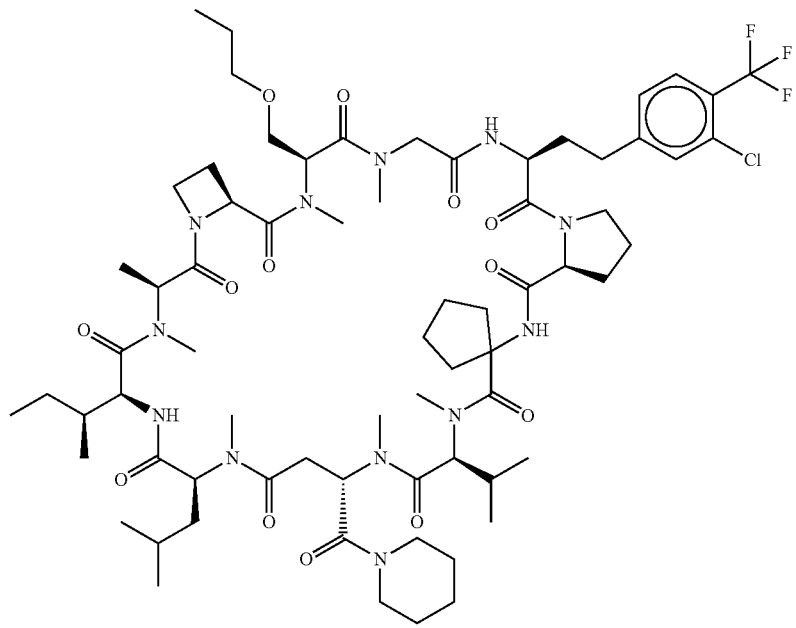 |

TABLE 24-continued
| Compound No. | Structural formula |
| --- | --- |
| 1647 | 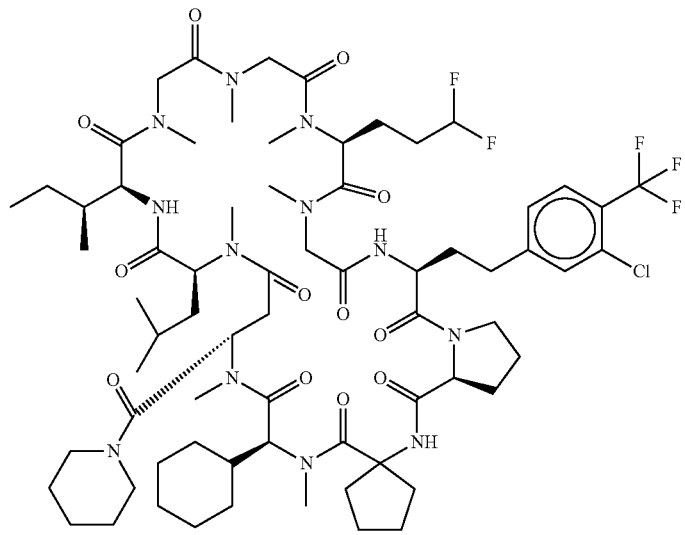 |
| 1648 | 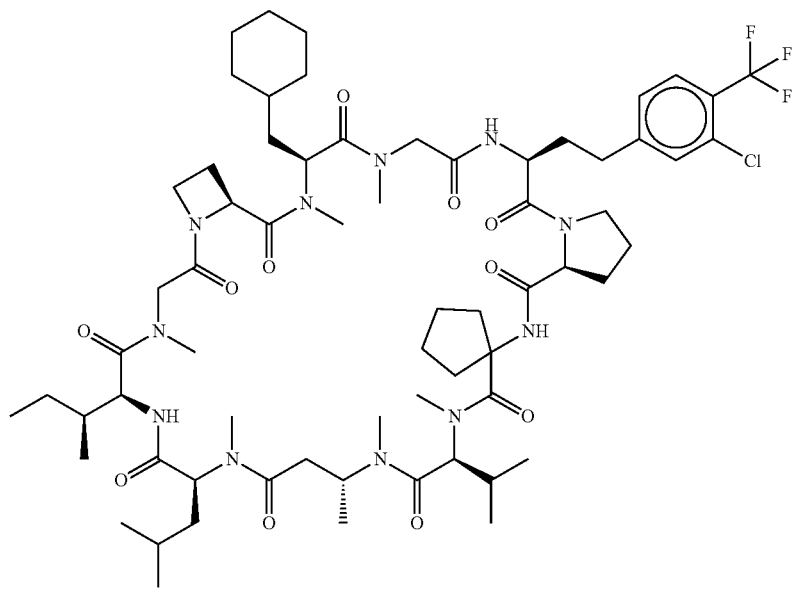 |

TABLE 24-continued
| Compound No. | Structural formula |
|---|---|
| 1649 | 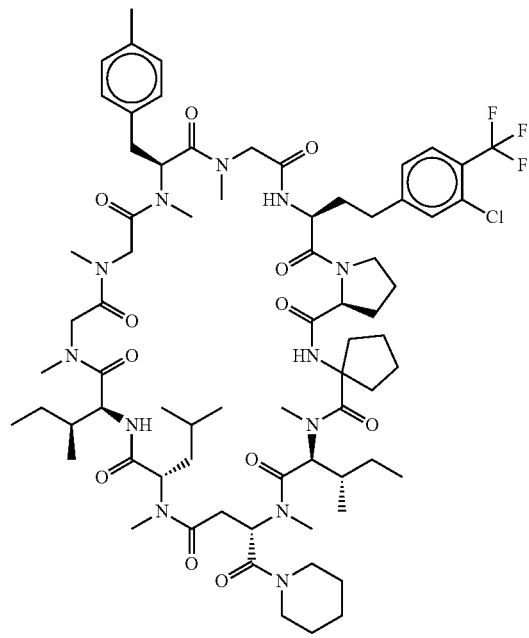 |
| 1650 | 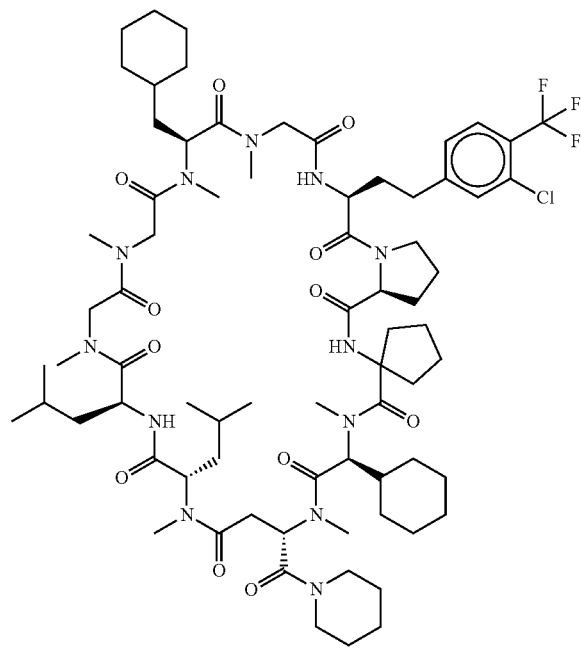 |

TABLE 24-continued
| Compound No. | Structural formula |
|---|---|
| 1651 | 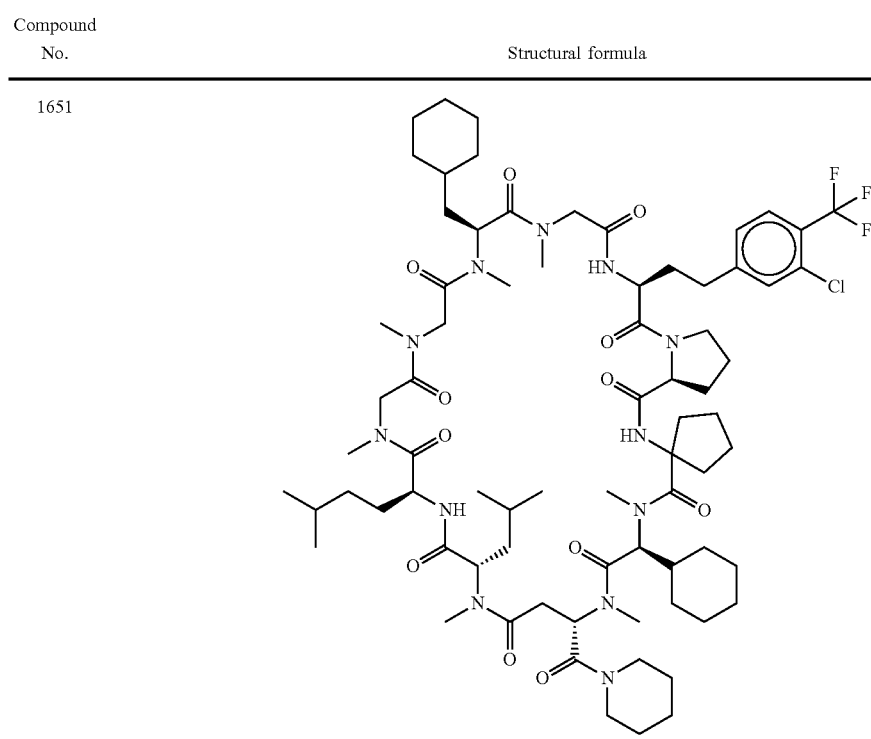 |
| 1652 | 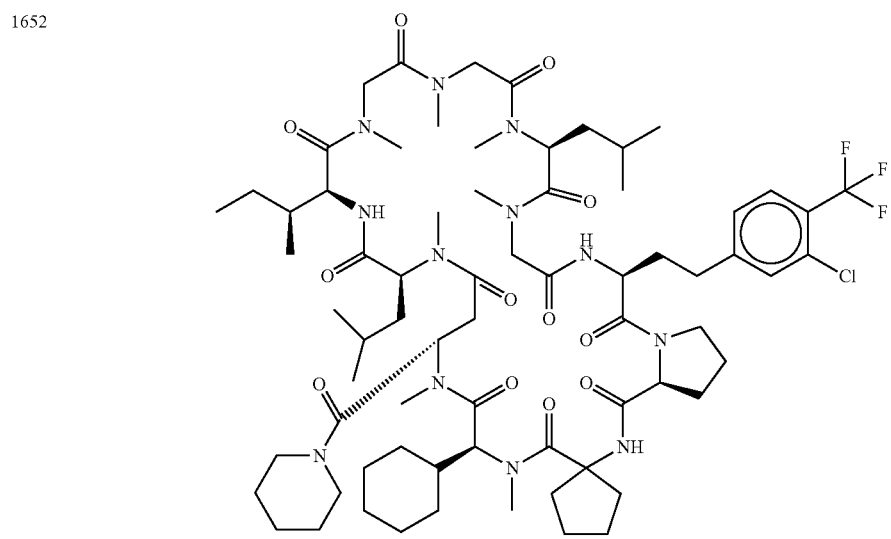 |

TABLE 24-continued
| Compound No. | Structural formula |
|---|---|
| 1653 | 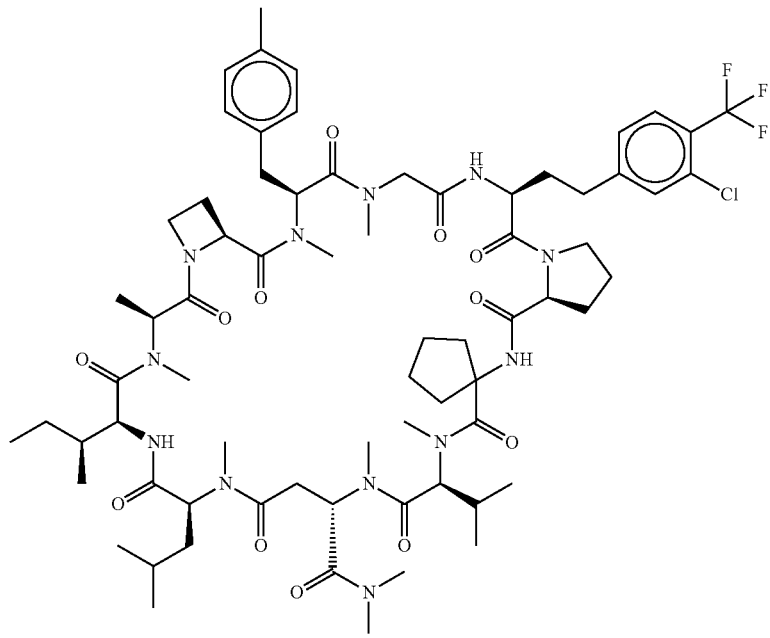 |
| 1654 | 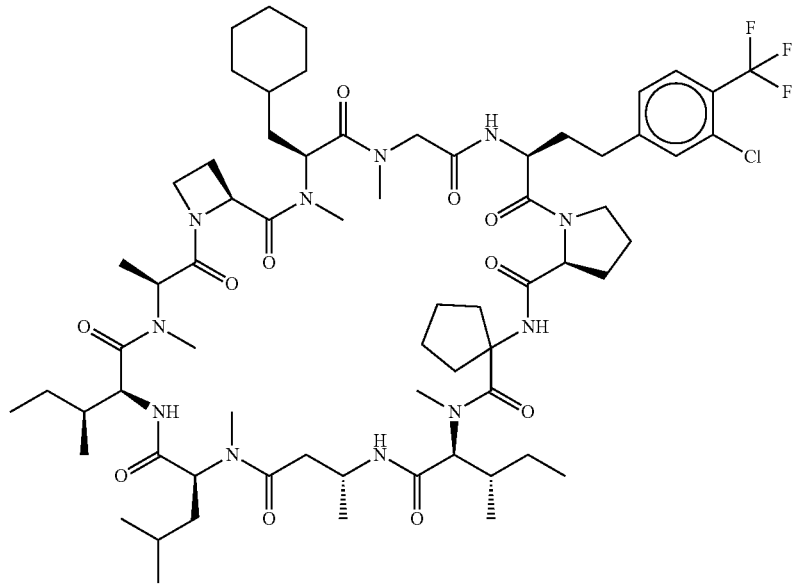 |

TABLE 24-continued
| Compound No. | Structural formula |
|---|---|
| 1655 | 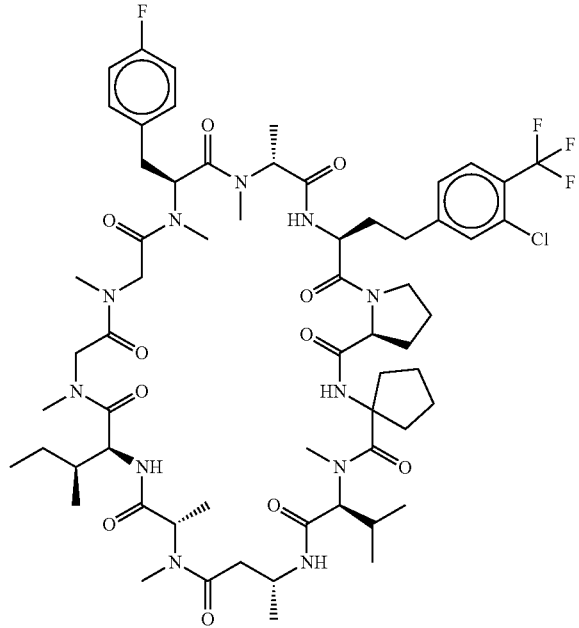 |
| 1656 | 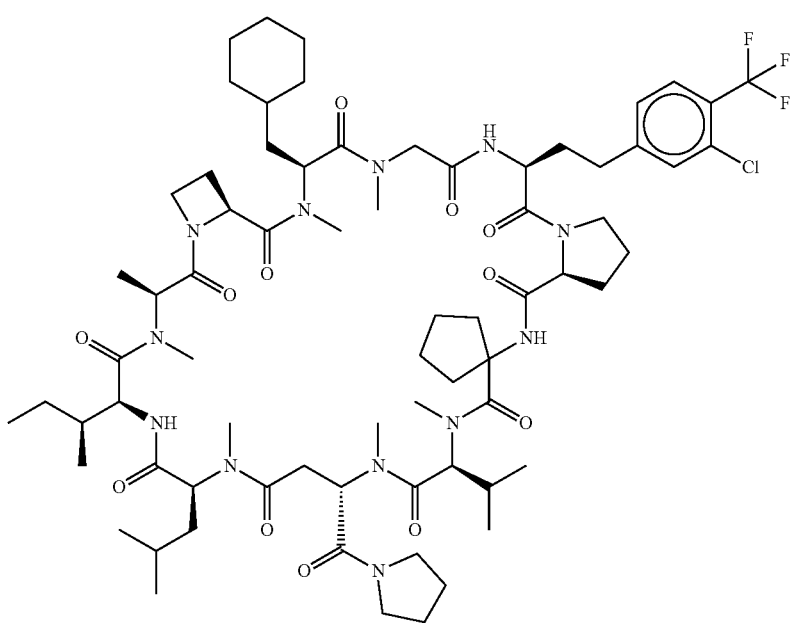 |

TABLE 24-continued
| Compound No. | Structural formula |
|---|---|
| 1657 | 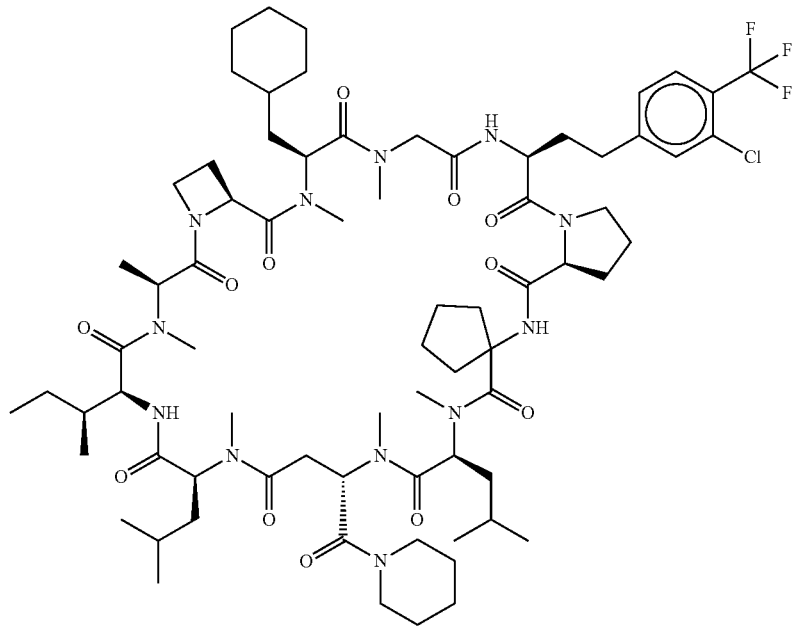 |
| 1658 | 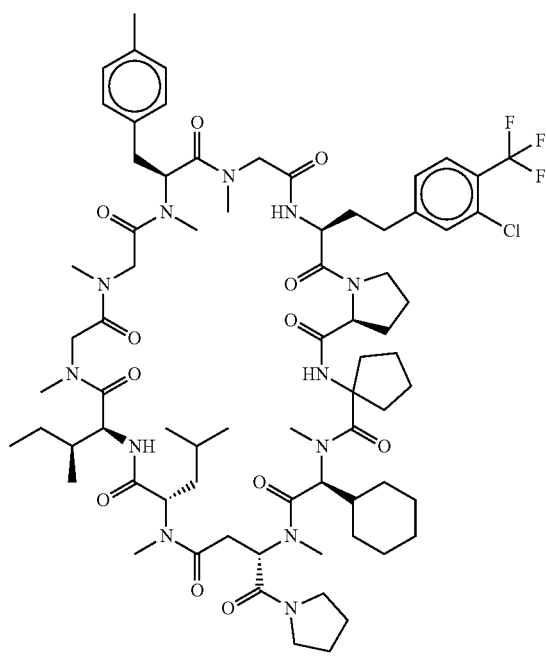 |

TABLE 24-continued
| Compound No. | Structural formula |
|---|---|
| 1659 | 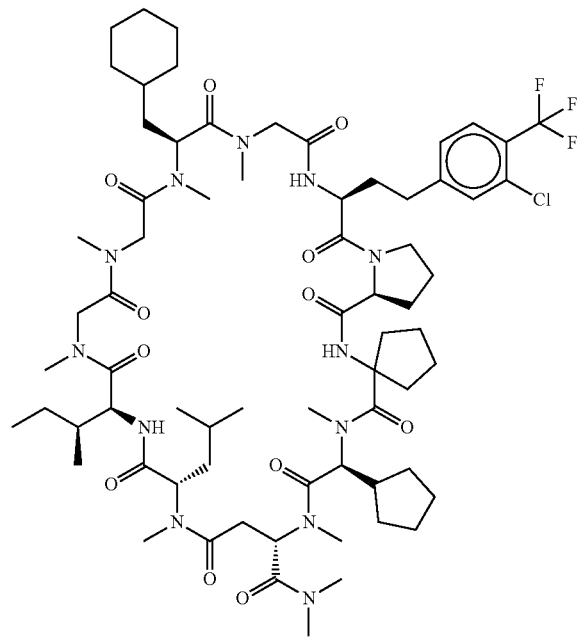 |
| 1660 | 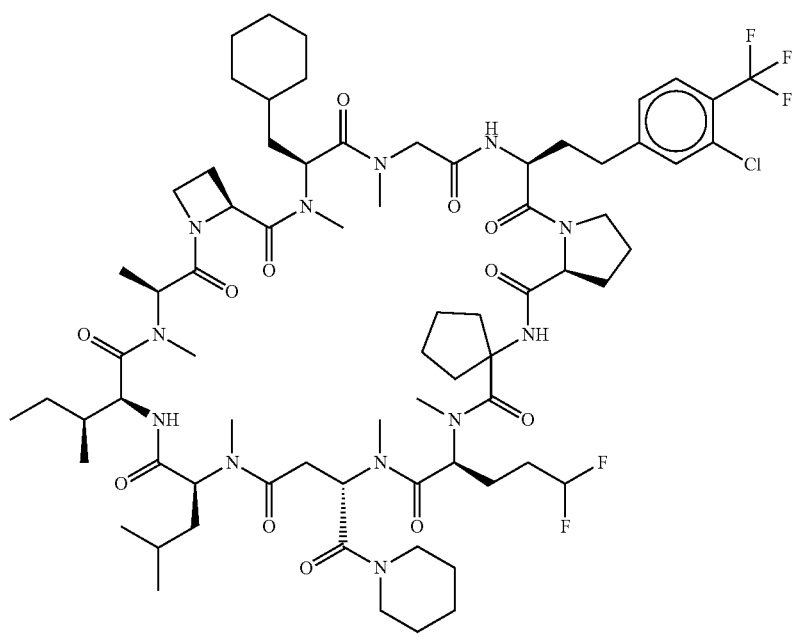 |

TABLE 24-continued
| Compound No. | Structural formula |
| --- | --- |
| 1661 | 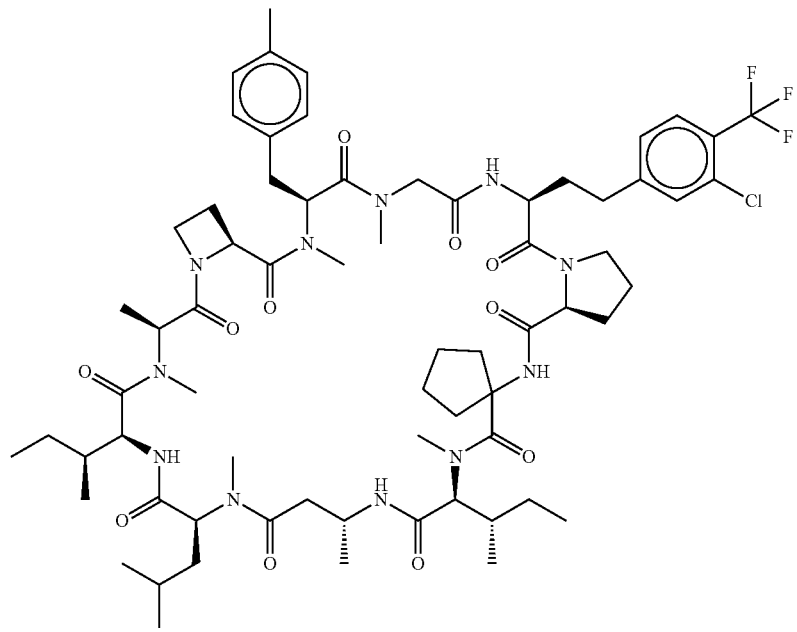 |
| 1662 | 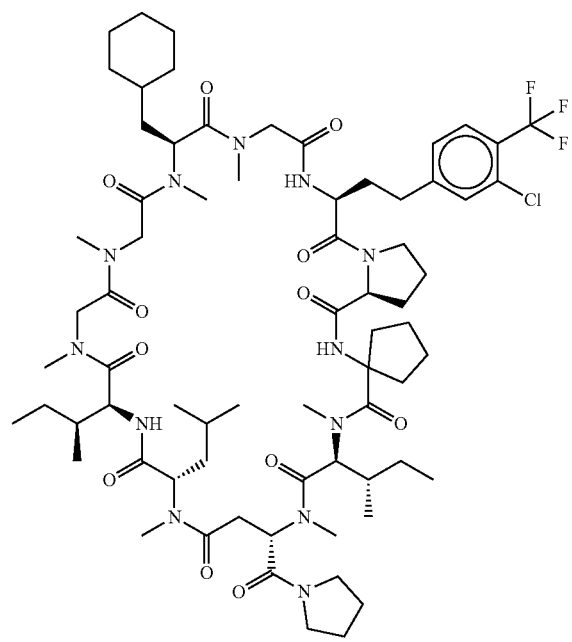 |

TABLE 24-continued
| Compound No. | Structural formula |
|---|---|
| 1663 | 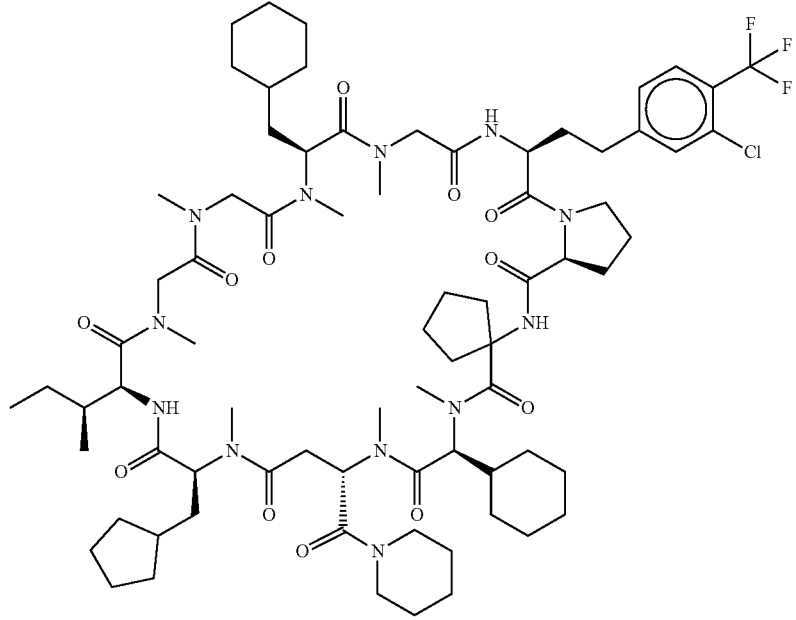 |
| 1664 | 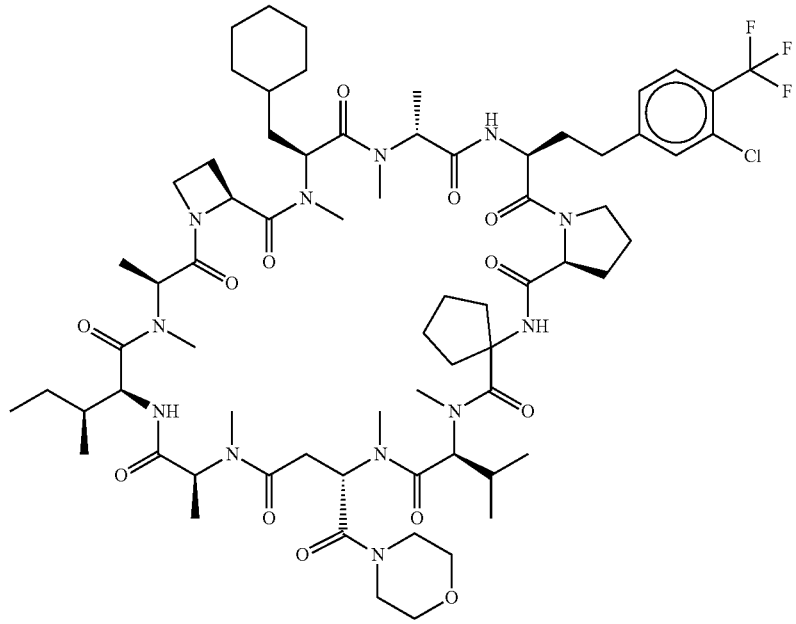 |

TABLE 24-continued
| Compound No. | Structural formula |
|---|---|
| 1665 | 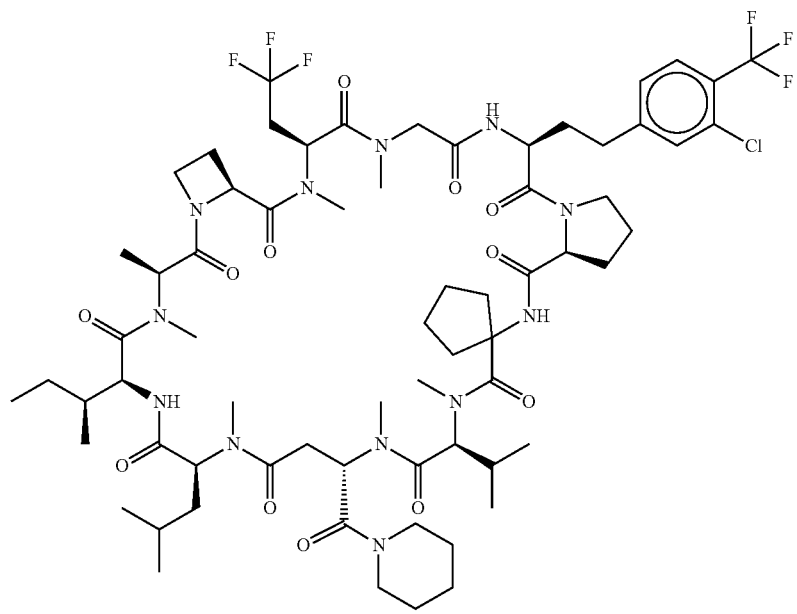 |
| 1666 | 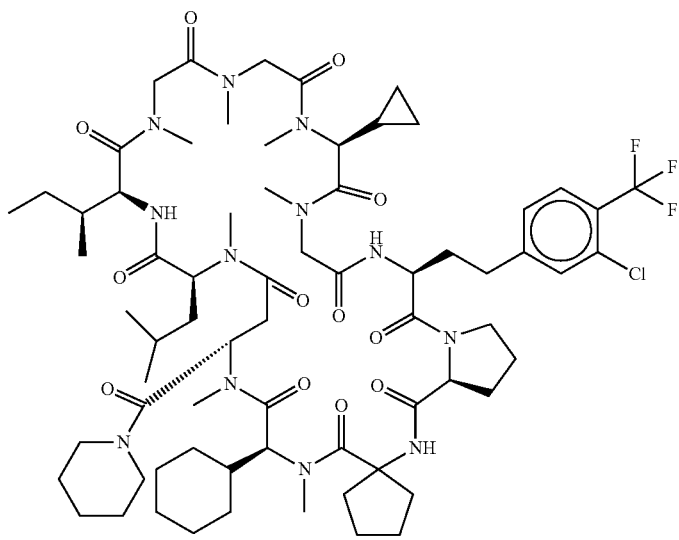 |

TABLE 24-continued
| Compound No. | Structural formula |
|---|---|
| 1667 | 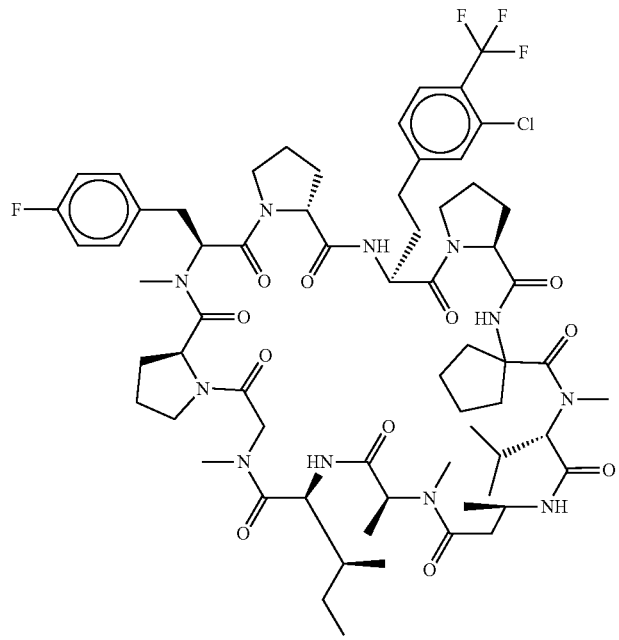 |
| 1668 | 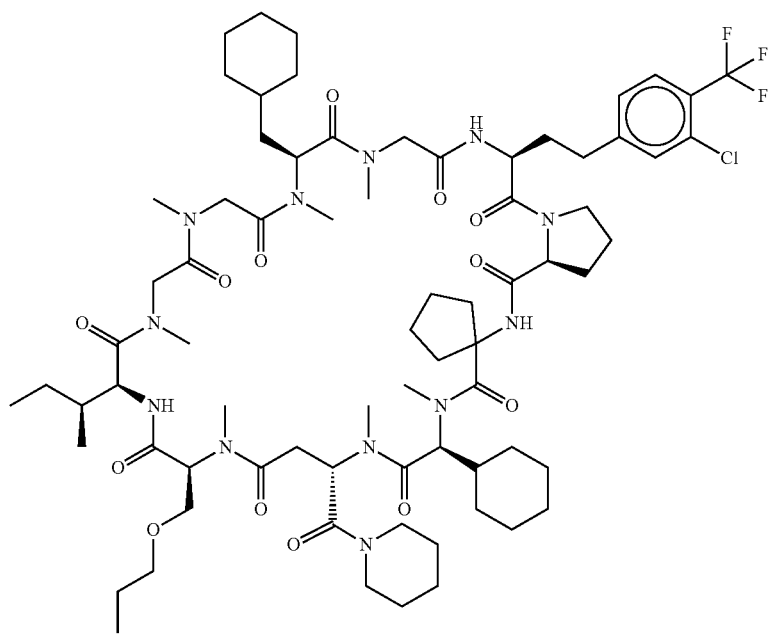 |

US 12,371,454 B2
TABLE 24-continued
| Compound No. | Structural formula |
|---|---|
| 1669 | 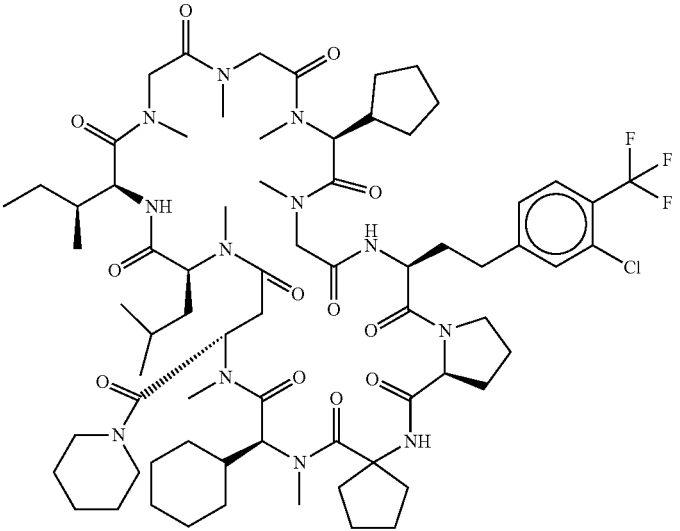 |
| 1670 | 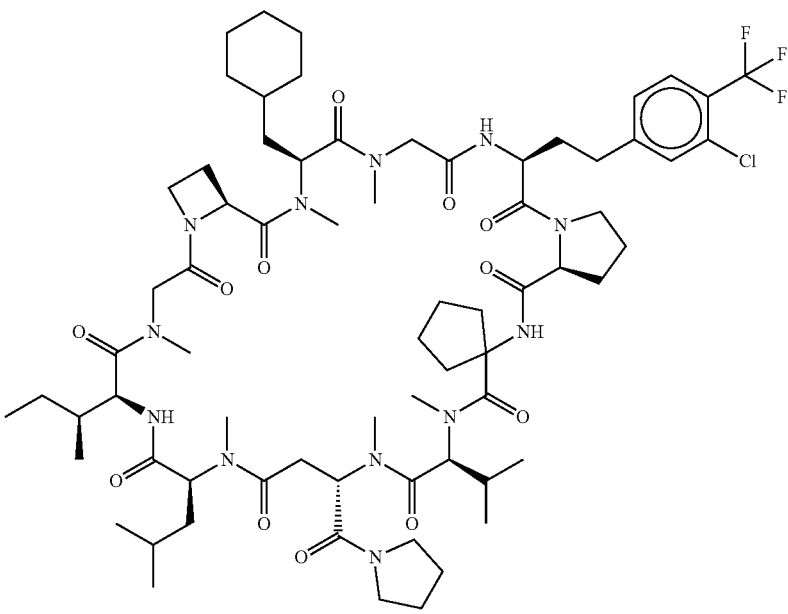 |

TABLE 24-continued
| Compound No. | Structural formula |
|---|---|
| 1671 | 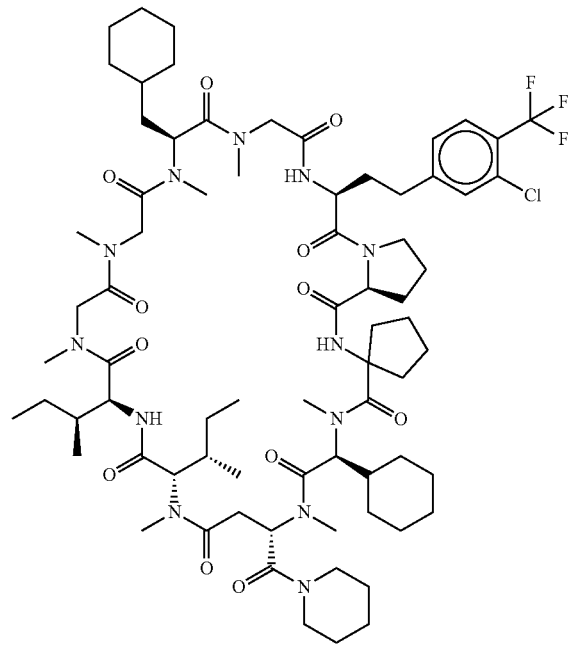 |
| 1672 | 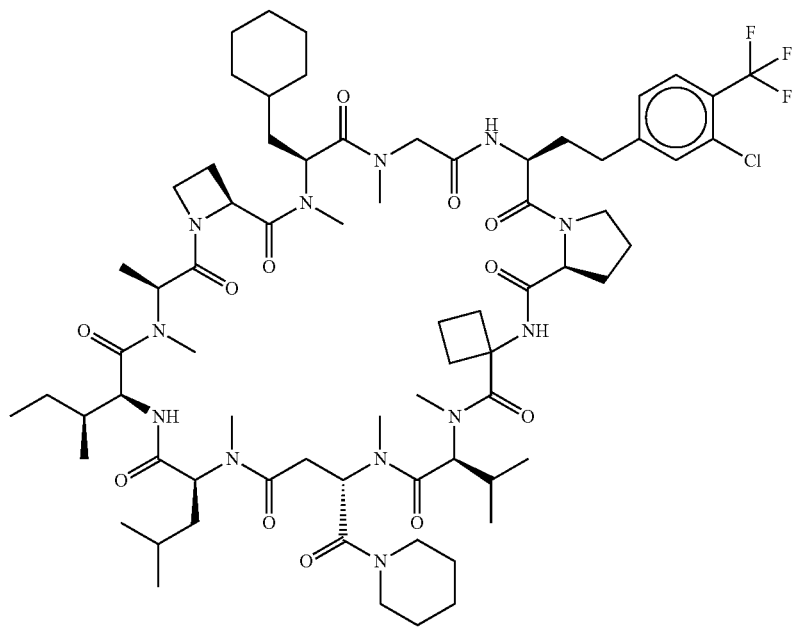 |

TABLE 24-continued
| Compound No. | Structural formula |
|---|---|
| 1673 | 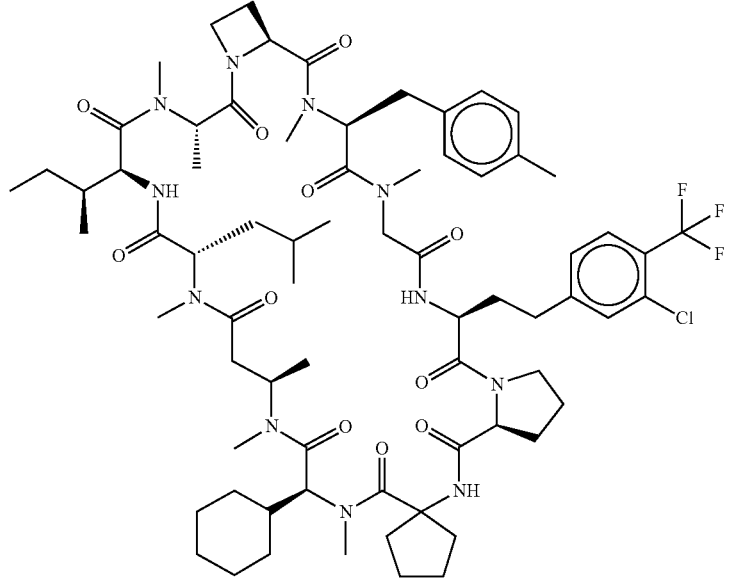 |
| 1674 | 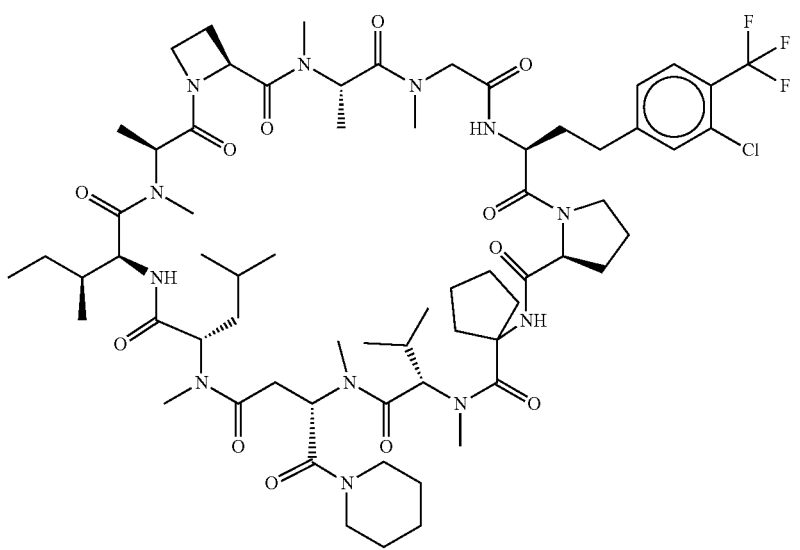 |

TABLE 24-continued
| Compound No. | Structural formula |
|---|---|
| 1675 | 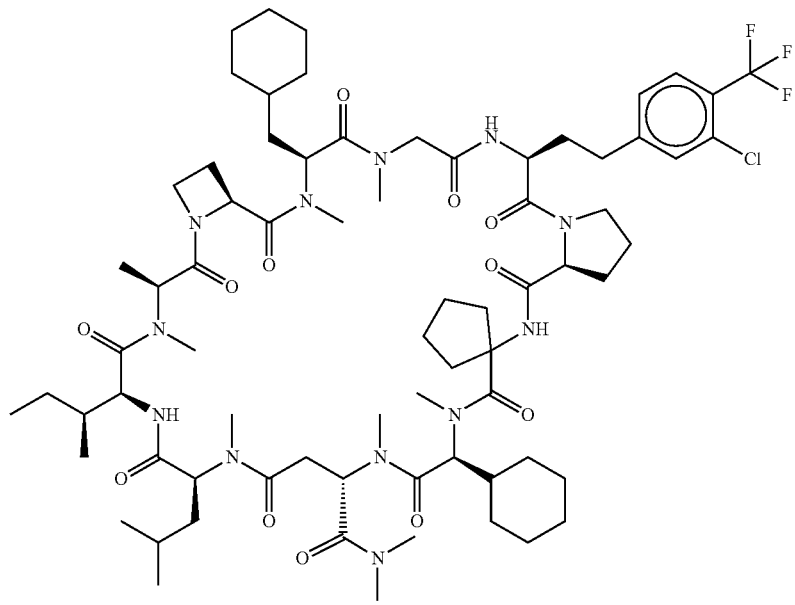 |
| 1676 | 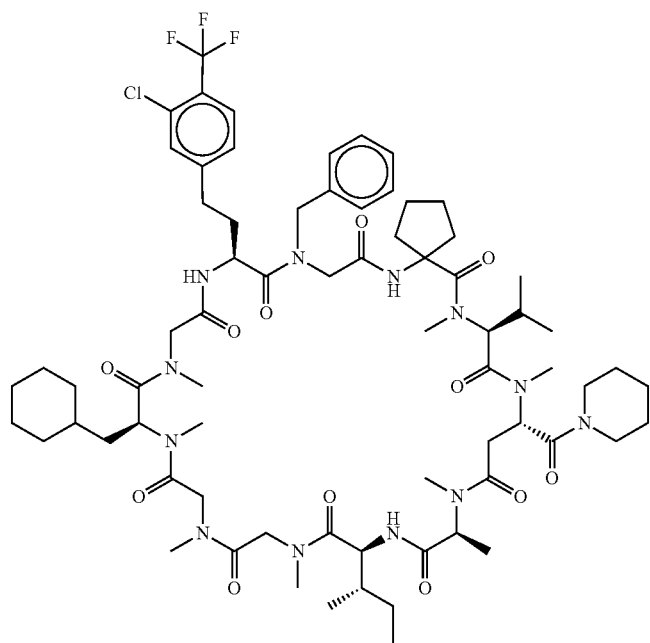 |

TABLE 24-continued
| Compound No. | Structural formula |
|---|---|
| 1677 | 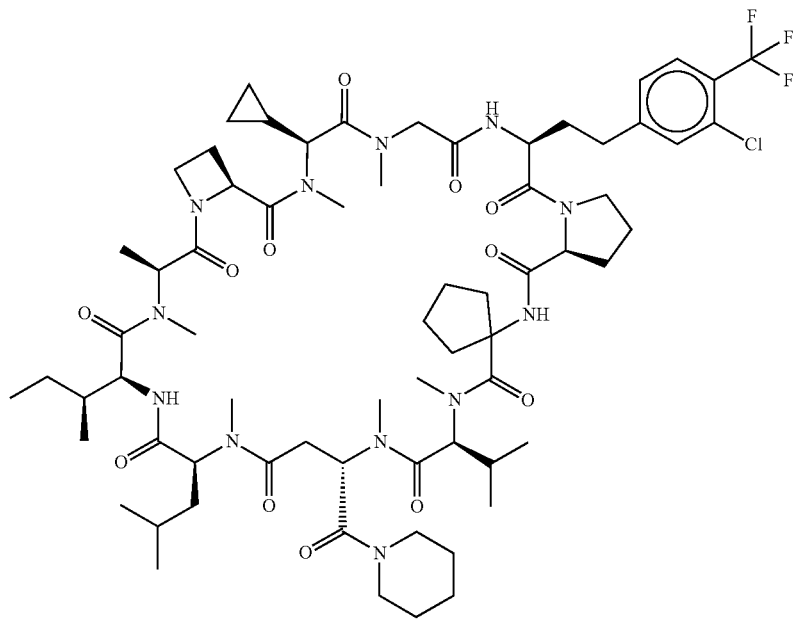 |
| 1678 | 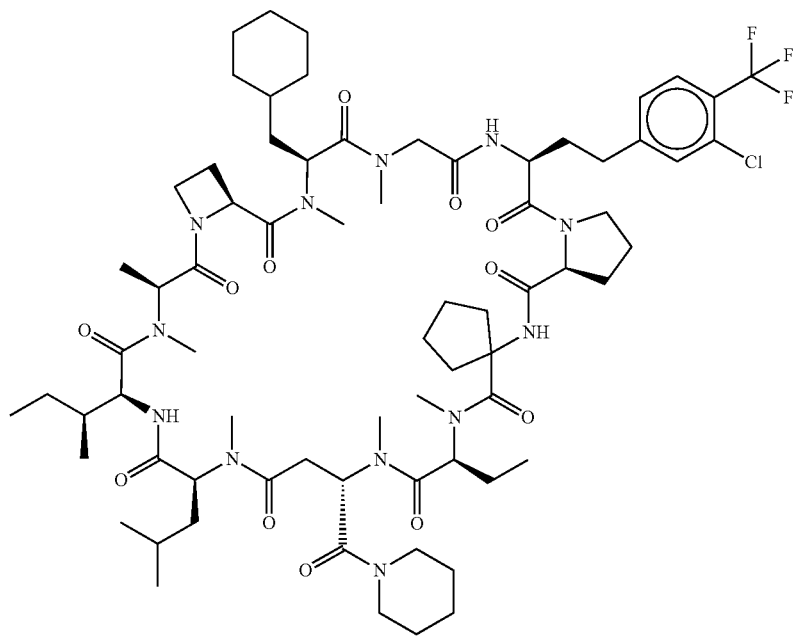 |

TABLE 24-continued
| Compound No. | Structural formula |
|---|---|
| 1679 | 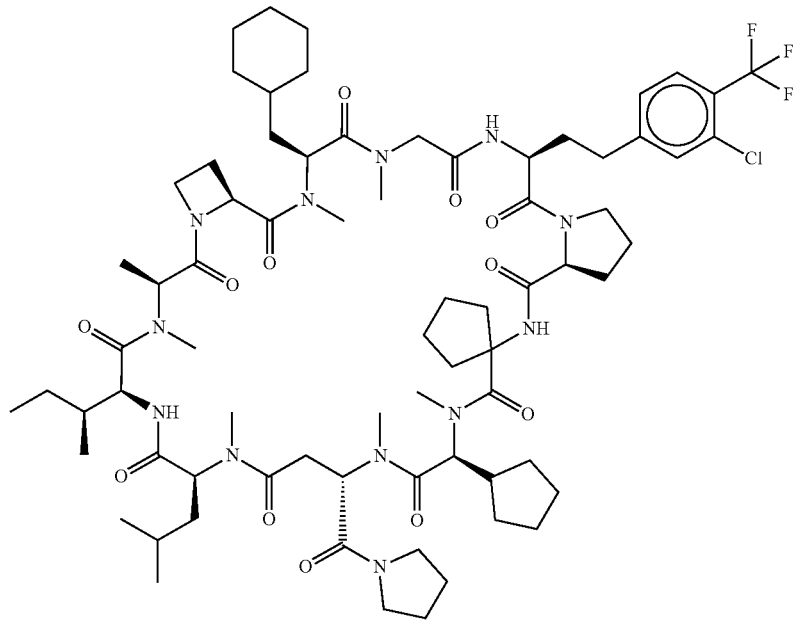 |
| 1680 | 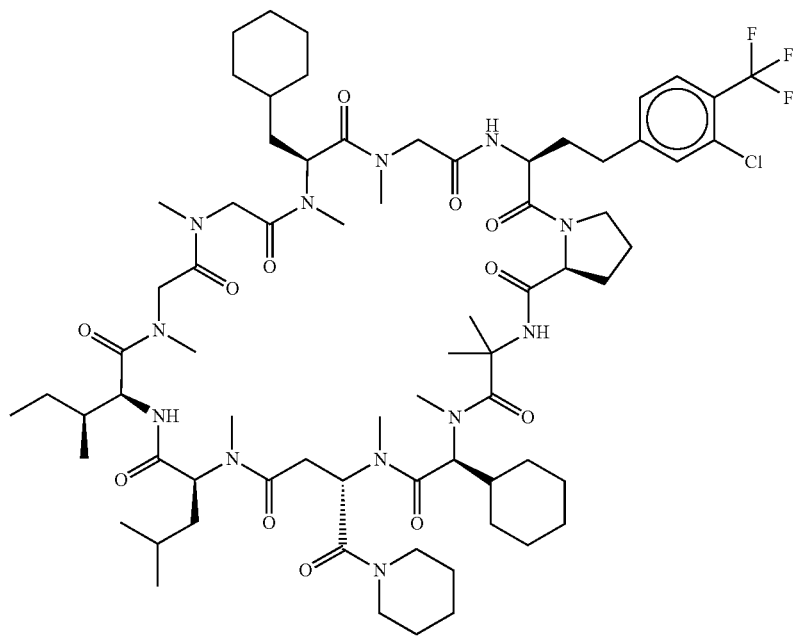 |

TABLE 24-continued
| Compound No. | Structural formula |
|---|---|
| 1681 | 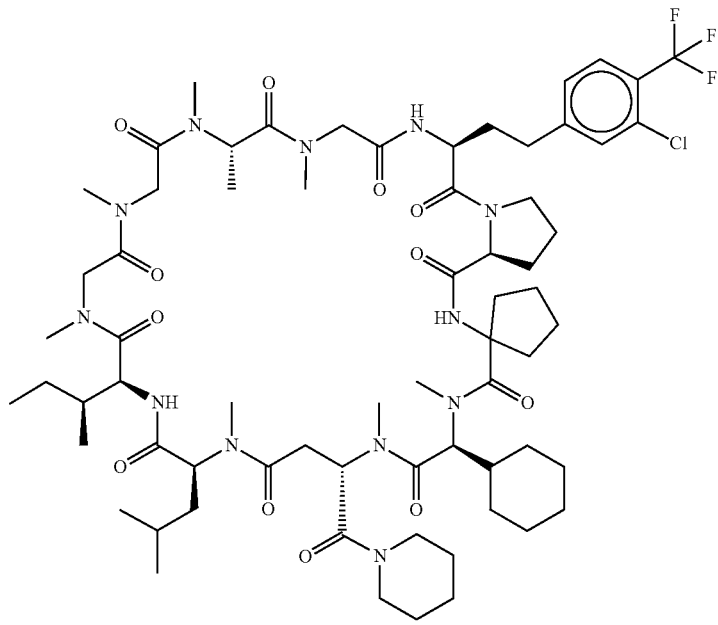 |
| 1682 | 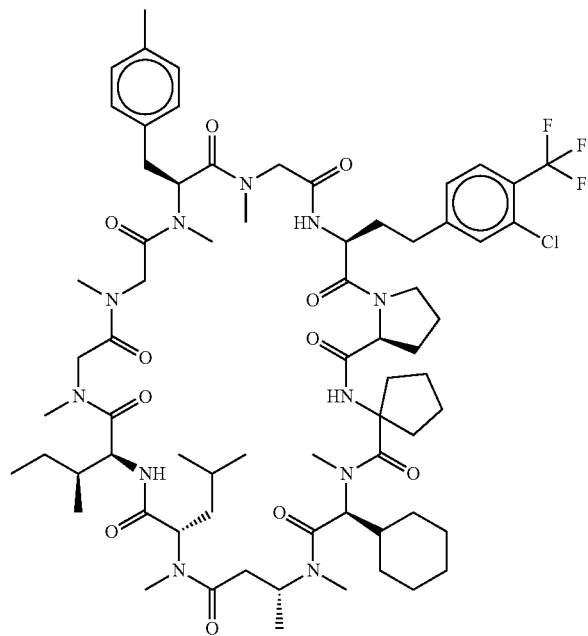 |

TABLE 24-continued
| Compound No. | Structural formula |
|---|---|
| 1683 | 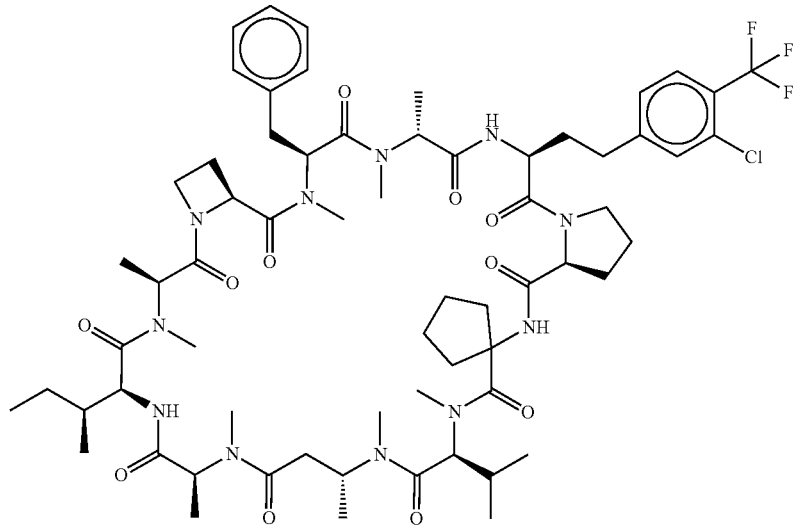 |
| 1684 | 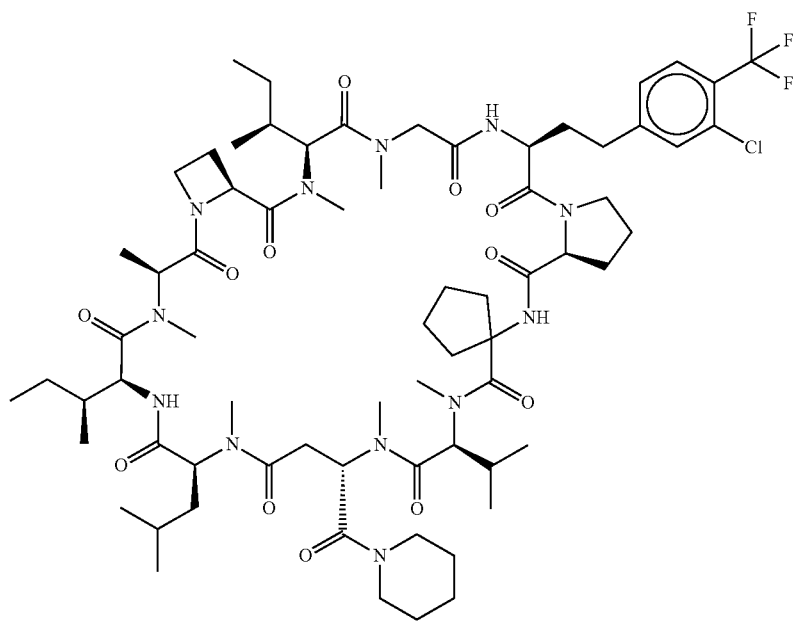 |

TABLE 24-continued
| Compound No. | Structural formula |
|---|---|
| 1685 | 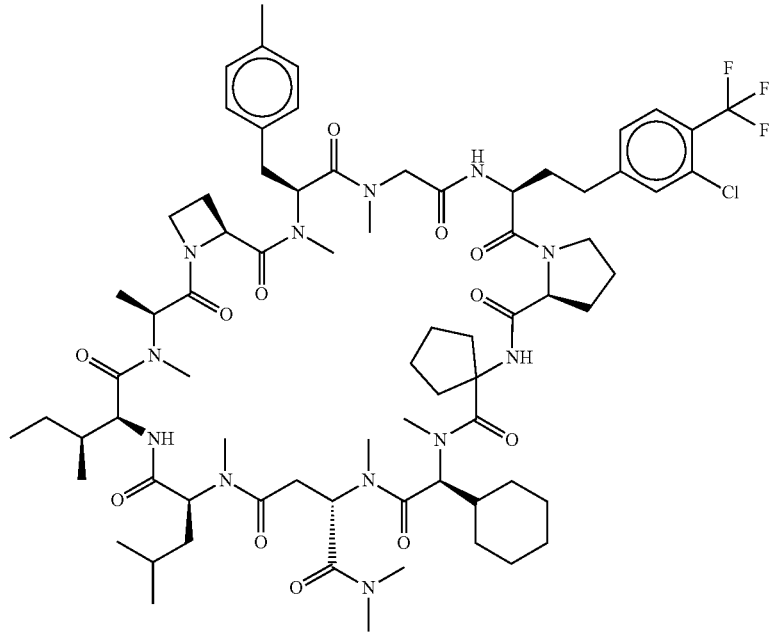 |
| 1686 | 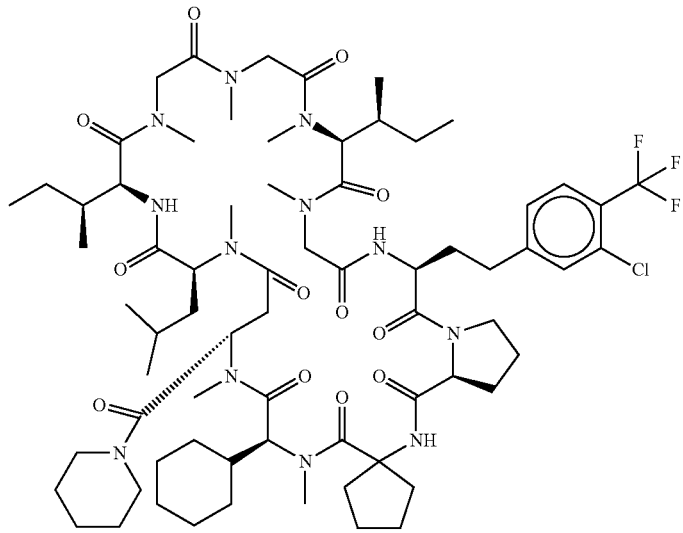 |

TABLE 24-continued
| Compound No. | Structural formula |
|---|---|
| 1687 | 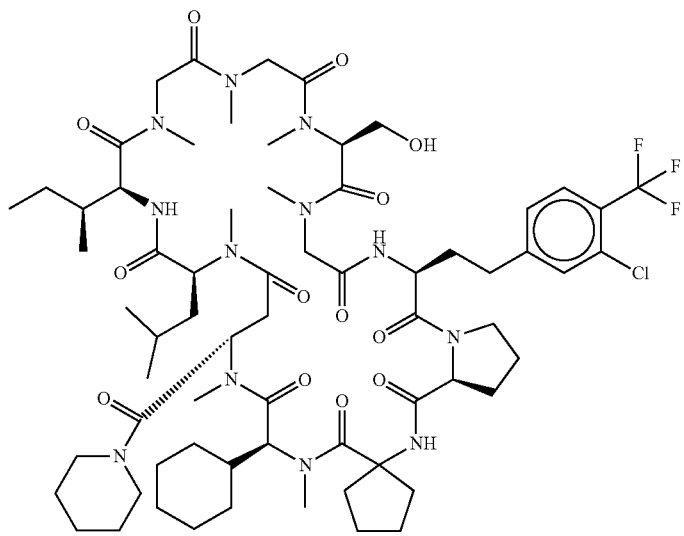 |
| 1688 | 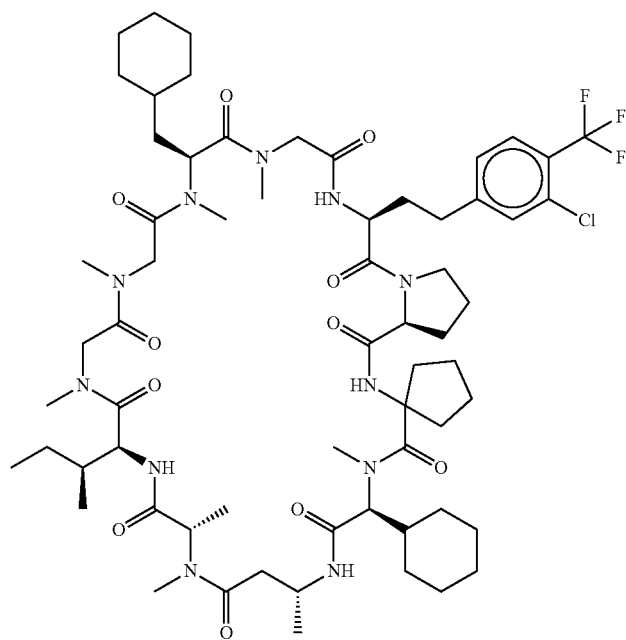 |

TABLE 24-continued
| Compound No. | Structural formula |
|---|---|
| 1689 | 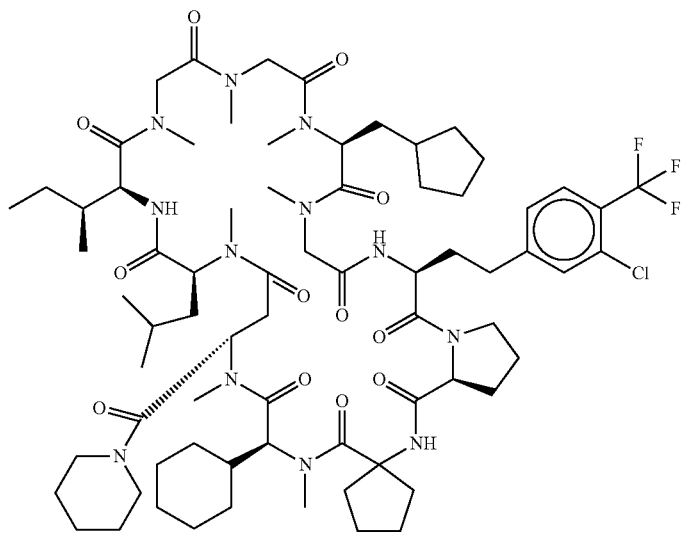 |
| 1690 | 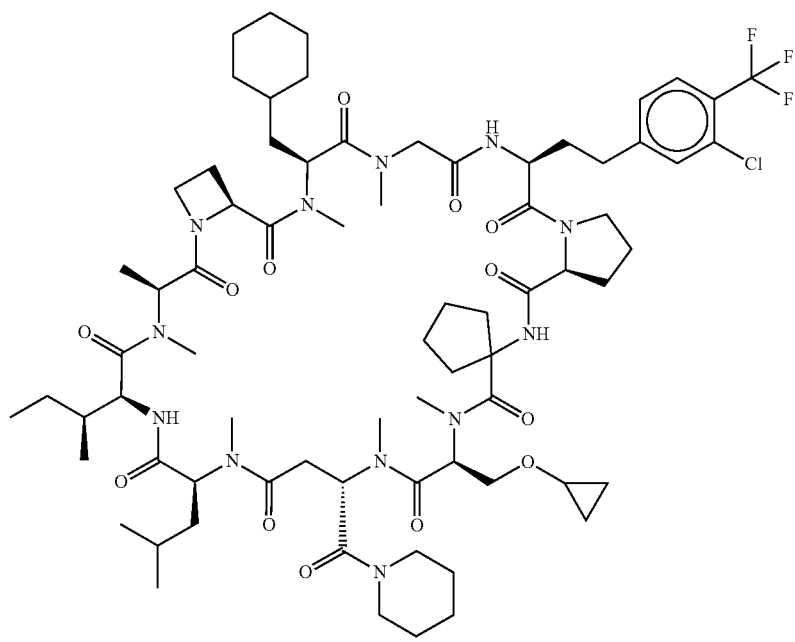 |

TABLE 24-continued
| Compound No. | Structural formula |
|---|---|
| 1691 | 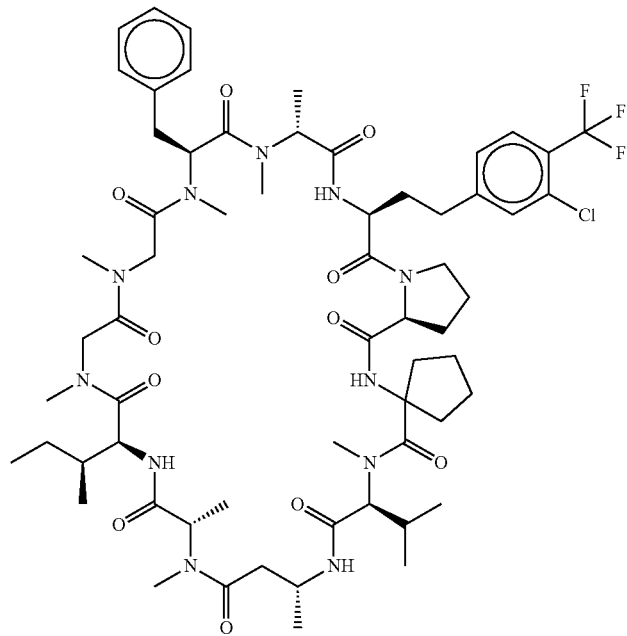 |
| 1692 | 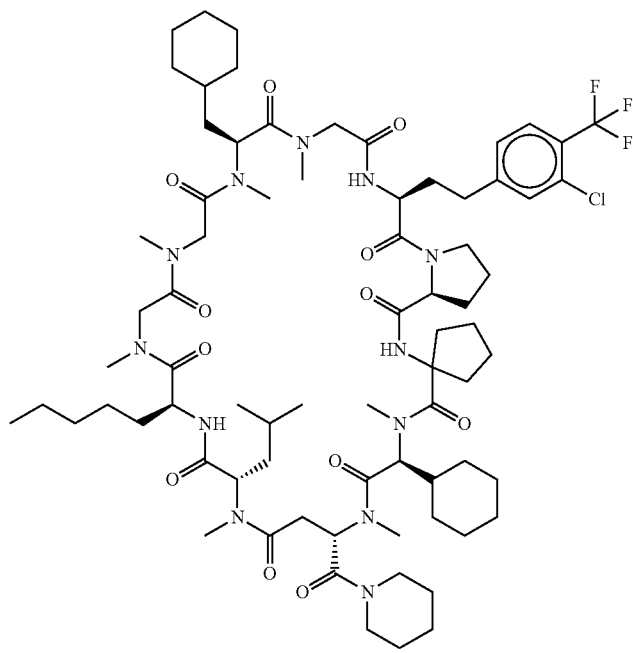 |

TABLE 24-continued
| Compound No. | Structural formula |
|---|---|
| 1693 | 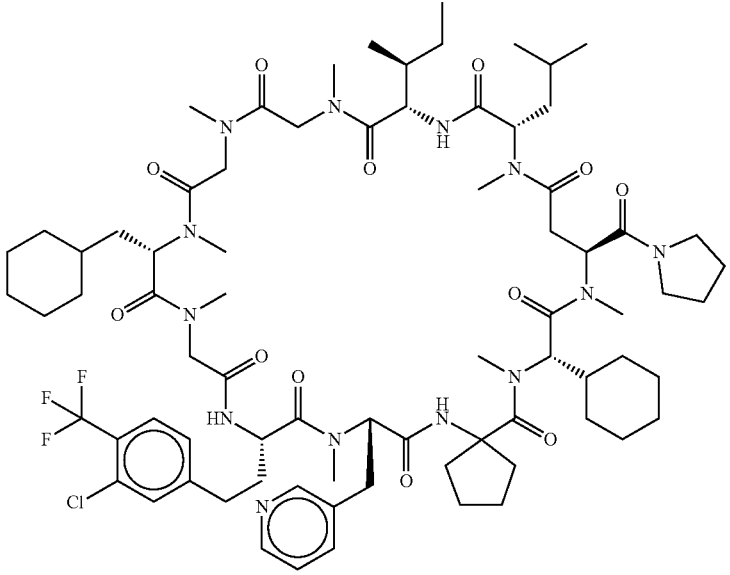 |
| 1694 | 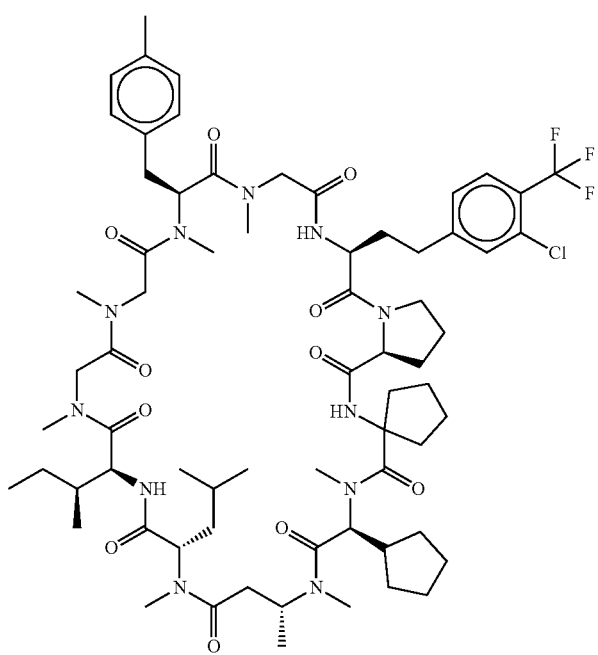 |

TABLE 24-continued
| Compound No. | Structural formula |
|---|---|
| 1695 | 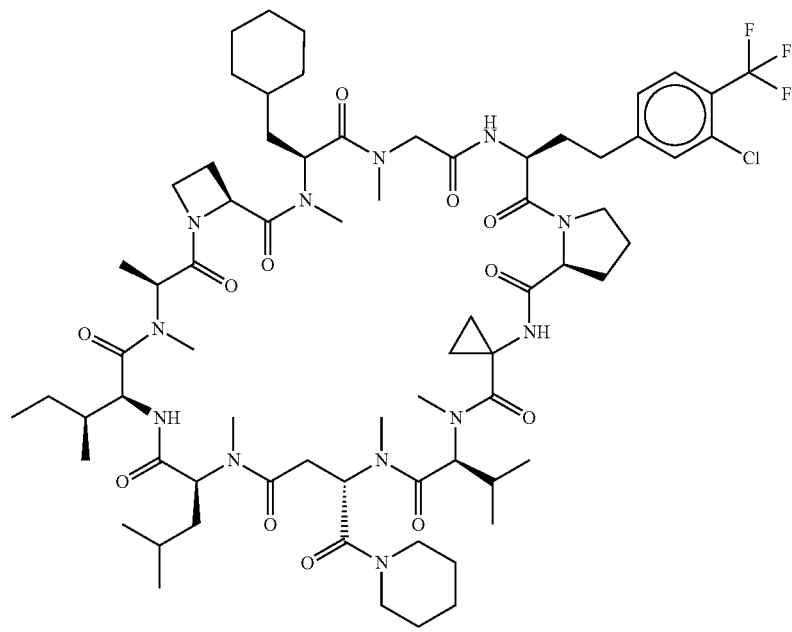 |
| 1696 | 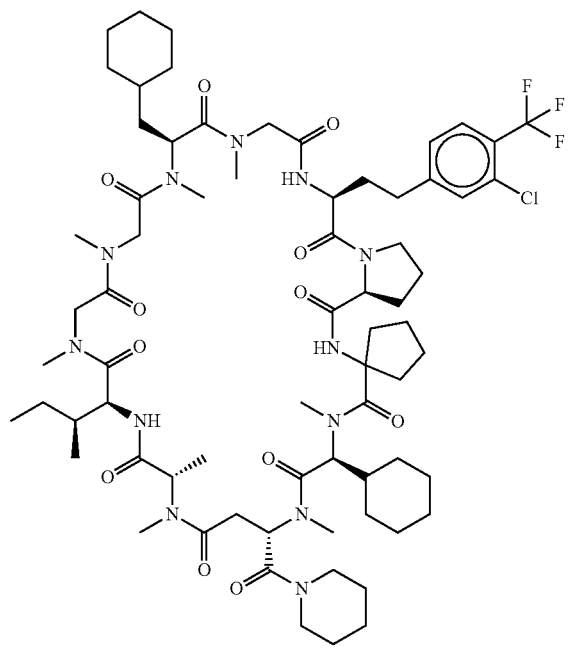 |

TABLE 24-continued
| Compound No. | Structural formula |
|---|---|
| 1697 | 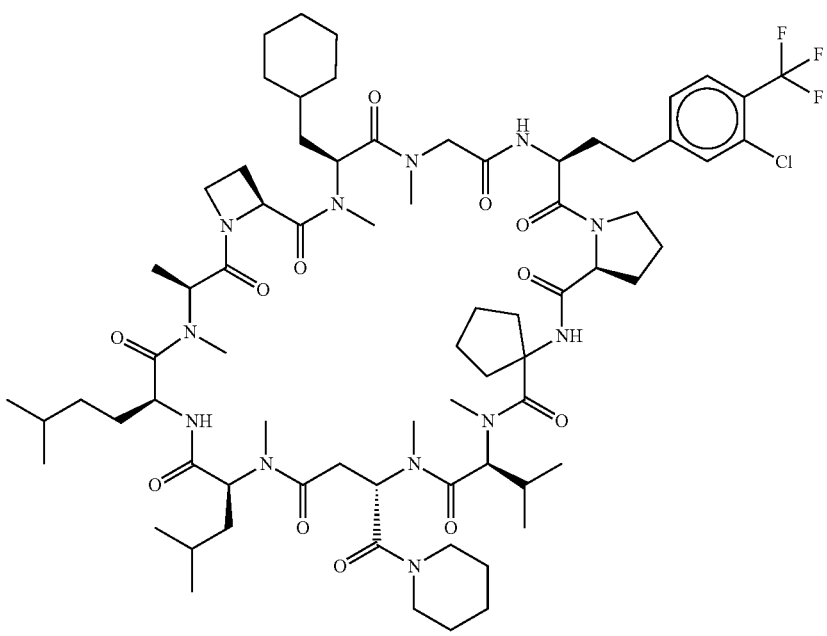 |
| 1698 | 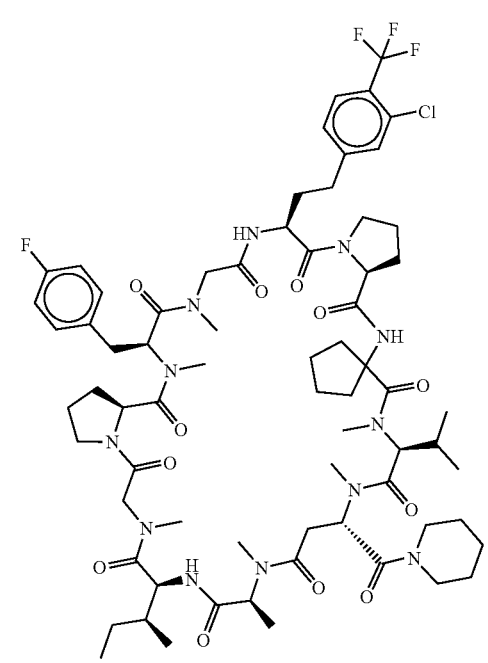 |

TABLE 24-continued
| Compound No. | Structural formula |
|---|---|
| 1699 | 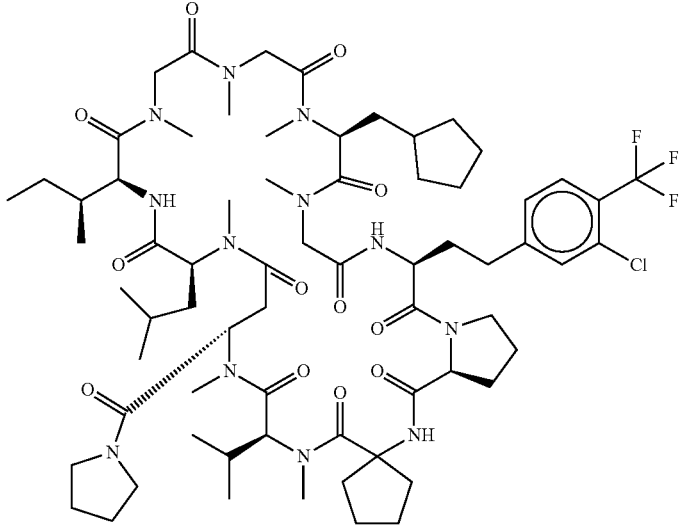 |
| 1700 | 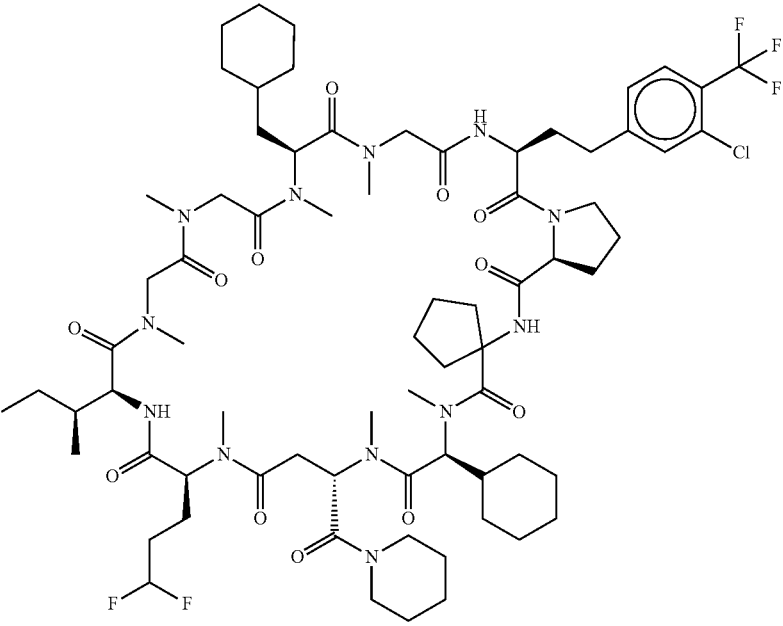 |

| Compound No. | Structural formula |
|---|---|
| 1701 | 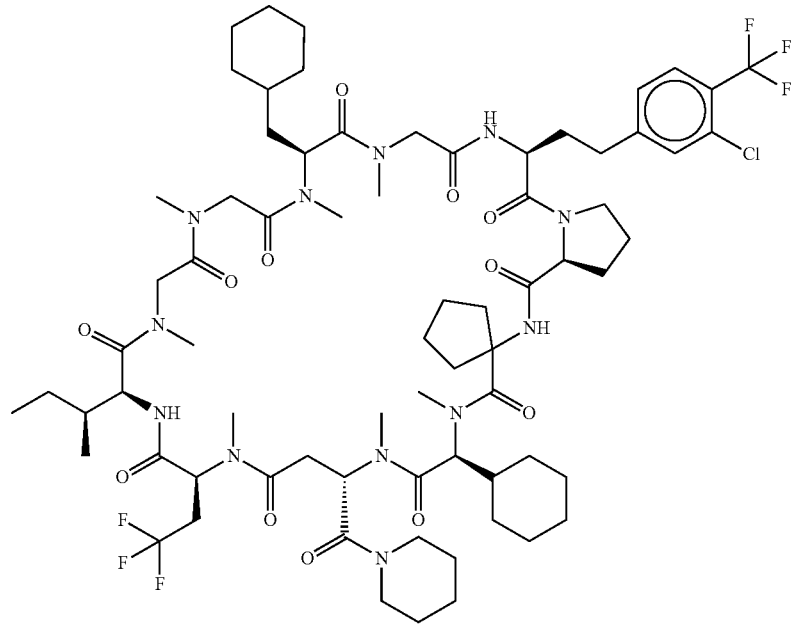 |
| 1702 | 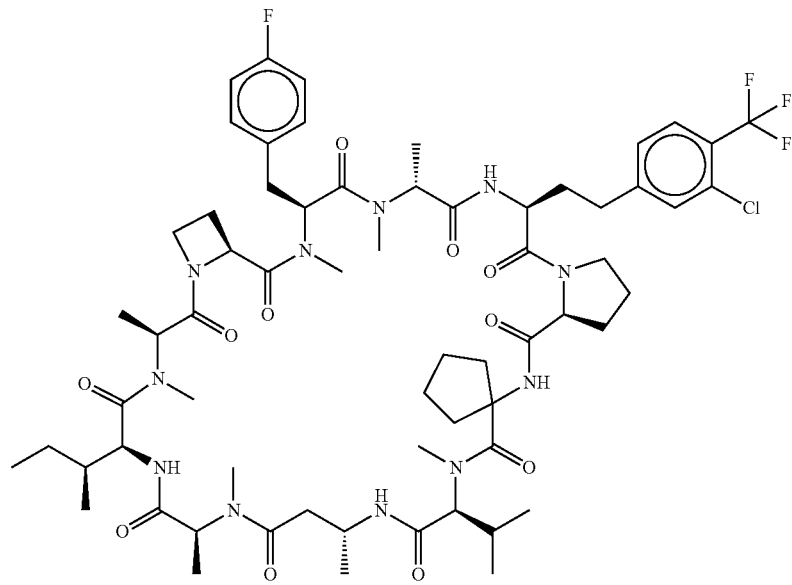 |

TABLE 24-continued
| Compound No. | Structural formula |
|---|---|
| 1703 | 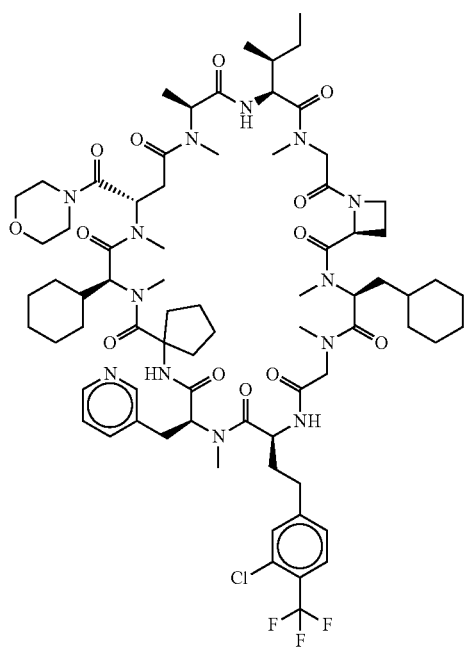 |
| 1704 | 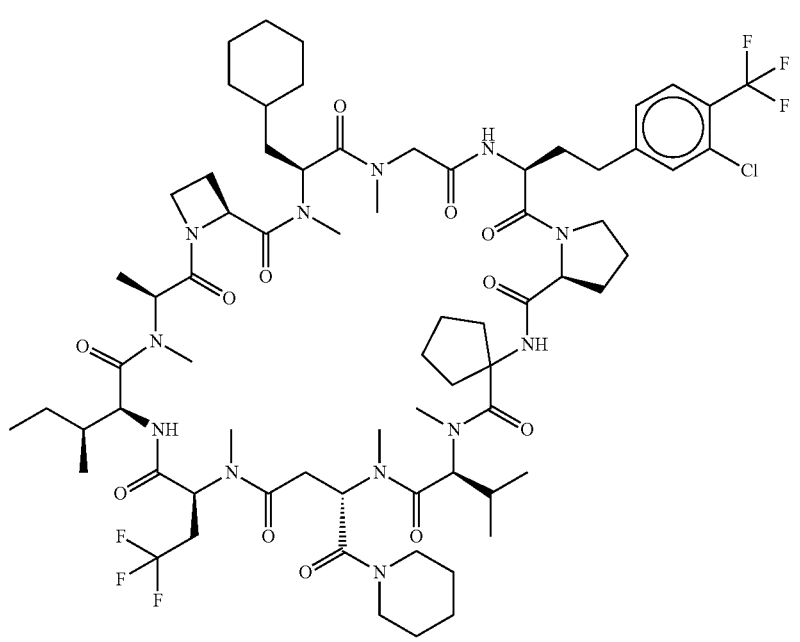 |

TABLE 24-continued
| Compound No. | Structural formula |
|---|---|
| 1705 | 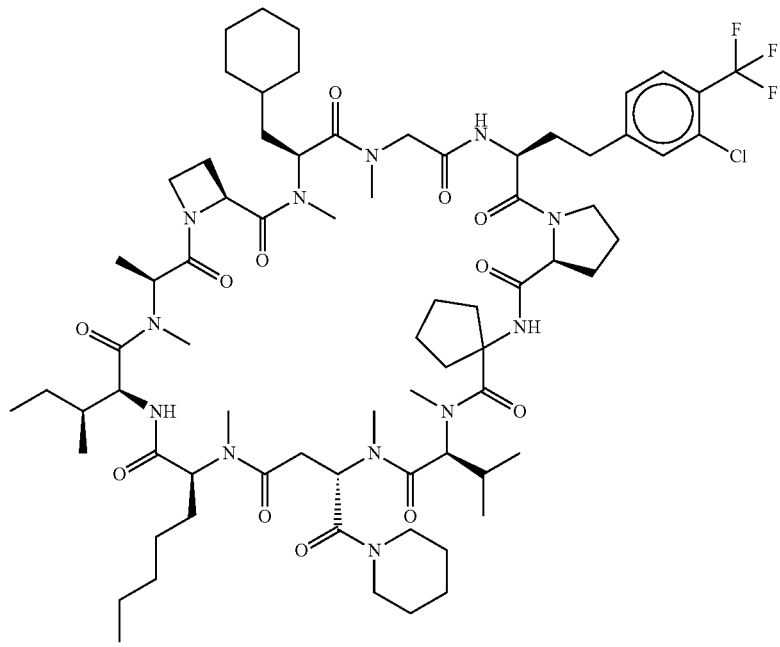 |
| 1706 | 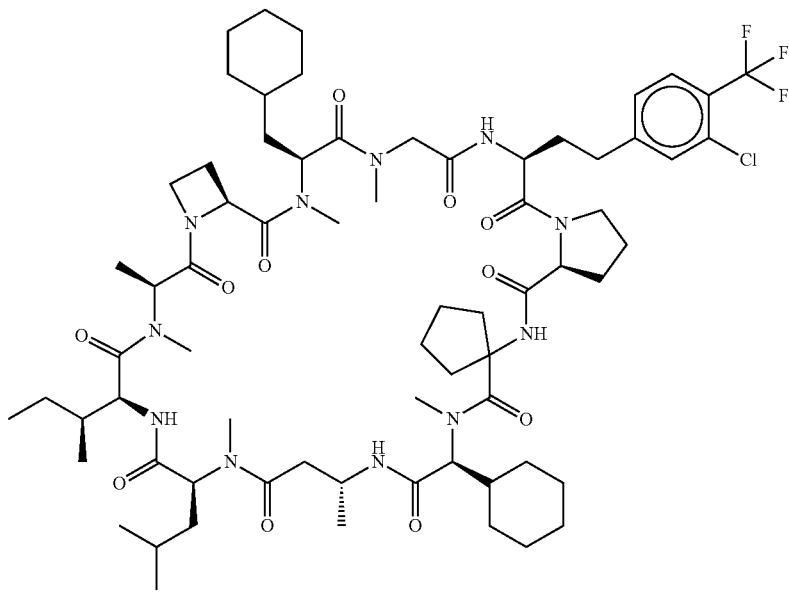 |

TABLE 24-continued
| Compound No. | Structural formula |
|---|---|
| 1707 | 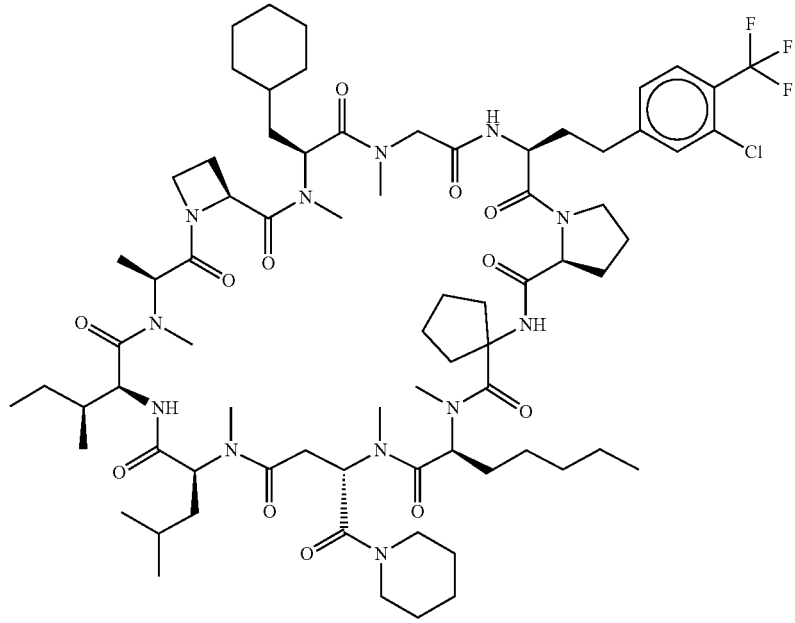 |
| 1708 | 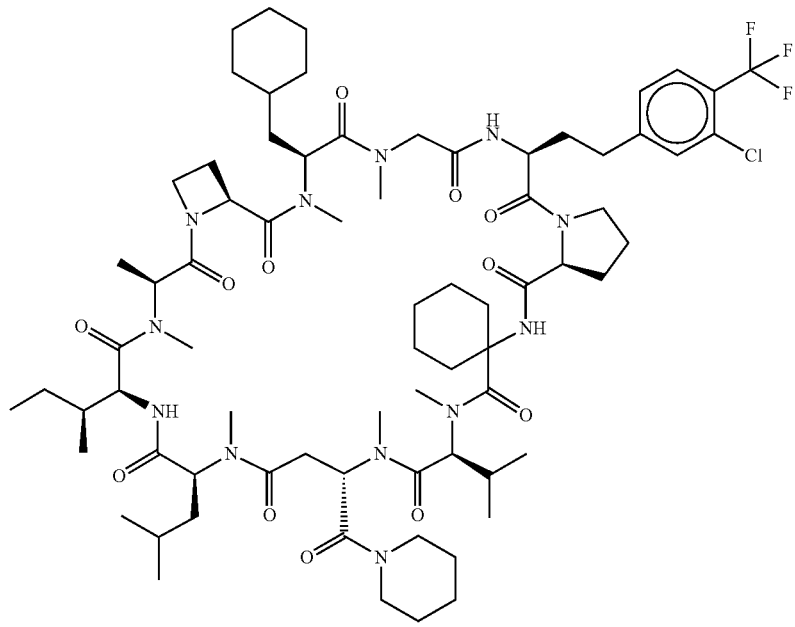 |

TABLE 24-continued
| Compound No. | Structural formula |
|---|---|
| 1709 | 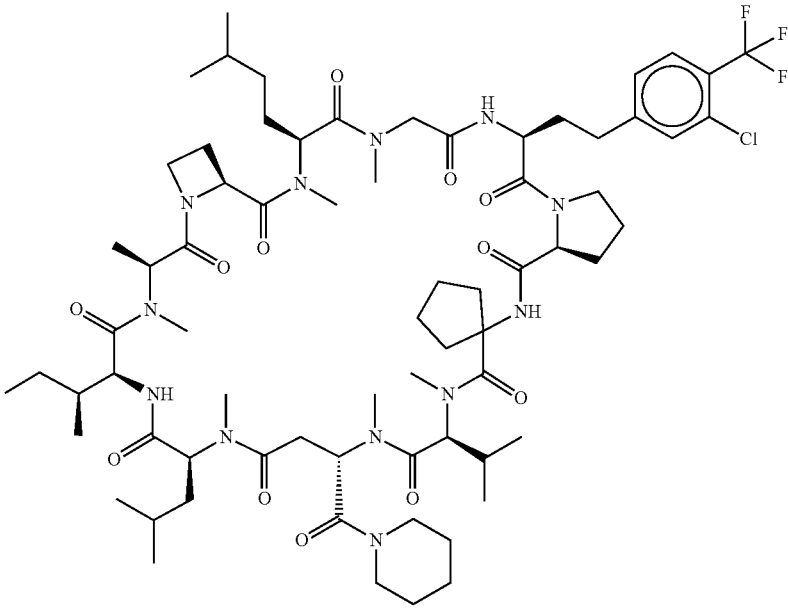 |
| 1710 | 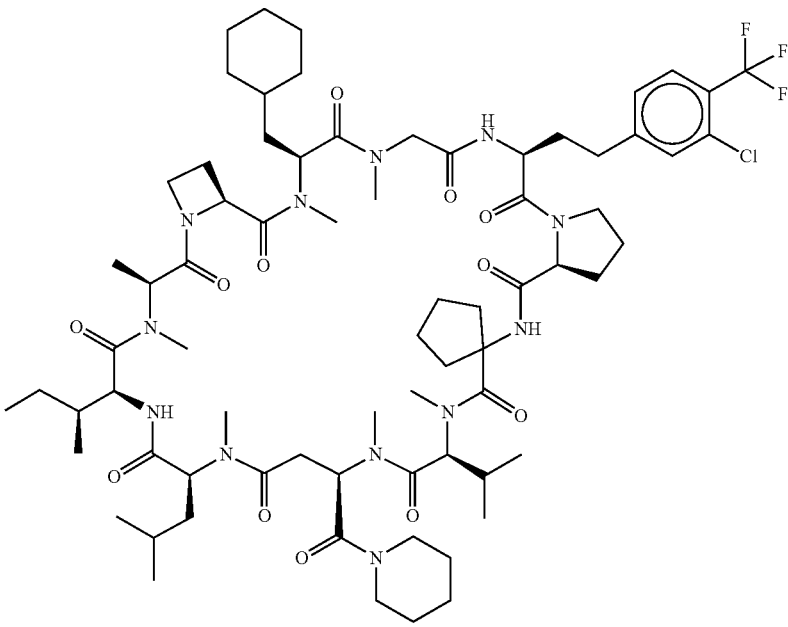 |

TABLE 24-continued
| Compound No. | Structural formula |
|---|---|
| 1711 | 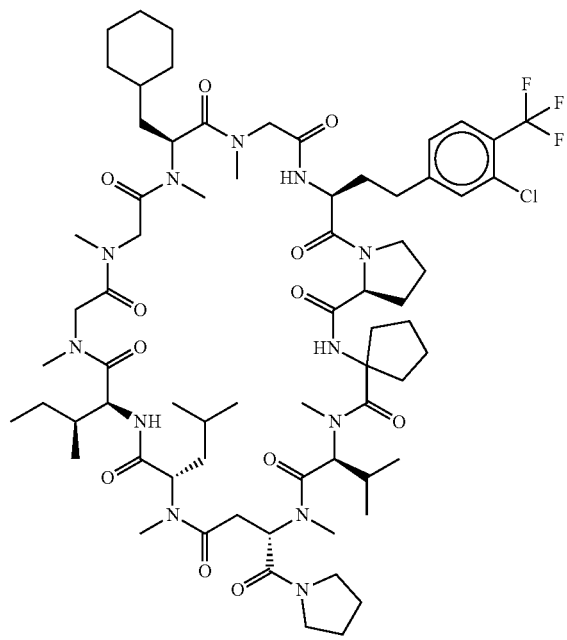 |
| 1712 | 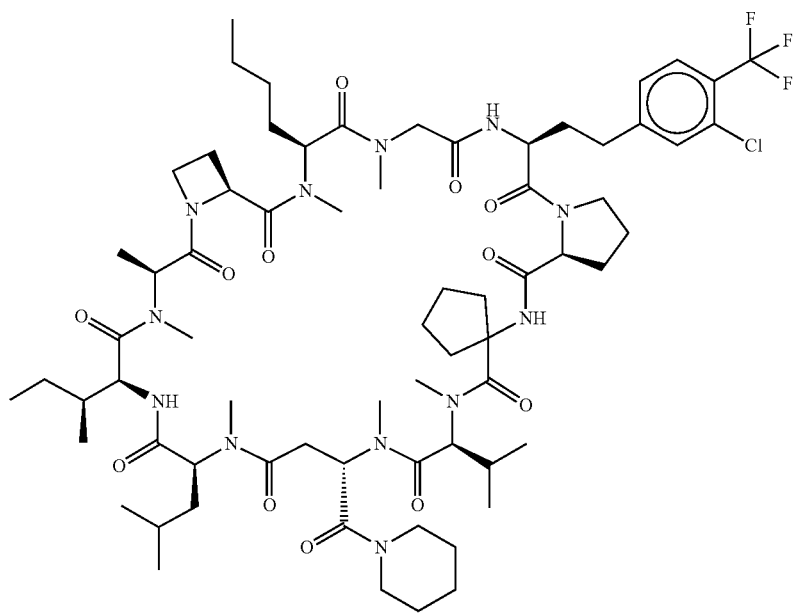 |

TABLE 24-continued
| Compound No. | Structural formula |
| --- | --- |
| 1713 | 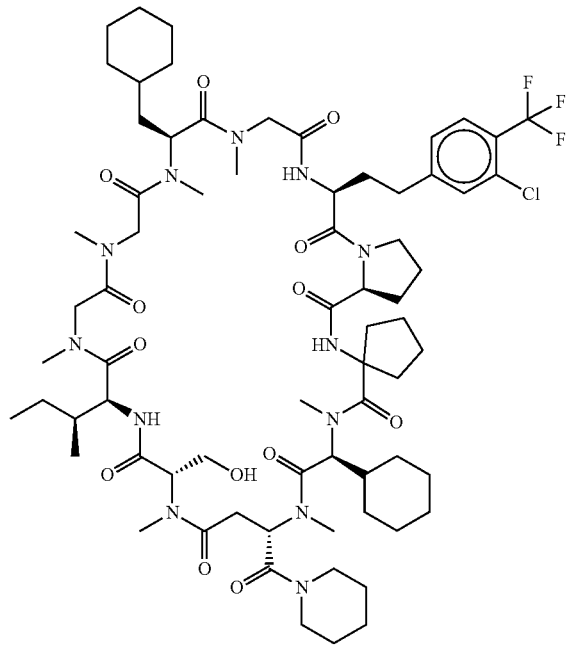 |
| 1714 | 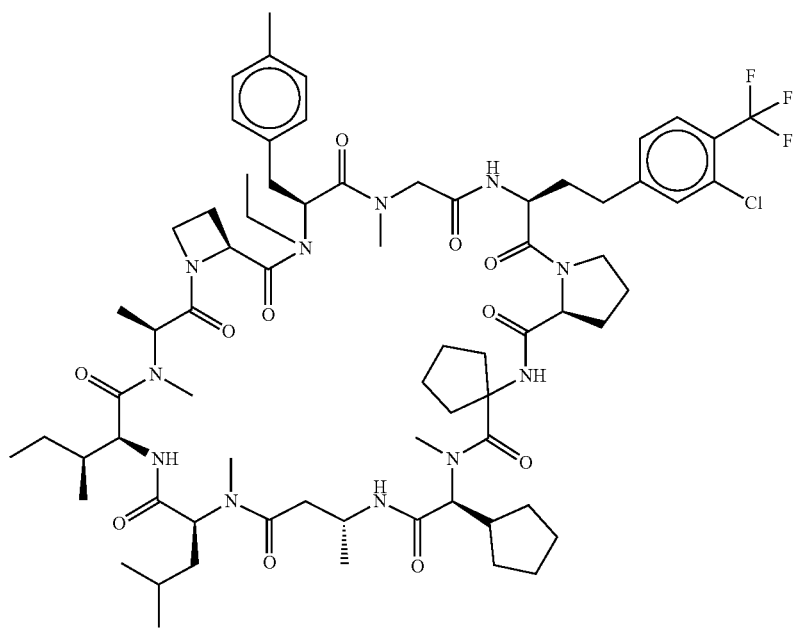 |

TABLE 24-continued
| Compound No. | Structural formula |
|---|---|
| 1715 | 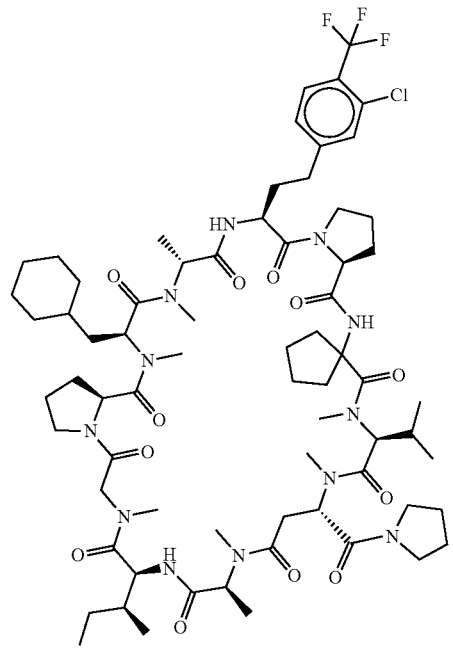 |
| 1716 | 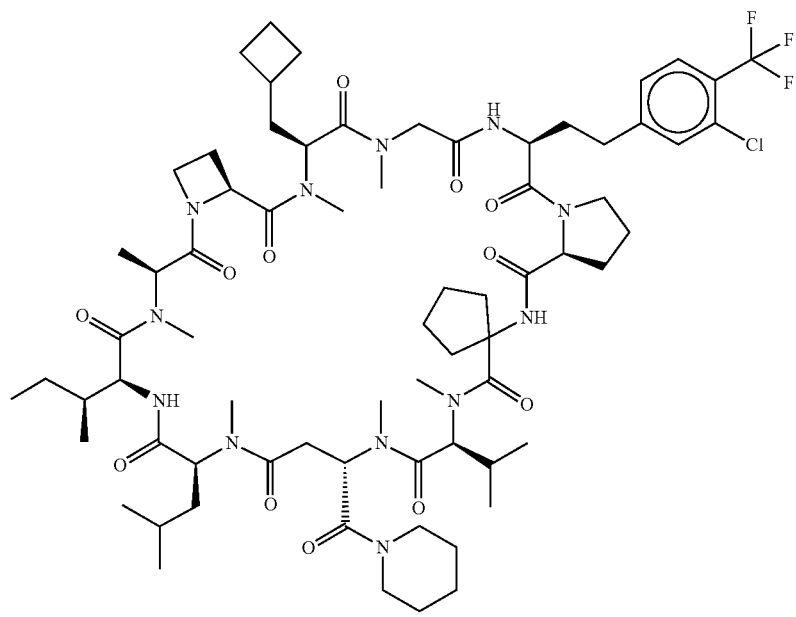 |

TABLE 24-continued
| Compound No. | Structural formula |
|---|---|
| 1717 | 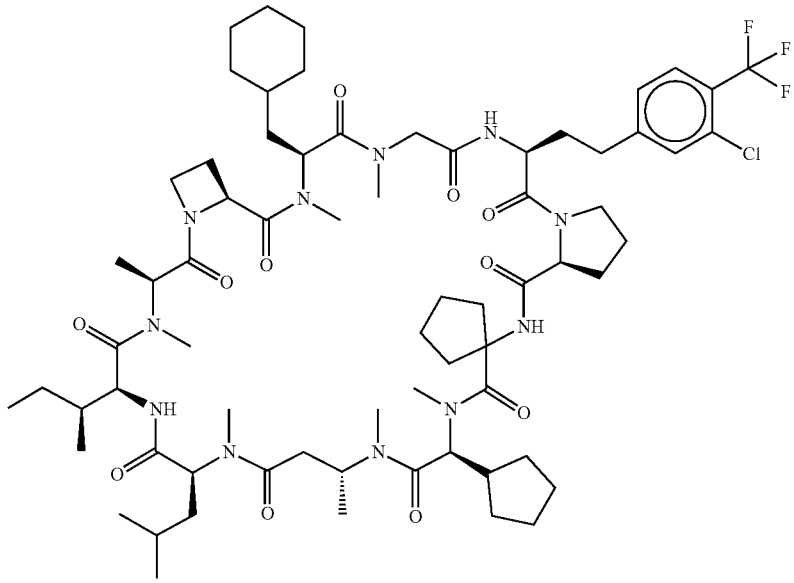 |
| 1718 | 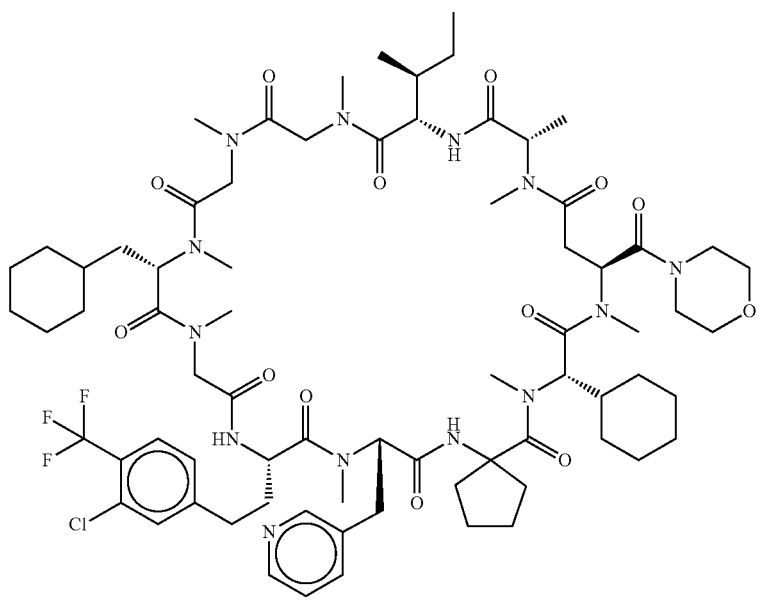 |

TABLE 24-continued
| Compound No. | Structural formula |
|---|---|
| 1719 | 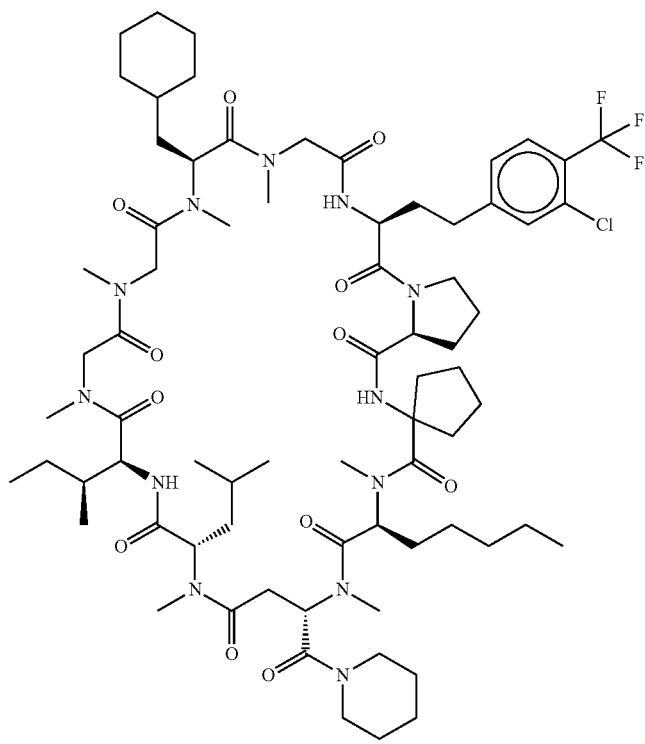 |
| 1720 | 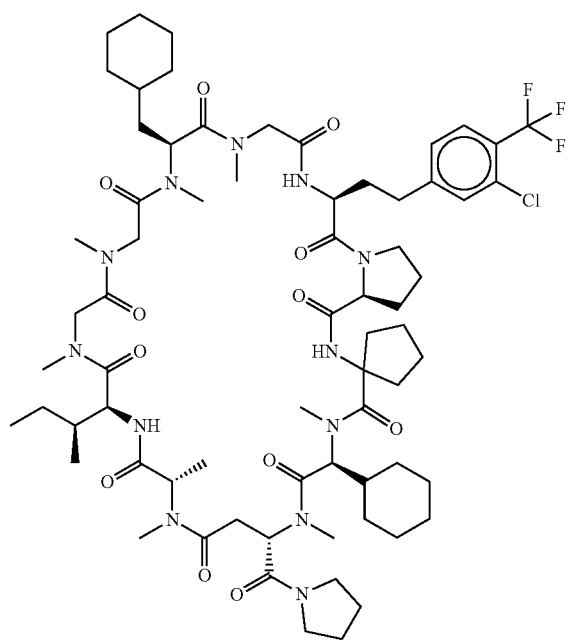 |

TABLE 24-continued
| Compound No. | Structural formula |
|---|---|
| 1721 | 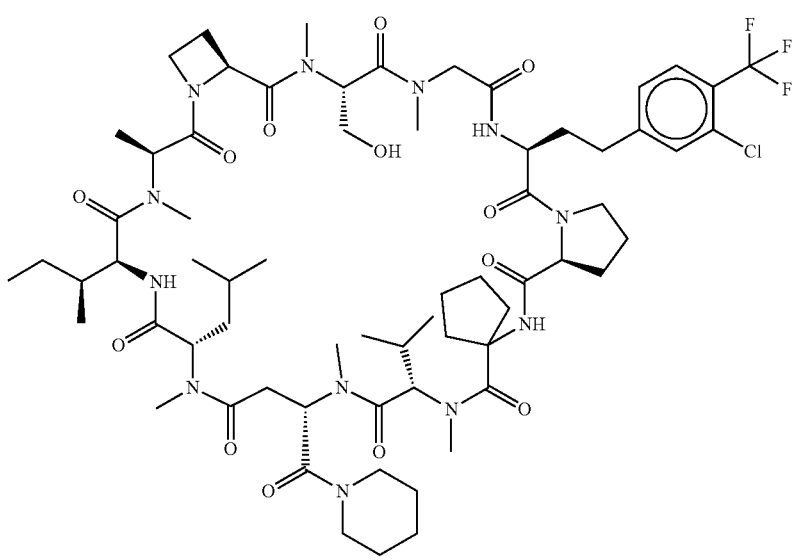 |
| 1722 | 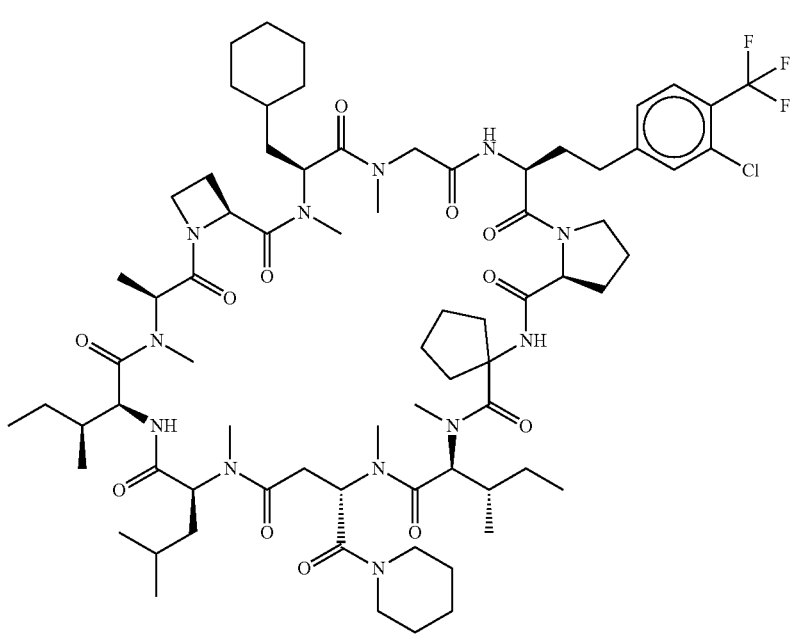 |

TABLE 24-continued
| Compound No. | Structural formula |
|---|---|
| 1723 | 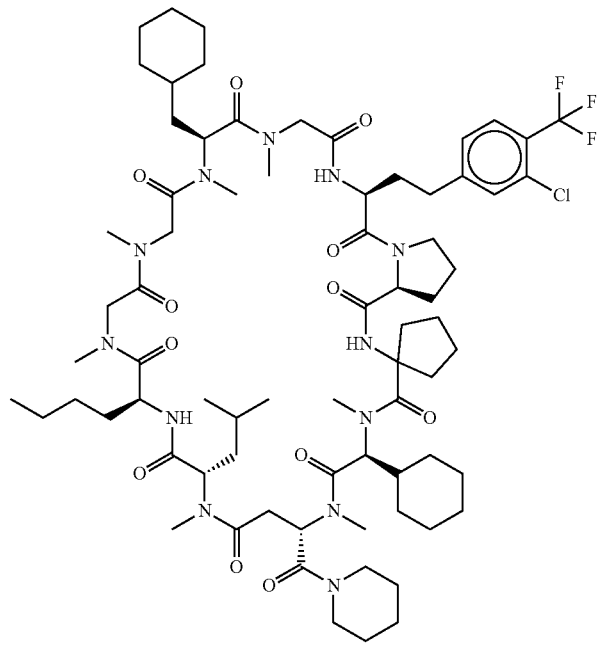 |
| 1724 | 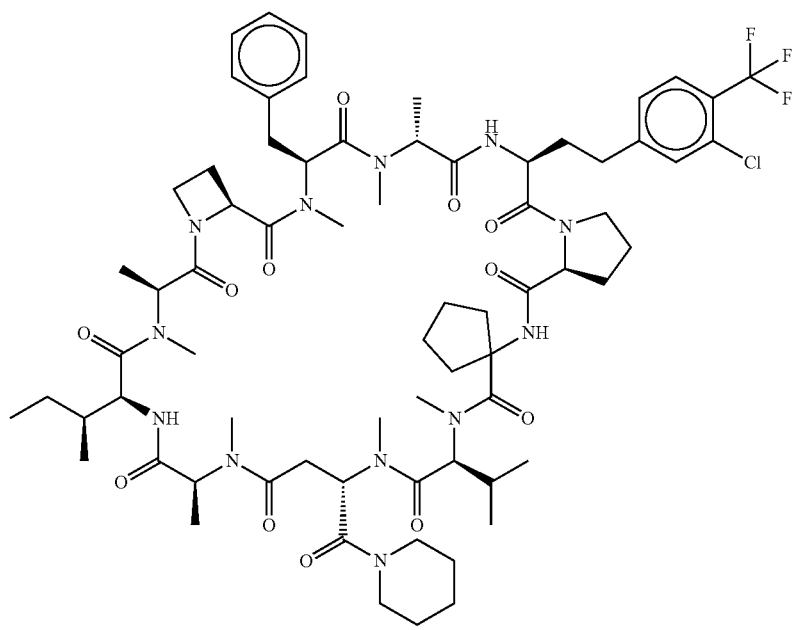 |

TABLE 24-continued
| Compound No. | Structural formula |
|---|---|
| 1725 | 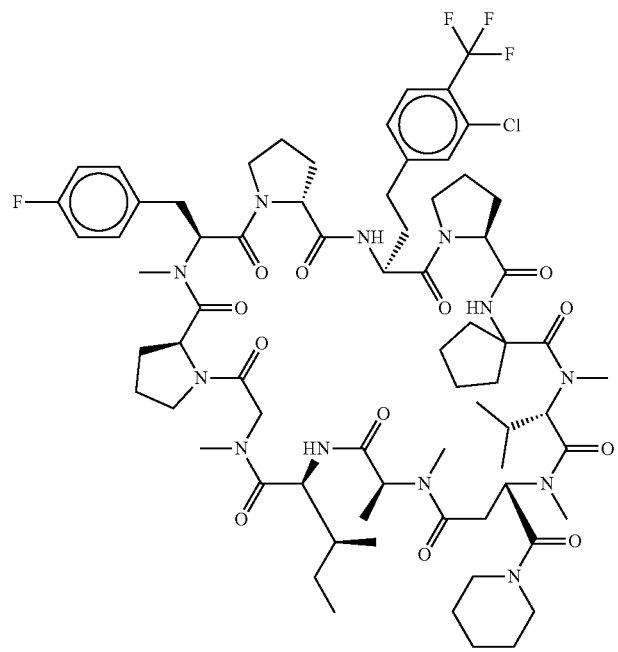 |
| 1726 | 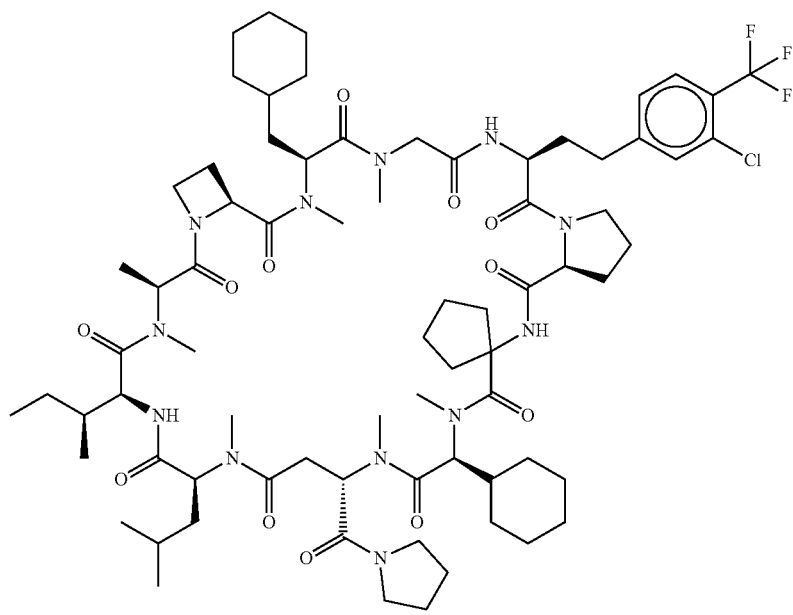 |

TABLE 24-continued
| Compound No. | Structural formula |
|---|---|
| 1727 | 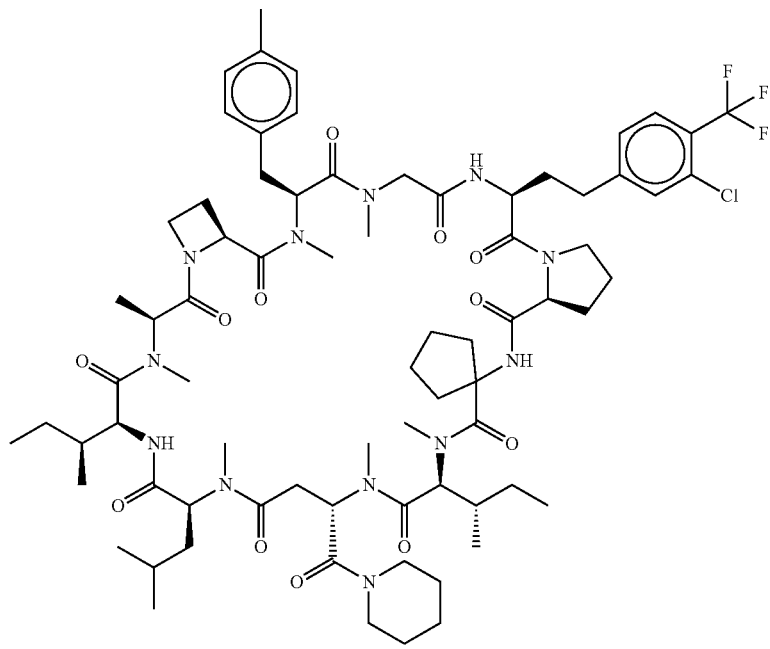 |
| 1728 | 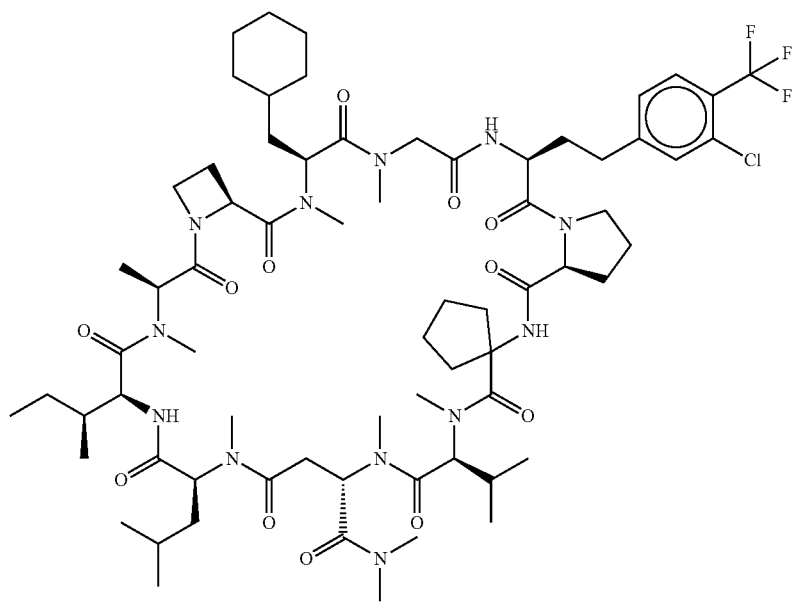 |

TABLE 24-continued
| Compound No. | Structural formula |
|---|---|
| 1729 | 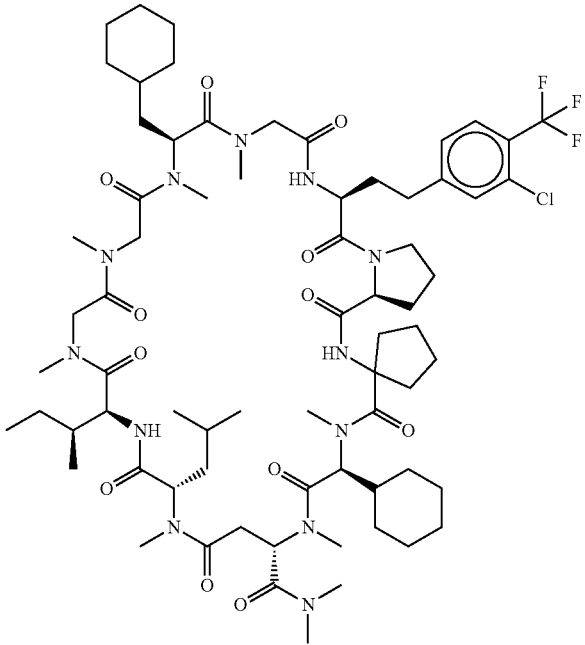 |
| 1730 | 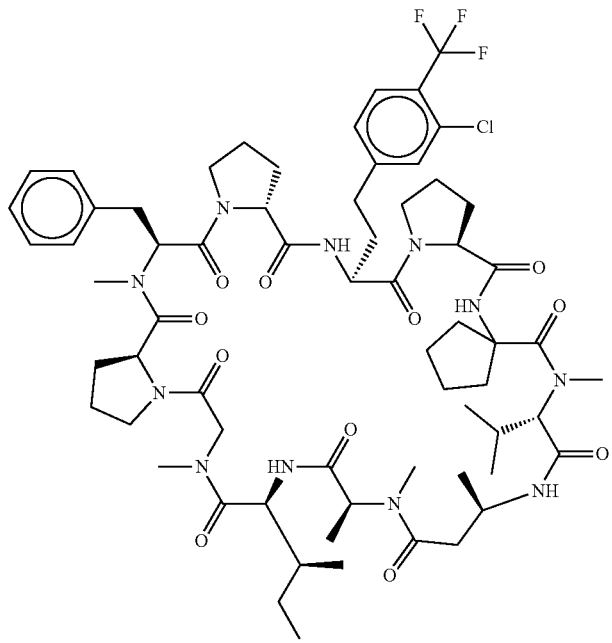 |

TABLE 24-continued
| Compound No. | Structural formula |
| --- | --- |
| 1731 | 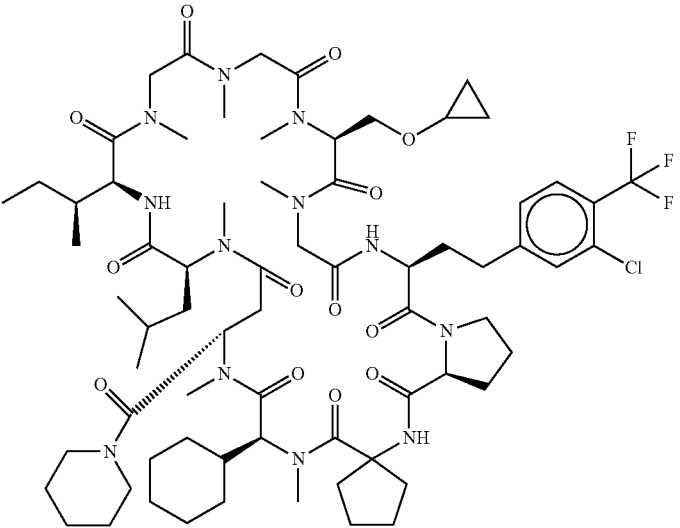 |
| 1732 | 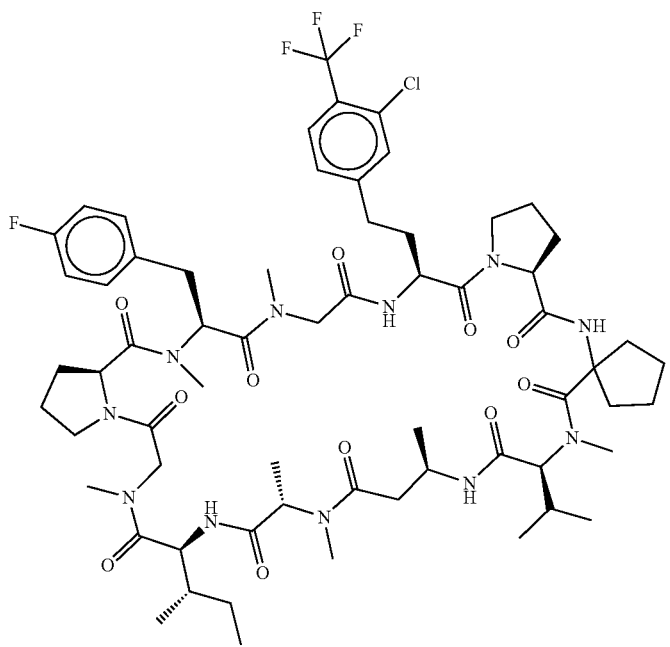 |

TABLE 24-continued
| Compound No. | Structural formula |
|---|---|
| 1733 | 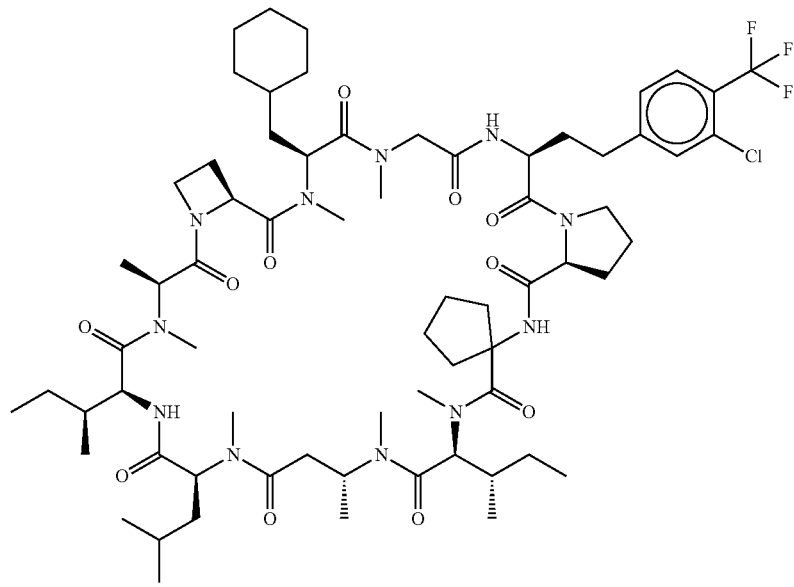 |
| 1734 | 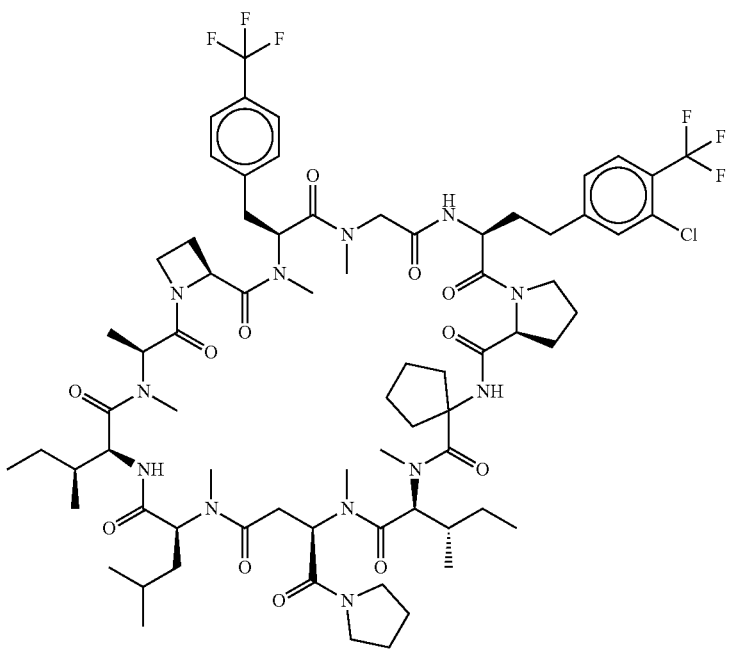 |

TABLE 24-continued
| Compound No. | Structural formula |
|---|---|
| 1735 | 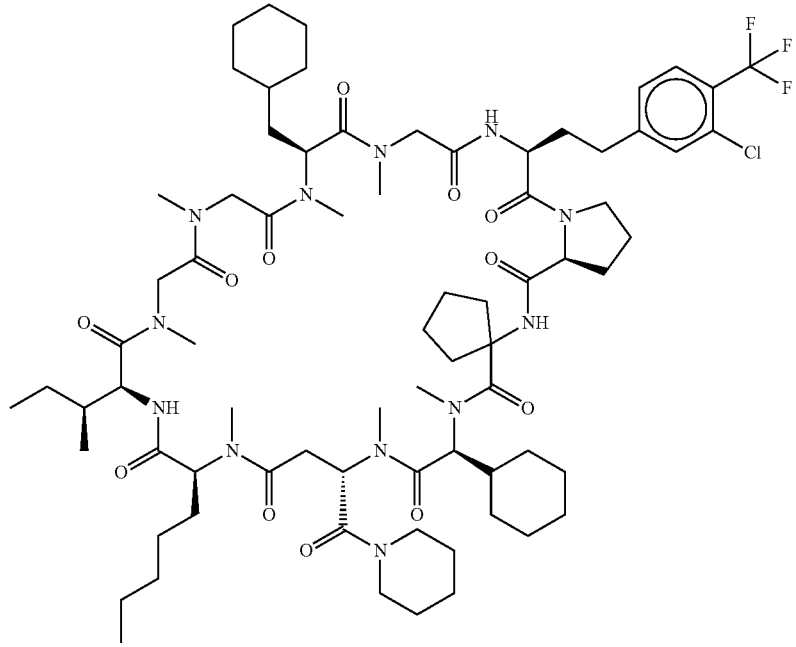 |
| 1736 | 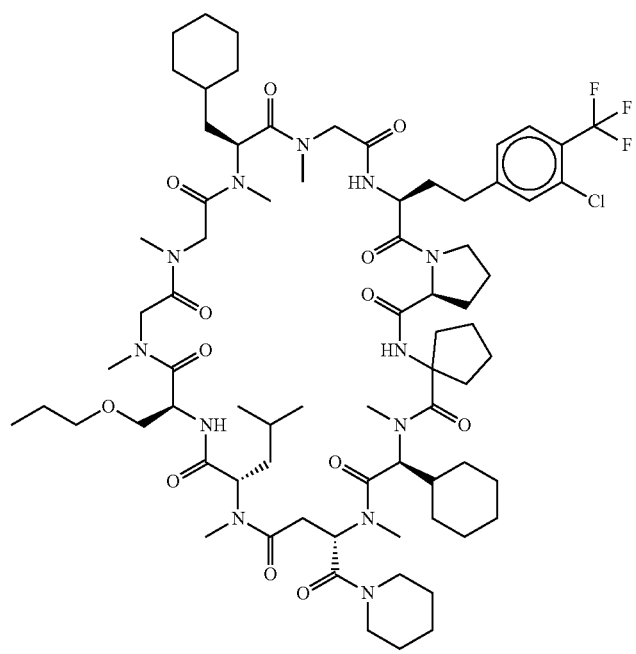 |

TABLE 24-continued
| Compound No. | Structural formula |
|---|---|
| 1737 | 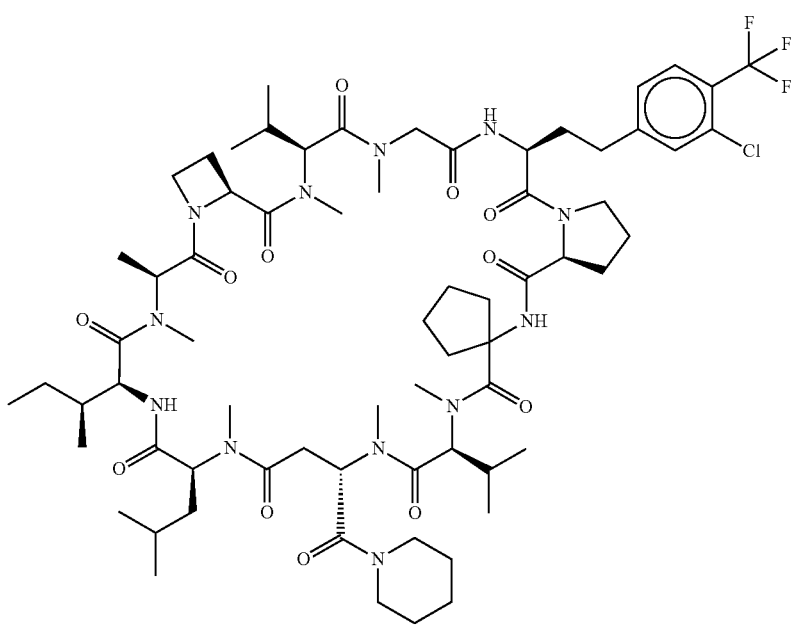 |
| 1738 | 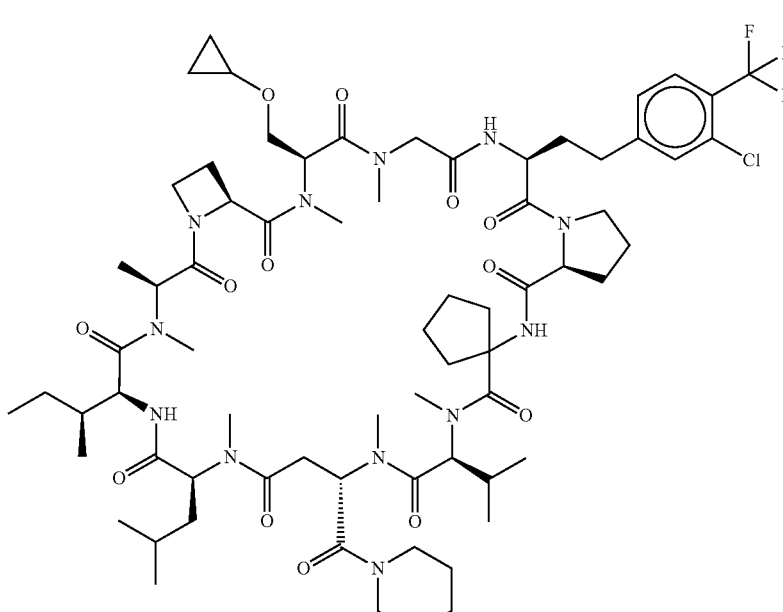 |

TABLE 24-continued
| Compound No. | Structural formula |
|---|---|
| 1739 | 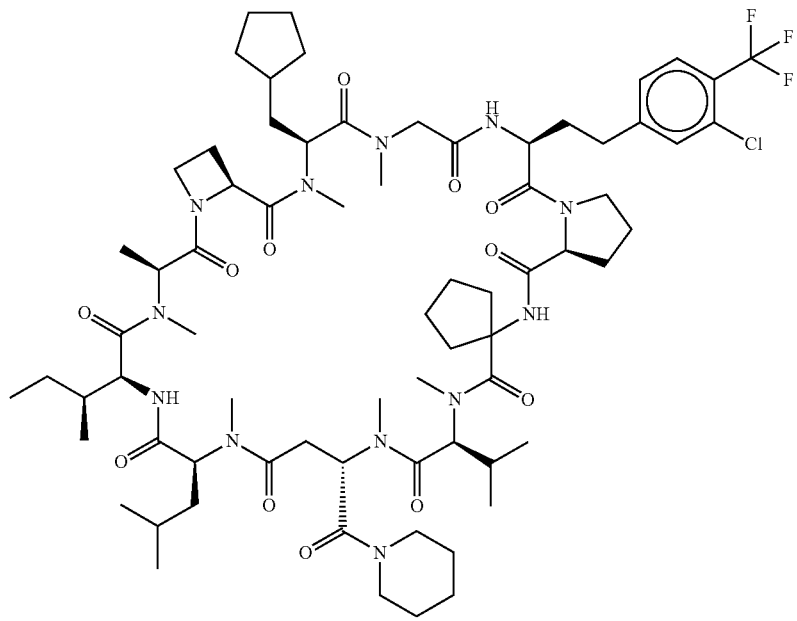 |
| 1740 | 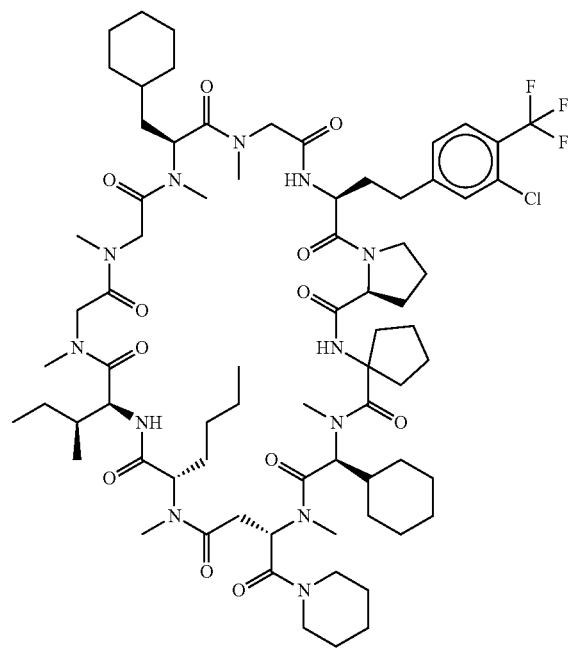 |

TABLE 24-continued
| Compound No. | Structural formula |
|---|---|
| 1741 | 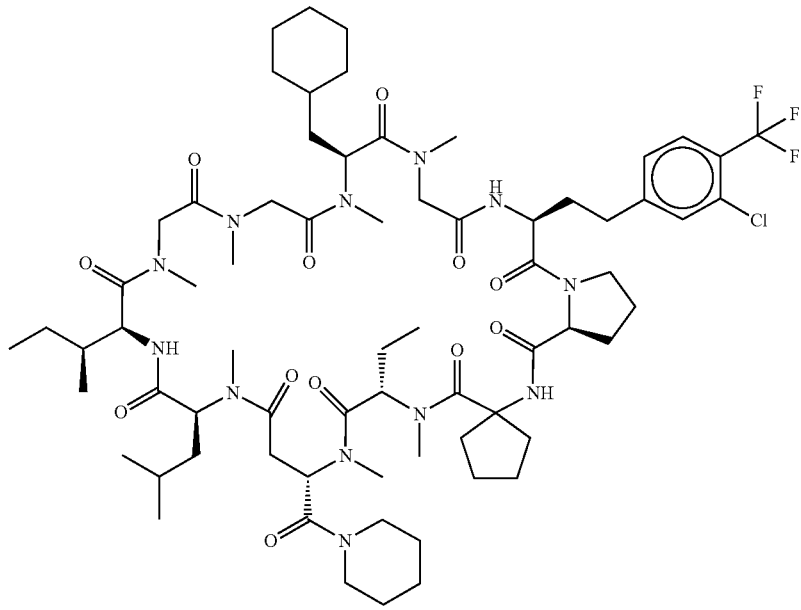 |
| 1742 | 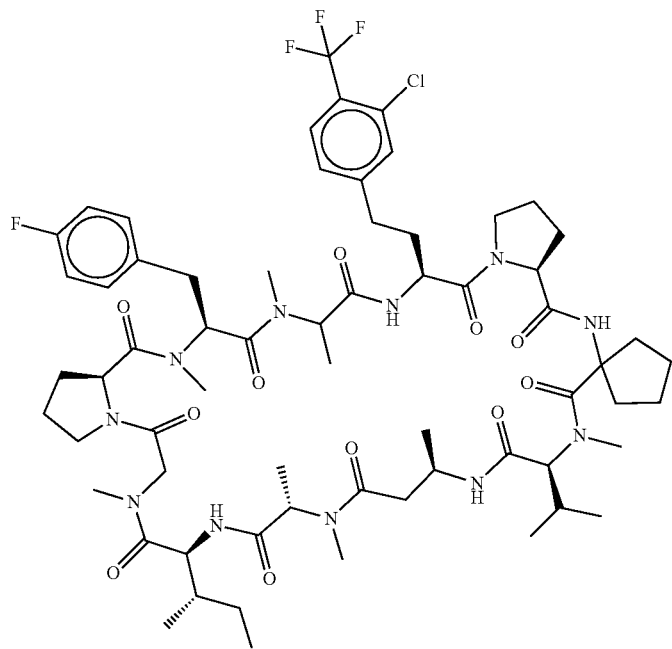 |

TABLE 24-continued
| Compound No. | Structural formula |
|---|---|
| 1743 | 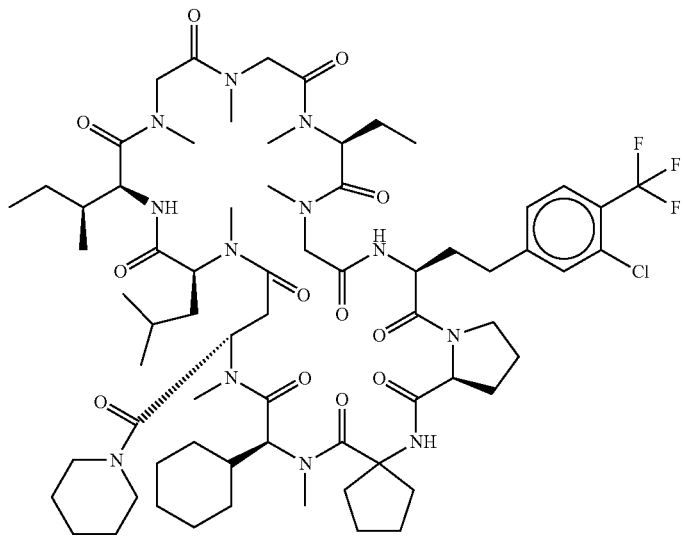 |
| 1744 | 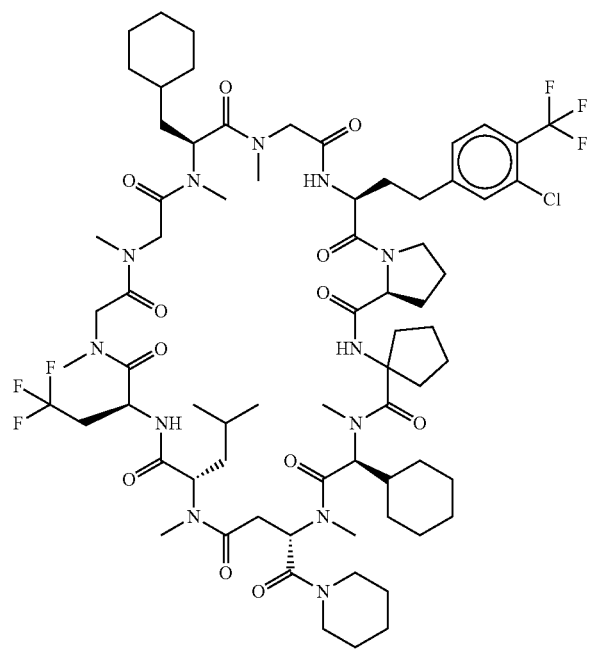 |

TABLE 24-continued
| Compound No. | Structural formula |
|---|---|
| 1745 | 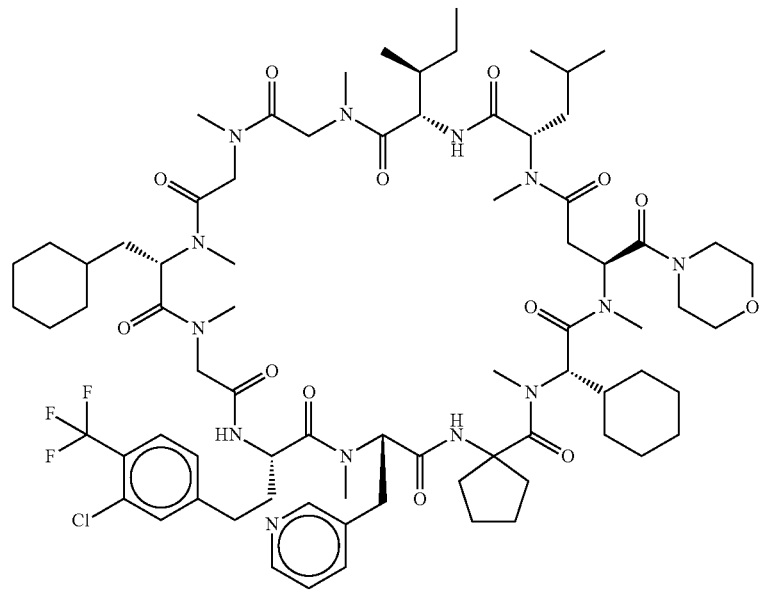 |
| 1746 | 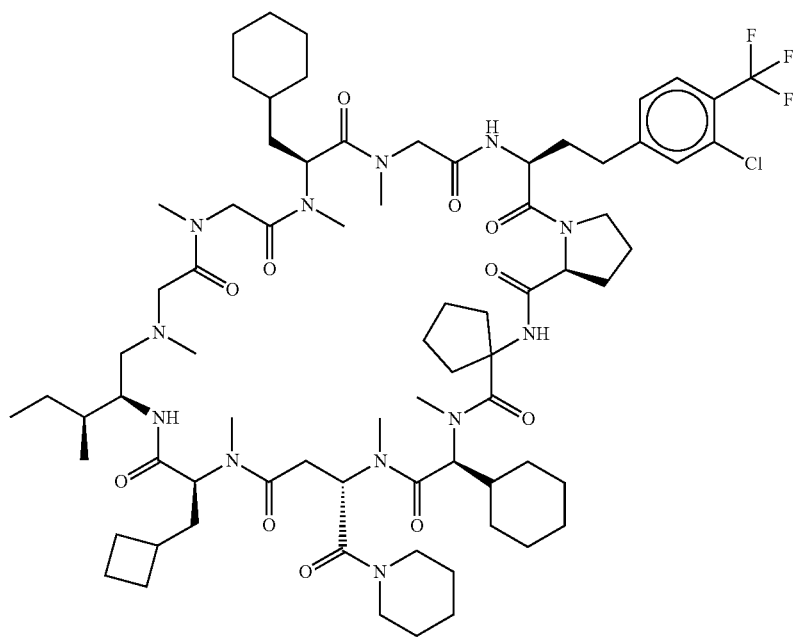 |

TABLE 24-continued
| Compound No. | Structural formula |
|---|---|
| 1747 | 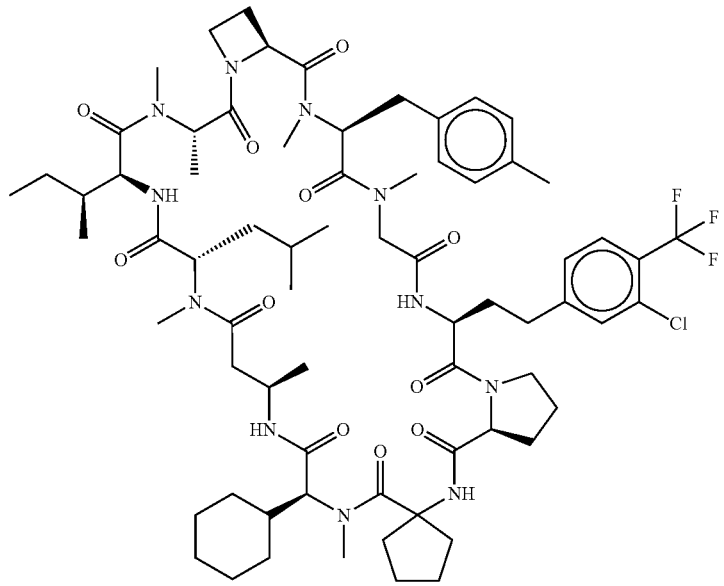 |
| 1748 | 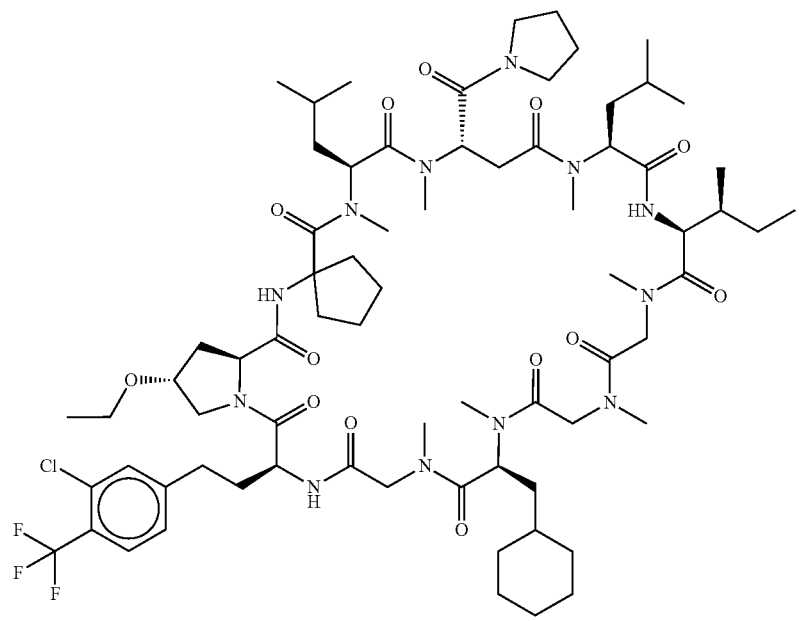 |

TABLE 24-continued
| Compound No. | Structural formula |
|---|---|
| 1749 | 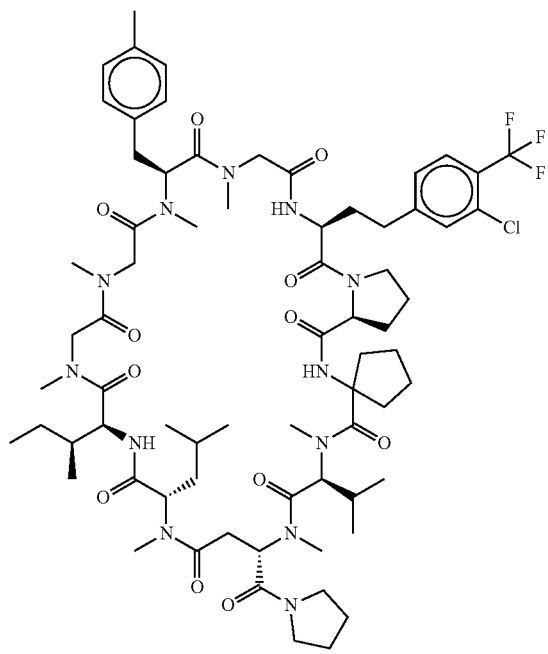 |
| 1750 | 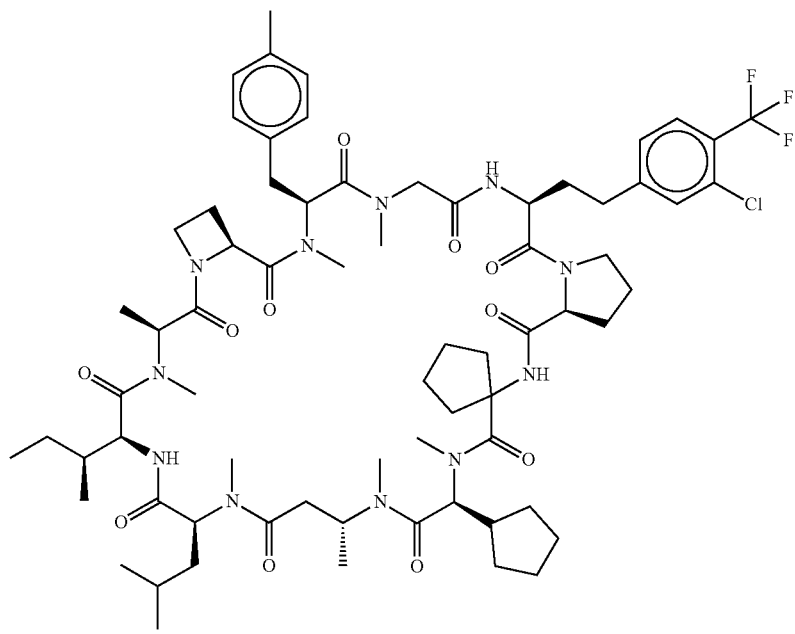 |

TABLE 24-continued
| Compound No. | Structural formula |
|---|---|
| 1751 | 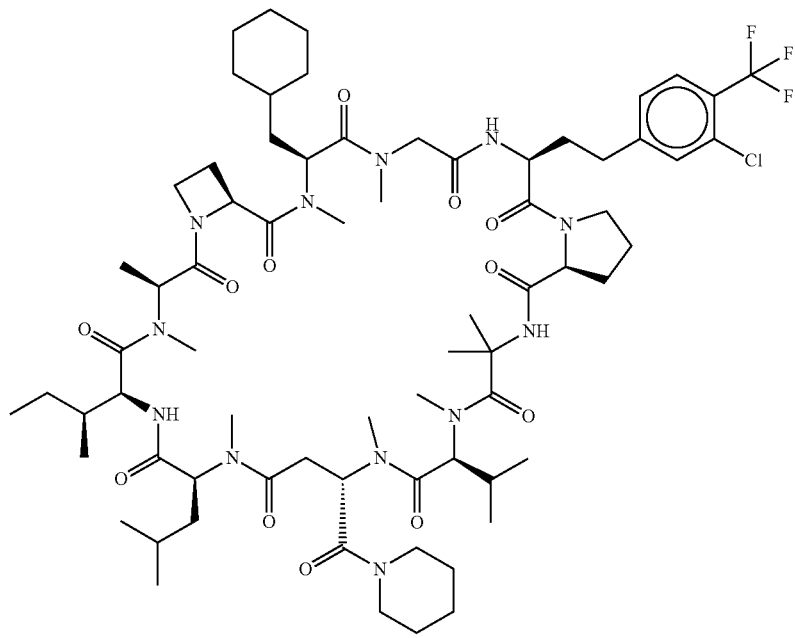 |
| 1752 | 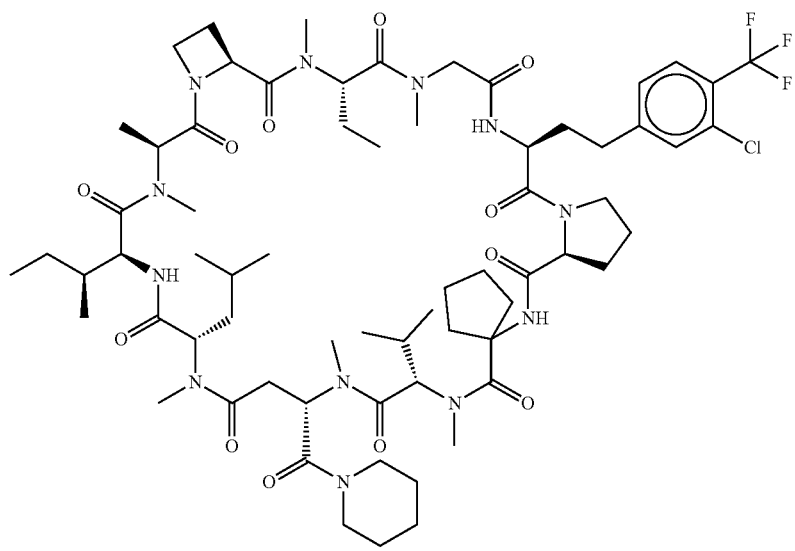 |

TABLE 24-continued
| Compound No. | Structural formula |
|---|---|
| 1753 | 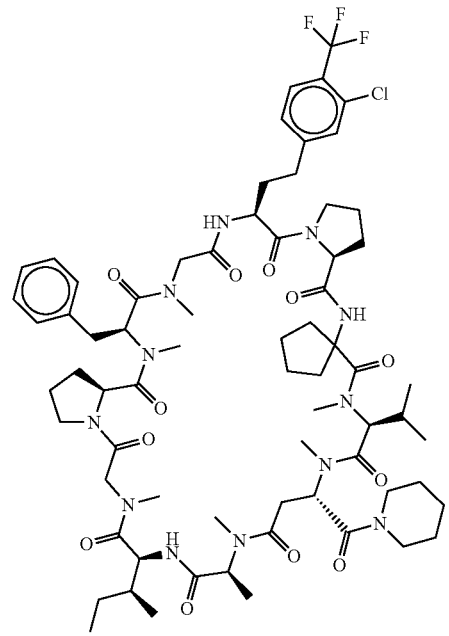 |
| 1754 | 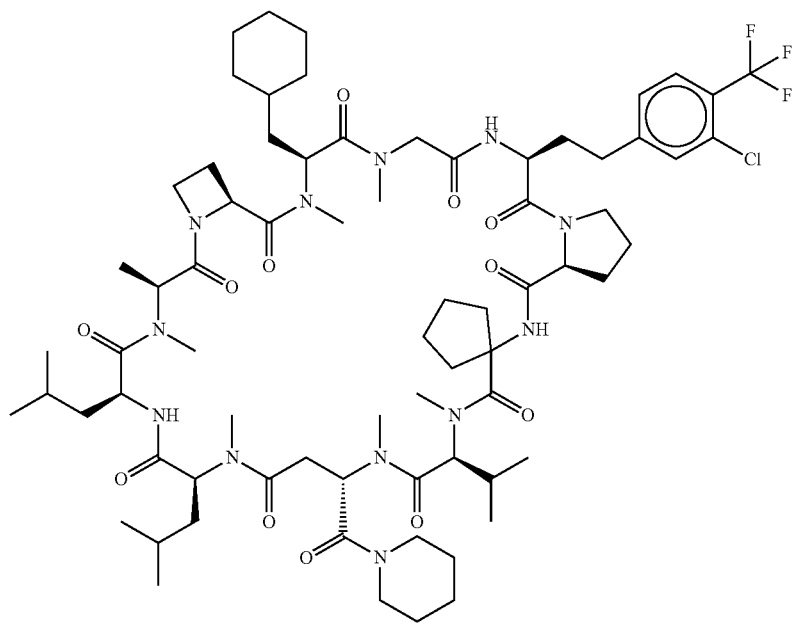 |

TABLE 24-continued
| Compound No. | Structural formula |
|---|---|
| 1755 | 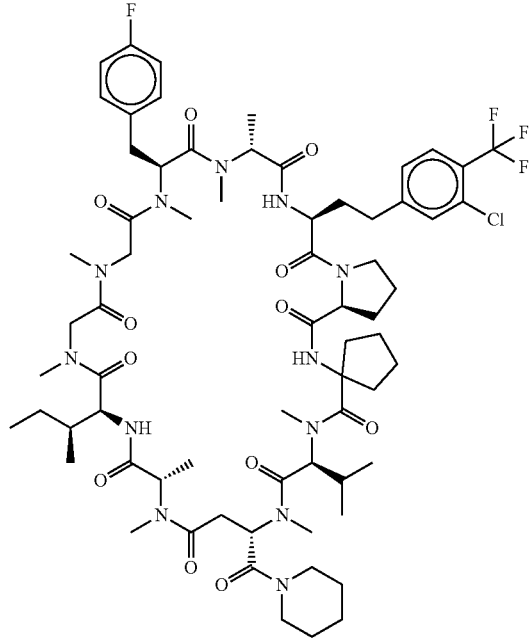 |
| 1756 | 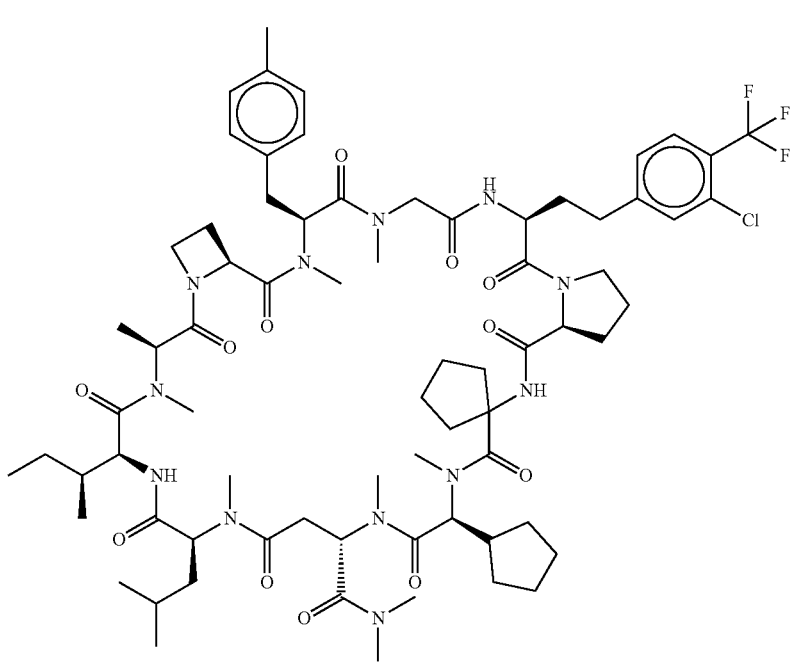 |

TABLE 24-continued
| Compound No. | Structural formula |
|---|---|
| 1757 | 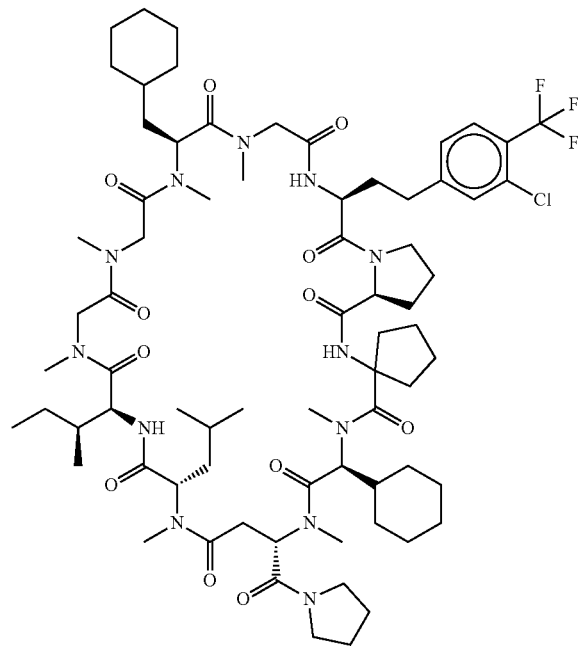 |
| 1758 | 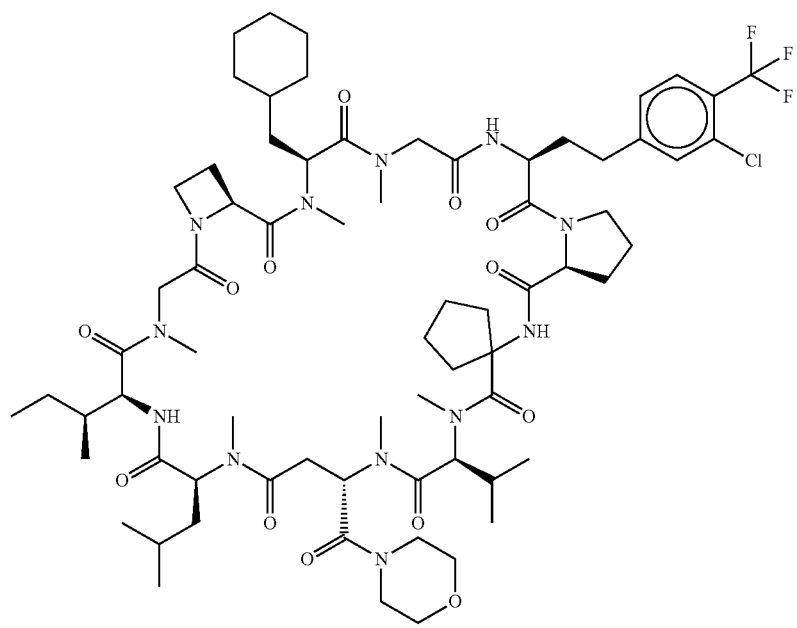 |

TABLE 24-continued
| Compound No. | Structural formula |
|---|---|
| 1759 | 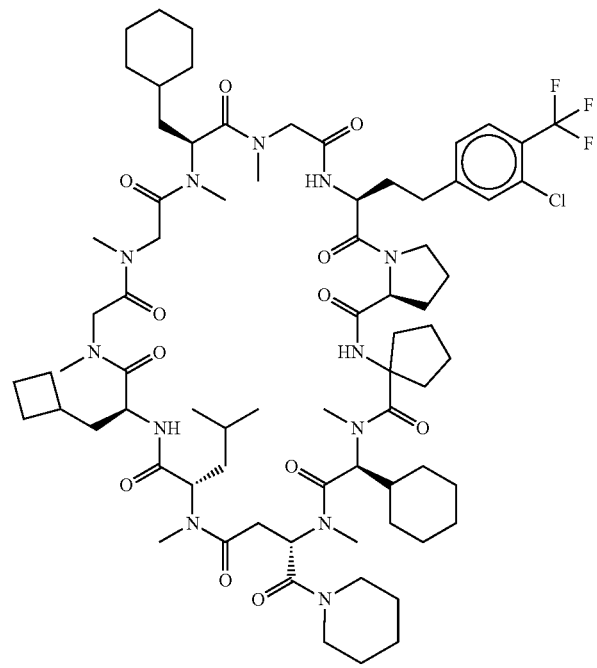 |
| 1760 | 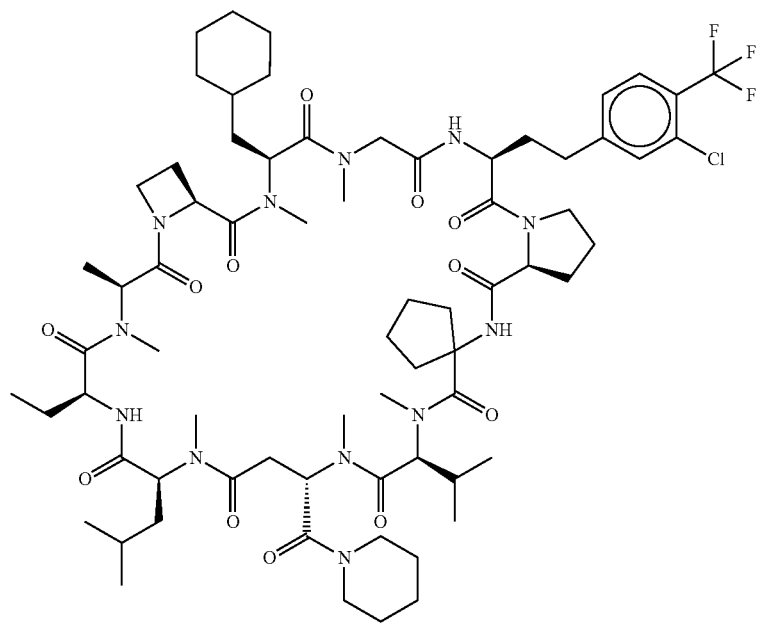 |

TABLE 24-continued
| Compound No. | Structural formula |
|---|---|
| 1761 | 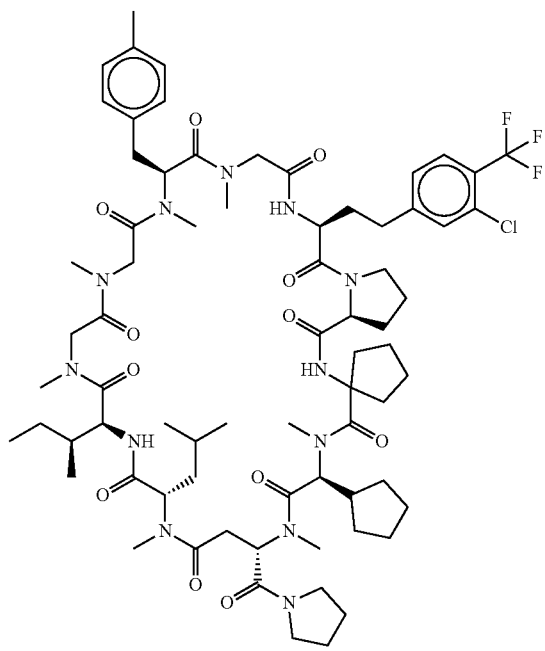 |
| 1762 | 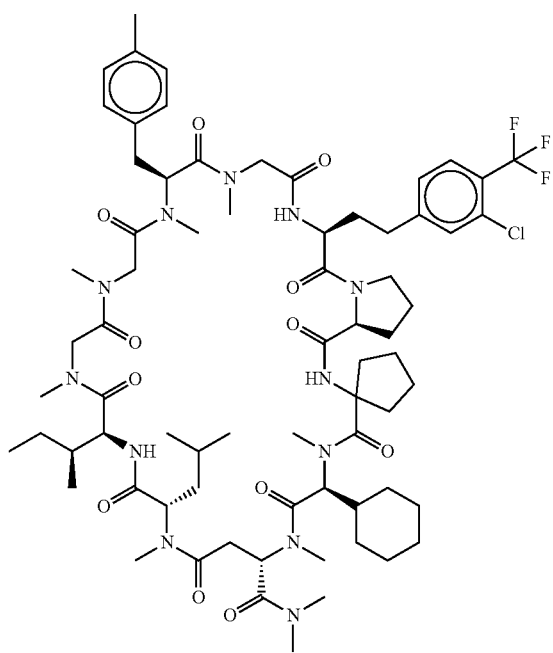 |

TABLE 24-continued
| Compound No. | Structural formula |
|---|---|
| 1763 | 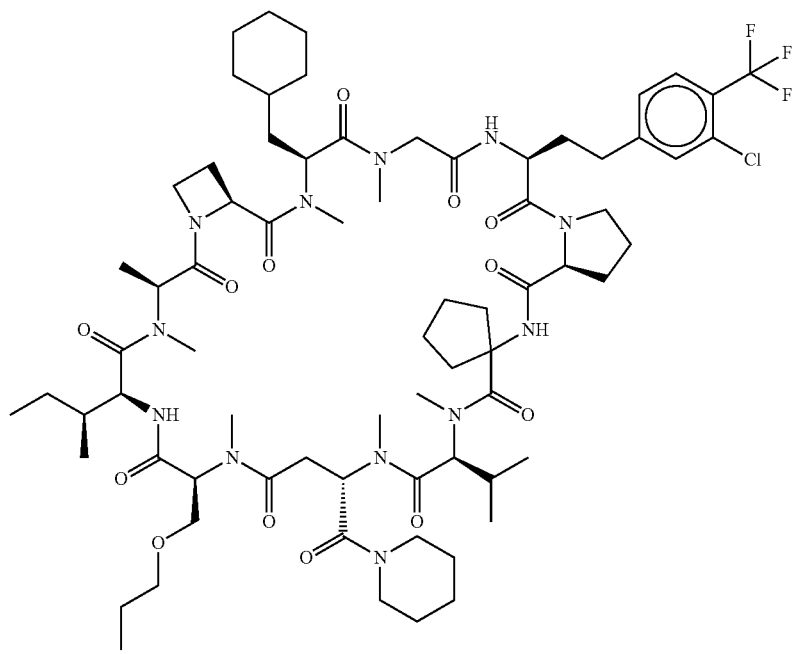 |
| 1764 | 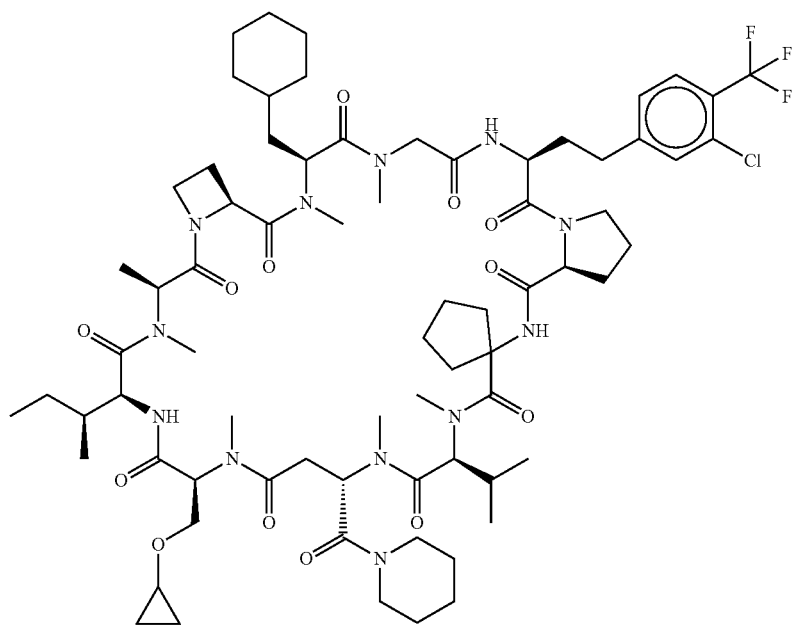 |

TABLE 24-continued
| Compound No. | Structural formula |
|---|---|
| 1765 | 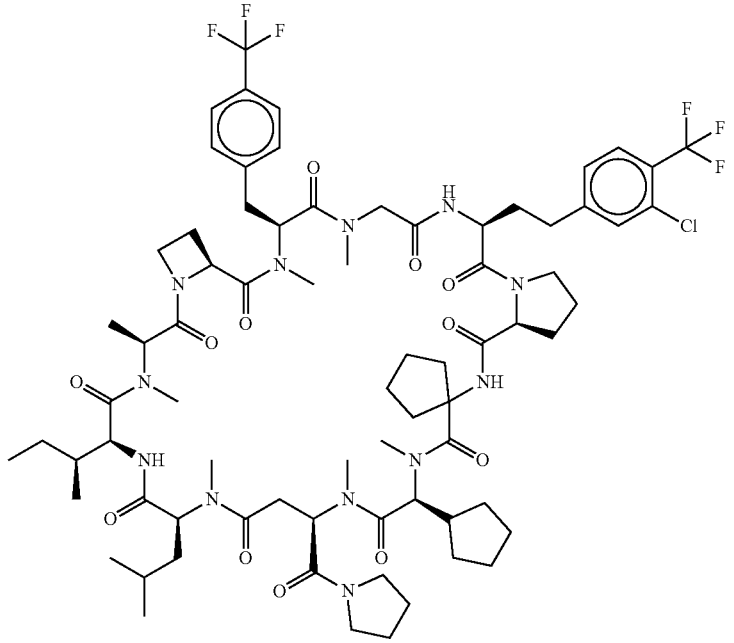 |
| 1766 | 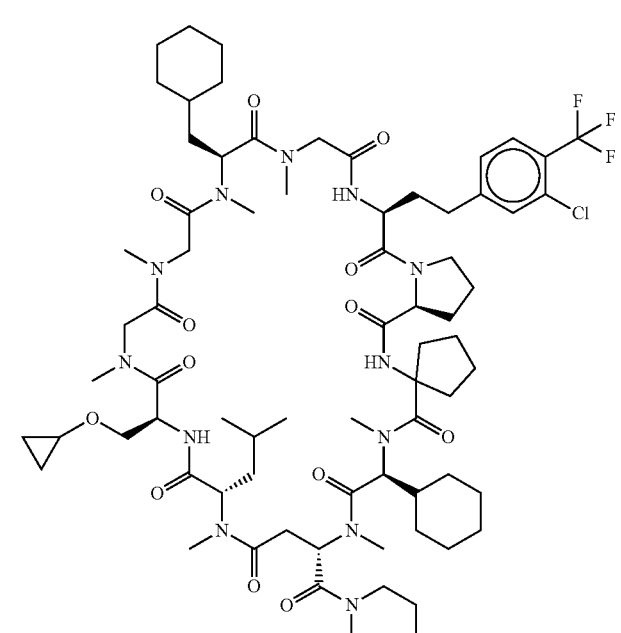 |

TABLE 24-continued
| Compound No. | Structural formula |
| --- | --- |
| 1767 | 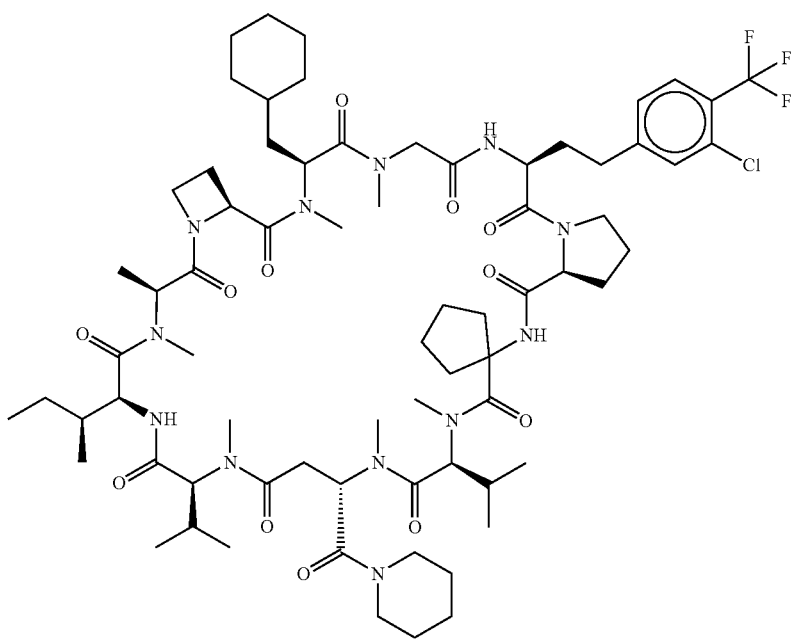 |
| 1768 | 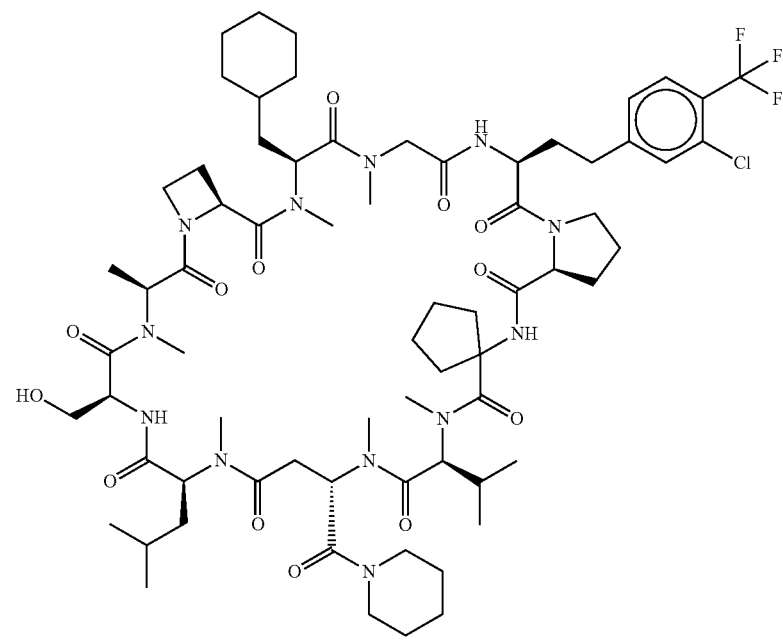 |

TABLE 24-continued
| Compound No. | Structural formula |
|---|---|
| 1769 | 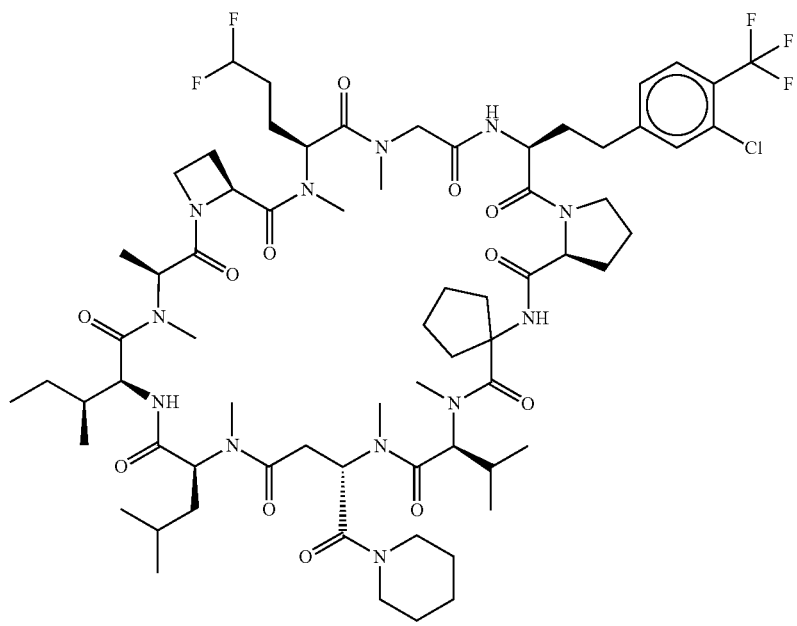 |
| 1770 | 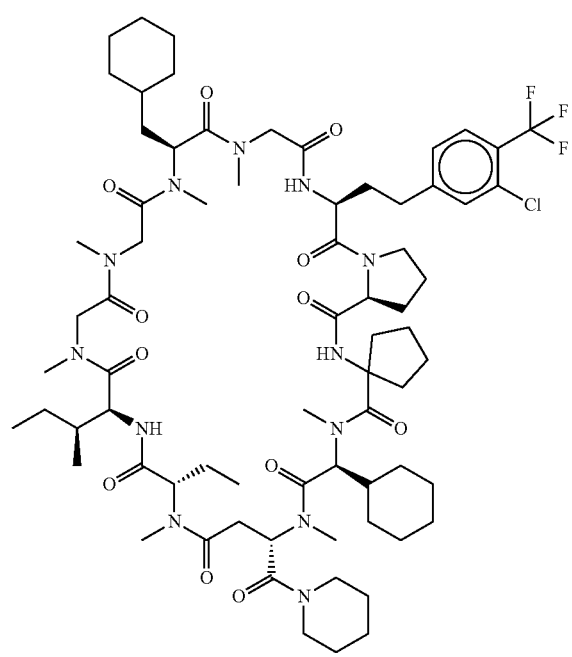 |

TABLE 24-continued
| Compound No. | Structural formula |
|---|---|
| 1771 | 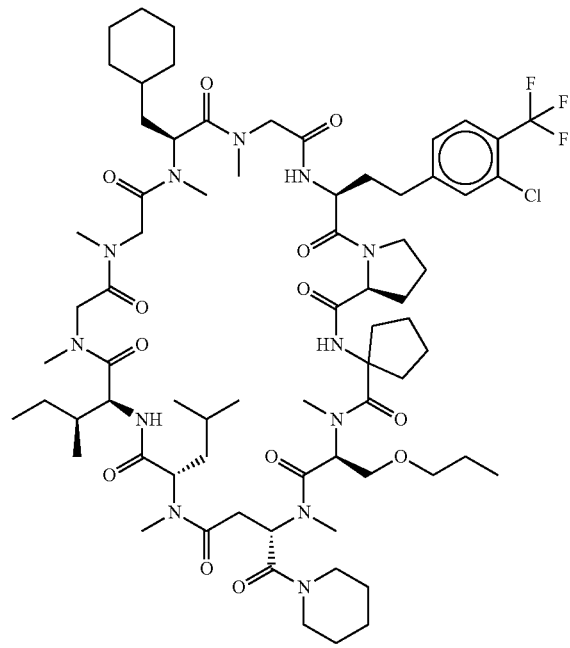 |
| 1772 | 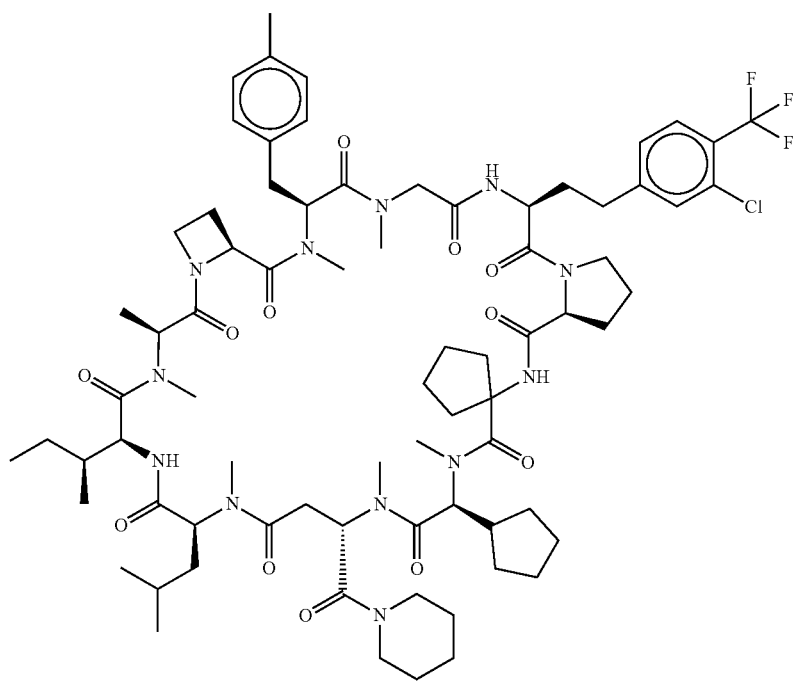 |

TABLE 24-continued
| Compound No. | Structural formula |
|---|---|
| 1773 | 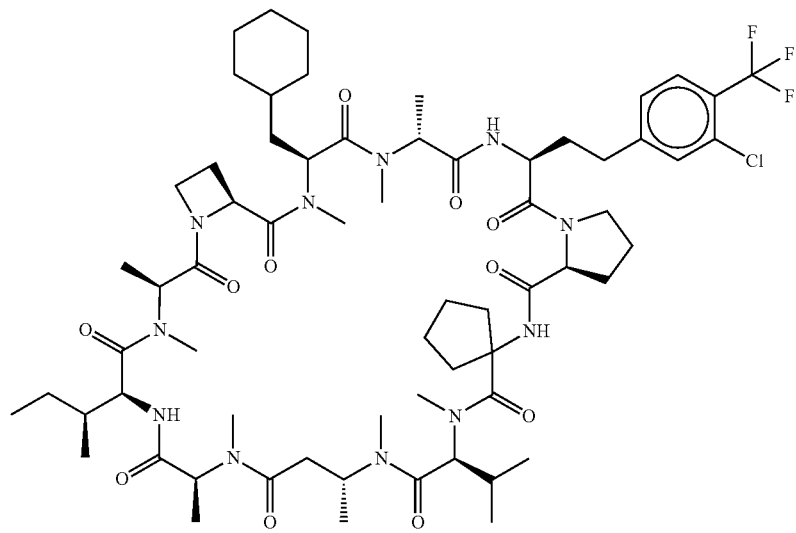 |
| 1774 | 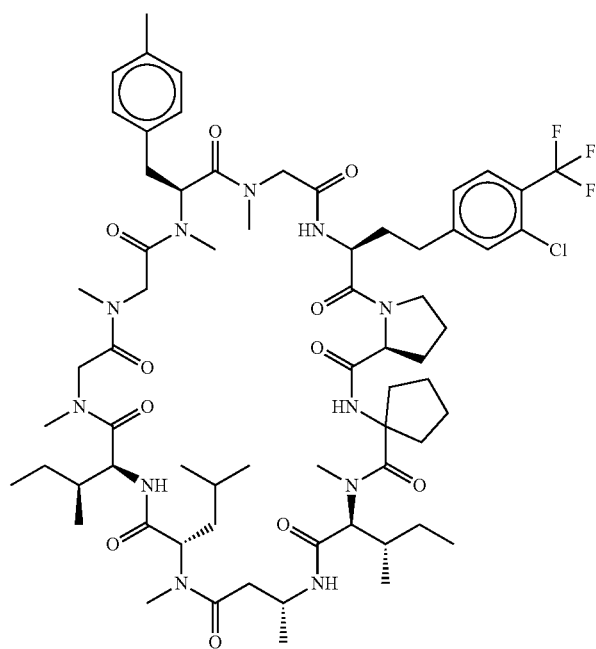 |

TABLE 24-continued
| Compound No. | Structural formula |
|---|---|
| 1775 | 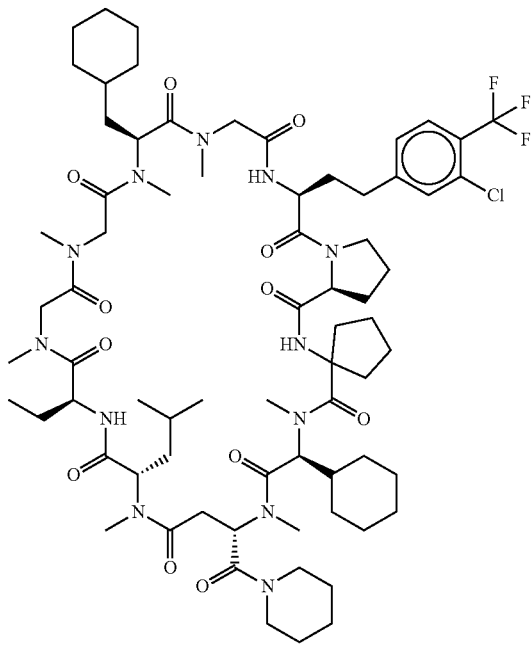 |
| 1776 | 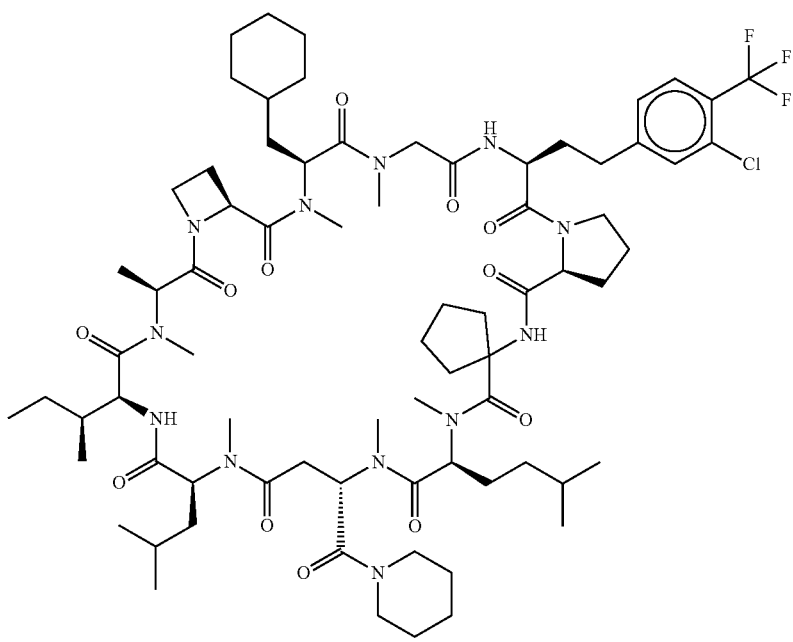 |

TABLE 24-continued
| Compound No. | Structural formula |
| --- | --- |
| 1777 | 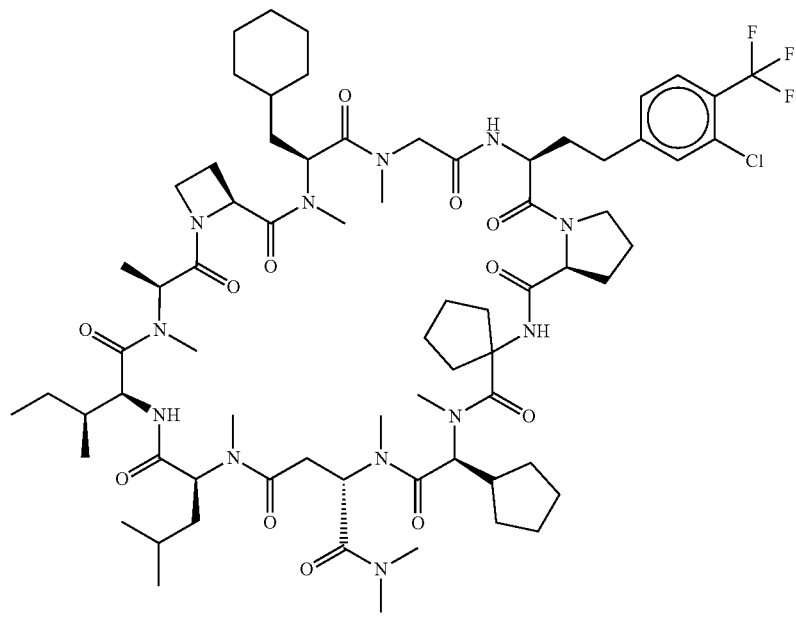 |
| 1778 | 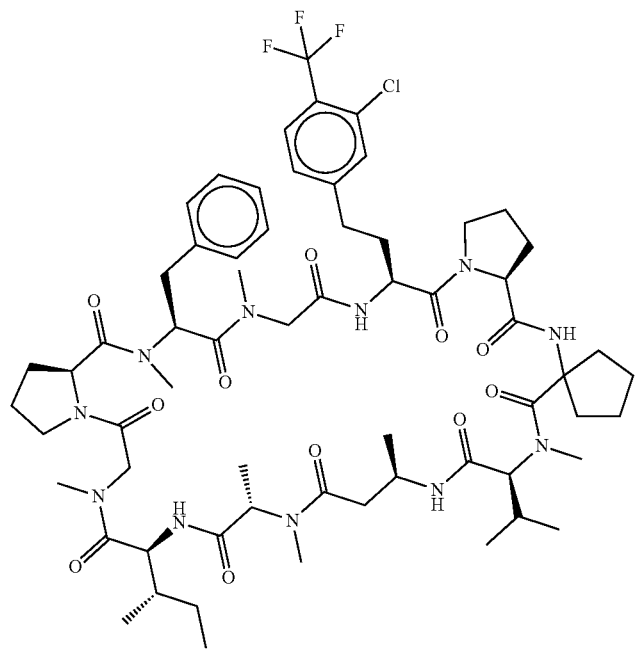 |

TABLE 24-continued
| Compound No. | Structural formula |
|---|---|
| 1779 | 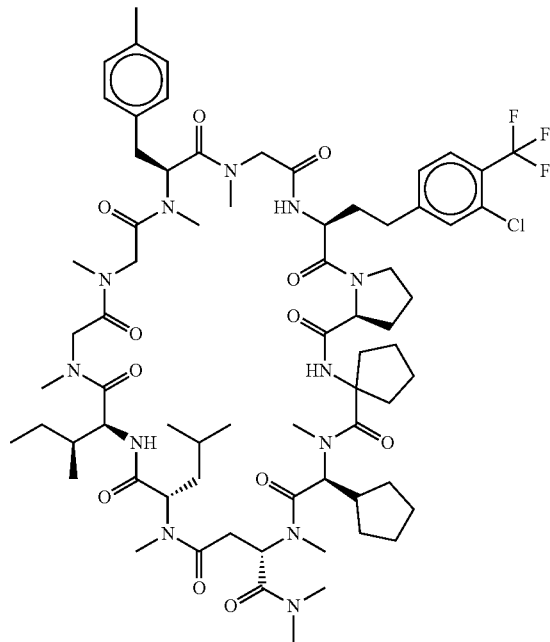 |
| 1780 | 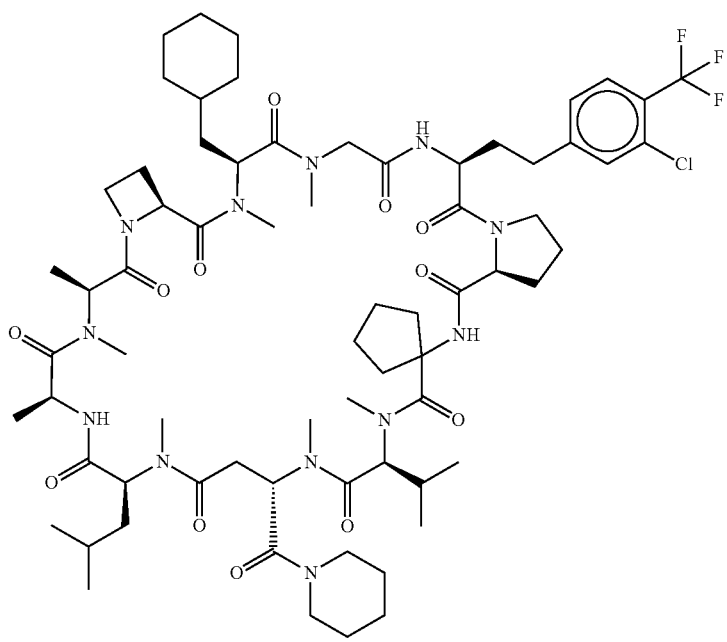 |

TABLE 24-continued
| Compound No. | Structural formula |
|---|---|
| 1781 | 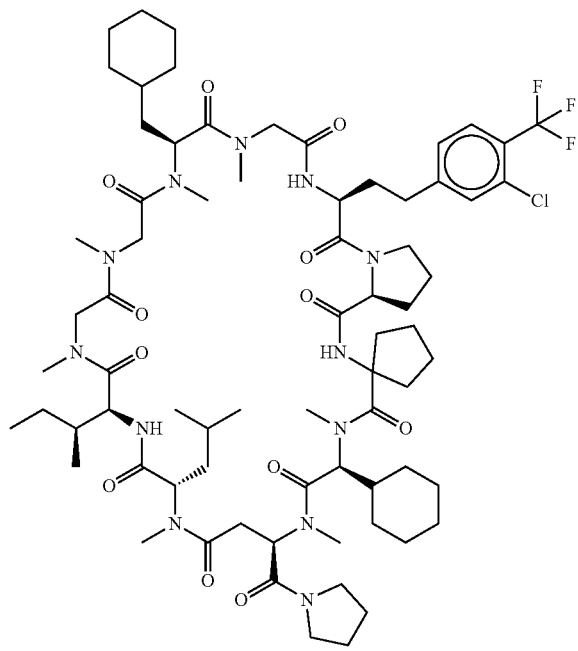 |
| 1782 | 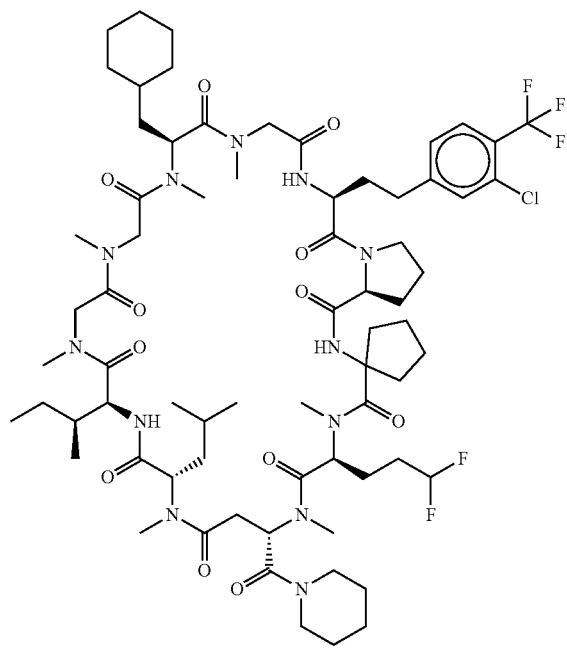 |

TABLE 24-continued

| Compound No. | Structural formula |
|---|---|
| 1783 | |
| 1784 | |

TABLE 24-continued
| Compound No. | Structural formula |
| --- | --- |
| 1785 | 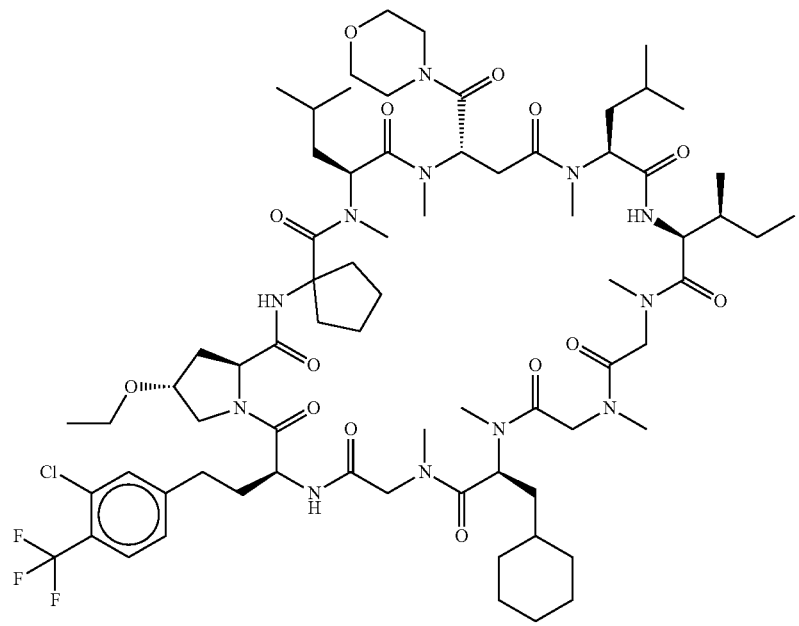 |
| 1786 | 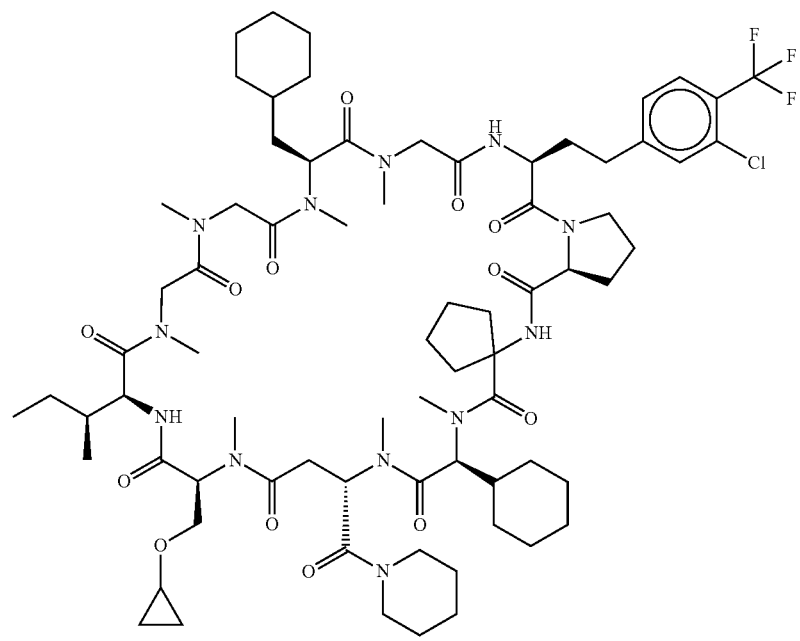 |

TABLE 24-continued
| Compound No. | Structural formula |
|---|---|
| 1787 | 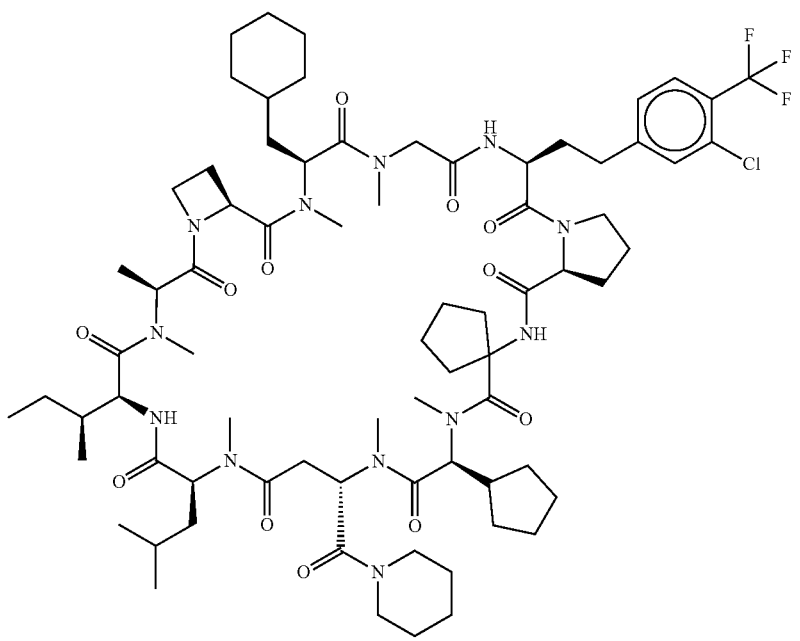 |
| 1788 | 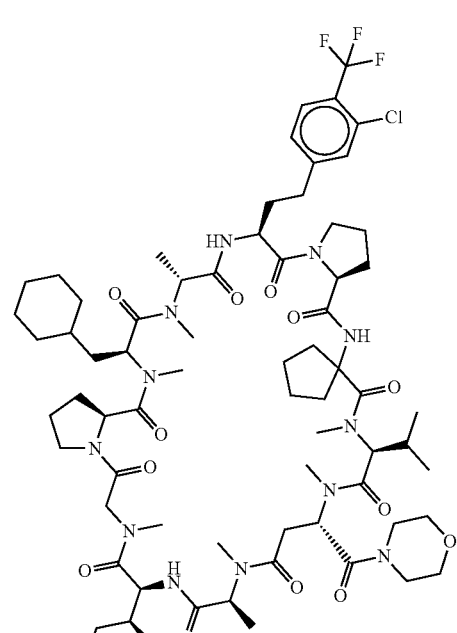 |

TABLE 24-continued
| Compound No. | Structural formula |
|---|---|
| 1789 | 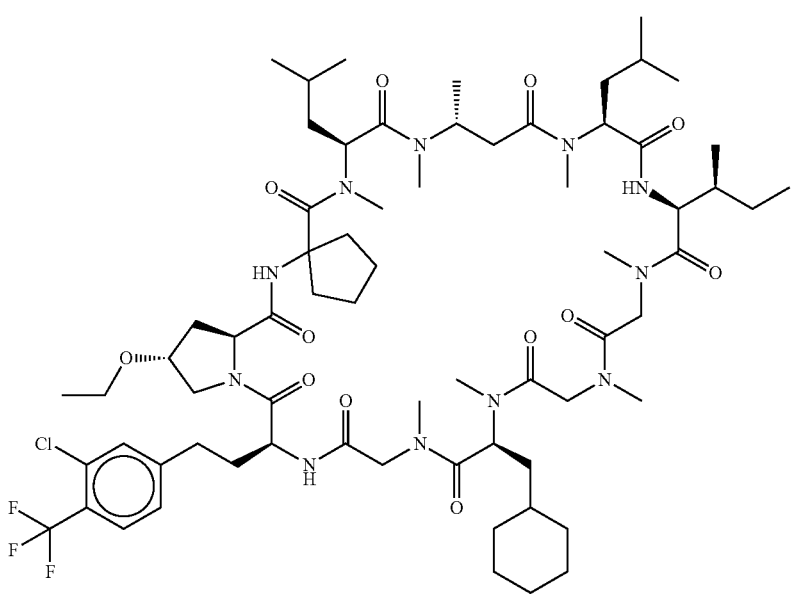 |
| 1790 | 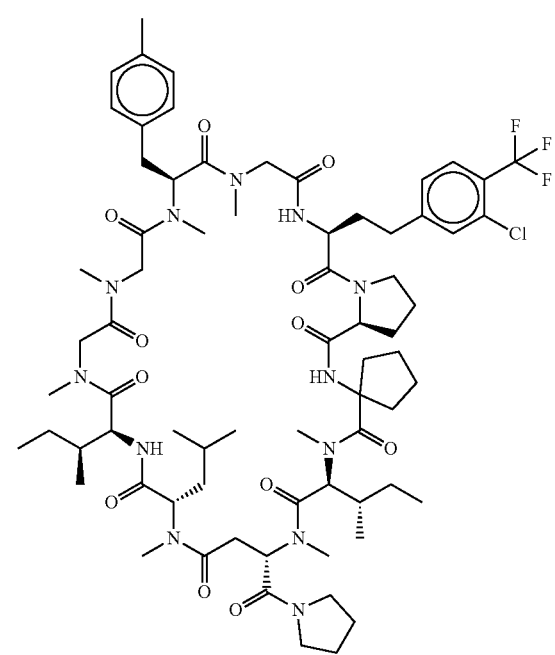 |

TABLE 24-continued
| Compound No. | Structural formula |
|---|---|
| 1791 | 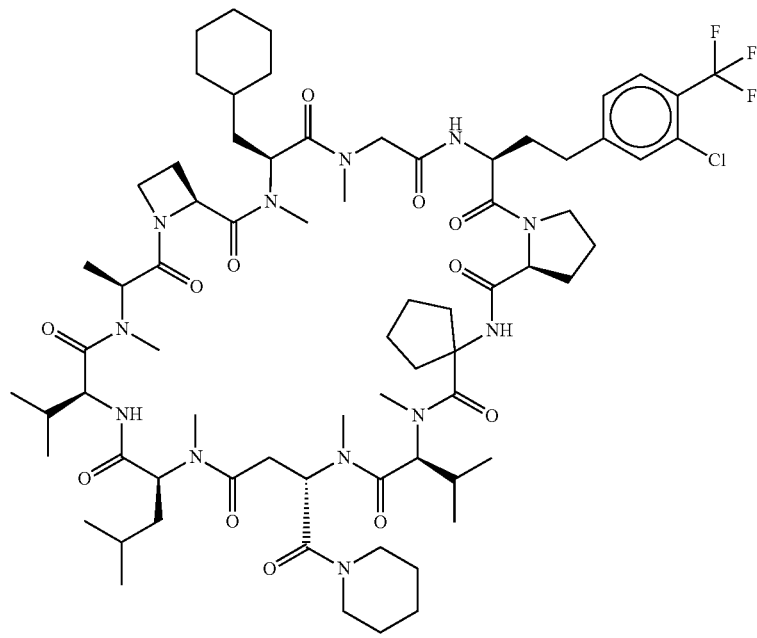 |
| 1792 | 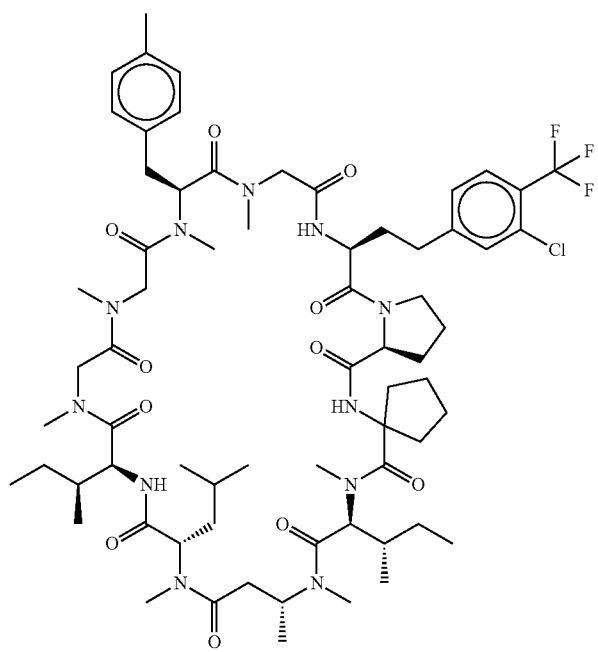 |

TABLE 24-continued
| Compound No. | Structural formula |
|---|---|
| 1793 | 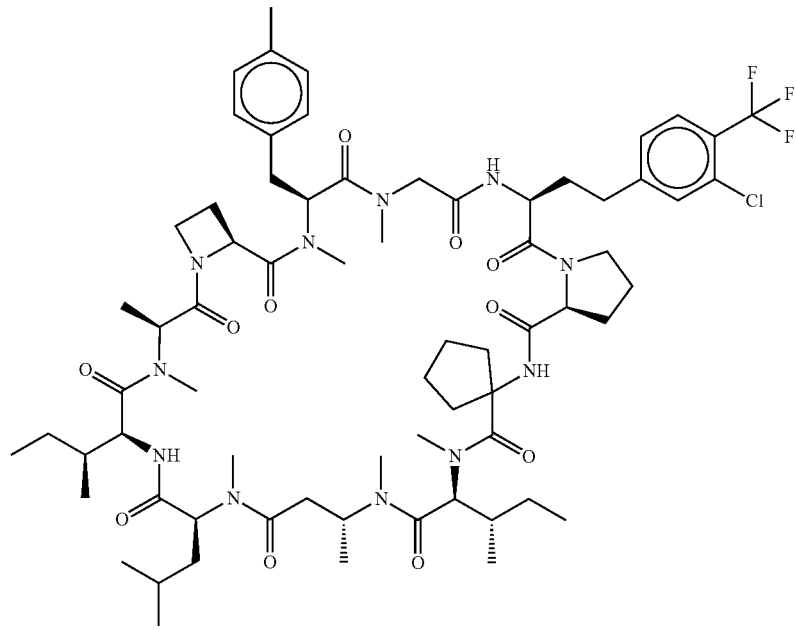 |
| 1794 | 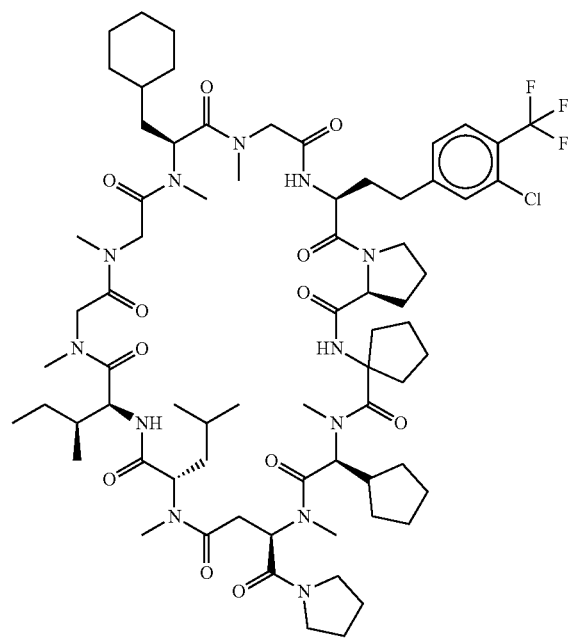 |

TABLE 24-continued
| Compound No. | Structural formula |
|---|---|
| 1795 | 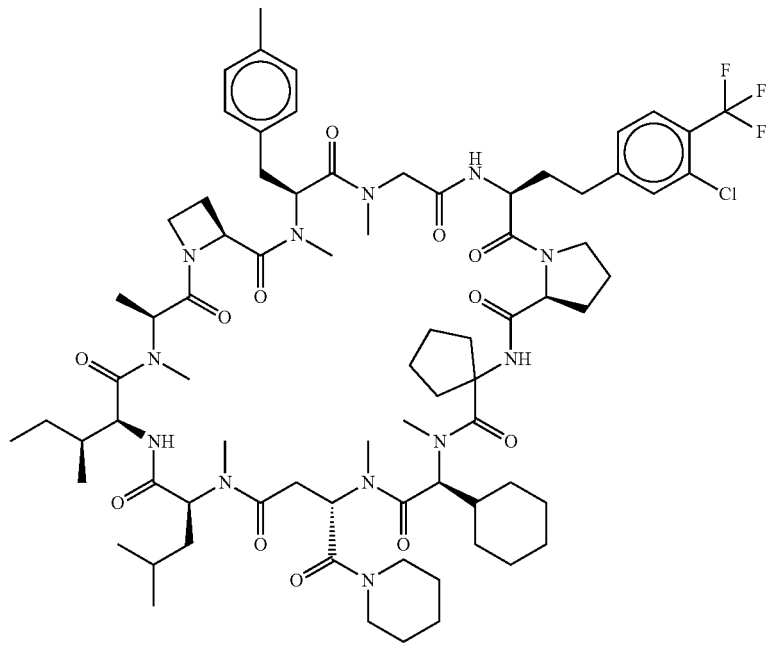 |
| 1796 | 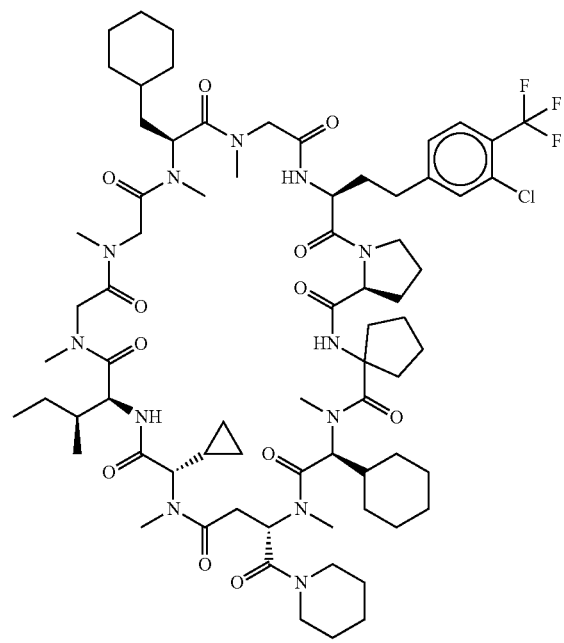 |

TABLE 24-continued
| Compound No. | Structural formula |
|---|---|
| 1797 | 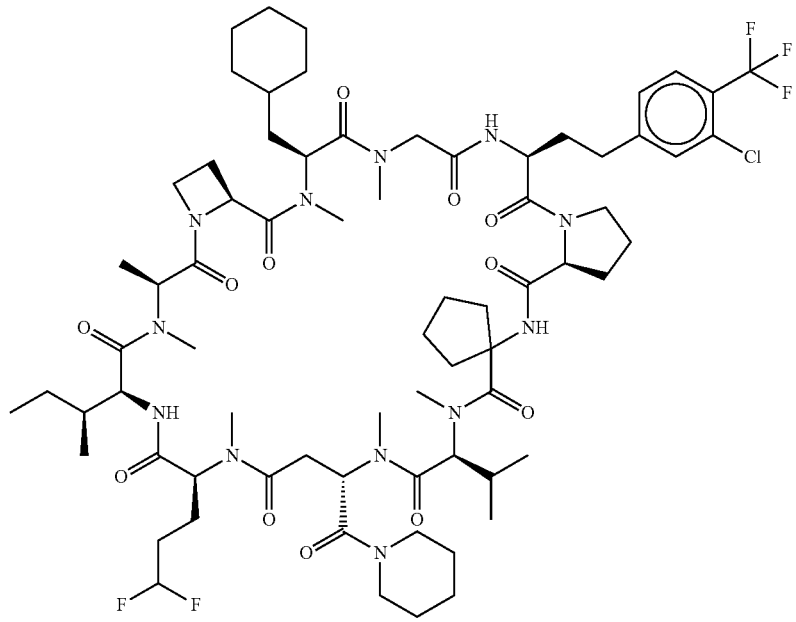 |
| 1798 | 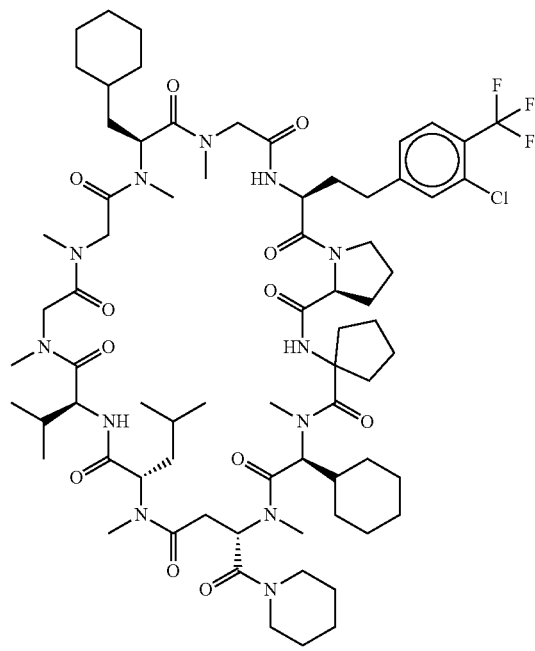 |

TABLE 24-continued
| Compound No. | Structural formula |
| --- | --- |
| 1799 | 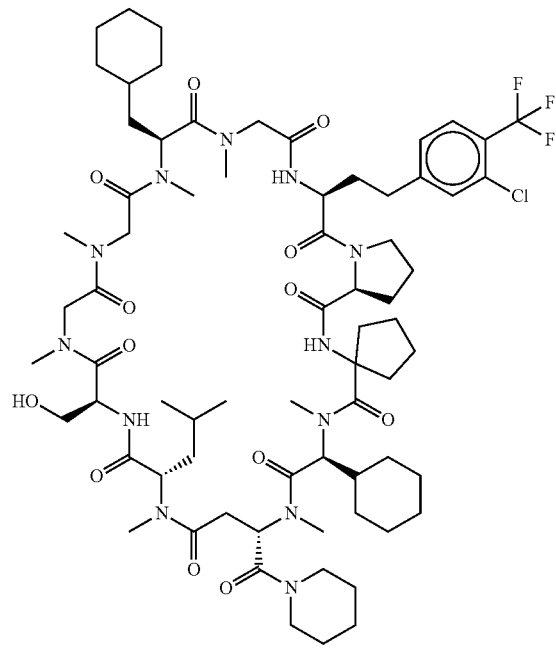 |
| 1800 | 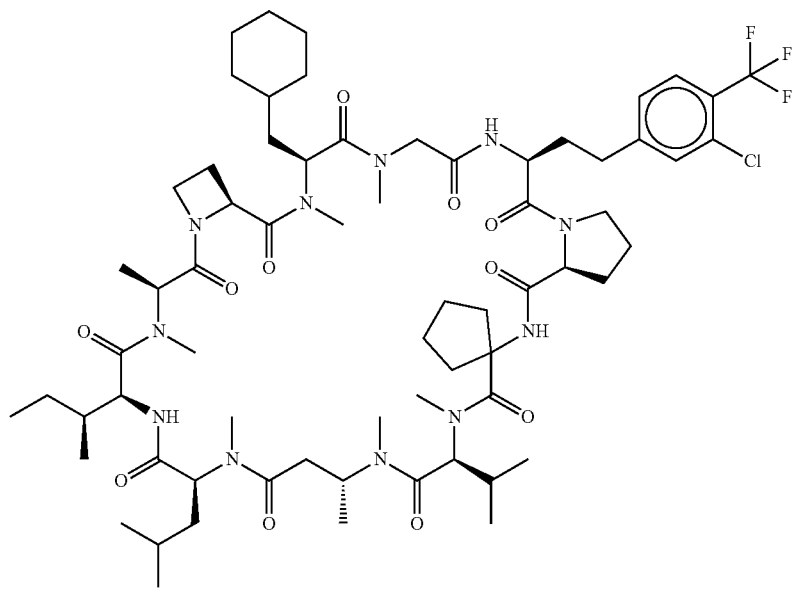 |

TABLE 24-continued
| Compound No. | Structural formula |
|---|---|
| 1801 | 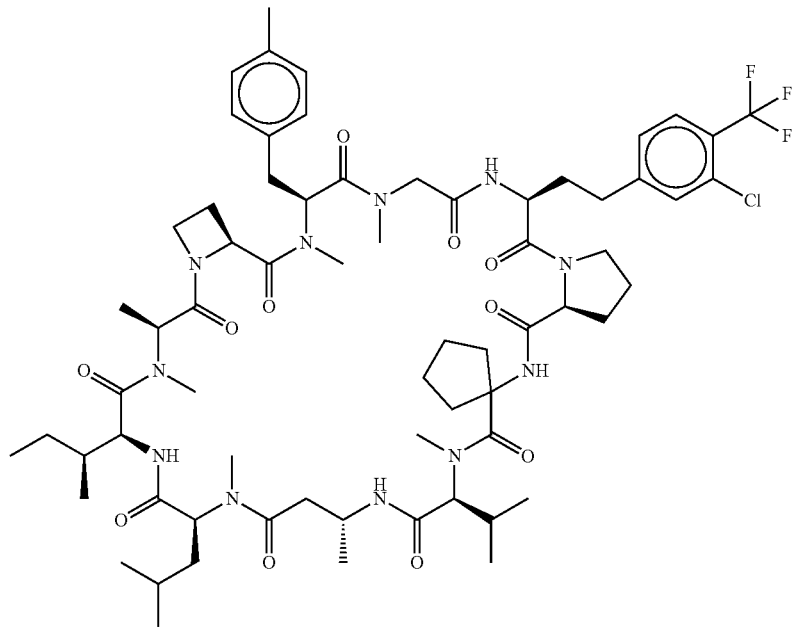 |
| 1802 | 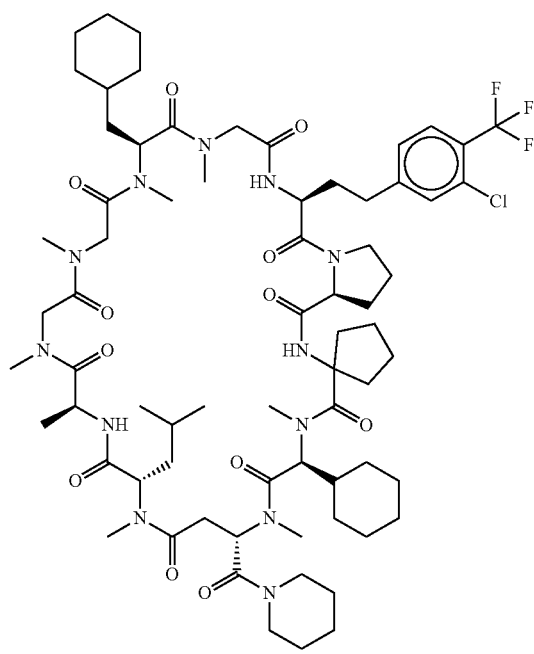 |

TABLE 24-continued
| Compound No. | Structural formula |
|---|---|
| 1803 | 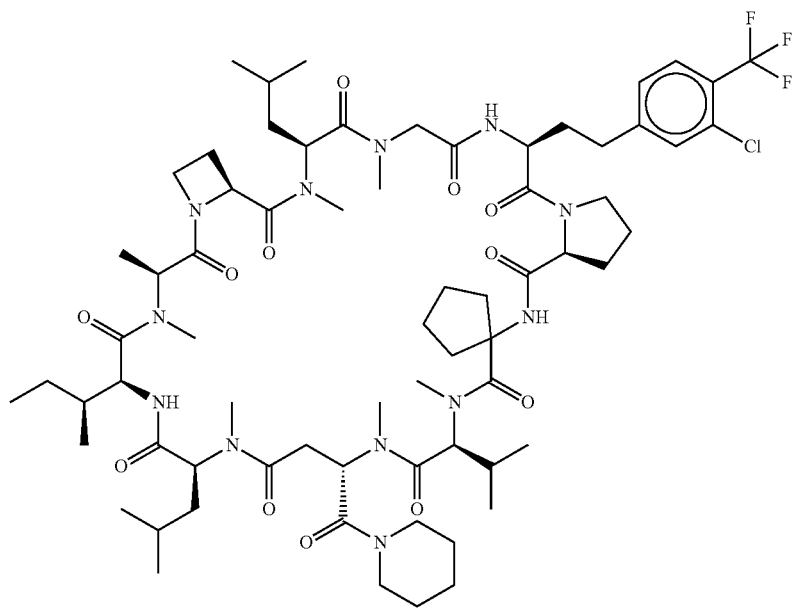 |
| 1804 | 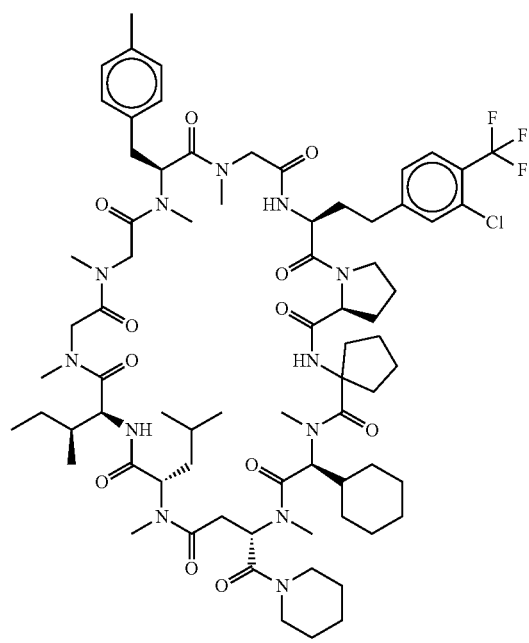 |

TABLE 24-continued
| Compound No. | Structural formula |
|---|---|
| 1805 | 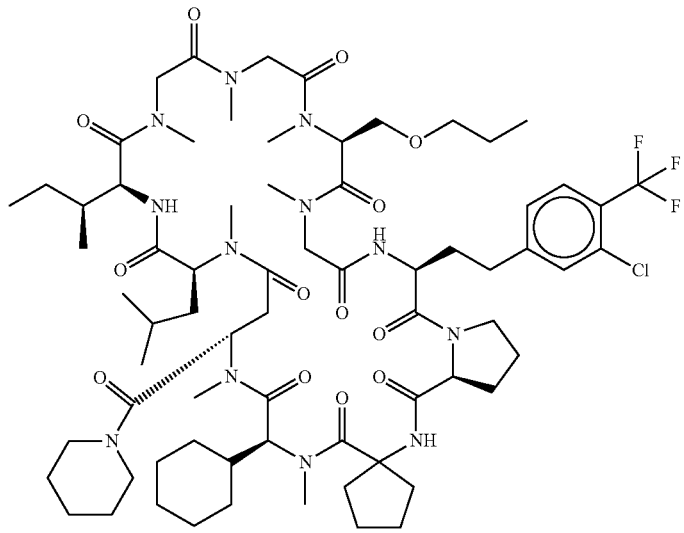 |
| 1806 | 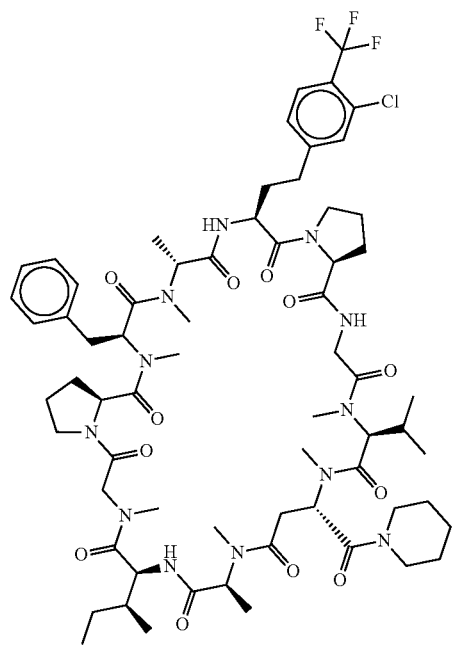 |

TABLE 24-continued
| Compound No. | Structural formula |
|---|---|
| 1807 | 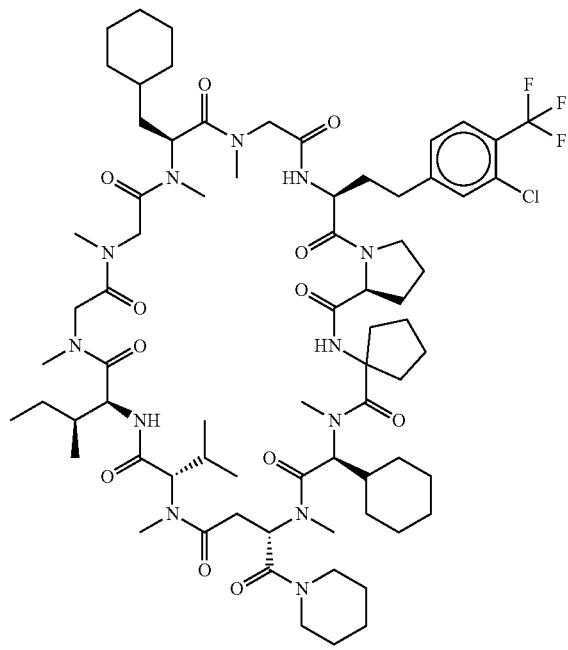 |
| 1808 | 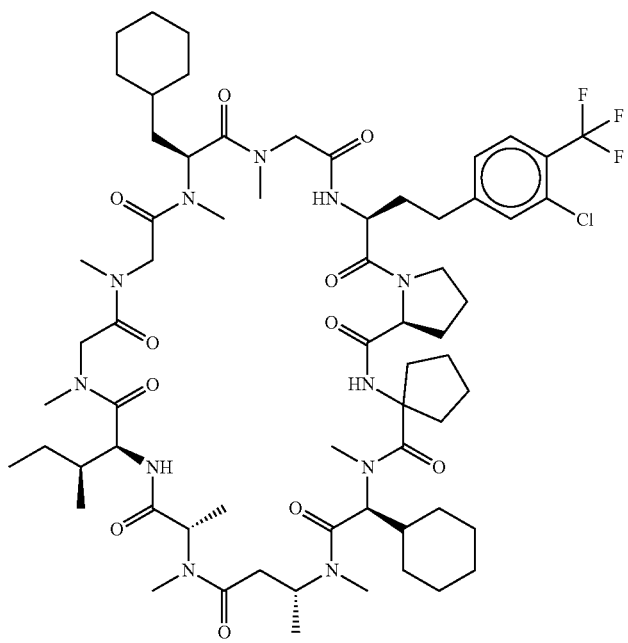 |

TABLE 24-continued
| Compound No. | Structural formula |
|---|---|
| 1809 | 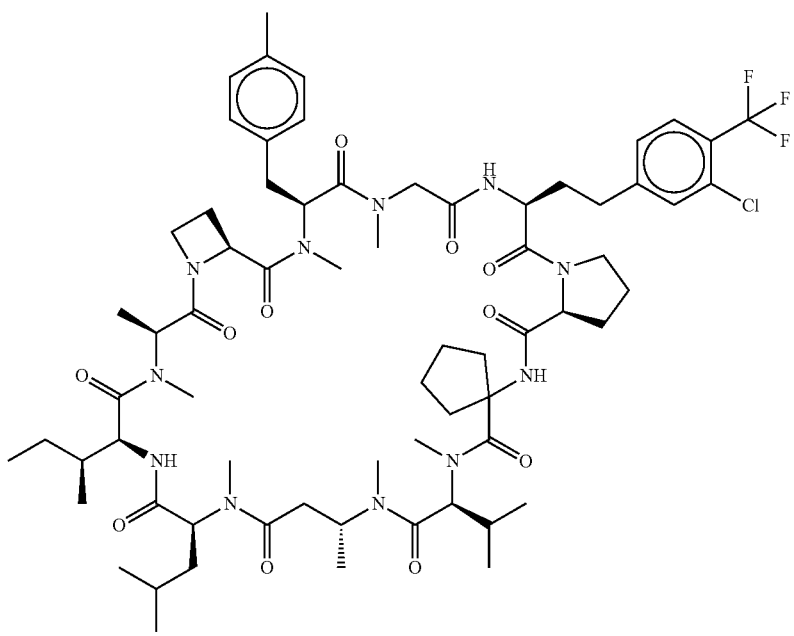 |
| 1810 | 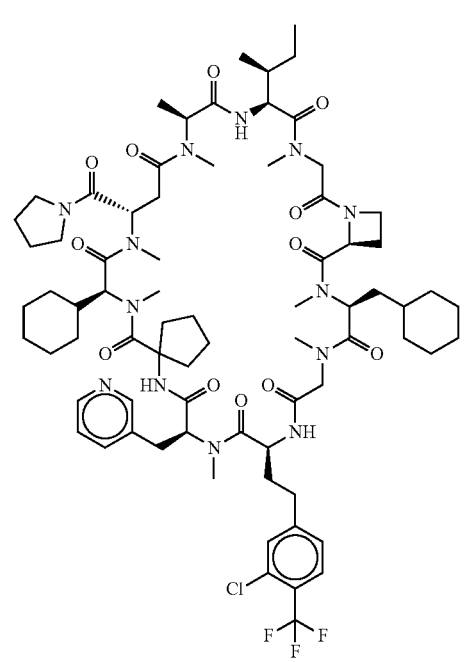 |

TABLE 24-continued
| Compound No. | Structural formula |
|---|---|
| 1811 | 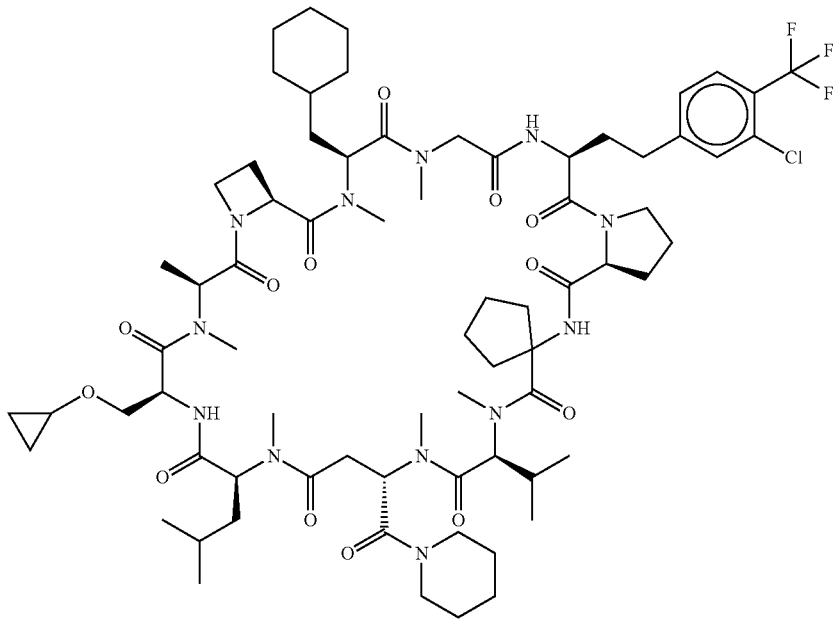 |
| 1812 | 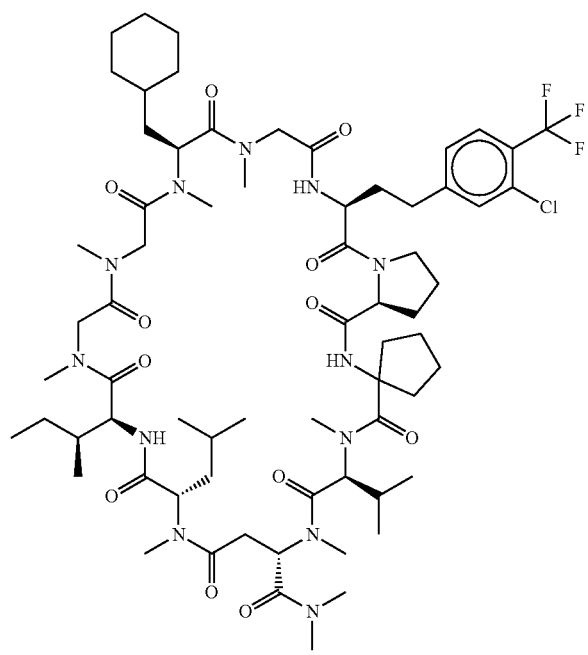 |

| Compound No. | Structural formula |
|---|---|
| 1813 | 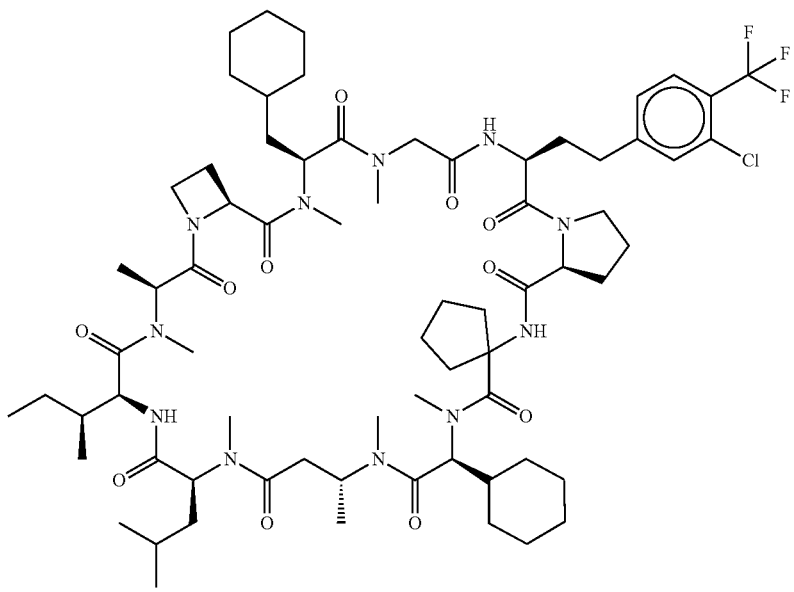 |
| 1814 | 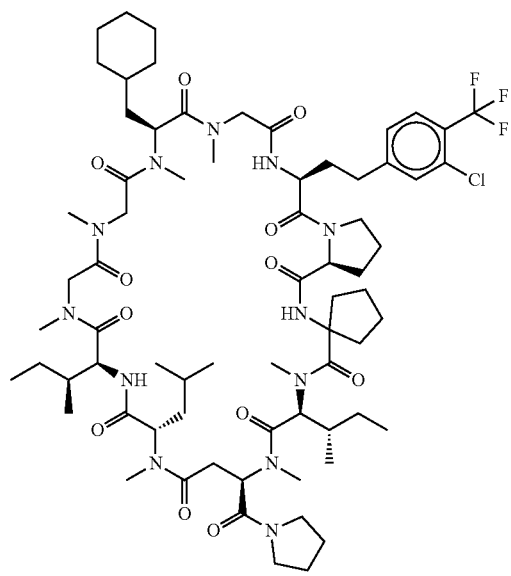 |

TABLE 24-continued
| Compound No. | Structural formula |
|---|---|
| 1815 | 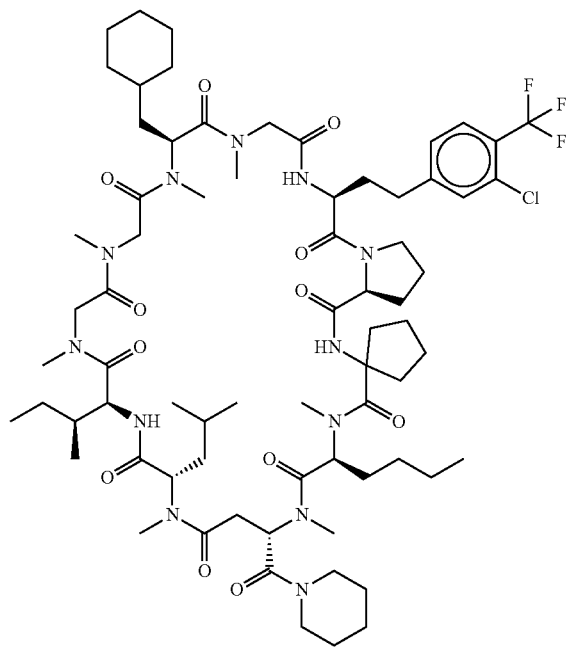 |
| 1816 | 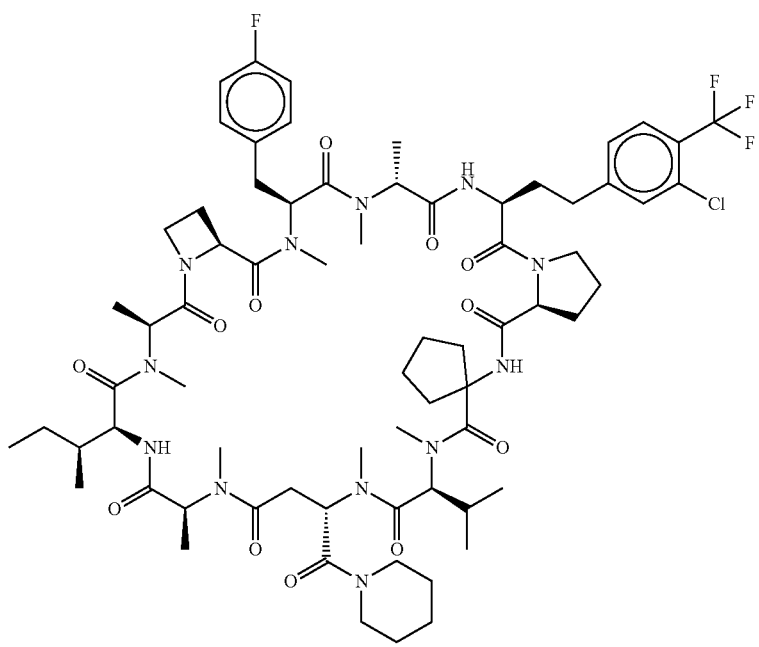 |

TABLE 24-continued
| Compound No. | Structural formula |
|---|---|
| 1817 | 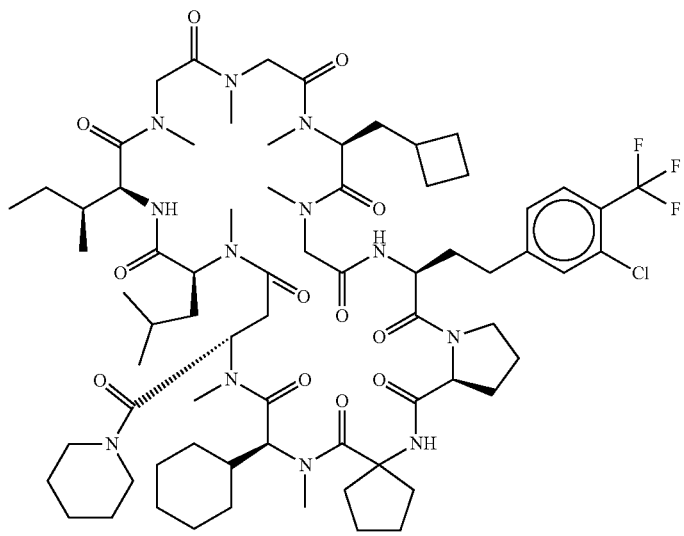 |
| 1818 | 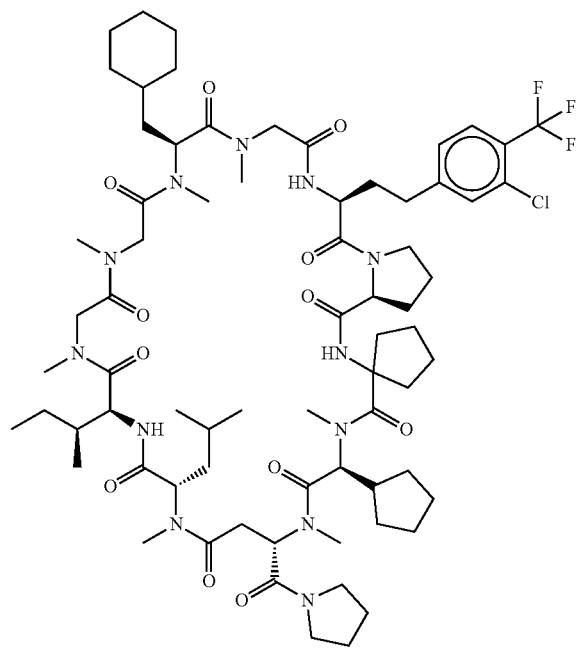 |

TABLE 24-continued
| Compound No. | Structural formula |
|---|---|
| 1819 | 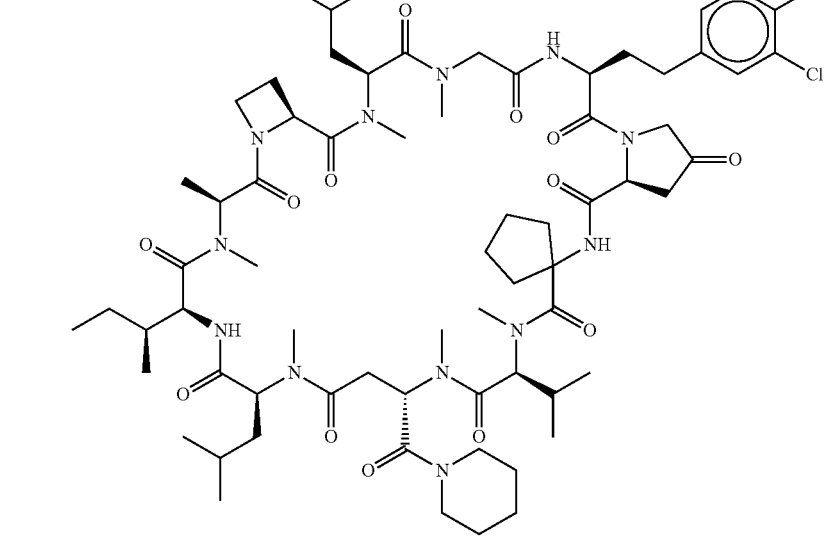 |
| 1820 | 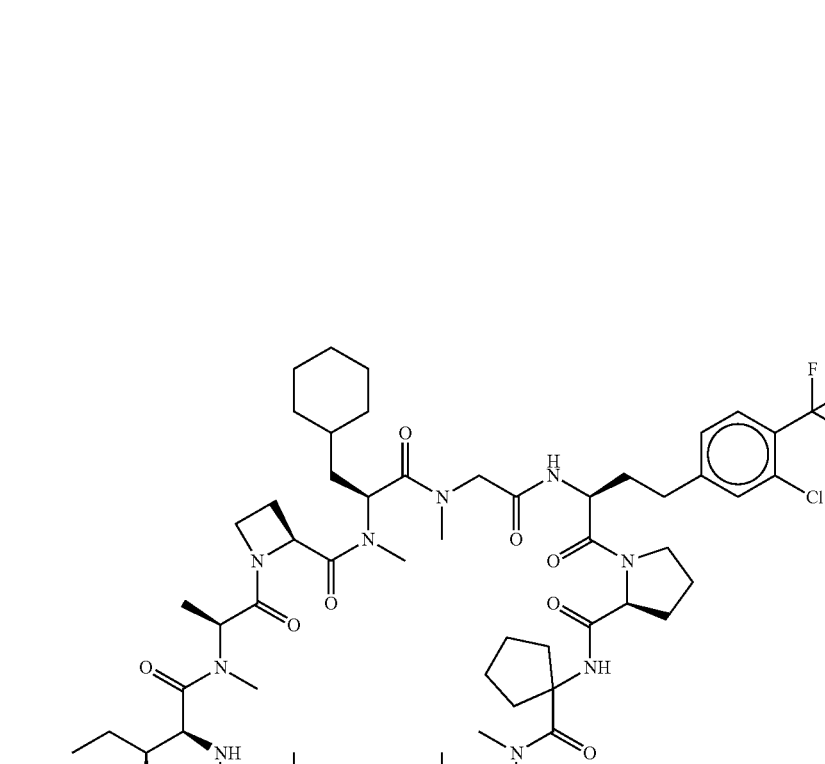 |

TABLE 24-continued
| Compound No. | Structural formula |
|---|---|
| 1821 | 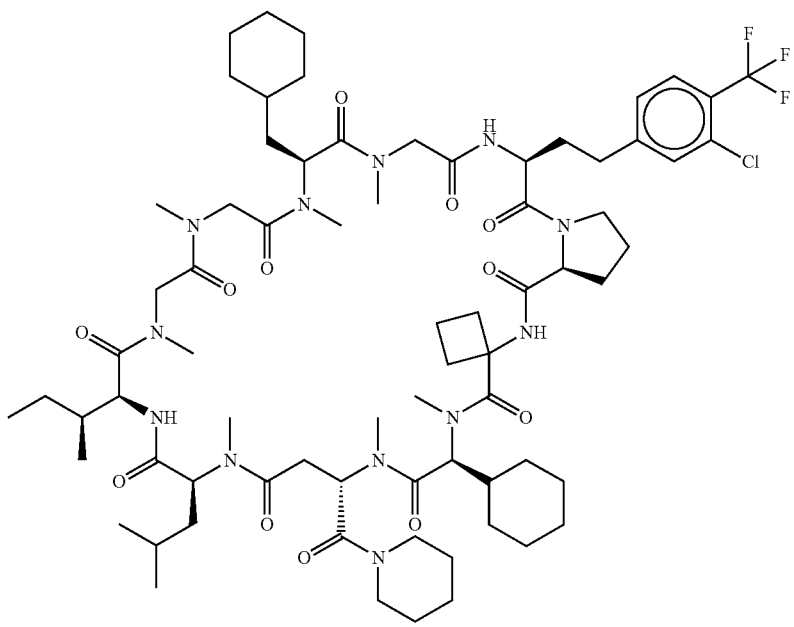 |
| 1822 | 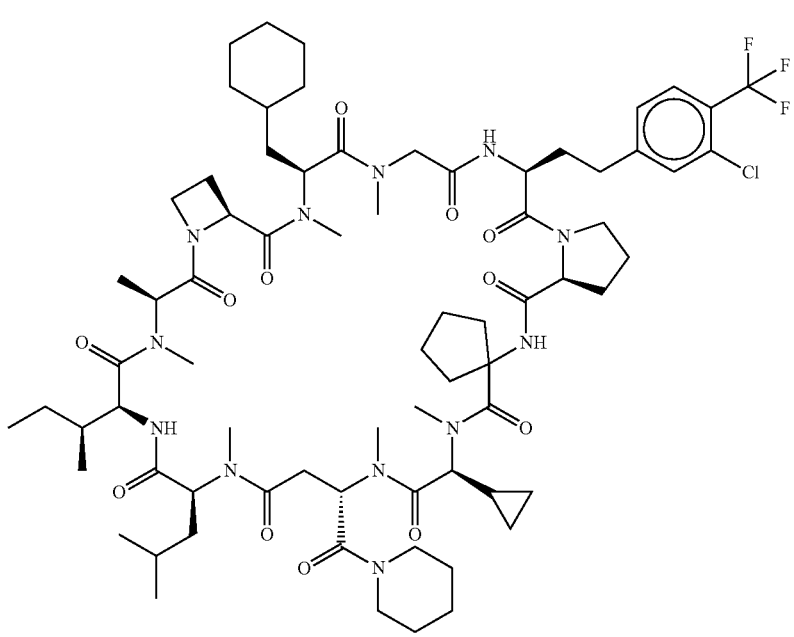 |

TABLE 24-continued
| Compound No. | Structural formula |
| --- | --- |
| 1823 | 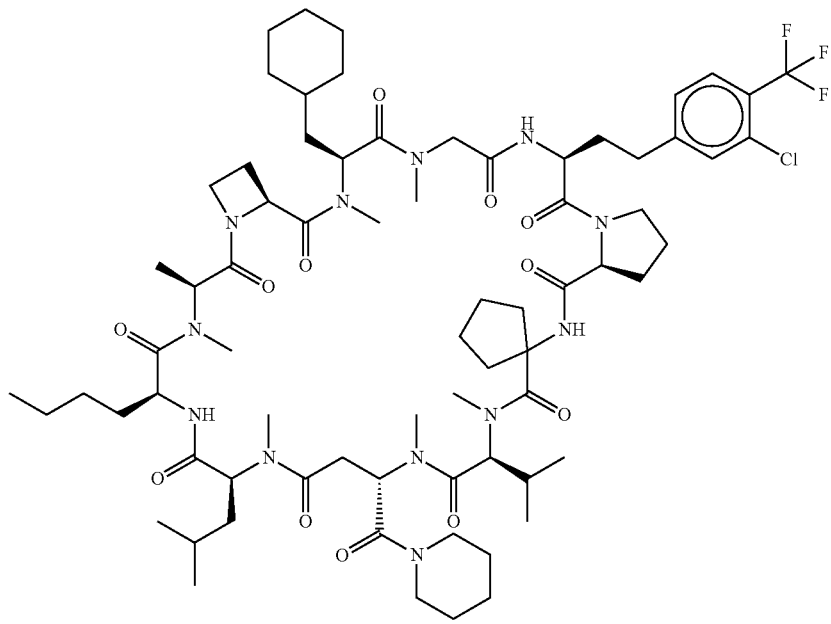 |
| 1824 | 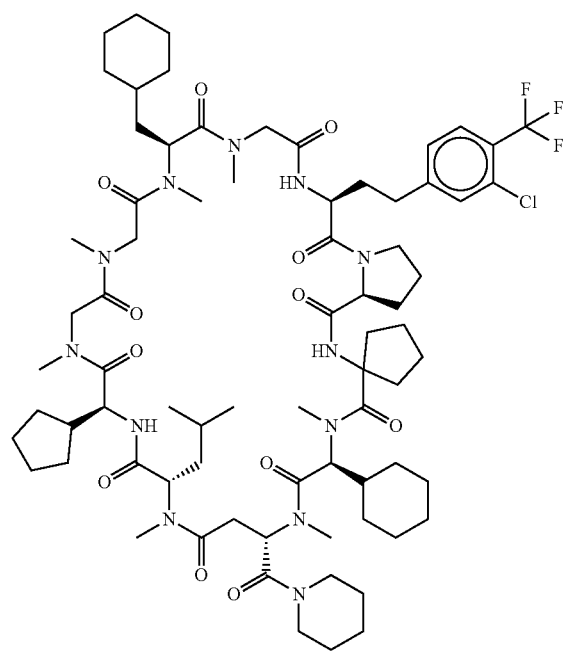 |

TABLE 24-continued
| Compound No. | Structural formula |
| --- | --- |
| 1825 | 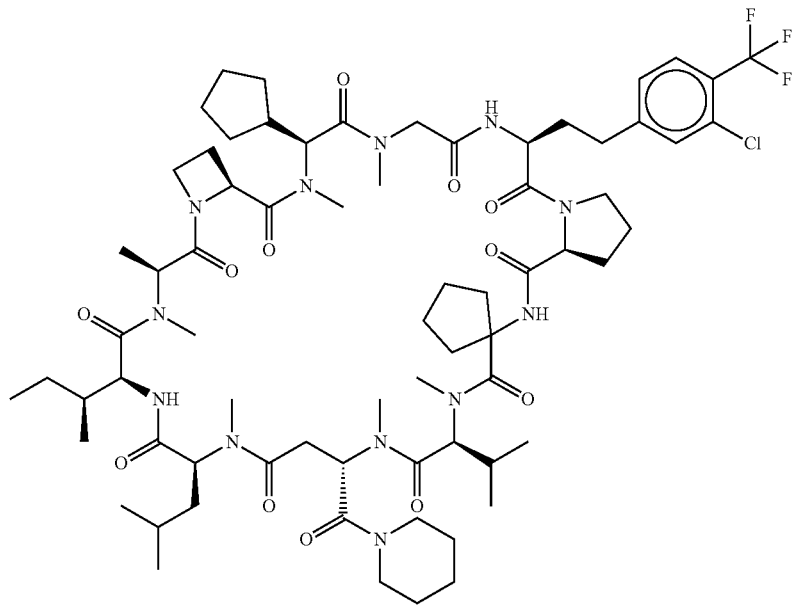 |
| 1826 | 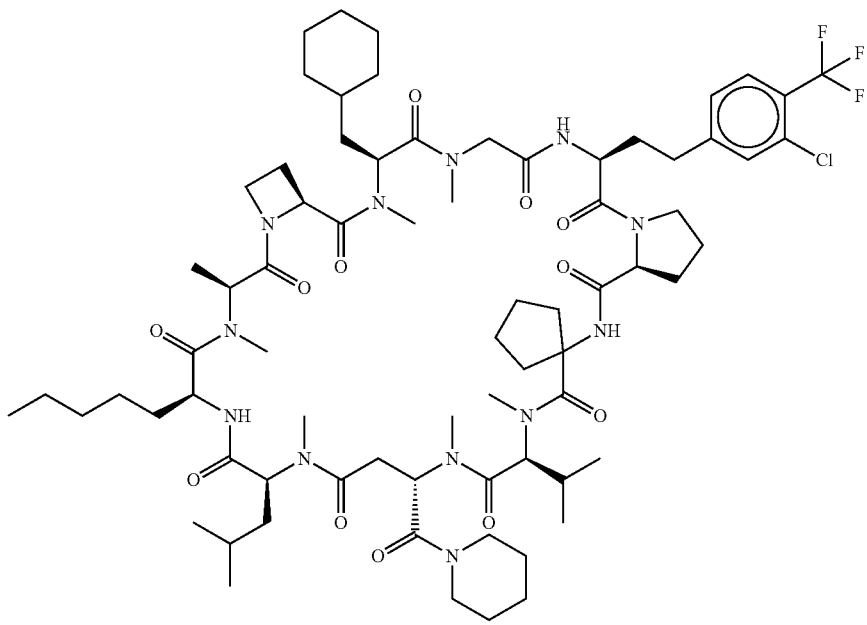 |

TABLE 24-continued
| Compound No. | Structural formula |
|---|---|
| 1827 | 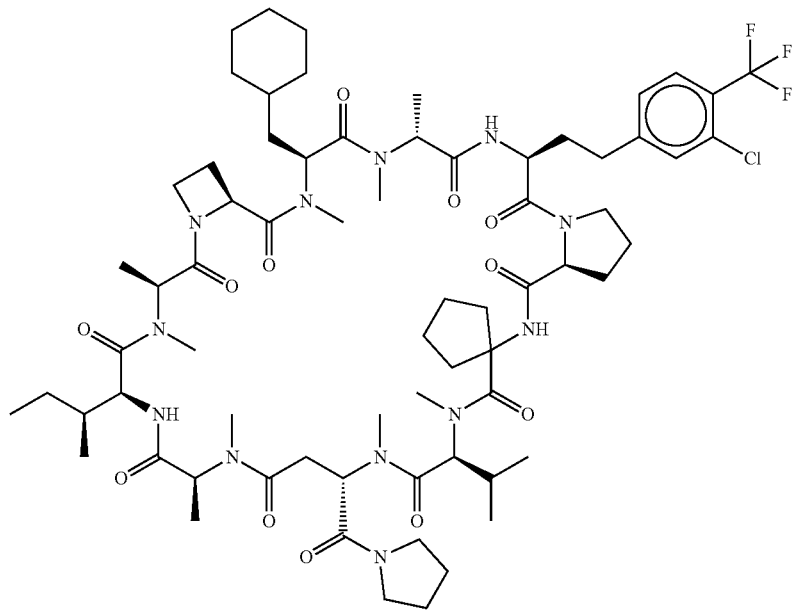 |
| 1828 | 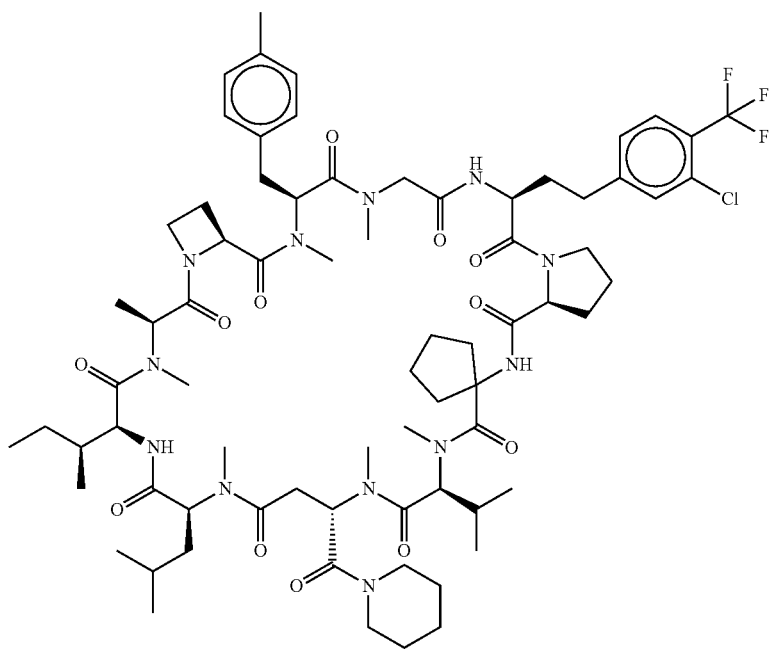 |

TABLE 24-continued
| Compound No. | Structural formula |
|---|---|
| 1829 | 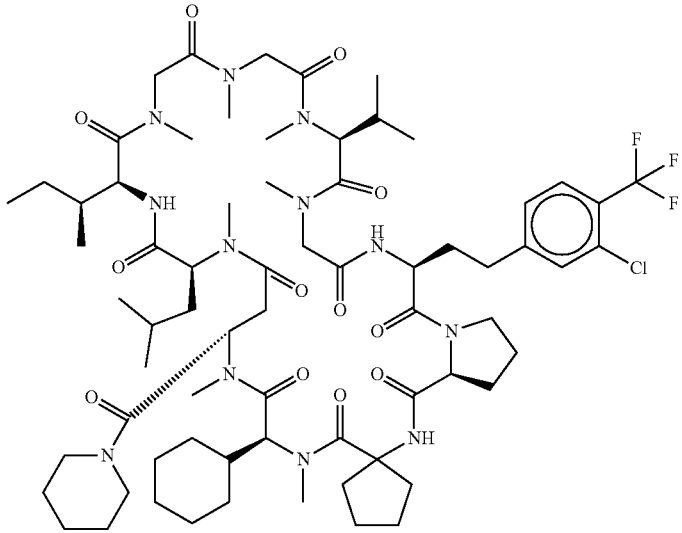 |
| 1830 | 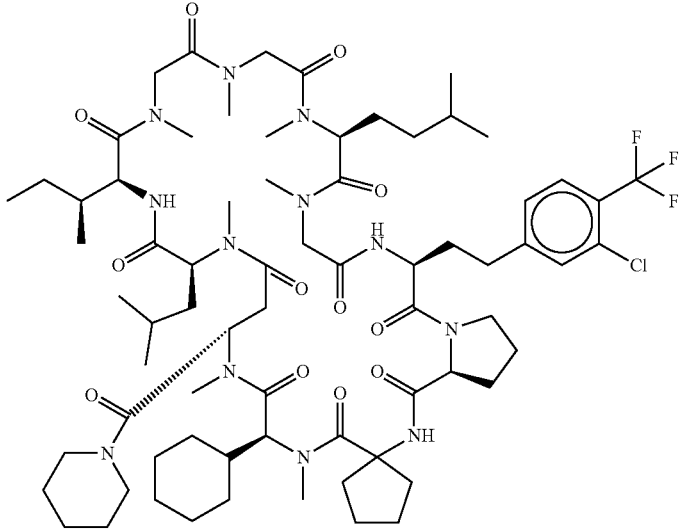 |

TABLE 24-continued
| Compound No. | Structural formula |
|---|---|
| 1831 | 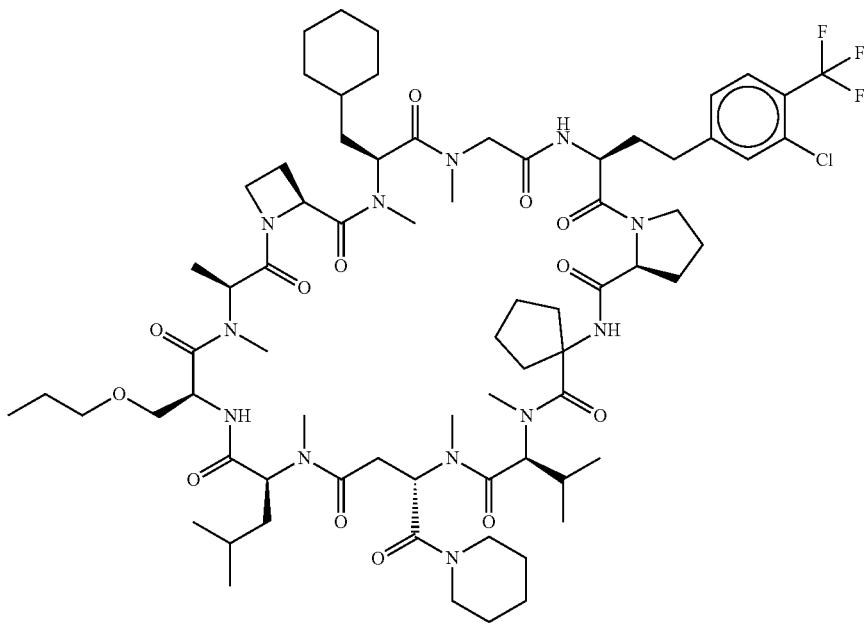 |
| 1832 | 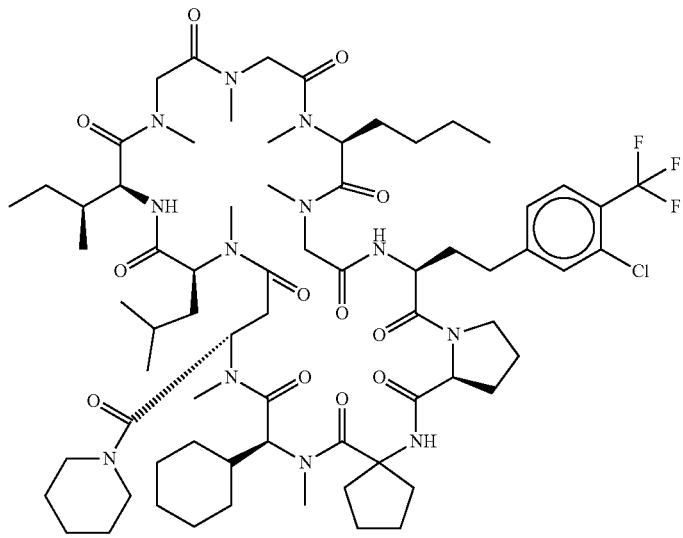 |

TABLE 24-continued
| Compound No. | Structural formula |
|---|---|
| 1833 | 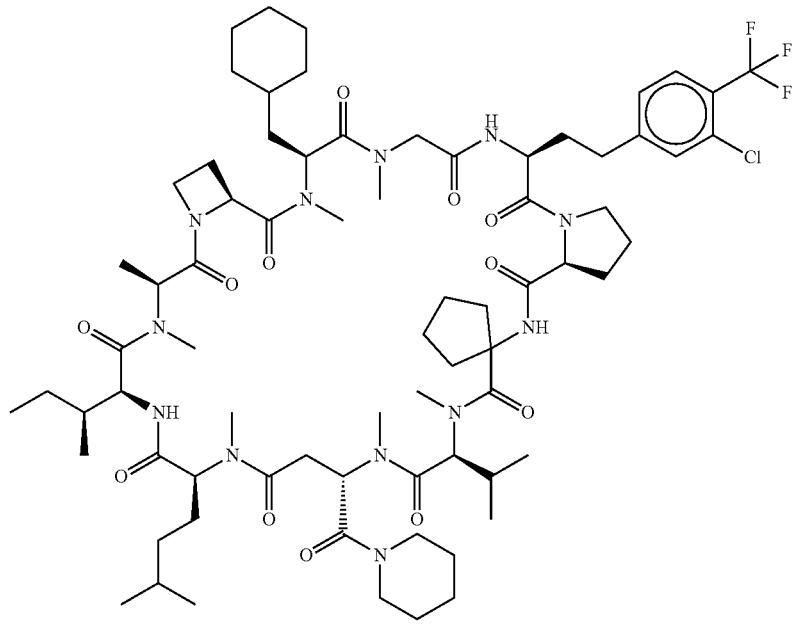 |
| 1834 | 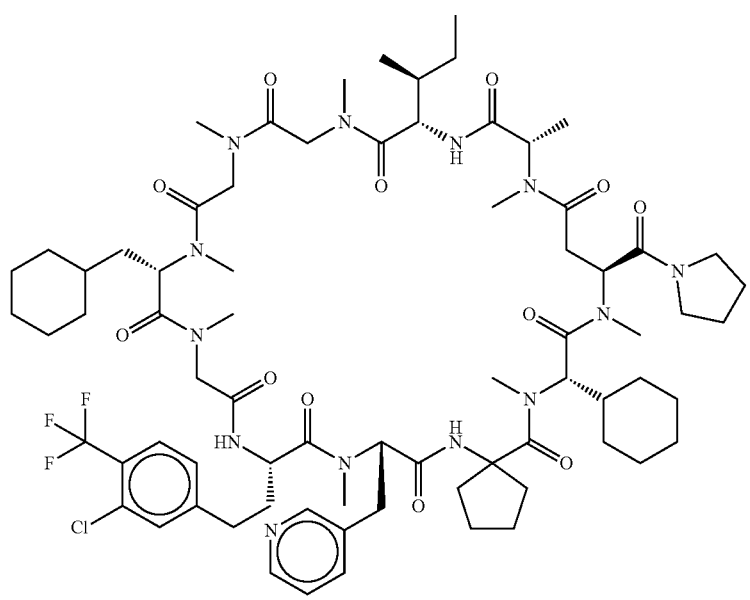 |

TABLE 24-continued
| Compound No. | Structural formula |
|---|---|
| 1835 | 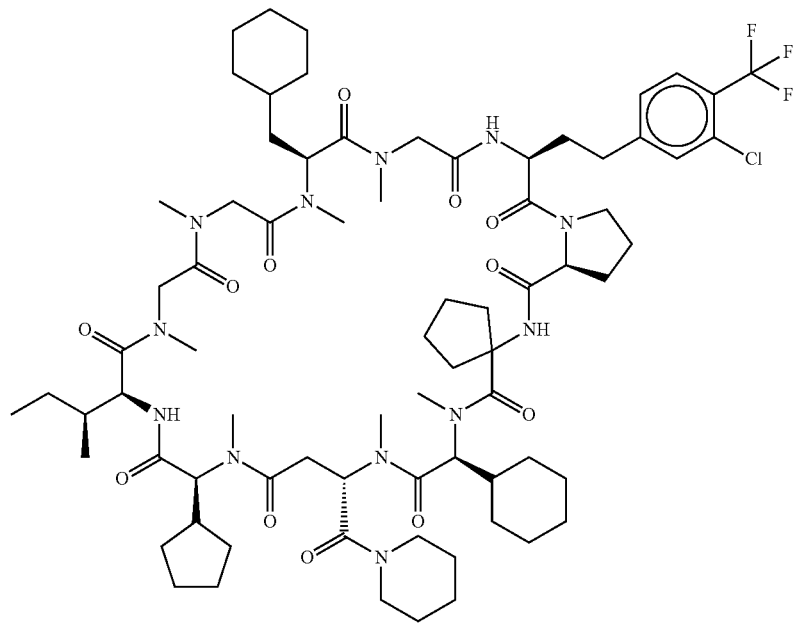 |
| 1836 | 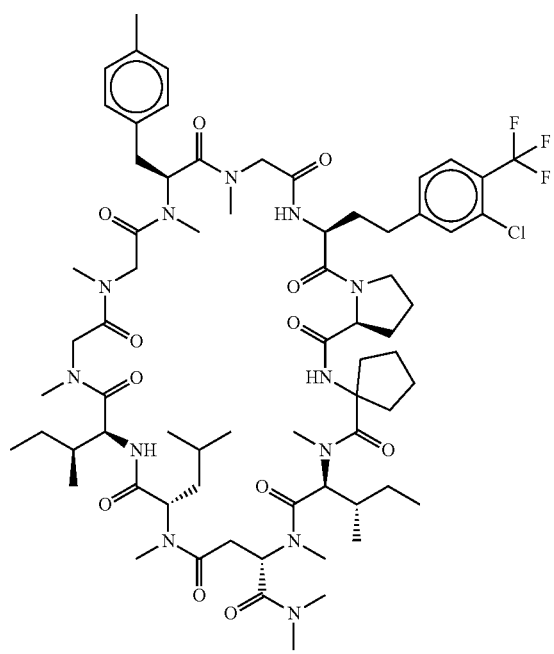 |

TABLE 24-continued
| Compound No. | Structural formula |
|---|---|
| 1837 | 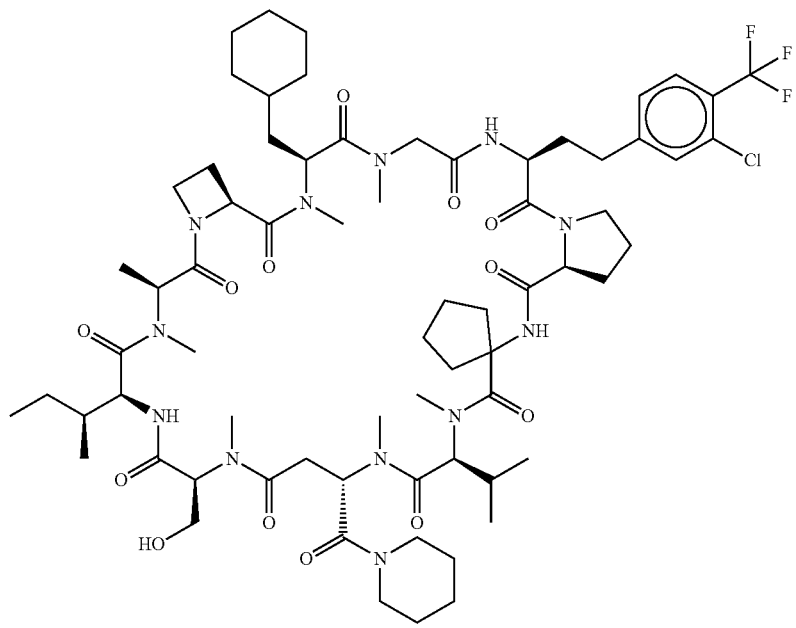 |
| 1838 | 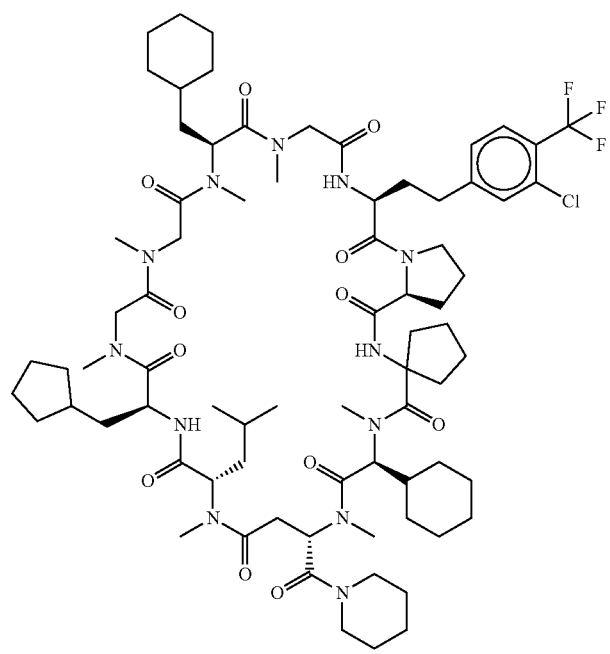 |

TABLE 24-continued
| Compound No. | Structural formula |
|---|---|
| 1839 | 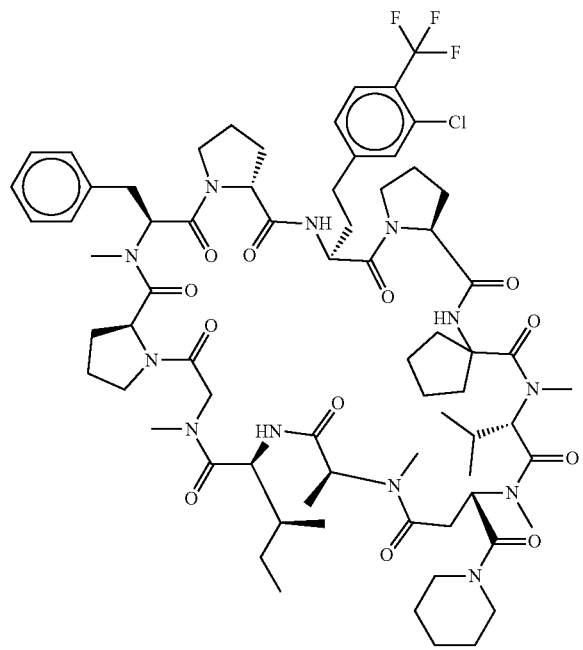 |
| 1840 | 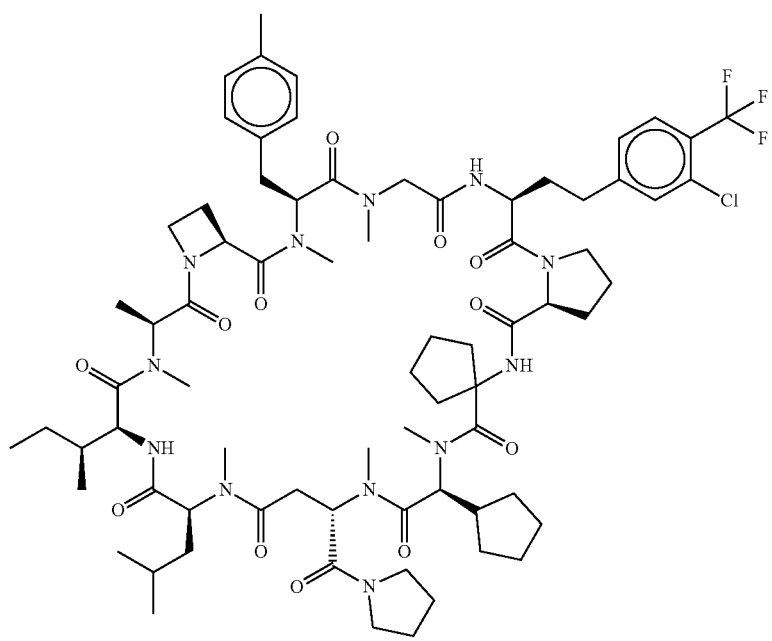 |

//
TABLE 24-continued
| Compound No. | Structural formula |
|---|---|
| 1841 | 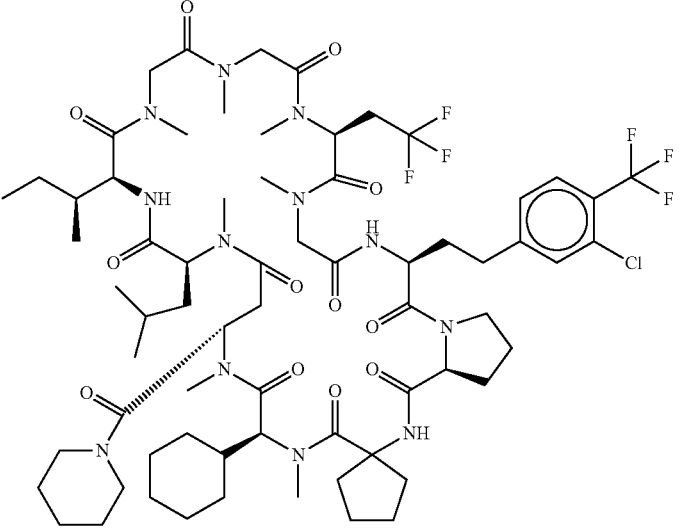 |
| 1842 | 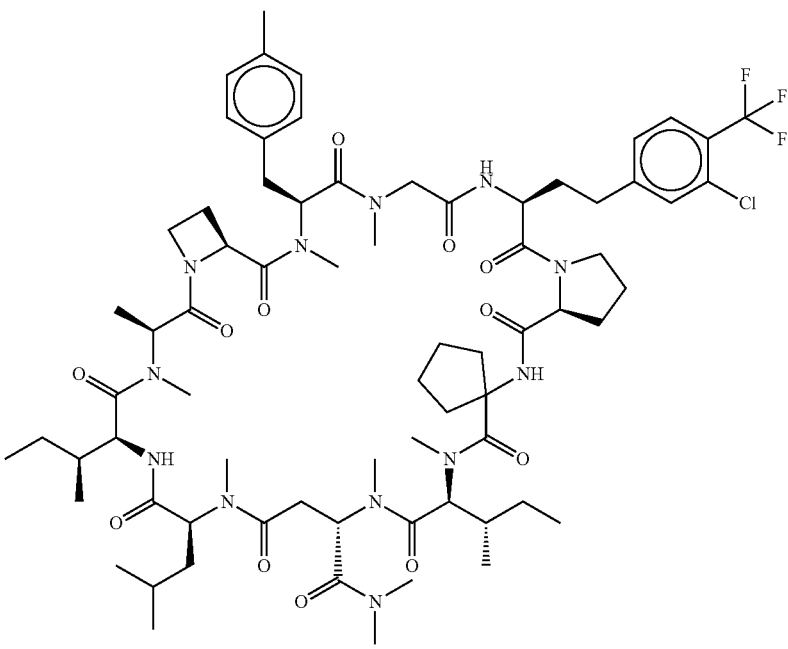 |

| Compound No. | Structural formula |
|---|---|
| 1843 | 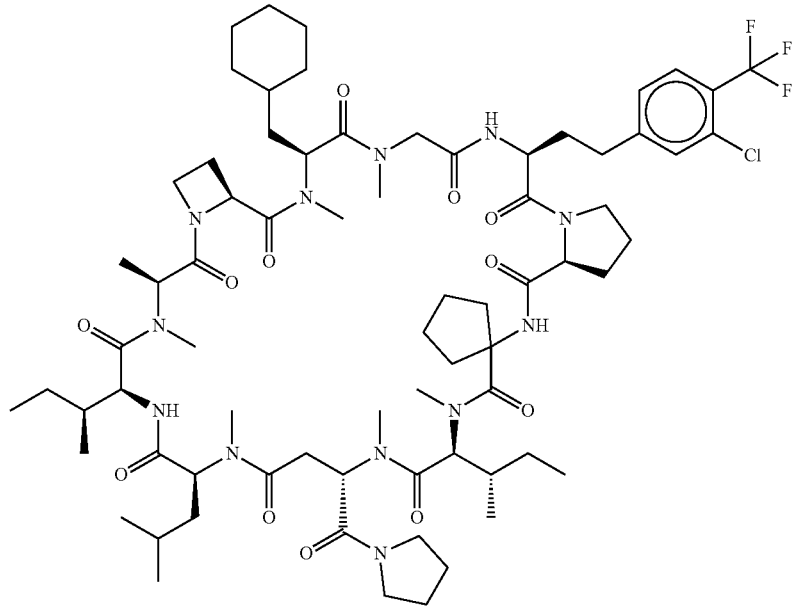 |
| 1844 | 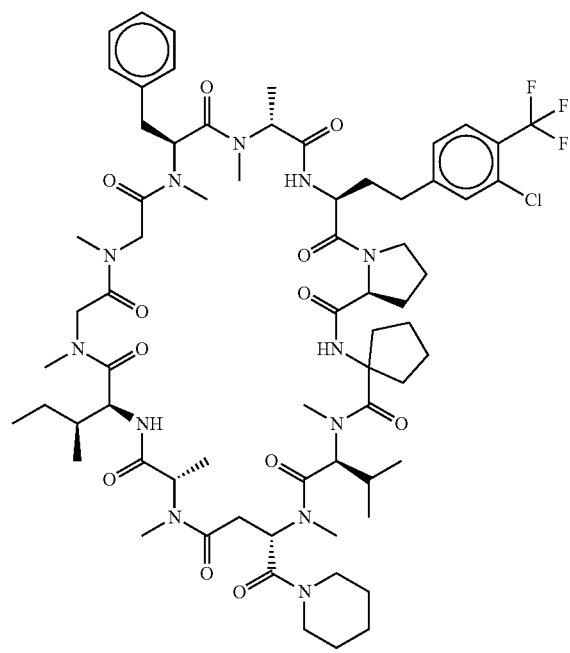 |

TABLE 24-continued
| Compound No. | Structural formula |
|---|---|
| 1845 | 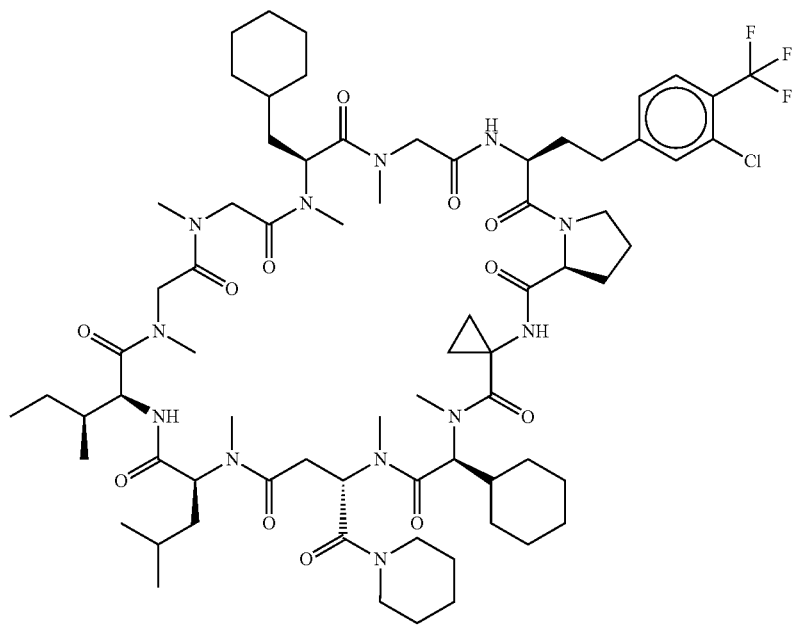 |
| 1846 | 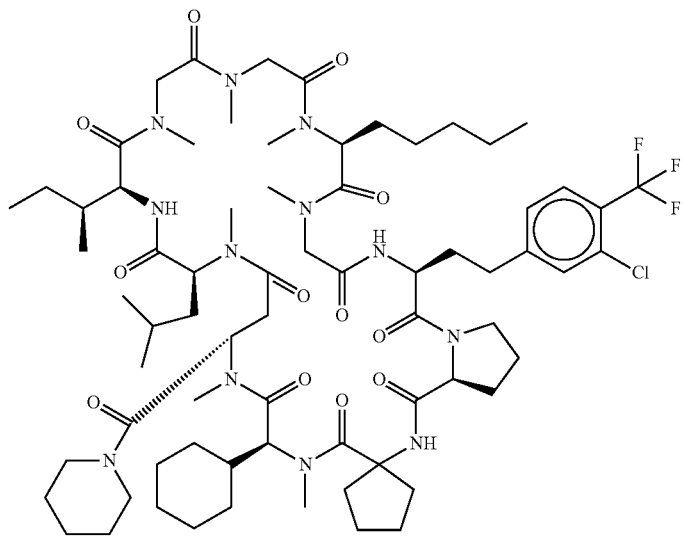 |

TABLE 24-continued
| Compound No. | Structural formula |
|---|---|
| 1847 | 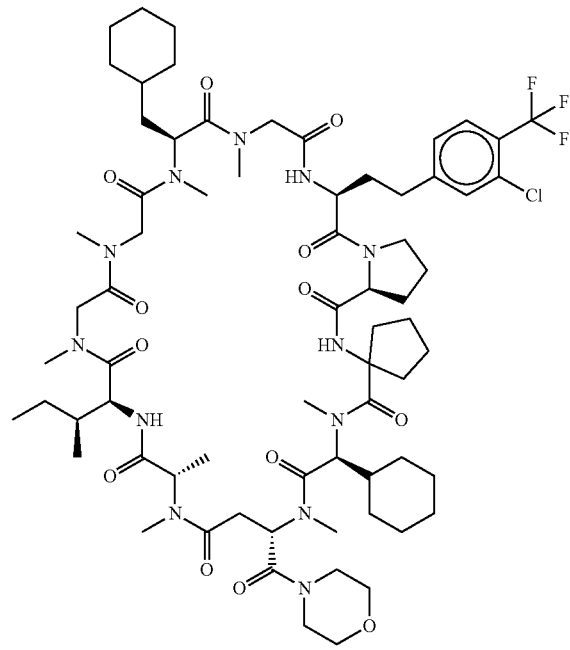 |
| 1848 | 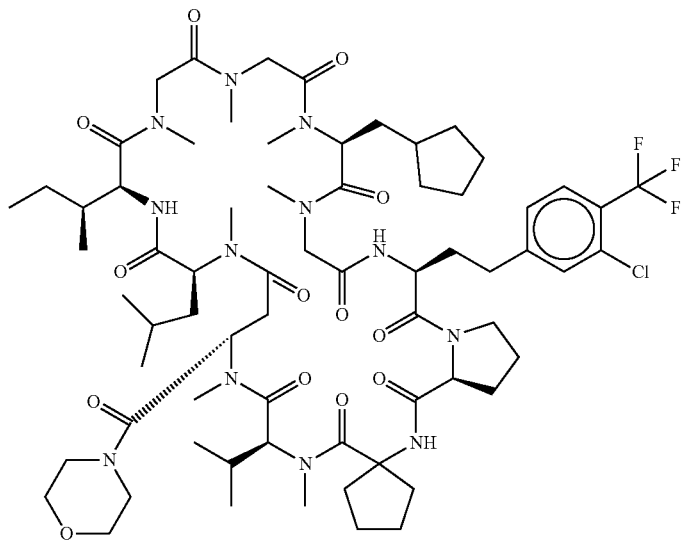 |

TABLE 24-continued
| Compound No. | Structural formula |
|---|---|
| 1849 | 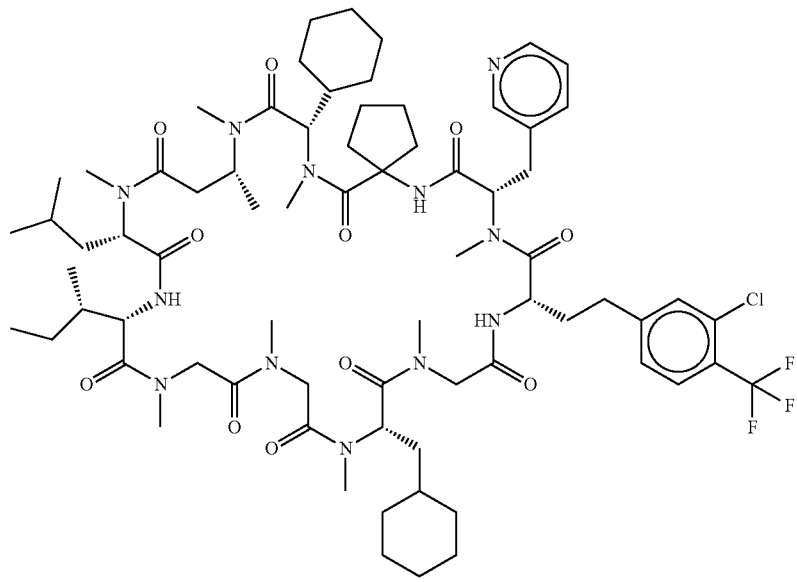 |
| 1850 | 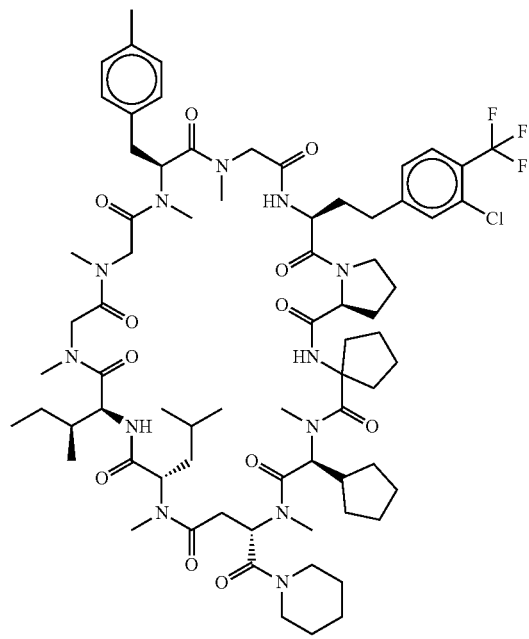 |

TABLE 24-continued
| Compound No. | Structural formula |
|---|---|
| 1851 | 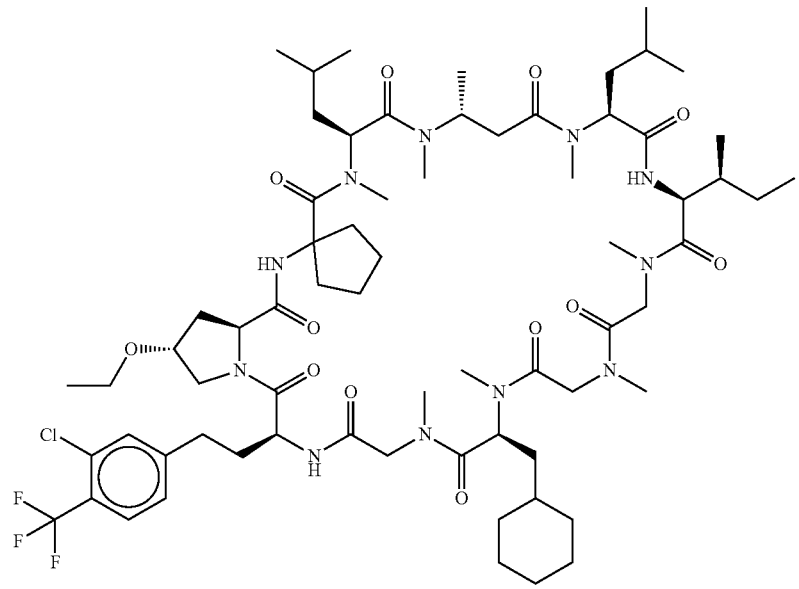 |
| 1852 | 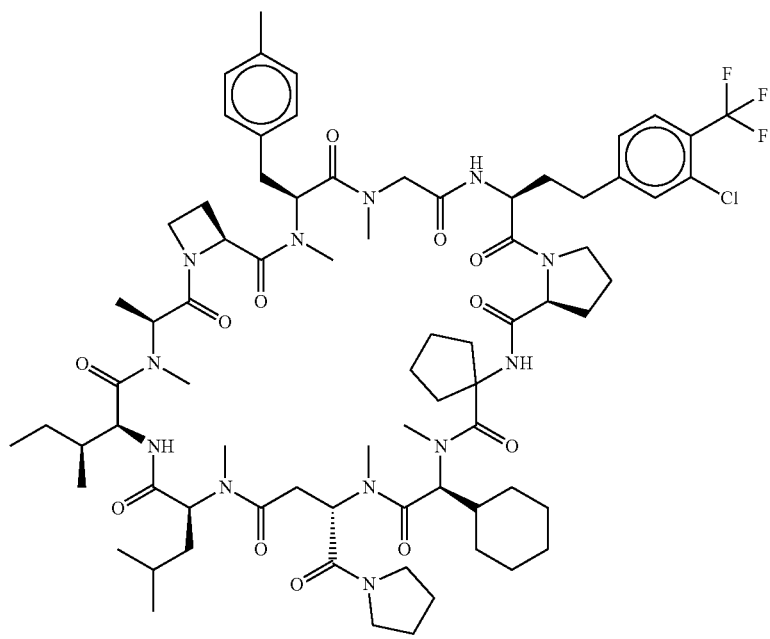 |

TABLE 24-continued
| Compound No. | Structural formula |
|---|---|
| 1853 | 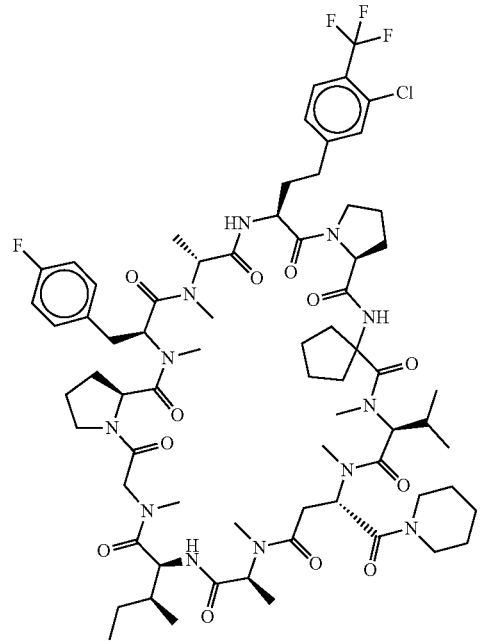 |
| 1854 | 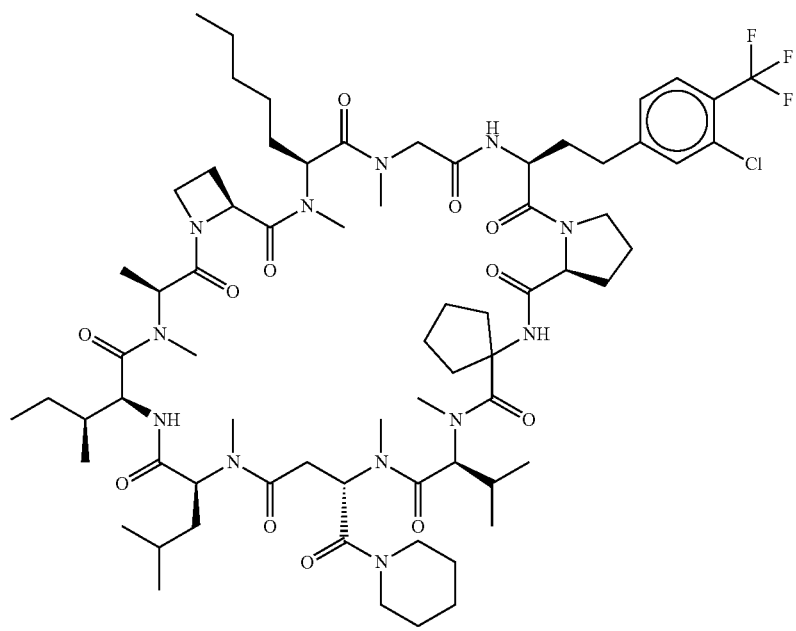 |

TABLE 24-continued
| Compound No. | Structural formula |
|---|---|
| 1855 | 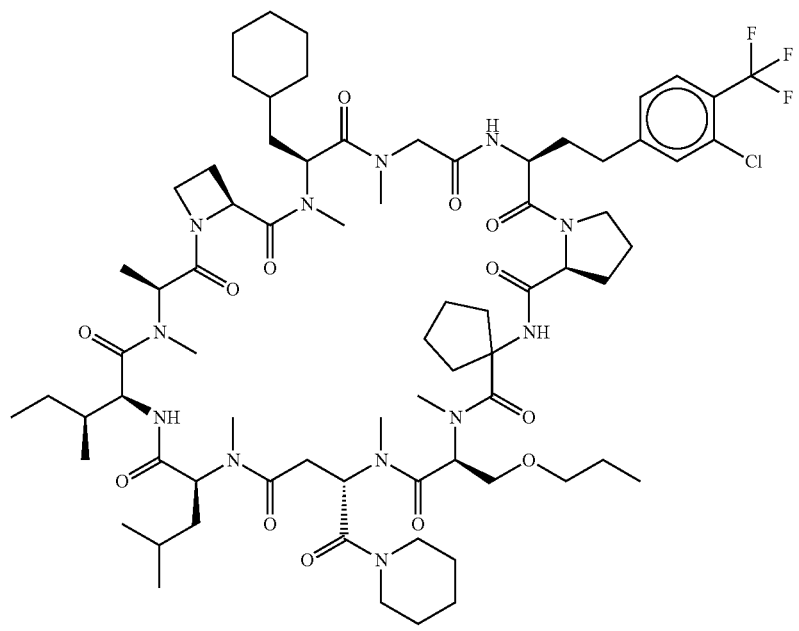 |
| 1856 | 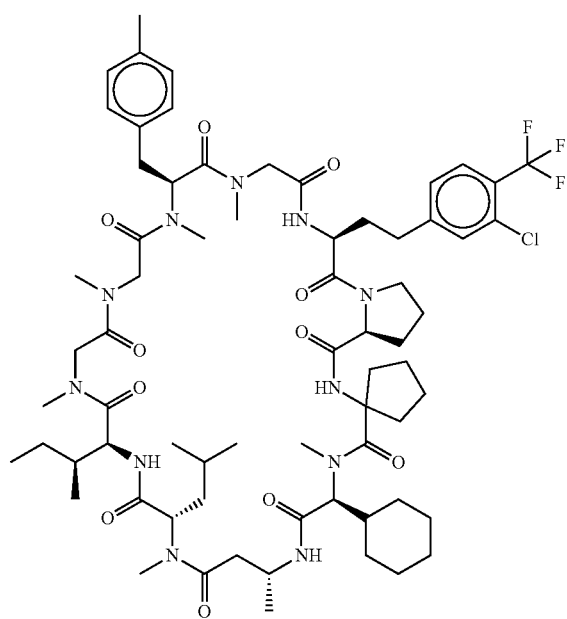 |

TABLE 24-continued
| Compound No. | Structural formula |
|---|---|
| 1857 | 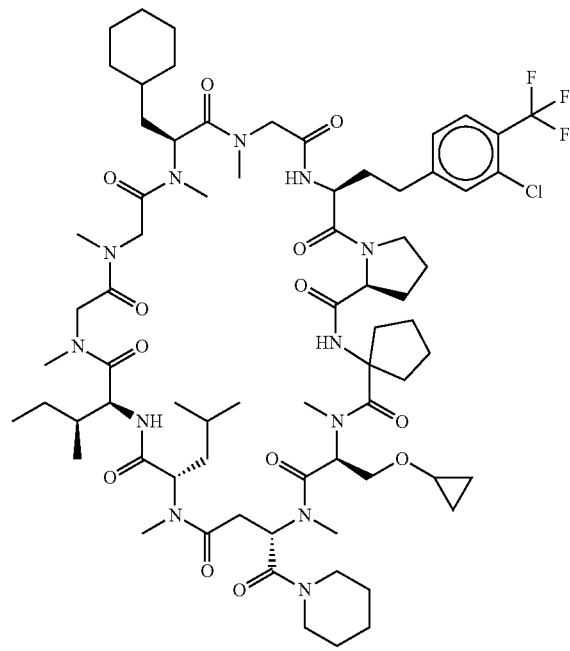 |
| 1858 | 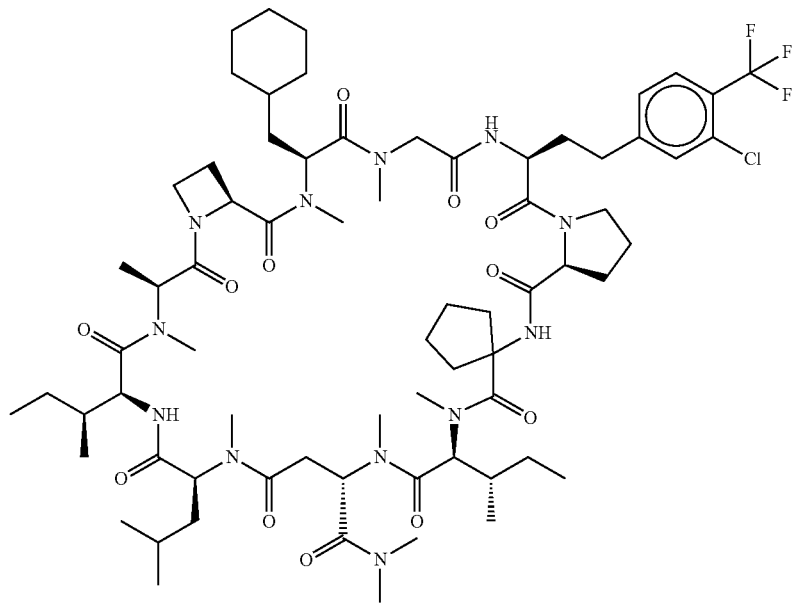 |

TABLE 24-continued
| Compound No. | Structural formula |
|---|---|
| 1859 | 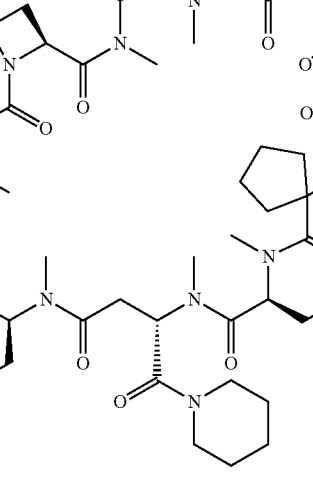 |
| 1860 | 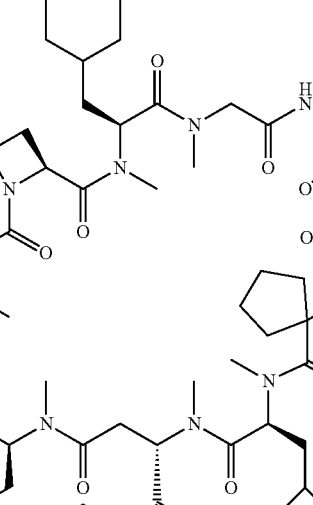 |

TABLE 24-continued
| Compound No. | Structural formula |
|---|---|
| 1861 | 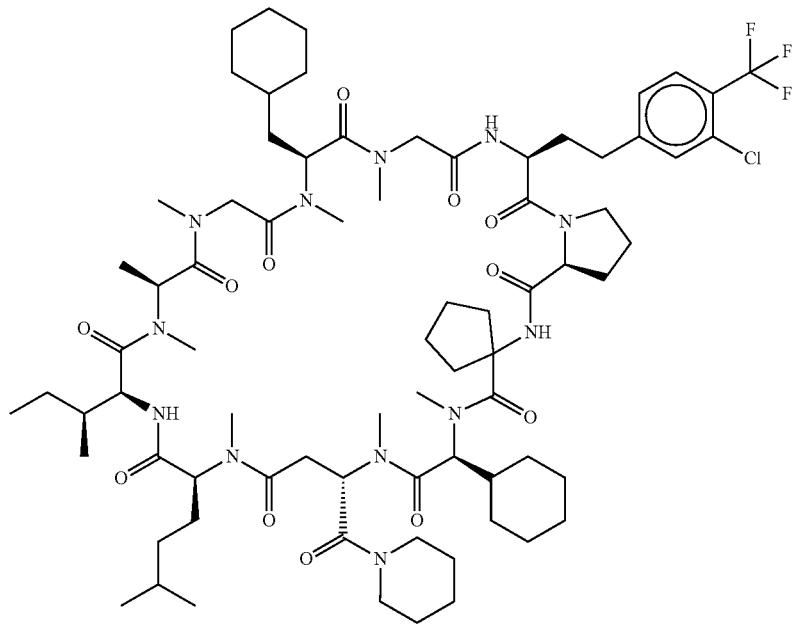 |
| 1862 | 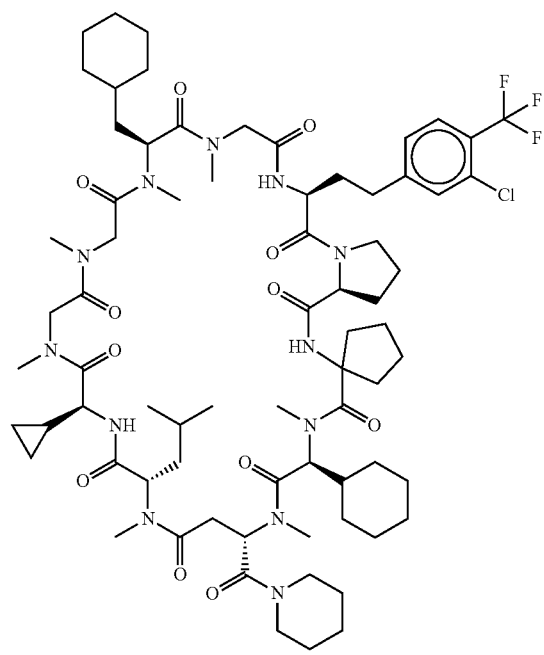 |

TABLE 24-continued
| Compound No. | Structural formula |
|---|---|
| 1863 | 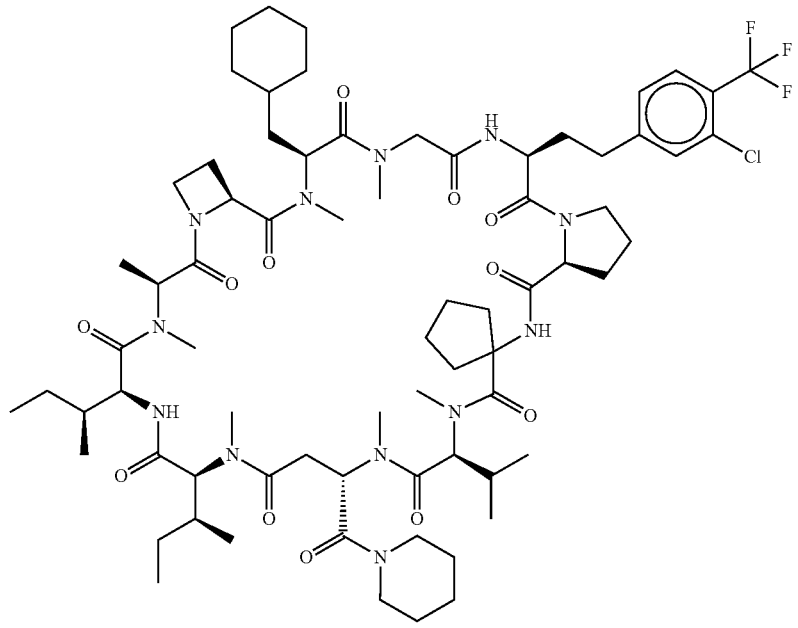 |
| 1864 | 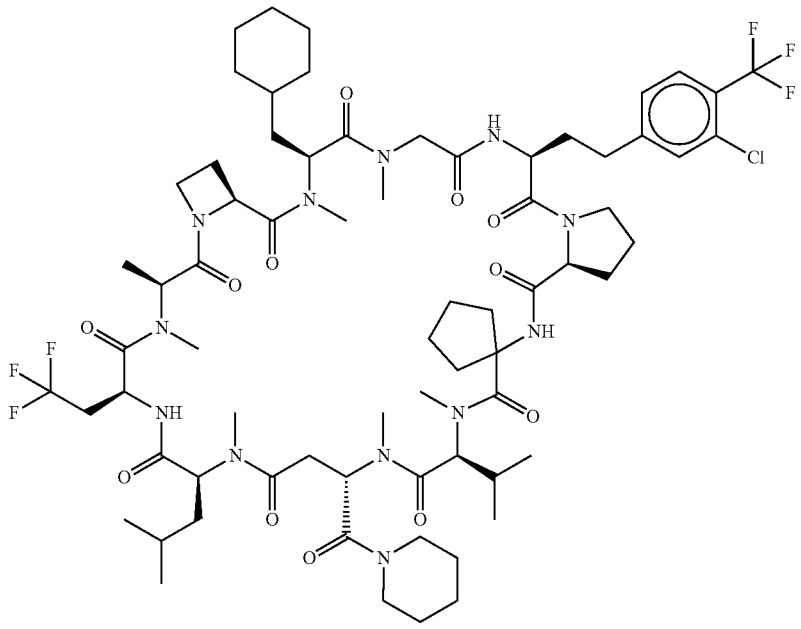 |

TABLE 24-continued
| Compound No. | Structural formula |
|---|---|
| 1865 | 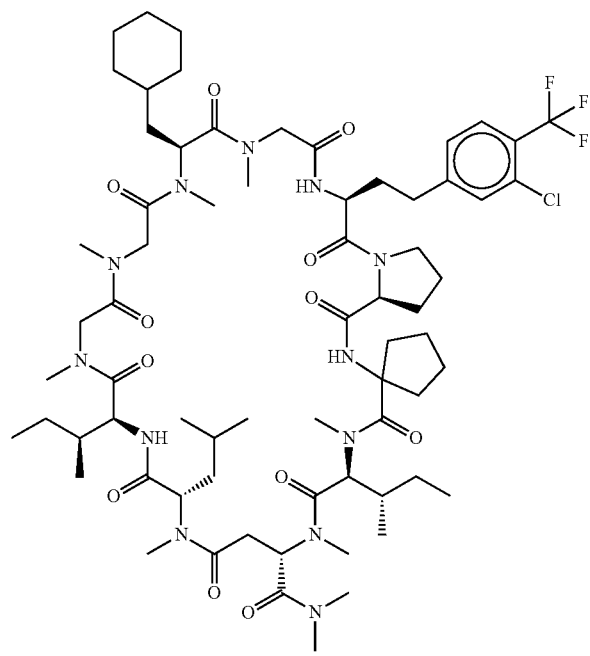 |
| 1866 | 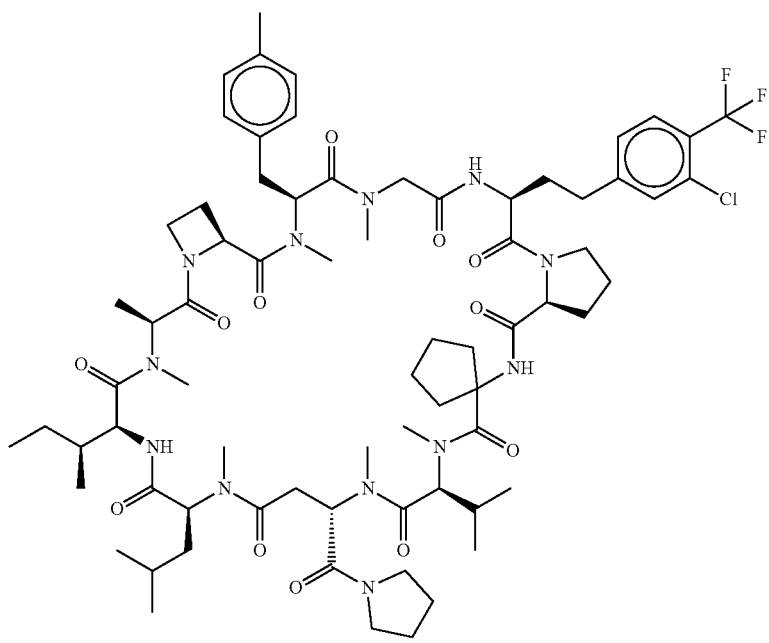 |

TABLE 24-continued
| Compound No. | Structural formula |
|---|---|
| 1867 | 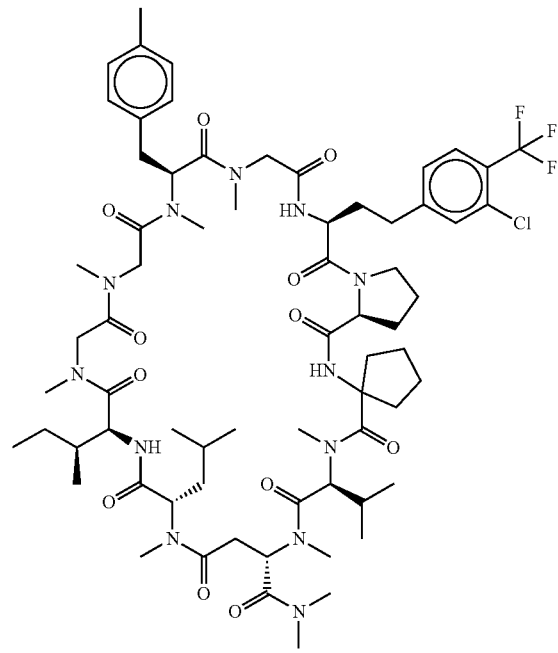 |
| 1868 | 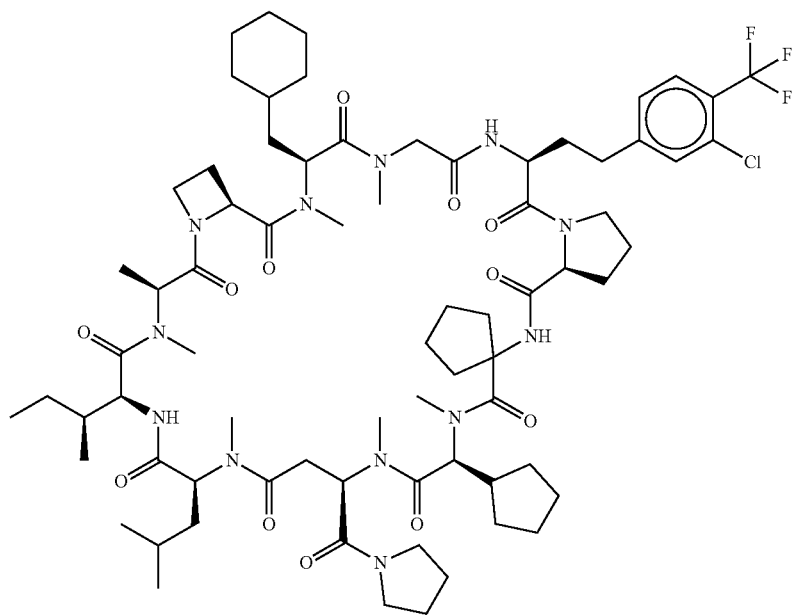 |

TABLE 24-continued
| Compound No. | Structural formula |
|---|---|
| 1869 | 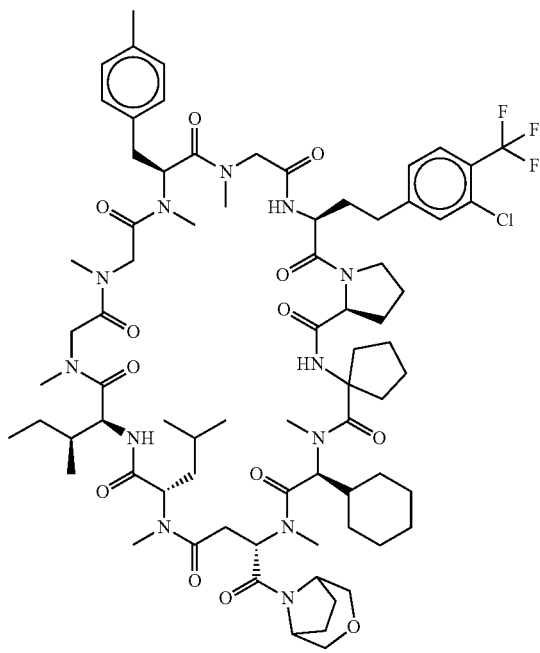 |
| 1870 | 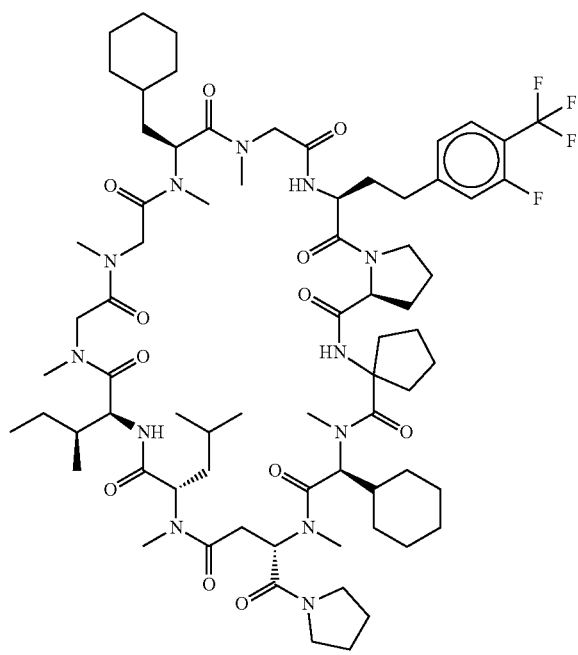 |

TABLE 24-continued
| Compound No. | Structural formula |
|---|---|
| 1871 | 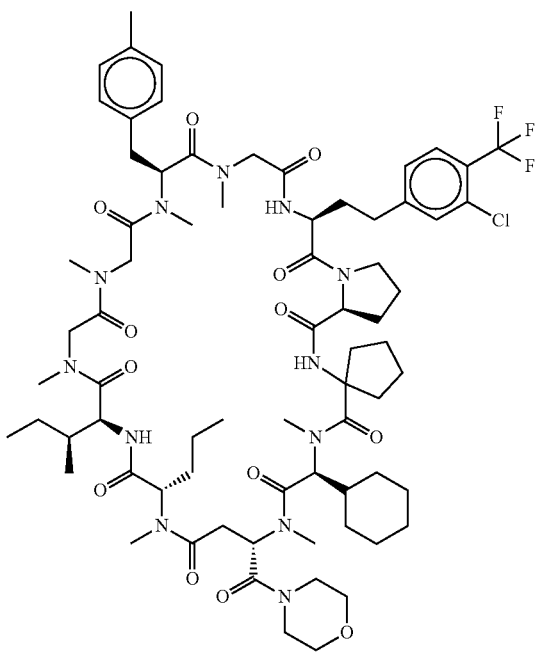 |
| 1872 | 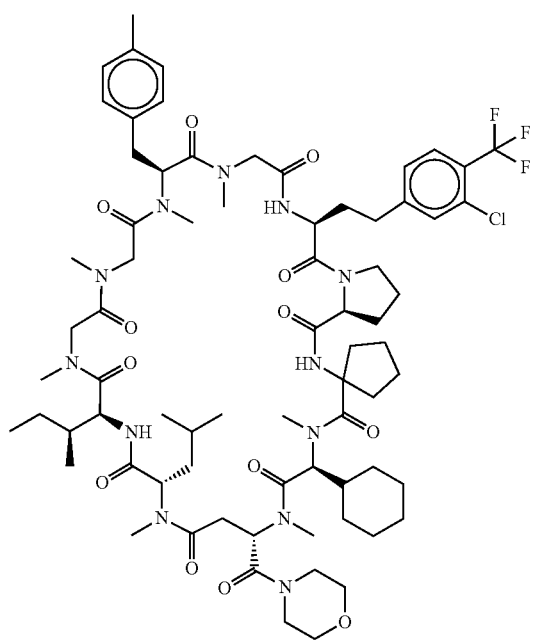 |

TABLE 24-continued
| Compound No. | Structural formula |
|---|---|
| 1873 | 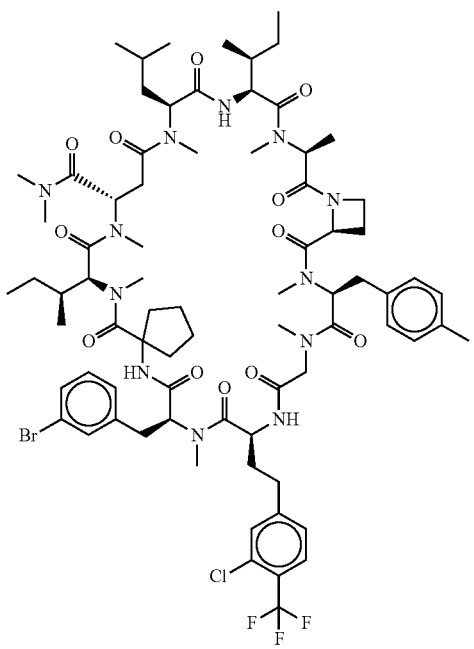 |
| 1874 | 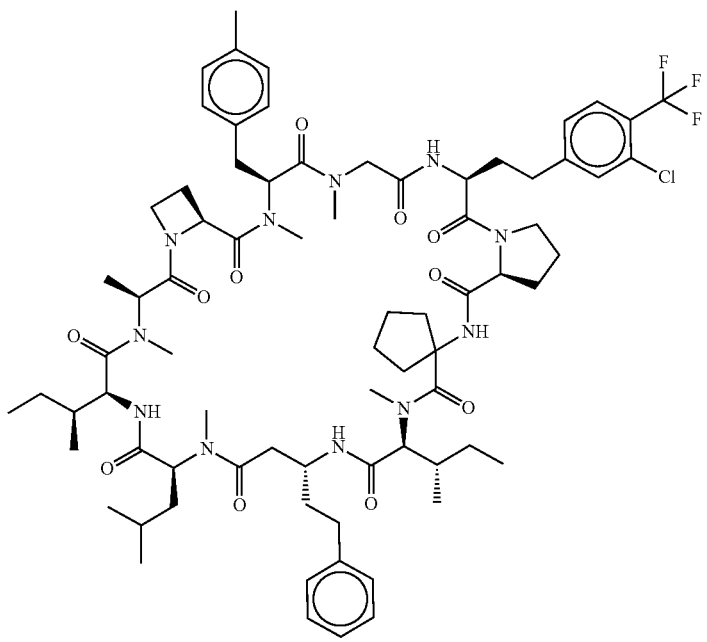 |

TABLE 24-continued
| Compound No. | Structural formula |
|---|---|
| 1875 | 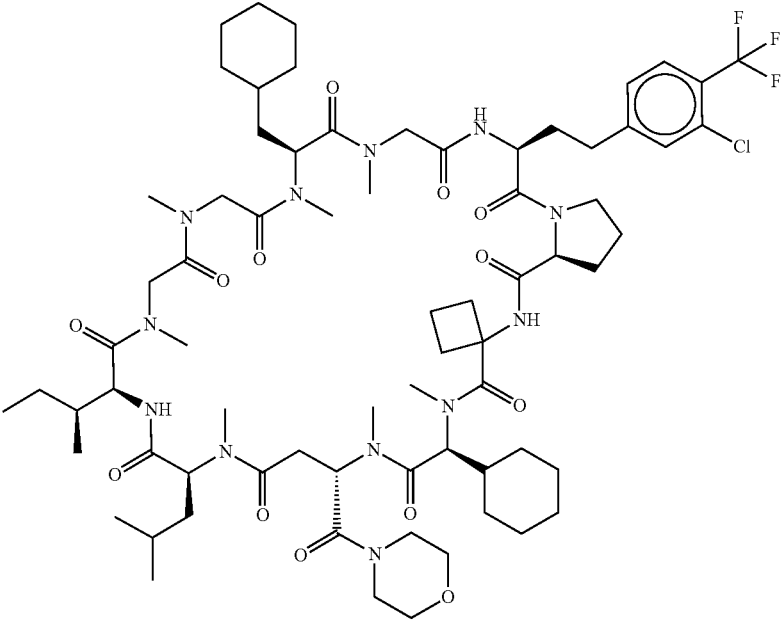 |
| 1876 | 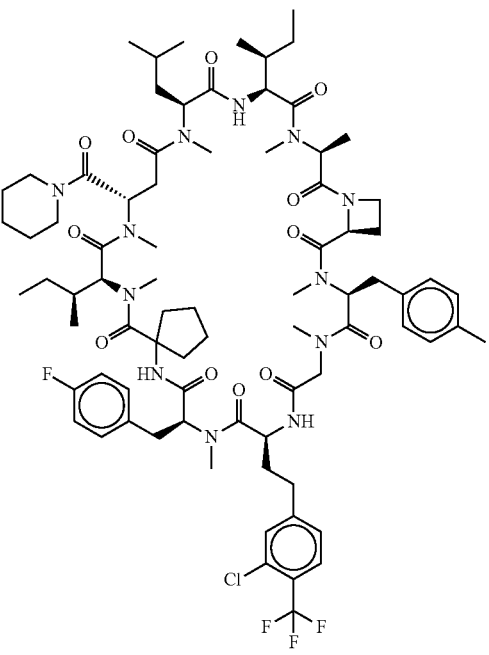 |

TABLE 24-continued
| Compound No. | Structural formula |
|---|---|
| 1877 | 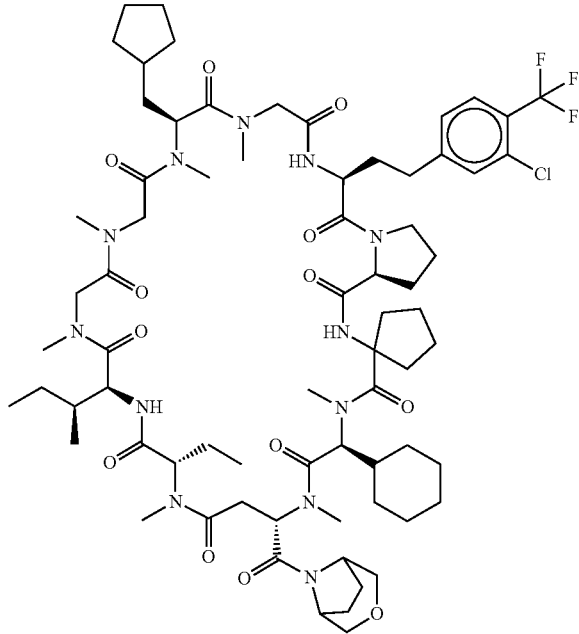 |
| 1878 | 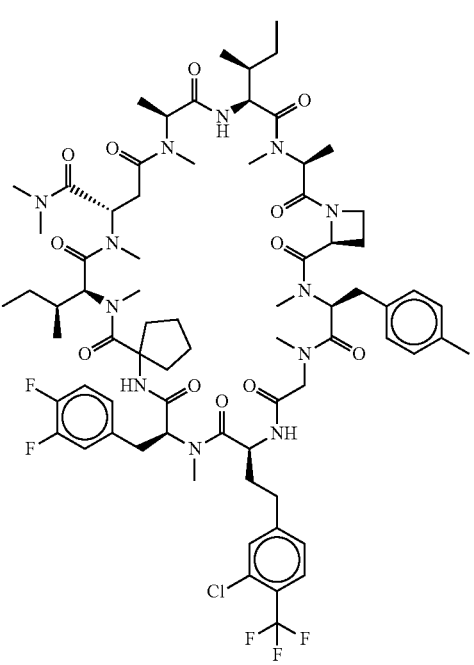 |

TABLE 24-continued
| Compound No. | Structural formula |
|---|---|
| 1879 | 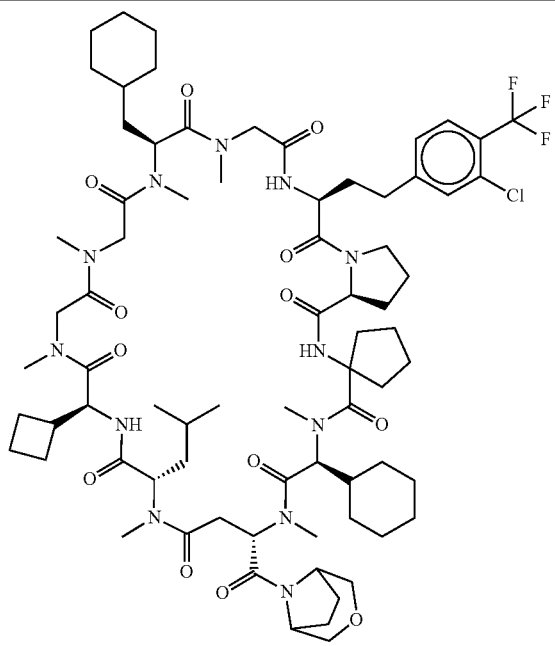 |
| 1880 | 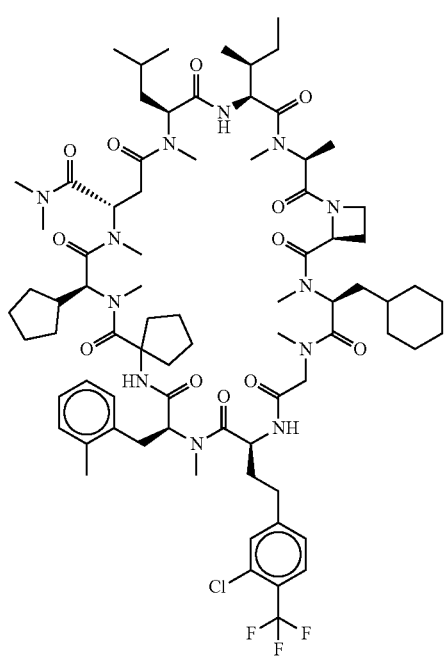 |

TABLE 24-continued
| Compound No. | Structural formula |
|---|---|
| 1881 | 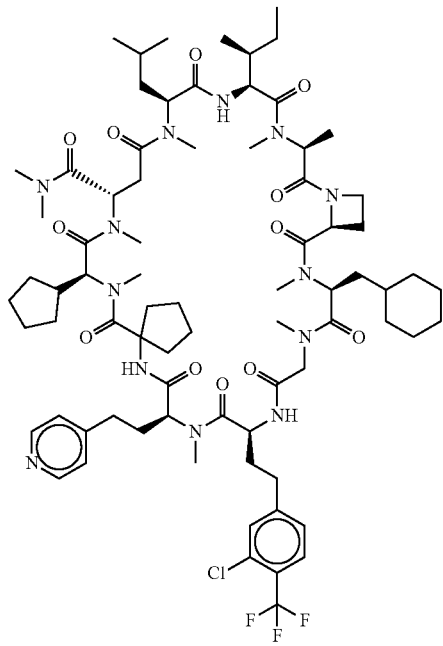 |
| 1882 | 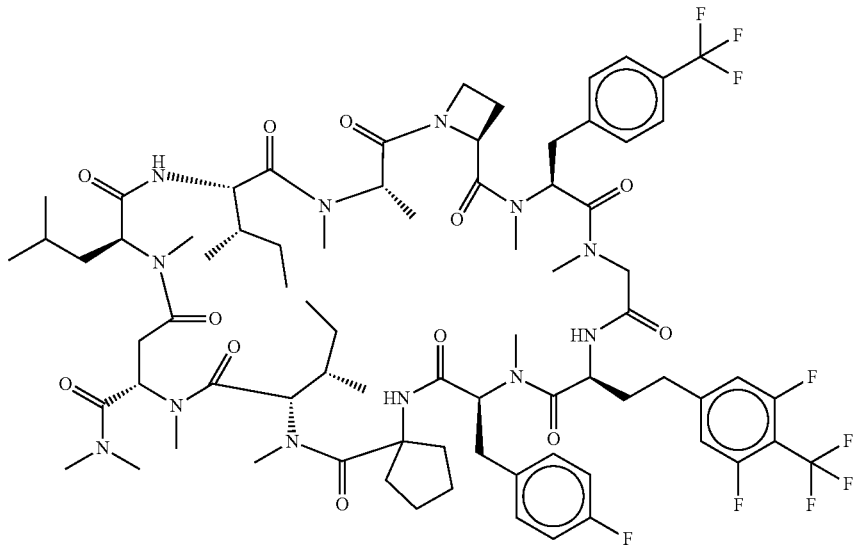 |

TABLE 24-continued
| Compound No. | Structural formula |
|---|---|
| 1883 | 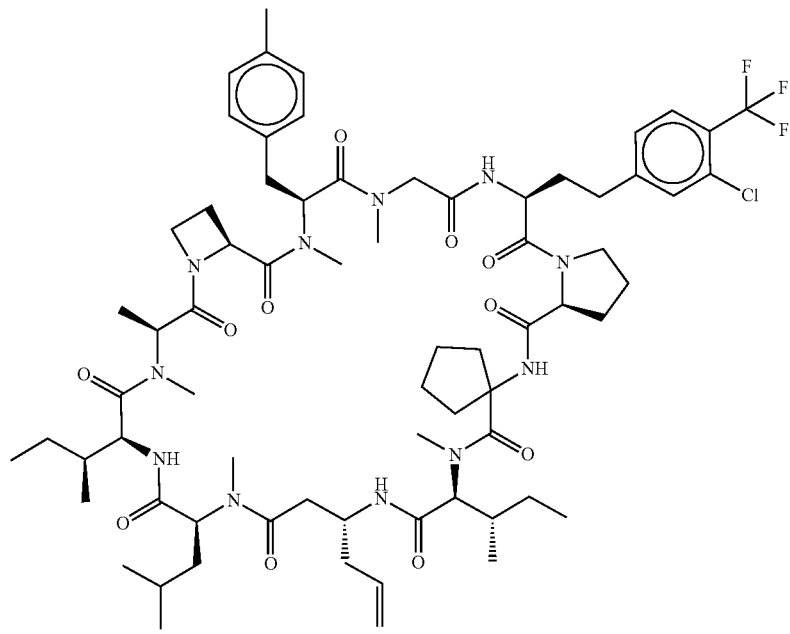 |
| 1884 | 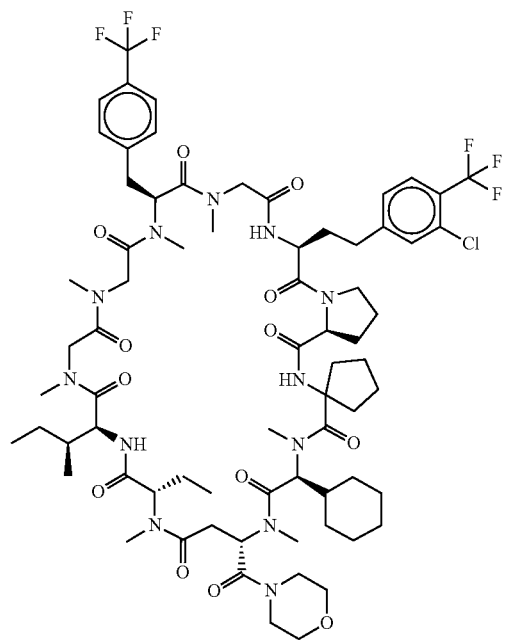 |

TABLE 24-continued
| Compound No. | Structural formula |
|---|---|
| 1885 | 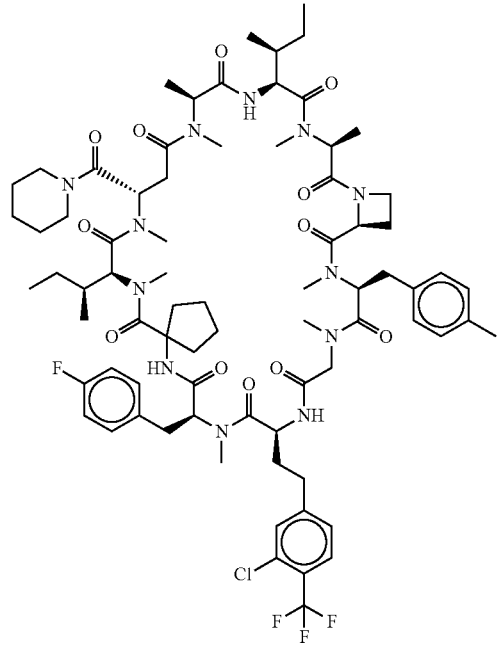 |
| 1886 | 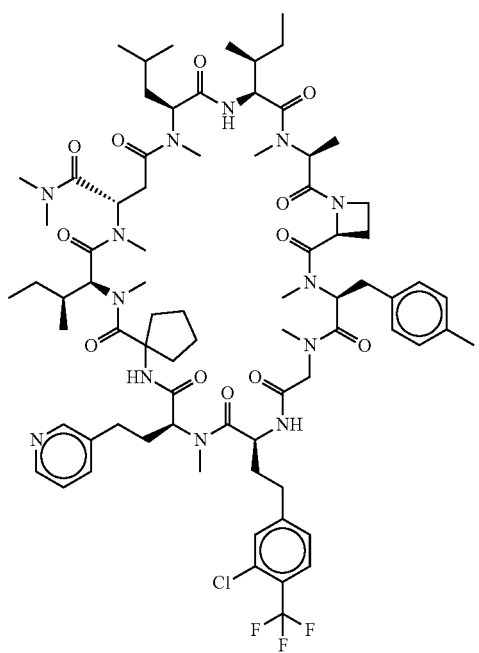 |

TABLE 24-continued
| Compound No. | Structural formula |
|---|---|
| 1887 | 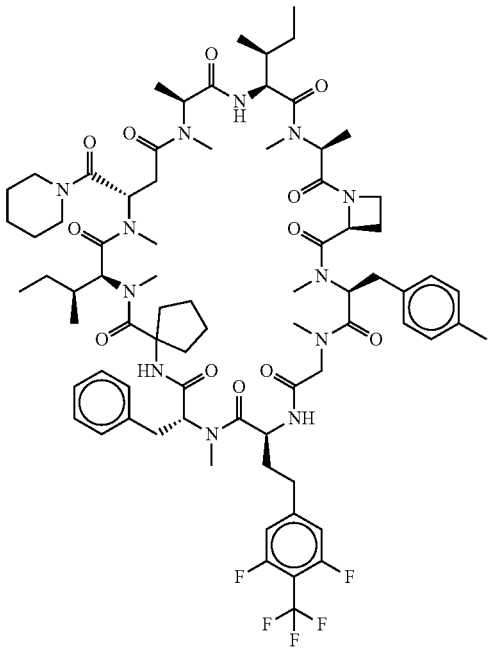 |
| 1888 | 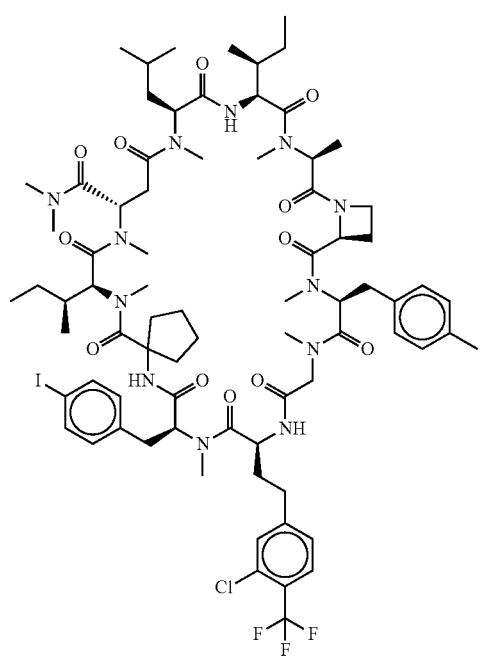 |

TABLE 24-continued
| Compound No. | Structural formula |
|---|---|
| 1889 | 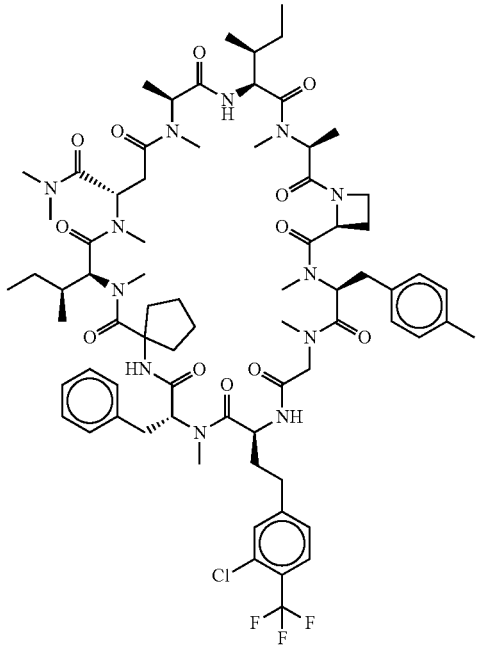 |
| 1890 | 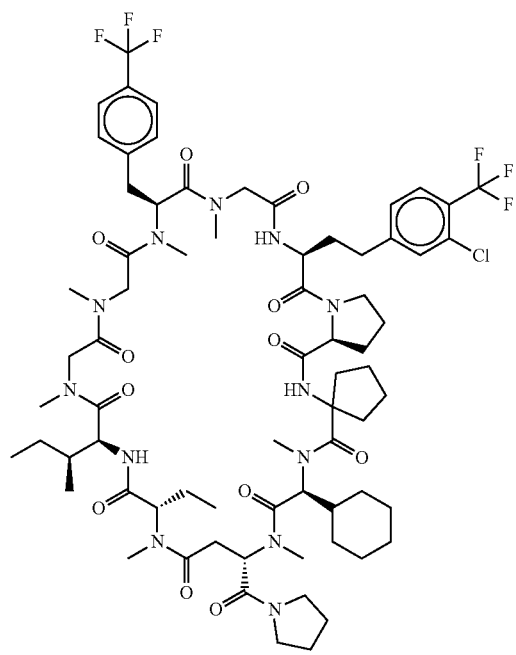 |

TABLE 24-continued
| Compound No. | Structural formula |
| --- | --- |
| 1891 | 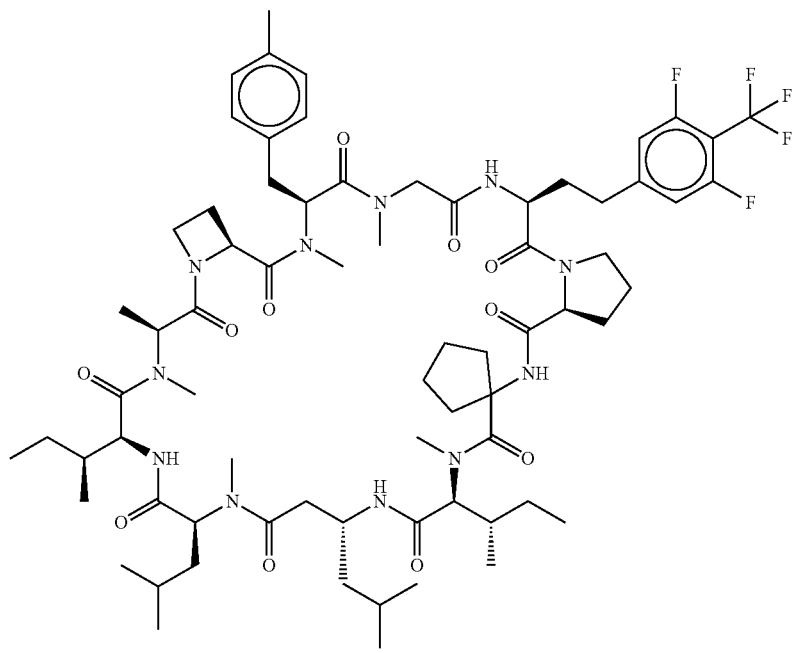 |
| 1892 | 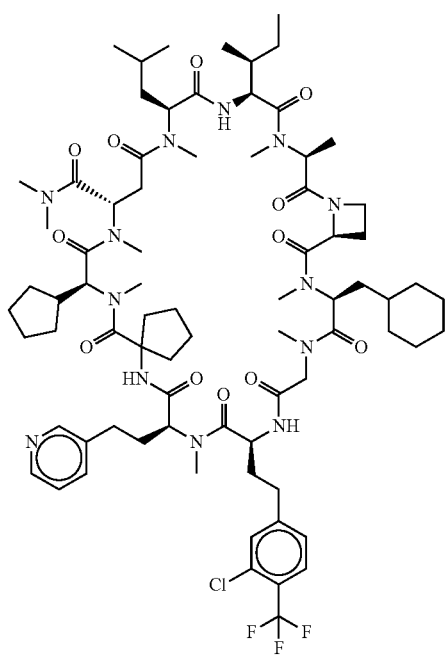 |

TABLE 24-continued
| Compound No. | Structural formula |
|---|---|
| 1893 | 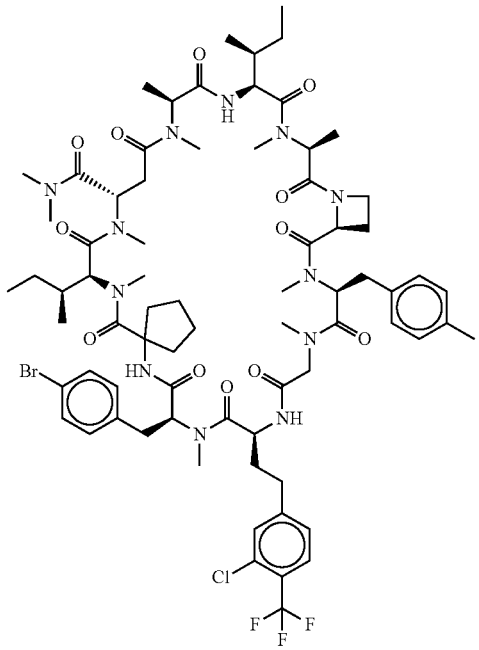 |
| 1894 | 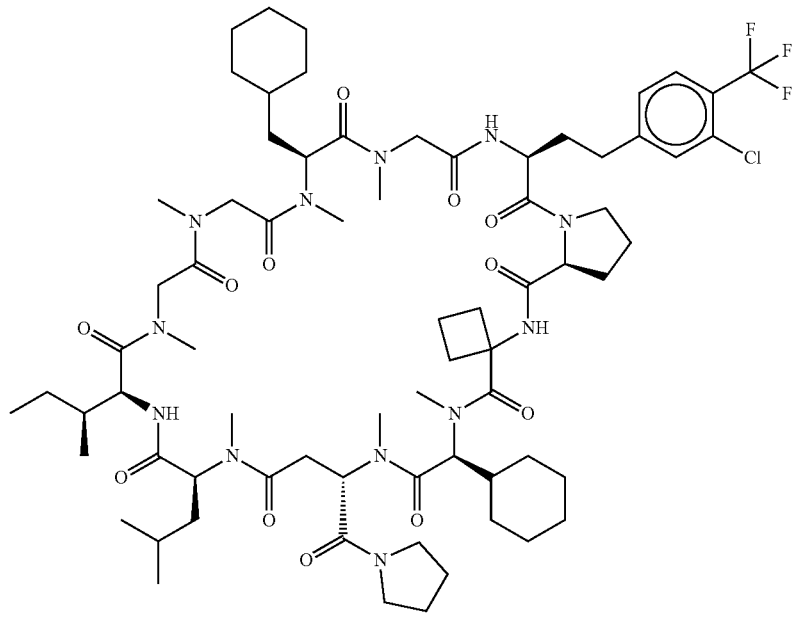 |

TABLE 24-continued
| Compound No. | Structural formula |
|---|---|
| 1895 | 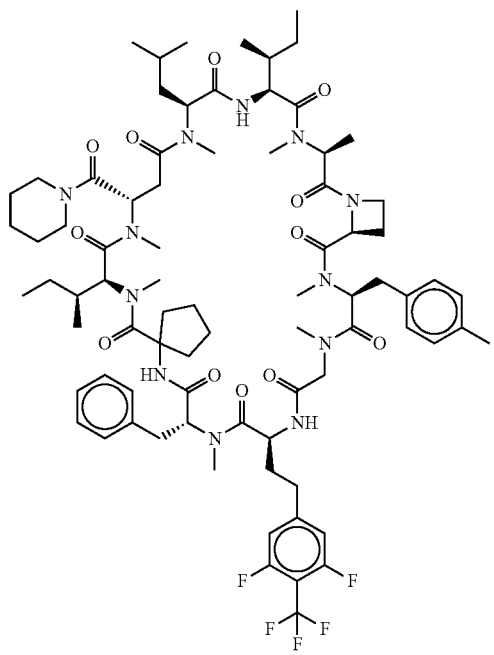 |
| 1896 | 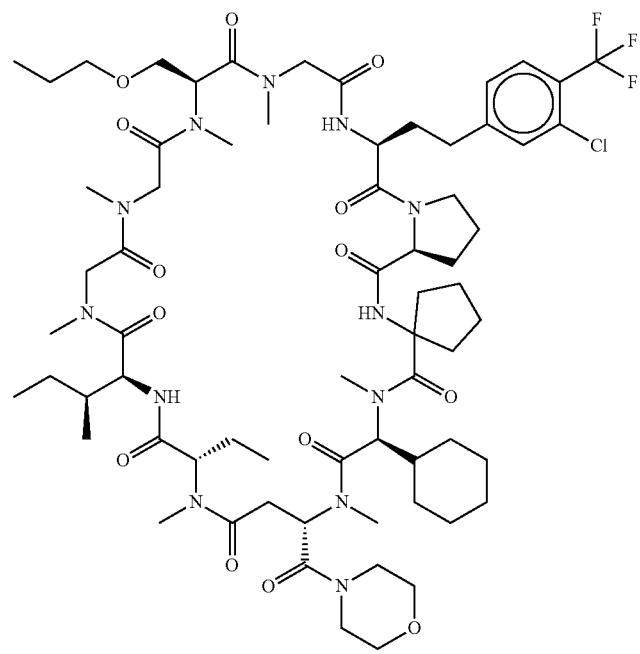 |

TABLE 24-continued
| Compound No. | Structural formula |
|---|---|
| 1897 | 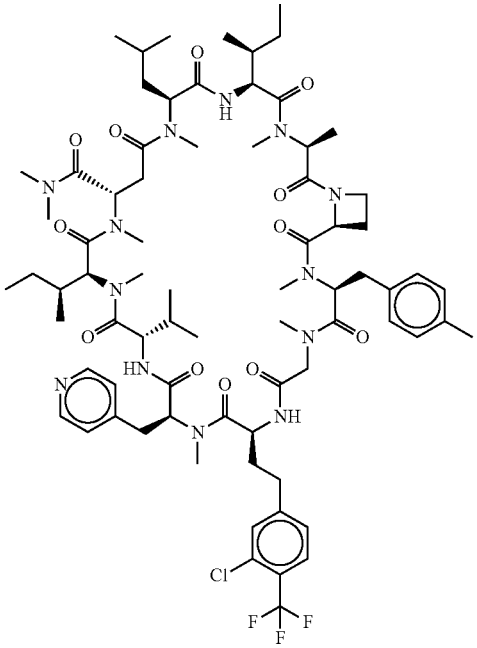 |
| 1898 | 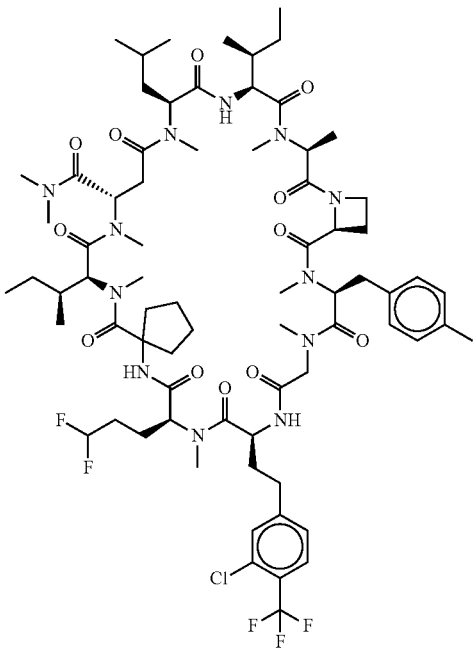 |

TABLE 24-continued
| Compound No. | Structural formula |
|---|---|
| 1899 | 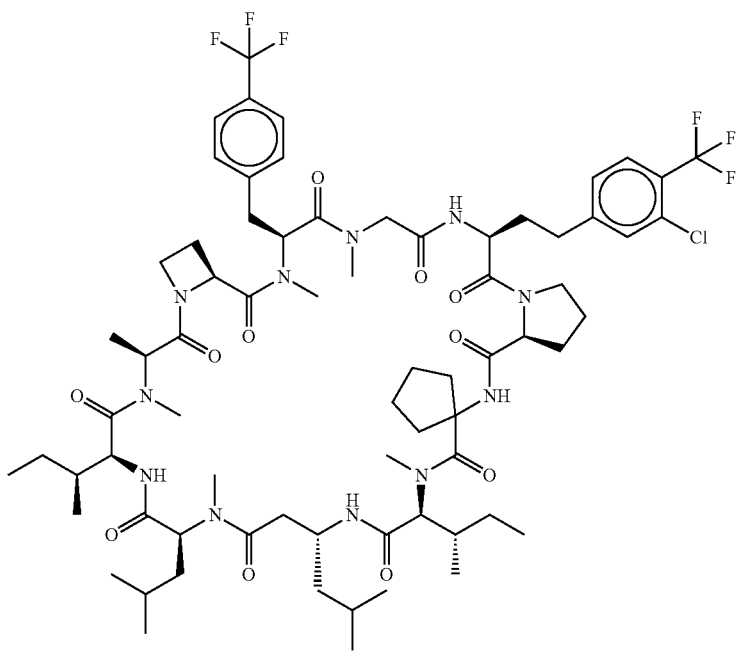 |
| 1900 | 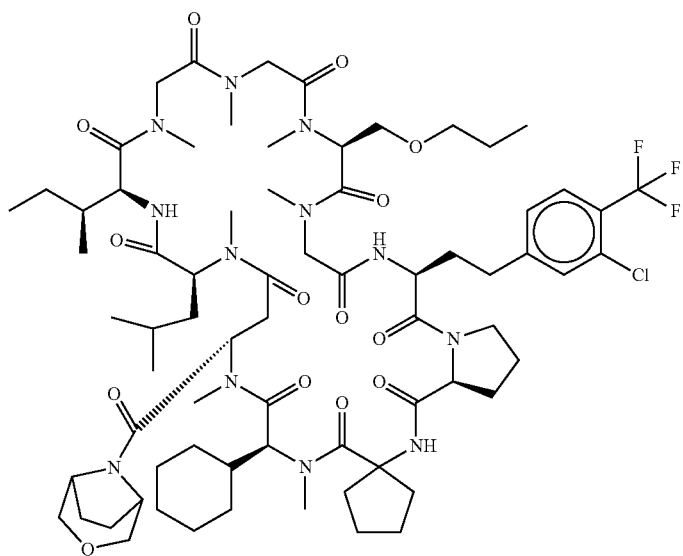 |

TABLE 24-continued
| Compound No. | Structural formula |
|---|---|
| 1901 | 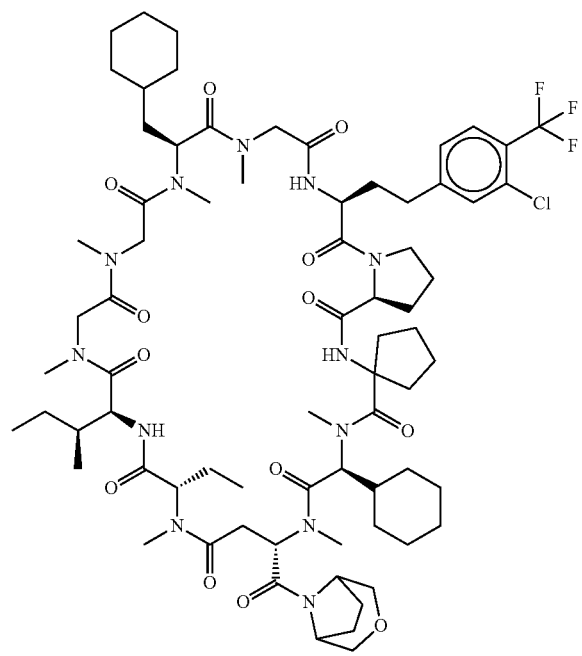 |
| 1902 | 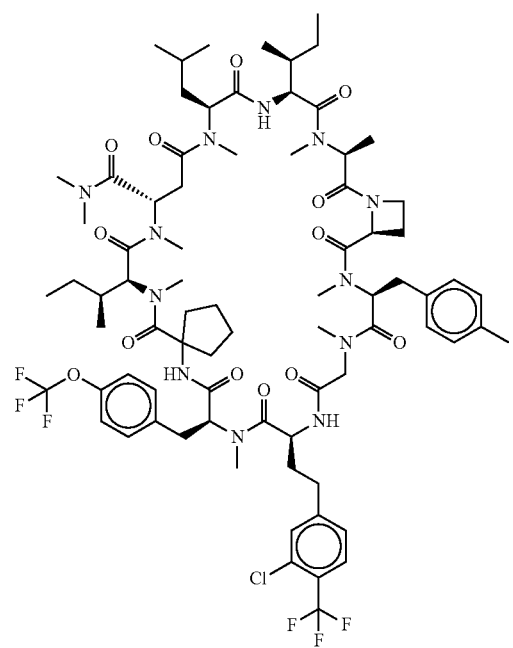 |

TABLE 24-continued
| Compound No. | Structural formula |
|---|---|
| 1903 | 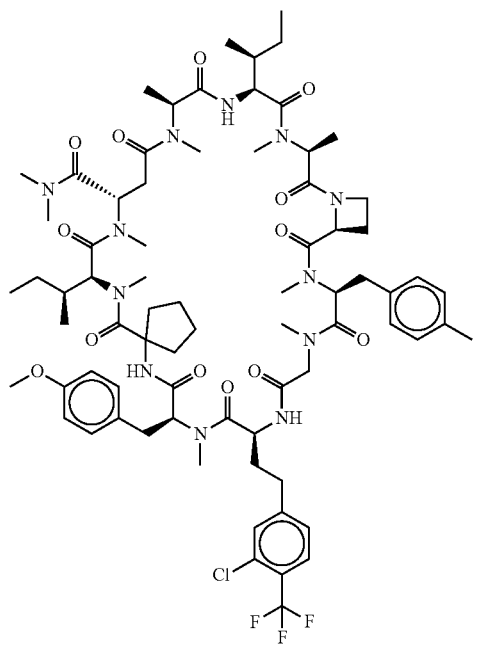 |
| 1904 | 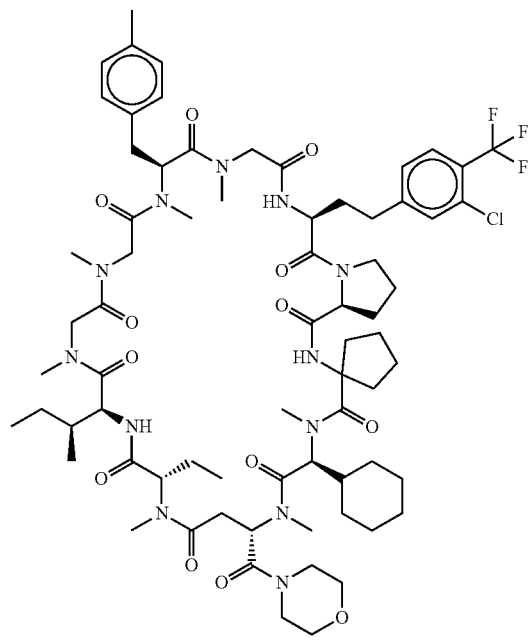 |

TABLE 24-continued
| Compound No. | Structural formula |
|---|---|
| 1905 | 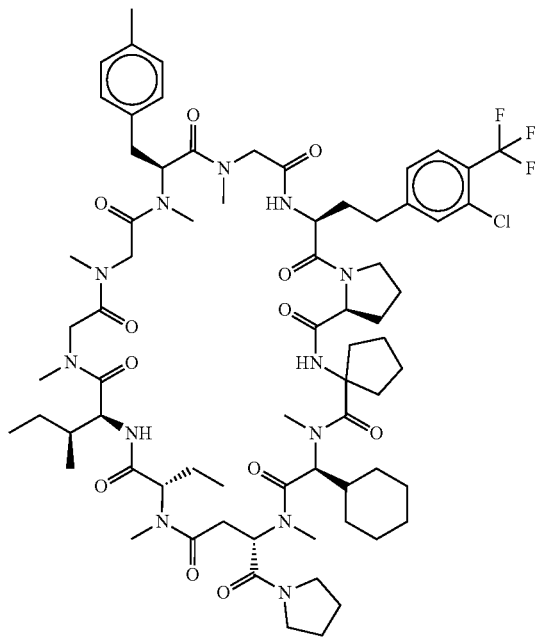 |
| 1906 | 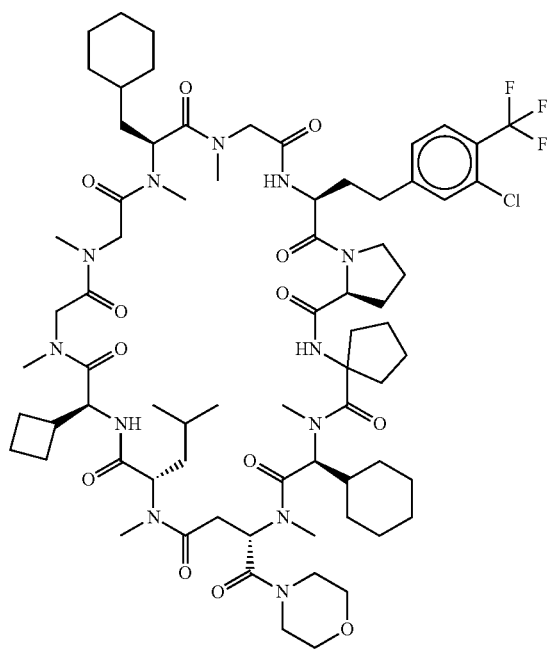 |

TABLE 24-continued
| Compound No. | Structural formula |
|---|---|
| 1907 | 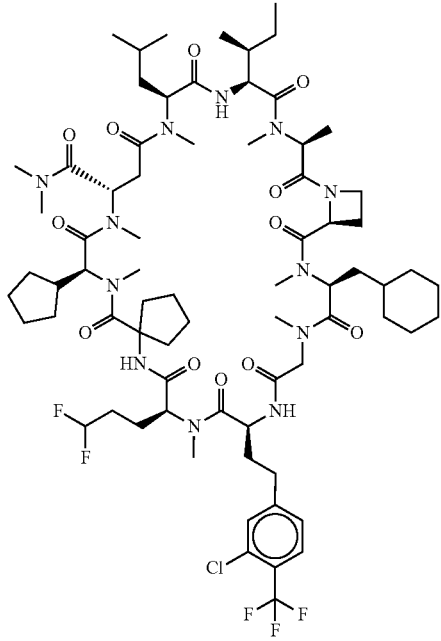 |
| 1908 | 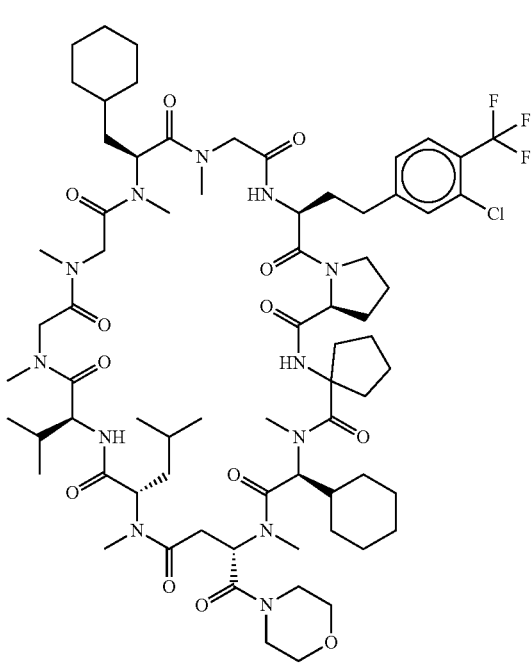 |

TABLE 24-continued
| Compound No. | Structural formula |
|---|---|
| 1909 | 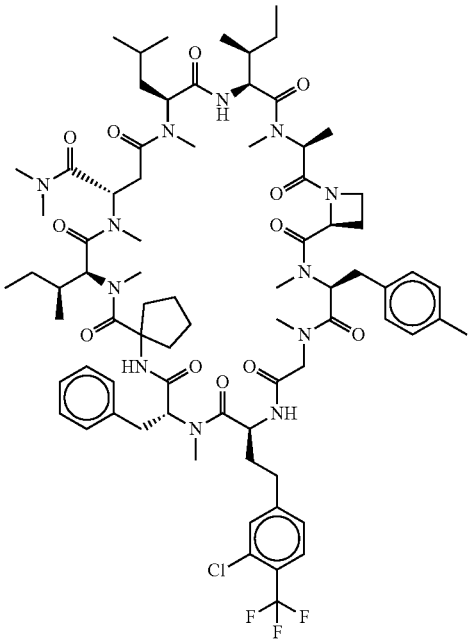 |
| 1910 | 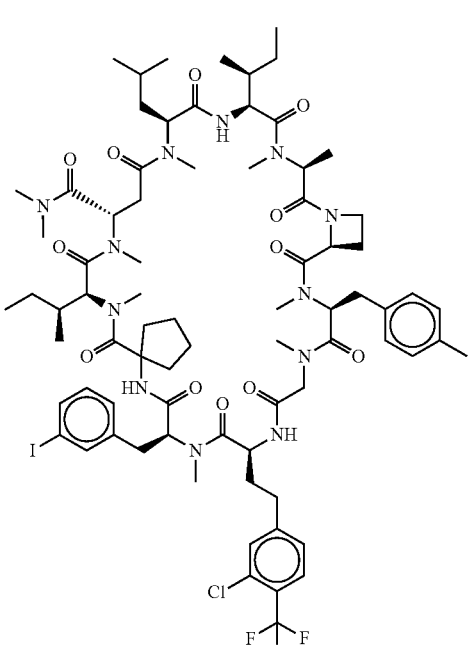 |

TABLE 24-continued
| Compound No. | Structural formula |
|---|---|
| 1911 | 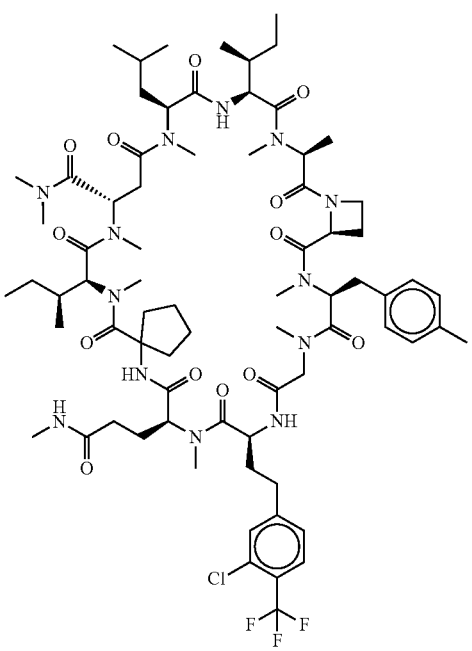 |
| 1912 | 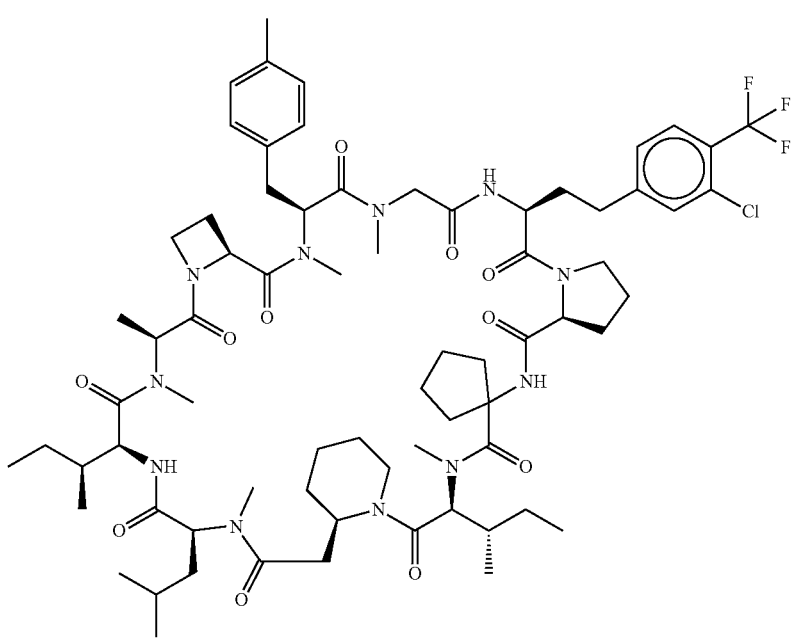 |

TABLE 24-continued
| Compound No. | Structural formula |
|---|---|
| 1913 | 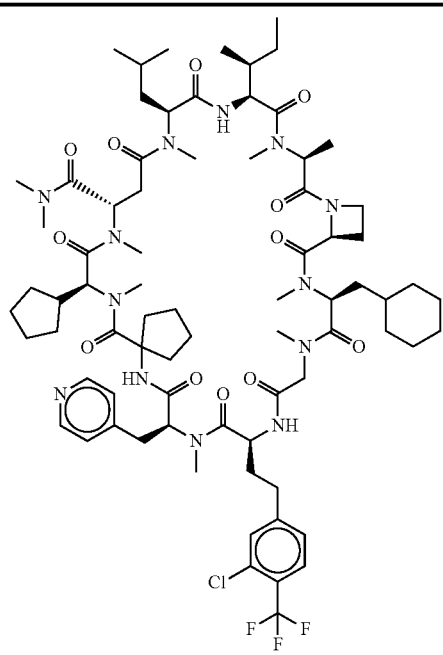 |
| 1914 | 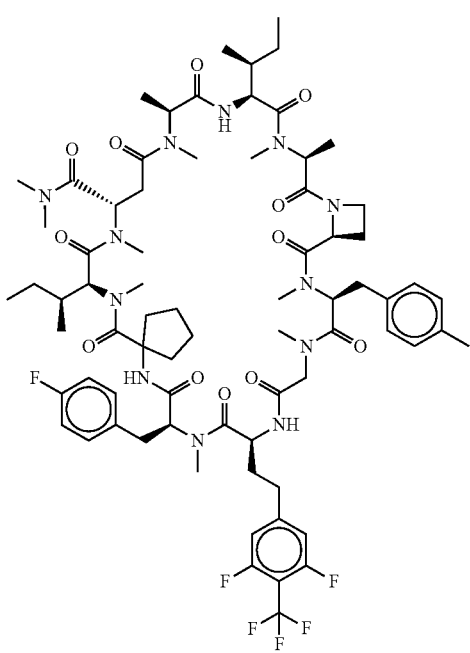 |

TABLE 24-continued
| Compound No. | Structural formula |
|---|---|
| 1915 | 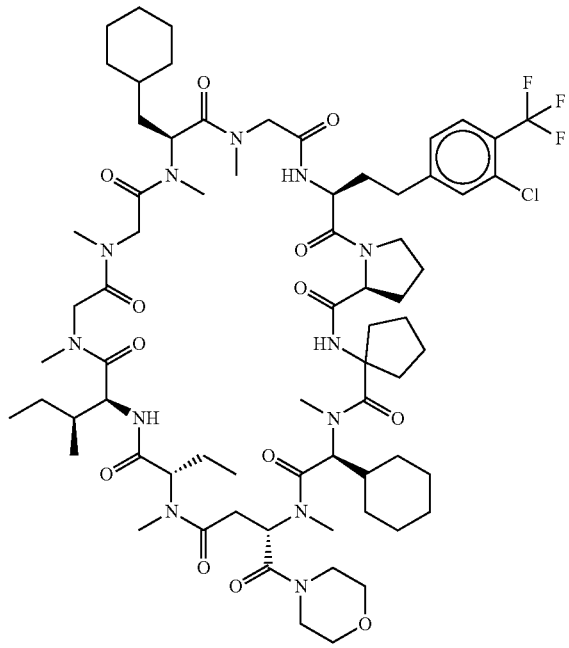 |
| 1916 | 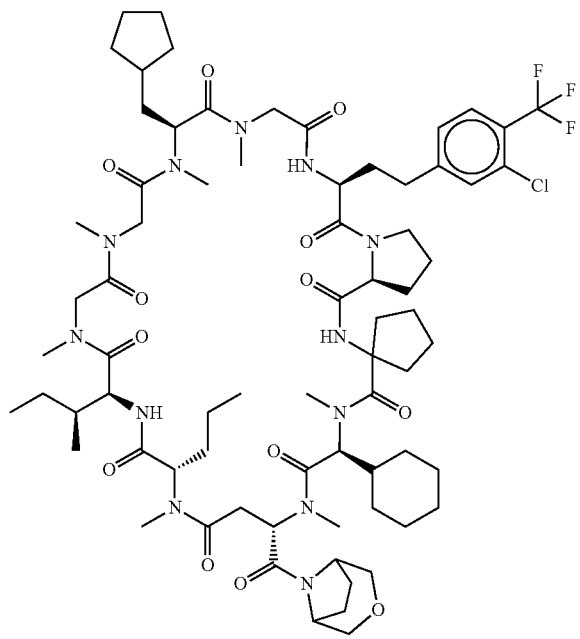 |

TABLE 24-continued
| Compound No. | Structural formula |
|---|---|
| 1917 | 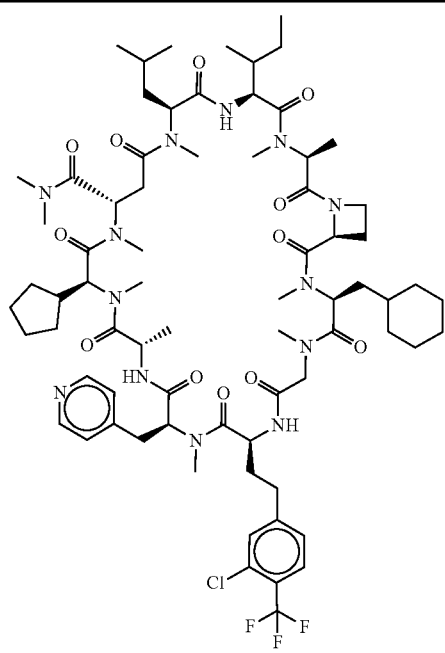 |
| 1918 | 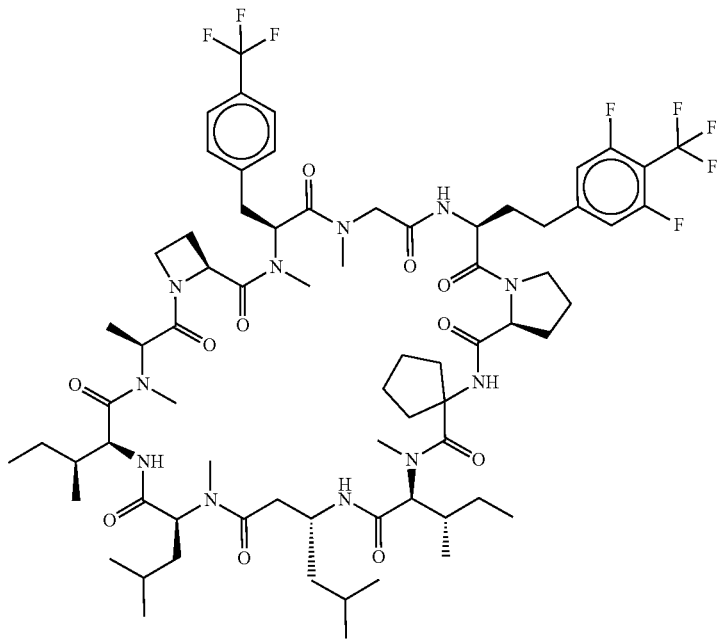 |

TABLE 24-continued
| Compound No. | Structural formula |
|---|---|
| 1919 | 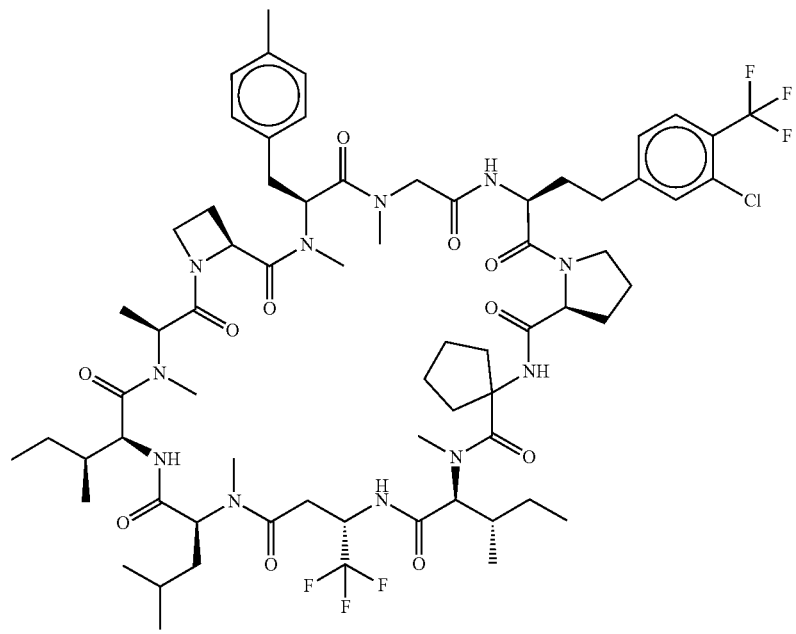 |
| 1920 | 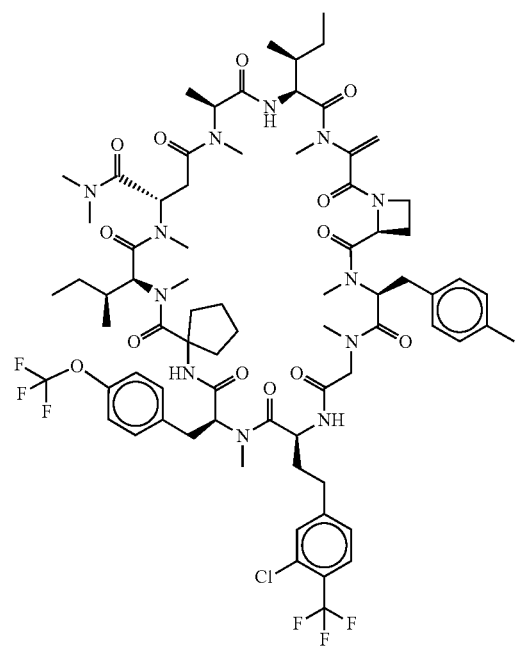 |

TABLE 24-continued
| Compound No. | Structural formula |
|---|---|
| 1921 | 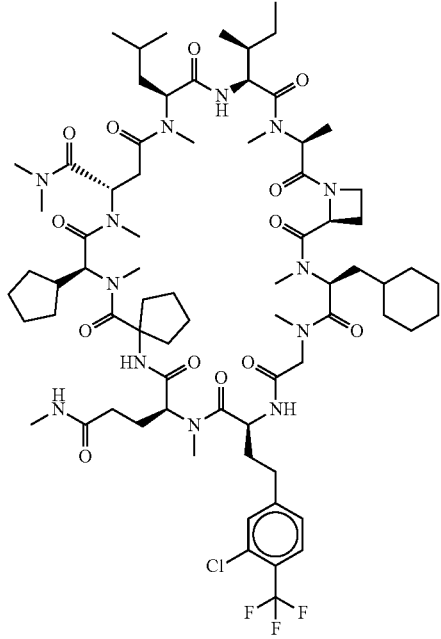 |
| 1922 | 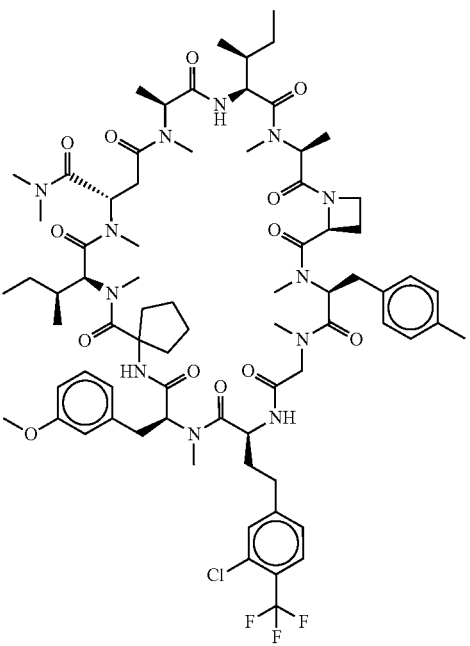 |

TABLE 24-continued
| Compound No. | Structural formula |
|---|---|
| 1923 | 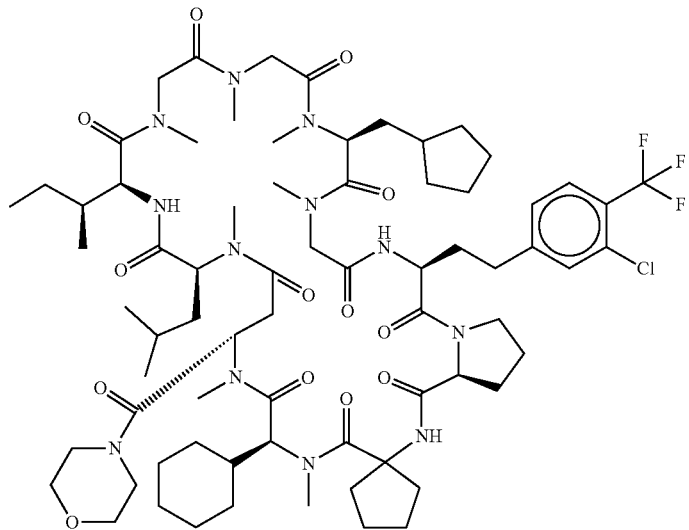 |
| 1924 | 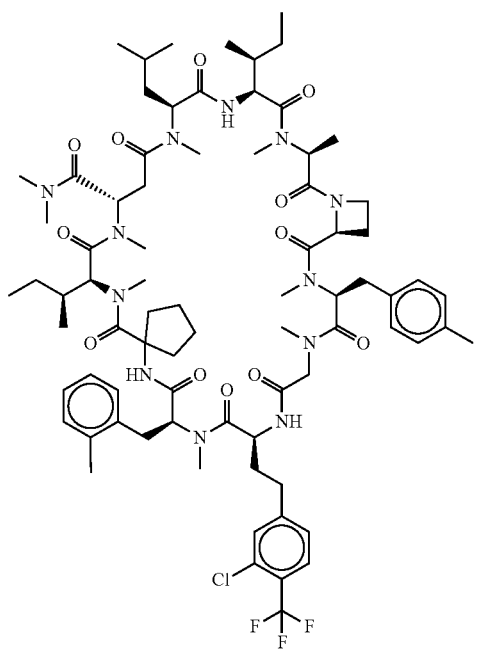 |

TABLE 24-continued
| Compound No. | Structural formula |
|---|---|
| 1925 | 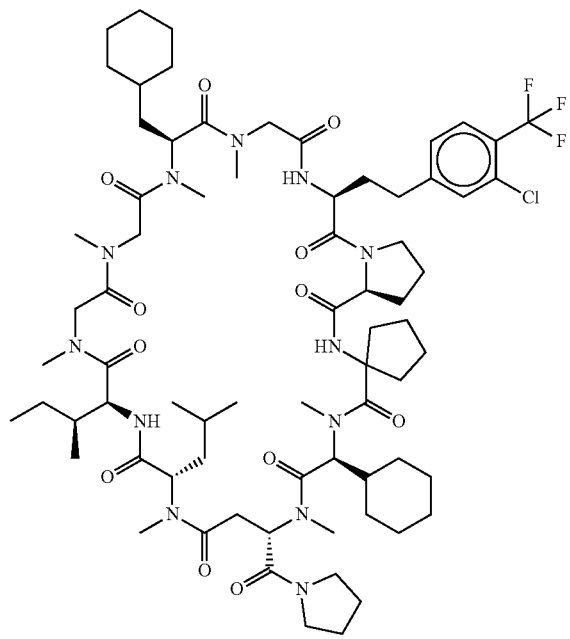 |
| 1926 | 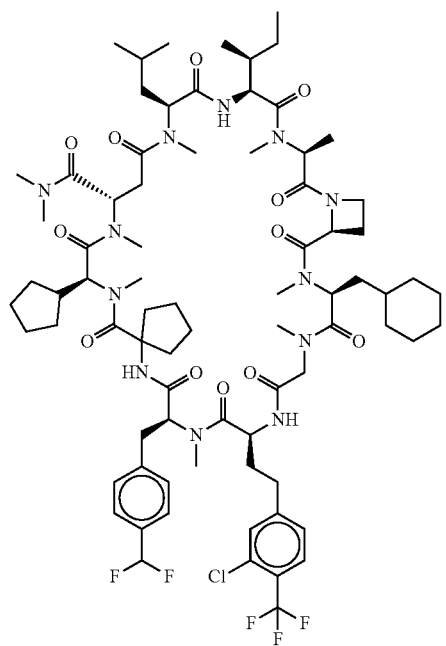 |

TABLE 24-continued
| Compound No. | Structural formula |
|---|---|
| 1927 | 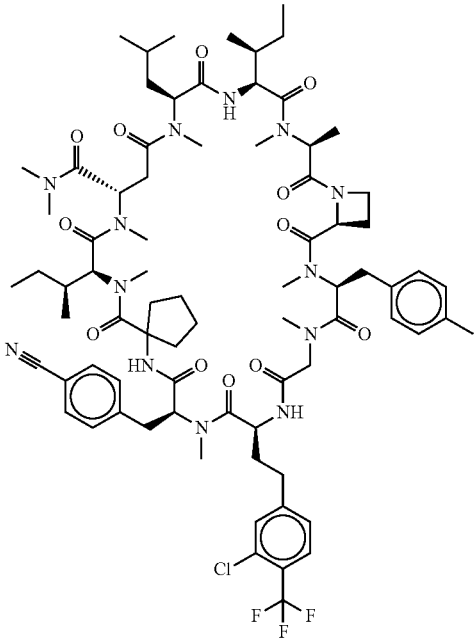 |
| 1928 | 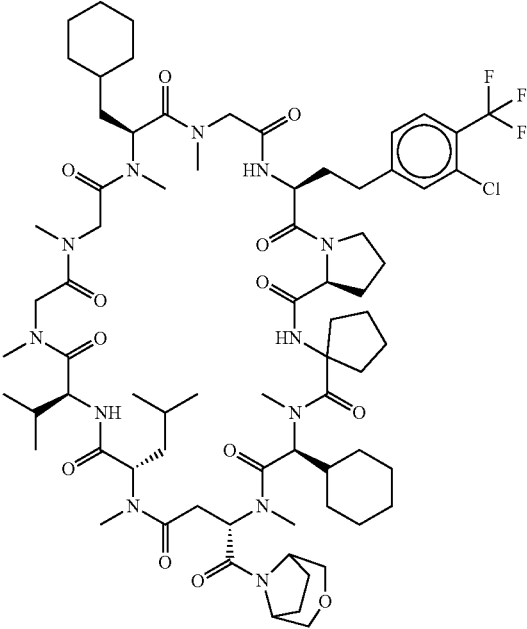 |

TABLE 24-continued
| Compound No. | Structural formula |
|---|---|
| 1929 | 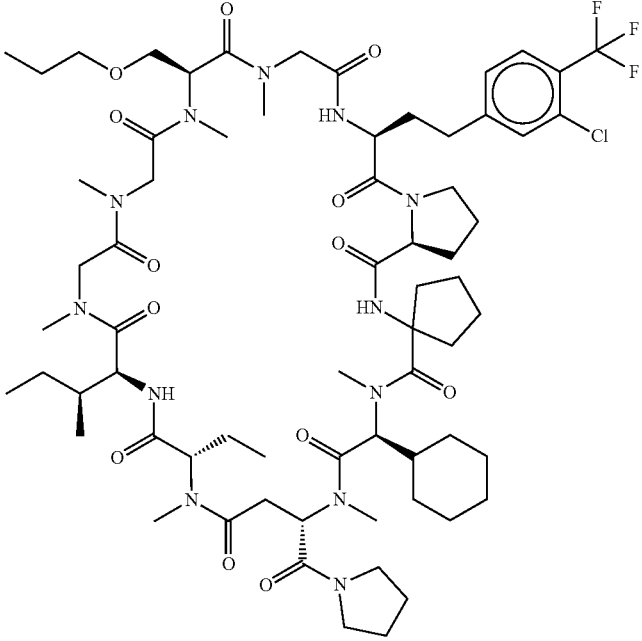 |
| 1930 | 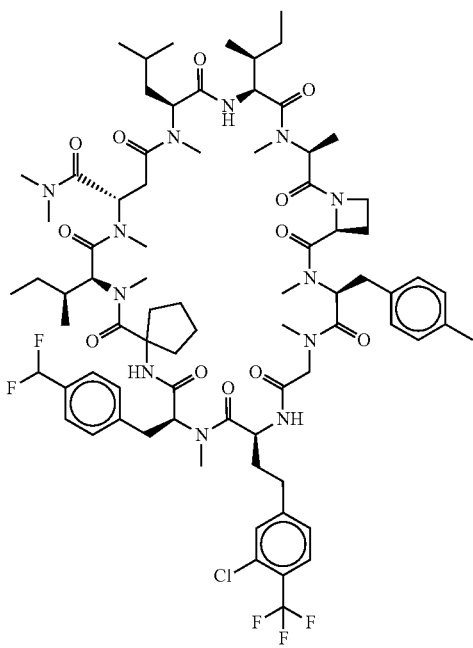 |

TABLE 24-continued
| Compound No. | Structural formula |
|---|---|
| 1931 | 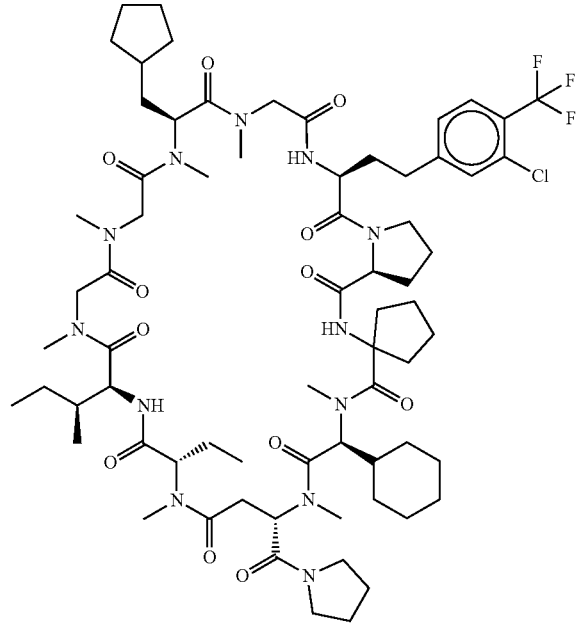 |
| 1932 | 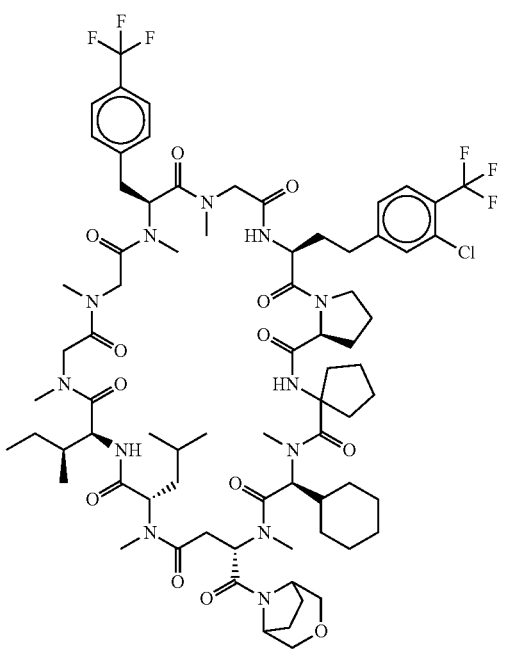 |

TABLE 24-continued
| Compound No. | Structural formula |
|---|---|
| 1933 | 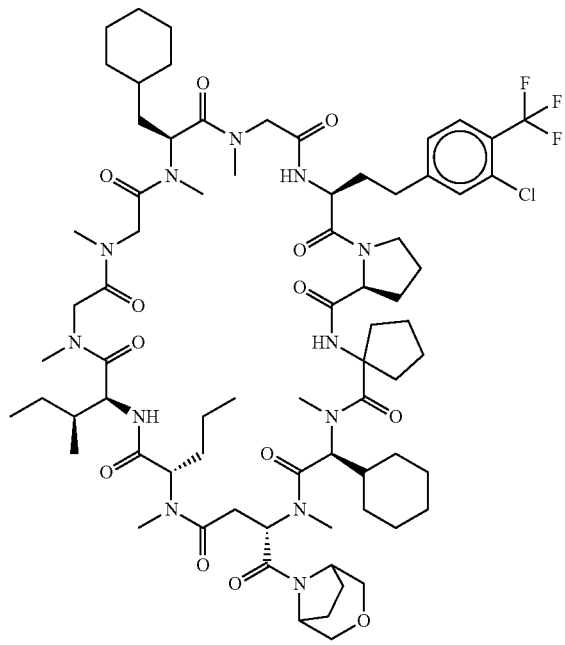 |
| 1934 | 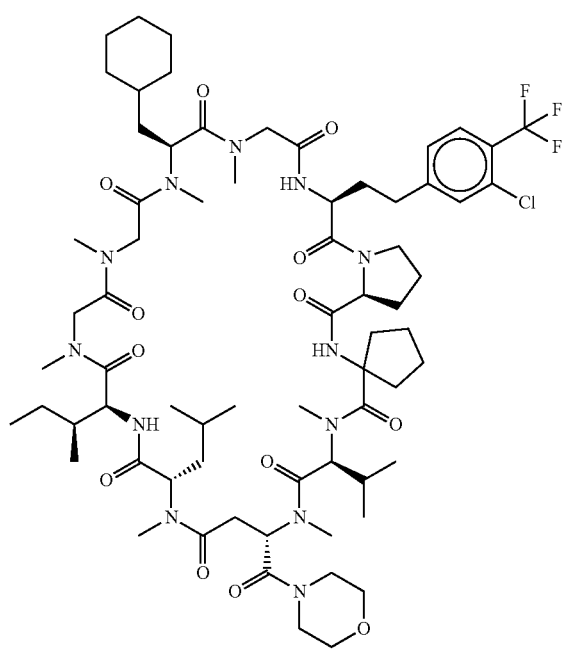 |

TABLE 24-continued
| Compound No. | Structural formula |
|---|---|
| 1935 | 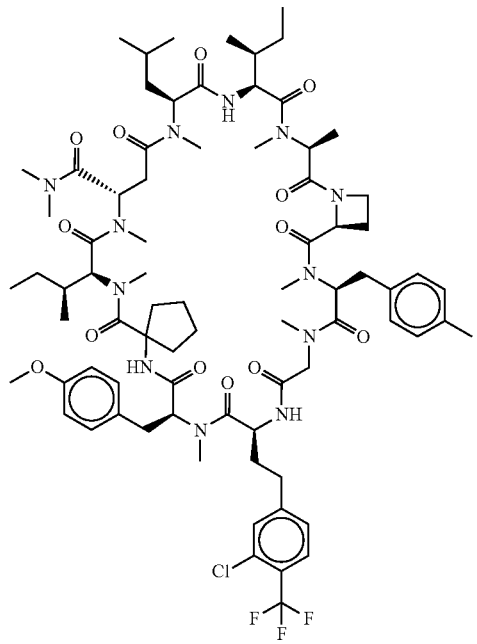 |
| 1936 | 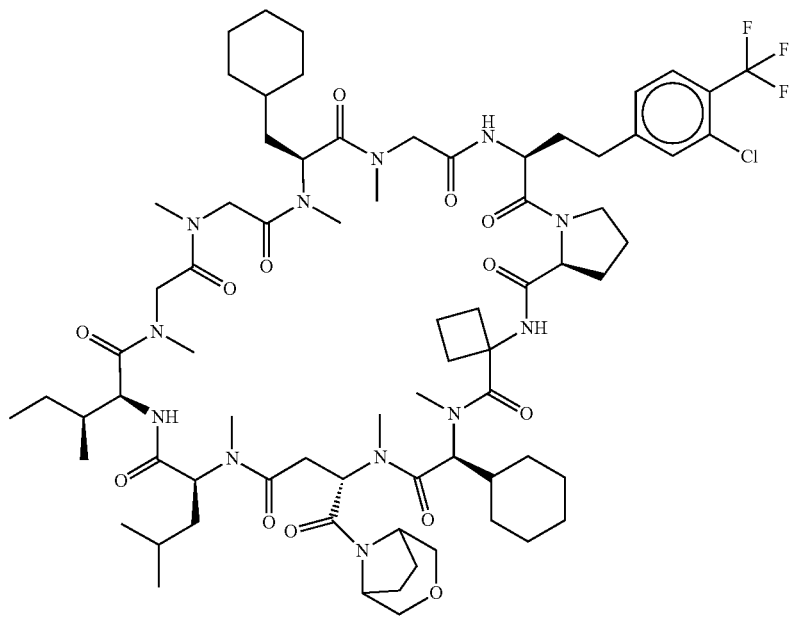 |

TABLE 24-continued
| Compound No. | Structural formula |
|---|---|
| 1937 | 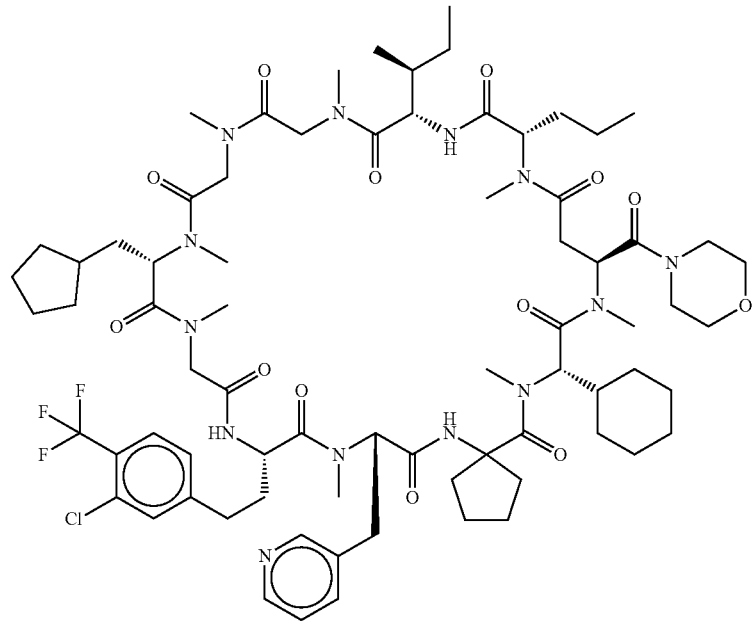 |
| 1938 | 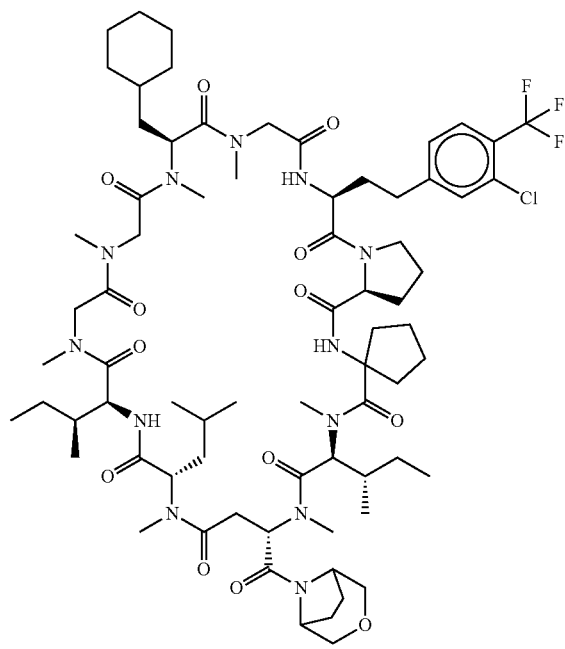 |

TABLE 24-continued
| Compound No. | Structural formula |
|---|---|
| 1939 | 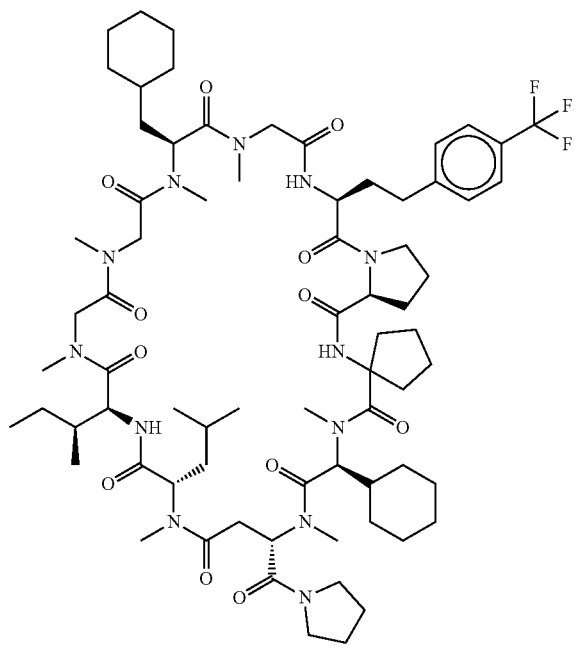 |
| 1940 | 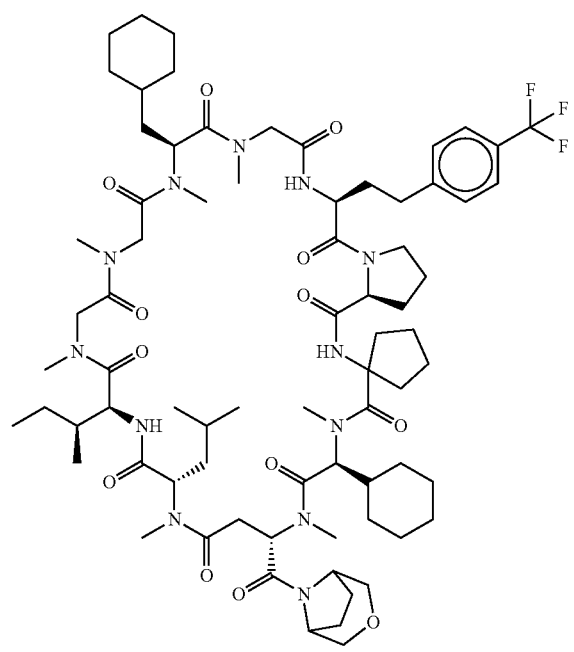 |

TABLE 24-continued
| Compound No. | Structural formula |
|---|---|
| 1941 | 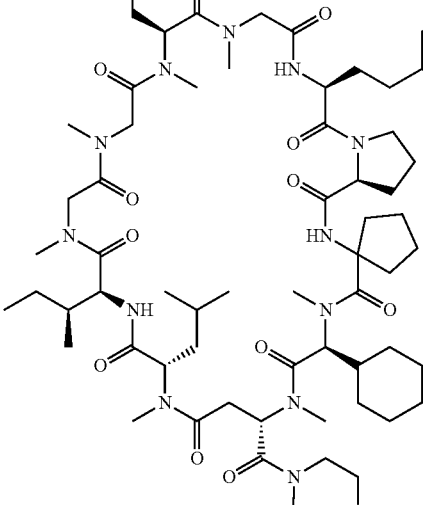 |
| 1942 | 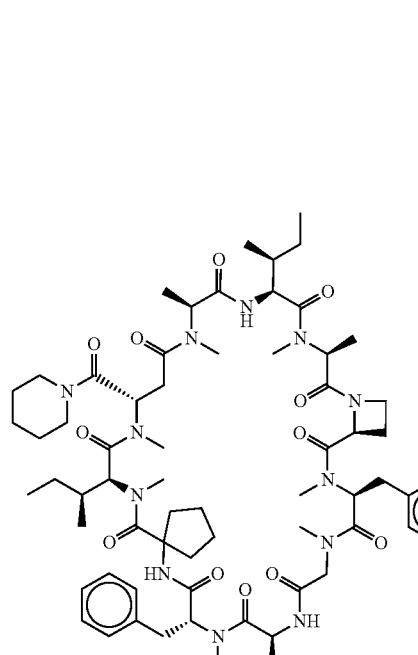 |

TABLE 24-continued
| Compound No. | Structural formula |
|---|---|
| 1943 | 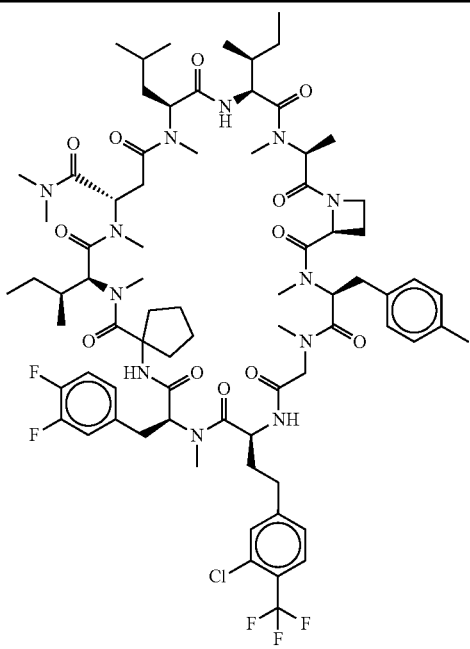 |
| 1944 | 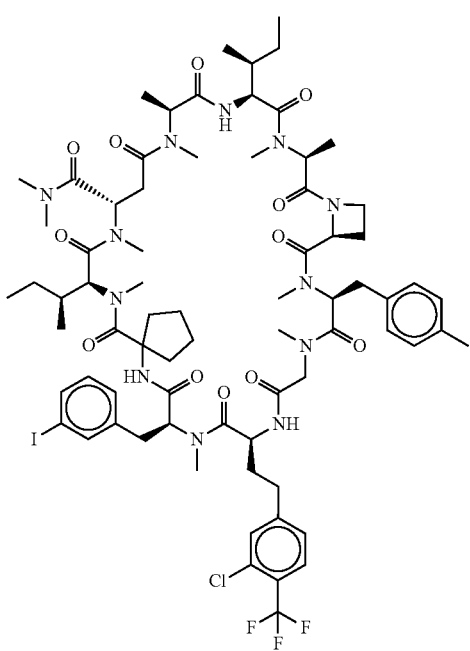 |

TABLE 24-continued
| Compound No. | Structural formula |
|---|---|
| 1945 | 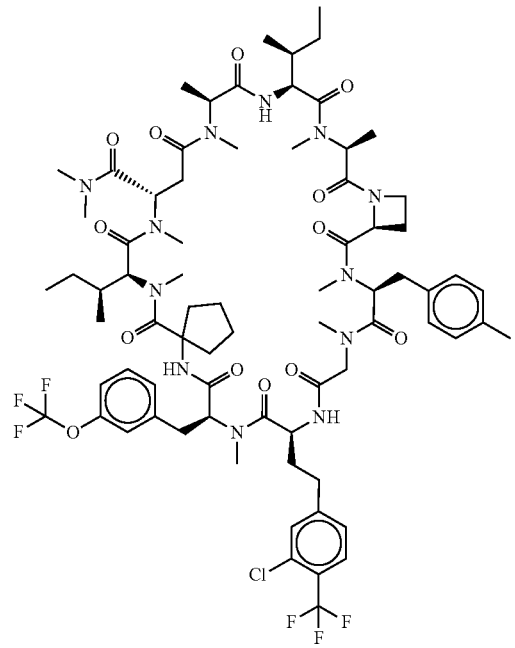 |
| 1946 | 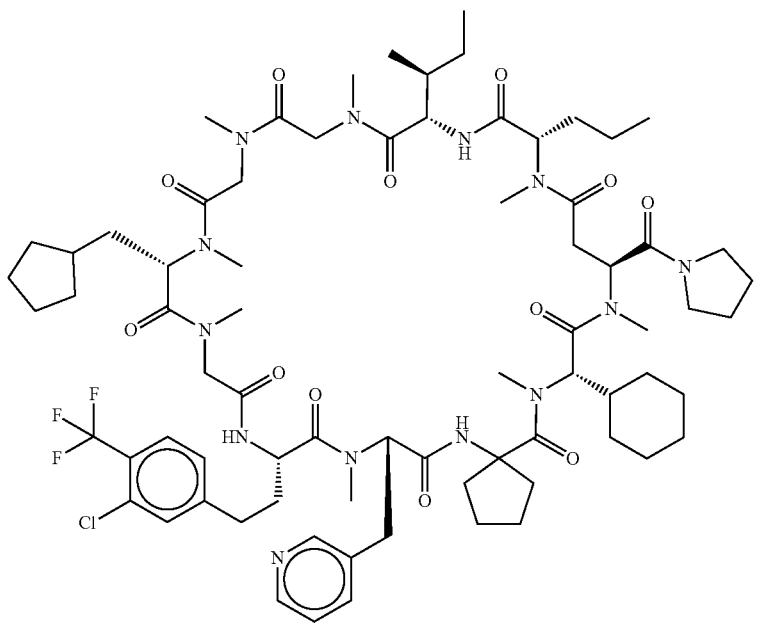 |

TABLE 24-continued
| Compound No. | Structural formula |
|---|---|
| 1947 | 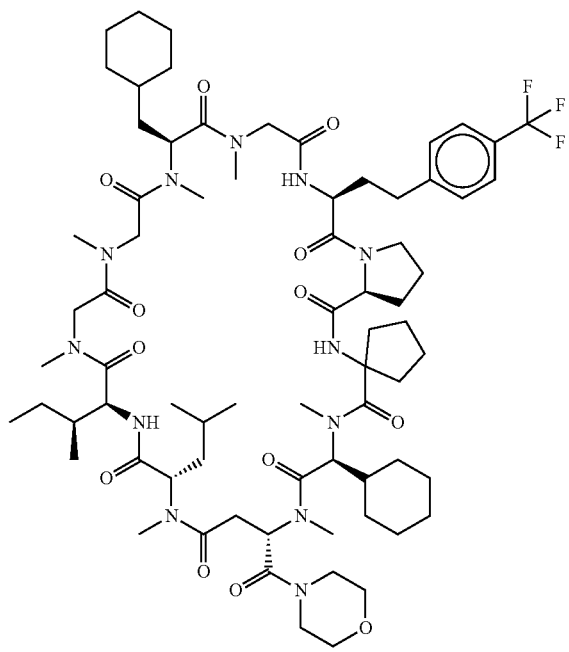 |
| 1948 | 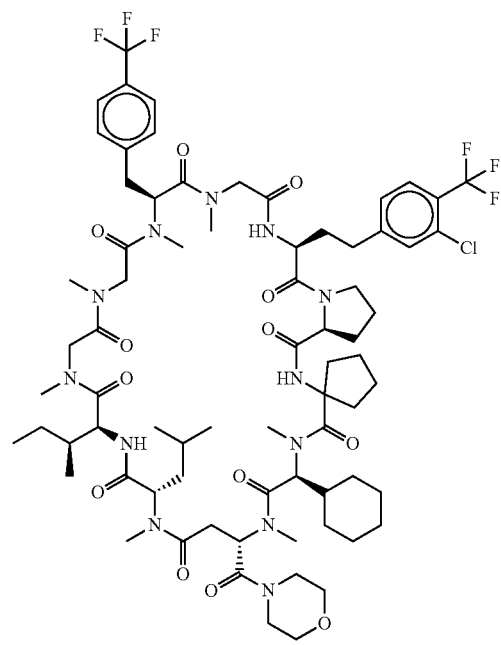 |

TABLE 24-continued

| Compound No. | Structural formula |
|---|---|
| 1949 | |
| 1950 | |

TABLE 24-continued
| Compound No. | Structural formula |
|---|---|
| 1951 | 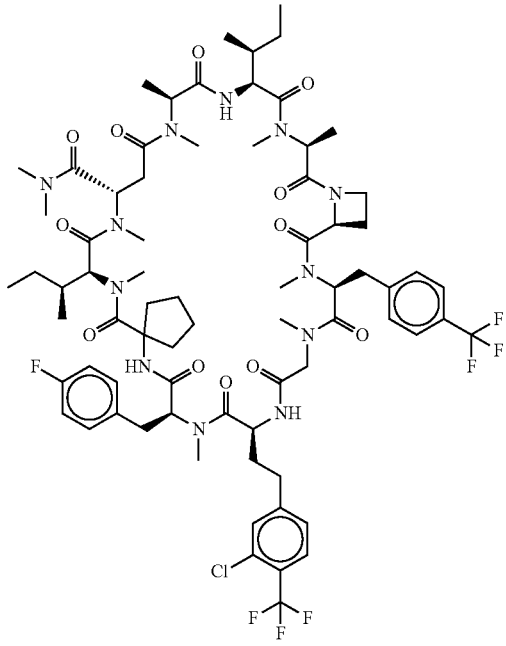 |
| 1952 | 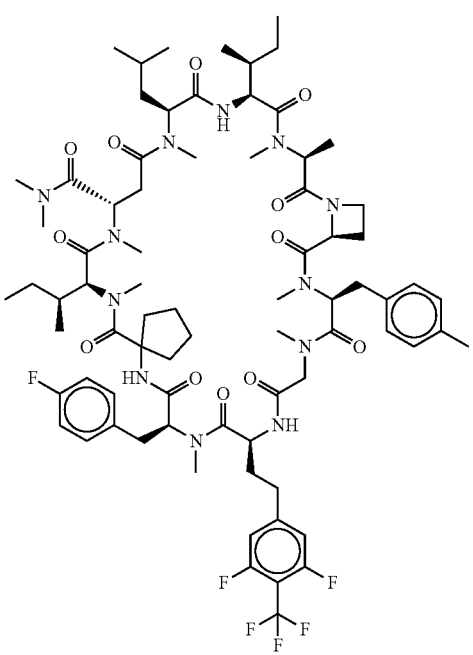 |

TABLE 24-continued
| Compound No. | Structural formula |
|---|---|
| 1953 | 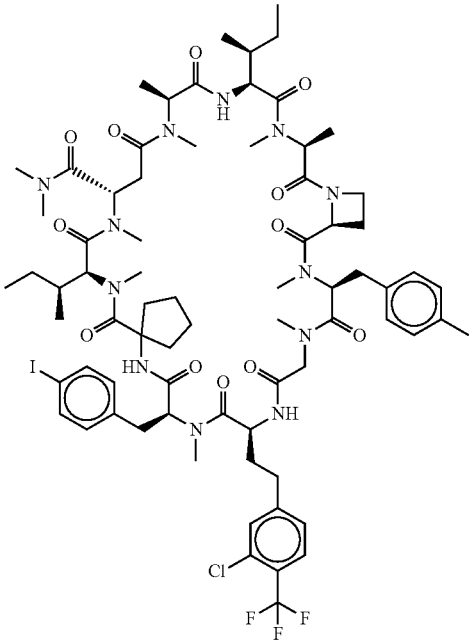 |
| 1954 | 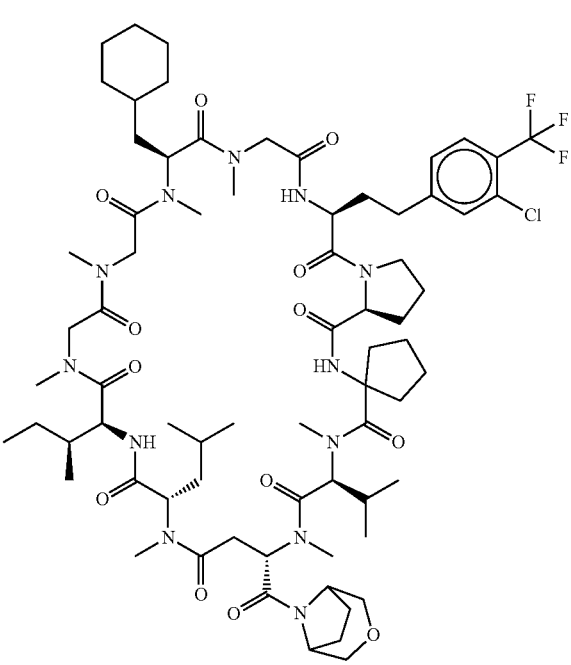 |

TABLE 24-continued
| Compound No. | Structural formula |
|---|---|
| 1955 | 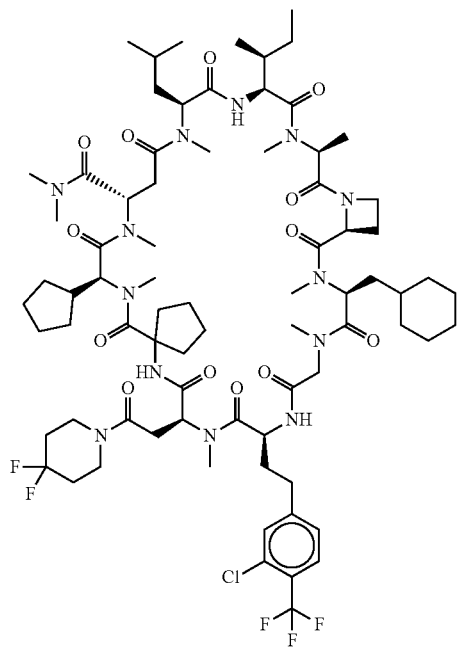 |
| 1956 | 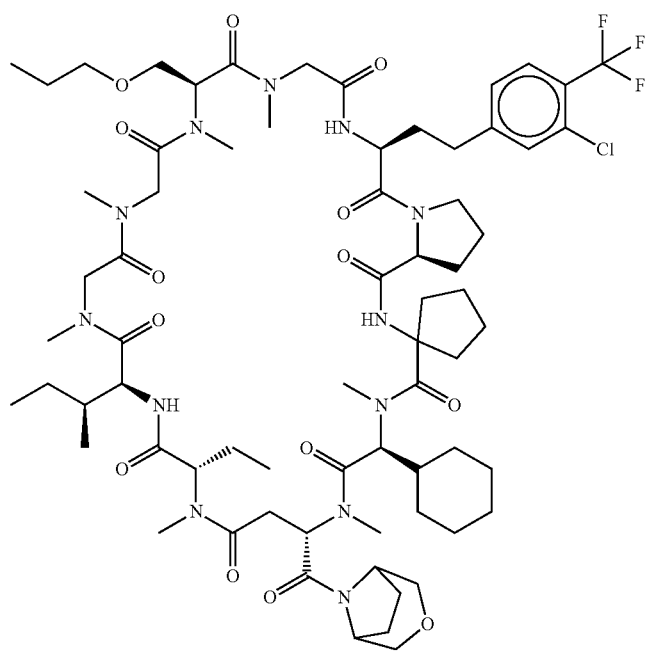 |

TABLE 24-continued
| Compound No. | Structural formula |
|---|---|
| 1957 | 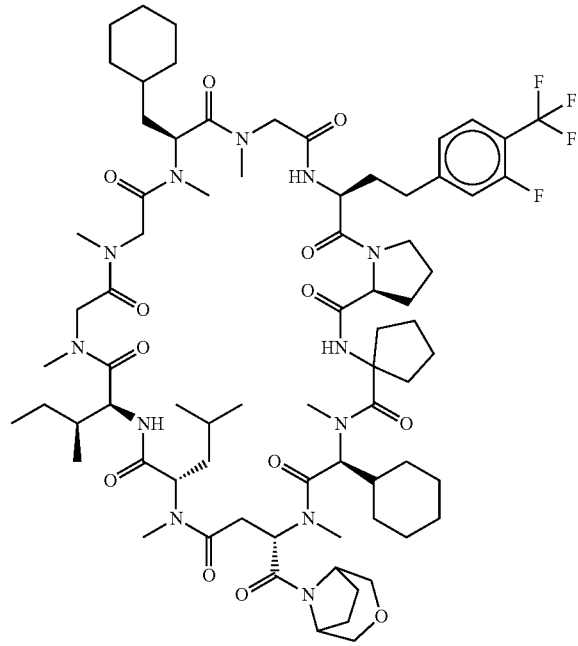 |
| 1958 | 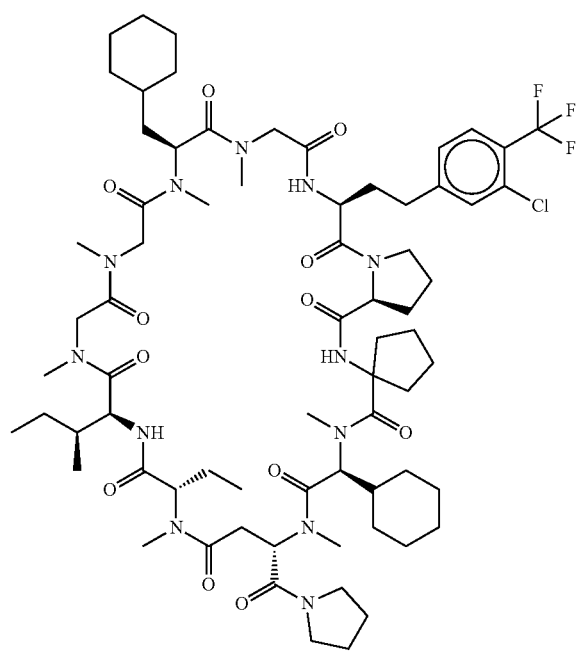 |

TABLE 24-continued
| Compound No. | Structural formula |
|---|---|
| 1959 | 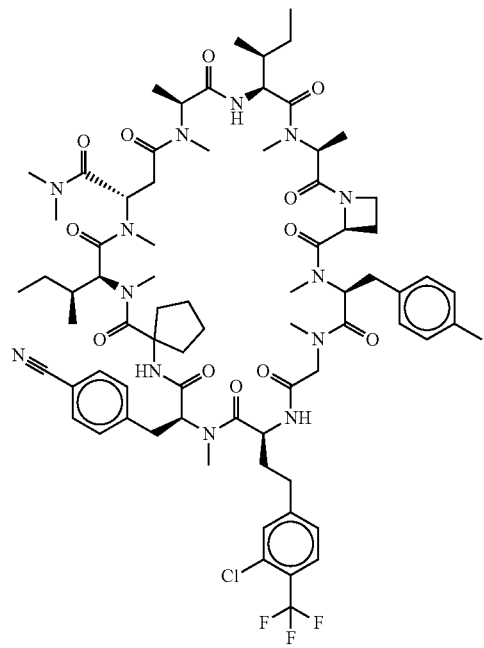 |
| 1960 | 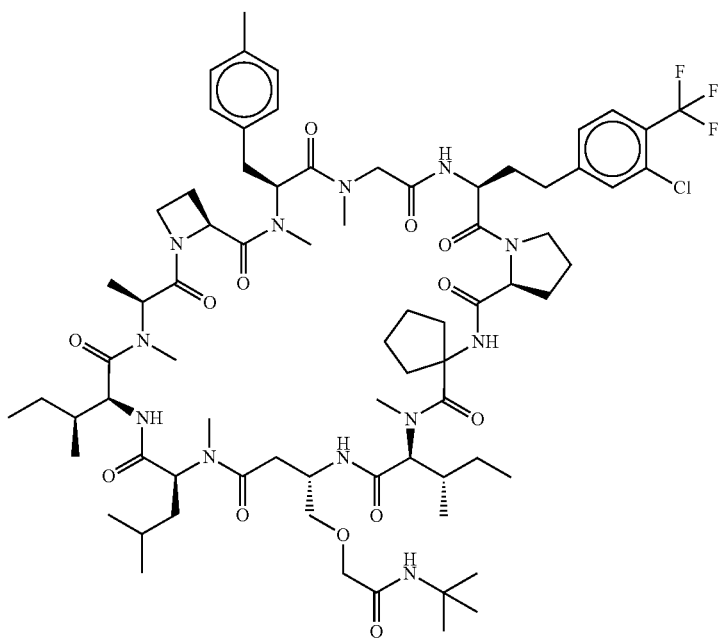 |

TABLE 24-continued
| Compound No. | Structural formula |
|---|---|
| 1961 | 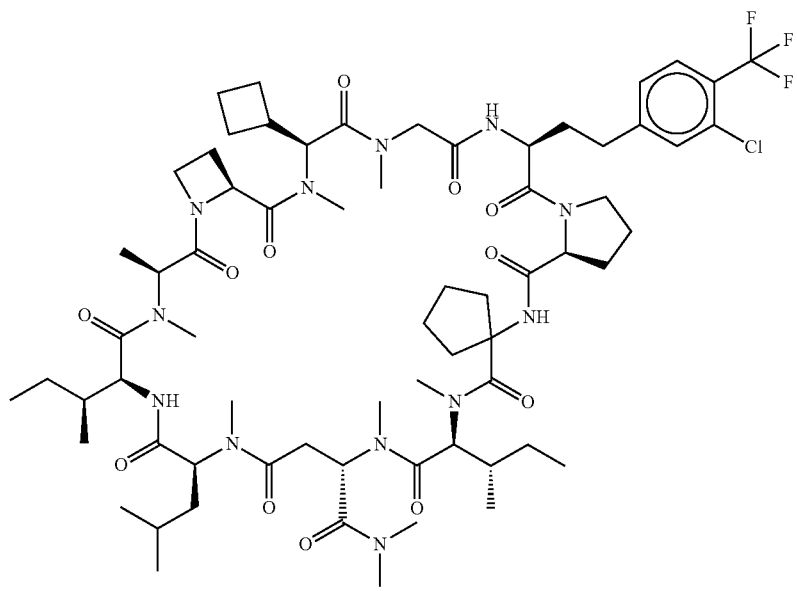 |
| 1962 | 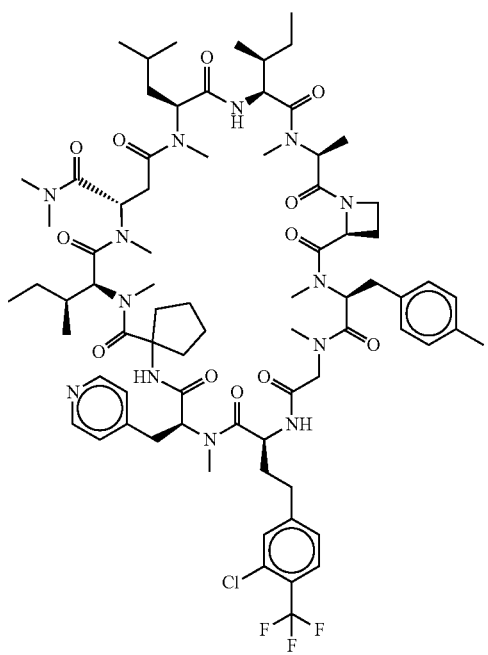 |

TABLE 24-continued
| Compound No. | Structural formula |
|---|---|
| 1963 | 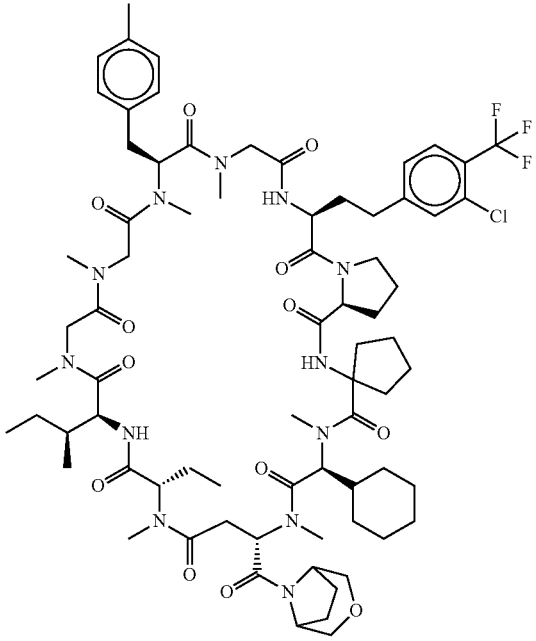 |
| 1964 | 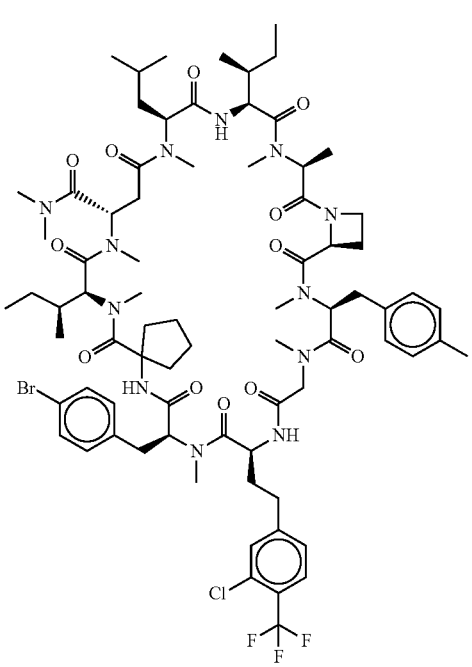 |

TABLE 24-continued
| Compound No. | Structural formula |
|---|---|
| 1965 | 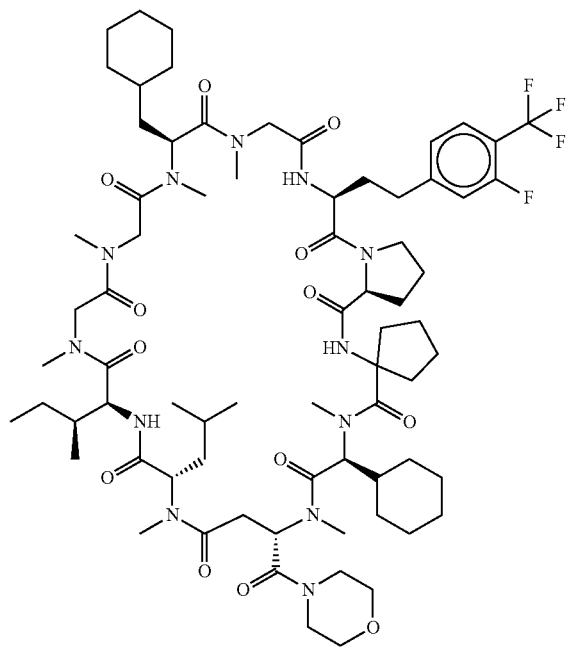 |
| 1966 | 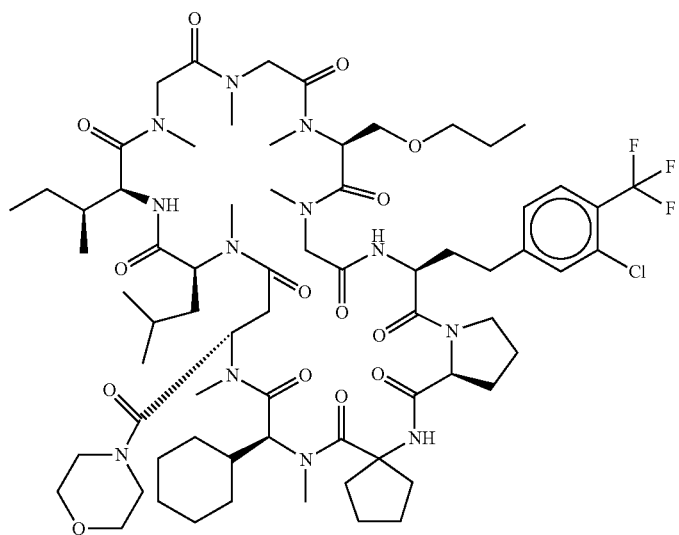 |

TABLE 24-continued
| Compound No. | Structural formula |
|---|---|
| 1967 | 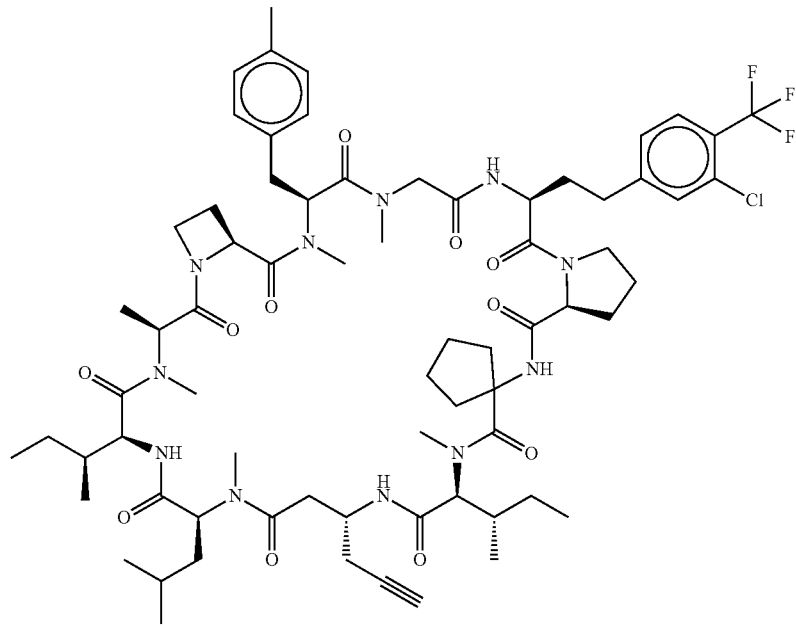 |
| 1968 | 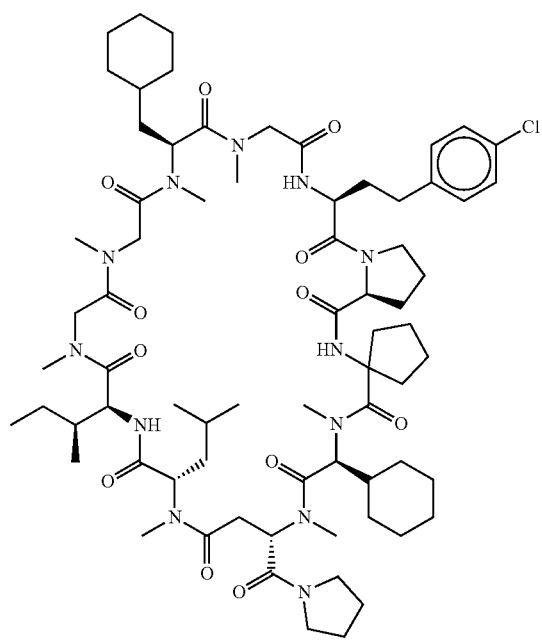 |

TABLE 24-continued
| Compound No. | Structural formula |
|---|---|
| 1969 | 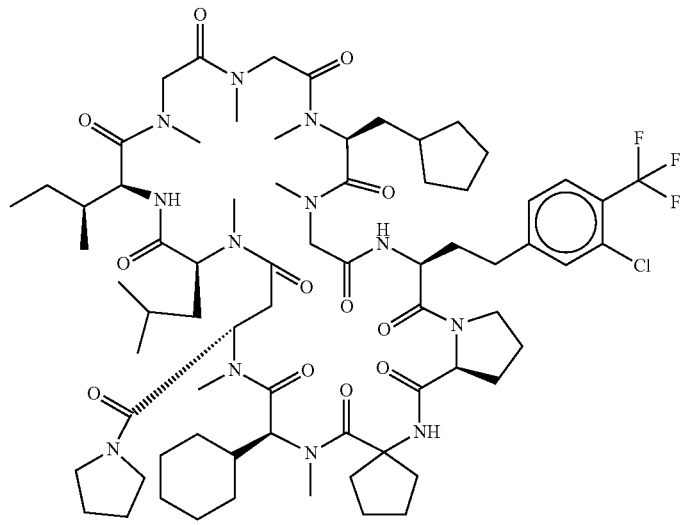 |
| 1970 | 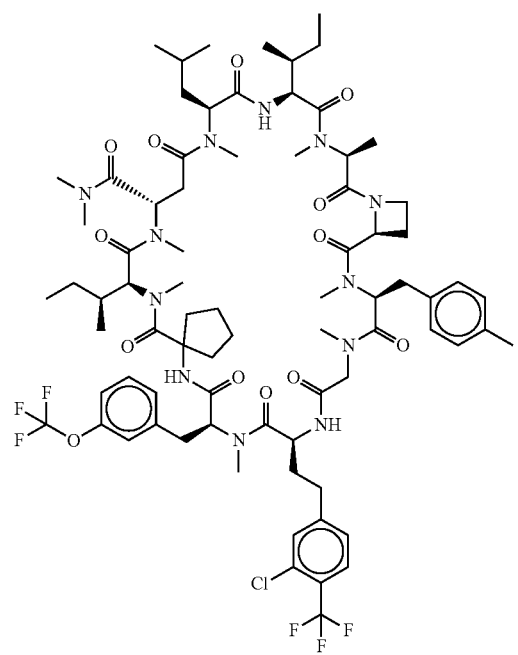 |

TABLE 24-continued
| Compound No. | Structural formula |
|---|---|
| 1971 | 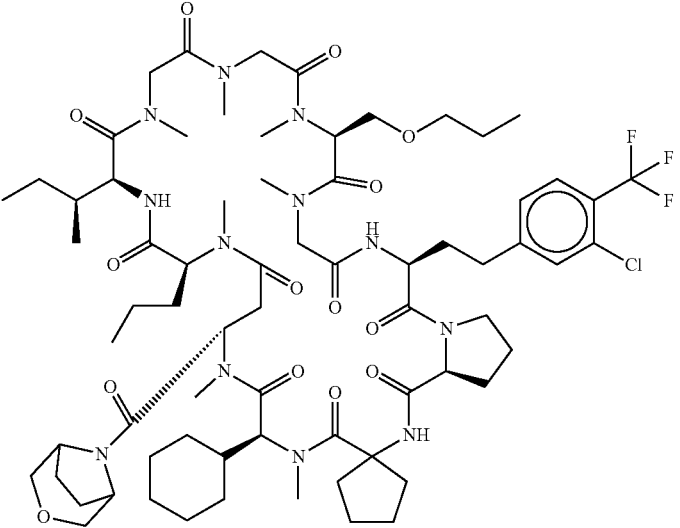 |
| 1972 | 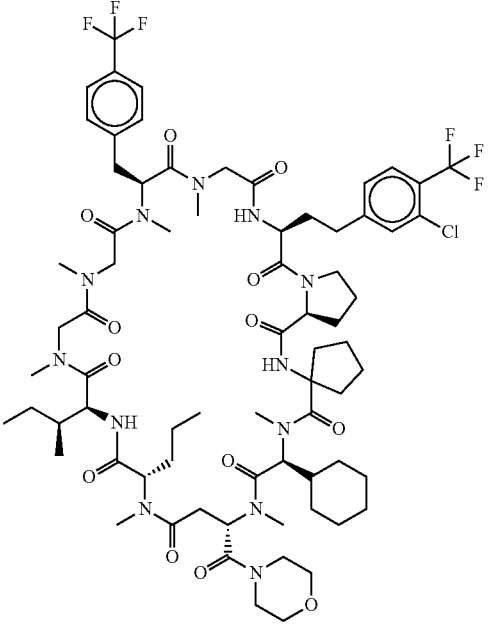 |

TABLE 24-continued
| Compound No. | Structural formula |
|---|---|
| 1973 | 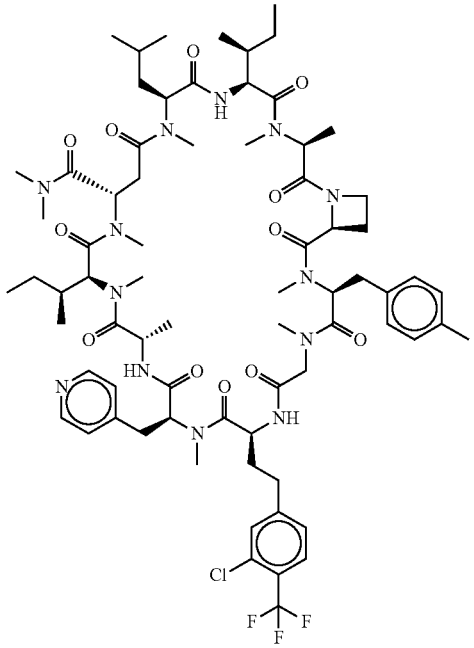 |
| 1974 | 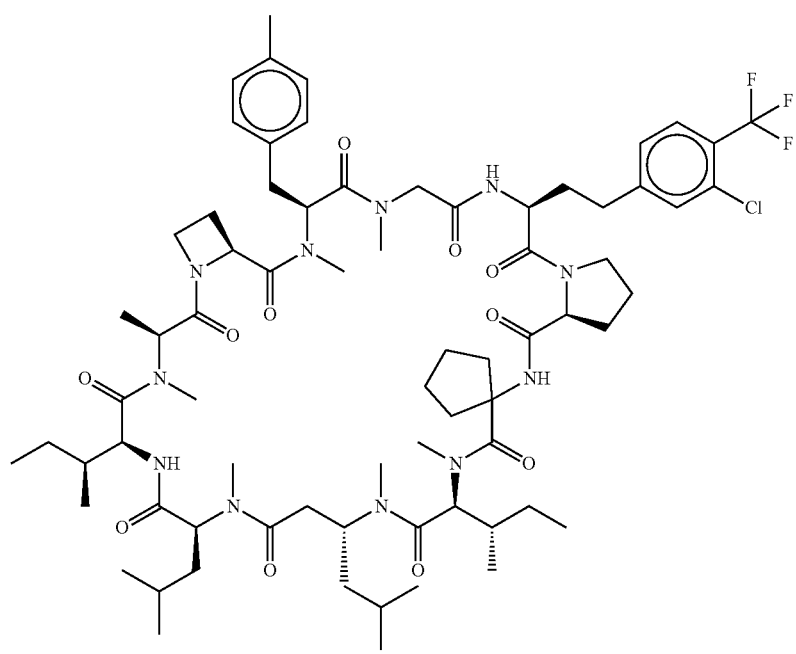 |

TABLE 24-continued
| Compound No. | Structural formula |
|---|---|
| 1975 | 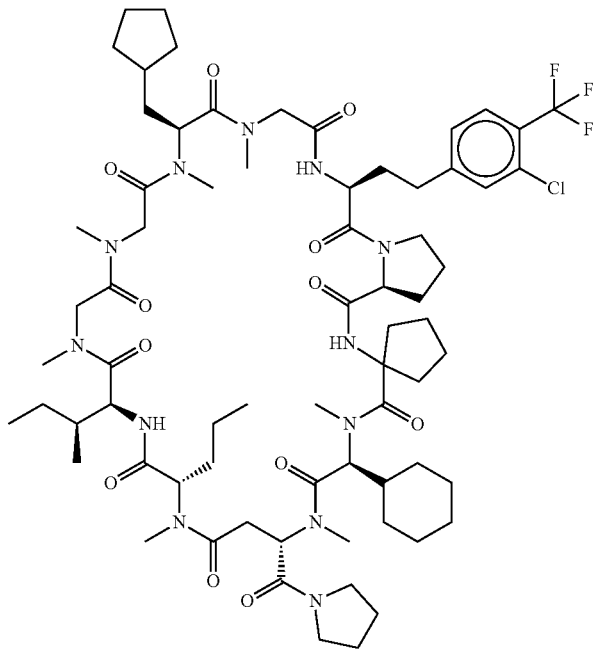 |
| 1976 | 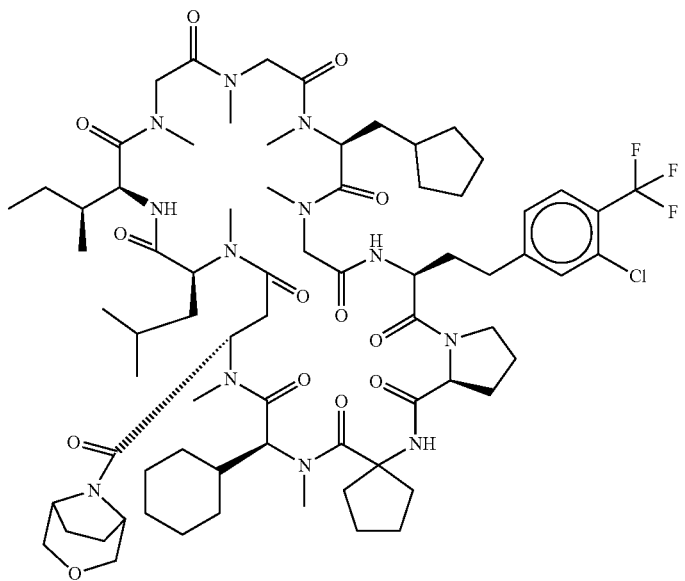 |

TABLE 24-continued
| Compound No. | Structural formula |
|---|---|
| 1977 | 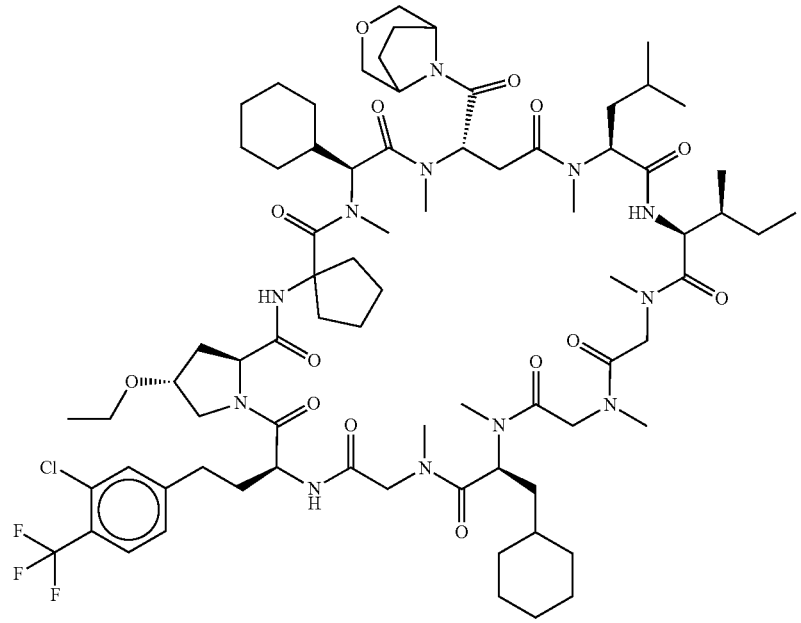 |
| 1978 | 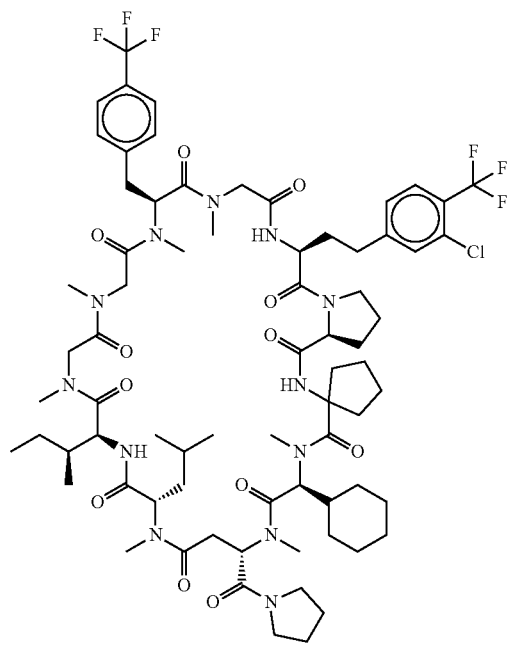 |

TABLE 24-continued
| Compound No. | Structural formula |
|---|---|
| 1979 | 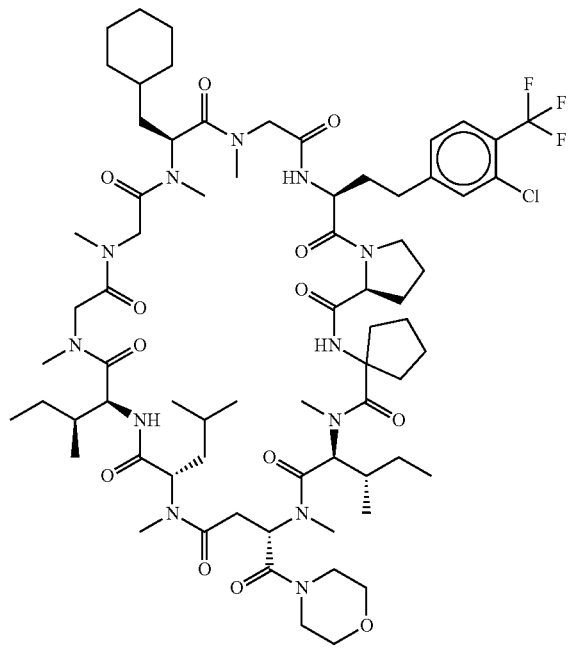 |
| 1980 | 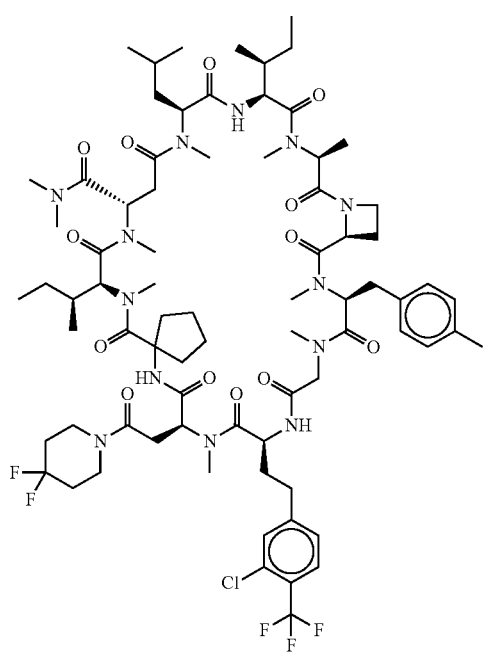 |

TABLE 24-continued
| Compound No. | Structural formula |
|---|---|
| 1981 | 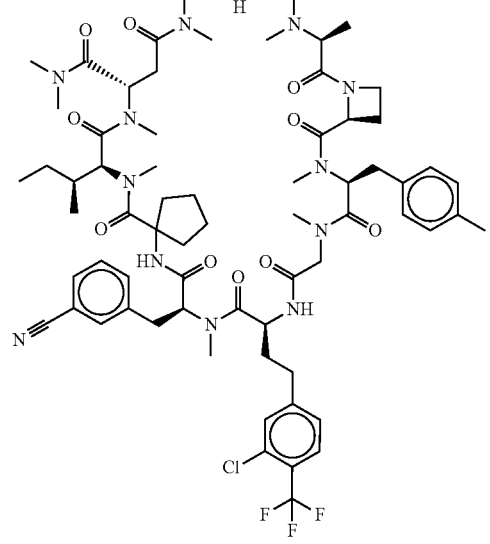 |
| 1982 | 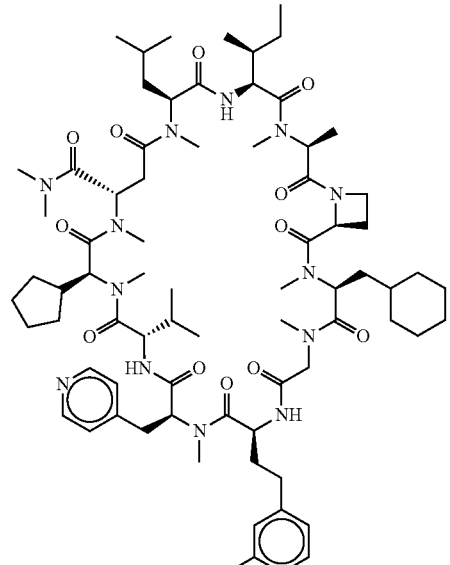 |

TABLE 24-continued
| Compound No. | Structural formula |
|---|---|
| 1983 | 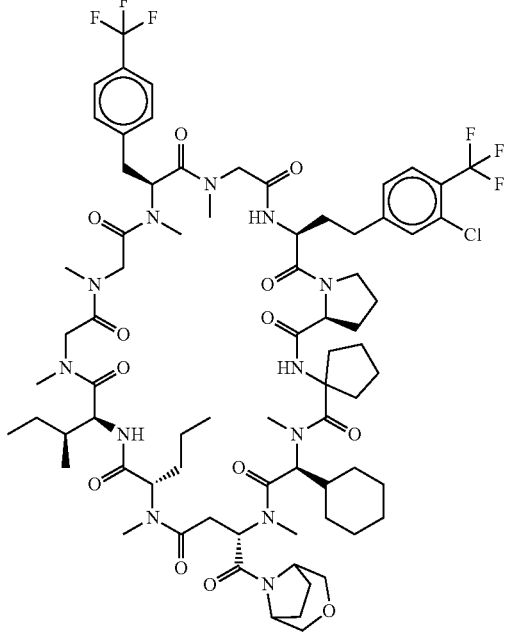 |
| 1984 | 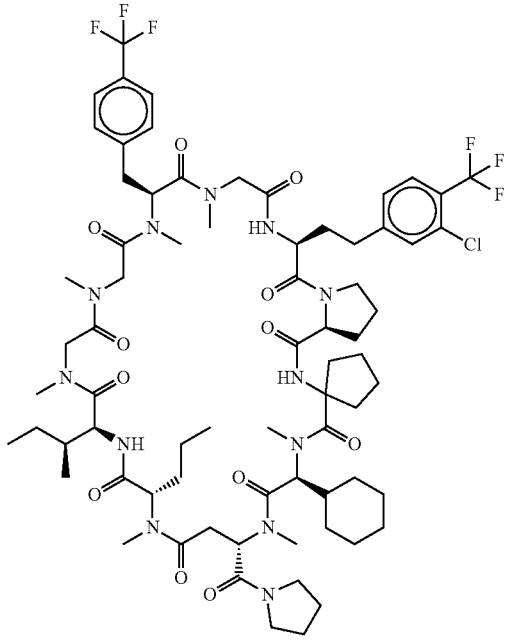 |

TABLE 24-continued
| Compound No. | Structural formula |
|---|---|
| 1985 | 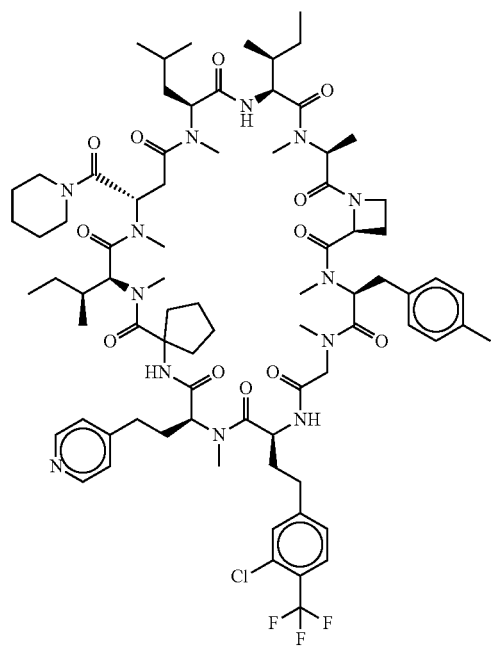 |
| 1986 | 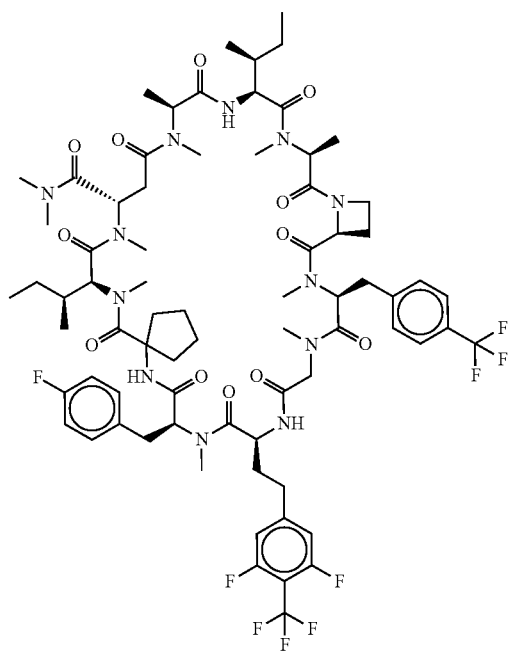 |

TABLE 24-continued
| Compound No. | Structural formula |
|---|---|
| 1987 | 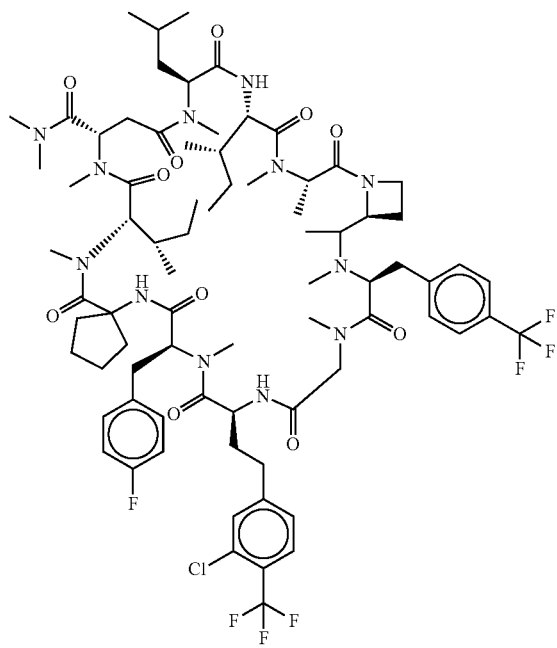 |
| 1988 | 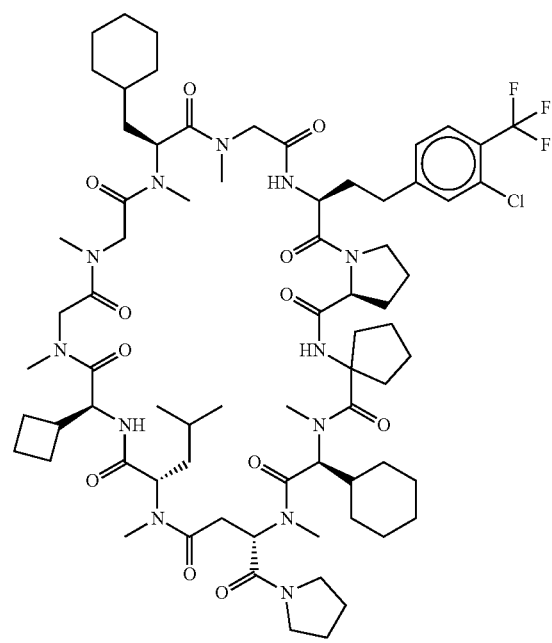 |

TABLE 24-continued
| Compound No. | Structural formula |
|---|---|
| 1989 | 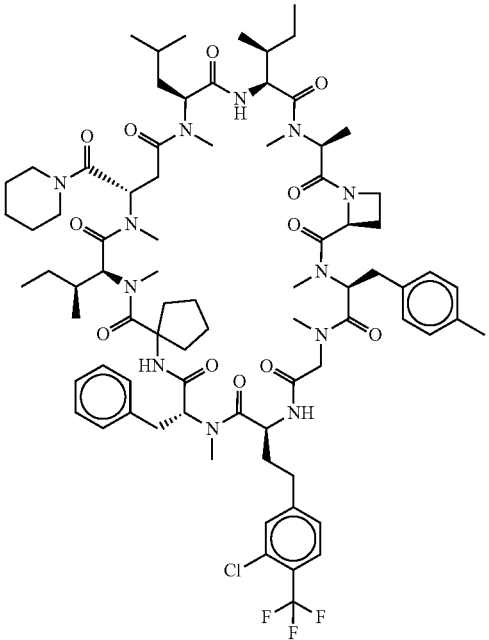 |
| 1990 | 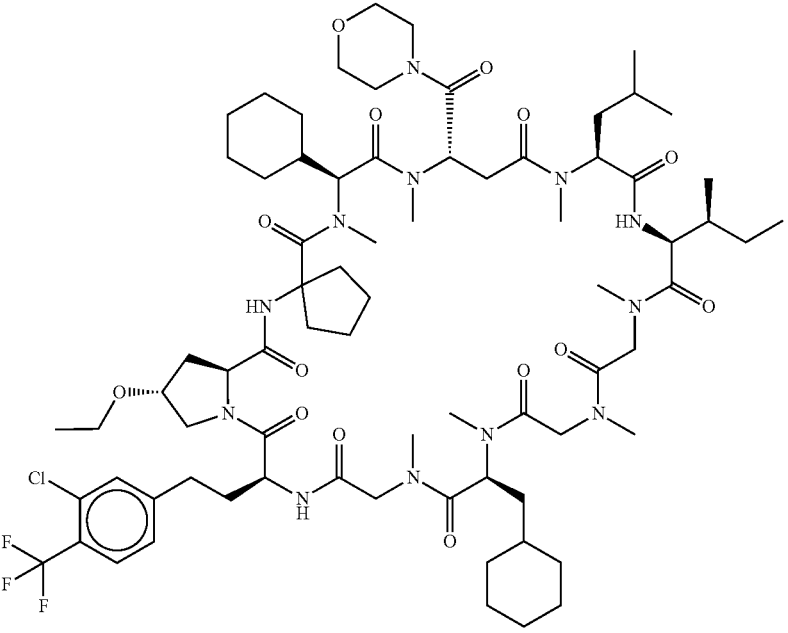 |

TABLE 24-continued
| Compound No. | Structural formula |
|---|---|
| 1991 | 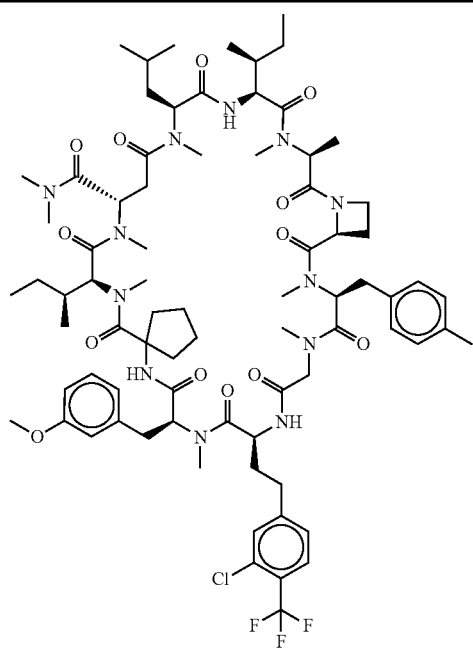 |
| 1992 | 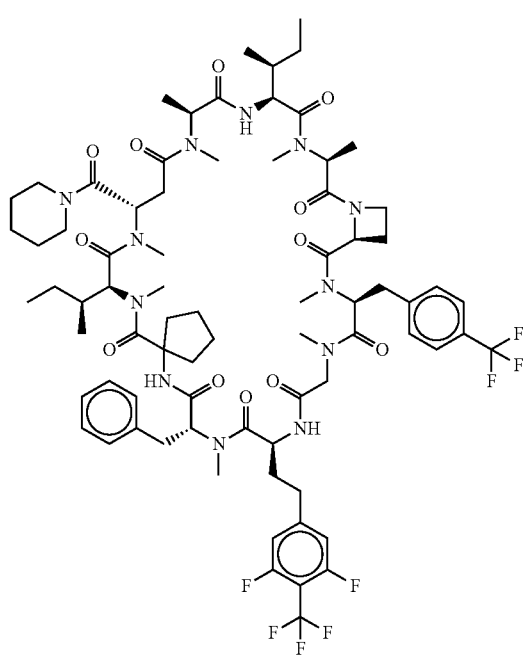 |

TABLE 24-continued
| Compound No. | Structural formula |
|---|---|
| 1993 | 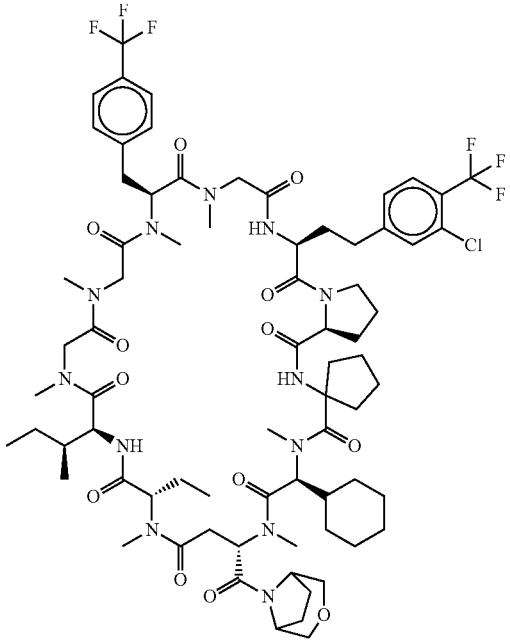 |
| 1994 | 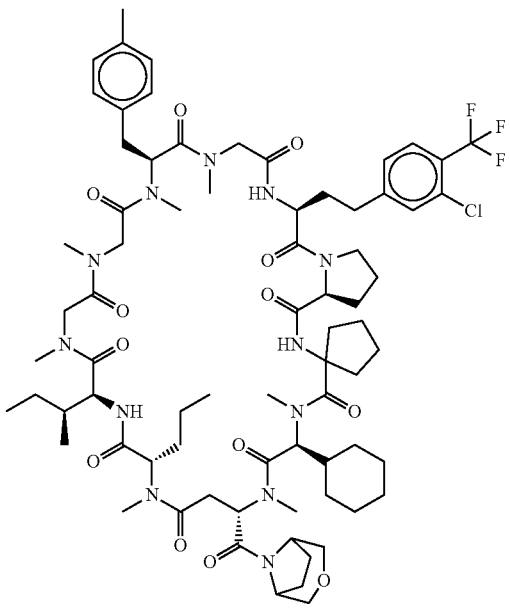 |

TABLE 24-continued
| Compound No. | Structural formula |
|---|---|
| 1995 | 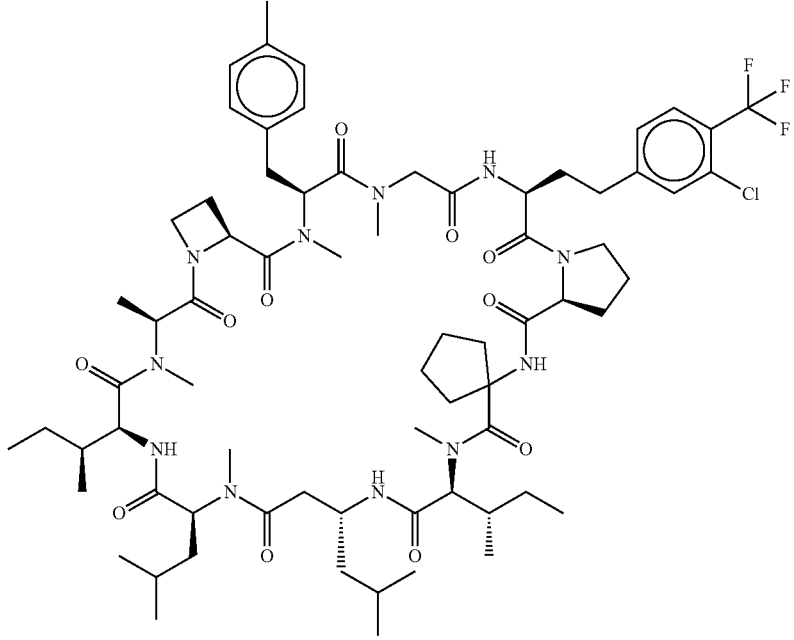 |
| 1996 | 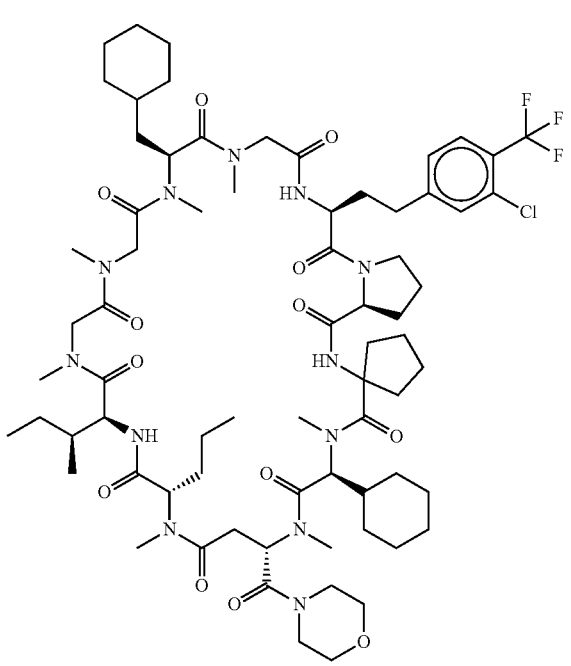 |

TABLE 24-continued
| Compound No. | Structural formula |
| --- | --- |
| 1997 | 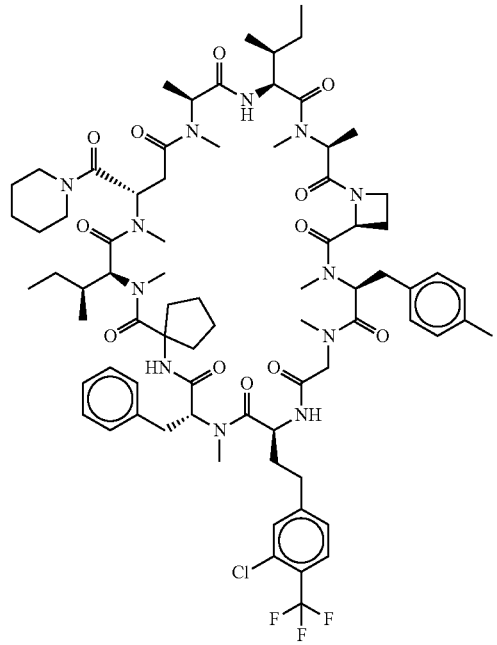 |
| 1998 | 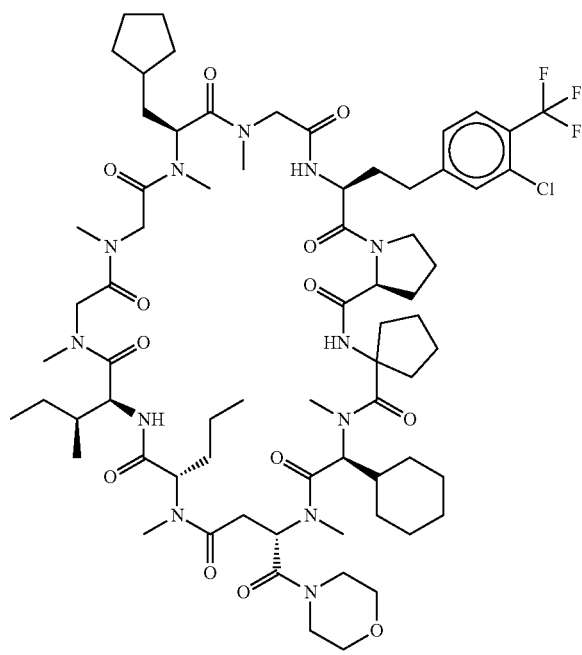 |

TABLE 24-continued
| Compound No. | Structural formula |
|---|---|
| 1999 | 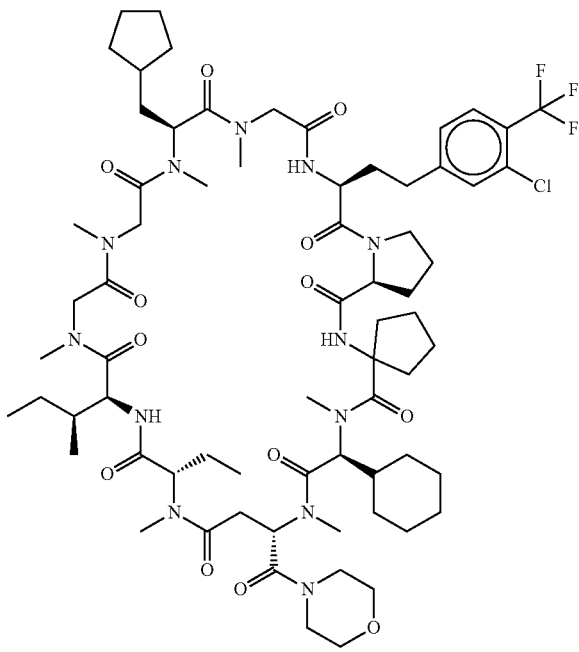 |
| 2000 | 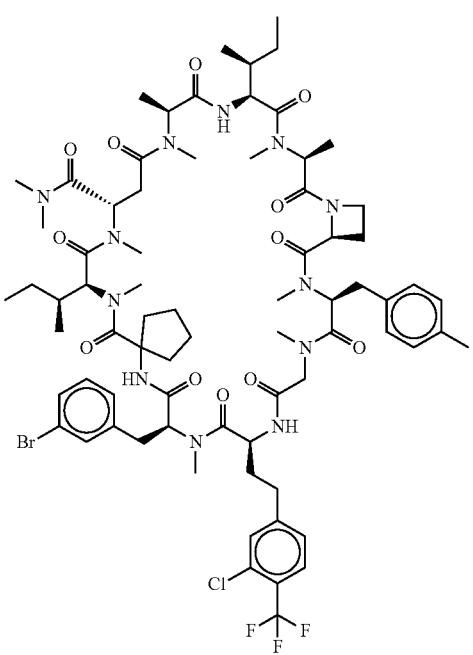 |

TABLE 24-continued
| Compound No. | Structural formula |
|---|---|
| 2001 | 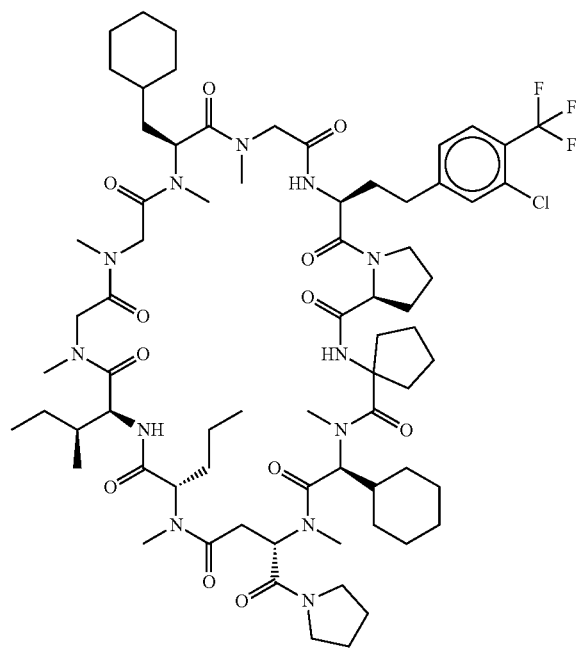 |
| 2002 | 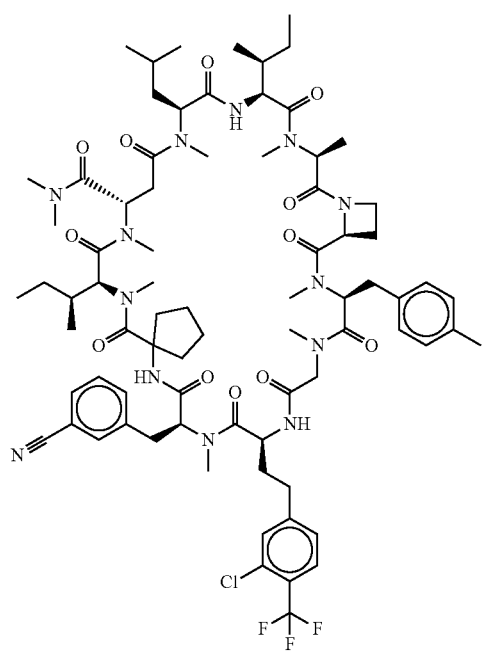 |

TABLE 24-continued
| Compound No. | Structural formula |
|---|---|
| 2003 | 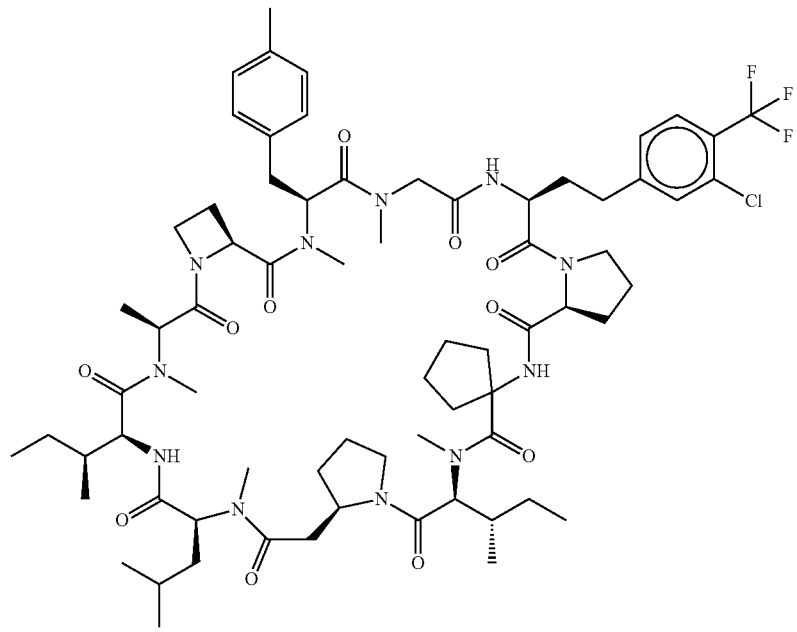 |
| 2004 | 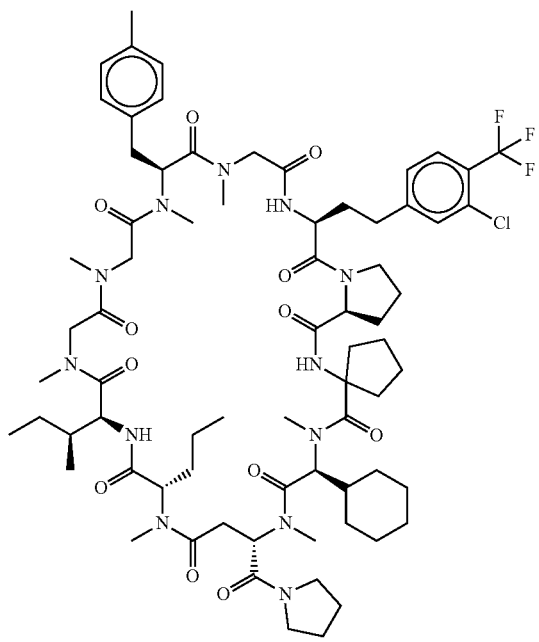 |

TABLE 24-continued
| Compound No. | Structural formula |
|---|---|
| 2005 | 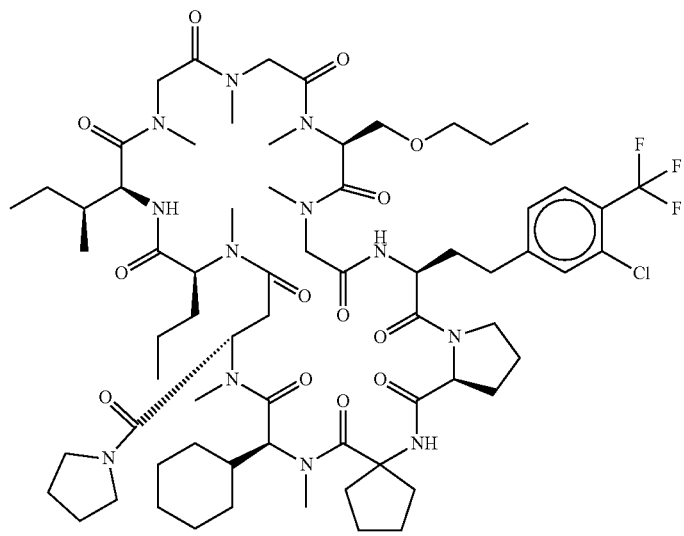 |
| 2006 | 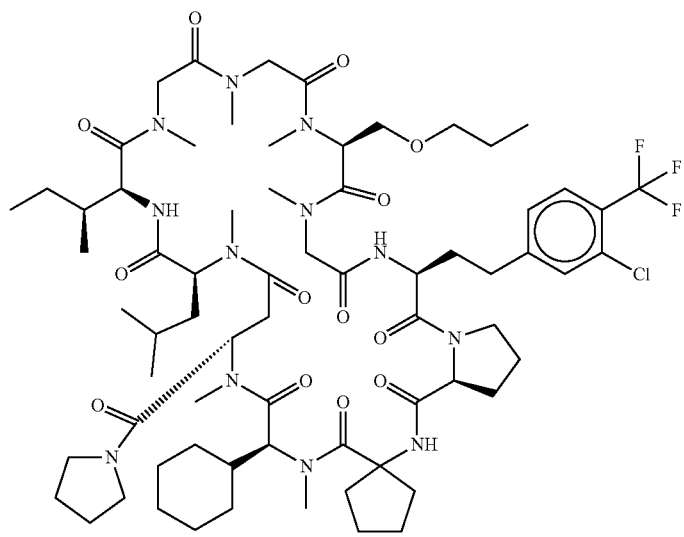 |

TABLE 24-continued
| Compound No. | Structural formula |
|---|---|
| 2007 | 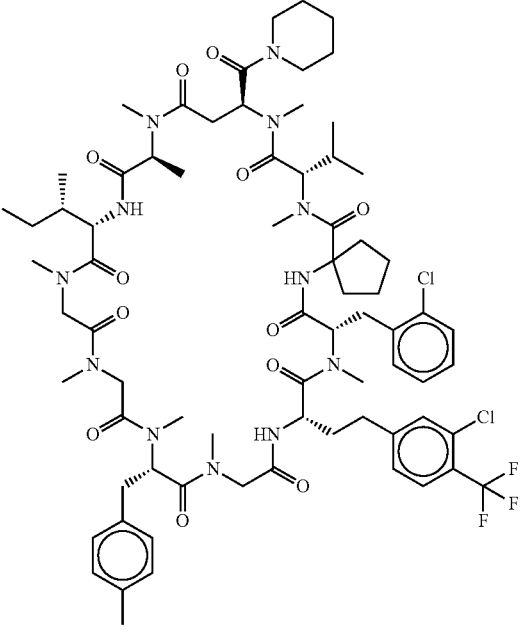 |
| 2008 | 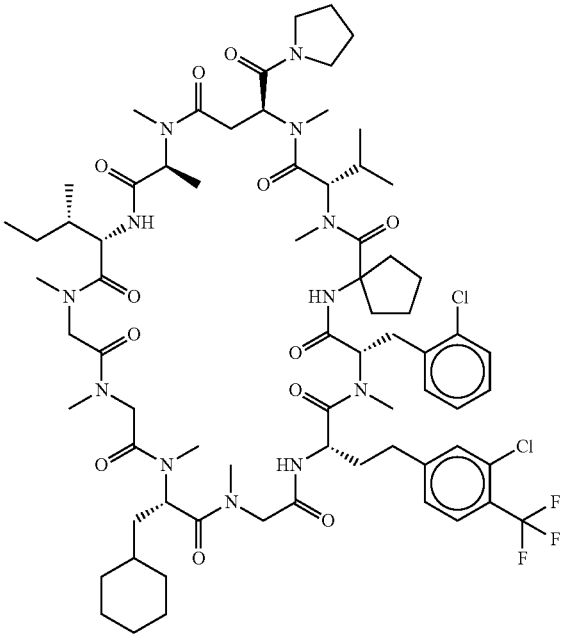 |

TABLE 24-continued
| Compound No. | Structural formula |
|---|---|
| 2009 | 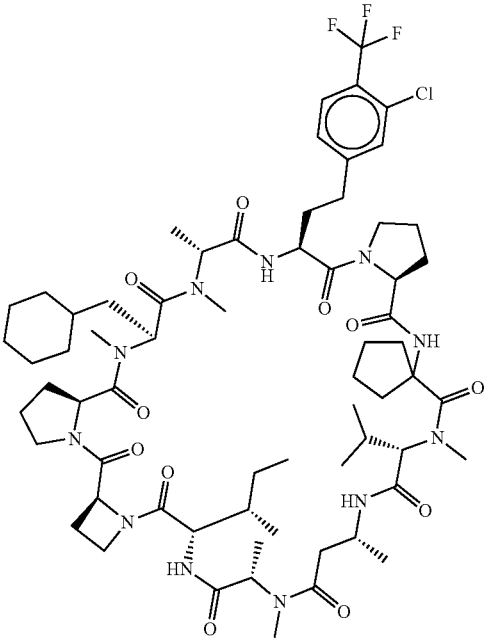 |
| 2010 | 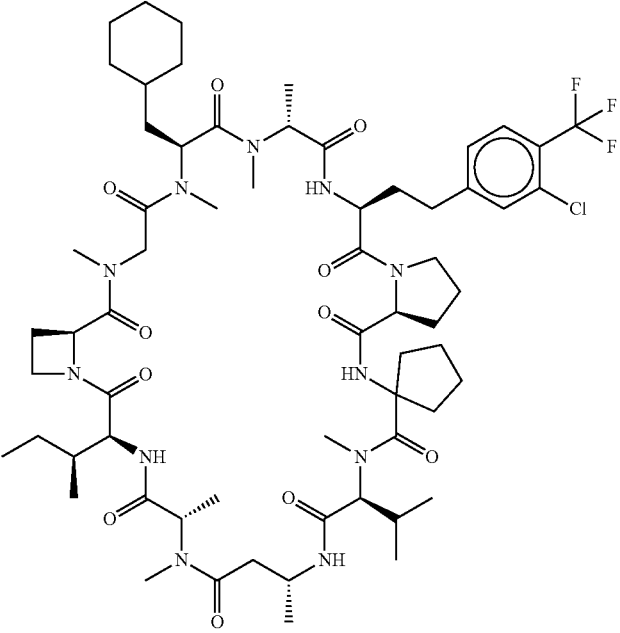 |

TABLE 24-continued
| Compound No. | Structural formula |
|---|---|
| 2011 | 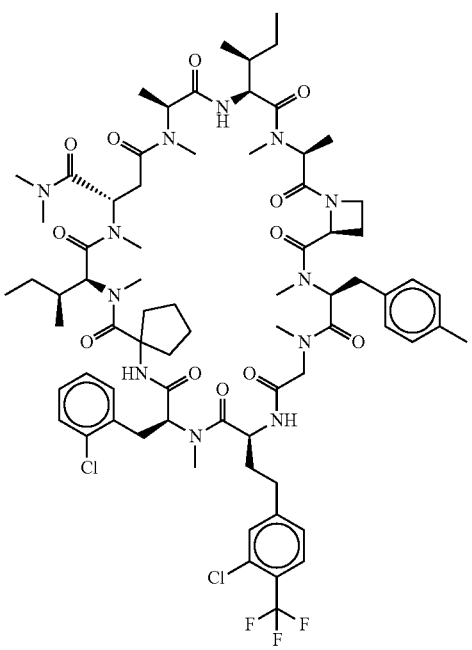 |
| 2012 | 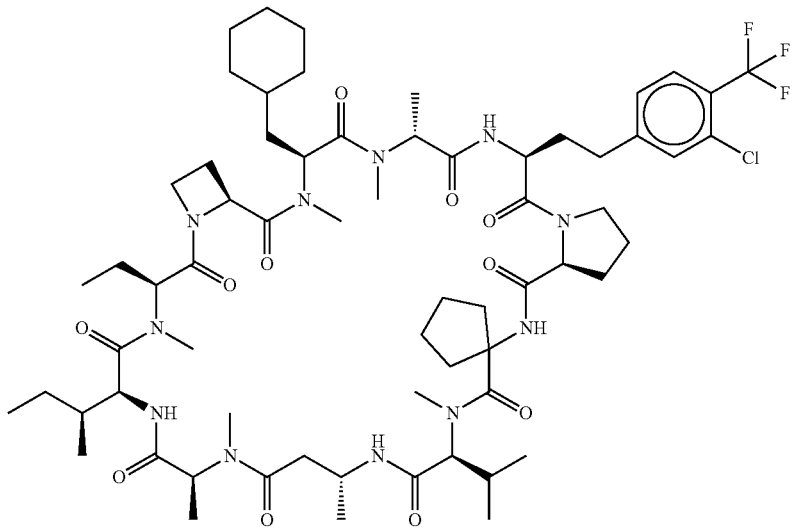 |

TABLE 24-continued
| Compound No. | Structural formula |
|---|---|
| 2013 | 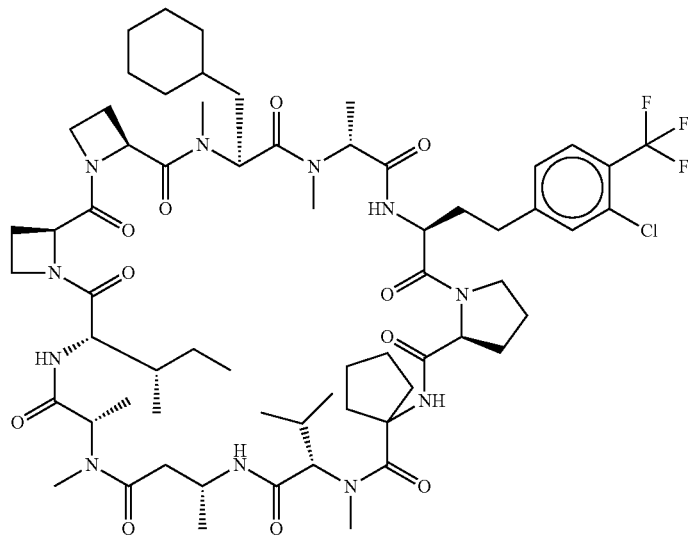 |
| 2014 | 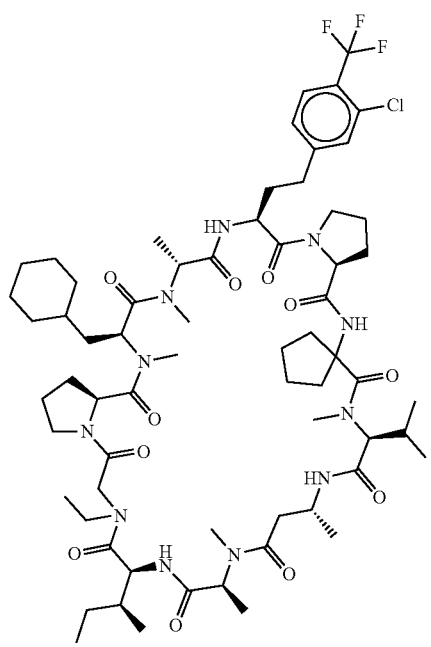 |

TABLE 24-continued
| Compound No. | Structural formula |
|---|---|
| 2015 | 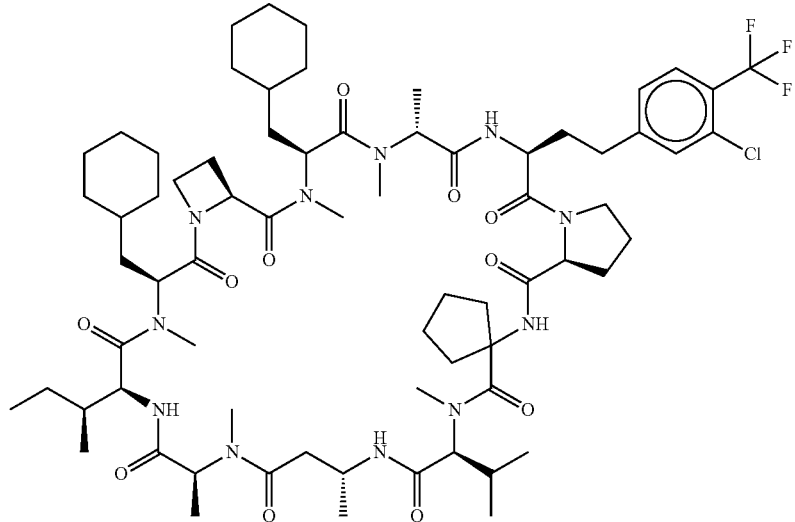 |
| 2016 | 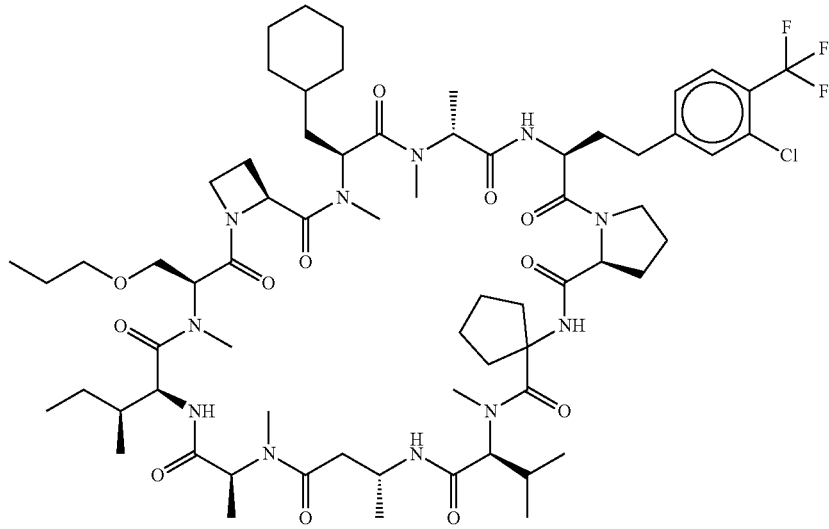 |
| 2017 | 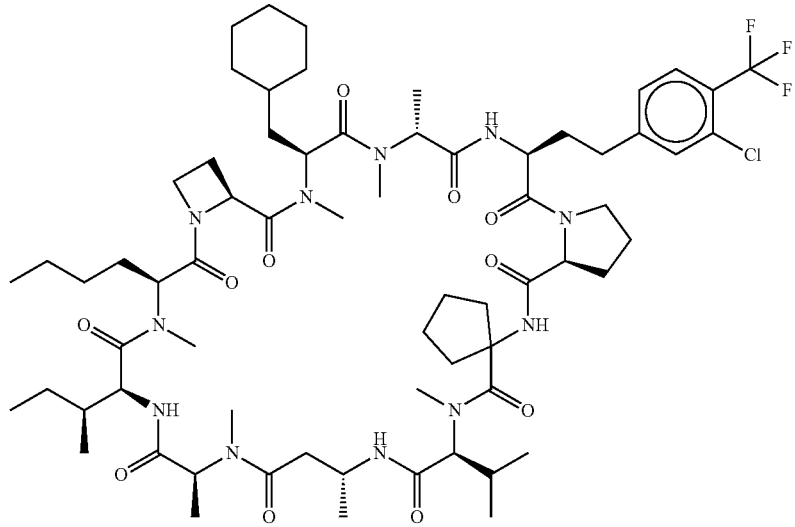 |

TABLE 24-continued
| Compound No. | Structural formula |
|---|---|
| 2018 | 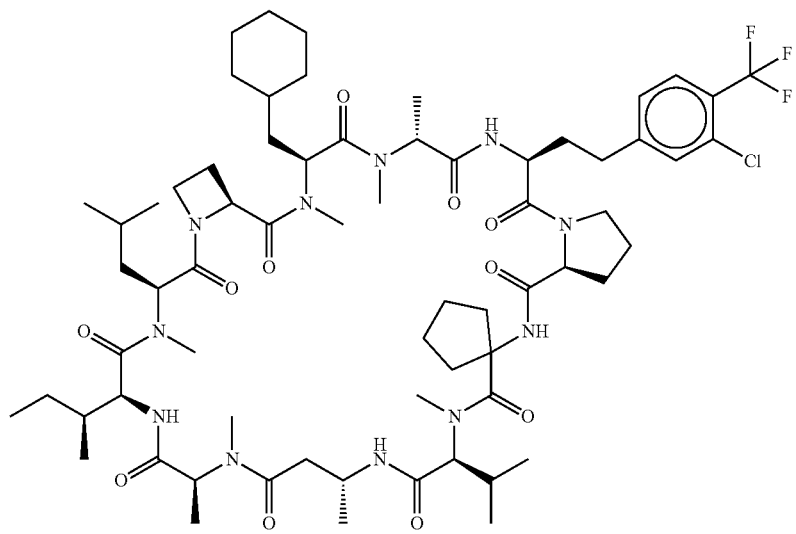 |
| 2019 | 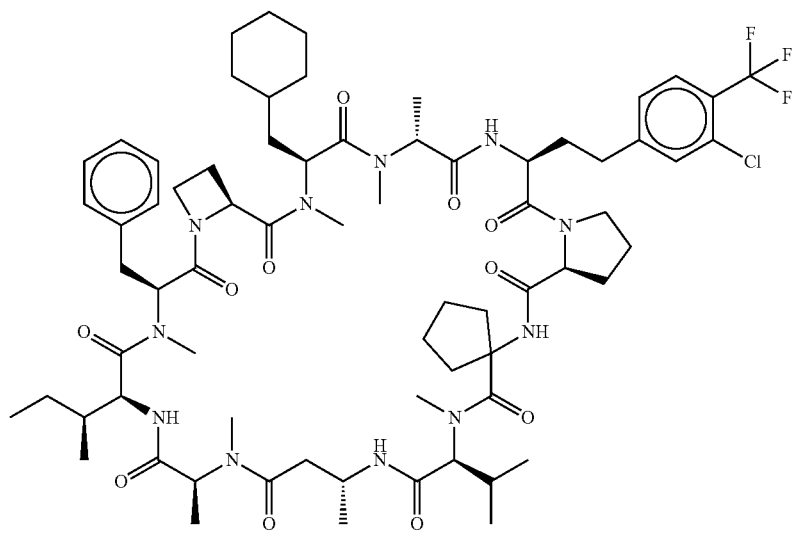 |

TABLE 24-continued
| Compound No. | Structural formula |
|---|---|
| 2020 | 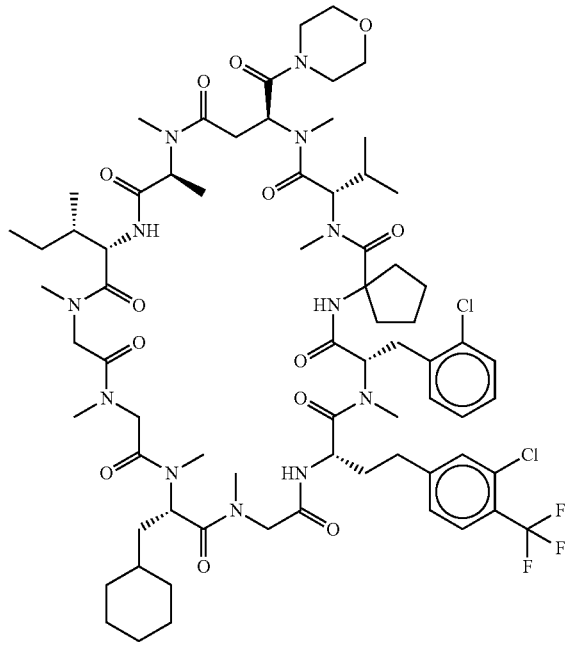 |
| 2021 | 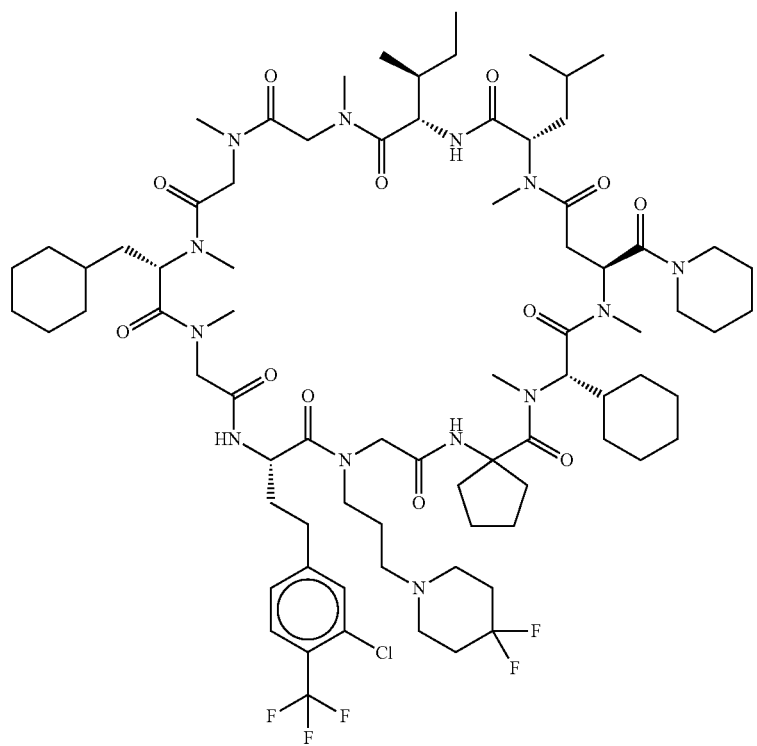 |

TABLE 24-continued
| Compound No. | Structural formula |
|---|---|
| 2022 | 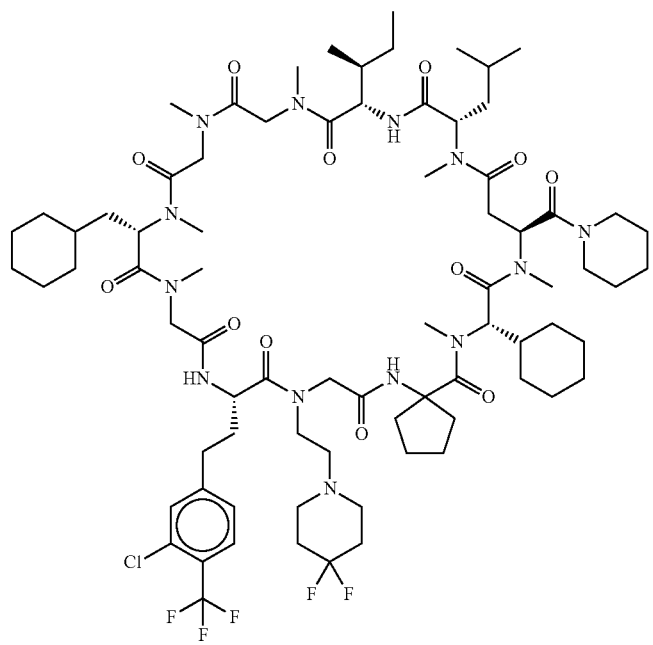 |
| 2023 | 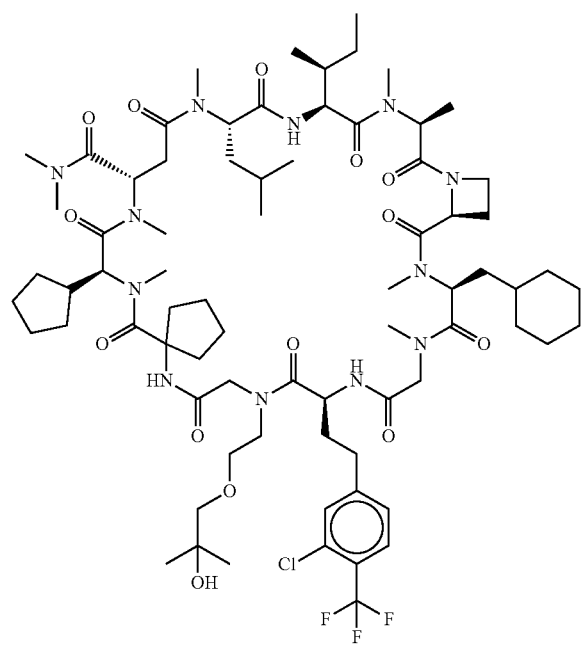 |

TABLE 24-continued
| Compound No. | Structural formula |
|---|---|
| 2024 | 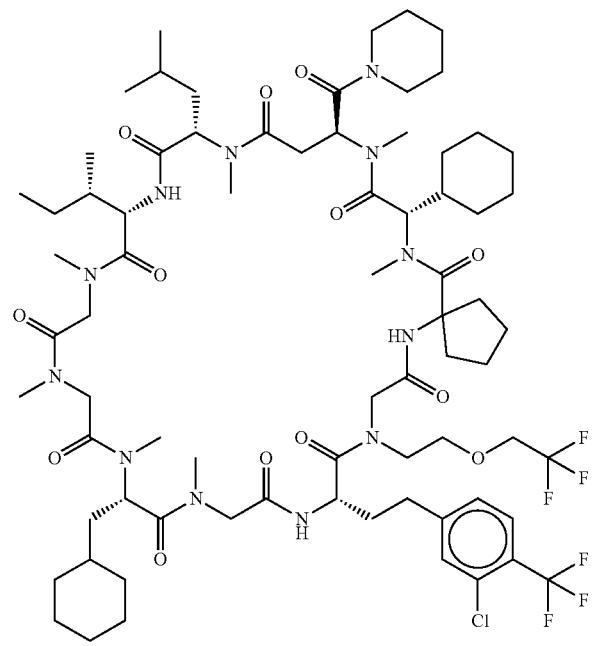 |
| 2025 | 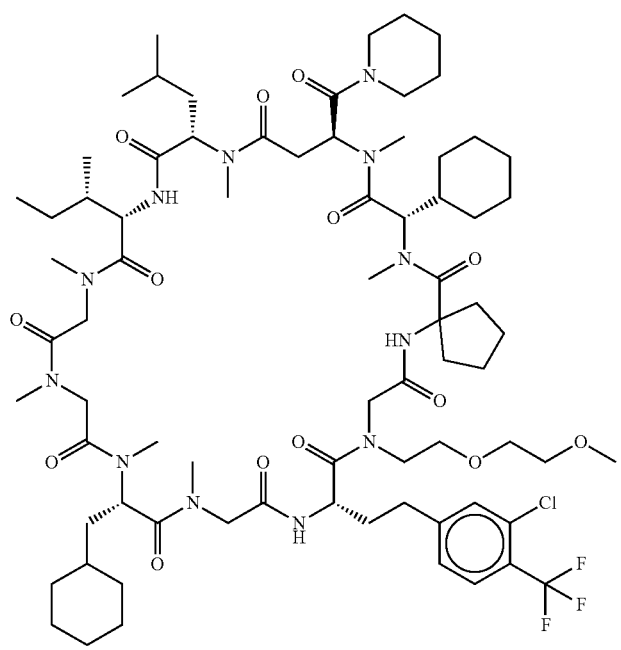 |

TABLE 24-continued
| Compound No. | Structural formula |
|---|---|
| 2026 | 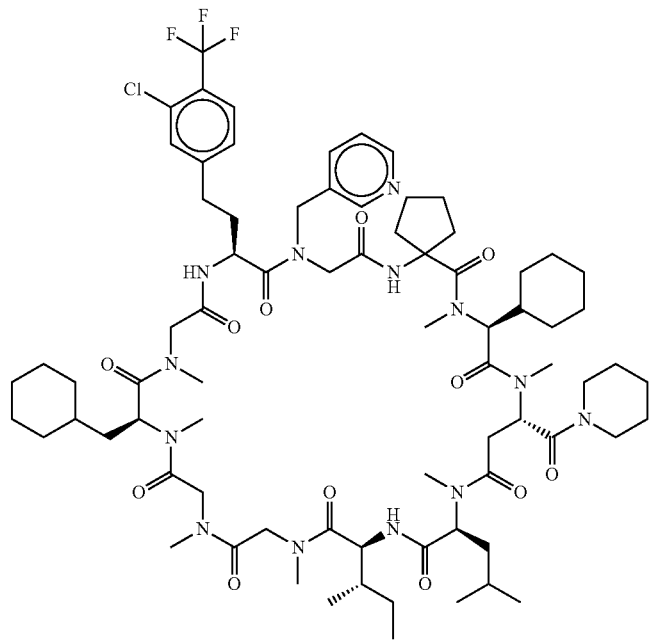 |
| 2027 | 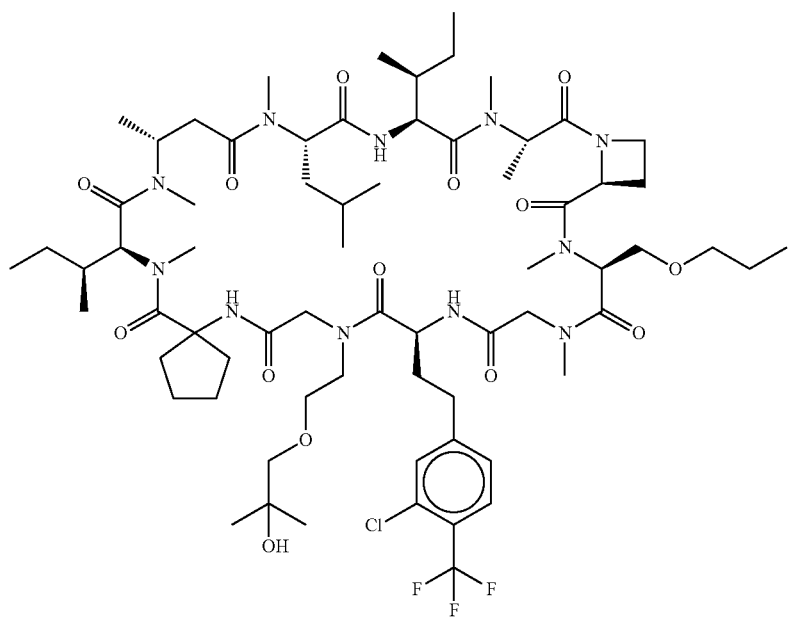 |

| Compound No. | Structural formula |
|---|---|
| 2028 | 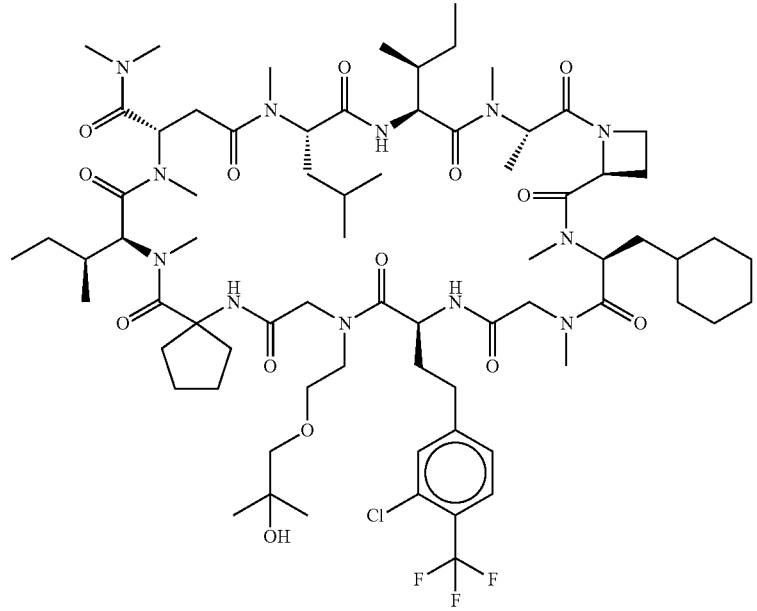 |
| 2029 | 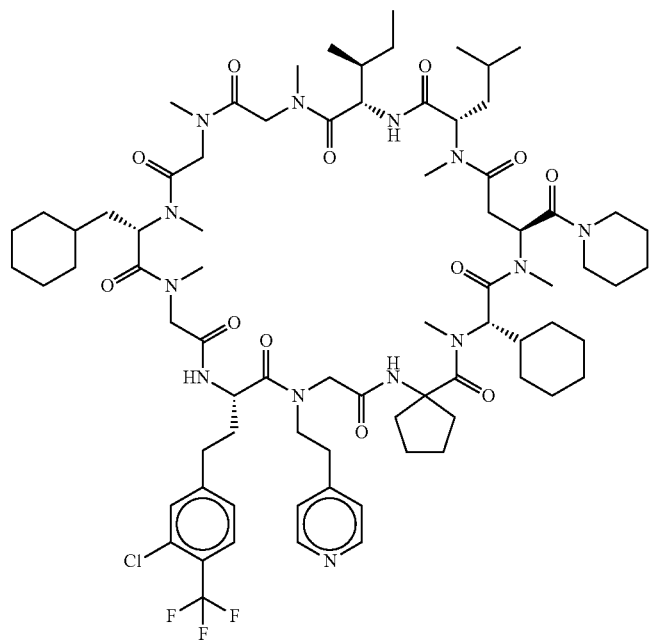 |

TABLE 24-continued
| Compound No. | Structural formula |
|---|---|
| 2030 | 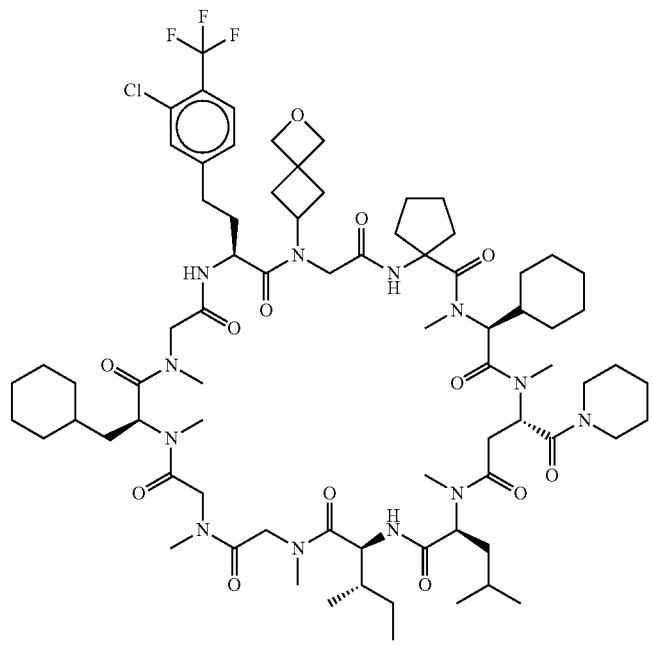 |
| 2031 | 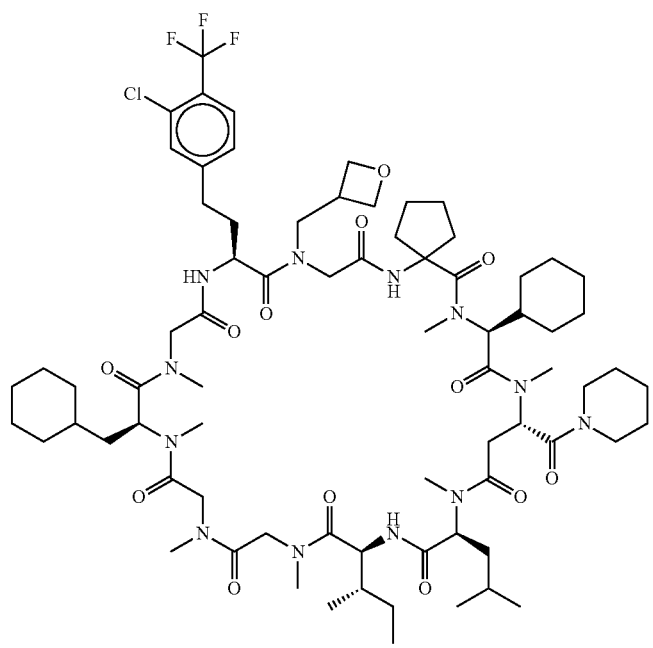 |

TABLE 24-continued
| Compound No. | Structural formula |
|---|---|
| 2032 | 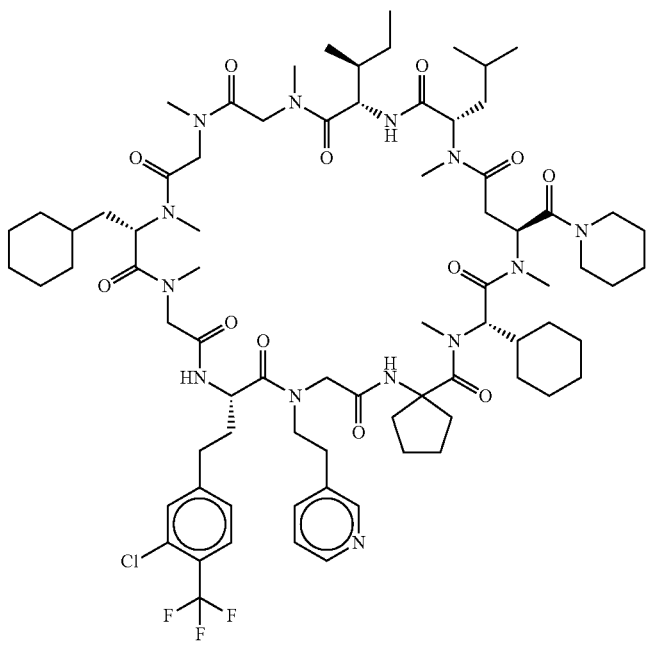 |
| 2033 | 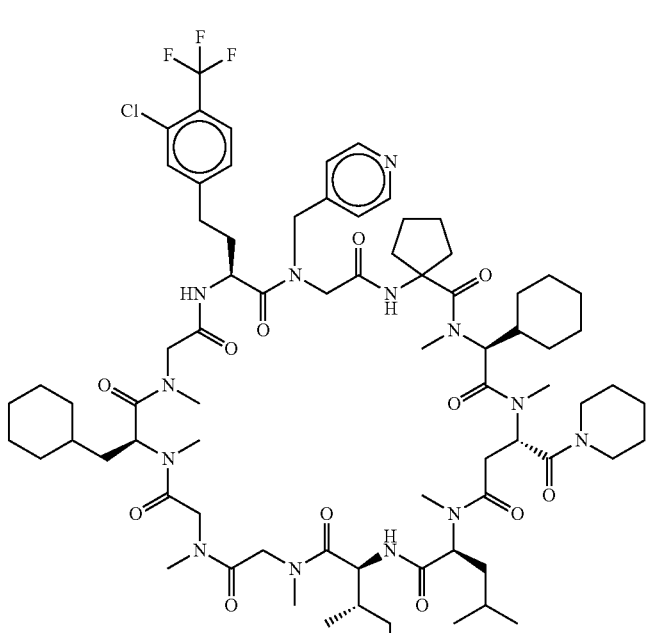 |

TABLE 24-continued
| Compound No. | Structural formula |
|---|---|
| 2034 | 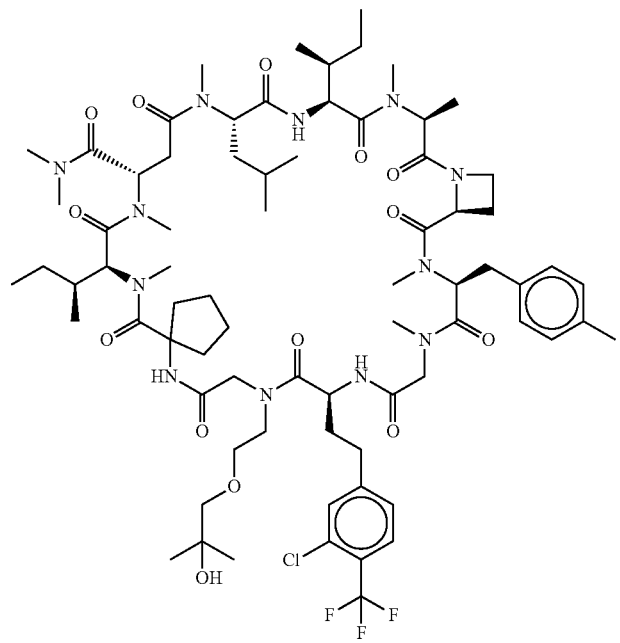 |
| 2035 | 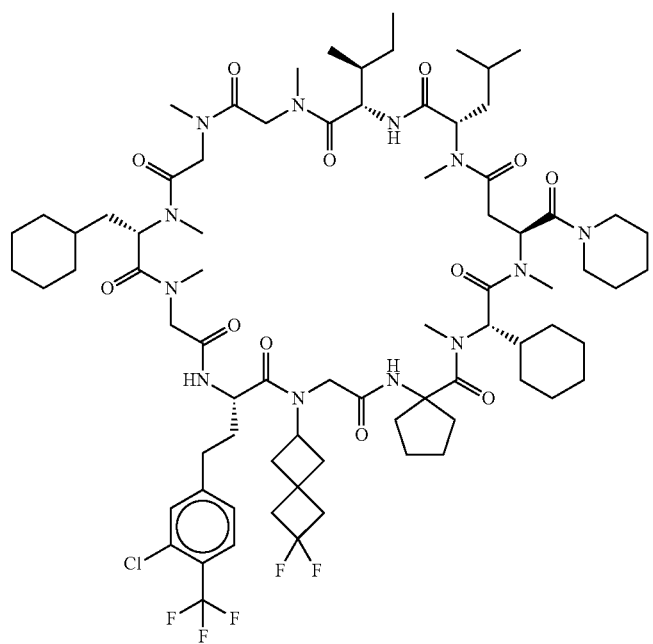 |

TABLE 24-continued
| Compound No. | Structural formula |
|---|---|
| 2036 | 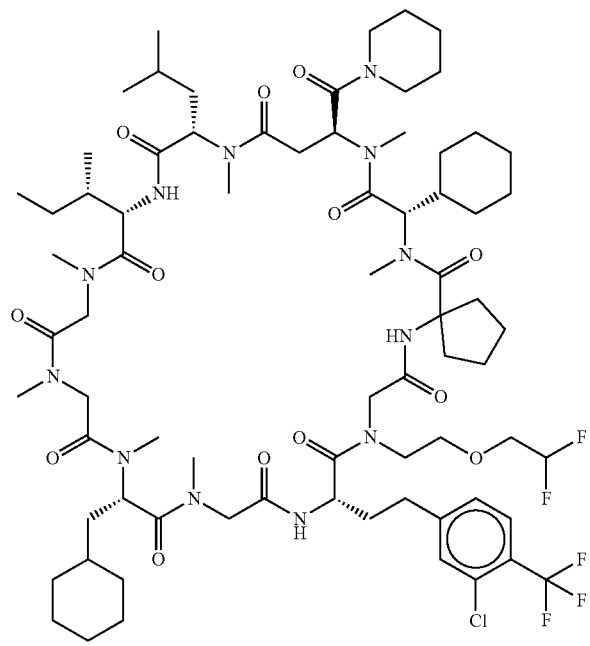 |
| 2037 | 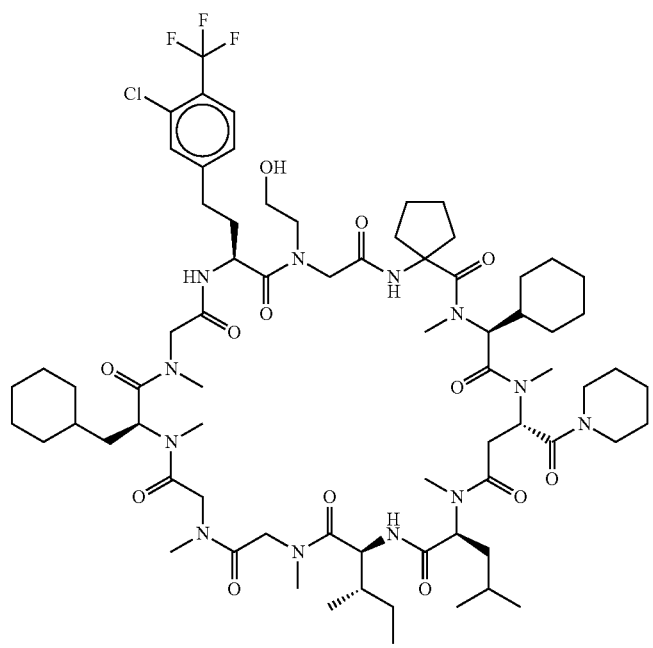 |

TABLE 24-continued
| Compound No. | Structural formula |
|---|---|
| 2038 | 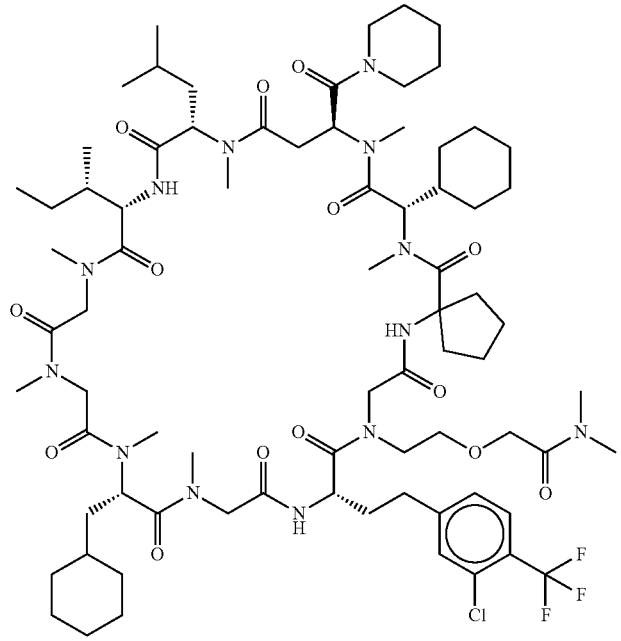 |
| 2039 | 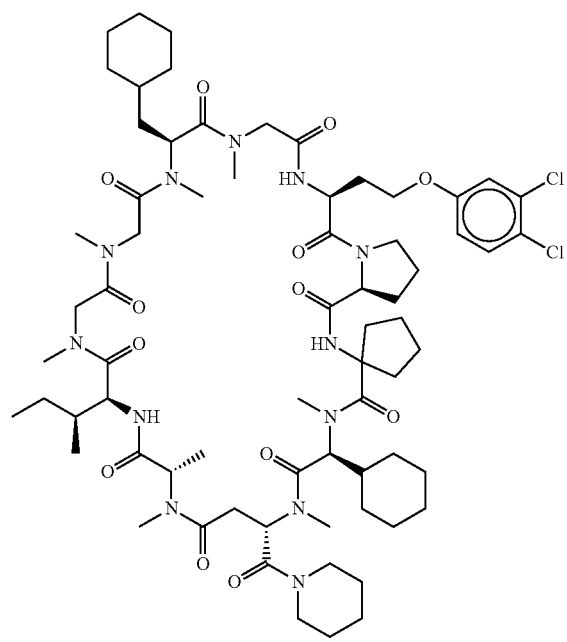 |

TABLE 24-continued
| Compound No. | Structural formula |
|---|---|
| 2040 | 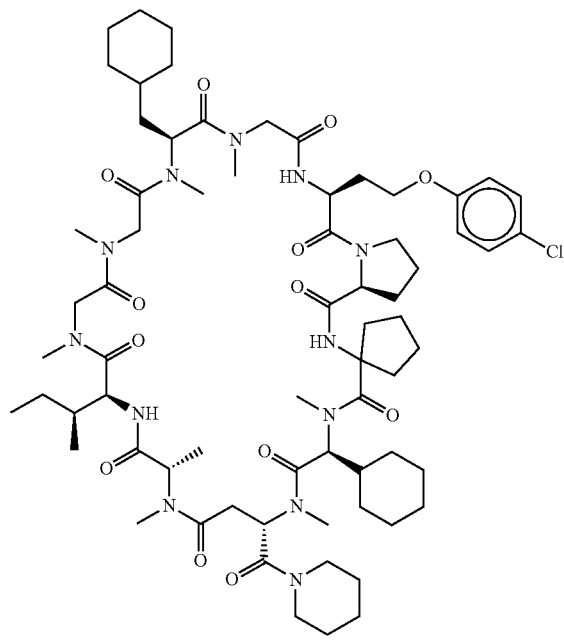 |
| 2041 | 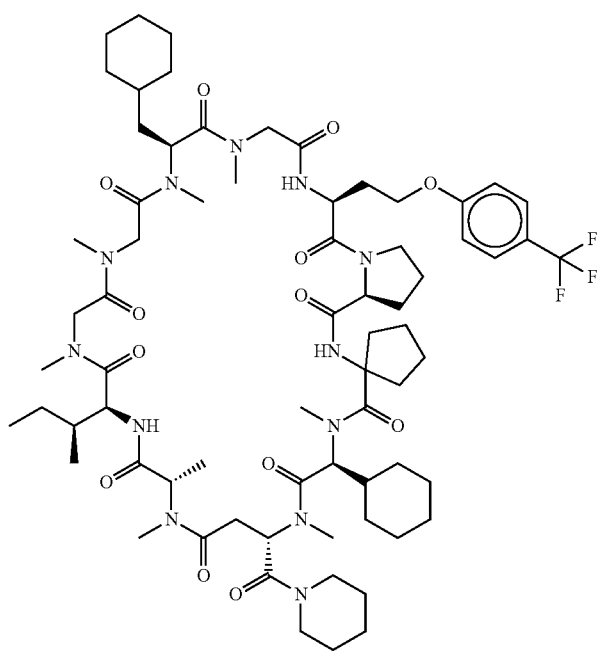 |

TABLE 24-continued
| Compound No. | Structural formula |
|---|---|
| 2042 | 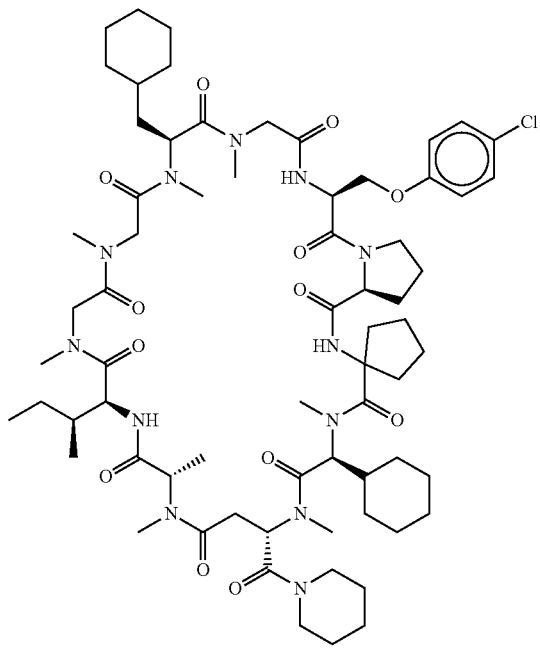 |
| 2043 | 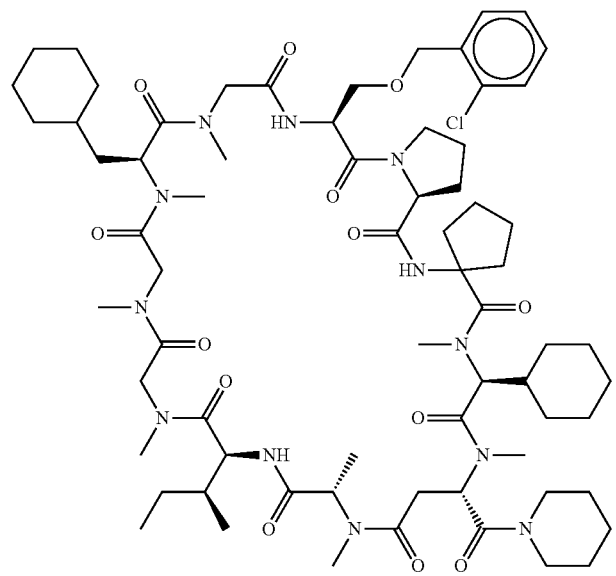 |

TABLE 24-continued
| Compound No. | Structural formula |
|---|---|
| 2044 | 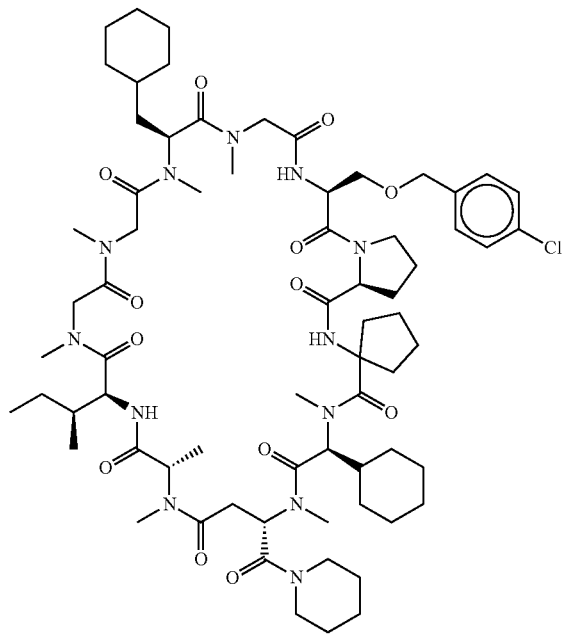 |
| 2045 | 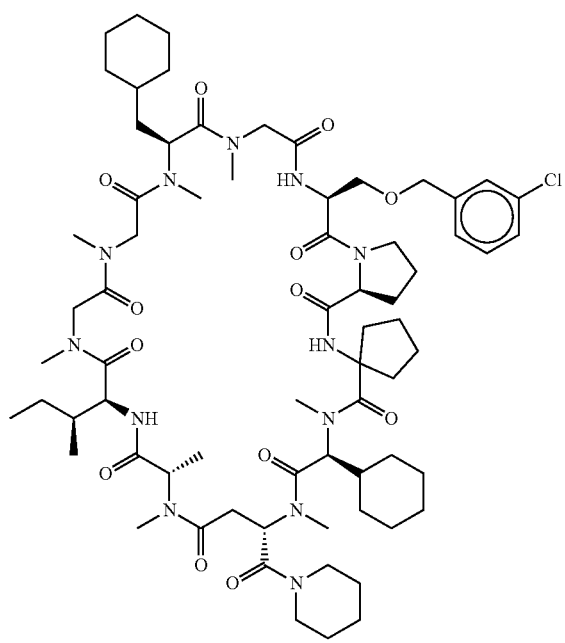 |

TABLE 24-continued
| Compound No. | Structural formula |
|---|---|
| 2046 | 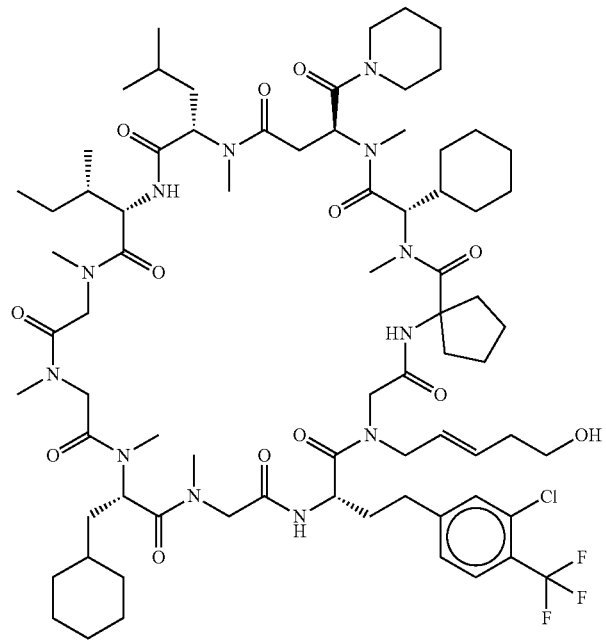 |
| 2047 | 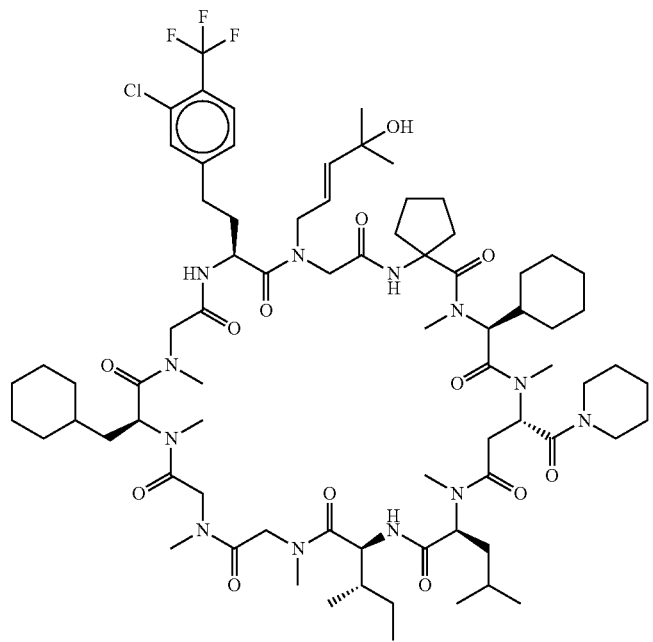 |

TABLE 24-continued
| Compound No. | Structural formula |
|---|---|
| 2048 | 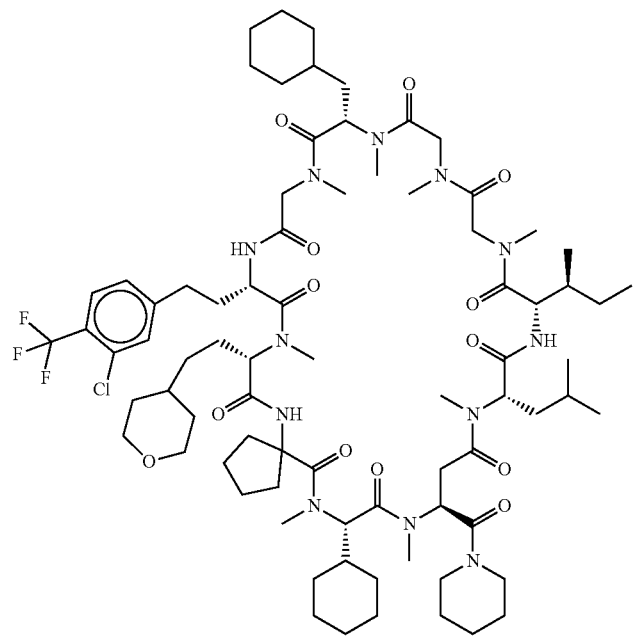 |
| 2049 | 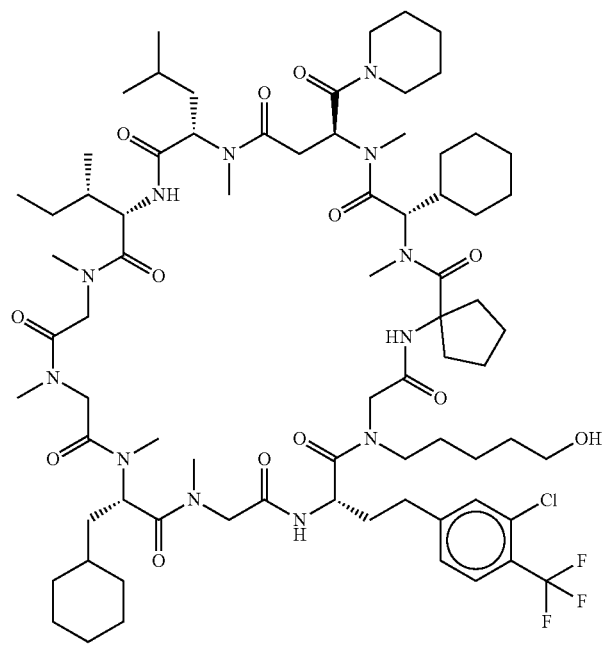 |

TABLE 24-continued
| Compound No. | Structural formula |
|---|---|
| 2050 | 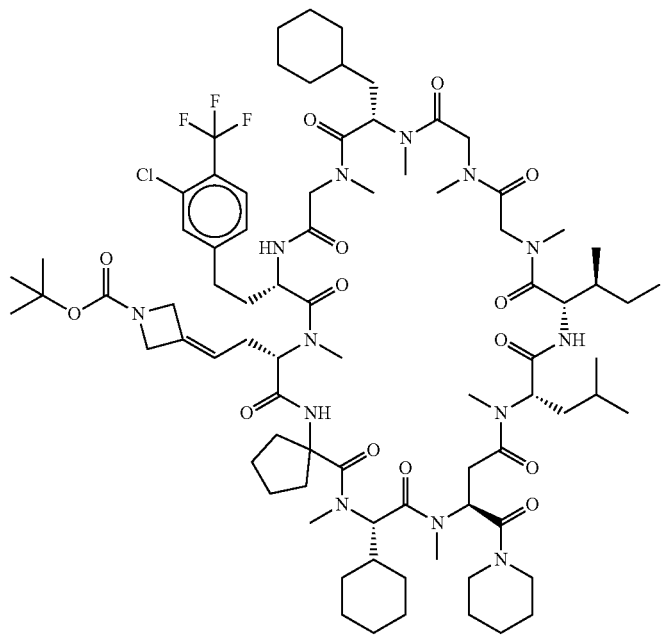 |
| 2051 | 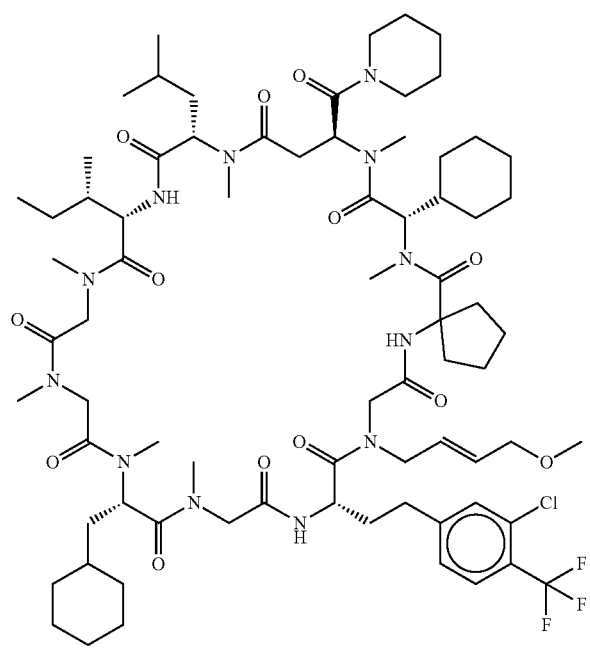 |

TABLE 24-continued
| Compound No. | Structural formula |
|---|---|
| 2052 | 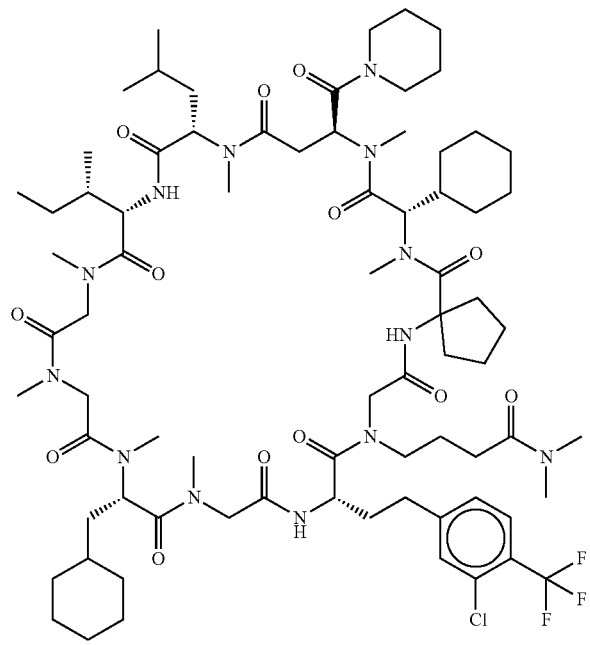 |
| 2053 | 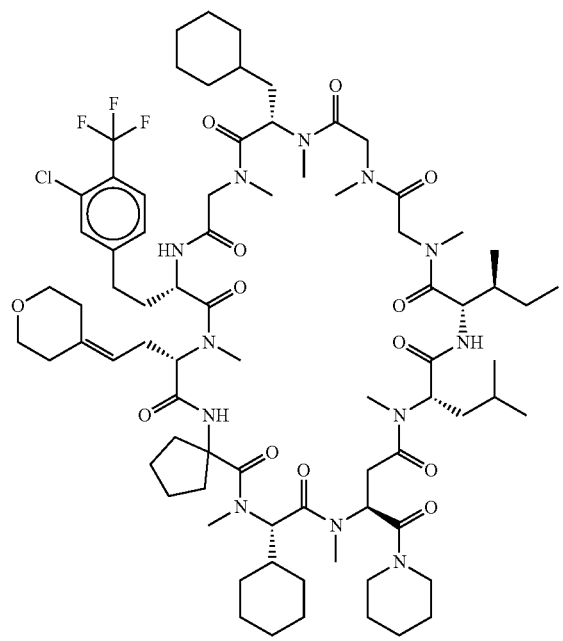 |

TABLE 24-continued
| Compound No. | Structural formula |
|---|---|
| 2054 | 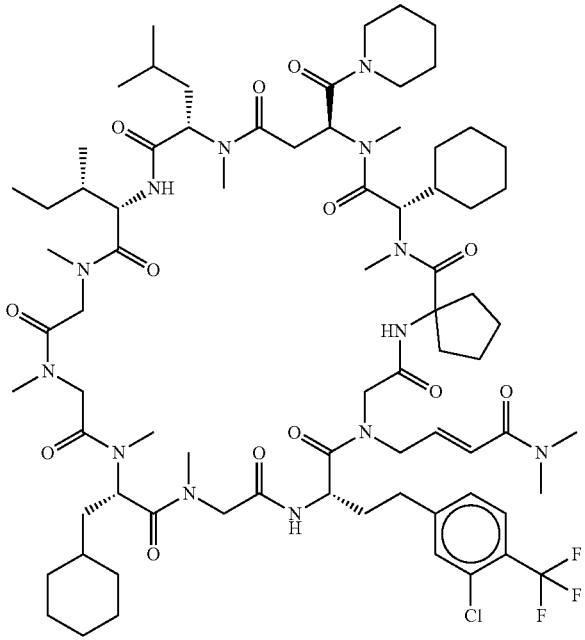 |
| 2055 | 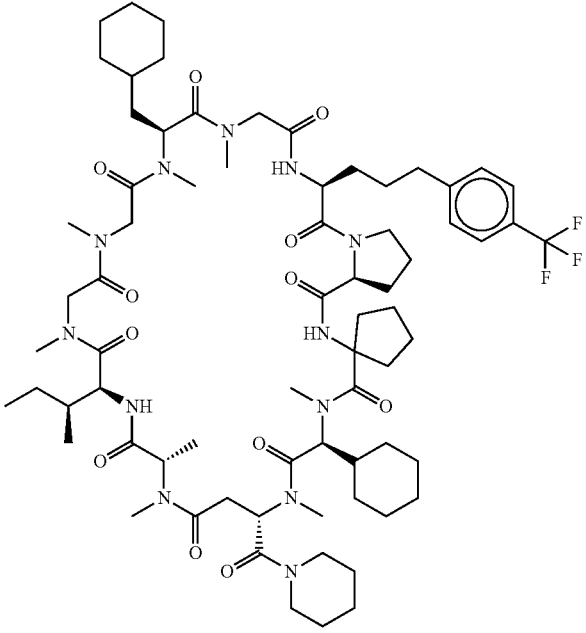 |

TABLE 24-continued
| Compound No. | Structural formula |
|---|---|
| 2056 | 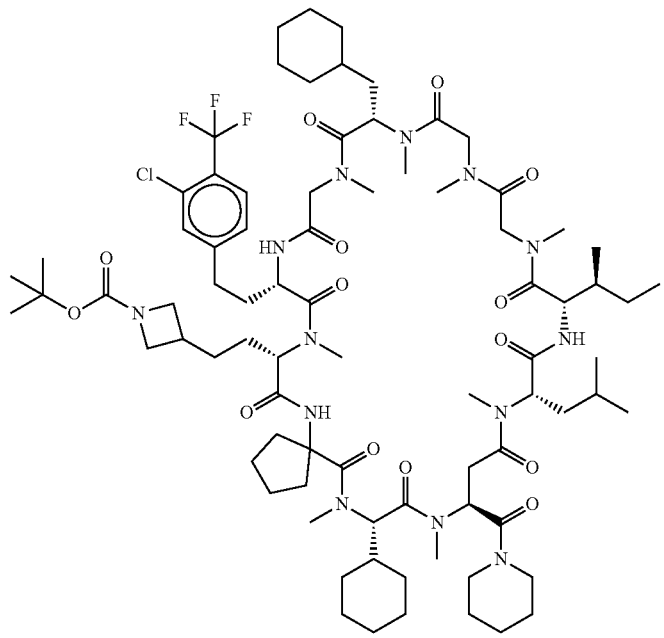 |
| 2057 | 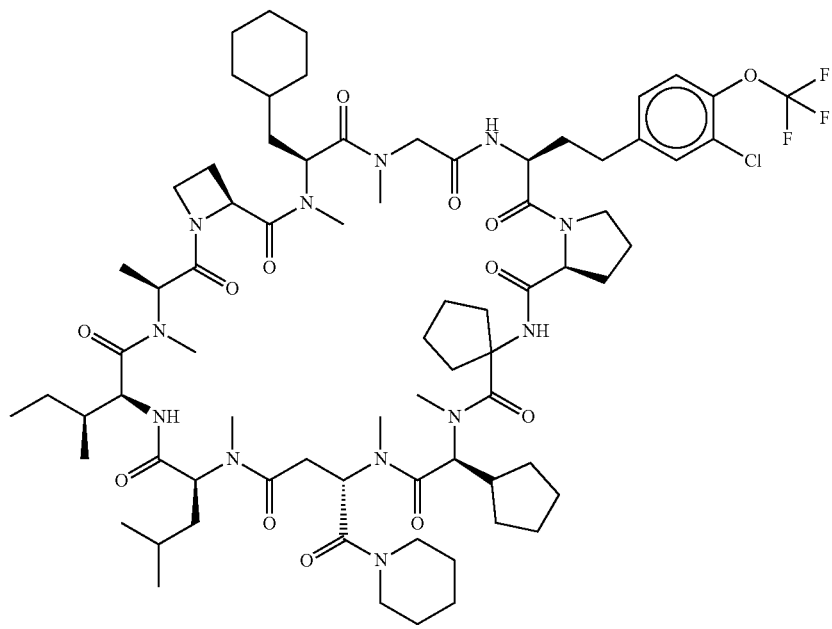 |

TABLE 24-continued
| Compound No. | Structural formula |
|---|---|
| 2058 | 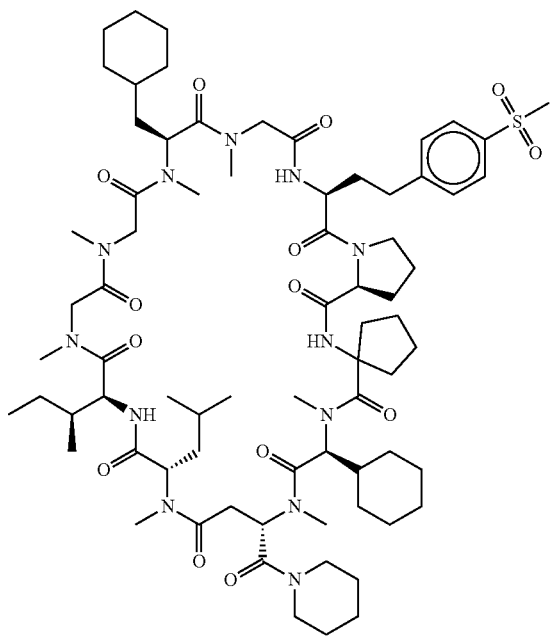 |
| 2059 | 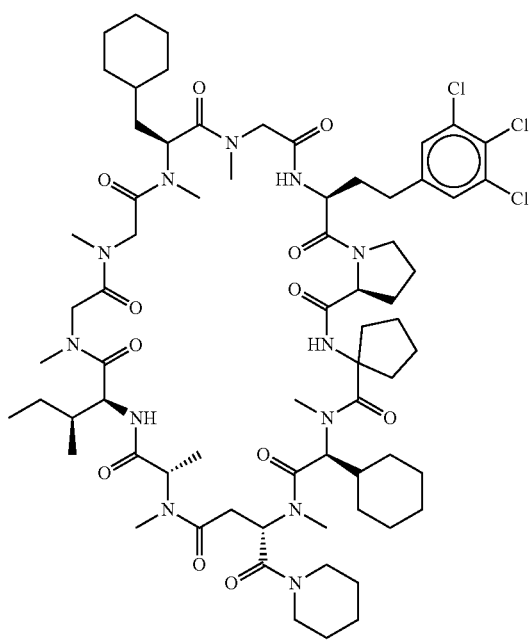 |

TABLE 24-continued
| Compound No. | Structural formula |
|---|---|
| 2060 | 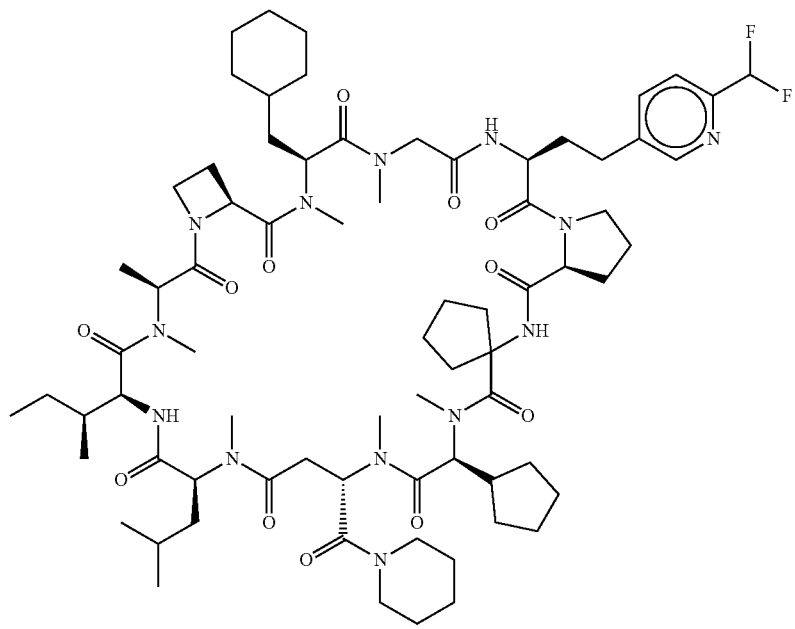 |
| 2061 | 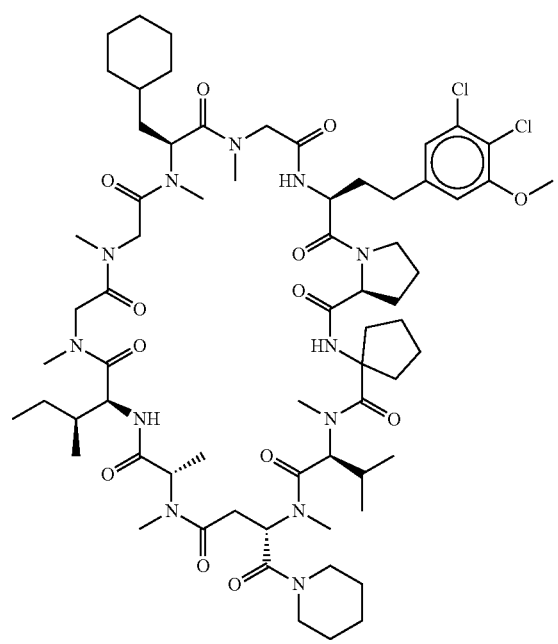 |

TABLE 24-continued
| Compound No. | Structural formula |
|---|---|
| 2062 | 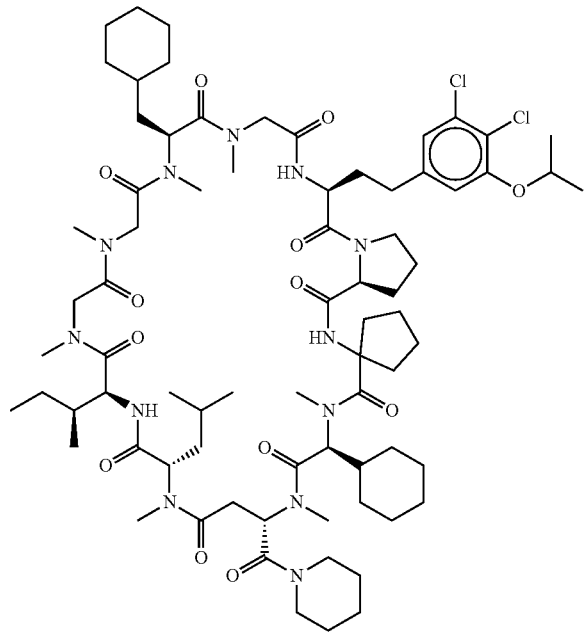 |
| 2063 | 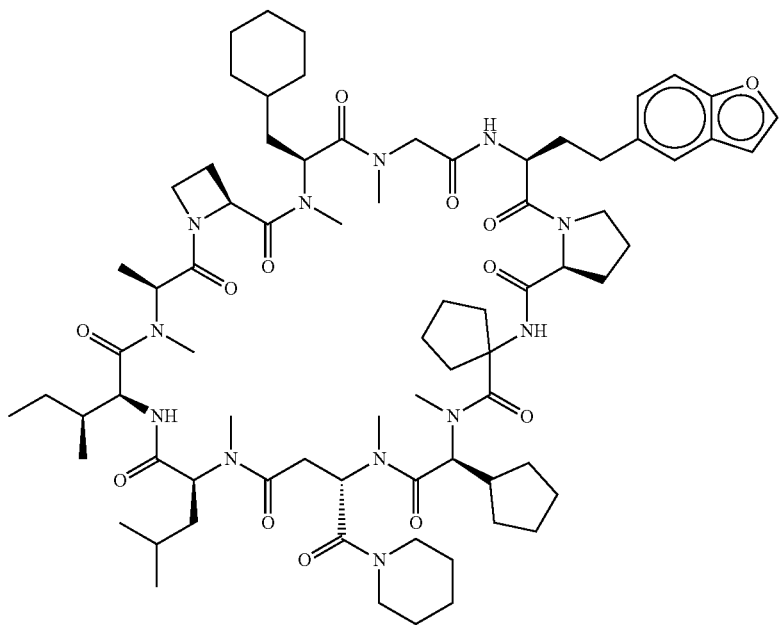 |

TABLE 24-continued
| Compound No. | Structural formula |
|---|---|
| 2064 | 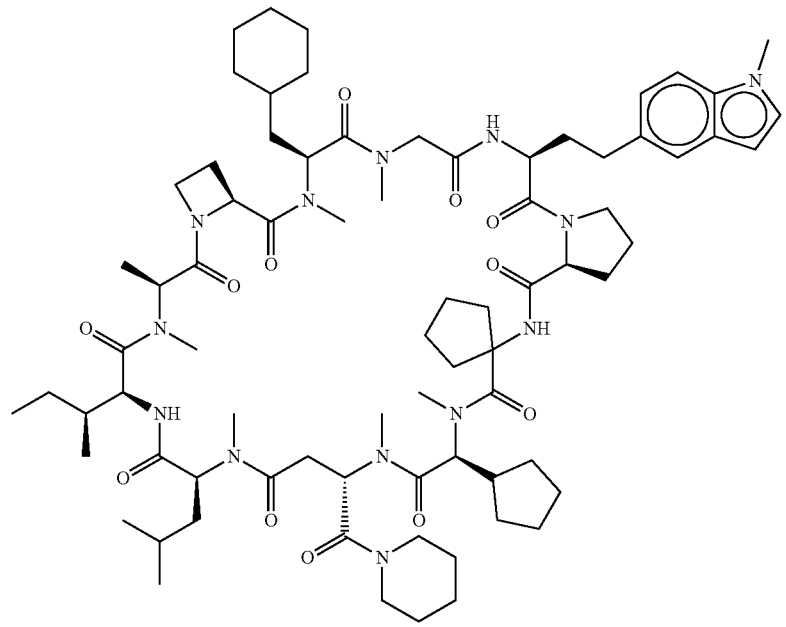 |
| 2065 | 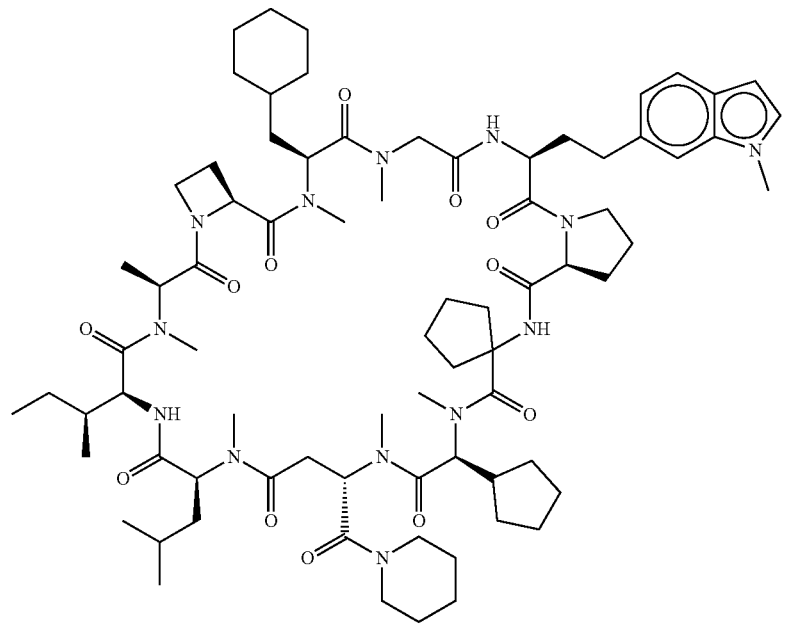 |

TABLE 24-continued
| Compound No. | Structural formula |
|---|---|
| 2066 | 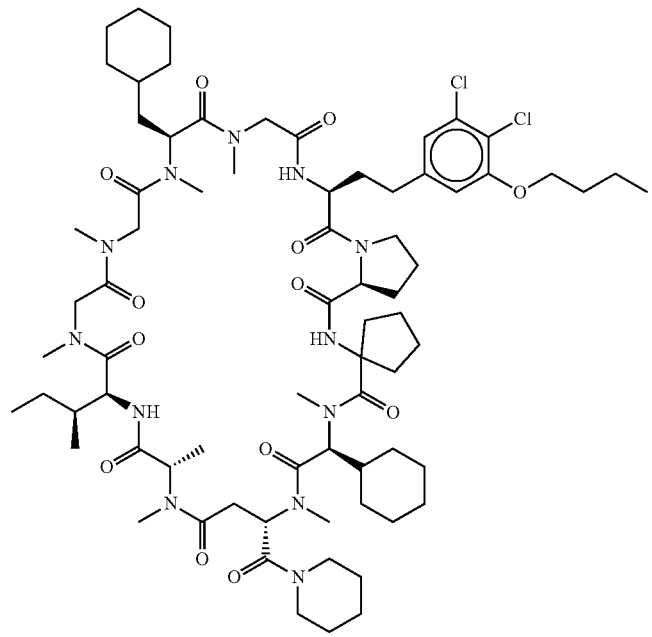 |
| 2067 | 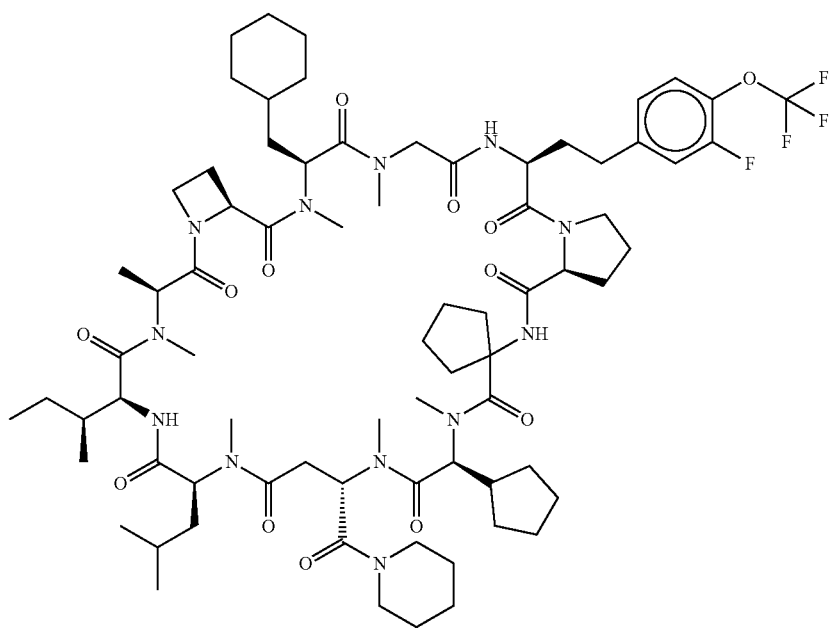 |

TABLE 24-continued
| Compound No. | Structural formula |
|---|---|
| 2068 | 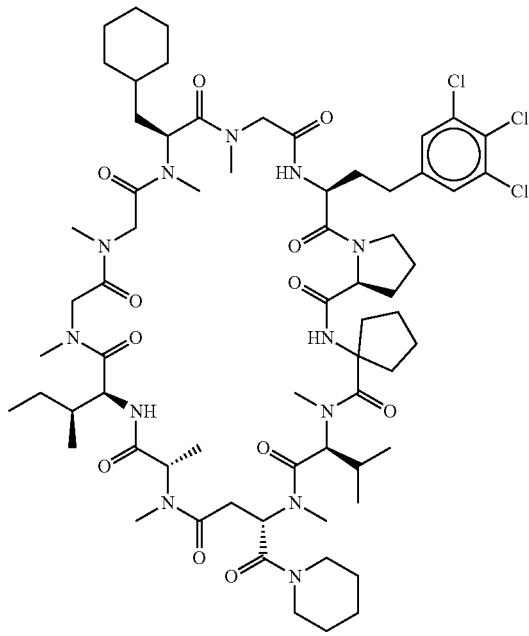 |
| 2069 | 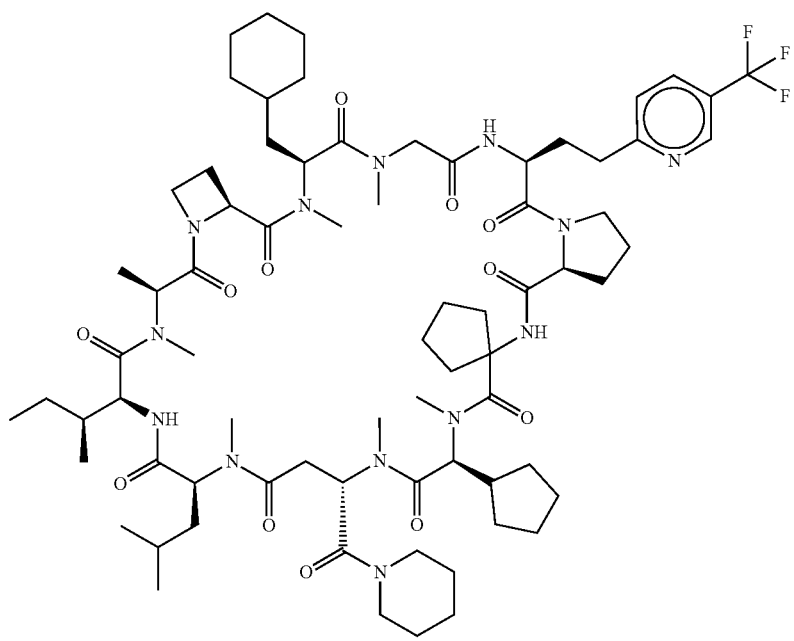 |

TABLE 24-continued
| Compound No. | Structural formula |
|---|---|
| 2070 | 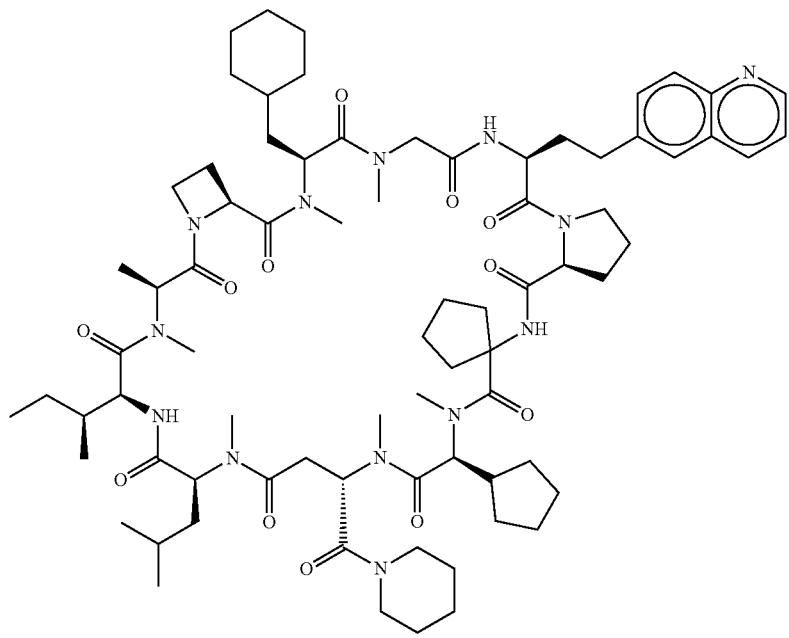 |
| 2071 | 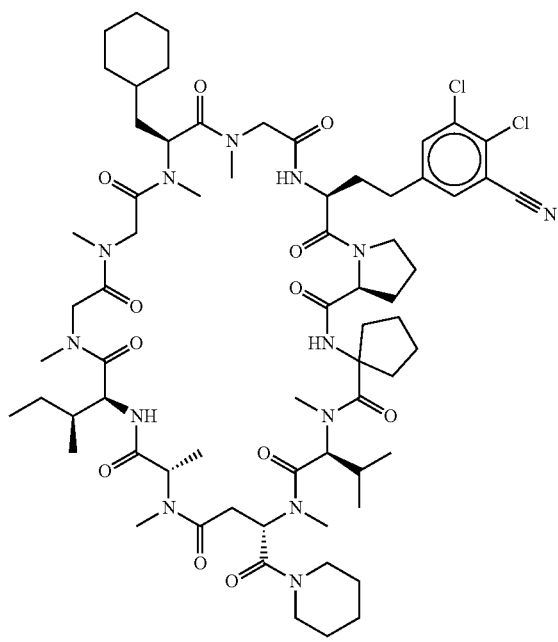 |

TABLE 24-continued
| Compound No. | Structural formula |
| --- | --- |
| 2072 | 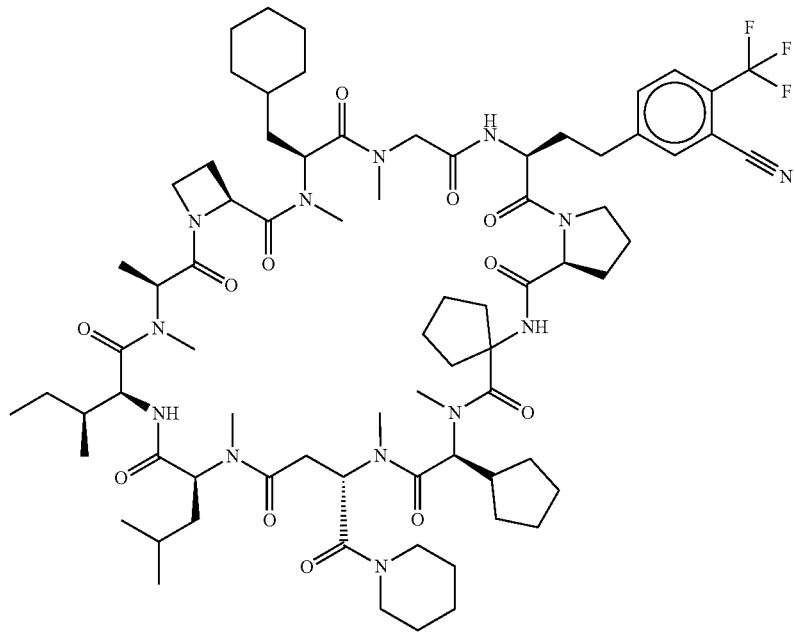 |
| 2073 | 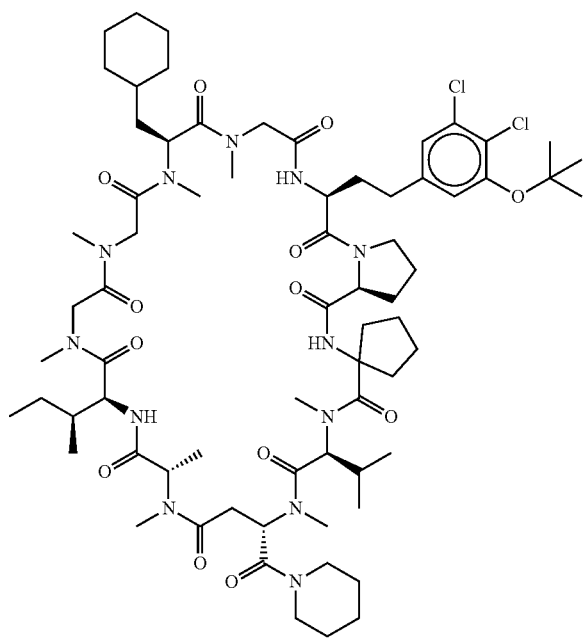 |

TABLE 24-continued
| Compound No. | Structural formula |
|---|---|
| 2074 | 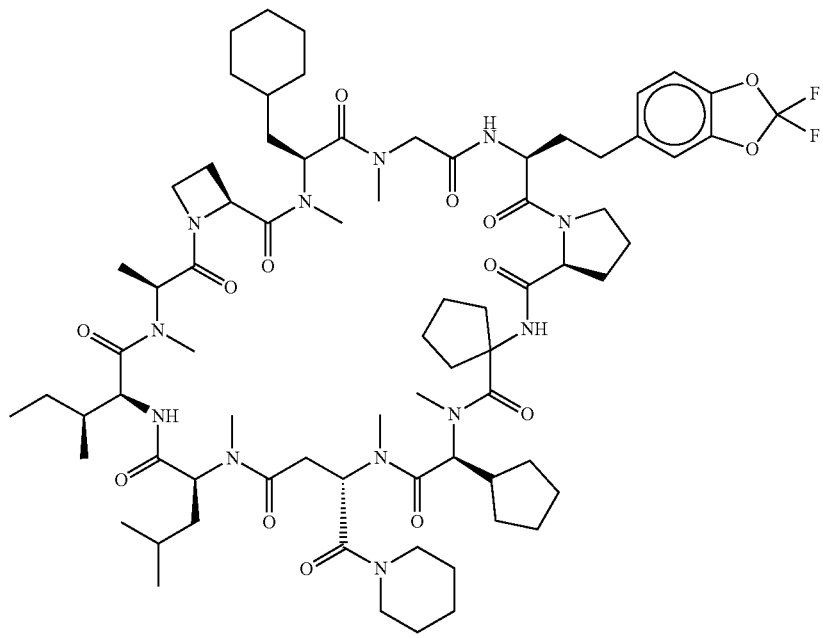 |
| 2075 | 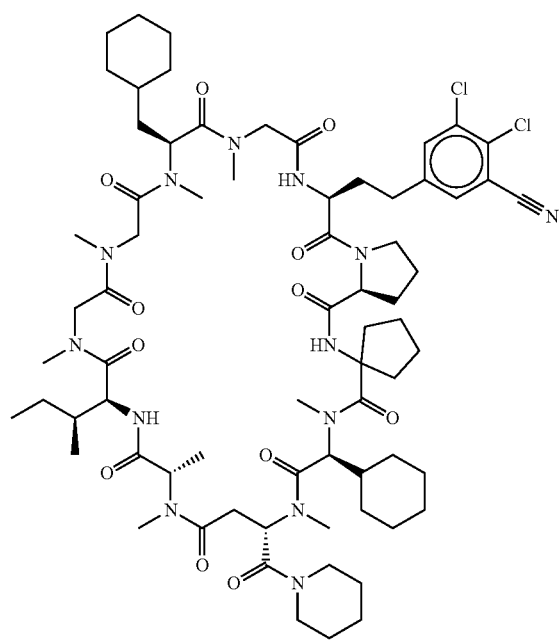 |

TABLE 24-continued
| Compound No. | Structural formula |
|---|---|
| 2076 | 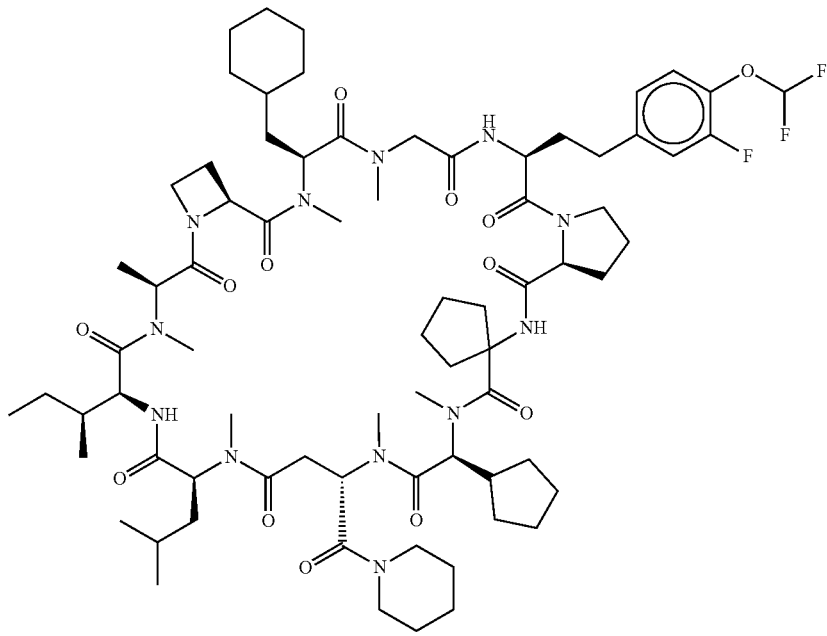 |
| 2077 | 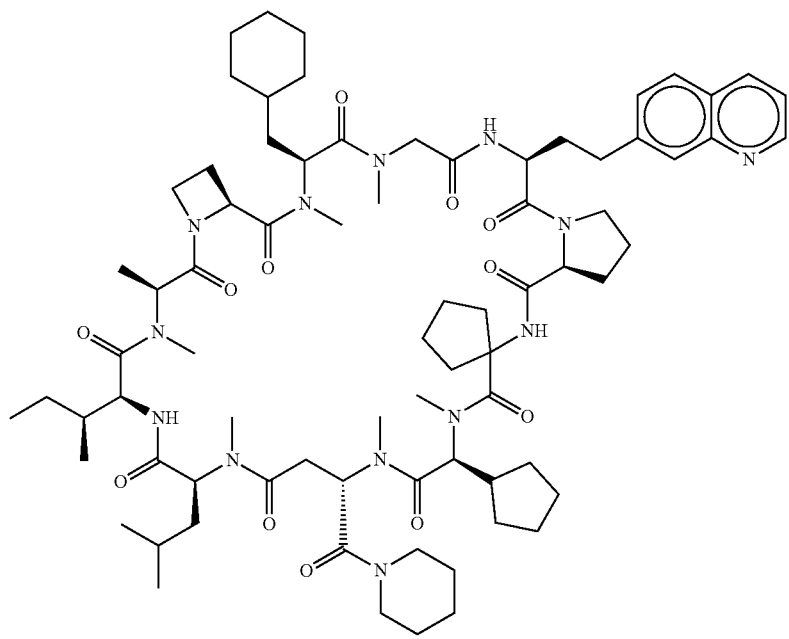 |

TABLE 24-continued
| Compound No. | Structural formula |
| --- | --- |
| 2078 | 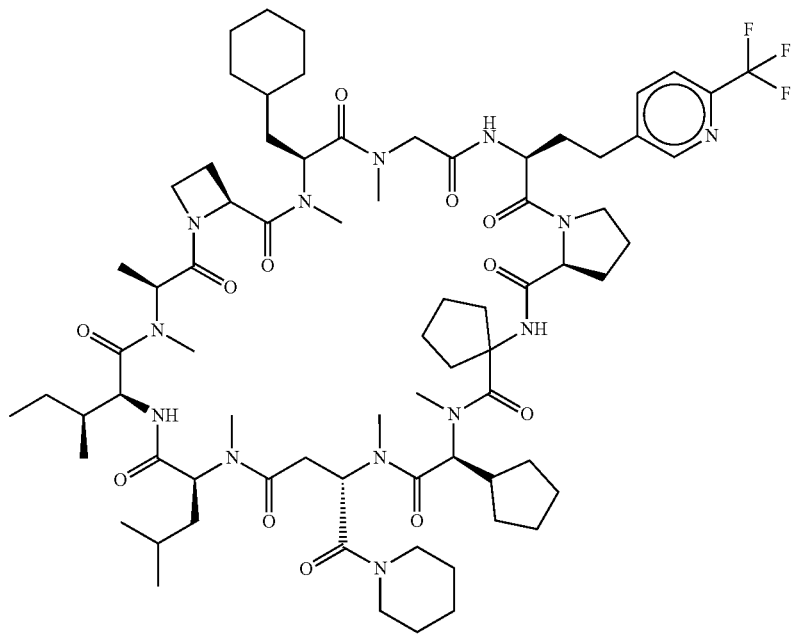 |
| 2079 | 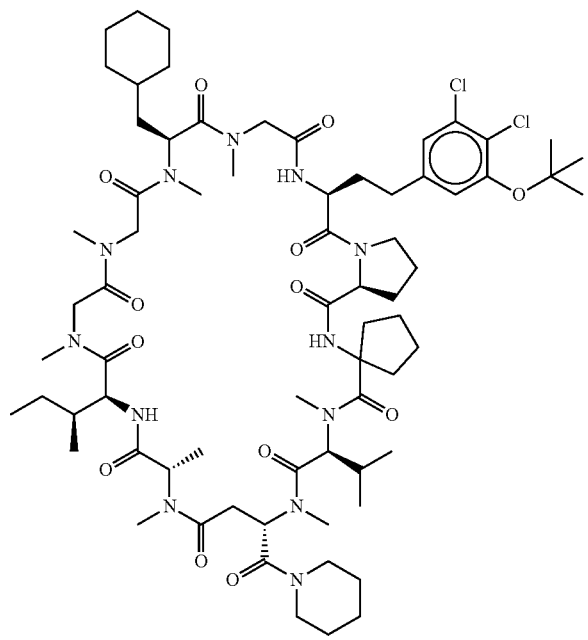 |

TABLE 24-continued
| Compound No. | Structural formula |
|---|---|
| 2080 | 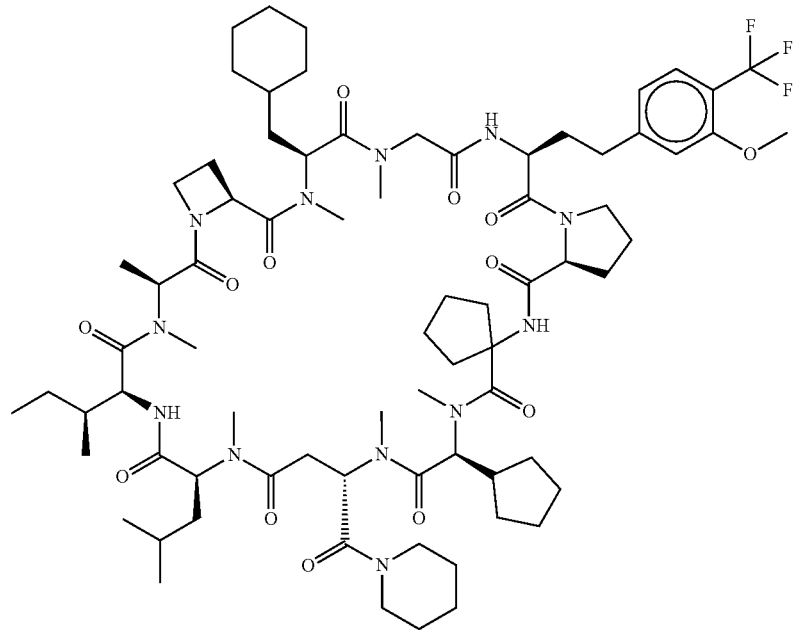 |
| 2081 | 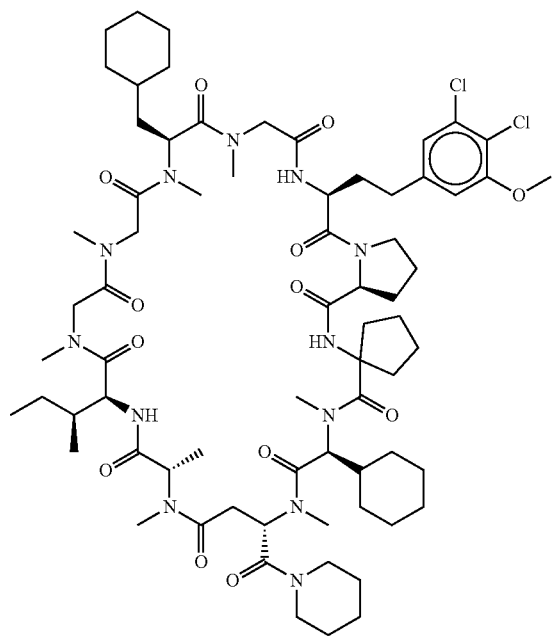 |

TABLE 24-continued
| Compound No. | Structural formula |
|---|---|
| 2082 | 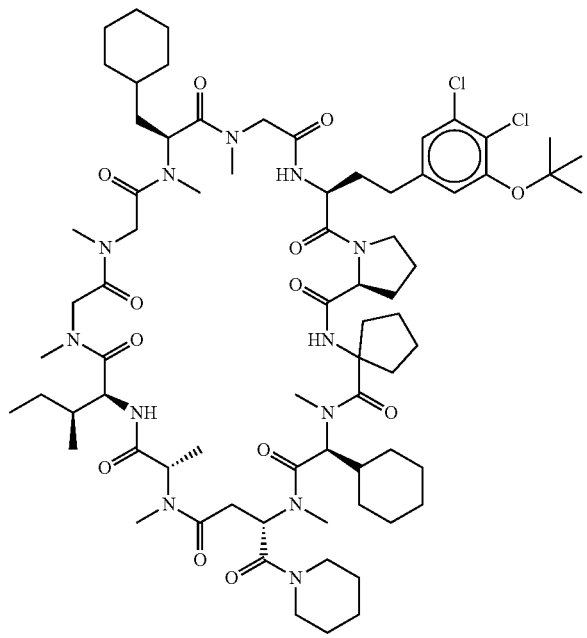 |
| 2083 | 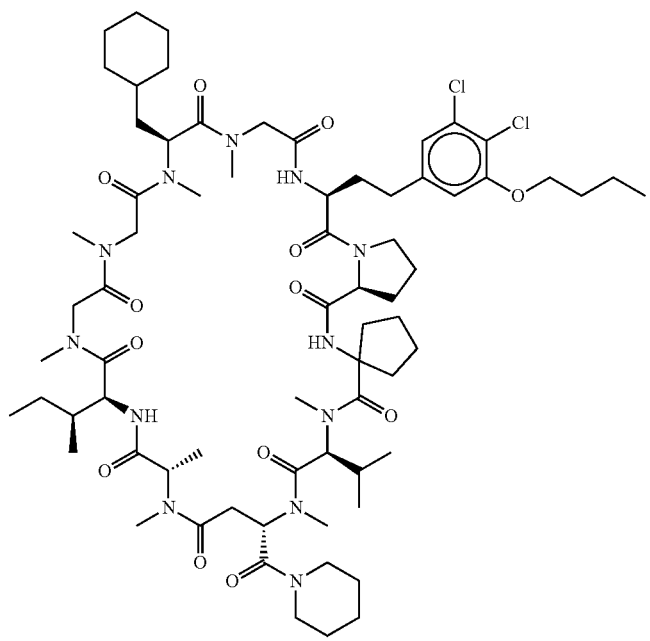 |

TABLE 24-continued
| Compound No. | Structural formula |
| --- | --- |
| 2084 | 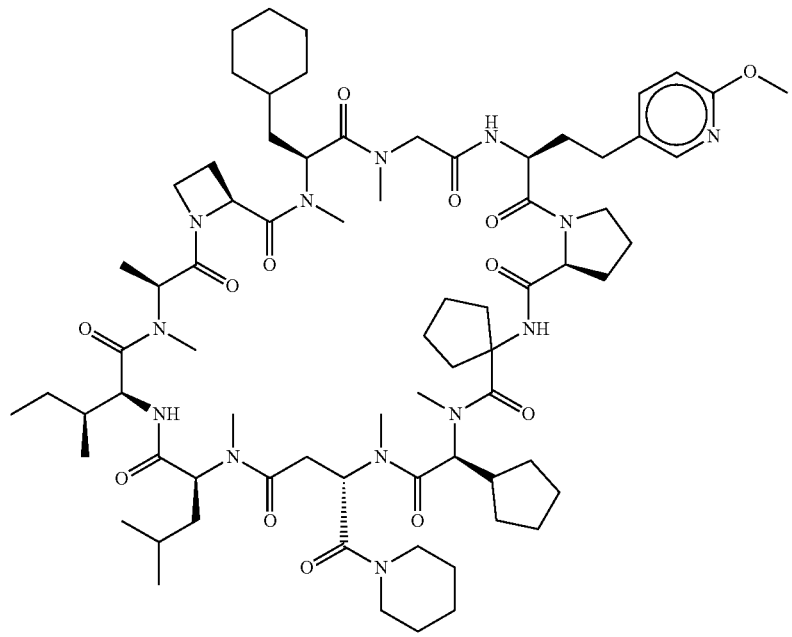 |
| 2085 | 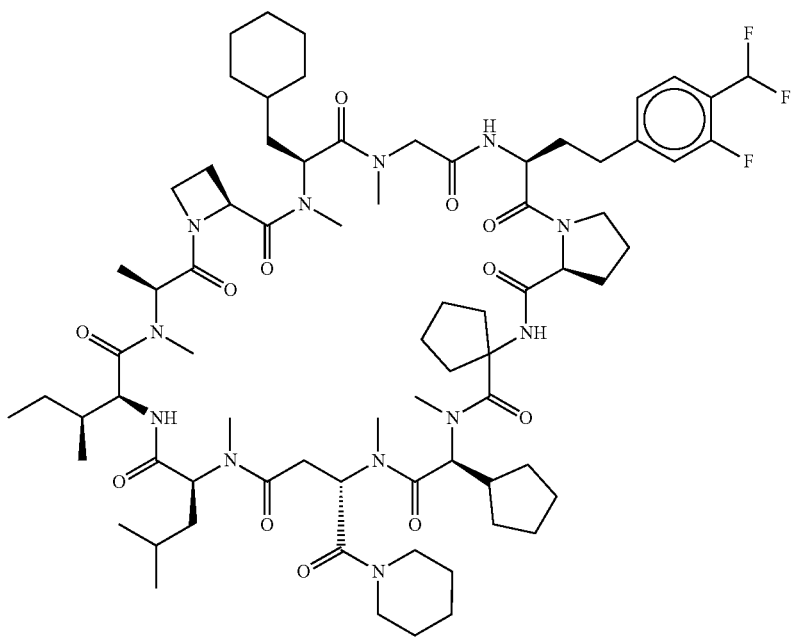 |

TABLE 24-continued
| Compound No. | Structural formula |
|---|---|
| 2086 | 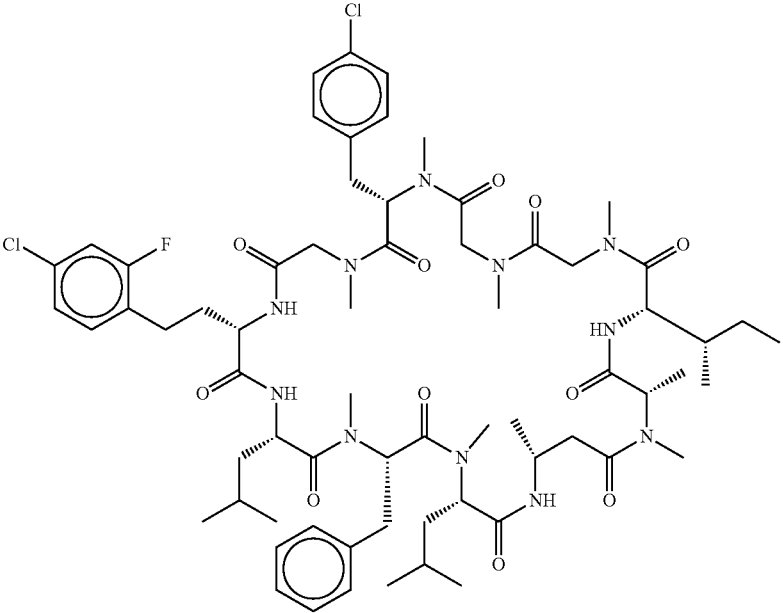 |
| 2087 | 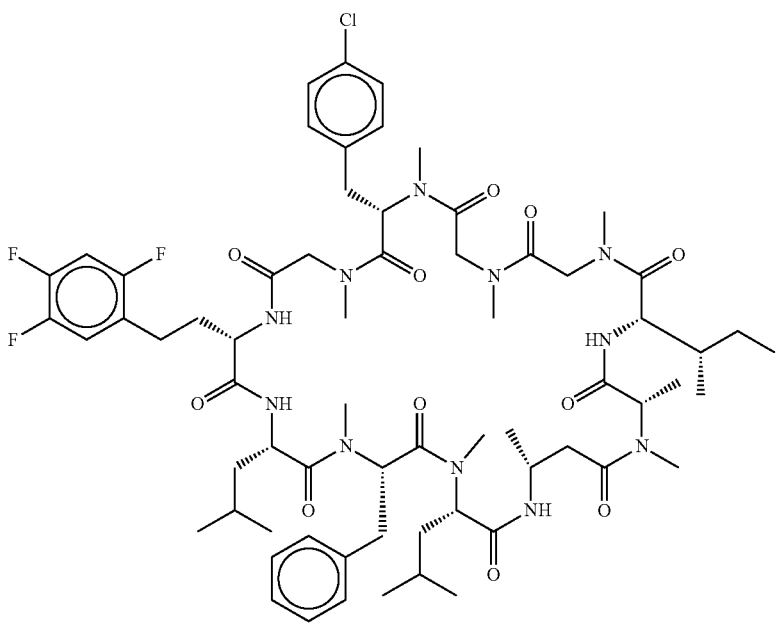 |

TABLE 24-continued
| Compound No. | Structural formula |
|---|---|
| 2088 | 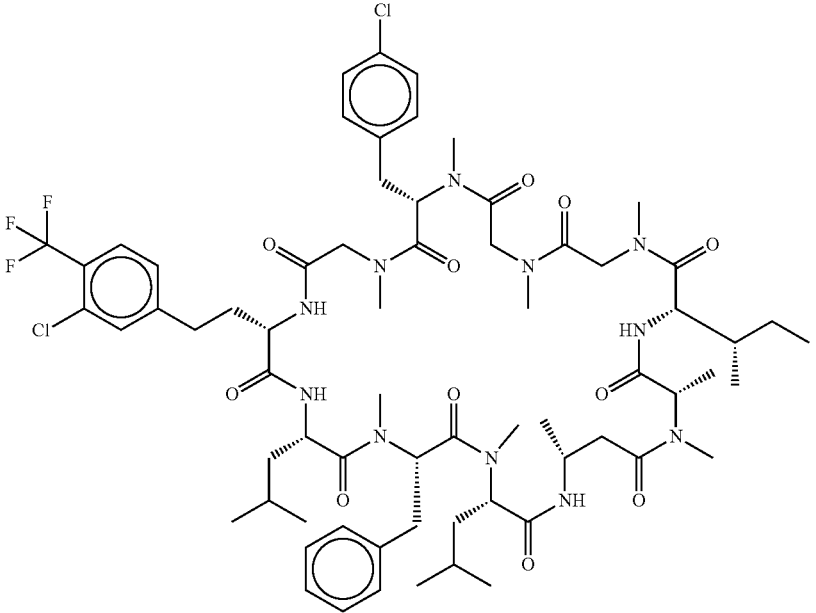 |
| 2089 | 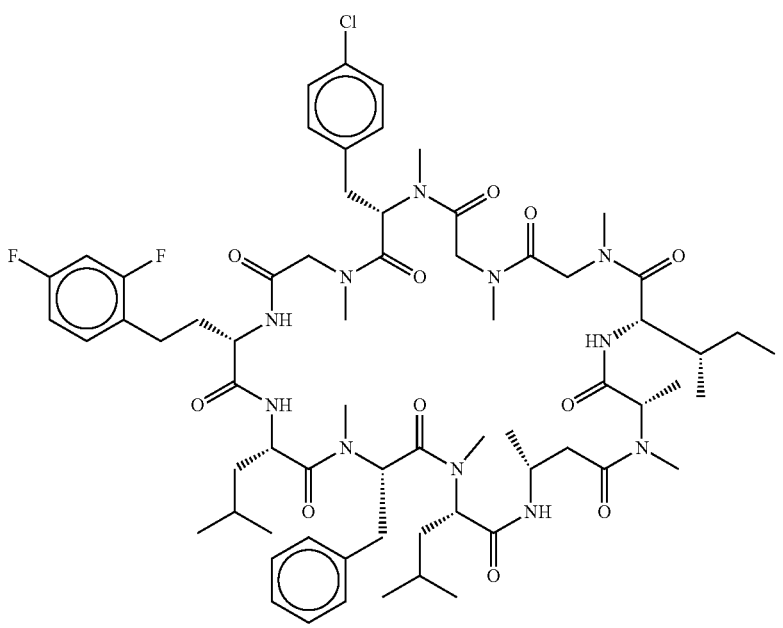 |

TABLE 24-continued
| Compound No. | Structural formula |
|---|---|
| 2090 | 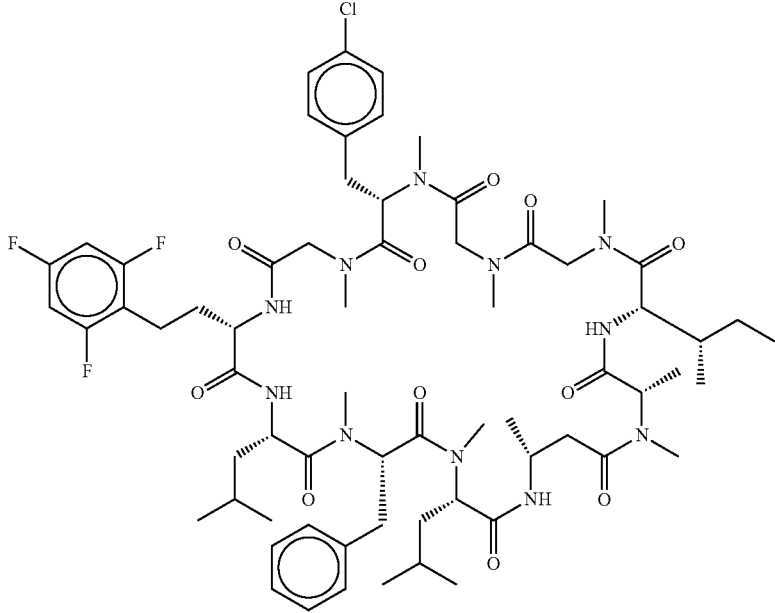 |
| 2091 | 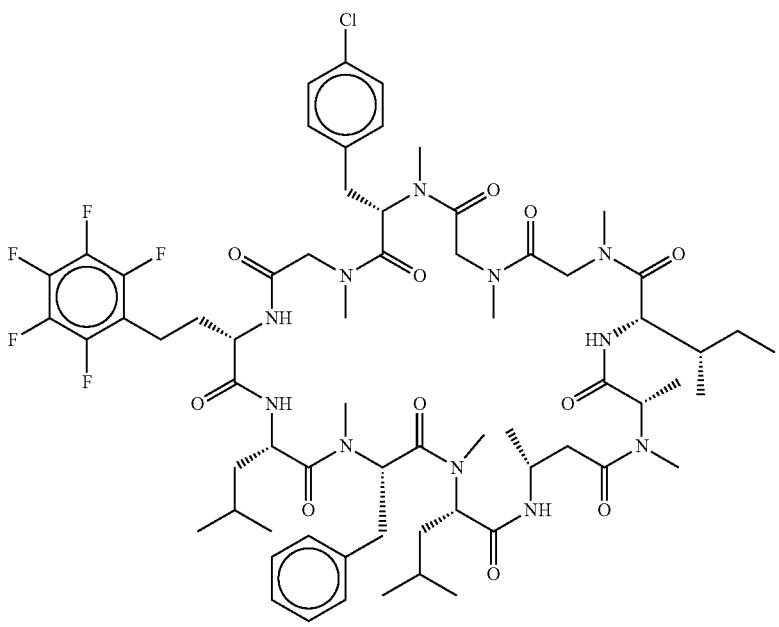 |

TABLE 24-continued
| Compound No. | Structural formula |
|---|---|
| 2092 | 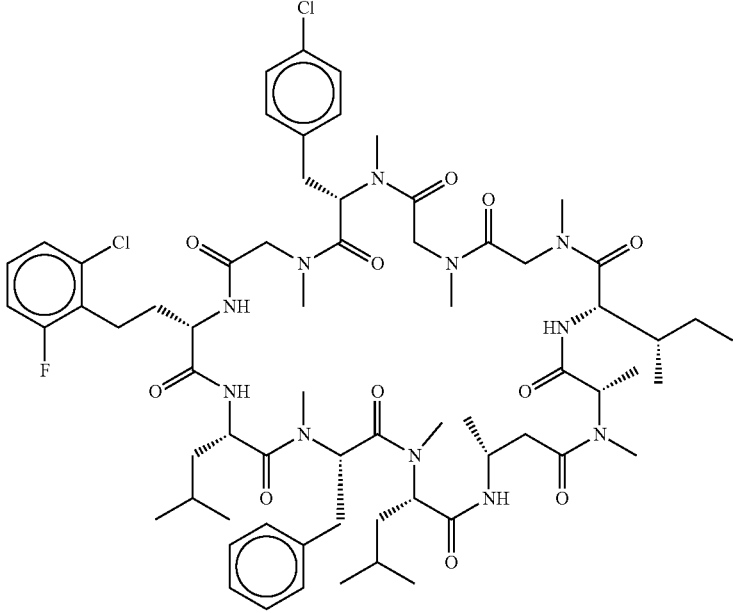 |
| 2093 | 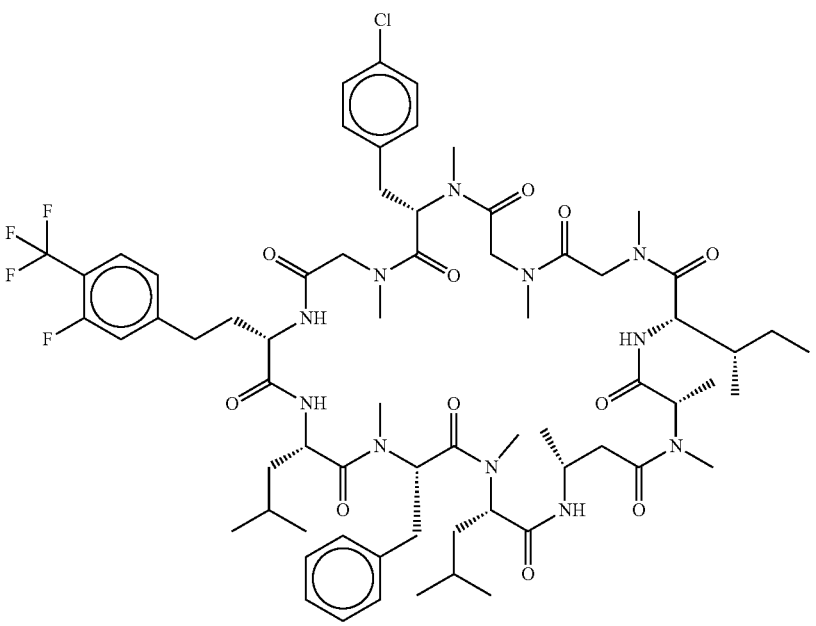 |

| Compound No. | Structural formula |
|---|---|
| 2094 | |
| 2095 | |

TABLE 24-continued
| Compound No. | Structural formula |
|---|---|
| 2096 | 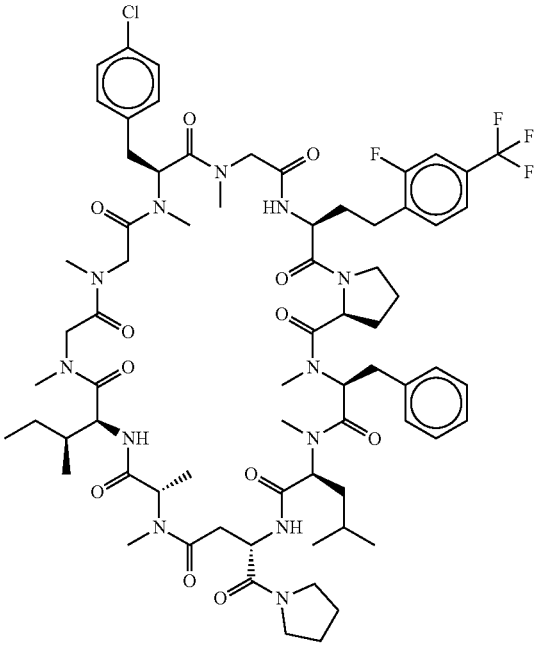 |
| 2097 | 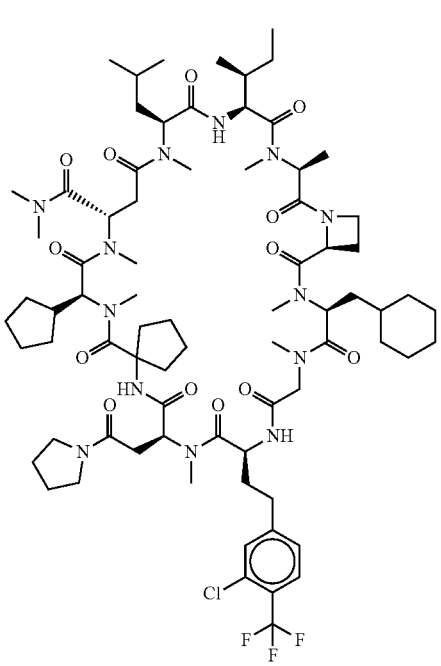 |

TABLE 24-continued
| Compound No. | Structural formula |
|---|---|
| 2098 | 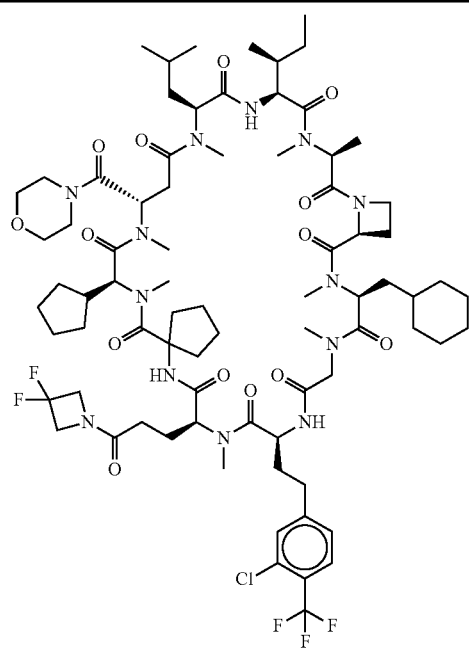 |
| 2099 | 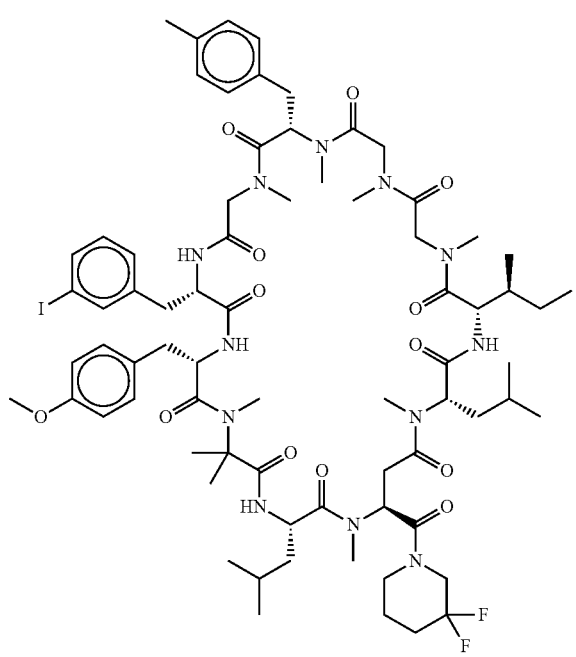 |

TABLE 24-continued
| Compound No. | Structural formula |
|---|---|
| 2100 | 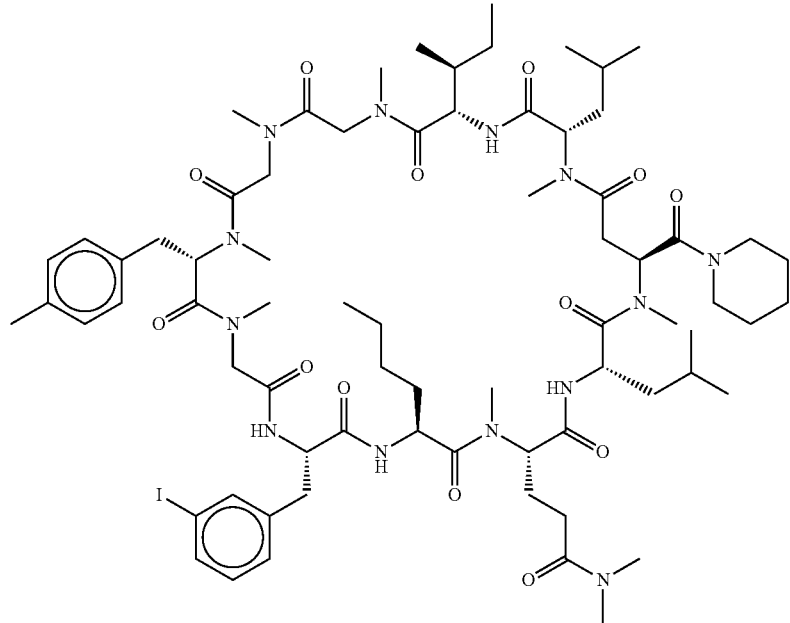 |
| 2101 | 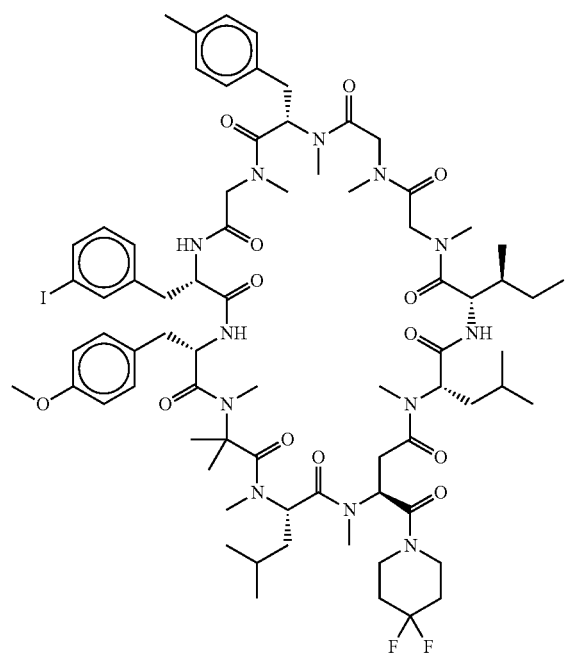 |

TABLE 24-continued
| Compound No. | Structural formula |
|---|---|
| 2102 | 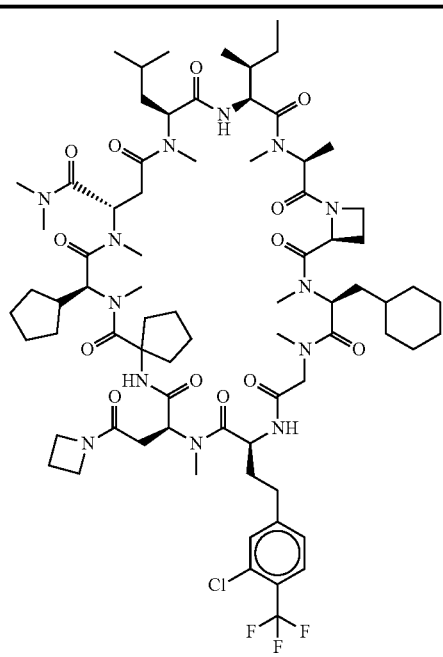 |
| 2103 | 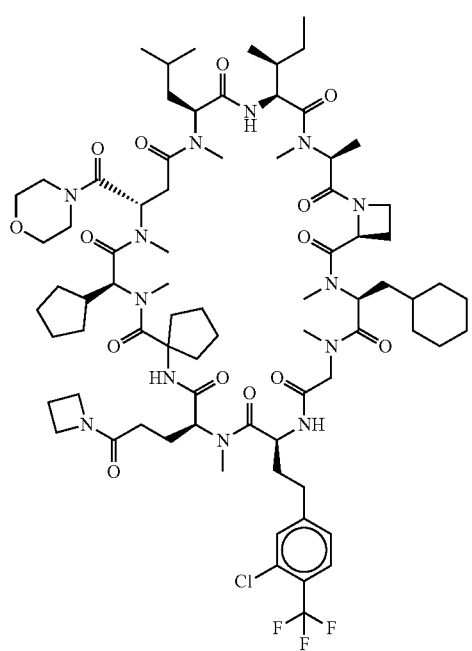 |

TABLE 24-continued
| Compound No. | Structural formula |
|---|---|
| 2104 | 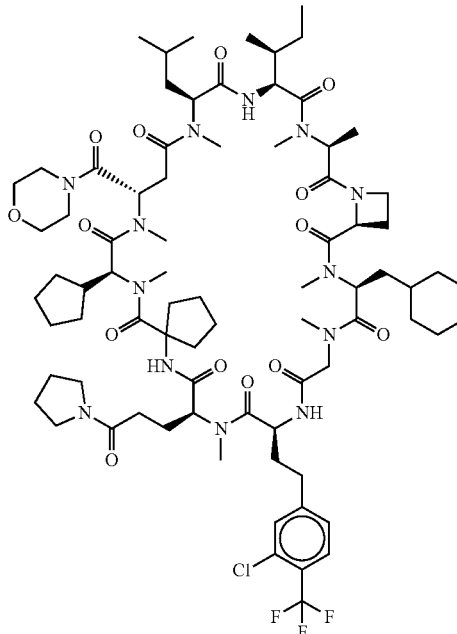 |
| 2105 | 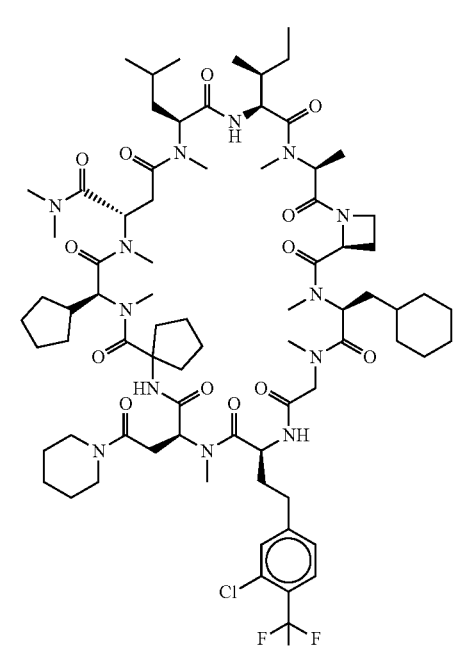 |

TABLE 24-continued
| Compound No. | Structural formula |
|---|---|
| 2106 | 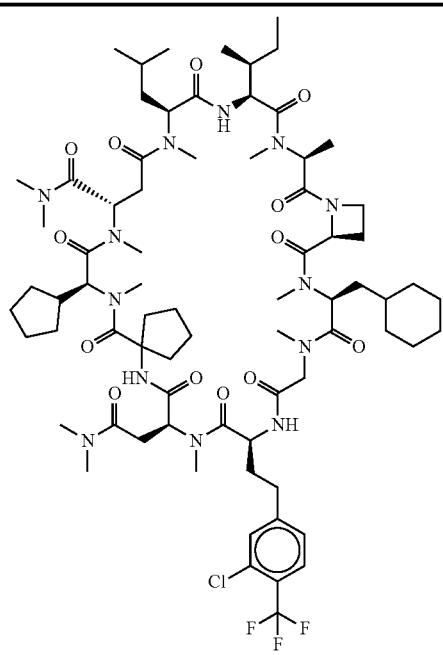 |
| 2107 | 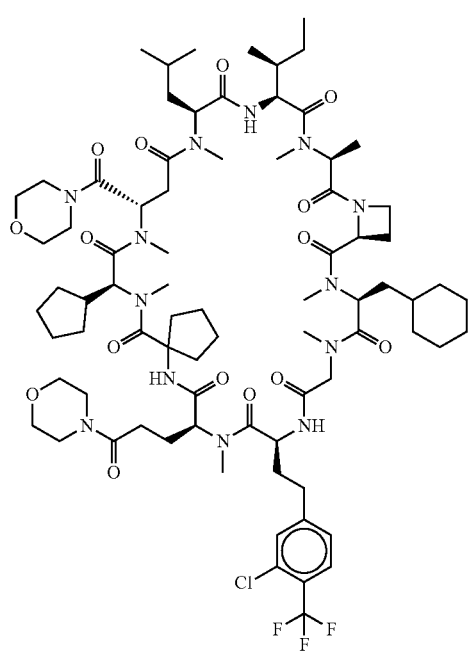 |

TABLE 24-continued
| Compound No. | Structural formula |
|---|---|
| 2108 | 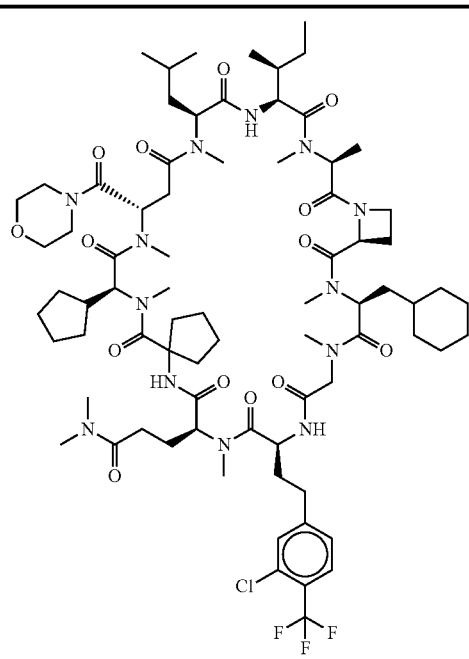 |
| 2109 | 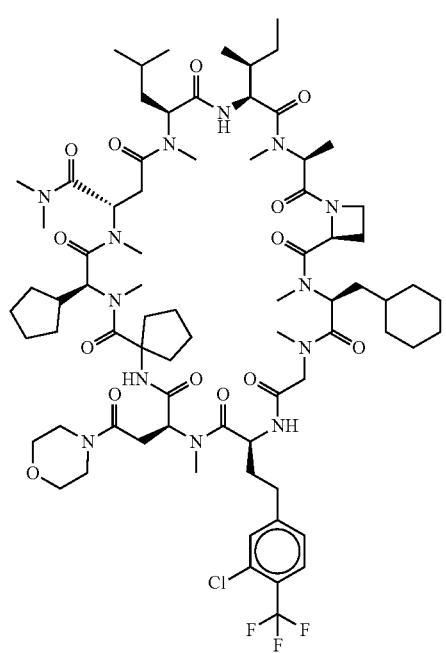 |

TABLE 24-continued
| Compound No. | Structural formula |
|---|---|
| 2110 | 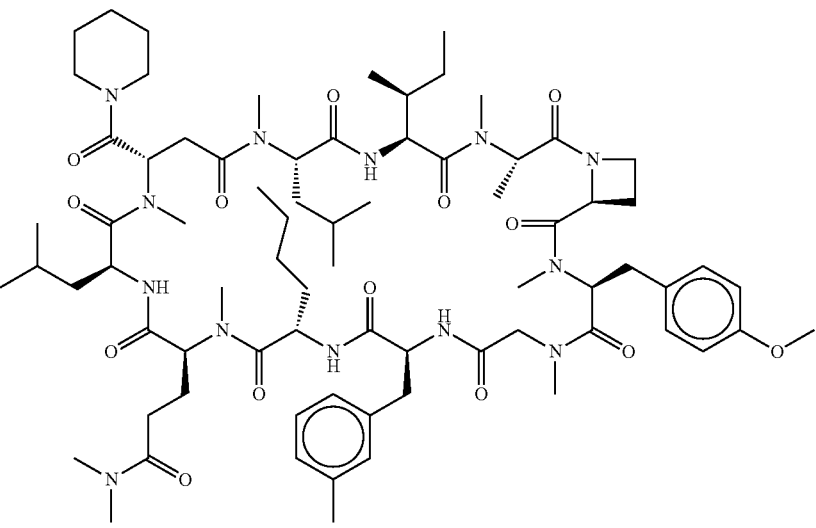 |
| 2111 | 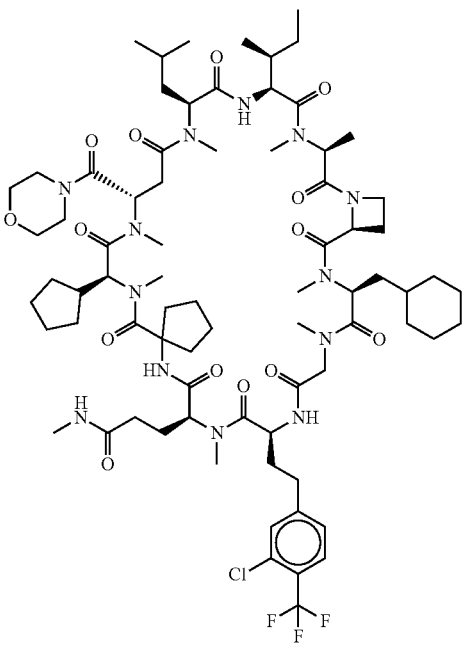 |

TABLE 24-continued
| Compound No. | Structural formula |
|---|---|
| 2112 | 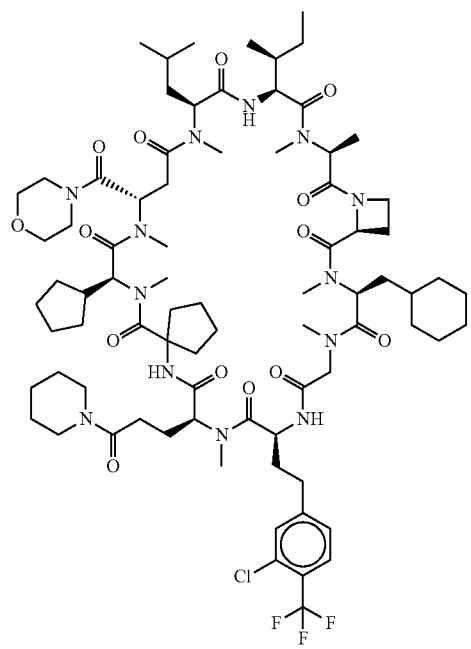 |
| 2113 | 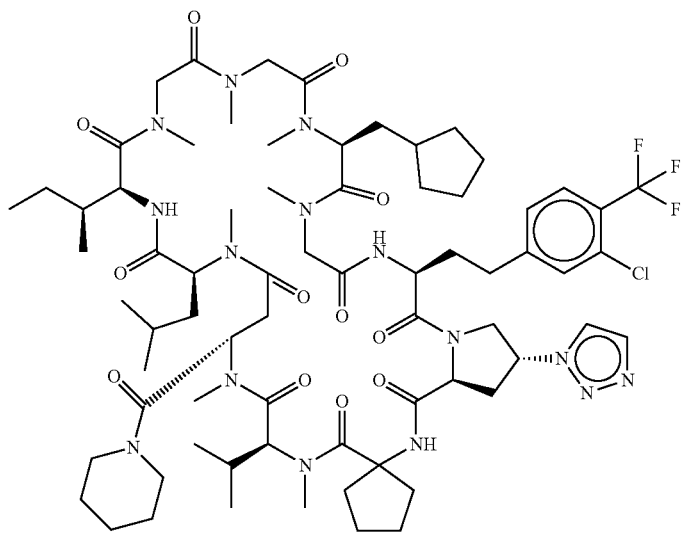 |

TABLE 24-continued
| Compound No. | Structural formula |
|---|---|
| 2114 | 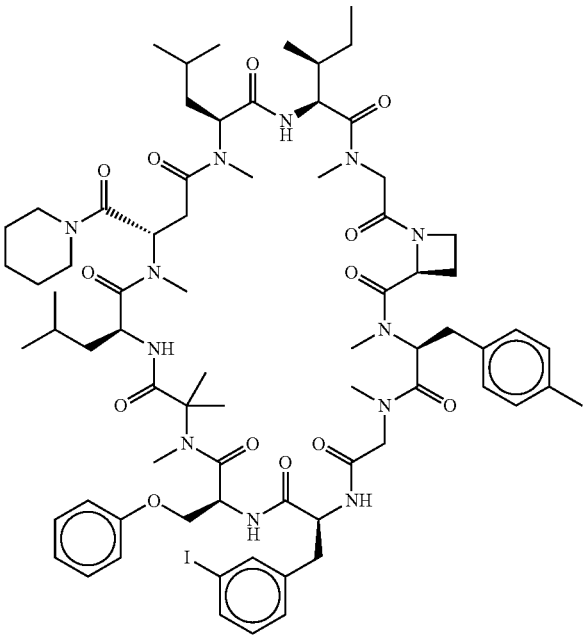 |
| 2115 | 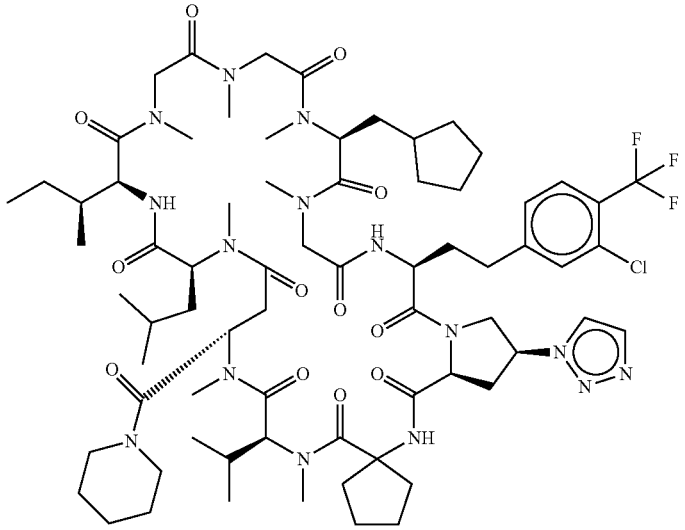 |

TABLE 24-continued
| Compound No. | Structural formula |
|---|---|
| 2116 | 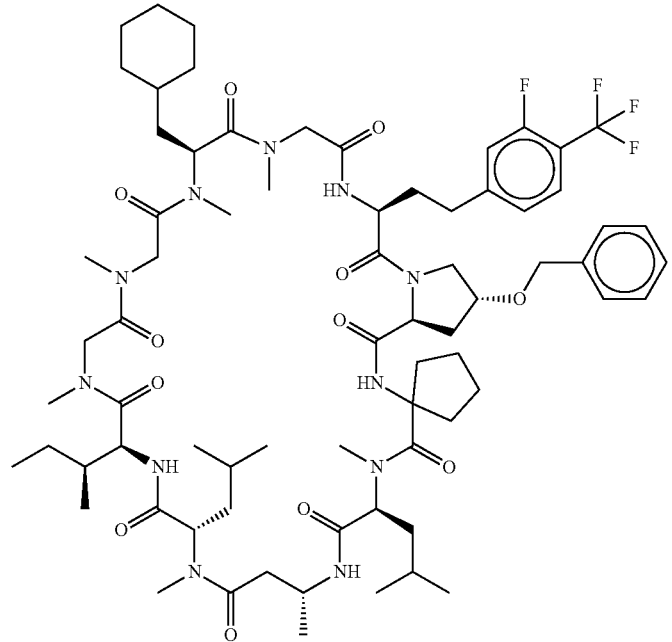 |
| 2117 | 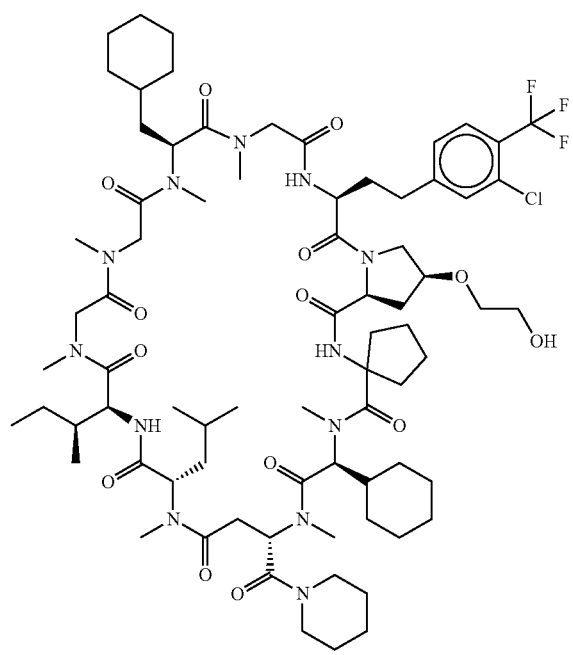 |

TABLE 24-continued
| Compound No. | Structural formula |
|---|---|
| 2118 | 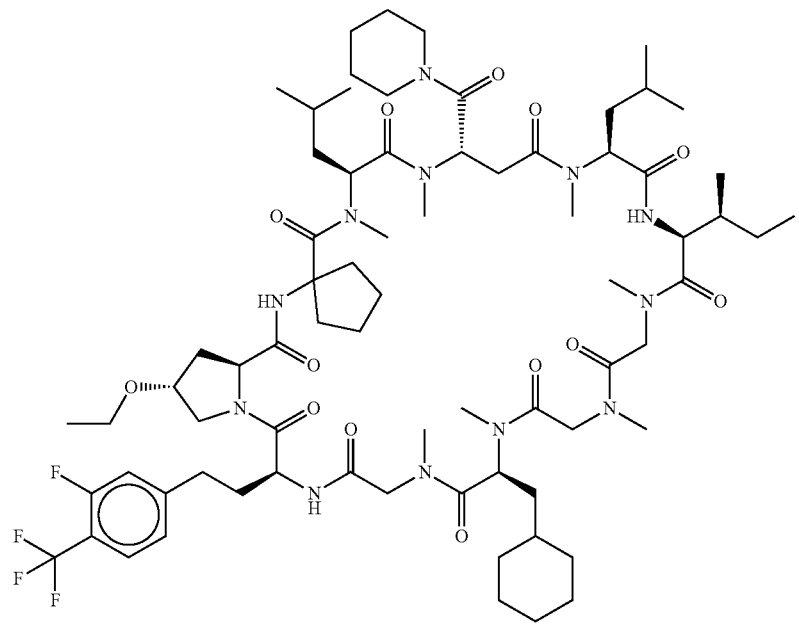 |
| 2119 | 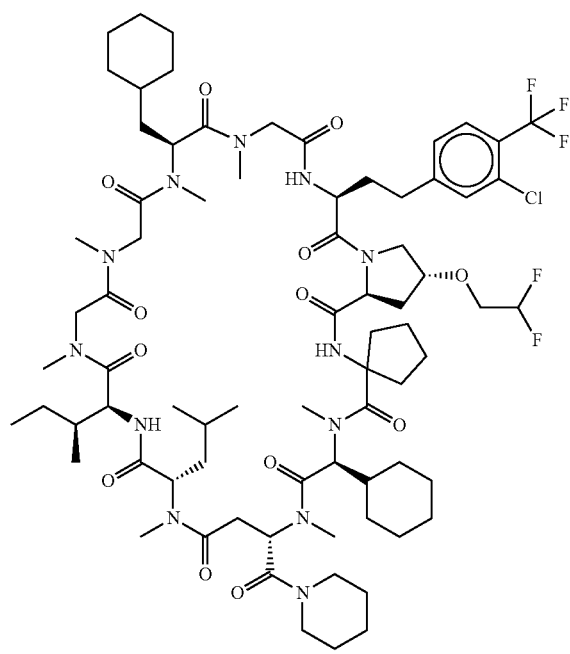 |

TABLE 24-continued
| Compound No. | Structural formula |
|---|---|
| 2120 | 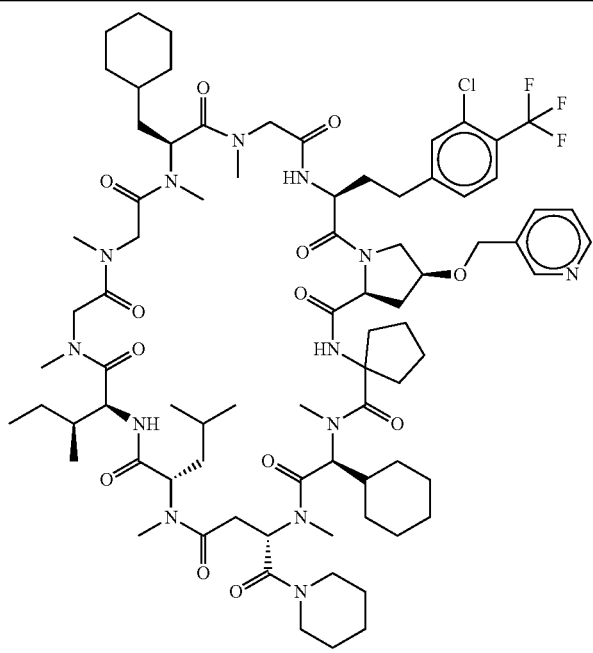 |
| 2121 | 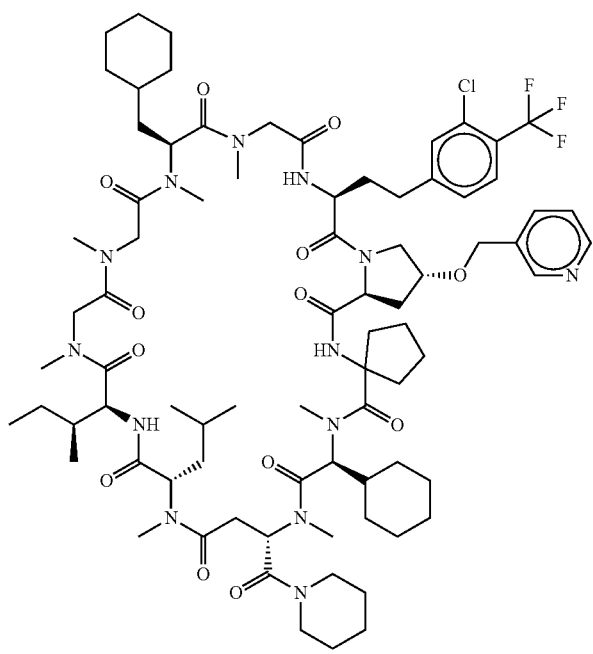 |

TABLE 24-continued
| Compound No. | Structural formula |
|---|---|
| 2122 | 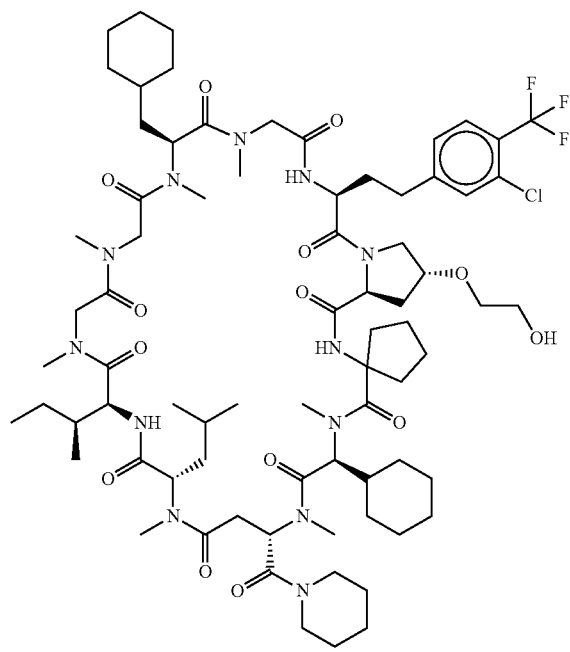 |
| 2123 | 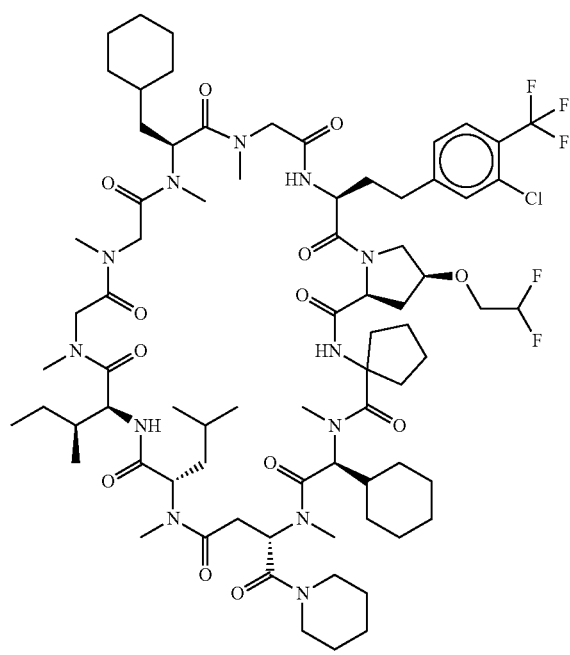 |

TABLE 24-continued
| Compound No. | Structural formula |
|---|---|
| 2124 | 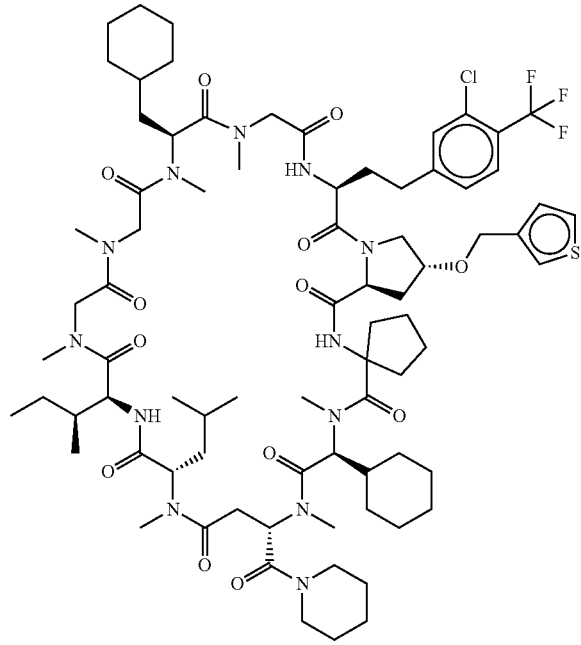 |
| 2125 | 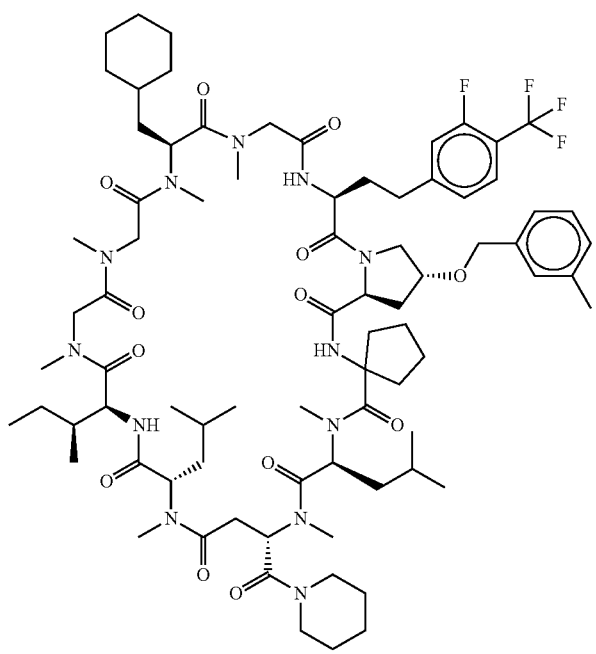 |

TABLE 24-continued
| Compound No. | Structural formula |
|---|---|
| 2126 | 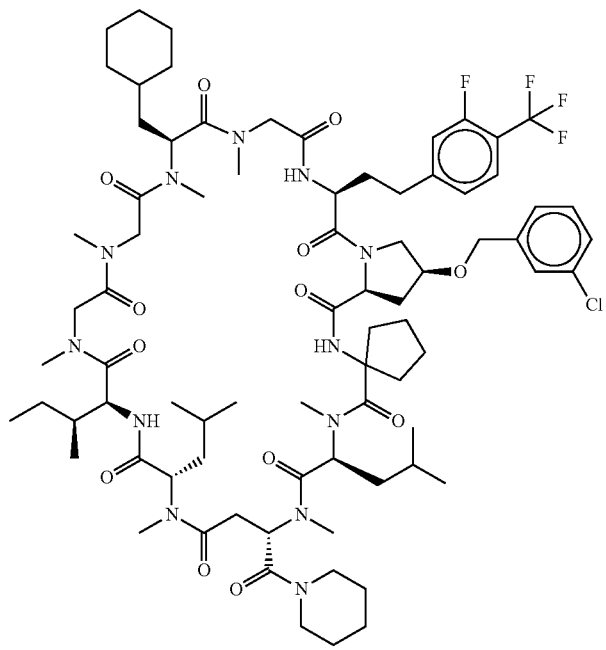 |
| 2127 | 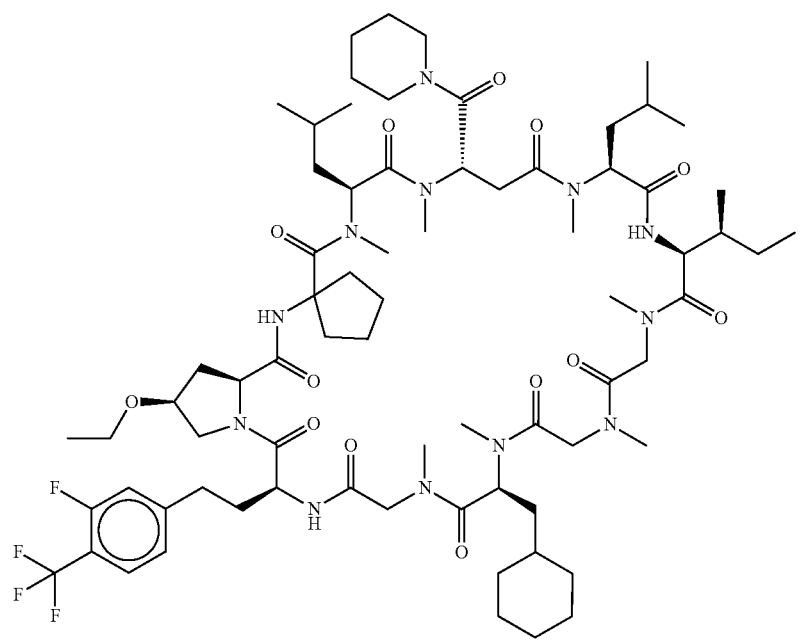 |

TABLE 24-continued
| Compound No. | Structural formula |
|---|---|
| 2128 | 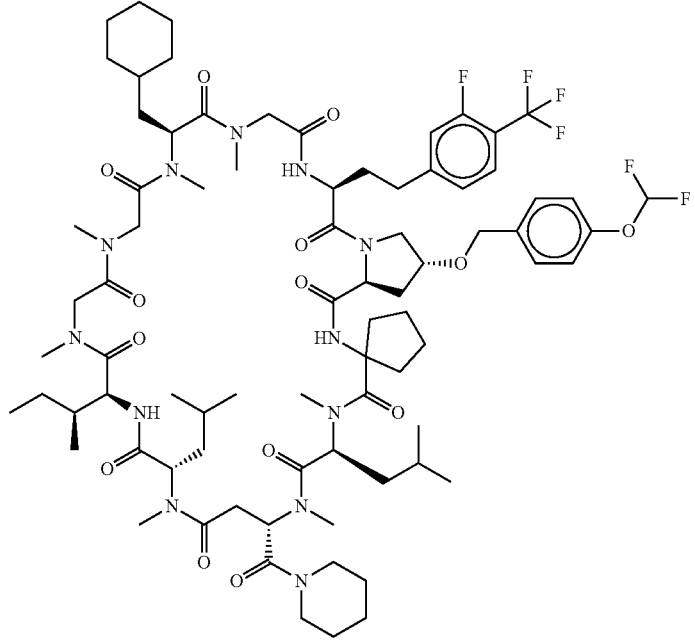 |
| 2129 | 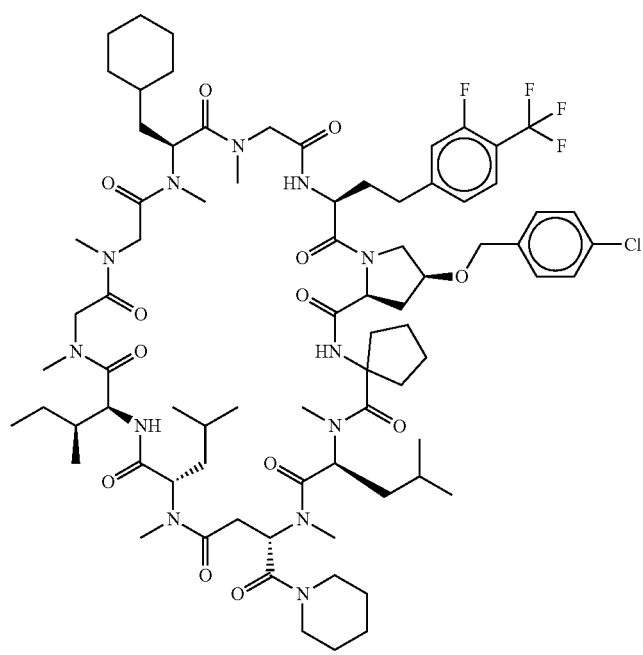 |

TABLE 24-continued
| Compound No. | Structural formula |
|---|---|
| 2130 | 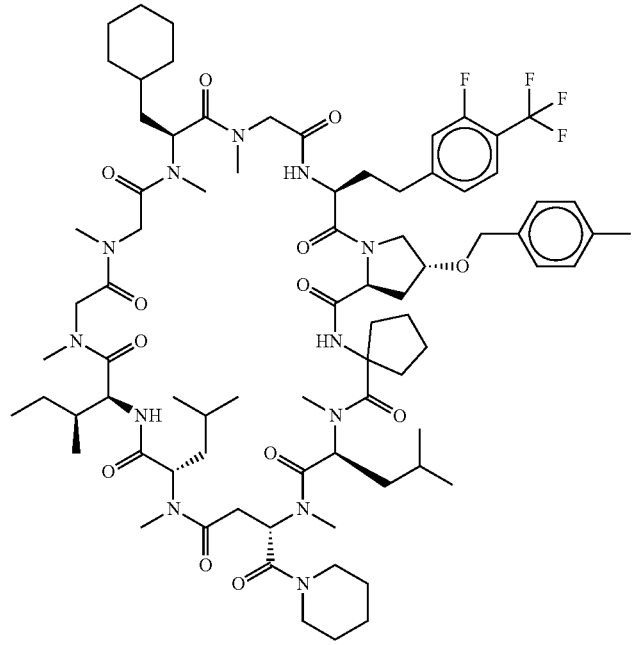 |
| 2131 | 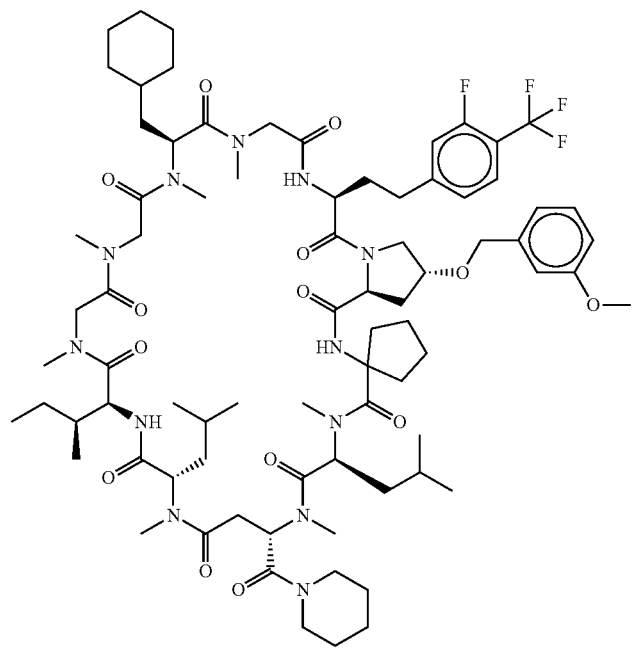 |

TABLE 24-continued
| Compound No. | Structural formula |
|---|---|
| 2132 | 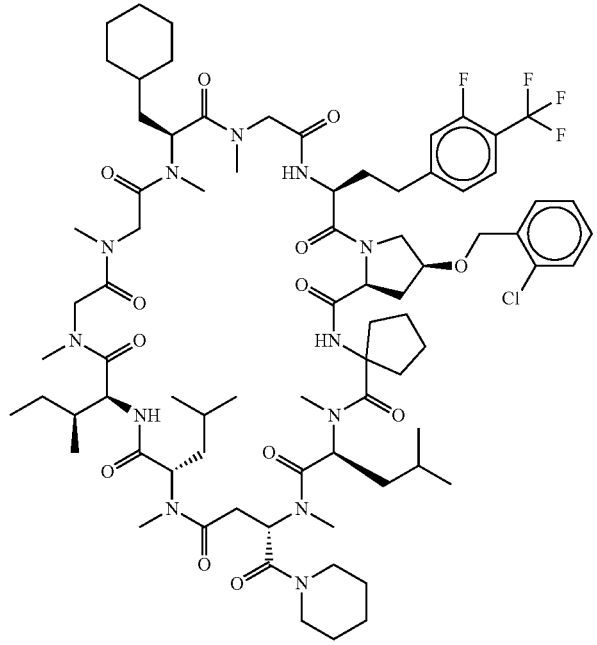 |
| 2133 | 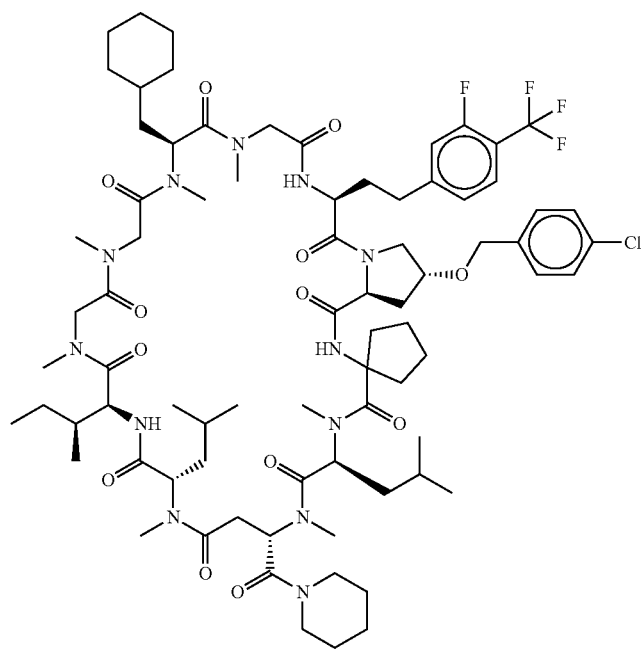 |

TABLE 24-continued
| Compound No. | Structural formula |
|---|---|
| 2134 | 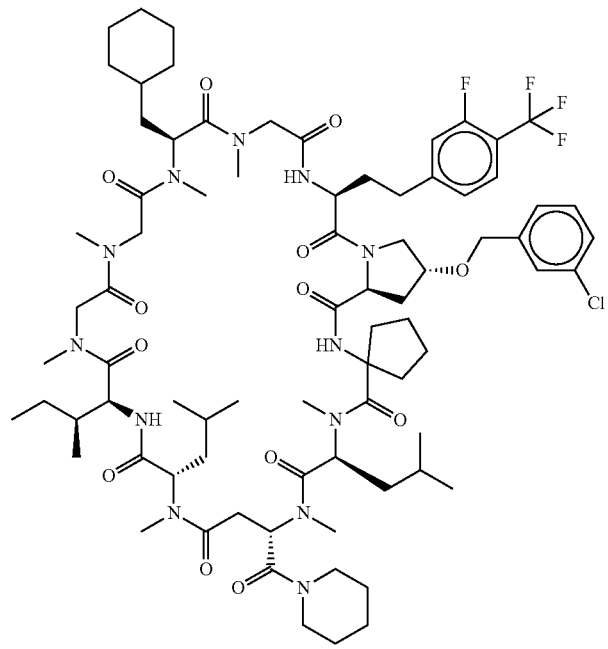 |
| 2135 | 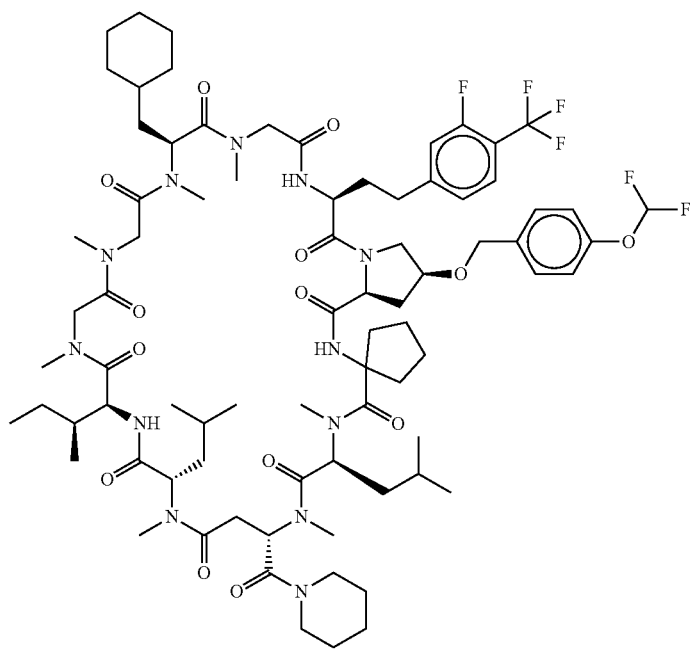 |

TABLE 24-continued
| Compound No. | Structural formula |
|---|---|
| 2136 | 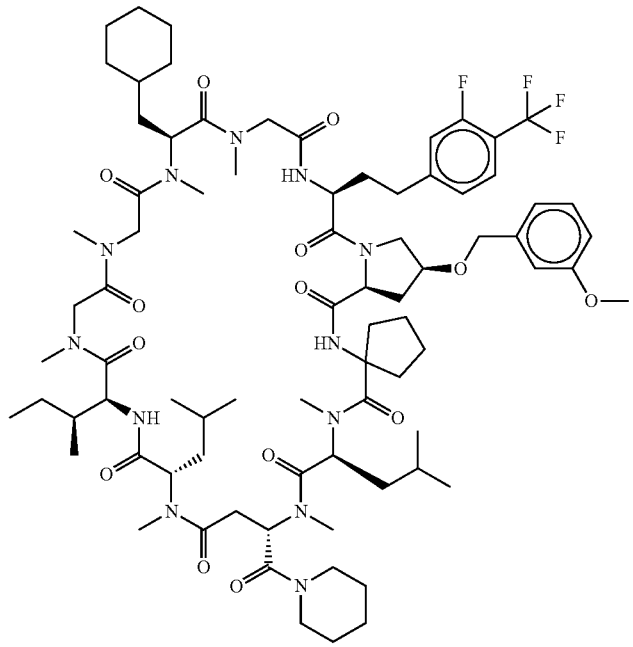 |
| 2137 | 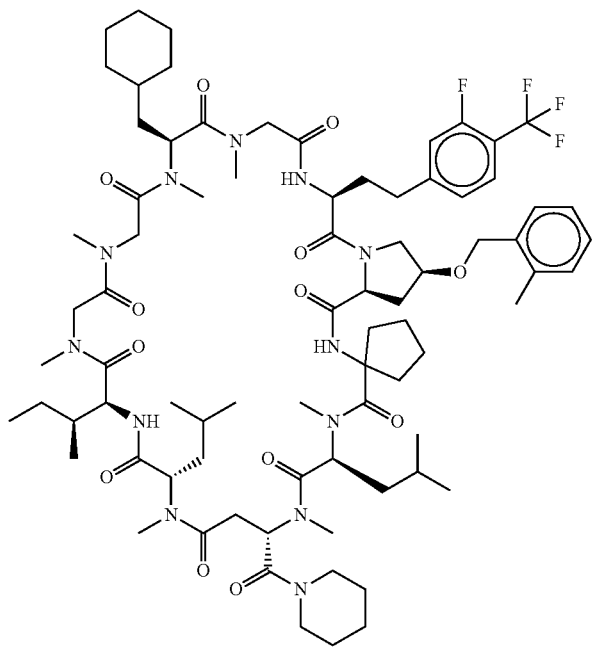 |

TABLE 24-continued
| Compound No. | Structural formula |
|---|---|
| 2138 | 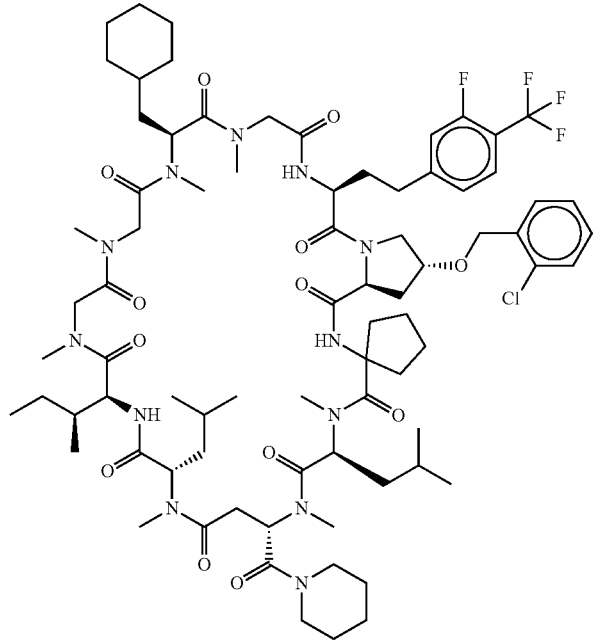 |
| 2139 | 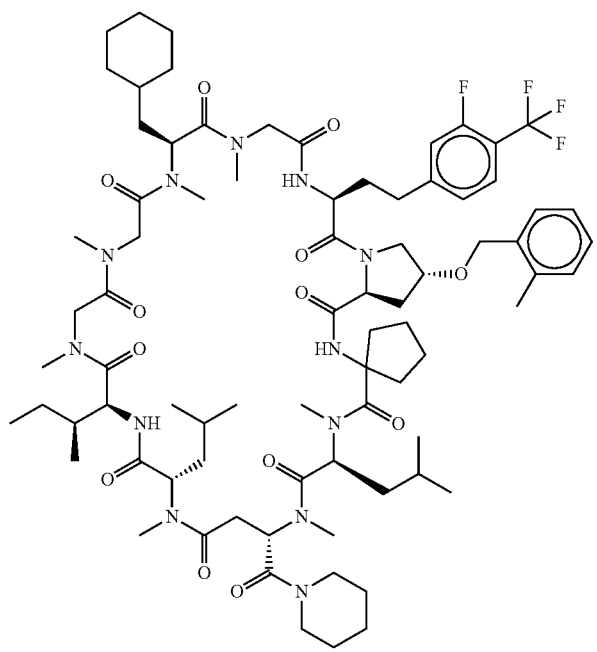 |

TABLE 24-continued
| Compound No. | Structural formula |
|---|---|
| 2140 | 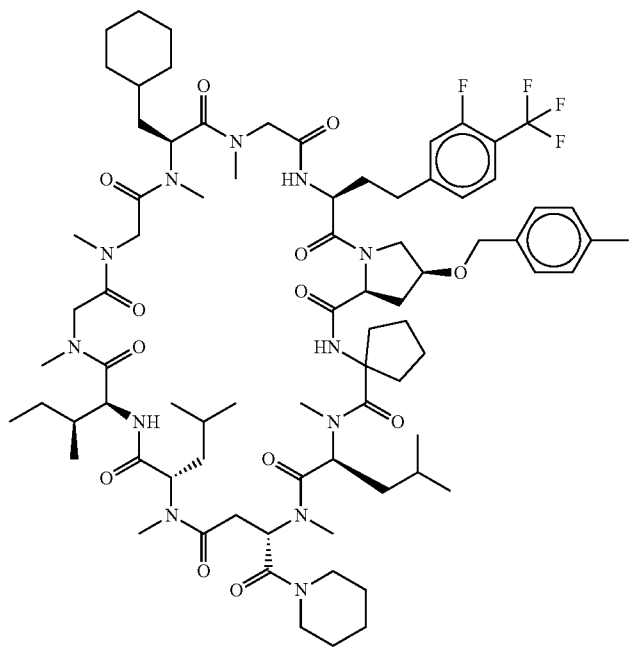 |
| 2141 | 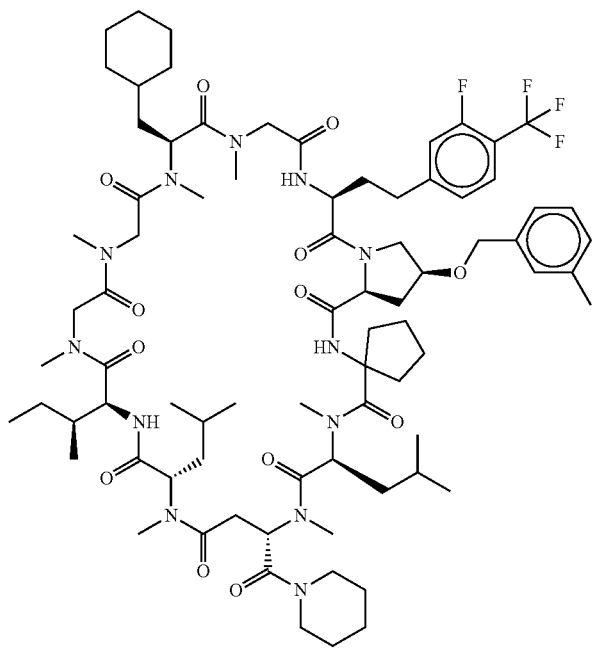 |

TABLE 24-continued
| Compound No. | Structural formula |
| --- | --- |
| 2142 | 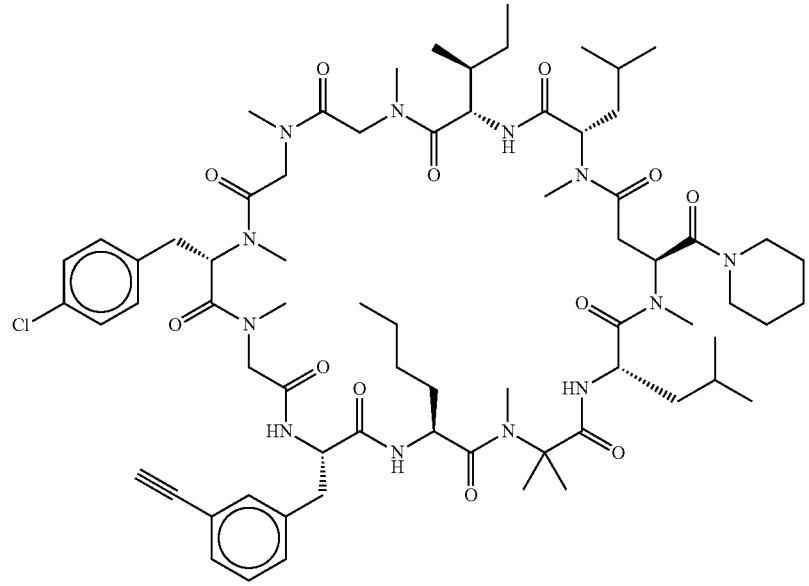 |
| 2143 | 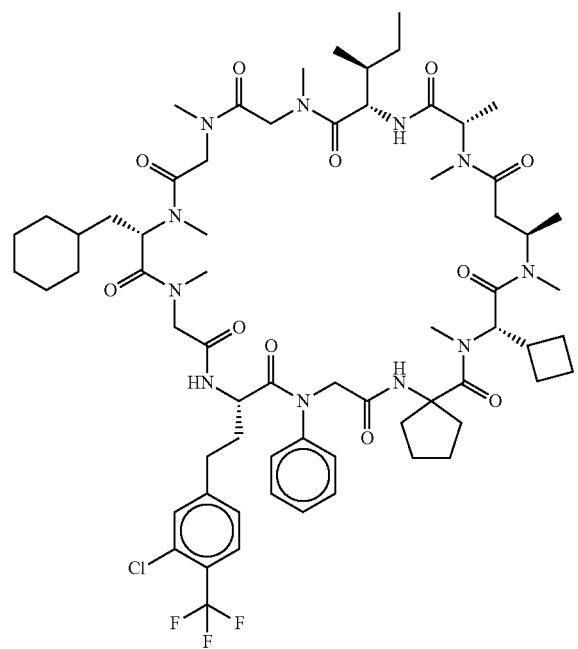 |

TABLE 24-continued
| Compound No. | Structural formula |
|---|---|
| 2144 | 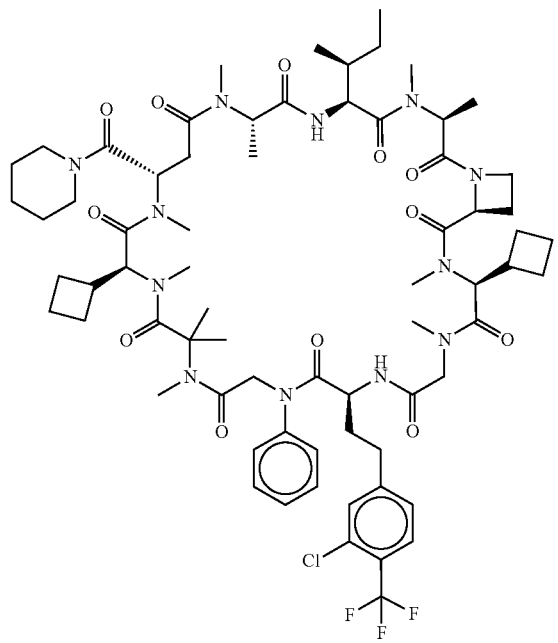 |
| 2145 | 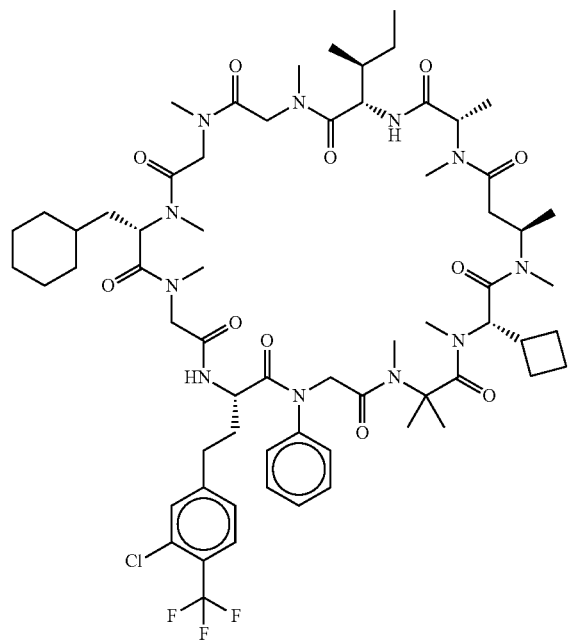 |

TABLE 24-continued
| Compound No. | Structural formula |
|---|---|
| 2146 | 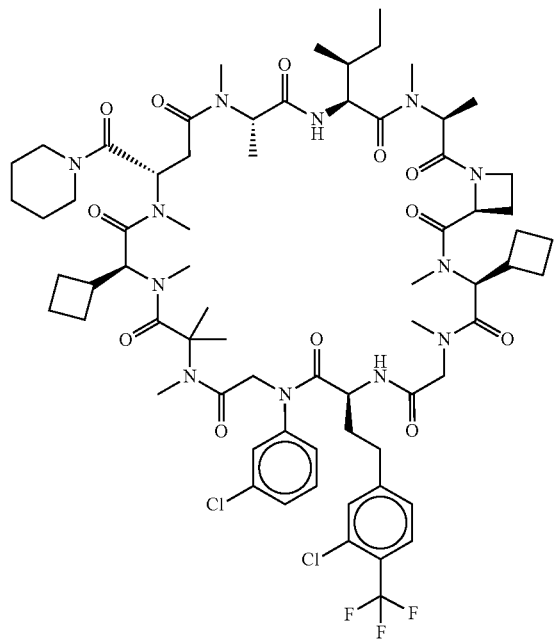 |
| 2147 | 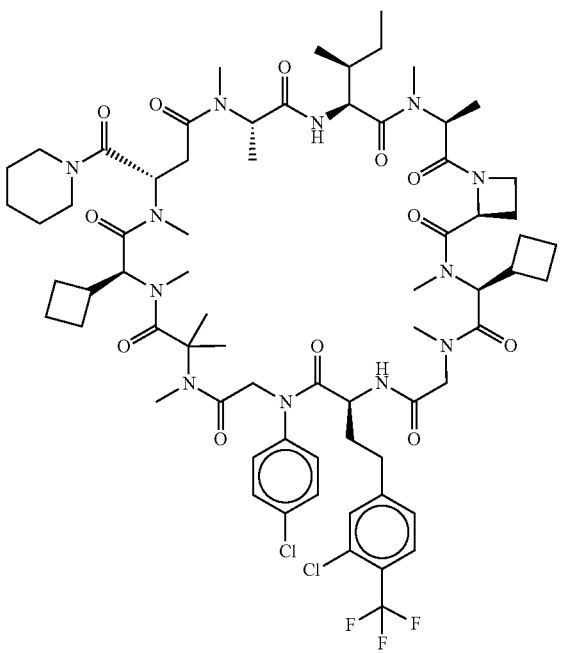 |

TABLE 24-continued
| Compound No. | Structural formula |
|---|---|
| 2148 | 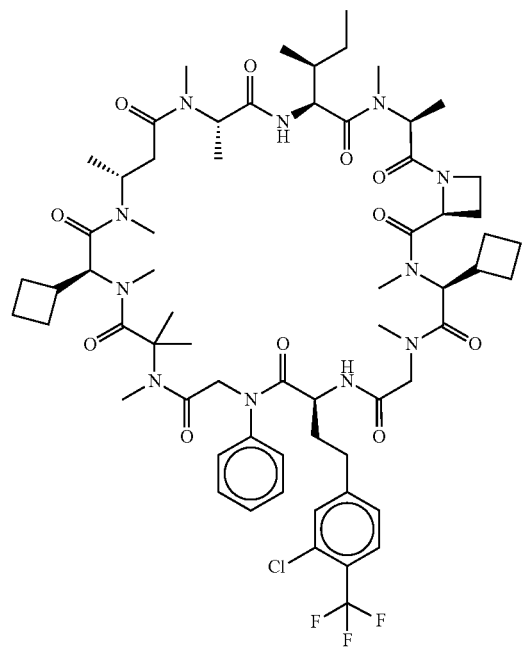 |
| 2149 | 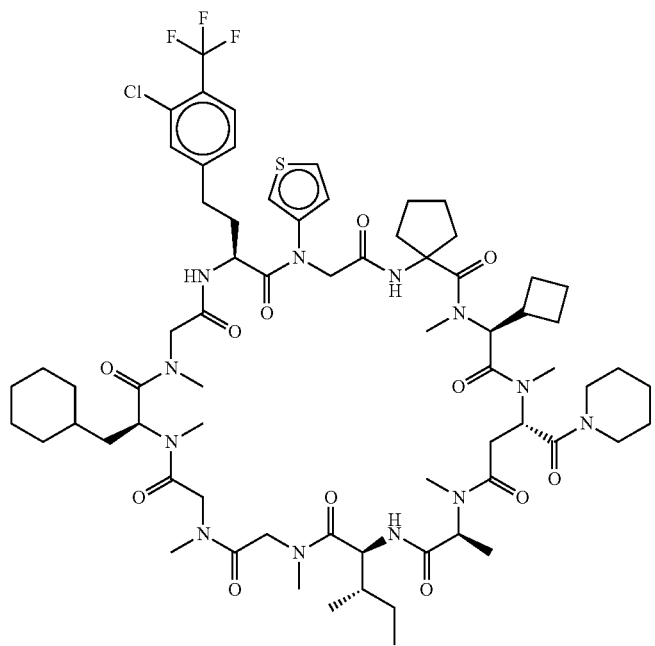 |

TABLE 24-continued
| Compound No. | Structural formula |
|---|---|
| 2150 | 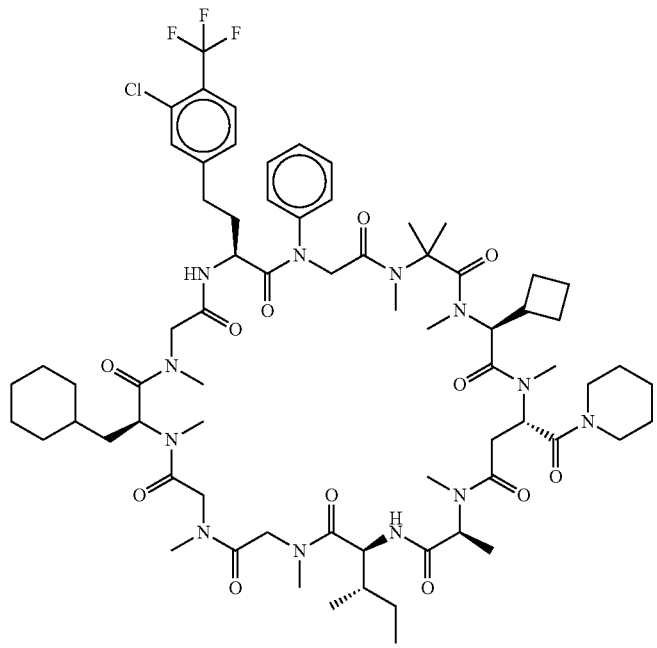 |
| 2151 | 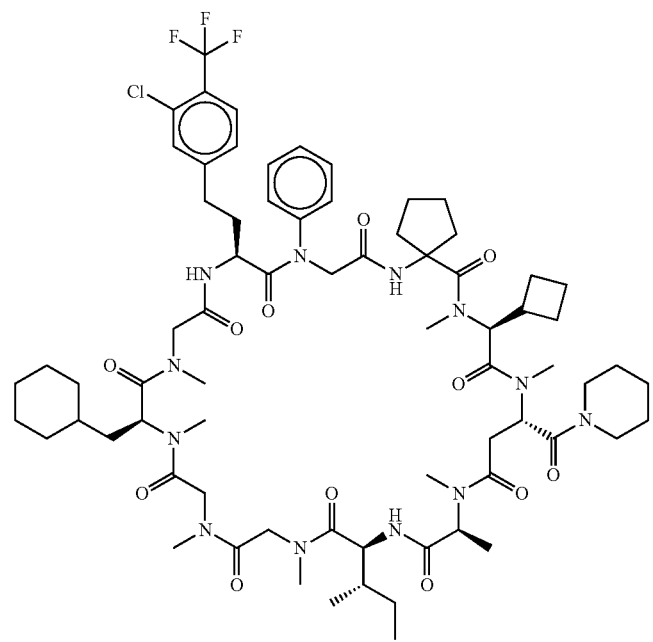 |

TABLE 24-continued
| Compound No. | Structural formula |
| --- | --- |
| 2152 | 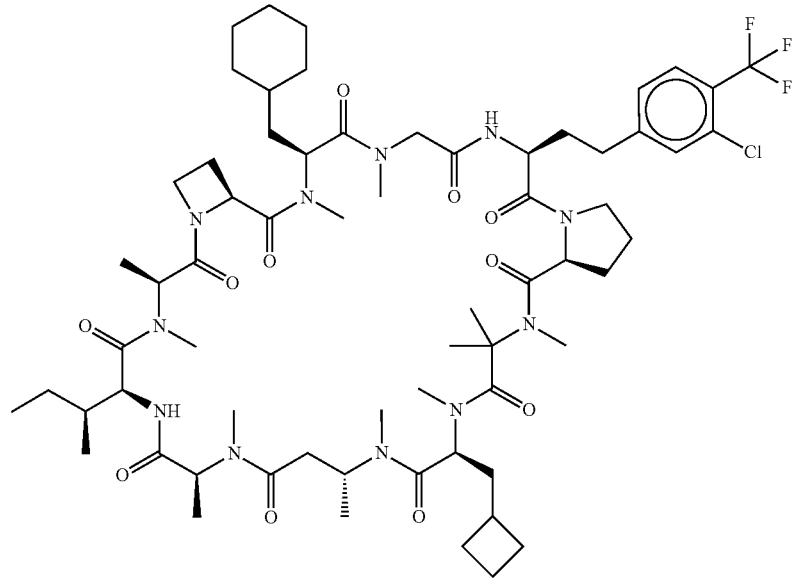 |
| 2153 | 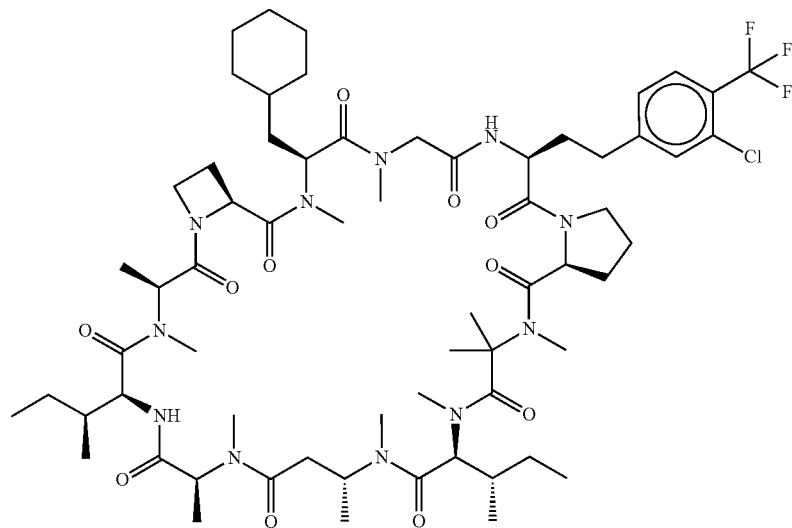 |

TABLE 24-continued
| Compound No. | Structural formula |
|---|---|
| 2154 | 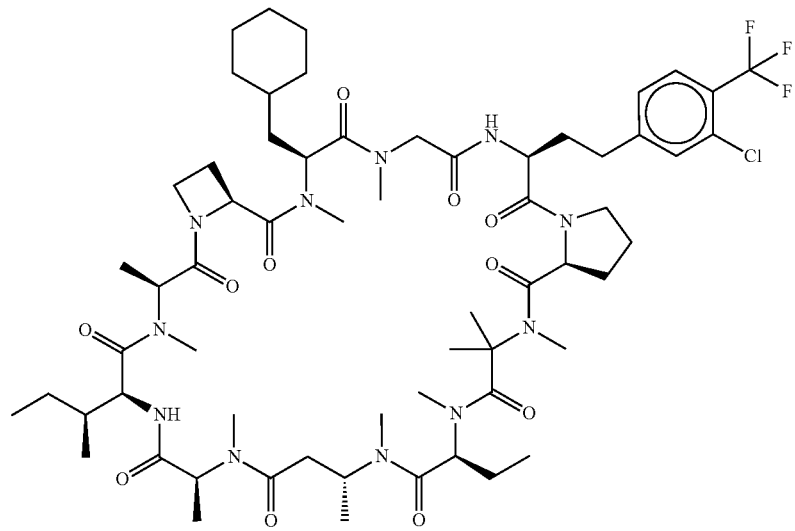 |
| 2155 | 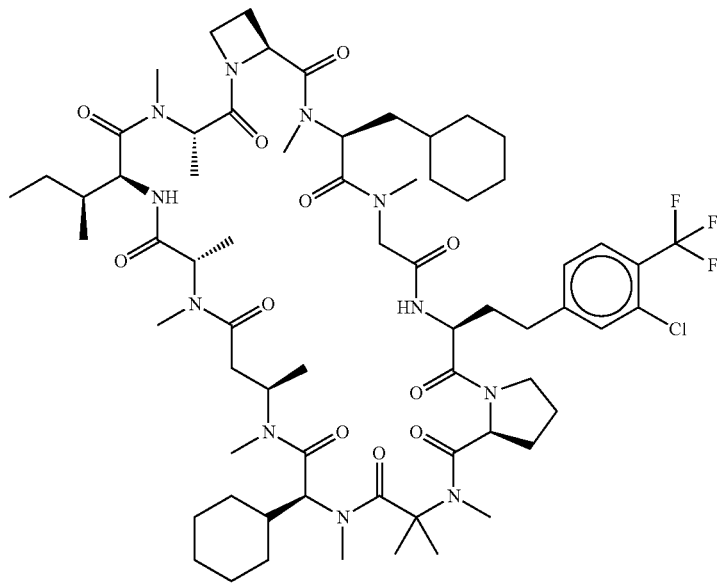 |

TABLE 24-continued
| Compound No. | Structural formula |
|---|---|
| 2156 | 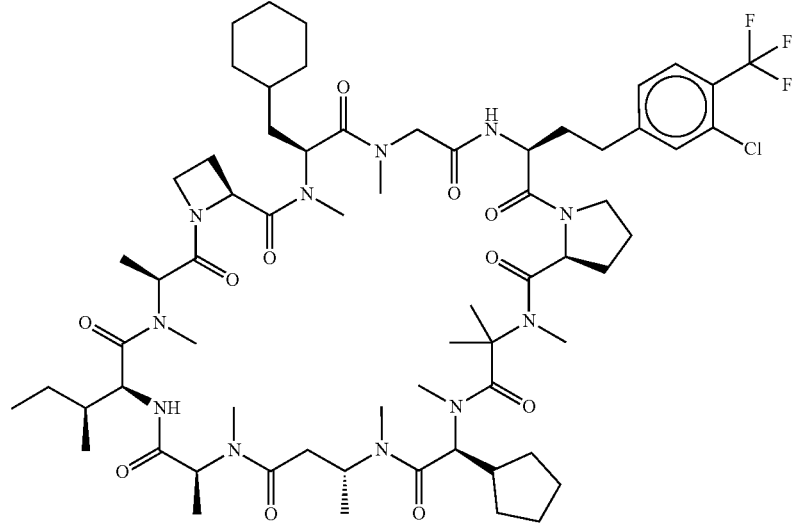 |
| 2157 | 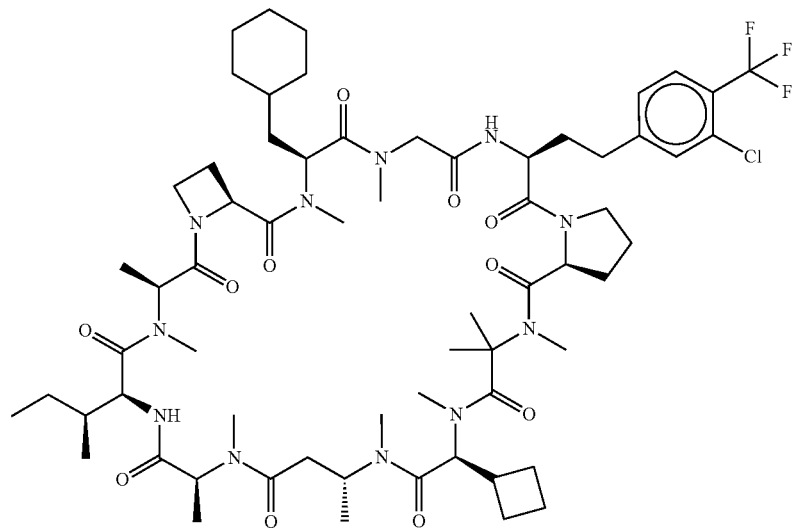 |

TABLE 24-continued
| Compound No. | Structural formula |
|---|---|
| 2158 | 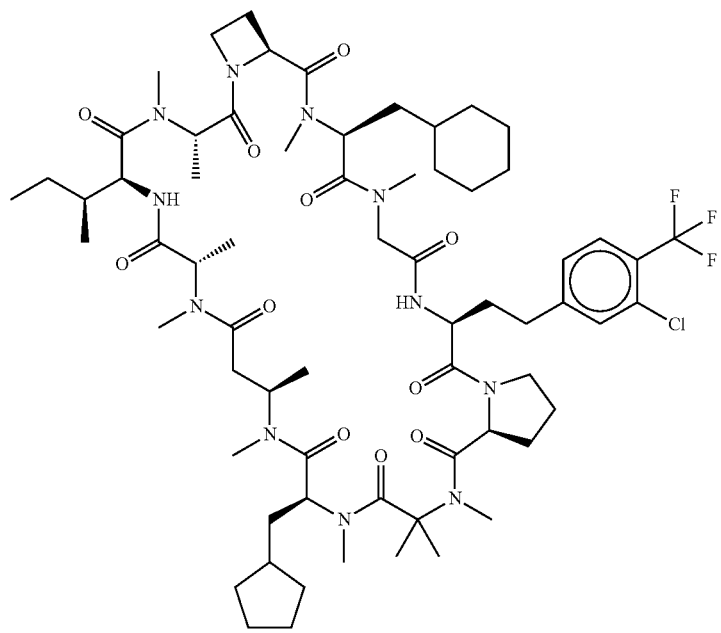 |
| 2159 | 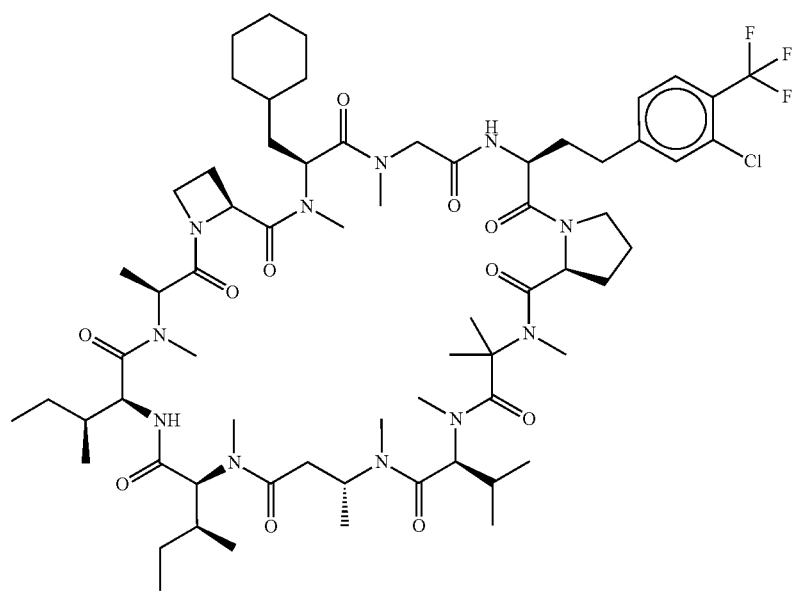 |

TABLE 24-continued
| Compound No. | Structural formula |
|---|---|
| 2160 | 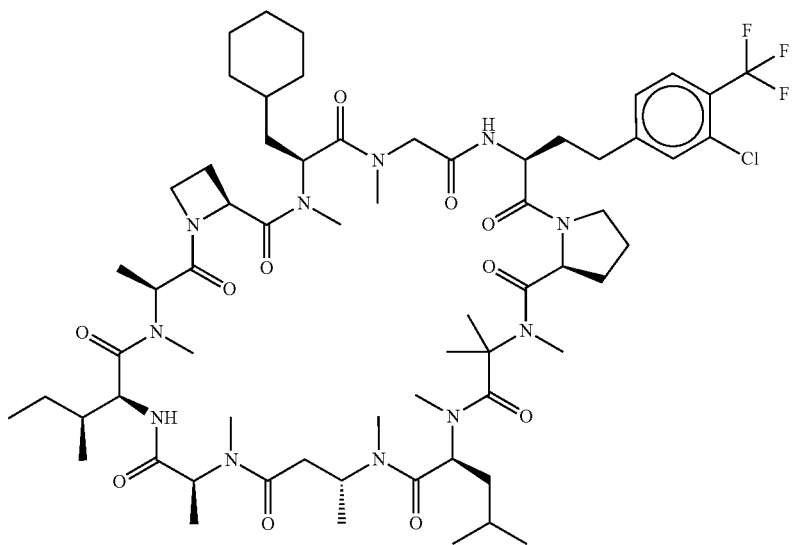 |
| 2161 | 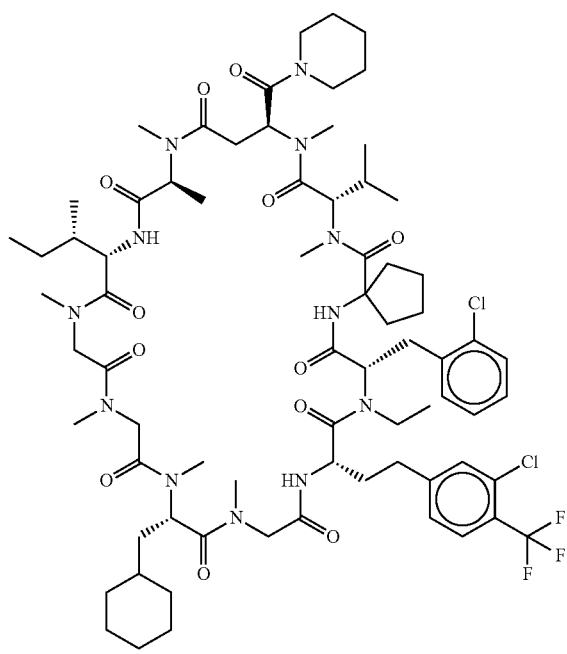 |

TABLE 24-continued
| Compound No. | Structural formula |
|---|---|
| 2162 | 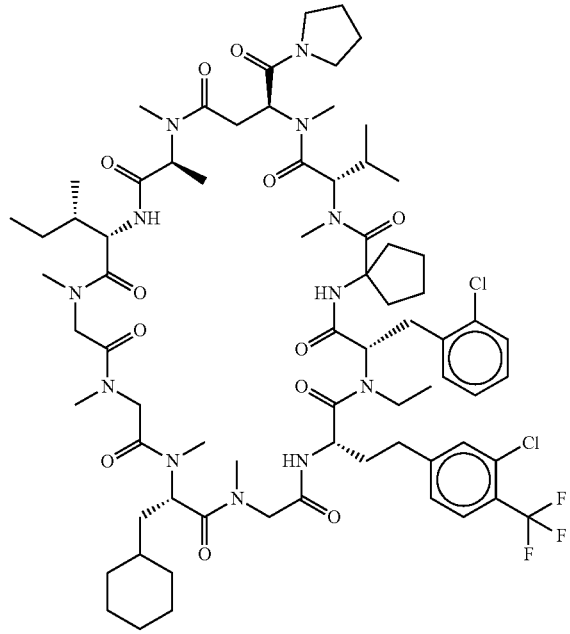 |
| 2163 | 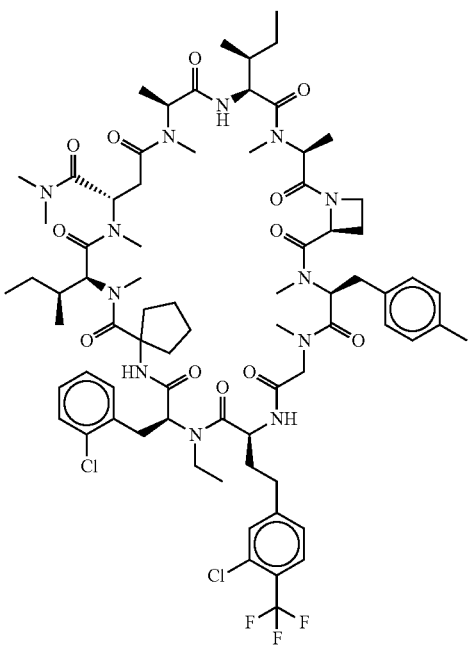 |

TABLE 24-continued
| Compound No. | Structural formula |
|---|---|
| 2164 | 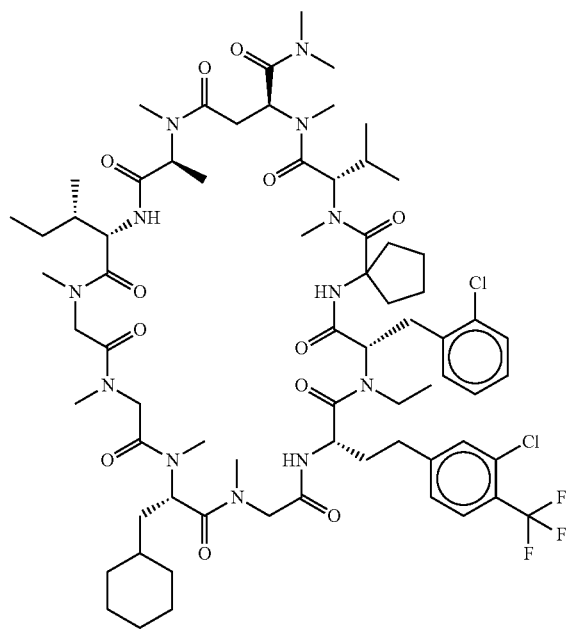 |
| 2165 | 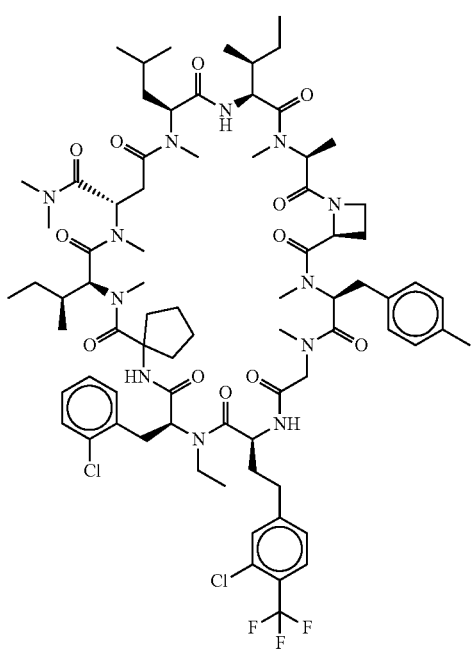 |

TABLE 24-continued
| Compound No. | Structural formula |
|---|---|
| 2166 | 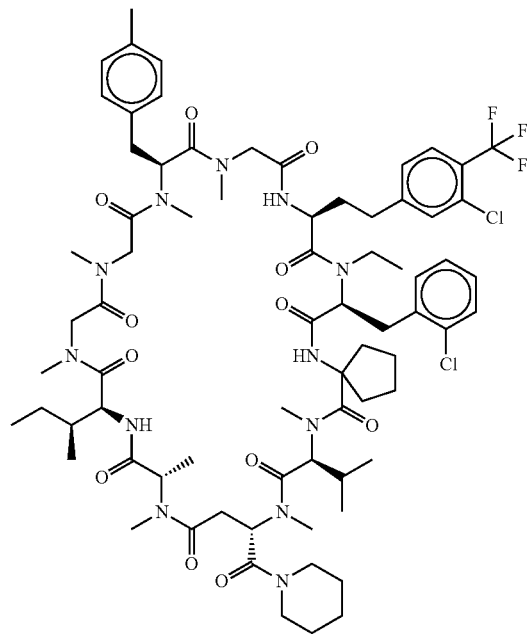 |
| 2167 | 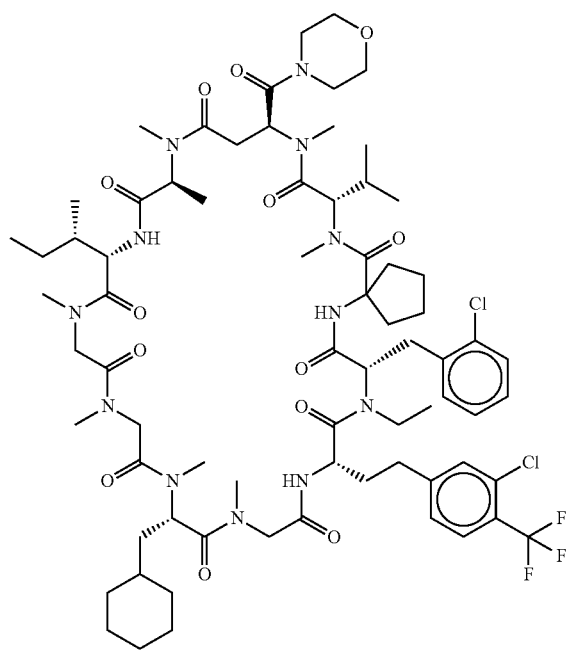 |

TABLE 24-continued
| Compound No. | Structural formula |
|---|---|
| 2168 | 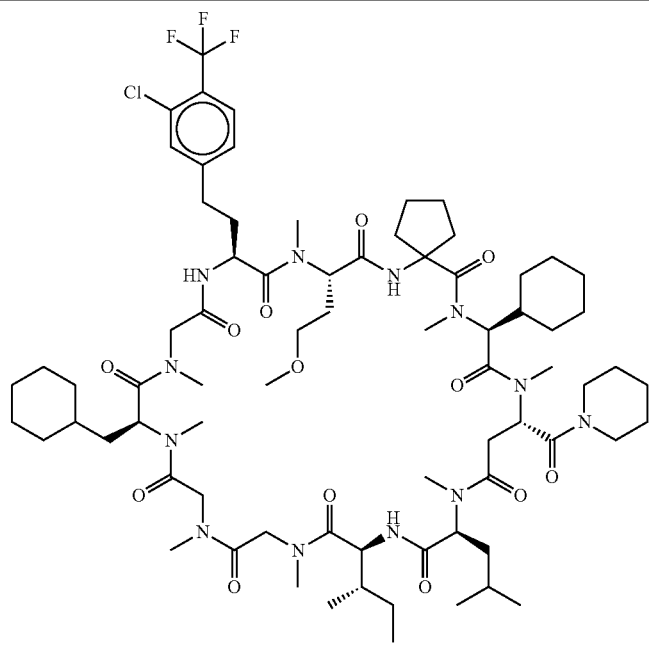 |
| 2169 | 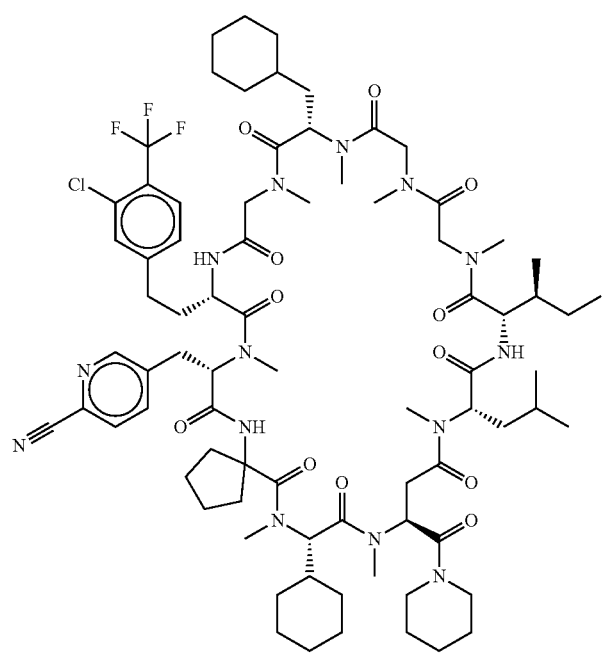 |

TABLE 24-continued
| Compound No. | Structural formula |
|---|---|
| 2170 | 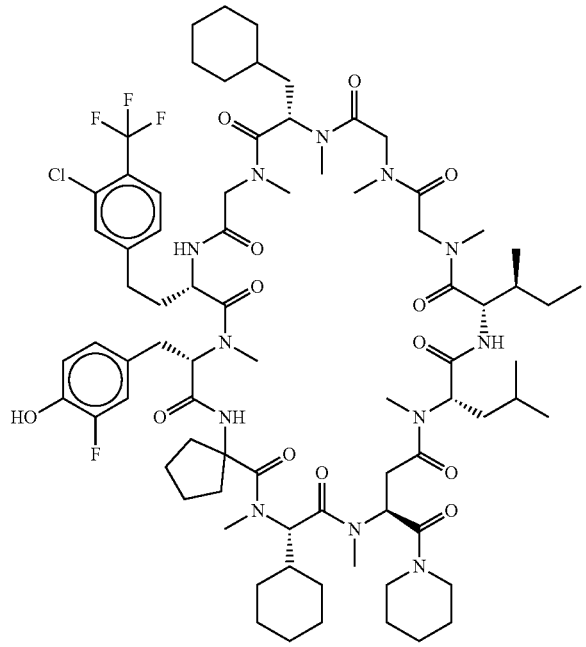 |
| 2171 | 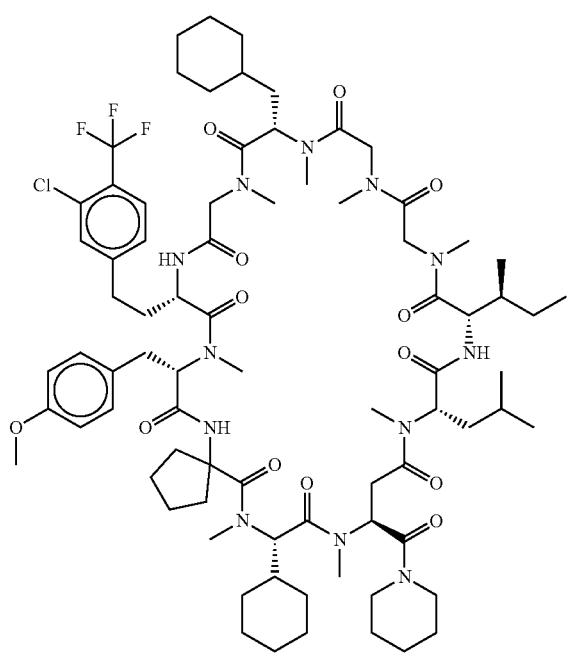 |

TABLE 24-continued
| Compound No. | Structural formula |
|---|---|
| 2172 | 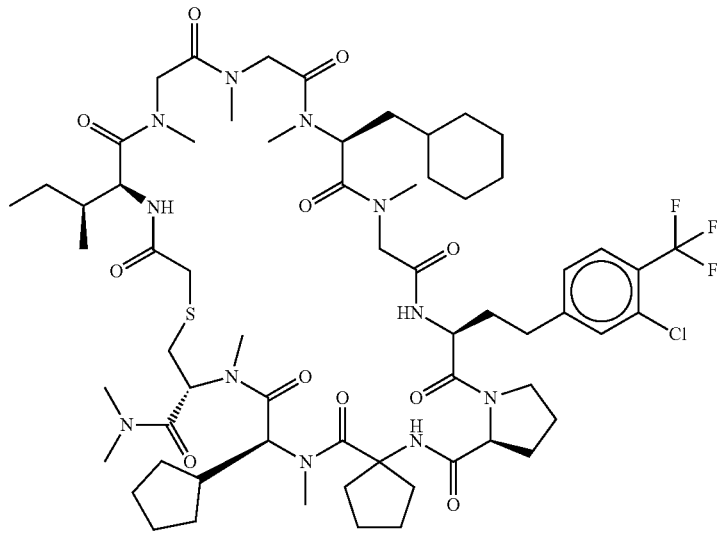 |
| 2173 | 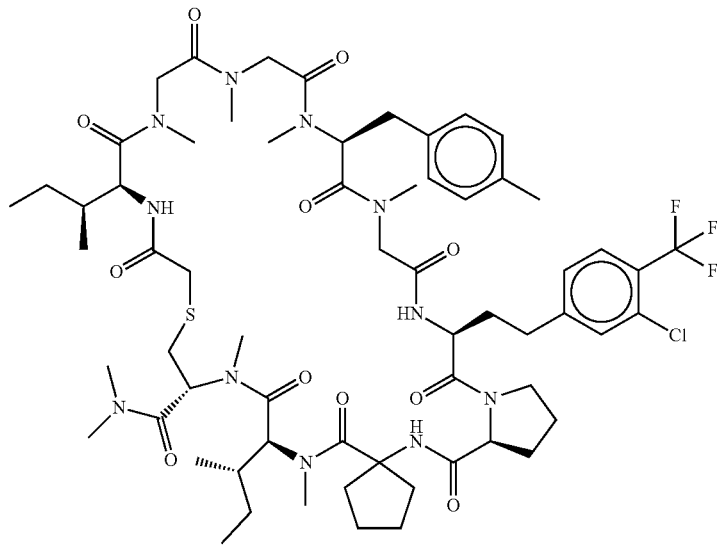 |

TABLE 24-continued
| Compound No. | Structural formula |
|---|---|
| 2174 | 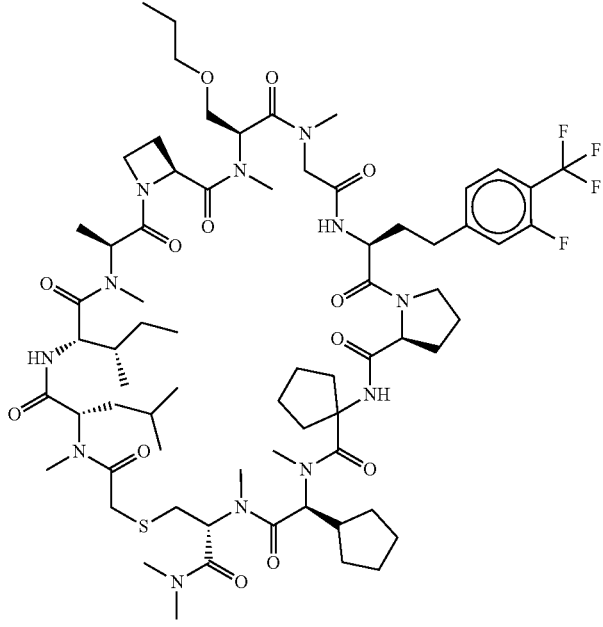 |
| 2175 | 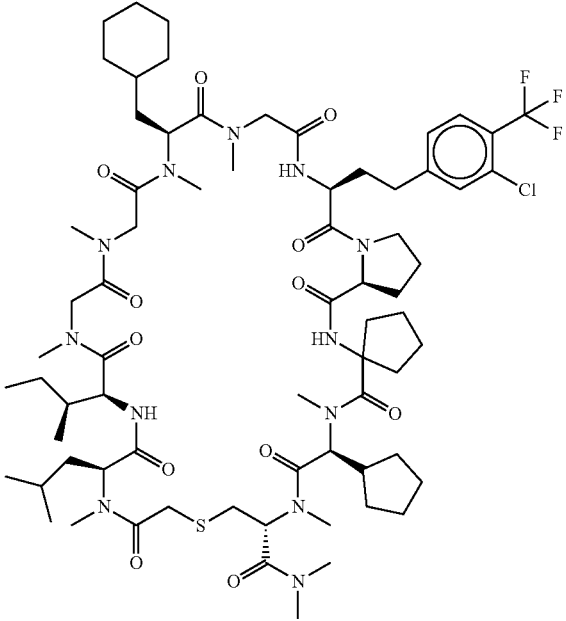 |

TABLE 24-continued
| Compound No. | Structural formula |
|---|---|
| 2176 | 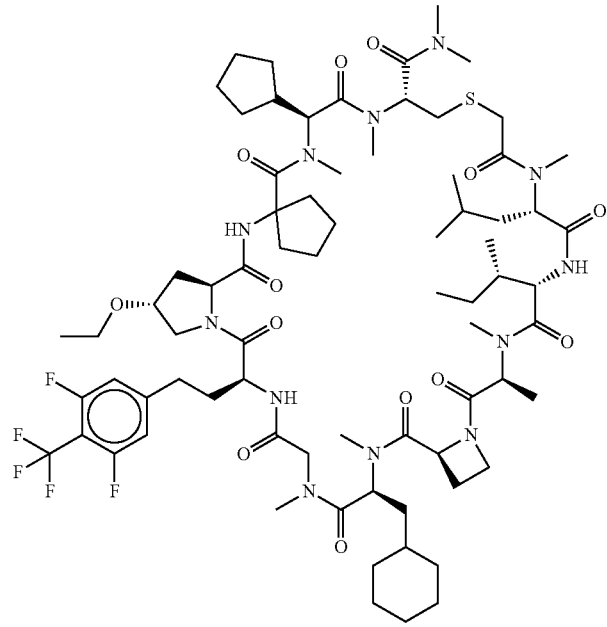 |
| 2177 | 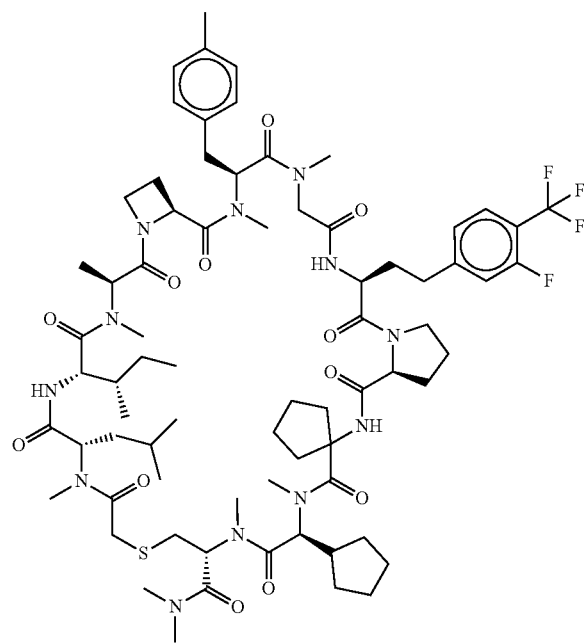 |

TABLE 24-continued
| Compound No. | Structural formula |
|---|---|
| 2178 | 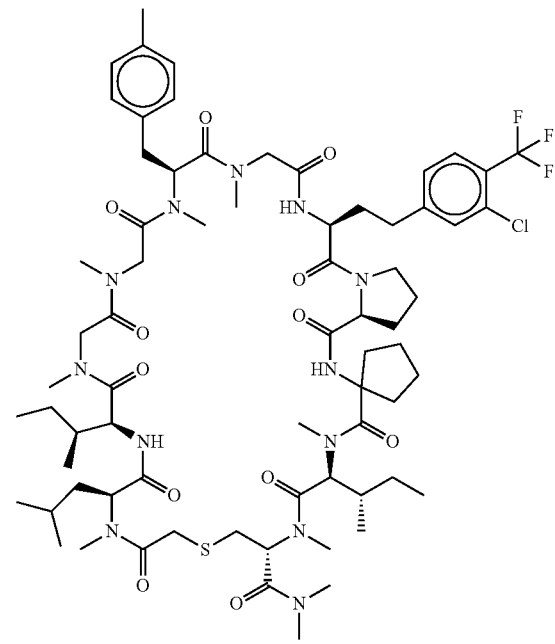 |
| 2179 | 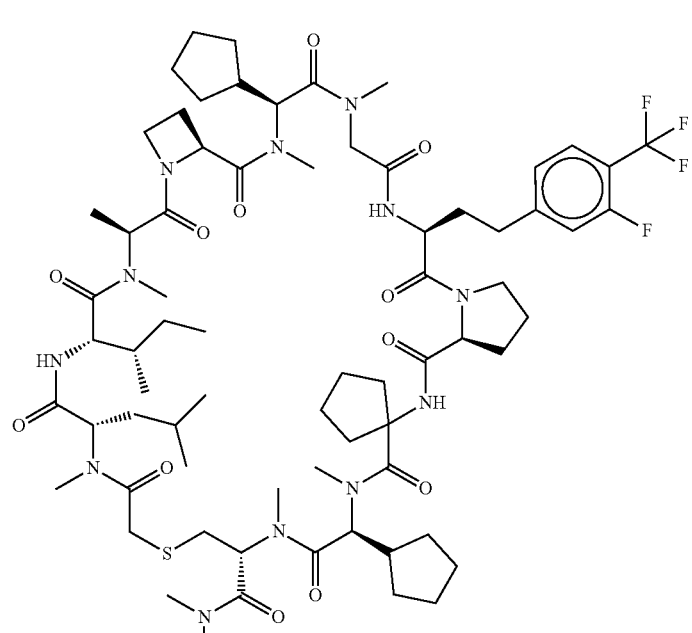 |

TABLE 24-continued
| Compound No. | Structural formula |
|---|---|
| 2180 | 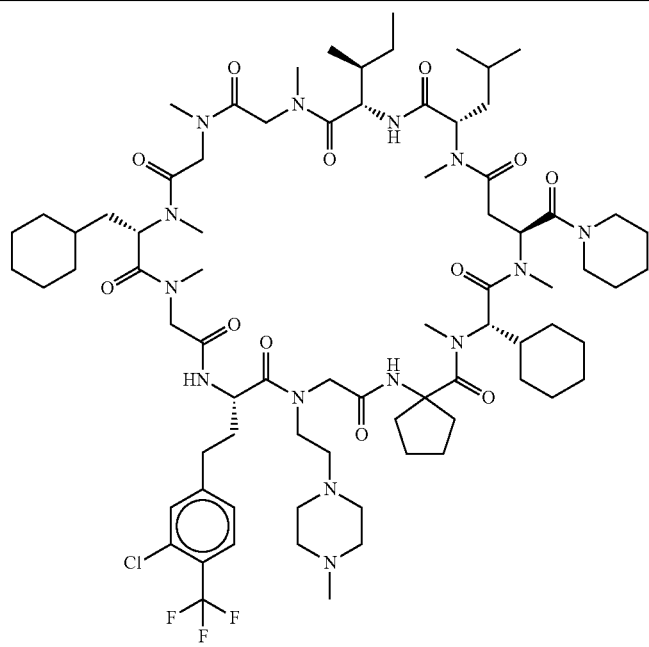 |
| 2181 | 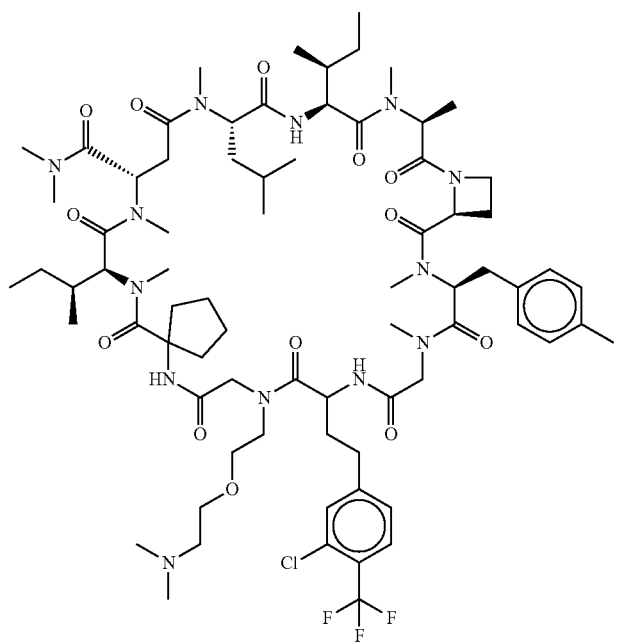 |

TABLE 24-continued
| Compound No. | Structural formula |
|---|---|
| 2182 | 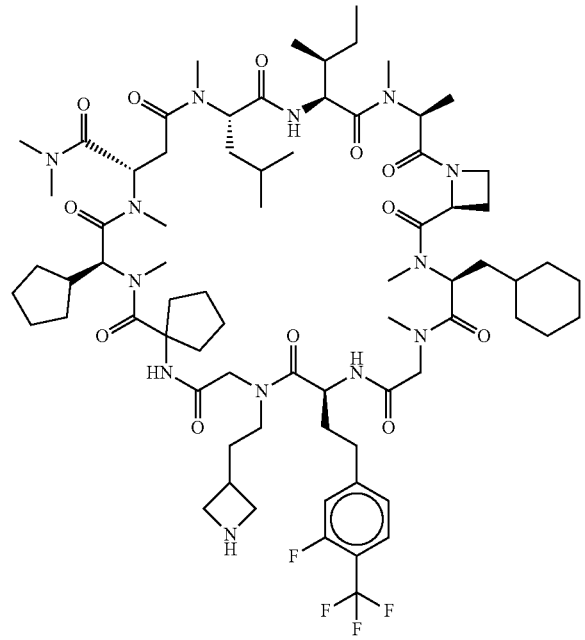 |
| 2183 | 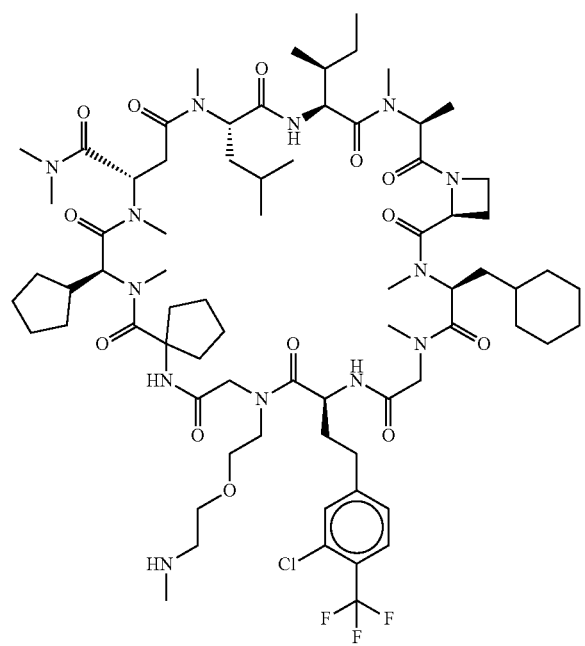 |

TABLE 24-continued
| Compound No. | Structural formula |
|---|---|
| 2184 | 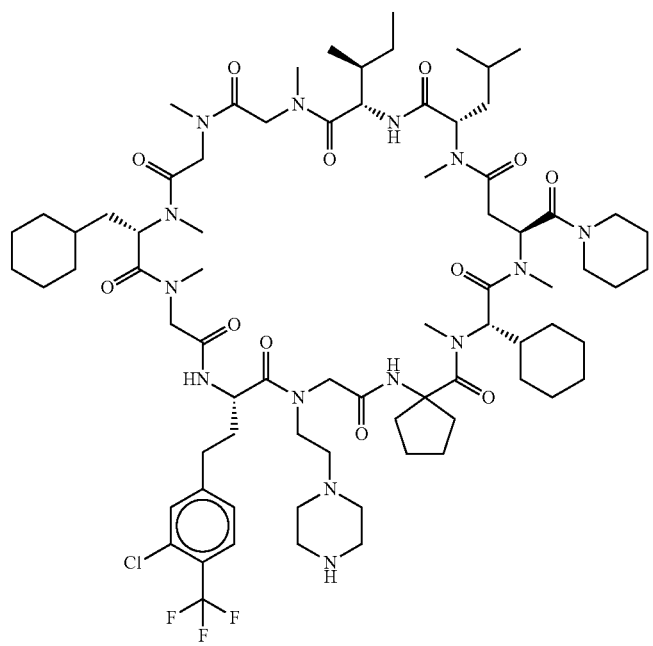 |
| 2185 | 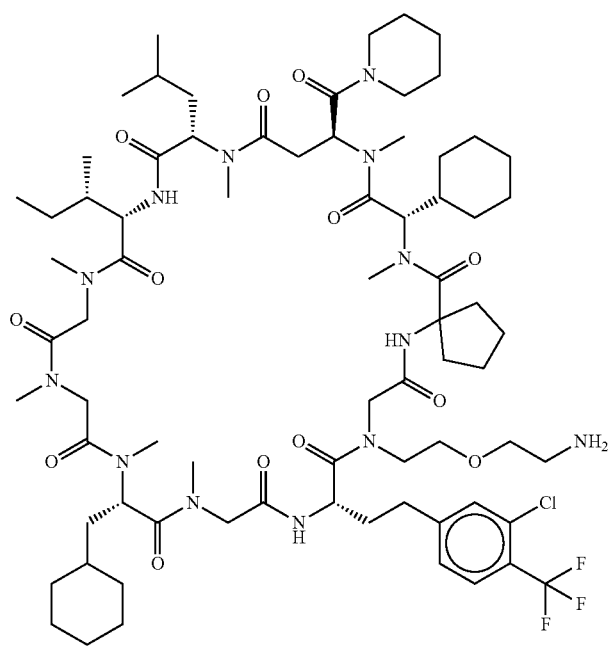 |

TABLE 24-continued

| Compound No. | Structural formula |
|---|---|
| 2186 | |

INDUSTRIAL APPLICABILITY

The present invention provides cyclic peptide compounds having a Kras inhibitory effect. The present invention also provides amino acids useful as raw materials for the cyclic peptide compounds.

The invention claimed is:

1. A compound, which is (5S,8S,11S,15S,18S,23aS,29S,35S,37aS)-8-((S)-sec-butyl)-18-cyclopentyl-29-(3,5-difluoro-4-(trifluoromethyl) phenethyl)-36-ethyl-11-isobutyl-N,N,5,6,12,16,19,33-octamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide.

2. A solvate of (5S,8S,11S,15S,18S,23aS,29S,35S,37aS)-8-((S)-sec-butyl)-18-cyclopentyl-29-(3,5-difluoro-4-(trifluoromethyl)phenethyl)-36-ethyl-11-isobutyl-N,N,5,6,12,16,19,33-octamethyl-35-(4-methylbenzyl)-4,7,10,13,17,20,23,28,31,34,37-undecaoxotetratriacontahydro-2H,4H-spiro[azeto[2,1-u]pyrrolo[2,1-i][1,4,7,10,13,16,19,22,25,28,31]undecaazacyclotetratriacontine-21,1'-cyclopentane]-15-carboxamide.

3. The solvate according to claim 2, which is a hydrate.

4. A pharmaceutical composition comprising the compound of claim 1.

5. A pharmaceutical composition comprising the solvate of claim 2.

6. A pharmaceutical composition comprising the solvate of claim 3.

7. A method of treating cancer in a subject, the method comprising administering to the subject a pharmaceutical composition comprising an effective amount of the compound of claim 1, wherein the cancer is pancreatic cancer.

8. The method of claim 7, wherein the subject is human.

9. A method of treating cancer in a subject, the method comprising administering to the subject a pharmaceutical composition comprising an effective amount of the solvate of claim 2, wherein the cancer is pancreatic cancer.

10. The method of claim 9, wherein the subject is human.

11. A method of treating cancer in a subject, the method comprising administering to the subject a pharmaceutical composition comprising an effective amount of the solvate of claim 3, wherein the cancer is pancreatic cancer.

12. The method of claim 11, wherein the subject is human.

* * * * *